(12) United States Patent
Wu et al.

(10) Patent No.: US 11,648,254 B2
(45) Date of Patent: May 16, 2023

(54) SUBSTITUTED PYRIDO[2,3-D]PYRIMIDINES AS INHIBITORS OF RAS PATHWAY SIGNALING

(71) Applicant: Kumquat Biosciences Inc., San Diego, CA (US)

(72) Inventors: Baogen Wu, San Diego, CA (US); Xiangzhu Wang, San Diego, CA (US); Xiaoming Li, San Diego, CA (US); Zhiyong Chen, San Diego, CA (US); Pingda Ren, San Diego, CA (US); Yi Liu, San Diego, CA (US)

(73) Assignee: Kumquat Biosciences Inc., San Diego, CA (US)

( * ) Notice: Subject to any disclaimer, the term of this patent is extended or adjusted under 35 U.S.C. 154(b) by 0 days.

(21) Appl. No.: 17/685,370

(22) Filed: Mar. 2, 2022

(65) Prior Publication Data
US 2023/0064360 A1      Mar. 2, 2023

Related U.S. Application Data

(60) Provisional application No. 63/200,353, filed on Mar. 2, 2021, provisional application No. 63/249,548, filed on Sep. 28, 2021, provisional application No. 63/249,549, filed on Sep. 28, 2021.

(51) Int. Cl.
| | | |
|---|---|---|
| *A61K 31/519* | (2006.01) | |
| *C07D 487/04* | (2006.01) | |
| *C07D 471/04* | (2006.01) | |
| *A61K 45/06* | (2006.01) | |
| *A61K 31/5377* | (2006.01) | |
| *A61K 31/506* | (2006.01) | |
| *A61P 35/00* | (2006.01) | |
| *A61K 31/541* | (2006.01) | |

(52) U.S. Cl.
CPC .......... *A61K 31/519* (2013.01); *A61K 31/506* (2013.01); *A61K 31/5377* (2013.01); *A61K 31/541* (2013.01); *A61K 45/06* (2013.01); *A61P 35/00* (2018.01); *C07D 471/04* (2013.01); *C07D 487/04* (2013.01)

(58) Field of Classification Search
CPC .......................... A61K 31/519; C07D 487/04
USPC ...................... 514/264.11; 544/279
See application file for complete search history.

(56) References Cited

U.S. PATENT DOCUMENTS 11,168,102 B1    11/2021   Gill et al.

FOREIGN PATENT DOCUMENTS

| | | |
|---|---|---|
| CN | 106565684 A | 4/2017 |
| CN | 113801114 A | 12/2021 |
| CN | 114436976 A | 5/2022 |
| CN | 114539245 A | 5/2022 |
| WO | WO-2005061497 A1 | 7/2005 |
| WO | WO-2011011522 A2 | 1/2011 |
| WO | WO-2014145512 A2 | 9/2014 |
| WO | WO-2015018797 A2 | 2/2015 |
| WO | WO-2018115380 A1 | 6/2018 |
| WO | WO-2018134685 A2 | 7/2018 |
| WO | WO-2018172250 A1 | 9/2018 |
| WO | WO-2019122129 A1 | 6/2019 |
| WO | WO-2019201848 A1 | 10/2019 |
| WO | WO-2019231271 A1 | 12/2019 |
| WO | WO-2021074227 A1 | 4/2021 |
| WO | WO-2021092115 A1 | 5/2021 |
| WO | WO-2021249519 A1 | 12/2021 |
| WO | WO-2022058344 A1 | 3/2022 |
| WO | WO-2022083657 A1 | 4/2022 |
| WO | WO-2022160931 A1 | 8/2022 |
| WO | WO-2022161461 A1 | 8/2022 |
| WO | WO-2022187411 A1 * | 9/2022 |

OTHER PUBLICATIONS

Jordan, V. C. Nature Reviews: Drug Discovery, 2, 2003, 205.*
Vippagunta, et al. Advanced Drug Delivery Reviews, 48, 2001, 18.*
International Search Report and Written Opinion dated Jun. 22, 2022 for PCT/US2022/018584.

* cited by examiner

*Primary Examiner* — Douglas M Willis
(74) *Attorney, Agent, or Firm* — Wilson Sonsini Goodrich & Rosati

(57) ABSTRACT

The present disclosure provides compounds represented by Formula (I-1):

Formula (I-1)

Figure 1:
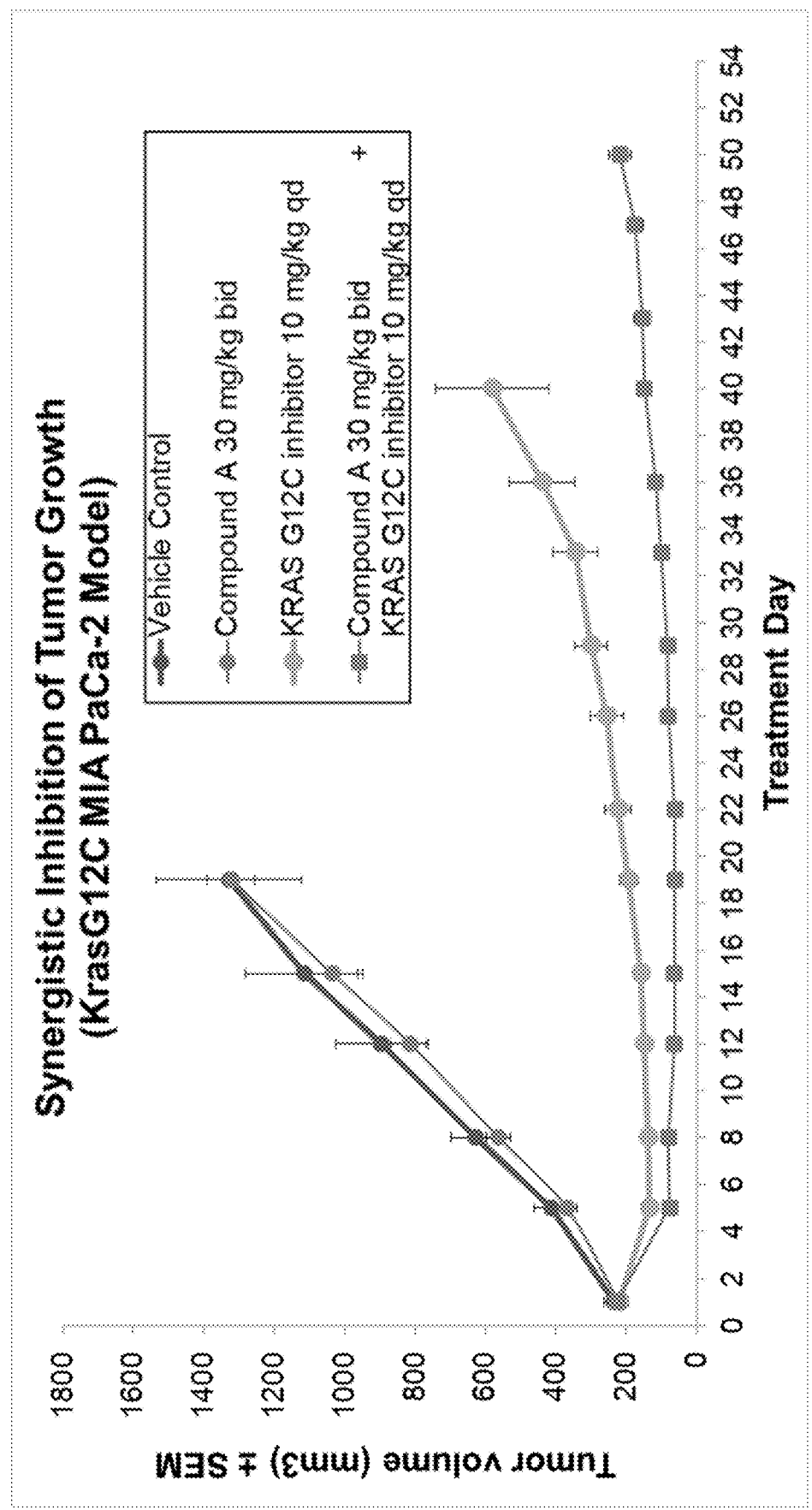

and pharmaceutically acceptable salts thereof, and methods of using the same. The compounds and methods have a range of utilities as therapeutics, diagnostics, and research tools. In particular, the subject compositions and methods are useful for reducing signaling output of oncogenic proteins.

30 Claims, 2 Drawing Sheets

Specification includes a Sequence Listing.

SUBSTITUTED PYRIDO[2,3-D]PYRIMIDINES AS INHIBITORS OF RAS PATHWAY SIGNALING

CROSS-REFERENCE

This application claims priority to U.S. Provisional Application Nos. 63/200,353 filed on Mar. 2, 2021, 63/249,548 filed on Sep. 28, 2021, and 63/249,549 filed on Sep. 28, 2021, each of which is incorporated by reference in its entirety.

SEQUENCE LISTING

The instant application contains a Sequence Listing which has been submitted electronically in ASCII format and is hereby incorporated by reference in its entirety. Said ASCII copy, created on Aug. 2, 2022, is named 56690_727_201_SL.txt and is 25,376 bytes in size.

BACKGROUND

Cancer (e.g., tumor, neoplasm, metastases) is the second leading cause of death worldwide estimated to be responsible for about 10 million deaths each year. Many types of cancers are marked with mutations in one or more proteins involved in various signaling pathways leading to unregulated growth of cancerous cells. In some cases, about 25 to 30 percent (%) of tumors are known to harbor Rat sarcoma (Ras) mutations.

Activated by guanine nucleotide exchange factors (GEFs), Ras in its GTP-bound state interacts with a number of effectors. Return to the inactive state is driven by GTPase-activating proteins (GAPs), which down-regulate active Ras by accelerating the weak intrinsic GTPase activity. For oncogenic Ras mutants, however, the GAP activity is impaired or greatly reduced, resulting in persistent activation, which drives the oncogenic Ras signaling through, e.g., the RAS-RAF-MEK-ERK and RAS-PI3K-PDK1-AKT pathways, both essential to cell survival and proliferation.

The most-studied GEF for Ras is the protein Son of Sevenless (SOS) for which two human isoforms, SOS1 and SOS2, are known. SOS1 is a human homologue of the originally identified *Drosophila* protein Son of Sevenless. SOS1 has two binding sites for Ras proteins; a catalytic site that binds GDP-bound Ras proteins to promote guanine nucleotide exchange and an allosteric site that binds GTP-bound Ras to further promote activation of Ras proteins. Son of Sevenless 2 (SOS2) is a homolog of SOS1 in mammalian cells. Double SOS1 and SOS2 knockout leads to rapid lethality in adult mice (Baltanas et al., Mol. Cell. Biol., 2013, 33(22):4562-78).

Although Kras is known to be an oncogenic driver, there is no clinically approved targeted therapy for Ras mutant cancers thus far. Ras proteins have long been considered to be "undruggable," due to, in part, high affinity to their substrate Guanosine-5'-triphosphate (GTP) and/or their smooth surfaces without any obvious targeting region. Recently, a specific G12C Ras gene mutation has been identified as a druggable target. However, such therapeutic approach is still limiting, as the G12C mutation in Ras has a low prevalence rate (e.g., about 3% in pancreatic ductal adenocarcinoma) as compared to other known Ras mutations including G12D and G12V.

SUMMARY

In view of the foregoing, there remains a considerable need for a new design of therapeutics and diagnostics that can specifically inhibit Ras pathway signaling by, e.g., inhibiting a GEF such as a SOS protein. Such compositions and methods can be particularly useful for treating a variety of the diseases including, but not limited to, cancers and neoplasia conditions. The present disclosure addresses these needs, and provides additional advantages applicable for diagnosis, prognosis, and treatment for a wide diversity of diseases.

In an aspect is provided a compound of Formula (I-1), or a pharmaceutically acceptable salt or solvate thereof:

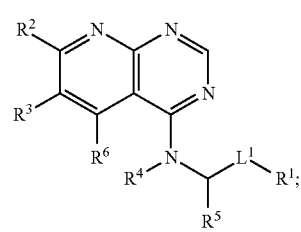

Formula (I-1)

wherein:
$R^1$ is a 6-10 membered aryl ring optionally substituted with one or more $R^{10}$;
$L^1$ is a bond;
$R^2$ is $-OR^{2a}$ or halogen;
$R^{2a}$ is selected from $C_{1-6}$alkyl, $C_{3-10}$cycloalkyl, $C_{2-9}$heterocycloalkyl, $C_{6-10}$aryl, $C_{1-9}$heteroaryl, wherein $C_{1-6}$alkyl, $C_{3-10}$cycloalkyl, $C_{2-9}$heterocycloalkyl, $C_{6-10}$aryl, and $C_{1-9}$heteroaryl are optionally substituted with one, two, or three $R^{20a}$;
$R^3$ is selected from halogen, $C_{1-6}$alkyl, $C_{3-14}$cycloalkyl, $C_{2-9}$heterocycloalkyl, $C_{6-10}$aryl, and $C_{1-9}$heteroaryl, wherein $C_{1-6}$alkyl, $C_{3-14}$cycloalkyl, $C_{2-9}$heterocycloalkyl, $C_{6-10}$aryl, and $C_{1-9}$heteroaryl are optionally substituted with one, two, or three $R^{20b}$;
$R^4$ is selected from hydrogen, $C_{1-6}$alkyl, and $C_{1-6}$haloalkyl;
$R^5$ is selected from hydrogen, $C_{1-6}$alkyl, and $C_{1-6}$haloalkyl;
$R^6$ is selected from hydrogen, halogen, $-CN$, and $C_{1-6}$alkyl, wherein $C_{1-6}$alkyl is optionally substituted with one, two, or three $R^{20c}$;
each $R^{10}$ is independently selected from halogen, $-CN$, $C_{1-6}$alkyl, $C_{3-7}$cycloalkyl, $C_{2-9}$heterocycloalkyl, $C_{6-10}$aryl, $C_{1-9}$heteroaryl, wherein $C_{1-6}$alkyl, $C_{3-7}$cycloalkyl, $C_{2-9}$heterocycloalkyl, $C_{6-10}$aryl, and $C_{1-9}$heteroaryl are optionally substituted with one, two, or three $R^{20d}$;
each $R^{20a}$, $R^{20b}$, $R^{20c}$, and $R^{20d}$ are each independently selected from halogen, oxo, $=NH$, $-CN$, $C_{1-6}$alkyl, $C_{2-6}$alkenyl, $C_{2-6}$alkynyl, $C_{3-10}$cycloalkyl, $-CH_2-C_{3-10}$cycloalkyl, $C_{2-9}$heterocycloalkyl, $-CH_2-C_{2-9}$heterocycloalkyl, $C_{6-10}$aryl, $-CH_2-C_{6-10}$aryl, $C_{1-9}$heteroaryl, $-OR^{21}$, $-SR^{21}$, $-N(R^{22})(R^{23})$, $-C(O)OR^{22}$, $-C(O)N(R^{22})(R^{23})$, $-C(O)C(O)N(R^{22})(R^{23})$, $-OC(O)N(R^{22})(R^{23})$, $-N(R^{24})C(O)N(R^{22})(R^{23})$, $-N(R^{24})C(O)OR^{25}$, $-N(R^{24})C(O)R^{25}$, $-N(R^{24})S(O)_2R^{25}$, $-C(O)R^{25}$, $-S(O)_2R^{25}$, $-S(O)_2N(R^{22})(R^{23})$, $-OCH_2C(O)OR^{22}$, and $-OC(O)R^{25}$, wherein $C_{1-6}$alkyl, $C_{2-6}$alkenyl, $C_{2-6}$alkynyl, $C_{3-10}$cycloalkyl, $-CH_2-C_{3-10}$cycloalkyl, $C_{2-9}$heterocycloalkyl, $-CH_2-C_{2-9}$heterocycloalkyl, $C_{6-10}$aryl, $-CH_2-C_{6-10}$aryl, and $C_{1-9}$heteroaryl are optionally substituted with one, two, or three groups independently selected from halogen, oxo, $=NH$, $-CN$, $C_{1-6}$alkyl, $C_{1-6}$haloalkyl, $C_{1-6}$alkoxy, $C_{1-6}$haloalkoxy, $-OR^{21}$, $-SR^{21}$, $-N(R^{22})(R^{23})$, $-C(O)OR^{22}$, $-C(O)N(R^{22})(R^{23})$, $-C(O)C(O)N(R^{22})(R^{23})$, $-OC(O)N(R^{22})$ ($R^{23}$), —N($R^{24}$)C(O)N($R^{22}$)($R^{23}$), —N($R^{24}$)C(O)O$R^{25}$, —N($R^{24}$)C(O)$R^{25}$, —N($R^{24}$)S(O)$_2R^{25}$, —C(O)$R^{25}$, —S(O)$_2R^{25}$, —S(O)$_2$N($R^{22}$)($R^{23}$), and —OC(O)$R^{25}$;

each $R^{21}$ is independently selected from H, $C_{1-6}$alkyl, $C_{1-6}$haloalkyl, $C_{2-6}$alkenyl, $C_{2-6}$alkynyl, $C_{3-7}$cycloalkyl, $C_{2-9}$heterocycloalkyl, $C_{6-10}$aryl, and $C_{1-9}$heteroaryl, wherein $C_{3-7}$cycloalkyl, $C_{2-9}$heterocycloalkyl, $C_{6-10}$aryl, and $C_{1-9}$heteroaryl are optionally substituted with one, two, or three groups independently selected from halogen and $C_{1-6}$alkyl;

each $R^{22}$ is independently selected from H, $C_{1-6}$alkyl, $C_{1-6}$haloalkyl, $C_{2-6}$alkenyl, $C_{2-6}$alkynyl, $C_{3-7}$cycloalkyl, $C_{2-9}$heterocycloalkyl, $C_{6-10}$aryl, and $C_{1-9}$heteroaryl, wherein $C_{3-7}$cycloalkyl, $C_{2-9}$heterocycloalkyl, $C_{6-10}$aryl, and $C_{1-9}$heteroaryl are optionally substituted with one, two, or three groups independently selected from halogen and $C_{1-6}$alkyl;

each $R^{23}$ is independently selected from H and $C_{1-6}$alkyl;
each $R^{24}$ is independently selected from H and $C_{1-6}$alkyl; and each $R^{25}$ is selected from $C_{1-6}$alkyl, $C_{2-6}$alkenyl, $C_{2-6}$alkynyl, $C_{3-7}$cycloalkyl, $C_{2-9}$heterocycloalkyl, $C_{6-10}$aryl, and $C_{1-9}$heteroaryl, wherein $C_{1-6}$alkyl, $C_{3-7}$cycloalkyl, $C_{2-9}$heterocycloalkyl, $C_{6-10}$aryl, and $C_{1-9}$heteroaryl are optionally substituted with one, two, or three groups independently selected from halogen, $C_{1-6}$alkyl, $C_{1-6}$haloalkyl, $C_{1-6}$alkoxy, $C_{3-7}$cycloalkyl, $C_{2-9}$heterocycloalkyl, $C_{6-10}$aryl, and $C_{1-9}$heteroaryl.

In some embodiments, the compound has the structure of Formula (Ia-1), or a pharmaceutically acceptable salt or solvate thereof:

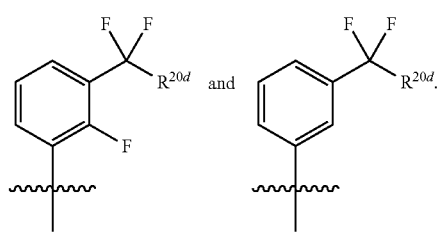

Formula (Ia-1)

In some embodiments, $R^{2a}$ is $C_{1-6}$alkyl optionally substituted with one, two, or three $R^{20a}$. In some embodiments, $R^{2a}$ is unsubstituted $C_{1-6}$alkyl. In some embodiments, $R^{2a}$ is —CH$_3$.

In some embodiments, $R^3$ is $C_{2-9}$heterocycloalkyl optionally substituted with one, two, or three $R^{20b}$. In some embodiments, $R^3$ is $C_{3-10}$cycloalkyl optionally substituted with one, two, or three $R^{20b}$. In some embodiments, $R^3$ is $C_{3-4}$cycloalkyl optionally substituted with one $R^{20b}$. In some embodiments, $R^{20b}$ is —CN or halogen. In some embodiments, $R^3$ is

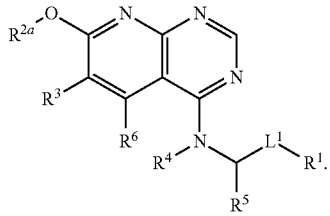

In some embodiments, $R^6$ is selected from hydrogen, halogen, and unsubstituted $C_{1-6}$alkyl. In some embodiments, $R^6$ is hydrogen.

In some embodiments, $R^5$ is $C_{1-6}$alkyl.
In some embodiments, $R^5$ is —CH$_3$.
In some embodiments, $R^4$ is hydrogen.
In some embodiments, $R^1$ is phenyl substituted with one or more $R^{10}$. In some embodiments, each $R^{10}$ is independently selected from halogen and $C_{1-6}$alkyl, wherein $C_{1-6}$alkyl is optionally substituted with one, two, or three $R^{20d}$. In some embodiments, each $R^{10}$ is independently selected from halogen and $C_{1-6}$alkyl, wherein $C_{1-6}$alkyl is substituted with one, two, or three $R^{20d}$, and each $R^{20d}$ is halogen or —OH.
In some embodiments, $R^1$ is independently selected from

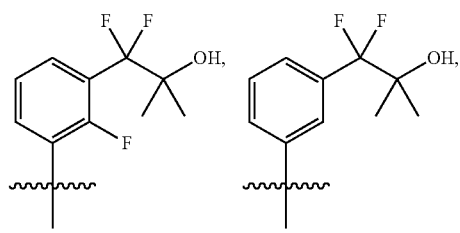

In some embodiments, $R^{20a}$ is $C_{1-6}$alkyl optionally substituted with one, two, or three groups independently selected from F and —OH. In some embodiments, $R^{20d}$ is $C_{1-3}$alkyl substituted with one —OH. In some embodiments, $R^1$ is selected from

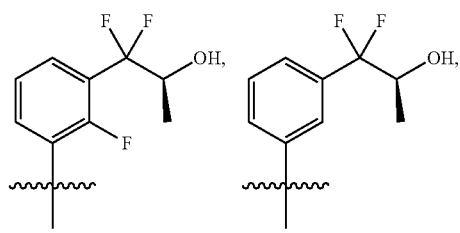

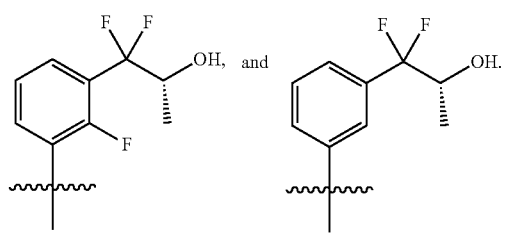

In an aspect is provided a compound selected from:
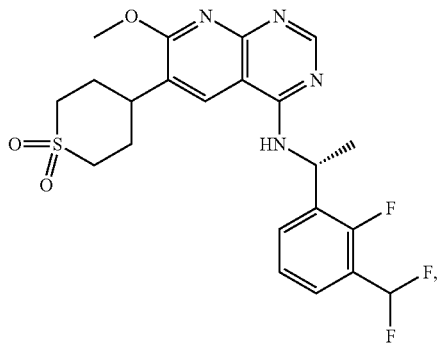
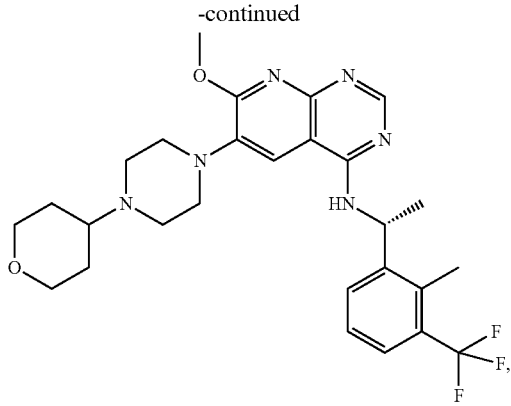
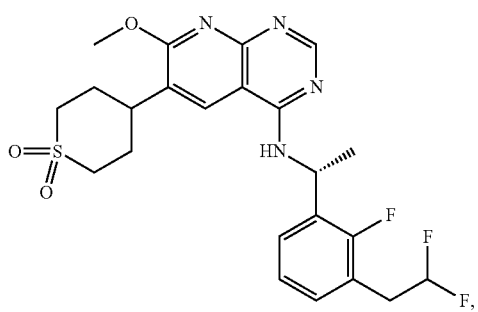
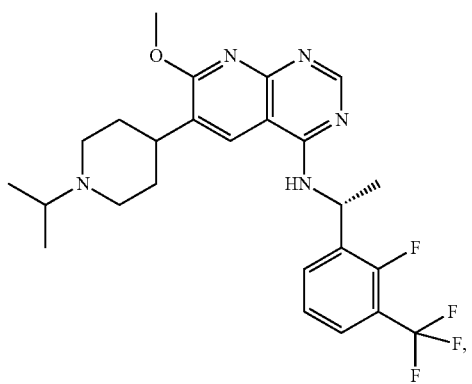
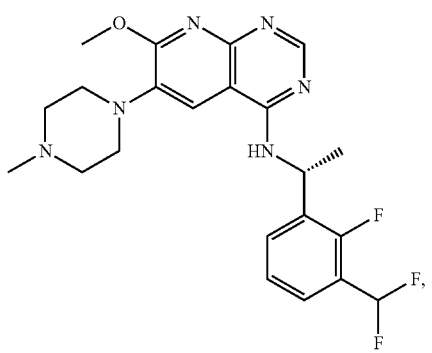
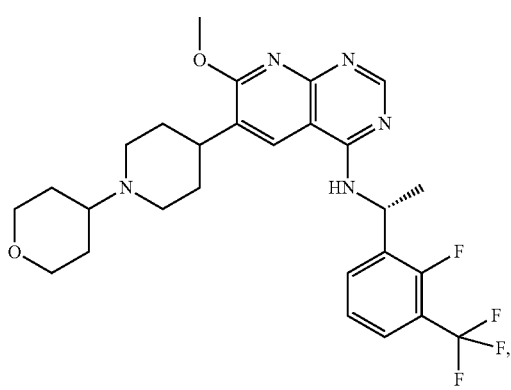
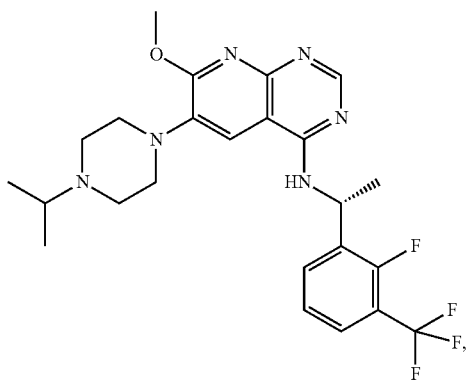
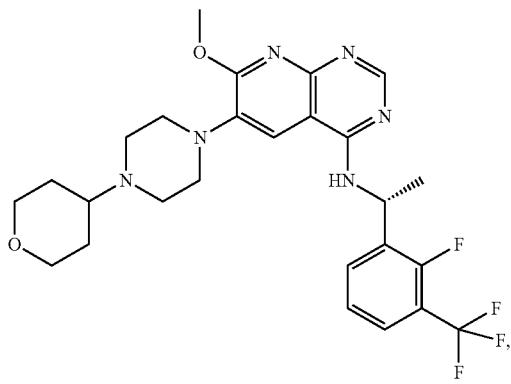

-continued
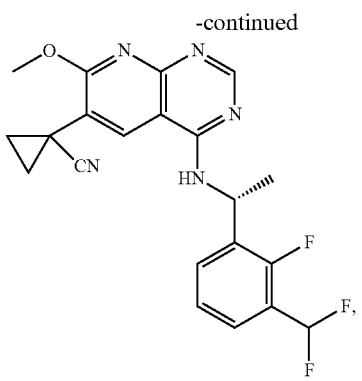
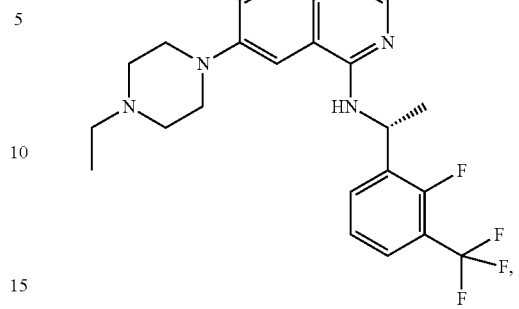
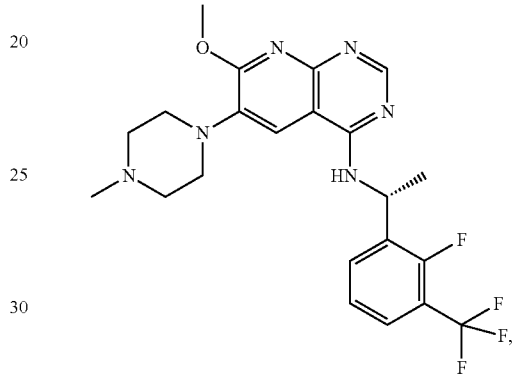
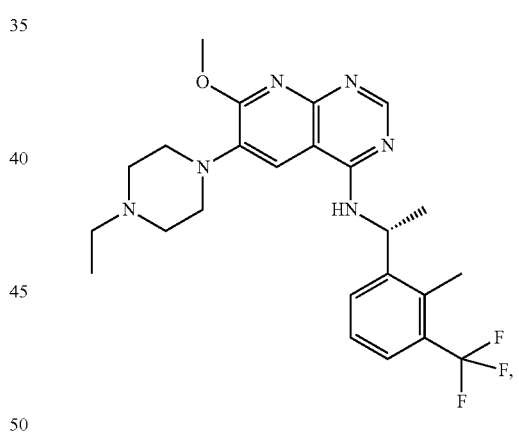
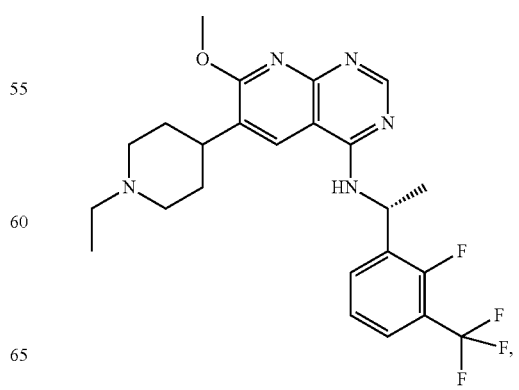

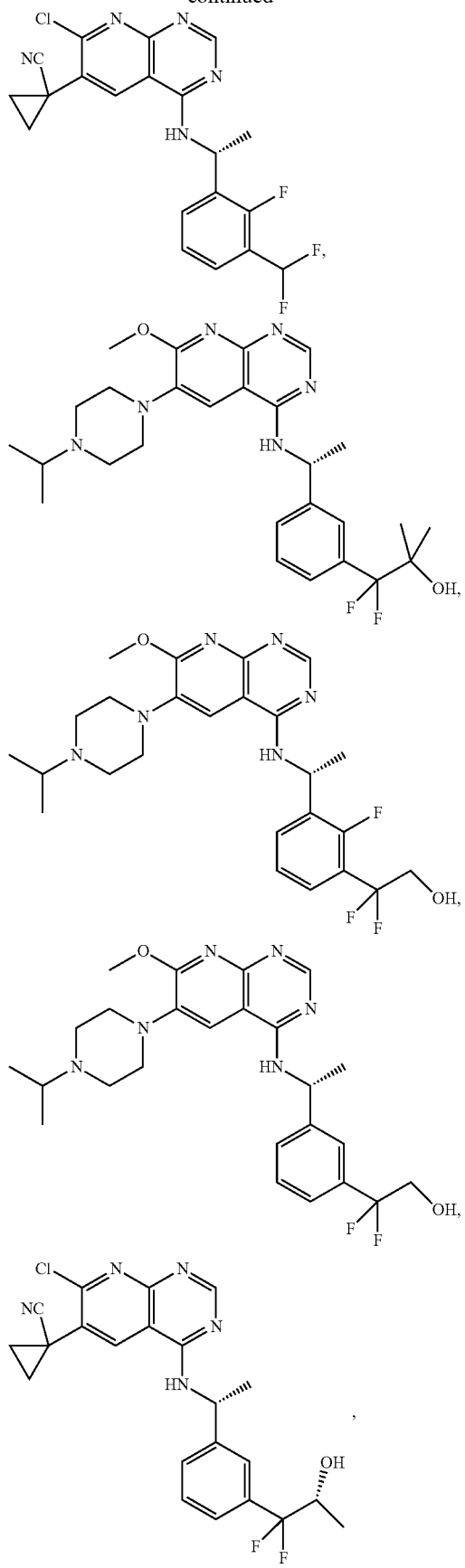
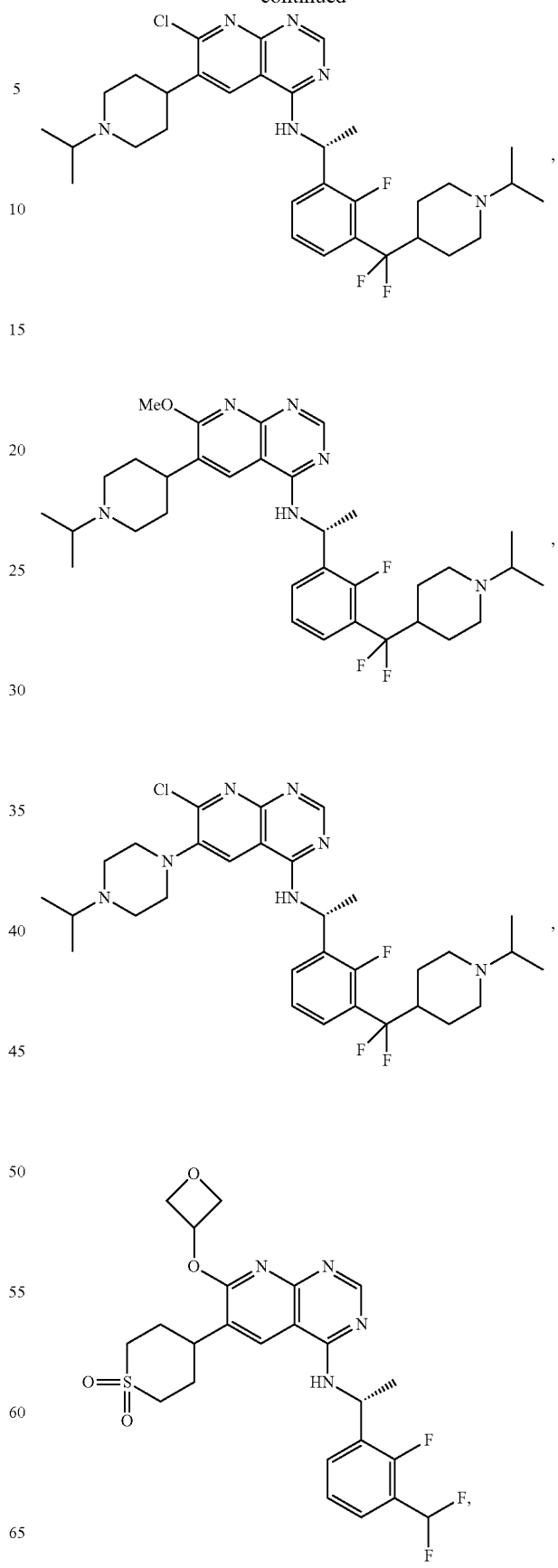

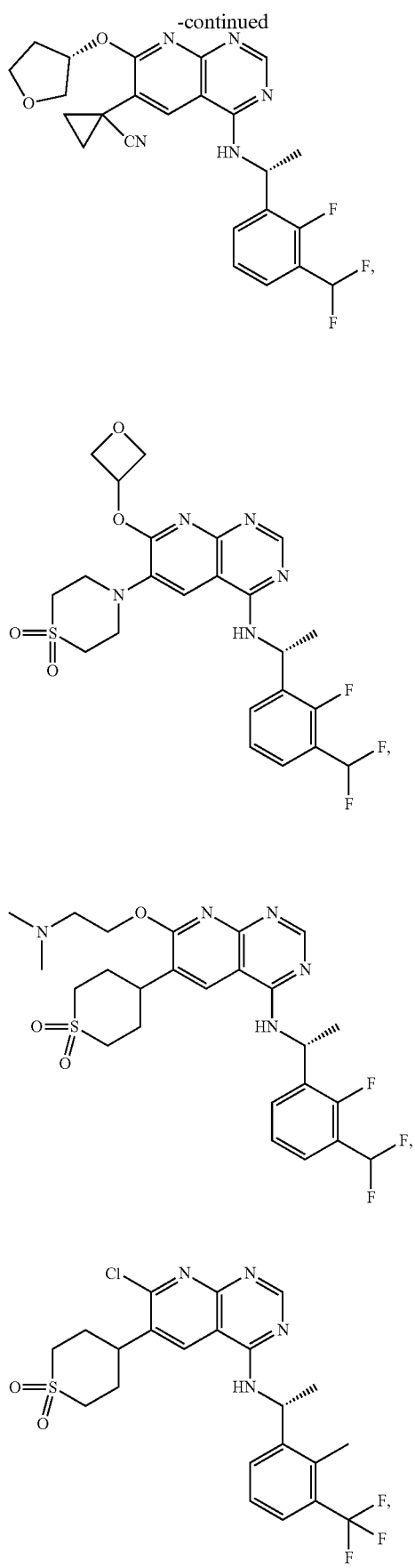
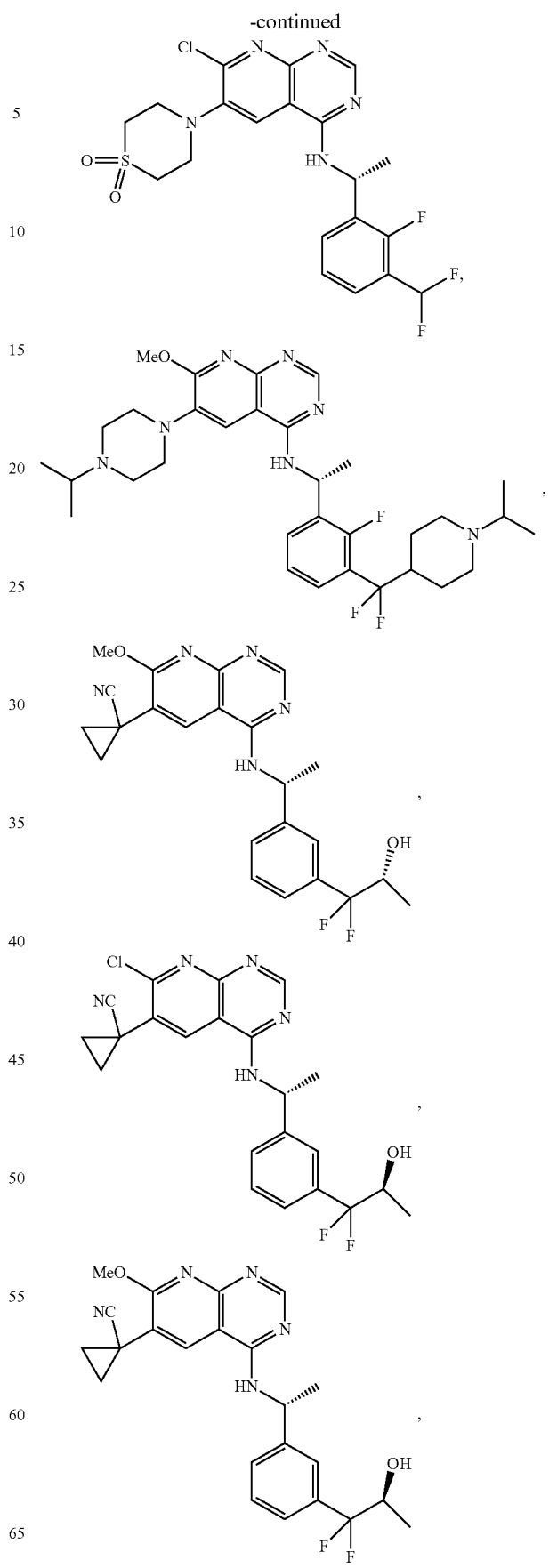

13
-continued
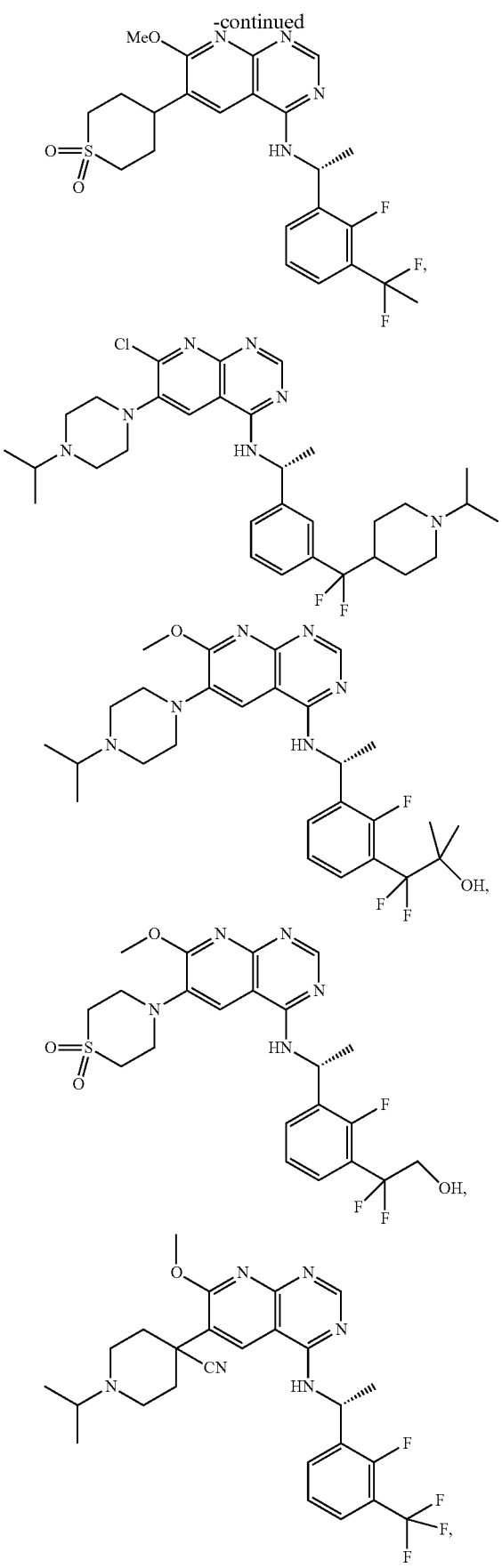
14
-continued
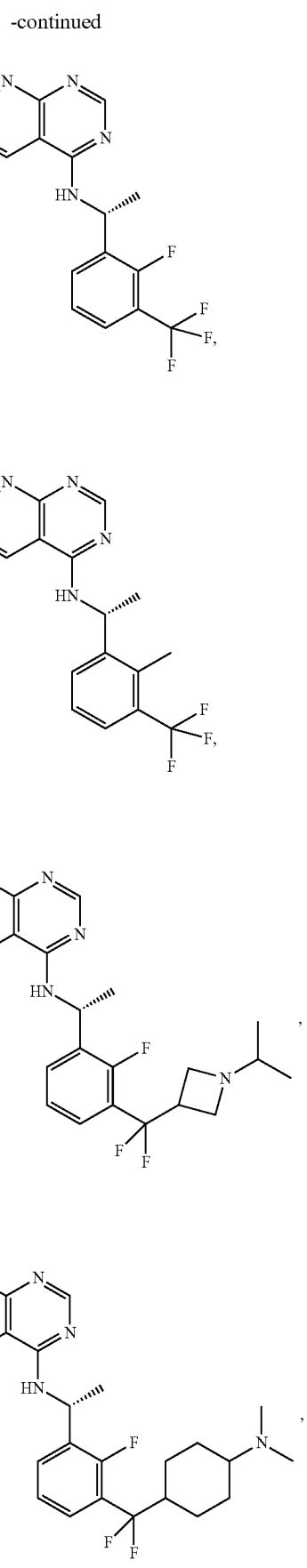

-continued
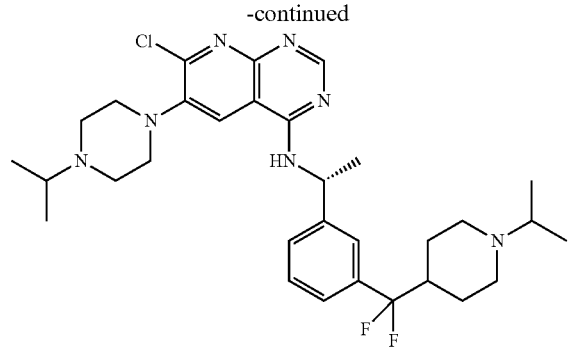
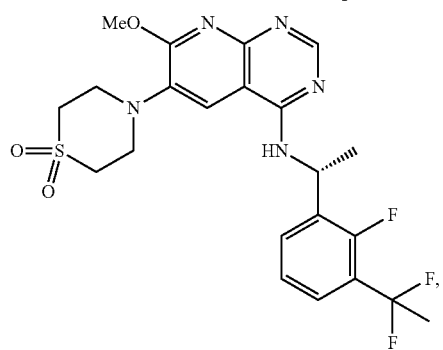
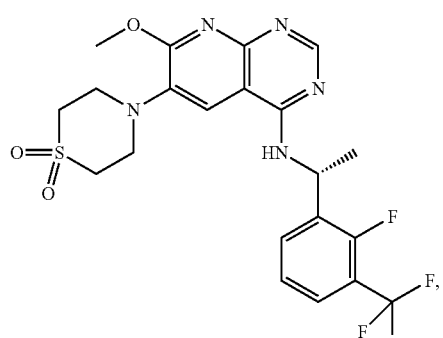
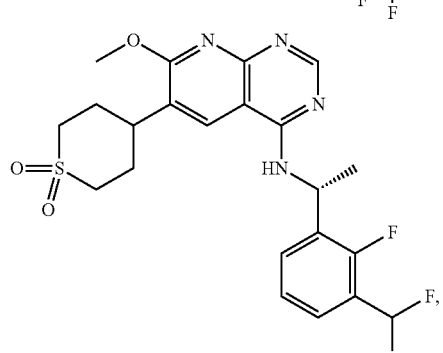
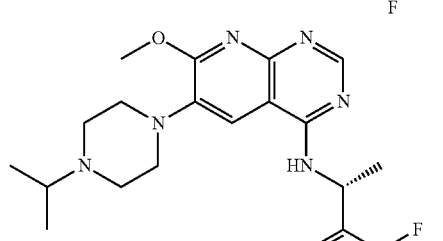
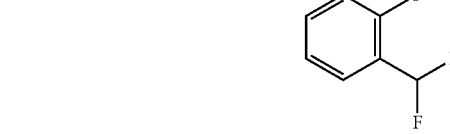
-continued
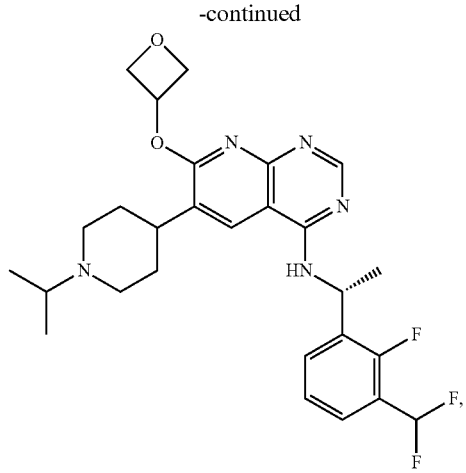
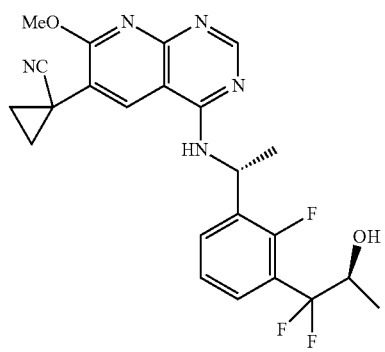
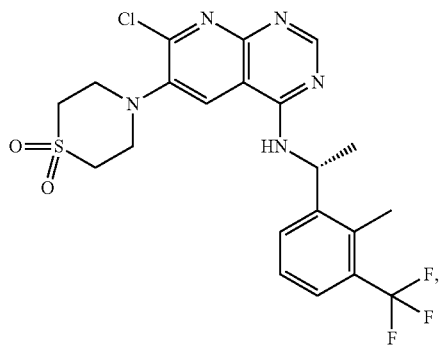
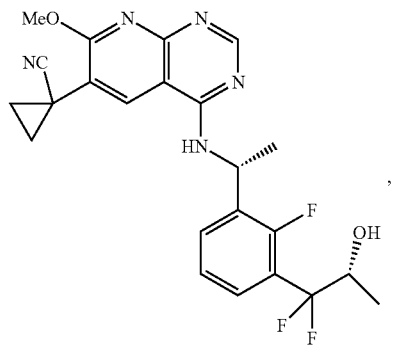

-continued
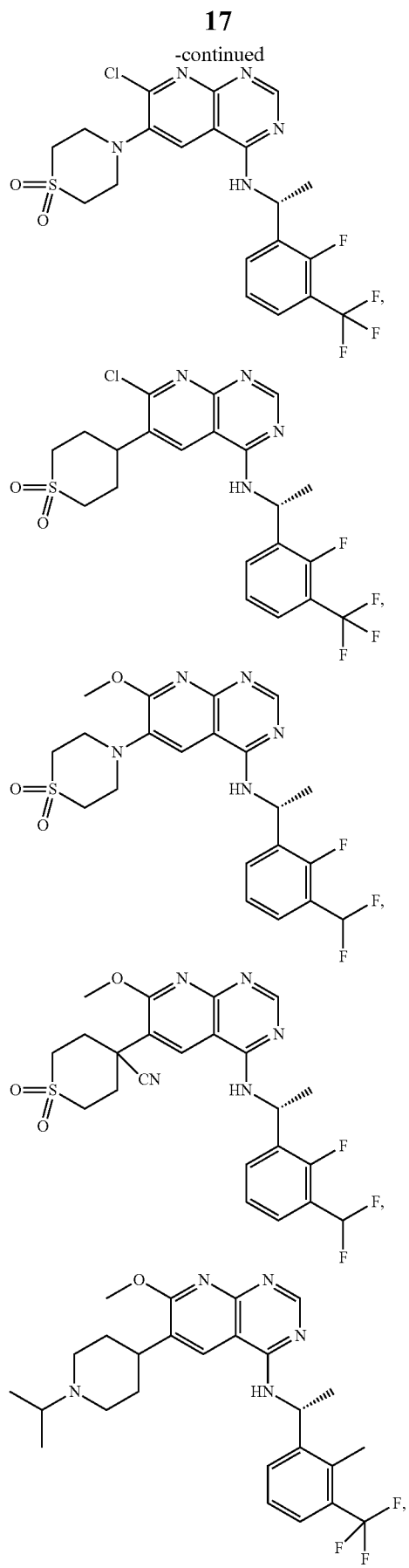
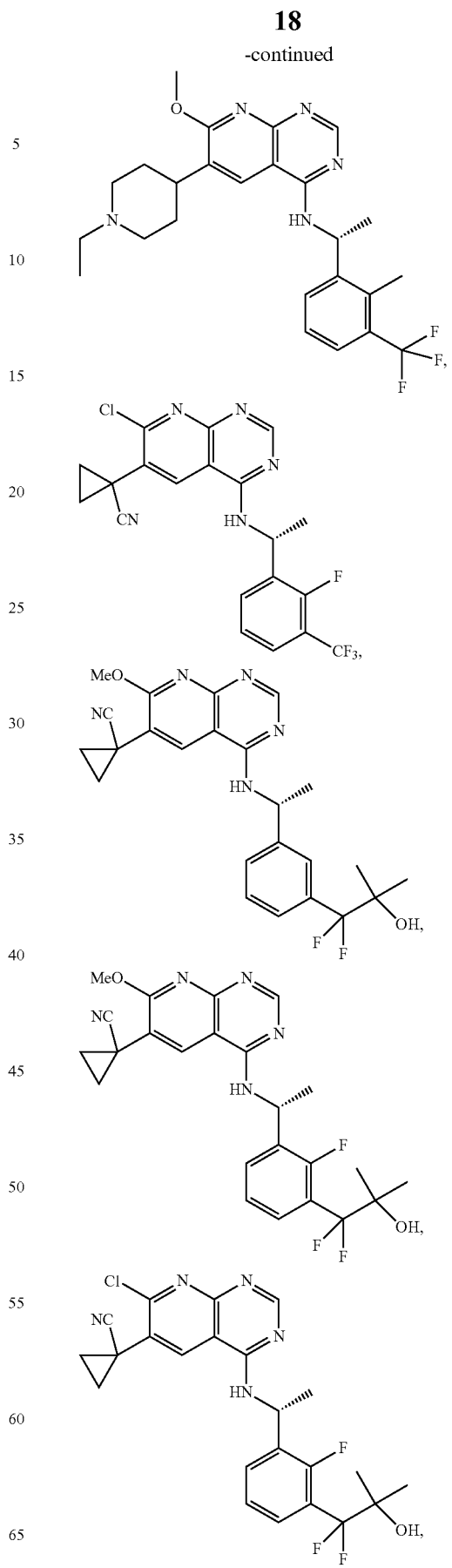

-continued
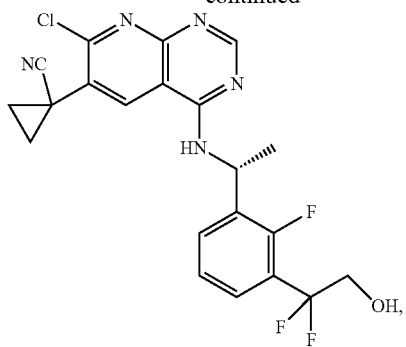
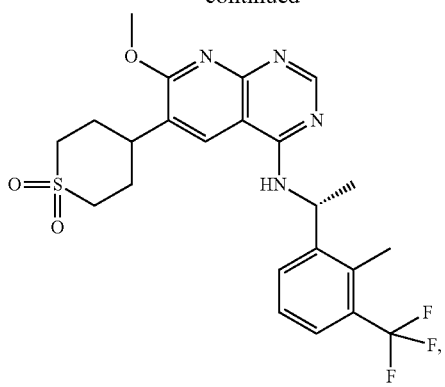
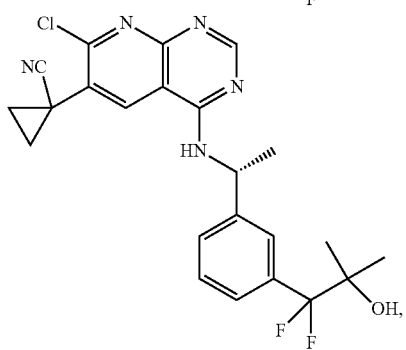
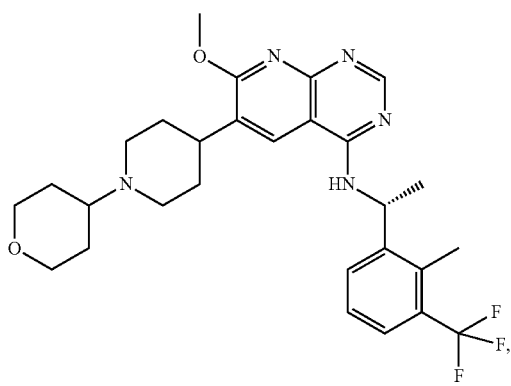
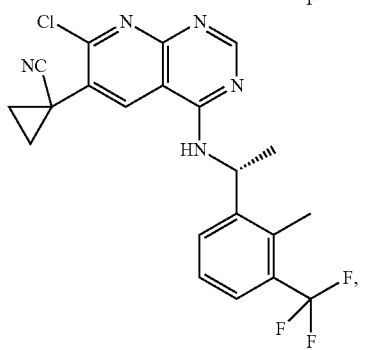
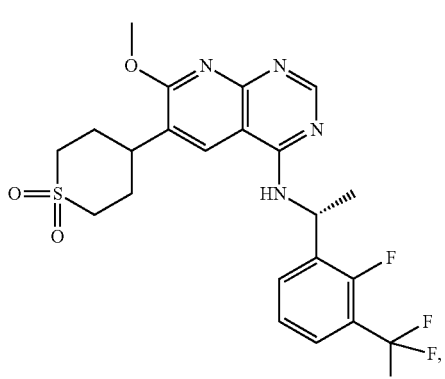
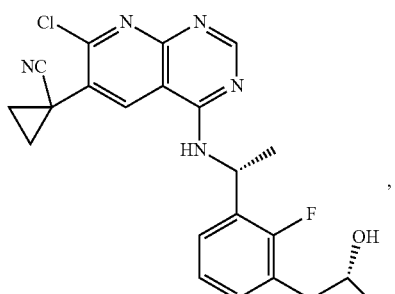
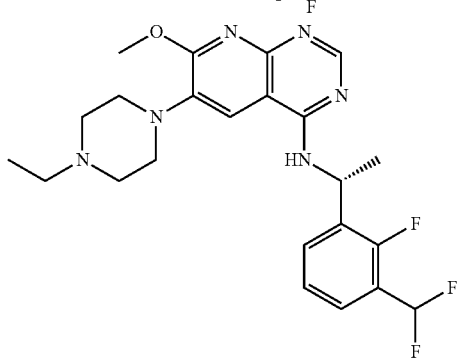
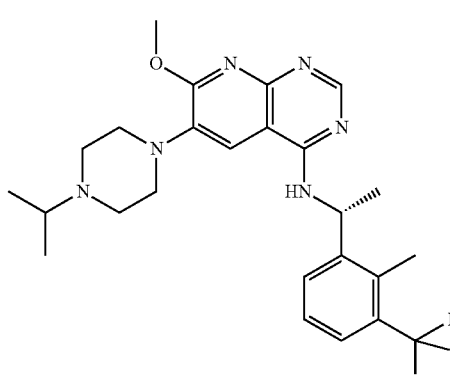

21
-continued
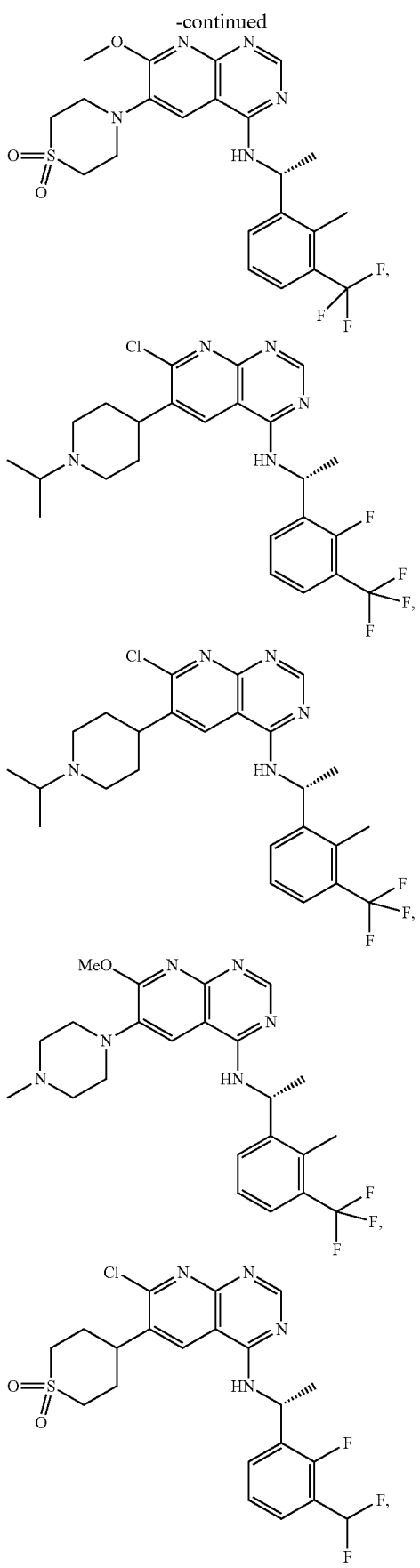
22
-continued
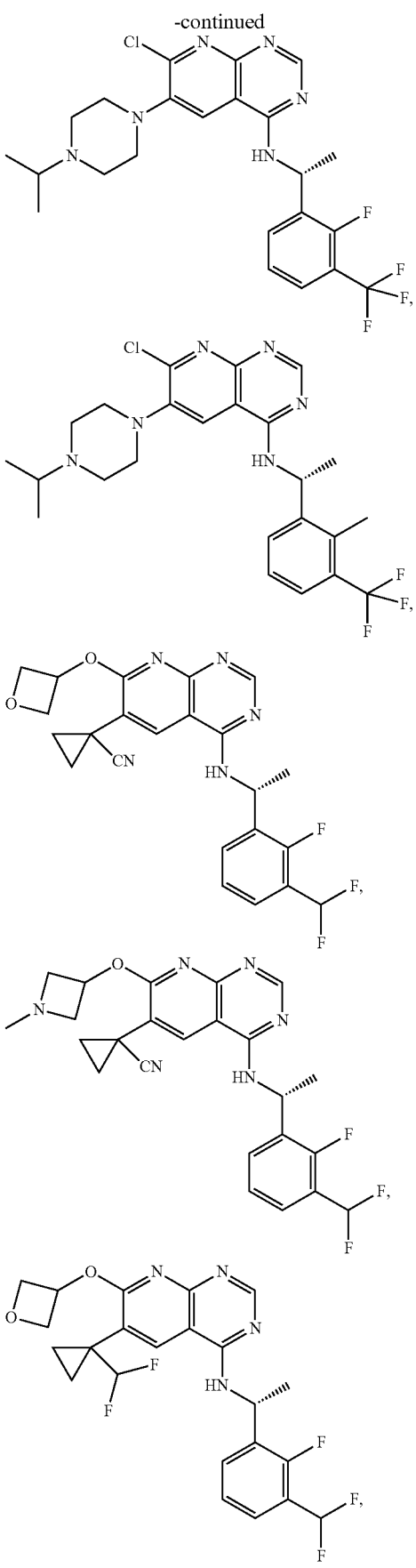

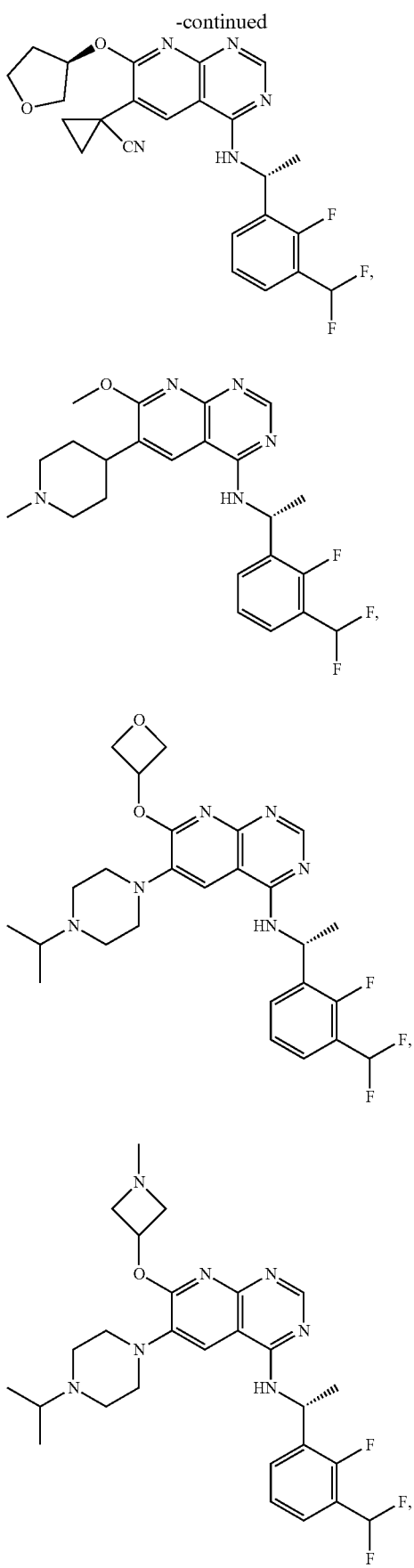
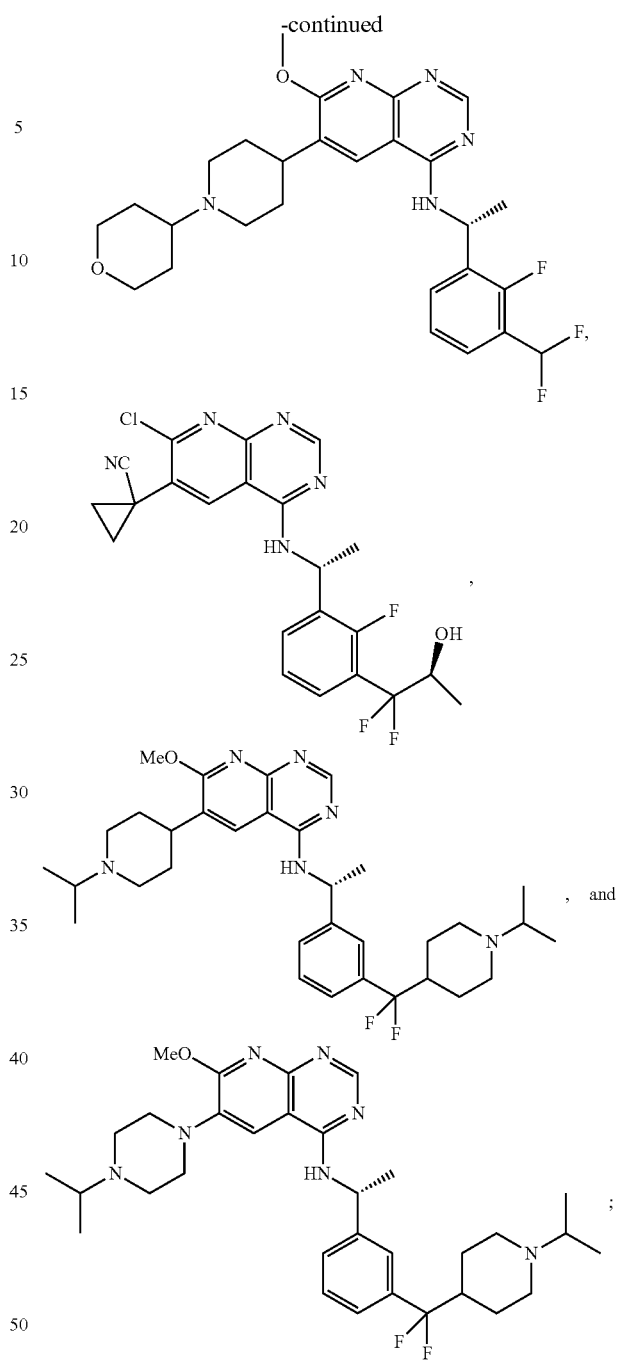

or a pharmaceutically acceptable salt or solvate thereof.

In an aspect is provided a pharmaceutical composition comprising a compound described herein, or a pharmaceutically acceptable salt or solvate thereof, and a pharmaceutically acceptable excipient.

In an aspect is provided a method of inhibiting cell growth, comprising administering a cell expressing SOS1 with an effective amount of a compound described herein, or a pharmaceutically acceptable salt or solvate thereof, thereby inhibiting growth of said cells.

In some embodiments, the cell is a cancer cell. In some embodiments, the method further comprises administering an additional agent to the cell.

In an aspect is provided a compound of Formula (I-1), or a pharmaceutically acceptable salt or solvate thereof:

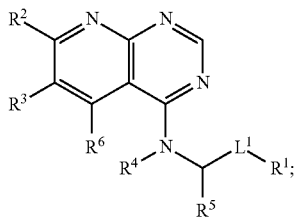

Formula (I-1)

wherein:
R[1] is a 3-12 membered cycloalkyl ring, 3-12 membered heterocycloalkyl ring, 6-10 membered aryl ring, or 5-10 membered heteroaryl ring, wherein the 3-12 membered cycloalkyl ring, 3-12 membered heterocycloalkyl ring, 6-10 membered aryl ring, and 5-10 membered heteroaryl ring are optionally substituted with one or more R[10];

L[1] is a bond or $C_{1-6}$alkyl;

R[2] is —OR[2a], —NR[2b]R[2c], —SR[2g], —S(O)R[2h], —S(O)$_2$R[2h], —S(O)$_2$NR[2b]R[2c], —C(R[2a])(R[2e])(R[2f]), C(O)NR[2b]R[2c], —CN, or halogen;

R[2a] is selected from $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —C(O)OR[12], —C(O)R[15], —C(O)N(R[12])(R[13]), —S(O)$_2$R[15], —S(O)$_2$N(R[12])(R[13]), and hydrogen, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three R[20a];

R[2b] is selected from hydrogen, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —C(O)OR[12], —C(O)R[15], —C(O)N(R[12])(R[13]), —S(O)$_2$R[15], and —S(O)$_2$N(R[12])(R[13]), wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three R[20a];

R[2c] is selected from hydrogen, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three R[20a]; or R[2b] and R[2c], together with the nitrogen to which they are attached, form a $C_{2-9}$heterocycloalkyl ring optionally substituted with one, two, or three R[20a];

R[2d] is selected from hydrogen, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —OR[12], —SR[12], —N(R[12])(R[13]), —C(O)OR[12], —OC(O)N(R[12])(R[13]), —N(R[14])C(O)N(R[12])(R[13]), —N(R[14])C(O)OR[15], —N(R[14])S(O)$_2$R[15], —C(O)R[15], —S(O)R[15], —OC(O)R[15], —C(O)N(R[12])(R[13]), —C(O)C(O)N(R[12])(R[13]), —N(R[14])C(O)R[15], —S(O)$_2$R[15], —S(O)$_2$N(R[12])(R[13]), —S(=O)(=NH)N(R[12])(R[13]), —CH$_2$C(O)N(R[12])(R[13]), —CH$_2$N(R[14])C(O)R[15], —CH$_2$S(O)$_2$R[15], —CH$_2$S(O)$_2$N(R[12])(R[13]), —CH$_2$N(R[12])S(O)$_2$(R[13]), and —P(O)(R[17])(R[17a]), wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three R[20a];

R[2e] is selected from hydrogen, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three R[20a];

R[2f] is selected from hydrogen, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three R[20a];

R[2g] is selected from hydrogen, $C_{2-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —C(O)OR[12], —C(O)R[15], —C(O)N(R[12])(R[13]), —S(O)$_2$R[15], —S(O)$_2$N(R[12])(R[13]), wherein $C_{2-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three R[20a];

R[2h] is selected from $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three R[20a];

R[3] is selected from halogen, $C_{1-6}$alkyl, $C_{2-6}$alkenyl, $C_{2-6}$alkynyl, $C_{3-14}$cycloalkyl, $C_{2-9}$heterocycloalkyl, $C_{6-10}$aryl, $C_{1-9}$heteroaryl, —SR[12], —N(R[12])(R[13]), —C(O)OR[12], —OC(O)N(R[12])(R[13]), —N(R[14])C(O)N(R[12])(R[13]), —N(R[14])C(O)OR[15], —N(R[14])S(O)$_2$R[15], N(R[14])S(O)R[15], —C(O)R[15], —S(O)R[15], —OC(O)R[15], —C(O)N(R[12])(R[13a]), —C(O)C(O)N(R[12])(R[13]), —N(R[14])C(O)R[15], —S(O)$_2$R[15], —S(O)$_2$N(R[12])(R[13]), —S(O)N(R[12])(R[13]), —S(=O)(=NH)N(R[12])(R[13]), —CH$_2$C(O)N(R[12])(R[13]), —CH$_2$N(R[14])C(O)R[15], —CH$_2$S(O)$_2$R[15], —CH$_2$S(O)$_2$N(R[12])(R[13]), —CH$_2$N(R[12])S(O)$_2$(R[13]), CH$_2$S(O) R[15], —CH$_2$S(O)N(R[12])(R[13]), —CH$_2$N(R[12])S(O)(R[13]) and —P(O)(R[17])(R[17a]), wherein $C_{1-6}$alkyl, $C_{2-6}$alkenyl, $C_{2-6}$alkynyl, $C_{3-14}$cycloalkyl, $C_{2-9}$heterocycloalkyl, $C_{6-10}$aryl, and $C_{1-9}$heteroaryl are optionally substituted with one, two, or three R[20b];

R[4] is selected from hydrogen, $C_{1-6}$alkyl, and $C_{1-6}$haloalkyl;
R[5] is selected from hydrogen, $C_{1-6}$alkyl, and $C_{1-6}$haloalkyl;
R[6] is selected from hydrogen, halogen, —CN, $C_{1-6}$alkyl, $C_{2-6}$alkenyl, $C_{2-6}$alkynyl, $C_{3-10}$cycloalkyl, $C_{2-9}$heterocycloalkyl, —OR[12], —SR[12], —N(R[12])(R[13]), —C(O)OR[12], —OC(O)N(R[12])(R[13]), —N(R[14])C(O)N(R[12])(R[13]), —N(R[14])C(O)OR[15], —N(R[14])S(O)$_2$R[15], —C(O)R[15], —S(O)R[15], —OC(O)R[15], —C(O)N(R[12])(R[13]), —C(O)C(O)N(R[12])(R[13]), —N(R[14])C(O)R[15], —S(O)$_2$R[15], —S(O)$_2$N(R[12])(R[13]), —S(=O)(=NH)N(R[12])(R[13]), —CH$_2$C(O)N(R[12])(R[13]), —CH$_2$N(R[14])C(O)R[15], —CH$_2$S(O)$_2$R[15], —CH$_2$S(O)$_2$N(R[12])(R[13]), —CH$_2$N(R[12])S(O)$_2$(R[13]), and —P(O)(R[17])(R[17a]), wherein $C_{1-6}$alkyl, $C_{2-6}$alkenyl, $C_{2-6}$alkynyl, $C_{3-10}$cycloalkyl, and $C_{2-9}$heterocycloalkyl are optionally substituted with one, two, or three R[20c];

each R[10] is independently selected from halogen, —CN, $C_{1-6}$alkyl, $C_{2-6}$alkenyl, $C_{2-6}$alkynyl, $C_{3-7}$cycloalkyl, $C_{2-9}$heterocycloalkyl, $C_{6-10}$aryl, $C_{1-9}$heteroaryl, —OR[12], —SR[12], —N(R[12])(R[13]), —C(O)OR[12], —OC(O)N(R[12])(R[13]), —N(R[14])C(O)N(R[12])(R[13]), —N(R[14])C(O)OR[15], —N(R[14])S(O)$_2$R[15], —C(O)R[15], —S(O)R[15], —OC(O)R[15], —C(O)N(R[12])(R[13]), —C(O)C(O)N(R[12])(R[13]), —N(R[14])C(O)R[15], —S(O)$_2$R[15], —S(O)$_2$N(R[12])(R[13]), —S(=O)(=NH)N(R[12])(R[13]), —C(O)N(R[12])(R[13]), —CH$_2$N(R[14])C(O)R[15], —CH$_2$S(O)$_2$R[15], —CH$_2$S(O)$_2$N(R[12])(R[13]), —CH$_2$N(R[12])S(O)$_2$(R[13]), and —P(O)(R[17])(R[17a]), wherein $C_{1-6}$alkyl, $C_{2-6}$alkenyl, $C_{2-6}$alkynyl, $C_{3-7}$cycloalkyl, $C_{2-9}$heterocycloalkyl, $C_{6-10}$aryl, and $C_{1-9}$heteroaryl are optionally substituted with one, two, or three $R^{20a}$;

each $R^{12}$ is independently selected from hydrogen, $C_{1-6}$alkyl, $C_{1-6}$ haloalkyl, $C_{2-6}$alkenyl, $C_{2-6}$alkynyl, $C_{3-7}$cycloalkyl, $C_{2-9}$heterocycloalkyl, $C_{6-10}$aryl, and $C_{1-9}$heteroaryl, wherein $C_{1-6}$alkyl, $C_{2-6}$alkenyl, $C_{2-6}$alkynyl, $C_{3-7}$cycloalkyl, $C_{2-9}$heterocycloalkyl, $C_{6-10}$aryl, and $C_{1-9}$heteroaryl are optionally substituted with one, two, or three $R^{20e}$;

each $R^{13}$ is independently selected from hydrogen, $C_{1-6}$alkyl, and $C_{1-6}$haloalkyl; or $R^{12}$ and $R^{13}$, together with the nitrogen to which they are attached, form a $C_{2-9}$heterocycloalkyl ring optionally substituted with one, two, or three $R^{20f}$;

$R^{13a}$ is selected from $C_{1-6}$alkyl and $C_{1-6}$haloalkyl; or $R^{12}$ and $R^{13a}$, together with the nitrogen to which they are attached, form a $C_{2-9}$heterocycloalkyl ring optionally substituted with one, two, or three $R^{20f}$;

each $R^{14}$ is independently selected from hydrogen, $C_{1-6}$alkyl, and $C_{1-6}$haloalkyl;

each $R^{15}$ is independently selected $C_{1-6}$alkyl, $C_{2-6}$alkenyl, $C_{2-6}$alkynyl, $C_{3-7}$cycloalkyl, $C_{2-9}$heterocycloalkyl, $C_{6-10}$aryl, and $C_{1-9}$ heteroaryl, wherein $C_{1-6}$alkyl, $C_{2-6}$alkenyl, $C_{2-6}$alkynyl, $C_{3-7}$cycloalkyl, $C_{2-9}$heterocycloalkyl, $C_{6-10}$aryl, and $C_{1-9}$heteroaryl are optionally substituted with one, two, or three $R^{20g}$;

each $R^{17}$ and each $R^{17a}$ are each independently selected from $C_{1-6}$alkyl and $C_{3-6}$cycloalkyl, wherein $C_{1-6}$alkyl and $C_{3-6}$cycloalkyl are optionally substituted with one, two or three of $R^{20h}$; or $R^{17}$ and $R^{17a}$ are combined to form a $C_{2-9}$heterocycloalkyl ring;

each $R^{20a}$, $R^{20b}$, $R^{20c}$, $R^{20d}$, $R^{20e}$, $R^{20f}$, $R^{20g}$, and $R^{20h}$ are each independently selected from halogen, oxo, =NH, —CN, $C_{1-6}$alkyl, $C_{2-6}$alkenyl, $C_{2-6}$alkynyl, $C_{3-10}$cycloalkyl, —$CH_2$—$C_{3-10}$cycloalkyl, $C_{2-9}$heterocycloalkyl, —$CH_2$—$C_{2-9}$heterocycloalkyl, $C_{6-10}$aryl, —$CH_2$—$C_{6-10}$ aryl, $C_{1-9}$heteroaryl, —$OR^{21}$, —$SR^{21}$, —$N(R^{22})(R^{23})$, —$C(O)OR^{22}$, —$C(O)N(R^{22})(R^{23})$, —$C(O)C(O)N(R^{22})(R^{23})$, —$OC(O)N(R^{22})(R^{23})$, —$N(R^{24})C(O)N(R^{22})(R^{23})$, —$N(R^{24})C(O)OR^{25}$, —$N(R^{24})C(O)R^{25}$, —$N(R^{24})S(O)_2R^{25}$, —$C(O)R^{25}$, —$S(O)_2R^{25}$, —$S(O)_2N(R^{22})(R^{23})$, —$OCH_2C(O)OR^{22}$, and —$OC(O)R^{25}$, wherein $C_{1-6}$alkyl, $C_{2-6}$alkenyl, $C_{2-6}$alkynyl, $C_{3-10}$cycloalkyl, —$CH_2$—$C_{3-10}$ cycloalkyl, $C_{2-9}$heterocycloalkyl, —$CH_2$—$C_{2-9}$heterocycloalkyl, $C_{6-10}$aryl, —$CH_2$—$C_{6-10}$aryl, and $C_{1-9}$heteroaryl are optionally substituted with one, two, or three groups independently selected from halogen, oxo, =NH, —CN, $C_{1-6}$alkyl, $C_{1-6}$haloalkyl, $C_{1-6}$alkoxy, $C_{1-6}$haloalkoxy, —$OR^{21}$, —$SR^{21}$, —$N(R^{22})(R^{23})$, —$C(O)OR^{22}$, —$C(O)N(R^{22})(R^{23})$, —$C(O)C(O)N(R^{22})(R^{23})$, —$OC(O)N(R^{22})(R^{23})$, —$N(R^{24})C(O)N(R^{22})(R^{23})$, —$N(R^{24})C(O)OR^{25}$, —$N(R^{24})C(O)R^{25}$, —$N(R^{24})S(O)_2R^{25}$, —$C(O)R^{25}$, —$S(O)_2R^{25}$, —$S(O)_2N(R^{22})(R^{23})$, and —$OC(O)R^{25}$;

each $R^{21}$ is independently selected from H, $C_{1-6}$alkyl, $C_{1-6}$haloalkyl, $C_{2-6}$alkenyl, $C_{2-6}$alkynyl, $C_{3-7}$cycloalkyl, $C_{2-9}$heterocycloalkyl, $C_{6-10}$aryl, and $C_{1-9}$heteroaryl, wherein $C_{3-7}$cycloalkyl, $C_{2-9}$heterocycloalkyl, $C_{6-10}$aryl, and $C_{1-9}$heteroaryl are optionally substituted with one, two, or three groups independently selected from halogen and $C_{1-6}$alkyl;

each $R^{22}$ is independently selected from H, $C_{1-6}$alkyl, $C_{1-6}$haloalkyl, $C_{2-6}$alkenyl, $C_{2-6}$alkynyl, $C_{3-7}$cycloalkyl, $C_{2-9}$heterocycloalkyl, $C_{6-10}$aryl, and $C_{1-9}$heteroaryl, wherein $C_{3-7}$cycloalkyl, $C_{2-9}$heterocycloalkyl, $C_{6-10}$aryl, and $C_{1-9}$heteroaryl are optionally substituted with one, two, or three groups independently selected from halogen and $C_{1-6}$alkyl;

each $R^{23}$ is independently selected from H and $C_{1-6}$alkyl;

each $R^{24}$ is independently selected from H and $C_{1-6}$alkyl; and each $R^{25}$ is selected from $C_{1-6}$alkyl, $C_{2-6}$alkenyl, $C_{2-6}$alkynyl, $C_{3-7}$cycloalkyl, $C_{2-9}$heterocycloalkyl, $C_{6-10}$aryl, and $C_{1-9}$heteroaryl, wherein $C_{1-6}$alkyl, $C_{3-7}$cycloalkyl, $C_{2-9}$heterocycloalkyl, $C_{6-10}$aryl, and $C_{1-9}$heteroaryl are optionally substituted with one, two, or three groups independently selected from halogen, $C_{1-6}$alkyl, $C_{1-6}$haloalkyl, $C_{1-6}$alkoxy, $C_{3-7}$cycloalkyl, $C_{2-9}$heterocycloalkyl, $C_{6-10}$aryl, and $C_{1-9}$heteroaryl.

In embodiments, the compound of Formula (I-1) is a compound of Formula (Ia-1), or a pharmaceutically acceptable salt or solvate thereof:

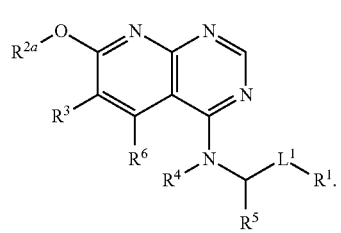

Formula (Ia-1)

In some embodiments of a compound of Formula (I-1) or (Ia-1), $R^{2a}$ is $C_{1-6}$alkyl optionally substituted with one, two, or three $R^{20a}$. In some embodiments of a compound of Formula (I-1) or (Ia-1), or a pharmaceutically acceptable salt or solvate thereof, $R^{2a}$ is unsubstituted $C_{1-6}$alkyl. In some embodiments of a compound of Formula (I-1) or (Ia-1), or a pharmaceutically acceptable salt or solvate thereof, $R^{2a}$ is —$CH_3$.

In embodiments, the compound of Formula (I-1) is a compound of Formula (Ib-1), or a pharmaceutically acceptable salt or solvate thereof:

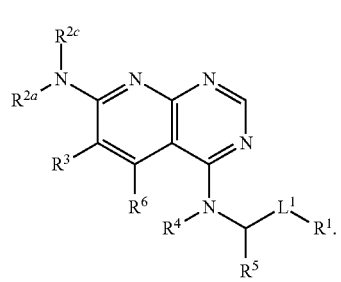

Formula (Ib-1)

In some embodiments of a compound of Formula (I-1) or (Ib-1), or a pharmaceutically acceptable salt or solvate thereof, $R^{2b}$ is $C_{1-6}$alkyl optionally substituted with one, two, or three $R^{20a}$.

In some embodiments of a compound of Formula (I-1) or (Ib-1), or a pharmaceutically acceptable salt or solvate thereof, $R^{2e}$ is $C_{1-6}$alkyl optionally substituted with one, two, or three $R^{20a}$.

In some embodiments of a compound of Formula (I-1) or (Ib-1), or a pharmaceutically acceptable salt or solvate thereof, $R^{2e}$ is hydrogen.

In embodiments, the compound of Formula (I-1) is a compound of Formula (Ic-1), or a pharmaceutically acceptable salt or solvate thereof:

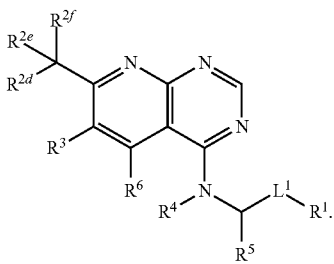

Formula (Ic-1)

In some embodiments of a compound of Formula (I-1) or (Ic-1), or a pharmaceutically acceptable salt or solvate thereof, $R^{2a}$ is hydrogen or $C_{1-6}$alkyl optionally substituted with one, two, or three $R^{20a}$.

In some embodiments of a compound of Formula (I-1) or (Ic-1), or a pharmaceutically acceptable salt or solvate thereof, $R^{2e}$ is hydrogen.

In some embodiments of a compound of Formula (I-1) or (Ic-1), or a pharmaceutically acceptable salt or solvate thereof, $R^{2f}$ is hydrogen.

In some embodiments of a compound of Formula (I-1), $R^2$ is halogen.

In an aspect is provided a compound of Formula (II), or a pharmaceutically acceptable salt or solvate thereof:

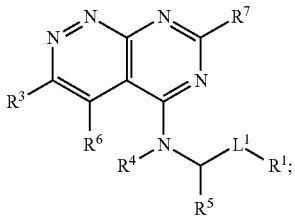

Formula (II)

wherein:
$R^1$ is a 3-12 membered cycloalkyl ring, 3-12 membered heterocycloalkyl ring, 6-10 membered aryl ring, or 5-10 membered heteroaryl ring, wherein the 3-12 membered cycloalkyl ring, 3-12 membered heterocycloalkyl ring, 6-10 membered aryl ring, and 5-10 membered heteroaryl ring are optionally substituted with one or more $R^{10}$;
$L^1$ is a bond or $C_{1-6}$alkyl;
$R^3$ is selected from hydrogen, halogen, —CN, $C_{1-6}$alkyl, $C_{2-6}$alkenyl, $C_{2-6}$alkynyl, $C_{3-14}$cycloalkyl, $C_{2-9}$heterocycloalkyl, $C_{6-10}$aryl, $C_{1-9}$ heteroaryl, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, $N(R^{14})S(O)R^{15}$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{15}$, —$S(O)_2R^{15}$, —$S(O)_2N(R^{12})(R^{13})$, —$S(O)N(R^{12})(R^{13})$, —$S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, —$CH_2S(O)_2N(R^{12})(R^{13})$, —$CH_2N(R^{12})S(O)_2(R^{13})$, $CH_2S(O)R^{15}$, —$CH_2S(O)N(R^{12})(R^{13})$, —$CH_2N(R^{12})S(O)(R^{13})$ and —$P(O)(R^{17})(R^{17a})$, wherein $C_{1-6}$alkyl, $C_{2-6}$alkenyl, $C_{2-6}$alkynyl, $C_{3-14}$cycloalkyl, $C_{2-9}$heterocycloalkyl, $C_{6-10}$aryl, and $C_{1-9}$heteroaryl are optionally substituted with one, two, or three $R^{20b}$;
$R^4$ is selected from hydrogen, $C_{1-6}$alkyl, and $C_{1-6}$haloalkyl;
$R^5$ is selected from hydrogen, $C_{1-6}$alkyl, and $C_{1-6}$haloalkyl;
$R^6$ and $R^7$ are each independently selected from hydrogen, halogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{1-9}$heteroaryl, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{15}$, —$S(O)_2R^{15}$, —$S(O)_2N(R^{12})(R^{13})$, —$S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, —$CH_2S(O)_2N(R^{12})(R^{13})$, —$CH_2N(R^{12})S(O)_2(R^{13})$, and —$P(O)(R^{17})(R^{17a})$, wherein $C_{1-6}$alkyl, $C_{2-6}$alkenyl, $C_{2-6}$alkynyl, $C_{3-10}$cycloalkyl, $C_{2-9}$heterocycloalkyl, and $C_{1-9}$heteroaryl are optionally substituted with one, two, or three $R^{20c}$;
each $R^{10}$ is independently selected from halogen, —CN, $C_{1-6}$alkyl, $C_{2-6}$alkenyl, $C_{2-6}$alkynyl, $C_{3-7}$cycloalkyl, $C_{2-9}$heterocycloalkyl, $C_{6-10}$aryl, $C_{1-9}$heteroaryl, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{15}$, —$S(O)_2R^{15}$, —$S(O)_2N(R^{12})(R^{13})$, —$S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, —$CH_2S(O)_2N(R^{12})(R^{13})$, —$CH_2N(R^{12})S(O)_2(R^{13})$, and —$P(O)(R^{17})(R^{17a})$, wherein $C_{1-6}$alkyl, $C_{2-6}$alkenyl, $C_{2-6}$alkynyl, $C_{3-7}$cycloalkyl, $C_{2-9}$heterocycloalkyl, $C_{6-10}$aryl, and $C_{1-9}$heteroaryl are optionally substituted with one, two, or three $R^{20a}$;
each $R^{12}$ is independently selected from hydrogen, $C_{1-6}$alkyl, $C_{1-6}$ haloalkyl, $C_{2-6}$alkenyl, $C_{2-6}$alkynyl, $C_{3-7}$cycloalkyl, $C_{2-9}$heterocycloalkyl, $C_{6-10}$aryl, and $C_{1-9}$heteroaryl, wherein $C_{1-6}$alkyl, $C_{2-6}$alkenyl, $C_{2-6}$alkynyl, $C_{3-7}$cycloalkyl, $C_{2-9}$heterocycloalkyl, $C_{6-10}$aryl, and $C_{1-9}$heteroaryl are optionally substituted with one, two, or three $R^{20e}$;
each $R^{13}$ is independently selected from hydrogen, $C_{1-6}$alkyl, and $C_{1-6}$haloalkyl; or $R^{12}$ and $R^{13}$, together with the nitrogen to which they are attached, form a $C_{2-9}$heterocycloalkyl ring optionally substituted with one, two, or three $R^{20f}$; each $R^{14}$ is independently selected from hydrogen, $C_{1-6}$alkyl, and $C_{1-6}$haloalkyl;
each $R^{15}$ is independently selected $C_{1-6}$alkyl, $C_{2-6}$alkenyl, $C_{2-6}$alkynyl, $C_{3-7}$cycloalkyl, $C_{2-9}$heterocycloalkyl, $C_{6-10}$aryl, and $C_{1-9}$ heteroaryl, wherein $C_{1-6}$alkyl, $C_{2-6}$alkenyl, $C_{2-6}$alkynyl, $C_{3-7}$cycloalkyl, $C_{2-9}$heterocycloalkyl, $C_{6-10}$aryl, and $C_{1-9}$heteroaryl are optionally substituted with one, two, or three $R^{20g}$;
each $R^{17}$ and each $R^{17a}$ are each independently selected from $C_{1-6}$alkyl and $C_{3-6}$cycloalkyl, wherein $C_{1-6}$alkyl and $C_{3-6}$cycloalkyl are optionally substituted with one, two or three of $R^{20h}$; or $R^{17}$ and $R^{17a}$ form a $C_{2-9}$heterocycloalkyl ring; each $R^{20a}$, $R^{20b}$, $R^{20c}$, $R^{20d}$, $R^{20e}$, $R^{20f}$, $R^{20g}$, and $R^{20h}$ are each independently selected from halogen, oxo, =NH, —CN, $C_{1-6}$alkyl, $C_{2-6}$alkenyl, $C_{2-6}$alkynyl, $C_{3-10}$cycloalkyl, —$CH_2$—$C_{3-10}$cycloalkyl, $C_{2-9}$heterocycloalkyl, —$CH_2$—$C_{2-9}$heterocycloalkyl, $C_{6-10}$aryl, —$CH_2$—$C_{6-10}$aryl, $C_{1-9}$heteroaryl, —$OR^{21}$, —$SR^{21}$, —$N(R^{22})(R^{23})$, —$C(O)OR^{22}$, —$C(O)N(R^{22})(R^{23})$, —$C(O)C(O)N(R^{22})(R^{23})$, —$OC(O)N(R^{22})(R^{23})$, —$N(R^{24})C(O)N(R^{22})(R^{23})$, —$N(R^{24})C(O)OR^{25}$, —$N(R^{24})C(O)R^{25}$, —$N(R^{24})S(O)_2R^{25}$, —$C(O)R^{25}$, —$S(O)_2R^{25}$, —$S(O)_2N(R^{22})(R^{23})$, —$OCH_2C(O)OR^{22}$, and —$OC(O)R^{25}$, wherein $C_{1-6}$alkyl, $C_{2-6}$alkenyl, $C_{2-6}$alkynyl, $C_{3-10}$cycloalkyl, —$CH_2$—$C_{3-10}$cycloalkyl, $C_{2-9}$heterocycloalkyl, —$CH_2$—$C_{2-9}$heterocycloalkyl, $C_{6-10}$aryl, —$CH_2$—$C_{6-10}$aryl, and $C_{1-9}$heteroaryl are optionally substituted with one, two, or three groups independently selected from halogen, oxo, =NH, —CN, $C_{1-6}$alkyl, $C_{1-6}$haloalkyl, $C_{1-6}$alkoxy, $C_{1-6}$haloalkoxy, —OR²¹, —SR²¹, —N(R²²)(R²³), —C(O)OR²², —C(O)N(R²²)(R²³), —C(O)C(O)N(R²²)(R²³), —OC(O)N(R²²)(R²³), —N(R²⁴)C(O)N(R²²)(R²³), —N(R²⁴)C(O)OR²⁵, —N(R²⁴)C(O)R²⁵, —N(R²⁴)S(O)₂R²⁵, —C(O)R²⁵, —S(O)₂R²⁵, —S(O)₂N(R²²)(R²³), and —OC(O)R²⁵;

each R²¹ is independently selected from H, $C_{1-6}$alkyl, $C_{1-6}$haloalkyl, $C_{2-6}$alkenyl, $C_{2-6}$alkynyl, $C_{3-7}$cycloalkyl, $C_{2-9}$heterocycloalkyl, $C_{6-10}$aryl, and $C_{1-9}$heteroaryl, wherein $C_{3-7}$cycloalkyl, $C_{2-9}$heterocycloalkyl, $C_{6-10}$aryl, and $C_{1-9}$heteroaryl are optionally substituted with one, two, or three groups independently selected from halogen and $C_{1-6}$alkyl;

each R²² is independently selected from H, $C_{1-6}$alkyl, $C_{1-6}$haloalkyl, $C_{2-6}$alkenyl, $C_{2-6}$alkynyl, $C_{3-7}$cycloalkyl, $C_{2-9}$heterocycloalkyl, $C_{6-10}$aryl, and $C_{1-9}$heteroaryl, wherein $C_{3-7}$cycloalkyl, $C_{2-9}$heterocycloalkyl, $C_{6-10}$aryl, and $C_{1-9}$heteroaryl are optionally substituted with one, two, or three groups independently selected from halogen and $C_{1-6}$alkyl;

each R²³ is independently selected from H and $C_{1-6}$alkyl;

each R²⁴ is independently selected from H and $C_{1-6}$alkyl; and each R²⁵ is selected from $C_{1-6}$alkyl, $C_{2-6}$alkenyl, $C_{2-6}$alkynyl, $C_{3-7}$cycloalkyl, $C_{2-9}$heterocycloalkyl, $C_{6-10}$aryl, and $C_{1-9}$heteroaryl, wherein $C_{1-6}$alkyl, $C_{3-7}$cycloalkyl, $C_{2-9}$heterocycloalkyl, $C_{6-10}$aryl, and $C_{1-9}$heteroaryl are optionally substituted with one, two, or three groups independently selected from halogen, $C_{1-6}$alkyl, $C_{1-6}$haloalkyl, $C_{1-6}$alkoxy, $C_{3-7}$cycloalkyl, $C_{2-9}$heterocycloalkyl, $C_{6-10}$aryl, and $C_{1-9}$heteroaryl.

In some embodiments, R³ is selected from —N(R¹²)(R¹³), —C(O)R¹⁵, —C(O)N(R¹²)(R¹³), —SO₂(R¹²)(R¹³), —SO₂N(R¹²)(R¹³), —P(O)(R¹⁷)(R¹⁷ᵃ), $C_{1-6}$alkyl, $C_{3-10}$cycloalkyl, $C_{2-9}$heterocycloalkyl, $C_{6-10}$aryl, and $C_{1-9}$heteroaryl, wherein $C_{1-6}$alkyl, $C_{3-10}$cycloalkyl, $C_{2-9}$heterocycloalkyl, $C_{6-10}$aryl, and $C_{1-9}$heteroaryl are optionally substituted with one, two, or three R²⁰ᵇ.

In some embodiments, R³ is selected from —N(R¹²)(R¹³), $C_{1-6}$alkyl, $C_{3-10}$cycloalkyl, and $C_{2-9}$heterocycloalkyl, wherein $C_{1-6}$alkyl, $C_{3-10}$cycloalkyl, and $C_{2-9}$heterocycloalkyl are optionally substituted with one, two, or three R²⁰ᵇ.

In embodiments, R³ is $C_{2-9}$heterocycloalkyl optionally substituted with one, two, or three R²⁰ᵇ.

In embodiments, R³ is $C_{3-10}$cycloalkyl optionally substituted with one, two, or three R²⁰ᵇ.

In embodiments, R³ is $C_{3-4}$cycloalkyl optionally substituted with one R²⁰ᵇ.

In some embodiments, R²⁰ᵇ is —CN.

In some embodiments, R³ is

In some embodiments, R³ is $C_{1-6}$alkyl optionally substituted with one, two, or three R²⁰ᵇ.

In some embodiments, R³ is —N(R¹²)(R¹³).

In an aspect is provided a compound of Formula (III), or a pharmaceutically acceptable salt or solvate thereof:

Formula (III)

wherein:

R¹ is a 3-12 membered cycloalkyl ring, 3-12 membered heterocycloalkyl ring, 6-10 membered aryl ring, or 5-10 membered heteroaryl ring, wherein the 3-12 membered cycloalkyl ring, 3-12 membered heterocycloalkyl ring, 6-10 membered aryl ring, and 5-10 membered heteroaryl ring are optionally substituted with one or more R¹⁰;

L¹ is a bond or $C_{1-6}$alkyl;

R⁴ is selected from hydrogen, $C_{1-6}$alkyl, and $C_{1-6}$haloalkyl;

R⁵ is selected from hydrogen, $C_{1-6}$alkyl, and $C_{1-6}$haloalkyl;

R⁶ is selected from hydrogen, halogen, —CN, $C_{1-6}$alkyl, $C_{2-6}$alkenyl, $C_{2-6}$alkynyl, $C_{3-10}$cycloalkyl, $C_{2-9}$heterocycloalkyl, —OR¹², —SR¹², —N(R¹²)(R¹³), —C(O)OR¹², —OC(O)N(R¹²)(R¹³), —N(R¹⁴)C(O)N(R¹²)(R¹³), —N(R¹⁴)C(O)OR¹⁵, —N(R¹⁴)S(O)₂R¹⁵, —C(O)R¹⁵, —S(O)R¹⁵, —OC(O)R¹⁵, —C(O)N(R¹²)(R¹³), —C(O)C(O)N(R¹²)(R¹³), —N(R¹⁴)C(O)R¹⁵, —S(O)₂R¹⁵, —S(O)₂N(R¹²)(R¹³), —S(=O)(=NH)N(R¹²)(R¹³), —CH₂C(O)N(R¹²)(R¹³), —CH₂N(R¹⁴)C(O)R¹⁵, —CH₂S(O)₂R¹⁵, —CH₂S(O)₂N(R¹²)(R¹³), —CH₂N(R¹²)S(O)₂(R¹³), and —P(O)(R¹⁷)(R¹⁷ᵃ), wherein $C_{1-6}$alkyl, $C_{2-6}$alkenyl, $C_{2-6}$alkynyl, $C_{3-10}$cycloalkyl, and $C_{2-9}$heterocycloalkyl are optionally substituted with one, two, or three R²⁰ᶜ;

R⁷ is selected from hydrogen, halogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{1-9}$heteroaryl, —OR¹², —SR¹², —N(R¹²)(R¹³), —C(O)OR¹², —OC(O)N(R¹²)(R¹³), —N(R¹⁴)C(O)N(R¹²)(R¹³), —N(R¹⁴)C(O)OR¹⁵, —N(R¹⁴)S(O)₂R¹⁵, —C(O)R¹⁵, —S(O)R¹⁵, —OC(O)R¹⁵, —C(O)N(R¹²)(R¹³), —C(O)C(O)N(R¹²)(R¹³), —N(R¹⁴)C(O)R¹⁵, —S(O)₂R¹⁵, —S(O)₂N(R¹²)(R¹³), —S(=O)(=NH)N(R¹²)(R¹³), —CH₂C(O)N(R¹²)(R¹³), —CH₂N(R¹⁴)C(O)R¹⁵, —CH₂S(O)₂R¹⁵, —CH₂S(O)₂N(R¹²)(R¹³), —CH₂N(R¹²)S(O)₂(R¹³), and —P(O)(R¹⁷)(R¹⁷ᵃ), wherein $C_{1-6}$alkyl, $C_{2-6}$alkenyl, $C_{2-6}$alkynyl, $C_{3-10}$cycloalkyl, $C_{2-9}$heterocycloalkyl, and $C_{1-9}$heteroaryl are optionally substituted with one, two, or three R²⁰ᶜ;

R⁸ is —OR⁹ᵃ, —NR⁹ᵇR⁹ᶜ, —SR⁹ᵇ, —S(O)R⁹ᵈ, —S(O)₂R⁹ᵈ, —S(O)₂NR⁹ᵇR⁹ᶜ, —C(R⁹ᵉ)(R⁹ᶠ)(R⁹ᵍ), and C(O)NR⁹ᵇR⁹ᶜ.

R⁹ᵃ is selected from hydrogen, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —C(O)OR¹², —C(O)R¹⁵, —C(O)N(R¹²)(R¹³), —S(O)₂R¹⁵, —S(O)₂N(R¹²)(R¹³), wherein $C_{1-6}$alkyl is substituted with one, two, or three R²⁰ᵃ, and wherein $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three R²⁰ᵃ;

R⁹ᵇ is selected from hydrogen, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —C(O)OR¹², —C(O)R¹⁵, —C(O)N(R¹²)(R¹³), —S(O)₂R¹⁵, and —S(O)₂N(R¹²)(R¹³), wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20a}$;

$R^{9c}$ is selected from hydrogen, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20a}$; or $R^{9b}$ and $R^{9c}$, together with the nitrogen to which they are attached, form a $C_{2-9}$heterocycloalkyl ring optionally substituted with one, two, or three $R^{20a}$;

$R^{9d}$ is selected from hydrogen, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl, wherein $C_{1-6}$alkyl is substituted with one, two, or three $R^{20a}$, and wherein $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20a}$;

$R^{9f}$ is selected from hydrogen, $C_{1-6}$alkyl, $C_{2-6}$alkenyl, $C_{2-6}$alkynyl, $C_{3-10}$cycloalkyl, $C_{2-9}$heterocycloalkyl, $C_{1-9}$heteroaryl, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{15}$, —$S(O)_2R^{15}$, —$S(O)_2N(R^{12})(R^{13})$, —$S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, —$CH_2S(O)_2N(R^{12})(R^{13})$, —$CH_2N(R^{12})S(O)_2(R^{13})$, and —$P(O)(R^{17})(R^{17a})$, wherein $C_{1-6}$alkyl, $C_{2-6}$alkenyl, $C_{2-6}$alkynyl, $C_{3-10}$cycloalkyl, $C_{2-9}$heterocycloalkyl, and $C_{1-9}$heteroaryl are optionally substituted with one, two, or three $R^{20a}$;

$R^{9f}$ is selected from hydrogen, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20a}$;

$R^{9g}$ is selected from $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20a}$;

each $R^{10}$ is independently selected from halogen, —CN, $C_{1-6}$alkyl, $C_{2-6}$alkenyl, $C_{2-6}$alkynyl, $C_{3-7}$cycloalkyl, $C_{2-9}$heterocycloalkyl, $C_{6-10}$aryl, $C_{1-9}$heteroaryl, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{15}$, —$S(O)_2R^{15}$, —$S(O)_2N(R^{12})(R^{13})$, —$S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, —$CH_2S(O)_2N(R^{12})(R^{13})$, —$CH_2N(R^{12})S(O)_2(R^{13})$, and —$P(O)(R^{17})(R^{17a})$, wherein $C_{1-6}$alkyl, $C_{2-6}$alkenyl, $C_{2-6}$alkynyl, $C_{3-7}$cycloalkyl, $C_{2-9}$heterocycloalkyl, $C_{6-10}$aryl, and $C_{1-9}$heteroaryl are optionally substituted with one, two, or three $R^{20a}$;

each $R^{12}$ is independently selected from hydrogen, $C_{1-6}$alkyl, $C_{1-6}$haloalkyl, $C_{2-6}$alkenyl, $C_{2-6}$alkynyl, $C_{3-7}$cycloalkyl, $C_{2-9}$heterocycloalkyl, $C_{6-10}$aryl, and $C_{1-9}$heteroaryl, wherein $C_{1-6}$alkyl, $C_{2-6}$alkenyl, $C_{2-6}$alkynyl, $C_{3-7}$cycloalkyl, $C_{2-9}$heterocycloalkyl, $C_{6-10}$aryl, and $C_{1-9}$heteroaryl are optionally substituted with one, two, or three $R^{20e}$;

each $R^{13}$ is independently selected from hydrogen, $C_{1-6}$alkyl, and $C_{1-6}$haloalkyl; or $R^{12}$ and $R^{13}$, together with the nitrogen to which they are attached, form a $C_{2-9}$heterocycloalkyl ring optionally substituted with one, two, or three $R^{20f}$;

each $R^{14}$ is independently selected from hydrogen, $C_{1-6}$alkyl, and $C_{1-6}$haloalkyl;

each $R^{15}$ is independently selected $C_{1-6}$alkyl, $C_{2-6}$alkenyl, $C_{2-6}$alkynyl, $C_{3-7}$cycloalkyl, $C_{2-9}$heterocycloalkyl, $C_{6-10}$aryl, and $C_{1-9}$ heteroaryl, wherein $C_{1-6}$alkyl, $C_{2-6}$alkenyl, $C_{2-6}$alkynyl, $C_{3-7}$cycloalkyl, $C_{2-9}$heterocycloalkyl, $C_{6-10}$aryl, and $C_{1-9}$heteroaryl are optionally substituted with one, two, or three $R^{20g}$;

each $R^{17}$ and each $R^{17a}$ are each independently selected from $C_{1-6}$alkyl and $C_{3-6}$cycloalkyl, wherein $C_{1-6}$alkyl and $C_{3-6}$cycloalkyl are optionally substituted with one, two or three of $R^{20h}$; or $R^{17}$ and $R^{17a}$ are combined to form a $C_{2-9}$heterocycloalkyl ring;

each $R^{20a}$, $R^{20b}$, $R^{20c}$, $R^{20d}$, $R^{20e}$, $R^{20f}$, $R^{20g}$, and $R^{20h}$ are each independently selected from halogen, oxo, =NH, —CN, $C_{1-6}$alkyl, $C_{2-6}$alkenyl, $C_{2-6}$alkynyl, $C_{3-10}$cycloalkyl, —$CH_2$—$C_{3-10}$cycloalkyl, $C_{2-9}$heterocycloalkyl, —$CH_2$—$C_{2-9}$heterocycloalkyl, $C_{6-10}$aryl, —$CH_2$—$C_{6-10}$aryl, $C_{1-9}$heteroaryl, —$OR^{21}$, —$SR^{21}$, —$N(R^{22})(R^{23})$, —$C(O)OR^{22}$, —$C(O)N(R^{22})(R^{23})$, —$C(O)C(O)N(R^{22})(R^{23})$, —$OC(O)N(R^{22})(R^{23})$, —$N(R^{24})C(O)N(R^{22})(R^{23})$, —$N(R^{24})C(O)OR^{25}$, —$N(R^{24})C(O)R^{25}$, —$N(R^{24})S(O)_2R^{25}$, —$C(O)R^{25}$, —$S(O)_2R^{25}$, —$S(O)_2N(R^{22})(R^{23})$, —$OCH_2C(O)OR^{22}$, and —$OC(O)R^{25}$, wherein $C_{1-6}$alkyl, $C_{2-6}$alkenyl, $C_{2-6}$alkynyl, $C_{3-10}$cycloalkyl, —$CH_2$—$C_{3-10}$cycloalkyl, $C_{2-9}$heterocycloalkyl, —$CH_2$—$C_{2-9}$heterocycloalkyl, $C_{6-10}$aryl, —$CH_2$—$C_{6-10}$aryl, and $C_{1-9}$heteroaryl are optionally substituted with one, two, or three groups independently selected from halogen, oxo, =NH, —CN, $C_{1-6}$alkyl, $C_{1-6}$haloalkyl, $C_{1-6}$alkoxy, $C_{1-6}$haloalkoxy, —$OR^{21}$, —$SR^{21}$, —$N(R^{22})(R^{23})$, —$C(O)OR^{22}$, —$C(O)N(R^{22})(R^{23})$, —$C(O)C(O)N(R^{22})(R^{23})$, —$OC(O)N(R^{22})(R^{23})$, —$N(R^{24})C(O)N(R^{22})(R^{23})$, —$N(R^{24})C(O)OR^{25}$, —$N(R^{24})C(O)R^{25}$, —$N(R^{24})S(O)_2R^{25}$, —$C(O)R^{25}$, —$S(O)_2R^{25}$, —$S(O)_2N(R^{22})(R^{23})$, and —$OC(O)R^{25}$;

each $R^{21}$ is independently selected from H, $C_{1-6}$alkyl, $C_{1-6}$haloalkyl, $C_{2-6}$alkenyl, $C_{2-6}$alkynyl, $C_{3-7}$cycloalkyl, $C_{2-9}$heterocycloalkyl, $C_{6-10}$aryl, and $C_{1-9}$heteroaryl, wherein $C_{3-7}$cycloalkyl, $C_{2-9}$heterocycloalkyl, $C_{6-10}$aryl, and $C_{1-9}$heteroaryl are optionally substituted with one, two, or three groups independently selected from halogen and $C_{1-6}$alkyl;

each $R^{22}$ is independently selected from H, $C_{1-6}$alkyl, $C_{1-6}$haloalkyl, $C_{2-6}$alkenyl, $C_{2-6}$alkynyl, $C_{3-7}$cycloalkyl, $C_{2-9}$heterocycloalkyl, $C_{6-10}$aryl, and $C_{1-9}$heteroaryl, wherein $C_{3-7}$cycloalkyl, $C_{2-9}$heterocycloalkyl, $C_{6-10}$aryl, and $C_{1-9}$heteroaryl are optionally substituted with one, two, or three groups independently selected from halogen and $C_{1-6}$alkyl;

each $R^{23}$ is independently selected from H and $C_{1-6}$alkyl;
each $R^{24}$ is independently selected from H and $C_{1-6}$alkyl; and each $R^{25}$ is selected from $C_{1-6}$alkyl, $C_{2-6}$alkenyl, $C_{2-6}$alkynyl, $C_{3-7}$cycloalkyl, $C_{2-9}$heterocycloalkyl, $C_{6-10}$aryl, and $C_{1-9}$heteroaryl, wherein $C_{1-6}$alkyl, $C_{3-7}$cycloalkyl, $C_{2-9}$heterocycloalkyl, $C_{6-10}$aryl, and $C_{1-9}$heteroaryl are optionally substituted with one, two, or three groups independently selected from halogen, $C_{1-6}$alkyl, $C_{1-6}$haloalkyl, $C_{1-6}$alkoxy, $C_{3-7}$cycloalkyl, $C_{2-9}$heterocycloalkyl, $C_{6-10}$aryl, and $C_{1-9}$heteroaryl.

In some embodiments, $R^1$ is $-OR^{9a}$. In some embodiments, $R^1$ is $-NR^{9b}R^{9c}$. In some embodiments, $R^1$ is $-C(R^{9e})(R^{9f})(R^{9g})$.

In some embodiments, $R^6$ is selected from hydrogen, halogen, $C_{1-6}$alkyl, $C_{3-10}$cycloalkyl, $C_{2-9}$heterocycloalkyl, and $C_{1-9}$heteroaryl, wherein $C_{1-6}$alkyl, $C_{3-10}$cycloalkyl, $C_{2-9}$heterocycloalkyl, and $C_{1-9}$heteroaryl are optionally substituted with one, two, or three $R^{20c}$. In some embodiments, $R^6$ is independently selected from hydrogen, halogen, and unsubstituted $C_{1-6}$alkyl. In some embodiments, $R^6$ is hydrogen.

In some embodiments, $R^7$ is selected from hydrogen, halogen, $C_{1-6}$alkyl, $C_{3-10}$cycloalkyl, $C_{2-9}$heterocycloalkyl, and $C_{1-9}$heteroaryl, wherein $C_{1-6}$alkyl, $C_{3-10}$cycloalkyl, $C_{2-9}$heterocycloalkyl, and $C_{1-9}$heteroaryl are optionally substituted with one, two, or three $R^{20c}$. In some embodiments, $R^7$ is independently selected from hydrogen, halogen, and unsubstituted $C_{1-6}$alkyl. In some embodiments, $R^7$ is unsubstituted $C_{1-6}$alkyl. In some embodiments, $R^7$ is hydrogen.

In some embodiments, $R^5$ is selected from $C_{1-6}$alkyl and $C_{1-6}$haloalkyl. In some embodiments, $R^5$ is $-CH_3$.

In some embodiments, $R^4$ is hydrogen.

In some embodiments, $L^1$ is a bond.

In some embodiments, $R^1$ is a 6-10 membered aryl ring substituted with one or more $R^{10}$.

In some embodiments, $R^1$ is phenyl substituted with one or more $R^{10}$.

In some embodiments, $R^1$ is phenyl substituted with one, two, or three $R^{10}$.

In some embodiments, each $R^{10}$ is independently selected from halogen, $C_{1-6}$alkyl, $C_{3-7}$cycloalkyl, $C_{2-9}$heterocycloalkyl, $C_{6-10}$aryl, $C_{1-9}$heteroaryl, $-OR^{12}$, and $N(R^{12})(R^{13})$, wherein $C_{1-6}$alkyl, $C_{3-7}$cycloalkyl, $C_{2-9}$heterocycloalkyl, $C_{6-10}$aryl, and $C_{1-9}$heteroaryl are optionally substituted with one, two, or three $R^{20d}$.

In some embodiments, each $R^{10}$ is independently selected from halogen, $C_{1-6}$alkyl, and $N(R^{12})(R^{13})$ wherein $C_{1-6}$alkyl is optionally substituted with one, two, or three $R^{20d}$.

In some embodiments, each $R^{10}$ is independently selected from halogen and $C_{1-6}$alkyl, wherein $C_{1-6}$alkyl is substituted with one, two, or three $R^{20d}$, and each $R^{20d}$ is halogen or $-OH$.

In some embodiments, $R^1$ is independently selected from

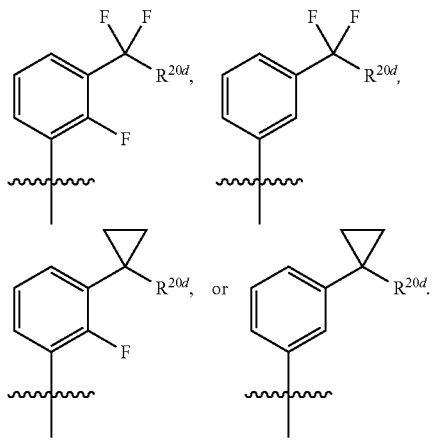

In some embodiments, $R^{20d}$ is $C_{1-6}$alkyl optionally substituted with one, two, or three groups independently selected from F and $-OH$.

In some embodiments, $R^{20d}$ is $C_{1-3}$alkyl substituted with one $-OH$.

In some embodiments, $R^1$ is selected from

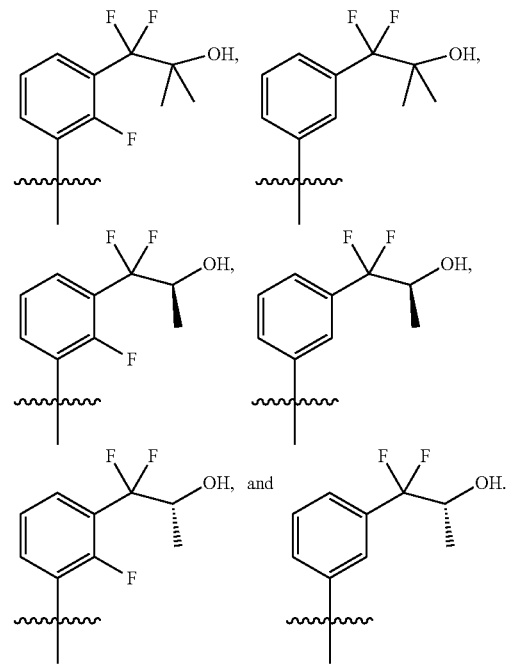

In an aspect is provided a compound of Formula (I-2), or a pharmaceutically acceptable salt or solvate thereof:

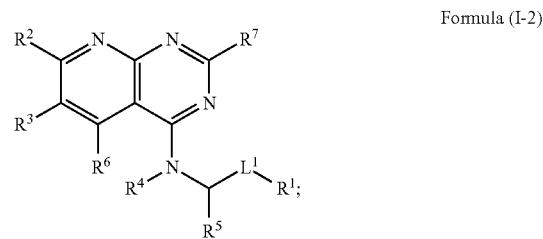

Formula (I-2)

wherein:
$R^1$ is a 3-12 membered cycloalkyl ring, 3-12 membered heterocycloalkyl ring, 6-10 membered aryl ring, or 5-10 membered heteroaryl ring, wherein the 3-12 membered cycloalkyl ring, 3-12 membered heterocycloalkyl ring, 6-10 membered aryl ring, and 5-10 membered heteroaryl ring are optionally substituted with one or more $R^{10}$;
$L^1$ is a bond or $C_{1-6}$alkyl;
$R^2$ is $-OR^{2a}$, $-NR^{2b}R^{2c}$, $-SR^{2g}$, $-S(O)R^{2h}$, $-S(O)_2R^{2h}$, $-S(O)_2NR^{2b}R^{2c}$, $-C(R^{2d})(R^{2e})(R^{2f})$, $C(O)NR^{2b}R^{2c}$, $-CN$, or halogen; $R^{2a}$ is selected from hydrogen, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, $-C(O)OR^{12}$, $-C(O)R^{15}$, $-C(O)N(R^{12})(R^{13})$, $-S(O)_2R^{15}$, $-S(O)_2N(R^{12})(R^{13})$, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20a}$;
$R^{2b}$ is selected from hydrogen, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, $-C(O)OR^{12}$, $-C(O)R^{15}$, —C(O)N($R^{12}$)($R^{13}$), —S(O)$_2$$R^{15}$, and —S(O)$_2$N($R^{12}$)($R^{13}$), wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20a}$;

$R^{2c}$ is selected from hydrogen, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20a}$; or $R^{2b}$ and $R^{2c}$, together with the nitrogen to which they are attached, form a $C_{2-9}$heterocycloalkyl ring optionally substituted with one, two, or three $R^{20a}$;

$R^{2d}$ is selected from hydrogen, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —O$R^{12}$, —S$R^{12}$, —N($R^{12}$)($R^{13}$), —C(O)O$R^{12}$, —OC(O)N($R^{12}$)($R^{13}$), —N($R^{14}$)C(O)N($R^{12}$)($R^{13}$), —N($R^{14}$)C(O)O$R^{15}$, —N($R^{14}$)S(O)$_2$$R^{15}$, —C(O)$R^{15}$, —S(O)$R^{15}$, —OC(O)$R^{15}$, —C(O)N($R^{12}$)($R^{13}$), —C(O)C(O)N($R^{12}$)($R^{13}$), —N($R^{14}$)C(O)$R^{15}$, —S(O)$_2$$R^{15}$, —S(O)$_2$N($R^{12}$)($R^{13}$), —S(=O)(=NH)N($R^{12}$)($R^{13}$), —CH$_2$C(O)N($R^{12}$)($R^{13}$), —CH$_2$N($R^{14}$)C(O)$R^{15}$, —CH$_2$S(O)$_2$$R^{15}$, —CH$_2$S(O)$_2$N($R^{12}$)($R^{13}$), —CH$_2$N($R^{12}$)S(O)$_2$($R^{13}$), and —P(O)($R^{17}$)($R^{17a}$), wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20a}$;

$R^{2e}$ is selected from hydrogen, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20a}$;

$R^{2f}$ is selected from hydrogen, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20a}$;

$R^{2g}$ is selected from hydrogen, $C_{2-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —C(O)O$R^{12}$, —C(O)$R^{15}$, —C(O)N($R^{12}$)($R^{13}$), —S(O)$_2$$R^{15}$, —S(O)$_2$N($R^{12}$)($R^{13}$), wherein $C_{2-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20a}$;

$R^{2h}$ is selected from $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20a}$;

$R^3$ is $C_{3-4}$cycloalkyl optionally substituted with one $R^{20b}$.

$R^4$ is selected from hydrogen, $C_{1-6}$alkyl, and $C_{1-6}$haloalkyl;

$R^5$ is selected from hydrogen, $C_{1-6}$alkyl, and $C_{1-6}$haloalkyl;

$R^6$ is selected from hydrogen, halogen, —CN, $C_{1-6}$alkyl, $C_{2-6}$alkenyl, $C_{2-6}$alkynyl, $C_{3-10}$cycloalkyl, $C_{2-9}$heterocycloalkyl, —O$R^{12}$, —S$R^{12}$, —N($R^{12}$)($R^{13}$), —C(O)O$R^{12}$, —OC(O)N($R^{12}$)($R^{13}$), —N($R^{14}$)C(O)N($R^{12}$)($R^{13}$), —N($R^{14}$)C(O)O$R^{15}$, —N($R^{14}$)S(O)$_2$$R^{15}$, —C(O)$R^{15}$, —S(O)$R^{15}$, —OC(O)$R^{15}$, —C(O)N($R^{12}$)($R^{13}$), —C(O)C(O)N($R^{12}$)($R^{13}$), —N($R^{14}$)C(O)$R^{15}$, —S(O)$_2$$R^{15}$, —S(O)$_2$N($R^{12}$)($R^{13}$), —S(=O)(=NH)N($R^{12}$)($R^{13}$), —CH$_2$C(O)N($R^{12}$)($R^{13}$), —CH$_2$N($R^{14}$)C(O)$R^{15}$, —CH$_2$S(O)$_2$$R^{15}$, —CH$_2$S(O)$_2$N($R^{12}$)($R^{13}$), —CH$_2$N($R^{12}$)S(O)$_2$($R^{13}$), and —P(O)($R^{17}$)($R^{17a}$), wherein $C_{1-6}$alkyl, $C_{2-6}$alkenyl, $C_{2-6}$alkynyl, $C_{3-10}$cycloalkyl, and $C_{2-9}$heterocycloalkyl are optionally substituted with one, two, or three $R^{20c}$.

$R^7$ is selected from hydrogen, halogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{1-9}$heteroaryl, —O$R^{12}$, —S$R^{12}$, —N($R^{12}$)($R^{13}$), —C(O)O$R^{12}$, —OC(O)N($R^{12}$)($R^{13}$), —N($R^{14}$)C(O)N($R^{12}$)($R^{13}$), —N($R^{14}$)C(O)O$R^{15}$, —N($R^{14}$)S(O)$_2$$R^{15}$, —C(O)$R^{15}$, —S(O)$R^{15}$, —OC(O)$R^{15}$, —C(O)N($R^{12}$)($R^{13}$), —C(O)C(O)N($R^{12}$)($R^{13}$), —N($R^{14}$)C(O)$R^{15}$, —S(O)$_2$$R^{15}$, —S(O)$_2$N($R^{12}$)($R^{13}$), —S(=O)(=NH)N($R^{12}$)($R^{13}$), —CH$_2$C(O)N($R^{12}$)($R^{13}$), —CH$_2$N($R^{14}$)C(O)$R^{15}$, —CH$_2$S(O)$_2$$R^{15}$, —CH$_2$S(O)$_2$N($R^{12}$)($R^{13}$), —CH$_2$N($R^{12}$)S(O)$_2$($R^{13}$), and —P(O)($R^{17}$)($R^{17a}$), wherein $C_{1-6}$alkyl, $C_{2-6}$alkenyl, $C_{2-6}$alkynyl, $C_{3-10}$cycloalkyl, $C_{2-9}$heterocycloalkyl, and $C_{1-9}$heteroaryl are optionally substituted with one, two, or three $R^{20c}$;

each $R^{10}$ is independently selected from halogen, —CN, $C_{1-6}$alkyl, $C_{2-6}$alkenyl, $C_{2-6}$alkynyl, $C_{3-7}$cycloalkyl, $C_{2-9}$heterocycloalkyl, $C_{6-10}$aryl, $C_{1-9}$heteroaryl, —O$R^{12}$, —S$R^{12}$, —N($R^{12}$)($R^{13}$), —C(O)O$R^{12}$, —OC(O)N($R^{12}$)($R^{13}$), —N($R^{14}$)C(O)N($R^{12}$)($R^{13}$), —N($R^{14}$)C(O)O$R^{15}$, —N($R^{14}$)S(O)$_2$$R^{15}$, —C(O)$R^{15}$, —S(O)$R^{15}$, —OC(O)$R^{15}$, —C(O)N($R^{12}$)($R^{13}$), —C(O)C(O)N($R^{12}$)($R^{13}$), —N($R^{14}$)C(O)$R^{15}$, —S(O)$_2$$R^{15}$, —S(O)$_2$N($R^{12}$)($R^{13}$), —S(=O)(=NH)N($R^{12}$)($R^{13}$), —CH$_2$C(O)N($R^{12}$)($R^{13}$), —CH$_2$N($R^{14}$)C(O)$R^{15}$, —CH$_2$S(O)$_2$$R^{15}$, —CH$_2$S(O)$_2$N($R^{12}$)($R^{13}$), —CH$_2$N($R^{12}$)S(O)$_2$($R^{13}$), and —P(O)($R^{17}$)($R^{17a}$), wherein $C_{1-6}$alkyl, $C_{2-6}$alkenyl, $C_{2-6}$alkynyl, $C_{3-7}$cycloalkyl, $C_{2-9}$heterocycloalkyl, $C_{6-10}$aryl, and $C_{1-9}$heteroaryl are optionally substituted with one, two, or three $R^{20a}$;

each $R^{12}$ is independently selected from hydrogen, $C_{1-6}$alkyl, $C_{1-6}$haloalkyl, $C_{2-6}$alkenyl, $C_{2-6}$alkynyl, $C_{3-7}$cycloalkyl, $C_{2-9}$heterocycloalkyl, $C_{6-10}$aryl, and $C_{1-9}$heteroaryl, wherein $C_{1-6}$alkyl, $C_{2-6}$alkenyl, $C_{2-6}$alkynyl, $C_{3-7}$cycloalkyl, $C_{2-9}$heterocycloalkyl, $C_{6-10}$aryl, and $C_{1-9}$heteroaryl are optionally substituted with one, two, or three $R^{20e}$;

each $R^{13}$ is independently selected from hydrogen, $C_{1-6}$alkyl, and $C_{1-6}$haloalkyl; or $R^{12}$ and $R^{13}$, together with the nitrogen to which they are attached, form a $C_{2-9}$heterocycloalkyl ring optionally substituted with one, two, or three $R^{20f}$;

$R^{13a}$ is selected from $C_{1-6}$alkyl and $C_{1-6}$haloalkyl; or $R^{12}$ and $R^{13a}$, together with the nitrogen to which they are attached, form a $C_{2-9}$heterocycloalkyl ring optionally substituted with one, two, or three $R^{20f}$;

each $R^{14}$ is independently selected from hydrogen, $C_{1-6}$alkyl, and $C_{1-6}$haloalkyl;

each $R^{15}$ is independently selected $C_{1-6}$alkyl, $C_{2-6}$alkenyl, $C_{2-6}$alkynyl, $C_{3-7}$cycloalkyl, $C_{2-9}$heterocycloalkyl, $C_{6-10}$aryl, and $C_{1-9}$ heteroaryl, wherein $C_{1-6}$alkyl, $C_{2-6}$alkenyl, $C_{2-6}$alkynyl, $C_{3-7}$cycloalkyl, $C_{2-9}$heterocycloalkyl, $C_{6-10}$aryl, and $C_{1-9}$heteroaryl are optionally substituted with one, two, or three $R^{20g}$;

each $R^{17}$ and each $R^{17a}$ are each independently selected from $C_{1-6}$alkyl and $C_{3-6}$cycloalkyl, wherein $C_{1-6}$alkyl and $C_{3-6}$cycloalkyl are optionally substituted with one, two or three of $R^{20h}$; or $R^{17}$ and $R^{17a}$ are combined to form a $C_{2-9}$heterocycloalkyl ring;

each $R^{20a}$, $R^{20b}$, $R^{20c}$, $R^{20d}$, $R^{20e}$, $R^{20f}$, $R^{20g}$, and $R^{20h}$ are each independently selected from halogen, oxo, =NH, —CN, $C_{1-6}$alkyl, $C_{2-6}$alkenyl, $C_{2-6}$alkynyl, $C_{3-10}$cycloalkyl, —CH$_2$—$C_{3-10}$cycloalkyl, $C_{2-9}$heterocycloalkyl, —CH$_2$—$C_{2-9}$heterocycloalkyl, $C_{6-10}$aryl, —CH$_2$—$C_{6-10}$aryl, $C_{1-9}$heteroaryl, —O$R^{21}$, —S$R^{21}$, —N($R^{22}$)($R^{23}$), —C(O)OR²², —C(O)N(R²²)(R²³), —C(O)C(O)N(R²²)(R²³), —OC(O)N(R²²)(R²³), —N(R²⁴)C(O)N(R²²)(R²³), —N(R²⁴)C(O)OR²⁵, —N(R²⁴)C(O)R²⁵, —N(R²⁴)S(O)₂R²⁵, —C(O)R²⁵, —S(O)₂R²⁵, —S(O)₂N(R²²)(R²³), —OCH₂C(O)OR²², and —OC(O)R²⁵, wherein $C_{1-6}$alkyl, $C_{2-6}$alkenyl, $C_{2-6}$alkynyl, $C_{3-10}$cycloalkyl, —CH₂—$C_{3-10}$cycloalkyl, $C_{2-9}$heterocycloalkyl, —CH₂—$C_{2-9}$heterocycloalkyl, $C_{6-10}$aryl, —CH₂—$C_{6-10}$aryl, and $C_{1-9}$heteroaryl are optionally substituted with one, two, or three groups independently selected from halogen, oxo, =NH, —CN, $C_{1-6}$alkyl, $C_{1-6}$haloalkyl, $C_{1-6}$alkoxy, $C_{1-6}$haloalkoxy, —OR²¹, —SR²¹, —N(R²²)(R²³), —C(O)OR²², —C(O)N(R²²)(R²³), —C(O)C(O)N(R²²)(R²³), —OC(O)N(R²²)(R²³), —N(R²⁴)C(O)N(R²²)(R²³), —N(R²⁴)C(O)OR²⁵, —N(R²⁴)C(O)R²⁵, —N(R²⁴)S(O)₂R²⁵, —C(O)R²⁵, —S(O)₂R²⁵, —S(O)₂N(R²²)(R²³), and —OC(O)R²⁵;

each R²¹ is independently selected from H, $C_{1-6}$alkyl, $C_{1-6}$haloalkyl, $C_{2-6}$alkenyl, $C_{2-6}$alkynyl, $C_{3-7}$cycloalkyl, $C_{2-9}$heterocycloalkyl, $C_{6-10}$aryl, and $C_{1-9}$heteroaryl, wherein $C_{3-7}$cycloalkyl, $C_{2-9}$heterocycloalkyl, $C_{6-10}$aryl, and $C_{1-9}$heteroaryl are optionally substituted with one, two, or three groups independently selected from halogen and $C_{1-6}$alkyl;

each R²² is independently selected from H, $C_{1-6}$alkyl, $C_{1-6}$haloalkyl, $C_{2-6}$alkenyl, $C_{2-6}$alkynyl, $C_{3-7}$cycloalkyl, $C_{2-9}$heterocycloalkyl, $C_{6-10}$aryl, and $C_{1-9}$heteroaryl, wherein $C_{3-7}$cycloalkyl, $C_{2-9}$heterocycloalkyl, $C_{6-10}$aryl, and $C_{1-9}$heteroaryl are optionally substituted with one, two, or three groups independently selected from halogen and $C_{1-6}$alkyl;

each R²³ is independently selected from H and $C_{1-6}$alkyl;

each R²⁴ is independently selected from H and $C_{1-6}$alkyl; and each R²¹ is selected from $C_{1-6}$alkyl, $C_{2-6}$alkenyl, $C_{2-6}$alkynyl, $C_{3-7}$cycloalkyl, $C_{2-9}$heterocycloalkyl, $C_{6-10}$aryl, and $C_{1-9}$heteroaryl, wherein $C_{1-6}$alkyl, $C_{3-7}$cycloalkyl, $C_{2-9}$heterocycloalkyl, $C_{6-10}$aryl, and $C_{1-9}$heteroaryl are optionally substituted with one, two, or three groups independently selected from halogen, $C_{1-6}$alkyl, $C_{1-6}$haloalkyl, $C_{1-6}$alkoxy, $C_{3-7}$cycloalkyl, $C_{2-9}$heterocycloalkyl, $C_{6-10}$aryl, and $C_{1-9}$heteroaryl.

In embodiments of the compound of Formula (I-2), the compound has the Formula (Ia-2), or a pharmaceutically acceptable salt or solvate thereof:

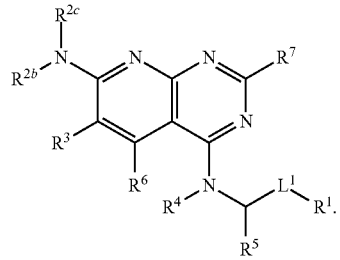

Formula (Ia-2)

In some embodiments, R²ᵃ is $C_{1-6}$alkyl optionally substituted with one, two, or three R²⁰ᵃ.

In some embodiments, R²ᵃ is unsubstituted $C_{1-6}$alkyl.

In some embodiments, R²ᵃ is —CH₃.

In embodiments of the compound of Formula (I-2), the compound has the Formula (Ib-2), or a pharmaceutically acceptable salt or solvate thereof:

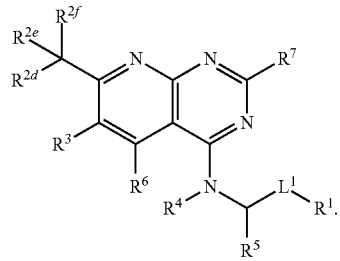

Formula (Ib-2)

In some embodiments, R²ᵇ is $C_{1-6}$alkyl optionally substituted with one, two, or three R²⁰ᵃ.

In some embodiments, R²ᵉ is $C_{1-6}$alkyl optionally substituted with one, two, or three R²⁰ᵃ.

In some embodiments, R²ᵉ is hydrogen.

In embodiments of the compound of Formula (I-2), the compound has the Formula (Ic-2), or a pharmaceutically acceptable salt or solvate thereof:

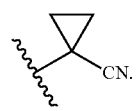

Formula (Ic-2)

In some embodiments, R²ᵈ is hydrogen or $C_{1-6}$alkyl optionally substituted with one, two, or three R²⁰ᵃ.

In some embodiments, R²ᵉ is hydrogen.
In some embodiments, R²¹ is hydrogen.
In some embodiments, R² is halogen.
In some embodiments, R²⁰ᵇ is —CN.
In some embodiments, R³ is

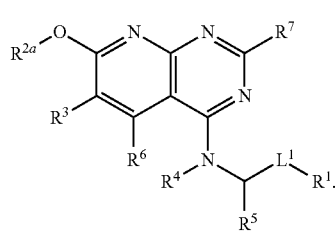

In some embodiments, R⁶ is selected from hydrogen, halogen, $C_{1-6}$alkyl, $C_{3-10}$cycloalkyl, $C_{2-9}$heterocycloalkyl, and $C_{1-9}$heteroaryl, wherein $C_{1-6}$alkyl, $C_{3-10}$cycloalkyl, $C_{2-9}$heterocycloalkyl, and $C_{1-9}$heteroaryl are optionally substituted with one, two, or three R²⁰ᵉ. In some embodiments, R⁶ is independently selected from hydrogen, halogen, and unsubstituted $C_{1-6}$alkyl. In some embodiments, R⁶ is hydrogen.

In some embodiments, R⁷ is selected from hydrogen, halogen, $C_{1-6}$alkyl, $C_{3-10}$cycloalkyl, $C_{2-9}$heterocycloalkyl, and $C_{1-9}$heteroaryl, wherein $C_{1-6}$alkyl, $C_{3-10}$cycloalkyl, $C_{2-9}$heterocycloalkyl, and $C_{1-9}$heteroaryl are optionally substituted with one, two, or three R²⁰ᵉ. In some embodiments, R⁷ is independently selected from hydrogen, halogen, and unsubstituted $C_{1-6}$alkyl. In some embodiments, R⁷ is hydrogen.

In some embodiments, R⁵ is selected from $C_{1-6}$alkyl and $C_{1-6}$haloalkyl. In some embodiments, R⁵ is —CH₃.

In some embodiments, $R^4$ is hydrogen.

In some embodiments, $L^1$ is a bond.

In some embodiments, $R^1$ is a 6-10 membered aryl ring substituted with one or more $R^{10}$. In some embodiments, $R^1$ is phenyl substituted with one or more $R^{10}$. In some embodiments, $R^1$ is phenyl substituted with one, two, or three $R^{10}$.

In some embodiments, each $R^{10}$ is independently selected from halogen, $C_{1-6}$alkyl, $C_{3-7}$cycloalkyl, $C_{2-9}$heterocycloalkyl, $C_{6-10}$aryl, $C_{1-9}$heteroaryl, $-OR^{12}$, and $N(R^{12})(R^{13})$, wherein $C_{1-6}$alkyl, $C_{3-7}$cycloalkyl, $C_{2-9}$heterocycloalkyl, $C_{6-10}$aryl, and $C_{1-9}$heteroaryl are optionally substituted with one, two, or three $R^{20d}$.

In some embodiments, each $R^{10}$ is independently selected from halogen, $C_{1-6}$alkyl, and $N(R^{12})(R^{13})$ wherein $C_{1-6}$alkyl is optionally substituted with one, two, or three $R^{20a}$d.

In some embodiments, each $R^{10}$ is independently selected from halogen and $C_{1-6}$alkyl, wherein $C_{1-6}$alkyl is substituted with one, two, or three $R^{20d}$, and each $R^{20d}$ is halogen or $-OH$.

In some embodiments, $R^1$ is independently selected from

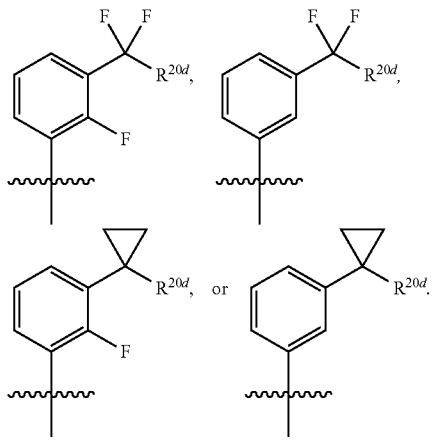

In some embodiments, $R^{20d}$ is $C_{1-6}$alkyl optionally substituted with one, two, or three groups independently selected from F and $-OH$.

In some embodiments, $R^{20d}$ is $C_{1-3}$alkyl substituted with one $-OH$.

In some embodiments, $R^1$ is selected from

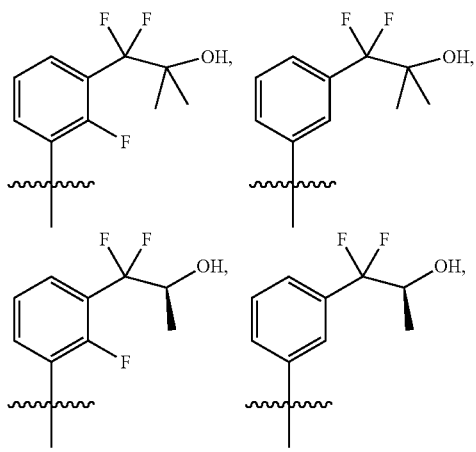

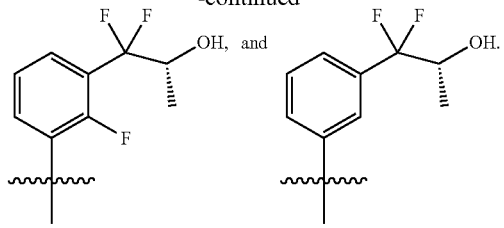

In an aspect is provided a pharmaceutical composition comprising a compound described herein, or a pharmaceutically acceptable salt or solvate thereof, and a pharmaceutically acceptable excipient.

In an aspect is provided a method of treating cancer in a subject in need thereof, comprising administering to the subject a therapeutically effective amount of a compound described herein, or a pharmaceutically acceptable salt or solvate thereof.

In some embodiments, the cancer is a solid tumor or a hematological cancer.

In some embodiments, the subject is administered with an additional agent or therapy.

In an aspect is provided a method of reducing Ras signaling output, comprising contacting a SOS1 protein with an effective amount of a compound described herein, or a pharmaceutically acceptable salt or solvate thereof, thereby reducing the Ras signaling output.

In some embodiments, the compound disrupts interaction between a Ras protein and SOS1.

In some embodiments, the Ras protein is a wildtype K-Ras or a mutant K-Ras.

In an aspect is provided a method of inhibiting cell growth, comprising administering a cell expressing SOS1 with an effective amount of a compound described herein, or a pharmaceutically acceptable salt or solvate thereof, thereby inhibiting growth of said cells.

In an aspect is provided a method of reducing Ras signaling output of a cell, comprising contacting the cell with an effective amount of a compound Formula (I), or a pharmaceutically acceptable salt or solvate thereof, in combination with an additional agent, wherein the additional agent is a chemotherapeutic agent, a radioactive agent, an immune modulator, or an inhibitor against one or more targets selected from the group of: MEK, epidermal growth factor receptor (EGFR), FGFR1, FGFR2, FGFR3, FGFR4, mitotic kinase, topoisomerase, ALK, c-MET, ErbB2, AXL, NTRK1, RET, A-Raf, B-Raf, C-Raf, ERK, MDM2, mTOR, BET, IGF1/2, IGF1-R, CDK9, SHC, GAB, GRB, PI3-kinase, MAPK, SHIP1, SHIP2, SHP1, SHP2, SRC, JAK, PARP, BTK, FLT3, HDAC, VEGFR, PDGFR, LCK, Bcr-Abl, AKT, wildtype KRas, KRas mutant (e.g., KrasG12C, KRas G12D, KRas G12S, KRas G12V, KRas G13D, KRas G13C, or KRas G13V), ROS1, CDK4/6, and a mutant of the one or more target thereof, wherein the compound of Formula (I) has the structure:

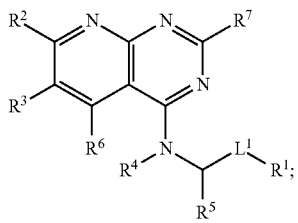

Formula (I)

wherein:
R[1] is a 3-12 membered cycloalkyl ring, 3-12 membered heterocycloalkyl ring, 6-10 membered aryl ring, or 5-10 membered heteroaryl ring, wherein the 3-12 membered cycloalkyl ring, 3-12 membered heterocycloalkyl ring, 6-10 membered aryl ring, and 5-10 membered heteroaryl ring are optionally substituted with one or more R[10];

L[1] is a bond or $C_{1-6}$alkyl;

R[2] is —OR[2a], —NR[2b]R[2c], —SR[2g], —S(O)R[2h], —S(O)$_2$R[2h], —S(O)$_2$NR[2b]R[2c], —C(R[2d])(R[2e])(R[2f]), C(O)NR[2b]R[2c], —CN, or halogen;

R[2a] is selected from hydrogen, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —C(O)OR[12], —C(O)R[15], —C(O)N(R[12])(R[13]), —S(O)$_2$R[15], —S(O)$_2$N(R[12])(R[13]), wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three R[20a];

R[2b] is selected from hydrogen, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —C(O)OR[12], —C(O)R[15], —C(O)N(R[12])(R[13]), —S(O)$_2$R[15], and —S(O)$_2$N(R[12])(R[13]), wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three R[20a];

R[2c] is selected from hydrogen, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three R[20a]; or R[2b] and R[2c], together with the nitrogen to which they are attached, form a $C_{2-9}$heterocycloalkyl ring optionally substituted with one, two, or three R[20a];

R[2d] is selected from hydrogen, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —OR[12], —SR[12], —N(R[12])(R[13]), —C(O)OR[12], —OC(O)N(R[12])(R[13]), —N(R[14])C(O)N(R[12])(R[13]), —N(R[14])C(O)OR[15], —N(R[14])S(O)$_2$R[15], —C(O)R[15], —S(O)R[15], —OC(O)R[15], —C(O)N(R[12])(R[13]), —C(O)C(O)N(R[12])(R[13]), —N(R[14])C(O)R[15], —S(O)$_2$R[15], —S(O)$_2$N(R[12])(R[13]), —S(=O)(=NH)N(R[12])(R[13]), —CH$_2$C(O)N(R[12])(R[13]), —CH$_2$N(R[14])C(O)R[15], —CH$_2$S(O)$_2$R[15], —CH$_2$S(O)$_2$N(R[12])(R[13]), —CH$_2$N(R[12])S(O)$_2$(R[13]), and —P(O)(R[17])(R[17a]), wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three R[20a];

R[2e] is selected from hydrogen, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three R[20a];

R[2f] is selected from hydrogen, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three R[20a];

R[2g] is selected from hydrogen, $C_{2-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —C(O)OR[12], —C(O)R[15], —C(O)N(R[12])(R[13]), —S(O)$_2$R[15], —S(O)$_2$N(R[12])(R[13]), wherein $C_{2-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three R[20a];

R[2h] is selected from $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three R[20a];

R[3] is selected from halogen, $C_{1-6}$alkyl, $C_{2-6}$alkenyl, $C_{2-6}$alkynyl, $C_{3-14}$cycloalkyl, $C_{2-9}$heterocycloalkyl, $C_{6-10}$aryl, $C_{1-9}$heteroaryl, —SR[12], —N(R[12])(R[13]), —C(O)OR[12], —OC(O)N(R[12])(R[13]), —N(R[14])C(O)N(R[12])(R[13]), —N(R[14])C(O)OR[15], —N(R[14])S(O)$_2$R[15], N(R[14])S(O)R[15], —C(O)R[15], —S(O)R[15], —OC(O)R[15], —C(O)N(R[12])(R[13a]), —C(O)C(O)N(R[12])(R[13]), —N(R[14])C(O)R[15], —S(O)$_2$R[15], —S(O)$_2$N(R[12])(R[13]) S(O)N(R[12])(R[13]), —S(=O)(=NH)N(R[12])(R[13]), —CH$_2$C(O)N(R[12])(R[13]), —CH$_2$N(R[14])C(O)R[15], —CH$_2$S(O)$_2$R[15], —CH$_2$S(O)$_2$N(R[12])(R[13]), —CH$_2$N(R[12])S(O)$_2$(R[13]), CH$_2$S(O) R[15], —CH$_2$S(O)N(R[12])(R[13]), —CH$_2$N(R[12])S(O)(R[13]) and —P(O)(R[17])(R[17a]), wherein $C_{1-6}$alkyl, $C_{2-6}$alkenyl, $C_{2-6}$alkynyl, $C_{3-14}$cycloalkyl, $C_{2-9}$heterocycloalkyl, $C_{6-10}$aryl, and $C_{1-9}$heteroaryl are optionally substituted with one, two, or three R[20b];

R[4] is selected from hydrogen, $C_{1-6}$alkyl, and $C_{1-6}$haloalkyl;
R[5] is selected from hydrogen, $C_{1-6}$alkyl, and $C_{1-6}$haloalkyl;
R[6] is selected from hydrogen, halogen, —CN, $C_{1-6}$alkyl, $C_{2-6}$alkenyl, $C_{2-6}$alkynyl, $C_{3-10}$cycloalkyl, $C_{2-9}$heterocycloalkyl, —OR[12], —SR[12], —N(R[12])(R[13]), —C(O)OR[12], —OC(O)N(R[12])(R[13]), —N(R[14])C(O)N(R[12])(R[13]), —N(R[14])C(O)OR[15], —N(R[14])S(O)$_2$R[15], —C(O)R[15], —S(O)R[15], —OC(O)R[15], —C(O)N(R[12])(R[13]), —C(O)C(O)N(R[12])(R[13]), —N(R[14])C(O)R[15], —S(O)$_2$R[15], —S(O)$_2$N(R[12])(R[13]), —S(=O)(=NH)N(R[12])(R[13]), —CH$_2$C(O)N(R[12])(R[13]), —CH$_2$N(R[14])C(O)R[15], —CH$_2$S(O)$_2$R[15], —CH$_2$S(O)$_2$N(R[12])(R[13]), —CH$_2$N(R[12])S(O)$_2$(R[13]), and —P(O)(R[17])(R[17a]) wherein $C_{1-6}$alkyl, $C_{2-6}$alkenyl, $C_{2-6}$alkynyl, $C_{3-10}$cycloalkyl, and $C_{2-9}$heterocycloalkyl are optionally substituted with one, two, or three R[20c];

R[7] is selected from hydrogen, halogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{1-9}$heteroaryl, —OR[12], —SR[12], —N(R[12])(R[13]), —C(O)OR[12], —OC(O)N(R[12])(R[13]), —N(R[14])C(O)N(R[12])(R[13]), —N(R[14])C(O)OR[15], —N(R[14])S(O)$_2$R[15], —C(O)R[15], —S(O)R[15], —OC(O)R[15], —C(O)N(R[12])(R[13]), —C(O)C(O)N(R[12])(R[13]), —N(R[14])C(O)R[15], —S(O)$_2$R[15], —S(O)$_2$N(R[12])(R[13]), —S(=O)(=NH)N(R[12])(R[13]), —CH$_2$C(O)N(R[12])(R[13]), —CH$_2$N(R[14])C(O)R[15], —CH$_2$S(O)$_2$R[15], —CH$_2$S(O)$_2$N(R[12])(R[13]), —CH$_2$N(R[12])S(O)$_2$(R[13]), and —P(O)(R[17])(R[17a]), wherein $C_{1-6}$alkyl, $C_{2-6}$alkenyl, $C_{2-6}$alkynyl, $C_{3-10}$cycloalkyl, $C_{2-9}$heterocycloalkyl, and $C_{1-9}$heteroaryl are optionally substituted with one, two, or three $R^{20c}$;

each $R^{10}$ is independently selected from halogen, —CN, $C_{1-6}$alkyl, $C_{2-6}$alkenyl, $C_{2-6}$alkynyl, $C_{3-7}$cycloalkyl, $C_{2-9}$heterocycloalkyl, $C_{6-10}$aryl, $C_{1-9}$heteroaryl, —OR$^{12}$, —SR$^{12}$, —N(R$^{12}$)(R$^{13}$), —C(O)OR$^{12}$, —OC(O)N(R$^{12}$)(R$^{13}$), —N(R$^{14}$)C(O)N(R$^{12}$)(R$^{13}$), —N(R$^{14}$)C(O)OR$^{15}$, —N(R$^{14}$)S(O)$_2$R$^{15}$, —C(O)R$^{15}$, —S(O)R$^{15}$, —OC(O)R$^{15}$, —C(O)N(R$^{12}$)(R$^{13}$), —C(O)C(O)N(R$^{12}$)(R$^{13}$), —N(R$^{14}$)C(O)R$^{15}$, —S(O)$_2$R$^{15}$, —S(O)$_2$N(R$^{12}$)(R$^{13}$), —S(=O)(=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, —CH$_2$S(O)$_2$N(R$^{12}$)(R$^{13}$), —CH$_2$N(R$^{12}$)S(O)$_2$(R$^{13}$), and —P(O)(R$^{17}$)(R$^{17a}$), wherein $C_{1-6}$alkyl, $C_{2-6}$alkenyl, $C_{2-6}$alkynyl, $C_{3-7}$cycloalkyl, $C_{2-9}$heterocycloalkyl, $C_{6-10}$aryl, and $C_{1-9}$heteroaryl are optionally substituted with one, two, or three $R^{20a}$;

each $R^{12}$ is independently selected from hydrogen, $C_{1-6}$alkyl, $C_{1-6}$haloalkyl, $C_{2-6}$alkenyl, $C_{2-6}$alkynyl, $C_{3-7}$cycloalkyl, $C_{2-9}$heterocycloalkyl, $C_{6-10}$aryl, and $C_{1-9}$heteroaryl, wherein $C_{1-6}$alkyl, $C_{2-6}$alkenyl, $C_{2-6}$alkynyl, $C_{3-7}$cycloalkyl, $C_{2-9}$heterocycloalkyl, $C_{6-10}$aryl, and $C_{1-9}$heteroaryl are optionally substituted with one, two, or three $R^{20e}$;

each $R^{13}$ is independently selected from hydrogen, $C_{1-6}$alkyl, and $C_{1-6}$haloalkyl; or $R^{12}$ and $R^{13}$, together with the nitrogen to which they are attached, form a $C_{2-9}$heterocycloalkyl ring optionally substituted with one, two, or three $R^{20f}$;

$R^{13a}$ is selected from $C_{1-6}$alkyl and $C_{1-6}$haloalkyl; or $R^{12}$ and $R^{13a}$, together with the nitrogen to which they are attached, form a $C_{2-9}$heterocycloalkyl ring optionally substituted with one, two, or three $R^{20f}$;

each $R^{14}$ is independently selected from hydrogen, $C_{1-6}$alkyl, and $C_{1-6}$haloalkyl;

each $R^{15}$ is independently selected $C_{1-6}$alkyl, $C_{2-6}$alkenyl, $C_{2-6}$alkynyl, $C_{3-7}$cycloalkyl, $C_{2-9}$heterocycloalkyl, $C_{6-10}$aryl, and $C_{1-9}$heteroaryl, wherein $C_{1-6}$alkyl, $C_{2-6}$alkenyl, $C_{2-6}$alkynyl, $C_{3-7}$cycloalkyl, $C_{2-9}$heterocycloalkyl, $C_{6-10}$aryl, and $C_{1-9}$heteroaryl are optionally substituted with one, two, or three $R^{20g}$;

each $R^{17}$ and each $R^{17a}$ are each independently selected from $C_{1-6}$alkyl and $C_{3-6}$cycloalkyl, wherein $C_{1-6}$alkyl and $C_{3-6}$cycloalkyl are optionally substituted with one, two or three of $R^{20h}$; or $R^{17}$ and $R^{17a}$ are combined to form a $C_{2-9}$heterocycloalkyl ring;

each $R^{20a}$, $R^{20b}$, $R^{20c}$, $R^{20d}$, $R^{20e}$, $R^{20f}$, $R^{20g}$, and $R^{20h}$ are each independently selected from halogen, oxo, =NH, —CN, $C_{1-6}$alkyl, $C_{2-6}$alkenyl, $C_{2-6}$alkynyl, $C_{3-10}$cycloalkyl, —CH$_2$—$C_{3-10}$cycloalkyl, $C_{2-9}$heterocycloalkyl, —CH$_2$—$C_{2-9}$heterocycloalkyl, $C_{6-10}$aryl, —CH$_2$—$C_{6-10}$aryl, $C_{1-9}$heteroaryl, —OR$^{21}$, —SR$^{21}$, —N(R$^{22}$)(R$^{23}$), —C(O)OR$^{22}$, —C(O)N(R$^{22}$)(R$^{23}$), —C(O)C(O)N(R$^{22}$)(R$^{23}$), —OC(O)N(R$^{22}$)(R$^{23}$), —N(R$^{24}$)C(O)N(R$^{22}$)(R$^{23}$), —N(R$^{24}$)C(O)OR$^{25}$, —N(R$^{24}$)C(O)R$^{25}$, —N(R$^{24}$)S(O)$_2$R$^{25}$, —C(O)R$^{25}$, —S(O)$_2$R$^{25}$, —S(O)$_2$N(R$^{22}$)(R$^{23}$), —OCH$_2$C(O)OR$^{22}$, and —OC(O)R$^{25}$, wherein $C_{1-6}$alkyl, $C_{2-6}$alkenyl, $C_{2-6}$alkynyl, $C_{3-10}$cycloalkyl, —CH$_2$—$C_{3-10}$cycloalkyl, $C_{2-9}$heterocycloalkyl, —CH$_2$—$C_{2-9}$heterocycloalkyl, $C_{6-10}$aryl, —CH$_2$—$C_{6-10}$aryl, and $C_{1-9}$heteroaryl are optionally substituted with one, two, or three groups independently selected from halogen, oxo, =NH, —CN, $C_{1-6}$alkyl, $C_{1-6}$haloalkyl, $C_{1-6}$alkoxy, $C_{1-6}$haloalkoxy, —OR$^{21}$, —SR$^{21}$, —N(R$^{22}$)(R$^{23}$), —C(O)OR$^{22}$, —C(O)N(R$^{22}$)(R$^{23}$), —C(O)C(O)N(R$^{22}$)(R$^{23}$), —OC(O)N(R$^{22}$)(R$^{23}$), —N(R$^{24}$)C(O)N(R$^{22}$)(R$^{23}$), —N(R$^{24}$)C(O)OR$^{25}$, —N(R$^{24}$)C(O)R$^{25}$, —N(R$^{24}$)S(O)$_2$R$^{25}$, —C(O)R$^{25}$, —S(O)$_2$R$^{25}$, —S(O)$_2$N(R$^{22}$)(R$^{23}$), and —OC(O)R$^{25}$;

each $R^{21}$ is independently selected from H, $C_{1-6}$alkyl, $C_{1-6}$haloalkyl, $C_{2-6}$alkenyl, $C_{2-6}$alkynyl, $C_{3-7}$cycloalkyl, $C_{2-9}$heterocycloalkyl, $C_{6-10}$aryl, and $C_{1-9}$heteroaryl, wherein $C_{3-7}$cycloalkyl, $C_{2-9}$heterocycloalkyl, $C_{6-10}$aryl, and $C_{1-9}$heteroaryl are optionally substituted with one, two, or three groups independently selected from halogen and $C_{1-6}$alkyl;

each $R^{22}$ is independently selected from H, $C_{1-6}$alkyl, $C_{1-6}$haloalkyl, $C_{2-6}$alkenyl, $C_{2-6}$alkynyl, $C_{3-7}$cycloalkyl, $C_{2-9}$heterocycloalkyl, $C_{6-10}$aryl, and $C_{1-9}$heteroaryl, wherein $C_{3-7}$cycloalkyl, $C_{2-9}$heterocycloalkyl, $C_{6-10}$aryl, and $C_{1-9}$heteroaryl are optionally substituted with one, two, or three groups independently selected from halogen and $C_{1-6}$alkyl;

each $R^{23}$ is independently selected from H and $C_{1-6}$alkyl;

each $R^{24}$ is independently selected from H and $C_{1-6}$alkyl; and each $R^{25}$ is selected from $C_{1-6}$alkyl, $C_{2-6}$alkenyl, $C_{2-6}$alkynyl, $C_{3-7}$cycloalkyl, $C_{2-9}$heterocycloalkyl, $C_{6-10}$aryl, and $C_{1-9}$heteroaryl, wherein $C_{1-6}$alkyl, $C_{3-7}$cycloalkyl, $C_{2-9}$heterocycloalkyl, $C_{6-10}$aryl, and $C_{1-9}$heteroaryl are optionally substituted with one, two, or three groups independently selected from halogen, $C_{1-6}$alkyl, $C_{1-6}$haloalkyl, $C_{1-6}$alkoxy, $C_{3-7}$cycloalkyl, $C_{2-9}$heterocycloalkyl, $C_{6-10}$aryl, and $C_{1-9}$heteroaryl In some embodiments, the additional agent is an inhibitor against one or more targets selected from the group of: MEK, epidermal growth factor receptor (EGFR), A-Raf, B-Raf, C-Raf, SHP2, wildtype KRas, a KRas mutant, and CDK4/6.

In some embodiments, the additional agent is a chemotherapeutic agent, a radioactive agent, or an immune modulator.

In an aspect is provided a SOS1 protein bound by a compound described herein, or a pharmaceutically acceptable salt or solvate thereof, wherein interaction of the SOS1 protein with a Ras protein is reduced as compared to a SOS1 protein unbound to said compound.

In an aspect is provided a compound selected from the compounds shown in Table 1.

In one aspect, the disclosure provides a compound of Formula (I), or a pharmaceutically acceptable salt or solvate thereof:

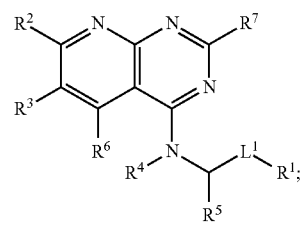

Formula (I)

wherein:

R$^1$ is a 3-12 membered cycloalkyl ring, 3-12 membered heterocycloalkyl ring, 6-10 membered aryl ring, or 5-10 membered heteroaryl ring, wherein the 3-12 membered cycloalkyl ring, 3-12 membered heterocycloalkyl ring, 6-10 membered aryl ring, and 5-10 membered heteroaryl ring are optionally substituted with one or more R$^{10}$;

L$^1$ is a bond or $C_{1-6}$alkyl;

R$^2$ is —OR$^{2a}$, —NR$^{2b}$R$^{2c}$, —SR$^{2g}$, —S(O)R$^{2h}$, —S(O)$_2$R$^{2h}$, —S(O)$_2$NR$^{2b}$R$^{2c}$, —C(R$^{2d}$)(R$^{2e}$)(R$^{2f}$), —C(O)NR$^{2b}$R$^{2c}$, —CN, or halogen;

$R^{2a}$ is selected from hydrogen, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —C(O)OR$^{12}$, —C(O)R$^{15}$, —C(O)N(R$^{12}$)(R$^{13}$), —S(O)$_2$R$^{15}$, —S(O)$_2$N(R$^{12}$)(R$^{13}$), wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20a}$;

$R^{2b}$ is selected from hydrogen, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —C(O)OR$^{12}$, —C(O)R$^{15}$, —C(O)N(R$^{12}$)(R$^{13}$), —S(O)$_2$R$^{15}$, and —S(O)$_2$N(R$^{12}$)(R$^{13}$), wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20a}$;

$R^{2c}$ is selected from hydrogen, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20a}$; or $R^{2b}$ and $R^{2c}$, together with the nitrogen to which they are attached, form a $C_{2-9}$heterocycloalkyl ring optionally substituted with one, two, or three $R^{20a}$;

$R^{2d}$ is selected from hydrogen, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —OR$^{12}$, —SR$^{12}$, —N(R$^{12}$)(R$^{13}$), —C(O)OR$^{12}$, —OC(O)N(R$^{12}$)(R$^{13}$), —N(R$^{14}$)C(O)N(R$^{12}$)(R$^{13}$), —N(R$^{14}$)C(O)OR$^{15}$, —N(R$^{14}$)S(O)$_2$R$^{15}$, —C(O)R$^{15}$, —S(O)R$^{15}$, —OC(O)R$^{15}$, —C(O)N(R$^{12}$)(R$^{13}$), —C(O)C(O)N(R$^{12}$)(R$^{13}$), —N(R$^{14}$)C(O)R$^{15}$, —S(O)$_2$R$^{15}$, —S(O)$_2$N(R$^{12}$)(R$^{13}$), —S(=O)(=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, —CH$_2$S(O)$_2$N(R$^{12}$)(R$^{13}$), —CH$_2$N(R$^{12}$)S(O)$_2$(R$^{13}$), and —P(O)(R$^{17}$)(R$^{17a}$), wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20a}$;

$R^{2e}$ is selected from hydrogen, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20a}$;

$R^{2f}$ is selected from hydrogen, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20a}$;

$R^{2g}$ is selected from hydrogen, $C_{2-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —C(O)OR$^{12}$, —C(O)R$^{15}$, —C(O)N(R$^{12}$)(R$^{13}$), —S(O)$_2$R$^{15}$, —S(O)$_2$N(R$^{12}$)(R$^{13}$), wherein $C_{2-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20a}$;

$R^{2h}$ is selected from $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20a}$;

$R^3$ is selected from halogen, $C_{1-6}$alkyl, $C_{2-6}$alkenyl, $C_{2-6}$alkynyl, $C_{3-14}$cycloalkyl, $C_{2-9}$heterocycloalkyl, $C_{6-10}$aryl, $C_{1-9}$heteroaryl, —SR$^{12}$, —N(R$^{12}$)(R$^{13}$), —C(O)OR$^{12}$, —OC(O)N(R$^{12}$)(R$^{13}$), —N(R$^{14}$)C(O)N(R$^{12}$)(R$^{13}$), —N(R$^{14}$)C(O)OR$^{15}$, —N(R$^{14}$)S(O)$_2$R$^{15}$, N(R$^{14}$)S(O)R$^{15}$, —C(O)R$^{15}$, —S(O)R$^{15}$, —OC(O)R$^{15}$, —C(O)N(R$^{12}$)(R$^{13a}$), —C(O)C(O)N(R$^{12}$)(R$^{13}$), —N(R$^{14}$)C(O)R$^{15}$, —S(O)$_2$R$^{15}$, —S(O)$_2$N(R$^{12}$)(R$^{13}$) S(O)N(R$^{12}$)(R$^{13}$), —S(=O)(=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, —CH$_2$S(O)$_2$N(R$^{12}$)(R$^{13}$), —CH$_2$N(R$^{12}$)S(O)$_2$(R$^{13}$), CH$_2$S(O) R$^{15}$, —CH$_2$S(O)N(R$^{12}$)(R$^{13}$), —CH$_2$N(R$^{12}$)S(O)(R$^{13}$) and —P(O)(R$^{17}$)(R$^{17a}$), wherein $C_{1-6}$alkyl, $C_{2-6}$alkenyl, $C_{2-6}$alkynyl, $C_{3-14}$cycloalkyl, $C_{2-9}$heterocycloalkyl, $C_{6-10}$aryl, and $C_{1-9}$heteroaryl are optionally substituted with one, two, or three $R^{20b}$;

$R^4$ is selected from hydrogen, $C_{1-6}$alkyl, and $C_{1-6}$haloalkyl;

$R^5$ is selected from hydrogen, $C_{1-6}$alkyl, and $C_{1-6}$haloalkyl;

$R^6$ is selected from hydrogen, halogen, —CN, $C_{1-6}$alkyl, $C_{2-6}$alkenyl, $C_{2-6}$alkynyl, $C_{3-10}$cycloalkyl, $C_{2-9}$heterocycloalkyl, —OR$^{12}$, —SR$^{12}$, —N(R$^{12}$)(R$^{13}$), —C(O)OR$^{12}$, —OC(O)N(R$^{12}$)(R$^{13}$), —N(R$^{14}$)C(O)N(R$^{12}$)(R$^{13}$), —N(R$^{14}$)C(O)OR$^{15}$, —N(R$^{14}$)S(O)$_2$R$^{15}$, —C(O)R$^{15}$, —S(O)R$^{15}$, —OC(O)R$^{15}$, —C(O)N(R$^{12}$)(R$^{13}$), —C(O)C(O)N(R$^{12}$)(R$^{13}$), —N(R$^{14}$)C(O)R$^{15}$, —S(O)$_2$R$^{15}$, —S(O)$_2$N(R$^{12}$)(R$^{13}$), —S(=O)(=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, —CH$_2$S(O)$_2$N(R$^{12}$)(R$^{13}$), —CH$_2$N(R$^{12}$)S(O)$_2$(R$^{13}$), and —P(O)(R$^{17}$)(R$^{17a}$) wherein $C_{1-6}$alkyl, $C_{2-6}$alkenyl, $C_{2-6}$alkynyl, $C_{3-10}$cycloalkyl, and $C_{2-9}$heterocycloalkyl are optionally substituted with one, two, or three $R^{20c}$;

$R^7$ is selected from hydrogen, halogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{1-9}$heteroaryl, —OR$^{12}$, —SR$^{12}$, —N(R$^{12}$)(R$^{13}$), —C(O)OR$^{12}$, —OC(O)N(R$^{12}$)(R$^{13}$), —N(R$^{14}$)C(O)N(R$^{12}$)(R$^{13}$), —N(R$^{14}$)C(O)OR$^{15}$, —N(R$^{14}$)S(O)$_2$R$^{15}$, —C(O)R$^{15}$, —S(O)R$^{15}$, —OC(O)R$^{15}$, —C(O)N(R$^{12}$)(R$^{13}$), —C(O)C(O)N(R$^{12}$)(R$^{13}$), —N(R$^{14}$)C(O)R$^{15}$, —S(O)$_2$R$^{15}$, —S(O)$_2$N(R$^{12}$)(R$^{13}$), —S(=O)(=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, —CH$_2$S(O)$_2$N(R$^{12}$)(R$^{13}$), —CH$_2$N(R$^{12}$)S(O)$_2$(R$^{13}$), and —P(O)(R$^{17}$)(R$^{17a}$), wherein $C_{1-6}$alkyl, $C_{2-6}$alkenyl, $C_{2-6}$alkynyl, $C_{3-10}$cycloalkyl, $C_{2-9}$heterocycloalkyl, and $C_{1-9}$heteroaryl are optionally substituted with one, two, or three $R^{20c}$;

each $R^{10}$ is independently selected from halogen, —CN, $C_{1-6}$alkyl, $C_{2-6}$alkenyl, $C_{2-6}$alkynyl, $C_{3-7}$cycloalkyl, $C_{2-9}$heterocycloalkyl, $C_{6-10}$aryl, $C_{1-9}$heteroaryl, —OR$^{12}$, —SR$^{12}$, —N(R$^{12}$)(R$^{13}$), —C(O)OR$^{12}$, —OC(O)N(R$^{12}$)(R$^{13}$), —N(R$^{14}$)C(O)N(R$^{12}$)(R$^{13}$), —N(R$^{14}$)C(O)OR$^{15}$, —N(R$^{14}$)S(O)$_2$R$^{15}$, —C(O)R$^{15}$, —S(O)R$^{15}$, —OC(O)R$^{15}$, —C(O)N(R$^{12}$)(R$^{13}$), —C(O)C(O)N(R$^{12}$)(R$^{13}$), —N(R$^{14}$)C(O)R$^{15}$, —S(O)$_2$R$^{15}$, —S(O)$_2$N(R$^{12}$)(R$^{13}$), —S(=O)(=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, —CH$_2$S(O)$_2$N(R$^{12}$)(R$^{13}$), —CH$_2$N(R$^{12}$)S(O)$_2$(R$^{13}$), and —P(O)(R$^{17}$)(R$^{17a}$), wherein $C_{1-6}$alkyl, $C_{2-6}$alkenyl, $C_{2-6}$alkynyl, $C_{3-7}$cycloalkyl, $C_{2-9}$heterocycloalkyl, $C_{6-10}$aryl, and $C_{1-9}$heteroaryl are optionally substituted with one, two, or three $R^{20a}$;

each $R^{12}$ is independently selected from hydrogen, $C_{1-6}$alkyl, $C_{1-6}$haloalkyl, $C_{2-6}$alkenyl, $C_{2-6}$alkynyl, $C_{3-7}$cycloalkyl, $C_{2-9}$heterocycloalkyl, $C_{6-10}$aryl, and $C_{1-9}$heteroaryl, wherein $C_{1-6}$alkyl, $C_{2-6}$alkenyl, $C_{2-6}$alkynyl, $C_{3-7}$cycloalkyl, $C_{2-9}$heterocycloalkyl, $C_{6-10}$aryl, and $C_{1-9}$heteroaryl are optionally substituted with one, two, or three $R^{20e}$;

each $R^{13}$ is independently selected from hydrogen, $C_{1-6}$alkyl, and $C_{1-6}$haloalkyl; or $R^{12}$ and $R^{13}$, together with the nitrogen to which they are attached, form a $C_{2-9}$heterocycloalkyl ring optionally substituted with one, two, or three $R^{20f}$;

$R^{13a}$ is selected from $C_{1-6}$alkyl and $C_{1-6}$haloalkyl; or $R^{12}$ and $R^{13a}$, together with the nitrogen to which they are attached, form a $C_{2-9}$heterocycloalkyl ring optionally substituted with one, two, or three $R^{20f}$;

each $R^{14}$ is independently selected from hydrogen, $C_{1-6}$alkyl, and $C_{1-6}$haloalkyl;

each $R^{15}$ is independently selected $C_{1-6}$alkyl, $C_{2-6}$alkenyl, $C_{2-6}$alkynyl, $C_{3-7}$cycloalkyl, $C_{2-9}$heterocycloalkyl, $C_{6-10}$aryl, and $C_{1-9}$heteroaryl, wherein $C_{1-6}$alkyl, $C_{2-6}$alkenyl, $C_{2-6}$alkynyl, $C_{3-7}$cycloalkyl, $C_{2-9}$heterocycloalkyl, $C_{6-10}$aryl, and $C_{1-9}$heteroaryl are optionally substituted with one, two, or three $R^{20g}$;

each $R^{17}$ and each $R^{17a}$ are each independently selected from $C_{1-6}$alkyl and $C_{3-6}$cycloalkyl, wherein $C_{1-6}$alkyl and $C_{3-6}$cycloalkyl are optionally substituted with one, two or three of $R^{20h}$; or $R^{17}$ and $R^{17a}$ are combined to form a $C_{2-9}$heterocycloalkyl ring;

each $R^{20a}$, $R^{20b}$, $R^{20c}$, $R^{20d}$, $R^{20e}$, $R^{20f}$, $R^{20g}$, and $R^{20h}$ are each independently selected from halogen, oxo, =NH, —CN, $C_{1-6}$alkyl, $C_{2-6}$alkenyl, $C_{2-6}$alkynyl, $C_{3-10}$cycloalkyl, —CH$_2$—$C_{3-10}$cycloalkyl, $C_{2-9}$heterocycloalkyl, —CH$_2$—$C_{2-9}$heterocycloalkyl, $C_{6-10}$aryl, —CH$_2$—$C_{6-10}$aryl, $C_{1-9}$heteroaryl, —OR$^{21}$, —SR$^{21}$, —N(R$^{22}$)(R$^{23}$), —C(O)OR$^{22}$, —C(O)N(R$^{22}$)(R$^{23}$), —C(O)C(O)N(R$^{22}$)(R$^{23}$), —OC(O)N(R$^{22}$)(R$^{23}$), —N(R$^{24}$)C(O)N(R$^{22}$)(R$^{23}$), —N(R$^{24}$)C(O)OR$^{25}$, —N(R$^{24}$)C(O)R$^{25}$, —N(R$^{24}$)S(O)$_2$R$^{25}$, —C(O)R$^{25}$, —S(O)$_2$R$^{25}$, —S(O)$_2$N(R$^{22}$)(R$^{23}$), —OCH$_2$C(O)OR$^{22}$, and —OC(O)R$^{25}$, wherein $C_{1-6}$alkyl, $C_{2-6}$alkenyl, $C_{2-6}$alkynyl, $C_{3-10}$cycloalkyl, —CH$_2$—$C_{3-10}$cycloalkyl, $C_{2-9}$heterocycloalkyl, —CH$_2$—$C_{2-9}$heterocycloalkyl, $C_{6-10}$aryl, —CH$_2$—$C_{6-10}$aryl, and $C_{1-9}$heteroaryl are optionally substituted with one, two, or three groups independently selected from halogen, oxo, =NH, —CN, $C_{1-6}$alkyl, $C_{1-6}$haloalkyl, $C_{1-6}$alkoxy, $C_{1-6}$haloalkoxy, —OR$^{21}$, —SR$^{21}$, —N(R$^{22}$)(R$^{23}$), —C(O)OR$^{22}$, —C(O)N(R$^{22}$)(R$^{23}$), —C(O)C(O)N(R$^{22}$)(R$^{23}$), —OC(O)N(R$^{22}$)(R$^{23}$), —N(R$^{24}$)C(O)N(R$^{22}$)(R$^{23}$), —N(R$^{24}$)C(O)OR$^{25}$, —N(R$^{24}$)C(O)R$^{25}$, —N(R$^{24}$)S(O)$_2$R$^{25}$, —C(O)R$^{25}$, —S(O)$_2$R$^{25}$, —S(O)$_2$N(R$^{22}$)(R$^{23}$), and —OC(O)R$^{25}$;

each $R^{21}$ is independently selected from H, $C_{1-6}$alkyl, $C_{1-6}$haloalkyl, $C_{2-6}$alkenyl, $C_{2-6}$alkynyl, $C_{3-7}$cycloalkyl, $C_{2-9}$heterocycloalkyl, $C_{6-10}$aryl, and $C_{1-9}$heteroaryl, wherein $C_{3-7}$cycloalkyl, $C_{2-9}$heterocycloalkyl, $C_{6-10}$aryl, and $C_{1-9}$heteroaryl are optionally substituted with one, two, or three groups independently selected from halogen and $C_{1-6}$alkyl;

each $R^{22}$ is independently selected from H, $C_{1-6}$alkyl, $C_{1-6}$haloalkyl, $C_{2-6}$alkenyl, $C_{2-6}$alkynyl, $C_{3-7}$cycloalkyl, $C_{2-9}$heterocycloalkyl, $C_{6-10}$aryl, and $C_{1-9}$heteroaryl, wherein $C_{3-7}$cycloalkyl, $C_{2-9}$heterocycloalkyl, $C_{6-10}$aryl, and $C_{1-9}$heteroaryl are optionally substituted with one, two, or three groups independently selected from halogen and $C_{1-6}$alkyl;

each $R^{23}$ is independently selected from H and $C_{1-6}$alkyl;

each $R^{24}$ is independently selected from H and $C_{1-6}$alkyl; and each $R^{25}$ is selected from $C_{1-6}$alkyl, $C_{2-6}$alkenyl, $C_{2-6}$alkynyl, $C_{3-7}$cycloalkyl, $C_{2-9}$heterocycloalkyl, $C_{6-10}$aryl, and $C_{1-9}$heteroaryl, wherein $C_{1-6}$alkyl, $C_{3-7}$cycloalkyl, $C_{2-9}$heterocycloalkyl, $C_{6-10}$aryl, and $C_{1-9}$heteroaryl are optionally substituted with one, two, or three groups independently selected from halogen, $C_{1-6}$alkyl, $C_{1-6}$haloalkyl, $C_{1-6}$alkoxy, $C_{3-7}$cycloalkyl, $C_{2-9}$heterocycloalkyl, $C_{6-10}$aryl, and $C_{1-9}$heteroaryl.

In some embodiments is a compound of Formula (I) having the structure of Formula (Ia), or a pharmaceutically acceptable salt or solvate thereof:

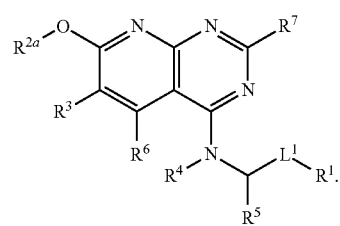

Formula (Ia)

In some embodiments is a compound of Formula (I) or (Ia), or a pharmaceutically acceptable salt or solvate thereof, wherein $R^{2a}$ is $C_{1-6}$alkyl optionally substituted with one, two, or three $R^{20a}$. In some embodiments is a compound of Formula (I) or (Ia), or a pharmaceutically acceptable salt or solvate thereof, wherein $R^{2a}$ is unsubstituted $C_{1-6}$alkyl. In some embodiments is a compound of Formula (I) or (Ia), or a pharmaceutically acceptable salt or solvate thereof, wherein $R^{2a}$ is —CH$_3$.

In some embodiments is a compound of Formula (I) having the structure of Formula (Ib), or a pharmaceutically acceptable salt or solvate thereof:

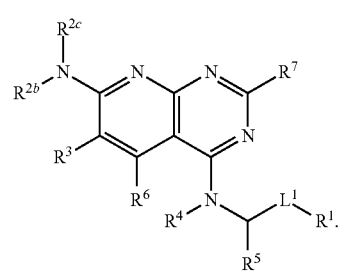

Formula (Ib)

In some embodiments is a compound of Formula (I) or (Ib), or a pharmaceutically acceptable salt or solvate thereof, wherein $R^{2b}$ is $C_{1-6}$alkyl optionally substituted with one, two, or three $R^{20a}$. In some embodiments is a compound of Formula (I) or (Ib), or a pharmaceutically acceptable salt or solvate thereof, wherein $R^{2e}$ is $C_{1-6}$alkyl optionally substituted with one, two, or three $R^{20a}$. In some embodiments is a compound of Formula (I) or (Ib), or a pharmaceutically acceptable salt or solvate thereof, wherein $R^{2e}$ is hydrogen.

In some embodiments is a compound of Formula (I) having the structure of Formula (Ic), or a pharmaceutically acceptable salt or solvate thereof:

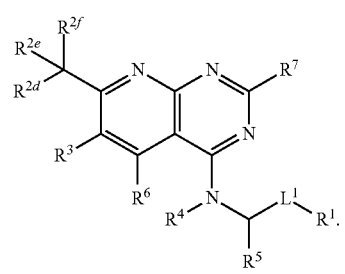

Formula (Ic)

In some embodiments is a compound of Formula (I) or (Ic), or a pharmaceutically acceptable salt or solvate thereof, wherein $R^{2d}$ is hydrogen or $C_{1-6}$alkyl optionally substituted with one, two, or three $R^{20a}$. In some embodiments is a compound of Formula (I) or (Ic), or a pharmaceutically acceptable salt or solvate thereof, wherein $R^{2e}$ is hydrogen. In some embodiments is a compound of Formula (I) or (Ic), or a pharmaceutically acceptable salt or solvate thereof, wherein $R^{2f}$ is hydrogen.

In some embodiments is a compound of Formula (I), or a pharmaceutically acceptable salt or solvate thereof, wherein $R^2$ is halogen.

In another aspect, the disclosure provides a compound of Formula (II), or a pharmaceutically acceptable salt or solvate thereof:

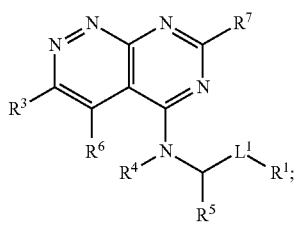

Formula (II)

wherein:
$R^1$ is a 3-12 membered cycloalkyl ring, 3-12 membered heterocycloalkyl ring, 6-10 membered aryl ring, or 5-10 membered heteroaryl ring, wherein the 3-12 membered cycloalkyl ring, 3-12 membered heterocycloalkyl ring, 6-10 membered aryl ring, and 5-10 membered heteroaryl ring are optionally substituted with one or more $R^{10}$;
$L^1$ is a bond or $C_{1-6}$alkyl;
$R^3$ is selected from hydrogen, halogen, —CN, $C_{1-6}$alkyl, $C_{2-6}$alkenyl, $C_{2-6}$alkynyl, $C_{3-14}$cycloalkyl, $C_{2-9}$heterocycloalkyl, $C_{6-10}$aryl, $C_{1-9}$ heteroaryl, —OR$^{12}$, —SR$^{12}$, —N(R$^{12}$)(R$^{13}$), —C(O)OR$^{12}$, —OC(O)N(R$^{12}$)(R$^{13}$), —N(R$^{14}$)C(O)N(R$^{12}$)(R$^{13}$), —N(R$^{14}$)C(O)OR$^{15}$, —N(R$^{14}$)S(O)$_2$R$^{15}$, N(R$^{14}$)S(O)R$^{15}$, —C(O)R$^{15}$, —S(O)R$^{15}$, —OC(O)R$^{15}$, —C(O)N(R$^{12}$)(R$^{13}$), —C(O)C(O)N(R$^{12}$)(R$^{13}$), —N(R$^{14}$)C(O)R$^{15}$, —S(O)$_2$R$^{15}$, —S(O)$_2$N(R$^{12}$)(R$^{13}$), —S(O)N(R$^{12}$)(R$^{13}$), —S(=O)(=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, —CH$_2$S(O)$_2$N(R$^{12}$)(R$^{13}$), —CH$_2$N(R$^{12}$)S(O)$_2$(R$^{13}$), CH$_2$S(O) R$^{15}$, —CH$_2$S(O)N(R$^{12}$)(R$^{13}$), —CH$_2$N(R$^{12}$)S(O)(R$^{13}$) and —P(O)(R$^{17}$)(R$^{17a}$), wherein $C_{1-6}$alkyl, $C_{2-6}$alkenyl, $C_{2-6}$alkynyl, $C_{3-14}$cycloalkyl, $C_{2-9}$heterocycloalkyl, $C_{6-10}$aryl, and $C_{1-9}$heteroaryl are optionally substituted with one, two, or three $R^{2b}$;
$R^4$ is selected from hydrogen, $C_{1-6}$alkyl, and $C_{1-6}$haloalkyl;
$R^5$ is selected from hydrogen, $C_{1-6}$alkyl, and $C_{1-6}$haloalkyl;
$R^6$ and $R^7$ are each independently selected from hydrogen, halogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{1-9}$heteroaryl, —OR$^{12}$, —SR$^{12}$, —N(R$^{12}$)(R$^{13}$), —C(O)OR$^{12}$, —OC(O)N(R$^{12}$)(R$^{13}$), —N(R$^{14}$)C(O)N(R$^{12}$)(R$^{13}$), —N(R$^{14}$)C(O)OR$^{15}$, —N(R$^{14}$)S(O)$_2$R$^{15}$, —C(O)R$^{15}$, —S(O)R$^{15}$, —OC(O)R$^{15}$, —C(O)N(R$^{12}$)(R$^{13}$), —C(O)C(O)N(R$^{12}$)(R$^{13}$), —N(R$^{14}$)C(O)R$^{15}$, —S(O)$_2$R$^{15}$, —S(O)$_2$N(R$^{12}$)(R$^{13}$), —S(=O)(=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, —CH$_2$S(O)$_2$N(R$^{12}$)(R$^{13}$), —CH$_2$N(R$^{12}$)S(O)$_2$(R$^{13}$), and —P(O)(R$^{17}$)(R$^{17a}$), wherein $C_{1-6}$alkyl, $C_{2-6}$alkenyl, $C_{2-6}$alkynyl, $C_{3-10}$cycloalkyl, $C_{2-9}$heterocycloalkyl, and $C_{1-9}$heteroaryl are optionally substituted with one, two, or three $R^{20c}$;
each $R^{10}$ is independently selected from halogen, —CN, $C_{1-6}$alkyl, $C_{2-6}$alkenyl, $C_{2-6}$alkynyl, $C_{3-7}$cycloalkyl, $C_{2-9}$heterocycloalkyl, $C_{6-10}$aryl, $C_{1-9}$heteroaryl, —OR$^{12}$, —SR$^{12}$, —N(R$^{12}$)(R$^{13}$), —C(O)OR$^{12}$, —OC(O)N(R$^{12}$)(R$^{13}$), —N(R$^{14}$)C(O)N(R$^{12}$)(R$^{13}$), —N(R$^{14}$)C(O)OR$^{15}$, —N(R$^{14}$)S(O)$_2$R$^{15}$, —C(O)R$^{15}$, —S(O)R$^{15}$, —OC(O)R$^{15}$, —C(O)N(R$^{12}$)(R$^{13}$), —C(O)C(O)N(R$^{12}$)(R$^{13}$), —N(R$^{14}$)C(O)R$^{15}$, —S(O)$_2$R$^{15}$, —S(O)$_2$N(R$^{12}$)(R$^{13}$), —S(=O)(=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, —CH$_2$S(O)$_2$N(R$^{12}$)(R$^{13}$), —CH$_2$N(R$^{12}$)S(O)$_2$(R$^{13}$), and —P(O)(R$^{17}$)(R$^{17a}$), wherein $C_{1-6}$alkyl, $C_{2-6}$alkenyl, $C_{2-6}$alkynyl, $C_{3-7}$cycloalkyl, $C_{2-9}$heterocycloalkyl, $C_{6-10}$aryl, and $C_{1-9}$heteroaryl are optionally substituted with one, two, or three $R^{20a}$;
each $R^{12}$ is independently selected from hydrogen, $C_{1-6}$alkyl, $C_{1-6}$ haloalkyl, $C_{2-6}$alkenyl, $C_{2-6}$alkynyl, $C_{3-7}$cycloalkyl, $C_{2-9}$heterocycloalkyl, $C_{6-10}$aryl, and $C_{1-9}$heteroaryl, wherein $C_{1-6}$alkyl, $C_{2-6}$alkenyl, $C_{2-6}$alkynyl, $C_{3-7}$cycloalkyl, $C_{2-9}$heterocycloalkyl, $C_{6-10}$aryl, and $C_{1-9}$heteroaryl are optionally substituted with one, two, or three $R^{20e}$;
each $R^{13}$ is independently selected from hydrogen, $C_{1-6}$alkyl, and $C_{1-6}$haloalkyl; or $R^{12}$ and $R^{13}$, together with the nitrogen to which they are attached, form a $C_{2-9}$heterocycloalkyl ring optionally substituted with one, two, or three $R^{20f}$;
each $R^{14}$ is independently selected from hydrogen, $C_{1-6}$alkyl, and $C_{1-6}$haloalkyl;
each $R^{15}$ is independently selected $C_{1-6}$alkyl, $C_{2-6}$alkenyl, $C_{2-6}$alkynyl, $C_{3-7}$cycloalkyl, $C_{2-9}$heterocycloalkyl, $C_{6-10}$aryl, and $C_{1-9}$ heteroaryl, wherein $C_{1-6}$alkyl, $C_{2-6}$alkenyl, $C_{2-6}$alkynyl, $C_{3-7}$cycloalkyl, $C_{2-9}$heterocycloalkyl, $C_{6-10}$aryl, and $C_{1-9}$heteroaryl are optionally substituted with one, two, or three $R^{20g}$;
each $R^{17}$ and each $R^{17a}$ are each independently selected from $C_{1-6}$alkyl and $C_{3-6}$cycloalkyl, wherein $C_{1-6}$alkyl and $C_{3-6}$cycloalkyl are optionally substituted with one, two or three of R$^{20h}$; or $R^{17}$ and $R^{17a}$ form a $C_{2-9}$heterocycloalkyl ring;
each $R^{20a}$, $R^{20b}$, $R^{20c}$, $R^{20d}$, $R^{20e}$, $R^{20f}$, $R^{20g}$, and $R^{20h}$ are each independently selected from halogen, oxo, =NH, —CN, $C_{1-6}$alkyl, $C_{2-6}$alkenyl, $C_{2-6}$alkynyl, $C_{3-10}$cycloalkyl, —CH$_2$—C$_{3-10}$cycloalkyl, $C_{2-9}$heterocycloalkyl, —CH$_2$—C$_{2-9}$heterocycloalkyl, $C_{6-10}$aryl, —CH$_2$—C$_{6-10}$aryl, $C_{1-9}$heteroaryl, —OR$^{21}$, —SR$^{21}$, —N(R$^{22}$)(R$^{23}$), —C(O)OR$^{22}$, —C(O)N(R$^{22}$)(R$^{23}$), —C(O)C(O)N(R$^{22}$)(R$^{23}$), —OC(O)N(R$^{22}$)(R$^{23}$), —N(R$^{24}$)C(O)N(R$^{22}$)(R$^{23}$), —N(R$^{24}$)C(O)OR$^{25}$, —N(R$^{24}$)C(O)R$^{25}$, —N(R$^{24}$)S(O)$_2$R$^{25}$, —C(O)R$^{25}$, —S(O)$_2$R$^{25}$, —S(O)$_2$N(R$^{22}$)(R$^{23}$), —OCH$_2$C(O)OR$^{22}$, and —OC(O)R$^{25}$, wherein $C_{1-6}$alkyl, $C_{2-6}$alkenyl, $C_{2-6}$alkynyl, $C_{3-10}$cycloalkyl, —CH$_2$—C$_{3-10}$cycloalkyl, $C_{2-9}$heterocycloalkyl, —CH$_2$—C$_{2-9}$heterocycloalkyl, $C_{6-10}$aryl, —CH$_2$—C$_{6-10}$aryl, and $C_{1-9}$heteroaryl are optionally substituted with one, two or three groups independently selected from halogen, oxo, =NH, —CN, $C_{1-6}$alkyl, $C_{1-6}$haloalkyl, $C_{1-6}$alkoxy, $C_{1-6}$haloalkoxy, —OR$^{21}$, —SR$^{21}$, —N(R$^{22}$)(R$^{23}$), —C(O)OR$^{22}$, —C(O)N(R$^{22}$)(R$^{23}$), —C(O)C(O)N(R$^{22}$)(R$^{23}$), —OC(O)N(R$^{22}$)(R$^{23}$), —N(R$^{24}$)C(O)N(R$^{22}$)(R$^{23}$), —N(R$^{24}$)C(O)OR$^{25}$, —N(R$^{24}$)C(O)R$^{25}$, —N(R$^{24}$)S(O)$_2$R$^{25}$, —C(O)R$^{25}$, —S(O)$_2$R$^{25}$, —S(O)$_2$N(R$^{22}$)(R$^{23}$), and —OC(O)R$^{25}$;
each $R^{21}$ is independently selected from H, $C_{1-6}$alkyl, $C_{1-6}$haloalkyl, $C_{2-6}$alkenyl, $C_{2-6}$alkynyl, $C_{3-7}$cycloalkyl, $C_{2-9}$heterocycloalkyl, $C_{6-10}$aryl, and $C_{1-9}$heteroaryl, wherein $C_{3-7}$cycloalkyl, $C_{2-9}$heterocycloalkyl, $C_{6-10}$aryl, and C$_{1-9}$heteroaryl are optionally substituted with one, two, or three groups independently selected from halogen and C$_{1-6}$alkyl;

each R$^{22}$ is independently selected from H, C$_{1-6}$alkyl, C$_{1-6}$haloalkyl, C$_{2-6}$alkenyl, C$_{2-6}$alkynyl, C$_{3-7}$cycloalkyl, C$_{2-9}$heterocycloalkyl, C$_{6-10}$aryl, and C$_{1-9}$heteroaryl, wherein C$_{3-7}$cycloalkyl, C$_{2-9}$heterocycloalkyl, C$_{6-10}$aryl, and C$_{1-9}$heteroaryl are optionally substituted with one, two, or three groups independently selected from halogen and C$_{1-6}$alkyl;

each R$^{23}$ is independently selected from H and C$_{1-6}$alkyl;

each R$^{24}$ is independently selected from H and C$_{1-6}$alkyl; and each R$^{25}$ is selected from C$_{1-6}$alkyl, C$_{2-6}$alkenyl, C$_{2-6}$alkynyl, C$_{3-7}$cycloalkyl, C$_{2-9}$heterocycloalkyl, C$_{6-10}$aryl, and C$_{1-9}$heteroaryl, wherein C$_{1-6}$alkyl, C$_{3-7}$cycloalkyl, C$_{2-9}$heterocycloalkyl, C$_{6-10}$aryl, and C$_{1-9}$heteroaryl are optionally substituted with one, two, or three groups independently selected from halogen, C$_{1-6}$alkyl, C$_{1-6}$haloalkyl, C$_{1-6}$alkoxy, C$_{3-7}$cycloalkyl, C$_{2-9}$heterocycloalkyl, C$_{6-10}$aryl, and C$_{1-9}$heteroaryl.

In some embodiments is a compound of Formula (I), (Ia), (Ib), (Ic), or (II), or a pharmaceutically acceptable salt or solvate thereof, wherein R$^3$ is selected from —N(R$^{12}$)(R$^{13}$), —C(O)R$^{15}$, —C(O)N(R$^{12}$)(R$^{13}$), —SO$_2$(R$^{12}$)(R$^{13}$), —SO$_2$N(R$^{12}$)(R$^{13}$), —P(O)(R$^{17}$)(R$^{17a}$), C$_{1-6}$ alkyl, C$_{3-10}$cycloalkyl, C$_{2-9}$heterocycloalkyl, C$_{6-10}$aryl, and C$_{1-9}$heteroaryl, wherein C$_{1-6}$alkyl, C$_{3-10}$cycloalkyl, C$_{2-9}$heterocycloalkyl, C$_{6-10}$aryl, and C$_{1-9}$heteroaryl are optionally substituted with one, two, or three R$^{20b}$. In some embodiments is a compound of Formula (I), (Ia), (Ib), (Ic), or (II), or a pharmaceutically acceptable salt or solvate thereof, wherein R$^3$ is selected from —N(R$^{12}$)(R$^{13}$), C$_{1-6}$alkyl, C$_{3-10}$cycloalkyl, and C$_{2-9}$heterocycloalkyl, wherein C$_{1-6}$alkyl, C$_{3-10}$cycloalkyl, and C$_{2-9}$heterocycloalkyl are optionally substituted with one, two, or three R$^{2b}$. In some embodiments is a compound of Formula (I), (Ia), (Ib), (Ic), or (II), or a pharmaceutically acceptable salt or solvate thereof, wherein R$^3$ is C$_{2-9}$heterocycloalkyl optionally substituted with one, two, or three R$^{2b}$. In some embodiments is a compound of Formula (I), (Ia), (Ib), (Ic), or (II), or a pharmaceutically acceptable salt or solvate thereof, wherein R$^3$ is C$_{3-10}$cycloalkyl optionally substituted with one, two, or three R$^{20b}$. In some embodiments is a compound of Formula (I), (Ia), (Ib), (Ic), or (II), or a pharmaceutically acceptable salt or solvate thereof, wherein R$^3$ is C$_{1-6}$alkyl optionally substituted with one, two, or three R$^{20b}$. In some embodiments is a compound of Formula (I), (Ia), (Ib), (Ic), or (II), or a pharmaceutically acceptable salt or solvate thereof, wherein R$^3$ is —N(R$^{12}$)(R$^{13}$).

In another aspect, the disclosure provides a compound of Formula (III), or a pharmaceutically acceptable salt or solvate thereof:

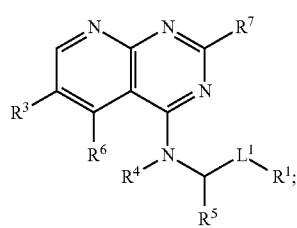

Formula (III)

wherein:

R$^1$ is a 3-12 membered cycloalkyl ring, 3-12 membered heterocycloalkyl ring, 6-10 membered aryl ring, or 5-10 membered heteroaryl ring, wherein the 3-12 membered cycloalkyl ring, 3-12 membered heterocycloalkyl ring, 6-10 membered aryl ring, and 5-10 membered heteroaryl ring are optionally substituted with one or more R$^{10}$;

L$^1$ is a bond or C$_{1-6}$alkyl;

R$^4$ is selected from hydrogen, C$_{1-6}$alkyl, and C$_{1-6}$haloalkyl;

R$^5$ is selected from hydrogen, C$_{1-6}$alkyl, and C$_{1-6}$haloalkyl;

R$^6$ is selected from hydrogen, halogen, —CN, C$_{1-6}$alkyl, C$_{2-6}$alkenyl, C$_{2-6}$alkynyl, C$_{3-10}$cycloalkyl, C$_{2-9}$heterocycloalkyl, —OR$^{12}$, —SR$^{12}$, —N(R$^{12}$)(R$^{13}$), —C(O)R$^{12}$, —OC(O)N(R$^{12}$)(R$^{13}$), —N(R$^{14}$)C(O)N(R$^{12}$)(R$^{13}$), —N(R$^{14}$)C(O)OR$^{15}$, —N(R$^{14}$)S(O)$_2$R$^{15}$, —C(O)R$^{15}$, —S(O)R$^{15}$, —OC(O)R$^{15}$, —C(O)N(R$^{12}$)(R$^{13}$), —C(O)C(O)N(R$^{12}$)(R$^{13}$), —N(R$^{14}$)C(O)R$^{15}$, —S(O)$_2$R$^{15}$, —S(O)$_2$N(R$^{12}$)(R$^{13}$), —S(=O)(=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, —CH$_2$S(O)$_2$N(R$^{12}$)(R$^{13}$), —CH$_2$N(R$^{12}$)S(O)$_2$(R$^{13}$), and —P(O)(R$^{17}$)(R$^{17a}$), wherein C$_{1-6}$alkyl, C$_{2-6}$alkenyl, C$_{2-6}$alkynyl, C$_{3-10}$cycloalkyl, and C$_{2-9}$heterocycloalkyl are optionally substituted with one, two, or three R$^{20c}$;

R$^7$ is selected from hydrogen, halogen, —CN, C$_{1-6}$alkyl, C$_{2-6}$alkenyl, C$_{2-6}$alkynyl, C$_{3-10}$cycloalkyl, C$_{2-9}$heterocycloalkyl, C$_{1-9}$heteroaryl, —OR$^{12}$, —SR$^{12}$, —N(R$^{12}$)(R$^{13}$), —C(O)OR$^{12}$, —OC(O)N(R$^{12}$)(R$^{13}$), —N(R$^{14}$)C(O)N(R$^{12}$)(R$^{13}$), —N(R$^{14}$)C(O)OR$^{15}$, —N(R$^{14}$)S(O)$_2$R$^{15}$, —C(O)R$^{15}$, —S(O)R$^{15}$, —OC(O)R$^{15}$, —C(O)N(R$^{12}$)(R$^{13}$), —C(O)C(O)N(R$^{12}$)(R$^{13}$), —N(R$^{14}$)C(O)R$^{15}$, —S(O)$_2$R$^{15}$, —S(O)$_2$N(R$^{12}$)(R$^{13}$), —S(=O)(=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, —CH$_2$S(O)$_2$N(R$^{12}$)(R$^{13}$), —CH$_2$N(R$^{12}$)S(O)$_2$(R$^{13}$), and —P(O)(R$^{17}$)(R$^{17a}$), wherein C$_{1-6}$alkyl, C$_{2-6}$alkenyl, C$_{2-6}$alkynyl, C$_{3-10}$cycloalkyl, C$_{2-9}$heterocycloalkyl, and C$_{1-9}$heteroaryl are optionally substituted with one, two, or three R$^{20c}$;

R$^8$ is —OR$^{9a}$, —NR$^{9b}$R$^{9c}$, —SR$^{9b}$, —S(O)R$^{9d}$, —S(O)$_2$R$^{9d}$, —S(O)$_2$NR$^{9b}$R$^{9c}$, —C(R$^{9e}$)(R$^{9f}$)(R$^{9g}$), and C(O)NR$^{9b}$R$^{9c}$;

R$^{9a}$ is selected from hydrogen, C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, C$_{1-9}$heteroaryl, —C(O)OR$^{12}$, —C(O)R$^{15}$, —C(O)N(R$^{12}$)(R$^{13}$), —S(O)$_2$R$^{15}$, —S(O)$_2$N(R$^{12}$)(R$^{13}$), wherein C$_{1-6}$alkyl is substituted with one, two, or three R$^{20a}$, and wherein C$_{2-6}$alkenyl, C$_{2-6}$alkynyl, C$_{3-10}$cycloalkyl, C$_{2-9}$heterocycloalkyl, C$_{6-10}$aryl, and C$_{1-9}$heteroaryl are optionally substituted with one, two, or three R$^{20a}$;

R$^{9b}$ is selected from hydrogen, C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, C$_{1-9}$heteroaryl, —C(O)OR$^{12}$, —C(O)R$^{15}$, —C(O)N(R$^{12}$)(R$^{13}$), —S(O)$_2$R$^{15}$, and —S(O)$_2$N(R$^{12}$)(R$^{13}$), wherein C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, and C$_{1-9}$heteroaryl are optionally substituted with one, two, or three R$^{20a}$;

R$^{9c}$ is selected from hydrogen, C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, and C$_{1-9}$heteroaryl, wherein C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, and C$_{1-9}$heteroaryl are optionally substituted with one, two, or three R$^{20a}$; or R$^{9b}$ and R$^{9c}$, together with the nitrogen to which they are attached, form a C$_{2-9}$heterocycloalkyl ring optionally substituted with one, two, or three R$^{20a}$;

R$^{9d}$ is selected from C$_{1-6}$alkyl, C$_{2-6}$alkenyl, C$_{2-6}$alkynyl, C$_{3-10}$cycloalkyl, C$_{2-9}$heterocycloalkyl, C$_{6-10}$aryl, and $C_{1-9}$heteroaryl, wherein $C_{1-6}$alkyl is substituted with one, two, or three $R^{20a}$, and wherein $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20a}$;

$R^{9e}$ is selected from hydrogen, $C_{1-6}$alkyl, $C_{2-6}$alkenyl, $C_{2-6}$alkynyl, $C_{3-10}$cycloalkyl, $C_{2-9}$heterocycloalkyl, $C_{1-9}$heteroaryl, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{15}$, —$S(O)_2R^{15}$, —$S(O)_2N(R^{12})(R^{13})$, —$S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, —$CH_2S(O)_2N(R^{12})(R^{13})$, —$CH_2N(R^{12})S(O)_2(R^{13})$, and —$P(O)(R^{17})(R^{17a})$, wherein $C_{1-6}$alkyl, $C_{2-6}$alkenyl, $C_{2-6}$alkynyl, $C_{3-10}$cycloalkyl, $C_{2-9}$heterocycloalkyl, and $C_{1-9}$heteroaryl are optionally substituted with one, two, or three $R^{20a}$;

$R^{9f}$ is selected from hydrogen, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20a}$;

$R^{9g}$ is selected from $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20a}$;

each $R^{10}$ is independently selected from halogen, —CN, $C_{1-6}$alkyl, $C_{2-6}$alkenyl, $C_{2-6}$alkynyl, $C_{3-7}$cycloalkyl, $C_{2-9}$heterocycloalkyl, $C_{6-10}$aryl, $C_{1-9}$heteroaryl, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{15}$, —$S(O)_2R^{15}$, —$S(O)_2N(R^{12})(R^{13})$, —$S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, —$CH_2S(O)_2N(R^{12})(R^{13})$, —$CH_2N(R^{12})S(O)_2(R^{13})$, and —$P(O)(R^{17})(R^{17a})$, wherein $C_{1-6}$alkyl, $C_{2-6}$alkenyl, $C_{2-6}$alkynyl, $C_{3-7}$cycloalkyl, $C_{2-9}$heterocycloalkyl, $C_{6-10}$aryl, and $C_{1-9}$heteroaryl are optionally substituted with one, two, or three $R^{20a}$;

each $R^{12}$ is independently selected from hydrogen, $C_{1-6}$alkyl, $C_{1-6}$haloalkyl, $C_{2-6}$alkenyl, $C_{2-6}$alkynyl, $C_{3-7}$cycloalkyl, $C_{2-9}$heterocycloalkyl, $C_{6-10}$aryl, and $C_{1-9}$heteroaryl, wherein $C_{1-6}$alkyl, $C_{2-6}$alkenyl, $C_{2-6}$alkynyl, $C_{3-7}$cycloalkyl, $C_{2-9}$heterocycloalkyl, $C_{6-10}$aryl, and $C_{1-9}$heteroaryl are optionally substituted with one, two, or three $R^{20e}$;

each $R^{13}$ is independently selected from hydrogen, $C_{1-6}$alkyl, and $C_{1-6}$haloalkyl; or $R^{12}$ and $R^{13}$, together with the nitrogen to which they are attached, form a $C_{2-9}$heterocycloalkyl ring optionally substituted with one, two, or three $R^{20f}$;

each $R^{14}$ is independently selected from hydrogen, $C_{1-6}$alkyl, and $C_{1-6}$haloalkyl;

each $R^{15}$ is independently selected $C_{1-6}$alkyl, $C_{2-6}$alkenyl, $C_{2-6}$alkynyl, $C_{3-7}$cycloalkyl, $C_{2-9}$heterocycloalkyl, $C_{6-10}$aryl, and $C_{1-9}$heteroaryl, wherein $C_{1-6}$alkyl, $C_{2-6}$alkenyl, $C_{2-6}$alkynyl, $C_{3-7}$cycloalkyl, $C_{2-9}$heterocycloalkyl, $C_{6-10}$aryl, and $C_{1-9}$heteroaryl are optionally substituted with one, two, or three $R^{20g}$;

each $R^{17}$ and each $R^{17a}$ are each independently selected from $C_{1-6}$alkyl and $C_{3-6}$cycloalkyl, wherein $C_{1-6}$alkyl and $C_{3-6}$cycloalkyl are optionally substituted with one, two or three of $R^{20h}$; or $R^{17}$ and $R^{17a}$ are combined to form a $C_{2-9}$heterocycloalkyl ring;

each $R^{20a}$, $R^{20b}$, $R^{20c}$, $R^{20d}$, $R^{20e}$, $R^{20f}$, $R^{20g}$, and $R^{20h}$ are each independently selected from halogen, oxo, =NH, —CN, $C_{1-6}$alkyl, $C_{2-6}$alkenyl, $C_{2-6}$alkynyl, $C_{3-10}$cycloalkyl, —$CH_2$—$C_{3-10}$cycloalkyl, $C_{2-9}$heterocycloalkyl, —$CH_2$—$C_{2-9}$heterocycloalkyl, $C_{6-10}$aryl, —$CH_2$—$C_{6-10}$aryl, $C_{1-9}$heteroaryl, —$OR^{21}$, —$SR^{21}$, —$N(R^{22})(R^{23})$, —$C(O)OR^{22}$, —$C(O)N(R^{22})(R^{23})$, —$C(O)C(O)N(R^{22})(R^{23})$, —$OC(O)N(R^{22})(R^{23})$, —$N(R^{24})C(O)N(R^{22})(R^{23})$, —$N(R^{24})C(O)OR^{25}$, —$N(R^{24})C(O)R^{25}$, —$N(R^{24})S(O)_2R^{25}$, —$C(O)R^{25}$, —$S(O)_2R^{25}$, —$S(O)_2N(R^{22})(R^{23})$, —$OCH_2C(O)OR^{22}$, and —$OC(O)R^{25}$, wherein $C_{1-6}$alkyl, $C_{2-6}$alkenyl, $C_{2-6}$alkynyl, $C_{3-10}$cycloalkyl, —$CH_2$—$C_{3-10}$cycloalkyl, $C_{2-9}$heterocycloalkyl, —$CH_2$—$C_{2-9}$heterocycloalkyl, $C_{6-10}$aryl, —$CH_2$—$C_{6-10}$aryl, and $C_{1-9}$heteroaryl are optionally substituted with one, two, or three groups independently selected from halogen, oxo, =NH, —CN, $C_{1-6}$alkyl, $C_{1-6}$haloalkyl, $C_{1-6}$alkoxy, $C_{1-6}$haloalkoxy, —$OR^{21}$, —$SR^{21}$, —$N(R^{22})(R^{23})$, —$C(O)OR^{22}$, —$C(O)N(R^{22})(R^{23})$, —$C(O)C(O)N(R^{22})(R^{23})$, —$OC(O)N(R^{22})(R^{23})$, —$N(R^{24})C(O)N(R^{22})(R^{23})$, —$N(R^{24})C(O)OR^{25}$, —$N(R^{24})C(O)R^{25}$, —$N(R^{24})S(O)_2R^{25}$, —$C(O)R^{25}$, —$S(O)_2R^{25}$, —$S(O)_2N(R^{22})(R^{23})$, and —$OC(O)R^{25}$;

each $R^{21}$ is independently selected from H, $C_{1-6}$alkyl, $C_{1-6}$haloalkyl, $C_{2-6}$alkenyl, $C_{2-6}$alkynyl, $C_{3-7}$cycloalkyl, $C_{2-9}$heterocycloalkyl, $C_{6-10}$aryl, and $C_{1-9}$heteroaryl, wherein $C_{3-7}$cycloalkyl, $C_{2-9}$heterocycloalkyl, $C_{6-10}$aryl, and $C_{1-9}$heteroaryl are optionally substituted with one, two, or three groups independently selected from halogen and $C_{1-6}$alkyl;

each $R^{22}$ is independently selected from H, $C_{1-6}$alkyl, $C_{1-6}$haloalkyl, $C_{2-6}$alkenyl, $C_{2-6}$alkynyl, $C_{3-7}$cycloalkyl, $C_{2-9}$heterocycloalkyl, $C_{6-10}$aryl, and $C_{1-9}$heteroaryl, wherein $C_{3-7}$cycloalkyl, $C_{2-9}$heterocycloalkyl, $C_{6-10}$aryl, and $C_{1-9}$heteroaryl are optionally substituted with one, two, or three groups independently selected from halogen and $C_{1-6}$alkyl;

each $R^{23}$ is independently selected from H and $C_{1-6}$alkyl;
each $R^{24}$ is independently selected from H and $C_{1-6}$alkyl; and each $R^{21}$ is selected from $C_{1-6}$alkyl, $C_{2-6}$alkenyl, $C_{2-6}$alkynyl, $C_{3-7}$cycloalkyl, $C_{2-9}$heterocycloalkyl, $C_{6-10}$aryl, and $C_{1-9}$heteroaryl, wherein $C_{1-6}$alkyl, $C_{3-7}$cycloalkyl, $C_{2-9}$heterocycloalkyl, $C_{6-10}$aryl, and $C_{1-9}$heteroaryl are optionally substituted with one, two, or three groups independently selected from halogen, $C_{1-6}$alkyl, $C_{1-6}$haloalkyl, $C_{1-6}$alkoxy, $C_{3-7}$cycloalkyl, $C_{2-9}$heterocycloalkyl, $C_{6-10}$aryl, and $C_{1-9}$heteroaryl.

In some embodiments is a compound of Formula (III), or a pharmaceutically acceptable salt or solvate thereof, wherein $R^8$ is —$OR^{9a}$. In some embodiments is a compound of Formula (III), or a pharmaceutically acceptable salt or solvate thereof, wherein $R^8$ is —$NR^{9b}R^{9c}$. In some embodiments is a compound of Formula (III), wherein $R^8$ is —$C(R^{9e})(R^{9f})(R^{9g})$.

In some embodiments is a compound of Formula (I), (Ia), (Ib), (Ic), (II), or (III), or a pharmaceutically acceptable salt or solvate thereof, wherein $R^6$ is selected from hydrogen, halogen, $C_{1-6}$alkyl, $C_{3-10}$cycloalkyl, $C_{2-9}$heterocycloalkyl, and $C_{1-9}$heteroaryl, wherein $C_{1-6}$alkyl, $C_{3-10}$cycloalkyl, $C_{2-9}$heterocycloalkyl, and $C_{1-9}$heteroaryl are optionally substituted with one, two, or three $R^{20c}$. In some embodiments is a compound of Formula (I), (Ia), (Ib), (Ic), (II), or (III), or a pharmaceutically acceptable salt or solvate thereof, wherein $R^6$ is independently selected from hydrogen, halogen, and unsubstituted $C_{1-6}$alkyl. In some embodiments is a compound of Formula (I), (Ia), (Ib), (Ic), (II), or (III), or a pharmaceutically acceptable salt or solvate thereof, wherein $R^6$ is hydrogen. In some embodiments is a compound of Formula (I), (Ia), (Ib), (Ic), (II), or (III), or a pharmaceutically acceptable salt or solvate thereof, wherein $R^7$ is selected from hydrogen, halogen, $C_{1-6}$alkyl, $C_{3-10}$cycloalkyl, $C_{2-9}$heterocycloalkyl, and $C_{1-9}$heteroaryl, wherein $C_{1-6}$alkyl, $C_{3-10}$cycloalkyl, $C_{2-9}$heterocycloalkyl, and $C_{1-9}$heteroaryl are optionally substituted with one, two, or three $R^{20c}$. In some embodiments is a compound of Formula (I), (Ia), (Ib), (Ic), (II), or (III), a pharmaceutically acceptable salt or solvate thereof, wherein $R^7$ is independently selected from hydrogen, halogen, and unsubstituted $C_{1-6}$alkyl. In some embodiments is a compound of Formula (I), (Ia), (Ib), (Ic), (II), or (III), or a pharmaceutically acceptable salt or solvate thereof, wherein $R^7$ is unsubstituted $C_{1-6}$alkyl. In some embodiments is a compound of Formula (I), (Ia), (Ib), (Ic), (II), or (III), or a pharmaceutically acceptable salt or solvate thereof, wherein $R^7$ is hydrogen. In some embodiments is a compound of Formula (I), (Ia), (Ib), (Ic), (II), or (III), or a pharmaceutically acceptable salt or solvate thereof, wherein $R^5$ is selected from $C_{1-6}$alkyl and $C_{1-6}$haloalkyl. In some embodiments is a compound of Formula (I), (Ia), (Ib), (Ic), (II), or (III), or a pharmaceutically acceptable salt or solvate thereof, wherein $R^5$ is —CH$_3$. In some embodiments is a compound of Formula (I), (Ia), (Ib), (Ic), (II), or (III), or a pharmaceutically acceptable salt or solvate thereof, wherein $R^4$ is hydrogen. In some embodiments is a compound of Formula (I), (Ia), (Ib), (Ic), (II), or (III), or a pharmaceutically acceptable salt or solvate thereof, wherein $L^1$ is a bond. In some embodiments is a compound of Formula (I), (Ia), (Ib), (Ic), (II), or (III), or a pharmaceutically acceptable salt or solvate thereof, wherein $R^1$ is a 6-10 membered aryl ring substituted with one or more $R^{10}$. In some embodiments is a compound of Formula (I), (Ia), (Ib), (Ic), (II), or (III), or a pharmaceutically acceptable salt or solvate thereof, wherein $R^1$ is phenyl substituted with one or more $R^{10}$. In some embodiments is a compound of Formula (I), (Ia), (Ib), (Ic), (II), or (III), or a pharmaceutically acceptable salt or solvate thereof, wherein $R^1$ is phenyl substituted with one, two, or three $R^{10}$. In some embodiments is a compound of Formula (I), (Ia), (Ib), (Ic), (II), or (III), or a pharmaceutically acceptable salt or solvate thereof, wherein $R^1$ is a 5-10 membered heteroaryl ring are substituted with one or more $R^{10}$. In some embodiments is a compound of Formula (I), (Ia), (Ib), (Ic), (II), or (III), or a pharmaceutically acceptable salt or solvate thereof, wherein $R^1$ is a 5-10 membered heteroaryl ring are substituted with one, two, or three $R^{10}$. In some embodiments is a compound of Formula (I), (Ia), (Ib), (Ic), (II), or (III), or a pharmaceutically acceptable salt or solvate thereof, wherein each $R^{10}$ is independently selected from halogen, $C_{1-6}$alkyl, $C_{3-7}$cycloalkyl, $C_{2-9}$heterocycloalkyl, $C_{6-10}$aryl, $C_{1-9}$heteroaryl, —OR$^{12}$, and N(R$^{12}$)(R$^{13}$), wherein $C_{1-6}$alkyl, $C_{3-7}$cycloalkyl, $C_{2-9}$heterocycloalkyl, $C_{6-10}$aryl, and $C_{1-9}$heteroaryl are optionally substituted with one, two, or three $R^{20d}$. In some embodiments is a compound of Formula (I), (Ia), (Ib), (Ic), (II), or (III), or a pharmaceutically acceptable salt or solvate thereof, wherein each $R^{10}$ is independently selected from halogen, $C_{1-6}$alkyl, and N(R$^{12}$)(R$^{13}$), wherein $C_{1-6}$alkyl is optionally substituted with one, two, or three $R^{20d}$. In some embodiments is a compound of Formula (I), (Ia), (Ib), (Ic), (II), or (III), or a pharmaceutically acceptable salt or solvate thereof, wherein each $R^{10}$ is independently selected from halogen and $C_{1-6}$alkyl, wherein $C_{1-6}$alkyl is substituted with one, two, or three $R^{20d}$, and each $R^{20d}$ is halogen.

Also provided herein is a pharmaceutical composition comprising a compound of Formula (I), (Ia), (Ib), (Ic), (II), or (III), or a pharmaceutically acceptable salt or solvate thereof, and a pharmaceutically acceptable excipient.

Also provided in the present disclosure is a method of treating cancer in a subject in need thereof comprising administering to the subject a therapeutically effective amount of a compound of Formula (I), (Ia), (Ib), (Ic), (II), or (III), or a pharmaceutically acceptable salt or solvate thereof. In some embodiments is a method of treating cancer in a subject in need thereof comprising administering to the subject a therapeutically effective amount of a compound of Formula (I), (Ia), (Ib), (Ic), (II), or (III), or a pharmaceutically acceptable salt or solvate thereof, wherein the cancer is a solid tumor or a hematological cancer.

Also provided herein is a method of reducing Ras signaling output comprising contacting a SOS1 protein with an effective amount of a compound of Formula (I), (Ia), (Ib), (Ic), (II), or (III), or a pharmaceutically acceptable salt or solvate thereof, thereby reducing the Ras signaling output. In some embodiments is a method of reducing Ras signaling output of a SOS1 protein comprising contacting a SOS1 protein with an effective amount of a compound of Formula (I), (Ia), (Ib), (Ic), (II), or (III), or a pharmaceutically acceptable salt or solvate thereof, wherein said reducing the Ras signaling output. In some embodiments, a subject compound interferes or disrupts the interaction or binding between a SOS protein (e.g., SOS1) with a Ras protein (e.g., wildtype or a mutant Ras).

Further provided herein is a method of inhibiting cell growth, comprising administering a cell expressing SOS1 with an effective amount of a compound of Formula (I), (Ia), (Ib), (Ic), (II), or (III), or a pharmaceutically acceptable salt or solvate thereof, thereby inhibiting growth of said cells. The method may further comprise administering to the cell an additional agent. Where desired, the additional agent can be an inhibitor against one or more targets including but not limited to: MEK, epidermal growth factor receptor (EGFR), FGFR1, FGFR2, FGFR3, FGFR4, mitotic kinase, topoisomerase, ALK, c-MET, ErbB2, AXL, NTRK1, RET, A-Raf, B-Raf, C-Raf, ERK, MDM2, mTOR, BET, IGF1/2, IGF1-R, CDK9, SHC, GAB, GRB, PI3-kinase, MAPK, SHIP1, SHIP2, SHP1, SHP2, SRC, JAK, PARP, BTK, FLT3, HDAC, VEGFR, PDGFR, LCK, Bcr-Abl, AKT, wildtype KRas, KRas mutant (e.g., KrasG12C, KRas G12D, KRas G12S, KRas G12V, KRas G13D, KRas G13C, or KRas G13V), ROS1, CDK4/6, and a mutant of any target thereof. In some embodiments, the additional agent is a chemotherapeutic agent, a radioactive agent, or an immune modulator.

Also provided herein is a modified SOS1 protein bound by a compound of Formula (I), (Ia), (Ib), (Ic), (II), or (III), or a pharmaceutically acceptable salt or solvate thereof, wherein interaction of the SOS1 protein with a Ras protein is reduced as compared to a SOS1 protein unbound to said compound.

INCORPORATION BY REFERENCE

All publications, patents, and patent applications mentioned in this specification are herein incorporated by reference to the same extent as if each individual publication, patent, or patent application was specifically and individually indicated to be incorporated by reference.

DRAWINGS

FIG. 1: A compound of the present invention, Compound A, inhibits growth of a Ras-driven tumor model (Xenograft with K-Ras G12C mutation) alone, and synergistically to a greater extent when administered in conjunction with a KrasG12C inhibitor.

Figure 2:
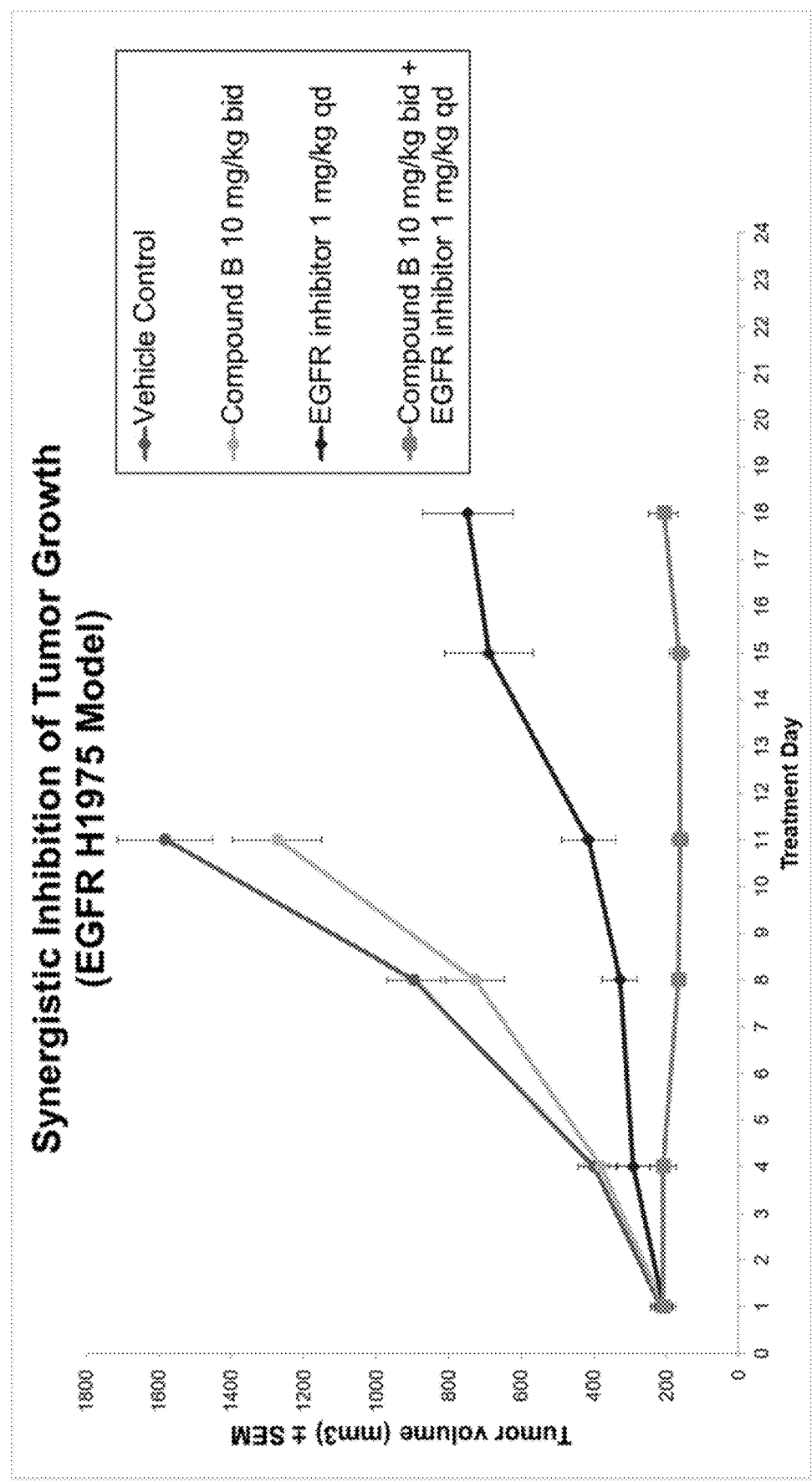

FIG. 2: A compound of the present invention, Compound B, inhibits growth of an EGFR-mutation driven tumor model (NCI-H1975 (ATCC CRL-5908)) alone, and synergistically to a greater extent when administered in conjunction with an EGFR inhibitor.

DETAILED DESCRIPTION

The practice of some embodiments disclosed herein employ, unless otherwise indicated, conventional techniques of immunology, biochemistry, chemistry, molecular biology, microbiology, cell biology, genomics and recombinant DNA, which are within the skill of the art. See for example Sambrook and Green, Molecular Cloning: A Laboratory Manual, 4th Edition (2012); the series Current Protocols in Molecular Biology (F. M. Ausubel, et al. eds.); the series Methods In Enzymology (Academic Press, Inc.), PCR 2: A Practical Approach (M. J. MacPherson, B. D. Hames and G. R. Taylor eds. (1995)), Harlow and Lane, eds. (1988) Antibodies, A Laboratory Manual, and Culture of Animal Cells: A Manual of Basic Technique and Specialized Applications, 6th Edition (R. I. Freshney, ed. (2010)).

Unless defined otherwise, all technical and scientific terms used herein have the same meaning as is commonly understood to which the claimed subject matter belongs. In the event that there are a plurality of definitions for terms herein, those in this section prevail. All patents, patent applications, publications and published nucleotide and amino acid sequences (e.g., sequences available in GenBank or other databases) referred to herein are incorporated by reference. Where reference is made to a URL or other such identifier or address, it is understood that such identifiers can change and particular information on the internet can come and go, but equivalent information can be found by searching the internet. Reference thereto evidences the availability and public dissemination of such information.

It is to be understood that the foregoing general description and the following detailed description are exemplary and explanatory only and are not restrictive of any subject matter claimed. In this application, the use of the singular includes the plural unless specifically stated otherwise. It must be noted that, as used in the specification and the appended claims, the singular forms "a," "an" and "the" include plural referents unless the context clearly dictates otherwise. In this application, the use of "or" means "and/or" unless stated otherwise. Furthermore, use of the term "including" as well as other forms, such as "include", "includes," and "included," is not limiting.

The section headings used herein are for organizational purposes only and are not to be construed as limiting the subject matter described.

Definition of standard chemistry terms may be found in reference works, including but not limited to, Carey and Sundberg "Advanced Organic Chemistry $4^{th}$ Ed." Vols. A (2000) and B (2001), Plenum Press, New York. Unless otherwise indicated, conventional methods of mass spectroscopy, NMR, HPLC, protein chemistry, biochemistry, recombinant DNA techniques and pharmacology.

Unless specific definitions are provided, the nomenclature employed in connection with, and the laboratory procedures and techniques of, analytical chemistry, synthetic organic chemistry, and medicinal and pharmaceutical chemistry described herein are those recognized in the field. Standard techniques can be used for chemical syntheses, chemical analyses, pharmaceutical preparation, formulation, and delivery, and treatment of patients. Standard techniques can be used for recombinant DNA, oligonucleotide synthesis, and tissue culture and transformation (e.g., electroporation, lipofection). Reactions and purification techniques can be performed e.g., using kits of manufacturer's specifications or as commonly accomplished in the art or as described herein. The foregoing techniques and procedures can be generally performed of conventional methods and as described in various general and more specific references that are cited and discussed throughout the present specification.

It is to be understood that the methods and compositions described herein are not limited to the particular methodology, protocols, cell lines, constructs, and reagents described herein and as such may vary. It is also to be understood that the terminology used herein is for the purpose of describing particular embodiments only, and is not intended to limit the scope of the methods, compounds, compositions described herein.

As used herein, $C_1$-$C_x$ includes $C_1$-$C_2$, $C_1$-$C_3$ ... $C_1$-$C_x$. $C_1$-$C_x$ refers to the number of carbon atoms that make up the moiety to which it designates (excluding optional substituents).

An "alkyl" group refers to a straight or branched hydrocarbon chain radical consisting solely of carbon and hydrogen atoms, containing no unsaturation. In some embodiments, the "alkyl" group may have 1 to 6 carbon atoms (whenever it appears herein, a numerical range such as "1 to 6" refers to each integer in the given range; e.g., "1 to 6 carbon atoms" means that the alkyl group may consist of 1 carbon atom, 2 carbon atoms, 3 carbon atoms, etc., up to and including 6 carbon atoms, although the present definition also covers the occurrence of the term "alkyl" where no numerical range is designated). The alkyl group of the compounds described herein may be designated as "$C_1$-$C_6$alkyl" or similar designations. By way of example only, "$C_1$-$C_6$alkyl" indicates that there are one to six carbon atoms in the alkyl chain, i.e., the alkyl chain is selected from the group consisting of methyl, ethyl, n-propyl, iso-propyl, n-butyl, iso-butyl, sec-butyl, t-butyl, n-pentyl, iso-pentyl, neo-pentyl, and hexyl. Alkyl groups can be substituted or unsubstituted. Depending on the structure, an alkyl group can be a monoradical or a diradical (i.e., an alkylene group).

An "alkoxy" refers to a "—O-alkyl" group, where alkyl is as defined herein.

The term "alkenyl" refers to a straight or branched hydrocarbon chain radical group consisting solely of carbon and hydrogen atoms, containing at least one carbon-carbon double bond. Non-limiting examples of an alkenyl group include —CH=CH$_2$, —C(CH$_3$)=CH$_2$, —CH=CHCH$_3$, —CH=C(CH$_3$)$_2$ and —C(CH$_3$)=CHCH$_3$. In some embodiments, an alkenyl groups may have 2 to 6 carbons. Alkenyl groups can be substituted or unsubstituted. Depending on the structure, an alkenyl group can be a monoradical or a diradical (i.e., an alkenylene group).

The term "alkynyl" refers to a straight or branched hydrocarbon chain radical group consisting solely of carbon and hydrogen atoms, containing at least one carbon-carbon triple bond. Non-limiting examples of an alkynyl group include —C≡CH, —C≡CCH₃, —C≡CCH₂CH₃ and —C≡CCH₂CH₂CH₃. In some embodiments, an alkynyl group can have 2 to 6 carbons. Alkynyl groups can be substituted or unsubstituted. Depending on the structure, an alkynyl group can be a monoradical or a diradical (i.e., an alkynylene group).

"Amino" refers to a —NH₂ group.

The term "alkylamine" or "alkylamino" refers to the —N(alkyl)$_x$H$_y$ group, where alkyl is as defined herein and x and y are selected from the group x=1, y=1 and x=2, y=0. When x=2, the alkyl groups, taken together with the nitrogen to which they are attached, can optionally form a cyclic ring system. "Dialkylamino" refers to a —N(alkyl)₂ group, where alkyl is as defined herein.

The term "aromatic" refers to a planar ring having a delocalized π-electron system containing 4n+2π electrons, where n is an integer. Aromatic rings can be formed from five, six, seven, eight, nine, or more than nine atoms. Aromatics can be optionally substituted. The term "aromatic" includes both aryl groups (e.g., phenyl, naphthalenyl) and heteroaryl groups (e.g., pyridinyl, quinolinyl).

As used herein, the term "aryl" refers to an aromatic ring wherein each of the atoms forming the ring is a carbon atom. Aryl rings can be formed by five, six, seven, eight, nine, or more than nine carbon atoms. Aryl groups can be optionally substituted. Examples of aryl groups include, but are not limited to phenyl, and naphthalenyl. Depending on the structure, an aryl group can be a monoradical or a diradical (i.e., an arylene group).

"Carboxy" refers to —CO₂H. In some embodiments, carboxy moieties may be replaced with a "carboxylic acid bioisostere", which refers to a functional group or moiety that exhibits similar physical and/or chemical properties as a carboxylic acid moiety. A carboxylic acid bioisostere has similar biological properties to that of a carboxylic acid group. A compound with a carboxylic acid moiety can have the carboxylic acid moiety exchanged with a carboxylic acid bioisostere and have similar physical and/or biological properties when compared to the carboxylic acid-containing compound. For example, in one embodiment, a carboxylic acid bioisostere would ionize at physiological pH to roughly the same extent as a carboxylic acid group. Examples of bioisosteres of a carboxylic acid include, but are not limited to,

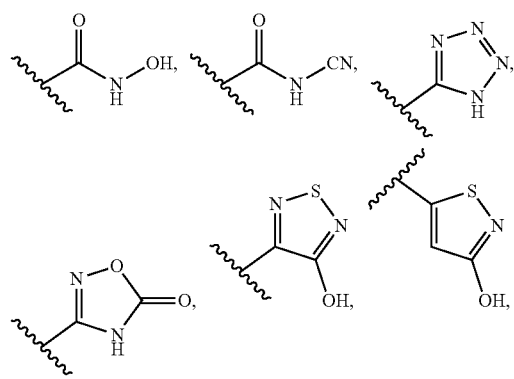

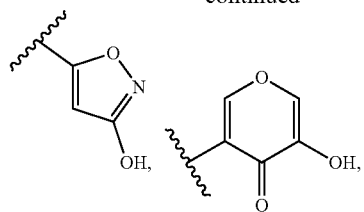

and the like.

The term "cycloalkyl" refers to a monocyclic or polycyclic non-aromatic radical, wherein each of the atoms forming the ring (i.e. skeletal atoms) is a carbon atom. Cycloalkyls may be saturated or partially unsaturated. In some embodiments, a cycloalkyl ring is fused with an aryl, heteroaryl, heterocycloalkyl, or a second cycloalkyl ring. In some embodiments, a cycloalkyl ring is a spirocyclic cycloalkyl ring. In some embodiments, cycloalkyl groups include groups having from 3 to 10 ring atoms. Depending on the structure, a cycloalkyl group can be a monoradical or a diradical (i.e., a cycloalkylene group).

The terms "heteroaryl" or, alternatively, "heteroaromatic" refers to an aryl group that includes one or more ring heteroatoms selected from nitrogen, oxygen and sulfur. As used herein, the heteroaryl radical is a monocyclic, bicyclic, or tricyclic ring system, wherein at least one of the rings in the ring system is fully unsaturated. An N-containing "heteroaromatic" or "heteroaryl" moiety refers to an aromatic group in which at least one of the skeletal atoms of the ring is a nitrogen atom. Depending on the structure, a heteroaryl group can be a monoradical or a diradical (i.e., a heteroarylene group).

A "heterocycloalkyl" group or "heteroalicyclic" group refers to a cycloalkyl group, wherein at least one skeletal ring atom is a heteroatom selected from nitrogen, oxygen and sulfur. Heterocycloalkyls may be saturated or partially unsaturated. In some embodiments, a heterocycloalkyl ring is fused with an aryl, heteroaryl, cycloalkyl, or a second heterocycloalkyl ring. The term heterocycloalkyl also includes all ring forms of the carbohydrates, including but not limited to the monosaccharides, the disaccharides and the oligosaccharides. In some embodiments, a heterocycloalkyl ring is a spirocyclic heterocycloalkyl ring. In some embodiments, a heterocycloalkyl ring is a bridged heterocycloalkyl ring. Unless otherwise noted, heterocycloalkyls have from 2 to 10 carbons in the ring. It is understood that when referring to the number of carbon atoms in a heterocycloalkyl, the number of carbon atoms in the heterocycloalkyl is not the same as the total number of atoms (including the heteroatoms) that make up the heterocycloalkyl (i.e. skeletal atoms of the heterocycloalkyl ring). Depending on the structure, a heterocycloalkyl group can be a monoradical or a diradical (i.e., a heterocycloalkylene group).

The term "halo" or, alternatively, "halogen" means fluoro, chloro, bromo and iodo.

The term "haloalkyl" refers to an alkyl group that is substituted with one or more halogens. The halogens may the same or they may be different. Non-limiting examples of haloalkyls include —CH₂Cl, —CF₃, —CHF₂, —CH₂CF₃, —CF₂CF₃, and the like.

The terms "fluoroalkyl" and "fluoroalkoxy" include alkyl and alkoxy groups, respectively, that are substituted with one or more fluorine atoms. Non-limiting examples of fluoroalkyls include —CF₃, —CHF₂, —CH₂F, —CH₂CF₃, —CF$_2$CF$_3$, —CF$_2$CF$_2$CF$_3$, —CF(CH$_3$)$_3$, and the like. Non-limiting examples of fluoroalkoxy groups, include —OCF$_3$, —OCHF$_2$, —OCH$_2$F, —OCH$_2$CF$_3$, —OCF$_2$CF$_3$, —OCF$_2$CF$_2$CF$_3$, —OCF(CH$_3$)$_2$, and the like.

The term "heteroalkyl" refers to an alkyl radical where one or more skeletal chain atoms is selected from an atom other than carbon, e.g., oxygen, nitrogen, sulfur, phosphorus, silicon, or combinations thereof. The heteroatom(s) may be placed at any interior position of the heteroalkyl group. Examples include, but are not limited to, —CH$_2$—O—CH$_3$, —CH$_2$—CH$_2$—O—CH$_3$, —CH$_2$—NH—CH$_3$, —CH$_2$—CH$_2$—NH—CH$_3$, —CH$_2$—N(CH$_3$)—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$—S(O)—CH$_3$, —CH$_2$—CH$_2$—S(O)$_2$—CH$_3$, —CH$_2$—NH—OCH$_3$, —CH$_2$—O—Si(CH$_3$)$_3$, —CH$_2$—CH=N—OCH$_3$, and —CH=CH—N(CH$_3$)—CH$_3$. In addition, up to two heteroatoms may be consecutive, such as, by way of example, —CH$_2$—NH—OCH$_3$ and —CH$_2$—O—Si(CH$_3$)$_3$. Excluding the number of heteroatoms, a "heteroalkyl" may have from 1 to 6 carbon atoms.

The term "oxo" refers to the =O radical.

The term "bond" or "single bond" refers to a chemical bond between two atoms, or two moieties when the atoms joined by the bond are considered to be part of larger substructure.

The term "moiety" refers to a specific segment or functional group of a molecule. Chemical moieties are often recognized chemical entities embedded in or appended to a molecule.

As used herein, the substituent "R" appearing by itself and without a number designation refers to a substituent selected from among from alkyl, haloalkyl, heteroalkyl, alkenyl, cycloalkyl, aryl, heteroaryl (bonded through a ring carbon), and heterocycloalkyl.

"Optional" or "optionally" means that a subsequently described event or circumstance may or may not occur and that the description includes instances when the event or circumstance occurs and instances in which it does not.

The term "optionally substituted" or "substituted" means that the referenced group may be substituted with one or more additional group(s) individually and independently selected from alkyl, cycloalkyl, aryl, heteroaryl, heterocycloalkyl, —OH, alkoxy, aryloxy, alkylthio, arylthio, alkylsulfoxide, arylsulfoxide, alkylsulfone, arylsulfone, —CN, alkyne, C$_1$-C$_6$alkylalkyne, halo, acyl, acyloxy, —CO$_2$H, —CO$_2$-alkyl, nitro, haloalkyl, fluoroalkyl, and amino, including mono- and di-substituted amino groups (e.g. —NH$_2$, —NHR, —N(R)$_2$), and the protected derivatives thereof. By way of example, an optional substituents may be L$^s$R$^5$, wherein each L$^s$ is independently selected from a bond, —O—, —C(=O)—, —S—, —S(=O)—, —S(=O)$_2$—, —NH—, —NHC(O)—, —C(O)NH—, S(=O)$_2$NH—, —NHS(=O)$_2$, —OC(O)NH—, —NHC(O) O—, —(C$_1$-C$_6$alkyl)-, or —(C$_2$-C$_6$alkenyl)-; and each R$^5$ is independently selected from among H, (C$_1$-C$_6$alkyl), (C$_3$-C$_8$cycloalkyl), aryl, heteroaryl, heterocycloalkyl, and C$_1$-C$_6$heteroalkyl. The protecting groups that may form the protective derivatives of the above substituents are found in sources such as Greene and Wuts, above.

"Pharmaceutically acceptable salt" includes both acid and base addition salts. A pharmaceutically acceptable salt of any one of the compounds described herein is intended to encompass any and all pharmaceutically suitable salt forms. Preferred pharmaceutically acceptable salts of the compounds described herein are pharmaceutically acceptable acid addition salts and pharmaceutically acceptable base addition salts.

"Pharmaceutically acceptable acid addition salt" refers to those salts which retain the biological effectiveness and properties of the free bases, which are not biologically or otherwise undesirable, and which are formed with inorganic acids such as hydrochloric acid, hydrobromic acid, sulfuric acid, nitric acid, phosphoric acid, hydroiodic acid, hydrofluoric acid, phosphorous acid, and the like. Also included are salts that are formed with organic acids such as aliphatic mono- and dicarboxylic acids, phenyl-substituted alkanoic acids, hydroxy alkanoic acids, alkanedioic acids, aromatic acids, aliphatic and, aromatic sulfonic acids, etc. and include, for example, acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Exemplary salts thus include sulfates, pyrosulfates, bisulfates, sulfites, bisulfites, nitrates, phosphates, monohydrogenphosphates, dihydrogenphosphates, metaphosphates, pyrophosphates, chlorides, bromides, iodides, acetates, trifluoroacetates, propionates, caprylates, isobutyrates, oxalates, malonates, succinate suberates, sebacates, fiumarates, maleates, mandelates, benzoates, chlorobenzoates, methylbenzoates, dinitrobenzoates, phthalates, benzenesulfonates, toluenesulfonates, phenylacetates, citrates, lactates, malates, tartrates, methanesulfonates, and the like. Also contemplated are salts of amino acids, such as arginates, gluconates, and galacturonates (see, for example, Berge S. M. et al., "Pharmaceutical Salts," *Journal of Pharmaceutical Science,* 66:1-19 (1997)). Acid addition salts of basic compounds are, in some embodiments, prepared by contacting the free base forms with a sufficient amount of the desired acid to produce the salt according to methods and techniques with which a skilled artisan is familiar.

"Pharmaceutically acceptable base addition salt" refers to those salts that retain the biological effectiveness and properties of the free acids, which are not biologically or otherwise undesirable. These salts are prepared from addition of an inorganic base or an organic base to the free acid. Pharmaceutically acceptable base addition salts are, in some embodiments, formed with metals or amines, such as alkali and alkaline earth metals or organic amines. Salts derived from inorganic bases include, but are not limited to, sodium, potassium, lithium, ammonium, calcium, magnesium, iron, zinc, copper, manganese, aluminum salts and the like. Salts derived from organic bases include, but are not limited to, salts of primary, secondary, and tertiary amines, substituted amines including naturally occurring substituted amines, cyclic amines and basic ion exchange resins, for example, isopropylamine, trimethylamine, diethylamine, triethylamine, tripropylamine, ethanolamine, diethanolamine, 2-dimethylaminoethanol, 2-diethylaminoethanol, dicyclohexylamine, lysine, arginine, histidine, caffeine, procaine, N,N-dibenzylethylenediamine, chloroprocaine, hydrabamine, choline, betaine, ethylenediamine, ethylenedianiline, N-methylglucamine, glucosamine, methylglucamine, theobromine, purines, piperazine, piperidine, N-ethylpiperidine, polyamine resins and the like. See Berge et al., supra.

The terms "polypeptide", "peptide" and "protein" are used interchangeably herein to refer to polymers of amino acids of any length. The polymer may be linear or branched, it may comprise modified amino acids, and it may be interrupted by non-amino acids. The terms also encompass an amino acid polymer that has been modified; for example, disulfide bond formation, glycosylation, lipidation, acetylation, phosphorylation, or any other manipulation, such as conjugation with a labeling component. As used herein the term "amino acid" refers to either natural and/or unnatural or synthetic amino acids, including glycine and both the D or L optical isomers, and amino acid analogs and peptidomimetics.

The terms "polynucleotide", "nucleotide", "nucleotide sequence", "nucleic acid" and "oligonucleotide" are used interchangeably. They refer to a polymeric form of nucleotides of any length, either deoxyribonucleotides or ribonucleotides, or analogs thereof. Polynucleotides may have any three dimensional structure, and may perform any function, known or unknown. The following are non-limiting examples of polynucleotides: coding or non-coding regions of a gene or gene fragment, loci (locus) defined from linkage analysis, exons, introns, messenger RNA (mRNA), transfer RNA, ribosomal RNA, short interfering RNA (siRNA), short-hairpin RNA (shRNA), micro-RNA (miRNA), ribozymes, cDNA, recombinant polynucleotides, branched polynucleotides, plasmids, vectors, isolated DNA of any sequence, isolated RNA of any sequence, nucleic acid probes, and primers. A polynucleotide may comprise one or more modified nucleotides, such as methylated nucleotides and nucleotide analogs, such as peptide nucleic acid (PNA), Morpholino and locked nucleic acid (LNA), glycol nucleic acid (GNA), threose nucleic acid (TNA), 2'-fluoro, 2'-OMe, and phosphorothiolated DNA. If present, modifications to the nucleotide structure may be imparted before or after assembly of the polymer. The sequence of nucleotides may be interrupted by non-nucleotide components. A polynucleotide may be further modified after polymerization, such as by conjugation with a labeling component or other conjugation target.

As used herein, "expression" refers to the process by which a polynucleotide is transcribed from a DNA template (such as into and mRNA or other RNA transcript) and/or the process by which a transcribed mRNA is subsequently translated into peptides, polypeptides, or proteins. Transcripts and encoded polypeptides may be collectively referred to as "gene product." If the polynucleotide is derived from genomic DNA, expression may include splicing of the mRNA in a eukaryotic cell.

The terms "subject," "individual," and "patient" are used interchangeably herein to refer to a vertebrate, preferably a mammal, more preferably a human. Mammals include, but are not limited to, murines, simians, humans, farm animals, sport animals, and pets. Tissues, cells, and their progeny of a biological entity obtained in vivo or cultured in vitro are also encompassed.

The terms "therapeutic agent", "therapeutic capable agent" or "treatment agent" are used interchangeably and refer to a molecule or compound that confers some beneficial effect upon administration to a subject. The beneficial effect includes enablement of diagnostic determinations; amelioration of a disease, symptom, disorder, or pathological condition; reducing or preventing the onset of a disease, symptom, disorder or condition; and generally counteracting a disease, symptom, disorder or pathological condition.

As used herein, "treatment" or "treating," or "palliating" or "ameliorating" are used interchangeably. These terms refer to an approach for obtaining beneficial or desired results including but not limited to a therapeutic benefit and/or a prophylactic benefit. By therapeutic benefit is meant any therapeutically relevant improvement in or effect on one or more diseases, conditions, or symptoms under treatment. For prophylactic benefit, the compositions may be administered to a subject at risk of developing a particular disease, condition, or symptom, or to a subject reporting one or more of the physiological symptoms of a disease, even though the disease, condition, or symptom may not have yet been manifested. Typically, prophylactic benefit includes reducing the incidence and/or worsening of one or more diseases, conditions, or symptoms under treatment (e.g. as between treated and untreated populations, or between treated and untreated states of a subject).

The term "effective amount" or "therapeutically effective amount" refers to the amount of an agent that is sufficient to effect beneficial or desired results. The therapeutically effective amount may vary depending upon one or more of: the subject and disease condition being treated, the weight and age of the subject, the severity of the disease condition, the manner of administration and the like, which can readily be determined by one of ordinary skill in the art. An effective amount of an active agent may be administered in a single dose or in multiple doses. A component may be described herein as having at least an effective amount, or at least an amount effective, such as that associated with a particular goal or purpose, such as any described herein. The term "effective amount" also applies to a dose that will provide an image for detection by an appropriate imaging method. The specific dose may vary depending on one or more of: the particular agent chosen, the dosing regimen to be followed, whether it is administered in combination with other compounds, timing of administration, the tissue to be imaged, and the physical delivery system in which it is carried.

An "antigen" is a moiety or molecule that contains an epitope, and, as such, also specifically binds to an antibody.

An "antigen binding unit" may be whole or a fragment (or fragments) of a full-length antibody, a structural variant thereof, a functional variant thereof, or a combination thereof. A full-length antibody may be, for example, a monoclonal, recombinant, chimeric, deimmunized, humanized and human antibody. Examples of a fragment of a full-length antibody may include, but are not limited to, variable heavy (VH), variable light (VL), a heavy chain found in camelids, such as camels, llamas, and alpacas (VHH or $V_HH$), a heavy chain found in sharks (V-NAR domain), a single domain antibody (sdAb, i.e., "nanobody") that comprises a single antigen-binding domain, Fv, Fd, Fab, Fab', F(ab')$_2$, and "r IgG" (or half antibody). Examples of modified fragments of antibodies may include, but are not limited to scFv, di-scFv or bi(s)-scFv, scFv-Fc, scFv-zipper, scFab, Fab2, Fab3, diabodies, single chain diabodies, tandem diabodies (Tandab's), tandem di-scFv, tandem tri-scFv, minibodies (e.g., (VH-VL-CH3)2, (scFv-CH3)2, ((scFv)2-CH3+CH3), ((scFv)2-CH3) or (scFv-CH3-scFv)2), and multibodies (e.g., triabodies or tetrabodies).

The term "antibody" and "antibodies" encompass any antigen binding units, including without limitation: monoclonal antibodies, human antibodies, humanized antibodies, camelised antibodies, chimeric antibodies, and any other epitope-binding fragments.

The term "in vivo" refers to an event that takes place in a subject's body.

The term "ex vivo" refers to an event that first takes place outside of the subject's body for a subsequent in vivo application into a subject's body. For example, an ex vivo preparation may involve preparation of cells outside of a subject's body for the purpose of introduction of the prepared cells into the same or a different subject's body.

The term "in vitro" refers to an event that takes place outside of a subject's body. For example, an in vitro assay encompasses any assay run outside of a subject's body. In vitro assays encompass cell-based assays in which cells alive or dead are employed. In vitro assays also encompass a cell-free assay in which no intact cells are employed.

The term "Ras" or "RAS" refers to a protein in the Rat sarcoma (Ras) superfamily of small GTPases, such as in the Ras subfamily. The Ras superfamily includes, but is not limited to, the Ras subfamily, Rho subfamily, Rab subfamily, Rap subfamily, Arf subfamily, Ran subfamily, Rheb subfamily, RGK subfamily, Rit subfamily, Miro subfamily, and Unclassified subfamily. In some embodiments, a Ras protein is selected from the group consisting of KRAS (K-Ras or K-ras or Kras), HRAS (or H-Ras), NRAS (or N-Ras), MRAS (or M-Ras), ERAS (or E-Ras), RRAS2 (or R-Ras2), RALA (or RalA), RALB (or RalB), RIT1, and any combination thereof, such as from KRAS, HRAS, NRAS, RALA, RALB, and any combination thereof.

The terms "Mutant Ras" and "Ras mutant," as used interchangeably herein, refer to a Ras protein with one or more amino acid mutations, such as with respect to a common reference sequence such as a wild-type (WT) sequence. In some embodiments, a mutant Ras is selected from a mutant KRAS, mutant HRAS, mutant NRAS, mutant MRAS, mutant ERAS, mutant RRAS2, mutant RALA, mutant RALB, mutant RIT1, and any combination thereof, such as from a mutant KRAS, mutant HRAS, mutant NRAS, mutant RALA, mutant RALB, and any combination thereof. In some embodiments, a mutation can be an introduced mutation, a naturally occurring mutation, or a non-naturally occurring mutation. In some embodiments, a mutation can be a substitution (e.g., a substituted amino acid), insertion (e.g., addition of one or more amino acids), or deletion (e.g., removal of one or more amino acids). In some embodiments, two or more mutations can be consecutive, non-consecutive, or a combination thereof. In some embodiments, a mutation can be present at any position of Ras. In some embodiments, a mutation can be present at position 12, 13, 62, 92, 95, or any combination thereof of Ras relative to SEQ ID No. 1 when optimally aligned. In some embodiments, a mutant Ras may comprise about or at least about 1, 2, 3, 4, 5, 6, 7, 8, 9, 10, 11, 12, 13, 14, 15, 16, 17, 18, 19, 20, 25, 30, 35, 40, 45, 50, or more than 50 mutations. In some embodiments, a mutant Ras may comprise up to about 1, 2, 3, 4, 5, 6, 7, 8, 9, 10, 11, 12, 13, 14, 15, 16, 17, 18, 19, 20, 25, 30, 35, 40, 45, or 50 mutations. In some embodiments, the mutant Ras is about or up to about 500, 400, 300, 250, 240, 233, 230, 220, 219, 210, 208, 206, 204, 200, 195, 190, 189, 188, 187, 186, 185, 180, 175, 174, 173, 172, 171, 170, 169, 168, 167, 166, 165, 160, 155, 150, 125, 100, 90, 80, 70, 60, 50, or fewer than 50 amino acids in length. In some embodiments, an amino acid of a mutation is a proteinogenic, natural, standard, non-standard, non-canonical, essential, non-essential, or non-natural amino acid. In some embodiments, an amino acid of a mutation has a positively charged side chain, a negatively charged side chain, a polar uncharged side chain, a non-polar side chain, a hydrophobic side chain, a hydrophilic side chain, an aliphatic side chain, an aromatic side chain, a cyclic side chain, an acyclic side chain, a basic side chain, or an acidic side chain. In some embodiments, a mutation comprises a reactive moiety. In some embodiments, a substituted amino acid comprises a reactive moiety. In some embodiments, a mutant Ras can be further modified, such as by conjugation with a detectable label. In some embodiments, a mutant Ras is a full-length or truncated polypeptide. For example, a mutant Ras can be a truncated polypeptide comprising residues 1-169 or residues 11-183 (e.g., residues 11-183 of a mutant RALA or mutant RALB).

Compounds

The compounds of Formula (I), (I'), (Ia), (Ia'), (Ib), (Ib'), (Ic), (Ic'), (II), (II'), (III), or (III'), or a pharmaceutically acceptable salt or solvate thereof, disclosed herein are SOS modulators and have a wide range of applications in therapeutics, diagnostics, and other biomedical research.

In some embodiments, the disclosure provides a compound of Formula (I), or a pharmaceutically acceptable salt or solvate thereof:

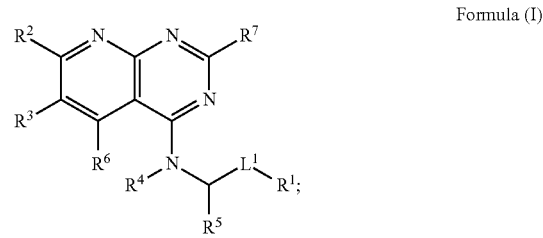

Formula (I)

wherein:

$R^1$ is a 3-12 membered cycloalkyl ring, 3-12 membered heterocycloalkyl ring, 6-10 membered aryl ring, or 5-10 membered heteroaryl ring, wherein the 3-12 membered cycloalkyl ring, 3-12 membered heterocycloalkyl ring, 6-10 membered aryl ring, and 5-10 membered heteroaryl ring are optionally substituted with one or more $R^{10}$;

$L^1$ is a bond or $C_{1-6}$alkyl;

$R^2$ is $-OR^{2a}$, $-NR^{2b}R^{2c}$, $-SR^{2g}$, $-S(O)R^{2h}$, $-S(O)_2R^{2h}$, $-S(O)_2NR^{2b}R^{2c}$, $-C(R^{2d})(R^{2e})(R^{2f})$, $C(O)NR^{2b}R^{2c}$, $-CN$, or halogen;

$R^{2a}$ is selected from hydrogen, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, $-C(O)OR^{12}$, $-C(O)R^{15}$, $-C(O)N(R^{12})(R^{13})$, $-S(O)_2R^{15}$, $-S(O)_2N(R^{12})(R^{13})$, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20a}$;

$R^{2b}$ is selected from hydrogen, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, $-C(O)OR^{12}$, $-C(O)R^{15}$, $-C(O)N(R^{12})(R^{13})$, $-S(O)_2R^{15}$, and $-S(O)_2N(R^{12})(R^{13})$, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20a}$;

$R^{2c}$ is selected from hydrogen, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20a}$; or $R^{2b}$ and $R^{2c}$, together with the nitrogen to which they are attached, form a $C_{2-9}$heterocycloalkyl ring optionally substituted with one, two, or three $R^{20a}$;

$R^{2a}$ is selected from hydrogen, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, $-OR^{12}$, $-SR^{12}$, $-N(R^{12})(R^{13})$, $-C(O)OR^{12}$, $-OC(O)N(R^{12})(R^{13})$, $-N(R^{14})C(O)N(R^{12})(R^{13})$, $-N(R^{14})C(O)OR^{15}$, $-N(R^{14})S(O)_2R^{15}$, $-C(O)R^{15}$, $-S(O)R^{15}$, $-OC(O)R^{15}$, $-C(O)N(R^{12})(R^{13})$, $-C(O)C(O)N(R^{12})(R^{13})$, $-N(R^{14})C(O)R^{15}$, $-S(O)_2R^{15}$, $-S(O)_2N(R^{12})(R^{13})$, $-S(=O)(=NH)N(R^{12})(R^{13})$, $-CH_2C(O)N(R^{12})(R^{13})$, $-CH_2N(R^{14})C(O)$ $R^{15}$, —$CH_2S(O)_2R^{15}$, —$CH_2S(O)_2N(R^{12})(R^{13})$, —$CH_2N(R^{12})S(O)_2(R^{13})$, and —$P(O)(R^{17})(R^{17a})$, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20a}$;

$R^{2e}$ is selected from hydrogen, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20a}$;

$R^{2f}$ is selected from hydrogen, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20a}$;

$R^{2g}$ is selected from hydrogen, $C_{2-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —$C(O)OR^{12}$, —$C(O)R^{15}$, —$C(O)N(R^{12})(R^{13})$, —$S(O)_2R^{15}$, —$S(O)_2N(R^{12})(R^{13})$, wherein $C_{2-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20a}$;

$R^{2h}$ is selected from $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20a}$;

$R^3$ is selected from halogen, $C_{1-6}$alkyl, $C_{2-6}$alkenyl, $C_{2-6}$alkynyl, $C_{3-14}$cycloalkyl, $C_{2-9}$heterocycloalkyl, $C_{6-10}$aryl, $C_{1-9}$heteroaryl, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, $N(R^{14})S(O)R^{15}$, —$C(O)R^{15}$, —$S(O)R^{15}$, —$OC(O)R^{15}$, —$C(O)N(R^{12})(R^{13a})$, —$C(O)C(O)N(R^{12})(R^{13})$, —$N(R^{14})C(O)R^{15}$, —$S(O)_2R^{15}$, —$S(O)_2N(R^{12})(R^{13})$, —$S(O)N(R^{12})(R^{13})$, —$S(=O)(=N))N(R^{12})(R^{13})$, —$CH_2C(O)N(R^{12})(R^{13})$, —$CH_2N(R^{14})C(O)R^{15}$, —$CH_2S(O)_2R^{15}$, —$CH_2S(O)_2N(R^{12})(R^{13})$, —$CH_2N(R^{12})S(O)_2(R^{13})$, $CH_2S(O) R^{15}$, —$CH_2S(O)N(R^{12})(R^{13})$, —$CH_2N(R^{12})S(O)(R^{13})$ and —$P(O)(R^{17})(R^{17a})$, wherein $C_{1-6}$alkyl, $C_{2-6}$alkenyl, $C_{2-6}$alkynyl, $C_{3-14}$cycloalkyl, $C_{2-9}$heterocycloalkyl, $C_{6-10}$aryl, and $C_{1-9}$heteroaryl are optionally substituted with one, two, or three $R^{20b}$;

$R^4$ is selected from hydrogen, $C_{1-6}$alkyl, and $C_{1-6}$haloalkyl;

$R^5$ is selected from hydrogen, $C_{1-6}$alkyl, and $C_{1-6}$haloalkyl;

$R^6$ is selected from hydrogen, halogen, —CN, $C_{1-6}$alkyl, $C_{2-6}$alkenyl, $C_{2-6}$alkynyl, $C_{3-10}$cycloalkyl, $C_{2-9}$heterocycloalkyl, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{15}$, —$S(O)_2R^{15}$, —$S(O)_2N(R^{12})(R^{13})$, —$S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, —$CH_2S(O)_2N(R^{12})(R^{13})$, —$CH_2N(R^{12})S(O)_2(R^{13})$, and —$P(O)(R^{17})(R^{17a})$ wherein $C_{1-6}$alkyl, $C_{2-6}$alkenyl, $C_{2-6}$alkynyl, $C_{3-10}$cycloalkyl, and $C_{2-9}$heterocycloalkyl are optionally substituted with one, two, or three $R^{20c}$;

$R^7$ is selected from hydrogen, halogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{1-9}$heteroaryl, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{15}$, —$S(O)_2R^{15}$, —$S(O)_2N(R^{12})(R^{13})$, —$S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, —$CH_2S(O)_2N(R^{12})(R^{13})$, —$CH_2N(R^{12})S(O)_2(R^{13})$, and —$P(O)(R^{17})(R^{17a})$, wherein $C_{1-6}$alkyl, $C_{2-6}$alkenyl, $C_{2-6}$alkynyl, $C_{3-10}$cycloalkyl, $C_{2-9}$heterocycloalkyl, and $C_{1-9}$heteroaryl are optionally substituted with one, two, or three $R^{20c}$;

each $R^{10}$ is independently selected from halogen, —CN, $C_{1-6}$alkyl, $C_{2-6}$alkenyl, $C_{2-6}$alkynyl, $C_{3-7}$cycloalkyl, $C_{2-9}$heterocycloalkyl, $C_{6-10}$aryl, $C_{1-9}$heteroaryl, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{15}$, —$S(O)_2R^{15}$, —$S(O)_2N(R^{12})(R^{13})$, —$S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, —$CH_2S(O)_2N(R^{12})(R^{13})$, —$CH_2N(R^{12})S(O)_2(R^{13})$, and —$P(O)(R^{17})(R^{17a})$, wherein $C_{1-6}$alkyl, $C_{2-6}$alkenyl, $C_{2-6}$alkynyl, $C_{3-7}$cycloalkyl, $C_{2-9}$heterocycloalkyl, $C_{6-10}$aryl, and $C_{1-9}$heteroaryl are optionally substituted with one, two, or three $R^{20a}$;

each $R^{12}$ is independently selected from hydrogen, $C_{1-6}$alkyl, $C_{1-6}$ haloalkyl, $C_{2-6}$alkenyl, $C_{2-6}$alkynyl, $C_{3-7}$cycloalkyl, $C_{2-9}$heterocycloalkyl, $C_{6-10}$aryl, and $C_{1-9}$heteroaryl, wherein $C_{1-6}$alkyl, $C_{2-6}$alkenyl, $C_{2-6}$alkynyl, $C_{3-7}$cycloalkyl, $C_{2-9}$heterocycloalkyl, $C_{6-10}$aryl, and $C_{1-9}$heteroaryl are optionally substituted with one, two, or three $R^{20e}$;

each $R^{13}$ is independently selected from hydrogen, $C_{1-6}$alkyl, and $C_{1-6}$haloalkyl; or $R^{12}$ and $R^{13}$, together with the nitrogen to which they are attached, form a $C_{2-9}$heterocycloalkyl ring optionally substituted with one, two, or three $R^{20f}$;

$R^{13a}$ is selected from $C_{1-6}$alkyl and $C_{1-6}$haloalkyl; or $R^{12}$ and $R^{13a}$, together with the nitrogen to which they are attached, form a $C_{2-9}$heterocycloalkyl ring optionally substituted with one, two, or three $R^{20f}$;

each $R^{14}$ is independently selected from hydrogen, $C_{1-6}$alkyl, and $C_{1-6}$haloalkyl;

each $R^{15}$ is independently selected $C_{1-6}$alkyl, $C_{2-6}$alkenyl, $C_{2-6}$alkynyl, $C_{3-7}$cycloalkyl, $C_{2-9}$heterocycloalkyl, $C_{6-10}$aryl, and $C_{1-9}$ heteroaryl, wherein $C_{1-6}$alkyl, $C_{2-6}$alkenyl, $C_{2-6}$alkynyl, $C_{3-7}$cycloalkyl, $C_{2-9}$heterocycloalkyl, $C_{6-10}$aryl, and $C_{1-9}$heteroaryl are optionally substituted with one, two, or three $R^{20g}$;

each $R^{17}$ and each $R^{17a}$ are each independently selected from $C_{1-6}$alkyl and $C_{3-6}$cycloalkyl, wherein $C_{1-6}$alkyl and $C_{3-6}$cycloalkyl are optionally substituted with one, two or three of $R^{20h}$; or $R^{17}$ and $R^{17a}$ are combined to form a $C_{2-9}$heterocycloalkyl ring;

each $R^{20a}$, $R^{20b}$, $R^{20c}$, $R^{20d}$, $R^{20e}$, $R^{20f}$, $R^{20g}$, and $R^{20h}$ are each independently selected from halogen, oxo, =NH, —CN, $C_{1-6}$alkyl, $C_{2-6}$alkenyl, $C_{2-6}$alkynyl, $C_{3-10}$cycloalkyl, —$CH_2$—$C_{3-10}$cycloalkyl, $C_{2-9}$heterocycloalkyl, —$CH_2$—$C_{2-9}$heterocycloalkyl, $C_{6-10}$aryl, —$CH_2$—$C_{6-10}$aryl, $C_{1-9}$heteroaryl, —$OR^{21}$, —$SR^{21}$, —$N(R^{22})(R^{23})$, —$C(O)OR^{22}$, —$C(O)N(R^{22})(R^{23})$, —$C(O)C(O)N(R^{22})(R^{23})$, —$OC(O)N(R^{22})(R^{23})$, —$N(R^{24})C(O)N(R^{22})(R^{23})$, —$N(R^{24})C(O)OR^{25}$, —$N(R^{24})C(O)R^{25}$, —$N(R^{24})S(O)_2R^{25}$, —$C(O)R^{25}$, —$S(O)_2R^{25}$, —$S(O)_2N(R^{22})(R^{23})$, —$OCH_2C(O)OR^{22}$, and —$OC(O)R^{25}$, wherein $C_{1-6}$alkyl, $C_{2-6}$alkenyl, $C_{2-6}$alkynyl, $C_{3-10}$cycloalkyl, —$CH_2$—$C_{3-10}$cycloalkyl, $C_{2-9}$heterocycloalkyl, —$CH_2$—$C_{2-9}$heterocycloalkyl, $C_{6-10}$aryl, —$CH_2$—$C_{6-10}$aryl, and $C_{1-9}$heteroaryl are optionally substituted with one, two, or three groups independently selected from halogen, oxo, =NH, —CN, $C_{1-6}$alkyl, $C_{1-6}$haloalkyl, $C_{1-6}$alkoxy, $C_{1-6}$haloalkoxy, —$OR^{21}$, —$SR^{21}$, —$N(R^{22})(R^{23})$, —$C(O)OR^{22}$, —$C(O)N(R^{22})(R^{23})$, —$C(O)C(O)N(R^{22})(R^{23})$, —$OC(O)N(R^{22})(R^{23})$, —$N(R^{24})C(O)N(R^{22})(R^{23})$, —$N(R^{24})C(O)OR^{25}$, —$N(R^{24})C(O)R^{25}$, —$N(R^{24})S(O)_2R^{25}$, —$C(O)R^{25}$, —$S(O)_2R^{25}$, —$S(O)_2N(R^{22})(R^{23})$, and —$OC(O)R^{25}$;

each $R^{21}$ is independently selected from H, $C_{1-6}$alkyl, $C_{1-6}$haloalkyl, $C_{2-6}$alkenyl, $C_{2-6}$alkynyl, $C_{3-7}$cycloalkyl, $C_{2-9}$heterocycloalkyl, $C_{6-10}$aryl, and $C_{1-9}$heteroaryl, wherein $C_{3-7}$cycloalkyl, $C_{2-9}$heterocycloalkyl, $C_{6-10}$aryl, and $C_{1-9}$heteroaryl are optionally substituted with one, two, or three groups independently selected from halogen and $C_{1-6}$alkyl;

each $R^{22}$ is independently selected from H, $C_{1-6}$alkyl, $C_{1-6}$haloalkyl, $C_{2-6}$alkenyl, $C_{2-6}$alkynyl, $C_{3-7}$cycloalkyl, $C_{2-9}$heterocycloalkyl, $C_{6-10}$aryl, and $C_{1-9}$heteroaryl, wherein $C_{3-7}$cycloalkyl, $C_{2-9}$heterocycloalkyl, $C_{6-10}$aryl, and $C_{1-9}$heteroaryl are optionally substituted with one, two, or three groups independently selected from halogen and $C_{1-6}$alkyl;

each $R^{23}$ is independently selected from H and $C_{1-6}$alkyl;

each $R^{24}$ is independently selected from H and $C_{1-6}$alkyl; and each $R^{25}$ is selected from $C_{1-6}$alkyl, $C_{2-6}$alkenyl, $C_{2-6}$alkynyl, $C_{3-7}$cycloalkyl, $C_{2-9}$heterocycloalkyl, $C_{6-10}$aryl, and $C_{1-9}$heteroaryl, wherein $C_{1-6}$alkyl, $C_{3-7}$cycloalkyl, $C_{2-9}$heterocycloalkyl, $C_{6-10}$aryl, and $C_{1-9}$heteroaryl are optionally substituted with one, two, or three groups independently selected from halogen, $C_{1-6}$alkyl, $C_{1-6}$haloalkyl, $C_{1-6}$alkoxy, $C_{3-7}$cycloalkyl, $C_{2-9}$heterocycloalkyl, $C_{6-10}$aryl, and $C_{1-9}$heteroaryl.

In some embodiments is a compound of Formula (I) or (I'), or a pharmaceutically acceptable salt or solvate thereof, wherein $R^2$ is —$OR^{2a}$. In some embodiments is a compound of Formula (I) or (I'), or a pharmaceutically acceptable salt or solvate thereof, wherein $R^2$ is —$NR^{2b}R^{2c}$. In some embodiments is a compound of Formula (I) or (I'), or a pharmaceutically acceptable salt or solvate thereof, wherein $R^2$ is —$SR^{2g}$. In some embodiments is a compound of Formula (I) or (I'), or a pharmaceutically acceptable salt or solvate thereof, wherein $R^2$ is —$C(R^{2a})(R^{2e})(R^{2f})$. In some embodiments is a compound of Formula (I) or (I'), or a pharmaceutically acceptable salt or solvate thereof, wherein $R^2$ is halogen.

In some embodiments is a compound of Formula (I) having the structure of Formula (Ia), or a pharmaceutically acceptable salt or solvate thereof:

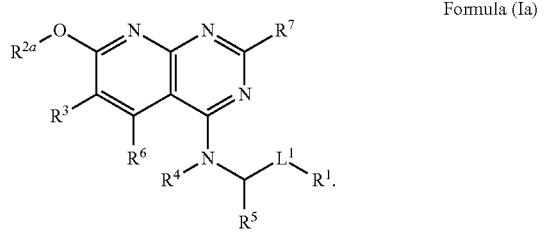

Formula (Ia)

In some embodiments is a compound of Formula (I) or (Ia), or a pharmaceutically acceptable salt or solvate thereof, wherein $R^{2a}$ is $C_{1-6}$alkyl optionally substituted with one, two, or three $R^{20a}$. In some embodiments is a compound of Formula (I) or (Ia), or a pharmaceutically acceptable salt or solvate thereof, wherein $R^{2a}$ is unsubstituted $C_{1-6}$alkyl. In some embodiments is a compound of Formula (I) or (Ia), or a pharmaceutically acceptable salt or solvate thereof, wherein $R^{2a}$ is —$CH_3$.

In some embodiments is a compound of Formula (I) having the structure of Formula (Ib), or a pharmaceutically acceptable salt or solvate thereof:

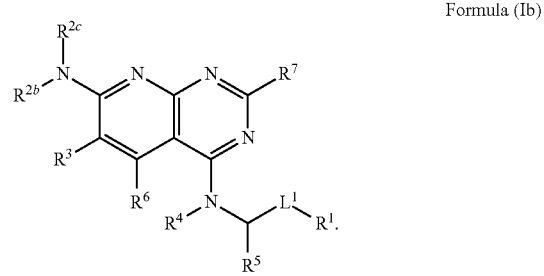

Formula (Ib)

In some embodiments is a compound of Formula (I) or (Ib), or a pharmaceutically acceptable salt or solvate thereof, wherein $R^{2b}$ is $C_{1-6}$alkyl optionally substituted with one, two, or three $R^{20a}$. In some embodiments is a compound of Formula (I) or (Ib), or a pharmaceutically acceptable salt or solvate thereof, wherein $R^{2b}$ is unsubstituted $C_{1-6}$alkyl. In some embodiments is a compound of Formula (I) or (Ib), or a pharmaceutically acceptable salt or solvate thereof, wherein $R^{2b}$ is —$CH_3$. In some embodiments is a compound of Formula (I) or (Ib), or a pharmaceutically acceptable salt or solvate thereof, wherein $R^{2b}$ is hydrogen. In some embodiments is a compound of Formula (I) or (Ib), or a pharmaceutically acceptable salt or solvate thereof, wherein $R^{2e}$ is $C_{1-6}$alkyl optionally substituted with one, two, or three $R^{20a}$. In some embodiments is a compound of Formula (I) or (Ib), or a pharmaceutically acceptable salt or solvate thereof, wherein $R^{2e}$ is unsubstituted $C_{1-6}$alkyl. In some embodiments is a compound of Formula (I) or (Ib), or a pharmaceutically acceptable salt or solvate thereof, wherein $R^{2e}$ is —$CH_3$. In some embodiments is a compound of Formula (I) or (Ib), or a pharmaceutically acceptable salt or solvate thereof, wherein $R^{2e}$ is hydrogen. In some embodiments is a compound of Formula (I) or (Ib), or a pharmaceutically acceptable salt or solvate thereof, wherein $R^{2b}$ and $R^{2c}$ are independently $C_{1-6}$alkyl optionally substituted with one, two, or three $R^{20a}$. In some embodiments is a compound of Formula (I) or (Ib), or a pharmaceutically acceptable salt or solvate thereof, wherein $R^{2b}$ and $R^{2c}$ are independently unsubstituted $C_{1-6}$alkyl. In some embodiments is a compound of Formula (I) or (Ib), or a pharmaceutically acceptable salt or solvate thereof, wherein $R^{2b}$ and $R^{2c}$ are —$CH_3$. In some embodiments is a compound of Formula (I) or (Ib), or a pharmaceutically acceptable salt or solvate thereof, wherein $R^{2b}$ and $R^{2c}$ are hydrogen.

In some embodiments is a compound of Formula (I) having the structure of Formula (Ic), or a pharmaceutically acceptable salt or solvate thereof:

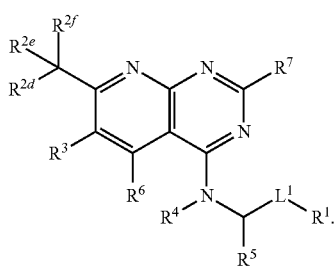

Formula (Ic)

In some embodiments is a compound of Formula (I) or (Ic), or a pharmaceutically acceptable salt or solvate thereof, wherein $R^{2d}$ is hydrogen or $C_{1-6}$alkyl optionally substituted with one, two, or three $R^{20a}$. In some embodiments is a compound of Formula (I) or (Ic), or a pharmaceutically acceptable salt or solvate thereof, wherein $R^{2a}$ is hydrogen. In some embodiments is a compound of Formula (I) or (Ic), or a pharmaceutically acceptable salt or solvate thereof, wherein $R^{2a}$ is $C_{1-6}$alkyl optionally substituted with one, two, or three $R^{20a}$. In some embodiments is a compound of Formula (I) or (Ic), or a pharmaceutically acceptable salt or solvate thereof, wherein $R^{2a}$ is unsubstituted $C_{1-6}$alkyl. In some embodiments is a compound of Formula (I) or (Ic), or a pharmaceutically acceptable salt or solvate thereof, wherein $R^{2a}$ is —$CH_3$. In some embodiments is a compound of Formula (I) or (Ic), or a pharmaceutically acceptable salt or solvate thereof, wherein $R^{2e}$ is hydrogen or $C_{1-6}$alkyl optionally substituted with one, two, or three $R^{20a}$. In some embodiments is a compound of Formula (I) or (Ic), or a pharmaceutically acceptable salt or solvate thereof, wherein $R^{2e}$ is hydrogen. In some embodiments is a compound of Formula (I) or (Ic), or a pharmaceutically acceptable salt or solvate thereof, wherein $R^{2e}$ is $C_{1-6}$ alkyl optionally substituted with one, two, or three $R^{20a}$. In some embodiments is a compound of Formula (I) or (Ic), or a pharmaceutically acceptable salt or solvate thereof, wherein $R^{2e}$ is unsubstituted $C_{1-6}$alkyl. In some embodiments is a compound of Formula (I) or (Ic), or a pharmaceutically acceptable salt or solvate thereof, wherein $R^{2e}$ is —$CH_3$. In some embodiments is a compound of Formula (I) or (Ic), or a pharmaceutically acceptable salt or solvate thereof, wherein $R^{2f}$ is hydrogen or $C_{1-6}$alkyl optionally substituted with one, two, or three $R^{20a}$. In some embodiments is a compound of Formula (I) or (Ic), or a pharmaceutically acceptable salt or solvate thereof, wherein $R^{2f}$ is hydrogen. In some embodiments is a compound of Formula (I) or (Ic), or a pharmaceutically acceptable salt or solvate thereof, wherein $R^{2f}$ is $C_{1-6}$alkyl optionally substituted with one, two, or three $R^{20a}$. In some embodiments is a compound of Formula (I) or (Ic), or a pharmaceutically acceptable salt or solvate thereof, wherein $R^{2f}$ is unsubstituted $C_{1-6}$alkyl. In some embodiments is a compound of Formula (I) or (Ic), or a pharmaceutically acceptable salt or solvate thereof, wherein $R^{2f}$ is —$CH_3$.

In some embodiments is a compound of Formula (I), (Ia), (Ib), or (Ic), or a pharmaceutically acceptable salt or solvate thereof, wherein $R^5$ is $C_{1-6}$alkyl. In some embodiments is a compound of Formula (I), (Ia), (Ib), or (Ic), or a pharmaceutically acceptable salt or solvate thereof, wherein $R^5$ is —$CH_3$. In some embodiments is a compound of Formula (I), (Ia), (Ib), or (Ic), or a pharmaceutically acceptable salt or solvate thereof, wherein $R^5$ is $C_{1-6}$haloalkyl. In some embodiments is a compound of Formula (I), (Ia), (Ib), or (Ic), or a pharmaceutically acceptable salt or solvate thereof, wherein $R^5$ is hydrogen.

In some embodiments is a compound of Formula (I) having the structure of Formula (I'), or a pharmaceutically acceptable salt or solvate thereof:

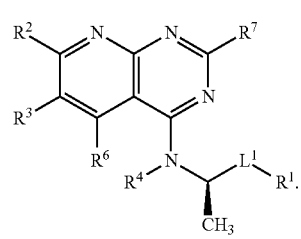

Formula (I')

In some embodiments is a compound of Formula (Ia) having the structure of Formula (Ia'), or a pharmaceutically acceptable salt or solvate thereof:

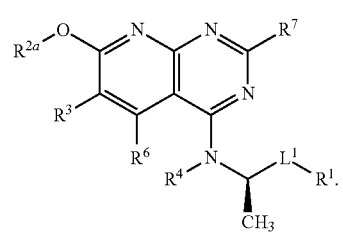

Formula (Ia')

In some embodiments is a compound of Formula (Ib) having the structure of Formula (Ib'), or a pharmaceutically acceptable salt or solvate thereof:

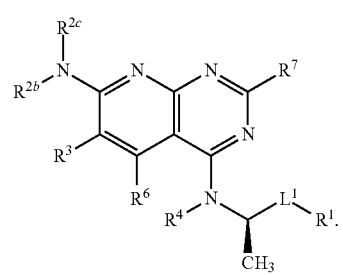

Formula (Ib')

In some embodiments is a compound of Formula (Ic) having the structure of Formula (Ic'), or a pharmaceutically acceptable salt or solvate thereof:

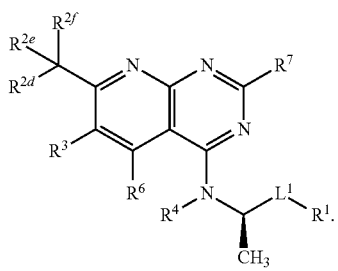

Formula (Ic')

In some embodiments is a compound of Formula (I), (I'), (Ia), (Ia'), (Ib), (Ib'), (Ic), or (Ic'), or a pharmaceutically acceptable salt or solvate thereof, wherein $R^3$ is selected from —$OR^{12}$, —$N(R^{12})(R^{13})$, —$C(O)R^{15}$, —$C(O)N(R^{12})(R^{13})$, —$SR^{12}$, —$SOR^{12}$, —$SO_2(R^{12})(R^{13})$, —$SO_2N(R^{12})(R^{13})$, —$P(O)(R^{17})(R^{17a})$, $C_{1-6}$alkyl, $C_{3-10}$cycloalkyl, $C_{2-9}$heterocycloalkyl, $C_{6-10}$aryl, and $C_{1-9}$heteroaryl, wherein $C_{1-6}$alkyl, $C_{3-10}$cycloalkyl, $C_{2-9}$heterocycloalkyl, $C_{6-10}$aryl, and $C_{1-9}$heteroaryl are optionally substituted with one, two, or three $R^{20b}$.

In some embodiments is a compound of Formula (I), (I'), (Ia), (Ia'), (Ib), (Ib'), (Ic), or (Ic'), or a pharmaceutically acceptable salt or solvate thereof, wherein $R^3$ is selected from —$C(O)R^{15}$, —$C(O)N(R^{12})(R^{13})$, $C_{2-9}$heterocycloalkyl, $C_{6-10}$aryl, and $C_{1-9}$heteroaryl, wherein $C_{2-9}$heterocycloalkyl, $C_{6-10}$aryl, and $C_{1-9}$heteroaryl are optionally substituted with one, two, or three $R^{20b}$. In some embodiments is a compound of Formula (I), (I'), (Ia), (Ia'), (Ib), (Ib'), (Ic), or (Ic'), wherein $R^3$ is selected from —$C(O)R^{15}$. In some embodiments is a compound of Formula (I), (Ia), (Ib), (Ic), (Id), (Ie) or (If), wherein $R^{15}$ is $C_{2-9}$heterocycloalkyl optionally substituted with one, two, or three $R^{20g}$.

In some embodiments is a compound of Formula (I), (I'), (Ia), (Ia'), (Ib), (Ib'), (Ic), or (Ic'), or a pharmaceutically acceptable salt or solvate thereof, wherein $R^3$ is $C_{2-9}$heterocycloalkyl optionally substituted with one, two, or three $R^{20b}$. In some embodiments is a compound of Formula (I), (I'), (Ia), (Ia'), (Ib), (Ib'), (Ic), or (Ic'), or a pharmaceutically acceptable salt or solvate thereof, wherein $R^3$ is spirocyclic $C_{2-9}$heterocycloalkyl optionally substituted with one, two, or three $R^{20b}$. In some embodiments is a compound of Formula (I), (I'), (Ia), (Ia'), (Ib), (Ib'), (Ic), or (Ic'), or a pharmaceutically acceptable salt or solvate thereof, wherein $R^3$ is fused $C_{2-9}$heterocycloalkyl optionally substituted with one, two, or three $R^{2b}$. In some embodiments is a compound of Formula (I), (I'), (Ia), (Ia'), (Ib), (Ib'), (Ic), or (Ic'), or a pharmaceutically acceptable salt or solvate thereof, wherein $R^3$ is $C_{6-10}$aryl optionally substituted with one, two, or three $R^{20b}$. In some embodiments is a compound of Formula (I), (I'), (Ia), (Ia'), (Ib), (Ib'), (Ic), or (Ic'), or a pharmaceutically acceptable salt or solvate thereof, wherein $R^3$ is fused $C_{6-10}$aryl optionally substituted with one, two, or three $R^{20b}$. In some embodiments is a compound of Formula (I), (I'), (Ia), (Ia'), (Ib), (Ib'), (Ic), or (Ic'), or a pharmaceutically acceptable salt or solvate thereof, wherein $R^3$ is $C_{1-9}$heteroaryl optionally substituted with one, two, or three $R^{2b}$. In some embodiments is a compound of Formula (I), (I'), (Ia), (Ia'), (Ib), (Ib'), (Ic), or (Ic'), or a pharmaceutically acceptable salt or solvate thereof, wherein $R^3$ is fused $C_{1-9}$heteroaryl optionally substituted with one, two, or three $R^{2b}$. In some embodiments is a compound of Formula (I), (I'), (Ia), (Ia'), (Ib), (Ib'), (Ic), or (Ic'), or a pharmaceutically acceptable salt or solvate thereof, wherein $R^3$ is —$C(O)N(R^{12})(R^{13})$.

In some embodiments is a compound of Formula (I), (I'), (Ia), (Ia'), (Ib), (Ib'), (Ic), or (Ic'), or a pharmaceutically acceptable salt or solvate thereof, wherein $R^{15}$ is $C_{2-9}$heterocycloalkyl optionally substituted with one, two, or three $R^{20g}$. In some embodiments is a compound of Formula (I), (I'), (Ia), (Ia'), (Ib), (Ib'), (Ic), or (Ic'), or a pharmaceutically acceptable salt or solvate thereof, wherein $R^{15}$ is spirocyclic $C_{2-9}$heterocycloalkyl optionally substituted with one, two, or three $R^{20g}$. In some embodiments is a compound of Formula (I), (I'), (Ia), (Ia'), (Ib), (Ib'), (Ic), or (Ic'), or a pharmaceutically acceptable salt or solvate thereof, wherein $R^{15}$ is fused $C_{2-9}$heterocycloalkyl optionally substituted with one, two, or three $R^{20g}$.

In some embodiments is a compound of Formula (I), (I'), (Ia), (Ia'), (Ib), (Ib'), (Ic), or (Ic'), or a pharmaceutically acceptable salt or solvate thereof, wherein $R^3$ is $C_{1-6}$alkyl optionally substituted with one, two, or three $R^{20b}$. In some embodiments is a compound of Formula (I), (I'), (Ia), (Ia'), (Ib), (Ib'), (Ic), or (Ic'), or a pharmaceutically acceptable salt or solvate thereof, wherein $R^3$ is —$OR^{12}$. In some embodiments is a compound of Formula (I), (I'), (Ia), (Ia'), (Ib), (Ib'), (Ic), or (Ic'), or a pharmaceutically acceptable salt or solvate thereof, wherein $R^3$ is —$N(R^{12})(R^{13})$. In some embodiments is a compound of Formula (I), (I'), (Ia), (Ia'), (Ib), (Ib'), (Ic), or (Ic'), or a pharmaceutically acceptable salt or solvate thereof, wherein $R^3$ is halogen.

In embodiments of a compound of Formula (I), (I'), (Ia), (Ia'), (Ib), (Ib'), (Ic), or (Ic'), or a pharmaceutically acceptable salt or solvate thereof, $R^3$ is $C_{3-14}$cycloalkyl, including $C_{6-14}$cycloalkyl, $C_9$cycloalkyl, $C_{3-7}$cycloalkyl, $C_{3-6}$cycloalkyl, $C_{3-5}$cycloalkyl, and $C_{3-4}$cycloalkyl, each of which being optionally substituted with one, two, or three $R^{20b}$. In embodiments of a compound of Formula (I), (I'), (Ia), (Ia'), (Ib), (Ib'), (Ic), or (Ic'), or a pharmaceutically acceptable salt or solvate thereof, $R^3$ is $C_{6-14}$cycloalkyl optionally substituted with one, two, or three $R^{20b}$. In embodiments of a compound of Formula (I), (I'), (Ia), (Ia'), (Ib), (Ib'), (Ic), or (Ic'), or a pharmaceutically acceptable salt or solvate thereof, $R^3$ is $C_{6-9}$cycloalkyl optionally substituted with one, two, or three $R^{20b}$. In embodiments of a compound of Formula (I), (I'), (Ia), (Ia'), (Ib), (Ib'), (Ic), or (Ic'), or a pharmaceutically acceptable salt or solvate thereof, $R^3$ is $C_{3-7}$cycloalkyl optionally substituted with one, two, or three $R^{20b}$. In embodiments of a compound of Formula (I), (I'), (Ia), (Ia'), (Ib), (Ib'), (Ic), or (Ic'), or a pharmaceutically acceptable salt or solvate thereof, $R^3$ is $C_{3-6}$cycloalkyl optionally substituted with one, two, or three $R^{20b}$. In embodiments of a compound of Formula (I), (I'), (Ia), (Ia'), (Ib), (Ib'), (Ic), or (Ic'), or a pharmaceutically acceptable salt or solvate thereof, $R^3$ is $C_{3-5}$cycloalkyl optionally substituted with one, two, or three $R^{20b}$. In embodiments of a compound of Formula (I), (I'), (Ia), (Ia'), (Ib), (Ib'), (Ic), or (Ic'), or a pharmaceutically acceptable salt or solvate thereof, $R^3$ is $C_{3-4}$cycloalkyl optionally substituted with one, two, or three $R^{20b}$.

In embodiments of a compound of Formula (I), (I'), (Ia), (Ia'), (Ib), (Ib'), (Ic), or (Ic'), or a pharmaceutically acceptable salt or solvate thereof, $R^3$ is $C_{3-14}$cycloalkyl, including $C_{6-14}$cycloalkyl, $C_9$cycloalkyl, $C_{3-7}$cycloalkyl, $C_{3-6}$cycloalkyl, $C_{3-5}$cycloalkyl, and $C_{3-4}$cycloalkyl, each of which being substituted with one, two, or three $R^{20b}$. In embodiments of a compound of Formula (I), (I'), (Ia), (Ia'), (Ib), (Ib'), (Ic), or (Ic'), or a pharmaceutically acceptable salt or solvate thereof, $R^3$ is $C_{6-14}$cycloalkyl substituted with one, two, or three $R^{20b}$. In embodiments of a compound of Formula (I), (I'), (Ia), (Ia'), (Ib), (Ib'), (Ic), or (Ic'), or a pharmaceutically acceptable salt or solvate thereof, $R^3$ is $C_{6-9}$cycloalkyl substituted with one, two, or three $R^{20b}$. In embodiments of a compound of Formula (I), (I'), (Ia), (Ia'), (Ib), (Ib'), (Ic), or (Ic'), or a pharmaceutically acceptable salt or solvate thereof, $R^3$ is $C_{3-7}$cycloalkyl substituted with one, two, or three $R^{20b}$. In embodiments of a compound of Formula (I), (I'), (Ia), (Ia'), (Ib), (Ib'), (Ic), or (Ic'), or a pharmaceutically acceptable salt or solvate thereof, $R^3$ is $C_{3-6}$cycloalkyl substituted with one, two, or three $R^{20b}$. In embodiments of a compound of Formula (I), (I'), (Ia), (Ia'), (Ib), (Ib'), (Ic), or (Ic'), or a pharmaceutically acceptable salt or solvate thereof, $R^3$ is $C_{3-5}$cycloalkyl substituted with one, two, or three $R^{20b}$. In embodiments of a compound of Formula (I), (I'), (Ia), (Ia'), (Ib), (Ib'), (Ic), or (Ic'), or a pharmaceutically acceptable salt or solvate thereof, $R^3$ is $C_{3-4}$cycloalkyl substituted with one, two, or three $R^{20b}$.

In embodiments of a compound of Formula (I), (I'), (Ia), (Ia'), (Ib), (Ib'), (Ic), or (Ic'), or a pharmaceutically acceptable salt or solvate thereof, $R^3$ is $C_{3-14}$cycloalkyl, including $C_{6-14}$cycloalkyl, $C_{6-9}$cycloalkyl, $C_{3-7}$cycloalkyl, $C_{3-6}$cycloalkyl, $C_{3-5}$cycloalkyl, and $C_{3-4}$cycloalkyl, each of which being optionally substituted with one $R^{20b}$. In embodiments of a compound of Formula (I), (I'), (Ia), (Ia'), (Ib), (Ib'), (Ic), or (Ic'), or a pharmaceutically acceptable salt or solvate thereof, $R^3$ is $C_{6-14}$cycloalkyl optionally substituted with one $R^{20b}$. In embodiments of a compound of Formula (I), (I'), (Ia), (Ia'), (Ib), (Ib'), (Ic), or (Ic'), or a pharmaceutically acceptable salt or solvate thereof, $R^3$ is $C_{6-9}$cycloalkyl optionally substituted with one $R^{20b}$. In embodiments of a compound of Formula (I), (I'), (Ia), (Ia'), (Ib), (Ib'), (Ic), or (Ic'), or a pharmaceutically acceptable salt or solvate thereof, $R^3$ is $C_{3-7}$cycloalkyl optionally substituted with one $R^{20b}$. In embodiments of a compound of Formula (I), (I'), (Ia), (Ia'), (Ib), (Ib'), (Ic), or (Ic'), or a pharmaceutically acceptable salt or solvate thereof, $R^3$ is $C_{3-6}$cycloalkyl optionally substituted with one $R^{20b}$. In embodiments of a compound of Formula (I), (I'), (Ia), (Ia'), (Ib), (Ib'), (Ic), or (Ic'), or a pharmaceutically acceptable salt or solvate thereof, $R^3$ is $C_{3-5}$cycloalkyl optionally substituted with one $R^{20b}$. In embodiments of a compound of Formula (I), (I'), (Ia), (Ia'), (Ib), (Ib'), (Ic), or (Ic'), or a pharmaceutically acceptable salt or solvate thereof, $R^3$ is $C_{3-4}$cycloalkyl optionally substituted with one $R^{20b}$.

In embodiments of a compound of Formula (I), (I'), (Ia), (Ia'), (Ib), (Ib'), (Ic), or (Ic'), or a pharmaceutically acceptable salt or solvate thereof, $R^3$ is $C_{3-14}$cycloalkyl, including $C_{6-14}$cycloalkyl, $C_{6-9}$cycloalkyl, $C_{3-7}$cycloalkyl, $C_{3-6}$cycloalkyl, $C_{3-5}$cycloalkyl, and $C_{3-4}$cycloalkyl, each of which being optionally substituted with two $R^{20b}$. In embodiments of a compound of Formula (I), (I'), (Ia), (Ia'), (Ib), (Ib'), (Ic), or (Ic'), or a pharmaceutically acceptable salt or solvate thereof, $R^3$ is $C_{6-14}$cycloalkyl optionally substituted with two $R^{20b}$. In embodiments of a compound of Formula (I), (I'), (Ia), (Ia'), (Ib), (Ib'), (Ic), or (Ic'), or a pharmaceutically acceptable salt or solvate thereof, $R^3$ is $C_{6-9}$cycloalkyl optionally substituted with two $R^{20b}$. In embodiments of a compound of Formula (I), (I'), (Ia), (Ia'), (Ib), (Ib'), (Ic), or (Ic'), or a pharmaceutically acceptable salt or solvate thereof, $R^3$ is $C_{3-7}$cycloalkyl optionally substituted with two $R^{20b}$. In embodiments of a compound of Formula (I), (I'), (Ia), (Ia'), (Ib), (Ib'), (Ic), or (Ic'), or a pharmaceutically acceptable salt or solvate thereof, $R^3$ is $C_{3-6}$cycloalkyl optionally substituted with one $R^{20b}$. In embodiments of a compound of Formula (I), (I'), (Ia), (Ia'), (Ib), (Ib'), (Ic), or (Ic'), or a pharmaceutically acceptable salt or solvate thereof, $R^3$ is $C_{3-5}$cycloalkyl optionally substituted with two $R^{20b}$. In embodiments of a compound of Formula (I), (I'), (Ia), (Ia'), (Ib), (Ib'), (Ic), or (Ic'), or a pharmaceutically acceptable salt or solvate thereof, $R^3$ is $C_{3-4}$cycloalkyl optionally substituted with two $R^{20b}$.

In each of the above embodiments, $R^{20b}$ is independently selected from amino, —CN, $C_{1-3}$alkyl, $C_{1-3}$alkoxy, $C_{1-3}$haloalkyl, —OH, —N($R^{24}$)C(O)$R^{25}$, and —C(O)N($R^{22}$)($R^{23}$). In some embodiments of a compound of Formula (I), (I'), (Ia), (Ia'), (Ib), (Ib'), (Ic), or (Ic'), or a pharmaceutically acceptable salt or solvate thereof, $R^{20b}$ is amino. In some embodiments of a compound of Formula (I), (I'), (Ia), (Ia'), (Ib), (Ib'), (Ic), or (Ic'), or a pharmaceutically acceptable salt or solvate thereof, $R^{20b}$ is —CN. In some embodiments of a compound of Formula (I), (I'), (Ia), (Ia'), (Ib), (Ib'), (Ic), or (Ic'), or a pharmaceutically acceptable salt or solvate thereof, $R^{20b}$ is $C_{1-3}$alkyl. In some embodiments of a compound of Formula (I), (I'), (Ia), (Ia'), (Ib), (Ib'), (Ic), or (Ic'), or a pharmaceutically acceptable salt or solvate thereof, $R^{20b}$ is $C_{1-3}$alkoxy. In some embodiments of a compound of Formula (I), (I'), (Ia), (Ia'), (Ib), (Ib'), (Ic), or (Ic'), or a pharmaceutically acceptable salt or solvate thereof, $R^{20b}$ is $C_{1-3}$haloalkyl. In some embodiments of a compound of Formula (I), (I'), (Ia), (Ia'), (Ib), (Ib'), (Ic), or (Ic'), or a pharmaceutically acceptable salt or solvate thereof, $R^{20b}$ is —OH. In some embodiments of a compound of Formula (I), (I'), (Ia), (Ia'), (Ib), (Ib'), (Ic), or (Ic'), or a pharmaceutically acceptable salt or solvate thereof, $R^{20b}$ is —N($R^{24}$)C(O)$R^{25}$. In some embodiments of a compound of Formula (I), (I'), (Ia), (Ia'), (Ib), (Ib'), (Ic), or (Ic'), or a pharmaceutically acceptable salt or solvate thereof, $R^{20b}$ is —C(O)N($R^{22}$)($R^{23}$). In some embodiments of a compound of Formula (I), (I'), (Ia), (Ia'), (Ib), (Ib'), (Ic), or (Ic'), or a pharmaceutically acceptable salt or solvate thereof, $R^{20b}$ is —NHC(O)$R^{25}$. In some embodiments of a compound of Formula (I), (I'), (Ia), (Ia'), (Ib), (Ib'), (Ic), or (Ic'), or a pharmaceutically acceptable salt or solvate thereof, $R^{20b}$ is —C(O)NH($R^{22}$). In some embodiments of a compound of Formula (I), (I'), (Ia), (Ia'), (Ib), (Ib'), (Ic), or (Ic'), or a pharmaceutically acceptable salt or solvate thereof, $R^{20b}$ is —NHC(O)$R^{25}$ and $R^{25}$ is $C_{2-9}$heterocycloalkyl optionally substituted with one, two, or three groups independently selected from halogen, $C_{1-6}$alkyl, $C_{1-6}$haloalkyl, $C_{1-6}$alkoxy, $C_{3-7}$cycloalkyl, $C_{2-9}$heterocycloalkyl, $C_{6-10}$aryl, and $C_{1-9}$heteroaryl. In some embodiments of a compound of Formula (I), (I'), (Ia), (Ia'), (Ib), (Ib'), (Ic), or (Ic'), or a pharmaceutically acceptable salt or solvate thereof, $R^{20b}$ is —C(O)NH($R^{22}$) and $R^{22}$ is $C_{2-9}$heterocycloalkyl optionally substituted with one, two, or three groups independently selected from halogen and $C_{1-6}$alkyl. In some embodiments of a compound of Formula (I), (I'), (Ia), (Ia'), (Ib), (Ib'), (Ic), or (Ic'), or a pharmaceutically acceptable salt or solvate thereof, $R^{20b}$ is —NHC(O)$R^{25}$ and $R^{25}$ is $C_{2-5}$heterocycloalkyl optionally substituted with one $C_{1-6}$alkyl. In some embodiments of a compound of Formula (I), (I'), (Ia), (Ia'), (Ib), (Ib'), (Ic), or (Ic'), or a pharmaceutically acceptable salt or solvate thereof, $R^{20b}$ is —C(O)NH($R^{22}$) and $R^{22}$ is $C_{2-5}$heterocycloalkyl optionally substituted with one $C_{1-6}$alkyl.

In embodiments of a compound of Formula (I), (I'), (Ia), (Ia'), (Ib), (Ib'), (Ic), or (Ic'), or a pharmaceutically acceptable salt or solvate thereof, $R^3$ is $C_{6-14}$cycloalkyl (including $C_{6-14}$cycloalkyl, $C_{6-9}$cycloalkyl, $C_{3-7}$cycloalkyl, $C_{3-6}$cycloalkyl, $C_{3-5}$cycloalkyl, and $C_{3-4}$cycloalkyl), optionally substituted with one, two, or three $R^{20b}$ that is amino. In embodiments of a compound of Formula (I), (I'), (Ia), (Ia'), (Ib), (Ib'), (Ic), or (Ic'), or a pharmaceutically acceptable salt or solvate thereof, $R^3$ is $C_{6-14}$cycloalkyl (including $C_{6-14}$cycloalkyl, $C_{6-9}$cycloalkyl, $C_{3-7}$cycloalkyl, $C_{3-6}$cycloalkyl, $C_{3-5}$cycloalkyl, and $C_{3-4}$cycloalkyl), optionally substituted with one, two, or three $R^{20b}$ that is —CN. In embodiments of a compound of Formula (I), (I'), (Ia), (Ia'), (Ib), (Ib'), (Ic), or (Ic'), or a pharmaceutically acceptable salt or solvate thereof, $R^3$ is $C_{6-14}$cycloalkyl (including $C_{6-14}$cycloalkyl, $C_{6-9}$cycloalkyl, $C_{3-7}$cycloalkyl, $C_{3-6}$cycloalkyl, $C_{3-5}$cycloalkyl, and $C_{3-4}$cycloalkyl), optionally substituted with one, two, or three $R^{20b}$ that is $C_{1-3}$alkyl. In embodiments of a compound of Formula (I), (I'), (Ia), (Ia'), (Ib), (Ib'), (Ic), or (Ic'), or a pharmaceutically acceptable salt or solvate thereof, $R^3$ is $C_{6-14}$cycloalkyl (including $C_{6-14}$cycloalkyl, $C_{6-9}$cycloalkyl, $C_{3-7}$cycloalkyl, $C_{3-6}$cycloalkyl, $C_{3-5}$cycloalkyl, and $C_{3-4}$cycloalkyl), optionally substituted with one, two, or three $R^{20b}$ that is $C_{1-3}$alkoxy. In embodiments of a compound of Formula (I), (I'), (Ia), (Ia'), (Ib), (Ib'), (Ic), or (Ic'), or a pharmaceutically acceptable salt or solvate thereof, $R^3$ is $C_{6-14}$cycloalkyl (including $C_{6-14}$cycloalkyl, $C_{6-9}$cycloalkyl, $C_{3-7}$cycloalkyl, $C_{3-6}$cycloalkyl, $C_{3-5}$cycloalkyl, and $C_{3-4}$cycloalkyl), optionally substituted with one, two, or three $R^{20b}$ that is $C_{1-3}$haloalkyl. In embodiments of a compound of Formula (I), (I'), (Ia), (Ia'), (Ib), (Ib'), (Ic), or (Ic'), or a pharmaceutically acceptable salt or solvate thereof, $R^3$ is $C_{6-14}$cycloalkyl (including $C_{6-14}$cycloalkyl, $C_{6-9}$cycloalkyl, $C_{3-7}$cycloalkyl, $C_{3-6}$cycloalkyl, $C_{3-5}$cycloalkyl, and $C_{3-4}$cycloalkyl), optionally substituted with one, two, or three $R^{20b}$ that is —OH. In embodiments of a compound of Formula (I), (I'), (Ia), (Ia'), (Ib), (Ib'), (Ic), or (Ic'), or a pharmaceutically acceptable salt or solvate thereof, $R^3$ is $C_{6-14}$cycloalkyl (including $C_{6-14}$cycloalkyl, $C_{6-9}$cycloalkyl, $C_{3-7}$cycloalkyl, $C_{3-6}$cycloalkyl, $C_{3-5}$cycloalkyl, and $C_{3-4}$cycloalkyl), optionally substituted with one, two, or three $R^{20b}$ that is oxo. In embodiments of a compound of Formula (I), (I'), (Ia), (Ia'), (Ib), (Ib'), (Ic), or (Ic'), or a pharmaceutically acceptable salt or solvate thereof, $R^3$ is $C_{6-14}$cycloalkyl (including $C_{6-14}$cycloalkyl, $C_{6-9}$cycloalkyl, $C_{3-7}$cycloalkyl, $C_{3-6}$cycloalkyl, $C_{3-5}$cycloalkyl, and $C_{3-4}$cycloalkyl), optionally substituted with one, two, or three $R^{20b}$ that is —N($R^{24}$)C(O)$R^{25}$. In embodiments of a compound of Formula (I), (I'), (Ia), (Ia'), (Ib), (Ib'), (Ic), or (Ic'), or a pharmaceutically acceptable salt or solvate thereof, $R^3$ is $C_{6-14}$cycloalkyl (including $C_{6-14}$cycloalkyl, $C_{6-9}$cycloalkyl, $C_{3-7}$cycloalkyl, $C_{3-6}$cycloalkyl, $C_{3-5}$cycloalkyl, and $C_{3-4}$cycloalkyl), optionally substituted with one, two, or three $R^{20b}$ that is —NHC(O)$R^{25}$. In embodiments of a compound of Formula (I), (I'), (Ia), (Ia'), (Ib), (Ib'), (Ic), or (Ic'), or a pharmaceutically acceptable salt or solvate thereof, $R^3$ is $C_{6-14}$cycloalkyl (including $C_{6-14}$cycloalkyl, $C_{6-9}$cycloalkyl, $C_{3-7}$cycloalkyl, $C_{3-6}$cycloalkyl, $C_{3-5}$cycloalkyl, and $C_{3-4}$cycloalkyl), optionally substituted with one, two, or three $R^{20b}$ that is —NHC(O)$R^{25}$ and $R^{25}$ is $C_{2-9}$heterocycloalkyl optionally substituted with one, two, or three groups independently selected from halogen, $C_{1-6}$alkyl, $C_{1-6}$haloalkyl, $C_{1-6}$alkoxy, $C_{3-7}$cycloalkyl, $C_{2-9}$heterocycloalkyl, $C_{6-10}$aryl, and $C_{1-9}$heteroaryl. In embodiments of a compound of Formula (I), (I'), (Ia), (Ia'), (Ib), (Ib'), (Ic), or (Ic'), or a pharmaceutically acceptable salt or solvate thereof, $R^3$ is $C_{6-14}$cycloalkyl (including $C_{6-14}$cycloalkyl, $C_{6-9}$cycloalkyl, $C_{3-7}$cycloalkyl, $C_{3-6}$cycloalkyl, $C_{3-5}$cycloalkyl, and $C_{3-4}$cycloalkyl), optionally substituted with one, two, or three $R^{20b}$ that is —NHC(O)$R^{25}$ and $R^{25}$ is $C_{2-5}$heterocycloalkyl optionally substituted with one $C_{1-6}$alkyl. In embodiments of a compound of Formula (I), (I'), (Ia), (Ia'), (Ib), (Ib'), (Ic), or (Ic'), or a pharmaceutically acceptable salt or solvate thereof, $R^3$ is $C_{6-14}$cycloalkyl (including $C_{6-14}$cycloalkyl, $C_{6-9}$cycloalkyl, $C_{3-7}$cycloalkyl, $C_{3-6}$cycloalkyl, $C_{3-5}$cycloalkyl, and $C_{3-4}$cycloalkyl), optionally substituted with one, two, or three $R^{20b}$ that is —C(O)N($R^{22}$)($R^{23}$). In embodiments of a compound of Formula (I), (I'), (Ia), (Ia'), (Ib), (Ib'), (Ic), or (Ic'), or a pharmaceutically acceptable salt or solvate thereof, $R^3$ is $C_{6-14}$cycloalkyl (including $C_{6-14}$cycloalkyl, $C_{6-9}$cycloalkyl, $C_{3-7}$cycloalkyl, $C_{3-6}$cycloalkyl, $C_{3-5}$cycloalkyl, and $C_{3-4}$cycloalkyl), optionally substituted with one, two, or three $R^{20b}$ that is —C(O)NH($R^{22}$). In embodiments of a compound of Formula (I), (I'), (Ia), (Ia'), (Ib), (Ib'), (Ic), or (Ic'), or a pharmaceutically acceptable salt or solvate thereof, $R^3$ is $C_{6-14}$cycloalkyl (including $C_{6-14}$cycloalkyl, $C_{6-9}$cycloalkyl, $C_{3-7}$cycloalkyl, $C_{3-6}$cycloalkyl, $C_{3-5}$cycloalkyl, and $C_{3-4}$cycloalkyl), optionally substituted with one, two, or three $R^{20b}$ that is —C(O)NH($R^{22}$) and $R^{22}$ is $C_{2-9}$heterocycloalkyl optionally substituted with one, two, or three groups independently selected from halogen and $C_{1-6}$alkyl. In embodiments of a compound of Formula (I), (I'), (Ia), (Ia'), (Ib), (Ib'), (Ic), or (Ic'), or a pharmaceutically acceptable salt or solvate thereof, $R^3$ is $C_{6-14}$cycloalkyl (including $C_{6-14}$cycloalkyl, $C_{6-9}$cycloalkyl, $C_{3-7}$cycloalkyl, $C_{3-6}$cycloalkyl, $C_{3-5}$cycloalkyl, and $C_{3-4}$cycloalkyl), optionally substituted with one, two, or three $R^{20b}$ that is —C(O)NH($R^{22}$) and $R^{22}$ is $C_{2-5}$heterocycloalkyl optionally substituted with one $C_{1-6}$alkyl.

In embodiments of a compound of Formula (I), (I'), (Ia), (Ia'), (Ib), (Ib'), (Ic), or (Ic'), or a pharmaceutically acceptable salt or solvate thereof, $R^3$ is $C_{2-9}$heterocycloalkyl, including $C_{6-9}$heterocycloalkyl, $C_{3-7}$heterocycloalkyl, $C_{3-6}$heterocycloalkyl, $C_{5-6}$ heterocycloalkyl, $C_{3-5}$heterocycloalkyl, $C_{3-4}$heterocycloalkyl, each of which being optionally substituted with one, two, or three $R^{20b}$. In embodiments of a compound of Formula (I), (I'), (Ia), (Ia'), (Ib), (Ib'), (Ic), or (Ic'), or a pharmaceutically acceptable salt or solvate thereof, $R^3$ is $C_{6-9}$heterocycloalkyl optionally substituted with one, two, or three $R^{20b}$. In embodiments of a compound of Formula (I), (I'), (Ia), (Ia'), (Ib), (Ib'), (Ic), or (Ic'), or a pharmaceutically acceptable salt or solvate thereof, $R^3$ is $C_{3-7}$heterocycloalkyl optionally substituted with one, two, or three $R^{20b}$. In embodiments of a compound of Formula (I), (I'), (Ia), (Ia'), (Ib), (Ib'), (Ic), or (Ic'), or a pharmaceutically acceptable salt or solvate thereof, $R^3$ is $C_{3-6}$heterocycloalkyl optionally substituted with one, two, or three $R^{20b}$. In embodiments of a compound of Formula (I), (I'), (Ia), (Ia'), (Ib), (Ib'), (Ic), or (Ic'), or a pharmaceutically acceptable salt or solvate thereof, $R^3$ is $C_{6-9}$heterocycloalkyl optionally substituted with one, two, or three $R^{20b}$. In embodiments of a compound of Formula (I), (I'), (Ia), (Ia'), (Ib), (Ib'), (Ic), or (Ic'), or a pharmaceutically acceptable salt or solvate thereof, $R^3$ is $C_{3-5}$ heterocycloalkyl optionally substituted with one, two, or three $R^{20b}$. In embodiments of a compound of Formula (I), (I'), (Ia), (Ia'), (Ib), (Ib'), (Ic), or (Ic'), or a pharmaceutically acceptable salt or solvate thereof, $R^3$ is $C_{3-4}$heterocycloalkyl optionally substituted with one, two, or three $R^{20b}$.

In embodiments, each of the $R^3$ described above including $C_{6-9}$heterocycloalkyl, $C_{3-7}$heterocycloalkyl, $C_{3-6}$heterocycloalkyl, $C_{5-6}$ heterocycloalkyl, $C_{3-5}$heterocycloalkyl, $C_{3-4}$heterocycloalkyl, is optionally substituted with one $R^{20b}$. In embodiments, each of the $R^3$ described above, including $C_{6-9}$heterocycloalkyl, $C_{3-7}$heterocycloalkyl, $C_{3-6}$heterocycloalkyl, $C_{5-6}$ heterocycloalkyl, $C_{3-5}$heterocycloalkyl, $C_{3-4}$heterocycloalkyl, is optionally substituted with two $R^{20b}$. In embodiments, each of the $R^3$ described above, including $C_{6-9}$heterocycloalkyl, $C_{3-7}$heterocycloalkyl, $C_{3-6}$heterocycloalkyl, $C_{5-6}$ heterocycloalkyl, $C_{3-5}$heterocycloalkyl, $C_{3-4}$heterocycloalkyl, is optionally substituted with three $R^{20b}$.

In each of the above embodiments, $R^{20b}$ is independently selected from amino, —CN, $C_{1-3}$alkyl, $C_{1-3}$alkoxy, $C_{1-3}$haloalkyl, —OH, —N($R^{24}$)C(O)$R^{25}$, and —C(O)N($R^{22}$)($R^{23}$).

In some embodiments of a compound of Formula (I), (I'), (Ia), (Ia'), (Ib), (Ib'), (Ic), or (Ic'), or a pharmaceutically acceptable salt or solvate thereof, $R^{20b}$ is amino. In some embodiments of a compound of Formula (I), (I'), (Ia), (Ia'), (Ib), (Ib'), (Ic), or (Ic'), or a pharmaceutically acceptable salt or solvate thereof, $R^{20b}$ is —CN. In some embodiments of a compound of Formula (I), (I'), (Ia), (Ia'), (Ib), (Ib'), (Ic), or (Ic'), or a pharmaceutically acceptable salt or solvate thereof, $R^{20b}$ is $C_{1-3}$alkyl. In some embodiments of a compound of Formula (I), (I'), (Ia), (Ia'), (Ib), (Ib'), (Ic), or (Ic'), or a pharmaceutically acceptable salt or solvate thereof, $R^{20b}$ is $C_{1-3}$alkoxy. In some embodiments of a compound of Formula (I), (I'), (Ia), (Ia'), (Ib), (Ib'), (Ic), or (Ic'), or a pharmaceutically acceptable salt or solvate thereof, $R^{20b}$ is $C_{1-3}$haloalkyl. In some embodiments of a compound of Formula (I), (I'), (Ia), (Ia'), (Ib), (Ib'), (Ic), or (Ic'), or a pharmaceutically acceptable salt or solvate thereof, $R^{20b}$ is —OH. In some embodiments of a compound of Formula (I), (I'), (Ia), (Ia'), (Ib), (Ib'), (Ic), or (Ic'), or a pharmaceutically acceptable salt or solvate thereof, $R^{20b}$ is —N($R^{24}$)C(O)$R^{25}$. In some embodiments of a compound of Formula (I), (I'), (Ia), (Ia'), (Ib), (Ib'), (Ic), or (Ic'), or a pharmaceutically acceptable salt or solvate thereof, $R^{20b}$ is —C(O)N($R^{22}$)($R^{23}$). In some embodiments of a compound of Formula (I), (I'), (Ia), (Ia'), (Ib), (Ib'), (Ic), or (Ic'), or a pharmaceutically acceptable salt or solvate thereof, $R^{20b}$ is —NHC(O)$R^{25}$. In some embodiments of a compound of Formula (I), (I'), (Ia), (Ia'), (Ib), (Ib'), (Ic), or (Ic'), or a pharmaceutically acceptable salt or solvate thereof, $R^{20b}$ is —C(O)NH($R^{22}$). In some embodiments of a compound of Formula (I), (I'), (Ia), (Ia'), (Ib), (Ib'), (Ic), or (Ic'), or a pharmaceutically acceptable salt or solvate thereof, $R^{20b}$ is —NHC(O)$R^{25}$ and $R^{25}$ is $C_{2-9}$heterocycloalkyl optionally substituted with one, two, or three groups independently selected from halogen, $C_{1-6}$alkyl, $C_{1-6}$haloalkyl, $C_{1-6}$alkoxy, $C_{3-7}$cycloalkyl, $C_{2-9}$heterocycloalkyl, $C_{6-10}$aryl, and $C_{1-9}$heteroaryl. In some embodiments of a compound of Formula (I), (I'), (Ia), (Ia'), (Ib), (Ib'), (Ic), or (Ic'), or a pharmaceutically acceptable salt or solvate thereof, $R^{20b}$ is —C(O)NH($R^{22}$) and $R^{22}$ is $C_{2-9}$heterocycloalkyl optionally substituted with one, two, or three groups independently selected from halogen and $C_{1-6}$alkyl. In some embodiments of a compound of Formula (I), (I'), (Ia), (Ia'), (Ib), (Ib'), (Ic), or (Ic'), or a pharmaceutically acceptable salt or solvate thereof, $R^{20b}$ is —NHC(O)$R^{25}$ and $R^{25}$ is $C_{2-5}$heterocycloalkyl optionally substituted with one $C_{1-6}$alkyl. In some embodiments of a compound of Formula (I), (I'), (Ia), (Ia'), (Ib), (Ib'), (Ic), or (Ic'), or a pharmaceutically acceptable salt or solvate thereof, $R^{20b}$ is —C(O)NH($R^{22}$) and $R^{22}$ is $C_{2-5}$heterocycloalkyl optionally substituted with one $C_{1-6}$alkyl.

In embodiments of a compound of Formula (I), (I'), (Ia), (Ia'), (Ib), (Ib'), (Ic), or (Ic'), or a pharmaceutically acceptable salt or solvate thereof, $R^3$ is $C_{2-9}$heterocycloalkyl (including $C_{6-9}$heterocycloalkyl, $C_{3-7}$heterocycloalkyl, $C_{3-6}$heterocycloalkyl, $C_{5-6}$heterocycloalkyl, $C_{3-5}$heterocycloalkyl, and $C_{3-4}$heterocycloalkyl), optionally substituted with one, two, or three $R^{20b}$ that is amino. In embodiments of a compound of Formula (I), (I'), (Ia), (Ia'), (Ib), (Ib'), (Ic), or (Ic'), or a pharmaceutically acceptable salt or solvate thereof, $R^3$ is $C_{2-9}$heterocycloalkyl (including $C_{6-9}$heterocycloalkyl, $C_{3-7}$heterocycloalkyl, $C_{3-6}$heterocycloalkyl, $C_{5-6}$heterocycloalkyl, $C_{3-5}$heterocycloalkyl, and $C_{3-4}$heterocycloalkyl), optionally substituted with one, two, or three $R^{20b}$ that is —CN. In embodiments of a compound of Formula (I), (I'), (Ia), (Ia'), (Ib), (Ib'), (Ic), or (Ic'), or a pharmaceutically acceptable salt or solvate thereof, $R^3$ is $C_{2-9}$heterocycloalkyl (including $C_{6-9}$heterocycloalkyl, $C_{3-7}$heterocycloalkyl, $C_{3-6}$heterocycloalkyl, $C_{5-6}$heterocycloalkyl, $C_{3-5}$heterocycloalkyl, and $C_{3-4}$heterocycloalkyl), optionally substituted with one, two, or three $R^{20b}$ that is $C_{1-3}$alkyl. In embodiments of a compound of Formula (I), (I'), (Ia), (Ia'), (Ib), (Ib'), (Ic), or (Ic'), or a pharmaceutically acceptable salt or solvate thereof, $R^3$ is $C_{2-9}$heterocycloalkyl (including $C_{6-9}$heterocycloalkyl, $C_{3-7}$heterocycloalkyl, $C_{3-6}$heterocycloalkyl, $C_{5-6}$heterocycloalkyl, $C_{3-5}$heterocycloalkyl, and $C_{3-4}$heterocycloalkyl), optionally substituted with one, two, or three $R^{20b}$ that is $C_{1-3}$alkoxy. In embodiments of a compound of Formula (I), (I'), (Ia), (Ia'), (Ib), (Ib'), (Ic), or (Ic'), or a pharmaceutically acceptable salt or solvate thereof, $R^3$ is $C_{2-9}$heterocycloalkyl (including $C_{6-9}$heterocycloalkyl, $C_{3-7}$heterocycloalkyl, $C_{3-6}$heterocycloalkyl, $C_{5-6}$heterocycloalkyl, $C_{3-5}$heterocycloalkyl, and $C_{3-4}$heterocycloalkyl), optionally substituted with one, two, or three $R^{20b}$ that is $C_{1-3}$haloalkyl. In embodiments of a compound of Formula (I), (I'), (Ia), (Ia'), (Ib), (Ib'), (Ic), or (Ic'), or a pharmaceutically acceptable salt or solvate thereof, $R^3$ is $C_{2-9}$heterocycloalkyl (including $C_{6-9}$heterocycloalkyl, $C_{3-7}$heterocycloalkyl, $C_{3-6}$heterocycloalkyl, $C_{5-6}$heterocycloalkyl, $C_{3-5}$heterocycloalkyl, and $C_{3-4}$heterocycloalkyl), optionally substituted with one, two, or three $R^{20b}$ that is —OH. In embodiments of a compound of Formula (I), (I'), (Ia), (Ia'), (Ib), (Ib'), (Ic), or (Ic'), or a pharmaceutically acceptable salt or solvate thereof, $R^3$ is $C_{2-9}$heterocycloalkyl (including $C_{6-9}$heterocycloalkyl, $C_{3-7}$heterocycloalkyl, $C_{3-6}$heterocycloalkyl, $C_{5-6}$heterocycloalkyl, $C_{3-5}$heterocycloalkyl, and $C_{3-4}$heterocycloalkyl), optionally substituted with one, two, or three $R^{20b}$ that is oxo. In embodiments of a compound of Formula (I), (I'), (Ia), (Ia'), (Ib), (Ib'), (Ic), or (Ic'), or a pharmaceutically acceptable salt or solvate thereof, $R^3$ is $C_{2-9}$heterocycloalkyl (including $C_{6-9}$heterocycloalkyl, $C_{3-7}$heterocycloalkyl, $C_{3-6}$heterocycloalkyl, $C_{5-6}$heterocycloalkyl, $C_{3-5}$heterocycloalkyl, and $C_{3-4}$heterocycloalkyl), optionally substituted with one, two, or three $R^{20b}$ that is —N($R^{24}$)C(O)$R^{25}$. In embodiments of a compound of Formula (I), (I'), (Ia), (Ia'), (Ib), (Ib'), (Ic), or (Ic'), or a pharmaceutically acceptable salt or solvate thereof, $R^3$ is $C_{2-9}$heterocycloalkyl (including $C_{6-9}$heterocycloalkyl, $C_{3-7}$heterocycloalkyl, $C_{3-6}$heterocycloalkyl, $C_{5-6}$heterocycloalkyl, $C_{3-5}$heterocycloalkyl, and $C_{3-4}$heterocycloalkyl), optionally substituted with one, two, or three $R^{20b}$ that is —NHC(O)$R^{25}$. In embodiments of a compound of Formula (I), (I'), (Ia), (Ia'), (Ib), (Ib'), (Ic), or (Ic'), or a pharmaceutically acceptable salt or solvate thereof, $R^3$ is $C_{2-9}$heterocycloalkyl (including $C_{6-9}$heterocycloalkyl, $C_{3-7}$heterocycloalkyl, $C_{3-6}$heterocycloalkyl, $C_{5-6}$heterocycloalkyl, $C_{3-5}$heterocycloalkyl, and $C_{3-4}$heterocycloalkyl), optionally substituted with one, two, or three $R^{20b}$ that is —NHC(O)$R^{25}$ and $R^{25}$ is $C_{2-9}$heterocycloalkyl optionally substituted with one, two, or three groups independently selected from halogen, $C_{1-6}$alkyl, $C_{1-6}$haloalkyl, $C_{1-6}$alkoxy, $C_{3-7}$cycloalkyl, $C_{2-9}$heterocycloalkyl, $C_{6-10}$aryl, and $C_{1-9}$heteroaryl. In embodiments of a compound of Formula (I), (I'), (Ia), (Ia'), (Ib), (Ib'), (Ic), or (Ic'), or a pharmaceutically acceptable salt or solvate thereof, $R^3$ is $C_{2-9}$heterocycloalkyl (including $C_{6-9}$heterocycloalkyl, $C_{3-7}$heterocycloalkyl, $C_{3-6}$heterocycloalkyl, $C_{5-6}$heterocycloalkyl, $C_{3-5}$heterocycloalkyl, and $C_{3-4}$heterocycloalkyl), optionally substituted with one, two, or three $R^{20b}$ that is —NHC(O)$R^{25}$ and $R^{25}$ is $C_{2-5}$heterocycloalkyl optionally substituted with one $C_{1-6}$alkyl. In embodiments of a compound of Formula (I), (I'), (Ia), (Ia'), (Ib), (Ib'), (Ic), or (Ic'), or a pharmaceutically acceptable salt or solvate thereof, $R^3$ is $C_{2-9}$heterocycloalkyl (including $C_{6-9}$heterocycloalkyl, $C_{3-7}$heterocycloalkyl, $C_{3-6}$heterocycloalkyl, $C_{5-6}$heterocycloalkyl, $C_{3-5}$heterocycloalkyl, and $C_{3-4}$heterocycloalkyl), optionally substituted with one, two, or three $R^{20b}$ that is —C(O)N($R^{22}$)($R^{23}$). In embodiments of a compound of Formula (I), (I'), (Ia), (Ia'), (Ib), (Ib'), (Ic), or (Ic'), or a pharmaceutically acceptable salt or solvate thereof, $R^3$ is $C_{2-9}$heterocycloalkyl (including $C_{6-9}$heterocycloalkyl, $C_{3-7}$heterocycloalkyl, $C_{3-6}$heterocycloalkyl, $C_{5-6}$heterocycloalkyl, $C_{3-5}$heterocycloalkyl, and $C_{3-4}$heterocycloalkyl), optionally substituted with one, two, or three $R^{20b}$ that is —C(O)NH($R^{22}$). In embodiments of a compound of Formula (I), (I'), (Ia), (Ia'), (Ib), (Ib'), (Ic), or (Ic'), or a pharmaceutically acceptable salt or solvate thereof, $R^3$ is $C_{2-9}$heterocycloalkyl (including $C_{6-9}$heterocycloalkyl, $C_{3-7}$heterocycloalkyl, $C_{3-6}$heterocycloalkyl, $C_{5-6}$heterocycloalkyl, $C_{3-5}$heterocycloalkyl, and $C_{3-4}$heterocycloalkyl), optionally substituted with one, two, or three $R^{20b}$ that is —C(O)NH($R^{22}$) and $R^{22}$ is $C_{2-9}$heterocycloalkyl optionally substituted with one, two, or three groups independently selected from halogen and $C_{1-6}$alkyl. In embodiments of a compound of Formula (I), (I'), (Ia), (Ia'), (Ib), (Ib'), (Ic), or (Ic'), or a pharmaceutically acceptable salt or solvate thereof, $R^3$ is $C_{2-9}$heterocycloalkyl (including $C_{6-9}$heterocycloalkyl, $C_{3-7}$heterocycloalkyl, $C_{3-6}$heterocycloalkyl, $C_{5-6}$heterocycloalkyl, $C_{3-5}$heterocycloalkyl, and $C_{3-4}$heterocycloalkyl), optionally substituted with one, two, or three $R^{20b}$ that is —C(O)NH($R^{22}$) and $R^{22}$ is $C_{2-5}$heterocycloalkyl optionally substituted with one $C_{1-6}$alkyl.

In embodiments of a compound of Formula (I), (I'), (Ia), (Ia'), (Ib), (Ib'), (Ic), or (Ic'), or a pharmaceutically acceptable salt or solvate thereof, $R^3$ is thianyl substituted with one, two, or three $R^{20b}$. In embodiments of a compound of Formula (I), (I'), (Ia), (Ia'), (Ib), (Ib'), (Ic), or (Ic'), or a pharmaceutically acceptable salt or solvate thereof, $R^3$ is monovalent tetrahydro-2H-thiopyran 1,1-dioxide substituted with one, two, or three $R^{20b}$. In embodiments of a compound of Formula (I), (I'), (Ia), (Ia'), (Ib), (Ib'), (Ic), or (Ic'), or a pharmaceutically acceptable salt or solvate thereof, $R^3$ is monovalent $4\lambda^2$-thiomorpholine substituted with two $R^{20b}$. In embodiments of a compound of Formula (I), (I'), (Ia), (Ia'), (Ib), (Ib'), (Ic), or (Ic'), or a pharmaceutically acceptable salt or solvate thereof, $R^3$ is tetrahydro-2H-thiopyranyl 1,1-dioxide. In embodiments of a compound of Formula (I), (I'), (Ia), (Ia'), (Ib), (Ib'), (Ic), or (Ic'), or a pharmaceutically acceptable salt or solvate thereof, $R^3$ is $4\lambda^2$-thiomorpholinyl substituted with two $R^{20b}$. In embodiments of a compound of Formula (I), (I'), (Ia), (Ia'), (Ib), (Ib'), (Ic), or (Ic'), or a pharmaceutically acceptable salt or solvate thereof, $R^3$ is piperidinyl substituted with one $R^{20b}$. In embodiments of a compound of Formula (I), (I'), (Ia), (Ia'), (Ib), (Ib'), (Ic), or (Ic'), or a pharmaceutically acceptable salt or solvate thereof, $R^3$ is piperazinyl substituted with one $R^{20b}$. In embodiments of a compound of Formula (I), (I'), (Ia), (Ia'), (Ib), (Ib'), (Ic), or (Ic'), or a pharmaceutically acceptable salt or solvate thereof, $R^3$ is pyrrolidinyl substituted with one $R^{20b}$.

In embodiments of a compound of Formula (I), (I'), (Ia), (Ia'), (Ib), (Ib'), (Ic), or (Ic'), or a pharmaceutically acceptable salt or solvate thereof, $R^3$ is $C_{2-9}$heterocycloalkyl substituted with one methyl. In embodiments of a compound of Formula (I), (I'), (Ia), (Ia'), (Ib), (Ib'), (Ic), or (Ic'), or a pharmaceutically acceptable salt or solvate thereof, $R^3$ is $C_{6-9}$heterocycloalkyl substituted with one methyl, one ethyl, or one propyl. In embodiments of a compound of Formula (I), (I'), (Ia), (Ia'), (Ib), (Ib'), (Ic), or (Ic'), or a pharmaceutically acceptable salt or solvate thereof, $R^3$ is $C_{3-7}$heterocycloalkyl substituted with one methyl, one ethyl, or one propyl. In embodiments of a compound of Formula (I), (I'), (Ia), (Ia'), (Ib), (Ib'), (Ic), or (Ic'), or a pharmaceutically acceptable salt or solvate thereof, $R^3$ is $C_{3-6}$heterocycloalkyl substituted with one methyl, one ethyl, or one propyl. In embodiments of a compound of Formula (I), (I'), (Ia), (Ia'), (Ib), (Ib'), (Ic), or (Ic'), or a pharmaceutically acceptable salt or solvate thereof, $R^3$ is $C_{5-6}$heterocycloalkyl substituted with one methyl, one ethyl, or one propyl. In embodiments of a compound of Formula (I), (I'), (Ia), (Ia'), (Ib), (Ib'), (Ic), or (Ic'), or a pharmaceutically acceptable salt or solvate thereof, $R^3$ is $C_{5-6}$heterocycloalkyl substituted with one methyl, one ethyl, or one propyl. In embodiments of a compound of Formula (I), (I'), (Ia), (Ia'), (Ib), (Ib'), (Ic), or (Ic'), or a pharmaceutically acceptable salt or solvate thereof, $R^3$ is $C_{3-4}$heterocycloalkyl substituted with one methyl, one ethyl, or one propyl. In embodiments of a compound of Formula (I), (I'), (Ia), (Ia'), (Ib), (Ib'), (Ic), or (Ic'), or a pharmaceutically acceptable salt or solvate thereof, $R^3$ is $C_{2-7}$heterocycloalkyl substituted with one methyl, one ethyl, or one propyl. In embodiments of a compound of Formula (I), (I'), (Ia), (Ia'), (Ib), (Ib'), (Ic), or (Ic'), or a pharmaceutically acceptable salt or solvate thereof, $R^3$ is $C_{4-7}$heterocycloalkyl substituted with one methyl, one ethyl, or one propyl. In embodiments of a compound of Formula (I), (I'), (Ia), (Ia'), (Ib), (Ib'), (Ic), or (Ic'), or a pharmaceutically acceptable salt or solvate thereof, $R^3$ is $C_{4-5}$heterocycloalkyl substituted with one methyl, one ethyl, or one propyl. In embodiments of a compound of Formula (I), (I'), (Ia), (Ia'), (Ib), (Ib'), (Ic), or (Ic'), or a pharmaceutically acceptable salt or solvate thereof, $R^3$ is $C_5$heterocycloalkyl substituted with one methyl, one ethyl, or one propyl. In embodiments of a compound of Formula (I), (I'), (Ia), (Ia'), (Ib), (Ib'), (Ic), or (Ic'), or a pharmaceutically acceptable salt or solvate thereof, $R^3$ is $C_4$heterocycloalkyl substituted with one methyl, one ethyl, or one propyl.

In embodiments of a compound of Formula (I), (I'), (Ia), (Ia'), (Ib), (Ib'), (Ic), or (Ic'), or a pharmaceutically acceptable salt or solvate thereof, $R^3$ is $C_{6-9}$heterocycloalkyl substituted with one propyl. In embodiments of a compound of Formula (I), (I'), (Ia), (Ia'), (Ib), (Ib'), (Ic), or (Ic'), or a pharmaceutically acceptable salt or solvate thereof, $R^3$ is $C_{3-7}$heterocycloalkyl substituted with one propyl. In embodiments of a compound of Formula (I), (I'), (Ia), (Ia'), (Ib), (Ib'), (Ic), or (Ic'), or a pharmaceutically acceptable salt or solvate thereof, $R^3$ is $C_{3-6}$heterocycloalkyl substituted with one propyl. In embodiments of a compound of Formula (I), (I'), (Ia), (Ia'), (Ib), (Ib'), (Ic), or (Ic'), or a pharmaceutically acceptable salt or solvate thereof, $R^3$ is $C_{5-6}$ heterocycloalkyl substituted with one propyl. In embodiments of a compound of Formula (I), (I'), (Ia), (Ia'), (Ib), (Ib'), (Ic), or (Ic'), or a pharmaceutically acceptable salt or solvate thereof, $R^3$ is $C_{5-6}$heterocycloalkyl substituted with one propyl. In embodiments of a compound of Formula (I), (I'), (Ia), (Ia'), (Ib), (Ib'), (Ic), or (Ic'), or a pharmaceutically acceptable salt or solvate thereof, $R^3$ is $C_{3-4}$heterocycloalkyl substituted with one propyl. In embodiments of a compound of Formula (I), (I'), (Ia), (Ia'), (Ib), (Ib'), (Ic), or (Ic'), or a pharmaceutically acceptable salt or solvate thereof, $R^3$ is $C_{4-5}$heterocycloalkyl substituted with one propyl. In embodiments of a compound of Formula (I), (I'), (Ia), (Ia'), (Ib), (Ib'), (Ic), or (Ic'), or a pharmaceutically acceptable salt or solvate thereof, $R^3$ is $C_5$heterocycloalkyl substituted with one propyl. In embodiments of a compound of Formula (I), (I'), (Ia), (Ia'), (Ib), (Ib'), (Ic), or (Ic'), or a pharmaceutically acceptable salt or solvate thereof, $R^3$ is $C_4$heterocycloalkyl substituted with one propyl.

In embodiments of a compound of Formula (I), (I'), (Ia), (Ia'), (Ib), (Ib'), (Ic), or (Ic'), or a pharmaceutically acceptable salt or solvate thereof, $R^3$ is $C_{2-9}$heterocycloalkyl substituted with one isopropyl. In embodiments of a compound of Formula (I), (I'), (Ia), (Ia'), (Ib), (Ib'), (Ic), or (Ic'), or a pharmaceutically acceptable salt or solvate thereof, $R^3$ is $C_{2-7}$heterocycloalkyl substituted with one isopropyl. In embodiments of a compound of Formula (I), (I'), (Ia), (Ia'), (Ib), (Ib'), (Ic), or (Ic'), or a pharmaceutically acceptable salt or solvate thereof, $R^3$ is $C_{4-7}$heterocycloalkyl substituted with one isopropyl. In embodiments of a compound of Formula (I), (I'), (Ia), (Ia'), (Ib), (Ib'), (Ic), or (Ic'), or a pharmaceutically acceptable salt or solvate thereof, $R^3$ is $C_{4-5}$heterocycloalkyl substituted with one isopropyl. In embodiments of a compound of Formula (I), (I'), (Ia), (Ia'), (Ib), (Ib'), (Ic), or (Ic'), or a pharmaceutically acceptable salt or solvate thereof, $R^3$ is $C_5$heterocycloalkyl substituted with one isopropyl. In embodiments of a compound of Formula (I), (I'), (Ia), (Ia'), (Ib), (Ib'), (Ic), or (Ic'), or a pharmaceutically acceptable salt or solvate thereof, $R^3$ is $C_4$heterocycloalkyl substituted with one isopropyl.

In embodiments of a compound of Formula (I), (I'), (Ia), (Ia'), (Ib), (Ib'), (Ic), or (Ic'), or a pharmaceutically acceptable salt or solvate thereof, $R^3$ is $C_{2-9}$heterocycloalkyl substituted with two oxo. In embodiments of a compound of Formula (I), (I'), (Ia), (Ia'), (Ib), (Ib'), (Ic), or (Ic'), or a pharmaceutically acceptable salt or solvate thereof, $R^3$ is $C_{2-7}$heterocycloalkyl substituted with two oxo. In embodiments of a compound of Formula (I), (I'), (Ia), (Ia'), (Ib), (Ib'), (Ic), or (Ic'), or a pharmaceutically acceptable salt or solvate thereof, $R^3$ is $C_{4-7}$heterocycloalkyl substituted with two oxo. In embodiments of a compound of Formula (I), (I'), (Ia), (Ia'), (Ib), (Ib'), (Ic), or (Ic'), or a pharmaceutically acceptable salt or solvate thereof, $R^3$ is $C_{6-9}$ heterocycloalkyl substituted with two oxo. In embodiments of a compound of Formula (I), (I'), (Ia), (Ia'), (Ib), (Ib'), (Ic), or (Ic'), or a pharmaceutically acceptable salt or solvate thereof, $R^3$ is $C_{3-7}$heterocycloalkyl substituted with two oxo. In embodiments of a compound of Formula (I), (I'), (Ia), (Ia'), (Ib), (Ib'), (Ic), or (Ic'), or a pharmaceutically acceptable salt or solvate thereof, $R^3$ is $C_{3-6}$heterocycloalkyl substituted with two oxo. In embodiments of a compound of Formula (I), (I'), (Ia), (Ia'), (Ib), (Ib'), (Ic), or (Ic'), or a pharmaceutically acceptable salt or solvate thereof, $R^3$ is $C_{5-6}$heterocycloalkyl substituted with two oxo. In embodiments of a compound of Formula (I), (I'), (Ia), (Ia'), (Ib), (Ib'), (Ic), or (Ic'), or a pharmaceutically acceptable salt or solvate thereof, $R^3$ is $C_{5-6}$ heterocycloalkyl substituted with two oxo. In embodiments of a compound of Formula (I), (I'), (Ia), (Ia'), (Ib), (Ib'), (Ic), or (Ic'), or a pharmaceutically acceptable salt or solvate thereof, $R^3$ is $C_{3-4}$heterocycloalkyl substituted with two oxo. In embodiments of a compound of Formula (I), (I'), (Ia), (Ia'), (Ib), (Ib'), (Ic), or (Ic'), or a pharmaceutically acceptable salt or solvate thereof, $R^3$ is $C_{4-5}$ heterocycloalkyl substituted with two oxo. In embodiments of a compound of Formula (I), (I'), (Ia), (Ia'), (Ib), (Ib'), (Ic), or (Ic'), or a pharmaceutically acceptable salt or solvate thereof, $R^3$ is $C_5$heterocycloalkyl substituted with two oxo. In embodiments of a compound of Formula (I), (I'), (Ia), (Ia'), (Ib), (Ib'), (Ic), or (Ic'), or a pharmaceutically acceptable salt or solvate thereof, $R^3$ is $C_4$heterocycloalkyl substituted with two oxo.

In embodiments of a compound of Formula (I), (I'), (Ia), (Ia'), (Ib), (Ib'), (Ic), or (Ic'), or a pharmaceutically acceptable salt or solvate thereof, $R^3$ is thianyl, optionally substituted with one, two, or three $R^{20b}$ that is amino. In embodiments of a compound of Formula (I), (I'), (Ia), (Ia'), (Ib), (Ib'), (Ic), or (Ic'), or a pharmaceutically acceptable salt or solvate thereof, $R^3$ is thianyl, optionally substituted with one, two, or three $R^{20b}$ that is —CN. In embodiments of a compound of Formula (I), (I'), (Ia), (Ia'), (Ib), (Ib'), (Ic), or (Ic'), or a pharmaceutically acceptable salt or solvate thereof, $R^3$ is thianyl, optionally substituted with one, two, or three $R^{20b}$ that is $C_{1-3}$alkyl. In embodiments of a compound of Formula (I), (I'), (Ia), (Ia'), (Ib), (Ib'), (Ic), or (Ic'), or a pharmaceutically acceptable salt or solvate thereof, $R^3$ is thianyl, optionally substituted with one, two, or three $R^{20b}$ that is $C_{1-3}$alkoxy. In embodiments of a compound of Formula (I), (I'), (Ia), (Ia'), (Ib), (Ib'), (Ic), or (Ic'), or a pharmaceutically acceptable salt or solvate thereof, $R^3$ is thianyl, optionally substituted with one, two, or three $R^{20b}$ that is $C_{1-3}$haloalkyl. In embodiments of a compound of Formula (I), (I'), (Ia), (Ia'), (Ib), (Ib'), (Ic), or (Ic'), or a pharmaceutically acceptable salt or solvate thereof, $R^3$ is thianyl, optionally substituted with one, two, or three $R^{20b}$ that is —OH. In embodiments of a compound of Formula (I), (I'), (Ia), (Ia'), (Ib), (Ib'), (Ic), or (Ic'), or a pharmaceutically acceptable salt or solvate thereof, $R^3$ is thianyl, optionally substituted with one, two, or three $R^{20b}$ that is oxo. In embodiments of a compound of Formula (I), (I'), (Ia), (Ia'), (Ib), (Ib'), (Ic), or (Ic'), or a pharmaceutically acceptable salt or solvate thereof, $R^3$ is thianyl, optionally substituted with one, two, or three $R^{20b}$ that is —N($R^{24}$)C(O)$R^{21}$. In embodiments of a compound of Formula (I), (I'), (Ia), (Ia'), (Ib), (Ib'), (Ic), or (Ic'), or a pharmaceutically acceptable salt or solvate thereof, $R^3$ is thianyl, optionally substituted with one, two, or three $R^{20b}$ that is —NHC(O)$R^{25}$. In embodiments of a compound of Formula (I), (I'), (Ia), (Ia'), (Ib), (Ib'), (Ic), or (Ic'), or a pharmaceutically acceptable salt or solvate thereof, $R^3$ is thianyl, optionally substituted with one, two, or three $R^{20b}$ that is —NHC(O)$R^{21}$ and $R^{25}$ is $C_{2-9}$heterocycloalkyl optionally substituted with one, two, or three groups independently selected from halogen, $C_{1-6}$alkyl, $C_{1-6}$haloalkyl, $C_{1-6}$alkoxy, $C_{3-7}$cycloalkyl, $C_{2-9}$heterocycloalkyl, $C_{6-10}$aryl, and $C_{1-9}$heteroaryl. In embodiments of a compound of Formula (I), (I'), (Ia), (Ia'), (Ib), (Ib'), (Ic), or (Ic'), or a pharmaceutically acceptable salt or solvate thereof, $R^3$ is thianyl, optionally substituted with one, two, or three $R^{20b}$ that is —NHC(O)$R^{25}$ and $R^{25}$ is $C_{2-5}$heterocycloalkyl optionally substituted with one $C_{1-6}$alkyl. In embodiments of a compound of Formula (I), (I'), (Ia), (Ia'), (Ib), (Ib'), (Ic), or (Ic'), or a pharmaceutically acceptable salt or solvate thereof, $R^3$ is thianyl, optionally substituted with one, two, or three $R^{20b}$ that is —C(O)N($R^{22}$)($R^{23}$). In embodiments of a compound of Formula (I), (I'), (Ia), (Ia'), (Ib), (Ib'), (Ic), or (Ic'), or a pharmaceutically acceptable salt or solvate thereof, $R^3$ is thianyl, optionally substituted with one, two, or three $R^{20b}$ that is —C(O)NH($R^{22}$). In embodiments of a compound of Formula (I), (I'), (Ia), (Ia'), (Ib), (Ib'), (Ic), or (Ic'), or a pharmaceutically acceptable salt or solvate thereof, $R^3$ is thianyl, optionally substituted with one, two, or three $R^{20b}$ that is —C(O)NH($R^{22}$) and $R^{22}$ is $C_{2-9}$heterocycloalkyl optionally substituted with one, two, or three groups independently selected from halogen and $C_{1-6}$alkyl. In embodiments of a compound of Formula (I), (I'), (Ia), (Ia'), (Ib), (Ib'), (Ic), or (Ic'), or a pharmaceutically acceptable salt or solvate thereof, $R^3$ is thianyl, optionally substituted with one, two, or three $R^{20b}$ that is —C(O)NH($R^{22}$) and $R^{22}$ is $C_{2-5}$heterocycloalkyl optionally substituted with one $C_{1-6}$alkyl.

In embodiments of a compound of Formula (I), (I'), (Ia), (Ia'), (Ib), (Ib'), (Ic), or (Ic'), or a pharmaceutically acceptable salt or solvate thereof, $R^3$ is monovalent tetrahydro-2H-thiopyran 1,1-dioxide, optionally substituted with one, two, or three $R^{20b}$ that is amino. In embodiments of a compound of Formula (I), (I'), (Ia), (Ia'), (Ib), (Ib'), (Ic), or (Ic'), or a pharmaceutically acceptable salt or solvate thereof, $R^3$ is monovalent tetrahydro-2H-thiopyran 1,1-dioxide, optionally substituted with one, two, or three $R^{20b}$ that is —CN. In embodiments of a compound of Formula (I), (I'), (Ia), (Ia'), (Ib), (Ib'), (Ic), or (Ic'), or a pharmaceutically acceptable salt or solvate thereof, $R^3$ is monovalent tetrahydro-2H-thiopyran 1,1-dioxide, optionally substituted with one, two, or three $R^{20b}$ that is $C_{1-3}$alkyl. In embodiments of a compound of Formula (I), (I'), (Ia), (Ia'), (Ib), (Ib'), (Ic), or (Ic'), or a pharmaceutically acceptable salt or solvate thereof, $R^3$ is monovalent tetrahydro-2H-thiopyran 1,1-dioxide, optionally substituted with one, two, or three $R^{2b}$ that is $C_{1-3}$alkoxy. In embodiments of a compound of Formula (I), (I'), (Ia), (Ia'), (Ib), (Ib'), (Ic), or (Ic'), or a pharmaceutically acceptable salt or solvate thereof, $R^3$ is thianyl, optionally substituted with one, two, or three $R^{20b}$ that is $C_{1-3}$ haloalkyl. In embodiments of a compound of Formula (I), (I'), (Ia), (Ia'), (Ib), (Ib'), (Ic), or (Ic'), or a pharmaceutically acceptable salt or solvate thereof, $R^3$ is monovalent tetrahydro-2H-thiopyran 1,1-dioxide, optionally substituted with one, two, or three $R^{20b}$ that is —OH. In embodiments of a compound of Formula (I), (I'), (Ia), (Ia'), (Ib), (Ib'), (Ic), or (Ic'), or a pharmaceutically acceptable salt or solvate thereof, $R^3$ is monovalent tetrahydro-2H-thiopyran 1,1-dioxide, optionally substituted with one, two, or three $R^{20b}$ that is oxo. In embodiments of a compound of Formula (I), (I'), (Ia), (Ia'), (Ib), (Ib'), (Ic), or (Ic'), or a pharmaceutically acceptable salt or solvate thereof, $R^3$ is monovalent tetrahydro-2H-thiopyran 1,1-dioxide, optionally substituted with one, two, or three $R^{20b}$ that is —N($R^{24}$)C(O)$R^{25}$. In embodiments of a compound of Formula (I), (I'), (Ia), (Ia'), (Ib), (Ib'), (Ic), or (Ic'), or a pharmaceutically acceptable salt or solvate thereof, $R^3$ is monovalent tetrahydro-2H-thiopyran 1,1-dioxide, optionally substituted with one, two, or three $R^{20b}$ that is —NHC(O)$R^{21}$. In embodiments of a compound of Formula (I), (I'), (Ia), (Ia'), (Ib), (Ib'), (Ic), or (Ic'), or a pharmaceutically acceptable salt or solvate thereof, $R^3$ is monovalent tetrahydro-2H-thiopyran 1,1-dioxide, optionally substituted with one, two, or three $R^{20b}$ that is —NHC(O)$R^{25}$ and $R^{25}$ is $C_{2-9}$heterocycloalkyl optionally substituted with one, two, or three groups independently selected from halogen, $C_{1-6}$alkyl, $C_{1-6}$haloalkyl, $C_{1-6}$alkoxy, $C_{3-7}$cycloalkyl, $C_{2-9}$heterocycloalkyl, $C_{6-10}$aryl, and $C_{1-9}$ heteroaryl. In embodiments of a compound of Formula (I), (I'), (Ia), (Ia'), (Ib), (Ib'), (Ic), or (Ic'), or a pharmaceutically acceptable salt or solvate thereof, $R^3$ is monovalent tetrahydro-2H-thiopyran 1,1-dioxide, optionally substituted with one, two, or three $R^{20b}$ that is —NHC(O)$R^{20e}$ and $R^{25}$ is $C_{2-5}$heterocycloalkyl optionally substituted with one $C_{1-6}$alkyl. In embodiments of a compound of Formula (I), (I'), (Ia), (Ia'), (Ib), (Ib'), (Ic), or (Ic'), or a pharmaceutically acceptable salt or solvate thereof, $R^3$ is monovalent tetrahydro-2H-thiopyran 1,1-dioxide, optionally substituted with one, two, or three $R^{20b}$ that is —C(O)N($R^{22}$)($R^{23}$). In embodiments of a compound of Formula (I), (I'), (Ia), (Ia'), (Ib), (Ib'), (Ic), or (Ic'), or a pharmaceutically acceptable salt or solvate thereof, $R^3$ is monovalent tetrahydro-2H-thiopyran 1,1-dioxide, optionally substituted with one, two, or three $R^{20b}$ that is —C(O)NH($R^{22}$). In embodiments of a compound of Formula (I), (I'), (Ia), (Ia'), (Ib), (Ib'), (Ic), or (Ic'), or a pharmaceutically acceptable salt or solvate thereof, $R^3$ is monovalent tetrahydro-2H-thiopyran 1,1-dioxide, optionally substituted with one, two, or three $R^{20b}$ that is —C(O)NH($R^{22}$) and $R^{22}$ is $C_{2-9}$heterocycloalkyl optionally substituted with one, two, or three groups independently selected from halogen and $C_{1-6}$alkyl. In embodiments of a compound of Formula (I), (I'), (Ia), (Ia'), (Ib), (Ib'), (Ic), or (Ic'), or a pharmaceutically acceptable salt or solvate thereof, $R^3$ is monovalent tetrahydro-2H-thiopyran 1,1-dioxide, optionally substituted with one, two, or three $R^{20b}$ that is —C(O)NH($R^{22}$) and $R^{22}$ is $C_{2-5}$heterocycloalkyl optionally substituted with one $C_{1-6}$alkyl.

In embodiments of a compound of Formula (I), (I'), (Ia), (Ia'), (Ib), (Ib'), (Ic), or (Ic'), or a pharmaceutically acceptable salt or solvate thereof, $R^3$ is $4\lambda^2$-thiomorpholinyl, optionally substituted with one, two, or three $R^{20b}$ that is amino. In embodiments of a compound of Formula (I), (I'), (Ia), (Ia'), (Ib), (Ib'), (Ic), or (Ic'), or a pharmaceutically acceptable salt or solvate thereof, $R^3$ is $4\lambda^2$-thiomorpholinyl, optionally substituted with one, two, or three $R^{20b}$ that is —CN. In embodiments of a compound of Formula (I), (I'), (Ia), (Ia'), (Ib), (Ib'), (Ic), or (Ic'), or a pharmaceutically acceptable salt or solvate thereof, $R^3$ is $4\lambda^2$-thiomorpholinyl, optionally substituted with one, two, or three $R^{20b}$ that is $C_{1-3}$alkyl. In embodiments of a compound of Formula (I), (I'), (Ia), (Ia'), (Ib), (Ib'), (Ic), or (Ic'), or a pharmaceutically acceptable salt or solvate thereof, $R^3$ is $4\lambda^2$-thiomorpholinyl, optionally substituted with one, two, or three $R^{20b}$ that is $C_{1-3}$alkoxy. In embodiments of a compound of Formula (I), (I'), (Ia), (Ia'), (Ib), (Ib'), (Ic), or (Ic'), or a pharmaceutically acceptable salt or solvate thereof, $R^3$ is $4\lambda^2$-thiomorpholinyl, optionally substituted with one, two, or three $R^{20b}$ that is $C_{1-3}$haloalkyl. In embodiments of a compound of Formula (I), (I'), (Ia), (Ia'), (Ib), (Ib'), (Ic), or (Ic'), or a pharmaceutically acceptable salt or solvate thereof, $R^3$ is $4\lambda^2$-thiomorpholinyl, optionally substituted with one, two, or three $R^{20b}$ that is —OH. In embodiments of a compound of Formula (I), (I'), (Ia), (Ia'), (Ib), (Ib'), (Ic), or (Ic'), or a pharmaceutically acceptable salt or solvate thereof, $R^3$ is $4\lambda^2$-thiomorpholinyl, optionally substituted with one, two, or three $R^{20b}$ that is oxo. In embodiments of a compound of Formula (I), (I'), (Ia), (Ia'), (Ib), (Ib'), (Ic), or (Ic'), or a pharmaceutically acceptable salt or solvate thereof, $R^3$ is $4\lambda^2$-thiomorpholinyl, optionally substituted with one, two, or three $R^{20b}$ that is —N($R^{24}$)C(O)$R^{25}$. In embodiments of a compound of Formula (I), (I'), (Ia), (Ia'), (Ib), (Ib'), (Ic), or (Ic'), or a pharmaceutically acceptable salt or solvate thereof, $R^3$ is $4\lambda^2$-thiomorpholinyl, optionally substituted with one, two, or three $R^{20b}$ that is —NHC(O)$R^{25}$. In embodiments of a compound of Formula (I), (I'), (Ia), (Ia'), (Ib), (Ib'), (Ic), or (Ic'), or a pharmaceutically acceptable salt or solvate thereof, $R^3$ is $4\lambda^2$-thiomorpholinyl, optionally substituted with one, two, or three $R^{20b}$ that is —NHC(O)$R^{25}$ and $R^{25}$ is $C_{2-9}$heterocycloalkyl optionally substituted with one, two, or three groups independently selected from halogen, $C_{1-6}$alkyl, $C_{1-6}$haloalkyl, $C_{1-6}$alkoxy, $C_{3-7}$cycloalkyl, $C_{2-9}$heterocycloalkyl, $C_{6-10}$aryl, and $C_{1-9}$heteroaryl. In embodiments of a compound of Formula (I), (I'), (Ia), (Ia'), (Ib), (Ib'), (Ic), or (Ic'), or a pharmaceutically acceptable salt or solvate thereof, $R^3$ is $4\lambda^2$-thiomorpholinyl, optionally substituted with one, two, or three $R^{20b}$ that is —NHC(O)$R^{25}$ and $R^{25}$ is $C_{2-5}$heterocycloalkyl optionally substituted with one $C_{1-6}$alkyl. In embodiments of a compound of Formula (I), (I'), (Ia), (Ia'), (Ib), (Ib'), (Ic), or (Ic'), or a pharmaceutically acceptable salt or solvate thereof, $R^3$ is $4\lambda^2$-thiomorpholinyl, optionally substituted with one, two, or three $R^{20b}$ that is —C(O)N($R^{22}$)($R^{23}$). In embodiments of a compound of Formula (I), (I'), (Ia), (Ia'), (Ib), (Ib'), (Ic), or (Ic'), or a pharmaceutically acceptable salt or solvate thereof, $R^3$ is $4\lambda^2$-thiomorpholinyl, optionally substituted with one, two, or three $R^{20b}$ that is —C(O)NH($R^{22}$). In embodiments of a compound of Formula (I), (I'), (Ia), (Ia'), (Ib), (Ib'), (Ic), or (Ic'), or a pharmaceutically acceptable salt or solvate thereof, $R^3$ is $4\lambda^2$-thiomorpholinyl, optionally substituted with one, two, or three $R^{20b}$ that is —C(O)NH($R^{22}$) and $R^{22}$ is $C_{2-9}$heterocycloalkyl optionally substituted with one, two, or three groups independently selected from halogen and $C_{1-6}$alkyl. In embodiments of a compound of Formula (I), (I'), (Ia), (Ia'), (Ib), (Ib'), (Ic), or (Ic'), or a pharmaceutically acceptable salt or solvate thereof, $R^3$ is $4\lambda^2$-thiomorpholinyl, optionally substituted with one, two, or three $R^{20b}$ that is —C(O)NH($R^{22}$) and $R^{22}$ is $C_{2-5}$heterocycloalkyl optionally substituted with one $C_{1-6}$alkyl.

In embodiments of a compound of Formula (I), (I'), (Ia), (Ia'), (Ib), (Ib'), (Ic), or (Ic'), or a pharmaceutically acceptable salt or solvate thereof, $R^3$ is piperidinyl, optionally substituted with one, two, or three $R^{20b}$ that is amino. In embodiments of a compound of Formula (I), (I'), (Ia), (Ia'), (Ib), (Ib'), (Ic), or (Ic'), or a pharmaceutically acceptable salt or solvate thereof, $R^3$ is piperidinyl, optionally substituted with one, two, or three $R^{20b}$ that is —CN. In embodiments of a compound of Formula (I), (I'), (Ia), (Ia'), (Ib), (Ib'), (Ic), or (Ic'), or a pharmaceutically acceptable salt or solvate thereof, $R^3$ is piperidinyl, optionally substituted with one, two, or three $R^{20b}$ that is $C_{1-3}$alkyl. In embodiments of a compound of Formula (I), (I'), (Ia), (Ia'), (Ib), (Ib'), (Ic), or (Ic'), or a pharmaceutically acceptable salt or solvate thereof, $R^3$ is piperidinyl, optionally substituted with one, two, or three $R^{20b}$ that is $C_{1-3}$alkoxy. In embodiments of a compound of Formula (I), (I'), (Ia), (Ia'), (Ib), (Ib'), (Ic), or (Ic'), or a pharmaceutically acceptable salt or solvate thereof, $R^3$ is piperidinyl, optionally substituted with one, two, or three $R^{20b}$ that is $C_{1-3}$haloalkyl. In embodiments of a compound of Formula (I), (I'), (Ia), (Ia'), (Ib), (Ib'), (Ic), or (Ic'), or a pharmaceutically acceptable salt or solvate thereof, $R^3$ is piperidinyl, optionally substituted with one, two, or three $R^{20b}$ that is —OH. In embodiments of a compound of Formula (I), (I'), (Ia), (Ia'), (Ib), (Ib'), (Ic), or (Ic'), or a pharmaceutically acceptable salt or solvate thereof, $R^3$ is piperidinyl, optionally substituted with one, two, or three $R^{20b}$ that is oxo. In embodiments of a compound of Formula (I), (I'), (Ia), (Ia'), (Ib), (Ib'), (Ic), or (Ic'), or a pharmaceutically acceptable salt or solvate thereof, $R^3$ is piperidinyl, optionally substituted with one, two, or three $R^{20b}$ that is —N($R^{24}$)C(O)$R^{25}$. In embodiments of a compound of Formula (I), (I'), (Ia), (Ia'), (Ib), (Ib'), (Ic), or (Ic'), or a pharmaceutically acceptable salt or solvate thereof, $R^3$ is piperidinyl, optionally substituted with one, two, or three $R^{20b}$ that is —NHC(O)$R^{25}$. In embodiments of a compound of Formula (I), (I'), (Ia), (Ia'), (Ib), (Ib'), (Ic), or (Ic'), or a pharmaceutically acceptable salt or solvate thereof, $R^3$ is piperidinyl, optionally substituted with one, two, or three $R^{20b}$ that is —NHC(O)$R^{25}$ and $R^{25}$ is $C_{2-9}$heterocycloalkyl optionally substituted with one, two, or three groups independently selected from halogen, $C_{1-6}$alkyl, $C_{1-6}$haloalkyl, $C_{1-6}$alkoxy, $C_{3-7}$cycloalkyl, $C_{2-9}$heterocycloalkyl, $C_{6-10}$aryl, and $C_{1-9}$heteroaryl. In embodiments of a compound of Formula (I), (I'), (Ia), (Ia'), (Ib), (Ib'), (Ic), or (Ic'), or a pharmaceutically acceptable salt or solvate thereof, $R^3$ is piperidinyl, optionally substituted with one, two, or three $R^{20b}$ that is —NHC(O)$R^{21}$ and $R^{25}$ is $C_{2-5}$heterocycloalkyl optionally substituted with one $C_{1-6}$alkyl. In embodiments of a compound of Formula (I), (I'), (Ia), (Ia'), (Ib), (Ib'), (Ic), or (Ic'), or a pharmaceutically acceptable salt or solvate thereof, $R^3$ is piperidinyl, optionally substituted with one, two, or three $R^{20b}$ that is —C(O)N($R^{22}$)($R^{23}$). In embodiments of a compound of Formula (I), (I'), (Ia), (Ia'), (Ib), (Ib'), (Ic), or (Ic'), or a pharmaceutically acceptable salt or solvate thereof, $R^3$ is piperidinyl, optionally substituted with one, two, or three $R^{20b}$ that is —C(O)NH($R^{22}$). In embodiments of a compound of Formula (I), (I'), (Ia), (Ia'), (Ib), (Ib'), (Ic), or (Ic'), or a pharmaceutically acceptable salt or solvate thereof, $R^3$ is piperidinyl, optionally substituted with one, two, or three $R^{20b}$ that is —C(O)NH($R^{22}$) and $R^{22}$ is $C_{2-9}$heterocycloalkyl optionally substituted with one, two, or three groups independently selected from halogen and $C_{1-6}$alkyl. In embodiments of a compound of Formula (I), (I'), (Ia), (Ia'), (Ib), (Ib'), (Ic), or (Ic'), or a pharmaceutically acceptable salt or solvate thereof, $R^3$ is piperidinyl, optionally substituted with one, two, or three $R^{20b}$ that is —C(O)NH($R^{22}$) and $R^{22}$ is $C_{2-5}$heterocycloalkyl optionally substituted with one $C_{1-6}$alkyl.

In embodiments of a compound of Formula (I), (I'), (Ia), (Ia'), (Ib), (Ib'), (Ic), or (Ic'), or a pharmaceutically acceptable salt or solvate thereof, $R^3$ is piperazinyl, optionally substituted with one, two, or three $R^{20b}$ that is amino. In embodiments of a compound of Formula (I), (I'), (Ia), (Ia'), (Ib), (Ib'), (Ic), or (Ic'), or a pharmaceutically acceptable salt or solvate thereof, $R^3$ is piperazinyl, optionally substituted with one, two, or three $R^{20b}$ that is —CN. In embodiments of a compound of Formula (I), (I'), (Ia), (Ia'), (Ib), (Ib'), (Ic), or (Ic'), or a pharmaceutically acceptable salt or solvate thereof, $R^3$ is piperazinyl, optionally substituted with one, two, or three $R^{20b}$ that is $C_{1-3}$alkyl. In embodiments of a compound of Formula (I), (I'), (Ia), (Ia'), (Ib), (Ib'), (Ic), or (Ic'), or a pharmaceutically acceptable salt or solvate thereof, $R^3$ is piperazinyl, optionally substituted with one, two, or three $R^{20b}$ that is $C_{1-3}$alkoxy. In embodiments of a compound of Formula (I), (I'), (Ia), (Ia'), (Ib), (Ib'), (Ic), or (Ic'), or a pharmaceutically acceptable salt or solvate thereof, $R^3$ is piperazinyl, optionally substituted with one, two, or three $R^{20b}$ that is $C_{1-3}$haloalkyl. In embodiments of a compound of Formula (I), (I'), (Ia), (Ia'), (Ib), (Ib'), (Ic), or (Ic'), or a pharmaceutically acceptable salt or solvate thereof, $R^3$ is piperazinyl, optionally substituted with one, two, or three $R^{20b}$ that is —OH. In embodiments of a compound of Formula (I), (I'), (Ia), (Ia'), (Ib), (Ib'), (Ic), or (Ic'), or a pharmaceutically acceptable salt or solvate thereof, $R^3$ is piperazinyl, optionally substituted with one, two, or three $R^{20b}$ that is oxo. In embodiments of a compound of Formula (I), (I'), (Ia), (Ia'), (Ib), (Ib'), (Ic), or (Ic'), or a pharmaceutically acceptable salt or solvate thereof, $R^3$ is piperazinyl, optionally substituted with one, two, or three $R^{20b}$ that is —N($R^{24}$)C(O)$R^{25}$. In embodiments of a compound of Formula (I), (I'), (Ia), (Ia'), (Ib), (Ib'), (Ic), or (Ic'), or a pharmaceutically acceptable salt or solvate thereof, $R^3$ is piperazinyl, optionally substituted with one, two, or three $R^{20b}$ that is —NHC(O)$R^{25}$. In embodiments of a compound of Formula (I), (I'), (Ia), (Ia'), (Ib), (Ib'), (Ic), or (Ic'), or a pharmaceutically acceptable salt or solvate thereof, $R^3$ is piperazinyl, optionally substituted with one, two, or three $R^{20b}$ that is —NHC(O)$R^{25}$ and $R^{25}$ is $C_{2-9}$heterocycloalkyl optionally substituted with one, two, or three groups independently selected from halogen, $C_{1-6}$alkyl, $C_{1-6}$haloalkyl, $C_{1-6}$alkoxy, $C_{3-7}$cycloalkyl, $C_{2-9}$heterocycloalkyl, $C_{6-10}$aryl, and $C_{1-9}$heteroaryl. In embodiments of a compound of Formula (I), (I'), (Ia), (Ia'), (Ib), (Ib'), (Ic), or (Ic'), or a pharmaceutically acceptable salt or solvate thereof, $R^3$ is piperazinyl, optionally substituted with one, two, or three $R^{20b}$ that is —NHC(O)$R^{25}$ and $R^{25}$ is $C_{2-5}$heterocycloalkyl optionally substituted with one $C_{1-6}$alkyl. In embodiments of a compound of Formula (I), (I'), (Ia), (Ia'), (Ib), (Ib'), (Ic), or (Ic'), or a pharmaceutically acceptable salt or solvate thereof, $R^3$ is piperazinyl, optionally substituted with one, two, or three $R^{20b}$ that is —C(O)N($R^{22}$)($R^{23}$). In embodiments of a compound of Formula (I), (I'), (Ia), (Ia'), (Ib), (Ib'), (Ic), or (Ic'), or a pharmaceutically acceptable salt or solvate thereof, $R^3$ is piperazinyl, optionally substituted with one, two, or three $R^{20b}$ that is —C(O)NH($R^{22}$). In embodiments of a compound of Formula (I), (I'), (Ia), (Ia'), (Ib), (Ib'), (Ic), or (Ic'), or a pharmaceutically acceptable salt or solvate thereof, $R^3$ is piperazinyl, optionally substituted with one, two, or three $R^{20b}$ that is —C(O)NH($R^{22}$) and $R^{22}$ is $C_{2-9}$heterocycloalkyl optionally substituted with one, two, or three groups independently selected from halogen and $C_{1-6}$alkyl. In embodiments of a compound of Formula (I), (I'), (Ia), (Ia'), (Ib), (Ib'), (Ic), or (Ic'), or a pharmaceutically acceptable salt or solvate thereof, $R^3$ is piperazinyl, optionally substituted with one, two, or three $R^{20b}$ that is —C(O)NH($R^{22}$) and $R^{22}$ is $C_{2-5}$heterocycloalkyl optionally substituted with one $C_{1-6}$alkyl.

In embodiments of a compound of Formula (I), (I'), (Ia), (Ia'), (Ib), (Ib'), (Ic), or (Ic'), or a pharmaceutically acceptable salt or solvate thereof, $R^3$ is pyrrolidinyl, optionally substituted with one, two, or three $R^{20b}$ that is amino. In embodiments of a compound of Formula (I), (I'), (Ia), (Ia'), (Ib), (Ib'), (Ic), or (Ic'), or a pharmaceutically acceptable salt or solvate thereof, $R^3$ is pyrrolidinyl, optionally substituted with one, two, or three $R^{20b}$ that is —CN. In embodiments of a compound of Formula (I), (I'), (Ia), (Ia'), (Ib), (Ib'), (Ic), or (Ic'), or a pharmaceutically acceptable salt or solvate thereof, $R^3$ is pyrrolidinyl, optionally substituted with one, two, or three $R^{20b}$ that is $C_{1-3}$alkyl. In embodiments of a compound of Formula (I), (I'), (Ia), (Ia'), (Ib), (Ib'), (Ic), or (Ic'), or a pharmaceutically acceptable salt or solvate thereof, $R^3$ is pyrrolidinyl, optionally substituted with one, two, or three $R^{20b}$ that is $C_{1-3}$alkoxy. In embodiments of a compound of Formula (I), (I'), (Ia), (Ia'), (Ib), (Ib'), (Ic), or (Ic'), or a pharmaceutically acceptable salt or solvate thereof, $R^3$ is pyrrolidinyl, optionally substituted with one, two, or three $R^{20b}$ that is $C_{1-3}$haloalkyl. In embodiments of a compound of Formula (I), (I'), (Ia), (Ia'), (Ib), (Ib'), (Ic), or (Ic'), or a pharmaceutically acceptable salt or solvate thereof, $R^3$ is pyrrolidinyl, optionally substituted with one, two, or three $R^{20b}$ that is —OH. In embodiments of a compound of Formula (I), (I'), (Ia), (Ia'), (Ib), (Ib'), (Ic), or (Ic'), or a pharmaceutically acceptable salt or solvate thereof, $R^3$ is pyrrolidinyl, optionally substituted with one, two, or three $R^{20b}$ that is oxo. In embodiments of a compound of Formula (I), (I'), (Ia), (Ia'), (Ib), (Ib'), (Ic), or (Ic'), or a pharmaceutically acceptable salt or solvate thereof, $R^3$ is pyrrolidinyl, optionally substituted with one, two, or three $R^{20b}$ that is —N($R^{24}$)C(O)$R^{25}$. In embodiments of a compound of Formula (I), (I'), (Ia), (Ia'), (Ib), (Ib'), (Ic), or (Ic'), or a pharmaceutically acceptable salt or solvate thereof, $R^3$ is pyrrolidinyl, optionally substituted with one, two, or three $R^{20b}$ that is —NHC(O)$R^{25}$. In embodiments of a compound of Formula (I), (I'), (Ia), (Ia'), (Ib), (Ib'), (Ic), or (Ic'), or a pharmaceutically acceptable salt or solvate thereof, $R^3$ is pyrrolidinyl, optionally substituted with one, two, or three $R^{20b}$ that is —NHC(O)$R^{25}$ and $R^{25}$ is $C_{2-9}$heterocycloalkyl optionally substituted with one, two, or three groups independently selected from halogen, $C_{1-6}$alkyl, $C_{1-6}$haloalkyl, $C_{1-6}$alkoxy, $C_{3-7}$cycloalkyl, $C_{2-9}$heterocycloalkyl, $C_{6-10}$aryl, and $C_{1-9}$heteroaryl. In embodiments of a compound of Formula (I), (I'), (Ia), (Ia'), (Ib), (Ib'), (Ic), or (Ic'), or a pharmaceutically acceptable salt or solvate thereof, $R^3$ is pyrrolidinyl, optionally substituted with one, two, or three $R^{20b}$ that is —NHC(O)$R^{25}$ and $R^{25}$ is $C_{2-5}$heterocycloalkyl optionally substituted with one $C_{1-6}$alkyl. In embodiments of a compound of Formula (I), (I'), (Ia), (Ia'), (Ib), (Ib'), (Ic), or (Ic'), or a pharmaceutically acceptable salt or solvate thereof, $R^3$ is pyrrolidinyl, optionally substituted with one, two, or three $R^{20b}$ that is —C(O)N($R^{22}$)($R^{23}$). In embodiments of a compound of Formula (I), (I'), (Ia), (Ia'), (Ib), (Ib'), (Ic), or (Ic'), or a pharmaceutically acceptable salt or solvate thereof, $R^3$ is pyrrolidinyl, optionally substituted with one, two, or three $R^{20b}$ that is —C(O)NH($R^{22}$). In embodiments of a compound of Formula (I), (I'), (Ia), (Ia'), (Ib), (Ib'), (Ic), or (Ic'), or a pharmaceutically acceptable salt or solvate thereof, $R^3$ is pyrrolidinyl, optionally substituted with one, two, or three $R^{20b}$ that is —C(O)NH($R^{22}$) and $R^{22}$ is $C_{2-9}$heterocycloalkyl optionally substituted with one, two, or three groups independently selected from halogen and $C_{1-6}$alkyl. In embodiments of a compound of Formula (I), (I'), (Ia), (Ia'), (Ib), (Ib'), (Ic), or (Ic'), or a pharmaceutically acceptable salt or solvate thereof, $R^3$ is pyrrolidinyl, optionally substituted with one, two, or three $R^{20b}$ that is —C(O)NH($R^{22}$) and $R^{22}$ is $C_{2-5}$heterocycloalkyl optionally substituted with one $C_{1-6}$alkyl.

In some embodiments is a compound of Formula (I), (I'), (Ia), (Ia'), (Ib), (Ib'), (Ic), or (Ic'), or a pharmaceutically acceptable salt or solvate thereof, wherein $R^3$ is cyclopropyl optionally substituted with one, two, or three $R^{20b}$. In some embodiments is a compound of Formula (I), (I'), (Ia), (Ia'), (Ib), (Ib'), (Ic), or (Ic'), or a pharmaceutically acceptable salt or solvate thereof, wherein $R^3$ is cyclobutyl optionally substituted with one, two, or three $R^{20b}$. In some embodiments is a compound of Formula (I), (I'), (Ia), (Ia'), (Ib), (Ib'), (Ic), or (Ic'), or a pharmaceutically acceptable salt or solvate thereof, wherein $R^3$ is cyclopentyl optionally substituted with one, two, or three $R^{20b}$. In some embodiments is a compound of Formula (I), (I'), (Ia), (Ia'), (Ib), (Ib'), (Ic), or (Ic'), or a pharmaceutically acceptable salt or solvate thereof, wherein $R^3$ is cyclohexyl optionally substituted with one, two, or three $R^{20b}$. In some embodiments is a compound of Formula (I), (I'), (Ia), (Ia'), (Ib), (Ib'), (Ic), or (Ic'), or a pharmaceutically acceptable salt or solvate thereof, wherein $R^3$ is aziridinyl optionally substituted with one, two, or three $R^{20b}$. In some embodiments is a compound of Formula (I), (I'), (Ia), (Ia'), (Ib), (Ib'), (Ic), or (Ic'), or a pharmaceutically acceptable salt or solvate thereof, wherein $R^3$ is azetidinyl optionally substituted with one, two, or three $R^{20b}$. In some embodiments is a compound of Formula (I), (I'), (Ia), (Ia'), (Ib), (Ib'), (Ic), or (Ic'), or a pharmaceutically acceptable salt or solvate thereof, wherein $R^3$ is pyrrolidinyl optionally substituted with one, two, or three $R^{20b}$. In some embodiments is a compound of Formula (I), (I'), (Ia), (Ia'), (Ib), (Ib'), (Ic), or (Ic'), or a pharmaceutically acceptable salt or solvate thereof, wherein $R^3$ is piperidinyl optionally substituted with one, two, or three $R^{20b}$. In some embodiments is a compound of Formula (I), (I'), (Ia), (Ia'), (Ib), (Ib'), (Ic), or (Ic'), or a pharmaceutically acceptable salt or solvate thereof, wherein $R^3$ is piperizinyl optionally substituted with one, two, or three $R^{20b}$. In some embodiments is a compound of Formula (I), (I'), (Ia), (Ia'), (Ib), (Ib'), (Ic), or (Ic'), or a pharmaceutically acceptable salt or solvate thereof, wherein $R^3$ is morpholinyl optionally substituted with one, two, or three $R^{20b}$. In some embodiments is a compound of Formula (I), (I'), (Ia), (Ia'), (Ib), (Ib'), (Ic), or (Ic'), or a pharmaceutically acceptable salt or solvate thereof, wherein $R^3$ is oxetanyl optionally substituted with one, two, or three $R^{20b}$. In some embodiments is a compound of Formula (I), (I'), (Ia), (Ia'), (Ib), (Ib'), (Ic), or (Ic'), or a pharmaceutically acceptable salt or solvate thereof, wherein $R^3$ is tetrahydrofuranyl optionally substituted with one, two, or three $R^{20b}$. In some embodiments is a compound of Formula (I), (I'), (Ia), (Ia'), (Ib), (Ib'), (Ic), or (Ic'), or a pharmaceutically acceptable salt or solvate thereof, wherein $R^3$ is tetrahydropyranyl optionally substituted with one, two, or three $R^{20b}$. In some embodiments is a compound of Formula (I), (I'), (Ia), (Ia'), (Ib), (Ib'), (Ic), or (Ic'), or a pharmaceutically acceptable salt or solvate thereof, wherein $R^3$ is pyridinyl optionally substituted with one, two, or three $R^{20b}$. In some embodiments is a compound of Formula (I), (I'), (Ia), (Ia'), (Ib), (Ib'), (Ic), or (Ic'), or a pharmaceutically acceptable salt or solvate thereof, wherein $R^3$ is pyrazinyl optionally substituted with one, two, or three $R^{20b}$. In some embodiments is a compound of Formula (I), (I'), (Ia), (Ia'), (Ib), (Ib'), (Ic), or (Ic'), or a pharmaceutically acceptable salt or solvate thereof, wherein $R^3$ is pyrimidinyl optionally substituted with one, two, or three $R^{20b}$. In some embodiments is a compound of Formula (I), (I'), (Ia), (Ia'), (Ib), (Ib'), (Ic), or (Ic'), or a pharmaceutically acceptable salt or solvate thereof, wherein $R^3$ is pyridazinyl optionally substituted with one, two, or three $R^{20b}$. In some embodiments is a compound of Formula (I), (I'), (Ia), (Ia'), (Ib), (Ib'), (Ic), or (Ic'), or a pharmaceutically acceptable salt or solvate thereof, wherein $R^3$ is phenyl optionally substituted with one, two, or three $R^{20b}$. In some embodiments is a compound of Formula (I), (I'), (Ia), (Ia'), (Ib), (Ib'), (Ic), or (Ic'), or a pharmaceutically acceptable salt or solvate thereof, wherein $R^3$ is pyrazolyl optionally substituted with one, two, or three $R^{20b}$. In some embodiments is a compound of Formula (I), (I'), (Ia), (Ia'), (Ib), (Ib'), (Ic), or (Ic'), or a pharmaceutically acceptable salt or solvate thereof, wherein $R^3$ is pyrrolyl optionally substituted with one, two, or three $R^{20b}$. In some embodiments is a compound of Formula (I), (I'), (Ia), (Ia'), (Ib), (Ib'), (Ic), or (Ic'), or a pharmaceutically acceptable salt or solvate thereof, wherein $R^3$ is thiophenyl optionally substituted with one, two, or three $R^{20b}$. In some embodiments is a compound of Formula (I), (I'), (Ia), (Ia'), (Ib), (Ib'), (Ic), or (Ic'), or a pharmaceutically acceptable salt or solvate thereof, wherein $R^3$ is thianyl optionally substituted with one, two, or three $R^{20b}$. In some embodiments is a compound of Formula (I), (I'), (Ia), (Ia'), (Ib), (Ib'), (Ic), or (Ic'), or a pharmaceutically acceptable salt or solvate thereof, wherein $R^3$ is 1,3-imidazolyl optionally substituted with one, two, or three $R^{20b}$. In some embodiments is a compound of Formula (I), (I'), (Ia), (Ia'), (Ib), (Ib'), (Ic), or (Ic'), or a pharmaceutically acceptable salt or solvate thereof, wherein $R^3$ is thiazolyl optionally substituted with one, two, or three $R^{20b}$. In some embodiments is a compound of Formula (I), (I'), (Ia), (Ia'), (Ib), (Ib'), (Ic), or (Ic'), or a pharmaceutically acceptable salt or solvate thereof, wherein $R^3$ is oxepanyl optionally substituted with one, two, or three $R^{20b}$. In some embodiments is a compound of Formula (I), (I'), (Ia), (Ia'), (Ib), (Ib'), (Ic), or (Ic'), or a pharmaceutically acceptable salt or solvate thereof, wherein $R^3$ is azepanyl optionally substituted with one, two, or three $R^{20b}$. In some embodiments is a compound of Formula (I), (I'), (Ia), (Ia'), (Ib), (Ib'), (Ic), or (Ic'), or a pharmaceutically acceptable salt or solvate thereof, wherein $R^3$ is 1,4-dioxapanyl optionally substituted with one, two, or three $R^{20b}$. In some embodiments is a compound of Formula (I), (I'), (Ia), (Ia'), (Ib), (Ib'), (Ic), or (Ic'), or a pharmaceutically acceptable salt or solvate thereof, wherein $R^3$ is 1,4-oxazepanyl optionally substituted with one, two, or three $R^{20b}$. In some embodiments is a compound of Formula (I), (I'), (Ia), (Ia'), (Ib), (Ib'), (Ic), or (Ic'), or a pharmaceutically acceptable salt or solvate thereof, wherein $R^3$ is 2,6-diazaspiro[3.3]heptanyl optionally substituted with one, two, or three $R^{20b}$. In some embodiments is a compound of Formula (I), (I'), (Ia), (Ia'), (Ib), (Ib'), (Ic), or (Ic'), or a pharmaceutically acceptable salt or solvate thereof, wherein $R^3$ is 2-oxa-6-azaspiro[3.3]heptanyl optionally substituted with one, two, or three $R^{20b}$.

In some embodiments is a compound of Formula (I), (I'), (Ia), (Ia'), (Ib), (Ib'), (Ic), or (Ic'), or a pharmaceutically acceptable salt or solvate thereof, wherein $R^3$ is

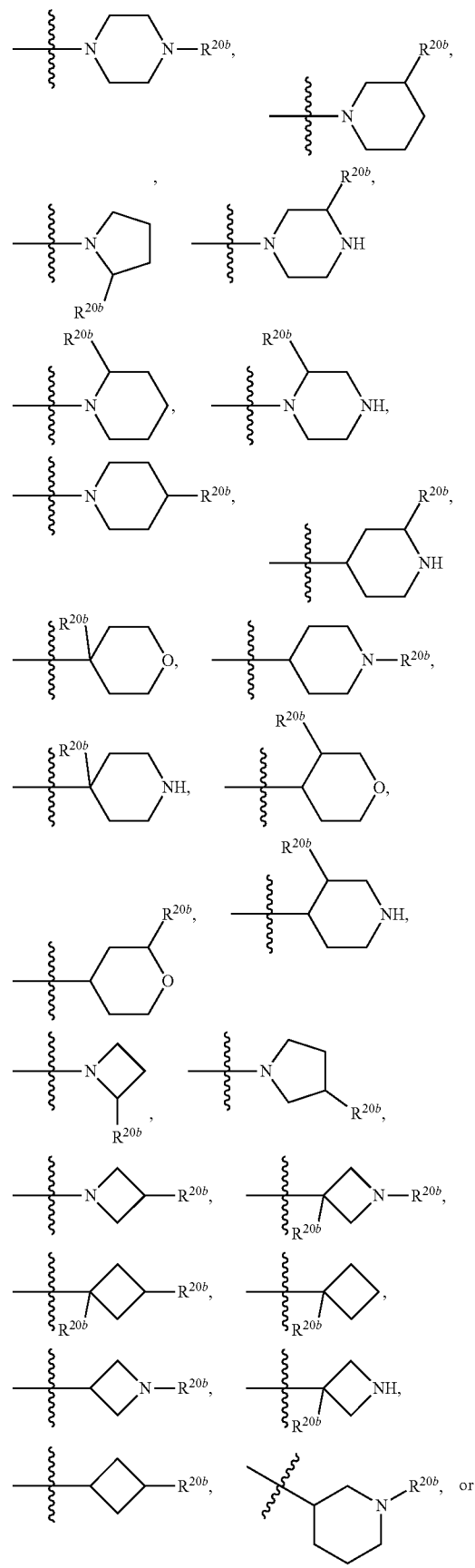

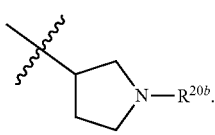
In some embodiments is a compound of Formula (I), (I'), (Ia), (Ia'), (Ib), (Ib'), (Ic), or (Ic'), or a pharmaceutically acceptable salt or solvate thereof, wherein $R^3$ is
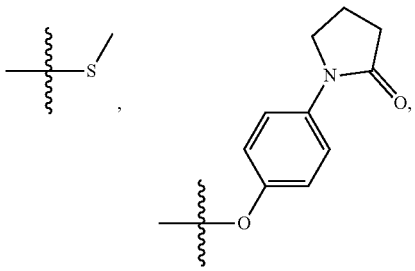
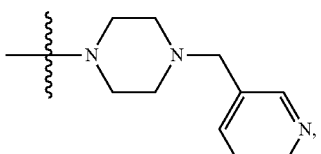
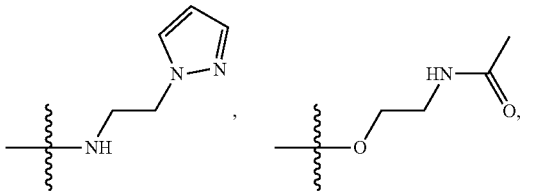
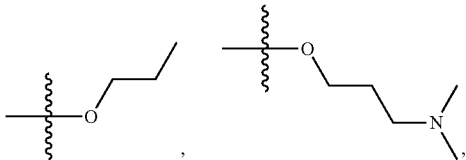
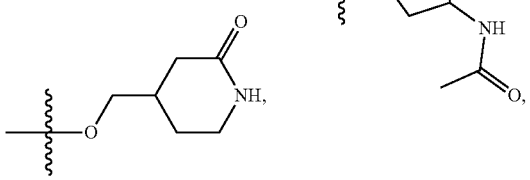
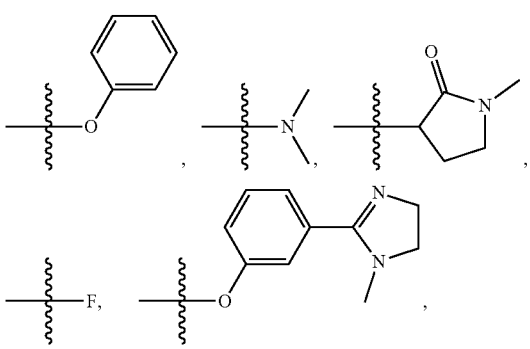
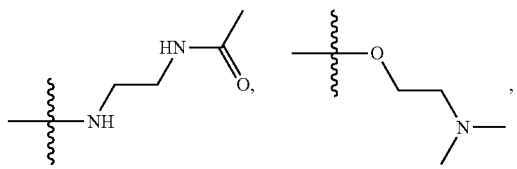
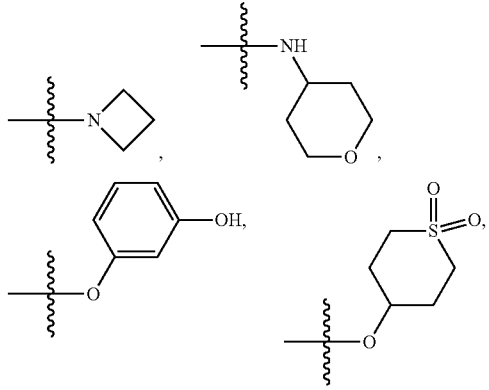
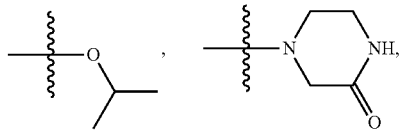
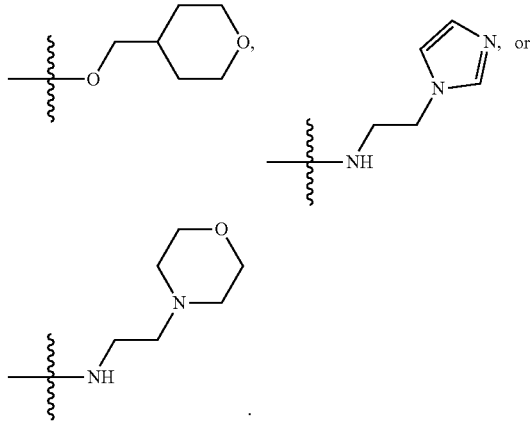
In some embodiments is a compound of Formula (I), (I'), (Ia) (Ia'), (Ib), (Ib'), (Ic), or (Ic'), or a pharmaceutically acceptable salt or solvate thereof, wherein $R^3$ is
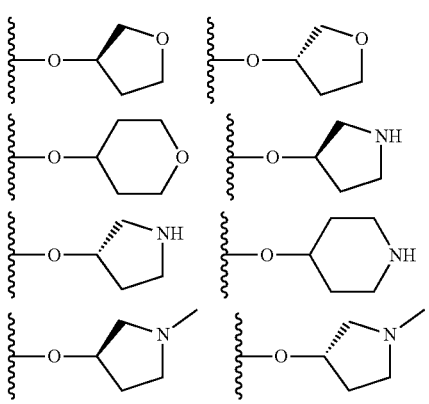

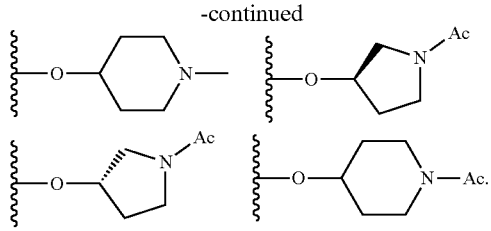
In some embodiments is a compound of Formula (I), (I'), (Ia), (Ia'), (Ib), (Ib'), (Ic), or (Ic'), or a pharmaceutically acceptable salt or solvate thereof, wherein $R^3$ is
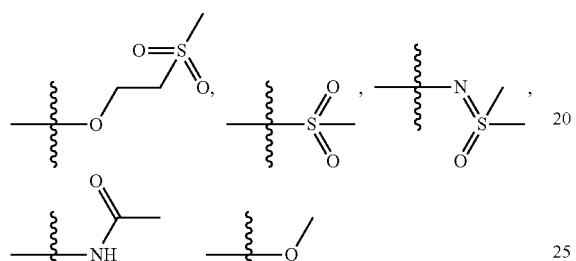
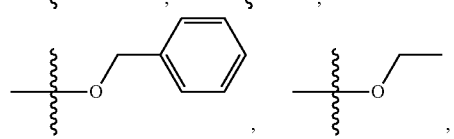
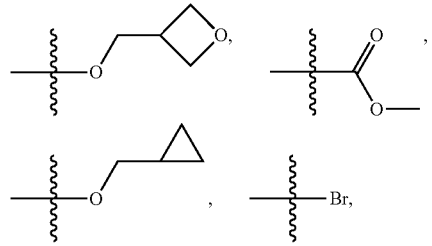
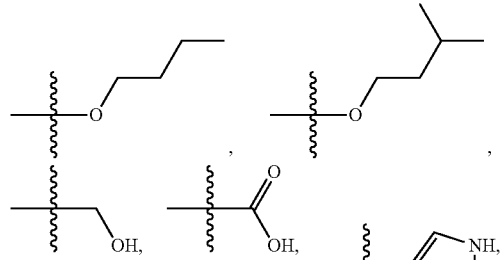
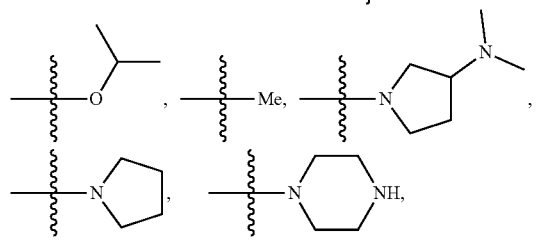
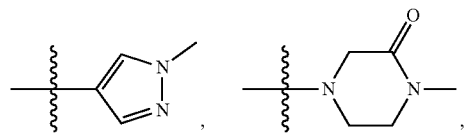
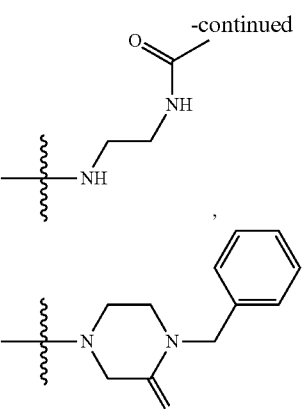
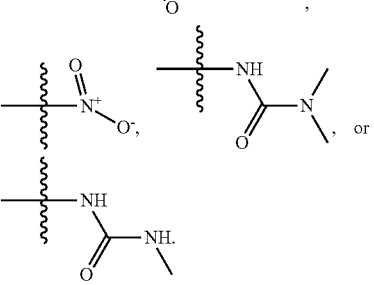
In some embodiments is a compound of Formula (I), (I'), (Ia), (Ia'), (Ib), (Ib'), (Ic), or (Ic'), or a pharmaceutically acceptable salt or solvate thereof, wherein $R^3$ is
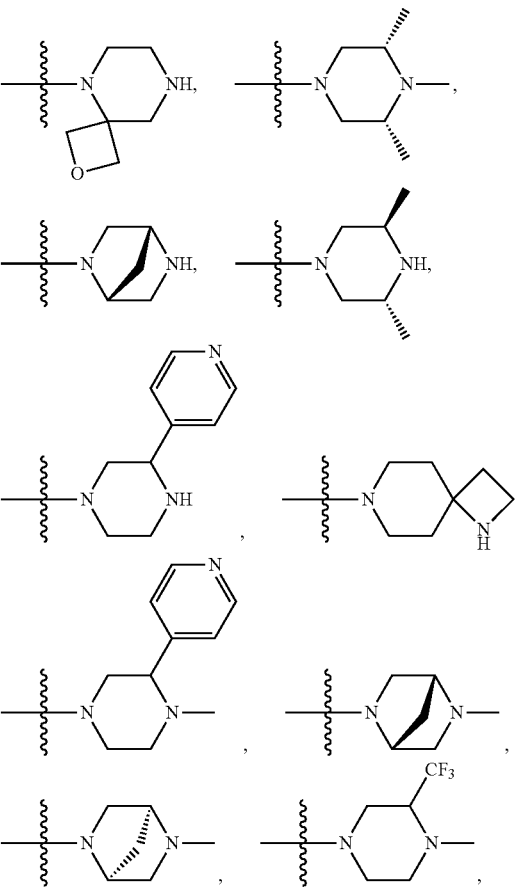

-continued
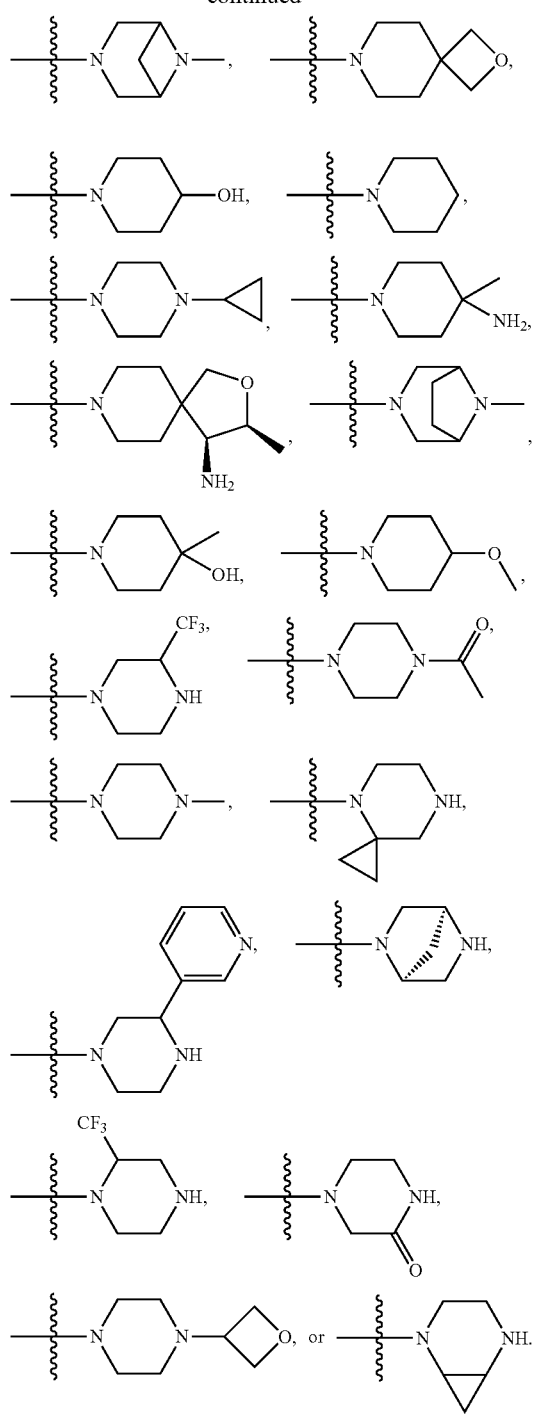
In some embodiments is a compound of Formula (I), (I'), (Ia), (Ia'), (Ib), (Ib'), (Ic), or (Ic'), or a pharmaceutically acceptable salt or solvate thereof, wherein $R^3$ is
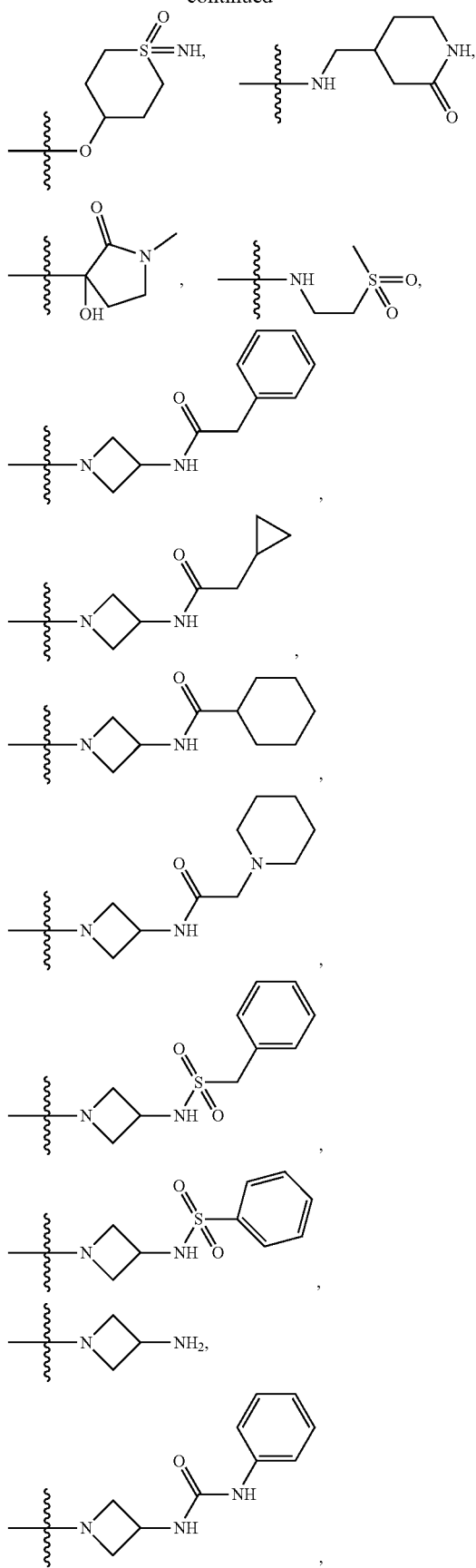

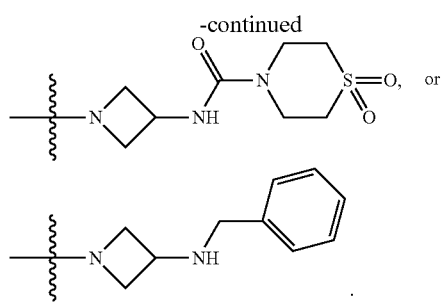
In some embodiments is a compound of Formula (I), (I'), (Ia), (Ia'), (Ib), (Ib'), (Ic), or (Ic') or a pharmaceutically acceptable salt or solvate thereof, wherein R³ is
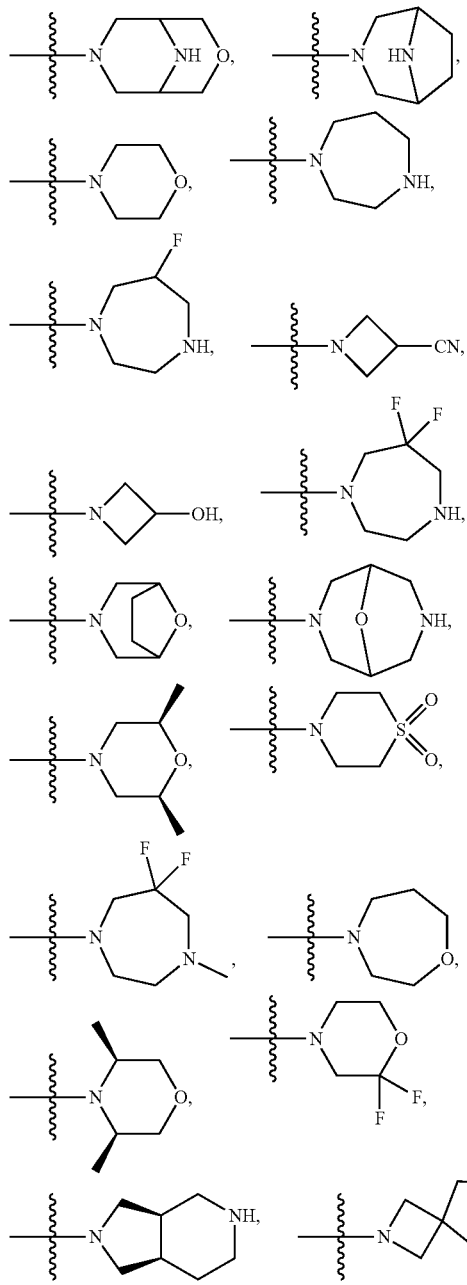
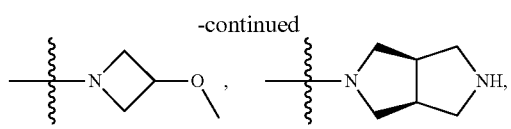
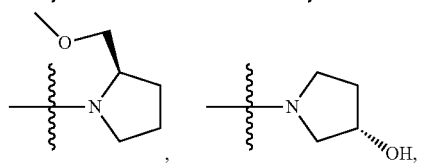
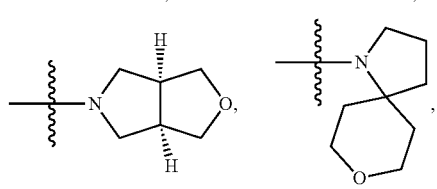
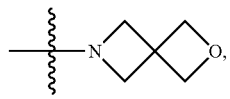
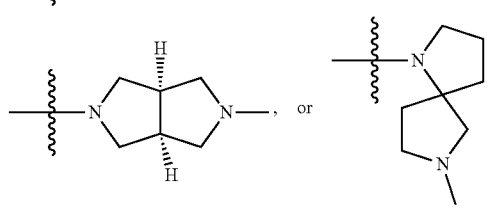
In some embodiments is a compound of Formula (I), (I'), (Ia), (Ia'), (Ib), (Ib'), (Ic), or (Ic'), or a pharmaceutically acceptable salt or solvate thereof, wherein R³ is
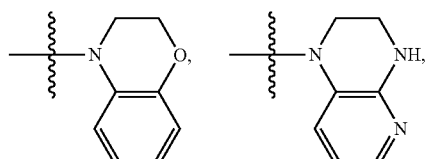
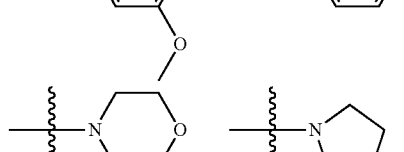
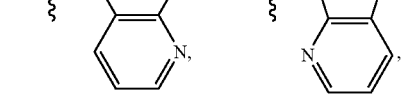
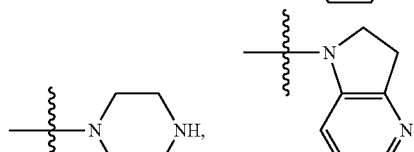
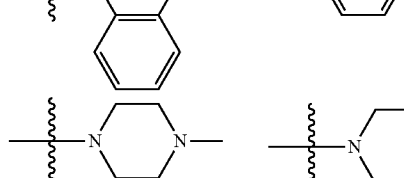

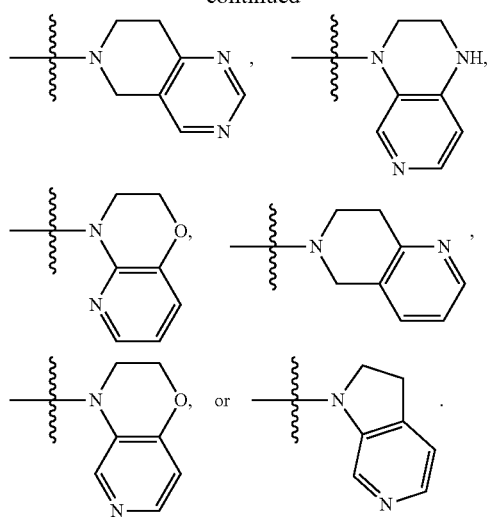
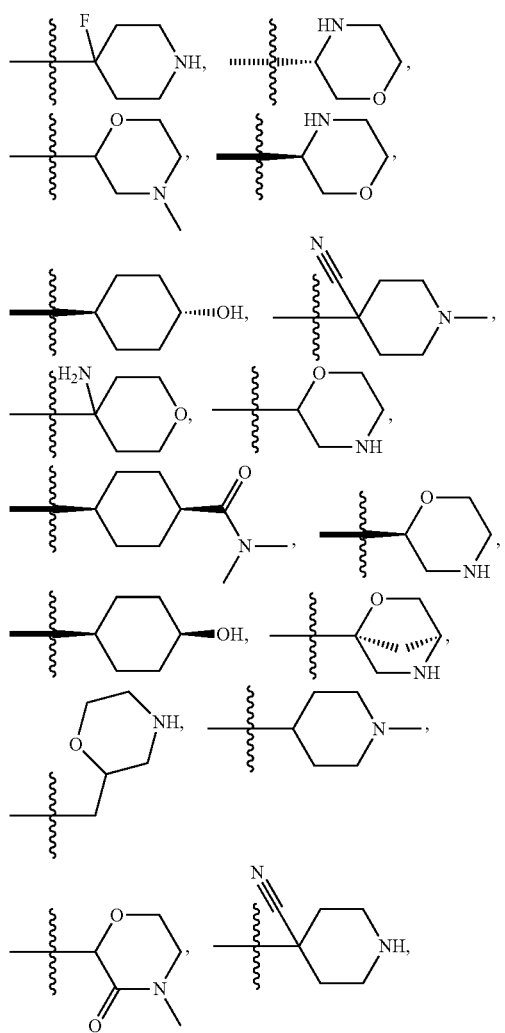
In some embodiments is a compound of Formula (I), (I'), (Ia), (Ia'), (Ib), (Ib'), (Ic), or (Ic'), or a pharmaceutically acceptable salt or solvate thereof, wherein R³ is
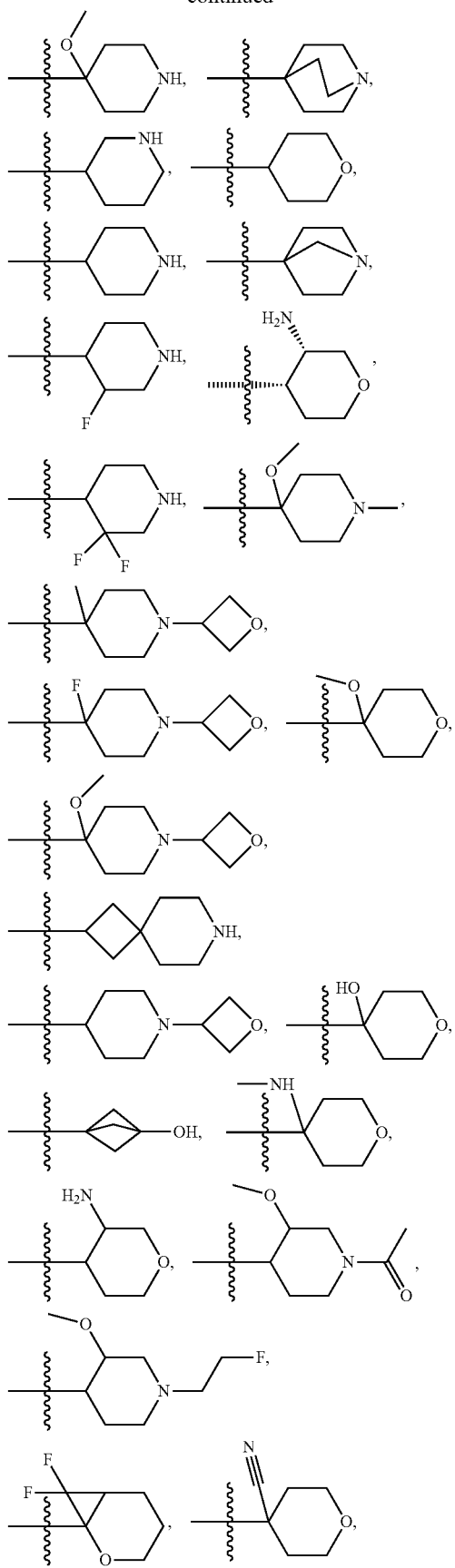

-continued
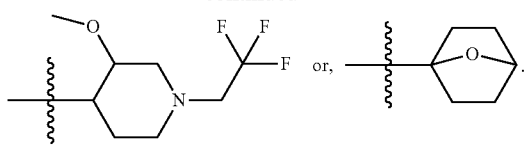
In some embodiments is a compound of Formula (I), (I'), (Ia), (Ia'), (Ib), (Ib'), (Ic), or (Ic'), or a pharmaceutically acceptable salt or solvate thereof, wherein $R^3$ is

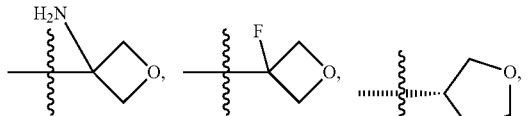
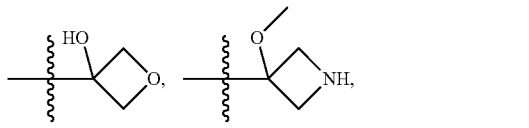
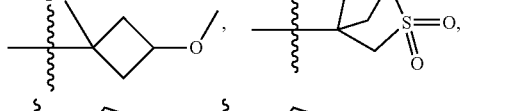

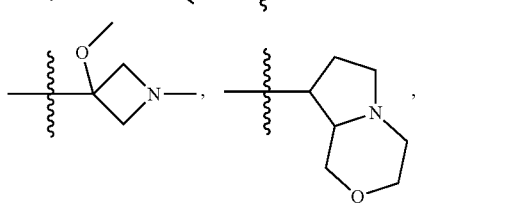
-continued
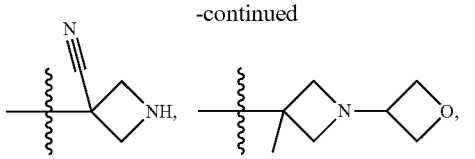
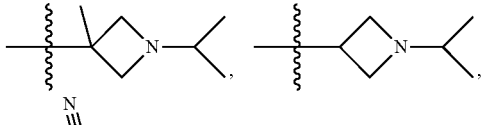
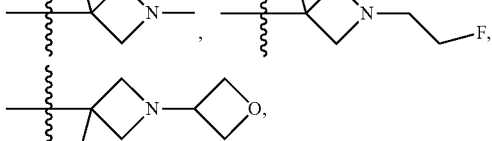
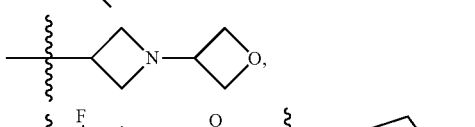
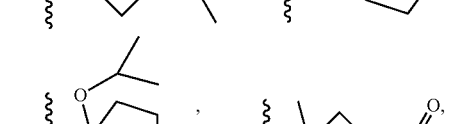
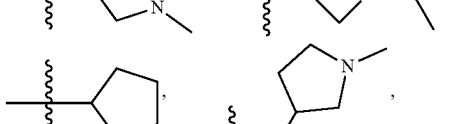
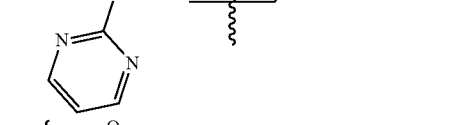
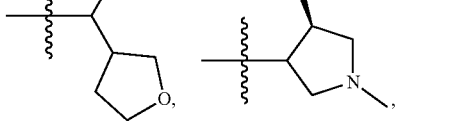
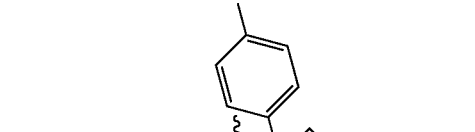
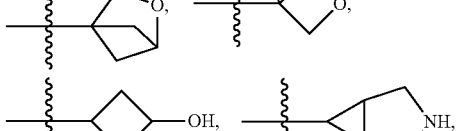
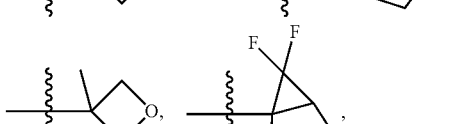

107
-continued
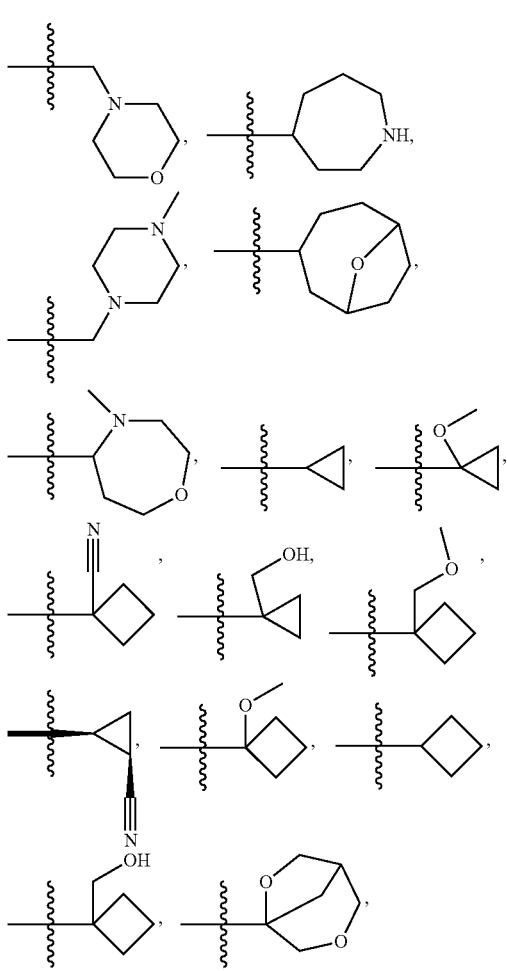
In some embodiments is a compound of Formula (I), (I'), (Ia), (Ia'), (Ib), (Ib'), (Ic), or (Ic'), or a pharmaceutically acceptable salt or solvate thereof, wherein R³ is
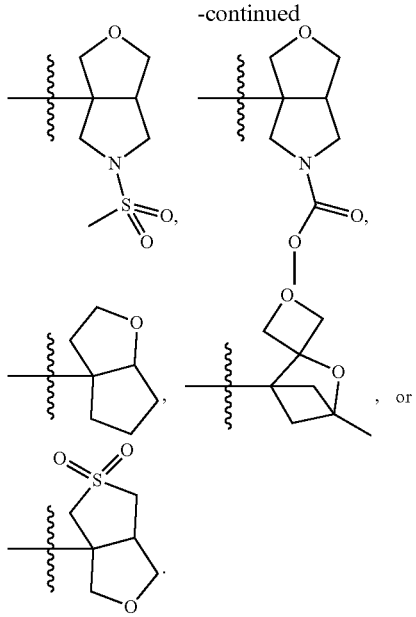
108
-continued
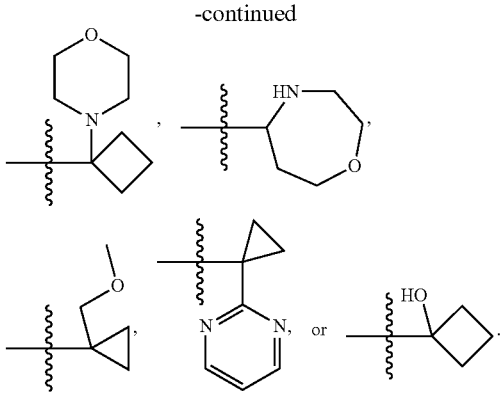
In some embodiments is a compound of Formula (I), (I'), (Ia), (Ia'), (Ib), (Ib'), (Ic), or (Ic'), or a pharmaceutically acceptable salt or solvate thereof, wherein R³ is
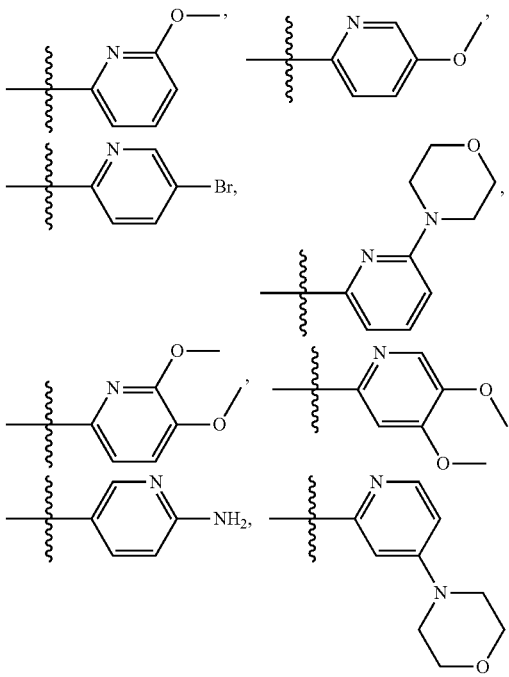

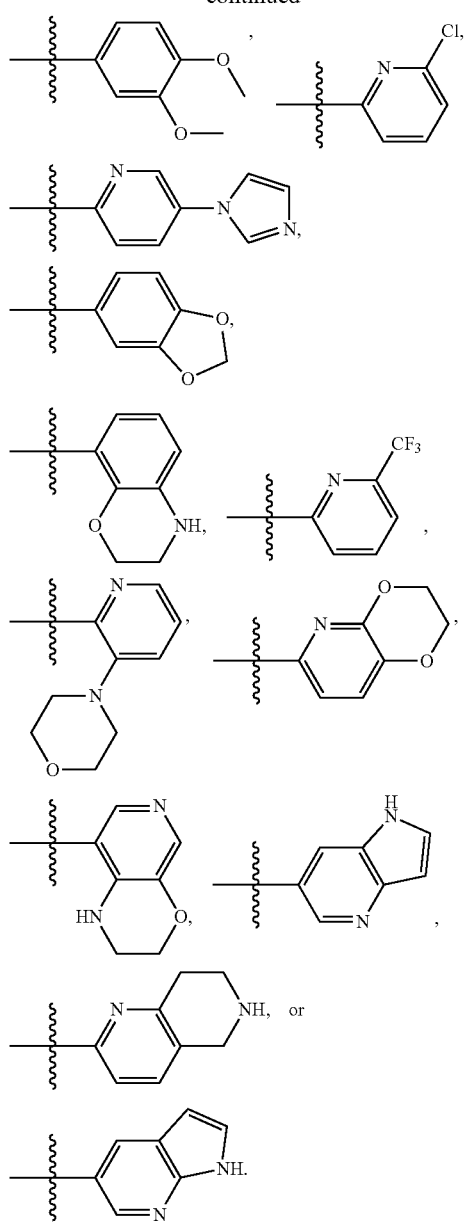
In some embodiments is a compound of Formula (I), (I'), (Ia), (Ia'), (Ib), (Ib'), (Ic), or (Ic'), or a pharmaceutically acceptable salt or solvate thereof, wherein R³ is
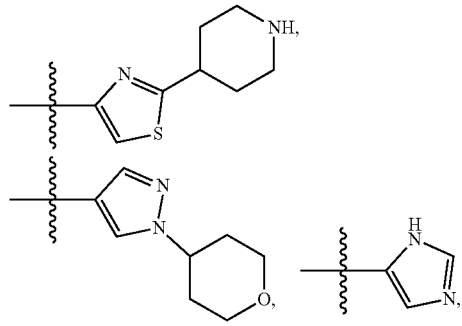
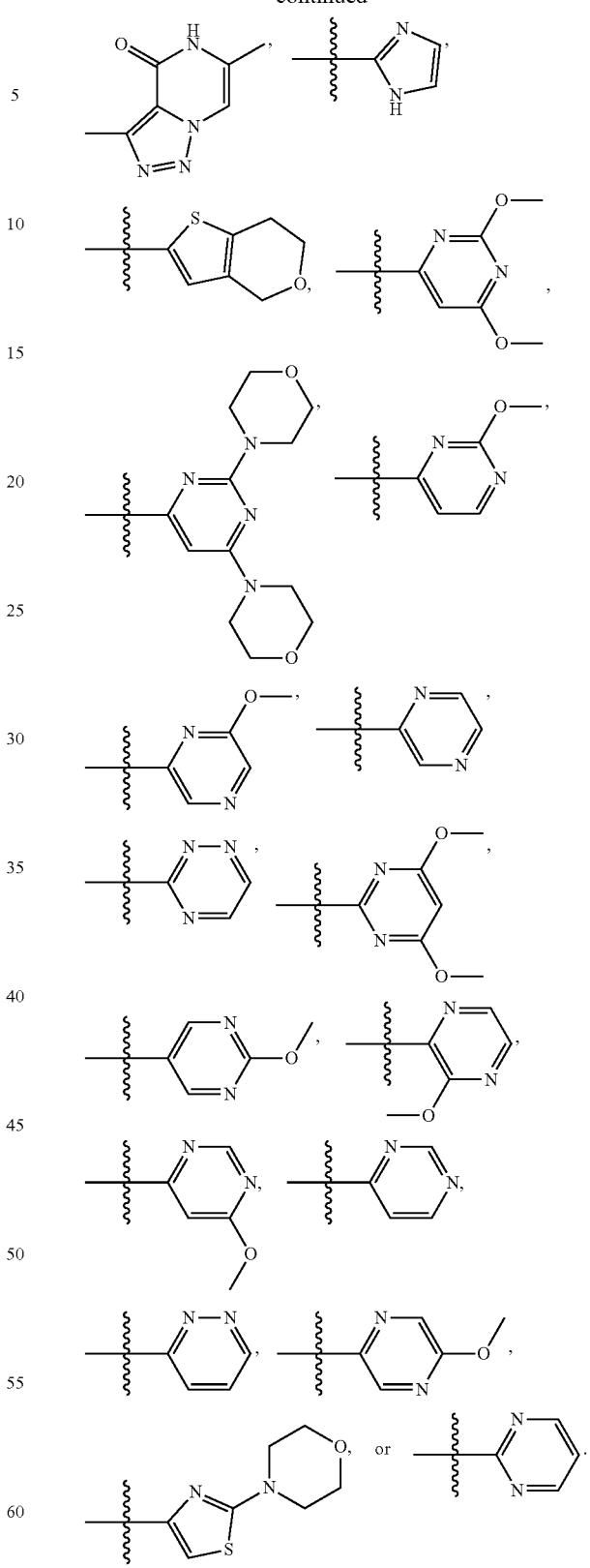
In some embodiments is a compound of Formula (I), (I'), (Ia), (Ia'), (Ib), (Ib'), (Ic), or (Ic'), or a pharmaceutically acceptable salt or solvate thereof, wherein R³ is 111 112
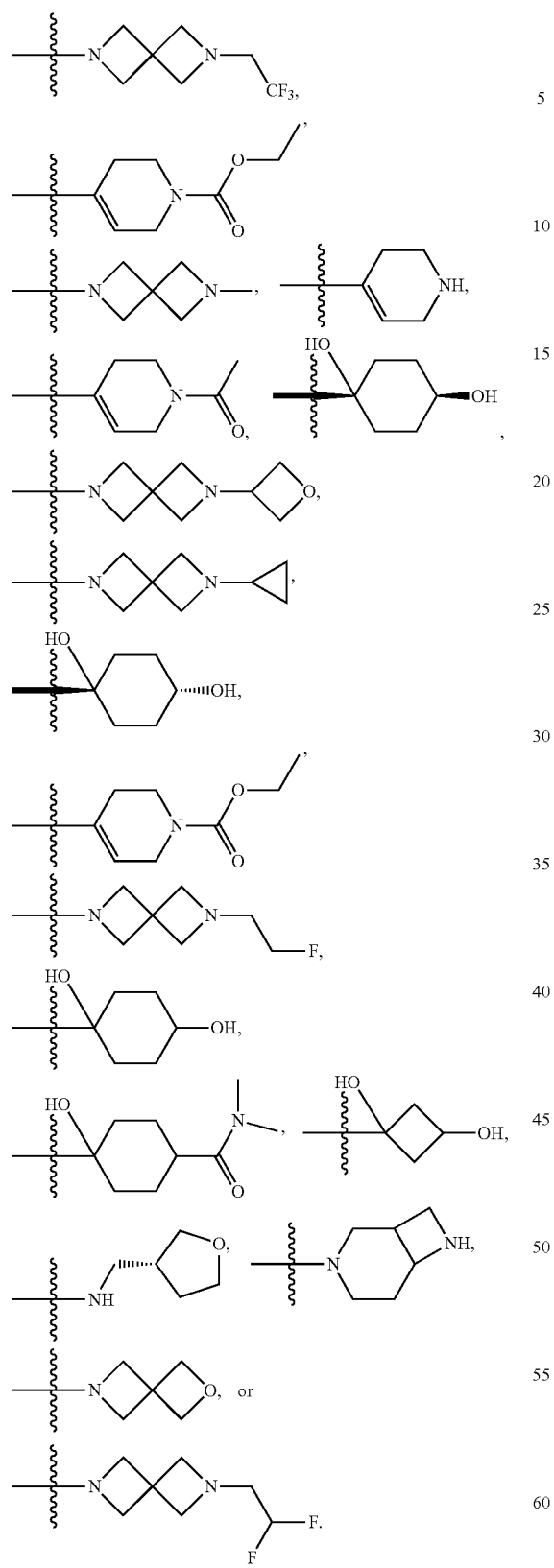
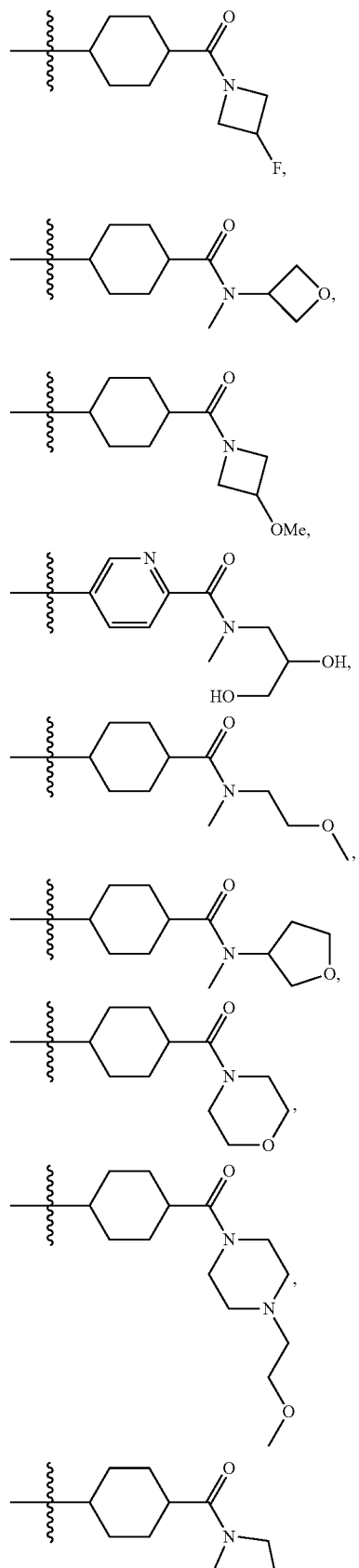
In some embodiments is a compound of Formula (I), (I'), (Ia), (Ia'), (Ib), (Ib'), (Ic), or (Ic'), or a pharmaceutically acceptable salt or solvate thereof, wherein $R^3$ is

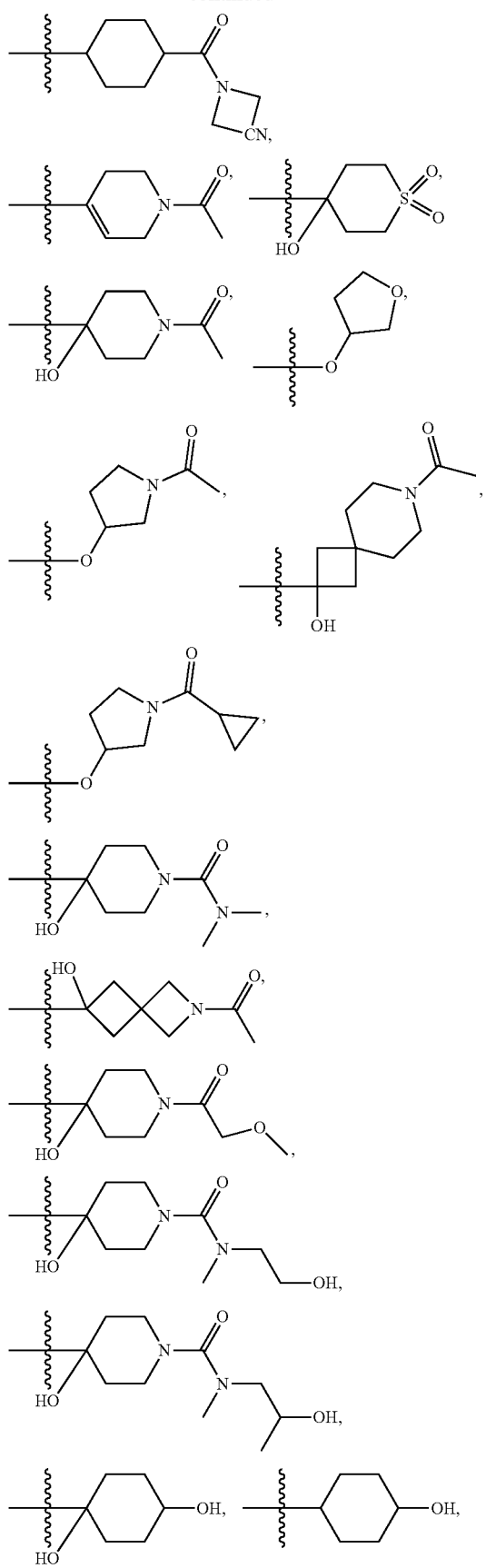
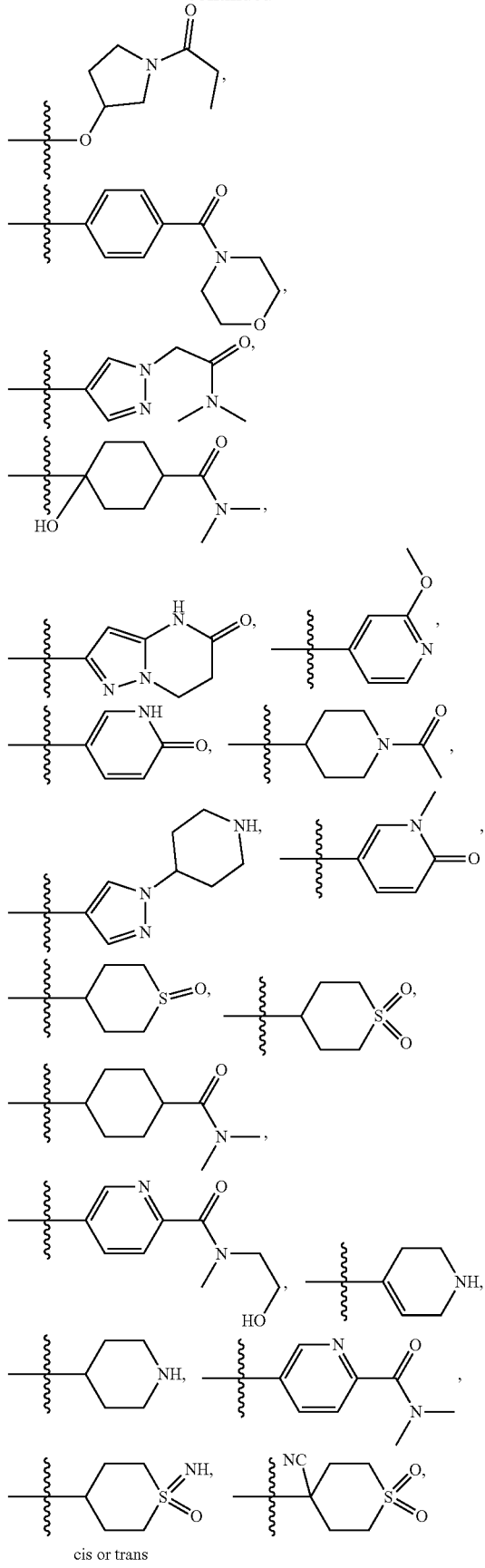
cis or trans

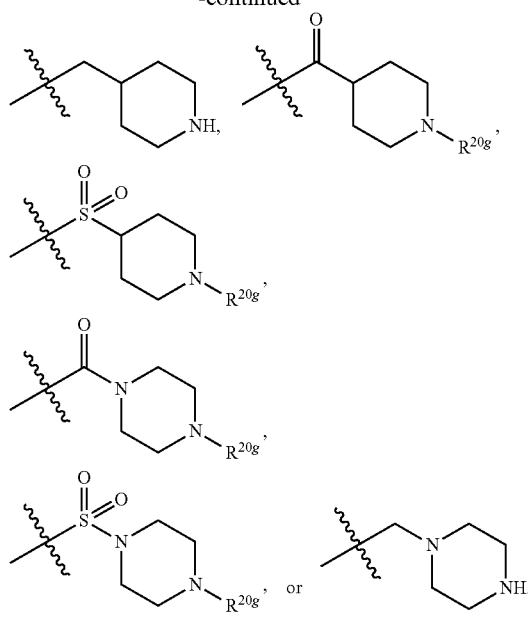
In some embodiments is a compound of Formula (I), (I'), (Ia), (Ia'), (Ib), (Ib'), (Ic), or (Ic'), or a pharmaceutically acceptable salt or solvate thereof, wherein $R^3$ is
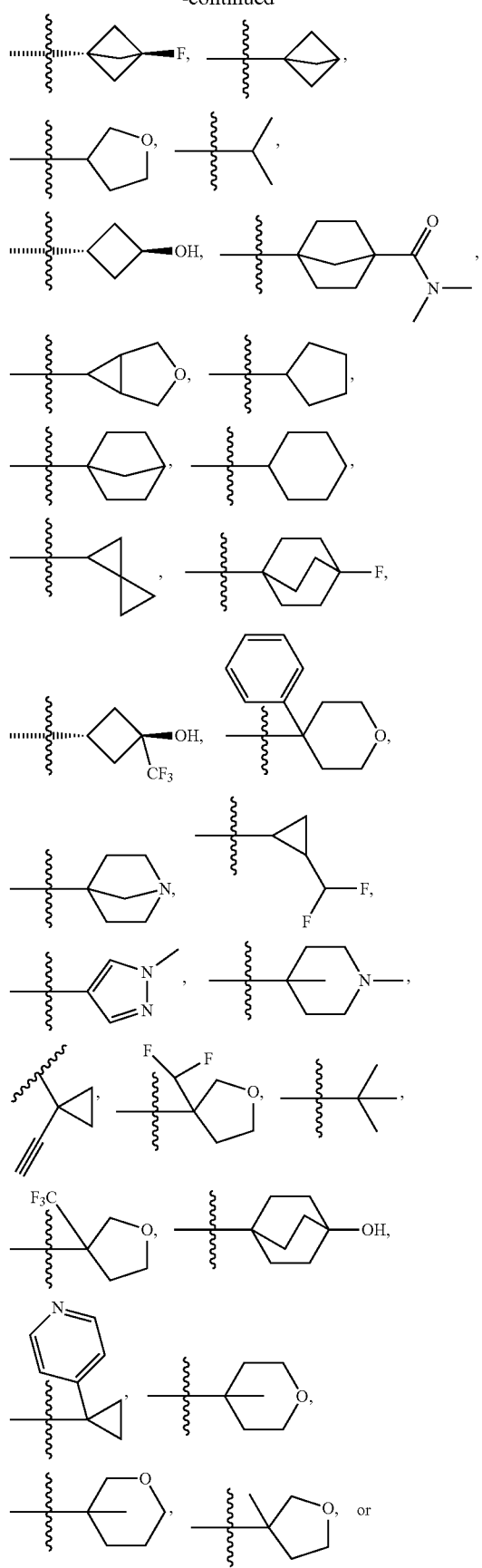

-continued

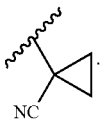

In some embodiments of a compound of Formula (I), (I'), (Ia), (Ia'), (Ib), (Ib'), (Ic), or (Ic'), or a pharmaceutically acceptable salt or solvate thereof, $R^3$ is

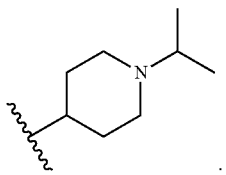 [SMILES: *C1CCN(C(C)C)CC1]

In some embodiments of a compound of Formula (I), (I'), (Ia), (Ia'), (Ib), (Ib'), (Ic), or (Ic'), or a pharmaceutically acceptable salt or solvate thereof, $R^3$ is

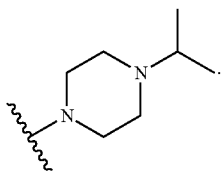 [SMILES: *N1CCN(C(C)C)CC1]

In some embodiments is a compound of Formula (I), (I'), (Ia), (Ia'), (Ib), (Ib'), (Ic), or (Ic'), or a pharmaceutically acceptable salt or solvate thereof, $R^3$ is

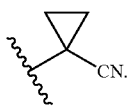

In some embodiments is a compound of Formula (I), (I'), (Ia), (Ia'), (Ib), (Ib'), (Ic), or (Ic'), or a pharmaceutically acceptable salt or solvate thereof, $R^3$ is

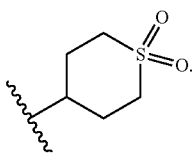 [SMILES: *C1CCS(=O)(=O)CC1]

In some embodiments is a compound of Formula (I), (I'), (Ia), (Ia'), (Ib), (Ib'), (Ic), or (Ic'), or a pharmaceutically acceptable salt or solvate thereof, $R^3$ is

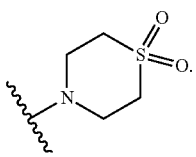 [SMILES: *N1CCS(=O)(=O)CC1]

In some embodiments is a compound of Formula (I), (I'), (Ia), (Ia'), (Ib), (Ib'), (Ic), or (Ic'), or a pharmaceutically acceptable salt or solvate thereof, wherein $R^6$ is selected from hydrogen, $C_{1-6}$alkyl, $C_{3-10}$cycloalkyl, $C_{2-9}$heterocycloalkyl, $C_{6-10}$aryl, and $C_{1-9}$heteroaryl, wherein $C_{1-6}$alkyl, $C_{3-10}$cycloalkyl, $C_{2-9}$heterocycloalkyl, $C_{6-10}$aryl, and $C_{1-9}$heteroaryl are optionally substituted with one, two, or three $R^{20c}$. In some embodiments is a compound of Formula (I), (I'), (Ia), (Ia'), (Ib), (Ib'), (Ic), or (Ic'), or a pharmaceutically acceptable salt or solvate thereof, wherein $R^6$ is selected from hydrogen and $C_{1-6}$alkyl optionally substituted with one, two, or three $R^{20c}$. In some embodiments is a compound of Formula (I), (I'), (Ia), (Ia'), (Ib), (Ib'), (Ic), or (Ic'), or a pharmaceutically acceptable salt or solvate thereof, wherein $R^6$ is $C_{1-6}$alkyl optionally substituted with one, two, or three $R^{20c}$. In some embodiments is a compound of Formula (I), (I'), (Ia), (Ia'), (Ib), (Ib'), (Ic), or (Ic'), or a pharmaceutically acceptable salt or solvate thereof, wherein $R^6$ is hydrogen. In some embodiments is a compound of Formula (I), (I'), (Ia), (Ia'), (Ib), (Ib'), (Ic), or (Ic'), or a pharmaceutically acceptable salt or solvate thereof, wherein $R^6$ is methyl.

In some embodiments is a compound of Formula (I), (I'), (Ia), (Ia'), (Ib), (Ib'), (Ic), or (Ic'), or a pharmaceutically acceptable salt or solvate thereof, wherein $R^7$ is selected from hydrogen, $C_{1-6}$alkyl, $C_{3-10}$cycloalkyl, $C_{2-9}$heterocycloalkyl, $C_{6-10}$aryl, and $C_{1-9}$ heteroaryl, wherein $C_{1-6}$alkyl, $C_{3-10}$cycloalkyl, $C_{2-9}$heterocycloalkyl, $C_{6-10}$aryl, and $C_{1-9}$heteroaryl are optionally substituted with one, two, or three $R^{20c}$. In some embodiments is a compound of Formula (I), (I'), (Ia), (Ia'), (Ib), (Ib'), (Ic), or (Ic'), or a pharmaceutically acceptable salt or solvate thereof, wherein $R^7$ is selected from hydrogen and $C_{1-6}$alkyl optionally substituted with one, two, or three $R^{20c}$. In some embodiments is a compound of Formula (I), (I'), (Ia), (Ia'), (Ib), (Ib'), (Ic), or (Ic'), or a pharmaceutically acceptable salt or solvate thereof, wherein $R^7$ is $C_{1-6}$alkyl optionally substituted with one, two, or three $R^{20c}$. In some embodiments is a compound of Formula (I), (I'), (Ia), (Ia'), (Ib), (Ib'), (Ic), or (Ic'), or a pharmaceutically acceptable salt or solvate thereof, wherein $R^7$ is hydrogen. In some embodiments is a compound of Formula (I), (I'), (Ia), (Ia'), (Ib), (Ib'), (Ic), or (Ic'), or a pharmaceutically acceptable salt or solvate thereof, wherein $R^7$ is methyl.

In some embodiments is a compound of Formula (I), (I'), (Ia), (Ia'), (Ib), (Ib'), (Ic), or (Ic'), or a pharmaceutically acceptable salt or solvate thereof, wherein $L^1$ is a bond. In some embodiments is a compound of Formula (I), (I'), (Ia), (Ia'), (Ib), (Ib'), (Ic), or (Ic'), or a pharmaceutically acceptable salt or solvate thereof, wherein $L^1$ is $C_{1-6}$alkyl.

In some embodiments is a compound of Formula (I), (I'), (Ia), (Ia'), (Ib), (Ib'), (Ic), or (Ic'), or a pharmaceutically acceptable salt or solvate thereof, wherein $R^1$ is a 6-10 membered aryl ring optionally substituted with one or more $R^{10}$. In some embodiments is a compound of Formula (I), (I'), (Ia), (Ia'), (Ib), (Ib'), (Ic), or (Ic'), or a pharmaceutically acceptable salt or solvate thereof, wherein $R^1$ is a phenyl optionally substituted with one or more $R^{10}$. In some embodiments is a compound of Formula (I), (I'), (Ia), (Ia'), (Ib), (Ib'), (Ic), or (Ic'), or a pharmaceutically acceptable salt or solvate thereof, wherein $R^1$ is a phenyl substituted with one or more $R^{10}$. In some embodiments is a compound of Formula (I), (I'), (Ia), (Ia'), (Ib), (Ib'), (Ic), or (Ic'), or a pharmaceutically acceptable salt or solvate thereof, wherein $R^1$ is phenyl substituted with one, two, or three $R^{10}$. In some embodiments is a compound of Formula (I), (I'), (Ia), (Ia'), (Ib), (Ib'), (Ic), or (Ic'), or a pharmaceutically acceptable salt or solvate thereof, wherein $R^1$ is phenyl substituted with one, two, or three $R^{10}$, wherein each $R^{10}$ is independently selected from halogen, $C_{1-6}$alkyl, $C_{3-7}$cycloalkyl, $C_{2-9}$heterocycloalkyl, $C_{6-10}$aryl, $C_{1-9}$ heteroaryl, —$OR^{12}$, and $N(R^{12})(R^{13})$, wherein $C_{1-6}$alkyl, $C_{3-7}$cycloalkyl, $C_{2-9}$heterocycloalkyl, $C_{6-10}$aryl, and $C_{1-9}$heteroaryl are optionally substituted with one, two, or three $R^{20d}$. In some embodiments is a compound of Formula (I), (I'), (Ia), (Ia'), (Ib), (Ib'), (Ic), or (Ic'), or a pharmaceutically acceptable salt or solvate thereof, wherein $R^1$ is phenyl substituted with one, two, or three $R^{10}$, wherein each $R^{10}$ is independently selected from halogen, $C_{1-6}$alkyl, and $N(R^{12})(R^{13})$, wherein $C_{1-6}$alkyl is optionally substituted with one, two, or three $R^{20d}$. In some embodiments is a compound of Formula (I), (I'), (Ia), (Ia'), (Ib), (Ib'), (Ic), or (Ic'), or a pharmaceutically acceptable salt or solvate thereof, wherein $R^1$ is phenyl substituted with one, two, or three $R^{10}$, wherein each $R^{10}$ is independently selected from halogen and $C_{1-6}$alkyl, wherein $C_{1-6}$alkyl is substituted with one, two, or three $R^{20d}$, and each $R^{20d}$ is halogen.

In some embodiments is a compound of Formula (I), (I'), (Ia), (Ia'), (Ib), (Ib'), (Ic), or (Ic'), or a pharmaceutically acceptable salt or solvate thereof, wherein $R^1$ is a 5-10 membered heteroaryl ring optionally substituted with one or more $R^{10}$. In some embodiments is a compound of Formula (I), (I'), (Ia), (Ia'), (Ib), (Ib'), (Ic), or (Ic'), or a pharmaceutically acceptable salt or solvate thereof, wherein $R^1$ is a 5-10 membered heteroaryl ring substituted with one or more $R^{10}$. In some embodiments is a compound of Formula (I), (I'), (Ia), (Ia'), (Ib), (Ib'), (Ic), or (Ic'), or a pharmaceutically acceptable salt or solvate thereof, wherein $R^1$ is a 5-10 membered heteroaryl ring substituted with one, two, or three $R^{10}$. In some embodiments is a compound of Formula (I), (I'), (Ia), (Ia'), (Ib), (Ib'), (Ic), or (Ic'), or a pharmaceutically acceptable salt or solvate thereof, wherein $R^1$ is a 5-10 membered heteroaryl ring substituted with one, two, or three $R^{10}$, wherein each $R^{10}$ is independently selected from halogen, $C_{1-6}$alkyl, $C_{3-7}$cycloalkyl, $C_{2-9}$heterocycloalkyl, $C_{6-10}$aryl, $C_{1-9}$heteroaryl, —$OR^{12}$, and $N(R^{12})(R^{13})$, wherein $C_{1-6}$alkyl, $C_{3-7}$cycloalkyl, $C_{2-9}$heterocycloalkyl, $C_{6-10}$aryl, and $C_{1-9}$heteroaryl are optionally substituted with one, two, or three $R^{20d}$. In some embodiments is a compound of Formula (I), (I'), (Ia), (Ia'), (Ib), (Ib'), (Ic), or (Ic'), or a pharmaceutically acceptable salt or solvate thereof, wherein $R^1$ is a 5-10 membered heteroaryl ring substituted with one, two, or three $R^{10}$, wherein each $R^{10}$ is independently selected from halogen, $C_{1-6}$alkyl, and $N(R^{12})(R^{13})$ wherein $C_{1-6}$alkyl is optionally substituted with one, two, or three $R^{20d}$. In some embodiments is a compound of Formula (I), (I'), (Ia), (Ia'), (Ib), (Ib'), (Ic), or (Ic'), or a pharmaceutically acceptable salt or solvate thereof, wherein $R^1$ is a 5-10 membered heteroaryl ring substituted with one, two, or three $R^{10}$, wherein each $R^{10}$ is independently selected from halogen and $C_{1-6}$alkyl, wherein $C_{1-6}$alkyl is substituted with one, two, or three $R^{20d}$, and each $R^{20d}$ is halogen. In some embodiments is a compound of Formula (I), (I'), (Ia), (Ia'), (Ib), (Ib'), (Ic), or (Ic'), or a pharmaceutically acceptable salt or solvate thereof, wherein $R^1$ is an unsubstituted 5-10 membered heteroaryl ring.

In some embodiments is a compound of Formula (I), (I'), (Ia), (Ia'), (Ib), (Ib'), (Ic), or (Ic'), or a pharmaceutically acceptable salt or solvate thereof, wherein $R^1$ is a 3-12 membered cycloalkyl ring optionally substituted with one or more $R^{10}$. In some embodiments is a compound of Formula (I), (I'), (Ia), (Ia'), (Ib), (Ib'), (Ic), or (Ic'), or a pharmaceutically acceptable salt or solvate thereof, wherein $R^1$ is a 3-12 membered cycloalkyl ring substituted with one or more $R^{10}$. In some embodiments is a compound of Formula (I), (I'), (Ia), (Ia'), (Ib), (Ib'), (Ic), or (Ic'), or a pharmaceutically acceptable salt or solvate thereof, wherein $R^1$ is an unsubstituted 3-12 membered cycloalkyl ring.

In some embodiments is a compound of Formula (I), (I'), (Ia), (Ia'), (Ib), (Ib'), (Ic), or (Ic'), or a pharmaceutically acceptable salt or solvate thereof, wherein $R^1$ is a 3-12 membered heterocycloalkyl ring optionally substituted with one or more $R^{10}$. In some embodiments is a compound of Formula (I), (I'), (Ia), (Ia'), (Ib), (Ib'), (Ic), or (Ic'), or a pharmaceutically acceptable salt or solvate thereof, wherein $R^1$ is a 3-12 membered heterocycloalkyl ring substituted with one or more $R^{10}$. In some embodiments is a compound of Formula (I), (I'), (Ia), (Ia'), (Ib), (Ib'), (Ic), or (Ic'), or a pharmaceutically acceptable salt or solvate thereof, wherein $R^1$ is an unsubstituted 3-12 membered heterocycloalkyl ring optionally substituted with one or more $R^{10}$.

In some embodiments is a compound of Formula (I), (I'), (Ia), (Ia'), (Ib), (Ib'), (Ic), or (Ic'), or a pharmaceutically acceptable salt or solvate thereof, wherein $R^4$ is hydrogen. In some embodiments is a compound of Formula (I), (I'), (Ia), (Ia'), (Ib), (Ib'), (Ic), or (Ic'), or a pharmaceutically acceptable salt or solvate thereof, wherein $R^4$ is $C_{1-6}$alkyl. In some embodiments is a compound of Formula (I), (I'), (Ia), (Ia'), (Ib), (Ib'), (Ic), or (Ic'), or a pharmaceutically acceptable salt or solvate thereof, wherein $R^4$ is —$CH_3$. In some embodiments is a compound of Formula (I), (I'), (Ia), (Ia'), (Ib), (Ib'), (Ic), or (Ic'), or a pharmaceutically acceptable salt or solvate thereof, wherein $R^4$ is $C_{1-6}$haloalkyl.

In some embodiments, the disclosure provides a compound of Formula (II), or a pharmaceutically acceptable salt or solvate thereof:

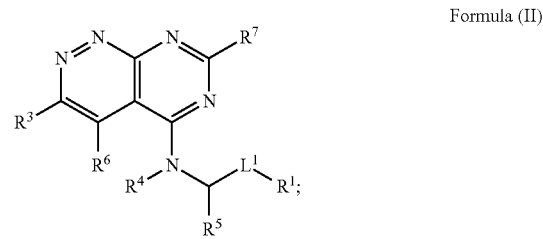

Formula (II)

$R^1$ is a 3-12 membered cycloalkyl ring, 3-12 membered heterocycloalkyl ring, 6-10 membered aryl ring, or 5-10 membered heteroaryl ring, wherein the 3-12 membered cycloalkyl ring, 3-12 membered heterocycloalkyl ring, 6-10 membered aryl ring, and 5-10 membered heteroaryl ring are optionally substituted with one or more $R^{10}$;

$L^1$ is a bond or $C_{1-6}$alkyl;

$R^3$ is selected from hydrogen, halogen, —CN, $C_{1-6}$alkyl, $C_{2-6}$alkenyl, $C_{2-6}$alkynyl, $C_{3-14}$cycloalkyl, $C_{2-9}$heterocycloalkyl, $C_{6-10}$aryl, $C_{1-9}$ heteroaryl, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, $N(R^{14})S(O)R^{15}$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{15}$, —$S(O)_2R^{15}$, —$S(O)_2N(R^{12})(R^{13})$, —$S(O)N(R^{12})(R^{13})$, —$S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, —$CH_2S(O)_2N(R^{12})(R^{13})$, —$CH_2N(R^{12})S(O)_2(R^{13})$, $CH_2S(O)$ $R^{15}$, —$CH_2S(O)N(R^{12})(R^{13})$, —$CH_2N(R^{12})S(O)(R^{13})$ and —$P(O)(R^{17})(R^{17a})$, wherein $C_{1-6}$alkyl, $C_{2-6}$alkenyl, $C_{2-6}$alkynyl, $C_{3-14}$cycloalkyl, $C_{2-9}$heterocycloalkyl, $C_{6-10}$aryl, and $C_{1-9}$heteroaryl are optionally substituted with one, two, or three $R^{20b}$;

$R^4$ is selected from hydrogen, $C_{1-6}$alkyl, and $C_{1-6}$haloalkyl;

$R^5$ is selected from hydrogen, $C_{1-6}$alkyl, and $C_{1-6}$haloalkyl;

$R^6$ and $R^7$ are each independently selected from hydrogen, halogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{1-9}$heteroaryl, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{15}$, —$S(O)_2R^{15}$, —$S(O)_2N(R^{12})(R^{13})$, —$S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, —$CH_2S(O)_2N(R^{12})(R^{13})$, —$CH_2N(R^{12})S(O)_2(R^{13})$, and —$P(O)(R^{17})(R^{17a})$, wherein $C_{1-6}$alkyl, $C_{2-6}$alkenyl, $C_{2-6}$alkynyl, $C_{3-10}$cycloalkyl, $C_{2-9}$heterocycloalkyl, and $C_{1-9}$heteroaryl are optionally substituted with one, two, or three $R^{20c}$;

each $R^{10}$ is independently selected from halogen, —CN, $C_{1-6}$alkyl, $C_{2-6}$alkenyl, $C_{2-6}$alkynyl, $C_{3-7}$cycloalkyl, $C_{2-9}$heterocycloalkyl, $C_{6-10}$aryl, $C_{1-9}$heteroaryl, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{15}$, —$S(O)_2R^{15}$, —$S(O)_2N(R^{12})(R^{13})$, —$S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, —$CH_2S(O)_2N(R^{12})(R^{13})$, —$CH_2N(R^{12})S(O)_2(R^{13})$, and —$P(O)(R^{17})(R^{17a})$, wherein $C_{1-6}$alkyl, $C_{2-6}$alkenyl, $C_{2-6}$alkynyl, $C_{3-7}$cycloalkyl, $C_{2-9}$heterocycloalkyl, $C_{6-10}$aryl, and $C_{1-9}$heteroaryl are optionally substituted with one, two, or three $R^{20d}$;

each $R^{12}$ is independently selected from hydrogen, $C_{1-6}$alkyl, $C_{1-6}$haloalkyl, $C_{2-6}$alkenyl, $C_{2-6}$alkynyl, $C_{3-7}$cycloalkyl, $C_{2-9}$heterocycloalkyl, $C_{6-10}$aryl, and $C_{1-9}$heteroaryl, wherein $C_{1-6}$alkyl, $C_{2-6}$alkenyl, $C_{2-6}$alkynyl, $C_{3-7}$cycloalkyl, $C_{2-9}$heterocycloalkyl, $C_{6-10}$aryl, and $C_{1-9}$heteroaryl are optionally substituted with one, two, or three $R^{20e}$;

each $R^{13}$ is independently selected from hydrogen, $C_{1-6}$alkyl, and $C_{1-6}$haloalkyl; or $R^{12}$ and $R^{13}$, together with the nitrogen to which they are attached, form a $C_{2-9}$heterocycloalkyl ring optionally substituted with one, two, or three $R^{20f}$;

each $R^{14}$ is independently selected from hydrogen, $C_{1-6}$alkyl, and $C_{1-6}$haloalkyl;

each $R^{15}$ is independently selected $C_{1-6}$alkyl, $C_{2-6}$alkenyl, $C_{2-6}$alkynyl, $C_{3-7}$cycloalkyl, $C_{2-9}$heterocycloalkyl, $C_{6-10}$aryl, and $C_{1-9}$ heteroaryl, wherein $C_{1-6}$alkyl, $C_{2-6}$alkenyl, $C_{2-6}$alkynyl, $C_{3-7}$cycloalkyl, $C_{2-9}$heterocycloalkyl, $C_{6-10}$aryl, and $C_{1-9}$heteroaryl are optionally substituted with one, two, or three $R^{20g}$;

each $R^{17}$ and each $R^{17a}$ are each independently selected from $C_{1-6}$alkyl and $C_{3-6}$cycloalkyl, wherein $C_{1-6}$alkyl and $C_{3-6}$cycloalkyl are optionally substituted with one, two or three of $R^{20h}$; or $R^{17}$ and $R^{17a}$ form a $C_{2-9}$heterocycloalkyl ring;

each $R^{20a}$, $R^{20b}$, $R^{20c}$, $R^{20d}$, $R^{20e}$, $R^{20f}$, $R^{20g}$, and $R^{20h}$ are each independently selected from halogen, oxo, =NH, —CN, $C_{1-6}$alkyl, $C_{2-6}$alkenyl, $C_{2-6}$alkynyl, $C_{3-10}$cycloalkyl, —$CH_2$—$C_{3-10}$cycloalkyl, $C_{2-9}$heterocycloalkyl, —$CH_2$—$C_{2-9}$heterocycloalkyl, $C_{6-10}$aryl, —$CH_2$—$C_{6-10}$aryl, $C_{1-9}$heteroaryl, —$OR^{21}$, —$SR^{21}$, —$N(R^{22})(R^{23})$, —$C(O)OR^{22}$, —$C(O)N(R^{22})(R^{23})$, —$C(O)C(O)N(R^{22})(R^{23})$, —$OC(O)N(R^{22})(R^{23})$, —$N(R^{24})C(O)N(R^{22})(R^{23})$, —$N(R^{24})C(O)OR^{25}$, —$N(R^{24})C(O)R^{25}$, —$N(R^{24})S(O)_2R^{25}$, —$C(O)R^{25}$, —$S(O)_2R^{25}$, —$S(O)_2N(R^{22})(R^{23})$, —$OCH_2C(O)OR^{22}$, and —$OC(O)R^{25}$, wherein $C_{1-6}$alkyl, $C_{2-6}$alkenyl, $C_{2-6}$alkynyl, $C_{3-10}$cycloalkyl, —$CH_2$—$C_{3-10}$cycloalkyl, $C_{2-9}$heterocycloalkyl, —$CH_2$—$C_{2-9}$heterocycloalkyl, $C_{6-10}$aryl, —$CH_2$—$C_{6-10}$aryl, and $C_{1-9}$heteroaryl are optionally substituted with one, two or three groups independently selected from halogen, oxo, =NH, —CN, $C_{1-6}$alkyl, $C_{1-6}$haloalkyl, $C_{1-6}$alkoxy, $C_{1-6}$haloalkoxy, —$OR^{21}$, —$SR^{21}$, —$N(R^{22})(R^{23})$, —$C(O)OR^{22}$, —$C(O)N(R^{22})(R^{23})$, —$C(O)C(O)N(R^{22})(R^{23})$, —$OC(O)N(R^{22})(R^{23})$, —$N(R^{24})C(O)N(R^{22})(R^{23})$, —$N(R^{24})C(O)OR^{25}$, —$N(R^{24})C(O)R^{25}$, —$N(R^{24})S(O)_2R^{25}$, —$C(O)R^{25}$, —$S(O)_2R^{25}$, —$S(O)_2N(R^{22})(R^{23})$, and —$OC(O)R^{25}$;

each $R^{21}$ is independently selected from H, $C_{1-6}$alkyl, $C_{1-6}$haloalkyl, $C_{2-6}$alkenyl, $C_{2-6}$alkynyl, $C_{3-7}$cycloalkyl, $C_{2-9}$heterocycloalkyl, $C_{6-10}$aryl, and $C_{1-9}$heteroaryl, wherein $C_{3-7}$cycloalkyl, $C_{2-9}$heterocycloalkyl, $C_{6-10}$aryl, and $C_{1-9}$heteroaryl are optionally substituted with one, two, or three groups independently selected from halogen and $C_{1-6}$alkyl;

each $R^{22}$ is independently selected from H, $C_{1-6}$alkyl, $C_{1-6}$haloalkyl, $C_{2-6}$alkenyl, $C_{2-6}$alkynyl, $C_{3-7}$cycloalkyl, $C_{2-9}$heterocycloalkyl, $C_{6-10}$aryl, and $C_{1-9}$heteroaryl, wherein $C_{3-7}$cycloalkyl, $C_{2-9}$heterocycloalkyl, $C_{6-10}$aryl, and $C_{1-9}$heteroaryl are optionally substituted with one, two, or three groups independently selected from halogen and $C_{1-6}$alkyl;

each $R^{23}$ is independently selected from H and $C_{1-6}$alkyl;

each $R^{24}$ is independently selected from H and $C_{1-6}$alkyl; and each $R^{25}$ is selected from $C_{1-6}$alkyl, $C_{2-6}$alkenyl, $C_{2-6}$alkynyl, $C_{3-7}$cycloalkyl, $C_{2-9}$heterocycloalkyl, $C_{6-10}$aryl, and $C_{1-9}$heteroaryl, wherein $C_{1-6}$alkyl, $C_{3-7}$cycloalkyl, $C_{2-9}$heterocycloalkyl, $C_{6-10}$aryl, and $C_{1-9}$heteroaryl are optionally substituted with one, two, or three groups independently selected from halogen, $C_{1-6}$alkyl, $C_{1-6}$haloalkyl, $C_{1-6}$alkoxy, $C_{3-7}$cycloalkyl, $C_{2-9}$heterocycloalkyl, $C_{6-10}$aryl, and $C_{1-9}$heteroaryl.

In some embodiments is a compound of Formula (II), or a pharmaceutically acceptable salt or solvate thereof, wherein $R^5$ is $C_{1-6}$alkyl. In some embodiments is a compound of Formula (II), or a pharmaceutically acceptable salt or solvate thereof, wherein $R^5$ is —$CH_3$. In some embodiments is a compound of Formula (II), or a pharmaceutically acceptable salt or solvate thereof, wherein $R^5$ is $C_{1-6}$ haloalkyl. In some embodiments is a compound of Formula (II), or a pharmaceutically acceptable salt or solvate thereof, wherein $R^5$ is hydrogen.

In some embodiments is a compound of Formula (II) having the structure of Formula (II'), or a pharmaceutically acceptable salt or solvate thereof:

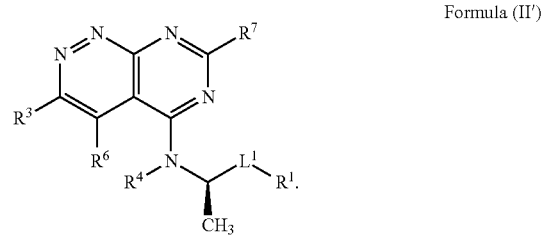

Formula (II')

In some embodiments is a compound of Formula (II) or (II'), or a pharmaceutically acceptable salt or solvate thereof, wherein $R^3$ is selected from —$OR^{12}$, —$N(R^{12})(R^{13})$, —$C(O)R^{15}$, —$C(O)N(R^{12})(R^{13})$, —$SR^{12}$, —$SOR^{12}$, —$SO_2$ $(R^{12})(R^{13})$, —SO$_2$N$(R^{12})(R^{13})$, —P(O)$(R^{17})(R^{17a})$, C$_{1-6}$alkyl, C$_{3-10}$cycloalkyl, C$_{2-9}$heterocycloalkyl, C$_{6-10}$aryl, and C$_{1-9}$heteroaryl, wherein C$_{1-6}$alkyl, C$_{3-10}$cycloalkyl, C$_{2-9}$heterocycloalkyl, C$_{6-10}$aryl, and C$_{1-9}$heteroaryl are optionally substituted with one, two, or three R$^{20b}$.

In some embodiments is a compound of Formula (II) or (II'), or a pharmaceutically acceptable salt or solvate thereof, wherein R$^3$ is selected from —C(O)R$^{15}$, —C(O)N(R$^{12}$)(R$^{13}$), C$_{2-9}$heterocycloalkyl, C$_{6-10}$aryl, and C$_{1-9}$heteroaryl, wherein C$_{2-9}$heterocycloalkyl, C$_{6-10}$aryl, and C$_{1-9}$heteroaryl are optionally substituted with one, two, or three R$^{20b}$. In some embodiments is a compound of Formula (II) or (II'), wherein R$^3$ is selected from —C(O)R$^{15}$. In some embodiments is a compound of Formula (I), (Ia), (Ib), (Ic), (Id), (Ie) or (If), wherein R$^{15}$ is C$_{2-9}$heterocycloalkyl optionally substituted with one, two, or three R$^{20g}$.

In some embodiments is a compound of Formula (II) or (II'), or a pharmaceutically acceptable salt or solvate thereof, wherein R$^3$ is C$_{2-9}$heterocycloalkyl optionally substituted with one, two, or three R$^{20b}$. In some embodiments is a compound of Formula (II) or (II'), or a pharmaceutically acceptable salt or solvate thereof, wherein R$^3$ is spirocyclic C$_{2-9}$heterocycloalkyl optionally substituted with one, two, or three R$^{20b}$. In some embodiments is a compound of Formula (II) or (II'), or a pharmaceutically acceptable salt or solvate thereof, wherein R$^3$ is fused C$_{2-9}$heterocycloalkyl optionally substituted with one, two, or three R$^{20b}$. In some embodiments is a compound of Formula (II) or (II'), or a pharmaceutically acceptable salt or solvate thereof, wherein R$^3$ is C$_{6-10}$aryl optionally substituted with one, two, or three R$^{20b}$. In some embodiments is a compound of Formula (II) or (II'), or a pharmaceutically acceptable salt or solvate thereof, wherein R$^3$ is fused C$_{6-10}$aryl optionally substituted with one, two, or three R$^{20b}$. In some embodiments is a compound of Formula (II) or (II'), or a pharmaceutically acceptable salt or solvate thereof, wherein R$^3$ is C$_{1-9}$heteroaryl optionally substituted with one, two, or three R$^{20b}$. In some embodiments is a compound of Formula (II) or (II'), or a pharmaceutically acceptable salt or solvate thereof, wherein R$^3$ is fused C$_{1-9}$heteroaryl optionally substituted with one, two, or three R$^{20b}$. In some embodiments is a compound of Formula (II) or (II'), or a pharmaceutically acceptable salt or solvate thereof, wherein R$^3$ is —C(O)N(R$^{12}$)(R$^{13}$).

In some embodiments is a compound of Formula (II) or (II'), or a pharmaceutically acceptable salt or solvate thereof, wherein R$^{15}$ is C$_{2-9}$heterocycloalkyl optionally substituted with one, two, or three R$^{20g}$. In some embodiments is a compound of Formula (II) or (II'), or a pharmaceutically acceptable salt or solvate thereof, wherein R$^{15}$ is spirocyclic C$_{2-9}$heterocycloalkyl optionally substituted with one, two, or three R$^{20g}$. In some embodiments is a compound of Formula (II) or (II'), or a pharmaceutically acceptable salt or solvate thereof, wherein R$^{15}$ is fused C$_{2-9}$heterocycloalkyl optionally substituted with one, two, or three R$^{20g}$.

In some embodiments is a compound of Formula (II) or (II'), or a pharmaceutically acceptable salt or solvate thereof, wherein R$^3$ is C$_{1-6}$alkyl optionally substituted with one, two, or three R$^{20b}$. In some embodiments is a compound of Formula (II) or (II'), or a pharmaceutically acceptable salt or solvate thereof, wherein R$^3$ is —OR$^{12}$. In some embodiments is a compound of Formula (II) or (II'), or a pharmaceutically acceptable salt or solvate thereof, wherein R$^3$ is —N(R$^{12}$)(R$^{13}$). In some embodiments is a compound of Formula (II) or (II'), or a pharmaceutically acceptable salt or solvate thereof, wherein R$^3$ is halogen.

In embodiments of a compound of Formula (II) or (II'), or a pharmaceutically acceptable salt or solvate thereof, R$^3$ is C$_{3-14}$cycloalkyl, including C$_{6-14}$cycloalkyl, C$_{6-9}$cycloalkyl, C$_{3-7}$cycloalkyl, C$_{3-6}$cycloalkyl, C$_{3-5}$cycloalkyl, and C$_{3-4}$cycloalkyl, each of which being optionally substituted with one, two, or three R$^{20b}$. In embodiments of a compound of Formula (II) or (II'), or a pharmaceutically acceptable salt or solvate thereof, R$^3$ is C$_{6-14}$cycloalkyl optionally substituted with one, two, or three R$^{20b}$. In embodiments of a compound of Formula (II) or (II'), or a pharmaceutically acceptable salt or solvate thereof, R$^3$ is C$_{6-9}$ cycloalkyl optionally substituted with one, two, or three R$^{20b}$. In embodiments of a compound of Formula (II) or (II'), or a pharmaceutically acceptable salt or solvate thereof, R$^3$ is C$_{3-7}$cycloalkyl optionally substituted with one, two, or three R$^{20b}$. In embodiments of a compound of Formula (II) or (II'), or a pharmaceutically acceptable salt or solvate thereof, R$^3$ is C$_{3-6}$cycloalkyl optionally substituted with one, two, or three R$^{20b}$. In embodiments of a compound of Formula (II) or (II'), or a pharmaceutically acceptable salt or solvate thereof, R$^3$ is C$_{3-5}$cycloalkyl optionally substituted with one, two, or three R$^{20b}$. In embodiments of a compound of Formula (II) or (II'), or a pharmaceutically acceptable salt or solvate thereof, R$^3$ is C$_{3-4}$cycloalkyl optionally substituted with one, two, or three R$^{20b}$.

In embodiments of a compound of Formula (II) or (II'), or a pharmaceutically acceptable salt or solvate thereof, R$^3$ is C$_{3-14}$cycloalkyl, including C$_{6-14}$cycloalkyl, C$_{6-9}$cycloalkyl, C$_{3-7}$cycloalkyl, C$_{3-6}$cycloalkyl, C$_{3-5}$cycloalkyl, and C$_{3-4}$cycloalkyl, each of which being substituted with one, two, or three R$^{20b}$. In embodiments of a compound of Formula (II) or (II'), or a pharmaceutically acceptable salt or solvate thereof, R$^3$ is C$_{6-14}$cycloalkyl substituted with one, two, or three R$^{20b}$. In embodiments of a compound of Formula (II) or (II'), or a pharmaceutically acceptable salt or solvate thereof, R$^3$ is C$_{6-9}$cycloalkyl substituted with one, two, or three R$^{20b}$. In embodiments of a compound of Formula (II) or (II'), or a pharmaceutically acceptable salt or solvate thereof, R$^3$ is C$_{3-7}$cycloalkyl substituted with one, two, or three R$^{20b}$. In embodiments of a compound of Formula (II) or (II'), or a pharmaceutically acceptable salt or solvate thereof, R$^3$ is C$_{3-6}$cycloalkyl substituted with one, two, or three R$^{20b}$. In embodiments of a compound of Formula (II) or (II'), or a pharmaceutically acceptable salt or solvate thereof, R$^3$ is C$_{3-5}$cycloalkyl substituted with one, two, or three R$^{20b}$. In embodiments of a compound of Formula (II) or (II'), or a pharmaceutically acceptable salt or solvate thereof, R$^3$ is C$_{3-4}$cycloalkyl substituted with one, two, or three R$^{20b}$.

In embodiments of a compound of Formula (II) or (II'), or a pharmaceutically acceptable salt or solvate thereof, R$^3$ is C$_{3-14}$cycloalkyl, including C$_{6-14}$cycloalkyl, C$_{6-9}$cycloalkyl, C$_{3-7}$cycloalkyl, C$_{3-6}$cycloalkyl, C$_{3-5}$cycloalkyl, and C$_{3-4}$cycloalkyl, each of which being optionally substituted with one R$^{20b}$. In embodiments of a compound of Formula (II) or (II'), or a pharmaceutically acceptable salt or solvate thereof, R$^3$ is C$_{6-14}$cycloalkyl optionally substituted with one R$^{20b}$. In embodiments of a compound of Formula (II) or (II'), or a pharmaceutically acceptable salt or solvate thereof, R$^3$ is C$_{6-9}$cycloalkyl optionally substituted with one R$^{20b}$. In embodiments of a compound of Formula (II) or (II'), or a pharmaceutically acceptable salt or solvate thereof, R$^3$ is C$_{3-7}$cycloalkyl optionally substituted with one R$^{20b}$. In embodiments of a compound of Formula (II) or (II'), or a pharmaceutically acceptable salt or solvate thereof, R$^3$ is C$_{3-6}$cycloalkyl optionally substituted with one R$^{20b}$. In embodiments of a compound of Formula (II) or (II'), or a pharmaceutically acceptable salt or solvate thereof, $R^3$ is $C_{3-5}$cycloalkyl optionally substituted with one $R^{20b}$. In embodiments of a compound of Formula (II) or (II'), or a pharmaceutically acceptable salt or solvate thereof, $R^3$ is $C_{3-4}$cycloalkyl optionally substituted with one $R^{20b}$.

In embodiments of a compound of Formula (II) or (II'), or a pharmaceutically acceptable salt or solvate thereof, $R^3$ is $C_{3-14}$cycloalkyl, including $C_{6-14}$cycloalkyl, $C_{6-9}$cycloalkyl, $C_{3-7}$cycloalkyl, $C_{3-6}$cycloalkyl, $C_{3-5}$cycloalkyl, and $C_{3-4}$cycloalkyl, each of which being optionally substituted with two $R^{20b}$. In embodiments of a compound of Formula (II) or (II'), or a pharmaceutically acceptable salt or solvate thereof, $R^3$ is $C_{6-14}$cycloalkyl optionally substituted with two $R^{20b}$. In embodiments of a compound of Formula (II) or (II'), or a pharmaceutically acceptable salt or solvate thereof, $R^3$ is $C_{6-9}$cycloalkyl optionally substituted with two $R^{20b}$. In embodiments of a compound of Formula (II) or (II'), or a pharmaceutically acceptable salt or solvate thereof, $R^3$ is $C_{3-7}$cycloalkyl optionally substituted with two $R^{20b}$. In embodiments of a compound of Formula (II) or (II'), or a pharmaceutically acceptable salt or solvate thereof, $R^3$ is $C_{3-6}$cycloalkyl optionally substituted with one $R^{20b}$. In embodiments of a compound of Formula (II) or (II'), or a pharmaceutically acceptable salt or solvate thereof, $R^3$ is $C_{3-5}$cycloalkyl optionally substituted with two $R^{20b}$. In embodiments of a compound of Formula (II) or (II'), or a pharmaceutically acceptable salt or solvate thereof, $R^3$ is $C_{3-4}$cycloalkyl optionally substituted with two $R^{20b}$.

In each of the above embodiments, $R^{2b}$ is independently selected from amino, —CN, $C_{1-3}$alkyl, $C_{1-3}$alkoxy, $C_{1-3}$haloalkyl, —OH, —N($R^{24}$)C(O)$R^{25}$, and —C(O)N($R^{22}$)($R^{23}$). In some embodiments of a compound of Formula (II) or (II'), or a pharmaceutically acceptable salt or solvate thereof, $R^{20b}$ is amino. In some embodiments of a compound of Formula (II) or (II'), or a pharmaceutically acceptable salt or solvate thereof, $R^{20b}$ is —CN. In some embodiments of a compound of Formula (II) or (II'), or a pharmaceutically acceptable salt or solvate thereof, $R^{20b}$ is $C_{1-3}$alkyl. In some embodiments of a compound of Formula (II) or (II'), or a pharmaceutically acceptable salt or solvate thereof, $R^{20b}$ is $C_{1-3}$alkoxy. In some embodiments of a compound of Formula (II) or (II'), or a pharmaceutically acceptable salt or solvate thereof, $R^{20b}$ is $C_{1-3}$haloalkyl. In some embodiments of a compound of Formula (II) or (II'), or a pharmaceutically acceptable salt or solvate thereof, $R^{20b}$ is —OH. In some embodiments of a compound of Formula (II) or (II'), or a pharmaceutically acceptable salt or solvate thereof, $R^{20b}$ is —N($R^{24}$)C(O)$R^{25}$. In some embodiments of a compound of Formula (II) or (II'), or a pharmaceutically acceptable salt or solvate thereof, $R^{20b}$ is —C(O)N($R^{22}$)($R^{23}$). In some embodiments of a compound of Formula (II) or (II'), or a pharmaceutically acceptable salt or solvate thereof, $R^{20b}$ is —NHC(O)$R^{25}$. In some embodiments of a compound of Formula (II) or (II'), or a pharmaceutically acceptable salt or solvate thereof, $R^{20b}$ is —C(O)NH($R^{22}$). In some embodiments of a compound of Formula (II) or (II'), or a pharmaceutically acceptable salt or solvate thereof, $R^{20b}$ is —NHC(O)$R^{25}$ and $R^{25}$ is $C_{2-9}$heterocycloalkyl optionally substituted with one, two, or three groups independently selected from halogen, $C_{1-6}$alkyl, $C_{1-6}$haloalkyl, $C_{1-6}$alkoxy, $C_{3-7}$cycloalkyl, $C_{2-9}$heterocycloalkyl, $C_{6-10}$aryl, and $C_{1-9}$heteroaryl. In some embodiments of a compound of Formula (II) or (II'), or a pharmaceutically acceptable salt or solvate thereof, $R^{20b}$ is —C(O)NH($R^{22}$) and $R^{22}$ is $C_{2-9}$heterocycloalkyl optionally substituted with one, two, or three groups independently selected from halogen and $C_{1-6}$alkyl. In some embodiments of a compound of Formula (II) or (II'), or a pharmaceutically acceptable salt or solvate thereof, $R^{20b}$ is —NHC(O)$R^{25}$ and $R^{25}$ is $C_{2-5}$heterocycloalkyl optionally substituted with one $C_{1-6}$alkyl. In some embodiments of a compound of Formula (II) or (II'), or a pharmaceutically acceptable salt or solvate thereof, $R^{20b}$ is —C(O)NH($R^{22}$) and $R^{22}$ is $C_{2-5}$heterocycloalkyl optionally substituted with one $C_{1-6}$alkyl.

In embodiments of a compound of Formula (II) or (II'), or a pharmaceutically acceptable salt or solvate thereof, $R^3$ is $C_{6-14}$cycloalkyl (including $C_{6-14}$cycloalkyl, $C_{6-9}$cycloalkyl, $C_{3-7}$cycloalkyl, $C_{3-6}$cycloalkyl, $C_{3-5}$cycloalkyl, and $C_{3-4}$cycloalkyl), optionally substituted with one, two, or three $R^{20b}$ that is amino. In embodiments of a compound of Formula (II) or (II'), or a pharmaceutically acceptable salt or solvate thereof, $R^3$ is $C_{6-14}$cycloalkyl (including $C_{6-14}$cycloalkyl, $C_{6-9}$cycloalkyl, $C_{3-7}$cycloalkyl, $C_{3-6}$cycloalkyl, $C_{3-5}$cycloalkyl, and $C_{3-4}$cycloalkyl), optionally substituted with one, two, or three $R^{20b}$ that is —CN. In embodiments of a compound of Formula (II) or (II'), or a pharmaceutically acceptable salt or solvate thereof, $R^3$ is $C_{6-14}$cycloalkyl (including $C_{6-14}$cycloalkyl, $C_{6-9}$cycloalkyl, $C_{3-7}$cycloalkyl, $C_{3-6}$cycloalkyl, $C_{3-5}$cycloalkyl, and $C_{3-4}$cycloalkyl), optionally substituted with one, two, or three $R^{20b}$ that is $C_{1-3}$alkyl. In embodiments of a compound of Formula (II) or (II'), or a pharmaceutically acceptable salt or solvate thereof, $R^3$ is $C_{6-14}$cycloalkyl (including $C_{6-14}$cycloalkyl, $C_{6-9}$cycloalkyl, $C_{3-7}$cycloalkyl, $C_{3-6}$cycloalkyl, $C_{3-5}$cycloalkyl, and $C_{3-4}$cycloalkyl), optionally substituted with one, two, or three $R^{20b}$ that is $C_{1-3}$alkoxy. In embodiments of a compound of Formula (II) or (II'), or a pharmaceutically acceptable salt or solvate thereof, $R^3$ is $C_{6-14}$cycloalkyl (including $C_{6-14}$cycloalkyl, $C_{6-9}$cycloalkyl, $C_{3-7}$cycloalkyl, $C_{3-6}$cycloalkyl, $C_{3-5}$cycloalkyl, and $C_{3-4}$cycloalkyl), optionally substituted with one, two, or three $R^{20b}$ that is $C_{1-3}$haloalkyl. In embodiments of a compound of Formula (II) or (II'), or a pharmaceutically acceptable salt or solvate thereof, $R^3$ is $C_{6-14}$cycloalkyl (including $C_{6-14}$cycloalkyl, $C_{6-9}$cycloalkyl, $C_{3-7}$cycloalkyl, $C_{3-6}$cycloalkyl, $C_{3-5}$cycloalkyl, and $C_{3-4}$cycloalkyl), optionally substituted with one, two, or three $R^{20b}$ that is —OH. In embodiments of a compound of Formula (II) or (II'), or a pharmaceutically acceptable salt or solvate thereof, $R^3$ is $C_{6-14}$cycloalkyl (including $C_{6-14}$cycloalkyl, $C_{6-9}$cycloalkyl, $C_{3-7}$cycloalkyl, $C_{3-6}$cycloalkyl, $C_{3-5}$cycloalkyl, and $C_{3-4}$cycloalkyl), optionally substituted with one, two, or three $R^{20b}$ that is oxo. In embodiments of a compound of Formula (II) or (II'), or a pharmaceutically acceptable salt or solvate thereof, $R^3$ is $C_{6-14}$cycloalkyl (including $C_{6-14}$cycloalkyl, $C_{6-9}$cycloalkyl, $C_{3-7}$cycloalkyl, $C_{3-6}$cycloalkyl, $C_{3-5}$cycloalkyl, and $C_{3-4}$cycloalkyl), optionally substituted with one, two, or three $R^{20b}$ that is —N($R^{24}$)C(O)$R^{25}$. In embodiments of a compound of Formula (II) or (II'), or a pharmaceutically acceptable salt or solvate thereof, $R^3$ is $C_{6-14}$cycloalkyl (including $C_{6-14}$cycloalkyl, $C_{6-9}$cycloalkyl, $C_{3-7}$cycloalkyl, $C_{3-6}$cycloalkyl, $C_{3-5}$cycloalkyl, and $C_{3-4}$cycloalkyl), optionally substituted with one, two, or three $R^{20b}$ that is —NHC(O)$R^{25}$. In embodiments of a compound of Formula (II) or (II'), or a pharmaceutically acceptable salt or solvate thereof, $R^3$ is $C_{6-14}$cycloalkyl (including $C_{6-14}$cycloalkyl, $C_{6-9}$cycloalkyl, $C_{3-7}$cycloalkyl, $C_{3-6}$cycloalkyl, $C_{3-5}$cycloalkyl, and $C_{3-4}$cycloalkyl), optionally substituted with one, two, or three $R^{20b}$ that is —NHC(O)$R^{25}$ and $R^{25}$ is $C_{2-9}$heterocycloalkyl optionally substituted with one, two, or three groups independently selected from halogen, $C_{1-6}$alkyl, $C_{1-6}$haloalkyl, $C_{1-6}$alkoxy, $C_{3-7}$cycloalkyl, $C_{2-9}$heterocycloalkyl, $C_{6-10}$aryl, and $C_{1-9}$heteroaryl. In embodiments of a compound of Formula (II) or (II'), or a pharmaceutically acceptable salt or solvate thereof, $R^3$ is $C_{6-14}$cycloalkyl (including $C_{6-14}$cycloalkyl, $C_{6-9}$cycloalkyl, $C_{3-7}$cycloalkyl, $C_{3-6}$cycloalkyl, $C_{3-5}$cycloalkyl, and $C_{3-4}$cycloalkyl), optionally substituted with one, two, or three $R^{20b}$ that is —NHC(O)$R^{25}$ and $R^{25}$ is $C_{2-5}$heterocycloalkyl optionally substituted with one $C_{1-6}$alkyl. In embodiments of a compound of Formula (II) or (II'), or a pharmaceutically acceptable salt or solvate thereof, $R^3$ is $C_{6-14}$cycloalkyl (including $C_{6-14}$cycloalkyl, $C_{6-9}$cycloalkyl, $C_{3-7}$cycloalkyl, $C_{3-6}$cycloalkyl, $C_{3-5}$cycloalkyl, and $C_{3-4}$cycloalkyl), optionally substituted with one, two, or three $R^{20b}$ that is —C(O)N($R^{22}$)($R^{23}$). In embodiments of a compound of Formula (II) or (II'), or a pharmaceutically acceptable salt or solvate thereof, $R^3$ is $C_{6-14}$cycloalkyl (including $C_{6-14}$cycloalkyl, $C_{6-9}$cycloalkyl, $C_{3-7}$cycloalkyl, $C_{3-6}$cycloalkyl, $C_{3-5}$cycloalkyl, and $C_{3-4}$cycloalkyl), optionally substituted with one, two, or three $R^{20b}$ that is —C(O)NH($R^{22}$). In embodiments of a compound of Formula (II) or (II'), or a pharmaceutically acceptable salt or solvate thereof, $R^3$ is $C_{6-14}$cycloalkyl (including $C_{6-14}$cycloalkyl, $C_{6-9}$cycloalkyl, $C_{3-7}$cycloalkyl, $C_{3-6}$cycloalkyl, $C_{3-5}$cycloalkyl, and $C_{3-4}$cycloalkyl), optionally substituted with one, two, or three $R^{20b}$ that is —C(O)NH($R^{22}$) and $R^{22}$ is $C_{2-9}$heterocycloalkyl optionally substituted with one, two, or three groups independently selected from halogen and $C_{1-6}$alkyl. In embodiments of a compound of Formula (II) or (II'), or a pharmaceutically acceptable salt or solvate thereof, $R^3$ is $C_{6-14}$cycloalkyl (including $C_{6-14}$cycloalkyl, $C_{6-9}$cycloalkyl, $C_{3-7}$cycloalkyl, $C_{3-6}$cycloalkyl, $C_{3-5}$cycloalkyl, and $C_{3-4}$cycloalkyl), optionally substituted with one, two, or three $R^{20b}$ that is —C(O)NH($R^{22}$) and $R^{22}$ is $C_{2-5}$heterocycloalkyl optionally substituted with one $C_{1-6}$alkyl.

In embodiments of a compound of Formula (II) or (II'), or a pharmaceutically acceptable salt or solvate thereof, $R^3$ is $C_{2-9}$heterocycloalkyl, including $C_{6-9}$heterocycloalkyl, $C_{3-7}$heterocycloalkyl, $C_{3-6}$heterocycloalkyl, $C_{5-6}$ heterocycloalkyl, $C_{3-5}$heterocycloalkyl, $C_{3-4}$heterocycloalkyl, each of which being optionally substituted with one, two, or three $R^{20b}$. In embodiments of a compound of Formula (II) or (II'), or a pharmaceutically acceptable salt or solvate thereof, $R^3$ is $C_{6-9}$heterocycloalkyl optionally substituted with one, two, or three $R^{20b}$. In embodiments of a compound of Formula (II) or (II'), or a pharmaceutically acceptable salt or solvate thereof, $R^3$ is $C_{3-7}$heterocycloalkyl optionally substituted with one, two, or three $R^{20b}$. In embodiments of a compound of Formula (II) or (II'), or a pharmaceutically acceptable salt or solvate thereof, $R^3$ is $C_{3-6}$heterocycloalkyl optionally substituted with one, two, or three $R^{20b}$. In embodiments of a compound of Formula (II) or (II'), or a pharmaceutically acceptable salt or solvate thereof, $R^3$ is $C_{5-6}$heterocycloalkyl optionally substituted with one, two, or three $R^{20b}$. In embodiments of a compound of Formula (II) or (II'), or a pharmaceutically acceptable salt or solvate thereof, $R^3$ is $C_{3-5}$ heterocycloalkyl optionally substituted with one, two, or three $R^{20b}$. In embodiments of a compound of Formula (II) or (II'), or a pharmaceutically acceptable salt or solvate thereof, $R^3$ is $C_{3-4}$heterocycloalkyl optionally substituted with one, two, or three $R^{20b}$.

In embodiments, each of the $R^3$ described above including $C_{6-9}$heterocycloalkyl, $C_{3-7}$heterocycloalkyl, $C_{3-6}$heterocycloalkyl, $C_{5-6}$ heterocycloalkyl, $C_{3-5}$heterocycloalkyl, $C_{3-4}$heterocycloalkyl, is optionally substituted with one $R^{20b}$. In embodiments, each of the $R^3$ described above, including $C_{6-9}$heterocycloalkyl, $C_{3-7}$heterocycloalkyl, $C_{3-6}$heterocycloalkyl, $C_{5-6}$ heterocycloalkyl, $C_{3-5}$heterocycloalkyl, $C_{3-4}$heterocycloalkyl, is optionally substituted with two $R^{20b}$. In embodiments, each of the $R^3$ described above, including $C_{6-9}$heterocycloalkyl, $C_{3-7}$heterocycloalkyl, $C_{3-6}$heterocycloalkyl, $C_{5-6}$ heterocycloalkyl, $C_{3-5}$heterocycloalkyl, $C_{3-4}$heterocycloalkyl, is optionally substituted with three $R^{20b}$.

In each of the above embodiments, $R^{20b}$ is independently selected from amino, —CN, $C_{1-3}$alkyl, $C_{1-3}$alkoxy, $C_{1-3}$haloalkyl, —OH, —N($R^{24}$)C(O)$R^{25}$, and —C(O)N($R^{22}$)($R^{23}$). In some embodiments of a compound of Formula (II) or (II'), or a pharmaceutically acceptable salt or solvate thereof, $R^{20b}$ is amino. In some embodiments of a compound of Formula (II) or (II'), or a pharmaceutically acceptable salt or solvate thereof, $R^{20b}$ is —CN. In some embodiments of a compound of Formula (II) or (II'), or a pharmaceutically acceptable salt or solvate thereof, $R^{20b}$ is $C_{1-3}$alkyl. In some embodiments of a compound of Formula (II) or (II'), or a pharmaceutically acceptable salt or solvate thereof, $R^{20b}$ is $C_{1-3}$alkoxy. In some embodiments of a compound of Formula (II) or (II'), or a pharmaceutically acceptable salt or solvate thereof, $R^{20b}$ is $C_{1-3}$haloalkyl. In some embodiments of a compound of Formula (II) or (II'), or a pharmaceutically acceptable salt or solvate thereof, $R^{20b}$ is —OH. In some embodiments of a compound of Formula (II) or (II'), or a pharmaceutically acceptable salt or solvate thereof, $R^{20b}$ is —N($R^{24}$)C(O)$R^{25}$. In some embodiments of a compound of Formula (II) or (II'), or a pharmaceutically acceptable salt or solvate thereof, $R^{20b}$ is —C(O)N($R^{22}$)($R^{23}$). In some embodiments of a compound of Formula (II) or (II'), or a pharmaceutically acceptable salt or solvate thereof, $R^{20b}$ is —NHC(O)$R^{25}$. In some embodiments of a compound of Formula (II) or (II'), or a pharmaceutically acceptable salt or solvate thereof, $R^{20b}$ is —C(O)NH($R^{22}$). In some embodiments of a compound of Formula (II) or (II'), or a pharmaceutically acceptable salt or solvate thereof, $R^{20b}$ is —NHC(O)$R^{25}$ and $R^{25}$ is $C_{2-9}$heterocycloalkyl optionally substituted with one, two, or three groups independently selected from halogen, $C_{1-6}$alkyl, $C_{1-6}$haloalkyl, $C_{1-6}$alkoxy, $C_{3-7}$cycloalkyl, $C_{2-9}$heterocycloalkyl, $C_{6-10}$aryl, and $C_{1-9}$heteroaryl. In some embodiments of a compound of Formula (II) or (II'), or a pharmaceutically acceptable salt or solvate thereof, $R^{20b}$ is —C(O)NH($R^{22}$) and $R^{22}$ is $C_{2-9}$heterocycloalkyl optionally substituted with one, two, or three groups independently selected from halogen and $C_{1-6}$alkyl. In some embodiments of a compound of Formula (II) or (II'), or a pharmaceutically acceptable salt or solvate thereof, $R^{20b}$ is —NHC(O)$R^{25}$ and $R^{25}$ is $C_{2-5}$heterocycloalkyl optionally substituted with one $C_{1-6}$alkyl. In some embodiments of a compound of Formula (II) or (II'), or a pharmaceutically acceptable salt or solvate thereof, $R^{20b}$ is —C(O)NH($R^{22}$) and $R^{22}$ is $C_{2-5}$heterocycloalkyl optionally substituted with one $C_{1-6}$alkyl.

In embodiments of a compound of Formula (II) or (II'), or a pharmaceutically acceptable salt or solvate thereof, $R^3$ is $C_{2-9}$heterocycloalkyl (including $C_{6-9}$heterocycloalkyl, $C_{3-7}$heterocycloalkyl, $C_{3-6}$heterocycloalkyl, $C_{5-6}$heterocycloalkyl, $C_{3-5}$heterocycloalkyl, and $C_{3-4}$heterocycloalkyl), optionally substituted with one, two, or three $R^{20b}$ that is amino. In embodiments of a compound of Formula (II) or (II'), or a pharmaceutically acceptable salt or solvate thereof, $R^3$ is $C_{2-9}$heterocycloalkyl (including $C_{6-9}$ heterocycloalkyl, $C_{3-7}$heterocycloalkyl, $C_{3-6}$heterocycloalkyl, $C_{5-6}$heterocycloalkyl, $C_{3-5}$heterocycloalkyl, and $C_{3-4}$heterocycloalkyl), optionally substituted with one, two, or three $R^{20b}$ that is —CN. In embodiments of a compound of Formula (II) or (II'), or a pharmaceutically acceptable salt or solvate thereof, $R^3$ is $C_{2-9}$heterocycloalkyl (including $C_{6-9}$heterocycloalkyl, $C_{3-7}$heterocycloalkyl, $C_{3-6}$heterocycloalkyl, $C_{5-6}$heterocycloalkyl, $C_{3-5}$heterocycloalkyl, and $C_{3-4}$heterocycloalkyl), optionally substituted with one, two, or three $R^{20b}$ that is $C_{1-3}$alkyl. In embodiments of a compound of Formula (II) or (II'), or a pharmaceutically acceptable salt or solvate thereof, $R^3$ is $C_{2-9}$heterocycloalkyl (including $C_{6-9}$heterocycloalkyl, $C_{3-7}$heterocycloalkyl, $C_{3-6}$heterocycloalkyl, $C_{5-6}$heterocycloalkyl, $C_{3-5}$heterocycloalkyl, and $C_{3-4}$heterocycloalkyl), optionally substituted with one, two, or three $R^{2b}$ that is $C_{1-3}$alkoxy. In embodiments of a compound of Formula (II) or (II'), or a pharmaceutically acceptable salt or solvate thereof, $R^3$ is $C_{2-9}$heterocycloalkyl (including $C_{6-9}$heterocycloalkyl, $C_{3-7}$heterocycloalkyl, $C_{3-6}$heterocycloalkyl, $C_{5-6}$heterocycloalkyl, $C_{3-5}$heterocycloalkyl, and $C_{3-4}$heterocycloalkyl), optionally substituted with one, two, or three $R^{20b}$ that is $C_{1-3}$haloalkyl. In embodiments of a compound of Formula (II) or (II'), or a pharmaceutically acceptable salt or solvate thereof, $R^3$ is $C_{2-9}$heterocycloalkyl (including $C_{6-9}$heterocycloalkyl, $C_{3-7}$heterocycloalkyl, $C_{3-6}$heterocycloalkyl, $C_{5-6}$heterocycloalkyl, $C_{3-5}$heterocycloalkyl, and $C_{3-4}$heterocycloalkyl), optionally substituted with one, two, or three $R^{20b}$ that is —OH. In embodiments of a compound of Formula (II) or (II'), or a pharmaceutically acceptable salt or solvate thereof, $R^3$ is $C_{2-9}$heterocycloalkyl (including $C_{6-9}$heterocycloalkyl, $C_{3-7}$heterocycloalkyl, $C_{3-6}$heterocycloalkyl, $C_{5-6}$heterocycloalkyl, $C_{3-5}$heterocycloalkyl, and $C_{3-4}$heterocycloalkyl), optionally substituted with one, two, or three $R^{20b}$ that is oxo. In embodiments of a compound of Formula (II) or (II'), or a pharmaceutically acceptable salt or solvate thereof, $R^3$ is $C_{2-9}$heterocycloalkyl (including $C_{6-9}$ heterocycloalkyl, $C_{3-7}$heterocycloalkyl, $C_{3-6}$heterocycloalkyl, $C_{5-6}$heterocycloalkyl, $C_{3-5}$heterocycloalkyl, and $C_{3-4}$heterocycloalkyl), optionally substituted with one, two, or three $R^{20b}$ that is —N($R^{24}$)C(O)$R^{25}$. In embodiments of a compound of Formula (II) or (II'), or a pharmaceutically acceptable salt or solvate thereof, $R^3$ is $C_{2-9}$heterocycloalkyl (including $C_{6-9}$heterocycloalkyl, $C_{3-7}$heterocycloalkyl, $C_{3-6}$heterocycloalkyl, $C_{5-6}$heterocycloalkyl, $C_{3-5}$heterocycloalkyl, and $C_{3-4}$heterocycloalkyl), optionally substituted with one, two, or three $R^{20b}$ that is —NHC(O)$R^{25}$. In embodiments of a compound of Formula (II) or (II'), or a pharmaceutically acceptable salt or solvate thereof, $R^3$ is $C_{2-9}$heterocycloalkyl (including $C_{6-9}$heterocycloalkyl, $C_{3-7}$heterocycloalkyl, $C_{3-6}$heterocycloalkyl, $C_{5-6}$ heterocycloalkyl, $C_{3-5}$heterocycloalkyl, and $C_{3-4}$heterocycloalkyl), optionally substituted with one, two, or three $R^{20b}$ that is —NHC(O)$R^{25}$ and $R^{25}$ is $C_{2-9}$heterocycloalkyl optionally substituted with one, two, or three groups independently selected from halogen, $C_{1-6}$alkyl, $C_{1-6}$haloalkyl, $C_{1-6}$alkoxy, $C_{3-7}$cycloalkyl, $C_{2-9}$heterocycloalkyl, $C_{6-10}$aryl, and $C_{1-9}$heteroaryl. In embodiments of a compound of Formula (II) or (II'), or a pharmaceutically acceptable salt or solvate thereof, $R^3$ is $C_{2-9}$heterocycloalkyl (including $C_{6-9}$ heterocycloalkyl, $C_{3-7}$heterocycloalkyl, $C_{3-6}$heterocycloalkyl, $C_{5-6}$heterocycloalkyl, $C_{3-5}$heterocycloalkyl, and $C_{3-4}$heterocycloalkyl), optionally substituted with one, two, or three $R^{20b}$ that is —NHC(O)$R^{25}$ and $R^{25}$ is $C_{2-5}$heterocycloalkyl optionally substituted with one $C_{1-6}$alkyl. In embodiments of a compound of Formula (II) or (II'), or a pharmaceutically acceptable salt or solvate thereof, $R^3$ is $C_{2-9}$heterocycloalkyl (including $C_{6-9}$heterocycloalkyl, $C_{3-7}$heterocycloalkyl, $C_{3-6}$heterocycloalkyl, $C_{5-6}$heterocycloalkyl, $C_{3-5}$heterocycloalkyl, and $C_{3-4}$heterocycloalkyl), optionally substituted with one, two, or three $R^{20b}$ that is —C(O)N($R^{22}$)($R^{23}$). In embodiments of a compound of Formula (II) or (II'), or a pharmaceutically acceptable salt or solvate thereof, $R^3$ is $C_{2-9}$heterocycloalkyl (including $C_{6-9}$heterocycloalkyl, $C_{3-7}$heterocycloalkyl, $C_{3-6}$heterocycloalkyl, $C_{5-6}$heterocycloalkyl, $C_{3-5}$heterocycloalkyl, and $C_{3-4}$heterocycloalkyl), optionally substituted with one, two, or three $R^{20b}$ that is —C(O)NH($R^{22}$). In embodiments of a compound of Formula (II) or (II'), or a pharmaceutically acceptable salt or solvate thereof, $R^3$ is $C_{2-9}$heterocycloalkyl (including $C_{6-9}$heterocycloalkyl, $C_{3-7}$heterocycloalkyl, $C_{3-6}$heterocycloalkyl, $C_{5-6}$heterocycloalkyl, $C_{3-5}$heterocycloalkyl, and $C_{3-4}$heterocycloalkyl), optionally substituted with one, two, or three $R^{20b}$ that is —C(O)NH($R^{22}$) and $R^{22}$ is $C_{2-9}$heterocycloalkyl optionally substituted with one, two, or three groups independently selected from halogen and $C_{1-6}$alkyl. In embodiments of a compound of Formula (II) or (II'), or a pharmaceutically acceptable salt or solvate thereof, $R^3$ is $C_{2-9}$heterocycloalkyl (including $C_{6-9}$heterocycloalkyl, $C_{3-7}$heterocycloalkyl, $C_{3-6}$heterocycloalkyl, $C_{5-6}$heterocycloalkyl, $C_{3-5}$heterocycloalkyl, and $C_{3-4}$heterocycloalkyl), optionally substituted with one, two, or three $R^{20b}$ that is —C(O)NH($R^{22}$) and $R^{22}$ is $C_{2-5}$heterocycloalkyl optionally substituted with one $C_{1-6}$alkyl.

In embodiments of a compound of Formula (II) or (II'), or a pharmaceutically acceptable salt or solvate thereof, $R^3$ is thianyl substituted with one, two, or three $R^{20b}$. In embodiments of a compound of Formula (II) or (II'), or a pharmaceutically acceptable salt or solvate thereof, $R^3$ is monovalent tetrahydro-2H-thiopyran 1,1-dioxide substituted with one, two, or three $R^{20b}$. In embodiments of a compound of Formula (II) or (II'), or a pharmaceutically acceptable salt or solvate thereof, $R^3$ is monovalent $4\lambda^2$-thiomorpholine substituted with two $R^{20b}$. In embodiments of a compound of Formula (II) or (II'), or a pharmaceutically acceptable salt or solvate thereof, $R^3$ is tetrahydro-2H-thiopyranyl 1,1-dioxide. In embodiments of a compound of Formula (II) or (II'), or a pharmaceutically acceptable salt or solvate thereof, $R^3$ is $4\lambda^2$-thiomorpholinyl substituted with two $R^{20b}$. In embodiments of a compound of Formula (II) or (II'), or a pharmaceutically acceptable salt or solvate thereof, $R^3$ is piperidinyl substituted with one $R^{20b}$. In embodiments of a compound of Formula (II) or (II'), or a pharmaceutically acceptable salt or solvate thereof, $R^3$ is piperazinyl substituted with one $R^{20b}$. In embodiments of a compound of Formula (II) or (II'), or a pharmaceutically acceptable salt or solvate thereof, $R^3$ is pyrrolidinyl substituted with one $R^{20b}$.

In embodiments of a compound of Formula (II) or (II'), or a pharmaceutically acceptable salt or solvate thereof, $R^3$ is $C_{2-9}$heterocycloalkyl substituted with one methyl. In embodiments of a compound of Formula (II) or (II'), or a pharmaceutically acceptable salt or solvate thereof, $R^3$ is $C_{6-9}$heterocycloalkyl substituted with one methyl, one ethyl, or one propyl. In embodiments of a compound of Formula (II) or (II'), or a pharmaceutically acceptable salt or solvate thereof, $R^3$ is $C_{3-7}$heterocycloalkyl substituted with one methyl, one ethyl, or one propyl. In embodiments of a compound of Formula (II) or (II'), or a pharmaceutically acceptable salt or solvate thereof, $R^3$ is $C_{3-6}$heterocycloalkyl substituted with one methyl, one ethyl, or one propyl. In embodiments of a compound of Formula (II) or (II'), or a pharmaceutically acceptable salt or solvate thereof, $R^3$ is $C_{5-6}$ heterocycloalkyl substituted with one methyl, one ethyl, or one propyl. In embodiments of a compound of Formula (II) or (II'), or a pharmaceutically acceptable salt or solvate thereof, $R^3$ is $C_{5-6}$heterocycloalkyl substituted with one methyl, one ethyl, or one propyl. In embodiments of a compound of Formula (II) or (II'), or a pharmaceutically acceptable salt or solvate thereof, $R^3$ is $C_{3-4}$heterocycloalkyl substituted with one methyl, one ethyl, or one propyl. In embodiments of a compound of Formula (II) or (II'), or a pharmaceutically acceptable salt or solvate thereof, $R^3$ is $C_{2-7}$heterocycloalkyl substituted with one methyl, one ethyl, or one propyl. In embodiments of a compound of Formula (II) or (II'), or a pharmaceutically acceptable salt or solvate thereof, $R^3$ is $C_{4-7}$ heterocycloalkyl substituted with one methyl, one ethyl, or one propyl. In embodiments of a compound of Formula (II) or (II'), or a pharmaceutically acceptable salt or solvate thereof, $R^3$ is $C_{4-5}$heterocycloalkyl substituted with one methyl, one ethyl, or one propyl. In embodiments of a compound of Formula (II) or (II'), or a pharmaceutically acceptable salt or solvate thereof, $R^3$ is $C_5$heterocycloalkyl substituted with one methyl, one ethyl, or one propyl. In embodiments of a compound of Formula (II) or (II'), or a pharmaceutically acceptable salt or solvate thereof, $R^3$ is $C_4$heterocycloalkyl substituted with one methyl, one ethyl, or one propyl.

In embodiments of a compound of Formula (II) or (II'), or a pharmaceutically acceptable salt or solvate thereof, $R^3$ is $C_{6-9}$heterocycloalkyl substituted with one propyl. In embodiments of a compound of Formula (II) or (II'), or a pharmaceutically acceptable salt or solvate thereof, $R^3$ is $C_{3-7}$heterocycloalkyl substituted with one propyl. In embodiments of a compound of Formula (II) or (II'), or a pharmaceutically acceptable salt or solvate thereof, $R^3$ is $C_{3-6}$heterocycloalkyl substituted with one propyl. In embodiments of a compound of Formula (II) or (II'), or a pharmaceutically acceptable salt or solvate thereof, $R^3$ is $C_{5-6}$ heterocycloalkyl substituted with one propyl. In embodiments of a compound of Formula (II) or (II'), or a pharmaceutically acceptable salt or solvate thereof, $R^3$ is $C_{5-6}$heterocycloalkyl substituted with one propyl. In embodiments of a compound of Formula (II) or (II'), or a pharmaceutically acceptable salt or solvate thereof, $R^3$ is $C_{3-4}$heterocycloalkyl substituted with one propyl. In embodiments of a compound of Formula (II) or (II'), or a pharmaceutically acceptable salt or solvate thereof, $R^3$ is $C_{4-5}$ heterocycloalkyl substituted with one propyl. In embodiments of a compound of Formula (II) or (II'), or a pharmaceutically acceptable salt or solvate thereof, $R^3$ is $C_4$heterocycloalkyl substituted with one propyl. In embodiments of a compound of Formula (II) or (II'), or a pharmaceutically acceptable salt or solvate thereof, $R^3$ is $C_4$heterocycloalkyl substituted with one propyl.

In embodiments of a compound of Formula (II) or (II'), or a pharmaceutically acceptable salt or solvate thereof, $R^3$ is $C_{2-9}$heterocycloalkyl substituted with one isopropyl. In embodiments of a compound of Formula (II) or (II'), or a pharmaceutically acceptable salt or solvate thereof, $R^3$ is $C_{2-7}$heterocycloalkyl substituted with one isopropyl. In embodiments of a compound of Formula (II) or (II'), or a pharmaceutically acceptable salt or solvate thereof, $R^3$ is $C_{4-7}$heterocycloalkyl substituted with one isopropyl. In embodiments of a compound of Formula (II) or (II'), or a pharmaceutically acceptable salt or solvate thereof, $R^3$ is $C_{4-5}$heterocycloalkyl substituted with one isopropyl. In embodiments of a compound of Formula (II) or (II'), or a pharmaceutically acceptable salt or solvate thereof, $R^3$ is $C_5$heterocycloalkyl substituted with one isopropyl. In embodiments of a compound of Formula (II) or (II'), or a pharmaceutically acceptable salt or solvate thereof, $R^3$ is $C_4$heterocycloalkyl substituted with one isopropyl.

In embodiments of a compound of Formula (II) or (II'), or a pharmaceutically acceptable salt or solvate thereof, $R^3$ is $C_{2-9}$heterocycloalkyl substituted with two oxo. In embodiments of a compound of Formula (II) or (II'), or a pharmaceutically acceptable salt or solvate thereof, $R^3$ is $C_{2-7}$heterocycloalkyl substituted with two oxo. In embodiments of a compound of Formula (II) or (II'), or a pharmaceutically acceptable salt or solvate thereof, $R^3$ is $C_{4-7}$heterocycloalkyl substituted with two oxo. In embodiments of a compound of Formula (II) or (II'), or a pharmaceutically acceptable salt or solvate thereof, $R^3$ is $C_{6-9}$heterocycloalkyl substituted with two oxo. In embodiments of a compound of Formula (II) or (II'), or a pharmaceutically acceptable salt or solvate thereof, $R^3$ is $C_{3-7}$heterocycloalkyl substituted with two oxo. In embodiments of a compound of Formula (II) or (II'), or a pharmaceutically acceptable salt or solvate thereof, $R^3$ is $C_{3-6}$heterocycloalkyl substituted with two oxo. In embodiments of a compound of Formula (II) or (II'), or a pharmaceutically acceptable salt or solvate thereof, $R^3$ is $C_{5-6}$heterocycloalkyl substituted with two oxo. In embodiments of a compound of Formula (II) or (II'), or a pharmaceutically acceptable salt or solvate thereof, $R^3$ is $C_{5-6}$heterocycloalkyl substituted with two oxo. In embodiments of a compound of Formula (II) or (II'), or a pharmaceutically acceptable salt or solvate thereof, $R^3$ is $C_{3-4}$heterocycloalkyl substituted with two oxo. In embodiments of a compound of Formula (II) or (II'), or a pharmaceutically acceptable salt or solvate thereof, $R^3$ is $C_{4-5}$heterocycloalkyl substituted with two oxo. In embodiments of a compound of Formula (II) or (II'), or a pharmaceutically acceptable salt or solvate thereof, $R^3$ is $C_5$heterocycloalkyl substituted with two oxo. In embodiments of a compound of Formula (II) or (II'), or a pharmaceutically acceptable salt or solvate thereof, $R^3$ is $C_4$heterocycloalkyl substituted with two oxo.

In embodiments of a compound of Formula (II) or (II'), or a pharmaceutically acceptable salt or solvate thereof, $R^3$ is thianyl, optionally substituted with one, two, or three $R^{20b}$ that is amino. In embodiments of a compound of Formula (II) or (II'), or a pharmaceutically acceptable salt or solvate thereof, $R^3$ is thianyl, optionally substituted with one, two, or three $R^{20b}$ that is —CN. In embodiments of a compound of Formula (II) or (II'), or a pharmaceutically acceptable salt or solvate thereof, $R^3$ is thianyl, optionally substituted with one, two, or three $R^{20b}$ that is $C_{1-3}$alkyl. In embodiments of a compound of Formula (II) or (II'), or a pharmaceutically acceptable salt or solvate thereof, $R^3$ is thianyl, optionally substituted with one, two, or three $R^{20b}$ that is $C_{1-3}$alkoxy. In embodiments of a compound of Formula (II) or (II'), or a pharmaceutically acceptable salt or solvate thereof, $R^3$ is thianyl, optionally substituted with one, two, or three $R^{20b}$ that is $C_{1-3}$haloalkyl. In embodiments of a compound of Formula (II) or (II'), or a pharmaceutically acceptable salt or solvate thereof, $R^3$ is thianyl, optionally substituted with one, two, or three $R^{20b}$ that is —OH. In embodiments of a compound of Formula (II) or (II'), or a pharmaceutically acceptable salt or solvate thereof, $R^3$ is thianyl, optionally substituted with one, two, or three $R^{20b}$ that is oxo. In embodiments of a compound of Formula (II) or (II'), or a pharmaceutically acceptable salt or solvate thereof, $R^3$ is thianyl, optionally substituted with one, two, or three $R^{20b}$ that is —N($R^{24}$)C(O)$R^{25}$. In embodiments of a compound of Formula (II) or (II'), or a pharmaceutically acceptable salt or solvate thereof, $R^3$ is thianyl, optionally substituted with one, two, or three $R^{20b}$ that is —NHC(O)$R^{25}$. In embodiments of a compound of Formula (II) or (II'), or a pharmaceutically acceptable salt or solvate thereof, $R^3$ is thianyl, optionally substituted with one, two, or three $R^{20b}$ that is —NHC(O)$R^{25}$ and $R^{25}$ is $C_{2-9}$heterocycloalkyl optionally substituted with one, two, or three groups independently selected from halogen, $C_{1-6}$alkyl, $C_{1-6}$haloalkyl, $C_{1-6}$alkoxy, $C_{3-7}$cycloalkyl, $C_{2-9}$heterocycloalkyl, $C_{6-10}$aryl, and $C_{1-9}$heteroaryl. In embodiments of a compound of Formula (II) or (II'), or a pharmaceutically acceptable salt or solvate thereof, $R^3$ is thianyl, optionally substituted with one, two, or three $R^{20b}$ that is —NHC(O)$R^{25}$ and $R^{25}$ is $C_{2-5}$heterocycloalkyl optionally substituted with one $C_{1-6}$alkyl. In embodiments of a compound of Formula (II) or (II'), or a pharmaceutically acceptable salt or solvate thereof, $R^3$ is thianyl, optionally substituted with one, two, or three $R^{20b}$ that is —C(O)N($R^{22}$)($R^{23}$). In embodiments of a compound of Formula (II) or (II'), or a pharmaceutically acceptable salt or solvate thereof, $R^3$ is thianyl, optionally substituted with one, two, or three $R^{20b}$ that is —C(O)NH($R^{22}$). In embodiments of a compound of Formula (II) or (II'), or a pharmaceutically acceptable salt or solvate thereof, $R^3$ is thianyl, optionally substituted with one, two, or three $R^{20b}$ that is —C(O)NH($R^{22}$) and $R^{22}$ is $C_{2-9}$heterocycloalkyl optionally substituted with one, two, or three groups independently selected from halogen and $C_{1-6}$alkyl. In embodiments of a compound of Formula (II) or (II'), or a pharmaceutically acceptable salt or solvate thereof, $R^3$ is thianyl, optionally substituted with one, two, or three $R^{20b}$ that is —C(O)NH($R^{22}$) and $R^{22}$ is $C_{2-5}$heterocycloalkyl optionally substituted with one $C_{1-6}$alkyl.

In embodiments of a compound of Formula (II) or (II'), or a pharmaceutically acceptable salt or solvate thereof, $R^3$ is monovalent tetrahydro-2H-thiopyran 1,1-dioxide, optionally substituted with one, two, or three $R^{20b}$ that is amino. In embodiments of a compound of Formula (II) or (II'), or a pharmaceutically acceptable salt or solvate thereof, $R^3$ is monovalent tetrahydro-2H-thiopyran 1,1-dioxide, optionally substituted with one, two, or three $R^{20b}$ that is —CN. In embodiments of a compound of Formula (II) or (II'), or a pharmaceutically acceptable salt or solvate thereof, $R^3$ is monovalent tetrahydro-2H-thiopyran 1,1-dioxide, optionally substituted with one, two, or three $R^{20b}$ that is $C_{1-3}$alkyl. In embodiments of a compound of Formula (II) or (II'), or a pharmaceutically acceptable salt or solvate thereof, $R^3$ is monovalent tetrahydro-2H-thiopyran 1,1-dioxide, optionally substituted with one, two, or three $R^{20b}$ that is $C_{1-3}$alkoxy. In embodiments of a compound of Formula (II) or (II'), or a pharmaceutically acceptable salt or solvate thereof, $R^3$ is thianyl, optionally substituted with one, two, or three $R^{20b}$ that is $C_{1-3}$haloalkyl. In embodiments of a compound of Formula (II) or (II'), or a pharmaceutically acceptable salt or solvate thereof, $R^3$ is monovalent tetrahydro-2H-thiopyran 1,1-dioxide, optionally substituted with one, two, or three $R^{20b}$ that is —OH. In embodiments of a compound of Formula (II) or (II'), or a pharmaceutically acceptable salt or solvate thereof, $R^3$ is monovalent tetrahydro-2H-thiopyran 1,1-dioxide, optionally substituted with one, two, or three $R^{20b}$ that is oxo. In embodiments of a compound of Formula (II) or (II'), or a pharmaceutically acceptable salt or solvate thereof, $R^3$ is monovalent tetrahydro-2H-thiopyran 1,1-dioxide, optionally substituted with one, two, or three $R^{20b}$ that is —N($R^{24}$)C(O)$R^{25}$. In embodiments of a compound of Formula (II) or (II'), or a pharmaceutically acceptable salt or solvate thereof, $R^3$ is monovalent tetrahydro-2H-thiopyran 1,1-dioxide, optionally substituted with one, two, or three $R^{20b}$ that is —NHC(O)$R^{25}$. In embodiments of a compound of Formula (II) or (II'), or a pharmaceutically acceptable salt or solvate thereof, $R^3$ is monovalent tetrahydro-2H-thiopyran 1,1-dioxide, optionally substituted with one, two, or three $R^{20b}$ that is —NHC(O)$R^{25}$ and $R^{25}$ is $C_{2-9}$heterocycloalkyl optionally substituted with one, two, or three groups independently selected from halogen, $C_{1-6}$alkyl, $C_{1-6}$haloalkyl, $C_{1-6}$alkoxy, $C_{3-7}$cycloalkyl, $C_{2-9}$heterocycloalkyl, $C_{6-10}$aryl, and $C_{1-9}$heteroaryl. In embodiments of a compound of Formula (II) or (II'), or a pharmaceutically acceptable salt or solvate thereof, $R^3$ is monovalent tetrahydro-2H-thiopyran 1,1-dioxide, optionally substituted with one, two, or three $R^{20b}$ that is —NHC(O)$R^{25}$ and $R^{25}$ is $C_{2-5}$heterocycloalkyl optionally substituted with one $C_{1-6}$alkyl. In embodiments of a compound of Formula (II) or (II'), or a pharmaceutically acceptable salt or solvate thereof, $R^3$ is monovalent tetrahydro-2H-thiopyran 1,1-dioxide, optionally substituted with one, two, or three $R^{20b}$ that is —C(O)N($R^{22}$)($R^{23}$). In embodiments of a compound of Formula (II) or (II'), or a pharmaceutically acceptable salt or solvate thereof, $R^3$ is monovalent tetrahydro-2H-thiopyran 1,1-dioxide, optionally substituted with one, two, or three $R^{20b}$ that is —C(O)NH($R^{22}$). In embodiments of a compound of Formula (II) or (II'), or a pharmaceutically acceptable salt or solvate thereof, $R^3$ is monovalent tetrahydro-2H-thiopyran 1,1-dioxide, optionally substituted with one, two, or three $R^{20b}$ that is —C(O)NH($R^{22}$) and $R^{22}$ is $C_{2-9}$heterocycloalkyl optionally substituted with one, two, or three groups independently selected from halogen and $C_{1-6}$alkyl. In embodiments of a compound of Formula (II) or (II'), or a pharmaceutically acceptable salt or solvate thereof, $R^3$ is monovalent tetrahydro-2H-thiopyran 1,1-dioxide, optionally substituted with one, two, or three $R^{20b}$ that is —C(O)NH($R^{22}$) and $R^{22}$ is $C_{2-5}$heterocycloalkyl optionally substituted with one $C_{1-6}$alkyl.

In embodiments of a compound of Formula (II) or (II'), or a pharmaceutically acceptable salt or solvate thereof, $R^3$ is $4\lambda^2$-thiomorpholinyl, optionally substituted with one, two, or three $R^{20b}$ that is amino. In embodiments of a compound of Formula (II) or (II'), or a pharmaceutically acceptable salt or solvate thereof, $R^3$ is $4\lambda^2$-thiomorpholinyl, optionally substituted with one, two, or three $R^{20b}$ that is —CN. In embodiments of a compound of Formula (II) or (II'), or a pharmaceutically acceptable salt or solvate thereof, $R^3$ is $4\lambda^2$-thiomorpholinyl, optionally substituted with one, two, or three $R^{20b}$ that is $C_{1-3}$alkyl. In embodiments of a compound of Formula (II) or (II'), or a pharmaceutically acceptable salt or solvate thereof, $R^3$ is $4\lambda^2$-thiomorpholinyl, optionally substituted with one, two, or three $R^{20b}$ that is $C_{1-3}$alkoxy. In embodiments of a compound of Formula (II) or (II'), or a pharmaceutically acceptable salt or solvate thereof, $R^3$ is $4\lambda^2$-thiomorpholinyl, optionally substituted with one, two, or three $R^{20b}$ that is $C_{1-3}$haloalkyl. In embodiments of a compound of Formula (II) or (II'), or a pharmaceutically acceptable salt or solvate thereof, $R^3$ is $4\lambda^2$-thiomorpholinyl, optionally substituted with one, two, or three $R^{20b}$ that is —OH. In embodiments of a compound of Formula (II) or (II'), or a pharmaceutically acceptable salt or solvate thereof, $R^3$ is $4\lambda^2$-thiomorpholinyl, optionally substituted with one, two, or three $R^{20b}$ that is oxo. In embodiments of a compound of Formula (II) or (II'), or a pharmaceutically acceptable salt or solvate thereof, $R^3$ is $4\lambda^2$-thiomorpholinyl, optionally substituted with one, two, or three $R^{20b}$ that is —N($R^{24}$)C(O)$R^{25}$. In embodiments of a compound of Formula (II) or (II'), or a pharmaceutically acceptable salt or solvate thereof, $R^3$ is $4\lambda^2$-thiomorpholinyl, optionally substituted with one, two, or three $R^{20b}$ that is —NHC(O)$R^{25}$. In embodiments of a compound of Formula (II) or (II'), or a pharmaceutically acceptable salt or solvate thereof, $R^3$ is $4\lambda^2$-thiomorpholinyl, optionally substituted with one, two, or three $R^{20b}$ that is —NHC(O)$R^{25}$ and $R^{25}$ is $C_{2-9}$heterocycloalkyl optionally substituted with one, two, or three groups independently selected from halogen, $C_{1-6}$alkyl, $C_{1-6}$haloalkyl, $C_{1-6}$alkoxy, $C_{3-7}$cycloalkyl, $C_{2-9}$heterocycloalkyl, $C_{6-10}$aryl, and $C_{1-9}$heteroaryl. In embodiments of a compound of Formula (II) or (II'), or a pharmaceutically acceptable salt or solvate thereof, $R^3$ is $4\lambda^2$-thiomorpholinyl, optionally substituted with one, two, or three $R^{20b}$ that is —NHC(O)$R^{25}$ and $R^{25}$ is $C_{2-9}$heterocycloalkyl optionally substituted with one $C_{1-6}$alkyl. In embodiments of a compound of Formula (II) or (II'), or a pharmaceutically acceptable salt or solvate thereof, $R^3$ is $4\lambda^2$-thiomorpholinyl, optionally substituted with one, two, or three $R^{20b}$ that is —C(O)N($R^{22}$)($R^{23}$). In embodiments of a compound of Formula (II) or (II'), or a pharmaceutically acceptable salt or solvate thereof, $R^3$ is $4\lambda^2$-thiomorpholinyl, optionally substituted with one, two, or three $R^{20b}$ that is —C(O)NH($R^{22}$). In embodiments of a compound of Formula (II) or (II'), or a pharmaceutically acceptable salt or solvate thereof, $R^3$ is $4\lambda^2$-thiomorpholinyl, optionally substituted with one, two, or three $R^{20b}$ that is —C(O)NH($R^{22}$) and $R^{22}$ is $C_{2-9}$heterocycloalkyl optionally substituted with one, two, or three groups independently selected from halogen and $C_{1-6}$alkyl. In embodiments of a compound of Formula (II) or (II'), or a pharmaceutically acceptable salt or solvate thereof, $R^3$ is $4\lambda^2$-thiomorpholinyl, optionally substituted with one, two, or three $R^{20b}$ that is —C(O)NH($R^{22}$) and $R^{22}$ is $C_{2-5}$heterocycloalkyl optionally substituted with one $C_{1-6}$alkyl.

In embodiments of a compound of Formula (II) or (II'), or a pharmaceutically acceptable salt or solvate thereof, $R^3$ is piperidinyl, optionally substituted with one, two, or three $R^{20b}$ that is amino. In embodiments of a compound of Formula (II) or (II'), or a pharmaceutically acceptable salt or solvate thereof, $R^3$ is piperidinyl, optionally substituted with one, two, or three $R^{20b}$ that is —CN. In embodiments of a compound of Formula (II) or (II'), or a pharmaceutically acceptable salt or solvate thereof, $R^3$ is piperidinyl, optionally substituted with one, two, or three $R^{20b}$ that is $C_{1-3}$alkyl. In embodiments of a compound of Formula (II) or (II'), or a pharmaceutically acceptable salt or solvate thereof, $R^3$ is piperidinyl, optionally substituted with one, two, or three $R^{20b}$ that is $C_{1-3}$alkoxy. In embodiments of a compound of Formula (II) or (II'), or a pharmaceutically acceptable salt or solvate thereof, $R^3$ is piperidinyl, optionally substituted with one, two, or three $R^{20b}$ that is $C_{1-3}$haloalkyl. In embodiments of a compound of Formula (II) or (II'), or a pharmaceutically acceptable salt or solvate thereof, $R^3$ is piperidinyl, optionally substituted with one, two, or three $R^{20b}$ that is —OH. In embodiments of a compound of Formula (II) or (II'), or a pharmaceutically acceptable salt or solvate thereof, $R^3$ is piperidinyl, optionally substituted with one, two, or three $R^{20b}$ that is oxo. In embodiments of a compound of Formula (II) or (II'), or a pharmaceutically acceptable salt or solvate thereof, $R^3$ is piperidinyl, optionally substituted with one, two, or three $R^{20b}$ that is —N($R^{24}$)C(O)$R^{25}$. In embodiments of a compound of Formula (II) or (II'), or a pharmaceutically acceptable salt or solvate thereof, $R^3$ is piperidinyl, optionally substituted with one, two, or three $R^{20b}$ that is —NHC(O)$R^{25}$. In embodiments of a compound of Formula (II) or (II'), or a pharmaceutically acceptable salt or solvate thereof, $R^3$ is piperidinyl, optionally substituted with one, two, or three $R^{20b}$ that is —NHC(O)$R^{25}$ and $R^{25}$ is $C_{2-9}$heterocycloalkyl optionally substituted with one, two, or three groups independently selected from halogen, $C_{1-6}$alkyl, $C_{1-6}$haloalkyl, $C_{1-6}$alkoxy, $C_{3-7}$cycloalkyl, $C_{2-9}$heterocycloalkyl, $C_{6-10}$aryl, and $C_{1-9}$heteroaryl. In embodiments of a compound of Formula (II) or (II'), or a pharmaceutically acceptable salt or solvate thereof, $R^3$ is piperidinyl, optionally substituted with one, two, or three $R^{20b}$ that is —NHC(O)$R^{21}$ and $R^{25}$ is $C_{2-5}$heterocycloalkyl optionally substituted with one $C_{1-6}$alkyl. In embodiments of a compound of Formula (II) or (II'), or a pharmaceutically acceptable salt or solvate thereof, $R^3$ is piperidinyl, optionally substituted with one, two, or three $R^{20b}$ that is —C(O)N($R^{22}$)($R^{23}$). In embodiments of a compound of Formula (II) or (II'), or a pharmaceutically acceptable salt or solvate thereof, $R^3$ is piperidinyl, optionally substituted with one, two, or three $R^{20b}$ that is —C(O)NH($R^{22}$). In embodiments of a compound of Formula (II) or (II'), or a pharmaceutically acceptable salt or solvate thereof, $R^3$ is piperidinyl, optionally substituted with one, two, or three $R^{20b}$ that is —C(O)NH ($R^{22}$) and $R^{22}$ is $C_{2-9}$heterocycloalkyl optionally substituted with one, two, or three groups independently selected from halogen and $C_{1-6}$alkyl. In embodiments of a compound of Formula (II) or (II'), or a pharmaceutically acceptable salt or solvate thereof, $R^3$ is piperidinyl, optionally substituted with one, two, or three $R^{20b}$ that is —C(O)NH($R^{22}$) and $R^{22}$ is $C_{2-5}$heterocycloalkyl optionally substituted with one $C_{1-6}$alkyl.

In embodiments of a compound of Formula (II) or (II'), or a pharmaceutically acceptable salt or solvate thereof, $R^3$ is piperazinyl, optionally substituted with one, two, or three $R^{20b}$ that is amino. In embodiments of a compound of Formula (II) or (II'), or a pharmaceutically acceptable salt or solvate thereof, $R^3$ is piperazinyl, optionally substituted with one, two, or three $R^{20b}$ that is —CN. In embodiments of a compound of Formula (II) or (II'), or a pharmaceutically acceptable salt or solvate thereof, $R^3$ is piperazinyl, optionally substituted with one, two, or three $R^{20b}$ that is $C_{1-3}$alkyl. In embodiments of a compound of Formula (II) or (II'), or a pharmaceutically acceptable salt or solvate thereof, $R^3$ is piperazinyl, optionally substituted with one, two, or three $R^{20b}$ that is $C_{1-3}$alkoxy. In embodiments of a compound of Formula (II) or (II'), or a pharmaceutically acceptable salt or solvate thereof, $R^3$ is piperazinyl, optionally substituted with one, two, or three $R^{20b}$ that is $C_{1-3}$haloalkyl. In embodiments of a compound of Formula (II) or (II'), or a pharmaceutically acceptable salt or solvate thereof, $R^3$ is piperazinyl, optionally substituted with one, two, or three $R^{20b}$ that is —OH. In embodiments of a compound of Formula (II) or (II'), or a pharmaceutically acceptable salt or solvate thereof, $R^3$ is piperazinyl, optionally substituted with one, two, or three $R^{20b}$ that is oxo. In embodiments of a compound of Formula (II) or (II'), or a pharmaceutically acceptable salt or solvate thereof, $R^3$ is piperazinyl, optionally substituted with one, two, or three $R^{20b}$ that is —N($R^{24}$)C(O)$R^{25}$. In embodiments of a compound of Formula (II) or (II'), or a pharmaceutically acceptable salt or solvate thereof, $R^3$ is piperazinyl, optionally substituted with one, two, or three $R^{20b}$ that is —NHC(O)$R^{25}$. In embodiments of a compound of Formula (II) or (II'), or a pharmaceutically acceptable salt or solvate thereof, $R^3$ is piperazinyl, optionally substituted with one, two, or three $R^{20b}$ that is —NHC(O)$R^{25}$ and $R^{25}$ is $C_{2-9}$heterocycloalkyl optionally substituted with one, two, or three groups independently selected from halogen, $C_{1-6}$alkyl, $C_{1-6}$haloalkyl, $C_{1-6}$alkoxy, $C_{3-7}$cycloalkyl, $C_{2-9}$heterocycloalkyl, $C_{6-10}$aryl, and $C_{1-9}$heteroaryl. In embodiments of a compound of Formula (II) or (II'), or a pharmaceutically acceptable salt or solvate thereof, $R^3$ is piperazinyl, optionally substituted with one, two, or three $R^{20b}$ that is —NHC(O)$R^{25}$ and $R^{25}$ is $C_{2-5}$heterocycloalkyl optionally substituted with one $C_{1-6}$alkyl. In embodiments of a compound of Formula (II) or (II'), or a pharmaceutically acceptable salt or solvate thereof, $R^3$ is piperazinyl, optionally substituted with one, two, or three $R^{2b}$ that is —C(O)N($R^{22}$)($R^{23}$). In embodiments of a compound of Formula (II) or (II'), or a pharmaceutically acceptable salt or solvate thereof, $R^3$ is piperazinyl, optionally substituted with one, two, or three $R^{20b}$ that is —C(O)NH($R^{22}$). In embodiments of a compound of Formula (II) or (II'), or a pharmaceutically acceptable salt or solvate thereof, $R^3$ is piperazinyl, optionally substituted with one, two, or three $R^{20b}$ that is —C(O)NH ($R^{22}$) and $R^{22}$ is $C_{2-9}$heterocycloalkyl optionally substituted with one, two, or three groups independently selected from halogen and $C_{1-6}$alkyl. In embodiments of a compound of Formula (II) or (II'), or a pharmaceutically acceptable salt or solvate thereof, $R^3$ is piperazinyl, optionally substituted with one, two, or three $R^{20b}$ that is —C(O)NH($R^{22}$) and $R^{22}$ is $C_{2-5}$heterocycloalkyl optionally substituted with one $C_{1-6}$alkyl.

In embodiments of a compound of Formula (II) or (II'), or a pharmaceutically acceptable salt or solvate thereof, $R^3$ is pyrrolidinyl, optionally substituted with one, two, or three $R^{20b}$ that is amino. In embodiments of a compound of Formula (II) or (II'), or a pharmaceutically acceptable salt or solvate thereof, $R^3$ is pyrrolidinyl, optionally substituted with one, two, or three $R^{20b}$ that is —CN. In embodiments of a compound of Formula (II) or (II'), or a pharmaceutically acceptable salt or solvate thereof, $R^3$ is pyrrolidinyl, optionally substituted with one, two, or three $R^{20b}$ that is $C_{1-3}$alkyl. In embodiments of a compound of Formula (II) or (II'), or a pharmaceutically acceptable salt or solvate thereof, $R^3$ is pyrrolidinyl, optionally substituted with one, two, or three $R^{20b}$ that is $C_{1-3}$alkoxy. In embodiments of a compound of Formula (II) or (II'), or a pharmaceutically acceptable salt or solvate thereof, $R^3$ is pyrrolidinyl, optionally substituted with one, two, or three $R^{20b}$ that is $C_{1-3}$haloalkyl. In embodiments of a compound of Formula (II) or (II'), or a pharmaceutically acceptable salt or solvate thereof, $R^3$ is pyrrolidinyl, optionally substituted with one, two, or three $R^{20b}$ that is —OH. In embodiments of a compound of Formula (II) or (II'), or a pharmaceutically acceptable salt or solvate thereof, $R^3$ is pyrrolidinyl, optionally substituted with one, two, or three $R^{20b}$ that is oxo. In embodiments of a compound of Formula (II) or (II'), or a pharmaceutically acceptable salt or solvate thereof, $R^3$ is pyrrolidinyl, optionally substituted with one, two, or three $R^{20b}$ that is —N($R^{24}$)C(O)$R^{25}$. In embodiments of a compound of Formula (II) or (II'), or a pharmaceutically acceptable salt or solvate thereof, $R^3$ is pyrrolidinyl, optionally substituted with one, two, or three $R^{20b}$ that is —NHC(O)$R^{25}$. In embodiments of a compound of Formula (II) or (II'), or a pharmaceutically acceptable salt or solvate thereof, $R^3$ is pyrrolidinyl, optionally substituted with one, two, or three $R^{20b}$ that is —NHC(O)$R^{25}$ and $R^{25}$ is $C_{2-9}$heterocycloalkyl optionally substituted with one, two, or three groups independently selected from halogen, $C_{1-6}$alkyl, $C_{1-6}$haloalkyl, $C_{1-6}$alkoxy, $C_{3-7}$cycloalkyl, $C_{2-9}$heterocycloalkyl, $C_{6-10}$aryl, and $C_{1-9}$ heteroaryl. In embodiments of a compound of Formula (II) or (II'), or a pharmaceutically acceptable salt or solvate thereof, $R^3$ is pyrrolidinyl, optionally substituted with one, two, or three $R^{20b}$ that is —NHC(O)$R^{25}$ and $R^{25}$ is $C_{2-5}$heterocycloalkyl optionally substituted with one $C_{1-6}$alkyl. In embodiments of a compound of Formula (II) or (II'), or a pharmaceutically acceptable salt or solvate thereof, $R^3$ is pyrrolidinyl, optionally substituted with one, two, or three $R^{20b}$ that is —C(O)N($R^{22}$)($R^{23}$). In embodiments of a compound of Formula (II) or (II'), or a pharmaceutically acceptable salt or solvate thereof, $R^3$ is pyrrolidinyl, optionally substituted with one, two, or three $R^{20b}$ that is —C(O)NH($R^{22}$). In embodiments of a compound of Formula (II) or (II'), or a pharmaceutically acceptable salt or solvate thereof, $R^3$ is pyrrolidinyl, optionally substituted with one, two, or three $R^{20b}$ that is —C(O)NH($R^{22}$) and $R^{22}$ is $C_{2-9}$heterocycloalkyl optionally substituted with one, two, or three groups independently selected from halogen and $C_{1-6}$alkyl. In embodiments of a compound of Formula (II) or (II'), or a pharmaceutically acceptable salt or solvate thereof, $R^3$ is pyrrolidinyl, optionally substituted with one, two, or three $R^{20b}$ that is —C(O)NH($R^{22}$) and $R^{22}$ is $C_{2-5}$heterocycloalkyl optionally substituted with one $C_{1-6}$alkyl.

In some embodiments is a compound of Formula (II) or (II'), or a pharmaceutically acceptable salt or solvate thereof, wherein $R^3$ is cyclopropyl optionally substituted with one, two, or three $R^{2b}$. In some embodiments is a compound of Formula (II) or (II'), or a pharmaceutically acceptable salt or solvate thereof, wherein $R^3$ is cyclobutyl optionally substituted with one, two, or three $R^{20b}$. In some embodiments is a compound of Formula (II) or (II'), or a pharmaceutically acceptable salt or solvate thereof, wherein $R^3$ is cyclopentyl optionally substituted with one, two, or three $R^{20b}$. In some embodiments is a compound of Formula (II) or (II'), or a pharmaceutically acceptable salt or solvate thereof, wherein $R^3$ is cyclohexyl optionally substituted with one, two, or three $R^{20b}$. In some embodiments is a compound of Formula (II) or (II'), or a pharmaceutically acceptable salt or solvate thereof, wherein $R^3$ is aziridinyl optionally substituted with one, two, or three $R^{20b}$. In some embodiments is a compound of Formula (II) or (II'), or a pharmaceutically acceptable salt or solvate thereof, wherein $R^3$ is azetidinyl optionally substituted with one, two, or three $R^{20b}$. In some embodiments is a compound of Formula (II) or (II'), or a pharmaceutically acceptable salt or solvate thereof, wherein $R^3$ is pyrrolidinyl optionally substituted with one, two, or three $R^{20b}$. In some embodiments is a compound of Formula (II) or (II'), or a pharmaceutically acceptable salt or solvate thereof, wherein $R^3$ is piperidinyl optionally substituted with one, two, or three $R^{20b}$. In some embodiments is a compound of Formula (II) or (II'), or a pharmaceutically acceptable salt or solvate thereof, wherein $R^3$ is piperizinyl optionally substituted with one, two, or three $R^{20b}$. In some embodiments is a compound of Formula (II) or (II'), or a pharmaceutically acceptable salt or solvate thereof, wherein $R^3$ is morpholinyl optionally substituted with one, two, or three $R^{20b}$. In some embodiments is a compound of Formula (II) or (II'), or a pharmaceutically acceptable salt or solvate thereof, wherein $R^3$ is oxetanyl optionally substituted with one, two, or three $R^{20b}$. In some embodiments is a compound of Formula (II) or (II'), or a pharmaceutically acceptable salt or solvate thereof, wherein $R^3$ is tetrahydrofuranyl optionally substituted with one, two, or three $R^{20b}$ In some embodiments is a compound of Formula (II) or (II'), or a pharmaceutically acceptable salt or solvate thereof, wherein $R^3$ is tetrahydropyranyl optionally substituted with one, two, or three $R^{20b}$. In some embodiments is a compound of Formula (II) or (II'), or a pharmaceutically acceptable salt or solvate thereof, wherein $R^3$ is pyridinyl optionally substituted with one, two, or three $R^{20b}$. In some embodiments is a compound of Formula (II) or (II'), or a pharmaceutically acceptable salt or solvate thereof, wherein $R^3$ is pyrazinyl optionally substituted with one, two, or three $R^{20b}$. In some embodiments is a compound of Formula (II) or (II'), or a pharmaceutically acceptable salt or solvate thereof, wherein $R^3$ is pyrimidinyl optionally substituted with one, two, or three $R^{20b}$. In some embodiments is a compound of Formula (II) or (II'), or a pharmaceutically acceptable salt or solvate thereof, wherein $R^3$ is pyridazinyl optionally substituted with one, two, or three $R^{20b}$. In some embodiments is a compound of Formula (II) or (II'), or a pharmaceutically acceptable salt or solvate thereof, wherein $R^3$ is phenyl optionally substituted with one, two, or three $R^{20b}$. In some embodiments is a compound of Formula (II) or (II'), or a pharmaceutically acceptable salt or solvate thereof, wherein $R^3$ is pyrazolyl optionally substituted with one, two, or three $R^{20b}$. In some embodiments is a compound of Formula (II) or (II'), or a pharmaceutically acceptable salt or solvate thereof, wherein $R^3$ is pyrrolyl optionally substituted with one, two, or three $R^{20b}$. In some embodiments is a compound of Formula (II) or (II'), or a pharmaceutically acceptable salt or solvate thereof, wherein $R^3$ is thiophenyl optionally substituted with one, two, or three $R^{20b}$. In some embodiments is a compound of Formula (II) or (II'), or a pharmaceutically acceptable salt or solvate thereof, wherein $R^3$ is thianyl optionally substituted with one, two, or three $R^{20b}$. In some embodiments is a compound of Formula (II) or (II'), or a pharmaceutically acceptable salt or solvate thereof, wherein $R^3$ is 1,3-imidazolyl optionally substituted with one, two, or three $R^{20b}$. In some embodiments is a compound of Formula (II) or (II'), or a pharmaceutically acceptable salt or solvate thereof, wherein $R^3$ is thiazolyl optionally substituted with one, two, or three $R^{20b}$. In some embodiments is a compound of Formula (II) or (II'), or a pharmaceutically acceptable salt or solvate thereof, wherein $R^3$ is oxepanyl optionally substituted with one, two, or three $R^{20b}$. In some embodiments is a compound of Formula (II) or (II'), or a pharmaceutically acceptable salt or solvate thereof, wherein $R^3$ is azepanyl optionally substituted with one, two, or three $R^{20b}$. In some embodiments is a compound of Formula (II) or (II'), or a pharmaceutically acceptable salt or solvate thereof, wherein $R^3$ is 1,4-dioxapanyl optionally substituted with one, two, or three $R^{20b}$. In some embodiments is a compound of Formula (II) or (II'), or a pharmaceutically acceptable salt or solvate thereof, wherein $R^3$ is 1,4-oxazepanyl optionally substituted with one, two, or three $R^{20b}$. In some embodiments is a compound of Formula (II) or (II'), or a pharmaceutically acceptable salt or solvate thereof, wherein $R^3$ is 2,6-diazaspiro[3.3]heptanyl optionally substituted with one, two, or three $R^{20b}$. In some embodiments is a compound of Formula (II) or (II'), or a pharmaceutically acceptable salt or solvate thereof, wherein $R^3$ is 2-oxa-6-azaspiro[3.3]heptanyl optionally substituted with one, two, or three $R^{20b}$.

In some embodiments is a compound of Formula (II) or (II'), or a pharmaceutically acceptable salt or solvate thereof, wherein $R^3$ is

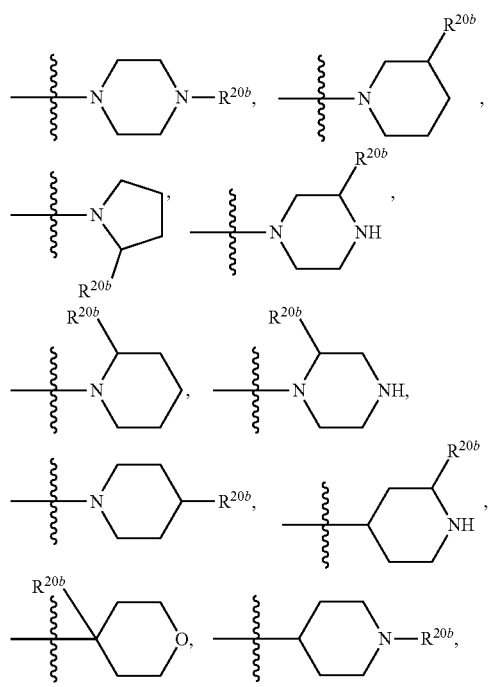

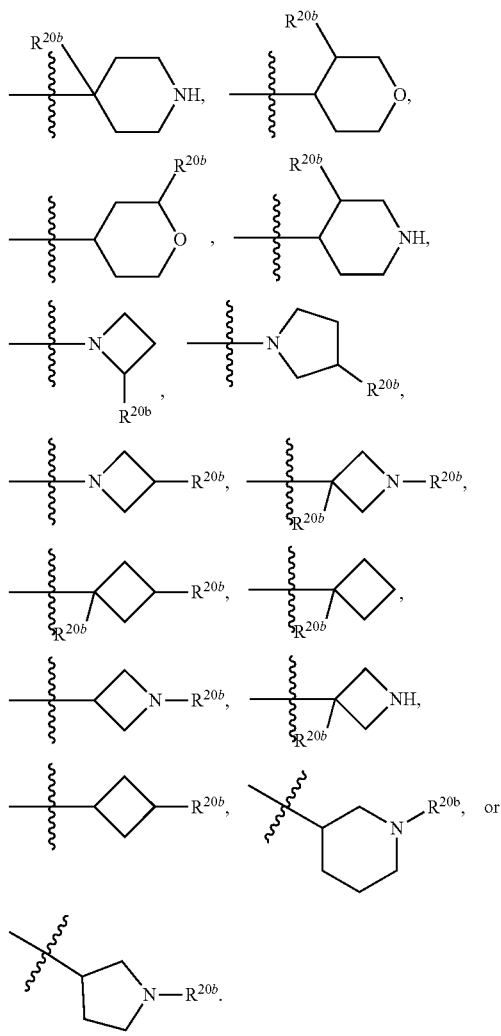

In some embodiments is a compound of Formula (II) or (II'), or a pharmaceutically acceptable salt or solvate thereof, wherein $R^3$ is

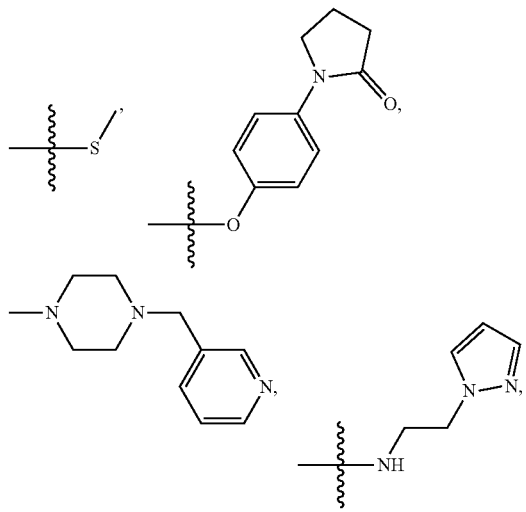

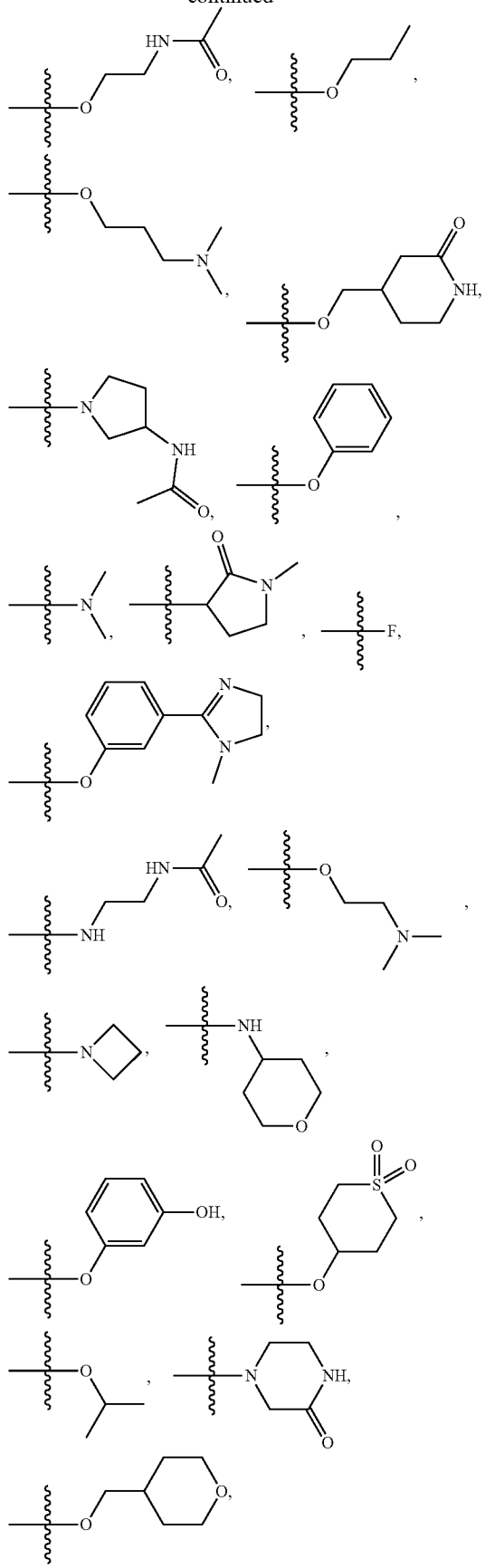
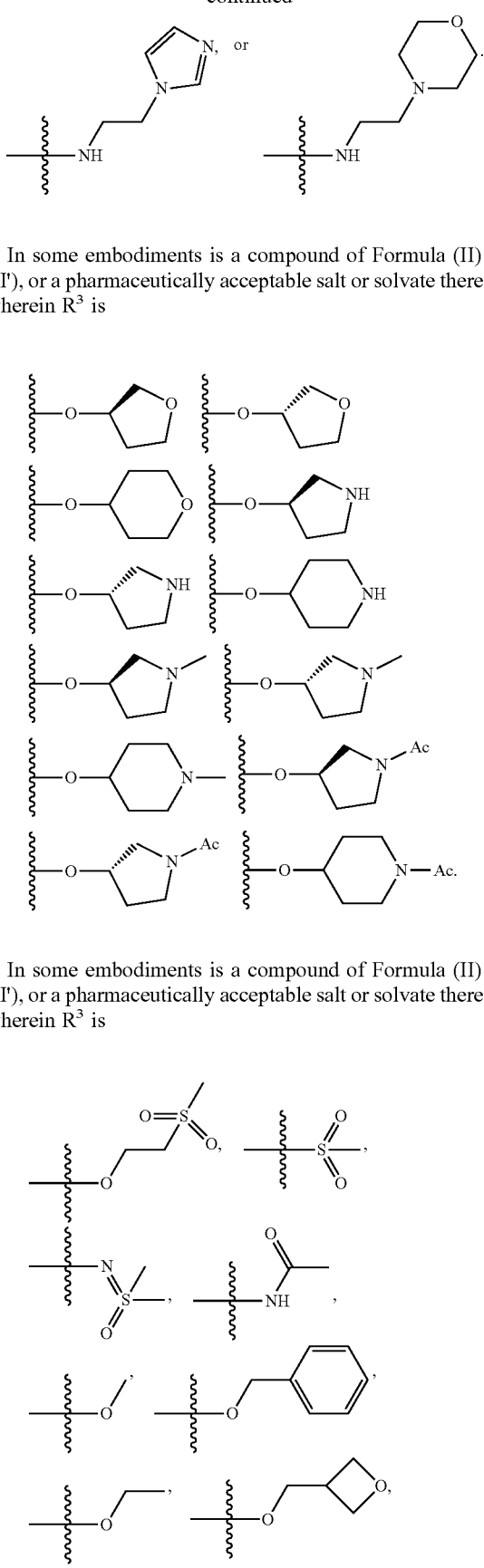
In some embodiments is a compound of Formula (II) or (II'), or a pharmaceutically acceptable salt or solvate thereof, wherein $R^3$ is
In some embodiments is a compound of Formula (II) or (II'), or a pharmaceutically acceptable salt or solvate thereof, wherein $R^3$ is

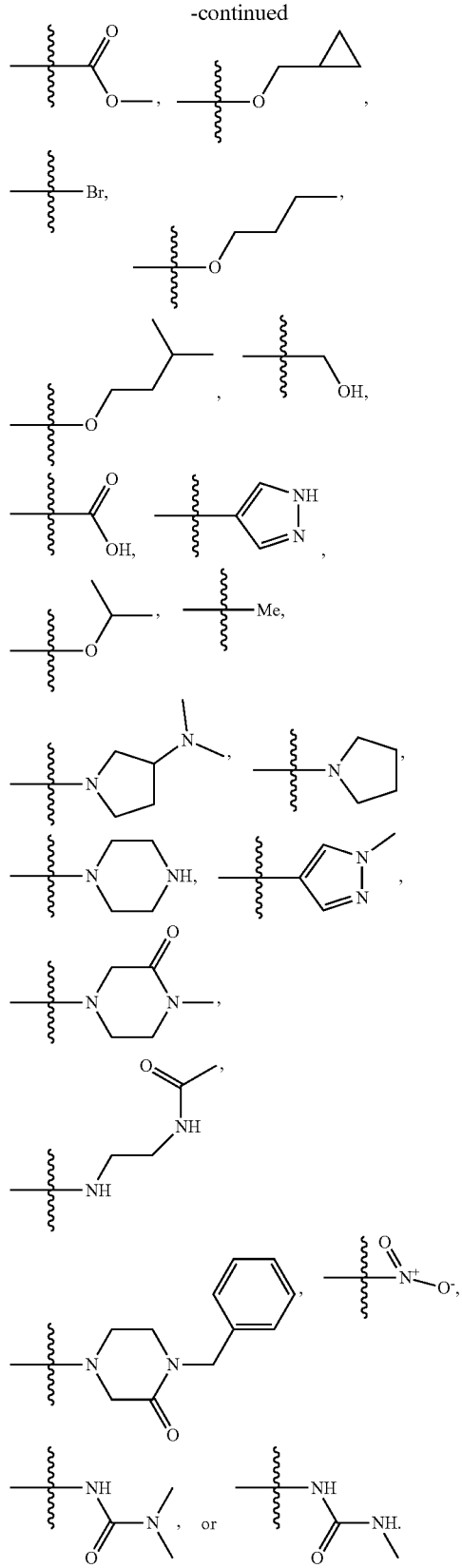
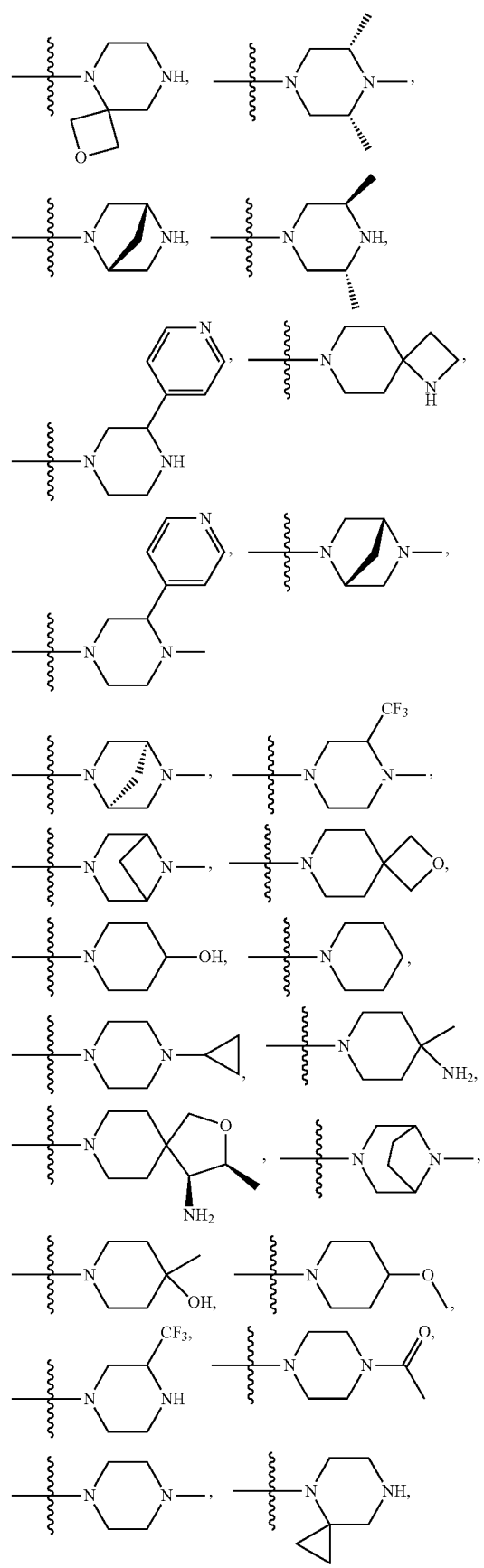
In some embodiments is a compound of Formula (II) or (II'), or a pharmaceutically acceptable salt or solvate thereof, wherein R³ is -continued
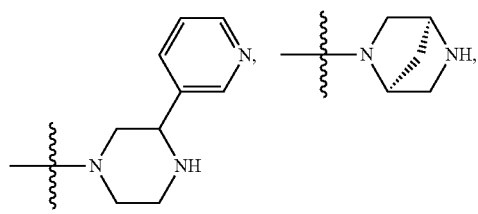
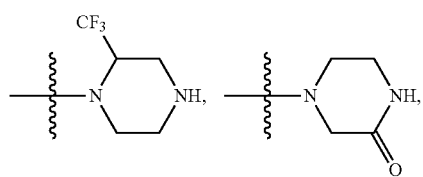
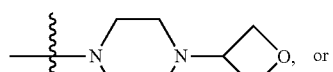
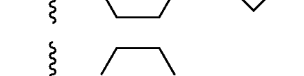
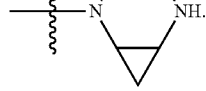
In some embodiments is a compound of Formula (II) or (II'), or a pharmaceutically acceptable salt or solvate thereof, wherein R³ is
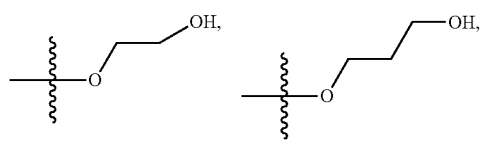
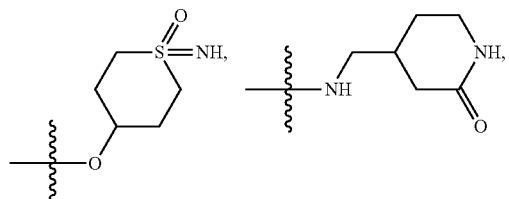
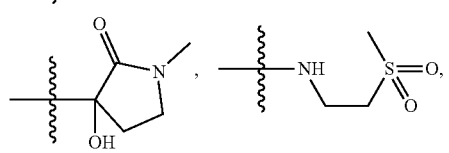
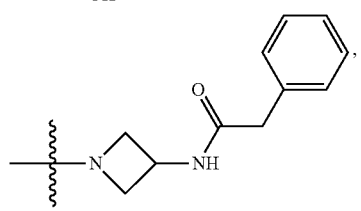
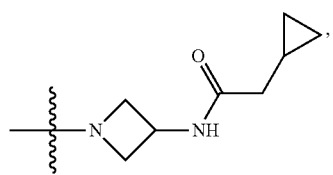
-continued
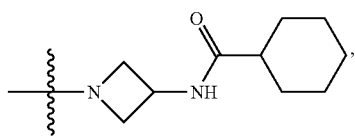
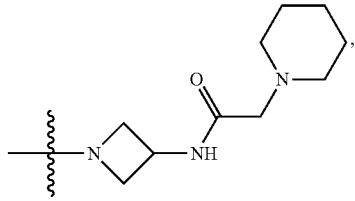
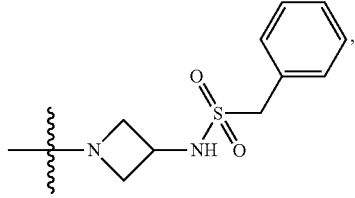
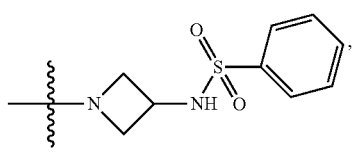
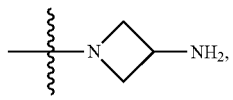
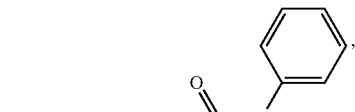
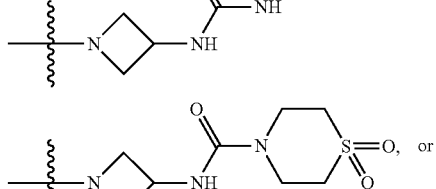
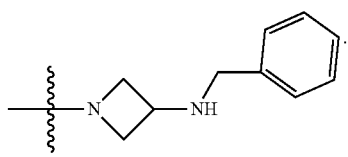
In some embodiments is a compound of Formula (II) or (II'), or a pharmaceutically acceptable salt or solvate thereof, wherein R³ is
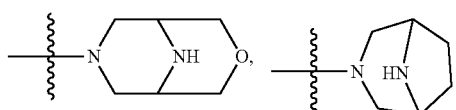
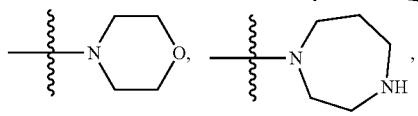

-continued
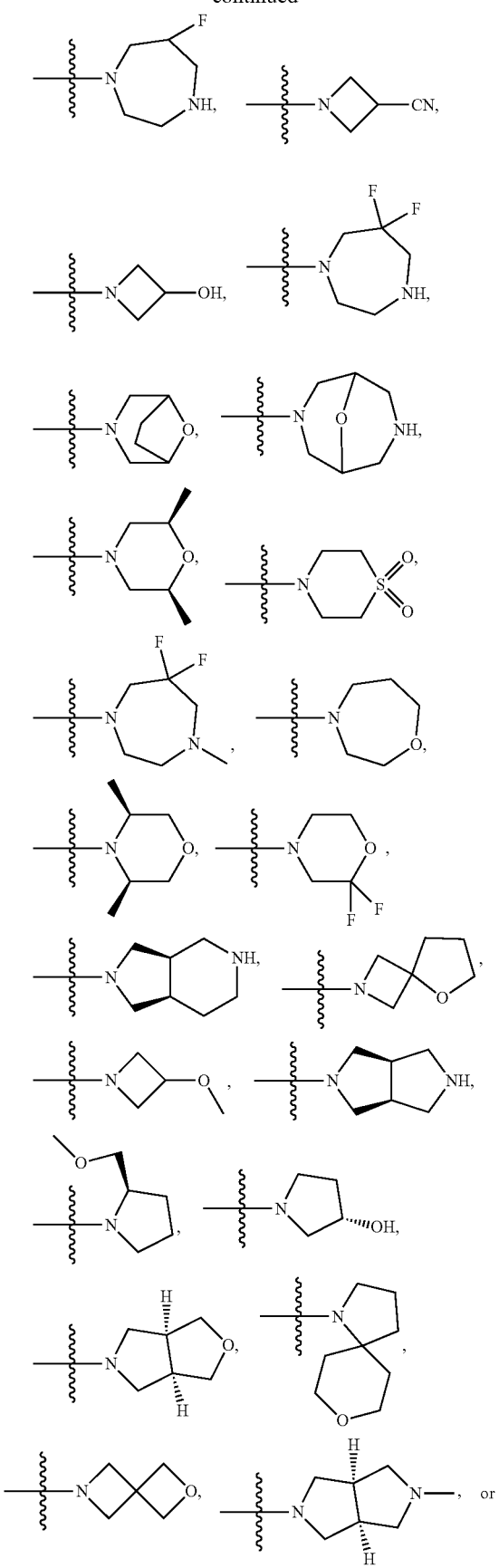
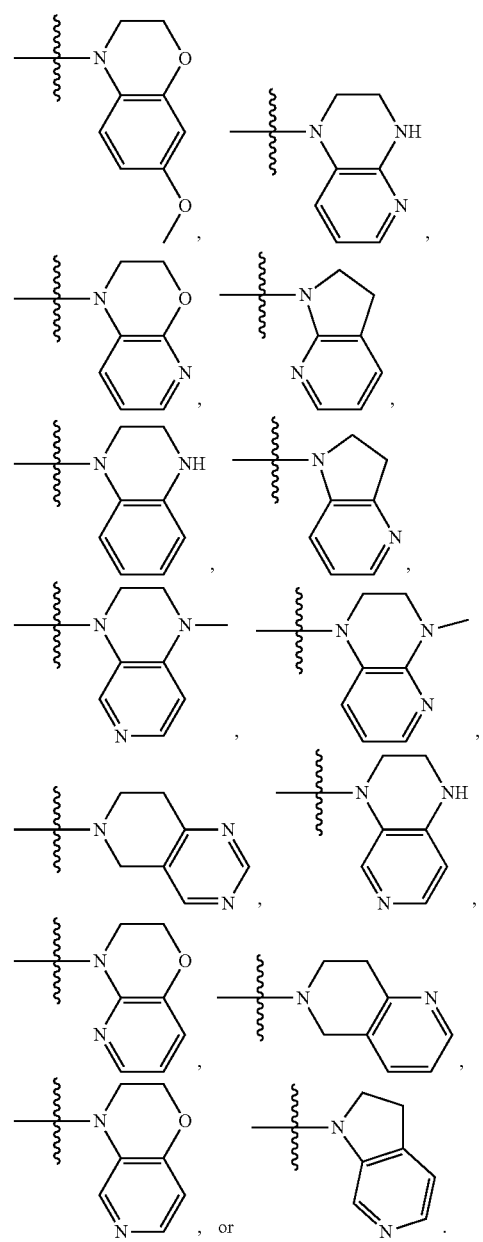
In some embodiments is a compound of Formula (II) or (II'), or a pharmaceutically acceptable salt or solvate thereof, wherein $R^3$ is
In some embodiments is a compound of Formula (II) or (II'), or a pharmaceutically acceptable salt or solvate thereof, wherein $R^3$ is

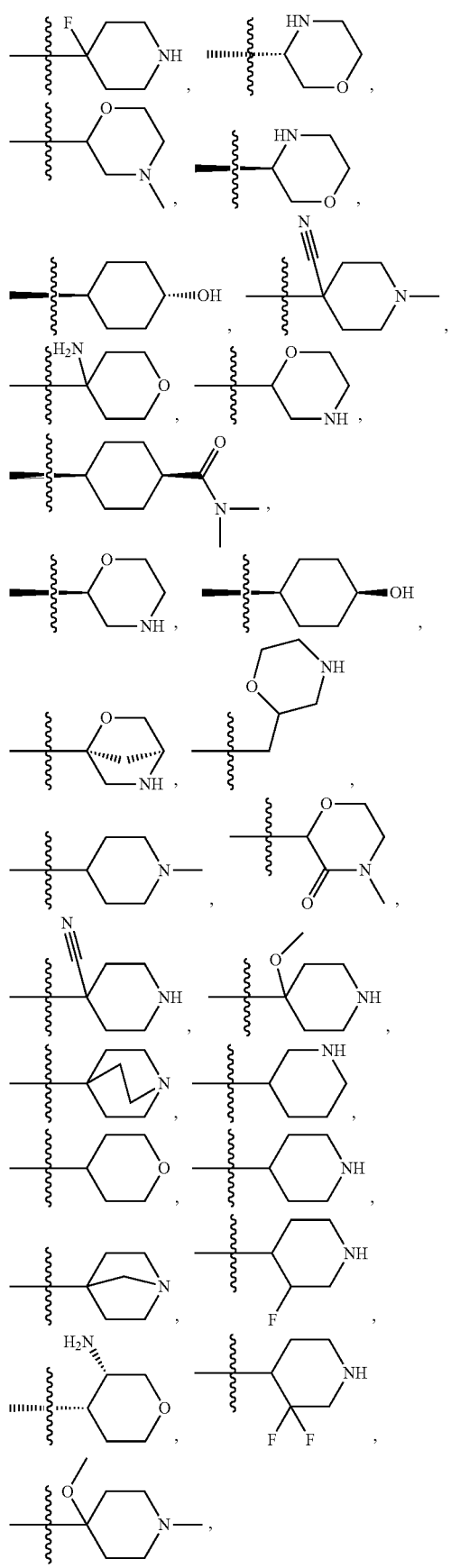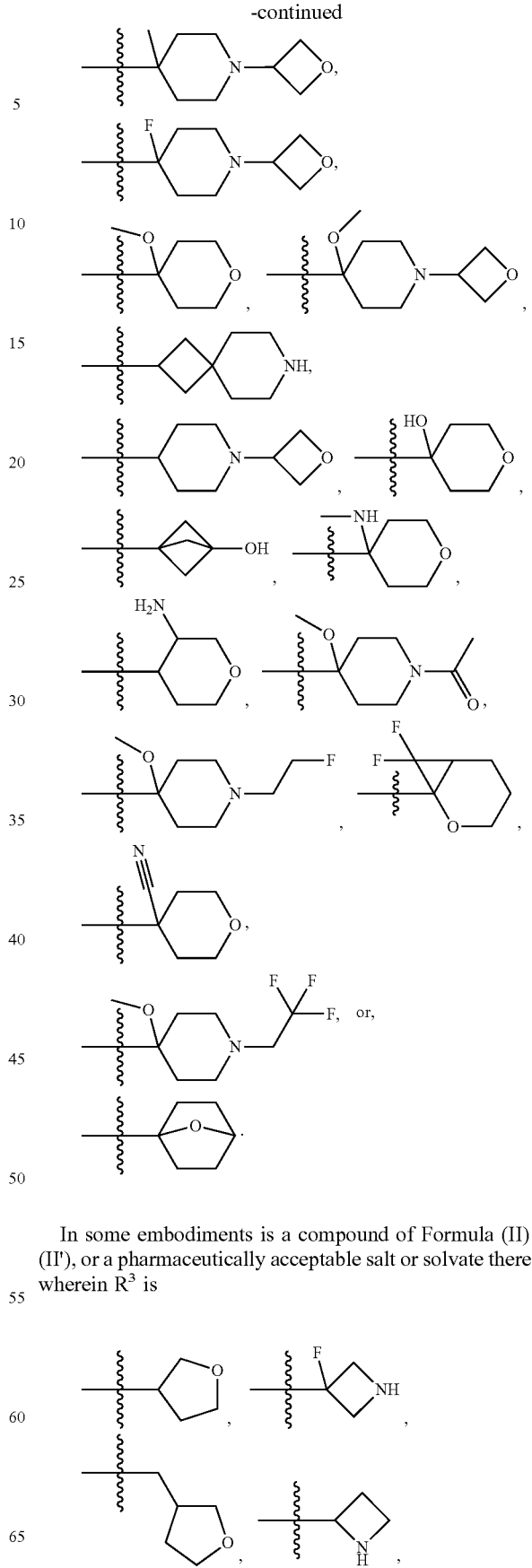
In some embodiments is a compound of Formula (II) or (II'), or a pharmaceutically acceptable salt or solvate thereof, wherein $R^3$ is
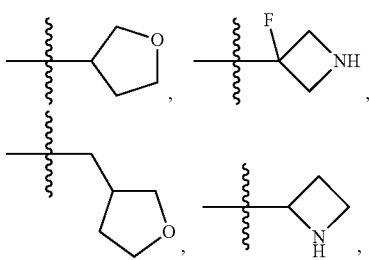

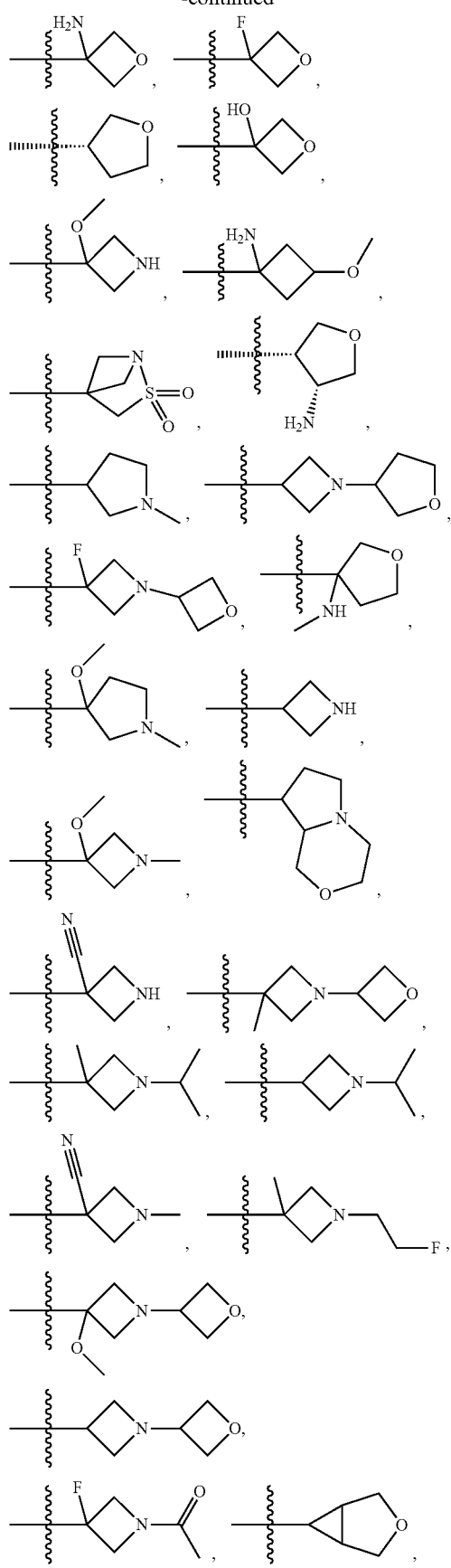
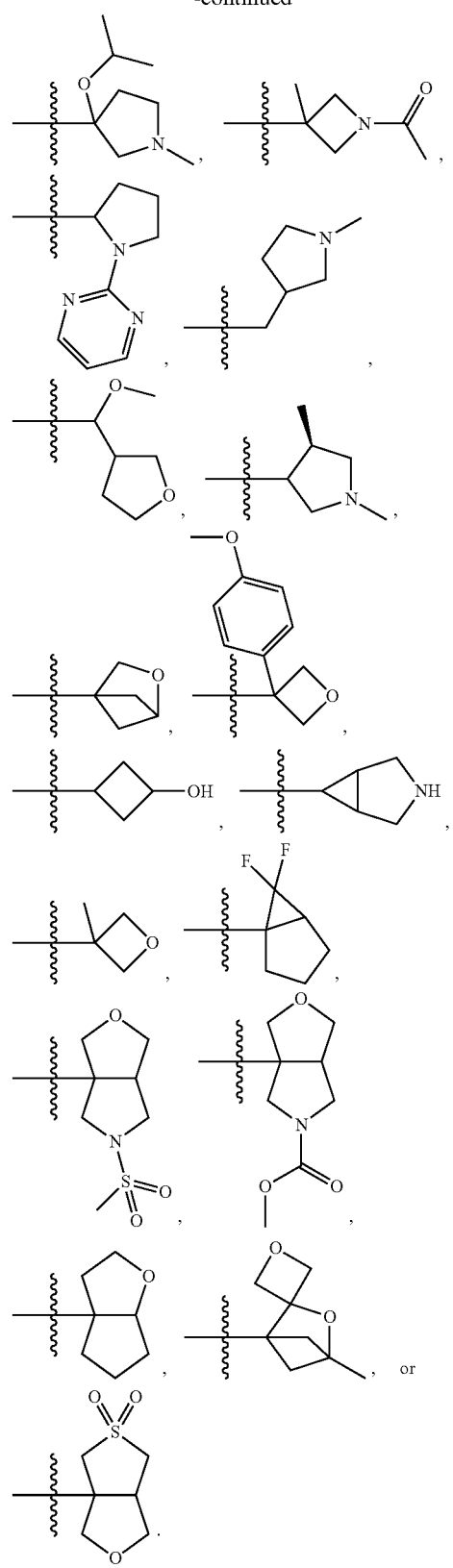
In some embodiments is a compound of Formula (II) or (II'), or a pharmaceutically acceptable salt or solvate thereof, wherein R³ is

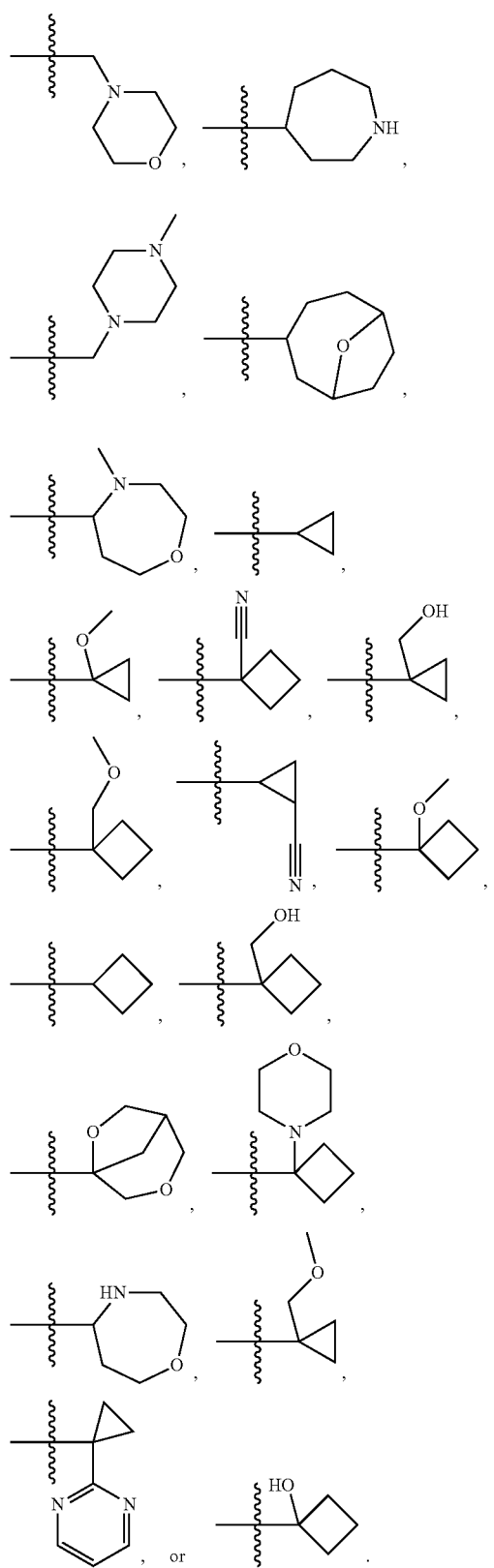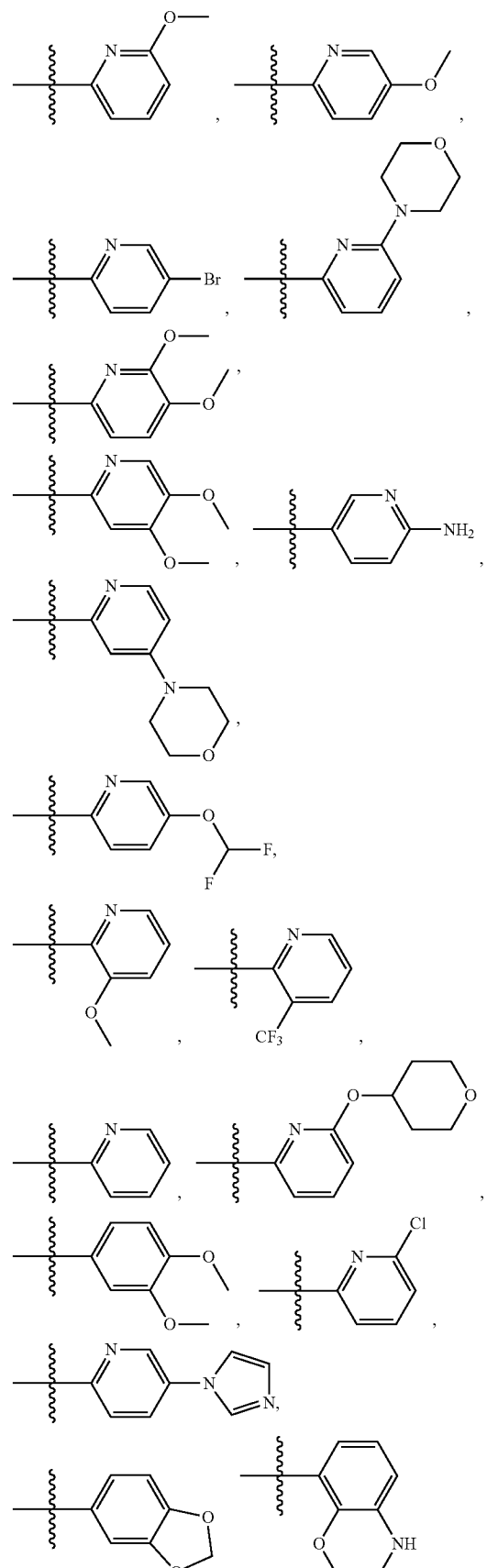
In some embodiments is a compound of Formula (II) or (II'), or a pharmaceutically acceptable salt or solvate thereof, wherein R³ is

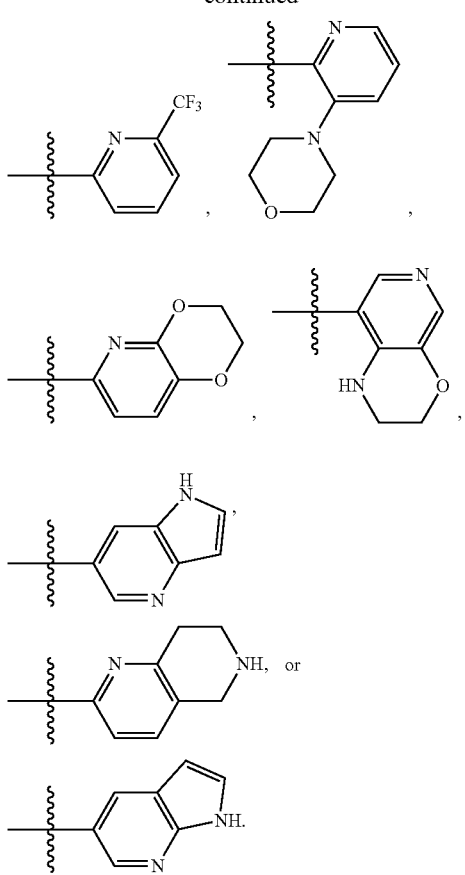
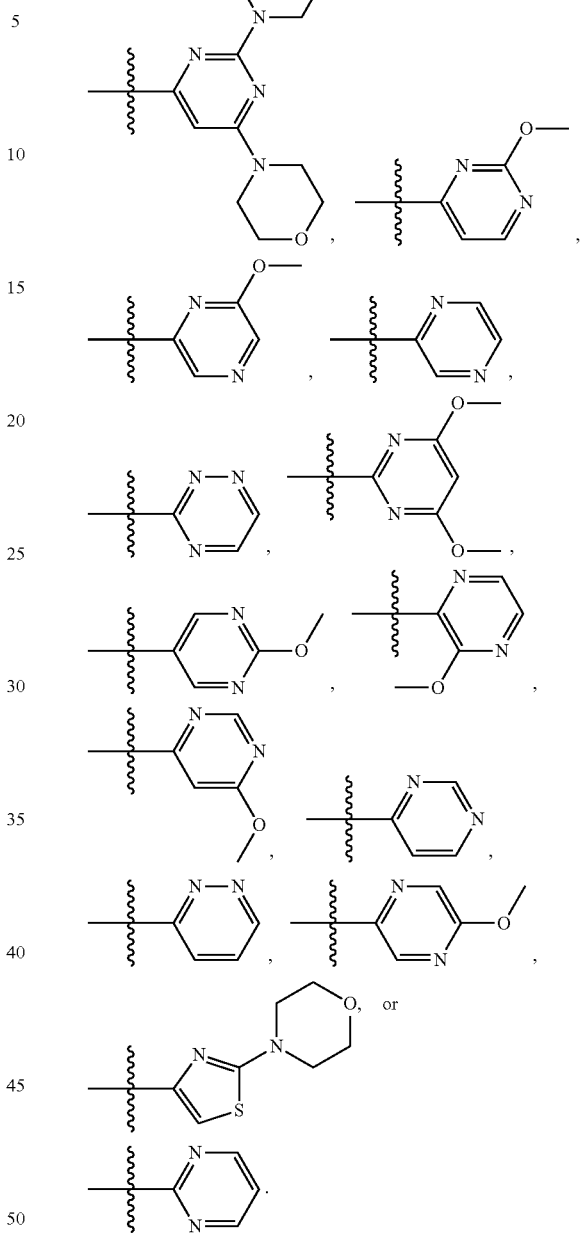
In some embodiments is a compound of Formula (II) or (II'), or a pharmaceutically acceptable salt or solvate thereof, wherein $R^3$ is
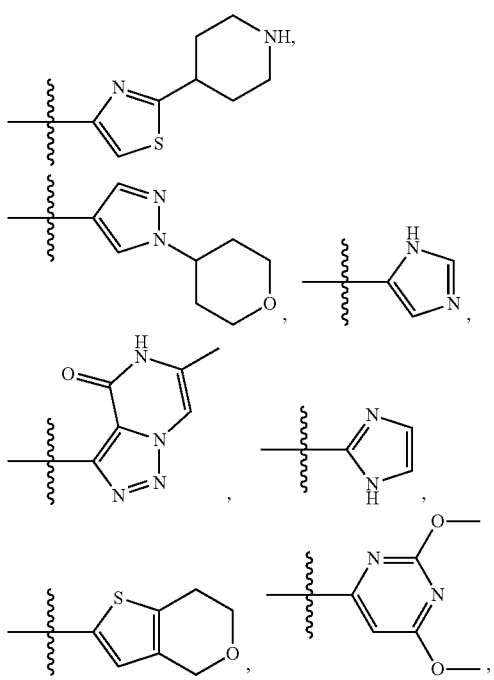
In some embodiments is a compound of Formula (II) or (II'), or a pharmaceutically acceptable salt or solvate thereof, wherein $R^3$ is
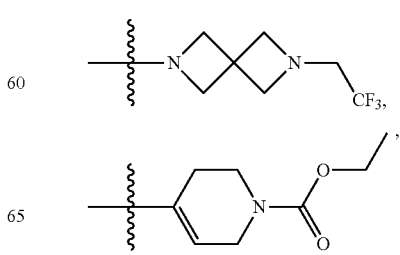

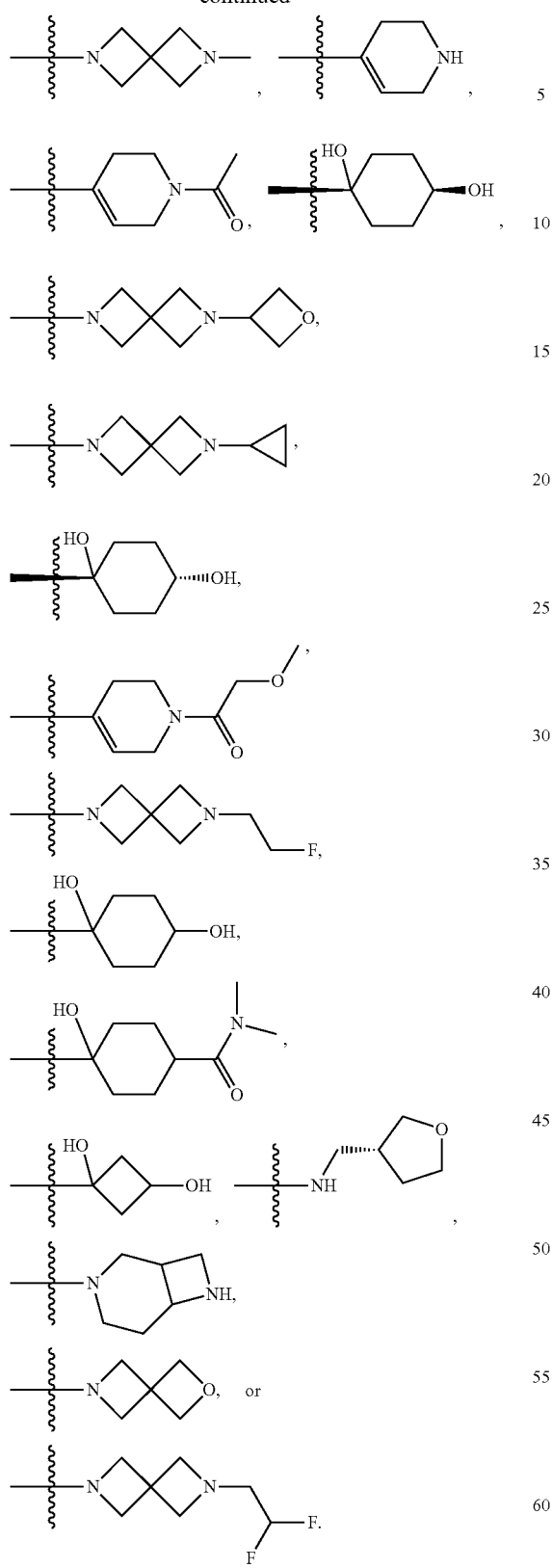
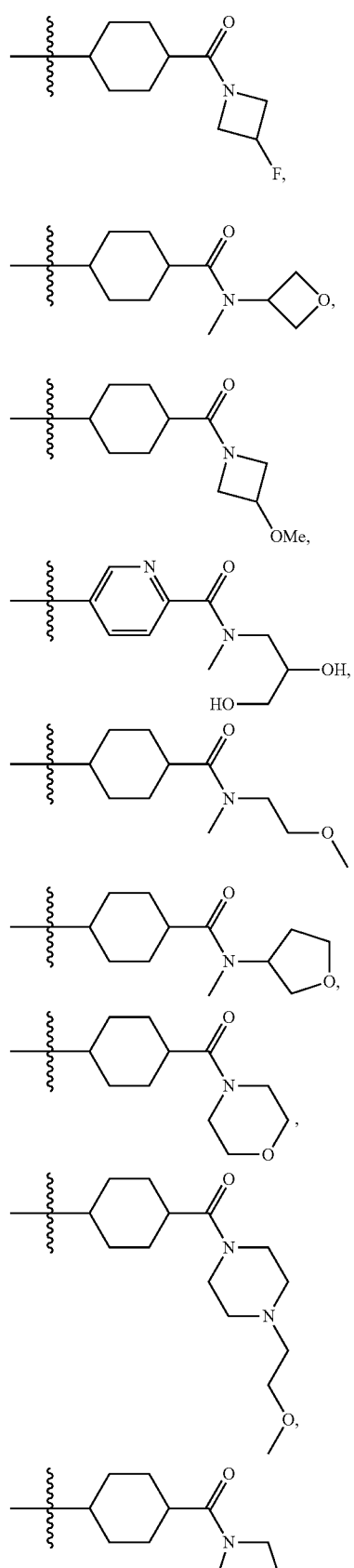
In some embodiments is a compound of Formula (II) or (II'), or a pharmaceutically acceptable salt or solvate thereof, wherein R³ is

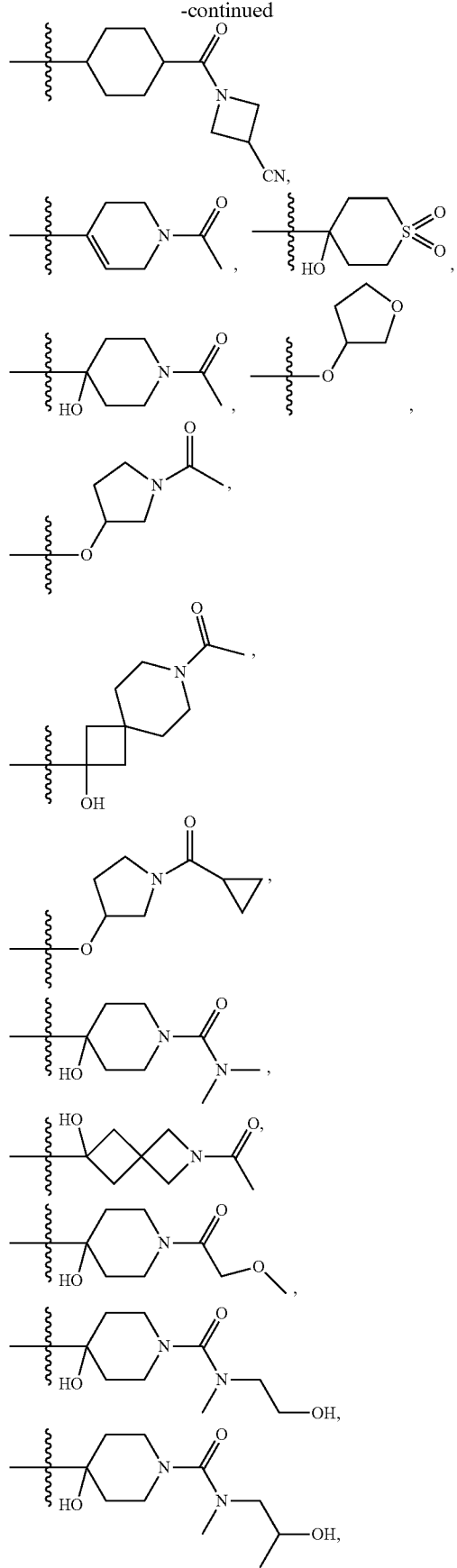
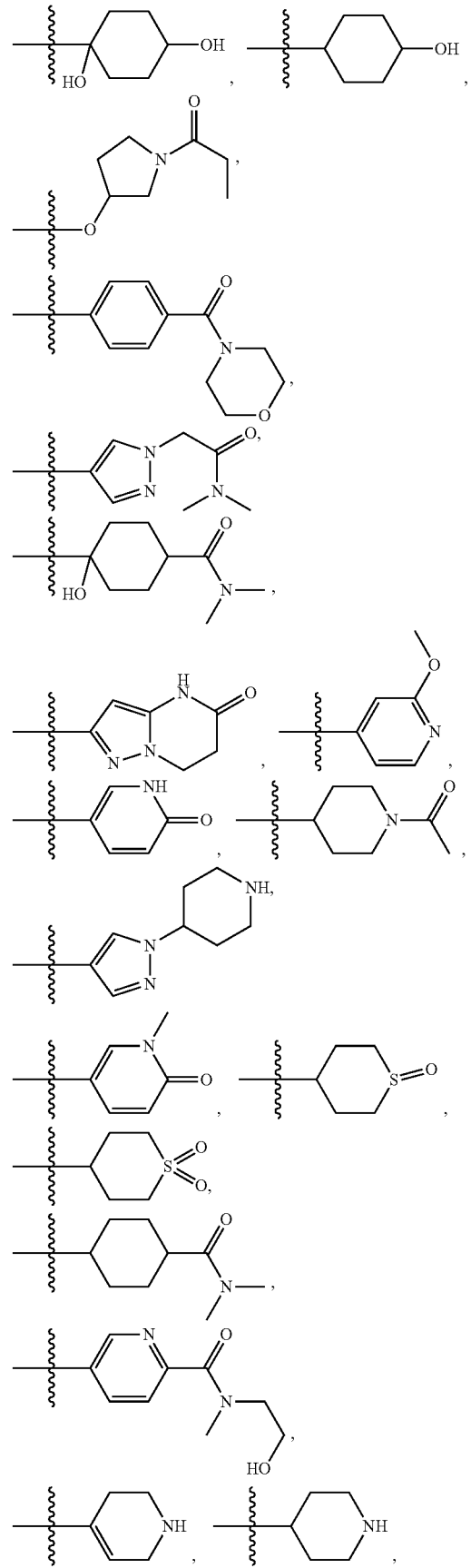

161
-continued
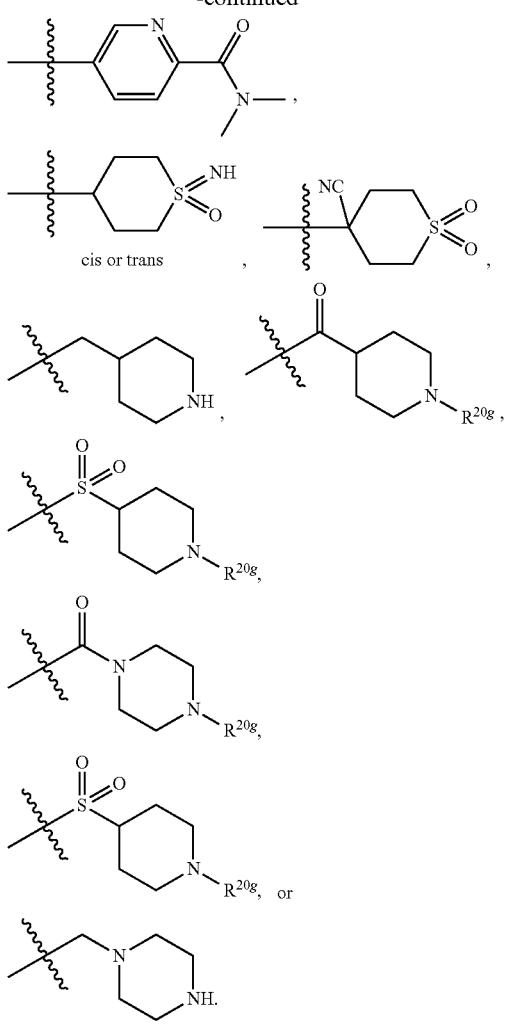
In some embodiments is a compound of Formula (II) or (II'), or a pharmaceutically acceptable salt or solvate thereof, wherein R³ is
162
-continued
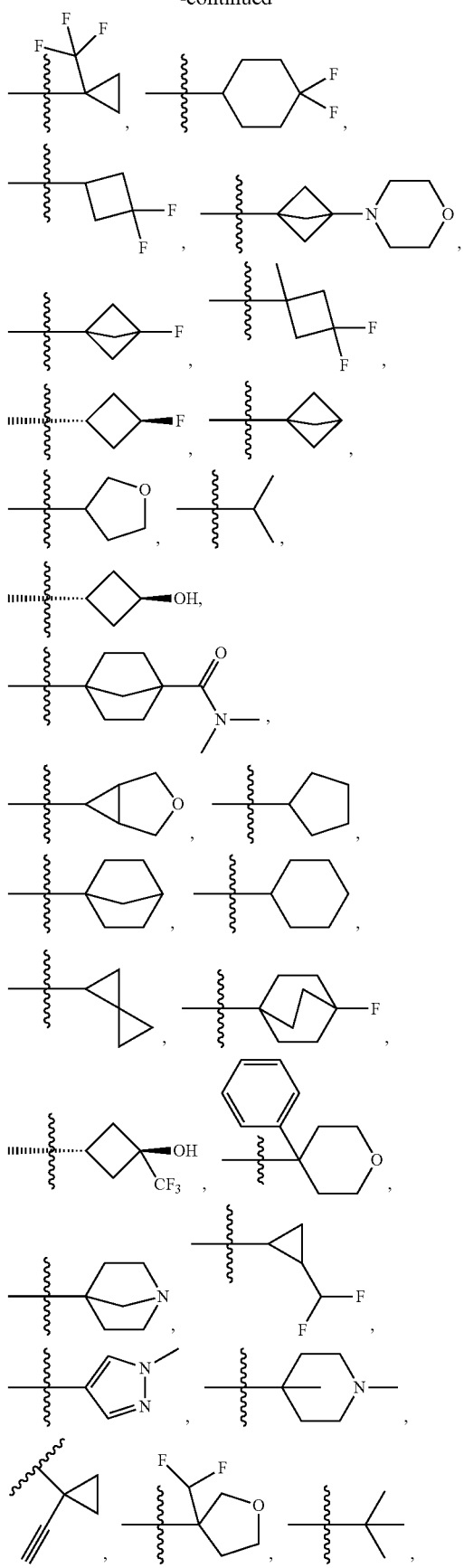

-continued

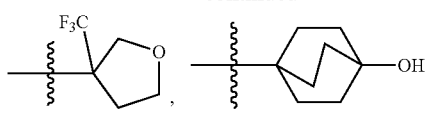

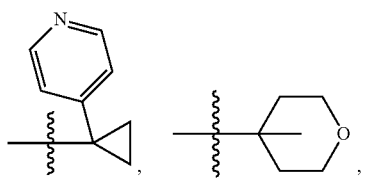

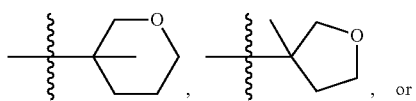

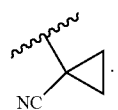

In some embodiments of a compound of Formula (II) or (II'), or a pharmaceutically acceptable salt or solvate thereof, $R^3$ is

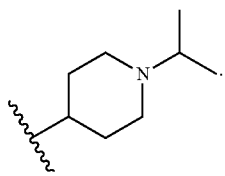 [SMILES: *C1CCN(C(C)C)CC1]

In some embodiments of a compound of Formula (II) or (II'), or a pharmaceutically acceptable salt or solvate thereof, $R^3$ is

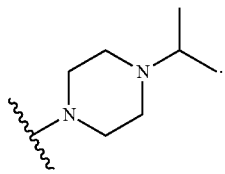 [SMILES: *N1CCN(C(C)C)CC1]

In some embodiments of a compound of Formula (II) or (II'), or a pharmaceutically acceptable salt or solvate thereof, $R^3$ is

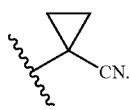

In some embodiments of a compound of Formula (II) or (II'), or a pharmaceutically acceptable salt or solvate thereof, $R^3$ is

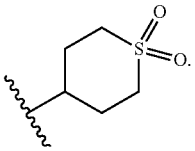 [SMILES: *C1CCS(=O)(=O)CC1]

In some embodiments of a compound of Formula (II) or (II'), or a pharmaceutically acceptable salt or solvate thereof, $R^3$ is

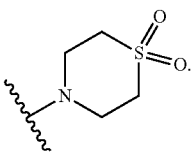 [SMILES: *N1CCS(=O)(=O)CC1]

In some embodiments is a compound of Formula (II) or (II'), or a pharmaceutically acceptable salt or solvate thereof, wherein $R^6$ is selected from hydrogen, $C_{1-6}$alkyl, $C_{3-10}$cycloalkyl, $C_{2-9}$heterocycloalkyl, $C_{6-10}$aryl, and $C_{1-9}$heteroaryl, wherein $C_{1-6}$alkyl, $C_{3-10}$cycloalkyl, $C_{2-9}$heterocycloalkyl, $C_{6-10}$aryl, and $C_{1-9}$heteroaryl are optionally substituted with one, two, or three $R^{20c}$. In some embodiments is a compound of Formula (II) or (II'), or a pharmaceutically acceptable salt or solvate thereof, wherein $R^6$ is selected from hydrogen and $C_{1-6}$alkyl optionally substituted with one, two, or three $R^{20c}$. In some embodiments is a compound of Formula (II) or (II'), or a pharmaceutically acceptable salt or solvate thereof, wherein $R^6$ is $C_{1-6}$alkyl optionally substituted with one, two, or three $R^{20c}$. In some embodiments is a compound of Formula (II) or (II'), or a pharmaceutically acceptable salt or solvate thereof, wherein $R^6$ is hydrogen. In some embodiments is a compound of Formula (II) or (II'), or a pharmaceutically acceptable salt or solvate thereof, wherein $R^6$ is methyl.

In some embodiments is a compound of Formula (II) or (II'), or a pharmaceutically acceptable salt or solvate thereof, wherein $R^7$ is selected from hydrogen, $C_{1-6}$alkyl, $C_{3-10}$cycloalkyl, $C_{2-9}$heterocycloalkyl, $C_{6-10}$aryl, and $C_{1-9}$heteroaryl, wherein $C_{1-6}$alkyl, $C_{3-10}$cycloalkyl, $C_{2-9}$heterocycloalkyl, $C_{6-10}$aryl, and $C_{1-9}$heteroaryl are optionally substituted with one, two, or three $R^{20c}$. In some embodiments is a compound of Formula (II) or (II'), or a pharmaceutically acceptable salt or solvate thereof, wherein $R^7$ is selected from hydrogen and $C_{1-6}$alkyl optionally substituted with one, two, or three $R^{20c}$. In some embodiments is a compound of Formula (II) or (II'), or a pharmaceutically acceptable salt or solvate thereof, wherein $R^7$ is $C_{1-6}$alkyl optionally substituted with one, two, or three $R^{20c}$. In some embodiments is a compound of Formula (II) or (II'), or a pharmaceutically acceptable salt or solvate thereof, wherein $R^7$ is hydrogen. In some embodiments is a compound of Formula (II) or (II'), or a pharmaceutically acceptable salt or solvate thereof, wherein $R^7$ is methyl.

In some embodiments is a compound of Formula (II) or (II'), or a pharmaceutically acceptable salt or solvate thereof, wherein $L^1$ is a bond. In some embodiments is a compound of Formula (II) or (II'), or a pharmaceutically acceptable salt or solvate thereof, wherein $L^1$ is $C_{1-6}$alkyl.

In some embodiments is a compound of Formula (II) or (II'), or a pharmaceutically acceptable salt or solvate thereof, wherein $R^1$ is a 6-10 membered aryl ring optionally substituted with one or more $R^{10}$. In some embodiments is a compound of Formula (II) or (II'), or a pharmaceutically acceptable salt or solvate thereof, wherein $R^1$ is a phenyl optionally substituted with one or more $R^{10}$. In some embodiments is a compound of Formula (II) or (II'), or a pharmaceutically acceptable salt or solvate thereof, wherein $R^1$ is a phenyl substituted with one or more $R^{10}$. In some embodiments is a compound of Formula (II) or (II'), or a pharmaceutically acceptable salt or solvate thereof, wherein $R^1$ is phenyl substituted with one, two, or three $R^{10}$. In some embodiments is a compound of Formula (II) or (II'), or a pharmaceutically acceptable salt or solvate thereof, wherein $R^1$ is phenyl substituted with one, two, or three $R^{10}$, wherein each $R^{10}$ is independently selected from halogen, $C_{1-6}$alkyl, $C_{3-7}$cycloalkyl, $C_{2-9}$heterocycloalkyl, $C_{6-10}$aryl, $C_{1-9}$heteroaryl, —$OR^{12}$, and $N(R^{12})(R^{13})$, wherein $C_{1-6}$alkyl, $C_{3-7}$cycloalkyl, $C_{2-9}$heterocycloalkyl, $C_{6-10}$aryl, and $C_{1-9}$heteroaryl are optionally substituted with one, two, or three $R^{20d}$. In some embodiments is a compound of Formula (II) or (II'), or a pharmaceutically acceptable salt or solvate thereof, wherein $R^1$ is phenyl substituted with one, two, or three $R^{10}$, wherein each $R^{10}$ is independently selected from halogen, $C_{1-6}$alkyl, and $N(R^{12})(R^{13})$, wherein $C_{1-6}$alkyl is optionally substituted with one, two, or three $R^{20d}$. In some embodiments is a compound of Formula (II) or (II'), or a pharmaceutically acceptable salt or solvate thereof, wherein $R^1$ is phenyl substituted with one, two, or three $R^{10}$, wherein each $R^{10}$ is independently selected from halogen and $C_{1-6}$alkyl, wherein $C_{1-6}$alkyl is substituted with one, two, or three $R^{20d}$, and each $R^{20d}$ is halogen.

In some embodiments is a compound of Formula (II) or (II'), or a pharmaceutically acceptable salt or solvate thereof, wherein $R^1$ is a 5-10 membered heteroaryl ring optionally substituted with one or more $R^{10}$. In some embodiments is a compound of Formula (II) or (II'), or a pharmaceutically acceptable salt or solvate thereof, wherein $R^1$ is a 5-10 membered heteroaryl ring substituted with one or more $R^{10}$. In some embodiments is a compound of Formula (II) or (II'), or a pharmaceutically acceptable salt or solvate thereof, wherein $R^1$ is a 5-10 membered heteroaryl ring substituted with one, two, or three $R^{10}$. In some embodiments is a compound of Formula (II) or (II'), or a pharmaceutically acceptable salt or solvate thereof, wherein $R^1$ is a 5-10 membered heteroaryl ring substituted with one, two, or three $R^{10}$, wherein each $R^{10}$ is independently selected from halogen, $C_{1-6}$alkyl, $C_{3-7}$cycloalkyl, $C_{2-9}$heterocycloalkyl, $C_{6-10}$aryl, $C_{1-9}$heteroaryl, —$OR^{12}$, and $N(R^{12})(R^{13})$, wherein $C_{1-6}$alkyl, $C_{3-7}$cycloalkyl, $C_{2-9}$heterocycloalkyl, $C_{6-10}$aryl, and $C_{1-9}$heteroaryl are optionally substituted with one, two, or three $R^{20d}$. In some embodiments is a compound of Formula (II) or (II'), or a pharmaceutically acceptable salt or solvate thereof, wherein $R^1$ is a 5-10 membered heteroaryl ring substituted with one, two, or three $R^{10}$, wherein each $R^{10}$ is independently selected from halogen, $C_{1-6}$alkyl, and $N(R^{12})(R^{13})$, wherein $C_{1-6}$alkyl is optionally substituted with one, two, or three $R^{20d}$. In some embodiments is a compound of Formula (II) or (II'), or a pharmaceutically acceptable salt or solvate thereof, wherein $R^1$ is a 5-10 membered heteroaryl ring substituted with one, two, or three $R^{10}$, wherein each $R^{10}$ is independently selected from halogen and $C_{1-6}$alkyl, wherein $C_{1-6}$alkyl is substituted with one, two, or three $R^{20d}$, and each $R^{20d}$ is halogen. In some embodiments is a compound of Formula (II) or (II'), or a pharmaceutically acceptable salt or solvate thereof, wherein $R^1$ is an unsubstituted 5-10 membered heteroaryl ring.

In some embodiments is a compound of Formula (II) or (II'), or a pharmaceutically acceptable salt or solvate thereof, wherein $R^1$ is a 3-12 membered cycloalkyl ring optionally substituted with one or more $R^{10}$. In some embodiments is a compound of Formula (II) or (II'), or a pharmaceutically acceptable salt or solvate thereof, wherein $R^1$ is a 3-12 membered cycloalkyl ring substituted with one or more $R^{10}$. In some embodiments is a compound of Formula (II) or (II'), or a pharmaceutically acceptable salt or solvate thereof, wherein $R^1$ is an unsubstituted 3-12 membered cycloalkyl ring.

In some embodiments is a compound of Formula (II) or (II'), or a pharmaceutically acceptable salt or solvate thereof, wherein $R^1$ is a 3-12 membered heterocycloalkyl ring optionally substituted with one or more $R^{10}$. In some embodiments is a compound of Formula (II) or (II'), or a pharmaceutically acceptable salt or solvate thereof, wherein $R^1$ is a 3-12 membered heterocycloalkyl ring substituted with one or more $R^{10}$. In some embodiments is a compound of Formula (II) or (II'), or a pharmaceutically acceptable salt or solvate thereof, wherein $R^1$ is an unsubstituted 3-12 membered heterocycloalkyl ring optionally substituted with one or more $R^{10}$.

In some embodiments is a compound of Formula (II) or (II'), or a pharmaceutically acceptable salt or solvate thereof, wherein $R^4$ is hydrogen. In some embodiments is a compound of Formula (II) or (II'), or a pharmaceutically acceptable salt or solvate thereof, wherein $R^4$ is $C_{1-6}$alkyl. In some embodiments is a compound of Formula (II) or (II'), or a pharmaceutically acceptable salt or solvate thereof, wherein $R^4$ is —$CH_3$. In some embodiments is a compound of Formula (II) or (II'), or a pharmaceutically acceptable salt or solvate thereof, wherein $R^4$ is $C_{1-6}$haloalkyl.

In some embodiments, the disclosure provides a compound of Formula (III), or a pharmaceutically acceptable salt or solvate thereof:

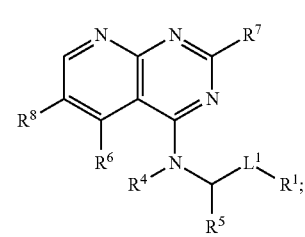

Formula (III)

$R^1$ is a 3-12 membered cycloalkyl ring, 3-12 membered heterocycloalkyl ring, 6-10 membered aryl ring, or 5-10 membered heteroaryl ring, wherein the 3-12 membered cycloalkyl ring, 3-12 membered heterocycloalkyl ring, 6-10 membered aryl ring, and 5-10 membered heteroaryl ring are optionally substituted with one or more $R^{10}$;

$L^1$ is a bond or $C_{1-6}$alkyl;

$R^4$ is selected from hydrogen, $C_{1-6}$alkyl, and $C_{1-6}$haloalkyl;

$R^5$ is selected from hydrogen, $C_{1-6}$alkyl, and $C_{1-6}$haloalkyl;

$R^6$ is selected from hydrogen, halogen, —CN, $C_{1-6}$alkyl, $C_{2-6}$alkenyl, $C_{2-6}$alkynyl, $C_{3-10}$cycloalkyl, $C_{2-9}$heterocycloalkyl, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{15}$, —$S(O)_2R^{15}$, —$S(O)_2$ $N(R^{12})(R^{13})$, —$S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, —$CH_2S(O)_2N(R^{12})(R^{13})$, —$CH_2N(R^{12})S(O)_2(R^{13})$, and —$P(O)(R^{17})(R^{17a})$ wherein $C_{1-6}$alkyl, $C_{2-6}$alkenyl, $C_{2-6}$alkynyl, $C_{3-10}$cycloalkyl, and $C_{2-9}$heterocycloalkyl are optionally substituted with one, two, or three $R^{20c}$;

$R^7$ is selected from hydrogen, halogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{1-9}$heteroaryl, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{15}$, —$S(O)_2R^{15}$, —$S(O)_2N(R^{12})(R^{13})$, —$S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, —$CH_2S(O)_2N(R^{12})(R^{13})$, —$CH_2N(R^{12})S(O)_2(R^{13})$, and —$P(O)(R^{17})(R^{17a})$, wherein $C_{1-6}$alkyl, $C_{2-6}$alkenyl, $C_{2-6}$alkynyl, $C_{3-10}$cycloalkyl, $C_{2-9}$heterocycloalkyl, and $C_{1-9}$heteroaryl are optionally substituted with one, two, or three $R^{20c}$;

$R^8$ is —$OR^{9a}$, —$NR^{9b}R^{9c}$, —$SR^{9b}$, —$S(O)R^{9d}$, —$S(O)_2R^{9d}$, —$S(O)_2NR^{9b}R^{9c}$, —$C(R^{9e})(R^{9f})(R^{9g})$, and $C(O)NR^{9b}R^{9c}$;

$R^{9a}$ is selected from hydrogen, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —$C(O)OR^{12}$, —$C(O)R^{15}$, —$C(O)N(R^{12})(R^{13})$, —$S(O)_2R^{15}$, —$S(O)_2N(R^{12})(R^{13})$, wherein $C_{1-6}$alkyl is substituted with one, two, or three $R^{20a}$, and wherein $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20a}$;

$R^{9b}$ is selected from hydrogen, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —$C(O)OR^{12}$, —$C(O)R^{15}$, —$C(O)N(R^{12})(R^{13})$, —$S(O)_2R^{15}$, and —$S(O)_2N(R^{12})(R^{13})$, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20a}$;

$R^{9c}$ is selected from hydrogen, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20a}$; or $R^{9b}$ and $R^{9c}$, together with the nitrogen to which they are attached, form a $C_{2-9}$heterocycloalkyl ring optionally substituted with one, two, or three $R^{20a}$;

$R^{9d}$ is selected from $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl, wherein $C_{1-6}$alkyl is substituted with one, two, or three $R^{20a}$, and wherein $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20a}$;

$R^{9e}$ is selected from hydrogen, $C_{1-6}$alkyl, $C_{2-6}$alkenyl, $C_{2-6}$alkynyl, $C_{3-10}$cycloalkyl, $C_{2-9}$heterocycloalkyl, $C_{1-9}$heteroaryl, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{15}$, —$S(O)_2R^{15}$, —$S(O)_2N(R^{12})(R^{13})$, —$S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, —$CH_2S(O)_2N(R^{12})(R^{13})$, —$CH_2N(R^{12})S(O)_2(R^{13})$, and —$P(O)(R^{17})(R^{17a})$, wherein $C_{1-6}$alkyl, $C_{2-6}$alkenyl, $C_{2-6}$alkynyl, $C_{3-10}$cycloalkyl, $C_{2-9}$heterocycloalkyl, and $C_{1-9}$heteroaryl are optionally substituted with one, two, or three $R^{20a}$;

$R^{9f}$ is selected from hydrogen, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20a}$;

$R^{9g}$ is selected from $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20a}$;

each $R^{10}$ is independently selected from halogen, —CN, $C_{1-6}$alkyl, $C_{2-6}$alkenyl, $C_{2-6}$alkynyl, $C_{3-7}$cycloalkyl, $C_{2-9}$heterocycloalkyl, $C_{6-10}$aryl, $C_{1-9}$heteroaryl, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{15}$, —$S(O)_2R^{15}$, —$S(O)_2N(R^{12})(R^{13})$, —$S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, —$CH_2S(O)_2N(R^{12})(R^{13})$, —$CH_2N(R^{12})S(O)_2(R^{13})$, and —$P(O)(R^{17})(R^{17a})$, wherein $C_{1-6}$alkyl, $C_{2-6}$alkenyl, $C_{2-6}$alkynyl, $C_{3-7}$cycloalkyl, $C_{2-9}$heterocycloalkyl, $C_{6-10}$aryl, and $C_{1-9}$heteroaryl are optionally substituted with one, two, or three $R^{20a}$;

each $R^{12}$ is independently selected from hydrogen, $C_{1-6}$alkyl, $C_{1-6}$ haloalkyl, $C_{2-6}$alkenyl, $C_{2-6}$alkynyl, $C_{3-7}$cycloalkyl, $C_{2-9}$heterocycloalkyl, $C_{6-10}$aryl, and $C_{1-9}$heteroaryl, wherein $C_{1-6}$alkyl, $C_{2-6}$alkenyl, $C_{2-6}$alkynyl, $C_{3-7}$cycloalkyl, $C_{2-9}$heterocycloalkyl, $C_{6-10}$aryl, and $C_{1-9}$heteroaryl are optionally substituted with one, two, or three $R^{20e}$;

each $R^{13}$ is independently selected from hydrogen, $C_{1-6}$alkyl, and $C_{1-6}$haloalkyl; or $R^{12}$ and $R^{13}$, together with the nitrogen to which they are attached, form a $C_{2-9}$heterocycloalkyl ring optionally substituted with one, two, or three $R^{20f}$;

each $R^{14}$ is independently selected from hydrogen, $C_{1-6}$alkyl, and $C_{1-6}$haloalkyl;

each $R^{15}$ is independently selected $C_{1-6}$alkyl, $C_{2-6}$alkenyl, $C_{2-6}$alkynyl, $C_{3-7}$cycloalkyl, $C_{2-9}$heterocycloalkyl, $C_{6-10}$aryl, and $C_{1-9}$ heteroaryl, wherein $C_{1-6}$alkyl, $C_{2-6}$alkenyl, $C_{2-6}$alkynyl, $C_{3-7}$cycloalkyl, $C_{2-9}$heterocycloalkyl, $C_{6-10}$aryl, and $C_{1-9}$heteroaryl are optionally substituted with one, two, or three $R^{20g}$;

each $R^{17}$ and each $R^{17a}$ are each independently selected from $C_{1-6}$alkyl and $C_{3-6}$cycloalkyl, wherein $C_{1-6}$alkyl and $C_{3-6}$cycloalkyl are optionally substituted with one, two or three of $R^{20h}$; or $R^{17}$ and $R^{17a}$ are combined to form a $C_{2-9}$heterocycloalkyl ring;

each $R^{20a}$, $R^{20b}$, $R^{20c}$, $R^{20d}$, $R^{20e}$, $R^{20f}$, $R^{20g}$, and $R^{20h}$ are each independently selected from halogen, oxo, =NH, —CN, $C_{1-6}$alkyl, $C_{2-6}$alkenyl, $C_{2-6}$alkynyl, $C_{3-10}$cycloalkyl, —$CH_2$—$C_{3-10}$cycloalkyl, $C_{2-9}$heterocycloalkyl, —$CH_2$—$C_{2-9}$heterocycloalkyl, $C_{6-10}$aryl, —$CH_2$—$C_{6-10}$aryl, $C_{1-9}$heteroaryl, —$OR^{21}$, —$SR^{21}$, —$N(R^{22})(R^{23})$, —$C(O)OR^{22}$, —$C(O)N(R^{22})(R^{23})$, —$C(O)C(O)N(R^{22})(R^{23})$, —$OC(O)N(R^{22})(R^{23})$, —$N(R^{24})C(O)N(R^{22})(R^{23})$, —$N(R^{24})C(O)OR^{25}$, —$N(R^{24})C(O)R^{25}$, —$N(R^{24})S(O)_2R^{25}$, —$C(O)R^{25}$, —$S(O)_2R^{25}$, —$S(O)_2N(R^{22})(R^{23})$, —$OCH_2C(O)OR^{22}$, and —$OC(O)R^{25}$, wherein $C_{1-6}$alkyl, $C_{2-6}$alkenyl, $C_{2-6}$alkynyl, $C_{3-10}$cycloalkyl, —$CH_2$—$C_{3-10}$cycloalkyl, $C_{2-9}$heterocycloalkyl, —$CH_2$—$C_{2-9}$heterocycloalkyl, $C_{6-10}$aryl, —$CH_2$—$C_{6-10}$aryl, and $C_{1-9}$heteroaryl are optionally substituted with one, two or three groups independently selected from halogen, oxo, =NH, —CN, $C_{1-6}$alkyl, $C_{1-6}$haloalkyl, $C_{1-6}$alkoxy, $C_{1-6}$haloalkoxy, —OR$^{21}$, —SR$^{21}$, —N(R$^{22}$)(R$^{23}$), —C(O)OR$^{22}$, —C(O)N(R$^{22}$)(R$^{23}$), —C(O)C(O)N(R$^{22}$)(R$^{23}$), —OC(O)N(R$^{22}$)(R$^{23}$), —N(R$^{24}$)C(O)N(R$^{22}$)(R$^{23}$), —N(R$^{24}$)C(O)OR$^{25}$, —N(R$^{24}$)C(O)R$^{25}$, —N(R$^{24}$)S(O)$_2$R$^{25}$, —C(O)R$^{25}$, —S(O)$_2$R$^{25}$, —S(O)$_2$N(R$^{22}$)(R$^{23}$), and —OC(O)R$^{25}$;

each R$^{21}$ is independently selected from H, $C_{1-6}$alkyl, $C_{1-6}$haloalkyl, $C_{2-6}$alkenyl, $C_{2-6}$alkynyl, $C_{3-7}$cycloalkyl, $C_{2-9}$heterocycloalkyl, $C_{6-10}$aryl, and $C_{1-9}$heteroaryl, wherein $C_{3-7}$cycloalkyl, $C_{2-9}$heterocycloalkyl, $C_{6-10}$aryl, and $C_{1-9}$heteroaryl are optionally substituted with one, two, or three groups independently selected from halogen and $C_{1-6}$alkyl;

each R$^{22}$ is independently selected from H, $C_{1-6}$alkyl, $C_{1-6}$haloalkyl, $C_{2-6}$alkenyl, $C_{2-6}$alkynyl, $C_{3-7}$cycloalkyl, $C_{2-9}$heterocycloalkyl, $C_{6-10}$aryl, and $C_{1-9}$heteroaryl, wherein $C_{3-7}$cycloalkyl, $C_{2-9}$heterocycloalkyl, $C_{6-10}$aryl, and $C_{1-9}$heteroaryl are optionally substituted with one, two, or three groups independently selected from halogen and $C_{1-6}$alkyl;

each R$^{23}$ is independently selected from H and $C_{1-6}$alkyl;
each R$^{24}$ is independently selected from H and $C_{1-6}$alkyl; and each R$^{25}$ is selected from $C_{1-6}$alkyl, $C_{2-6}$alkenyl, $C_{2-6}$alkynyl, $C_{3-7}$cycloalkyl, $C_{2-9}$heterocycloalkyl, $C_{6-10}$aryl, and $C_{1-9}$heteroaryl, wherein $C_{1-6}$alkyl, $C_{3-7}$cycloalkyl, $C_{2-9}$heterocycloalkyl, $C_{6-10}$aryl, and $C_{1-9}$heteroaryl are optionally substituted with one, two, or three groups independently selected from halogen, $C_{1-6}$alkyl, $C_{1-6}$haloalkyl, $C_{1-6}$alkoxy, $C_{3-7}$cycloalkyl, $C_{2-9}$heterocycloalkyl, $C_{6-10}$aryl, and $C_{1-9}$heteroaryl.

In some embodiments is a compound of Formula (III), or a pharmaceutically acceptable salt or solvate thereof, wherein R$^5$ is $C_{1-6}$alkyl. In some embodiments is a compound of Formula (III), or a pharmaceutically acceptable salt or solvate thereof, wherein R$^5$ is —CH$_3$. In some embodiments is a compound of Formula (III), or a pharmaceutically acceptable salt or solvate thereof, wherein R$^5$ is $C_{1-6}$ haloalkyl. In some embodiments is a compound of Formula (III), or a pharmaceutically acceptable salt or solvate thereof, wherein R$^5$ is hydrogen.

In some embodiments is a compound of Formula (III) having the structure of Formula (III'), or a pharmaceutically acceptable salt or solvate thereof:

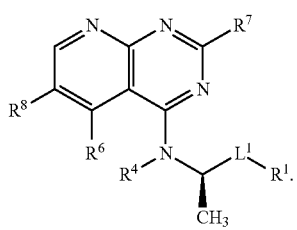

Formula (III')

In some embodiments is a compound of Formula (III) or (III'), or a pharmaceutically acceptable salt or solvate thereof, wherein R$^8$ is —OR$^{9a}$. In some embodiments is a compound of Formula (III) or (III'), or a pharmaceutically acceptable salt or solvate thereof, wherein R$^{9a}$ is $C_{1-6}$alkyl optionally substituted with one, two, or three R$^{20a}$. In some embodiments is a compound of Formula (III) or (III'), or a pharmaceutically acceptable salt or solvate thereof, wherein R$^{9a}$ is unsubstituted $C_{1-6}$alkyl. In some embodiments is a compound of Formula (III) or (III'), or a pharmaceutically acceptable salt or solvate thereof, wherein R$^{9a}$ is —CH$_3$.

In some embodiments is a compound of Formula (III) or (III'), or a pharmaceutically acceptable salt or solvate thereof, wherein R$^8$ is —NR$^{9b}$R$^{9c}$. In some embodiments is a compound of Formula (III) or (III'), or a pharmaceutically acceptable salt or solvate thereof, wherein R$^{9b}$ is $C_{1-6}$alkyl optionally substituted with one, two, or three R$^{20a}$. In some embodiments is a compound of Formula (III) or (III'), or a pharmaceutically acceptable salt or solvate thereof, wherein R$^{9b}$ is unsubstituted $C_{1-6}$alkyl. In some embodiments is a compound of Formula (III) or (III'), or a pharmaceutically acceptable salt or solvate thereof, wherein R$^{9b}$ is —CH$_3$. In some embodiments is a compound of Formula (III) or (III'), or a pharmaceutically acceptable salt or solvate thereof, wherein R$^{9b}$ is hydrogen. In some embodiments is a compound of Formula (III) or (III'), or a pharmaceutically acceptable salt or solvate thereof, wherein R$^{9c}$ is $C_{1-6}$alkyl optionally substituted with one, two, or three R$^{20a}$. In some embodiments is a compound of Formula (III) or (III'), or a pharmaceutically acceptable salt or solvate thereof, wherein R$^{9c}$ is unsubstituted $C_{1-6}$alkyl. In some embodiments is a compound of Formula (III) or (III'), or a pharmaceutically acceptable salt or solvate thereof, wherein R$^{9c}$ is —CH$_3$. In some embodiments is a compound of Formula (III) or (III'), or a pharmaceutically acceptable salt or solvate thereof, wherein R$^{9c}$ is hydrogen. In some embodiments is a compound of Formula (III) or (III'), or a pharmaceutically acceptable salt or solvate thereof, wherein R$^{9b}$ and R$^{9c}$ are independently $C_{1-6}$alkyl optionally substituted with one, two, or three R$^{20a}$. In some embodiments is a compound of Formula (III) or (III'), or a pharmaceutically acceptable salt or solvate thereof, wherein R$^{9b}$ and R$^{9c}$ are independently unsubstituted $C_{1-6}$alkyl. In some embodiments is a compound of Formula (III) or (III'), or a pharmaceutically acceptable salt or solvate thereof, wherein R$^{9b}$ and R$^{9c}$ are —CH$_3$. In some embodiments is a compound of Formula (III) or (III'), or a pharmaceutically acceptable salt or solvate thereof, wherein R$^{9b}$ and R$^{9c}$ are hydrogen.

In some embodiments is a compound of Formula (III) or (III'), or a pharmaceutically acceptable salt or solvate thereof, wherein R$^8$ is —C(R$^{9e}$)(R$^{9f}$)(R$^{9g}$). In some embodiments is a compound of Formula (III) or (III'), or a pharmaceutically acceptable salt or solvate thereof, wherein R$^{9e}$ is hydrogen or $C_{1-6}$alkyl optionally substituted with one, two, or three R$^{20a}$. In some embodiments is a compound of Formula (III) or (III'), or a pharmaceutically acceptable salt or solvate thereof, wherein R$^{9e}$ is hydrogen. In some embodiments is a compound of Formula (III) or (III'), or a pharmaceutically acceptable salt or solvate thereof, wherein R$^{9e}$ is $C_{1-6}$alkyl optionally substituted with one, two, or three R$^{20a}$. In some embodiments is a compound of Formula (III) or (III'), or a pharmaceutically acceptable salt or solvate thereof, wherein R$^{9e}$ is unsubstituted $C_{1-6}$alkyl. In some embodiments is a compound of Formula (III) or (III'), or a pharmaceutically acceptable salt or solvate thereof, wherein R$^{9e}$ is —CH$_3$. In some embodiments is a compound of Formula (III) or (III'), or a pharmaceutically acceptable salt or solvate thereof, wherein R$^{9f}$ is hydrogen or $C_{1-6}$alkyl optionally substituted with one, two, or three R$^{20a}$. In some embodiments is a compound of Formula (III) or (III'), or a pharmaceutically acceptable salt or solvate thereof, wherein R$^{9f}$ is hydrogen. In some embodiments is a compound of Formula (III) or (III'), or a pharmaceutically acceptable salt or solvate thereof, wherein R$^{9f}$ is $C_{1-6}$alkyl optionally substituted with one, two, or three R$^{20a}$. In some embodiments is a compound of Formula (III) or (III'), or a pharmaceutically acceptable salt or solvate thereof, wherein $R^{9f}$ is unsubstituted $C_{1-6}$alkyl. In some embodiments is a compound of Formula (III) or (III'), or a pharmaceutically acceptable salt or solvate thereof, wherein $R^{9f}$ is —CH$_3$. In some embodiments is a compound of Formula (III) or (III'), or a pharmaceutically acceptable salt or solvate thereof, wherein $R^{9g}$ is hydrogen or $C_{1-6}$alkyl optionally substituted with one, two, or three $R^{20a}$. In some embodiments is a compound of Formula (III) or (III'), or a pharmaceutically acceptable salt or solvate thereof, wherein $R^{9g}$ is hydrogen. In some embodiments is a compound of Formula (III) or (III'), or a pharmaceutically acceptable salt or solvate thereof, wherein $R^{9g}$ is $C_{1-6}$alkyl optionally substituted with one, two, or three $R^{20a}$. In some embodiments is a compound of Formula (III) or (III'), or a pharmaceutically acceptable salt or solvate thereof, wherein $R^{9g}$ is unsubstituted $C_{1-6}$alkyl. In some embodiments is a compound of Formula (III) or (III'), or a pharmaceutically acceptable salt or solvate thereof, wherein $R^{9g}$ is —CH$_3$.

In some embodiments is a compound of Formula (III) or (III'), or a pharmaceutically acceptable salt or solvate thereof, wherein $R^8$ is —SR$^{9b}$.

In some embodiments is a compound of Formula (III) or (III'), or a pharmaceutically acceptable salt or solvate thereof, wherein $R^8$ is halogen.

In some embodiments is a compound of Formula (III) or (III'), or a pharmaceutically acceptable salt or solvate thereof, wherein $R^8$ is

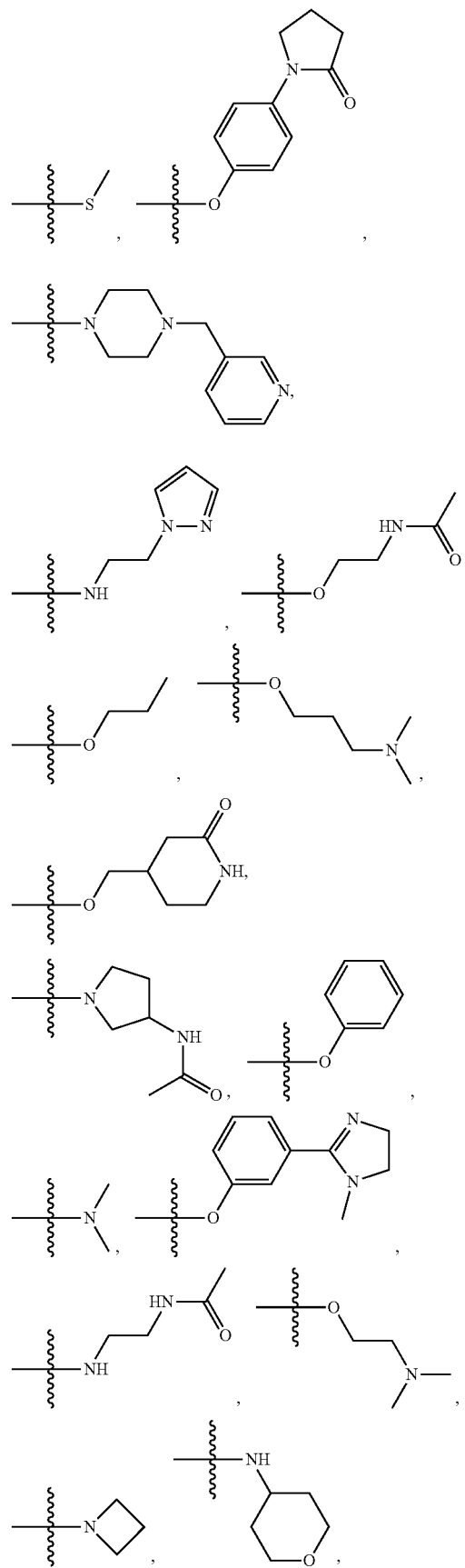

In some embodiments is a compound of Formula (III) or (III'), or a pharmaceutically acceptable salt or solvate thereof, wherein $R^8$ is -continued

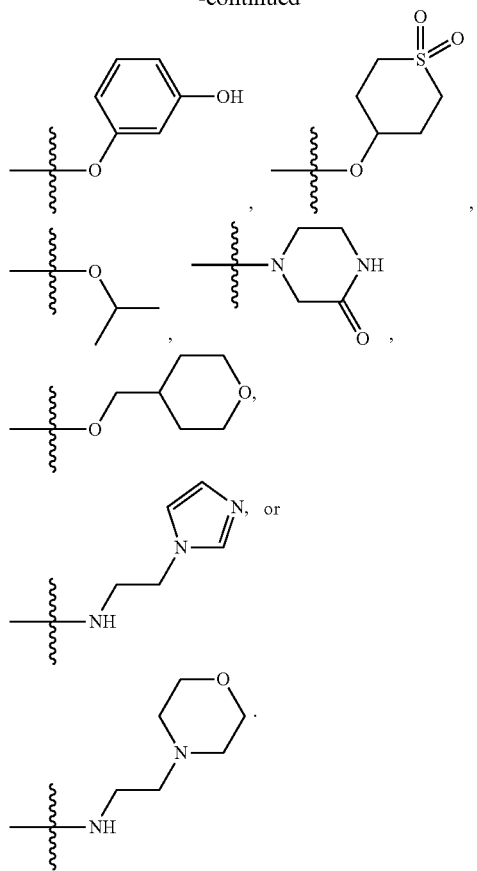

In some embodiments is a compound of Formula (III) or (III'), or a pharmaceutically acceptable salt or solvate thereof, wherein $R^8$ is

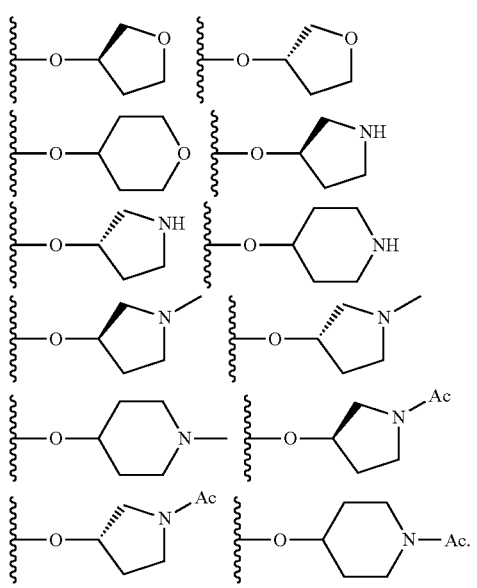

In some embodiments is a compound of Formula (III) or (III'), or a pharmaceutically acceptable salt or solvate thereof, wherein $R^8$ is

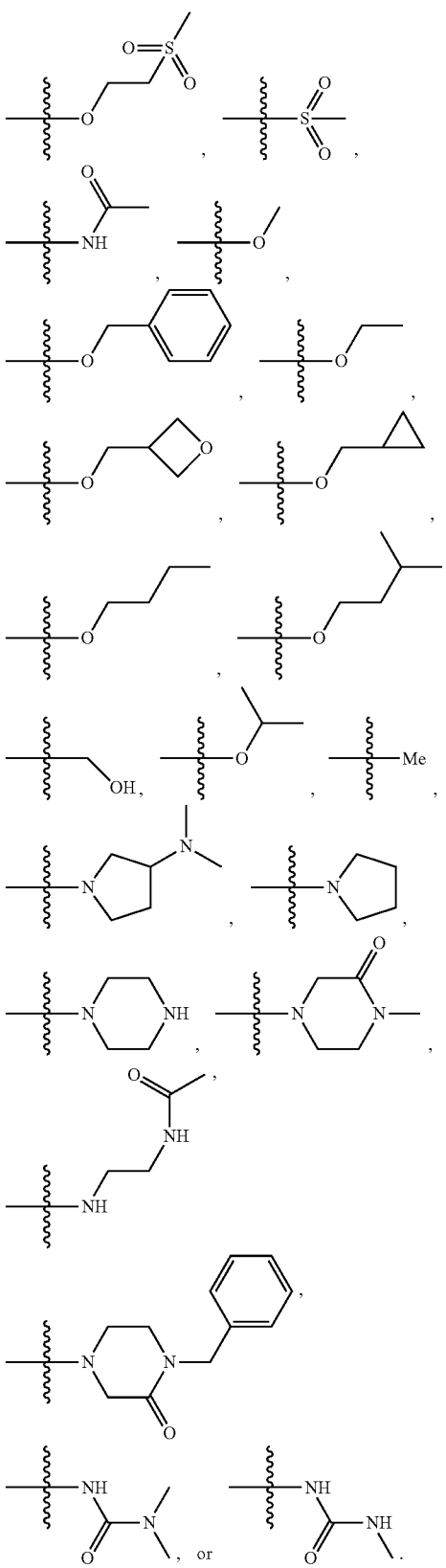

In some embodiments is a compound of Formula (III) or (III'), or a pharmaceutically acceptable salt or solvate thereof, wherein $R^8$ is

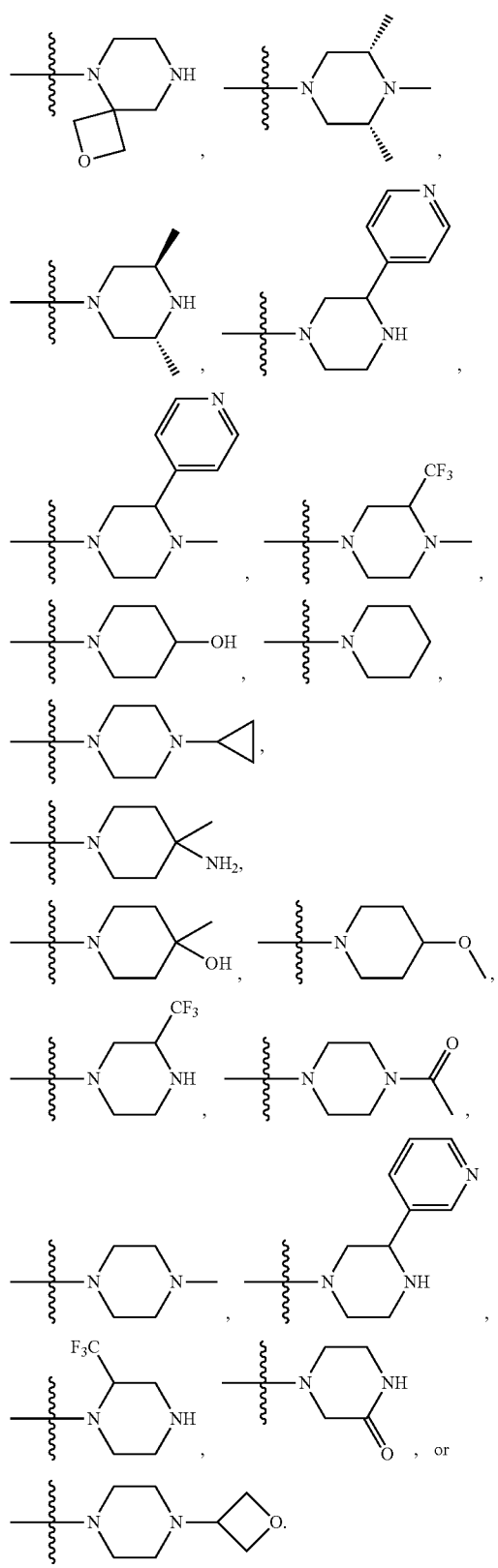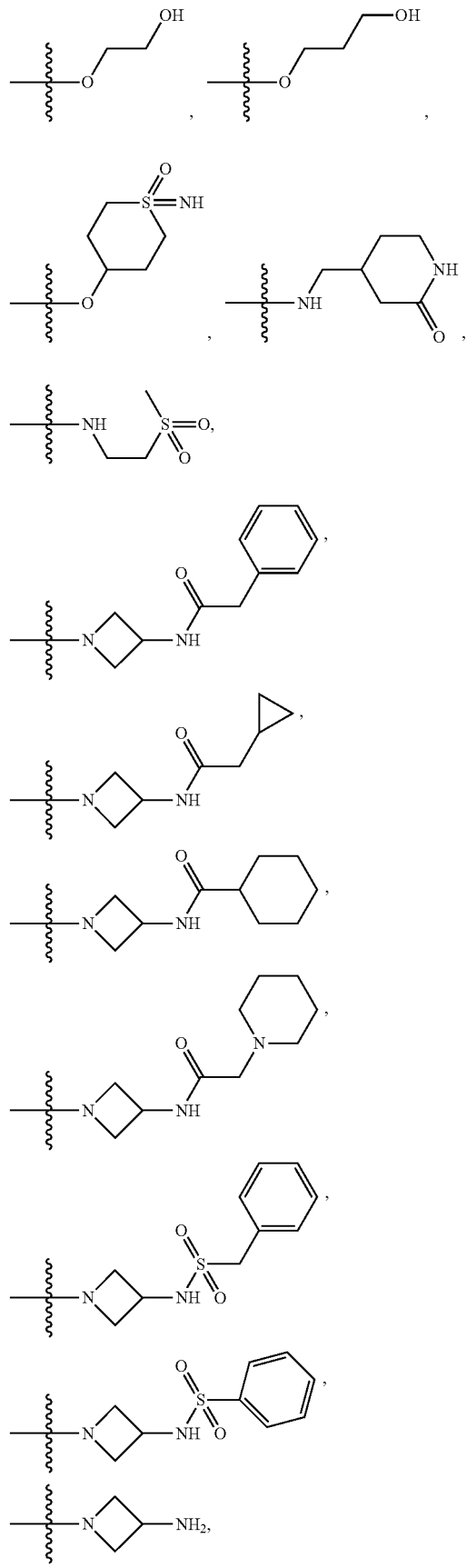
In some embodiments is a compound of Formula (III) or (III'), or a pharmaceutically acceptable salt or solvate thereof, wherein $R^8$ is In some embodiments is a compound of Formula (III) or (III'), or a pharmaceutically acceptable salt or solvate thereof, wherein $R^8$ is

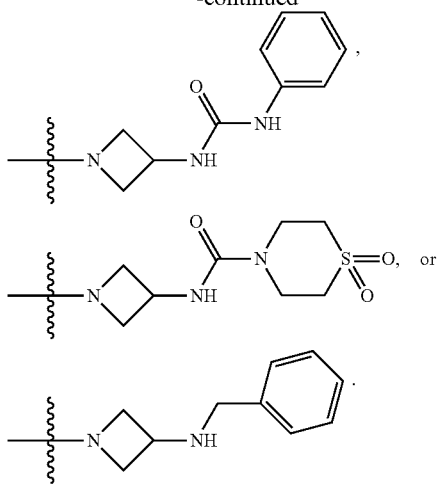

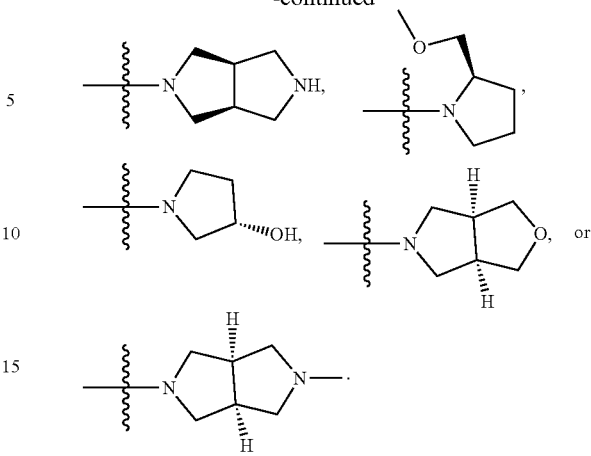

In embodiments of a compound of Formula (III) or (III'), $R^8$ is $C_{2-9}$heterocycloalkyl, including $C_{6-9}$heterocycloalkyl, $C_{3-7}$heterocycloalkyl, $C_{3-6}$heterocycloalkyl, $C_{5-6}$ heterocycloalkyl, $C_{3-5}$heterocycloalkyl, $C_{3-4}$heterocycloalkyl, each of which being optionally substituted with one, two, or three $R^{20a}$. In embodiments of a compound of Formula (III) or (III'), $R^8$ is $C_{6-9}$heterocycloalkyl optionally substituted with one, two, or three $R^{20a}$. In embodiments of a compound of Formula (III) or (III'), $R^8$ is $C_{3-7}$heterocycloalkyl optionally substituted with one, two, or three $R^{20a}$. In embodiments of a compound of Formula (III) or (III'), $R^8$ is $C_{3-6}$heterocycloalkyl optionally substituted with one, two, or three $R^{20a}$. In embodiments of a compound of Formula (III) or (III'), $R^8$ is $C_{5-6}$heterocycloalkyl optionally substituted with one, two, or three $R^{20a}$. In embodiments of a compound of Formula (III) or (III'), $R^8$ is $C_{3-5}$ heterocycloalkyl optionally substituted with one, two, or three $R^{20a}$. In embodiments of a compound of Formula (III) or (III'), $R^8$ is $C_{3-4}$heterocycloalkyl optionally substituted with one, two, or three $R^{20a}$.

In embodiments of a compound of Formula (III) or (III'), each of the $R^8$ described above including $C_{6-9}$heterocycloalkyl, $C_{3-7}$heterocycloalkyl, $C_{3-6}$heterocycloalkyl, $C_{5-6}$ heterocycloalkyl, $C_{3-5}$heterocycloalkyl, $C_{3-4}$heterocycloalkyl, is optionally substituted with one $R^{20a}$. In embodiments of a compound of Formula (III) or (III'), each of the $R^8$ described above, including $C_{6-9}$heterocycloalkyl, $C_{3-7}$heterocycloalkyl, $C_{3-6}$heterocycloalkyl, $C_{5-6}$ heterocycloalkyl, $C_{3-5}$heterocycloalkyl, $C_{3-4}$heterocycloalkyl, is optionally substituted with two $R^{20a}$. In embodiments of a compound of Formula (III) or (III'), each of the $R^8$ described above, including $C_{6-9}$heterocycloalkyl, $C_{3-7}$heterocycloalkyl, $C_{3-6}$heterocycloalkyl, $C_{5-6}$ heterocycloalkyl, $C_{3-5}$heterocycloalkyl, $C_{3-4}$heterocycloalkyl, is optionally substituted with three $R^{20a}$.

In each of the above embodiments of a compound of Formula (III) or (III'), $R^{20a}$ is independently selected from amino, —CN, $C_{1-3}$alkyl, $C_{1-3}$alkoxy, $C_{1-3}$haloalkyl, —OH, —N($R^{24}$)C(O)$R^{25}$, and —C(O)N($R^{22}$)($R^{23}$). In some embodiments of a compound of Formula (III) or (III'), $R^{20a}$ is amino. In some embodiments of a compound of Formula (III) or (III'), $R^{20a}$ is —CN. In some embodiments of a compound of Formula (III) or (III'), $R^{20a}$ is $C_{1-3}$alkyl. In some embodiments of a compound of Formula (III) or (III'), $R^{20a}$ is $C_{1-3}$alkoxy. In some embodiments of a compound of Formula (III) or (III'), $R^{20a}$ is $C_{1-3}$haloalkyl. In some embodiments of a compound of Formula (III) or (III'), $R^{20a}$ is —OH. In some embodiments of a compound of Formula (III) or (III'), $R^{20a}$ is —N($R^{24}$)C(O)$R^{25}$. In some embodiments of a compound of Formula (III) or (III'), $R^{20a}$ is —C(O)N($R^{22}$)($R^{23}$). In some embodiments of a compound of Formula (III) or (III'), $R^{20a}$ is —NHC(O)$R^{25}$. In some embodiments of a compound of Formula (III) or (III'), $R^{20a}$ is —C(O)NH($R^{22}$). In some embodiments of a compound of Formula (III) or (III'), $R^{20a}$ is —NHC(O)$R^{25}$ and $R^{25}$ is $C_{2-9}$heterocycloalkyl optionally substituted with one, two, or three groups independently selected from halogen, $C_{1-6}$alkyl, $C_{1-6}$haloalkyl, $C_{1-6}$alkoxy, $C_{3-7}$cycloalkyl, $C_{2-9}$heterocycloalkyl, $C_{6-10}$aryl, and $C_{1-9}$heteroaryl. In some embodiments of a compound of Formula (III) or (III'), $R^{20a}$ is —C(O)NH($R^{22}$) and $R^{22}$ is $C_{2-9}$heterocycloalkyl optionally substituted with one, two, or three groups independently selected from halogen and $C_{1-6}$alkyl. In some embodiments of a compound of Formula (III) or (III'), $R^{20a}$ is —NHC(O)$R^{25}$ and $R^{25}$ is $C_{2-5}$heterocycloalkyl optionally substituted with one $C_{1-6}$alkyl. In some embodiments of a compound of Formula (III) or (III'), $R^{20a}$ is —C(O)NH($R^{22}$) and $R^{22}$ is $C_{2-5}$heterocycloalkyl optionally substituted with one $C_{1-6}$alkyl.

In embodiments of a compound of Formula (III) or (III'), $R^8$ is $C_{2-9}$heterocycloalkyl (including $C_{6-9}$ heterocycloalkyl, $C_{3-7}$heterocycloalkyl, $C_{3-6}$heterocycloalkyl, $C_{5-6}$heterocycloalkyl, $C_{3-5}$heterocycloalkyl, and $C_{3-4}$heterocycloalkyl), optionally substituted with one, two, or three $R^{20a}$ that is amino. In embodiments of a compound of Formula (III) or (III'), $R^8$ is $C_{2-9}$heterocycloalkyl (including $C_{6-9}$heterocycloalkyl, $C_{3-7}$heterocycloalkyl, $C_{3-6}$heterocycloalkyl, $C_{5-6}$heterocycloalkyl, $C_{3-5}$heterocycloalkyl, and $C_{3-4}$heterocycloalkyl), optionally substituted with one, two, or three $R^{20a}$ that is —CN. In embodiments of a compound of Formula (III) or (III'), $R^8$ is $C_{2-9}$heterocycloalkyl (including $C_{6-9}$heterocycloalkyl, $C_{3-7}$heterocycloalkyl, $C_{3-6}$heterocycloalkyl, $C_{5-6}$heterocycloalkyl, $C_{3-5}$heterocycloalkyl, and $C_{3-4}$heterocycloalkyl), optionally substituted with one, two, or three $R^{20a}$ that is $C_{1-3}$alkyl. In embodiments of a compound of Formula (III) or (III'), $R^8$ is $C_{2-9}$heterocycloalkyl (including $C_{6-9}$ heterocycloalkyl, $C_{3-7}$heterocycloalkyl, $C_{3-6}$heterocycloalkyl, $C_{5-6}$heterocycloalkyl, $C_{3-5}$heterocycloalkyl, and $C_{3-4}$heterocycloalkyl), optionally substituted with one, two, or three $R^{20a}$ that is $C_{1-3}$alkoxy. In embodiments of a compound of Formula (III) or (III'), $R^8$ is $C_{2-9}$heterocycloalkyl (including $C_{6-9}$heterocycloalkyl, $C_{3-7}$heterocycloalkyl, $C_{3-6}$heterocycloalkyl, $C_{5-6}$heterocycloalkyl, $C_{3-5}$heterocycloalkyl, and $C_{3-4}$heterocycloalkyl), optionally substituted with one, two, or three $R^{20a}$ that is $C_{1-3}$haloalkyl. In embodiments of a compound of Formula (III) or (III'), $R^8$ is $C_{2-9}$heterocycloalkyl (including $C_{6-9}$heterocycloalkyl, $C_{3-7}$heterocycloalkyl, $C_{3-6}$heterocycloalkyl, $C_{5-6}$heterocycloalkyl, $C_{3-5}$heterocycloalkyl, and $C_{3-4}$heterocycloalkyl), optionally substituted with one, two, or three $R^{20a}$ that is —OH. In embodiments of a compound of Formula (III) or (III'), $R^8$ is $C_{2-9}$heterocycloalkyl (including $C_{6-9}$heterocycloalkyl, $C_{3-7}$heterocycloalkyl, $C_{3-6}$heterocycloalkyl, $C_{5-6}$heterocycloalkyl, $C_{3-5}$heterocycloalkyl, and $C_{3-4}$heterocycloalkyl), optionally substituted with one, two, or three $R^{20a}$ that is oxo. In embodiments of a compound of Formula (III) or (III'), $R^8$ is $C_{2-9}$heterocycloalkyl (including $C_{6-9}$heterocycloalkyl, $C_{3-7}$heterocycloalkyl, $C_{3-6}$heterocycloalkyl, $C_{5-6}$heterocycloalkyl, $C_{3-5}$heterocycloalkyl, and $C_{3-4}$heterocycloalkyl), optionally substituted with one, two, or three $R^{20a}$ that is —N($R^{24}$)C(O)$R^{25}$. In embodiments of a compound of Formula (III) or (III'), $R^8$ is $C_{2-9}$heterocycloalkyl (including $C_{6-9}$heterocycloalkyl, $C_{3-7}$heterocycloalkyl, $C_{3-6}$heterocycloalkyl, $C_{5-6}$heterocycloalkyl, $C_{3-5}$heterocycloalkyl, and $C_{3-4}$heterocycloalkyl), optionally substituted with one, two, or three $R^{20a}$ that is —NHC(O)$R^{25}$. In embodiments of a compound of Formula (III) or (III'), $R^8$ is $C_{2-9}$heterocycloalkyl (including $C_{6-9}$heterocycloalkyl, $C_{3-7}$heterocycloalkyl, $C_{3-6}$heterocycloalkyl, $C_{5-6}$heterocycloalkyl, $C_{3-5}$heterocycloalkyl, and $C_{3-4}$heterocycloalkyl), optionally substituted with one, two, or three $R^{20a}$ that is —NHC(O)$R^{25}$ and $R^{25}$ is $C_{2-9}$heterocycloalkyl optionally substituted with one, two, or three groups independently selected from halogen, $C_{1-6}$alkyl, $C_{1-6}$haloalkyl, $C_{1-6}$alkoxy, $C_{3-7}$cycloalkyl, $C_{2-9}$heterocycloalkyl, $C_{6-10}$aryl, and $C_{1-9}$heteroaryl. In embodiments of a compound of Formula (III) or (III'), $R^8$ is $C_{2-9}$heterocycloalkyl (including $C_{6-9}$heterocycloalkyl, $C_{3-7}$heterocycloalkyl, $C_{3-6}$heterocycloalkyl, $C_{5-6}$heterocycloalkyl, $C_{3-5}$heterocycloalkyl, and $C_{3-4}$heterocycloalkyl), optionally substituted with one, two, or three $R^{20a}$ that is —NHC(O)$R^{25}$ and $R^{25}$ is $C_{2-5}$heterocycloalkyl optionally substituted with one $C_{1-6}$alkyl. In embodiments of a compound of Formula (III) or (III'), $R^8$ is $C_{2-9}$heterocycloalkyl (including $C_{6-9}$heterocycloalkyl, $C_{3-7}$heterocycloalkyl, $C_{3-6}$heterocycloalkyl, $C_{5-6}$heterocycloalkyl, $C_{3-5}$heterocycloalkyl, and $C_{3-4}$heterocycloalkyl), optionally substituted with one, two, or three $R^{20a}$ that is —C(O)N($R^{22}$)($R^{23}$). In embodiments of a compound of Formula (III) or (III'), $R^8$ is $C_{2-9}$heterocycloalkyl (including $C_{6-9}$heterocycloalkyl, $C_{3-7}$heterocycloalkyl, $C_{3-6}$heterocycloalkyl, $C_{5-6}$heterocycloalkyl, $C_{3-5}$heterocycloalkyl, and $C_{3-4}$heterocycloalkyl), optionally substituted with one, two, or three $R^{20a}$ that is —C(O)NH($R^{22}$). In embodiments of a compound of Formula (III) or (III'), $R^8$ is $C_{2-9}$heterocycloalkyl (including $C_{6-9}$heterocycloalkyl, $C_{3-7}$heterocycloalkyl, $C_{3-6}$heterocycloalkyl, $C_{5-6}$heterocycloalkyl, $C_{3-5}$heterocycloalkyl, and $C_{3-4}$heterocycloalkyl), optionally substituted with one, two, or three $R^{20a}$ that is —C(O)NH($R^{22}$) and $R^{22}$ is $C_{2-9}$heterocycloalkyl optionally substituted with one, two, or three groups independently selected from halogen and $C_{1-6}$alkyl. In embodiments of a compound of Formula (III) or (III'), $R^8$ is $C_{2-9}$heterocycloalkyl (including $C_{6-9}$heterocycloalkyl, $C_{3-7}$heterocycloalkyl, $C_{3-6}$heterocycloalkyl, $C_{5-6}$heterocycloalkyl, $C_{3-5}$heterocycloalkyl, and $C_{3-4}$heterocycloalkyl), optionally substituted with one, two, or three $R^{20a}$ that is —C(O)NH($R^{22}$) and $R^{22}$ is $C_{2-5}$heterocycloalkyl optionally substituted with one $C_{1-6}$alkyl.

In embodiments of a compound of Formula (III) or (III'), $R^8$ is monovalent $4\lambda^2$-thiomorpholine substituted with two $R^{20a}$. In embodiments of a compound of Formula (III) or (III'), $R^8$ is tetrahydro-2H-thiopyranyl 1,1-dioxide. In embodiments of a compound of Formula (III) or (III'), $R^8$ is $4\lambda^2$-thiomorpholinyl substituted with two $R^{20a}$. In embodiments of a compound of Formula (III) or (III'), $R^8$ is piperidinyl substituted with one $R^{20a}$. In embodiments of a compound of Formula (III) or (III'), $R^8$ is piperazinyl substituted with one $R^{20a}$. In embodiments of a compound of Formula (III) or (III'), $R^8$ is pyrrolidinyl substituted with one $R^{20a}$.

In embodiments of a compound of Formula (III) or (III'), $R^8$ is $C_{2-9}$heterocycloalkyl substituted with one methyl. In embodiments of a compound of Formula (III) or (III'), $R^8$ is $C_{6-9}$heterocycloalkyl substituted with one methyl, one ethyl, or one propyl. In embodiments of a compound of Formula (III) or (III'), $R^8$ is $C_{3-7}$heterocycloalkyl substituted with one methyl, one ethyl, or one propyl. In embodiments of a compound of Formula (III) or (III'), $R^8$ is $C_{3-6}$heterocycloalkyl substituted with one methyl, one ethyl, or one propyl. In embodiments of a compound of Formula (III) or (III'), $R^8$ is $C_{5-6}$heterocycloalkyl substituted with one methyl, one ethyl, or one propyl. In embodiments of a compound of Formula (III) or (III'), $R^8$ is $C_{5-6}$heterocycloalkyl substituted with one methyl, one ethyl, or one propyl. In embodiments of a compound of Formula (III) or (III'), $R^8$ is $C_{3-4}$heterocycloalkyl substituted with one methyl, one ethyl, or one propyl. In embodiments of a compound of Formula (III) or (III'), $R^8$ is $C_{2-7}$heterocycloalkyl substituted with one methyl, one ethyl, or one propyl. In embodiments of a compound of Formula (III) or (III'), $R^8$ is $C_{4-7}$ heterocycloalkyl substituted with one methyl, one ethyl, or one propyl. In embodiments of a compound of Formula (III) or (III'), $R^8$ is $C_{4-5}$heterocycloalkyl substituted with one methyl, one ethyl, or one propyl. In embodiments of a compound of Formula (III) or (III'), $R^8$ is $C_5$heterocycloalkyl substituted with one methyl, one ethyl, or one propyl. In embodiments of a compound of Formula (III) or (III'), $R^8$ is $C_4$heterocycloalkyl substituted with one methyl, one ethyl, or one propyl.

In embodiments of a compound of Formula (III) or (III'), $R^8$ is $C_{6-9}$heterocycloalkyl substituted with one propyl. In embodiments of a compound of Formula (III) or (III'), $R^8$ is $C_{3-7}$heterocycloalkyl substituted with one propyl. In embodiments of a compound of Formula (III) or (III'), $R^8$ is $C_{3-6}$heterocycloalkyl substituted with one propyl. In embodiments of a compound of Formula (III) or (III'), $R^8$ is $C_{5-6}$heterocycloalkyl substituted with one propyl. In embodiments of a compound of Formula (III) or (III'), $R^8$ is $C_{5-6}$heterocycloalkyl substituted with one propyl. In embodiments of a compound of Formula (III) or (III'), $R^8$ is $C_{3-4}$heterocycloalkyl substituted with one propyl. In embodiments of a compound of Formula (III) or (III'), $R^8$ is $C_{4-5}$ heterocycloalkyl substituted with one propyl. In embodiments of a compound of Formula (III) or (III'), $R^8$ is $C_5$heterocycloalkyl substituted with one propyl. In embodiments of a compound of Formula (III) or (III'), $R^8$ is $C_4$heterocycloalkyl substituted with one propyl.

In embodiments of a compound of Formula (III) or (III'), $R^8$ is $C_{2-9}$heterocycloalkyl substituted with one isopropyl. In embodiments of a compound of Formula (III) or (III'), $R^8$ is $C_{2-7}$heterocycloalkyl substituted with one isopropyl. In embodiments of a compound of Formula (III) or (III'), $R^8$ is $C_{4-7}$heterocycloalkyl substituted with one isopropyl. In embodiments of a compound of Formula (III) or (III'), $R^8$ is $C_{4-5}$heterocycloalkyl substituted with one isopropyl. In embodiments of a compound of Formula (III) or (III'), $R^8$ is $C_5$heterocycloalkyl substituted with one isopropyl. In embodiments of a compound of Formula (III) or (III'), $R^8$ is $C_4$heterocycloalkyl substituted with one isopropyl.

In embodiments of a compound of Formula (III) or (III'), $R^8$ is $C_{2-9}$heterocycloalkyl substituted with two oxo. In embodiments of a compound of Formula (III) or (III'), $R^8$ is $C_{2-7}$heterocycloalkyl substituted with two oxo. In embodiments of a compound of Formula (III) or (III'), $R^8$ is $C_{4-7}$heterocycloalkyl substituted with two oxo. In embodiments of a compound of Formula (III) or (III'), $R^8$ is $C_{6-9}$heterocycloalkyl substituted with two oxo. In embodiments of a compound of Formula (III) or (III'), $R^8$ is $C_{3-7}$heterocycloalkyl substituted with two oxo. In embodiments of a compound of Formula (III) or (III'), $R^8$ is $C_{3-6}$heterocycloalkyl substituted with two oxo. In embodiments of a compound of Formula (III) or (III'), $R^8$ is $C_{5-6}$heterocycloalkyl substituted with two oxo. In embodiments of a compound of Formula (III) or (III'), $R^8$ is $C_{5-6}$heterocycloalkyl substituted with two oxo. In embodiments of a compound of Formula (III) or (III'), $R^8$ is $C_{3-4}$heterocycloalkyl substituted with two oxo. In embodiments of a compound of Formula (III) or (III'), $R^8$ is $C_{4-5}$heterocycloalkyl substituted with two oxo. In embodiments of a compound of Formula (III) or (III'), $R^8$ is $C_5$heterocycloalkyl substituted with two oxo. In embodiments of a compound of Formula (III) or (III'), $R^8$ is $C_4$heterocycloalkyl substituted with two oxo.

In embodiments of a compound of Formula (III) or (III'), $R^8$ is $4\lambda^2$-thiomorpholinyl, optionally substituted with one, two, or three $R^{20a}$ that is amino. In embodiments of a compound of Formula (III) or (III'), $R^8$ is $4\lambda^2$-thiomorpholinyl, optionally substituted with one, two, or three $R^{20a}$ that is —CN. In embodiments of a compound of Formula (III) or (III'), $R^8$ is $4\lambda^2$-thiomorpholinyl, optionally substituted with one, two, or three $R^{20a}$ that is $C_{1-3}$alkyl. In embodiments of a compound of Formula (III) or (III'), $R^8$ is $4\lambda^2$-thiomorpholinyl, optionally substituted with one, two, or three $R^{20a}$ that is $C_{1-3}$alkoxy. In embodiments of a compound of Formula (III) or (III'), $R^8$ is $4\lambda^2$-thiomorpholinyl, optionally substituted with one, two, or three $R^{20a}$ that is $C_{1-3}$haloalkyl. In embodiments of a compound of Formula (III) or (III'), $R^8$ is $4\lambda^2$-thiomorpholinyl, optionally substituted with one, two, or three $R^{20a}$ that is —OH. In embodiments of a compound of Formula (III) or (III'), $R^8$ is $4\lambda^2$-thiomorpholinyl, optionally substituted with one, two, or three $R^{20a}$ that is oxo. In embodiments of a compound of Formula (III) or (III'), $R^8$ is $4\lambda^2$-thiomorpholinyl, optionally substituted with one, two, or three $R^{20a}$ that is —N($R^{24}$)C(O)$R^{25}$. In embodiments of a compound of Formula (III) or (III'), $R^8$ is $4\lambda^2$-thiomorpholinyl, optionally substituted with one, two, or three $R^{20a}$ that is —NHC(O)$R^{25}$. In embodiments of a compound of Formula (III) or (III'), $R^8$ is $4\lambda^2$-thiomorpholinyl, optionally substituted with one, two, or three $R^{20a}$ that is —NHC(O)$R^{25}$ and $R^{25}$ is $C_{2-9}$heterocycloalkyl optionally substituted with one, two, or three groups independently selected from halogen, $C_{1-6}$alkyl, $C_{1-6}$haloalkyl, $C_{1-6}$alkoxy, $C_{3-7}$cycloalkyl, $C_{2-9}$heterocycloalkyl, $C_{6-10}$aryl, and $C_{1-9}$heteroaryl. In embodiments of a compound of Formula (III) or (III'), $R^8$ is $4\lambda^2$-thiomorpholinyl, optionally substituted with one, two, or three $R^{20a}$ that is —NHC(O)$R^{25}$ and $R^{25}$ is $C_{2-5}$heterocycloalkyl optionally substituted with one $C_{1-6}$alkyl. In embodiments of a compound of Formula (III) or (III'), $R^8$ is $4\lambda^2$-thiomorpholinyl, optionally substituted with one, two, or three $R^{20a}$ that is —C(O)N($R^{22}$)($R^{23}$). In embodiments of a compound of Formula (III) or (III'), $R^8$ is $4\lambda^2$-thiomorpholinyl, optionally substituted with one, two, or three $R^{20a}$ that is —C(O)NH($R^{22}$). In embodiments of a compound of Formula (III) or (III'), $R^8$ is $4\lambda^2$-thiomorpholinyl, optionally substituted with one, two, or three $R^{20a}$ that is —C(O)NH($R^{22}$) and $R^{22}$ is $C_{2-9}$heterocycloalkyl optionally substituted with one, two, or three groups independently selected from halogen and $C_{1-6}$alkyl. In embodiments of a compound of Formula (III) or (III'), $R^1$ is $4\lambda^2$-thiomorpholinyl, optionally substituted with one, two, or three $R^{20a}$ that is —C(O)NH($R^{22}$) and $R^{22}$ is $C_{2-5}$heterocycloalkyl optionally substituted with one $C_{1-6}$alkyl.

In embodiments of a compound of Formula (III) or (III'), $R^8$ is piperidinyl, optionally substituted with one, two, or three $R^{20a}$ that is amino. In embodiments of a compound of Formula (III) or (III'), $R^8$ is piperidinyl, optionally substituted with one, two, or three $R^{20a}$ that is —CN. In embodiments of a compound of Formula (III) or (III'), $R^8$ is piperidinyl, optionally substituted with one, two, or three $R^{20a}$ that is $C_{1-3}$alkyl. In embodiments of a compound of Formula (III) or (III'), $R^8$ is piperidinyl, optionally substituted with one, two, or three $R^{20a}$ that is $C_{1-3}$alkoxy. In embodiments of a compound of Formula (III) or (III'), $R^8$ is piperidinyl, optionally substituted with one, two, or three $R^{20a}$ that is $C_{1-3}$haloalkyl. In embodiments of a compound of Formula (III) or (III'), $R^8$ is piperidinyl, optionally substituted with one, two, or three $R^{20a}$ that is —OH. In embodiments of a compound of Formula (III) or (III'), $R^8$ is piperidinyl, optionally substituted with one, two, or three $R^{20a}$ that is oxo. In embodiments of a compound of Formula (III) or (III'), $R^8$ is piperidinyl, optionally substituted with one, two, or three $R^{20a}$ that is —N($R^{24}$)C(O)$R^{25}$. In embodiments of a compound of Formula (III) or (III'), $R^8$ is piperidinyl, optionally substituted with one, two, or three $R^{20a}$ that is —NHC(O)$R^{25}$. In embodiments of a compound of Formula (III) or (III'), $R^8$ is piperidinyl, optionally substituted with one, two, or three $R^{20a}$ that is —NHC(O)$R^{25}$ and $R^{25}$ is $C_{2-9}$heterocycloalkyl optionally substituted with one, two, or three groups independently selected from halogen, $C_{1-6}$alkyl, $C_{1-6}$haloalkyl, $C_{1-6}$alkoxy, $C_{3-7}$cycloalkyl, $C_{2-9}$heterocycloalkyl, $C_{6-10}$aryl, and $C_{1-9}$heteroaryl. In embodiments of a compound of Formula (III) or (III'), $R^1$ is piperidinyl, optionally substituted with one, two, or three $R^{20a}$ that is —NHC(O)$R^{21}$ and $R^{25}$ is $C_{2-5}$heterocycloalkyl optionally substituted with one $C_{1-6}$alkyl. In embodiments of a compound of Formula (III) or (III'), $R^1$ is piperidinyl, optionally substituted with one, two, or three $R^{20a}$ that is —C(O)N($R^{22}$)($R^{23}$). In embodiments of a compound of Formula (III) or (III'), $R^8$ is piperidinyl, optionally substituted with one, two, or three $R^{20a}$ that is —C(O)NH($R^{22}$). In embodiments of a compound of Formula (III) or (III'), $R^8$ is piperidinyl, optionally substituted with one, two, or three $R^{20a}$ that is —C(O)NH($R^{22}$) and $R^{22}$ is $C_{2-9}$heterocycloalkyl optionally substituted with one, two, or three groups independently selected from halogen and $C_{1-6}$alkyl. In embodiments of a compound of Formula (III) or (III'), $R^8$ is piperidinyl, optionally substituted with one, two, or three $R^{20a}$ that is —C(O)NH($R^{22}$) and $R^{22}$ is $C_{2-5}$heterocycloalkyl optionally substituted with one $C_{1-6}$alkyl.

In embodiments of a compound of Formula (III) or (III'), $R^8$ is piperazinyl, optionally substituted with one, two, or three $R^{20a}$ that is amino. In embodiments of a compound of Formula (III) or (III'), $R^8$ is piperazinyl, optionally substituted with one, two, or three $R^{20a}$ that is —CN. In embodiments of a compound of Formula (III) or (III'), $R^8$ is piperazinyl, optionally substituted with one, two, or three $R^{20a}$ that is $C_{1-3}$alkyl. In embodiments of a compound of Formula (III) or (III'), $R^8$ is piperazinyl, optionally substituted with one, two, or three $R^{20a}$ that is $C_{1-3}$alkoxy. In embodiments of a compound of Formula (III) or (III'), $R^8$ is piperazinyl, optionally substituted with one, two, or three $R^{20a}$ that is $C_{1-3}$haloalkyl. In embodiments of a compound of Formula (III) or (III'), $R^8$ is piperazinyl, optionally substituted with one, two, or three $R^{20a}$ that is —OH. In embodiments of a compound of Formula (III) or (III'), $R^8$ is piperazinyl, optionally substituted with one, two, or three $R^{20a}$ that is oxo. In embodiments of a compound of Formula (III) or (III'), $R^8$ is piperazinyl, optionally substituted with one, two, or three $R^{20a}$ that is —N($R^{24}$)C(O)$R^{25}$. In embodiments of a compound of Formula (III) or (III'), $R^8$ is piperazinyl, optionally substituted with one, two, or three $R^{20a}$ that is —NHC(O)$R^{25}$. In embodiments of a compound of Formula (III) or (III'), $R^8$ is piperazinyl, optionally substituted with one, two, or three $R^{20a}$ that is —NHC(O)$R^{25}$ and $R^{25}$ is $C_{2-9}$heterocycloalkyl optionally substituted with one, two, or three groups independently selected from halogen, $C_{1-6}$alkyl, $C_{1-6}$haloalkyl, $C_{1-6}$alkoxy, $C_{3-7}$cycloalkyl, $C_{2-9}$heterocycloalkyl, $C_{6-10}$aryl, and $C_{1-9}$heteroaryl. In embodiments of a compound of Formula (III) or (III'), $R^8$ is piperazinyl, optionally substituted with one, two, or three $R^{20a}$ that is —NHC(O)$R^{25}$ and $R^{25}$ is $C_{2-5}$heterocycloalkyl optionally substituted with one $C_{1-6}$alkyl. In embodiments of a compound of Formula (III) or (III'), $R^8$ is piperazinyl, optionally substituted with one, two, or three $R^{20a}$ that is —C(O)N($R^{22}$)($R^{23}$). In embodiments of Formula (III) or (III'), $R^8$ is piperazinyl, optionally substituted with one, two, or three $R^{20a}$ that is —C(O)NH($R^{22}$). In embodiments of a compound of Formula (III) or (III'), $R^8$ is piperazinyl, optionally substituted with one, two, or three $R^{20a}$ that is —C(O)NH($R^{22}$) and $R^{22}$ is $C_{2-9}$heterocycloalkyl optionally substituted with one, two, or three groups independently selected from halogen and $C_{1-6}$alkyl. In embodiments of a compound of Formula (III) or (III'), $R^8$ is piperazinyl, optionally substituted with one, two, or three $R^{20a}$ that is —C(O)NH($R^{22}$) and $R^{22}$ is $C_{2-5}$heterocycloalkyl optionally substituted with one $C_{1-6}$alkyl.

In embodiments of a compound of Formula (III) or (III'), $R^8$ is pyrrolidinyl, optionally substituted with one, two, or three $R^{20a}$ that is amino. In embodiments of a compound of Formula (III) or (III'), $R^8$ is pyrrolidinyl, optionally substituted with one, two, or three $R^{20a}$ that is —CN. In embodiments of a compound of Formula (III) or (III'), $R^8$ is pyrrolidinyl, optionally substituted with one, two, or three $R^{20a}$ that is $C_{1-3}$alkyl. In embodiments of a compound of Formula (III) or (III'), $R^8$ is pyrrolidinyl, optionally substituted with one, two, or three $R^{20a}$ that is $C_{1-3}$alkoxy. In embodiments of a compound of Formula (III) or (III'), $R^8$ is pyrrolidinyl, optionally substituted with one, two, or three $R^{20a}$ that is $C_{1-3}$haloalkyl. In embodiments of a compound of Formula (III) or (III'), $R^8$ is pyrrolidinyl, optionally substituted with one, two, or three $R^{20a}$ that is —OH. In embodiments of a compound of Formula (III) or (III'), $R^8$ is pyrrolidinyl, optionally substituted with one, two, or three $R^{20a}$ that is oxo. In embodiments of a compound of Formula (III) or (III'), $R^8$ is pyrrolidinyl, optionally substituted with one, two, or three $R^{20a}$ that is —N($R^{24}$)C(O)$R^{25}$. In embodiments of a compound of Formula (III) or (III'), $R^8$ is pyrrolidinyl, optionally substituted with one, two, or three $R^{20a}$ that is —NHC(O)$R^{25}$. In embodiments of a compound of Formula (III) or (III'), $R^8$ is pyrrolidinyl, optionally substituted with one, two, or three $R^{20a}$ that is —NHC(O)$R^{25}$ and $R^{25}$ is $C_{2-9}$heterocycloalkyl optionally substituted with one, two, or three groups independently selected from halogen, $C_{1-6}$alkyl, $C_{1-6}$haloalkyl, $C_{1-6}$alkoxy, $C_{3-7}$cycloalkyl, $C_{2-9}$heterocycloalkyl, $C_{6-10}$aryl, and $C_{1-9}$heteroaryl. In embodiments of a compound of Formula (III) or (III'), $R^8$ is pyrrolidinyl, optionally substituted with one, two, or three $R^{20a}$ that is —NHC(O)$R^{25}$ and $R^{25}$ is $C_{2-5}$heterocycloalkyl optionally substituted with one $C_{1-6}$alkyl. In embodiments of a compound of Formula (III) or (III'), $R^8$ is pyrrolidinyl, optionally substituted with one, two, or three $R^{20a}$ that is —C(O)N($R^{22}$)($R^{23}$). In embodiments of a compound of Formula (III) or (III'), $R^8$ is pyrrolidinyl, optionally substituted with one, two, or three $R^{20a}$ that is —C(O)NH($R^{22}$). In embodiments of a compound of Formula (III) or (III'), $R^8$ is pyrrolidinyl, optionally substituted with one, two, or three $R^{20a}$ that is —C(O)NH($R^{22}$) and $R^{22}$ is $C_{2-9}$heterocycloalkyl optionally substituted with one, two, or three groups independently selected from halogen and $C_{1-6}$alkyl. In embodiments of a compound of Formula (III) or (III'), $R^8$ is pyrrolidinyl, optionally substituted with one, two, or three $R^{20a}$ that is —C(O)NH($R^{22}$) and $R^{22}$ is $C_{2-5}$heterocycloalkyl optionally substituted with one $C_{1-6}$alkyl.

In some embodiments of a compound of Formula (III) or (III'), $R^8$ is

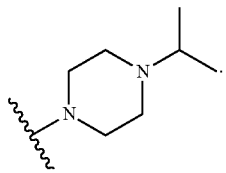 [SMILES: *N1CCN(C(C)C)CC1]

In some embodiments of a compound of Formula (III) or (III'), $R^8$ is

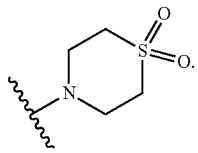 [SMILES: *N1CCS(=O)(=O)CC1]

In some embodiments is a compound of Formula (III) or (III'), or a pharmaceutically acceptable salt or solvate thereof, wherein $R^6$ is selected from hydrogen, $C_{1-6}$alkyl, $C_{3-10}$cycloalkyl, $C_{2-9}$heterocycloalkyl, $C_{6-10}$aryl, and $C_{1-9}$heteroaryl, wherein $C_{1-6}$alkyl, $C_{3-10}$cycloalkyl, $C_{2-9}$heterocycloalkyl, $C_{6-10}$aryl, and $C_{1-9}$heteroaryl are optionally substituted with one, two, or three $R^{20c}$. In some embodiments is a compound of Formula (III) or (III'), or a pharmaceutically acceptable salt or solvate thereof, wherein $R^6$ is selected from hydrogen and $C_{1-6}$alkyl optionally substituted with one, two, or three $R^{20c}$. In some embodiments is a compound of Formula (III) or (III'), or a pharmaceutically acceptable salt or solvate thereof, wherein $R^6$ is $C_{1-6}$alkyl optionally substituted with one, two, or three $R^{20c}$. In some embodiments is a compound of Formula (III) or (III'), or a pharmaceutically acceptable salt or solvate thereof, wherein $R^6$ is hydrogen. In some embodiments is a compound of Formula (III) or (III'), or a pharmaceutically acceptable salt or solvate thereof, wherein $R^6$ is methyl.

In some embodiments is a compound of Formula (III) or (III'), or a pharmaceutically acceptable salt or solvate thereof, wherein $R^7$ is selected from hydrogen, $C_{1-6}$alkyl, $C_{3-10}$cycloalkyl, $C_{2-9}$heterocycloalkyl, $C_{6-10}$aryl, and $C_{1-9}$heteroaryl, wherein $C_{1-6}$alkyl, $C_{3-10}$cycloalkyl, $C_{2-9}$heterocycloalkyl, $C_{6-10}$aryl, and $C_{1-9}$heteroaryl are optionally substituted with one, two, or three $R^{20c}$. In some embodiments is a compound of Formula (III) or (III'), or a pharmaceutically acceptable salt or solvate thereof, wherein $R^7$ is selected from hydrogen and $C_{1-6}$alkyl optionally substituted with one, two, or three $R^{20c}$. In some embodiments is a compound of Formula (III) or (III'), or a pharmaceutically acceptable salt or solvate thereof, wherein $R^7$ is $C_{1-6}$alkyl optionally substituted with one, two, or three $R^{20c}$. In some embodiments is a compound of Formula (III) or (III'), or a pharmaceutically acceptable salt or solvate thereof, wherein $R^7$ is hydrogen. In some embodiments is a compound of Formula (III) or (III'), or a pharmaceutically acceptable salt or solvate thereof, wherein $R^7$ is methyl.

In some embodiments is a compound of Formula (III) or (III'), or a pharmaceutically acceptable salt or solvate thereof, wherein $L^1$ is a bond. In some embodiments is a compound of Formula (III) or (III'), or a pharmaceutically acceptable salt or solvate thereof, wherein $L^1$ is $C_{1-6}$alkyl.

In some embodiments is a compound of Formula (III) or (III'), or a pharmaceutically acceptable salt or solvate thereof, wherein $R^1$ is a 6-10 membered aryl ring optionally substituted with one or more $R^{10}$. In some embodiments is a compound of Formula (III) or (III'), or a pharmaceutically acceptable salt or solvate thereof, wherein $R^1$ is a phenyl optionally substituted with one or more $R^{10}$. In some embodiments is a compound of Formula (III) or (III'), or a pharmaceutically acceptable salt or solvate thereof, wherein $R^1$ is a phenyl substituted with one or more $R^{10}$. In some embodiments is a compound of Formula (III) or (III'), or a pharmaceutically acceptable salt or solvate thereof, wherein $R^1$ is phenyl substituted with one, two, or three $R^{10}$. In some embodiments is a compound of Formula (III) or (III'), or a pharmaceutically acceptable salt or solvate thereof, wherein $R^1$ is phenyl substituted with one, two, or three $R^{10}$, wherein each $R^{10}$ is independently selected from halogen, $C_{1-6}$alkyl, $C_{3-7}$cycloalkyl, $C_{2-9}$heterocycloalkyl, $C_{6-10}$aryl, $C_{1-9}$heteroaryl, —$OR^{12}$, and $N(R^{12})(R^{13})$, wherein $C_{1-6}$alkyl, $C_{3-7}$cycloalkyl, $C_{2-9}$heterocycloalkyl, $C_{6-10}$aryl, and $C_{1-9}$heteroaryl are optionally substituted with one, two, or three $R^{20d}$. In some embodiments is a compound of Formula (III) or (III'), or a pharmaceutically acceptable salt or solvate thereof, wherein $R^1$ is phenyl substituted with one, two, or three $R^{10}$, wherein each $R^{10}$ is independently selected from halogen, $C_{1-6}$alkyl, and $N(R^{12})(R^{13})$, wherein $C_{1-6}$alkyl is optionally substituted with one, two, or three $R^{20d}$. In some embodiments is a compound of Formula (III) or (III'), or a pharmaceutically acceptable salt or solvate thereof, wherein $R^1$ is phenyl substituted with one, two, or three $R^{10}$, wherein each $R^{10}$ is independently selected from halogen and $C_{1-6}$alkyl, wherein $C_{1-6}$alkyl is substituted with one, two, or three $R^{20d}$, and each $R^{20d}$ is halogen.

In some embodiments is a compound of Formula (III) or (III'), or a pharmaceutically acceptable salt or solvate thereof, wherein $R^1$ is a 5-10 membered heteroaryl ring optionally substituted with one or more $R^{10}$. In some embodiments is a compound of Formula (III) or (III'), or a pharmaceutically acceptable salt or solvate thereof, wherein $R^1$ is a 5-10 membered heteroaryl ring substituted with one or more $R^{10}$. In some embodiments is a compound of Formula (III) or (III'), or a pharmaceutically acceptable salt or solvate thereof, wherein $R^1$ is a 5-10 membered heteroaryl ring substituted with one, two, or three $R^{10}$. In some embodiments is a compound of Formula (III) or (III'), or a pharmaceutically acceptable salt or solvate thereof, wherein $R^1$ is a 5-10 membered heteroaryl ring substituted with one, two, or three $R^{10}$, wherein each $R^{10}$ is independently selected from halogen, $C_{1-6}$alkyl, $C_{3-7}$cycloalkyl, $C_{2-9}$heterocycloalkyl, $C_{6-10}$aryl, $C_{1-9}$heteroaryl, —$OR^{12}$, and $N(R^{12})(R^{13})$, wherein $C_{1-6}$alkyl, $C_{3-7}$cycloalkyl, $C_{2-9}$heterocycloalkyl, $C_{6-10}$aryl, and $C_{1-9}$heteroaryl are optionally substituted with one, two, or three $R^{20d}$. In some embodiments is a compound of Formula (III) or (III'), or a pharmaceutically acceptable salt or solvate thereof, wherein $R^1$ is a 5-10 membered heteroaryl ring substituted with one, two, or three $R^{10}$, wherein each $R^{10}$ is independently selected from halogen, $C_{1-6}$alkyl, and $N(R^{12})(R^{13})$, wherein $C_{1-6}$alkyl is optionally substituted with one, two, or three $R^{20d}$. In some embodiments is a compound of Formula (III) or (III'), or a pharmaceutically acceptable salt or solvate thereof, wherein $R^1$ is a 5-10 membered heteroaryl ring substituted with one, two, or three $R^{10}$, wherein each $R^{10}$ is independently selected from halogen and $C_{1-6}$alkyl, wherein $C_{1-6}$alkyl is substituted with one, two, or three $R^{20d}$, and each $R^{20d}$ is halogen. In some embodiments is a compound of Formula (III) or (III'), or a pharmaceutically acceptable salt or solvate thereof, wherein $R^1$ is an unsubstituted 5-10 membered heteroaryl ring.

In some embodiments is a compound of Formula (III) or (III'), or a pharmaceutically acceptable salt or solvate thereof, wherein $R^1$ is a 3-12 membered cycloalkyl ring optionally substituted with one or more $R^{10}$. In some embodiments is a compound of Formula (III) or (III'), or a pharmaceutically acceptable salt or solvate thereof, wherein $R^1$ is a 3-12 membered cycloalkyl ring substituted with one or more $R^{10}$. In some embodiments is a compound of Formula (III) or (III'), or a pharmaceutically acceptable salt or solvate thereof, wherein $R^1$ is an unsubstituted 3-12 membered cycloalkyl ring.

In some embodiments is a compound of Formula (III) or (III'), or a pharmaceutically acceptable salt or solvate thereof, wherein $R^1$ is a 3-12 membered heterocycloalkyl ring optionally substituted with one or more $R^{10}$. In some embodiments is a compound of Formula (III) or (III'), or a pharmaceutically acceptable salt or solvate thereof, wherein $R^1$ is a 3-12 membered heterocycloalkyl ring substituted with one or more $R^{10}$. In some embodiments is a compound of Formula (III) or (III'), or a pharmaceutically acceptable salt or solvate thereof, wherein $R^1$ is an unsubstituted 3-12 membered heterocycloalkyl ring optionally substituted with one or more $R^{10}$.

In some embodiments is a compound of Formula (III) or (III'), or a pharmaceutically acceptable salt or solvate thereof, wherein $R^4$ is hydrogen. In some embodiments is a compound of Formula (III) or (III'), or a pharmaceutically acceptable salt or solvate thereof, wherein $R^4$ is $C_{1-6}$alkyl. In some embodiments is a compound of Formula (III) or (III'), or a pharmaceutically acceptable salt or solvate thereof, wherein $R^4$ is $-CH_3$. In some embodiments is a compound of Formula (III) or (III'), or a pharmaceutically acceptable salt or solvate thereof, wherein $R^4$ is $C_{1-6}$haloalkyl.

In embodiments of a compound of Formula (I), (I'), (Ia), (Ia'), (Ib), (Ib'), (Ic), (Ic'), (II), (II'), (III), or (III'), $R^{20b}$ is $C_{1-6}$alkyl (e.g., methyl, ethyl, or propyl) optionally substituted with one, two, or three $-N(R^{22})(R^{23})$ and $R^{22}$ and $R^{23}$ are independently selected from H and $C_{1-6}$alkyl (e.g., methyl). In embodiments of a compound of Formula (I), (I'), (Ia), (Ia'), (Ib), (Ib'), (Ic), (Ic'), (II), (II'), (III), or (III'), $R^{20b}$ is $C_{1-6}$alkyl (e.g., methyl, ethyl, or propyl) optionally substituted with one, two, or three $-OR^{21}$ and $R^{21}$ is independently selected from H and $C_{1-6}$alky. In embodiments of a compound of Formula (I), (I'), (Ia), (Ia'), (Ib), (Ib'), (Ic), (Ic'), (II), (II'), (III), or (III'), $R^{20b}$ is selected from $-CH_2-C_{6-10}$aryl and $-CN$. In embodiments of a compound of Formula (I), (I'), (Ia), (Ia'), (Ib), (Ib'), (Ic), (Ic'), (II), (II'), (III), or (III'), $R^{20b}$ is selected from oxo and $=NH$. In embodiments of a compound of Formula (I), (I'), (Ia), (Ia'), (Ib), (Ib'), (Ic), (Ic'), (II), (II'), (III), or (III'), $R^{20b}$ is $C_{2-9}$heterocycloalkyl. In embodiments of a compound of Formula (I), (I'), (Ia), (Ia'), (Ib), (Ib'), (Ic), (Ic'), (II), (II'), (III), or (III'), $R^{20b}$ is $-C(O)R^{20e}$ and $R^{25}$ is $C_{1-6}$alkyl. In embodiments of a compound of Formula (I), (I'), (Ia), (Ia'), (Ib), (Ib'), (Ic), (Ic'), (II), (II'), (III), or (III'), $R^{20b}$ is $-C(O)R^{25}$ and $R^{25}$ is $C_{2-6}$heterocycloalkyl optionally substituted with one, two, or three $C_{1-6}$alkyl. In embodiments of a compound of Formula (I), (I'), (Ia), (Ia'), (Ib), (Ib'), (Ic), (Ic'), (II), (II'), (III), or (III'), $R^{20b}$ is $C_{1-6}$alkyl optionally substituted with one, two, or three groups independently selected from oxo, $-OR^{21}$, and $-N(R^{22})(R^{23})$, $R^{21}$ is H, and $R^{22}$ and $R^{23}$ are independently selected from H and $C_{1-6}$alkyl (e.g., methyl).

In embodiments of a compound of Formula (I), (I'), (Ia), (Ia'), (Ib), (Ib'), (Ic), (Ic'), (II), (II'), (III), or (III'), $R^{20a}$ is $C_{1-6}$alkyl (e.g., methyl, ethyl, or propyl) optionally substituted with one, two, or three $-N(R^{22})(R^{23})$ and $R^{22}$ and $R^{23}$ are independently selected from H and $C_{1-6}$alkyl (e.g., methyl). In embodiments of a compound of Formula (I), (I'), (Ia), (Ia'), (Ib), (Ib'), (Ic), (Ic'), (II), (II'), (III), or (III'), $R^{20a}$ is $C_{1-6}$alkyl (e.g., methyl, ethyl, or propyl) optionally substituted with one, two, or three $-OR^{21}$ and $R^{21}$ is independently selected from H and $C_{1-6}$alky. In embodiments of a compound of Formula (I), (I'), (Ia), (Ia'), (Ib), (Ib'), (Ic), (Ic'), (II), (II'), (III), or (III'), $R^{20a}$ selected from $-CH_2-C_{6-10}$aryl and $-CN$. In embodiments of a compound of Formula (I), (I'), (Ia), (Ia'), (Ib), (Ib'), (Ic), (Ic'), (II), (II'), (III), or (III'), $R^{20a}$ is selected from oxo and $=NH$. In embodiments of a compound of Formula (I), (I'), (Ia), (Ia'), (Ib), (Ib'), (Ic), (Ic'), (II), (II'), (III), or (III'), $R^{20a}$ is $C_{2-9}$heterocycloalkyl. In embodiments of a compound of Formula (I), (I'), (Ia), (Ia'), (Ib), (Ib'), (Ic), (Ic'), (II), (II'), (III), or (III'), $R^{20a}$ is $-C(O)R^{25}$ and $R^{21}$ is $C_{1-6}$alkyl. In embodiments of a compound of Formula (I), (I'), (Ia), (Ia'), (Ib), (Ib'), (Ic), (Ic'), (II), (II'), (III), or (III'), $R^{20a}$ is $-C(O)R^{21}$ and $R^{21}$ is $C_{2-6}$heterocycloalkyl optionally substituted with one, two, or three $C_{1-6}$alkyl. In embodiments of a compound of Formula (I), (I'), (Ia), (Ia'), (Ib), (Ib'), (Ic), (Ic'), (II), (II'), (III), or (III'), $R^{20a}$ is $C_{1-6}$alkyl optionally substituted with one, two, or three groups independently selected from oxo, $-OR^{21}$, and $-N(R^{22})(R^{23})$, $R^{21}$ is H, and $R^{22}$ and $R^{23}$ are independently selected from H and $C_{1-6}$alkyl (e.g., methyl).

In embodiments of a compound of Formula (I), (I'), (Ia), (Ia'), (Ib), (Ib'), (Ic), (Ic'), (II), (II'), (III), or (III'), $R^2$ is $-NR^{2b}R^{2c}$ and $R^{2b}$ and $R^{2c}$ are selected from hydrogen and $C_{2-5}$heterocycloalkyl. In embodiments of a compound of Formula (I), (I'), (Ia), (Ia'), (Ib), (Ib'), (Ic), (Ic'), (II), (II'), (III), or (III'), $R^2$ is $-NHR^{2c}$ and $R^{2c}$ is $C_{2-5}$heterocycloalkyl optionally substituted with one, two, or three $R^{20a}$ and $R^{20a}$ is $C_{1-6}$alkyl (e.g., methyl). In embodiments of a compound of Formula (I), (I'), (Ia), (Ia'), (Ib), (Ib'), (Ic), (Ic'), (II), (II'), (III), or (III'), $R^2$ is $-OR^{2a}$ and $R^{2a}$ is $C_{2-5}$heterocycloalkyl optionally substituted with one, two, or three $R^{20a}$ and $R^{20a}$ is $C_{1-6}$alkyl (e.g., methyl). In embodiments of a compound of Formula (I), (I'), (Ia), (Ia'), (Ib), (Ib'), (Ic), (Ic'), (II), (II'), (III), or (III'), $R^2$ is $-OR^{2a}$ and $R^{2a}$ is $C_{1-6}$alkyl (e.g., methyl) optionally substituted with one, two, or three $R^{20a}$ and $R^{20a}$ is $C_{2-5}$heterocycloalkyl. In embodiments of a compound of Formula (I), (I'), (Ia), (Ia'), (Ib), (Ib'), (Ic), (Ic'), (II), (II'), (III), or (III'), $R^2$ is $-OR^{2a}$ and $R^{2a}$ is $C_{1-6}$alkyl (e.g., methyl) optionally substituted with one, two, or three $R^{20a}$ and $R^{20a}$ is $C_{2-5}$heterocycloalkyl optionally substituted with one, two, or three groups independently selected from halogen and $C_{1-6}$alkyl (e.g., methyl).

In embodiments of a compound of Formula (I), (I'), (Ia), (Ia'), (Ib), (Ib'), (Ic), (Ic'), (II), (II'), (III), or (III'), $R^7$ is $C_{1-6}$alkyl (e.g., methyl, ethyl, or propyl) optionally substituted with one, two, or three $R^{20c}$ and $R^{20c}$ is $C_{2-5}$heterocycloalkyl. In embodiments of a compound of Formula (I), (I'), (Ia), (Ia'), (Ib), (Ib'), (Ic), (Ic'), (II), (II'), (III), or (III'), $R^7$ is $C_{2-5}$heterocycloalkyl optionally substituted with one, two, or three $R^{2c}$ and $-N(R^{22})(R^{23})$ and $R^{22}$ and $R^{23}$ are independently selected from H and $C_{1-6}$alkyl (e.g., methyl). In embodiments of a compound of Formula (I), (I'), (Ia), (Ia'), (Ib), (Ib'), (Ic), (Ic'), (II), (II'), (III), or (III'), $R^7$ is $-OR^{12}$, $R^{12}$ is $C_{2-9}$heterocycloalkyl optionally substituted with one, two, or three $R^{20e}$ and $R^{20e}$ is $C_{1-6}$alkyl (e.g., methyl, ethyl, or propyl). In embodiments of a compound of Formula (I), (I'), (Ia), (Ia'), (Ib), (Ib'), (Ic), (Ic'), (II), (II'), (III), or (III'), $R^7$ is $-OR^{12}$, $R^{12}$ is $C_{1-6}$alkyl optionally substituted with one, two, or three $R^{20e}$, and $R^{20e}$ is $C_{2-5}$heterocycloalkyl optionally substituted with one, two, or three $C_{1-6}$alkyl (e.g., methyl, ethyl, or propyl).

In some embodiments of a compound of Formula (I), (I'), (Ia), (Ia'), (Ib), (Ib'), (Ic), (Ic'), (II), (II'), (III), or (III'), $R^{10}$ is independently selected from halogen and $C_{1-6}$alkyl optionally substituted with one, two, or three $R^{20d}$ and $R^{20d}$ is independently selected from halogen and $C_{2-5}$heterocycloalkyl optionally substituted with one, two, or three $C_{1-6}$alkyl (e.g., methyl, ethyl, or propyl). In some embodiments of a compound of Formula (I), (I'), (Ia), (Ia'), (Ib), (Ib'), (Ic), (Ic'), (II), (II'), (III), or (III'), $R^{10}$ is independently selected from halogen and $C_{1-6}$alkyl optionally substituted with one, two, or three $R^{20d}$ and $R^{20d}$ is independently selected from halogen and $C_{2-5}$heterocycloalkyl optionally substituted with one, two, or three —C(O)OR$^{22}$ and $R^{22}$ is $C_{1-6}$alkyl (e.g., methyl, ethyl, propyl, or butyl). In some embodiments of a compound of Formula (I), (I'), (Ia), (Ia'), (Ib), (Ib'), (Ic), (Ic'), (II), (II'), (III), or (III'), $R^{10}$ is independently selected from halogen and $C_{1-6}$alkyl optionally substituted with one, two, or three $R^{20d}$ and $R^{20d}$ is independently selected from halogen and —OR$^{21}$, wherein $R^{21}$ is $C_{2-5}$heterocycloalkyl optionally substituted with one, two, or three $C_{1-6}$alkyl (e.g., methyl, ethyl, propyl, or butyl). In some embodiments of a compound of Formula (I), (I'), (Ia), (Ia'), (Ib), (Ib'), (Ic), (Ic'), (II), (II'), (III), or (III'), $R^1$ is

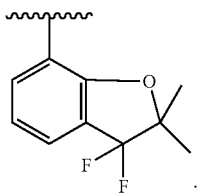 [SMILES: *c1cccc2c1OC(C)(C)C2(F)F]

In some embodiments of a compound of Formula (I), (I'), (Ia), (Ia'), (Ib), (Ib'), (Ic), (Ic'), (II), (II'), (III), or (III'), $R^{10}$ is independently selected from halogen and $C_{1-6}$alkyl optionally substituted with one, two, or three $R^{20d}$ and $R^{20d}$ is independently selected from halogen and $C_{3-5}$cycloalkyl optionally substituted with one, two, or three —N(R$^{22}$)(R$^{23}$), wherein $R^{22}$ and $R^{23}$ are each independently selected hydrogen and $C_{1-6}$alkyl (e.g., methyl, ethyl, or propyl).

In one aspect, the disclosure provides a compound of Formula (I), or a pharmaceutically acceptable salt or solvate thereof:

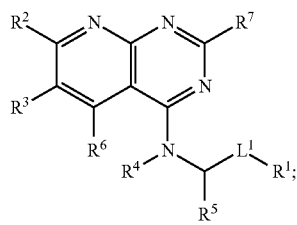

Formula (I)

wherein:
$L^1$, $R^2$, $R^3$, $R^4$, $R^5$, $R^6$, $R^7$, $R^{12}$, $R^{13}$, $R^{13a}$, $R^{14}$, $R^{15}$, $R^{17}$, $R^{17a}$, $R^{21}$, $R^{22}$, $R^{23}$, $R^{24}$, and $R^{25}$ are as described herein.
$R^1$ is a 3-12 membered cycloalkyl ring, 3-12 membered heterocycloalkyl ring, 6-10 membered aryl ring, or 5-10 membered heteroaryl ring, wherein the 3-12 membered cycloalkyl ring, 3-12 membered heterocycloalkyl ring, 6-10 membered aryl ring, and 5-10 membered heteroaryl ring are optionally substituted with one or more $R^{10}$;
each $R^{10}$ is independently selected from halogen, —CN, $C_{1-6}$alkyl, $C_{2-6}$alkenyl, $C_{2-6}$alkynyl, $C_{3-7}$cycloalkyl, $C_{2-9}$heterocycloalkyl, $C_{6-10}$aryl, $C_{1-9}$heteroaryl, —OR$^{12}$, —SR$^{12}$, —N(R$^{12}$)(R$^{13}$), —C(O)OR$^{12}$, —OC(O)N(R$^{12}$)(R$^{13}$), —N(R$^{14}$)C(O)N(R$^{12}$)(R$^{13}$), —N(R$^{14}$)C(O)OR$^{15}$, —N(R$^{14}$)S(O)$_2$R$^{15}$, —C(O)R$^{15}$, —S(O)R$^{15}$, —OC(O)R$^{15}$, —C(O)N(R$^{12}$)(R$^{13}$), —C(O)C(O)N(R$^{12}$)(R$^{13}$), —N(R$^{14}$)C(O)R$^{15}$, —S(O)$_2$R$^{15}$, —S(O)$_2$N(R$^{12}$)(R$^{13}$), —S(=O)(=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, —CH$_2$S(O)$_2$N(R$^{12}$)(R$^{13}$), —CH$_2$N(R$^{12}$)S(O)$_2$(R$^{13}$), —P(O)(R$^{17}$)(R$^{17a}$), and $C_{1-6}$alkyl-O—$C_{1-6}$alkyl, wherein $C_{1-6}$alkyl, $C_{2-6}$alkenyl, $C_{2-6}$alkynyl, $C_{3-7}$cycloalkyl, $C_{2-9}$heterocycloalkyl, $C_{6-10}$aryl, $C_{1-9}$heteroaryl, and $C_{1-6}$alkyl-O—$C_{1-6}$alkyl are optionally substituted with one, two, or three $R^{20d}$;
each $R^{20d}$ is independently selected from halogen, oxo, =NH, —CN, $C_{1-6}$alkyl, $C_{2-6}$alkenyl, $C_{2-6}$alkynyl, $C_{3-10}$cycloalkyl, —CH$_2$—$C_{3-10}$cycloalkyl, $C_{2-9}$heterocycloalkyl, —CH$_2$—$C_{2-9}$heterocycloalkyl, $C_{6-10}$aryl, —CH$_2$—$C_{6-10}$aryl, $C_{1-9}$heteroaryl, —OR$^{21}$, —SR$^{21}$, —N(R$^{22}$)(R$^{23}$), —C(O)OR$^{22}$, —C(O)N(R$^{22}$)(R$^{23}$), —C(O)C(O)N(R$^{22}$)(R$^{23}$), —OC(O)N(R$^{22}$)(R$^{23}$), —N(R$^{24}$)C(O)N(R$^{22}$)(R$^{23}$), —N(R$^{24}$)C(O)OR$^{25}$, —N(R$^{24}$)C(O)R$^{25}$, —N(R$^{24}$)S(O)$_2$R$^{25}$, —C(O)R$^{25}$, —S(O)$_2$R$^{25}$, —S(O)$_2$N(R$^{22}$)(R$^{23}$), —OCH$_2$C(O)OR$^{22}$, and —OC(O)R$^{25}$, wherein $C_{1-6}$alkyl, $C_{2-6}$alkenyl, $C_{2-6}$alkynyl, $C_{3-10}$cycloalkyl, —CH$_2$—$C_{3-10}$cycloalkyl, $C_{2-9}$heterocycloalkyl, —CH$_2$—$C_{2-9}$heterocycloalkyl, $C_{6-10}$aryl, —CH$_2$—$C_{6-10}$aryl, and $C_{1-9}$heteroaryl are optionally substituted with one, two, or three groups independently selected from halogen, oxo, =NH, —CN, $C_{1-6}$alkyl, $C_{1-6}$haloalkyl, $C_{1-6}$alkoxy, $C_{1-6}$haloalkoxy, —OR$^{21}$, —SR$^{21}$, —N(R$^{22}$)(R$^{23}$), —C(O)OR$^{22}$, —C(O)N(R$^{22}$)(R$^{23}$), —C(O)C(O)N(R$^{22}$)(R$^{23}$), —OC(O)N(R$^{22}$)(R$^{23}$), —N(R$^{24}$)C(O)N(R$^{22}$)(R$^{23}$), —N(R$^{24}$)C(O)OR$^{25}$, —N(R$^{24}$)C(O)R$^{25}$, —N(R$^{24}$)S(O)$_2$R$^{25}$, —C(O)R$^{25}$, —S(O)$_2$R$^{25}$, —S(O)$_2$N(R$^{22}$)(R$^{23}$), and —OC(O)R$^{25}$.

In some embodiments of a compound of Formula (I), $R^{10}$ is independently selected from halogen and $C_{1-6}$ alkyl-O—$C_{1-6}$alkyl optionally substituted with one, two, or three $R^{20d}$ and $R^{20d}$ is independently selected from halogen and —N(R$^{22}$)(R$^{23}$), wherein $R^{22}$ and $R^{23}$ are each independently selected hydrogen and $C_{1-6}$alkyl (e.g., methyl, ethyl, or propyl).

In some embodiments is a compound of Formula (I), (I'), (Ia), (Ia'), (Ib), (Ib'), (Ic), (Ic'), (II), (II'), (III), or (III'), or a pharmaceutically acceptable salt or solvate thereof, wherein $R^1$ is a 6-10 membered aryl ring substituted with one or more $R^{10}$. In some embodiments is a compound of Formula (I), (I'), (Ia), (Ia'), (Ib), (Ib'), (Ic), (Ic'), (II), (II'), (III), or (III'), or a pharmaceutically acceptable salt or solvate thereof, wherein $R^1$ is phenyl substituted with one or more $R^{10}$. In some embodiments is a compound of Formula (I), (I'), (Ia), (Ia'), (Ib), (Ib'), (Ic), (Ic'), (II), (II'), (III), or (III'), or a pharmaceutically acceptable salt or solvate thereof, wherein $R^1$ is phenyl substituted with one, two, or three $R^{10}$. In some embodiments is a compound of Formula (I), (I'), (Ia), (Ia'), (Ib), (Ib'), (Ic), (Ic'), (II), (II'), (III), or (III'), or a pharmaceutically acceptable salt or solvate thereof, wherein $R^1$ is a 5-10 membered heteroaryl ring are substituted with one or more $R^{10}$. In some embodiments is a compound of Formula (I), (I'), (Ia), (Ia'), (Ib), (Ib'), (Ic), (Ic'), (II), (II'), (III), or (III'), or a pharmaceutically acceptable salt or solvate thereof, wherein $R^1$ is a 5-10 membered heteroaryl ring are substituted with one, two, or three $R^{10}$. In some embodiments is a compound of Formula (I), (I'), (Ia), (Ia'), (Ib), (Ib'), (Ic), (Ic'), (II), (II'), (III), or (III'), or a pharmaceutically acceptable salt or solvate thereof, wherein each $R^{10}$ is independently selected from halogen, $C_{1-6}$alkyl, $C_{3-7}$cycloalkyl, $C_{2-9}$heterocycloalkyl, $C_{6-10}$aryl, $C_{1-9}$heteroaryl, —OR$^{12}$, and N(R$^{12}$)(R$^{13}$), wherein C$_{1-6}$alkyl, C$_{3-7}$cycloalkyl, C$_{2-9}$heterocycloalkyl, C$_{6-10}$aryl, and C$_{1-9}$heteroaryl are optionally substituted with one, two, or three R$^{20d}$. In some embodiments is a compound of Formula (I), (I'), (Ia), (Ia'), (Ib), (Ib'), (Ic), (Ic'), (II), (II'), (III), or (III'), or a pharmaceutically acceptable salt or solvate thereof, wherein each R$^{10}$ is independently selected from halogen, C$_{1-6}$alkyl, and N(R$^{12}$)(R$^{13}$), wherein C$_{1-6}$ alkyl is optionally substituted with one, two, or three R$^{20d}$. In some embodiments is a compound of Formula (I), (I'), (Ia), (Ia'), (Ib), (Ib'), (Ic), (Ic'), (II), (II'), (III), or (III'), or a pharmaceutically acceptable salt or solvate thereof, wherein each R$^{10}$ is independently selected from halogen, C$_{1-6}$alkyl, and N(R$^{12}$)(R$^{13}$), wherein C$_{1-6}$alkyl is substituted with one, two, or three R$^{20d}$, and each R$^{20d}$ is halogen.

In some embodiments is a compound of Formula (I), (I'), (Ia), (Ia'), (Ib), (Ib'), (Ic), (Ic'), (II), (II'), (III), or (III'), wherein R$^1$ is benzothiazolyl optionally substituted with one or more R$^{10}$. In some embodiments is a compound of Formula (I), (I'), (Ia), (Ia'), (Ib), (Ib'), (Ic), (Ic'), (II), (II'), (III), or (III'), wherein R$^1$ is 1H-benzo[d]imidazolyl optionally substituted with one or more R$^{10}$. In some embodiments is a compound of Formula (I), (I'), (Ia), (Ia'), (Ib), (Ib'), (Ic), (Ic'), (II), (II'), (III), or (III'), wherein R$^1$ is benzo[c]thiophenyl optionally substituted with one or more R$^{10}$. In some embodiments is a compound of Formula (I), (I'), (Ia), (Ia'), (Ib), (Ib'), (Ic), (Ic'), (II), (II'), (III), or (III'), wherein R$^1$ is benzo[b]thiophenyl optionally substituted with one or more R$^{10}$. In some embodiments is a compound of Formula (I), (I'), (Ia), (Ia'), (Ib), (Ib'), (Ic), (Ic'), (II), (II'), (III), or (III'), wherein R$^1$ is indanyl optionally substituted with one or more R$^{10}$. In some embodiments is a compound of Formula (I), (I'), (Ia), (Ia'), (Ib), (Ib'), (Ic), (Ic'), (II), (II'), (III), or (III'), wherein R$^1$ is indenyl optionally substituted with one or more R$^{10}$. In some embodiments is a compound of Formula (I), (I'), (Ia), (Ia'), (Ib), (Ib'), (Ic), (Ic'), (II), (II'), (III), or (III'), wherein R$^1$ is tetralinyl optionally substituted with one or more R$^{10}$. In some embodiments is a compound of Formula (I), (I'), (Ia), (Ia'), (Ib), (Ib'), (Ic), (Ic'), (II), (II'), (III), or (III'), wherein R$^1$ is coumaranyl optionally substituted with one or more R$^{10}$. In some embodiments is a compound of Formula (I), (I'), (Ia), (Ia'), (Ib), (Ib'), (Ic), (Ic'), (II), (II'), (III), or (III'), wherein R$^1$ is furanyl optionally substituted with one or more R$^{10}$. In some embodiments is a compound of Formula (I), (I'), (Ia), (Ia'), (Ib), (Ib'), (Ic), (Ic'), (II), (II'), (III), or (III'), wherein R$^1$ is thiophenyl optionally substituted with one or more R$^{10}$. In some embodiments is a compound of Formula (I), (I'), (Ia), (Ia'), (Ib), (Ib'), (Ic), (Ic'), (II), (II'), (III), or (III'), wherein R$^1$ is oxazolyl optionally substituted with one or more R$^{10}$. In some embodiments is a compound of Formula (I), (I'), (Ia), (Ia'), (Ib), (Ib'), (Ic), (Ic'), (II), (II'), (III), or (III'), wherein R$^1$ is thiazolyl optionally substituted with one or more R$^{10}$. In some embodiments is a compound of Formula (I), (I'), (Ia), (Ia'), (Ib), (Ib'), (Ic), (Ic'), (II), (II'), (III), or (III'), wherein R$^1$ is 1H-indazolyl optionally substituted with one or more R$^{10}$. In some embodiments is a compound of Formula (I), (I'), (Ia), (Ia'), (Ib), (Ib'), (Ic), (Ic'), (II), (II'), (III), or (III'), wherein R$^1$ is imidazo[1,2-a]pyridinyl optionally substituted with one or more R$^{10}$. In some embodiments is a compound of Formula (I), (I'), (Ia), (Ia'), (Ib), (Ib'), (Ic), (Ic'), (II), (II'), (III), or (III'), wherein R$^1$ is pyrazolyl optionally substituted with one or more R$^{10}$. In some embodiments is a compound of Formula (I), (I'), (Ia), (Ia'), (Ib), (Ib'), (Ic), (Ic'), (II), (II'), (III), or (III'), wherein R$^1$ is 1H-indolyl optionally substituted with one or more R$^{10}$. In some embodiments is a compound of Formula (I), (I'), (Ia), (Ia'), (Ib), (Ib'), (Ic), (Ic'), (II), (II'), (III), or (III'), wherein R$^1$ is pyridinyl optionally substituted with one or more R$^{10}$. In some embodiments is a compound of Formula (I), (I'), (Ia), (Ia'), (Ib), (Ib'), (Ic), (Ic'), (II), (II'), (III), or (III'), wherein R$^1$ is pyrimidinyl optionally substituted with one or more R$^{10}$. In some embodiments is a compound of Formula (I), (I'), (Ia), (Ia'), (Ib), (Ib'), (Ic), (Ic'), (II), (II'), (III), or (III'), wherein R$^1$ is pyrizinyl optionally substituted with one or more R$^{10}$. In some embodiments is a compound of Formula (I), (I'), (Ia), (Ia'), (Ib), (Ib'), (Ic), (Ic'), (II), (II'), (III), or (III'), wherein R$^1$ is 1H-imidazolyl optionally substituted with one or more R$^{10}$. In some embodiments is a compound of Formula (I), (I'), (Ia), (Ia'), (Ib), (Ib'), (Ic), (Ic'), (II), (II'), (III), or (III'), wherein R$^1$ is 1,4-benzodioxanyl optionally substituted with one or more R$^{10}$. In some embodiments is a compound of Formula (I), (I'), (Ia), (Ia'), (Ib), (Ib'), (Ic), (Ic'), (II), (II'), (III), or (III'), wherein R$^1$ is 3,4-dihydrobenzo[1,4]oxazinyl optionally substituted with one or more R$^{10}$. In some embodiments is a compound of Formula (I), (I'), (Ia), (Ia'), (Ib), (Ib'), (Ic), (Ic'), (II), (II'), (III), or (III'), wherein R$^1$ is benzo[b]furanyl optionally substituted with one or more R$^{10}$. In some embodiments is a compound of Formula (I), (I'), (Ia), (Ia'), (Ib), (Ib'), (Ic), (Ic'), (II), (II'), (III), or (III'), wherein R$^1$ is benzo[c]furanyl optionally substituted with one or more R$^{10}$. In some embodiments is a compound of Formula (I), (I'), (Ia), (Ia'), (Ib), (Ib'), (Ic), (Ic'), (II), (II'), (III), or (III'), wherein R$^1$ is phenyl optionally substituted with one or more R$^{10}$. In some embodiments is a compound of Formula (I), (I'), (Ia), (Ia'), (Ib), (Ib'), (Ic), (Ic'), (II), (II'), (III), or (III'), wherein R$^1$ is naphthalenyl optionally substituted with one or more R$^{10}$.

In some embodiments is a compound of Formula (I), (I'), (Ia), (Ia'), (Ib), (Ib'), (Ic), (Ic'), (II), (II'), (III), or (III'), wherein R$^1$ is (benzo[d][1,3]dioxol-4-yl, 1,8a-dihydroimidazo[1,2-a]pyridin-8-yl, 1H-indazol-4-yl, 1H-indazol-5-yl, 1H-indazol-6-yl, 1H-indazol-7-yl, 1H-inden-4-yl, 1H-inden-5-yl, 1H-inden-6-yl, 1H-inden-7-yl, 2,3-dihydro-1H-inden-4-yl, 2,3-dihydro-1H-inden-5-yl, 2,3-dihydrobenzo[b][1,4]dioxin-5-yl, 2,3-dihydrobenzo[b][1,4]dioxin-6-yl, 2,3-dihydrobenzofuran-4-yl, 2,3-dihydrobenzofuran-5-yl, 2,3-dihydrobenzofuran-6-yl, 2,3-dihydrobenzofuran-7-yl, 3,4-dihydro-2H-benzo[b][1,4]oxazin-5-yl, 3,4-dihydro-2H-benzo[b][1,4]oxazin-6-yl, 3,4-dihydro-2H-benzo[b][1,4]oxazin-7-yl, 3,4-dihydro-2H-benzo[b][1,4]oxazin-8-yl, 4-(benzo[d][1,3]dioxol-5-yl, 5,6,7,8-tetrahydronaphthalen-1-yl, 5,6,7,8-tetrahydronaphthalen-2-yl, benzo[b]thiophen-4-yl, benzo[b]thiophen-5-yl, benzo[b]thiophen-6-yl, benzo[b]thiophen-7-yl, benzo[d]thiazol-4-yl, benzo[d]thiazol-5-yl, benzo[d]thiazol-6-yl, benzo[d]thiazol-7-yl, benzofuran-4-yl, benzofuran-5-yl, benzofuran-6-yl, benzofuran-7-yl, chroman-5-yl, chroman-6-yl, chroman-7-yl, chroman-8-yl, furan-2-yl, furan-3-yl, imidazo[1,2-a]pyridin-5-yl, imidazo[1,2-a]pyridin-6-yl, imidazo[1,2-a]pyridin-7-yl, naphthalen-1-yl, naphthalen-2-yl, oxazol-2-yl, oxazol-4-yl, oxazol-5-yl, pyrazin-2-yl, pyridazin-3-yl, pyridazin-4-yl, pyridin-2-yl, pyridin-3-yl, pyridin-4-yl, pyrimidin-4-yl, pyrimidin-4-yl, pyrimidin-5-yl, thiazol-2-yl, thiazol-4-yl, thiazol-5-yl, or thiophen-3-yl, any of which is optionally substituted with one or more R$^{10}$.

In some embodiments of a compound of Formula (I), (I'), (Ia), (Ia'), (Ib), (Ib'), (Ic), (Ic'), (II), (II'), (III), or (III'), R¹ is

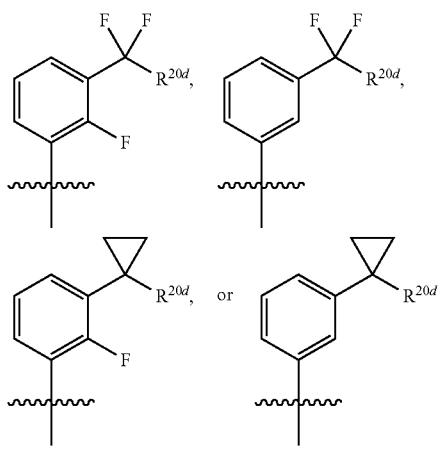

wherein each $R^{20d}$ is as described herein.

In embodiments of a compound of Formula (I), (I'), (Ia), (Ia'), (Ib), (Ib'), (Ic), (Ic'), (II), (II'), (III), or (III'), $R^{20d}$ is $C_{1-6}$alkyl optionally substituted with one, two, or three groups independently selected from halogen and —OR²¹. In embodiments of a compound of Formula (I), (I'), (Ia), (Ia'), (Ib), (Ib'), (Ic), (Ic'), (II), (II'), (III), or (III'), $R^{20d}$ is $C_{1-6}$alkyl optionally substituted with one, two, or three groups independently selected from halogen and —OH. In embodiments of a compound of Formula (I), (I'), (Ia), (Ia'), (Ib), (Ib'), (Ic), (Ic'), (II), (II'), (III), or (III'), $R^{20a}$ is $C_{1-6}$alkyl optionally substituted with one, two, or three groups independently selected from F and —OH. In embodiments of a compound of Formula (I), (I'), (Ia), (Ia'), (Ib), (Ib'), (Ic), (Ic'), (II), (II'), (III), or (III'), $R^{20d}$ is $C_{1-6}$alkyl optionally substituted with one —OH. In embodiments of a compound of Formula (I), (I'), (Ia), (Ia'), (Ib), (Ib'), (Ic), (Ic'), (II), (II'), (III), or (III'), $R^{20d}$ is $C_{1-6}$alkyl optionally substituted with one, two, or three F.

In embodiments of a compound of Formula (I), (I'), (Ia), (Ia'), (Ib), (Ib'), (Ic), (Ic'), (II), (II'), (III), or (III'), $R^{20d}$ is $C_{1-3}$alkyl optionally substituted with one, two, or three groups independently selected from halogen and —OR²¹. In embodiments of a compound of Formula (I), (I'), (Ia), (Ia'), (Ib), (Ib'), (Ic), (Ic'), (II), (II'), (III), or (III'), $R^{20d}$ is $C_{1-3}$alkyl optionally substituted with one, two, or three groups independently selected from halogen and —OH. In embodiments of a compound of Formula (I), (I'), (Ia), (Ia'), (Ib), (Ib'), (Ic), (Ic'), (II), (II'), (III), or (III'), $R^{20d}$ is $C_{1-3}$alkyl optionally substituted with one, two, or three groups independently selected from F and —OH. In embodiments of a compound of Formula (I), (I'), (Ia), (Ia'), (Ib), (Ib'), (Ic), (Ic'), (II), (II'), (III), or (III'), $R^{20d}$ is $C_{1-3}$alkyl substituted with one, two, or three groups independently selected from halogen and —OR²¹. In embodiments of a compound of Formula (I), (I'), (Ia), (Ia'), (Ib), (Ib'), (Ic), (Ic'), (II), (II'), (III), or (III'), $R^{20d}$ is $C_{1-3}$alkyl substituted with one, two, or three groups independently selected from halogen and —OH. In embodiments of a compound of Formula (I), (I'), (Ia), (Ia'), (Ib), (Ib'), (Ic), (Ic'), (II), (II'), (III), or (III'), $R^{20d}$ is $C_{1-3}$alkyl substituted with one, two, or three groups independently selected from F and —OH. In embodiments of a compound of Formula (I), (I'), (Ia), (Ia'), (Ib), (Ib'), (Ic), (Ic'), (II), (II'), (III), or (III'), $R^{20d}$ is $C_{1-3}$alkyl substituted with one —OH. In embodiments of a compound of Formula (I), (I'), (Ia), (Ia'), (Ib), (Ib'), (Ic), (Ic'), (II), (II'), (III), or (III'), $R^{20d}$ is $C_{1-3}$alkyl substituted with one, two, or three F.

In embodiments of a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), $R^{20d}$ is $C_{1-6}$alkyl optionally substituted with one, two, or three groups independently selected from halogen and —OR²¹. In embodiments of a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), $R^{20d}$ is $C_{1-6}$alkyl optionally substituted with one, two, or three groups independently selected from halogen and —OH. In embodiments of a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), $R^{20d}$ is $C_{1-6}$alkyl optionally substituted with one, two, or three groups independently selected from F and —OH. In embodiments of a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), $R^{20d}$ is $C_{1-6}$alkyl optionally substituted with one —OH. In embodiments of a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), $R^{20d}$ is $C_{1-6}$alkyl optionally substituted with one, two, or three F.

In embodiments of a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), $R^{20d}$ is $C_{1-3}$alkyl optionally substituted with one, two, or three groups independently selected from halogen and —OR²¹. In embodiments of a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), $R^{20d}$ is $C_{1-3}$alkyl optionally substituted with one, two, or three groups independently selected from halogen and —OH. In embodiments of a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), $R^{20d}$ is $C_{1-4}$alkyl optionally substituted with one, two, or three groups independently selected from F and —OH. In embodiments of a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), $R^{20d}$ is $C_{1-4}$alkyl substituted with one, two, or three groups independently selected from halogen and —OR²¹. In embodiments of a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), $R^{20d}$ is $C_{1-4}$alkyl substituted with one, two, or three groups independently selected from halogen and —OH. In embodiments of a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), $R^{20d}$ is $C_{1-4}$alkyl substituted with one, two, or three groups independently selected from F and —OH. In embodiments of a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), $R^{20d}$ is $C_{1-4}$alkyl substituted with one —OH. In embodiments of a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib- 2), (Ib'-2), (Ic-2), or (Ic'-2), $R^{20d}$ is $C_{1-4}$alkyl substituted with one, two, or three F.

In embodiments of a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), $R^{20d}$ is butyl optionally substituted with one, two, or three groups independently selected from halogen and —OR²¹. In embodiments of a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), $R^{20d}$ is butyl optionally substituted with one, two, or three groups independently selected from halogen and —OH. In embodiments of a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), $R^{20d}$ is butyl optionally substituted with one, two, or three groups independently selected from F and —OH. In embodiments of a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), $R^{20d}$ is butyl substituted with one, two, or three groups independently selected from halogen and —OR$^{21}$. In embodiments of a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), $R^{20d}$ is butyl substituted with one, two, or three groups independently selected from halogen and —OH. In embodiments of a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), $R^{20d}$ is butyl substituted with one, two, or three groups independently selected from F and —OH. In embodiments of a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), $R^{20d}$ is butyl substituted with one —OH. In embodiments of a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), $R^{20d}$ is butyl substituted with one, two, or three F.

In embodiments of a compound of Formula (I), (I'), (Ia), (Ia'), (Ib), (Ib'), (Ic), (Ic'), (II), (II'), (III), or (III'), $R^{20d}$ is isopropyl optionally substituted with one, two, or three groups independently selected from halogen and —OR$^{21}$. In embodiments of a compound of Formula (I), (I'), (Ia), (Ia'), (Ib), (Ib'), (Ic), (Ic'), (II), (II'), (III), or (III'), $R^{20d}$ is isopropyl optionally substituted with one, two, or three groups independently selected from halogen and —OH. In embodiments of a compound of Formula (I), (I'), (Ia), (Ia'), (Ib), (Ib'), (Ic), (Ic'), (II), (II'), (III), or (III'), $R^{20d}$ is isopropyl optionally substituted with one, two, or three groups independently selected from F and —OH. In embodiments of a compound of Formula (I), (I'), (Ia), (Ia'), (Ib), (Ib'), (Ic), (Ic'), (II), (II'), (III), or (III'), $R^{20d}$ is isopropyl substituted with one, two, or three groups independently selected from halogen and —OR$^{21}$. In embodiments of a compound of Formula (I), (I'), (Ia), (Ia'), (Ib), (Ib'), (Ic), (Ic'), (II), (II'), (III), or (III'), $R^{20d}$ is isopropyl substituted with one, two, or three groups independently selected from halogen and —OH. In embodiments of a compound of Formula (I), (I'), (Ia), (Ia'), (Ib), (Ib'), (Ic), (Ic'), (II), (II'), (III), or (III'), $R^{20d}$ is isopropyl substituted with one, two, or three groups independently selected from F and —OH. In embodiments of a compound of Formula (I), (I'), (Ia), (Ia'), (Ib), (Ib'), (Ic), (Ic'), (II), (II'), (III), or (III'), $R^{20d}$ is isopropyl substituted with one —OH. In embodiments of a compound of Formula (I), (I'), (Ia), (Ia'), (Ib), (Ib'), (Ic), (Ic'), (II), (II'), (III), or (III'), $R^{20d}$ is isopropyl substituted with one, two, or three F.

In embodiments of a compound of Formula (I), (I'), (Ia), (Ia'), (Ib), (Ib'), (Ic), (Ic'), (II), (II'), (III), or (III'), $R^{20d}$ is ethyl optionally substituted with one, two, or three groups independently selected from halogen and —OR$^{21}$. In embodiments of a compound of Formula (I), (I'), (Ia), (Ia'), (Ib), (Ib'), (Ic), (Ic'), (II), (II'), (III), or (III'), $R^{20d}$ is ethyl optionally substituted with one, two, or three groups independently selected from halogen and —OH. In embodiments of a compound of Formula (I), (I'), (Ia), (Ia'), (Ib), (Ib'), (Ic), (Ic'), (II), (II'), (III), or (III'), $R^{20d}$ is ethyl optionally substituted with one, two, or three groups independently selected from F and —OH. In embodiments of a compound of Formula (I), (I'), (Ia), (Ia'), (Ib), (Ib'), (Ic), (Ic'), (II), (II'), (III), or (III'), $R^{20d}$ is ethyl substituted with one, two, or three groups independently selected from halogen and —OR$^{21}$. In embodiments of a compound of Formula (I), (I'), (Ia), (Ia'), (Ib), (Ib'), (Ic), (Ic'), (II), (II'), (III), or (III'), $R^{20d}$ is ethyl substituted with one, two, or three groups independently selected from halogen and —OH. In embodiments of a compound of Formula (I), (I'), (Ia), (Ia'), (Ib), (Ib'), (Ic), (Ic'), (II), (II'), (III), or (III'), $R^{20d}$ is ethyl substituted with one, two, or three groups independently selected from F and —OH. In embodiments of a compound of Formula (I), (I'), (Ia), (Ia'), (Ib), (Ib'), (Ic), (Ic'), (II), (II'), (III), or (III'), $R^{20d}$ is ethyl substituted with one —OH. In embodiments of a compound of Formula (I), (I'), (Ia), (Ia'), (Ib), (Ib'), (Ic), (Ic'), (II), (II'), (III), or (III'), $R^{20d}$ is ethyl substituted with one, two, or three F.

In embodiments of a compound of Formula (I), (I'), (Ia), (Ia'), (Ib), (Ib'), (Ic), (Ic'), (II), (II'), (III), or (III'), $R^{20d}$ is methyl optionally substituted with one, two, or three groups independently selected from halogen and —OR$^{21}$. In embodiments of a compound of Formula (I), (I'), (Ia), (Ia'), (Ib), (Ib'), (Ic), (Ic'), (II), (II'), (III), or (III'), $R^{20d}$ is methyl optionally substituted with one, two, or three groups independently selected from halogen and —OH. In embodiments of a compound of Formula (I), (I'), (Ia), (Ia'), (Ib), (Ib'), (Ic), (Ic'), (II), (II'), (III), or (III'), $R^{20d}$ is methyl optionally substituted with one, two, or three groups independently selected from F and —OH. In embodiments of a compound of Formula (I), (I'), (Ia), (Ia'), (Ib), (Ib'), (Ic), (Ic'), (II), (II'), (III), or (III'), $R^{20d}$ is methyl substituted with one, two, or three groups independently selected from halogen and —OR$^{21}$. In embodiments of a compound of Formula (I), (I'), (Ia), (Ia'), (Ib), (Ib'), (Ic), (Ic'), (II), (II'), (III), or (III'), $R^{20d}$ is methyl substituted with one, two, or three groups independently selected from halogen and —OH. In embodiments of a compound of Formula (I), (I'), (Ia), (Ia'), (Ib), (Ib'), (Ic), (Ic'), (II), (II'), (III), or (III'), $R^{20d}$ is methyl substituted with one, two, or three groups independently selected from F and —OH. In embodiments of a compound of Formula (I), (I'), (Ia), (Ia'), (Ib), (Ib'), (Ic), (Ic'), (II), (II'), (III), or (III'), $R^{20d}$ is methyl substituted with one —OH. In embodiments of a compound of Formula (I), (I'), (Ia), (Ia'), (Ib), (Ib'), (Ic), (Ic'), (II), (II'), (III), or (III'), $R^{20d}$ is methyl substituted with one, two, or three F.

In embodiments of a compound of Formula (I), (I'), (Ia), (Ia'), (Ib), (Ib'), (Ic), (Ic'), (II), (II'), (III), or (III'), $R^{20d}$ is $C_{2-9}$heterocycloalkyl optionally substituted with one, two, or three groups independently selected from $C_{1-6}$alkyl, $C_{1-6}$haloalkyl, $C_{1-6}$alkoxy, and $C_{1-6}$haloalkoxy. In embodiments of a compound of Formula (I), (I'), (Ia), (Ia'), (Ib), (Ib'), (Ic), (Ic'), (II), (II'), (III), or (III'), $R^{20d}$ is $C_{2-9}$heterocycloalkyl optionally substituted with one, two, or three groups independently selected from $C_{1-4}$alkyl, $C_{1-4}$haloalkyl, $C_{1-4}$alkoxy, and $C_{1-4}$haloalkoxy. In embodiments of a compound of Formula (I), (I'), (Ia), (Ia'), (Ib), (Ib'), (Ic), (Ic'), (II), (II'), (III), or (III'), $R^{20d}$ is $C_{2-9}$heterocycloalkyl optionally substituted with one, two, or three groups independently selected from $C_{1-3}$alkyl, $C_{1-3}$haloalkyl, $C_{1-3}$alkoxy, and $C_{1-3}$haloalkoxy. In embodiments of a compound of Formula (I), (I'), (Ia), (Ia'), (Ib), (Ib'), (Ic), (Ic'), (II), (II'), (III), or (III'), $R^{20d}$ is $C_{2-9}$heterocycloalkyl optionally substituted with one $C_{1-6}$alkyl or one $C_{1-6}$haloalkyl. In embodiments of a compound of Formula (I), (I'), (Ia), (Ia'), (Ib), (Ib'), (Ic), (Ic'), (II), (II'), (III), or (III'), $R^{20d}$ is $C_{2-9}$heterocycloalkyl optionally substituted with one $C_{1-3}$alkyl or one $C_{1-3}$haloalkyl. In embodiments of a compound of Formula (I), (I'), (Ia), (Ia'), (Ib), (Ib'), (Ic), (Ic'), (II), (II'), (III), or (III'), $R^{20d}$ is $C_{2-9}$heterocycloalkyl optionally substituted with one $C_{1-6}$alkyl. In embodiments of a compound of Formula (I), (I'), (Ia), (Ia'), (Ib), (Ib'), (Ic), (Ic'), (II), (II'), (III), or (III'), $R^{20d}$ is $C_{2-9}$heterocycloalkyl optionally substituted with one $C_{1-3}$alkyl. In embodiments of a compound of Formula (I), (I'), (Ia), (Ia'), (Ib), (Ib'), (Ic), (Ic'), (II), (II'), (III), or (III'), $R^{20d}$ is $C_{2-9}$heterocycloalkyl optionally substituted with one methyl. In embodiments of a compound of Formula (I), (I'), (Ia), (Ia'), (Ib), (Ib'), (Ic), (Ic'), (II), (II'), (III), or (III'), $R^{20d}$ is $C_{2-9}$heterocycloalkyl optionally substituted with one ethyl. In embodiments of a compound of Formula (I), (I'), (Ia), (Ia'), (Ib), (Ib'), (Ic), (Ic'), (II), (II'), (III), or (III'), $R^{20d}$ is $C_{2-9}$heterocycloalkyl optionally substituted with one propyl. In embodiments of a compound of Formula (I), (I'), (Ia), (Ia'), (Ib), (Ib'), (Ic), (Ic'), (II), (II'), (III), or (III'), $R^{20d}$ is $C_{2-9}$heterocycloalkyl optionally substituted with one isopropyl. In embodiments of a compound of Formula (I), (I'), (Ia), (Ia'), (Ib), (Ib'), (Ic), (Ic'), (II), (II'), (III), or (III'), $R^{20d}$ is $C_{2-9}$heterocycloalkyl optionally substituted with one butyl. In embodiments of a compound of Formula (I), (I'), (Ia), (Ia'), (Ib), (Ib'), (Ic), (Ic'), (II), (II'), (III), or (III'), $R^{20d}$ is $C_{2-9}$heterocycloalkyl optionally substituted with one tert-butyl.

In embodiments of a compound of Formula (I), (I'), (Ia), (Ia'), (Ib), (Ib'), (Ic), (Ic'), (II), (II'), (III), or (III'), $R^{20d}$ is $C_{5-9}$heterocycloalkyl optionally substituted with one, two, or three groups independently selected from $C_{1-6}$alkyl, $C_{1-6}$haloalkyl, $C_{1-6}$alkoxy, and $C_{1-6}$haloalkoxy. In embodiments of a compound of Formula (I), (I'), (Ia), (Ia'), (Ib), (Ib'), (Ic), (Ic'), (II), (II'), (III), or (III'), $R^{20d}$ is $C_{5-9}$heterocycloalkyl optionally substituted with one, two, or three groups independently selected from $C_{1-4}$ alkyl, $C_{1-4}$haloalkyl, $C_{1-4}$alkoxy, and $C_{1-4}$haloalkoxy. In embodiments of a compound of Formula (I), (I'), (Ia), (Ia'), (Ib), (Ib'), (Ic), (Ic'), (II), (II'), (III), or (III'), $R^{20d}$ is $C_{5-9}$heterocycloalkyl optionally substituted with one, two, or three groups independently selected from $C_{1-3}$alkyl, $C_{1-3}$haloalkyl, $C_{1-3}$alkoxy, and $C_{1-3}$haloalkoxy. In embodiments of a compound of Formula (I), (I'), (Ia), (Ia'), (Ib), (Ib'), (Ic), (Ic'), (II), (II'), (III), or (III'), $R^{20d}$ is $C_{5-9}$heterocycloalkyl optionally substituted with one $C_{1-6}$alkyl or one $C_{1-6}$haloalkyl. In embodiments of a compound of Formula (I), (I'), (Ia), (Ia'), (Ib), (Ib'), (Ic), (Ic'), (II), (II'), (III), or (III'), $R^{20d}$ is $C_{5-9}$heterocycloalkyl optionally substituted with one $C_{1-3}$alkyl or one $C_{1-3}$haloalkyl. In embodiments of a compound of Formula (I), (I'), (Ia), (Ia'), (Ib), (Ib'), (Ic), (Ic'), (II), (II'), (III), or (III'), $R^{20d}$ is $C_{5-9}$heterocycloalkyl optionally substituted with one $C_{1-6}$alkyl. In embodiments of a compound of Formula (I), (I'), (Ia), (Ia'), (Ib), (Ib'), (Ic), (Ic'), (II), (II'), (III), or (III'), $R^{20d}$ is $C_{5-9}$heterocycloalkyl optionally substituted with one $C_{1-3}$alkyl. In embodiments of a compound of Formula (I), (I'), (Ia), (Ia'), (Ib), (Ib'), (Ic), (Ic'), (II), (II'), (III), or (III'), $R^{20d}$ is $C_{5-9}$heterocycloalkyl optionally substituted with one methyl. In embodiments of a compound of Formula (I), (I'), (Ia), (Ia'), (Ib), (Ib'), (Ic), (Ic'), (II), (II'), (III), or (III'), $R^{20d}$ is $C_{5-9}$heterocycloalkyl optionally substituted with one ethyl. In embodiments of a compound of Formula (I), (I'), (Ia), (Ia'), (Ib), (Ib'), (Ic), (Ic'), (II), (II'), (III), or (III'), $R^{20d}$ is $C_{5-9}$heterocycloalkyl optionally substituted with one propyl. In embodiments of a compound of Formula (I), (I'), (Ia), (Ia'), (Ib), (Ib'), (Ic), (Ic'), (II), (II'), (III), or (III'), $R^{20d}$ is $C_{5-9}$heterocycloalkyl optionally substituted with one isopropyl. In embodiments of a compound of Formula (I), (I'), (Ia), (Ia'), (Ib), (Ib'), (Ic), (Ic'), (II), (II'), (III), or (III'), $R^{20d}$ is $C_{5-9}$heterocycloalkyl optionally substituted with one butyl. In embodiments of a compound of Formula (I), (I'), (Ia), (Ia'), (Ib), (Ib'), (Ic), (Ic'), (II), (II'), (III), or (III'), $R^{20d}$ is $C_{5-9}$heterocycloalkyl optionally substituted with one tert-butyl.

In embodiments of a compound of Formula (I), (I'), (Ia), (Ia'), (Ib), (Ib'), (Ic), (Ic'), (II), (II'), (III), or (III'), $R^{20d}$ is $C_{2-6}$heterocycloalkyl optionally substituted with one, two, or three groups independently selected from $C_{1-6}$alkyl, $C_{1-6}$haloalkyl, $C_{1-6}$alkoxy, and $C_{1-6}$haloalkoxy. In embodiments of a compound of Formula (I), (I'), (Ia), (Ia'), (Ib), (Ib'), (Ic), (Ic'), (II), (II'), (III), or (III'), $R^{20d}$ is $C_{2-6}$heterocycloalkyl optionally substituted with one, two, or three groups independently selected from $C_{1-4}$ alkyl, $C_{1-4}$haloalkyl, $C_{1-4}$alkoxy, and $C_{1-4}$haloalkoxy. In embodiments of a compound of Formula (I), (I'), (Ia), (Ia'), (Ib), (Ib'), (Ic), (Ic'), (II), (II'), (III), or (III'), $R^{20d}$ is $C_{2-6}$heterocycloalkyl optionally substituted with one, two, or three groups independently selected from $C_{1-3}$alkyl, $C_{1-3}$haloalkyl, $C_{1-3}$alkoxy, and $C_{1-3}$haloalkoxy. In embodiments of a compound of Formula (I), (I'), (Ia), (Ia'), (Ib), (Ib'), (Ic), (Ic'), (II), (II'), (III), or (III'), $R^{20d}$ is $C_{2-6}$heterocycloalkyl optionally substituted with one $C_{1-6}$alkyl or one $C_{1-6}$haloalkyl. In embodiments of a compound of Formula (I), (I'), (Ia), (Ia'), (Ib), (Ib'), (Ic), (Ic'), (II), (II'), (III), or (III'), $R^{20d}$ is $C_{2-6}$heterocycloalkyl optionally substituted with one $C_{1-3}$alkyl or one $C_{1-3}$haloalkyl. In embodiments of a compound of Formula (I), (I'), (Ia), (Ia'), (Ib), (Ib'), (Ic), (Ic'), (II), (II'), (III), or (III'), $R^{20d}$ is $C_{2-6}$heterocycloalkyl optionally substituted with one $C_{1-6}$alkyl. In embodiments of a compound of Formula (I), (I'), (Ia), (Ia'), (Ib), (Ib'), (Ic), (Ic'), (II), (II'), (III), or (III'), $R^{20d}$ is $C_{2-6}$heterocycloalkyl optionally substituted with one $C_{1-3}$alkyl. In embodiments of a compound of Formula (I), (I'), (Ia), (Ia'), (Ib), (Ib'), (Ic), (Ic'), (II), (II'), (III), or (III'), $R^{20d}$ is $C_{2-6}$heterocycloalkyl optionally substituted with one methyl. In embodiments of a compound of Formula (I), (I'), (Ia), (Ia'), (Ib), (Ib'), (Ic), (Ic'), (II), (II'), (III), or (III'), $R^{20d}$ is $C_{2-6}$heterocycloalkyl optionally substituted with one ethyl. In embodiments of a compound of Formula (I), (I'), (Ia), (Ia'), (Ib), (Ib'), (Ic), (Ic'), (II), (II'), (III), or (III'), $R^{20d}$ is $C_{2-6}$heterocycloalkyl optionally substituted with one propyl. In embodiments of a compound of Formula (I), (I'), (Ia), (Ia'), (Ib), (Ib'), (Ic), (Ic'), (II), (II'), (III), or (III'), $R^{20d}$ is $C_{2-6}$heterocycloalkyl optionally substituted with one isopropyl. In embodiments of a compound of Formula (I), (I'), (Ia), (Ia'), (Ib), (Ib'), (Ic), (Ic'), (II), (II'), (III), or (III'), $R^{20d}$ is $C_{2-6}$heterocycloalkyl optionally substituted with one butyl. In embodiments of a compound of Formula (I), (I'), (Ia), (Ia'), (Ib), (Ib'), (Ic), (Ic'), (II), (II'), (III), or (III'), $R^{20d}$ is $C_{2-6}$heterocycloalkyl optionally substituted with one tert-butyl.

In embodiments of a compound of Formula (I), (I'), (Ia), (Ia'), (Ib), (Ib'), (Ic), (Ic'), (II), (II'), (III), or (III'), $R^{20d}$ is $C_{4-5}$heterocycloalkyl optionally substituted with one, two, or three groups independently selected from $C_{1-6}$alkyl, $C_{1-6}$haloalkyl, $C_{1-6}$alkoxy, and $C_{1-6}$haloalkoxy. In embodiments of a compound of Formula (I), (I'), (Ia), (Ia'), (Ib), (Ib'), (Ic), (Ic'), (II), (II'), (III), or (III'), $R^{20d}$ is $C_{4-5}$heterocycloalkyl optionally substituted with one, two, or three groups independently selected from $C_{1-4}$ alkyl, $C_{1-4}$haloalkyl, $C_{1-4}$alkoxy, and $C_{1-4}$haloalkoxy. In embodiments of a compound of Formula (I), (I'), (Ia), (Ia'), (Ib), (Ib'), (Ic), (Ic'), (II), (II'), (III), or (III'), $R^{20d}$ is $C_{4-5}$heterocycloalkyl optionally substituted with one, two, or three groups independently selected from $C_{1-3}$alkyl, $C_{1-3}$haloalkyl, $C_{1-3}$alkoxy, and $C_{1-3}$haloalkoxy. In embodiments of a compound of Formula (I), (I'), (Ia), (Ia'), (Ib), (Ib'), (Ic), (Ic'), (II), (II'), (III), or (III'), $R^{20d}$ is $C_{4-5}$heterocycloalkyl optionally substituted with one $C_{1-6}$alkyl or one $C_{1-6}$haloalkyl. In embodiments of a compound of Formula (I), (I'), (Ia), (Ia'), (Ib), (Ib'), (Ic), (Ic'), (II), (II'), (III), or (III'), $R^{20d}$ is $C_{4-5}$heterocycloalkyl optionally substituted with one $C_{1-3}$alkyl or one $C_{1-3}$haloalkyl. In embodiments of a compound of Formula (I), (I'), (Ia), (Ia'), (Ib), (Ib'), (Ic), (Ic'), (II), (II'), (III), or (III'), $R^{20d}$ is $C_{4-5}$heterocycloalkyl optionally substituted with one $C_{1-6}$alkyl. In embodiments of a compound of Formula (I), (I'), (Ia), (Ia'), (Ib), (Ib'), (Ic), (Ic'), (II), (II'), (III), or (III'), $R^{20d}$ is $C_{4-5}$heterocycloalkyl optionally substituted with one $C_{1-3}$alkyl. In embodiments of a compound of Formula (I), (I'), (Ia), (Ia'), (Ib), (Ib'), (Ic), (Ic'), (II), (II'), (III), or (III'), $R^{20d}$ $C_{4-5}$heterocycloalkyl optionally substituted with one methyl. In embodiments of a compound of Formula (I), (I'), (Ia), (Ia'), (Ib), (Ib'), (Ic), (Ic'), (II), (II'), (III), or (III'), $R^{20d}$ is $C_{4-5}$heterocycloalkyl optionally substituted with one ethyl. In embodiments of a compound of Formula (I), (I'), (Ia), (Ia'), (Ib), (Ib'), (Ic), (Ic'), (II), (II'), (III), or (III'), $R^{20d}$ is $C_{4-5}$heterocycloalkyl optionally substituted with one propyl. In embodiments of a compound of Formula (I), (I'), (Ia), (Ia'), (Ib), (Ib'), (Ic), (Ic'), (II), (II'), (III), or (III'), $R^{20d}$ is $C_{4-5}$heterocycloalkyl optionally substituted with one isopropyl. In embodiments of a compound of Formula (I), (I'), (Ia), (Ia'), (Ib), (Ib'), (Ic), (Ic'), (II), (II'), (III), or (III'), $R^{20d}$ is $C_{4-5}$heterocycloalkyl optionally substituted with one butyl. In embodiments of a compound of Formula (I), (I'), (Ia), (Ia'), (Ib), (Ib'), (Ic), (Ic'), (II), (II'), (III), or (III'), $R^{20d}$ is $C_{4-5}$heterocycloalkyl optionally substituted with one tert-butyl.

In embodiments of a compound of Formula (I), (I'), (Ia), (Ia'), (Ib), (Ib'), (Ic), (Ic'), (II), (II'), (III), or (III'), $R^{20d}$ is pyrrolidinyl optionally substituted with one, two, or three groups independently selected from $C_{1-6}$alkyl, $C_{1-6}$haloalkyl, $C_{1-6}$alkoxy, and $C_{1-6}$haloalkoxy. In embodiments of a compound of Formula (I), (I'), (Ia), (Ia'), (Ib), (Ib'), (Ic), (Ic'), (II), (II'), (III), or (III'), $R^{20d}$ is pyrrolidinyl optionally substituted with one, two, or three groups independently selected from $C_{1-4}$alkyl, $C_{1-4}$haloalkyl, $C_{1-4}$alkoxy, and $C_{1-4}$haloalkoxy. In embodiments of a compound of Formula (I), (I'), (Ia), (Ia'), (Ib), (Ib'), (Ic), (Ic'), (II), (II'), (III), or (III'), $R^{20d}$ is pyrrolidinyl optionally substituted with one, two, or three groups independently selected from $C_{1-3}$alkyl, $C_{1-3}$haloalkyl, $C_{1-3}$alkoxy, and $C_{1-3}$haloalkoxy. In embodiments of a compound of Formula (I), (I'), (Ia), (Ia'), (Ib), (Ib'), (Ic), (Ic'), (II), (II'), (III), or (III'), $R^{20d}$ is pyrrolidinyl optionally substituted with one $C_{1-6}$alkyl or one $C_{1-6}$haloalkyl. In embodiments of a compound of Formula (I), (I'), (Ia), (Ia'), (Ib), (Ib'), (Ic), (Ic'), (II), (II'), (III), or (III'), $R^{20d}$ is pyrrolidinyl optionally substituted with one $C_{1-3}$alkyl or one $C_{1-3}$haloalkyl. In embodiments of a compound of Formula (I), (I'), (Ia), (Ia'), (Ib), (Ib'), (Ic), (Ic'), (II), (II'), (III), or (III'), $R^{20d}$ is pyrrolidinyl optionally substituted with one $C_{1-6}$alkyl. In embodiments of a compound of Formula (I), (I'), (Ia), (Ia'), (Ib), (Ib'), (Ic), (Ic'), (II), (II'), (III), or (III'), $R^{20d}$ is pyrrolidinyl optionally substituted with one $C_{1-3}$alkyl. In embodiments of a compound of Formula (I), (I'), (Ia), (Ia'), (Ib), (Ib'), (Ic), (Ic'), (II), (II'), (III), or (III'), $R^{20d}$ pyrrolidinyl optionally substituted with one methyl. In embodiments of a compound of Formula (I), (I'), (Ia), (Ia'), (Ib), (Ib'), (Ic), (Ic'), (II), (II'), (III), or (III'), $R^{20d}$ is pyrrolidinyl optionally substituted with one ethyl. In embodiments of a compound of Formula (I), (I'), (Ia), (Ia'), (Ib), (Ib'), (Ic), (Ic'), (II), (II'), (III), or (III'), $R^{20d}$ is pyrrolidinyl optionally substituted with one propyl. In embodiments of a compound of Formula (I), (I'), (Ia), (Ia'), (Ib), (Ib'), (Ic), (Ic'), (II), (II'), (III), or (III'), $R^{20d}$ is pyrrolidinyl optionally substituted with one isopropyl. In embodiments of a compound of Formula (I), (I'), (Ia), (Ia'), (Ib), (Ib'), (Ic), (Ic'), (II), (II'), (III), or (III'), $R^{20d}$ is pyrrolidinyl optionally substituted with one butyl. In embodiments of a compound of Formula (I), (I'), (Ia), (Ia'), (Ib), (Ib'), (Ic), (Ic'), (II), (II'), (III), or (III'), $R^{20d}$ is pyrrolidinyl optionally substituted with one tert-butyl.

In embodiments of a compound of Formula (I), (I'), (Ia), (Ia'), (Ib), (Ib'), (Ic), (Ic'), (II), (II'), (III), or (III'), $R^{20d}$ is piperidinyl optionally substituted with one, two, or three groups independently selected from $C_{1-6}$alkyl, $C_{1-6}$haloalkyl, $C_{1-6}$ alkoxy, and $C_{1-6}$haloalkoxy. In embodiments of a compound of Formula (I), (I'), (Ia), (Ia'), (Ib), (Ib'), (Ic), (Ic'), (II), (II'), (III), or (III'), $R^{20d}$ is piperidinyl optionally substituted with one, two, or three groups independently selected from $C_{1-4}$alkyl, $C_{1-4}$haloalkyl, $C_{1-4}$ alkoxy, and $C_{1-4}$haloalkoxy. In embodiments of a compound of Formula (I), (I'), (Ia), (Ia'), (Ib), (Ib'), (Ic), (Ic'), (II), (II'), (III), or (III'), $R^{20d}$ is piperidinyl optionally substituted with one, two, or three groups independently selected from $C_{1-3}$alkyl, $C_{1-3}$haloalkyl, $C_{1-3}$ alkoxy, and $C_{1-3}$haloalkoxy. In embodiments of a compound of Formula (I), (I'), (Ia), (Ia'), (Ib), (Ib'), (Ic), (Ic'), (II), (II'), (III), or (III'), $R^{20d}$ is piperidinyl optionally substituted with one $C_{1-6}$alkyl or one $C_{1-6}$haloalkyl. In embodiments of a compound of Formula (I), (I'), (Ia), (Ia'), (Ib), (Ib'), (Ic), (Ic'), (II), (II'), (III), or (III'), $R^{20d}$ is piperidinyl optionally substituted with one $C_{1-3}$alkyl or one $C_{1-3}$ haloalkyl. In embodiments of a compound of Formula (I), (I'), (Ia), (Ia'), (Ib), (Ib'), (Ic), (Ic'), (II), (II'), (III), or (III'), $R^{20d}$ is piperidinyl optionally substituted with one $C_{1-6}$alkyl. In embodiments of a compound of Formula (I), (I'), (Ia), (Ia'), (Ib), (Ib'), (Ic), (Ic'), (II), (II'), (III), or (III'), $R^{20d}$ is piperidinyl optionally substituted with one $C_{1-3}$alkyl. In embodiments of a compound of Formula (I), (I'), (Ia), (Ia'), (Ib), (Ib'), (Ic), (Ic'), (II), (II'), (III), or (III'), $R^{20d}$ piperidinyl optionally substituted with one methyl. In embodiments of a compound of Formula (I), (I'), (Ia), (Ia'), (Ib), (Ib'), (Ic), (Ic'), (II), (II'), (III), or (III'), $R^{20d}$ is piperidinyl optionally substituted with one ethyl. In embodiments of a compound of Formula (I), (I'), (Ia), (Ia'), (Ib), (Ib'), (Ic), (Ic'), (II), (II'), (III), or (III'), $R^{20d}$ is piperidinyl optionally substituted with one propyl. In embodiments of a compound of Formula (I), (I'), (Ia), (Ia'), (Ib), (Ib'), (Ic), (Ic'), (II), (II'), (III), or (III'), $R^{20d}$ is piperidinyl optionally substituted with one isopropyl. In embodiments of a compound of Formula (I), (I'), (Ia), (Ia'), (Ib), (Ib'), (Ic), (Ic'), (II), (II'), (III), or (III'), $R^{20d}$ is piperidinyl optionally substituted with one butyl. In embodiments of a compound of Formula (I), (I'), (Ia), (Ia'), (Ib), (Ib'), (Ic), (Ic'), (II), (II'), (III), or (III'), $R^{20d}$ is piperidinyl optionally substituted with one tert-butyl.

In embodiments of a compound of Formula (I), (I'), (Ia), (Ia'), (Ib), (Ib'), (Ic), (Ic'), (II), (II'), (III), or (III'), $R^{20d}$ is piperazinyl optionally substituted with one, two, or three groups independently selected from $C_{1-6}$alkyl, $C_{1-6}$haloalkyl, $C_{1-6}$ alkoxy, and $C_{1-6}$haloalkoxy. In embodiments of a compound of Formula (I), (I'), (Ia), (Ia'), (Ib), (Ib'), (Ic), (Ic'), (II), (II'), (III), or (III'), $R^{20d}$ is piperazinyl optionally substituted with one, two, or three groups independently selected from $C_{1-4}$alkyl, $C_{1-4}$haloalkyl, $C_{1-4}$ alkoxy, and $C_{1-4}$haloalkoxy. In embodiments of a compound of Formula (I), (I'), (Ia), (Ia'), (Ib), (Ib'), (Ic), (Ic'), (II), (II'), (III), or (III'), $R^{20d}$ is piperazinyl optionally substituted with one, two, or three groups independently selected from $C_{1-3}$alkyl, $C_{1-3}$haloalkyl, $C_{1-3}$ alkoxy, and $C_{1-3}$haloalkoxy. In embodiments of a compound of Formula (I), (I'), (Ia), (Ia'), (Ib), (Ib'), (Ic), (Ic'), (II), (II'), (III), or (III'), $R^{20d}$ is piperazinyl optionally substituted with one $C_{1-6}$alkyl or one $C_{1-6}$haloalkyl. In embodiments of a compound of Formula (I), (I'), (Ia), (Ia'), (Ib), (Ib'), (Ic), (Ic'), (II), (II'), (III), or (III'), $R^{20d}$ is piperazinyl optionally substituted with one $C_{1-3}$alkyl or one $C_{1-3}$ haloalkyl. In embodiments of a compound of Formula (I), (I'), (Ia), (Ia'), (Ib), (Ib'), (Ic), (Ic'), (II), (II'), (III), or (III'), $R^{20d}$ is piperazinyl optionally substituted with one $C_{1-6}$alkyl. In embodiments of a compound of Formula (I), (I'), (Ia), (Ia'), (Ib), (Ib'), (Ic), (Ic'), (II), (II'), (III), or (III'), $R^{20d}$ is piperazinyl optionally substituted with one $C_{1-3}$alkyl. In embodiments of a compound of Formula (I), (I'), (Ia), (Ia'), (Ib), (Ib'), (Ic), (Ic'), (II), (II'), (III), or (III'), $R^{20d}$ piperazinyl optionally substituted with one methyl. In embodiments of a compound of Formula (I), (I'), (Ia), (Ia'), (Ib), (Ib'), (Ic), (Ic'), (II), (II'), (III), or (III'), $R^{20d}$ is piperidinyl optionally substituted with one ethyl. In embodiments of a compound of Formula (I), (I'), (Ia), (Ia'), (Ib), (Ib'), (Ic), (Ic'), (II), (II'), (III), or (III'), $R^{20d}$ is piperazinyl optionally substituted with one propyl. In embodiments of a compound of Formula (I), (I'), (Ia), (Ia'), (Ib), (Ib'), (Ic), (Ic'), (II), (II'), (III), or (III'), $R^{20d}$ is piperazinyl optionally substituted with one isopropyl. In embodiments of a compound of Formula (I), (I'), (Ia), (Ia'), (Ib), (Ib'), (Ic), (Ic'), (II), (II'), (III), or (III'), $R^{20d}$ is piperidinyl optionally substituted with one butyl. In embodiments of a compound of Formula (I), (I'), (Ia), (Ia'), (Ib), (Ib'), (Ic), (Ic'), (II), (II'), (III), or (III'), $R^{20d}$ is piperazinyl optionally substituted with one tert-butyl.

In some embodiments is a compound of Formula (I), (I'), (Ia), (Ia'), (Ib), (Ib'), (Ic), (Ic'), (II), (II'), (III), or (III'), wherein $R^1$ is

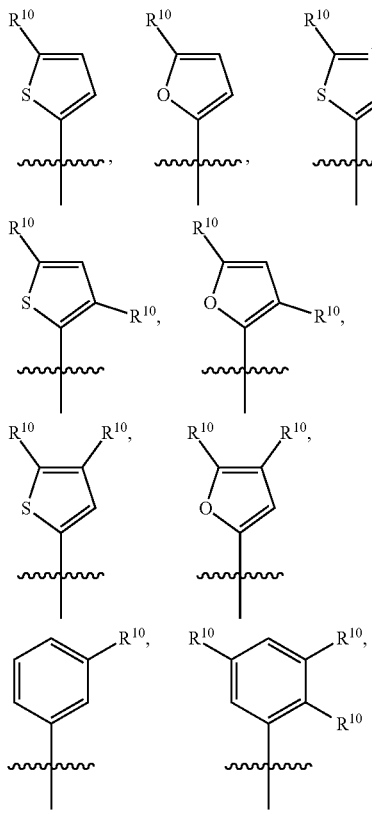

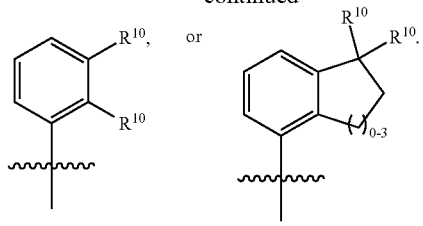

In some embodiments is a compound of Formula (I), (I'), (Ia), (Ia'), (Ib), (Ib'), (Ic), (Ic'), (II), (II'), (III), or (III'), wherein $R^1$ is

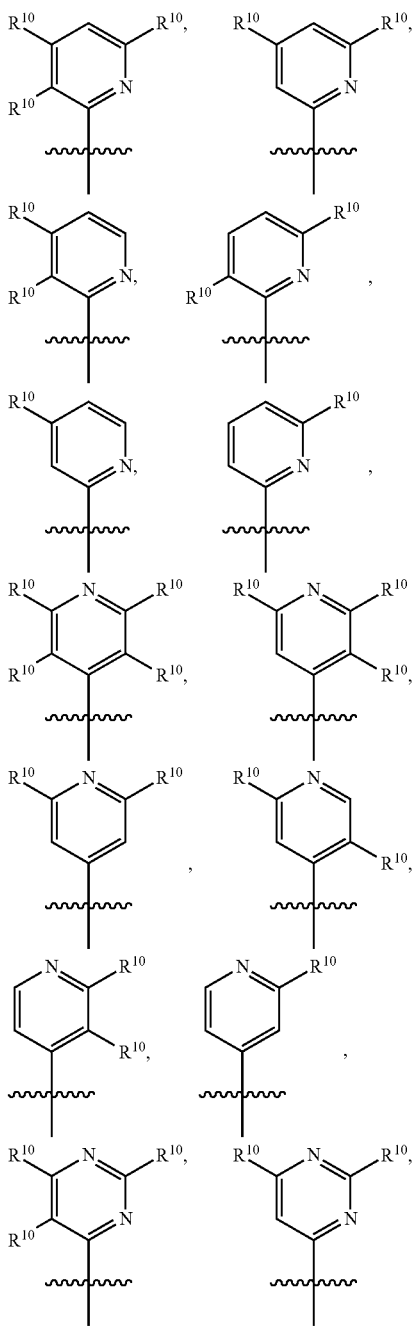

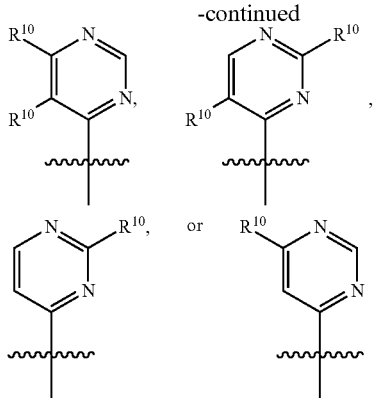

In some embodiments is a compound of Formula (I), (I'), (Ia), (Ia'), (Ib), (Ib'), (Ic), (Ic'), (II), (II'), (III), or (III'), wherein R¹ is

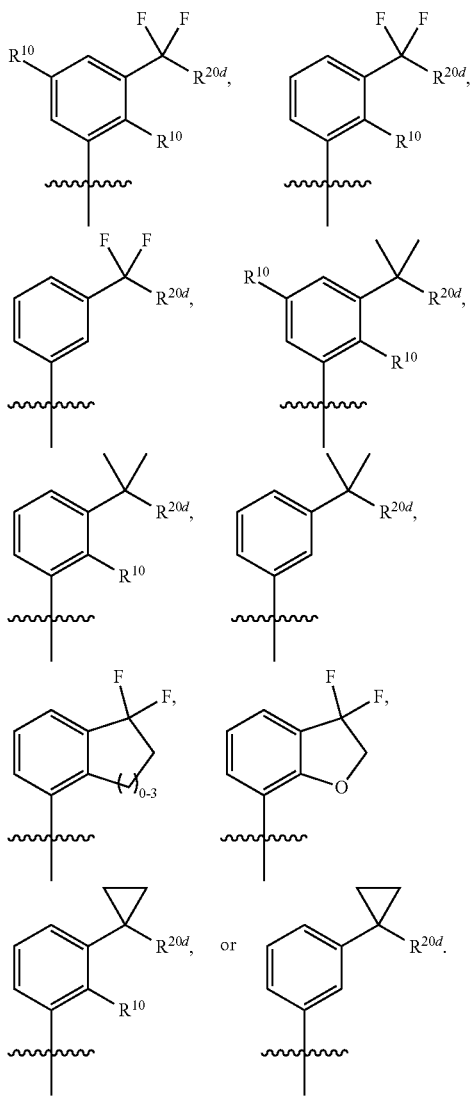

In some embodiments of a compound of Formula (I), (I'), (Ia), (Ia'), (Ib), (Ib'), (Ic), (Ic'), (II), (II'), (III), or (III'), R¹ is

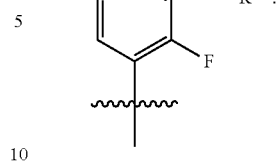

In some embodiments of a compound of Formula (I), (I'), (Ia), (Ia'), (Ib), (Ib'), (Ic), (Ic'), (II), (II'), (III), or (III'), R¹ is

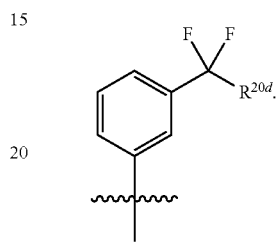

In some embodiments of a compound of Formula (I), (I'), (Ia), (Ia'), (Ib), (Ib'), (Ic), (Ic'), (II), (II'), (III), or (III'), R¹ is

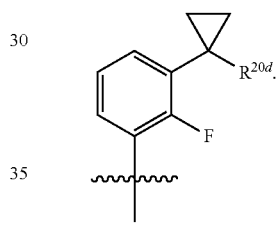

In some embodiments of a compound of Formula (I), (I'), (Ia), (Ia'), (Ib), (Ib'), (Ic), (Ic'), (II), (II'), (III), or (III'), R¹ is

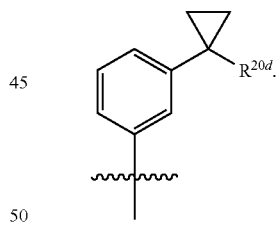

In some embodiments of a compound of Formula (I), (I'), (Ia), (Ia'), (Ib), (Ib'), (Ic), (Ic'), (II), (II'), (III), or (III'), R¹ is

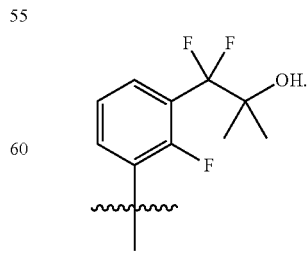

In some embodiments of a compound of Formula (I), (I'), (Ia), (Ia'), (Ib), (Ib'), (Ic), (Ic'), (II), (II'), (III), or (III'), R¹ is

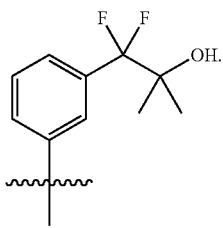 [SMILES: *c1cccc(C(F)(F)C(C)(C)O)c1]

In some embodiments of a compound of Formula (I), (I'), (Ia), (Ia'), (Ib), (Ib'), (Ic), (Ic'), (II), (II'), (III), or (III'), R¹ is


In some embodiments of a compound of Formula (I), (I'), (Ia), (Ia'), (Ib), (Ib'), (Ic), (Ic'), (II), (II'), (III), or (III'), R¹ is

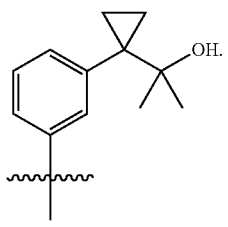 [SMILES: *c1cccc(C2(C(C)(C)O)CC2)c1]

In some embodiments of a compound of Formula (I), (I'), (Ia), (Ia'), (Ib), (Ib'), (Ic), (Ic'), (II), (II'), (III), or (III'), R¹ is

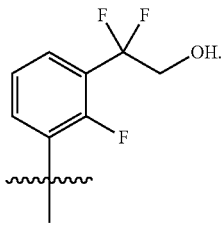 [SMILES: *c1cccc(C(F)(F)CO)c1F]

In some embodiments of a compound of Formula (I), (I'), (Ia), (Ia'), (Ib), (Ib'), (Ic), (Ic'), (II), (II'), (III), or (III'), R¹ is

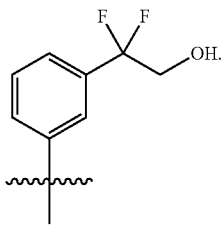 [SMILES: *c1cccc(C(F)(F)CO)c1]

In some embodiments of a compound of Formula (I), (I'), (Ia), (Ia'), (Ib), (Ib'), (Ic), (Ic'), (II), (II'), (III), or (III'), R¹ is

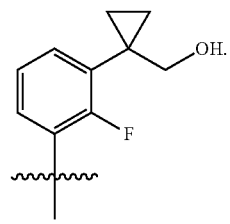 [SMILES: *c1cccc(C2(CO)CC2)c1F]

In some embodiments of a compound of Formula (I), (I'), (Ia), (Ia'), (Ib), (Ib'), (Ic), (Ic'), (II), (II'), (III), or (III'), R¹ is


In some embodiments of a compound of Formula (I), (I'), (Ia), (Ia'), (Ib), (Ib'), (Ic), (Ic'), (II), (II'), (III), or (III'), R¹ is


In some embodiments of a compound of Formula (I), (I'), (Ia), (Ia'), (Ib), (Ib'), (Ic), (Ic'), (II), (II'), (III), or (III'), R¹ is

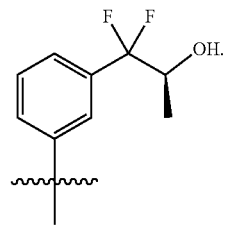 [SMILES: *c1cccc(C(F)(F)[C@H](C)O)c1]

In some embodiments of a compound of Formula (I), (I'), (Ia), (Ia'), (Ib), (Ib'), (Ic), (Ic'), (II), (II'), (III), or (III'), R¹ is

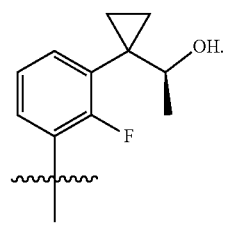 [SMILES: *c1cccc(C2([C@H](C)O)CC2)c1F]

In some embodiments of a compound of Formula (I), (I'), (Ia), (Ia'), (Ib), (Ib'), (Ic), (Ic'), (II), (II'), (III), or (III'), R¹ is

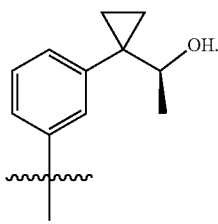

In some embodiments of a compound of Formula (I), (I'), (Ia), (Ia'), (Ib), (Ib'), (Ic), (Ic'), (II), (II'), (III), or (III'), R¹ is

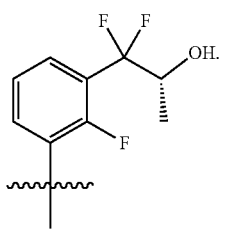 [SMILES: *c1cccc(C(F)(F)[C@@H](C)O)c1F]

In some embodiments of a compound of Formula (I), (I'), (Ia), (Ia'), (Ib), (Ib'), (Ic), (Ic'), (II), (II'), (III), or (III'), R¹ is

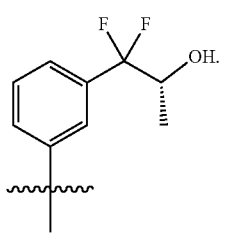 [SMILES: *c1cccc(C(F)(F)[C@@H](C)O)c1]

In some embodiments of a compound of Formula (I), (I'), (Ia), (Ia'), (Ib), (Ib'), (Ic), (Ic'), (II), (II'), (III), or (III'), R¹ is

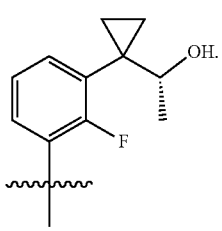 [SMILES: *c1cccc(C2([C@@H](C)O)CC2)c1F]

In some embodiments of a compound of Formula (I), (I'), (Ia), (Ia'), (Ib), (Ib'), (Ic), (Ic'), (II), (II'), (III), or (III'), R¹ is

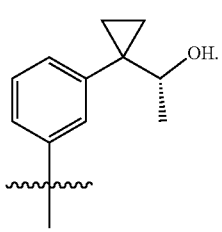 [SMILES: *c1cccc(C2([C@@H](C)O)CC2)c1]

In some embodiments of a compound of Formula (I), (I'), (Ia), (Ia'), (Ib), (Ib'), (Ic), (Ic'), (II), (II'), (III), or (III'), R¹ is

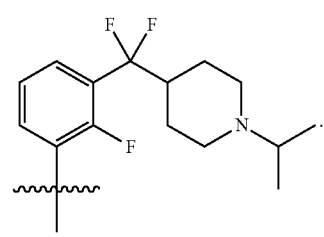 [SMILES: *c1cccc(C(F)(F)C2CCN(C(C)C)CC2)c1F]

In some embodiments of a compound of Formula (I), (I'), (Ia), (Ia'), (Ib), (Ib'), (Ic), (Ic'), (II), (II'), (III), or (III'), R¹ is

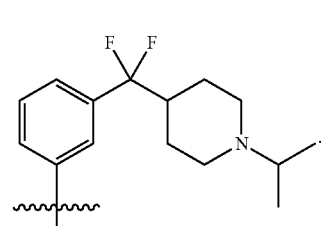

In some embodiments of a compound of Formula (I), (I'), (Ia), (Ia'), (Ib), (Ib'), (Ic), (Ic'), (II), (II'), (III), or (III'), R¹ is

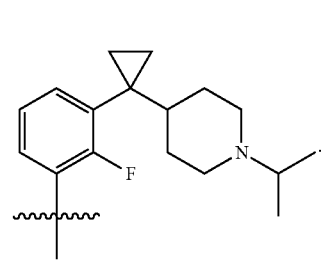 [SMILES: *c1cccc(C2(C3CCN(C(C)C)CC3)CC2)c1F]

In some embodiments of a compound of Formula (I), (I'), (Ia), (Ia'), (Ib), (Ib'), (Ic), (Ic'), (II), (II'), (III), or (III'), R¹ is

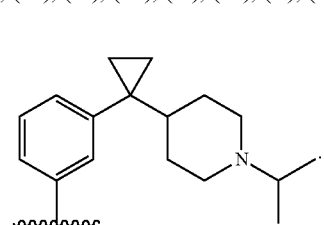

In some embodiments is a compound of Formula (I), (I'), (Ia), (Ia'), (Ib), (Ib'), (Ic), (Ic'), (II), (II'), (III), or (III'), wherein R¹ is


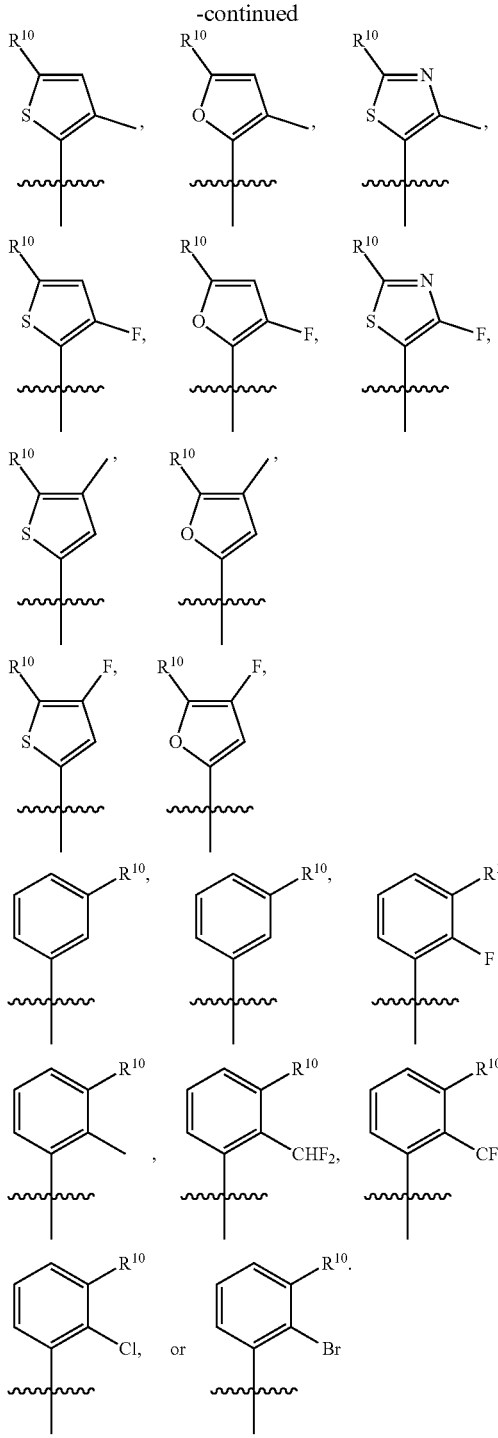
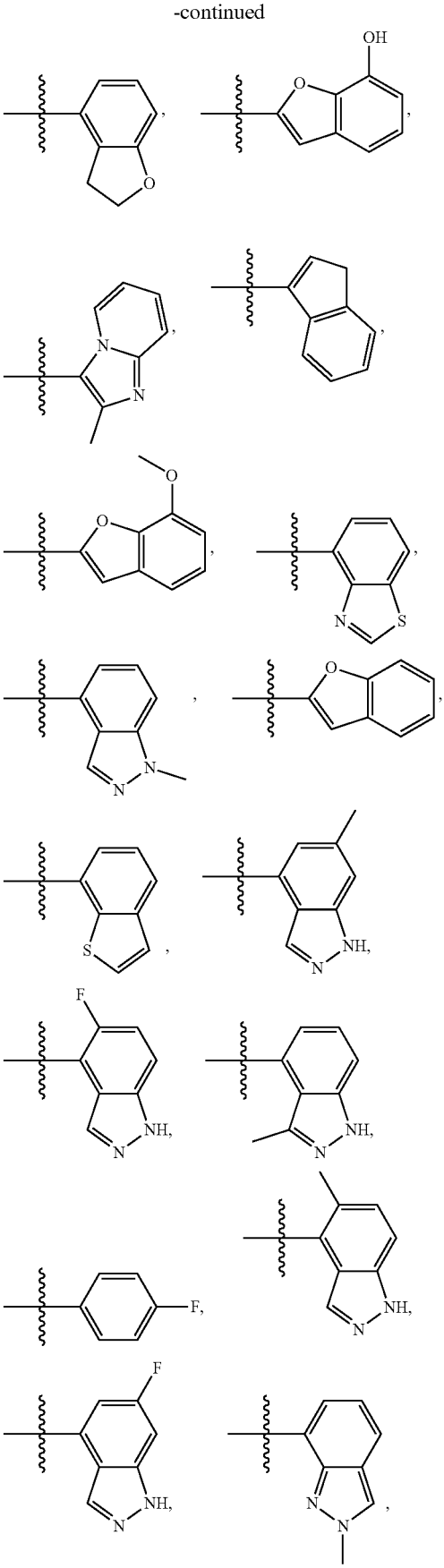
In some embodiments is a compound of Formula (I), (I'), (Ia), (Ia'), (Ib), (Ib'), (Ic), (Ic'), (II), (II'), (III), or (III'), wherein $R^1$ is

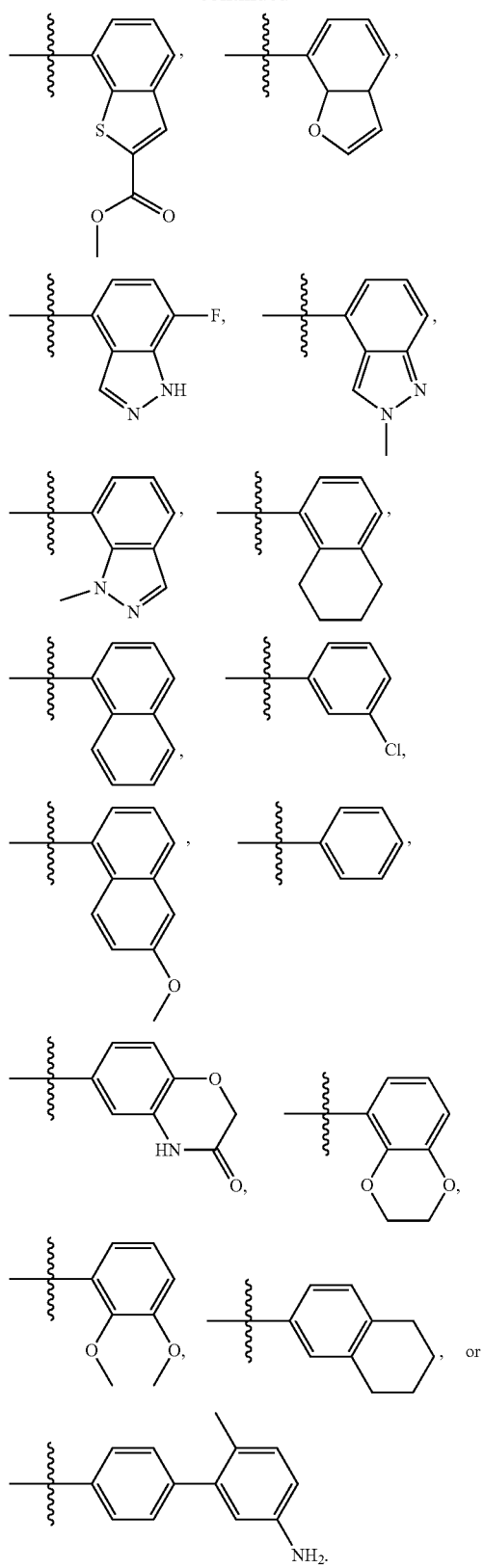
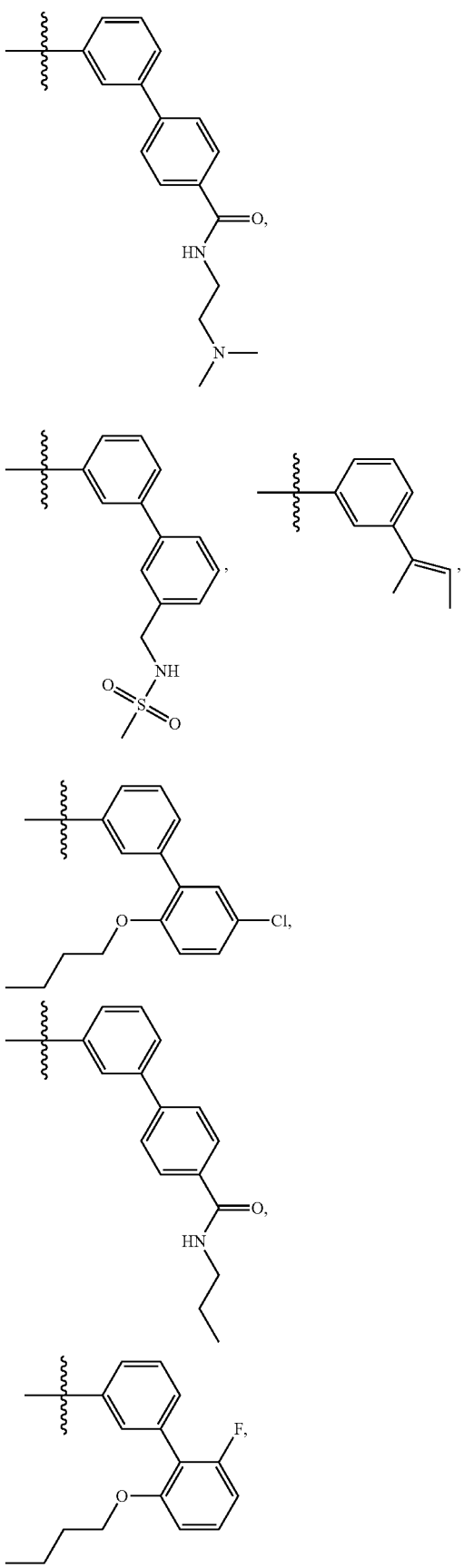
In some embodiments is a compound of Formula (I), (I'), (Ia), (Ia'), (Ib), (Ib'), (Ic), (Ic'), (II), (II'), (III), or (III'), wherein $R^1$ is

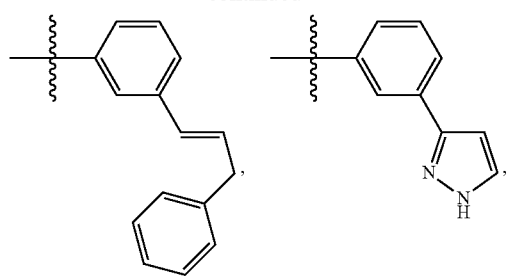
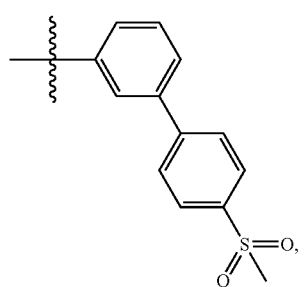
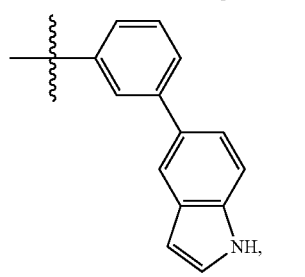
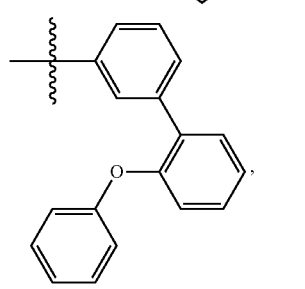
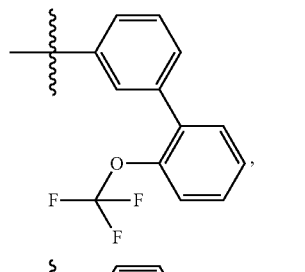
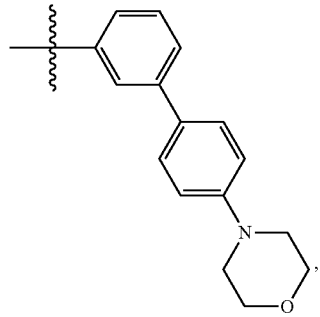
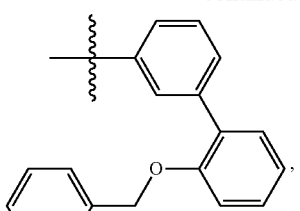
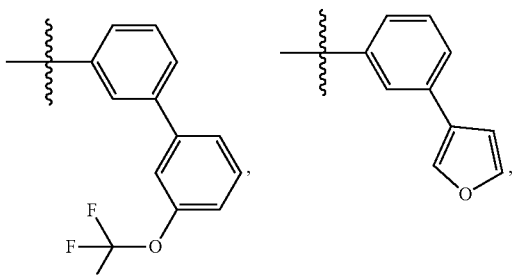
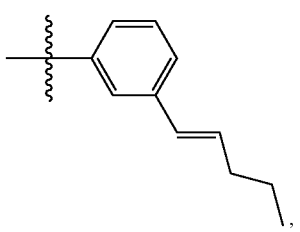
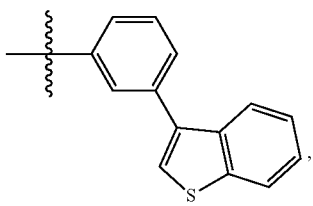
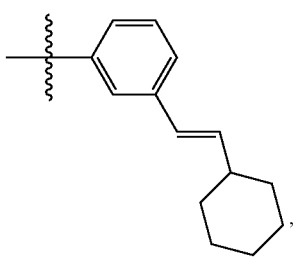
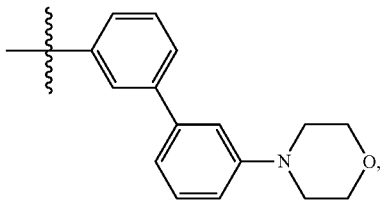
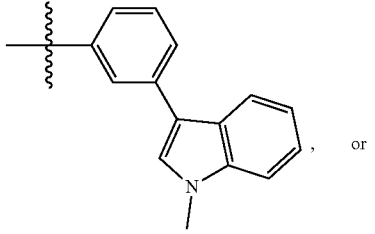, or

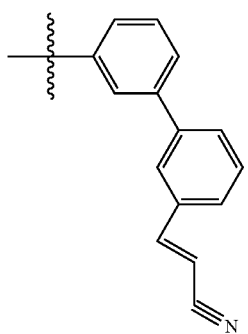
In some embodiments is a compound of Formula (I), (I'), (Ia), (Ia'), (Ib), (Ib'), (Ic), (Ic'), (II), (II'), (III), or (III'), wherein R¹ is
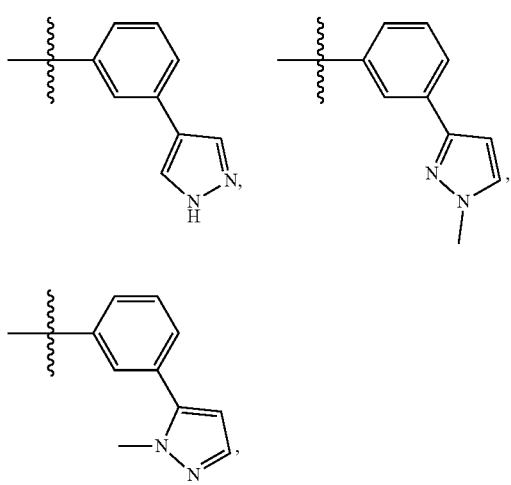
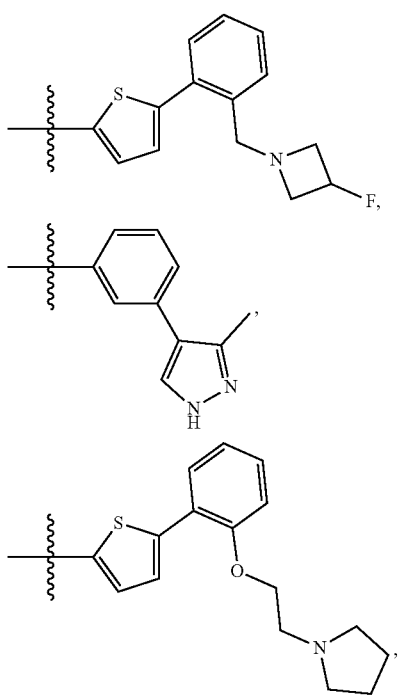
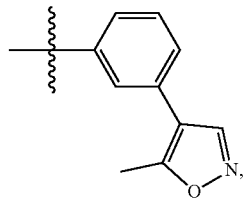
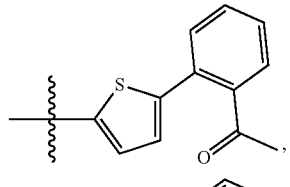
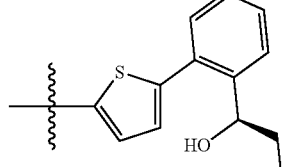
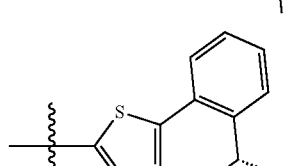
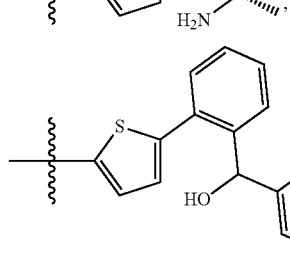
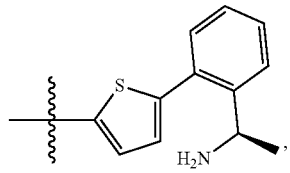
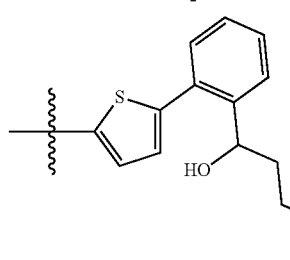
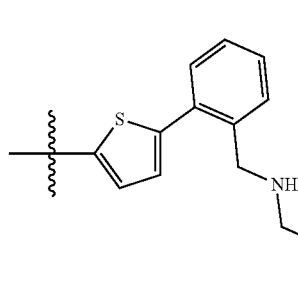

217
-continued
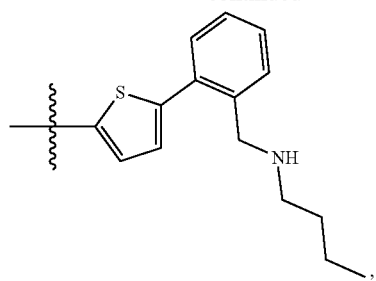
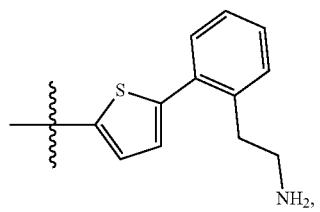
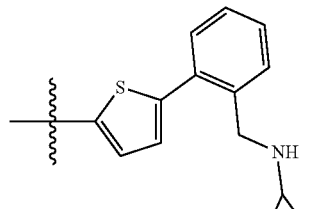
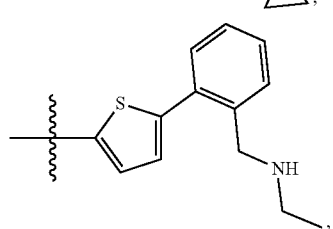
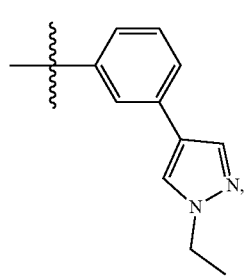
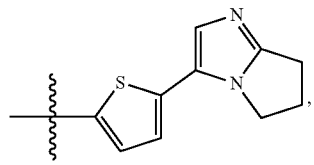
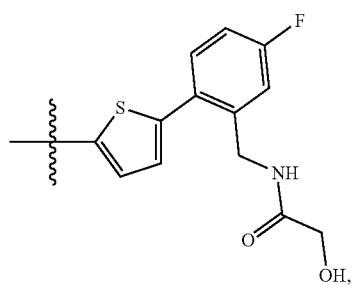
218
-continued
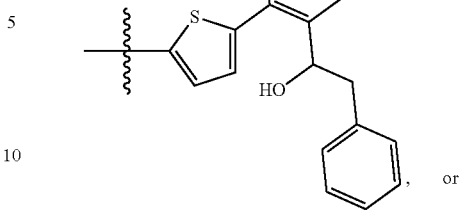, or
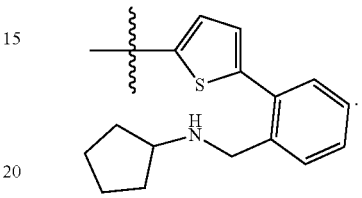.
In some embodiments is a compound of Formula (I), (I'), (Ia), (Ia'), (Ib), (Ib'), (Ic), (Ic'), (II), (II'), (III), or (III'), wherein $R^1$ is
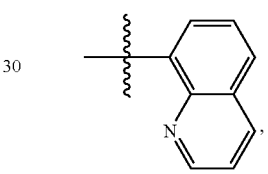,
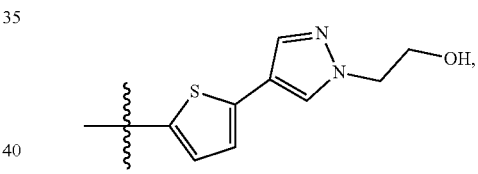,
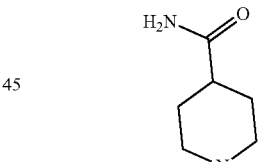,
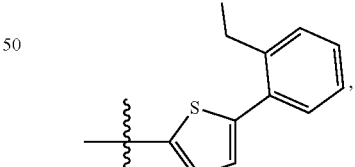,
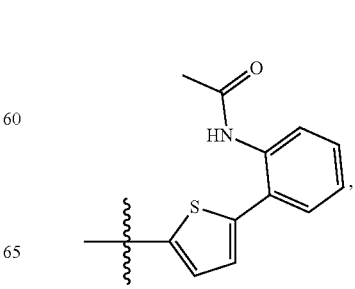, 219
-continued
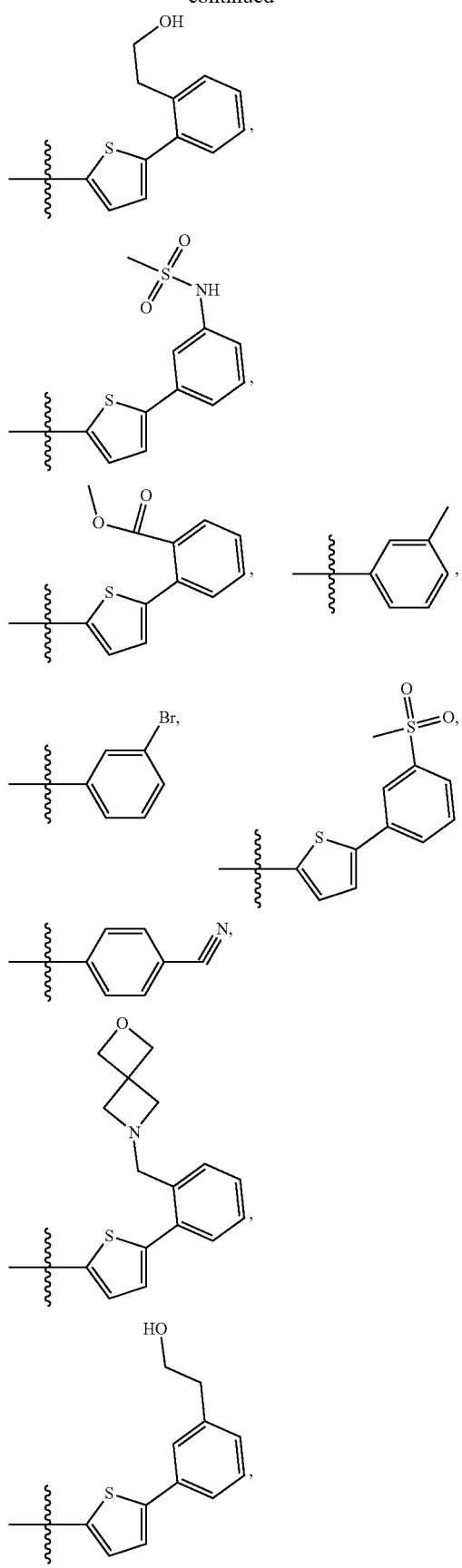
220
-continued
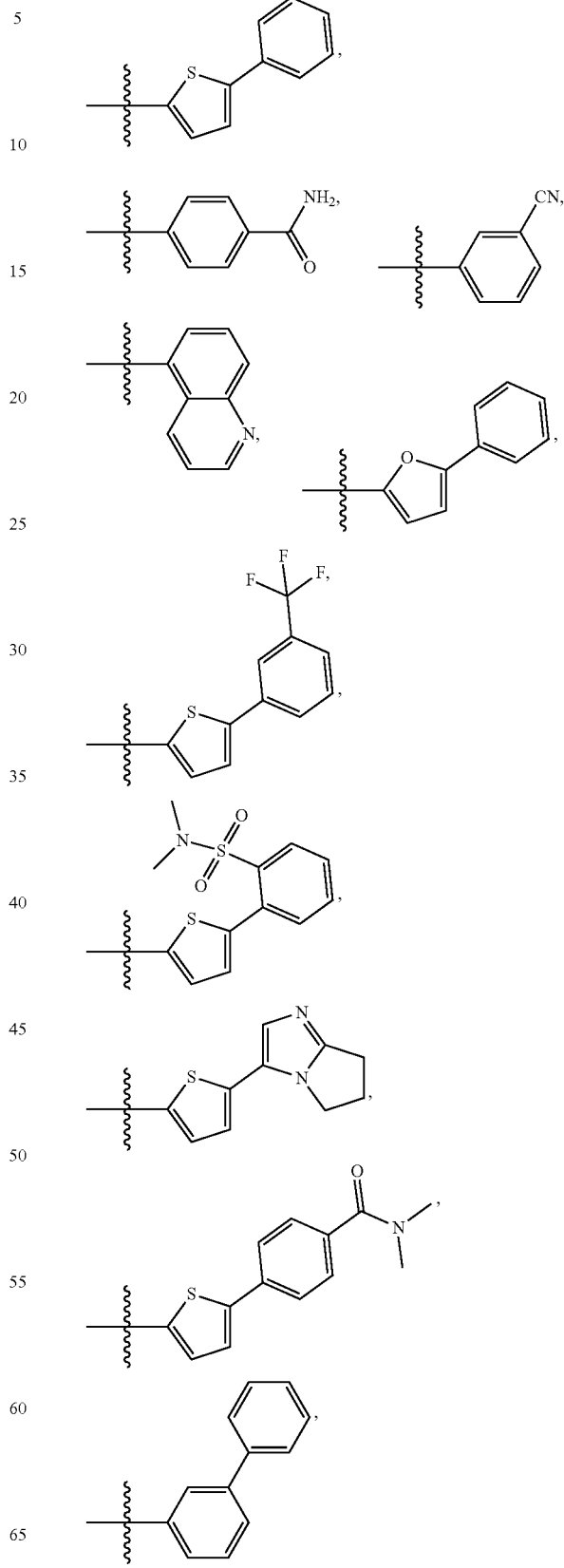

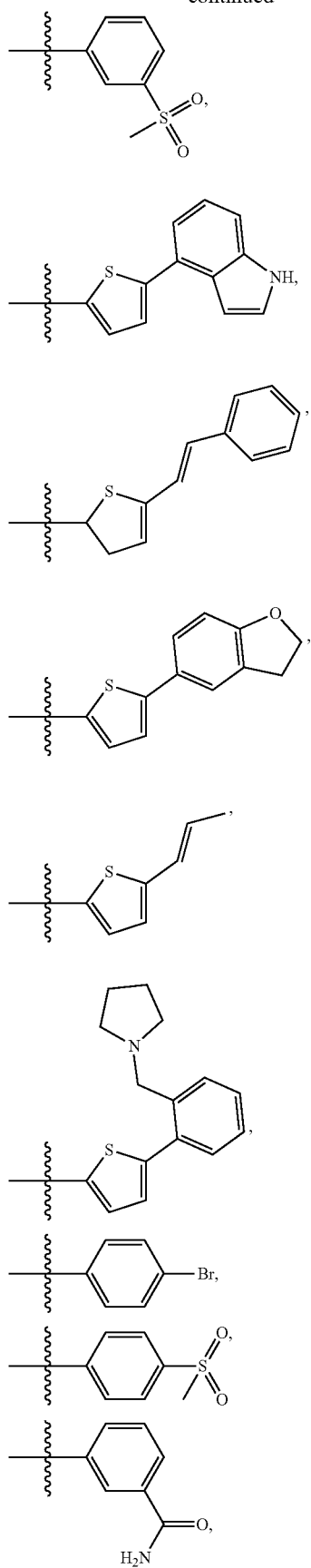
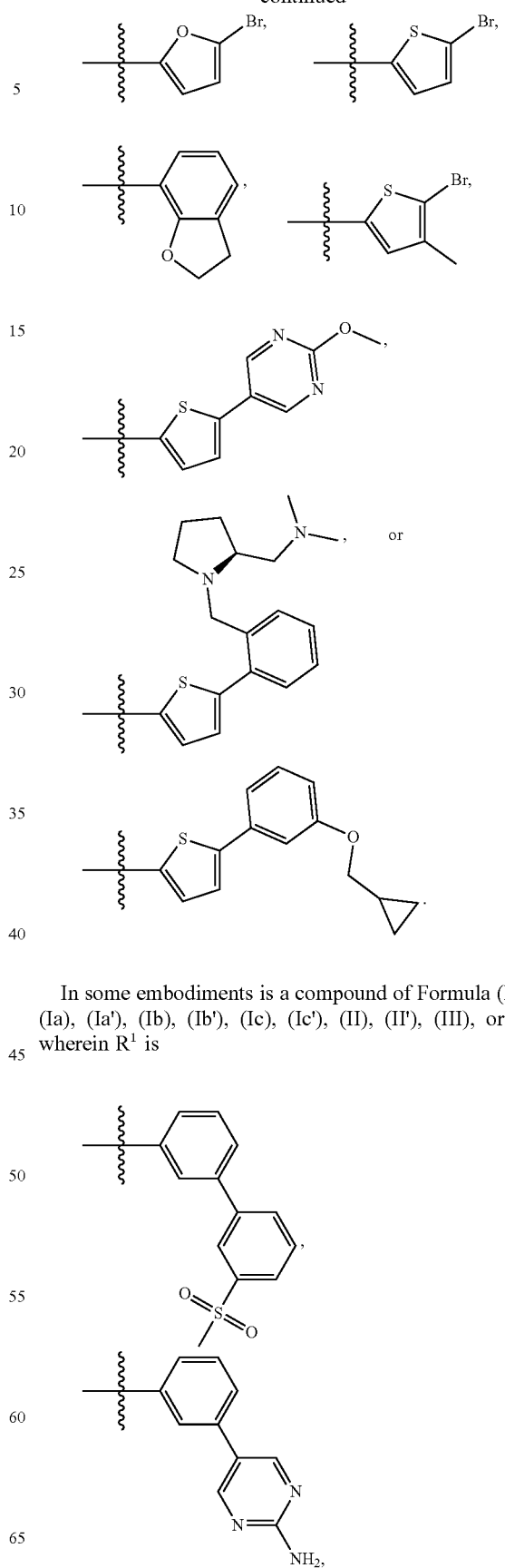
In some embodiments is a compound of Formula (I), (I'), (Ia), (Ia'), (Ib), (Ib'), (Ic), (Ic'), (II), (II'), (III), or (III'), wherein R¹ is

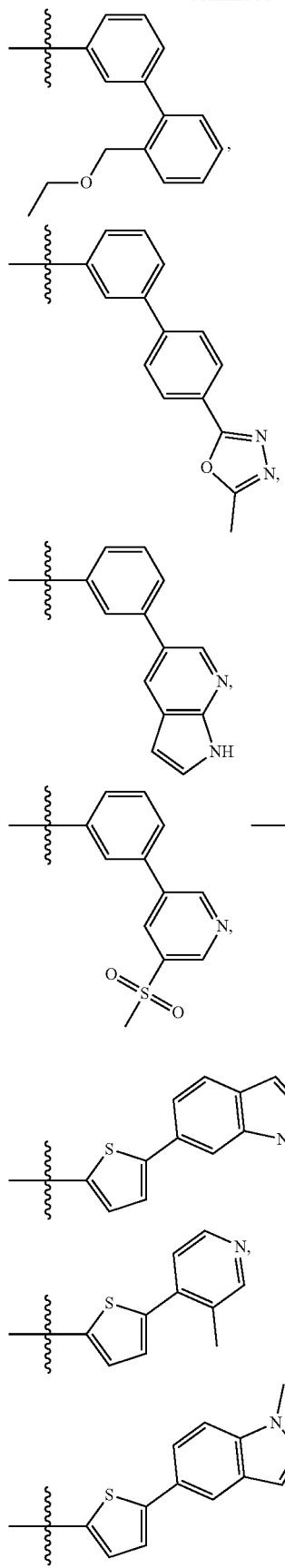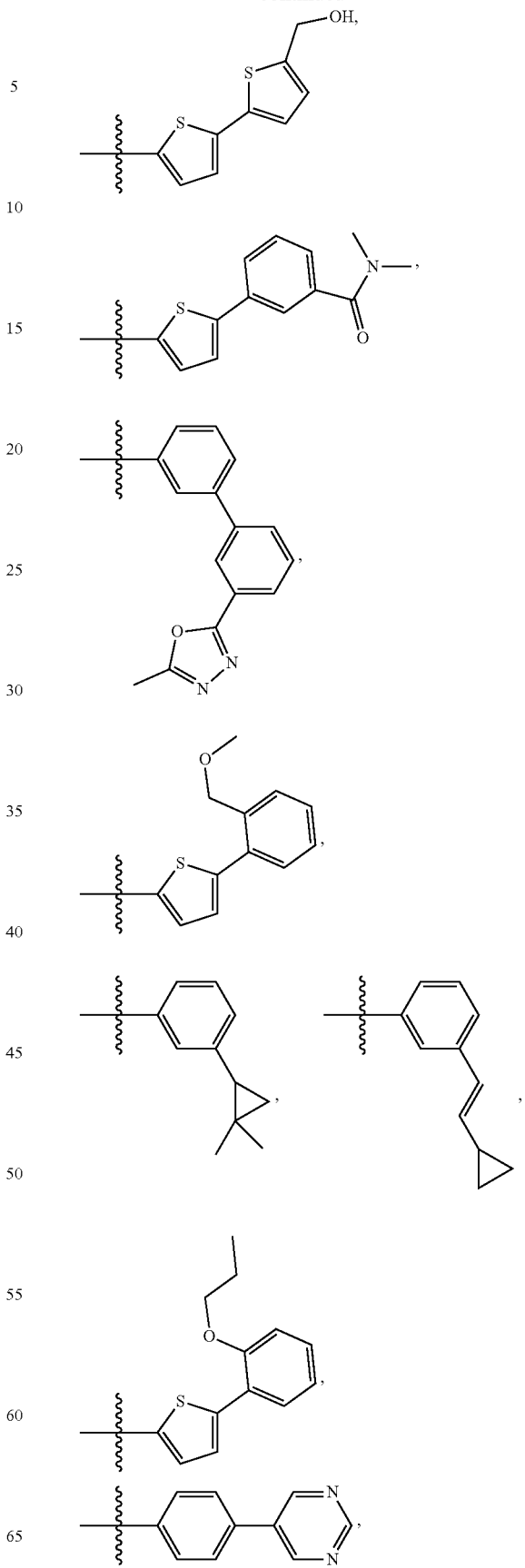

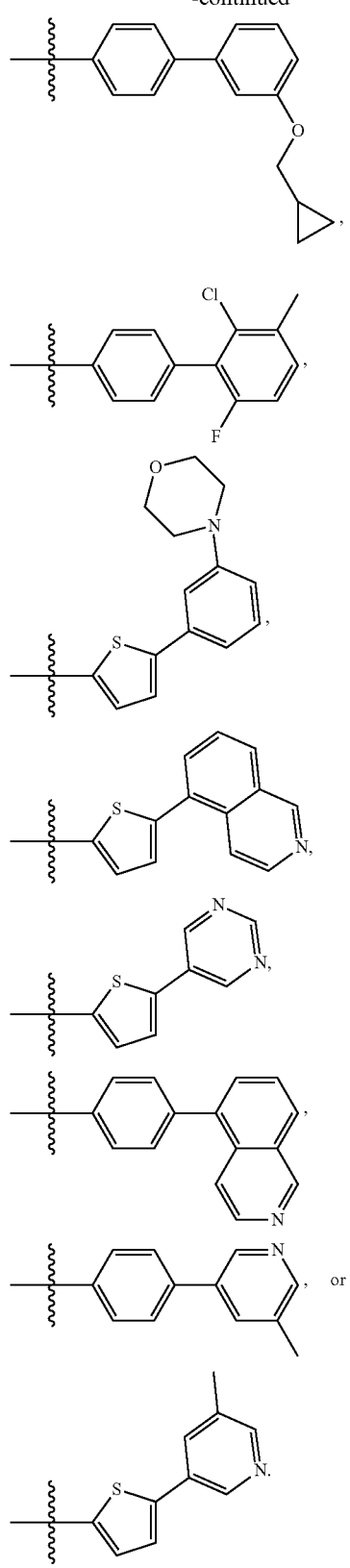
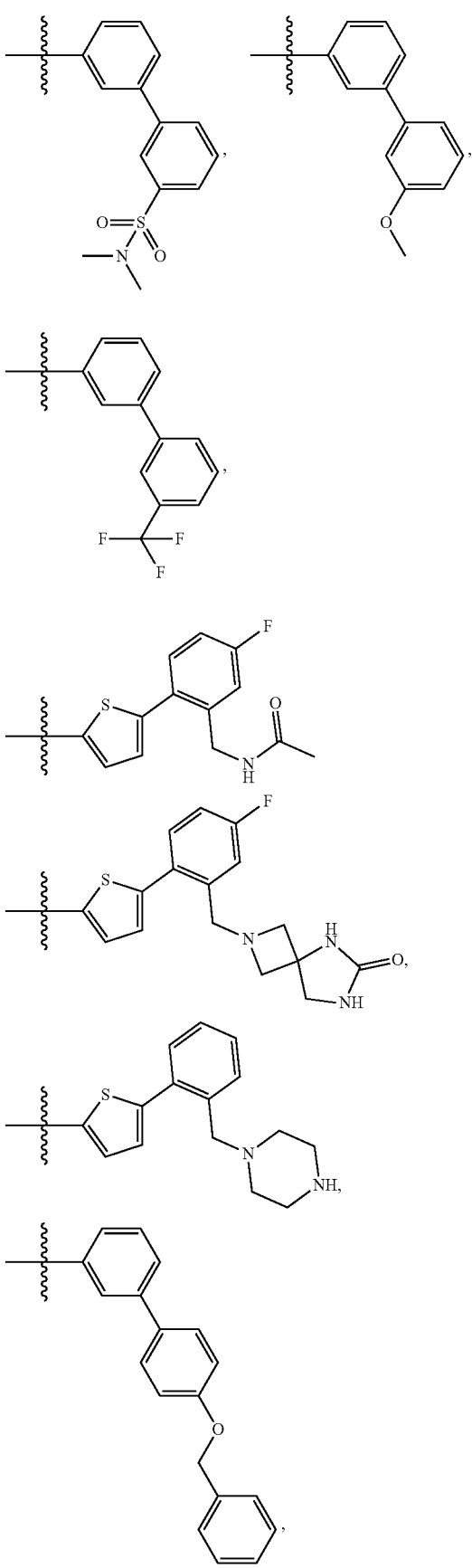
In some embodiments is a compound of Formula (I), (I'), (Ia), (Ia'), (Ib), (Ib'), (Ic), (Ic'), (II), (II'), (III), or (III'), wherein R[1] is

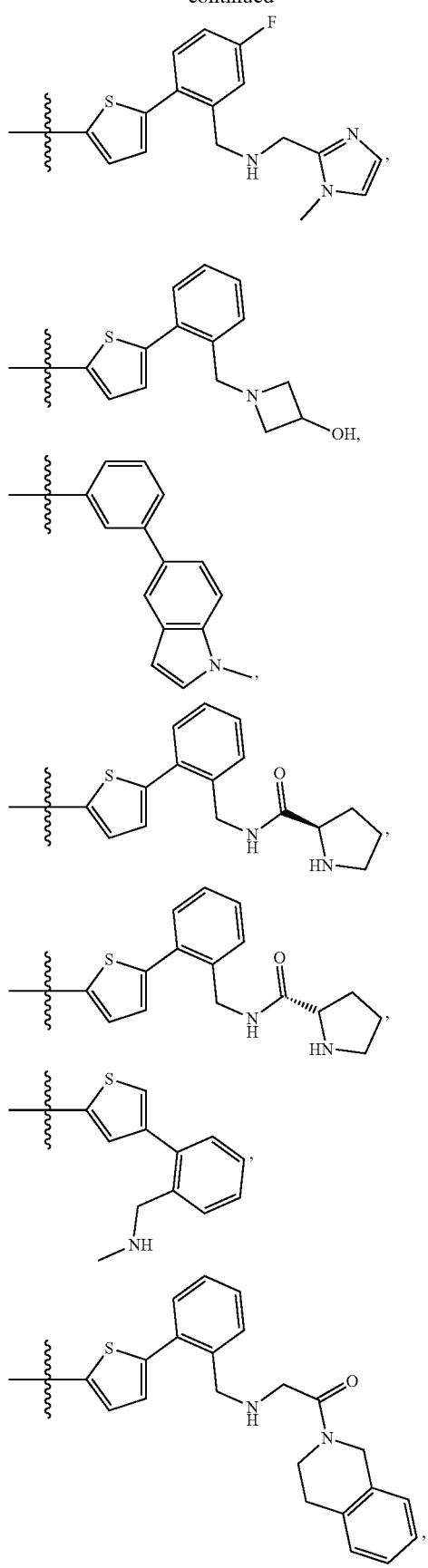
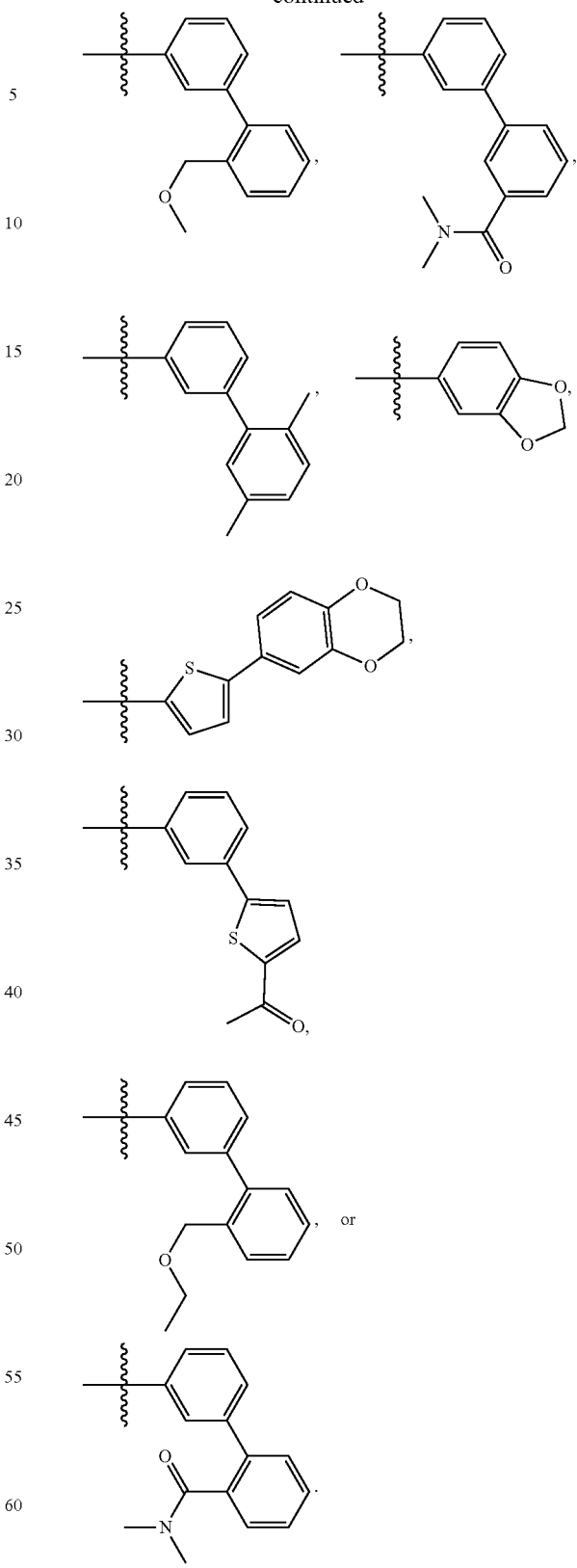
In some embodiments is a compound of Formula (I), (I'), (Ia), (Ia'), (Ib), (Ib'), (Ic), (Ic'), (II), (II'), (III), or (III'), wherein $R^1$ is

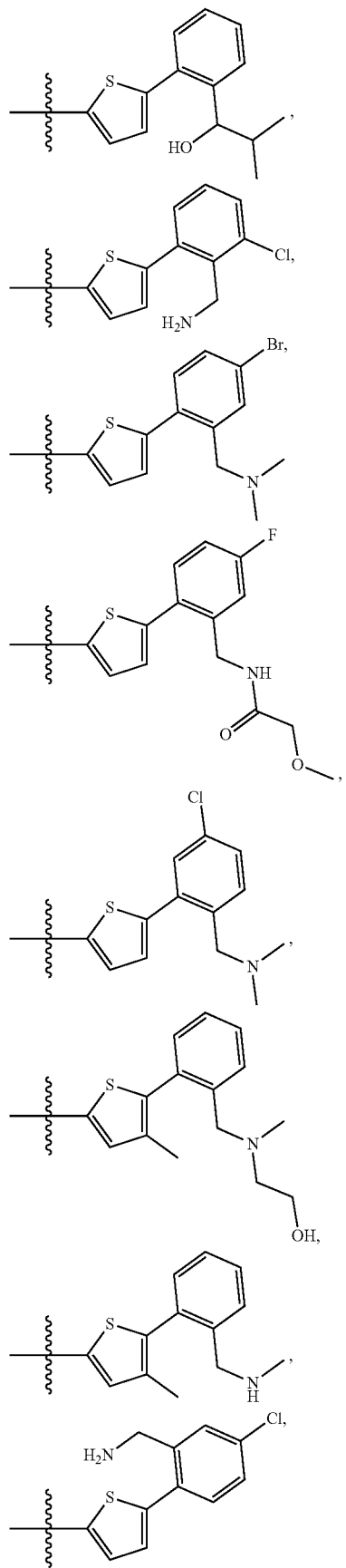
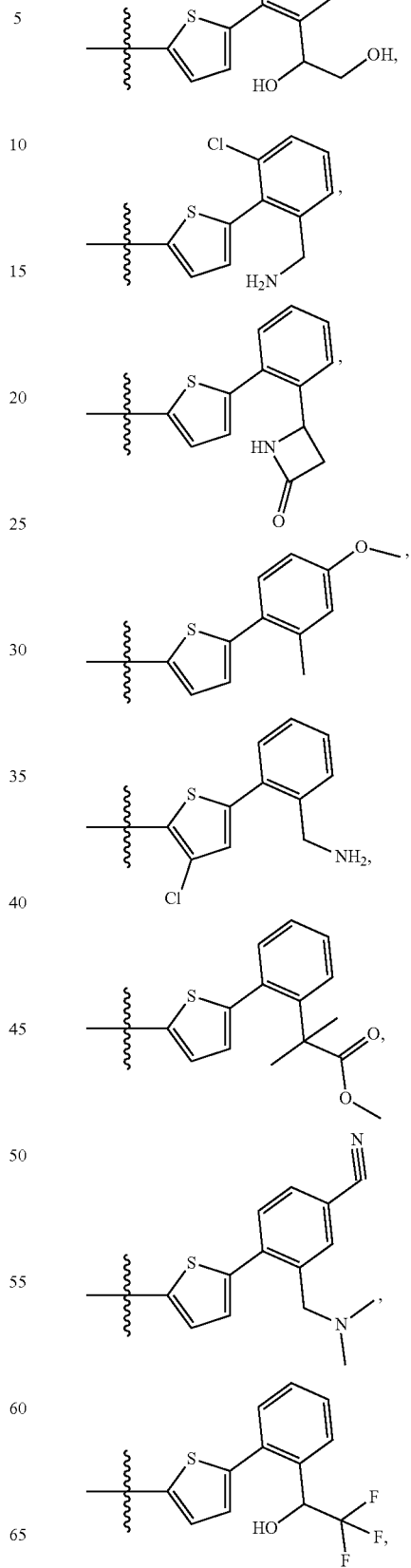

-continued
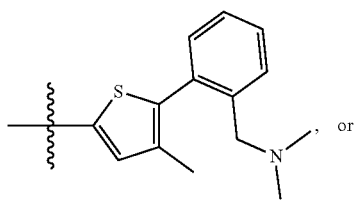, or
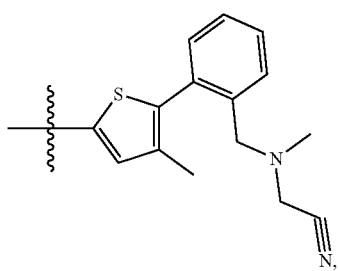,
In some embodiments is a compound of Formula (I), (I'), (Ia), (Ia'), (Ib), (Ib'), (Ic), (Ic'), (II), (II'), (III), or (III'), wherein $R^1$ is
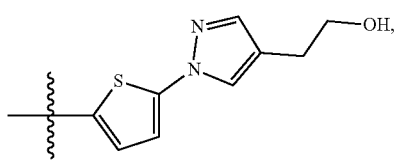,
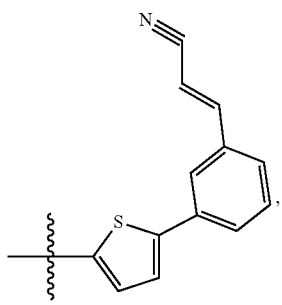,
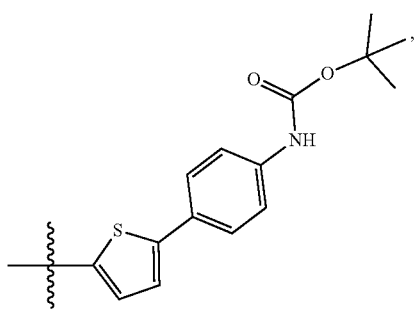,
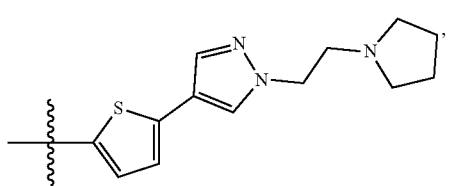,
-continued
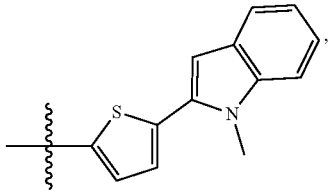,
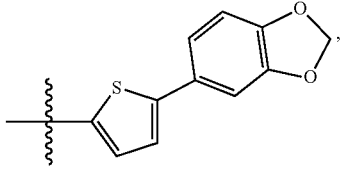,
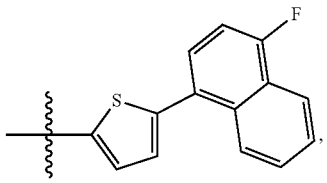,
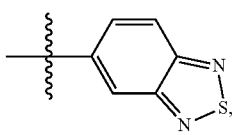,
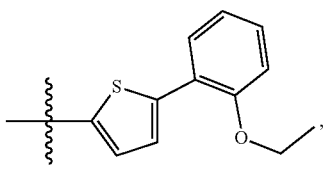,
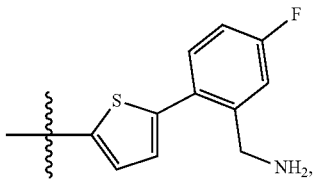,
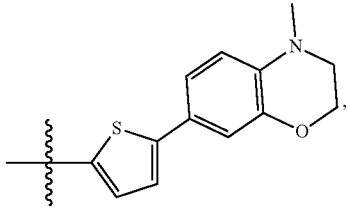,
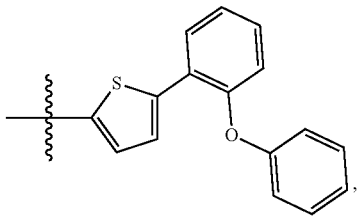,
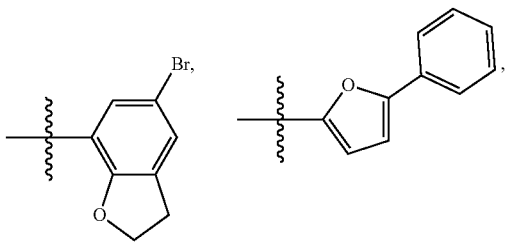, -continued
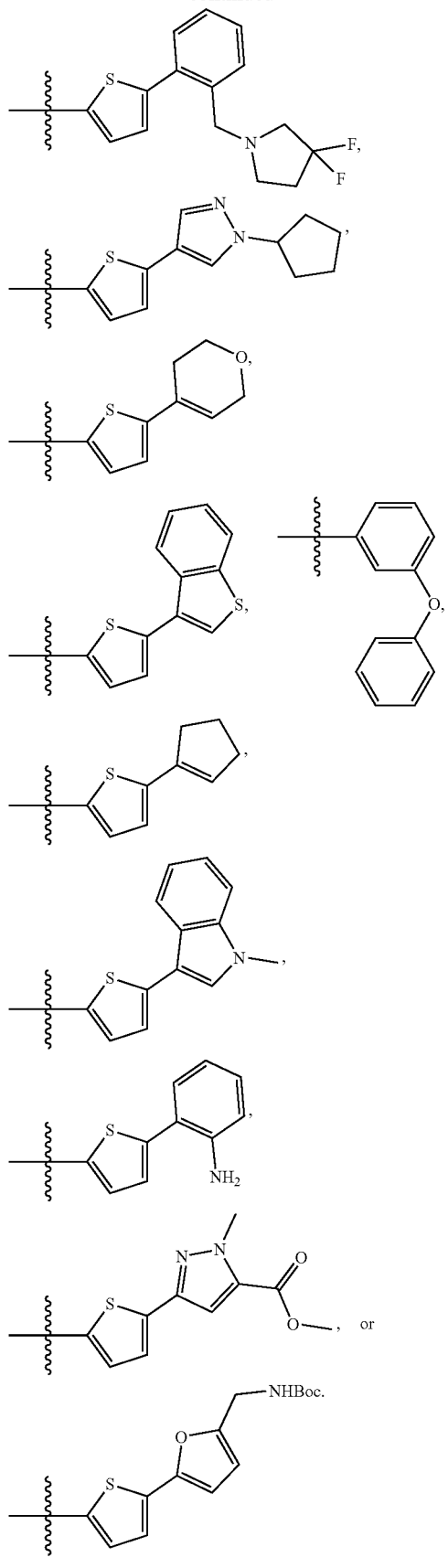
In some embodiments is a compound of Formula (I), (I'), (Ia), (Ia'), (Ib), (Ib'), (Ic), (Ic'), (II), (II'), (III), or (III'), wherein R¹ is
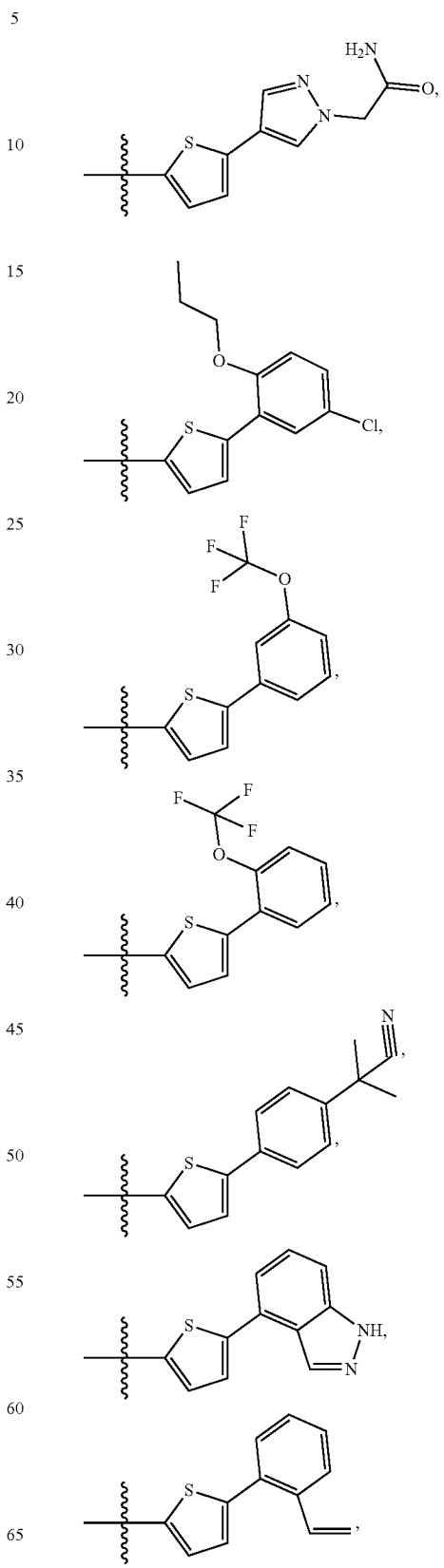

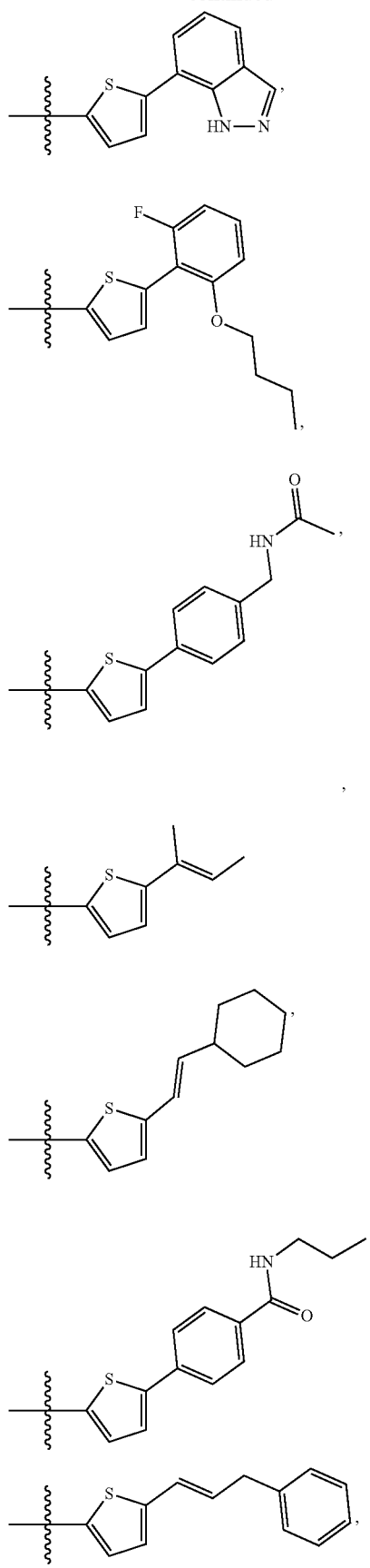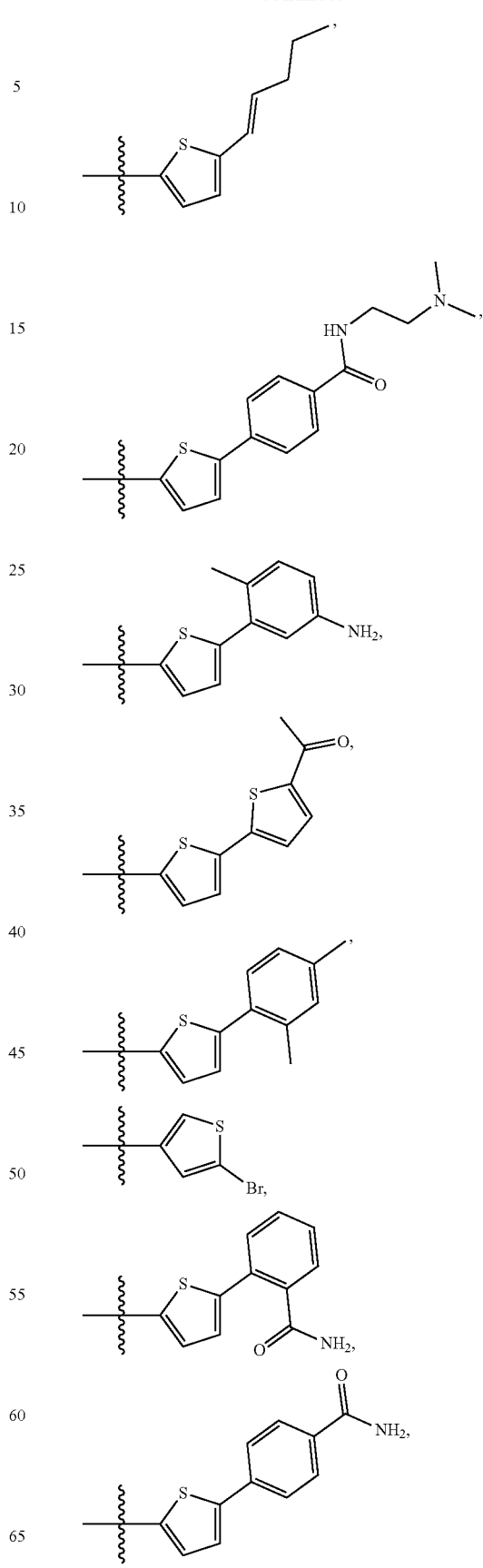

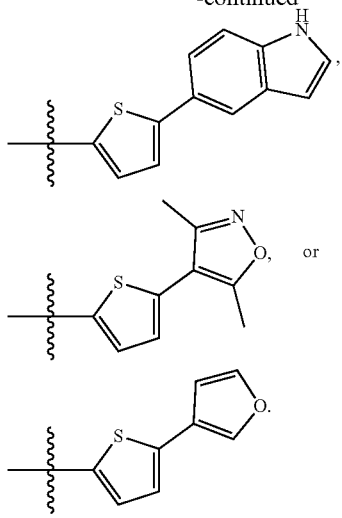
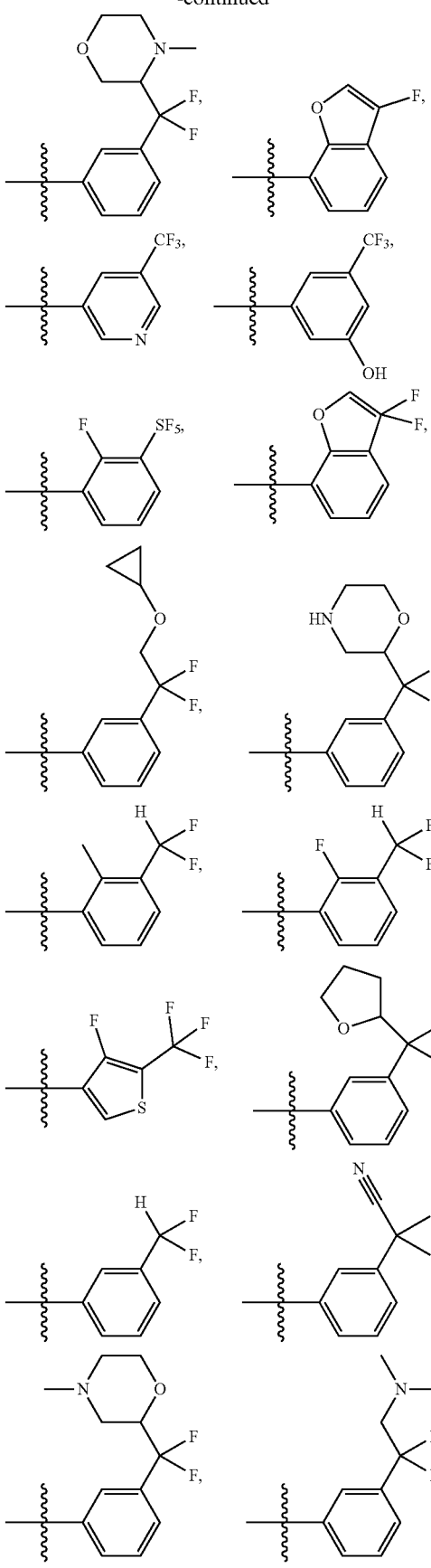
In some embodiments is a compound of Formula (I), (I'), (Ia), (Ia'), (Ib), (Ib'), (Ic), (Ic'), (II), (II'), (III), or (III'), wherein R¹ is
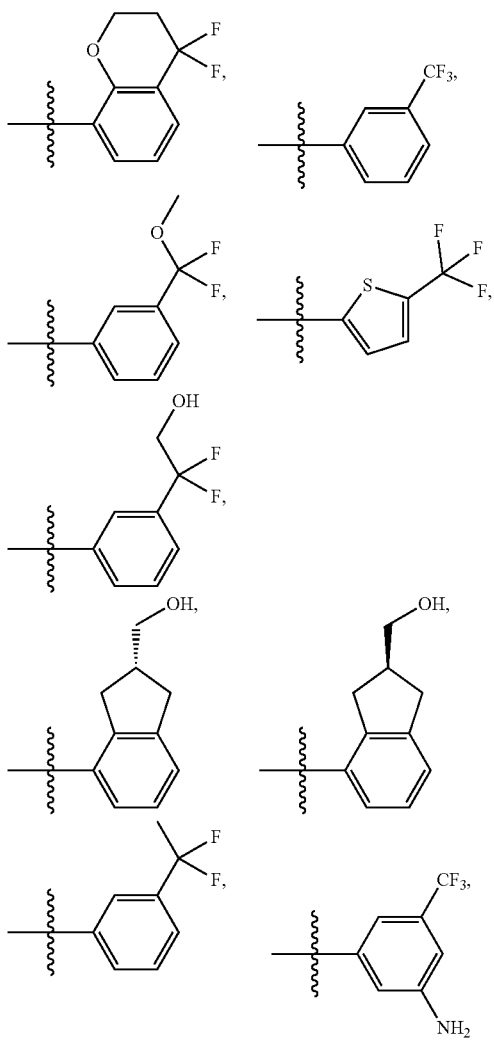

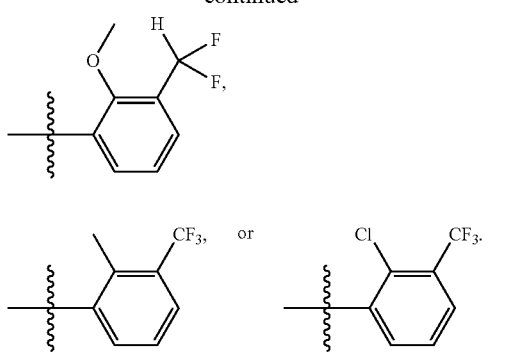
In some embodiments is a compound of Formula (I), (I'), (Ia), (Ia'), (Ib), (Ib'), (Ic), (Ic'), (II), (II'), (III), or (III'), wherein R¹ is
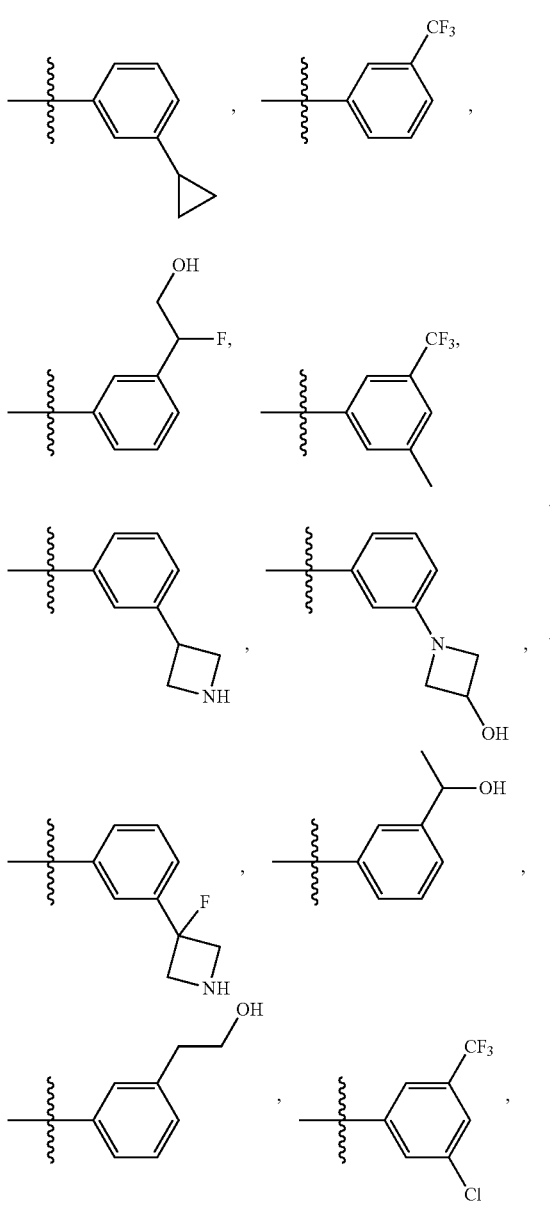
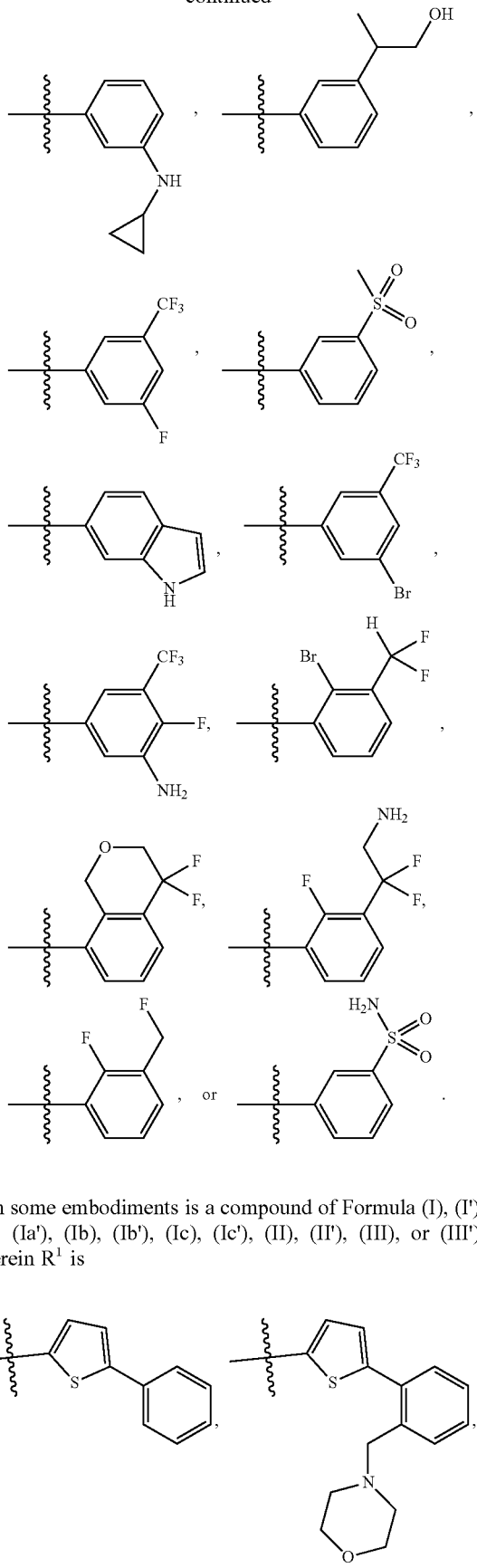
In some embodiments is a compound of Formula (I), (I'), (Ia), (Ia'), (Ib), (Ib'), (Ic), (Ic'), (II), (II'), (III), or (III'), wherein R¹ is -continued

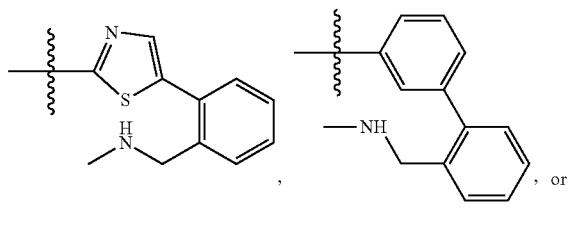

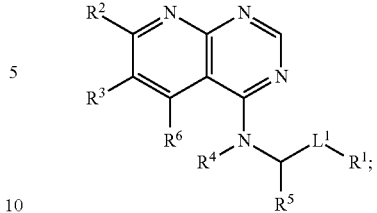

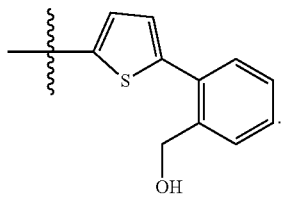

In some embodiments is a compound of Formula (I), (I'), (Ia), (Ia'), (Ib), (Ib'), (Ic), (Ic'), (II), (II'), (III), or (III'), wherein R¹ is

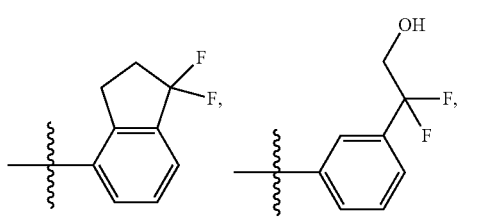

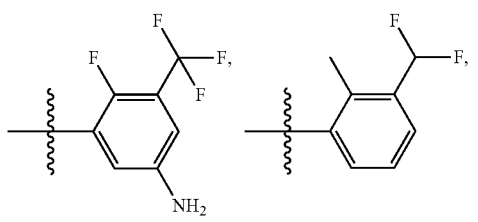

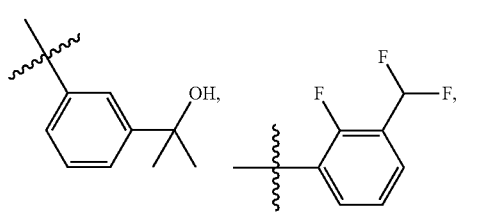

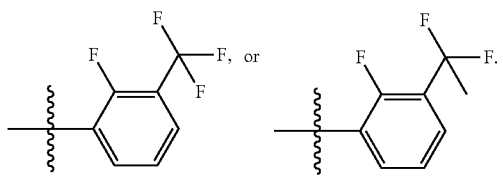

In an aspect is provided a compound of Formula (I-1), or a pharmaceutically acceptable salt or solvate thereof:

Formula (I-1)

wherein:
R¹ is a 3-12 membered cycloalkyl ring, 3-12 membered heterocycloalkyl ring, 6-10 membered aryl ring, or 5-10 membered heteroaryl ring, wherein the 3-12 membered cycloalkyl ring, 3-12 membered heterocycloalkyl ring, 6-10 membered aryl ring, and 5-10 membered heteroaryl ring are optionally substituted with one or more $R^{10}$;

$L^1$ is a bond or $C_{1-6}$alkyl;

$R^2$ is —$OR^{2a}$, —$NR^{2b}R^{2c}$, —$SR^{2g}$, —$S(O)R^{2h}$, —$S(O)_2R^{2h}$, —$S(O)_2NR^{2b}R^{2c}$, —$C(R^{2d})(R^{2e})(R^{2f})$, $C(O)NR^{2b}R^{2c}$, —CN, or halogen;

$R^{2a}$ is selected from $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —$C(O)OR^{12}$, —$C(O)R^{15}$, —$C(O)N(R^{12})(R^{13})$, —$S(O)_2R^{15}$, —$S(O)_2N(R^{12})(R^{13})$, and hydrogen, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20a}$;

$R^{2b}$ is selected from hydrogen, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —$C(O)OR^{12}$, —$C(O)R^{15}$, —$C(O)N(R^{12})(R^{13})$, —$S(O)_2R^{15}$, and —$S(O)_2N(R^{12})(R^{13})$, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20a}$;

$R^{2c}$ is selected from hydrogen, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20a}$; or $R^{2b}$ and $R^{2c}$, together with the nitrogen to which they are attached, form a $C_{2-9}$heterocycloalkyl ring optionally substituted with one, two, or three $R^{20a}$;

$R^{2d}$ is selected from hydrogen, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{15}$, —$S(O)_2R^{15}$, —$S(O)_2N(R^{12})(R^{13})$, —$S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, —$CH_2S(O)_2N(R^{12})(R^{13})$, —$CH_2N(R^{12})S(O)_2(R^{13})$, and —$P(O)(R^{17})(R^{17a})$, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20a}$;

$R^{2e}$ is selected from hydrogen, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20a}$;

$R^{21}$ is selected from hydrogen, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20a}$;

$R^{2g}$ is selected from hydrogen, $C_{2-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —C(O)OR$^{12}$, —C(O)R$^{15}$, —C(O)N(R$^{12}$)(R$^{13}$), —S(O)$_2$R$^{15}$, —S(O)$_2$N(R$^{12}$)(R$^{13}$), wherein $C_{2-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20a}$;

$R^{2h}$ is selected from $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20a}$;

$R^3$ is selected from halogen, $C_{1-6}$alkyl, $C_{2-6}$alkenyl, $C_{2-6}$alkynyl, $C_{3-14}$cycloalkyl, $C_{2-9}$heterocycloalkyl, $C_{6-10}$aryl, $C_{1-9}$heteroaryl, —SR$^{12}$, —N(R$^{12}$)(R$^{13}$), —C(O)OR$^{12}$, —OC(O)N(R$^{12}$)(R$^{13}$), —N(R$^{14}$)C(O)N(R$^{12}$)(R$^{13}$), —N(R$^{14}$)C(O)OR$^{15}$, —N(R$^{14}$)S(O)$_2$R$^{15}$, N(R$^{14}$)S(O)R$^{15}$, —C(O)R$^{15}$, —S(O)R$^{15}$, —OC(O)R$^{15}$, —C(O)N(R$^{12}$)(R$^{13a}$), —C(O)C(O)N(R$^{12}$)(R$^{13}$), —N(R$^{14}$)C(O)R$^{15}$, —S(O)$_2$R$^{15}$, —S(O)$_2$N(R$^{12}$)(R$^{13}$), —S(O)N(R$^{12}$)(R$^{13}$), —S(=O)(=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, —CH$_2$S(O)$_2$N(R$^{12}$)(R$^{13}$), —CH$_2$N(R$^{12}$)S(O)$_2$(R$^{13}$), CH$_2$S(O) R$^{15}$, —CH$_2$S(O)N(R$^{12}$)(R$^{13}$), —CH$_2$N(R$^{12}$)S(O)(R$^{13}$) and —P(O)(R$^{17}$)(R$^{17a}$), wherein $C_{1-6}$alkyl, $C_{2-6}$alkenyl, $C_{2-6}$alkynyl, $C_{3-14}$cycloalkyl, $C_{2-9}$heterocycloalkyl, $C_{6-10}$aryl, and $C_{1-9}$heteroaryl are optionally substituted with one, two, or three $R^{20b}$;

$R^4$ is selected from hydrogen, $C_{1-6}$alkyl, and $C_{1-6}$haloalkyl;

$R^5$ is selected from hydrogen, $C_{1-6}$alkyl, and $C_{1-6}$haloalkyl;

$R^6$ is selected from hydrogen, halogen, —CN, $C_{1-6}$alkyl, $C_{2-6}$alkenyl, $C_{2-6}$alkynyl, $C_{3-10}$cycloalkyl, $C_{2-9}$heterocycloalkyl, —OR$^{12}$, —SR$^{12}$, —N(R$^{12}$)(R$^{13}$), —C(O)OR$^{12}$, —OC(O)N(R$^{12}$)(R$^{13}$), —N(R$^{14}$)C(O)N(R$^{12}$)(R$^{13}$), —N(R$^{14}$)C(O)OR$^{15}$, —N(R$^{14}$)S(O)$_2$R$^{15}$, —C(O)R$^{15}$, —S(O)R$^{15}$, —OC(O)R$^{15}$, —C(O)N(R$^{12}$)(R$^{13}$), —C(O)C(O)N(R$^{12}$)(R$^{13}$), —N(R$^{14}$)C(O)R$^{15}$, —S(O)$_2$R$^{15}$, —S(O)$_2$N(R$^{12}$)(R$^{13}$), —S(=O)(=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, —CH$_2$S(O)$_2$N(R$^{12}$)(R$^{13}$), —CH$_2$N(R$^{12}$)S(O)$_2$(R$^{13}$), and —P(O)(R$^{17}$)(R$^{17a}$) wherein $C_{1-6}$alkyl, $C_{2-6}$alkenyl, $C_{2-6}$alkynyl, $C_{3-10}$cycloalkyl, and $C_{2-9}$heterocycloalkyl are optionally substituted with one, two, or three $R^{20c}$;

each $R^{10}$ is independently selected from halogen, —CN, $C_{1-6}$alkyl, $C_{2-6}$alkenyl, $C_{2-6}$alkynyl, $C_{3-7}$cycloalkyl, $C_{2-9}$heterocycloalkyl, $C_{6-10}$aryl, $C_{1-9}$heteroaryl, —OR$^{12}$, —SR$^{12}$, —N(R$^{12}$)(R$^{13}$), —C(O)OR$^{12}$, —OC(O)N(R$^{12}$)(R$^{13}$), —N(R$^{14}$)C(O)N(R$^{12}$)(R$^{13}$), —N(R$^{14}$)C(O)OR$^{15}$, —N(R$^{14}$)S(O)$_2$R$^{15}$, —C(O)R$^{15}$, —S(O)R$^{15}$, —OC(O)R$^{15}$, —C(O)N(R$^{12}$)(R$^{13}$), —C(O)C(O)N(R$^{12}$)(R$^{13}$), —N(R$^{14}$)C(O)R$^{15}$, —S(O)$_2$R$^{15}$, —S(O)$_2$N(R$^{12}$)(R$^{13}$), —S(=O)(=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, —CH$_2$S(O)$_2$N(R$^{12}$)(R$^{13}$), —CH$_2$N(R$^{12}$)S(O)$_2$(R$^{13}$), and —P(O)(R$^{17}$)(R$^{17a}$), wherein $C_{1-6}$alkyl, $C_{2-6}$alkenyl, $C_{2-6}$alkynyl, $C_{3-7}$cycloalkyl, $C_{2-9}$heterocycloalkyl, $C_{6-10}$aryl, and $C_{1-9}$heteroaryl are optionally substituted with one, two, or three $R^{20a}$;

each $R^{12}$ is independently selected from hydrogen, $C_{1-6}$alkyl, $C_{1-6}$haloalkyl, $C_{2-6}$alkenyl, $C_{2-6}$alkynyl, $C_{3-7}$cycloalkyl, $C_{2-9}$heterocycloalkyl, $C_{6-10}$aryl, and $C_{1-9}$heteroaryl, wherein $C_{1-6}$alkyl, $C_{2-6}$alkenyl, $C_{2-6}$alkynyl, $C_{3-7}$cycloalkyl, $C_{2-9}$heterocycloalkyl, $C_{6-10}$aryl, and $C_{1-9}$heteroaryl are optionally substituted with one, two, or three $R^{20e}$;

each $R^{13}$ is independently selected from hydrogen, $C_{1-6}$alkyl, and $C_{1-6}$haloalkyl; or $R^{12}$ and $R^{13}$, together with the nitrogen to which they are attached, form a $C_{2-9}$heterocycloalkyl ring optionally substituted with one, two, or three $R^{20f}$;

$R^{13a}$ is selected from $C_{1-6}$alkyl and $C_{1-6}$haloalkyl; or $R^{12}$ and $R^{13a}$, together with the nitrogen to which they are attached, form a $C_{2-9}$heterocycloalkyl ring optionally substituted with one, two, or three $R^{20f}$;

each $R^{14}$ is independently selected from hydrogen, $C_{1-6}$alkyl, and $C_{1-6}$haloalkyl;

each $R^{15}$ is independently selected $C_{1-6}$alkyl, $C_{2-6}$alkenyl, $C_{2-6}$alkynyl, $C_{3-7}$cycloalkyl, $C_{2-9}$heterocycloalkyl, $C_{6-10}$aryl, and $C_{1-9}$ heteroaryl, wherein $C_{1-6}$alkyl, $C_{2-6}$alkenyl, $C_{2-6}$alkynyl, $C_{3-7}$cycloalkyl, $C_{2-9}$heterocycloalkyl, $C_{6-10}$aryl, and $C_{1-9}$heteroaryl are optionally substituted with one, two, or three $R^{20g}$;

each $R^{17}$ and each $R^{17a}$ are each independently selected from $C_{1-6}$alkyl and $C_{3-6}$cycloalkyl, wherein $C_{1-6}$alkyl and $C_{3-6}$cycloalkyl are optionally substituted with one, two or three of $R^{20h}$; or $R^{17}$ and $R^{17a}$ are combined to form a $C_{2-9}$heterocycloalkyl ring;

each $R^{20a}$, $R^{20b}$, $R^{20c}$, $R^{20d}$, $R^{20e}$, $R^{20f}$, $R^{20g}$, and $R^{20h}$ are each independently selected from halogen, oxo, =NH, —CN, $C_{1-6}$alkyl, $C_{2-6}$alkenyl, $C_{2-6}$alkynyl, $C_{3-10}$cycloalkyl, —CH$_2$—$C_{3-10}$cycloalkyl, $C_{2-9}$heterocycloalkyl, —CH$_2$—$C_{2-9}$heterocycloalkyl, $C_{6-10}$aryl, —CH$_2$—$C_{6-10}$aryl, $C_{1-9}$heteroaryl, —OR$^{21}$, —SR$^{21}$, —N(R$^{22}$)(R$^{23}$), —C(O)OR$^{22}$, —C(O)N(R$^{22}$)(R$^{23}$), —C(O)C(O)N(R$^{22}$)(R$^{23}$), —OC(O)N(R$^{22}$)(R$^{23}$), —N(R$^{24}$)C(O)N(R$^{22}$)(R$^{23}$), —N(R$^{24}$)C(O)OR$^{25}$, —N(R$^{24}$)C(O)R$^{25}$, —N(R$^{24}$)S(O)$_2$R$^{25}$, —C(O)R$^{25}$, —S(O)$_2$R$^{25}$, —S(O)$_2$N(R$^{22}$)(R$^{23}$), —OCH$_2$C(O)OR$^{22}$, and —OC(O)R$^{25}$, wherein $C_{1-6}$alkyl, $C_{2-6}$alkenyl, $C_{2-6}$alkynyl, $C_{3-10}$cycloalkyl, —CH$_2$—$C_{3-10}$cycloalkyl, $C_{2-9}$heterocycloalkyl, —CH$_2$—$C_{2-9}$heterocycloalkyl, $C_{6-10}$aryl, —CH$_2$—$C_{6-10}$aryl, and $C_{1-9}$heteroaryl are optionally substituted with one, two, or three groups independently selected from halogen, oxo, =NH, —CN, $C_{1-6}$alkyl, $C_{1-6}$haloalkyl, $C_{1-6}$alkoxy, $C_{1-6}$haloalkoxy, —OR$^{21}$, —SR$^{21}$, —N(R$^{22}$)(R$^{23}$), —C(O)OR$^{22}$, —C(O)N(R$^{22}$)(R$^{23}$), —C(O)C(O)N(R$^{22}$)(R$^{23}$), —OC(O)N(R$^{22}$)(R$^{23}$), —N(R$^{24}$)C(O)N(R$^{22}$)(R$^{23}$), —N(R$^{24}$)C(O)OR$^{25}$, —N(R$^{24}$)C(O)R$^{25}$, —N(R$^{24}$)S(O)$_2$R$^{25}$, —C(O)R$^{25}$, —S(O)$_2$R$^{25}$, —S(O)$_2$N(R$^{22}$)(R$^{23}$), and —OC(O)R$^{25}$;

each $R^{21}$ is independently selected from H, $C_{1-6}$alkyl, $C_{1-6}$haloalkyl, $C_{2-6}$alkenyl, $C_{2-6}$alkynyl, $C_{3-7}$cycloalkyl, $C_{2-9}$heterocycloalkyl, $C_{6-10}$aryl, and $C_{1-9}$heteroaryl, wherein $C_{3-7}$cycloalkyl, $C_{2-9}$heterocycloalkyl, $C_{6-10}$aryl, and $C_{1-9}$heteroaryl are optionally substituted with one, two, or three groups independently selected from halogen and $C_{1-6}$alkyl;

each $R^{22}$ is independently selected from H, $C_{1-6}$alkyl, $C_{1-6}$haloalkyl, $C_{2-6}$alkenyl, $C_{2-6}$alkynyl, $C_{3-7}$cycloalkyl, $C_{2-9}$heterocycloalkyl, $C_{6-10}$aryl, and $C_{1-9}$heteroaryl, wherein $C_{3-7}$cycloalkyl, $C_{2-9}$heterocycloalkyl, $C_{6-10}$aryl, and $C_{1-9}$heteroaryl are optionally substituted with one, two, or three groups independently selected from halogen and $C_{1-6}$alkyl;

each $R^{23}$ is independently selected from H and $C_{1-6}$alkyl;
each $R^{24}$ is independently selected from H and $C_{1-6}$alkyl; and each $R^{25}$ is selected from $C_{1-6}$alkyl, $C_{2-6}$alkenyl, $C_{2-6}$alkynyl, $C_{3-7}$cycloalkyl, $C_{2-9}$heterocycloalkyl, $C_{6-10}$aryl, and $C_{1-9}$heteroaryl, wherein $C_{1-6}$alkyl, $C_{3-7}$cycloalkyl, $C_{2-9}$heterocycloalkyl, $C_{6-10}$aryl, and $C_{1-9}$heteroaryl are optionally substituted with one, two, or three groups independently selected from halogen, $C_{1-6}$alkyl, $C_{1-6}$haloalkyl, $C_{1-6}$alkoxy, $C_{3-7}$cycloalkyl, $C_{2-9}$heterocycloalkyl, $C_{6-10}$aryl, and $C_{1-9}$heteroaryl.

In embodiments, the compound of Formula (I-1) is a compound of Formula (Ia-1), or a pharmaceutically acceptable salt or solvate thereof:

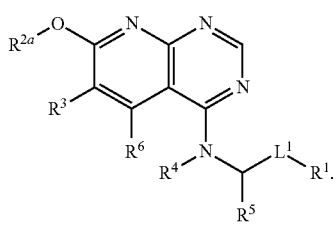

Formula (Ia-1)

In some embodiments of a compound of Formula (I-1) or (Ia-1), $R^{2a}$ is $C_{1-6}$alkyl optionally substituted with one, two, or three $R^{20a}$. In some embodiments of a compound of Formula (I-1) or (Ia-1), or a pharmaceutically acceptable salt or solvate thereof, $R^{2a}$ is unsubstituted $C_{1-6}$alkyl. In some embodiments of a compound of Formula (I-1) or (Ia-1), or a pharmaceutically acceptable salt or solvate thereof, $R^{2a}$ is —$CH_3$.

In embodiments, the compound of Formula (I-1) is a compound of Formula (Ib-1), or a pharmaceutically acceptable salt or solvate thereof:

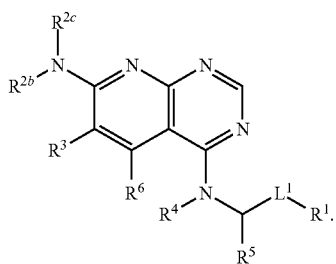

Formula (Ib-1)

In some embodiments of a compound of Formula (I-1) or (Ib-1), or a pharmaceutically acceptable salt or solvate thereof, $R^{2b}$ is $C_{1-6}$alkyl optionally substituted with one, two, or three $R^{20a}$.

In some embodiments of a compound of Formula (I-1) or (Ib-1), or a pharmaceutically acceptable salt or solvate thereof, $R^{2c}$ is $C_{1-6}$alkyl optionally substituted with one, two, or three $R^{20a}$.

In some embodiments of a compound of Formula (I-1) or (Ib-1), or a pharmaceutically acceptable salt or solvate thereof, $R^{2c}$ is hydrogen.

In embodiments, the compound of Formula (I-1) is a compound of Formula (Ic-1), or a pharmaceutically acceptable salt or solvate thereof:

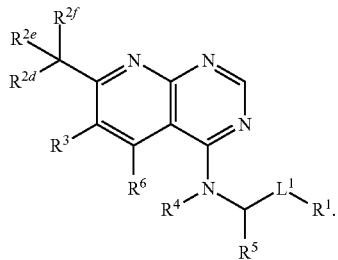

Formula (Ic-1)

In some embodiments of a compound of Formula (I-1) or (Ic-1), or a pharmaceutically acceptable salt or solvate thereof, $R^{2d}$ is hydrogen or $C_{1-6}$alkyl optionally substituted with one, two, or three $R^{20a}$.

In some embodiments of a compound of Formula (I-1) or (Ic-1), or a pharmaceutically acceptable salt or solvate thereof, $R^{2e}$ is hydrogen.

In some embodiments of a compound of Formula (I-1) or (Ic-1), or a pharmaceutically acceptable salt or solvate thereof, $R^{2f}$ is hydrogen.

In some embodiments of a compound of Formula (I-1), $R^2$ is halogen.

In an aspect is provided a compound of Formula (II), or a pharmaceutically acceptable salt or solvate thereof:

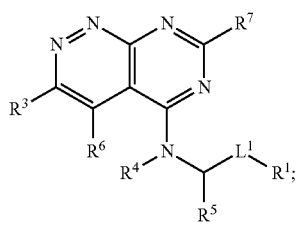

Formula (II)

wherein:
$R^1$ is a 3-12 membered cycloalkyl ring, 3-12 membered heterocycloalkyl ring, 6-10 membered aryl ring, or 5-10 membered heteroaryl ring, wherein the 3-12 membered cycloalkyl ring, 3-12 membered heterocycloalkyl ring, 6-10 membered aryl ring, and 5-10 membered heteroaryl ring are optionally substituted with one or more $R^{10}$;

$L^1$ is a bond or $C_{1-6}$alkyl;

$R^3$ is selected from hydrogen, halogen, —CN, $C_{1-6}$alkyl, $C_{2-6}$alkenyl, $C_{2-6}$alkynyl, $C_{3-14}$cycloalkyl, $C_{2-9}$heterocycloalkyl, $C_{6-10}$aryl, $C_{1-9}$ heteroaryl, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, $N(R^{14})S(O)R^{15}$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{15}$, —$S(O)_2R^{15}$, —$S(O)_2N(R^{12})(R^{13})$, —$S(O)N(R^{12})(R^{13})$, —$S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, —$CH_2S(O)_2N(R^{12})(R^{13})$, —$CH_2N(R^{12})S(O)_2(R^{13})$, $CH_2S(O)R^{15}$, —$CH_2S(O)N(R^{12})(R^{13})$, —$CH_2N(R^{12})S(O)(R^{13})$ and —$P(O)(R^{17})(R^{17a})$, wherein $C_{1-6}$alkyl, $C_{2-6}$alkenyl, $C_{2-6}$alkynyl, $C_{3-14}$cycloalkyl, $C_{2-9}$heterocycloalkyl, $C_{6-10}$aryl, and $C_{1-9}$heteroaryl are optionally substituted with one, two, or three $R^{20b}$;

$R^4$ is selected from hydrogen, $C_{1-6}$alkyl, and $C_{1-6}$haloalkyl;
$R^5$ is selected from hydrogen, $C_{1-6}$alkyl, and $C_{1-6}$haloalkyl;

$R^6$ and $R^7$ are each independently selected from hydrogen, halogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{1-9}$heteroaryl, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{15}$, —$S(O)_2R^{15}$, —$S(O)_2N(R^{12})(R^{13})$, —$S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, —$CH_2S(O)_2N(R^{12})(R^{13})$, —$CH_2N(R^{12})S(O)_2(R^{13})$, and —$P(O)(R^{17})(R^{17a})$, wherein $C_{1-6}$alkyl, $C_{2-6}$alkenyl, $C_{2-6}$alkynyl, $C_{3-10}$cycloalkyl, $C_{2-9}$heterocycloalkyl, and $C_{1-9}$heteroaryl are optionally substituted with one, two, or three $R^{20c}$;

each $R^{10}$ is independently selected from halogen, —CN, $C_{1-6}$alkyl, $C_{2-6}$alkenyl, $C_{2-6}$alkynyl, $C_{3-7}$cycloalkyl, $C_{2-9}$heterocycloalkyl, $C_{6-10}$aryl, $C_{1-9}$heteroaryl, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{15}$, —$S(O)_2R^{15}$, —$S(O)_2N(R^{12})(R^{13})$, —$S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, —$CH_2S(O)_2N(R^{12})(R^{13})$, —$CH_2N(R^{12})S(O)_2(R^{13})$, and —$P(O)(R^{17})(R^{17a})$, wherein $C_{1-6}$alkyl, $C_{2-6}$alkenyl, $C_{2-6}$alkynyl, $C_{3-7}$cycloalkyl, $C_{2-9}$heterocycloalkyl, $C_{6-10}$aryl, and $C_{1-9}$heteroaryl are optionally substituted with one, two, or three $R^{20d}$;

each $R^{12}$ is independently selected from hydrogen, $C_{1-6}$alkyl, $C_{1-6}$haloalkyl, $C_{2-6}$alkenyl, $C_{2-6}$alkynyl, $C_{3-7}$cycloalkyl, $C_{2-9}$heterocycloalkyl, $C_{6-10}$aryl, and $C_{1-9}$heteroaryl, wherein $C_{1-6}$alkyl, $C_{2-6}$alkenyl, $C_{2-6}$alkynyl, $C_{3-7}$cycloalkyl, $C_{2-9}$heterocycloalkyl, $C_{6-10}$aryl, and $C_{1-9}$heteroaryl are optionally substituted with one, two, or three $R^{20e}$;

each $R^{13}$ is independently selected from hydrogen, $C_{1-6}$alkyl, and $C_{1-6}$haloalkyl; or $R^{12}$ and $R^{13}$, together with the nitrogen to which they are attached, form a $C_{2-9}$heterocycloalkyl ring optionally substituted with one, two, or three $R^{20f}$;

each $R^{14}$ is independently selected from hydrogen, $C_{1-6}$alkyl, and $C_{1-6}$haloalkyl;

each $R^{15}$ is independently selected $C_{1-6}$alkyl, $C_{2-6}$alkenyl, $C_{2-6}$alkynyl, $C_{3-7}$cycloalkyl, $C_{2-9}$heterocycloalkyl, $C_{6-10}$aryl and $C_{1-9}$ heteroaryl, wherein $C_{1-6}$alkyl, $C_{2-6}$alkenyl, $C_{2-6}$alkynyl, $C_{3-7}$cycloalkyl, $C_{2-9}$heterocycloalkyl, $C_{6-10}$aryl, and $C_{1-9}$heteroaryl are optionally substituted with one, two, or three $R^{20g}$;

each $R^{17}$ and each $R^{17a}$ are each independently selected from $C_{1-6}$alkyl and $C_{3-6}$cycloalkyl, wherein $C_{1-6}$alkyl and $C_{3-6}$cycloalkyl are optionally substituted with one, two or three of $R^{20h}$; or $R^{17}$ and $R^{17a}$ form a $C_{2-9}$heterocycloalkyl ring;

each $R^{20a}$, $R^{20b}$, $R^{20c}$, $R^{20d}$, $R^{20e}$, $R^{20f}$, $R^{20g}$, and $R^{20h}$ are each independently selected from halogen, oxo, =NH, —CN, $C_{1-6}$alkyl, $C_{2-6}$alkenyl, $C_{2-6}$alkynyl, $C_{3-10}$cycloalkyl, —$CH_2$—$C_{3-10}$cycloalkyl, $C_{2-9}$heterocycloalkyl, —$CH_2$—$C_{2-9}$heterocycloalkyl, $C_{6-10}$aryl, —$CH_2$—$C_{6-10}$aryl, $C_{1-9}$heteroaryl, —$OR^{21}$, —$SR^{21}$, —$N(R^{22})(R^{23})$, —$C(O)OR^{22}$, —$C(O)N(R^{22})(R^{23})$, —$C(O)C(O)N(R^{22})(R^{23})$, —$OC(O)N(R^{22})(R^{23})$, —$N(R^{24})C(O)N(R^{22})(R^{23})$, —$N(R^{24})C(O)OR^{25}$, —$N(R^{24})C(O)R^{25}$, —$N(R^{24})S(O)_2R^{25}$, —$C(O)R^{25}$, —$S(O)_2R^{25}$, —$S(O)_2N(R^{22})(R^{23})$, —$OCH_2C(O)OR^{22}$, and —$OC(O)R^{25}$, wherein $C_{1-6}$alkyl, $C_{2-6}$alkenyl, $C_{2-6}$alkynyl, $C_{3-10}$cycloalkyl, —$CH_2$—$C_{3-10}$cycloalkyl, $C_{2-9}$heterocycloalkyl, —$CH_2$—$C_{2-9}$heterocycloalkyl, $C_{6-10}$aryl, —$CH_2$—$C_{6-10}$aryl, and $C_{1-9}$heteroaryl are optionally substituted with one, two, or three groups independently selected from halogen, oxo, =NH, —CN, $C_{1-6}$alkyl, $C_{1-6}$haloalkyl, $C_{1-6}$alkoxy, $C_{1-6}$haloalkoxy, —$OR^{21}$, —$SR^{21}$, —$N(R^{22})(R^{23})$, —$C(O)OR^{22}$, —$C(O)N(R^{22})(R^{23})$, —$C(O)C(O)N(R^{22})(R^{23})$, —$OC(O)N(R^{22})(R^{23})$, —$N(R^{24})C(O)N(R^{22})(R^{23})$, —$N(R^{24})C(O)OR^{25}$, —$N(R^{24})C(O)R^{25}$, —$N(R^{24})S(O)_2R^{25}$, —$C(O)R^{25}$, —$S(O)_2R^{25}$, —$S(O)_2N(R^{22})(R^{23})$, and —$OC(O)R^{25}$;

each $R^{21}$ is independently selected from H, $C_{1-6}$alkyl, $C_{1-6}$haloalkyl, $C_{2-6}$alkenyl, $C_{2-6}$alkynyl, $C_{3-7}$cycloalkyl, $C_{2-9}$heterocycloalkyl, $C_{6-10}$aryl, and $C_{1-9}$heteroaryl, wherein $C_{3-7}$cycloalkyl, $C_{2-9}$heterocycloalkyl, $C_{6-10}$aryl, and $C_{1-9}$heteroaryl are optionally substituted with one, two, or three groups independently selected from halogen and $C_{1-6}$alkyl;

each $R^{22}$ is independently selected from H, $C_{1-6}$alkyl, $C_{1-6}$haloalkyl, $C_{2-6}$alkenyl, $C_{2-6}$alkynyl, $C_{3-7}$cycloalkyl, $C_{2-9}$heterocycloalkyl, $C_{6-10}$aryl, and $C_{1-9}$heteroaryl, wherein $C_{3-7}$cycloalkyl, $C_{2-9}$heterocycloalkyl, $C_{6-10}$aryl, and $C_{1-9}$heteroaryl are optionally substituted with one, two, or three groups independently selected from halogen and $C_{1-6}$alkyl;

each $R^{23}$ is independently selected from H and $C_{1-6}$alkyl;

each $R^{24}$ is independently selected from H and $C_{1-6}$alkyl; and each $R^{25}$ is selected from $C_{1-6}$alkyl, $C_{2-6}$alkenyl, $C_{2-6}$alkynyl, $C_{3-7}$cycloalkyl, $C_{2-9}$heterocycloalkyl, $C_{6-10}$aryl, and $C_{1-9}$heteroaryl, wherein $C_{1-6}$alkyl, $C_{3-7}$cycloalkyl, $C_{2-9}$heterocycloalkyl, $C_{6-10}$aryl, and $C_{1-9}$heteroaryl are optionally substituted with one, two, or three groups independently selected from halogen, $C_{1-6}$alkyl, $C_{1-6}$haloalkyl, $C_{1-6}$alkoxy, $C_{3-7}$cycloalkyl, $C_{2-9}$heterocycloalkyl, $C_{6-10}$aryl, and $C_{1-9}$heteroaryl.

In some embodiments, $R^3$ is selected from —$N(R^{12})(R^{13})$, —$C(O)R^{15}$, —$C(O)N(R^{12})(R^{13})$, —$SO_2(R^{12})(R^{13})$, —$SO_2N(R^{12})(R^{13})$, —$P(O)(R^{17})(R^{17a})$, $C_{1-6}$alkyl, $C_{3-10}$cycloalkyl, $C_{2-9}$heterocycloalkyl, $C_{6-10}$aryl, and $C_{1-9}$heteroaryl, wherein $C_{1-6}$alkyl, $C_{3-10}$cycloalkyl, $C_{2-9}$heterocycloalkyl, $C_{6-10}$aryl, and $C_{1-9}$heteroaryl are optionally substituted with one, two, or three $R^{20b}$.

In some embodiments, $R^3$ is selected from —$N(R^{12})(R^{13})$, $C_{1-6}$alkyl, $C_{3-10}$cycloalkyl, and $C_{2-9}$heterocycloalkyl, wherein $C_{1-6}$alkyl, $C_{3-10}$cycloalkyl, and $C_{2-9}$heterocycloalkyl are optionally substituted with one, two, or three $R^{20b}$.

In embodiments, $R^3$ is $C_{2-9}$heterocycloalkyl optionally substituted with one, two, or three $R^{20b}$.

In embodiments, $R^3$ is $C_{3-10}$cycloalkyl optionally substituted with one, two, or three $R^{20b}$.

In embodiments, $R^3$ is $C_{3-4}$cycloalkyl optionally substituted with one $R^{20b}$.

In some embodiments, $R^{20b}$ is —CN.

In some embodiments, $R^3$ is

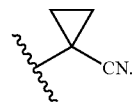

In some embodiments, $R^3$ is $C_{1-6}$alkyl optionally substituted with one, two, or three $R^{20b}$.

In some embodiments, $R^3$ is —$N(R^{12})(R^{13})$.

In an aspect is provided a compound of Formula (III), or a pharmaceutically acceptable salt or solvate thereof:

Formula (III)

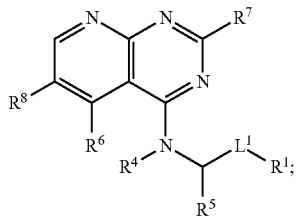

wherein:
$R^1$ is a 3-12 membered cycloalkyl ring, 3-12 membered heterocycloalkyl ring, 6-10 membered aryl ring, or 5-10 membered heteroaryl ring, wherein the 3-12 membered cycloalkyl ring, 3-12 membered heterocycloalkyl ring, 6-10 membered aryl ring, and 5-10 membered heteroaryl ring are optionally substituted with one or more $R^{10}$;
$L^1$ is a bond or $C_{1-6}$alkyl;
$R^4$ is selected from hydrogen, $C_{1-6}$alkyl, and $C_{1-6}$haloalkyl;
$R^5$ is selected from hydrogen, $C_{1-6}$alkyl, and $C_{1-6}$haloalkyl;
$R^6$ is selected from hydrogen, halogen, —CN, $C_{1-6}$alkyl, $C_{2-6}$alkenyl, $C_{2-6}$alkynyl, $C_{3-10}$cycloalkyl, $C_{2-9}$heterocycloalkyl, —OR$^{12}$, —SR$^{12}$, —N(R$^{12}$)(R$^{13}$), —C(O)OR$^{12}$, —OC(O)N(R$^{12}$)(R$^{13}$), —N(R$^{14}$)C(O)N(R$^{12}$)(R$^{13}$), —N(R$^{14}$)C(O)OR$^{15}$, —N(R$^{14}$)S(O)$_2$R$^{15}$, —C(O)R$^{15}$, —S(O)R$^{15}$, —OC(O)R$^{15}$, —C(O)N(R$^{12}$)(R$^{13}$), —C(O)C(O)N(R$^{12}$)(R$^{13}$), —N(R$^{14}$)C(O)R$^{15}$, —S(O)$_2$R$^{15}$, —S(O)$_2$N(R$^{12}$)(R$^{13}$), —S(=O)(=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, —CH$_2$S(O)$_2$N(R$^{12}$)(R$^{13}$), —CH$_2$N(R$^{12}$)S(O)$_2$(R$^{13}$), and —P(O)(R$^{17}$)(R$^{17a}$), wherein $C_{1-6}$alkyl, $C_{2-6}$alkenyl, $C_{2-6}$alkynyl, $C_{3-10}$cycloalkyl, and $C_{2-9}$heterocycloalkyl are optionally substituted with one, two, or three $R^{20c}$;
$R^7$ is selected from hydrogen, halogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{1-9}$heteroaryl, —OR$^{12}$, —SR$^{12}$, —N(R$^{12}$)(R$^{13}$), —C(O)OR$^{12}$, —OC(O)N(R$^{12}$)(R$^{13}$), —N(R$^{14}$)C(O)N(R$^{12}$)(R$^{13}$), —N(R$^{14}$)C(O)OR$^{15}$, —N(R$^{14}$)S(O)$_2$R$^{15}$, —C(O)R$^{15}$, —S(O)R$^{15}$, —OC(O)R$^{15}$, —C(O)N(R$^{12}$)(R$^{13}$), —C(O)C(O)N(R$^{12}$)(R$^{13}$), —N(R$^{14}$)C(O)R$^{15}$, —S(O)$_2$R$^{15}$, —S(O)$_2$N(R$^{12}$)(R$^{13}$), —S(=O)(=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, —CH$_2$S(O)$_2$N(R$^{12}$)(R$^{13}$), —CH$_2$N(R$^{12}$)S(O)$_2$(R$^{13}$), and —P(O)(R$^{17}$)(R$^{17a}$), wherein $C_{1-6}$alkyl, $C_{2-6}$alkenyl, $C_{2-6}$alkynyl, $C_{3-10}$cycloalkyl, $C_{2-9}$heterocycloalkyl, and $C_{1-9}$heteroaryl are optionally substituted with one, two, or three $R^{20c}$;
$R^8$ is —OR$^{9a}$, —NR$^{9b}$R$^{9c}$, —SR$^{9b}$, —S(O)R$^{9d}$, —S(O)$_2$R$^{9d}$, —S(O)$_2$NR$^{9b}$R$^{9c}$, —C(R$^{9e}$)(R$^{9f}$)(R$^{9g}$), and C(O)NR$^{9b}$R$^{9c}$;
$R^{9a}$ is selected from hydrogen, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —C(O)OR$^{12}$, —C(O)R$^{15}$, —C(O)N(R$^{12}$)(R$^{13}$), —S(O)$_2$R$^{15}$, —S(O)$_2$N(R$^{12}$)(R$^{13}$), wherein $C_{1-6}$alkyl is substituted with one, two, or three $R^{20a}$, and wherein $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20a}$;
$R^{9b}$ is selected from hydrogen, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —C(O)OR$^{12}$, —C(O)R$^{15}$, —C(O)N(R$^{12}$)(R$^{13}$), —S(O)$_2$R$^{15}$, and —S(O)$_2$N(R$^{12}$)(R$^{13}$), wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20a}$;
$R^{9c}$ is selected from hydrogen, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20a}$; or $R^{9b}$ and $R^{9c}$, together with the nitrogen to which they are attached, form a $C_{2-9}$heterocycloalkyl ring optionally substituted with one, two, or three $R^{20a}$;
$R^{9d}$ is selected from hydrogen, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl, wherein $C_{1-6}$alkyl is substituted with one, two, or three $R^{20a}$, and wherein $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20a}$;
$R^{9e}$ is selected from hydrogen, $C_{1-6}$alkyl, $C_{2-6}$alkenyl, $C_{2-6}$alkynyl, $C_{3-10}$cycloalkyl, $C_{2-9}$heterocycloalkyl, $C_{1-9}$heteroaryl, —OR$^{12}$, —SR$^{12}$, —N(R$^{12}$)(R$^{13}$), —C(O)OR$^{12}$, —OC(O)N(R$^{12}$)(R$^{13}$), —N(R$^{14}$)C(O)N(R$^{12}$)(R$^{13}$), —N(R$^{14}$)C(O)OR$^{15}$, —N(R$^{14}$)S(O)$_2$R$^{15}$, —C(O)R$^{15}$, —S(O)R$^{15}$, —OC(O)R$^{15}$, —C(O)N(R$^{12}$)(R$^{13}$), —C(O)C(O)N(R$^{12}$)(R$^{13}$), —N(R$^{14}$)C(O)R$^{15}$, —S(O)$_2$R$^{15}$, —S(O)$_2$N(R$^{12}$)(R$^{13}$), —S(=O)(=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, —CH$_2$S(O)$_2$N(R$^{12}$)(R$^{13}$), —CH$_2$N(R$^{12}$)S(O)$_2$(R$^{13}$), and —P(O)(R$^{17}$)(R$^{17a}$), wherein $C_{1-6}$alkyl, $C_{2-6}$alkenyl, $C_{2-6}$alkynyl, $C_{3-10}$cycloalkyl, $C_{2-9}$heterocycloalkyl, and $C_{1-9}$heteroaryl are optionally substituted with one, two, or three $R^{20a}$;
$R^{9f}$ is selected from hydrogen, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20a}$;
$R^{9g}$ is selected from $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20a}$;
each $R^{10}$ is independently selected from halogen, —CN, $C_{1-6}$alkyl, $C_{2-6}$alkenyl, $C_{2-6}$alkynyl, $C_{3-7}$cycloalkyl, $C_{2-9}$heterocycloalkyl, $C_{6-10}$aryl, $C_{1-9}$heteroaryl, —OR$^{12}$, —SR$^{12}$, —N(R$^{12}$)(R$^{13}$), —C(O)OR$^{12}$, —OC(O)N(R$^{12}$)(R$^{13}$), —N(R$^{14}$)C(O)N(R$^{12}$)(R$^{13}$), —N(R$^{14}$)C(O)OR$^{15}$, —N(R$^{14}$)S(O)$_2$R$^{15}$, —C(O)R$^{15}$, —S(O)R$^{15}$, —OC(O)R$^{15}$, —C(O)N(R$^{12}$)(R$^{13}$), —C(O)C(O)N(R$^{12}$)(R$^{13}$), —N(R$^{14}$)C(O)R$^{15}$, —S(O)$_2$R$^{15}$, —S(O)$_2$N(R$^{12}$)(R$^{13}$), —S(=O)(=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, —CH$_2$S(O)$_2$N(R$^{12}$)(R$^{13}$), —CH$_2$N(R$^{12}$)S(O)$_2$(R$^{13}$), and —P(O)(R$^{17}$)(R$^{17a}$), wherein $C_{1-6}$alkyl, $C_{2-6}$alkenyl, $C_{2-6}$alkynyl, $C_{3-7}$cycloalkyl, $C_{2-9}$heterocycloalkyl, $C_{6-10}$aryl, and $C_{1-9}$heteroaryl are optionally substituted with one, two, or three $R^{20a}$;
each $R^{12}$ is independently selected from hydrogen, $C_{1-6}$alkyl, $C_{1-6}$haloalkyl, $C_{2-6}$alkenyl, $C_{2-6}$alkynyl, $C_{3-7}$cycloalkyl, $C_{2-9}$heterocycloalkyl, $C_{6-10}$aryl, and $C_{1-9}$heteroaryl, wherein $C_{1-6}$alkyl, $C_{2-6}$alkenyl, $C_{2-6}$alkynyl, $C_{3-7}$cycloalkyl, $C_{2-9}$heterocycloalkyl, $C_{6-10}$aryl, and $C_{1-9}$heteroaryl are optionally substituted with one, two, or three $R^{20e}$;

each $R^{13}$ is independently selected from hydrogen, $C_{1-6}$alkyl, and $C_{1-6}$haloalkyl; or $R^{12}$ and $R^{13}$, together with the nitrogen to which they are attached, form a $C_{2-9}$heterocycloalkyl ring optionally substituted with one, two, or three $R^{20f}$;

each $R^{14}$ is independently selected from hydrogen, $C_{1-6}$alkyl, and $C_{1-6}$haloalkyl;

each $R^{15}$ is independently selected $C_{1-6}$alkyl, $C_{2-6}$alkenyl, $C_{2-6}$alkynyl, $C_{3-7}$cycloalkyl, $C_{2-9}$heterocycloalkyl, $C_{6-10}$aryl, and $C_{1-9}$ heteroaryl, wherein $C_{1-6}$alkyl, $C_{2-6}$alkenyl, $C_{2-6}$alkynyl, $C_{3-7}$cycloalkyl, $C_{2-9}$heterocycloalkyl, $C_{6-10}$aryl, and $C_{1-9}$heteroaryl are optionally substituted with one, two, or three $R^{20g}$;

each $R^{17}$ and each $R^{17a}$ are each independently selected from $C_{1-6}$alkyl and $C_{3-6}$cycloalkyl, wherein $C_{1-6}$alkyl and $C_{3-6}$cycloalkyl are optionally substituted with one, two or three of $R^{20h}$; or $R^{17}$ and $R^{17a}$ are combined to form a $C_{2-9}$heterocycloalkyl ring;

each $R^{20a}$, $R^{20b}$, $R^{20c}$, $R^{20d}$, $R^{20e}$, $R^{20f}$, $R^{20g}$, and $R^{20h}$ are each independently selected from halogen, oxo, $=NH$, $-CN$, $C_{1-6}$alkyl, $C_{2-6}$alkenyl, $C_{2-6}$alkynyl, $C_{3-10}$cycloalkyl, $-CH_2-C_{3-10}$cycloalkyl, $C_{2-9}$heterocycloalkyl, $-CH_2-C_{2-9}$heterocycloalkyl, $C_{6-10}$aryl, $-CH_2-C_{6-10}$aryl, $C_{1-9}$heteroaryl, $-OR^{21}$, $-SR^{21}$, $-N(R^{22})(R^{23})$, $-C(O)OR^{22}$, $-C(O)N(R^{22})(R^{23})$, $-C(O)C(O)N(R^{22})(R^{23})$, $-OC(O)N(R^{22})(R^{23})$, $-N(R^{24})C(O)N(R^{22})(R^{23})$, $-N(R^{24})C(O)OR^{25}$, $-N(R^{24})C(O)R^{25}$, $-N(R^{24})S(O)_2R^{25}$, $-C(O)R^{25}$, $-S(O)_2R^{25}$, $-S(O)_2N(R^{22})(R^{23})$, $-OCH_2C(O)OR^{22}$, and $-OC(O)R^{25}$, wherein $C_{1-6}$alkyl, $C_{2-6}$alkenyl, $C_{2-6}$alkynyl, $C_{3-10}$cycloalkyl, $-CH_2-C_{3-10}$cycloalkyl, $C_{2-9}$heterocycloalkyl, $-CH_2-C_{2-9}$heterocycloalkyl, $C_{6-10}$aryl, $-CH_2-C_{6-10}$aryl, and $C_{1-9}$heteroaryl are optionally substituted with one, two, or three groups independently selected from halogen, oxo, $=NH$, $-CN$, $C_{1-6}$alkyl, $C_{1-6}$haloalkyl, $C_{1-6}$alkoxy, $C_{1-6}$haloalkoxy, $-OR^{21}$, $-SR^{21}$, $-N(R^{22})(R^{23})$, $-C(O)OR^{22}$, $-C(O)N(R^{22})(R^{23})$, $-C(O)C(O)N(R^{22})(R^{23})$, $-OC(O)N(R^{22})(R^{23})$, $-N(R^{24})C(O)N(R^{22})(R^{23})$, $-N(R^{24})C(O)OR^{25}$, $-N(R^{24})C(O)R^{25}$, $-N(R^{24})S(O)_2R^{25}$, $-C(O)R^{25}$, $-S(O)_2R^{25}$, $-S(O)_2N(R^{22})(R^{23})$, and $-OC(O)R^{25}$;

each $R^{21}$ is independently selected from H, $C_{1-6}$alkyl, $C_{1-6}$haloalkyl, $C_{2-6}$alkenyl, $C_{2-6}$alkynyl, $C_{3-7}$cycloalkyl, $C_{2-9}$heterocycloalkyl, $C_{6-10}$aryl, and $C_{1-9}$heteroaryl, wherein $C_{3-7}$cycloalkyl, $C_{2-9}$heterocycloalkyl, $C_{6-10}$aryl, and $C_{1-9}$heteroaryl are optionally substituted with one, two, or three groups independently selected from halogen and $C_{1-6}$alkyl;

each $R^{22}$ is independently selected from H, $C_{1-6}$alkyl, $C_{1-6}$haloalkyl, $C_{2-6}$alkenyl, $C_{2-6}$alkynyl, $C_{3-7}$cycloalkyl, $C_{2-9}$heterocycloalkyl, $C_{6-10}$aryl, and $C_{1-9}$heteroaryl, wherein $C_{3-7}$cycloalkyl, $C_{2-9}$heterocycloalkyl, $C_{6-10}$aryl, and $C_{1-9}$heteroaryl are optionally substituted with one, two, or three groups independently selected from halogen and $C_{1-6}$alkyl;

each $R^{23}$ is independently selected from H and $C_{1-6}$alkyl;

each $R^{24}$ is independently selected from H and $C_{1-6}$alkyl; and each $R^{25}$ is selected from $C_{1-6}$alkyl, $C_{2-6}$alkenyl, $C_{2-6}$alkynyl, $C_{3-7}$cycloalkyl, $C_{2-9}$heterocycloalkyl, $C_{6-10}$aryl, and $C_{1-9}$heteroaryl, wherein $C_{1-6}$alkyl, $C_{3-7}$cycloalkyl, $C_{2-9}$heterocycloalkyl, $C_{6-10}$aryl, and $C_{1-9}$heteroaryl are optionally substituted with one, two, or three groups independently selected from halogen, $C_{1-6}$alkyl, $C_{1-6}$haloalkyl, $C_{1-6}$alkoxy, $C_{3-7}$cycloalkyl, $C_{2-9}$heterocycloalkyl, $C_{6-10}$aryl, and $C_{1-9}$heteroaryl.

In some embodiments, $R^8$ is $-OR^{9a}$. In some embodiments, $R^8$ is $-NR^{9b}R^{9c}$. In some embodiments, $R^8$ is $-C(R^{9e})(R^{9f})(R^{9g})$.

In some embodiments, $R^6$ is selected from hydrogen, halogen, $C_{1-6}$alkyl, $C_{3-10}$cycloalkyl, $C_{2-9}$heterocycloalkyl, and $C_{1-9}$heteroaryl, wherein $C_{1-6}$alkyl, $C_{3-10}$cycloalkyl, $C_{2-9}$heterocycloalkyl, and $C_{1-9}$heteroaryl are optionally substituted with one, two, or three $R^{20c}$. In some embodiments, $R^6$ is independently selected from hydrogen, halogen, and unsubstituted $C_{1-6}$alkyl. In some embodiments, $R^6$ is hydrogen.

In some embodiments, $R^7$ is selected from hydrogen, halogen, $C_{1-6}$alkyl, $C_{3-10}$cycloalkyl, $C_{2-9}$heterocycloalkyl, and $C_{1-9}$heteroaryl, wherein $C_{1-6}$alkyl, $C_{3-10}$cycloalkyl, $C_{2-9}$heterocycloalkyl, and $C_{1-9}$heteroaryl are optionally substituted with one, two, or three $R^{20c}$. In some embodiments, $R^7$ is independently selected from hydrogen, halogen, and unsubstituted $C_{1-6}$alkyl. In some embodiments, $R^7$ is unsubstituted $C_{1-6}$alkyl. In some embodiments, $R^7$ is hydrogen.

In some embodiments, $R^5$ is selected from $C_{1-6}$alkyl and $C_{1-6}$haloalkyl. In some embodiments, $R^5$ is $-CH_3$.

In some embodiments, $R^4$ is hydrogen.

In some embodiments, $L^1$ is a bond.

In some embodiments, $R^1$ is a 6-10 membered aryl ring substituted with one or more $R^{10}$.

In some embodiments, $R^1$ is phenyl substituted with one or more $R^{10}$.

In some embodiments, $R^1$ is phenyl substituted with one, two, or three $R^{10}$.

In some embodiments, each $R^{10}$ is independently selected from halogen, $C_{1-6}$alkyl, $C_{3-7}$cycloalkyl, $C_{2-9}$heterocycloalkyl, $C_{6-10}$aryl, $C_{1-9}$heteroaryl, $-OR^{12}$, and $N(R^{12})(R^{13})$, wherein $C_{1-6}$alkyl, $C_{3-7}$cycloalkyl, $C_{2-9}$heterocycloalkyl, $C_{6-10}$aryl, and $C_{1-9}$heteroaryl are optionally substituted with one, two, or three $R^{20a}$.

In some embodiments, each $R^{10}$ is independently selected from halogen, $C_{1-6}$alkyl, and $N(R^{12})(R^{13})$ wherein $C_{1-6}$alkyl is optionally substituted with one, two, or three $R^{20a}$.

In some embodiments, each $R^{10}$ is independently selected from halogen and $C_{1-6}$alkyl, wherein $C_{1-6}$alkyl is substituted with one, two, or three $R^{20d}$, and each $R^{20d}$ is halogen.

In some embodiments, $R^1$ is independently selected from

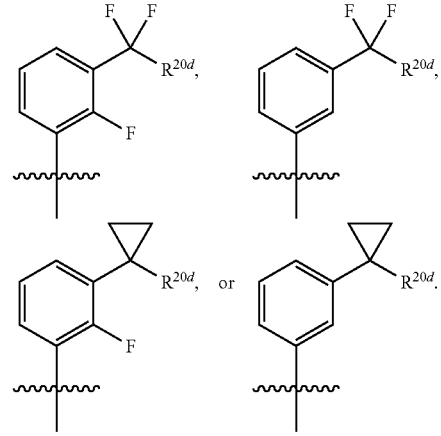

In some embodiments, $R^{20d}$ is $C_{1-6}$alkyl optionally substituted with one, two, or three groups independently selected from F and $-OH$.

In some embodiments, $R^{20d}$ is $C_{1-3}$alkyl substituted with one $-OH$.

253

In some embodiments, $R^1$ is selected from

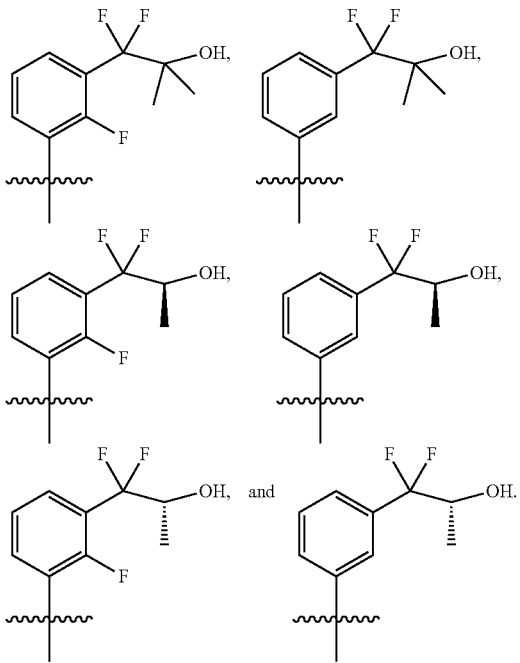

In an aspect is provided a compound of Formula (I-2), or a pharmaceutically acceptable salt or solvate thereof:

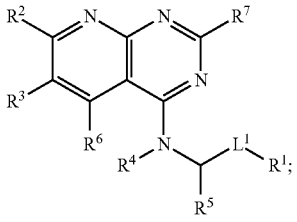

Formula (I-2)

wherein:
$R^1$ is a 3-12 membered cycloalkyl ring, 3-12 membered heterocycloalkyl ring, 6-10 membered aryl ring, or 5-10 membered heteroaryl ring, wherein the 3-12 membered cycloalkyl ring, 3-12 membered heterocycloalkyl ring, 6-10 membered aryl ring, and 5-10 membered heteroaryl ring are optionally substituted with one or more $R^{10}$;

$L^1$ is a bond or $C_{1-6}$alkyl;

$R^2$ is $-OR^{2a}$, $-NR^{2b}R^{2c}$, $-SR^{2g}$, $-S(O)R^{2h}$, $-S(O)_2R^{2h}$, $-S(O)_2NR^{2b}R^{2c}$, $-C(R^{2d})(R^{2e})(R^{2f})$, $C(O)NR^{2b}R^{2c}$, $-CN$, or halogen;

$R^{2a}$ is selected from hydrogen, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, $-C(O)OR^{12}$, $-C(O)R^{15}$, $-C(O)N(R^{12})(R^{13})$, $-S(O)_2R^{15}$, $-S(O)_2N(R^{12})(R^{13})$, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20a}$;

$R^{2b}$ is selected from hydrogen, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, $-C(O)OR^{12}$, $-C(O)R^{15}$, $-C(O)N(R^{12})(R^{13})$, $-S(O)_2R^{15}$, and $-S(O)_2N(R^{12})$

254

$(R^{13})$, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20a}$;

$R^{2c}$ is selected from hydrogen, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20a}$; or $R^{2b}$ and $R^{2c}$, together with the nitrogen to which they are attached, form a $C_{2-9}$heterocycloalkyl ring optionally substituted with one, two, or three $R^{20a}$;

$R^{2d}$ is selected from hydrogen, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, $-OR^{12}$, $-SR^{12}$, $-N(R^{12})(R^{13})$, $-C(O)OR^{12}$, $-OC(O)N(R^{12})(R^{13})$, $-N(R^{14})C(O)N(R^{12})(R^{13})$, $-N(R^{14})C(O)OR^{15}$, $-N(R^{14})S(O)_2R^{15}$, $-C(O)R^{15}$, $-S(O)R^{15}$, $-OC(O)R^{15}$, $-C(O)N(R^{12})(R^{13})$, $-C(O)C(O)N(R^{12})(R^{13})$, $-N(R^{14})C(O)R^{15}$, $-S(O)_2R^{15}$, $-S(O)_2N(R^{12})(R^{13})$, $-S(=O)(=NH)N(R^{12})(R^{13})$, $-CH_2C(O)N(R^{12})(R^{13})$, $-CH_2N(R^{14})C(O)R^{15}$, $-CH_2S(O)_2R^{15}$, $-CH_2S(O)_2N(R^{12})(R^{13})$, $-CH_2N(R^{12})S(O)_2(R^{13})$, and $-P(O)(R^{17})(R^{17a})$, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20a}$;

$R^{2e}$ is selected from hydrogen, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20a}$;

$R^{2f}$ is selected from hydrogen, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20a}$;

$R^{2g}$ is selected from hydrogen, $C_{2-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, $-C(O)OR^{12}$, $-C(O)R^{15}$, $-C(O)N(R^{12})(R^{13})$, $-S(O)_2R^{15}$, $-S(O)_2N(R^{12})(R^{13})$, wherein $C_{2-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20a}$;

$R^{2h}$ is selected from $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20a}$;

$R^3$ is $C_{3-4}$cycloalkyl optionally substituted with one $R^{20b}$.

$R^4$ is selected from hydrogen, $C_{1-6}$alkyl, and $C_{1-6}$haloalkyl;

$R^5$ is selected from hydrogen, $C_{1-6}$alkyl, and $C_{1-6}$haloalkyl;

$R^6$ is selected from hydrogen, halogen, $-CN$, $C_{1-6}$alkyl, $C_{2-6}$alkenyl, $C_{2-6}$alkynyl, $C_{3-10}$cycloalkyl, $C_{2-9}$heterocycloalkyl, $-OR^{12}$, $-SR^{12}$, $-N(R^{12})(R^{13})$, $-C(O)OR^{12}$, $-OC(O)N(R^{12})(R^{13})$, $-N(R^{14})C(O)N(R^{12})(R^{13})$, $-N(R^{14})C(O)OR^{15}$, $-N(R^{14})S(O)_2R^{15}$, $-C(O)R^{15}$, $-S(O)R^{15}$, $-OC(O)R^{15}$, $-C(O)N(R^{12})(R^{13})$, $-C(O)C(O)N(R^{12})(R^{13})$, $-N(R^{14})C(O)R^{15}$, $-S(O)_2R^{15}$, $-S(O)_2N(R^{12})(R^{13})$, $-S(=O)(=NH)N(R^{12})(R^{13})$, $-CH_2C(O)N(R^{12})(R^{13})$, $-CH_2N(R^{14})C(O)R^{15}$, $-CH_2S(O)_2R^{15}$, $-CH_2S(O)_2N(R^{12})(R^{13})$, $-CH_2N(R^{12})S(O)_2(R^{13})$, and $-P(O)(R^{17})(R^{17a})$ wherein $C_{1-6}$alkyl, $C_{2-6}$alkenyl, $C_{2-6}$alkynyl, $C_{3-10}$cycloalkyl, and $C_{2-9}$heterocycloalkyl are optionally substituted with one, two, or three $R^{20c}$;

$R^7$ is selected from hydrogen, halogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{1-9}$heteroaryl, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{15}$, —$S(O)_2R^{15}$, —$S(O)_2N(R^{12})(R^{13})$, —$S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, —$CH_2S(O)_2N(R^{12})(R^{13})$, —$CH_2N(R^{12})S(O)_2(R^{13})$, and —$P(O)(R^{17})(R^{17a})$, wherein $C_{1-6}$alkyl, $C_{2-6}$alkenyl, $C_{2-6}$alkynyl, $C_{3-10}$cycloalkyl, $C_{2-9}$heterocycloalkyl, and $C_{1-9}$heteroaryl are optionally substituted with one, two, or three $R^{20c}$;

each $R^{10}$ is independently selected from halogen, —CN, $C_{1-6}$alkyl, $C_{2-6}$alkenyl, $C_{2-6}$alkynyl, $C_{3-7}$cycloalkyl, $C_{2-9}$heterocycloalkyl, $C_{6-10}$aryl, $C_{1-9}$heteroaryl, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{15}$, —$S(O)R^{15}$, —$OC(O)R^{15}$, —$C(O)N(R^{12})(R^{13})$, —$C(O)N(R^{12})(R^{13})$, —$N(R^{14})C(O)R^{15}$, —$S(O)_2R^{15}$, —$S(O)_2N(R^{12})(R^{13})$, —$S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, —$CH_2S(O)_2N(R^{12})(R^{13})$, —$CH_2N(R^{12})S(O)_2(R^{13})$, and —$P(O)(R^{17})(R^{17a})$, wherein $C_{1-6}$alkyl, $C_{2-6}$alkenyl, $C_{2-6}$alkynyl, $C_{3-7}$cycloalkyl, $C_{2-9}$heterocycloalkyl, $C_{6-10}$aryl, and $C_{1-9}$heteroaryl are optionally substituted with one, two, or three $R^{20a}$;

each $R^{12}$ is independently selected from hydrogen, $C_{1-6}$alkyl, $C_{1-6}$haloalkyl, $C_{2-6}$alkenyl, $C_{2-6}$alkynyl, $C_{3-7}$cycloalkyl, $C_{2-9}$heterocycloalkyl, $C_{6-10}$aryl, and $C_{1-9}$heteroaryl, wherein $C_{1-6}$alkyl, $C_{2-6}$alkenyl, $C_{2-6}$alkynyl, $C_{3-7}$cycloalkyl, $C_{2-9}$heterocycloalkyl, $C_{6-10}$aryl, and $C_{1-9}$heteroaryl are optionally substituted with one, two, or three $R^{20e}$;

each $R^{13}$ is independently selected from hydrogen, $C_{1-6}$alkyl, and $C_{1-6}$haloalkyl; or $R^{12}$ and $R^{13}$, together with the nitrogen to which they are attached, form a $C_{2-9}$heterocycloalkyl ring optionally substituted with one, two, or three $R^{20f}$;

$R^{13a}$ is selected from $C_{1-6}$alkyl and $C_{1-6}$haloalkyl; or $R^{12}$ and $R^{13a}$, together with the nitrogen to which they are attached, form a $C_{2-9}$heterocycloalkyl ring optionally substituted with one, two, or three $R^{20f}$;

each $R^{14}$ is independently selected from hydrogen, $C_{1-6}$alkyl, and $C_{1-6}$haloalkyl;

each $R^{15}$ is independently selected $C_{1-6}$alkyl, $C_{2-6}$alkenyl, $C_{2-6}$alkynyl, $C_{3-7}$cycloalkyl, $C_{2-9}$heterocycloalkyl, $C_{6-10}$aryl, and $C_{1-9}$heteroaryl, wherein $C_{1-6}$alkyl, $C_{2-6}$alkenyl, $C_{2-6}$alkynyl, $C_{3-7}$cycloalkyl, $C_{2-9}$heterocycloalkyl, $C_{6-10}$aryl, and $C_{1-9}$heteroaryl are optionally substituted with one, two, or three $R^{20g}$;

each $R^{17}$ and each $R^{17a}$ are each independently selected from $C_{1-6}$alkyl and $C_{3-6}$cycloalkyl, wherein $C_{1-6}$alkyl and $C_{3-6}$cycloalkyl are optionally substituted with one, two or three of $R^{20h}$; or $R^{17}$ and $R^{17a}$ are combined to form a $C_{2-9}$heterocycloalkyl ring;

each $R^{20a}$, $R^{20b}$, $R^{20c}$, $R^{20d}$, $R^{20e}$, $R^{20f}$, $R^{20g}$, and $R^{20h}$ are each independently selected from halogen, oxo, =NH, —CN, $C_{1-6}$alkyl, $C_{2-6}$alkenyl, $C_{2-6}$alkynyl, $C_{3-10}$cycloalkyl, —$CH_2$—$C_{3-10}$cycloalkyl, $C_{2-9}$heterocycloalkyl, —$CH_2$—$C_{2-9}$heterocycloalkyl, $C_{6-10}$aryl, —$CH_2$—$C_{6-10}$aryl, $C_{1-9}$heteroaryl, —$OR^{21}$, —$SR^{21}$, —$N(R^{22})(R^{23})$, —$C(O)OR^{22}$, —$C(O)N(R^{22})(R^{23})$, —$C(O)C(O)N(R^{22})$ ($R^{23}$), —$OC(O)N(R^{22})(R^{23})$, —$N(R^{24})C(O)N(R^{22})(R^{23})$, —$N(R^{24})C(O)OR^{25}$, —$N(R^{24})C(O)R^{25}$, —$N(R^{24})S(O)_2R^{25}$, —$C(O)R^{25}$, —$S(O)_2R^{25}$, —$S(O)_2N(R^{22})(R^{23})$, —$OCH_2C(O)OR^{22}$, and —$OC(O)R^{25}$, wherein $C_{1-6}$alkyl, $C_{2-6}$alkenyl, $C_{2-6}$alkynyl, $C_{3-10}$cycloalkyl, —$CH_2$—$C_{3-10}$cycloalkyl, $C_{2-9}$heterocycloalkyl, —$CH_2$—$C_{2-9}$heterocycloalkyl, $C_{6-10}$aryl, —$CH_2$—$C_{6-10}$aryl, and $C_{1-9}$heteroaryl are optionally substituted with one, two, or three groups independently selected from halogen, oxo, =NH, —CN, $C_{1-6}$alkyl, $C_{1-6}$haloalkyl, $C_{1-6}$alkoxy, $C_{1-6}$haloalkoxy, —$OR^{21}$, —$SR^{21}$, —$N(R^{22})(R^{23})$, —$C(O)OR^{22}$, —$C(O)N(R^{22})(R^{23})$, —$C(O)C(O)N(R^{22})(R^{23})$, —$OC(O)N(R^{22})(R^{23})$, —$N(R^{24})C(O)N(R^{22})(R^{23})$, —$N(R^{24})C(O)OR^{25}$, —$N(R^{24})C(O)R^{25}$, —$N(R^{24})S(O)_2R^{25}$, —$C(O)R^{25}$, —$S(O)_2R^{25}$, —$S(O)_2N(R^{22})(R^{23})$, and —$OC(O)R^{25}$;

each $R^{21}$ is independently selected from H, $C_{1-6}$alkyl, $C_{1-6}$haloalkyl, $C_{2-6}$alkenyl, $C_{2-6}$alkynyl, $C_{3-7}$cycloalkyl, $C_{2-9}$heterocycloalkyl, $C_{6-10}$aryl, and $C_{1-9}$heteroaryl, wherein $C_{3-7}$cycloalkyl, $C_{2-9}$heterocycloalkyl, $C_{6-10}$aryl, and $C_{1-9}$heteroaryl are optionally substituted with one, two, or three groups independently selected from halogen and $C_{1-6}$alkyl;

each $R^{22}$ is independently selected from H, $C_{1-6}$alkyl, $C_{1-6}$haloalkyl, $C_{2-6}$alkenyl, $C_{2-6}$alkynyl, $C_{3-7}$cycloalkyl, $C_{2-9}$heterocycloalkyl, $C_{6-10}$aryl, and $C_{1-9}$heteroaryl, wherein $C_{3-7}$cycloalkyl, $C_{2-9}$heterocycloalkyl, $C_{6-10}$aryl, and $C_{1-9}$heteroaryl are optionally substituted with one, two, or three groups independently selected from halogen and $C_{1-6}$alkyl;

each $R^{23}$ is independently selected from H and $C_{1-6}$alkyl;

each $R^{24}$ is independently selected from H and $C_{1-6}$alkyl; and each $R^{25}$ is selected from $C_{1-6}$alkyl, $C_{2-6}$alkenyl, $C_{2-6}$alkynyl, $C_{3-7}$cycloalkyl, $C_{2-9}$heterocycloalkyl, $C_{6-10}$aryl, and $C_{1-9}$heteroaryl, wherein $C_{1-6}$alkyl, $C_{3-7}$cycloalkyl, $C_{2-9}$heterocycloalkyl, $C_{6-10}$aryl, and $C_{1-9}$heteroaryl are optionally substituted with one, two, or three groups independently selected from halogen, $C_{1-6}$alkyl, $C_{1-6}$haloalkyl, $C_{1-6}$alkoxy, $C_{3-7}$cycloalkyl, $C_{2-9}$heterocycloalkyl, $C_{6-10}$aryl, and $C_{1-9}$heteroaryl.

In embodiments of the compound of Formula (I-2), the compound has the Formula (Ia-2), or a pharmaceutically acceptable salt or solvate thereof:

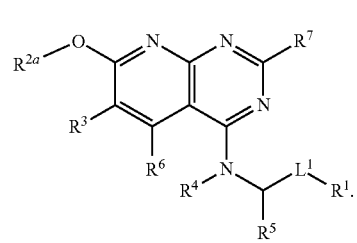

Formula (Ia-2)

In some embodiments, $R^{2a}$ is $C_{1-6}$alkyl optionally substituted with one, two, or three $R^{20a}$.

In some embodiments, $R^{2a}$ is unsubstituted $C_{1-6}$alkyl.

In some embodiments, $R^{2a}$ is —$CH_3$.

In embodiments of the compound of Formula (I-2), the compound has the Formula (Ib-2), or a pharmaceutically acceptable salt or solvate thereof:

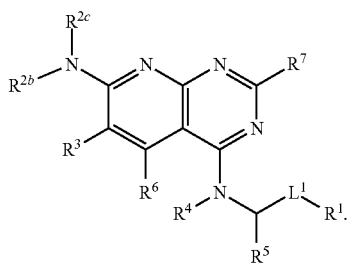

Formula (Ib-2)

In some embodiments, $R^{2b}$ is $C_{1-6}$alkyl optionally substituted with one, two, or three $R^{20a}$.

In some embodiments, $R^{2c}$ is $C_{1-6}$alkyl optionally substituted with one, two, or three $R^{20a}$.

In some embodiments, $R^{2c}$ is hydrogen.

In embodiments of the compound of Formula (I-2), the compound has the Formula (Ic-2), or a pharmaceutically acceptable salt or solvate thereof:

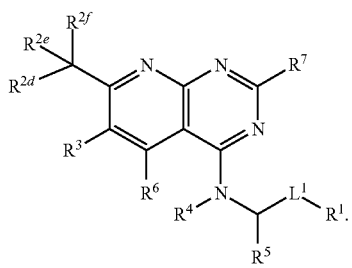

Formula (Ic-2)

In some embodiments, $R^{2a}$ is hydrogen or $C_{1-6}$alkyl optionally substituted with one, two, or three $R^{20a}$.

In some embodiments, $R^{2e}$ is hydrogen.
In some embodiments, $R^{2f}$ is hydrogen.
In some embodiments, $R^2$ is halogen.
In some embodiments, $R^{20b}$ is —CN.
In some embodiments, $R^3$ is

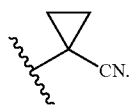

In some embodiments, $R^6$ is selected from hydrogen, halogen, $C_{1-6}$alkyl, $C_{3-10}$cycloalkyl, $C_{2-9}$heterocycloalkyl, and $C_{1-9}$heteroaryl, wherein $C_{1-6}$alkyl, $C_{3-10}$cycloalkyl, $C_{2-9}$heterocycloalkyl, and $C_{1-9}$heteroaryl are optionally substituted with one, two, or three $R^{20c}$. In some embodiments, $R^6$ is independently selected from hydrogen, halogen, and unsubstituted $C_{1-6}$alkyl. In some embodiments, $R^6$ is hydrogen.

In some embodiments, $R^7$ is selected from hydrogen, halogen, $C_{1-6}$alkyl, $C_{3-10}$cycloalkyl, $C_{2-9}$heterocycloalkyl, and $C_{1-9}$heteroaryl, wherein $C_{1-6}$alkyl, $C_{3-10}$cycloalkyl, $C_{2-9}$heterocycloalkyl, and $C_{1-9}$heteroaryl are optionally substituted with one, two, or three $R^{20c}$. In some embodiments, $R^7$ is independently selected from hydrogen, halogen, and unsubstituted $C_{1-6}$alkyl. In some embodiments, $R^7$ is unsubstituted $C_{1-6}$alkyl. In some embodiments, $R^7$ is hydrogen.

In some embodiments, $R^5$ is selected from $C_{1-6}$alkyl and $C_{1-6}$haloalkyl. In some embodiments, $R^5$ is —$CH_3$.

In some embodiments, $R^4$ is hydrogen.
In some embodiments, $L^1$ is a bond.
In some embodiments, $R^1$ is a 6-10 membered aryl ring substituted with one or more $R^{10}$. In some embodiments, $R^1$ is phenyl substituted with one or more $R^{10}$. In some embodiments, $R^1$ is phenyl substituted with one, two, or three $R^{10}$.

In some embodiments, each $R^{10}$ is independently selected from halogen, $C_{1-6}$alkyl, $C_{3-7}$cycloalkyl, $C_{2-9}$heterocycloalkyl, $C_{6-10}$aryl, $C_{1-9}$heteroaryl, —$OR^{12}$, and $N(R^{12})(R^{13})$, wherein $C_{1-6}$alkyl, $C_{3-7}$cycloalkyl, $C_{2-9}$heterocycloalkyl, $C_{6-10}$aryl, and $C_{1-9}$heteroaryl are optionally substituted with one, two, or three $R^{20a}$.

In some embodiments, each $R^{10}$ is independently selected from halogen, $C_{1-6}$alkyl, and $N(R^{12})(R^{13})$ wherein $C_{1-6}$alkyl is optionally substituted with one, two, or three $R^{20a}$.

In some embodiments, each $R^{10}$ is independently selected from halogen and $C_{1-6}$alkyl, wherein $C_{1-6}$alkyl is substituted with one, two, or three $R^{20d}$, and each $R^{20d}$ is halogen.

In some embodiments, $R^1$ is independently selected from

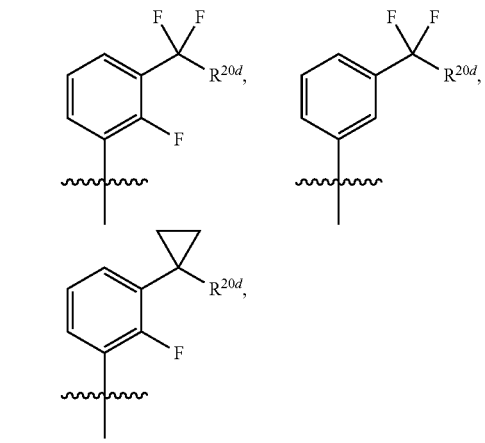

or

In some embodiments, $R^{20d}$ is $C_{1-6}$alkyl optionally substituted with one, two, or three groups independently selected from F and —OH.

In some embodiments, $R^{20d}$ is $C_{1-3}$alkyl substituted with one —OH.

In some embodiments, $R^1$ is selected from

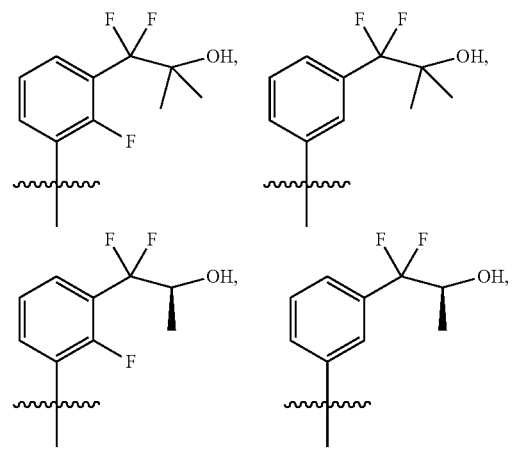

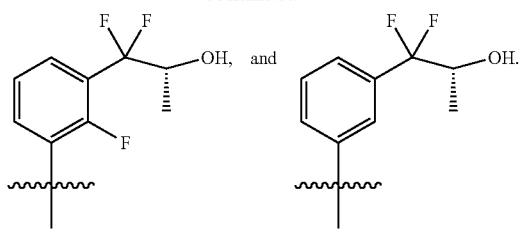
Also provided is a compound selected from:
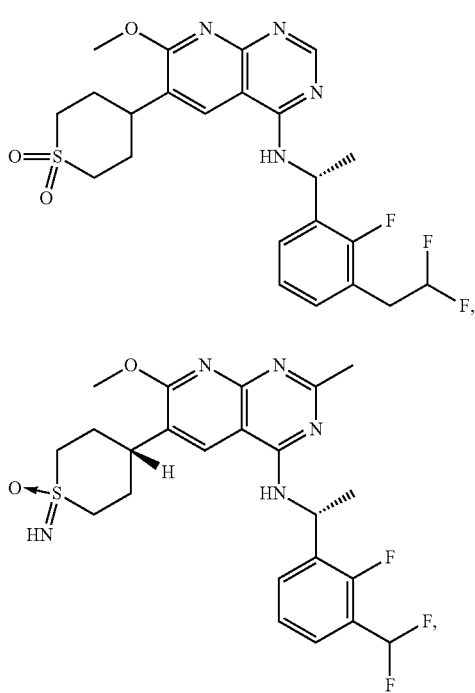
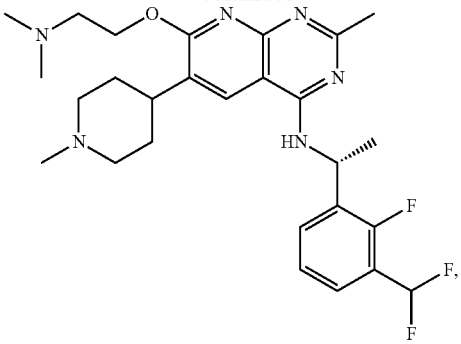
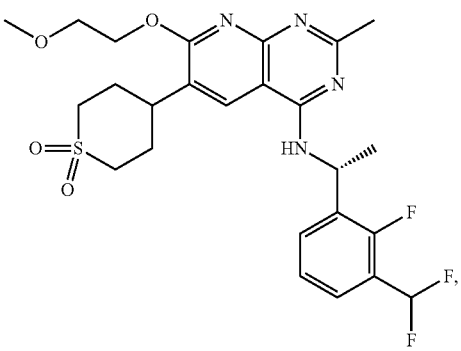
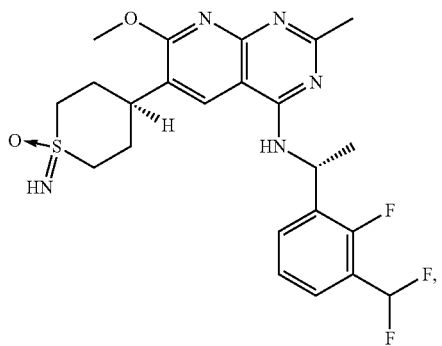
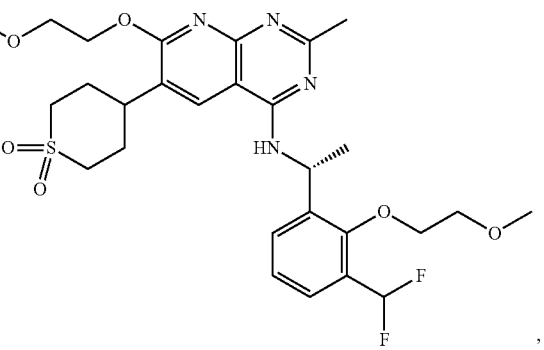

261
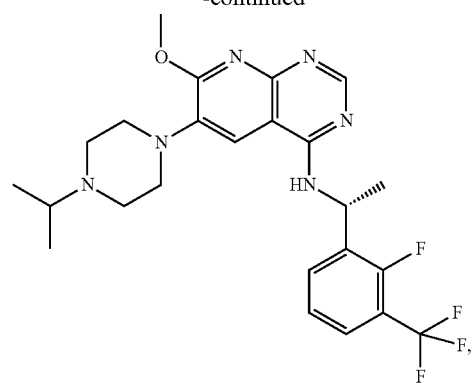
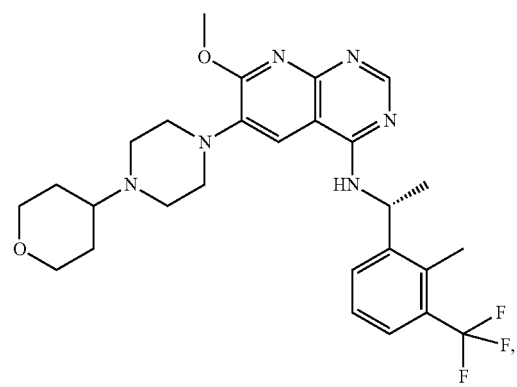
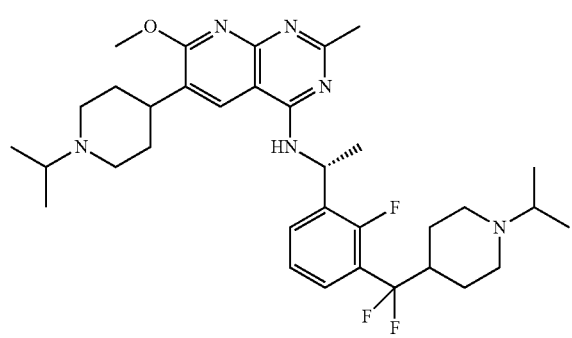
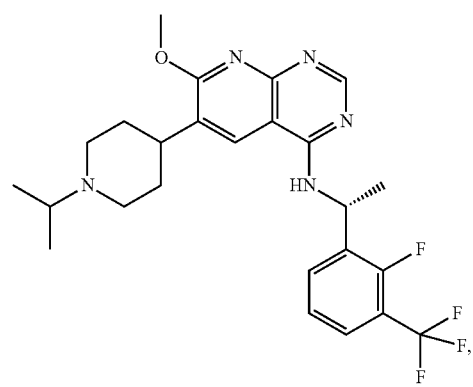
262
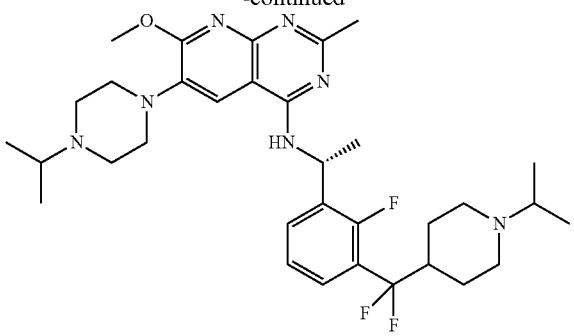
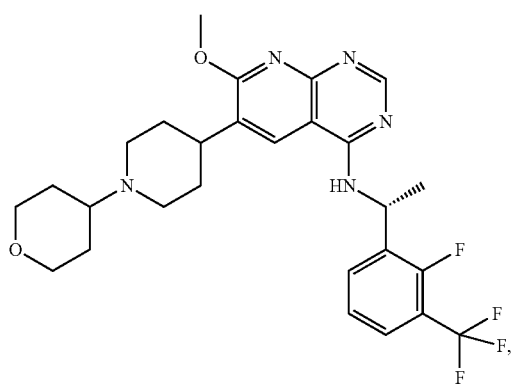
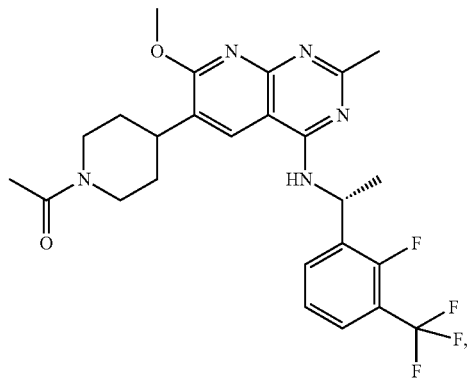
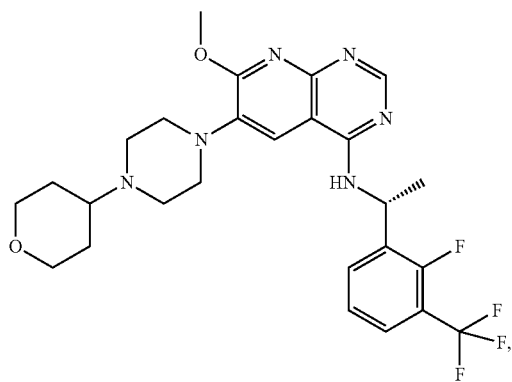

263
-continued
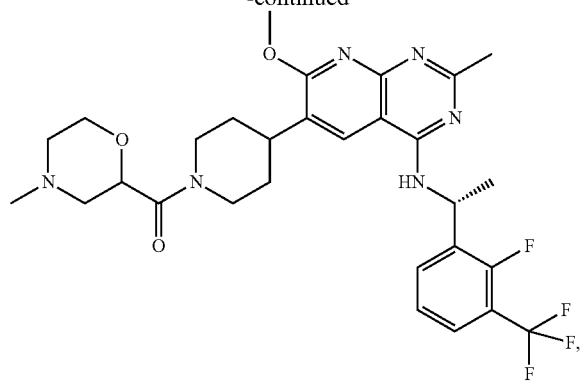
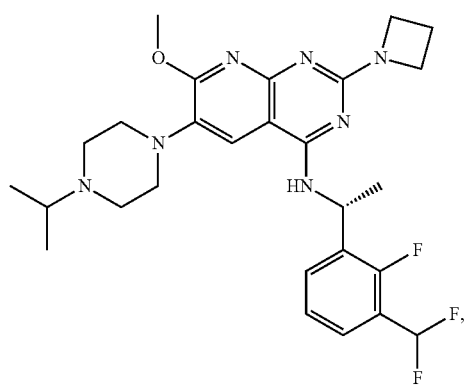
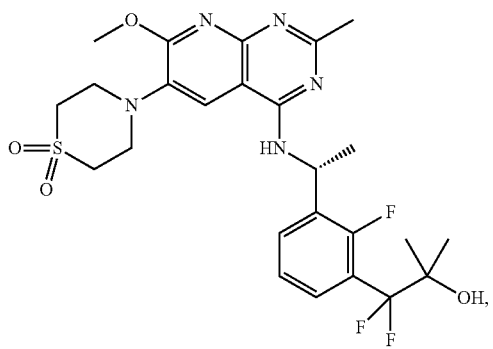
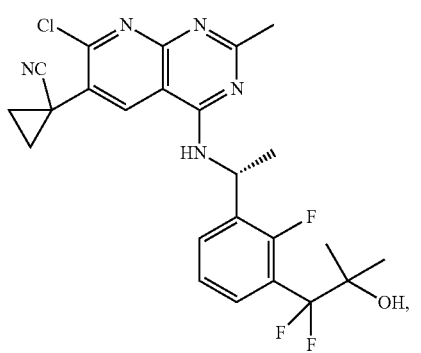
264
-continued
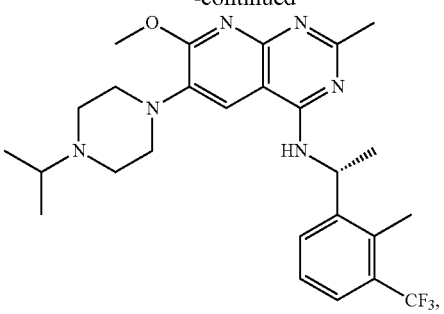
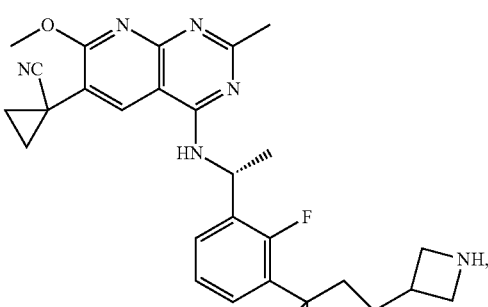
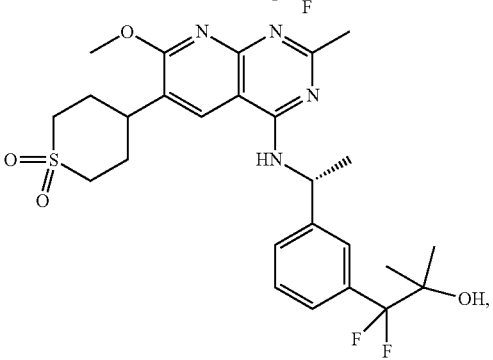
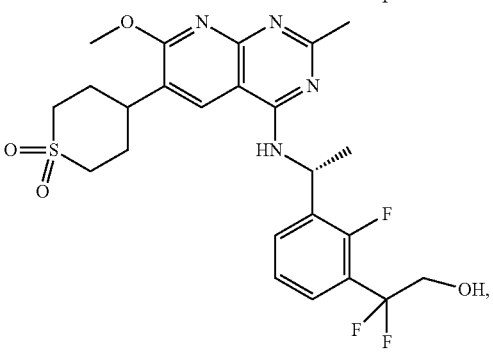

265
-continued
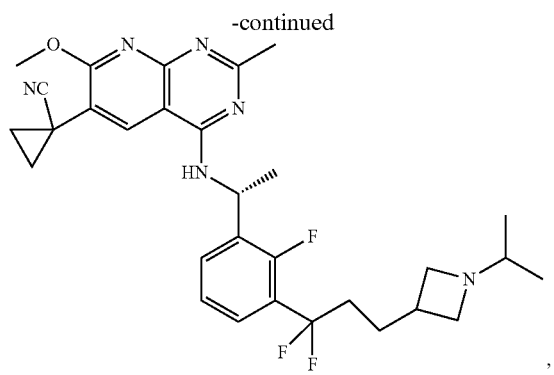
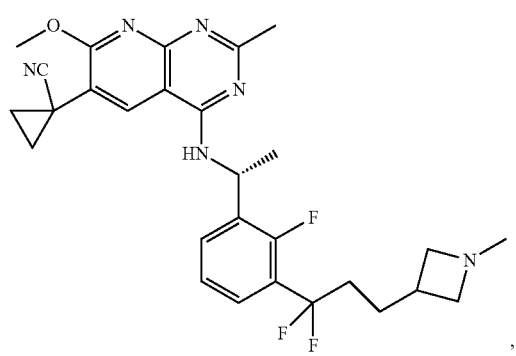
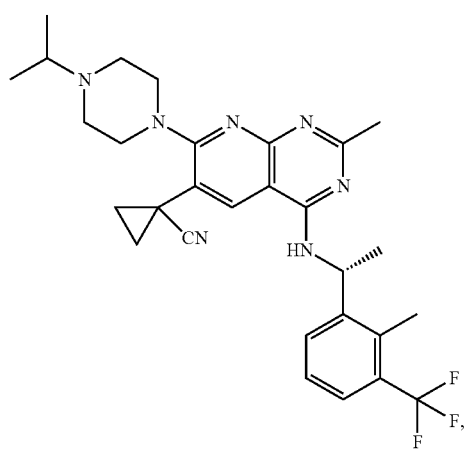
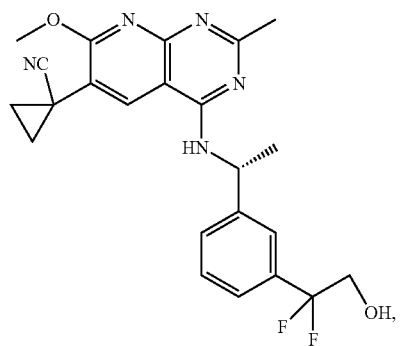
266
-continued
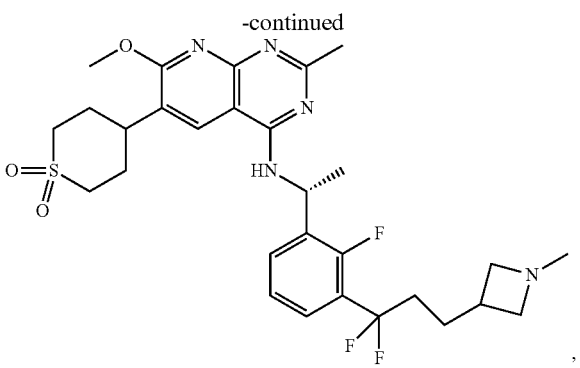
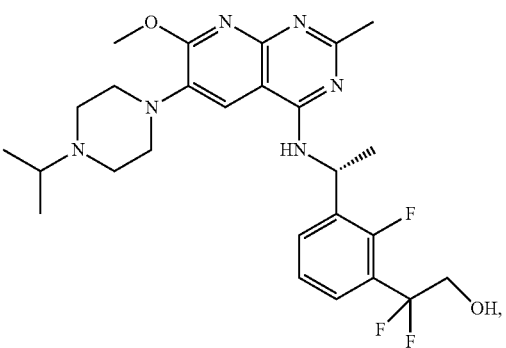
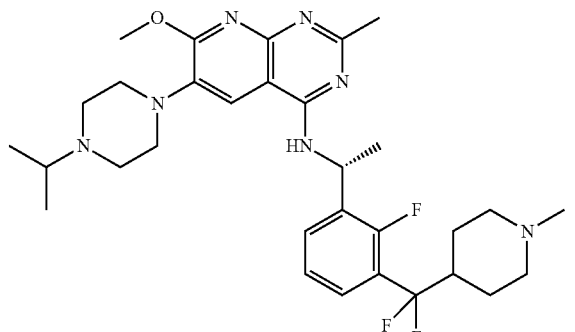
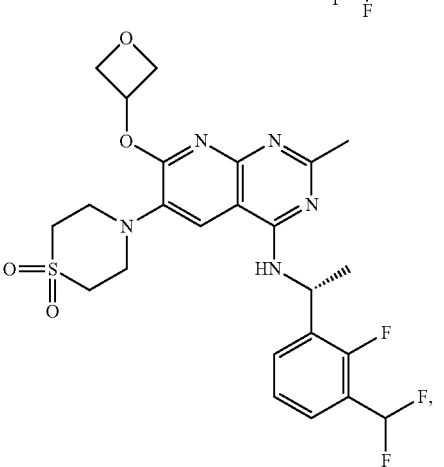

267
-continued
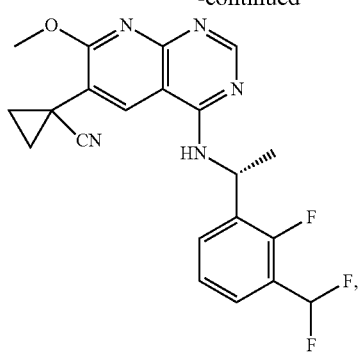
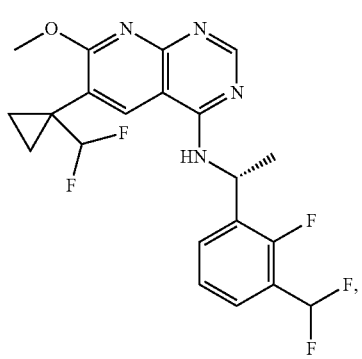
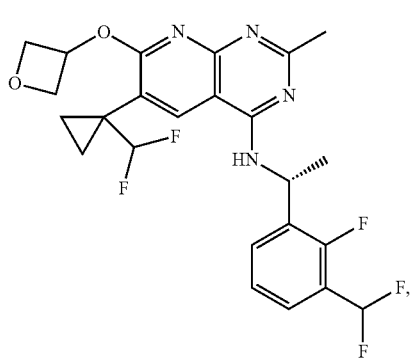
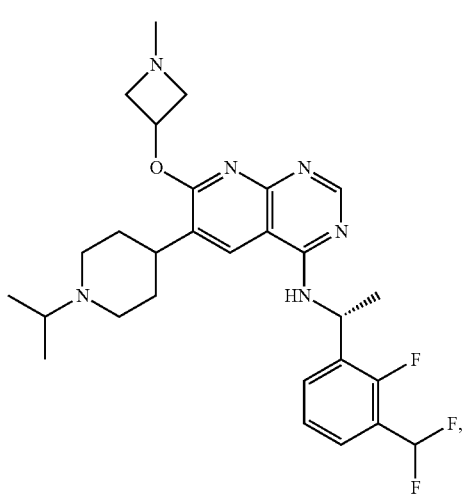
268
-continued
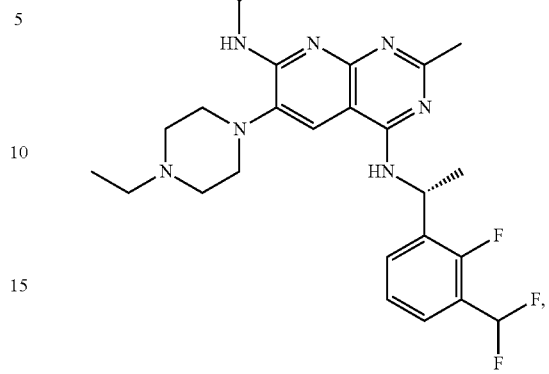
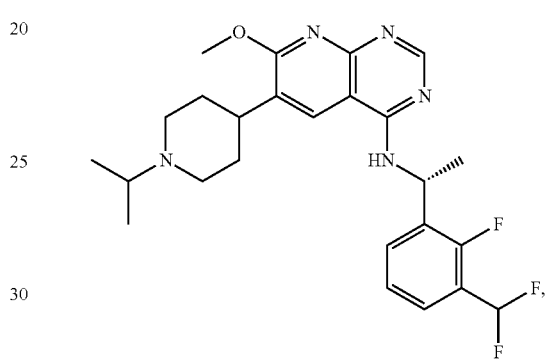
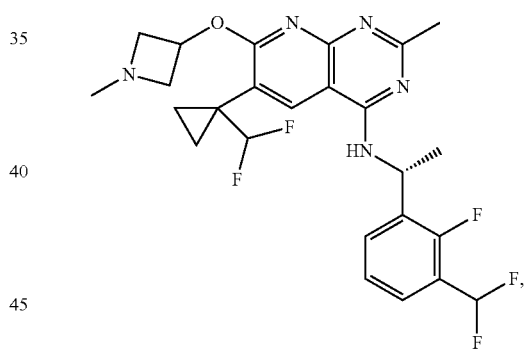
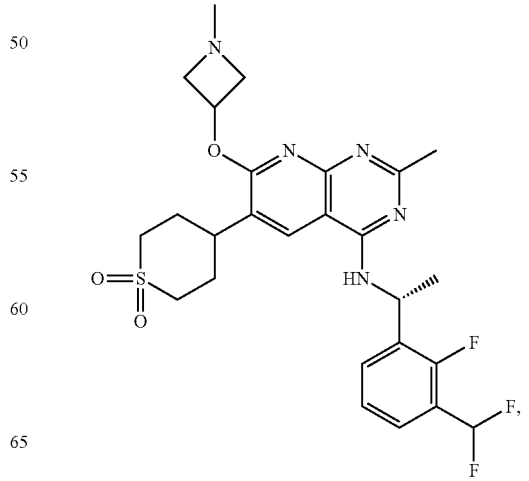

269
-continued
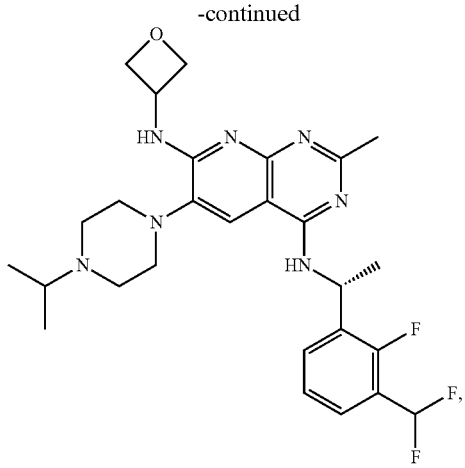
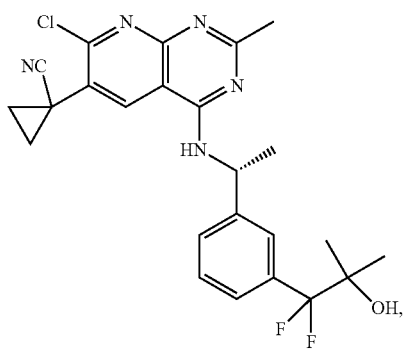
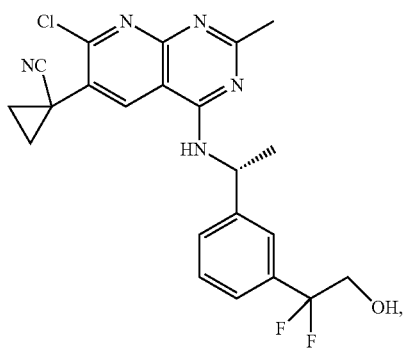
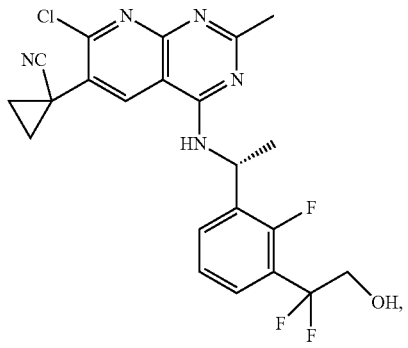
270
-continued
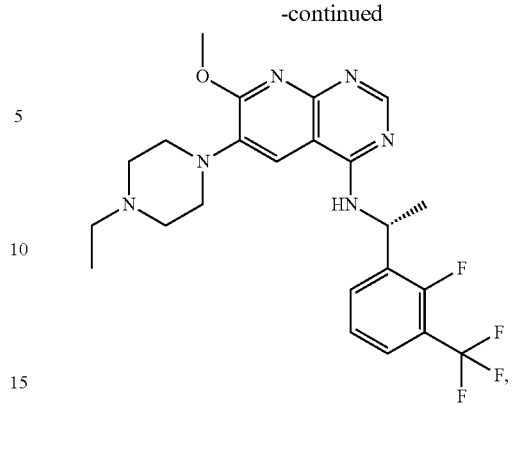
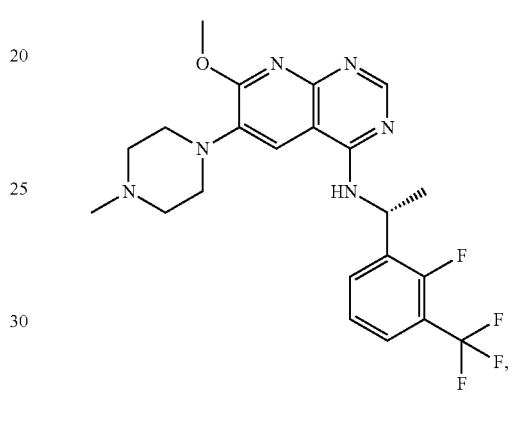
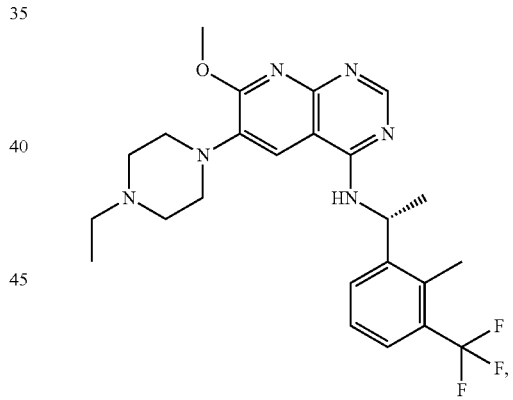
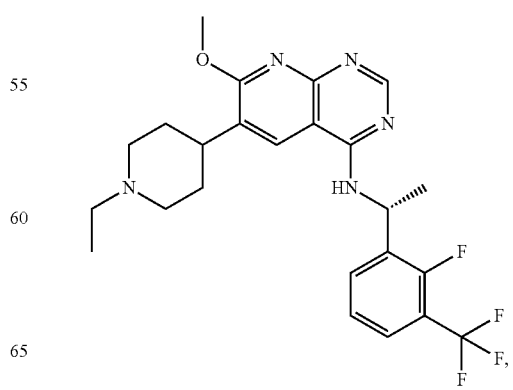

271
-continued
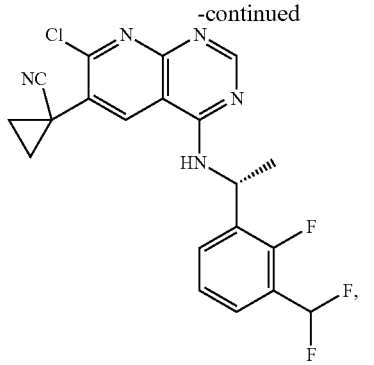
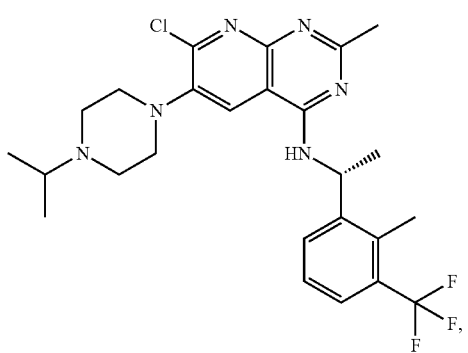
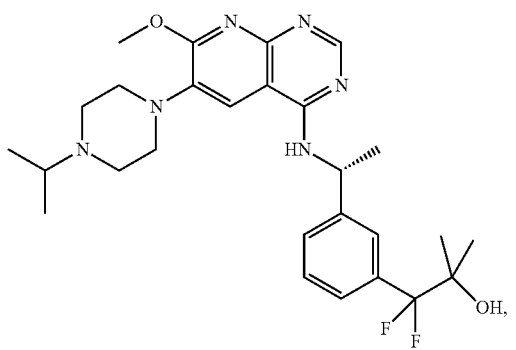
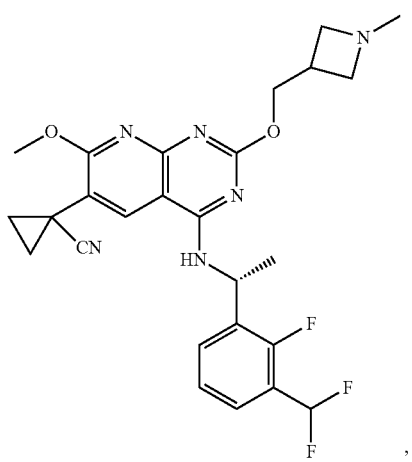
272
-continued
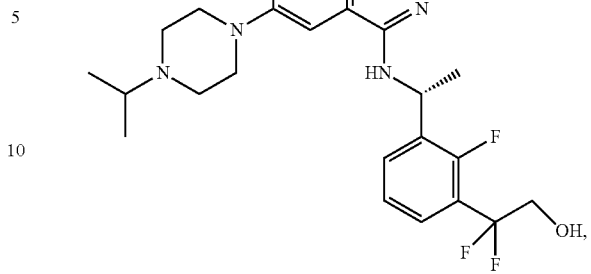
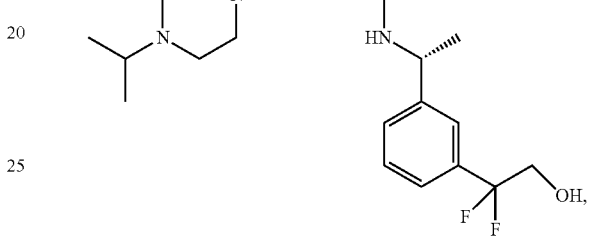
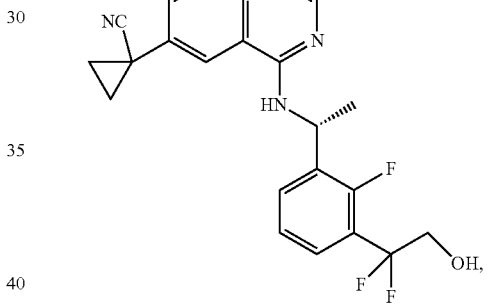
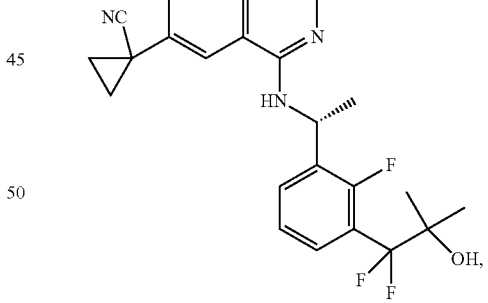
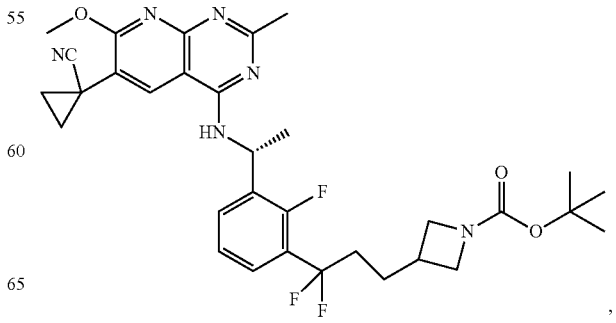

273
-continued
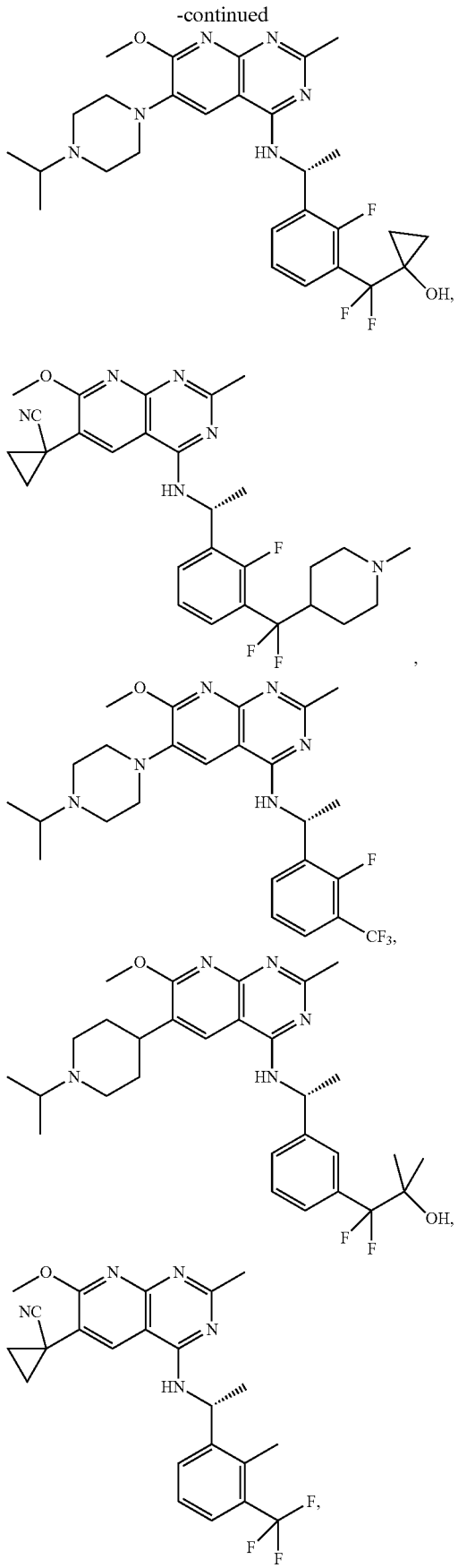
274
-continued
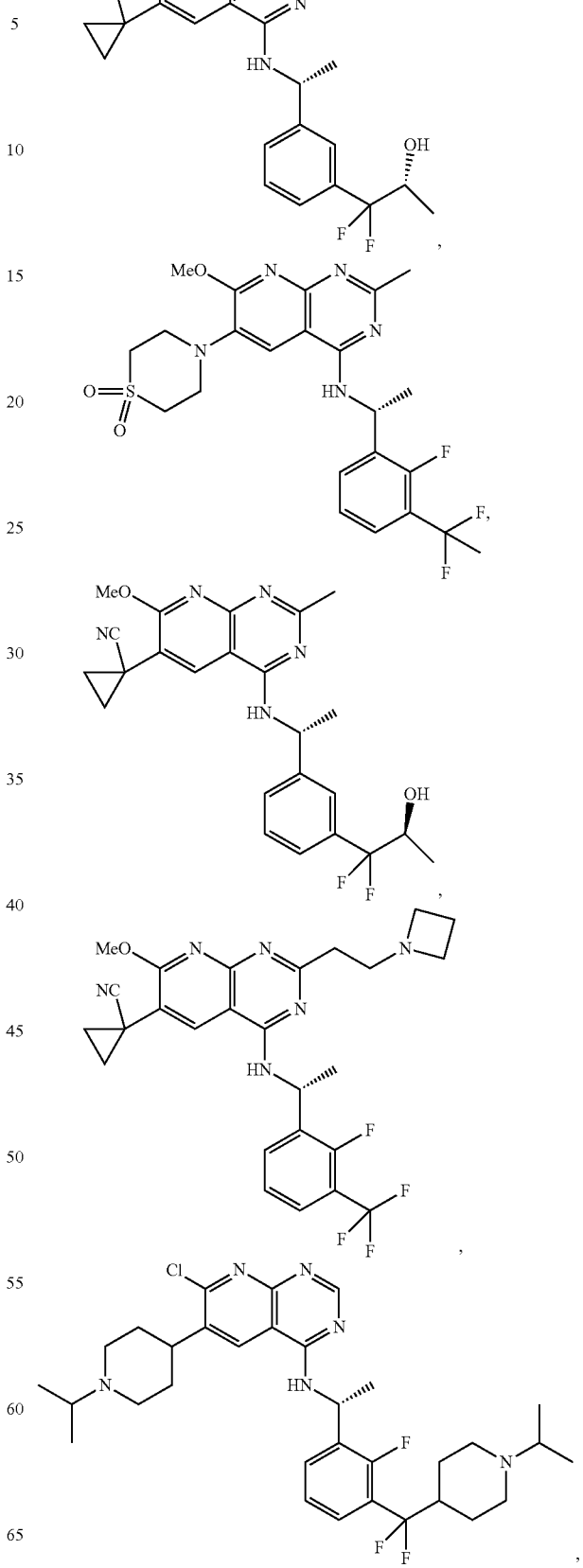

275
-continued
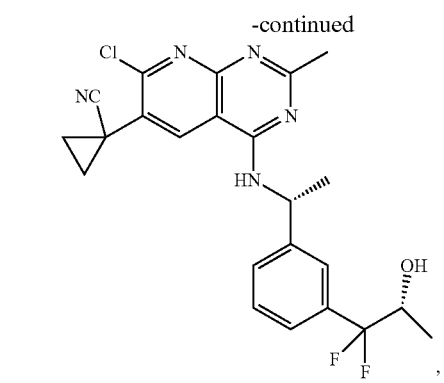
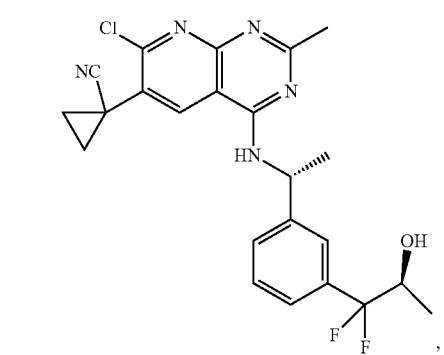
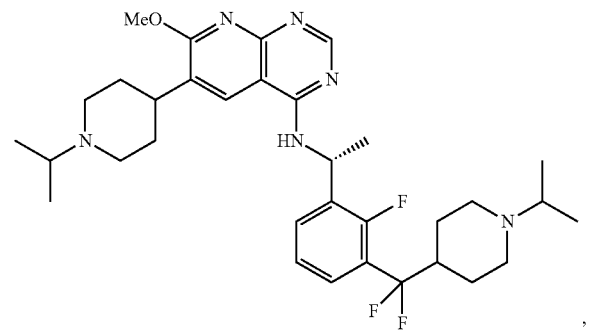
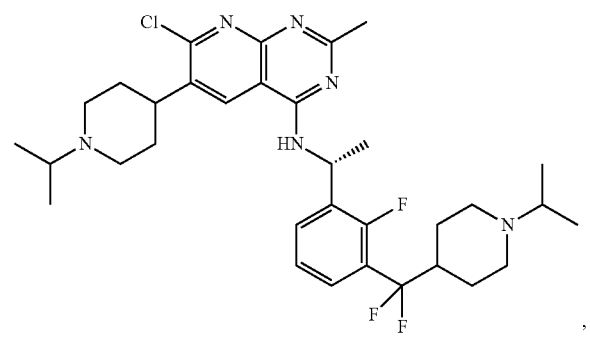
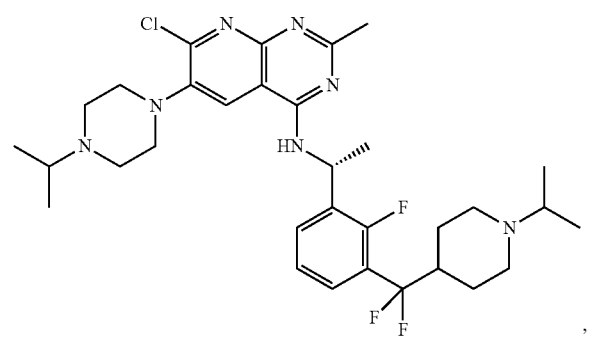
276
-continued
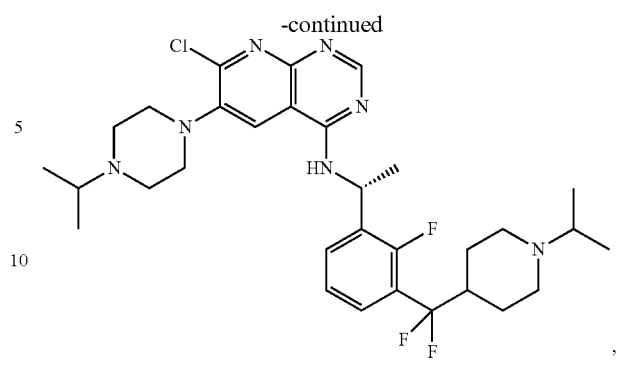
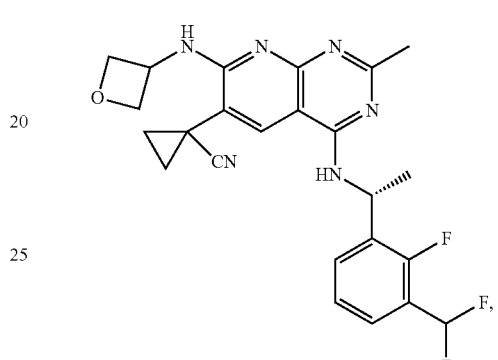
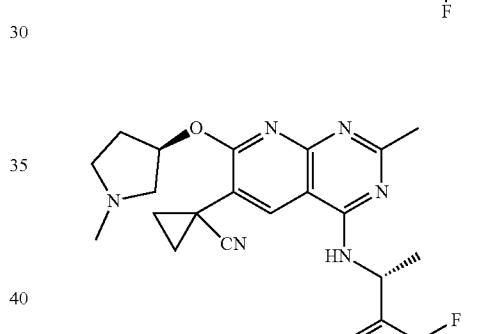
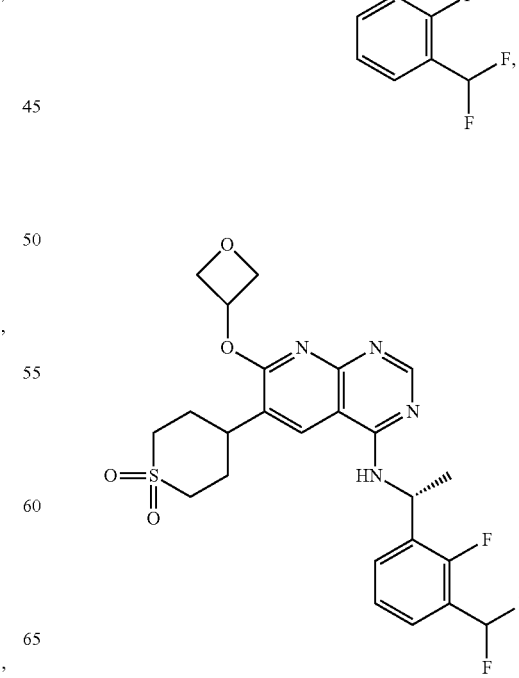

277
-continued
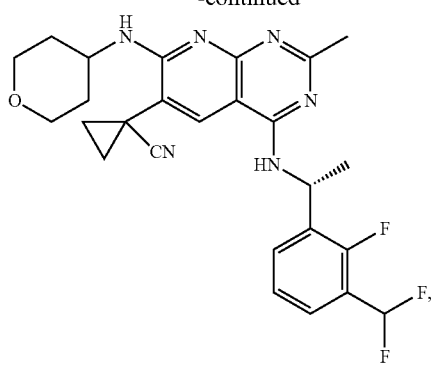
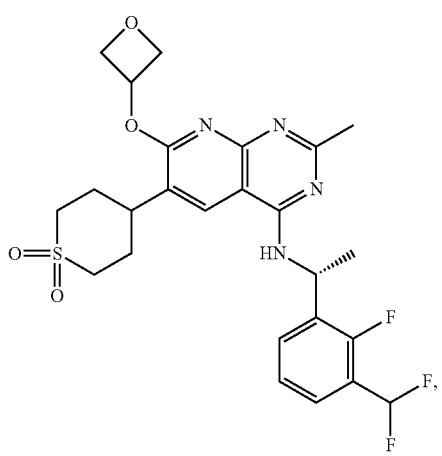
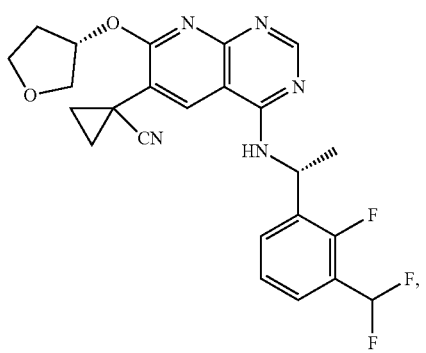
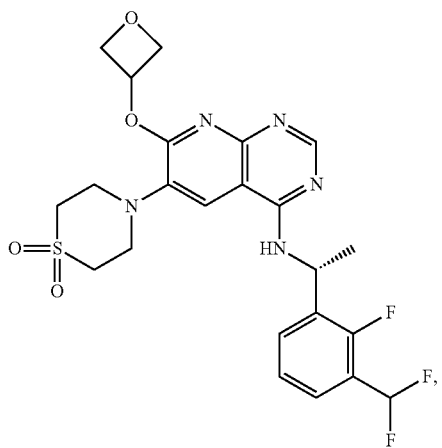
278
-continued
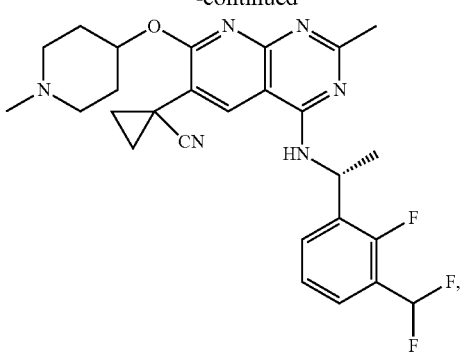
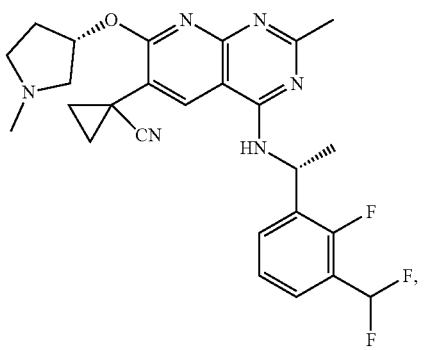
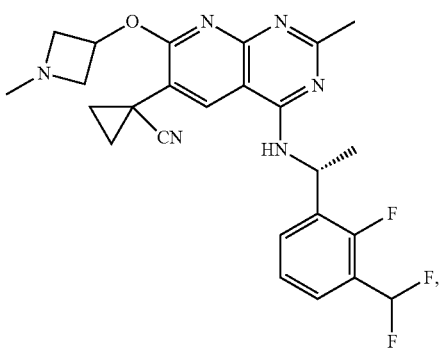
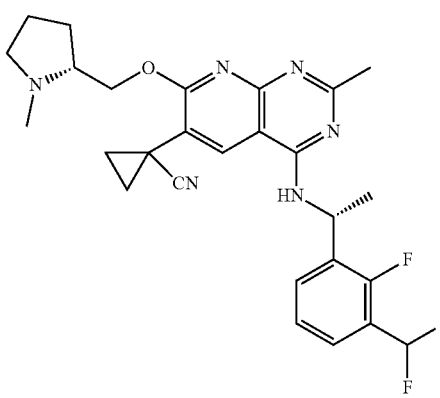

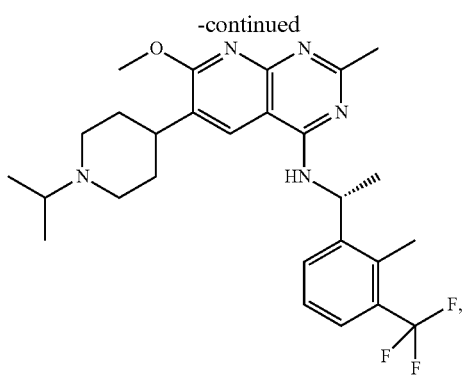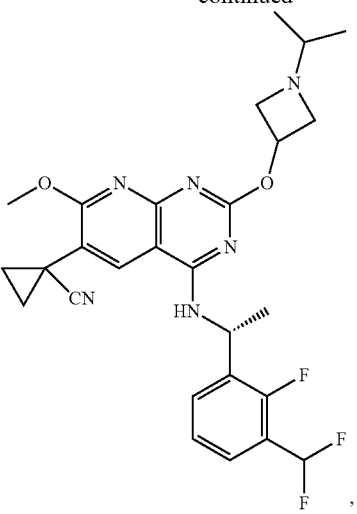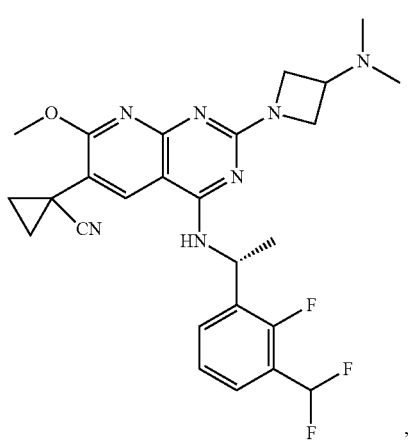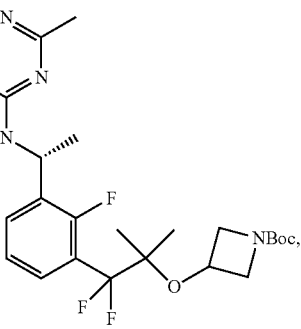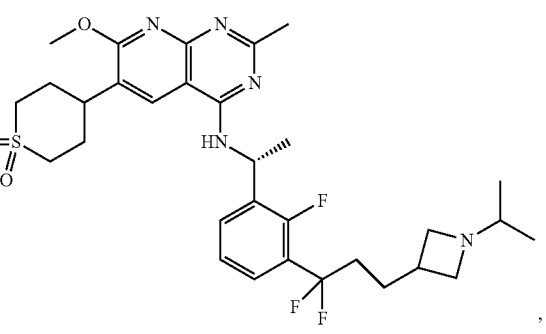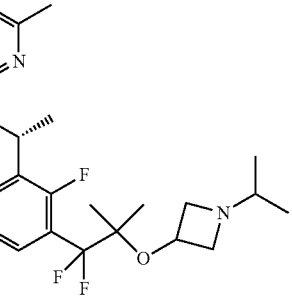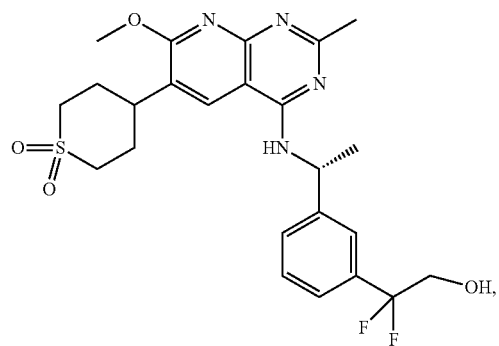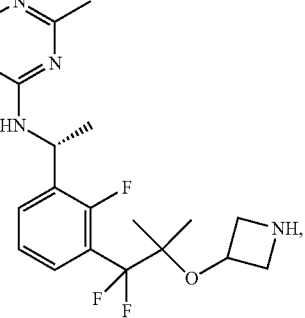

281
-continued
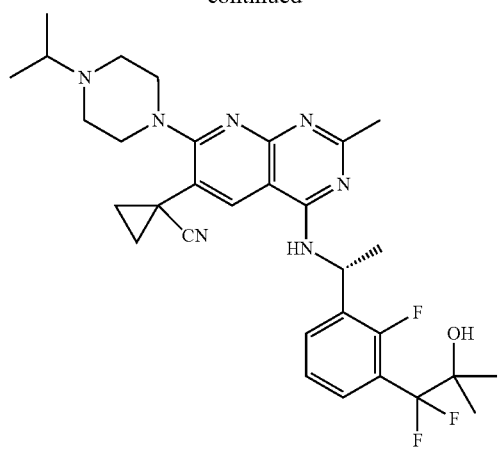
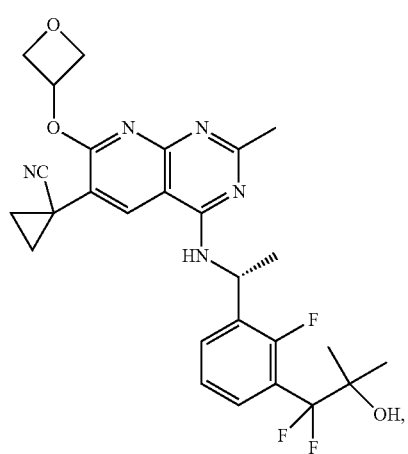
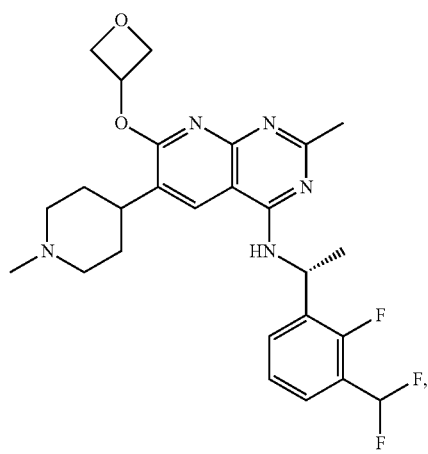
282
-continued
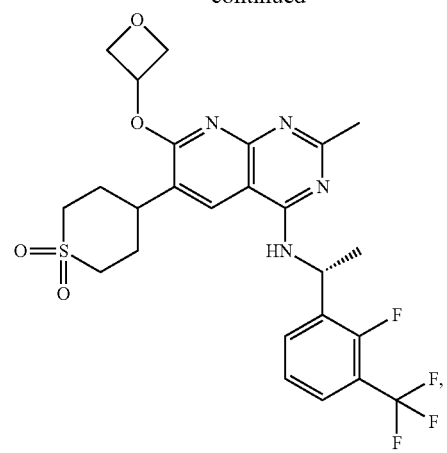
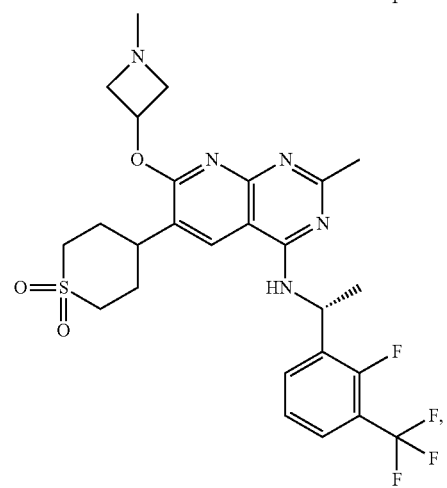
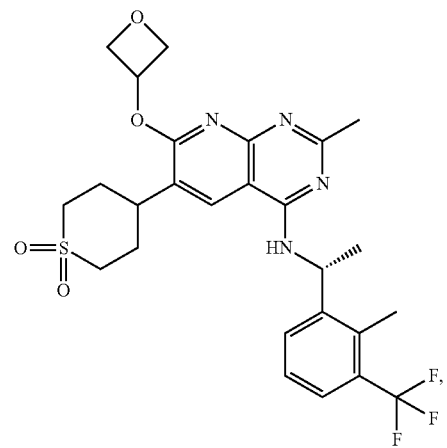
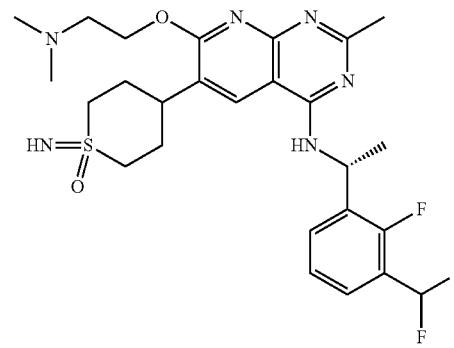

283
-continued
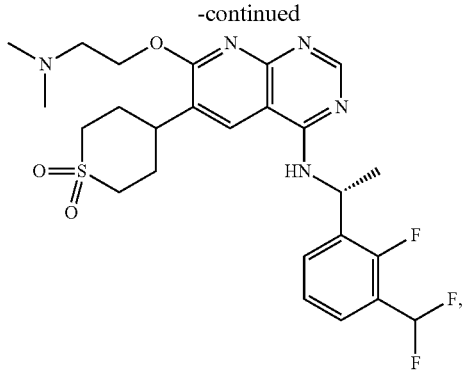
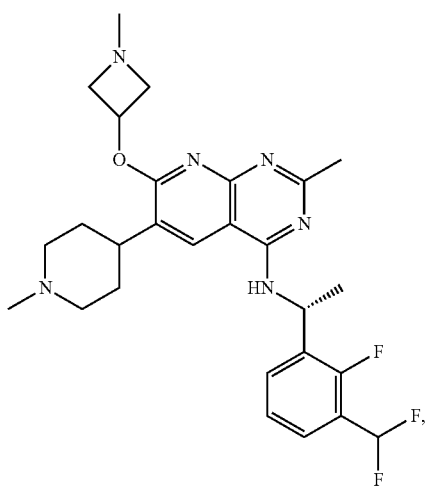
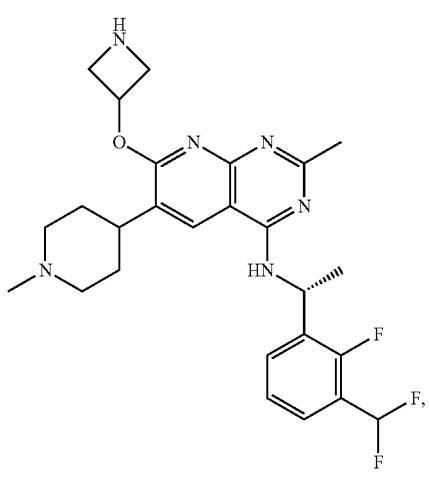
284
-continued
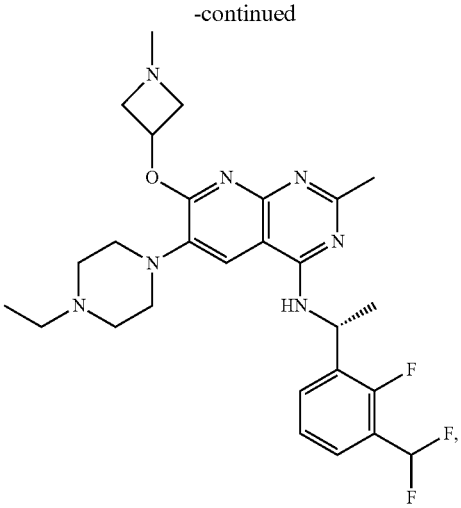
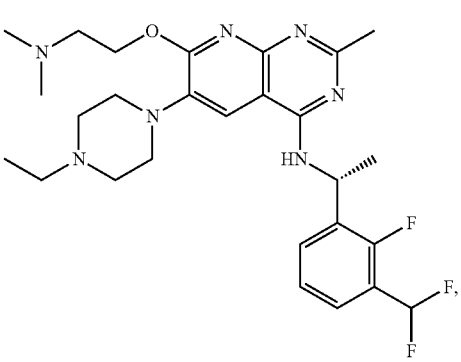
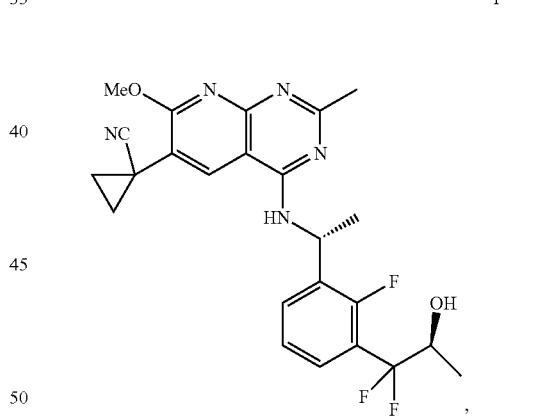
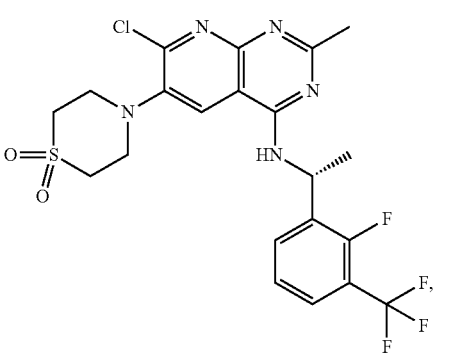

285
-continued
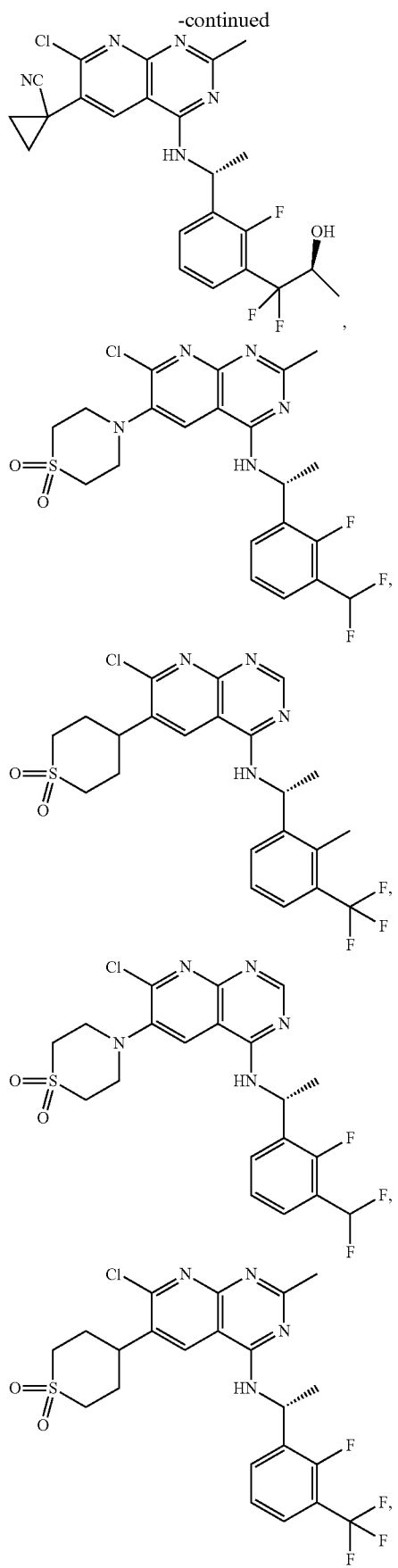
286
-continued
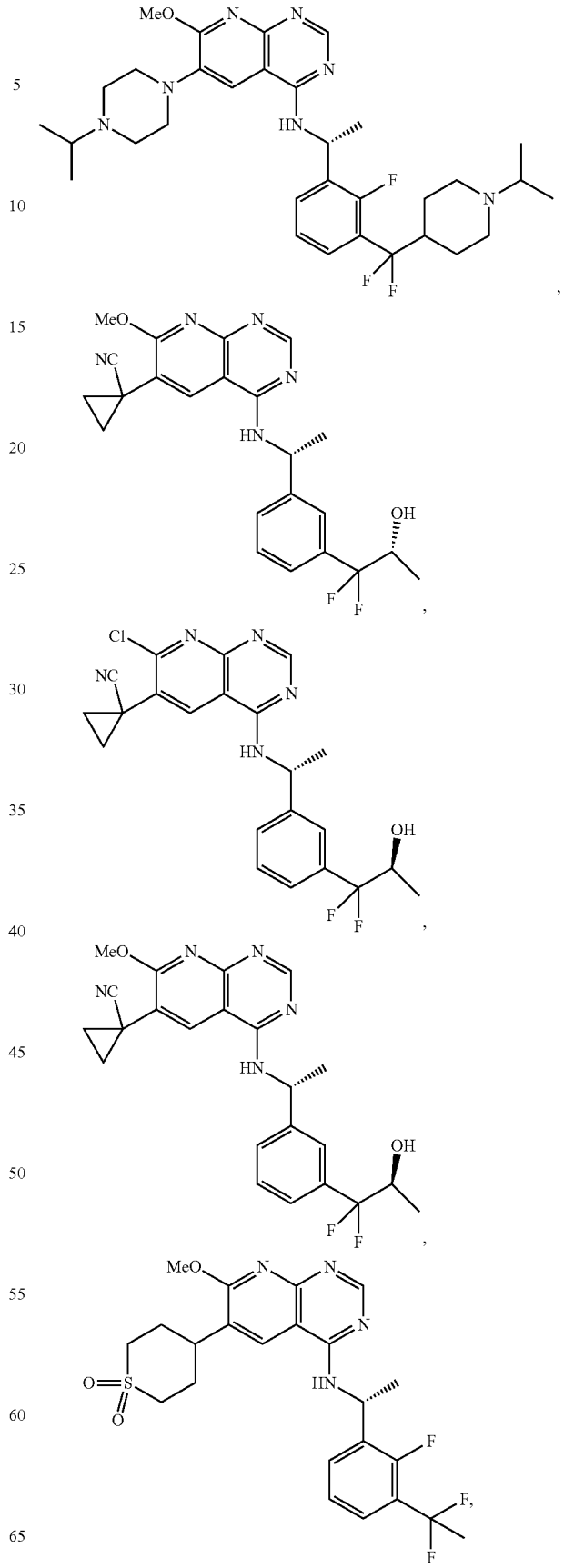

287
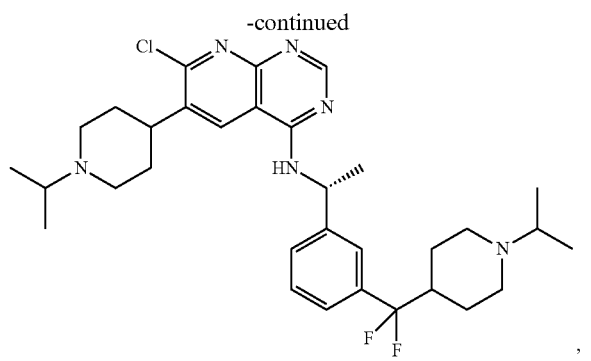
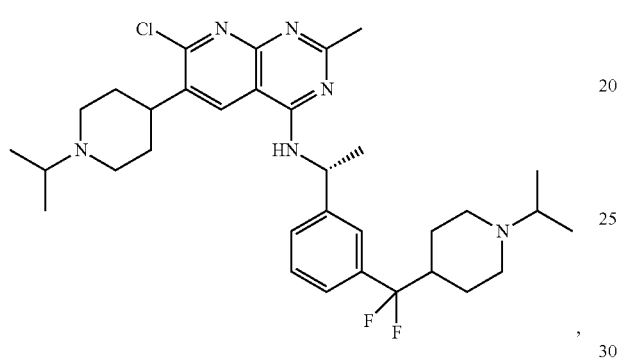
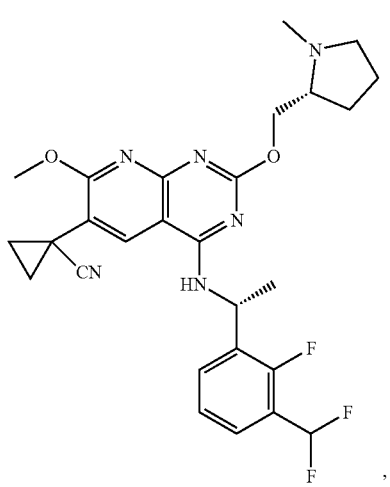
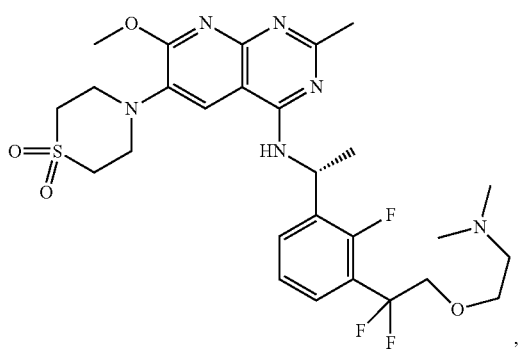
288
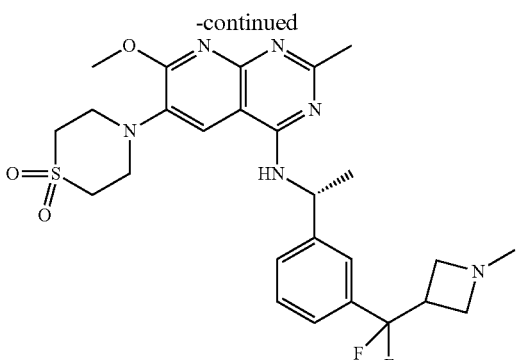
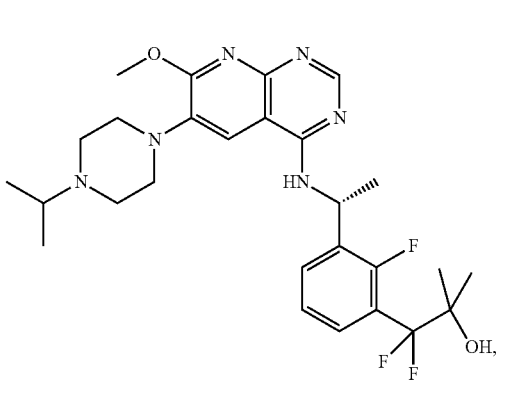
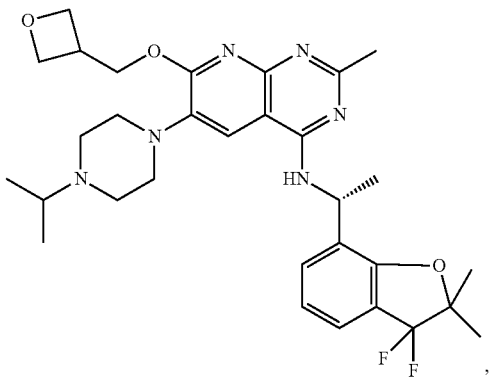
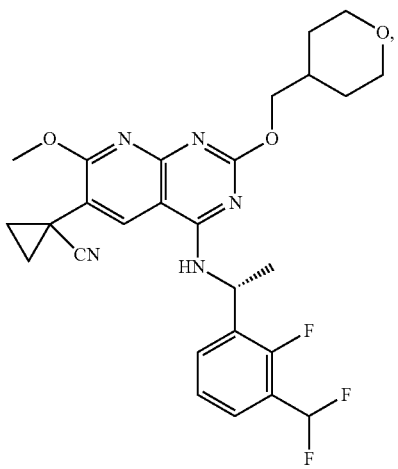

289
-continued
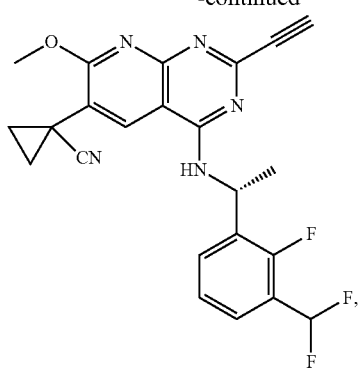
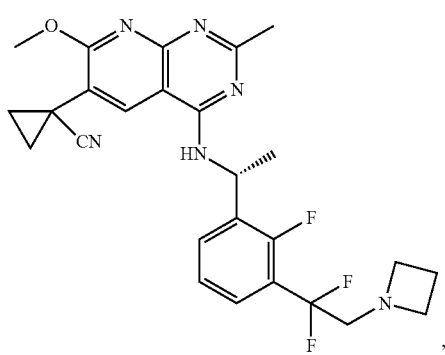
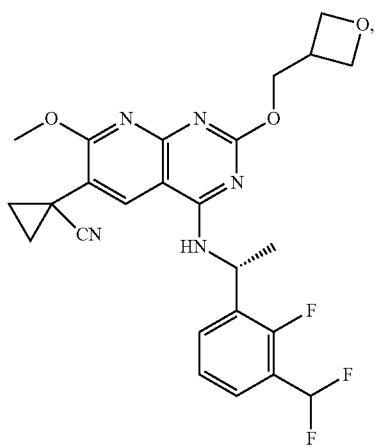
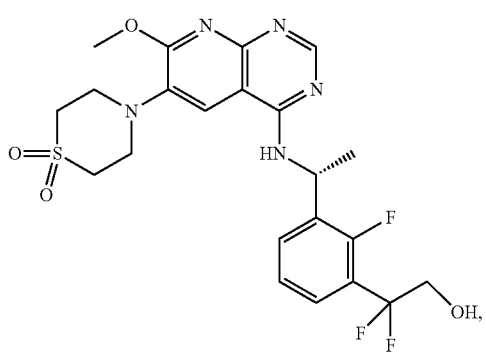
290
-continued
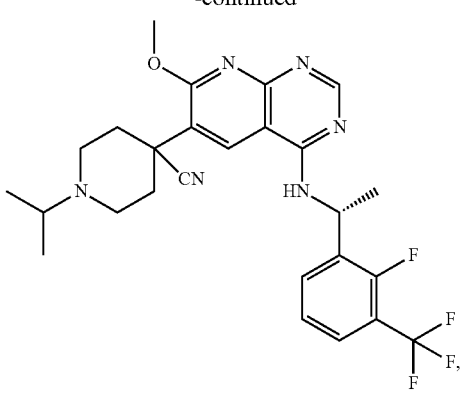
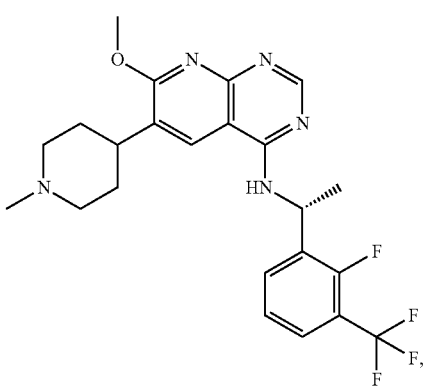
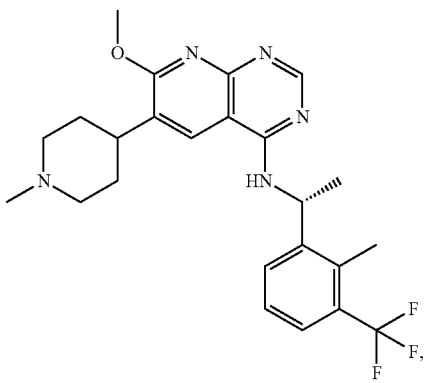
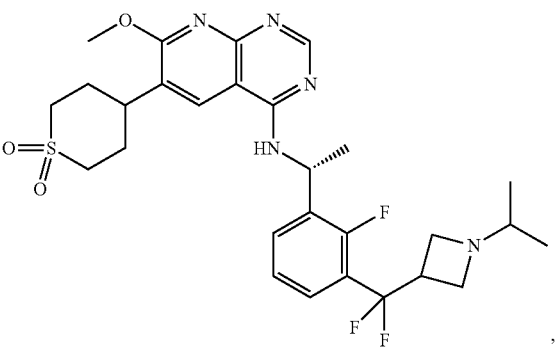

291
-continued
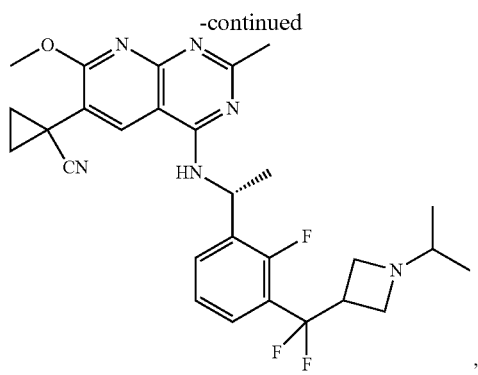
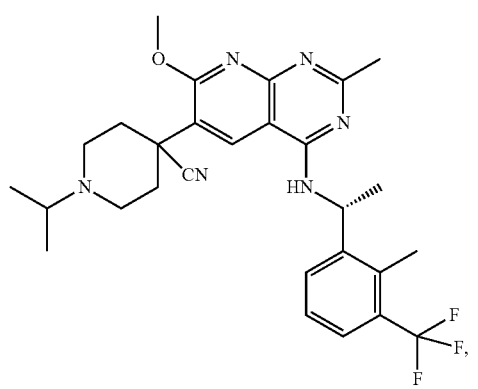
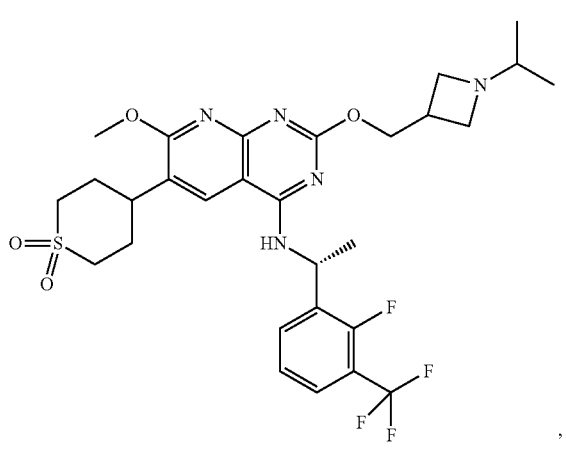
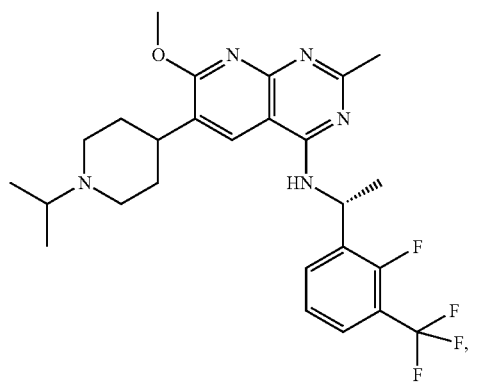
292
-continued
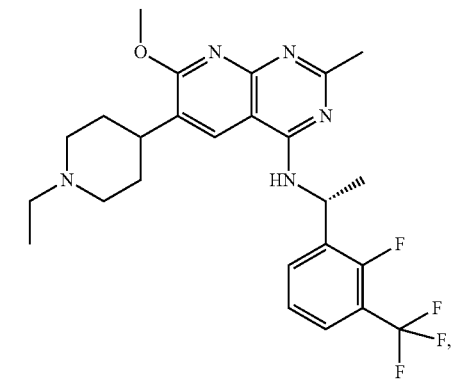
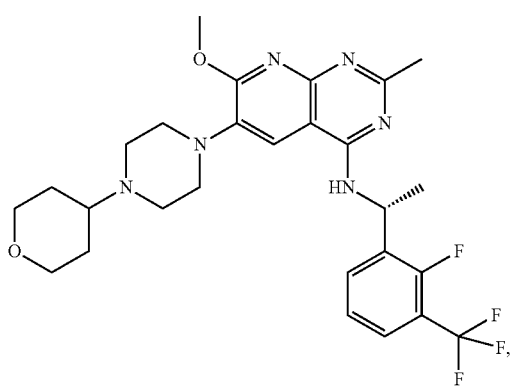
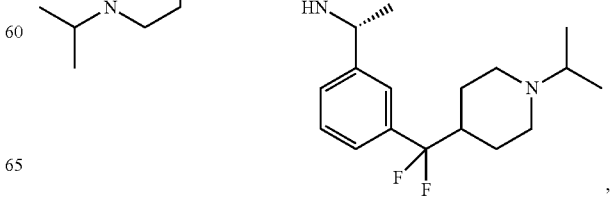

293
-continued
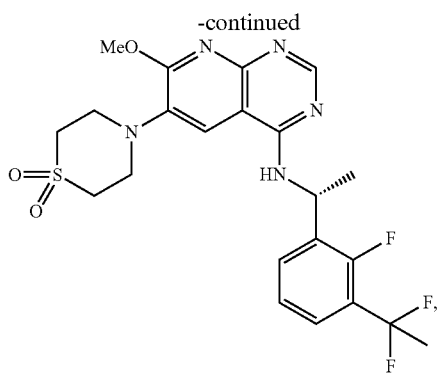
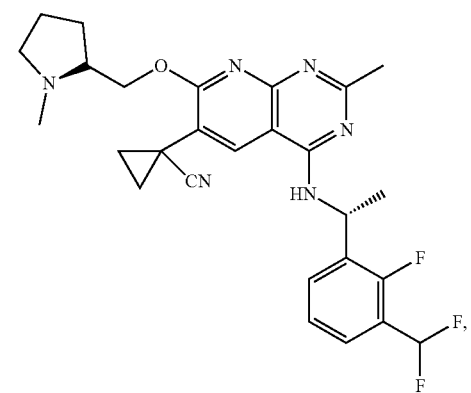
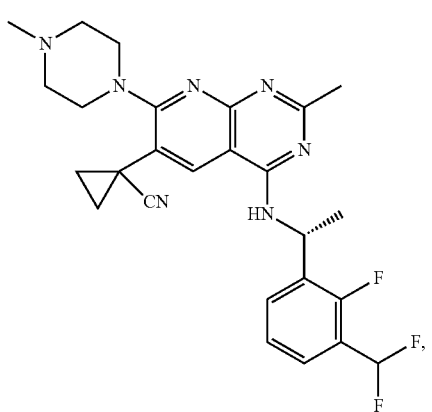
294
-continued
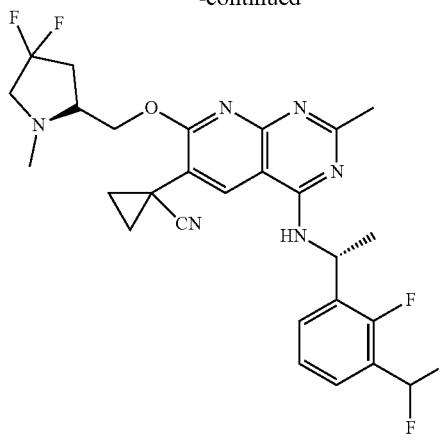
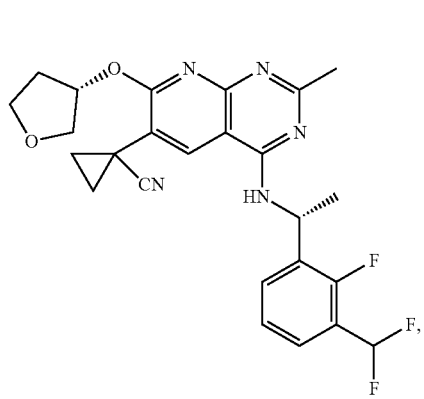
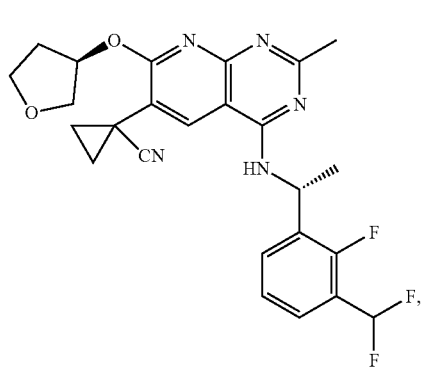
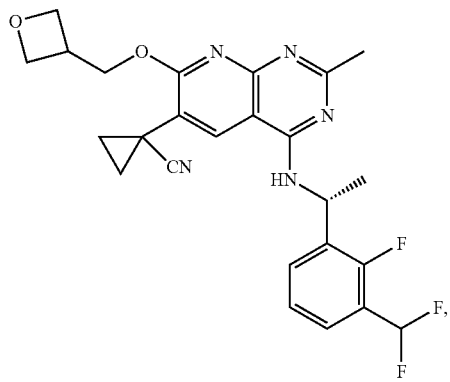

295
-continued
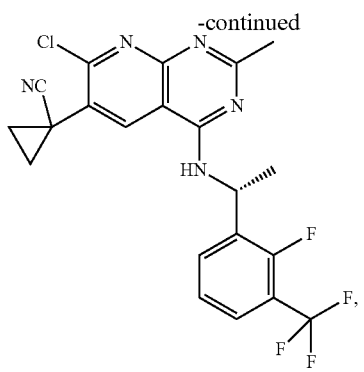
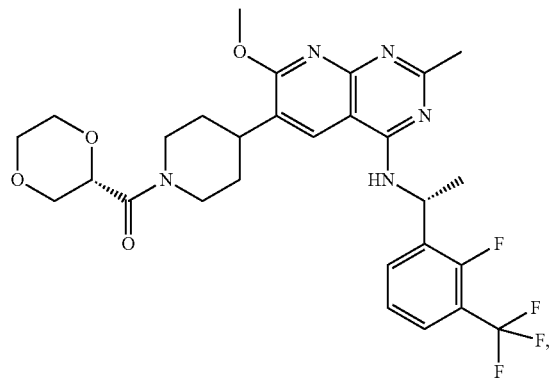
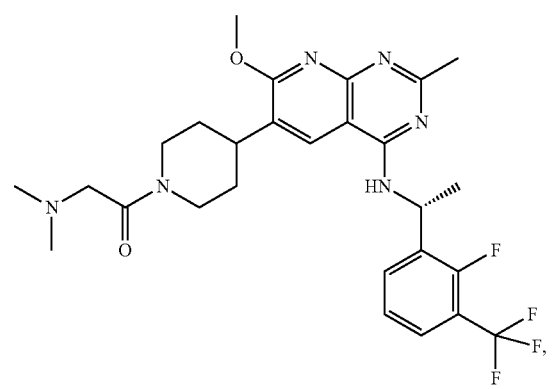
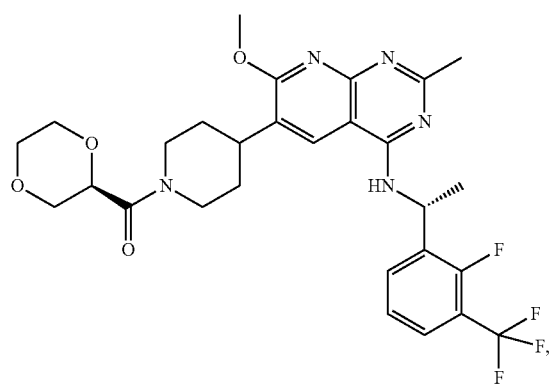
296
-continued
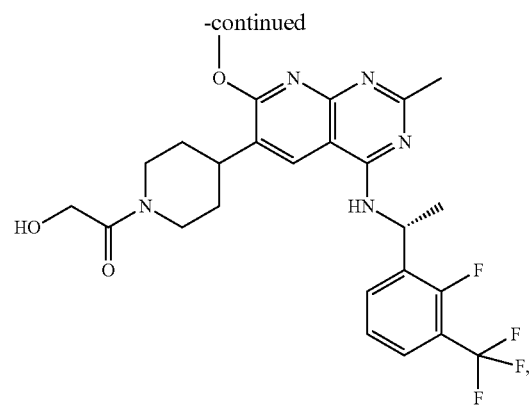
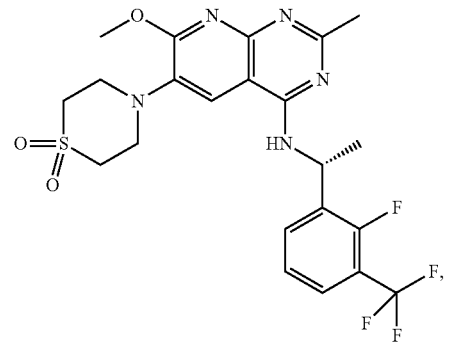
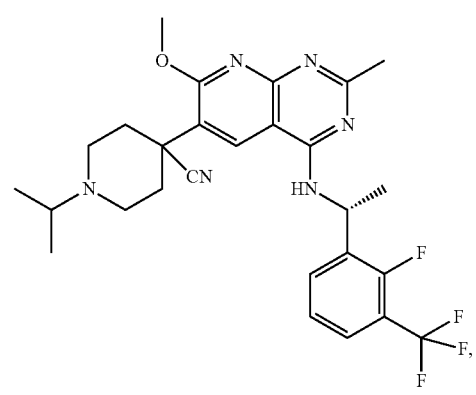
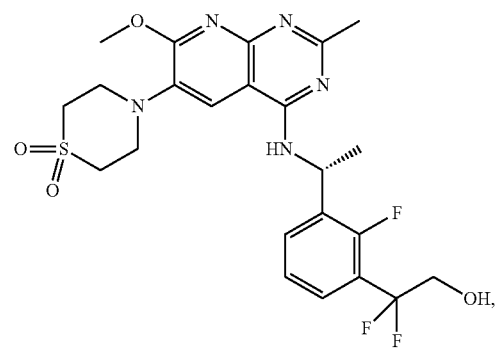

297
-continued
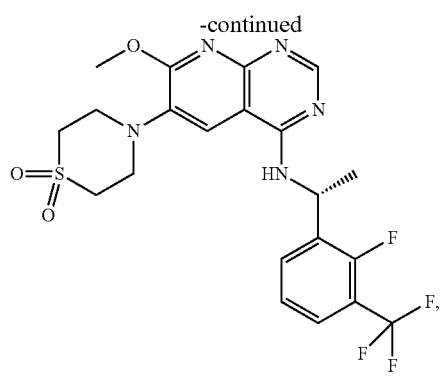
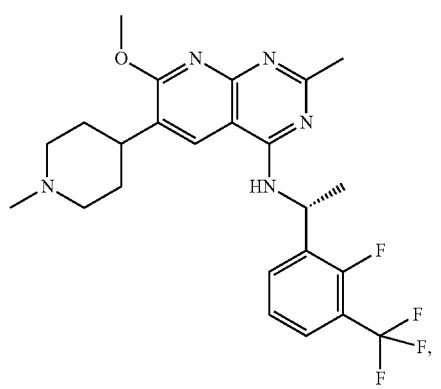
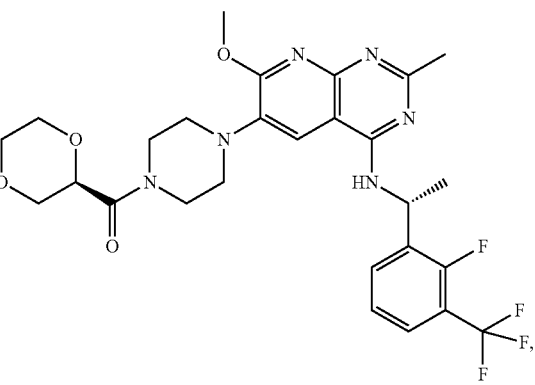
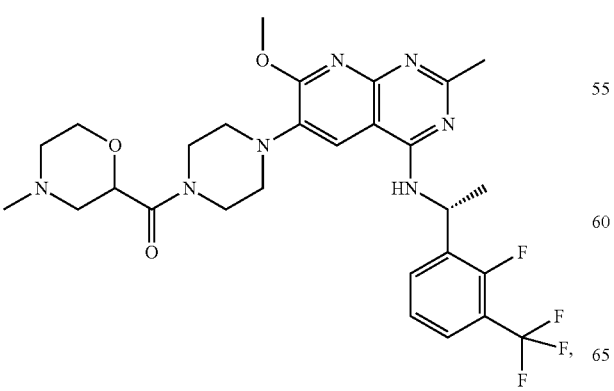
298
-continued
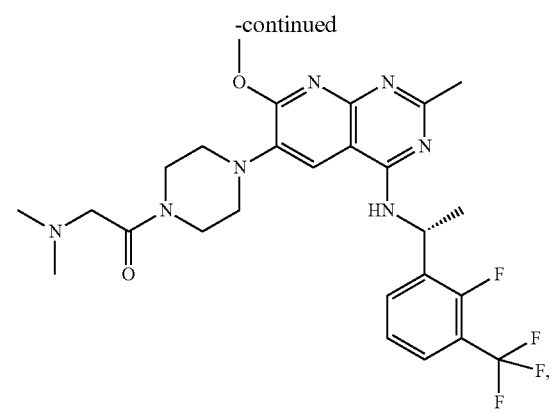

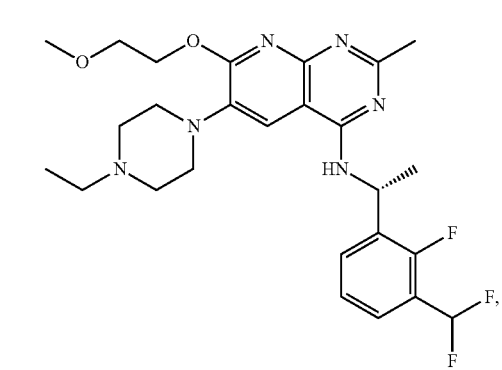
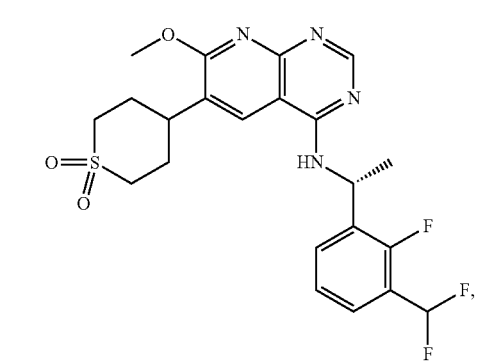

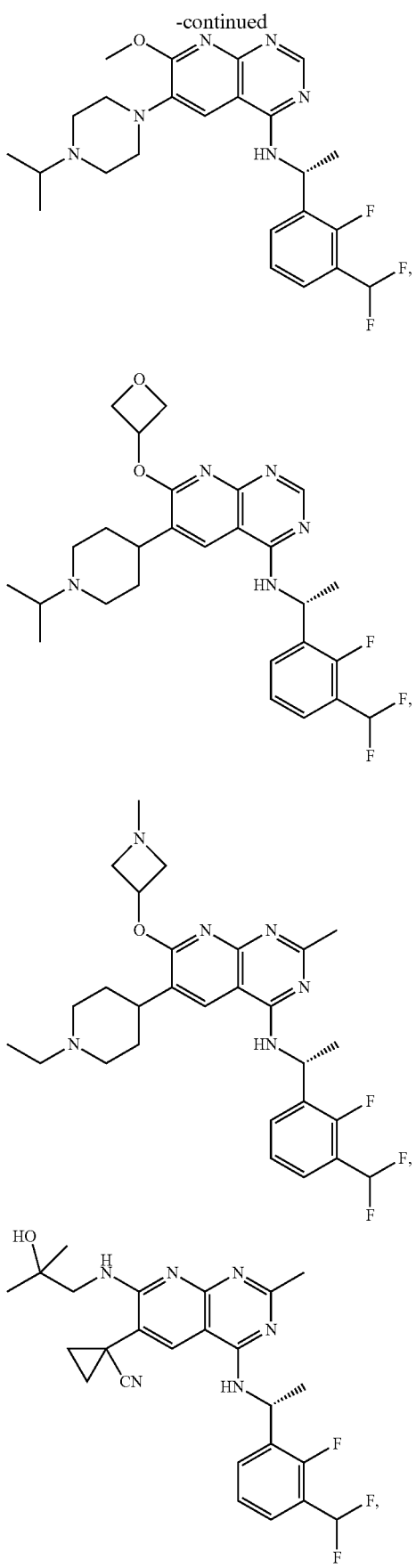

301
-continued
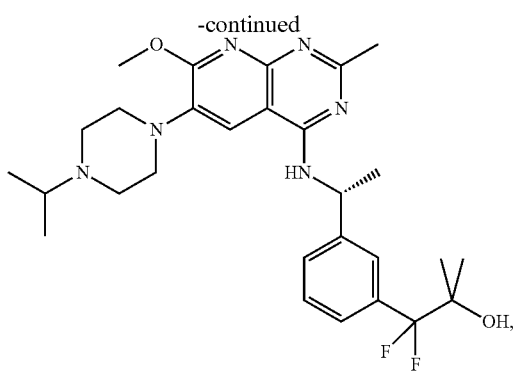
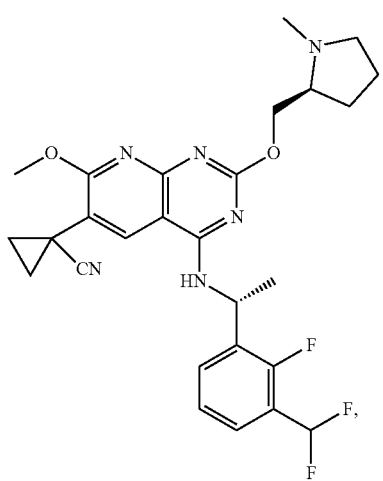
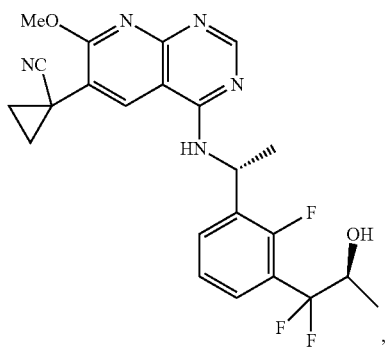
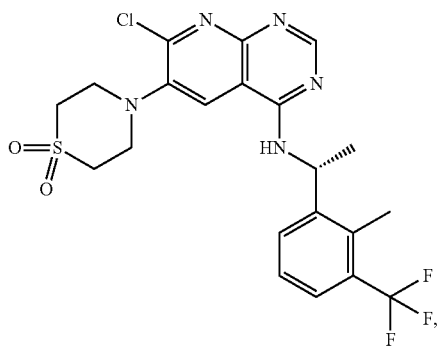
302
-continued
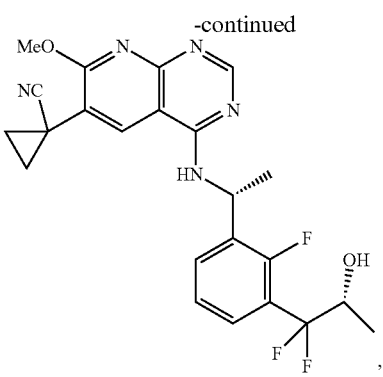
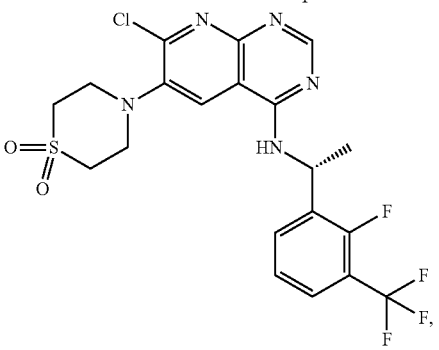
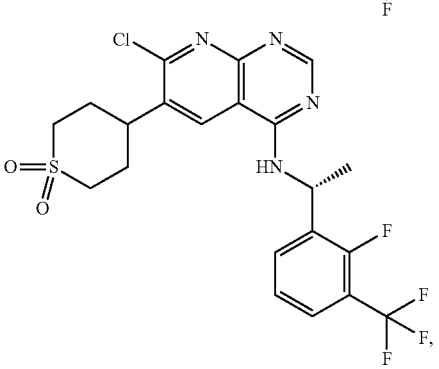
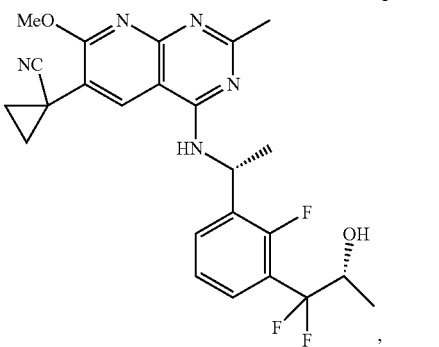
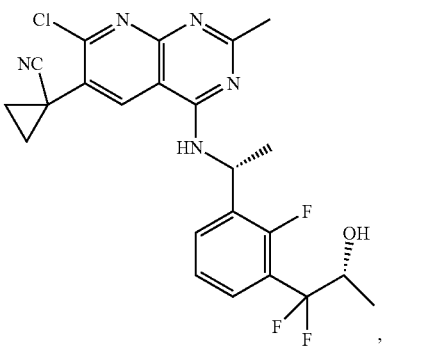

303
-continued
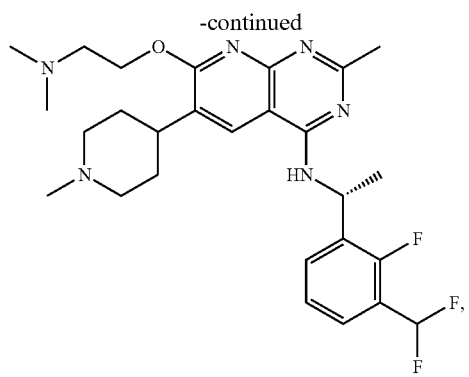
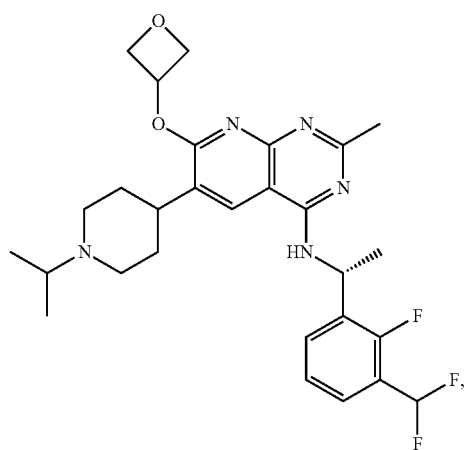
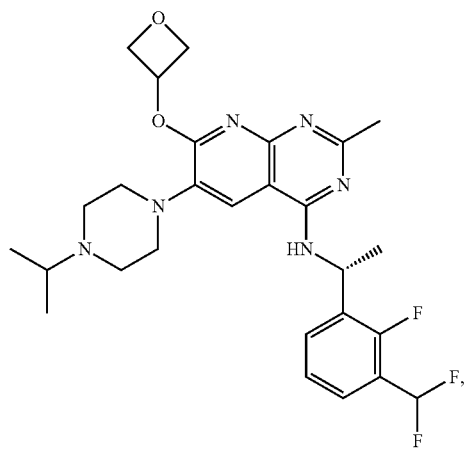
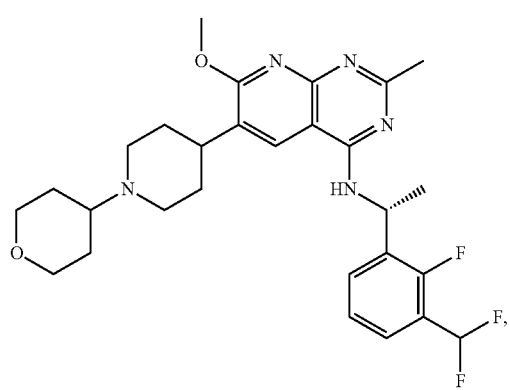
304
-continued
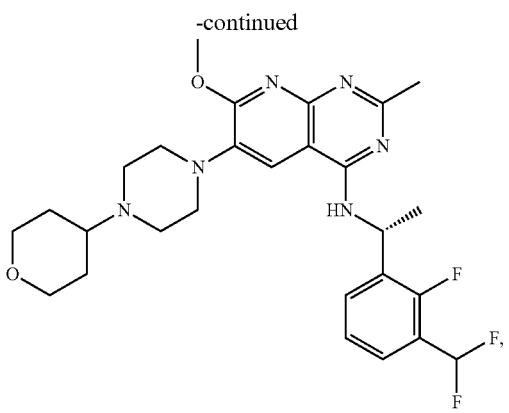
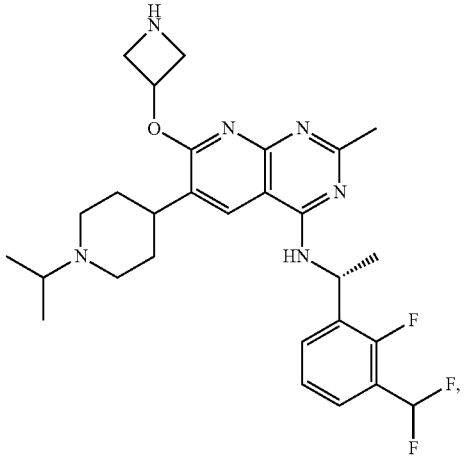
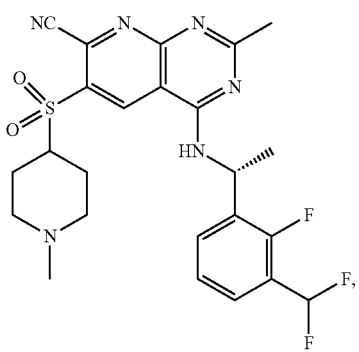

305
-continued
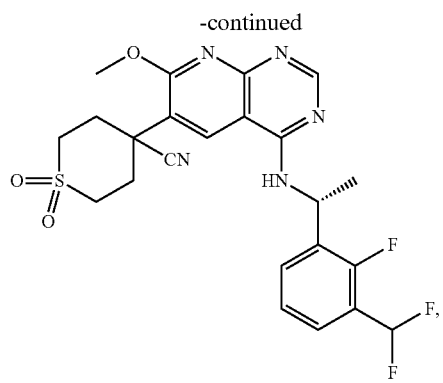
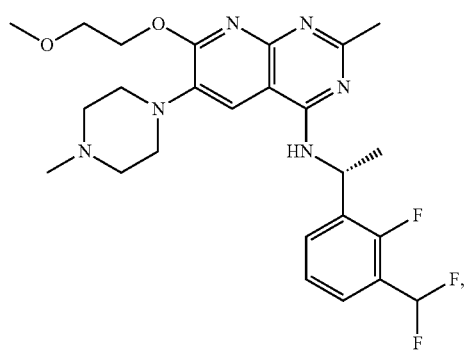
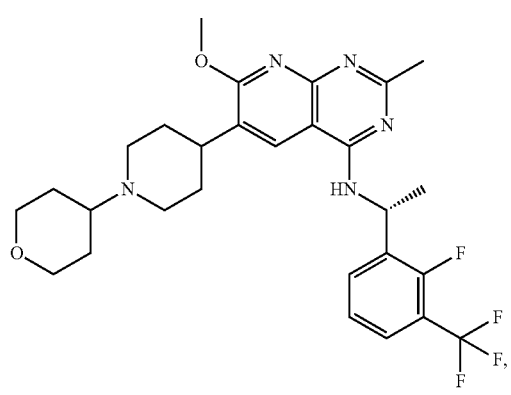
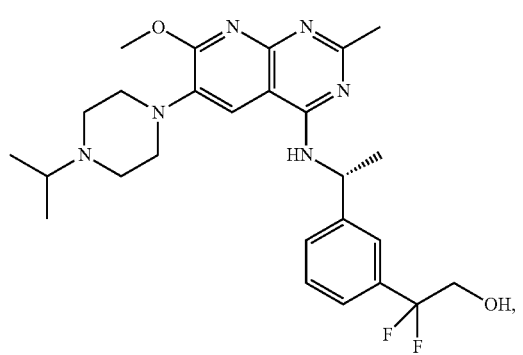
306
-continued
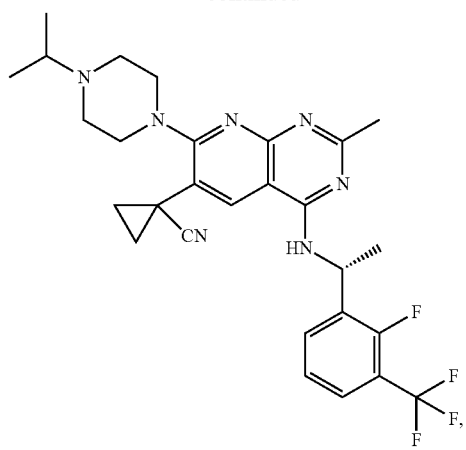
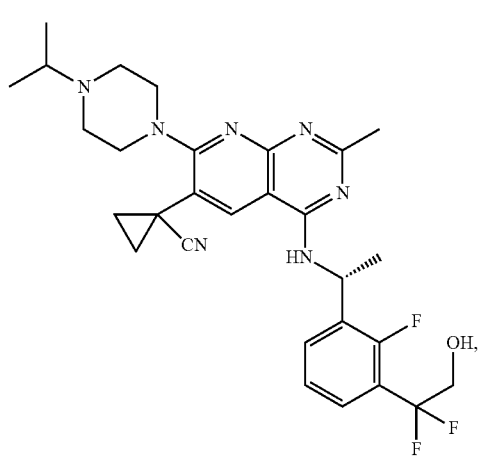
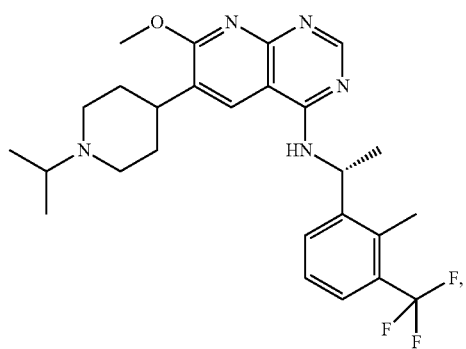
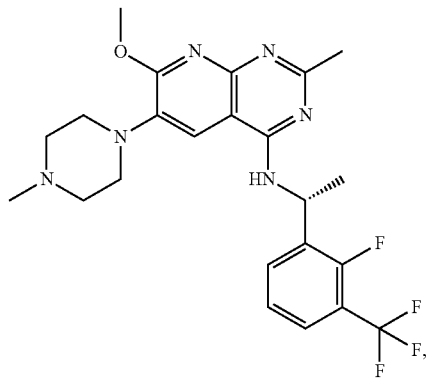

307
-continued
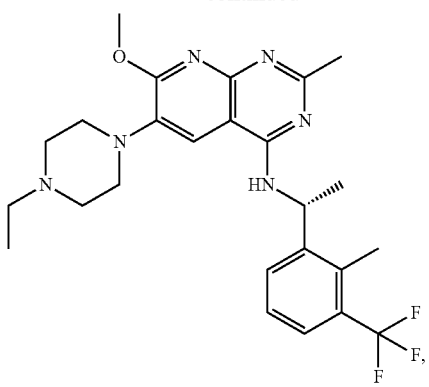
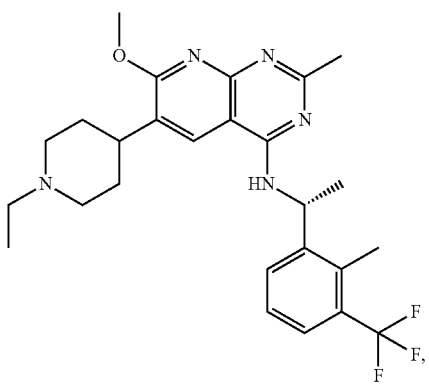
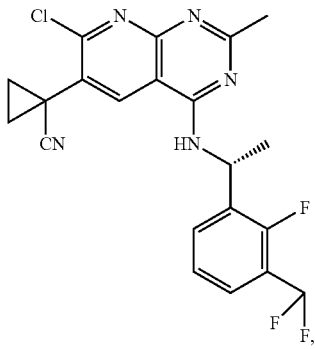
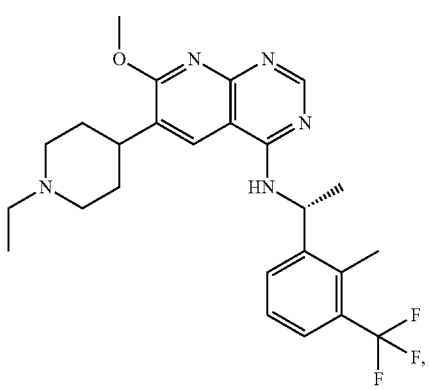
308
-continued
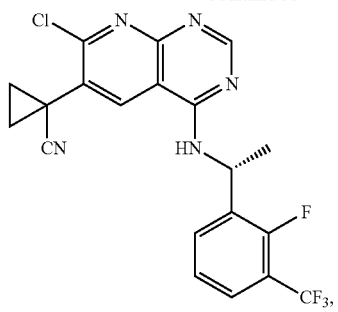
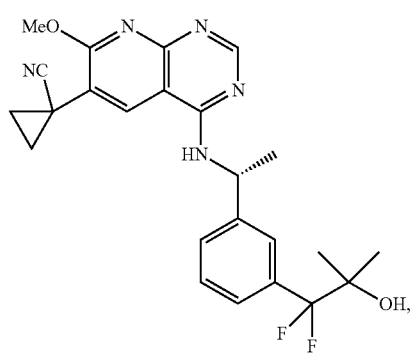
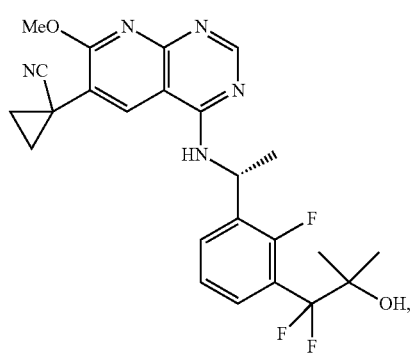
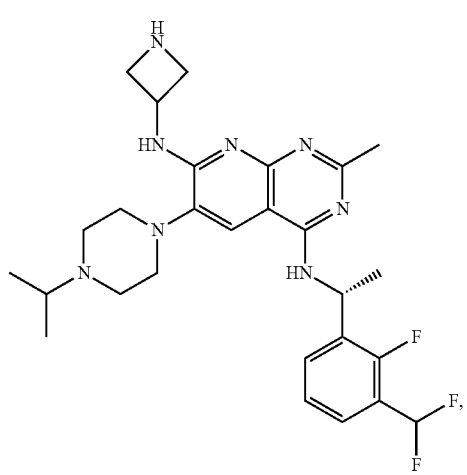

309
-continued
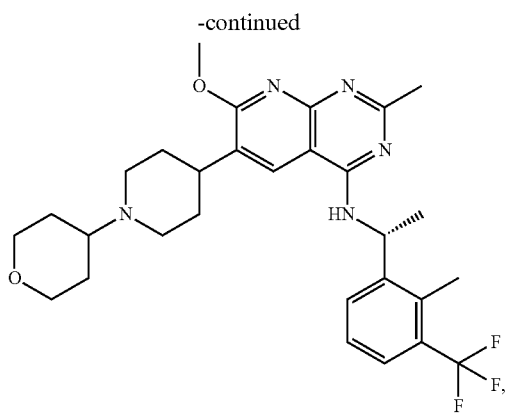
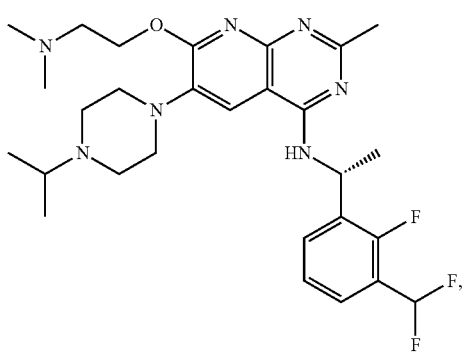
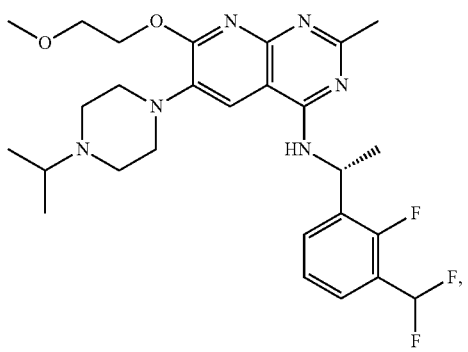
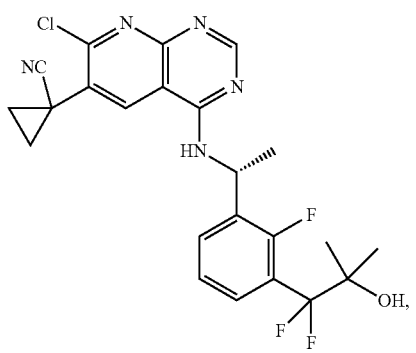
310
-continued
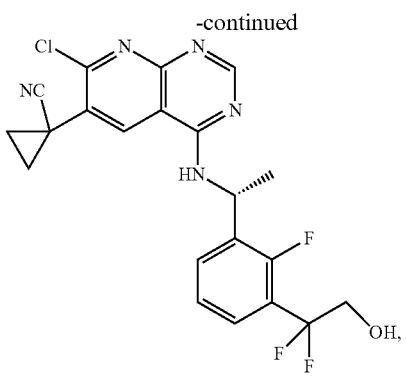
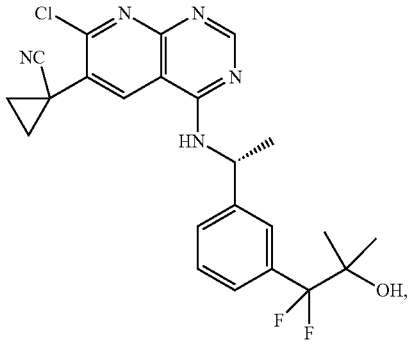
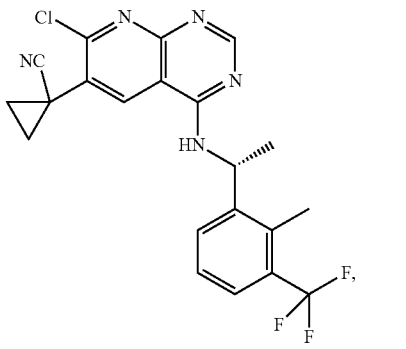
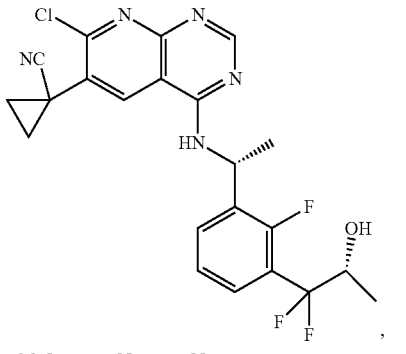
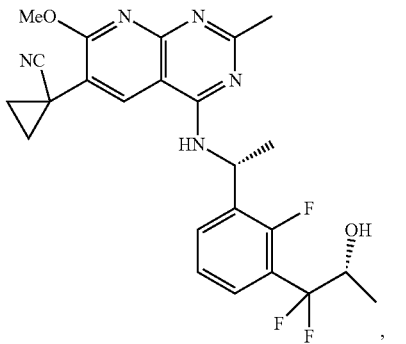

311
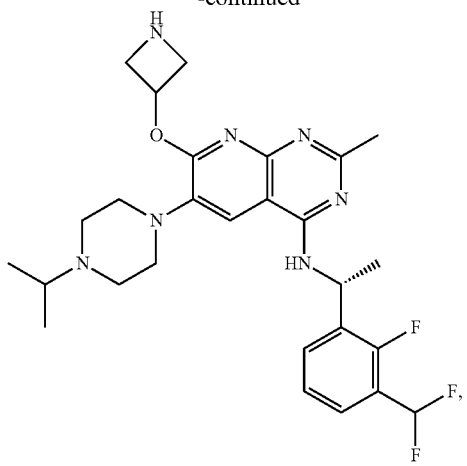
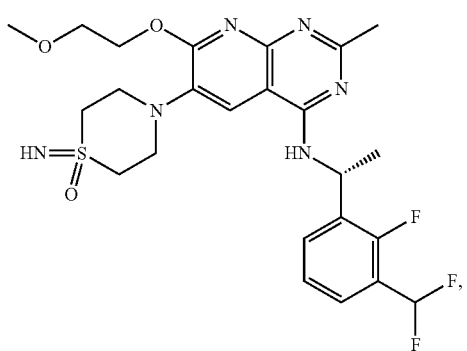
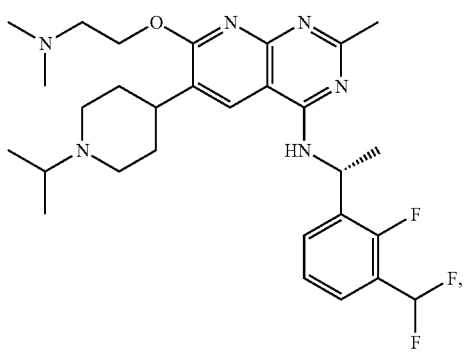
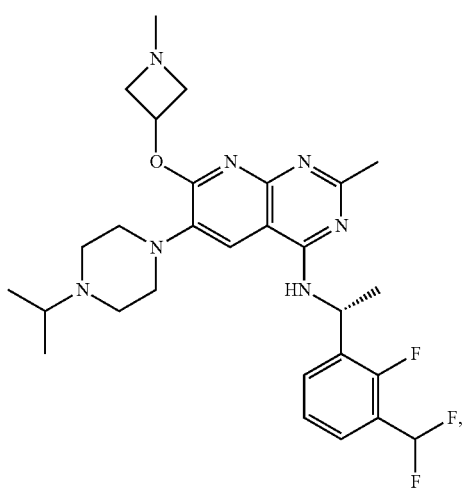
312
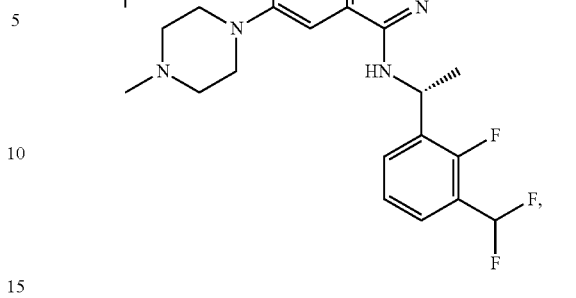
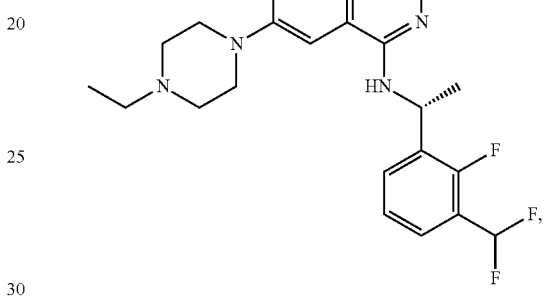
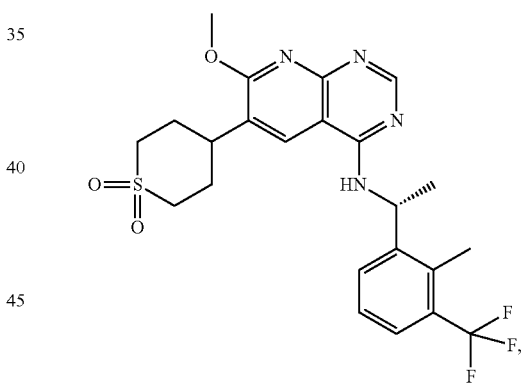
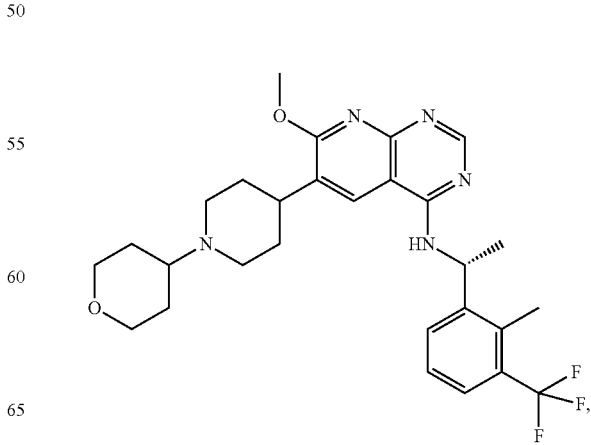

313
-continued
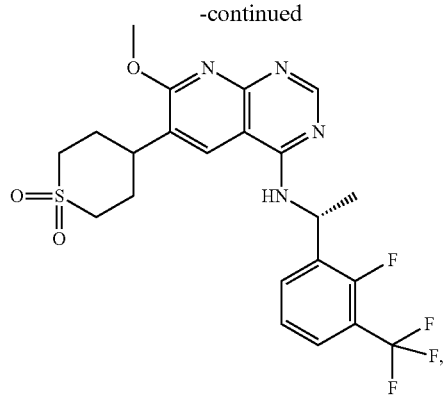
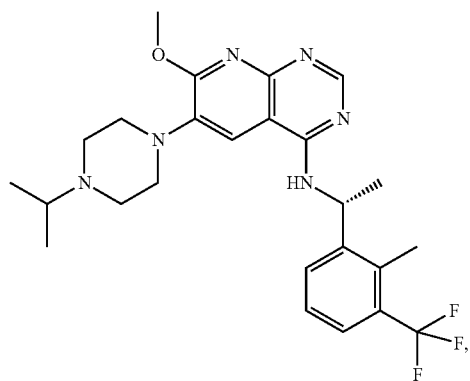
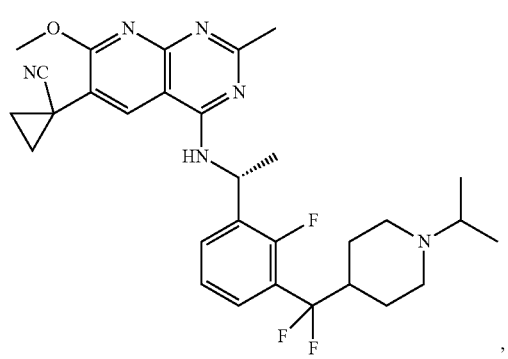
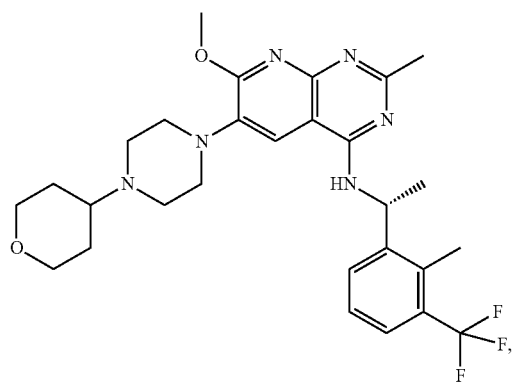
314
-continued
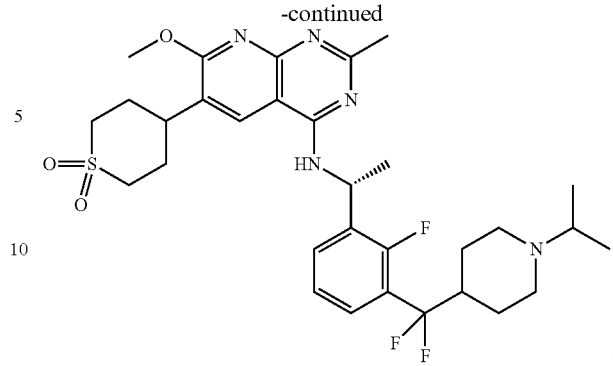
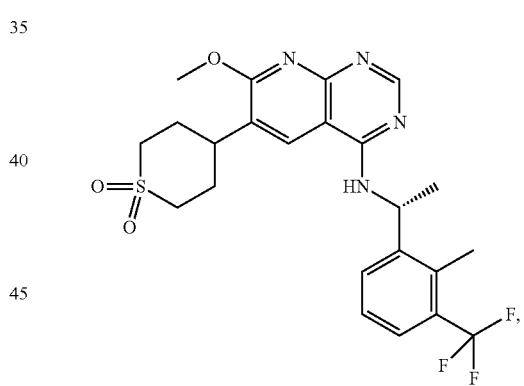
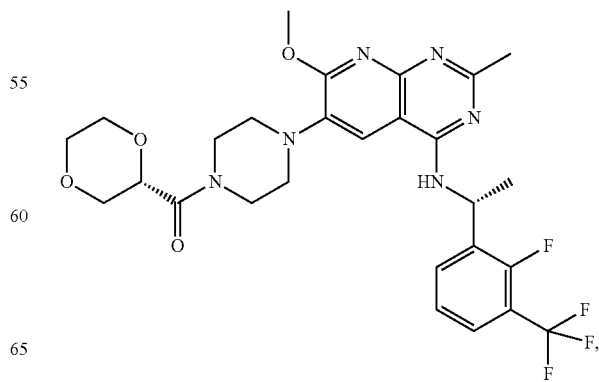

315
-continued
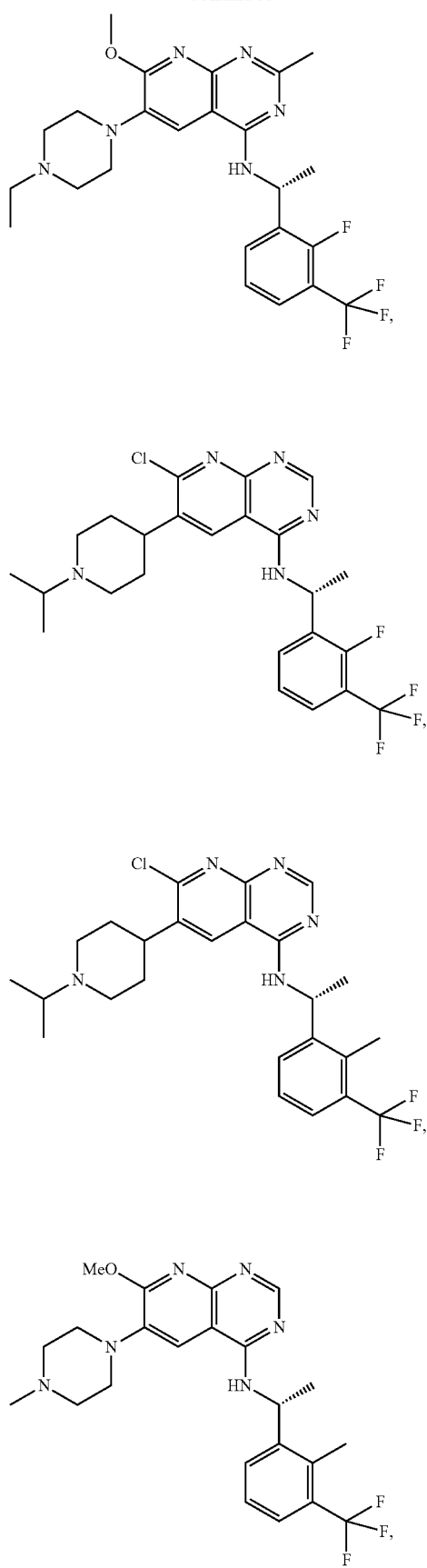
316
-continued
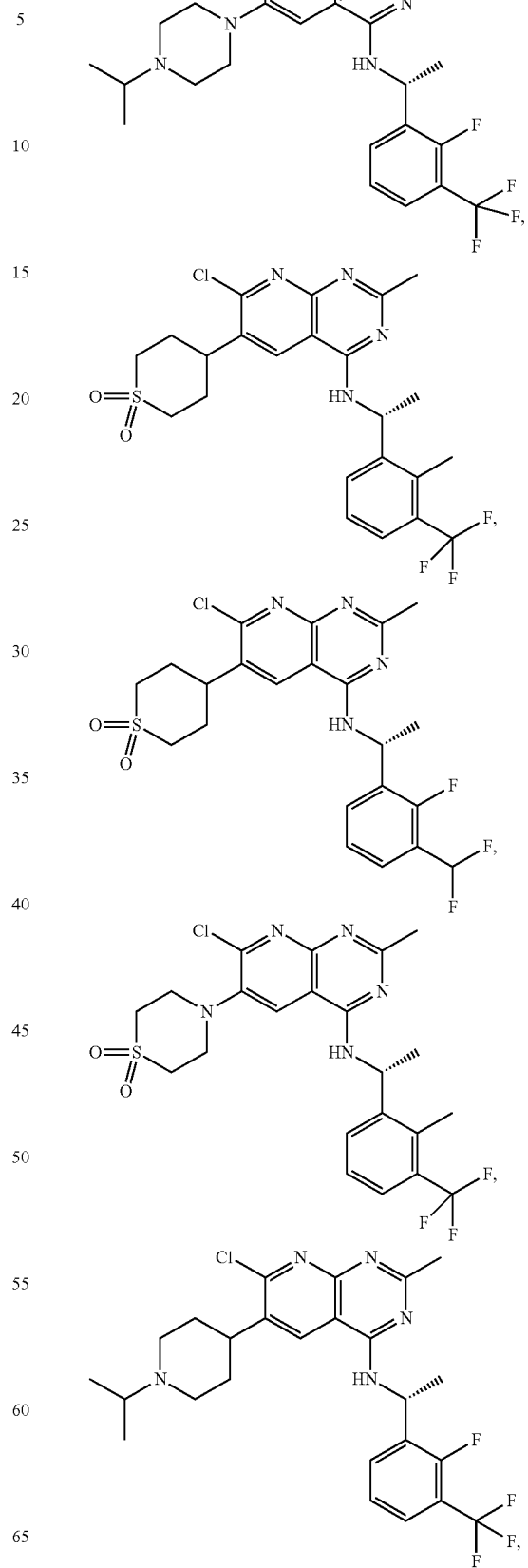

317
-continued
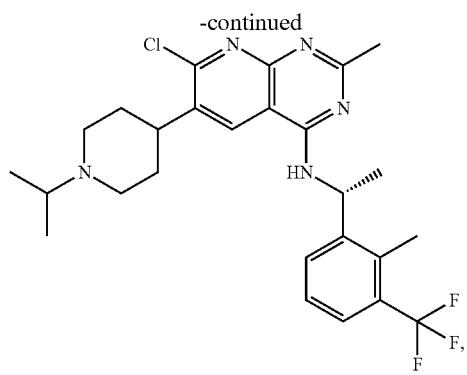
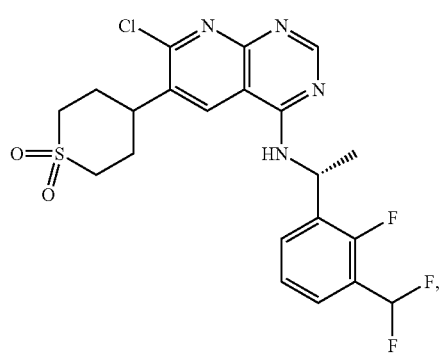
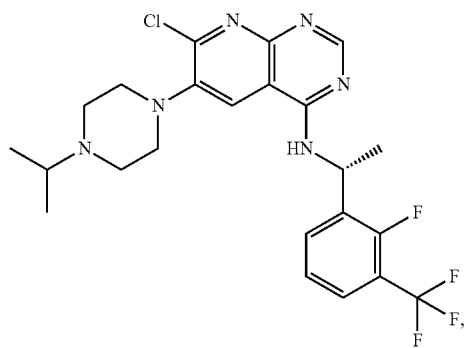
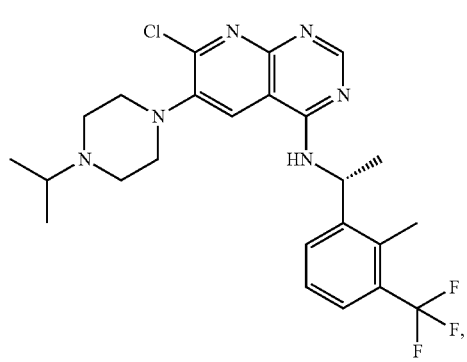
318
-continued
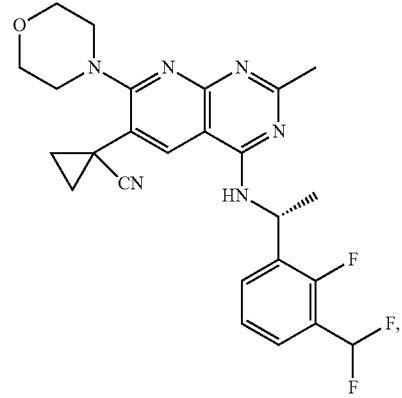
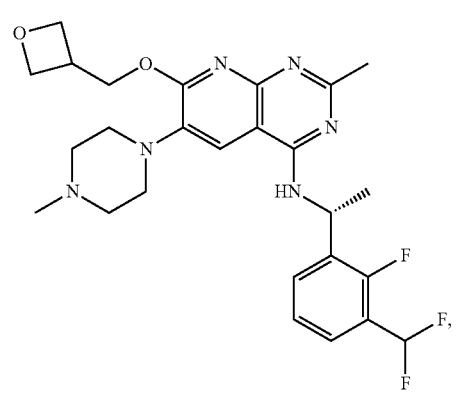
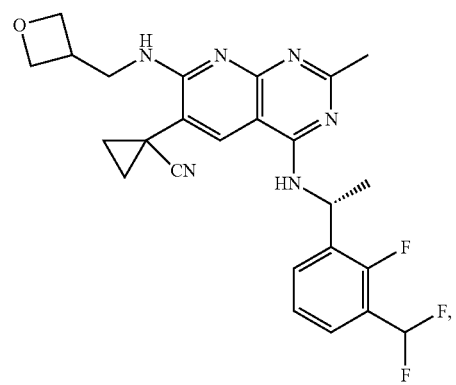
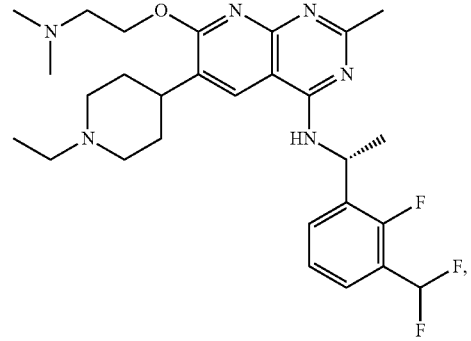

319
-continued
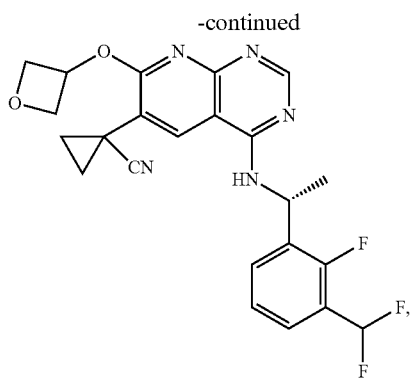
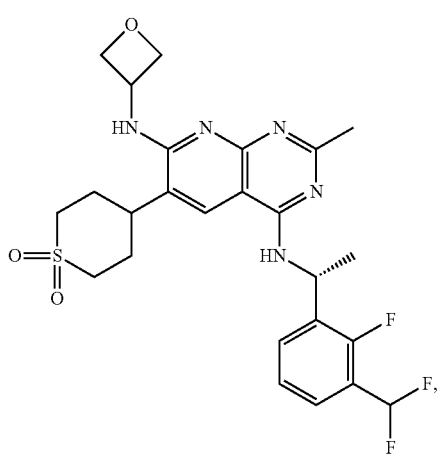
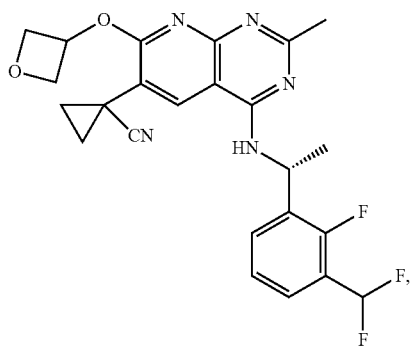
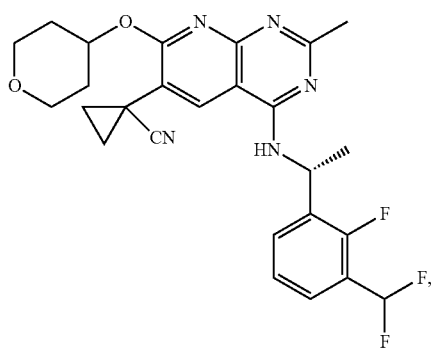
320
-continued
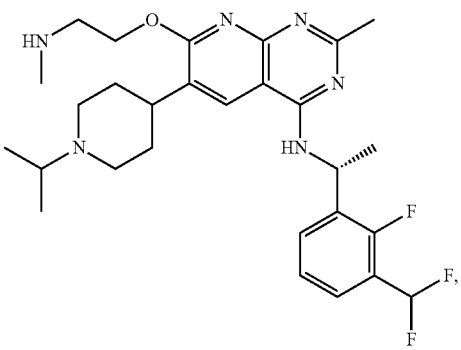
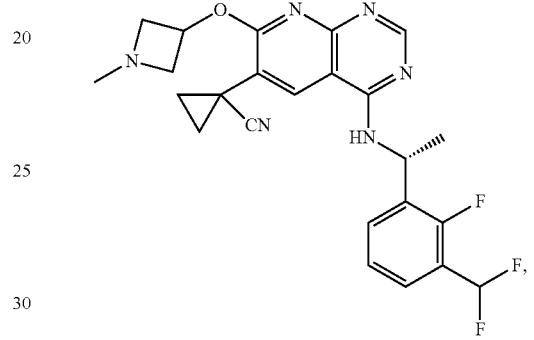
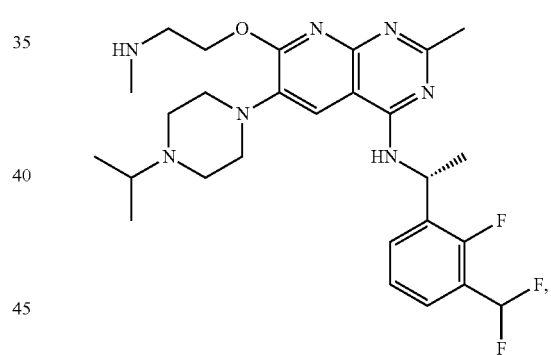
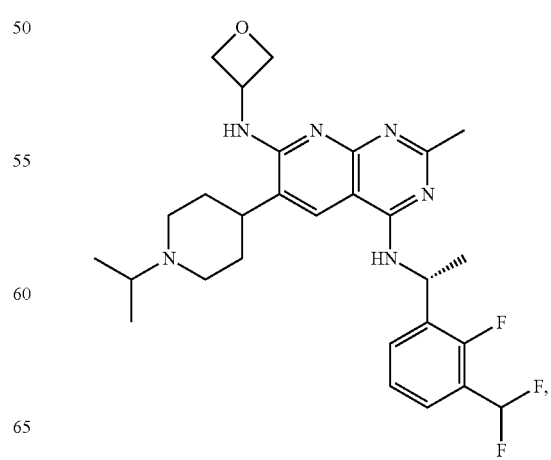

321
-continued
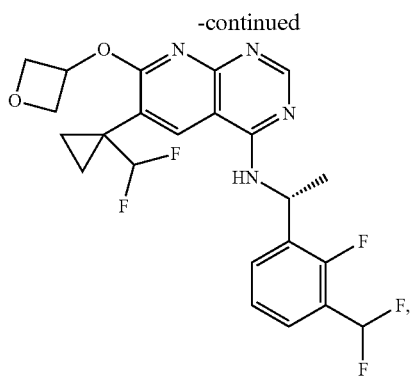
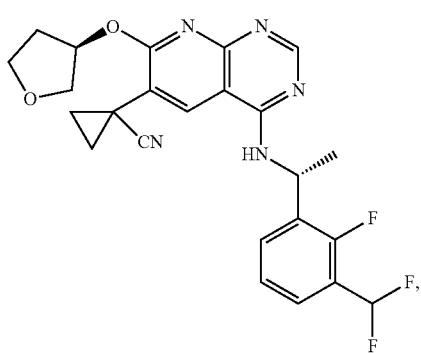
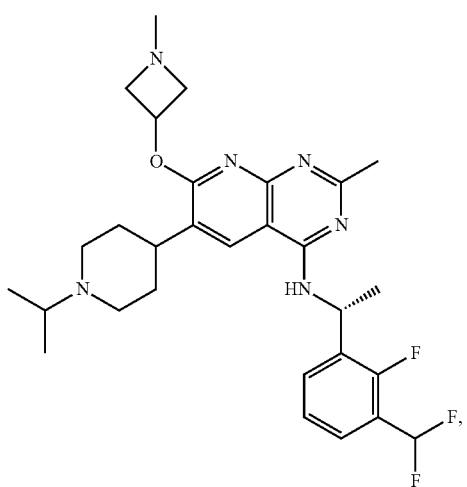
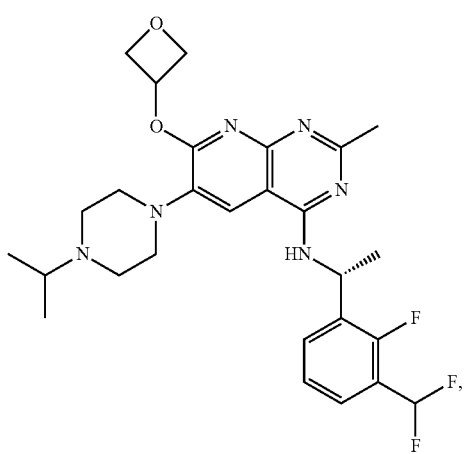
322
-continued
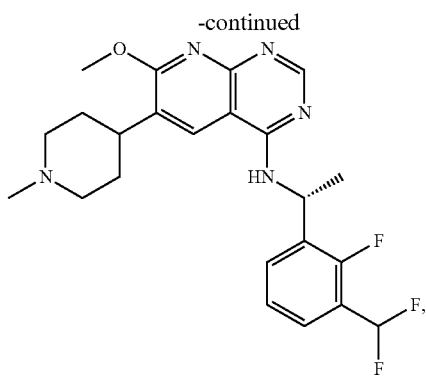
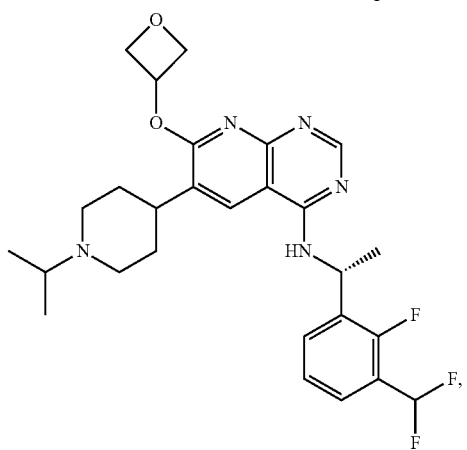
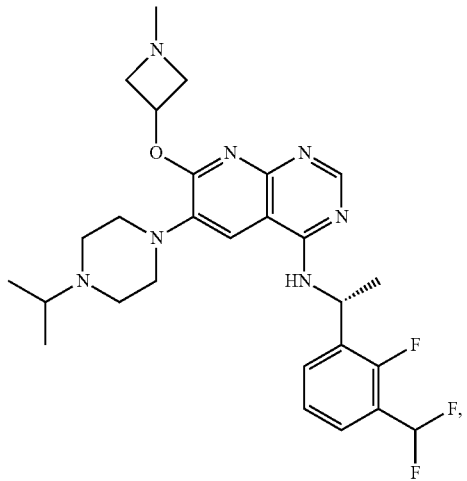
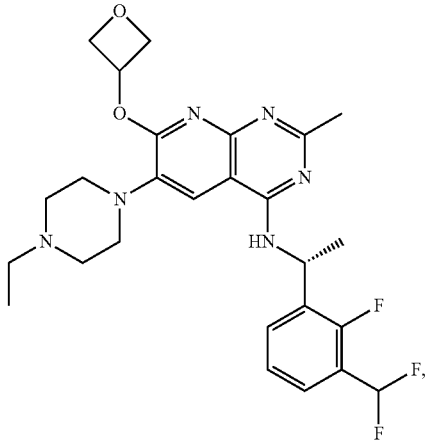

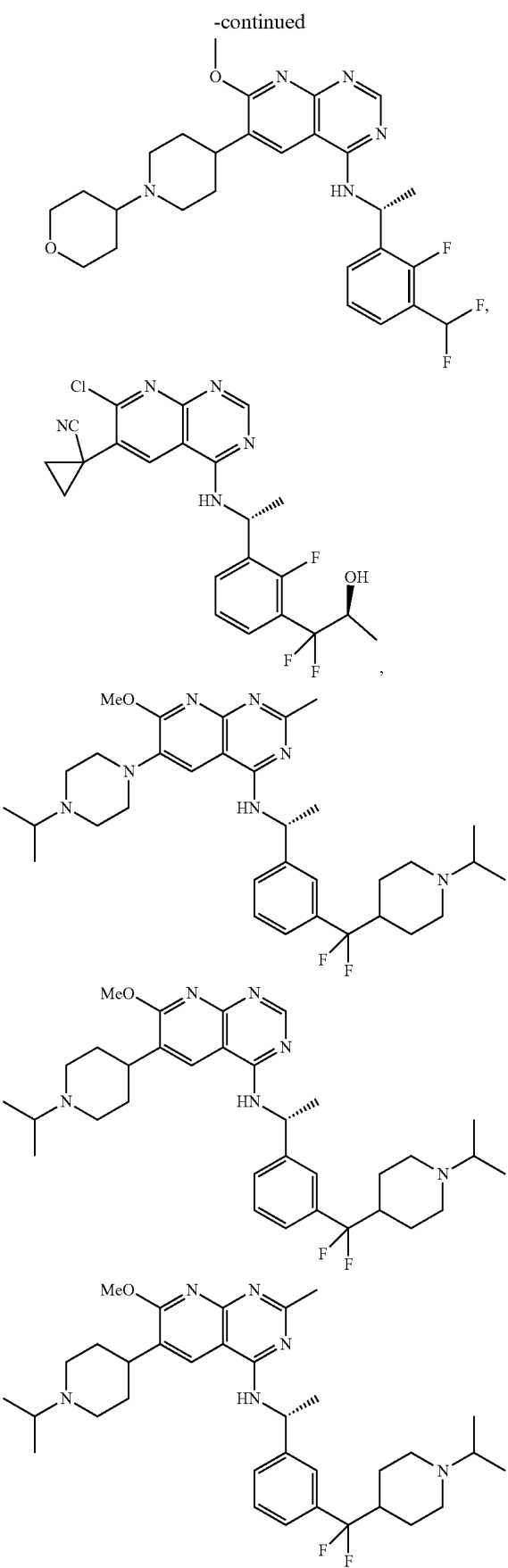
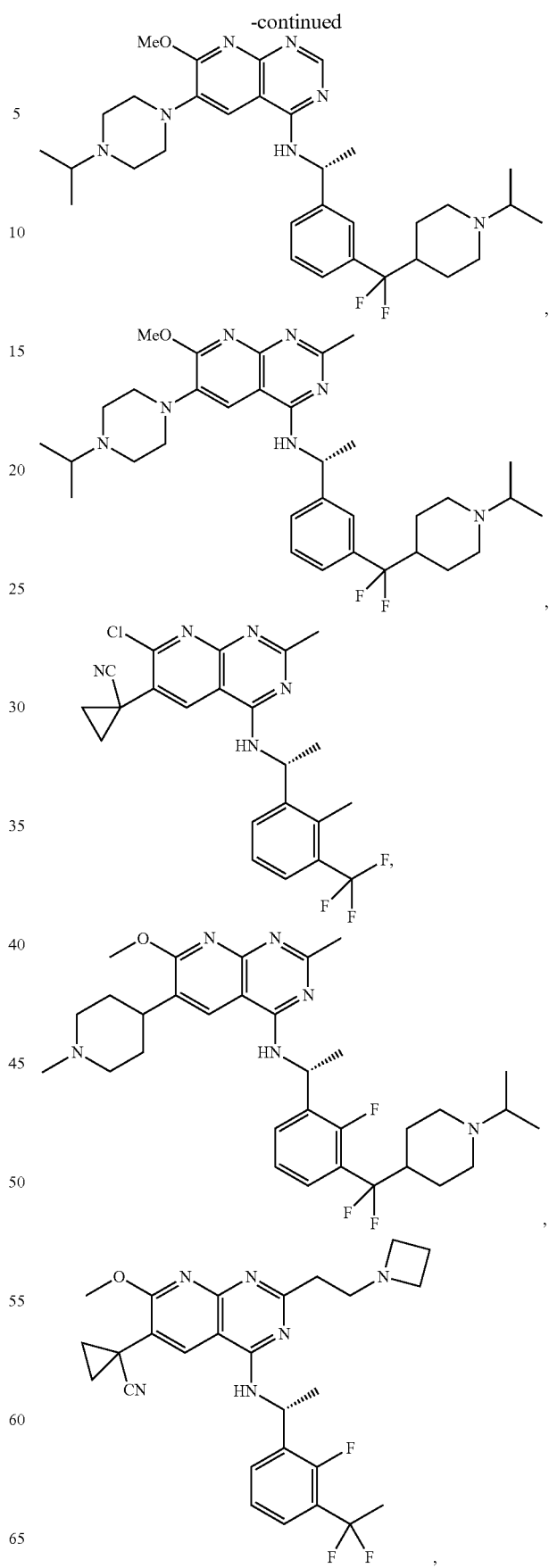

325
-continued
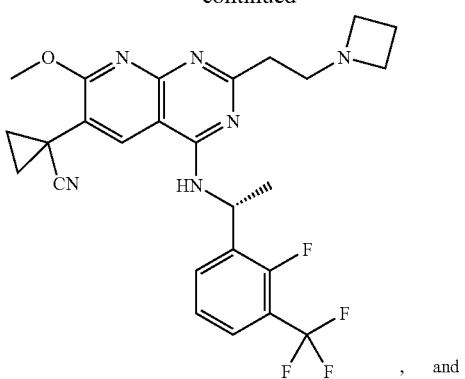
, and
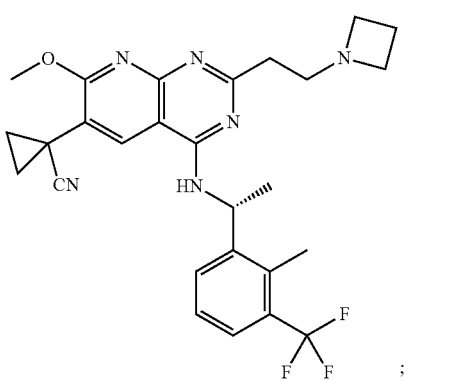
;
or a pharmaceutically acceptable salt or solvate thereof.
A compound selected from:
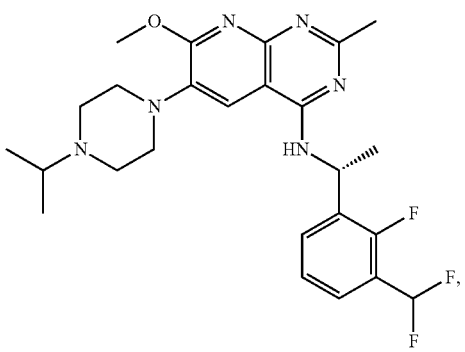
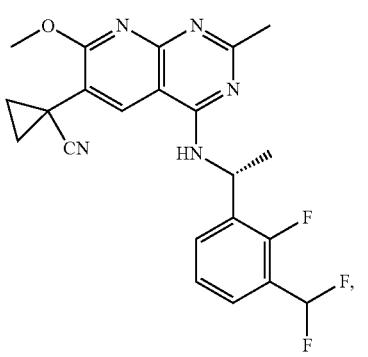
326
-continued
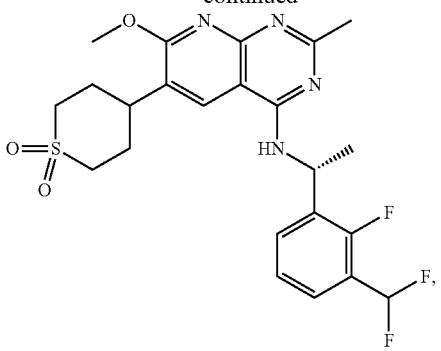
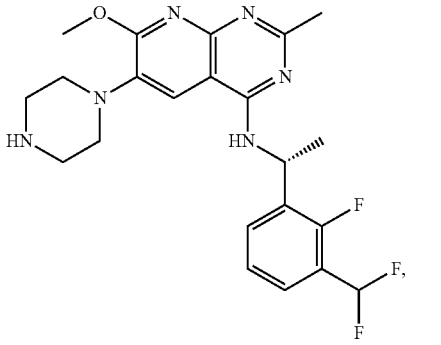
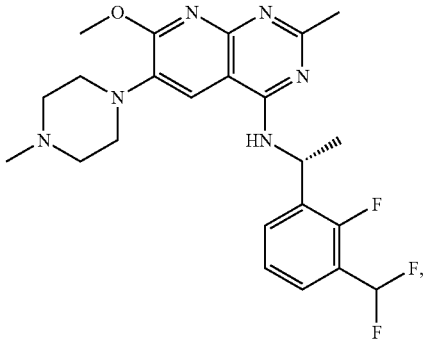
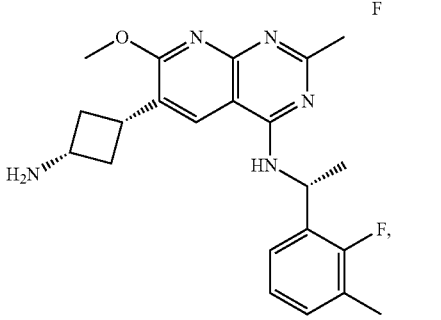
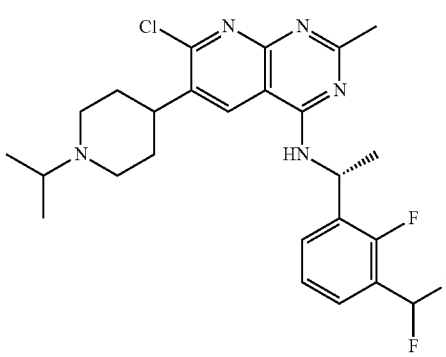

327
-continued
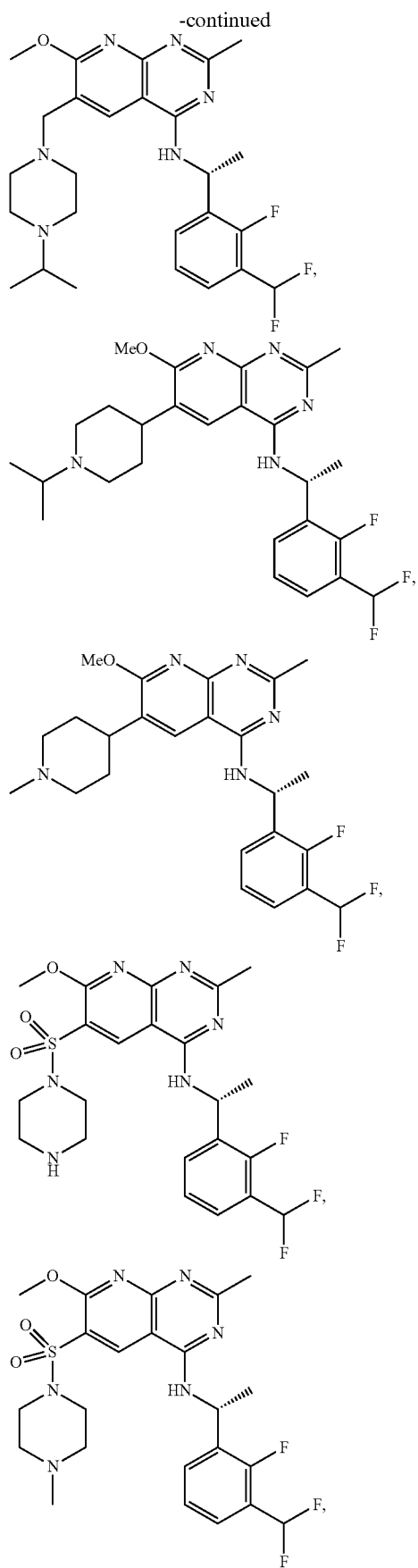
328
-continued
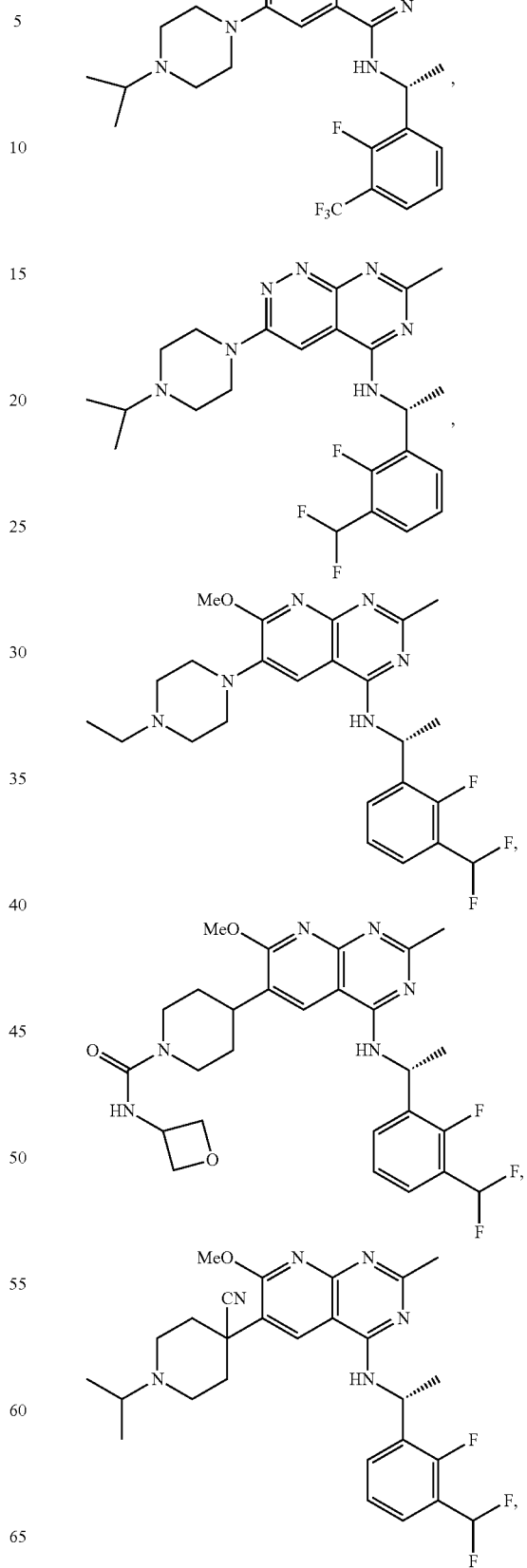

329
-continued
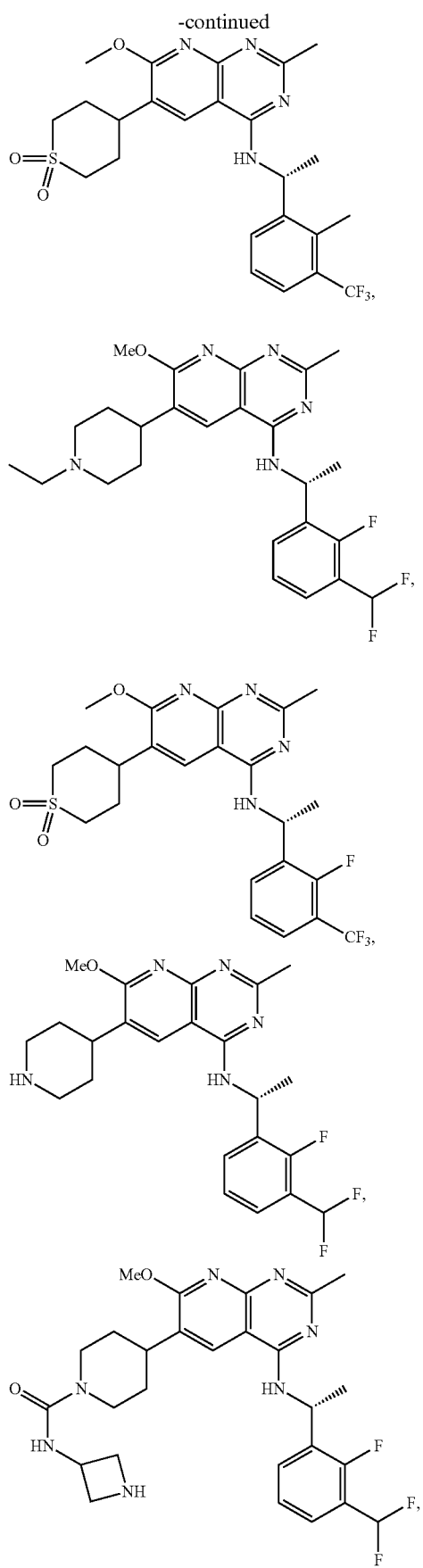
330
-continued
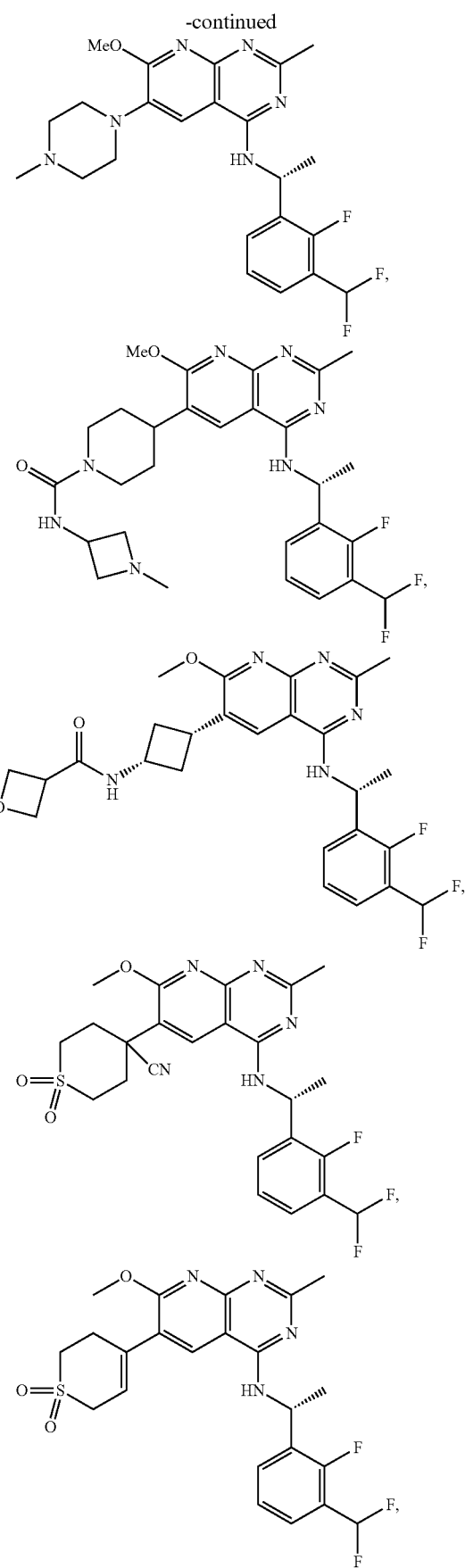

331
-continued
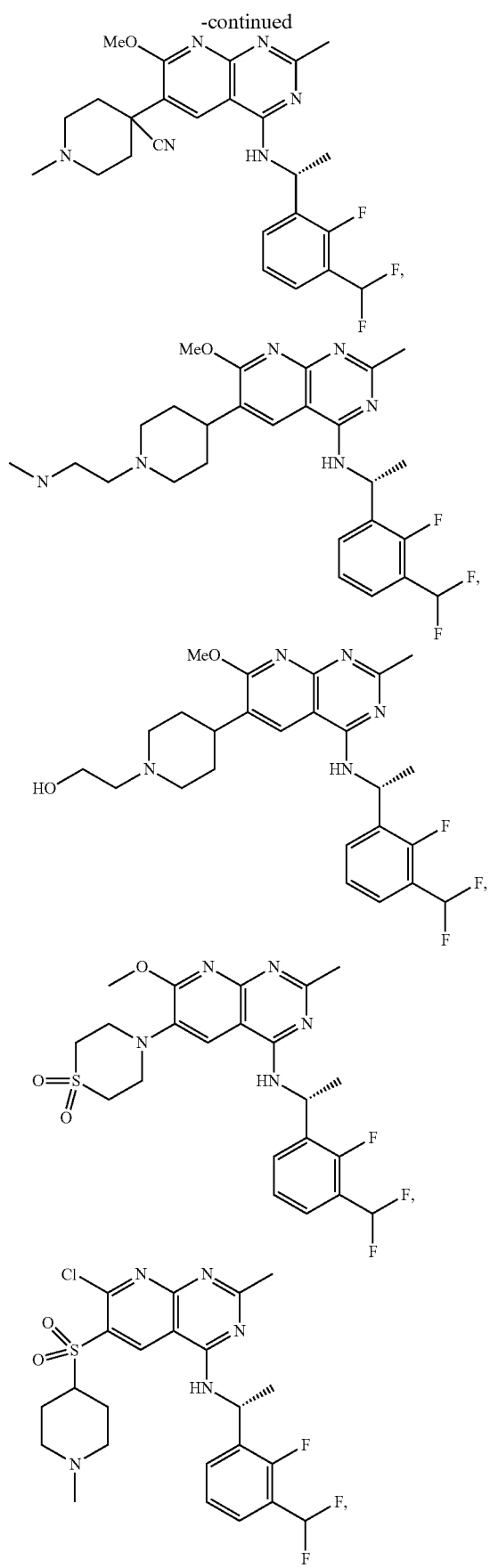
332
-continued
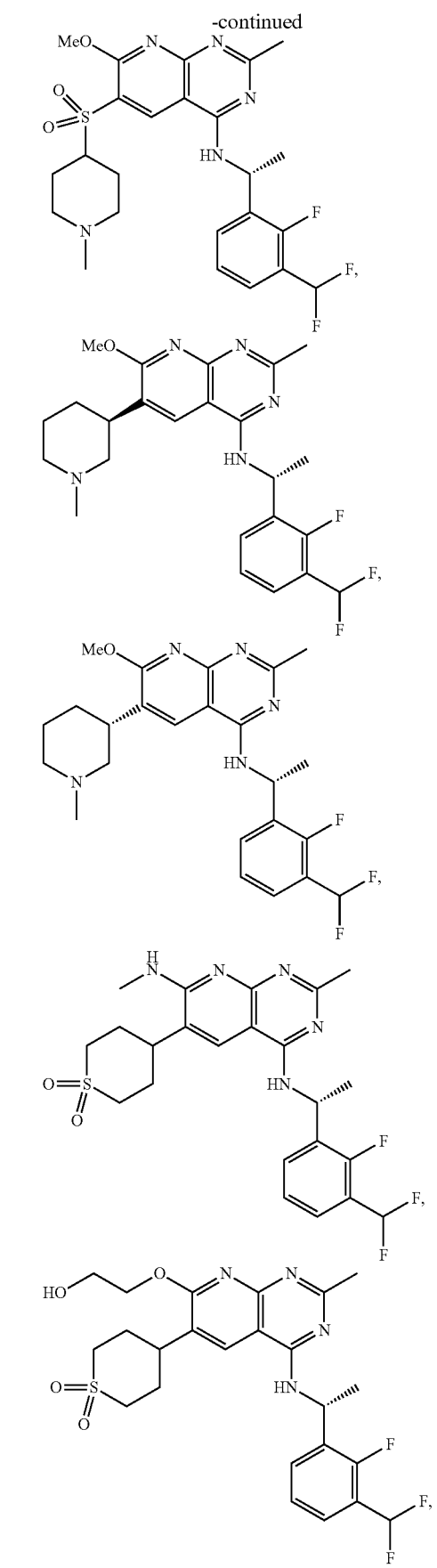

333
-continued
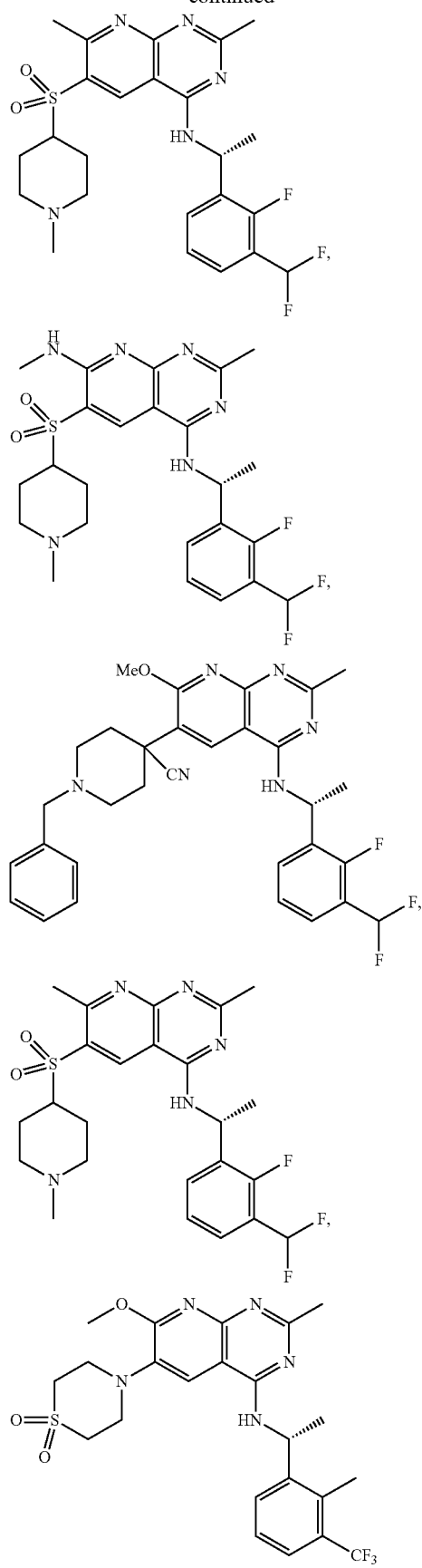
334
-continued
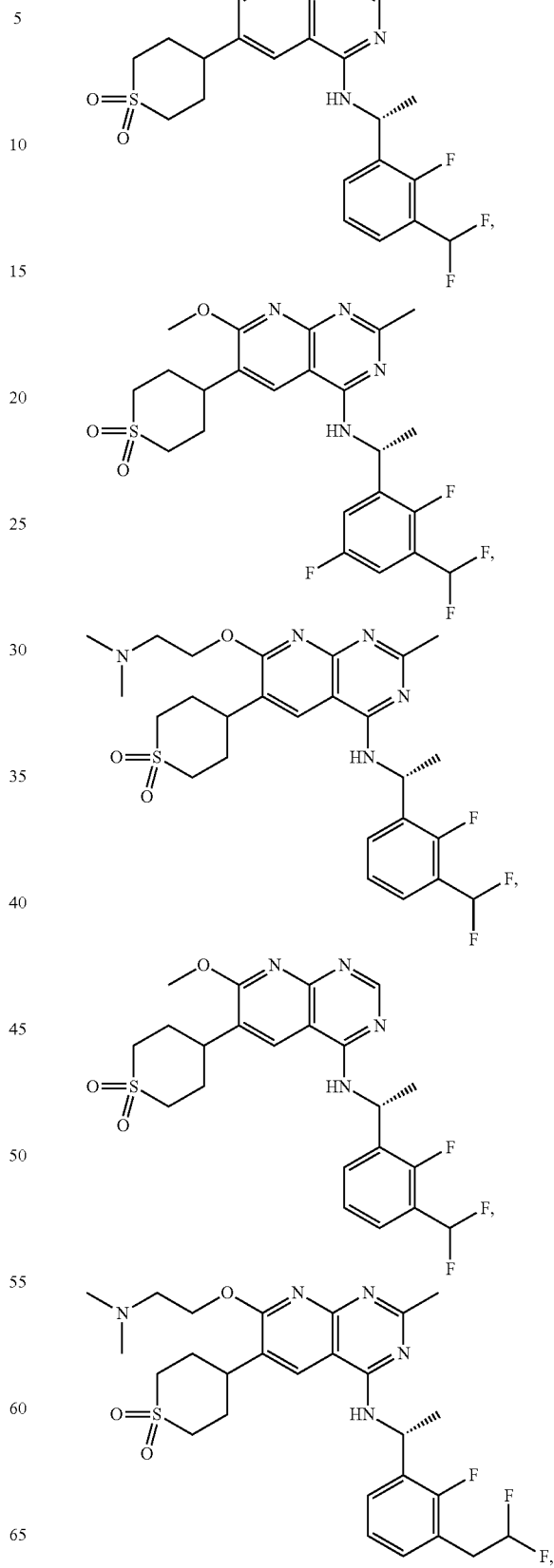

-continued

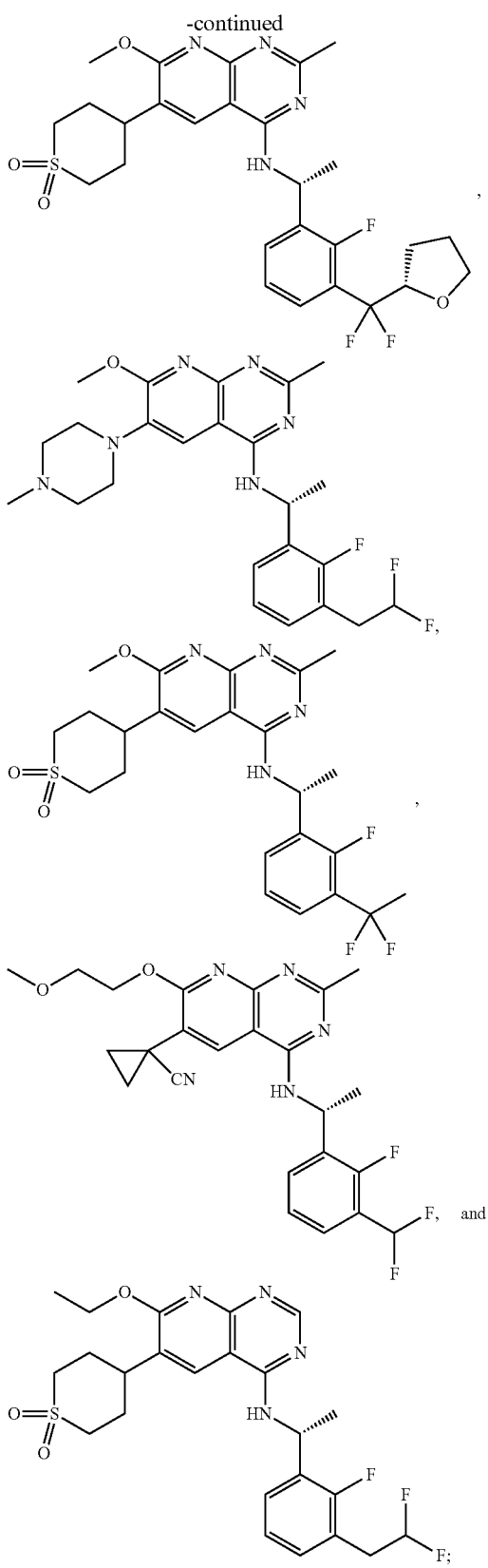

or a pharmaceutically acceptable salt or solvate thereof.

In an aspect is provided a compound selected from the compounds shown in Table 1.

In some embodiments is a compound of Formula (I-1) having the structure of Formula (I'-1), or a pharmaceutically acceptable salt or solvate thereof:

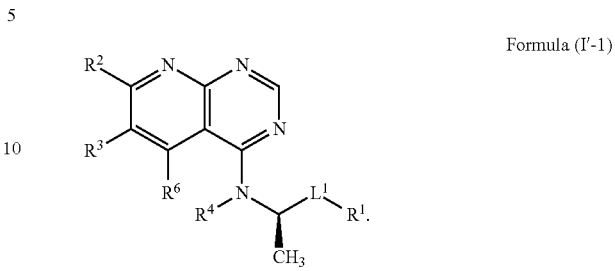

Formula (I'-1)

In some embodiments is a compound of Formula (Ia-1) having the structure of Formula (Ia'-1), or a pharmaceutically acceptable salt or solvate thereof:


Formula (Ia'-1)

In some embodiments is a compound of Formula (Ib-1) having the structure of Formula (Ib'-1), or a pharmaceutically acceptable salt or solvate thereof:

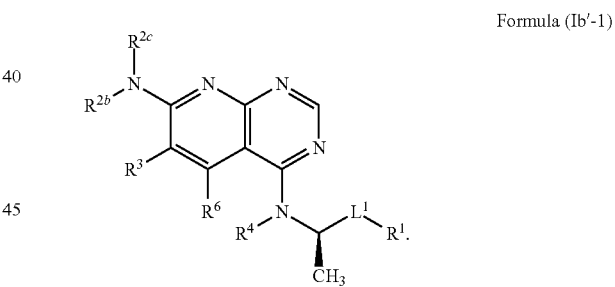

Formula (Ib'-1)

In some embodiments is a compound of Formula (Ic-1) having the structure of Formula (Ic'-1), or a pharmaceutically acceptable salt or solvate thereof:

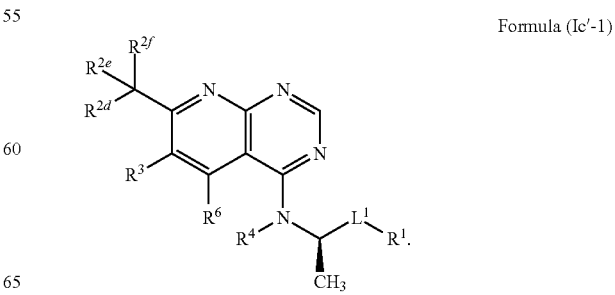

Formula (Ic'-1)

In some embodiments is a compound of Formula (Ia-2) having the structure of Formula (Ia'-2), or a pharmaceutically acceptable salt or solvate thereof:

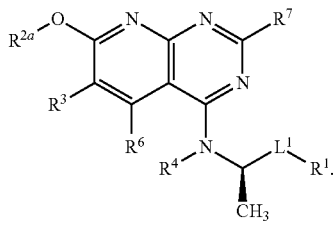

Formula (Ia'-2)

In some embodiments is a compound of Formula (Ib-2) having the structure of Formula (Ib'-2), or a pharmaceutically acceptable salt or solvate thereof:

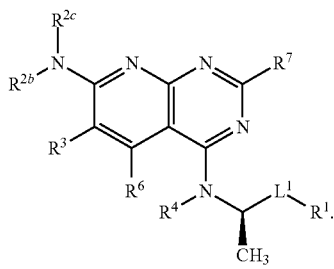

Formula (Ib'-2)

In some embodiments is a compound of Formula (Ic-2) having the structure of Formula (Ic'-2), or a pharmaceutically acceptable salt or solvate thereof:

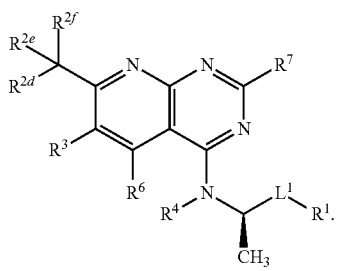

Formula (Ic'-2)

The compounds of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), or a pharmaceutically acceptable salt or solvate thereof, disclosed herein are SOS modulators and have a wide range of applications in therapeutics, diagnostics, and other biomedical research.

In some embodiments is a compound of Formula (I-1), (I'-1), (I-2), or (I'-2), or a pharmaceutically acceptable salt or solvate thereof, wherein $R^2$ is $-OR^{2a}$. In some embodiments is a compound of Formula (I-1), (I'-1), (I-2), or (I'-2), or a pharmaceutically acceptable salt or solvate thereof, wherein $R^2$ is $-NR^{2b}R^{2c}$. In some embodiments is a compound of Formula (I-1), (I'-1), (I-2), or (I'-2), or a pharmaceutically acceptable salt or solvate thereof, wherein $R^2$ is $-SR^{2g}$. In some embodiments is a compound of Formula (I-1), (I'-1), (I-2), or (I'-2), or a pharmaceutically acceptable salt or solvate thereof, wherein $R^2$ is $-C(R^{2d})(R^{2e})(R^{2f})$. In some embodiments is a compound of Formula (I-1), (I'-1), (I-2), or (I'-2), or a pharmaceutically acceptable salt or solvate thereof, wherein $R^2$ is halogen.

In some embodiments is a compound of Formula (I-1), (Ia-1), (Ia'-1), (I-2), (Ia-2), or (Ia'-2), or a pharmaceutically acceptable salt or solvate thereof, wherein $R^{2a}$ is $C_{1-6}$alkyl optionally substituted with one, two, or three $R^{20a}$. In some embodiments is a compound of Formula (I-1), (Ia-1), (Ia'-1), (I-2), (Ia-2), or (Ia'-2), or a pharmaceutically acceptable salt or solvate thereof, wherein $R^{2a}$ is unsubstituted $C_{1-6}$alkyl. In some embodiments is a compound of Formula (I-1), (Ia-1), (Ia'-1), (I-2), (Ia-2), or (Ia'-2), or a pharmaceutically acceptable salt or solvate thereof, wherein $R^{2a}$ is $-CH_3$.

In some embodiments is a compound of Formula (I-1), (Ib-1), (Ib'-1), (I-2), (Ib-2), or (Ib'-2), or a pharmaceutically acceptable salt or solvate thereof, wherein $R^{2b}$ is $C_{1-6}$alkyl optionally substituted with one, two, or three $R^{20a}$. In some embodiments is a compound of Formula (I-1), (Ib-1), (Ib'-1), (I-2), (Ib-2), or (Ib'-2), or a pharmaceutically acceptable salt or solvate thereof, wherein $R^{2b}$ is unsubstituted $C_{1-6}$alkyl. In some embodiments is a compound of Formula (I-1), (Ib-1), (Ib'-1), (I-2), (Ib-2), or (Ib'-2), or a pharmaceutically acceptable salt or solvate thereof, wherein $R^{2b}$ is $-CH_3$. In some embodiments is a compound of Formula (I-1), (Ib-1), (Ib'-1), (I-2), (Ib-2), or (Ib'-2), or a pharmaceutically acceptable salt or solvate thereof, wherein $R^{2b}$ is hydrogen. In some embodiments is a compound of Formula (I-1), (Ib-1), (Ib'-1), (I-2), (Ib-2), or (Ib'-2), or a pharmaceutically acceptable salt or solvate thereof, wherein $R^{2e}$ is $C_{1-6}$alkyl optionally substituted with one, two, or three $R^{20a}$. In some embodiments is a compound of Formula (I-1), (Ib-1), (Ib'-1), (I-2), (Ib-2), or (Ib'-2), or a pharmaceutically acceptable salt or solvate thereof, wherein $R^{2e}$ is unsubstituted $C_{1-6}$ alkyl. In some embodiments is a compound of Formula (I-1), (Ib-1), (Ib'-1), (I-2), (Ib-2), or (Ib'-2), or a pharmaceutically acceptable salt or solvate thereof, wherein $R^{2e}$ is $-CH_3$. In some embodiments is a compound of Formula (I-1), (Ib-1), (Ib'-1), (I-2), (Ib-2), or (Ib'-2), or a pharmaceutically acceptable salt or solvate thereof, wherein $R^{2e}$ is hydrogen. In some embodiments is a compound of Formula (I-1), (Ib-1), (Ib'-1), (I-2), (Ib-2), or (Ib'-2), or a pharmaceutically acceptable salt or solvate thereof, wherein $R^{2b}$ and $R^{2c}$ are independently $C_{1-6}$alkyl optionally substituted with one, two, or three $R^{20a}$. In some embodiments is a compound of Formula (I-1), (Ib-1), (Ib'-1), (I-2), (Ib-2), or (Ib'-2), or a pharmaceutically acceptable salt or solvate thereof, wherein $R^{2b}$ and $R^{2c}$ are independently unsubstituted $C_{1-6}$alkyl. In some embodiments is a compound of Formula (I-1), (Ib-1), (Ib'-1), (I-2), (Ib-2), or (Ib'-2), or a pharmaceutically acceptable salt or solvate thereof, wherein $R^{2b}$ and $R^{2c}$ are $-CH_3$. In some embodiments is a compound of Formula (I-1), (Ib-1), (Ib'-1), (I-2), (Ib-2), or (Ib'-2), or a pharmaceutically acceptable salt or solvate thereof, wherein $R^{2b}$ and $R^{2c}$ are hydrogen.

In some embodiments is a compound of Formula (I-1), (Ic-1), (Ic'-1), (I-2), (Ic-2), or (Ic'-2), or a pharmaceutically acceptable salt or solvate thereof, wherein $R^{2d}$ is hydrogen or $C_{1-6}$alkyl optionally substituted with one, two, or three $R^{20a}$. In some embodiments is a compound of Formula (I-1), (Ic-1), (Ic'-1), (I-2), (Ic-2), or (Ic'-2), or a pharmaceutically acceptable salt or solvate thereof, wherein $R^{2d}$ is hydrogen. In some embodiments is a compound of Formula (I-1), (Ic-1), (Ic'-1), (I-2), (Ic-2), or (Ic'-2), or a pharmaceutically acceptable salt or solvate thereof, wherein $R^{2d}$ is $C_{1-6}$alkyl optionally substituted with one, two, or three $R^{20a}$. In some embodiments is a compound of Formula (I-1), (Ic-1), (Ic'-1), (I-2), (Ic-2), or (Ic'-2), or a pharmaceutically acceptable salt or solvate thereof, wherein $R^{2d}$ is unsubstituted $C_{1-6}$alkyl. In some embodiments is a compound of Formula (I-1), (Ic-1), (Ic'-1), (I-2), (Ic-2), or (Ic'-2), or a pharmaceutically acceptable salt or solvate thereof, wherein $R^{2d}$ is —CH$_3$. In some embodiments is a compound of Formula (I-1), (Ic-1), (Ic'-1), (I-2), (Ic-2), or (Ic'-2), or a pharmaceutically acceptable salt or solvate thereof, wherein $R^{2e}$ is hydrogen or C$_{1-6}$ alkyl optionally substituted with one, two, or three $R^{20a}$. In some embodiments is a compound of Formula (I-1), (Ic-1), (Ic'-1), (I-2), (Ic-2), or (Ic'-2), or a pharmaceutically acceptable salt or solvate thereof, wherein $R^{2e}$ is hydrogen. In some embodiments is a compound of Formula (I-1), (Ic-1), (Ic'-1), (I-2), (Ic-2), or (Ic'-2), or a pharmaceutically acceptable salt or solvate thereof, wherein $R^{2e}$ is C$_{1-6}$alkyl optionally substituted with one, two, or three $R^{20a}$. In some embodiments is a compound of Formula (I-1), (Ic-1), (Ic'-1), (I-2), (Ic-2), or (Ic'-2), or a pharmaceutically acceptable salt or solvate thereof, wherein $R^{2e}$ is unsubstituted C$_{1-6}$alkyl. In some embodiments is a compound of Formula (I-1), (Ic-1), (Ic'-1), (I-2), (Ic-2), or (Ic'-2), or a pharmaceutically acceptable salt or solvate thereof, wherein $R^{2e}$ is —CH$_3$. In some embodiments is a compound of Formula (I-1), (Ic-1), (Ic'-1), (I-2), (Ic-2), or (Ic'-2), or a pharmaceutically acceptable salt or solvate thereof, wherein $R^{21}$ is hydrogen or C$_{1-6}$alkyl optionally substituted with one, two, or three $R^{20a}$. In some embodiments is a compound of Formula (I-1), (Ic-1), (Ic'-1), (I-2), (Ic-2), or (Ic'-2), or a pharmaceutically acceptable salt or solvate thereof, wherein $R^{21}$ is hydrogen. In some embodiments is a compound of Formula (I-1), (Ic-1), (Ic'-1), (I-2), (Ic-2), or (Ic'-2), or a pharmaceutically acceptable salt or solvate thereof, wherein $R^{21}$ is C$_{1-6}$alkyl optionally substituted with one, two, or three $R^{20a}$. In some embodiments is a compound of Formula (I-1), (Ic-1), (Ic'-1), (I-2), (Ic-2), or (Ic'-2), or a pharmaceutically acceptable salt or solvate thereof, wherein $R^{21}$ is unsubstituted C$_{1-6}$alkyl. In some embodiments is a compound of Formula (I-1), (Ic-1), (Ic'-1), (I-2), (Ic-2), or (Ic'-2), or a pharmaceutically acceptable salt or solvate thereof, wherein $R^{21}$ is —CH$_3$.

In some embodiments is a compound of Formula (I-1), (Ia-1), (Ib-1), or (Ic-1), or a pharmaceutically acceptable salt or solvate thereof, wherein $R^5$ is C$_{1-6}$alkyl. In some embodiments is a compound of Formula (I-1), (Ia-1), (Ib-1), or (Ic-1), or a pharmaceutically acceptable salt or solvate thereof, wherein $R^5$ is —CH$_3$. In some embodiments is a compound of Formula (I-1), (Ia-1), (Ib-1), or (Ic-1), or a pharmaceutically acceptable salt or solvate thereof, wherein $R^5$ is C$_{1-6}$haloalkyl. In some embodiments is a compound of Formula (I-1), (Ia-1), (Ib-1), or (Ic-1), or a pharmaceutically acceptable salt or solvate thereof, wherein $R^5$ is hydrogen.

In some embodiments is a compound of Formula (I-1), (I'-1), (Ia-1), (Ia'-1), (Ib-1), (Ib'-1), (Ic-1), or (Ic'-1), or a pharmaceutically acceptable salt or solvate thereof, wherein $R^3$ is selected from —OR$^{12}$, —N(R$^{12}$)(R$^{13}$), —C(O)R$^{15}$, —C(O)N(R$^{12}$)(R$^{13}$), —SR$^{12}$, —SOR$^{12}$, —SO$_2$(R$^{12}$)(R$^{13}$), —SO$_2$N(R$^{12}$)(R$^{13}$), —P(O)(R$^{17}$)(R$^{17a}$), C$_{1-6}$alkyl, C$_{3-10}$cycloalkyl, C$_{2-9}$heterocycloalkyl, C$_{6-10}$aryl, and C$_{1-9}$ heteroaryl, wherein C$_{1-6}$alkyl, C$_{3-10}$cycloalkyl, C$_{2-9}$heterocycloalkyl, C$_{6-10}$aryl, and C$_{1-9}$heteroaryl are optionally substituted with one, two, or three $R^{20b}$.

In some embodiments is a compound of Formula (I-1), (I'-1), (Ia-1), (Ia'-1), (Ib-1), (Ib'-1), (Ic-1), or (Ic'-1), or a pharmaceutically acceptable salt or solvate thereof, wherein $R^3$ is selected from —C(O)R$^{15}$, —C(O)N(R$^{12}$)(R$^{13}$), C$_{2-9}$heterocycloalkyl, C$_{6-10}$aryl, and C$_{1-9}$heteroaryl, wherein C$_{2-9}$heterocycloalkyl, C$_{6-10}$aryl, and C$_{1-9}$heteroaryl are optionally substituted with one, two, or three $R^{20b}$. In some embodiments is a compound of Formula (I-1), (I'-1), (Ia-1), (Ia'-1), (Ib-1), (Ib'-1), (Ic-1), or (Ic'-1), wherein $R^3$ is selected from —C(O)R$^{15}$. In some embodiments is a compound of Formula (I-1), (Ia-1), (Ib-1), (Ic-1), (Id), (Ie) or (If), wherein $R^{15}$ is C$_{2-9}$heterocycloalkyl optionally substituted with one, two, or three $R^{20g}$.

In some embodiments is a compound of Formula (I-1), (I'-1), (Ia-1), (Ia'-1), (Ib-1), (Ib'-1), (Ic-1), or (Ic'-1), or a pharmaceutically acceptable salt or solvate thereof, wherein $R^3$ is C$_{2-9}$heterocycloalkyl optionally substituted with one, two, or three $R^{20b}$. In some embodiments is a compound of Formula (I-1), (I'-1), (Ia-1), (Ia'-1), (Ib-1), (Ib'-1), (Ic-1), or (Ic'-1), or a pharmaceutically acceptable salt or solvate thereof, wherein $R^3$ is spirocyclic C$_{2-9}$heterocycloalkyl optionally substituted with one, two, or three $R^{20b}$. In some embodiments is a compound of Formula (I-1), (I'-1), (Ia-1), (Ia'-1), (Ib-1), (Ib'-1), (Ic-1), or (Ic'-1), or a pharmaceutically acceptable salt or solvate thereof, wherein $R^3$ is fused C$_{2-9}$heterocycloalkyl optionally substituted with one, two, or three $R^{20b}$. In some embodiments is a compound of Formula (I-1), (I'-1), (Ia-1), (Ia'-1), (Ib-1), (Ib'-1), (Ic-1), or (Ic'-1), or a pharmaceutically acceptable salt or solvate thereof, wherein $R^3$ is C$_{6-10}$aryl optionally substituted with one, two, or three $R^{20b}$. In some embodiments is a compound of Formula (I-1), (I'-1), (Ia-1), (Ia'-1), (Ib-1), (Ib'-1), (Ic-1), or (Ic'-1), or a pharmaceutically acceptable salt or solvate thereof, wherein $R^3$ is fused C$_{6-10}$aryl optionally substituted with one, two, or three $R^{20b}$. In some embodiments is a compound of Formula (I-1), (I'-1), (Ia-1), (Ia'-1), (Ib-1), (Ib'-1), (Ic-1), or (Ic'-1), or a pharmaceutically acceptable salt or solvate thereof, wherein $R^3$ is C$_{1-9}$heteroaryl optionally substituted with one, two, or three $R^{20b}$. In some embodiments is a compound of Formula (I-1), (I'-1), (Ia-1), (Ia'-1), (Ib-1), (Ib'-1), (Ic-1), or (Ic'-1), or a pharmaceutically acceptable salt or solvate thereof, wherein $R^3$ is fused C$_{1-9}$heteroaryl optionally substituted with one, two, or three $R^{20b}$. In some embodiments is a compound of Formula (I-1), (I'-1), (Ia-1), (Ia'-1), (Ib-1), (Ib'-1), (Ic-1), or (Ic'-1), or a pharmaceutically acceptable salt or solvate thereof, wherein $R^3$ is —C(O)N(R$^{12}$)(R$^{13}$).

In some embodiments is a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), or a pharmaceutically acceptable salt or solvate thereof, wherein $R^{15}$ is C$_{2-9}$heterocycloalkyl optionally substituted with one, two, or three $R^{20g}$. In some embodiments is a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), or a pharmaceutically acceptable salt or solvate thereof, wherein $R^{15}$ is spirocyclic C$_{2-9}$heterocycloalkyl optionally substituted with one, two, or three $R^{20g}$. In some embodiments is a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), or a pharmaceutically acceptable salt or solvate thereof, wherein $R^{15}$ is fused C$_{2-9}$heterocycloalkyl optionally substituted with one, two, or three $R^{20g}$.

In some embodiments is a compound of Formula (I-1), (I'-1), (Ia-1), (Ia'-1), (Ib-1), (Ib'-1), (Ic-1), or (Ic'-1), or a pharmaceutically acceptable salt or solvate thereof, wherein $R^3$ is C$_{1-6}$alkyl optionally substituted with one, two or three $R^{20b}$. In some embodiments is a compound of Formula (I-1), (I'-1), (Ia-1), (Ia'-1), (Ib-1), (Ib'-1), (Ic-1), or (Ic'-1), or a pharmaceutically acceptable salt or solvate thereof, wherein $R^3$ is —OR$^{12}$. In some embodiments is a compound of Formula (I-1), (I'-1), (Ia-1), (Ia'-1), (Ib-1), (Ib'-1), (Ic-1), or (Ic'-1), or a pharmaceutically acceptable salt or solvate thereof, wherein $R^3$ is —N(R$^{12}$)(R$^{13}$). In some embodiments is a compound of Formula (I-1), (I'-1), (Ia-1), (Ia'-1), (Ib-1), (Ib'-1), (Ic-1), or (Ic'-1), or a pharmaceutically acceptable salt or solvate thereof, wherein $R^3$ is halogen.

In embodiments of a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), or a pharmaceutically acceptable salt or solvate thereof, $R^3$ is $C_{3-14}$cycloalkyl, including $C_{6-14}$cycloalkyl, $C_{6-9}$cycloalkyl, $C_{3-7}$cycloalkyl, $C_{3-6}$cycloalkyl, $C_{3-5}$cycloalkyl, and $C_{3-4}$cycloalkyl, each of which being optionally substituted with one, two, or three $R^{20b}$. In embodiments of a compound of Formula (I-1), (I'-1), (Ia-1), (Ia'-1), (Ib-1), (Ib'-1), (Ic-1), or (Ic'-1), or a pharmaceutically acceptable salt or solvate thereof, $R^3$ is $C_{6-14}$cycloalkyl optionally substituted with one, two, or three $R^{20b}$. In embodiments of a compound of Formula (I-1), (I'-1), (Ia-1), (Ia'-1), (Ib-1), (Ib'-1), (Ic-1), or (Ic'-1), or a pharmaceutically acceptable salt or solvate thereof, $R^3$ is $C_{6-9}$cycloalkyl optionally substituted with one, two, or three $R^{20b}$. In embodiments of a compound of Formula (I-1), (I'-1), (Ia-1), (Ia'-1), (Ib-1), (Ib'-1), (Ic-1), or (Ic'-1), or a pharmaceutically acceptable salt or solvate thereof, $R^3$ is $C_{3-7}$cycloalkyl optionally substituted with one, two, or three $R^{20b}$. In embodiments of a compound of Formula (I-1), (I'-1), (Ia-1), (Ia'-1), (Ib-1), (Ib'-1), (Ic-1), or (Ic'-1), or a pharmaceutically acceptable salt or solvate thereof, $R^3$ is $C_{3-6}$cycloalkyl optionally substituted with one, two, or three $R^{20b}$. In embodiments of a compound of Formula (I-1), (I'-1), (Ia-1), (Ia'-1), (Ib-1), (Ib'-1), (Ic-1), or (Ic'-1), or a pharmaceutically acceptable salt or solvate thereof, $R^3$ is $C_{3-5}$cycloalkyl optionally substituted with one, two, or three $R^{20b}$. In embodiments of a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), or a pharmaceutically acceptable salt or solvate thereof, $R^3$ is $C_{3-4}$cycloalkyl optionally substituted with one, two, or three $R^{20b}$.

In embodiments of a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), or a pharmaceutically acceptable salt or solvate thereof, $R^3$ is $C_{3-14}$cycloalkyl, including $C_{6-14}$cycloalkyl, $C_{6-9}$cycloalkyl, $C_{3-7}$cycloalkyl, $C_{3-6}$cycloalkyl, $C_{3-5}$cycloalkyl, and $C_{3-4}$cycloalkyl, each of which being substituted with one, two, or three $R^{20b}$. In embodiments of a compound of Formula (I-1), (I'-1), (Ia-1), (Ia'-1), (Ib-1), (Ib'-1), (Ic-1), or (Ic'-1), or a pharmaceutically acceptable salt or solvate thereof, $R^3$ is $C_{6-14}$cycloalkyl substituted with one, two, or three $R^{20b}$. In embodiments of a compound of Formula (I-1), (I'-1), (Ia-1), (Ia'-1), (Ib-1), (Ib'-1), (Ic-1), or (Ic'-1), or a pharmaceutically acceptable salt or solvate thereof, $R^3$ is $C_{6-9}$cycloalkyl substituted with one, two, or three $R^{20b}$. In embodiments of a compound of Formula (I-1), (I'-1), (Ia-1), (Ia'-1), (Ib-1), (Ib'-1), (Ic-1), or (Ic'-1), or a pharmaceutically acceptable salt or solvate thereof, $R^3$ is $C_{3-7}$cycloalkyl substituted with one, two, or three $R^{20b}$. In embodiments of a compound of Formula (I-1), (I'-1), (Ia-1), (Ia'-1), (Ib-1), (Ib'-1), (Ic-1), or (Ic'-1), or a pharmaceutically acceptable salt or solvate thereof, $R^3$ is $C_{3-6}$cycloalkyl substituted with one, two, or three $R^{20b}$. In embodiments of a compound of Formula (I-1), (I'-1), (Ia-1), (Ia'-1), (Ib-1), (Ib'-1), (Ic-1), or (Ic'-1), or a pharmaceutically acceptable salt or solvate thereof, $R^3$ is $C_{3-5}$cycloalkyl substituted with one, two, or three $R^{20b}$. In embodiments of a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), or a pharmaceutically acceptable salt or solvate thereof, $R^3$ is $C_{3-4}$cycloalkyl substituted with one, two, or three $R^{20b}$. In embodiments of a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), or a pharmaceutically acceptable salt or solvate thereof, $R^3$ is $C_3$cycloalkyl substituted with one, two, or three $R^{20b}$.

In embodiments of a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), or a pharmaceutically acceptable salt or solvate thereof, $R^3$ is $C_{3-14}$cycloalkyl, including $C_{6-14}$cycloalkyl, $C_{6-9}$cycloalkyl, $C_{3-7}$cycloalkyl, $C_{3-6}$cycloalkyl, $C_{3-5}$cycloalkyl, and $C_{3-4}$cycloalkyl, each of which being optionally substituted with one $R^{20b}$. In embodiments of a compound of Formula (I-1), (I'-1), (Ia-1), (Ia'-1), (Ib-1), (Ib'-1), (Ic-1), or (Ic'-1), or a pharmaceutically acceptable salt or solvate thereof, $R^3$ is $C_{6-14}$cycloalkyl optionally substituted with one $R^{20b}$. In embodiments of a compound of Formula (I-1), (I'-1), (Ia-1), (Ia'-1), (Ib-1), (Ib'-1), (Ic-1), or (Ic'-1), or a pharmaceutically acceptable salt or solvate thereof, $R^3$ is $C_{6-9}$cycloalkyl optionally substituted with one $R^{20b}$. In embodiments of a compound of Formula (I-1), (I'-1), (Ia-1), (Ia'-1), (Ib-1), (Ib'-1), (Ic-1), or (Ic'-1), or a pharmaceutically acceptable salt or solvate thereof, $R^3$ is $C_{3-7}$cycloalkyl optionally substituted with one $R^{20b}$. In embodiments of a compound of Formula (I-1), (I'-1), (Ia-1), (Ia'-1), (Ib-1), (Ib'-1), (Ic-1), or (Ic'-1), or a pharmaceutically acceptable salt or solvate thereof, $R^3$ is $C_{3-6}$cycloalkyl optionally substituted with one $R^{20b}$. In embodiments of a compound of Formula (I-1), (I'-1), (Ia-1), (Ia'-1), (Ib-1), (Ib'-1), (Ic-1), or (Ic'-1), or a pharmaceutically acceptable salt or solvate thereof, $R^3$ is $C_{3-5}$cycloalkyl optionally substituted with one $R^{20b}$. In embodiments of a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), or a pharmaceutically acceptable salt or solvate thereof, $R^3$ is $C_{3-4}$cycloalkyl optionally substituted with one $R^{20b}$. In embodiments of a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), or a pharmaceutically acceptable salt or solvate thereof, $R^3$ is $C_3$cycloalkyl optionally substituted with one $R^{20b}$. In embodiments of a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), or a pharmaceutically acceptable salt or solvate thereof, $R^3$ is $C_3$cycloalkyl substituted with one $R^{20b}$.

In embodiments of a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), or a pharmaceutically acceptable salt or solvate thereof, $R^3$ is $C_{3-14}$cycloalkyl, including $C_{6-14}$cycloalkyl, $C_{6-9}$cycloalkyl, $C_{3-7}$cycloalkyl, $C_{3-6}$cycloalkyl, $C_{3-5}$cycloalkyl, and $C_{3-4}$cycloalkyl, each of which being optionally substituted with two $R^{20b}$. In embodiments of a compound of Formula (I-1), (I'-1), (Ia-1), (Ia'-1), (Ib-1), (Ib'-1), (Ic-1), or (Ic'-1), or a pharmaceutically acceptable salt or solvate thereof, $R^3$ is $C_{6-14}$cycloalkyl optionally substituted with two $R^{20b}$. In embodiments of a compound of Formula (I-1), (I'-1), (Ia-1), (Ia'-1), (Ib-1), (Ib'-1), (Ic-1), or (Ic'-1), or a pharmaceutically acceptable salt or solvate thereof, $R^3$ is $C_{6-9}$cycloalkyl optionally substituted with two $R^{20b}$. In embodiments of a compound of Formula (I-1), (I'-1), (Ia-1), (Ia'-1), (Ib-1), (Ib'-1), (Ic-1), or (Ic'-1), or a pharmaceutically acceptable salt or solvate thereof, $R^3$ is $C_{3-7}$cycloalkyl optionally substituted with two $R^{20b}$. In embodiments of a compound of Formula (I-1), (I'-1), (Ia-1), (Ia'-1), (Ib-1), (Ib'-1), (Ic-1), or (Ic'-1), or a pharmaceutically acceptable salt or solvate thereof, $R^3$ is $C_{3-6}$cycloalkyl optionally substituted with one $R^{20b}$. In embodiments of a compound of Formula (I-1), (I'-1), (Ia-1), (Ia'-1), (Ib-1), (Ib'-1), (Ic-1), or (Ic'-1), or a pharmaceutically acceptable salt or solvate thereof, $R^3$ is $C_{3-5}$cycloalkyl optionally substituted with two $R^{20b}$. In embodiments of a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), or a pharmaceutically acceptable salt or solvate thereof, $R^3$ is $C_{3-4}$cycloalkyl optionally substituted with two $R^{20b}$. In embodiments of a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), or a pharmaceutically acceptable salt or solvate thereof, $R^3$ is $C_3$cycloalkyl optionally substituted with two $R^{20b}$. In embodiments of a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), or a pharmaceutically acceptable salt or solvate thereof, $R^3$ is $C_3$cycloalkyl substituted with two $R^{20b}$.

In each of the above embodiments, $R^{20b}$ is independently selected from amino, —CN, $C_{1-3}$alkyl, $C_{1-3}$alkoxy, $C_{1-3}$haloalkyl, —OH, —N($R^{24}$)C(O)$R^{25}$, and —C(O)N($R^{22}$)($R^{23}$). In some embodiments of a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), or a pharmaceutically acceptable salt or solvate thereof, $R^{20b}$ is amino. In some embodiments of a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), or a pharmaceutically acceptable salt or solvate thereof, $R^{20b}$ is —CN. In some embodiments of a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), or a pharmaceutically acceptable salt or solvate thereof, $R^{20b}$ is $C_{1-3}$alkyl. In some embodiments of a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib- 2), (Ib'-2), (Ic-2), or (Ic'-2), or a pharmaceutically acceptable salt or solvate thereof, $R^{20b}$ is $C_{1-3}$alkoxy. In some embodiments of a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), or a pharmaceutically acceptable salt or solvate thereof, $R^{20b}$ is $C_{1-3}$haloalkyl. In some embodiments of a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), or a pharmaceutically acceptable salt or solvate thereof, $R^{20b}$ is —OH. In some embodiments of a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), or a pharmaceutically acceptable salt or solvate thereof, $R^{20b}$ is —N($R^{24}$)C(O)$R^{25}$. In some embodiments of a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), or a pharmaceutically acceptable salt or solvate thereof, $R^{20b}$ is —C(O)N($R^{22}$)($R^{23}$). In some embodiments of a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), or a pharmaceutically acceptable salt or solvate thereof, $R^{20b}$ is —NHC(O)$R^{25}$. In some embodiments of a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), or a pharmaceutically acceptable salt or solvate thereof, $R^{20b}$ is —C(O)NH($R^{22}$). In some embodiments of a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib- 2), (Ib'-2), (Ic-2), or (Ic'-2), or a pharmaceutically acceptable salt or solvate thereof, $R^{20b}$ is —NHC(O)$R^{25}$ and $R^{25}$ is $C_{2-9}$heterocycloalkyl optionally substituted with one, two, or three groups independently selected from halogen, $C_{1-6}$alkyl, $C_{1-6}$haloalkyl, $C_{1-6}$alkoxy, $C_{3-7}$cycloalkyl, $C_{2-9}$heterocycloalkyl, $C_{6-10}$aryl, and $C_{1-9}$heteroaryl. In some embodiments of a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), or a pharmaceutically acceptable salt or solvate thereof, $R^{20b}$ is —C(O)NH($R^{22}$) and $R^{22}$ is $C_{2-9}$heterocycloalkyl optionally substituted with one, two, or three groups independently selected from halogen and $C_{1-6}$alkyl. In some embodiments of a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), or a pharmaceutically acceptable salt or solvate thereof, $R^{20b}$ is —NHC(O)$R^{25}$ and $R^{25}$ is $C_{2-5}$heterocycloalkyl optionally substituted with one $C_{1-6}$alkyl. In some embodiments of a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), or a pharmaceutically acceptable salt or solvate thereof, $R^{20b}$ is —C(O)NH($R^{22}$) and $R^{22}$ is $C_{2-5}$heterocycloalkyl optionally substituted with one $C_{1-6}$alkyl.

In embodiments of a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), or a pharmaceutically acceptable salt or solvate thereof, $R^3$ is $C_{6-14}$cycloalkyl (including $C_{6-14}$cycloalkyl, $C_{6-9}$cycloalkyl, $C_{3-7}$cycloalkyl, $C_{3-6}$cycloalkyl, $C_{3-5}$cycloalkyl, and $C_{3-4}$cycloalkyl), optionally substituted with one, two, or three $R^{20b}$ that is amino. In embodiments of a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), or a pharmaceutically acceptable salt or solvate thereof, $R^3$ is $C_{6-14}$cycloalkyl (including $C_{6-14}$cycloalkyl, $C_{6-9}$cycloalkyl, $C_{3-7}$cycloalkyl, $C_{3-6}$cycloalkyl, $C_{3-5}$cycloalkyl, and $C_{3-4}$cycloalkyl), optionally substituted with one, two, or three $R^{20b}$ that is —CN. In embodiments of a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), or a pharmaceutically acceptable salt or solvate thereof, $R^3$ is $C_{6-14}$cycloalkyl (including $C_{6-14}$cycloalkyl, $C_{6-9}$cycloalkyl, $C_{3-7}$cycloalkyl, $C_{3-6}$cycloalkyl, $C_{3-5}$cycloalkyl, and $C_{3-4}$cycloalkyl), optionally substituted with one, two, or three $R^{20b}$ that is $C_{1-3}$alkyl. In embodiments of a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), or a pharmaceutically acceptable salt or solvate thereof, $R^3$ is $C_{6-14}$cycloalkyl (including $C_{6-14}$cycloalkyl, $C_{6-9}$cycloalkyl, $C_{3-7}$cycloalkyl, $C_{3-6}$cycloalkyl, $C_{3-5}$cycloalkyl, and $C_{3-4}$cycloalkyl), optionally substituted with one, two, or three $R^{20b}$ that is $C_{1-3}$alkoxy. In embodiments of a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), or a pharmaceutically acceptable salt or solvate thereof, $R^3$ is $C_{6-14}$cycloalkyl (including $C_{6-14}$cycloalkyl, $C_{6-9}$cycloalkyl, $C_{3-7}$cycloalkyl, $C_{3-6}$cycloalkyl, $C_{3-5}$cycloalkyl, and $C_{3-4}$cycloalkyl), optionally substituted with one, two, or three $R^{20b}$ that is $C_{1-3}$haloalkyl. In embodiments of a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib- 2), (Ib'-2), (Ic-2), or (Ic'-2), or a pharmaceutically acceptable salt or solvate thereof, $R^3$ is $C_{6-14}$cycloalkyl (including $C_{6-14}$cycloalkyl, $C_{6-9}$cycloalkyl, $C_{3-7}$cycloalkyl, $C_{3-6}$cycloalkyl, $C_{3-5}$cycloalkyl, and $C_{3-4}$cycloalkyl), optionally substituted with one, two, or three $R^{20b}$ that is —OH. In embodiments of a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), or a pharmaceutically acceptable salt or solvate thereof, $R^3$ is $C_{6-14}$cycloalkyl (including $C_{6-14}$cycloalkyl, $C_{6-9}$cycloalkyl, $C_{3-7}$cycloalkyl, $C_{3-6}$cycloalkyl, $C_{3-5}$cycloalkyl, and $C_{3-4}$cycloalkyl), optionally substituted with one, two, or three $R^{20b}$ that is oxo. In embodiments of a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), or a pharmaceutically acceptable salt or solvate thereof, $R^3$ is $C_{6-14}$cycloalkyl (including $C_{6-14}$cycloalkyl, $C_{6-9}$cycloalkyl, $C_{3-7}$cycloalkyl, $C_{3-6}$cycloalkyl, $C_{3-5}$cycloalkyl, and $C_{3-4}$cycloalkyl), optionally substituted with one, two, or three $R^{20b}$ that is $-N(R^{24})C(O)R^{25}$. In embodiments of a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), or a pharmaceutically acceptable salt or solvate thereof, $R^3$ is $C_{6-14}$cycloalkyl (including $C_{6-14}$cycloalkyl, $C_{6-9}$cycloalkyl, $C_{3-7}$cycloalkyl, $C_{3-6}$cycloalkyl, $C_{3-5}$cycloalkyl, and $C_{3-4}$cycloalkyl), optionally substituted with one, two, or three $R^{20b}$ that is $-NHC(O)R^{25}$. In embodiments of a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), or a pharmaceutically acceptable salt or solvate thereof, $R^3$ is $C_{6-14}$cycloalkyl (including $C_{6-14}$cycloalkyl, $C_{6-9}$cycloalkyl, $C_{3-7}$cycloalkyl, $C_{3-6}$cycloalkyl, $C_{3-5}$cycloalkyl, and $C_{3-4}$cycloalkyl), optionally substituted with one, two, or three $R^{20b}$ that is $-NHC(O)R^{25}$ and $R^{25}$ is $C_{2-9}$heterocycloalkyl optionally substituted with one, two, or three groups independently selected from halogen, $C_{1-6}$alkyl, $C_{1-6}$haloalkyl, $C_{1-6}$alkoxy, $C_{3-7}$cycloalkyl, $C_{2-9}$heterocycloalkyl, $C_{6-10}$aryl, and $C_{1-9}$heteroaryl. In embodiments of a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), or a pharmaceutically acceptable salt or solvate thereof, $R^3$ is $C_{6-14}$cycloalkyl (including $C_{6-14}$cycloalkyl, $C_{6-9}$cycloalkyl, $C_{3-7}$cycloalkyl, $C_{3-6}$cycloalkyl, $C_{3-5}$cycloalkyl, and $C_{3-4}$cycloalkyl), optionally substituted with one, two, or three $R^{20b}$ that is $-NHC(O)R^{25}$ and $R^{25}$ is $C_{2-5}$heterocycloalkyl optionally substituted with one $C_{1-6}$alkyl. In embodiments of a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), or a pharmaceutically acceptable salt or solvate thereof, $R^3$ is $C_{6-14}$cycloalkyl (including $C_{6-14}$cycloalkyl, $C_{6-9}$cycloalkyl, $C_{3-7}$cycloalkyl, $C_{3-6}$cycloalkyl, $C_{3-5}$cycloalkyl, and $C_{3-4}$cycloalkyl), optionally substituted with one, two, or three $R^{20b}$ that is $-C(O)N(R^{22})(R^{23})$. In embodiments of a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), or a pharmaceutically acceptable salt or solvate thereof, $R^3$ is $C_{6-14}$cycloalkyl (including $C_{6-14}$cycloalkyl, $C_{6-9}$cycloalkyl, $C_{3-7}$cycloalkyl, $C_{3-6}$cycloalkyl, $C_{3-5}$cycloalkyl, and $C_{3-4}$cycloalkyl), optionally substituted with one, two, or three $R^{20b}$ that is $-C(O)NH(R^{22})$. In embodiments of a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), or a pharmaceutically acceptable salt or solvate thereof, $R^3$ is $C_{6-14}$cycloalkyl (including $C_{6-14}$cycloalkyl, $C_{6-9}$cycloalkyl, $C_{3-7}$cycloalkyl, $C_{3-6}$cycloalkyl, $C_{3-5}$cycloalkyl, and $C_{3-4}$cycloalkyl), optionally substituted with one, two, or three $R^{20b}$ that is $-C(O)NH(R^{22})$ and $R^{22}$ is $C_{2-9}$heterocycloalkyl optionally substituted with one, two, or three groups independently selected from halogen and $C_{1-6}$alkyl. In embodiments of a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), or a pharmaceutically acceptable salt or solvate thereof, $R^3$ is $C_{6-14}$cycloalkyl (including $C_{6-14}$cycloalkyl, $C_{6-9}$cycloalkyl, $C_{3-7}$cycloalkyl, $C_{3-6}$cycloalkyl, $C_{3-5}$cycloalkyl, and $C_{3-4}$cycloalkyl), optionally substituted with one, two, or three $R^{20b}$ that is $-C(O)NH(R^{22})$ and $R^{22}$ is $C_{2-5}$heterocycloalkyl optionally substituted with one $C_{1-6}$alkyl.

In embodiments of a compound of Formula (I-1), (I'-1), (Ia-1), (Ia'-1), (Ib-1), (Ib'-1), (Ic-1), or (Ic'-1), or a pharmaceutically acceptable salt or solvate thereof, $R^3$ is $C_{2-9}$heterocycloalkyl, including $C_{6-9}$heterocycloalkyl, $C_{3-7}$heterocycloalkyl, $C_{3-6}$heterocycloalkyl, $C_{5-6}$ heterocycloalkyl, $C_{3-5}$heterocycloalkyl, $C_{3-4}$heterocycloalkyl, each of which being optionally substituted with one, two, or three $R^{20b}$. In embodiments of a compound of Formula (I-1), (I'-1), (Ia-1), (Ia'-1), (Ib-1), (Ib'-1), (Ic-1), or (Ic'-1), or a pharmaceutically acceptable salt or solvate thereof, $R^3$ is $C_{6-9}$heterocycloalkyl optionally substituted with one, two, or three $R^{20b}$. In embodiments of a compound of Formula (I-1), (I'-1), (Ia-1), (Ia'-1), (Ib-1), (Ib'-1), (Ic-1), or (Ic'-1), or a pharmaceutically acceptable salt or solvate thereof, $R^3$ is $C_{3-7}$heterocycloalkyl optionally substituted with one, two, or three $R^{20b}$. In embodiments of a compound of Formula (I-1), (I'-1), (Ia-1), (Ia'-1), (Ib-1), (Ib'-1), (Ic-1), or (Ic'-1), or a pharmaceutically acceptable salt or solvate thereof, $R^3$ is $C_{3-6}$heterocycloalkyl optionally substituted with one, two, or three $R^{20b}$. In embodiments of a compound of Formula (I-1), (I'-1), (Ia-1), (Ia'-1), (Ib-1), (Ib'-1), (Ic-1), or (Ic'-1), or a pharmaceutically acceptable salt or solvate thereof, $R^3$ is $C_{5-6}$ heterocycloalkyl optionally substituted with one, two, or three $R^{20b}$. In embodiments of a compound of Formula (I-1), (I'-1), (Ia-1), (Ia'-1), (Ib-1), (Ib'-1), (Ic-1), or (Ic'-1), or a pharmaceutically acceptable salt or solvate thereof, $R^3$ is $C_{3-5}$ heterocycloalkyl optionally substituted with one, two, or three $R^{20b}$. In embodiments of a compound of Formula (I-1), (I'-1), (Ia-1), (Ia'-1), (Ib-1), (Ib'-1), (Ic-1), or (Ic'-1), or a pharmaceutically acceptable salt or solvate thereof, $R^3$ is $C_{3-4}$heterocycloalkyl optionally substituted with one, two, or three $R^{20b}$.

In embodiments, each of the $R^3$ described above including $C_{6-9}$heterocycloalkyl, $C_{3-7}$heterocycloalkyl, $C_{3-6}$heterocycloalkyl, $C_{5-6}$ heterocycloalkyl, $C_{3-5}$heterocycloalkyl, $C_{3-4}$heterocycloalkyl, is optionally substituted with one $R^{20b}$. In embodiments, each of the $R^3$ described above, including $C_{6-9}$heterocycloalkyl, $C_{3-7}$heterocycloalkyl, $C_{3-6}$heterocycloalkyl, $C_{5-6}$ heterocycloalkyl, $C_{3-5}$heterocycloalkyl, $C_{3-4}$heterocycloalkyl, is optionally substituted with two $R^{20b}$. In embodiments, each of the $R^3$ described above, including $C_{6-9}$heterocycloalkyl, $C_{3-7}$heterocycloalkyl, $C_{3-6}$heterocycloalkyl, $C_{5-6}$ heterocycloalkyl, $C_{3-5}$heterocycloalkyl, $C_{3-4}$heterocycloalkyl, is optionally substituted with three $R^{20b}$.

In each of the above embodiments, $R^{20b}$ is independently selected from amino, $-CN$, $C_{1-3}$alkyl, $C_{1-3}$alkoxy, $C_{1-3}$haloalkyl, $-OH$, $-N(R^{24})C(O)R^{25}$, and $-C(O)N(R^{22})(R^{23})$. In some embodiments of a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), or a pharmaceutically acceptable salt or solvate thereof, $R^{20b}$ is amino. In some embodiments of a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), or a pharmaceutically acceptable salt or solvate thereof, $R^{20b}$ is $-CN$. In some embodiments of a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), or a pharmaceutically acceptable salt or solvate thereof, $R^{20b}$ is $C_{1-3}$alkyl. In some embodiments of a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), or a pharmaceutically acceptable salt or solvate thereof, $R^{20b}$ is $C_{1-3}$alkoxy. In some embodiments of a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), or a pharmaceutically acceptable salt or solvate thereof, $R^{20b}$ is $C_{1-3}$haloalkyl. In some embodiments of a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), or a pharmaceutically acceptable salt or solvate thereof, $R^{20b}$ is —OH. In some embodiments of a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), or a pharmaceutically acceptable salt or solvate thereof, $R^{20b}$ is —$N(R^{24})C(O)R^{25}$. In some embodiments of a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), or a pharmaceutically acceptable salt or solvate thereof, $R^{20b}$ is —$C(O)N(R^{22})(R^{23})$. In some embodiments of a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), or a pharmaceutically acceptable salt or solvate thereof, $R^{20b}$ is —$NHC(O)R^{25}$. In some embodiments of a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), or a pharmaceutically acceptable salt or solvate thereof, $R^{20b}$ is —$C(O)NH(R^{22})$. In some embodiments of a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), or a pharmaceutically acceptable salt or solvate thereof, $R^{20b}$ is —$NHC(O)R^{25}$ and $R^{25}$ is $C_{2-9}$heterocycloalkyl optionally substituted with one, two, or three groups independently selected from halogen, $C_{1-6}$alkyl, $C_{1-6}$haloalkyl, $C_{1-6}$alkoxy, $C_{3-7}$cycloalkyl, $C_{2-9}$heterocycloalkyl, $C_{6-10}$aryl, and $C_{1-9}$heteroaryl. In some embodiments of a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), or a pharmaceutically acceptable salt or solvate thereof, $R^{20b}$ is —$C(O)NH(R^{22})$ and $R^{22}$ is $C_{2-9}$heterocycloalkyl optionally substituted with one, two, or three groups independently selected from halogen and $C_{1-6}$alkyl. In some embodiments of a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), or a pharmaceutically acceptable salt or solvate thereof, $R^{20b}$ is —$NHC(O)R^{25}$ and $R^{25}$ is $C_{2-5}$heterocycloalkyl optionally substituted with one $C_{1-6}$alkyl. In some embodiments of a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), or a pharmaceutically acceptable salt or solvate thereof, $R^{20b}$ is —$C(O)NH(R^{22})$ and $R^{22}$ is $C_{2-5}$heterocycloalkyl optionally substituted with one $C_{1-6}$alkyl. In some embodiments of a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), or a pharmaceutically acceptable salt or solvate thereof, $R^{20b}$ is $C_{1-3}$alkyl substituted with one, two, or three halogen. In some embodiments of a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), or a pharmaceutically acceptable salt or solvate thereof, $R^{20b}$ is $C_{1-3}$alkyl substituted with one, two, or three F. In some embodiments of a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), or a pharmaceutically acceptable salt or solvate thereof, $R^{20b}$ is $C_{1-3}$alkyl substituted with two halogen. In some embodiments of a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), or a pharmaceutically acceptable salt or solvate thereof, $R^{20b}$ is $C_{1-3}$alkyl substituted with two F. In some embodiments of a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), or a pharmaceutically acceptable salt or solvate thereof, $R^{20b}$ is methyl substituted with one, two, or three halogen. In some embodiments of a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), or a pharmaceutically acceptable salt or solvate thereof, $R^{2b}$ is methyl substituted with one, two, or three F. In some embodiments of a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), or a pharmaceutically acceptable salt or solvate thereof, $R^{20b}$ is methyl substituted with two halogen. In some embodiments of a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), or a pharmaceutically acceptable salt or solvate thereof, $R^{20b}$ is methyl substituted with two F. In some embodiments of a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), or a pharmaceutically acceptable salt or solvate thereof, $R^{20b}$ is methyl substituted with one halogen. In some embodiments of a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), or a pharmaceutically acceptable salt or solvate thereof, $R^{20b}$ is methyl substituted with one F. In some embodiments of a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), or a pharmaceutically acceptable salt or solvate thereof, $R^{20b}$ is methyl substituted with three halogen. In some embodiments of a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), or a pharmaceutically acceptable salt or solvate thereof, $R^{20b}$ is methyl substituted with three F.

In embodiments of a compound of Formula (I-1), (I'-1), (Ia-1), (Ia'-1), (Ib-1), (Ib'-1), (Ic-1), or (Ic'-1), or a pharmaceutically acceptable salt or solvate thereof, $R^3$ is $C_{2-9}$heterocycloalkyl (including $C_{6-9}$heterocycloalkyl, $C_{3-7}$heterocycloalkyl, $C_{3-6}$heterocycloalkyl, $C_{5-6}$heterocycloalkyl, $C_{3-5}$heterocycloalkyl, and $C_{3-4}$heterocycloalkyl), optionally substituted with one, two, or three $R^{20b}$ that is amino. In embodiments of a compound of Formula (I-1), (I'-1), (Ia-1), (Ia'-1), (Ib-1), (Ib'-1), (Ic-1), or (Ic'-1), or a pharmaceutically acceptable salt or solvate thereof, $R^3$ is $C_{2-9}$heterocycloalkyl (including $C_{6-9}$heterocycloalkyl, $C_{3-7}$heterocycloalkyl, $C_{3-6}$heterocycloalkyl, $C_{5-6}$heterocycloalkyl, $C_{3-5}$heterocycloalkyl, and $C_{3-4}$heterocycloalkyl), optionally substituted with one, two, or three $R^{20b}$ that is —CN. In embodiments of a compound of Formula (I-1), (I'-1), (Ia-1), (Ia'-1), (Ib-1), (Ib'-1), (Ic-1), or (Ic'-1), or a pharmaceutically acceptable salt or solvate thereof, $R^3$ is $C_{2-9}$heterocycloalkyl (including $C_{6-9}$heterocycloalkyl, $C_{3-7}$heterocycloalkyl, $C_{3-6}$heterocycloalkyl, $C_{5-6}$heterocycloalkyl, $C_{3-5}$heterocycloalkyl, and $C_{3-4}$heterocycloalkyl), optionally substituted with one, two, or three $R^{20b}$ that is $C_{1-3}$alkyl. In embodiments of a compound of Formula (I-1), (I'-1), (Ia-1), (Ia'-1), (Ib-1), (Ib'-1), (Ic-1), or (Ic'-1), or a pharmaceutically acceptable salt or solvate thereof, $R^3$ is $C_{2-9}$heterocycloalkyl (including $C_{6-9}$heterocycloalkyl, $C_{3-7}$heterocycloalkyl, $C_{3-6}$heterocycloalkyl, $C_{5-6}$heterocycloalkyl, $C_{3-5}$heterocycloalkyl, and $C_{3-4}$heterocycloalkyl), optionally substituted with one, two, or three $R^{20b}$ that is $C_{1-3}$alkoxy. In embodiments of a compound of Formula (I-1), (I'-1), (Ia-1), (Ia'-1), (Ib-1), (Ib'-1), (Ic-1), or (Ic'-1), or a pharmaceutically acceptable salt or solvate thereof, $R^3$ is $C_{2-9}$heterocycloalkyl (including $C_{6-9}$heterocycloalkyl, $C_{3-7}$heterocycloalkyl, $C_{3-6}$heterocycloalkyl, $C_{5-6}$heterocycloalkyl, $C_{3-5}$heterocycloalkyl, and $C_{3-4}$heterocycloalkyl), optionally substituted with one, two, or three $R^{20b}$ that is $C_{1-3}$haloalkyl. In embodiments of a compound of Formula (I-1), (I'-1), (Ia-1), (Ia'-1), (Ib-1), (Ib'-1), (Ic-1), or (Ic'-1), or a pharmaceutically acceptable salt or solvate thereof, $R^3$ is $C_{2-9}$heterocycloalkyl (including $C_{6-9}$ heterocycloalkyl, $C_{3-7}$heterocycloalkyl, $C_{3-6}$heterocycloalkyl, $C_{5-6}$heterocycloalkyl, $C_{3-5}$heterocycloalkyl, and $C_{3-4}$heterocycloalkyl), optionally substituted with one, two, or three $R^{20b}$ that is —OH. In embodiments of a compound of Formula (I-1), (I'-1), (Ia-1), (Ia'-1), (Ib-1), (Ib'-1), (Ic-1), or (Ic'-1), or a pharmaceutically acceptable salt or solvate thereof, $R^3$ is $C_{2-9}$heterocycloalkyl (including $C_{6-9}$ heterocycloalkyl, $C_{3-7}$heterocycloalkyl, $C_{3-6}$heterocycloalkyl, $C_{5-6}$heterocycloalkyl, $C_{3-5}$heterocycloalkyl, and $C_{3-4}$heterocycloalkyl), optionally substituted with one, two, or three $R^{2b}$ that is oxo. In embodiments of a compound of Formula (I-1), (I'-1), (Ia-1), (Ia'-1), (Ib-1), (Ib'-1), (Ic-1), or (Ic'-1), or a pharmaceutically acceptable salt or solvate thereof, $R^3$ is $C_{2-9}$heterocycloalkyl (including $C_{6-9}$ heterocycloalkyl, $C_{3-7}$heterocycloalkyl, $C_{3-6}$heterocycloalkyl, $C_{5-6}$heterocycloalkyl, $C_{3-5}$heterocycloalkyl, and $C_{3-4}$heterocycloalkyl), optionally substituted with one, two, or three $R^{20b}$ that is —N($R^{24}$)C(O)$R^{25}$. In embodiments of a compound of Formula (I-1), (I'-1), (Ia-1), (Ia'-1), (Ib-1), (Ib'-1), (Ic-1), or (Ic'-1), or a pharmaceutically acceptable salt or solvate thereof, $R^3$ is $C_{2-9}$heterocycloalkyl (including $C_{6-9}$heterocycloalkyl, $C_{3-7}$heterocycloalkyl, $C_{3-6}$heterocycloalkyl, $C_{5-6}$heterocycloalkyl, $C_{3-5}$heterocycloalkyl, and $C_{3-4}$heterocycloalkyl), optionally substituted with one, two, or three $R^{20b}$ that is —NHC(O)$R^{25}$. In embodiments of a compound of Formula (I-1), (I'-1), (Ia-1), (Ia'-1), (Ib-1), (Ib'-1), (Ic-1), or (Ic'-1), or a pharmaceutically acceptable salt or solvate thereof, $R^3$ is $C_{2-9}$heterocycloalkyl (including $C_{6-9}$heterocycloalkyl, $C_{3-7}$heterocycloalkyl, $C_{3-6}$heterocycloalkyl, $C_{5-6}$heterocycloalkyl, $C_{3-5}$heterocycloalkyl, and $C_{3-4}$heterocycloalkyl), optionally substituted with one, two, or three $R^{20b}$ that is —NHC(O)$R^{25}$ and $R^{25}$ is $C_{2-9}$heterocycloalkyl optionally substituted with one, two, or three groups independently selected from halogen, $C_{1-6}$alkyl, $C_{1-6}$haloalkyl, $C_{1-6}$alkoxy, $C_{3-7}$cycloalkyl, $C_{2-9}$heterocycloalkyl, $C_{6-10}$aryl, and $C_{1-9}$heteroaryl. In embodiments of a compound of Formula (I-1), (I'-1), (Ia-1), (Ia'-1), (Ib-1), (Ib'-1), (Ic-1), or (Ic'-1), or a pharmaceutically acceptable salt or solvate thereof, $R^3$ is $C_{2-9}$heterocycloalkyl (including $C_{6-9}$heterocycloalkyl, $C_{3-7}$heterocycloalkyl, $C_{3-6}$heterocycloalkyl, $C_{5-6}$heterocycloalkyl, $C_{3-5}$heterocycloalkyl, and $C_{3-4}$heterocycloalkyl), optionally substituted with one, two, or three $R^{20b}$ that is —NHC(O)$R^{25}$ and $R^{25}$ is $C_{2-5}$heterocycloalkyl optionally substituted with one $C_{1-6}$alkyl. In embodiments of a compound of Formula (I-1), (I'-1), (Ia-1), (Ia'-1), (Ib-1), (Ib'-1), (Ic-1), or (Ic'-1), or a pharmaceutically acceptable salt or solvate thereof, $R^3$ is $C_{2-9}$heterocycloalkyl (including $C_{6-9}$heterocycloalkyl, $C_{3-7}$heterocycloalkyl, $C_{3-6}$heterocycloalkyl, $C_{5-6}$heterocycloalkyl, $C_{3-5}$heterocycloalkyl, and $C_{3-4}$heterocycloalkyl), optionally substituted with one, two, or three $R^{20b}$ that is —C(O)N($R^{22}$)($R^{23}$). In embodiments of a compound of Formula (I-1), (I'-1), (Ia-1), (Ia'-1), (Ib-1), (Ib'-1), (Ic-1), or (Ic'-1), or a pharmaceutically acceptable salt or solvate thereof, $R^3$ is $C_{2-9}$heterocycloalkyl (including $C_{6-9}$ heterocycloalkyl, $C_{3-7}$heterocycloalkyl, $C_{3-6}$heterocycloalkyl, $C_{5-6}$heterocycloalkyl, $C_{3-5}$heterocycloalkyl, and $C_{3-4}$heterocycloalkyl), optionally substituted with one, two, or three $R^{20b}$ that is —C(O)NH($R^{22}$). In embodiments of a compound of Formula (I-1), (I'-1), (Ia-1), (Ia'-1), (Ib-1), (Ib'-1), (Ic-1), or (Ic'-1), or a pharmaceutically acceptable salt or solvate thereof, $R^3$ is $C_{2-9}$heterocycloalkyl (including $C_{6-9}$heterocycloalkyl, $C_{3-7}$heterocycloalkyl, $C_{3-6}$heterocycloalkyl, $C_{5-6}$heterocycloalkyl, $C_{3-5}$heterocycloalkyl, and $C_{3-4}$heterocycloalkyl), optionally substituted with one, two, or three $R^{20b}$ that is —C(O)NH($R^{22}$) and $R^{22}$ is $C_{2-9}$heterocycloalkyl optionally substituted with one, two, or three groups independently selected from halogen and $C_{1-6}$alkyl. In embodiments of a compound of Formula (I-1), (I'-1), (Ia-1), (Ia'-1), (Ib-1), (Ib'-1), (Ic-1), or (Ic'-1), or a pharmaceutically acceptable salt or solvate thereof, $R^3$ is $C_{2-9}$heterocycloalkyl (including $C_{6-9}$heterocycloalkyl, $C_{3-7}$heterocycloalkyl, $C_{3-6}$heterocycloalkyl, $C_{5-6}$heterocycloalkyl, $C_{3-5}$heterocycloalkyl, and $C_{3-4}$heterocycloalkyl), optionally substituted with one, two, or three $R^{20b}$ that is —C(O)NH($R^{22}$) and $R^{22}$ is $C_{2-5}$heterocycloalkyl optionally substituted with one $C_{1-6}$alkyl.

In embodiments of a compound of Formula (I-1), (I'-1), (Ia-1), (Ia'-1), (Ib-1), (Ib'-1), (Ic-1), or (Ic'-1), or a pharmaceutically acceptable salt or solvate thereof, $R^3$ is thianyl substituted with one, two, or three $R^{20b}$. In embodiments of a compound of Formula (I-1), (I'-1), (Ia-1), (Ia'-1), (Ib-1), (Ib'-1), (Ic-1), or (Ic'-1), or a pharmaceutically acceptable salt or solvate thereof, $R^3$ is monovalent tetrahydro-2H-thiopyran 1,1-dioxide substituted with one, two, or three $R^{20b}$. In embodiments of a compound of Formula (I-1), (I'-1), (Ia-1), (Ia'-1), (Ib-1), (Ib'-1), (Ic-1), or (Ic'-1), or a pharmaceutically acceptable salt or solvate thereof, $R^3$ is monovalent $4\lambda^2$-thiomorpholine substituted with two $R^{20b}$. In embodiments of a compound of Formula (I-1), (I'-1), (Ia-1), (Ia'-1), (Ib-1), (Ib'-1), (Ic-1), or (Ic'-1), or a pharmaceutically acceptable salt or solvate thereof, $R^3$ is tetrahydro-2H-thiopyranyl 1,1-dioxide. In embodiments of a compound of Formula (I-1), (I'-1), (Ia-1), (Ia'-1), (Ib-1), (Ib'-1), (Ic-1), or (Ic'-1), or a pharmaceutically acceptable salt or solvate thereof, $R^3$ is $4\lambda^2$-thiomorpholinyl substituted with two $R^{20b}$. In embodiments of a compound of Formula (I-1), (I'-1), (Ia-1), (Ia'-1), (Ib-1), (Ib'-1), (Ic-1), or (Ic'-1), or a pharmaceutically acceptable salt or solvate thereof, $R^3$ is piperidinyl substituted with one $R^{20b}$. In embodiments of a compound of Formula (I-1), (I'-1), (Ia-1), (Ia'-1), (Ib-1), (Ib'-1), (Ic-1), or (Ic'-1), or a pharmaceutically acceptable salt or solvate thereof, $R^3$ is piperazinyl substituted with one $R^{20b}$. In embodiments of a compound of Formula (I-1), (I'-1), (Ia-1), (Ia'-1), (Ib-1), (Ib'-1), (Ic-1), or (Ic'-1), or a pharmaceutically acceptable salt or solvate thereof, $R^3$ is pyrrolidinyl substituted with one $R^{20b}$.

In embodiments of a compound of Formula (I-1), (I'-1), (Ia-1), (Ia'-1), (Ib-1), (Ib'-1), (Ic-1), or (Ic'-1), or a pharmaceutically acceptable salt or solvate thereof, $R^3$ is $C_{2-9}$heterocycloalkyl substituted with one methyl. In embodiments of a compound of Formula (I-1), (I'-1), (Ia-1), (Ia'-1), (Ib-1), (Ib'-1), (Ic-1), or (Ic'-1), or a pharmaceutically acceptable salt or solvate thereof, $R^3$ is $C_{6-9}$heterocycloalkyl substituted with one methyl, one ethyl, or one propyl. In embodiments of a compound of Formula (I-1), (I'-1), (Ia-1), (Ia'-1), (Ib-1), (Ib'-1), (Ic-1), or (Ic'-1), or a pharmaceutically acceptable salt or solvate thereof, $R^3$ is $C_{3-7}$heterocycloalkyl substituted with one methyl, one ethyl, or one propyl. In embodiments of a compound of Formula (I-1), (I'-1), (Ia-1), (Ia'-1), (Ib-1), (Ib'-1), (Ic-1), or (Ic'-1), or a pharmaceutically acceptable salt or solvate thereof, $R^3$ is $C_{3-6}$heterocycloalkyl substituted with one methyl, one ethyl, or one propyl. In embodiments of a compound of Formula (I-1), (I'-1), (Ia-1), (Ia'-1), (Ib-1), (Ib'-1), (Ic-1), or (Ic'-1), or a pharmaceutically acceptable salt or solvate thereof, $R^3$ is $C_{5-6}$heterocycloalkyl substituted with one methyl, one ethyl, or one propyl. In embodiments of a compound of Formula (I-1), (I'-1), (Ia-1), (Ia'-1), (Ib-1), (Ib'-1), (Ic-1), or (Ic'-1), or a pharmaceutically acceptable salt or solvate thereof, $R^3$ is $C_{5-6}$heterocycloalkyl substituted with one methyl, one ethyl, or one propyl. In embodiments of a compound of Formula (I-1), (I'-1), (Ia-1), (Ia'-1), (Ib-1), (Ib'-1), (Ic-1), or (Ic'-1), or a pharmaceutically acceptable salt or solvate thereof, $R^3$ is $C_{3-4}$heterocycloalkyl substituted with one methyl, one ethyl, or one propyl. In embodiments of a compound of Formula (I-1), (I'-1), (Ia-1), (Ia'-1), (Ib-1), (Ib'-1), (Ic-1), or (Ic'-1), or a pharmaceutically acceptable salt or solvate thereof, $R^3$ is $C_{2-7}$heterocycloalkyl substituted with one methyl, one ethyl, or one propyl. In embodiments of a compound of Formula (I-1), (I'-1), (Ia-1), (Ia'-1), (Ib-1), (Ib'-1), (Ic-1), or (Ic'-1), or a pharmaceutically acceptable salt or solvate thereof, $R^3$ is $C_{4-7}$heterocycloalkyl substituted with one methyl, one ethyl, or one propyl. In embodiments of a compound of Formula (I-1), (I'-1), (Ia-1), (Ia'-1), (Ib-1), (Ib'-1), (Ic-1), or (Ic'-1), or a pharmaceutically acceptable salt or solvate thereof, $R^3$ is $C_{4-5}$heterocycloalkyl substituted with one methyl, one ethyl, or one propyl. In embodiments of a compound of Formula (I-1), (I'-1), (Ia-1), (Ia'-1), (Ib-1), (Ib'-1), (Ic-1), or (Ic'-1), or a pharmaceutically acceptable salt or solvate thereof, $R^3$ is $C_5$heterocycloalkyl substituted with one methyl, one ethyl, or one propyl. In embodiments of a compound of Formula (I-1), (I'-1), (Ia-1), (Ia'-1), (Ib-1), (Ib'-1), (Ic-1), or (Ic'-1), or a pharmaceutically acceptable salt or solvate thereof, $R^3$ is $C_4$heterocycloalkyl substituted with one methyl, one ethyl, or one propyl.

In embodiments of a compound of Formula (I-1), (I'-1), (Ia-1), (Ia'-1), (Ib-1), (Ib'-1), (Ic-1), or (Ic'-1), or a pharmaceutically acceptable salt or solvate thereof, $R^3$ is $C_{6-9}$heterocycloalkyl substituted with one propyl. In embodiments of a compound of Formula (I-1), (I'-1), (Ia-1), (Ia'-1), (Ib-1), (Ib'-1), (Ic-1), or (Ic'-1), or a pharmaceutically acceptable salt or solvate thereof, $R^3$ is $C_{3-7}$heterocycloalkyl substituted with one propyl. In embodiments of a compound of Formula (I-1), (I'-1), (Ia-1), (Ia'-1), (Ib-1), (Ib'-1), (Ic-1), or (Ic'-1), or a pharmaceutically acceptable salt or solvate thereof, $R^3$ is $C_{3-6}$heterocycloalkyl substituted with one propyl. In embodiments of a compound of Formula (I-1), (I'-1), (Ia-1), (Ia'-1), (Ib-1), (Ib'-1), (Ic-1), or (Ic'-1), or a pharmaceutically acceptable salt or solvate thereof, $R^3$ is $C_{5-6}$heterocycloalkyl substituted with one propyl. In embodiments of a compound of Formula (I-1), (I'-1), (Ia-1), (Ia'-1), (Ib-1), (Ib'-1), (Ic-1), or (Ic'-1), or a pharmaceutically acceptable salt or solvate thereof, $R^3$ is $C_{5-6}$heterocycloalkyl substituted with one propyl. In embodiments of a compound of Formula (I-1), (I'-1), (Ia-1), (Ia'-1), (Ib-1), (Ib'-1), (Ic-1), or (Ic'-1), or a pharmaceutically acceptable salt or solvate thereof, $R^3$ is $C_{3-4}$heterocycloalkyl substituted with one propyl. In embodiments of a compound of Formula (I-1), (I'-1), (Ia-1), (Ia'-1), (Ib-1), (Ib'-1), (Ic-1), or (Ic'-1), or a pharmaceutically acceptable salt or solvate thereof, $R^3$ is $C_{4-5}$heterocycloalkyl substituted with one propyl. In embodiments of a compound of Formula (I-1), (I'-1), (Ia-1), (Ia'-1), (Ib-1), (Ib'-1), (Ic-1), or (Ic'-1), or a pharmaceutically acceptable salt or solvate thereof, $R^3$ is $C_5$heterocycloalkyl substituted with one propyl. In embodiments of a compound of Formula (I-1), (I'-1), (Ia-1), (Ia'-1), (Ib-1), (Ib'-1), (Ic-1), or (Ic'-1), or a pharmaceutically acceptable salt or solvate thereof, $R^3$ is $C_4$heterocycloalkyl substituted with one propyl.

In embodiments of a compound of Formula (I-1), (I'-1), (Ia-1), (Ia'-1), (Ib-1), (Ib'-1), (Ic-1), or (Ic'-1), or a pharmaceutically acceptable salt or solvate thereof, $R^3$ is $C_{2-9}$heterocycloalkyl substituted with one isopropyl. In embodiments of a compound of Formula (I-1), (I'-1), (Ia-1), (Ia'-1), (Ib-1), (Ib'-1), (Ic-1), or (Ic'-1), or a pharmaceutically acceptable salt or solvate thereof, $R^3$ is $C_{2-7}$heterocycloalkyl substituted with one isopropyl. In embodiments of a compound of Formula (I-1), (I'-1), (Ia-1), (Ia'-1), (Ib-1), (Ib'-1), (Ic-1), or (Ic'-1), or a pharmaceutically acceptable salt or solvate thereof, $R^3$ is $C_{4-7}$heterocycloalkyl substituted with one isopropyl. In embodiments of a compound of Formula (I-1), (I'-1), (Ia-1), (Ia'-1), (Ib-1), (Ib'-1), (Ic-1), or (Ic'-1), or a pharmaceutically acceptable salt or solvate thereof, $R^3$ is $C_{4-5}$heterocycloalkyl substituted with one isopropyl. In embodiments of a compound of Formula (I-1), (I'-1), (Ia-1), (Ia'-1), (Ib-1), (Ib'-1), (Ic-1), or (Ic'-1), or a pharmaceutically acceptable salt or solvate thereof, $R^3$ is $C_5$heterocycloalkyl substituted with one isopropyl. In embodiments of a compound of Formula (I-1), (I'-1), (Ia-1), (Ia'-1), (Ib-1), (Ib'-1), (Ic-1), or (Ic'-1), or a pharmaceutically acceptable salt or solvate thereof, $R^3$ is $C_4$heterocycloalkyl substituted with one isopropyl.

In embodiments of a compound of Formula (I-1), (I'-1), (Ia-1), (Ia'-1), (Ib-1), (Ib'-1), (Ic-1), or (Ic'-1), or a pharmaceutically acceptable salt or solvate thereof, $R^3$ is $C_{2-9}$heterocycloalkyl substituted with two oxo. In embodiments of a compound of Formula (I-1), (I'-1), (Ia-1), (Ia'-1), (Ib-1), (Ib'-1), (Ic-1), or (Ic'-1), or a pharmaceutically acceptable salt or solvate thereof, $R^3$ is $C_{2-7}$heterocycloalkyl substituted with two oxo. In embodiments of a compound of Formula (I-1), (I'-1), (Ia-1), (Ia'-1), (Ib-1), (Ib'-1), (Ic-1), or (Ic'-1), or a pharmaceutically acceptable salt or solvate thereof, $R^3$ is $C_{4-7}$heterocycloalkyl substituted with two oxo. In embodiments of a compound of Formula (I-1), (I'-1), (Ia-1), (Ia'-1), (Ib-1), (Ib'-1), (Ic-1), or (Ic'-1), or a pharmaceutically acceptable salt or solvate thereof, $R^3$ is $C_{6-9}$heterocycloalkyl substituted with two oxo. In embodiments of a compound of Formula (I-1), (I'-1), (Ia-1), (Ia'-1), (Ib-1), (Ib'-1), (Ic-1), or (Ic'-1), or a pharmaceutically acceptable salt or solvate thereof, $R^3$ is $C_{3-7}$heterocycloalkyl substituted with two oxo. In embodiments of a compound of Formula (I-1), (I'-1), (Ia-1), (Ia'-1), (Ib-1), (Ib'-1), (Ic-1), or (Ic'-1), or a pharmaceutically acceptable salt or solvate thereof, $R^3$ is $C_{3-6}$heterocycloalkyl substituted with two oxo. In embodiments of a compound of Formula (I-1), (I'-1), (Ia-1), (Ia'-1), (Ib-1), (Ib'-1), (Ic-1), or (Ic'-1), or a pharmaceutically acceptable salt or solvate thereof, $R^3$ is $C_{5-6}$heterocycloalkyl substituted with two oxo. In embodiments of a compound of Formula (I-1), (I'-1), (Ia-1), (Ia'-1), (Ib-1), (Ib'-1), (Ic-1), or (Ic'-1), or a pharmaceutically acceptable salt or solvate thereof, $R^3$ is $C_{5-6}$heterocycloalkyl substituted with two oxo. In embodiments of a compound of Formula (I-1), (I'-1), (Ia-1), (Ia'-1), (Ib-1), (Ib'-1), (Ic-1), or (Ic'-1), or a pharmaceutically acceptable salt or solvate thereof, $R^3$ is $C_{3-4}$heterocycloalkyl substituted with two oxo. In embodiments of a compound of Formula (I-1), (I'-1), (Ia-1), (Ia'-1), (Ib-1), (Ib'-1), (Ic-1), or (Ic'-1), or a pharmaceutically acceptable salt or solvate thereof, $R^3$ is $C_{4-5}$heterocycloalkyl substituted with two oxo. In embodiments of a compound of Formula (I-1), (I'-1), (Ia-1), (Ia'-1), (Ib-1), (Ib'-1), (Ic-1), or (Ic'-1), or a pharmaceutically acceptable salt or solvate thereof, $R^3$ is $C_5$heterocycloalkyl substituted with two oxo. In embodiments of a compound of Formula (I-1), (I'-1), (Ia-1), (Ia'-1), (Ib-1), (Ib'-1), (Ic-1), or (Ic'-1), or a pharmaceutically acceptable salt or solvate thereof, $R^3$ is $C_4$heterocycloalkyl substituted with two oxo.

In embodiments of a compound of Formula (I-1), (I'-1), (Ia-1), (Ia'-1), (Ib-1), (Ib'-1), (Ic-1), or (Ic'-1), or a pharmaceutically acceptable salt or solvate thereof, $R^3$ is thianyl, optionally substituted with one, two, or three $R^{20b}$ that is amino. In embodiments of a compound of Formula (I-1), (I'-1), (Ia-1), (Ia'-1), (Ib-1), (Ib'-1), (Ic-1), or (Ic'-1), or a pharmaceutically acceptable salt or solvate thereof, $R^3$ is thianyl, optionally substituted with one, two, or three $R^{20b}$ that is —CN. In embodiments of a compound of Formula (I-1), (I'-1), (Ia-1), (Ia'-1), (Ib-1), (Ib'-1), (Ic-1), or (Ic'-1), or a pharmaceutically acceptable salt or solvate thereof, $R^3$ is thianyl, optionally substituted with one, two, or three $R^{20b}$ that is $C_{1-3}$alkyl. In embodiments of a compound of Formula (I-1), (I'-1), (Ia-1), (Ia'-1), (Ib-1), (Ib'-1), (Ic-1), or (Ic'-1), or a pharmaceutically acceptable salt or solvate thereof, $R^3$ is thianyl, optionally substituted with one, two, or three $R^{20b}$ that is $C_{1-3}$alkoxy. In embodiments of a compound of Formula (I-1), (I'-1), (Ia-1), (Ia'-1), (Ib-1), (Ib'-1), (Ic-1), or (Ic'-1), or a pharmaceutically acceptable salt or solvate thereof, $R^3$ is thianyl, optionally substituted with one, two, or three $R^{20b}$ that is $C_{1-3}$haloalkyl. In embodiments of a compound of Formula (I-1), (I'-1), (Ia-1), (Ia'-1), (Ib-1), (Ib'-1), (Ic-1), or (Ic'-1), or a pharmaceutically acceptable salt or solvate thereof, $R^3$ is thianyl, optionally substituted with one, two, or three $R^{20b}$ that is —OH. In embodiments of a compound of Formula (I-1), (I'-1), (Ia-1), (Ia'-1), (Ib-1), (Ib'-1), (Ic-1), or (Ic'-1), or a pharmaceutically acceptable salt or solvate thereof, $R^3$ is thianyl, optionally substituted with one, two, or three $R^{20b}$ that is oxo. In embodiments of a compound of Formula (I-1), (I'-1), (Ia-1), (Ia'-1), (Ib-1), (Ib'-1), (Ic-1), or (Ic'-1), or a pharmaceutically acceptable salt or solvate thereof, $R^3$ is thianyl, optionally substituted with one, two, or three $R^{20b}$ that is —N($R^{24}$)C(O)$R^{25}$. In embodiments of a compound of Formula (I-1), (I'-1), (Ia-1), (Ia'-1), (Ib-1), (Ib'-1), (Ic-1), or (Ic'-1), or a pharmaceutically acceptable salt or solvate thereof, $R^3$ is thianyl, optionally substituted with one, two, or three $R^{20b}$ that is —NHC(O)$R^{25}$. In embodiments of a compound of Formula (I-1), (I'-1), (Ia-1), (Ia'-1), (Ib-1), (Ib'-1), (Ic-1), or (Ic'-1), or a pharmaceutically acceptable salt or solvate thereof, $R^3$ is thianyl, optionally substituted with one, two, or three $R^{20b}$ that is —NHC(O)$R^{25}$ and $R^{25}$ is $C_{2-9}$heterocycloalkyl optionally substituted with one, two, or three groups independently selected from halogen, $C_{1-6}$alkyl, $C_{1-6}$haloalkyl, $C_{1-6}$alkoxy, $C_{3-7}$cycloalkyl, $C_{2-9}$heterocycloalkyl, $C_{6-10}$aryl, and $C_{1-9}$heteroaryl. In embodiments of a compound of Formula (I-1), (I'-1), (Ia-1), (Ia'-1), (Ib-1), (Ib'-1), (Ic-1), or (Ic'-1), or a pharmaceutically acceptable salt or solvate thereof, $R^3$ is thianyl, optionally substituted with one, two, or three $R^{20b}$ that is —NHC(O)$R^{25}$ and $R^{25}$ is $C_{2-5}$heterocycloalkyl optionally substituted with one $C_{1-6}$alkyl. In embodiments of a compound of Formula (I-1), (I'-1), (Ia-1), (Ia'-1), (Ib-1), (Ib'-1), (Ic-1), or (Ic'-1), or a pharmaceutically acceptable salt or solvate thereof, $R^3$ is thianyl, optionally substituted with one, two, or three $R^{20b}$ that is —C(O)N($R^{22}$)($R^{23}$). In embodiments of a compound of Formula (I-1), (I'-1), (Ia-1), (Ia'-1), (Ib-1), (Ib'-1), (Ic-1), or (Ic'-1), or a pharmaceutically acceptable salt or solvate thereof, $R^3$ is thianyl, optionally substituted with one, two, or three $R^{20b}$ that is —C(O)NH($R^{22}$). In embodiments of a compound of Formula (I-1), (I'-1), (Ia-1), (Ia'-1), (Ib-1), (Ib'-1), (Ic-1), or (Ic'-1), or a pharmaceutically acceptable salt or solvate thereof, $R^3$ is thianyl, optionally substituted with one, two, or three $R^{20b}$ that is —C(O)NH($R^{22}$) and $R^{22}$ is $C_{2-9}$heterocycloalkyl optionally substituted with one, two, or three groups independently selected from halogen and $C_{1-6}$alkyl. In embodiments of a compound of Formula (I-1), (I'-1), (Ia-1), (Ia'-1), (Ib-1), (Ib'-1), (Ic-1), or (Ic'-1), or a pharmaceutically acceptable salt or solvate thereof, $R^3$ is thianyl, optionally substituted with one, two, or three $R^{20b}$ that is —C(O)NH($R^{22}$) and $R^{22}$ is $C_{2-5}$heterocycloalkyl optionally substituted with one $C_{1-6}$alkyl.

In embodiments of a compound of Formula (I-1), (I'-1), (Ia-1), (Ia'-1), (Ib-1), (Ib'-1), (Ic-1), or (Ic'-1), or a pharmaceutically acceptable salt or solvate thereof, $R^3$ is monovalent tetrahydro-2H-thiopyran 1,1-dioxide, optionally substituted with one, two, or three $R^{20b}$ that is amino. In embodiments of a compound of Formula (I-1), (I'-1), (Ia-1), (Ia'-1), (Ib-1), (Ib'-1), (Ic-1), or (Ic'-1), or a pharmaceutically acceptable salt or solvate thereof, $R^3$ is monovalent tetrahydro-2H-thiopyran 1,1-dioxide, optionally substituted with one, two, or three $R^{20b}$ that is —CN. In embodiments of a compound of Formula (I-1), (I'-1), (Ia-1), (Ia'-1), (Ib-1), (Ib'-1), (Ic-1), or (Ic'-1), or a pharmaceutically acceptable salt or solvate thereof, $R^3$ is monovalent tetrahydro-2H-thiopyran 1,1-dioxide, optionally substituted with one, two, or three $R^{20b}$ that is $C_{1-3}$alkyl. In embodiments of a compound of Formula (I-1), (I'-1), (Ia-1), (Ia'-1), (Ib-1), (Ib'-1), (Ic-1), or (Ic'-1), or a pharmaceutically acceptable salt or solvate thereof, $R^3$ is monovalent tetrahydro-2H-thiopyran 1,1-dioxide, optionally substituted with one, two, or three $R^{20b}$ that is $C_{1-3}$alkoxy. In embodiments of a compound of Formula (I-1), (I'-1), (Ia-1), (Ia'-1), (Ib-1), (Ib'-1), (Ic-1), or (Ic'-1), or a pharmaceutically acceptable salt or solvate thereof, $R^3$ is thianyl, optionally substituted with one, two, or three $R^{20b}$ that is $C_{1-3}$haloalkyl. In embodiments of a compound of Formula (I-1), (I'-1), (Ia-1), (Ia'-1), (Ib-1), (Ib'-1), (Ic-1), or (Ic'-1), or a pharmaceutically acceptable salt or solvate thereof, $R^3$ is monovalent tetrahydro-2H-thiopyran 1,1-dioxide, optionally substituted with one, two, or three $R^{20b}$ that is —OH. In embodiments of a compound of Formula (I-1), (I'-1), (Ia-1), (Ia'-1), (Ib-1), (Ib'-1), (Ic-1), or (Ic'-1), or a pharmaceutically acceptable salt or solvate thereof, $R^3$ is monovalent tetrahydro-2H-thiopyran 1,1-dioxide, optionally substituted with one, two, or three $R^{20b}$ that is oxo. In embodiments of a compound of Formula (I-1), (I'-1), (Ia-1), (Ia'-1), (Ib-1), (Ib'-1), (Ic-1), or (Ic'-1), or a pharmaceutically acceptable salt or solvate thereof, $R^3$ is monovalent tetrahydro-2H-thiopyran 1,1-dioxide, optionally substituted with one, two, or three $R^{20b}$ that is —N($R^{24}$)C(O)$R^{25}$. In embodiments of a compound of Formula (I-1), (I'-1), (Ia-1), (Ia'-1), (Ib-1), (Ib'-1), (Ic-1), or (Ic'-1), or a pharmaceutically acceptable salt or solvate thereof, $R^3$ is monovalent tetrahydro-2H-thiopyran 1,1-dioxide, optionally substituted with one, two, or three $R^{20b}$ that is —NHC(O)$R^{25}$. In embodiments of a compound of Formula (I-1), (I'-1), (Ia-1), (Ia'-1), (Ib-1), (Ib'-1), (Ic-1), or (Ic'-1), or a pharmaceutically acceptable salt or solvate thereof, $R^3$ is monovalent tetrahydro-2H-thiopyran 1,1-dioxide, optionally substituted with one, two, or three $R^{20b}$ that is —NHC(O)$R^{25}$ and $R^{25}$ is $C_{2-9}$heterocycloalkyl optionally substituted with one, two, or three groups independently selected from halogen, $C_{1-6}$alkyl, $C_{1-6}$haloalkyl, $C_{1-6}$alkoxy, $C_{3-7}$cycloalkyl, $C_{2-9}$heterocycloalkyl, $C_{6-10}$aryl, and $C_{1-9}$heteroaryl. In embodiments of a compound of Formula (I-1), (I'-1), (Ia-1), (Ia'-1), (Ib-1), (Ib'-1), (Ic-1), or (Ic'-1), or a pharmaceutically acceptable salt or solvate thereof, $R^3$ is monovalent tetrahydro-2H-thiopyran 1,1-dioxide, optionally substituted with one, two, or three $R^{20b}$ that is —NHC(O)$R^{20e}$ and $R^{25}$ is $C_{2-5}$heterocycloalkyl optionally substituted with one $C_{1-6}$alkyl. In embodiments of a compound of Formula (I-1), (I'-1), (Ia-1), (Ia'-1), (Ib-1), (Ib'-1), (Ic-1), or (Ic'-1), or a pharmaceutically acceptable salt or solvate thereof, $R^3$ is monovalent tetrahydro-2H-thiopyran 1,1-dioxide, optionally substituted with one, two, or three $R^{20b}$ that is —C(O)N($R^{22}$)($R^{23}$). In embodiments of a compound of Formula (I-1), (I'-1), (Ia-1), (Ia'-1), (Ib-1), (Ib'-1), (Ic-1), or (Ic'-1), or a pharmaceutically acceptable salt or solvate thereof, $R^3$ is monovalent tetrahydro-2H-thiopyran 1,1-dioxide, optionally substituted with one, two, or three $R^{20b}$ that is —C(O)NH($R^{22}$). In embodiments of a compound of Formula (I-1), (I'-1), (Ia-1), (Ia'-1), (Ib-1), (Ib'-1), (Ic-1), or (Ic'-1), or a pharmaceutically acceptable salt or solvate thereof, $R^3$ is monovalent tetrahydro-2H-thiopyran 1,1-dioxide, optionally substituted with one, two, or three $R^{20b}$ that is —C(O)NH($R^{22}$) and $R^{22}$ is $C_{2-9}$heterocycloalkyl optionally substituted with one, two, or three groups independently selected from halogen and $C_{1-6}$alkyl. In embodiments of a compound of Formula (I-1), (I'-1), (Ia-1), (Ia'-1), (Ib-1), (Ib'-1), (Ic-1), or (Ic'-1), or a pharmaceutically acceptable salt or solvate thereof, $R^3$ is monovalent tetrahydro-2H-thiopyran 1,1-dioxide, optionally substituted with one, two, or three $R^{20b}$ that is —C(O)NH($R^{22}$) and $R^{22}$ is $C_{2-5}$heterocycloalkyl optionally substituted with one $C_{1-6}$alkyl.

In embodiments of a compound of Formula (I-1), (I'-1), (Ia-1), (Ia'-1), (Ib-1), (Ib'-1), (Ic-1), or (Ic'-1), or a pharmaceutically acceptable salt or solvate thereof, $R^3$ is $4\lambda^2$-thiomorpholinyl, optionally substituted with one, two, or three $R^{20b}$ that is amino. In embodiments of a compound of Formula (I-1), (I'-1), (Ia-1), (Ia'-1), (Ib-1), (Ib'-1), (Ic-1), or (Ic'-1), or a pharmaceutically acceptable salt or solvate thereof, $R^3$ is $4\lambda^2$-thiomorpholinyl, optionally substituted with one, two, or three $R^{20b}$ that is —CN. In embodiments of a compound of Formula (I-1), (I'-1), (Ia-1), (Ia'-1), (Ib-1), (Ib'-1), (Ic-1), or (Ic'-1), or a pharmaceutically acceptable salt or solvate thereof, $R^3$ is $4\lambda^2$-thiomorpholinyl, optionally substituted with one, two, or three $R^{20b}$ that is $C_{1-3}$alkyl. In embodiments of a compound of Formula (I-1), (I'-1), (Ia-1), (Ia'-1), (Ib-1), (Ib'-1), (Ic-1), or (Ic'-1), or a pharmaceutically acceptable salt or solvate thereof, $R^3$ is $4\lambda^2$-thiomorpholinyl, optionally substituted with one, two, or three $R^{20b}$ that is $C_{1-3}$alkoxy. In embodiments of a compound of Formula (I-1), (I'-1), (Ia-1), (Ia'-1), (Ib-1), (Ib'-1), (Ic-1), or (Ic'-1), or a pharmaceutically acceptable salt or solvate thereof, $R^3$ is $4\lambda^2$-thiomorpholinyl, optionally substituted with one, two, or three $R^{20b}$ that is $C_{1-3}$haloalkyl. In embodiments of a compound of Formula (I-1), (I'-1), (Ia-1), (Ia'-1), (Ib-1), (Ib'-1), (Ic-1), or (Ic'-1), or a pharmaceutically acceptable salt or solvate thereof, $R^3$ is $4\lambda^2$-thiomorpholinyl, optionally substituted with one, two, or three $R^{20b}$ that is —OH. In embodiments of a compound of Formula (I-1), (I'-1), (Ia-1), (Ia'-1), (Ib-1), (Ib'-1), (Ic-1), or (Ic'-1), or a pharmaceutically acceptable salt or solvate thereof, $R^3$ is $4\lambda^2$-thiomorpholinyl, optionally substituted with one, two, or three $R^{20b}$ that is oxo. In embodiments of a compound of Formula (I-1), (I'-1), (Ia-1), (Ia'-1), (Ib-1), (Ib'-1), (Ic-1), or (Ic'-1), or a pharmaceutically acceptable salt or solvate thereof, $R^3$ is $4\lambda^2$-thiomorpholinyl, optionally substituted with one, two, or three $R^{20b}$ that is —N($R^{24}$)C(O)$R^{25}$. In embodiments of a compound of Formula (I-1), (I'-1), (Ia-1), (Ia'-1), (Ib-1), (Ib'-1), (Ic-1), or (Ic'-1), or a pharmaceutically acceptable salt or solvate thereof, $R^3$ is $4\lambda^2$-thiomorpholinyl, optionally substituted with one, two, or three $R^{20b}$ that is —NHC(O)$R^{25}$. In embodiments of a compound of Formula (I-1), (I'-1), (Ia-1), (Ia'-1), (Ib-1), (Ib'-1), (Ic-1), or (Ic'-1), or a pharmaceutically acceptable salt or solvate thereof, $R^3$ is $4\lambda^2$-thiomorpholinyl, optionally substituted with one, two, or three $R^{20b}$ that is —NHC(O)$R^{25}$ and $R^{25}$ is $C_{2-9}$heterocycloalkyl optionally substituted with one, two, or three groups independently selected from halogen, $C_{1-6}$alkyl, $C_{1-6}$haloalkyl, $C_{1-6}$alkoxy, $C_{3-7}$cycloalkyl, $C_{2-9}$heterocycloalkyl, $C_{6-10}$aryl, and $C_{1-9}$heteroaryl. In embodiments of a compound of Formula (I-1), (I'-1), (Ia-1), (Ia'-1), (Ib-1), (Ib'-1), (Ic-1), or (Ic'-1), or a pharmaceutically acceptable salt or solvate thereof, $R^3$ is $4\lambda^2$-thiomorpholinyl, optionally substituted with one, two, or three $R^{20b}$ that is —NHC(O)$R^{25}$ and $R^{25}$ is $C_{2-5}$heterocycloalkyl optionally substituted with one $C_{1-6}$alkyl. In embodiments of a compound of Formula (I-1), (I'-1), (Ia-1), (Ia'-1), (Ib-1), (Ib'-1), (Ic-1), or (Ic'-1), or a pharmaceutically acceptable salt or solvate thereof, $R^3$ is $4\lambda^2$-thiomorpholinyl, optionally substituted with one, two, or three $R^{20b}$ that is —C(O)N($R^{22}$)($R^{23}$). In embodiments of a compound of Formula (I-1), (I'-1), (Ia-1), (Ia'-1), (Ib-1), (Ib'-1), (Ic-1), or (Ic'-1), or a pharmaceutically acceptable salt or solvate thereof, $R^3$ is $4\lambda^2$-thiomorpholinyl, optionally substituted with one, two, or three $R^{20b}$ that is —C(O)NH($R^{22}$). In embodiments of a compound of Formula (I-1), (I'-1), (Ia-1), (Ia'-1), (Ib-1), (Ib'-1), (Ic-1), or (Ic'-1), or a pharmaceutically acceptable salt or solvate thereof, $R^3$ is $4\lambda^2$-thiomorpholinyl, optionally substituted with one, two, or three $R^{20b}$ that is —C(O)NH($R^{22}$) and $R^{22}$ is $C_{2-9}$heterocycloalkyl optionally substituted with one, two, or three groups independently selected from halogen and $C_{1-6}$alkyl. In embodiments of a compound of Formula (I-1), (I'-1), (Ia-1), (Ia'-1), (Ib-1), (Ib'-1), (Ic-1), or (Ic'-1), or a pharmaceutically acceptable salt or solvate thereof, $R^3$ is $4\lambda^2$-thiomorpholinyl, optionally substituted with one, two, or three $R^{20b}$ that is —C(O)NH($R^{22}$) and $R^{22}$ is $C_{2-5}$heterocycloalkyl optionally substituted with one $C_{1-6}$alkyl.

In embodiments of a compound of Formula (I-1), (I'-1), (Ia-1), (Ia'-1), (Ib-1), (Ib'-1), (Ic-1), or (Ic'-1), or a pharmaceutically acceptable salt or solvate thereof, $R^3$ is piperidinyl, optionally substituted with one, two, or three $R^{20b}$ that is amino. In embodiments of a compound of Formula (I-1), (I'-1), (Ia-1), (Ia'-1), (Ib-1), (Ib'-1), (Ic-1), or (Ic'-1), or a pharmaceutically acceptable salt or solvate thereof, $R^3$ is piperidinyl, optionally substituted with one, two, or three $R^{20b}$ that is —CN. In embodiments of a compound of Formula (I-1), (I'-1), (Ia-1), (Ia'-1), (Ib-1), (Ib'-1), (Ic-1), or (Ic'-1), or a pharmaceutically acceptable salt or solvate thereof, $R^3$ is piperidinyl, optionally substituted with one, two, or three $R^{20b}$ that is $C_{1-3}$alkyl. In embodiments of a compound of Formula (I-1), (I'-1), (Ia-1), (Ia'-1), (Ib-1), (Ib'-1), (Ic-1), or (Ic'-1), or a pharmaceutically acceptable salt or solvate thereof, $R^3$ is piperidinyl, optionally substituted with one, two, or three $R^{20b}$ that is $C_{1-3}$alkoxy. In embodiments of a compound of Formula (I-1), (I'-1), (Ia-1), (Ia'-1), (Ib-1), (Ib'-1), (Ic-1), or (Ic'-1), or a pharmaceutically acceptable salt or solvate thereof, $R^3$ is piperidinyl, optionally substituted with one, two, or three $R^{20b}$ that is $C_{1-3}$haloalkyl. In embodiments of a compound of Formula (I-1), (I'-1), (Ia-1), (Ia'-1), (Ib-1), (Ib'-1), (Ic-1), or (Ic'-1), or a pharmaceutically acceptable salt or solvate thereof, $R^3$ is piperidinyl, optionally substituted with one, two, or three $R^{20b}$ that is —OH. In embodiments of a compound of Formula (I-1), (I'-1), (Ia-1), (Ia'-1), (Ib-1), (Ib'-1), (Ic-1), or (Ic'-1), or a pharmaceutically acceptable salt or solvate thereof, $R^3$ is piperidinyl, optionally substituted with one, two, or three $R^{20b}$ that is oxo. In embodiments of a compound of Formula (I-1), (I'-1), (Ia-1), (Ia'-1), (Ib-1), (Ib'-1), (Ic-1), or (Ic'-1), or a pharmaceutically acceptable salt or solvate thereof, $R^3$ is piperidinyl, optionally substituted with one, two, or three $R^{20b}$ that is —N($R^{24}$)C(O)$R^{25}$. In embodiments of a compound of Formula (I-1), (I'-1), (Ia-1), (Ia'-1), (Ib-1), (Ib'-1), (Ic-1), or (Ic'-1), or a pharmaceutically acceptable salt or solvate thereof, $R^3$ is piperidinyl, optionally substituted with one, two, or three $R^{20b}$ that is —NHC(O)$R^{25}$. In embodiments of a compound of Formula (I-1), (I'-1), (Ia-1), (Ia'-1), (Ib-1), (Ib'-1), (Ic-1), or (Ic'-1), or a pharmaceutically acceptable salt or solvate thereof, $R^3$ is piperidinyl, optionally substituted with one, two, or three $R^{20b}$ that is —NHC(O)$R^{25}$ and $R^{25}$ is $C_{2-9}$heterocycloalkyl optionally substituted with one, two, or three groups independently selected from halogen, $C_{1-6}$alkyl, $C_{1-6}$haloalkyl, $C_{1-6}$alkoxy, $C_{3-7}$cycloalkyl, $C_{2-9}$heterocycloalkyl, $C_{6-10}$aryl, and $C_{1-9}$heteroaryl. In embodiments of a compound of Formula (I-1), (I'-1), (Ia-1), (Ia'-1), (Ib-1), (Ib'-1), (Ic-1), or (Ic'-1), or a pharmaceutically acceptable salt or solvate thereof, $R^3$ is piperidinyl, optionally substituted with one, two, or three $R^{20b}$ that is —NHC(O)$R^{25}$ and $R^{25}$ is $C_{2-5}$heterocycloalkyl optionally substituted with one $C_{1-6}$alkyl. In embodiments of a compound of Formula (I-1), (I'-1), (Ia-1), (Ia'-1), (Ib-1), (Ib'-1), (Ic-1), or (Ic'-1), or a pharmaceutically acceptable salt or solvate thereof, $R^3$ is piperidinyl, optionally substituted with one, two, or three $R^{20b}$ that is —C(O)N($R^{22}$)($R^{23}$). In embodiments of a compound of Formula (I-1), (I'-1), (Ia-1), (Ia'-1), (Ib-1), (Ib'-1), (Ic-1), or (Ic'-1), or a pharmaceutically acceptable salt or solvate thereof, $R^3$ is piperidinyl, optionally substituted with one, two, or three $R^{20b}$ that is —C(O)NH($R^{22}$). In embodiments of a compound of Formula (I-1), (I'-1), (Ia-1), (Ia'-1), (Ib-1), (Ib'-1), (Ic-1), or (Ic'-1), or a pharmaceutically acceptable salt or solvate thereof, $R^3$ is piperidinyl, optionally substituted with one, two, or three $R^{20b}$ that is —C(O)NH($R^{22}$) and $R^{22}$ is $C_{2-9}$heterocycloalkyl optionally substituted with one, two, or three groups independently selected from halogen and $C_{1-6}$alkyl. In embodiments of a compound of Formula (I-1), (I'-1), (Ia-1), (Ia'-1), (Ib-1), (Ib'-1), (Ic-1), or (Ic'-1), or a pharmaceutically acceptable salt or solvate thereof, $R^3$ is piperidinyl, optionally substituted with one, two, or three $R^{20b}$ that is —C(O)NH($R^{22}$) and $R^{22}$ is $C_{2-5}$heterocycloalkyl optionally substituted with one $C_{1-6}$alkyl.

In embodiments of a compound of Formula (I-1), (I'-1), (Ia-1), (Ia'-1), (Ib-1), (Ib'-1), (Ic-1), or (Ic'-1), or a pharmaceutically acceptable salt or solvate thereof, $R^3$ is piperazinyl, optionally substituted with one, two, or three $R^{20b}$ that is amino. In embodiments of a compound of Formula (I-1), (I'-1), (Ia-1), (Ia'-1), (Ib-1), (Ib'-1), (Ic-1), or (Ic'-1), or a pharmaceutically acceptable salt or solvate thereof, $R^3$ is piperazinyl, optionally substituted with one, two, or three $R^{20b}$ that is —CN. In embodiments of a compound of Formula (I-1), (I'-1), (Ia-1), (Ia'-1), (Ib-1), (Ib'-1), (Ic-1), or (Ic'-1), or a pharmaceutically acceptable salt or solvate thereof, $R^3$ is piperazinyl, optionally substituted with one, two, or three $R^{20b}$ that is $C_{1-3}$alkyl. In embodiments of a compound of Formula (I-1), (I'-1), (Ia-1), (Ia'-1), (Ib-1), (Ib'-1), (Ic-1), or (Ic'-1), or a pharmaceutically acceptable salt or solvate thereof, $R^3$ is piperazinyl, optionally substituted with one, two, or three $R^{20b}$ that is $C_{1-3}$alkoxy. In embodiments of a compound of Formula (I-1), (I'-1), (Ia-1), (Ia'-1), (Ib-1), (Ib'-1), (Ic-1), or (Ic'-1), or a pharmaceutically acceptable salt or solvate thereof, $R^3$ is piperazinyl, optionally substituted with one, two, or three $R^{20b}$ that is $C_{1-3}$haloalkyl. In embodiments of a compound of Formula (I-1), (I'-1), (Ia-1), (Ia'-1), (Ib-1), (Ib'-1), (Ic-1), or (Ic'-1), or a pharmaceutically acceptable salt or solvate thereof, $R^3$ is piperazinyl, optionally substituted with one, two, or three $R^{20b}$ that is —OH. In embodiments of a compound of Formula (I-1), (I'-1), (Ia-1), (Ia'-1), (Ib-1), (Ib'-1), (Ic-1), or (Ic'-1), or a pharmaceutically acceptable salt or solvate thereof, $R^3$ is piperazinyl, optionally substituted with one, two, or three $R^{20b}$ that is oxo. In embodiments of a compound of Formula (I-1), (I'-1), (Ia-1), (Ia'-1), (Ib-1), (Ib'-1), (Ic-1), or (Ic'-1), or a pharmaceutically acceptable salt or solvate thereof, $R^3$ is piperazinyl, optionally substituted with one, two, or three $R^{20b}$ that is —N($R^{24}$)C(O)$R^{25}$. In embodiments of a compound of Formula (I-1), (I'-1), (Ia-1), (Ia'-1), (Ib-1), (Ib'-1), (Ic-1), or (Ic'-1), or a pharmaceutically acceptable salt or solvate thereof, $R^3$ is piperazinyl, optionally substituted with one, two, or three $R^{20b}$ that is —NHC(O)$R^{25}$. In embodiments of a compound of Formula (I-1), (I'-1), (Ia-1), (Ia'-1), (Ib-1), (Ib'-1), (Ic-1), or (Ic'-1), or a pharmaceutically acceptable salt or solvate thereof, $R^3$ is piperazinyl, optionally substituted with one, two, or three $R^{20b}$ that is —NHC(O)$R^{25}$ and $R^{25}$ is $C_{2-9}$heterocycloalkyl optionally substituted with one, two, or three groups independently selected from halogen, $C_{1-6}$alkyl, $C_{1-6}$haloalkyl, $C_{1-6}$alkoxy, $C_{3-7}$cycloalkyl, $C_{2-9}$heterocycloalkyl, $C_{6-10}$aryl, and $C_{1-9}$heteroaryl. In embodiments of a compound of Formula (I-1), (I'-1), (Ia-1), (Ia'-1), (Ib-1), (Ib'-1), (Ic-1), or (Ic'-1), or a pharmaceutically acceptable salt or solvate thereof, $R^3$ is piperazinyl, optionally substituted with one, two, or three $R^{20b}$ that is —NHC(O)$R^{20e}$ and $R^{25}$ is $C_{2-5}$heterocycloalkyl optionally substituted with one $C_{1-6}$alkyl. In embodiments of a compound of Formula (I-1), (I'-1), (Ia-1), (Ia'-1), (Ib-1), (Ib'-1), (Ic-1), or (Ic'-1), or a pharmaceutically acceptable salt or solvate thereof, $R^3$ is piperazinyl, optionally substituted with one, two, or three $R^{20b}$ that is —C(O)N($R^{22}$)($R^{23}$). In embodiments of a compound of Formula (I-1), (I'-1), (Ia-1), (Ia'-1), (Ib-1), (Ib'-1), (Ic-1), or (Ic'-1), or a pharmaceutically acceptable salt or solvate thereof, $R^3$ is piperazinyl, optionally substituted with one, two, or three $R^{20b}$ that is —C(O)NH($R^{22}$). In embodiments of a compound of Formula (I-1), (I'-1), (Ia-1), (Ia'-1), (Ib-1), (Ib'-1), (Ic-1), or (Ic'-1), or a pharmaceutically acceptable salt or solvate thereof, $R^3$ is piperazinyl, optionally substituted with one, two, or three $R^{20b}$ that is —C(O)NH($R^{22}$) and $R^{22}$ is $C_{2-9}$heterocycloalkyl optionally substituted with one, two, or three groups independently selected from halogen and $C_{1-6}$alkyl. In embodiments of a compound of Formula (I-1), (I'-1), (Ia-1), (Ia'-1), (Ib-1), (Ib'-1), (Ic-1), or (Ic'-1), or a pharmaceutically acceptable salt or solvate thereof, $R^3$ is piperazinyl, optionally substituted with one, two, or three $R^{20b}$ that is —C(O)NH($R^{22}$) and $R^{22}$ is $C_{2-5}$heterocycloalkyl optionally substituted with one $C_{1-6}$alkyl.

In embodiments of a compound of Formula (I-1), (I'-1), (Ia-1), (Ia'-1), (Ib-1), (Ib'-1), (Ic-1), or (Ic'-1), or a pharmaceutically acceptable salt or solvate thereof, $R^3$ is pyrrolidinyl, optionally substituted with one, two, or three $R^{20b}$ that is amino. In embodiments of a compound of Formula (I-1), (I'-1), (Ia-1), (Ia'-1), (Ib-1), (Ib'-1), (Ic-1), or (Ic'-1), or a pharmaceutically acceptable salt or solvate thereof, $R^3$ is pyrrolidinyl, optionally substituted with one, two, or three $R^{20b}$ that is —CN. In embodiments of a compound of Formula (I-1), (I'-1), (Ia-1), (Ia'-1), (Ib-1), (Ib'-1), (Ic-1), or (Ic'-1), or a pharmaceutically acceptable salt or solvate thereof, $R^3$ is pyrrolidinyl, optionally substituted with one, two, or three $R^{20b}$ that is $C_{1-3}$alkyl. In embodiments of a compound of Formula (I-1), (I'-1), (Ia-1), (Ia'-1), (Ib-1), (Ib'-1), (Ic-1), or (Ic'-1), or a pharmaceutically acceptable salt or solvate thereof, $R^3$ is pyrrolidinyl, optionally substituted with one, two, or three $R^{20b}$ that is $C_{1-3}$alkoxy. In embodiments of a compound of Formula (I-1), (I'-1), (Ia-1), (Ia'-1), (Ib-1), (Ib'-1), (Ic-1), or (Ic'-1), or a pharmaceutically acceptable salt or solvate thereof, $R^3$ is pyrrolidinyl, optionally substituted with one, two, or three $R^{20b}$ that is $C_{1-3}$haloalkyl. In embodiments of a compound of Formula (I-1), (I'-1), (Ia-1), (Ia'-1), (Ib-1), (Ib'-1), (Ic-1), or (Ic'-1), or a pharmaceutically acceptable salt or solvate thereof, $R^3$ is pyrrolidinyl, optionally substituted with one, two, or three $R^{20b}$ that is —OH. In embodiments of a compound of Formula (I-1), (I'-1), (Ia-1), (Ia'-1), (Ib-1), (Ib'-1), (Ic-1), or (Ic'-1), or a pharmaceutically acceptable salt or solvate thereof, $R^3$ is pyrrolidinyl, optionally substituted with one, two, or three $R^{20b}$ that is oxo. In embodiments of a compound of Formula (I-1), (I'-1), (Ia-1), (Ia'-1), (Ib-1), (Ib'-1), (Ic-1), or (Ic'-1), or a pharmaceutically acceptable salt or solvate thereof, $R^3$ is pyrrolidinyl, optionally substituted with one, two, or three $R^{20b}$ that is —N($R^{24}$)C(O)$R^{25}$. In embodiments of a compound of Formula (I-1), (I'-1), (Ia-1), (Ia'-1), (Ib-1), (Ib'-1), (Ic-1), or (Ic'-1), or a pharmaceutically acceptable salt or solvate thereof, $R^3$ is pyrrolidinyl, optionally substituted with one, two, or three $R^{20b}$ that is —NHC(O)$R^{25}$. In embodiments of a compound of Formula (I-1), (I'-1), (Ia-1), (Ia'-1), (Ib-1), (Ib'-1), (Ic-1), or (Ic'-1), or a pharmaceutically acceptable salt or solvate thereof, $R^3$ is pyrrolidinyl, optionally substituted with one, two, or three $R^{20b}$ that is —NHC(O)$R^{25}$ and $R^{25}$ is $C_{2-9}$heterocycloalkyl optionally substituted with one, two, or three groups independently selected from halogen, $C_{1-6}$alkyl, $C_{1-6}$haloalkyl, $C_{1-6}$alkoxy, $C_{3-7}$cycloalkyl, $C_{2-9}$heterocycloalkyl, $C_{6-10}$aryl, and $C_{1-9}$heteroaryl. In embodiments of a compound of Formula (I-1), (I'-1), (Ia-1), (Ia'-1), (Ib-1), (Ib'-1), (Ic-1), or (Ic'-1), or a pharmaceutically acceptable salt or solvate thereof, $R^3$ is pyrrolidinyl, optionally substituted with one, two, or three $R^{20b}$ that is —NHC(O)$R^{25}$ and $R^{25}$ is $C_{2-5}$heterocycloalkyl optionally substituted with one $C_{1-6}$alkyl. In embodiments of a compound of Formula (I-1), (I'-1), (Ia-1), (Ia'-1), (Ib-1), (Ib'-1), (Ic-1), or (Ic'-1), or a pharmaceutically acceptable salt or solvate thereof, $R^3$ is pyrrolidinyl, optionally substituted with one, two, or three $R^{20b}$ that is —C(O)N($R^{22}$)($R^{23}$). In embodiments of a compound of Formula (I-1), (I'-1), (Ia-1), (Ia'-1), (Ib-1), (Ib'-1), (Ic-1), or (Ic'-1), or a pharmaceutically acceptable salt or solvate thereof, $R^3$ is pyrrolidinyl, optionally substituted with one, two, or three $R^{20b}$ that is —C(O)NH($R^{22}$). In embodiments of a compound of Formula (I-1), (I'-1), (Ia-1), (Ia'-1), (Ib-1), (Ib'-1), (Ic-1), or (Ic'-1), or a pharmaceutically acceptable salt or solvate thereof, $R^3$ is pyrrolidinyl, optionally substituted with one, two, or three $R^{20b}$ that is —C(O)NH($R^{22}$) and $R^{22}$ is $C_{2-9}$heterocycloalkyl optionally substituted with one, two, or three groups independently selected from halogen and $C_{1-6}$alkyl. In embodiments of a compound of Formula (I-1), (I'-1), (Ia-1), (Ia'-1), (Ib-1), (Ib'-1), (Ic-1), or (Ic'-1), or a pharmaceutically acceptable salt or solvate thereof, $R^3$ is pyrrolidinyl, optionally substituted with one, two, or three $R^{20b}$ that is —C(O)NH($R^{22}$) and $R^{22}$ is $C_{2-5}$heterocycloalkyl optionally substituted with one $C_{1-6}$alkyl.

In some embodiments is a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), or a pharmaceutically acceptable salt or solvate thereof, wherein $R^3$ is cyclopropyl optionally substituted with one, two, or three $R^{20b}$. In some embodiments is a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), or a pharmaceutically acceptable salt or solvate thereof, wherein $R^3$ is cyclobutyl optionally substituted with one, two, or three $R^{20b}$. In some embodiments is a compound of Formula (I-1), (I'-1), (Ia-1), (Ia'-1), (Ib-1), (Ib'-1), (Ic-1), or (Ic'-1), or a pharmaceutically acceptable salt or solvate thereof, wherein $R^3$ is cyclopentyl optionally substituted with one, two, or three $R^{20b}$. In some embodiments is a compound of Formula (I-1), (I'-1), (Ia-1), (Ia'-1), (Ib-1), (Ib'-1), (Ic-1), or (Ic'-1), or a pharmaceutically acceptable salt or solvate thereof, wherein $R^3$ is cyclohexyl optionally substituted with one, two, or three $R^{20b}$. In some embodiments is a compound of Formula (I-1), (I'-1), (Ia-1), (Ia'-1), (Ib-1), (Ib'-1), (Ic-1), or (Ic'-1), or a pharmaceutically acceptable salt or solvate thereof, wherein $R^3$ is aziridinyl optionally substituted with one, two, or three $R^{20b}$. In some embodiments is a compound of Formula (I-1), (I'-1), (Ia-1), (Ia'-1), (Ib-1), (Ib'-1), (Ic-1), or (Ic'-1), or a pharmaceutically acceptable salt or solvate thereof, wherein $R^3$ is azetidinyl optionally substituted with one, two, or three $R^{20b}$. In some embodiments is a compound of Formula (I-1), (I'-1), (Ia-1), (Ia'-1), (Ib-1), (Ib'-1), (Ic-1), or (Ic'-1), or a pharmaceutically acceptable salt or solvate thereof, wherein $R^3$ is pyrrolidinyl optionally substituted with one, two, or three $R^{20b}$. In some embodiments is a compound of Formula (I-1), (I'-1), (Ia-1), (Ia'-1), (Ib-1), (Ib'-1), (Ic-1), or (Ic'-1), or a pharmaceutically acceptable salt or solvate thereof, wherein $R^3$ is piperidinyl optionally substituted with one, two, or three $R^{20b}$. In some embodiments is a compound of Formula (I-1), (I'-1), (Ia-1), (Ia'-1), (Ib-1), (Ib'-1), (Ic-1), or (Ic'-1), or a pharmaceutically acceptable salt or solvate thereof, wherein $R^3$ is piperizinyl optionally substituted with one, two, or three $R^{20b}$. In some embodiments is a compound of Formula (I-1), (I'-1), (Ia-1), (Ia'-1), (Ib-1), (Ib'-1), (Ic-1), or (Ic'-1), or a pharmaceutically acceptable salt or solvate thereof, wherein $R^3$ is morpholinyl optionally substituted with one, two, or three $R^{20b}$. In some embodiments is a compound of Formula (I-1), (I'-1), (Ia-1), (Ia'-1), (Ib-1), (Ib'-1), (Ic-1), or (Ic'-1), or a pharmaceutically acceptable salt or solvate thereof, wherein $R^3$ is oxetanyl optionally substituted with one, two, or three $R^{20b}$. In some embodiments is a compound of Formula (I-1), (I'-1), (Ia-1), (Ia'-1), (Ib-1), (Ib'-1), (Ic-1), or (Ic'-1), or a pharmaceutically acceptable salt or solvate thereof, wherein $R^3$ is tetrahydrofuranyl optionally substituted with one, two, or three $R^{20b}$. In some embodiments is a compound of Formula (I-1), (I'-1), (Ia-1), (Ia'-1), (Ib-1), (Ib'-1), (Ic-1), or (Ic'-1), or a pharmaceutically acceptable salt or solvate thereof, wherein $R^3$ is tetrahydropyranyl optionally substituted with one, two, or three $R^{20b}$. In some embodiments is a compound of Formula (I-1), (I'-1), (Ia-1), (Ia'-1), (Ib-1), (Ib'-1), (Ic-1), or (Ic'-1), or a pharmaceutically acceptable salt or solvate thereof, wherein $R^3$ is pyridinyl optionally substituted with one, two, or three $R^{20b}$. In some embodiments is a compound of Formula (I-1), (I'-1), (Ia-1), (Ia'-1), (Ib-1), (Ib'-1), (Ic-1), or (Ic'-1), or a pharmaceutically acceptable salt or solvate thereof, wherein $R^3$ is pyrazinyl optionally substituted with one, two, or three $R^{20b}$. In some embodiments is a compound of Formula (I-1), (I'-1), (Ia-1), (Ia'-1), (Ib-1), (Ib'-1), (Ic-1), or (Ic'-1), or a pharmaceutically acceptable salt or solvate thereof, wherein $R^3$ is pyrimidinyl optionally substituted with one, two, or three $R^{20b}$. In some embodiments is a compound of Formula (I-1), (I'-1), (Ia-1), (Ia'-1), (Ib-1), (Ib'-1), (Ic-1), or (Ic'-1), or a pharmaceutically acceptable salt or solvate thereof, wherein $R^3$ is pyridazinyl optionally substituted with one, two, or three $R^{20b}$. In some embodiments is a compound of Formula (I-1), (I'-1), (Ia-1), (Ia'-1), (Ib-1), (Ib'-1), (Ic-1), or (Ic'-1), or a pharmaceutically acceptable salt or solvate thereof, wherein $R^3$ is phenyl optionally substituted with one, two, or three $R^{20b}$. In some embodiments is a compound of Formula (I-1), (I'-1), (Ia-1), (Ia'-1), (Ib-1), (Ib'-1), (Ic-1), or (Ic'-1), or a pharmaceutically acceptable salt or solvate thereof, wherein $R^3$ is pyrazolyl optionally substituted with one, two, or three $R^{20b}$. In some embodiments is a compound of Formula (I-1), (I'-1), (Ia-1), (Ia'-1), (Ib-1), (Ib'-1), (Ic-1), or (Ic'-1), or a pharmaceutically acceptable salt or solvate thereof, wherein $R^3$ is pyrrolyl optionally substituted with one, two, or three $R^{20b}$. In some embodiments is a compound of Formula (I-1), (I'-1), (Ia-1), (Ia'-1), (Ib-1), (Ib'-1), (Ic-1), or (Ic'-1), or a pharmaceutically acceptable salt or solvate thereof, wherein $R^3$ is thiophenyl optionally substituted with one, two, or three $R^{20b}$. In some embodiments is a compound of Formula (I-1), (I'-1), (Ia-1), (Ia'-1), (Ib-1), (Ib'-1), (Ic-1), or (Ic'-1), or a pharmaceutically acceptable salt or solvate thereof, wherein R³ is thianyl optionally substituted with one, two, or three R²⁰ᵇ. In some embodiments is a compound of Formula (I-1), (I'-1), (Ia-1), (Ia'-1), (Ib-1), (Ib'-1), (Ic-1), or (Ic'-1), or a pharmaceutically acceptable salt or solvate thereof, wherein R³ is 1,3-imidazolyl optionally substituted with one, two, or three R²⁰ᵇ. In some embodiments is a compound of Formula (I-1), (I'-1), (Ia-1), (Ia'-1), (Ib-1), (Ib'-1), (Ic-1), or (Ic'-1), or a pharmaceutically acceptable salt or solvate thereof, wherein R³ is thiazolyl optionally substituted with one, two, or three R²⁰ᵇ. In some embodiments is a compound of Formula (I-1), (I'-1), (Ia-1), (Ia'-1), (Ib-1), (Ib'-1), (Ic-1), or (Ic'-1), or a pharmaceutically acceptable salt or solvate thereof, wherein R³ is oxepanyl optionally substituted with one, two, or three R²⁰ᵇ. In some embodiments is a compound of Formula (I-1), (I'-1), (Ia-1), (Ia'-1), (Ib-1), (Ib'-1), (Ic-1), or (Ic'-1), or a pharmaceutically acceptable salt or solvate thereof, wherein R³ is azepanyl optionally substituted with one, two, or three R²⁰ᵇ. In some embodiments is a compound of Formula (I-1), (I'-1), (Ia-1), (Ia'-1), (Ib-1), (Ib'-1), (Ic-1), or (Ic'-1), or a pharmaceutically acceptable salt or solvate thereof, wherein R³ is 1,4-dioxapanyl optionally substituted with one, two, or three R²⁰ᵇ. In some embodiments is a compound of Formula (I-1), (I'-1), (Ia-1), (Ia'-1), (Ib-1), (Ib'-1), (Ic-1), or (Ic'-1), or a pharmaceutically acceptable salt or solvate thereof, wherein R³ is 1,4-oxazepanyl optionally substituted with one, two, or three R²⁰ᵇ. In some embodiments is a compound of Formula (I-1), (I'-1), (Ia-1), (Ia'-1), (Ib-1), (Ib'-1), (Ic-1), or (Ic'-1), or a pharmaceutically acceptable salt or solvate thereof, wherein R³ is 2,6-diazaspiro[3.3]heptanyl optionally substituted with one, two, or three R²⁰ᵇ. In some embodiments is a compound of Formula (I-1), (I'-1), (Ia-1), (Ia'-1), (Ib-1), (Ib'-1), (Ic-1), or (Ic'-1), or a pharmaceutically acceptable salt or solvate thereof, wherein R³ is 2-oxa-6-azaspiro[3.3]heptanyl optionally substituted with one, two, or three R²⁰ᵇ.

In some embodiments is a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), or a pharmaceutically acceptable salt or solvate thereof, wherein R³ is

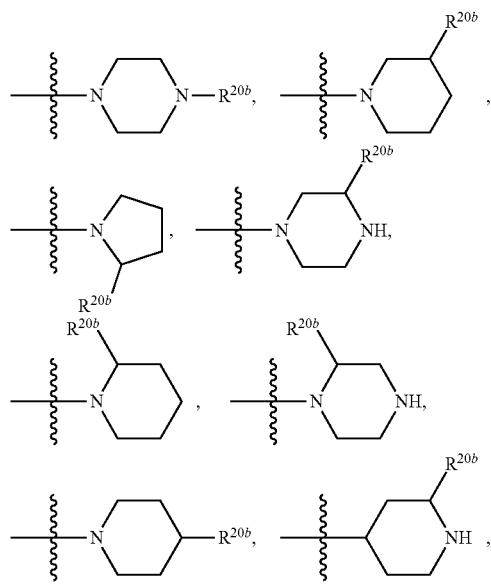

-continued

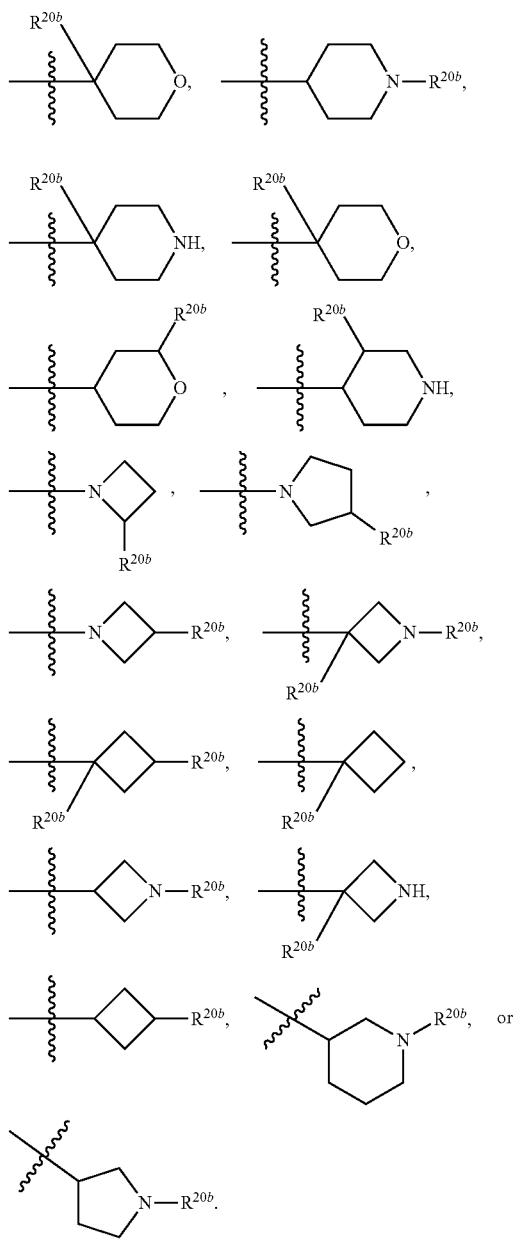

In some embodiments is a compound of Formula (I-1), (I'-1), (Ia-1), (Ia'-1), (Ib-1), (Ib'-1), (Ic-1), or (Ic'-1), or a pharmaceutically acceptable salt or solvate thereof, wherein R³ is

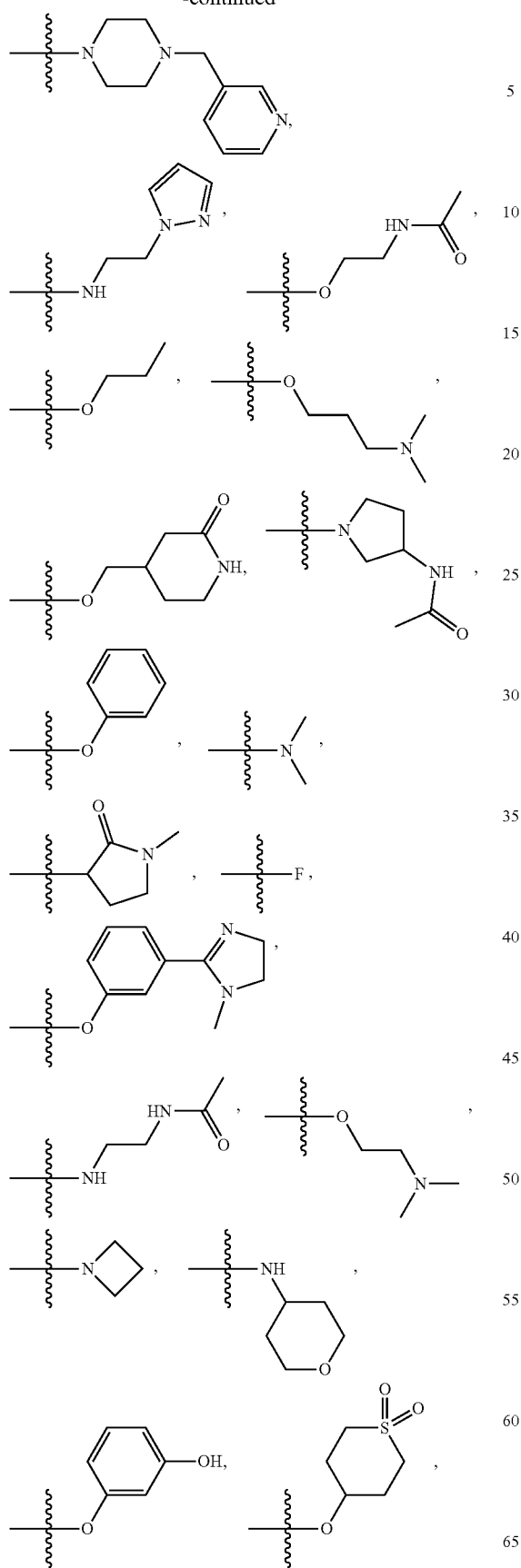
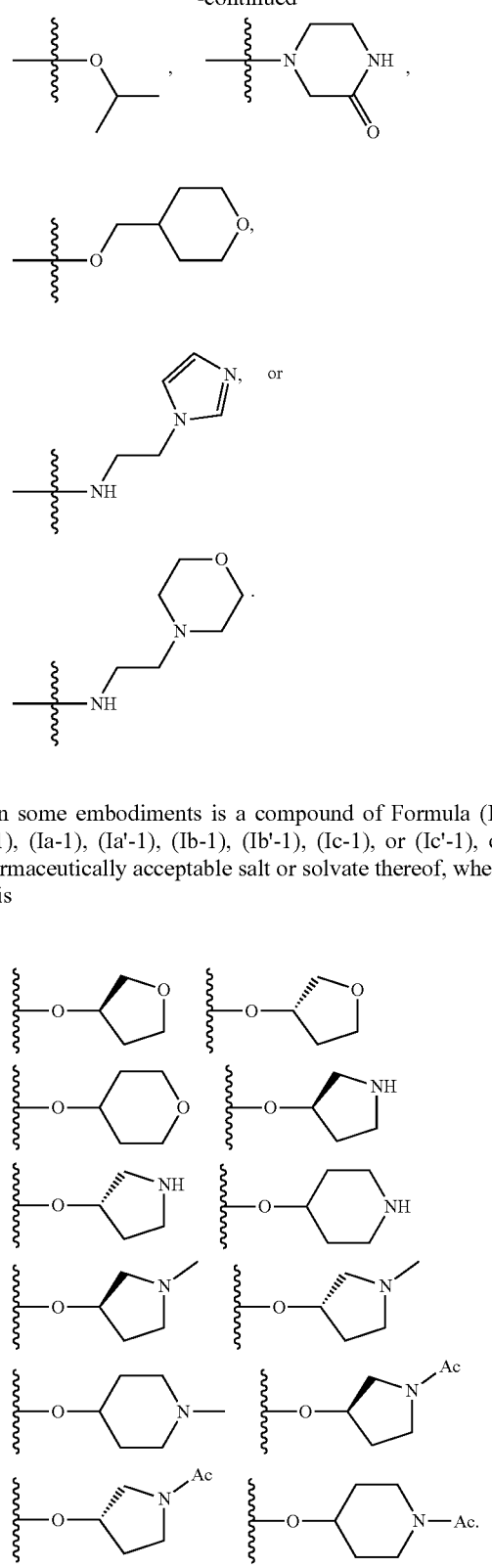
In some embodiments is a compound of Formula (I-1), (I'-1), (Ia-1), (Ia'-1), (Ib-1), (Ib'-1), (Ic-1), or (Ic'-1), or a pharmaceutically acceptable salt or solvate thereof, wherein R³ is
In some embodiments is a compound of Formula (I-1), (I'-1), (Ia-1), (Ia'-1), (Ib-1), (Ib'-1), (Ic-1), or (Ic'-1), or a pharmaceutically acceptable salt or solvate thereof, wherein R³ is

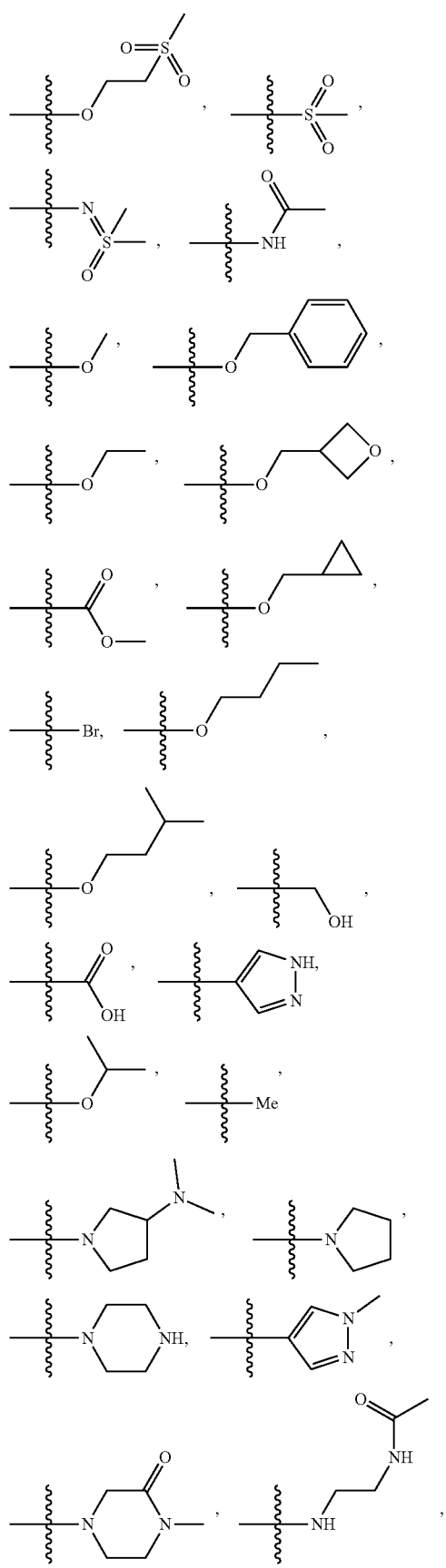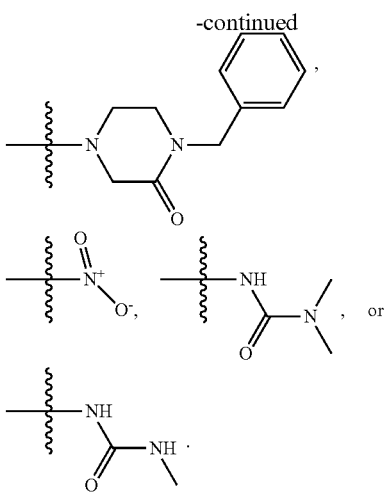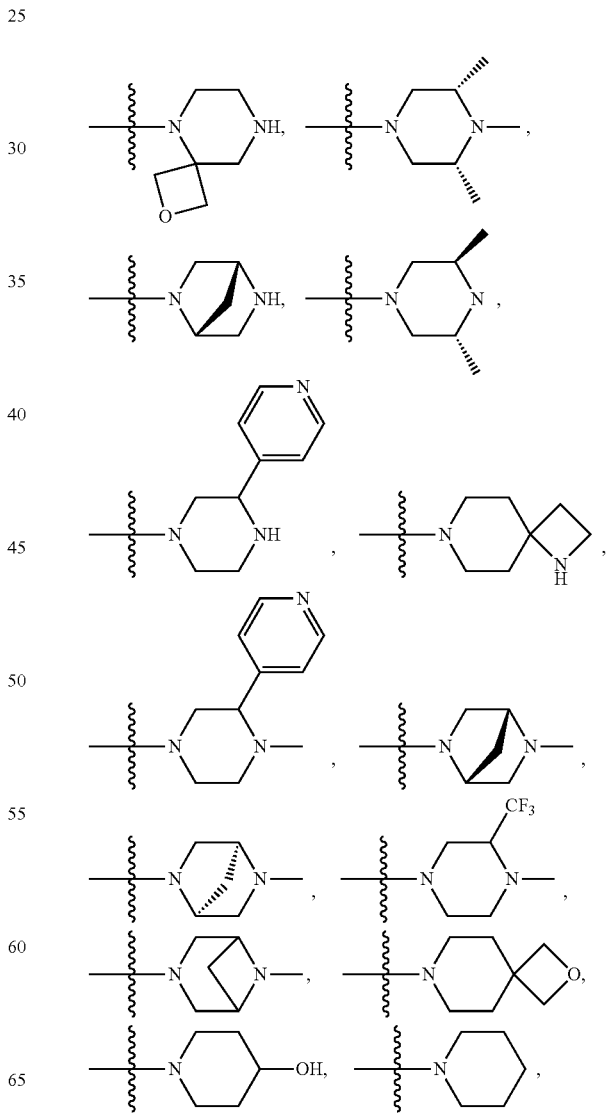
In some embodiments is a compound of Formula (I-1), (I'-1), (Ia-1), (Ia'-1), (Ib-1), (Ib'-1), (Ic-1), or (Ic'-1), or a pharmaceutically acceptable salt or solvate thereof, wherein $R^3$ is

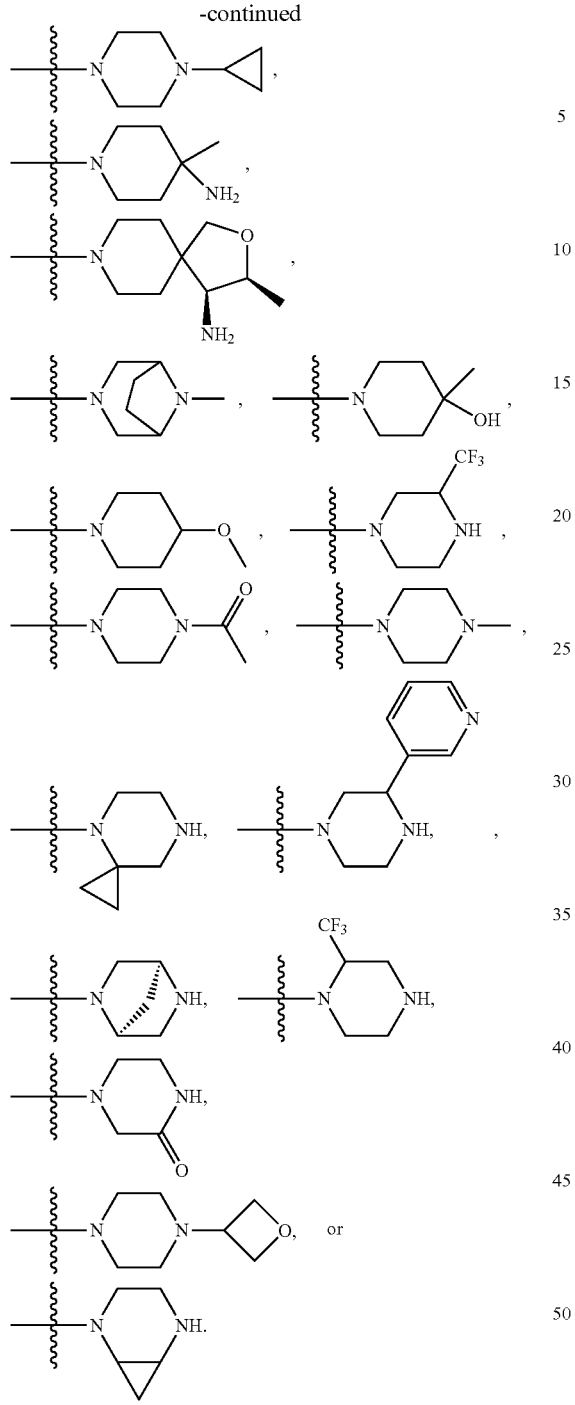
In some embodiments is a compound of Formula (I-1), (I'-1), (Ia-1), (Ia'-1), (Ib-1), (Ib'-1), (Ic-1), or (Ic'-1), or a pharmaceutically acceptable salt or solvate thereof, wherein $R^3$ is
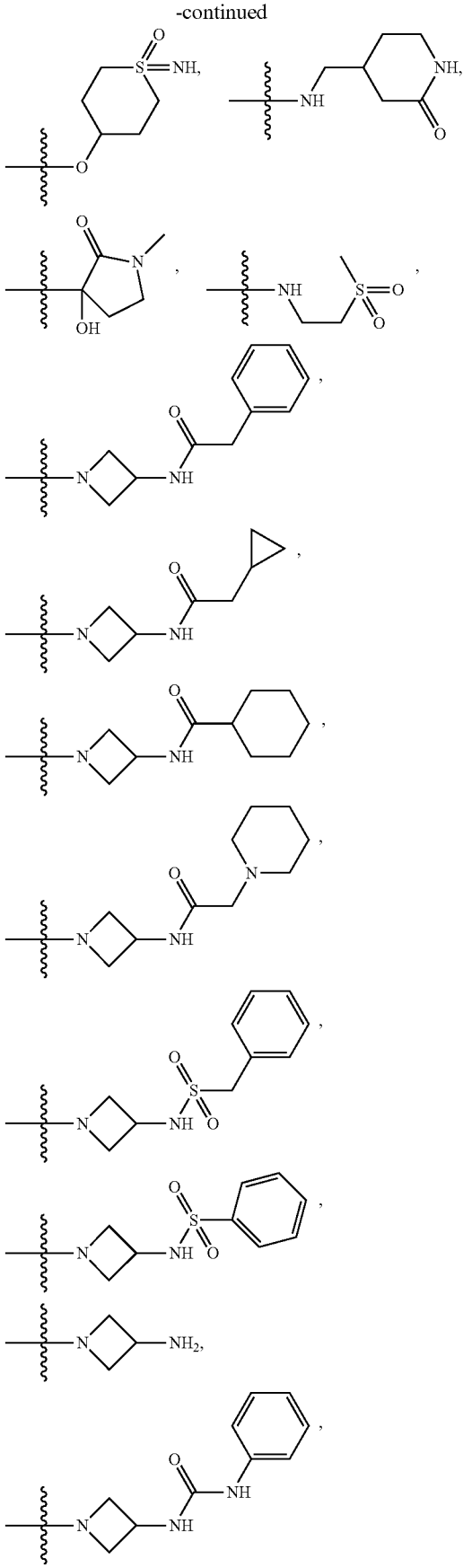

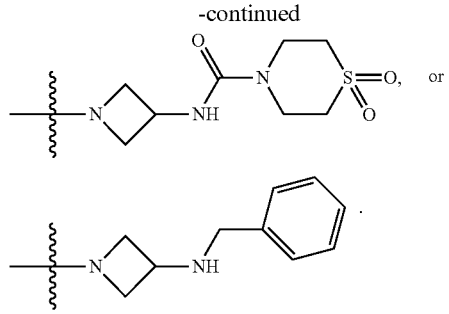
In some embodiments is a compound of Formula (I-1), (I'-1) (Ia-1), (Ia'-1), (Ib-1), (Ib'-1) (Ic-1), or (Ic'-1), or a pharmaceutically acceptable salt or solvate thereof, wherein R³ is
In some embodiments is a compound of Formula (I-1), (I'-1), (Ia-1), (Ia'-1), (Ib-1), (Ib'-1), (Ic-1), or (Ic'-1), or a pharmaceutically acceptable salt or solvate thereof, wherein R³ is

-continued
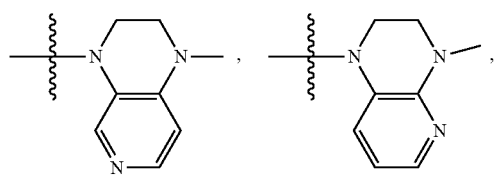
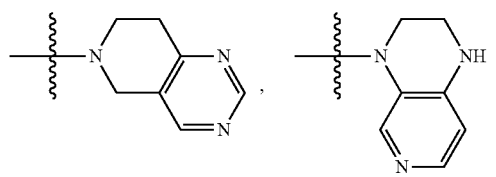
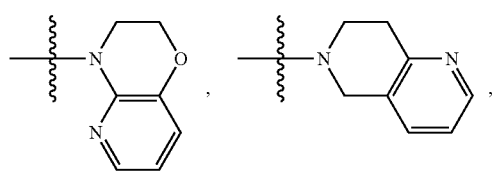
In some embodiments is a compound of Formula (I-1), (I'-1) (Ia-1), (Ia'-1), (Ib-1), (Ib'-1) (Ic-1), or (Ic'-1), or a pharmaceutically acceptable salt or solvate thereof, wherein R$^3$ is
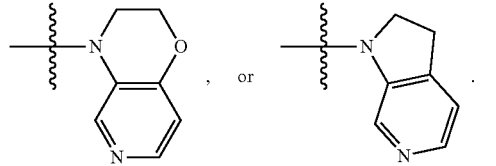
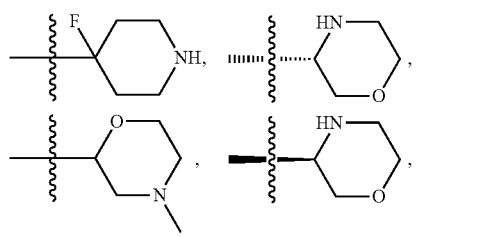
-continued
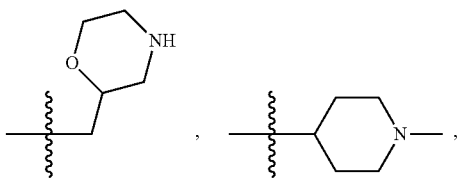
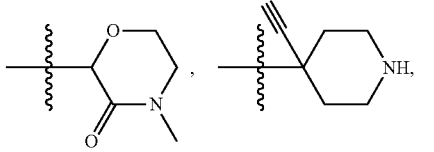
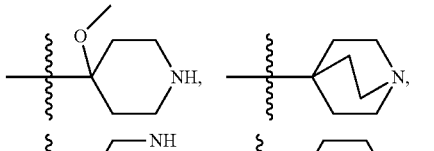
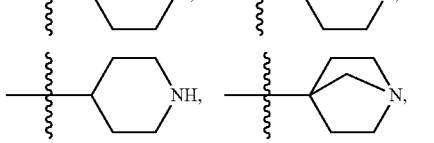
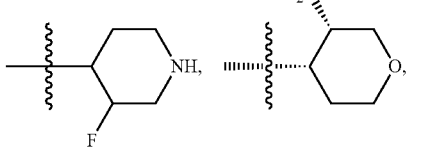
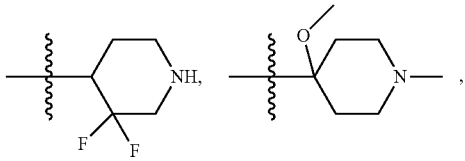
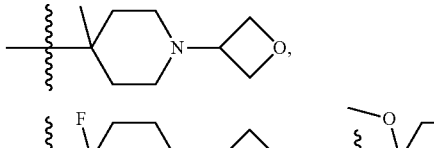
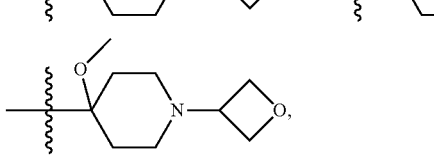
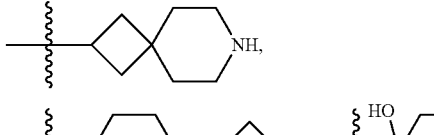
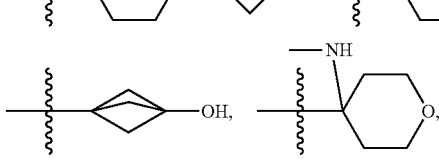

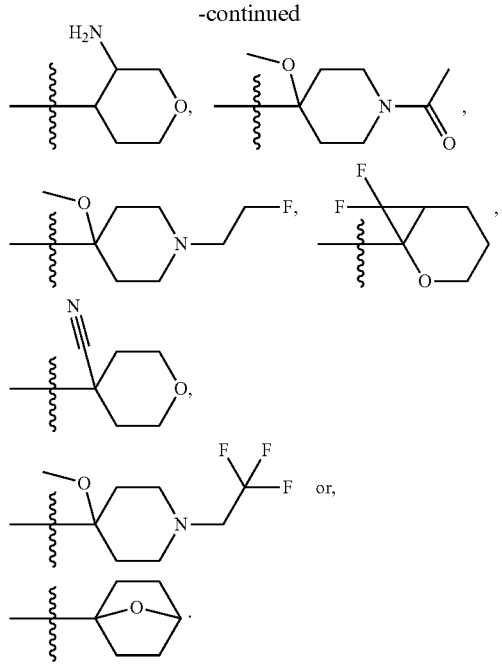
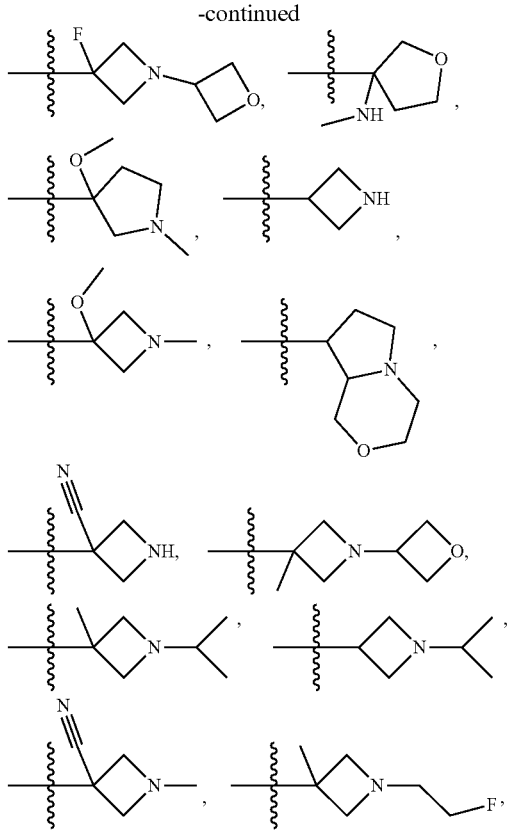
In some embodiments is a compound of Formula (I-1), (I'-1), (Ia-1), (Ia'-1), (Ib-1), (Ib'-1), (Ic-1), or (Ic'-1), or a pharmaceutically acceptable salt or solvate thereof, wherein $R^3$ is
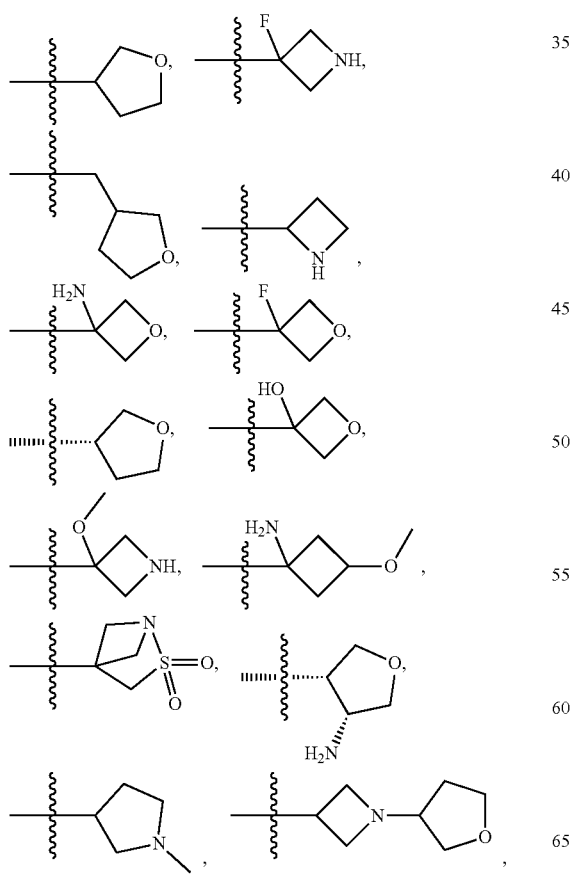

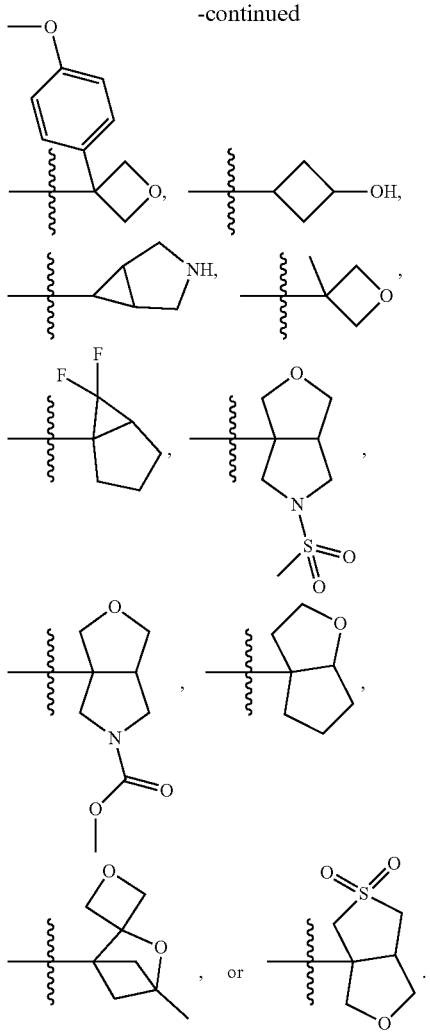
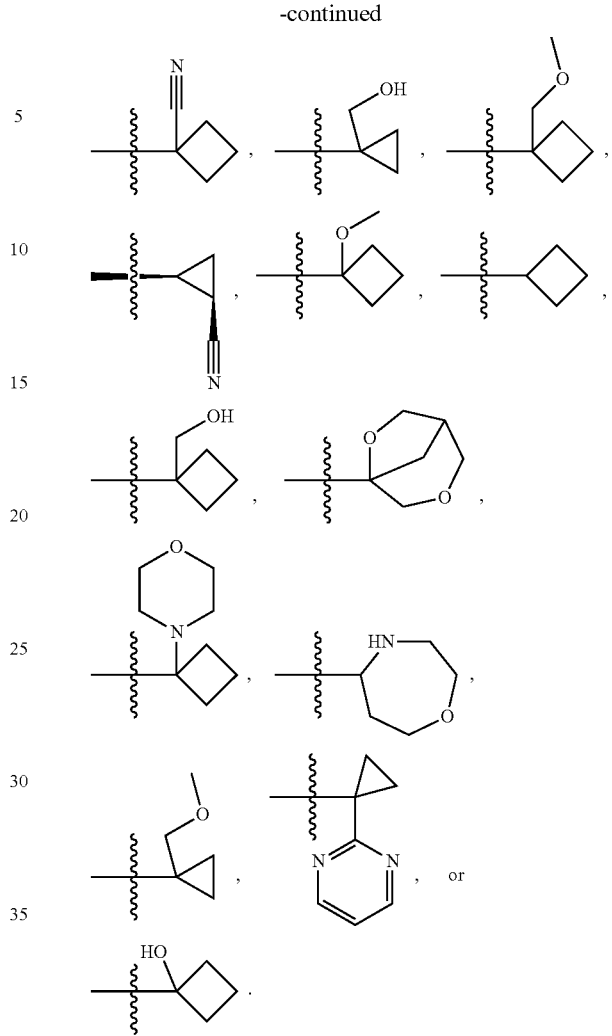
In some embodiments is a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), or a pharmaceutically acceptable salt or solvate thereof, wherein $R^3$ is
In some embodiments is a compound of Formula (I-1), (I'-1), (Ia-1), (Ia'-1), (Ib-1), (Ib'-1), (Ic-1), or (Ic'-1), or a pharmaceutically acceptable salt or solvate thereof, wherein $R^3$ is
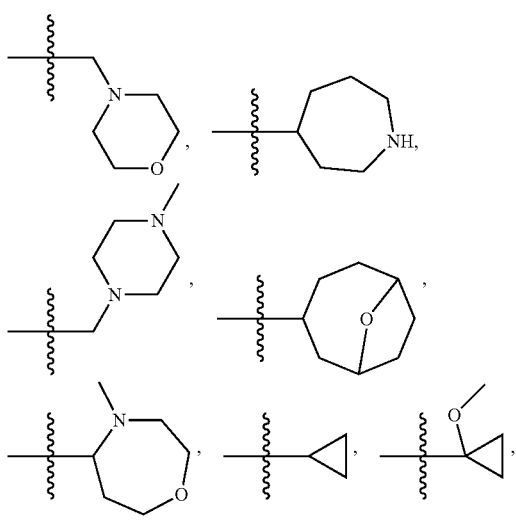
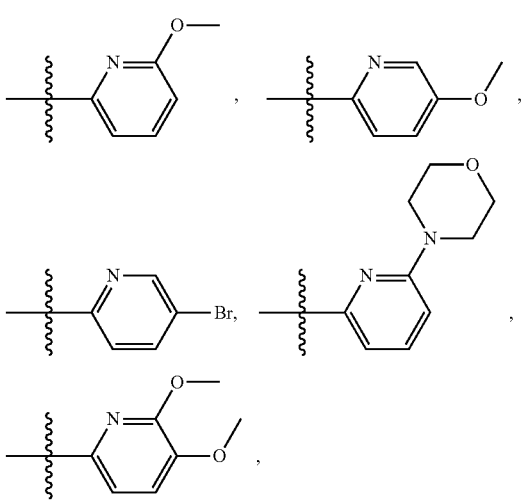

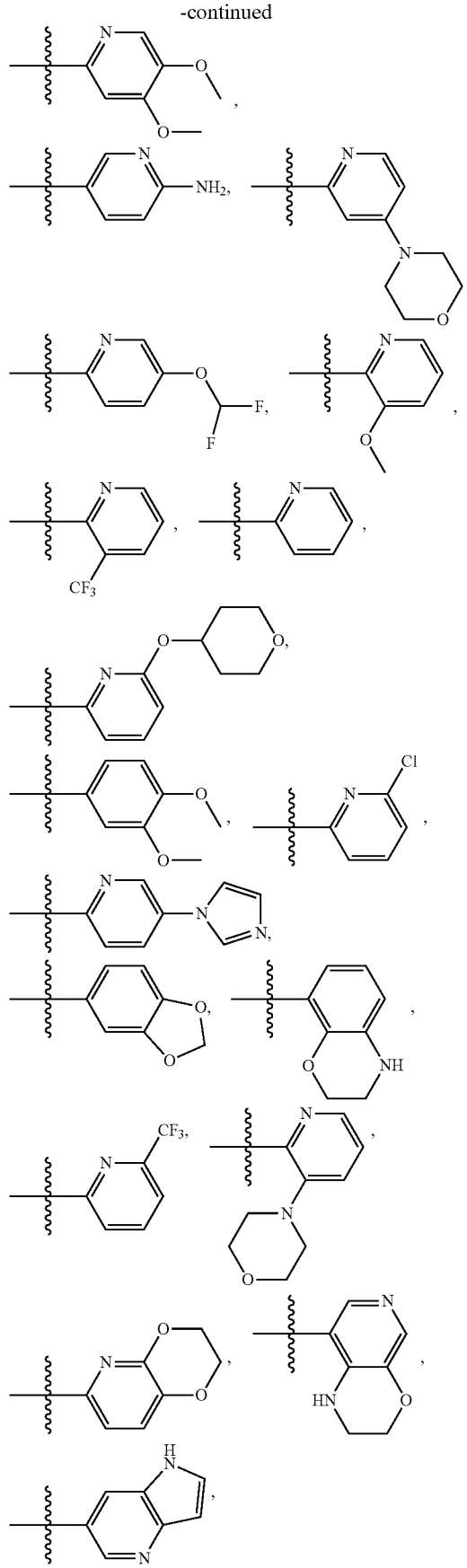
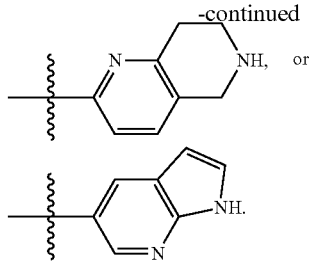
In some embodiments is a compound of Formula (I-1), (I'-1) (Ia-1), (Ia'-1), (Ib-1), (Ib-1), (Ic-1), or (Ic'-1), or a pharmaceutically acceptable salt or solvate thereof, wherein R³ is
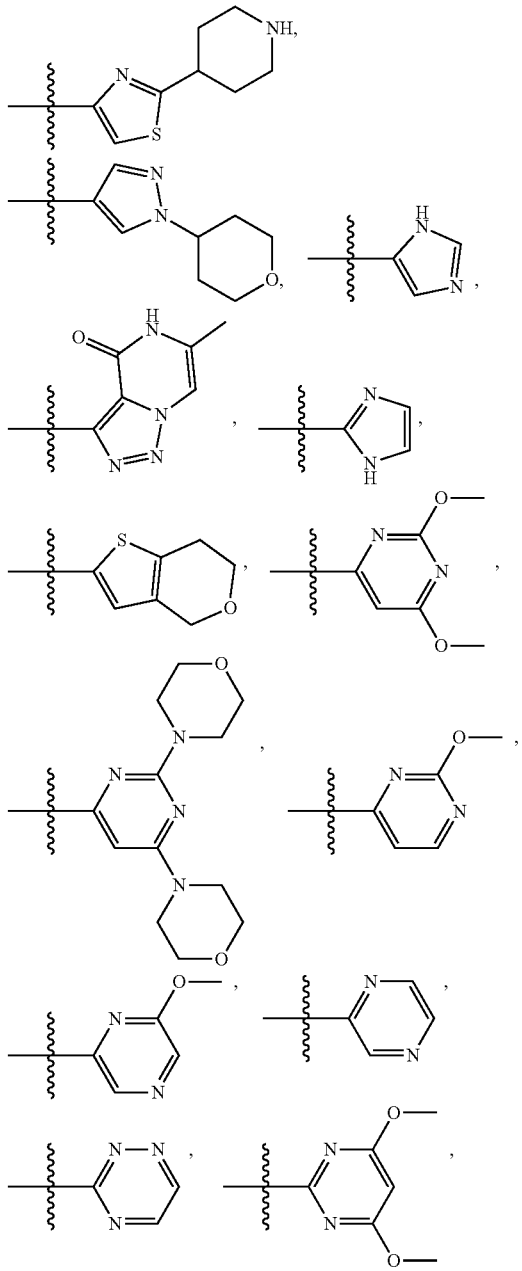

-continued
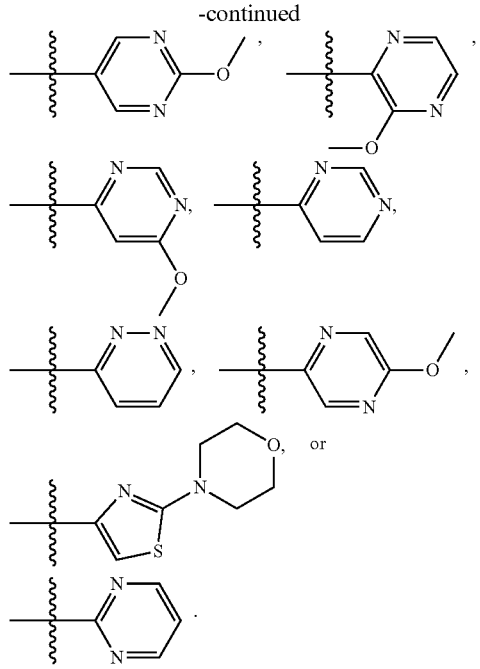
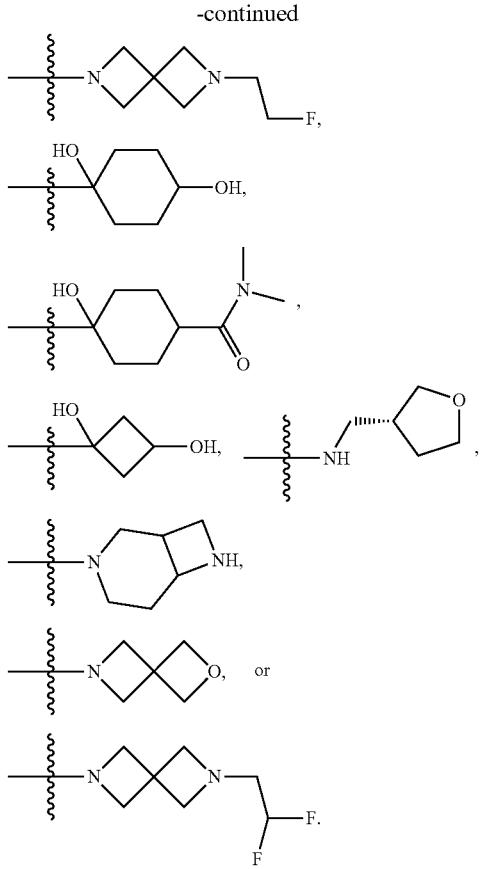
In some embodiments is a compound of Formula (I-1), (I'-1), (Ia-1), (Ia'-1), (Ib-1), (Ib'-1), (Ic-1), or (Ic'-1), or a pharmaceutically acceptable salt or solvate thereof, wherein R³ is
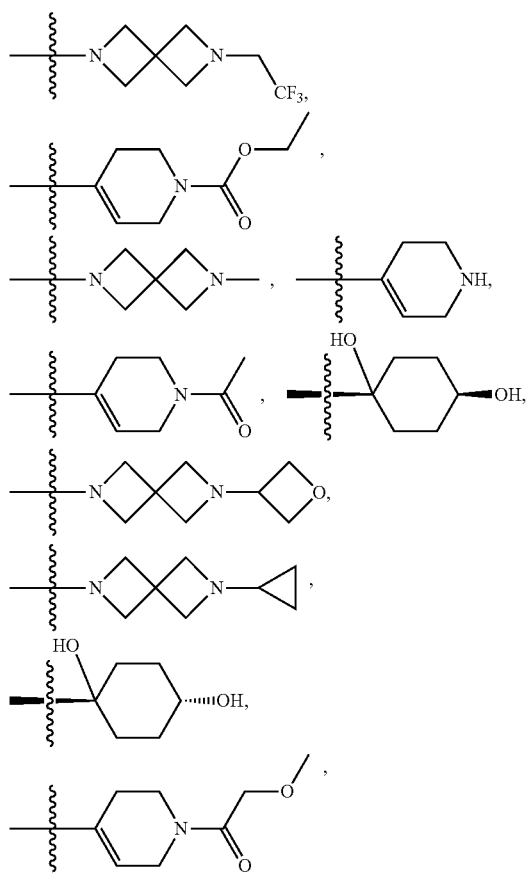
In some embodiments is a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), or a pharmaceutically acceptable salt or solvate thereof, wherein R³ is
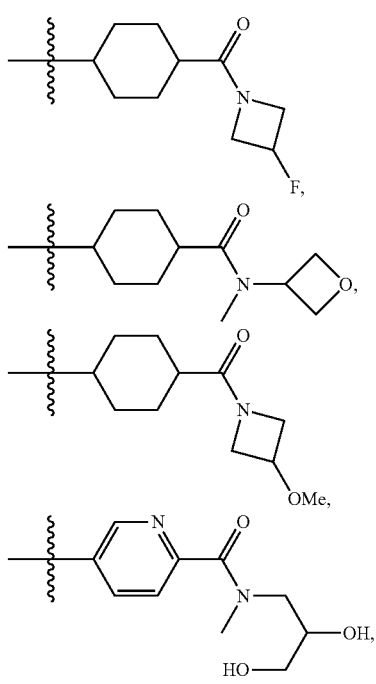

-continued
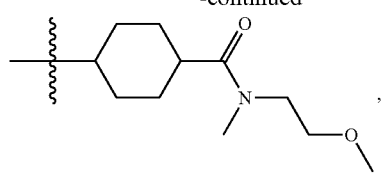,
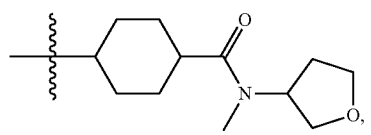,
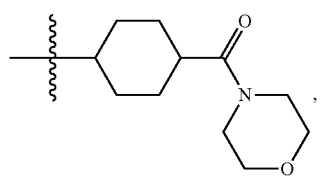,
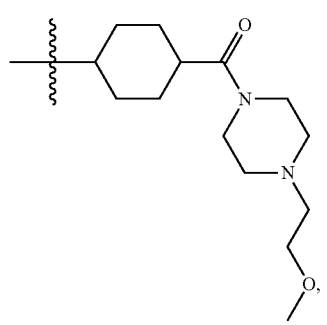,
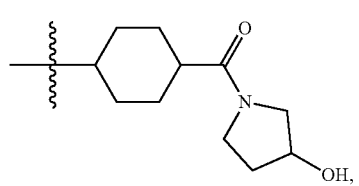,
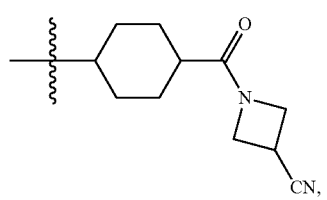,
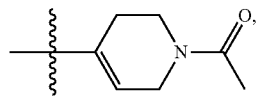,
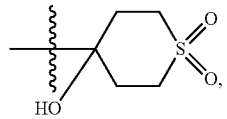,
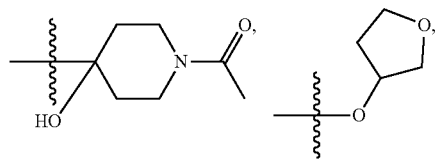
-continued
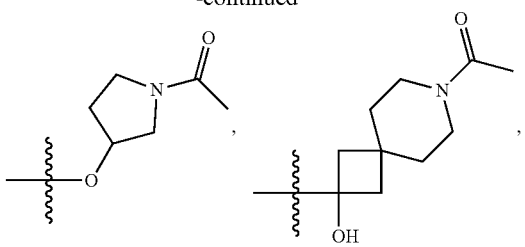,
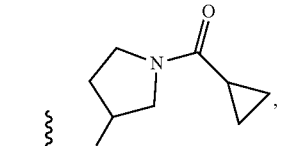,
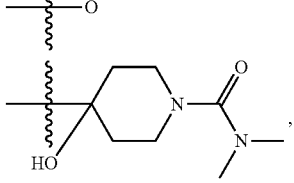,
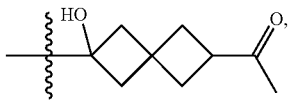,
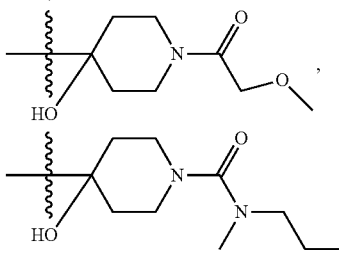,
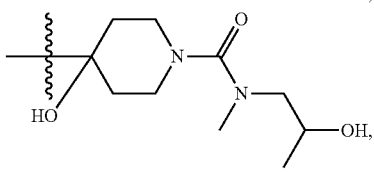,
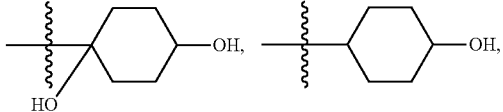,
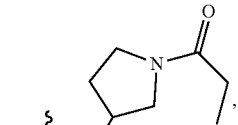,
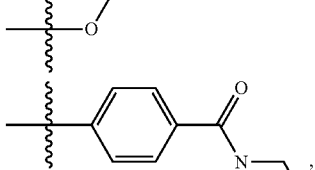,
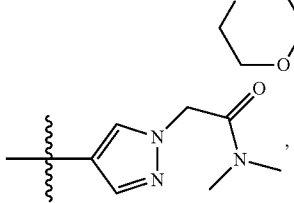,

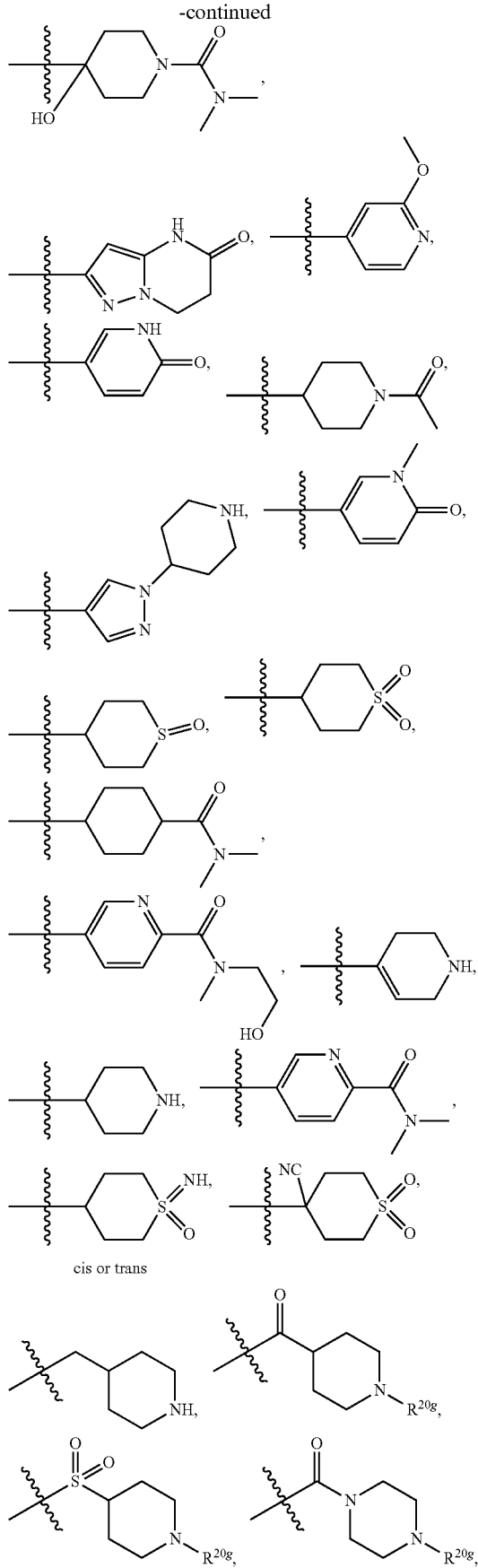
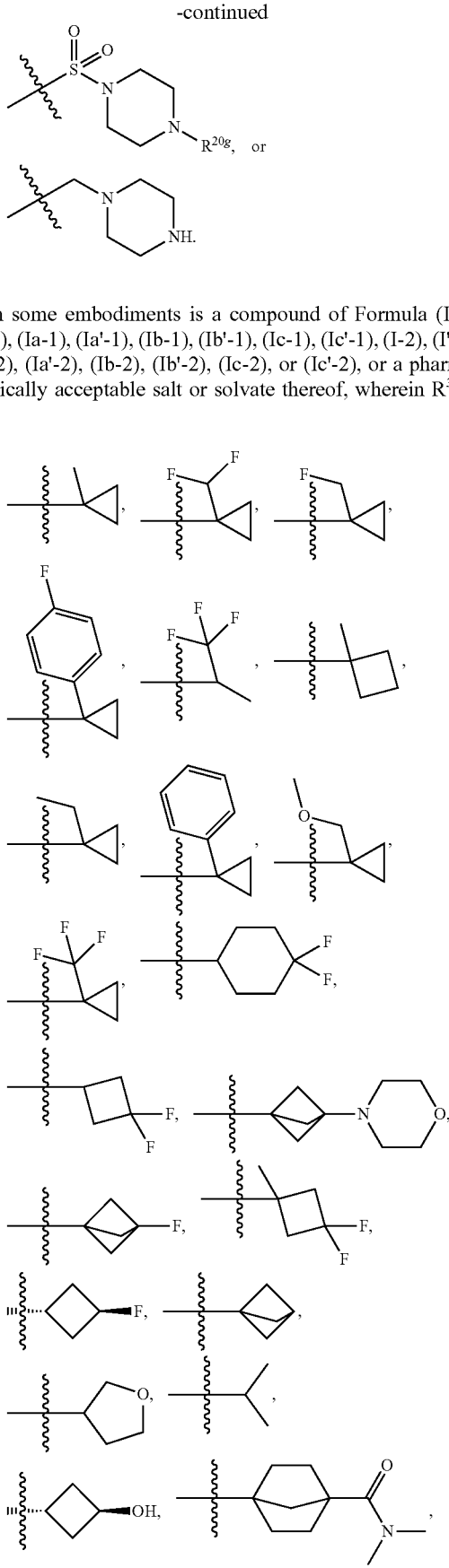
In some embodiments is a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), or a pharmaceutically acceptable salt or solvate thereof, wherein $R^3$ is -continued

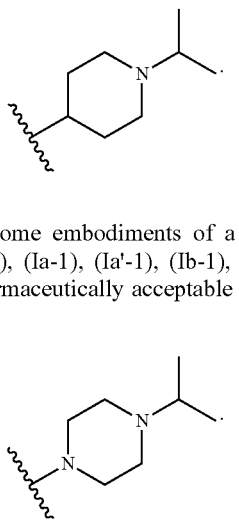

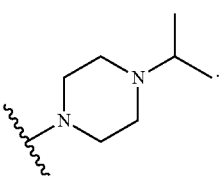 [SMILES: *N1CCN(C(C)C)CC1]

In some embodiments of a compound of Formula (I-1), (I'-1), (Ia-1), (Ia'-1), (Ib-1), (Ib'-1), (Ic-1), or (Ic'-1), or a pharmaceutically acceptable salt or solvate thereof, $R^3$ is

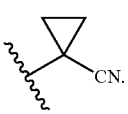

In some embodiments of a compound of Formula (I-1), (I'-1), (Ia-1), (Ia'-1), (Ib-1), (Ib'-1), (Ic-1), (Ic'-1) (I-2), (I'-2), (Ia-2), (Ia'-2), (Ib-2), (Ib'-2), (Ic-2), or (Ic'-2), or a pharmaceutically acceptable salt or solvate thereof, $R^3$ is In some embodiments of a compound of Formula (I-1), (I'-1), (Ia-1), (Ia'-1), (Ib-1), (Ib'-1), (Ic-1), or (Ic'-1), or a pharmaceutically acceptable salt or solvate thereof, $R^3$ is

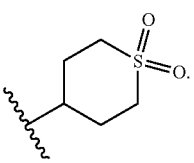 [SMILES: *C1CCS(=O)(=O)CC1]

In some embodiments of a compound of Formula (I-1), (I'-1), (Ia-1), (Ia'-1), (Ib-1), (Ib'-1), (Ic-1), or (Ic'-1), or a pharmaceutically acceptable salt or solvate thereof, $R^3$ is

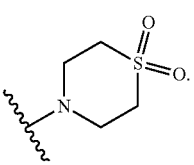 [SMILES: *N1CCS(=O)(=O)CC1]

In some embodiments of a compound of Formula (I-1), (I'-1), (Ia-1), (Ia'-1), (Ib-1), (Ib'-1), (Ic-1), or (Ic'-1), or a pharmaceutically acceptable salt or solvate thereof, $R^3$ is In some embodiments is a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), or a pharmaceutically acceptable salt or solvate thereof, wherein $R^6$ is selected from hydrogen, $C_{1-6}$alkyl, $C_{3-10}$cycloalkyl, $C_{2-9}$heterocycloalkyl, $C_{6-10}$aryl, and $C_{1-9}$heteroaryl, wherein $C_{1-6}$alkyl, $C_{3-10}$cycloalkyl, $C_{2-9}$heterocycloalkyl, $C_{6-10}$aryl, and $C_{1-9}$heteroaryl are optionally substituted with one, two, or three $R^{20c}$. In some embodiments is a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), or a pharmaceutically acceptable salt or solvate thereof, wherein $R^6$ is selected from hydrogen and $C_{1-6}$alkyl optionally substituted with one, two, or three $R^{20c}$. In some embodiments is a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), or a pharmaceutically acceptable salt or solvate thereof, wherein $R^6$ is $C_{1-6}$ alkyl optionally substituted with one, two, or three $R^{20c}$. In some embodiments is a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), or a pharmaceutically acceptable salt or solvate thereof, wherein $R^6$ is hydrogen. In some embodiments is a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), or a pharmaceutically acceptable salt or solvate thereof, wherein $R^6$ is methyl.

In some embodiments is a compound of Formula (I-2), (I'-2), (Ia-2), (Ia'-2), (Ib-2), (Ib'-2), (Ic-2), or (Ic'-2), or a pharmaceutically acceptable salt or solvate thereof, wherein $R^7$ is selected from hydrogen, $C_{1-6}$alkyl, $C_{3-10}$cycloalkyl, $C_{2-9}$heterocycloalkyl, $C_{6-10}$aryl, and $C_{1-9}$heteroaryl, wherein $C_{1-6}$alkyl, $C_{3-10}$cycloalkyl, $C_{2-9}$heterocycloalkyl, $C_{6-10}$aryl, and $C_{1-9}$heteroaryl are optionally substituted with one, two, or three $R^{20c}$. In some embodiments is a compound of Formula (I-2), (I'-2), (Ia-2), (Ia'-2), (Ib-2), (Ib'-2), (Ic-2), or (Ic'-2), or a pharmaceutically acceptable salt or solvate thereof, wherein $R^7$ is selected from hydrogen and $C_{1-6}$ alkyl optionally substituted with one, two, or three $R^{20c}$. In some embodiments is a compound of Formula (I-2), (I'-2), (Ia-2), (Ia'-2), (Ib-2), (Ib'-2), (Ic-2), or (Ic'-2), or a pharmaceutically acceptable salt or solvate thereof, wherein $R^7$ is $C_{1-6}$alkyl optionally substituted with one, two, or three $R^{20c}$. In some embodiments is a compound of Formula (I-2), (I'-2), (Ia-2), (Ia'-2), (Ib-2), (Ib'-2), (Ic-2), or (Ic'-2), or a pharmaceutically acceptable salt or solvate thereof, wherein $R^7$ is hydrogen. In some embodiments is a compound of Formula (I-2), (I'-2), (Ia-2), (Ia'-2), (Ib-2), (Ib'-2), (Ic-2), or (Ic'-2), or a pharmaceutically acceptable salt or solvate thereof, wherein $R^7$ is methyl.

In some embodiments is a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), or a pharmaceutically acceptable salt or solvate thereof, wherein $L^1$ is a bond. In some embodiments is a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), or a pharmaceutically acceptable salt or solvate thereof, wherein $L^1$ is $C_{1-6}$alkyl.

In some embodiments is a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), or a pharmaceutically acceptable salt or solvate thereof, wherein $R^1$ is a 6-10 membered aryl ring optionally substituted with one or more $R^{10}$. In some embodiments is a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), or a pharmaceutically acceptable salt or solvate thereof, wherein $R^1$ is a phenyl optionally substituted with one or more $R^{10}$. In some embodiments is a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), or a pharmaceutically acceptable salt or solvate thereof, wherein $R^1$ is a phenyl substituted with one or more $R^{10}$. In some embodiments is a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), or a pharmaceutically acceptable salt or solvate thereof, wherein $R^1$ is phenyl substituted with one, two, or three $R^{10}$. In some embodiments is a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), or a pharmaceutically acceptable salt or solvate thereof, wherein $R^1$ is phenyl substituted with one, two, or three $R^{10}$, wherein each $R^{10}$ is independently selected from halogen, $C_{1-6}$alkyl, $C_{3-7}$cycloalkyl, $C_{2-9}$heterocycloalkyl, $C_{6-10}$aryl, $C_{1-9}$heteroaryl, $-OR^{12}$, and $N(R^{12})(R^{13})$, wherein $C_{1-6}$alkyl, $C_{3-7}$cycloalkyl, $C_{2-9}$heterocycloalkyl, $C_{6-10}$aryl, and $C_{1-9}$heteroaryl are optionally substituted with one, two, or three $R^{20d}$. In some embodiments is a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), or a pharmaceutically acceptable salt or solvate thereof, wherein $R^1$ is phenyl substituted with one, two, or three $R^{10}$, wherein each $R^{10}$ is independently selected from halogen, $C_{1-6}$alkyl, and $N(R^{12})(R^{13})$ wherein $C_{1-6}$alkyl is optionally substituted with one, two, or three $R^{20d}$. In some embodiments is a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), or a pharmaceutically acceptable salt or solvate thereof, wherein $R^1$ is phenyl substituted with one, two, or three $R^{10}$, wherein each $R^{10}$ is independently selected from halogen and $C_{1-6}$alkyl, wherein $C_{1-6}$alkyl is substituted with one, two, or three $R^{20d}$, and each $R^{20d}$ is halogen.

In some embodiments is a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), or a pharmaceutically acceptable salt or solvate thereof, wherein $R^1$ is a 5-10 membered heteroaryl ring optionally substituted with one or more $R^{10}$. In some embodiments is a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), or a pharmaceutically acceptable salt or solvate thereof, wherein $R^1$ is a 5-10 membered heteroaryl ring substituted with one or more $R^{10}$. In some embodiments is a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), or a pharmaceutically acceptable salt or solvate thereof, wherein $R^1$ is a 5-10 membered heteroaryl ring substituted with one, two, or three $R^{10}$. In some embodiments is a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), or a pharmaceutically acceptable salt or solvate thereof, wherein $R^1$ is a 5-10 membered heteroaryl ring substituted with one, two, or three $R^{10}$, wherein each $R^{10}$ is independently selected from halogen, $C_{1-6}$alkyl, $C_{3-7}$cycloalkyl, $C_{2-9}$heterocycloalkyl, $C_{6-10}$aryl, $C_{1-9}$heteroaryl, $-OR^{12}$, and $N(R^{12})(R^{13})$, wherein $C_{1-6}$alkyl, $C_{3-7}$cycloalkyl, $C_{2-9}$heterocycloalkyl, $C_{6-10}$aryl, and $C_{1-9}$heteroaryl are optionally substituted with one, two, or three $R^{20d}$. In some embodiments is a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), or a pharmaceutically acceptable salt or solvate thereof, wherein $R^1$ is a 5-10 membered heteroaryl ring substituted with one, two, or three $R^{10}$, wherein each $R^{10}$ is independently selected from halogen, $C_{1-6}$alkyl, and $N(R^{12})(R^{13})$, wherein $C_{1-6}$alkyl is optionally substituted with one, two, or three $R^{20d}$. In some embodiments is a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), or a pharmaceutically acceptable salt or solvate thereof, wherein $R^1$ is a 5-10 membered heteroaryl ring substituted with one, two, or three $R^{10}$, wherein each $R^{10}$ is independently selected from halogen and $C_{1-6}$alkyl, wherein $C_{1-6}$alkyl is substituted with one, two, or three $R^{20d}$, and each $R^{20d}$ is halogen. In some embodiments is a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib- 2), (Ib'-2), (Ic-2), or (Ic'-2), or a pharmaceutically acceptable salt or solvate thereof, wherein $R^1$ is an unsubstituted 5-10 membered heteroaryl ring.

In some embodiments is a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), or a pharmaceutically acceptable salt or solvate thereof, wherein $R^1$ is a 3-12 membered cycloalkyl ring optionally substituted with one or more $R^{10}$. In some embodiments is a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), or a pharmaceutically acceptable salt or solvate thereof, wherein $R^1$ is a 3-12 membered cycloalkyl ring substituted with one or more $R^{10}$. In some embodiments is a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), or a pharmaceutically acceptable salt or solvate thereof, wherein $R^1$ is an unsubstituted 3-12 membered cycloalkyl ring.

In some embodiments is a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), or a pharmaceutically acceptable salt or solvate thereof, wherein $R^1$ is a 3-12 membered heterocycloalkyl ring optionally substituted with one or more $R^{10}$. In some embodiments is a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), or a pharmaceutically acceptable salt or solvate thereof, wherein $R^1$ is a 3-12 membered heterocycloalkyl ring substituted with one or more $R^{10}$. In some embodiments is a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), or a pharmaceutically acceptable salt or solvate thereof, wherein $R^1$ is an unsubstituted 3-12 membered heterocycloalkyl ring optionally substituted with one or more $R^{10}$.

In some embodiments is a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), or a pharmaceutically acceptable salt or solvate thereof, wherein $R^4$ is hydrogen. In some embodiments is a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib- 2), (Ib'-2), (Ic-2), or (Ic'-2), or a pharmaceutically acceptable salt or solvate thereof, wherein $R^4$ is $C_{1-6}$alkyl. In some embodiments is a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), or a pharmaceutically acceptable salt or solvate thereof, wherein $R^4$ is —$CH_3$. In some embodiments is a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), or a pharmaceutically acceptable salt or solvate thereof, wherein $R^4$ is $C_{1-6}$haloalkyl.

In embodiments of a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), $R^{20b}$ is $C_{1-6}$alkyl (e.g., methyl, ethyl, or propyl) optionally substituted with one, two, or three —$N(R^{22})(R^{23})$ and $R^{22}$ and $R^{23}$ are independently selected from H and $C_{1-6}$alkyl (e.g., methyl). In embodiments of a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), $R^{20b}$ is $C_{1-6}$alkyl (e.g., methyl, ethyl, or propyl) optionally substituted with one, two, or three —$OR^{21}$ and $R^{21}$ is independently selected from H and $C_{1-6}$alky. In embodiments of a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), $R^{20b}$ is selected from —$CH_2$—$C_{6-10}$aryl and —CN. In embodiments of a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), $R^{20b}$ is selected from oxo and =NH. In embodiments of a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), $R^{20b}$ is $C_{2-9}$heterocycloalkyl. In embodiments of a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), $R^{20b}$ is —C(O)$R^{25}$ and $R^{25}$ is $C_{1-6}$alkyl. In embodiments of a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), $R^{20b}$ is —C(O)$R^{25}$ and $R^{25}$ is $C_{2-6}$heterocycloalkyl optionally substituted with one, two, or three $C_{1-6}$alkyl. In embodiments of a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), $R^{20b}$ is $C_{1-6}$alkyl optionally substituted with one, two, or three groups independently selected from oxo, —$OR^{21}$, and —$N(R^{22})(R^{23})$, $R^{21}$ is H, and $R^{22}$ and $R^{23}$ are independently selected from H and $C_{1-6}$alkyl (e.g., methyl).

In embodiments of a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), $R^{20a}$ is $C_{1-6}$alkyl (e.g., methyl, ethyl, or propyl) optionally substituted with one, two, or three —$N(R^{22})(R^{23})$ and $R^{22}$ and $R^{23}$ are independently selected from H and $C_{1-6}$alkyl (e.g., methyl). In embodiments of a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), $R^{20a}$ is $C_{1-6}$alkyl (e.g., methyl, ethyl, or propyl) optionally substituted with one, two, or three —$OR^{21}$ and $R^{21}$ is independently selected from H and $C_{1-6}$alky. In embodiments of a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), $R^{20a}$ selected from —$CH_2$—$C_{6-10}$aryl and —CN. In embodiments of a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), $R^{20a}$ is selected from oxo and =NH. In embodiments of a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), $R^{20a}$ is $C_{2-9}$heterocycloalkyl. In embodiments of a compound of Formula (I-1), (I'-1), (Ia-1), (Ia'-1), (Ib-1), (Ib'-1), (Ic-1), (Ic'-1), (1-2), (I'-2), (Ia-2), (Ia'-2), (Ib-2), (Ib'-2), (Ic-2), or (Ic'-2), $R^{20a}$ is —C(O)$R^{25}$ and $R^{25}$ is $C_{1-6}$alkyl. In embodiments of a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), $R^{20a}$ is —C(O)$R^{25}$ and $R^{25}$ is $C_{2-6}$heterocycloalkyl optionally substituted with one, two, or three $C_{1-6}$alkyl. In embodiments of a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), $R^{20a}$ is $C_{1-6}$alkyl optionally substituted with one, two, or three groups independently selected from oxo, —$OR^{21}$, and —$N(R^{22})(R^{23})$, $R^{21}$ is H, and $R^{22}$ and $R^{23}$ are independently selected from H and $C_{1-6}$alkyl (e.g., methyl).

In embodiments of a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), $R^2$ is —$NR^{2b}R^{2c}$ and $R^{2b}$ and $R^{2c}$ are selected from hydrogen and $C_{2-5}$heterocycloalkyl. In embodiments of a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), $R^2$ is —$NHR^{2c}$ and $R^{2e}$ is $C_{2-5}$heterocycloalkyl optionally substituted with one, two, or three $R^{20a}$ and $R^{20a}$ is $C_{1-6}$alkyl (e.g., methyl). In embodiments of a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), $R^2$ is —$OR^{2a}$ and $R^{2a}$ is $C_{2-5}$heterocycloalkyl optionally substituted with one, two, or three $R^{20a}$ and $R^{20a}$ is $C_{1-6}$alkyl (e.g., methyl). In embodiments of a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), $R^2$ is —$OR^{2a}$ and $R^{2a}$ is $C_{1-6}$ alkyl (e.g., methyl) optionally substituted with one, two, or three $R^{20a}$ and $R^{20a}$ is $C_{2-5}$heterocycloalkyl. In embodiments of a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), $R^2$ is —$OR^{2a}$ and $R^{2a}$ is $C_{1-6}$alkyl (e.g., methyl) optionally substituted with one, two, or three $R^{20a}$ and $R^{20a}$ is $C_{2-5}$heterocycloalkyl optionally substituted with one, two, or three groups independently selected from halogen and $C_{1-6}$alkyl (e.g., methyl).

In embodiments of a compound of Formula (I-2), (I'-2), (Ia-2), (Ia'-2), (Ib-2), (Ib'-2), (Ic-2), or (Ic'-2), $R^7$ is $C_{1-6}$alkyl (e.g., methyl, ethyl, or propyl) optionally substituted with one, two, or three $R^{20c}$ and $R^{20c}$ is $C_{2-5}$heterocycloalkyl. In embodiments of a compound of Formula (I-2), (I'-2), (Ia-2), (Ia'-2), (Ib-2), (Ib'-2), (Ic-2), or (Ic'-2), $R^7$ is $C_{2-5}$heterocycloalkyl optionally substituted with one, two, or three $R^{20c}$ and —$N(R^{22})(R^{23})$ and $R^{22}$ and $R^{23}$ are independently selected from H and $C_{1-6}$alkyl (e.g., methyl). In embodiments of a compound of Formula (I-2), (I'-2), (Ia-2), (Ia'-2), (Ib-2), (Ib'-2), (Ic-2), or (Ic'-2), $R^7$ is —$OR^{12}$, $R^{12}$ is $C_{2-9}$heterocycloalkyl optionally substituted with one, two, or three $R^{20e}$ and $R^{20e}$ is $C_{1-6}$alkyl (e.g., methyl, ethyl, or propyl). In embodiments of a compound of Formula (I-2), (I'-2), (Ia-2), (Ia'-2), (Ib-2), (Ib'-2), (Ic-2), or (Ic'-2), $R^7$ is —$OR^{12}$, $R^{12}$ is $C_{1-6}$alkyl optionally substituted with one, two, or three $R^{20e}$, and $R^{20e}$ is $C_{2-5}$heterocycloalkyl optionally substituted with one, two, or three $C_{1-6}$ alkyl (e.g., methyl, ethyl, or propyl).

In some embodiments of a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), $R^{10}$ is independently selected from halogen and $C_{1-6}$alkyl optionally substituted with one, two, or three $R^{20d}$ and $R^{20d}$ is independently selected from halogen and $C_{2-5}$heterocycloalkyl optionally substituted with one, two, or three $C_{1-6}$alkyl (e.g., methyl, ethyl, or propyl). In some embodiments of a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), $R^{10}$ is independently selected from halogen and $C_{1-6}$alkyl optionally substituted with one, two, or three $R^{20d}$ and $R^{20d}$ is independently selected from halogen and $C_{2-5}$heterocycloalkyl optionally substituted with one, two, or three —$C(O)OR^{22}$ and $R^{22}$ is $C_{1-6}$alkyl (e.g., methyl, ethyl, propyl, or butyl). In some embodiments of a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), $R^{10}$ is independently selected from halogen and $C_{1-6}$alkyl optionally substituted with one, two, or three $R^{20d}$ and $R^{20d}$ is independently selected from halogen and —$OR^{21}$, wherein $R^{21}$ is $C_{2-5}$heterocycloalkyl optionally substituted with one, two, or three $C_{1-6}$alkyl (e.g., methyl, ethyl, propyl, or butyl). In some embodiments of a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), $R^1$ is

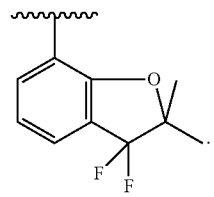

In some embodiments of a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), $R^{10}$ is independently selected from halogen and $C_{1-6}$alkyl optionally substituted with one, two, or three $R^{20d}$ and $R^{20d}$ is independently selected from halogen and $C_{3-5}$cycloalkyl optionally substituted with one, two, or three —$N(R^{22})(R^{23})$, wherein $R^{22}$ and $R^{23}$ are each independently selected hydrogen and $C_{1-6}$alkyl (e.g., methyl, ethyl, or propyl).

In some embodiments of a compound of Formula (I-1), $R^{10}$ is independently selected from halogen and $C_{1-6}$ alkyl-O—$C_{1-6}$alkyl optionally substituted with one, two, or three $R^{20d}$ and $R^{20d}$ is independently selected from halogen and —$N(R^{22})(R^{23})$, wherein $R^{22}$ and $R^{23}$ are each independently selected hydrogen and $C_{1-6}$alkyl (e.g., methyl, ethyl, or propyl).

In some embodiments is a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), or a pharmaceutically acceptable salt or solvate thereof, wherein $R^1$ is a 6-10 membered aryl ring substituted with one or more $R^{10}$. In some embodiments is a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), or a pharmaceutically acceptable salt or solvate thereof, wherein $R^1$ is phenyl substituted with one or more $R^{10}$. In some embodiments is a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), or a pharmaceutically acceptable salt or solvate thereof, wherein $R^1$ is phenyl substituted with one, two, or three $R^{10}$. In some embodiments is a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), or a pharmaceutically acceptable salt or solvate thereof, wherein $R^1$ is a 5-10 membered heteroaryl ring are substituted with one or more $R^{10}$. In some embodiments is a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib- 2), (Ib'-2), (Ic-2), or (Ic'-2), or a pharmaceutically acceptable salt or solvate thereof, wherein $R^1$ is a 5-10 membered heteroaryl ring are substituted with one, two, or three $R^{10}$. In some embodiments is a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), or a pharmaceutically acceptable salt or solvate thereof, wherein each $R^{10}$ is independently selected from halogen, $C_{1-6}$alkyl, $C_{3-7}$cycloalkyl, $C_{2-9}$heterocycloalkyl, $C_{6-10}$aryl, $C_{1-9}$heteroaryl, —$OR^{12}$, and $N(R^{12})(R^{13})$, wherein $C_{1-6}$alkyl, $C_{3-7}$cycloalkyl, $C_{2-9}$heterocycloalkyl, $C_{6-10}$aryl, and $C_{1-9}$heteroaryl are optionally substituted with one, two, or three $R^{20d}$. In some embodiments is a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), or a pharmaceutically acceptable salt or solvate thereof, wherein each $R^{10}$ is independently selected from halogen, $C_{1-6}$alkyl, and $N(R^{12})(R^{13})$, wherein $C_{1-6}$alkyl is optionally substituted with one, two, or three $R^{20d}$. In some embodiments is a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), or a pharmaceutically acceptable salt or solvate thereof, wherein each $R^{10}$ is independently selected from halogen, $C_{1-6}$alkyl, and $N(R^{12})(R^{13})$, wherein $C_{1-6}$alkyl is substituted with one, two, or three $R^{20d}$, and each $R^{20d}$ is halogen.

In some embodiments is a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), wherein $R^1$ is benzothiazolyl optionally substituted with one or more $R^{10}$. In some embodiments is a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib- 2), (Ib'-2), (Ic-2), or (Ic'-2), wherein $R^1$ is 1H-benzo[d]imidazolyl optionally substituted with one or more $R^{10}$. In some embodiments is a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), wherein $R^1$ is benzo[c]thiophenyl optionally substituted with one or more $R^{10}$. In some embodiments is a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), wherein $R^1$ is benzo[b]thiophenyl optionally substituted with one or more $R^{10}$. In some embodiments is a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), wherein $R^1$ is indanyl optionally substituted with one or more $R^{10}$. In some embodiments is a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), wherein $R^1$ is indenyl optionally substituted with one or more $R^{10}$. In some embodiments is a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), wherein $R^1$ is tetralinyl optionally substituted with one or more $R^{10}$. In some embodiments is a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), wherein $R^1$ is coumaranyl optionally substituted with one or more $R^{10}$. In some embodiments is a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), wherein $R^1$ is furanyl optionally substituted with one or more $R^{10}$. In some embodiments is a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), wherein $R^1$ is thiophenyl optionally substituted with one or more $R^{10}$. In some embodiments is a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), wherein $R^1$ is oxazolyl optionally substituted with one or more $R^{10}$. In some embodiments is a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib- 2), (Ib'-2), (Ic-2), or (Ic'-2), wherein $R^1$ is thiazolyl optionally substituted with one or more $R^{10}$. In some embodiments is a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), wherein $R^1$ is 1H-indazolyl optionally substituted with one or more $R^{10}$. In some embodiments is a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), wherein $R^1$ is imidazo[1,2-a]pyridinyl optionally substituted with one or more $R^{10}$. In some embodiments is a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), wherein $R^1$ is pyrazolyl optionally substituted with one or more $R^{10}$. In some embodiments is a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), wherein $R^1$ is 1H-indolyl optionally substituted with one or more $R^{10}$. In some embodiments is a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), wherein $R^1$ is pyridinyl optionally substituted with one or more $R^{10}$. In some embodiments is a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), wherein $R^1$ is pyrimidinyl optionally substituted with one or more $R^{10}$. In some embodiments is a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), wherein $R^1$ is pyrizinyl optionally substituted with one or more $R^{10}$. In some embodiments is a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), wherein $R^1$ is 1H-imidazolyl optionally substituted with one or more $R^{10}$. In some embodiments is a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), wherein $R^1$ is 1,4-benzodioxanyl optionally substituted with one or more $R^{10}$. In some embodiments is a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), wherein $R^1$ is 3,4-dihydrobenzo[1,4]oxazinyl optionally substituted with one or more $R^{10}$. In some embodiments is a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib- 2), (Ib'-2), (Ic-2), or (Ic'-2), wherein $R^1$ is benzo[b]furanyl optionally substituted with one or more $R^{10}$. In some embodiments is a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), wherein $R^1$ is benzo[c]furanyl optionally substituted with one or more $R^{10}$. In some embodiments is a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), wherein $R^1$ is phenyl optionally substituted with one or more $R^{10}$. In some embodiments is a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), wherein $R^1$ is naphthalenyl optionally substituted with one or more $R^{10}$.

In some embodiments is a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), wherein $R^1$ is (benzo[d][1,3]dioxol-4-yl, 1,8a-dihydroimidazo[1,2-a]pyridin-8-yl, 1H- indazol-4-yl, 1H-indazol-5-yl, 1H-indazol-6-yl, 1H-indazol-7-yl, 1H-inden-4-yl, 1H-inden-5-yl, 1H-inden-6-yl, 1H-inden-7-yl, 2,3-dihydro-1H-inden-4-yl, 2,3-dihydro-1H-inden-5-yl, 2,3-dihydrobenzo[b][1,4]dioxin-5-yl, 2,3-dihydrobenzo[b][1,4]dioxin-6-yl, 2,3-dihydrobenzofuran-4-yl, 2,3-dihydrobenzofuran-5-yl, 2,3-dihydrobenzofuran-6-yl, 2,3-dihydrobenzofuran-7-yl, 3,4-dihydro-2H-benzo[b][1,4]oxazin-5-yl, 3,4-dihydro-2H-benzo[b][1,4]oxazin-6-yl, 3,4-dihydro-2H-benzo[b][1,4]oxazin-7-yl, 3,4-dihydro-2H-benzo[b][1,4]oxazin-8-yl, 4-(benzo[d][1,3]dioxol-5-yl, 5,6,7,8-tetrahydronaphthalen-1-yl, 5,6,7,8-tetrahydronaphthalen-2-yl, benzo[b]thiophen- 4-yl, benzo[b]thiophen-5-yl, benzo[b]thiophen-6-yl, benzo[b]thiophen-7-yl, benzo[d]thiazol-4-yl, benzo[d]thiazol-5-yl, benzo[d]thiazol-6-yl, benzo[d]thiazol-7-yl, benzofuran-4-yl, benzofuran-5-yl, benzofuran-6-yl, benzofuran-7-yl, chroman-5-yl, chroman-6-yl, chroman-7-yl, chroman-8-yl, furan-2-yl, furan-3-yl, imidazo[1,2-a]pyridin-5-yl, imidazo[1,2-a]pyridin-6-yl, imidazo[1,2-a]pyridin-7-yl, naphthalen-1-yl, naphthalen-2-yl, oxazol-2-yl, oxazol-4-yl, oxazol-5-yl, pyrazin-2-yl, pyridazin-3-yl, pyridazin-4-yl, pyridin-2-yl, pyridin-3-yl, pyridin-4-yl, pyrimidin-4-yl, pyrimidin-4-yl, pyrimidin-5-yl, thiazol-2-yl, thiazol-4-yl, thiazol-5-yl, or thiophen-3-yl, any of which is optionally substituted with one or more $R^{10}$.

In some embodiments of a compound of Formula (I-1), (I'-1) (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), $R^1$ is

[chemical structures]

wherein each $R^{20d}$ is as described herein.

In embodiments of a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), $R^{20d}$ is $C_{1-6}$alkyl optionally substituted with one, two, or three groups independently selected from halogen and —$OR^{21}$. In embodiments of a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), $R^{20d}$ is $C_{1-6}$alkyl optionally substituted with one, two, or three groups independently selected from halogen and —OH. In embodiments of a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), $R^{20d}$ is $C_{1-6}$alkyl optionally substituted with one, two, or three groups independently selected from F and —OH. In embodiments of a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), $R^{20d}$ is $C_{1-6}$alkyl optionally substituted with one —OH. In embodiments of a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), $R^{20d}$ is $C_{1-6}$alkyl optionally substituted with one, two, or three F.

In embodiments of a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), $R^{20d}$ is $C_{1-3}$alkyl optionally substituted with one, two, or three groups independently selected from halogen and —$OR^{21}$. In embodiments of a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), $R^{20d}$ is $C_{1-3}$alkyl optionally substituted with one, two, or three groups independently selected from halogen and —OH. In embodiments of a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), $R^{20d}$ is $C_{1-3}$alkyl optionally substituted with one, two, or three groups independently selected from F and —OH. In embodiments of a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), $R^{20d}$ is $C_{1-3}$alkyl substituted with one, two, or three groups independently selected from halogen and —$OR^{21}$. In embodiments of a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), $R^{20d}$ is $C_{1-3}$alkyl substituted with one, two, or three groups independently selected from halogen and —OH. In embodiments of a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), $R^{20d}$ is $C_{1-3}$alkyl substituted with one, two, or three groups independently selected from F and —OH. In embodiments of a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), $R^{20d}$ is $C_{1-3}$alkyl substituted with one —OH. In embodiments of a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib- 2), (Ib'-2), (Ic-2), or (Ic'-2), $R^{20d}$ is $C_{1-3}$alkyl substituted with one, two, or three F.

In embodiments of a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), $R^{20d}$ is isopropyl optionally substituted with one, two, or three groups independently selected from halogen and —$OR^{21}$. In embodiments of a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), $R^{20d}$ is isopropyl optionally substituted with one, two, or three groups independently selected from halogen and —OH. In embodiments of a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), $R^{20d}$ is isopropyl optionally substituted with one, two, or three groups independently selected from F and —OH. In embodiments of a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), $R^{20d}$ is isopropyl substituted with one, two, or three groups independently selected from halogen and —$OR^{21}$. In embodiments of a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), $R^{20d}$ is isopropyl substituted with one, two, or three groups independently selected from halogen and —OH. In embodiments of a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), $R^{20d}$ is isopropyl substituted with one, two, or three groups independently selected from F and —OH. In embodiments of a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), $R^{20d}$ is isopropyl substituted with one —OH. In embodiments of a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), $R^{20d}$ is isopropyl substituted with one, two, or three F.

In embodiments of a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), $R^{20d}$ is ethyl optionally substituted with one, two, or three groups independently selected from halogen and —OR$^{21}$. In embodiments of a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), R$^{20d}$ is ethyl optionally substituted with one, two, or three groups independently selected from halogen and —OH. In embodiments of a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), R$^{20d}$ is ethyl optionally substituted with one, two, or three groups independently selected from F and —OH. In embodiments of a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), R$^{20d}$ is ethyl substituted with one, two, or three groups independently selected from halogen and —OR$^{21}$. In embodiments of a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), R$^{20d}$ is ethyl substituted with one, two, or three groups independently selected from halogen and —OH. In embodiments of a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), R$^{20d}$ is ethyl substituted with one, two, or three groups independently selected from F and —OH. In embodiments of a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), R$^{20d}$ is ethyl substituted with one —OH. In embodiments of a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), R$^{20d}$ is ethyl substituted with one, two, or three F.

In embodiments of a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), R$^{20d}$ is methyl optionally substituted with one, two, or three groups independently selected from halogen and —OR$^{21}$. In embodiments of a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), R$^{20d}$ is methyl optionally substituted with one, two, or three groups independently selected from halogen and —OH. In embodiments of a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), R$^{20d}$ is methyl optionally substituted with one, two, or three groups independently selected from F and —OH. In embodiments of a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), R$^{20d}$ is methyl substituted with one, two, or three groups independently selected from halogen and —OR$^{21}$. In embodiments of a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), R$^{20d}$ is methyl substituted with one, two, or three groups independently selected from halogen and —OH. In embodiments of a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), R$^{20d}$ is methyl substituted with one, two, or three groups independently selected from F and —OH. In embodiments of a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), R$^{20d}$ is methyl substituted with one —OH. In embodiments of a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), R$^{20d}$ is methyl substituted with one, two, or three F.

In embodiments of a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), R$^{20d}$ is C$_{2-9}$heterocycloalkyl optionally substituted with one, two, or three groups independently selected from C$_{1-6}$alkyl, C$_{1-6}$haloalkyl, C$_{1-6}$alkoxy, and C$_{1-6}$haloalkoxy. In embodiments of a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), R$^{20d}$ is C$_{2-9}$heterocycloalkyl optionally substituted with one, two, or three groups independently selected from C$_{1-4}$alkyl, C$_{1-4}$haloalkyl, C$_{1-4}$alkoxy, and C$_{1-4}$haloalkoxy. In embodiments of a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), R$^{20d}$ is C$_{2-9}$heterocycloalkyl optionally substituted with one, two, or three groups independently selected from C$_{1-3}$alkyl, C$_{1-3}$haloalkyl, C$_{1-3}$alkoxy, and C$_{1-3}$haloalkoxy. In embodiments of a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), R$^{20d}$ is C$_{2-9}$heterocycloalkyl optionally substituted with one C$_{1-6}$alkyl or one C$_{1-6}$haloalkyl. In embodiments of a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), R$^{21d}$ is C$_{2-9}$heterocycloalkyl optionally substituted with one C$_{1-3}$alkyl or one C$_{1-3}$haloalkyl. In embodiments of a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), R$^{20d}$ is C$_{2-9}$heterocycloalkyl optionally substituted with one C$_{1-6}$alkyl. In embodiments of a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), R$^{20d}$ is C$_{2-9}$heterocycloalkyl optionally substituted with one C$_{1-3}$ alkyl. In embodiments of a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), R$^{20d}$ is C$_{2-9}$heterocycloalkyl optionally substituted with one methyl. In embodiments of a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), R$^{20d}$ is C$_{2-9}$heterocycloalkyl optionally substituted with one ethyl. In embodiments of a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), R$^{20d}$ is C$_{2-9}$heterocycloalkyl optionally substituted with one propyl. In embodiments of a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), R$^{20d}$ is C$_{2-9}$heterocycloalkyl optionally substituted with one isopropyl. In embodiments of a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), R$^{20d}$ is C$_{2-9}$heterocycloalkyl optionally substituted with one butyl. In embodiments of a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), R$^{20d}$ is C$_{2-9}$heterocycloalkyl optionally substituted with one tert-butyl.

In embodiments of a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), R$^{20d}$ is C$_{5-9}$heterocycloalkyl optionally substituted with one, two, or three groups independently selected from C$_{1-6}$alkyl, C$_{1-6}$haloalkyl, C$_{1-6}$alkoxy, and C$_{1-6}$haloalkoxy. In embodiments of a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), R$^{20d}$ is C$_{5-9}$heterocycloalkyl optionally substituted with one, two, or three groups independently selected from $C_{1-4}$alkyl, $C_{1-4}$haloalkyl, $C_{1-4}$alkoxy, and $C_{1-4}$haloalkoxy. In embodiments of a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), $R^{20d}$ is $C_{5-9}$heterocycloalkyl optionally substituted with one, two, or three groups independently selected from $C_{1-3}$alkyl, $C_{1-3}$haloalkyl, $C_{1-3}$alkoxy, and $C_{1-3}$haloalkoxy. In embodiments of a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), $R^{20d}$ is $C_{5-9}$heterocycloalkyl optionally substituted with one $C_{1-6}$alkyl or one $C_{1-6}$haloalkyl. In embodiments of a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), $R^{20d}$ is $C_{5-9}$heterocycloalkyl optionally substituted with one $C_{1-3}$alkyl or one $C_{1-3}$haloalkyl. In embodiments of a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), $R^{20d}$ is $C_{5-9}$heterocycloalkyl optionally substituted with one $C_{1-6}$alkyl. In embodiments of a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), $R^{20d}$ is $C_{5-9}$heterocycloalkyl optionally substituted with one $C_{1-3}$ alkyl. In embodiments of a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), $R^{20d}$ is $C_{5-9}$heterocycloalkyl optionally substituted with one methyl. In embodiments of a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), $R^{20d}$ is $C_{5-9}$heterocycloalkyl optionally substituted with one ethyl. In embodiments of a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), $R^{20d}$ is $C_{5-9}$heterocycloalkyl optionally substituted with one propyl. In embodiments of a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), $R^{20d}$ is $C_{5-9}$heterocycloalkyl optionally substituted with one isopropyl. In embodiments of a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), $R^{20d}$ is $C_{5-9}$heterocycloalkyl optionally substituted with one butyl. In embodiments of a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), $R^{20d}$ is $C_{5-9}$heterocycloalkyl optionally substituted with one tert-butyl.

In embodiments of a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), $R^{20d}$ is $C_{2-6}$heterocycloalkyl optionally substituted with one, two, or three groups independently selected from $C_{1-6}$alkyl, $C_{1-6}$haloalkyl, $C_{1-6}$alkoxy, and $C_{1-6}$haloalkoxy. In embodiments of a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), $R^{20d}$ is $C_{2-6}$heterocycloalkyl optionally substituted with one, two, or three groups independently selected from $C_{1-4}$alkyl, $C_{1-4}$haloalkyl, $C_{1-4}$alkoxy, and $C_{1-4}$haloalkoxy. In embodiments of a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), $R^{20d}$ is $C_{2-6}$heterocycloalkyl optionally substituted with one, two, or three groups independently selected from $C_{1-3}$alkyl, $C_{1-3}$haloalkyl, $C_{1-3}$alkoxy, and $C_{1-3}$haloalkoxy. In embodiments of a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), $R^{20d}$ is $C_{2-6}$heterocycloalkyl optionally substituted with one $C_{1-6}$alkyl or one $C_{1-6}$haloalkyl. In embodiments of a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), $R^{20d}$ is $C_{2-6}$heterocycloalkyl optionally substituted with one $C_{1-3}$alkyl or one $C_{1-3}$haloalkyl. In embodiments of a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), $R^{20d}$ is $C_{2-6}$heterocycloalkyl optionally substituted with one $C_{1-6}$alkyl. In embodiments of a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), $R^{20d}$ is $C_{2-6}$heterocycloalkyl optionally substituted with one $C_{1-3}$ alkyl. In embodiments of a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), $R^{20d}$ is $C_{2-6}$heterocycloalkyl optionally substituted with one methyl. In embodiments of a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), $R^{20d}$ is $C_{2-6}$heterocycloalkyl optionally substituted with one ethyl. In embodiments of a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), $R^{20d}$ is $C_{2-6}$heterocycloalkyl optionally substituted with one propyl. In embodiments of a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), $R^{20d}$ is $C_{2-6}$heterocycloalkyl optionally substituted with one isopropyl. In embodiments of a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), $R^{20d}$ is $C_{2-6}$heterocycloalkyl optionally substituted with one butyl. In embodiments of a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), $R^{20d}$ is $C_{2-6}$heterocycloalkyl optionally substituted with one tert-butyl.

In embodiments of a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), $R^{20d}$ is $C_{4-5}$heterocycloalkyl optionally substituted with one, two, or three groups independently selected from $C_{1-6}$alkyl, $C_{1-6}$haloalkyl, $C_{1-6}$alkoxy, and $C_{1-6}$haloalkoxy. In embodiments of a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), $R^{20d}$ is $C_{4-5}$heterocycloalkyl optionally substituted with one, two, or three groups independently selected from $C_{1-4}$alkyl, $C_{1-4}$haloalkyl, $C_{1-4}$alkoxy, and $C_{1-4}$haloalkoxy. In embodiments of a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), $R^{20d}$ is $C_{4-5}$heterocycloalkyl optionally substituted with one, two, or three groups independently selected from $C_{1-3}$alkyl, $C_{1-3}$haloalkyl, $C_{1-3}$alkoxy, and $C_{1-3}$haloalkoxy. In embodiments of a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), $R^{20d}$ is $C_{4-5}$heterocycloalkyl optionally substituted with one $C_{1-6}$alkyl or one $C_{1-6}$haloalkyl. In embodiments of a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), $R^{21d}$ is $C_{4-5}$heterocycloalkyl optionally substituted with one $C_{1-3}$alkyl or one $C_{1-3}$haloalkyl. In embodiments of a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), $R^{20d}$ is $C_{4-5}$heterocycloalkyl optionally substituted with one $C_{1-6}$alkyl. In embodiments of a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), $R^{20d}$ is $C_{4-5}$heterocycloalkyl optionally substituted with one $C_{1-3}$ alkyl. In embodiments of a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), $R^{20d}$ $C_{4-5}$heterocycloalkyl optionally substituted with one methyl. In embodiments of a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), $R^{20d}$ is $C_{4-5}$heterocycloalkyl optionally substituted with one ethyl. In embodiments of a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), $R^{20d}$ is $C_{4-5}$heterocycloalkyl optionally substituted with one propyl. In embodiments of a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), $R^{20d}$ is $C_{4-5}$heterocycloalkyl optionally substituted with one isopropyl. In embodiments of a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib- 2), (Ib'-2), (Ic-2), or (Ic'-2), $R^{20d}$ is $C_{4-5}$heterocycloalkyl optionally substituted with one butyl. In embodiments of a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), $R^{20d}$ is $C_{4-5}$heterocycloalkyl optionally substituted with one tert-butyl.

In embodiments of a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), $R^{20d}$ is pyrrolidinyl optionally substituted with one, two, or three groups independently selected from $C_{1-6}$alkyl, $C_{1-6}$haloalkyl, $C_{1-6}$alkoxy, and $C_{1-6}$haloalkoxy. In embodiments of a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), $R^{20d}$ is pyrrolidinyl optionally substituted with one, two, or three groups independently selected from $C_{1-4}$alkyl, $C_{1-4}$haloalkyl, $C_{1-4}$alkoxy, and $C_{1-4}$ haloalkoxy. In embodiments of a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), $R^{20d}$ is pyrrolidinyl optionally substituted with one, two, or three groups independently selected from $C_{1-3}$alkyl, $C_{1-3}$haloalkyl, $C_{1-3}$alkoxy, and $C_{1-3}$haloalkoxy. In embodiments of a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), $R^{20d}$ is pyrrolidinyl optionally substituted with one $C_{1-6}$alkyl or one $C_{1-6}$haloalkyl. In embodiments of a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), $R^{20d}$ is pyrrolidinyl optionally substituted with one $C_{1-3}$alkyl or one $C_{1-3}$haloalkyl. In embodiments of a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), $R^{20d}$ is pyrrolidinyl optionally substituted with one $C_{1-6}$alkyl. In embodiments of a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib- 2), (Ib'-2), (Ic-2), or (Ic'-2), $R^{20d}$ is pyrrolidinyl optionally substituted with one $C_{1-3}$alkyl. In embodiments of a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), $R^{20d}$ pyrrolidinyl optionally substituted with one methyl. In embodiments of a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), $R^{20d}$ is pyrrolidinyl optionally substituted with one ethyl. In embodiments of a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib- 2), (Ib'-2), (Ic-2), or (Ic'-2), $R^{20d}$ is pyrrolidinyl optionally substituted with one propyl. In embodiments of a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), $R^{20d}$ is pyrrolidinyl optionally substituted with one isopropyl. In embodiments of a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), $R^{20d}$ is pyrrolidinyl optionally substituted with one butyl. In embodiments of a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib- 2), (Ib'-2), (Ic-2), or (Ic'-2), $R^{20d}$ is pyrrolidinyl optionally substituted with one tert-butyl.

In embodiments of a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), $R^{20d}$ is piperidinyl optionally substituted with one, two, or three groups independently selected from $C_{1-6}$alkyl, $C_{1-6}$haloalkyl, $C_{1-6}$alkoxy, and $C_{1-6}$haloalkoxy. In embodiments of a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), $R^{20d}$ is piperidinyl optionally substituted with one, two, or three groups independently selected from $C_{1-4}$alkyl, $C_{1-4}$haloalkyl, $C_{1-4}$alkoxy, and $C_{1-4}$ haloalkoxy. In embodiments of a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), $R^{20d}$ is piperidinyl optionally substituted with one, two, or three groups independently selected from $C_{1-3}$alkyl, $C_{1-3}$haloalkyl, $C_{1-3}$alkoxy, and $C_{1-3}$haloalkoxy. In embodiments of a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), $R^{20d}$ is piperidinyl optionally substituted with one $C_{1-6}$alkyl or one $C_{1-6}$haloalkyl. In embodiments of a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), $R^{20d}$ is piperidinyl optionally substituted with one $C_{1-3}$alkyl or one $C_{1-3}$ haloalkyl. In embodiments of a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), $R^{20d}$ is piperidinyl optionally substituted with one $C_{1-6}$alkyl. In embodiments of a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), $R^{20d}$ is piperidinyl optionally substituted with one $C_{1-3}$alkyl. In embodiments of a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib'-2), (Ic-2), or (Ic'-2), $R^{20d}$ piperidinyl optionally substituted with one methyl. In embodiments of a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), $R^{20d}$ is piperidinyl optionally substituted with one ethyl. In embodiments of a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), $R^{20d}$ is piperidinyl optionally substituted with one propyl. In embodiments of a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), $R^{20d}$ is piperidinyl optionally substituted with one isopropyl. In embodiments of a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), $R^{20d}$ is piperidinyl optionally substituted with one butyl. In embodiments of a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), $R^{20d}$ is piperidinyl optionally substituted with one tert-butyl.

In embodiments of a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), $R^{20d}$ is piperazinyl optionally substituted with one, two, or three groups independently selected from $C_{1-6}$alkyl, $C_{1-6}$haloalkyl, $C_{1-6}$alkoxy, and $C_{1-6}$haloalkoxy. In embodiments of a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), $R^{20d}$ is piperazinyl optionally substituted with one, two, or three groups independently selected from $C_{1-4}$alkyl, $C_{1-4}$haloalkyl, $C_{1-4}$alkoxy, and $C_{1-4}$ haloalkoxy. In embodiments of a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), $R^{20d}$ is piperazinyl optionally substituted with one, two, or three groups independently selected from $C_{1-3}$alkyl, $C_{1-3}$haloalkyl, $C_{1-3}$alkoxy, and $C_{1-3}$haloalkoxy. In embodiments of a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), $R^{20d}$ is piperazinyl optionally substituted with one $C_{1-6}$alkyl or one $C_{1-6}$haloalkyl. In embodiments of a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), $R^{20d}$ is piperazinyl optionally substituted with one $C_{1-3}$alkyl or one $C_{1-3}$ haloalkyl. In embodiments of a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), $R^{20d}$ is piperazinyl optionally substituted with one $C_{1-6}$alkyl. In embodiments of a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), $R^{20d}$ is piperazinyl optionally substituted with one $C_{1-3}$alkyl. In embodiments of a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), $R^{20d}$ piperazinyl optionally substituted with one methyl. In embodiments of a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), $R^{20d}$ is piperidinyl optionally substituted with one ethyl. In embodiments of a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), $R^{20d}$ is piperazinyl optionally substituted with one propyl. In embodiments of a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), $R^{20d}$ is piperazinyl optionally substituted with one isopropyl. In embodiments of a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), $R^{20d}$ is piperidinyl optionally substituted with one butyl. In embodiments of a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), $R^{20d}$ is piperazinyl optionally substituted with one tert-butyl.

In some embodiments is a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), wherein $R^1$ is In some embodiments is a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), wherein $R^1$ is

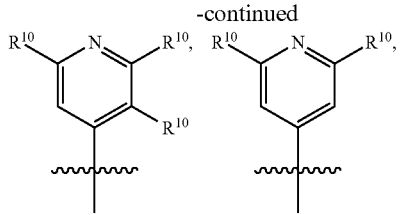
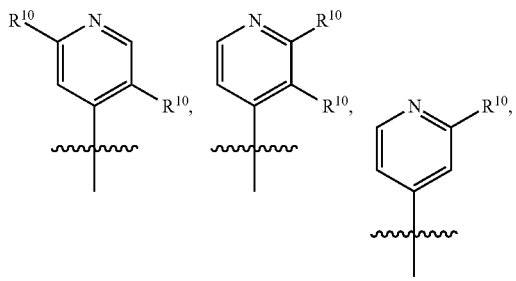
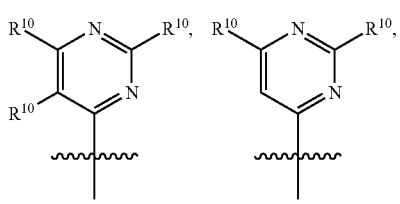
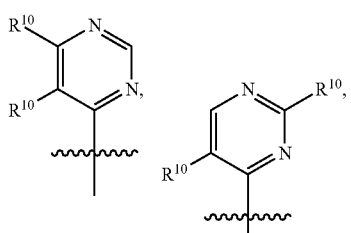
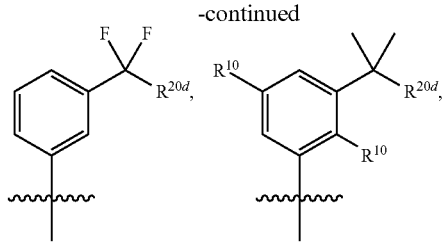
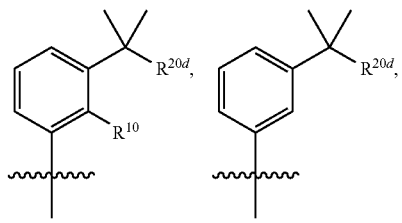
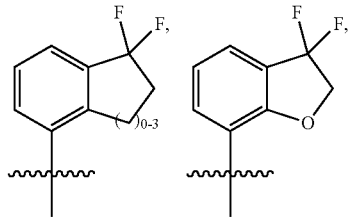
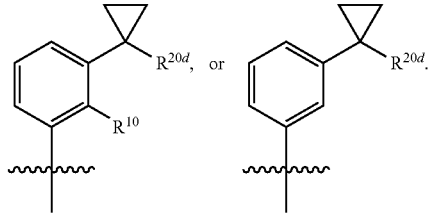
In some embodiments of a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), $R^1$ is
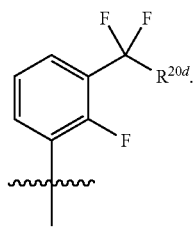
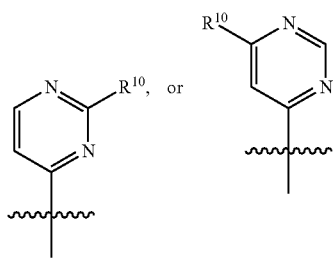
In some embodiments is a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), wherein $R^1$ is
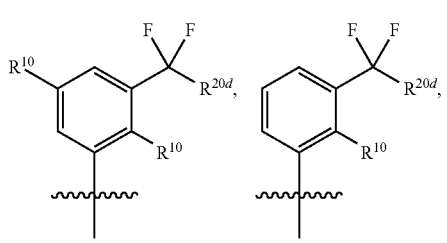
In some embodiments of a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), $R^1$ is
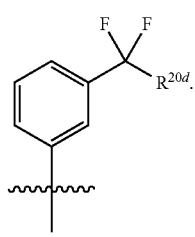

In some embodiments of a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), $R^1$ is

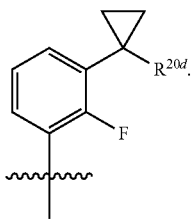

In some embodiments of a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), $R^1$ is

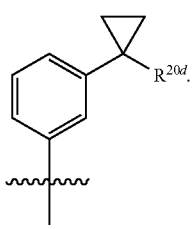

In some embodiments of a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), $R^1$ is

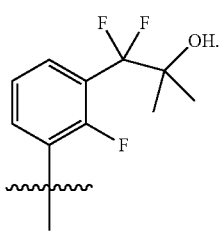 [SMILES: *c1cccc(C(F)(F)C(C)(C)O)c1F]

In some embodiments of a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), $R^1$ is

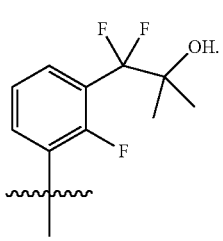 [SMILES: *c1cccc(C(F)(F)C(C)(C)O)c1F]

In some embodiments of a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib- 2), (Ib'-2), (Ic-2), or (Ic'-2), $R^1$ is

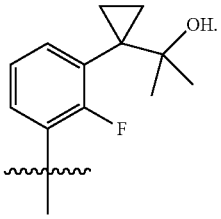 [SMILES: *c1cccc(C2(C(C)(C)O)CC2)c1F]

In some embodiments of a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), $R^1$ is

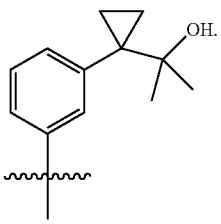 [SMILES: *c1cccc(C2(C(C)(C)O)CC2)c1]

In some embodiments of a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib- 2), (Ib'-2), (Ic-2), or (Ic'-2), $R^1$ is

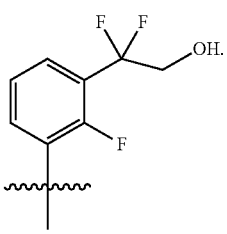 [SMILES: *c1cccc(C(F)(F)CO)c1F]

In some embodiments of a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), $R^1$ is

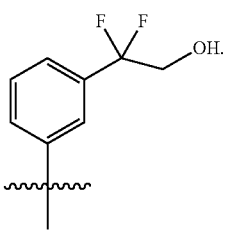 [SMILES: *c1cccc(C(F)(F)CO)c1]

In some embodiments of a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib- 2), (Ib'-2), (Ic-2), or (Ic'-2), $R^1$ is

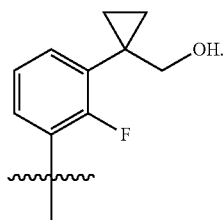 [SMILES: *c1cccc(C2(CO)CC2)c1F]

In some embodiments of a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), R¹ is

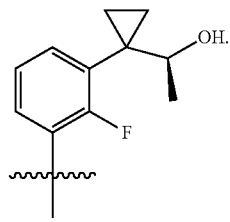

In some embodiments of a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), R¹ is

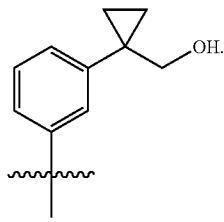 [SMILES: *c1cccc(C2(CO)CC2)c1]

In some embodiments of a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib- 2), (Ib'-2), (Ic-2), or (Ic'-2), R¹ is

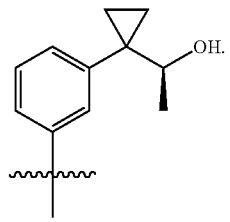

In some embodiments of a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib- 2), (Ib'-2), (Ic-2), or (Ic'-2), R¹ is

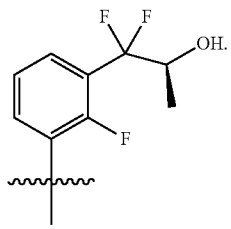 [SMILES: *c1cccc(C(F)(F)[C@H](C)O)c1F]

In some embodiments of a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), R¹ is

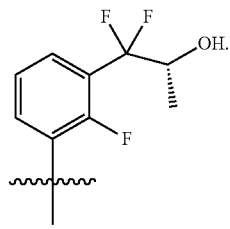

In some embodiments of a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), R¹ is

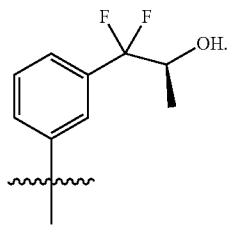 [SMILES: *c1cccc(C(F)(F)[C@H](C)O)c1]

In some embodiments of a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib- 2), (Ib'-2), (Ic-2), or (Ic'-2), R¹ is

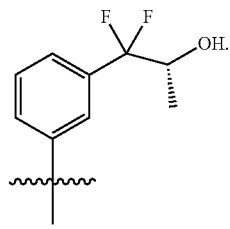 [SMILES: *c1cccc(C(F)(F)[C@@H](C)O)c1]

In some embodiments of a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib- 2), (Ib'-2), (Ic-2), or (Ic'-2), R¹ is

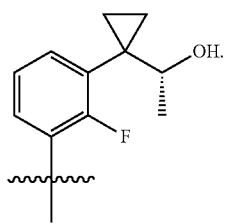 [SMILES: *c1cccc(C2([C@@H](C)O)CC2)c1F]

In some embodiments of a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), R¹ is

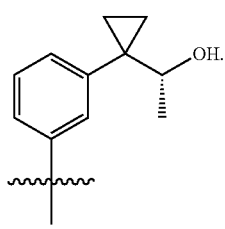 [SMILES: *c1cccc(C2([C@@H](C)O)CC2)c1]

In some embodiments of a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), R¹ is

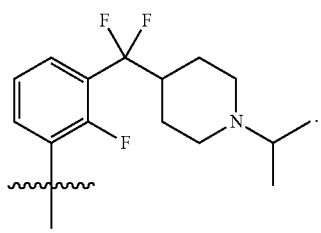 [SMILES: *c1cccc(C(F)(F)C2CCN(C(C)C)CC2)c1F]

In some embodiments of a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), R¹ is

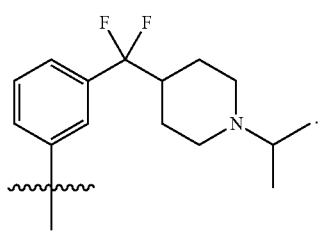 [SMILES: *c1cccc(C(F)(F)C2CCN(C(C)C)CC2)c1]

In some embodiments of a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), R¹ is

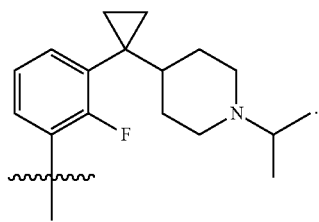 [SMILES: *c1cccc(C2(C3CCN(C(C)C)CC3)CC2)c1F]

In some embodiments of a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), R¹ is

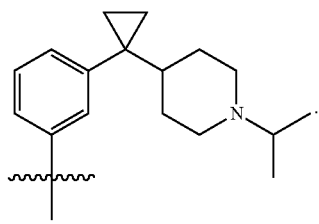 [SMILES: *c1cccc(C2(C3CCN(C(C)C)CC3)CC2)c1]

In some embodiments is a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), wherein R¹ is

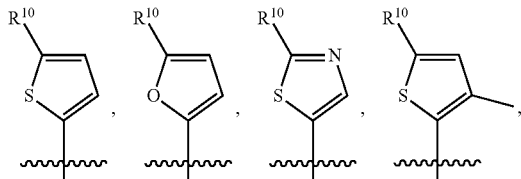

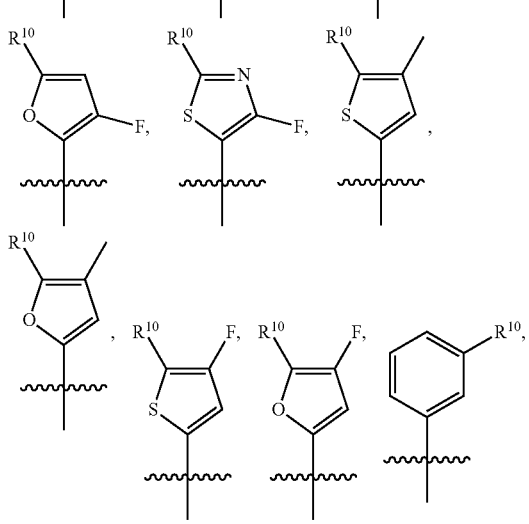

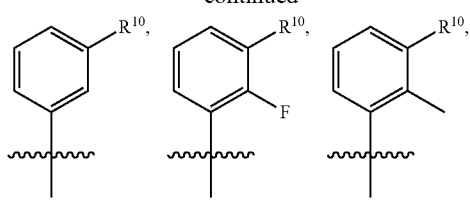
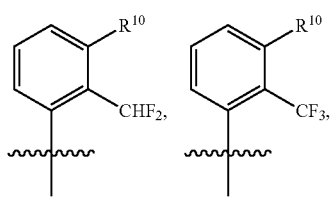
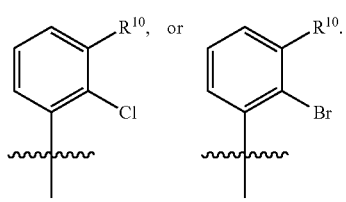
In some embodiments is a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), wherein R¹ is
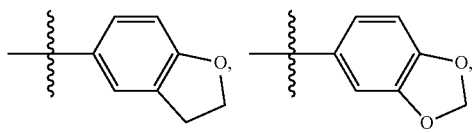
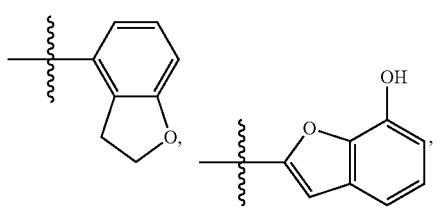
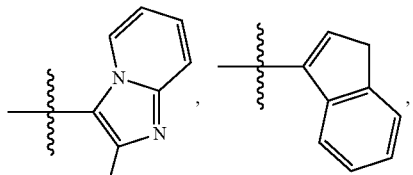
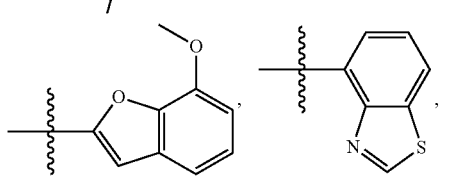
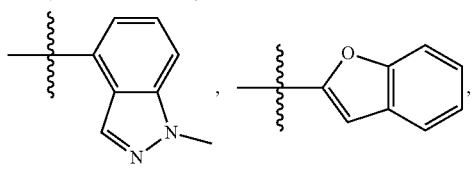
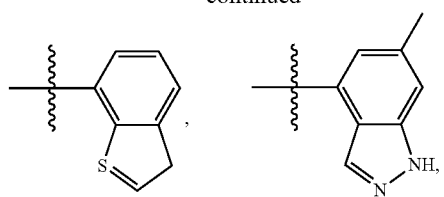
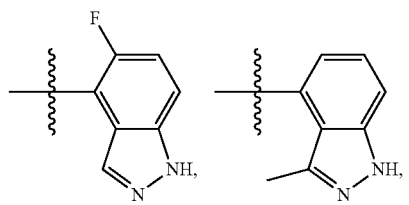
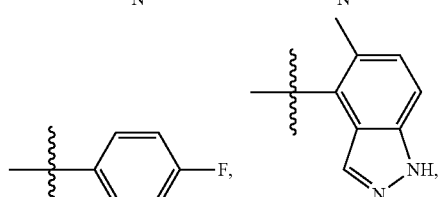
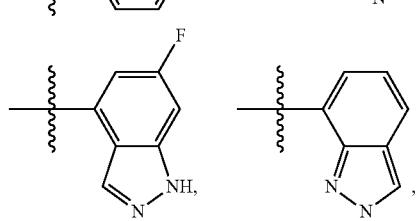

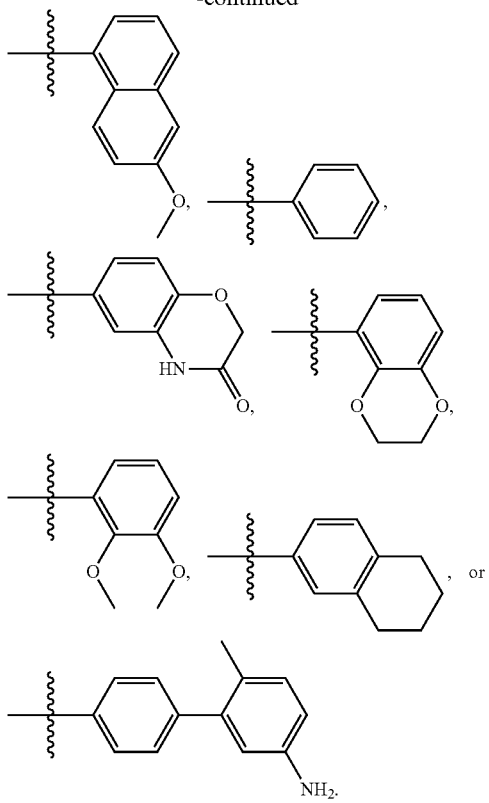
In some embodiments is a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), wherein $R^1$ is
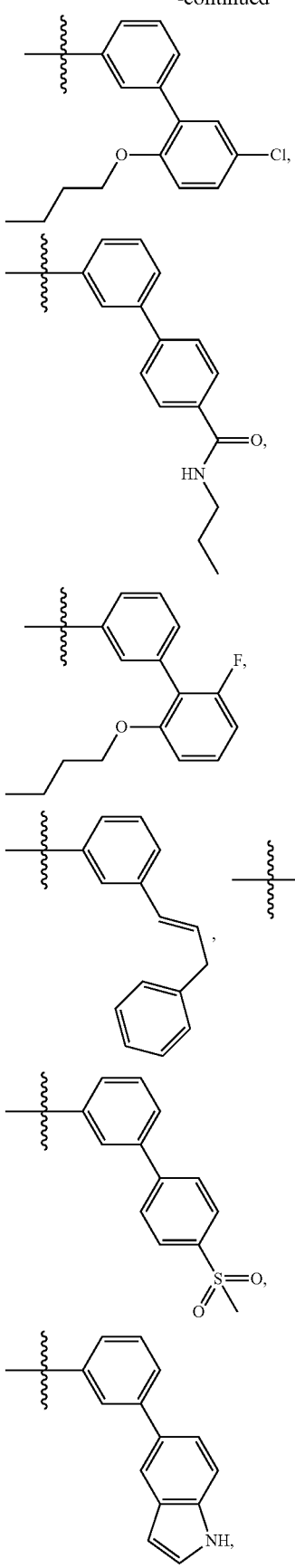

417
-continued
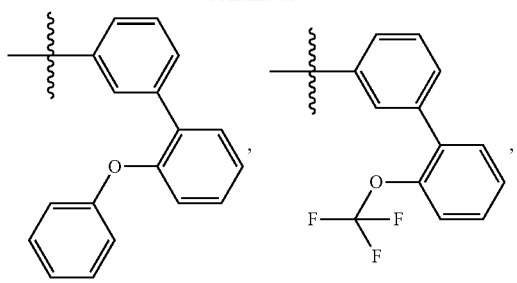
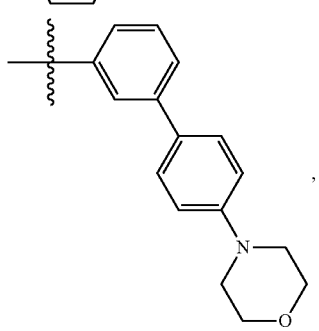
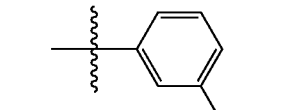
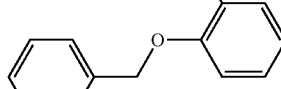
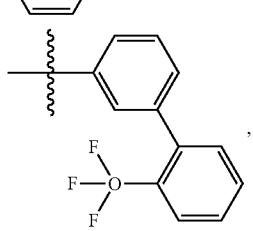
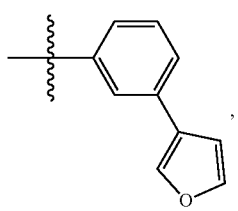
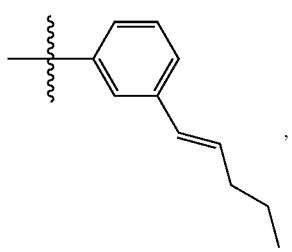
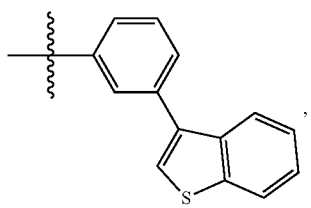
418
-continued
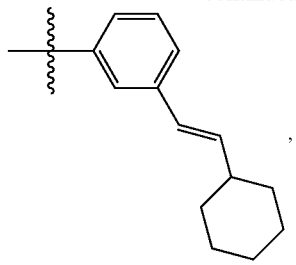
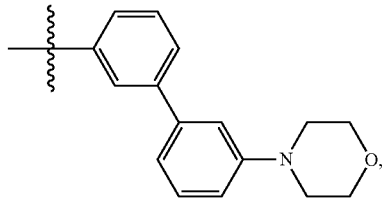
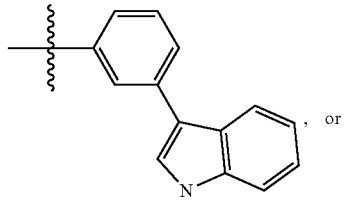, or
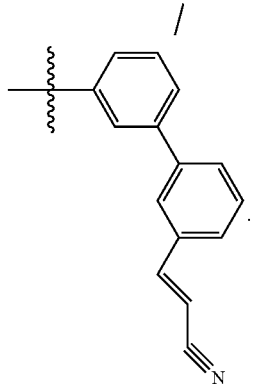
In some embodiments is a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), wherein R¹ is
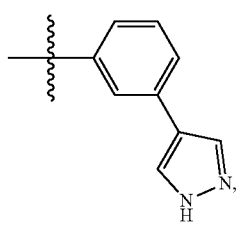
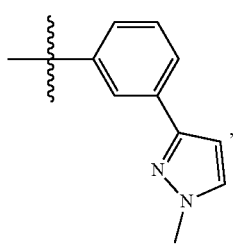
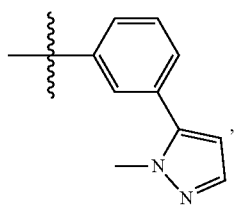

419
-continued
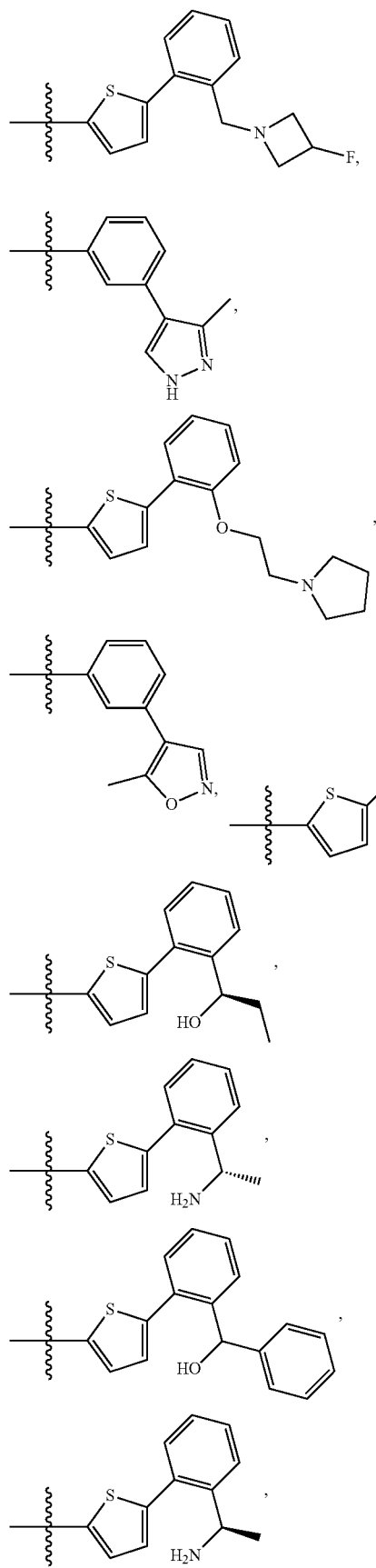
420
-continued
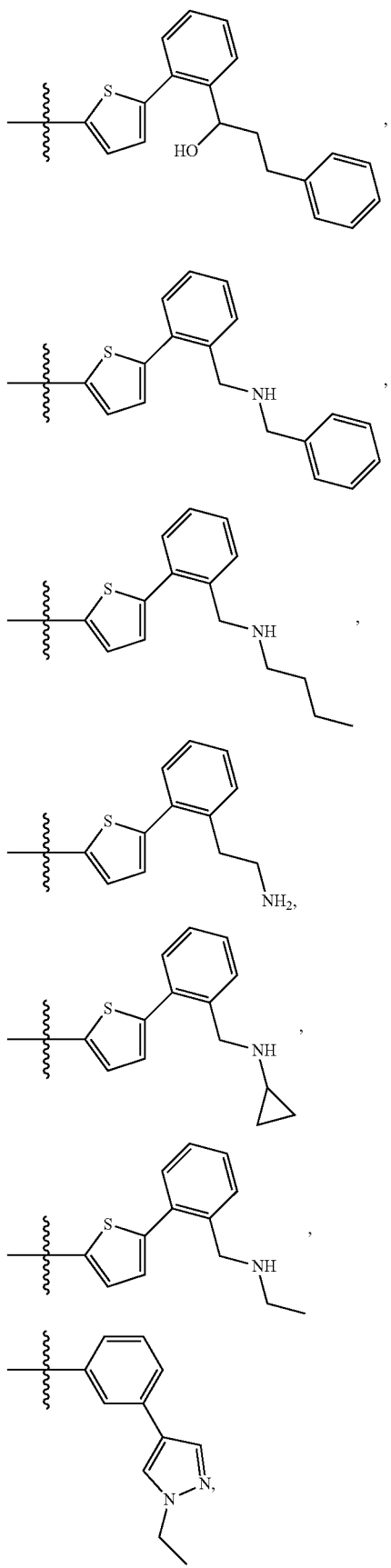

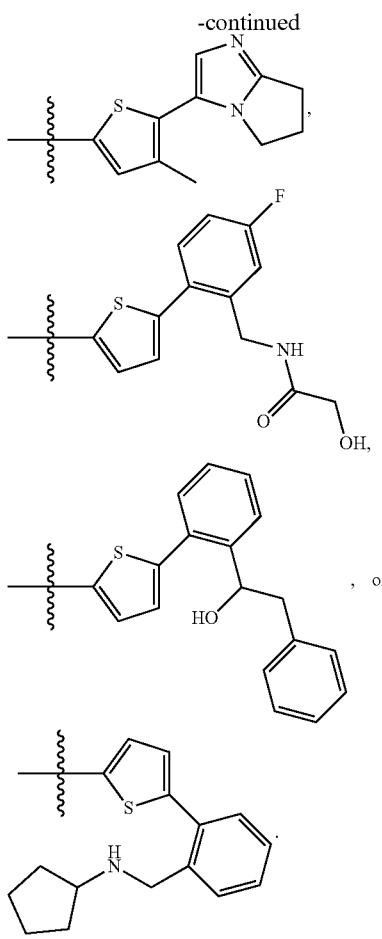
In some embodiments is a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), wherein $R^1$ is
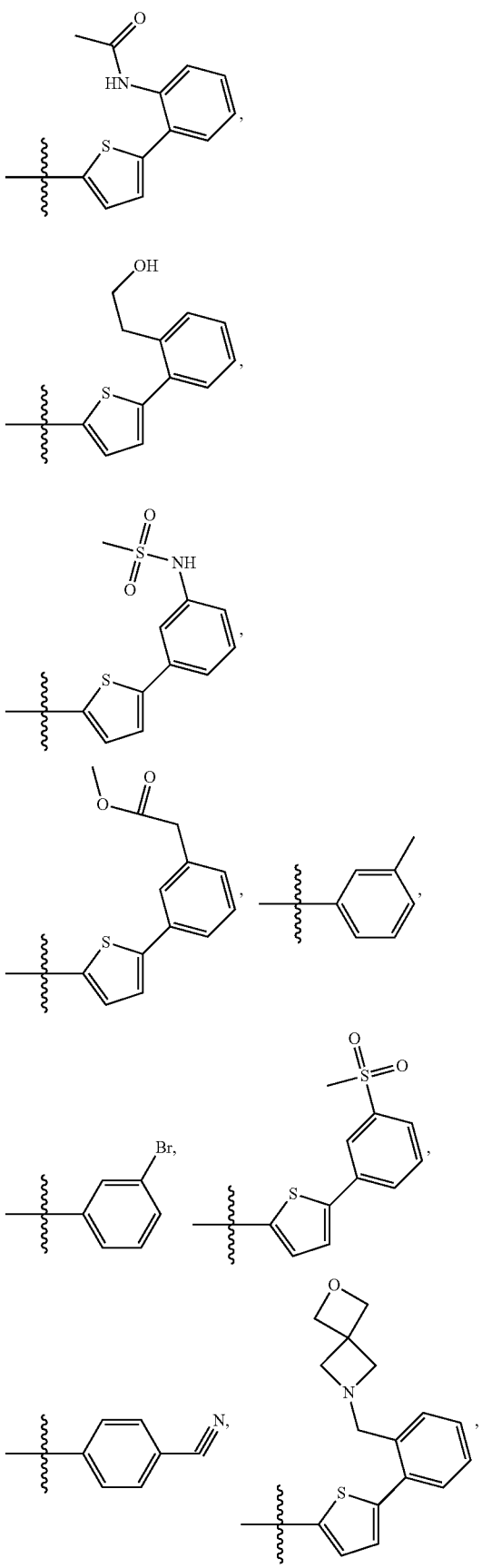

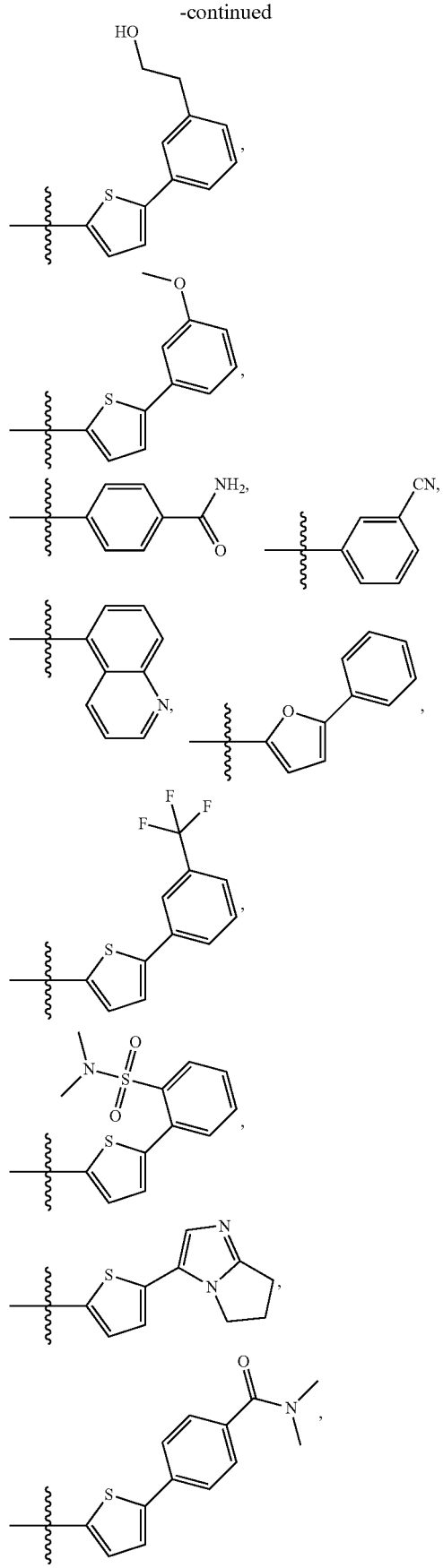
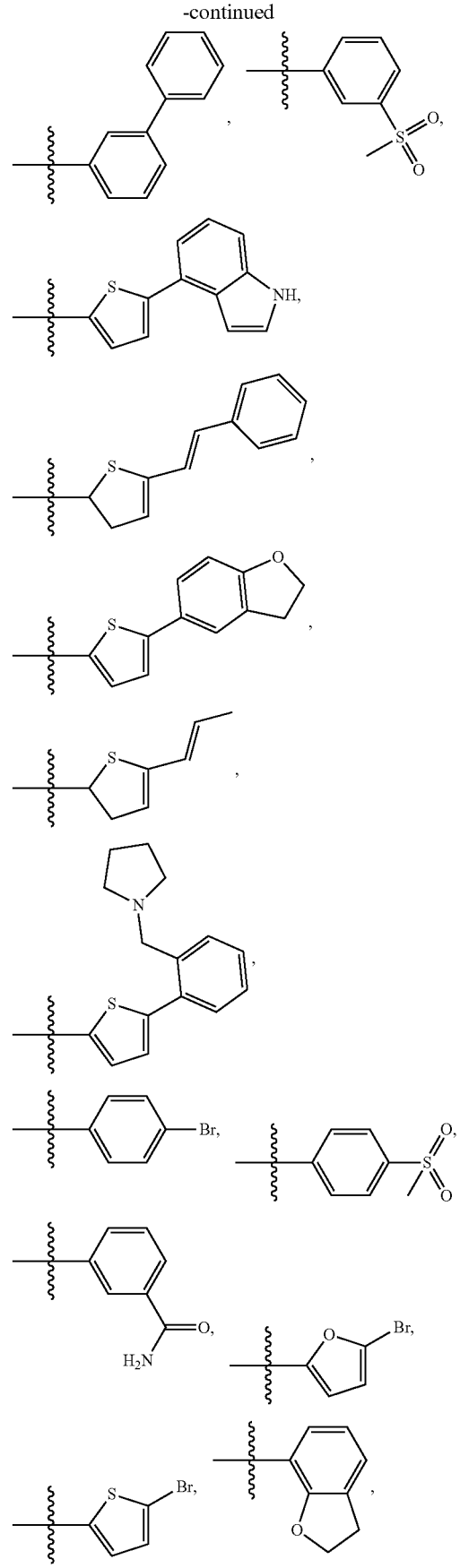

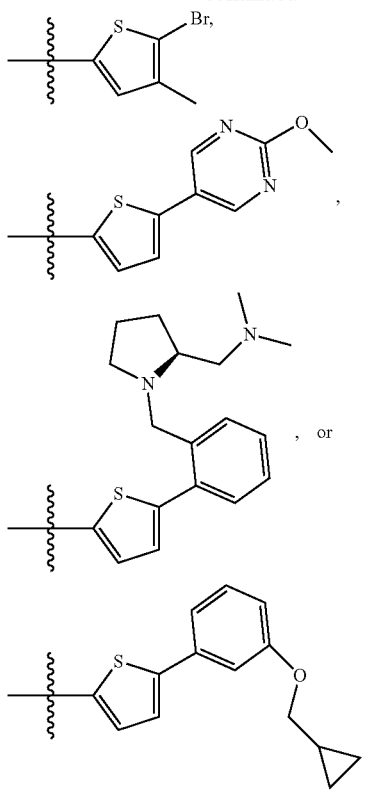
In some embodiments is a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), wherein R¹ is
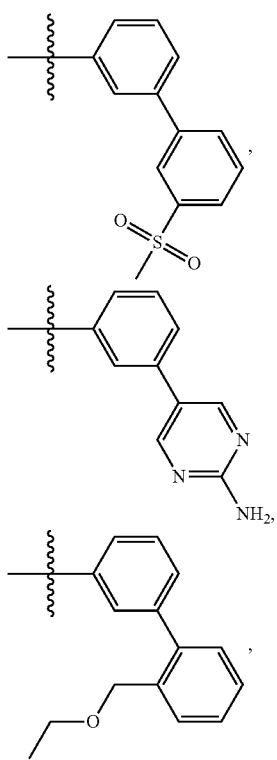
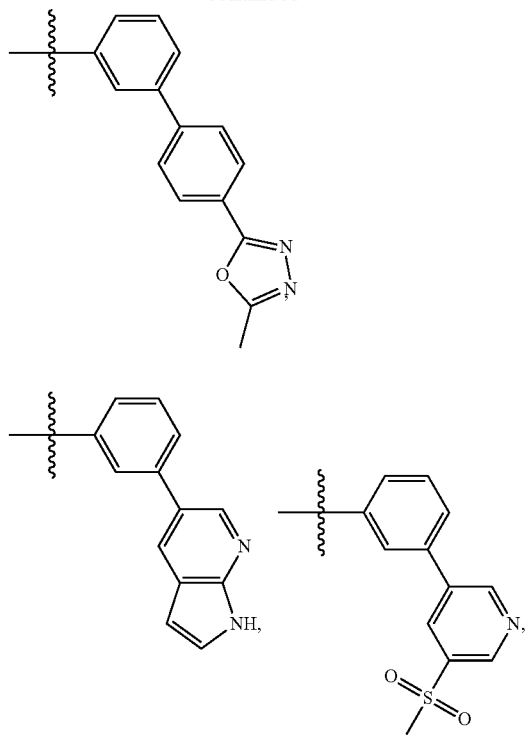

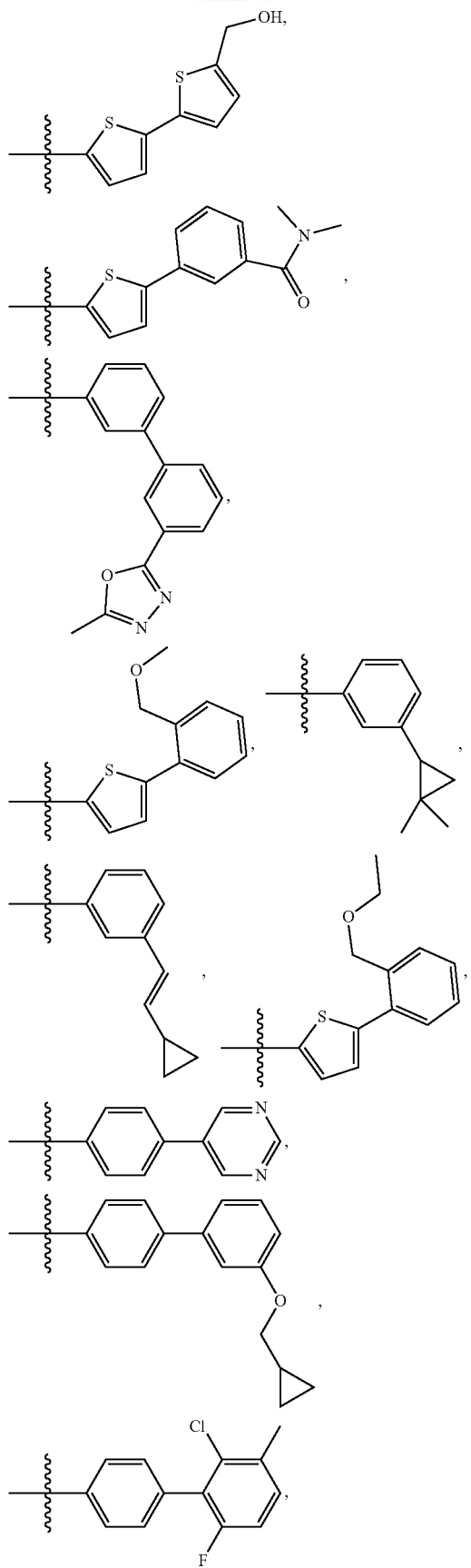
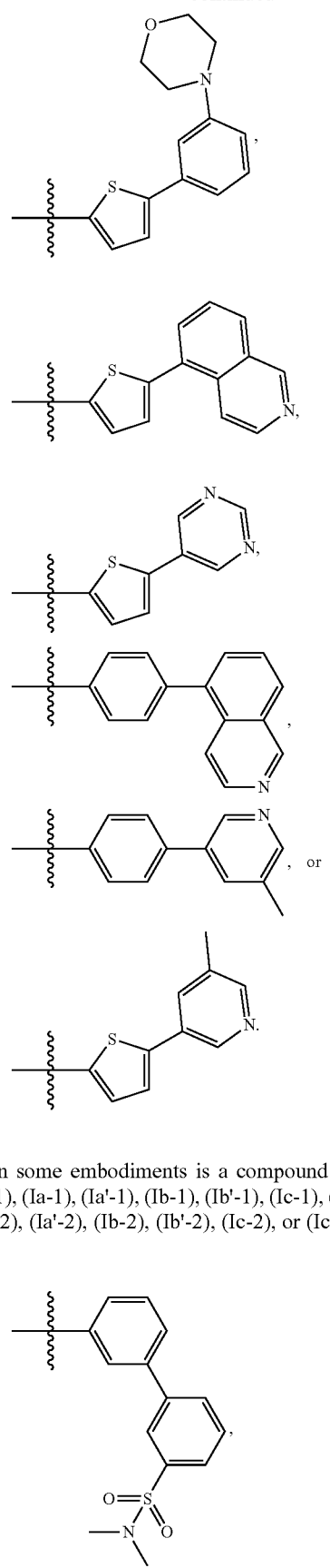
In some embodiments is a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), wherein $R^1$ is 429
-continued
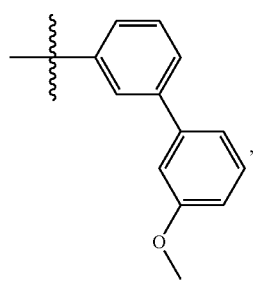
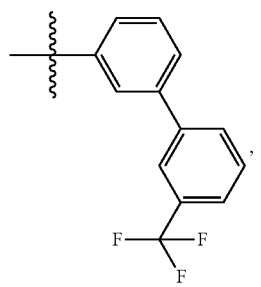
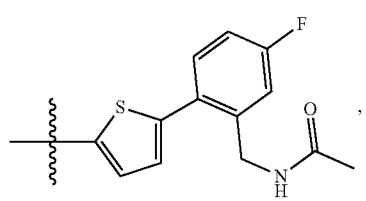
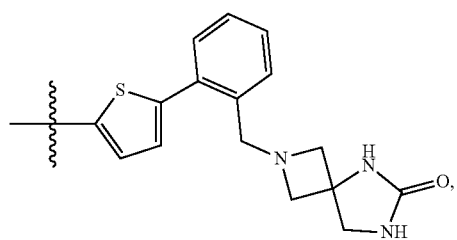
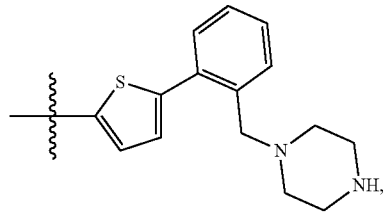
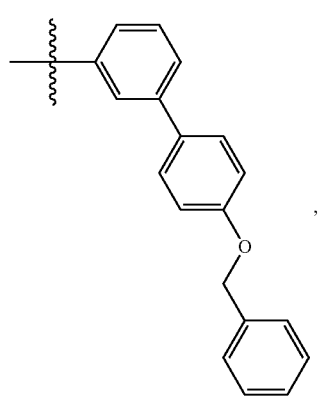
430
-continued
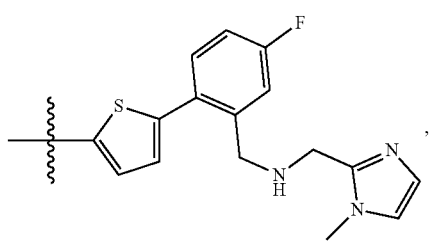
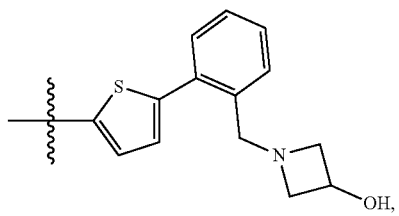
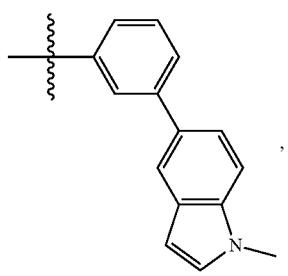
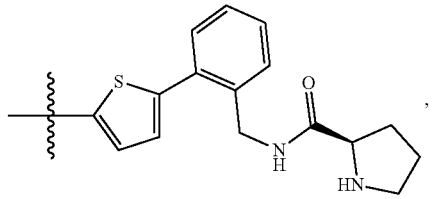
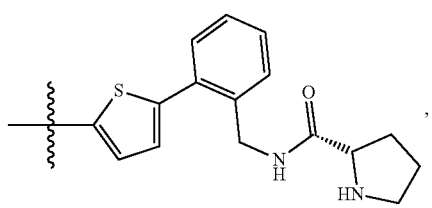
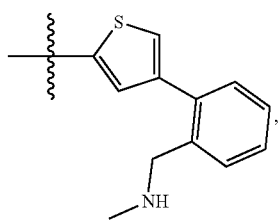
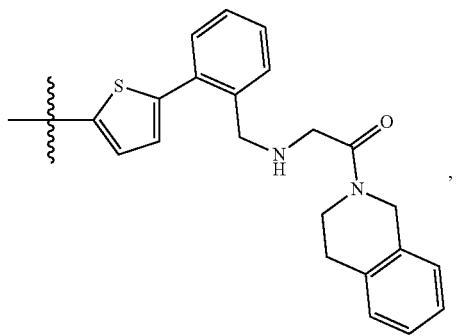

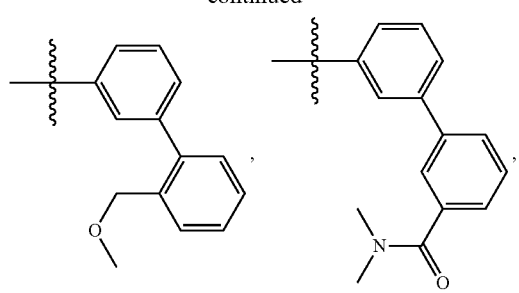
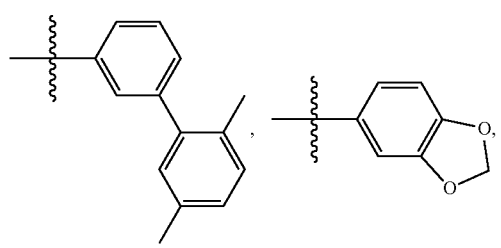
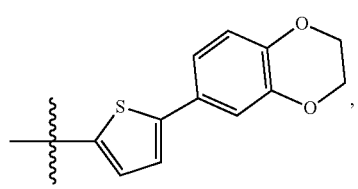
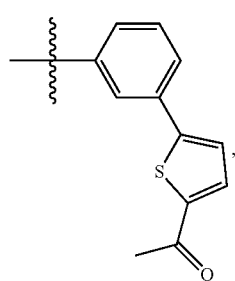
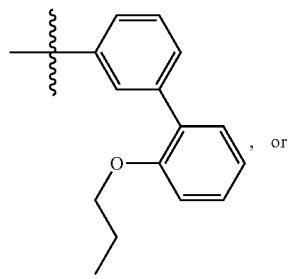
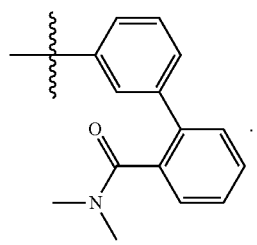, or
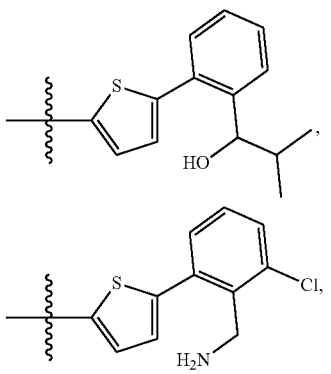
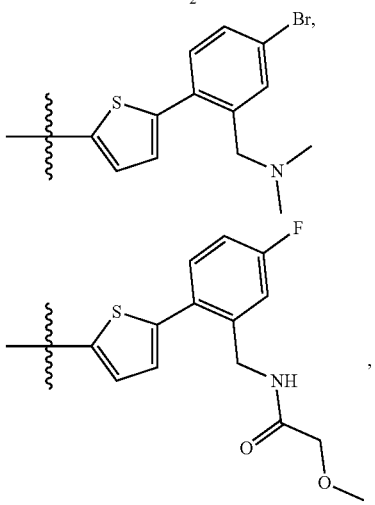
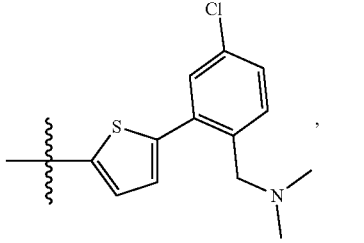
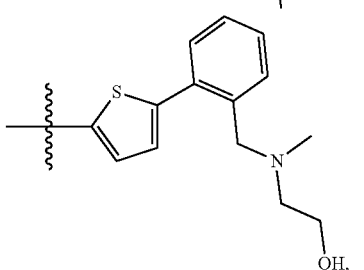
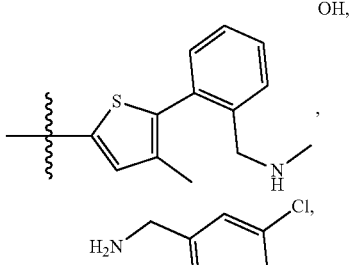
In some embodiments is a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), wherein $R^1$ is

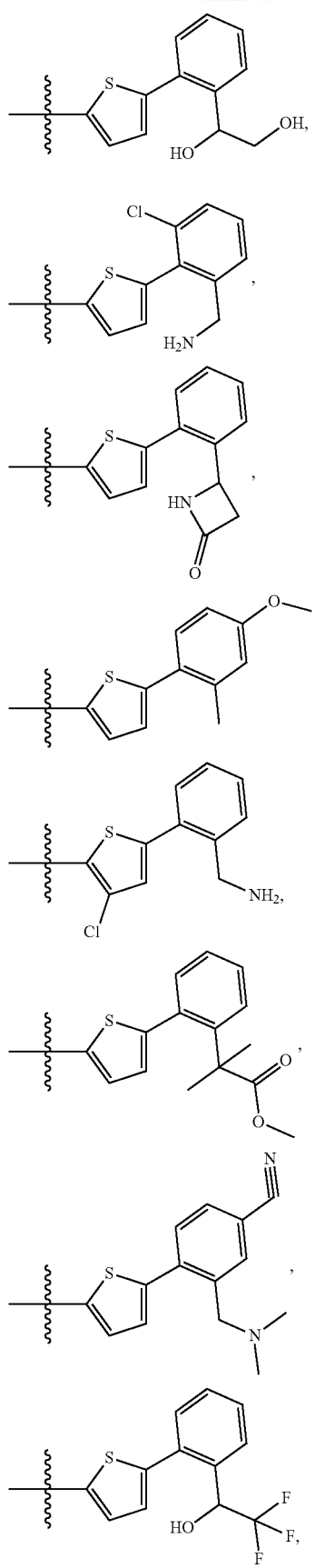
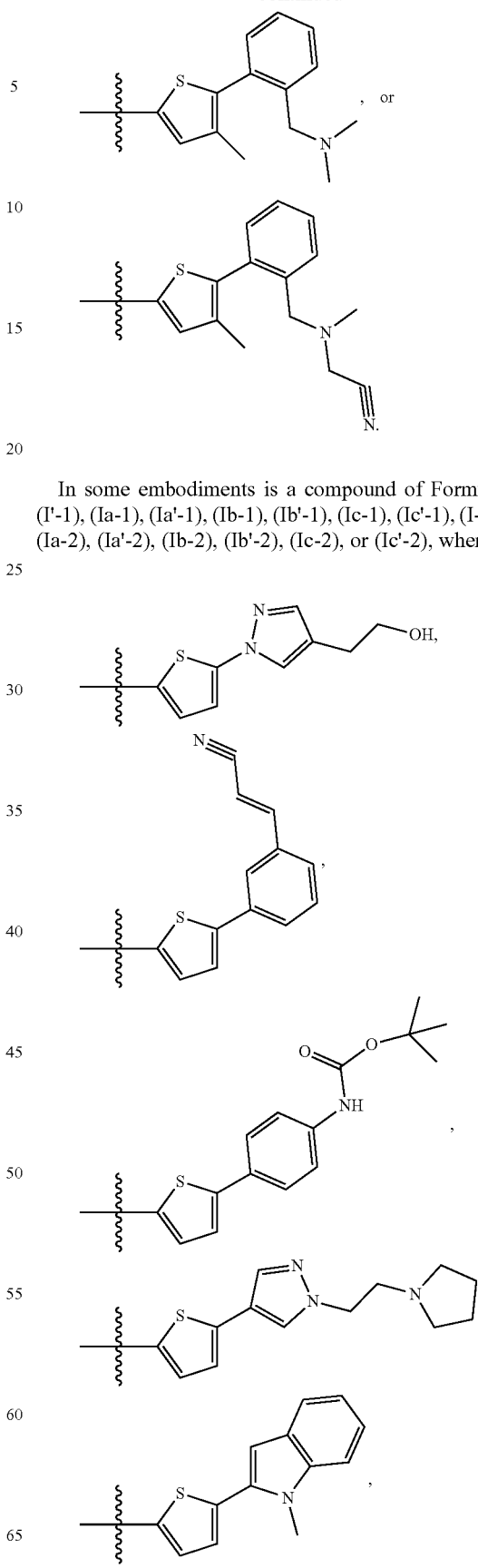
In some embodiments is a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), wherein $R^1$ is

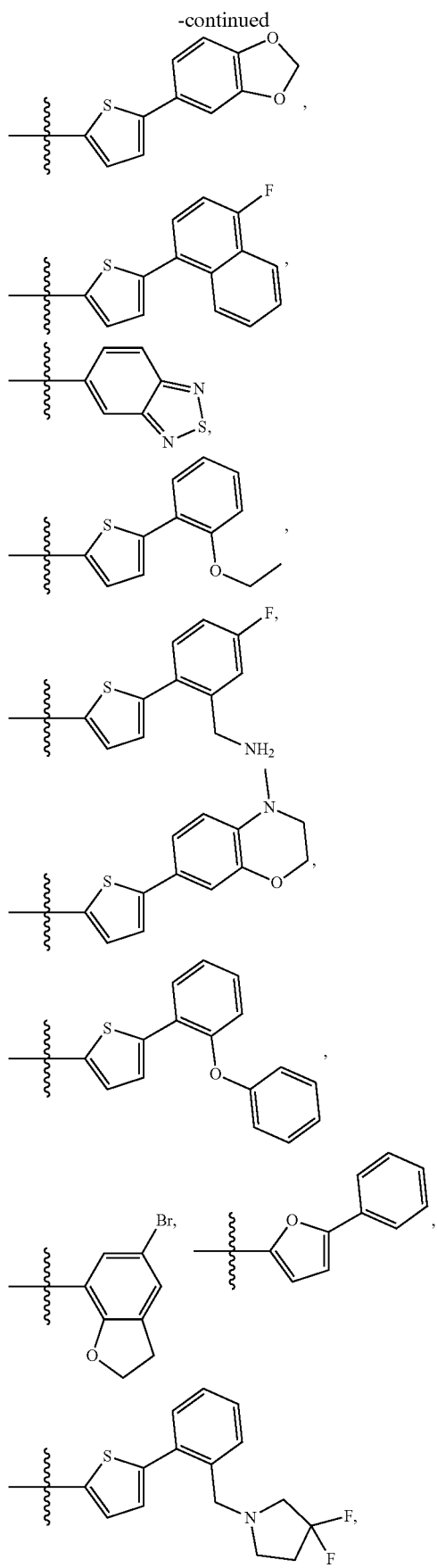
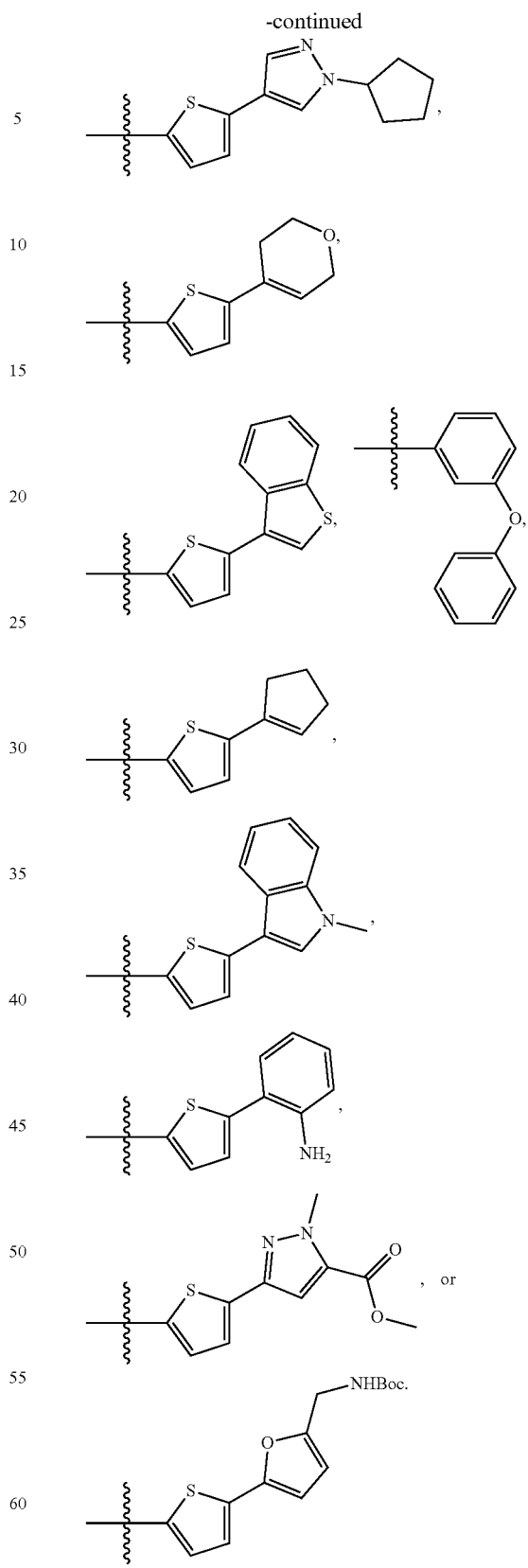
In some embodiments is a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), wherein $R^1$ is

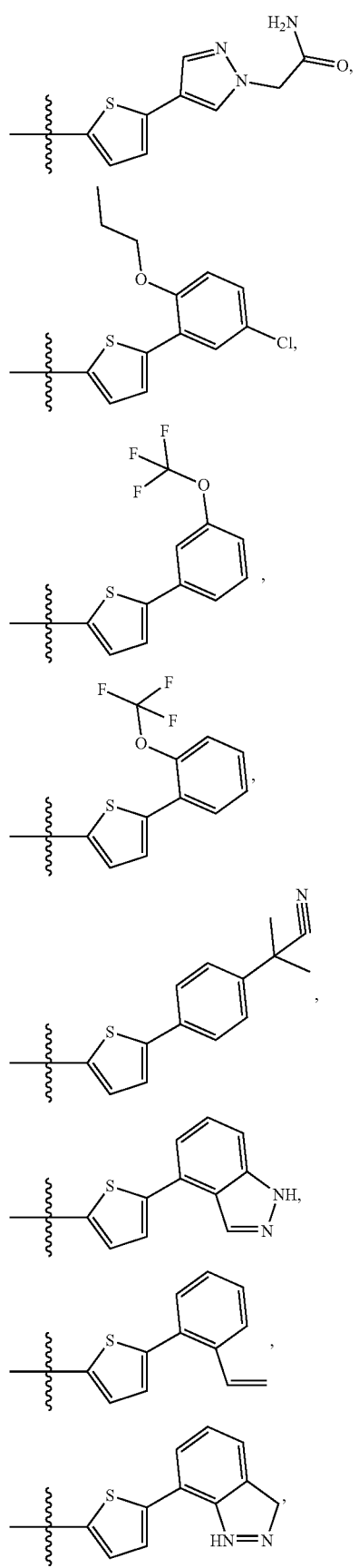
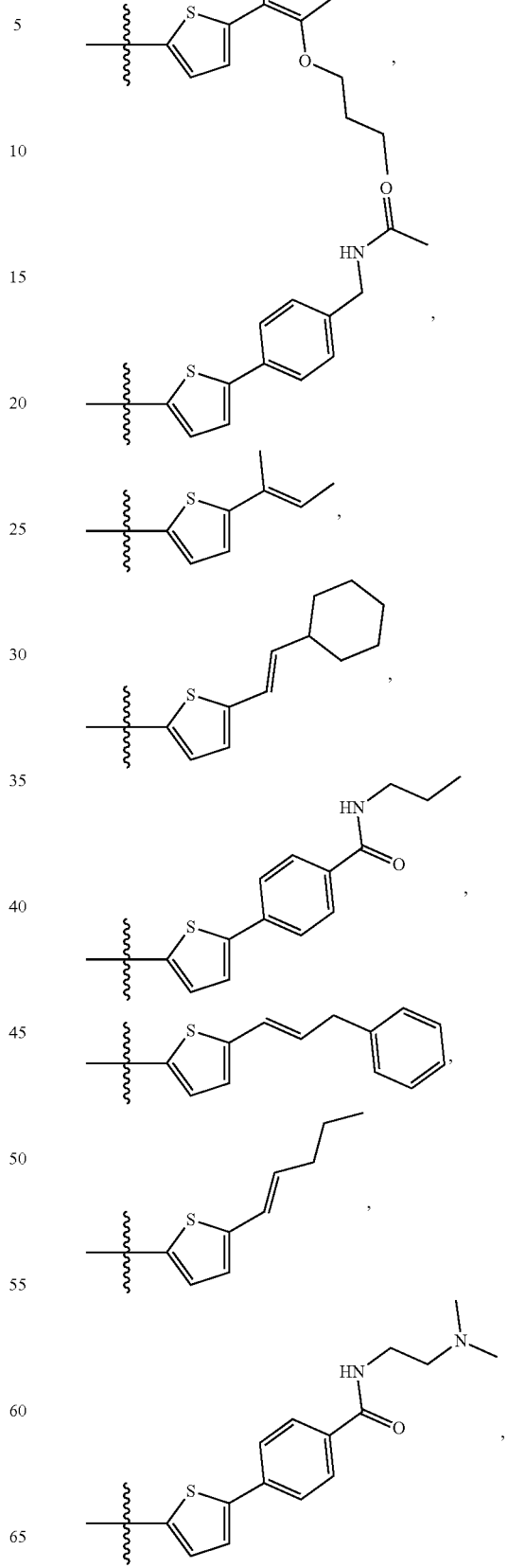

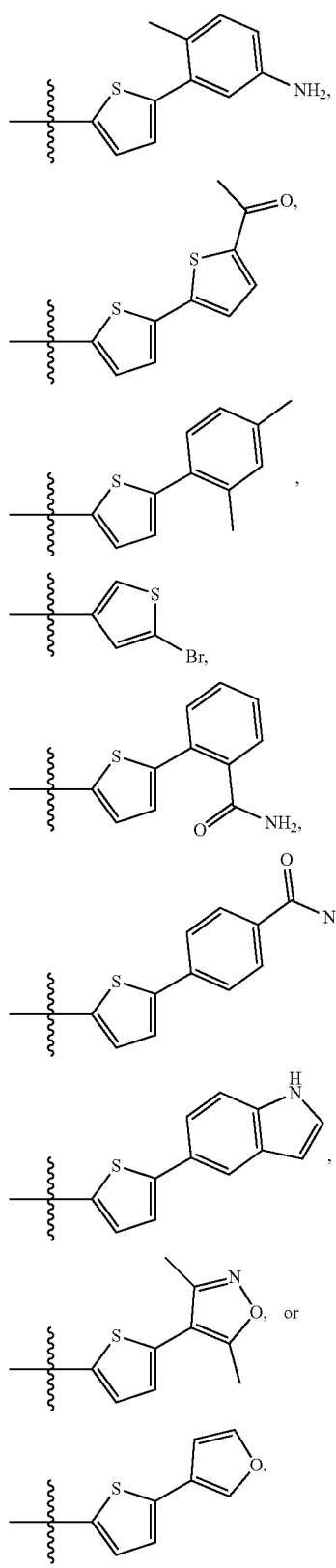
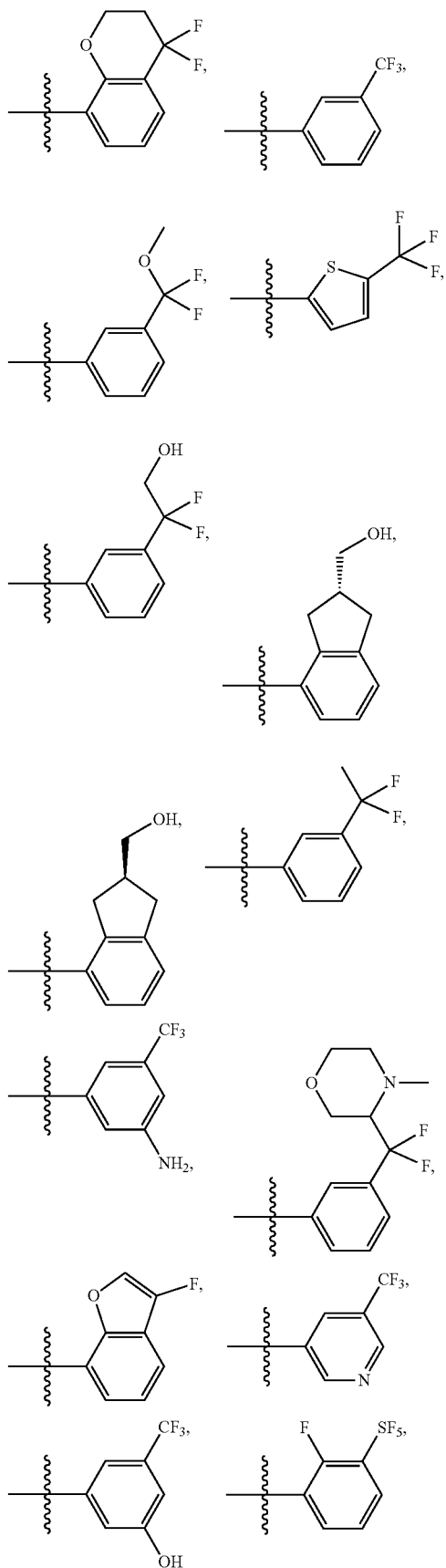
In some embodiments is a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), wherein $R^1$ is

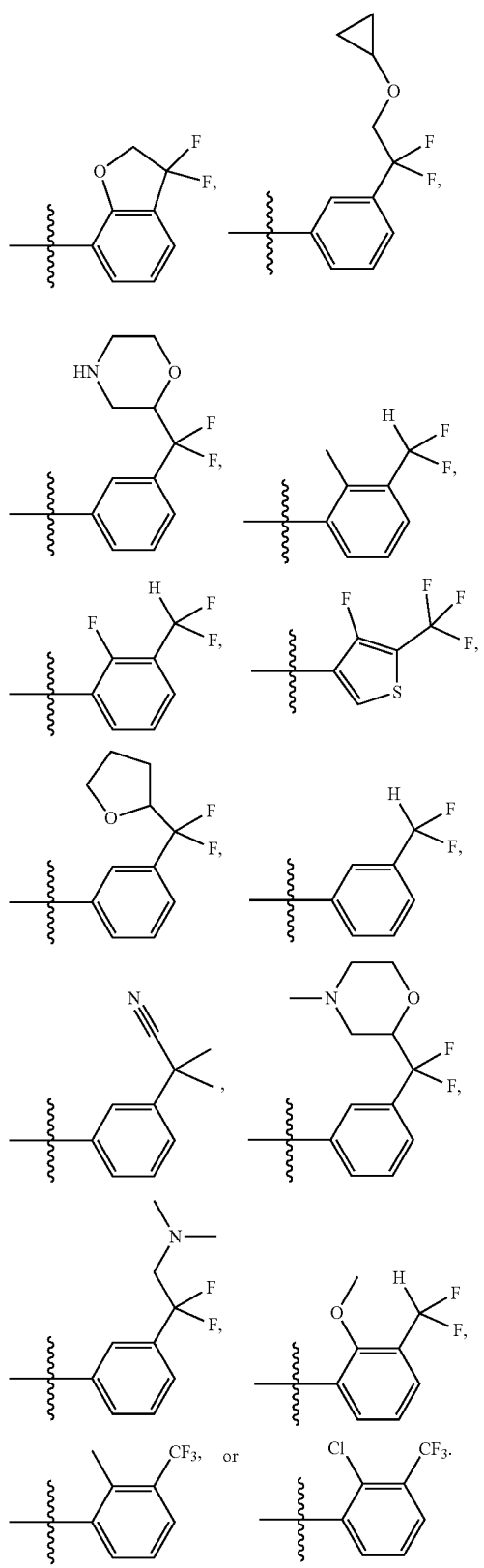
In some embodiments is a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), wherein $R^1$ is

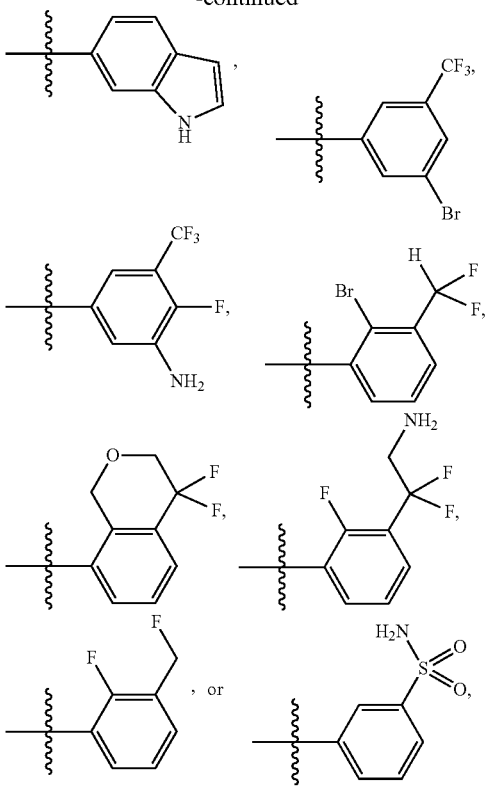

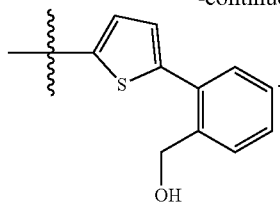

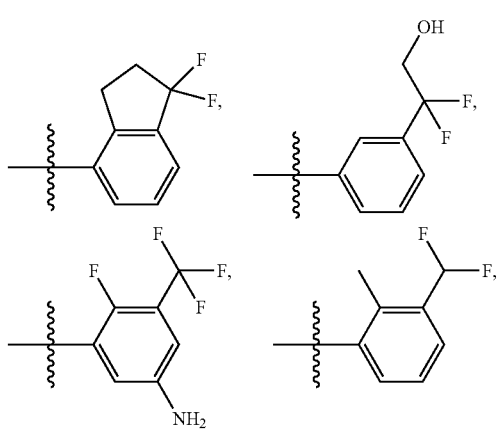

In some embodiments is a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), wherein $R^1$ is

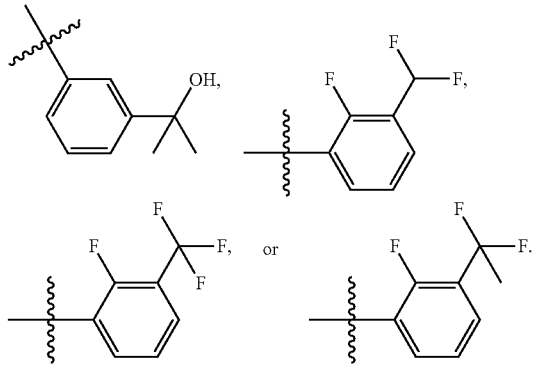

In some embodiments is a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), wherein $R^1$ is

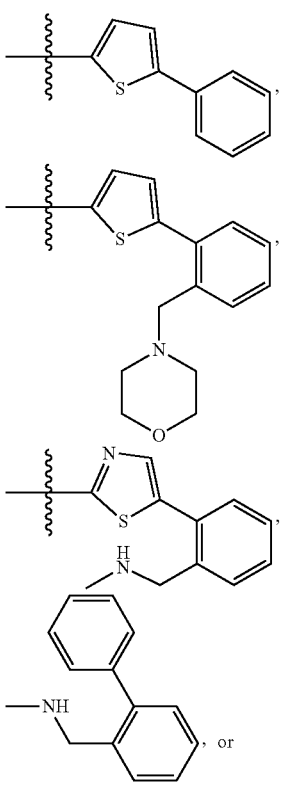

In some embodiments a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), may include one or more substituents of any aspect or embodiment of Formula (I), (I'), (Ia), (Ia'), (Ib), (Ib), (Ic), (Ic'), (II), (II'), (III), or (III').

In embodiments of a compound of Formula (I'-1); $L^1$ is a bond; $R^4$ is hydrogen; $R^6$ is hydrogen; $R^1$ is a

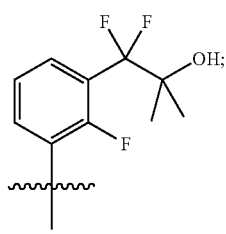 [SMILES: *c1cccc(C(F)(F)C(C)(C)O)c1F]

$R^2$ is —$OR^{2a}$; $R^{2a}$ is methyl; and $R^3$ is

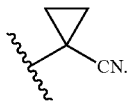

In embodiments of a compound of Formula (I'-1); $L^1$ is a bond; $R^4$ is hydrogen; $R^6$ is hydrogen; $R^1$ is a

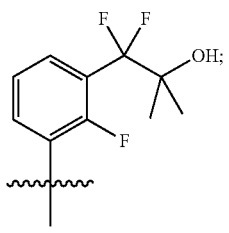 [SMILES: *c1cccc(C(F)(F)C(C)(C)O)c1F]

$R^2$ is —$OR^{2a}$; $R^{2a}$ is methyl; $R^3$ is cyclopropyl optionally substituted with one $R^{20b}$; and $R^{20b}$ is —CN. In embodiments of a compound of Formula (I'-1); $L^1$ is a bond; $R^4$ is hydrogen; $R^6$ is hydrogen; $R^1$ is a

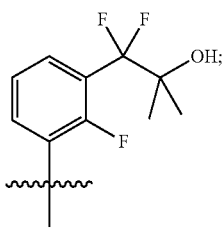 [SMILES: *c1cccc(C(F)(F)C(C)(C)O)c1F]

$R^2$ is —$OR^{2a}$; $R^{2a}$ is methyl; $R^3$ is $C_{3-4}$cycloalkyl optionally substituted with one $R^{20b}$; and $R^{20b}$ is —CN. In embodiments of a compound of Formula (I'-1); $L^1$ is a bond; $R^4$ is hydrogen; $R^6$ is hydrogen; $R^1$ is a

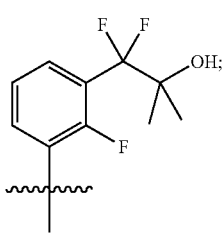 [SMILES: *c1cccc(C(F)(F)C(C)(C)O)c1F]

$R^2$ is —$OR^{2a}$; $R^{2a}$ is methyl; $R^3$ is $C_{3-4}$cycloalkyl optionally substituted with one, two, or three $R^{20b}$; and $R^{20b}$ is —CN. In embodiments of a compound of Formula (I'-1); $L^1$ is a bond; $R^4$ is hydrogen; $R^6$ is hydrogen; $R^1$ is

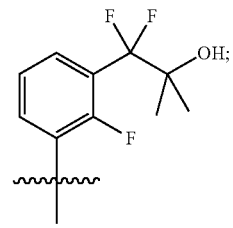 [SMILES: *c1cccc(C(F)(F)C(C)(C)O)c1F]

$R^2$ is —$OR^{2a}$; $R^{2a}$ is methyl; $R^3$ is $C_{3-4}$cycloalkyl optionally substituted with one, two, or three $R^{20b}$; and each $R^{20b}$ is independently —CN or $C_{1-3}$haloalkyl. In embodiments of a compound of Formula (I'-1); $L^1$ is a bond; $R^4$ is hydrogen; $R^6$ is hydrogen; $R^1$ is a

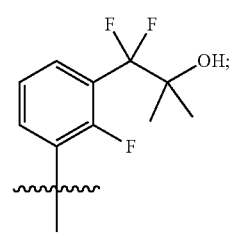

$R^2$ is —$OR^{2a}$; $R^{2a}$ is methyl; $R^3$ is $C_{3-6}$cycloalkyl optionally substituted with one, two, or three $R^{20b}$; and each $R^{20b}$ is independently —CN or $C_{1-3}$haloalkyl. In embodiments of a compound of Formula (I'-1); $L^1$ is a bond; $R^4$ is hydrogen; $R^6$ is hydrogen; $R^1$ is a

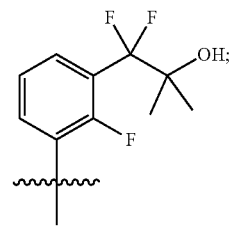 [SMILES: *c1cccc(C(F)(F)C(C)(C)O)c1F]

$R^2$ is —$OR^{2a}$; $R^{2a}$ is methyl; $R^3$ is $C_{3-10}$cycloalkyl optionally substituted with one, two, or three $R^{20b}$; and each $R^{20b}$ is independently —CN or $C_{1-3}$haloalkyl. In embodiments of a compound of Formula (I'-1); $L^1$ is a bond; $R^4$ is hydrogen; $R^6$ is hydrogen; $R^1$ is a $R^2$ is —$OR^{2a}$; $R^{2a}$ is methyl; $R^3$ is $C_{3-10}$cycloalkyl optionally substituted with one, two, or three $R^{20b}$; and each $R^{20b}$ is independently selected from amino; —CN; $C_{1-3}$alkyl; $C_{1-3}$alkoxy; $C_{1-3}$haloalkyl; —OH; —N($R^{24}$)C(O)$R^{25}$; and —C(O)N($R^{22}$)($R^{23}$).

In embodiments of a compound of Formula (I'-1); $L^1$ is a bond; $R^4$ is hydrogen; $R^6$ is hydrogen; $R^1$ is a

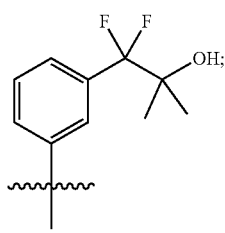 [SMILES: *c1cccc(C(F)(F)C(C)(C)O)c1]

R² is —OR²ᵃ; R²ᵃ is methyl; and R³ is

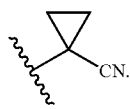

In embodiments of a compound of Formula (I'-1); L¹ is a bond; R⁴ is hydrogen; R⁶ is hydrogen; R¹ is a

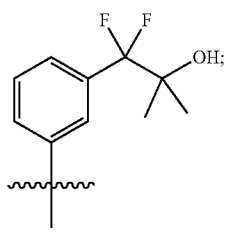 [SMILES: *c1cccc(C(F)(F)C(C)(C)O)c1]

R² is —OR²ᵃ; R²ᵃ is methyl; R³ is cyclopropyl optionally substituted with one R²⁰ᵇ; and R²⁰ᵇ is —CN. In embodiments of a compound of Formula (I'-1); L¹ is a bond; R⁴ is hydrogen; R⁶ is hydrogen; R¹ is a

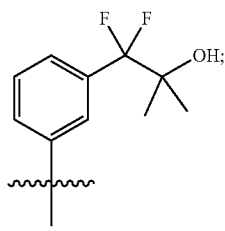 [SMILES: *c1cccc(C(F)(F)C(C)(C)O)c1]

R² is —OR²ᵃ; R²ᵃ is methyl; R³ is $C_{3-4}$cycloalkyl optionally substituted with one R²⁰ᵇ; and R²⁰ᵇ is —CN. In embodiments of a compound of Formula (I'-1); L¹ is a bond; R⁴ is hydrogen; R⁶ is hydrogen; R¹ is

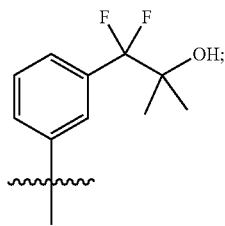 [SMILES: *c1cccc(C(F)(F)C(C)(C)O)c1]

R² is —OR²ᵃ; R²ᵃ is methyl; R³ is $C_{3-4}$cycloalkyl optionally substituted with one, two, or three R²⁰ᵇ; and R²⁰ᵇ is —CN.

In embodiments of a compound of Formula (I'-1); L¹ is a bond; R⁴ is hydrogen; R⁶ is hydrogen; R¹ is a

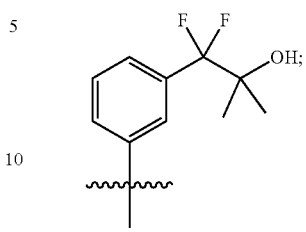

R² is —OR²ᵃ; R²ᵃ is methyl; R³ is $C_{3-4}$cycloalkyl optionally substituted with one, two, or three R²⁰ᵇ; and each R²⁰ᵇ is independently —CN or $C_{1-3}$haloalkyl. In embodiments of a compound of Formula (I'-1); L¹ is a bond; R⁴ is hydrogen; R⁶ is hydrogen; R¹ is a

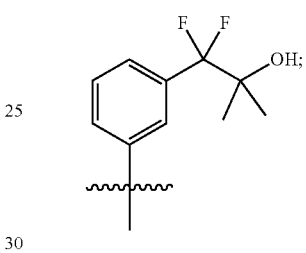

R² is —OR²ᵃ; R²ᵃ is methyl; R³ is $C_{3-6}$cycloalkyl optionally substituted with one, two, or three R²⁰ᵇ; and each R²⁰ᵇ is independently —CN or $C_{1-3}$haloalkyl. In embodiments of a compound of Formula (I'-1); L¹ is a bond; R⁴ is hydrogen; R⁶ is hydrogen; R¹ is a

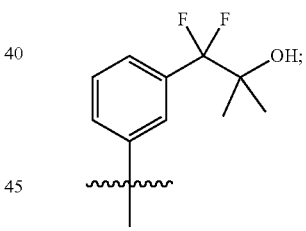

R² is —OR²ᵃ; R²ᵃ is methyl; R³ is $C_{3-10}$cycloalkyl optionally substituted with one, two, or three R²⁰ᵇ; and each R²⁰ᵇ is independently —CN or $C_{1-3}$ haloalkyl. In embodiments of a compound of Formula (I'-1); L¹ is a bond; R⁴ is hydrogen; R⁶ is hydrogen; R¹ is a


R² is —OR²ᵃ; R²ᵃ is methyl; R³ is $C_{3-10}$cycloalkyl optionally substituted with one, two, or three R²⁰ᵇ is independently selected from amino; —CN; $C_{1-3}$alkyl; $C_{1-3}$alkoxy; $C_{1-3}$haloalkyl; —OH; —N($R^{24}$)C(O)$R^{21}$; and —C(O)N($R^{22}$)($R^{23}$).

In embodiments of a compound of Formula (I'-1); $L^1$ is a bond; $R^4$ is hydrogen; $R^6$ is hydrogen; $R^1$ is a

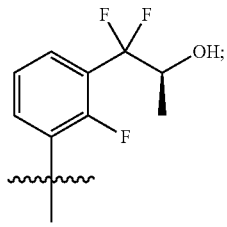 [SMILES: *c1cccc(C(F)(F)[C@H](C)O)c1F]

$R^2$ is —O$R^{2a}$; $R^{2a}$ is methyl; and $R^3$ is

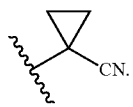

In embodiments of a compound of Formula (I'-1); $L^1$ is a bond; $R^4$ is hydrogen; $R^6$ is hydrogen; $R^1$ is a

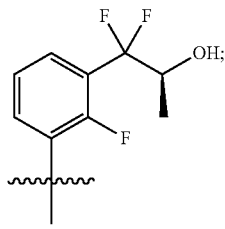 [SMILES: *c1cccc(C(F)(F)[C@H](C)O)c1F]

$R^2$ is —O$R^{2a}$; $R^{2a}$ is methyl; $R^3$ is cyclopropyl optionally substituted with one $R^{20b}$; and $R^{20b}$ is —CN. In embodiments of a compound of Formula (I'-1); $L^1$ is a bond; $R^4$ is hydrogen; $R^6$ is hydrogen; $R^1$ is a

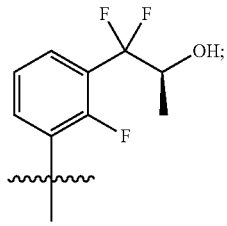 [SMILES: *c1cccc(C(F)(F)[C@H](C)O)c1F]

$R^2$ is —O$R^{2a}$; $R^{2a}$ is methyl; $R^3$ is $C_{3-4}$cycloalkyl optionally substituted with one $R^{20b}$; and $R^{20b}$ is —CN. In embodiments of a compound of Formula (I'-1); $L^1$ is a bond; $R^4$ is hydrogen; $R^6$ is hydrogen; $R^1$ is a

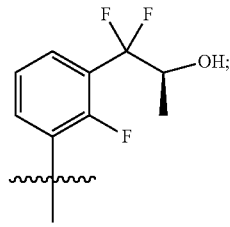 [SMILES: *c1cccc(C(F)(F)[C@H](C)O)c1F]

$R^2$ is —O$R^{2a}$; $R^{2a}$ is methyl; $R^3$ is $C_{3-4}$cycloalkyl optionally substituted with one, two, or three $R^{20b}$; and $R^{20b}$ is —CN.

In embodiments of a compound of Formula (I'-1); $L^1$ is a bond; $R^4$ is hydrogen; $R^6$ is hydrogen; $R^1$ is a

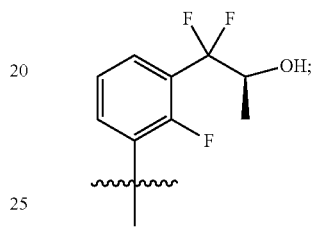

$R^2$ is —O$R^{2a}$; $R^{2a}$ is methyl; $R^3$ is $C_{3-4}$cycloalkyl optionally substituted with one, two, or three $R^{20b}$; and each $R^{20b}$ is independently —CN or $C_{1-3}$haloalkyl. In embodiments of a compound of Formula (I'-1); $L^1$ is a bond; $R^4$ is hydrogen; $R^6$ is hydrogen; $R^1$ is a

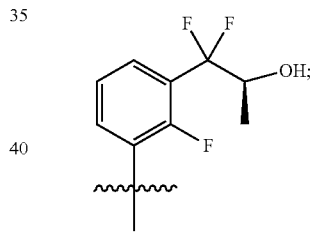

$R^2$ is —O$R^{2a}$; $R^{2a}$ is methyl; $R^3$ is $C_{3-6}$cycloalkyl optionally substituted with one, two, or three $R^{20b}$; and each $R^{20b}$ is independently —CN or $C_{1-3}$haloalkyl. In embodiments of a compound of Formula (I'-1); $L^1$ is a bond; $R^4$ is hydrogen; $R^6$ is hydrogen; $R^1$ is a

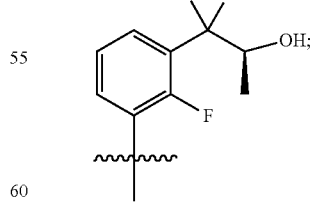

$R^2$ is —O$R^{2a}$; $R^{2a}$ is methyl; $R^3$ is $C_{3-10}$cycloalkyl optionally substituted with one, two, or three $R^{20b}$; and each $R^{20b}$ is independently —CN or $C_{1-3}$haloalkyl. In embodiments of a compound of Formula (I'-1); $L^1$ is a bond; $R^4$ is hydrogen; $R^6$ is hydrogen; $R^1$ is a

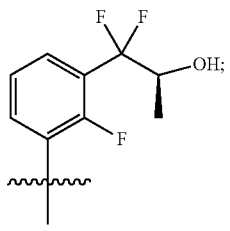 [SMILES: *c1cccc(C(F)(F)[C@H](C)O)c1F]

$R^2$ is —$OR^{2a}$; $R^{2a}$ is methyl; $R^3$ is $C_{3-10}$cycloalkyl optionally substituted with one, two, or three $R^{20b}$; and each $R^{20b}$ is independently selected from amino; —CN; $C_{1-3}$alkyl; $C_{1-3}$alkoxy; $C_{1-3}$haloalkyl; —OH; —N($R^{24}$)C(O)$R^{25}$; and —C(O)N($R^{22}$)($R^{23}$).

In embodiments of a compound of Formula (I'-1); $L^1$ is a bond; $R^4$ is hydrogen; $R^6$ is hydrogen; $R^1$ is a

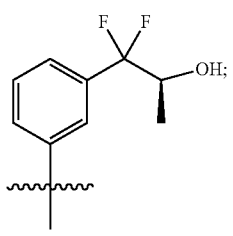 [SMILES: *c1cccc(C(F)(F)[C@H](C)O)c1]

$R^2$ is —$OR^{2a}$; $R^{2a}$ is methyl; and $R^3$ is

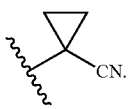

In embodiments of a compound of Formula (I'-1); $L^1$ is a bond; $R^4$ is hydrogen; $R^6$ is hydrogen; $R^1$ is a

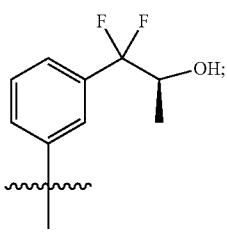 [SMILES: *c1cccc(C(F)(F)[C@H](C)O)c1]

$R^2$ is —$OR^{2a}$; $R^{2a}$ is methyl; $R^3$ is cyclopropyl optionally substituted with one $R^{20b}$; and $R^{20b}$ is —CN. In embodiments of a compound of Formula (I'-1); $L^1$ is a bond; $R^4$ is hydrogen; $R^6$ is hydrogen; $R^1$ is a

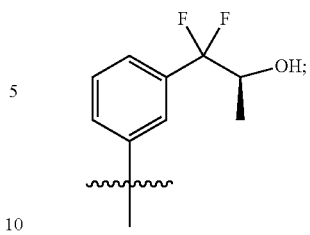

$R^2$ is —$OR^{2a}$; $R^{2a}$ is methyl; $R^3$ is $C_{3-4}$cycloalkyl optionally substituted with one $R^{20b}$; and $R^{20b}$ is —CN. In embodiments of a compound of Formula (I'-1); $L^1$ is a bond; $R^4$ is hydrogen; $R^6$ is hydrogen; $R^1$ is a

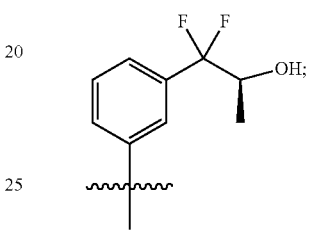

$R^2$ is —$OR^{2a}$; $R^{2a}$ is methyl; $R^3$ is $C_{3-4}$cycloalkyl optionally substituted with one, two, or three $R^{20b}$; and $R^{20b}$ is —CN. In embodiments of a compound of Formula (I'-1); $L^1$ is a bond; $R^4$ is hydrogen; $R^6$ is hydrogen; $R^1$ is a

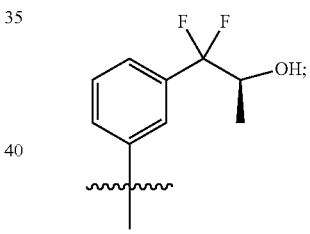

$R^2$ is —$OR^{2a}$; $R^{2a}$ is methyl; $R^3$ is $C_{3-4}$cycloalkyl optionally substituted with one, two, or three $R^{20b}$; and each $R^{20b}$ is independently —CN or $C_{1-3}$haloalkyl. In embodiments of a compound of Formula (I'-1); $L^1$ is a bond; $R^4$ is hydrogen; $R^6$ is hydrogen; $R^1$ is a

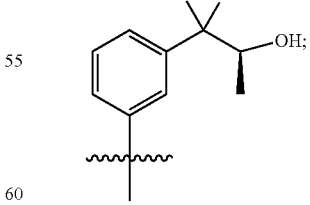

$R^2$ is —$OR^{2a}$; $R^{2a}$ is methyl; $R^3$ is $C_{3-6}$cycloalkyl optionally substituted with one, two, or three $R^{20b}$; and each $R^{20b}$ is independently —CN or $C_{1-3}$haloalkyl. In embodiments of a compound of Formula (I'-1); $L^1$ is a bond; $R^4$ is hydrogen; $R^6$ is hydrogen; $R^1$ is a

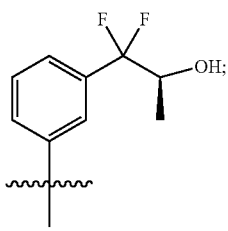 [SMILES: *c1cccc(C(F)(F)[C@H](C)O)c1]

$R^2$ is —$OR^{2a}$; $R^{2a}$ is methyl; $R^3$ is $C_{3-10}$cycloalkyl optionally substituted with one, two, or three $R^{20b}$; and each $R^{20b}$ is independently —CN or $C_{1-3}$ haloalkyl. In embodiments of a compound of Formula (I'-1); $L^1$ is a bond; $R^4$ is hydrogen; $R^6$ is hydrogen; $R^1$ is a

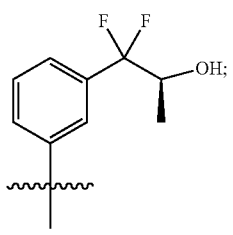 [SMILES: *c1cccc(C(F)(F)[C@H](C)O)c1]

$R^2$ is —$OR^{2a}$; $R^{2a}$ is methyl; $R^3$ is $C_{3-10}$cycloalkyl optionally substituted with one, two, or three $R^{20b}$; and each $R^{20b}$ is independently selected from amino; —CN; $C_{1-3}$alkyl; $C_{1-3}$alkoxy; $C_{1-3}$haloalkyl; —OH; —N($R^{24}$)C(O)$R^{25}$; and —C(O)N($R^{22}$)($R^{23}$).

In embodiments of a compound of Formula (I'-1); $L^1$ is a bond; $R^4$ is hydrogen; $R^6$ is hydrogen; $R^1$ is a

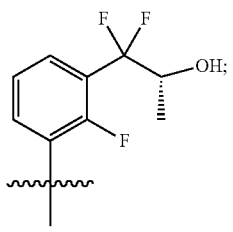 [SMILES: *c1cccc(C(F)(F)[C@@H](C)O)c1F]

$R^2$ is —$OR^{2a}$; $R^{2a}$ is methyl; and $R^3$ is

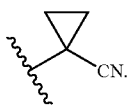 [SMILES: *C1(C#N)CC1]

In embodiments of a compound of Formula (I'-1); $L^1$ is a bond; $R^4$ is hydrogen; $R^6$ is hydrogen; $R^1$ is a


$R^2$ is —$OR^{2a}$; $R^{2a}$ is methyl; $R^3$ is cyclopropyl optionally substituted with one $R^{20b}$; and $R^{20b}$ is —CN. In embodiments of a compound of Formula (I'-1); $L^1$ is a bond; $R^4$ is hydrogen; $R^6$ is hydrogen; $R^1$ is a


$R^2$ is —$OR^{2a}$; $R^{2a}$ is methyl; $R^3$ is $C_{3-4}$cycloalkyl optionally substituted with one $R^{20b}$; and $R^{20b}$ is —CN. In embodiments of a compound of Formula (I'-1); $L^1$ is a bond; $R^4$ is hydrogen; $R^6$ is hydrogen; $R^1$ is a

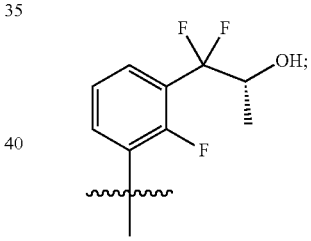

$R^2$ is —$OR^{2a}$; $R^{2a}$ is methyl; $R^3$ is $C_{3-4}$cycloalkyl optionally substituted with one, two, or three $R^{20b}$; and $R^{20b}$ is —CN. In embodiments of a compound of Formula (I'-1); $L^1$ is a bond; $R^4$ is hydrogen; $R^6$ is hydrogen; $R^1$ is a

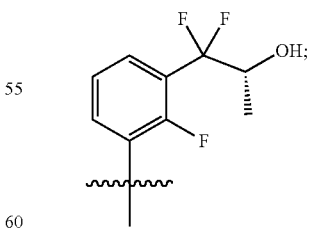

$R^2$ is —$OR^{2a}$; $R^{2a}$ is methyl; $R^3$ is $C_{3-4}$cycloalkyl optionally substituted with one, two, or three $R^{20b}$; and each $R^{20b}$ is independently —CN or $C_{1-3}$haloalkyl. In embodiments of a compound of Formula (I'-1); $L^1$ is a bond; $R^4$ is hydrogen; $R^6$ is hydrogen; $R^1$ is

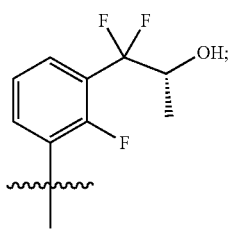 [SMILES: *c1cccc(C(F)(F)[C@@H](C)O)c1F]

$R^2$ is —$OR^{2a}$; $R^{2a}$ is methyl; $R^3$ is $C_{3-6}$cycloalkyl optionally substituted with one, two, or three $R^{20b}$; and each $R^{20b}$ is independently —CN or $C_{1-3}$haloalkyl. In embodiments of a compound of Formula (I'-1); $L^1$ is a bond; $R^4$ is hydrogen; $R^6$ is hydrogen; $R^1$ is a

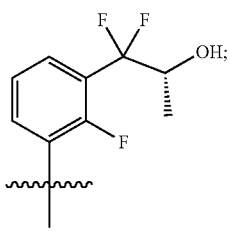 [SMILES: *c1cccc(C(F)(F)[C@@H](C)O)c1F]

$R^2$ is —$OR^{2a}$; $R^{2a}$ is methyl; $R^3$ is $C_{3-10}$cycloalkyl optionally substituted with one, two, or three $R^{20b}$; and each $R^{20b}$ is independently —CN or $C_{1-3}$ haloalkyl. In embodiments of a compound of Formula (I'-1); $L^1$ is a bond; $R^4$ is hydrogen; $R^6$ is hydrogen; $R^1$ is a

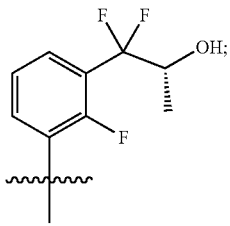 [SMILES: *c1cccc(C(F)(F)[C@@H](C)O)c1F]

$R^2$ is —$OR^{2a}$; $R^{2a}$ is methyl; $R^3$ is $C_{3-10}$cycloalkyl optionally substituted with one, two, or three $R^{20b}$; and each $R^{20b}$ is independently selected from amino; —CN; $C_{1-3}$alkyl; $C_{1-3}$alkoxy; $C_{1-3}$haloalkyl; —OH; —N($R^{24}$)C(O)$R^{25}$; and —C(O)N($R^{22}$)($R^{23}$).

In embodiments of a compound of Formula (I'-1); $L^1$ is a bond; $R^4$ is hydrogen; $R^6$ is hydrogen; $R^1$ is a

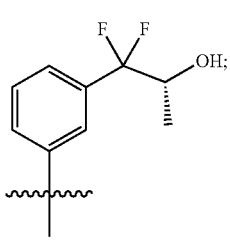 [SMILES: *c1cccc(C(F)(F)[C@@H](C)O)c1]

$R^2$ is —$OR^{2a}$; $R^{2a}$ is methyl; and $R^3$

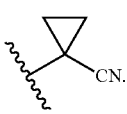

In embodiments of a compound of Formula (I'-1); $L^1$ is a bond; $R^4$ is hydrogen; $R^6$ is hydrogen; $R^1$ is a

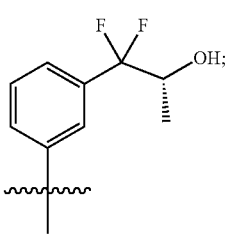 [SMILES: *c1cccc(C(F)(F)[C@@H](C)O)c1]

$R^2$ is —$OR^{2a}$; $R^{2a}$ is methyl; $R^3$ is cyclopropyl optionally substituted with one $R^{20b}$; and $R^{20b}$ is —CN. In embodiments of a compound of Formula (I'-1); $L^1$ is a bond; $R^4$ is hydrogen; $R^6$ is hydrogen; $R^1$ is a

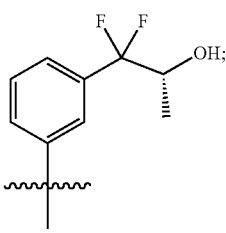 [SMILES: *c1cccc(C(F)(F)[C@@H](C)O)c1]

$R^2$ is —$OR^{2a}$; $R^{2a}$ is methyl; $R^3$ is $C_{3-4}$cycloalkyl optionally substituted with one $R^{20b}$; and $R^{20b}$ is —CN. In embodiments of a compound of Formula (I'-1); $L^1$ is a bond; $R^4$ is hydrogen; $R^6$ is hydrogen; $R^1$ is a

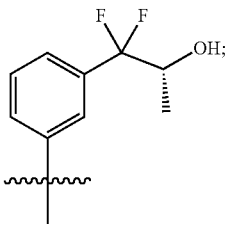 [SMILES: *c1cccc(C(F)(F)[C@@H](C)O)c1]

$R^2$ is —$OR^{2a}$; $R^{2a}$ is methyl; $R^3$ is $C_{3-4}$cycloalkyl optionally substituted with one, two, or three $R^{20b}$; and $R^{20b}$ is —CN. In embodiments of a compound of Formula (I'-1); $L^1$ is a bond; $R^4$ is hydrogen; $R^6$ is hydrogen; $R^1$ is a

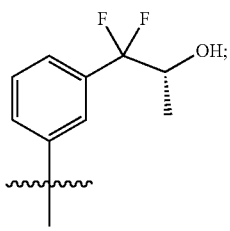 [SMILES: *c1cccc(C(F)(F)[C@@H](C)O)c1]

$R^2$ is —$OR^{2a}$; $R^{2a}$ is methyl; $R^3$ is $C_{3-4}$cycloalkyl optionally substituted with one, two, or three $R^{20b}$; and each $R^{20b}$ is independently —CN or $C_{1-3}$haloalkyl. In embodiments of a compound of Formula (I'-1); $L^1$ is a bond; $R^4$ is hydrogen; $R^6$ is hydrogen; $R^1$ is a

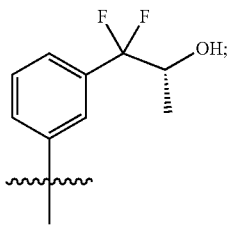 [SMILES: *c1cccc(C(F)(F)[C@@H](C)O)c1]

$R^2$ is —$OR^{2a}$; $R^{2a}$ is methyl; $R^3$ is $C_{3-6}$cycloalkyl optionally substituted with one, two, or three $R^{20b}$; and each $R^{20b}$ is independently —CN or $C_{1-3}$haloalkyl. In embodiments of a compound of Formula (I'-1); $L^1$ is a bond; $R^4$ is hydrogen; $R^6$ is hydrogen; $R^1$ is a

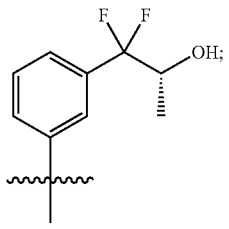 [SMILES: *c1cccc(C(F)(F)[C@@H](C)O)c1]

$R^2$ is —$OR^{2a}$; $R^{2a}$ is methyl; $R^3$ is $C_{3-10}$cycloalkyl optionally substituted with one, two, or three $R^{20b}$; and each $R^{20b}$ is independently —CN or $C_{1-3}$ haloalkyl. In embodiments of a compound of Formula (I'-1); $L^1$ is a bond; $R^4$ is hydrogen; $R^6$ is hydrogen; $R^1$ is a

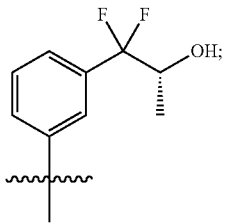 [SMILES: *c1cccc(C(F)(F)[C@@H](C)O)c1]

$R^2$ is —$OR^{2a}$; $R^{2a}$ is methyl; $R^3$ is $C_{3-10}$cycloalkyl optionally substituted with one, two, or three $R^{20b}$; and each $R^{20b}$ is independently selected from amino; —CN; $C_{1-3}$alkyl; $C_{1-3}$alkoxy; $C_{1-3}$haloalkyl; —OH; —N($R^{24}$)C(O)$R^{25}$; and —C(O)N($R^{22}$)($R^{23}$).

In embodiments of a compound of Formula (I'-1); $L^1$ is a bond; $R^4$ is hydrogen; $R^6$ is hydrogen; $R^1$ is a phenyl substituted with one or more $R^{10}$; each $R^{10}$ is independently selected from halogen and $C_{1-4}$alkyl optionally substituted with one, two, or three $R^{20d}$; each $R^{20d}$ is independently selected from halogen and —OH; $R^2$ is —$OR^{2a}$; $R^{2a}$ is methyl; and $R^3$ is a

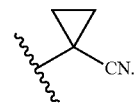 [SMILES: *C1(C#N)CC1]

In embodiments of a compound of Formula (I'-1); $L^1$ is a bond; $R^4$ is hydrogen; $R^6$ is hydrogen; $R^1$ is a phenyl substituted with one or more $R^{10}$; each $R^{10}$ is independently selected from halogen and $C_{1-4}$alkyl optionally substituted with one, two, or three $R^{20d}$; each $R^{20d}$ is independently selected from halogen and —OH; $R^2$ is —$OR^{2a}$; $R^{2a}$ is methyl; $R^3$ is cyclopropyl optionally substituted with one $R^{20b}$, and $R^{20b}$ is —CN. In embodiments of a compound of Formula (I'-1); $L^1$ is a bond; $R^4$ is hydrogen; $R^6$ is hydrogen; $R^1$ is a phenyl substituted with one or more $R^{10}$; each $R^{10}$ is independently selected from halogen and $C_{1-4}$alkyl optionally substituted with one, two, or three $R^{20d}$; each $R^{20d}$ is independently selected from halogen and —OH; $R^2$ is —$OR^{2a}$; $R^{2a}$ is methyl; $R^3$ is $C_{3-4}$cycloalkyl optionally substituted with one $R^{20b}$; and $R^{20b}$ is —CN. In embodiments of a compound of Formula (I'-1); $L^1$ is a bond; $R^4$ is hydrogen; $R^6$ is hydrogen; $R^1$ is a phenyl substituted with one or more $R^{10}$; each $R^{10}$ is independently selected from halogen and $C_{1-4}$alkyl optionally substituted with one, two, or three $R^{20d}$; each $R^{20d}$ is independently selected from halogen and —OH; $R^2$ is —$OR^{2a}$; $R^{2a}$ is methyl; $R^3$ is $C_{3-4}$cycloalkyl optionally substituted with one, two, or three $R^{20b}$; and $R^{20b}$ is —CN. In embodiments of a compound of Formula (I'-1); $L^1$ is a bond; $R^4$ is hydrogen; $R^6$ is hydrogen; $R^1$ is a phenyl substituted with one or more $R^{10}$; each $R^{10}$ is independently selected from halogen and $C_{1-4}$alkyl optionally substituted with one, two, or three $R^{20d}$; each $R^{20d}$ is independently selected from halogen and —OH; $R^2$ is —$OR^{2a}$; $R^{2a}$ is methyl; $R^3$ is $C_{3-4}$cycloalkyl optionally substituted with one, two, or three $R^{20b}$; and each $R^{20b}$ is independently —CN or $C_{1-3}$haloalkyl. In embodiments of a compound of Formula (I'-1); $L^1$ is a bond; $R^4$ is hydrogen; $R^6$ is hydrogen; $R^1$ is a phenyl substituted with one or more $R^{10}$; each $R^{10}$ is independently selected from halogen and $C_{1-4}$alkyl optionally substituted with one, two, or three $R^{20d}$; each $R^{20d}$ is independently selected from halogen and —OH; $R^2$ is —$OR^{2a}$; $R^{2a}$ is methyl; $R^3$ is $C_{3-6}$cycloalkyl optionally substituted with one, two, or three $R^{20b}$; and each $R^{20b}$ is independently —CN or $C_{1-3}$haloalkyl. In embodiments of a compound of Formula (I'-1); $L^1$ is a bond; $R^4$ is hydrogen; $R^6$ is hydrogen; $R^1$ is a phenyl substituted with one or more $R^{10}$; each $R^{10}$ is independently selected from halogen and $C_{1-4}$alkyl optionally substituted with one, two, or three $R^{20d}$; each $R^{20d}$ is independently selected from halogen and —OH; $R^2$ is —$OR^{2a}$; $R^{2a}$ is methyl; $R^3$ is $C_{3-10}$cycloalkyl optionally substituted with one, two, or three $R^{20b}$; and each $R^{20b}$ is independently —CN or $C_{1-3}$haloalkyl. In embodiments of a compound of Formula (I'-1); $L^1$ is a bond; $R^4$ is hydrogen; $R^6$ is hydrogen; $R^1$ is a phenyl substituted with one or more $R^{10}$; each $R^{10}$ is independently selected from halogen and $C_{1-4}$alkyl optionally substituted with one, two, or three $R^{20d}$; each $R^{20d}$ is independently selected from halogen and —OH; $R^2$ is —OR$^{2a}$; $R^{2a}$ is methyl; $R^3$ is $C_{3-10}$cycloalkyl optionally substituted with one, two, or three $R^{20b}$; and each $R^{20b}$ is independently selected from amino; —CN; $C_{1-3}$alkyl; $C_{1-3}$alkoxy; $C_{1-3}$haloalkyl; —OH; —N(R$^{24}$)C(O)R$^{25}$; and —C(O)N(R$^{22}$)(R$^{23}$).

In embodiments of a compound of Formula (I'-1); $L^1$ is a bond; $R^4$ is hydrogen; $R^6$ is hydrogen; $R^1$ is a phenyl substituted with one or more $R^{10}$; each $R^{10}$ is independently selected from halogen and $C_{1-4}$alkyl optionally substituted with one, two, or three $R^{20d}$; each $R^{20d}$ is independently selected from halogen, —OH, $C_{2-5}$heterocycloalkyl optionally substituted with one, two, or three $C_{1-6}$alkyl (e.g., methyl, ethyl, or propyl), and —OR$^{21}$, wherein $R^{21}$ is $C_{2-5}$heterocycloalkyl optionally substituted with one, two, or three $C_{1-6}$alkyl (e.g., methyl, ethyl, propyl, or butyl); $R^2$ is —OR$^{2a}$; $R^{2a}$ is methyl; and $R^3$ is

[structure: cyclopropyl with CN]

In embodiments of a compound of Formula (I'-1); $L^1$ is a bond; $R^4$ is hydrogen; $R^6$ is hydrogen; $R^1$ is a phenyl substituted with one or more $R^{10}$; each $R^{10}$ is independently selected from halogen and $C_{1-4}$alkyl optionally substituted with one, two, or three $R^{20d}$; each $R^{20d}$ is independently selected from halogen, —OH, $C_{2-5}$heterocycloalkyl optionally substituted with one, two, or three $C_{1-6}$alkyl (e.g., methyl, ethyl, or propyl), and —OR$^{21}$, wherein $R^{21}$ is $C_{2-5}$heterocycloalkyl optionally substituted with one, two, or three $C_{1-6}$alkyl (e.g., methyl, ethyl, propyl, or butyl); $R^3$ is cyclopropyl optionally substituted with one $R^{20b}$; and $R^{20b}$ is —CN. In embodiments of a compound of Formula (I'-1); $L^1$ is a bond; $R^4$ is hydrogen; $R^6$ is hydrogen; $R^1$ is a phenyl substituted with one or more $R^{10}$; each $R^{10}$ is independently selected from halogen and $C_{1-4}$alkyl optionally substituted with one, two, or three $R^{20d}$; each $R^{20d}$ is independently selected from halogen, —OH, $C_{2-5}$heterocycloalkyl optionally substituted with one, two, or three $C_{1-6}$alkyl (e.g., methyl, ethyl, or propyl), and —OR$^{21}$, wherein $R^{21}$ is $C_{2-5}$heterocycloalkyl optionally substituted with one, two, or three $C_{1-6}$alkyl (e.g., methyl, ethyl, propyl, or butyl); $R^2$ is —OR$^{2a}$; $R^{2a}$ is methyl; $R^3$ is $C_{3-4}$cycloalkyl optionally substituted with one $R^{20b}$; and $R^{20b}$ is —CN. In embodiments of a compound of Formula (I'-1); $L^1$ is a bond; $R^4$ is hydrogen; $R^6$ is hydrogen; $R^1$ is a phenyl substituted with one or more $R^{10}$; each $R^{10}$ is independently selected from halogen and $C_{1-4}$alkyl optionally substituted with one, two, or three $R^{20d}$; each $R^{20d}$ is independently selected from halogen, —OH, $C_{2-5}$heterocycloalkyl optionally substituted with one, two, or three $C_{1-6}$alkyl (e.g., methyl, ethyl, or propyl), and —OR$^{21}$, wherein $R^{21}$ is $C_{2-5}$heterocycloalkyl optionally substituted with one, two, or three $C_{1-6}$alkyl (e.g., methyl, ethyl, propyl, or butyl); $R^2$ is —OR$^{2a}$; $R^{2a}$ is methyl; $R^3$ is $C_{3-4}$cycloalkyl optionally substituted with one, two, or three $R^{20b}$; and each $R^{20b}$ is independently —CN or $C_{1-3}$haloalkyl. In embodiments of a compound of Formula (I'-1); $L^1$ is a bond; $R^4$ is hydrogen; $R^6$ is hydrogen; $R^1$ is a phenyl substituted with one or more $R^{10}$; each $R^{10}$ is independently selected from halogen and $C_{1-4}$alkyl optionally substituted with one, two, or three $R^{20d}$; each $R^{20d}$ is independently selected from halogen, —OH, $C_{2-5}$heterocycloalkyl optionally substituted with one, two, or three $C_{1-6}$alkyl (e.g., methyl, ethyl, or propyl), and —OR$^{21}$, wherein $R^{21}$ is $C_{2-5}$heterocycloalkyl optionally substituted with one, two, or three $C_{1-6}$alkyl (e.g., methyl, ethyl, propyl, or butyl); $R^2$ is —OR$^{2a}$; $R^{2a}$ is methyl; $R^3$ is $C_{3-6}$cycloalkyl optionally substituted with one, two, or three $R^{20b}$; and each $R^{20b}$ is independently —CN or $C_{1-3}$haloalkyl. In embodiments of a compound of Formula (I'-1); $L^1$ is a bond; $R^4$ is hydrogen; $R^6$ is hydrogen; $R^1$ is a phenyl substituted with one or more $R^{10}$; each $R^{10}$ is independently selected from halogen and $C_{1-4}$alkyl optionally substituted with one, two, or three $R^{20d}$; each $R^{20d}$ is independently selected from halogen, —OH, $C_{2-5}$heterocycloalkyl optionally substituted with one, two, or three $C_{1-6}$alkyl (e.g., methyl, ethyl, or propyl), and —OR$^{21}$, wherein $R^{21}$ is $C_{2-5}$heterocycloalkyl optionally substituted with one, two, or three $C_{1-6}$alkyl (e.g., methyl, ethyl, propyl, or butyl); $R^2$ is —OR$^{2a}$; $R^{2a}$ is methyl; $R^3$ is $C_{3-10}$cycloalkyl optionally substituted with one, two, or three $R^{20b}$; and each $R^{20b}$ is independently —CN or $C_{1-3}$haloalkyl. In embodiments of a compound of Formula (I'-1); $L^1$ is a bond; $R^4$ is hydrogen; $R^6$ is hydrogen; $R^1$ is a phenyl substituted with one or more $R^{10}$; each $R^{10}$ is independently selected from halogen and $C_{1-4}$alkyl optionally substituted with one, two, or three $R^{20d}$; each $R^{20d}$ is independently selected from halogen, —OH, $C_{2-5}$heterocycloalkyl optionally substituted with one, two, or three $C_{1-6}$alkyl (e.g., methyl, ethyl, or propyl), and —OR$^{21}$, wherein $R^{21}$ is $C_{2-5}$heterocycloalkyl optionally substituted with one, two, or three $C_{1-6}$alkyl (e.g., methyl, ethyl, propyl, or butyl); $R^2$ is —OR$^{2a}$; $R^{2a}$ is methyl; $R^3$ is $C_{3-10}$cycloalkyl optionally substituted with one, two, or three $R^{20b}$; and each $R^{20b}$ is independently selected from amino; —CN; $C_{1-3}$alkyl; $C_{1-3}$alkoxy; $C_{1-3}$haloalkyl; —OH; —N(R$^{24}$)C(O)R$^{25}$; and —C(O)N(R$^{22}$)(R$^{23}$).

In embodiments of a compound of Formula (I'-1); $L^1$ is a bond; $R^4$ is hydrogen; $R^6$ is hydrogen; $R^1$ is a 6-10 membered aryl ring substituted with one or more $R^{10}$; each $R^{10}$ is independently selected from halogen and $C_{1-4}$alkyl optionally substituted with one, two, or three $R^{20d}$; each $R^{20d}$ is independently selected from halogen, —OH, $C_{2-5}$heterocycloalkyl optionally substituted with one, two, or three $C_{1-6}$alkyl (e.g., methyl, ethyl, or propyl), and —OR$^{21}$, wherein $R^{21}$ is $C_{2-5}$heterocycloalkyl optionally substituted with one, two, or three $C_{1-6}$alkyl (e.g., methyl, ethyl, propyl, or butyl); $R^2$ is —OR$^{2a}$; $R^{2a}$ is methyl; and $R^3$ is

[structure: cyclopropyl with CN]

In embodiments of a compound of Formula (I'-1); $L^1$ is a bond; $R^4$ is hydrogen; $R^6$ is hydrogen; $R^1$ is a 6-10 membered aryl ring substituted with one or more $R^{10}$; each $R^{10}$ is independently selected from halogen and $C_{1-4}$alkyl optionally substituted with one, two, or three $R^{20d}$; each $R^{20d}$ is independently selected from halogen, —OH, $C_{2-5}$heterocycloalkyl optionally substituted with one, two, or three $C_{1-6}$alkyl (e.g., methyl, ethyl, or propyl), and —$OR^{21}$, wherein $R^{21}$ is $C_{2-5}$heterocycloalkyl optionally substituted with one, two, or three $C_{1-6}$alkyl (e.g., methyl, ethyl, propyl, or butyl); $R^3$ is cyclopropyl optionally substituted with one $R^{20b}$; and $R^{20b}$ is —CN. In embodiments of a compound of Formula (I'-1); $L^1$ is a bond; $R^4$ is hydrogen; $R^6$ is hydrogen; $R^1$ is a 6-10 membered aryl ring substituted with one or more $R^{10}$; each $R^{10}$ is independently selected from halogen and $C_{1-4}$alkyl optionally substituted with one, two, or three $R^{20d}$; each $R^{20d}$ is independently selected from halogen, —OH, $C_{2-5}$heterocycloalkyl optionally substituted with one, two, or three $C_{1-6}$alkyl (e.g., methyl, ethyl, or propyl), and —$OR^{21}$, wherein $R^{21}$ is $C_{2-5}$heterocycloalkyl optionally substituted with one, two, or three $C_{1-6}$alkyl (e.g., methyl, ethyl, propyl, or butyl); $R^2$ is —$OR^{2a}$; $R^{2a}$ is methyl; $R^3$ is $C_{3-4}$cycloalkyl optionally substituted with one $R^{20b}$; and $R^{20b}$ is —CN. In embodiments of a compound of Formula (I'-1); $L^1$ is a bond; $R^4$ is hydrogen; $R^6$ is hydrogen; $R^1$ is a 6-10 membered aryl ring substituted with one or more $R^{10}$; each $R^{10}$ is independently selected from halogen and $C_{1-4}$alkyl optionally substituted with one, two, or three $R^{20d}$; each $R^{20d}$ is independently selected from halogen, —OH, $C_{2-5}$heterocycloalkyl optionally substituted with one, two, or three $C_{1-6}$alkyl (e.g., methyl, ethyl, or propyl), and —$OR^{21}$, wherein $R^{21}$ is $C_{2-5}$heterocycloalkyl optionally substituted with one, two, or three $C_{1-6}$alkyl (e.g., methyl, ethyl, propyl, or butyl); $R^2$ is —$OR^{2a}$; $R^{2a}$ is methyl; $R^3$ is $C_{3-4}$cycloalkyl optionally substituted with one, two, or three $R^{20b}$; and each $R^{20b}$ is independently —CN or $C_{1-3}$haloalkyl. In embodiments of a compound of Formula (I'-1); $L^1$ is a bond; $R^4$ is hydrogen; $R^6$ is hydrogen; $R^1$ is a 6-10 membered aryl ring substituted with one or more $R^{10}$; each $R^{10}$ is independently selected from halogen and $C_{1-4}$alkyl optionally substituted with one, two, or three $R^{20d}$; each $R^{20d}$ is independently selected from halogen, —OH, $C_{2-5}$heterocycloalkyl optionally substituted with one, two, or three $C_{1-6}$alkyl (e.g., methyl, ethyl, or propyl), and —$OR^{21}$, wherein $R^{21}$ is $C_{2-5}$heterocycloalkyl optionally substituted with one, two, or three $C_{1-6}$alkyl (e.g., methyl, ethyl, propyl, or butyl); $R^2$ is —$OR^{2a}$; $R^{2a}$ is methyl; $R^3$ is $C_{3-6}$cycloalkyl optionally substituted with one, two, or three $R^{20b}$; and each $R^{20b}$ is independently —CN or $C_{1-3}$haloalkyl. In embodiments of a compound of Formula (I'-1); $L^1$ is a bond; $R^4$ is hydrogen; $R^6$ is hydrogen; $R^1$ is a 6-10 membered aryl ring substituted with one or more $R^{10}$; each $R^{10}$ is independently selected from halogen and $C_{1-4}$alkyl optionally substituted with one, two, or three $R^{20d}$; each $R^{20d}$ is independently selected from halogen, —OH, $C_{2-5}$heterocycloalkyl optionally substituted with one, two, or three $C_{1-6}$alkyl (e.g., methyl, ethyl, or propyl), and —$OR^{21}$, wherein $R^{21}$ is $C_{2-5}$heterocycloalkyl optionally substituted with one, two, or three $C_{1-6}$alkyl (e.g., methyl, ethyl, propyl, or butyl); $R^2$ is —$OR^{2a}$; $R^{2a}$ is methyl; $R^3$ is $C_{3-10}$cycloalkyl optionally substituted with one, two, or three $R^{20b}$; and each $R^{20b}$ is independently —CN or $C_{1-3}$haloalkyl. In embodiments of a compound of Formula (I'-1); $L^1$ is a bond; $R^4$ is hydrogen; $R^6$ is hydrogen; $R^1$ is a 6-10 membered aryl ring substituted with one or more $R^{10}$; each $R^{10}$ is independently selected from halogen and $C_{1-4}$alkyl optionally substituted with one, two, or three $R^{20d}$; each $R^{20d}$ is independently selected from halogen, —OH, $C_{2-5}$heterocycloalkyl optionally substituted with one, two, or three $C_{1-6}$alkyl (e.g., methyl, ethyl, or propyl), and —$OR^{21}$, wherein $R^{21}$ is $C_{2-5}$heterocycloalkyl optionally substituted with one, two, or three $C_{1-6}$alkyl (e.g., methyl, ethyl, propyl, or butyl); $R^2$ is —$OR^{2a}$; $R^{2a}$ is methyl; $R^3$ is $C_{3-10}$cycloalkyl optionally substituted with one, two, or three $R^{20b}$; and each $R^{20b}$ is independently selected from amino; —CN; $C_{1-3}$alkyl; $C_{1-3}$alkoxy; $C_{1-3}$haloalkyl; —OH; —$N(R^{24})C(O)R^{25}$; and —$C(O)N(R^{22})(R^{23})$.

In embodiments of a compound of Formula (I-1); $L^1$ is a bond; $R^4$ is hydrogen; $R^5$ is methyl; $R^6$ is hydrogen; $R^1$ is a

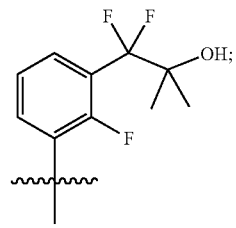 [SMILES: *c1cccc(C(F)(F)C(C)(C)O)c1F]

$R^2$ is —$OR^{2a}$; $R^{2a}$ is methyl; and $R^3$ is

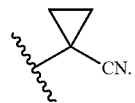

In embodiments of a compound of Formula (I-1); $L^1$ is a bond; $R^4$ is hydrogen; $R^5$ is methyl; $R^6$ is hydrogen; $R^1$ is a

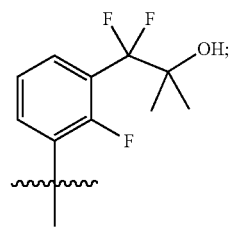 [SMILES: *c1cccc(C(F)(F)C(C)(C)O)c1F]

$R^2$ is —$OR^{2a}$; $R^{2a}$ is methyl; $R^3$ is cyclopropyl optionally substituted with one $R^{20b}$; and $R^{20b}$ is —CN. In embodiments of a compound of Formula (I-1); $L^1$ is a bond; $R^4$ is hydrogen; $R^5$ is methyl; $R^6$ is hydrogen; $R^1$ is a

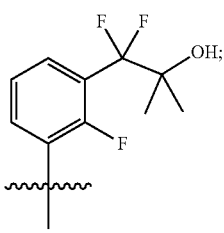 [SMILES: *c1cccc(C(F)(F)C(C)(C)O)c1F]

$R^2$ is —$OR^{2a}$; $R^{2a}$ is methyl; $R^3$ is $C_{3-4}$cycloalkyl optionally substituted with one $R^{20b}$; and $R^{20b}$ is —CN. In embodiments of a compound of Formula (I-1); $L^1$ is a bond; $R^4$ is hydrogen; $R^5$ is methyl; $R^6$ is hydrogen; $R^1$ is a

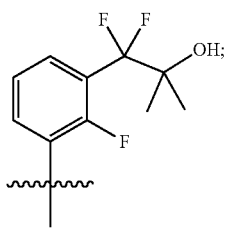 [SMILES: *c1cccc(C(F)(F)C(C)(C)O)c1F]

$R^2$ is —$OR^{2a}$; $R^{2a}$ is methyl; $R^3$ is $C_{3-4}$cycloalkyl optionally substituted with one, two, or three $R^2$; is $R^{20b}$ is —CN. In embodiments of a (I-1); $L^1$ is a bond; $R^4$ is hydrogen; $R_5$ is methyl; $R^6$ is hydrogen; $R^1$ is a

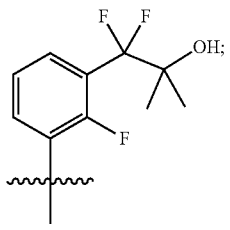 [SMILES: *c1cccc(C(F)(F)C(C)(C)O)c1F]

$R^2$ is —$OR^{2a}$; $R^{2a}$ is methyl; $R^3$ is $C_{3-4}$cycloalkyl optionally substituted with one, two, or three $R^{20b}$; and each $R^{20b}$ is independently —CN or $C_{1-3}$haloalkyl. In embodiments of a compound of Formula (I-1); $L^1$ is a bond; $R^4$ is hydrogen; $R^5$ is methyl; $R^6$ is hydrogen; $R^1$ is a

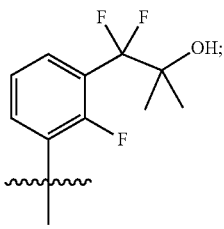

$R^2$ is —$OR^{2a}$; $R^{2a}$ is methyl; $R^3$ is $C_{3-6}$cycloalkyl optionally substituted with one, two, or three $R^{20b}$; and each $R^{20b}$ is independently —CN or $C_{1-3}$haloalkyl. In embodiments of a compound of Formula (I-1); $L^1$ is a bond; $R^4$ is hydrogen; $R^5$ is methyl; $R^6$ is hydrogen; $R^1$ is a

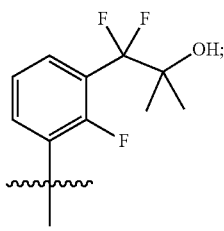 [SMILES: *c1cccc(C(F)(F)C(C)(C)O)c1F]

$R^2$ is —$OR^{2a}$; $R^{2a}$ is methyl; $R^3$ is $C_{3-10}$cycloalkyl optionally substituted with one, two, or three $R^{20b}$; and each $R^{20b}$ is independently —CN or $C_{1-3}$haloalkyl. In embodiments of a compound of Formula (I-1); $L^1$ is a bond; $R^4$ is hydrogen; $R^5$ is methyl; $R^6$ is hydrogen; $R^1$ is a

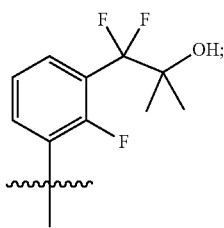 [SMILES: *c1cccc(C(F)(F)C(C)(C)O)c1F]

$R^2$ is —$OR^{2a}$; $R^{2a}$ is methyl; $R^3$ is $C_{3-10}$cycloalkyl optionally substituted with one, two, or three $R^{20b}$; and each $R^{20b}$ is independently selected from amino; —CN; $C_{1-3}$alkyl; $C_{1-3}$alkoxy; $C_{1-3}$haloalkyl; —OH; —$N(R^{24})C(O)R^{25}$; and —$C(O)N(R^{22})(R^{23})$.

In embodiments of a compound of Formula (I-1); $L^1$ is a bond; $R^4$ is hydrogen; $R^5$ is methyl; $R^6$ is hydrogen; $R^1$ is a

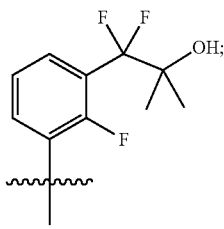 [SMILES: *c1cccc(C(F)(F)C(C)(C)O)c1F]

$R^2$ is —$OR^{2a}$; $R^{2a}$ is methyl; and $R^3$ is

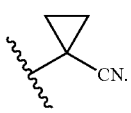 [SMILES: *C1(C#N)CC1]

In embodiments of a compound of Formula (I-1); $L^1$ is a bond; $R^4$ is hydrogen; $R^5$ is methyl; $R^6$ is hydrogen; $R^1$ is a

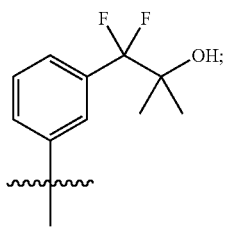 [SMILES: *c1cccc(C(F)(F)C(C)(C)O)c1]

$R^2$ is —$OR^{2a}$; $R^{2a}$ is methyl; $R^3$ is cyclopropyl optionally substituted with one $R^{20b}$; and $R^{20b}$ is —CN. In embodiments of a compound of Formula (I-1); $L^1$ is a bond; $R^4$ is hydrogen; $R^5$ is methyl; $R^6$ is hydrogen; $R^1$ is a

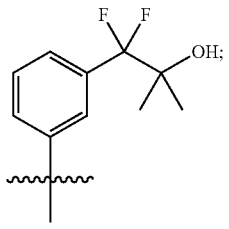 [SMILES: *c1cccc(C(F)(F)C(C)(C)O)c1]

$R^2$ is —$OR^{2a}$; $R^{2a}$ is methyl; $R^3$ is $C_{3-4}$cycloalkyl optionally substituted with one $R^{20b}$; and $R^{20b}$ is —CN. In embodiments of a compound of Formula (I-1); $L^1$ is a bond; $R^4$ is hydrogen; $R^5$ is methyl; $R^6$ is hydrogen; $R^1$ is a

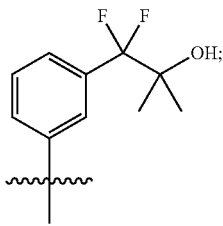 [SMILES: *c1cccc(C(F)(F)C(C)(C)O)c1]

$R^2$ is —$OR^{2a}$; $R^{2a}$ is methyl; $R^3$ is $C_{3-4}$cycloalkyl optionally substituted with one, two, or three $R^{20b}$; and $R^{20b}$ is —CN. In embodiments of a compound of Formula (I-1); $L^1$ is a bond; $R^4$ is hydrogen; $R^5$ is methyl; $R^6$ is hydrogen; $R^1$ is

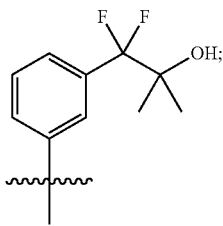 [SMILES: *c1cccc(C(F)(F)C(C)(C)O)c1]

$R^2$ is —$OR^{2a}$; $R^{2a}$ is methyl; $R^3$ is $C_{3-4}$cycloalkyl optionally substituted with one, two, or three $R^{20b}$; and each $R^{20b}$ is independently —CN or $C_{1-3}$haloalkyl. In embodiments of a compound of Formula (I-1); $L^1$ is a bond; $R^5$ is methyl; $R^6$ is hydrogen; $R^1$ is a

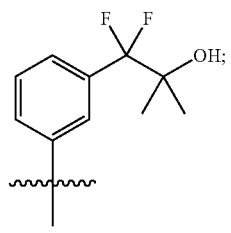 [SMILES: *c1cccc(C(F)(F)C(C)(C)O)c1]

$R^2$ is —$OR^{2a}$; $R^{2a}$ is methyl; $R^3$ is $C_{3-6}$cycloalkyl optionally substituted with one, two, or three $R^{20b}$; and each $R^{20b}$ is independently —CN or $C_{1-3}$haloalkyl. In embodiments of a compound of Formula (I-1); $L^1$ is a bond; $R^4$ is hydrogen; $R^5$ is methyl; $R^6$ is hydrogen; $R^1$ is a

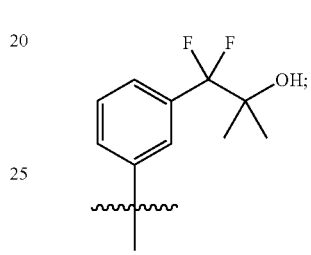

$R^2$ is —$OR^{2a}$; $R^{2a}$ is methyl; $R^3$ is $C_{3-10}$cycloalkyl optionally substituted with one, two, or three $R^{20b}$; and each $R^{20b}$ is independently —CN or $C_{1-3}$haloalkyl. In embodiments of a compound of Formula (I-1); $L^1$ is a bond; $R^4$ is hydrogen; $R^5$ is methyl; $R^6$ is hydrogen; $R^1$ is a

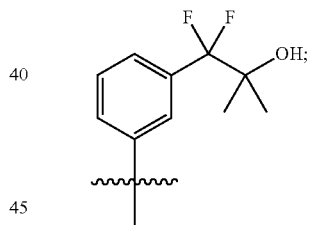

$R^2$ is —$OR^{2a}$; $R^{2a}$ is methyl; $R^3$ is $C_{3-10}$cycloalkyl optionally substituted with one, two, or three $R^{20b}$; and each $R^{20b}$ is independently selected from amino; —CN; $C_{1-3}$alkyl; $C_{1-3}$alkoxy; $C_{1-3}$haloalkyl; —OH; —$N(R^{24})C(O)R^{25}$; and —$C(O)N(R^{22})(R^{23})$.

In embodiments of a compound of Formula (I-1); $L^1$ is a bond; $R^4$ is hydrogen; $R^5$ is methyl; $R^6$ is hydrogen; $R^1$ is a

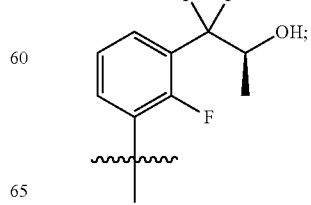

$R^2$ is —$OR^{2a}$; $R^{2a}$ is methyl; and $R^3$ is

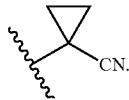

In embodiments of a compound of Formula (I-1); $L^1$ is a bond; $R^4$ is hydrogen; $R^5$ is methyl; $R^6$ is hydrogen; $R^1$ is a

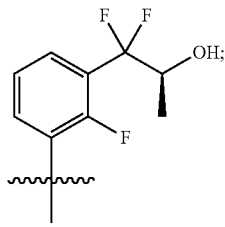 [SMILES: *c1cccc(C(F)(F)[C@H](C)O)c1F]

$R^2$ is —$OR^{2a}$; $R^{2a}$ is methyl; $R^3$ is cyclopropyl optionally substituted with one $R^{20b}$; and $R^{20b}$ is —CN. In embodiments of a compound of Formula (I-1); $L^1$ is a bond; $R^4$ is hydrogen; $R^5$ is methyl; $R^6$ is hydrogen; $R^1$ is a

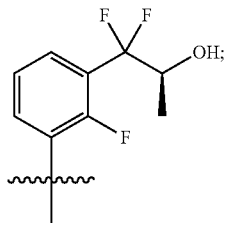 [SMILES: *c1cccc(C(F)(F)[C@H](C)O)c1F]

$R^2$ is —$OR^{2a}$; $R^{2a}$ is methyl; $R^3$ is $C_{3-4}$cycloalkyl optionally substituted with one $R^{20b}$; and $R^{20b}$ is —CN. In embodiments of a compound of Formula (I-1); $L^1$ is a bond; $R^4$ is hydrogen; $R^5$ is methyl; $R^6$ is hydrogen; $R^1$ is a

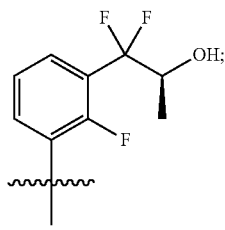 [SMILES: *c1cccc(C(F)(F)[C@H](C)O)c1F]

$R^2$ is —$OR^{2a}$; $R^{2a}$ is methyl; $R^3$ is $C_{3-4}$cycloalkyl optionally substituted with one, two, or three $R^{20b}$; and $R^{20b}$ is —CN. In embodiments of a compound of Formula (I-1); $L^1$ is a bond; $R^4$ is hydrogen; $R^5$ is methyl; $R^6$ is hydrogen; $R^1$ is a

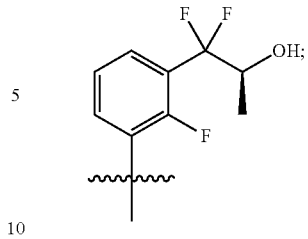

$R^2$ is —$OR^{2a}$; $R^{2a}$ is methyl; $R^3$ is $C_{3-4}$cycloalkyl optionally substituted with one, two, or three $R^{20b}$; and each $R^{20b}$ is independently —CN or $C_{1-3}$haloalkyl. In embodiments of a compound of Formula (I-1); $L^1$ is a bond; $R^4$ is hydrogen; $R^5$ is methyl; $R^6$ is hydrogen; $R^1$ is

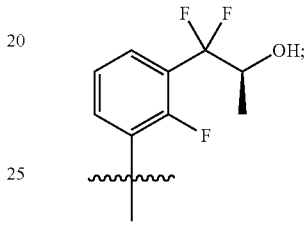

$R^2$ is —$OR^{2a}$; $R^{2a}$ is methyl; $R^3$ is $C_{3-6}$cycloalkyl optionally substituted with one, two, or three $R^{20b}$; and each $R^{20b}$ is independently —CN or $C_{1-3}$haloalkyl. In embodiments of a compound of Formula (I-1); $L^1$ is a bond; $R^4$ is hydrogen; $R^5$ is methyl; $R^6$ is hydrogen; $R^1$ is a

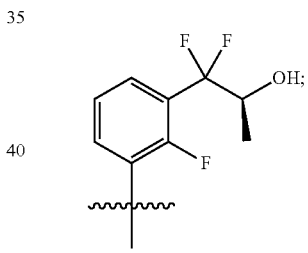

$R^2$ is —$OR^{2a}$; $R^{2a}$ is methyl; $R^3$ is $C_{3-10}$cycloalkyl optionally substituted with one, two, or three $R^{21b}$; and each $R^{20b}$ is independently —CN or $C_{1-3}$haloalkyl. In embodiments of a compound of Formula (I-1); $L^1$ is a bond; $R^4$ is hydrogen; $R^5$ is methyl; $R^6$ is hydrogen; $R^1$ is a

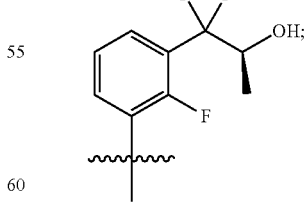

$R^2$ is —$OR^{2a}$; $R^{2a}$ is methyl; $R^3$ is $C_{3-10}$cycloalkyl optionally substituted with one, two, or three $R^{20b}$; and each $R^{20b}$ is independently selected from amino; —CN; $C_{1-3}$alkyl; $C_{1-3}$alkoxy; $C_{1-3}$haloalkyl; —OH; —$N(R^{24})C(O)R^{25}$; and —$C(O)N(R^{22})(R^{23})$.

In embodiments of a compound of Formula (I-1); LF is a bond; $R^4$ is hydrogen; $R^5$ is methyl; $R^6$ is hydrogen; $R^1$ is a

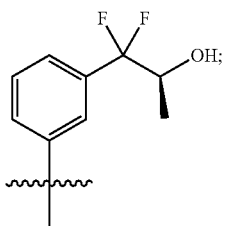 [SMILES: *c1cccc(C(F)(F)[C@H](C)O)c1]

$R^2$ is —$OR^{2a}$; $R^{2a}$ is methyl; and $R^3$ is

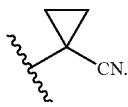

In embodiments of a compound of Formula (I-1); $L^1$ is a bond; $R^4$ is hydrogen; $R^5$ is methyl; $R^6$ is hydrogen; $R^1$ is a

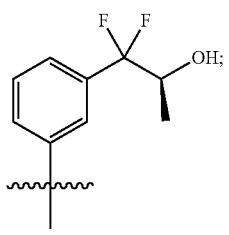 [SMILES: *c1cccc(C(F)(F)[C@H](C)O)c1]

$R^2$ is —$OR^{2a}$; $R^{2a}$ is methyl; $R^3$ is cyclopropyl optionally substituted with one $R^{20b}$; and $R^{20b}$ is —CN. In embodiments of a compound of Formula (I-1); $L^1$ is a bond; $R^4$ is hydrogen; $R^5$ is methyl; $R^6$ is hydrogen; $R^1$ is a

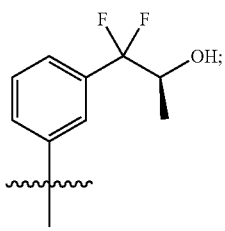 [SMILES: *c1cccc(C(F)(F)[C@H](C)O)c1]

$R^2$ is —$OR^{2a}$; $R^{2a}$ is methyl; $R^3$ is $C_{3-4}$cycloalkyl optionally substituted with one $R^{20b}$; and $R^{20b}$ is —CN. In embodiments of a compound of Formula (I-1); $L^1$ is a bond; $R^4$ is hydrogen; $R^5$ is methyl; $R^6$ is hydrogen; $R^1$ is a

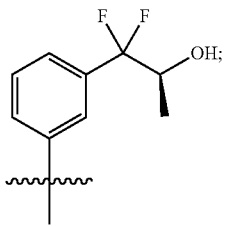 [SMILES: *c1cccc(C(F)(F)[C@H](C)O)c1]

$R^2$ is —$OR^{2a}$; $R^{2a}$ is methyl; $R^3$ is $C_{3-4}$cycloalkyl optionally substituted with one, two, or three $R^{20b}$; and $R^{20b}$ is —CN. In embodiments of a compound of Formula (I-1); $L^1$ is a bond; $R^4$ is hydrogen; $R^5$ is methyl; $R^6$ is hydrogen; $R^1$ is a

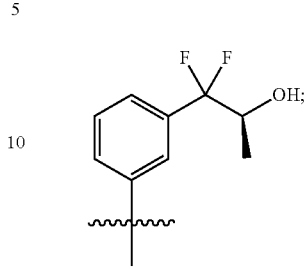

$R^2$ is —$OR^{2a}$; $R^{2a}$ is methyl; $R^3$ is $C_{3-4}$cycloalkyl optionally substituted with one, two, or three $R^{20b}$; and each $R^{20b}$ is independently —CN or $C_{1-3}$haloalkyl. In embodiments of a compound of Formula (I-1); $L^1$ is a bond; $R^4$ is hydrogen; $R^5$ is methyl; $R^6$ is hydrogen; $R^1$ is a

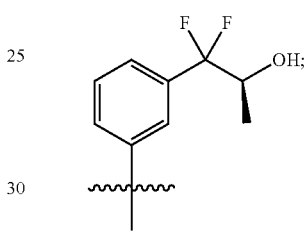

$R^2$ is —$OR^{2a}$; $R^{2a}$ is methyl; $R^3$ is $C_{3-6}$cycloalkyl optionally substituted with one, two, or three $R^{20b}$; and each $R^{20b}$ is independently —CN or $C_{1-3}$haloalkyl. In embodiments of a compound of Formula (I-1); $L^1$ is a bond; $R^4$ is hydrogen; $R^5$ is methyl; $R^6$ is hydrogen; $R^1$ is a

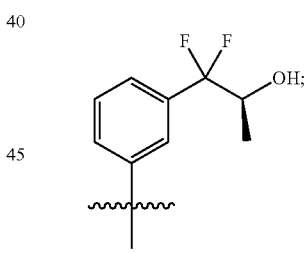

$R^2$ is —$OR^{2a}$; $R^{2a}$ is methyl; $R^3$ is $C_{3-10}$cycloalkyl optionally substituted with one, two, or three $R^{20b}$; and each $R^{20b}$ is independently —CN or $C_{1-3}$haloalkyl. In embodiments of a compound of Formula (I-1); $L^1$ is a bond; $R^4$ is hydrogen; $R^5$ is methyl; $R^6$ is hydrogen; $R^1$ is a

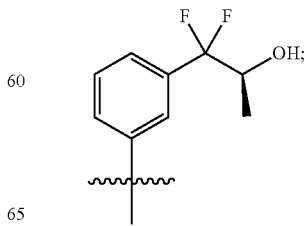

$R^2$ is —$OR^{2a}$; $R^{2a}$ is methyl; $R^3$ is $C_{3-10}$cycloalkyl optionally substituted with one, two, or three $R^{20b}$; and each $R^{20b}$ is independently selected from amino; —CN; $C_{1-3}$alkyl; $C_{1-3}$alkoxy; $C_{1-3}$haloalkyl; —OH; —N($R^{24}$)C(O)$R^{25}$; and —C(O)N($R^{22}$)($R^{23}$).

In embodiments of a compound of Formula (I-1); $L^1$ is a bond; $R^4$ is hydrogen; $R^5$ is methyl; $R^6$ is hydrogen; $R^1$ is a

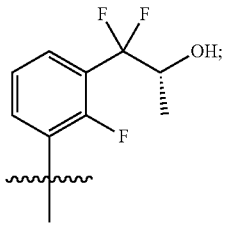 [SMILES: *c1cccc(C(F)(F)[C@@H](C)O)c1F]

$R^2$ is —$OR^{2a}$; $R^{2a}$ is methyl; and $R^3$ is

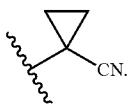

In embodiments of a compound of Formula (I-1); $L^1$ is a bond; $R^4$ is hydrogen; $R^5$ is methyl; $R^6$ is hydrogen; $R^1$ is a

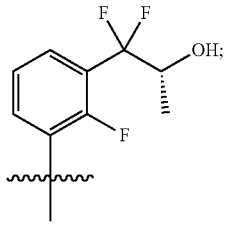 [SMILES: *c1cccc(C(F)(F)[C@@H](C)O)c1F]

$R^2$ is —$OR^{2a}$; $R^{2a}$ is methyl; $R^3$ is cyclopropyl optionally substituted with one $R^{20b}$; and $R^{20b}$ is —CN. In embodiments of a compound of Formula (I-1); $L^1$ is a bond; $R^4$ is hydrogen; $R^5$ is methyl; $R^6$ is hydrogen; $R^1$ is a

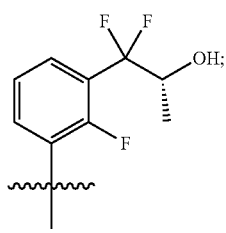

$R^2$ is —$OR^{2a}$; $R^{2a}$ is methyl; $R^3$ is $C_{3-4}$cycloalkyl optionally substituted with one $R^{20b}$; and $R^{20b}$ is —CN. In embodiments of a compound of Formula (I-1); $L^1$ is a bond; $R^4$ is hydrogen; $R^5$ is methyl; $R^6$ is hydrogen; $R^1$ is a

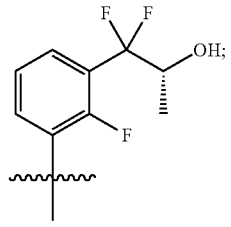 [SMILES: *c1cccc(C(F)(F)[C@@H](C)O)c1F]

$R^2$ is —$OR^{2a}$; $R^{2a}$ is methyl; $R^3$ is $C_{3-4}$cycloalkyl optionally substituted with one, two, or three $R^{20b}$; and $R^{20b}$ is —CN. In embodiments of a compound of Formula (I-1); $L^1$ is a bond; $R^4$ is hydrogen; $R^5$ is methyl; $R^6$ is hydrogen; $R^1$ is a

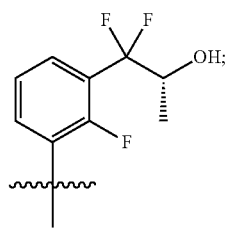 [SMILES: *c1cccc(C(F)(F)[C@@H](C)O)c1F]

$R^2$ is —$OR^{2a}$; $R^{2a}$ is methyl; $R^3$ is $C_{3-4}$cycloalkyl optionally substituted with one, two, or three $R^{20b}$; and each $R^{20b}$ is independently —CN or $C_{1-3}$haloalkyl. In embodiments of a compound of Formula (I-1); $L^1$ is a bond; $R^4$ is hydrogen; $R^5$ is methyl; $R^6$ is hydrogen; $R^1$ is a

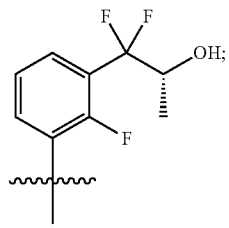 [SMILES: *c1cccc(C(F)(F)[C@@H](C)O)c1F]

$R^2$ is —$OR^{2a}$; $R^{2a}$ is methyl; $R^3$ is $C_{3-6}$cycloalkyl optionally substituted with one, two, or three $R^{20b}$; and each $R^{20b}$ is independently —CN or $C_{1-3}$haloalkyl. In embodiments of a compound of Formula (I-1); $L^1$ is a bond; $R^4$ is hydrogen; $R^5$ is methyl; $R^6$ is hydrogen; $R^1$ is a

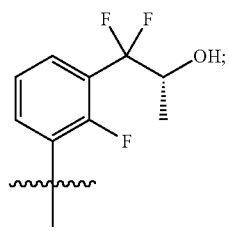 [SMILES: *c1cccc(C(F)(F)[C@@H](C)O)c1F]

$R^2$ is —$OR^{2a}$; $R^{2a}$ is methyl; $R^3$ is $C_{3-10}$cycloalkyl optionally substituted with one, two, or three $R^{20b}$; and each $R^{20b}$ is independently —CN or $C_{1-3}$haloalkyl. In embodiments of a compound of Formula (I-1); $L^1$ is a bond; $R^4$ is hydrogen; $R^5$ is methyl; $R^6$ is hydrogen; $R^1$ is a

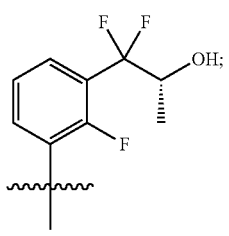 [SMILES: *c1cccc(C(F)(F)[C@@H](C)O)c1F]

$R^2$ is —$OR^{2a}$; $R^{2a}$ is methyl; $R^3$ is $C_{3-10}$cycloalkyl optionally substituted with one, two, or three $R^{20b}$; and each $R^{20b}$ is independently selected from amino; —CN; $C_{1-3}$alkyl; $C_{1-3}$alkoxy; $C_{1-3}$haloalkyl; —OH; —$N(R^{24})C(O)R^{25}$; and —$C(O)N(R^{22})(R^{23})$.

In embodiments of a compound of Formula (I-1); $L^1$ is a bond; $R^4$ is hydrogen; $R^5$ is methyl; $R^6$ is hydrogen; $R^1$ is a

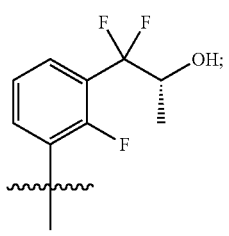 [SMILES: *c1cccc(C(F)(F)[C@@H](C)O)c1F]

$R^2$ is —$OR^{2a}$; $R^{2a}$ is methyl; and $R^3$ is

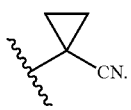

In embodiments of a compound of Formula (I-1); $L^1$ is a bond; $R^4$ is hydrogen; $R^5$ is methyl; $R^6$ is hydrogen; $R^1$ is a

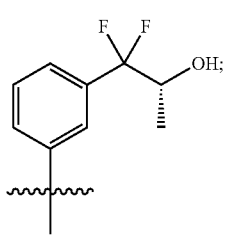 [SMILES: *c1cccc(C(F)(F)[C@@H](C)O)c1]

$R^2$ is —$OR^{2a}$; $R^{2a}$ is methyl; $R^3$ is cyclopropyl optionally substituted with one $R^{20b}$; and $R^{20b}$ is —CN. In embodiments of a compound of Formula (I-1); $L^1$ is a bond; $R^4$ is hydrogen; $R^5$ is methyl; $R^6$ is hydrogen; $R^1$ is a

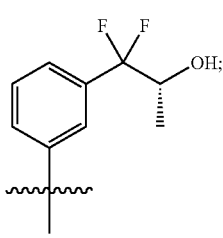 [SMILES: *c1cccc(C(F)(F)[C@@H](C)O)c1]

$R^2$ is —$OR^{2a}$; $R^{2a}$ is methyl; $R^3$ is $C_{3-4}$cycloalkyl optionally substituted with one $R^{20b}$; and $R^{20b}$ is —CN. In embodiments of a compound of Formula (I-1); $L^1$ is a bond; $R^4$ is hydrogen; $R^5$ is methyl; $R^6$ is hydrogen; $R^1$ is a

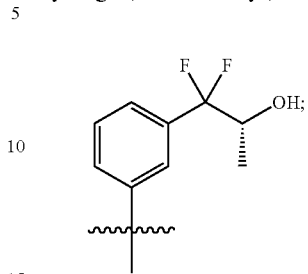

$R^2$ is —$OR^{2a}$; $R^{2a}$ is methyl; $R^3$ is $C_{3-4}$cycloalkyl optionally substituted with one, two, or three $R^{20b}$; and $R^{20b}$ is —CN. In embodiments of a compound of Formula (I-1); $L^1$ is a bond; $R^4$ is hydrogen; $R^5$ is methyl; $R^6$ is hydrogen; $R^1$ is a

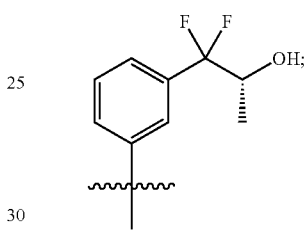

$R^2$ is —$OR^{2a}$; $R^{2a}$ is methyl; $R^3$ is $C_{3-4}$cycloalkyl optionally substituted with one, two, or three $R^{20b}$; and each $R^{20b}$ is independently —CN or $C_{1-3}$haloalkyl. In embodiments of a compound of Formula (I-1); $L^1$ is a bond; $R^4$ is hydrogen; $R^5$ is methyl; $R^6$ is hydrogen; $R^1$ is a

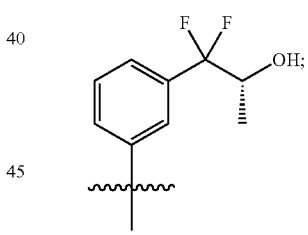

$R^2$ is —$OR^{2a}$; $R^{2a}$ is methyl; $R^3$ is $C_{3-6}$cycloalkyl optionally substituted with one, two, or three $R^{20b}$; and each $R^{20b}$ is independently —CN or $C_{1-3}$haloalkyl. In embodiments of a compound of Formula (I-1); $L^1$ is a bond; $R^4$ is hydrogen; $R^5$ is methyl; $R^6$ is hydrogen; $R^1$ is a

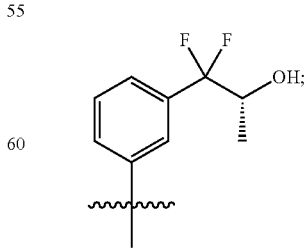

$R^2$ is —$OR^{2a}$; $R^{2a}$ is methyl; $R^3$ is $C_{3-10}$cycloalkyl optionally substituted with one, two, or three $R^{20b}$;

is independently —CN or $C_{1-3}$haloalkyl. In embodiments of a compound of Formula (I-1); $L^1$ is a bond; $R^4$ is hydrogen; $R^5$ is methyl; $R^6$ is hydrogen; $R^1$ is a

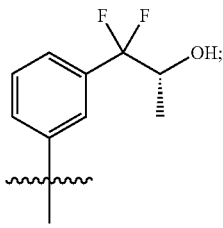 [SMILES: *c1cccc(C(F)(F)[C@@H](C)O)c1]

$R^2$ is —$OR^{2a}$; $R^{2a}$ is methyl; $R^3$ is $C_{3-10}$cycloalkyl optionally substituted with one, two, or three $R^{20b}$; and each $R^{20b}$ is independently selected from amino; —CN; $C_{1-3}$alkyl; $C_{1-3}$alkoxy; $C_{1-3}$haloalkyl; —OH; —$N(R^{24})C(O)R^{25}$; and —$C(O)N(R^{22})(R^{23})$.

In embodiments of a compound of Formula (I-1); $L^1$ is a bond; $R^4$ is hydrogen; $R^5$ is methyl; $R^6$ is hydrogen; $R^1$ is a phenyl substituted with one or more $R^{10}$; each $R^{10}$ is independently selected from halogen and $C_{1-4}$alkyl optionally substituted with one, two, or three $R^{20d}$; each $R^{20d}$ is independently selected from halogen and —OH; $R^2$ is —$OR^{2a}$; $R^{2a}$ is methyl; and $R^3$ is

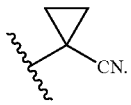 [SMILES: *C1(C#N)CC1]

In embodiments of a compound of Formula (I-1); $L^1$ is a bond; $R^4$ is hydrogen; $R^5$ is methyl; $R^6$ is hydrogen; $R^1$ is a phenyl substituted with one or more $R^{10}$; each $R^{10}$ is independently selected from halogen and $C_{1-4}$alkyl optionally substituted with one, two, or three $R^{20d}$; each $R^{20d}$ is independently selected from halogen and —OH; $R^2$ is —$OR^{2a}$; $R^{2a}$ is methyl; $R^3$ is cyclopropyl optionally substituted with one $R^{20b}$; and $R^{20b}$ is —CN. In embodiments of a compound of Formula (I-1); $L^1$ is a bond; $R^4$ is hydrogen; $R^5$ is methyl; $R^6$ is hydrogen; $R^1$ is a phenyl substituted with one or more $R^{10}$; each $R^{10}$ is independently selected from halogen and $C_{1-4}$ alkyl optionally substituted with one, two, or three $R^{20d}$; each $R^{20d}$ is independently selected from halogen and —OH; $R^2$ is —$OR^{2a}$; $R^{2a}$ is methyl; $R^3$ is $C_{3-4}$cycloalkyl optionally substituted with one $R^{20b}$; and $R^{20b}$ is —CN. In embodiments of a compound of Formula (I-1); $L^1$ is a bond; $R^4$ is hydrogen; $R^5$ is methyl; $R^6$ is hydrogen; $R^1$ is a phenyl substituted with one or more $R^{10}$; each $R^{10}$ is independently selected from halogen and $C_{1-4}$alkyl optionally substituted with one, two, or three $R^{20d}$; each $R^{20d}$ is independently selected from halogen and —OH; $R^2$ is —$OR^{2a}$; $R^{2a}$ is methyl; $R^3$ is $C_{3-4}$cycloalkyl optionally substituted with one, two, or three $R^{20b}$; and each $R^{20b}$ is independently —CN or $C_{1-3}$haloalkyl. In embodiments of a compound of Formula (I-1); $L^1$ is a bond; $R^4$ is hydrogen; $R^5$ is methyl; $R^6$ is hydrogen; $R^1$ is a phenyl substituted with one or more $R^{10}$; each $R^{10}$ is independently selected from halogen and $C_{1-4}$alkyl optionally substituted with one, two, or three $R^{20d}$; each $R^{20d}$ is independently selected from halogen and —OH; $R^2$ is —$OR^{2a}$; $R^{2a}$ is methyl; $R^3$ is $C_{3-6}$cycloalkyl optionally substituted with one, two, or three $R^{20b}$; and each $R^{20b}$ is independently —CN or $C_{1-3}$haloalkyl. In embodiments of a compound of Formula (I-1); $L^1$ is a bond; $R^4$ is hydrogen; $R^5$ is methyl; $R^6$ is hydrogen; $R^1$ is a phenyl substituted with one or more $R^{10}$; each $R^{10}$ is independently selected from halogen and $C_{1-4}$alkyl optionally substituted with one, two, or three $R^{20d}$; each $R^{20d}$ is independently selected from halogen and —OH; $R^2$ is —$OR^{2a}$; $R^{2a}$ is methyl; $R^3$ is $C_{3-10}$cycloalkyl optionally substituted with one, two, or three $R^{20b}$; and each $R^{20b}$ is independently —CN or $C_{1-3}$haloalkyl. In embodiments of a compound of Formula (I-1); $L^1$ is a bond; $R^4$ is hydrogen; $R^5$ is methyl; $R^6$ is hydrogen; $R^1$ is a phenyl substituted with one or more $R^{10}$; each $R^{10}$ is independently selected from halogen and $C_{1-4}$alkyl optionally substituted with one, two, or three $R^{20d}$; each $R^{20d}$ is independently selected from halogen and —OH; $R^2$ is —$OR^{2a}$; $R^{2a}$ is methyl; $R^3$ is $C_{3-10}$cycloalkyl optionally substituted with one, two, or three $R^{20b}$; and each $R^{20b}$ is independently selected from amino; —CN; $C_{1-3}$alkyl; $C_{1-3}$alkoxy; $C_{1-3}$haloalkyl; —OH; —$N(R^{24})C(O)R^{21}$; and —$C(O)N(R^{22})(R^{23})$.

In embodiments of a compound of Formula (I-1); $L^1$ is a bond; $R^4$ is hydrogen; $R^5$ is methyl; $R^6$ is hydrogen; $R^1$ is a phenyl substituted with one or more $R^{10}$; each $R^{10}$ is independently selected from halogen and $C_{1-4}$alkyl optionally substituted with one, two, or three $R^{20d}$; each $R^{20d}$ is independently selected from halogen, —OH, $C_{2-5}$heterocycloalkyl optionally substituted with one, two, or three $C_{1-6}$alkyl (e.g., methyl, ethyl, or propyl), and —$OR^{21}$, wherein $R^{21}$ is $C_{2-5}$heterocycloalkyl optionally substituted with one, two, or three $C_{1-6}$alkyl (e.g., methyl, ethyl, propyl, or butyl); $R^2$ is —$OR^{2a}$; $R^{2a}$ is methyl; and $R^3$ is

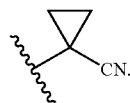 [SMILES: *C1(C#N)CC1]

In embodiments of a compound of Formula (I-1); $L^1$ is a bond; $R^4$ is hydrogen; $R^5$ is methyl; $R^6$ is hydrogen; $R^1$ is a phenyl substituted with one or more $R^{10}$; each $R^{10}$ is independently selected from halogen and $C_{1-4}$alkyl optionally substituted with one, two, or three $R^{20d}$; each $R^{20d}$ is independently selected from halogen, —OH, $C_{2-5}$heterocycloalkyl optionally substituted with one, two, or three $C_{1-6}$ alkyl (e.g., methyl, ethyl, or propyl), and —$OR^{21}$, wherein $R^{21}$ is $C_{2-5}$heterocycloalkyl optionally substituted with one, two, or three $C_{1-6}$alkyl (e.g., methyl, ethyl, propyl, or butyl); $R^3$ is cyclopropyl optionally substituted with one $R^{20b}$; and $R^{20b}$ is —CN. In embodiments of a compound of Formula (I-1); $L^1$ is a bond; $R^4$ is hydrogen; $R^5$ is methyl; $R^6$ is hydrogen; $R^1$ is a phenyl substituted with one or more $R^{10}$; each $R^{10}$ is independently selected from halogen and $C_{1-4}$alkyl optionally substituted with one, two, or three $R^{20d}$; each $R^{20d}$ is independently selected from halogen, —OH, $C_{2-5}$heterocycloalkyl optionally substituted with one, two, or three $C_{1-6}$alkyl (e.g., methyl, ethyl, or propyl), and —$OR^{21}$, wherein $R^{21}$ is $C_{2-5}$heterocycloalkyl optionally substituted with one, two, or three $C_{1-6}$alkyl (e.g., methyl, ethyl, propyl, or butyl); $R^2$ is —$OR^{2a}$; $R^{2a}$ is methyl; $R^3$ $C_{3-4}$cycloalkyl optionally substituted with one $R^{20b}$; and $R^{20b}$ is —CN. In embodiments of a compound of Formula (I-1); $L^1$ is a bond; $R^4$ is hydrogen; $R^5$ is methyl; $R^6$ is hydrogen; $R^1$ is a phenyl substituted with one or more $R^{10}$; each $R^{10}$ is independently selected from halogen and $C_{1-4}$alkyl optionally substituted with one, two, or three $R^{20d}$; each $R^{20d}$ is independently selected from halogen, —OH, $C_{2-5}$heterocycloalkyl optionally substituted with one, two, or three $C_{1-6}$ alkyl (e.g., methyl, ethyl, or propyl), and —$OR^{21}$, wherein $R^{21}$ is $C_{2-5}$heterocycloalkyl optionally substituted with one, two, or three $C_{1-6}$ alkyl (e.g., methyl, ethyl, propyl, or butyl); $R^2$ is —$OR^{2a}$; $R^{2a}$ is methyl; $R^3$ is $C_{3-4}$cycloalkyl optionally substituted with one, two, or three $R^{20b}$; and $R^{20b}$ is —CN. In embodiments of a compound of Formula (I-1); $L^1$ is a bond; $R^4$ is hydrogen; $R^5$ is methyl; $R^6$ is hydrogen; $R^1$ is a phenyl substituted with one or more $R^{10}$; each $R^{10}$ is independently selected from halogen and $C_{1-4}$alkyl optionally substituted with one, two, or three $R^{20d}$; each $R^{20d}$ is independently selected from halogen, —OH, $C_{2-5}$heterocycloalkyl optionally substituted with one, two, or three $C_{1-6}$alkyl (e.g., methyl, ethyl, or propyl), and —$OR^{21}$, wherein $R^{21}$ is $C_{2-5}$heterocycloalkyl optionally substituted with one, two, or three $C_{1-6}$alkyl (e.g., methyl, ethyl, propyl, or butyl); $R^2$ is —$OR^{2a}$; $R^{2a}$ is methyl; $R^3$ is $C_{3-4}$cycloalkyl optionally substituted with one, two, or three $R^{20b}$; and each $R^{20b}$ is independently —CN or $C_{1-3}$haloalkyl. In embodiments of a compound of Formula (I-1); $L^1$ is a bond; $R^4$ is hydrogen; $R^5$ is methyl; $R^6$ is hydrogen; $R^1$ is a phenyl substituted with one or more $R^{10}$; each $R^{10}$ is independently selected from halogen and $C_{1-4}$alkyl optionally substituted with one, two, or three $R^{20d}$; each $R^{20d}$ is independently selected from halogen, —OH, $C_{2-5}$heterocycloalkyl optionally substituted with one, two, or three $C_{1-6}$alkyl (e.g., methyl, ethyl, or propyl), and —$OR^{21}$, wherein $R^{21}$ is $C_{2-5}$heterocycloalkyl optionally substituted with one, two, or three $C_{1-6}$alkyl (e.g., methyl, ethyl, propyl, or butyl); $R^2$ is —$OR^{2a}$; $R^{2a}$ is methyl; $R^3$ is $C_{3-6}$cycloalkyl optionally substituted with one, two, or three $R^{20b}$; and each $R^{20b}$ is independently —CN or $C_{1-3}$haloalkyl. In embodiments of a compound of Formula (I-1); $L^1$ is a bond; $R^4$ is hydrogen; $R^5$ is methyl; $R^6$ is hydrogen; $R^1$ is a phenyl substituted with one or more $R^{10}$; each $R^{10}$ is independently selected from halogen and $C_{1-4}$alkyl optionally substituted with one, two, or three $R^{20d}$; each $R^{20d}$ is independently selected from halogen, —OH, $C_{2-5}$heterocycloalkyl optionally substituted with one, two, or three $C_{1-6}$alkyl (e.g., methyl, ethyl, or propyl), and —$OR^{21}$, wherein $R^{21}$ is $C_{2-5}$heterocycloalkyl optionally substituted with one, two, or three $C_{1-6}$alkyl (e.g., methyl, ethyl, propyl, or butyl); $R^2$ is —$OR^{2a}$; $R^{2a}$ is methyl; $R^3$ is $C_{3-10}$cycloalkyl optionally substituted with one, two, or three $R^{20b}$; and each $R^{20b}$ is independently —CN or $C_{1-3}$haloalkyl. In embodiments of a compound of Formula (I-1); $L^1$ is a bond; $R^4$ is hydrogen; $R^5$ is methyl; $R^6$ is hydrogen; $R^1$ is a phenyl substituted with one or more $R^{10}$; each $R^{10}$ is independently selected from halogen and $C_{1-4}$alkyl optionally substituted with one, two, or three $R^{20d}$; each $R^{20d}$ is independently selected from halogen, —OH, $C_{2-5}$heterocycloalkyl optionally substituted with one, two, or three $C_{1-6}$alkyl (e.g., methyl, ethyl, or propyl), and —$OR^{21}$, wherein $R^{21}$ is $C_{2-5}$heterocycloalkyl optionally substituted with one, two, or three $C_{1-6}$alkyl (e.g., methyl, ethyl, propyl, or butyl); $R^2$ is —$OR^{2a}$; $R^{2a}$ is methyl; $R^3$ is $C_{3-10}$cycloalkyl optionally substituted with one, two, or three $R^{20b}$; and each $R^{20b}$ is independently selected from amino; —CN; $C_{1-3}$alkyl; $C_{1-3}$alkoxy; $C_{1-3}$haloalkyl; —OH; —$N(R^{24})C(O)R^{25}$; and —$C(O)N(R^{22})(R^{23})$.

In embodiments of a compound of Formula (I-1); $L^1$ is a bond; $R^4$ is hydrogen; $R^5$ is methyl; $R^6$ is hydrogen; $R^1$ is a 6-10 membered aryl ring substituted with one or more $R^{10}$; each $R^{10}$ is independently selected from halogen and $C_{1-4}$alkyl optionally substituted with one, two, or three $R^{20d}$; each $R^{20d}$ is independently selected from halogen, —OH, $C_{2-5}$heterocycloalkyl optionally substituted with one, two, or three $C_{1-6}$alkyl (e.g., methyl, ethyl, or propyl), and —$OR^{21}$, wherein $R^{21}$ is $C_{2-5}$heterocycloalkyl optionally substituted with one, two, or three $C_{1-6}$alkyl (e.g., methyl, ethyl, propyl, or butyl); $R^2$ is —$OR^{2a}$; $R^{2a}$ is methyl; and $R^3$ is In embodiments of a compound of Formula (I-1); $L^1$ is a bond; $R^4$ is hydrogen; $R^5$ is methyl; $R^6$ is hydrogen; $R^1$ is a 6-10 membered aryl ring substituted with one or more $R^{10}$; each $R^{10}$ is independently selected from halogen and $C_{1-4}$alkyl optionally substituted with one, two, or three $R^{20d}$; each $R^{20d}$ is independently selected from halogen, —OH, $C_{2-5}$heterocycloalkyl optionally substituted with one, two, or three $C_{1-6}$alkyl (e.g., methyl, ethyl, or propyl), and —$OR^{21}$, wherein $R^{21}$ is $C_{2-5}$heterocycloalkyl optionally substituted with one, two, or three $C_{1-6}$alkyl (e.g., methyl, ethyl, propyl, or butyl); $R^3$ is cyclopropyl optionally substituted with one $R^{20b}$; and $R^{20b}$ is —CN. In embodiments of a compound of Formula (I-1); $L^1$ is a bond; $R^4$ is hydrogen; $R^5$ is methyl; $R^6$ is hydrogen; $R^1$ is a 6-10 membered aryl ring substituted with one or more $R^{10}$; each $R^{10}$ is independently selected from halogen and $C_{1-4}$alkyl optionally substituted with one, two, or three $R^{20d}$; each $R^{20d}$ is independently selected from halogen, —OH, $C_{2-5}$heterocycloalkyl optionally substituted with one, two, or three $C_{1-6}$alkyl (e.g., methyl, ethyl, or propyl), and —$OR^{21}$, wherein $R^{21}$ is $C_{2-5}$heterocycloalkyl optionally substituted with one, two, or three $C_{1-6}$alkyl (e.g., methyl, ethyl, propyl, or butyl); $R^2$ is —$OR^{2a}$; $R^{2a}$ is methyl; $R^3$ is $C_{3-4}$cycloalkyl optionally substituted with one $R^{20b}$; and $R^{20b}$ is —CN. In embodiments of a compound of Formula (I-1); $L^1$ is a bond; $R^4$ is hydrogen; $R^5$ is methyl; $R^6$ is hydrogen; $R^1$ is a 6-10 membered aryl ring substituted with one or more $R^{10}$; each $R^{10}$ is independently selected from halogen and $C_{1-4}$alkyl optionally substituted with one, two, or three $R^{20d}$; each $R^{20d}$ is independently selected from halogen, —OH, $C_{2-5}$heterocycloalkyl optionally substituted with one, two, or three $C_{1-6}$alkyl (e.g., methyl, ethyl, or propyl), and —$OR^{21}$, wherein $R^{21}$ is $C_{2-5}$heterocycloalkyl optionally substituted with one, two, or three $C_{1-6}$alkyl (e.g., methyl, ethyl, propyl, or butyl); $R^2$ is —$OR^{2a}$; $R^{2a}$ is methyl; $R^3$ is $C_{3-4}$cycloalkyl optionally substituted with one, two, or three $R^{20b}$; and $R^{20b}$ is —CN. In embodiments of a compound of Formula (I-1); $L^1$ is a bond; $R^4$ is hydrogen; $R^5$ is methyl; $R^6$ is hydrogen; $R^1$ is a 6-10 membered aryl ring substituted with one or more $R^{10}$; each $R^{10}$ is independently selected from halogen and $C_{1-4}$alkyl optionally substituted with one, two, or three $R^{20d}$; each $R^{20d}$ is independently selected from halogen, —OH, $C_{2-5}$heterocycloalkyl optionally substituted with one, two, or three $C_{1-6}$ alkyl (e.g., methyl, ethyl, or propyl), and —$OR^{21}$, wherein $R^{21}$ is $C_{2-5}$heterocycloalkyl optionally substituted with one, two, or three $C_{1-6}$alkyl (e.g., methyl, ethyl, propyl, or butyl); $R^2$ is —$OR^{2a}$; $R^{2a}$ is methyl;

R³ is C₃₋₄cycloalkyl optionally substituted with one, two, or three R²⁰ᵇ; and each R²⁰ᵇ is independently —CN or C₁₋₃haloalkyl. In embodiments of a compound of Formula (I-1); L¹ is a bond; R⁴ is hydrogen; R⁵ is methyl; R⁶ is hydrogen; R¹ is a 6-10 membered aryl ring substituted with one or more R¹⁰; each R¹⁰ is independently selected from halogen and C₁₋₄alkyl optionally substituted with one, two, or three R²⁰ᵈ; each R²⁰ᵈ is independently selected from halogen, —OH, C₂₋₅heterocycloalkyl optionally substituted with one, two, or three C₁₋₆alkyl (e.g., methyl, ethyl, or propyl), and —OR²¹, wherein R²¹ is C₂₋₅heterocycloalkyl optionally substituted with one, two, or three C₁₋₆alkyl (e.g., methyl, ethyl, propyl, or butyl); R² is —OR²ᵃ; R²ᵃ is methyl; R³ is C₃₋₆cycloalkyl optionally substituted with one, two, or three R²⁰ᵇ; and each R²⁰ᵇ is independently —CN or C₁₋₃haloalkyl. In embodiments of a compound of Formula (I-1); L¹ is a bond; R⁴ is hydrogen; R⁵ is methyl; R⁶ is hydrogen; R¹ is a 6-10 membered aryl ring substituted with one or more R¹⁰; each R¹⁰ is independently selected from halogen and C₁₋₄alkyl optionally substituted with one, two, or three R²⁰ᵈ; each R²⁰ᵈ is independently selected from halogen, —OH, C₂₋₅heterocycloalkyl optionally substituted with one, two, or three C₁₋₆alkyl (e.g., methyl, ethyl, or propyl), and —OR²¹, wherein R²¹ is C₂₋₅heterocycloalkyl optionally substituted with one, two, or three C₁₋₆alkyl (e.g., methyl, ethyl, propyl, or butyl); R² is —OR²ᵃ; R²ᵃ is methyl; R³ is C₃₋₁₀cycloalkyl optionally substituted with one, two, or three R²⁰ᵇ; and each R²⁰ᵇ is independently —CN or C₁₋₃haloalkyl. In embodiments of a compound of Formula (I-1); L¹ is a bond; R⁴ is hydrogen; R⁵ is methyl; R⁶ is hydrogen; R¹ is a 6-10 membered aryl ring substituted with one or more R¹⁰; each R¹⁰ is independently selected from halogen and C₁₋₄alkyl optionally substituted with one, two, or three R²⁰ᵈ; each R²⁰ᵈ is independently selected from halogen, —OH, C₂₋₅heterocycloalkyl optionally substituted with one, two, or three C₁₋₆alkyl (e.g., methyl, ethyl, or propyl), and —OR²¹, wherein R²¹ is C₂₋₅heterocycloalkyl optionally substituted with one, two, or three C₁₋₆ alkyl (e.g., methyl, ethyl, propyl, or butyl); R² is —OR²ᵃ; R²ᵃ is methyl; R³ is C₃₋₁₀cycloalkyl optionally substituted with one, two, or three R²⁰ᵇ; and each R²⁰ᵇ is independently selected from amino; —CN; C₁₋₃alkyl; C₁₋₃alkoxy; C₁₋₃haloalkyl; —OH; —N(R²⁴)C(O)R²⁵; and —C(O)N(R²²)(R²³).

In embodiments of a compound of Formula (I'-2); R⁷ is methyl; L¹ is a bond; R⁴ is hydrogen; R⁶ is hydrogen; R¹ is a

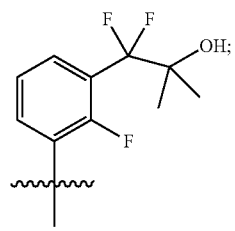

R² is —OR²ᵃ; R²ᵃ is methyl; and R³ is

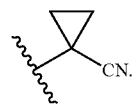

In embodiments of a compound of Formula (I'-2); R⁷ is methyl; L¹ is a bond; R⁴ is hydrogen; R⁶ is hydrogen; R¹ is a

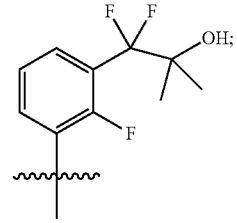 [SMILES: *c1cccc(C(F)(F)C(C)(C)O)c1F]

R² is —OR²ᵃ; R²ᵃ is methyl; R³ is cyclopropyl optionally substituted with one R²⁰ᵇ; and R²⁰ᵇ is —CN. In embodiments of a compound of Formula (I'-2); R⁷ is methyl; L¹ is a bond; R⁴ is hydrogen; R⁶ is hydrogen; R¹ is a

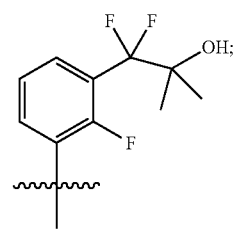 [SMILES: *c1cccc(C(F)(F)C(C)(C)O)c1F]

R² is —OR²ᵃ; R²ᵃ is methyl; R³ is C₃₋₄cycloalkyl optionally substituted with one R²⁰ᵇ; and R²⁰ᵇ is —CN. In embodiments of a compound of Formula (I'-2); R⁷ is methyl; L¹ is a bond; R⁴ is hydrogen; R⁶ is hydrogen; R¹ is a

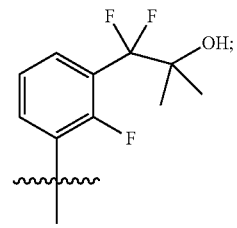 [SMILES: *c1cccc(C(F)(F)C(C)(C)O)c1F]

R² is —OR²ᵃ; R²ᵃ is methyl; R³ is C₃₋₄cycloalkyl optionally substituted with one, two, or three R²⁰ᵇ; and R²⁰ᵇ is —CN. In embodiments of a compound of Formula (I'-2); R⁷ is methyl; L¹ is a bond; R⁴ is hydrogen; R⁶ is hydrogen; R¹ is a

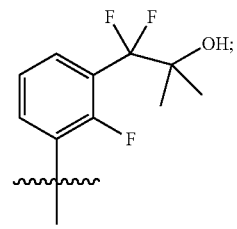 [SMILES: *c1cccc(C(F)(F)C(C)(C)O)c1F]

R² is —OR²ᵃ; R²ᵃ is methyl; R³ is C₃₋₄cycloalkyl optionally substituted with one, two, or three R²⁰ᵇ; and each R²⁰ᵇ is independently —CN or C₁₋₃haloalkyl. In embodiments of a compound of Formula (I'-2); R⁷ is methyl; L¹ is a bond; R⁴ is hydrogen; R⁶ is hydrogen; R¹ is a

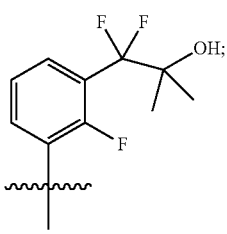

$R^2$ is —$OR^{2a}$; $R^{2a}$ is methyl; $R^3$ is $C_{3-4}$cycloalkyl optionally substituted with one, two, or three $R^{20b}$; and each $R^{20b}$ is independently —CN or $C_{1-3}$haloalkyl. In embodiments of a compound of Formula (I'-2); $R^7$ is methyl; $L^1$ is a bond; $R^4$ is hydrogen; $R^6$ is hydrogen; $R^1$ is a

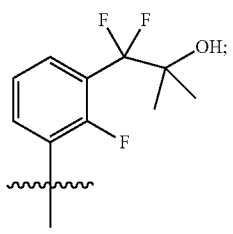

$R^2$ is —$OR^{2a}$; $R^{2a}$ is methyl; $R^3$ is $C_{3-4}$cycloalkyl optionally substituted with one, two, or three $R^{20b}$; and each $R^{20b}$ is independently —CN or $C_{1-3}$haloalkyl. In embodiments of a compound of Formula (I'-2); $R^7$ is methyl; $L^1$ is a bond; $R^4$ is hydrogen; $R^6$ is hydrogen; $R^1$ is a

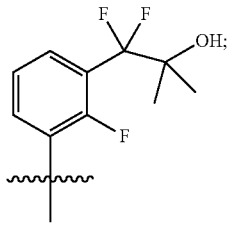

$R^2$ is —$OR^{2a}$; $R^{2a}$ is methyl; $R^3$ is $C_{3-4}$cycloalkyl optionally substituted with one, two, or three $R^{20b}$; and each $R^{20b}$ is independently selected from amino; —CN; $C_{1-3}$alkyl; $C_{1-3}$alkoxy; $C_{1-3}$haloalkyl; —OH; —N($R^{24}$)C(O)$R^{25}$; and —C(O)N($R^{22}$)($R^{23}$).

In embodiments of a compound of Formula (I'-2); $R^7$ is methyl; $L^1$ is a bond; $R^4$ is hydrogen; $R^6$ is hydrogen; $R^1$ is a

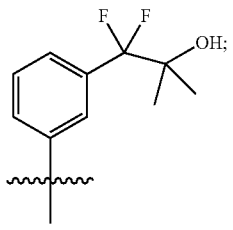 [SMILES: *c1cccc(C(F)(F)C(C)(C)O)c1]

$R^2$ is —$OR^{2a}$; $R^{2a}$ is methyl; and $R^3$ is

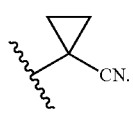 [SMILES: *C1(C#N)CC1]

In embodiments of a compound of Formula (I'-2); $R^7$ is methyl; $L^1$ is a bond; $R^4$ is hydrogen; $R^6$ is hydrogen; $R^1$ is

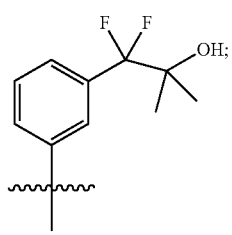 [SMILES: *c1cccc(C(F)(F)C(C)(C)O)c1]

$R^2$ is —$OR^{2a}$; $R^{2a}$ is methyl; $R^3$ is cyclopropyl optionally substituted with one $R^{20b}$; and $R^{20b}$ is —CN. In embodiments of a compound of Formula (I'-2); $R^7$ is methyl; $L^1$ is a bond; $R^4$ is hydrogen; $R^6$ is hydrogen; $R^1$ is a

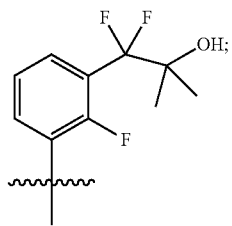 [SMILES: *c1cccc(C(F)(F)C(C)(C)O)c1F]

$R^2$ is —$OR^{2a}$; $R^{2a}$ is methyl; $R^3$ is $C_{3-4}$cycloalkyl optionally substituted with one $R^{20b}$; and $R^{20b}$ is —CN. In embodiments of a compound of Formula (I'-2); $R^7$ is methyl; $L^1$ is a bond; $R^4$ is hydrogen; $R^6$ is hydrogen; $R^1$ is a

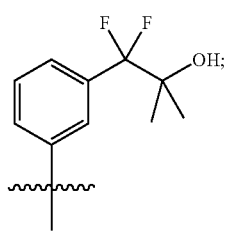 [SMILES: *c1cccc(C(F)(F)C(C)(C)O)c1]

$R^2$ is —$OR^{2a}$; $R^{2a}$ is methyl; $R^3$ is $C_{3-4}$cycloalkyl optionally substituted with one, two, or three $R^{20b}$; and $R^{20b}$ is —CN. In embodiments of a compound of Formula (I'-2); $R^7$ is methyl; $L^1$ is a bond; $R^4$ is hydrogen; $R^6$ is hydrogen; $R^1$ is a

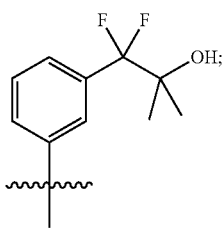 [SMILES: *c1cccc(C(F)(F)C(C)(C)O)c1]

$R^2$ is —$OR^{2a}$; $R^{2a}$ is methyl; $R^3$ is $C_{3-4}$cycloalkyl optionally substituted with one, two, or three $R^{20b}$; and each $R^{20b}$ is independently —CN or $C_{1-3}$haloalkyl. In embodiments of a compound of Formula (I'-2); $R^7$ is methyl; $L^1$ is a bond; $R^4$ is hydrogen; $R^6$ is hydrogen; $R^1$ is a

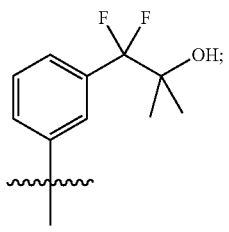 [SMILES: *c1cccc(C(F)(F)C(C)(C)O)c1]

$R^2$ is —$OR^{2a}$; $R^{2a}$ is methyl; $R^3$ is $C_{3-4}$cycloalkyl optionally substituted with one, two, or three $R^{20b}$; and each $R^{20b}$ is independently —CN or $C_{1-3}$haloalkyl. In embodiments of a compound of Formula (I'-2); $R^7$ is methyl; $L^1$ is a bond; $R^4$ is hydrogen; $R^6$ is hydrogen; $R^1$ is a

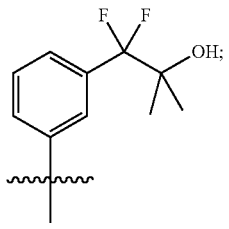 [SMILES: *c1cccc(C(F)(F)C(C)(C)O)c1]

$R^2$ is —$OR^{2a}$; $R^{2a}$ is methyl; $R^3$ is $C_{3-4}$cycloalkyl optionally substituted with one, two, or three $R^{20b}$; and each $R^{20b}$ is independently —CN or $C_{1-3}$haloalkyl. In embodiments of a compound of Formula (I'-2); $R^7$ is methyl; $L^1$ is a bond; $R^4$ is hydrogen; $R^6$ is hydrogen; $R^1$ is a

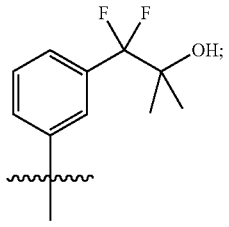 [SMILES: *c1cccc(C(F)(F)C(C)(C)O)c1]

$R^2$ is —$OR^{2a}$; $R^{2a}$ is methyl; $R^3$ is $C_{3-4}$cycloalkyl optionally substituted with one, two, or three $R^{20b}$; and each $R^{20b}$ is independently selected from amino; —CN; $C_{1-3}$alkyl; $C_{1-3}$alkoxy; $C_{1-3}$haloalkyl; —OH; —N($R^{24}$)C(O)$R^2$; and —C(O)N($R^{22}$)($R^{23}$).

In embodiments of a compound of Formula (I'-2); $R^7$ is methyl; $L^1$ is a bond; $R^4$ is hydrogen; $R^6$ is hydrogen; $R^1$ is a

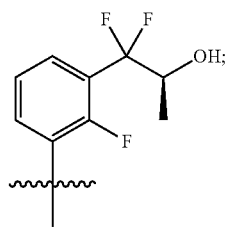 [SMILES: *c1cccc(C(F)(F)[C@H](C)O)c1F]

$R^2$ is —$OR^{2a}$; $R^{2a}$ is methyl and $R^3$ is

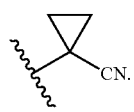

In embodiments of a compound of Formula (I'-2); $R^7$ is methyl; $L^1$ is a bond; $R^4$ is hydrogen; $R^6$ is hydrogen; $R^1$ is a

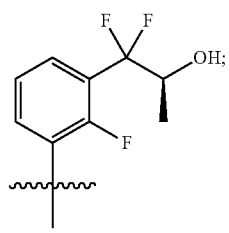 [SMILES: *c1cccc(C(F)(F)[C@H](C)O)c1F]

$R^2$ is —$OR^{2a}$; $R^{2a}$ is methyl; $R^3$ is cyclopropyl optionally substituted with one $R^{20b}$; and $R^{20b}$ is —CN. In embodiments of a compound of Formula (I'-2); $R^7$ is methyl; $L^1$ is a bond; $R^4$ is hydrogen; $R^6$ is hydrogen; $R^1$ is a

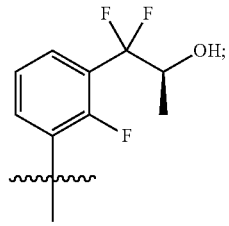 [SMILES: *c1cccc(C(F)(F)[C@H](C)O)c1F]

$R^2$ is —$OR^{2a}$; $R^{2a}$ is methyl; $R^3$ is $C_{3-4}$cycloalkyl optionally substituted with one $R^{20b}$; and $R^{20b}$ is —CN. In embodiments of a compound of Formula (I'-2); $R^7$ is methyl; $L^1$ is a bond; $R^4$ is hydrogen; $R^6$ is hydrogen; $R^1$ is a

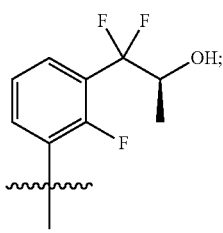 [SMILES: *c1cccc(C(F)(F)[C@H](C)O)c1F]

$R^2$ is —$OR^{2a}$; $R^{2a}$ is methyl; $R^3$ is $C_{3-4}$cycloalkyl optionally substituted with one, two, or three $R^{20b}$; and $R^{20b}$ is —CN. In embodiments of a compound of Formula (I'-2); $R^7$ is methyl; $L^1$ is a bond; $R^4$ is hydrogen; $R^6$ is hydrogen; $R^1$ is a

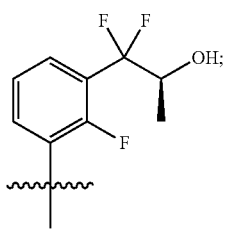 [SMILES: *c1cccc(C(F)(F)[C@H](C)O)c1F]

$R^2$ is —$OR^{2a}$; $R^{2a}$ is methyl; $R^3$ is $C_{3-4}$cycloalkyl optionally substituted with one, two, or three $R^{20b}$; and each $R^{20b}$ is independently —CN or $C_{1-3}$haloalkyl. In embodiments of a compound of Formula (I'-2); $R^7$ is methyl; $L^1$ is a bond; $R^4$ is hydrogen; $R^6$ is hydrogen; $R^1$ is a

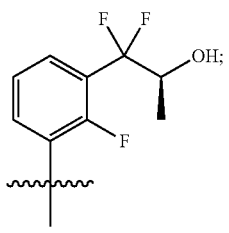 [SMILES: *c1cccc(C(F)(F)[C@H](C)O)c1F]

$R^2$ is —$OR^{2a}$; $R^{2a}$ is methyl; $R^3$ is $C_{3-4}$cycloalkyl optionally substituted with one, two, or three $R^{20b}$; and each $R^{20b}$ is independently —CN or $C_{1-3}$haloalkyl. In embodiments of a compound of Formula (I'-2); $R^7$ is methyl; $L^1$ is a bond; $R^4$ is hydrogen; $R^6$ is hydrogen; $R^1$ is a

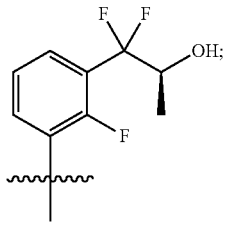 [SMILES: *c1cccc(C(F)(F)[C@H](C)O)c1F]

$R^2$ is —$OR^{2a}$; $R^{2a}$ is methyl; $R^3$ is $C_{3-y}$ optionally substituted with one, two, or three $R^{20b}$; and each $R^{20b}$ is independently —CN or $C_{1-3}$haloalkyl. In embodiments of a compound of Formula (I'-2); $R^7$ is methyl; $L^1$ is a bond; $R^4$ is hydrogen; $R^6$ is hydrogen; $R^1$ is a

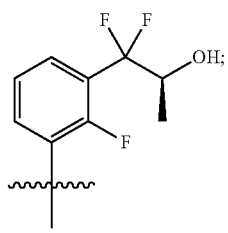 [SMILES: *c1cccc(C(F)(F)[C@H](C)O)c1F]

$R^2$ is —$OR^{2a}$; $R^{2a}$ is methyl; $R^3$ is $C_{3-4}$cycloalkyl optionally substituted with one, two, or three $R^{21b}$; and each $R^{2b}$ is independently selected from amino; —CN; $C_{1-3}$alkyl; $C_{1-3}$alkoxy; $C_{1-3}$haloalkyl; —OH; —N($R^{24}$)C(O)$R^{2'}$; and —C(O)N($R^{22}$)($R^{23}$).

In embodiments of a compound of Formula (I'-2); $R^7$ is methyl; $L^1$ is a bond; $R^4$ is hydrogen; $R^6$ is hydrogen; $R^1$ is a

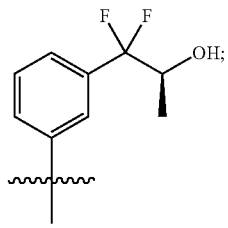 [SMILES: *c1cccc(C(F)(F)[C@H](C)O)c1]

$R^2$ is —$OR^{2a}$; $R^{2a}$ is methyl; and $R^3$ is

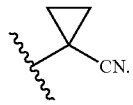

In embodiments of a compound of Formula (I'-2); $R^7$ is methyl; $L^1$ is a bond; $R^4$ is hydrogen; $R^6$ is hydrogen; $R^1$ is a

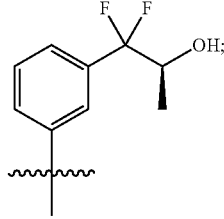 [SMILES: *c1cccc(C(F)(F)[C@H](C)O)c1]

$R^2$ is —$OR^{2a}$; $R^{2a}$ is methyl; $R^3$ is cyclopropyl optionally substituted with one $R^{20b}$; and $R^{20b}$ is —CN. In embodiments of a compound of Formula (I'-2); $R^7$ is methyl; $L^1$ is a bond; $R^4$ is hydrogen; $R^6$ is hydrogen; $R^1$ is a

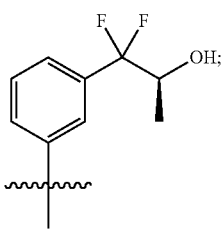 [SMILES: *c1cccc(C(F)(F)[C@H](C)O)c1]

$R^2$ is —$OR^{2a}$; $R^{2a}$ is methyl; $R^3$ is $C_{3-4}$cycloalkyl optionally substituted with one $R^{20b}$; and $R^{20b}$ is —CN. In embodiments of a compound of Formula (I'-2); $R^7$ is methyl; $L^1$ is a bond; $R^4$ is hydrogen; $R^6$ is hydrogen; $R^1$ is a

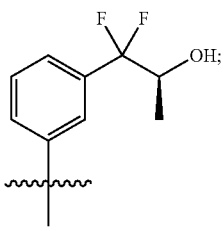 [SMILES: *c1cccc(C(F)(F)[C@H](C)O)c1]

$R^2$ is —$OR^{2a}$; $R^{2a}$ is methyl; $R^3$ is $C_{3-4}$cycloalkyl optionally substituted with one, two, or three $R^{20b}$; and $R^{20b}$ is —CN. In embodiments of a compound of Formula (I'-2); $R^7$ is methyl; $L^1$ is a bond; $R^4$ is hydrogen; $R^6$ is hydrogen; $R^1$ is a

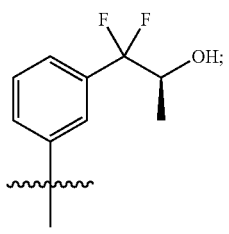 [SMILES: *c1cccc(C(F)(F)[C@H](C)O)c1]

$R^2$ is —$OR^{2a}$; $R^{2a}$ is methyl; $R^3$ is $C_{3-4}$cycloalkyl optionally substituted with one, two, or three $R^{20b}$; and each $R^{20b}$ is independently —CN or $C_{1-3}$haloalkyl. In embodiments of a compound of Formula (I'-2); $R^7$ is methyl; $L^1$ is a bond; $R^4$ is hydrogen; $R^6$ is hydrogen; $R^1$ is a

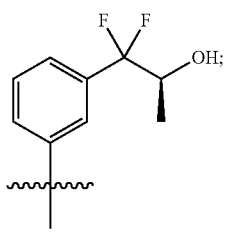 [SMILES: *c1cccc(C(F)(F)[C@H](C)O)c1]

$R^2$ is —$OR^{2a}$; $R^{2a}$ is methyl; $R^3$ is $C_{3-v}$ optionally substituted with one, two, or three $R^{20b}$; and each $R^{20b}$ is independently —CN or $C_{1-3}$haloalkyl. In embodiments of a compound of Formula (I'-2); $R^7$ is methyl; $L^1$ is a bond; $R^4$ is hydrogen; $R^6$ is hydrogen; $R^1$ is a

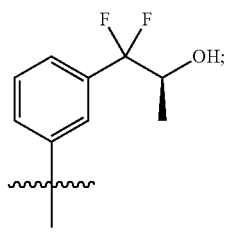 [SMILES: *c1cccc(C(F)(F)[C@H](C)O)c1]

$R^2$ is —$OR^{2a}$; $R^{2a}$ is methyl; $R^3$ is $C_{3-4}$cycloalkyl optionally substituted with one, two, or three $R^{20b}$; and each $R^{20b}$ is independently —CN or $C_{1-3}$haloalkyl. In embodiments of a compound of Formula (I'-2); $R^7$ is methyl; $L^1$ is a bond; $R^4$ is hydrogen; $R^6$ is hydrogen; $R^1$ is a

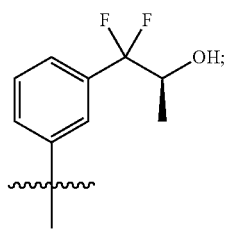 [SMILES: *c1cccc(C(F)(F)[C@H](C)O)c1]

$R^2$ is —$OR^{2a}$; $R^{2a}$ is methyl; $R^3$ is $C_{3-4}$cycloalkyl optionally substituted with one, two, or three $R^{20b}$; and each $R^{20b}$ is independently selected from amino; —CN; $C_{1-3}$alkyl; $C_{1-3}$alkoxy; $C_{1-3}$haloalkyl; —OH; —N($R^{24}$)C(O)$R^{25}$; and —C(O)N($R^{22}$)($R^{23}$).

In embodiments of a compound of Formula (I'-2); $R^7$ is methyl; $L^1$ is a bond; $R^4$ is hydrogen; $R^6$ is hydrogen; $R^1$ is a

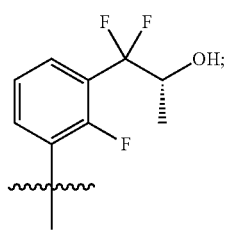 [SMILES: *c1cccc(C(F)(F)[C@@H](C)O)c1F]

$R^2$ is —$OR^{2a}$; $R^{2a}$ is methyl; and $R^3$ is

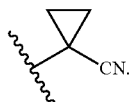

In embodiments of a compound of Formula (I'-2); $R^7$ is methyl; $L^1$ is a bond; $R^4$ is hydrogen; $R^6$ is hydrogen; $R^1$ is a

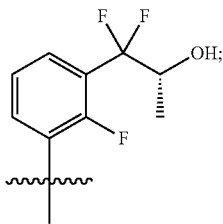 [SMILES: *c1cccc(C(F)(F)[C@@H](C)O)c1F]

$R^2$ is —$OR^{2a}$; $R^{2a}$ is methyl; $R^3$ is cyclopropyl optionally substituted with one $R^{20b}$; and $R^{20b}$ is —CN. In embodiments of a compound of Formula (I'-2); $R^7$ is methyl; $L^1$ is a bond; $R^4$ is hydrogen; $R^6$ is hydrogen; $R^1$ is

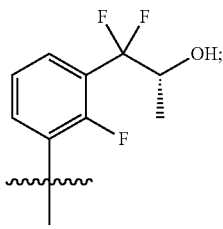 [SMILES: *c1cccc(C(F)(F)[C@@H](C)O)c1F]

$R^2$ is —$OR^{2a}$; $R^{2a}$ is methyl; $R^3$ is $C_{3-4}$cycloalkyl optionally substituted with one $R^{20b}$; and $R^{20b}$ is —CN. In embodiments of a compound of Formula (I'-2); $R^7$ is methyl; $L^1$ is a bond; $R^4$ is hydrogen; $R^6$ is hydrogen; $R^1$ is a

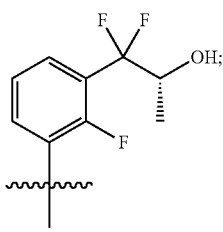 [SMILES: *c1cccc(C(F)(F)[C@@H](C)O)c1F]

$R^2$ is —$OR^{2a}$; $R^{2a}$ is methyl; $R^3$ is $C_{3-4}$cycloalkyl optionally substituted with one, two, or three $R^{20b}$; and $R^{20b}$ is —CN. In embodiments of a compound of Formula (I'-2); $R^7$ is methyl; $L^1$ is a bond; $R^4$ is hydrogen; $R^6$ is hydrogen; $R^1$ is a

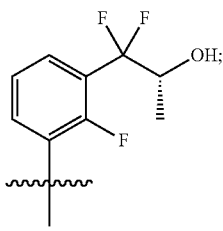 [SMILES: *c1cccc(C(F)(F)[C@@H](C)O)c1F]

$R^2$ is —$OR^{2a}$; $R^{2a}$ is methyl; $R^3$ is $C_{3-4}$cycloalkyl optionally substituted with one, two, or three $R^{20b}$; and each $R^{20b}$ is independently —CN or $C_{1-3}$haloalkyl. In embodiments of a compound of Formula (I'-2); $R^7$ is methyl; $L^1$ is a bond; $R^4$ is hydrogen; $R^6$ is hydrogen; $R^1$ is a

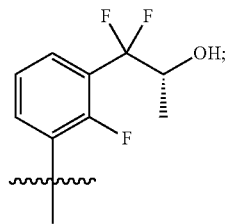 [SMILES: *c1cccc(C(F)(F)[C@@H](C)O)c1F]

$R^2$ is —$OR^{2a}$; $R^{2a}$ is methyl; $R^3$ is $C_{3-4}$cycloalkyl optionally substituted with one, two, or three $R^{20b}$; and each $R^{20b}$ is independently —CN or $C_{1-3}$haloalkyl. In embodiments of a compound of Formula (I'-2); $R^7$ is methyl; $L^1$ is a bond; $R^4$ is hydrogen; $R^6$ is hydrogen; $R^1$ is a

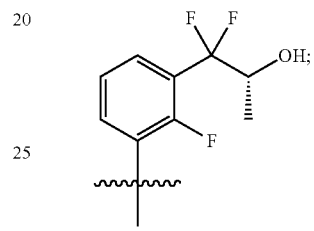

$R^2$ is —$OR^{2a}$; $R^{2a}$ is methyl; $R^3$ is $C_{3-4}$cycloalkyl optionally substituted with one, two, or three $R^{20b}$; and each $R^{20b}$ is independently —CN or $C_{1-3}$haloalkyl. In embodiments of a compound of Formula (I'-2); $R^7$ is methyl; $L^1$ is a bond; $R^4$ is hydrogen; $R^6$ is hydrogen; $R^1$ is a

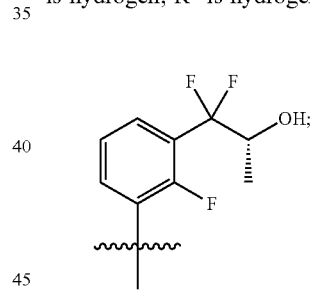

$R^2$ is —$OR^{2a}$; $R^{2a}$ is methyl; $R^3$ is $C_{3-4}$cycloalkyl optionally substituted with one, two, or three $R^{20b}$; and each $R^{20b}$ is independently selected from amino; —CN; $C_{1-3}$alkyl; $C_{1-3}$alkoxy; $C_{1-3}$haloalkyl; —OH; —N($R^{24}$)C(O)$R^{25}$; and —C(O)N($R^{22}$)($R^{23}$).

In embodiments of a compound of Formula (I'-2); $R^7$ is methyl; $L^1$ is a bond; $R^4$ is hydrogen; $R^6$ is hydrogen; $R^1$ is

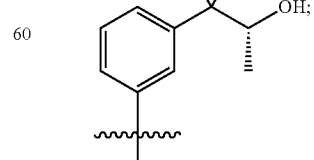

$R^2$ is —$OR^{2a}$; $R^{2a}$ is methyl; and $R^3$ is

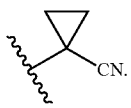

In embodiments of a compound of Formula (I'-2); $R^7$ is methyl; $L^1$ is a bond; $R^4$ is hydrogen; $R^6$ is hydrogen; $R^1$ is a

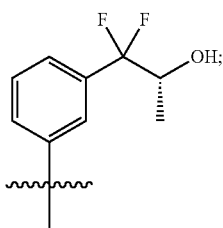 [SMILES: *c1cccc(C(F)(F)[C@@H](C)O)c1]

$R^2$ is —$OR^{2a}$; $R^{2a}$ is methyl; $R^3$ is cyclopropyl optionally substituted with one $R^{20b}$; and $R^{20b}$ is —CN. In embodiments of a compound of Formula (I'-2); $R^7$ is methyl; $L^1$ is a bond; $R^4$ is hydrogen; $R^6$ is hydrogen; $R^1$ is a

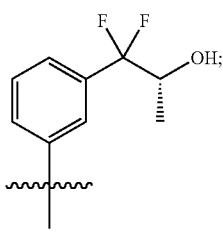 [SMILES: *c1cccc(C(F)(F)[C@@H](C)O)c1]

$R^2$ is —$OR^{2a}$; $R^{2a}$ is methyl; $R^3$ is $C_{3-4}$cycloalkyl optionally substituted with one $R^{20b}$; and $R^{20b}$ is —CN. In embodiments of a compound of Formula (I'-2); $R^7$ is methyl; $L^1$ is a bond; $R^4$ is hydrogen; $R^6$ is hydrogen; $R^1$ is a

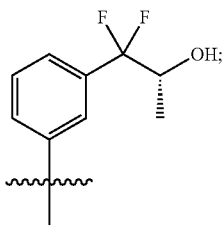 [SMILES: *c1cccc(C(F)(F)[C@@H](C)O)c1]

$R^2$ is —$OR^{2a}$; $R^{2a}$ is methyl; $R^3$ is $C_{3-4}$cycloalkyl optionally substituted with one, two, or three $R^{20b}$; and $R^{20b}$ is —CN. In embodiments of a compound of Formula (I'-2); $R^7$ is methyl; $L^1$ is a bond; $R^4$ is hydrogen; $R^6$ is hydrogen; $R^1$ is a

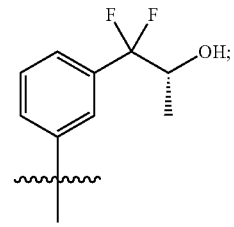 [SMILES: *c1cccc(C(F)(F)[C@@H](C)O)c1]

$R^2$ is —$OR^{2a}$; $R^{2a}$ is methyl; $R^3$ is $C_{3-4}$cycloalkyl optionally substituted with one, two, or three $R^{20b}$; and each $R^{20b}$ is independently —CN or $C_{1-3}$haloalkyl. In embodiments of a compound of Formula (I'-2); $R^7$ is methyl; $L^1$ is a bond; $R^4$ is hydrogen; $R^6$ is hydrogen; $R^1$ is a

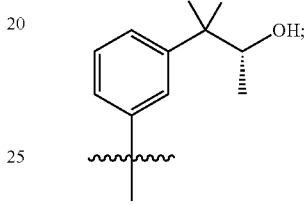

$R^2$ is —$OR^{2a}$; $R^{2a}$ is methyl; $R^3$ is $C_{3-4}$cycloalkyl optionally substituted with one, two, or three $R^{20b}$; and each $R^{20b}$ is independently —CN or $C_{1-3}$haloalkyl. In embodiments of a compound of Formula (I'-2); $R^7$ is methyl; $L^1$ is a bond; $R^4$ is hydrogen; $R^6$ is hydrogen; $R^1$ is a

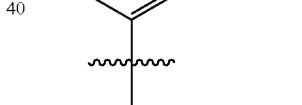

$R^2$ is —$OR^{2a}$; $R^{2a}$ is methyl; $R^3$ is $C_{3-4}$cycloalkyl optionally substituted with one, two, or three $R^{20b}$; and each $R^{20b}$ is independently —CN or $C_{1-3}$haloalkyl. In embodiments of a compound of Formula (I'-2); $R^7$ is methyl; $L^1$ is a bond; $R^4$ is hydrogen; $R^6$ is hydrogen; $R^1$ is

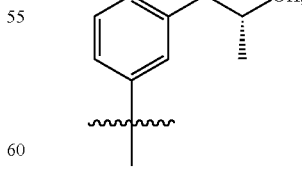

$R^2$ is —$OR^{2a}$; $R^{2a}$ is methyl; $R^3$ is $C_{3-4}$cycloalkyl optionally substituted with one, two, or three $R^{20b}$; and each $R^{20b}$ is independently selected from amino; —CN; $C_{1-3}$alkyl; $C_{1-3}$alkoxy; $C_{1-3}$haloalkyl; —OH; —$N(R^{24})C(O)R^{25}$; and —$C(O)N(R^{22})(R^{23})$.

In embodiments of a compound of Formula (I'-2); $R^7$ is methyl; $L^1$ is a bond; $R^4$ is hydrogen; $R^6$ is hydrogen; $R^1$ is a phenyl substituted with one or more $R^{10}$; each $R^{10}$ is independently selected from halogen and $C_{1-4}$alkyl optionally substituted with one, two, or three $R^{20d}$; each $R^{20d}$ is independently selected from halogen and —OH; $R^2$ is —$OR^{2a}$; $R^{2a}$ is methyl; and $R^3$ is

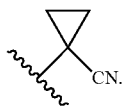

In embodiments of a compound of Formula (I'-2); $R^7$ is methyl; $L^1$ is a bond; $R^4$ is hydrogen; $R^6$ is hydrogen; $R^1$ is a phenyl substituted with one or more $R^{10}$; each $R^{10}$ is independently selected from halogen and $C_{1-4}$alkyl optionally substituted with one, two, or three $R^{20d}$; each $R^{20d}$ is independently selected from halogen and —OH; $R^2$ is —$OR^{2a}$; $R^{2a}$ is methyl; $R^3$ is cyclopropyl optionally substituted with one $R^{20b}$; and $R^{20b}$ is —CN. In embodiments of a compound of Formula (I'-2); $R^7$ is methyl; $L^1$ is a bond; $R^4$ is hydrogen; $R^6$ is hydrogen; $R^1$ is a phenyl substituted with one or more $R^{10}$; each $R^{10}$ is independently selected from halogen and $C_{1-4}$ alkyl optionally substituted with one, two, or three $R^{20d}$; each $R^{20d}$ is independently selected from halogen and —OH; $R^2$ is —$OR^{2a}$; $R^{2a}$ is methyl; $R^3$ is $C_{3-4}$cycloalkyl optionally substituted with one $R^{20b}$; and $R^{20b}$ is —CN. In embodiments of a compound of Formula (I'-2); $R^7$ is methyl; $L^1$ is a bond; $R^4$ is hydrogen; $R^6$ is hydrogen; $R^1$ is a phenyl substituted with one or more $R^{10}$; each $R^{10}$ is independently selected from halogen and $C_{1-4}$alkyl optionally substituted with one, two, or three $R^{20d}$; each $R^{20d}$ is independently selected from halogen and —OH; $R^2$ is —$OR^{2a}$; $R^{2a}$ is methyl; $R^3$ is $C_{3-4}$cycloalkyl optionally substituted with one, two, or three $R^{20b}$; and $R^{20b}$ is —CN. In embodiments of a compound of Formula (I'-2); $R^7$ is methyl; $L^1$ is a bond; $R^4$ is hydrogen; $R^6$ is hydrogen; $R^1$ is a phenyl substituted with one or more $R^{10}$; each $R^{10}$ is independently selected from halogen and $C_{1-4}$alkyl optionally substituted with one, two, or three $R^{20d}$; each $R^{20d}$ is independently selected from halogen and —OH; $R^2$ is —$OR^{2a}$; $R^{2a}$ is methyl; $R^3$ is $C_{3-4}$cycloalkyl optionally substituted with one, two, or three $R^{20b}$; and each $R^{20b}$ is independently —CN or $C_{1-3}$haloalkyl. In embodiments of a compound of Formula (I'-2); $R^7$ is methyl; $L^1$ is a bond; $R^4$ is hydrogen; $R^6$ is hydrogen; $R^1$ is a phenyl substituted with one or more $R^{10}$; each $R^{10}$ is independently selected from halogen and $C_{1-4}$alkyl optionally substituted with one, two, or three $R^{20d}$; each $R^{20d}$ is independently selected from halogen and —OH; $R^2$ is —$OR^{2a}$; $R^{2a}$ is methyl; $R^3$ is $C_{3-4}$cycloalkyl optionally substituted with one, two, or three $R^{20b}$; and each $R^{20b}$ is independently —CN or $C_{1-3}$haloalkyl. In embodiments of a compound of Formula (I'-2); $R^7$ is methyl; $L^1$ is a bond; $R^4$ is hydrogen; $R^6$ is hydrogen; $R^1$ is a phenyl substituted with one or more $R^{10}$; each $R^{10}$ is independently selected from halogen and $C_{1-4}$alkyl optionally substituted with one, two, or three $R^{20d}$; each $R^{20d}$ is independently selected from halogen and —OH; $R^2$ is —$OR^{2a}$; $R^{2a}$ is methyl; $R^3$ is $C_{3-4}$cycloalkyl optionally substituted with one, two, or three $R^{20b}$; and each $R^{20b}$ is independently —CN or $C_{1-3}$haloalkyl. In embodiments of a compound of Formula (I'-2); $R^7$ is methyl; $L^1$ is a bond; $R^4$ is hydrogen; $R^6$ is hydrogen; $R^1$ is a phenyl substituted with one or more $R^{10}$; each $R^{10}$ is independently selected from halogen and $C_{1-4}$alkyl optionally substituted with one, two, or three $R^{20d}$; each $R^{20d}$ is independently selected from halogen and —OH; $R^2$ is —$OR^{2a}$; $R^{2a}$ is methyl; $R^3$ is $C_{3-4}$cycloalkyl optionally substituted with one, two, or three $R^{20b}$; and each $R^{20b}$ is independently selected from amino; —CN; $C_{1-3}$alkyl; $C_{1-3}$alkoxy; $C_{1-3}$ haloalkyl; —OH; —$N(R^{24})C(O)R^{21}$; and —$C(O)N(R^{22})(R^{23})$.

In embodiments of a compound of Formula (I'-2); $R^7$ is methyl; $L^1$ is a bond; $R^4$ is hydrogen; $R^6$ is hydrogen; $R^1$ is a phenyl substituted with one or more $R^{10}$; each $R^{10}$ is independently selected from halogen and $C_{1-4}$alkyl optionally substituted with one, two, or three $R^{20d}$; each $R^{20d}$ is independently selected from halogen, —OH, $C_{2-5}$heterocycloalkyl optionally substituted with one, two, or three $C_{1-6}$alkyl (e.g., methyl, ethyl, or propyl), and —$OR^{21}$, wherein $R^{21}$ is $C_{2-5}$heterocycloalkyl optionally substituted with one, two, or three $C_{1-6}$alkyl (e.g., methyl, ethyl, propyl, or butyl); $R^2$ is —$OR^{2a}$; $R^{2a}$ is methyl; and $R^3$ is

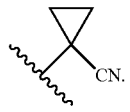 [SMILES: *C1(C#N)CC1]

In embodiments of a compound of Formula (I'-2); $R^7$ is methyl; $L^1$ is a bond; $R^4$ is hydrogen; $R^6$ is hydrogen; $R^1$ is a phenyl substituted with one or more $R^{10}$; each $R^{10}$ is independently selected from halogen and $C_{1-4}$alkyl optionally substituted with one, two, or three $R^{20d}$; each $R^{20d}$ is independently selected from halogen, —OH, $C_{2-5}$heterocycloalkyl optionally substituted with one, two, or three $C_{1-6}$ alkyl (e.g., methyl, ethyl, or propyl), and —$OR^{21}$, wherein $R^{21}$ is $C_{2-5}$heterocycloalkyl optionally substituted with one, two, or three $C_{1-6}$alkyl (e.g., methyl, ethyl, propyl, or butyl); $R^3$ is cyclopropyl optionally substituted with one $R^{20b}$; and $R^{20b}$ is —CN. In embodiments of a compound of Formula (I'-2); $R^7$ is methyl; $L^1$ is a bond; $R^4$ is hydrogen; $R^6$ is hydrogen; $R^1$ is a phenyl substituted with one or more $R^{10}$; each $R^{10}$ is independently selected from halogen and $C_{1-4}$alkyl optionally substituted with one, two, or three $R^{20d}$; each $R^{20a}$ is independently selected from halogen, —OH, $C_{2-5}$heterocycloalkyl optionally substituted with one, two, or three $C_{1-6}$alkyl (e.g., methyl, ethyl, or propyl), and —$OR^{21}$, wherein $R^{21}$ is $C_{2-5}$heterocycloalkyl optionally substituted with one, two, or three $C_{1-6}$alkyl (e.g., methyl, ethyl, propyl, or butyl); $R^2$ is —$OR^{2a}$; $R^{2a}$ is methyl; $R^3$ is $C_{3-4}$cycloalkyl optionally substituted with one $R^{20b}$; and $R^{20b}$ is —CN. In embodiments of a compound of Formula (I'-2); $R^7$ is methyl; $L^1$ is a bond; $R^4$ is hydrogen; $R^6$ is hydrogen; $R^1$ is a phenyl substituted with one or more $R^{10}$; each $R^{10}$ is independently selected from halogen and $C_{1-4}$alkyl optionally substituted with one, two, or three $R^{20d}$; each $R^{20d}$ is independently selected from halogen, —OH, $C_{2-5}$heterocycloalkyl optionally substituted with one, two, or three $C_{1-6}$alkyl (e.g., methyl, ethyl, or propyl), and —$OR^{21}$, wherein $R^{21}$ is $C_{2-5}$heterocycloalkyl optionally substituted with one, two, or three $C_{1-6}$alkyl (e.g., methyl, ethyl, propyl, or butyl); $R^2$ is —$OR^{2a}$; $R^{2a}$ is methyl; $R^3$ is $C_{3-4}$cycloalkyl optionally substituted with one, two, or three $R^{20b}$; and $R^{20b}$ is —CN. In embodiments of a compound of Formula (I'-2); $R^7$ is methyl; $L^1$ is a bond; $R^4$ is hydrogen; $R^6$ is hydrogen; $R^1$ is a phenyl substituted with one or more $R^{10}$; each $R^{10}$ is independently selected from halogen and $C_{1-4}$alkyl optionally substituted with one, two, or three $R^{20d}$; each $R^{20d}$ is independently selected from halogen, —OH, $C_{2-5}$heterocycloalkyl optionally substituted with one, two, or three $C_{1-6}$alkyl (e.g., methyl, ethyl, or propyl), and —$OR^{21}$, wherein $R^{21}$ is $C_{2-5}$heterocycloalkyl optionally substituted with one, two, or three $C_{1-6}$alkyl (e.g., methyl, ethyl, propyl, or butyl); $R^2$ is —$OR^{2a}$; $R^{2a}$ is methyl; $R^3$ is $C_{3-4}$cycloalkyl optionally substituted with one, two, or three $R^{20b}$; and each $R^{20b}$ is independently —CN or $C_{1-3}$haloalkyl. In embodiments of a compound of Formula (I'-2); $R^7$ is methyl; $L^1$ is a bond; $R^4$ is hydrogen; $R^6$ is hydrogen; $R^1$ is a phenyl substituted with one or more $R^{10}$; each $R^{10}$ is independently selected from halogen and $C_{1-4}$alkyl optionally substituted with one, two, or three $R^{20d}$; each $R^{20d}$ is independently selected from halogen, —OH, $C_{2-5}$heterocycloalkyl optionally substituted with one, two, or three $C_{1-6}$alkyl (e.g., methyl, ethyl, or propyl), and —$OR^{21}$, wherein $R^{21}$ is $C_{2-5}$heterocycloalkyl optionally substituted with one, two, or three $C_{1-6}$alkyl (e.g., methyl, ethyl, propyl, or butyl); $R^2$ is —$OR^{2a}$; $R^{2a}$ is methyl; $R^3$ is $C_{3-4}$cycloalkyl optionally substituted with one, two, or three $R^{20b}$; and each $R^{20b}$ is independently —CN or $C_{1-3}$haloalkyl. In embodiments of a compound of Formula (I'-2); $R^7$ is methyl; $L^1$ is a bond; $R^4$ is hydrogen; $R^6$ is hydrogen; $R^1$ is a phenyl substituted with one or more $R^{10}$; each $R^{10}$ is independently selected from halogen and $C_{1-4}$ alkyl optionally substituted with one, two, or three $R^{20d}$; each $R^{20d}$ is independently selected from halogen, —OH, $C_{2-5}$heterocycloalkyl optionally substituted with one, two, or three $C_{1-6}$alkyl (e.g., methyl, ethyl, or propyl), and —$OR^{21}$, wherein $R^{21}$ is $C_{2-5}$heterocycloalkyl optionally substituted with one, two, or three $C_{1-6}$alkyl (e.g., methyl, ethyl, propyl, or butyl); $R^2$ is —$OR^{2a}$; $R^{2a}$ is methyl; $R^3$ is $C_{3-4}$cycloalkyl optionally substituted with one, two, or three $R^{20b}$; and each $R^{20b}$ is independently —CN or $C_{1-3}$haloalkyl. In embodiments of a compound of Formula (I'-2); $R^7$ is methyl; $L^1$ is a bond; $R^4$ is hydrogen; $R^6$ is hydrogen; $R^1$ is a phenyl substituted with one or more $R^{10}$; each $R^{10}$ is independently selected from halogen and $C_{1-4}$alkyl optionally substituted with one, two, or three $R^{20d}$; each $R^{20a}$ is independently selected from halogen, —OH, $C_{2-5}$heterocycloalkyl optionally substituted with one, two, or three $C_{1-6}$alkyl (e.g., methyl, ethyl, or propyl), and —$OR^{21}$, wherein $R^{21}$ is $C_{2-5}$heterocycloalkyl optionally substituted with one, two, or three $C_{1-6}$alkyl (e.g., methyl, ethyl, propyl, or butyl); $R^2$ is —$OR^{2a}$; $R^{2a}$ is methyl; $R^3$ is $C_{3-4}$cycloalkyl optionally substituted with one, two, or three $R^{20b}$; and each $R^{20b}$ is independently selected from amino; —CN; $C_{1-3}$alkyl; $C_{1-3}$alkoxy; $C_{1-3}$haloalkyl; —OH; —N($R^{24}$)C(O)$R^{25}$; and —C(O)N($R^{22}$)($R^{23}$).

In embodiments of a compound of Formula (I'-2); $R^7$ is methyl; $L^1$ is a bond; $R^4$ is hydrogen; $R^6$ is hydrogen; $R^1$ is a 6-10 membered aryl ring substituted with one or more $R^{10}$; each $R^{10}$ is independently selected from halogen and $C_{1-4}$alkyl optionally substituted with one, two, or three $R^{20d}$; each $R^{20d}$ is independently selected from halogen, —OH, $C_{2-5}$heterocycloalkyl optionally substituted with one, two, or three $C_{1-6}$alkyl (e.g., methyl, ethyl, or propyl), and —$OR^{21}$, wherein $R^{21}$ is $C_{2-5}$heterocycloalkyl optionally substituted with one, two, or three $C_{1-6}$alkyl (e.g., methyl, ethyl, propyl, or butyl); $R^2$ is —$OR^{2a}$; $R^{2a}$ is methyl; and $R^3$ is

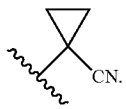

In embodiments of a compound of Formula (I'-2); $R^7$ is methyl; $L^1$ is a bond; $R^4$ is hydrogen; $R^6$ is hydrogen; $R^1$ is a 6-10 membered aryl ring substituted with one or more $R^{10}$; each $R^{10}$ is independently selected from halogen and $C_{1-4}$alkyl optionally substituted with one, two, or three $R^{20d}$; each $R^{20d}$ is independently selected from halogen, —OH, $C_{2-5}$heterocycloalkyl optionally substituted with one, two, or three $C_{1-6}$alkyl (e.g., methyl, ethyl, or propyl), and —$OR^{21}$, wherein $R^{21}$ is $C_{2-5}$heterocycloalkyl optionally substituted with one, two, or three $C_{1-6}$alkyl (e.g., methyl, ethyl, propyl, or butyl); $R^3$ is cyclopropyl optionally substituted with one $R^{20b}$; and $R^{20b}$ is —CN. In embodiments of a compound of Formula (I'-2); $R^7$ is methyl; $L^1$ is a bond; $R^4$ is hydrogen; $R^6$ is hydrogen; $R^1$ is a 6-10 membered aryl ring substituted with one or more $R^{10}$; each $R^{10}$ is independently selected from halogen and $C_{1-4}$alkyl optionally substituted with one, two, or three $R^{20d}$; each $R^{20d}$ is independently selected from halogen, —OH, $C_{2-5}$heterocycloalkyl optionally substituted with one, two, or three $C_{1-6}$alkyl (e.g., methyl, ethyl, or propyl), and —$OR^{21}$, wherein $R^{21}$ is $C_{2-5}$heterocycloalkyl optionally substituted with one, two, or three $C_{1-6}$alkyl (e.g., methyl, ethyl, propyl, or butyl); $R^2$ is —$OR^{2a}$; $R^{2a}$ is methyl; $R^3$ is $C_{3-4}$cycloalkyl optionally substituted with one, two, or three $R^{20b}$; and $R^{20b}$ is —CN. In embodiments of a compound of Formula (I'-2); $R^7$ is methyl; $L^1$ is a bond; $R^4$ is hydrogen; $R^6$ is hydrogen; $R^1$ is a 6-10 membered aryl ring substituted with one or more $R^{10}$; each $R^{10}$ is independently selected from halogen and $C_{1-4}$alkyl optionally substituted with one, two, or three $R^{20d}$; each $R^{20d}$ is independently selected from halogen, —OH, $C_{2-5}$heterocycloalkyl optionally substituted with one, two, or three $C_{1-6}$alkyl (e.g., methyl, ethyl, or propyl), and —$OR^{21}$, wherein $R^{21}$ is $C_{2-5}$heterocycloalkyl optionally substituted with one, two, or three $C_{1-6}$alkyl (e.g., methyl, ethyl, propyl, or butyl); $R^2$ is —$OR^{2a}$; $R^{2a}$ is methyl; $R^3$ is $C_{3-4}$cycloalkyl optionally substituted with one, two, or three $R^{20b}$; and $R^{20b}$ is —CN. In embodiments of a compound of Formula (I'-2); $R^7$ is methyl; $L^1$ is a bond; $R^4$ is hydrogen; $R^6$ is hydrogen; $R^1$ is a 6-10 membered aryl ring substituted with one or more $R^{10}$; each $R^{10}$ is independently selected from halogen and $C_{1-4}$alkyl optionally substituted with one, two, or three $R^{20d}$; each $R^{20d}$ is independently selected from halogen, —OH, $C_{2-5}$heterocycloalkyl optionally substituted with one, two, or three $C_{1-6}$ alkyl (e.g., methyl, ethyl, or propyl), and —$OR^{21}$, wherein $R^{21}$ is $C_{2-5}$heterocycloalkyl optionally substituted with one, two, or three $C_{1-6}$alkyl (e.g., methyl, ethyl, propyl, or butyl); $R^2$ is —$OR^{2a}$; $R^{2a}$ is methyl; $R^3$ is $C_{3-4}$cycloalkyl optionally substituted with one, two, or three $R^{20b}$; and each $R^{20b}$ is independently —CN or $C_{1-3}$haloalkyl. In embodiments of a compound of Formula (I'-2); $R^7$ is methyl; $L^1$ is a bond; $R^4$ is hydrogen; $R^6$ is hydrogen; $R^1$ is a 6-10 membered aryl ring substituted with one or more $R^{10}$; each $R^{10}$ is independently selected from halogen and $C_{1-4}$alkyl optionally substituted with one, two, or three $R^{20d}$; each $R^{20d}$ is independently selected from halogen, —OH, $C_{2-5}$heterocycloalkyl optionally substituted with one, two, or three $C_{1-6}$alkyl (e.g., methyl, ethyl, or propyl), and —$OR^{21}$, wherein $R^{21}$ is $C_{2-5}$heterocycloalkyl optionally substituted with one, two, or three $C_{1-6}$alkyl (e.g., methyl, ethyl, propyl, or butyl); $R^2$ is —$OR^{2a}$; $R^{2a}$ is methyl; $R^3$ is $C_{3-4}$cycloalkyl optionally substituted with one, two, or three $R^{20b}$; and each $R^{20b}$ is independently —CN or $C_{1-3}$ haloalkyl. In embodiments of a compound of Formula (I'-2); $R^7$ is methyl; $L^1$ is a bond; $R^4$ is hydrogen; $R^6$ is hydrogen; $R^1$ is a 6-10 membered aryl ring substituted with one or more $R^{10}$; each $R^{10}$ is independently selected from halogen and $C_{1-4}$alkyl optionally substituted with one, two, or three $R^{20d}$; each $R^{20d}$ is independently selected from halogen, —OH, $C_{2-5}$heterocycloalkyl optionally substituted with one, two, or three $C_{1-6}$alkyl (e.g., methyl, ethyl, or propyl), and —$OR^{21}$, wherein $R^{21}$ is $C_{2-5}$heterocycloalkyl optionally substituted with one, two, or three $C_{1-6}$alkyl (e.g., methyl, ethyl, propyl, or butyl); $R^2$ is —$OR^{2a}$; $R^{2a}$ is methyl; $R^3$ is $C_{3-4}$cycloalkyl optionally substituted with one, two, or three $R^{20b}$; and each $R^{20b}$ is independently —CN or $C_{1-3}$haloalkyl. In embodiments of a compound of Formula (I'-2); $R^7$ is methyl; $L^1$ is a bond; $R^4$ is hydrogen; $R^6$ is hydrogen; $R^1$ is a 6-10 membered aryl ring substituted with one or more $R^{10}$; each $R^{10}$ is independently selected from halogen and $C_{1-4}$alkyl optionally substituted with one, two, or three $R^{20d}$; each $R^{20d}$ is independently selected from halogen, —OH, $C_{2-5}$heterocycloalkyl optionally substituted with one, two, or three $C_{1-6}$alkyl (e.g., methyl, ethyl, or propyl), and —$OR^{21}$, wherein $R^{21}$ is $C_{2-5}$heterocycloalkyl optionally substituted with one, two, or three $C_{1-6}$ alkyl (e.g., methyl, ethyl, propyl, or butyl); $R^2$ is —$OR^{2a}$; $R^{2a}$ is methyl; $R^3$ is $C_{3-4}$cycloalkyl optionally substituted with one, two, or three $R^{20b}$; and each $R^{20b}$ is independently selected from amino; —CN; $C_{1-3}$alkyl; $C_{1-3}$alkoxy; $C_{1-3}$haloalkyl; —OH; —$N(R^{24})C(O)R^{25}$; and —$C(O)N(R^{22})(R^{23})$.

In embodiments of a compound of Formula (I-2); $R^7$ is methyl; $L^1$ is a bond; $R^4$ is hydrogen; $R^8$ is methyl; $R^6$ is hydrogen; $R^1$ is a

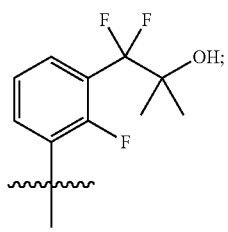 [SMILES: *c1cccc(C(F)(F)C(C)(C)O)c1F]

$R^2$ is —$OR^{2a}$; $R^{2a}$ is methyl; and $R^3$ is

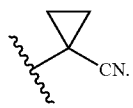 [SMILES: *C1(C#N)CC1]

In embodiments of a compound of Formula (I-2); $R^7$ is methyl; $L^1$ is a bond; $R^4$ is hydrogen; $R^5$ is methyl; $R^6$ is hydrogen; $R^1$ is a

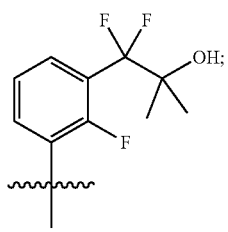 [SMILES: *c1cccc(C(F)(F)C(C)(C)O)c1F]

$R^2$ is —$OR^{2a}$; $R^{2a}$ is methyl; $R^3$ is cyclopropyl optionally substituted with one $R^{20b}$; and $R^{20b}$ is —CN. In embodiments of a compound of Formula (I-2); $R^7$ is methyl; $L^1$ is a bond; $R^4$ is hydrogen; $R^5$ is methyl; $R^6$ is hydrogen; $R^1$ is

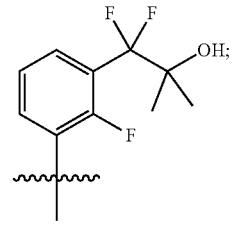 [SMILES: *c1cccc(C(F)(F)C(C)(C)O)c1F]

$R^2$ is —$OR^{2a}$; $R^{2a}$ is methyl; $R^3$ is $C_{3-4}$cycloalkyl optionally substituted with one $R^{21b}$; and $R^{2b}$ is —CN. In embodiments of a compound of Formula (I-2); $R^7$ is methyl; $L^1$ is a bond; $R^4$ is hydrogen; $R^5$ is methyl; $R^6$ is hydrogen; $R^1$ is a

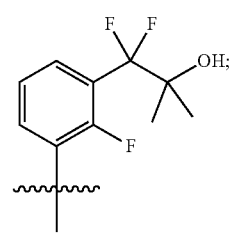 [SMILES: *c1cccc(C(F)(F)C(C)(C)O)c1F]

$R^2$ is —$OR^{2a}$; $R^{2a}$ is methyl; $R^3$ is $C_{3-4}$cycloalkyl optionally substituted with one, two, or three $R^{20b}$; and $R^{20b}$ is —CN. In embodiments of a compound of Formula (I-2); $R^7$ is methyl; $L^1$ is a bond; $R^4$ is hydrogen; $R^5$ is methyl; $R^6$ is hydrogen; $R^1$ is a

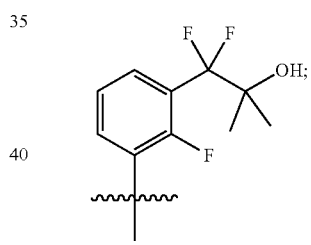

$R^2$ is —$OR^{2a}$; $R^{2a}$ is methyl; $R^3$ is $C_{3-4}$cycloalkyl optionally substituted with one, two, or three $R^{20b}$; and each $R^{20b}$ is independently —CN or $C_{1-3}$haloalkyl. In embodiments of a compound of Formula (I-2); $R^7$ is methyl; $L^1$ is a bond; $R^4$ is hydrogen; $R^5$ is methyl; $R^6$ is hydrogen; $R^1$ is a

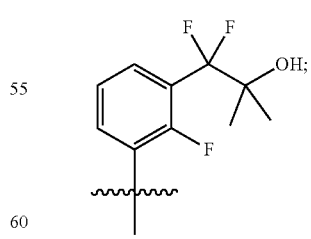

$R^2$ is —$OR^{2a}$; $R^{2a}$ is methyl; $R^3$ is $C_{3-4}$cycloalkyl optionally substituted with one, two, or three $R^{20b}$; and each $R^{20b}$ is independently —CN or $C_{1-3}$ haloalkyl. In embodiments of a compound of Formula (I-2); $R^7$ is methyl; $L^1$ is a bond; $R^4$ is hydrogen; $R^5$ is methyl; $R^6$ is hydrogen; $R^1$ is a

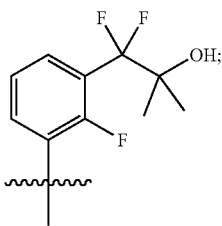 [SMILES: *c1cccc(C(F)(F)C(C)(C)O)c1F]

$R^2$ is —$OR^{2a}$; $R^{2a}$ is methyl; $R^3$ is $C_{3-4}$cycloalkyl optionally substituted with one, two, or three $R^{20b}$; and each $R^{20b}$ is independently —CN or $C_{1-3}$haloalkyl. In embodiments of a compound of Formula (I-2); $R^7$ is methyl; $L^1$ is a bond; $R^4$ is hydrogen; $R^5$ is methyl; $R^6$ is hydrogen; $R^1$ is a

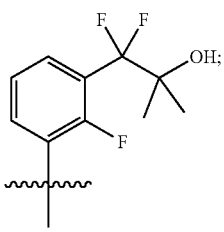 [SMILES: *c1cccc(C(F)(F)C(C)(C)O)c1F]

$R^2$ is —$OR^{2a}$; $R^{2a}$ is methyl; $R^3$ is $C_{3-4}$cycloalkyl optionally substituted with one, two, or three $R^{20b}$; and each $R^{20b}$ is independently selected from amino; —CN; $C_{1-3}$alkyl; $C_{1-3}$alkoxy; $C_{1-3}$haloalkyl; —OH; —N($R^{24}$)C(O)$R^{25}$; and —C(O)N($R^{22}$)($R^{23}$).

In embodiments of a compound of Formula (I-2); $R^7$ is methyl; $L^1$ is a bond; $R^4$ is hydrogen; $R^5$ is methyl; $R^6$ is hydrogen; $R^1$ is a

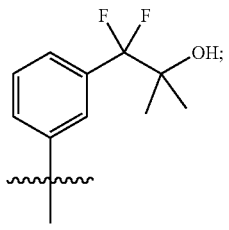 [SMILES: *c1cccc(C(F)(F)C(C)(C)O)c1]

$R^2$ is —$OR^{2a}$; $R^{2a}$ is methyl; and $R^3$ is

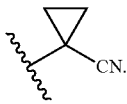

In embodiments of a compound of Formula (I-2); $R^7$ is methyl; $L^1$ is a bond; $R^4$ is hydrogen; $R^5$ is methyl; $R^6$ is hydrogen; $R^1$ is a

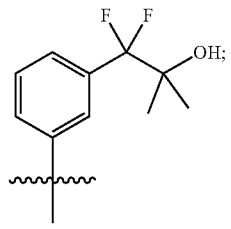 [SMILES: *c1cccc(C(F)(F)C(C)(C)O)c1]

$R^2$ is —$OR^{2a}$; $R^{2a}$ is methyl; $R^3$ is cyclopropyl optionally substituted with one $R^{20b}$; and $R^{20b}$ is —CN. In embodiments of a compound of Formula (I-2); $R^7$ is methyl; $L^1$ is a bond; $R^4$ is hydrogen; $R^5$ is methyl; $R^6$ is hydrogen; $R^1$ is a

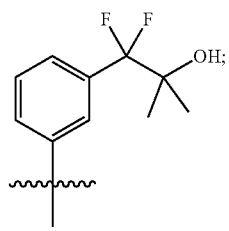 [SMILES: *c1cccc(C(F)(F)C(C)(C)O)c1]

$R^2$ is —$OR^{2a}$; $R^{2a}$ is methyl; $R^3$ is $C_{3-4}$cycloalkyl optionally substituted with one $R^{20b}$; and $R^{20b}$ is —CN. In embodiments of a compound of Formula (I-2); $R^7$ is methyl; $L^1$ is a bond; $R^4$ is hydrogen; $R^5$ is methyl; $R^6$ is hydrogen; $R^1$ is a

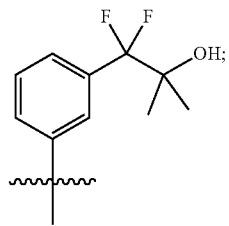 [SMILES: *c1cccc(C(F)(F)C(C)(C)O)c1]

$R^2$ is —$OR^{2a}$; $R^{2a}$ is methyl; $R^3$ is $C_{3-4}$cycloalkyl optionally substituted with one, two, or three $R^{20b}$; and $R^{20b}$ is —CN. In embodiments of a compound of Formula (I-2); $R^7$ is methyl; $L^1$ is a bond; $R^4$ is hydrogen; $R^5$ is methyl; $R^6$ is hydrogen; $R^1$ is a

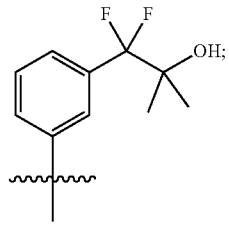 [SMILES: *c1cccc(C(F)(F)C(C)(C)O)c1]

$R^2$ is —$OR^{2a}$; $R^{2a}$ is methyl; $R^3$ is $C_{3-4}$cycloalkyl optionally substituted with one, two, or three $R^{20b}$; and each $R^{20b}$ is independently —CN or $C_{1-3}$haloalkyl. In embodiments of a compound of Formula (I-2); $R^7$ is methyl; $L^1$ is a bond; $R^4$ is hydrogen; $R^5$ is methyl; $R^6$ is hydrogen; $R^1$ is a

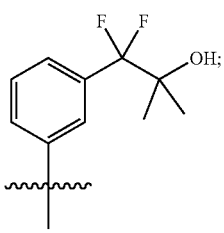 [SMILES: *c1cccc(C(F)(F)C(C)(C)O)c1]

$R^2$ is —$OR^{2a}$; $R^{2a}$ is methyl; $R^3$ is $C_{3-4}$cycloalkyl optionally substituted with one, two, or three $R^{20b}$; and each $R^{20b}$ is independently —CN or $C_{1-3}$ haloalkyl. In embodiments of a compound of Formula (I-2); $R^7$ is methyl; $L^1$ is a bond; $R^4$ is hydrogen; $R^5$ is methyl; $R^6$ is hydrogen; $R^1$ is a

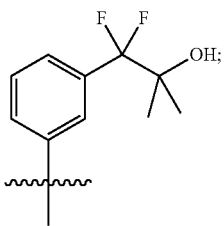 [SMILES: *c1cccc(C(F)(F)C(C)(C)O)c1]

$R^2$ is —$OR^{2a}$; $R^{2a}$ is methyl; $R^3$ is $C_{3-4}$cycloalkyl optionally substituted with one, two, or three $R^{20b}$; and each $R^{20b}$ is independently —CN or $C_{1-3}$ haloalkyl. In embodiments of a compound of Formula (I-2); $R^7$ is methyl; $L^1$ is a bond; $R^4$ is hydrogen; $R^5$ is methyl; $R^6$ is hydrogen; $R^1$ is a

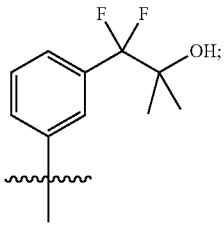 [SMILES: *c1cccc(C(F)(F)C(C)(C)O)c1]

$R^2$ is —$OR^{2a}$; $R^{2a}$ is methyl; $R^3$ is $C_{3-4}$cycloalkyl optionally substituted with one, two, or three $R^{20b}$; and each $R^{20b}$ is independently selected from amino; —CN; $C_{1-3}$alkyl; $C_{1-3}$alkoxy; $C_{1-3}$haloalkyl; —OH; —N($R^{24}$)C(O)$R^{21}$; and —C(O)N($R^{22}$)($R^{23}$).

In embodiments of a compound of Formula (I-2); $R^7$ is methyl; $L^1$ is a bond; $R^4$ is hydrogen; $R^5$ is methyl; $R^6$ is hydrogen; $R^1$ is a

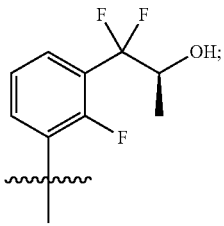 [SMILES: *c1cccc(C(F)(F)[C@H](C)O)c1F]

$R^2$ is —$OR^{2a}$; $R^{2a}$ is methyl; and $R^3$ is

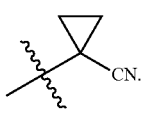 [SMILES: *C1(C#N)CC1]

In embodiments of a compound of Formula (I-2); $R^7$ is methyl; $L^1$ is a bond; $R^4$ is hydrogen; $R^5$ is methyl; $R^6$ is hydrogen; $R^1$ is a

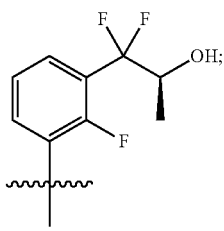 [SMILES: *c1cccc(C(F)(F)[C@H](C)O)c1F]

$R^2$ is —$OR^{2a}$; $R^{2a}$ is methyl; $R^3$ is cyclopropyl optionally substituted with one $R^{20b}$; and $R^{20b}$ is —CN. In embodiments of a compound of Formula (I-2); $R^7$ is methyl; $L^1$ is a bond; $R^4$ is hydrogen; $R^5$ is methyl; $R^6$ is hydrogen; $R^1$ is a

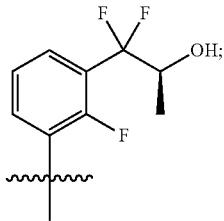 [SMILES: *c1cccc(C(F)(F)[C@H](C)O)c1F]

$R^2$ is —$OR^{2a}$; $R^{2a}$ is methyl; $R^3$ is $C_{3-4}$cycloalkyl optionally substituted with one $R^{20b}$; and $R^{20b}$ is —CN. In embodiments of a compound of Formula (I-2); $R^7$ is methyl; $L^1$ is a bond; $R^4$ is hydrogen; $R^5$ is methyl; $R^6$ is hydrogen; $R^1$ is a

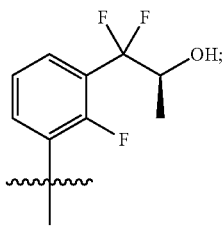 [SMILES: *c1cccc(C(F)(F)[C@H](C)O)c1F]

$R^2$ is —$OR^{2a}$; $R^{2a}$ is methyl; $R^3$ is $C_{3-4}$cycloalkyl optionally substituted with one, two, or three $R^{20b}$; and $R^{20b}$ is —CN. In embodiments of a compound of Formula (I-2); Ra is methyl; $L^1$ is a bond; $R^4$ is hydrogen; $R^5$ is methyl; $R^6$ is hydrogen; $R^1$ is a

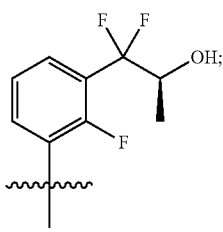 [SMILES: *c1cccc(C(F)(F)[C@H](C)O)c1F]

$R^2$ is —$OR^{2a}$; $R^{2a}$ is methyl; $R^3$ is $C_{3-4}$cycloalkyl optionally substituted with one, two, or three $R^{20b}$; and each $R^{20b}$ is independently —CN or $C_{1-3}$haloalkyl. In embodiments of a compound of Formula (I-2); $R^7$ is methyl; $L^1$ is a bond; $R^4$ is hydrogen; $R^5$ is methyl; $R^6$ is hydrogen; $R^1$ is

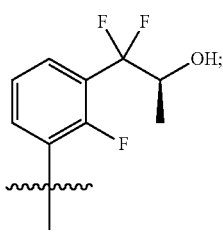 [SMILES: *c1cccc(C(F)(F)[C@H](C)O)c1F]

$R^2$ is —$OR^{2a}$; $R^{2a}$ is methyl; $R^3$ is $C_{3-4}$cycloalkyl optionally substituted with one, two, or three $R^{21b}$; and each $R^{2b}$ is independently —CN or $C_{1-3}$ haloalkyl. In embodiments of a compound of Formula (I-2); $R^7$ is methyl; $L^1$ is a bond; $R^4$ is hydrogen; $R^5$ is methyl; $R^6$ is hydrogen; $R^1$ is a

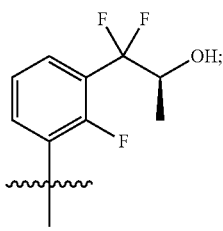 [SMILES: *c1cccc(C(F)(F)[C@H](C)O)c1F]

$R^2$ is —$OR^{2a}$; $R^{2a}$ is methyl; $R^3$ is $C_{3-4}$cycloalkyl optionally substituted with one, two, or three $R^{20b}$; and each $R^{20b}$ is independently —CN or $C_{1-3}$haloalkyl. In embodiments of a compound of Formula (I-2); $R^7$ is methyl; $L^1$ is a bond; $R^4$ is hydrogen; $R^5$ is methyl; $R^6$ is hydrogen; $R^1$ is a $R^2$ is —$OR^{2a}$; $R^{2a}$ is methyl; $R^3$ is $C_{3-4}$cycloalkyl optionally substituted with one, two, or three $R^{20b}$; and each $R^{20b}$ is independently selected from amino; —CN; $C_{1-3}$alkyl; $C_{1-3}$alkoxy; $C_{1-3}$haloalkyl; —OH; —N($R^{24}$)C(O)$R^{21}$; and —C(O)N($R^{22}$)($R^{23}$).

In embodiments of a compound of Formula (I-2); $R^7$ is methyl; $L^1$ is a bond; $R^4$ is hydrogen; $R^5$ is methyl; $R^6$ is hydrogen; $R^1$ is a

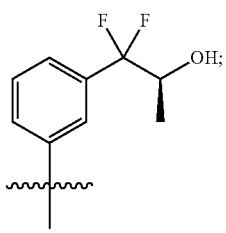 [SMILES: *c1cccc(C(F)(F)[C@H](C)O)c1]

$R^2$ is —$OR^{2a}$; $R^{2a}$ is methyl; and $R^3$ is

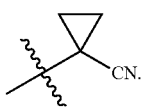 [SMILES: *C1(C#N)CC1]

In embodiments of a compound of Formula (I-2); $R^7$ is methyl; $L^1$ is a bond; $R^4$ is hydrogen; $R^5$ is methyl; $R^6$ is hydrogen; $R^1$ is a

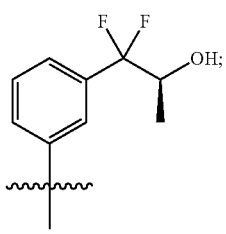

$R^2$ is —$OR^{2a}$; $R^{2a}$ is methyl; $R^3$ is cyclopropyl optionally substituted with one $R^{20b}$; and $R^{20b}$ is —CN. In embodiments of a compound of Formula (I-2); $R^7$ is methyl; $L^1$ is a bond; $R^4$ is hydrogen; $R^5$ is methyl; $R^6$ is hydrogen; $R^1$ is a

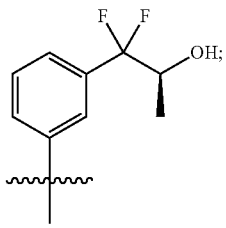 [SMILES: *c1cccc(C(F)(F)[C@H](C)O)c1]

$R^2$ is —$OR^{2a}$; $R^{2a}$ is methyl; $R^3$ is $C_{3-4}$cycloalkyl optionally substituted with one $R^{20b}$; and $R^{20b}$ is —CN. In embodiments of a compound of Formula (I-2); $R^7$ is methyl; $L^1$ is a bond; $R^4$ is hydrogen; $R^5$ is methyl; $R^6$ is hydrogen; $R^1$ is a

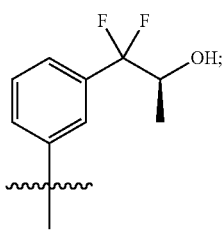 [SMILES: *c1cccc(C(F)(F)[C@H](C)O)c1]

$R^2$ is —$OR^{2a}$; $R^{2a}$ is methyl; $R^3$ is $C_{3-4}$cycloalkyl optionally substituted with one, two, or three $R^{20b}$; and $R^{20b}$ is —CN. In embodiments of a compound of Formula (I-2); $R^7$ is methyl; $L^1$ is a bond; $R^4$ is hydrogen; $R^5$ is methyl; $R^6$ is hydrogen; $R^1$ is a

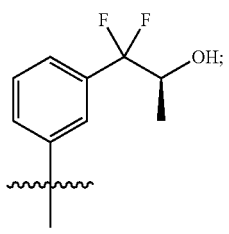 [SMILES: *c1cccc(C(F)(F)[C@H](C)O)c1]

$R^2$ is —$OR^{2a}$; $R^{2a}$ is methyl; $R^3$ is $C_{3-4}$cycloalkyl optionally substituted with one, two, or three $R^{20b}$; and each $R^{20b}$ is independently —CN or $C_{1-3}$haloalkyl. In embodiments of a compound of Formula (I-2); $R^7$ is methyl; $L^1$ is a bond; $R^4$ is hydrogen; $R^5$ is methyl; $R^6$ is hydrogen; $R^1$ is a

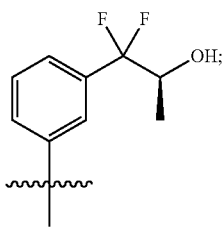 [SMILES: *c1cccc(C(F)(F)[C@H](C)O)c1]

$R^2$ is —$OR^{2a}$; $R^{2a}$ is methyl; $R^3$ is $C_{3-4}$cycloalkyl optionally substituted with one, two, or three $R^{20b}$; and each $R^{20b}$ is independently —CN or $C_{1-3}$haloalkyl. In embodiments of a compound of Formula (I-2); $R^7$ is methyl; $L^1$ is a bond; $R^4$ is hydrogen; $R^5$ is methyl; $R^6$ is hydrogen; $R^1$ is a

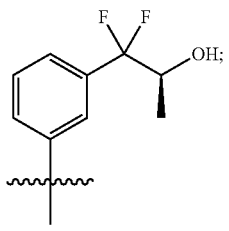 [SMILES: *c1cccc(C(F)(F)[C@H](C)O)c1]

$R^2$ is —$OR^{2a}$; $R^{2a}$ is methyl; $R^3$ is $C_{3-4}$cycloalkyl optionally substituted with one, two, or three $R^{20b}$; and each $R^{20b}$ is independently —CN or $C_{1-3}$haloalkyl. In embodiments of a compound of Formula (I-2); $R^7$ is methyl; $L^1$ is a bond; $R^4$ is hydrogen; $R^5$ is methyl; $R^6$ is hydrogen; $R^1$ is a

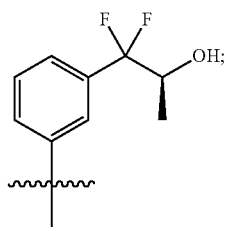

$R^2$ is —$OR^{2a}$; $R^{2a}$ is methyl; $R^3$ is $C_{3-4}$cycloalkyl optionally substituted with one, two, or three $R^{20b}$; and each $R^{20b}$ is independently selected from amino; —CN; $C_{1-3}$alkyl; $C_{1-3}$alkoxy; $C_{1-3}$haloalkyl; —OH; —$N(R^{24})C(O)R^{25}$; and —$C(O)N(R^{22})(R^{23})$.

In embodiments of a compound of Formula (I-2); $R^7$ is methyl; $L^1$ is a bond; $R^4$ is hydrogen; $R^5$ is methyl; $R^6$ is hydrogen; $R^1$ is a

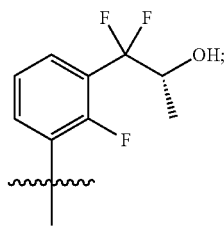 [SMILES: *c1cccc(C(F)(F)[C@@H](C)O)c1F]

$R^2$ is —$OR^{2a}$; $R^{2a}$ is methyl; and $R^3$ is

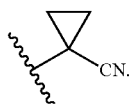 [SMILES: *C1(C#N)CC1]

In embodiments of a compound of Formula (I-2); $R^7$ is methyl; $L^1$ is a bond; $R^4$ is hydrogen; $R^5$ is methyl; $R^6$ is hydrogen; $R^1$ is a

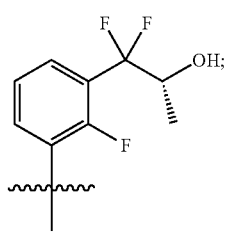 [SMILES: *c1cccc(C(F)(F)[C@@H](C)O)c1F]

$R^2$ is —$OR^{2a}$; $R^{2a}$ is methyl; $R^3$ is cyclopropyl optionally substituted with one $R^{20b}$; and $R^{20b}$ is —CN. In embodiments of a compound of Formula (I-2); $R^7$ is methyl; $L^1$ is a bond; $R^4$ is hydrogen; $R^5$ is methyl; $R^6$ is hydrogen; $R^1$ is a

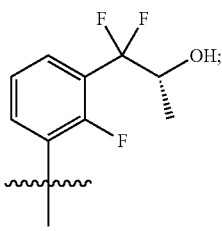 [SMILES: *c1cccc(C(F)(F)[C@@H](C)O)c1F]

$R^2$ is —$OR^{2a}$; $R^{2a}$ is methyl; $R^3$ is $C_{3-4}$cycloalkyl optionally substituted with one $R^{20b}$; and $R^{20b}$ is —CN. In embodiments of a compound of Formula (I-2); $R^7$ is methyl; $L^1$ is a bond; $R^4$ is hydrogen; $R^6$ is methyl; $R^6$ is hydrogen; $R^1$ is a

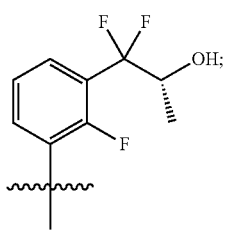 [SMILES: *c1cccc(C(F)(F)[C@@H](C)O)c1F]

$R^2$ is —$OR^{2a}$; $R^{2a}$ is methyl; $R^3$ is $C_{3-4}$cycloalkyl optionally substituted with one, two, or three $R^{20b}$; and $R^{20b}$ is —CN. In embodiments of a compound of Formula (I-2); $R^7$ is methyl; $L^1$ is a bond; $R^4$ is hydrogen; $R^5$ is methyl; $R^6$ is hydrogen; $R^1$ is a

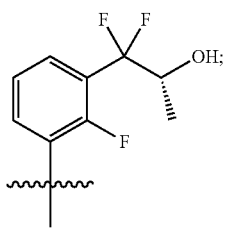 [SMILES: *c1cccc(C(F)(F)[C@@H](C)O)c1F]

$R^2$ is —$OR^{2a}$; $R^{2a}$ is methyl; $R^3$ is $C_{3-4}$cycloalkyl optionally substituted with one, two, or three $R^{20b}$; and each $R^{20b}$ is independently —CN or $C_{1-3}$haloalkyl. In embodiments of a compound of Formula (I-2); $R^7$ is methyl; $L^1$ is a bond; $R^4$ is hydrogen; $R^5$ is methyl; $R^6$ is hydrogen; $R^1$ is a

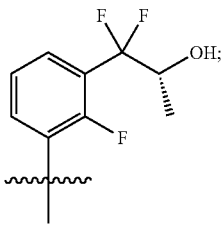 [SMILES: *c1cccc(C(F)(F)[C@@H](C)O)c1F]

$R^2$ is —$OR^{2a}$; $R^{2a}$ is methyl; $R^3$ is $C_{3-4}$cycloalkyl optionally substituted with one, two, or three $R^{20b}$; and each $R^{20b}$ is independently —CN or $C_{1-3}$ haloalkyl. In embodiments of a compound of Formula (I-2); $R^7$ is methyl; $L^1$ is a bond; $R^4$ is hydrogen; $R^5$ is methyl; $R^6$ is hydrogen; $R^1$ is a

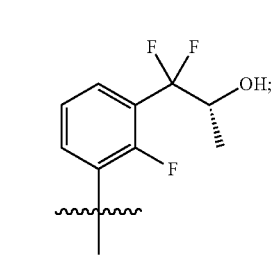 [SMILES: *c1cccc(C(F)(F)[C@@H](C)O)c1F]

$R^2$ is —$OR^{2a}$; $R^{2a}$ is methyl; $R^3$ is $C_{3-4}$cycloalkyl optionally substituted with one, two, or three $R^{20b}$; and each $R^{20b}$ is independently —CN or $C_{1-3}$ haloalkyl. In embodiments of a compound of Formula (I-2); $R^7$ is methyl; $L^1$ is a bond; $R^4$ is hydrogen; $R^5$ is methyl; $R^6$ is hydrogen; $R^1$ is a

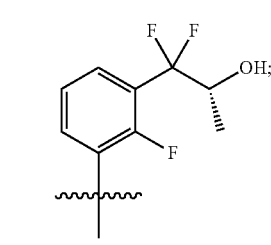 [SMILES: *c1cccc(C(F)(F)[C@@H](C)O)c1F]

$R^2$ is —$OR^{2a}$; $R^{2a}$ is methyl; $R^3$ is $C_{3-4}$cycloalkyl optionally substituted with one, two, or three $R^{20b}$; and each $R^{20b}$ is independently selected from amino; —CN; $C_{1-3}$alkyl; $C_{1-3}$alkoxy; $C_{1-3}$haloalkyl; —OH; —$N(R^{24})C(O)R^{25}$; and —$C(O)N(R^{22})(R^{23})$.

In embodiments of a compound of Formula (I-2); $R^7$ is methyl; $L^1$ is a bond; $R^4$ is hydrogen; $R^5$ is methyl; $R^6$ is hydrogen; $R^1$ is a

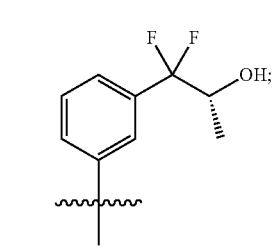 [SMILES: *c1cccc(C(F)(F)[C@@H](C)O)c1]

$R^2$ is —$OR^{2a}$; $R^{2a}$ is methyl; and $R^3$ is

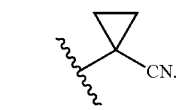 [SMILES: *C1(C#N)CC1]

In embodiments of a compound of Formula (I-2); $R^7$ is methyl; $L^1$ is a bond; $R^4$ is hydrogen; $R^5$ is methyl; $R^6$ is hydrogen; $R^1$ is a

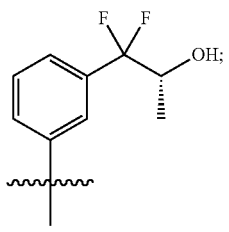 [SMILES: *c1cccc(C(F)(F)[C@@H](C)O)c1]

$R^2$ is —$OR^{2a}$; $R^{2a}$ is methyl; $R^3$ is cyclopropyl optionally substituted with one $R^{20b}$; and $R^{20b}$ is —CN. In embodiments of a compound of Formula (I-2); $R^7$ is methyl; $L^1$ is a bond; $R^4$ is hydrogen; $R^5$ is methyl; $R^6$ is hydrogen; $R^1$ is a

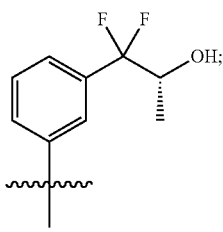 [SMILES: *c1cccc(C(F)(F)[C@@H](C)O)c1]

$R^2$ is —$OR^{2a}$; $R^{2a}$ is methyl; $R^3$ is $C_{3-4}$cycloalkyl optionally substituted with one $R^{20b}$; and $R^{20b}$ is —CN. In embodiments of a compound of Formula (I-2); $R^7$ is methyl; $L^1$ is a bond; $R^4$ is hydrogen; $R^5$ is methyl; $R^6$ is hydrogen; $R^1$ is a

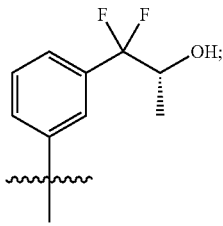 [SMILES: *c1cccc(C(F)(F)[C@@H](C)O)c1]

$R^2$ is —$OR^{2a}$; $R^{2a}$ is methyl; $R^3$ is $C_{3-4}$cycloalkyl optionally substituted with one, two, or three $R^{20b}$; and $R^{20b}$ is —CN. In embodiments of a compound of Formula (I-2); $R^7$ is methyl; $L^1$ is a bond; $R^4$ is hydrogen; $R^5$ is methyl; $R^6$ is hydrogen; $R^1$ is a

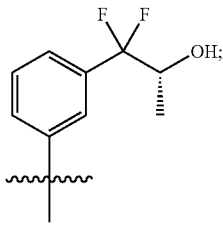 [SMILES: *c1cccc(C(F)(F)[C@@H](C)O)c1]

$R^2$ is —$OR^{2a}$; $R^{2a}$ is methyl; $R^3$ is $C_{3-4}$cycloalkyl optionally substituted with one, two, or three $R^{20b}$; and each $R^{20b}$ is independently —CN or $C_{1-3}$haloalkyl. In embodiments of a compound of Formula (I-2); $R^7$ is methyl; $L^1$ is a bond; $R^4$ is hydrogen; $R^5$ is methyl; $R^6$ is hydrogen; $R^1$ is a

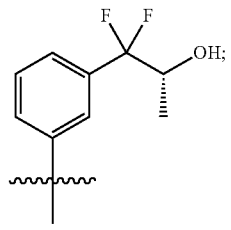 [SMILES: *c1cccc(C(F)(F)[C@@H](C)O)c1]

$R^2$ is —$OR^{2a}$; $R^{2a}$ is methyl; $R^3$ is $C_{3-4}$cycloalkyl optionally substituted with one, two, or three $R^{20b}$; and each $R^{20b}$ is independently —CN or $C_{1-3}$haloalkyl. In embodiments of a compound of Formula (I-2); $R^7$ is methyl; $L^1$ is a bond; $R^4$ is hydrogen; $R^5$ is methyl; $R^6$ is hydrogen; $R^1$ is a

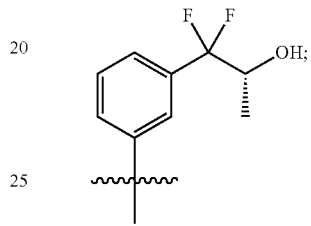

$R^2$ is —$OR^{2a}$; $R^{2a}$ is methyl; $R^3$ is $C_{3-4}$cycloalkyl optionally substituted with one, two, or three $R^{20b}$; and each $R^{20b}$ is independently —CN or $C_{1-3}$haloalkyl. In embodiments of a compound of Formula (I-2); $R^7$ is methyl; $L^1$ is a bond; $R^4$ is hydrogen; $R^5$ is methyl; $R^6$ is hydrogen; $R^1$ is a

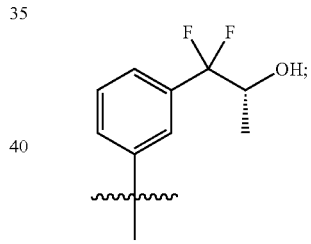

$R^2$ is —$OR^{2a}$; $R^{2a}$ is methyl; $R^3$ is $C_{3-4}$cycloalkyl optionally substituted with one, two, or three $R^{20b}$; and each $R^{20b}$ is independently selected from amino; —CN; $C_{1-3}$alkyl; $C_{1-3}$alkoxy; $C_{1-3}$haloalkyl; —OH; —$N(R^{24})C(O)R^{25}$; and —$C(O)N(R^{22})(R^{23})$.

In embodiments of a compound of Formula (I-2); $R^7$ is methyl; $L^1$ is a bond; $R^4$ is hydrogen; $R^5$ is methyl; $R^6$ is hydrogen; $R^1$ is a phenyl substituted with one or more $R^{10}$; each $R^{10}$ is independently selected from halogen and $C_{1-4}$alkyl optionally substituted with one, two, or three $R^{20d}$; each $R^{20d}$ is independently selected from halogen and —OH; $R^2$ is —$OR^{2a}$; $R^{2a}$ is methyl; and $R^3$ is

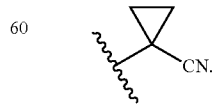

In embodiments of a compound of Formula (I-2); $R^7$ is methyl; $L^1$ is a bond; $R^4$ is hydrogen; $R^5$ is methyl; $R^6$ is hydrogen; $R^1$ is a phenyl substituted with one or more $R^{10}$;

each $R^{10}$ is independently selected from halogen and $C_{1-4}$alkyl optionally substituted with one, two, or three $R^{20d}$; each $R^{20d}$ is independently selected from halogen and —OH; $R^2$ is —OR$^{2a}$; $R^{2a}$ is methyl; $R^3$ is cyclopropyl optionally substituted with one $R^{20b}$; and $R^{20b}$ is —CN. In embodiments of a compound of Formula (I-2); $R^7$ is methyl; $L^1$ is a bond; $R^4$ is hydrogen; $R^5$ is methyl; $R^6$ is hydrogen; $R^1$ is a phenyl substituted with one or more $R^{10}$; each $R^{10}$ is independently selected from halogen and $C_{1-4}$alkyl optionally substituted with one, two, or three $R^{20d}$; each $R^{20d}$ is independently selected from halogen and —OH; $R^2$ is —OR$^{2a}$; $R^{2a}$ is methyl; $R^3$ is $C_{3-4}$cycloalkyl optionally substituted with one $R^{20b}$; and $R^{20b}$ is —CN. In embodiments of a compound of Formula (I-2); $R^7$ is methyl; $L^1$ is a bond; $R^4$ is hydrogen; $R^5$ is methyl; $R^6$ is hydrogen; $R^1$ is a phenyl substituted with one or more $R^{10}$; each $R^{10}$ is independently selected from halogen and $C_{1-4}$alkyl optionally substituted with one, two, or three $R^{20d}$; each $R^{20d}$ is independently selected from halogen and —OH; $R^2$ is —OR$^{2a}$; $R^{2a}$ is methyl; $R^3$ is $C_{3-4}$cycloalkyl optionally substituted with one, two, or three $R^{20b}$; and $R^{20b}$ is —CN. In embodiments of a compound of Formula (I-2); $R^7$ is methyl; $L^1$ is a bond; $R^4$ is hydrogen; $R^5$ is methyl; $R^6$ is hydrogen; $R^1$ is a phenyl substituted with one or more $R^{10}$; each $R^{10}$ is independently selected from halogen and $C_{1-4}$alkyl optionally substituted with one, two, or three $R^{20d}$; each $R^{20d}$ is independently selected from halogen and —OH; $R^2$ is —OR$^{2a}$; $R^{2a}$ is methyl; $R^3$ is $C_{3-4}$cycloalkyl optionally substituted with one, two, or three $R^{20b}$; and each $R^{20b}$ is independently —CN or $C_{1-3}$haloalkyl. In embodiments of a compound of Formula (I-2); $R^7$ is methyl; $L^1$ is a bond; $R^4$ is hydrogen; $R^5$ is methyl; $R^6$ is hydrogen; $R^1$ is a phenyl substituted with one or more $R^{10}$; each $R^{10}$ is independently selected from halogen and $C_{1-4}$ alkyl optionally substituted with one, two, or three $R^{20d}$; each $R^{20d}$ is independently selected from halogen and —OH; $R^2$ is —OR$^{2a}$; $R^{2a}$ is methyl; $R^3$ is $C_{3-4}$cycloalkyl optionally substituted with one, two, or three $R^{20b}$; and each $R^{20b}$ is independently —CN or $C_{1-3}$haloalkyl. In embodiments of a compound of Formula (I-2); $R^7$ is methyl; $L^1$ is a bond; $R^4$ is hydrogen; $R^5$ is methyl; $R^6$ is hydrogen; $R^1$ is a phenyl substituted with one or more $R^{10}$; each $R^{10}$ is independently selected from halogen and $C_{1-4}$alkyl optionally substituted with one, two, or three $R^{20d}$; each $R^{20d}$ is independently selected from halogen and —OH; $R^2$ is —OR$^{2a}$; $R^{2a}$ is methyl; $R^3$ is $C_{3-4}$cycloalkyl optionally substituted with one, two, or three $R^{20b}$; and each $R^{20b}$ is independently selected from amino; —CN; $C_{1-3}$alkyl; $C_{1-3}$alkoxy; $C_{1-3}$haloalkyl; —OH; —N(R$^{24}$)C(O)R$^{21}$; and —C(O)N(R$^{22}$)(R$^{23}$).

In embodiments of a compound of Formula (I-2); $R^7$ is methyl; $L^1$ is a bond; $R^4$ is hydrogen; $R^5$ is methyl; $R^6$ is hydrogen; $R^1$ is a phenyl substituted with one or more $R^{10}$; each $R^{10}$ is independently selected from halogen and $C_{1-4}$alkyl optionally substituted with one, two, or three $R^{20d}$; each $R^{20d}$ is independently selected from halogen, —OH, $C_{2-5}$heterocycloalkyl optionally substituted with one, two, or three $C_{1-6}$alkyl (e.g., methyl, ethyl, or propyl), and —OR$^{21}$, wherein $R^{21}$ is $C_{2-5}$heterocycloalkyl optionally substituted with one, two, or three $C_{1-6}$alkyl (e.g., methyl, ethyl, propyl, or butyl); $R^2$ is —OR$^{2a}$; $R^{2a}$ is methyl; and $R^3$ is

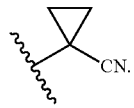 [SMILES: *C1(C#N)CC1]

In embodiments of a compound of Formula (I-2); $R^7$ is methyl; $L^1$ is a bond; $R^4$ is hydrogen; $R^5$ is methyl; $R^6$ is hydrogen; $R^1$ is a phenyl substituted with one or more $R^{10}$; each $R^{10}$ is independently selected from halogen and $C_{1-4}$alkyl optionally substituted with one, two, or three $R^{20d}$; each $R^{20d}$ is independently selected from halogen, —OH, $C_{2-5}$heterocycloalkyl optionally substituted with one, two, or three $C_{1-6}$alkyl (e.g., methyl, ethyl, or propyl), and —OR$^{21}$, wherein $R^{21}$ is $C_{2-5}$heterocycloalkyl optionally substituted with one, two, or three $C_{1-6}$alkyl (e.g., methyl, ethyl, propyl, or butyl); $R^2$ is —OR$^{2a}$; $R^{2a}$ is methyl; $R^3$ is cyclopropyl optionally substituted with one $R^{20b}$; and $R^{20b}$ is —CN. In embodiments of a compound of Formula (I-2); $R^7$ is methyl; $L^1$ is a bond; $R^4$ is hydrogen; $R^5$ is methyl; $R^6$ is hydrogen; $R^1$ is a phenyl substituted with one or more $R^{10}$; each $R^{10}$ is independently selected from halogen and $C_{1-4}$alkyl optionally substituted with one, two, or three $R^{20d}$; each $R^{20d}$ is independently selected from halogen, —OH, $C_{2-5}$heterocycloalkyl optionally substituted with one, two, or three $C_{1-6}$alkyl (e.g., methyl, ethyl, or propyl), and —OR$^{21}$, wherein $R^{21}$ is $C_{2-5}$heterocycloalkyl optionally substituted with one, two, or three $C_{1-6}$alkyl (e.g., methyl, ethyl, propyl, or butyl); $R^2$ is —OR$^{2a}$; $R^{2a}$ is methyl; $R^3$ is $C_{3-4}$cycloalkyl optionally substituted with one $R^{20b}$; and $R^{20b}$ is —CN. In embodiments of a compound of Formula (I-2); $R^7$ is methyl; $L^1$ is a bond; $R^4$ is hydrogen; $R^5$ is methyl; $R^6$ is hydrogen; $R^1$ is a phenyl substituted with one or more $R^{10}$; each $R^{10}$ is independently selected from halogen and $C_{1-4}$alkyl optionally substituted with one, two, or three $R^{20d}$; each $R^{20d}$ is independently selected from halogen, —OH, $C_{2-5}$heterocycloalkyl optionally substituted with one, two, or three $C_{1-6}$alkyl (e.g., methyl, ethyl, or propyl), and —OR$^{21}$, wherein $R^{21}$ is $C_{2-5}$heterocycloalkyl optionally substituted with one, two, or three $C_{1-6}$alkyl (e.g., methyl, ethyl, propyl, or butyl); $R^2$ is —OR$^{2a}$; $R^{2a}$ is methyl; $R^3$ is $C_{3-4}$cycloalkyl optionally substituted with one, two, or three $R^{20b}$; and $R^{20b}$ is —CN. In embodiments of a compound of Formula (I-2); $R^7$ is methyl; $L^1$ is a bond; $R^4$ is hydrogen; $R^5$ is methyl; $R^6$ is hydrogen; $R^1$ is a phenyl substituted with one or more $R^{10}$; each $R^{10}$ is independently selected from halogen and $C_{1-4}$alkyl optionally substituted with one, two, or three $R^{20d}$; each $R^{20d}$ is independently selected from halogen, —OH, $C_{2-5}$heterocycloalkyl optionally substituted with one, two, or three $C_{1-6}$alkyl (e.g., methyl, ethyl, or propyl), and —$OR^{21}$, wherein $R^{21}$ is $C_{2-5}$heterocycloalkyl optionally substituted with one, two, or three $C_{1-6}$alkyl (e.g., methyl, ethyl, propyl, or butyl); $R^2$ is —$OR^{2a}$; $R^{2a}$ is methyl; $R^3$ is $C_{3-4}$cycloalkyl optionally substituted with one, two, or three $R^{20b}$; and each $R^{20b}$ is independently —CN or $C_{1-3}$haloalkyl. In embodiments of a compound of Formula (I-2); $R^7$ is methyl; $L^1$ is a bond; $R^4$ is hydrogen; $R^5$ is methyl; $R^6$ is hydrogen; $R^1$ is a phenyl substituted with one or more $R^{10}$; each $R^{10}$ is independently selected from halogen and $C_{1-4}$alkyl optionally substituted with one, two, or three $R^{20d}$; each $R^{20d}$ is independently selected from halogen, —OH, $C_{2-5}$heterocycloalkyl optionally substituted with one, two, or three $C_{1-6}$alkyl (e.g., methyl, ethyl, or propyl), and —$OR^{21}$, wherein $R^{21}$ is $C_{2-5}$heterocycloalkyl optionally substituted with one, two, or three $C_{1-6}$alkyl (e.g., methyl, ethyl, propyl, or butyl); $R^2$ is —$OR^{2a}$; $R^{2a}$ is methyl; $R^3$ is $C_{3-4}$cycloalkyl optionally substituted with one, two, or three $R^{20b}$; and each $R^{20b}$ is independently —CN or $C_{1-3}$haloalkyl. In embodiments of a compound of Formula (I-2); $R^7$ is methyl; $L^1$ is a bond; $R^4$ is hydrogen; $R^5$ is methyl; $R^6$ is hydrogen; $R^1$ is a phenyl substituted with one or more $R^{10}$; each $R^{10}$ is independently selected from halogen and $C_{1-4}$alkyl optionally substituted with one, two, or three $R^{20d}$; each $R^{20d}$ is independently selected from halogen, —OH, $C_{2-5}$heterocycloalkyl optionally substituted with one, two, or three $C_{1-6}$alkyl (e.g., methyl, ethyl, or propyl), and —$OR^{21}$, wherein $R^{21}$ is $C_{2-5}$heterocycloalkyl optionally substituted with one, two, or three $C_{1-6}$alkyl (e.g., methyl, ethyl, propyl, or butyl); $R^2$ is —$OR^{2a}$; $R^{2a}$ is methyl; $R^3$ is $C_{3-4}$cycloalkyl optionally substituted with one, two, or three $R^{20b}$; and each $R^{20b}$ is independently selected from amino; —CN; $C_{1-3}$alkyl; $C_{1-3}$alkoxy; $C_{1-3}$haloalkyl; —OH; —$N(R^{24})C(O)R^{25}$; and —$C(O)N(R^{22})(R^{23})$.

In embodiments of a compound of Formula (I-2); $R^7$ is methyl; $L^1$ is a bond; $R^4$ is hydrogen; $R^5$ is methyl; $R^6$ is hydrogen; $R^1$ is a 6-10 membered aryl ring substituted with one or more $R^{10}$; each $R^{10}$ is independently selected from halogen and $C_{1-4}$alkyl optionally substituted with one, two, or three $R^{20d}$; each $R^{20d}$ is independently selected from halogen, —OH, $C_{2-5}$heterocycloalkyl optionally substituted with one, two, or three $C_{1-6}$alkyl (e.g., methyl, ethyl, or propyl), and —$OR^{21}$, wherein $R^{21}$ is $C_{2-5}$heterocycloalkyl optionally substituted with one, two, or three $C_{1-6}$alkyl (e.g., methyl, ethyl, propyl, or butyl); $R^2$ is —$OR^{2a}$; $R^{2a}$ is methyl; and $R^3$ is

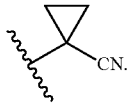

In embodiments of a compound of Formula (I-2); $R^7$ is methyl; $L^1$ is a bond; $R^4$ is hydrogen; $R^5$ is methyl; $R^6$ is hydrogen; $R^1$ is a 6-10 membered aryl ring substituted with one or more $R^{10}$; each $R^{10}$ is independently selected from halogen and $C_{1-4}$alkyl optionally substituted with one, two, or three $R^{20d}$; each $R^{20d}$ is independently selected from halogen, —OH, $C_{2-5}$heterocycloalkyl optionally substituted with one, two, or three $C_{1-6}$alkyl (e.g., methyl, ethyl, or propyl), and —$OR^{21}$, wherein $R^{21}$ is $C_{2-5}$heterocycloalkyl optionally substituted with one, two, or three $C_{1-6}$alkyl (e.g., methyl, ethyl, propyl, or butyl); $R^2$ is —$OR^{2a}$; $R^{2a}$ is methyl; $R^3$ is cyclopropyl optionally substituted with one $R^{20b}$; and $R^{20b}$ is —CN. In embodiments of a compound of Formula (I-2); $R^7$ is methyl; $L^1$ is a bond; $R^4$ is hydrogen; $R^5$ is methyl; $R^6$ is hydrogen; $R^1$ is a 6-10 membered aryl ring substituted with one or more $R^{10}$; each $R^{10}$ is independently selected from halogen and $C_{1-4}$alkyl optionally substituted with one, two, or three $R^{20d}$; each $R^{20d}$ is independently selected from halogen, —OH, $C_{2-5}$heterocycloalkyl optionally substituted with one, two, or three $C_{1-6}$alkyl (e.g., methyl, ethyl, or propyl), and —$OR^{21}$, wherein $R^{21}$ is $C_{2-5}$heterocycloalkyl optionally substituted with one, two, or three $C_{1-6}$alkyl (e.g., methyl, ethyl, propyl, or butyl); $R^2$ is —$OR^{2a}$; $R^{2a}$ is methyl; $R^3$ is $C_{3-4}$cycloalkyl optionally substituted with one $R^{20b}$; and $R^{20b}$ is —CN. In embodiments of a compound of Formula (I-2); $R^7$ is methyl; $L^1$ is a bond; $R^4$ is hydrogen; $R^5$ is methyl; $R^6$ is hydrogen; $R^1$ is a 6-10 membered aryl ring substituted with one or more $R^{10}$; each $R^{10}$ is independently selected from halogen and $C_{1-4}$alkyl optionally substituted with one, two, or three $R^{20d}$; each $R^{20d}$ is independently selected from halogen, —OH, $C_{2-5}$heterocycloalkyl optionally substituted with one, two, or three $C_{1-6}$alkyl (e.g., methyl, ethyl, or propyl), and —$OR^{21}$, wherein $R^{21}$ is $C_{2-5}$heterocycloalkyl optionally substituted with one, two, or three $C_{1-6}$alkyl (e.g., methyl, ethyl, propyl, or butyl); $R^2$ is —$OR^{2a}$; $R^{2a}$ is methyl; $R^3$ is $C_{3-4}$cycloalkyl optionally substituted with one, two, or three $R^{20b}$; and each $R^{20b}$ is independently —CN or $C_{1-3}$haloalkyl. In embodiments of a compound of Formula (I-2); $R^7$ is methyl; $L^1$ is a bond; $R^4$ is hydrogen; $R^5$ is methyl; $R^6$ is hydrogen; $R^1$ is a 6-10 membered aryl ring substituted with one or more $R^{10}$; each $R^{10}$ is independently selected from halogen and $C_{1-4}$alkyl optionally substituted with one, two, or three $R^{20d}$; each $R^{20d}$ is independently selected from halogen, —OH, $C_{2-5}$heterocycloalkyl optionally substituted with one, two, or three $C_{1-6}$alkyl (e.g., methyl, ethyl, or propyl), and —$OR^{21}$, wherein $R^{21}$ is $C_{2-5}$heterocycloalkyl optionally substituted with one, two, or three $C_{1-6}$alkyl (e.g., methyl, ethyl, propyl, or butyl); $R^2$ is —$OR^{2a}$; $R^{2a}$ is methyl; $R^3$ is $C_{3-4}$cycloalkyl optionally substituted with one, two, or three $R^{20b}$; and each $R^{20b}$ is independently —CN or $C_{1-3}$haloalkyl. In embodiments of a compound of Formula (I-2); $R^7$ is methyl; $L^1$ is a bond; $R^4$ is hydrogen; $R^5$ is methyl; $R^6$ is hydrogen; $R^1$ is a 6-10 membered aryl ring substituted with one or more $R^{10}$; each $R^{10}$ is independently selected from halogen and $C_{1-4}$alkyl optionally substituted with one, two, or three $R^{20d}$; each $R^{20d}$ is independently selected from halogen, —OH, $C_{2-5}$heterocycloalkyl optionally substituted with one, two, or three $C_{1-6}$alkyl (e.g., methyl, ethyl, or propyl), and —$OR^{21}$, wherein $R^{21}$ is $C_{2-5}$heterocycloalkyl optionally substituted with one, two, or three $C_{1-6}$alkyl (e.g., methyl, ethyl, propyl, or butyl); $R^2$ is —$OR^{2a}$; $R^{2a}$ is methyl; $R^3$ is $C_{3-4}$cycloalkyl optionally substituted with one, two, or three $R^{20b}$; and each $R^{20b}$ is independently —CN or $C_{1-3}$haloalkyl. In embodiments of a compound of Formula (I-2); $R^7$ is methyl; $L^1$ is a bond; $R^4$ is hydrogen; $R^5$ is methyl; $R^6$ is hydrogen; $R^1$ is a 6-10 membered aryl ring substituted with one or more $R^{10}$; each $R^{10}$ is independently selected from halogen and $C_{1-4}$alkyl optionally substituted with one, two, or three $R^{20d}$; each $R^{20d}$ is independently selected from halogen, —OH, $C_{2-5}$heterocycloalkyl optionally substituted with one, two, or three $C_{1-6}$alkyl (e.g., methyl, ethyl, or propyl), and —$OR^{21}$, wherein $R^{21}$ is $C_{2-5}$heterocycloalkyl optionally substituted with one, two, or three $C_{1-6}$alkyl (e.g., methyl, ethyl, propyl, or butyl); $R^2$ is —$OR^{2a}$; $R^{2a}$ is methyl; $R^3$ is $C_{3-4}$cycloalkyl optionally substituted with one, two, or three $R^{20b}$; and each $R^{20b}$ is independently selected from amino; —CN; $C_{1-3}$alkyl; $C_{1-3}$alkoxy; $C_{1-3}$haloalkyl; —OH; —$N(R^{24})C(O)R^{25}$; and —$C(O)N(R^{22})(R^{23})$.

In embodiments of a compound of Formula (I'-2); $R^7$ is methyl optionally substituted with one, two, or three $R^{20c}$; each $R^{20c}$ is independently selected from halogen, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl; $L^1$ is a bond; $R^4$ is hydrogen; $R^6$ is hydrogen; $R^1$ is a

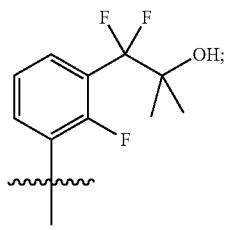 [SMILES: *c1cccc(C(F)(F)C(C)(C)O)c1F]

$R^2$ is —$OR^{2a}$; $R^{2a}$ is methyl; and $R^3$ is

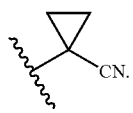 [SMILES: *C1(C#N)CC1]

In embodiments of a compound of Formula (I'-2); $R^7$ is methyl optionally substituted with one, two, or three $R^{20c}$; each $R^{20c}$ is independently selected from halogen, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl; $L^1$ is a bond; $R^4$ is hydrogen; $R^6$ is hydrogen; $R^1$ is a

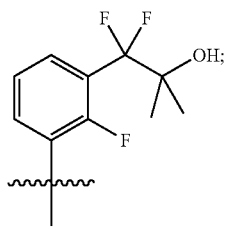 [SMILES: *c1cccc(C(F)(F)C(C)(C)O)c1F]

$R^2$ is —$OR^{2a}$; $R^{2a}$ is methyl; $R^3$ is cyclopropyl optionally substituted with one $R^{21b}$; and $R^{20b}$ is —CN. In embodiments of a compound of Formula (I'-2); $R^7$ is methyl optionally substituted with one, two, or three $R^{20c}$; each $R^{20c}$ is independently selected from halogen, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl; $L^1$ is a bond; $R^4$ is hydrogen; $R^6$ is hydrogen; $R^1$ is a

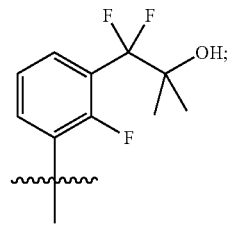 [SMILES: *c1cccc(C(F)(F)C(C)(C)O)c1F]

$R^2$ is —$OR^{2a}$; $R^{2a}$ is methyl; $R^3$ is $C_{3-4}$cycloalkyl optionally substituted with one $R^{20b}$; and $R^{20b}$ is —CN. In embodiments of a compound of Formula (I'-2); $R^7$ is methyl optionally substituted with one, two, or three $R^{20c}$; each $R^{20c}$ is independently selected from halogen, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl; $L^1$ is a bond; $R^4$ is hydrogen; $R^6$ is hydrogen; $R^1$ is a

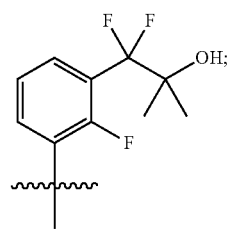 [SMILES: *c1cccc(C(F)(F)C(C)(C)O)c1F]

$R^2$ is —$OR^{2a}$; $R^{2a}$ is methyl; $R^3$ is $C_{3-4}$cycloalkyl optionally substituted with one, two, or three $R^{20b}$; and $R^{20b}$ is —CN. In embodiments of a compound of Formula (I'-2); $R^7$ is methyl optionally substituted with one, two, or three $R^{20c}$; each $R^{20c}$ is independently selected from halogen, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl; $L^1$ is a bond; $R^4$ is hydrogen; $R^6$ is hydrogen; $R^1$ is a

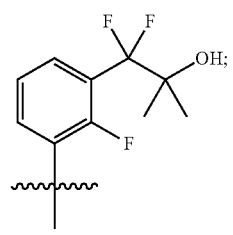 [SMILES: *c1cccc(C(F)(F)C(C)(C)O)c1F]

$R^2$ is —$OR^{2a}$; $R^{2a}$ is methyl; $R^3$ is $C_{3-4}$cycloalkyl optionally substituted with one, two, or three $R^{20b}$; and each $R^{20b}$ is independently —CN or $C_{1-3}$haloalkyl. In embodiments of a compound of Formula (I'-2); $R^7$ is methyl optionally substituted with one, two, or three $R^{20c}$; each $R^{20c}$ is independently selected from halogen, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl; $L^1$ is a bond; $R^4$ is hydrogen; $R^6$ is hydrogen; $R^1$ is a

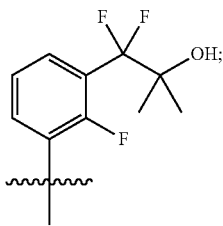 [SMILES: *c1cccc(C(F)(F)C(C)(C)O)c1F]

$R^2$ is —$OR^{2a}$; $R^{2a}$ is methyl; $R^3$ is $C_{3-4}$cycloalkyl optionally substituted with one, two, or three $R^{20b}$; and each $R^{20b}$ is independently —CN or $C_{1-3}$haloalkyl. In embodiments of a compound of Formula (I'-2); $R^7$ is methyl optionally substituted with one, two, or three $R^{20c}$; each $R^{20c}$ is independently selected from halogen, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl; $L^1$ is a bond; $R^4$ is hydrogen; $R^6$ is hydrogen; $R^1$ is a

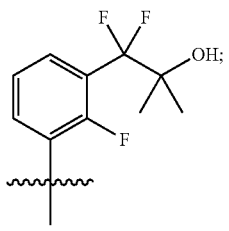 [SMILES: *c1cccc(C(F)(F)C(C)(C)O)c1F]

$R^2$ is —$OR^{2a}$; $R^{2a}$ is methyl; $R^3$ is $C_{3-4}$cycloalkyl optionally substituted with one, two, or three $R^{20b}$; and each $R^{20b}$ is independently —CN or $C_{1-3}$ haloalkyl. In embodiments of a compound of Formula (I'-2); $R^7$ is methyl optionally substituted with one, two, or three $R^{20c}$; each $R^{20c}$ is independently selected from halogen, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl; $L^1$ is a bond; $R^4$ is hydrogen; $R^6$ is hydrogen; $R^1$ is a

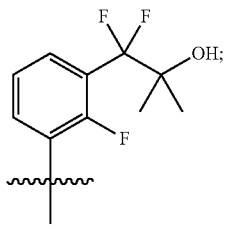 [SMILES: *c1cccc(C(F)(F)C(C)(C)O)c1F]

$R^2$ is —$OR^{2a}$; $R^{2a}$ is methyl; $R^3$ is $C_{3-4}$cycloalkyl optionally substituted with one, two, or three $R^{20b}$; and each $R^{20b}$ is independently selected from amino; —CN; $C_{1-3}$alkyl; $C_{1-3}$alkoxy; $C_{1-3}$ haloalkyl; —OH; —N($R^{24}$)C(O)$R^{21}$; and —C(O)N($R^{22}$)($R^{23}$).

In embodiments of a compound of Formula (I'-2); $R^7$ is methyl optionally substituted with one, two, or three $R^{20c}$; each $R^{20c}$ is independently selected from halogen, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl; $L^1$ is a bond; $R^4$ is hydrogen; $R^6$ is hydrogen; $R^1$ is a

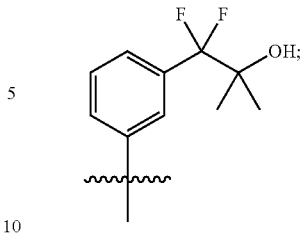

$R^2$ is —$OR^{2a}$; $R^{2a}$ is methyl; and $R^3$ is

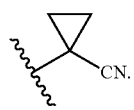 [SMILES: *C1(C#N)CC1]

In embodiments of a compound of Formula (I'-2); $R^7$ is methyl optionally substituted with one, two, or three $R^{20c}$; each $R^{20c}$ is independently selected from halogen, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl; $L^1$ is a bond; $R^4$ is hydrogen; $R^6$ is hydrogen; $R^1$ is a

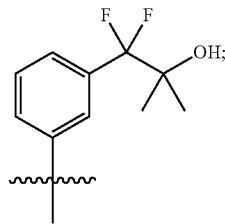 [SMILES: *c1cccc(C(F)(F)C(C)(C)O)c1]

$R^2$ is —$OR^{2a}$; $R^{2a}$ is methyl; $R^3$ is cyclopropyl optionally substituted with one $R^{20b}$; and $R^{20b}$ is —CN. In embodiments of a compound of Formula (I'-2); $R^7$ is methyl optionally substituted with one, two, or three $R^{20c}$; each $R^{20c}$ is independently selected from halogen, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl; $L^1$ is a bond; $R^4$ is hydrogen; $R^6$ is hydrogen; $R^1$ is a

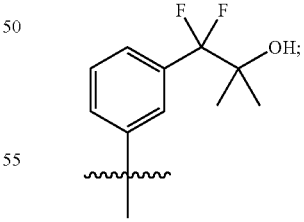

$R^2$ is —$OR^{2a}$; $R^{2a}$ is methyl; $R^3$ is $C_{3-4}$cycloalkyl optionally substituted with one $R^{20b}$; and $R^{20b}$ is —CN. In embodiments of a compound of Formula (I'-2); $R^7$ is methyl optionally substituted with one, two, or three $R^{20c}$; each $R^{20c}$ is independently selected from halogen, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl; $L^1$ is a bond; $R^4$ is hydrogen; $R^6$ is hydrogen; $R^1$ is a

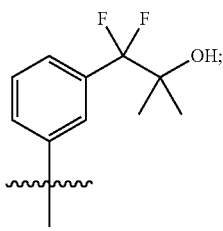 [SMILES: *c1cccc(C(F)(F)C(C)(C)O)c1]

$R^2$ is —$OR^{2a}$; $R^{2a}$ is methyl; $R^3$ is $C_{3-4}$cycloalkyl optionally substituted with one, two, or three $R^{20b}$; and $R^{20b}$ is —CN. In embodiments of a compound of Formula (I'-2); $R^7$ is methyl optionally substituted with one, two, or three $R^{20c}$; each $R^{20c}$ is independently selected from halogen, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl; $L^1$ is a bond; $R^4$ is hydrogen; $R^6$ is hydrogen; $R^1$ is a

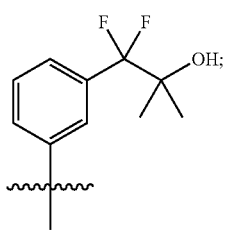 [SMILES: *c1cccc(C(F)(F)C(C)(C)O)c1]

$R^2$ is —$OR^{2a}$; $R^{2a}$ is methyl; $R^3$ is $C_{3-4}$cycloalkyl optionally substituted with one, two, or three $R^{20b}$; and each $R^{20b}$ is independently —CN or $C_{1-3}$haloalkyl. In embodiments of a compound of Formula (I'-2); $R^7$ is methyl optionally substituted with one, two, or three $R^{20c}$; each $R^{20c}$ is independently selected from halogen, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl; $L^1$ is a bond; $R^4$ is hydrogen; $R^6$ is hydrogen; $R^1$ is a

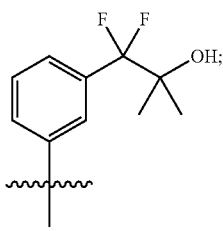 [SMILES: *c1cccc(C(F)(F)C(C)(C)O)c1]

$R^2$ is —$OR^{2a}$; $R^{2a}$ is methyl; $R^3$ is $C_{3-4}$cycloalkyl optionally substituted with one, two, or three $R^{20b}$; and each $R^{20b}$ is independently —CN or $C_{1-3}$haloalkyl. In embodiments of a compound of Formula (I-2); $R^7$ is methyl optionally substituted with one, two, or three $R^{20c}$; each $R^{20c}$ is independently selected from halogen, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl; $L^1$ is a bond; $R^4$ is hydrogen; $R^6$ is hydrogen; $R^1$ is a

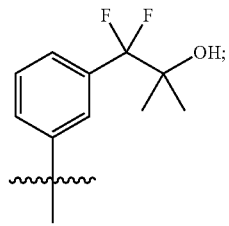 [SMILES: *c1cccc(C(F)(F)C(C)(C)O)c1]

$R^2$ is —$OR^{2a}$; $R^{2a}$ is methyl; $R^3$ is $C_{3-4}$cycloalkyl optionally substituted with one, two, or three $R^{20b}$; and each $R^{20b}$ is independently —CN or $C_{1-3}$ haloalkyl. In embodiments of a compound of Formula (I'-2); $R^7$ is methyl optionally substituted with one, two, or three $R^{20c}$; each $R^{20c}$ is independently selected from halogen, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl; $L^1$ is a bond; $R^4$ is hydrogen; $R^6$ is hydrogen; $R^1$ is a

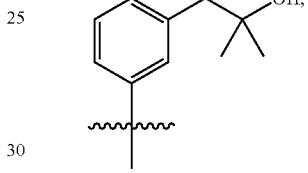

$R^2$ is —$OR^{2a}$; $R^{2a}$ is methyl; $R^3$ is $C_{3-4}$cycloalkyl optionally substituted with one, two, or three $R^{20b}$; and each $R^{20b}$ is independently selected from amino; —CN; $C_{1-3}$alkyl; $C_{1-3}$alkoxy; $C_{1-3}$ haloalkyl; —OH; —$N(R^{24})C(O)R^{25}$; and —$C(O)N(R^{22})(R^{23})$.

In embodiments of a compound of Formula (I'-2); $R^7$ is methyl optionally substituted with one, two, or three $R^{20c}$; each $R^{20c}$ is independently selected from halogen, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl; $L^1$ is a bond; $R^4$ is hydrogen; $R^6$ is hydrogen; $R^1$ is a

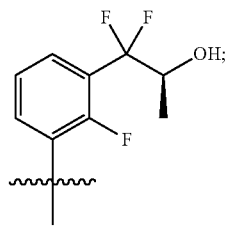 [SMILES: *c1cccc(C(F)(F)[C@H](C)O)c1F]

$R^2$ is —$OR^{2a}$; $R^{2a}$ is methyl; and $R^3$ is

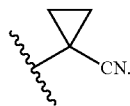

In embodiments of a compound of Formula (I'-2); $R^7$ is methyl optionally substituted with one, two, or three $R^{20c}$; each $R^{20c}$ is independently selected from halogen, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl; $L^1$ is a bond; $R^4$ is hydrogen; $R^6$ is hydrogen; $R^1$ is a

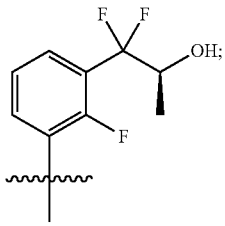 [SMILES: *c1cccc(C(F)(F)[C@H](C)O)c1F]

$R^2$ is —$OR^{2a}$; $R^{2a}$ is methyl; $R^3$ is cyclopropyl optionally substituted with one $R^{21b}$; and $R^{20b}$ is —CN. In embodiments of a compound of Formula (I'-2); $R^7$ is methyl optionally substituted with one, two, or three $R^{20c}$; each $R^{20c}$ is independently selected from halogen, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl; $L^1$ is a bond; $R^4$ is hydrogen; $R^6$ is hydrogen; $R^1$ is a

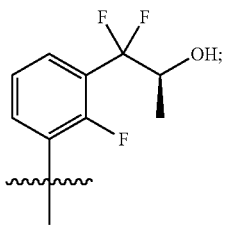 [SMILES: *c1cccc(C(F)(F)[C@H](C)O)c1F]

$R^2$ is —$OR^{2a}$; $R^{2a}$ is methyl; $R^3$ is $C_{3-4}$cycloalkyl optionally substituted with one $R^{20b}$; and $R^{20b}$ is —CN. In embodiments of a compound of Formula (I'-2); $R^7$ is methyl optionally substituted with one, two, or three $R^{20c}$; each $R^{20c}$ is independently selected from halogen, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl; $L^1$ is a bond; $R^4$ is hydrogen; $R^6$ is hydrogen; $R^1$ is a

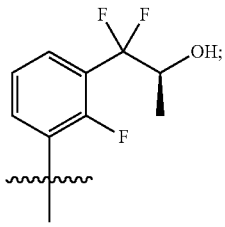 [SMILES: *c1cccc(C(F)(F)[C@H](C)O)c1F]

$R^2$ is —$OR^{2a}$; $R^{2a}$ is methyl; $R^3$ is $C_{3-4}$cycloalkyl optionally substituted with one, two, or three $R^{20b}$; and $R^{20b}$ is —CN. In embodiments of a compound of Formula (I'-2); $R^7$ is methyl optionally substituted with one, two, or three $R^{20c}$; each $R^{20c}$ is independently selected from halogen, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl; $L^1$ is a bond; $R^4$ is hydrogen; $R^6$ is hydrogen; $R^1$ is a

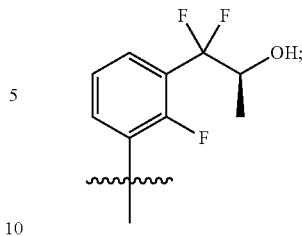

$R^2$ is —$OR^{2a}$; $R^{2a}$ is methyl; $R^3$ is $C_{3-4}$cycloalkyl optionally substituted with one, two, or three $R^{20b}$; and each $R^{20b}$ is independently —CN or $C_{1-3}$haloalkyl. In embodiments of a compound of Formula (I'-2); $R^7$ is methyl optionally substituted with one, two, or three $R^{20c}$; each $R^{20c}$ is independently selected from halogen, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl; $L^1$ is a bond; $R^4$ is hydrogen; $R^6$ is hydrogen; $R^1$ is a

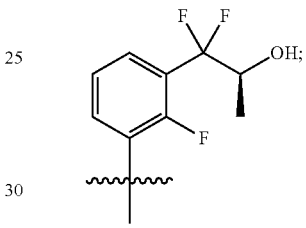

$R^2$ is —$OR^{2a}$; $R^{2a}$ is methyl; $R^3$ is $C_{3-4}$cycloalkyl optionally substituted with one, two, or three $R^{20b}$; and each $R^{20b}$ is independently —CN or $C_{1-3}$haloalkyl. In embodiments of a compound of Formula (I'-2); $R^7$ is methyl optionally substituted with one, two, or three $R^{20c}$; each $R^{20c}$ is independently selected from halogen, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl; $L^1$ is a bond; $R^4$ is hydrogen; $R^6$ is hydrogen; $R^1$ is a

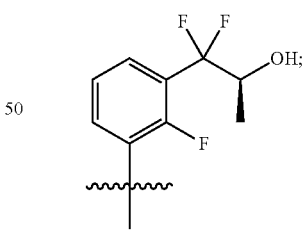

$R^2$ is —$OR^{2a}$; $R^{2a}$ is methyl; $R^3$ is $C_{3-4}$cycloalkyl optionally substituted with one, two, or three $R^{20b}$; and each $R^{20b}$ is independently —CN or $C_{1-3}$ haloalkyl. In embodiments of a compound of Formula (I'-2); $R^7$ is methyl optionally substituted with one, two, or three $R^{20c}$; each $R^{20c}$ is independently selected from halogen, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl; $L^1$ is a bond; $R^4$ is hydrogen; $R^6$ is hydrogen; $R^1$ is a

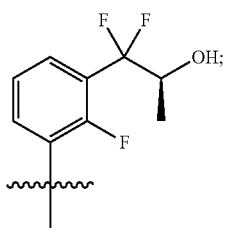 [SMILES: *c1cccc(C(F)(F)[C@H](C)O)c1F]

R² is —OR²ᵃ; R²ᵃ is methyl; R³ is C₃₋₄cycloalkyl optionally substituted with one, two, or three R²⁰ᵇ; and each R²⁰ᵇ is independently selected from amino; —CN; C₁₋₃alkyl; C₁₋₃alkoxy; C₁₋₃ haloalkyl; —OH; —N(R²⁴)C(O)R²⁵; and —C(O)N(R²²)(R²³).

In embodiments of a compound of Formula (I'-2); R⁷ is methyl optionally substituted with one, two, or three R²⁰ᶜ; each R²⁰ᶜ is independently selected from halogen, C₂₋₆alkenyl, C₂₋₆alkynyl, C₃₋₁₀cycloalkyl, C₂₋₉heterocycloalkyl, C₆₋₁₀aryl, and C₁₋₉heteroaryl; L¹ is a bond; R⁴ is hydrogen; R⁶ is hydrogen; R¹ is a

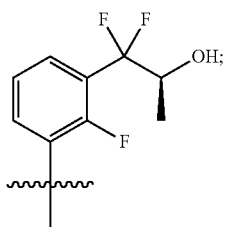 [SMILES: *c1cccc(C(F)(F)[C@H](C)O)c1F]

R² is —OR²ᵃ; R²ᵃ is methyl; and R³ is

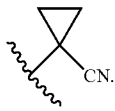

In embodiments of a compound of Formula (I'-2); R⁷ is methyl optionally substituted with one, two, or three R²⁰ᶜ; each R²⁰ᶜ is independently selected from halogen, C₂₋₆alkenyl, C₂₋₆alkynyl, C₃₋₁₀cycloalkyl, C₂₋₉heterocycloalkyl, C₆₋₁₀aryl, and C₁₋₉heteroaryl; L¹ is a bond; R⁴ is hydrogen; R⁶ is hydrogen; R¹ is a

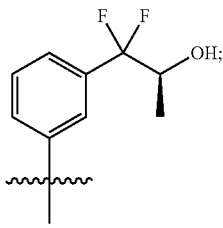 [SMILES: *c1cccc(C(F)(F)[C@H](C)O)c1]

R² is —OR²ᵃ; R²ᵃ is methyl; R³ is cyclopropyl optionally substituted with one R²⁰ᵇ; and R²⁰ᵇ is —CN. In embodiments of a compound of Formula (I'-2); R⁷ is methyl optionally substituted with one, two, or three R²⁰ᶜ; each R²⁰ᶜ is independently selected from halogen, C₂₋₆alkenyl, C₂₋₆alkynyl, C₃₋₁₀cycloalkyl, C₂₋₉heterocycloalkyl, C₆₋₁₀aryl, and C₁₋₉heteroaryl; L¹ is a bond; R⁴ is hydrogen; R⁶ is hydrogen; R¹ is a

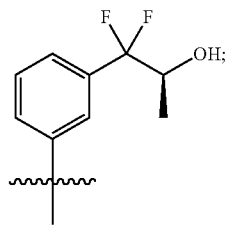 [SMILES: *c1cccc(C(F)(F)[C@H](C)O)c1]

R² is —OR²ᵃ; R²ᵃ is methyl; R³ is C₃₋₄cycloalkyl optionally substituted with one R²⁰ᵇ; and R²⁰ᵇ is —CN. In embodiments of a compound of Formula (I'-2); R⁷ is methyl optionally substituted with one, two, or three R²⁰ᶜ; each R²⁰ᶜ is independently selected from halogen, C₂₋₆alkenyl, C₂₋₆alkynyl, C₃₋₁₀cycloalkyl, C₂₋₉heterocycloalkyl, C₆₋₁₀aryl, and C₁₋₉heteroaryl; L¹ is a bond; R⁴ is hydrogen; R⁶ is hydrogen; R¹ is a

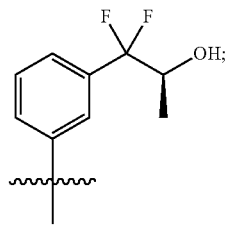 [SMILES: *c1cccc(C(F)(F)[C@H](C)O)c1]

R² is —OR²ᵃ; R²ᵃ is methyl; R³ is C₃₋₄cycloalkyl optionally substituted with one, two, or three R²⁰ᵇ; and R²⁰ᵇ is —CN. In embodiments of a compound of Formula (I'-2); R⁷ is methyl optionally substituted with one, two, or three R²⁰ᶜ; each R²⁰ᶜ is independently selected from halogen, C₂₋₆alkenyl, C₂₋₆alkynyl, C₃₋₁₀cycloalkyl, C₂₋₉heterocycloalkyl, C₆₋₁₀aryl, and C₁₋₉heteroaryl; L¹ is a bond; R⁴ is hydrogen; R⁶ is hydrogen; R¹ is a

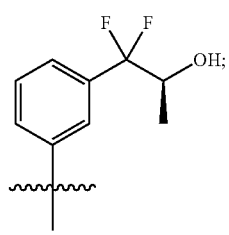 [SMILES: *c1cccc(C(F)(F)[C@H](C)O)c1]

R² is —OR²ᵃ; R²ᵃ is methyl; R³ is C₃₋₄cycloalkyl optionally substituted with one, two, or three R²⁰ᵇ; and each R²⁰ᵇ is independently —CN or C₁₋₃haloalkyl. In embodiments of a compound of Formula (I'-2); R⁷ is methyl optionally substituted with one, two, or three R²⁰ᶜ; each R²⁰ᶜ is independently selected from halogen, C₂₋₆alkenyl, C₂₋₆alkynyl, C₃₋₁₀cycloalkyl, C₂₋₉heterocycloalkyl, C₆₋₁₀aryl, and C₁₋₉heteroaryl; L¹ is a bond; R⁴ is hydrogen; R⁶ is hydrogen; R¹ is a

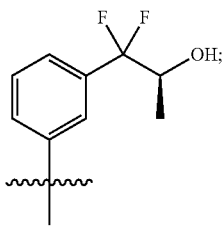 [SMILES: *c1cccc(C(F)(F)[C@H](C)O)c1]

$R^2$ is —$OR^{2a}$; $R^{2a}$ is methyl; $R^3$ is $C_{3-4}$cycloalkyl optionally substituted with one, two, or three $R^{20b}$; and each $R^{20b}$ is independently —CN or $C_{1-3}$haloalkyl. In embodiments of a compound of Formula (I-2); $R^7$ is methyl optionally substituted with one, two, or three $R^{20c}$; each $R^{20c}$ is independently selected from halogen, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl; $L^1$ is a bond; $R^4$ is hydrogen; $R^6$ is hydrogen; $R^1$ is a

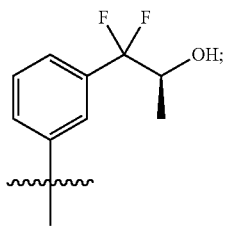 [SMILES: *c1cccc(C(F)(F)[C@H](C)O)c1]

$R^2$ is —$OR^{2a}$; $R^{2a}$ is methyl; $R^3$ is $C_{3-4}$cycloalkyl optionally substituted with one, two, or three $R^{20b}$; and each $R^{20b}$ is independently —CN or $C_{1-3}$ haloalkyl. In embodiments of a compound of Formula (I'-2); $R^7$ is methyl optionally substituted with one, two, or three $R^{20c}$; each $R^{20c}$ is independently selected from halogen, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl; $L^1$ is a bond; $R^4$ is hydrogen; $R^6$ is hydrogen; $R^1$ is a

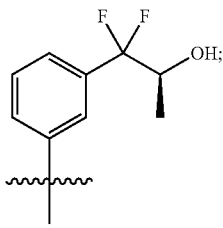 [SMILES: *c1cccc(C(F)(F)[C@H](C)O)c1]

$R^2$ is —$OR^{2a}$; $R^{2a}$ is methyl; $R^3$ is $C_{3-4}$cycloalkyl optionally substituted with one, two, or three $R^{20b}$; and each $R^{20b}$ is independently selected from amino; —CN; $C_{1-3}$alkyl; $C_{1-3}$alkoxy; $C_{1-3}$ haloalkyl; —OH; —$N(R^{24})C(O)R^{25}$; and —$C(O)N(R^{22})(R^{23})$.

In embodiments of a compound of Formula (I'-2); $R^7$ is methyl optionally substituted with one, two, or three $R^{20c}$; each $R^{20c}$ is independently selected from halogen, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl; $L^1$ is a bond; $R^4$ is hydrogen; $R^6$ is hydrogen; $R^1$ is a

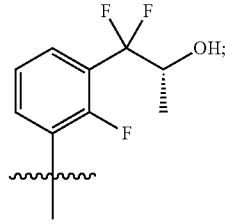 [SMILES: *c1cccc(C(F)(F)[C@@H](C)O)c1F]

$R^2$ is —$OR^{2a}$; $R^{2a}$ is methyl; and $R^3$ is

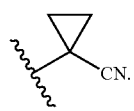 [SMILES: *C1(C#N)CC1]

In embodiments of a compound of Formula (I'-2); $R^7$ is methyl optionally substituted with one, two, or three $R^{20c}$; each $R^{20c}$ is independently selected from halogen, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl; $L^1$ is a bond; $R^4$ is hydrogen; $R^6$ is hydrogen; $R^1$ is a

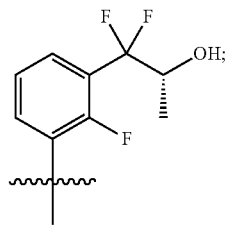 [SMILES: *c1cccc(C(F)(F)[C@@H](C)O)c1F]

$R^2$ is —$OR^{2a}$; $R^{2a}$ is methyl; $R^3$ is cyclopropyl optionally substituted with one $R^{20b}$; and $R^{20b}$ is —CN. In embodiments of a compound of Formula (I'-2); $R^7$ is methyl optionally substituted with one, two, or three $R^{20c}$; each $R^{20c}$ is independently selected from halogen, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl; $L^1$ is a bond; $R^4$ is hydrogen; $R^6$ is hydrogen; $R^1$ is a

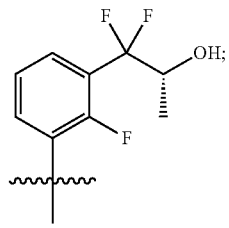 [SMILES: *c1cccc(C(F)(F)[C@@H](C)O)c1F]

$R^2$ is —$OR^{2a}$. $R^{2a}$ is methyl; $R^3$ is $C_{3-4}$cycloalkyl optionally substituted with one $R^{20b}$; and $R^{20b}$ is —CN. In embodiments of a compound of Formula (I'-2); $R^7$ is methyl optionally substituted with one, two, or three $R^{20c}$; each $R^{20c}$ is independently selected from halogen, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl; $L^1$ is a bond; $R^4$ is hydrogen; $R^6$ is hydrogen; $R^1$ is a

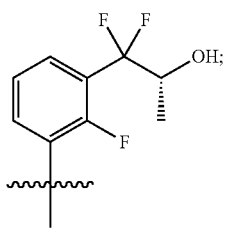 [SMILES: *c1cccc(C(F)(F)[C@@H](C)O)c1F]

$R^2$ is —$OR^{2a}$; $R^{2a}$ is methyl; $R^3$ is $C_{3-4}$cycloalkyl optionally substituted with one, two, or three $R^{20b}$; and $R^{20b}$ is —CN. In embodiments of a compound of Formula (I'-2); $R^7$ is methyl optionally substituted with one, two, or three $R^{20c}$; each $R^{20c}$ is independently selected from halogen, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl; $L^1$ is a bond; $R^4$ is hydrogen; $R^6$ is hydrogen; $R^1$ is a

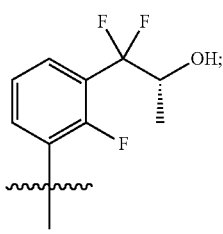 [SMILES: *c1cccc(C(F)(F)[C@@H](C)O)c1F]

$R^2$ is —$OR^{2a}$; $R^{2a}$ is methyl; $R^3$ is $C_{3-4}$cycloalkyl optionally substituted with one, two, or three $R^{20b}$; and each $R^{20b}$ is independently —CN or $C_{1-3}$haloalkyl. In embodiments of a compound of Formula (I'-2); $R^7$ is methyl optionally substituted with one, two, or three $R^{20c}$; each $R^{20c}$ is independently selected from halogen, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl; $L^1$ is a bond; $R^4$ is hydrogen; $R^6$ is hydrogen; $R^1$ is a

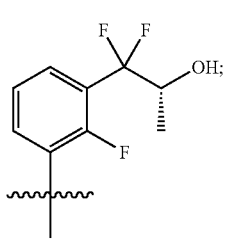 [SMILES: *c1cccc(C(F)(F)[C@@H](C)O)c1F]

$R^2$ is —$OR^{2a}$; $R^{2a}$ is methyl; $R^3$ is $C_{3-4}$cycloalkyl optionally substituted with one, two, or three $R^{20b}$; and each $R^{20b}$ is independently —CN or $C_{1-3}$haloalkyl. In embodiments of a compound of Formula (I'-2); $R^7$ is methyl optionally substituted with one, two, or three $R^{20c}$; each $R^{20c}$ is independently selected from halogen, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl; $L^1$ is a bond; $R^4$ is hydrogen; $R^6$ is hydrogen; $R^1$ is a

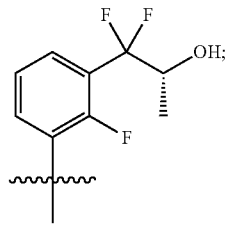 [SMILES: *c1cccc(C(F)(F)[C@@H](C)O)c1F]

$R^2$ is —$OR^{2a}$; $R^{2a}$ is methyl; $R^3$ is $C_{3-4}$cycloalkyl optionally substituted with one, two, or three $R^{20b}$; and each $R^{20b}$ is independently —CN or $C_{1-3}$ haloalkyl. In embodiments of a compound of Formula (I'-2); $R^7$ is methyl optionally substituted with one, two, or three $R^{20c}$; each $R^{20c}$ is independently selected from halogen, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl; $L^1$ is a bond; $R^4$ is hydrogen; $R^6$ is hydrogen; $R^1$ is

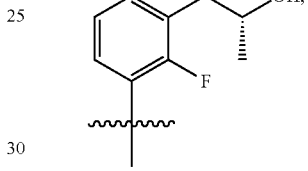

$R^2$ is —$OR^{2a}$; $R^{2a}$ is methyl; $R^3$ is $C_{3-4}$cycloalkyl optionally substituted with one, two, or three $R^{20b}$; and each $R^{20b}$ is independently selected from amino; —CN; $C_{1-3}$alkyl; $C_{1-3}$alkoxy; $C_{1-3}$ haloalkyl; —OH; —$N(R^{24})C(O)R^{25}$; and —$C(O)N(R^{22})(R^{23})$.

In embodiments of a compound of Formula (I'-2); $R^7$ is methyl optionally substituted with one, two, or three $R^{20c}$; each $R^{20c}$ is independently selected from halogen, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl; $L^1$ is a bond; $R^4$ is hydrogen; $R^6$ is hydrogen; $R^1$ is a

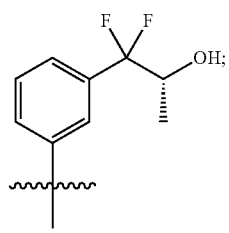 [SMILES: *c1cccc(C(F)(F)[C@@H](C)O)c1]

$R^2$ is —$OR^{2a}$; $R^{2a}$ is methyl; and $R^3$ is

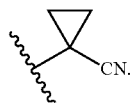

In embodiments of a compound of Formula (I'-2); $R^7$ is methyl optionally substituted with one, two, or three $R^{20c}$; each $R^{20c}$ is independently selected from halogen, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl; $L^1$ is a bond; $R^4$ is hydrogen; $R^6$ is hydrogen; $R^1$ is a

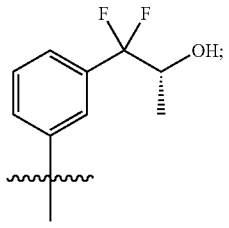 [SMILES: *c1cccc(C(F)(F)[C@@H](C)O)c1]

$R^2$ is —$OR^{2a}$; $R^{2a}$ is methyl; $R^3$ is cyclopropyl optionally substituted with one $R^{20b}$; and $R^{20b}$ is —CN. In embodiments of a compound of Formula (I'-2); $R^7$ is methyl optionally substituted with one, two, or three $R^{20c}$; each $R^{20c}$ is independently selected from halogen, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl; $L^1$ is a bond; $R^4$ is hydrogen; $R^6$ is hydrogen; $R^1$ is a

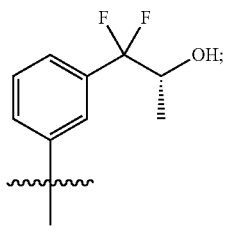 [SMILES: *c1cccc(C(F)(F)[C@@H](C)O)c1]

$R^2$ is —$OR^{2a}$; $R^{2a}$ is methyl; $R^3$ is $C_{3-4}$cycloalkyl optionally substituted with one $R^{20b}$; and $R^{20b}$ is —CN. In embodiments of a compound of Formula (I'-2); $R^7$ is methyl optionally substituted with one, two, or three $R^{20c}$; each $R^{20c}$ is independently selected from halogen, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl; $L^1$ is a bond; $R^4$ is hydrogen; $R^6$ is hydrogen; $R^1$ is a

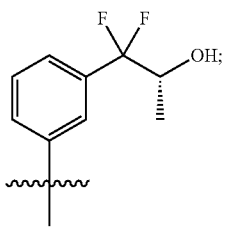 [SMILES: *c1cccc(C(F)(F)[C@@H](C)O)c1]

$R^2$ is —$OR^{2a}$; $R^{2a}$ is methyl; $R^3$ is $C_{3-4}$cycloalkyl optionally substituted with one, two, or three $R^{20b}$; and $R^{20b}$ is —CN. In embodiments of a compound of Formula (I'-2); $R^7$ is methyl optionally substituted with one, two, or three $R^{20c}$; each $R^{20c}$ is independently selected from halogen, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl; $L^1$ is a bond; $R^4$ is hydrogen; $R^6$ is hydrogen; $R^1$ is a

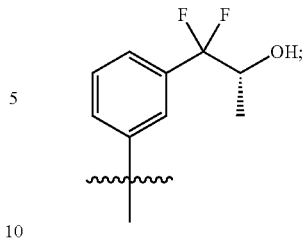

$R^2$ is —$OR^{2a}$; $R^{2a}$ is methyl; $R^3$ is $C_{3-4}$cycloalkyl optionally substituted with one, two, or three $R^{20b}$; and each $R^{20b}$ is independently —CN or $C_{1-3}$haloalkyl. In embodiments of a compound of Formula (I'-2); $R^7$ is methyl optionally substituted with one, two, or three $R^{20c}$; each $R^{20c}$ is independently selected from halogen, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl; $L^1$ is a bond; $R^4$ is hydrogen; $R^6$ is hydrogen; $R^1$ is a

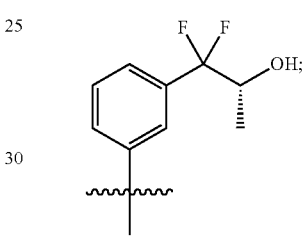

$R^2$ is —$OR^{2a}$; $R^{2a}$ is methyl; $R^3$ is $C_{3-4}$cycloalkyl optionally substituted with one, two, or three $R^{20b}$; and each $R^{20b}$ is independently —CN or $C_{1-3}$haloalkyl. In embodiments of a compound of Formula (I-2); $R^7$ is methyl optionally substituted with one, two, or three $R^{20c}$; each $R^{20c}$ is independently selected from halogen, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl; $L^1$ is a bond; $R^4$ is hydrogen; $R^6$ is hydrogen; $R^1$ is a

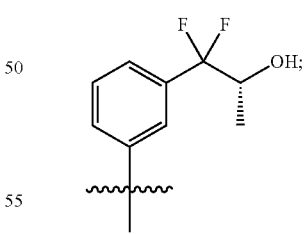

$R^2$ is —$OR^{2a}$; $R^{2a}$ is methyl; $R^3$ is $C_{3-4}$cycloalkyl optionally substituted with one, two, or three $R^{20b}$; and each $R^{20b}$ is independently —CN or $C_{1-3}$ haloalkyl. In embodiments of a compound of Formula (I'-2); $R^7$ is methyl optionally substituted with one, two, or three $R^{20c}$; each $R^{20c}$ is independently selected from halogen, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl; $L^1$ is a bond; $R^4$ is hydrogen; $R^6$ is hydrogen; $R^1$ is a

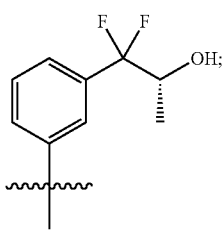 [SMILES: *c1cccc(C(F)(F)[C@@H](C)O)c1]

$R^2$ is $-OR^{2a}$; $R^{2a}$ is methyl; $R^3$ is $C_{3-4}$cycloalkyl optionally substituted with one, two, or three $R^{20b}$; and each $R^{20b}$ is independently selected from amino; $-CN$; $C_{1-3}$alkyl; $C_{1-3}$alkoxy; $C_{1-3}$ haloalkyl; $-OH$; $-N(R^{24})C(O)R^{25}$; and $-C(O)N(R^{22})(R^{23})$.

In embodiments of a compound of Formula (I'-2); $R^7$ is methyl optionally substituted with one, two, or three $R^{20c}$; each $R^{20c}$ is independently selected from halogen, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl; $L^1$ is a bond; $R^4$ is hydrogen; $R^6$ is hydrogen; $R^1$ is a phenyl substituted with one or more $R^{10}$; each $R^{10}$ is independently selected from halogen and $C_{1-4}$alkyl optionally substituted with one, two, or three $R^{20d}$; each $R^{20d}$ is independently selected from halogen and $-OH$; $R^2$ is $-OR^{2a}$; $R^{2a}$ is methyl; and $R^3$ is

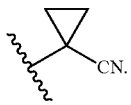

In embodiments of a compound of Formula (I'-2); $R^7$ is methyl optionally substituted with one, two, or three $R^{20c}$; each $R^{20c}$ is independently selected from halogen, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl; $L^1$ is a bond; $R^4$ is hydrogen; $R^6$ is hydrogen; $R^1$ is a phenyl substituted with one or more $R^{10}$; each $R^{10}$ is independently selected from halogen and $C_{1-4}$alkyl optionally substituted with one, two, or three $R^{20d}$; each $R^{20d}$ is independently selected from halogen and $-OH$; $R^2$ is $-OR^{2a}$; $R^{2a}$ is methyl; $R^3$ is cyclopropyl optionally substituted with one $R^{20b}$; and $R^{20b}$ is $-CN$. In embodiments of a compound of Formula (I'-2); $R^7$ is methyl optionally substituted with one, two, or three $R^{20c}$; each $R^{20c}$ is independently selected from halogen, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl; $L^1$ is a bond; $R^4$ is hydrogen; $R^6$ is hydrogen; $R^1$ is a phenyl substituted with one or more $R^{10}$; each $R^{10}$ is independently selected from halogen and $C_{1-4}$alkyl optionally substituted with one, two, or three $R^{20d}$; each $R^{20d}$ is independently selected from halogen and $-OH$; $R^2$ is $-OR^{2a}$; $R^{2a}$ is methyl; $R^3$ is $C_{3-4}$cycloalkyl optionally substituted with one, two, or three $R^{20b}$; and $R^{20b}$ is $-CN$. In embodiments of a compound of Formula (I'-2); $R^7$ is methyl optionally substituted with one, two, or three $R^{20c}$; each $R^{20c}$ is independently selected from halogen, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl; $L^1$ is a bond; $R^4$ is hydrogen; $R^6$ is hydrogen; $R^1$ is a phenyl substituted with one or more $R^{10}$; each $R^{10}$ is independently selected from halogen and $C_{1-4}$alkyl optionally substituted with one, two, or three $R^{20d}$; each $R^{20d}$ is independently selected from halogen and $-OH$; $R^2$ is $-OR^{2a}$; $R^{2a}$ is methyl; $R^3$ is $C_{3-4}$cycloalkyl optionally substituted with one, two, or three $R^{20b}$; and each $R^{20b}$ is independently $-CN$ or $C_{1-3}$haloalkyl. In embodiments of a compound of Formula (I'-2); $R^7$ is methyl optionally substituted with one, two, or three $R^{20c}$; each $R^{20c}$ is independently selected from halogen, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl; $L^1$ is a bond; $R^4$ is hydrogen; $R^6$ is hydrogen; $R^1$ is a phenyl substituted with one or more $R^{10}$; each $R^{10}$ is independently selected from halogen and $C_{1-4}$alkyl optionally substituted with one, two, or three $R^{20d}$; each $R^{20d}$ is independently selected from halogen and $-OH$; $R^2$ is $-OR^{2a}$; $R^{2a}$ is methyl; $R^3$ is $C_{3-4}$cycloalkyl optionally substituted with one, two, or three $R^{20b}$; and each $R^{20b}$ is independently $-CN$ or $C_{1-3}$haloalkyl. In embodiments of a compound of Formula (I'-2); $R^7$ is methyl optionally substituted with one, two, or three $R^{20c}$; each $R^{20c}$ is independently selected from halogen, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl; $L^1$ is a bond; $R^4$ is hydrogen; $R^6$ is hydrogen; $R^1$ is a phenyl substituted with one or more $R^{10}$; each $R^{10}$ is independently selected from halogen and $C_{1-4}$alkyl optionally substituted with one, two, or three $R^{20d}$; each $R^{20d}$ is independently selected from halogen and $-OH$; $R^2$ is $-OR^{2a}$; $R^{2a}$ is methyl; $R^3$ is $C_{3-4}$cycloalkyl optionally substituted with one, two, or three $R^{20b}$; and each $R^{20b}$ is independently $-CN$ or $C_{1-3}$haloalkyl. In embodiments of a compound of Formula (I'-2); $R^7$ is methyl optionally substituted with one, two, or three $R^{20c}$; each $R^{20c}$ is independently selected from halogen, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl; $L^1$ is a bond; $R^4$ is hydrogen; $R^6$ is hydrogen; $R^1$ is a phenyl substituted with one or more $R^{10}$; each $R^{10}$ is independently selected from halogen and $C_{1-4}$alkyl optionally substituted with one, two, or three $R^{20d}$; each $R^{20a}$ is independently selected from halogen and $-OH$; $R^2$ is $-OR^{2a}$; $R^{2a}$ is methyl; $R^3$ is $C_{3-4}$cycloalkyl optionally substituted with one, two, or three $R^{20b}$; and each $R^{20b}$ is independently selected from amino; $-CN$; $C_{1-3}$alkyl; $C_{1-3}$alkoxy; $C_{1-3}$haloalkyl; $-OH$; $-N(R^{24})C(O)R^{21}$; and $-C(O)N(R^{22})(R^{23})$.

In embodiments of a compound of Formula (I'-2); $R^7$ is methyl optionally substituted with one, two, or three $R^{20c}$; each $R^{20c}$ is independently selected from halogen, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl; $L^1$ is a bond; $R^4$ is hydrogen; $R^6$ is hydrogen; $R^1$ is a phenyl substituted with one or more $R^{10}$; each $R^{10}$ is independently selected from halogen and $C_{1-4}$alkyl optionally substituted with one, two, or three $R^{20d}$; each $R^{20d}$ is independently selected from halogen, $-OH$, $C_{2-5}$heterocycloalkyl optionally substituted with one, two, or three $C_{1-6}$alkyl (e.g., methyl, ethyl, or propyl), and $-OR^{21}$, wherein $R^{21}$ is $C_{2-5}$heterocycloalkyl optionally substituted with one, two, or three $C_{1-6}$alkyl (e.g., methyl, ethyl, propyl, or butyl); $R^2$ is $-OR^{2a}$; $R^{2a}$ is methyl; and $R^3$ is

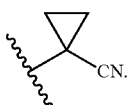 [SMILES: *C1(C#N)CC1]

In embodiments of a compound of Formula (I'-2); $R^7$ is methyl optionally substituted with one, two, or three $R^{20c}$; each $R^{20c}$ is independently selected from halogen, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl; $L^1$ is a bond; $R^4$ is hydrogen; $R^6$ is hydrogen; $R^1$ is a phenyl substituted with one or more $R^{10}$; each $R^{10}$ is independently selected from halogen and $C_{1-4}$alkyl optionally substituted with one, two, or three $R^{20d}$; each $R^{20d}$ is independently selected from halogen, —OH, $C_{2-5}$heterocycloalkyl optionally substituted with one, two, or three $C_{1-6}$alkyl (e.g., methyl, ethyl, or propyl), and —$OR^{21}$, wherein $R^{21}$ is $C_{2-5}$heterocycloalkyl optionally substituted with one, two, or three $C_{1-6}$alkyl (e.g., methyl, ethyl, propyl, or butyl); $R^2$ is —$OR^{2a}$; $R^{2a}$ is methyl; $R^3$ is cyclopropyl optionally substituted with one $R^{20b}$; and $R^{20b}$ is —CN. In embodiments of a compound of Formula (I'-2); $R^7$ is methyl optionally substituted with one, two, or three $R^{20c}$; each $R^{20c}$ is independently selected from halogen, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl; $L^1$ is a bond; $R^4$ is hydrogen; $R^6$ is hydrogen; $R^1$ is a phenyl substituted with one or more $R^{10}$; each $R^{10}$ is independently selected from halogen and $C_{1-4}$alkyl optionally substituted with one, two, or three $R^{20d}$; each $R^{20d}$ is independently selected from halogen, —OH, $C_{2-5}$heterocycloalkyl optionally substituted with one, two, or three $C_{1-6}$alkyl (e.g., methyl, ethyl, or propyl), and —$OR^{21}$, wherein $R^{21}$ is $C_{2-5}$heterocycloalkyl optionally substituted with one, two, or three $C_{1-6}$alkyl (e.g., methyl, ethyl, propyl, or butyl); $R^2$ is —$OR^{2a}$; $R^{2a}$ is methyl; $R^3$ is $C_{3-4}$cycloalkyl optionally substituted with one, two, or three $R^{20b}$; and $R^{20b}$ is —CN. In embodiments of a compound of Formula (I'-2); $R^7$ is methyl optionally substituted with one, two, or three $R^{20c}$; each $R^{20c}$ is independently selected from halogen, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl; $L^1$ is a bond; $R^4$ is hydrogen; $R^6$ is hydrogen; $R^1$ is a phenyl substituted with one or more $R^{10}$; each $R^{10}$ is independently selected from halogen and $C_{1-4}$alkyl optionally substituted with one, two, or three $R^{20a}$; each $R^{20a}$ is independently selected from halogen, —OH, $C_{2-5}$heterocycloalkyl optionally substituted with one, two, or three $C_{1-6}$alkyl (e.g., methyl, ethyl, or propyl), and —$OR^{21}$, wherein $R^{21}$ is $C_{2-5}$heterocycloalkyl optionally substituted with one, two, or three $C_{1-6}$alkyl (e.g., methyl, ethyl, propyl, or butyl); $R^2$ is —$OR^{2a}$; $R^{2a}$ is methyl; $R^3$ is $C_{3-4}$cycloalkyl optionally substituted with one, two, or three $R^{21b}$; and each $R^{20b}$ is independently —CN or $C_{1-3}$haloalkyl. In embodiments of a compound of Formula (I'-2); $R^7$ is methyl optionally substituted with one, two, or three $R^{20c}$; each $R^{20c}$ is independently selected from halogen, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl; $L^1$ is a bond; $R^4$ is hydrogen; $R^6$ is hydrogen; $R^1$ is a phenyl substituted with one or more $R^{10}$; each $R^{10}$ is independently selected from halogen and $C_{1-4}$alkyl optionally substituted with one, two, or three $R^{20d}$; each $R^{20d}$ is independently selected from halogen, —OH, $C_{2-5}$heterocycloalkyl optionally substituted with one, two, or three $C_{1-6}$alkyl (e.g., methyl, ethyl, or propyl), and —$OR^{21}$, wherein $R^{21}$ is $C_{2-5}$heterocycloalkyl optionally substituted with one, two, or three $C_{1-6}$alkyl (e.g., methyl, ethyl, propyl, or butyl); $R^2$ is —$OR^{2a}$; $R^{2a}$ is methyl; $R^3$ is $C_{3-4}$cycloalkyl optionally substituted with one, two, or three $R^{20b}$; and each $R^{20b}$ is independently —CN or $C_{1-3}$haloalkyl. In embodiments of a compound of Formula (I'-2); $R^7$ is methyl optionally substituted with one, two, or three $R^{20c}$; each $R^{20c}$ is independently selected from halogen, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl; $L^1$ is a bond; $R^4$ is hydrogen; $R^6$ is hydrogen; $R^1$ is a phenyl substituted with one or more $R^{10}$; each $R^{10}$ is independently selected from halogen and $C_{1-4}$alkyl optionally substituted with one, two, or three $R^{20d}$; each $R^{20d}$ is independently selected from halogen, —OH, $C_{2-5}$heterocycloalkyl optionally substituted with one, two, or three $C_{1-6}$alkyl (e.g., methyl, ethyl, or propyl), and —$OR^{21}$, wherein $R^{21}$ is $C_{2-5}$heterocycloalkyl optionally substituted with one, two, or three $C_{1-6}$alkyl (e.g., methyl, ethyl, propyl, or butyl); $R^2$ is —$OR^{2a}$; $R^{2a}$ is methyl; $R^3$ is $C_{3-4}$cycloalkyl optionally substituted with one, two, or three $R^{20b}$; and each $R^{20b}$ is independently selected from amino; —CN; $C_{1-3}$alkyl; $C_{1-3}$alkoxy; $C_{1-3}$haloalkyl; —OH; —$N(R^{24})C(O)R^{25}$; and —$C(O)N(R^{22})(R^{23})$.

In embodiments of a compound of Formula (I'-2); $R^7$ is methyl optionally substituted with one, two, or three $R^{20c}$; each $R^{20c}$ is independently selected from halogen, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl; $L^1$ is a bond; $R^4$ is hydrogen; $R^6$ is hydrogen; $R^1$ is a 6-10 membered aryl ring substituted with one or more $R^{10}$; each $R^{10}$ is independently selected from halogen and $C_{1-4}$alkyl optionally substituted with one, two, or three $R^{20d}$; each $R^{20d}$ is independently selected from halogen, —OH, $C_{2-5}$heterocycloalkyl optionally substituted with one, two, or three $C_{1-6}$alkyl (e.g., methyl, ethyl, or propyl), and —$OR^{21}$, wherein $R^{21}$ is $C_{2-5}$heterocycloalkyl optionally substituted with one, two, or three $C_{1-6}$alkyl (e.g., methyl, ethyl, propyl, or butyl); $R^2$ is —$OR^{2a}$; $R^{2a}$ is methyl; and $R^3$ is

535

[Structure: cyclopropyl group with CN substituent]

In embodiments of a compound of Formula (I'-2); $R^7$ is methyl optionally substituted with one, two, or three $R^{20c}$; each $R^{20c}$ is independently selected from halogen, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl; $L^1$ is a bond; $R^4$ is hydrogen; $R^6$ is hydrogen; $R^1$ is a 6-10 membered aryl ring substituted with one or more $R^{10}$; each $R^{10}$ is independently selected from halogen and $C_{1-4}$alkyl optionally substituted with one, two, or three $R^{20d}$; each $R^{20d}$ is independently selected from halogen, —OH, $C_{2-5}$heterocycloalkyl optionally substituted with one, two, or three $C_{1-6}$alkyl (e.g., methyl, ethyl, or propyl), and —$OR^{21}$, wherein $R^{21}$ is $C_{2-5}$heterocycloalkyl optionally substituted with one, two, or three $C_{1-6}$alkyl (e.g., methyl, ethyl, propyl, or butyl); $R^3$ is cyclopropyl optionally substituted with one $R^{20b}$; and $R^{20b}$ is —CN. In embodiments of a compound of Formula (I'-2); $R^7$ is methyl optionally substituted with one, two, or three $R^{20c}$; each $R^{20c}$ is independently selected from halogen, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl; $L^1$ is a bond; $R^4$ is hydrogen; $R^6$ is hydrogen; $R^1$ is a 6-10 membered aryl ring substituted with one or more $R^{10}$; each $R^{10}$ is independently selected from halogen and $C_{1-4}$alkyl optionally substituted with one, two, or three $R^{20d}$; each $R^{20d}$ is independently selected from halogen, —OH, $C_{2-5}$heterocycloalkyl optionally substituted with one, two, or three $C_{1-6}$alkyl (e.g., methyl, ethyl, or propyl), and —$OR^{21}$, wherein $R^{21}$ is $C_{2-5}$heterocycloalkyl optionally substituted with one, two, or three $C_{1-6}$alkyl (e.g., methyl, ethyl, propyl, or butyl); $R^2$ is —$OR^{2a}$; $R^{2a}$ is methyl; $R^3$ is $C_{3-4}$cycloalkyl optionally substituted with one $R^{21b}$; and $R^{20b}$ is —CN. In embodiments of a compound of Formula (I'-2); $R^7$ is methyl optionally substituted with one, two, or three $R^{20c}$; each $R^{20c}$ is independently selected from halogen, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl; $L^1$ is a bond; $R^4$ is hydrogen; $R^6$ is hydrogen; $R^1$ is a 6-10 membered aryl ring substituted with one or more $R^{10}$; each $R^{10}$ is independently selected from halogen and $C_{1-4}$alkyl optionally substituted with one, two, or three $R^{20d}$; each $R^{20d}$ is independently selected from halogen, —OH, $C_{2-5}$heterocycloalkyl optionally substituted with one, two, or three $C_{1-6}$alkyl (e.g., methyl, ethyl, or propyl), and —$OR^{21}$, wherein $R^{21}$ is $C_{2-5}$heterocycloalkyl optionally substituted with one, two, or three $C_{1-6}$alkyl (e.g., methyl, ethyl, propyl, or butyl); $R^2$ is —$OR^{2a}$; $R^{2a}$ is methyl; $R^3$ is $C_{3-4}$cycloalkyl optionally substituted with one, two, or three $R^{20b}$; and $R^{20b}$ is —CN. In embodiments of a compound of Formula (I'-2); $R^7$ is methyl optionally substituted with one, two, or three $R^{20c}$; each $R^{20c}$ is independently selected from halogen, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl; $L^1$ is a bond; $R^4$ is hydrogen; $R^6$ is hydrogen; $R^1$ is a 6-10 membered aryl ring substituted with one or more $R^{10}$; each $R^{10}$ is independently selected from halogen and $C_{1-4}$alkyl optionally substituted with one, two, or three $R^{20d}$; each $R^{20d}$ is independently selected from

536 halogen, —OH, $C_{2-5}$heterocycloalkyl optionally substituted with one, two, or three $C_{1-6}$alkyl (e.g., methyl, ethyl, or propyl), and —$OR^{21}$, wherein $R^{21}$ is $C_{2-5}$heterocycloalkyl optionally substituted with one, two, or three $C_{1-6}$alkyl (e.g., methyl, ethyl, propyl, or butyl); $R^2$ is —$OR^{2a}$; $R^{2a}$ is methyl; $R^3$ is $C_{3-4}$cycloalkyl optionally substituted with one, two, or three $R^{20b}$; and each $R^{20b}$ is independently —CN or $C_{1-3}$haloalkyl. In embodiments of a compound of Formula (I'-2); $R^7$ is methyl optionally substituted with one, two, or three $R^{20c}$; each $R^{20c}$ is independently selected from halogen, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl; $L^1$ is a bond; $R^4$ is hydrogen; $R^6$ is hydrogen; $R^1$ is a 6-10 membered aryl ring substituted with one or more $R^{10}$; each $R^{10}$ is independently selected from halogen and $C_{1-4}$alkyl optionally substituted with one, two, or three $R^{20d}$; each $R^{20d}$ is independently selected from halogen, —OH, $C_{2-5}$heterocycloalkyl optionally substituted with one, two, or three $C_{1-6}$alkyl (e.g., methyl, ethyl, or propyl), and —$OR^{21}$, wherein $R^{21}$ is $C_{2-5}$heterocycloalkyl optionally substituted with one, two, or three $C_{1-6}$alkyl (e.g., methyl, ethyl, propyl, or butyl); $R^2$ is —$OR^{2a}$; $R^{2a}$ is methyl; $R^3$ is $C_{3-4}$cycloalkyl optionally substituted with one, two, or three $R^{20b}$; and each $R^{20b}$ is independently —CN or $C_{1-3}$ haloalkyl. In embodiments of a compound of Formula (I'-2); $R^7$ is methyl optionally substituted with one, two, or three $R^{20c}$; each $R^{20c}$ is independently selected from halogen, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl; $L^1$ is a bond; $R^4$ is hydrogen; $R^6$ is hydrogen; $R^1$ is a 6-10 membered aryl ring substituted with one or more $R^{10}$; each $R^{10}$ is independently selected from halogen and $C_{1-4}$alkyl optionally substituted with one, two, or three $R^{20d}$; each $R^{20d}$ is independently selected from halogen, —OH, $C_{2-5}$heterocycloalkyl optionally substituted with one, two, or three $C_{1-6}$alkyl (e.g., methyl, ethyl, or propyl), and —$OR^{21}$, wherein $R^{21}$ is $C_{2-5}$heterocycloalkyl optionally substituted with one, two, or three $C_{1-6}$alkyl (e.g., methyl, ethyl, propyl, or butyl); $R^2$ is —$OR^{2a}$; $R^{2a}$ is methyl; $R^3$ is $C_{3-4}$cycloalkyl optionally substituted with one, two, or three $R^{20b}$; and each $R^{20b}$ is independently —CN or $C_{1-3}$haloalkyl. In embodiments of a compound of Formula (I'-2); $R^7$ is methyl optionally substituted with one, two, or three $R^{20c}$; each $R^{20c}$ is independently selected from halogen, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl; $L^1$ is a bond; $R^4$ is hydrogen; $R^6$ is hydrogen; $R^1$ is a 6-10 membered aryl ring substituted with one or more $R^{10}$; each $R^{10}$ is independently selected from halogen and $C_{1-4}$alkyl optionally substituted with one, two, or three $R^{20d}$; each $R^{20a}$ is independently selected from halogen, —OH, $C_{2-5}$heterocycloalkyl optionally substituted with one, two, or three $C_{1-6}$alkyl (e.g., methyl, ethyl, or propyl), and —$OR^{21}$, wherein $R^{21}$ is $C_{2-5}$heterocycloalkyl optionally substituted with one, two, or three $C_{1-6}$alkyl (e.g., methyl, ethyl, propyl, or butyl); $R^2$ is —$OR^{2a}$; $R^{2a}$ is methyl; $R^3$ is $C_{3-4}$cycloalkyl optionally substituted with one, two, or three $R^{20b}$; and each $R^{20b}$ is independently selected from amino; —CN; $C_{1-3}$alkyl; $C_{1-3}$alkoxy; $C_{1-3}$haloalkyl; —OH; —$N(R^{24})C(O)R^{25}$; and —$C(O)N(R^{22})(R^{23})$.

In embodiments of a compound of Formula (I-2); $R^7$ is methyl optionally substituted with one, two, or three $R^{20c}$; each $R^{20c}$ is independently selected from halogen, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl; $L^1$ is a bond; $R^4$ is hydrogen; $R^5$ is methyl; $R^6$ is hydrogen; $R^1$ is a

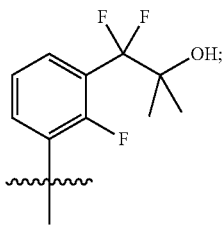 [SMILES: *c1cccc(C(F)(F)C(C)(C)O)c1F]

$R^2$ is —$OR^{2a}$; $R^{2a}$ is methyl; and $R^3$ is

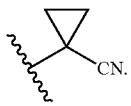

In embodiments of a compound of Formula (I-2); $R^7$ is methyl optionally substituted with one, two, or three $R^{20c}$; each $R^{20c}$ is independently selected from halogen, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl; $L^1$ is a bond; $R^4$ is hydrogen; $R^5$ is methyl; $R^6$ is hydrogen; $R^1$ is a

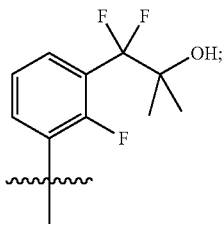 [SMILES: *c1cccc(C(F)(F)C(C)(C)O)c1F]

$R^2$ is —$OR^{2a}$; $R^{2a}$ is methyl; $R^3$ is cyclopropyl optionally substituted with one $R^{20b}$; and $R^{20b}$ is —CN. In embodiments of a compound of Formula (I-2); $R^7$ is methyl optionally substituted with one, two, or three $R^{20c}$; each $R^{20c}$ is independently selected from halogen, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl; $L^1$ is a bond; $R^4$ is hydrogen; $R^5$ is methyl; $R^6$ is hydrogen; $R^1$ is a

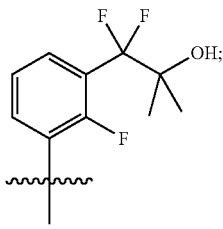 [SMILES: *c1cccc(C(F)(F)C(C)(C)O)c1F]

$R^2$ is —$OR^{2a}$; $R^{2a}$ is methyl; $R^3$ is $C_{3-4}$cycloalkyl optionally substituted with one $R^{20b}$; and $R^{20b}$ is —CN. In embodiments of a compound of Formula (I-2); $R^7$ is methyl optionally substituted with one, two, or three $R^{20c}$; each $R^{20c}$ is independently selected from halogen, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl; $L^1$ is a bond; $R^4$ is hydrogen; $R^5$ is methyl; $R^6$ is hydrogen; $R^1$ is a

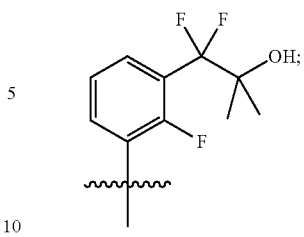

$R^2$ is —$OR^{2a}$; $R^{2a}$ is methyl; $R^3$ is $C_{3-4}$cycloalkyl optionally substituted with one, two, or three $R^{20b}$; and $R^{20b}$ is —CN. In embodiments of a compound of Formula (I-2); $R^7$ is methyl optionally substituted with one, two, or three $R^{20c}$; each $R^{20c}$ is independently selected from halogen, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl; $L^1$ is a bond; $R^4$ is hydrogen; $R^5$ is methyl; $R^6$ is hydrogen; $R^1$ is a

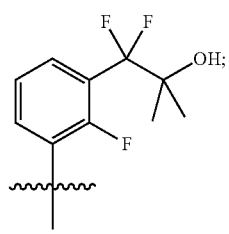 [SMILES: *c1cccc(C(F)(F)C(C)(C)O)c1F]

$R^2$ is —$OR^{2a}$; $R^{2a}$ is methyl; $R^3$ is $C_{3-4}$cycloalkyl optionally substituted with one, two, or three $R^{20b}$; and each $R^{20b}$ is independently —CN or $C_{1-3}$haloalkyl. In embodiments of a compound of Formula (I-2); $R^7$ is methyl optionally substituted with one, two, or three $R^{20c}$; each $R^{20c}$ is independently selected from halogen, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl; $L^1$ is a bond; $R^4$ is hydrogen; $R^5$ is methyl; $R^6$ is hydrogen; $R^1$ is a

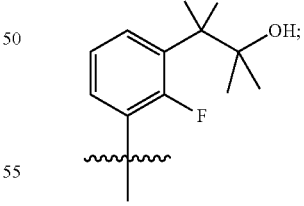

$R^2$ is —$OR^{2a}$; $R^{2a}$ is methyl; $R^3$ is $C_{3-4}$cycloalkyl optionally substituted with one, two, or three $R^{20b}$; and each $R^{20b}$ is independently —CN or $C_{1-3}$haloalkyl. In embodiments of a compound of Formula (I-2); $R^7$ is methyl optionally substituted with one, two, or three $R^{20c}$; each $R^{20c}$ is independently selected from halogen, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl; $L^1$ is a bond; $R^4$ is hydrogen; $R^5$ is methyl; $R^6$ is hydrogen; $R^1$ is a

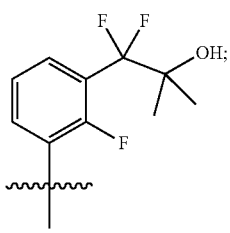 [SMILES: *c1cccc(C(F)(F)C(C)(C)O)c1F]

$R^2$ is —$OR^{2a}$; $R^{2a}$ is methyl; $R^3$ is $C_{3-4}$cycloalkyl optionally substituted with one, two, or three $R^{20b}$; and each $R^{20b}$ is independently —CN or $C_{1-3}$haloalkyl. In embodiments of a compound of Formula (I-2); $R^7$ is methyl optionally substituted with one, two, or three $R^{20c}$; each $R^{20c}$ is independently selected from halogen, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl; $L^1$ is a bond; $R^4$ is hydrogen; $R^5$ is methyl; $R^6$ is hydrogen; $R^1$ is a

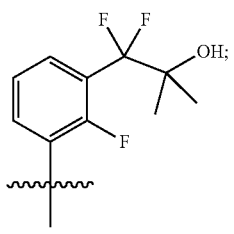 [SMILES: *c1cccc(C(F)(F)C(C)(C)O)c1F]

$R^2$ is —$OR^{2a}$; $R^{2a}$ is methyl; $R^3$ is $C_{3-4}$cycloalkyl optionally substituted with one, two, or three $R^{20b}$; and each $R^{20b}$ is independently selected from amino; —CN; $C_{1-3}$alkyl; $C_{1-3}$alkoxy; $C_{1-3}$haloalkyl; —OH; —N($R^{24}$)C(O)$R^{25}$; and —C(O)N($R^{22}$)($R^{23}$).

In embodiments of a compound of Formula (I-2); $R^7$ is methyl optionally substituted with one, two, or three $R^{20c}$; each $R^{20c}$ is independently selected from halogen, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl; $L^1$ is a bond; $R^4$ is hydrogen; $R^5$ is methyl; $R^6$ is hydrogen; $R^1$ is a

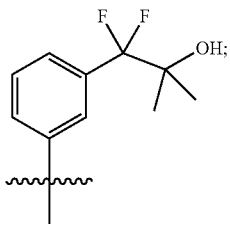 [SMILES: *c1cccc(C(F)(F)C(C)(C)O)c1]

$R^2$ is —$OR^{2a}$; $R^{2a}$ is methyl; and $R^3$ is

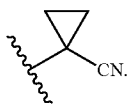 [SMILES: *C1(C#N)CC1]

In embodiments of a compound of Formula (I-2); $R^7$ is methyl optionally substituted with one, two, or three $R^{20c}$; each $R^{20c}$ is independently selected from halogen, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl; $L^1$ is a bond; $R^4$ is hydrogen; $R^5$ is methyl; $R^6$ is hydrogen; $R^1$ is a

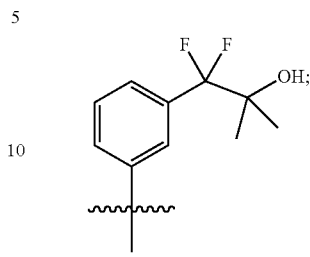

$R^2$ is —$OR^{2a}$; $R^{2a}$ is methyl; $R^3$ is cyclopropyl optionally substituted with one $R^{20b}$; and $R^{20b}$ is —CN. In embodiments of a compound of Formula (I-2); $R^7$ is methyl optionally substituted with one, two, or three $R^{20c}$; each $R^{20c}$ is independently selected from halogen, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl; $L^1$ is a bond; $R^4$ is hydrogen; $R^5$ is methyl; $R^6$ is hydrogen; $R^1$ is a

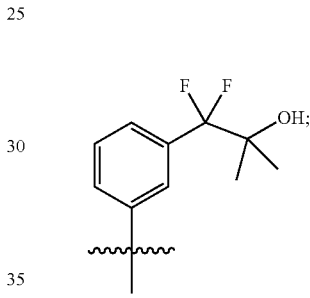

$R^2$ is —$OR^{2a}$; $R^{2a}$ is methyl; $R^3$ is $C_{3-4}$cycloalkyl optionally substituted with one $R^{20b}$; and $R^{20b}$ is —CN. In embodiments of a compound of Formula (I-2); $R^7$ is methyl optionally substituted with one, two, or three $R^{20c}$; each $R^{20c}$ is independently selected from halogen, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl; $L^1$ is a bond; $R^4$ is hydrogen; $R^5$ is methyl; $R^6$ is hydrogen; $R^1$ is a

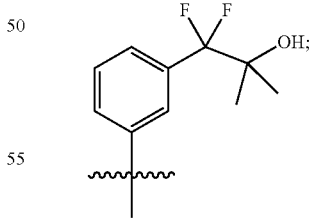

$R^2$ is —$OR^{2a}$; $R^{2a}$ is methyl; $R^3$ is $C_{3-4}$cycloalkyl optionally substituted with one, two, or three $R^{20b}$; and $R^{20b}$ is —CN. In embodiments of a compound of Formula (I-2); $R^7$ is methyl optionally substituted with one, two, or three $R^{20c}$; each $R^{20c}$ is independently selected from halogen, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl; $L^1$ is a bond; $R^4$ is hydrogen; $R^5$ is methyl; $R^6$ is hydrogen; $R^1$ is a

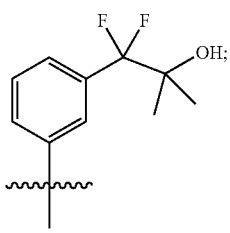 [SMILES: *c1cccc(C(F)(F)C(C)(C)O)c1]

$R^2$ is —$OR^{2a}$; $R^{2a}$ is methyl; $R^3$ is $C_{3-4}$cycloalkyl optionally substituted with one, two, or three $R^{20b}$; and each $R^{20b}$ is independently —CN or $C_{1-3}$haloalkyl. In embodiments of a compound of Formula (I-2); $R^7$ is methyl optionally substituted with one, two, or three $R^{20c}$; each $R^{20c}$ is independently selected from halogen, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl; $L^1$ is a bond; $R^4$ is hydrogen; $R^5$ is methyl; $R^6$ is hydrogen; $R^1$ is a

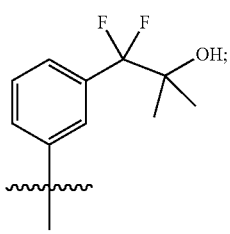 [SMILES: *c1cccc(C(F)(F)C(C)(C)O)c1]

$R^2$ is —$OR^{2a}$; $R^{2a}$ is methyl; $R^3$ is $C_{3-4}$cycloalkyl optionally substituted with one, two, or three $R^{20b}$; and each $R^{20b}$ is independently —CN or $C_{1-3}$haloalkyl. In embodiments of a compound of Formula (I-2); $R^7$ is methyl optionally substituted with one, two, or three $R^{20c}$; each $R^{20c}$ is independently selected from halogen, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl; $L^1$ is a bond; $R^4$ is hydrogen; $R^5$ is methyl; $R^6$ is hydrogen; $R^1$ is a

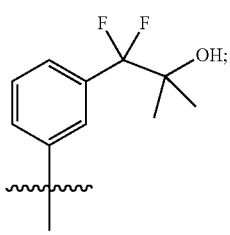 [SMILES: *c1cccc(C(F)(F)C(C)(C)O)c1]

$R^2$ is —$OR^{2a}$; $R^{2a}$ is methyl; $R^3$ is $C_{3-4}$cycloalkyl optionally substituted with one, two, or three $R^{20b}$; and each $R^{20b}$ is independently —CN or $C_{1-3}$haloalkyl. In embodiments of a compound of Formula (I-2); $R^7$ is methyl optionally substituted with one, two, or three $R^{20c}$; each $R^{20c}$ is independently selected from halogen, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl; $L^1$ is a bond; $R^4$ is hydrogen; $R^5$ is methyl; $R^6$ is hydrogen; $R^1$ is a

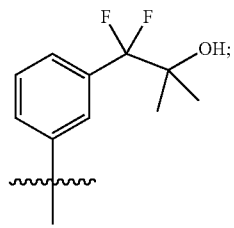 [SMILES: *c1cccc(C(F)(F)C(C)(C)O)c1]

$R^2$ is —$OR^{2a}$; $R^{2a}$ is methyl; $R^3$ is $C_{3-4}$cycloalkyl optionally substituted with one, two, or three $R^{20b}$; and each $R^{20b}$ is independently selected from amino; —CN; $C_{1-3}$alkyl; $C_{1-3}$alkoxy; $C_{1-3}$haloalkyl; —OH; —N($R^{24}$)C(O)$R^{25}$; and —C(O)N($R^{22}$)($R^{23}$).

In embodiments of a compound of Formula (I-2); $R^7$ is methyl optionally substituted with one, two, or three $R^{20c}$; each $R^{20c}$ is independently selected from halogen, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl; $L^1$ is a bond; $R^4$ is hydrogen; $R^5$ is methyl; $R^6$ is hydrogen; $R^1$ is a

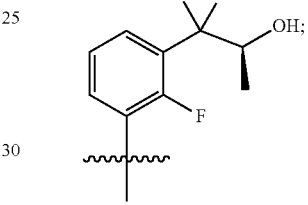

$R^2$ is —$OR^{2a}$; $R^{2a}$ is methyl; and $R^3$ is

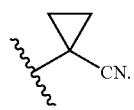

In embodiments of a compound of Formula (I-2); $R^7$ is methyl optionally substituted with one, two, or three $R^{20c}$; each $R^{20c}$ is independently selected from halogen, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl; $L^1$ is a bond; $R^4$ is hydrogen; $R^5$ is methyl; $R^6$ is hydrogen; $R^1$ is a

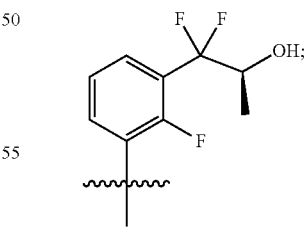

$R^2$ is —$OR^{2a}$; $R^{2a}$ is methyl; $R^3$ is cyclopropyl optionally substituted with one $R^{20b}$; and $R^{20b}$ is —CN. In embodiments of a compound of Formula (I-2); $R^7$ is methyl optionally substituted with one, two, or three $R^{20c}$; each $R^{20c}$ is independently selected from halogen, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl; $L^1$ is a bond; $R^4$ is hydrogen; $R^5$ is methyl; $R^6$ is hydrogen; $R^1$ is a

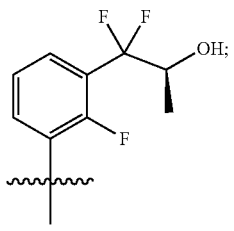 [SMILES: *c1cccc(C(F)(F)[C@H](C)O)c1F]

$R^2$ is —$OR^{2a}$; $R^{2a}$ is methyl; $R^3$ is $C_{3-4}$cycloalkyl optionally substituted with one $R^{20b}$; and $R^{20b}$ is —CN. In embodiments of a compound of Formula (I-2); $R^7$ is methyl optionally substituted with one, two, or three $R^{20c}$; each $R^{20c}$ is independently selected from halogen, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl; $L^1$ is a bond; $R^4$ is hydrogen; $R^5$ is methyl; $R^6$ is hydrogen; $R^1$ is a

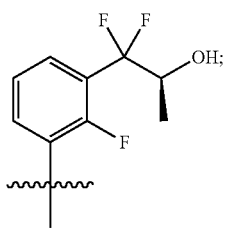 [SMILES: *c1cccc(C(F)(F)[C@H](C)O)c1F]

$R^2$ is —$OR^{2a}$; $R^{2a}$ is methyl; $R^3$ is $C_{3-4}$cycloalkyl optionally substituted with one, two, or three $R^{20b}$; and $R^{20b}$ is —CN. In embodiments of a compound of Formula (I-2); $R^7$ is methyl optionally substituted with one, two, or three $R^{20c}$; each $R^{20c}$ is independently selected from halogen, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl; $L^1$ is a bond; $R^4$ is hydrogen; $R^5$ is methyl; $R^6$ is hydrogen; $R^1$ is a

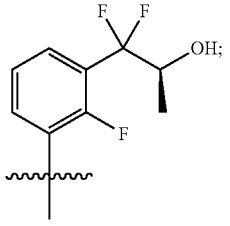 [SMILES: *c1cccc(C(F)(F)[C@H](C)O)c1F]

$R^2$ is —$OR^{2a}$; $R^{2a}$ is methyl; $R^3$ is $C_{3-4}$cycloalkyl optionally substituted with one, two, or three $R^{20b}$; and each $R^{20b}$ is independently —CN or $C_{1-3}$haloalkyl. In embodiments of a compound of Formula (I-2); $R^7$ is methyl optionally substituted with one, two, or three $R^{20c}$; each $R^{20c}$ is independently selected from halogen, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl; $L^1$ is a bond; $R^4$ is hydrogen; $R^5$ is methyl; $R^6$ is hydrogen; $R^1$ is a

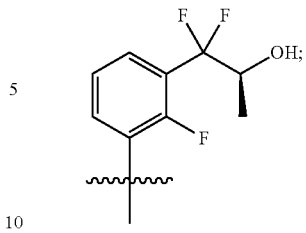

$R^2$ is —$OR^{2a}$; $R^{2a}$ is methyl; $R^3$ is $C_{3-4}$cycloalkyl optionally substituted with one, two, or three $R^{20b}$; and each $R^{20b}$ is independently —CN or $C_{1-3}$haloalkyl. In embodiments of a compound of Formula (I-2); $R^7$ is methyl optionally substituted with one, two, or three $R^{20c}$; each $R^{20c}$ is independently selected from halogen, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl; $L^1$ is a bond; $R^4$ is hydrogen; $R^5$ is methyl; $R^6$ is hydrogen; $R^1$ is a

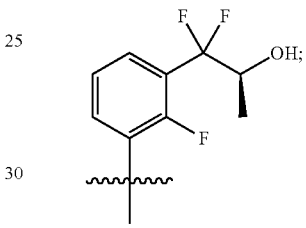

$R^2$ is —$OR^{2a}$; $R^{2a}$ is methyl; $R^3$ is $C_{3-4}$cycloalkyl optionally substituted with one, two, or three $R^{20b}$; and each $R^{20b}$ is independently —CN or $C_{1-3}$haloalkyl. In embodiments of a compound of Formula (I-2); $R^7$ is methyl optionally substituted with one, two, or three $R^{20c}$; each $R^{20c}$ is independently selected from halogen, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl; $L^1$ is a bond; $R^4$ is hydrogen; $R^5$ is methyl; $R^6$ is hydrogen; $R^1$ is a

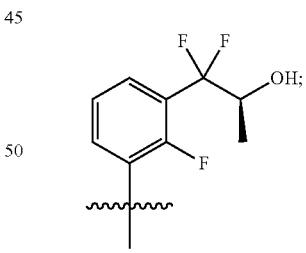

$R^2$ is —$OR^{2a}$; $R^{2a}$ is methyl; $R^3$ is $C_{3-4}$cycloalkyl optionally substituted with one, two, or three $R^{20b}$; and each $R^{20b}$ is independently selected from amino; —CN; $C_{1-3}$alkyl; $C_{1-3}$alkoxy; $C_{1-3}$haloalkyl; —OH; —$N(R^{24})C(O)R^{25}$; and —$C(O)N(R^{22})(R^{23})$.

In embodiments of a compound of Formula (I-2); $R^7$ is methyl optionally substituted with one, two, or three $R^{20c}$; each $R^{20c}$ is independently selected from halogen, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl; $L^1$ is a bond; $R^4$ is hydrogen; $R^5$ is methyl; $R^6$ is hydrogen; $R^1$ is a

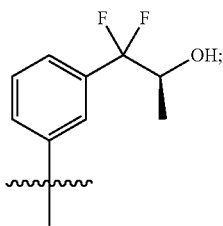 [SMILES: *c1cccc(C(F)(F)[C@H](C)O)c1]

$R^2$ is —$OR^{2a}$; $R^{2a}$ is methyl; and $R^3$ is

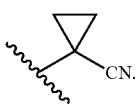

In embodiments of a compound of Formula (I-2); $R^7$ is methyl optionally substituted with one, two, or three $R^{20c}$; each $R^{20c}$ is independently selected from halogen, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl; $L^1$ is a bond; $R^4$ is hydrogen; $R^5$ is methyl; $R^6$ is hydrogen; $R^1$ is a

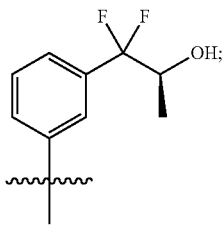 [SMILES: *c1cccc(C(F)(F)[C@H](C)O)c1]

$R^2$ is —$OR^{2a}$; $R^{2a}$ is methyl; $R^3$ is cyclopropyl optionally substituted with one $R^{20b}$; and $R^{20b}$ is —CN. In embodiments of a compound of Formula (I-2); $R^7$ is methyl optionally substituted with one, two, or three $R^{20c}$; each $R^{20c}$ is independently selected from halogen, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl; $L^1$ is a bond; $R^4$ is hydrogen; $R^5$ is methyl; $R^6$ is hydrogen; $R^1$ is a

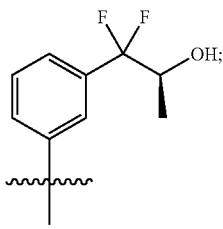 [SMILES: *c1cccc(C(F)(F)[C@H](C)O)c1]

$R^2$ is —$OR^{2a}$; $R^{2a}$ is methyl; $R^3$ is $C_{3-4}$cycloalkyl optionally substituted with one $R^{20b}$; and $R^{20b}$ is —CN. In embodiments of a compound of Formula (I-2); $R^7$ is methyl optionally substituted with one, two, or three $R^{20c}$; each $R^{20c}$ is independently selected from halogen, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl; $L^1$ is a bond; $R^4$ is hydrogen; $R^5$ is methyl; $R^6$ is hydrogen; $R^1$ is

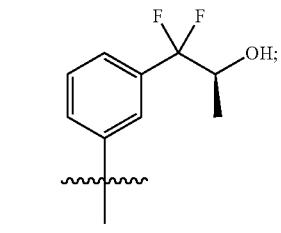 [SMILES: *c1cccc(C(F)(F)[C@H](C)O)c1]

$R^2$ is —$OR^{2a}$; $R^{2a}$ is methyl; $R^3$ is $C_{3-4}$cycloalkyl optionally substituted with one, two, or three $R^{20b}$; and $R^{20b}$ is —CN. In embodiments of a compound of Formula (I-2); $R^7$ is methyl optionally substituted with one, two, or three $R^{20c}$; each $R^{20c}$ is independently selected from halogen, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl; $L^1$ is a bond; $R^4$ is hydrogen; $R^5$ is methyl; $R^6$ is hydrogen; $R^1$ is a

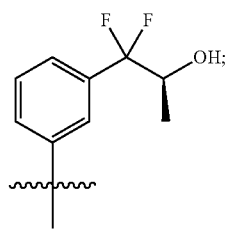 [SMILES: *c1cccc(C(F)(F)[C@H](C)O)c1]

$R^2$ is —$OR^{2a}$; $R^{2a}$ is methyl; $R^3$ is $C_{3-4}$cycloalkyl optionally substituted with one, two, or three $R^{20b}$; and each $R^{20b}$ is independently —CN or $C_{1-3}$haloalkyl. In embodiments of a compound of Formula (I-2); $R^7$ is methyl optionally substituted with one, two, or three $R^{20c}$; each $R^{20c}$ is independently selected from halogen, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl; $L^1$ is a bond; $R^4$ is hydrogen; $R^5$ is methyl; $R^6$ is hydrogen; $R^1$ is a

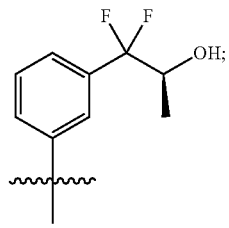 [SMILES: *c1cccc(C(F)(F)[C@H](C)O)c1]

$R^2$ is —$OR^{2a}$; $R^{2a}$ is methyl; $R^3$ is $C_{3-4}$cycloalkyl optionally substituted with one, two, or three $R^{20b}$; and each $R^{20b}$ is independently —CN or $C_{1-3}$haloalkyl. In embodiments of a compound of Formula (I-2); $R^7$ is methyl optionally substituted with one, two, or three $R^{20c}$; each $R^{20c}$ is independently selected from halogen, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl; $L^1$ is a bond; $R^4$ is hydrogen; $R^5$ is methyl; $R^6$ is hydrogen; $R^1$ is a

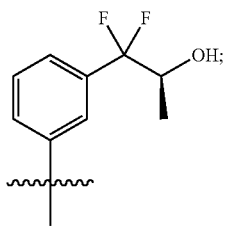 [SMILES: *c1cccc(C(F)(F)[C@H](C)O)c1]

R² is —OR²ᵃ; R²ᵃ is methyl; R³ is C₃₋₄cycloalkyl optionally substituted with one, two, or three R²⁰ᵇ; and each R²⁰ᵇ is independently —CN or C₁₋₃haloalkyl. In embodiments of a compound of Formula (I-2); R⁷ is methyl optionally substituted with one, two, or three R²⁰ᶜ; each R²⁰ᶜ is independently selected from halogen, C₂₋₆alkenyl, C₂₋₆alkynyl, C₃₋₁₀cycloalkyl, C₂₋₉heterocycloalkyl, C₆₋₁₀aryl, and C₁₋₉heteroaryl; L¹ is a bond; R⁴ is hydrogen; R⁵ is methyl; R⁶ is hydrogen; R¹ is a

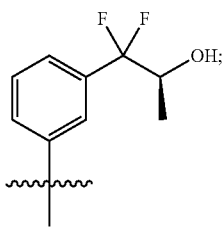 [SMILES: *c1cccc(C(F)(F)[C@H](C)O)c1]

R² is —OR²ᵃ; R²ᵃ is methyl; R³ is C₃₋₄cycloalkyl optionally substituted with one, two, or three R²⁰ᵇ; and each R²⁰ᵇ is independently selected from amino; —CN; C₁₋₃alkyl; C₁₋₃alkoxy; C₁₋₃haloalkyl; —OH; —N(R²⁴)C(O)R²⁵; and —C(O)N(R²²)(R²³).

In embodiments of a compound of Formula (I-2); R⁷ is methyl optionally substituted with one, two, or three R²⁰ᶜ; each R²⁰ᶜ is independently selected from halogen, C₂₋₆alkenyl, C₂₋₆alkynyl, C₃₋₁₀cycloalkyl, C₂₋₉heterocycloalkyl, C₆₋₁₀aryl, and C₁₋₉heteroaryl; L¹ is a bond; R⁴ is hydrogen; R⁵ is methyl; R⁶ is hydrogen; R¹ is a

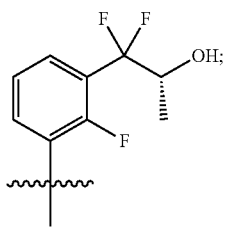 [SMILES: *c1cccc(C(F)(F)[C@@H](C)O)c1F]

R² is —OR²ᵃ; R²ᵃ is methyl; and R³ is

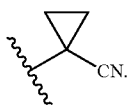

In embodiments of a compound of Formula (I-2); R⁷ is methyl optionally substituted with one, two, or three R²⁰ᶜ; each R²⁰ᶜ is independently selected from halogen, C₂₋₆alkenyl, C₂₋₆alkynyl, C₃₋₁₀cycloalkyl, C₂₋₉heterocycloalkyl, C₆₋₁₀aryl, and C₁₋₉heteroaryl; L¹ is a bond; R⁴ is hydrogen; R⁵ is methyl; R⁶ is hydrogen; R¹ is

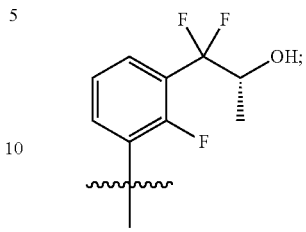

R² is —OR²ᵃ; R²ᵃ is methyl; R³ is cyclopropyl optionally substituted with one R²⁰ᵇ; and R²⁰ᵇ is —CN. In embodiments of a compound of Formula (I-2); R⁷ is methyl optionally substituted with one, two, or three R²⁰ᶜ; each R²⁰ᶜ is independently selected from halogen, C₂₋₆alkenyl, C₂₋₆alkynyl, C₃₋₁₀cycloalkyl, C₂₋₉heterocycloalkyl, C₆₋₁₀aryl, and C₁₋₉heteroaryl; L¹ is a bond; R⁴ is hydrogen; R⁵ is methyl; R⁶ is hydrogen; R¹ is a

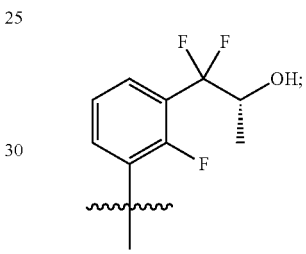

R² is —OR²ᵃ; R²ᵃ is methyl; R³ is C₃₋₄cycloalkyl optionally substituted with one R²⁰ᵇ; and R²⁰ᵇ is —CN. In embodiments of a compound of Formula (I-2); R⁷ is methyl optionally substituted with one, two, or three R²⁰ᶜ; each R²⁰ᶜ is independently selected from halogen, C₂₋₆alkenyl, C₂₋₆alkynyl, C₃₋₁₀cycloalkyl, C₂₋₉heterocycloalkyl, C₆₋₁₀aryl, and C₁₋₉heteroaryl; L¹ is a bond; R⁴ is hydrogen; R⁵ is methyl; R⁶ is hydrogen; R¹ is a

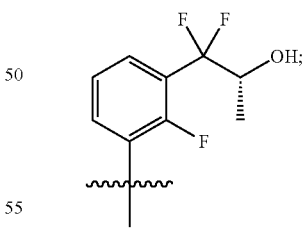

R² is —OR²ᵃ; R²ᵃ is methyl; R³ is C₃₋₄cycloalkyl optionally substituted with one, two, or three R²⁰ᵇ; and R²⁰ᵇ is —CN. In embodiments of a compound of Formula (I-2); R⁷ is methyl optionally substituted with one, two, or three R²⁰ᶜ; each R²⁰ᶜ is independently selected from halogen, C₂₋₆alkenyl, C₂₋₆alkynyl, C₃₋₁₀cycloalkyl, C₂₋₉heterocycloalkyl, C₆₋₁₀aryl, and C₁₋₉heteroaryl; L¹ is a bond; R⁴ is hydrogen; R⁵ is methyl; R⁶ is hydrogen; R¹ is a

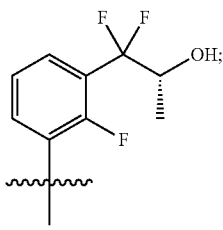 [SMILES: *c1cccc(C(F)(F)[C@@H](C)O)c1F]

R² is —OR²ᵃ; R²ᵃ is methyl; R³ is $C_{3-4}$cycloalkyl optionally substituted with one, two, or three R²⁰ᵇ; and each R²⁰ᵇ is independently —CN or $C_{1-3}$haloalkyl. In embodiments of a compound of Formula (I-2); R⁷ is methyl optionally substituted with one, two, or three R²⁰ᶜ; each R²⁰ᶜ is independently selected from halogen, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl; L¹ is a bond; R⁴ is hydrogen; R⁵ is methyl; R⁶ is hydrogen; R¹ is a

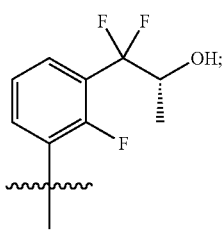 [SMILES: *c1cccc(C(F)(F)[C@@H](C)O)c1F]

R² is —OR²ᵃ; R²ᵃ is methyl; R³ is $C_{3-4}$cycloalkyl optionally substituted with one, two, or three R²⁰ᵇ; and each R²⁰ᵇ is independently —CN or $C_{1-3}$haloalkyl. In embodiments of a compound of Formula (I-2); R⁷ is methyl optionally substituted with one, two, or three R²⁰ᶜ; each R²⁰ᶜ is independently selected from halogen, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl; L¹ is a bond; R⁴ is hydrogen; R⁵ is methyl; R⁶ is hydrogen; R¹ is

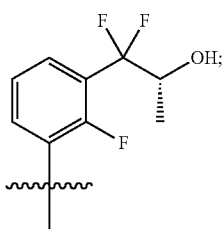 [SMILES: *c1cccc(C(F)(F)[C@@H](C)O)c1F]

R² is —OR²ᵃ; R²ᵃ is methyl; R³ is $C_{3-4}$cycloalkyl optionally substituted with one, two, or three R²⁰ᵇ; and each R²⁰ᵇ is independently —CN or $C_{1-3}$haloalkyl. In embodiments of a compound of Formula (I-2); R⁷ is methyl optionally substituted with one, two, or three R²⁰ᶜ; each R²⁰ᶜ is independently selected from halogen, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl; L¹ is a bond; R⁴ is hydrogen; R⁵ is methyl; R⁶ is hydrogen; R¹ is a

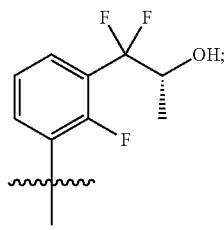 [SMILES: *c1cccc(C(F)(F)[C@@H](C)O)c1F]

R² is —OR²ᵃ; R²ᵃ is methyl; R³ is $C_{3-4}$cycloalkyl optionally substituted with one, two, or three R²⁰ᵇ; and each R²⁰ᵇ is independently selected from amino; —CN; $C_{1-3}$alkyl; $C_{1-3}$alkoxy; $C_{1-3}$haloalkyl; —OH; —N(R²⁴)C(O)R²⁵; and —C(O)N(R²²)(R²³).

In embodiments of a compound of Formula (I-2); R⁷ is methyl optionally substituted with one, two, or three R²⁰ᶜ; each R²⁰ᶜ is independently selected from halogen, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl; L¹ is a bond; R⁴ is hydrogen; R⁵ is methyl; R⁶ is hydrogen; R¹ is a

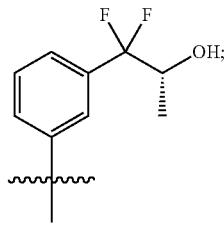 [SMILES: *c1cccc(C(F)(F)[C@@H](C)O)c1]

R² is —OR²ᵃ; R²ᵃ is methyl; and R³ is

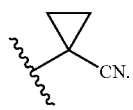

In embodiments of a compound of Formula (I-2); R⁷ is methyl optionally substituted with one, two, or three R²⁰ᶜ; each R²⁰ᶜ is independently selected from halogen, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl; L¹ is a bond; R⁴ is hydrogen; R⁵ is methyl; R⁶ is hydrogen; R¹ is a

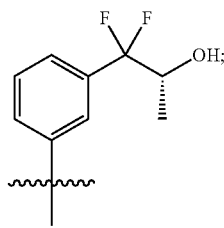 [SMILES: *c1cccc(C(F)(F)[C@@H](C)O)c1]

R² is —OR²ᵃ; R²ᵃ is methyl; R³ is cyclopropyl optionally substituted with one R²⁰ᵇ; and R²⁰ᵇ is —CN. In embodiments of a compound of Formula (I-2); R⁷ is methyl optionally substituted with one, two, or three R²⁰ᶜ; each R²⁰ᶜ is independently selected from halogen, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl; L¹ is a bond; R⁴ is hydrogen; R⁵ is methyl; R⁶ is hydrogen; R¹ is a

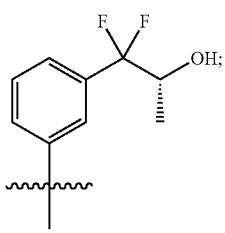 [SMILES: *c1cccc(C(F)(F)[C@@H](C)O)c1]

$R^2$ is —$OR^{2a}$; $R^{2a}$ is methyl; $R^3$ is $C_{3-4}$cycloalkyl optionally substituted with one $R^{20b}$; and $R^{20b}$ is —CN. In embodiments of a compound of Formula (I-2); $R^7$ is methyl optionally substituted with one, two, or three $R^{20c}$; each $R^{20c}$ is independently selected from halogen, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl; $L^1$ is a bond; $R^4$ is hydrogen; $R^5$ is methyl; $R^6$ is hydrogen; $R^1$ is a

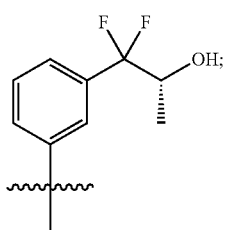 [SMILES: *c1cccc(C(F)(F)[C@@H](C)O)c1]

$R^2$ is —$OR^{2a}$; $R^{2a}$ is methyl; $R^3$ is $C_{3-4}$cycloalkyl optionally substituted with one, two, or three $R^{20b}$; and $R^{20b}$ is —CN. In embodiments of a compound of Formula (I-2); $R^7$ is methyl optionally substituted with one, two, or three $R^{20c}$; each $R^{20c}$ is independently selected from halogen, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl; $L^1$ is a bond; $R^4$ is hydrogen; $R^5$ is methyl; $R^6$ is hydrogen; $R^1$ is a

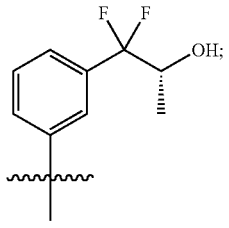 [SMILES: *c1cccc(C(F)(F)[C@@H](C)O)c1]

$R^2$ is —$OR^{2a}$; $R^{2a}$ is methyl; $R^3$ is $C_{3-4}$cycloalkyl optionally substituted with one, two, or three $R^{20b}$; and each $R^{20b}$ is independently —CN or $C_{1-3}$haloalkyl. In embodiments of a compound of Formula (I-2); $R^7$ is methyl optionally substituted with one, two, or three $R^{20c}$; each $R^{20c}$ is independently selected from halogen, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl; $L^1$ is a bond; $R^4$ is hydrogen; $R^5$ is methyl; $R^6$ is hydrogen; $R^1$ is a

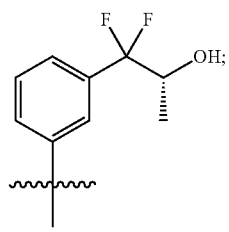 [SMILES: *c1cccc(C(F)(F)[C@@H](C)O)c1]

$R^2$ is —$OR^{2a}$; $R^{2a}$ is methyl; $R^3$ is $C_{3-4}$cycloalkyl optionally substituted with one, two, or three $R^{20b}$; and each $R^{20b}$ is independently —CN or $C_{1-3}$haloalkyl. In embodiments of a compound of Formula (I-2); $R^7$ is methyl optionally substituted with one, two, or three $R^{20c}$; each $R^{20c}$ is independently selected from halogen, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl; $L^1$ is a bond; $R^4$ is hydrogen; $R^5$ is methyl; $R^6$ is hydrogen; $R^1$ is a

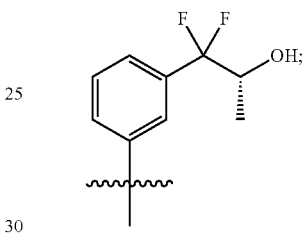

$R^2$ is —$OR^{2a}$; $R^{2a}$ is methyl; $R^3$ is $C_{3-4}$cycloalkyl optionally substituted with one, two, or three $R^{20b}$; and each $R^{20b}$ is independently —CN or $C_{1-3}$haloalkyl. In embodiments of a compound of Formula (I-2); $R^7$ is methyl optionally substituted with one, two, or three $R^{20c}$; each $R^{20c}$ is independently selected from halogen, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl; $L^1$ is a bond; $R^4$ is hydrogen; $R^5$ is methyl; $R^6$ is hydrogen; $R^1$ is a

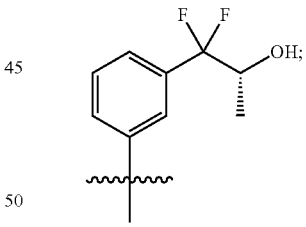

$R^2$ is —$OR^{2a}$; $R^{2a}$ is methyl; $R^3$ is $C_{3-4}$cycloalkyl optionally substituted with one, two, or three $R^{20b}$; and each $R^{20b}$ is independently selected from amino; —CN; $C_{1-3}$alkyl; $C_{1-3}$alkoxy; $C_{1-3}$haloalkyl; —OH; —N($R^{24}$)C(O)$R^{25}$; and —C(O)N($R^{22}$)($R^{23}$).

In embodiments of a compound of Formula (I-2); $R^7$ is methyl optionally substituted with one, two, or three $R^{20c}$; each $R^{20c}$ is independently selected from halogen, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl; $L^1$ is a bond; $R^4$ is hydrogen; $R^5$ is methyl; $R^6$ is hydrogen; $R^1$ is a phenyl substituted with one or more $R^{10}$; each $R^{10}$ is independently selected from halogen and $C_{1-4}$alkyl optionally substituted with one, two, or three $R^{20d}$; each $R^{20d}$ is independently selected from halogen and —OH; $R^2$ is —$OR^{2a}$; $R^{2a}$ is methyl; and $R^3$ is

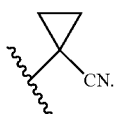 [SMILES: *C1(C#N)CC1]

In embodiments of a compound of Formula (I-2); $R^7$ is methyl optionally substituted with one, two, or three $R^{20c}$; each $R^{20c}$ is independently selected from halogen, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl; $L^1$ is a bond; $R^4$ is hydrogen; $R^5$ is methyl; $R^6$ is hydrogen; $R^1$ is a phenyl substituted with one or more $R^{10}$; each $R^{10}$ is independently selected from halogen and $C_{1-4}$alkyl optionally substituted with one, two, or three $R^{20d}$; each $R^{20d}$ is independently selected from halogen and —OH; $R^2$ is —OR$^{2a}$; $R^{2a}$ is methyl; $R^3$ is cyclopropyl optionally substituted with one $R^{20b}$; and $R^{20b}$ is —CN. In embodiments of a compound of Formula (I-2); $R^7$ is methyl optionally substituted with one, two, or three $R^{20c}$; each $R^{20c}$ is independently selected from halogen, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl; $L^1$ is a bond; $R^4$ is hydrogen; $R^5$ is methyl; $R^6$ is hydrogen; $R^1$ is a phenyl substituted with one or more $R^{10}$; each $R^{10}$ is independently selected from halogen and $C_{1-4}$alkyl optionally substituted with one, two, or three $R^{20d}$; each $R^{20d}$ is independently selected from halogen and —OH; $R^2$ is —OR$^{2a}$; $R^{2a}$ is methyl; $R^3$ is $C_{3-4}$cycloalkyl optionally substituted with one, two, or three $R^{20b}$; and $R^{20b}$ is —CN. In embodiments of a compound of Formula (I-2); $R^7$ is methyl optionally substituted with one, two, or three $R^{20c}$; each $R^{20c}$ is independently selected from halogen, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl; $L^1$ is a bond; $R^4$ is hydrogen; $R^5$ is methyl; $R^6$ is hydrogen; $R^1$ is a phenyl substituted with one or more $R^{10}$; each $R^{10}$ is independently selected from halogen and $C_{1-4}$alkyl optionally substituted with one, two, or three $R^{20d}$; each $R^{20d}$ is independently selected from halogen and —OH; $R^2$ is —OR$^{2a}$; $R^{2a}$ is methyl; $R^3$ is $C_{3-4}$cycloalkyl optionally substituted with one, two, or three $R^{20b}$; and each $R^{20b}$ is independently —CN or $C_{1-3}$haloalkyl. In embodiments of a compound of Formula (I-2); $R^7$ is methyl optionally substituted with one, two, or three $R^{20c}$; each $R^{20c}$ is independently selected from halogen, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl; $L^1$ is a bond; $R^4$ is hydrogen; $R^5$ is methyl; $R^6$ is hydrogen; $R^1$ is a phenyl substituted with one or more $R^{10}$; each $R^{10}$ is independently selected from halogen and $C_{1-4}$alkyl optionally substituted with one, two, or three $R^{20d}$; each $R^{20d}$ is independently selected from halogen and —OH; $R^2$ is —OR$^{2a}$; $R^{2a}$ is methyl; $R^3$ is $C_{3-4}$cycloalkyl optionally substituted with one, two, or three $R^{20b}$; and each $R^{20b}$ is independently —CN or $C_{1-3}$haloalkyl. In embodiments of a compound of Formula (I-2); $R^7$ is methyl optionally substituted with one, two, or three $R^{20c}$; each $R^{20c}$ is independently selected from halogen, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl; $L^1$ is a bond; $R^4$ is hydrogen; $R^5$ is methyl; $R^6$ is hydrogen; $R^1$ is a phenyl substituted with one or more $R^{10}$; each $R^{10}$ is independently selected from halogen and $C_{1-4}$alkyl optionally substituted with one, two, or three $R^{20d}$; each $R^{20d}$ is independently selected from halogen and —OH; $R^2$ is —OR$^{2a}$; $R^{2a}$ is methyl; $R^3$ is $C_{3-4}$cycloalkyl optionally substituted with one, two, or three $R^{20b}$; and each $R^{20b}$ is independently selected from amino; —CN; $C_{1-3}$alkyl; $C_{1-3}$alkoxy; $C_{1-3}$haloalkyl; —OH; —N(R$^{24}$)C(O)R$^{21}$; and —C(O)N(R$^{22}$)(R$^{23}$).

In embodiments of a compound of Formula (I-2); $R^7$ is methyl optionally substituted with one, two, or three $R^{20c}$; each $R^{20c}$ is independently selected from halogen, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl; $L^1$ is a bond; $R^4$ is hydrogen; $R^5$ is methyl; $R^6$ is hydrogen; $R^1$ is a phenyl substituted with one or more $R^{10}$; each $R^{10}$ is independently selected from halogen and $C_{1-4}$alkyl optionally substituted with one, two, or three $R^{20d}$; each $R^{20d}$ is independently selected from halogen, —OH, $C_{2-5}$heterocycloalkyl optionally substituted with one, two, or three $C_{1-6}$alkyl (e.g., methyl, ethyl, or propyl), and —OR$^{21}$, wherein $R^{21}$ is $C_{2-5}$heterocycloalkyl optionally substituted with one, two, or three $C_{1-6}$alkyl (e.g., methyl, ethyl, propyl, or butyl); $R^2$ is —OR$^{2a}$; $R^{2a}$ is methyl; and $R^3$ is

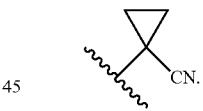

In embodiments of a compound of Formula (I-2); $R^7$ is methyl optionally substituted with one, two, or three $R^{20c}$; each $R^{20c}$ is independently selected from halogen, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl; $L^1$ is a bond; $R^4$ is hydrogen; $R^5$ is methyl; $R^6$ is hydrogen; $R^1$ is a phenyl substituted with one or more $R^{10}$; each $R^{10}$ is independently selected from halogen and $C_{1-4}$alkyl optionally substituted with one, two, or three $R^{20d}$; each $R^{20d}$ is independently selected from halogen, —OH, $C_{2-5}$heterocycloalkyl optionally substituted with one, two, or three $C_{1-6}$alkyl (e.g., methyl, ethyl, or propyl), and —OR$^{21}$, wherein $R^{21}$ is $C_{2-5}$heterocycloalkyl optionally substituted with one, two, or three $C_{1-6}$alkyl (e.g., methyl, ethyl, propyl, or butyl); $R^3$ is cyclopropyl optionally substituted with one $R^{20b}$; and $R^{20b}$ is —CN. In embodiments of a compound of Formula (I-2); $R^7$ is methyl optionally substituted with one, two, or three $R^{20c}$; each $R^{20c}$ is independently selected from halogen, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl; $L^1$ is a bond; $R^4$ is hydrogen; $R^5$ is methyl;

$R^6$ is hydrogen; $R^1$ is a phenyl substituted with one or more $R^{10}$; each $R^{10}$ is independently selected from halogen and $C_{1-4}$alkyl optionally substituted with one, two, or three $R^{20d}$; each $R^{20d}$ is independently selected from halogen, —OH, $C_{2-5}$heterocycloalkyl optionally substituted with one, two, or three $C_{1-6}$alkyl (e.g., methyl, ethyl, or propyl), and —$OR^{21}$, wherein $R^{21}$ is $C_{2-5}$heterocycloalkyl optionally substituted with one, two, or three $C_{1-6}$alkyl (e.g., methyl, ethyl, propyl, or butyl); $R^2$ is —$OR^{2a}$; $R^{2a}$ is methyl; $R^3$ is $C_{3-4}$cycloalkyl optionally substituted with one $R^{20b}$; and $R^{20b}$ is —CN. In embodiments of a compound of Formula (I-2); $R^7$ is methyl optionally substituted with one, two, or three $R^{20c}$; each $R^{20c}$ is independently selected from halogen, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl; $L^1$ is a bond; $R^4$ is hydrogen; $R^5$ is methyl; $R^6$ is hydrogen; $R^1$ is a phenyl substituted with one or more $R^{10}$; each $R^{10}$ is independently selected from halogen and $C_{1-4}$alkyl optionally substituted with one, two, or three $R^{20d}$; each $R^{20d}$ is independently selected from halogen, —OH, $C_{2-5}$heterocycloalkyl optionally substituted with one, two, or three $C_{1-6}$alkyl (e.g., methyl, ethyl, or propyl), and —$OR^{21}$, wherein $R^{21}$ is $C_{2-5}$heterocycloalkyl optionally substituted with one, two, or three $C_{1-6}$alkyl (e.g., methyl, ethyl, propyl, or butyl); $R^2$ is —$OR^{2a}$; $R^{2a}$ is methyl; $R^3$ is $C_{3-4}$cycloalkyl optionally substituted with one, two, or three $R^{20b}$; and each $R^{20b}$ is independently —CN or $C_{1-3}$haloalkyl. In embodiments of a compound of Formula (I-2); $R^7$ is methyl optionally substituted with one, two, or three $R^{20c}$; each $R^{20c}$ is independently selected from halogen, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl; $L^1$ is a bond; $R^4$ is hydrogen; $R^5$ is methyl; $R^6$ is hydrogen; $R^1$ is a phenyl substituted with one or more $R^{10}$; each $R^{10}$ is independently selected from halogen and $C_{1-4}$alkyl optionally substituted with one, two, or three $R^{20d}$; each $R^{20d}$ is independently selected from halogen, —OH, $C_{2-5}$heterocycloalkyl optionally substituted with one, two, or three $C_{1-6}$alkyl (e.g., methyl, ethyl, or propyl), and —$OR^{21}$, wherein $R^{21}$ is $C_{2-5}$heterocycloalkyl optionally substituted with one, two, or three $C_{1-6}$alkyl (e.g., methyl, ethyl, propyl, or butyl); $R^2$ is —$OR^{2a}$; $R^{2a}$ is methyl; $R^3$ is $C_{3-4}$cycloalkyl optionally substituted with one, two, or three $R^{20b}$; and each $R^{20b}$ is independently —CN or $C_{1-3}$haloalkyl. In embodiments of a compound of Formula (I-2); $R^7$ is methyl optionally substituted with one, two, or three $R^{20c}$; each $R^{20c}$ is independently selected from halogen, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl; $L^1$ is a bond; $R^4$ is hydrogen; $R^5$ is methyl; $R^6$ is hydrogen; $R^1$ is a phenyl substituted with one or more $R^{10}$; each $R^{10}$ is independently selected from halogen and $C_{1-4}$alkyl optionally substituted with one, two, or three $R^{20d}$; each $R^{20d}$ is independently selected from halogen, —OH, $C_{2-5}$heterocycloalkyl optionally substituted with one, two, or three $C_{1-6}$alkyl (e.g., methyl, ethyl, or propyl), and —$OR^{21}$, wherein $R^{21}$ is $C_{2-5}$heterocycloalkyl optionally substituted with one, two, or three $C_{1-6}$alkyl (e.g., methyl, ethyl, propyl, or butyl); $R^2$ is —$OR^{2a}$; $R^{2a}$ is methyl; $R^3$ is $C_{3-4}$cycloalkyl optionally substituted with one, two, or three $R^{20b}$; and each $R^{20b}$ is independently —CN or $C_{1-3}$haloalkyl. In embodiments of a compound of Formula (I-2); $R^7$ is methyl optionally substituted with one, two, or three $R^{20c}$; each $R^{20c}$ is independently selected from halogen, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl; $L^1$ is a bond; $R^4$ is hydrogen; $R^5$ is methyl; $R^6$ is hydrogen; $R^1$ is a 6-10 membered aryl ring substituted with one or more $R^{10}$; each $R^{10}$ is independently selected from halogen and $C_{1-4}$alkyl optionally substituted with one, two, or three $R^{20d}$; each $R^{20d}$ is independently selected from halogen, —OH, $C_{2-5}$heterocycloalkyl optionally substituted with one, two, or three $C_{1-6}$alkyl (e.g., methyl, ethyl, or propyl), and —$OR^{21}$, wherein $R^{21}$ is $C_{2-5}$heterocycloalkyl optionally substituted with one, two, or three $C_{1-6}$alkyl (e.g., methyl, ethyl, propyl, or butyl); $R^2$ is —$OR^{2a}$; $R^{2a}$ is methyl; $R^3$ is $C_{3-4}$cycloalkyl optionally substituted with one, two, or three $R^{20b}$; and each $R^{20b}$ is independently selected from amino; —CN; $C_{1-3}$alkyl; $C_{1-3}$alkoxy; $C_{1-3}$haloalkyl; —OH; —$N(R^{24})C(O)R^{25}$; and —$C(O)N(R^{22})(R^{23})$).

In embodiments of a compound of Formula (I-2); $R^7$ is methyl optionally substituted with one, two, or three $R^{20c}$; each $R^{20c}$ is independently selected from halogen, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl; $L^1$ is a bond; $R^4$ is hydrogen; $R^5$ is methyl; $R^6$ is hydrogen; $R^1$ is a 6-10 membered aryl ring substituted with one or more $R^{10}$; each $R^{10}$ is independently selected from halogen and $C_{1-4}$alkyl optionally substituted with one, two, or three $R^{20d}$; each $R^{20d}$ is independently selected from halogen, —OH, $C_{2-5}$heterocycloalkyl optionally substituted with one, two, or three $C_{1-6}$alkyl (e.g., methyl, ethyl, or propyl), and —$OR^{21}$, wherein $R^{21}$ is $C_{2-5}$heterocycloalkyl optionally substituted with one, two, or three $C_{1-6}$alkyl (e.g., methyl, ethyl, propyl, or butyl); $R^2$ is —$OR^{2a}$; $R^{2a}$ is methyl; and $R^3$ is

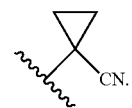 [SMILES: *C1(C#N)CC1]

In embodiments of a compound of Formula (I-2); $R^7$ is methyl optionally substituted with one, two, or three $R^{20c}$; each $R^{20c}$ is independently selected from halogen, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl; $L^1$ is a bond; $R^4$ is hydrogen; $R^5$ is methyl; $R^6$ is hydrogen; $R^1$ is a 6-10 membered aryl ring substituted with one or more $R^{10}$; each $R^{10}$ is independently selected from halogen and $C_{1-4}$ alkyl optionally substituted with one, two, or three $R^{20d}$; each $R^{20d}$ is independently selected from halogen, —OH, $C_{2-5}$heterocycloalkyl optionally substituted with one, two, or three $C_{1-6}$alkyl (e.g., methyl, ethyl, or propyl), and —$OR^{21}$, wherein $R^{21}$ is $C_{2-5}$heterocycloalkyl optionally substituted with one, two, or three $C_{1-6}$alkyl (e.g., methyl, ethyl, propyl, or butyl); $R^3$ is cyclopropyl optionally substituted with one $R^{20b}$; and $R^{20b}$ is —CN. In embodiments of a compound of Formula (I-2); $R^7$ is methyl optionally substituted with one, two, or three $R^{20c}$; each $R^{20c}$ is independently selected from halogen, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl; $L^1$ is a bond; $R^4$ is hydrogen; $R^5$ is methyl; $R^6$ is hydrogen; $R^1$ is a 6-10 membered aryl ring substituted with one or more $R^{10}$; each $R^{10}$ is independently selected from halogen and $C_{1-4}$alkyl optionally substituted with one, two, or three $R^{20d}$; each $R^{20d}$ is independently selected from halogen, —OH, $C_{2-5}$heterocycloalkyl optionally substituted with one, two, or three $C_{1-6}$alkyl (e.g., methyl, ethyl, or propyl), and —$OR^{21}$, wherein $R^{21}$ is $C_{2-5}$heterocycloalkyl optionally substituted with one, two, or three $C_{1-6}$alkyl (e.g., methyl, ethyl, propyl, or butyl); $R^2$ is —$OR^{2a}$; $R^{2a}$ is methyl; $R^3$ is $C_{3-4}$cycloalkyl optionally substituted with one $R^{20b}$; and $R^{20b}$ is —CN. In embodiments of a compound of Formula (I-2); $R^7$ is methyl optionally substituted with one, two, or three $R^{20c}$; each $R^{20c}$ is independently selected from halogen, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl; $L^1$ is a bond; $R^4$ is hydrogen; $R^5$ is methyl; $R^6$ is hydrogen; $R^1$ is a 6-10 membered aryl ring substituted with one or more $R^{10}$; each $R^{10}$ is independently selected from halogen and $C_{1-4}$alkyl optionally substituted with one, two, or three $R^{20d}$; each $R^{20d}$ is independently selected from halogen, —OH, $C_{2-5}$heterocycloalkyl optionally substituted with one, two, or three $C_{1-6}$alkyl (e.g., methyl, ethyl, or propyl), and —$OR^{21}$, wherein $R^{21}$ is $C_{2-5}$heterocycloalkyl optionally substituted with one, two, or three $C_{1-6}$alkyl (e.g., methyl, ethyl, propyl, or butyl); $R^2$ is —$OR^{2a}$; $R^{2a}$ is methyl; $R^3$ is $C_{3-4}$cycloalkyl optionally substituted with one, two, or three $R^{20b}$; and $R^{20b}$ is —CN. In embodiments of a compound of Formula (I-2); $R^7$ is methyl optionally substituted with one, two, or three $R^{20c}$; each $R^{20c}$ is independently selected from halogen, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl; $L^1$ is a bond; $R^4$ is hydrogen; $R^5$ is methyl; $R^6$ is hydrogen; $R^1$ is a 6-10 membered aryl ring substituted with one or more $R^{10}$; each $R^{10}$ is independently selected from halogen and $C_{1-4}$alkyl optionally substituted with one, two, or three $R^{20d}$; each $R^{20d}$ is independently selected from halogen, —OH, $C_{2-5}$heterocycloalkyl optionally substituted with one, two, or three $C_{1-6}$ alkyl (e.g., methyl, ethyl, or propyl), and —$OR^{21}$, wherein $R^{21}$ is $C_{2-5}$heterocycloalkyl optionally substituted with one, two, or three $C_{1-6}$alkyl (e.g., methyl, ethyl, propyl, or butyl); $R^2$ is —$OR^{2a}$; $R^{2a}$ is methyl; $R^3$ is $C_{3-4}$cycloalkyl optionally substituted with one, two, or three $R^{20b}$; and each $R^{20b}$ is independently —CN or $C_{1-3}$haloalkyl. In embodiments of a compound of Formula (I-2); $R^7$ is methyl optionally substituted with one, two, or three $R^{20c}$; each $R^{20c}$ is independently selected from halogen, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl; $L^1$ is a bond; $R^4$ is hydrogen; $R^5$ is methyl;

$R^6$ is hydrogen; $R^1$ is a 6-10 membered aryl ring substituted with one or more $R^{10}$; each $R^{10}$ is independently selected from halogen and $C_{1-4}$alkyl optionally substituted with one, two, or three $R^{20d}$; each $R^{20d}$ is independently selected from halogen, —OH, $C_{2-5}$heterocycloalkyl optionally substituted with one, two, or three $C_{1-6}$alkyl (e.g., methyl, ethyl, or propyl), and —$OR^{21}$, wherein $R^{21}$ is $C_{2-5}$heterocycloalkyl optionally substituted with one, two, or three $C_{1-6}$alkyl (e.g., methyl, ethyl, propyl, or butyl); $R^2$ is —$OR^{2a}$; $R^{2a}$ is methyl; $R^3$ is $C_{3-4}$cycloalkyl optionally substituted with one, two, or three $R^{20b}$; and each $R^{20b}$ is independently —CN or $C_{1-3}$haloalkyl. In embodiments of a compound of Formula (I-2); $R^7$ is methyl optionally substituted with one, two, or three $R^{20c}$; each $R^{20c}$ is independently selected from halogen, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl; $L^1$ is a bond; $R^4$ is hydrogen; $R^5$ is methyl; $R^6$ is hydrogen; $R^1$ is a 6-10 membered aryl ring substituted with one or more $R^{10}$; each $R^{10}$ is independently selected from halogen and $C_{1-4}$alkyl optionally substituted with one, two, or three $R^{20d}$; each $R^{20d}$ is independently selected from halogen, —OH, $C_{2-5}$heterocycloalkyl optionally substituted with one, two, or three $C_{1-6}$alkyl (e.g., methyl, ethyl, or propyl), and —$OR^{21}$, wherein $R^{21}$ is $C_{2-5}$heterocycloalkyl optionally substituted with one, two, or three $C_{1-6}$alkyl (e.g., methyl, ethyl, propyl, or butyl); $R^2$ is —$OR^{2a}$; $R^{2a}$ is methyl; $R^3$ is $C_{3-4}$cycloalkyl optionally substituted with one, two, or three $R^{20b}$; and each $R^{20b}$ is independently selected from amino; —CN; $C_{1-3}$alkyl; $C_{1-3}$alkoxy; $C_{1-3}$haloalkyl; —OH; —$N(R^{24})C(O)R^{25}$; and —$C(O)N(R^{22})(R^{23})$.

In embodiments of a compound of Formula (I'-2); $R^7$ is $C_{1-6}$alkyl optionally substituted with one, two, or three $R^{20c}$; each $R^{20c}$ is independently selected from halogen, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl; $L^1$ is a bond; $R^4$ is hydrogen; $R^6$ is hydrogen; $R^1$ is a

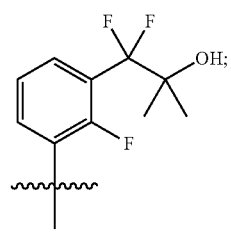 [SMILES: *c1cccc(C(F)(F)C(C)(C)O)c1F]

$R^2$ is —$OR^{2a}$; $R^{2a}$ is methyl; and $R^3$ is

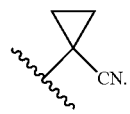

In embodiments of a compound of Formula (I'-2); $R^7$ is $C_{1-6}$alkyl optionally substituted with one, two, or three $R^{20c}$; each $R^{20c}$ is independently selected from halogen, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl; $L^1$ is a bond; $R^4$ is hydrogen; $R^6$ is hydrogen; $R^1$ is

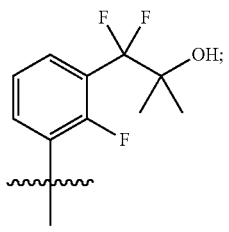 [SMILES: *c1cccc(C(F)(F)C(C)(C)O)c1F]

R² is —OR²ᵃ; R²ᵃ is methyl; R³ is cyclopropyl optionally substituted with one R²⁰ᵇ; and R²⁰ᵇ is —CN. In embodiments of a compound of Formula (I'-2); R⁷ is $C_{1-6}$alkyl optionally substituted with one, two, or three R²⁰ᶜ; each R²⁰ᶜ is independently selected from halogen, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl; L¹ is a bond; R⁴ is hydrogen; R⁶ is hydrogen; R¹ is a

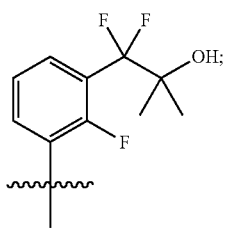 [SMILES: *c1cccc(C(F)(F)C(C)(C)O)c1F]

R² is —OR²ᵃ; R²ᵃ is methyl; R³ is $C_{3-4}$cycloalkyl optionally substituted with one R²⁰ᵇ; and R²⁰ᵇ is —CN. In embodiments of a compound of Formula (I'-2); R⁷ is $C_{1-6}$alkyl optionally substituted with one, two, or three R²⁰ᶜ; each R²⁰ᶜ is independently selected from halogen, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl; L¹ is a bond; R⁴ is hydrogen; R⁶ is hydrogen; R¹ is a

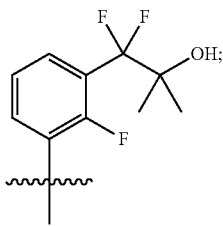 [SMILES: *c1cccc(C(F)(F)C(C)(C)O)c1F]

R² is —OR²ᵃ; R²ᵃ is methyl; R³ is $C_{3-4}$cycloalkyl optionally substituted with one, two, or three R²⁰ᵇ; and R²⁰ᵇ is —CN. In embodiments of a compound of Formula (I'-2); R⁷ is $C_{1-6}$alkyl optionally substituted with one, two, or three R²⁰ᶜ; each R²⁰ᶜ is independently selected from halogen, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl; L¹ is a bond; R⁴ is hydrogen; R⁶ is hydrogen; R¹ is a

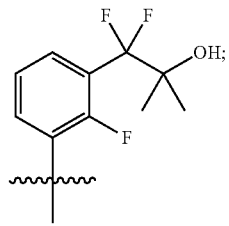 [SMILES: *c1cccc(C(F)(F)C(C)(C)O)c1F]

R² is —OR²ᵃ; R²ᵃ is methyl; R³ is $C_{3-4}$cycloalkyl optionally substituted with one, two, or three R²⁰ᵇ; and each R²⁰ᵇ is independently —CN or $C_{1-3}$haloalkyl. In embodiments of a compound of Formula (I'-2); R⁷ is $C_{1-6}$alkyl optionally substituted with one, two, or three R²⁰ᶜ; each R²⁰ᶜ is independently selected from halogen, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl; L¹ is a bond; R⁴ is hydrogen; R⁶ is hydrogen; R¹ is a

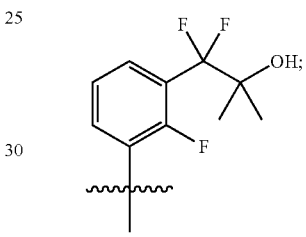

R² is —OR²ᵃ; R²ᵃ is methyl; R³ is $C_{3-4}$cycloalkyl optionally substituted with one, two, or three R²⁰ᵇ; and each R²⁰ᵇ is independently —CN or $C_{1-3}$haloalkyl. In embodiments of a compound of Formula (I'-2); R⁷ is $C_{1-6}$alkyl optionally substituted with one, two, or three R²⁰ᶜ; each R²⁰ᶜ is independently selected from halogen, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl; L¹ is a bond; R⁴ is hydrogen; R⁶ is hydrogen; R¹ is a

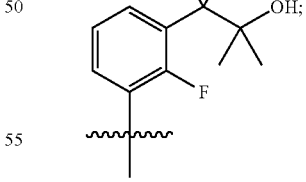

R² is —OR²ᵃ; R²ᵃ is methyl; R³ is $C_{3-4}$cycloalkyl optionally substituted with one, two, or three R²⁰ᵇ; and each R²⁰ᵇ is independently —CN or $C_{1-3}$ haloalkyl. In embodiments of a compound of Formula (I-2); R⁷ is $C_{1-6}$alkyl optionally substituted with one, two, or three R²⁰ᶜ; each R²⁰ᶜ is independently selected from halogen, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl; L¹ is a bond; R⁴ is hydrogen; R⁶ is hydrogen; R¹ is a

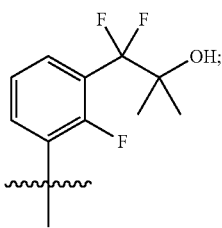 [SMILES: *c1cccc(C(F)(F)C(C)(C)O)c1F]

$R^2$ is —$OR^{2a}$; $R^{2a}$ is methyl; $R^3$ is $C_{3-4}$cycloalkyl optionally substituted with one, two, or three $R^{20b}$; and each $R^{20b}$ is independently selected from amino; —CN; $C_{1-3}$alkyl; $C_{1-3}$alkoxy; $C_{1-3}$ haloalkyl; —OH; —N($R^{24}$)C(O)$R^{25}$; and —C(O)N($R^{22}$)($R^{23}$).

In embodiments of a compound of Formula (I'-2); $R^7$ is $C_{1-6}$alkyl optionally substituted with one, two, or three $R^{20c}$; each $R^{20c}$ is independently selected from halogen, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl; $L^1$ is a bond; $R^4$ is hydrogen; $R^6$ is hydrogen; $R^1$ is a

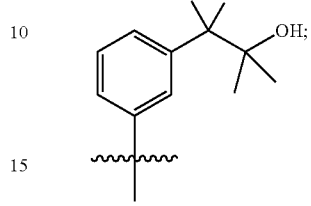

$R^2$ is —$OR^{2a}$; $R^{2a}$ is methyl; and $R^3$ is

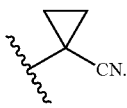

In embodiments of a compound of Formula (I'-2); $R^7$ is $C_{1-6}$alkyl optionally substituted with one, two, or three $R^{20c}$; each $R^{20c}$ is independently selected from halogen, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl; $L^1$ is a bond; $R^4$ is hydrogen; $R^6$ is hydrogen; $R^1$ is

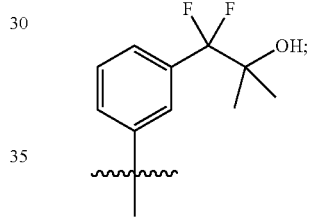

$R^2$ is —$OR^{2a}$; $R^{2a}$ is methyl; $R^3$ is cyclopropyl optionally substituted with one $R^{20b}$; and $R^{20b}$ is —CN. In embodiments of a compound of Formula (I'-2); $R^7$ is $C_{1-6}$alkyl optionally substituted with one, two, or three $R^{20c}$; each $R^{20c}$ is independently selected from halogen, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl; $L^1$ is a bond; $R^4$ is hydrogen; $R^6$ is hydrogen; $R^1$ is a

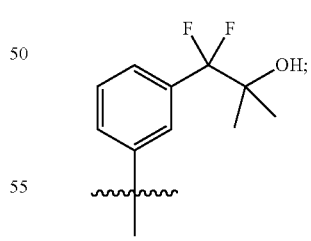

$R^2$ is —$OR^{2a}$; $R^{2a}$ is methyl; $R^3$ is $C_{3-4}$cycloalkyl optionally substituted with one $R^{20b}$; and $R^{20b}$ is —CN. In embodiments of a compound of Formula (I'-2); $R^7$ is $C_{1-6}$alkyl optionally substituted with one, two, or three $R^{20c}$; each $R^{20c}$ is independently selected from halogen, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl; $L^1$ is a bond; $R^4$ is hydrogen; $R^6$ is hydrogen; $R^1$ is a

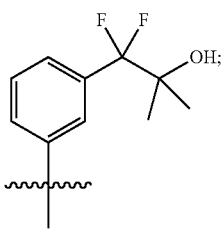 [SMILES: *c1cccc(C(F)(F)C(C)(C)O)c1]

$R^2$ is —$OR^{2a}$; $R^{2a}$ is methyl; $R^3$ is $C_{3-4}$cycloalkyl optionally substituted with one, two, or three $R^{20b}$; and $R^{20b}$ is —CN. In embodiments of a compound of Formula (I'-2); $R^7$ is $C_{1-6}$alkyl optionally substituted with one, two, or three $R^{20c}$; each $R^{20c}$ is independently selected from halogen, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl; $L^1$ is a bond; $R^4$ is hydrogen; $R^6$ is hydrogen; $R^1$ is a $R^2$ is —$OR^{2a}$; $R^{2a}$ is methyl; $R^3$ is $C_{3-4}$cycloalkyl optionally substituted with one, two, or three $R^{20b}$; and each $R^{20b}$ is independently —CN or $C_{1-3}$haloalkyl. In embodiments of a compound of Formula (I'-2); $R^7$ is $C_{1-6}$alkyl optionally substituted with one, two, or three $R^{20c}$; each $R^{20c}$ is independently selected from halogen, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl; $L^1$ is a bond; $R^4$ is hydrogen; $R^6$ is hydrogen; $R^1$ is

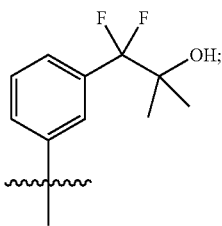 [SMILES: *c1cccc(C(F)(F)C(C)(C)O)c1]

R² is —OR²ᵃ; R²ᵃ is methyl; R³ is C₃₋₄cycloalkyl optionally substituted with one, two, or three R²⁰ᵇ; and each R²⁰ᵇ is independently —CN or C₁₋₃haloalkyl. In embodiments of a compound of Formula (I'-2); R⁷ is C₁₋₆alkyl optionally substituted with one, two, or three R²⁰ᶜ; each R²⁰ᶜ is independently selected from halogen, C₂₋₆alkenyl, C₂₋₆alkynyl, C₃₋₁₀cycloalkyl, C₂₋₉heterocycloalkyl, C₆₋₁₀aryl, and C₁₋₉heteroaryl; L¹ is a bond; R⁴ is hydrogen; R⁶ is hydrogen; R¹ is a

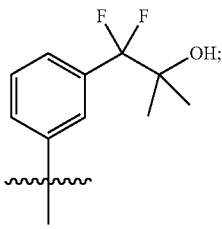 [SMILES: *c1cccc(C(F)(F)C(C)(C)O)c1]

R² is —OR²ᵃ; R²ᵃ is methyl; R³ is C₃₋₄cycloalkyl optionally substituted with one, two, or three R²⁰ᵇ; and each R²⁰ᵇ is independently —CN or C₁₋₃ haloalkyl. In embodiments of a compound of Formula (I'-2); R⁷ is C₁₋₆alkyl optionally substituted with one, two, or three R²⁰ᶜ; each R²⁰ᶜ is independently selected from halogen, C₂₋₆alkenyl, C₂₋₆alkynyl, C₃₋₁₀cycloalkyl, C₂₋₉heterocycloalkyl, C₆₋₁₀aryl, and C₁₋₉heteroaryl; L¹ is a bond; R⁴ is hydrogen; R⁶ is hydrogen; R¹ is a

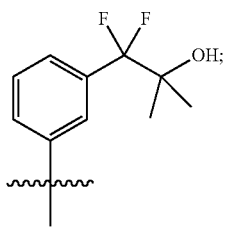 [SMILES: *c1cccc(C(F)(F)C(C)(C)O)c1]

R² is —OR²ᵃ; R²ᵃ is methyl; R³ is C₃₋₄cycloalkyl optionally substituted with one, two, or three R²⁰ᵇ; and each R²⁰ᵇ is independently selected from amino; —CN; C₁₋₃alkyl; C₁₋₃alkoxy; C₁₋₃ haloalkyl; —OH; —N(R²⁴)C(O)R²¹; and —C(O)N(R²²)(R²³).

In embodiments of a compound of Formula (I'-2); R⁷ is C₁₋₆alkyl optionally substituted with one, two, or three R²⁰ᶜ; each R²⁰ᶜ is independently selected from halogen, C₂₋₆alkenyl, C₂₋₆alkynyl, C₃₋₁₀cycloalkyl, C₂₋₉heterocycloalkyl, C₆₋₁₀aryl, and C₁₋₉heteroaryl; L¹ is a bond; R⁴ is hydrogen; R⁶ is hydrogen; R¹ is a

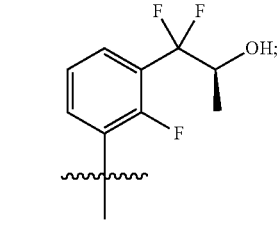

R² is —OR²ᵃ; R²ᵃ is methyl; and R³ is

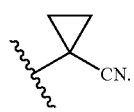

In embodiments of a compound of Formula (I'-2); R⁷ is C₁₋₆alkyl optionally substituted with one, two, or three R²⁰ᶜ; each R²⁰ᶜ is independently selected from halogen, C₂₋₆alkenyl, C₂₋₆alkynyl, C₃₋₁₀cycloalkyl, C₂₋₉heterocycloalkyl, C₆₋₁₀aryl, and C₁₋₉heteroaryl; L¹ is a bond; R⁴ is hydrogen; R⁶ is hydrogen; R¹ is a

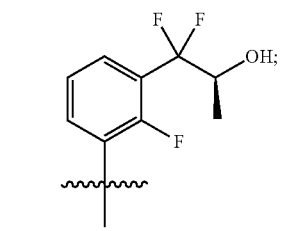 [SMILES: *c1cccc(C(F)(F)[C@H](C)O)c1F]

R² is —OR²ᵃ; R²ᵃ is methyl; R³ is cyclopropyl optionally substituted with one R²⁰ᵇ; and R²⁰ᵇ is —CN. In embodiments of a compound of Formula (I'-2); R⁷ is C₁₋₆alkyl optionally substituted with one, two, or three R²⁰ᶜ; each R²⁰ᶜ is independently selected from halogen, C₂₋₆alkenyl, C₂₋₆alkynyl, C₃₋₁₀cycloalkyl, C₂₋₉heterocycloalkyl, C₆₋₁₀aryl, and C₁₋₉heteroaryl; L¹ is a bond; R⁴ is hydrogen; R⁶ is hydrogen; R¹ is a

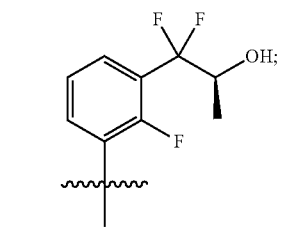 [SMILES: *c1cccc(C(F)(F)[C@H](C)O)c1F]

R² is —OR²ᵃ; R²ᵃ is methyl; R³ is C₃₋₄cycloalkyl optionally substituted with one R²⁰ᵇ; and R²⁰ᵇ is —CN. In embodiments of a compound of Formula (I'-2); R⁷ is C₁₋₆alkyl optionally substituted with one, two, or three R²⁰ᶜ; each R²⁰ᶜ is independently selected from halogen, C₂₋₆alkenyl, C₂₋₆alkynyl, C₃₋₁₀cycloalkyl, C₂₋₉heterocycloalkyl, C₆₋₁₀aryl, and C₁₋₉heteroaryl; L¹ is a bond; R⁴ is hydrogen; R⁶ is hydrogen; R¹ is a

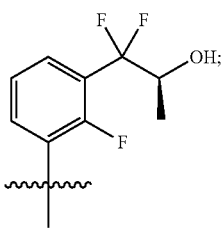 [SMILES: *c1cccc(C(F)(F)[C@H](C)O)c1F]

$R^2$ is —OR$^{2a}$; $R^{2a}$ is methyl; $R^3$ is $C_{3-4}$cycloalkyl optionally substituted with one, two, or three $R^{20b}$; and $R^{20b}$ is —CN. In embodiments of a compound of Formula (I'-2); $R^7$ is $C_{1-6}$alkyl optionally substituted with one, two, or three $R^{20c}$; each $R^{20c}$ is independently selected from halogen, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl; $L^1$ is a bond; $R^4$ is hydrogen; $R^6$ is hydrogen; $R^1$ is a

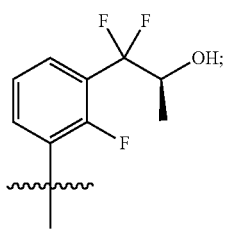 [SMILES: *c1cccc(C(F)(F)[C@H](C)O)c1F]

$R^2$ is —OR$^{2a}$; $R^{2a}$ is methyl; $R^3$ is $C_{3-4}$cycloalkyl optionally substituted with one, two, or three $R^{20b}$; and each $R^{20b}$ is independently —CN or $C_{1-3}$haloalkyl. In embodiments of a compound of Formula (I'-2); $R^7$ is $C_{1-6}$alkyl optionally substituted with one, two, or three $R^{20c}$; each $R^{20c}$ is independently selected from halogen, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl; $L^1$ is a bond; $R^4$ is hydrogen; $R^6$ is hydrogen; $R^1$ is a

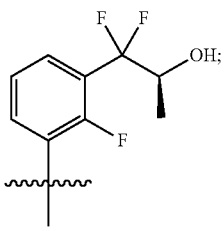 [SMILES: *c1cccc(C(F)(F)[C@H](C)O)c1F]

$R^2$ is —OR$^{2a}$; $R^{2a}$ is methyl; $R^3$ is $C_{3-4}$cycloalkyl optionally substituted with one, two, or three $R^{20b}$; and each $R^{20b}$ is independently —CN or $C_{1-3}$haloalkyl. In embodiments of a compound of Formula (I'-2); $R^7$ is $C_{1-6}$alkyl optionally substituted with one, two, or three $R^{20c}$; each $R^{20c}$ is independently selected from halogen, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl; $L^1$ is a bond; $R^4$ is hydrogen; $R^6$ is hydrogen; $R^1$ is a

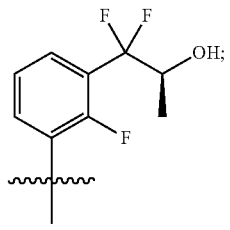 [SMILES: *c1cccc(C(F)(F)[C@H](C)O)c1F]

$R^2$ is —OR$^{2a}$; $R^{2a}$ is methyl; $R^3$ is $C_{3-4}$cycloalkyl optionally substituted with one, two, or three $R^{20b}$; and each $R^{20b}$ is independently —CN or $C_{1-3}$ haloalkyl. In embodiments of a compound of Formula (I-2); $R^7$ is $C_{1-6}$alkyl optionally substituted with one, two, or three $R^{20c}$; each $R^{20c}$ is independently selected from halogen, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl; $L^1$ is a bond; $R^4$ is hydrogen; $R^6$ is hydrogen; $R^1$ is

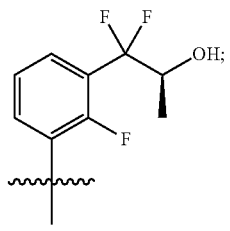 [SMILES: *c1cccc(C(F)(F)[C@H](C)O)c1F]

$R^2$ is —OR$^{2a}$; $R^{2a}$ is methyl; $R^3$ is $C_{3-4}$cycloalkyl optionally substituted with one, two, or three $R^{20b}$; and each $R^{20b}$ is independently selected from amino; —CN; $C_{1-3}$alkyl; $C_{1-3}$alkoxy; $C_{1-3}$ haloalkyl; —OH; —N(R$^{24}$)C(O)R$^{25}$; and —C(O)N(R$^{22}$)(R$^{23}$).

In embodiments of a compound of Formula (I'-2); $R^7$ is $C_{1-6}$alkyl optionally substituted with one, two, or three $R^{20c}$; each $R^{20c}$ is independently selected from halogen, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl; $L^1$ is a bond; $R^4$ is hydrogen; $R^6$ is hydrogen; $R^1$ is a

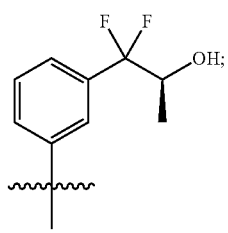 [SMILES: *c1cccc(C(F)(F)[C@H](C)O)c1]

$R^2$ is —OR$^{2a}$; $R^{2a}$ is methyl; and $R^3$ is

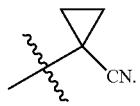 [SMILES: *C1(C#N)CC1]

In embodiments of a compound of Formula (I'-2); $R^7$ is $C_{1-6}$alkyl optionally substituted with one, two, or three $R^{20c}$; each $R^{20c}$ is independently selected from halogen, $C_{2-6}$alkenyl, C$_{2-6}$alkynyl, C$_{3-10}$cycloalkyl, C$_{2-9}$heterocycloalkyl, C$_{6-10}$aryl, and C$_{1-9}$heteroaryl; L$^1$ is a bond; R$^4$ is hydrogen; R$^6$ is hydrogen; R$^1$ is a

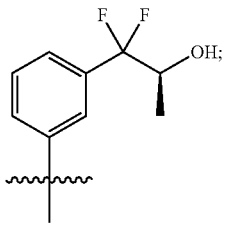 [SMILES: *c1cccc(C(F)(F)[C@H](C)O)c1]

R$^2$ is —OR$^{2a}$; R$^{2a}$ is methyl; R$^3$ is cyclopropyl optionally substituted with one R$^{20b}$; and R$^{20b}$ is —CN. In embodiments of a compound of Formula (I'-2); R$^7$ is C$_{1-6}$alkyl optionally substituted with one, two, or three R$^{20c}$; each R$^{20c}$ is independently selected from halogen, C$_{2-6}$alkenyl, C$_{2-6}$alkynyl, C$_{3-10}$cycloalkyl, C$_{2-9}$heterocycloalkyl, C$_{6-10}$aryl, and C$_{1-9}$heteroaryl; L$^1$ is a bond; R$^4$ is hydrogen; R$^6$ is hydrogen; R$^1$ is a

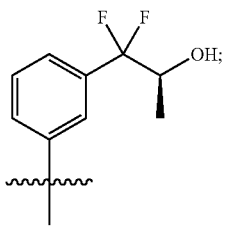 [SMILES: *c1cccc(C(F)(F)[C@H](C)O)c1]

R$^2$ is —OR$^{2a}$; R$^{2a}$ is methyl; R$^3$ is C$_{3-4}$cycloalkyl optionally substituted with one R$^{20b}$; and R$^{20b}$ is —CN. In embodiments of a compound of Formula (I'-2); R$^7$ is C$_{1-6}$alkyl optionally substituted with one, two, or three R$^{20c}$; each R$^{20c}$ is independently selected from halogen, C$_{2-6}$alkenyl, C$_{2-6}$alkynyl, C$_{3-10}$cycloalkyl, C$_{2-9}$heterocycloalkyl, C$_{6-10}$aryl, and C$_{1-9}$heteroaryl; L$^1$ is a bond; R$^4$ is hydrogen; R$^6$ is hydrogen; R$^1$ is a

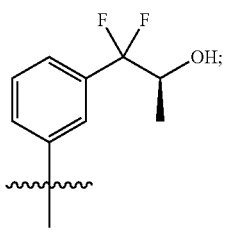 [SMILES: *c1cccc(C(F)(F)[C@H](C)O)c1]

R$^2$ is —OR$^{2a}$; R$^{2a}$ is methyl; R$^3$ is C$_{3-4}$cycloalkyl optionally substituted with one, two, or three R$^{20b}$; and R$^{20b}$ is —CN. In embodiments of a compound of Formula (I'-2); R$^7$ is C$_{1-6}$alkyl optionally substituted with one, two, or three R$^{20c}$; each R$^{20c}$ is independently selected from halogen, C$_{2-6}$alkenyl, C$_{2-6}$alkynyl, C$_{3-10}$cycloalkyl, C$_{2-9}$heterocycloalkyl, C$_{6-10}$aryl, and C$_{1-9}$heteroaryl; L$^1$ is a bond; R$^4$ is hydrogen; R$^6$ is hydrogen; R$^1$ is a

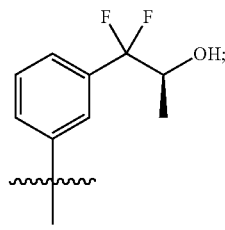 [SMILES: *c1cccc(C(F)(F)[C@H](C)O)c1]

R$^2$ is —OR$^{2a}$; R$^{2a}$ is methyl; R$^3$ is C$_{3-4}$cycloalkyl optionally substituted with one, two, or three R$^{20b}$; and each R$^{20b}$ is independently —CN or C$_{1-3}$haloalkyl. In embodiments of a compound of Formula (I'-2); R$^7$ is C$_{1-6}$alkyl optionally substituted with one, two, or three R$^{20c}$; each R$^{20c}$ is independently selected from halogen, C$_{2-6}$alkenyl, C$_{2-6}$alkynyl, C$_{3-10}$cycloalkyl, C$_{2-9}$heterocycloalkyl, C$_{6-10}$aryl, and C$_{1-9}$heteroaryl; L$^1$ is a bond; R$^4$ is hydrogen; R$^6$ is hydrogen; R$^1$ is

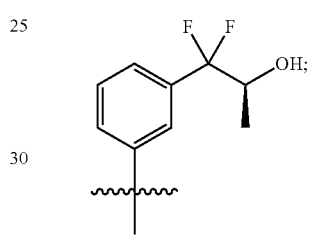

R$^2$ is —OR$^{2a}$; R$^{2a}$ is methyl; R$^3$ is C$_{3-4}$cycloalkyl optionally substituted with one, two, or three R$^{20b}$; and each R$^{20b}$ is independently —CN or C$_{1-3}$haloalkyl. In embodiments of a compound of Formula (I'-2); R$^7$ is C$_{1-6}$alkyl optionally substituted with one, two, or three R$^{20c}$; each R$^{20c}$ is independently selected from halogen, C$_{2-6}$alkenyl, C$_{2-6}$alkynyl, C$_{3-10}$cycloalkyl, C$_{2-9}$heterocycloalkyl, C$_{6-10}$aryl, and C$_{1-9}$heteroaryl; L$^1$ is a bond; R$^4$ is hydrogen; R$^6$ is hydrogen; R$^1$ is a

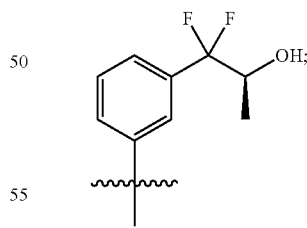

R$^2$ is —OR$^{2a}$; R$^{2a}$ is methyl; R$^3$ is C$_{3-4}$cycloalkyl optionally substituted with one, two, or three R$^{20b}$; and each R$^{20b}$ is independently —CN or C$_{1-3}$ haloalkyl. In embodiments of a compound of Formula (I'-2); R$^7$ is C$_{1-6}$alkyl optionally substituted with one, two, or three R$^{20c}$; each R$^{20c}$ is independently selected from halogen, C$_{2-6}$alkenyl, C$_{2-6}$alkynyl, C$_{3-10}$cycloalkyl, C$_{2-9}$heterocycloalkyl, C$_{6-10}$aryl, and C$_{1-9}$heteroaryl; L$^1$ is a bond; R$^4$ is hydrogen; R$^6$ is hydrogen; R$^1$ is a

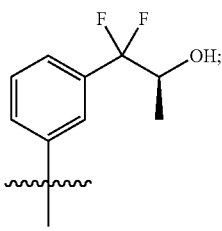 [SMILES: *c1cccc(C(F)(F)[C@H](C)O)c1]

R² is —OR²ᵃ; R²ᵃ is methyl; R³ is C₃₋₄cycloalkyl optionally substituted with one, two, or three R²⁰ᵇ; and each R²⁰ᵇ is independently selected from amino; —CN; C₁₋₃alkyl; C₁₋₃alkoxy; C₁₋₃ haloalkyl; —OH; —N(R²⁴)C(O)R²¹; and —C(O)N(R²²)(R²³).

In embodiments of a compound of Formula (I'-2); R⁷ is C₁₋₆alkyl optionally substituted with one, two, or three R²⁰ᶜ; each R²⁰ᶜ is independently selected from halogen, C₂₋₆alkenyl, C₂₋₆alkynyl, C₃₋₁₀cycloalkyl, C₂₋₉heterocycloalkyl, C₆₋₁₀aryl, and C₁₋₉heteroaryl; L¹ is a bond; R⁴ is hydrogen; R⁶ is hydrogen; R¹ is a

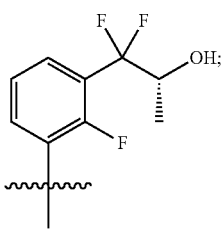 [SMILES: *c1cccc(C(F)(F)[C@@H](C)O)c1F]

R² is —OR²ᵃ; R²ᵃ is methyl; and R³ is

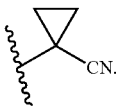 [SMILES: *C1(C#N)CC1]

In embodiments of a compound of Formula (I'-2); R⁷ is C₁₋₆alkyl optionally substituted with one, two, or three R²⁰ᶜ; each R²⁰ᶜ is independently selected from halogen, C₂₋₆alkenyl, C₂₋₆alkynyl, C₃₋₁₀cycloalkyl, C₂₋₉heterocycloalkyl, C₆₋₁₀aryl, and C₁₋₉heteroaryl; L¹ is a bond; R⁴ is hydrogen; R⁶ is hydrogen; R¹ is a

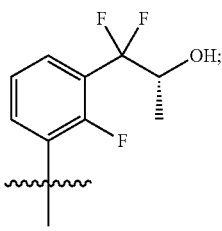 [SMILES: *c1cccc(C(F)(F)[C@@H](C)O)c1F]

R² is —OR²ᵃ; R²ᵃ is methyl; R³ is cyclopropyl optionally substituted with one R²⁰ᵇ; and R²⁰ᵇ is —CN. In embodiments of a compound of Formula (I'-2); R⁷ is C₁₋₆alkyl optionally substituted with one, two, or three R²⁰ᶜ; each R²⁰ᶜ is independently selected from halogen, C₂₋₆alkenyl, C₂₋₆alkynyl, C₃₋₁₀cycloalkyl, C₂₋₉heterocycloalkyl, C₆₋₁₀aryl, and C₁₋₉heteroaryl; L¹ is a bond; R⁴ is hydrogen; R⁶ is hydrogen; R¹ is a

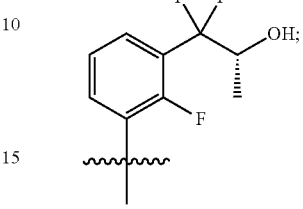

R² is —OR²ᵃ; R²ᵃ is methyl; R³ is C₃₋₄cycloalkyl optionally substituted with one R²⁰ᵇ; and R²⁰ᵇ is —CN. In embodiments of a compound of Formula (I'-2); R⁷ is C₁₋₆alkyl optionally substituted with one, two, or three R²⁰ᶜ; each R²⁰ᶜ is independently selected from halogen, C₂₋₆alkenyl, C₂₋₆alkynyl, C₃₋₁₀cycloalkyl, C₂₋₉heterocycloalkyl, C₆₋₁₀aryl, and C₁₋₉heteroaryl; L¹ is a bond; R⁴ is hydrogen; R⁶ is hydrogen; R¹ is a

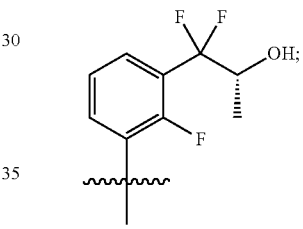

R² is —OR²ᵃ; R²ᵃ is methyl; R³ is C₃₋₄cycloalkyl optionally substituted with one, two, or three R²⁰ᵇ; and R²⁰ᵇ is —CN. In embodiments of a compound of Formula (I'-2); R⁷ is C₁₋₆alkyl optionally substituted with one, two, or three R²⁰ᶜ; each R²⁰ᶜ is independently selected from halogen, C₂₋₆alkenyl, C₂₋₆alkynyl, C₃₋₁₀cycloalkyl, C₂₋₉heterocycloalkyl, C₆₋₁₀aryl, and C₁₋₉heteroaryl; L¹ is a bond; R⁴ is hydrogen; R⁶ is hydrogen; R¹ is a

R² is —OR²ᵃ; R²ᵃ is methyl; R³ is C₃₋₄cycloalkyl optionally substituted with one, two, or three R²⁰ᵇ; and each R²⁰ᵇ is independently —CN or C₁₋₃haloalkyl. In embodiments of a compound of Formula (I'-2); R⁷ is C₁₋₆alkyl optionally substituted with one, two, or three R²⁰ᶜ; each R²⁰ᶜ is independently selected from halogen, C₂₋₆alkenyl, C₂₋₆alkynyl, C₃₋₁₀cycloalkyl, C₂₋₉heterocycloalkyl, C₆₋₁₀aryl, and C₁₋₉heteroaryl; L¹ is a bond; R⁴ is hydrogen; R⁶ is hydrogen; R¹ is a

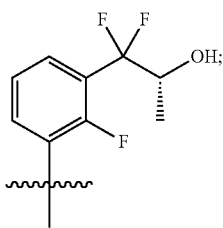 [SMILES: *c1cccc(C(F)(F)[C@@H](C)O)c1F]

$R^2$ is —$OR^{2a}$; $R^{2a}$ is methyl; $R^3$ is $C_{3-4}$cycloalkyl optionally substituted with one, two, or three $R^{20b}$; and each $R^{20b}$ is independently —CN or $C_{1-3}$haloalkyl. In embodiments of a compound of Formula (I'-2); $R^7$ is $C_{1-6}$alkyl optionally substituted with one, two, or three $R^{20c}$; each $R^{20c}$ is independently selected from halogen, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl; $L^1$ is a bond; $R^4$ is hydrogen; $R^6$ is hydrogen; $R^1$ is a

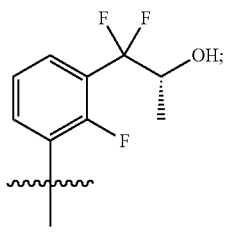 [SMILES: *c1cccc(C(F)(F)[C@@H](C)O)c1F]

$R^2$ is —$OR^{2a}$; $R^{2a}$ is methyl; $R^3$ is $C_{3-4}$cycloalkyl optionally substituted with one, two, or three $R^{20b}$; and each $R^{20b}$ is independently —CN or $C_{1-3}$ haloalkyl. In embodiments of a compound of Formula (I-2); $R^7$ is $C_{1-6}$alkyl optionally substituted with one, two, or three $R^{20c}$; each $R^{20c}$ is independently selected from halogen, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl; $L^1$ is a bond; $R^4$ is hydrogen; $R^6$ is hydrogen; $R^1$ is a

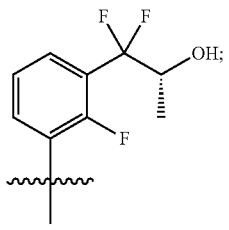 [SMILES: *c1cccc(C(F)(F)[C@@H](C)O)c1F]

$R^2$ is —$OR^{2a}$; $R^{2a}$ is methyl; $R^3$ is $C_{3-4}$cycloalkyl optionally substituted with one, two, or three $R^{20b}$; and each $R^{20b}$ is independently selected from amino; —CN; $C_{1-3}$alkyl; $C_{1-3}$alkoxy; $C_{1-3}$ haloalkyl; —OH; —$N(R^{24})C(O)R^{25}$; and —$C(O)N(R^{22})(R^{23})$.

In embodiments of a compound of Formula (I'-2); $R^7$ is $C_{1-6}$alkyl optionally substituted with one, two, or three $R^{20c}$; each $R^{20c}$ is independently selected from halogen, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl; $L^1$ is a bond; $R^4$ is hydrogen; $R^6$ is hydrogen; $R^1$ is a

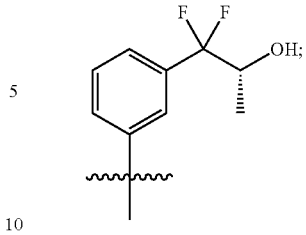

$R^2$ is —$OR^{2a}$; $R^{2a}$ is methyl; and $R^3$ is

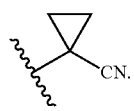

In embodiments of a compound of Formula (I'-2); $R^7$ is $C_{1-6}$alkyl optionally substituted with one, two, or three $R^{20c}$; each $R^{20c}$ is independently selected from halogen, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl; $L^1$ is a bond; $R^4$ is hydrogen; $R^6$ is hydrogen; $R^1$ is a

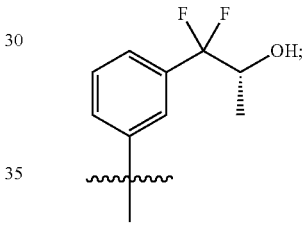

$R^2$ is —$OR^{2a}$; $R^{2a}$ is methyl; $R^3$ is cyclopropyl optionally substituted with one $R^{20b}$; and $R^{20b}$ is —CN. In embodiments of a compound of Formula (I'-2); $R^7$ is $C_{1-6}$alkyl optionally substituted with one, two, or three $R^{20c}$; each $R^{20c}$ is independently selected from halogen, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl; $L^1$ is a bond; $R^4$ is hydrogen; $R^6$ is hydrogen; $R^1$ is a

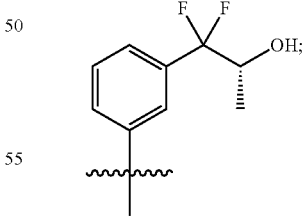

$R^2$ is —$OR^{2a}$; $R^{2a}$ is methyl; $R^3$ is $C_{3-4}$cycloalkyl optionally substituted with one $R^{20b}$; and $R^{20b}$ is —CN. In embodiments of a compound of Formula (I'-2); $R^7$ is $C_{1-6}$alkyl optionally substituted with one, two, or three $R^{20c}$; each $R^{20c}$ is independently selected from halogen, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl; $L^1$ is a bond; $R^4$ is hydrogen; $R^6$ is hydrogen; $R^1$ is a

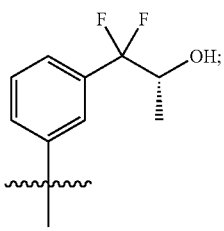 [SMILES: *c1cccc(C(F)(F)[C@@H](C)O)c1]

R² is —OR²ᵃ; R²ᵃ is methyl; R³ is $C_{3-4}$cycloalkyl optionally substituted with one, two, or three R²⁰ᵇ; and R²⁰ᵇ is —CN. In embodiments of a compound of Formula (I'-2); R⁷ is $C_{1-6}$alkyl optionally substituted with one, two, or three R²⁰ᶜ; each R²⁰ᶜ is independently selected from halogen, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl; L¹ is a bond; R⁴ is hydrogen; R⁶ is hydrogen; R¹ is

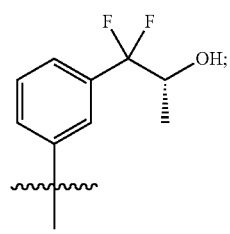 [SMILES: *c1cccc(C(F)(F)[C@@H](C)O)c1]

R² is —OR²ᵃ; R²ᵃ is methyl; R³ is $C_{3-4}$cycloalkyl optionally substituted with one, two, or three R²⁰ᵇ; and each R²⁰ᵇ is independently —CN or $C_{1-3}$haloalkyl. In embodiments of a compound of Formula (I'-2); R⁷ is $C_{1-6}$alkyl optionally substituted with one, two, or three R²⁰ᶜ; each R²⁰ᶜ is independently selected from halogen, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl; L¹ is a bond; R⁴ is hydrogen; R⁶ is hydrogen; R¹ is

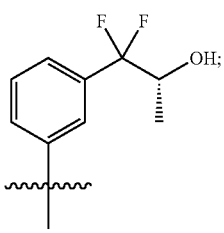 [SMILES: *c1cccc(C(F)(F)[C@@H](C)O)c1]

R² is —OR²ᵃ; R²ᵃ is methyl; R³ is $C_{3-4}$cycloalkyl optionally substituted with one, two, or three R²⁰ᵇ; and each R²⁰ᵇ is independently —CN or $C_{1-3}$haloalkyl. In embodiments of a compound of Formula (I'-2); R⁷ is $C_{1-6}$alkyl optionally substituted with one, two, or three R²⁰ᶜ; each R²⁰ᶜ is independently selected from halogen, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl; L¹ is a bond; R⁴ is hydrogen; R⁶ is hydrogen; R¹ is a

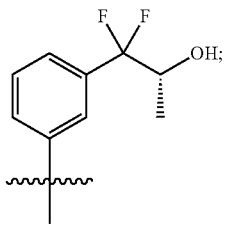 [SMILES: *c1cccc(C(F)(F)[C@@H](C)O)c1]

R² is —OR²ᵃ; R²ᵃ is methyl; R³ is $C_{3-4}$cycloalkyl optionally substituted with one, two, or three R²⁰ᵇ; and each R²⁰ᵇ is independently —CN or $C_{1-3}$haloalkyl. In embodiments of a compound of Formula (I'-2); R⁷ is $C_{1-6}$alkyl optionally substituted with one, two, or three R²⁰ᶜ; each R²⁰ᶜ is independently selected from halogen, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl; L¹ is a bond; R⁴ is hydrogen; R⁶ is hydrogen; R¹ is a

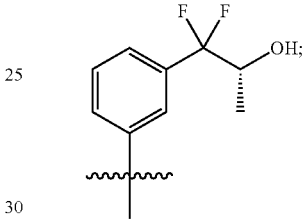

R² is —OR²ᵃ; R²ᵃ is methyl; R³ is $C_{3-4}$cycloalkyl optionally substituted with one, two, or three R²⁰ᵇ; and each R²⁰ᵇ is independently selected from amino; —CN; $C_{1-3}$alkyl; $C_{1-3}$alkoxy; $C_{1-3}$ haloalkyl; —OH; —N(R²⁴)C(O)R²¹; and —C(O)N(R²²)(R²³).

₃haloalkyl; —OH; —N(R²⁴)C(O)R²¹; and —C(O)N(R²²) (R²³).

In embodiments of a compound of Formula (I'-2); R⁷ is $C_{1-6}$alkyl optionally substituted with one, two, or three R²⁰ᶜ; each R²⁰ᶜ is independently selected from halogen, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl; L¹ is a bond; R⁴ is hydrogen; R⁶ is hydrogen; R¹ is a phenyl substituted with one or more R¹⁰; each R¹⁰ is independently selected from halogen and $C_{1-4}$alkyl optionally substituted with one, two, or three R²⁰ᵈ; each R²⁰ᵈ is independently selected from halogen and —OH; R² is —OR²ᵃ; R²ᵃ is methyl; and R³ is

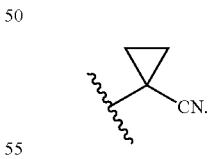

In embodiments of a compound of Formula (I'-2); R⁷ is $C_{1-6}$alkyl optionally substituted with one, two, or three R²⁰ᶜ; each R²⁰ᶜ is independently selected from halogen, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl; L¹ is a bond; R⁴ is hydrogen; R⁶ is hydrogen; R¹ is a phenyl substituted with one or more R¹⁰; each R¹⁰ is independently selected from halogen and $C_{1-4}$alkyl optionally substituted with one, two, or three R²⁰ᵈ; each R²⁰ᵈ is independently selected from halogen and —OH; R² is —OR²ᵃ; R²ᵃ is methyl; R³ is cyclopropyl optionally substituted with one R²⁰ᵇ; and R²⁰ᵇ is —CN. In embodiments of a compound of Formula (I'-2); $R^7$ is $C_{1-6}$alkyl optionally substituted with one, two, or three $R^{20c}$; each $R^{20c}$ is independently selected from halogen, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl; $L^1$ is a bond; $R^4$ is hydrogen; $R^6$ is hydrogen; $R^1$ is a phenyl substituted with one or more $R^{10}$; each $R^{10}$ is independently selected from halogen and $C_{1-4}$alkyl optionally substituted with one, two, or three $R^{20d}$; each $R^{20d}$ is independently selected from halogen and —OH; $R^2$ is —OR$^{2a}$; $R^{2a}$ is methyl; $R^3$ is $C_{3-4}$cycloalkyl optionally substituted with one $R^{20b}$; and $R^{20b}$ is —CN. In embodiments of a compound of Formula (I'-2); $R^7$ is $C_{1-6}$alkyl optionally substituted with one, two, or three $R^{20c}$; each $R^{20c}$ is independently selected from halogen, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl; $L^1$ is a bond; $R^4$ is hydrogen; $R^6$ is hydrogen; $R^1$ is a phenyl substituted with one or more $R^{10}$; each $R^{10}$ is independently selected from halogen and $C_{1-4}$alkyl optionally substituted with one, two, or three $R^{20d}$; each $R^{20d}$ is independently selected from halogen and —OH; $R^2$ is —OR$^{2a}$; $R^{2a}$ is methyl; $R^3$ is $C_{3-4}$cycloalkyl optionally substituted with one, two, or three $R^{20b}$; and $R^{20b}$ is —CN. In embodiments of a compound of Formula (I'-2); $R^7$ is $C_{1-6}$alkyl optionally substituted with one, two, or three $R^{20c}$; each $R^{20c}$ is independently selected from halogen, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl; $L^1$ is a bond; $R^4$ is hydrogen; $R^6$ is hydrogen; $R^1$ is a phenyl substituted with one or more $R^{10}$; each $R^{10}$ is independently selected from halogen and $C_{1-4}$alkyl optionally substituted with one, two, or three $R^{20d}$; each $R^{20d}$ is independently selected from halogen and —OH; $R^2$ is —OR$^{2a}$; $R^{2a}$ is methyl; $R^3$ is $C_{3-4}$cycloalkyl optionally substituted with one, two, or three $R^{20b}$; and each $R^{20b}$ is independently —CN or $C_{1-3}$haloalkyl. In embodiments of a compound of Formula (I'-2); $R^7$ is $C_{1-6}$alkyl optionally substituted with one, two, or three $R^{20c}$; each $R^{20c}$ is independently selected from halogen, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl; $L^1$ is a bond; $R^4$ is hydrogen; $R^6$ is hydrogen; $R^1$ is a phenyl substituted with one or more $R^{10}$; each $R^{10}$ is independently selected from halogen and $C_{1-4}$alkyl optionally substituted with one, two, or three $R^{20d}$; each $R^{20d}$ is independently selected from halogen and —OH; $R^2$ is —OR$^{2a}$; $R^{2a}$ is methyl; $R^3$ is $C_{3-4}$cycloalkyl optionally substituted with one, two, or three $R^{20b}$; and each $R^{20b}$ is independently —CN or $C_{1-3}$haloalkyl. In embodiments of a compound of Formula (I'-2); $R^7$ is $C_{1-6}$alkyl optionally substituted with one, two, or three $R^{20c}$; each $R^{20c}$ is independently selected from halogen, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl; $L^1$ is a bond; $R^4$ is hydrogen; $R^6$ is hydrogen; $R^1$ is a phenyl substituted with one or more $R^{10}$; each $R^{10}$ is independently selected from halogen and $C_{1-4}$alkyl optionally substituted with one, two, or three $R^{20d}$; each $R^{20d}$ is independently selected from halogen and —OH; $R^2$ is —OR$^{2a}$; $R^{2a}$ is methyl; $R^3$ is $C_{3-4}$cycloalkyl optionally substituted with one, two, or three $R^{20b}$; and each $R^{20b}$ is independently selected from amino; —CN; $C_{1-3}$alkyl; $C_{1-3}$alkoxy; $C_{1-3}$haloalkyl; —OH; —N(R$^{24}$)C(O)R$^{21}$; and —C(O)N(R$^{22}$)(R$^{23}$).

In embodiments of a compound of Formula (I'-2); $R^7$ is $C_{1-6}$alkyl optionally substituted with one, two, or three $R^{20c}$; each $R^{20c}$ is independently selected from halogen, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl; $L^1$ is a bond; $R^4$ is hydrogen; $R^6$ is hydrogen; $R^1$ is a phenyl substituted with one or more $R^{10}$; each $R^{10}$ is independently selected from halogen and $C_{1-4}$alkyl optionally substituted with one, two, or three $R^{20d}$; each $R^{20d}$ is independently selected from halogen, —OH, $C_{2-5}$heterocycloalkyl optionally substituted with one, two, or three $C_{1-6}$alkyl (e.g., methyl, ethyl, or propyl), and —OR$^{21}$, wherein $R^{21}$ is $C_{2-5}$heterocycloalkyl optionally substituted with one, two, or three $C_{1-6}$alkyl (e.g., methyl, ethyl, propyl, or butyl); $R^2$ is —OR$^{2a}$; $R^{2a}$ is methyl; and $R^3$ is

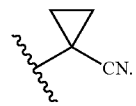

In embodiments of a compound of Formula (I'-2); $R^7$ is $C_{1-6}$alkyl optionally substituted with one, two, or three $R^{20c}$; each $R^{20c}$ is independently selected from halogen, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl; $L^1$ is a bond; $R^4$ is hydrogen; $R^6$ is hydrogen; $R^1$ is a phenyl substituted with one or more $R^{10}$; each $R^{10}$ is independently selected from halogen and $C_{1-4}$alkyl optionally substituted with one, two, or three $R^{20d}$; each $R^{20d}$ is independently selected from halogen, —OH, $C_{2-5}$heterocycloalkyl optionally substituted with one, two, or three $C_{1-6}$alkyl (e.g., methyl, ethyl, or propyl), and —OR$^{21}$, wherein $R^{21}$ is $C_{2-5}$heterocycloalkyl optionally substituted with one, two, or three $C_{1-6}$alkyl (e.g., methyl, ethyl, propyl, or butyl); $R^3$ is cyclopropyl optionally substituted with one $R^{20b}$; and $R^{20b}$ is —CN. In embodiments of a compound of Formula (I'-2); $R^7$ is $C_{1-6}$alkyl optionally substituted with one, two, or three $R^{20c}$; each $R^{20c}$ is independently selected from halogen, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl; $L^1$ is a bond; $R^4$ is hydrogen; $R^6$ is hydrogen; $R^1$ is a phenyl substituted with one or more $R^{10}$; each $R^{10}$ is independently selected from halogen and $C_{1-4}$alkyl optionally substituted with one, two, or three $R^{20d}$; each $R^{20d}$ is independently selected from halogen, —OH, $C_{2-5}$heterocycloalkyl optionally substituted with one, two, or three $C_{1-6}$alkyl (e.g., methyl, ethyl, or propyl), and —OR$^{21}$, wherein $R^{21}$ is $C_{2-5}$heterocycloalkyl optionally substituted with one, two, or three $C_{1-6}$alkyl (e.g., methyl, ethyl, propyl, or butyl); $R^2$ is —OR$^{2a}$; $R^{2a}$ is methyl; $R^3$ is $C_{3-4}$cycloalkyl optionally substituted with one $R^{20b}$; and $R^{20b}$ is —CN. In embodiments of a compound of Formula (I'-2); $R^7$ is $C_{1-6}$alkyl optionally substituted with one, two, or three $R^{20c}$; each $R^{20c}$ is independently selected from halogen, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl; $L^1$ is a bond; $R^4$ is hydrogen; $R^6$ is hydrogen; $R^1$ is a phenyl substituted with one or more $R^{10}$; each $R^{10}$ is independently selected from halogen and $C_{1-4}$alkyl optionally substituted with one, two, or three $R^{20d}$; each $R^{20d}$ is independently selected from halogen, —OH, $C_{2-5}$heterocycloalkyl optionally substituted with one, two, or three $C_{1-6}$alkyl (e.g., methyl, ethyl, or propyl), and —$OR^{21}$, wherein $R^{21}$ is $C_{2-5}$heterocycloalkyl optionally substituted with one, two, or three $C_{1-6}$alkyl (e.g., methyl, ethyl, propyl, or butyl); $R^2$ is —$OR^{2a}$; $R^{2a}$ is methyl; $R^3$ is $C_{3-4}$cycloalkyl optionally substituted with one, two, or three $R^{20b}$; and $R^{20b}$ is —CN. In embodiments of a compound of Formula (I'-2); $R^7$ is $C_{1-6}$alkyl optionally substituted with one, two, or three $R^{20c}$; each $R^{20c}$ is independently selected from halogen, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl; $L^1$ is a bond; $R^4$ is hydrogen; $R^6$ is hydrogen; $R^1$ is a phenyl substituted with one or more $R^{10}$; each $R^{10}$ is independently selected from halogen and $C_{1-4}$alkyl optionally substituted with one, two, or three $R^{20d}$; each $R^{20d}$ is independently selected from halogen, —OH, $C_{2-5}$heterocycloalkyl optionally substituted with one, two, or three $C_{1-6}$alkyl (e.g., methyl, ethyl, or propyl), and —$OR^{21}$, wherein $R^{21}$ is $C_{2-5}$heterocycloalkyl optionally substituted with one, two, or three $C_{1-6}$alkyl (e.g., methyl, ethyl, propyl, or butyl); $R^2$ is —$OR^{2a}$; $R^{2a}$ is methyl; $R^3$ is $C_{3-4}$cycloalkyl optionally substituted with one, two, or three $R^{20b}$; and each $R^{20b}$ is independently —CN or $C_{1-3}$haloalkyl. In embodiments of a compound of Formula (I'-2); $R^7$ is $C_{1-6}$alkyl optionally substituted with one, two, or three $R^{20c}$; each $R^{20c}$ is independently selected from halogen, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl; $L^1$ is a bond; $R^4$ is hydrogen; $R^6$ is hydrogen; $R^1$ is a phenyl substituted with one or more $R^{10}$; each $R^{10}$ is independently selected from halogen and $C_{1-4}$alkyl optionally substituted with one, two, or three $R^{20d}$; each $R^{20d}$ is independently selected from halogen, —OH, $C_{2-5}$heterocycloalkyl optionally substituted with one, two, or three $C_{1-6}$alkyl (e.g., methyl, ethyl, or propyl), and —$OR^{21}$, wherein $R^{21}$ is $C_{2-5}$heterocycloalkyl optionally substituted with one, two, or three $C_{1-6}$alkyl (e.g., methyl, ethyl, propyl, or butyl); $R^2$ is —$OR^{2a}$; $R^{2a}$ is methyl; $R^3$ is $C_{3-4}$cycloalkyl optionally substituted with one, two, or three $R^{20b}$; and each $R^{20b}$ is independently —CN or $C_{1-3}$haloalkyl. In embodiments of a compound of Formula (I'-2); $R^7$ is $C_{1-6}$alkyl optionally substituted with one, two, or three $R^{20c}$; each $R^{20c}$ is independently selected from halogen, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl; $L^1$ is a bond; $R^4$ is hydrogen; $R^6$ is hydrogen; $R^1$ is a phenyl substituted with one or more $R^{10}$; each $R^{10}$ is independently selected from halogen and $C_{1-4}$alkyl optionally substituted with one, two, or three $R^{20d}$; each $R^{20d}$ is independently selected from halogen, —OH, $C_{2-5}$heterocycloalkyl optionally substituted with one, two, or three $C_{1-6}$alkyl (e.g., methyl, ethyl, or propyl), and —$OR^{21}$, wherein $R^{21}$ is $C_{2-5}$heterocycloalkyl optionally substituted with one, two, or three $C_{1-6}$alkyl (e.g., methyl, ethyl, propyl, or butyl); $R^2$ is —$OR^{2a}$; $R^{2a}$ is methyl; $R^3$ is $C_{3-4}$cycloalkyl optionally substituted with one, two, or three $R^{20b}$; and each $R^{20b}$ is independently selected from amino; —CN; $C_{1-3}$alkyl; $C_{1-3}$alkoxy; $C_{1-3}$haloalkyl; —OH; —$N(R^{24})C(O)R^{25}$; and —$C(O)N(R^{22})(R^{23})$.

In embodiments of a compound of Formula (I'-2); $R^7$ is $C_{1-6}$alkyl optionally substituted with one, two, or three $R^{20c}$; each $R^{20c}$ is independently selected from halogen, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl; $L^1$ is a bond; $R^4$ is hydrogen; $R^6$ is hydrogen; $R^1$ is a 6-10 membered aryl ring substituted with one or more $R^{10}$; each $R^{10}$ is independently selected from halogen and $C_{1-4}$alkyl optionally substituted with one, two, or three $R^{20d}$; each $R^{20d}$ is independently selected from halogen, —OH, $C_{2-5}$heterocycloalkyl optionally substituted with one, two, or three $C_{1-6}$alkyl (e.g., methyl, ethyl, or propyl), and —$OR^{21}$, wherein $R^{21}$ is $C_{2-5}$heterocycloalkyl optionally substituted with one, two, or three $C_{1-6}$alkyl (e.g., methyl, ethyl, propyl, or butyl); $R^2$ is —$OR^{2a}$; $R^{2a}$ is methyl; and $R^3$ is In embodiments of a compound of Formula (I'-2); $R^7$ is $C_{1-6}$alkyl optionally substituted with one, two, or three $R^{20c}$; each $R^{20c}$ is independently selected from halogen, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl; $L^1$ is a bond; $R^4$ is hydrogen; $R^6$ is hydrogen; $R^1$ is a 6-10 membered aryl ring substituted with one or more $R^{10}$; each $R^{10}$ is independently selected from halogen and $C_{1-4}$alkyl optionally substituted with one, two, or three $R^{20d}$; each $R^{20d}$ is independently selected from halogen, —OH, $C_{2-5}$heterocycloalkyl optionally substituted with one, two, or three $C_{1-6}$alkyl (e.g., methyl, ethyl, or propyl), and —$OR^{21}$, wherein $R^{21}$ is $C_{2-5}$heterocycloalkyl optionally substituted with one, two, or three $C_{1-6}$alkyl (e.g., methyl, ethyl, propyl, or butyl); $R^3$ is cyclopropyl optionally substituted with one $R^{20b}$; and $R^{20b}$ is —CN. In embodiments of a compound of Formula (I'-2); $R^7$ is $C_{1-6}$alkyl optionally substituted with one, two, or three $R^{20c}$; each $R^{20c}$ is independently selected from halogen, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl; $L^1$ is a bond; $R^4$ is hydrogen; $R^6$ is hydrogen; $R^1$ is a 6-10 membered aryl ring substituted with one or more $R^{10}$; each $R^{10}$ is independently selected from halogen and $C_{1-4}$alkyl optionally substituted with one, two, or three $R^{20d}$; each $R^{20d}$ is independently selected from halogen, —OH, $C_{2-5}$heterocycloalkyl optionally substituted with one, two, or three $C_{1-6}$alkyl (e.g., methyl, ethyl, or propyl), and —$OR^{21}$, wherein $R^{21}$ is $C_{2-5}$heterocycloalkyl optionally substituted with one, two, or three $C_{1-6}$alkyl (e.g., methyl, ethyl, propyl, or butyl); $R^2$ is —$OR^{2a}$; $R^{2a}$ is methyl; $R^3$ is $C_{3-4}$cycloalkyl optionally substituted with one $R^{20b}$; and $R^{20b}$ is —CN. In embodiments of a compound of Formula (I'-2); $R^7$ is $C_{1-6}$alkyl optionally substituted with one, two, or three $R^{20c}$; each $R^{20c}$ is independently selected from halogen, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl; $L^1$ is a bond; $R^4$ is hydrogen; $R^6$ is hydrogen; $R^1$ is a 6-10 membered aryl ring substituted with one or more $R^{10}$; each $R^{10}$ is independently selected from halogen and $C_{1-4}$alkyl optionally substituted with one, two, or three $R^{20d}$; each $R^{20d}$ is independently selected from halogen, —OH, $C_{2-5}$heterocycloalkyl optionally substituted with one, two, or three $C_{1-6}$alkyl (e.g., methyl, ethyl, or propyl), and —$OR^{21}$, wherein $R^{21}$ is $C_{2-5}$heterocycloalkyl optionally substituted with one, two, or three $C_{1-6}$alkyl (e.g., methyl, ethyl, propyl, or butyl); $R^2$ is —$OR^{2a}$; $R^{2a}$ is methyl; $R^3$ is $C_{3-4}$cycloalkyl optionally substituted with one, two, or three $R^{20b}$; and $R^{20b}$ is —CN. In embodiments of a compound of Formula (I'-2); $R^7$ is $C_{1-6}$alkyl optionally substituted with one, two, or three $R^{20c}$; each $R^{20c}$ is independently selected from halogen, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl; $L^1$ is a bond; $R^4$ is hydrogen; $R^6$ is hydrogen; $R^1$ is a 6-10 membered aryl ring substituted with one or more $R^{10}$; each $R^{10}$ is independently selected from halogen and $C_{1-4}$alkyl optionally substituted with one, two, or three $R^{20d}$; each $R^{20d}$ is independently selected from halogen, —OH, $C_{2-5}$heterocycloalkyl optionally substituted with one, two, or three $C_{1-6}$alkyl (e.g., methyl, ethyl, or propyl), and —$OR^{21}$, wherein $R^{21}$ is $C_{2-5}$heterocycloalkyl optionally substituted with one, two, or three $C_{1-6}$alkyl (e.g., methyl, ethyl, propyl, or butyl); $R^2$ is —$OR^{2a}$; $R^{2a}$ is methyl; $R^3$ is $C_{3-4}$cycloalkyl optionally substituted with one, two, or three $R^{20b}$; and each $R^{20b}$ is independently —CN or $C_{1-3}$haloalkyl. In embodiments of a compound of Formula (I'-2); $R^7$ is $C_{1-6}$alkyl optionally substituted with one, two, or three $R^{20c}$; each $R^{20c}$ is independently selected from halogen, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl; $L^1$ is a bond; $R^4$ is hydrogen; $R^6$ is hydrogen; $R^1$ is a 6-10 membered aryl ring substituted with one or more $R^{10}$; each $R^{10}$ is independently selected from halogen and $C_{1-4}$alkyl optionally substituted with one, two, or three $R^{20d}$; each $R^{20d}$ is independently selected from halogen, —OH, $C_{2-5}$heterocycloalkyl optionally substituted with one, two, or three $C_{1-6}$alkyl (e.g., methyl, ethyl, or propyl), and —$OR^{21}$, wherein $R^{21}$ is $C_{2-5}$heterocycloalkyl optionally substituted with one, two, or three $C_{1-6}$alkyl (e.g., methyl, ethyl, propyl, or butyl); $R^2$ is —$OR^{2a}$; $R^{2a}$ is methyl; $R^3$ is $C_{3-4}$cycloalkyl optionally substituted with one, two, or three $R^{20b}$; and each $R^{20b}$ is independently —CN or $C_{1-3}$haloalkyl. In embodiments of a compound of Formula (I'-2); $R^7$ is $C_{1-6}$alkyl optionally substituted with one, two, or three $R^{20c}$; each $R^{20c}$ is independently selected from halogen, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl; $L^1$ is a bond; $R^4$ is hydrogen; $R^6$ is hydrogen; $R^1$ is a 6-10 membered aryl ring substituted with one or more $R^{10}$; each $R^{10}$ is independently selected from halogen and $C_{1-4}$alkyl optionally substituted with one, two, or three $R^{20d}$; each $R^{20d}$ is independently selected from halogen, —OH, $C_{2-5}$heterocycloalkyl optionally substituted with one, two, or three $C_{1-6}$alkyl (e.g., methyl, ethyl, or propyl), and —$OR^{21}$, wherein $R^{21}$ is $C_{2-5}$heterocycloalkyl optionally substituted with one, two, or three $C_{1-6}$alkyl (e.g., methyl, ethyl, propyl, or butyl); $R^2$ is —$OR^{2a}$; $R^{2a}$ is methyl; $R^3$ is $C_{3-4}$cycloalkyl optionally substituted with one, two, or three $R^{20b}$; and each $R^{20b}$ is independently —CN or $C_{1-3}$haloalkyl. In embodiments of a compound of Formula (I'-2); $R^7$ is $C_{1-6}$alkyl optionally substituted with one, two, or three $R^{20c}$; each $R^{20c}$ is independently selected from halogen, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl; $L^1$ is a bond; $R^4$ is hydrogen; $R^6$ is hydrogen; $R^1$ is a 6-10 membered aryl ring substituted with one or more $R^{10}$; each $R^{10}$ is independently selected from halogen and $C_{1-4}$alkyl optionally substituted with one, two, or three $R^{20d}$; each $R^{20d}$ is independently selected from halogen, —OH, $C_{2-5}$heterocycloalkyl optionally substituted with one, two, or three $C_{1-6}$alkyl (e.g., methyl, ethyl, or propyl), and —$OR^{21}$, wherein $R^{21}$ is $C_{2-5}$heterocycloalkyl optionally substituted with one, two, or three $C_{1-6}$alkyl (e.g., methyl, ethyl, propyl, or butyl); $R^2$ is —$OR^{2a}$; $R^{2a}$ is methyl; $R^3$ is $C_{3-4}$cycloalkyl optionally substituted with one, two, or three $R^{20b}$; and each $R^{20b}$ is independently selected from amino; —CN; $C_{1-3}$alkyl; $C_{1-3}$alkoxy; $C_{1-3}$haloalkyl; —OH; —$N(R^{24})C(O)R^{25}$; and —$C(O)N(R^{22})(R^{23})$.

In embodiments of a compound of Formula (I-2); $R^7$ is $C_{1-6}$alkyl optionally substituted with one, two, or three $R^{20c}$; each $R^{20c}$ is independently selected from halogen, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl; $L^1$ is a bond; $R^4$ is hydrogen; $R^5$ is methyl; $R^6$ is hydrogen; $R^1$ is

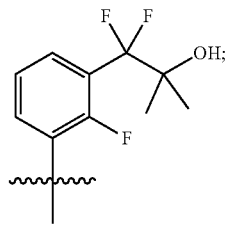 [SMILES: *c1cccc(C(F)(F)C(C)(C)O)c1F]

$R^2$ is —$OR^{2a}$; $R^{2a}$ is methyl; and $R^3$ is

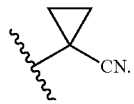

In embodiments of a compound of Formula (I-2); $R^7$ is $C_{1-6}$alkyl optionally substituted with one, two, or three $R^{20c}$; each $R^{20c}$ is independently selected from halogen, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl; $L^1$ is a bond; $R^4$ is hydrogen; $R^5$ is methyl; $R^6$ is hydrogen; $R^1$ is a

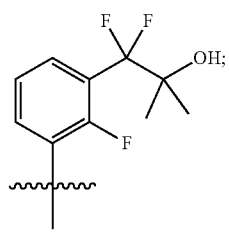 [SMILES: *c1cccc(C(F)(F)C(C)(C)O)c1F]

$R^2$ is —$OR^{2a}$; $R^{2a}$ is methyl; $R^3$ is cyclopropyl optionally substituted with one $R^{20b}$; and $R^{20b}$ is —CN. In embodiments of a compound of Formula (I-2); $R^7$ is $C_{1-6}$alkyl optionally substituted with one, two, or three $R^{20c}$; each $R^{20c}$ is independently selected from halogen, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl; $L^1$ is a bond; $R^4$ is hydrogen; $R^5$ is methyl; $R^6$ is hydrogen; $R^1$ is a

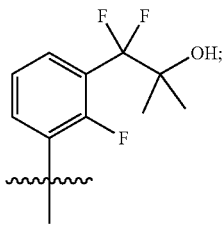 [SMILES: *c1cccc(C(F)(F)C(C)(C)O)c1F]

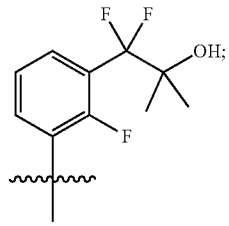 [SMILES: *c1cccc(C(F)(F)C(C)(C)O)c1F]

$R^2$ is —$OR^{2a}$; $R^{2a}$ is methyl; $R^3$ is $C_{3-4}$cycloalkyl optionally substituted with one $R^{20b}$; and $R^{20b}$ is —CN. In embodiments of a compound of Formula (I-2); $R^7$ is $C_{1-6}$alkyl optionally substituted with one, two, or three $R^{20c}$; each $R^{20c}$ is independently selected from halogen, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl; $L^1$ is a bond; $R^4$ is hydrogen; $R^5$ is methyl; $R^6$ is hydrogen; $R^1$ is a $R^2$ is —$OR^{2a}$; $R^{2a}$ is methyl; $R^3$ is $C_{3-4}$cycloalkyl optionally substituted with one, two, or three $R^{20b}$; and each $R^{20b}$ is independently —CN or $C_{1-3}$haloalkyl. In embodiments of a compound of Formula (I-2); $R^7$ is $C_{1-6}$alkyl optionally substituted with one, two, or three $R^{20c}$; each $R^{20c}$ is independently selected from halogen, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl; $L^1$ is a bond; $R^4$ is hydrogen; $R^5$ is methyl; $R^6$ is hydrogen; $R^1$ is a

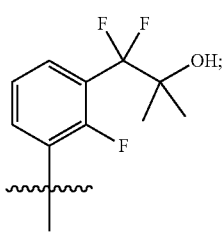 [SMILES: *c1cccc(C(F)(F)C(C)(C)O)c1F]

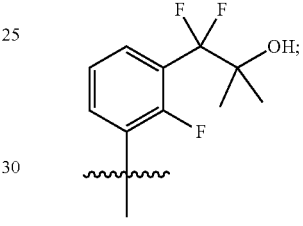

$R^2$ is —$OR^{2a}$; $R^{2a}$ is methyl; $R^3$ is $C_{3-4}$cycloalkyl optionally substituted with one, two, or three $R^{20b}$; and $R^{20b}$ is —CN. In embodiments of a compound of Formula (I-2); $R^7$ is $C_{1-6}$alkyl optionally substituted with one, two, or three $R^{20c}$; each $R^{20c}$ is independently selected from halogen, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl; $L^1$ is a bond; $R^4$ is hydrogen; $R^5$ is methyl; $R^6$ is hydrogen; $R^1$ is a $R^2$ is —$OR^{2a}$; $R^{2a}$ is methyl; $R^3$ is $C_{3-4}$cycloalkyl optionally substituted with one, two, or three $R^{20b}$; and each $R^{20b}$ is independently —CN or $C_{1-3}$haloalkyl. In embodiments of a compound of Formula (I-2); $R^7$ is $C_{1-6}$alkyl optionally substituted with one, two, or three $R^{20c}$; each $R^{20c}$ is independently selected from halogen, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl; $L^1$ is a bond; $R^4$ is hydrogen; $R^5$ is methyl; $R^6$ is hydrogen; $R^1$ is a

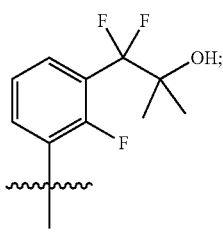 [SMILES: *c1cccc(C(F)(F)C(C)(C)O)c1F]

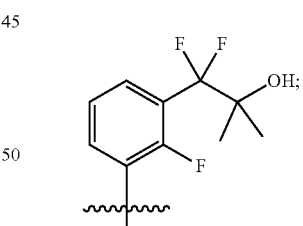

$R^2$ is —$OR^{2a}$; $R^{2a}$ is methyl; $R^3$ is $C_{3-4}$cycloalkyl optionally substituted with one, two, or three $R^{20b}$; and each $R^{20b}$ is independently —CN or $C_{1-3}$haloalkyl. In embodiments of a compound of Formula (I-2); $R^7$ is $C_{1-6}$alkyl optionally substituted with one, two, or three $R^{20c}$; each $R^{20c}$ is independently selected from halogen, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl; $L^1$ is a bond; $R^4$ is hydrogen; $R^5$ is methyl; $R^6$ is hydrogen; $R^1$ is a $R^2$ is —$OR^{2a}$; $R^{2a}$ is methyl; $R^3$ is $C_{3-4}$cycloalkyl optionally substituted with one, two, or three $R^{20b}$; and each $R^{20b}$ is independently selected from amino; —CN; $C_{1-3}$alkyl; $C_{1-3}$alkoxy; $C_{1-3}$ haloalkyl; —OH; —$N(R^{24})C(O)R^{25}$; and —$C(O)N(R^{22})(R^{23})$.

In embodiments of a compound of Formula (I-2); $R^7$ is $C_{1-6}$alkyl optionally substituted with one, two, or three $R^{20c}$; each $R^{20c}$ is independently selected from halogen, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl; $L^1$ is a bond; $R^4$ is hydrogen; $R^5$ is methyl; $R^6$ is hydrogen; $R^1$ is a

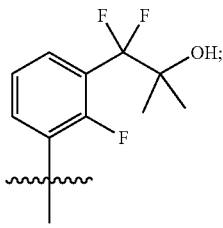 [SMILES: *c1cccc(C(F)(F)C(C)(C)O)c1F]

$R^2$ is —$OR^{2a}$; $R^{2a}$ is methyl; and $R^3$ is

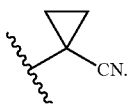

In embodiments of a compound of Formula (I-2); $R^7$ is $C_{1-6}$alkyl optionally substituted with one, two, or three $R^{20c}$; each $R^{20c}$ is independently selected from halogen, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl; $L^1$ is a bond; $R^4$ is hydrogen; $R^5$ is methyl; $R^6$ is hydrogen; $R^1$ is a

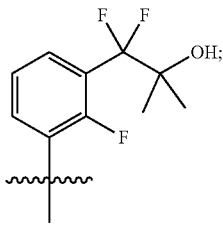 [SMILES: *c1cccc(C(F)(F)C(C)(C)O)c1F]

$R^2$ is —$OR^{2a}$; $R^{2a}$ is methyl; $R^3$ is cyclopropyl optionally substituted with one $R^{20b}$; and $R^{20b}$ is —CN. In embodiments of a compound of Formula (I-2); $R^7$ is $C_{1-6}$alkyl optionally substituted with one, two, or three $R^{20c}$; each $R^{20c}$ is independently selected from halogen, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl; $L^1$ is a bond; $R^4$ is hydrogen; $R^5$ is methyl; $R^6$ is hydrogen; $R^1$ is a

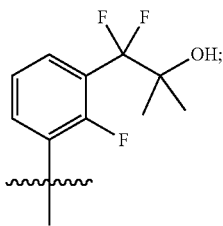 [SMILES: *c1cccc(C(F)(F)C(C)(C)O)c1F]

$R^2$ is —$OR^{2a}$; $R^{2a}$ is methyl; $R^3$ is $C_{3-4}$cycloalkyl optionally substituted with one $R^{20b}$; and $R^{20b}$ is —CN. In embodiments of a compound of Formula (I-2); $R^7$ is $C_{1-6}$alkyl optionally substituted with one, two, or three $R^{20c}$; each $R^{20c}$ is independently selected from halogen, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl; $L^1$ is a bond; $R^4$ is hydrogen; $R^5$ is methyl; $R^6$ is hydrogen; $R^1$ is a

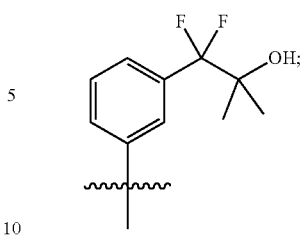

$R^2$ is —$OR^{2a}$; $R^{2a}$ is methyl; $R^3$ is $C_{3-4}$cycloalkyl optionally substituted with one, two, or three $R^{20b}$; and $R^{20b}$ is —CN. In embodiments of a compound of Formula (I-2); $R^7$ is $C_{1-6}$alkyl optionally substituted with one, two, or three $R^{20c}$; each $R^{20c}$ is independently selected from halogen, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl; $L^1$ is a bond; $R^4$ is hydrogen; $R^5$ is methyl; $R^6$ is hydrogen; $R^1$ is a

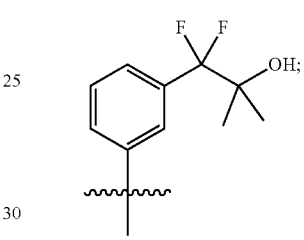

$R^2$ is —$OR^{2a}$; $R^{2a}$ is methyl; $R^3$ is $C_{3-4}$cycloalkyl optionally substituted with one, two, or three $R^{20b}$; and each $R^{20b}$ is independently —CN or $C_{1-3}$haloalkyl. In embodiments of a compound of Formula (I-2); $R^7$ is $C_{1-6}$alkyl optionally substituted with one, two, or three $R^{20c}$; each $R^{20c}$ is independently selected from halogen, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl; $L^1$ is a bond; $R^4$ is hydrogen; $R^5$ is methyl; $R^6$ is hydrogen; $R^1$ is a

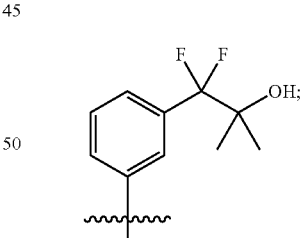

$R^2$ is —$OR^{2a}$; $R^{2a}$ is methyl; $R^3$ is $C_{3-4}$cycloalkyl optionally substituted with one, two, or three $R^{20b}$; and each $R^{20b}$ is independently —CN or $C_{1-3}$haloalkyl. In embodiments of a compound of Formula (I-2); $R^7$ is $C_{1-6}$alkyl optionally substituted with one, two, or three $R^{20c}$; each $R^{20c}$ is independently selected from halogen, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl; $L^1$ is a bond; $R^4$ is hydrogen; $R^5$ is methyl; $R^6$ is hydrogen; $R^1$ is

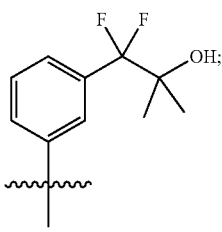 [SMILES: *c1cccc(C(F)(F)C(C)(C)O)c1]

R² is —OR²ᵃ; R²ᵃ is methyl; R³ is $C_{3-4}$cycloalkyl optionally substituted with one, two, or three R²⁰ᵇ; and each R²⁰ᵇ is independently —CN or $C_{1-3}$haloalkyl. In embodiments of a compound of Formula (I-2); R⁷ is $C_{1-6}$alkyl optionally substituted with one, two, or three R²⁰ᶜ; each R²⁰ᶜ is independently selected from halogen, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl; L¹ is a bond; R⁴ is hydrogen; R⁵ is methyl; R⁶ is hydrogen; R¹ is a

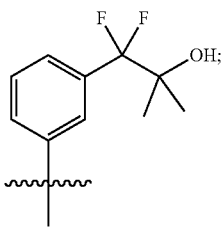 [SMILES: *c1cccc(C(F)(F)C(C)(C)O)c1]

R² is —OR²ᵃ; R²ᵃ is methyl; R³ is $C_{3-4}$cycloalkyl optionally substituted with one, two, or three R²⁰ᵇ; and each R²⁰ᵇ is independently selected from amino; —CN; $C_{1-3}$alkyl; $C_{1-3}$alkoxy; $C_{1-3}$ haloalkyl; —OH; —N(R²⁴)C(O)R²¹; and —C(O)N(R²²)(R²³).

In embodiments of a compound of Formula (I-2); R⁷ is $C_{1-6}$alkyl optionally substituted with one, two, or three R²⁰ᶜ; each R²⁰ᶜ is independently selected from halogen, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl; L¹ is a bond; R⁴ is hydrogen; R⁵ is methyl; R⁶ is hydrogen; R¹ is a

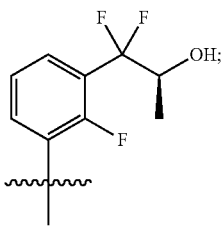 [SMILES: *c1cccc(C(F)(F)[C@H](C)O)c1F]

R² is —OR²ᵃ; R²ᵃ is methyl; and R³ is

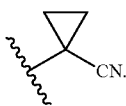 [SMILES: *C1(C#N)CC1]

In embodiments of a compound of Formula (I-2); R⁷ is $C_{1-6}$alkyl optionally substituted with one, two, or three R²⁰ᶜ; each R²⁰ᶜ is independently selected from halogen, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl; L¹ is a bond; R⁴ is hydrogen; R⁵ is methyl; R⁶ is hydrogen; R¹ is a

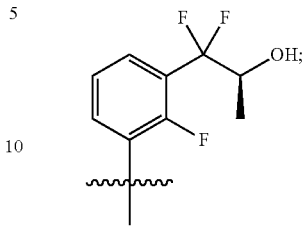

R² is —OR²ᵃ; R²ᵃ is methyl; R³ is cyclopropyl optionally substituted with one R²⁰ᵇ; and R²⁰ᵇ is —CN. In embodiments of a compound of Formula (I-2); R⁷ is $C_{1-6}$alkyl optionally substituted with one, two, or three R²⁰ᶜ; each R²⁰ᶜ is independently selected from halogen, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl; L¹ is a bond; R⁴ is hydrogen; R⁵ is methyl; R⁶ is hydrogen; R¹ is a

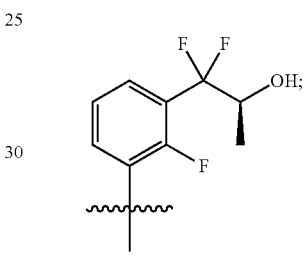

R² is —OR²ᵃ; R²ᵃ is methyl; R³ is $C_{3-4}$cycloalkyl optionally substituted with one R²⁰ᵇ; and R²⁰ᵇ is —CN. In embodiments of a compound of Formula (I-2); R⁷ is $C_{1-6}$alkyl optionally substituted with one, two, or three R²⁰ᶜ; each R²⁰ᶜ is independently selected from halogen, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl; L¹ is a bond; R⁴ is hydrogen; R⁵ is methyl; R⁶ is hydrogen; R¹ is a

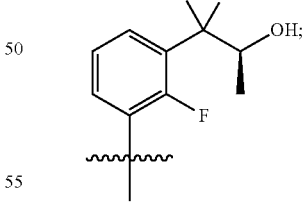

R² is —OR²ᵃ; R²ᵃ is methyl; R³ is $C_{3-4}$cycloalkyl optionally substituted with one, two, or three R²⁰ᵇ; and R²ᵇ is —CN. In embodiments of a compound of Formula (I-2); R⁷ is $C_{1-6}$alkyl optionally substituted with one, two, or three R²⁰ᶜ; each R²⁰ᶜ is independently selected from halogen, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl; L¹ is a bond; R⁴ is hydrogen; R⁵ is methyl; R⁶ is hydrogen; R¹ is a

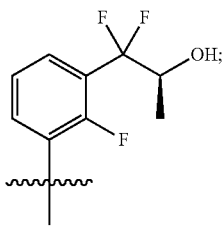 [SMILES: *c1cccc(C(F)(F)[C@H](C)O)c1F]

$R^2$ is —$OR^{2a}$; $R^{2a}$ is methyl; $R^3$ is $C_{3-4}$cycloalkyl optionally substituted with one, two, or three $R^{20b}$; and each $R^{20b}$ is independently —CN or $C_{1-3}$haloalkyl. In embodiments of a compound of Formula (I-2); $R^7$ is $C_{1-6}$alkyl optionally substituted with one, two, or three $R^{20c}$; each $R^{20c}$ is independently selected from halogen, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl; $L^1$ is a bond; $R^4$ is hydrogen; $R^5$ is methyl; $R^6$ is hydrogen; $R^1$ is a

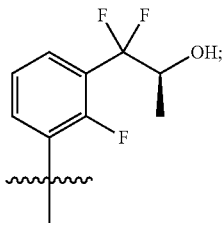 [SMILES: *c1cccc(C(F)(F)[C@H](C)O)c1F]

$R^2$ is —$OR^{2a}$; $R^{2a}$ is methyl; $R^3$ is $C_{3-4}$cycloalkyl optionally substituted with one, two, or three $R^{20b}$; and each $R^{20b}$ is independently —CN or $C_{1-3}$haloalkyl. In embodiments of a compound of Formula (I-2); $R^7$ is $C_{1-6}$alkyl optionally substituted with one, two, or three $R^{20c}$; each $R^{20c}$ is independently selected from halogen, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl; $L^1$ is a bond; $R^4$ is hydrogen; $R^5$ is methyl; $R^6$ is hydrogen; $R^1$ is

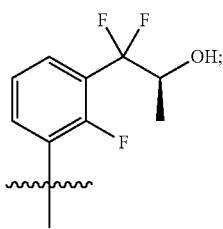 [SMILES: *c1cccc(C(F)(F)[C@H](C)O)c1F]

$R^2$ is —$OR^{2a}$; $R^{2a}$ is methyl; $R^3$ is $C_{3-4}$cycloalkyl optionally substituted with one, two, or three $R^{20b}$; and each $R^{20b}$ is independently —CN or $C_{1-3}$haloalkyl. In embodiments of a compound of Formula (I-2); $R^7$ is $C_{1-6}$alkyl optionally substituted with one, two, or three $R^{20c}$; each $R^{20c}$ is independently selected from halogen, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl; $L^1$ is a bond; $R^4$ is hydrogen; $R^5$ is methyl; $R^6$ is hydrogen; $R^1$ is a

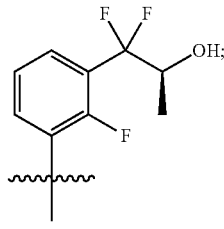 [SMILES: *c1cccc(C(F)(F)[C@H](C)O)c1F]

$R^2$ is —$OR^{2a}$; $R^{2a}$ is methyl; $R^3$ is $C_{3-4}$cycloalkyl optionally substituted with one, two, or three $R^{20b}$; and each $R^{20b}$ is independently selected from amino; —CN; $C_{1-3}$alkyl; $C_{1-3}$alkoxy; $C_{1-3}$ haloalkyl; —OH; —$N(R^{24})C(O)R^{21}$; and —$C(O)N(R^{22})(R^{23})$.

In embodiments of a compound of Formula (I-2); $R^7$ is $C_{1-6}$alkyl optionally substituted with one, two, or three $R^{20c}$; each $R^{20c}$ is independently selected from halogen, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl; $L^1$ is a bond; $R^4$ is hydrogen; $R^5$ is methyl; $R^6$ is hydrogen; $R^1$ is a $R^2$ is —$OR^{2a}$; $R^{2a}$ is methyl; and $R^3$ is

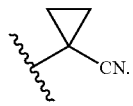

In embodiments of a compound of Formula (I-2); $R^7$ is $C_{1-6}$alkyl optionally substituted with one, two, or three $R^{20c}$; each $R^{20c}$ is independently selected from halogen, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl; $L^1$ is a bond; $R^4$ is hydrogen; $R^5$ is methyl; $R^6$ is hydrogen; $R^1$ is a

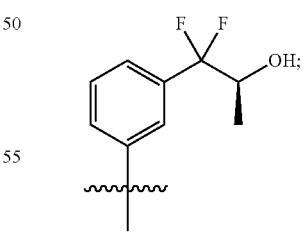

$R^2$ is —$OR^{2a}$; $R^{2a}$ is methyl; $R^3$ is cyclopropyl optionally substituted with one $R^{20b}$; and $R^{20b}$ is —CN. In embodiments of a compound of Formula (I-2); $R^7$ is $C_{1-6}$alkyl optionally substituted with one, two, or three $R^{20c}$; each $R^{20c}$ is independently selected from halogen, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl; $L^1$ is a bond; $R^5$ is methyl; $R^6$ is hydrogen; $R^1$ is a

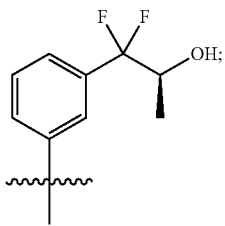 [SMILES: *c1cccc(C(F)(F)[C@H](C)O)c1]

$R^2$ is —$OR^{2a}$; $R^{2a}$ is methyl; $R^3$ is $C_{3-4}$cycloalkyl optionally substituted with one $R^{20b}$; and $R^{20b}$ is —CN. In embodiments of a compound of Formula (I-2); $R^7$ is $C_{1-6}$alkyl optionally substituted with one, two, or three $R^{20c}$; each $R^{20c}$ is independently selected from halogen, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl; $L^1$ is a bond; $R^4$ is hydrogen; $R^5$ is methyl; $R^6$ is hydrogen; $R^1$ is a

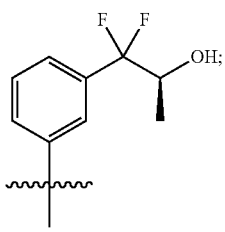 [SMILES: *c1cccc(C(F)(F)[C@H](C)O)c1]

$R^2$ is —$OR^{2a}$; $R^{2a}$ is methyl; $R^3$ is $C_{3-4}$cycloalkyl optionally substituted with one, two, or three $R^{20b}$; and $R^{20b}$ is —CN. In embodiments of a compound of Formula (I-2); $R^7$ is $C_{1-6}$alkyl optionally substituted with one, two, or three $R^{20c}$; each $R^{20c}$ is independently selected from halogen, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl; $L^1$ is a bond; $R^4$ is hydrogen; $R^5$ is methyl; $R^6$ is hydrogen; $R^1$ is a

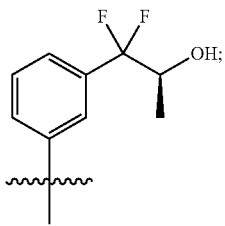 [SMILES: *c1cccc(C(F)(F)[C@H](C)O)c1]

$R^2$ is —$OR^{2a}$; $R^{2a}$ is methyl; $R^3$ is $C_{3-4}$cycloalkyl optionally substituted with one, two, or three $R^{20b}$; and each $R^{20b}$ is independently —CN or $C_{1-3}$haloalkyl. In embodiments of a compound of Formula (I-2); $R^7$ is $C_{1-6}$alkyl optionally substituted with one, two, or three $R^{20c}$; each $R^{20c}$ is independently selected from halogen, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl; $L^1$ is a bond; $R^4$ is hydrogen; $R^5$ is methyl; $R^6$ is hydrogen; $R^1$ is

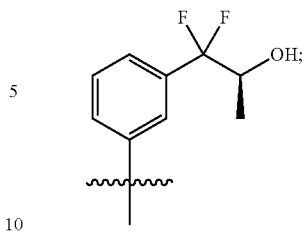

$R^2$ is —$OR^{2a}$; $R^{2a}$ is methyl; $R^3$ is $C_{3-4}$cycloalkyl optionally substituted with one, two, or three $R^{20b}$; and each $R^{20b}$ is independently —CN or $C_{1-3}$haloalkyl. In embodiments of a compound of Formula (I-2); $R^7$ is $C_{1-6}$alkyl optionally substituted with one, two, or three $R^{20c}$; each $R^{20c}$ is independently selected from halogen, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl; $L^1$ is a bond; $R^4$ is hydrogen; $R^5$ is methyl; $R^6$ is hydrogen; $R^1$ is a

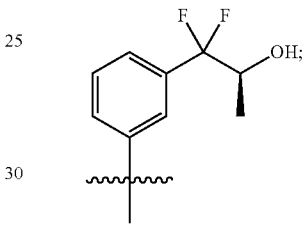

$R^2$ is —$OR^{2a}$; $R^{2a}$ is methyl; $R^3$ is $C_{3-4}$cycloalkyl optionally substituted with one, two, or three $R^{20b}$; and each $R^{20b}$ is independently —CN or $C_{1-3}$haloalkyl. In embodiments of a compound of Formula (I-2); $R^7$ is $C_{1-6}$alkyl optionally substituted with one, two, or three $R^{20c}$; each $R^{20c}$ is independently selected from halogen, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl; $L^1$ is a bond; $R^4$ is hydrogen; $R^5$ is methyl; $R^6$ is hydrogen; $R^1$ is a

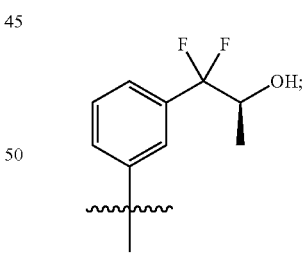

$R^2$ is —$OR^{2a}$; $R^{2a}$ is methyl; $R^3$ is $C_{3-4}$cycloalkyl optionally substituted with one, two, or three $R^{20b}$; and each $R^{20b}$ is independently selected from amino; —CN; $C_{1-3}$alkyl; $C_{1-3}$alkoxy; $C_{1-3}$ haloalkyl; —OH; —$N(R^{24})C(O)R^{21}$; and —$C(O)N(R^{22})(R^{23})$.

In embodiments of a compound of Formula (I-2); $R^7$ is $C_{1-6}$alkyl optionally substituted with one, two, or three $R^{20c}$; each $R^{20c}$ is independently selected from halogen, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl; $L^1$ is a bond; $R^4$ is hydrogen; $R^5$ is methyl; $R^6$ is hydrogen; $R^1$ is a

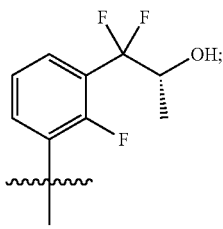 [SMILES: *c1cccc(C(F)(F)[C@@H](C)O)c1F]

$R^2$ is —$OR^{2a}$; $R^{2a}$ is methyl; and $R^3$ is

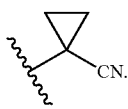

In embodiments of a compound of Formula (I-2); $R^7$ is $C_{1-6}$alkyl optionally substituted with one, two, or three $R^{20c}$; each $R^{20c}$ is independently selected from halogen, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl; $L^1$ is a bond; $R^4$ is hydrogen; $R^5$ is methyl; $R^6$ is hydrogen; $R^1$ is a

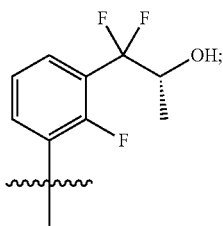 [SMILES: *c1cccc(C(F)(F)[C@@H](C)O)c1F]

$R^2$ is —$OR^{2a}$; $R^{2a}$ is methyl; $R^3$ is cyclopropyl optionally substituted with one $R^{20b}$; and $R^{20b}$ is —CN. In embodiments of a compound of Formula (I-2); $R^7$ is $C_{1-6}$alkyl optionally substituted with one, two, or three $R^{20c}$; each $R^{20c}$ is independently selected from halogen, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl; $L^1$ is a bond; $R^4$ is hydrogen; $R^5$ is methyl; $R^6$ is hydrogen; $R^1$ is a

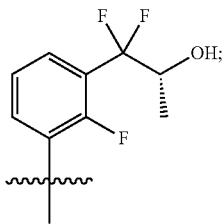 [SMILES: *c1cccc(C(F)(F)[C@@H](C)O)c1F]

$R^2$ is —$OR^{2a}$; $R^{2a}$ is methyl; $R^3$ is $C_{3-4}$cycloalkyl optionally substituted with one $R^{20b}$; and $R^{20b}$ is —CN. In embodiments of a compound of Formula (I-2); $R^7$ is $C_{1-6}$alkyl optionally substituted with one, two, or three $R^{20c}$; each $R^{20c}$ is independently selected from halogen, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl; $L^1$ is a bond; $R^4$ is hydrogen; $R^5$ is methyl; $R^6$ is hydrogen; $R^1$ is a

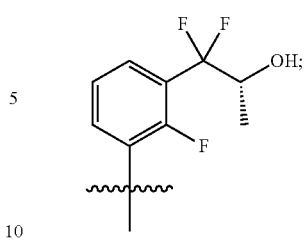

$R^2$ is —$OR^{2a}$; $R^{2a}$ is methyl; $R^3$ is $C_{3-4}$cycloalkyl optionally substituted with one, two, or three $R^{20b}$; and $R^{20b}$ is —CN. In embodiments of a compound of Formula (I-2); $R^7$ is $C_{1-6}$alkyl optionally substituted with one, two, or three $R^{20c}$; each $R^{20c}$ is independently selected from halogen, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl; $L^1$ is a bond; $R^4$ is hydrogen; $R^5$ is methyl; $R^6$ is hydrogen; $R^1$ is a

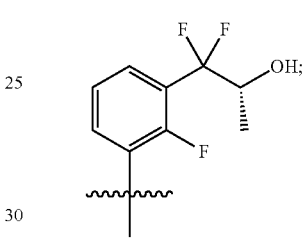

$R^2$ is —$OR^{2a}$; $R^{2a}$ is methyl; $R^3$ is $C_{3-4}$cycloalkyl optionally substituted with one, two, or three $R^{20b}$; and each $R^{20b}$ is independently —CN or $C_{1-3}$haloalkyl. In embodiments of a compound of Formula (I-2); $R^7$ is $C_{1-6}$alkyl optionally substituted with one, two, or three $R^{20c}$; each $R^{20c}$ is independently selected from halogen, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl; $L^1$ is a bond; $R^4$ is hydrogen; $R^5$ is methyl; $R^6$ is hydrogen; $R^1$ is a

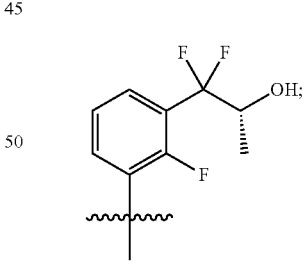

$R^2$ is —$OR^{2a}$; $R^{2a}$ is methyl; $R^3$ is $C_{3-4}$cycloalkyl optionally substituted with one, two, or three $R^{20b}$; and each $R^{20b}$ is independently —CN or $C_{1-3}$haloalkyl. In embodiments of a compound of Formula (I-2); $R^7$ is $C_{1-6}$alkyl optionally substituted with one, two, or three $R^{20c}$; each $R^{20c}$ is independently selected from halogen, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl; $L^1$ is a bond; $R^5$ is methyl; $R^6$ is hydrogen; $R^1$ is a

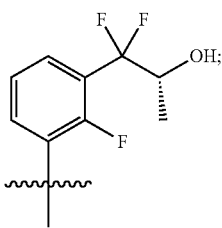 [SMILES: *c1cccc(C(F)(F)[C@@H](C)O)c1F]

$R^2$ is —$OR^{2a}$; $R^{2a}$ is methyl; $R^3$ is $C_{3-4}$cycloalkyl optionally substituted with one, two, or three $R^{20b}$; and each $R^{20b}$ is independently —CN or $C_{1-3}$haloalkyl. In embodiments of a compound of Formula (I-2); $R^7$ is $C_{1-6}$alkyl optionally substituted with one, two, or three $R^{20c}$; each $R^{20c}$ is independently selected from halogen, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl; $L^1$ is a bond; $R^4$ is hydrogen; $R^5$ is methyl; $R^6$ is hydrogen; $R^1$ is

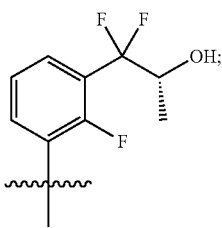 [SMILES: *c1cccc(C(F)(F)[C@@H](C)O)c1F]

$R^2$ is —$OR^{2a}$; $R^{2a}$ is methyl; $R^3$ is $C_{3-4}$cycloalkyl optionally substituted with one, two, or three $R^{20b}$; and each $R^{20b}$ is independently selected from amino; —CN; $C_{1-3}$alkyl; $C_{1-3}$alkoxy; $C_{1-3}$ haloalkyl; —OH; —N($R^{24}$)C(O)$R^{25}$; and —C(O)N($R^{22}$)($R^{23}$).

In embodiments of a compound of Formula (I-2); $R^7$ is $C_{1-6}$alkyl optionally substituted with one, two, or three $R^{20c}$; each $R^{20c}$ is independently selected from halogen, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl; $L^1$ is a bond; $R^4$ is hydrogen; $R^5$ is methyl; $R^6$ is hydrogen; $R^1$ is a

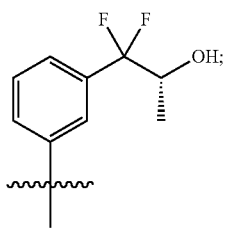 [SMILES: *c1cccc(C(F)(F)[C@@H](C)O)c1]

$R^2$ is —$OR^{2a}$; $R^{2a}$ is methyl; and $R^3$ is

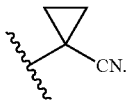

In embodiments of a compound of Formula (I-2); $R^7$ is $C_{1-6}$alkyl optionally substituted with one, two, or three $R^{20c}$; each $R^{20c}$ is independently selected from halogen, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl; $L^1$ is a bond; $R^4$ is hydrogen; $R^5$ is methyl; $R^6$ is hydrogen; $R^1$ is a

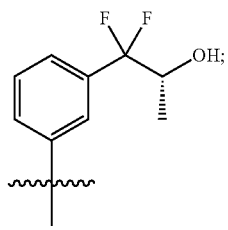 [SMILES: *c1cccc(C(F)(F)[C@@H](C)O)c1]

$R^2$ is —$OR^{2a}$; $R^{2a}$ is methyl; $R^3$ is cyclopropyl optionally substituted with one $R^{20b}$; and $R^{20b}$ is —CN. In embodiments of a compound of Formula (I-2); $R^7$ is $C_{1-6}$alkyl optionally substituted with one, two, or three $R^{20c}$; each $R^{20c}$ is independently selected from halogen, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl; $L^1$ is a bond; $R^4$ is hydrogen; $R^5$ is methyl; $R^6$ is hydrogen; $R^1$ is a

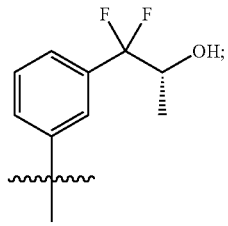 [SMILES: *c1cccc(C(F)(F)[C@@H](C)O)c1]

$R^2$ is —$OR^{2a}$; $R^{2a}$ is methyl; $R^3$ is $C_{3-4}$cycloalkyl optionally substituted with one $R^{20b}$; and $R^{20b}$ is —CN. In embodiments of a compound of Formula (I-2); $R^7$ is $C_{1-6}$alkyl optionally substituted with one, two, or three $R^{20c}$; each $R^{20c}$ is independently selected from halogen, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl; $L^1$ is a bond; $R^4$ is hydrogen; $R^5$ is methyl; $R^6$ is hydrogen; $R^1$ is a

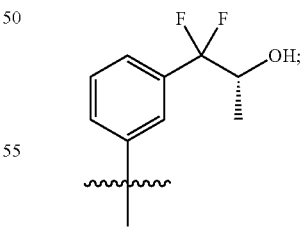

$R^2$ is —$OR^{2a}$; $R^{2a}$ is methyl; $R^3$ is $C_{3-4}$cycloalkyl optionally substituted with one, two, or three $R^{20b}$; and $R^{20b}$ is —CN. In embodiments of a compound of Formula (I-2); $R^7$ is $C_{1-6}$alkyl optionally substituted with one, two, or three $R^{20c}$; each $R^{20c}$ is independently selected from halogen, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl; $L^1$ is a bond; $R^4$ is hydrogen; $R^5$ is methyl; $R^6$ is hydrogen; $R^1$ is a

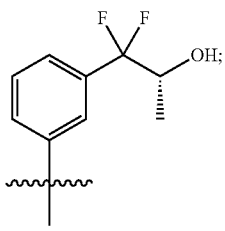 [SMILES: *c1cccc(C(F)(F)[C@@H](C)O)c1]

$R^2$ is —$OR^{2a}$; $R^{2a}$ is methyl; $R^3$ is $C_{3-4}$cycloalkyl optionally substituted with one, two, or three $R^{20b}$; and each $R^{20b}$ is independently —CN or $C_{1-3}$haloalkyl. In embodiments of a compound of Formula (I-2); $R^7$ is $C_{1-6}$alkyl optionally substituted with one, two, or three $R^{20c}$; each $R^{20c}$ is independently selected from halogen, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl; $L^1$ is a bond; $R^4$ is hydrogen; $R^5$ is methyl; $R^6$ is hydrogen; $R^1$ is a

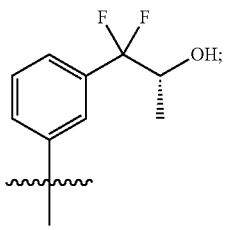 [SMILES: *c1cccc(C(F)(F)[C@@H](C)O)c1]

$R^2$ is —$OR^{2a}$; $R^{2a}$ is methyl; $R^3$ is $C_{3-4}$cycloalkyl optionally substituted with one, two, or three $R^{20b}$; and each $R^{20b}$ is independently —CN or $C_{1-3}$haloalkyl. In embodiments of a compound of Formula (I-2); $R^7$ is $C_{1-6}$alkyl optionally substituted with one, two, or three $R^{20c}$; each $R^{20c}$ is independently selected from halogen, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl; $L^1$ is a bond; $R^4$ is hydrogen; $R^5$ is methyl; $R^6$ is hydrogen; $R^1$ is a

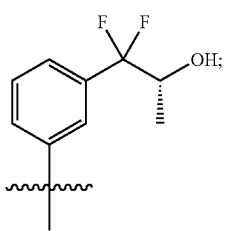 [SMILES: *c1cccc(C(F)(F)[C@@H](C)O)c1]

$R^2$ is —$OR^{2a}$; $R^{2a}$ is methyl; $R^3$ is $C_{3-4}$cycloalkyl optionally substituted with one, two, or three $R^{20b}$; and each $R^{20b}$ is independently —CN or $C_{1-3}$haloalkyl. In embodiments of a compound of Formula (I-2); $R^7$ is $C_{1-6}$alkyl optionally substituted with one, two, or three $R^{20c}$; each $R^{20c}$ is independently selected from halogen, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl; $L^1$ is a bond; $R^4$ is hydrogen; $R^5$ is methyl; $R^6$ is hydrogen; $R^1$ is a

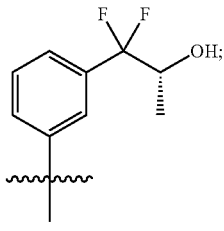 [SMILES: *c1cccc(C(F)(F)[C@@H](C)O)c1]

$R^2$ is —$OR^{2a}$; $R^{2a}$ is methyl; $R^3$ is $C_{3-4}$cycloalkyl optionally substituted with one, two, or three $R^{20b}$; and each $R^{20b}$ is independently selected from amino; —CN; $C_{1-3}$alkyl; $C_{1-3}$alkoxy; $C_{1-3}$ haloalkyl; —OH; —$N(R^{24})C(O)R^{21}$; and —$C(O)N(R^{22})(R^{23})$.

In embodiments of a compound of Formula (I-2); $R^7$ is $C_{1-6}$alkyl optionally substituted with one, two, or three $R^{20c}$; each $R^{20c}$ is independently selected from halogen, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl; $L^1$ is a bond; $R^4$ is hydrogen; $R^5$ is methyl; $R^6$ is hydrogen; $R^1$ is a phenyl substituted with one or more $R^{10}$; each $R^{10}$ is independently selected from halogen and $C_{1-4}$alkyl optionally substituted with one, two, or three $R^{20d}$; each $R^{20d}$ is independently selected from halogen and —OH; $R^2$ is —$OR^{2a}$; $R^{2a}$ is methyl; and $R^3$ is

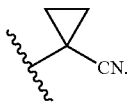

In embodiments of a compound of Formula (I-2); $R^7$ is $C_{1-6}$alkyl optionally substituted with one, two, or three $R^{20c}$; each $R^{20c}$ is independently selected from halogen, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl; $L^1$ is a bond; $R^4$ is hydrogen; $R^5$ is methyl; $R^6$ is hydrogen; $R^1$ is a phenyl substituted with one or more $R^{10}$; each $R^{10}$ is independently selected from halogen and $C_{1-4}$alkyl optionally substituted with one, two, or three $R^{20d}$; each $R^{20d}$ is independently selected from halogen and —OH; $R^2$ is —$OR^{2a}$; $R^{2a}$ is methyl; $R^3$ is cyclopropyl optionally substituted with one $R^{20b}$; and $R^{20b}$ is —CN. In embodiments of a compound of Formula (I-2); $R^7$ is $C_{1-6}$alkyl optionally substituted with one, two, or three $R^{20c}$; each $R^{20c}$ is independently selected from halogen, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl; $L^1$ is a bond; $R^4$ is hydrogen; $R^5$ is methyl; $R^6$ is hydrogen; $R^1$ is a phenyl substituted with one or more $R^{10}$; each $R^{10}$ is independently selected from halogen and $C_{1-4}$alkyl optionally substituted with one, two, or three $R^{20d}$; each $R^{20d}$ is independently selected from halogen and —OH; $R^2$ is —$OR^{2a}$; $R^{2a}$ is methyl; $R^3$ is $C_{3-4}$cycloalkyl optionally substituted with one $R^{20b}$; and $R^{20b}$ is —CN. In embodiments of a compound of Formula (I-2); $R^7$ is $C_{1-6}$alkyl optionally substituted with one, two, or three $R^{20c}$; each $R^{20c}$ is independently selected from halogen, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl; $L^1$ is a bond; $R^4$ is hydrogen; $R^5$ is methyl; $R^6$ is hydrogen; $R^1$ is a phenyl substituted with one or more $R^{10}$; each $R^{10}$ is independently selected from halogen and $C_{1-4}$alkyl optionally substituted with one, two, or three $R^{20d}$; each $R^{20d}$ is independently selected from halogen and —OH; $R^2$ is —$OR^{2a}$; $R^{2a}$ is methyl; $R^3$ is $C_{3-4}$cycloalkyl optionally substituted with one, two, or three $R^{20b}$; and $R^{20b}$ is —CN. In embodiments of a compound of Formula (I-2); $R^7$ is $C_{1-6}$alkyl optionally substituted with one, two, or three $R^{20c}$; each $R^{20c}$ is independently selected from halogen, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl; $L^1$ is a bond; $R^4$ is hydrogen; $R^5$ is methyl; $R^6$ is hydrogen; $R^1$ is a phenyl substituted with one or more $R^{10}$; each $R^{10}$ is independently selected from halogen and $C_{1-4}$alkyl optionally substituted with one, two, or three $R^{20d}$; each $R^{20d}$ is independently selected from halogen and —OH; $R^2$ is —$OR^{2a}$; $R^{2a}$ is methyl; $R^3$ is $C_{3-4}$cycloalkyl optionally substituted with one, two, or three $R^{20b}$; and each $R^{20b}$ is independently —CN or $C_{1-3}$haloalkyl. In embodiments of a compound of Formula (I-2); $R^7$ is $C_{1-6}$alkyl optionally substituted with one, two, or three $R^{20c}$; each $R^{20c}$ is independently selected from halogen, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl; $L^1$ is a bond; $R^4$ is hydrogen; $R^5$ is methyl; $R^6$ is hydrogen; $R^1$ is a phenyl substituted with one or more $R^{10}$; each $R^{10}$ is independently selected from halogen and $C_{1-4}$alkyl optionally substituted with one, two, or three $R^{20d}$; each $R^{20d}$ is independently selected from halogen and —OH; $R^2$ is —$OR^{2a}$; $R^{2a}$ is methyl; $R^3$ is $C_{3-4}$cycloalkyl optionally substituted with one, two, or three $R^{20b}$; and each $R^{20b}$ is independently —CN or $C_{1-3}$haloalkyl. In embodiments of a compound of Formula (I-2); $R^7$ is $C_{1-6}$alkyl optionally substituted with one, two, or three $R^{20c}$; each $R^{20c}$ is independently selected from halogen, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl; $L^1$ is a bond; $R^4$ is hydrogen; $R^5$ is methyl; $R^6$ is hydrogen; $R^1$ is a phenyl substituted with one or more $R^{10}$; each $R^{10}$ is independently selected from halogen and $C_{1-4}$alkyl optionally substituted with one, two, or three $R^{20d}$; each $R^{20d}$ is independently selected from halogen and —OH; $R^2$ is —$OR^{2a}$; $R^{2a}$ is methyl; $R^3$ is $C_{3-4}$cycloalkyl optionally substituted with one, two, or three $R^{20b}$; and each $R^{20b}$ is independently —CN or $C_{1-3}$haloalkyl. In embodiments of a compound of Formula (I-2); $R^7$ is $C_{1-6}$alkyl optionally substituted with one, two, or three $R^{20c}$; each $R^{20c}$ is independently selected from halogen, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl; $L^1$ is a bond; $R^4$ is hydrogen; $R^5$ is methyl; $R^6$ is hydrogen; $R^1$ is a phenyl substituted with one or more $R^{10}$; each $R^{10}$ is independently selected from halogen and $C_{1-4}$alkyl optionally substituted with one, two, or three $R^{20d}$; each $R^{20d}$ is independently selected from halogen and —OH; $R^2$ is —$OR^{2a}$; $R^{2a}$ is methyl; $R^3$ is $C_{3-4}$cycloalkyl optionally substituted with one, two, or three $R^{20b}$; and each $R^{20b}$ is independently selected from amino; —CN; $C_{1-3}$alkyl; $C_{1-3}$alkoxy; $C_{1-3}$haloalkyl; —OH; —N($R^{24}$)C(O)$R^{21}$; and —C(O)N($R^{22}$)($R^{23}$).

In embodiments of a compound of Formula (I-2); $R^7$ is $C_{1-6}$alkyl optionally substituted with one, two, or three $R^{20c}$; each $R^{20c}$ is independently selected from halogen, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl; $L^1$ is a bond; $R^4$ is hydrogen; $R^5$ is methyl; $R^6$ is hydrogen; $R^1$ is a phenyl substituted with one or more $R^{10}$; each $R^{10}$ is independently selected from halogen and $C_{1-4}$alkyl optionally substituted with one, two, or three $R^{20d}$; each $R^{20d}$ is independently selected from halogen, —OH, $C_{2-5}$heterocycloalkyl optionally substituted with one, two, or three $C_{1-6}$alkyl (e.g., methyl, ethyl, or propyl), and —$OR^{21}$, wherein $R^{21}$ is $C_{2-5}$heterocycloalkyl optionally substituted with one, two, or three $C_{1-6}$alkyl (e.g., methyl, ethyl, propyl, or butyl); $R^2$ is —$OR^{2a}$; $R^{2a}$ is methyl; and $R^3$ is In embodiments of a compound of Formula (I-2); $R^7$ is $C_{1-6}$alkyl optionally substituted with one, two, or three $R^{20c}$; each $R^{20c}$ is independently selected from halogen, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl; $L^1$ is a bond; $R^4$ is hydrogen; $R^5$ is methyl; $R^6$ is hydrogen; $R^1$ is a phenyl substituted with one or more $R^{10}$; each $R^{10}$ is independently selected from halogen and $C_{1-4}$alkyl optionally substituted with one, two, or three $R^{20d}$; each $R^{20d}$ is independently selected from halogen, —OH, $C_{2-5}$heterocycloalkyl optionally substituted with one, two, or three $C_{1-6}$alkyl (e.g., methyl, ethyl, or propyl), and —$OR^{21}$, wherein $R^{21}$ is $C_{2-5}$heterocycloalkyl optionally substituted with one, two, or three $C_{1-6}$alkyl (e.g., methyl, ethyl, propyl, or butyl); $R^3$ is cyclopropyl optionally substituted with one $R^{20b}$; and $R^{20b}$ is —CN. In embodiments of a compound of Formula (I-2); $R^7$ is $C_{1-6}$alkyl optionally substituted with one, two, or three $R^{20c}$; each $R^{20c}$ is independently selected from halogen, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl; $L^1$ is a bond; $R^4$ is hydrogen; $R^5$ is methyl; $R^6$ is hydrogen; $R^1$ is a phenyl substituted with one or more $R^{10}$; each $R^{10}$ is independently selected from halogen and $C_{1-4}$alkyl optionally substituted with one, two, or three $R^{20d}$; each $R^{20d}$ is independently selected from halogen, —OH, $C_{2-5}$heterocycloalkyl optionally substituted with one, two, or three $C_{1-6}$alkyl (e.g., methyl, ethyl, or propyl), and —$OR^{21}$, wherein $R^{21}$ is $C_{2-5}$heterocycloalkyl optionally substituted with one, two, or three $C_{1-6}$alkyl (e.g., methyl, ethyl, propyl, or butyl); $R^2$ is —$OR^{2a}$; $R^{2a}$ is methyl; $R^3$ is $C_{3-4}$cycloalkyl optionally substituted with one $R^{20b}$; and $R^{20b}$ is —CN. In embodiments of a compound of Formula (I-2); $R^7$ is $C_{1-6}$alkyl optionally substituted with one, two, or three $R^{20c}$; each $R^{20c}$ is independently selected from halogen, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl; $L^1$ is a bond; $R^4$ is hydrogen; $R^5$ is methyl; $R^6$ is hydrogen; $R^1$ is a phenyl substituted with one or more $R^{10}$; each $R^{10}$ is independently selected from halogen and $C_{1-4}$alkyl optionally substituted with one, two, or three $R^{20d}$; each $R^{20d}$ is independently selected from halogen, —OH, $C_{2-5}$heterocycloalkyl optionally substituted with one, two, or three $C_{1-6}$alkyl (e.g., methyl, ethyl, or propyl), and —$OR^{21}$, wherein $R^{21}$ is $C_{2-5}$heterocycloalkyl optionally substituted with one, two, or three $C_{1-6}$alkyl (e.g., methyl, ethyl, propyl, or butyl); $R^2$ is —OR$^{2a}$; R$^{2a}$ is methyl; R$^3$ is C$_{3-4}$cycloalkyl optionally substituted with one, two, or three R$^{20b}$; and each R$^{20b}$ is independently —CN or C$_{1-3}$haloalkyl. In embodiments of a compound of Formula (I-2); R$^7$ is C$_{1-6}$alkyl optionally substituted with one, two, or three R$^{20c}$; each R$^{20c}$ is independently selected from halogen, C$_{2-6}$alkenyl, C$_{2-6}$alkynyl, C$_{3-10}$cycloalkyl, C$_{2-9}$heterocycloalkyl, C$_{6-10}$aryl, and C$_{1-9}$heteroaryl; L$^1$ is a bond; R$^4$ is hydrogen; R$^5$ is methyl; R$^6$ is hydrogen; R$^1$ is a phenyl substituted with one or more R$^{10}$; each R$^{10}$ is independently selected from halogen and C$_{1-4}$alkyl optionally substituted with one, two, or three R$^{20d}$; each R$^{20d}$ is independently selected from halogen, —OH, C$_{2-5}$heterocycloalkyl optionally substituted with one, two, or three C$_{1-6}$alkyl (e.g., methyl, ethyl, or propyl), and —OR$^{21}$, wherein R$^{21}$ is C$_{2-5}$heterocycloalkyl optionally substituted with one, two, or three C$_{1-6}$alkyl (e.g., methyl, ethyl, propyl, or butyl); R$^2$ is —OR$^{2a}$; R$^{2a}$ is methyl; R$^3$ is C$_{3-4}$cycloalkyl optionally substituted with one, two, or three R$^{20b}$; and each R$^{20b}$ is independently —CN or C$_{1-3}$haloalkyl. In embodiments of a compound of Formula (I-2); R$^7$ is C$_{1-6}$alkyl optionally substituted with one, two, or three R$^{20c}$; each R$^{20c}$ is independently selected from halogen, C$_{2-6}$alkenyl, C$_{2-6}$alkynyl, C$_{3-10}$cycloalkyl, C$_{2-9}$heterocycloalkyl, C$_{6-10}$aryl, and C$_{1-9}$heteroaryl; L$^1$ is a bond; R$^4$ is hydrogen; R$^5$ is methyl; R$^6$ is hydrogen; R$^1$ is a phenyl substituted with one or more R$^{10}$; each R$^{10}$ is independently selected from halogen and C$_{1-4}$alkyl optionally substituted with one, two, or three R$^{20d}$; each R$^{20d}$ is independently selected from halogen, —OH, C$_{2-5}$heterocycloalkyl optionally substituted with one, two, or three C$_{1-6}$alkyl (e.g., methyl, ethyl, or propyl), and —OR$^{21}$, wherein R$^{21}$ is C$_{2-5}$heterocycloalkyl optionally substituted with one, two, or three C$_{1-6}$alkyl (e.g., methyl, ethyl, propyl, or butyl); R$^2$ is —OR$^{2a}$; R$^{2a}$ is methyl; R$^3$ is C$_{3-4}$cycloalkyl optionally substituted with one, two, or three R$^{20b}$; and each R$^{20b}$ is independently selected from amino; —CN; C$_{1-3}$alkyl; C$_{1-3}$alkoxy; C$_{1-3}$haloalkyl; —OH; —N(R$^{24}$)C(O)R$^{25}$; and —C(O)N(R$^{22}$)(R$^{23}$).

In embodiments of a compound of Formula (I-2); R$^7$ is C$_{1-6}$alkyl optionally substituted with one, two, or three R$^{20c}$; each R$^{20c}$ is independently selected from halogen, C$_{2-6}$alkenyl, C$_{2-6}$alkynyl, C$_{3-10}$cycloalkyl, C$_{2-9}$heterocycloalkyl, C$_{6-10}$aryl, and C$_{1-9}$heteroaryl; L$^1$ is a bond; R$^4$ is hydrogen; R$^5$ is methyl; R$^6$ is hydrogen; R$^1$ is a 6-10 membered aryl ring substituted with one or more R$^{10}$; each R$^{10}$ is independently selected from halogen and C$_{1-4}$alkyl optionally substituted with one, two, or three R$^{20d}$; each R$^{20d}$ is independently selected from halogen, —OH, C$_{2-5}$heterocycloalkyl optionally substituted with one, two, or three C$_{1-6}$alkyl (e.g., methyl, ethyl, or propyl), and —OR$^{21}$, wherein R$^{21}$ is C$_{2-5}$heterocycloalkyl optionally substituted with one, two, or three C$_{1-6}$alkyl (e.g., methyl, ethyl, propyl, or butyl); R$^2$ is —OR$^{2a}$; R$^{2a}$ is methyl; and R$^3$ is In embodiments of a compound of Formula (I-2); R$^7$ is C$_{1-6}$alkyl optionally substituted with one, two, or three R$^{20c}$; each R$^{20c}$ is independently selected from halogen, C$_{2-6}$alkenyl, C$_{2-6}$alkynyl, C$_{3-10}$cycloalkyl, C$_{2-9}$heterocycloalkyl, C$_{6-10}$aryl, and C$_{1-9}$heteroaryl; L$^1$ is a bond; R$^4$ is hydrogen; R$^5$ is methyl; R$^6$ is hydrogen; R$^1$ is a 6-10 membered aryl ring substituted with one or more R$^{10}$; each R$^{10}$ is independently selected from halogen and C$_{1-4}$ alkyl optionally substituted with one, two, or three R$^{20d}$; each R$^{20d}$ is independently selected from halogen, —OH, C$_{2-5}$heterocycloalkyl optionally substituted with one, two, or three C$_{1-6}$alkyl (e.g., methyl, ethyl, or propyl), and —OR$^{21}$, wherein R$^{21}$ is C$_{2-5}$heterocycloalkyl optionally substituted with one, two, or three C$_{1-6}$alkyl (e.g., methyl, ethyl, propyl, or butyl); R$^3$ is cyclopropyl optionally substituted with one R$^{20b}$; and R$^{20b}$ is —CN. In embodiments of a compound of Formula (I-2); R$^7$ is C$_{1-6}$alkyl optionally substituted with one, two, or three R$^{20c}$; each R$^{20c}$ is independently selected from halogen, C$_{2-6}$alkenyl, C$_{2-6}$alkynyl, C$_{3-10}$cycloalkyl, C$_{2-9}$heterocycloalkyl, C$_{6-10}$aryl, and C$_{1-9}$heteroaryl; L$^1$ is a bond; R$^4$ is hydrogen; R$^5$ is methyl; R$^6$ is hydrogen; R$^1$ is a 6-10 membered aryl ring substituted with one or more R$^{10}$; each R$^{10}$ is independently selected from halogen and C$_{1-4}$alkyl optionally substituted with one, two, or three R$^{20d}$; each R$^{20d}$ is independently selected from halogen, —OH, C$_{2-5}$heterocycloalkyl optionally substituted with one, two, or three C$_{1-6}$alkyl (e.g., methyl, ethyl, or propyl), and —OR$^{21}$, wherein R$^{21}$ is C$_{2-5}$heterocycloalkyl optionally substituted with one, two, or three C$_{1-6}$alkyl (e.g., methyl, ethyl, propyl, or butyl); R$^2$ is —OR$^{2a}$; R$^{2a}$ is methyl; R$^3$ is C$_{3-4}$cycloalkyl optionally substituted with one R$^{20b}$; and R$^{20b}$ is —CN. In embodiments of a compound of Formula (I-2); R$^7$ is C$_{1-6}$alkyl optionally substituted with one, two, or three R$^{20c}$; each R$^{20c}$ is independently selected from halogen, C$_{2-6}$alkenyl, C$_{2-6}$alkynyl, C$_{3-10}$cycloalkyl, C$_{2-9}$heterocycloalkyl, C$_{6-10}$aryl, and C$_{1-9}$heteroaryl; L$^1$ is a bond; R$^4$ is hydrogen; R$^5$ is methyl; R$^6$ is hydrogen; R$^1$ is a 6-10 membered aryl ring substituted with one or more R$^{10}$; each R$^{10}$ is independently selected from halogen and C$_{1-4}$alkyl optionally substituted with one, two, or three R$^{20d}$; each R$^{20d}$ is independently selected from halogen, —OH, C$_{2-5}$heterocycloalkyl optionally substituted with one, two, or three C$_{1-6}$alkyl (e.g., methyl, ethyl, or propyl), and —OR$^{21}$, wherein R$^{21}$ is C$_{2-5}$heterocycloalkyl optionally substituted with one, two, or three C$_{1-6}$alkyl (e.g., methyl, ethyl, propyl, or butyl); R$^2$ is —OR$^{2a}$; R$^{2a}$ is methyl; R$^3$ is C$_{3-4}$cycloalkyl optionally substituted with one, two, or three R$^{20b}$; and R$^{20b}$ is —CN. In embodiments of a compound of Formula (I-2); R$^7$ is C$_{1-6}$alkyl optionally substituted with one, two, or three R$^{20c}$; each R$^{20c}$ is independently selected from halogen, C$_{2-6}$alkenyl, C$_{2-6}$alkynyl, C$_{3-10}$cycloalkyl, C$_{2-9}$heterocycloalkyl, C$_{6-10}$aryl, and C$_{1-9}$heteroaryl; L$^1$ is a bond; R$^4$ is hydrogen; R$^5$ is methyl; R$^6$ is hydrogen; R$^1$ is a 6-10 membered aryl ring substituted with one or more R$^{10}$; each R$^{10}$ is independently selected from halogen and C$_{1-4}$alkyl optionally substituted with one, two, or three R$^{20d}$; each R$^{20d}$ is independently selected from halogen, —OH, $C_{2-5}$heterocycloalkyl optionally substituted with one, two, or three $C_{1-6}$alkyl (e.g., methyl, ethyl, or propyl), and —OR$^{21}$, wherein R$^{21}$ is $C_{2-5}$heterocycloalkyl optionally substituted with one, two, or three $C_{1-6}$alkyl (e.g., methyl, ethyl, propyl, or butyl); R$^2$ is —OR$^{2a}$; R$^{2a}$ is methyl; R$^3$ is $C_{3-4}$cycloalkyl optionally substituted with one, two, or three R$^{20b}$; and each R$^{20b}$ is independently —CN or $C_{1-3}$haloalkyl. In embodiments of a compound of Formula (I-2); R$^7$ is $C_{1-6}$alkyl optionally substituted with one, two, or three R$^{20c}$; each R$^{20c}$ is independently selected from halogen, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl; L$^1$ is a bond; R$^4$ is hydrogen; R$^5$ is methyl; R$^6$ is hydrogen; R$^1$ is a 6-10 membered aryl ring substituted with one or more R$^{10}$; each R$^{10}$ is independently selected from halogen and $C_{1-4}$alkyl optionally substituted with one, two, or three R$^{20d}$; each R$^{20d}$ is independently selected from halogen, —OH, $C_{2-5}$heterocycloalkyl optionally substituted with one, two, or three $C_{1-6}$ alkyl (e.g., methyl, ethyl, or propyl), and —OR$^{21}$, wherein R$^{21}$ is $C_{2-5}$heterocycloalkyl optionally substituted with one, two, or three $C_{1-6}$alkyl (e.g., methyl, ethyl, propyl, or butyl); R$^2$ is —OR$^{2a}$; R$^{2a}$ is methyl; R$^3$ is $C_{3-4}$cycloalkyl optionally substituted with one, two, or three R$^{20b}$; and each R$^{20b}$ is independently —CN or $C_{1-3}$haloalkyl. In embodiments of a compound of Formula (I-2); R$^7$ is $C_{1-6}$alkyl optionally substituted with one, two, or three R$^{20c}$; each R$^{20c}$ is independently selected from halogen, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl; L$^1$ is a bond; R$^4$ is hydrogen; R$^5$ is methyl; R$^6$ is hydrogen; R$^1$ is a 6-10 membered aryl ring substituted with one or more R$^{10}$; each R$^{10}$ is independently selected from halogen and $C_{1-4}$alkyl optionally substituted with one, two, or three R$^{20d}$; each R$^{20d}$ is independently selected from halogen, —OH, $C_{2-5}$heterocycloalkyl optionally substituted with one, two, or three $C_{1-6}$alkyl (e.g., methyl, ethyl, or propyl), and —OR$^{21}$, wherein R$^{21}$ is $C_{2-5}$heterocycloalkyl optionally substituted with one, two, or three $C_{1-6}$alkyl (e.g., methyl, ethyl, propyl, or butyl); R$^2$ is —OR$^{2a}$; R$^{2a}$ is methyl; R$^3$ is $C_{3-4}$cycloalkyl optionally substituted with one, two, or three R$^{20b}$; and each R$^{20b}$ is independently selected from amino; —CN; $C_{1-3}$alkyl; $C_{1-3}$alkoxy; $C_{1-3}$haloalkyl; —OH; —N(R$^{24}$)C(O)R$^{25}$; and —C(O)N(R$^{22}$)(R$^{23}$).

In some embodiments is a compound selected from:

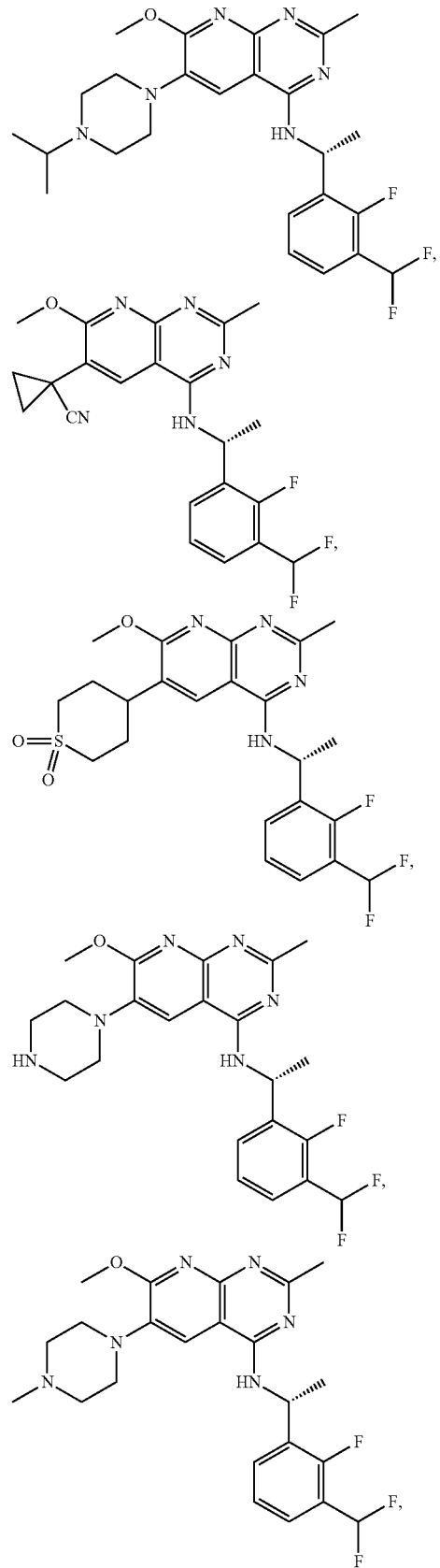

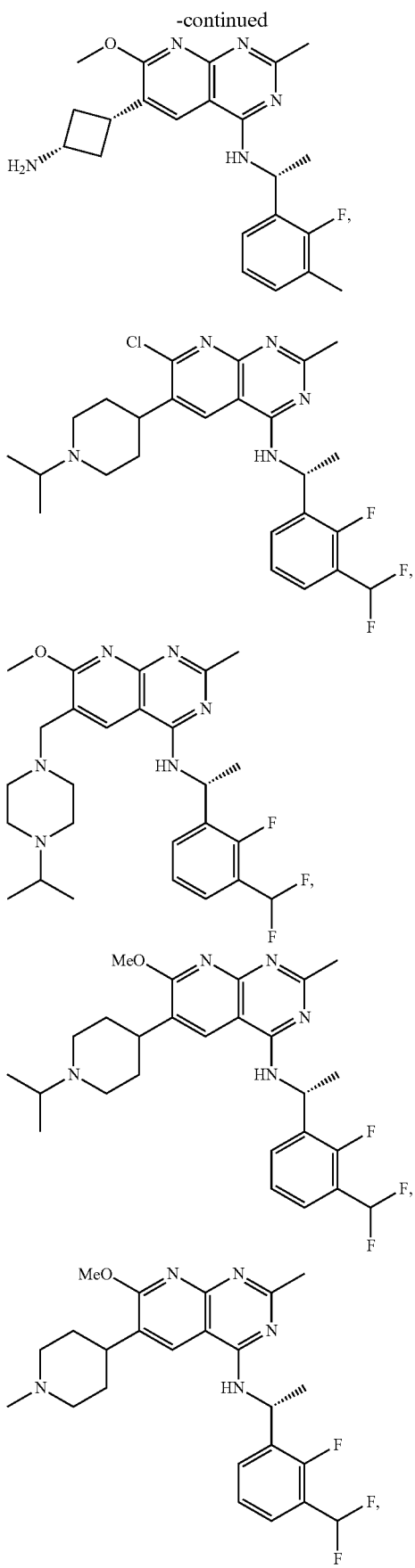

605
-continued
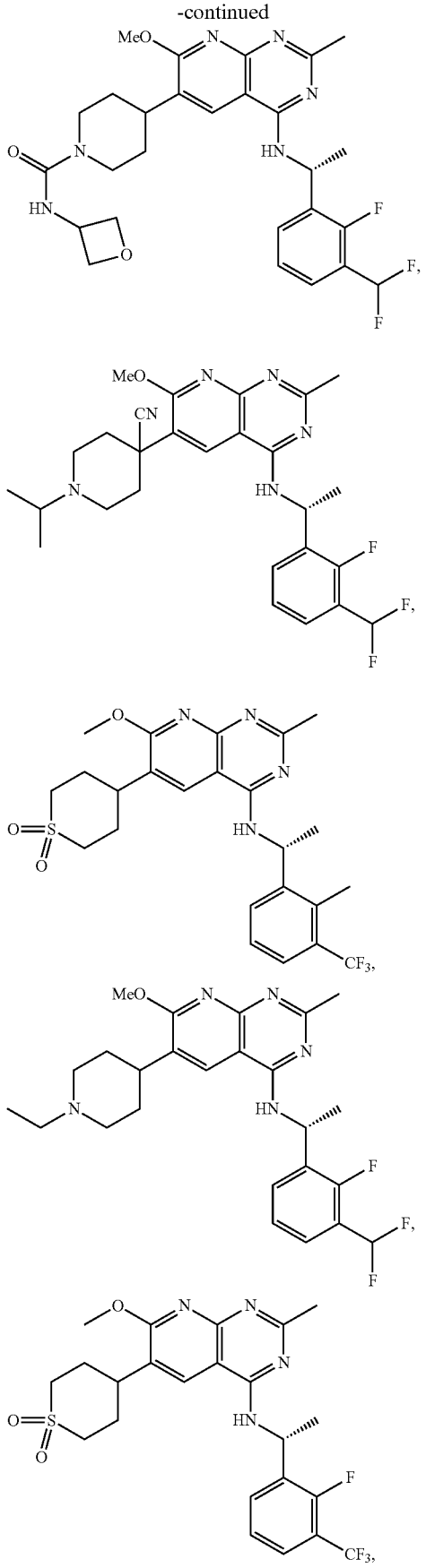
606
-continued
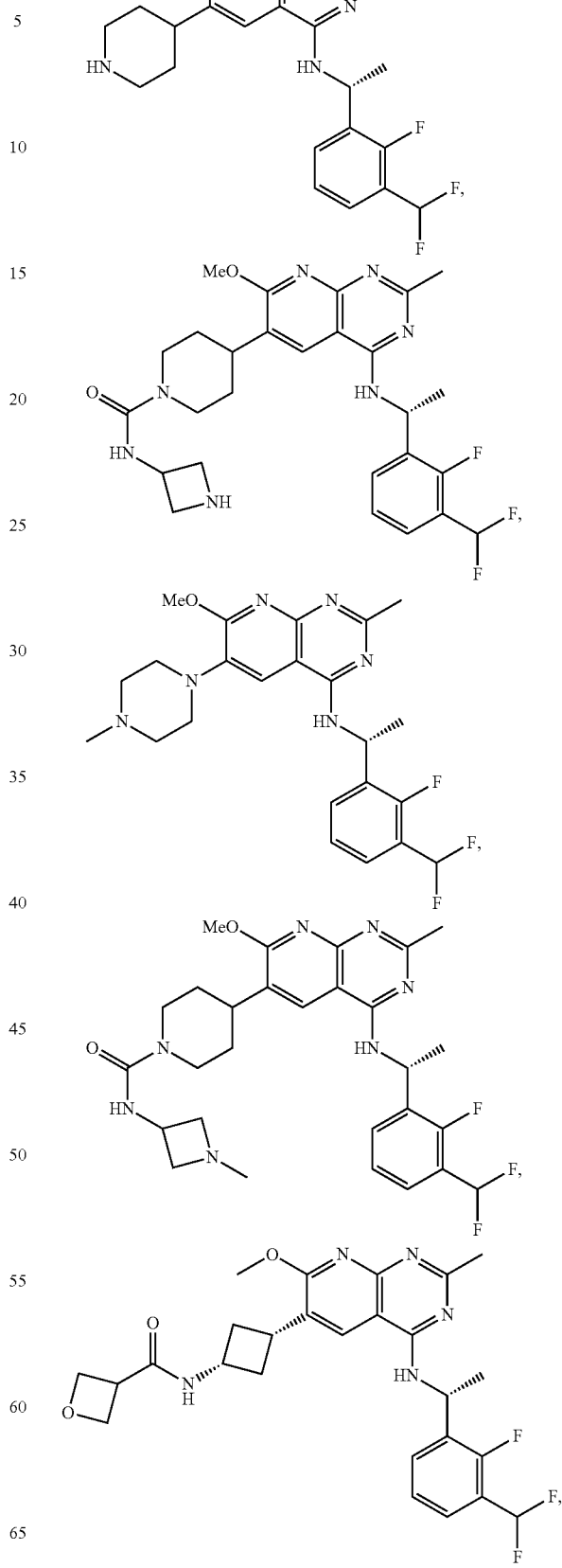

607
-continued
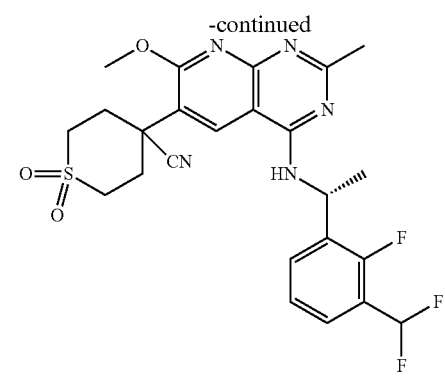
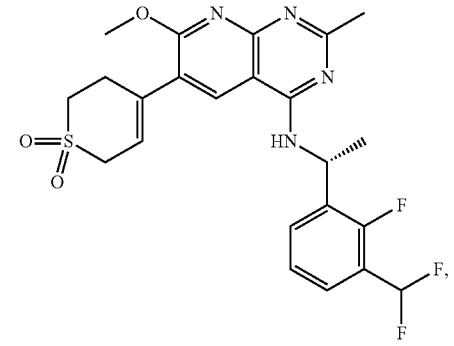
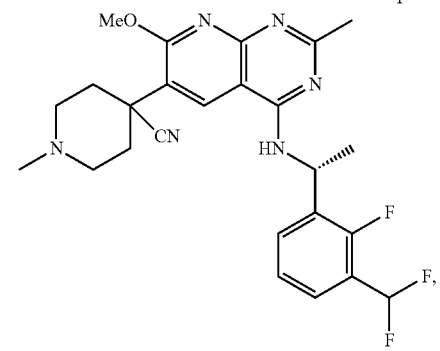
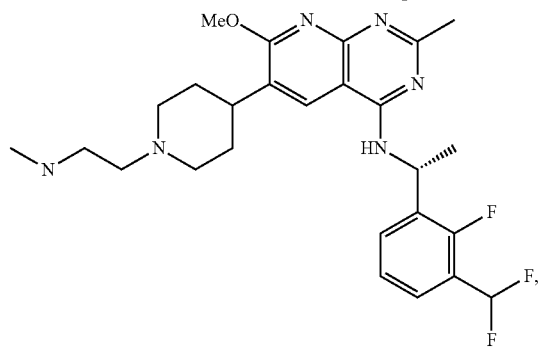
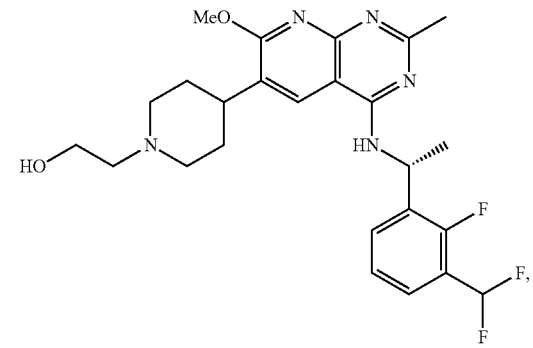
608
-continued
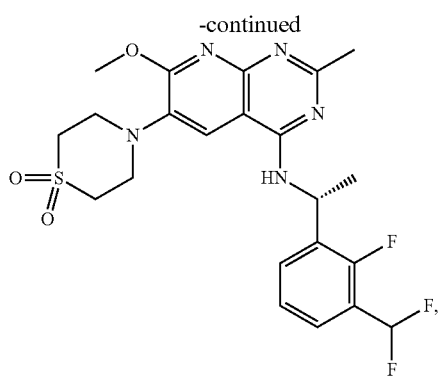
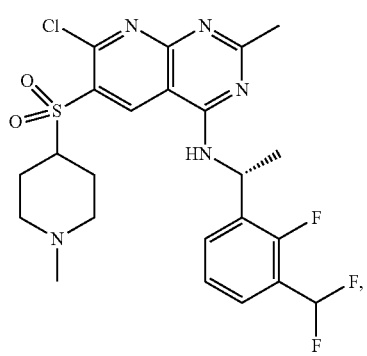
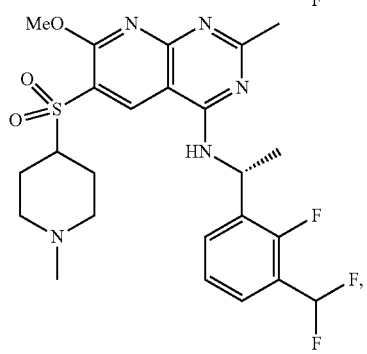
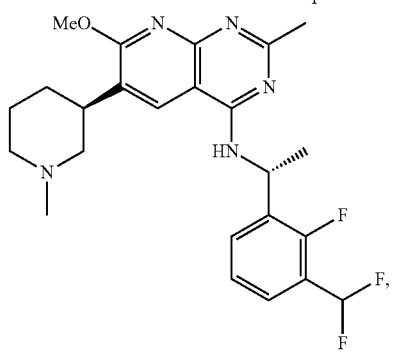
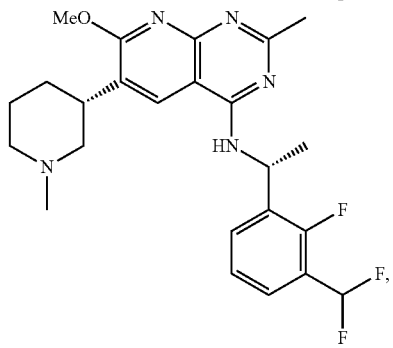

609
-continued
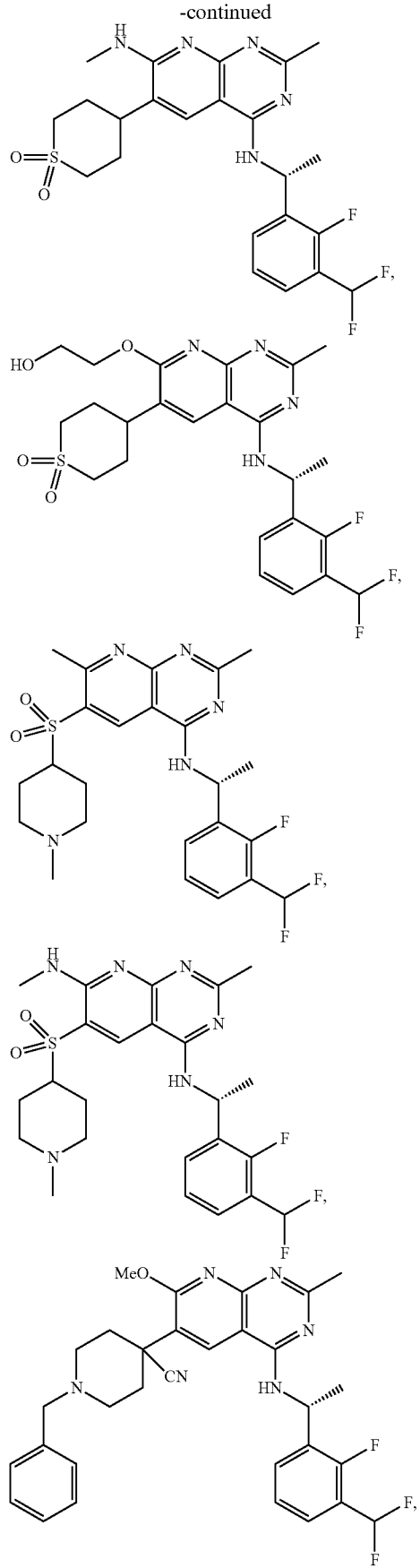
610
-continued
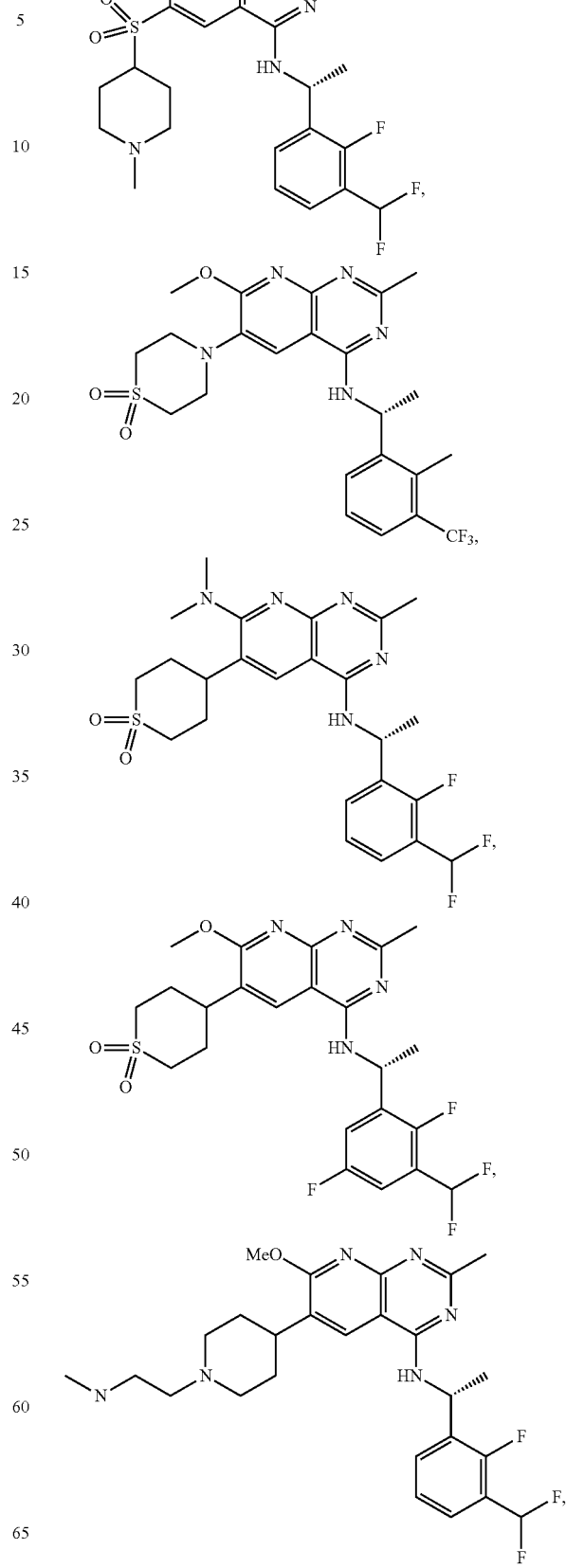

611
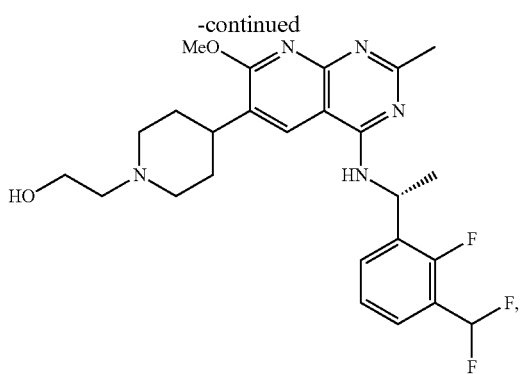
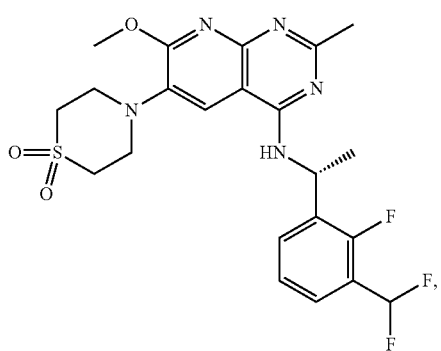
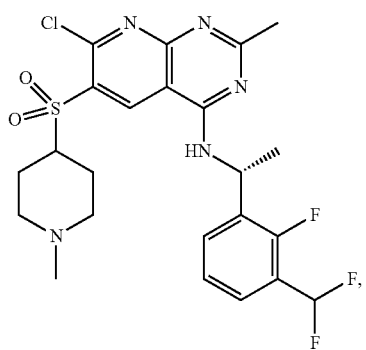
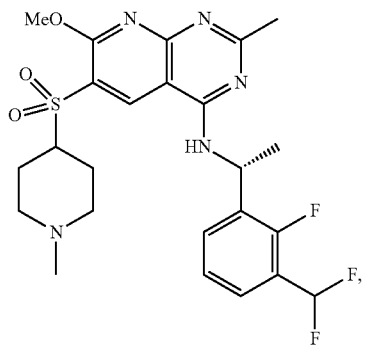
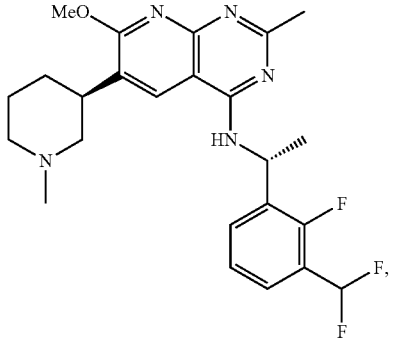
612
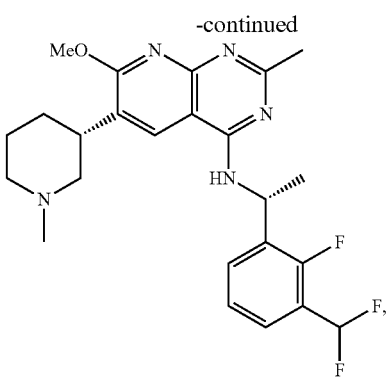
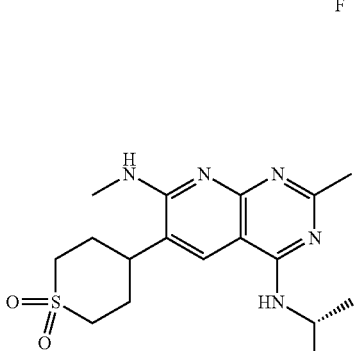
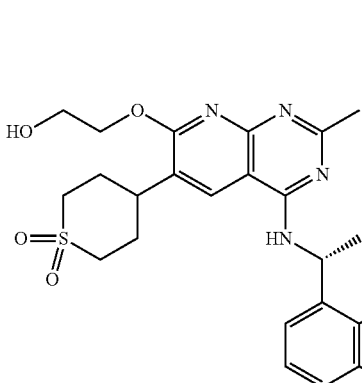

613
-continued
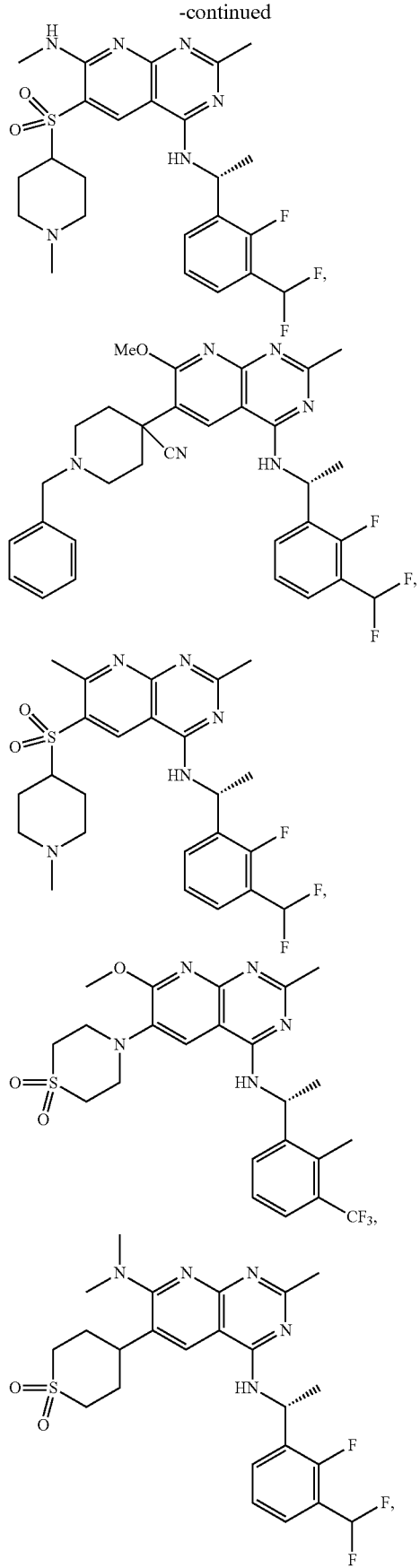
614
-continued
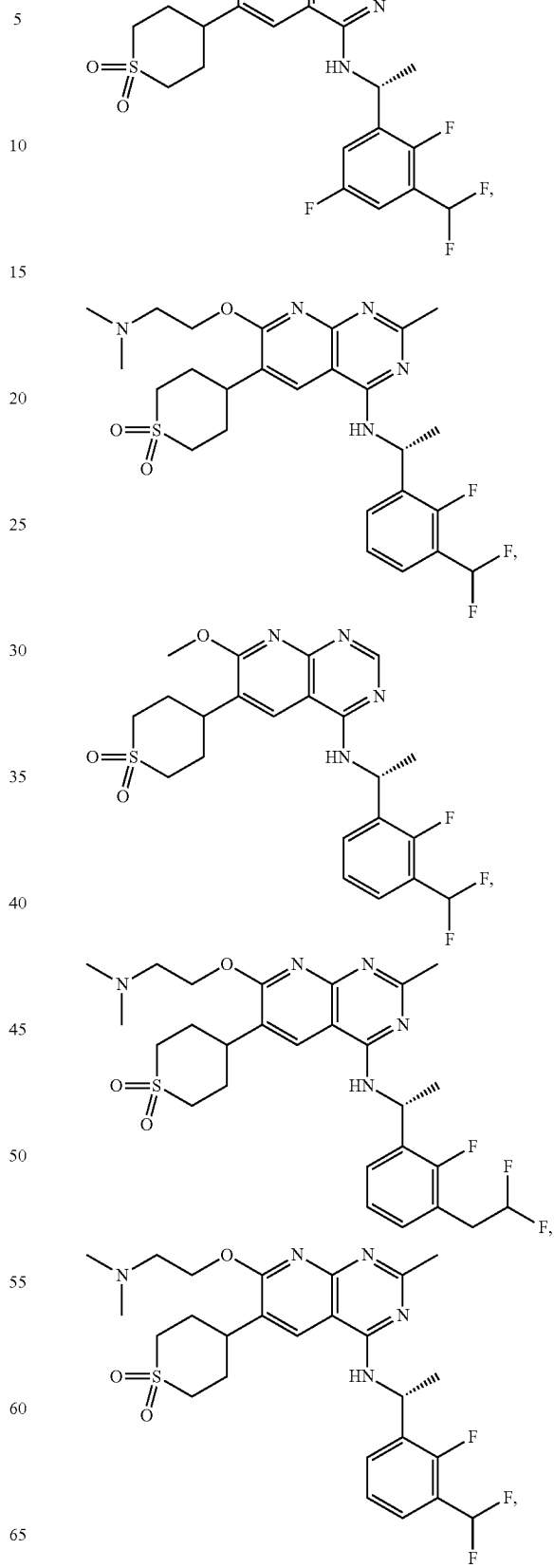

615
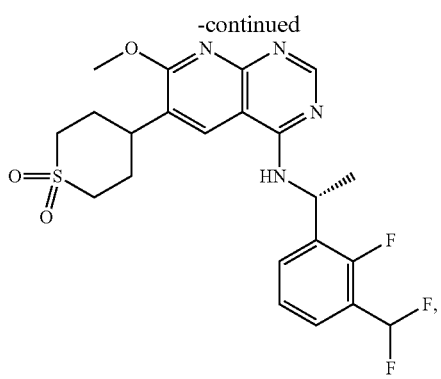
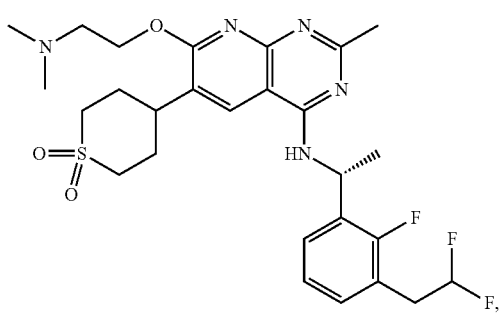
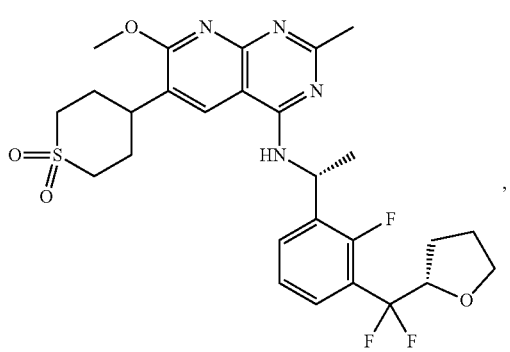
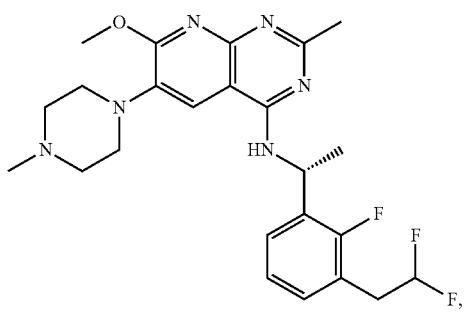
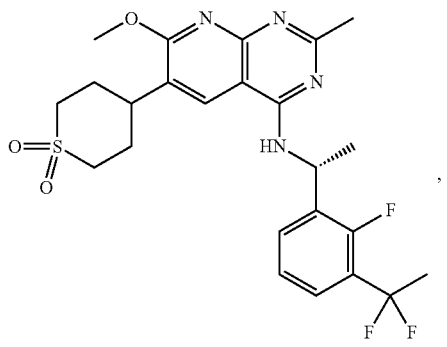
616
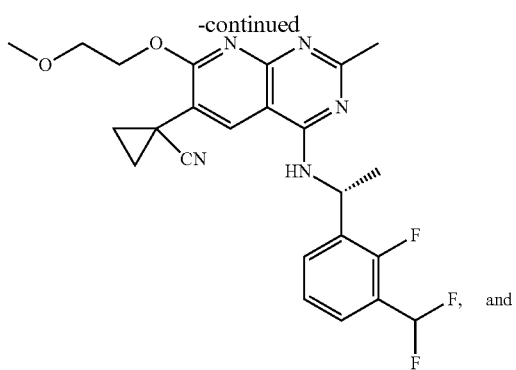
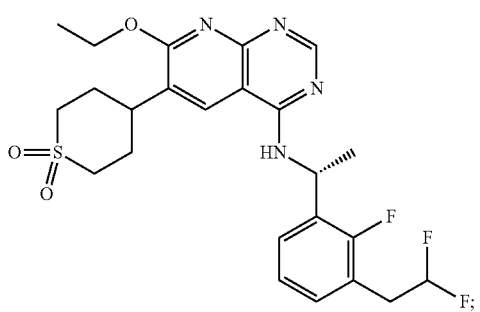
or a pharmaceutically acceptable salt or solvate thereof.
In some embodiments is a compound selected from:
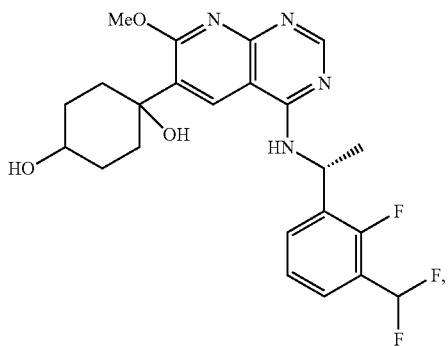
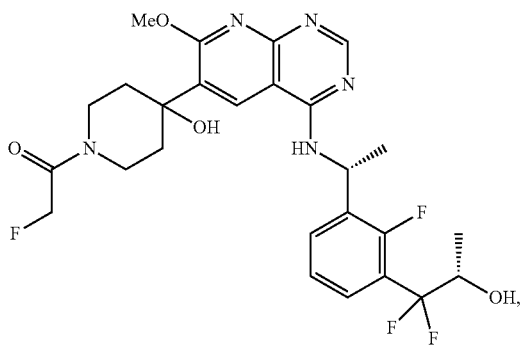

617
-continued
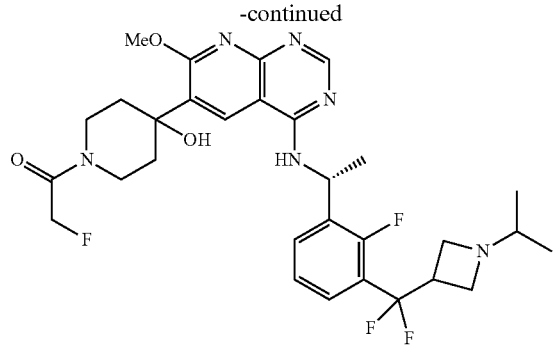
,
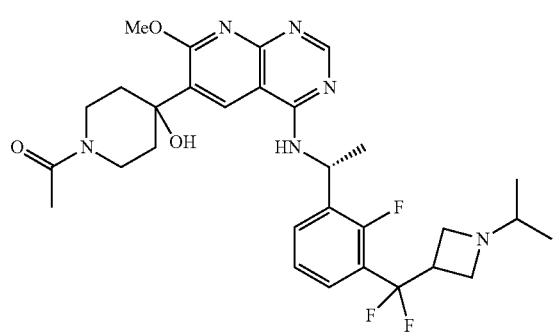
,
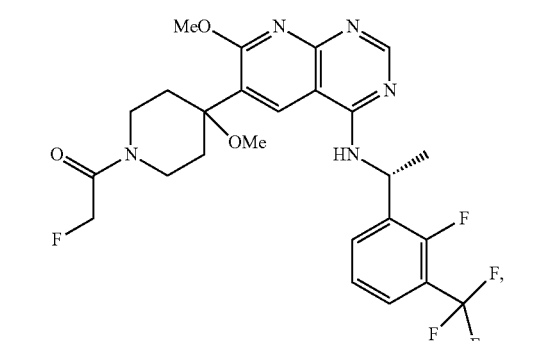
,
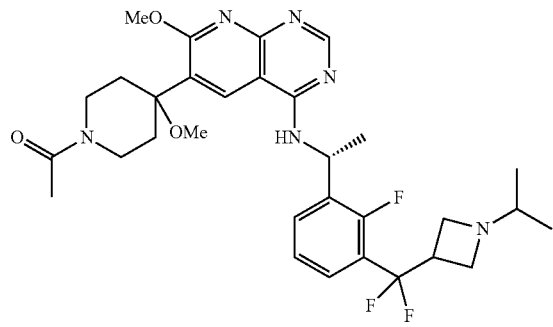
,
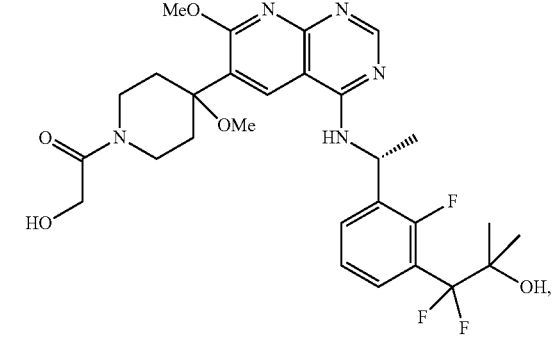
,
618
-continued
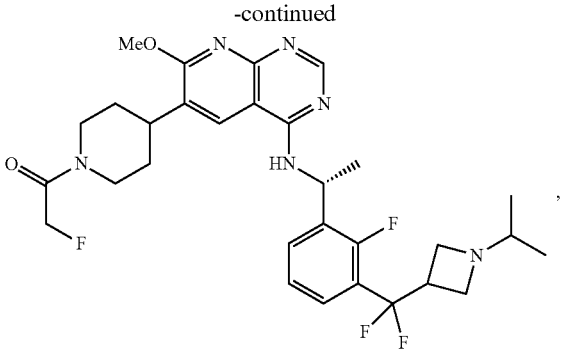
,
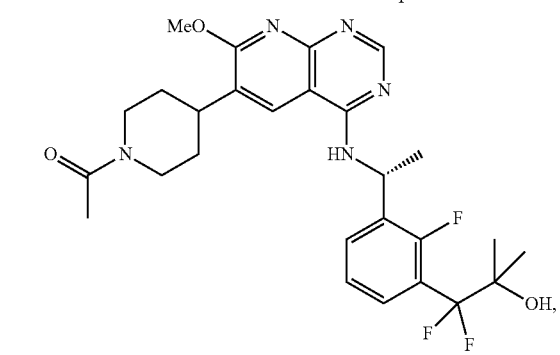
,
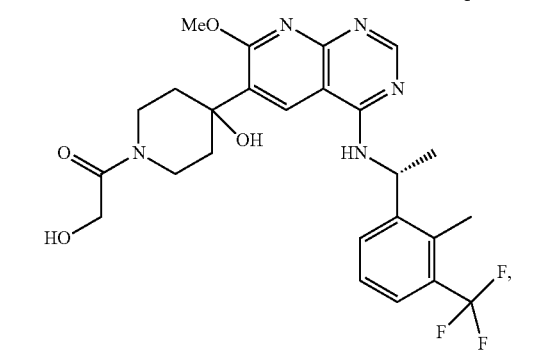
,
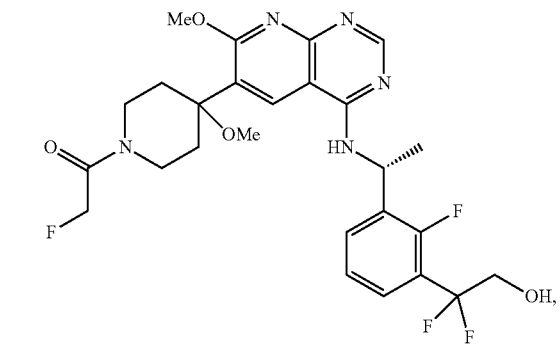
,
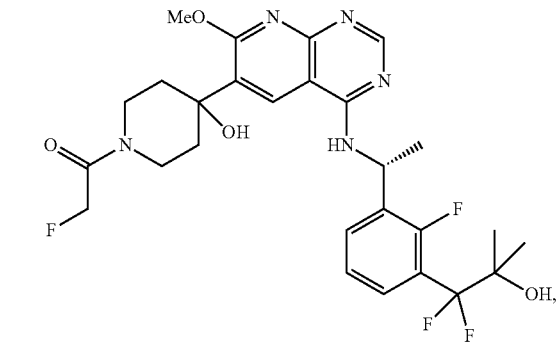
, 619
-continued
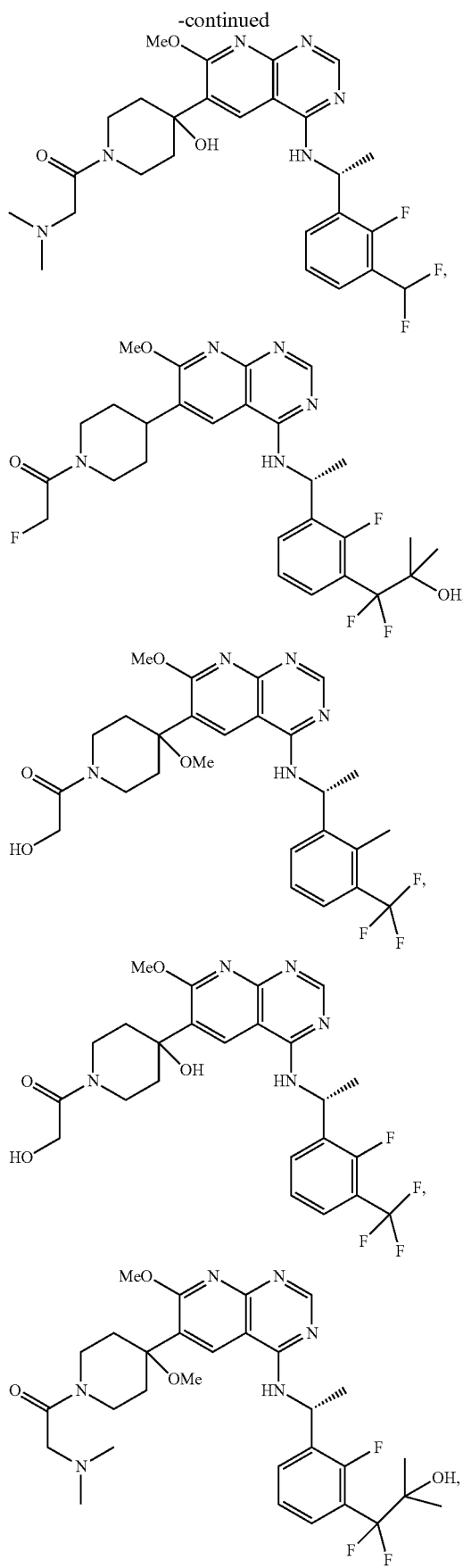
620
-continued
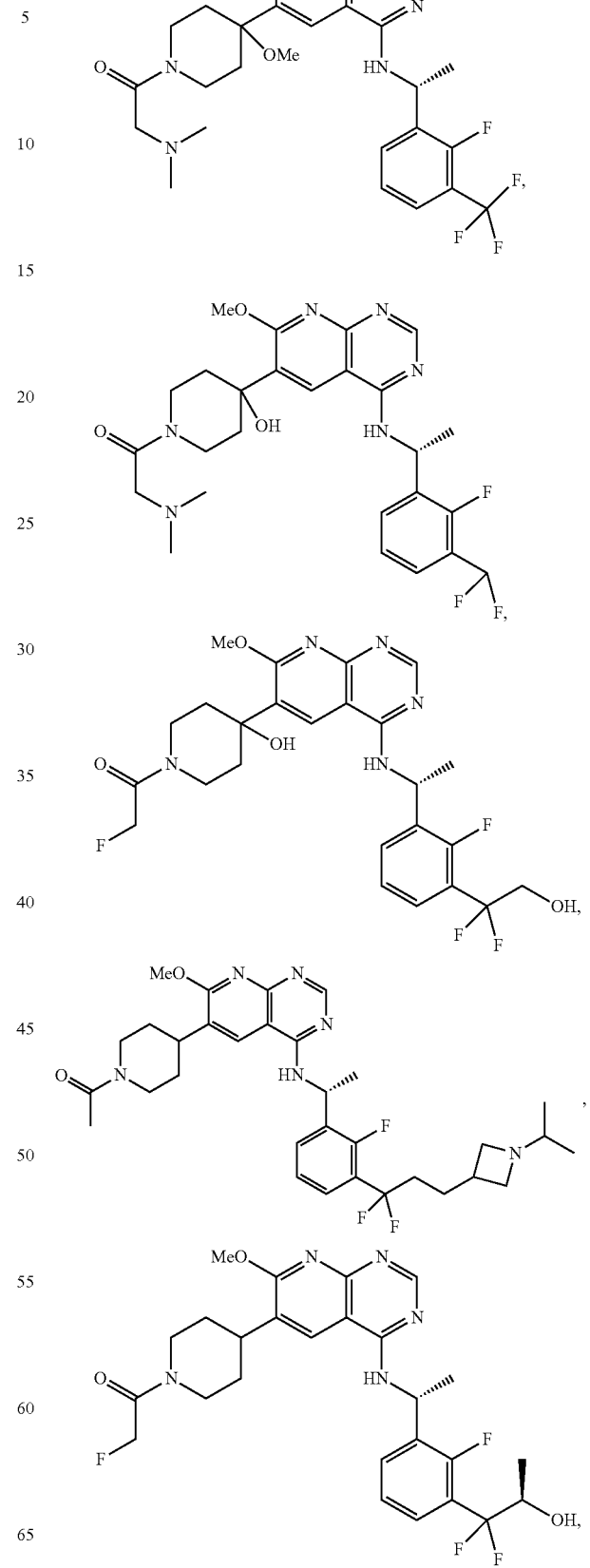

621
-continued
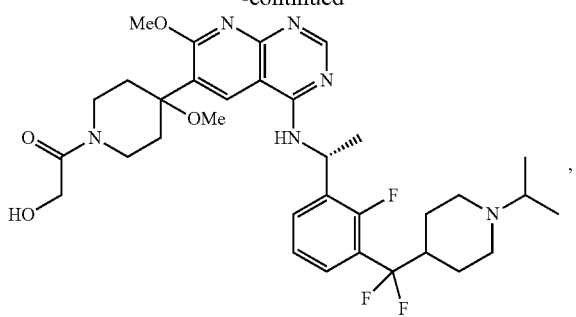
,
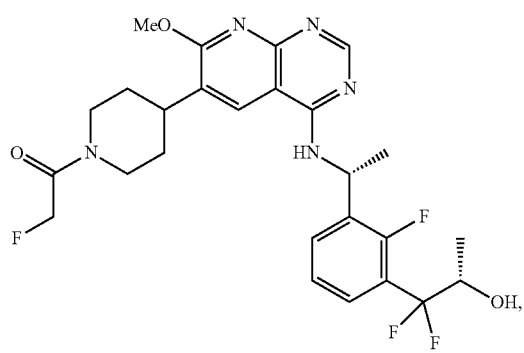
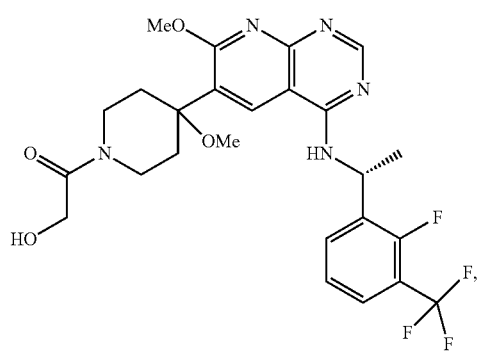
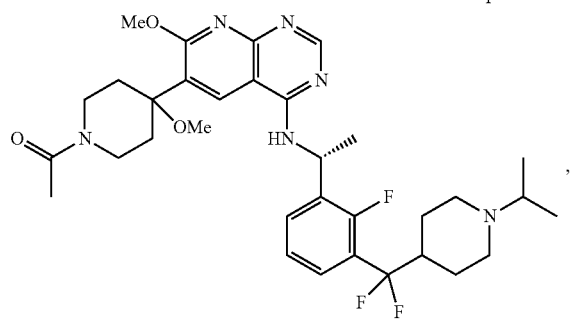
,
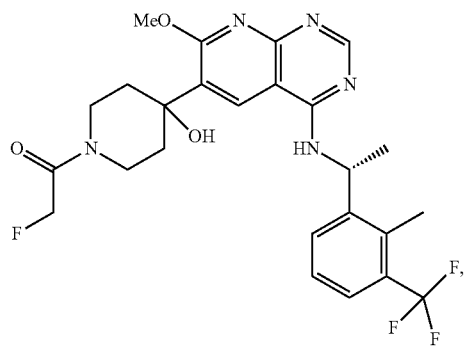
622
-continued
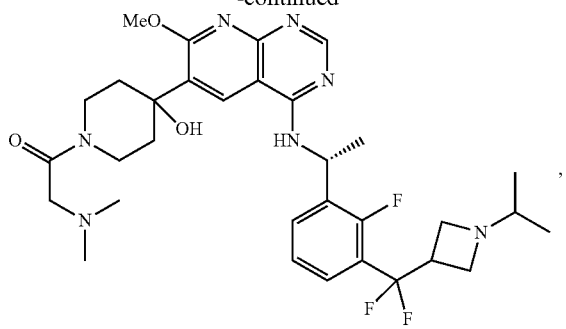
,
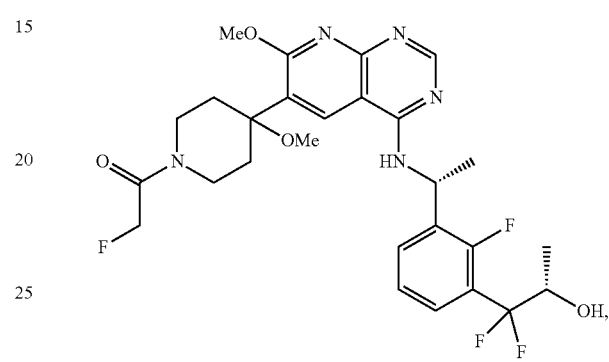
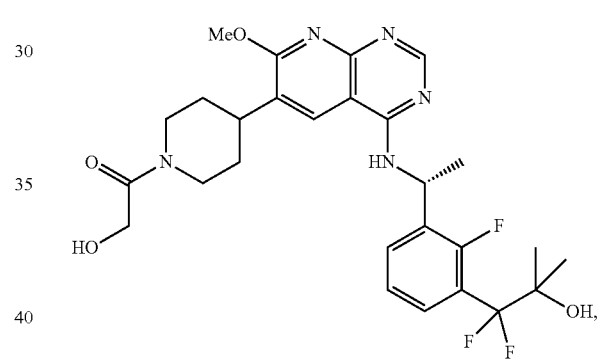
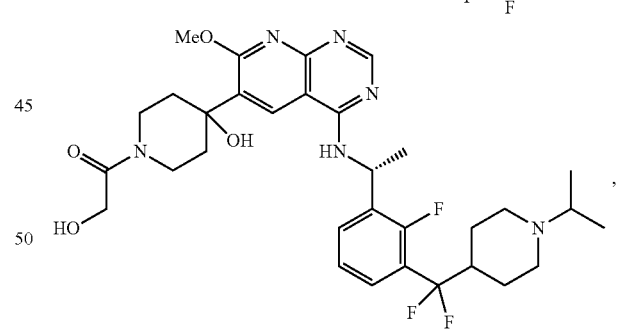
,
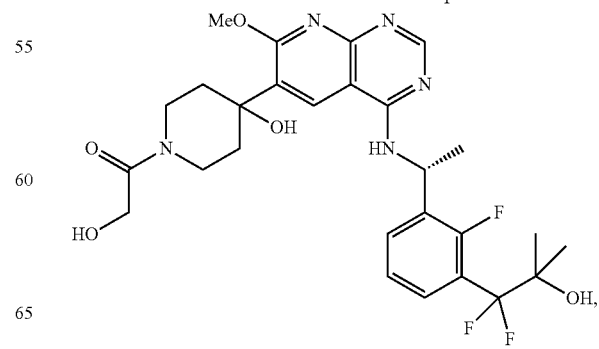

-continued
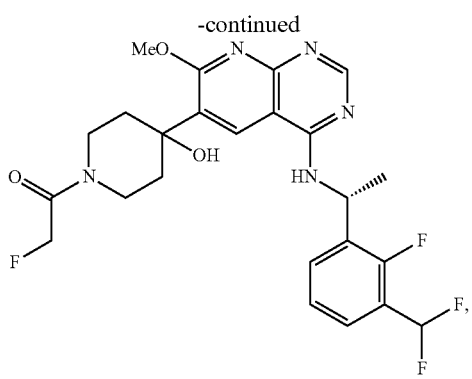
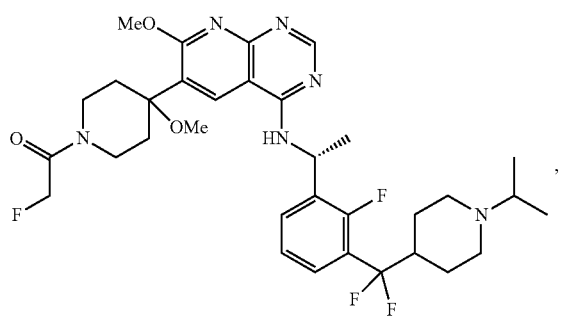
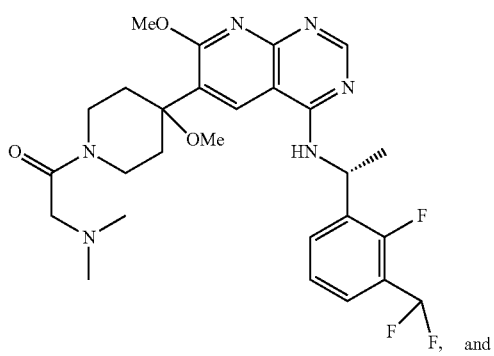
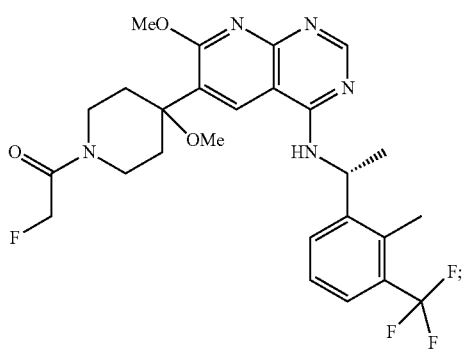
or a pharmaceutically acceptable salt or solvate thereof.
In some embodiments is a compound selected from:
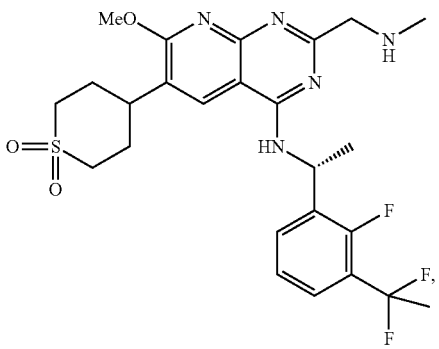
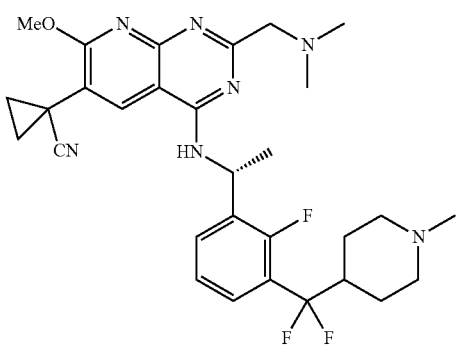
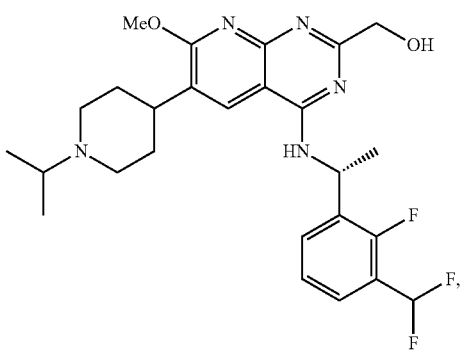
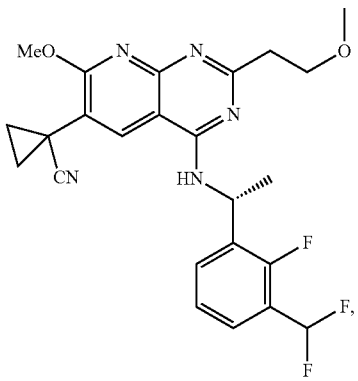

625
-continued
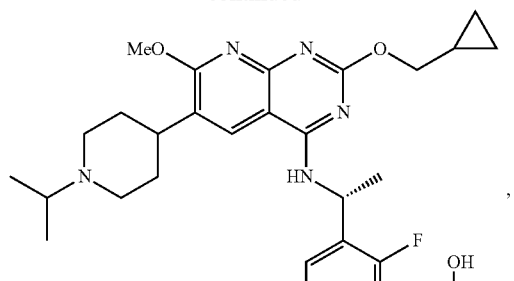
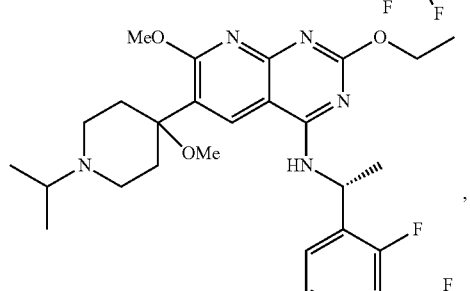
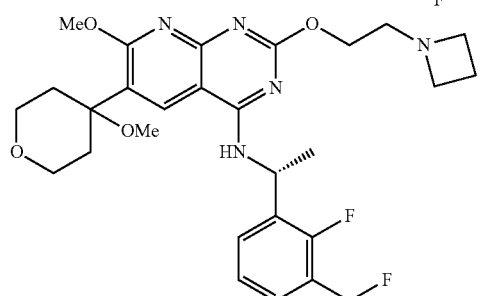
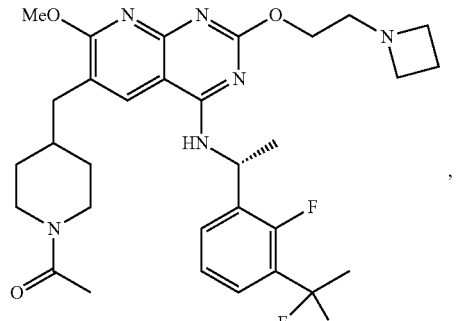
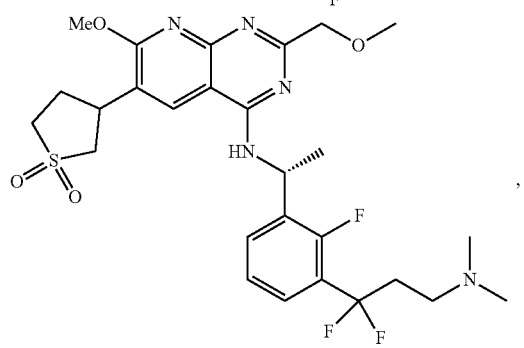
626
-continued
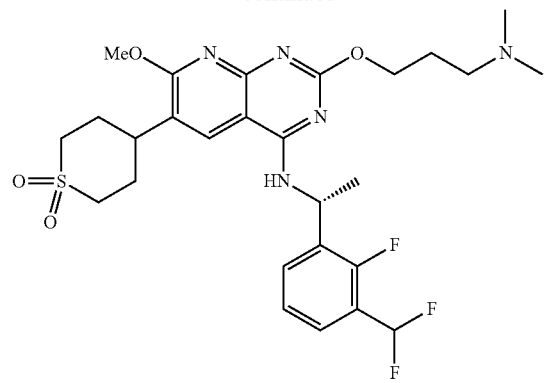
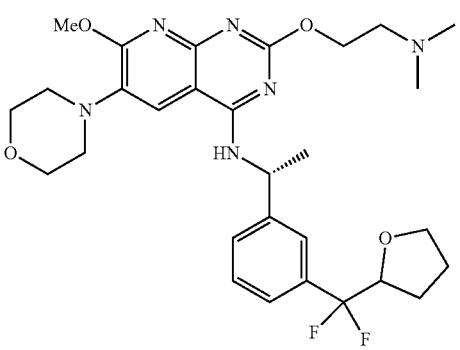
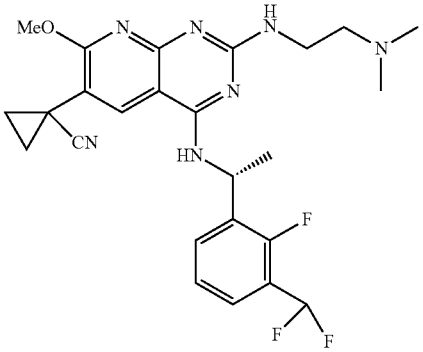
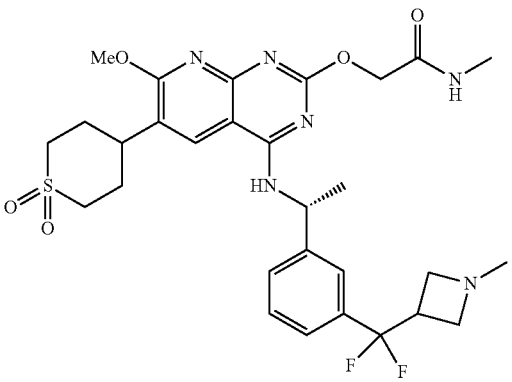

627
-continued
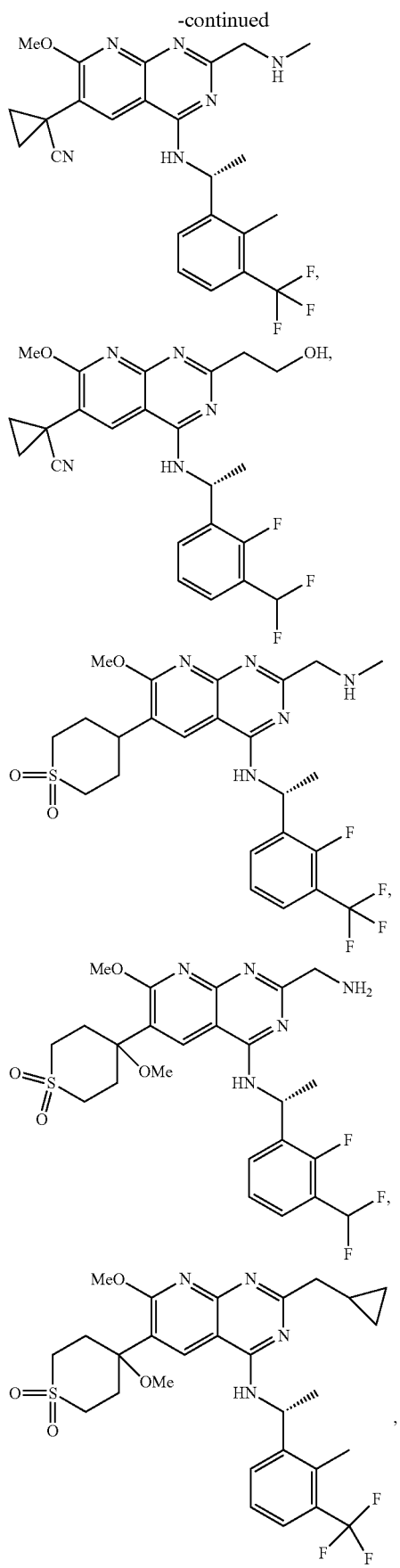
628
-continued
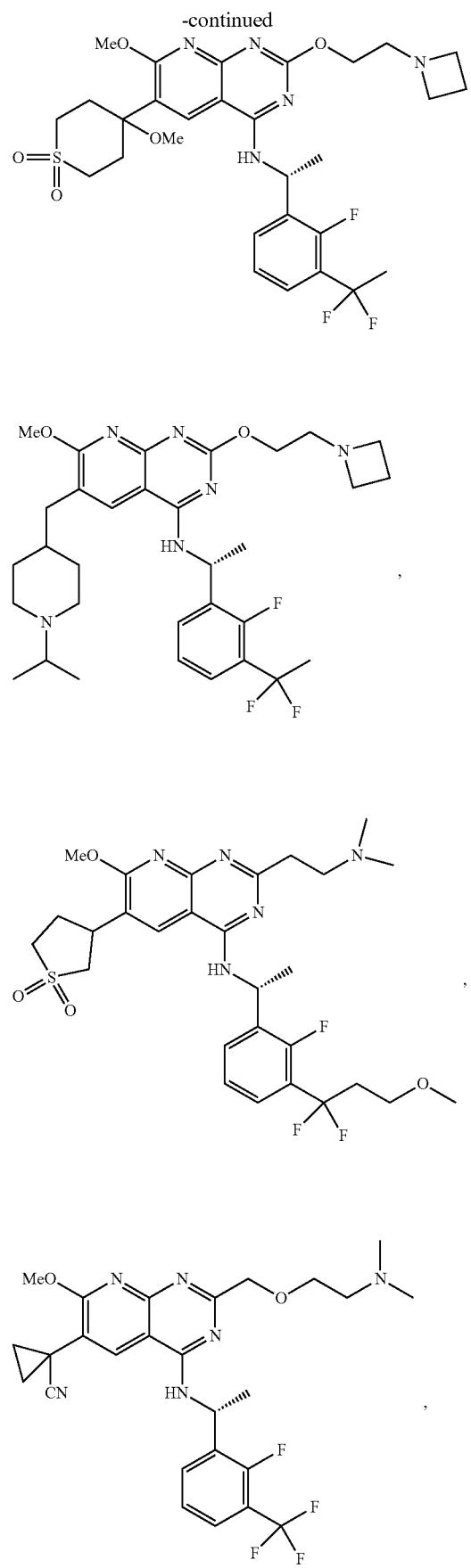

629                                              630
-continued                                    -continued
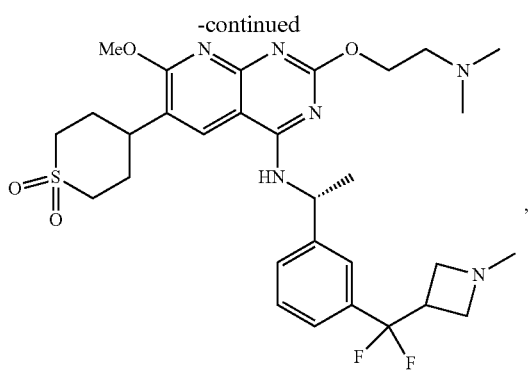
,
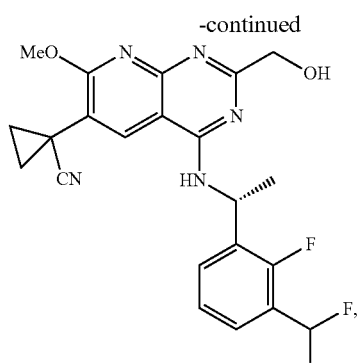
,
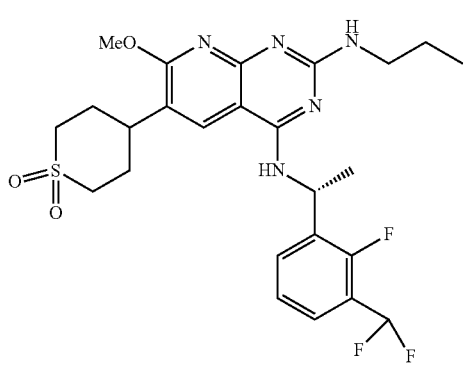
,
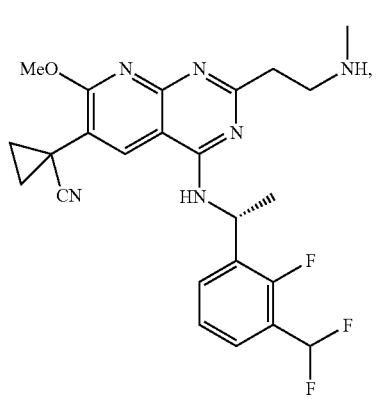
,
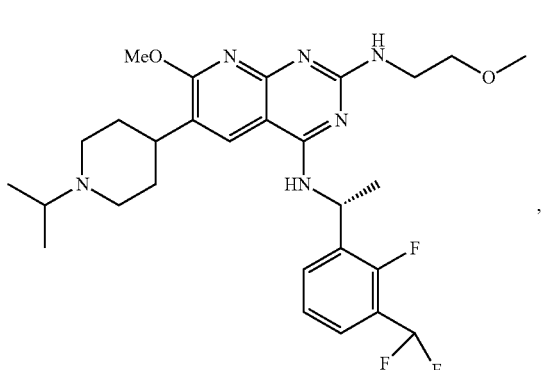
,
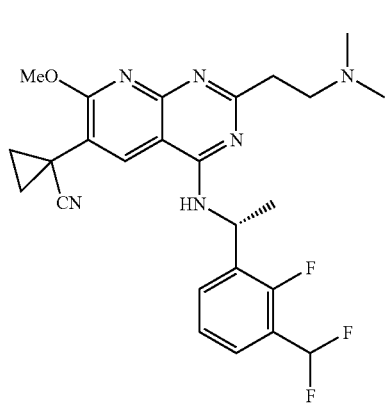
,
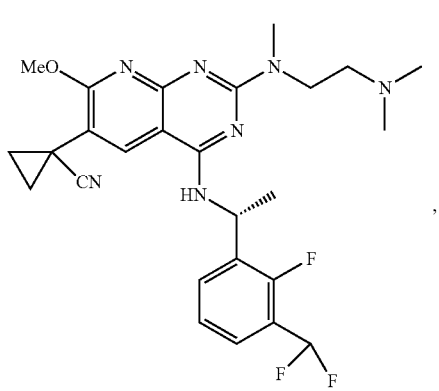
,
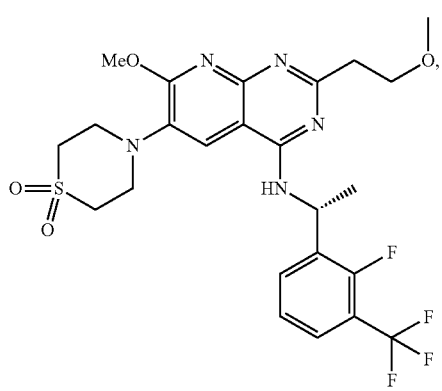
, 631
-continued
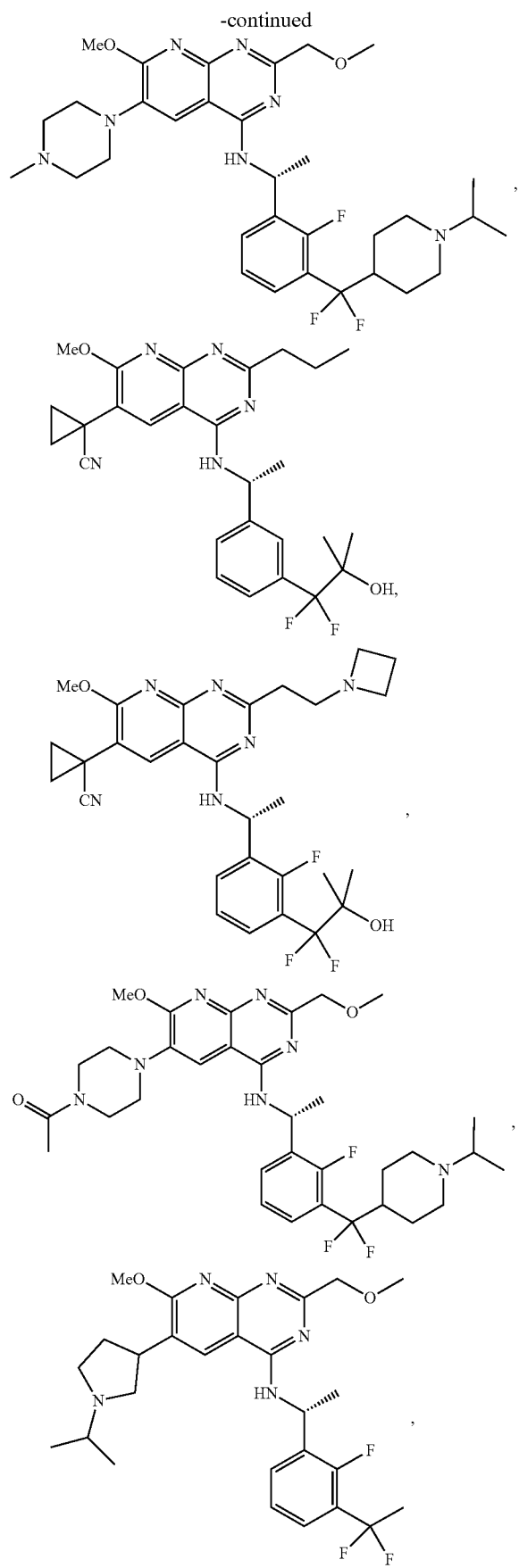
632
-continued
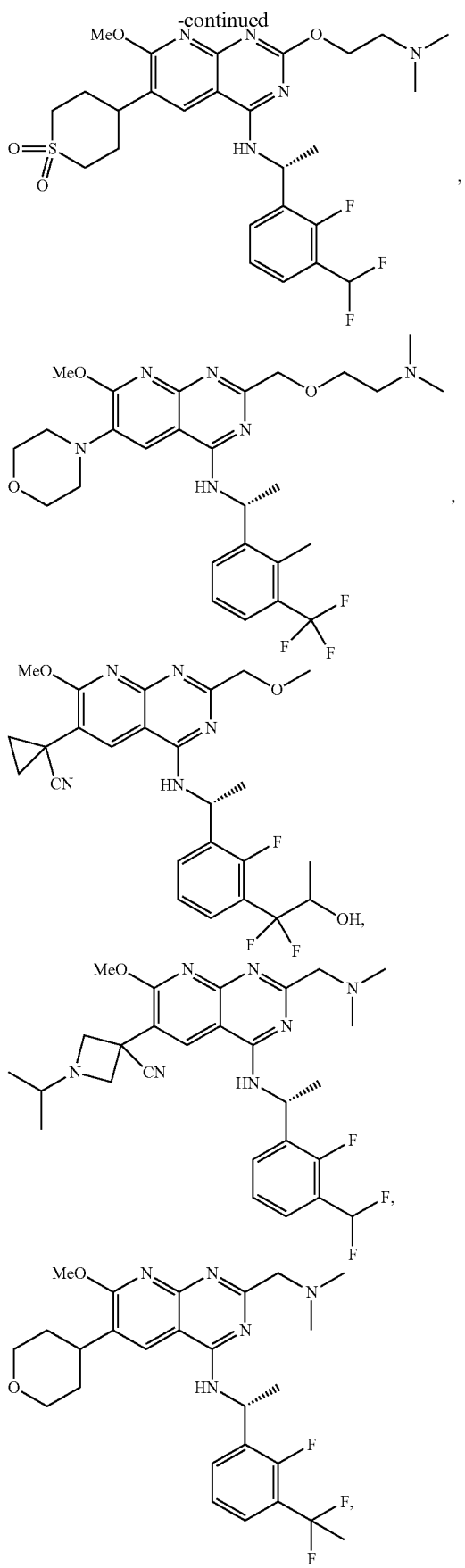

633
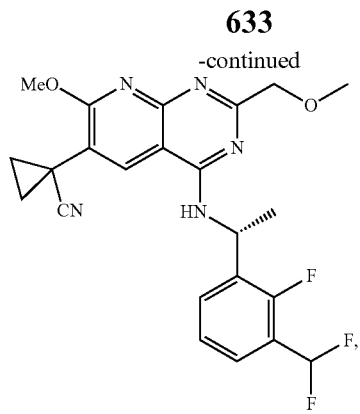
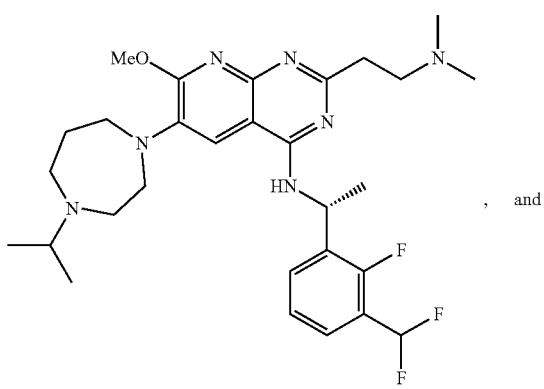
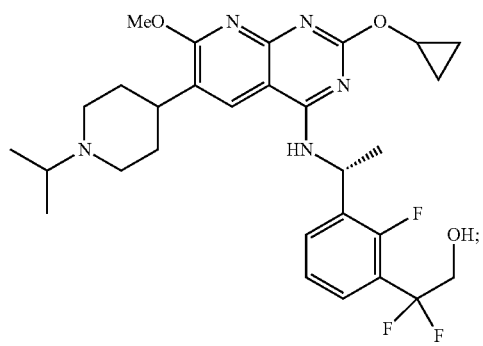
or a pharmaceutically acceptable salt or solvate thereof.
In some embodiments is a compound selected from:
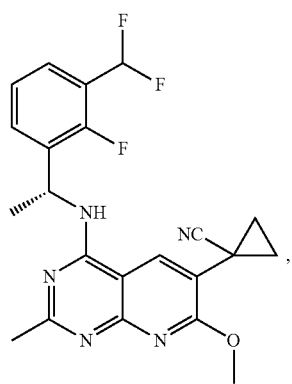
634
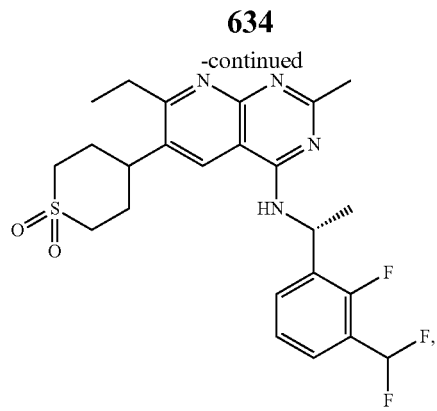
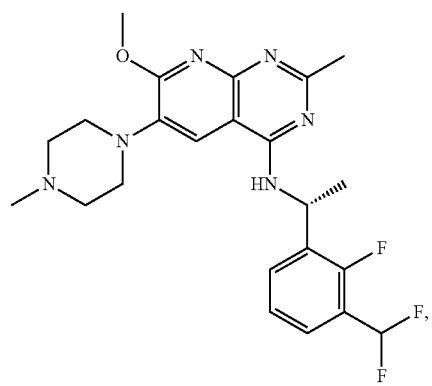
, and
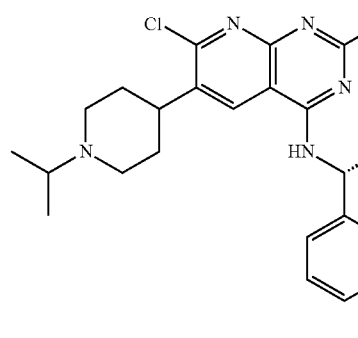
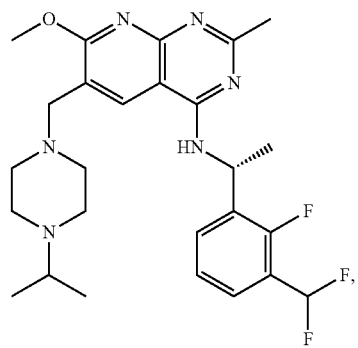

635
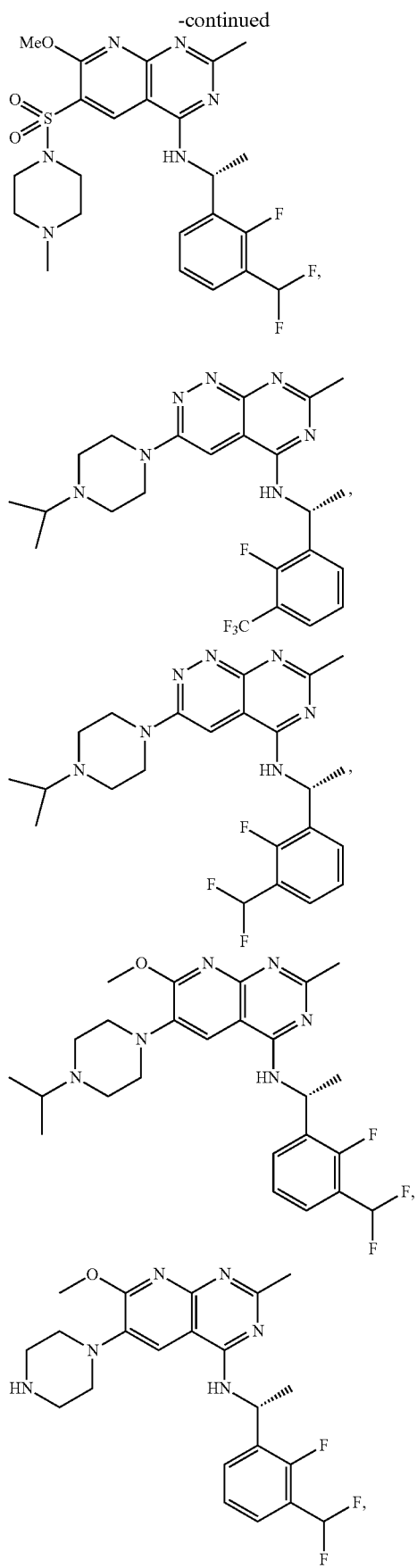
636
-continued
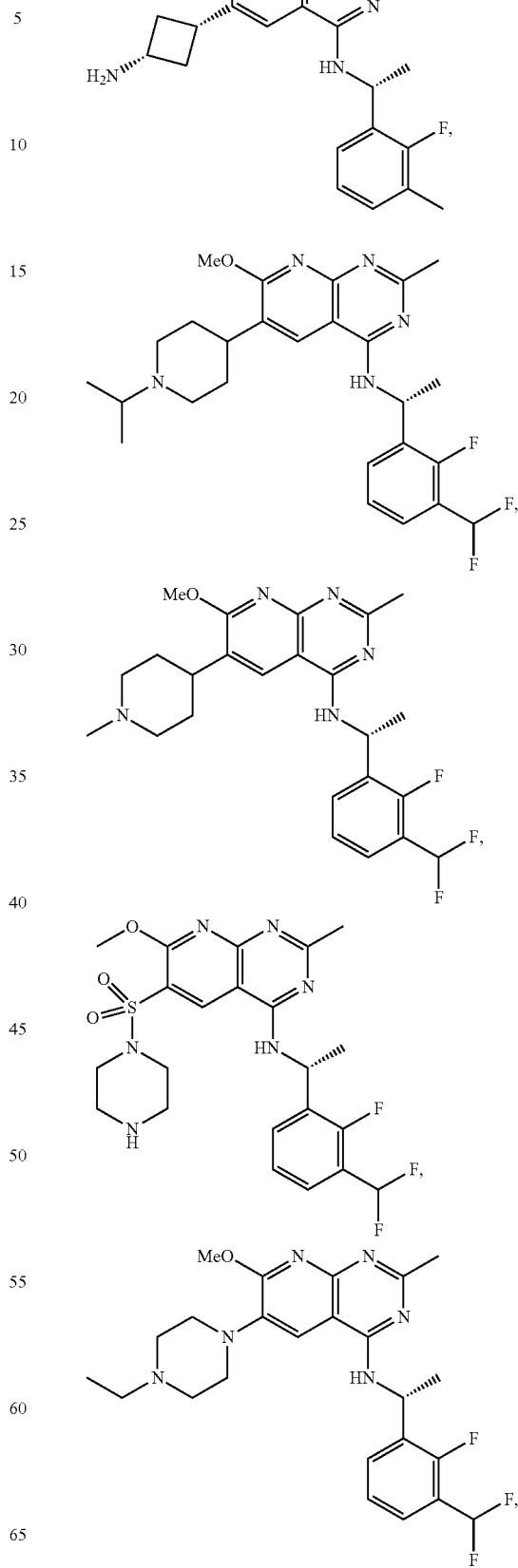

637
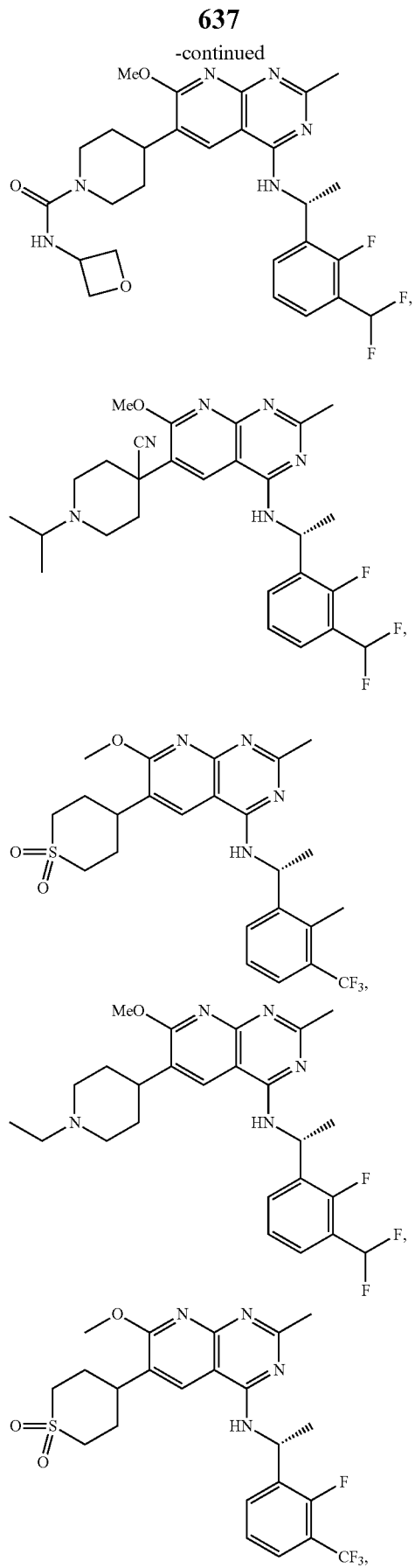
638
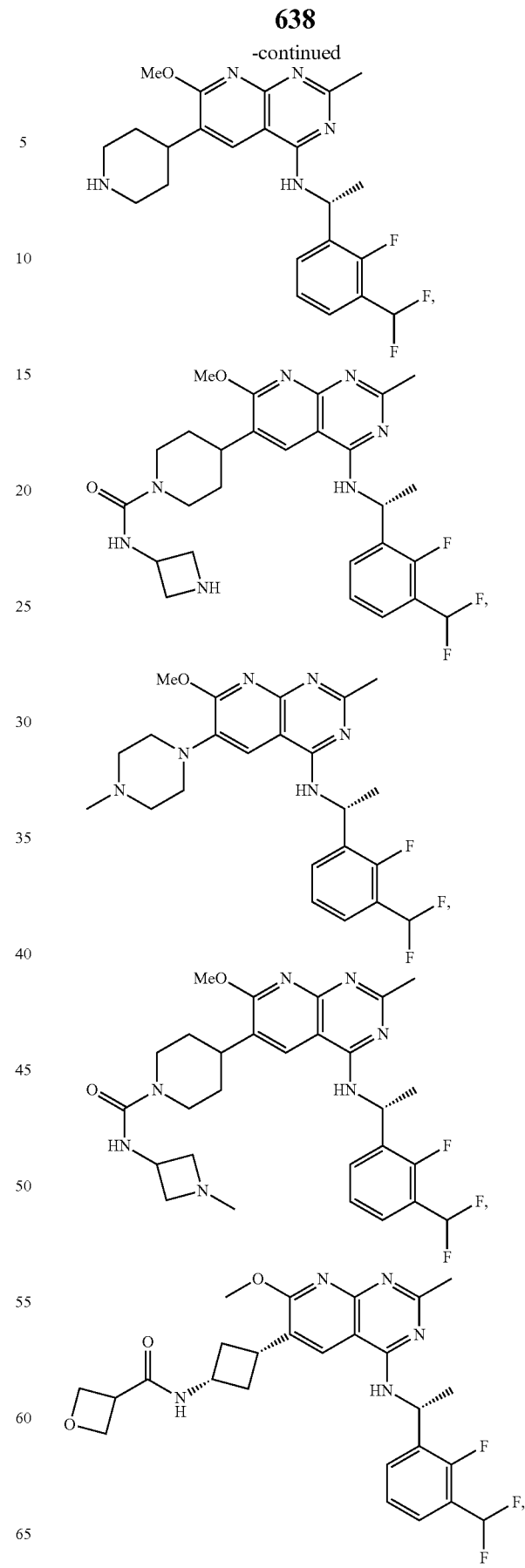

639 -continued
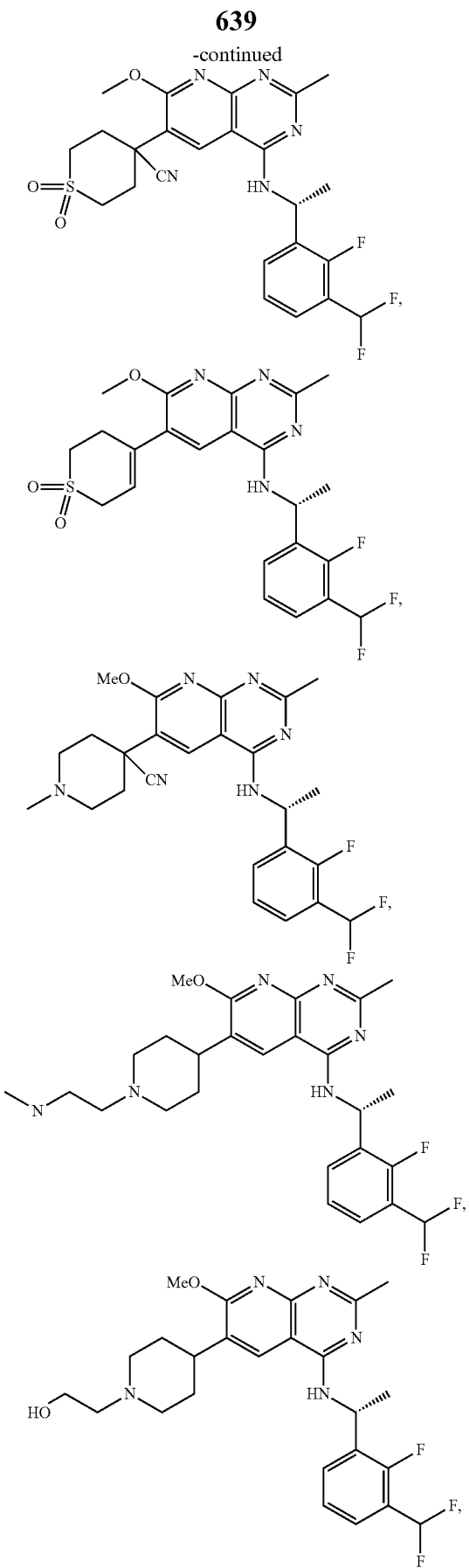
640 -continued
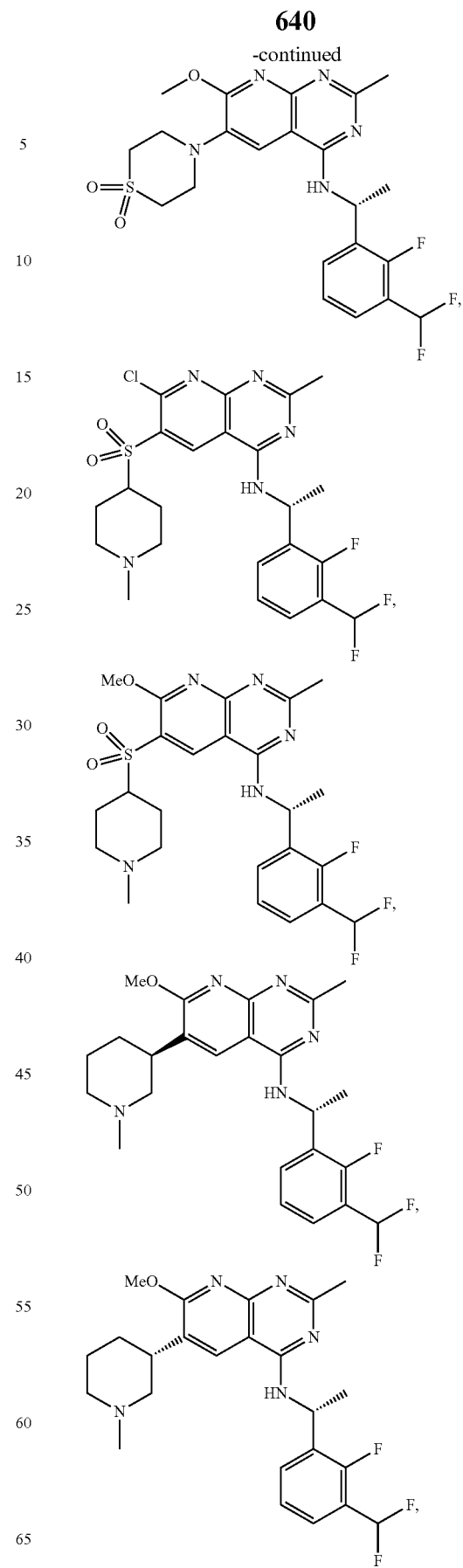

641
-continued
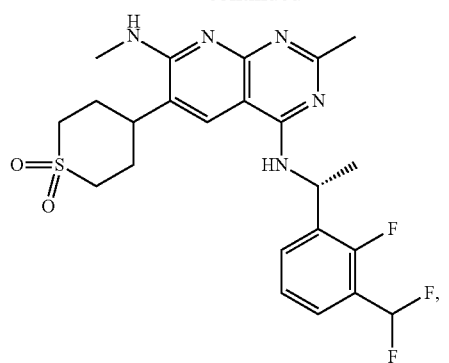
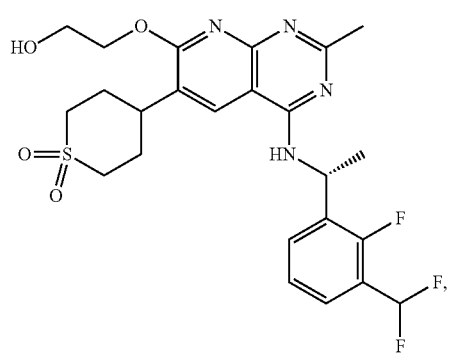
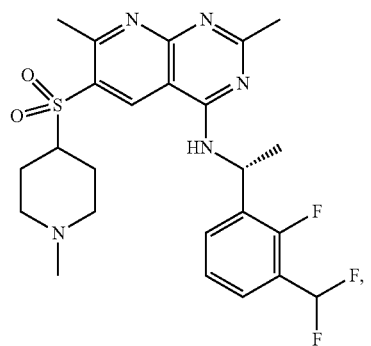
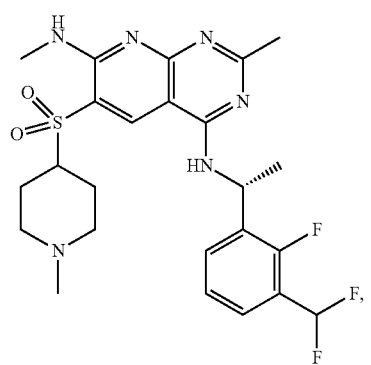
642
-continued
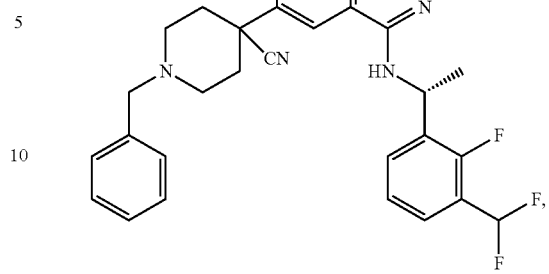
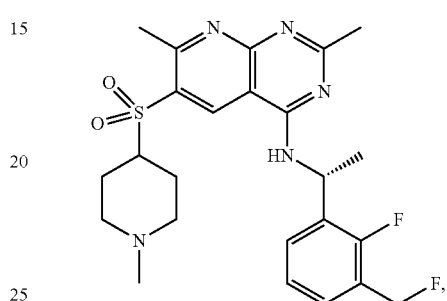
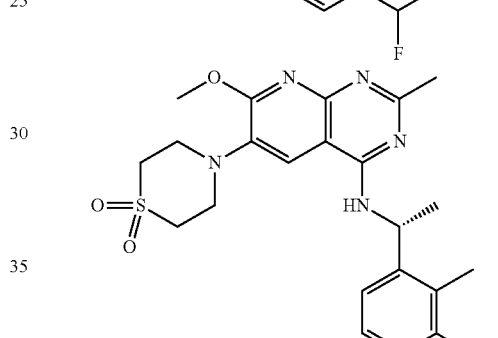
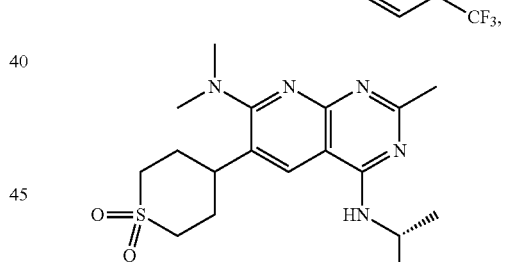
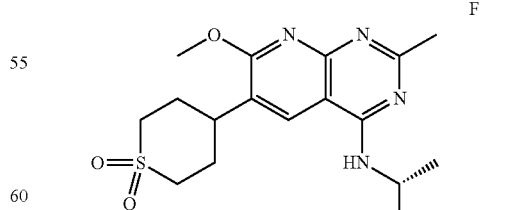
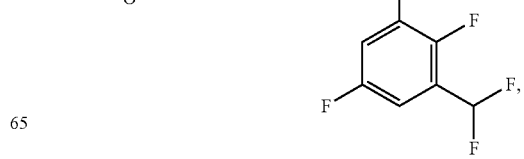

643
-continued
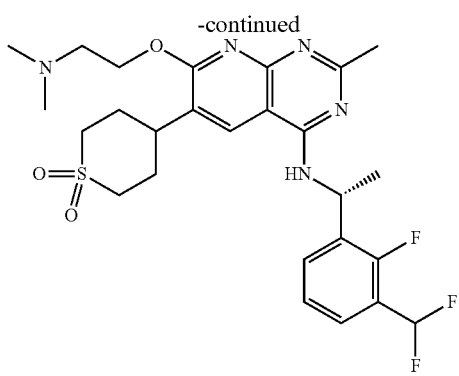
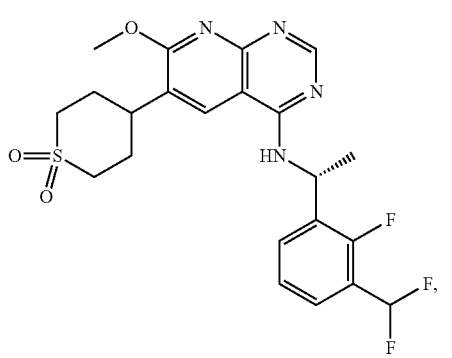
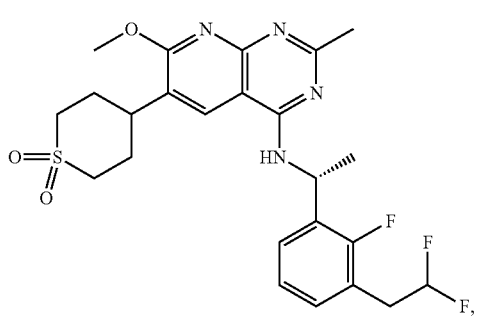
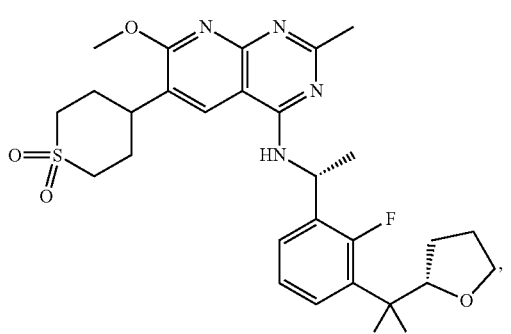
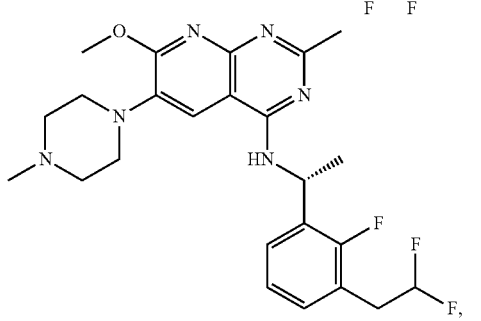
644
-continued
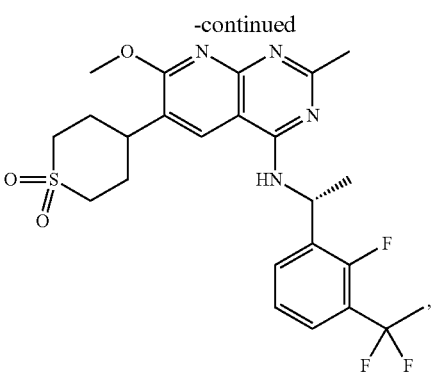
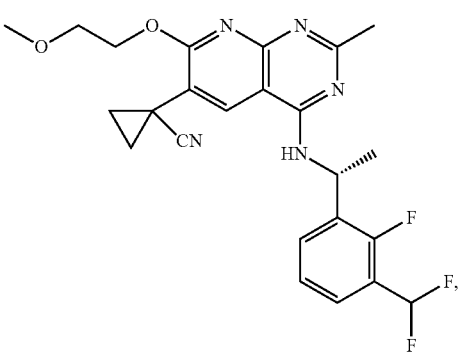
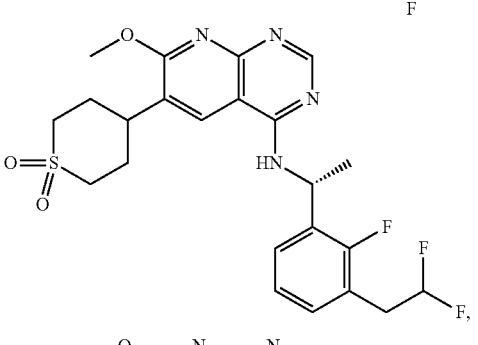
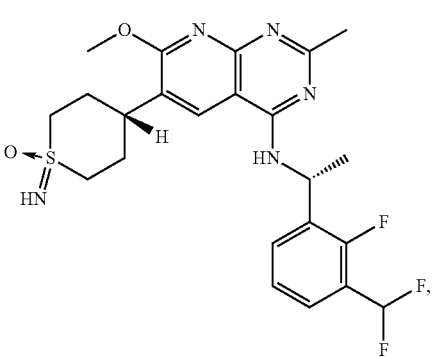
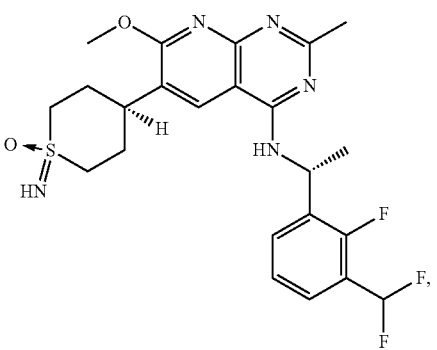

645
-continued
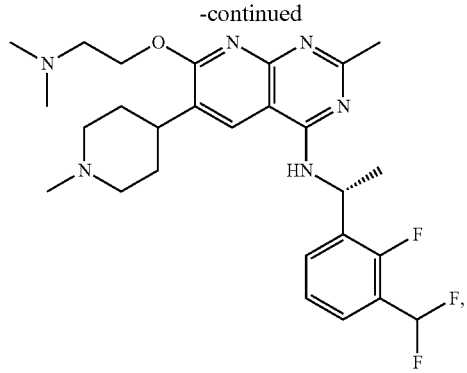
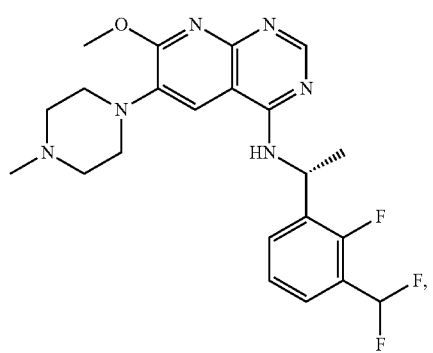
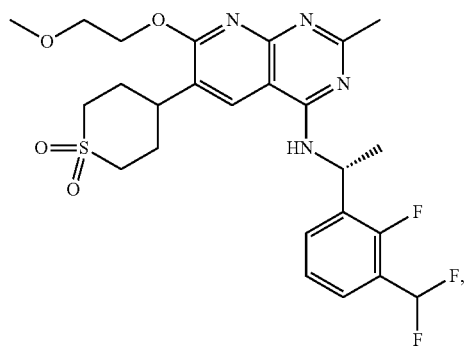
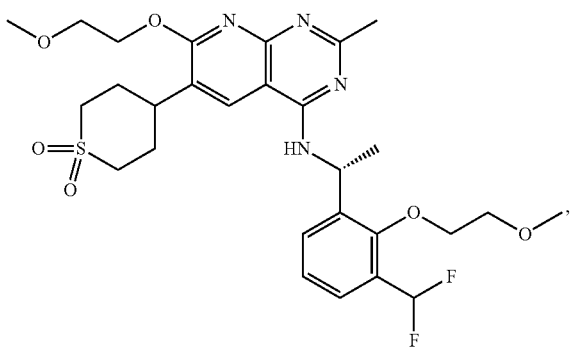
646
-continued
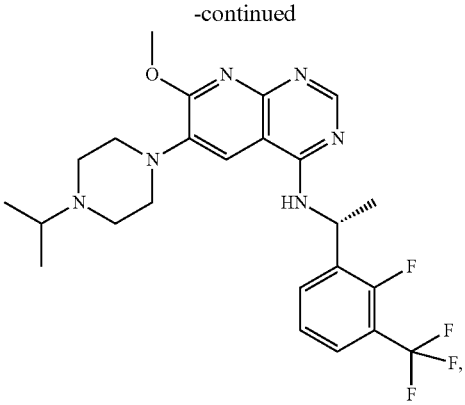
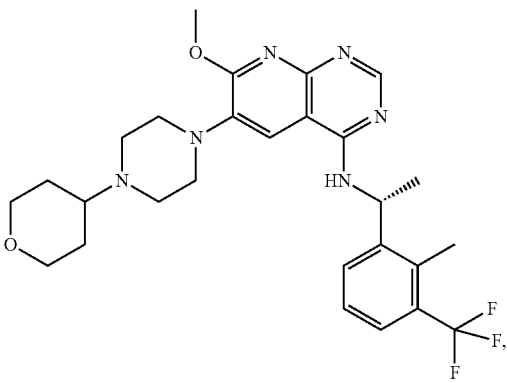
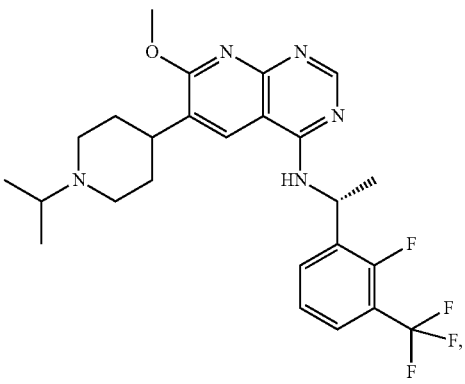

647
-continued
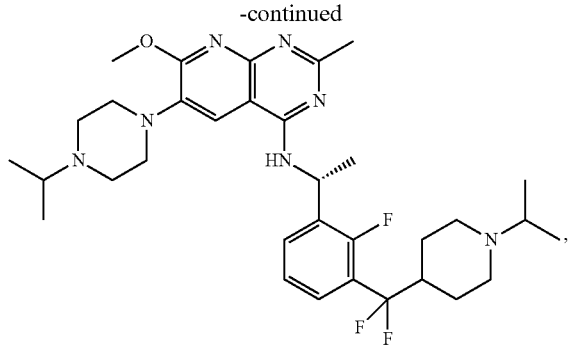
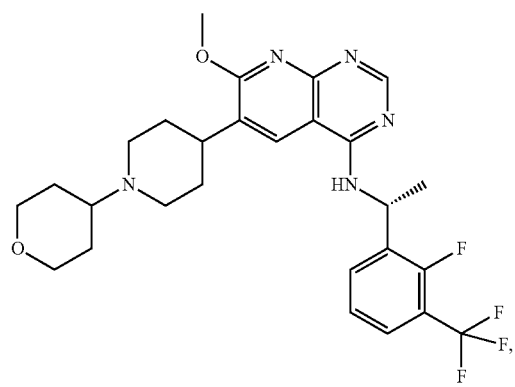
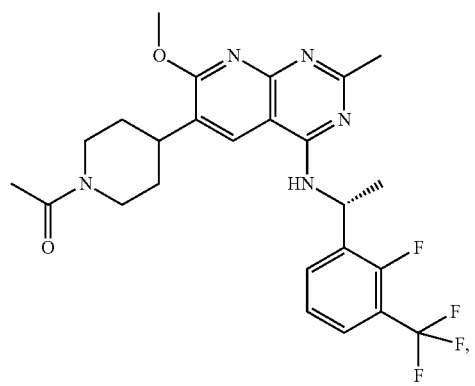
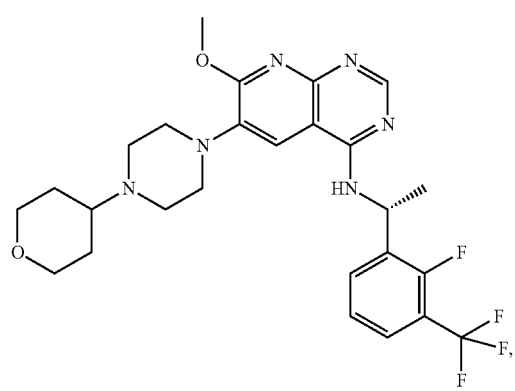
648
-continued
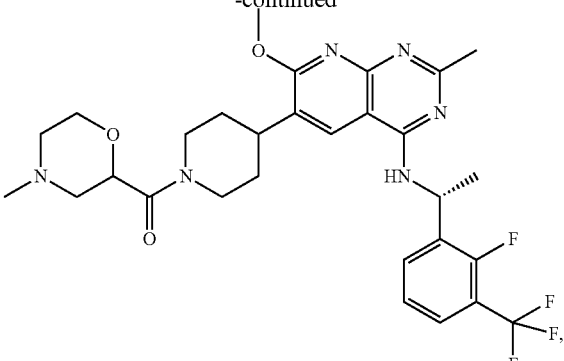
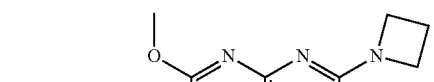

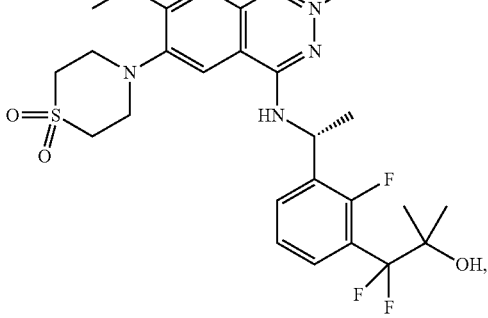
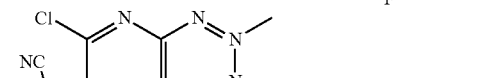
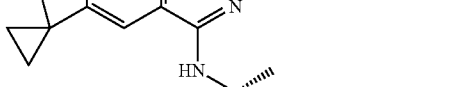

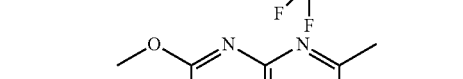

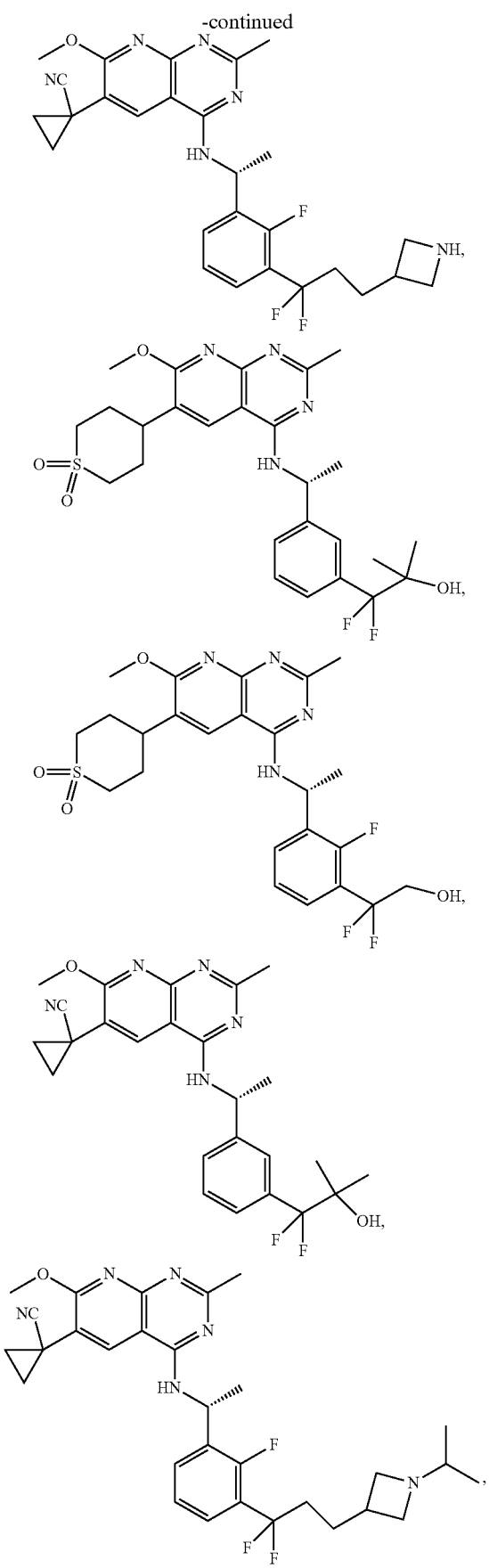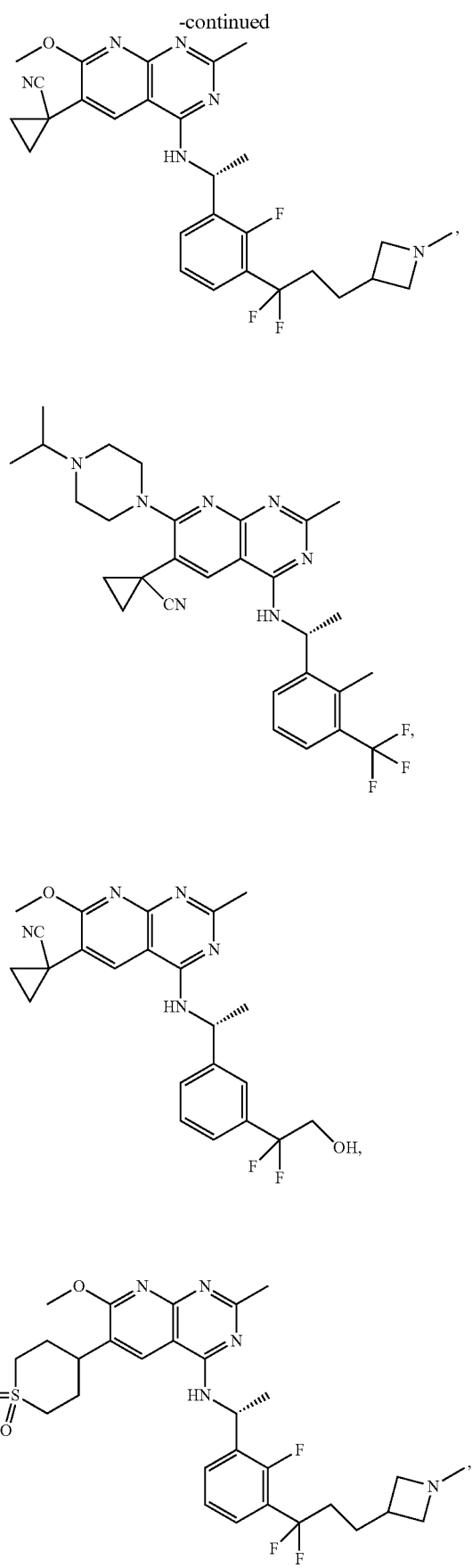

651
-continued
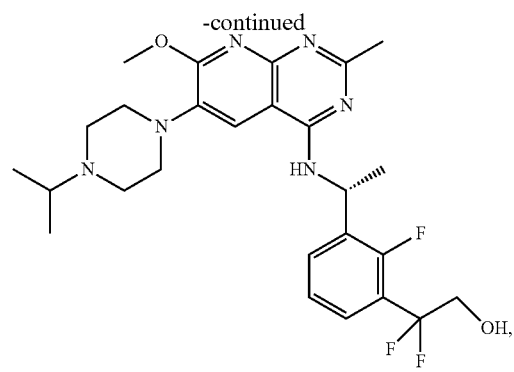
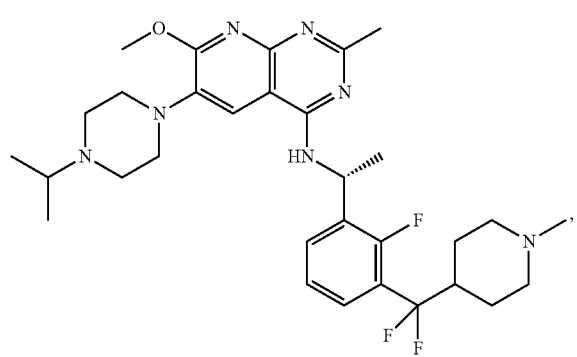
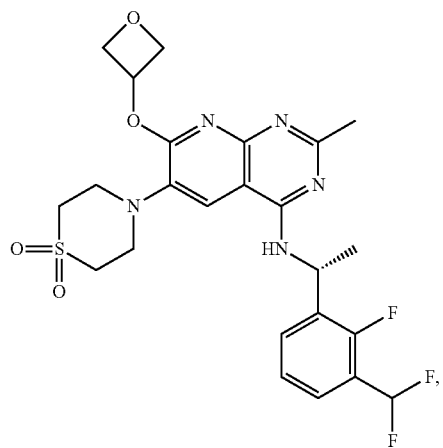
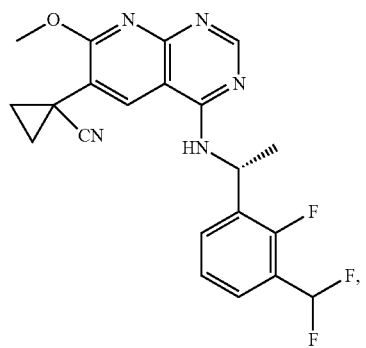
652
-continued
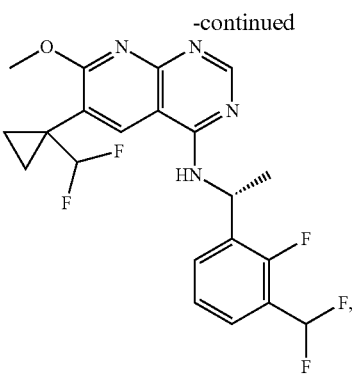
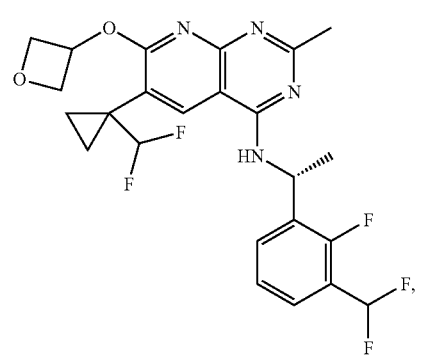
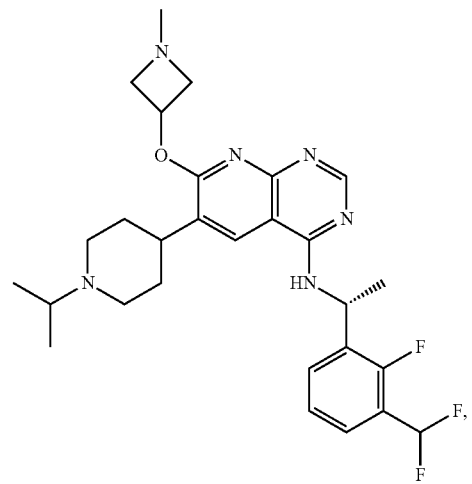
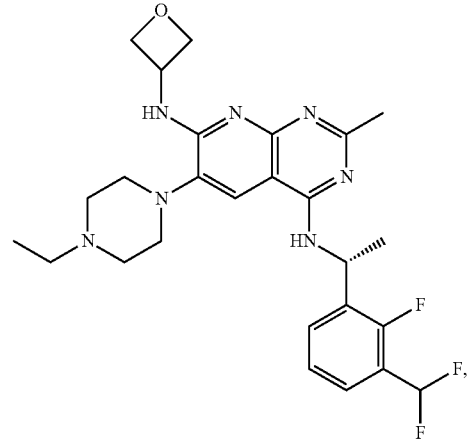

653
-continued
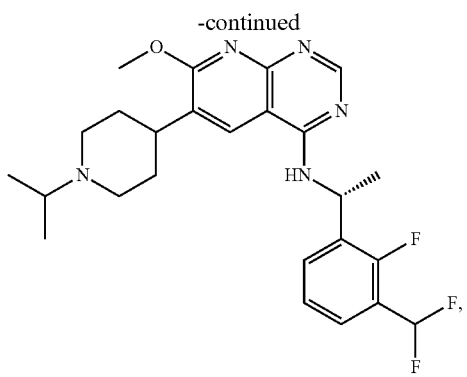
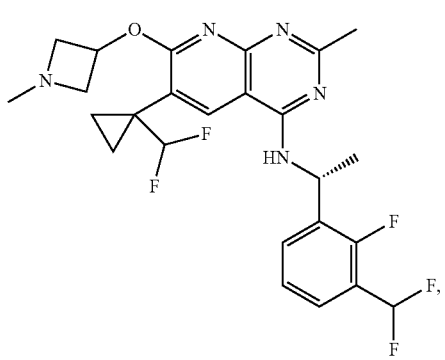
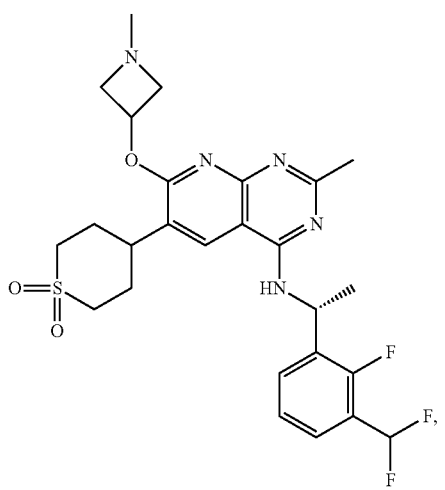
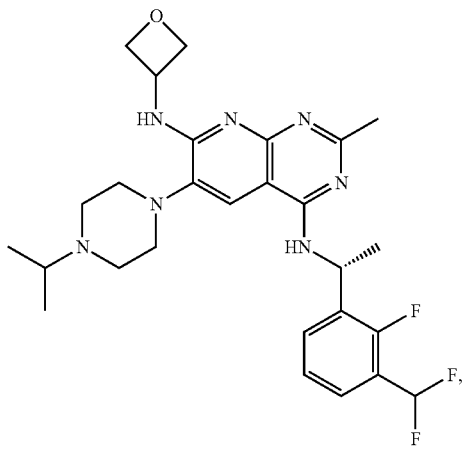
654
-continued
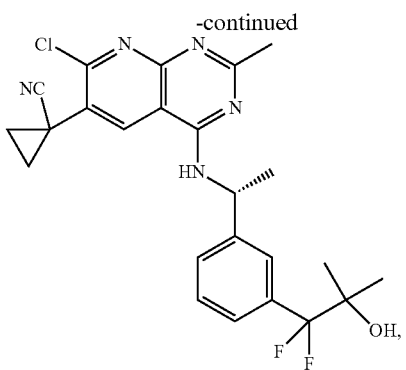
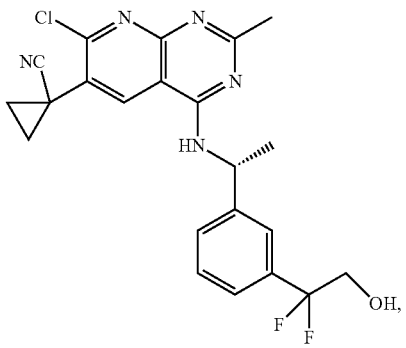
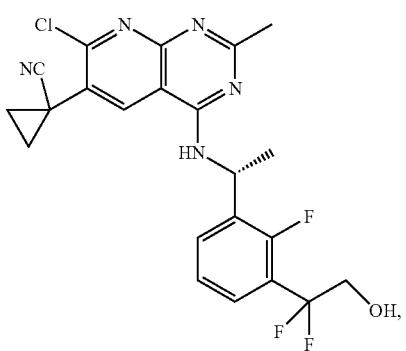
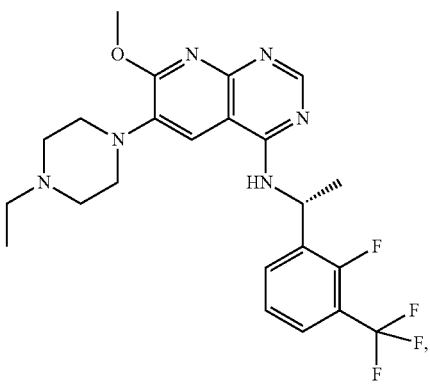

655
-continued
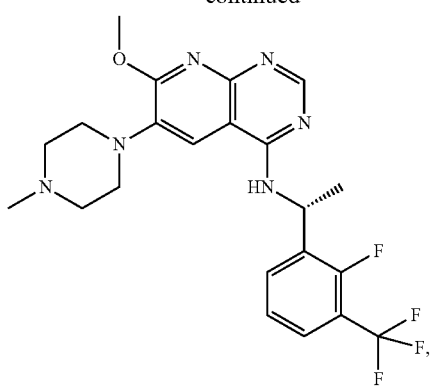
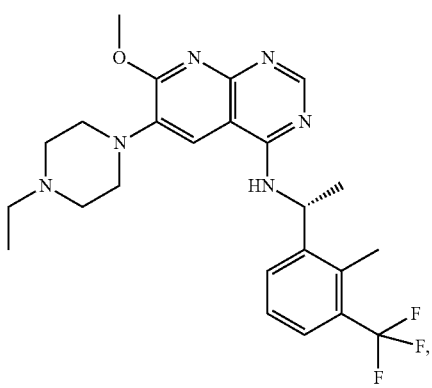
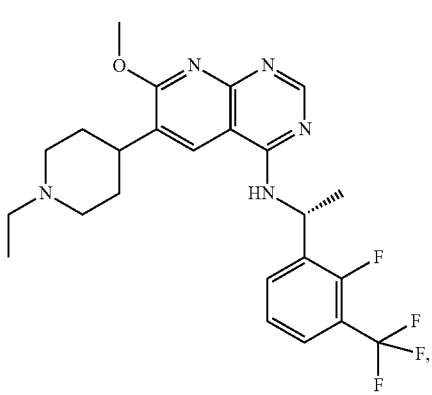
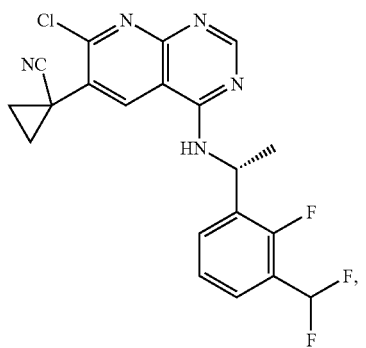
656
-continued
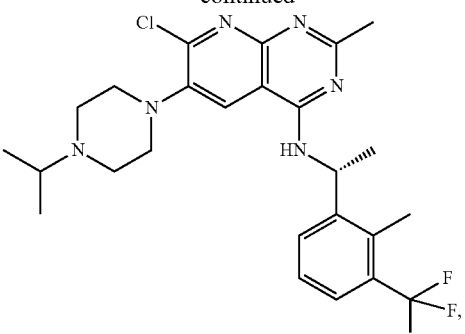
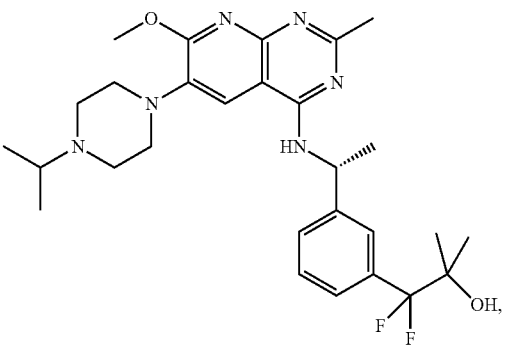
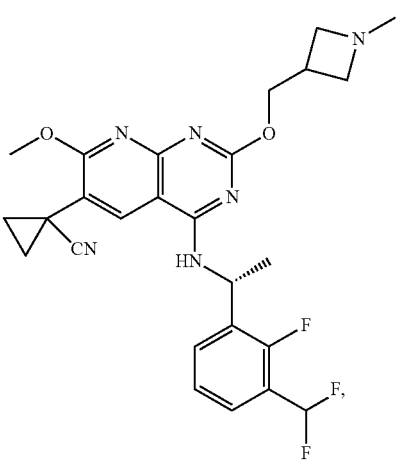
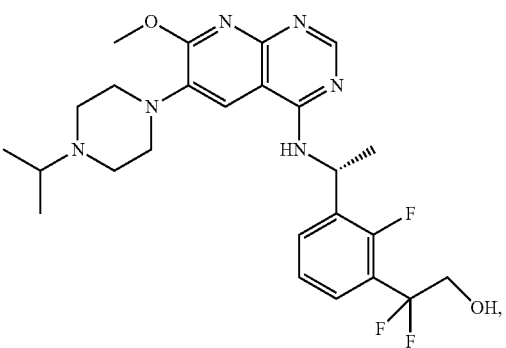

657
-continued
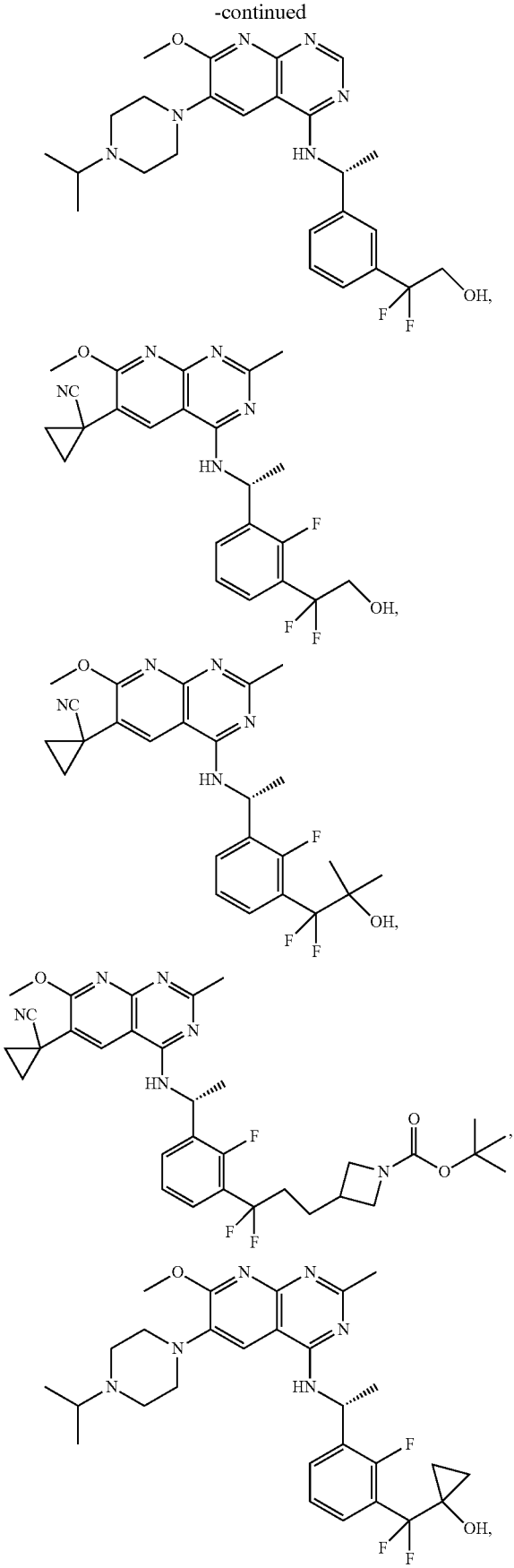
658
-continued
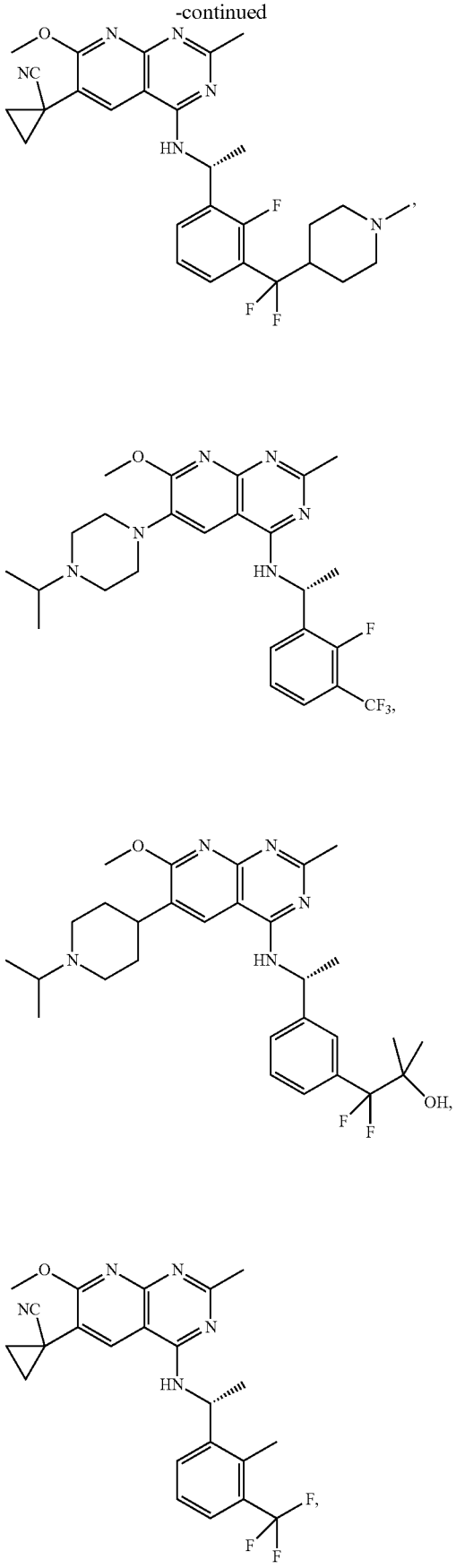

659
-continued
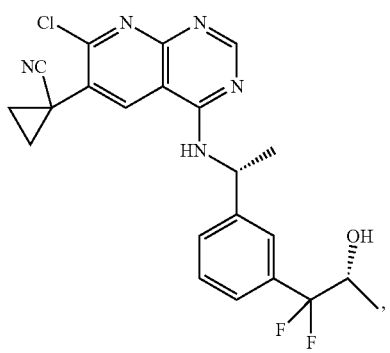
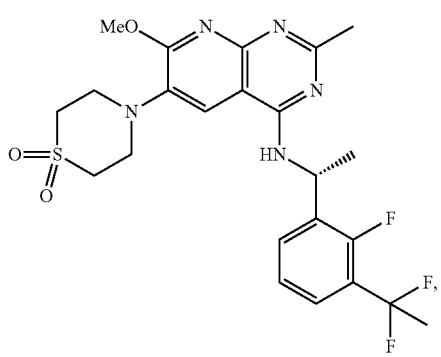
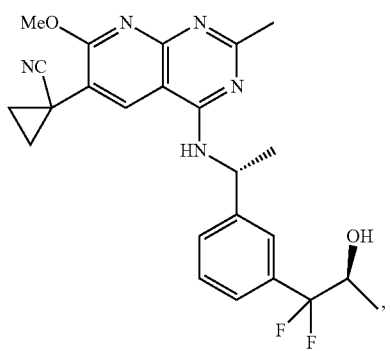
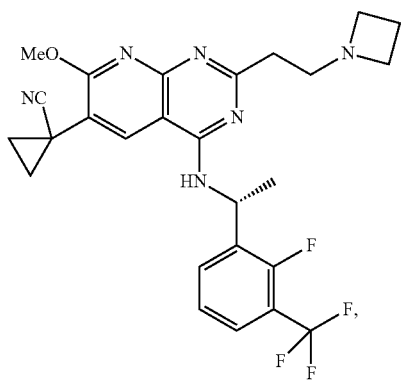
660
-continued
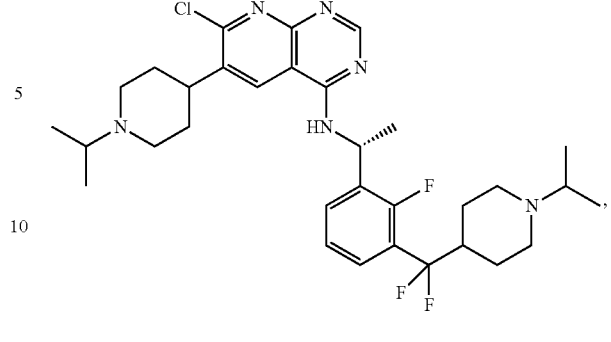
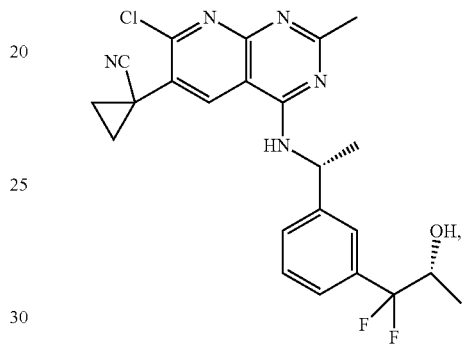
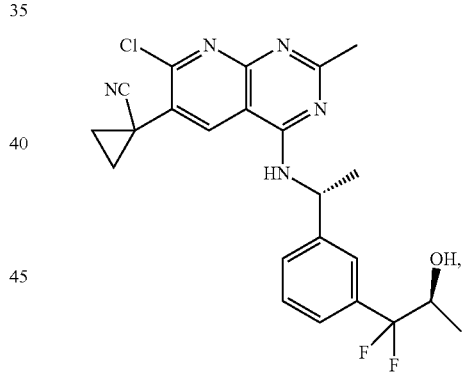
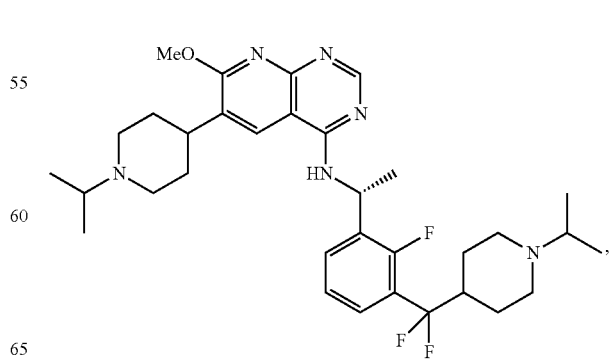

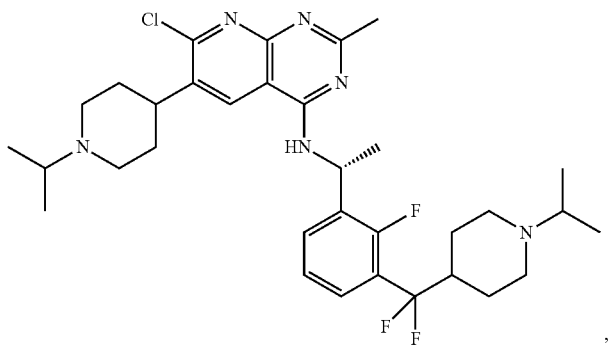
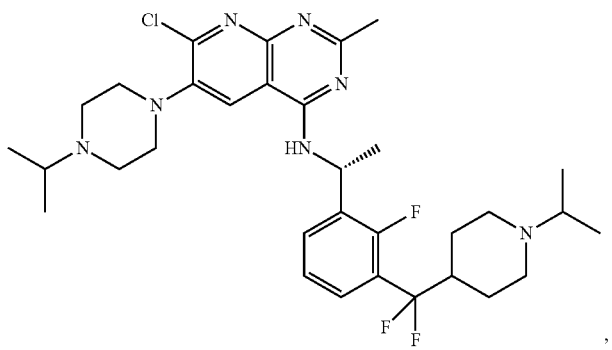
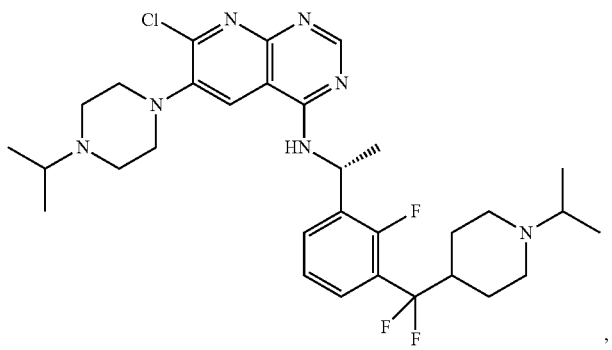
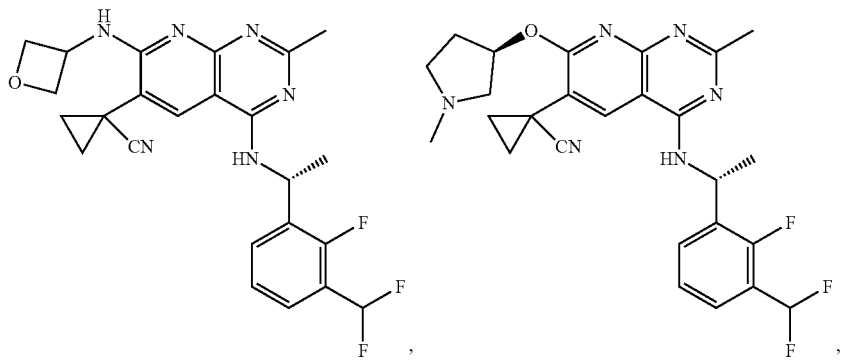

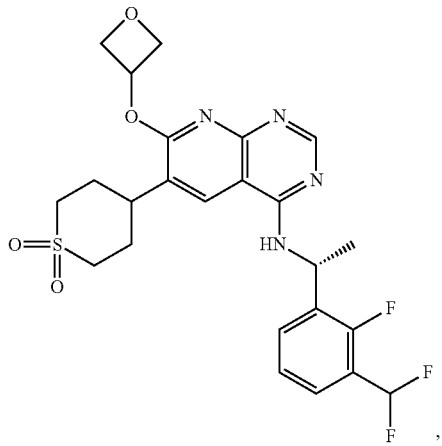
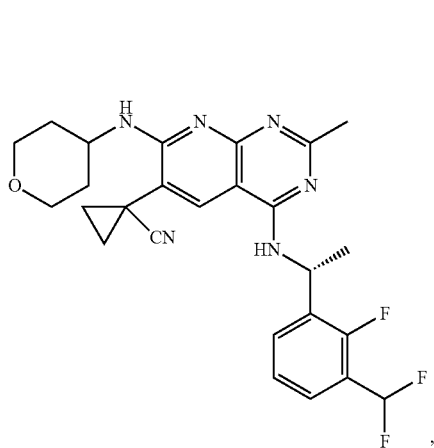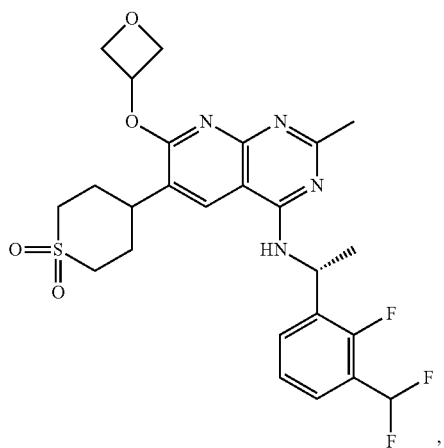
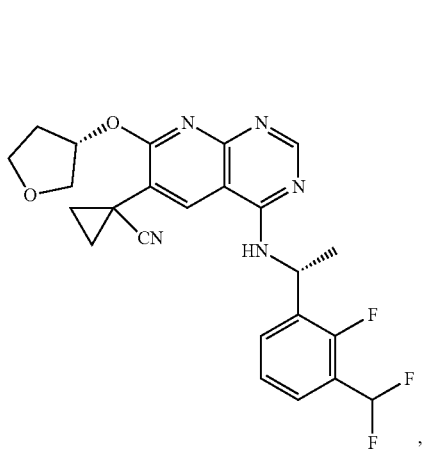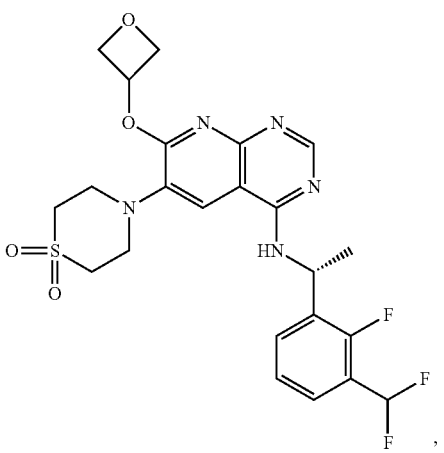
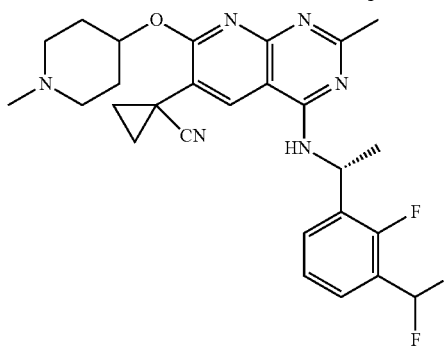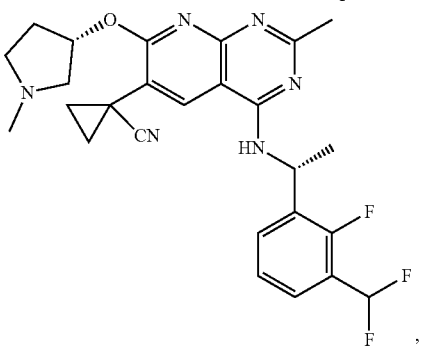

-continued
665
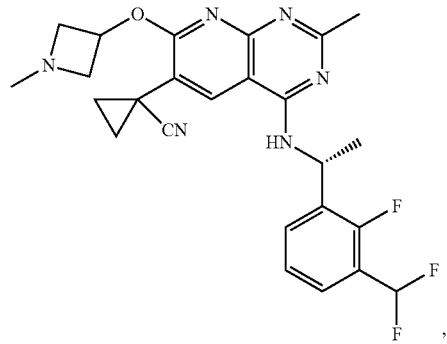
666
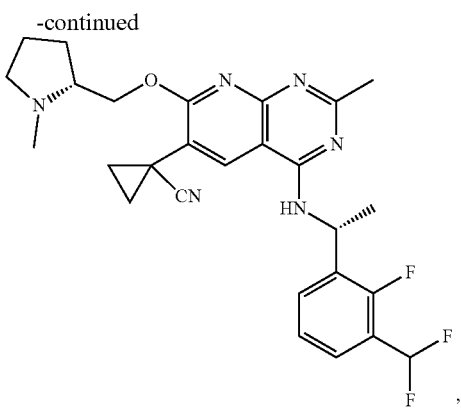
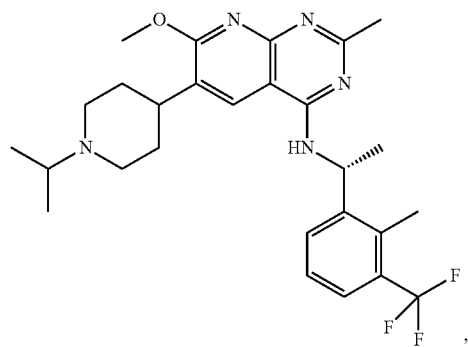
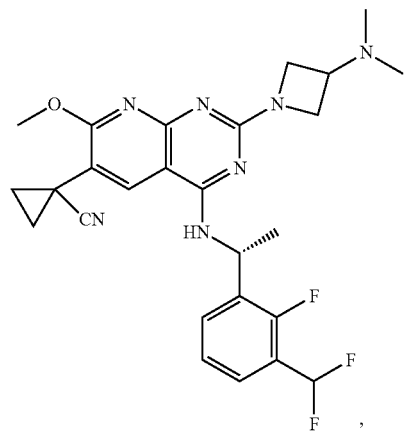
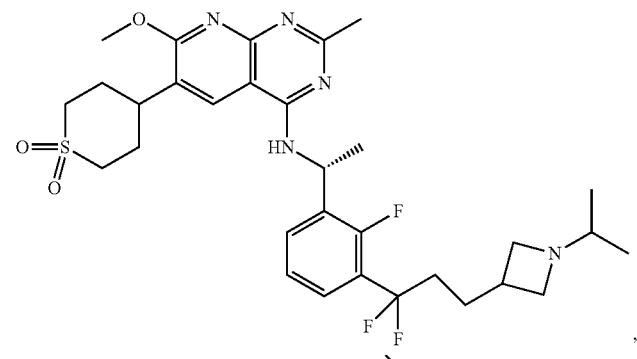
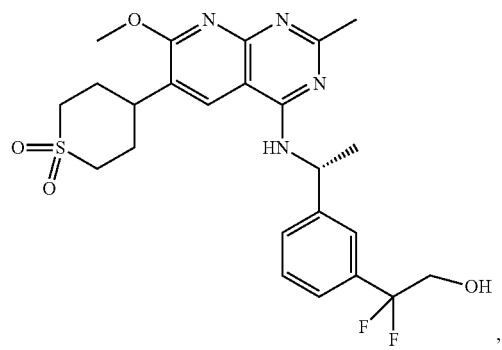
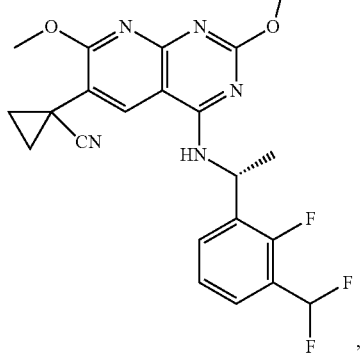

667
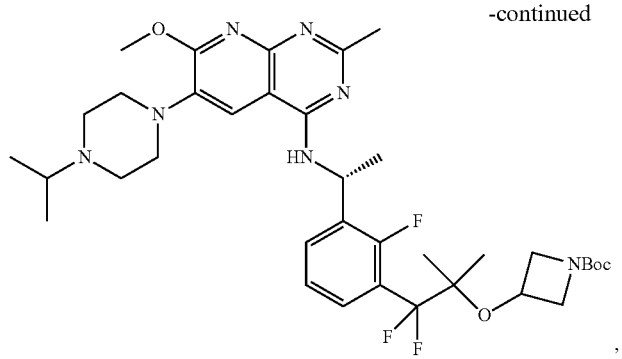
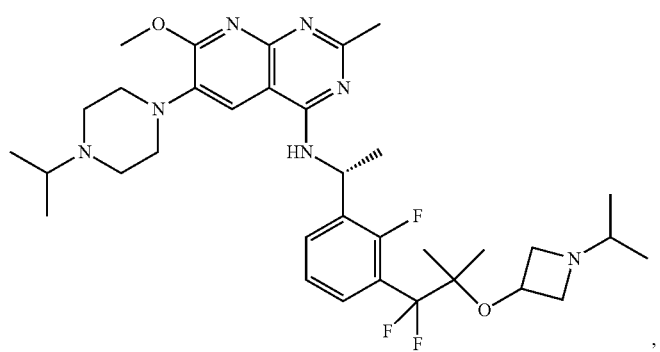
-continued
668
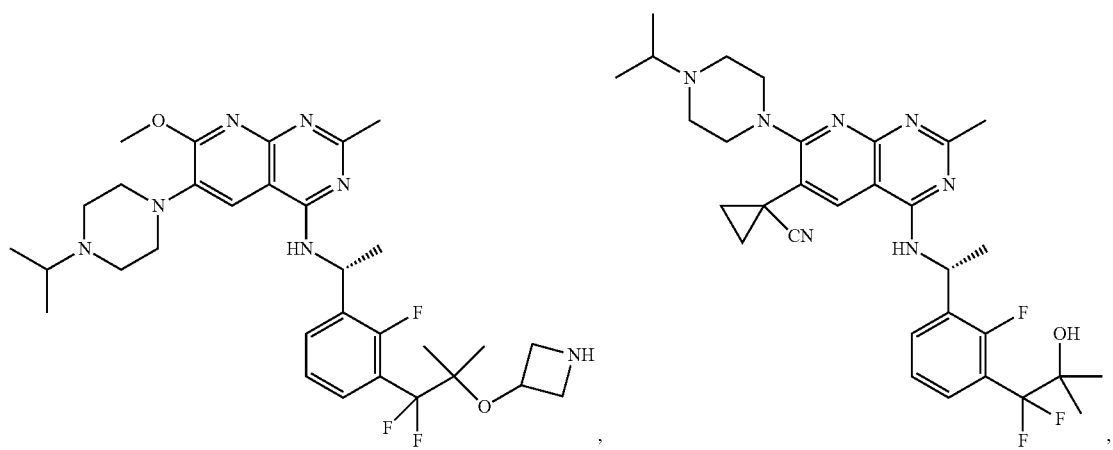
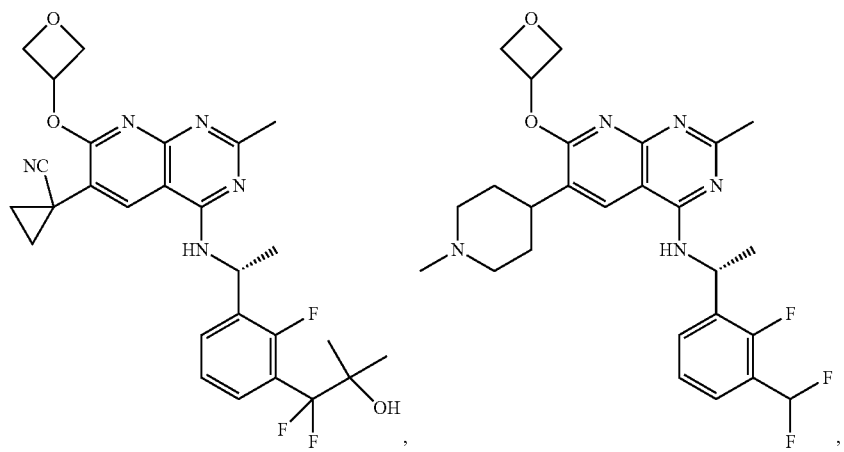

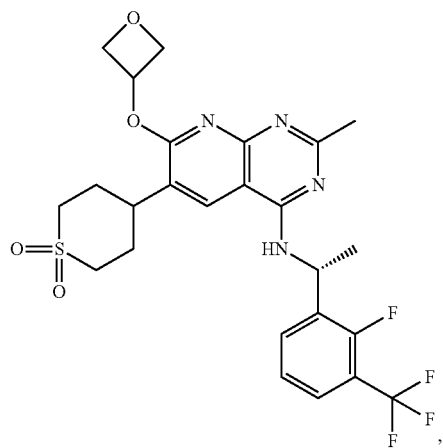
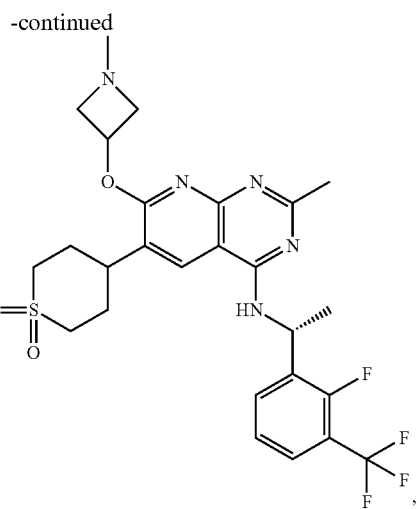
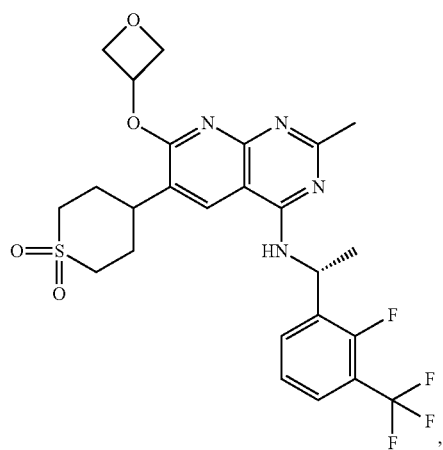
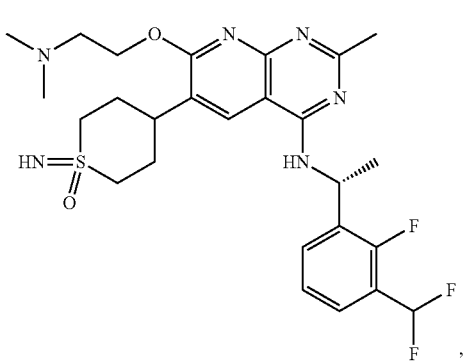
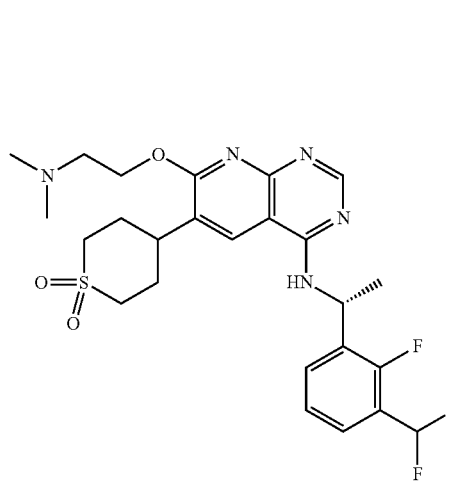
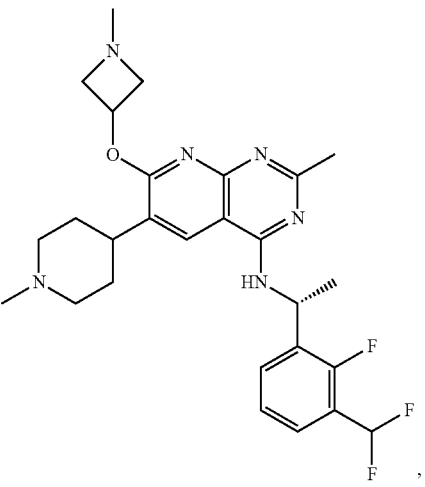

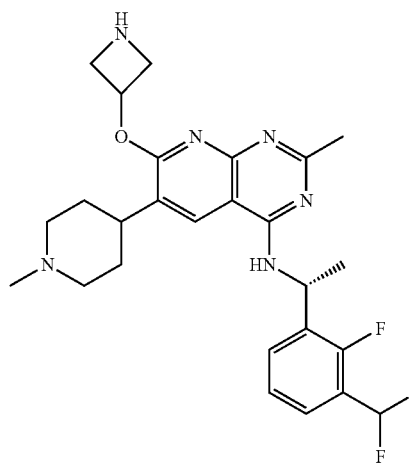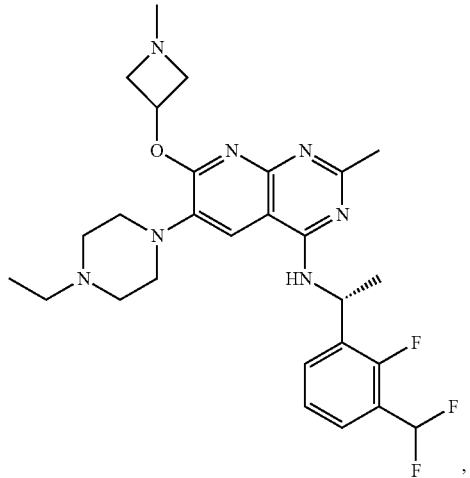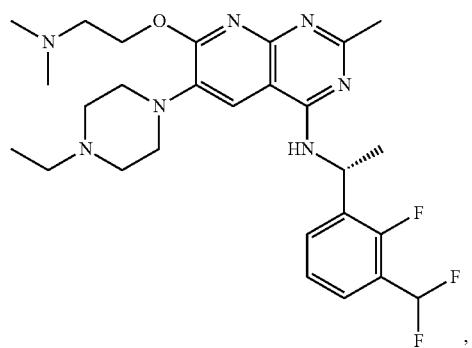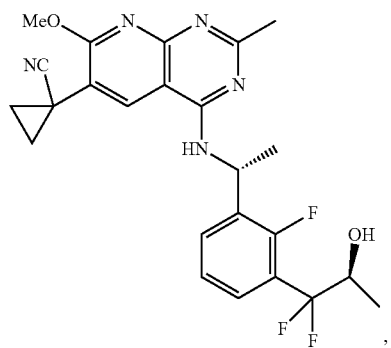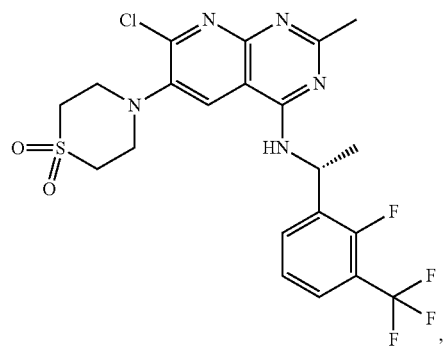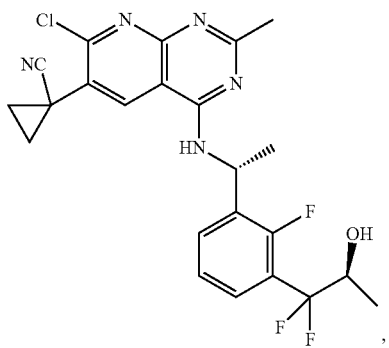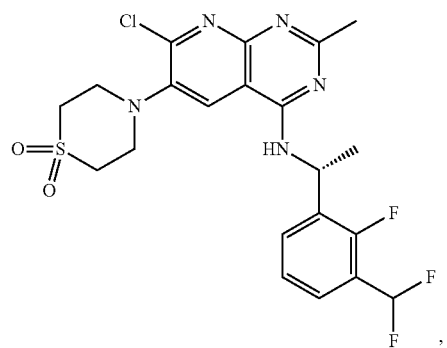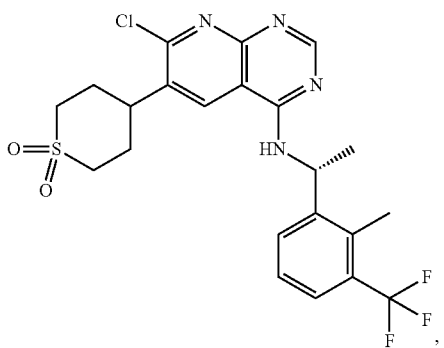

673
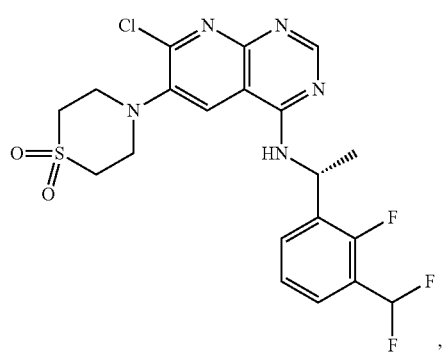
,
-continued
674
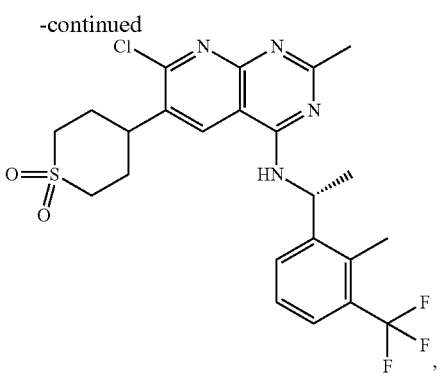
,
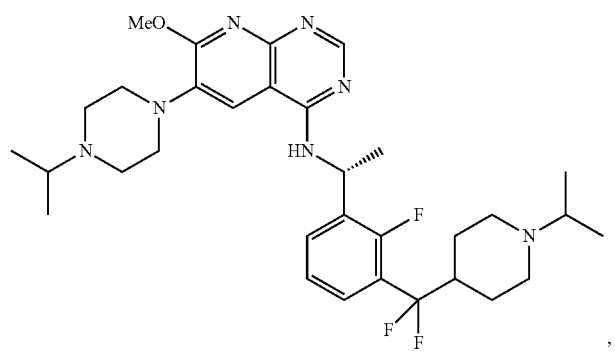
,
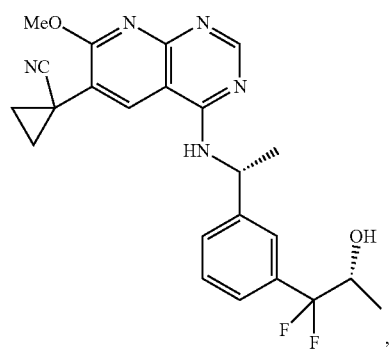
,
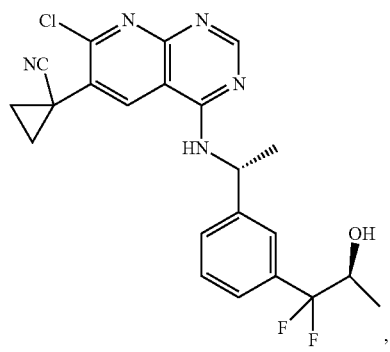
,
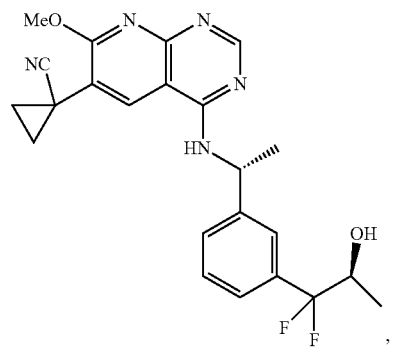
,
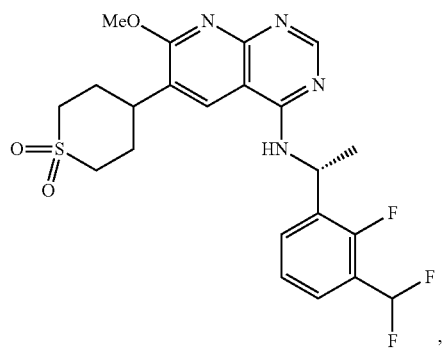
,
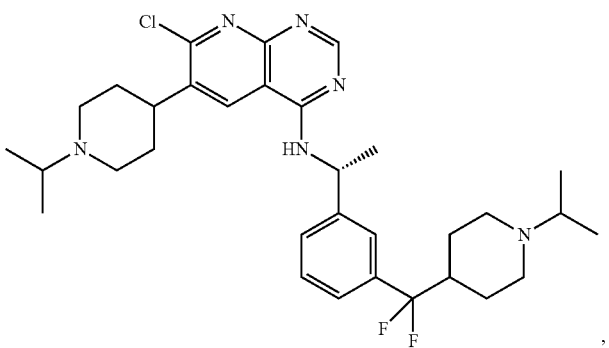
, 675
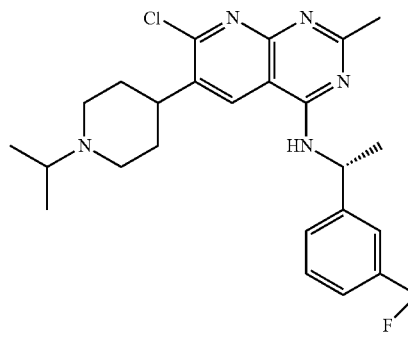
676
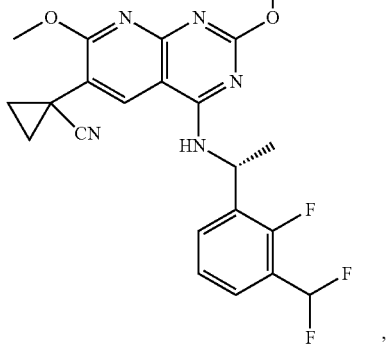
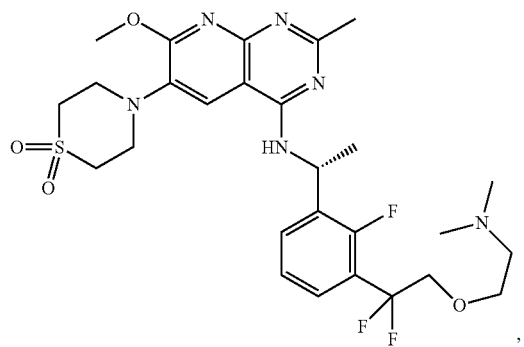,
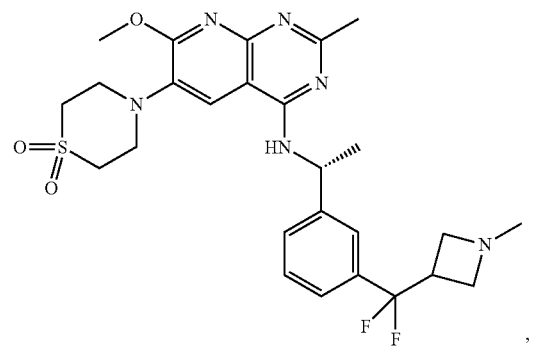,
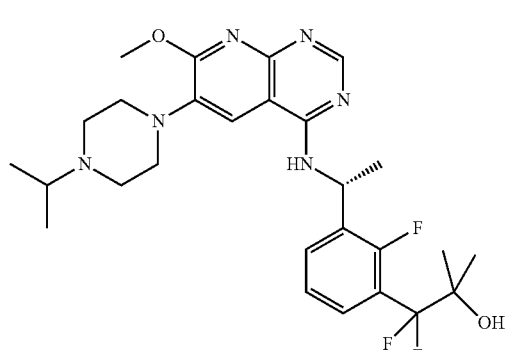,
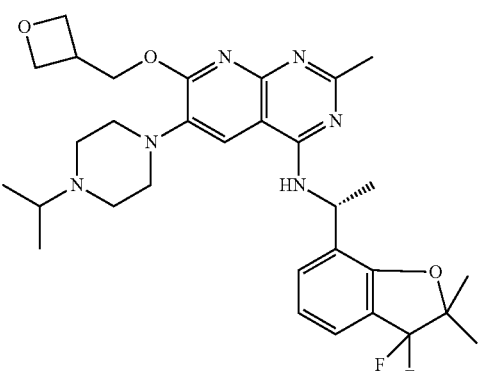,
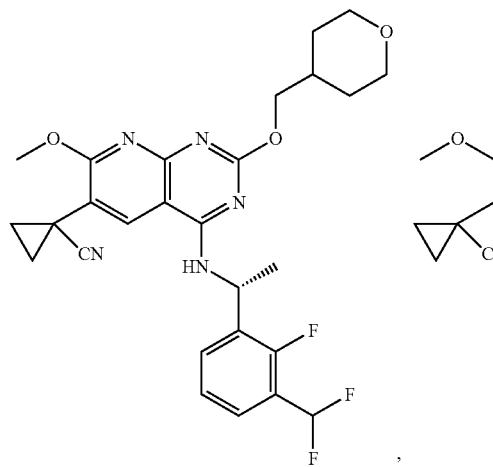,
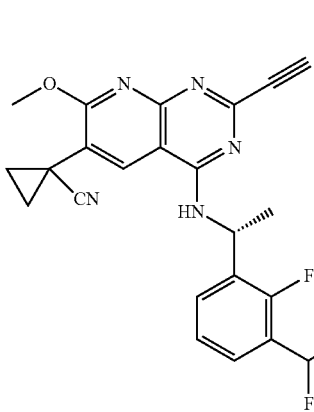, -continued
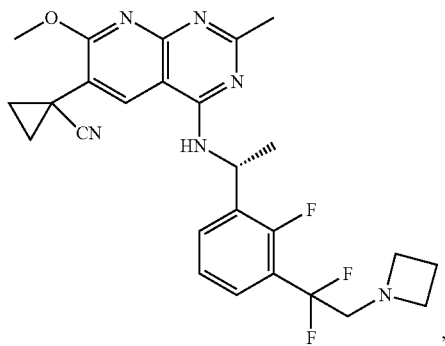
,
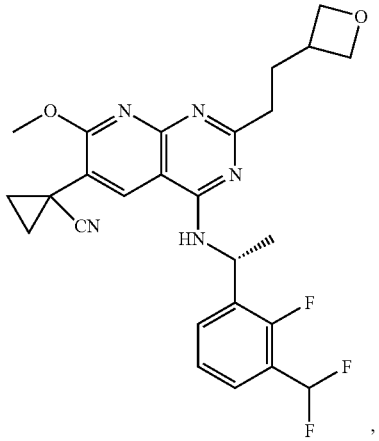
,
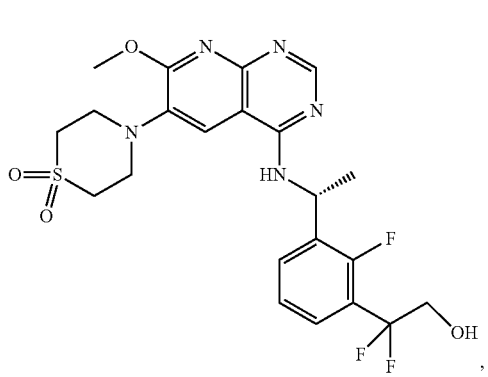
,
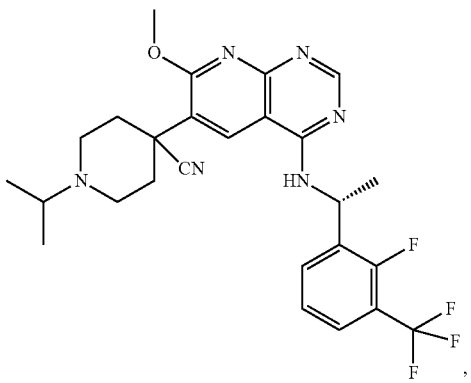
,
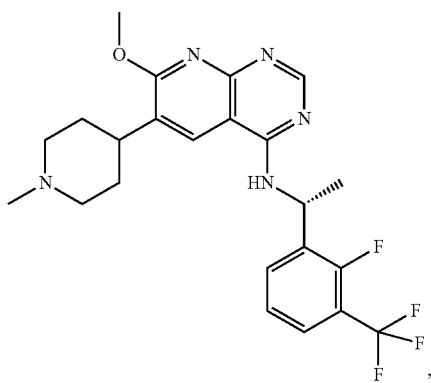
,
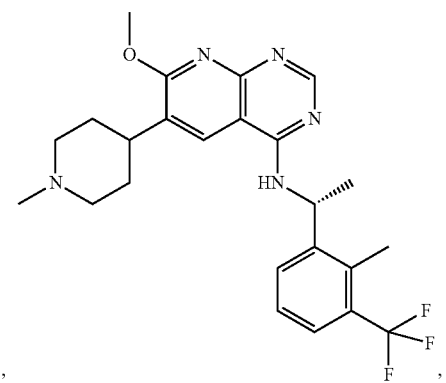
,
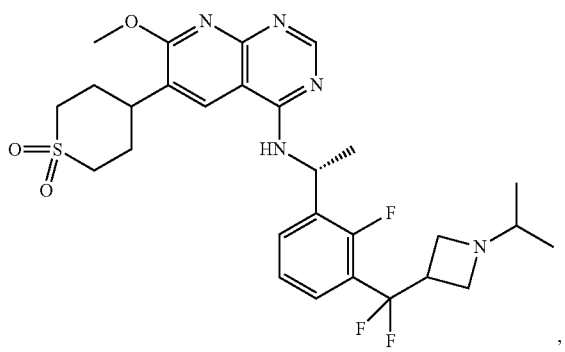
,
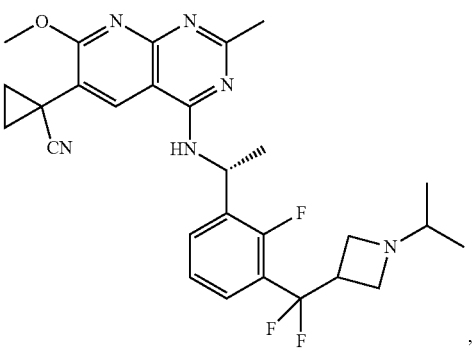
, -continued
679
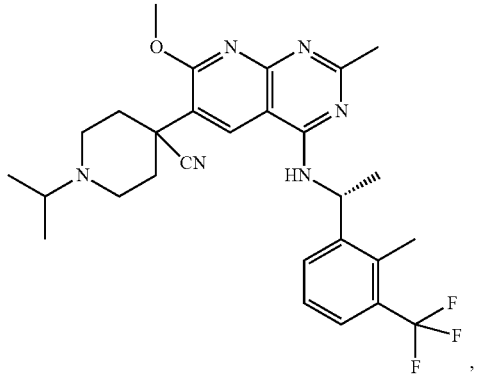
680
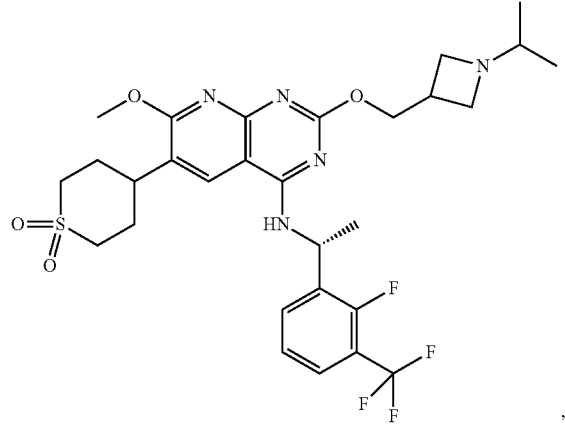
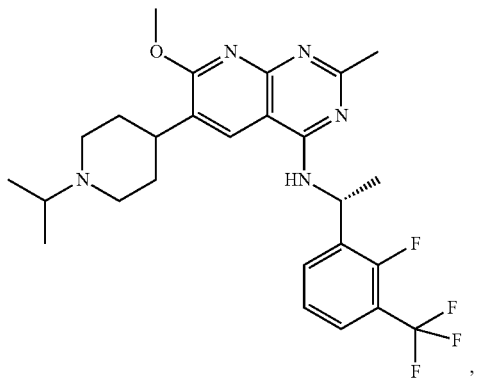
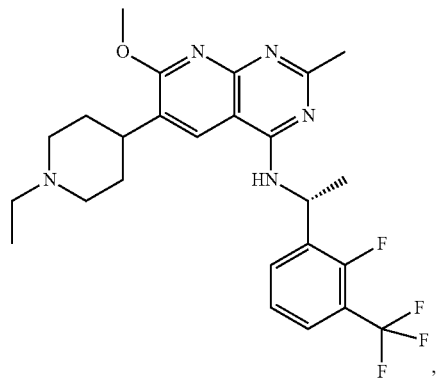
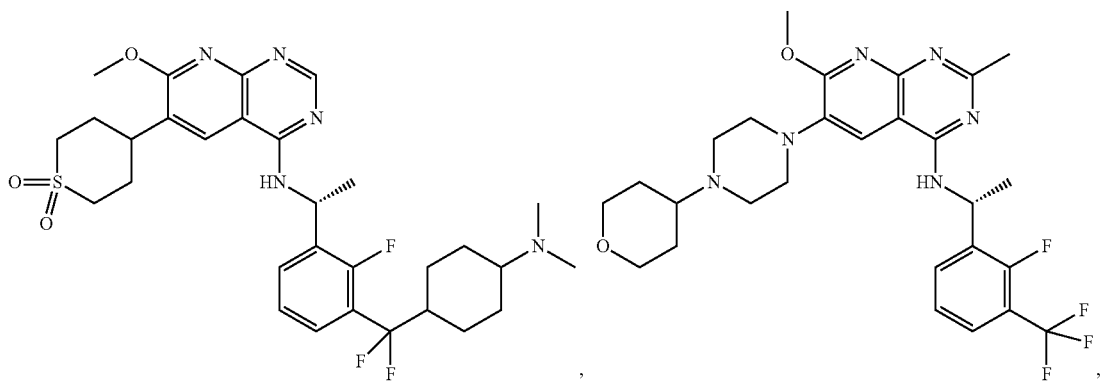
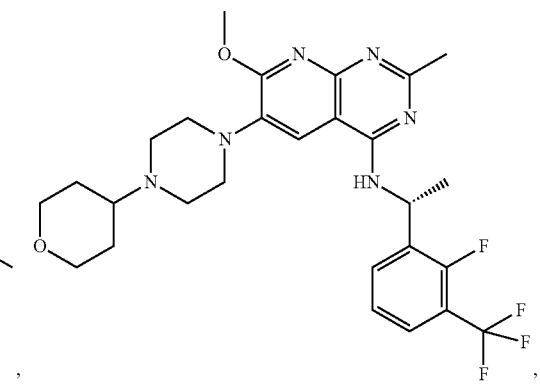
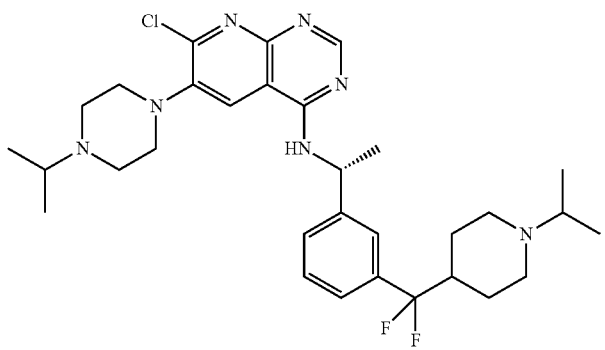
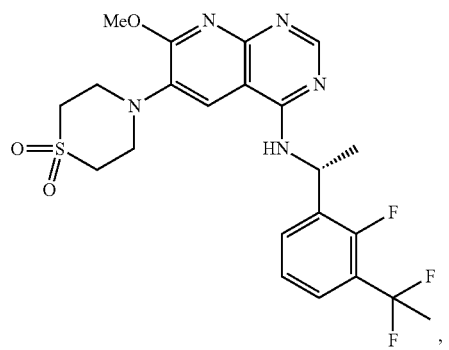

681
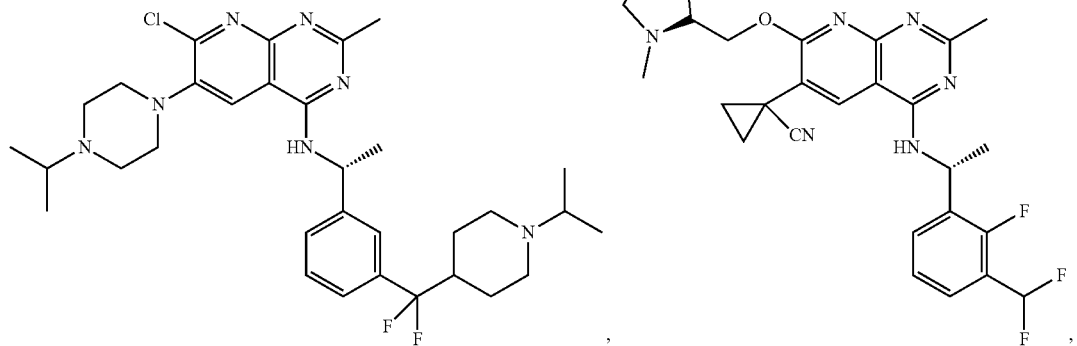
682
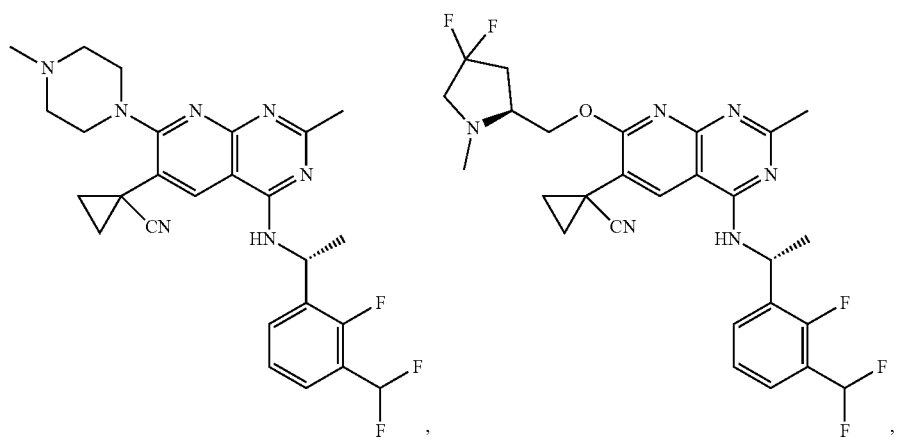
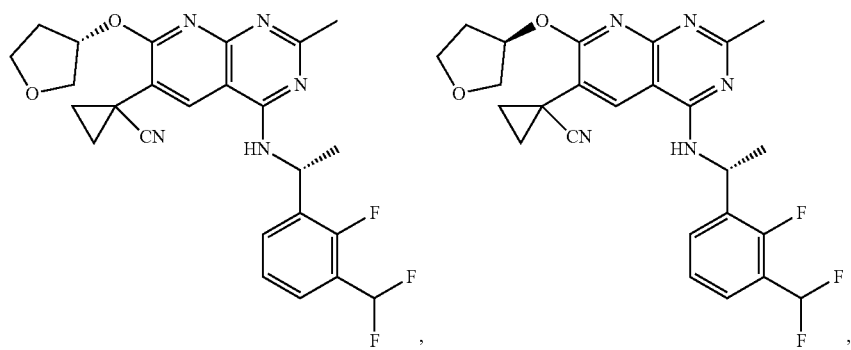
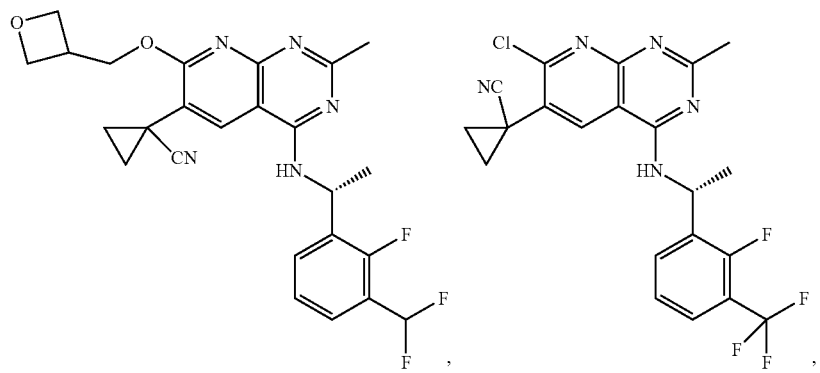

-continued
683
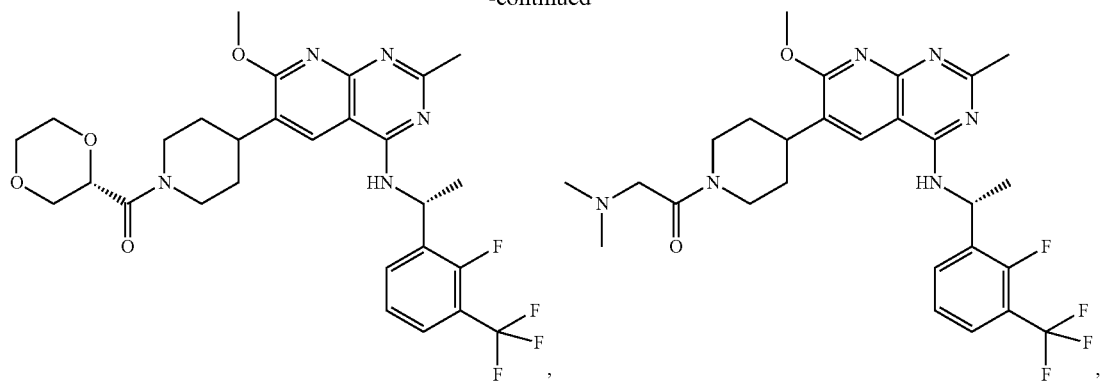
684
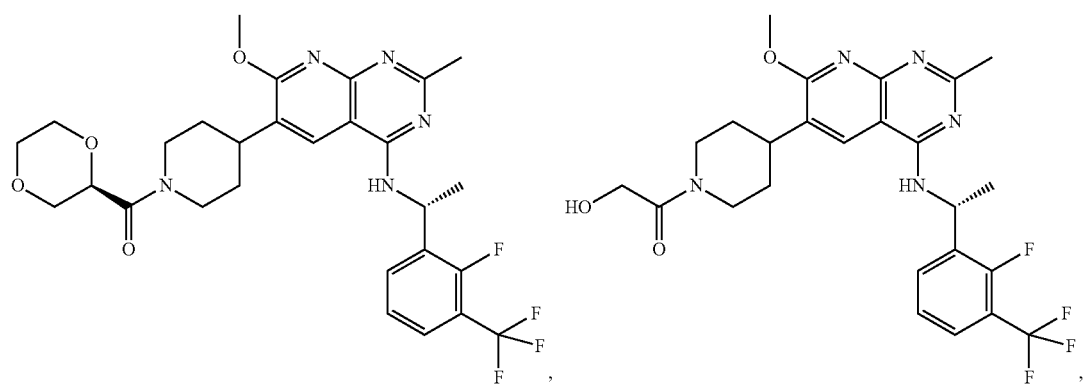
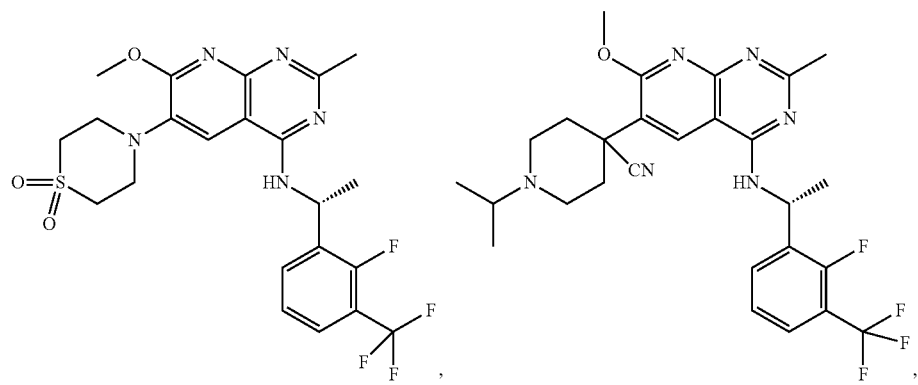
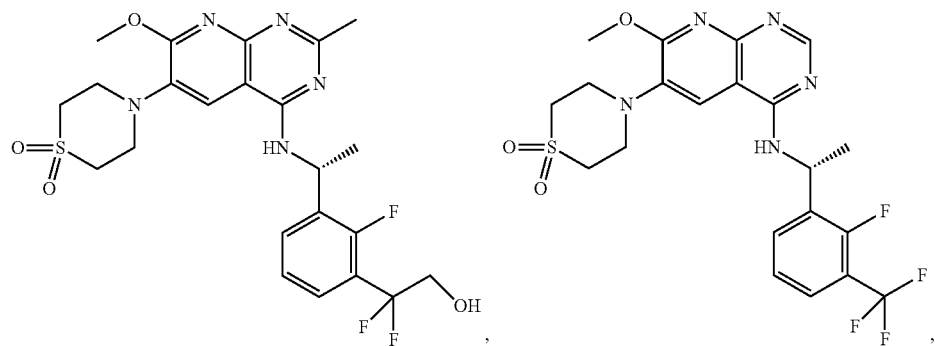

-continued
685
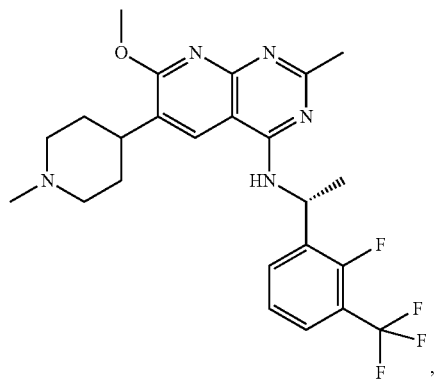
686
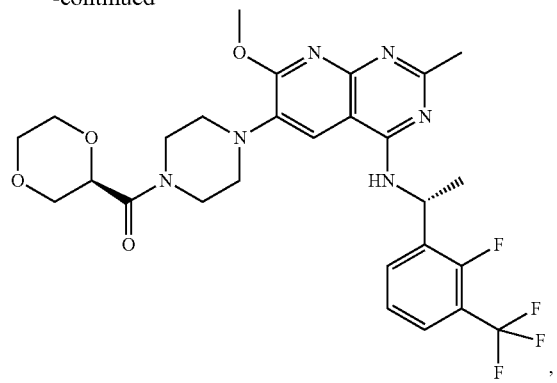
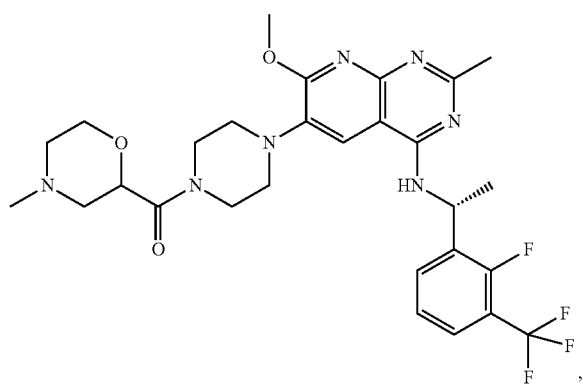
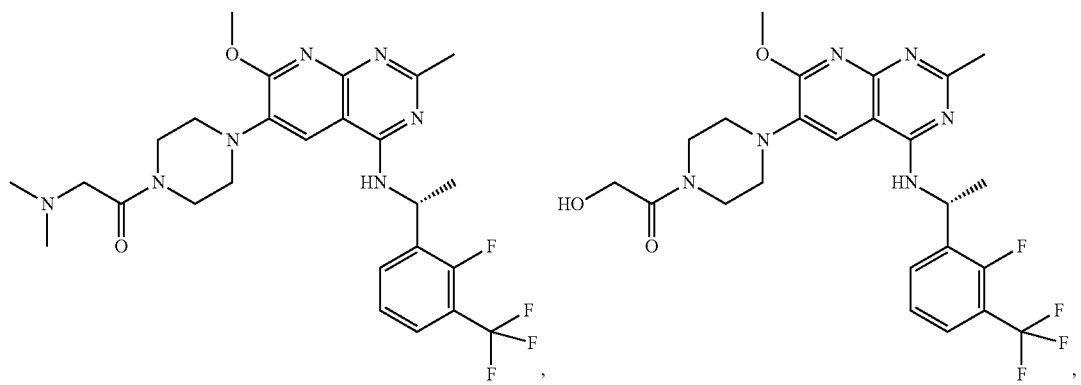
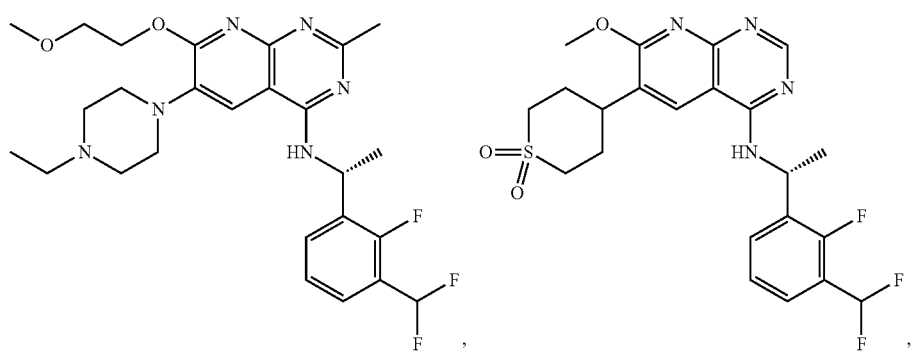

-continued
687
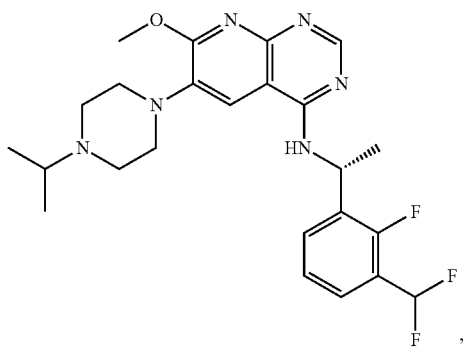
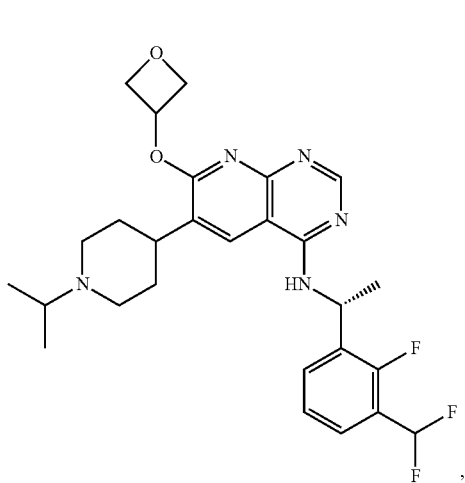
688
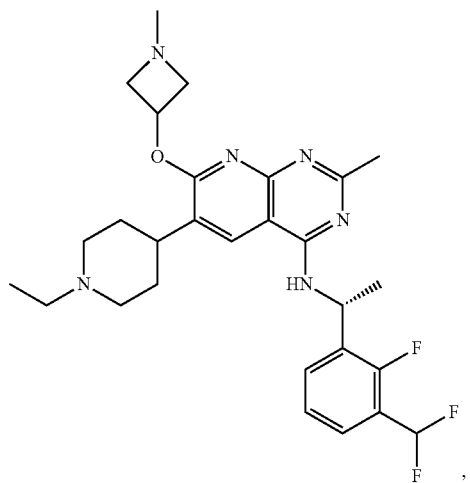
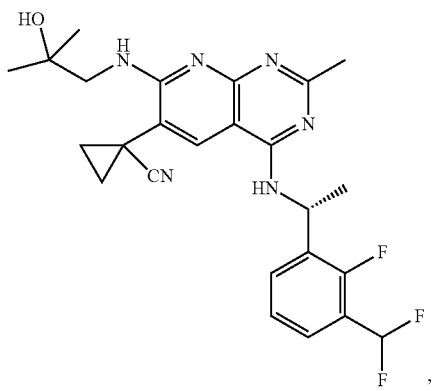
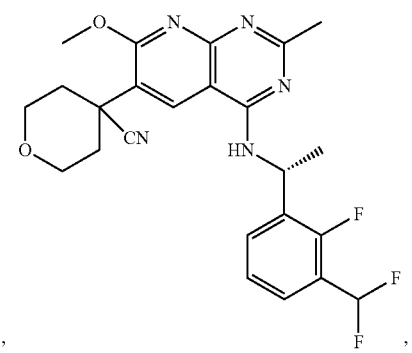
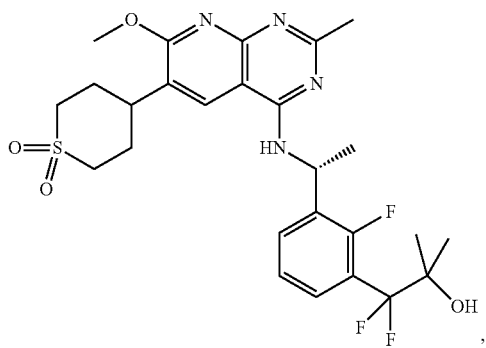
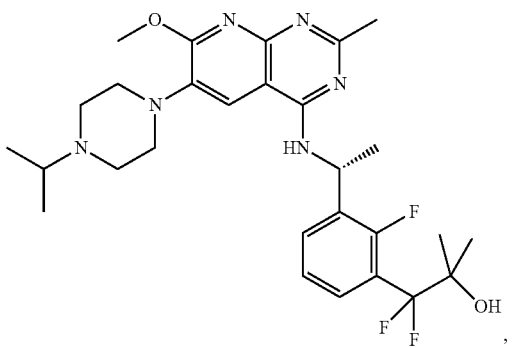

-continued
689
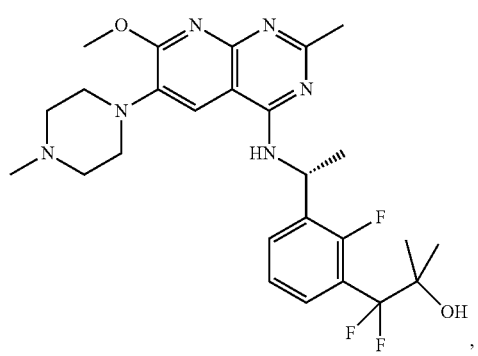
690
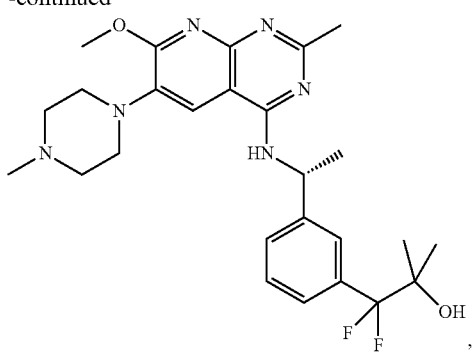
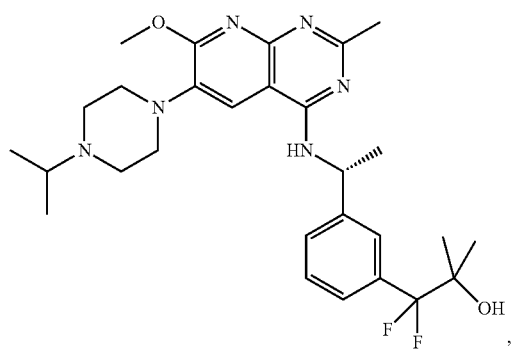
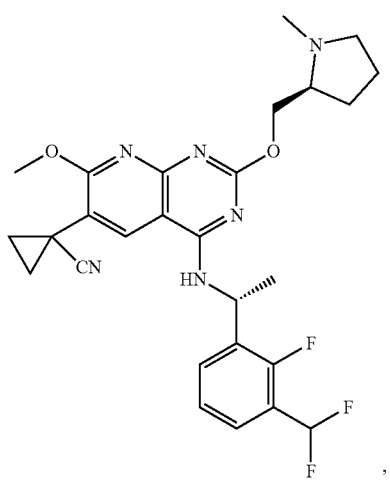
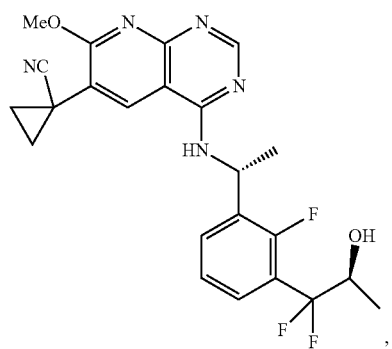
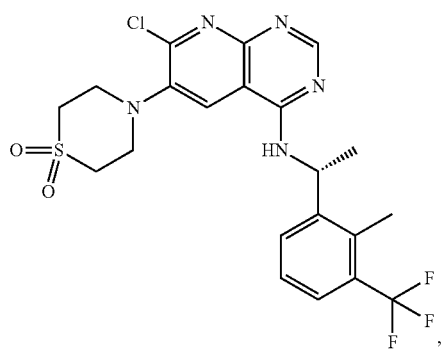
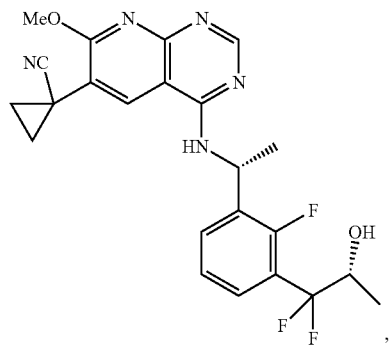
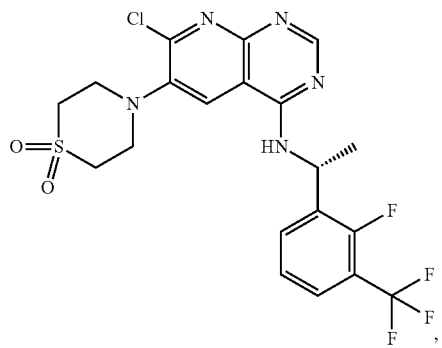

691
-continued
692
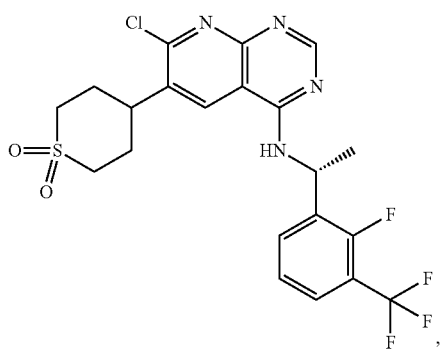
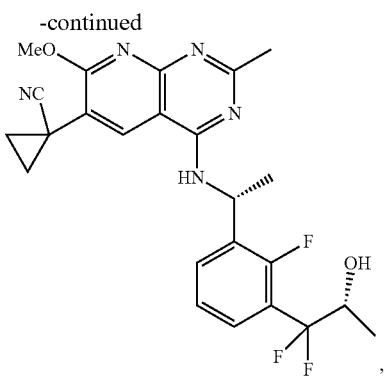
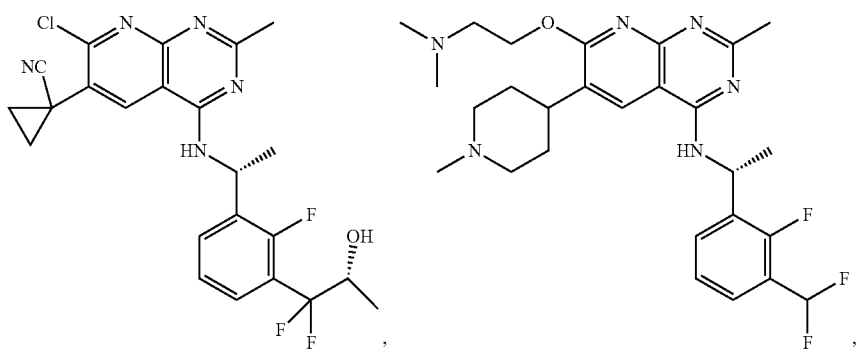
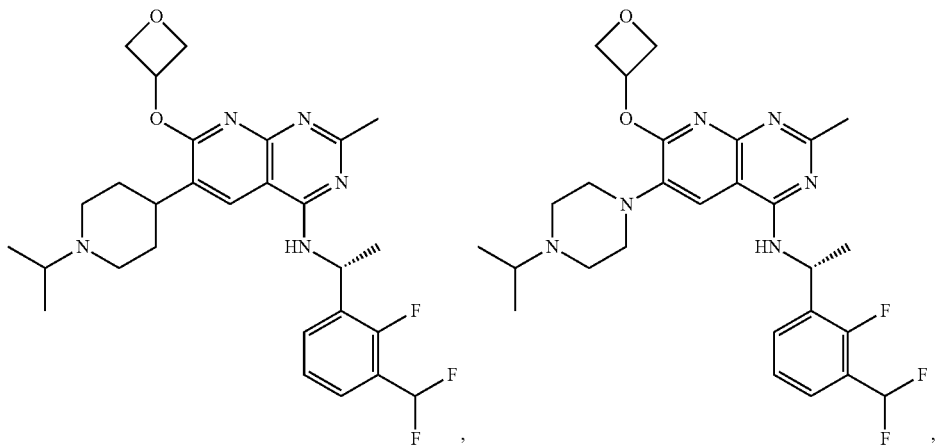
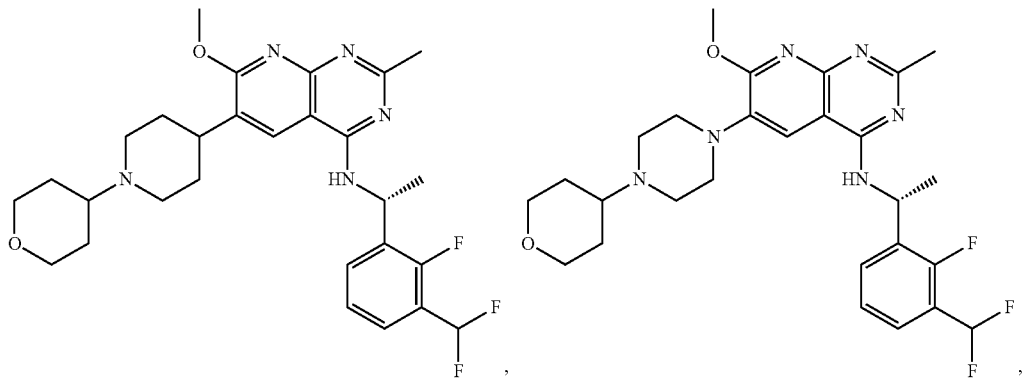

693
694
-continued
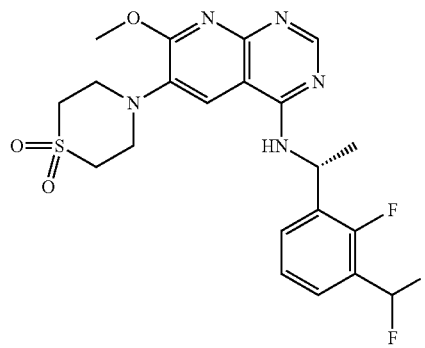
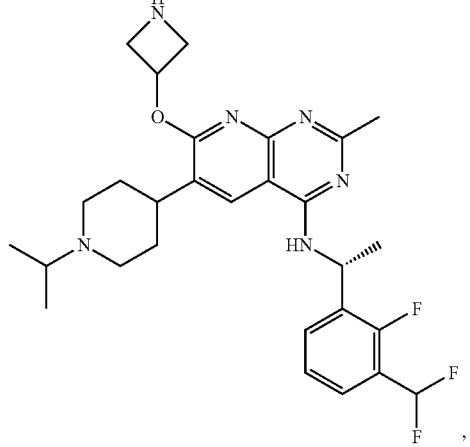
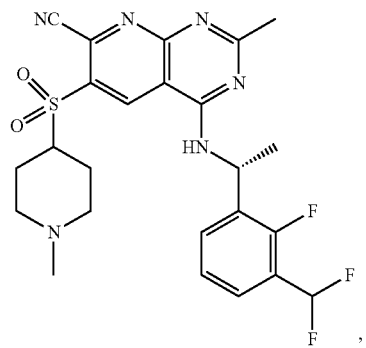
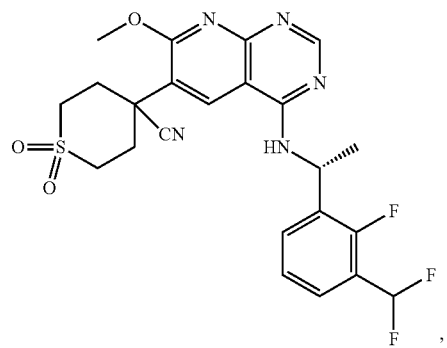
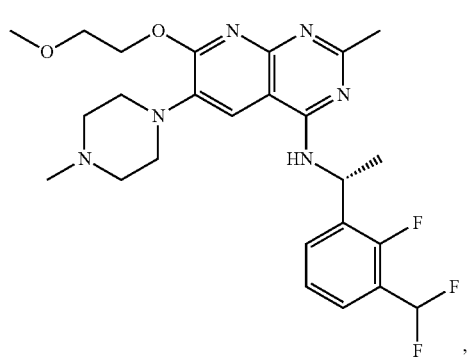
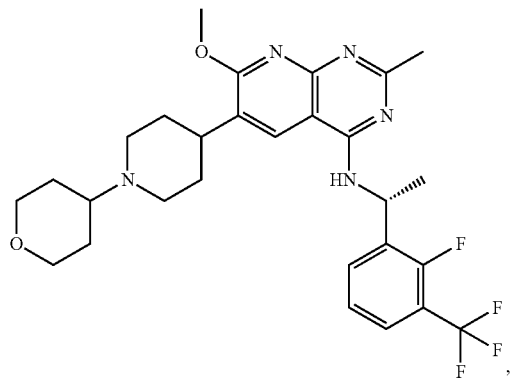
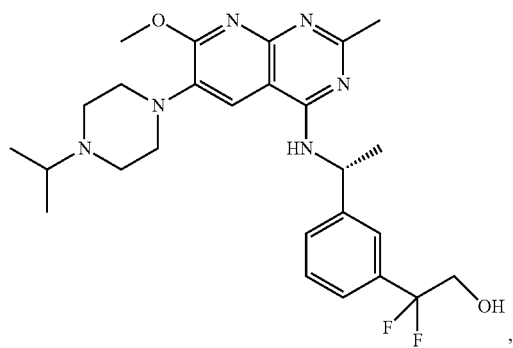
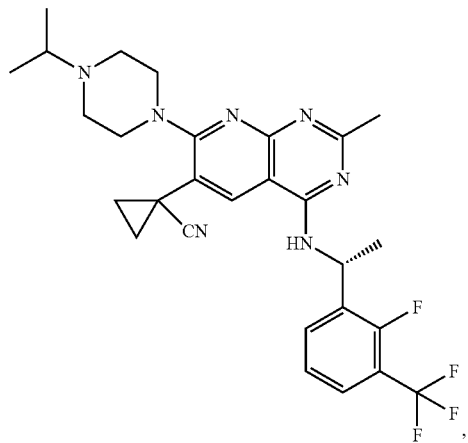

695
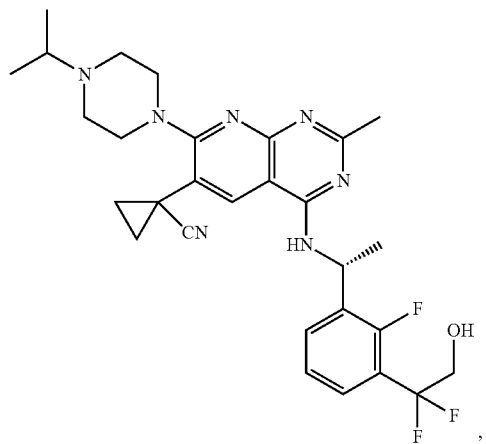
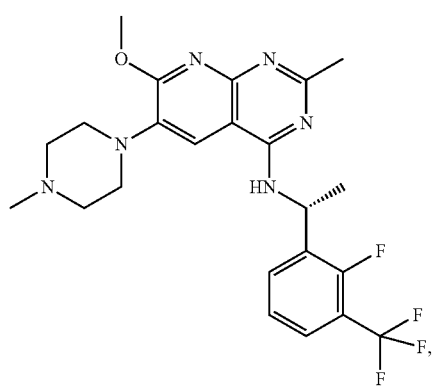
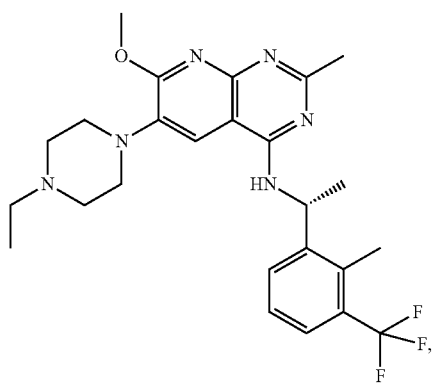
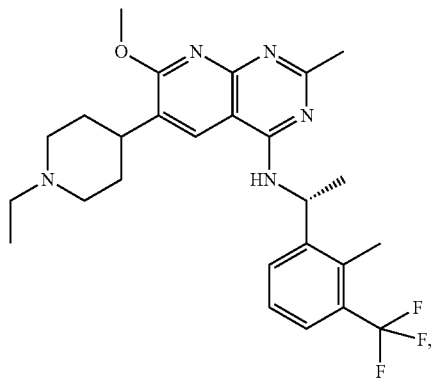
696
-continued
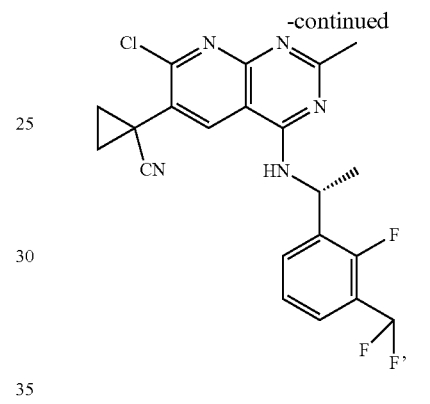
-continued
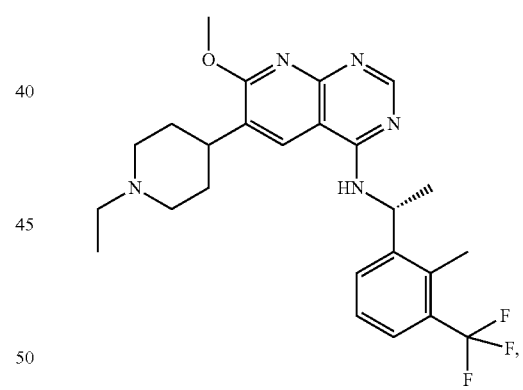
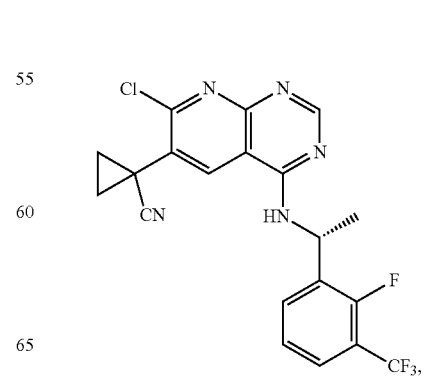

697
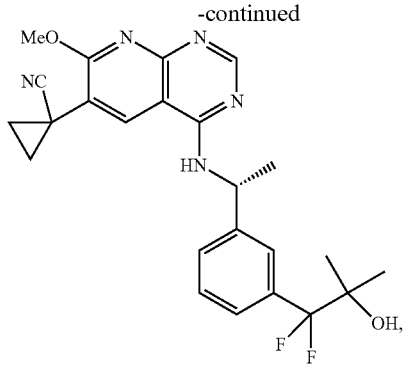
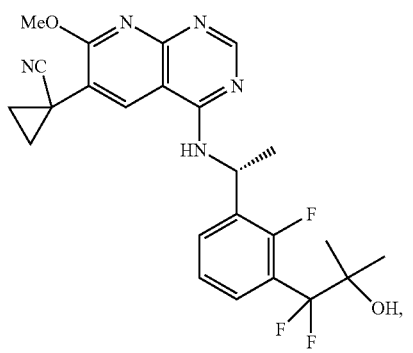
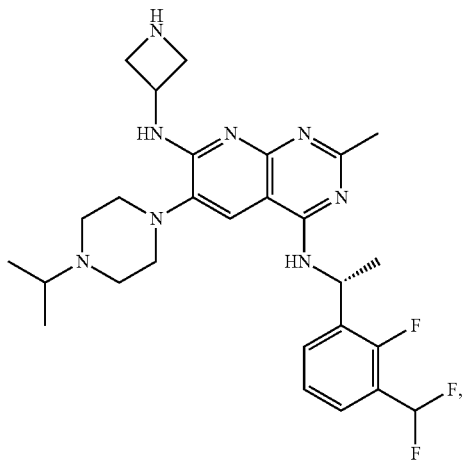
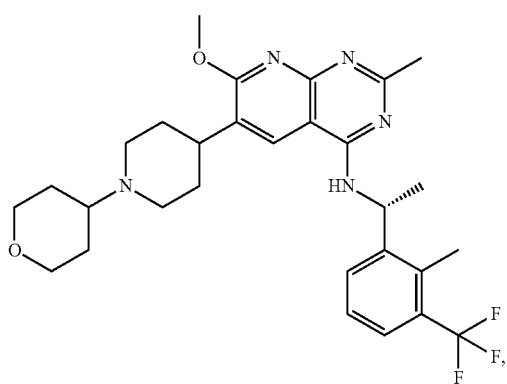
698
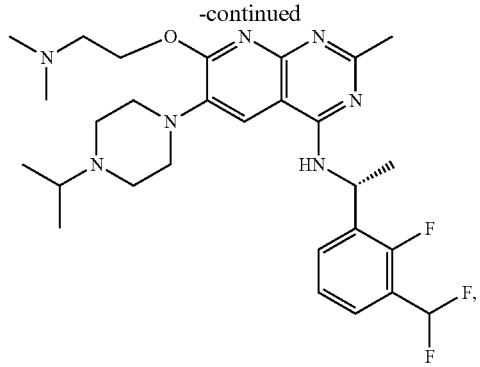
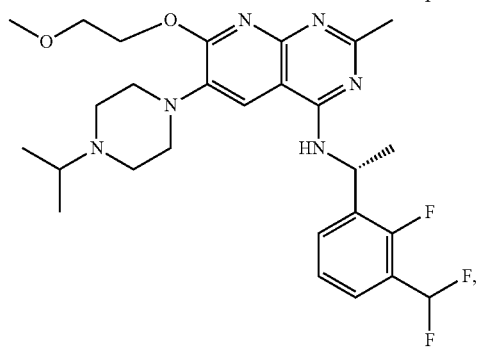
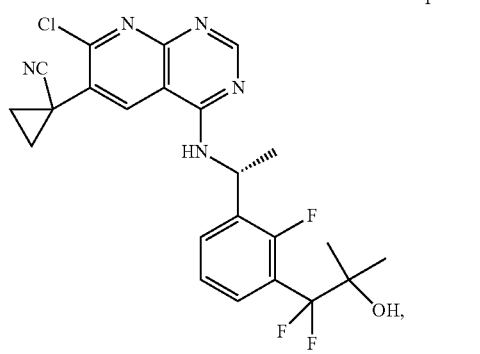
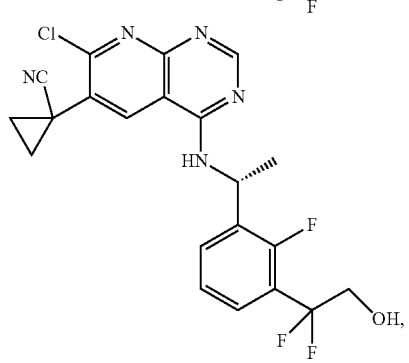
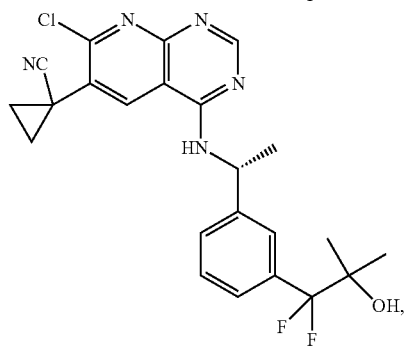

699
-continued
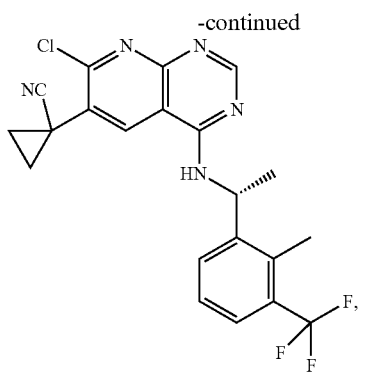
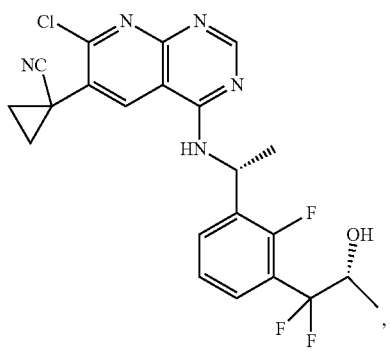
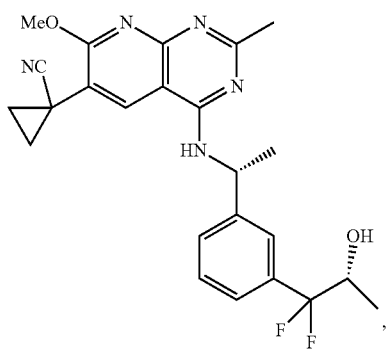
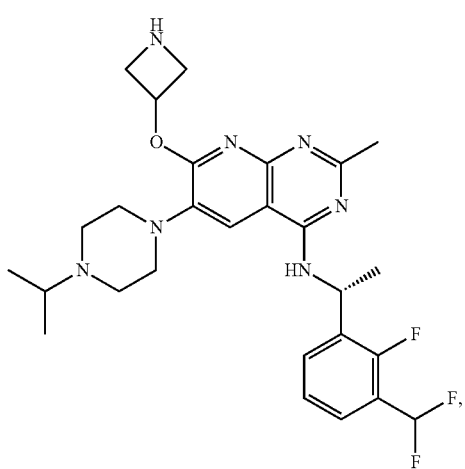
700
-continued
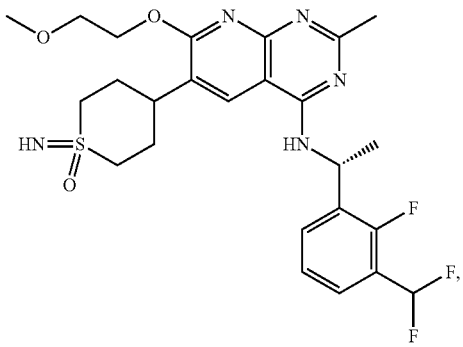
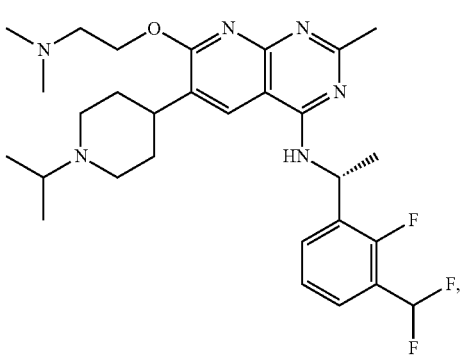
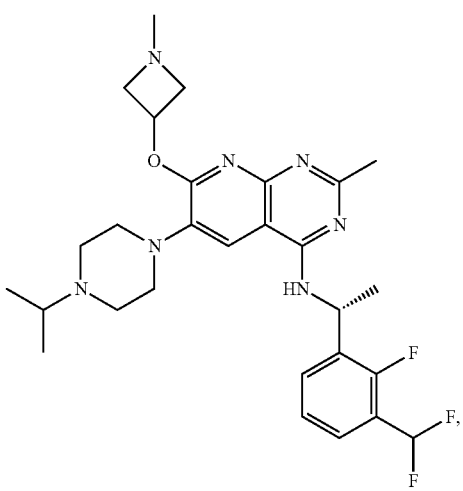
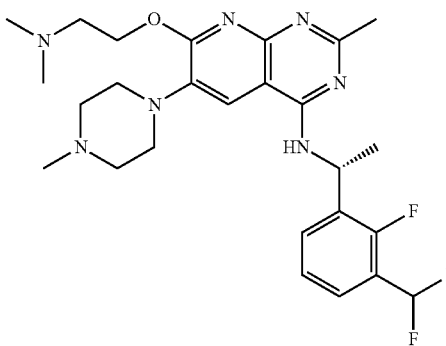

701
-continued
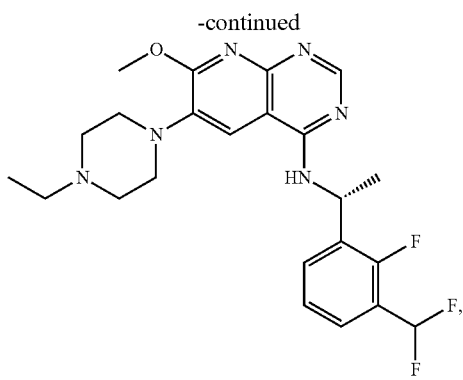
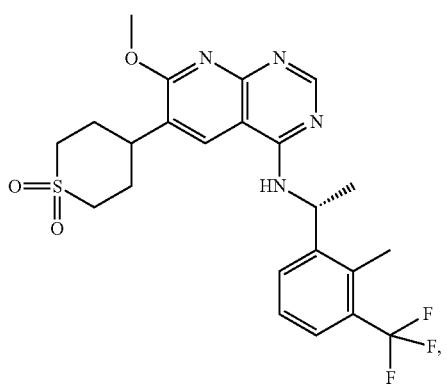
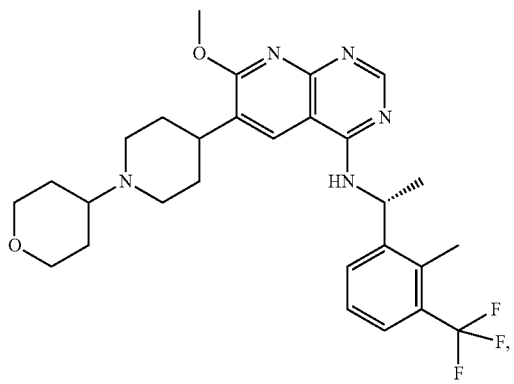
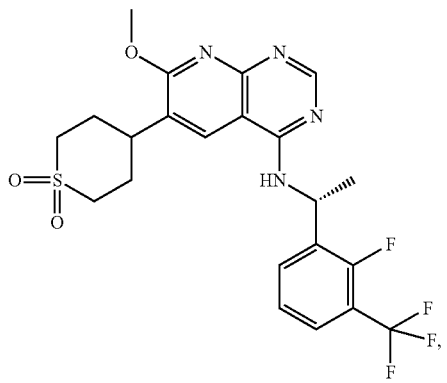
702
-continued
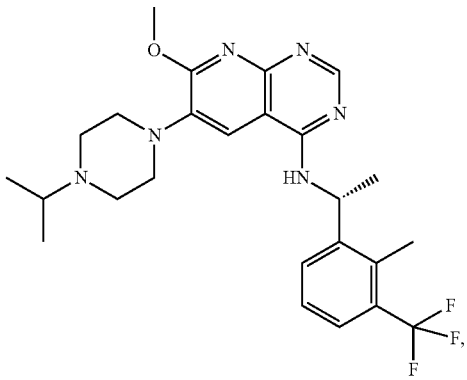
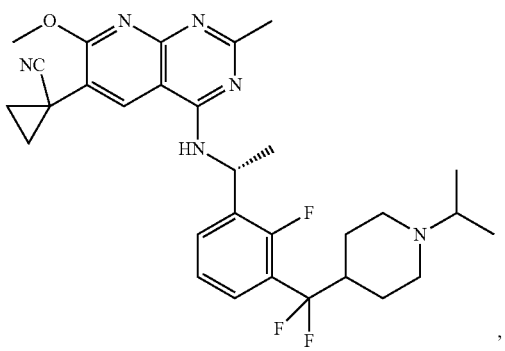
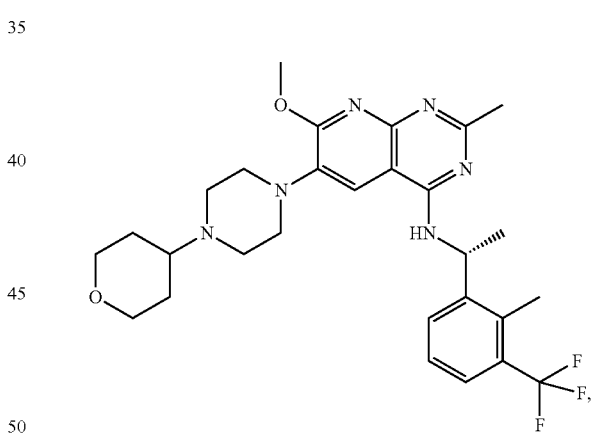
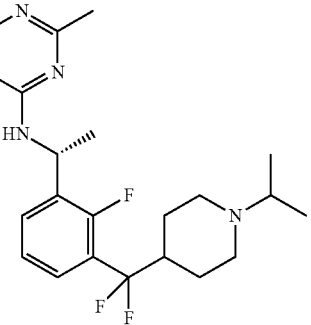

703
-continued
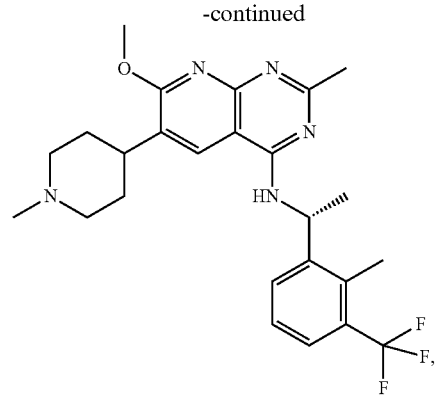
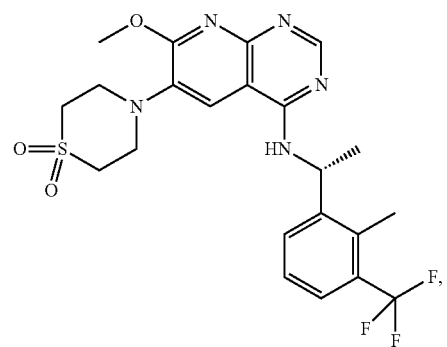
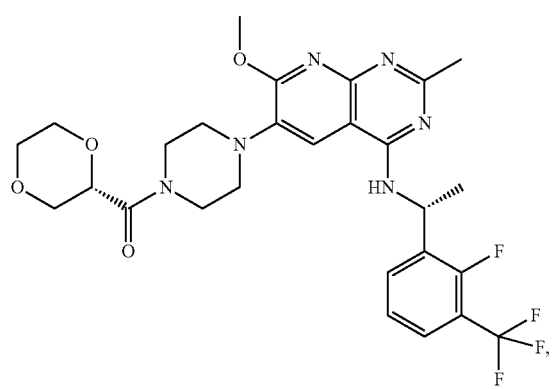
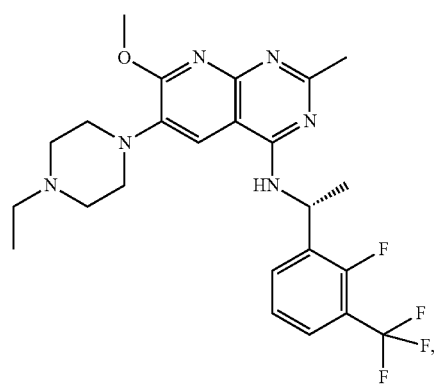
704
-continued
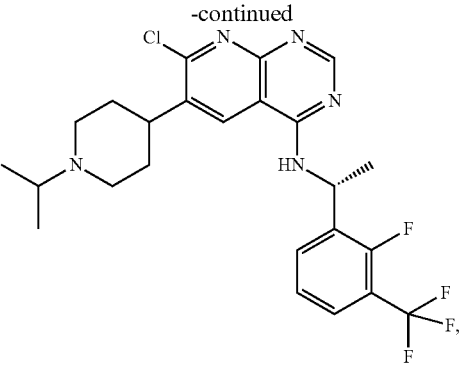
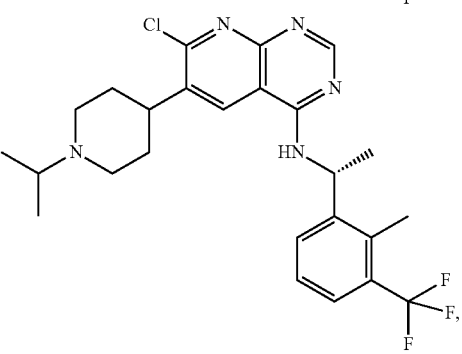
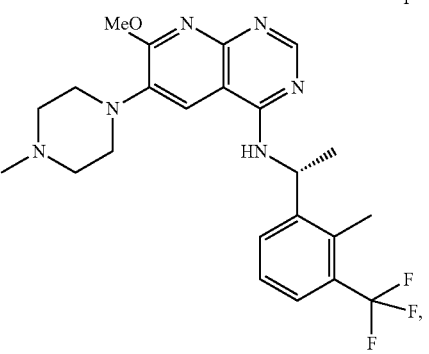
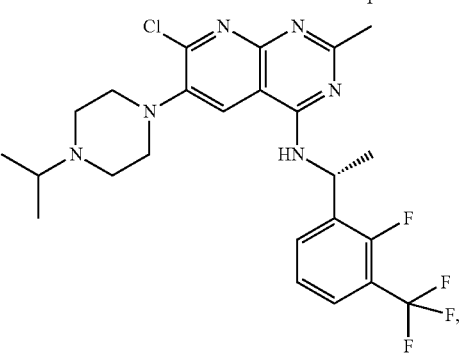
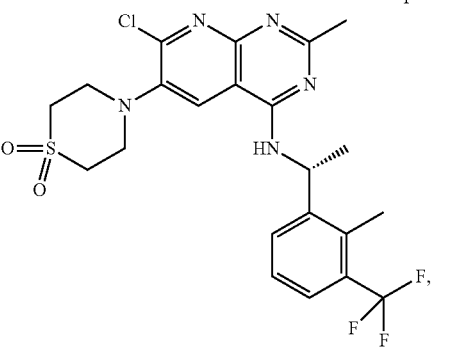

705
-continued
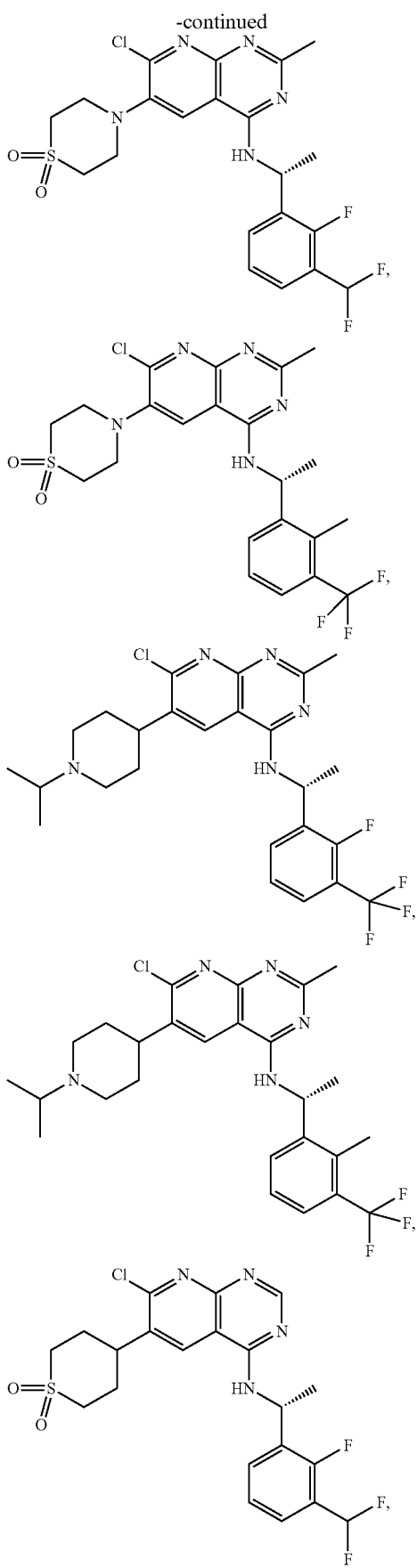
706
-continued
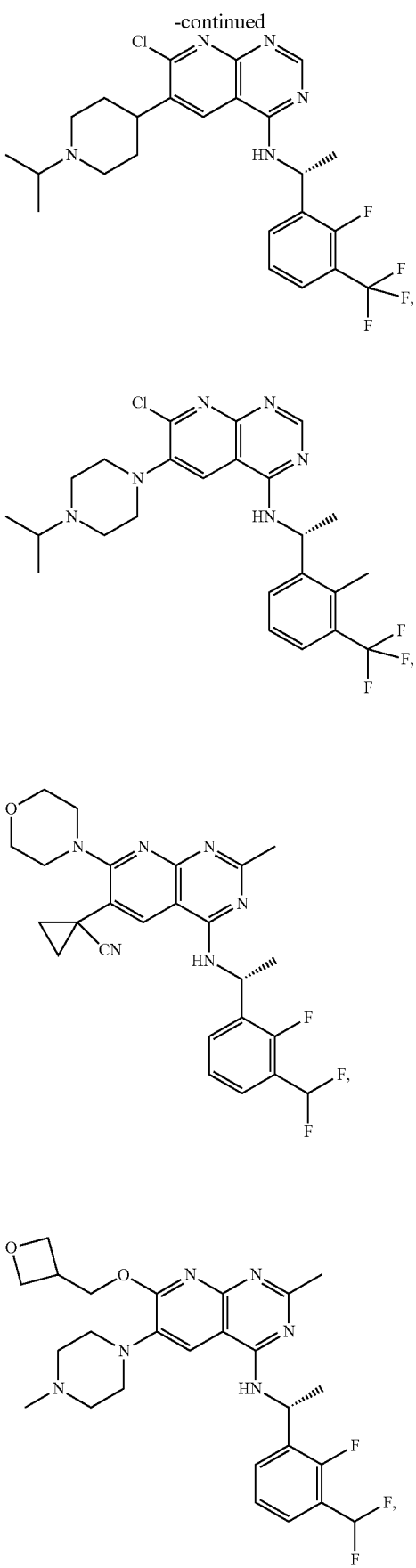

707
-continued
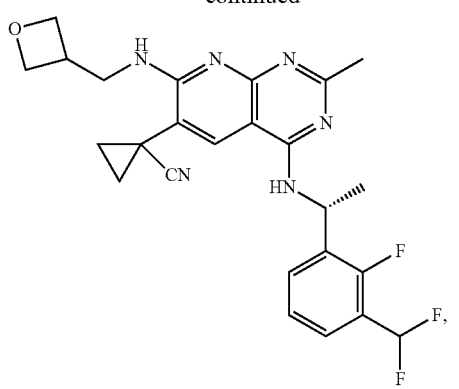
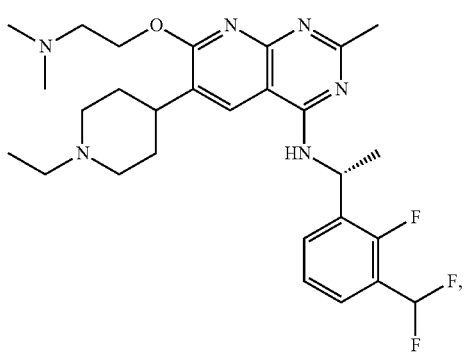
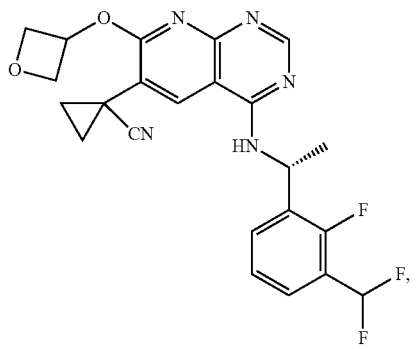
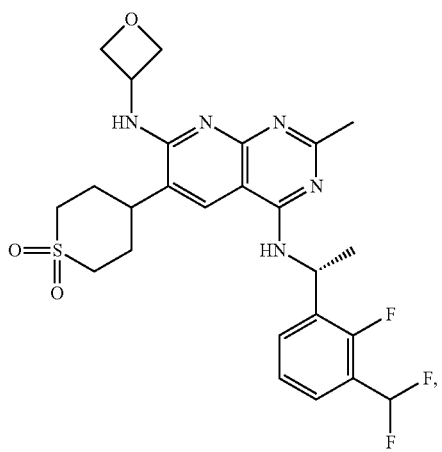
708
-continued
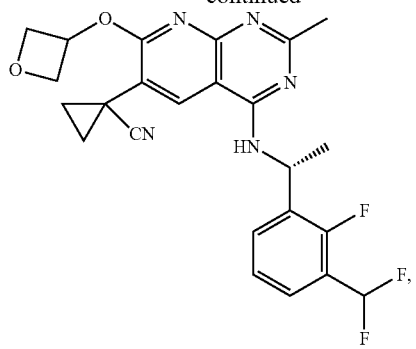
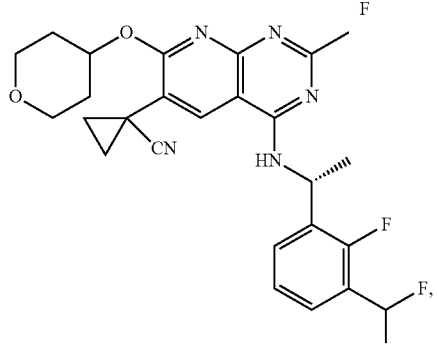
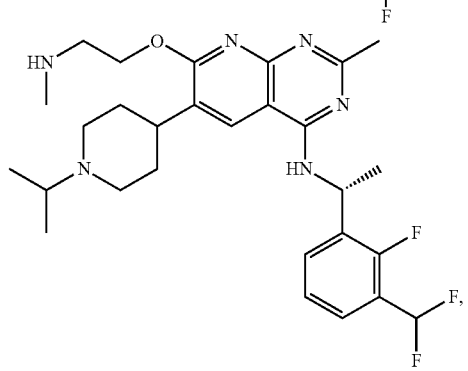
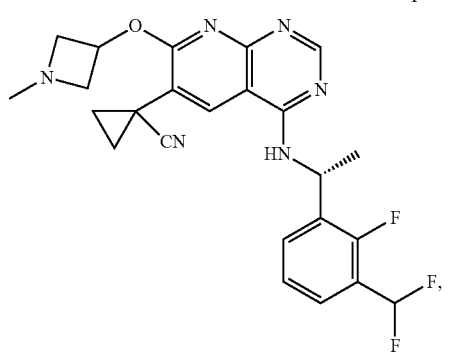
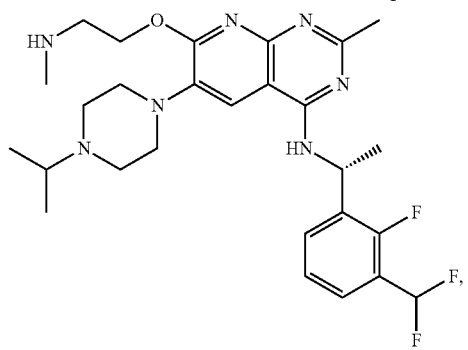

709
-continued
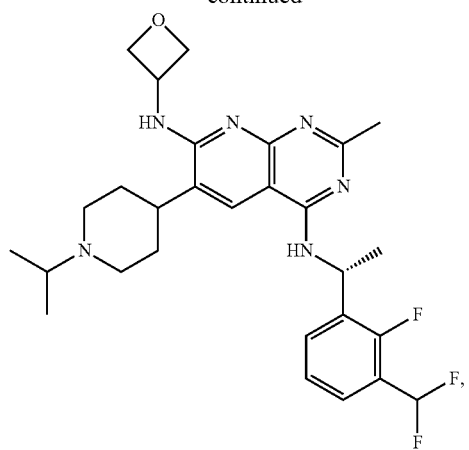
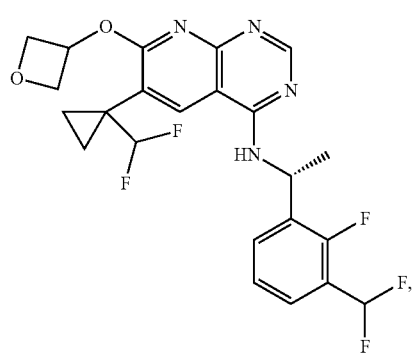
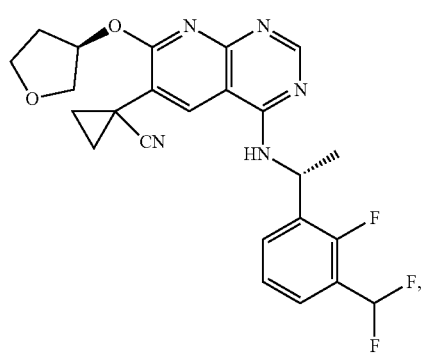
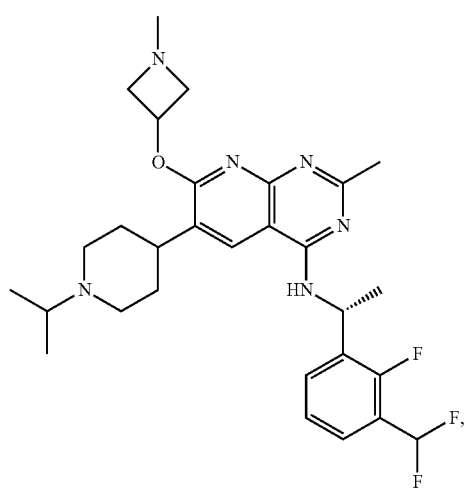
710
-continued
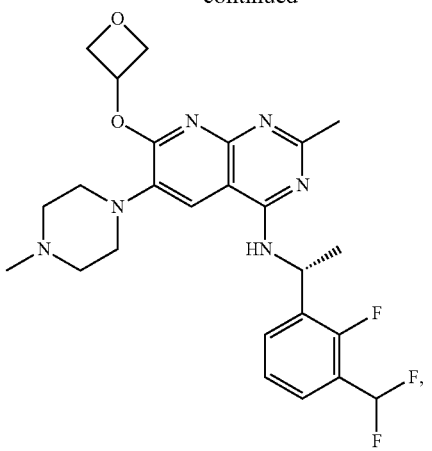
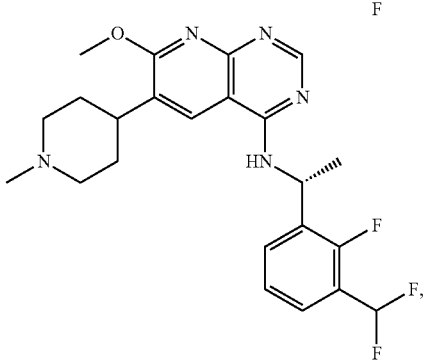
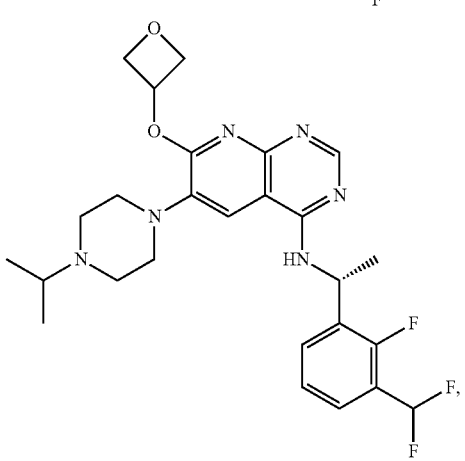
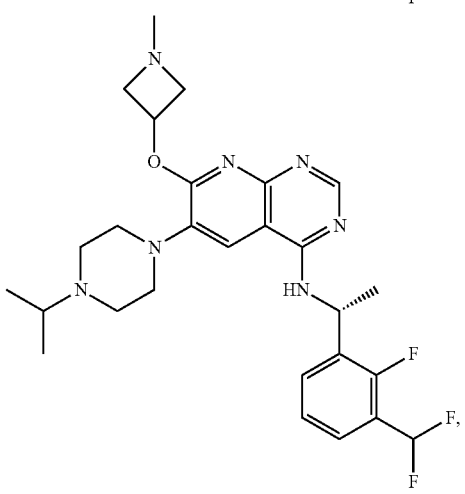

711
-continued
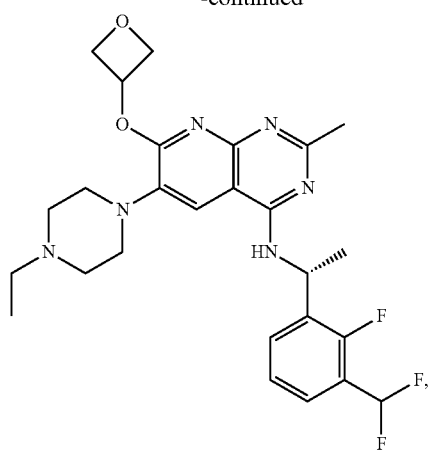
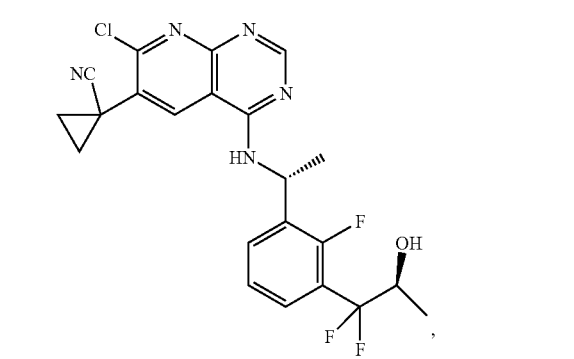
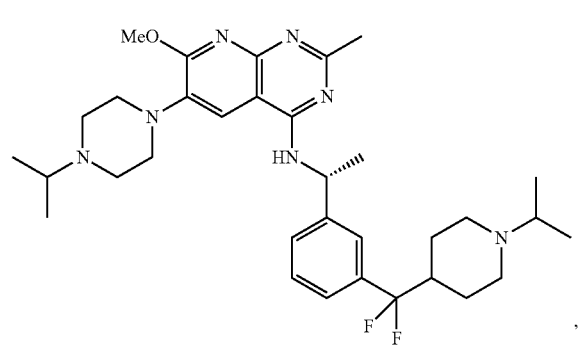
712
-continued
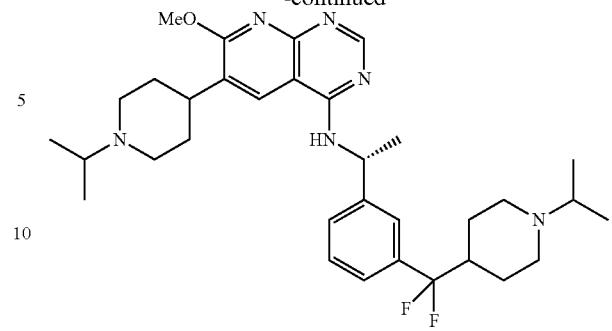
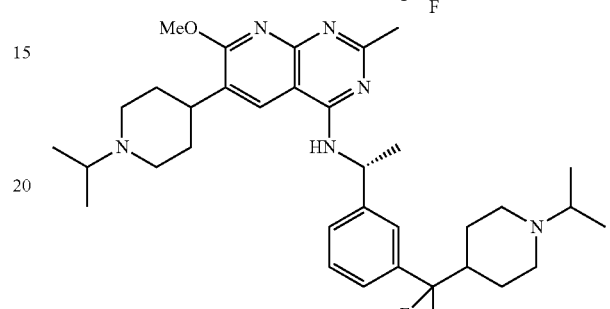
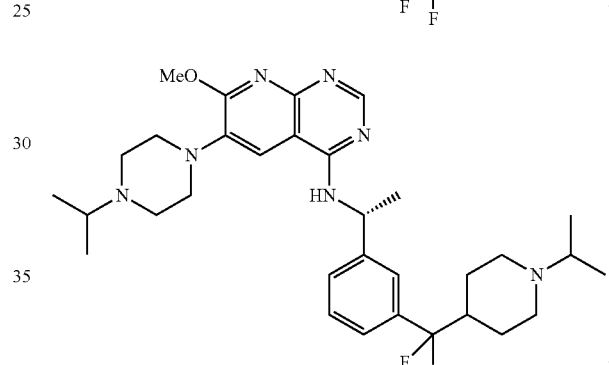
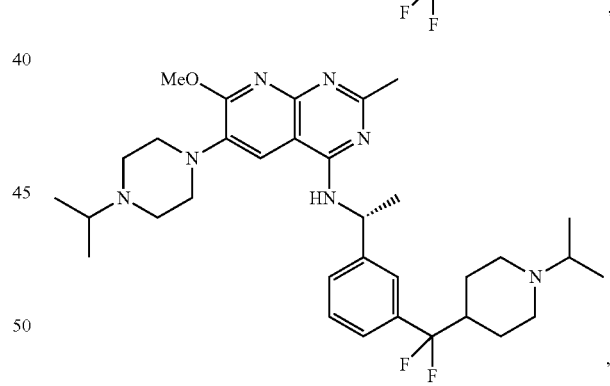
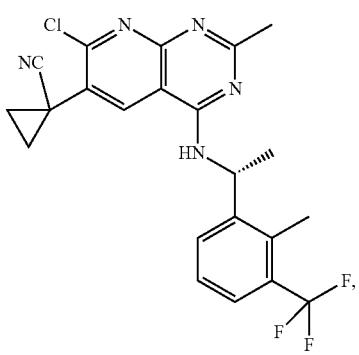

713
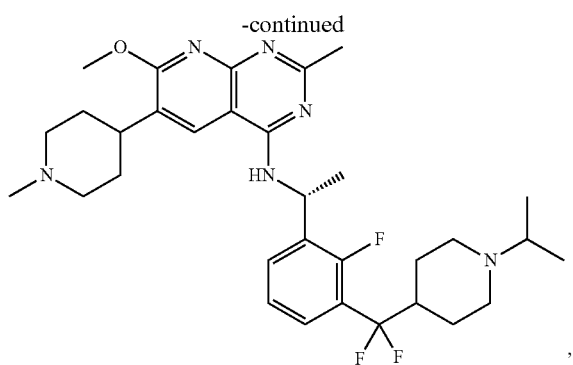
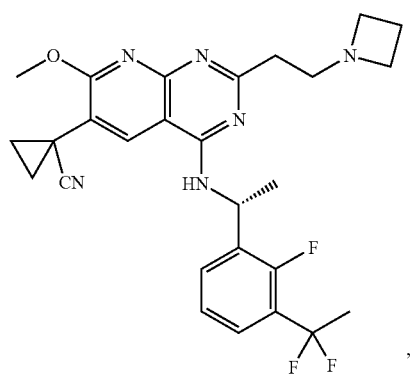
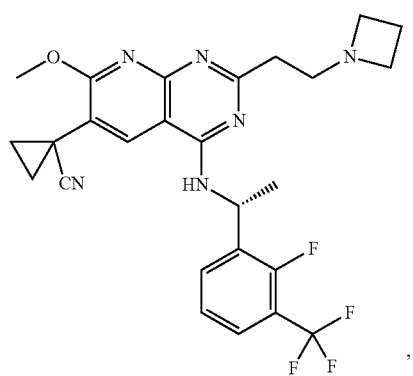
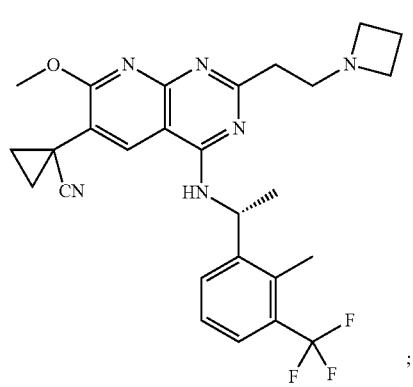
or a pharmaceutically acceptable salt or solvate thereof.
714
In some embodiments is a compound selected from:
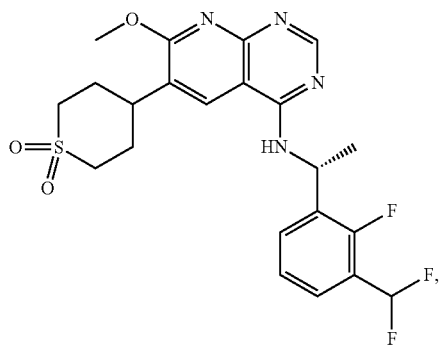
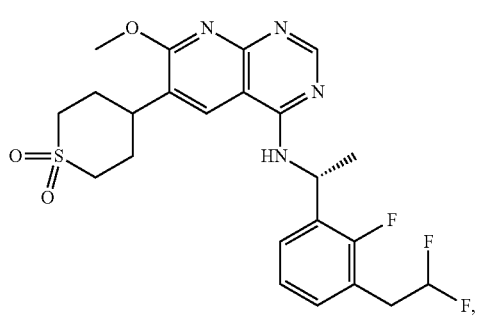
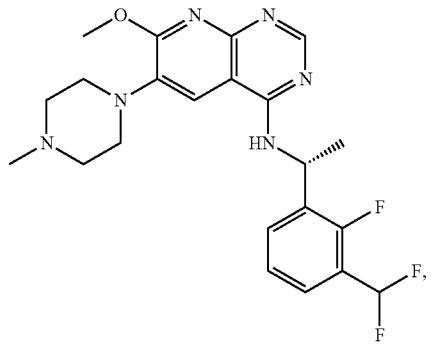
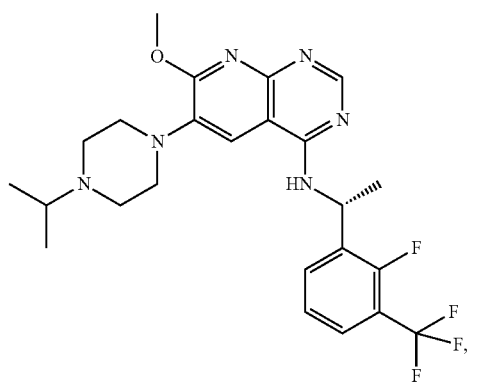

715
-continued
716
-continued
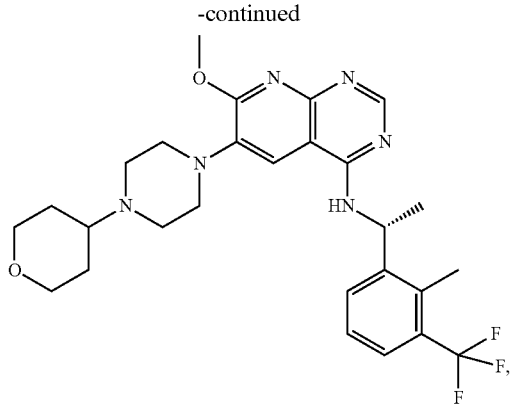
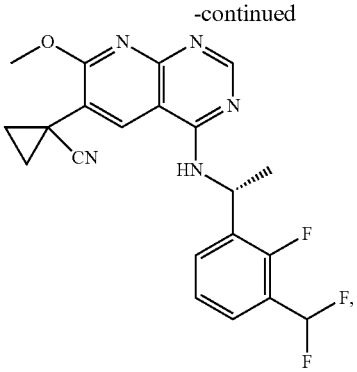
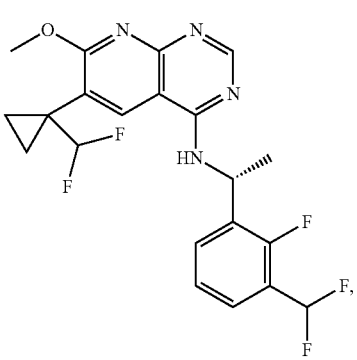

717
-continued
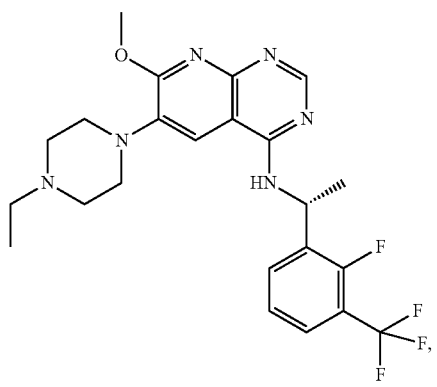
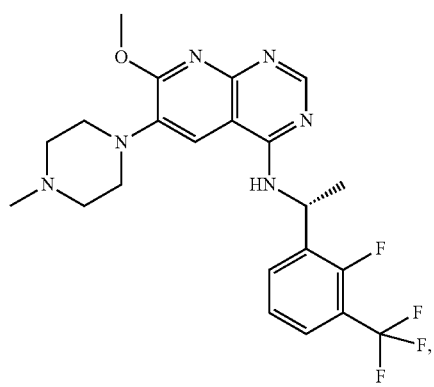
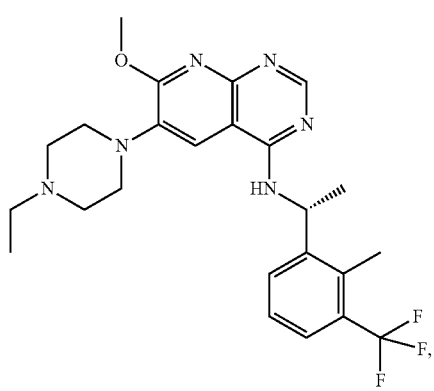
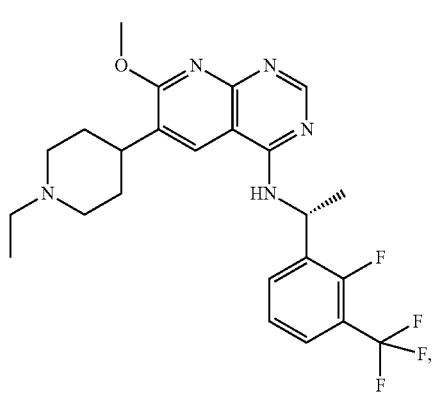
718
-continued
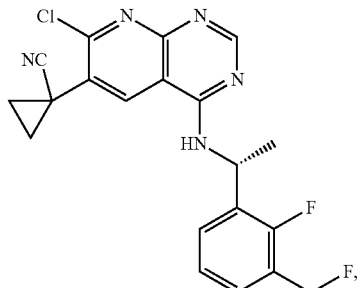
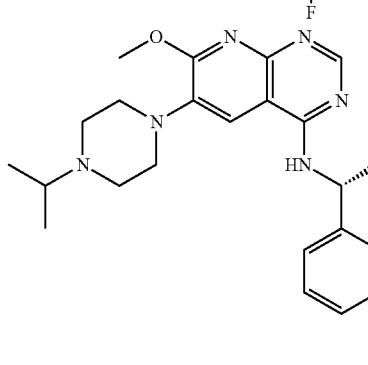
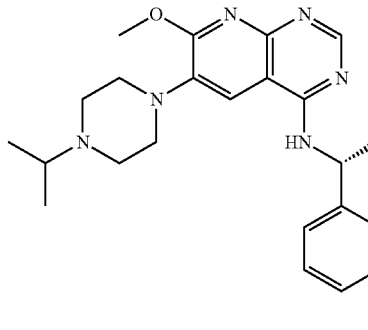
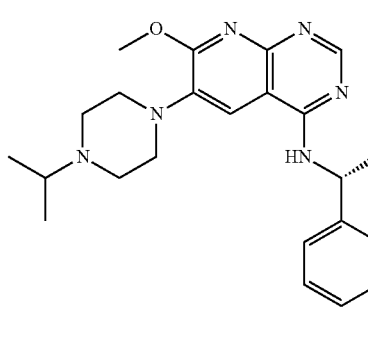
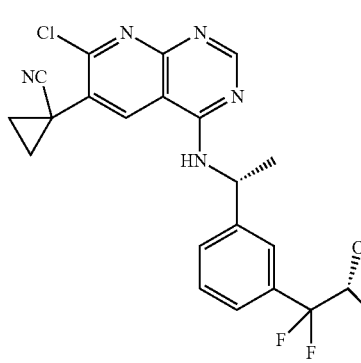

719
-continued
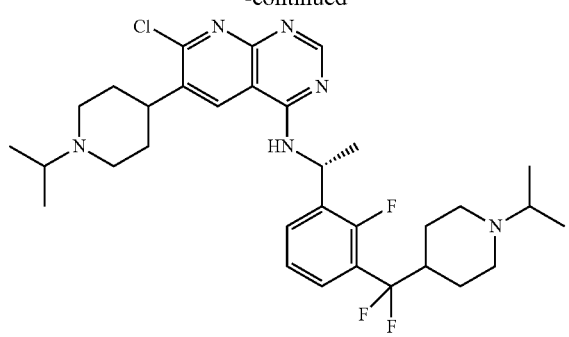
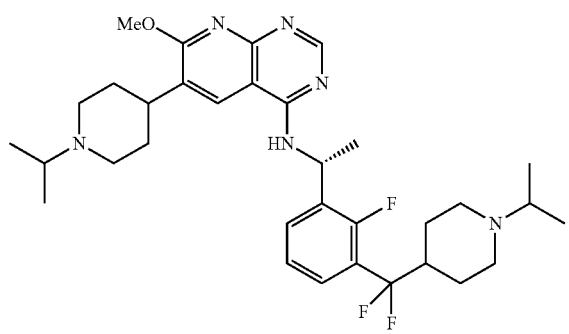
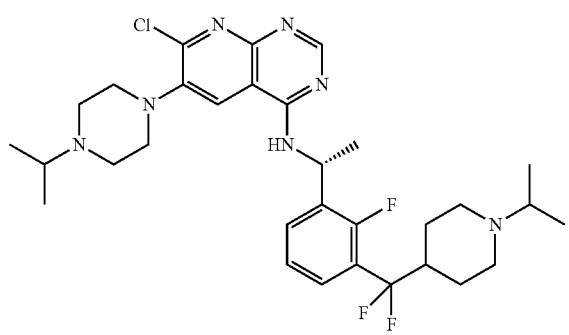
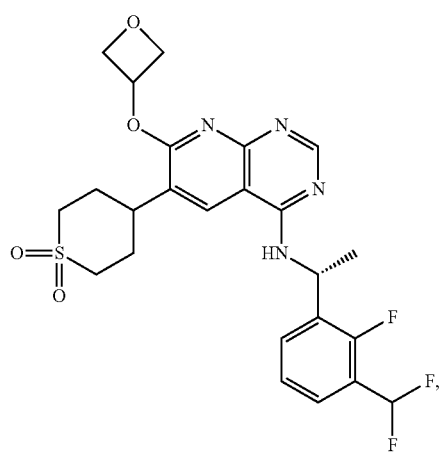
720
-continued
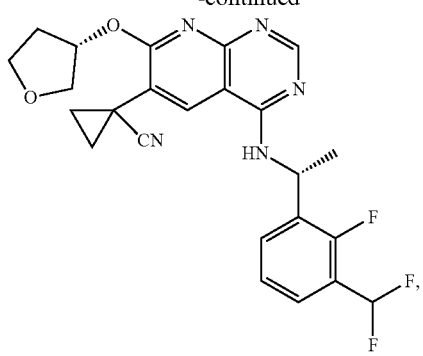
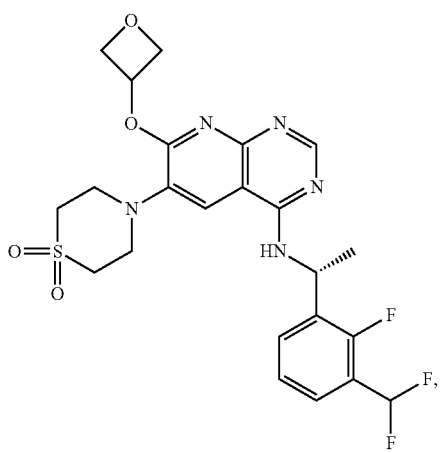
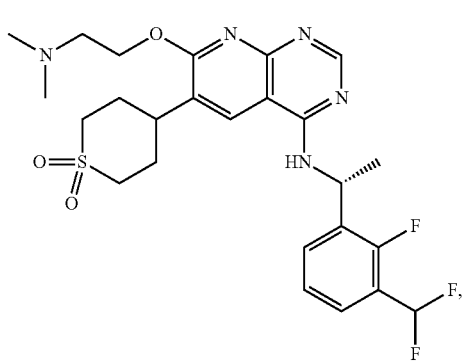
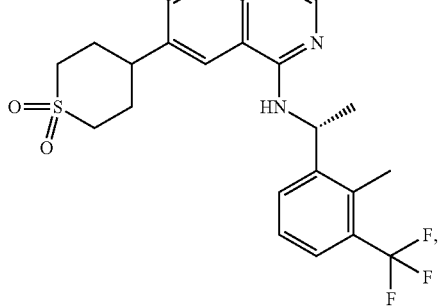

721
-continued
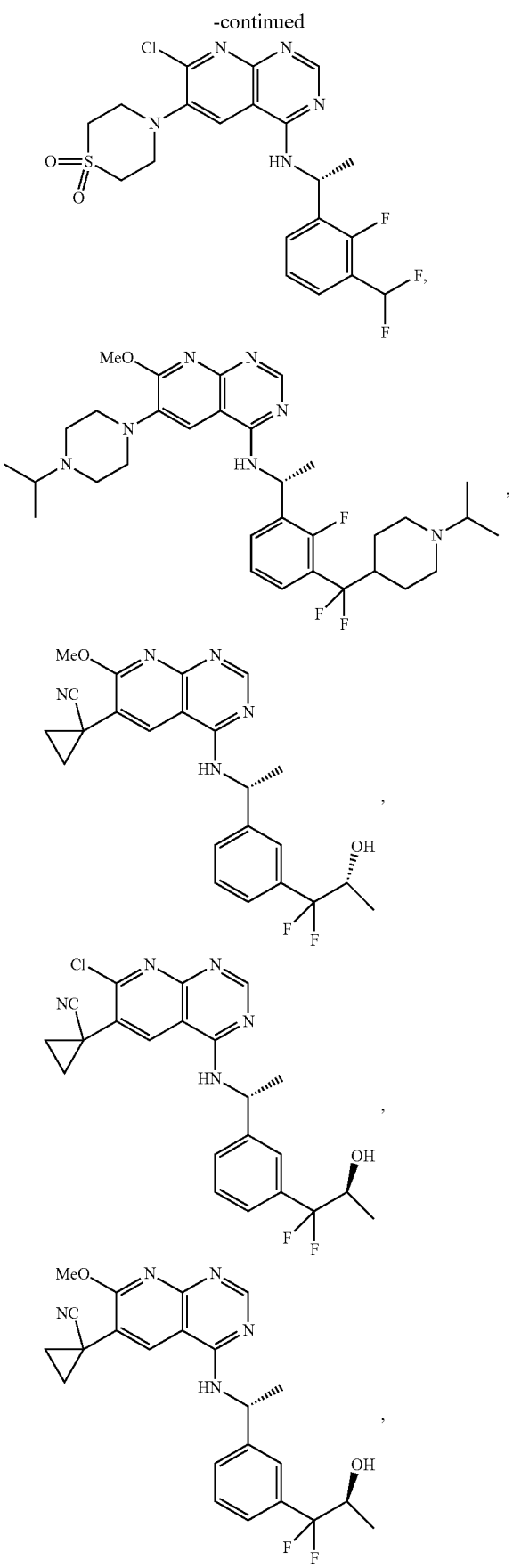
722
-continued
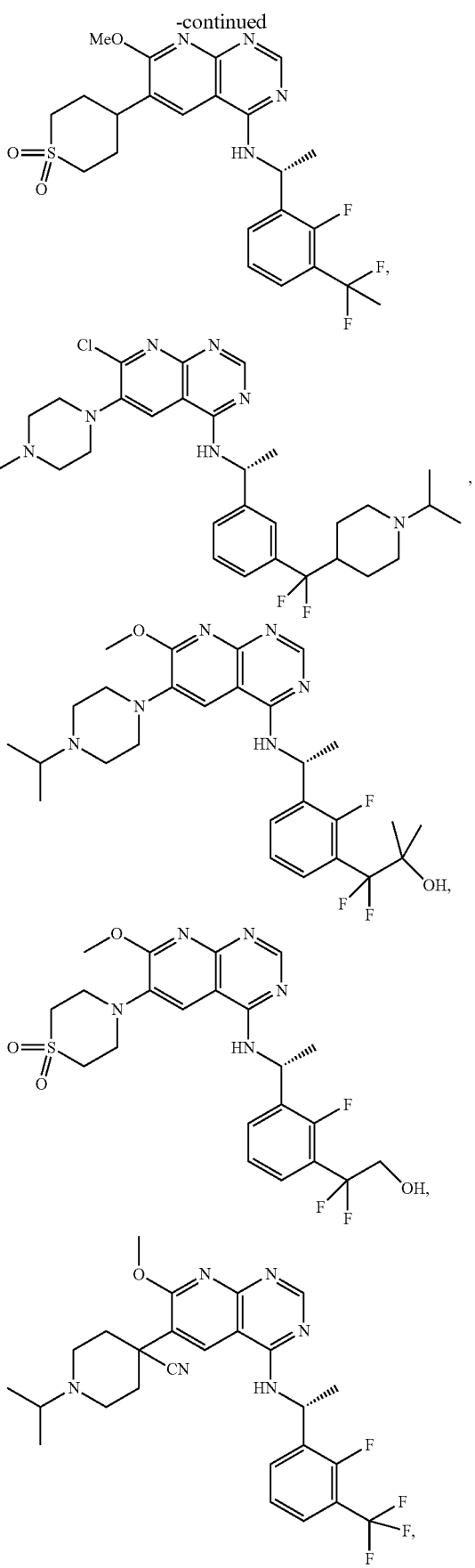

723
-continued
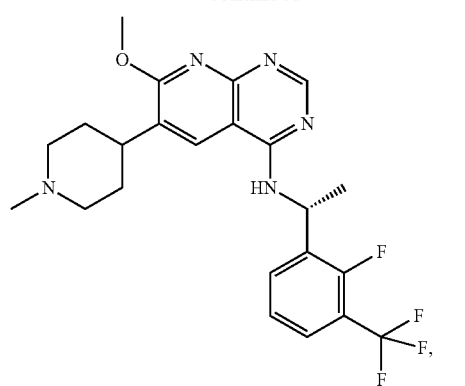
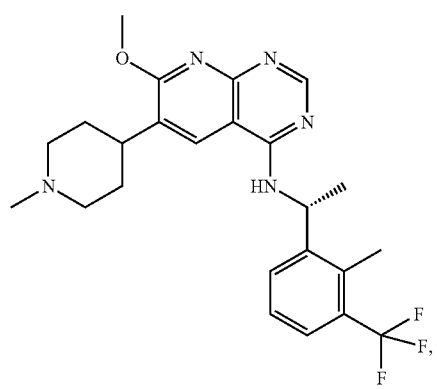
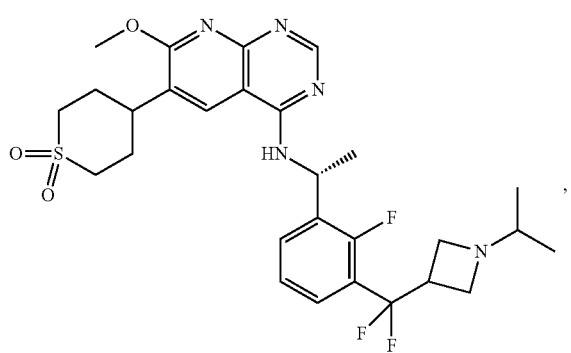
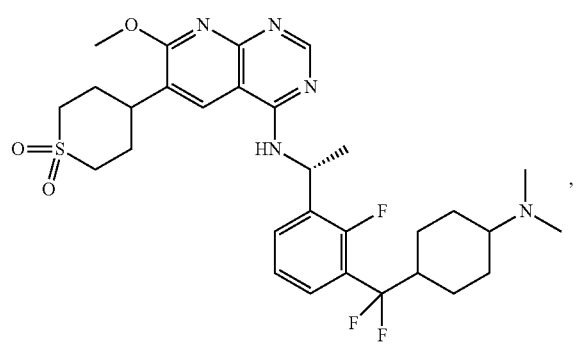
724
-continued
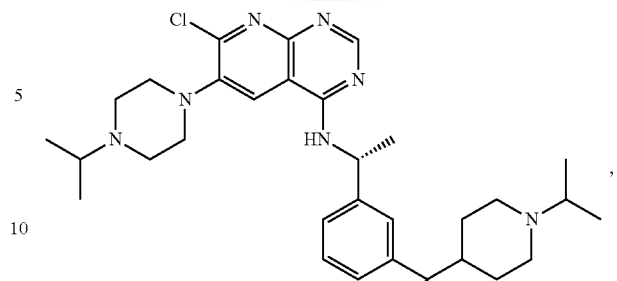
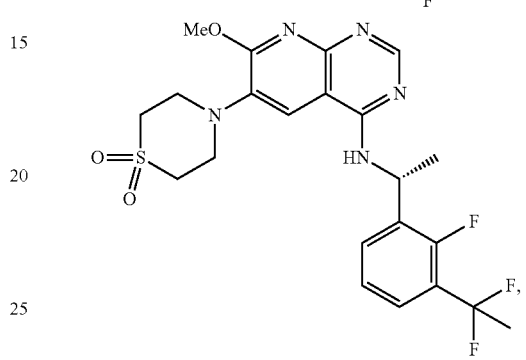
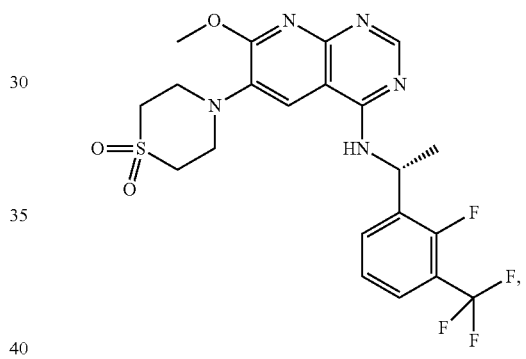
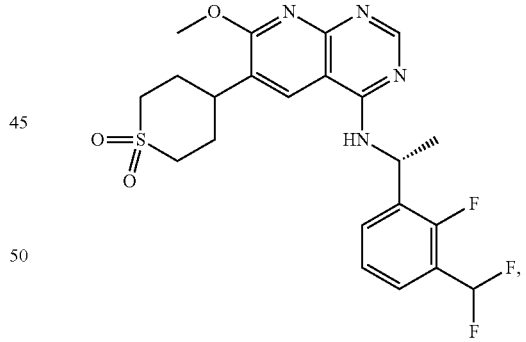
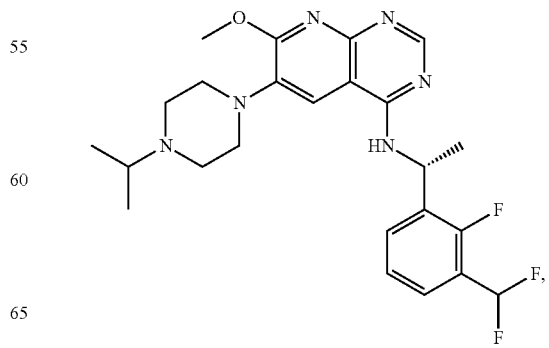

725
-continued
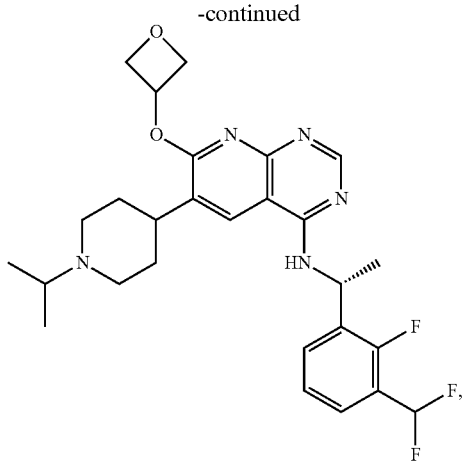
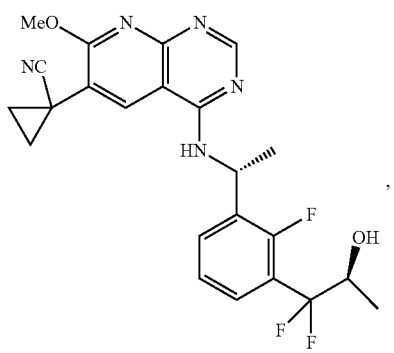
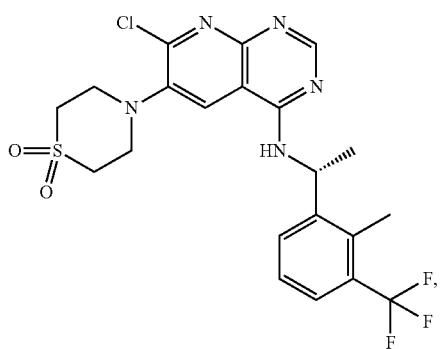
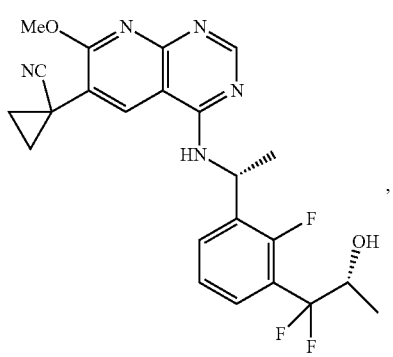
726
-continued
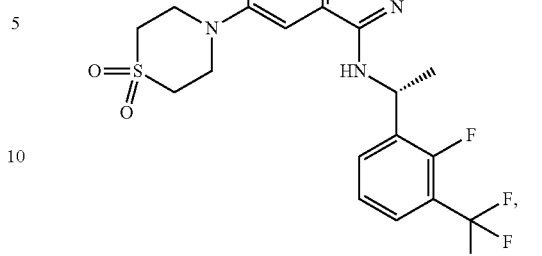
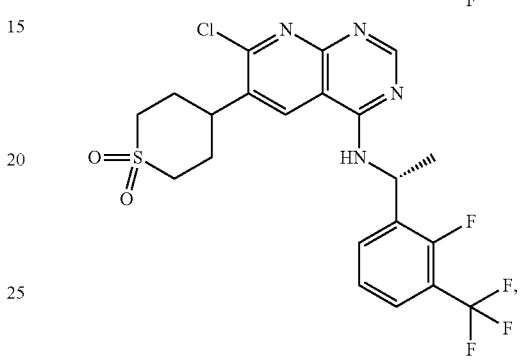
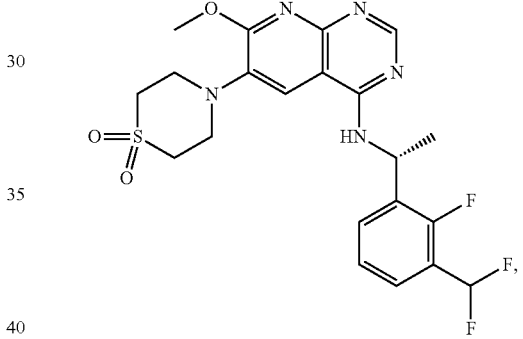
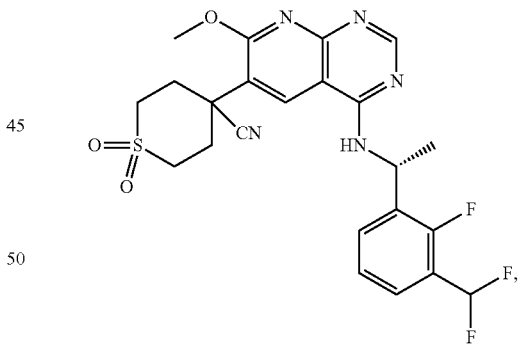
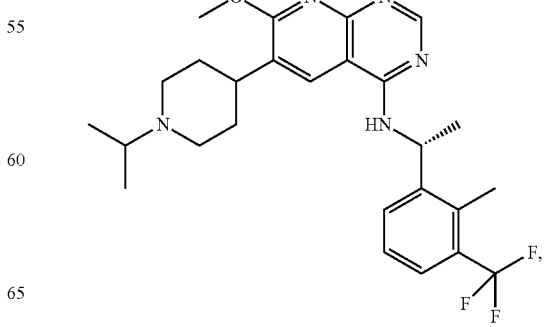

727
-continued
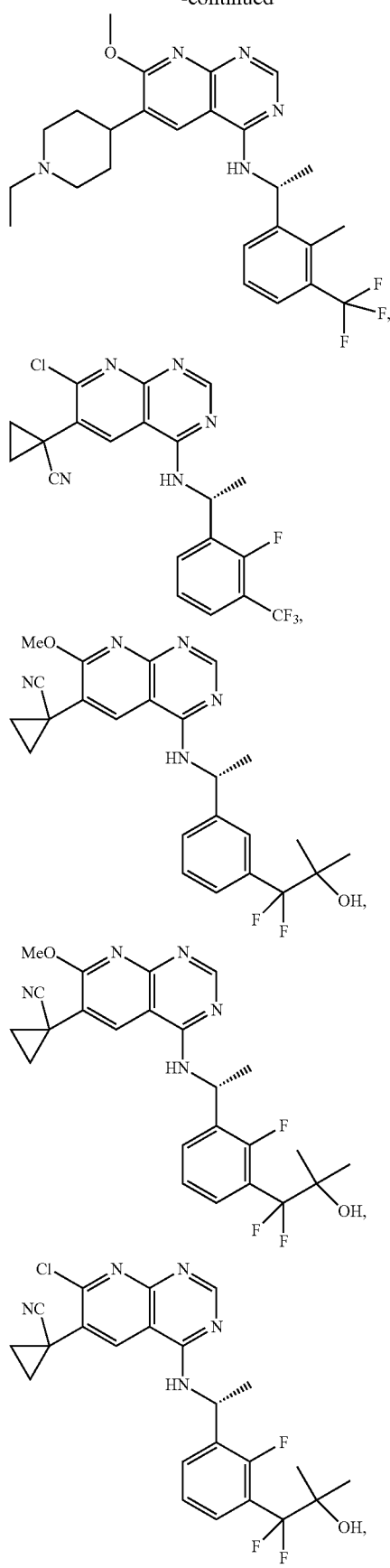
728
-continued
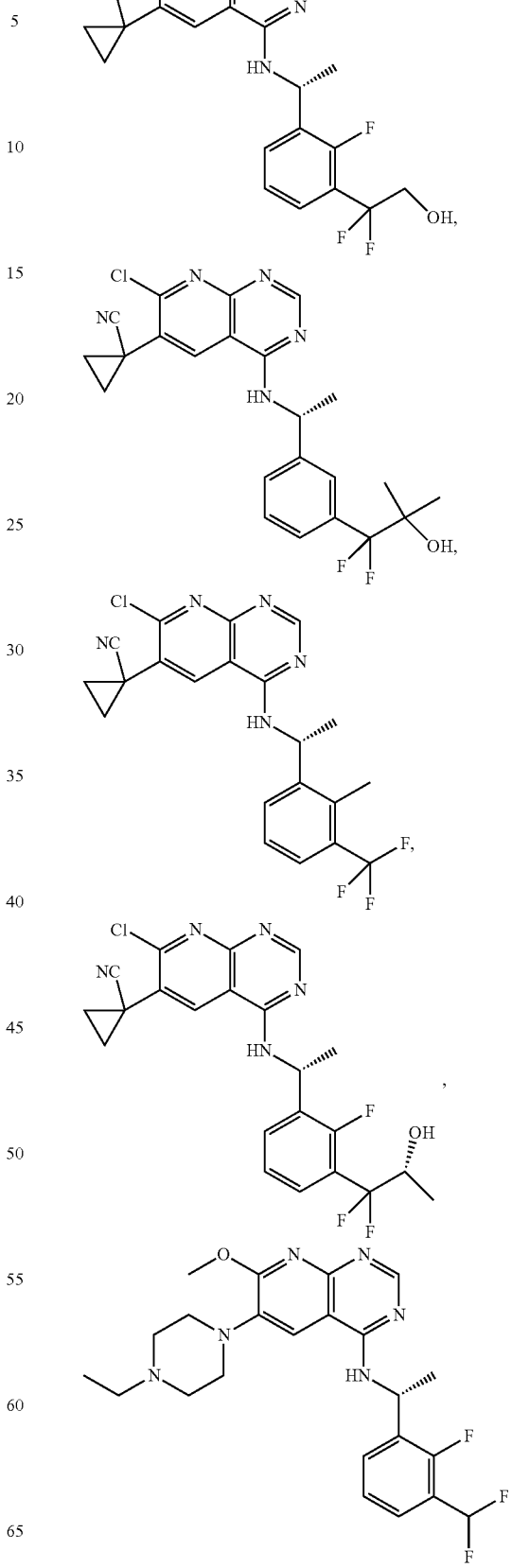

729
-continued
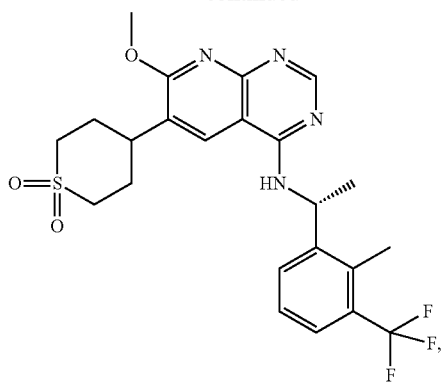
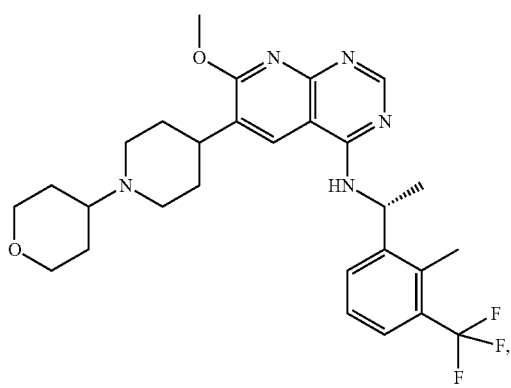
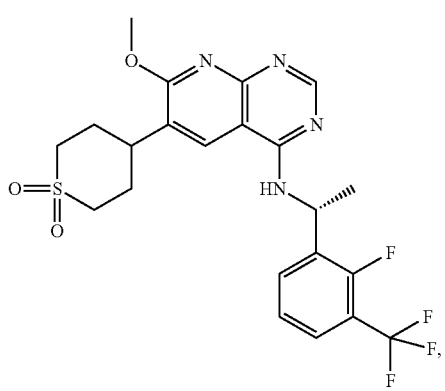
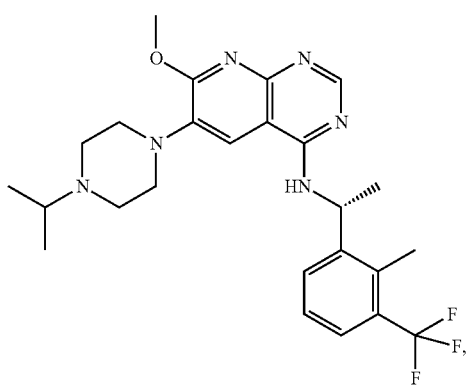
730
-continued
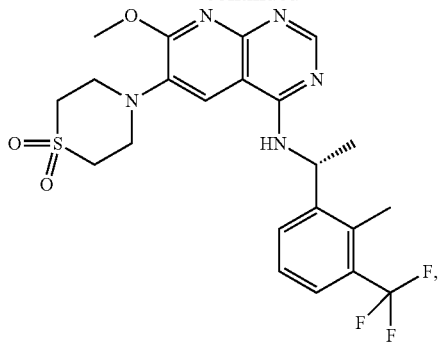
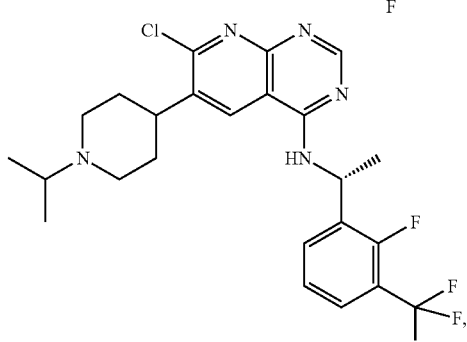
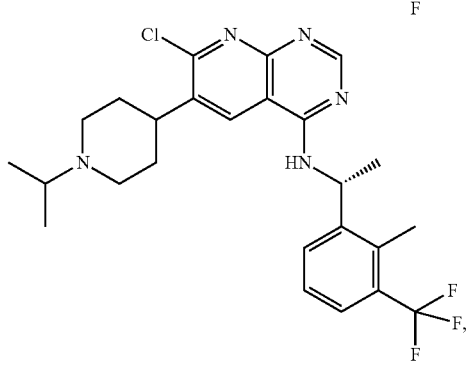
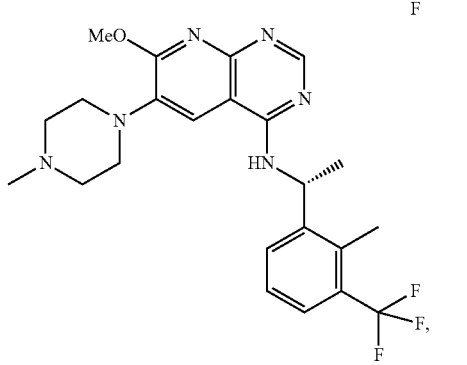
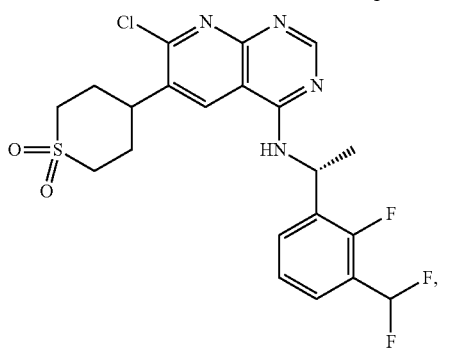

731
-continued
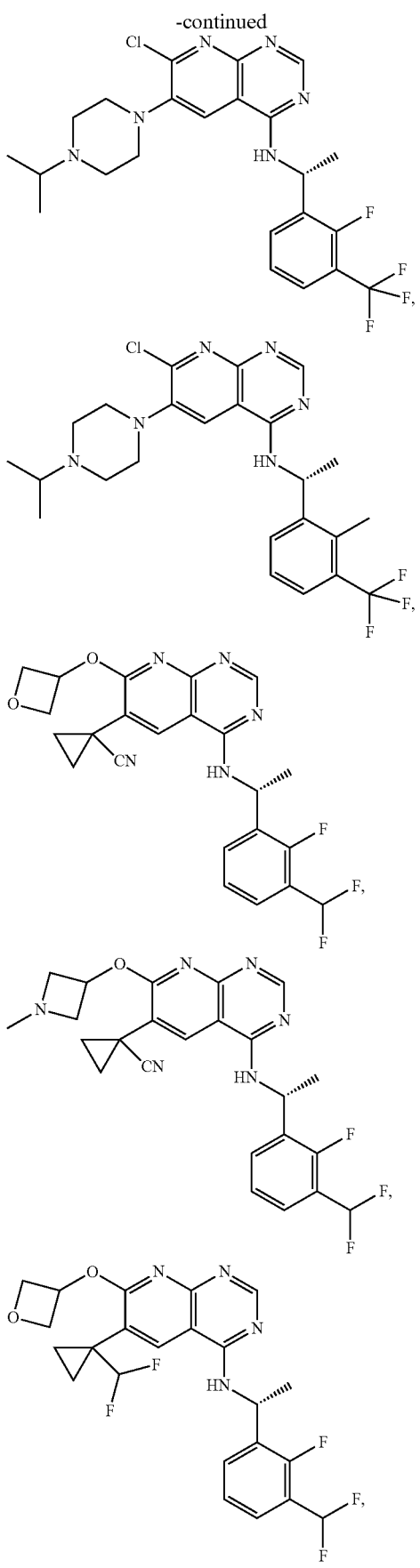
732
-continued
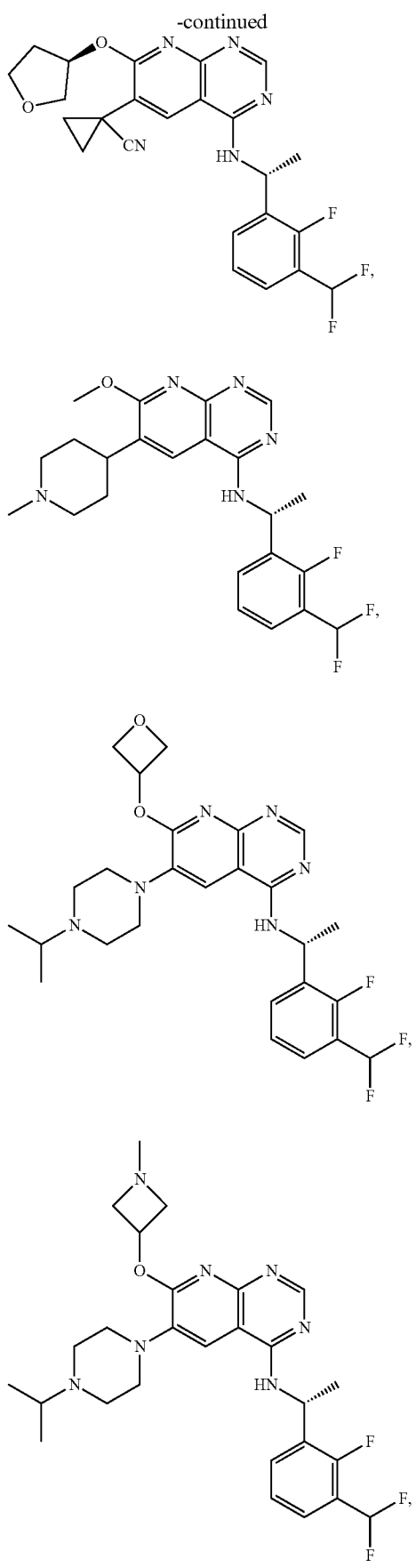

-continued
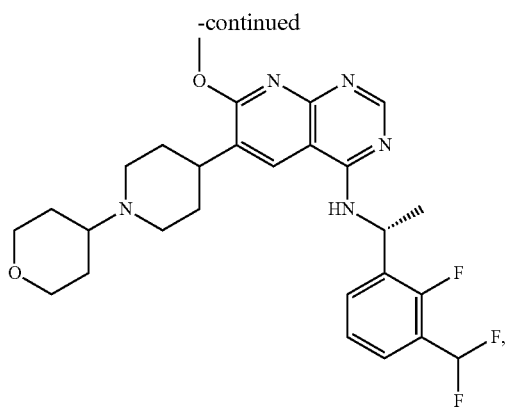
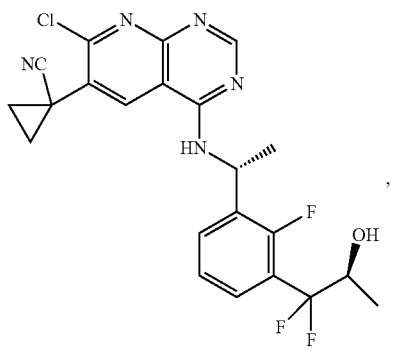
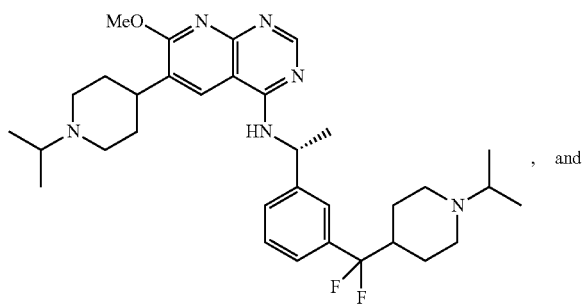
, and
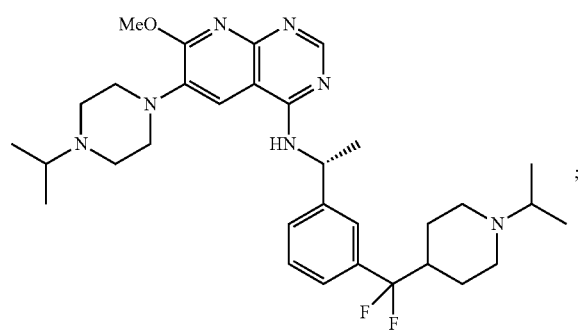
;
or a pharmaceutically acceptable salt or solvate thereof.
In some embodiments is a compound selected from:
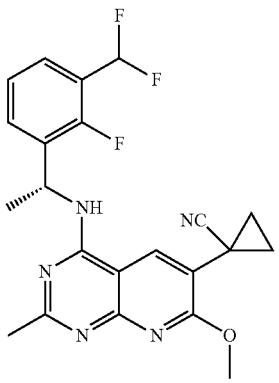
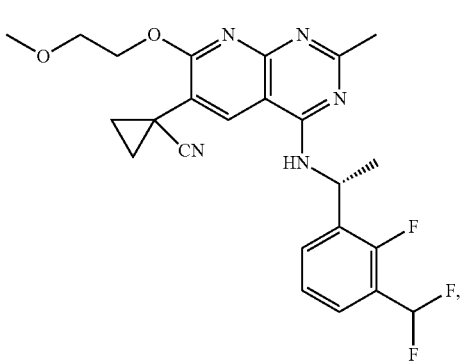
,
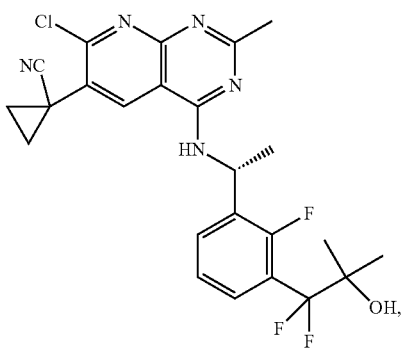
,
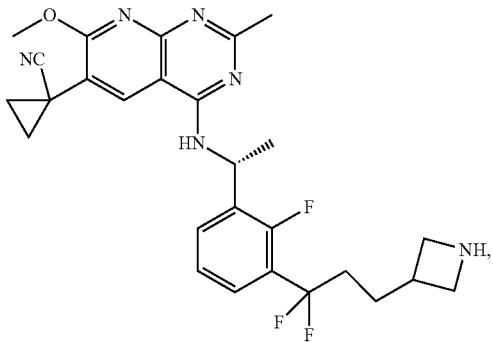

735
-continued
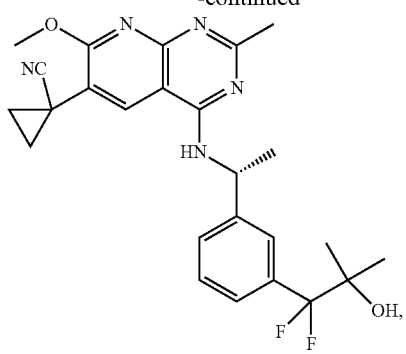
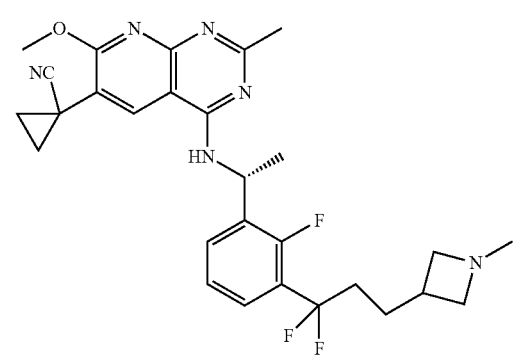
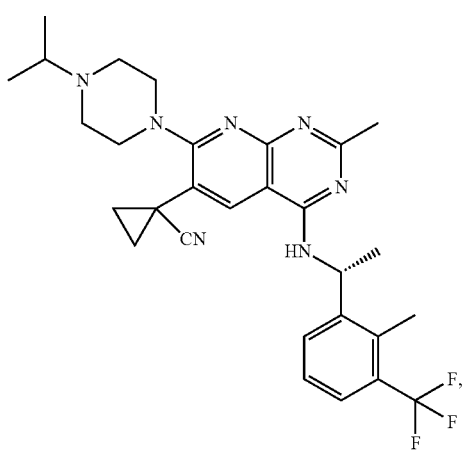
736
-continued
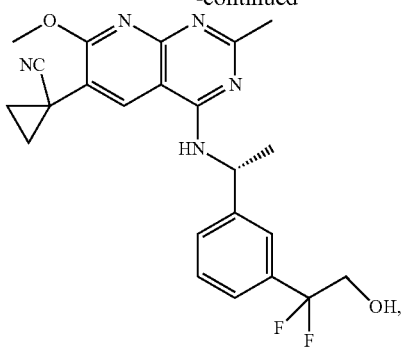
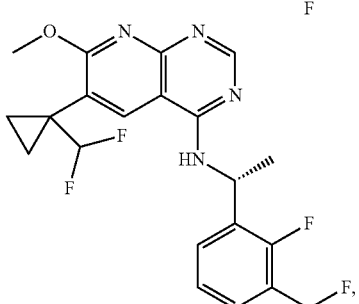
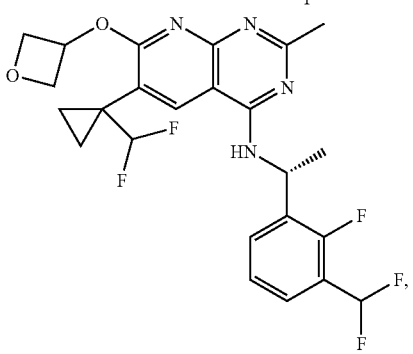

737
-continued
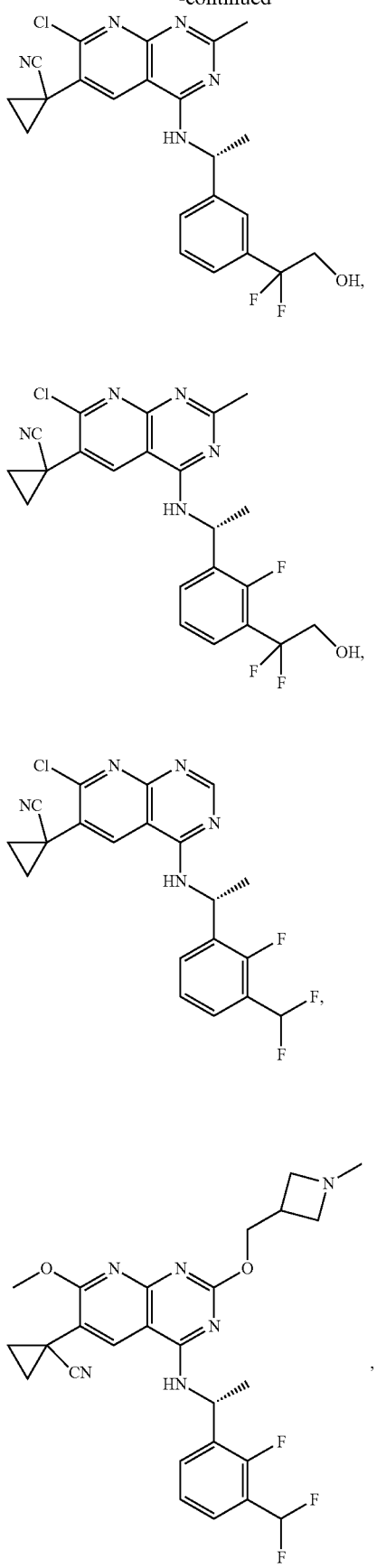
738
-continued
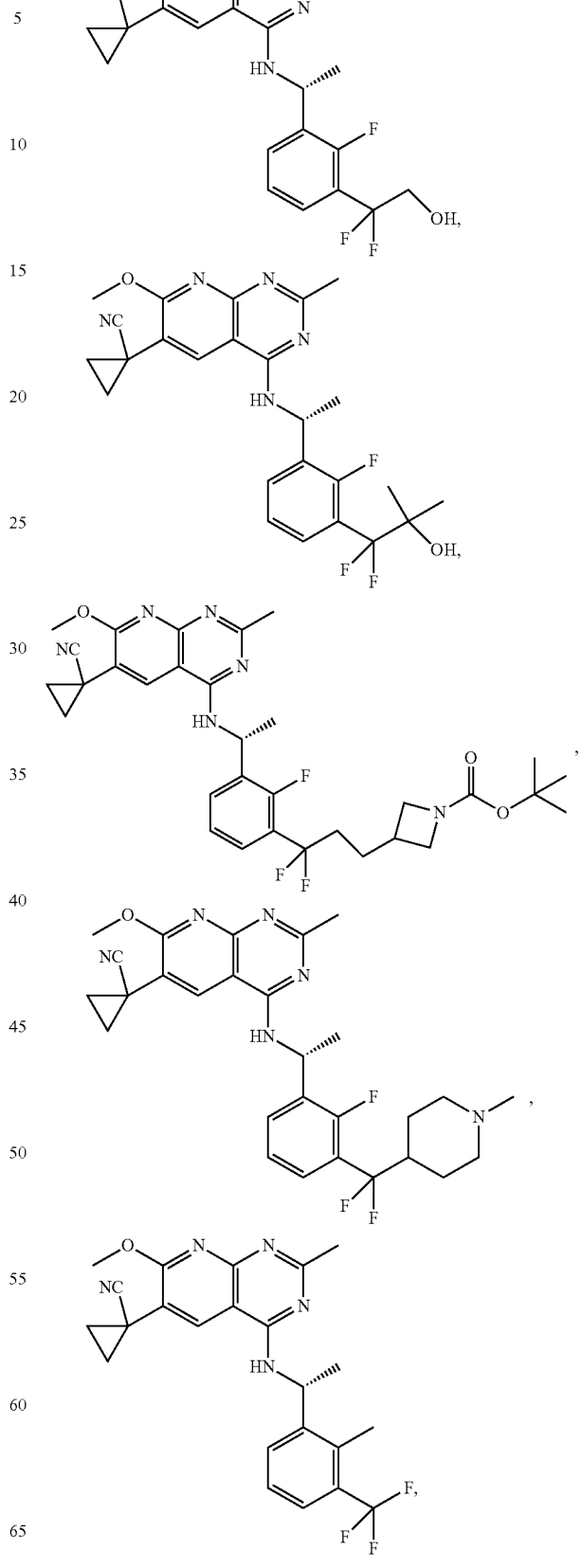

739
-continued
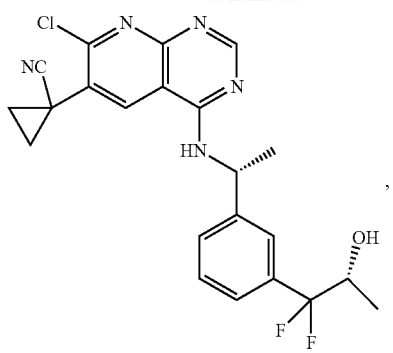
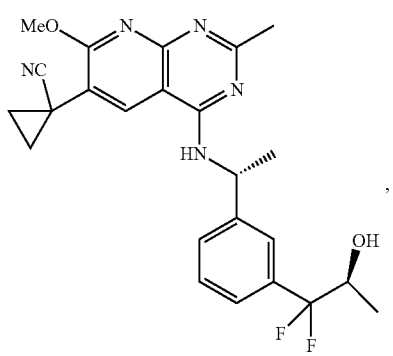
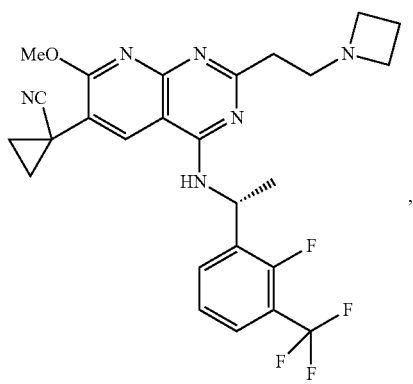
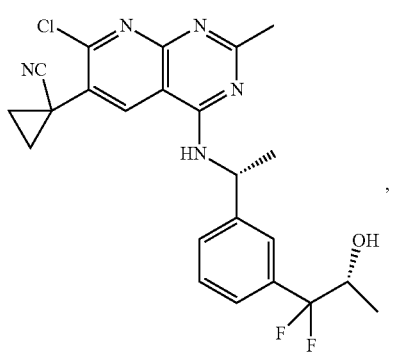
740
-continued
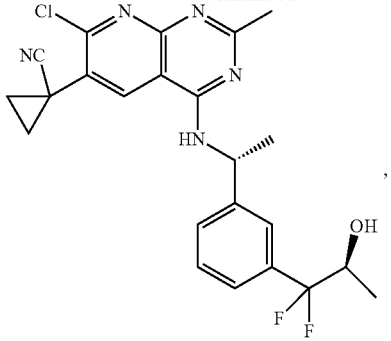
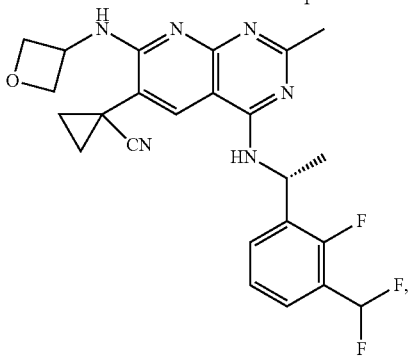
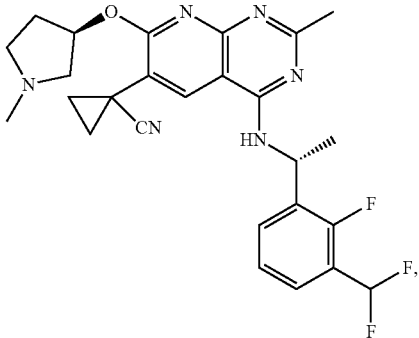
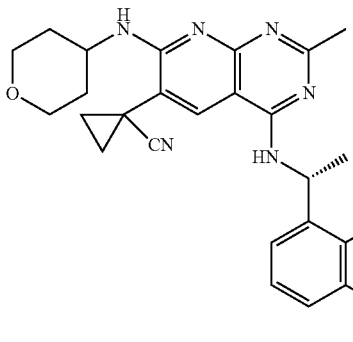
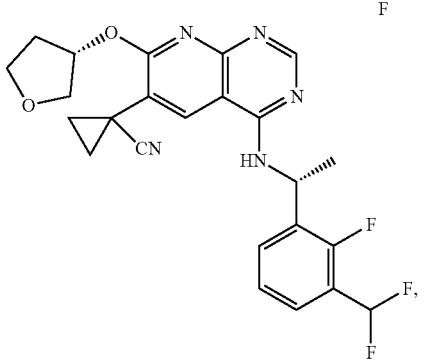

| 741 | 742 |
|---|---|
| 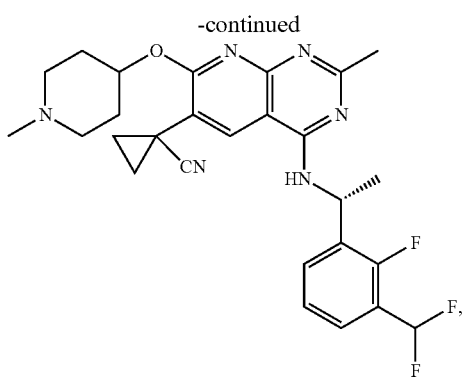 | 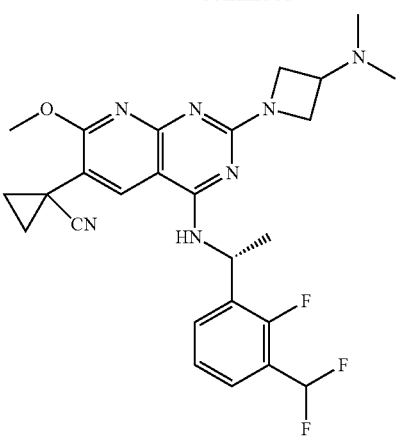 |
| 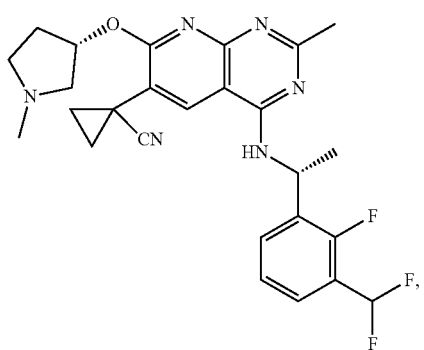 | 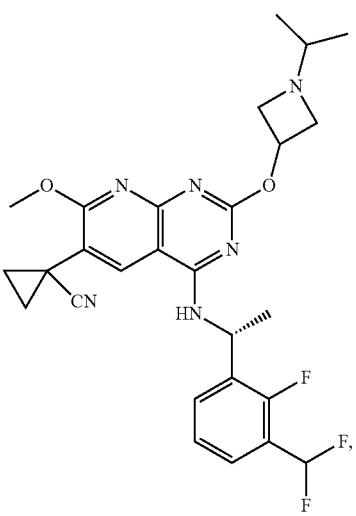 |
| 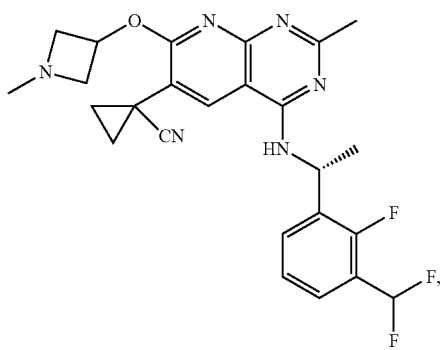 | |
| 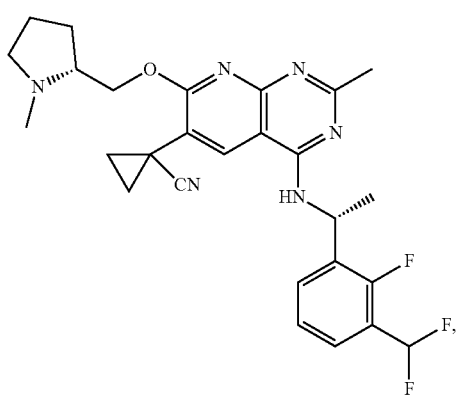 | 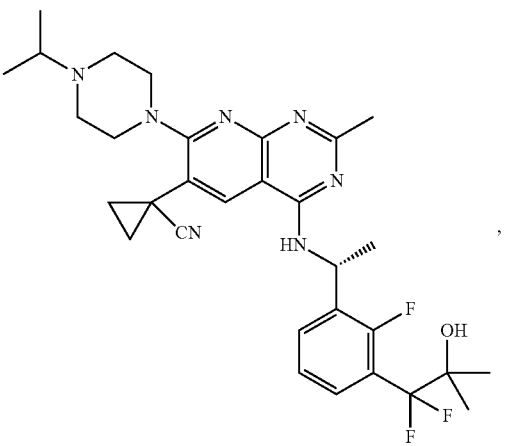 |

743
-continued
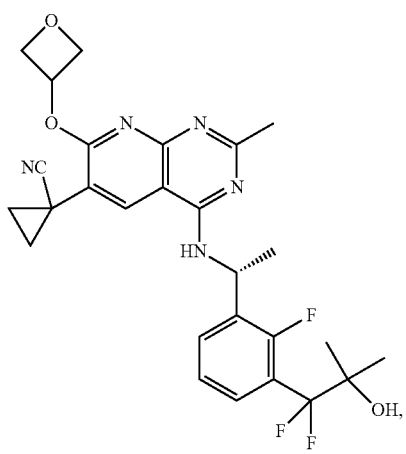
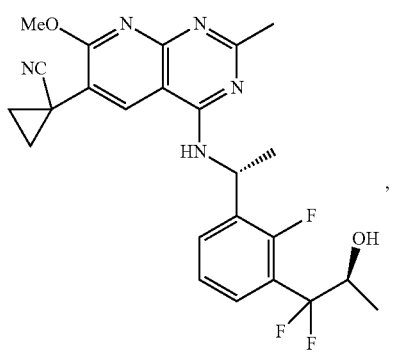
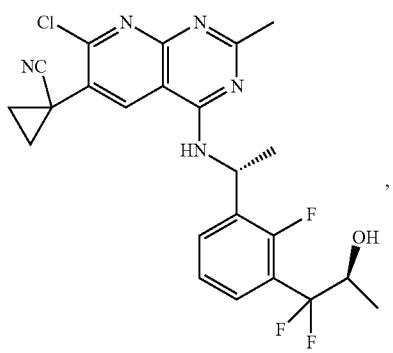
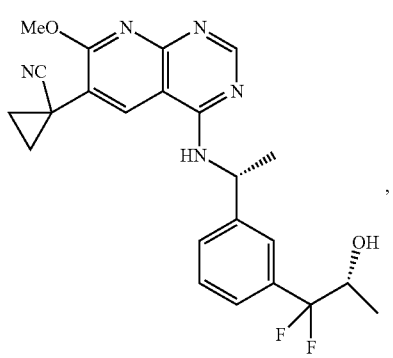
744
-continued
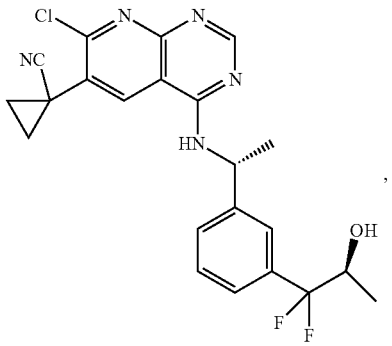
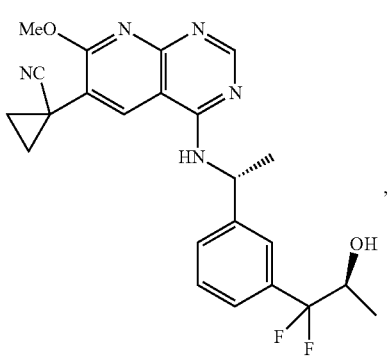
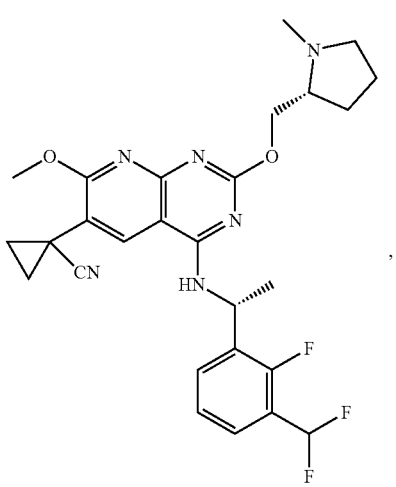
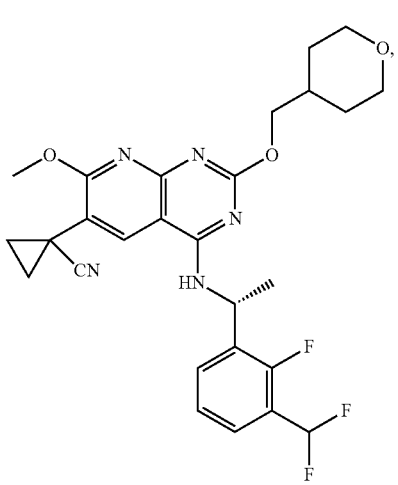

745
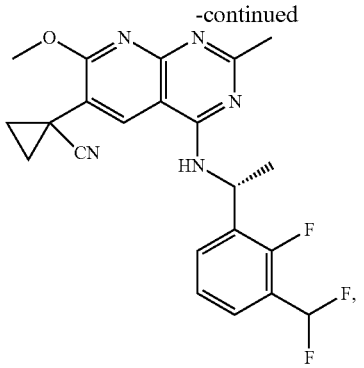
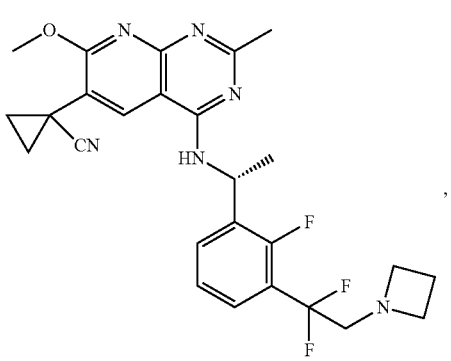
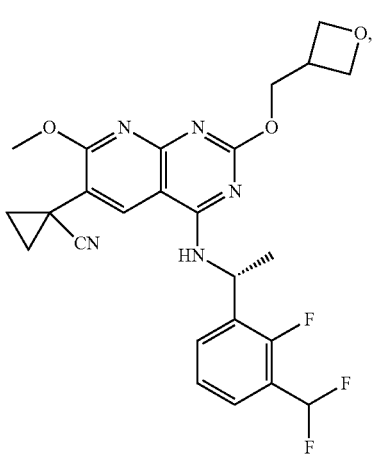
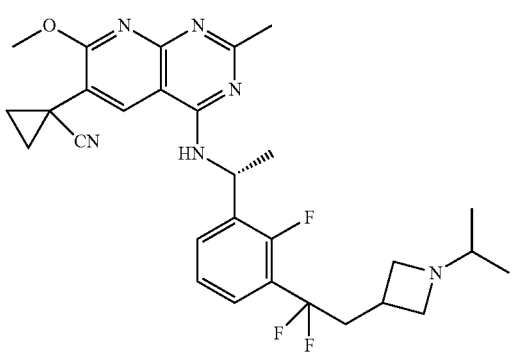
746
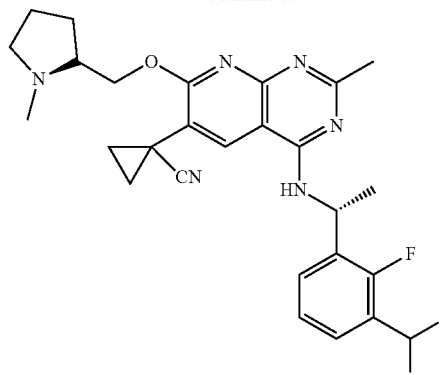
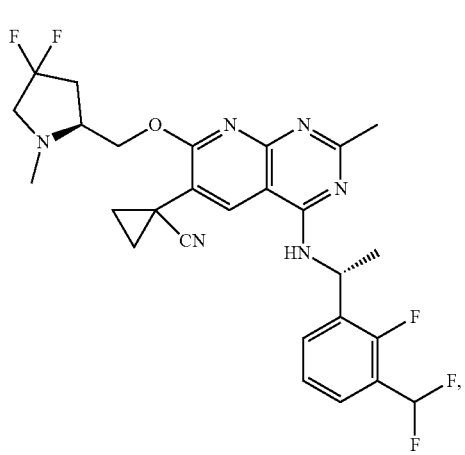
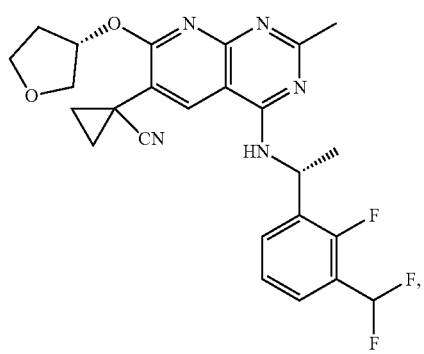

747
-continued
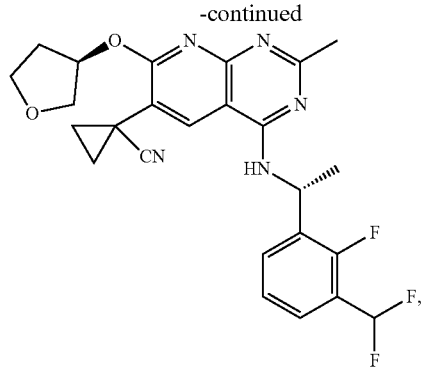
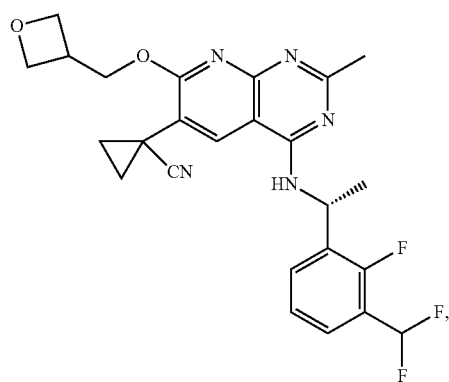
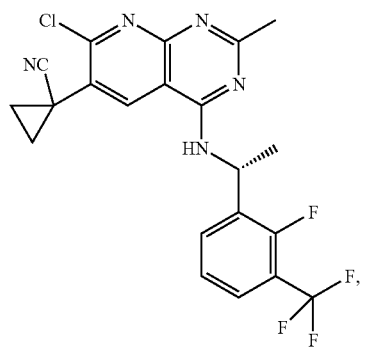
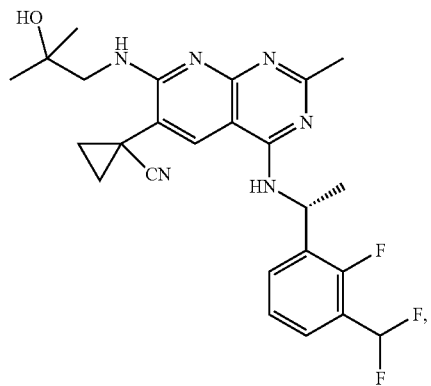
748
-continued
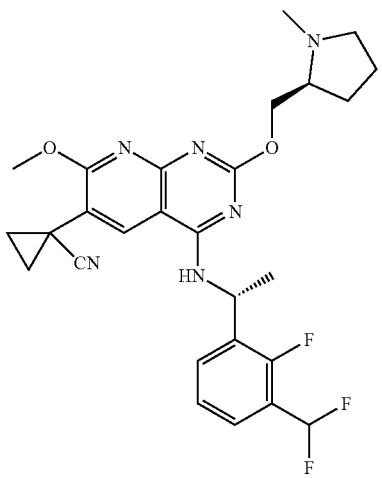
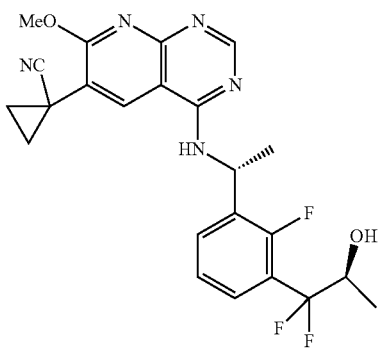
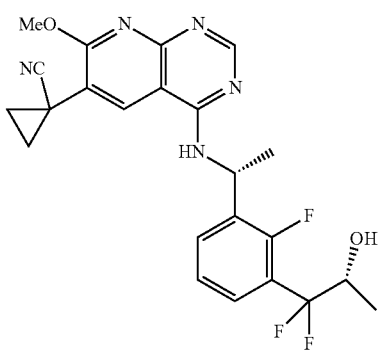
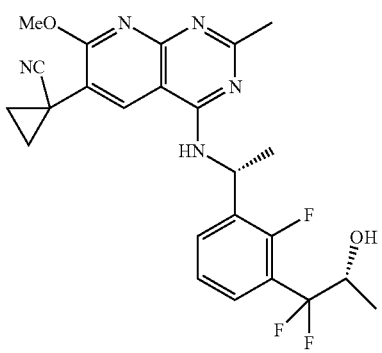

749
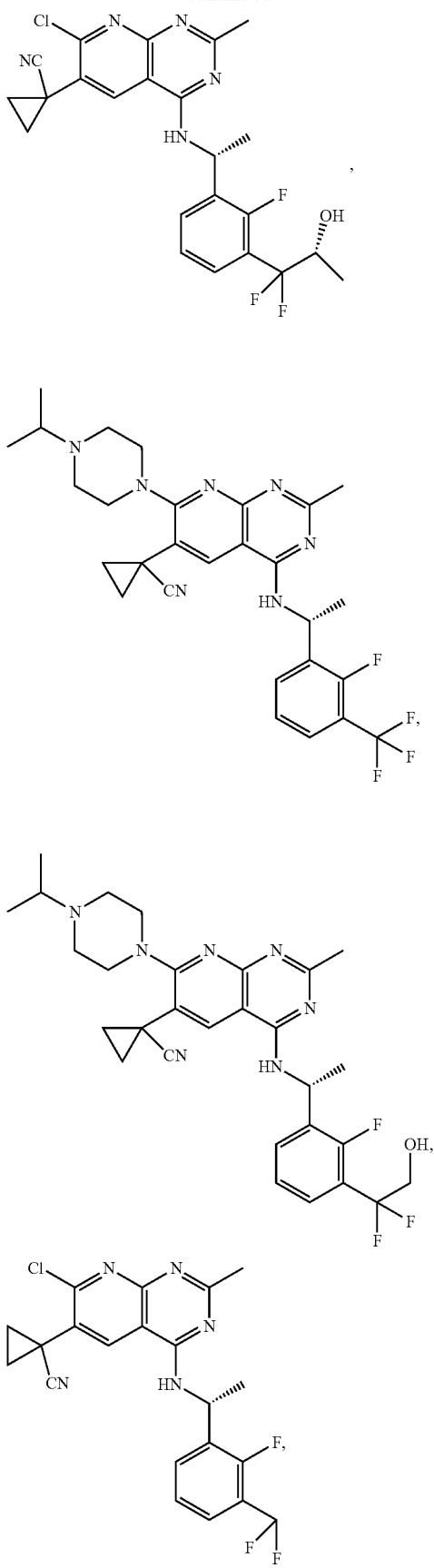
750
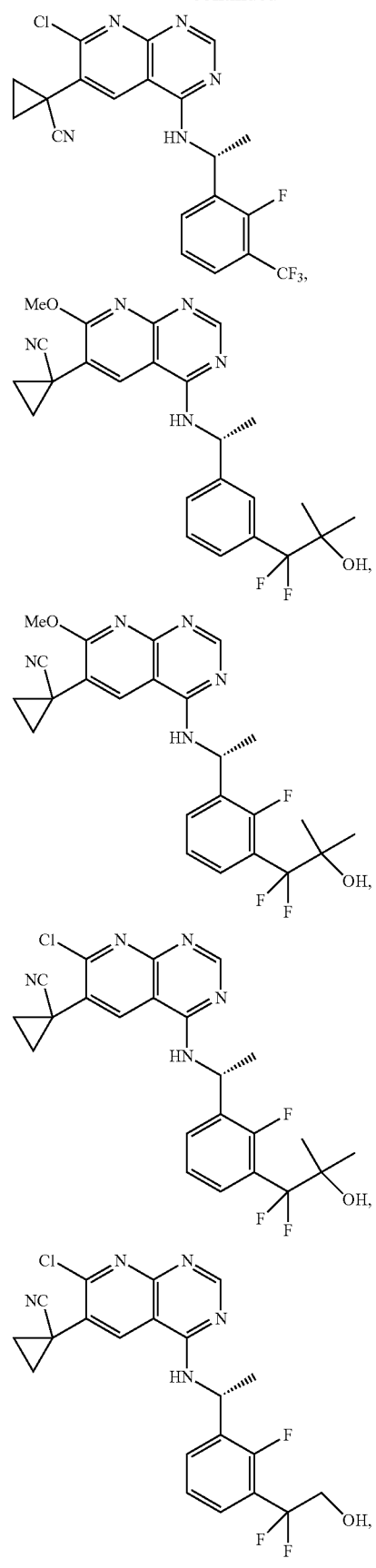

751
-continued
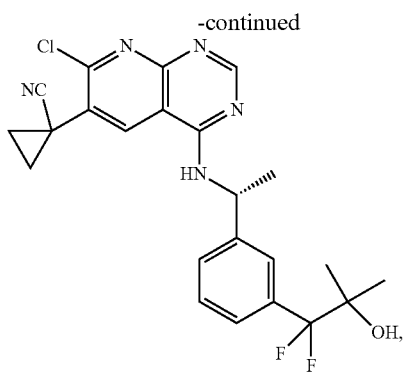
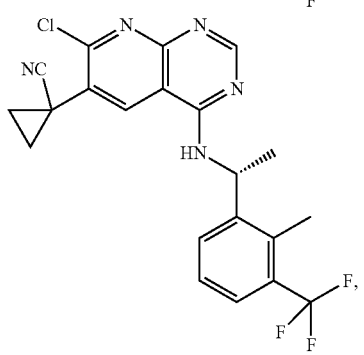
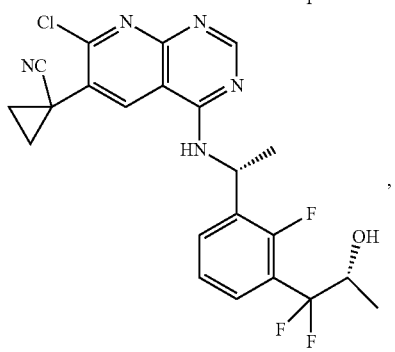
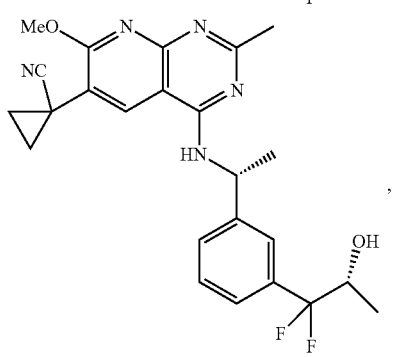
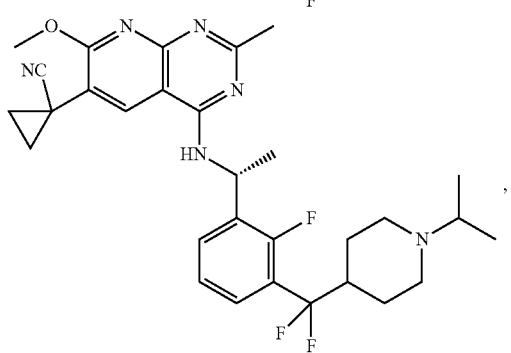
752
-continued
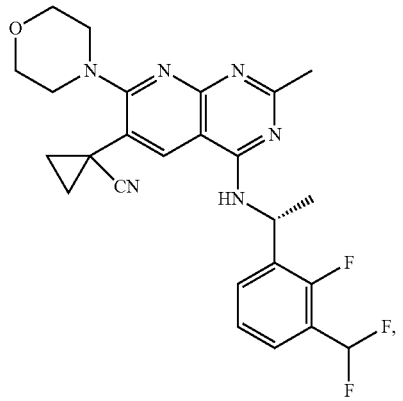
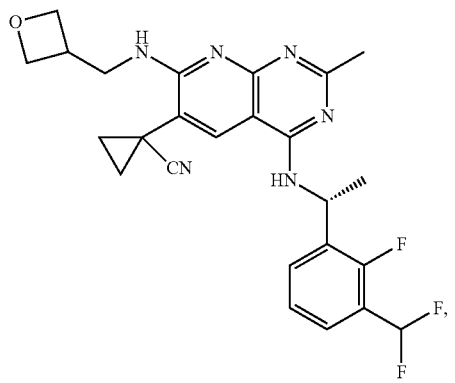
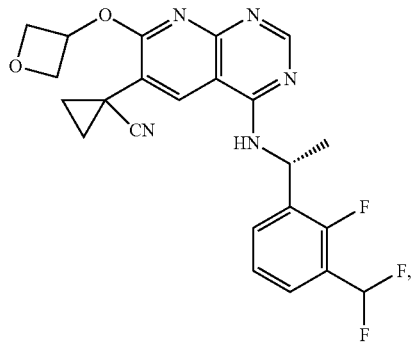
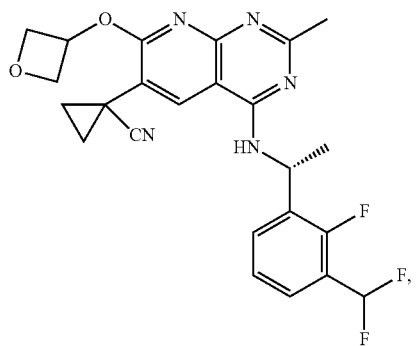

753
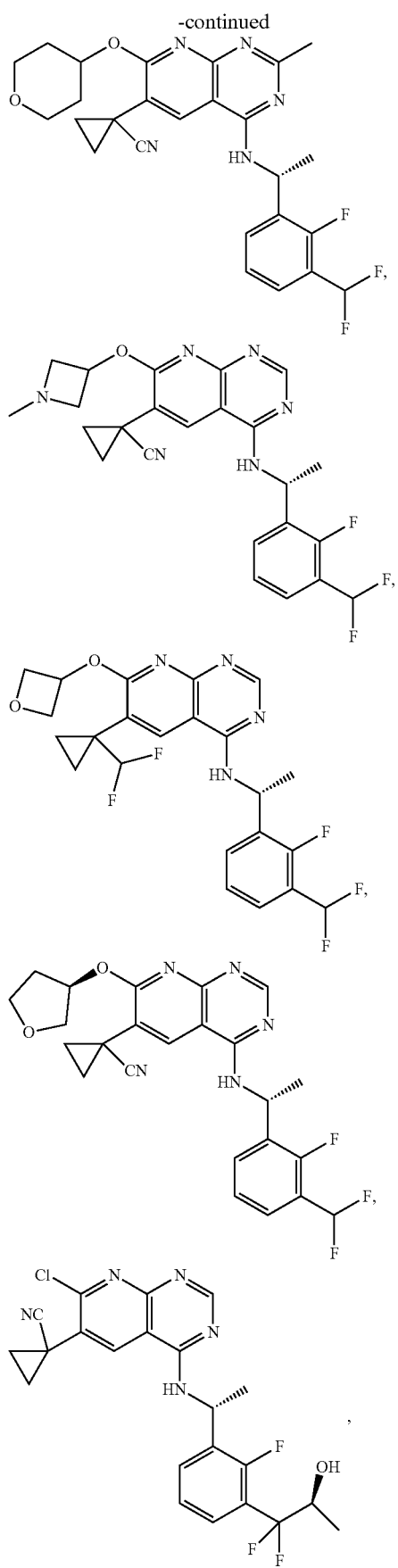
754
-continued
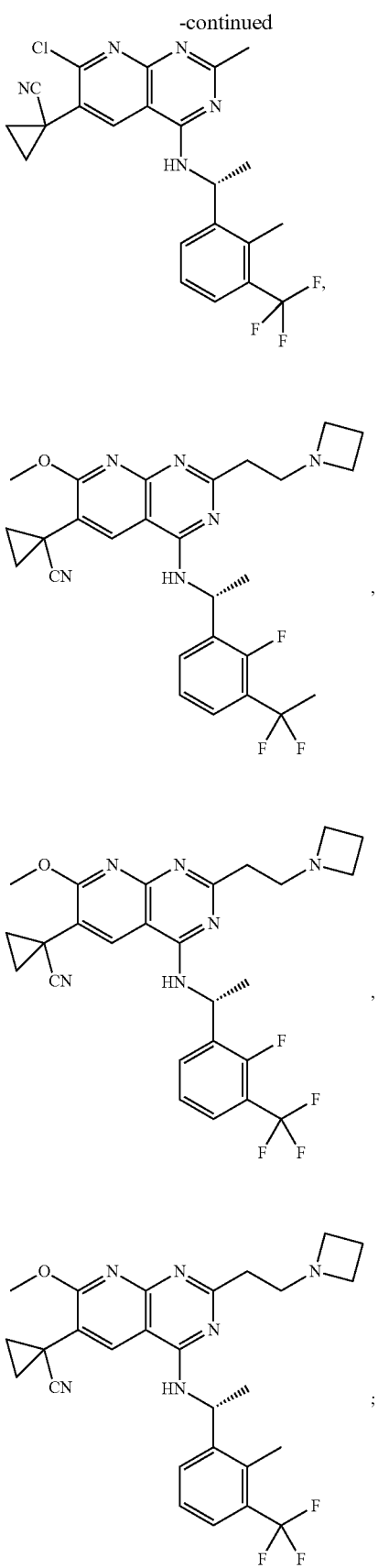
or a pharmaceutically acceptable salt or solvate thereof.

In some embodiments is a compound selected from:
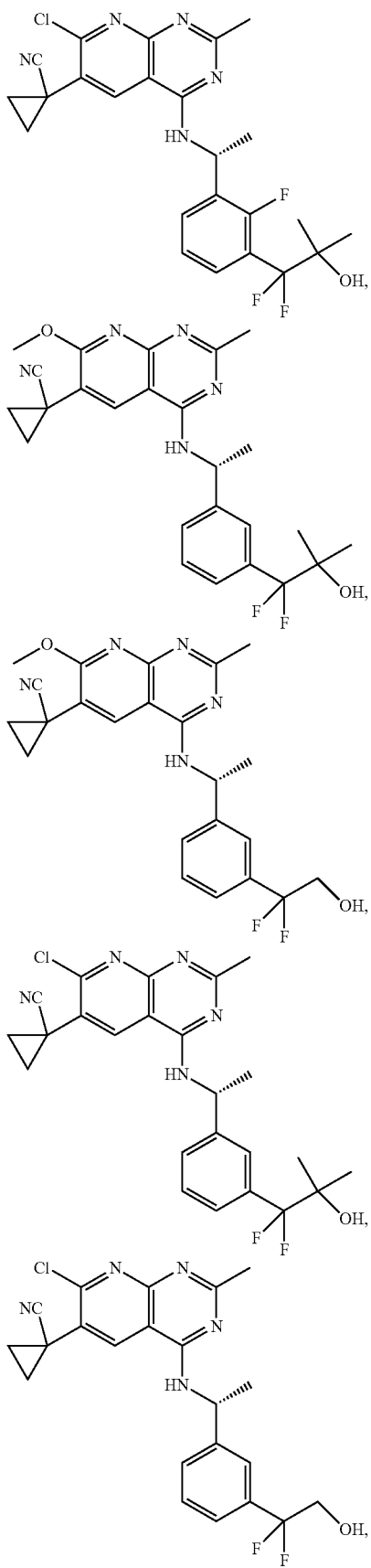
-continued
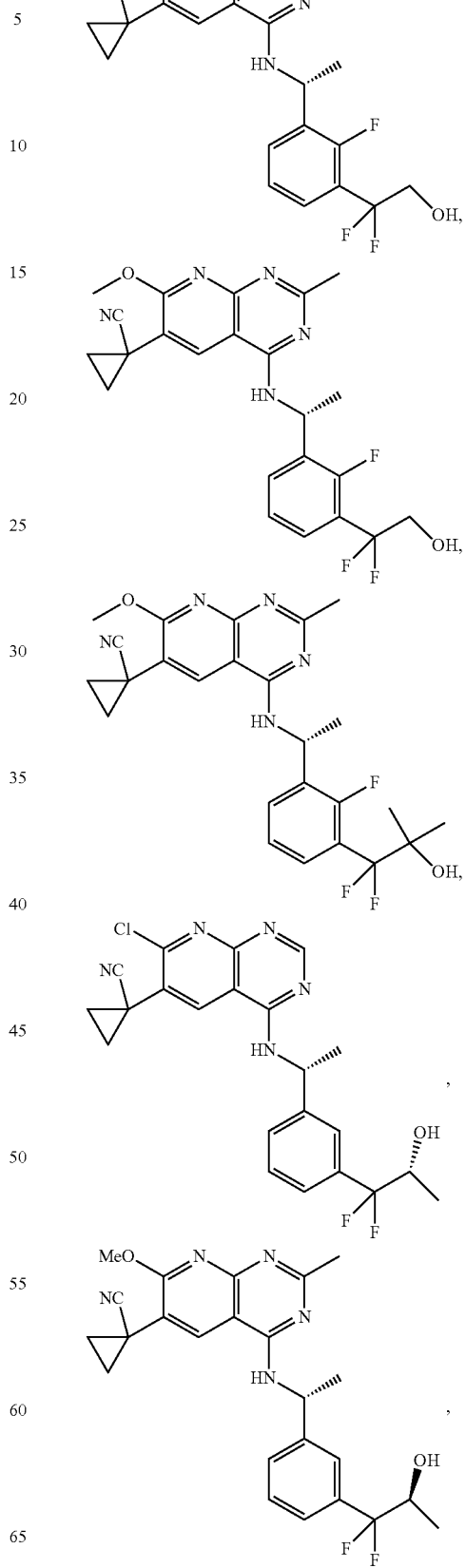

757
-continued
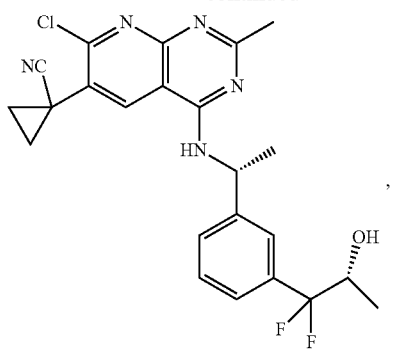
,
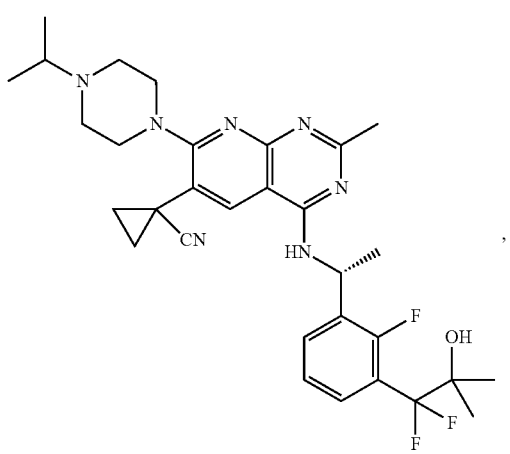
,
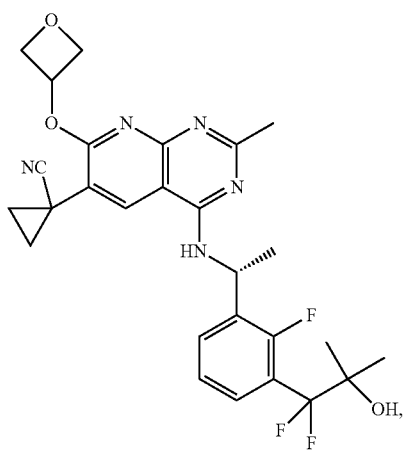
,
758
-continued
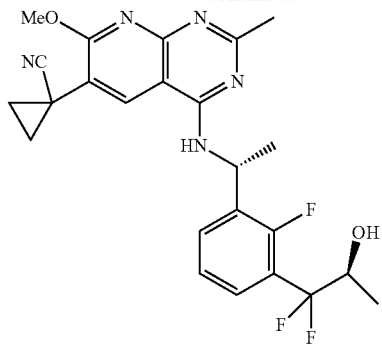
,
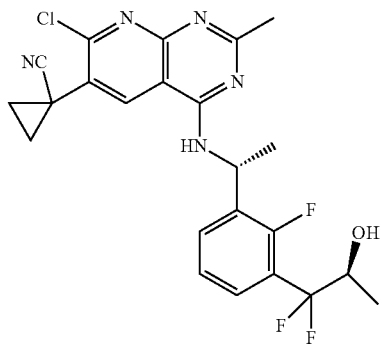
,
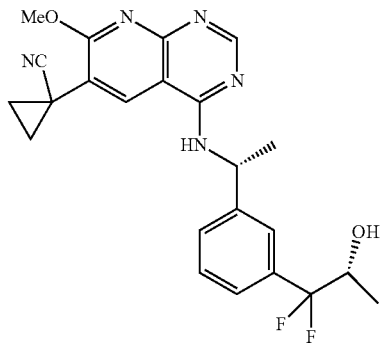
,
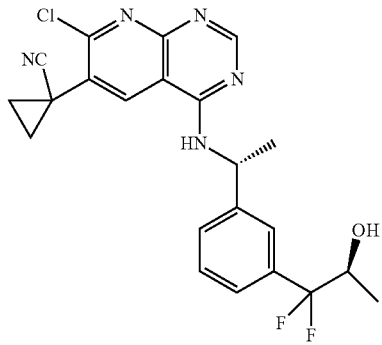
,
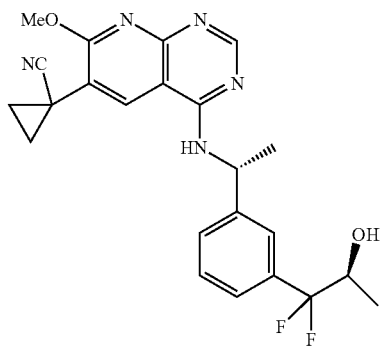
, 759
-continued
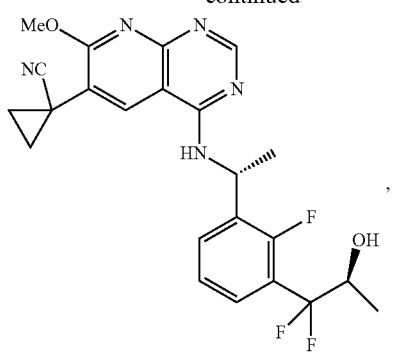
,
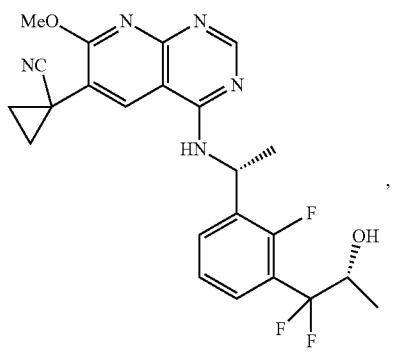
,
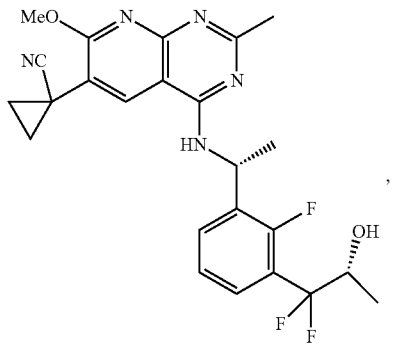
,
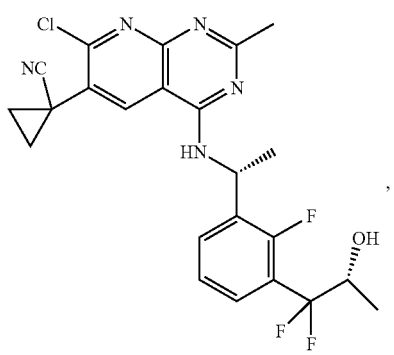
,
760
-continued
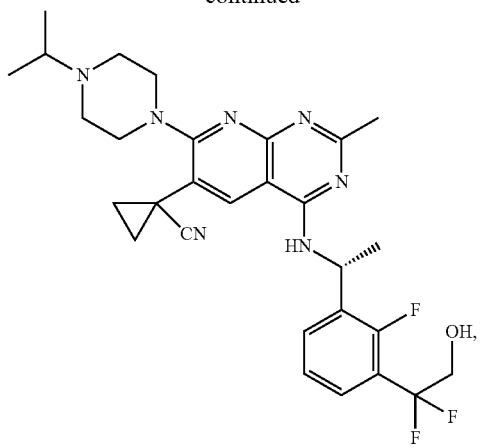
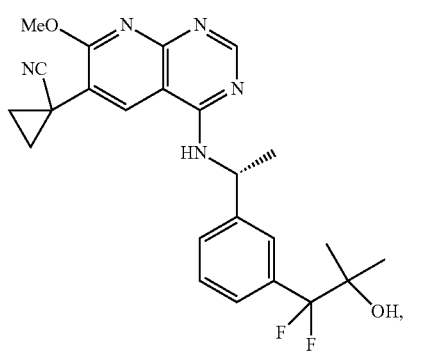
,
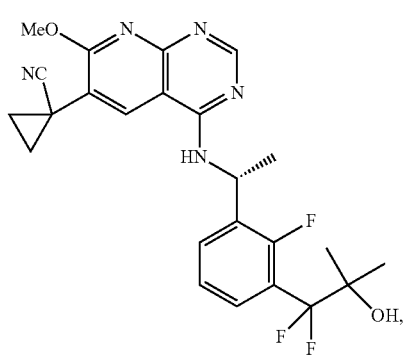
,
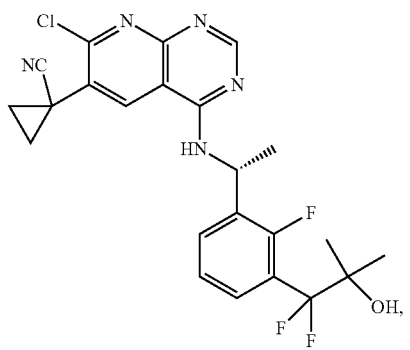
, 761
-continued
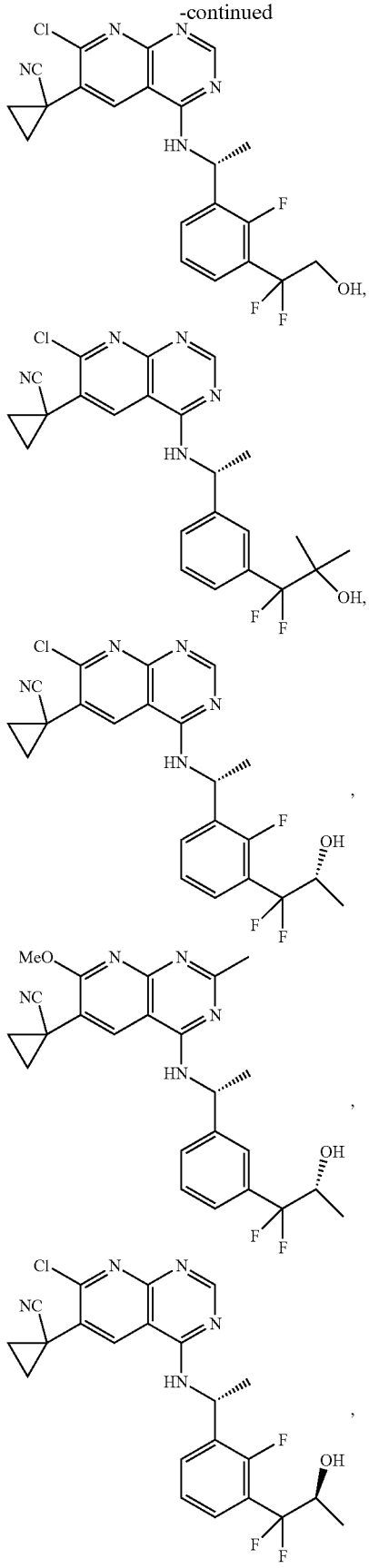
or a pharmaceutically acceptable salt or solvate thereof.
762
In some embodiments is a compound selected from:
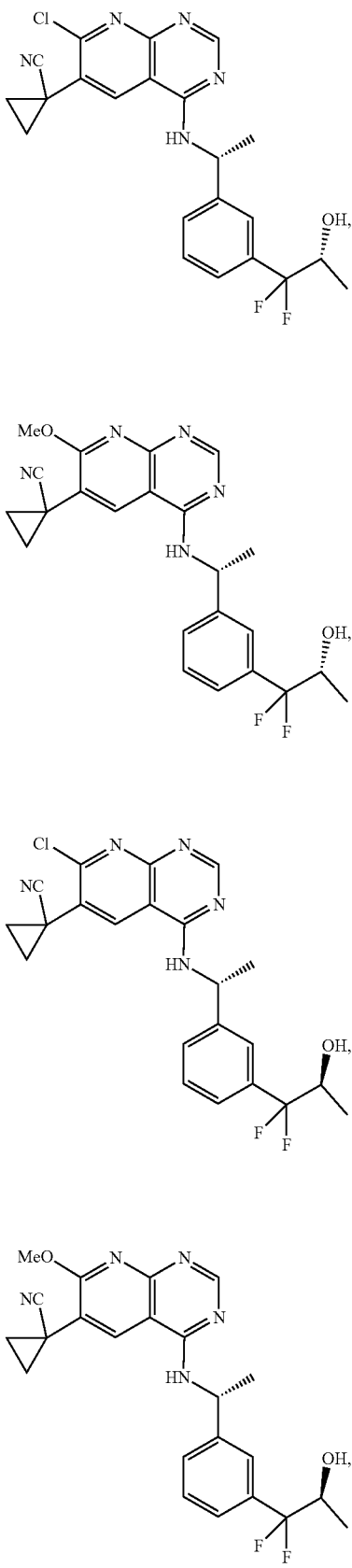

763
-continued
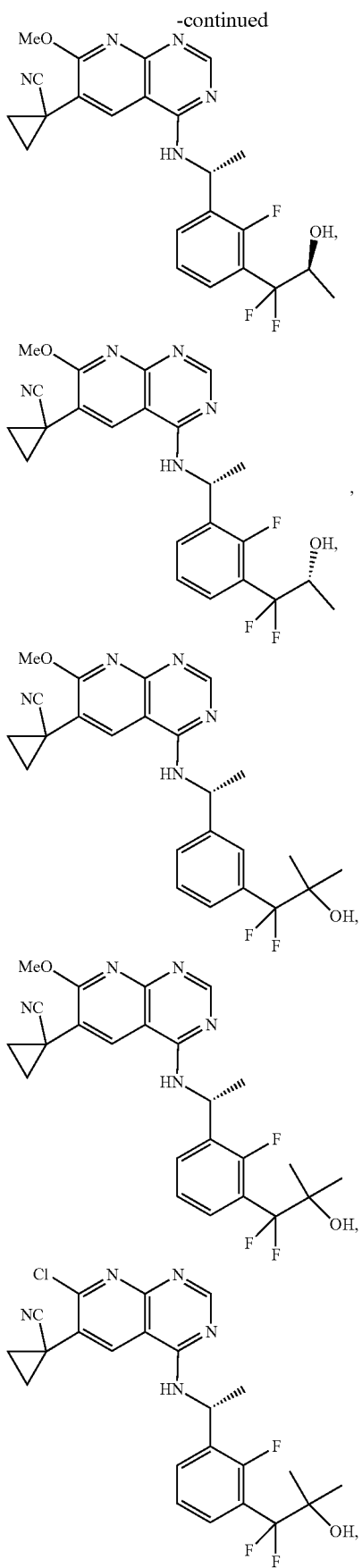
764
-continued
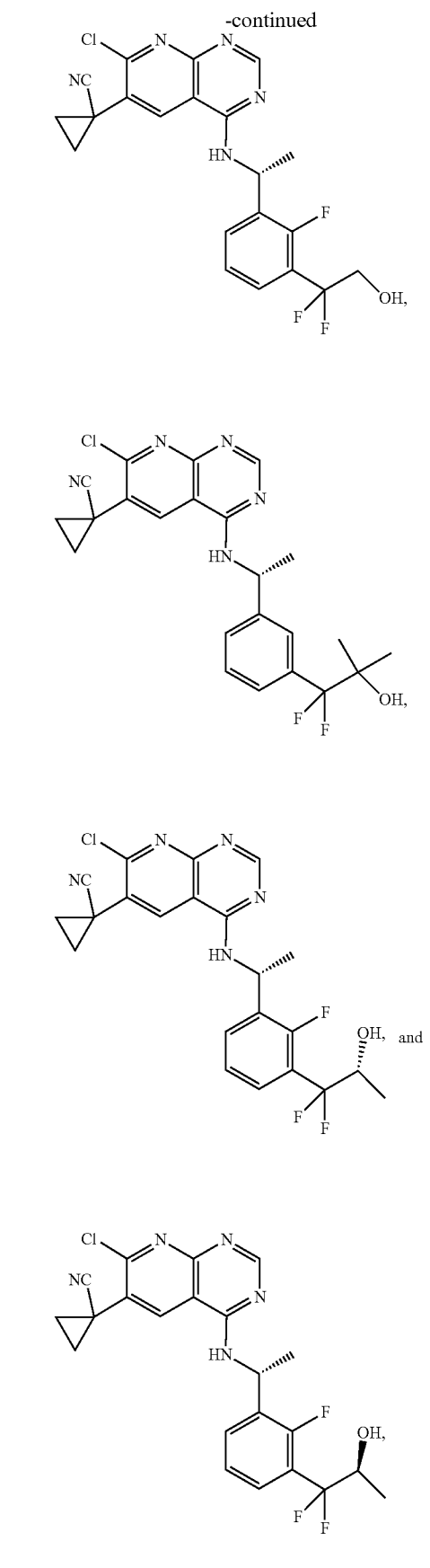
or a pharmaceutically acceptable salt or solvate thereof.

765
In some embodiments is a compound selected from:
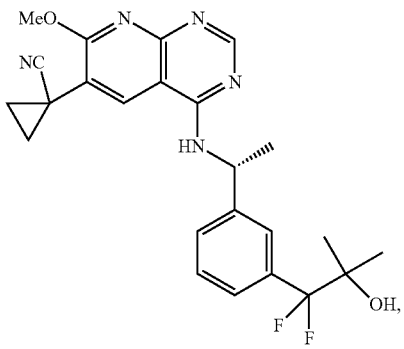
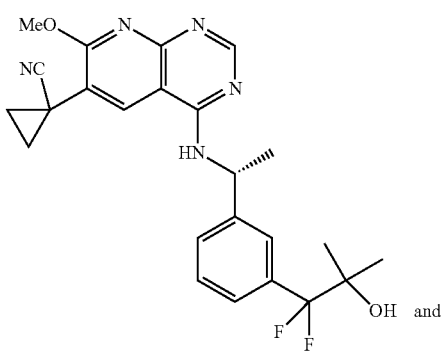 and
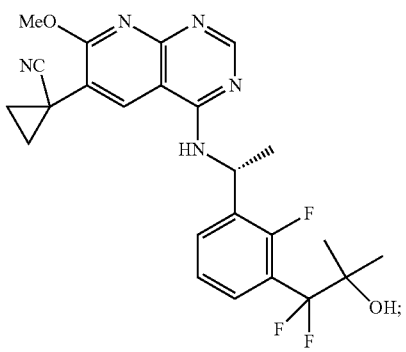
or a pharmaceutically acceptable salt or solvate thereof.
In some embodiments is a compound selected from:
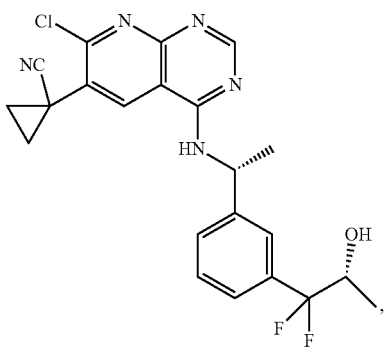
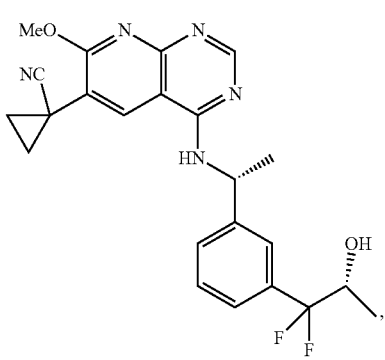
766

-continued
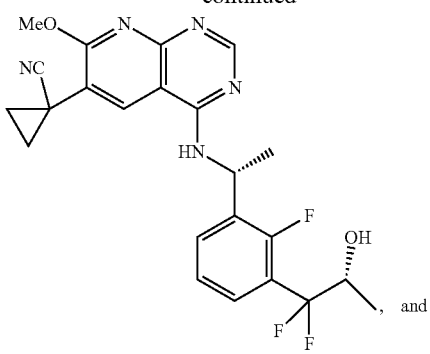
, and
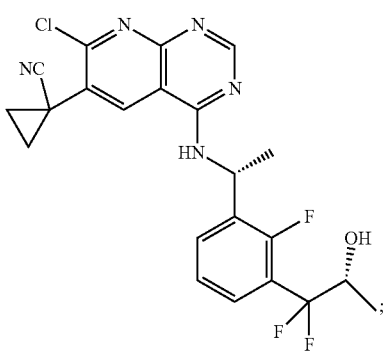
;
or a pharmaceutically acceptable salt or solvate thereof.
In some embodiments is a compound selected from:
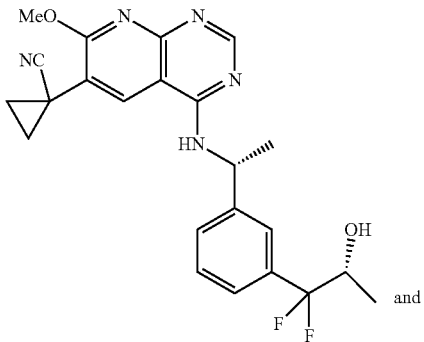
and
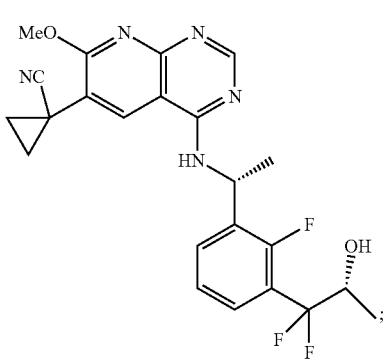
;
or a pharmaceutically acceptable salt or solvate thereof.
In some embodiments is a compound selected from:
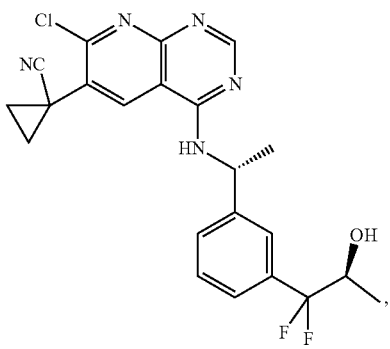
,
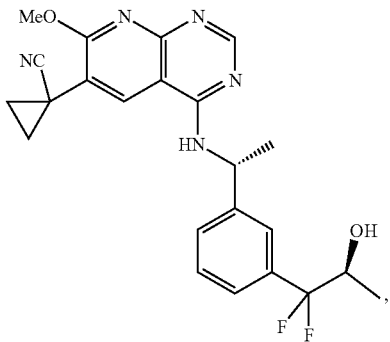
,
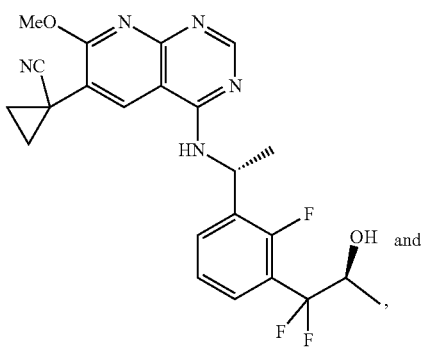
and
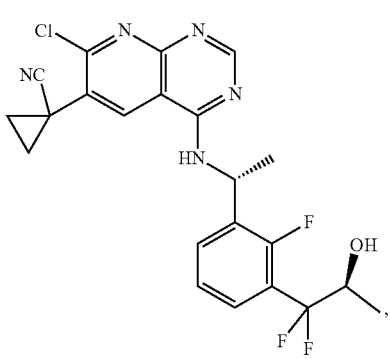
,
or a pharmaceutically acceptable salt or solvate thereof.

In some embodiments is a compound selected from:
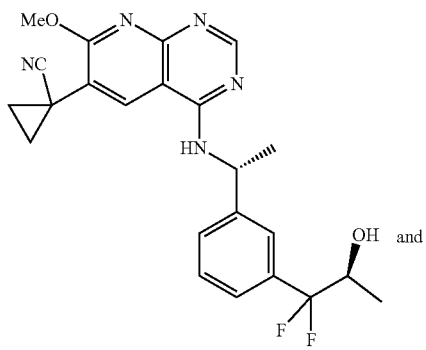
and
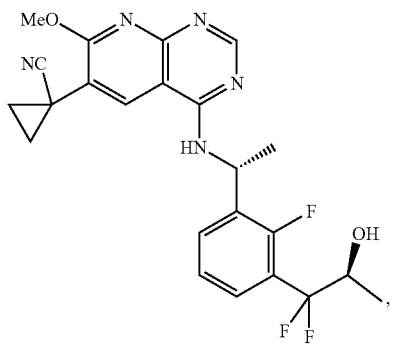
or a pharmaceutically acceptable salt or solvate thereof.
In some embodiments is a compound selected from:
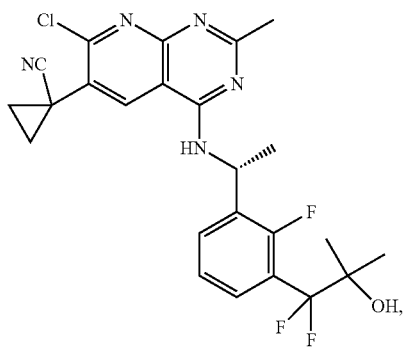
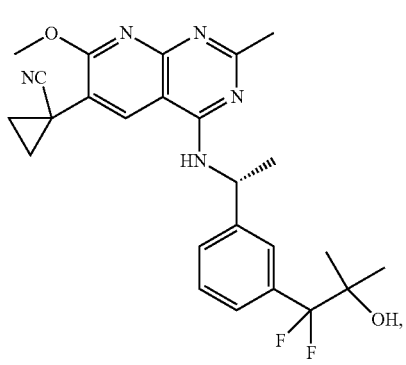
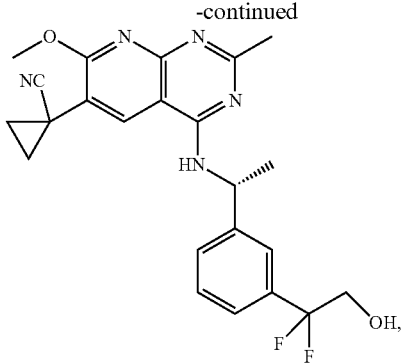
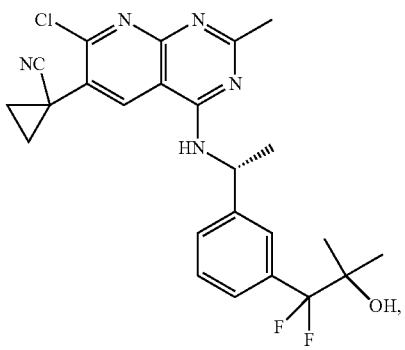
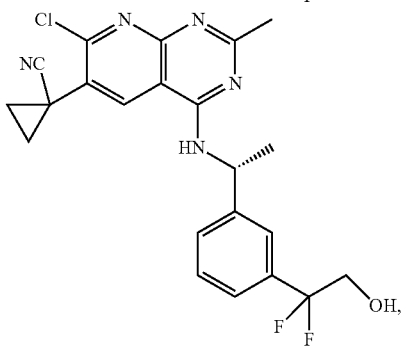
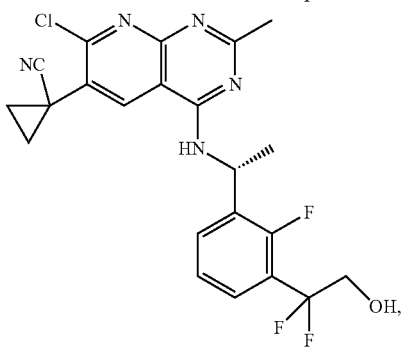
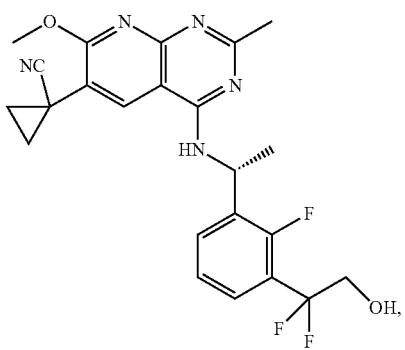

771
-continued
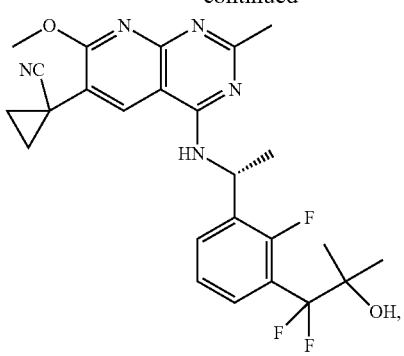
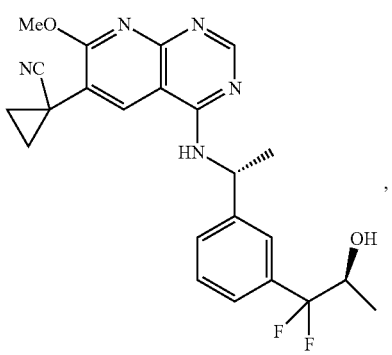
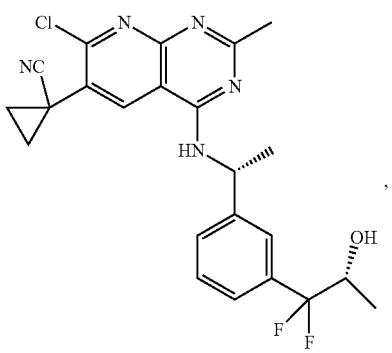
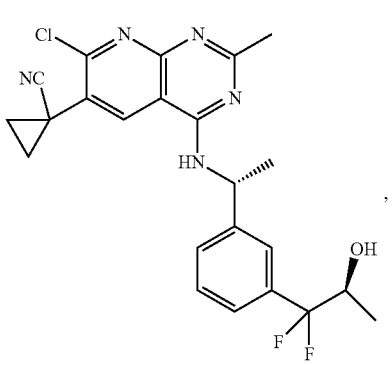
772
-continued
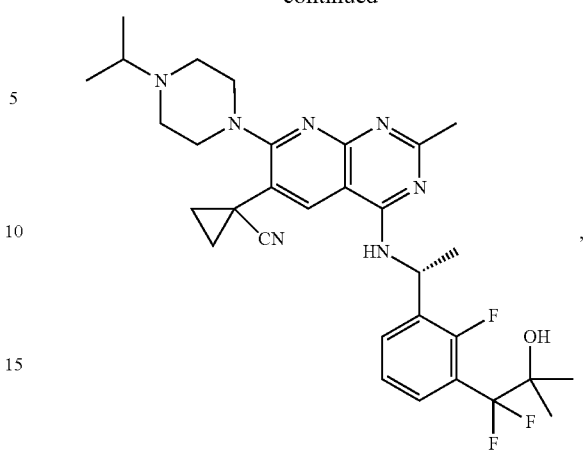

-continued
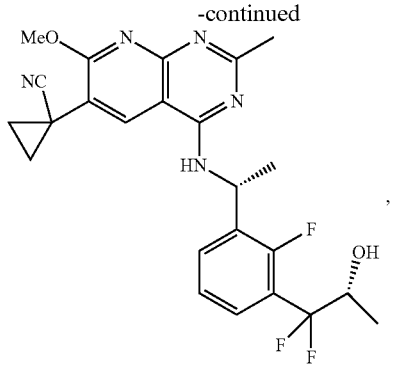
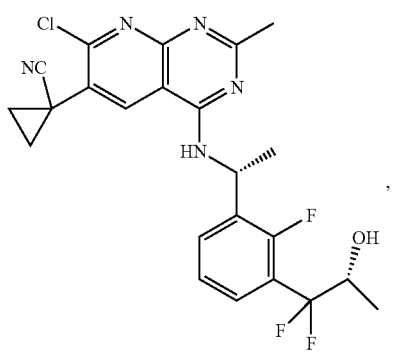
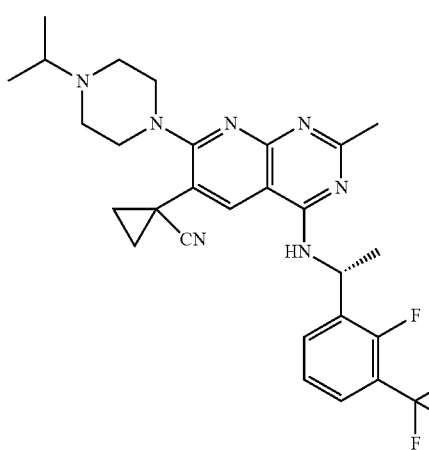
, and
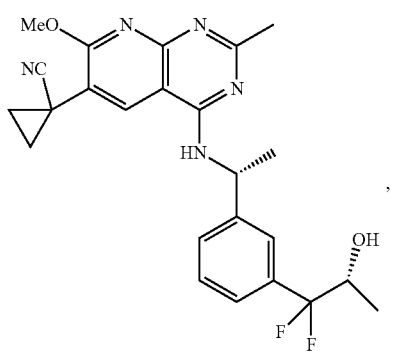
,
or a pharmaceutically acceptable salt or solvate thereof.
In some embodiments is a compound selected from:
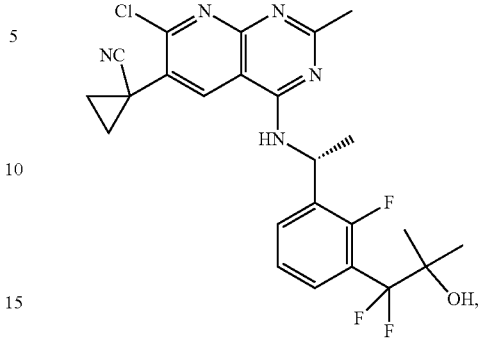
,
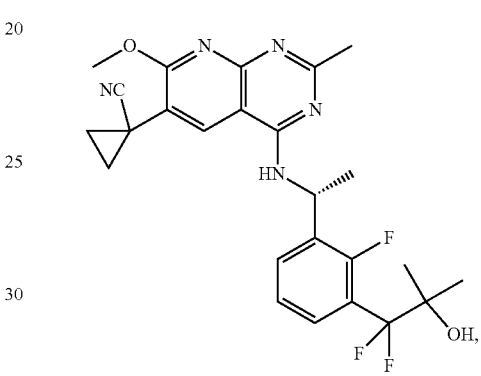
,
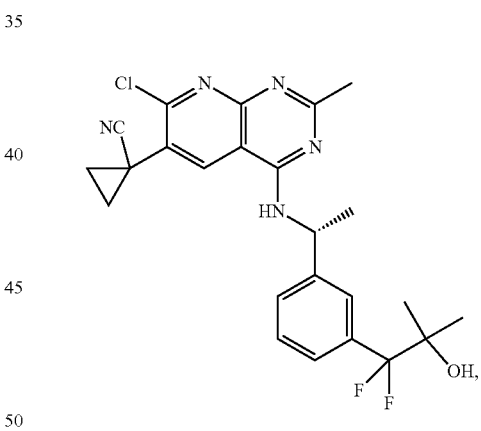
,
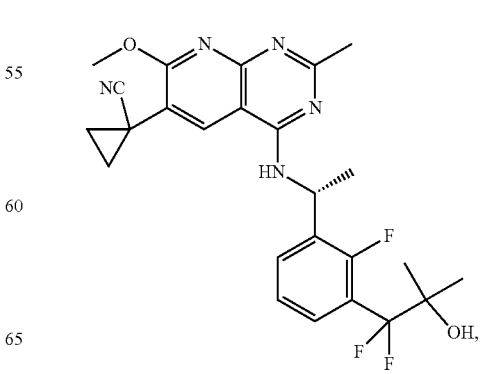
, -continued
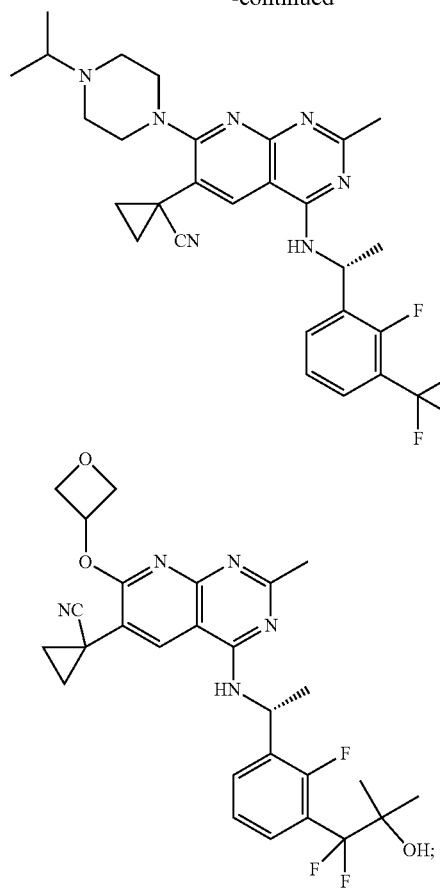
, and
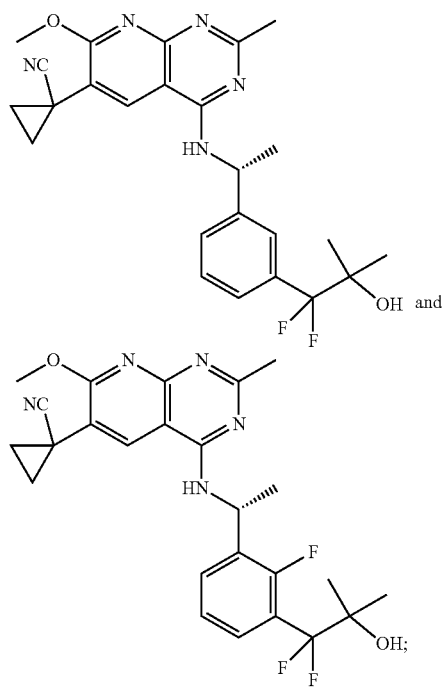
or a pharmaceutically acceptable salt or solvate thereof.
In some embodiments is a compound selected from:
[second column]
In some embodiments is a compound selected from:
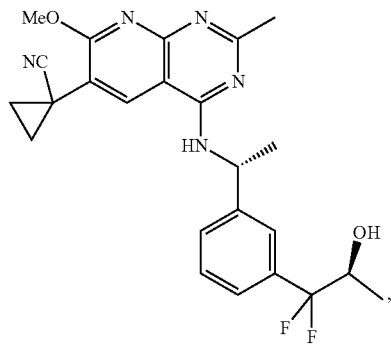
,
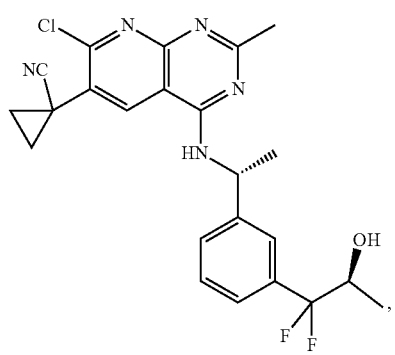
,
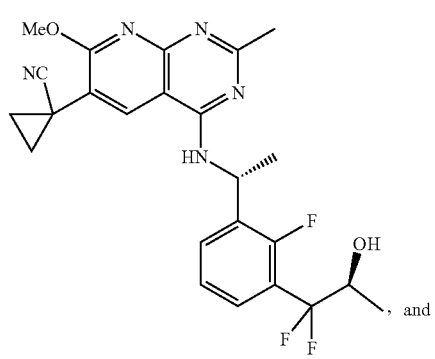
, and
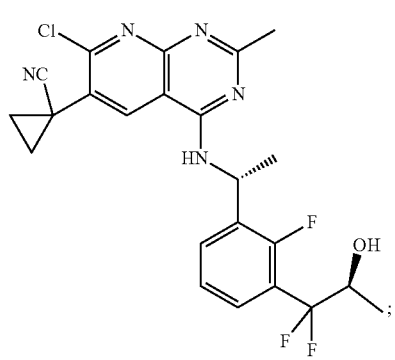
;
or a pharmaceutically acceptable salt or solvate thereof.

In some embodiments is a compound selected from:

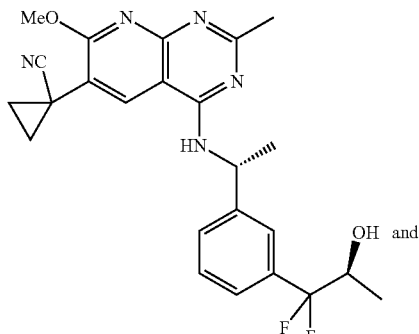

and

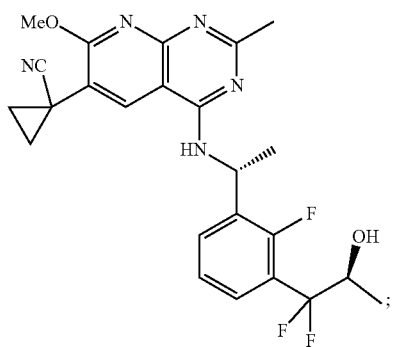

;

or a pharmaceutically acceptable salt or solvate thereof.

In some embodiments is a compound selected from:

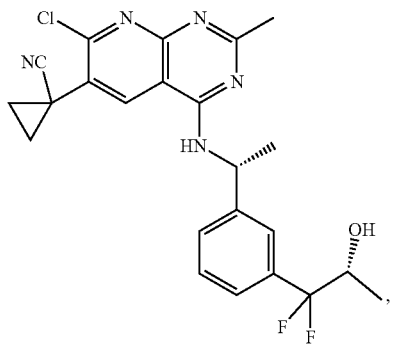

,

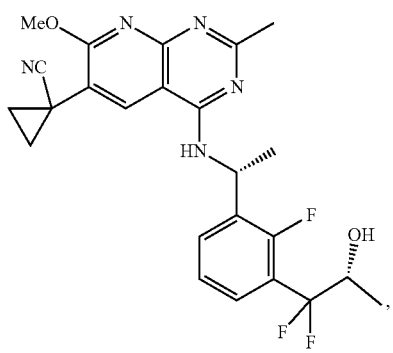

,

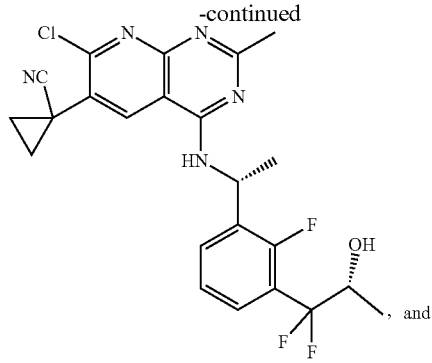

, and

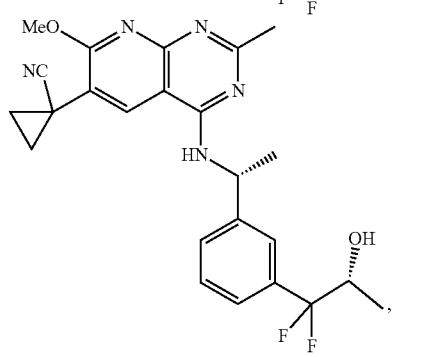

, or a pharmaceutically acceptable salt or solvate thereof.

In some embodiments is a compound selected from:

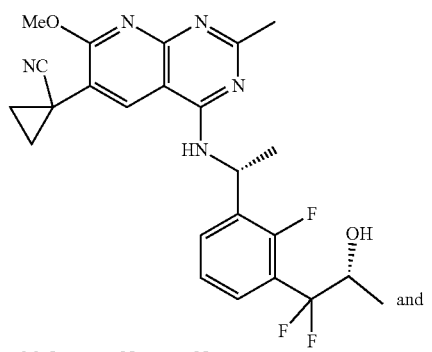

and

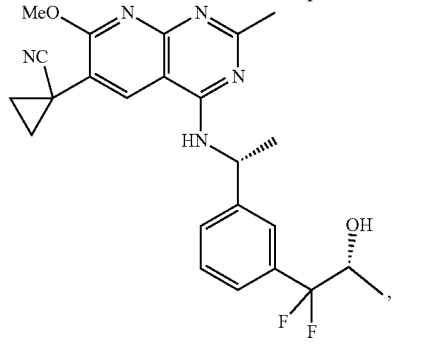

, or a pharmaceutically acceptable salt or solvate thereof.

In embodiments of a compound of Formula I-1,
R$^1$ is a 6-10 membered aryl ring optionally substituted with one or more R$^{10}$;
L$^1$ is a bond or C$_{1-6}$alkyl;
R$^2$ is —OR$^{2a}$, —NR$^{2b}$R$^{2c}$, —SR$^{2g}$, —S(O)R$^{2h}$, —S(O)$_2$R$^{2h}$, —S(O)$_2$NR$^{2b}$R$^{2c}$, —C(R$^{2d}$)(R$^{2e}$)(R$^{2f}$), C(O)NR$^{2b}$R$^{2c}$, —CN, or halogen;

$R^{2a}$ is selected from $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —C(O)OR$^{12}$, —C(O)R$^{15}$, —C(O)N(R$^{12}$)(R$^{13}$), —S(O)$_2$R$^{15}$, —S(O)$_2$N(R$^{12}$)(R$^{13}$), wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three R$^{20a}$;

$R^{2b}$ is selected from hydrogen, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —C(O)OR$^{12}$, —C(O)R$^{15}$, —C(O)N(R$^{12}$)(R$^{13}$), —S(O)$_2$R$^{15}$, and —S(O)$_2$N(R$^{12}$)(R$^{13}$), wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three R$^{20a}$;

$R^{2c}$ is selected from hydrogen, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three R$^{20a}$; or R$^{2b}$ and R$^{2c}$, together with the nitrogen to which they are attached, form a $C_{2-9}$heterocycloalkyl ring optionally substituted with one, two, or three R$^{20a}$;

$R^{2d}$ is selected from hydrogen, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —OR$^{12}$, —SR$^{12}$, —N(R$^{12}$)(R$^{13}$), —C(O)OR$^{12}$, —OC(O)N(R$^{12}$)(R$^{13}$), —N(R$^{14}$)C(O)N(R$^{12}$)(R$^{13}$), —N(R$^{14}$)C(O)OR$^{15}$, —N(R$^{14}$)S(O)$_2$R$^{15}$, —C(O)R$^{15}$, —S(O)R$^{15}$, —OC(O)R$^{15}$, —C(O)N(R$^{12}$)(R$^{13}$), —C(O)C(O)N(R$^{12}$)(R$^{13}$), —N(R$^{14}$)C(O)R$^{15}$, —S(O)$_2$R$^{15}$, —S(O)$_2$N(R$^{12}$)(R$^{13}$), —S(=O)(=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, —CH$_2$S(O)$_2$N(R$^{12}$)(R$^{13}$), —CH$_2$N(R$^{12}$)S(O)$_2$(R$^{13}$), and —P(O)(R$^{17}$)(R$^{17a}$), wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three R$^{20a}$;

$R^{2e}$ is selected from hydrogen, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three R$^{20a}$;

$R^{2f}$ is selected from hydrogen, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three R$^{20a}$;

$R^{2g}$ is selected from hydrogen, $C_{2-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —C(O)OR$^{12}$, —C(O)R$^{15}$, —C(O)N(R$^{12}$)(R$^{13}$), —S(O)$_2$R$^{15}$, —S(O)$_2$N(R$^{12}$)(R$^{13}$), wherein $C_{2-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three R$^{20a}$;

$R^{2h}$ is selected from $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three R$^{20a}$;

$R^3$ is cyclopropyl optionally substituted with one, two, or three CN;
$R^4$ is selected from hydrogen;
$R^5$ is selected from $C_{1-6}$alkyl;
$R^6$ is hydrogen;
$R^7$ is hydrogen;

each $R^{10}$ is independently selected from halogen, —CN, $C_{1-6}$alkyl, $C_{2-6}$alkenyl, $C_{2-6}$alkynyl, $C_{3-7}$cycloalkyl, $C_{2-9}$heterocycloalkyl, $C_{6-10}$aryl, $C_{1-9}$heteroaryl, —OR$^{12}$, —SR$^{12}$, —N(R$^{12}$)(R$^{13}$), —C(O)OR$^{12}$, —OC(O)N(R$^{12}$)(R$^{13}$), —N(R$^{14}$)C(O)N(R$^{12}$)(R$^{13}$), —N(R$^{14}$)C(O)OR$^{15}$, —N(R$^{14}$)S(O)$_2$R$^{15}$, —C(O)R$^{15}$, —S(O)R$^{15}$, —OC(O)R$^{15}$, —C(O)N(R$^{12}$)(R$^{13}$), —C(O)C(O)N(R$^{12}$)(R$^{13}$), —N(R$^{14}$)C(O)R$^{15}$, —S(O)$_2$R$^{15}$, —S(O)$_2$N(R$^{12}$)(R$^{13}$), —S(=O)(=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, —CH$_2$S(O)$_2$N(R$^{12}$)(R$^{13}$), —CH$_2$N(R$^{12}$)S(O)$_2$(R$^{13}$), and —P(O)(R$^{17}$)(R$^{17a}$), wherein $C_{1-6}$alkyl, $C_{2-6}$alkenyl, $C_{2-6}$alkynyl, $C_{3-7}$cycloalkyl, $C_{2-9}$heterocycloalkyl, $C_{6-10}$aryl, and $C_{1-9}$heteroaryl are optionally substituted with one, two, or three R$^{20a}$;

each $R^{12}$ is independently selected from hydrogen, $C_{1-6}$alkyl, $C_{1-6}$haloalkyl, $C_{2-6}$alkenyl, $C_{2-6}$alkynyl, $C_{3-7}$cycloalkyl, $C_{2-9}$heterocycloalkyl, $C_{6-10}$aryl, and $C_{1-9}$heteroaryl, wherein $C_{1-6}$alkyl, $C_{2-6}$alkenyl, $C_{2-6}$alkynyl, $C_{3-7}$cycloalkyl, $C_{2-9}$heterocycloalkyl, $C_{6-10}$aryl, and $C_{1-9}$heteroaryl are optionally substituted with one, two, or three R$^{20e}$;

each $R^{13}$ is independently selected from hydrogen, $C_{1-6}$alkyl, and $C_{1-6}$haloalkyl; or R$^{12}$ and R$^{13}$, together with the nitrogen to which they are attached, form a $C_{2-9}$heterocycloalkyl ring optionally substituted with one, two, or three R$^{20f}$;

$R^{13a}$ is selected from $C_{1-6}$alkyl and $C_{1-6}$haloalkyl; or R$^{12}$ and R$^{13a}$, together with the nitrogen to which they are attached, form a $C_{2-9}$heterocycloalkyl ring optionally substituted with one, two, or three R$^{20f}$;

each $R^{14}$ is independently selected from hydrogen, $C_{1-6}$alkyl, and $C_{1-6}$haloalkyl;

each $R^{15}$ is independently selected $C_{1-6}$alkyl, $C_{2-6}$alkenyl, $C_{2-6}$alkynyl, $C_{3-7}$cycloalkyl, $C_{2-9}$heterocycloalkyl, $C_{6-10}$aryl, and $C_{1-9}$heteroaryl, wherein $C_{1-6}$alkyl, $C_{2-6}$alkenyl, $C_{2-6}$alkynyl, $C_{3-7}$cycloalkyl, $C_{2-9}$heterocycloalkyl, $C_{6-10}$aryl, and $C_{1-9}$heteroaryl are optionally substituted with one, two, or three R$^{20g}$;

each $R^{17}$ and each $R^{17a}$ are each independently selected from $C_{1-6}$alkyl and $C_{3-6}$cycloalkyl, wherein $C_{1-6}$alkyl and $C_{3-6}$cycloalkyl are optionally substituted with one, two or three of R$^{20h}$; or R$^{17}$ and R$^{17a}$ are combined to form a $C_{2-9}$heterocycloalkyl ring;

each $R^{20a}$, $R^{20d}$, $R^{20e}$, $R^{20f}$, $R^{20g}$, and $R^{20h}$ are each independently selected from halogen, oxo, =NH, —CN, $C_{1-6}$alkyl, $C_{2-6}$alkenyl, $C_{2-6}$alkynyl, $C_{3-10}$cycloalkyl, —CH$_2$—$C_{3-10}$cycloalkyl, $C_{2-9}$heterocycloalkyl, —CH$_2$—$C_{2-9}$heterocycloalkyl, $C_{6-10}$aryl, —CH$_2$—$C_{6-10}$aryl, $C_{1-9}$ heteroaryl, —OR$^{21}$, —SR$^{21}$, —N(R$^{22}$)(R$^{23}$), —C(O)OR$^{22}$, —C(O)N(R$^{22}$)(R$^{23}$), —C(O)C(O)N(R$^{22}$)(R$^{23}$), —OC(O)N(R$^{22}$)(R$^{23}$), —N(R$^{24}$)C(O)N(R$^{22}$)(R$^{23}$), —N(R$^{24}$)C(O)OR$^{25}$, —N(R$^{24}$)C(O)R$^{25}$, —N(R$^{24}$)S(O)$_2$R$^{25}$, —C(O)R$^{25}$, —S(O)$_2$R$^{25}$, —S(O)$_2$N(R$^{22}$)(R$^{23}$), —OCH$_2$C(O)OR$^{22}$, and —OC(O)R$^{25}$, wherein $C_{1-6}$alkyl, $C_{2-6}$alkenyl, $C_{2-6}$alkynyl, $C_{3-10}$cycloalkyl, —CH$_2$—$C_{3-10}$cycloalkyl, $C_{2-9}$heterocycloalkyl, —CH$_2$—$C_{2-9}$heterocycloalkyl, $C_{6-10}$aryl, —CH$_2$—$C_{6-10}$aryl, and $C_{1-9}$heteroaryl are optionally substituted with one, two, or three groups independently selected from halogen, oxo, =NH, —CN, $C_{1-6}$alkyl, $C_{1-6}$haloalkyl, $C_{1-6}$alkoxy, $C_{1-6}$haloalkoxy, —OR$^{21}$, —SR$^{21}$, —N(R$^{22}$)(R$^{23}$), —C(O)OR$^{22}$, —C(O)N(R$^{22}$)(R$^{23}$), —C(O)C(O)N(R$^{22}$)(R$^{23}$), —OC(O)N(R$^{22}$)(R$^{23}$), —N(R$^{24}$)C(O)N(R$^{22}$)(R$^{23}$), —N(R$^{24}$)C(O)OR$^{25}$, —N(R$^{24}$)C(O)R$^{25}$, —N(R$^{24}$)S(O)$_2$R$^{25}$, —C(O)

$R^{25}$, $-S(O)_2R^{25}$, $-S(O)_2N(R^{22})(R^{23})$, and $-OC(O)R^{25}$;

each $R^{21}$ is independently selected from H, $C_{1-6}$alkyl, $C_{1-6}$haloalkyl, $C_{2-6}$alkenyl, $C_{2-6}$alkynyl, $C_{3-7}$cycloalkyl, $C_{2-9}$heterocycloalkyl, $C_{6-10}$aryl, and $C_{1-9}$heteroaryl, wherein $C_{3-7}$cycloalkyl, $C_{2-9}$heterocycloalkyl, $C_{6-10}$aryl, and $C_{1-9}$heteroaryl are optionally substituted with one, two, or three groups independently selected from halogen and $C_{1-6}$alkyl;

each $R^{22}$ is independently selected from H, $C_{1-6}$alkyl, $C_{1-6}$haloalkyl, $C_{2-6}$alkenyl, $C_{2-6}$alkynyl, $C_{3-7}$cycloalkyl, $C_{2-9}$heterocycloalkyl, $C_{6-10}$aryl, and $C_{1-9}$heteroaryl, wherein $C_{3-7}$cycloalkyl, $C_{2-9}$heterocycloalkyl, $C_{6-10}$aryl, and $C_{1-9}$heteroaryl are optionally substituted with one, two, or three groups independently selected from halogen and $C_{1-6}$alkyl;

each $R^{23}$ is independently selected from H and $C_{1-6}$alkyl;

each $R^{24}$ is independently selected from H and $C_{1-6}$alkyl; and each $R^{25}$ is selected from $C_{1-6}$alkyl, $C_{2-6}$alkenyl, $C_{2-6}$alkynyl, $C_{3-7}$cycloalkyl, $C_{2-9}$heterocycloalkyl, $C_{6-10}$aryl, and $C_{1-9}$heteroaryl, wherein $C_{1-6}$alkyl, $C_{3-7}$cycloalkyl, $C_{2-9}$heterocycloalkyl, $C_{6-10}$aryl, and $C_{1-9}$heteroaryl are optionally substituted with one, two, or three groups independently selected from halogen, $C_{1-6}$alkyl, $C_{1-6}$haloalkyl, $C_{1-6}$alkoxy, $C_{3-7}$cycloalkyl, $C_{2-9}$heterocycloalkyl, $C_{6-10}$aryl, and $C_{1-9}$heteroaryl.

In embodiments, $R^{2a}$ is $C_{1-6}$alkyl optionally substituted with one, two, or three $R^{20a}$. In embodiments, $R^{2a}$ is unsubstituted $C_{1-6}$alkyl. In embodiments, $R^{2a}$ is $-CH_3$. In embodiments, $R^{2b}$ is $C_{1-6}$alkyl optionally substituted with one, two, or three $R^{20a}$. In embodiments, $R^{2c}$ is $C_{1-6}$alkyl optionally substituted with one, two, or three $R^{20a}$. In embodiments, $R^{2c}$ is hydrogen. In embodiments, $R^{2d}$ is hydrogen or $C_{1-6}$alkyl optionally substituted with one, two, or three $R^{20a}$. In embodiments, $R^{2e}$ is hydrogen. In embodiments, $R^2$ is hydrogen. In embodiments, $R^2$ is halogen. In embodiments, $R^1$ is a phenyl optionally substituted with one or more $R^{10}$. In embodiments, $R^1$ is a phenyl optionally substituted with one, two, or three $R^{10}$, wherein each $R^{10}$ is independently selected from halogen, $C_{1-6}$alkyl, and $N(R^{12})(R^{13})$, and further wherein $C_{1-6}$alkyl is optionally substituted with one, two, or three $R^{20d}$. In embodiments, $R^1$ is a phenyl optionally substituted with one, two, or three $R^{10}$, wherein each $R^{10}$ is independently selected from halogen and $C_{1-6}$alkyl, and further wherein $C_{1-6}$alkyl is substituted with one, two, or three $R^{20d}$, and each $R^{20d}$ is halogen. In embodiments, $R^1$ is independently selected from

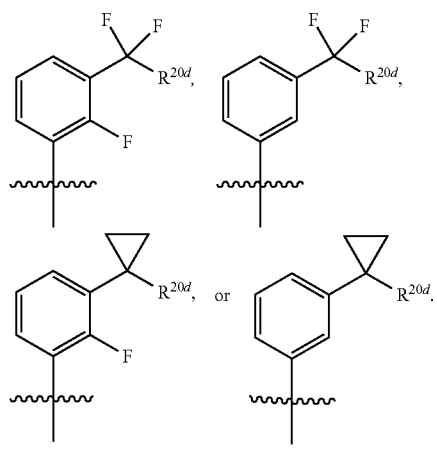

In embodiments, $R^{20d}$ is $C_{1-6}$alkyl optionally substituted with one, two, or three groups independently selected from F and $-OH$. In embodiments, $R^{20d}$ is $C_{1-3}$alkyl substituted with one $-OH$. In embodiments, $R^1$ is selected from

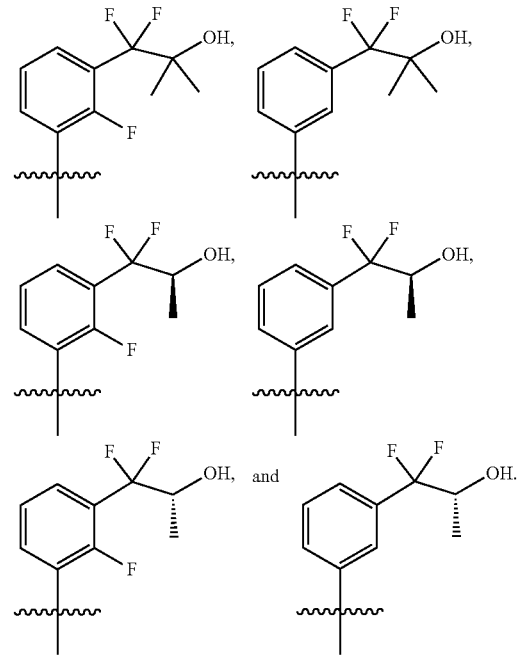

In embodiments, of a compound of Formula I-2, $R^1$ is a 3-12 membered cycloalkyl ring, 3-12 membered heterocycloalkyl ring, 6-10 membered aryl ring, or 5-10 membered heteroaryl ring, wherein the 3-12 membered cycloalkyl ring, 3-12 membered heterocycloalkyl ring, 6-10 membered aryl ring, and 5-10 membered heteroaryl ring are optionally substituted with one or more $R^{10}$;

$L^1$ is a bond or $C_{1-6}$alkyl;

$R^2$ is $-OR^{2a}$, $-NR^{2b}R^{2c}$, $-SR^{2g}$, $-S(O)R^{2h}$, $-S(O)_2R^{2h}$, $-S(O)_2NR^{2b}R^{2c}$, $-C(R^{2d})(R^{2e})(R^{2f})$, $C(O)NR^{2b}R^{2c}$, $-CN$, or halogen;

$R^{2a}$ is selected from $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, $-C(O)OR^{12}$, $-C(O)R^{15}$, $-C(O)N(R^{12})(R^{13})$, $-S(O)_2R^{15}$, $-S(O)_2N(R^{12})(R^{13})$, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20a}$;

$R^{2b}$ is selected from hydrogen, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, $-C(O)OR^{12}$, $-C(O)R^{15}$, $-C(O)N(R^{12})(R^{13})$, $-S(O)_2R^{15}$, and $-S(O)_2N(R^{12})(R^{13})$, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20a}$;

$R^{2c}$ is selected from hydrogen, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20a}$; or $R^{2b}$ and $R^{2c}$, together with the nitrogen to which they are attached, form a $C_{2-9}$heterocycloalkyl ring optionally substituted with one, two, or three $R^{20a}$;

$R^{2d}$ is selected from hydrogen, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2 R^{15}$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{15}$, —$S(O)_2 R^{15}$, —$S(O)_2 N(R^{12})(R^{13})$, —$S(=O)(=NH)N(R^{12})(R^{13})$, —$CH_2C(O)N(R^{12})(R^{13})$, —$CH_2N(R^{14})C(O)R^{15}$, —$CH_2S(O)_2 R^{15}$, —$CH_2S(O)_2 N(R^{12})(R^{13})$, —$CH_2N(R^{12})S(O)_2(R^{13})$, and —$P(O)(R^{17})(R^{17a})$, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20a}$;

$R^{2e}$ is selected from hydrogen, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20a}$;

$R^{2f}$ is selected from hydrogen, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20a}$;

$R^{2g}$ is selected from hydrogen, $C_{2-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —$C(O)OR^{12}$, —$C(O)R^{15}$, —$C(O)N(R^{12})(R^{13})$, —$S(O)_2 R^{15}$, —$S(O)_2 N(R^{12})(R^{13})$, wherein $C_{2-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20a}$;

$R^{2h}$ is selected from $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20a}$;

$R^3$ is $C_3$cycloalkyl, wherein $C_3$cycloalkyl is optionally substituted with one $R^{21}$;

$R^4$ is selected from hydrogen, $C_{1-6}$alkyl, and $C_{1-6}$haloalkyl;

$R^5$ is selected from hydrogen, $C_{1-6}$alkyl, and $C_{1-6}$haloalkyl;

$R^6$ is selected from hydrogen, halogen, —CN, $C_{1-6}$alkyl, $C_{2-6}$alkenyl, $C_{2-6}$alkynyl, $C_{3-10}$cycloalkyl, $C_{2-9}$heterocycloalkyl, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2 R^{15}$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{15}$, —$S(O)_2 R^{15}$, —$S(O)_2 N(R^{12})(R^{13})$, —$S(=O)(=NH)N(R^{12})(R^{13})$, —$CH_2C(O)N(R^{12})(R^{13})$, —$CH_2N(R^{14})C(O)R^{15}$, —$CH_2S(O)_2 R^{15}$, —$CH_2S(O)_2 N(R^{12})(R^{13})$, —$CH_2N(R^{12})S(O)_2(R^{13})$, and —$P(O)(R^{17})(R^{17a})$, wherein $C_{1-6}$alkyl, $C_{2-6}$alkenyl, $C_{2-6}$alkynyl, $C_{3-10}$cycloalkyl, and $C_{2-9}$heterocycloalkyl are optionally substituted with one, two, or three $R^{20c}$.

$R^7$ is selected from hydrogen, halogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{1-9}$heteroaryl, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2 R^{15}$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{15}$, —$S(O)_2 R^{15}$, —$S(O)_2 N(R^{12})(R^{13})$, —$S(=O)(=NH)N(R^{12})(R^{13})$, —$CH_2C(O)N(R^{12})(R^{13})$, —$CH_2N(R^{14})C(O)R^{15}$, —$CH_2S(O)_2 R^{15}$, —$CH_2S(O)_2 N(R^{12})(R^{13})$, —$CH_2N(R^{12})S(O)_2(R^{13})$, and —$P(O)(R^{17})(R^{17a})$, wherein $C_{1-6}$alkyl, $C_{2-6}$alkenyl, $C_{2-6}$alkynyl, $C_{3-10}$cycloalkyl, $C_{2-9}$heterocycloalkyl, and $C_{1-9}$heteroaryl are optionally substituted with one, two, or three $R^{20c}$;

each $R^{10}$ is independently selected from halogen, —CN, $C_{1-6}$alkyl, $C_{2-6}$alkenyl, $C_{2-6}$alkynyl, $C_{3-7}$cycloalkyl, $C_{2-9}$heterocycloalkyl, $C_{6-10}$aryl, $C_{1-9}$heteroaryl, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2 R^{15}$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{15}$, —$S(O)_2 R^{15}$, —$S(O)_2 N(R^{12})(R^{13})$, —$S(=O)(=NH)N(R^{12})(R^{13})$, —$CH_2C(O)N(R^{12})(R^{13})$, —$CH_2N(R^{14})C(O)R^{15}$, —$CH_2S(O)_2 R^{15}$, —$CH_2S(O)_2 N(R^{12})(R^{13})$, —$CH_2N(R^{12})S(O)_2(R^{13})$, and —$P(O)(R^{17})(R^{17a})$, wherein $C_{1-6}$alkyl, $C_{2-6}$alkenyl, $C_{2-6}$alkynyl, $C_{3-7}$cycloalkyl, $C_{2-9}$heterocycloalkyl, $C_{6-10}$aryl, and $C_{1-9}$heteroaryl are optionally substituted with one, two, or three $R^{20a}$;

each $R^{12}$ is independently selected from hydrogen, $C_{1-6}$alkyl, $C_{1-6}$ haloalkyl, $C_{2-6}$alkenyl, $C_{2-6}$alkynyl, $C_{3-7}$cycloalkyl, $C_{2-9}$heterocycloalkyl, $C_{6-10}$aryl, and $C_{1-9}$heteroaryl, wherein $C_{1-6}$alkyl, $C_{2-6}$alkenyl, $C_{2-6}$alkynyl, $C_{3-7}$cycloalkyl, $C_{2-9}$heterocycloalkyl, $C_{6-10}$aryl, and $C_{1-9}$heteroaryl are optionally substituted with one, two, or three $R^{20e}$;

each $R^{13}$ is independently selected from hydrogen, $C_{1-6}$alkyl, and $C_{1-6}$haloalkyl; or $R^{12}$ and $R^{13}$, together with the nitrogen to which they are attached, form a $C_{2-9}$heterocycloalkyl ring optionally substituted with one, two, or three $R^{20f}$;

$R^{13a}$ is selected from $C_{1-6}$alkyl and $C_{1-6}$haloalkyl; or $R^{12}$ and $R^{13a}$, together with the nitrogen to which they are attached, form a $C_{2-9}$heterocycloalkyl ring optionally substituted with one, two, or three $R^{20f}$;

each $R^{14}$ is independently selected from hydrogen, $C_{1-6}$alkyl, and $C_{1-6}$haloalkyl;

each $R^{15}$ is independently selected $C_{1-6}$alkyl, $C_{2-6}$alkenyl, $C_{2-6}$alkynyl, $C_{3-7}$cycloalkyl, $C_{2-9}$heterocycloalkyl, $C_{6-10}$aryl, and $C_{1-9}$heteroaryl, wherein $C_{1-6}$alkyl, $C_{2-6}$alkenyl, $C_{2-6}$alkynyl, $C_{3-7}$cycloalkyl, $C_{2-9}$heterocycloalkyl, $C_{6-10}$aryl, and $C_{1-9}$heteroaryl are optionally substituted with one, two, or three $R^{20g}$;

each $R^{17}$ and each $R^{17a}$ are each independently selected from $C_{1-6}$alkyl and $C_{3-6}$cycloalkyl, wherein $C_{1-6}$alkyl and $C_{3-6}$cycloalkyl are optionally substituted with one, two or three of $R^{20h}$; or $R^{17}$ and $R^{17a}$ are combined to form a $C_{2-9}$heterocycloalkyl ring;

each $R^{20a}$, $R^{20b}$, $R^{20c}$, $R^{20d}$, $R^{20e}$, $R^{20f}$, $R^{20g}$, and $R^{20h}$ are each independently selected from halogen, oxo, =NH, —CN, $C_{1-6}$alkyl, $C_{2-6}$alkenyl, $C_{2-6}$alkynyl, $C_{3-10}$cycloalkyl, —$CH_2$—$C_{3-10}$cycloalkyl, $C_{2-9}$heterocycloalkyl, —$CH_2$—$C_{2-9}$heterocycloalkyl, $C_{6-10}$aryl, —$CH_2$—$C_{6-10}$aryl, $C_{1-9}$heteroaryl, —$OR^{21}$, —$SR^{21}$, —$N(R^{22})(R^{23})$, —$C(O)OR^{22}$, —$C(O)N(R^{22})(R^{23})$, —$C(O)C(O)N(R^{22})(R^{23})$, —$OC(O)N(R^{22})(R^{23})$, —$N(R^{24})C(O)N(R^{22})(R^{23})$, —$N(R^{24})C(O)OR^{25}$, —$N(R^{24})C(O)R^{25}$, —$N(R^{24})S(O)_2 R^{25}$, —$C(O)R^{25}$, —$S(O)_2 R^{25}$, —$S(O)_2 N(R^{22})(R^{23})$, —$OCH_2C(O)OR^{22}$, and —$OC(O)R^{25}$, wherein $C_{1-6}$alkyl, $C_{2-6}$alkenyl, $C_{2-6}$alkynyl, $C_{3-10}$cycloalkyl, —$CH_2$—$C_{3-10}$cycloalkyl, $C_{2-9}$heterocycloalkyl, —$CH_2$—$C_{2-9}$heterocycloalkyl, $C_{6-10}$aryl, —$CH_2$—$C_{6-10}$aryl, and $C_{1-9}$heteroaryl are optionally substituted with one, two, or three groups independently selected from halogen, oxo, =NH, —CN, $C_{1-6}$alkyl, $C_{1-6}$haloalkyl, $C_{1-6}$alkoxy, $C_{1-6}$haloalkoxy, —$OR^{21}$, —$SR^{21}$, —$N(R^{22})(R^{23})$, —$C(O)OR^{22}$, —$C(O)N(R^{22})(R^{23})$, —$C(O)C(O)N(R^{22})(R^{23})$, —$OC(O)$ N($R^{22}$)($R^{23}$), —N($R^{24}$)C(O)N($R^{22}$)($R^{23}$), —N($R^{24}$)C(O)O$R^{25}$, —N($R^{24}$)C(O)$R^{25}$, —N($R^{24}$)S(O)$_2$$R^{25}$, —C(O)$R^{25}$, —S(O)$_2$$R^{25}$, —S(O)$_2$N($R^{22}$)($R^{23}$), and —OC(O)$R^{25}$;

each $R^{21}$ is independently selected from H, $C_{1-6}$alkyl, $C_{1-6}$haloalkyl, $C_{2-6}$alkenyl, $C_{2-6}$alkynyl, $C_{3-7}$cycloalkyl, $C_{2-9}$heterocycloalkyl, $C_{6-10}$aryl, and $C_{1-9}$heteroaryl, wherein $C_{3-7}$cycloalkyl, $C_{2-9}$heterocycloalkyl, $C_{6-10}$aryl, and $C_{1-9}$heteroaryl are optionally substituted with one, two, or three groups independently selected from halogen and $C_{1-6}$alkyl;

each $R^{22}$ is independently selected from H, $C_{1-6}$alkyl, $C_{1-6}$haloalkyl, $C_{2-6}$alkenyl, $C_{2-6}$alkynyl, $C_{3-7}$cycloalkyl, $C_{2-9}$heterocycloalkyl, $C_{6-10}$aryl, and $C_{1-9}$heteroaryl, wherein $C_{3-7}$cycloalkyl, $C_{2-9}$heterocycloalkyl, $C_{6-10}$aryl, and $C_{1-9}$heteroaryl are optionally substituted with one, two, or three groups independently selected from halogen and $C_{1-6}$alkyl;

each $R^{23}$ is independently selected from H and $C_{1-6}$alkyl;
each $R^{24}$ is independently selected from H and $C_{1-6}$alkyl; and
each $R^{25}$ is selected from $C_{1-6}$alkyl, $C_{2-6}$alkenyl, $C_{2-6}$alkynyl, $C_{3-7}$cycloalkyl, $C_{2-9}$heterocycloalkyl, $C_{6-10}$aryl, and $C_{1-9}$heteroaryl, wherein $C_{1-6}$alkyl, $C_{3-7}$cycloalkyl, $C_{2-9}$heterocycloalkyl, $C_{6-10}$aryl, and $C_{1-9}$heteroaryl are optionally substituted with one, two, or three groups independently selected from halogen, $C_{1-6}$alkyl, $C_{1-6}$haloalkyl, $C_{1-6}$alkoxy, $C_{3-7}$cycloalkyl, $C_{2-9}$heterocycloalkyl, $C_{6-10}$aryl, and $C_{1-9}$heteroaryl.

In embodiments, $R^{2a}$ is $C_{1-6}$alkyl optionally substituted with one, two, or three $R^{20a}$. In embodiments, $R^{2a}$ is unsubstituted $C_{1-6}$alkyl. In embodiments, $R^{2a}$ is —CH$_3$. In embodiments, $R^{2b}$ is $C_{1-6}$alkyl optionally substituted with one, two, or three $R^{20a}$. In embodiments, $R^{2c}$ is $C_{1-6}$alkyl optionally substituted with one, two, or three $R^{20a}$. In embodiments, $R^{2c}$ is hydrogen. In embodiments, $R^{2a}$ is hydrogen or $C_{1-6}$alkyl optionally substituted with one, two, or three $R^{20a}$. In embodiments, $R^{2e}$ is hydrogen. In embodiments, $R^2$ is hydrogen. In embodiments, $R^{20b}$ is CN. In embodiments, $R^7$ is hydrogen or methyl. In embodiments, $R^7$ is hydrogen. In embodiments, $R^6$ is selected from hydrogen, halogen, $C_{1-6}$alkyl, $C_{3-10}$cycloalkyl, $C_{2-9}$heterocycloalkyl, and $C_{1-9}$heteroaryl, wherein $C_{1-6}$alkyl, $C_{3-10}$cycloalkyl, $C_{2-9}$heterocycloalkyl, and $C_{1-9}$heteroaryl are optionally substituted with one, two, or three $R^{20c}$. In embodiments, $R^6$ is independently selected from hydrogen, halogen, and unsubstituted $C_{1-6}$alkyl. In embodiments, $R^6$ is hydrogen. In embodiments, $R^5$ is selected from $C_{1-6}$alkyl and $C_{1-6}$haloalkyl. In embodiments, $R^5$ is —CH$_3$. In embodiments, $R^4$ is hydrogen. In embodiments, $L^1$ is a bond. In embodiments, $R^1$ is a 6-10 membered aryl ring substituted with one or more $R^{10}$. In embodiments, $R^1$ is phenyl substituted with one or more $R^{10}$. In embodiments, $R^1$ is phenyl substituted with one, two, or three $R^{10}$. In embodiments, $R^1$ is a 5-10 membered heteroaryl ring are substituted with one or more $R^{10}$. In embodiments, $R^1$ is a 5-10 membered heteroaryl ring are substituted with one, two, or three $R^{10}$. In embodiments, each $R^{10}$ is independently selected from halogen, $C_{1-6}$alkyl, $C_{3-7}$cycloalkyl, $C_{2-9}$heterocycloalkyl, $C_{6-10}$aryl, $C_{1-9}$heteroaryl, —O$R^{12}$, and N($R^{12}$)($R^{13}$), wherein $C_{1-6}$alkyl, $C_{3-7}$cycloalkyl, $C_{2-9}$heterocycloalkyl, $C_{6-10}$aryl, and $C_{1-9}$heteroaryl are optionally substituted with one, two, or three $R^{20a}$. In embodiments, each $R^{10}$ is independently selected from halogen, $C_{1-6}$alkyl, and N($R^{12}$)($R^{13}$), wherein $C_{1-6}$alkyl is optionally substituted with one, two, or three $R^{20a}$. In embodiments, each $R^{10}$ is independently selected from halogen and $C_{1-6}$alkyl, wherein $C_{1-6}$alkyl is substituted with one, two, or three $R^{20a}$, and each $R^{20a}$ is halogen. In embodiments, each $R^{10}$ is independently selected from halogen, $C_{1-6}$alkyl, and N($R^{12}$)($R^{13}$), wherein $C_{1-6}$alkyl is optionally substituted with one, two, or three $R^{20a}$. In embodiments, each $R^{10}$ is independently selected from halogen and $C_{1-6}$alkyl, wherein $C_{1-6}$ alkyl is optionally substituted with one, two, or three $R^{20d}$.

In some embodiments of a compound of Formula (I), (I'), (Ia), (Ia'), (Ib), (Ib'), (Ic), (Ic'), (II), (II'), (III), (III'), (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), $R^{2a}$ is selected from $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —C(O)O$R^{12}$, —C(O)$R^{15}$, —C(O)N($R^{12}$)($R^{13}$), —S(O)$_2$$R^{15}$, —S(O)$_2$N($R^{12}$)($R^{13}$), wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20a}$.

Also provided are compounds 101-146 and 148-151 of Table 1 individually or collectively, pharmaceutically acceptable salt or solvate thereof. Also provided are compounds 147 and 152-423 of Table 1 individually or collectively, pharmaceutically acceptable salt or solvate thereof. Further provided are compounds 424-427 of Table 1 individually or collectively, pharmaceutically acceptable salt or solvate thereof.

Besides the inhibitory effect and high potency in reducing Kras signaling output by targeting SOS1, a molecule in the Ras signaling pathway, compounds disclosed herein exhibit advantageous solubility and DMPK properties. Fine-tuned pharmacological properties embodied in the subject compounds are of great significance for improving efficacy and safety of SOS1 inhibitors for therapeutic clinical applications. Moreover, compounds disclosed herein exhibit minimal cross reactivity to a wide spectrum of kinases and hence reducing undesired off-target side effects.

In some embodiments, compounds of Formula I-1, (I'-1), (Ia-1), (Ia'-1), (Ib-1), (Ib'-1), (Ic-1), or (Ic'-1) exhibit at least one, two, three or multiple salient superior pharmacological and/or safety properties as compared to compounds having the same core scaffold with R7 being non-hydrogen, but comprising a substitution. Exemplary superior DMPK properties associated with the subject compounds include but are not limited to improved metabolic stability, reduced hERG liability, decreased CYP inhibition, increased oral exposure, and decreased serum protein binding (hence increasing the free and available compounds circulating in a subject's blood upon administration of the compounds).

In some embodiments, a compound of Formula I-1 exhibits a decreased serum protein binding as compared to a compound having the same core scaffold with $R^7$ being non-hydrogen. In an embodiment, such subject compound of Formula (I-1), (I'-1), (Ia-1), (Ia'-1), (Ib-1), (Ib'-1), (Ic-1), or (Ic'-1) exhibits a decreased serum protein binding as compared to a compound having the same core scaffold of a Formula (I), (I'), (Ia), (Ia'), (Ib), (Ib'), (Ic), (Ic'), (I-2), (I'-2), (Ia-2), (Ia'-2), (Ib-2), (Ib'-2), (Ic-2), or (Ic'-2) wherein $R^7$ is $C_{1-6}$alkyl optionally substituted with one, two, or three $R^{20c}$. In an embodiment, decreased serum protein binding is observed as compared to a compound having the same core scaffold of a Formula (I), (I'), (Ia), (Ia'), (Ib), (Ib'), (Ic), (Ic'), (I-2), (I'-2), (Ia-2), (Ia'-2), (Ib-2), (Ib'-2), (Ic-2), or (Ic'-2), wherein R7 is methyl. A comparison of such subject compound Formula (I-1), (I'-1), (Ia-1), (Ia'-1), (Ib-1), (Ib'-1), (Ic-1), or (Ic'-1) to compounds of the same core where R7 is non-hydrogen reveals a remarkable increase in unbound/free compound present in plasma by at least, 10%, 20%, 30%, 40%, 50%, 100%, 200%, 300%, 400%, 500%, 600%, 700%, 800%, 900%, or even higher.

In an embodiment, an increase in unbound/free compound present in plasma is associated with compounds of Formula (I-1), (I'-1), (Ia-1), (Ia'-1), (Ib-1), (Ib'-1), (Ic-1), or (Ic'-1), wherein $R^3$ is selected from $C_{1-6}$alkyl, $C_{2-6}$alkenyl, $C_{2-6}$alkynyl, $C_{3-14}$cycloalkyl, $C_{2-9}$heterocycloalkyl, $C_{6-10}$aryl, $C_{1-9}$heteroaryl, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, $N(R^{14})S(O)R^{15}$, —$C(O)R^{15}$, —$S(O)R^{15}$, —$OC(O)R^{15}$, —$C(O)N(R^{12})(R^{13a})$, —$C(O)C(O)N(R^{12})(R^{13})$, —$N(R^{14})C(O)R^{15}$, —$S(O)_2R^{15}$, —$S(O)_2N(R^{12})(R^{13})$, —$S(O)N(R^{12})(R^{13})$, —$S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, —$CH_2S(O)_2N(R^{12})(R^{13})$, —$CH_2N(R^{12})S(O)_2(R^{13})$, $CH_2S(O)R^{15}$, —$CH_2S(O)N(R^{12})(R^{13})$, —$CH_2N(R^{12})S(O)(R^{13})$ and —$P(O)(R^{17})(R^{17a})$, wherein $C_{1-6}$alkyl, $C_{2-6}$alkenyl, $C_{2-6}$alkynyl, $C_{3-14}$cycloalkyl, $C_{2-9}$heterocycloalkyl, $C_{6-10}$aryl, and $C_{1-9}$heteroaryl are optionally substituted with one, two, or three $R^{20b}$.

In an embodiment, an increase in unbound/free compound present in plasma is associated with compounds of Formula (I-1), (I'-1), (Ia-1), (Ia'-1), (Ib-1), (Ib'-1), (Ic-1), or (Ic'-1), wherein $R^3$ is selected from —$N(R^{12})(R^{13})$, —$C(O)R^{15}$, —$C(O)N(R^{12})(R^{13})$, —$SO_2(R^{12})(R^{13})$, —$SO_2N(R^{12})(R^{13})$, —$P(O)(R^{17})(R^{17a})$, $C_{1-6}$alkyl, $C_{3-10}$cycloalkyl, $C_{2-9}$heterocycloalkyl, $C_{6-10}$aryl, and $C_{1-9}$heteroaryl, wherein $C_{1-6}$alkyl, $C_{3-10}$cycloalkyl, $C_{2-9}$heterocycloalkyl, $C_{6-10}$aryl, and $C_{1-9}$heteroaryl are optionally substituted with one, two, or three $R^{20b}$.

In an embodiment, an increase in unbound/free compound present in plasma is associated with compounds of Formula (I-1), (I'-1), (Ia-1), (Ia'-1), (Ib-1), (Ib'-1), (Ic-1), or (Ic'-1), wherein $R^3$ is selected from $C_{2-9}$heterocycloalkyl optionally substituted with one, two, or three $R^{20b}$. In an embodiment, an increase in unbound/free compound present in plasma is associated with compounds of Formula (I-1), (I'-1), (Ia-1), (Ia'-1), (Ib-1), (Ib'-1), (Ic-1), or (Ic'-1), wherein $R^3$ is selected from $C_{3-10}$cycloalkyl optionally substituted with one, two, or three $R^{20b}$. In an embodiment, a decreased serum protein binding is associated with compounds of Formula (I-1), (I'-1), (Ia-1), (Ia'-1), (Ib-1), (Ib'-1), (Ic-1), or (Ic'-1), wherein is $C_{3-4}$cycloalkyl optionally substituted with one $R^{20b}$. In an embodiment, an increase in unbound/free compound present in plasma is associated with compounds of Formula (I-1), (I'-1), (Ia-1), (Ia'-1), (Ib-1), (Ib'-1), (Ic-1), or (Ic'-1), wherein $R^3$ is $C_{3-4}$cycloalkyl, optionally substituted with one, two, or three $R^{20b}$, where $R^{20b}$ is H or CN. In an embodiment, a decreased serum protein binding is associated with compounds of Formula of (I-1), (I'-1), (Ia-1), (Ia'-1), (Ib-1), (Ib'-1), (Ic-1), or (Ic'-1), wherein $R^3$ is $C_{3-4}$cycloalkyl, optionally substituted with one $R^{20b}$, where $R^{20b}$ is CN.

In an embodiment, an increase in unbound/free compound present in plasma is associated with compounds of Formula (I-1), (I'-1), (Ia-1), (Ia'-1), (Ib-1), (Ib'-1), (Ic-1), or (Ic'-1), wherein $R^3$ is $C_{3-4}$cycloalkyl, optionally substituted with one, two, or three $R^{20b}$, where $R^{20b}$ is $C_{1-3}$alkyl substituted with one, two, or three halogen. In an embodiment, a decreased serum protein binding is associated with compounds of Formula (I-1), (I'-1), (Ia-1), (Ia'-1), (Ib-1), (Ib'-1), (Ic-1), or (Ic'-1), wherein $R^3$ is $C_{3-4}$cycloalkyl, optionally substituted with one, two, or three $R^{20b}$, where $R^{20b}$ is $C_{1-3}$alkyl substituted with one, two, or three F.

In an embodiment, an increase in unbound/free compound present in plasma is associated with compounds of Formula (I-1), (I'-1), (Ia-1), (Ia'-1), (Ib-1), (Ib'-1), (Ic-1), or (Ic'-1), wherein $R^3$ is $C_{3-4}$cycloalkyl, optionally substituted with one $R^{20b}$, where $R^{20b}$ is methyl substituted with one F. In an embodiment, a decreased serum protein binding is associated with compounds of Formula (I-1), (I'-1), (Ia-1), (Ia'-1), (Ib-1), (Ib'-1), (Ic-1), or (Ic'-1), wherein $R^3$ is $C_{3-4}$cycloalkyl, optionally substituted with one $R^{20b}$, where $R^{20b}$ is methyl substituted with two F. In an embodiment, a decreased serum protein binding is associated with compounds of Formula (I-1), (I'-1), (Ia-1), (Ia'-1), (Ib-1), (Ib'-1), (Ic-1), or (Ic'-1), wherein $R^3$ is $C_{3-4}$cycloalkyl, optionally substituted with one $R^{20b}$, where $R^{20b}$ is methyl substituted with three F.

In an embodiment, an increase in unbound/free compound present in plasma is associated with compounds of Formula (I-1), (I'-1), (Ia-1), (Ia'-1), (Ib-1), (Ib'-1), (Ic-1), or (Ic'-1), wherein $R^3$ is cyclopropyl substituted with one CN.

In an embodiment, an increase in unbound/free compound present in plasma is associated with compounds of Formula (I-1), (I'-1), (Ia-1), (Ia'-1), (Ib-1), (Ib'-1), (Ic-1), or (Ic'-1), wherein $R^3$ is cyclopropyl, optionally substituted with one, two, or three $R^{20b}$, where $R^{20b}$ is $C_{1-3}$alkyl substituted with one, two, or three halogen. In an embodiment, a decreased serum protein binding is associated with compounds of Formula (I-1), (I'-1), (Ia-1), (Ia'-1), (Ib-1), (Ib'-1), (Ic-1), or (Ic'-1), wherein $R^3$ is cyclopropyl, optionally substituted with one, two, or three $R^{20b}$, where $R^{20b}$ is $C_{1-3}$alkyl substituted with one, two, or three F. In an embodiment, a decreased serum protein binding is associated with compounds of Formula (I-1), (I'-1), (Ia-1), (Ia'-1), (Ib-1), (Ib'-1), (Ic-1), or (Ic'-1), wherein $R^3$ is cyclopropyl, optionally substituted with one $R^{20b}$, where $R^{20b}$ is methyl substituted with one F. In an embodiment, a decreased serum protein binding is associated with compounds of Formula (I-1), (I'-1), (Ia-1), (Ia'-1), (Ib-1), (Ib'-1), (Ic-1), or (Ic'-1), wherein $R^3$ is cyclopropyl, optionally substituted with one $R^{20b}$, where $R^{20b}$ is methyl substituted with two F. In an embodiment, a decreased serum protein binding is associated with compounds of Formula (I-1), (I'-1), (Ia-1), (Ia'-1), (Ib-1), (Ib'-1), (Ic-1), or (Ic'-1), wherein $R^3$ is cyclopropyl, optionally substituted with one $R^{20b}$, where $R^{20b}$ is methyl substituted with three F.

In an embodiment, an increase in unbound/free compound present in plasma is associated with compounds of Formula (I-1), (I'-1), (Ia-1), (Ia'-1), (Ib-1), (Ib'-1), (Ic-1), or (Ic'-1), wherein $R^3$ is a sulfone, piperazinyl, cyclopropyl, thiomorpholinyl, or piperidinyl moiety.

Table 4 below summarizes sets of direct comparative data showing percentage of free/unbound compounds present in plasma.

TABLE 4

| Compound No. | Structure | DMPK-invitro-PPB (Mouse Unbound) [%] |
|---|---|---|
| 354 | 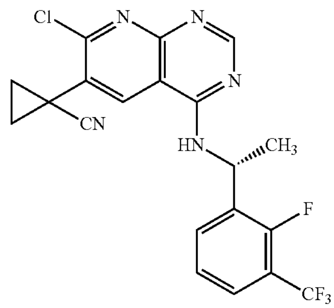 [SMILES: C[C@@H](Nc1ncnc2nc(Cl)c(C3(C#N)CC3)cc12)c1cccc(C(F)(F)F)c1F] | 0.52 |
| 300 | 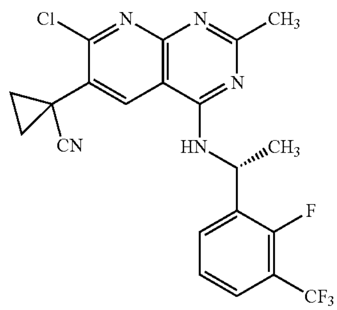 [SMILES: Cc1nc(N[C@H](C)c2cccc(C(F)(F)F)c2F)c2cc(C3(C#N)CC3)c(Cl)nc2n1] | 0.47 |
| 355 | 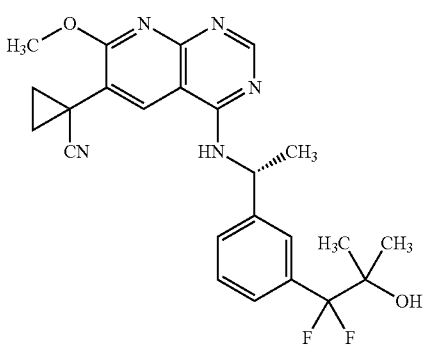 [SMILES: COc1nc2ncnc(N[C@H](C)c3cccc(C(F)(F)C(C)(C)O)c3)c2cc1C1(C#N)CC1] | 0.89 |
| 175 | 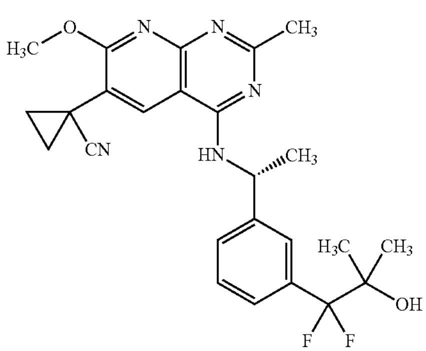 [SMILES: COc1nc2nc(C)nc(N[C@H](C)c3cccc(C(F)(F)C(C)(C)O)c3)c2cc1C1(C#N)CC1] | 0.11 |

TABLE 4-continued

| Compound No. | Structure | DMPK-invitro-PPB (Mouse Unbound) [%] |
| --- | --- | --- |
| 356 | 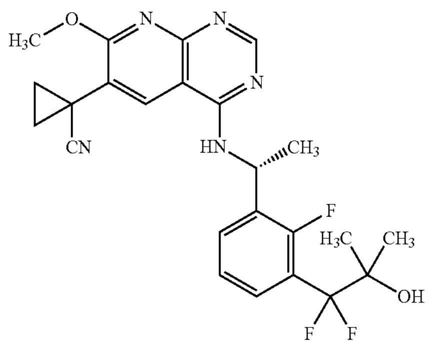 [SMILES: COc1nc2ncnc(N[C@H](C)c3cccc(C(F)(F)C(C)(C)O)c3F)c2cc1C1(C#N)CC1] | 0.48 |
| 207 | 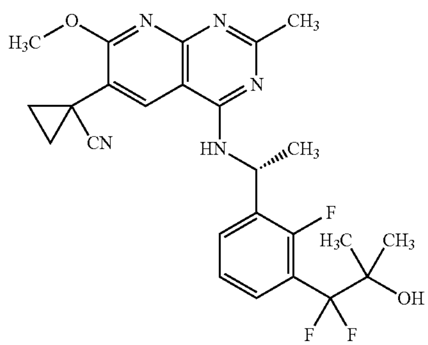 [SMILES: COc1nc2nc(C)nc(N[C@H](C)c3cccc(C(F)(F)C(C)(C)O)c3F)c2cc1C1(C#N)CC1] | 0.06 |
| 327 | 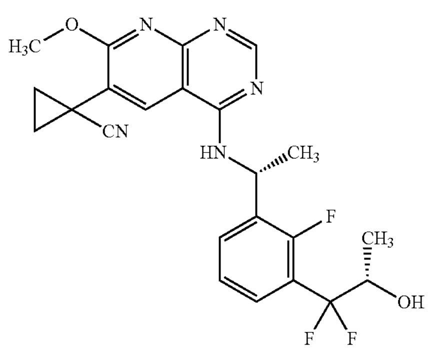 [SMILES: COc1nc2ncnc(N[C@H](C)c3cccc(C(F)(F)[C@H](C)O)c3F)c2cc1C1(C#N)CC1] | 2.34 |
| 256 | 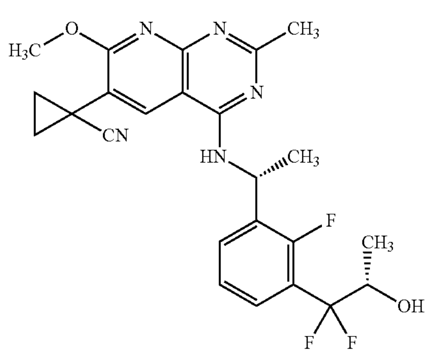 [SMILES: COc1nc2nc(C)nc(N[C@H](C)c3cccc(C(F)(F)[C@H](C)O)c3F)c2cc1C1(C#N)CC1] | 0.77 |

TABLE 4-continued

| Compound No. | Structure | DMPK-invitro-PPB (Mouse Unbound) [%] |
|---|---|---|
| 329 | 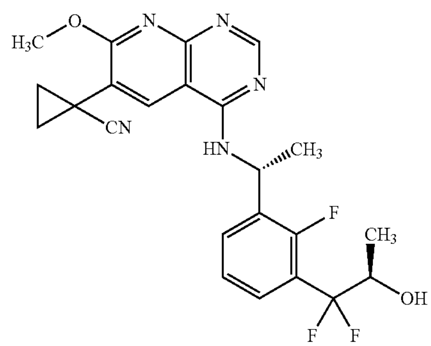 [SMILES: COc1nc2ncnc(N[C@H](C)c3cccc(C(F)(F)[C@@H](C)O)c3F)c2cc1C1(C#N)CC1] | 2.72 |
| 332 | 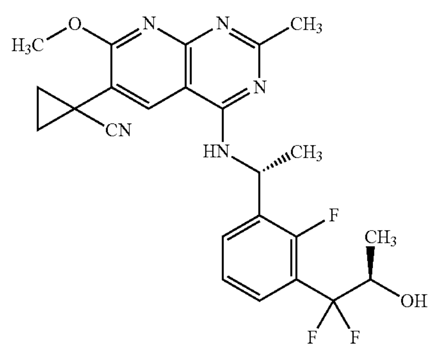 [SMILES: COc1nc2nc(C)nc(N[C@H](C)c3cccc(C(F)(F)[C@@H](C)O)c3F)c2cc1C1(C#N)CC1] | 0.3 |
| 264 | 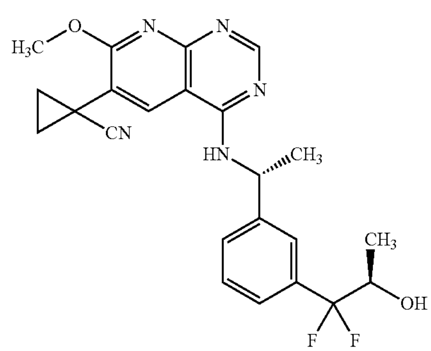 [SMILES: COc1nc2ncnc(N[C@H](C)c3cccc(C(F)(F)[C@@H](C)O)c3)c2cc1C1(C#N)CC1] | 4.94 |
| 366 | 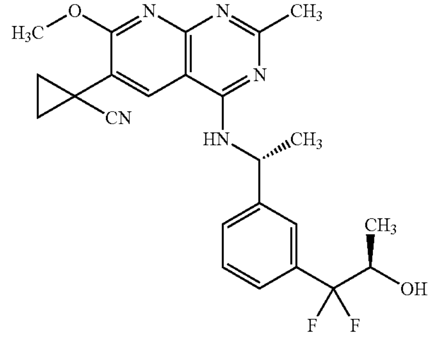 [SMILES: COc1nc2nc(C)nc(N[C@H](C)c3cccc(C(F)(F)[C@@H](C)O)c3)c2cc1C1(C#N)CC1] | 1.32 |

TABLE 4-continued
| Compound No. | Structure | DMPK-invitro-PPB (Mouse Unbound) [%] |
|---|---|---|
| 348 | 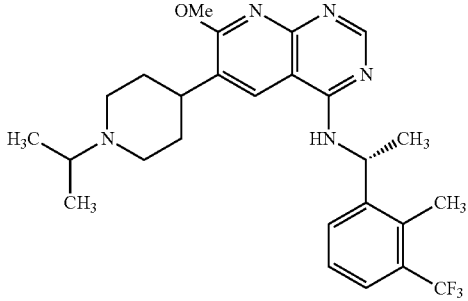 [SMILES: COc1nc2ncnc(N[C@H](C)c3cccc(C(F)(F)F)c3C)c2cc1C1CCN(C(C)C)CC1] | 1.03 |
| 236 | 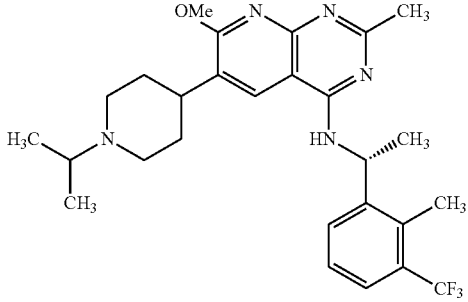 [SMILES: COc1nc2nc(C)nc(N[C@H](C)c3cccc(C(F)(F)F)c3C)c2cc1C1CCN(C(C)C)CC1] | 0.11 |
| 374 | 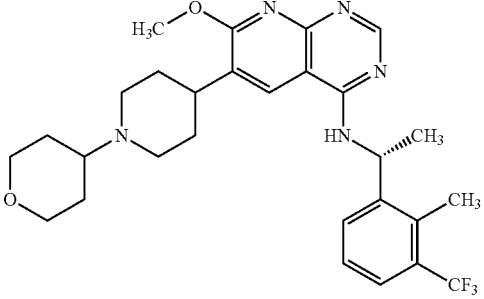 [SMILES: COc1nc2ncnc(N[C@H](C)c3cccc(C(F)(F)F)c3C)c2cc1C1CCN(C2CCOCC2)CC1] | 0.45 |
| 358 | 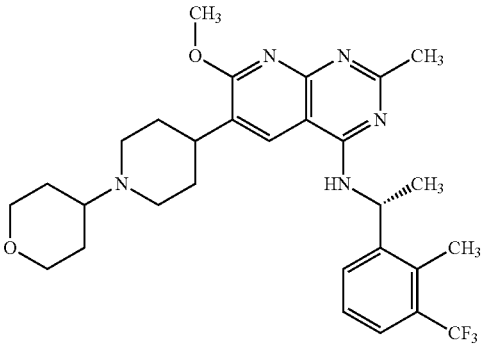 [SMILES: COc1nc2nc(C)nc(N[C@H](C)c3cccc(C(F)(F)F)c3C)c2cc1C1CCN(C2CCOCC2)CC1] | 0.065 |

TABLE 4-continued

| Compound No. | Structure | DMPK-invitro-PPB (Mouse Unbound) [%] |
|---|---|---|
| 162 | 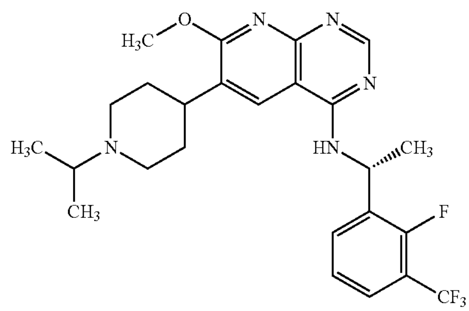 [SMILES: COc1nc2ncnc(N[C@H](C)c3cccc(C(F)(F)F)c3F)c2cc1C1CCN(C(C)C)CC1] | 2.19 |
| 287 | 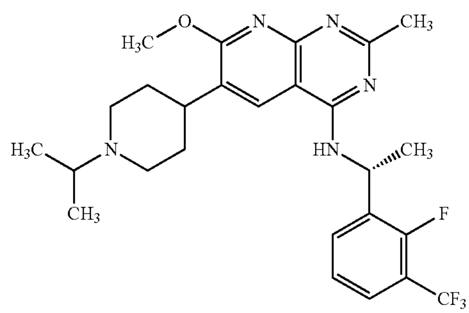 [SMILES: COc1nc2nc(C)nc(N[C@H](C)c3cccc(C(F)(F)F)c3F)c2cc1C1CCN(C(C)C)CC1] | 0.39 |
| 164 | 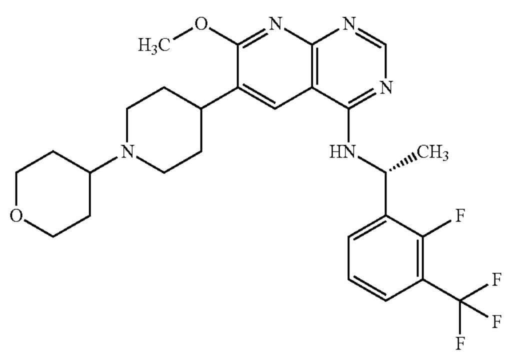 [SMILES: COc1nc2ncnc(N[C@H](C)c3cccc(C(F)(F)F)c3F)c2cc1C1CCN(C2CCOCC2)CC1] | 1.6 |
| 344 | 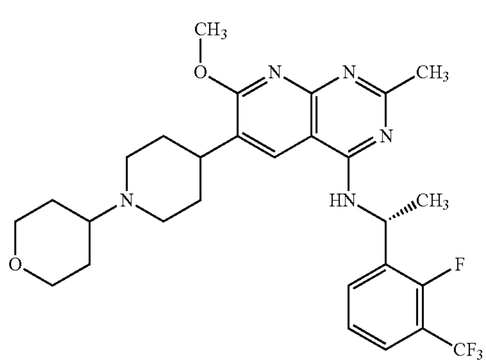 [SMILES: COc1nc2nc(C)nc(N[C@H](C)c3cccc(C(F)(F)F)c3F)c2cc1C1CCN(C2CCOCC2)CC1] | 0.29 |

TABLE 4-continued

| Compound No. | Structure | DMPK-invitro-PPB (Mouse Unbound) [%] |
|---|---|---|
| 353 | 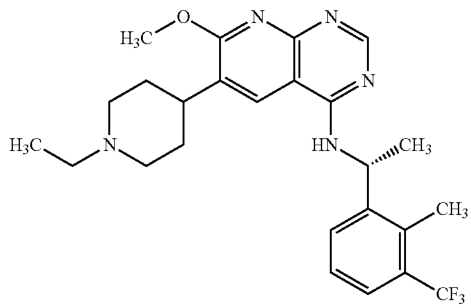 [SMILES: CCN1CCC(c2cc3c(N[C@H](C)c4cccc(C(F)(F)F)c4C)ncnc3nc2OC)CC1] | 0.74 |
| 351 | 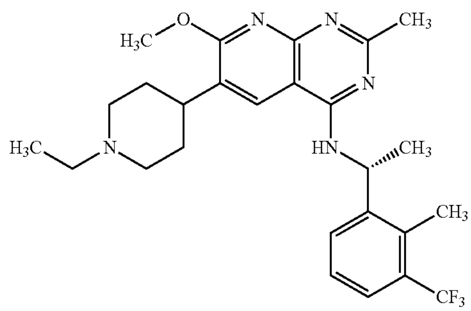 [SMILES: CCN1CCC(c2cc3c(N[C@H](C)c4cccc(C(F)(F)F)c4C)nc(C)nc3nc2OC)CC1] | 0.22 |
| 156 | 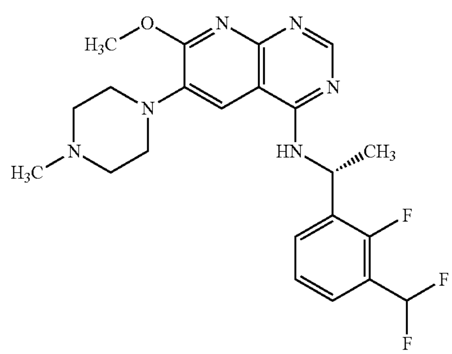 [SMILES: COc1nc2ncnc(N[C@H](C)c3cccc(C(F)F)c3F)c2cc1N1CCN(C)CC1] | 14.53 |
| 103 | 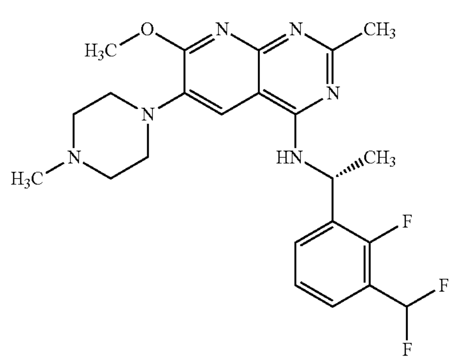 [SMILES: COc1nc2nc(C)nc(N[C@H](C)c3cccc(C(F)F)c3F)c2cc1N1CCN(C)CC1] | 5.15 |

TABLE 4-continued
| Compound No. | Structure | DMPK-invitro-PPB (Mouse Unbound) [%] |
|---|---|---|
| 316 | 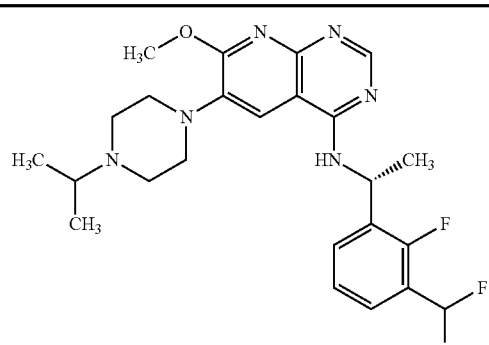 | 9.83 |
| 109 | 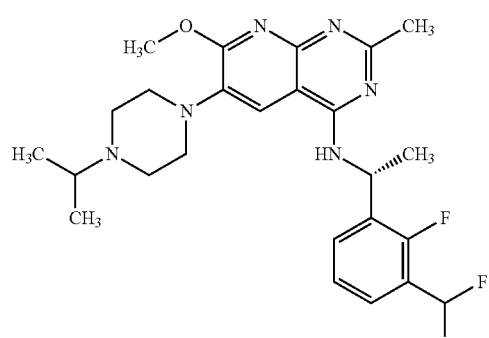 | 3.51 |
| 273 | 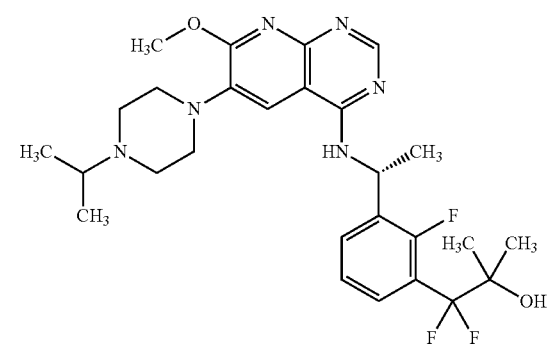 [SMILES: COc1nc2ncnc(N[C@H](C)c3cccc(C(F)(F)C(C)(C)O)c3F)c2cc1N1CCN(C(C)C)CC1] | 12.22 |
| 322 | 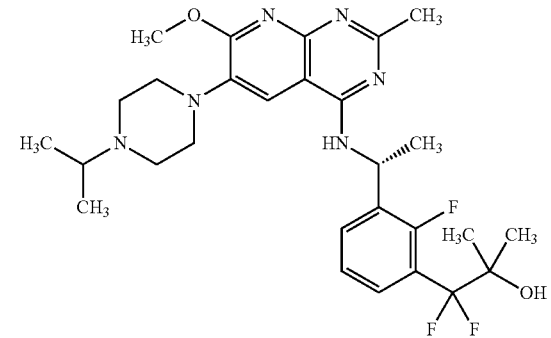 [SMILES: COc1nc2nc(C)nc(N[C@H](C)c3cccc(C(F)(F)C(C)(C)O)c3F)c2cc1N1CCN(C(C)C)CC1] | 6.33 |

TABLE 4-continued
| Compound No. | Structure | DMPK-invitro-PPB (Mouse Unbound) [%] |
|---|---|---|
| 202 | 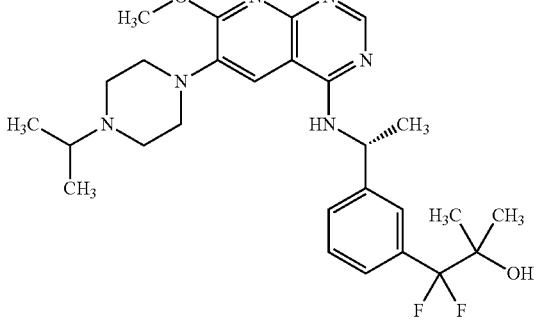 | 19.85 |
| 325 | 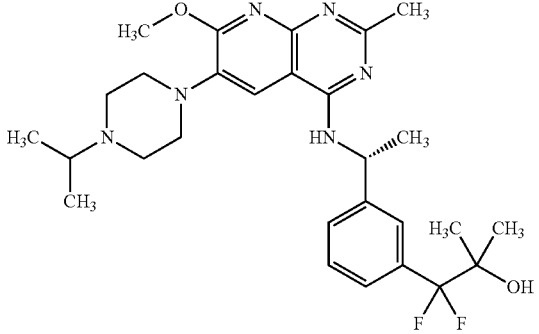 [SMILES: COc1nc2nc(C)nc(N[C@H](C)c3cccc(C(F)(F)C(C)(C)O)c3)c2cc1N1CCN(C(C)C)CC1] | 12.8 |
| 376 | 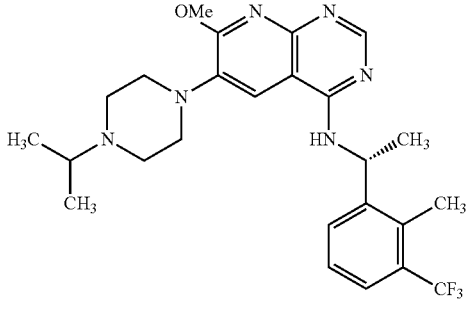 [SMILES: COc1nc2ncnc(N[C@H](C)c3cccc(C(F)(F)F)c3C)c2cc1N1CCN(C(C)C)CC1] | 0.91 |
| 171 | 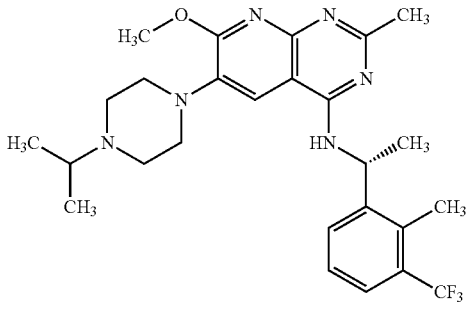 [SMILES: COc1nc2nc(C)nc(N[C@H](C)c3cccc(C(F)(F)F)c3C)c2cc1N1CCN(C(C)C)CC1] | 0.12 |

TABLE 4-continued

| Compound No. | Structure | DMPK-invitro-PPB (Mouse Unbound) [%] |
|---|---|---|
| 159 | 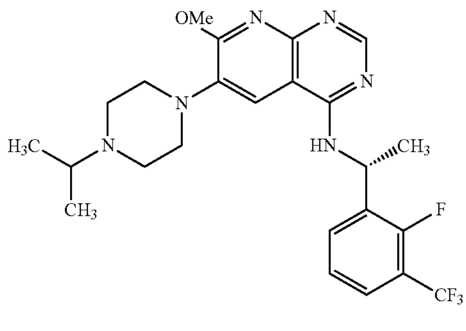 [SMILES: COc1nc2ncnc(N[C@H](C)c3cccc(C(F)(F)F)c3F)c2cc1N1CCN(C(C)C)CC1] | 3.43 |
| 211 | 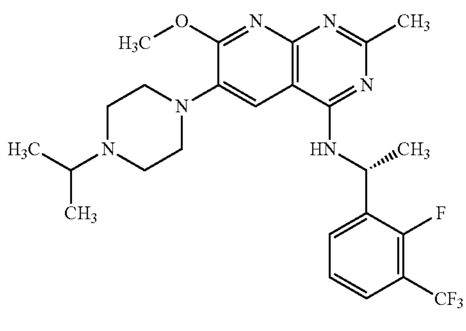 [SMILES: COc1nc2nc(C)nc(N[C@H](C)c3cccc(C(F)(F)F)c3F)c2cc1N1CCN(C(C)C)CC1] | 0.41 |
| 160 | 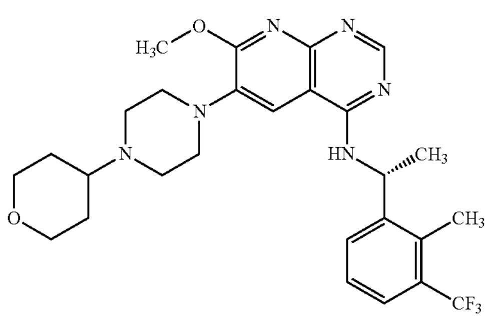 | 1.05 |
| 378 | 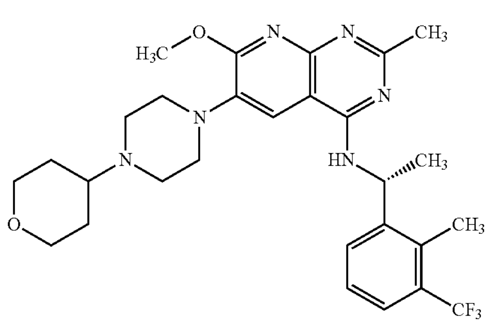 [SMILES: COc1nc2nc(C)nc(N[C@H](C)c3cccc(C(F)(F)F)c3C)c2cc1N1CCN(C2CCOCC2)CC1] | 0.14 |

TABLE 4-continued
| Compound No. | Structure | DMPK-invitro-PPB (Mouse Unbound) [%] |
|---|---|---|
| 146 | 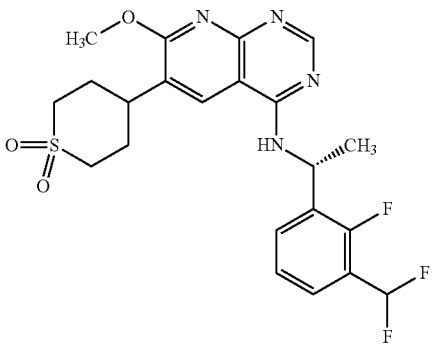 [SMILES: COc1nc2ncnc(N[C@H](C)c3cccc(C(F)F)c3F)c2cc1C1CCS(=O)(=O)CC1] | 3.58 |
| 102 | 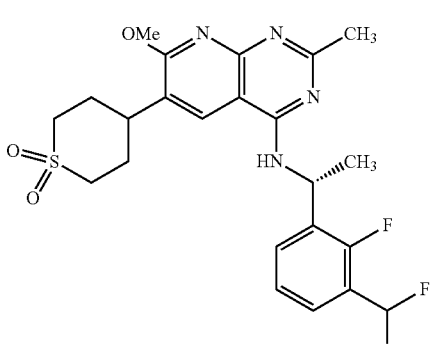 | 2.56 |
| 373 | 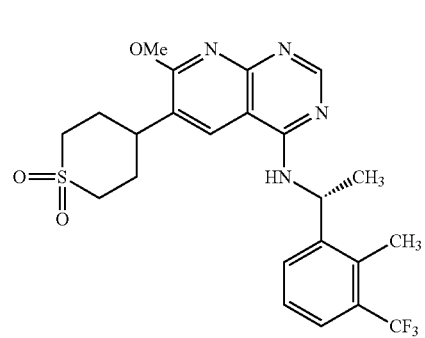 [SMILES: COc1nc2ncnc(N[C@H](C)c3cccc(C(F)(F)F)c3C)c2cc1C1CCS(=O)(=O)CC1] | 2.93 |
| 118 | 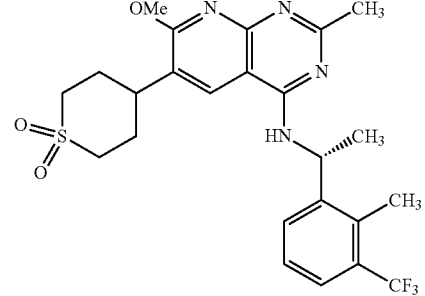 [SMILES: COc1nc2nc(C)nc(N[C@H](C)c3cccc(C(F)(F)F)c3C)c2cc1C1CCS(=O)(=O)CC1] | 0.31 |

TABLE 4-continued

| Compound No. | Structure | DMPK-invitro-PPB (Mouse Unbound) [%] |
|---|---|---|
| 375 | 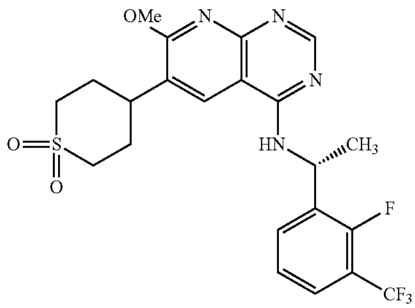 | 2.67 |
| 120 | 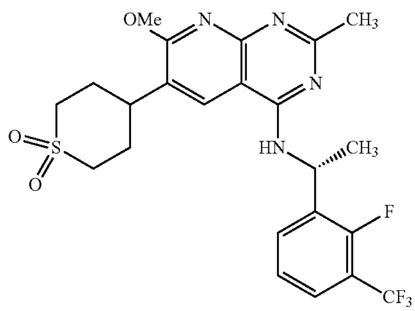 [SMILES: COc1nc2nc(C)nc(N[C@H](C)c3cccc(C(F)(F)F)c3F)c2cc1C1CCS(=O)(=O)CC1] | 0.73 |
| 267 | 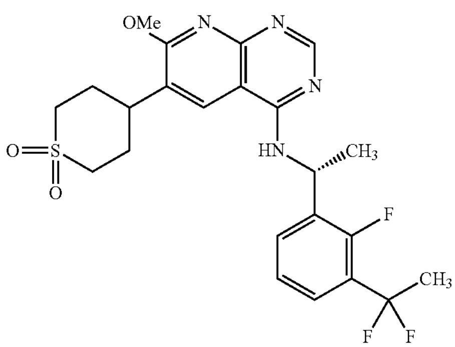 [SMILES: COc1nc2ncnc(N[C@H](C)c3cccc(C(C)(F)F)c3F)c2cc1C1CCS(=O)(=O)CC1] | 5.6 |
| 150 | 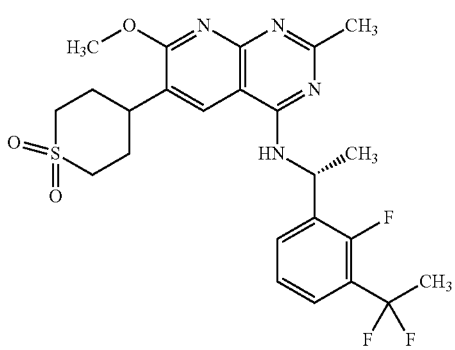 [SMILES: COc1nc2nc(C)nc(N[C@H](C)c3cccc(C(C)(F)F)c3F)c2cc1C1CCS(=O)(=O)CC1] | 2.65 |

TABLE 4-continued

| Compound No. | Structure | DMPK-invitro-PPB (Mouse Unbound) [%] |
|---|---|---|
| 339 | 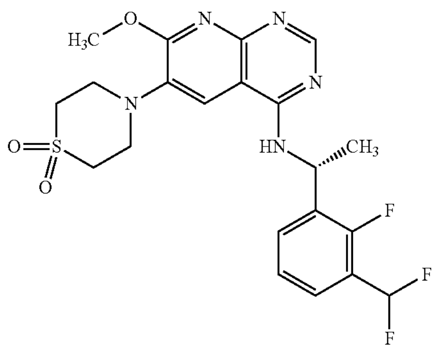 [SMILES: COc1nc2ncnc(N[C@H](C)c3cccc(C(F)F)c3F)c2cc1N1CCS(=O)(=O)CC1] | 15.32 |
| 131 | 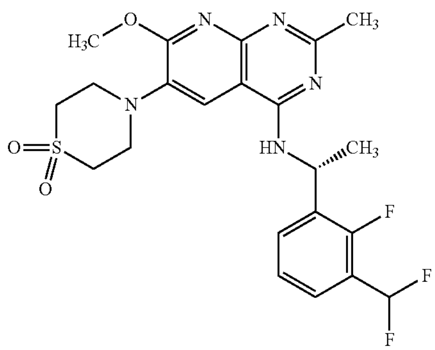 [SMILES: COc1nc2nc(C)nc(N[C@H](C)c3cccc(C(F)F)c3F)c2cc1N1CCS(=O)(=O)CC1] | 4.01 |
| 308 | 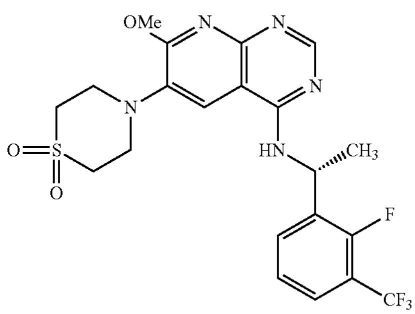 [SMILES: COc1nc2ncnc(N[C@H](C)c3cccc(C(F)(F)F)c3F)c2cc1N1CCS(=O)(=O)CC1] | 2.91 |
| 305 | 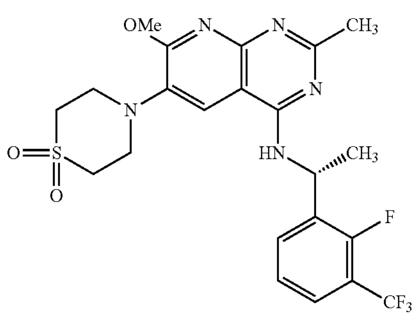 [SMILES: COc1nc2nc(C)nc(N[C@H](C)c3cccc(C(F)(F)F)c3F)c2cc1N1CCS(=O)(=O)CC1] | 1.24 |

The above direct comparison (compound pairs differ only at R7) clearly demonstrates that the subject compounds having R7 being H exhibit significantly higher percentage of unbound/free compounds in plasma. In some instances, a remarkable decrease in serum protein binding (or increase in free/unbound compound present in plasma) by at least, 100%, 200%, 300%, 400%, 500%, 600%, 700%, 800%, 900%, or even higher is observed. Such unexpected, superior structure and correlated functional attribute is observed in a variety of compounds of Formula (I-1), (I'-1), (Ia-1), (Ia'-1), (Ib-1), (Ib'-1), (Ic-1), or (Ic'-1) where R7 is hydrogen. In particular, such unexpected property is observed in compounds of Formula (I-1), (I'-1), (Ia-1), (Ia'-1), (Ib-1), (Ib'-1), (Ic-1), or (Ic'-1), wherein $R^3$ is selected from $C_{3-14}$cycloalkyl and $C_{2-9}$heterocycloalkyl, wherein $C_{3-14}$cycloalkyl and $C_{2-9}$heterocycloalkyl are optionally substituted with one, two, or three $R^{20b}$, wherein each $R^{20b}$ is independently selected from $C_{1-6}$alkyl, —CN, oxo, and $C_{2-9}$heterocycloalkyl. Of particular significance is that such superior property is embodied in compounds of Formula (I-1), (I'-1), (Ia-1), or (Ia'-1), wherein $R^3$ is cyclopropyl, optionally substituted with one $R^{20b}$, where $R^{20b}$ is CN. Of also significance is that such superior property is embodied in compounds of Formula (I-1), (I'-1), (Ia-1), (Ia'-1), (Ib-1), (Ib'-1), (Ic-1), or (Ic'-1), wherein $R^3$ is $C_6$heterocycloalkyl including sulfone-containing heterocycloalkyl and piperidinyl.

In some embodiments, a compound of Formula I-1, (I'-1), (Ia-1), (Ia'-1), (Ib-1), (Ib'-1), (Ic-1), or (Ic'-1) exhibit superior metabolic stability as compared to a compound having the same core scaffold with R7 being non-hydrogen. In an embodiment, such subject compound of Formula (I-1), (I'-1), (Ia-1), (Ia'-1), (Ib-1), (Ib'-1), (Ic-1), or (Ic'-1) exhibits an improved microsomal metabolic stability as compared to a compound having the same core scaffold of a Formula (I), (I'), (Ia), (Ia'), (Ib), (Ib'), (Ic), (Ic'), (I-2), (I'-2), (Ia-2), (Ia'-2), (Ib-2), (Ib'-2), (Ic-2), or (Ic'-2) wherein R7 is $C_{1-6}$alkyl optionally substituted with one, two, or three $R^{20c}$. In an embodiment, improved microsomal metabolic stability is observed as compared to a compound having the same core scaffold of a Formula (I), (I'), (Ia), (Ia'), (Ib), (Ib'), (Ic), (Ic'), (I-2), (I'-2), (Ia-2), (Ia'-2), (Ib-2), (Ib'-2), (Ic-2), or (Ic'-2), wherein R7 is methyl. In some embodiments, a comparison of such subject compound Formula (I-1), (I'-1), (Ia-1), (Ia'-1), (Ib-1), (Ib'-1), (Ic-1), or (Ic'-1) to compounds of the same core where R7 is non-hydrogen reveals remarkable improvements in microsomal metabolic stability by at least, 10%, 20%, 30%, 40%, 50%, 100%, 200%, 300%, 400%, 500%, or even higher.

In an embodiment, an improved microsomal metabolic stability is associated with compounds of Formula (I-1), (I'-1), (Ia-1), (Ia'-1), (Ib-1), (Ib'-1), (Ic-1), or (Ic'-1), wherein $R^3$ is selected from $C_{1-6}$alkyl, $C_{2-6}$alkenyl, $C_{2-6}$alkynyl, $C_{3-14}$cycloalkyl, $C_{2-9}$heterocycloalkyl, $C_{6-10}$aryl, $C_{1-9}$heteroaryl, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, $N(R^{14})S(O)R^{15}$, —$C(O)R^{15}$, —$S(O)R^{15}$, —$OC(O)R^{15}$, —$C(O)N(R^{12})(R^{13a})$, —$C(O)C(O)N(R^{12})(R^{13})$, —$N(R^{14})C(O)R^{15}$, —$S(O)_2R^{15}$, —$S(O)_2N(R^{12})(R^{13})$, —$S(O)N(R^{12})(R^{13})$, —$S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, —$CH_2S(O)_2N(R^{12})(R^{13})$, —$CH_2N(R^{12})S(O)_2(R^{13})$, $CH_2S(O)R^{15}$, —$CH_2S(O)N(R^{12})(R^{13})$, —$CH_2N(R^{12})S(O)(R^{13})$ and —$P(O)(R^{17})(R^{17a})$, wherein $C_{1-6}$alkyl, $C_{2-6}$alkenyl, $C_{2-6}$alkynyl, $C_{3-14}$cycloalkyl, $C_{2-9}$heterocycloalkyl, $C_{6-10}$aryl, and $C_{1-9}$heteroaryl are optionally substituted with one, two, or three $R^{20b}$.

In an embodiment, an improved microsomal metabolic stability is associated with compounds of Formula (I-1), (I'-1), (Ia-1), (Ia'-1), (Ib-1), (Ib'-1), (Ic-1), or (Ic'-1), wherein $R^3$ is selected from —$N(R^{12})(R^{13})$, —$C(O)R^{15}$, —$C(O)N(R^{12})(R^{13})$, —$SO_2(R^{12})(R^{13})$, —$SO_2N(R^{12})(R^{13})$, —$P(O)(R^{17})(R^{17a})$, $C_{1-6}$alkyl, $C_{3-10}$cycloalkyl, $C_{2-9}$heterocycloalkyl, $C_{6-10}$aryl, and $C_{1-9}$heteroaryl, wherein $C_{1-6}$alkyl, $C_{3-10}$cycloalkyl, $C_{2-9}$heterocycloalkyl, $C_{6-10}$aryl, and $C_{1-9}$heteroaryl are optionally substituted with one, two, or three $R^{20b}$.

In an embodiment, an improved microsomal metabolic stability is associated with compounds of Formula (I-1), (I'-1), (Ia-1), (Ia'-1), (Ib-1), (Ib'-1), (Ic-1), or (Ic'-1), wherein $R^3$ is selected from $C_{2-9}$heterocycloalkyl optionally substituted with one, two, or three $R^{20b}$.

In an embodiment, an improved microsomal metabolic stability is associated with compounds of Formula (I-1), (I'-1), (Ia-1), (Ia'-1), (Ib-1), (Ib'-1), (Ic-1), or (Ic'-1), wherein $R^3$ is selected from $C_{3-10}$cycloalkyl optionally substituted with one, two, or three $R^{20b}$ In an embodiment, an improved microsomal metabolic stability is associated with compounds of Formula (I-1), (I'-1), (Ia-1), (Ia'-1), (Ib-1), (Ib'-1), (Ic-1), or (Ic'-1), wherein is $C_{3-4}$cycloalkyl optionally substituted with one $R^{20b}$.

In an embodiment, an improved microsomal metabolic stability is associated with compounds of Formula (I-1), (I'-1), (Ia-1), (Ia'-1), (Ib-1), (Ib'-1), (Ic-1), or (Ic'-1), wherein $R^3$ is $C_{3-4}$cycloalkyl, optionally substituted with one, two, or three $R^{20b}$, where $R^{20b}$ is H or CN. In an embodiment, an improved microsomal metabolic stability is associated with compounds of Formula of (I-1), (I'-1), (Ia-1), (Ia'-1), (Ib-1), (Ib'-1), (Ic-1), or (Ic'-1), wherein $R^3$ is $C_{3-4}$cycloalkyl, optionally substituted with one $R^{20b}$, where $R^{20b}$ is CN.

In an embodiment, an improved microsomal metabolic stability is associated with compounds of Formula (I-1), (I'-1), (Ia-1), (Ia'-1), (Ib-1), (Ib'-1), (Ic-1), or (Ic'-1), wherein $R^3$ is $C_{3-4}$cycloalkyl, optionally substituted with one, two, or three $R^{20b}$, where $R^{20b}$ is $C_{1-3}$alkyl substituted with one, two, or three halogen. In an embodiment, an improved microsomal metabolic stability is associated with compounds of Formula (I-1), (I'-1), (Ia-1), (Ia'-1), (Ib-1), (Ib'-1), (Ic-1), or (Ic'-1), wherein $R^3$ is $C_{3-4}$cycloalkyl, optionally substituted with one, two, or three $R^{20b}$, where $R^{20b}$ is $C_{1-3}$alkyl substituted with one, two, or three F.

In an embodiment, an improved microsomal metabolic stability is associated with compounds of Formula (I-1), (I'-1), (Ia-1), (Ia'-1), (Ib-1), (Ib'-1), (Ic-1), or (Ic'-1), wherein $R^3$ is $C_{3-4}$cycloalkyl, optionally substituted with one $R^{20b}$, where $R^{20b}$ is methyl substituted with one F. In an embodiment, an improved microsomal metabolic stability is associated with compounds of Formula (I-1), (I'-1), (Ia-1), (Ia'-1), (Ib-1), (Ib'-1), (Ic-1), or (Ic'-1), wherein $R^3$ is $C_{3-4}$cycloalkyl, optionally substituted with one $R^{20b}$, where $R^{20b}$ is methyl substituted with two F. In an embodiment, an improved microsomal metabolic stability is associated with compounds of Formula (I-1), (I'-1), (Ia-1), (Ia'-1), (Ib-1), (Ib'-1), (Ic-1), or (Ic'-1), wherein $R^3$ is $C_{3-4}$cycloalkyl, optionally substituted with one $R^{20b}$, where $R^{20b}$ is methyl substituted with three F.

In an embodiment, an improved microsomal metabolic stability is associated with compounds of Formula (I-1), (I'-1), (Ia-1), (Ia'-1), (Ib-1), (Ib'-1), (Ic-1), or (Ic'-1), wherein $R^3$ is cyclopropyl substituted with one CN.

In an embodiment, an improved microsomal metabolic stability is associated with compounds of Formula (I-1), (I'-1), (Ia-1), (Ia'-1), (Ib-1), (Ib'-1), (Ic-1), or (Ic'-1), wherein $R^3$ is cyclopropyl, optionally substituted with one, two, or three $R^{20b}$, where $R^{20b}$ is $C_{1-3}$alkyl substituted with one, two, or three halogen. In an embodiment, an improved microsomal metabolic stability is associated with compounds of Formula (I-1), (I'-1), (Ia-1), (Ia'-1), (Ib-1), (Ib'-1), (Ic-1), or (Ic'-1), wherein $R^3$ is cyclopropyl, optionally substituted with one, two, or three $R^{20b}$, where $R^{20b}$ is $C_{1-3}$alkyl substituted with one, two, or three F. In an embodiment, an improved microsomal metabolic stability is associated with compounds of Formula (I-1), (I'-1), (Ia-1), (Ia'-1), (Ib-1), (Ib'-1), (Ic-1), or (Ic'-1), wherein $R^3$ is cyclopropyl, optionally substituted with one $R^{20b}$, where $R^{20b}$ is methyl substituted with one F. In an embodiment, an improved microsomal metabolic stability is associated with compounds of Formula (I-1), (I'-1), (Ia-1), (Ia'-1), (Ib-1), (Ib'-1), (Ic-1), or (Ic'-1), wherein $R^3$ is cyclopropyl, optionally substituted with one $R^{20b}$, where $R^{20b}$ is methyl substituted with two F. In an embodiment, an improved microsomal metabolic stability is associated with compounds of Formula (I-1), (I'-1), (Ia-1), (Ia'-1), (Ib-1), (Ib'-1), (Ic-1), or (Ic'-1), wherein $R^3$ is cyclopropyl, optionally substituted with one $R^{20b}$, where $R^{20b}$ is methyl substituted with three F. In an embodiment, an improved microsomal metabolic stability is associated with compounds of Formula (I-1), (I'-1), (Ia-1), (Ia'-1), (Ib-1), (Ib'-1), (Ic-1), or (Ic'-1), wherein $R^3$ is $C_{3-4}$cycloalkyl, substituted with one, two, or three $R^{20b}$, where $R^{20b}$ is H or CN.

In an embodiment, an improved microsomal metabolic stability is associated with compounds of Formula (I-1), (I'-1), (Ia-1), (Ia'-1), (Ib-1), (Ib'-1), (Ic-1), or (Ic'-1), wherein $R^2$ is —$OR^{2a}$, —$NR^{2b}R^{2c}$, —$SR^{2g}$, —$S(O)R^{2h}$, —$S(O)_2R^{2h}$, —$S(O)_2NR^{2b}R^{2c}$, —$C(R^{2d})(R^{2e})(R^{21})$, $C(O)NR^{2b}R^{2c}$, —CN, or halogen. In an embodiment, such superior property is associated with compounds of Formula (I-1), (I'-1), (Ia-1), or (Ia'-1), wherein $R^2$ is —$OR^{2a}$ or halogen. In an embodiment, such superior property is associated with compounds of Formula (I-1), (I'-1), (Ia-1), or (Ia'-1), wherein $R^2$ is —$OR^{2a}$, where $R^{2a}$ is selected from $C_{1-6}$alkyl, $C_{3-10}$cycloalkyl, $C_{2-9}$heterocycloalkyl, $C_{6-10}$aryl, $C_{1-9}$heteroaryl, and wherein $C_{1-6}$alkyl, $C_{3-10}$cycloalkyl, $C_{2-9}$heterocycloalkyl, $C_{6-10}$aryl, and $C_{1-9}$heteroaryl are optionally substituted with one, two, or three $R^{20a}$. In an embodiment, such superior property is associated with compounds of Formula (I-1), (I'-1), (Ia-1), or (Ia'-1), wherein $R^2$ is —$OR^{2a}$, where $R^{2a}$ is $C_{1-6}$alkyl. In an embodiment, such superior property is associated with compounds of Formula (I-1), (I'-1), (Ia-1), (Ia'-1), (Ib-1), (Ib'-1), (Ic-1), or (Ic'-1), wherein $R^2$ is —$OR^{2a}$, where $R^{2a}$ is methyl. In an embodiment, such superior property is associated with compounds of Formula (I-1), (I'-1), (Ia-1), or (Ia'-1), wherein $R^2$ is —$OR^{2a}$, where $R^{2a}$ is $C_{2-9}$heterocycloalkyl, optionally substituted with one, two, or three $R^{20a}$. In an embodiment, such superior property is associated with compounds of Formula (I-1), (I'-1), (Ia-1), (Ia'-1), (Ib-1), (Ib'-1), (Ic-1), or (Ic'-1), wherein $R^2$ is —$OR^{2a}$, where $R^{2a}$ is $C_{4-5}$heterocycloalkyl, optionally substituted with one, two, or three $R^{20a}$. In an embodiment, such superior property is associated with compounds of Formula (I-1), (I'-1), (Ia-1), or (Ia'-1), wherein $R^2$ is —$OR^{2a}$, where $R^{2a}$ is $C_4$heterocycloalkyl, optionally substituted with one, two, or three $R^{20a}$. In an embodiment, such superior property is associated with compounds of Formula (I-1), (I'-1), (Ia-1), or (Ia'-1), wherein $R^2$ is —$OR^{2a}$, where $R^{2a}$ is $C_5$heterocycloalkyl, optionally substituted with one, two, or three $R^{20a}$.

In an embodiment, such superior property is associated with compounds of Formula (I-1), (I'-1), (Ia-1), or (Ia'-1), wherein $R^2$ is —$OR^{2a}$, and $R^3$ is selected from $C_{3-10}$cycloalkyl optionally substituted with one, two, or three $R^{20b}$.

In an embodiment, such superior property is associated with compounds of Formula (I-1), (I'-1), (Ia-1), or (Ia'-1), wherein $R^2$ is —$OR^{2a}$, and $R^3$ is selected from cyclopropyl optionally substituted with one, two, or three $R^{20b}$. In an embodiment, such superior property is associated with compounds of Formula (I-1), (I'-1), (Ia-1), or (Ia'-1), wherein $R^2$ is —$OR^{2a}$, and $R^3$ is selected from cyclopropyl optionally substituted one CN. In an embodiment, such superior property is associated with compounds of Formula (I-1), (I'-1), (Ia-1), (Ia'-1), or (Ia'-1), wherein $R^2$ is —$OR^{2a}$, where $R^{2a}$ is methyl, and $R^3$ is cyclopropyl optionally substituted one CN. In an embodiment, such superior property is associated with compounds of Formula (I-1), (I'-1), (Ia-1), or (Ia'-1), wherein $R^2$ is —$OR^{2a}$, where $R^{2a}$ is $C_{4-5}$heterocycloalkyl optionally substituted with one, two, or three $R^{20a}$, and $R^3$ is selected from cyclopropyl optionally substituted one CN. In an embodiment, such superior property is associated with compounds of Formula (I-1), (I'-1), (Ia-1), or (Ia'-1), wherein $R^2$ is —$OR^{2a}$, where $R^{2a}$ is $C_4$heterocycloalkyl optionally substituted with one, two, or three $R^{20a}$, and $R^3$ is selected from cyclopropyl optionally substituted one CN. In an embodiment, such superior property is associated with compounds of Formula (I-1), (I'-1), (Ia-1), or (Ia'-1), wherein $R^2$ is —$OR^{2a}$, where $R^{2a}$ is $C_4$heterocycloalkyl optionally substituted with one, two, or three $R^{20a}$, and $R^3$ is selected from cyclopropyl optionally substituted one CN. In an embodiment, such superior property is associated with compounds of Formula (I-1), (I'-1), (Ia-1), or (Ia'-1), wherein $R^2$ is —$OR^{2a}$; where $R^{2a}$ is methyl; $R^3$ is selected from cyclopropyl optionally substituted one CN; $R^1$ is a phenyl substituted with one or more $R^{10}$; each $R^{10}$ is independently selected from halogen and $C_{1-6}$alkyl optionally substituted with one, two, or three $R^{20d}$; each $R^{20a}$ is independently selected from halogen, —OH, $C_{2-5}$heterocycloalkyl optionally substituted with one, two, or three $C_{1-6}$alkyl (e.g., methyl, ethyl, or propyl), and —$OR^{21}$; wherein $R^{21}$ is $C_{2-5}$heterocycloalkyl optionally substituted with one, two, or three $C_{1-6}$alkyl (e.g., methyl, ethyl, propyl, or butyl). In an embodiment, such superior property is associated with compounds of Formula (I-1), (I'-1), (Ia-1), or (Ia'-1), wherein $R^2$ is —$OR^{2a}$; $R^{2a}$ is methyl; $R^3$ is selected from cyclopropyl optionally substituted one CN; $R^1$ is a phenyl substituted with one or more $R^{10}$; each $R^{10}$ is independently selected from halogen and $C_{1-3}$alkyl optionally substituted with one, two, or three $R^{20a}$; each $R^{20a}$ is independently selected from halogen and —OH. In an embodiment, such superior property is associated with compounds of Formula (I-1), (I'-1), (Ia-1), or (Ia'-1), wherein $R^2$ is —$OR^{2a}$; $R^{2a}$ is methyl; $R^3$ is selected from cyclopropyl optionally substituted one CN; $R^1$ is a phenyl substituted with one or more $R^{10}$; each $R^{10}$ is independently selected from $C_{1-3}$alkyl optionally substituted with one, two, or three $R^{20a}$; each $R^{20a}$ is independently selected from halogen and —OH.

Table 5 below summarizes a set of direct comparative data showing the improvement of the in vitro microsomal metabolic stability of compounds of Formula (I-1), (I'-1), (Ia-1), or (Ia'-1), relative to the corresponding compounds in which R7 is non-hydrogen (e.g., methyl).

TABLE 5

| Compound No. | Structure | DMPK-invitro-metabolic Stability (Mouse T1/2) [min] |
|---|---|---|
| 400 | 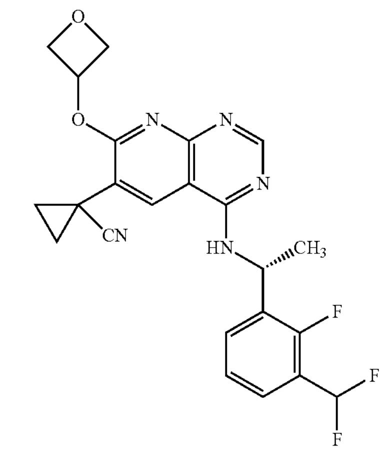 [SMILES: C[C@@H](Nc1ncnc2nc(OC3COC3)c(C3(C#N)CC3)cc12)c1cccc(C(F)F)c1F] | 29.4 |
| 402 | 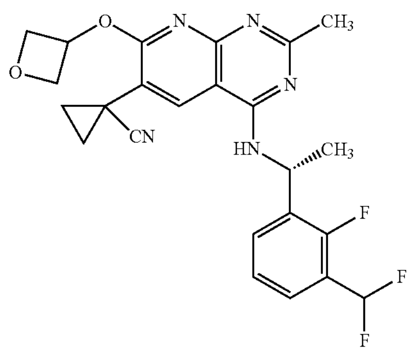 [SMILES: Cc1nc(N[C@H](C)c2cccc(C(F)F)c2F)c2cc(C3(C#N)CC3)c(OC3COC3)nc2n1] | 19.3 |
| 405 | 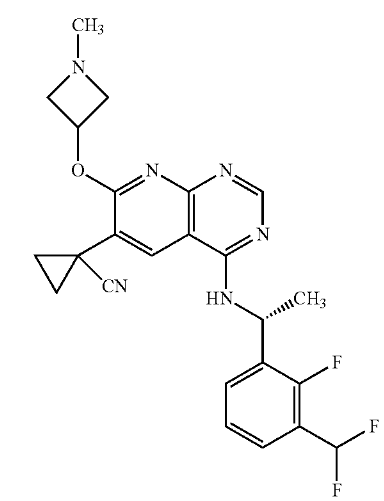 [SMILES: C[C@@H](Nc1ncnc2nc(OC3CN(C)C3)c(C3(C#N)CC3)cc12)c1cccc(C(F)F)c1F] | >200 |

TABLE 5-continued
| Compound No. | Structure | DMPK-invitro-metabolic Stability (Mouse T1/2) [min] |
|---|---|---|
| 234 | 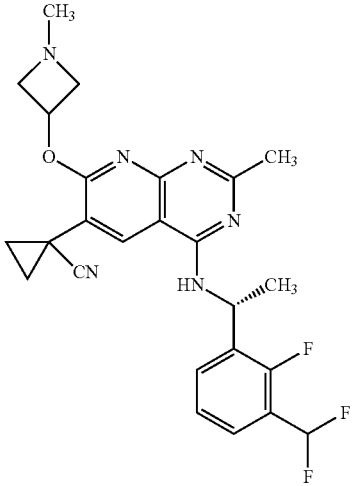 [SMILES: Cc1nc(N[C@H](C)c2cccc(C(F)F)c2F)c2cc(C3(C#N)CC3)c(OC3CN(C)C3)nc2n1] | 42.2 |
| 409 | 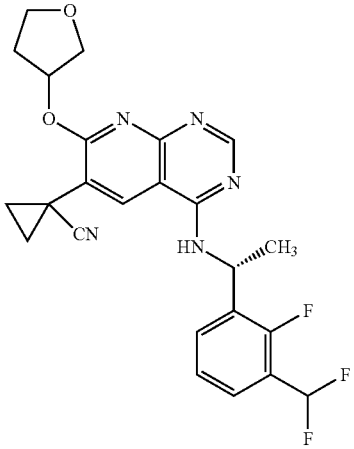 [SMILES: C[C@@H](Nc1ncnc2nc(OC3CCOC3)c(C3(C#N)CC3)cc12)c1cccc(C(F)F)c1F] | 5.6 |
| 298 | 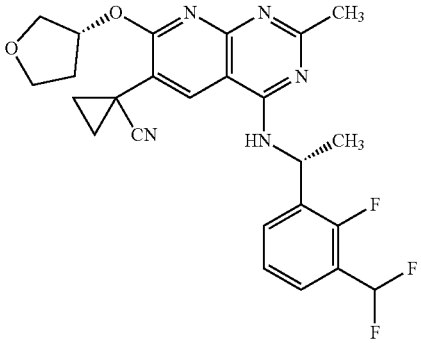 [SMILES: Cc1nc(N[C@H](C)c2cccc(C(F)F)c2F)c2cc(C3(C#N)CC3)c(O[C@@H]3CCOC3)nc2n1] | 1.5 |

TABLE 5-continued

| Compound No. | Structure | DMPK-invitro-metabolic Stability (Mouse T1/2) [min] |
|---|---|---|
| 354 | 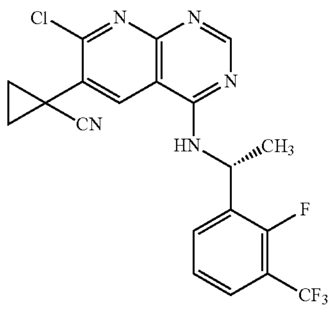 [SMILES: C[C@@H](Nc1ncnc2nc(Cl)c(C3(C#N)CC3)cc12)c1cccc(C(F)(F)F)c1F] | >200 |
| 300 | 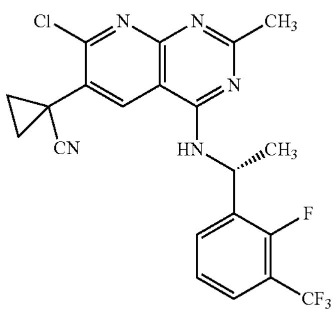 [SMILES: Cc1nc(N[C@H](C)c2cccc(C(F)(F)F)c2F)c2cc(C3(C#N)CC3)c(Cl)nc2n1] | 70.6 |
| 356 | 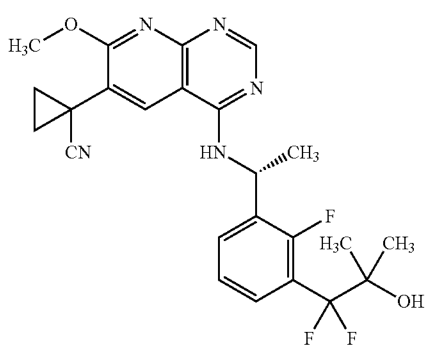 [SMILES: COc1nc2ncnc(N[C@H](C)c3cccc(C(F)(F)C(C)(C)O)c3F)c2cc1C1(C#N)CC1] | >200 |
| 207 | 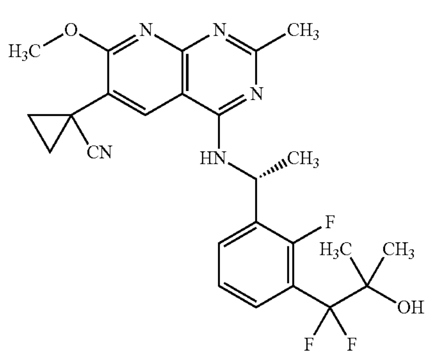 [SMILES: COc1nc2nc(C)nc(N[C@H](C)c3cccc(C(F)(F)C(C)(C)O)c3F)c2cc1C1(C#N)CC1] | >200 |

TABLE 5-continued

| Compound No. | Structure | DMPK-invitro-metabolic Stability (Mouse T1/2) [min] |
|---|---|---|
| 200 | 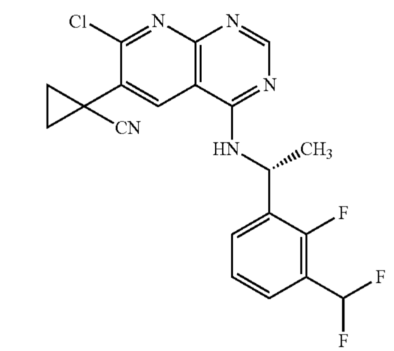 [SMILES: C[C@@H](Nc1ncnc2nc(Cl)c(C3(C#N)CC3)cc12)c1cccc(C(F)F)c1F] | 154 |
| 352 | 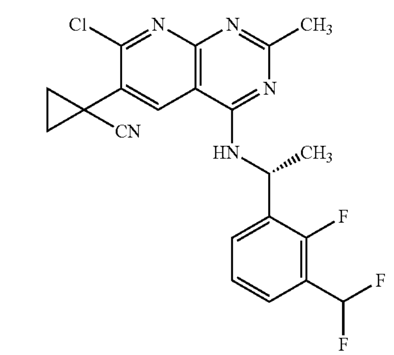 [SMILES: Cc1nc(N[C@H](C)c2cccc(C(F)F)c2F)c2cc(C3(C#N)CC3)c(Cl)nc2n1] | 31 |
| 327 | 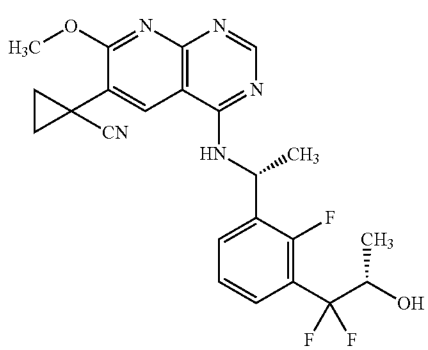 [SMILES: COc1nc2ncnc(N[C@H](C)c3cccc(C(F)(F)[C@H](C)O)c3F)c2cc1C1(C#N)CC1] | 131 |
| 256 | 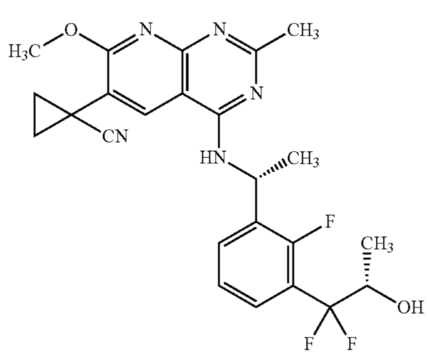 [SMILES: COc1nc2nc(C)nc(N[C@H](C)c3cccc(C(F)(F)[C@H](C)O)c3F)c2cc1C1(C#N)CC1] | 37.2 |

TABLE 5-continued

| Compound No. | Structure | DMPK-invitro-metabolic Stability (Mouse T1/2) [min] |
|---|---|---|
| 355 | 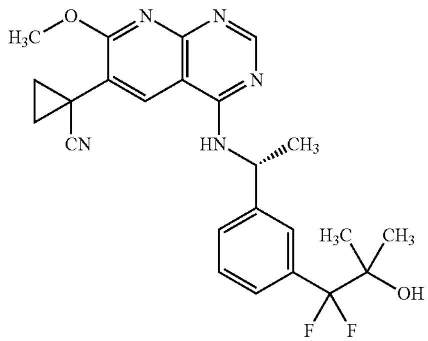 [SMILES: COc1nc2ncnc(N[C@H](C)c3cccc(C(F)(F)C(C)(C)O)c3)c2cc1C1(C#N)CC1] | >200 |
| 175 | 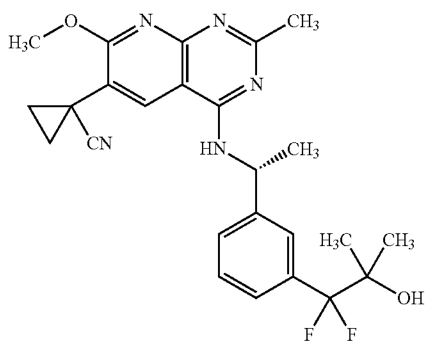 [SMILES: COc1nc2nc(C)nc(N[C@H](C)c3cccc(C(F)(F)C(C)(C)O)c3)c2cc1C1(C#N)CC1] | 198.5 |
| 329 | 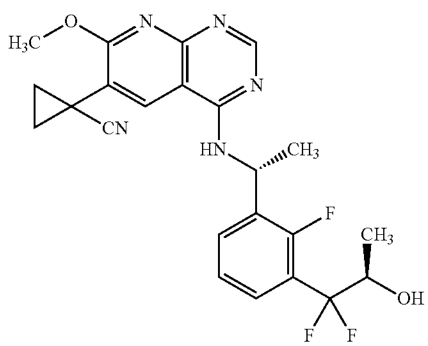 [SMILES: COc1nc2ncnc(N[C@H](C)c3cccc(C(F)(F)[C@@H](C)O)c3F)c2cc1C1(C#N)CC1] | 120.3 |
| 332 | 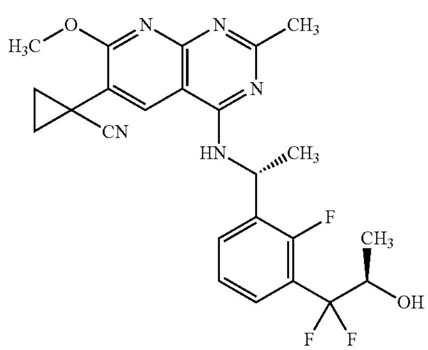 [SMILES: COc1nc2nc(C)nc(N[C@H](C)c3cccc(C(F)(F)[C@@H](C)O)c3F)c2cc1C1(C#N)CC1] | 30.1 |

TABLE 5-continued
| Compound No. | Structure | DMPK-invitro-metabolic Stability (Mouse T1/2) [min] |
|---|---|---|
| 361 | 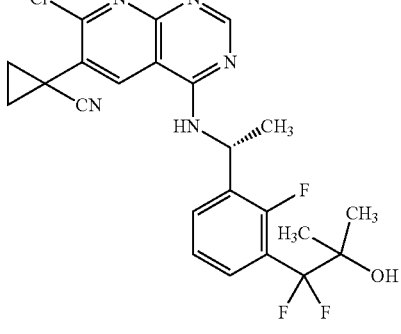 | >200 |
| 170 | 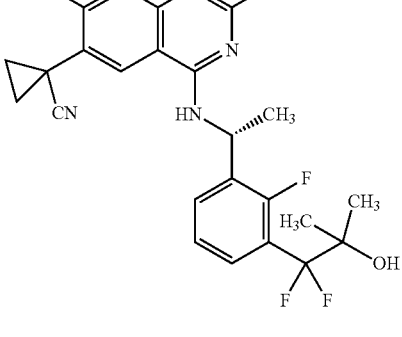 | >200 |
| 362 | 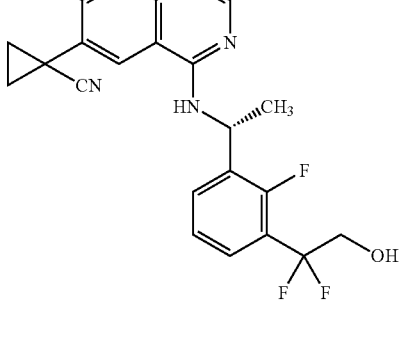 | 49 |
| 195 | 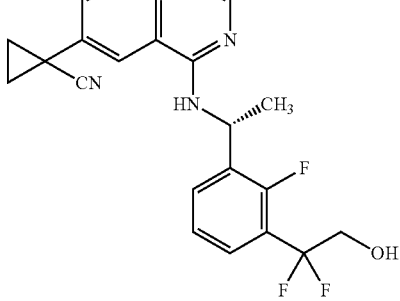 | 21.1 |

TABLE 5-continued

| Compound No. | Structure | DMPK-invitro-metabolic Stability (Mouse T1/2) [min] |
|---|---|---|
| 363 | 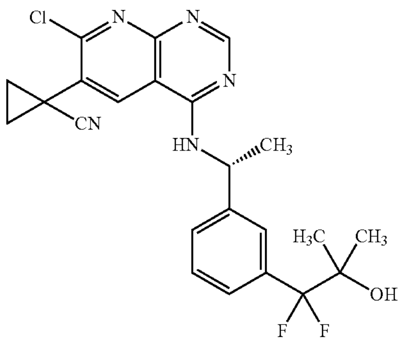 [SMILES: C[C@@H](Nc1ncnc2nc(Cl)c(C3(C#N)CC3)cc12)c1cccc(C(F)(F)C(C)(C)O)c1] | >200 |
| 193 | 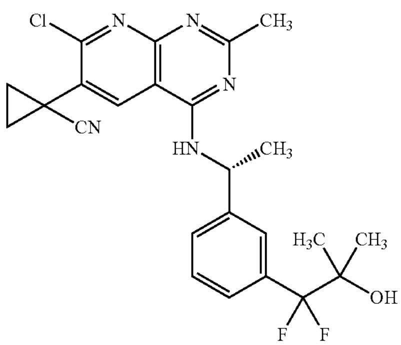 [SMILES: Cc1nc(N[C@H](C)c2cccc(C(F)(F)C(C)(C)O)c2)c2cc(C3(C#N)CC3)c(Cl)nc2n1] | >200 |
| 214 | 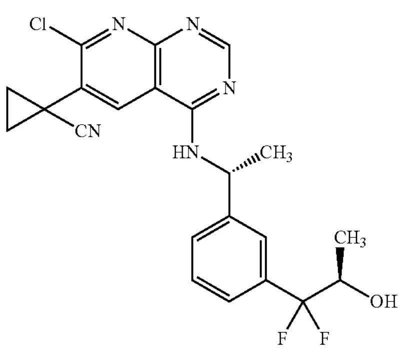 [SMILES: C[C@@H](Nc1ncnc2nc(Cl)c(C3(C#N)CC3)cc12)c1cccc(C(F)(F)[C@@H](C)O)c1] | >200 |
| 219 | 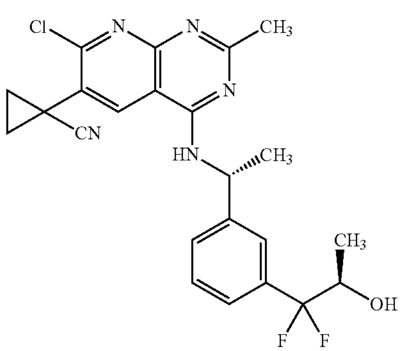 [SMILES: Cc1nc(N[C@H](C)c2cccc(C(F)(F)[C@@H](C)O)c2)c2cc(C3(C#N)CC3)c(Cl)nc2n1] | 99 |

TABLE 5-continued

| Compound No. | Structure | DMPK-invitro-metabolic Stability (Mouse T1/2) [min] |
|---|---|---|
| 417 | 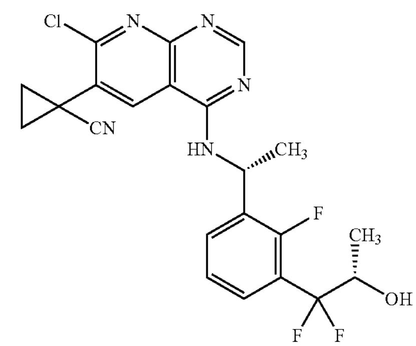 [SMILES: C[C@H](O)C(F)(F)c1cccc([C@@H](C)Nc2ncnc3nc(Cl)c(C4(C#N)CC4)cc23)c1F] | >200 |
| 220 | 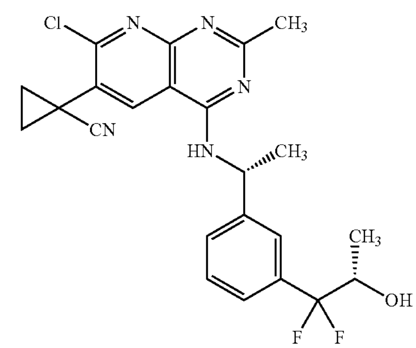 [SMILES: Cc1nc(N[C@H](C)c2cccc(C(F)(F)[C@H](C)O)c2)c2cc(C3(C#N)CC3)c(Cl)nc2n1] | 100.4 |
| 264 | 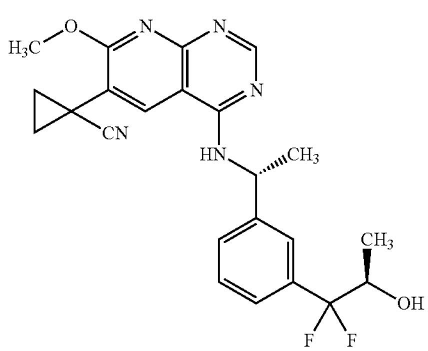 [SMILES: COc1nc2ncnc(N[C@H](C)c3cccc(C(F)(F)[C@@H](C)O)c3)c2cc1C1(C#N)CC1] | 55.1 |
| 366 | 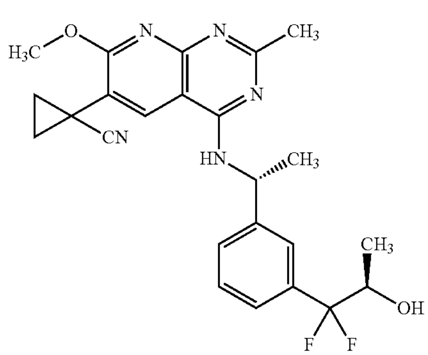 [SMILES: COc1nc2nc(C)nc(N[C@H](C)c3cccc(C(F)(F)[C@@H](C)O)c3)c2cc1C1(C#N)CC1] | 25.7 |

TABLE 5-continued

| Compound No. | Structure | DMPK-invitro-metabolic Stability (Mouse T1/2) [min] |
|---|---|---|
| 365 | 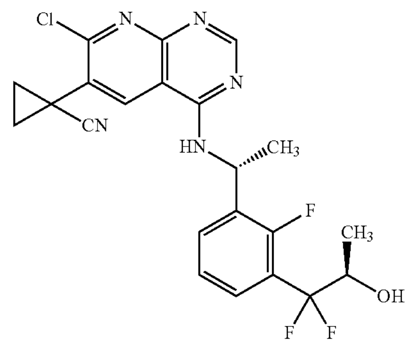 [SMILES: C[C@@H](Nc1ncnc2nc(Cl)c(C3(C#N)CC3)cc12)c1cccc(C(F)(F)[C@@H](C)O)c1F] | >200 |

The above direct comparison (compound pairs differ only at R7) clearly demonstrates that the subject compounds having R7 being H exhibit significantly longer metabolic stability as ascertained by the T½ of liver microsomal metabolism (see Example 12 for experimental procedures). In some instances, a remarkable increase in T½ by at least, 10%, 20%, 30%, 40%, 50%, 100%, 200%, 300%, 400%, or even higher is observed. Such unexpected, superior structure and correlated functional attribute is observed in a variety of compounds of Formula (I-1), (I'-1), (Ia-1), or (Ia'-1), where R7 is hydrogen. In particular, such unexpected property is observed in compounds of Formula (I-1), (I'-1), (Ia-1), or (Ia'-1), wherein $R^3$ is selected from $C_{3-14}$cycloalkyl optionally substituted with one, two, or three $R^{20b}$, wherein each $R^{20b}$ is independently selected from $C_{1-6}$alkyl, —CN, and $C_{2-9}$heterocycloalkyl. Of particular significance is that such superior property is embodied in compounds of Formula (I-1), (I'-1), (Ia-1), or (Ia'-1), wherein $R^3$ is cyclopropyl, optionally substituted with one $R^{2b}$, where $R^{20b}$ is CN.

The above results further demonstrate an improved metabolic stability of compounds of Formula (I), (I'), (Ia), (Ia'), (I-1), (I'-1), (Ia-1), and (Ia'-1), wherein $R^1$ is independently selected from

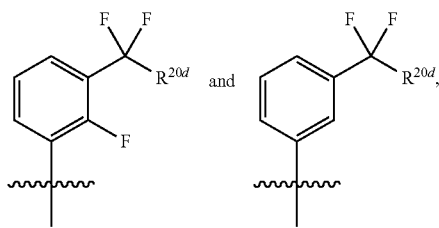

and wherein $R^{20d}$ is $C_{1-3}$alkyl substituted with one —OH, and one or two methyl. See comparative results of compound no. 362 relative to compound nos. 365, 417 or 361; and comparative results of compound no. 195 relative to compound no. 170; and also comparative results of compound no. 332 relative to compound no. 356. T½ of compounds having $R^{20d}$ as $C_{1-3}$alkyl that is substituted with one —OH and two methyl, is longer than that of a corresponding compound substituted with one methyl, and even longer than that of a corresponding compound without methyl at the corresponding position, regardless whether R7 is hydrogen or a non-hydrogen moiety such as methyl.

In some embodiments, compounds disclosed herein exhibit minimal cross reactivity to a wide spectrum of kinases, and hence with reduced possibility of undesired off-target side effects or drug-drug interaction. When tested against KINOMEscan scanEDGE™ 97Panel (commercially available via Euro Eurofins DiscoverX (USA), and further described in Example 17), compounds exemplified herein exhibit insignificant binding to any of the 97 tested kinase at 10 uM. Unlike other known core scaffolds such as quinazoline or the like, methyl substitution at the position corresponding to R7 of Formula (I), (I'), (Ia), (Ia'), (Ib), (Ib'), (Ic), (Ic'), (II), (II'), (III), (III'), (1-2), (I'-2), (Ia-2), (Ia'-2), (Ib-2), (Ib'-2), (Ic-2), or (Ic'-2), is not required to dial out cross-kinase activity, particularly anti-EGFR activity. It has been reported that a methyl substitution at the R7 position is essential in the context of the quinazoline core for mitigating EGFR and other kinase cross-reactivity (Ramharter et. al. J. Med Chem. 2021 64(10), 6569-6580). As demonstrated herein, a large number of exemplary compounds comprise H at R7, and exhibit one or more superior pharmacological and/or safety properties as compared to those compounds with substitutions at R7 of any of the formulae disclosed herein.

In some embodiments, superior DMPK properties are observed with compounds of Formula (I), (I'), (Ia), (Ia'), (Ib), (Ib'), (Ic), (Ic'), (II), (II'), (III), (III'), (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), wherein $R^3$ is cyclopropyl optionally substituted one or more CN. In some embodiments, superior DMPK properties are observed with compounds of Formula (I), (I'), (Ia), (Ia'), (Ib), (Ib'), (Ic), (Ic'), (II), (II'), (III), (III'), (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), where $R^3$ is cyclopropyl substituted with one CN. In some embodiments, superior DMPK properties are observed with compounds of Formula (I), (I'), (Ia), (Ia'), (Ib), (Ib'), (Ic), (Ic'), (II), (II'), (III), (III'), (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), wherein $R^3$ is cyclopropyl substituted with one CN, wherein $R^1$ is independently selected from

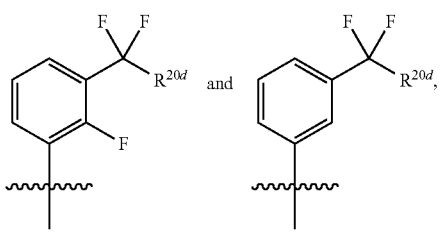

and wherein $R^{20d}$ is $C_{1-3}$alkyl substituted with one —OH, and one or two methyl.

Such compounds exhibit improved cell permeability, oral exposure, and/or reduced hERG liability. In particular, such compounds exhibit a PAMPA value great than −6 (e.g., −5 is considered greater than −6), with much higher permeability as compared to corresponding compounds having $R^3$ as a $C_6$heterocycloalkyl including sulfone-containing $C_6$heterocycloalkyl. In addition, such compounds exhibt less hERG liability (see Example 15 for experimental procedures) as compared to corresponding compounds having $R^3$ as a $C_6$heterocycloalkyl including a piperidinyl group or a piperazinyl group.

Further Forms of Compounds Disclosed Herein

Isomers

Furthermore, in some embodiments, the compounds described herein exist as geometric isomers. In some embodiments, the compounds described herein possess one or more double bonds. The compounds presented herein include all cis, trans, syn, anti, entgegen (E), and zusammen (Z) isomers as well as the corresponding mixtures thereof. In some situations, compounds exist as tautomers. The compounds described herein include all possible tautomers within the formulas described herein. In some situations, the compounds described herein possess one or more chiral centers and each center exists in the R configuration or S configuration. The compounds described herein include all diastereomeric, enantiomeric, and epimeric forms as well as the corresponding mixtures thereof. In additional embodiments of the compounds and methods provided herein, mixtures of enantiomers and/or diastereoisomers, resulting from a single preparative step, combination, or interconversion, are useful for the applications described herein. In some embodiments, the compounds described herein are prepared as optically pure enantiomers by chiral chromatographic resolution of the racemic mixture. In some embodiments, the compounds described herein are prepared as their individual stereoisomers by reacting a racemic mixture of the compound with an optically active resolving agent to form a pair of diastereoisomeric compounds, separating the diastereomers, and recovering the optically pure enantiomers. In some embodiments, dissociable complexes are preferred (e.g., crystalline diastereomeric salts). In some embodiments, the diastereomers have distinct physical properties (e.g., melting points, boiling points, solubilities, reactivity, etc.) and are separated by taking advantage of these dissimilarities. In some embodiments, the diastereomers are separated by chiral chromatography, or preferably, by separation/resolution techniques based upon differences in solubility. In some embodiments, the optically pure enantiomer is then recovered, along with the resolving agent, by any practical means that does not result in racemization.

Labeled Compounds

In some embodiments, the compounds described herein exist in their isotopically-labeled forms. In some embodiments, the methods disclosed herein include methods of treating diseases by administering such isotopically-labeled compounds. In some embodiments, the methods disclosed herein include methods of treating diseases by administering such isotopically-labeled compounds as pharmaceutical compositions. Thus, in some embodiments, the compounds disclosed herein include isotopically-labeled compounds, which are identical to those recited herein, but for the fact that one or more atoms are replaced by an atom having an atomic mass or mass number different from the atomic mass or mass number usually found in nature. Examples of isotopes that are incorporated into compounds described herein include isotopes of hydrogen, carbon, nitrogen, oxygen, phosphorous, sulfur, fluorine, and chloride, such as $^2H$, $^3H$, $^{13}C$, $^{14}C$, $^{15}N$, $^{17}O$, $^{18}O$, $^{31}P$, $^{32}P$, $^{35}S$, $^{18}F$, and $^{36}Cl$, respectively. Compounds described herein, and pharmaceutically acceptable salts, esters, solvate, hydrates, or derivatives thereof which contain the aforementioned isotopes and/or other isotopes of other atoms are within the scope of this invention. Certain isotopically-labeled compounds, for example those into which radioactive isotopes such as $^3H$ and $^{14}C$ are incorporated, are useful in drug and/or substrate tissue distribution assays. Tritiated, i. e., $^3H$ and carbon-14, i.e., $^{14}C$, isotopes are particularly preferred for their ease of preparation and detectability. Further, substitution with heavy isotopes such as deuterium, i.e., $^2H$, produces certain therapeutic advantages resulting from greater metabolic stability, for example increased in vivo half-life or reduced dosage requirements. In some embodiments, the isotopically labeled compounds, pharmaceutically acceptable salt, ester, solvate, hydrate, or derivative thereof is prepared by any suitable method.

In some embodiments, the compounds described herein are labeled by other means, including, but not limited to, the use of chromophores or fluorescent moieties, bioluminescent labels, or chemiluminescent labels.

Pharmaceutically Acceptable Salts

In some embodiments, the compounds described herein exist as their pharmaceutically acceptable salts. In some embodiments, the methods disclosed herein include methods of treating diseases by administering such pharmaceutically acceptable salts. In some embodiments, the methods disclosed herein include methods of treating diseases by administering such pharmaceutically acceptable salts as pharmaceutical compositions.

In some embodiments, the compounds described herein possess acidic or basic groups and therefore react with any of a number of inorganic or organic bases, and inorganic and organic acids, to form a pharmaceutically acceptable salt. In some embodiments, these salts are prepared in situ during the final isolation and purification of the compounds described herein, or by separately reacting a purified compound in its free form with a suitable acid or base, and isolating the salt thus formed.

Solvates

In some embodiments, the compounds described herein exist as solvates. In some embodiments are methods of treating diseases by administering such solvates. Further described herein are methods of treating diseases by administering such solvates as pharmaceutical compositions.

Solvates contain either stoichiometric or non-stoichiometric amounts of a solvent, and, in some embodiments, are formed during the process of crystallization with pharmaceutically acceptable solvents such as water, ethanol, and the like. Hydrates are formed when the solvent is water, or alcoholates are formed when the solvent is alcohol. Solvates of the compounds described herein are conveniently prepared or formed during the processes described herein. By way of example only, hydrates of the compounds described herein are conveniently prepared by recrystallization from an aqueous/organic solvent mixture, using organic solvents including, but not limited to, dioxane, tetrahydrofuran, or MeOH. In addition, the compounds provided herein exist in unsolvated as well as solvated forms. In general, the solvated forms are considered equivalent to the unsolvated forms for the purposes of the compounds and methods provided herein.

In an aspect is provided a compound having the formula A-$L^{AB}$-B wherein
A is a monovalent form of a compound described herein;
$L^{AB}$ is a covalent linker bonded to A and B; and
B is a monovalent form of a degradation enhancer.

A "degradation enhancer" is a compound capable of binding a ubiquitin ligase protein (e.g., E3 ubiquitin ligase protein) or a compound capable of binding a protein that is capable of binding to a ubiquitin ligase protein to form a protein complex capable of conjugating a ubiquitin protein to a target protein. In embodiments, the degradation enhancer is capable of binding to an E3 ubiquitin ligase protein or a protein complex comprising an E3 ubiquitin ligase protein. In embodiments, the degradation enhancer is capable of binding to an E2 ubiquitin-conjugating enzyme. In embodiments, the degradation enhancer is capable of binding to a protein complex comprising an E2 ubiquitin-conjugating enzyme and an E3 ubiquitin ligase protein.

In embodiments, the degradation enhancer is capable of binding a protein selected from E3A, mdm2, APC, EDD1, SOCS/BC-box/eloBC/CUL5/RING, LNXp80, CBX4, CBLL1, HACE1, HECTD1, HECTD2, HECTD3, HECTD4, HECW1, HECW2, HERC1, HERC2, HERC3, HERC4, HER5, HERC6, HUWE1, ITCH, NEDD4, NEDD4L, PPIL2, PRPF19, PIAS1, PIAS2, PIAS3, PIAS4, RANBP2, RNF4, RBX1, SMURF1, SMURF2, STUB1, TOPORS, TRIP12, UBE3A, UBE3B, UBE3C, UBE3D, UBE4A, UBE4B, UBOX5, UBR5, VHL (von-Hippel-Lindau ubiquitin ligase), WWP1, WWP2, Parkin, MKRN1, CMA (chaperon-mediated autophage), SCFb-TRCP (Skip-Cullin-F box (Beta-TRCP) ubiquitin complex), b-TRCP (b-transducing repeat-containing protein), cIAP1 (cellular inhibitor of apoptosis protein 1), APC/C (anaphase-promoting complex/cyclosome), CRBN (cereblon), CUL4-RBX1-DDB1-CRBN ($CRL4^{CRBN}$) ubiquitin ligase, XIAP, IAP, KEAP1, DCAF15, RNF114, DCAF16, AhR, SOCS2, KLHL12, UBR2, SPOP, KLHL3, KLHL20, KLHDC2, SPSB1, SPSB2, SPSB4, SOCS6, FBXO4, FBXO31, BTRC, FBW7, CDC20, PML, TRIM21, TRIM24, TRIM33, GID4, avadomide, iberdomide, and CC-885.

In embodiments, the degradation enhancer is capable of binding a protein selected from UBE2A, UBE2B, UBE2C, UBE2D1, UBE2D2, UBE2D3, UBE2DR, UBE2E1, UBE2E2, UBE2E3, UBE2F, UBE2G1, UBE2G2, UBE2H, UBE2I, UBE2J1, UBE2J2, UBE2K, UBE2L3, UBE2L6, UBE2L1, UBE2L2, UBE2L4, UBE2M, UBE2N, UBE2O, UBE2Q1, UBE2Q2, UBE2R1, UBE2R2, UBE2S, UBE2T, UBE2U, UBE2V1, UBE2V2, UBE2W, UBE2Z, ATG3, BIRC6, and UFC1.

In embodiments, the degradation enhancer is a compound described in Ishida and Ciulli, SLAS Discovery 2021, Vol. 25(4) 484-502, which is incorporated by reference in its entirety for any purpose, for example VH032, VH101, VH298, thalidomide, bestatin, methyl bestatin, nutlin, idasanutlin, bardoxolone, bardoxolone methyl, indisulam (E7070), E7820, chloroquinoxaline sulfonamide (CQS), nimbolide, KB02, ASTX660, lenalidomide, or pomalidomide.

In embodiments, the degradation enhancer is a compound described in US20180050021, WO2016146985, WO2018189554, WO2018119441, WO2018140809, WO2018119448, WO2018119357, WO2018118598, WO2018102067, WO201898280, WO201889736, WO201881530, WO201871606, WO201864589, WO201852949, WO2017223452, WO2017204445, WO2017197055, WO2017197046, WO2017180417, WO2017176958, WO201711371, WO2018226542, WO2018223909, WO2018189554, WO2016169989, WO2016146985, CN105085620B, CN106543185B, U.S. Pat. Nos. 10,040,804, 9,938,302, 10,144,745, 10,145,848, 9,938,264, 9,632,089, 9,821,068, 9,758,522, 9,500,653, 9,765,019, 8,507,488, 8,299,057, US20180298027, US20180215731, US20170065719, US20170037004, US20160272639, US20150291562, or US20140356322, which are incorporated by reference in their entirety for any purpose.

In embodiments $L^{AB}$ is -$L^{AB1}$-$L^{AB2}$-$L^{AB3}$-$L^{AB4}$-$L^{AB5}$-.
$L^{AB1}$, $L^{AB2}$, $L^{AB3}$, $L^{AB4}$, and $L^{AB5}$ are independently a bond, —O—, —N($R^{14}$)—, —C(O)—, —N($R^{14}$)C(O)—, —C(O)N($R^{14}$)—, —S—, —S(O)$_2$—, —S(O)—, —S(O)$_2$N($R^{14}$)—, —S(O)N($R^{14}$)—, —N($R^{14}$)S(O)—, —N($R^{14}$)S(O)$_2$—, $C_{1-6}$alkylene, (—O—$C_{1-6}$alkyl)$_z$-, (—$C_{1-6}$alkyl-O)$_z$—, $C_{2-6}$alkenylene, $C_{2-6}$alkynylene, $C_{1-6}$haloalkylene, $C_{3-12}$cycloalkylene, $C_{1-11}$heterocycloalkylene, $C_{6-12}$arylene, or $C_{1-11}$heteroarylene, wherein $C_{1-6}$alkylene, $C_{2-6}$alkenylene, $C_{2-6}$alkynylene, $C_{1-6}$haloalkylene, $C_{3-12}$cycloalkylene, $C_{1-11}$heterocycloalkylene, $C_{6-12}$arylene, or $C_{1-11}$ heteroarylene, are optionally substituted with one, two, or three $R^{20j}$; wherein each $C_{1-6}$alkyl of (—O—$C_{1-6}$alkyl)$_z$- and (—$C_{1-6}$alkyl-O)$_z$— is optionally substituted with one, two, or three $R^{20j}$;

z is independently an integer from 0 to 10;

each $R^{12}$ is independently selected from hydrogen, $C_{1-6}$alkyl, $C_{2-6}$alkenyl, $C_{2-6}$alkynyl, $C_{3-6}$cycloalkyl, —CH$_2$—$C_{3-6}$cycloalkyl, $C_{2-9}$heterocycloalkyl, —CH$_2$—$C_{2-9}$heterocycloalkyl, $C_{6-10}$aryl, —CH$_2$—$C_{6-10}$aryl, —CH$_2$—$C_{1-9}$heteroaryl, and $C_{1-9}$heteroaryl, wherein $C_{1-6}$ alkyl, $C_{2-6}$alkenyl, $C_{2-6}$alkynyl, $C_{3-6}$cycloalkyl, —CH$_2$—$C_{3-6}$cycloalkyl, $C_{2-9}$heterocycloalkyl, —CH$_2$—$C_{2-9}$heterocycloalkyl, $C_{6-10}$aryl, —CH$_2$—$C_{6-10}$aryl, —CH$_2$—$C_{1-9}$heteroaryl, and $C_{1-9}$heteroaryl are optionally substituted with one, two, or three $R^{20a}$;

each $R^{13}$ is independently selected from hydrogen, $C_{1-6}$alkyl, and $C_{1-6}$haloalkyl; or $R^{12}$ and $R^{13}$, together with the nitrogen to which they are attached, form a $C_{2-9}$heterocycloalkyl ring optionally substituted with one, two, or three $R^{20e}$;

each $R^{14}$ is independently selected from hydrogen, $C_{1-6}$alkyl, and $C_{1-6}$haloalkyl;

each $R^{15}$ is independently selected $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$ heteroaryl, wherein $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl are optionally substituted with one, two, or three $R^{20f}$;

each $R^{20a}$, $R^{20e}$, $R^{20f}$, and $R^{20j}$ are each independently selected from halogen, —CN, $C_{1-6}$alkyl, $C_{2-6}$alkenyl, $C_{2-6}$alkynyl, $C_{3-6}$cycloalkyl, —CH$_2$—$C_{3-6}$cycloalkyl, $C_{2-9}$heterocycloalkyl, —CH$_2$—$C_{2-9}$heterocycloalkyl, $C_{6-10}$aryl, —CH$_2$—$C_{6-10}$aryl, —CH$_2$—$C_{1-9}$heteroaryl, $C_{1-9}$ heteroaryl, —OR$^{21}$, —SR$^{21}$, —N(R$^{22}$)(R$^{23}$), —C(O)OR$^{22}$, —C(O)N(R$^{22}$)(R$^{23}$), —C(O)C(O)N(R$^{22}$)(R$^{23}$), —OC(O)N(R$^{22}$)(R$^{23}$), —N(R$^{24}$)C(O)N(R$^{22}$)(R$^{23}$), —N(R$^{24}$)C(O)OR$^{25}$, —N(R$^{24}$)C(O)R$^{25}$, —N(R$^{24}$)S(O)$_2$R$^{25}$, —C(O)R$^{25}$, —S(O)$_2$R$^{25}$, —S(O)$_2$N(R$^{22}$)(R$^{23}$), —OCH₂C(O)OR²², and —OC(O)R²⁵, wherein C₁₋₆alkyl, C₂₋₆alkenyl, C₂₋₆alkynyl, C₃₋₆cycloalkyl, —CH₂—C₃₋₆cycloalkyl, C₂₋₉heterocycloalkyl, —CH₂—C₂₋₉heterocycloalkyl, C₆₋₁₀aryl, —CH₂—C₆₋₁₀aryl, —CH₂—C₁₋₉heteroaryl, and C₁₋₉heteroaryl are optionally substituted with one, two, or three groups independently selected from halogen, oxo, —CN, C₁₋₆alkyl, C₁₋₆haloalkyl, C₁₋₆alkoxy, C₁₋₆haloalkoxy, —OR²¹, —SR²¹, —N(R²²)(R²³), —C(O)OR²², —C(O)N(R²²)(R²³), —C(O)C(O)N(R²²)(R²³), —OC(O)N(R²²)(R²³), —N(R²⁴)C(O)N(R²²)(R²³), —N(R²⁴)C(O)OR²⁵, —N(R²⁴)C(O)R²⁵, —N(R²⁴)S(O)₂R²⁵, —C(O)R²⁵, —S(O)₂R²⁵, —S(O)₂N(R²²)(R²³), and —OC(O)R²⁵;

each R²¹ is independently selected from H, C₁₋₆alkyl, C₁₋₆haloalkyl, C₂₋₆alkenyl, C₂₋₆alkynyl, C₃₋₆cycloalkyl, C₂₋₉heterocycloalkyl, C₆₋₁₀aryl, and C₁₋₉heteroaryl;

each R²² is independently selected from H, C₁₋₆alkyl, C₁₋₆haloalkyl, C₂₋₆alkenyl, C₂₋₆alkynyl, C₃₋₆cycloalkyl, C₂₋₉heterocycloalkyl, C₆₋₁₀aryl, and C₁₋₉heteroaryl;

each R²³ is independently selected from H and C₁₋₆alkyl;

each R²⁴ is independently selected from H and C₁₋₆alkyl; and each R²⁵ is selected from C₁₋₆alkyl, C₂₋₆alkenyl, C₂₋₆alkynyl, C₃₋₆cycloalkyl, C₂₋₉heterocycloalkyl, C₆₋₁₀aryl, and C₁₋₉heteroaryl.

In embodiments, $L^{AB}$ is —(O—C₂alkyl)$_z$- and z is an integer from 1 to 10.

In embodiments, $L^{AB}$ is —(C₂alkyl-O—)$_z$— and z is an integer from 1 to 10.

In embodiments, $L^{AB}$ is —(CH₂)$_{zz1}$L$^{AB2}$(CH₂O)$_{zz2}$—, wherein L$^{AB2}$ is a bond, a 5 or 6 membered heterocycloalkylene or heteroarylene, phenylene, —(C₂-C₄)alkynylene, —SO₂— or —NH—; and zz1 and zz2 are independently an integer from 0 to 10.

In embodiments, $L^{AB}$ is —(CH₂)$_{zz1}$(CH₂O)$_{zz2}$—, wherein zz1 and zz2 are each independently an integer from 0 to 10.

In embodiments, $L^{AB}$ is a PEG linker (e.g., divalent linker of 1 to 10 ethylene glycol subunits).

In embodiments, B is a monovalent form of a compound selected from

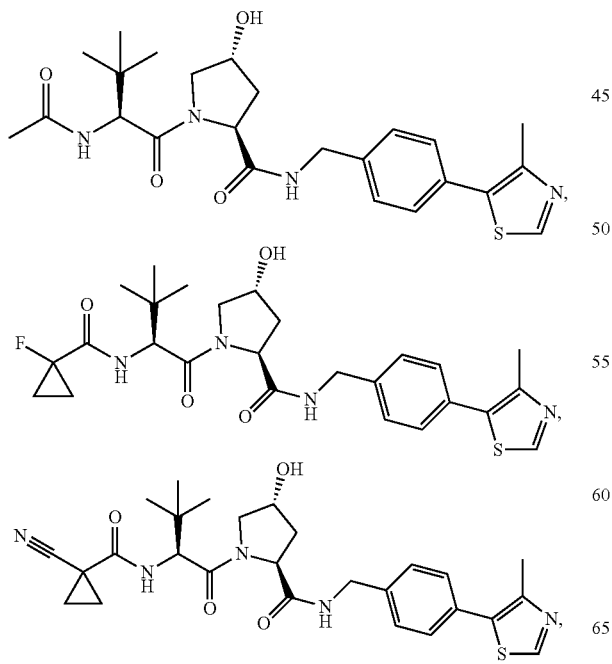

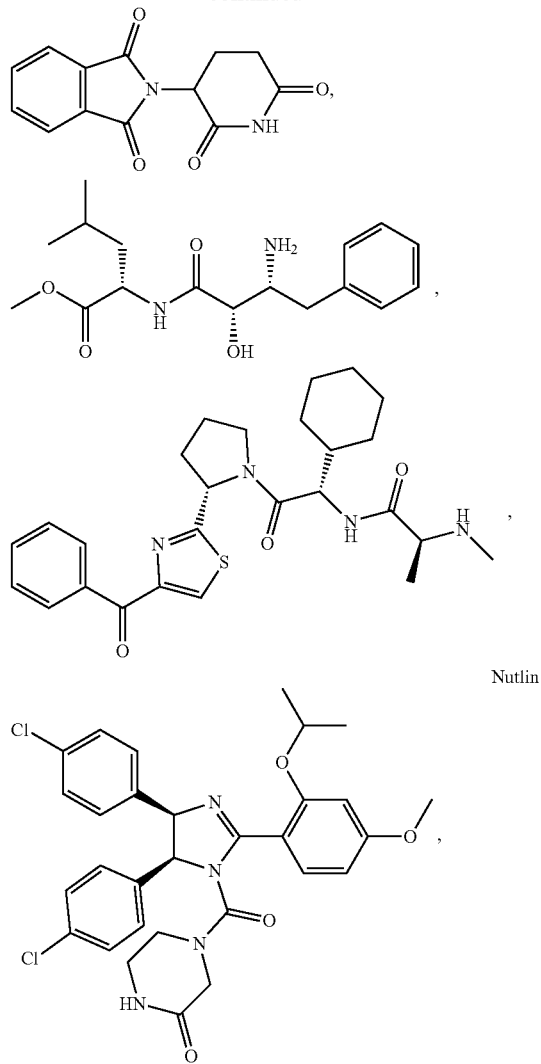

Nutlin

Idasanutlin

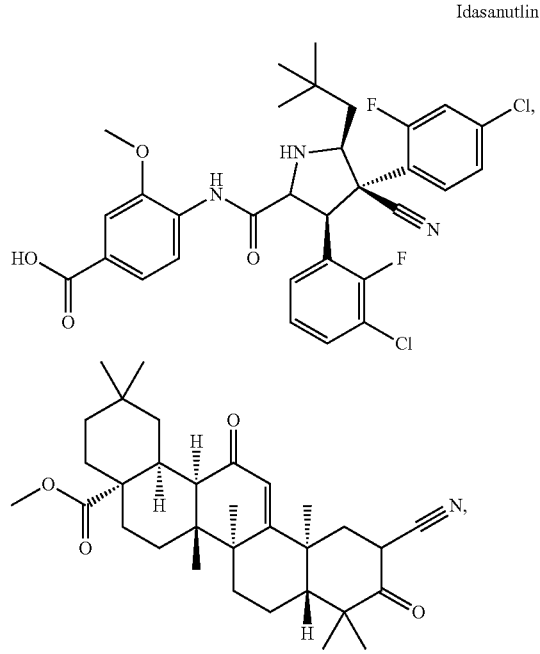

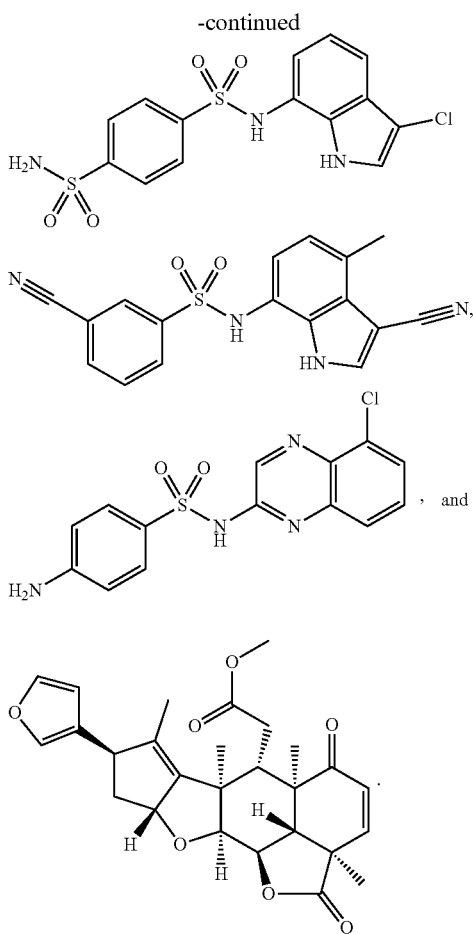

Synthesis of Compounds

In some embodiments, the synthesis of compounds described herein are accomplished using means described in the chemical literature, using the methods described herein, or by a combination thereof. In addition, solvents, temperatures and other reaction conditions presented herein may vary.

In other embodiments, the starting materials and reagents used for the synthesis of the compounds described herein are synthesized or are obtained from commercial sources, such as, but not limited to, Sigma-Aldrich, FischerScientific (Fischer Chemicals), and AcrosOrganics.

In further embodiments, the compounds described herein, and other related compounds having different substituents are synthesized using techniques and materials described herein as well as those that are recognized in the field, such as described, for example, in Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991), Larock's Comprehensive Organic Transformations (VCH Publishers Inc., 1989), March, Advanced Organic Chemistry 4$^{th}$ Ed., (Wiley 1992); Carey and Sundberg, Advanced Organic Chemistry 4$^{th}$ Ed., Vols. A and B (Plenum 2000, 2001), and Green and Wuts, Protective Groups in Organic Synthesis 3$^{rd}$ Ed., (Wiley 1999) (all of which are incorporated by reference for such disclosure). General methods for the preparation of compound as disclosed herein may be derived from reactions and the reactions may be modified by the use of appropriate reagents and conditions, for the introduction of the various moieties found in the formulae as provided herein. In some embodiments, the following synthetic methods may be utilized.

General synthetic method for Formula (Ia)

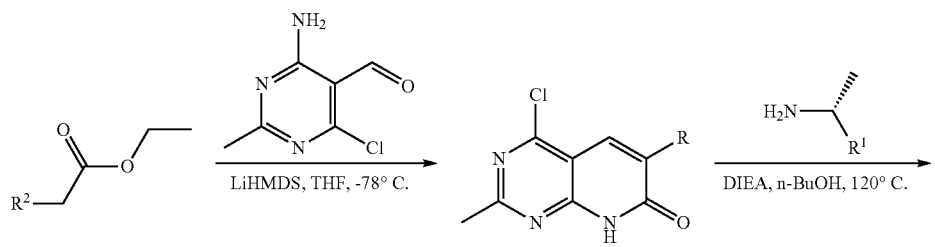

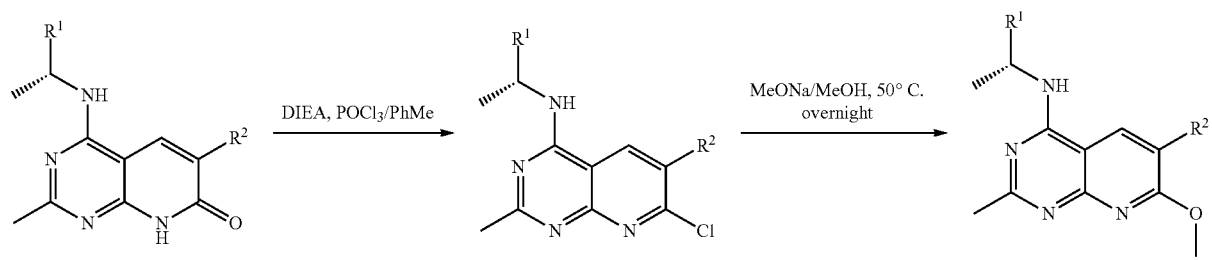

-continued
Alternative general scheme for formula (Ia)
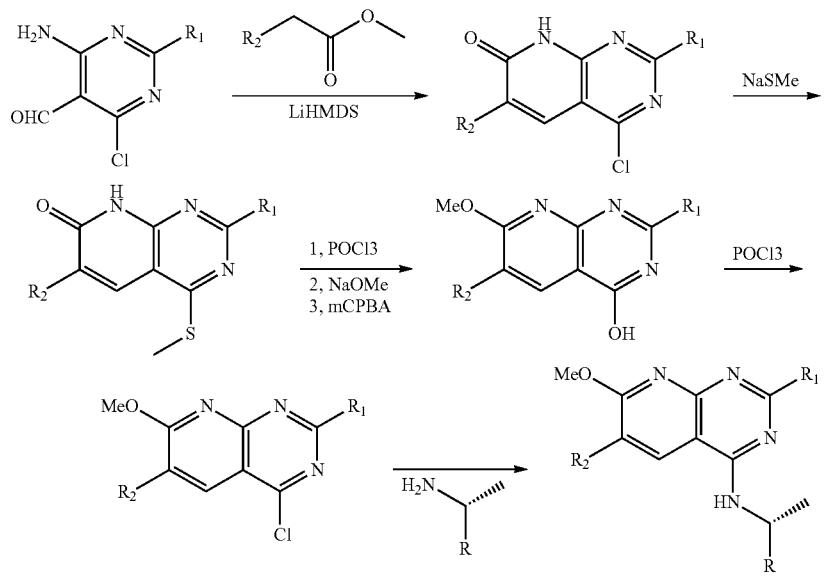
Alternative general Scheme for formula (Ia)
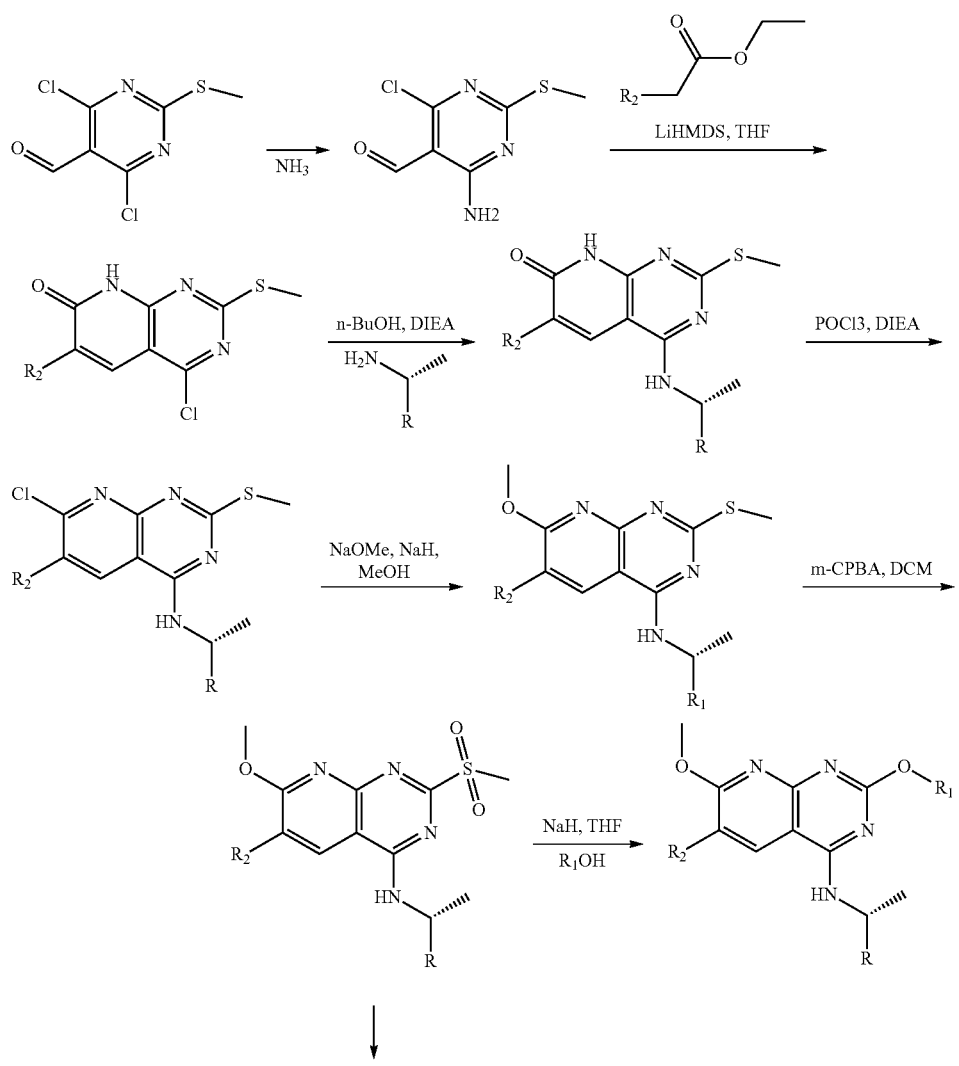

-continued
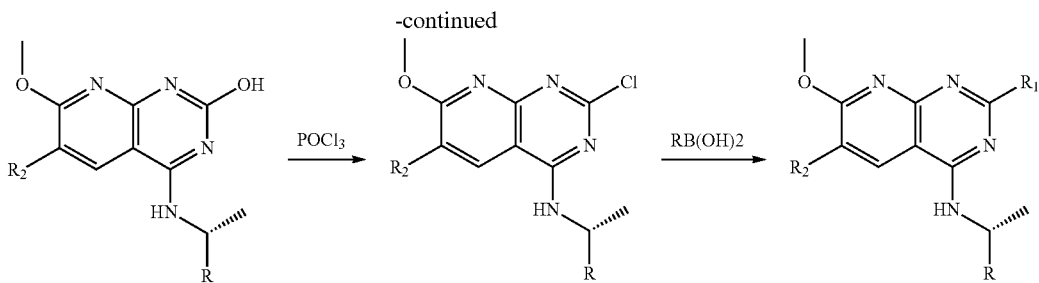
General synthetic method for Formula (Ib)
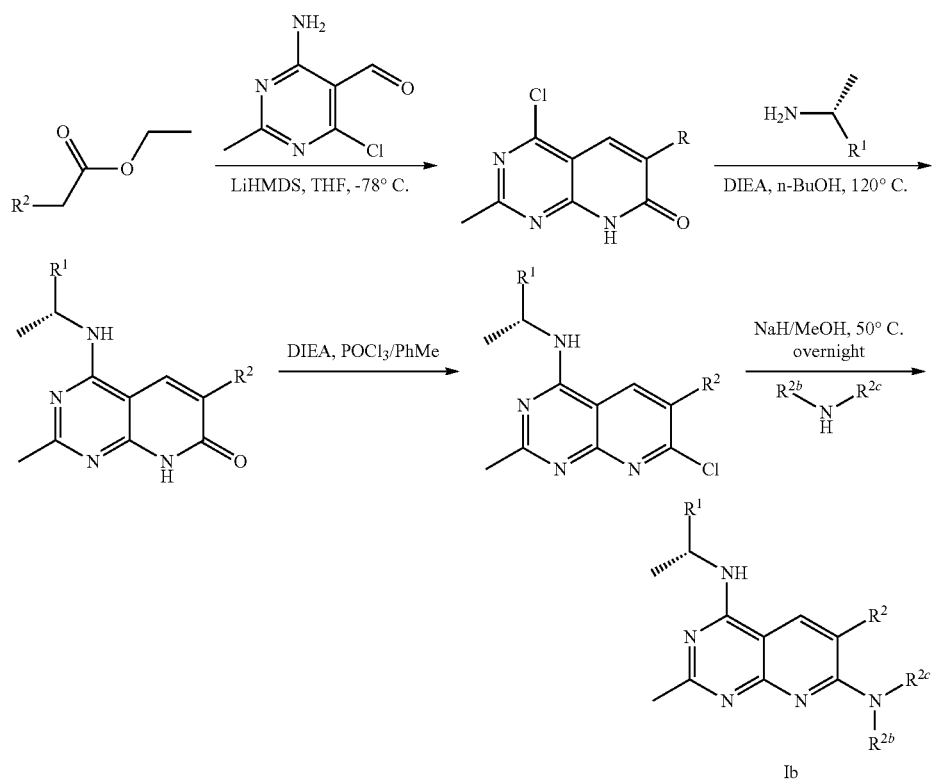
General synthetic method for Formula (Ic)
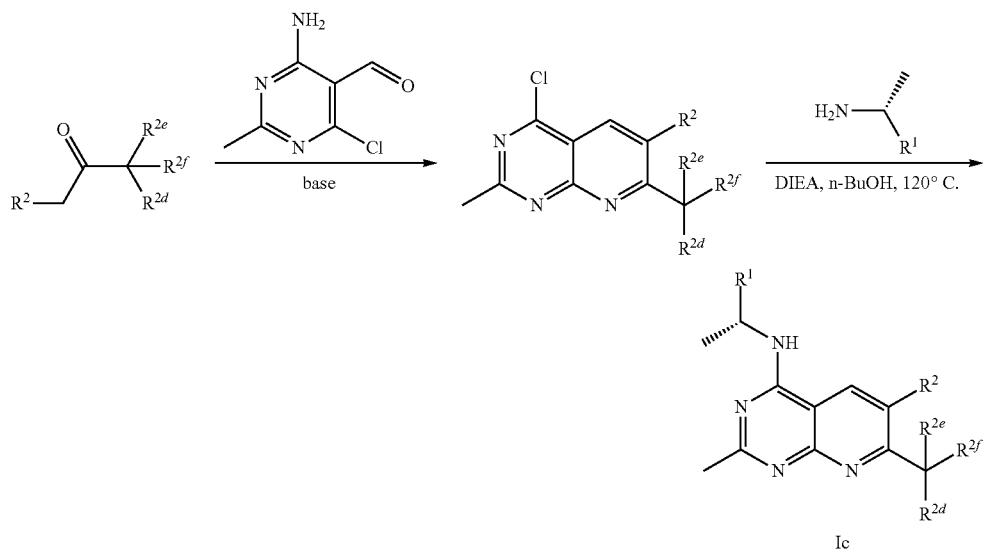

-continued
General synthetic method for Formula (II)
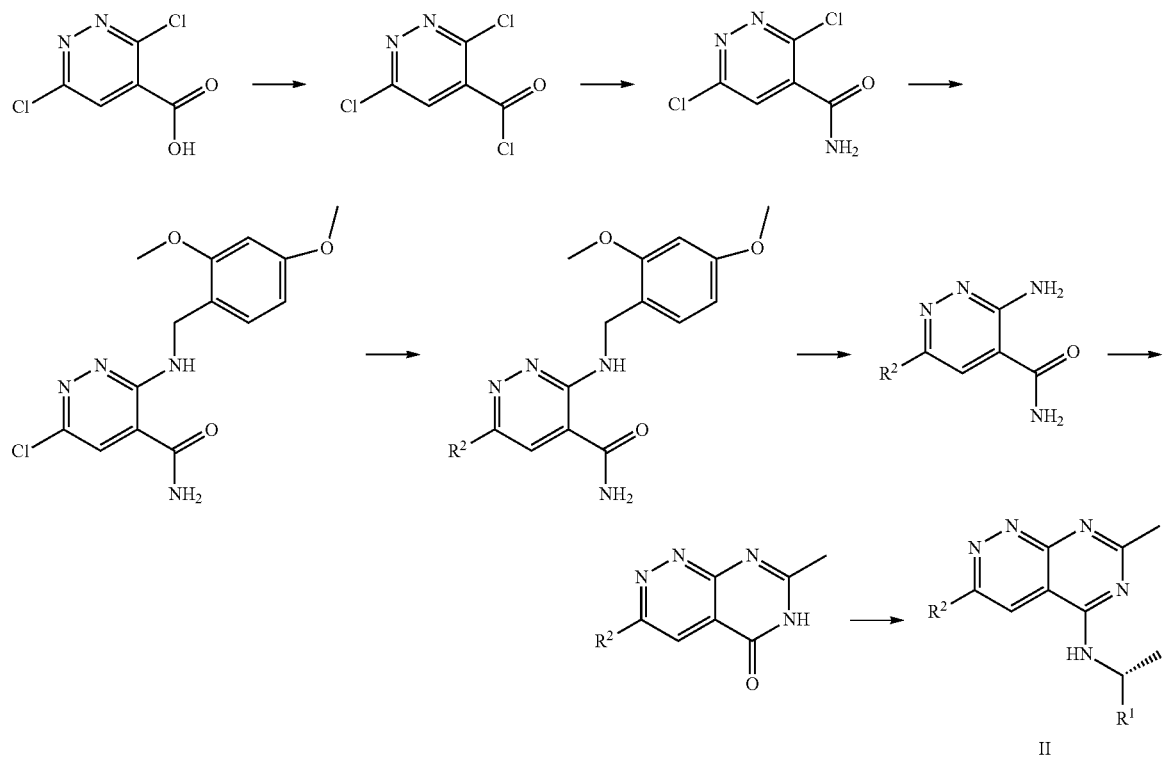
II
General synthetic method for Formula (III)
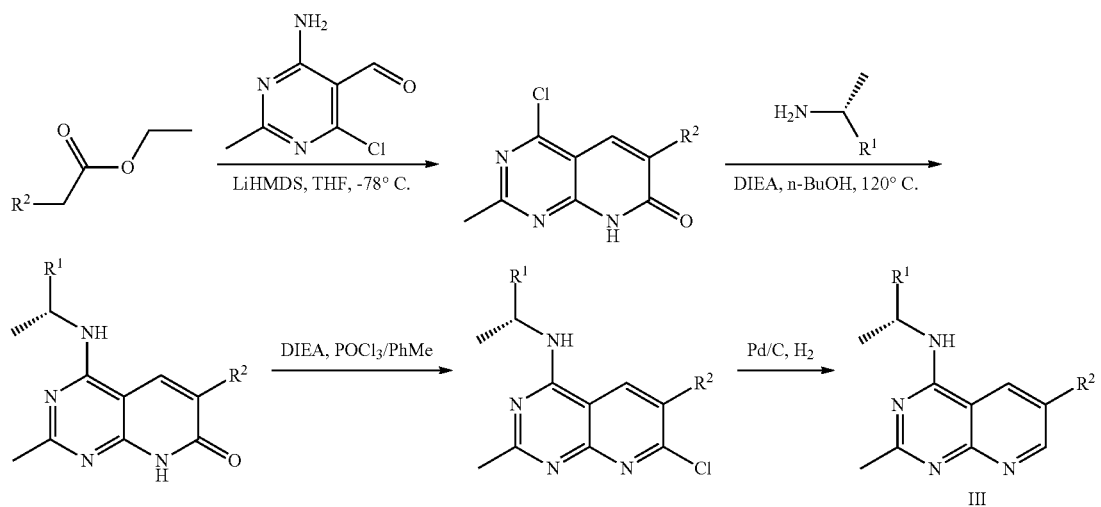
III
Alternative synthetic method for Formula (III)
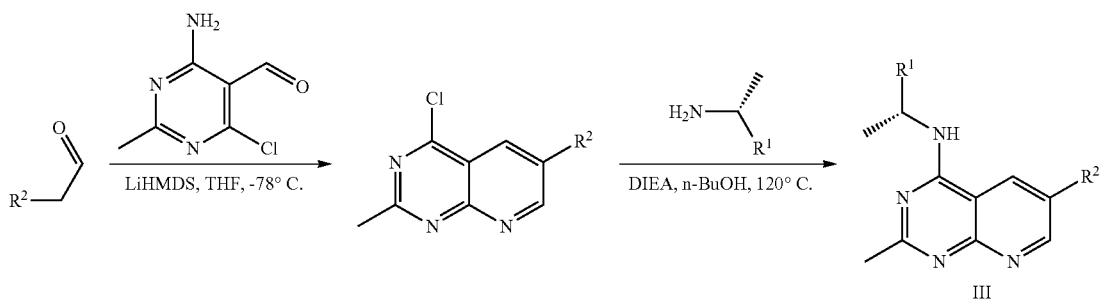
III In some embodiments, the compounds of the present invention exhibit one or more functional characteristics disclosed herein. For example, a subject compound is capable of reducing Ras signaling output. In some instances, a subject compound is capable of disrupting Ras-SOS interaction, including disrupting interaction or binding between a mutant Kras (e.g., Kras G12C) and SOS1, or between a wildtype Kras and SOS1, thereby reducing Ras signaling output. In some embodiments, a subject compound binds specifically to a SOS protein, including SOS1. In some embodiments, the IC50 of a subject compound (including those shown in Table 1) for a SOS protein is less than about less than about 5 uM, less than about 1 uM, less than about 50 nM, less than about 10 nM, less than about 1 nM, less than about 0.5 nM, less than about 100 pM, or less than about 50 pM, as measured in an in vitro assay known in the art or exemplified herein.

A reduction in Ras signaling output can be evidenced by one or more members of the following: (i) an increase in steady state level of GDP-bound Ras protein; (ii) a reduction of phosphorylated AKTs473, (iii) a reduction of phosphorylated ERKT202/y204, (iv) a reduction of phosphorylated S6S235/236, (v) reduction (e.g., inhibition) of cell growth of Ras-driven tumor cells (e.g., those derived from a tumor cell line disclosed herein), and (vi) an interference or disruption of the interaction or binding between a SOS protein (e.g., SOS1) with a Ras protein such as a wildtype or a mutant Ras. In some cases, the reduction in Ras signaling output can be evidenced by two, three, four, five, or all of (i)-(vi) above.

It shall be understood that different aspects of the invention can be appreciated individually, collectively, or in combination with each other. Various aspects of the invention described herein may be applied to any of the particular applications disclosed herein. The compositions of matter including compounds of any formulae disclosed herein in the composition section of the present disclosure may be utilized in the method section including methods of use and production disclosed herein, or vice versa.

Methods

In an aspect is provided a method of treating cancer in a subject in need thereof, comprising administering to the subject a therapeutically effective amount of a compound described herein, or a pharmaceutically acceptable salt or solvate thereof.

In some embodiments, the cancer is a solid tumor or a hematological cancer.

In some embodiments, the subject is administered with an additional agent or therapy.

In an aspect is provided a method of reducing Ras signaling output, comprising contacting a SOS1 protein with an effective amount of a compound described herein, or a pharmaceutically acceptable salt or solvate thereof, thereby reducing the Ras signaling output.

In some embodiments, the compound disrupts interaction between a Ras protein and SOS1.

In some embodiments, the Ras protein is a wildtype K-Ras or a mutant K-Ras.

In an aspect is provided a method of inhibiting cell growth, comprising administering a cell expressing SOS1 with an effective amount of a compound described herein, or a pharmaceutically acceptable salt or solvate thereof, thereby inhibiting growth of said cells.

In an aspect is provided a method of reducing Ras signaling output of a cell, comprising contacting the cell with an effective amount of a compound Formula (I), or a pharmaceutically acceptable salt or solvate thereof, in combination with an additional agent, wherein the additional agent is a chemotherapeutic agent, a radioactive agent, an immune modulator, or an inhibitor against one or more targets selected from the group of: MEK, epidermal growth factor receptor (EGFR), FGFR1, FGFR2, FGFR3, FGFR4, mitotic kinase, topoisomerase, ALK, c-MET, ErbB2, AXL, NTRK1, RET, A-Raf, B-Raf, C-Raf, ERK, MDM2, mTOR, BET, IGF1/2, IGF1-R, CDK9, SHC, GAB, GRB, PI3-kinase, MAPK, SHIP1, SHIP2, SHP1, SHP2, SRC, JAK, PARP, BTK, FLT3, HDAC, VEGFR, PDGFR, LCK, Bcr-Abl, AKT, wildtype KRas, KRas mutant (e.g., KrasG12C, KRas G12D, KRas G12S, KRas G12V, KRas G13D, KRas G13C, or KRas G13V), ROS1, CDK4/6, and a mutant of the one or more target thereof, wherein the compound of Formula (I) has the structure:

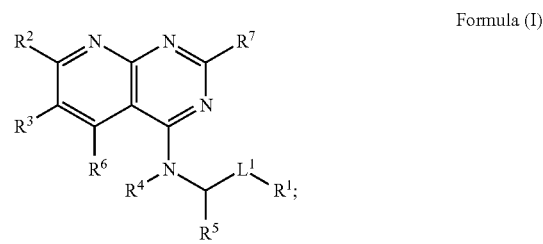

Formula (I)

wherein:
$R^1$ is a 3-12 membered cycloalkyl ring, 3-12 membered heterocycloalkyl ring, 6-10 membered aryl ring, or 5-10 membered heteroaryl ring, wherein the 3-12 membered cycloalkyl ring, 3-12 membered heterocycloalkyl ring, 6-10 membered aryl ring, and 5-10 membered heteroaryl ring are optionally substituted with one or more $R^{10}$;
$L^1$ is a bond or $C_{1-6}$alkyl;
$R^2$ is $-OR^{2a}$, $-NR^{2b}R^{2c}$, $-SR^{2g}$, $-S(O)R^{2h}$, $-S(O)_2R^{2h}$, $-S(O)_2NR^{2b}R^{2c}$, $-C(R^{2d})(R^{2e})(R^{2f})$, $C(O)NR^{2b}R^{2c}$, $-CN$, or halogen;
$R^{2a}$ is selected from hydrogen, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, $-C(O)OR^{12}$, $-C(O)R^{15}$, $-C(O)N(R^{12})(R^{13})$, $-S(O)_2R^{15}$, $-S(O)_2N(R^{12})(R^{13})$, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20a}$;
$R^{2b}$ is selected from hydrogen, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, $-C(O)OR^{12}$, $-C(O)R^{15}$, $-C(O)N(R^{12})(R^{13})$, $-S(O)_2R^{15}$, and $-S(O)_2N(R^{12})(R^{13})$, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20a}$;
$R^{2c}$ is selected from hydrogen, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20a}$; or $R^{2b}$ and $R^{2c}$, together with the nitrogen to which they are attached, form a $C_{2-9}$heterocycloalkyl ring optionally substituted with one, two, or three $R^{20a}$;
$R^{2d}$ is selected from hydrogen, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, $-OR^{12}$, $-SR^{12}$, $-N(R^{12})(R^{13})$, $-C(O)OR^{12}$, $-OC(O)N(R^{12})(R^{13})$, $-N(R^{14})C(O)N(R^{12})(R^{13})$, $-N(R^{14})C(O)OR^{15}$, $-N(R^{14})S(O)_2R^{15}$, $-C(O)R^{15}$, $-S(O)R^{15}$, $-OC(O)R^{15}$, $-C(O)N(R^{12})(R^{13})$, $-C(O)C(O)N(R^{12})(R^{13})$, $-N(R^{14})C(O)R^{15}$, $-S(O)_2R^{15}$, $-S(O)_2N(R^{12})(R^{13})$, $-S(=O)(=NH)N$ $(R^{12})(R^{13})$, $-CH_2C(O)N(R^{12})(R^{13})$, $-CH_2N(R^{14})C(O)R^{15}$, $-CH_2S(O)_2R^{15}$, $-CH_2S(O)_2N(R^{12})(R^{13})$, $-CH_2N(R^{12})S(O)_2(R^{13})$, and $-P(O)(R^{17})(R^{17a})$, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20a}$;

$R^{2e}$ is selected from hydrogen, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20a}$;

$R^{2f}$ is selected from hydrogen, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20a}$;

$R^{2g}$ is selected from hydrogen, $C_{2-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, $-C(O)OR^{12}$, $-C(O)R^{15}$, $-C(O)N(R^{12})(R^{13})$, $-S(O)_2R^{15}$, $-S(O)_2N(R^{12})(R^{13})$, wherein $C_{2-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20a}$;

$R^{2h}$ is selected from $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20a}$;

$R^3$ is selected from halogen, $C_{1-6}$alkyl, $C_{2-6}$alkenyl, $C_{2-6}$alkynyl, $C_{3-14}$cycloalkyl, $C_{2-9}$heterocycloalkyl, $C_{6-10}$aryl, $C_{1-9}$heteroaryl, $-SR^{12}$, $-N(R^{12})(R^{13})$, $-C(O)OR^{12}$, $-OC(O)N(R^{12})(R^{13})$, $-N(R^{14})C(O)N(R^{12})(R^{13})$, $-N(R^{14})C(O)OR^{15}$, $-N(R^{14})S(O)_2R^{15}$, $N(R^{14})S(O)R^{15}$, $-C(O)R^{15}$, $-S(O)R^{15}$, $-OC(O)R^{15}$, $-C(O)N(R^{12})(R^{13a})$, $-C(O)C(O)N(R^{12})(R^{13})$, $-N(R^{14})C(O)R^{15}$, $-S(O)_2R^{15}$, $-S(O)_2N(R^{12})(R^{13})$, $-S(O)N(R^{12})(R^{13})$, $-S(=O)(=NH)N(R^{12})(R^{13})$, $-CH_2C(O)N(R^{12})(R^{13})$, $-CH_2N(R^{14})C(O)R^{15}$, $-CH_2S(O)_2R^{15}$, $-CH_2S(O)_2N(R^{12})(R^{13})$, $-CH_2N(R^{12})S(O)_2(R^{13})$, $CH_2S(O)R^{15}$, $-CH_2S(O)N(R^{12})(R^{13})$, $-CH_2N(R^{12})S(O)(R^{13})$ and $-P(O)(R^{17})(R^{17a})$, wherein $C_{1-6}$alkyl, $C_{2-6}$alkenyl, $C_{2-6}$alkynyl, $C_{3-14}$cycloalkyl, $C_{2-9}$heterocycloalkyl, $C_{6-10}$aryl, and $C_{1-9}$heteroaryl are optionally substituted with one, two, or three $R^{20b}$;

$R^4$ is selected from hydrogen, $C_{1-6}$alkyl, and $C_{1-6}$haloalkyl;

$R^5$ is selected from hydrogen, $C_{1-6}$alkyl, and $C_{1-6}$haloalkyl;

$R^6$ is selected from hydrogen, halogen, $-CN$, $C_{1-6}$alkyl, $C_{2-6}$alkenyl, $C_{2-6}$alkynyl, $C_{3-10}$cycloalkyl, $C_{2-9}$heterocycloalkyl, $-OR^{12}$, $-SR^{12}$, $-N(R^{12})(R^{13})$, $-C(O)OR^{12}$, $-OC(O)N(R^{12})(R^{13})$, $-N(R^{14})C(O)N(R^{12})(R^{13})$, $-N(R^{14})C(O)OR^{15}$, $-N(R^{14})S(O)_2R^{15}$, $-C(O)R^{15}$, $-S(O)R^{15}$, $-OC(O)R^{15}$, $-C(O)N(R^{12})(R^{13})$, $-C(O)C(O)N(R^{12})(R^{13})$, $-N(R^{14})C(O)R^{15}$, $-S(O)_2R^{15}$, $-S(O)_2N(R^{12})(R^{13})$, $-S(=O)(=NH)N(R^{12})(R^{13})$, $-CH_2C(O)N(R^{12})(R^{13})$, $-CH_2N(R^{14})C(O)R^{15}$, $-CH_2S(O)_2R^{15}$, $-CH_2S(O)_2N(R^{12})(R^{13})$, $-CH_2N(R^{12})S(O)_2(R^{13})$, and $-P(O)(R^{17})(R^{17a})$ wherein $C_{1-6}$alkyl, $C_{2-6}$alkenyl, $C_{2-6}$alkynyl, $C_{3-10}$cycloalkyl, and $C_{2-9}$heterocycloalkyl are optionally substituted with one, two, or three $R^{20c}$;

$R^7$ is selected from hydrogen, halogen, $-CN$, $C_{1-6}$alkyl, $C_{2-6}$alkenyl, $C_{2-6}$alkynyl, $C_{3-10}$cycloalkyl, $C_{2-9}$heterocycloalkyl, $C_{1-9}$heteroaryl, $-OR^{12}$, $-SR^{12}$, $-N(R^{12})(R^{13})$, $-C(O)OR^{12}$, $-OC(O)N(R^{12})(R^{13})$, $-N(R^{14})C(O)N(R^{12})(R^{13})$, $-N(R^{14})C(O)OR^{15}$, $-N(R^{14})S(O)_2R^{15}$, $-C(O)R^{15}$, $-S(O)R^{15}$, $-OC(O)R^{15}$, $-C(O)N(R^{12})(R^{13})$, $-C(O)C(O)N(R^{12})(R^{13})$, $-N(R^{14})C(O)R^{15}$, $-S(O)_2R^{15}$, $-S(O)_2N(R^{12})(R^{13})$, $-S(=O)(=NH)N(R^{12})(R^{13})$, $-CH_2C(O)N(R^{12})(R^{13})$, $-CH_2N(R^{14})C(O)R^{15}$, $-CH_2S(O)_2R^{15}$, $-CH_2S(O)_2N(R^{12})(R^{13})$, $-CH_2N(R^{12})S(O)_2(R^{13})$, and $-P(O)(R^{17})(R^{17a})$, wherein $C_{1-6}$alkyl, $C_{2-6}$alkenyl, $C_{2-6}$alkynyl, $C_{3-10}$cycloalkyl, $C_{2-9}$heterocycloalkyl, and $C_{1-9}$heteroaryl are optionally substituted with one, two, or three $R^{20c}$;

each $R^{10}$ is independently selected from halogen, $-CN$, $C_{1-6}$alkyl, $C_{2-6}$alkenyl, $C_{2-6}$alkynyl, $C_{3-7}$cycloalkyl, $C_{2-9}$heterocycloalkyl, $C_{6-10}$aryl, $C_{1-9}$heteroaryl, $-OR^{12}$, $-SR^{12}$, $-N(R^{12})(R^{13})$, $-C(O)OR^{12}$, $-OC(O)N(R^{12})(R^{13})$, $-N(R^{14})C(O)N(R^{12})(R^{13})$, $-N(R^{14})C(O)OR^{15}$, $-N(R^{14})S(O)_2R^{15}$, $-C(O)R^{15}$, $-S(O)R^{15}$, $-OC(O)R^{15}$, $-C(O)N(R^{12})(R^{13})$, $-C(O)C(O)N(R^{12})(R^{13})$, $-N(R^{14})C(O)R^{15}$, $-S(O)_2R^{15}$, $-S(O)_2N(R^{12})(R^{13})$, $-S(=O)(=NH)N(R^{12})(R^{13})$, $-CH_2C(O)N(R^{12})(R^{13})$, $-CH_2N(R^{14})C(O)R^{15}$, $-CH_2S(O)_2R^{15}$, $-CH_2S(O)_2N(R^{12})(R^{13})$, $-CH_2N(R^{12})S(O)_2(R^{13})$, and $-P(O)(R^{17})(R^{17a})$, wherein $C_{1-6}$alkyl, $C_{2-6}$alkenyl, $C_{2-6}$alkynyl, $C_{3-7}$cycloalkyl, $C_{2-9}$heterocycloalkyl, $C_{6-10}$aryl, and $C_{1-9}$heteroaryl are optionally substituted with one, two, or three $R^{20a}$;

each $R^{12}$ is independently selected from hydrogen, $C_{1-6}$alkyl, $C_{1-6}$haloalkyl, $C_{2-6}$alkenyl, $C_{2-6}$alkynyl, $C_{3-7}$cycloalkyl, $C_{2-9}$heterocycloalkyl, $C_{6-10}$aryl, and $C_{1-9}$heteroaryl, wherein $C_{1-6}$alkyl, $C_{2-6}$alkenyl, $C_{2-6}$alkynyl, $C_{3-7}$cycloalkyl, $C_{2-9}$heterocycloalkyl, $C_{6-10}$aryl, and $C_{1-9}$heteroaryl are optionally substituted with one, two, or three $R^{20e}$;

each $R^{13}$ is independently selected from hydrogen, $C_{1-6}$alkyl, and $C_{1-6}$haloalkyl; or $R^{12}$ and $R^{13}$, together with the nitrogen to which they are attached, form a $C_{2-9}$heterocycloalkyl ring optionally substituted with one, two, or three $R^{20f}$;

$R^{13a}$ is selected from $C_{1-6}$alkyl and $C_{1-6}$haloalkyl; or $R^{12}$ and $R^{13a}$, together with the nitrogen to which they are attached, form a $C_{2-9}$heterocycloalkyl ring optionally substituted with one, two, or three $R^{20f}$;

each $R^{14}$ is independently selected from hydrogen, $C_{1-6}$alkyl, and $C_{1-6}$haloalkyl;

each $R^{15}$ is independently selected $C_{1-6}$alkyl, $C_{2-6}$alkenyl, $C_{2-6}$alkynyl, $C_{3-7}$cycloalkyl, $C_{2-9}$heterocycloalkyl, $C_{6-10}$aryl, and $C_{1-9}$ heteroaryl, wherein $C_{1-6}$alkyl, $C_{2-6}$alkenyl, $C_{2-6}$alkynyl, $C_{3-7}$cycloalkyl, $C_{2-9}$heterocycloalkyl, $C_{6-10}$aryl, and $C_{1-9}$heteroaryl are optionally substituted with one, two, or three $R^{20g}$;

each $R^{17}$ and each $R^{17a}$ are each independently selected from $C_{1-6}$alkyl and $C_{3-6}$cycloalkyl, wherein $C_{1-6}$alkyl and $C_{3-6}$cycloalkyl are optionally substituted with one, two or three of $R^{20h}$; or $R^{17}$ and $R^{17a}$ are combined to form a $C_{2-9}$heterocycloalkyl ring; each $R^{20a}$, $R^{20b}$, $R^{20c}$, $R^{20a}$, $R^{20e}$, $R^{20f}$, $R^{20g}$, and $R^{20h}$ are each independently selected from halogen, oxo, $=NH$, $-CN$, $C_{1-6}$alkyl, $C_{2-6}$alkenyl, $C_{2-6}$alkynyl, $C_{3-10}$cycloalkyl, $-CH_2-C_{3-10}$cycloalkyl, $C_{2-9}$heterocycloalkyl, $-CH_2-C_{2-9}$heterocycloalkyl, $C_{6-10}$aryl, $-CH_2-C_{6-10}$aryl, $C_{1-9}$heteroaryl, $-OR^{21}$, $-SR^{21}$, $-N(R^{22})(R^{23})$, $-C(O)OR^{22}$, $-C(O)N(R^{22})(R^{23})$, $-C(O)C(O)N(R^{22})(R^{23})$, $-OC(O)N(R^{22})(R^{23})$, $-N(R^{24})C(O)N(R^{22})(R^{23})$, $-N(R^{24})C(O)OR^{25}$, $-N(R^{24})C(O)R^{25}$, $-N(R^{24})S(O)_2R^{25}$, $-C(O)R^{25}$, $-S(O)_2R^{25}$, $-S(O)_2N(R^{22})(R^{23})$, $-OCH_2C(O)OR^{22}$, and $-OC(O)R^{25}$, wherein $C_{1-6}$alkyl, $C_{2-6}$alkenyl, $C_{2-6}$alkynyl, $C_{3-10}$cycloalkyl, $-CH_2-C_{3-10}$cycloalkyl, $C_{2-9}$heterocycloalkyl, $-CH_2-C_{2-9}$heterocycloalkyl, $C_{6-10}$aryl, —$CH_2$—$C_{6-10}$aryl, and $C_{1-9}$heteroaryl are optionally substituted with one, two, or three groups independently selected from halogen, oxo, =NH, —CN, $C_{1-6}$alkyl, $C_{1-6}$haloalkyl, $C_{1-6}$alkoxy, $C_{1-6}$haloalkoxy, —$OR^{21}$, —$SR^{21}$, —$N(R^{22})(R^{23})$, —$C(O)OR^{22}$, —$C(O)N(R^{22})(R^{23})$, —$C(O)C(O)N(R^{22})(R^{23})$, —$OC(O)N(R^{22})(R^{23})$, —$N(R^{24})C(O)N(R^{22})(R^{23})$, —$N(R^{24})C(O)OR^{25}$, —$N(R^{24})C(O)R^{25}$, —$N(R^{24})S(O)_2R^{25}$, —$C(O)R^{25}$, —$S(O)_2R^{25}$, —$S(O)_2N(R^{22})(R^{23})$, and —$OC(O)R^{25}$;

each $R^{21}$ is independently selected from H, $C_{1-6}$alkyl, $C_{1-6}$haloalkyl, $C_{2-6}$alkenyl, $C_{2-6}$alkynyl, $C_{3-7}$cycloalkyl, $C_{2-9}$heterocycloalkyl, $C_{6-10}$aryl, and $C_{1-9}$heteroaryl, wherein $C_{3-7}$cycloalkyl, $C_{2-9}$heterocycloalkyl, $C_{6-10}$aryl, and $C_{1-9}$heteroaryl are optionally substituted with one, two, or three groups independently selected from halogen and $C_{1-6}$alkyl;

each $R^{22}$ is independently selected from H, $C_{1-6}$alkyl, $C_{1-6}$haloalkyl, $C_{2-6}$alkenyl, $C_{2-6}$alkynyl, $C_{3-7}$cycloalkyl, $C_{2-9}$heterocycloalkyl, $C_{6-10}$aryl, and $C_{1-9}$heteroaryl, wherein $C_{3-7}$cycloalkyl, $C_{2-9}$heterocycloalkyl, $C_{6-10}$aryl, and $C_{1-9}$heteroaryl are optionally substituted with one, two, or three groups independently selected from halogen and $C_{1-6}$alkyl;

each $R^{23}$ is independently selected from H and $C_{1-6}$alkyl;

each $R^{24}$ is independently selected from H and $C_{1-6}$alkyl; and each $R^{25}$ is selected from $C_{1-6}$alkyl, $C_{2-6}$alkenyl, $C_{2-6}$alkynyl, $C_{3-7}$cycloalkyl, $C_{2-9}$heterocycloalkyl, $C_{6-10}$aryl, and $C_{1-9}$heteroaryl, wherein $C_{1-6}$alkyl, $C_{3-7}$cycloalkyl, $C_{2-9}$heterocycloalkyl, $C_{6-10}$aryl, and $C_{1-9}$heteroaryl are optionally substituted with one, two, or three groups independently selected from halogen, $C_{1-6}$alkyl, $C_{1-6}$haloalkyl, $C_{1-6}$alkoxy, $C_{3-7}$cycloalkyl, $C_{2-9}$heterocycloalkyl, $C_{6-10}$aryl, and $C_{1-9}$heteroaryl In some embodiments, the additional agent is an inhibitor against one or more targets selected from the group of: MEK, epidermal growth factor receptor (EGFR), A-Raf, B-Raf, C-Raf, SHP2, wildtype KRas, a KRas mutant, and CDK4/6.

In some embodiments, the additional agent is a chemotherapeutic agent, a radioactive agent, or an immune modulator.

In an aspect is provided a SOS1 protein bound by a compound described herein, or a pharmaceutically acceptable salt or solvate thereof, wherein interaction of the SOS1 protein with a Ras protein is reduced as compared to a SOS1 protein unbound to said compound.

In some embodiments is a method of treating cancer in a subject in need thereof, comprising administering to the subject a therapeutically effective amount of a compound Formula (I), (I'), (Ia), (Ia'), (Ib), (Ib'), (Ic), (Ic'), (II), (II'), (III), or (III'), or a pharmaceutically acceptable salt or solvate thereof. In some embodiments is a method of treating cancer in a subject in need thereof, comprising administering to the subject a therapeutically effective amount of a compound Formula (I), (I'), (Ia), (Ia'), (Ib), (Ib'), (Ic), (Ic'), (II), (II'), (III), or (III'), or a pharmaceutically acceptable salt or solvate thereof, wherein the cancer is a solid tumor or a hematological cancer. In some embodiments is a method of treating cancer in a subject in need thereof, comprising administering to the subject a therapeutically effective amount of a compound Formula (I), (I'), (Ia), (Ia'), (Ib), (Ib'), (Ic), (Ic'), (II), (II'), (III), or (III'), or a pharmaceutically acceptable salt or solvate thereof, wherein the cancer is a solid tumor. In some embodiments is a method of treating cancer in a subject in need thereof, comprising administering to the subject a therapeutically effective amount of a compound Formula (I), (I'), (Ia), (Ia'), (Ib), (Ib'), (Ic), (Ic'), (II), (II'), (III), or (III'), or a pharmaceutically acceptable salt or solvate thereof, wherein the cancer is selected from prostate cancer, brain cancer, colon cancer, rectal cancer, renal-cell carcinoma, liver cancer, non-small cell carcinoma of the lung, cancer of the small intestine, cancer of the esophagus, melanoma, bone cancer, pancreatic cancer, skin cancer, cancer of the head or neck, cutaneous or intraocular malignant melanoma, uterine cancer, ovarian cancer, rectal cancer, cancer of the anal region, stomach cancer, testicular cancer, uterine cancer, carcinoma of the fallopian tubes, carcinoma of the endometrium, carcinoma of the cervix, carcinoma of the vagina, carcinoma of the vulva, Hodgkin's Disease, non-Hodgkin's lymphoma, cancer of the endocrine system, cancer of the thyroid gland, cancer of the parathyroid gland, cancer of the adrenal gland, sarcoma of soft tissue, cancer of the urethra, cancer of the penis, solid tumors of childhood, cancer of the bladder, cancer of the kidney or ureter, carcinoma of the renal pelvis, neoplasm of the central nervous system (CNS), primary CNS lymphoma, tumor angiogenesis, spinal axis tumor, brain stem glioma, pituitary adenoma, Kaposi's sarcoma, epidermoid cancer, squamous cell cancer, T-cell lymphoma, environmentally induced cancers, combinations of said cancers, and metastatic lesions of said cancers. In some embodiments is a method of treating cancer in a subject in need thereof, comprising administering to the subject a therapeutically effective amount of a compound Formula (I), (I'), (Ia), (Ia'), (Ib), (Ib'), (Ic), (Ic'), (II), (II'), (III), or (III'), or a pharmaceutically acceptable salt or solvate thereof, wherein the cancer is a hematological cancer. In some embodiments is a method of treating cancer in a subject in need thereof, comprising administering to the subject a therapeutically effective amount of a compound Formula (I), (I'), (Ia), (Ia'), (Ib), (Ib'), (Ic), (Ic'), (II), (II'), (III), or (III'), or a pharmaceutically acceptable salt or solvate thereof, wherein the cancer is a hematological cancer selected from one or more of chronic lymphocytic leukemia (CLL), acute leukemias, acute lymphoid leukemia (ALL), B-cell acute lymphoid leukemia (B-ALL), T-cell acute lymphoid leukemia (T-ALL), chronic myelogenous leukemia (CML), B cell prolymphocytic leukemia, blastic plasmacytoid dendritic cell neoplasm, Burkitt's lymphoma, diffuse large B cell lymphoma, follicular lymphoma, hairy cell leukemia, small cell- or a large cell-follicular lymphoma, malignant lymphoproliferative conditions, MALT lymphoma, mantle cell lymphoma, marginal zone lymphoma, multiple myeloma, myelodysplasia and myelodysplastic syndrome, non-Hodgkin's lymphoma, Hodgkin's lymphoma, plasmablastic lymphoma, plasmacytoid dendritic cell neoplasm, Waldenstrom macroglobulinemia, and pre-leukemia. In some embodiments is a method of treating cancer in a subject in need thereof, comprising administering to the subject a therapeutically effective amount of a compound Formula (I), (I'), (Ia), (Ia'), (Ib), (Ib'), (Ic), (Ic'), (II), (II'), (III), or (III'), or a pharmaceutically acceptable salt or solvate thereof, wherein the cancer is one or more cancers selected from the group consisting of chronic lymphocytic leukemia (CLL), acute myeloid leukemia (AML), T-cell acute lymphoblastic leukemia (T-ALL), B cell acute lymphoblastic leukemia (B-ALL), and/or acute lymphoblastic leukemia (ALL).

In some embodiments is a method of treating cancer in a subject in need thereof, comprising administering to the subject a therapeutically effective amount of a compound Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), or a pharmaceutically acceptable salt or solvate thereof. In some embodiments is a method of treating cancer in a subject in need thereof, comprising administering to the subject a therapeutically effective amount of a compound Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), or a pharmaceutically acceptable salt or solvate thereof, wherein the cancer is a solid tumor or a hematological cancer. In some embodiments is a method of treating cancer in a subject in need thereof, comprising administering to the subject a therapeutically effective amount of a compound Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), or a pharmaceutically acceptable salt or solvate thereof, wherein the cancer is a solid tumor. In some embodiments is a method of treating cancer in a subject in need thereof, comprising administering to the subject a therapeutically effective amount of a compound Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), or a pharmaceutically acceptable salt or solvate thereof, wherein the cancer is selected from prostate cancer, brain cancer, colon cancer, rectal cancer, renal-cell carcinoma, liver cancer, non-small cell carcinoma of the lung, cancer of the small intestine, cancer of the esophagus, melanoma, bone cancer, pancreatic cancer, skin cancer, cancer of the head or neck, cutaneous or intraocular malignant melanoma, uterine cancer, ovarian cancer, rectal cancer, cancer of the anal region, stomach cancer, testicular cancer, uterine cancer, carcinoma of the fallopian tubes, carcinoma of the endometrium, carcinoma of the cervix, carcinoma of the vagina, carcinoma of the vulva, Hodgkin's Disease, non-Hodgkin's lymphoma, cancer of the endocrine system, cancer of the thyroid gland, cancer of the parathyroid gland, cancer of the adrenal gland, sarcoma of soft tissue, cancer of the urethra, cancer of the penis, solid tumors of childhood, cancer of the bladder, cancer of the kidney or ureter, carcinoma of the renal pelvis, neoplasm of the central nervous system (CNS), primary CNS lymphoma, tumor angiogenesis, spinal axis tumor, brain stem glioma, pituitary adenoma, Kaposi's sarcoma, epidermoid cancer, squamous cell cancer, T-cell lymphoma, environmentally induced cancers, combinations of said cancers, and metastatic lesions of said cancers. In some embodiments is a method of treating cancer in a subject in need thereof, comprising administering to the subject a therapeutically effective amount of a compound Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), or a pharmaceutically acceptable salt or solvate thereof, wherein the cancer is a hematological cancer. In some embodiments is a method of treating cancer in a subject in need thereof, comprising administering to the subject a therapeutically effective amount of a compound Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), or a pharmaceutically acceptable salt or solvate thereof, wherein the cancer is a hematological cancer selected from one or more of chronic lymphocytic leukemia (CLL), acute leukemias, acute lymphoid leukemia (ALL), B-cell acute lymphoid leukemia (B-ALL), T-cell acute lymphoid leukemia (T-ALL), chronic myelogenous leukemia (CML), B cell prolymphocytic leukemia, blastic plasmacytoid dendritic cell neoplasm, Burkitt's lymphoma, diffuse large B cell lymphoma, follicular lymphoma, hairy cell leukemia, small cell- or a large cell-follicular lymphoma, malignant lymphoproliferative conditions, MALT lymphoma, mantle cell lymphoma, marginal zone lymphoma, multiple myeloma, myelodysplasia and myelodysplastic syndrome, non-Hodgkin's lymphoma, Hodgkin's lymphoma, plasmablastic lymphoma, plasmacytoid dendritic cell neoplasm, Waldenstrom macroglobulinemia, and pre-leukemia. In some embodiments is a method of treating cancer in a subject in need thereof, comprising administering to the subject a therapeutically effective amount of a compound Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), or a pharmaceutically acceptable salt or solvate thereof, wherein the cancer is one or more cancers selected from the group consisting of chronic lymphocytic leukemia (CLL), acute myeloid leukemia (AML), T-cell acute lymphoblastic leukemia (T-ALL), B cell acute lymphoblastic leukemia (B-ALL), and/or acute lymphoblastic leukemia (ALL).

Any of the treatment methods disclosed herein can be administered alone or in combination or in conjunction with another therapy or another agent. By "combination" it is meant to include (a) formulating a subject composition containing a subject compound together with another agent, and (b) using the subject composition separate from the another agent as an overall treatment regimen. By "conjunction" it is meant that the another therapy or agent is administered either simultaneously, concurrently or sequentially with a subject composition comprising a compound disclosed herein, with no specific time limits, wherein such conjunctive administration provides a therapeutic effect.

In some embodiment, a subject treatment method is combined with surgery, cellular therapy, chemotherapy, radiation, and/or immunosuppressive agents. Additionally, compositions of the present disclosure can be combined with other therapeutic agents, such as other anti-cancer agents, anti-allergic agents, anti-nausea agents (or anti-emetics), pain relievers, cytoprotective agents, immunostimulants, and combinations thereof.

In one embodiment, a subject treatment method is combined with a chemotherapeutic agent.

Exemplary chemotherapeutic agents include an anthracycline (e.g., doxorubicin (e.g., liposomal doxorubicin)), a vinca alkaloid (e.g., vinblastine, vincristine, vindesine, vinorelbine), an alkylating agent (e.g., cyclophosphamide, decarbazine, melphalan, ifosfamide, temozolomide), an immune cell antibody (e.g., alemtuzamab, gemtuzumab, rituximab, ofatumumab, tositumomab, brentuximab), an antimetabolite (including, e.g., folic acid antagonists, pyrimidine analogs, purine analogs and adenosine deaminase inhibitors (e.g., fludarabine)), a TNFR glucocorticoid induced TNFR related protein (GITR) agonist, a proteasome inhibitor (e.g., aclacinomycin A, gliotoxin or bortezomib), an immunomodulator such as thalidomide or a thalidomide derivative (e.g., lenalidomide). Additional chemotherapeutic agents contemplated for use in combination include busulfan (Myleran®), busulfan injection (Busulfex®), cladribine (Leustatin®), cyclophosphamide (Cytoxan® or Neosar®), cytarabine, cytosine arabinoside (Cytosar-U®), cytarabine liposome injection (DepoCyt®), daunorubicin hydrochloride (Cerubidine®), daunorubicin citrate liposome injection (DaunoXome®), dexamethasone, doxorubicin hydrochloride (Adriamycin®, Rubex®), etoposide (Vepesid®), fludarabine phosphate (Fludara®), hydroxyurea (Hydrea®), Idarubicin (Idamycin®), mitoxantrone (Novantrone®), Gemtuzumab Ozogamicin (Mylotarg®), anastrozole (Arimidex®), bicalutamide (Casodex®), bleomycin sulfate (Blenoxane®), busulfan injection (Busulfex®), capecitabine (Xeloda®), N4-pentoxycarbonyl-5-deoxy-5-fluorocytidine, carboplatin (Paraplatin®), carmustine (BiCNU®), chlorambucil (Leukeran®), cisplatin (Platinol®), dacarbazine (DTIC-Dome®), dactinomycin (Actinomycin D, Cosmegan), dexamethasone, docetaxel (Taxotere®), 5-fluorouracil (Adrucil®, Efudex®), flutamide (Eulexin®), tezacitibine, Gemcitabine (difluorodeoxycitidine), ifosfamide (IFEX®), irinotecan (Camptosar®), L-asparaginase (ELSPAR®), leucovorin calcium, melphalan (Alkeran®), 6-mercaptopurine (Purinethol®), methotrexate (Folex®), mitoxantrone (Novantrone®), mylotarg, paclitaxel (Taxol®), phoenix (Yttrium90/MX-DTPA), pentostatin, polifeprosan 20 with carmustine implant (Gliadel®), tamoxifen citrate (Nolvadex®), teniposide (Vumon®), 6-thioguanine, thiotepa, tirapazamine (Tirazone®), topotecan hydrochloride for injection (Hycamptin®), vinblastine (Velban®), vincristine (Oncovin®), and vinorelbine (Navelbine®).

Anti-cancer agents of particular interest for combinations with a compound of the present invention include: anthracyclines; alkylating agents; antimetabolites; drugs that inhibit either the calcium dependent phosphatase calcineurin or the p70S6 kinase FK506) or inhibit the p70S6 kinase; mTOR inhibitors; immunomodulators; anthracyclines; vinca alkaloids; proteosome inhibitors; GITR agonists; protein tyrosine phosphatase inhibitors; a CDK4 kinase inhibitor; a BTK inhibitor; a MKN kinase inhibitor; a DGK kinase inhibitor; or an oncolytic virus.

Exemplary antimetabolites include, without limitation, pyrimidine analogs, purine analogs and adenosine deaminase inhibitors): methotrexate (Rheumatrex®, Trexall®), 5-fluorouracil (Adrucil®, Efudex®, Fluoroplex®), floxuridine (FUDF®), cytarabine (Cytosar-U®, Tarabine PFS), 6-mercaptopurine (Puri-Nethol®)), 6-thioguanine (Thioguanine Tabloid®), fludarabine phosphate (Fludara®), pentostatin (Nipent®), pemetrexed (Alimta®), raltitrexed (Tomudex®), cladribine (Leustatin®), clofarabine (Clofarex®, Clolar®), azacitidine (Vidaza®), decitabine and gemcitabine (Gemzar®). Preferred antimetabolites include, cytarabine, clofarabine and fludarabine.

Exemplary alkylating agents include, without limitation, nitrogen mustards, ethylenimine derivatives, alkyl sulfonates, nitrosoureas and triazenes): uracil mustard (Aminouracil Mustard®, Chlorethaminacil®, Demethyldopan®, Desmethyldopan®, Haemanthamine®, Nordopan®, Uracil nitrogen Mustard®, Uracillost®, Uracilmostaza®, Uramustin®, Ummustine®), chlormethine (Mustargen®), cyclophosphamide (Cytoxan®, Neosar®, Clafen®, Endoxan®, Procytox®, Revimmune$^T$), ifosfamide (Mitoxana®), melphalan (Alkeran®), Chlommbucil (Leukeran®), pipobroman (Amedel®, Vercyte®), triethylenemelamine (Hemel®, Hexalen®, Hexastat®), triethylenethiophosphoramine, Temozolomide (Temodar®), thiotepa (Thioplex®), busulfan (Busilvex®, Myleran®), carmustine (BiCNU®), lomustine (CeeNU®), streptozocin (Zanosar®), and Dacarbazine (DTIC-Dome®). Additional exemplary alkylating agents include, without limitation, Oxaliplatin (Eloxatin®); Temozolomide (Temodar® and Temodal®); Dactinomycin (also known as actinomycin-D, Cosmegen®); Melphalan (also known as L-PAM, L-sarcolysin, and phenylalanine mustard, Alkeran®); Altretamine (also known as hexamethylmelamine (HMM), Hexalen®); Carmustine (BiCNU®); Bendamustine (Treanda®); Busulfan (Busulfex® and Myleran®); Carboplatin (Paraplatin®); Lomustine (also known as CCNU, CeeNU®); Cisplatin (also known as CDDP, Platinol® and Platinol®-AQ); Chlorambucil (Leukeran®); Cyclophosphamide (Cytoxan® and Neosar®); Dacarbazine (also known as DTIC, DIC and imidazole carboxamide, DTIC-Dome®); Altretamine (also known as hexamethylmelamine (HMM), Hexalen®); Ifosfamide (Ifex®); Prednumustine; Procarbazine (Matulane®); Mechlorethamine (also known as nitrogen mustard, mustine and mechloroethamine hydrochloride, Mustargen®); Streptozocin (Zanosar®); Thiotepa (also known as thiophosphoamide, TESPA and TSPA, Thioplex®); Cyclophosphamide (Endoxan®, Cytoxan®, Neosar®, Procytox®, Revimmune®); and Bendamustine HCl (Treanda®).

In an aspect, compositions provided herein can be administered in combination with radiotherapy such as radiation. Whole body radiation may be administered at 12 Gy. A radiation dose may comprise a cumulative dose of 12 Gy to the whole body, including healthy tissues. A radiation dose may comprise from 5 Gy to 20 Gy. A radiation dose may be 5 Gy, 6 Gy, 7 Gy, 8 Gy, 9 Gy, 10 Gy, 11 Gy, 12, Gy, 13 Gy, 14 Gy, 15 Gy, 16 Gy, 17 Gy, 18 Gy, 19 Gy, or up to 20 Gy. Radiation may be whole body radiation or partial body radiation. In the case that radiation is whole body radiation it may be uniform or not uniform. For example, when radiation may not be uniform, narrower regions of a body such as the neck may receive a higher dose than broader regions such as the hips.

Where desirable, an immunosuppressive agent can be used in conjunction with a subject treatment method. Exemplary immunosuppressive agents include but are not limited to cyclosporin, azathioprine, methotrexate, mycophenolate, and FK506, antibodies, or other immunoablative agents such as CAMPATH, anti-CD3 antibodies (e.g., muromonab, otelixizumab) or other antibody therapies, cytoxin, fludarabine, cyclosporin, FK506, rapamycin, mycophenolic acid, steroids, FR901228, cytokines, and irradiation, peptide vaccine, and any combination thereof. In accordance with the presently disclosed subject matter, the above-described various methods can comprise administering at least one immunomodulatory agent. In certain embodiments, the at least one immunomodulatory agent is selected from the group consisting of immunostimulatory agents, checkpoint immune blockade agents (e.g., blockade agents or inhibitors of immune checkpoint genes, such as, for example, PD-1, PD-L1, CTLA-4, IDO, TIM3, LAG3, TIGIT, BTLA, VISTA, ICOS, KIRs and CD39), radiation therapy agents, chemotherapy agents, and combinations thereof. In some embodiments, the immunostimulatory agents are selected from the group consisting of IL-12, an agonist costimulatory monoclonal antibody, and combinations thereof. In one embodiment, the immunostimulatory agent is IL-12. In some embodiments, the agonist costimulatory monoclonal antibody is selected from the group consisting of an anti-4-1BB antibody (e.g., urelumab, PF-05082566), an anti-OX40 antibody (pogalizumab, tavolixizumab, PF-04518600), an anti-ICOS antibody (BMS986226, MEDI-570, GSK3359609, JTX-2011), and combinations thereof. In one embodiment, the agonist costimulatory monoclonal antibody is an anti-4-1 BB antibody. In some embodiments, the checkpoint immune blockade agents are selected from the group consisting of anti-PD-L1 antibodies (atezolizumab, avelumab, durvalumab, BMS-936559), anti-CTLA-4 antibodies (e.g., tremelimumab, ipilimumab), anti-PD-1 antibodies (e.g., pembrolizumab, nivolumab), anti-LAG3 antibodies (e.g., C9B7W, 410C9), anti-B7-H3 antibodies (e.g., DS-5573a), anti-TIM3 antibodies (e.g., F38-2E2), and combinations thereof. In one embodiment, the checkpoint immune blockade agent is an anti-PD-L1 antibody. In some cases, a compound of the present disclosure can be administered to a subject in conjunction with (e.g., before, simultaneously or following) bone marrow transplantation, T cell ablative therapy using either chemotherapy agents such as, fludarabine, external-beam radiation therapy (XRT), cyclophosphamide, or antibodies such as OKT3 or CAMPATH. In some cases, expanded cells can be administered before or following surgery. Alternatively, compositions comprising a compound described herein can be administered with immunostimulants. Immunostimulants can be vaccines, colony stimulating agents, interferons, interleukins, viruses, antigens, co-stimulatory agents, immunogenicity agents, immunomodulators, or immunotherapeutic agents. An immunostimulant can be a cytokine such as an interleukin. One or more cytokines can be introduced with modified cells provided herein. Cytokines can be utilized to boost function of modified T lymphocytes (including adoptively transferred tumor-specific cytotoxic T lymphocytes) to expand within a tumor microenvironment. In some cases, IL-2 can be used to facilitate expansion of the modified cells described herein. Cytokines such as IL-15 can also be employed. Other relevant cytokines in the field of immunotherapy can also be utilized, such as IL-2, IL-7, IL-12, IL-15, IL-21, or any combination thereof. An interleukin can be IL-2, or aldesleukin. Aldesleukin can be administered in low dose or high dose. A high dose aldesleukin regimen can involve administering aldesleukin intravenously every 8 hours, as tolerated, for up to about 14 doses at about 0.037 mg/kg (600,000 IU/kg). An immunostimulant (e.g., aldesleukin) can be administered within 24 hours after a cellular administration. An immunostimulant (e.g., aldesleukin) can be administered in as an infusion over about 15 minutes about every 8 hours for up to about 4 days after a cellular infusion. An immunostimulant (e.g., aldesleukin) can be administered at a dose from about 100,000 IU/kg, 200,000 IU/kg, 300,000 IU/kg, 400,000 IU/kg, 500,000 IU/kg, 600,000 IU/kg, 700,000 IU/kg, 800,000 IU/kg, 900,000 IU/kg, or up to about 1,000,000 IU/kg. In some cases, aldesleukin can be administered at a dose from about 100,000 IU/kg to 300,000 IU/kg, from 300,000 IU/kg to 500,000 IU/kg, from 500,000 IU/kg to 700,000 IU/kg, from 700,000 IU/kg to about 1,000,000 IU/kg.

In some other embodiments, any of the compounds herein that is capable of modulating a SOS protein (e.g., SOS1) to reduce Ras signaling output may be administered in combination or in conjunction with one or more pharmacologically active agents including but not limited to: (1) an inhibitor of MEK (e.g., MEK1, MEK2) or of mutants thereof (e.g., trametinib, cobimetinib, binimetinib, selumetinib, refametinib, AZD6244); (2) an inhibitor of epidermal growth factor receptor (EGFR) and/or of mutants thereof (e.g., afatinib, erlotinib, gefitinib, lapatinib, cetuximab panitumumab, osimertinib, olmutinib, EGF-816); (3) an immunotherapeutic agent (e.g., checkpoint immune blockade agents, as disclosed herein); (4) a taxane (e.g., paclitaxel, docetaxel); (5) an anti-metabolite (e.g. antifolates such as methotrexate, raltitrexed, pyrimidine analogues such as 5-fluorouracil (5-FU), ribonucleoside and deoxyribonucleoside analogues, capecitabine and gemcitabine, purine and adenosine analogues such as mercaptopurine, thioguanine, cladribine and pentostatin, cytarabine (ara C), fludarabine); (6) an inhibitor of FGFR1 and/or FGFR2 and/or FGFR3 and/or of mutants thereof (e.g., nintedanib); (7) a mitotic kinase inhibitor (e.g., a CDK4/6 inhibitor, such as, for example, palbociclib, ribociclib, abemaciclib); (8) an anti-angiogenic drug (e.g., an anti-VEGF antibody, such as, for example, bevacizumab); (9) a topoisomerase inhibitor (e.g. epipodophyllotoxins such as for example etoposide and etopophos, teniposide, amsacrin, topotecan, irinotecan, mitoxantrone); (10) a platinum-containing compound (e.g. cisplatin, oxaliplatin, carboplatin); (11) an inhibitor of ALK and/or of mutants thereof (e.g. crizotinib, alectinib, entrectinib, brigatinib); (12) an inhibitor of c-MET and/or of mutants thereof (e.g., K252a, SU11274, PHA665752, PF2341066); (13) an inhibitor of BCR-ABL and/or of mutants thereof (e.g., imatinib, dasatinib, nilotinib); (14) an inhibitor of ErbB2 (Her2) and/or of mutants thereof (e.g., afatinib, lapatinib, trastuzumab, pertuzumab); (15) an inhibitor of AXL and/or of mutants thereof (e.g., R428, amuvatinib, XL-880); (16) an inhibitor of NTRK1 and/or of mutants thereof (e.g., Merestinib); (17) an inhibitor of RET and/or of mutants thereof (e.g., BLU-667, Lenvatinib); (18) an inhibitor of A-Raf, B-Raf (e.g., Sorafenib, Vemurafenib, Debrafenib, Encorafenib) and/or C-Raf and/or of mutants thereof (RAF-709, LY-3009120); (19) an inhibitor of ERK and/or of mutants thereof (e.g., ulixertinib); (20) an MDM2 inhibitor (e.g., HDM-201, NVP-CGM097, RG-71 12, MK-8242, RG-7388, SAR405838, AMG-232, DS-3032, RG-7775, APG-115); (21) an inhibitor of mTOR (e.g., rapamycin, temsirolimus, everolimus, ridaforolimus); (22) an inhibitor of BET (e.g., I-BET 151, I-BET 762, OTX-015, TEN-010, CPI-203, CPI-0610, olionon, RVX-208, ABBC-744, LY294002, AZD5153, MT-1, MS645); (23) an inhibitor of IGF1/2 and/or of IGF1-R (e.g., xentuzumab, MEDI-573); (24) an inhibitor of CDK9 (e.g., DRB, flavopiridol, CR8, AZD 5438, purvalanol B, AT7519, dinaciclib, SNS-032); (25) an inhibitor of farnesyl transferase (e.g., tipifarnib); (26) an inhibitor of SHIP pathway including SHIP2 inhibitor (e.g., 6-(4-amino-4-methylpiperidin-1-yl)-3-(2,3-dichlorophenyl)pyrazin-2-amine), as well as SHIP1 inhibitors; (27) an inhibitor of SRC (e.g., dasatinib); (28) an inhibitor of JAK (e.g., tofacitinib); (29) a PARP inhibitor (e.g. Olaparib, Rucaparib, Niraparib, Talazoparib), (30) a BTK inhibitor (e.g. Ibrutinib, Acalabrutinib, Zanubrutinib), (31) a ROS1 inhibitor (e.g., entrectinib), (32) an inhibitor of FLT3, HDAC, VEGFR, PDGFR, LCK, Bcr-Abl or AKT, (33) an inhibitor of Kras12C mutant (e.g., including but not limited to AMG510, MRTX849, and any covalent inhibitors binding to the cysteine residue 12 of Kras, the structures of these compounds are publicly known)(e.g., an inhibitor of Ras G12C as described in US20180334454, US20190144444, US20150239900, U.S. Ser. No. 10/246,424, US20180086753, WO2018143315, WO2018206539, WO20191107519, WO2019141250, WO2019150305, U.S. Pat. No. 9,862,701, US20170197945, US20180086753, U.S. Pat. No. 10,144,724, US20190055211, US20190092767, US20180127396, US20180273523, U.S. Pat. No. 10,280,172, US20180319775, US20180273515, US20180282307, US20180282308, WO2019051291, WO2019213526, WO2019213516, WO2019217691, WO2019241157, WO2019217307, WO2020047192, WO2017087528, WO2018218070, WO2018218069, WO2018218071, WO2020027083, WO2020027084, WO2019215203, WO2019155399, WO2020035031, WO2014160200, WO2018195349, WO2018112240, WO2019204442, WO2019204449, WO2019104505, WO2016179558, WO2016176338, or related patents and applications, each of which is incorporated by reference in its entirety), (34) a SHC inhibitor (e.g., PP2, AID371185), (35) a GAB inhibitor (e.g., GAB-0001), (36) a GRB inhibitor, (37) a PI-3 kinase inhibitor (e.g., Idelalisib, Copanlisib, Duvelisib, Alpelisib, Taselisib, Perifosine, Buparlisib, Umbralisib, NVP-BEZ235-AN), (38) a MARPK inhibitor, (39) CDK4/6 (e.g., palbociclib, ribociclib, abemaciclib), or (40) MAPK inhibitor (e.g., VX-745, VX-702, RO-4402257, SCIO-469, BIRB-796, SD-0006, PH-797804, AMG-548, LY2228820, SB-681323, GW-856553, RWJ67657, BCT-197), or (41) an inhibitor of SHP pathway including SHP2 inhibitor (e.g., 6-(4-amino-4-methylpiperidin-1-yl)-3-(2,3-dichlorophenyl)pyrazin-2-amine,

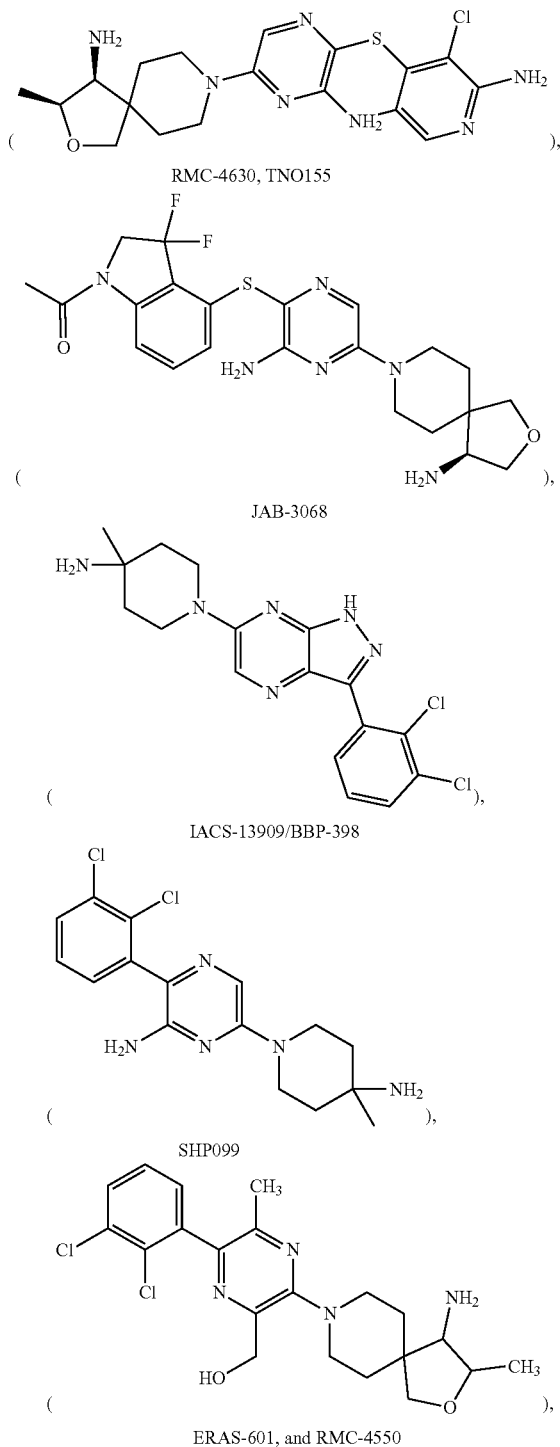

as well as SHP1 inhibitors; or (42) an inhibitor of a wildtype KRas or a Kras mutant (e.g., Kras G12D including a compound described in WO2021041671, KRas G12C, KRas G12D, KRas G12S, KRas G12V, KRas G13D, KRas G13C, or KRas G13V). Inhibitors of any of the exemplary targets are applicable to the corresponding mutant targets having one or more mutations therein. In some embodiments, any of the compounds herein that is capable of inhibiting a SOS protein (e.g., SOS1) to reduce Ras signaling output may be administered in combination or in conjunction with one or more checkpoint immune blockade agents (e.g., anti-PD-1 and/or anti-PD-L1 antibody, anti-CLTA-4 antibody).

In combination therapy, a compound provided herein and other anti-cancer agent(s) may be administered either simultaneously, concurrently or sequentially with no specific time limits, wherein such administration provides therapeutically effective levels of the two compounds in the body of the patient.

In some embodiments, a compound of the present disclosure and the other anti-cancer agent(s) are generally administered sequentially in any order by infusion or orally. The dosing regimen may vary depending upon the stage of the disease, physical fitness of the patient, safety profiles of the individual drugs, and tolerance of the individual drugs, as well as other criteria well-known to the attending physician and medical practitioner(s) administering the combination. The compound of the present invention and other anti-cancer agent(s) may be administered within minutes of each other, hours, days, or even weeks apart depending upon the particular cycle being used for treatment. In addition, the cycle could include administration of one drug more often than the other during the treatment cycle and at different doses per administration of the drug.

An antibiotic can be administered to a subject as part of a therapeutic regime. An antibiotic can be administered at a therapeutically effective dose. An antibiotic can kill or inhibit growth of bacteria. An antibiotic can be a broad spectrum antibiotic that can target a wide range of bacteria. Broad spectrum antibiotics, either a $3^{rd}$ or $4^{th}$ generation, can be cephalosporin or a quinolone. An antibiotic can also be a narrow spectrum antibiotic that can target specific types of bacteria. An antibiotic can target a bacterial cell wall such as penicillins and cephalosporins. An antibiotic can target a cellular membrane such as polymyxins. An antibiotic can interfere with essential bacterial enzymes such as antibiotics: rifamycins, lipiarmycins, quinolones, and sulfonamides. An antibiotic can also be a protein synthesis inhibitor such as macrolides, lincosamides, and tetracyclines. An antibiotic can also be a cyclic lipopeptide such as daptomycin, glycylcyclines such as tigecycline, oxazolidiones such as linezolid, and lipiarmycins such as fidaxomicin. In some cases, an antibiotic can be $1^{st}$ generation, $2^{nd}$ generation, $3^{rd}$ generation, $4^{th}$ generation, or $5^{th}$ generation. A first-generation antibiotic can have a narrow spectrum. Examples of 1 t generation antibiotics can be penicillins (Penicillin G or Penicillin V), Cephalosporins (Cephazolin, Cephalothin, Cephapirin, Cephalethin, Cephradin, or Cephadroxin). In some cases, an antibiotic can be $2^{nd}$ generation. $2^{nd}$ generation antibiotics can be a penicillin (Amoxicillin or Ampicillin), Cephalosporin (Cefuroxime, Cephamandole, Cephoxitin, Cephaclor, Cephrozil, Loracarbef). In some cases, an antibiotic can be $3^{rd}$ generation. A $3^{rd}$ generation antibiotic can be penicillin (carbenicillin and ticarcillin) or cephalosporin (Cephixime, Cephtriaxone, Cephotaxime, Cephtizoxime, and Cephtazidime). An antibiotic can also be a $4^{th}$ generation antibiotic. A $4^{th}$ generation antibiotic can be Cephipime. An antibiotic can also be $5^{th}$ generation. $5^{th}$ generation antibiotics can be Cephtaroline or Cephtobiprole.

In some cases, an anti-viral agent may be administered as part of a treatment regime. In some cases, a herpes virus prophylaxis can be administered to a subject as part of a treatment regime. A herpes virus prophylaxis can be valacyclovir (Valtrex). Valtrex can be used orally to prevent the occurrence of herpes virus infections in subjects with positive HSV serology. It can be supplied in 500 mg tablets. Valacyclovir can be administered at a therapeutically effective amount.

In some cases, a treatment regime may be dosed according to a body weight of a subject. In subjects who are determined obese (BMI>35) a practical weight may need to be utilized. BMI is calculated by: BMI=weight (kg)/[height (m)]$^2$.

Body weight may be calculated for men as 50 kg+2.3* (number of inches over 60 inches) or for women 45.5 kg+2.3 (number of inches over 60 inches). An adjusted body weight may be calculated for subjects who are more than 20% of their ideal body weight. An adjusted body weight may be the sum of an ideal body weight+(0.4×(Actual body weight−ideal body weight)). In some cases, a body surface area may be utilized to calculate a dosage. A body surface area (BSA) may be calculated by: BSA (m2)=√Height (cm)*Weight (kg)/3600.

In some embodiments is a method of reducing Ras signaling output, comprising contacting a SOS protein (e.g., SOS1) with an effective amount of a compound of Formula (I), (I'), (Ia), (Ia'), (Ib), (Ib'), (Ic), (Ic'), (II), (II'), (III), or (III'), or a pharmaceutically acceptable salt or solvate thereof, thereby reducing the Ras signaling output. In some embodiments is a method of reducing Ras signaling output, comprising contacting a SOS protein (e.g., SOS1) with an effective amount of a compound of Formula (I), (I'), (Ia), (Ia'), (Ib), (Ib'), (Ic), (Ic'), (II), (II'), (III), or (III'), or a pharmaceutically acceptable salt or solvate thereof, wherein said the compound inhibits the SOS1 protein activity or disrupt interaction or binding between a SOS1 protein and a Ras protein. In some embodiments, a compound of Formula (I), (I'), (Ia), (Ia'), (Ib), (Ib'), (Ic), (Ic'), (II), (II'), (III), or (III') inhibits SOS1 or disrupts interaction or binding between SOS1 and one or more of the following: a K-Ras protein including wildtype and any mutant thereof. In some embodiments, a compound of Formula (I), (I'), (Ia), (Ia'), (Ib), (Ib'), (Ic), (Ic'), (II), (II'), (III), or (III') inhibits SOS1 activity or disrupts interaction or binding between SOS1 and one or more of the following: K-RasG12D mutant and K-RasG12V mutant.

In some embodiments is a method of reducing Ras signaling output, comprising contacting a SOS protein (e.g., SOS1) with an effective amount of a compound of Formula (I-1), (I'-1), (Ia-1), (Ia'-1), (Ib-1), (Ib'-1), (Ic-1), (Ic'-1), (1-2), (I'-2), (Ia-2), (Ia'- 2), (Ib-2), (Ib'-2), (Ic-2), or (Ic'-2), or a pharmaceutically acceptable salt or solvate thereof, thereby reducing the Ras signaling output. In some embodiments is a method of reducing Ras signaling output, comprising contacting a SOS protein (e.g., SOS1) with an effective amount of a compound of Formula (I-1), (I'-1), (Ia-1), (Ia'-1), (Ib-1), (Ib'-1), (Ic-1), (Ic'-1), (1-2), (I'-2), (Ia-2), (Ia'-2), (Ib-2), (Ib'-2), (Ic-2), or (Ic'-2), or a pharmaceutically acceptable salt or solvate thereof, wherein said the compound inhibits the SOS1 protein activity or disrupt interaction or binding between a SOS1 protein and a Ras protein. In some embodiments, a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2) inhibits SOS1 or disrupts interaction or binding between SOS1 and one or more of the following: a K-Ras protein including wildtype and any mutant thereof. In some embodiments, a compound of Formula (I-1), (I'-1), (Ia-1), (Ia'-1), (Ib-1), (Ib'-1), (Ic-1), (Ic'-1), (1-2), (I'-2), (Ia-2), (Ia'-2), (Ib-2), (Ib'-2), (Ic-2), or (Ic'-2) inhibits SOS1 activity or disrupts interaction or binding between SOS1 and one or more of the following: K-RasG12D mutant and K-RasG12V mutant.

In some embodiments, provided is a method of reducing Ras signaling output in a cell by contacting the cell with a compound of the present disclosure. A reduction in Ras signaling can be evidenced by one or more members of the following: (i) an increase in steady state level of GDP-bound Ras protein; (ii) a reduction of phosphorylated AKTs473, (iii) a reduction of phosphorylated ERKT202/y204, (iv) a reduction of phosphorylated S6S235/236, (v) reduction (e.g., inhibition) of cell growth of Ras-driven tumor cells (e.g., those derived from a tumor cell line disclosed herein), and (vi) an interference or disruption of the interaction or binding between a SOS protein (e.g., SOS1) with a Ras protein such as a wildtype or a mutant Ras. In some cases, the reduction in Ras signaling output can be evidenced by two, three, four, five or all of (i)-(vi) above. In some embodiments, the reduction any one or more of (i)-(vi) can be 0.1-fold, 0.2-fold, 0.3-fold, 0.4-fold, 0.5-fold, 0.6-fold, 0.7-fold, 0.8-fold, 0.9-fold, 1-fold, 2-fold, 3-fold, 4-fold, 5-fold, 6-fold, 7-fold, 8-fold, 9-fold, 10-fold, 20-fold, 30-fold, 40-fold, 50-fold, 60-fold, 70-fold, 80-fold, 90-fold, 100-fold, 200-fold, 300-fold, 400-fold, 500-fold, 600-fold, 700-fold, 800-fold, 900-fold, 1000-fold, 2000-fold, 3000-fold, 4000-fold, 5000-fold, or more as compared to control untreated with a subject compound. A reduction in cell growth can be demonstrated with the use of tumor cells or cell lines. A tumor cell line can be derived from a tumor in one or more tissues, e.g., pancreas, lung, ovary, biliary tract, intestine (e.g., small intestine, large intestine (i.e. colon)), endometrium, stomach, hematopoietic tissue (e.g., lymphoid tissue), etc. Examples of the tumor cell line with a K-Ras mutation may include, but are not limited to, A549 (e.g., K-Ras G12S), AGS (e.g., K-Ras G12D), ASPC1 (e.g., K-Ras G12D), Calu-6 (e.g., K-Ras Q61K), CFPAC-1 (e.g., K-Ras G12V), CL40 (e.g., K-Ras G12D), COL0678 (e.g., K-Ras G12D), COR-L23 (e.g., K-Ras G12V), DAN-G (e.g., K-Ras G12V), GP2D (e.g., K-Ras G12D), GSU (e.g., K-Ras G12F), HCT116 (e.g., K-Ras G13D), HEC1A (e.g., K-Ras G12D), HEC1B (e.g., K-Ras G12F), HEC50B (e.g., K-Ras G12F), HEYA8 (e.g., K-Ras G12D or G13D), HPAC (e.g., K-Ras G12D), HPAFII (e.g., K-Ras G12D), HUCCT1 (e.g., K-Ras G12D), KARPAS620 (e.g., K-Ras G13D), KOPN8 (e.g., K-Ras G13D), KP-3 (e.g., K-Ras G12V), KP-4 (e.g., K-Ras G12D), L3.3 (e.g., K-Ras G12D), LoVo (e.g., K-Ras G13D), LS180 (e.g., K-Ras G12D), LS513 (e.g., K-Ras G12D), MCAS (e.g., K-Ras G12D), NB4 (e.g., K-Ras A18D), NCI-H1355 (e.g., K-Ras G13C), NCI-H1573 (e.g., K-Ras G12A), NCI-H1944 (e.g., K-Ras G13D), NCI-H2009 (e.g., K-Ras G12A), NCI-H441 (e.g., K-Ras G12V), NCI-H747 (e.g., K-Ras G13D), NOMO-1 (e.g., K-Ras G12D), OV7 (e.g., K-Ras G12D), PANC0203 (e.g., K-Ras G12D), PANC0403 (e.g., K-Ras G12D), PANC0504 (e.g., K-Ras G12D), PANC0813 (e.g., K-Ras G12D), PANC1 (e.g., K-Ras G12D), Panc-10.05 (e.g., K-Ras G12D), PaTu-8902 (e.g., K-Ras G12V), PK1 (e.g., K-Ras G12D), PK45H (e.g., K-Ras G12D), PK59 (e.g., K-Ras G12D), SK-CO-1 (e.g., K-Ras G12V), SKLU1 (e.g., K-Ras G12D), SKM-1 (e.g., K-Ras K117N), SNU1 (e.g., K-Ras G12D), SNU1033 (e.g., K-Ras G12D), SNU1197 (e.g., K-Ras G12D), SNU407 (e.g., K-Ras G12D), SNU410 (e.g., K-Ras G12D), SNU601 (e.g., K-Ras G12D), SNU61 (e.g., K-Ras G12D), SNU8 (e.g., K-Ras G12D), SNU869 (e.g., K-Ras G12D), SNU-C2A (e.g., K-Ras G12D), SU.86.86 (e.g., K-Ras G12D), SUIT2 (e.g., K-Ras G12D), SW1990 (e.g., K-Ras G12D), SW403 (e.g., K-Ras G12V), SW480 (e.g., K-Ras G12V), SW620 (e.g., K-Ras G12V), SW948 (e.g., K-Ras Q61L), T3M10 (e.g., K-Ras G12D), TCC-PAN2 (e.g., K-Ras G12R), TGBC11TKB (e.g., K-Ras G12D), and MIA Pa-Ca (e.g., MIA Pa-Ca 2 (e.g., K-Ras G12C)).

In some embodiments is a SOS protein (e.g., SOS1) bound by a compound of Formula (I), (I'), (Ia), (Ia'), (Ib), (Ib'), (Ic), (Ic'), (II), (II'), (III), or (III'), or a pharmaceutically acceptable salt or solvate thereof, wherein interaction of SOS1 protein with a Ras protein is reduced as compared to a SOS1 protein unbound to said compound. In some embodiments is a SOS protein (e.g., SOS1) bound by a compound of Formula (I-1), (I'-1), (Ia-1), (Ia'-1), (Ib-1), (Ib'-1), (Ic-1), (Ic'-1), (1-2), (I'-2), (Ia-2), (Ia'-2), (Ib-2), (Ib'-2), (Ic-2), or (Ic'-2), or a pharmaceutically acceptable salt or solvate thereof, wherein interaction of SOS1 protein with a Ras protein is reduced as compared to a SOS1 protein unbound to said compound.

Pharmaceutical Compositions and Methods of Administration

In an aspect is provided a pharmaceutical composition comprising a compound described herein, or a pharmaceutically acceptable salt or solvate thereof, and a pharmaceutically acceptable excipient.

The compounds of Formula (I), (I'), (Ia), (Ia'), (Ib), (Ib'), (Ic), (Ic'), (II), (II'), (III), or (III'), or a pharmaceutically acceptable salt or solvate thereof, described herein are administered to subjects in a biologically compatible form suitable for administration to treat or prevent diseases, disorders or conditions. Administration of the compounds described herein can be in any pharmacological form including a therapeutically effective amount of a compound of Formula (I), (I'), (Ia), (Ia'), (Ib), (Ib'), (Ic), (Ic'), (II), (II'), (III), or (III'), or a pharmaceutically acceptable salt or solvate thereof, alone or in combination with a pharmaceutically acceptable carrier. The compounds of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), or a pharmaceutically acceptable salt or solvate thereof, described herein are administered to subjects in a biologically compatible form suitable for administration to treat or prevent diseases, disorders or conditions. Administration of the compounds described herein can be in any pharmacological form including a therapeutically effective amount of a compound of Formula (I-1), (I'-1), (Ia-1), (Ia'-1), (Ib-1), (Ib'-1), (Ic-1), (Ic'-1), (I-2), (I'-2), (Ia-2), (Ia'-2), (Ib-2), (Ib'-2), (Ic-2), or (Ic'-2), or a pharmaceutically acceptable salt or solvate thereof, alone or in combination with a pharmaceutically acceptable carrier.

In certain embodiments, the compounds described herein are administered as a pure chemical. In other embodiments, the compounds described herein are combined with a pharmaceutically suitable or acceptable carrier (also referred to herein as a pharmaceutically suitable (or acceptable) excipient, physiologically suitable (or acceptable) excipient, or physiologically suitable (or acceptable) carrier) selected on the basis of a chosen route of administration and standard pharmaceutical practice as described, for example, in Remington: The Science and Practice of Pharmacy (Gennaro, 21st Ed. Mack Pub. Co., Easton, Pa. (2005)).

Accordingly, provided herein is a pharmaceutical composition comprising at least one compound described herein, or a pharmaceutically acceptable salt, together with one or more pharmaceutically acceptable excipients. The excipient(s) (or carrier(s)) is acceptable or suitable if the excipient is compatible with the other ingredients of the composition and not deleterious to the recipient (i.e., the subject) of the composition.

In some embodiments is a pharmaceutical composition comprising a pharmaceutically acceptable excipient and a compound of Formula (I), (I'), (Ia), (Ia'), (Tb), (Ib'), (Ic), (Ic'), (II), (II'), (III), or (III'), or a pharmaceutically acceptable salt or solvate thereof. In some embodiments is a pharmaceutical composition comprising a pharmaceutically acceptable excipient and a compound of Formula (I), or a pharmaceutically acceptable salt or solvate thereof. In some embodiments is a pharmaceutical composition comprising a pharmaceutically acceptable excipient and a compound of Formula (I'), or a pharmaceutically acceptable salt or solvate thereof. In some embodiments is a pharmaceutical composition comprising a pharmaceutically acceptable excipient and a compound of Formula (Ia), or a pharmaceutically acceptable salt or solvate thereof. In some embodiments is a pharmaceutical composition comprising a pharmaceutically acceptable excipient and a compound of Formula (Ia'), or a pharmaceutically acceptable salt or solvate thereof. In some embodiments is a pharmaceutical composition comprising a pharmaceutically acceptable excipient and a compound of Formula (Ib), or a pharmaceutically acceptable salt or solvate thereof. In some embodiments is a pharmaceutical composition comprising a pharmaceutically acceptable excipient and a compound of Formula (Ib'), or a pharmaceutically acceptable salt or solvate thereof. In some embodiments is a pharmaceutical composition comprising a pharmaceutically acceptable excipient and a compound of Formula (Ic), or a pharmaceutically acceptable salt or solvate thereof. In some embodiments is a pharmaceutical composition comprising a pharmaceutically acceptable excipient and a compound of Formula (Ic'), or a pharmaceutically acceptable salt or solvate thereof. In some embodiments is a pharmaceutical composition comprising a pharmaceutically acceptable excipient and a compound of Formula (If), or a pharmaceutically acceptable salt or solvate thereof. In some embodiments is a pharmaceutical composition comprising a pharmaceutically acceptable excipient and a compound of Formula (II), or a pharmaceutically acceptable salt or solvate thereof. In some embodiments is a pharmaceutical composition comprising a pharmaceutically acceptable excipient and a compound of Formula (II'), or a pharmaceutically acceptable salt or solvate thereof. In some embodiments is a pharmaceutical composition comprising a pharmaceutically acceptable excipient and a compound of Formula (III), or a pharmaceutically acceptable salt or solvate thereof. In some embodiments is a pharmaceutical composition comprising a pharmaceutically acceptable excipient and a compound of Formula (III'), or a pharmaceutically acceptable salt or solvate thereof. In some embodiments is a pharmaceutical composition comprising a pharmaceutically acceptable excipient and a compound of Formula (I-1), (I'-1), (Ia-1), (Ia'-1), (Ib-1), (Ib'-1), (Ic-1), (Ic'-1), (1-2), (I'-2), (Ia-2), (Ia'-2), (Ib-2), (Ib'-2), (Ic-2), or (Ic'-2), or a pharmaceutically acceptable salt or solvate thereof. In some embodiments is a pharmaceutical composition comprising a pharmaceutically acceptable excipient and a compound of Formula (I-1), or a pharmaceutically acceptable salt or solvate thereof. In some embodiments is a pharmaceutical composition comprising a pharmaceutically acceptable excipient and a compound of Formula (I'-1), or a pharmaceutically acceptable salt or solvate thereof. In some embodiments is a pharmaceutical composition comprising a pharmaceutically acceptable excipient and a compound of Formula (Ia-1), or a pharmaceutically acceptable salt or solvate thereof. In some embodiments is a pharmaceutical composition comprising a pharmaceutically acceptable excipient and a compound of Formula (Ia'-1), or a pharmaceutically acceptable salt or solvate thereof. In some embodiments is a pharmaceutical composition comprising a pharmaceutically acceptable excipient and a compound of Formula (Ib-1), or a pharmaceutically acceptable salt or solvate thereof. In some embodiments is a pharmaceutical composition comprising a pharmaceutically acceptable excipient and a compound of Formula (Ib'-1), or a pharmaceutically acceptable salt or solvate thereof. In some embodiments is a pharmaceutical composition comprising a pharmaceutically acceptable excipient and a compound of Formula (Ic-1), or a pharmaceutically acceptable salt or solvate thereof. In some embodiments is a pharmaceutical composition comprising a pharmaceutically acceptable excipient and a compound of Formula (Ic'-1), or a pharmaceutically acceptable salt or solvate thereof. In some embodiments is a pharmaceutical composition comprising a pharmaceutically acceptable excipient and a compound of Formula (1-2), or a pharmaceutically acceptable salt or solvate thereof. In some embodiments is a pharmaceutical composition comprising a pharmaceutically acceptable excipient and a compound of Formula (I'-2), or a pharmaceutically acceptable salt or solvate thereof. In some embodiments is a pharmaceutical composition comprising a pharmaceutically acceptable excipient and a compound of Formula (Ia-2), or a pharmaceutically acceptable salt or solvate thereof. In some embodiments is a pharmaceutical composition comprising a pharmaceutically acceptable excipient and a compound of Formula (Ia'-2), or a pharmaceutically acceptable salt or solvate thereof. In some embodiments is a pharmaceutical composition comprising a pharmaceutically acceptable excipient and a compound of Formula (Ib-2), or a pharmaceutically acceptable salt or solvate thereof. In some embodiments is a pharmaceutical composition comprising a pharmaceutically acceptable excipient and a compound of Formula (Ib'-2), or a pharmaceutically acceptable salt or solvate thereof. In some embodiments is a pharmaceutical composition comprising a pharmaceutically acceptable excipient and a compound of Formula (Ic-2), or a pharmaceutically acceptable salt or solvate thereof. In some embodiments is a pharmaceutical composition comprising a pharmaceutically acceptable excipient and a compound of Formula (Ic'-2), or a pharmaceutically acceptable salt or solvate thereof.

In some embodiments of the methods described herein, the compounds described herein are administered either alone or in combination with pharmaceutically acceptable carriers, excipients or diluents, in a pharmaceutical composition. Administration of the compounds and compositions described herein can be affected by any method that enables delivery of the compounds to the site of action. These methods include, though are not limited to delivery via enteral routes (including oral, gastric or duodenal feeding tube, rectal suppository and rectal enema), parenteral routes (injection or infusion, including intraarterial, intracardiac, intradermal, intraduodenal, intramedullary, intramuscular, intraosseous, intraperitoneal, intrathecal, intravascular, intravenous, intravitreal, epidural and subcutaneous), inhalational, transdermal, transmucosal, sublingual, buccal and topical (including epicutaneous, dermal, enema, eye drops, ear drops, intranasal, vaginal) administration, although the most suitable route may depend upon for example the condition and disorder of the recipient. By way of example only, compounds described herein can be administered locally to the area in need of treatment, by for example, local infusion during surgery, topical application such as creams or ointments, injection, catheter, or implant. The administration can also be by direct injection at the site of a diseased tissue or organ.

In some embodiments of the methods described herein, pharmaceutical compositions suitable for oral administration are presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. In some embodiments, the active ingredient is presented as a bolus, electuary or paste.

Pharmaceutical compositions which can be used orally include tablets, push-fit capsules made of gelatin, as well as soft, sealed capsules made of gelatin and a plasticizer, such as glycerol or sorbitol. Tablets may be made by compression or molding, optionally with one or more accessory ingredients. Compressed tablets may be prepared by compressing in a suitable machine the active ingredient in a free-flowing form such as a powder or granules, optionally mixed with binders, inert diluents, or lubricating, surface active or dispersing agents. Molded tablets may be made by molding in a suitable machine a mixture of the powdered compound moistened with an inert liquid diluent. In some embodiments, the tablets are coated or scored and are formulated so as to provide slow or controlled release of the active ingredient therein. All formulations for oral administration should be in dosages suitable for such administration. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In some embodiments, stabilizers are added. Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or Dragee coatings for identification or to characterize different combinations of active compound doses.

In some embodiments of the methods described herein, pharmaceutical compositions are formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. The compositions may be presented in unit-dose or multi-dose containers, for example sealed ampoules and vials, and may be stored in powder form or in a freeze-dried (lyophilized) condition requiring only the addition of the sterile liquid carrier, for example, saline or sterile pyrogen-free water, immediately prior to use. Extemporaneous injection solutions and suspensions may be prepared from sterile powders, granules and tablets of the kind previously described.

Pharmaceutical compositions for parenteral administration include aqueous and non-aqueous (oily) sterile injection solutions of the active compounds which may contain antioxidants, buffers, bacteriostats and solutes which render the formulation isotonic with the blood of the intended recipient; and aqueous and non-aqueous sterile suspensions which may include suspending agents and thickening agents. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Pharmaceutical compositions may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example, as an emulsion in an acceptable oil) or ion exchange resins, or as sparingly soluble derivatives, for example, as a sparingly soluble salt.

Additional Embodiments

Embodiment 1. A compound of Formula (I-1), or a pharmaceutically acceptable salt or solvate thereof:

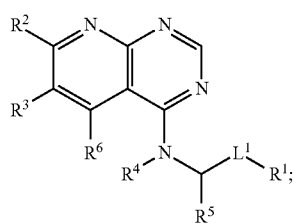

Formula (I-I)

wherein:
$R^1$ is a 6-10 membered aryl ring optionally substituted with one or more $R^{10}$;
$L^1$ is a bond;
$R^2$ is $-OR^{2a}$ or halogen;
$R^{2a}$ is selected from hydrogen, $C_{1-6}$alkyl, $C_{3-10}$cycloalkyl, $C_{2-9}$heterocycloalkyl, $C_{6-10}$aryl, $C_{1-9}$heteroaryl, wherein $C_{1-6}$alkyl, $C_{3-10}$cycloalkyl, $C_{2-9}$heterocycloalkyl, $C_{6-10}$aryl, and $C_{1-9}$heteroaryl are optionally substituted with one, two, or three $R^{20a}$;
$R^3$ is selected from halogen, $C_{1-6}$alkyl, $C_{3-14}$cycloalkyl, $C_{2-9}$heterocycloalkyl, $C_{6-10}$aryl, and $C_{1-9}$heteroaryl, wherein $C_{1-6}$alkyl, $C_{3-14}$cycloalkyl, $C_{2-9}$heterocycloalkyl, $C_{6-10}$aryl, and $C_{1-9}$heteroaryl are optionally substituted with one, two, or three $R^{20b}$;
$R^4$ is selected from hydrogen, $C_{1-6}$alkyl, and $C_{1-6}$haloalkyl;
$R^5$ is selected from hydrogen, $C_{1-6}$alkyl, and $C_{1-6}$haloalkyl;
$R^6$ is selected from hydrogen, halogen, $-CN$, and $C_{1-6}$alkyl, wherein $C_{1-6}$alkyl is optionally substituted with one, two, or three $R^{20c}$;
each $R^{10}$ is independently selected from halogen, $-CN$, $C_{1-6}$alkyl, $C_{3-7}$cycloalkyl, $C_{2-9}$heterocycloalkyl, $C_{6-10}$aryl, $C_{1-9}$heteroaryl, wherein $C_{1-6}$alkyl, $C_{3-7}$cycloalkyl, $C_{2-9}$heterocycloalkyl, $C_{6-10}$aryl, and $C_{1-9}$heteroaryl are optionally substituted with one, two, or three $R^{20d}$;
each $R^{20a}$, $R^{20b}$, $R^{20c}$, and $R^{20d}$ are each independently selected from halogen, oxo, $=NH$, $-CN$, $C_{1-6}$alkyl, $C_{2-6}$alkenyl, $C_{2-6}$alkynyl, $C_{3-10}$cycloalkyl, $-CH_2-C_{3-10}$cycloalkyl, $C_{2-9}$heterocycloalkyl, $-CH_2-C_{2-9}$heterocycloalkyl, $C_{6-10}$aryl, $-CH_2-C_{6-10}$aryl, $C_{1-9}$heteroaryl, $-OR^{21}$, $-SR^{21}$, $-N(R^{22})(R^{23})$, $-C(O)OR^{22}$, $-C(O)N(R^{22})(R^{23})$, $-C(O)C(O)N(R^{22})(R^{23})$, $-OC(O)N(R^{22})(R^{23})$, $-N(R^{24})C(O)N(R^{22})(R^{23})$, $-N(R^{24})C(O)OR^{25}$, $-N(R^{24})C(O)R^{25}$, $-N(R^{24})S(O)_2R^{25}$, $-C(O)R^{25}$, $-S(O)_2R^{25}$, $-S(O)_2N(R^{22})(R^{23})$, $-OCH_2C(O)OR^{22}$, and $-OC(O)R^{25}$, wherein $C_{1-6}$alkyl, $C_{2-6}$alkenyl, $C_{2-6}$alkynyl, $C_{3-10}$cycloalkyl, $-CH_2-C_{3-10}$cycloalkyl, $C_{2-9}$heterocycloalkyl, $-CH_2-C_{2-9}$heterocycloalkyl, $C_{6-10}$aryl, $-CH_2-C_{6-10}$aryl, and $C_{1-9}$heteroaryl are optionally substituted with one, two, or three groups independently selected from halogen, oxo, $=NH$, $-CN$, $C_{1-6}$alkyl, $C_{1-6}$haloalkyl, $C_{1-6}$alkoxy, $C_{1-6}$haloalkoxy, $-OR^{21}$, $-SR^{21}$, $-N(R^{22})(R^{23})$, $-C(O)OR^{22}$, $-C(O)N(R^{22})(R^{23})$, $-C(O)C(O)N(R^{22})(R^{23})$, $-OC(O)N(R^{22})(R^{23})$, $-N(R^{24})C(O)N(R^{22})(R^{23})$, $-N(R^{24})C(O)OR^{25}$, $-N(R^{24})C(O)R^{25}$, $-N(R^{24})S(O)_2R^{25}$, $-C(O)R^{25}$, $-S(O)_2R^{25}$, $-S(O)_2N(R^{22})(R^{23})$, and $-OC(O)R^{25}$;
each $R^{21}$ is independently selected from H, $C_{1-6}$alkyl, $C_{1-6}$haloalkyl, $C_{2-6}$alkenyl, $C_{2-6}$alkynyl, $C_{3-7}$cycloalkyl, $C_{2-9}$heterocycloalkyl, $C_{6-10}$aryl, and $C_{1-9}$heteroaryl, wherein $C_{3-7}$cycloalkyl, $C_{2-9}$heterocycloalkyl, $C_{6-10}$aryl, and $C_{1-9}$heteroaryl are optionally substituted with one, two, or three groups independently selected from halogen and $C_{1-6}$alkyl;
each $R^{22}$ is independently selected from H, $C_{1-6}$alkyl, $C_{1-6}$haloalkyl, $C_{2-6}$alkenyl, $C_{2-6}$alkynyl, $C_{3-7}$cycloalkyl, $C_{2-9}$heterocycloalkyl, $C_{6-10}$aryl, and $C_{1-9}$heteroaryl, wherein $C_{3-7}$cycloalkyl, $C_{2-9}$heterocycloalkyl, $C_{6-10}$aryl, and $C_{1-9}$heteroaryl are optionally substituted with one, two, or three groups independently selected from halogen and $C_{1-6}$alkyl;
each $R^{23}$ is independently selected from H and $C_{1-6}$alkyl;
each $R^{24}$ is independently selected from H and $C_{1-6}$alkyl; and
each $R^{25}$ is selected from $C_{1-6}$alkyl, $C_{2-6}$alkenyl, $C_{2-6}$alkynyl, $C_{3-7}$cycloalkyl, $C_{2-9}$heterocycloalkyl, $C_{6-10}$aryl, and $C_{1-9}$heteroaryl, wherein $C_{1-6}$alkyl, $C_{3-7}$cycloalkyl, $C_{2-9}$heterocycloalkyl, $C_{6-10}$aryl, and $C_{1-9}$heteroaryl are optionally substituted with one, two, or three groups independently selected from halogen, $C_{1-6}$alkyl, $C_{1-6}$haloalkyl, $C_{1-6}$alkoxy, $C_{3-7}$cycloalkyl, $C_{2-9}$heterocycloalkyl, $C_{6-10}$aryl, and $C_{1-9}$heteroaryl.

Embodiment 2. The compound of Embodiment 1 having the structure of Formula (Ia-1), or a pharmaceutically acceptable salt or solvate thereof:

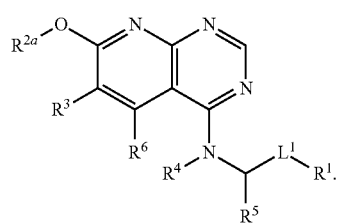

Formula (Ia-1)

Embodiment 3. The compound of Embodiment 2, or a pharmaceutically acceptable salt or solvate thereof, wherein $R^{2a}$ is $C_{1-6}$alkyl optionally substituted with one, two, or three $R^{20a}$.

Embodiment 4. The compound of Embodiment 3, or a pharmaceutically acceptable salt or solvate thereof, wherein $R^{2a}$ is unsubstituted $C_{1-6}$alkyl.

Embodiment 5. The compound of Embodiment 4, or a pharmaceutically acceptable salt or solvate thereof, wherein $R^{2a}$ is $-CH_3$.

Embodiment 6. The compound of Embodiment 1, or a pharmaceutically acceptable salt or solvate thereof, wherein $R^3$ is $C_{2-9}$heterocycloalkyl optionally substituted with one, two, or three $R^{20b}$.

Embodiment 7. The compound of Embodiment 1, or a pharmaceutically acceptable salt or solvate thereof, wherein $R^3$ is $C_{3-10}$cycloalkyl optionally substituted with one, two, or three $R^{20b}$.

Embodiment 8. The compound of Embodiment 7, or a pharmaceutically acceptable salt or solvate thereof, wherein $R^3$ is $C_{3-4}$cycloalkyl optionally substituted with one $R^{20b}$.

Embodiment 9. The compound of Embodiment 8, or a pharmaceutically acceptable salt or solvate thereof, wherein $R^{20b}$ is —CN or halogen.

Embodiment 10. The compound of Embodiment 9, or a pharmaceutically acceptable salt or solvate thereof, wherein $R^3$ is

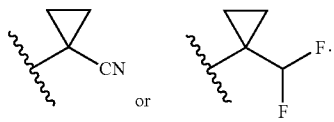

Embodiment 11. The compound of Embodiment 1, or a pharmaceutically acceptable salt or solvate thereof, wherein $R^6$ is selected from hydrogen, halogen, and unsubstituted $C_{1-6}$alkyl.

Embodiment 12. The compound of Embodiment 11, or a pharmaceutically acceptable salt or solvate thereof, wherein $R^6$ is hydrogen.

Embodiment 13. The compound of Embodiment 1, or a pharmaceutically acceptable salt or solvate thereof, wherein $R^5$ is $C_{1-6}$alkyl.

Embodiment 14. The compound of Embodiment 13, or a pharmaceutically acceptable salt or solvate thereof, wherein $R^5$ is —CH$_3$.

Embodiment 15. The compound of Embodiment 1, or a pharmaceutically acceptable salt or solvate thereof, wherein $R^4$ is hydrogen.

Embodiment 16. The compound of Embodiment 1, or a pharmaceutically acceptable salt or solvate thereof, wherein $R^1$ is phenyl substituted with one or more $R^{10}$.

Embodiment 17. The compound of Embodiment 16, or a pharmaceutically acceptable salt or solvate thereof, wherein each $R^1$ is independently selected from halogen and $C_{1-6}$alkyl, wherein $C_{1-6}$alkyl is optionally substituted with one, two, or three $R^{20a}$.

Embodiment 18. The compound of Embodiment 17 any one of Embodiments 37-43, or a pharmaceutically acceptable salt or solvate thereof, wherein each $R^1$ is independently selected from halogen and $C_{1-6}$alkyl, wherein $C_{1-6}$alkyl is substituted with one, two, or three $R^{20d}$, and each $R^{20d}$ is halogen or —OH.

Embodiment 19. The compound of Embodiment 17, or a pharmaceutically acceptable salt or solvate thereof, wherein $R^1$ is independently selected from

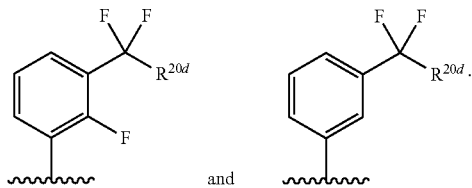

Embodiment 20. The compound of Embodiment 19, or a pharmaceutically acceptable salt or solvate thereof, wherein $R^{20d}$ is $C_{1-6}$alkyl optionally substituted with one, two, or three groups independently selected from F and —OH.

Embodiment 21. The compound of Embodiment 20, or a pharmaceutically acceptable salt or solvate thereof, wherein $R^{20d}$ is $C_{1-3}$alkyl substituted with one —OH.

Embodiment 22. The compound of Embodiment 21, or a pharmaceutically acceptable salt or solvate thereof, wherein $R^1$ is selected from

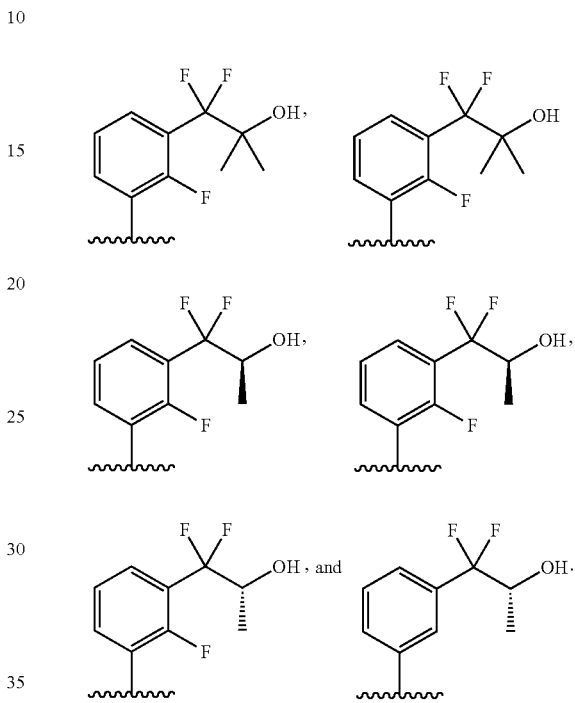

Embodiment 23. A compound selected from:

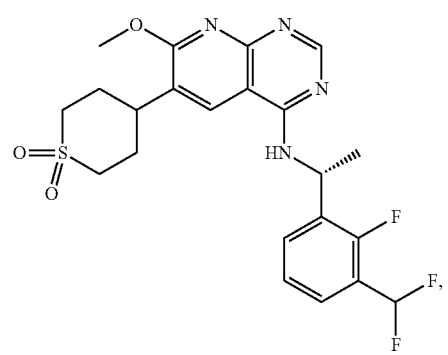

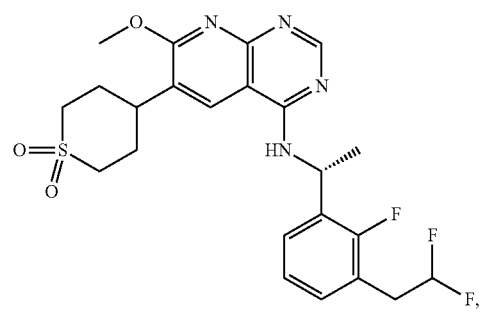

873
-continued
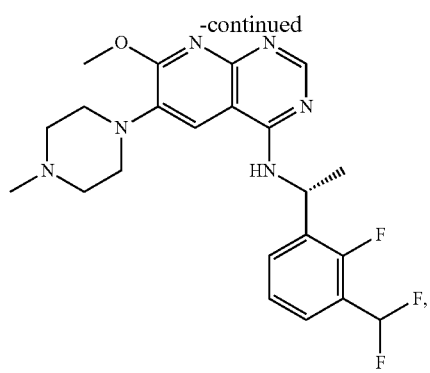
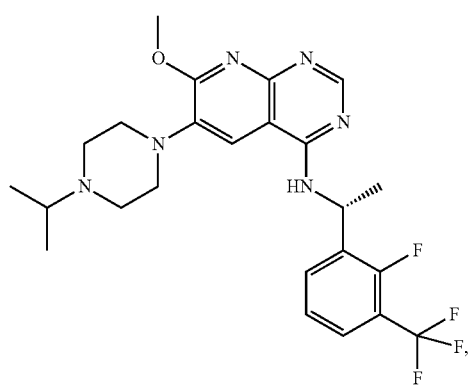
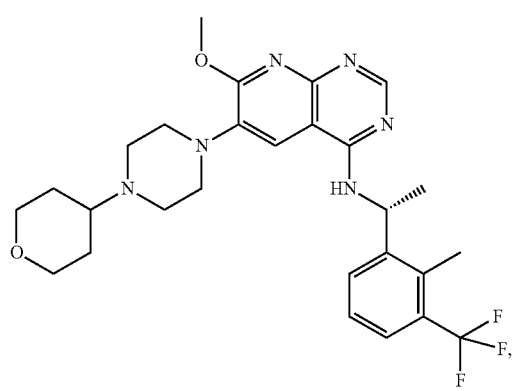
874
-continued
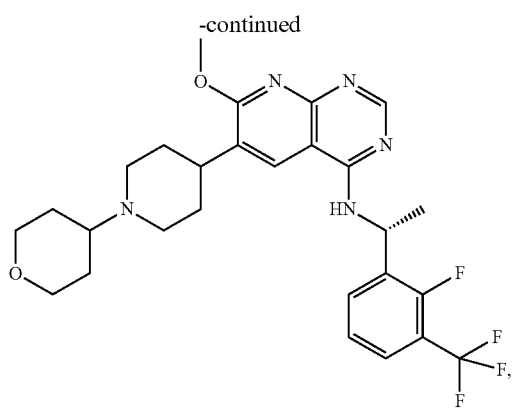
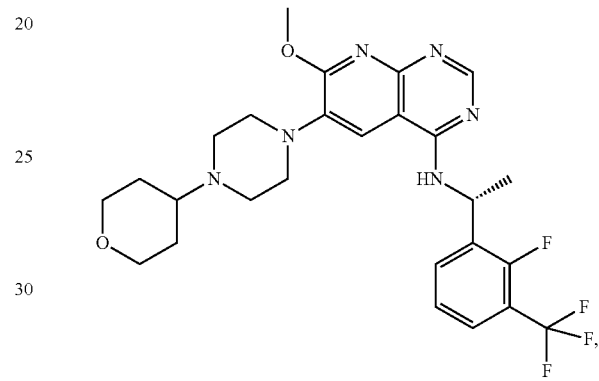

875
-continued
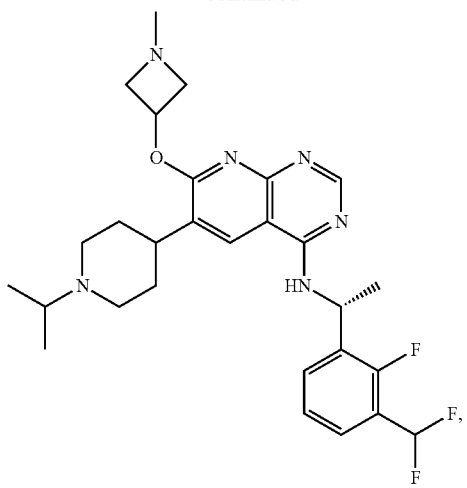
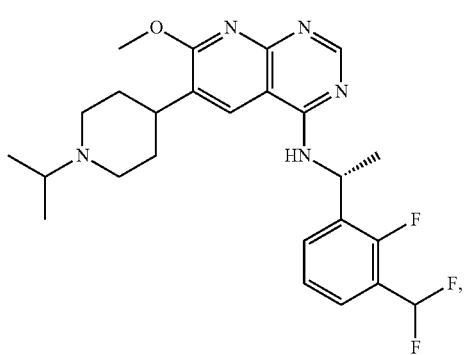
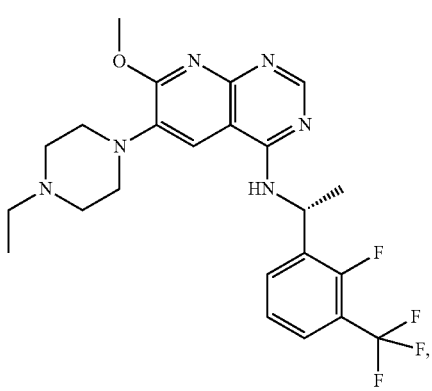
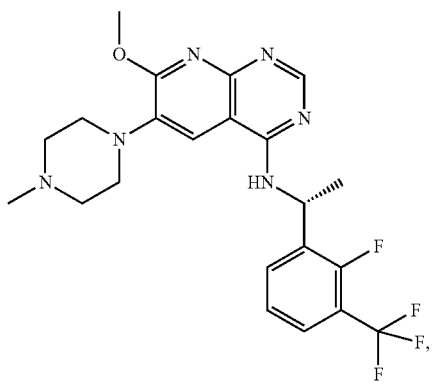
876
-continued
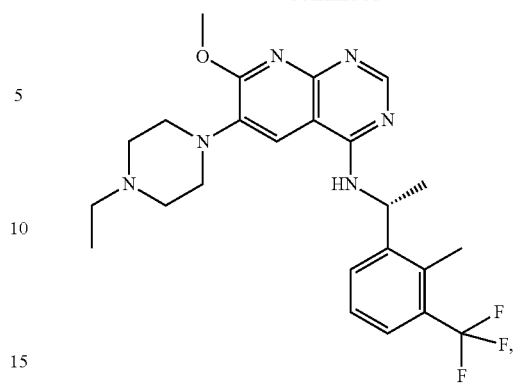
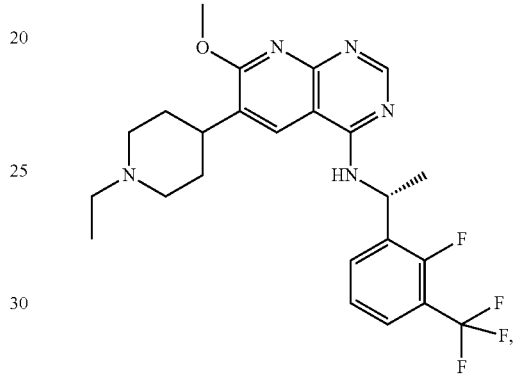
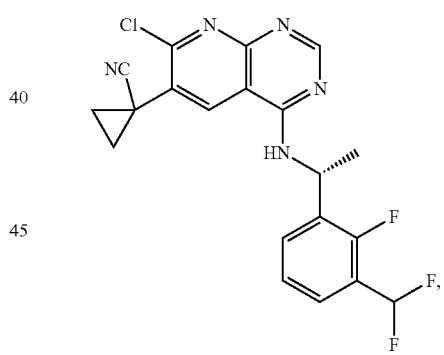
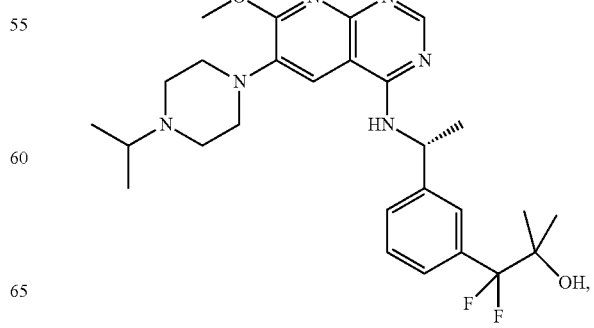

877
-continued
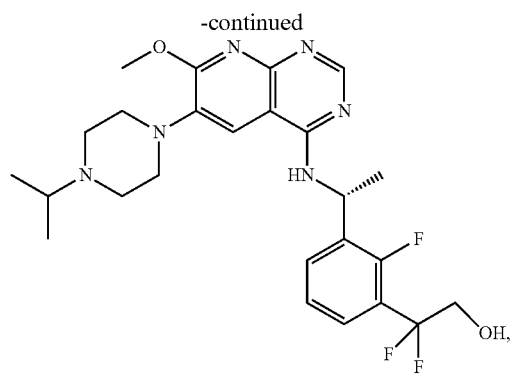
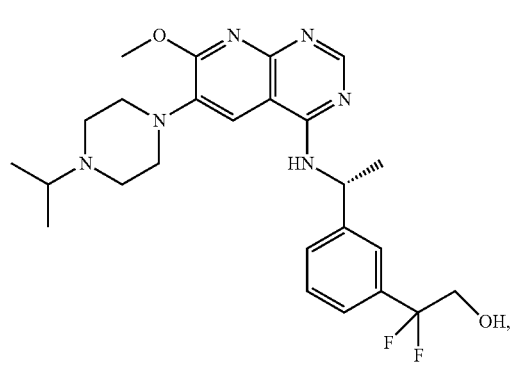
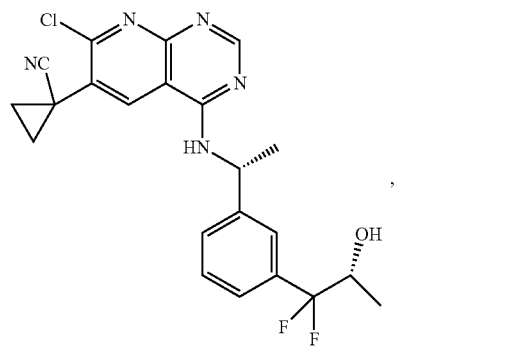
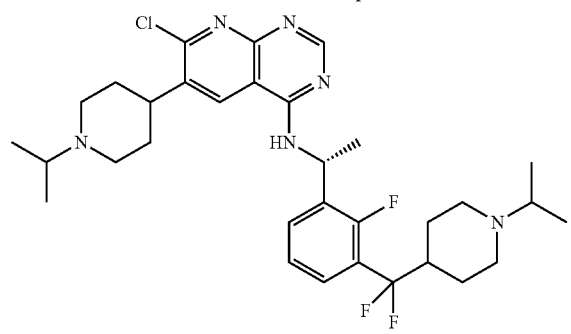
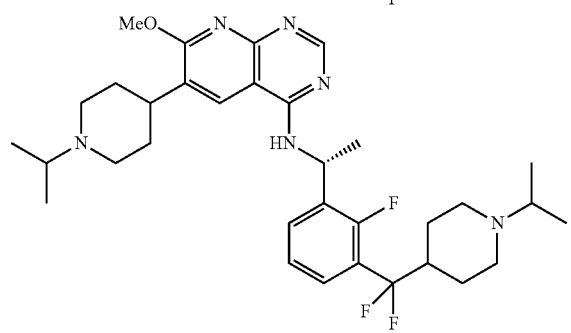
878
-continued
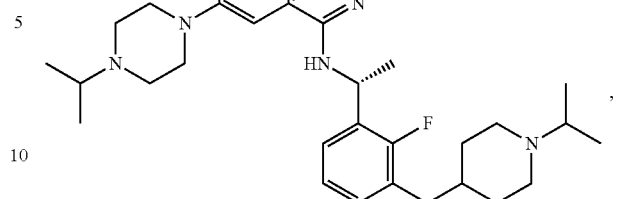
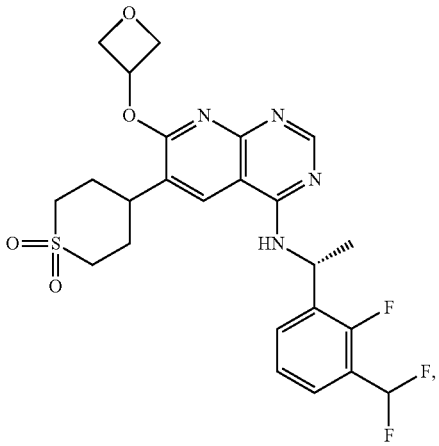
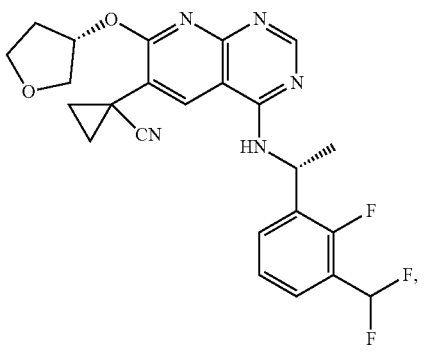
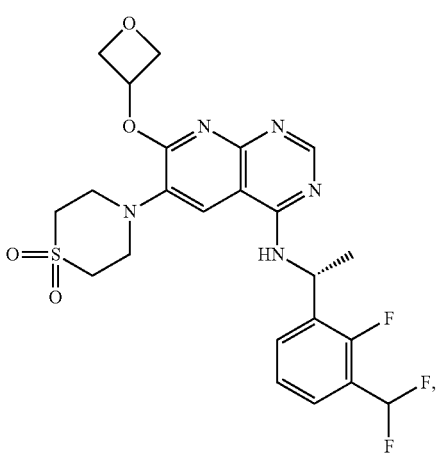

879
-continued
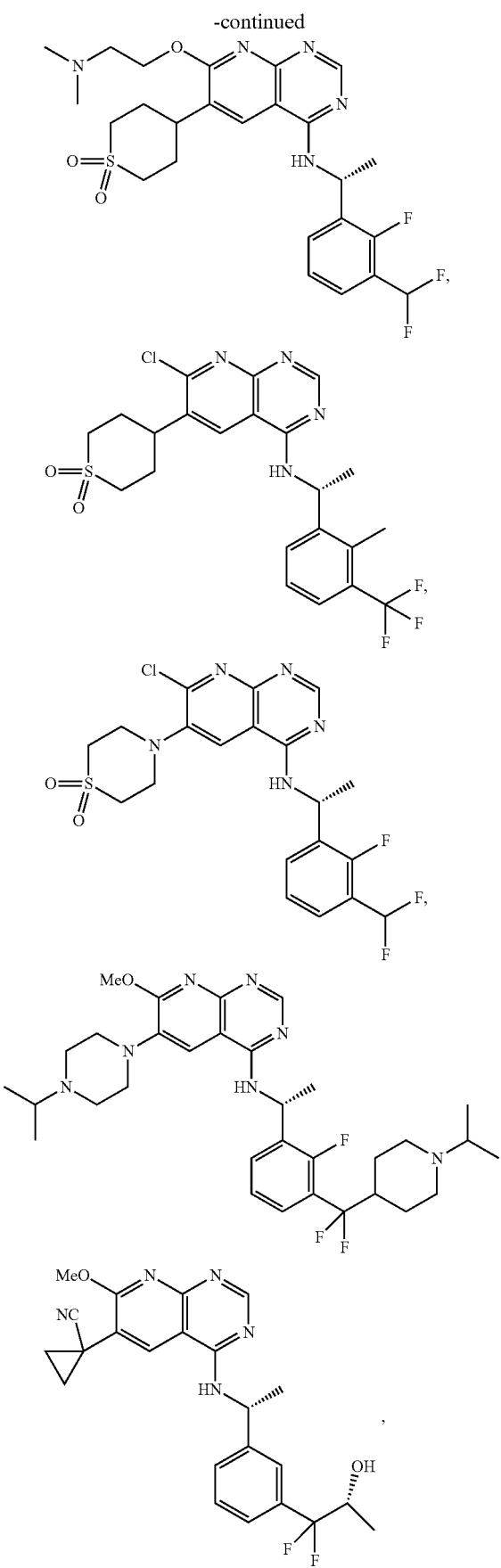
880
-continued
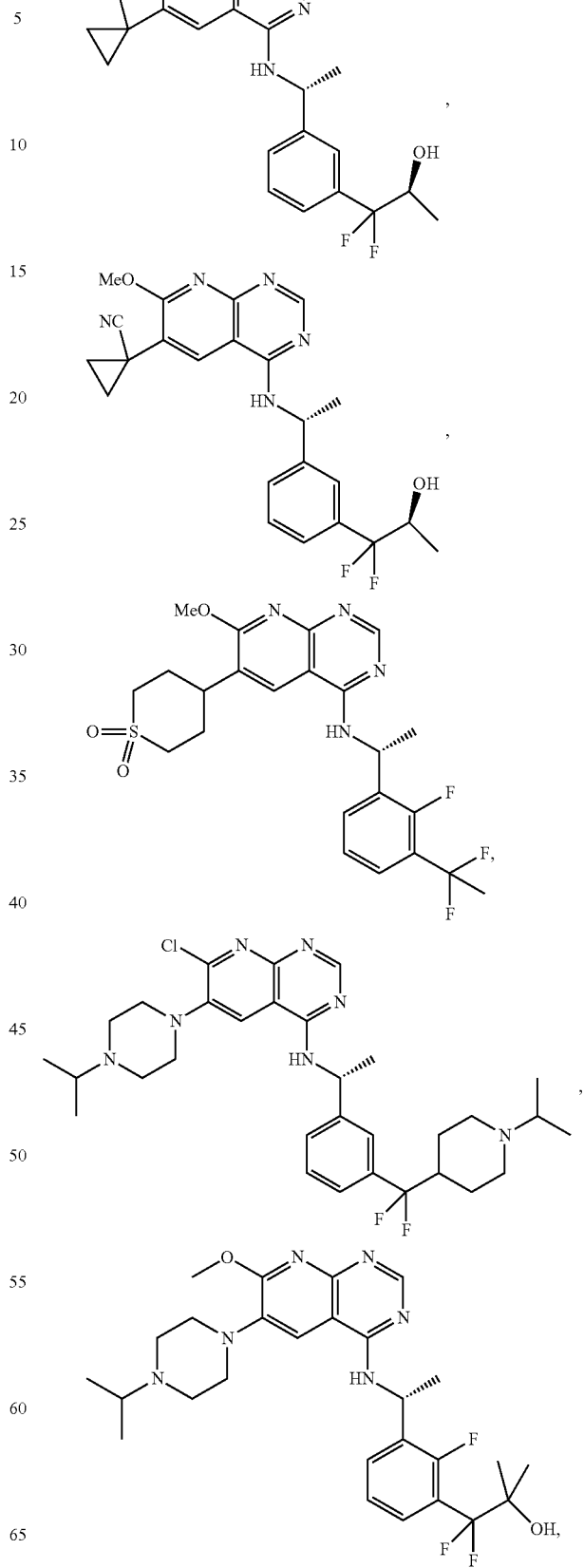

881
-continued
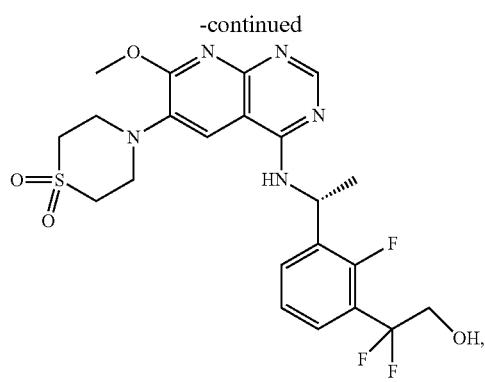
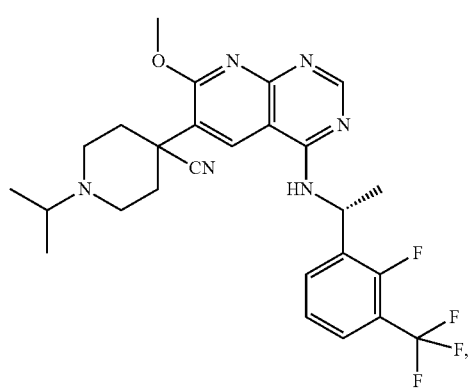
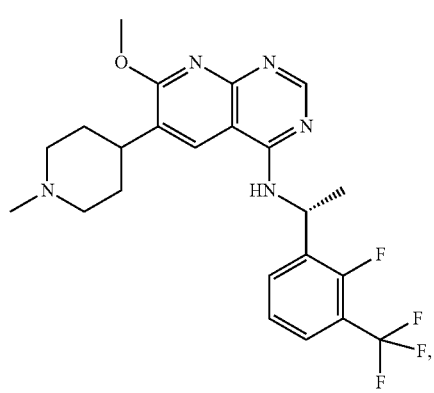
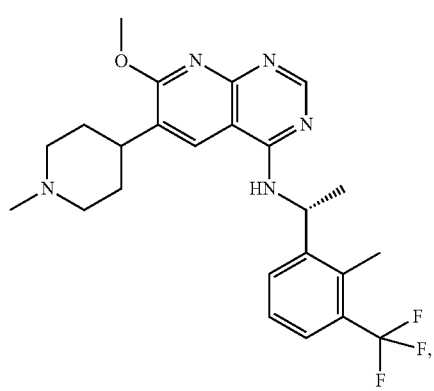
882
-continued
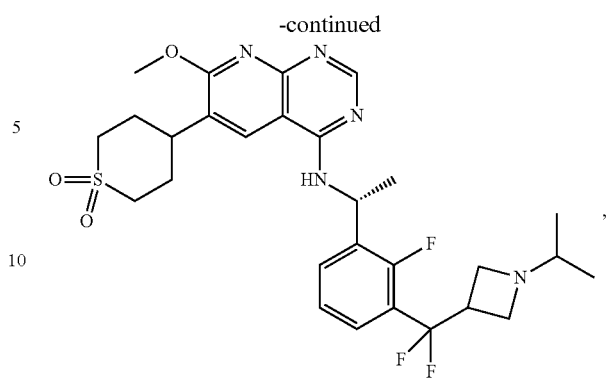
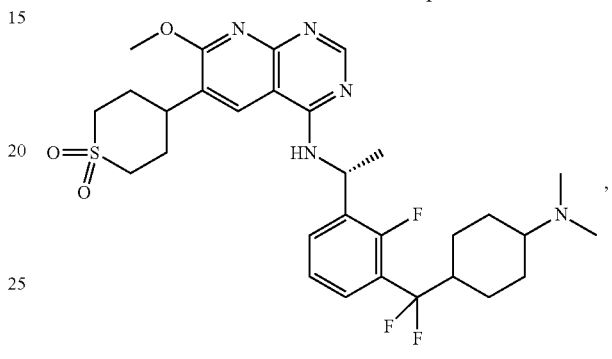
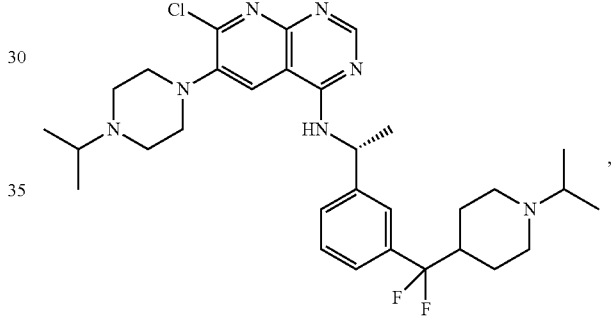
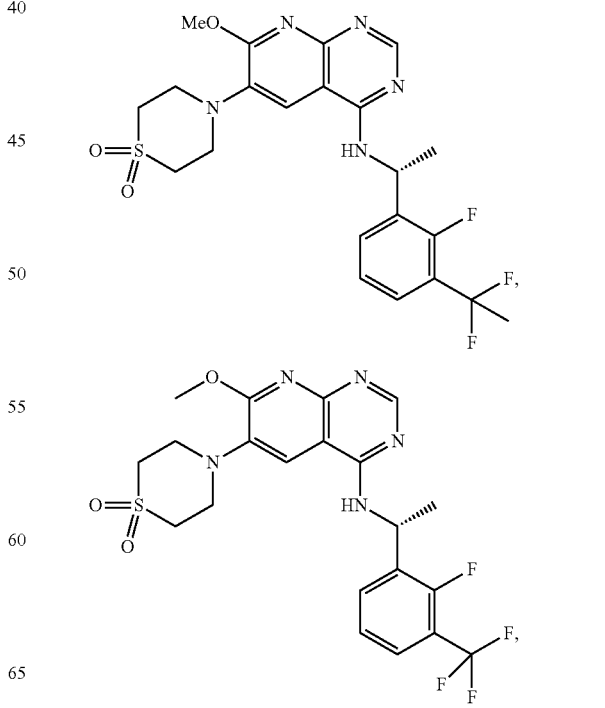

883
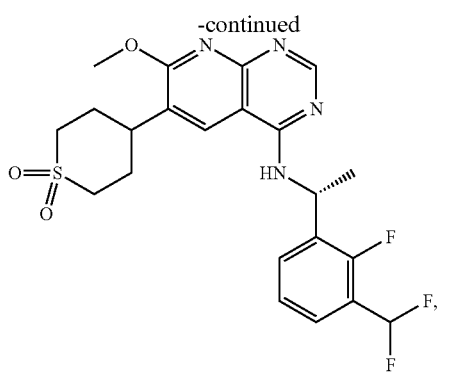
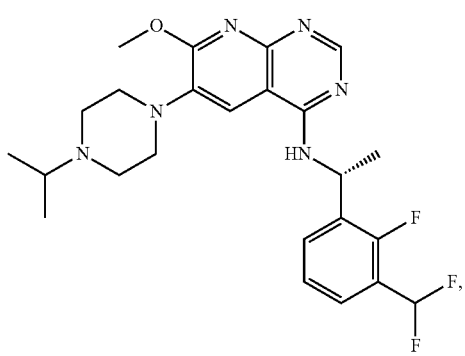
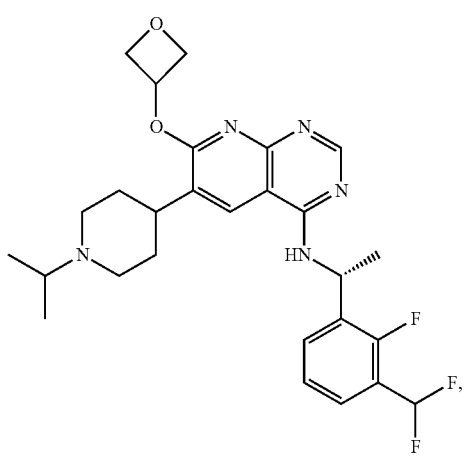
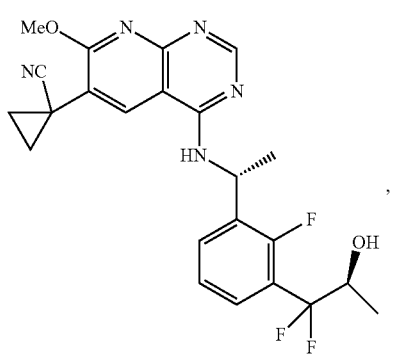
884
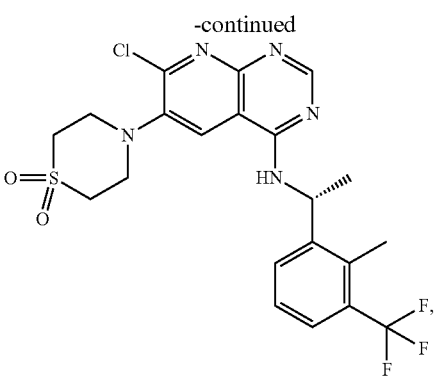
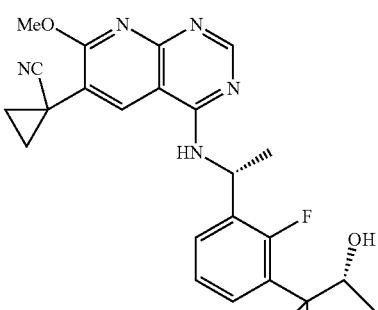
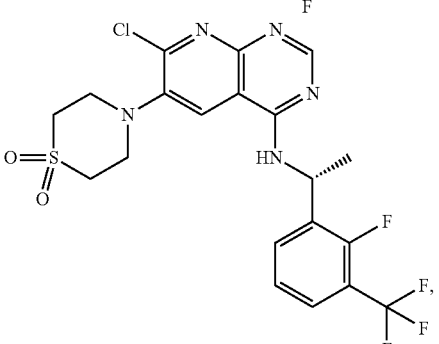
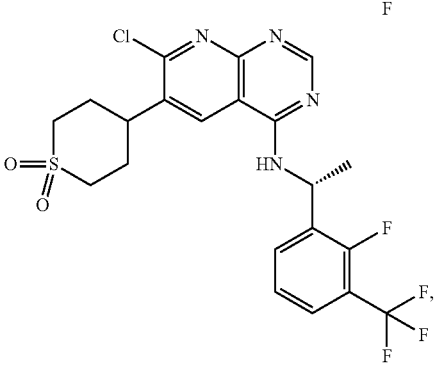
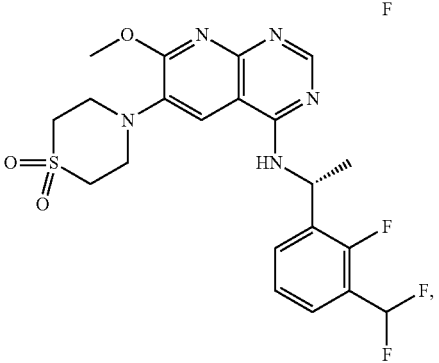

885
-continued
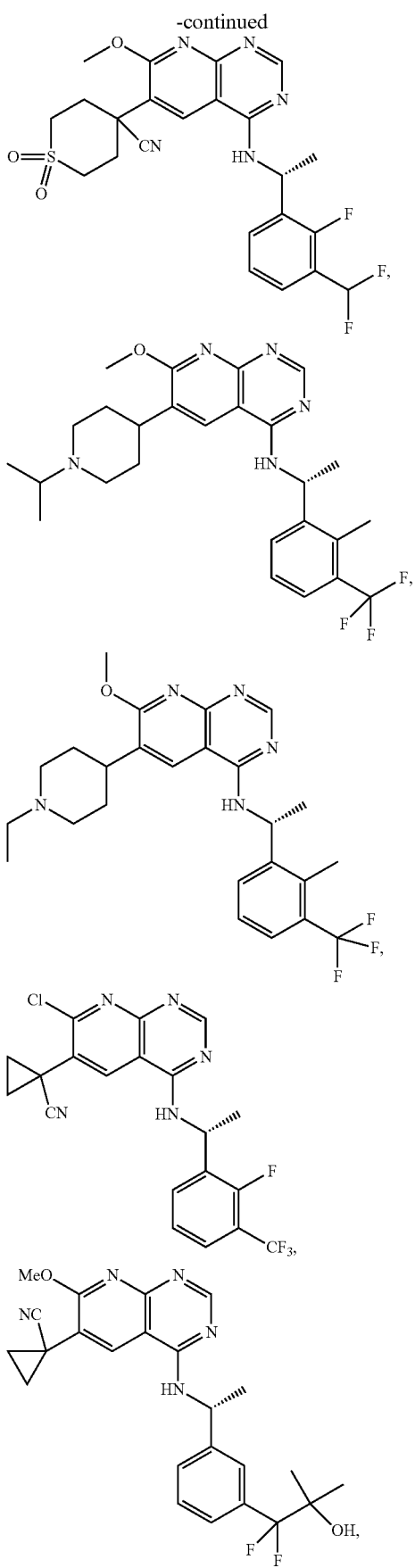
886
-continued
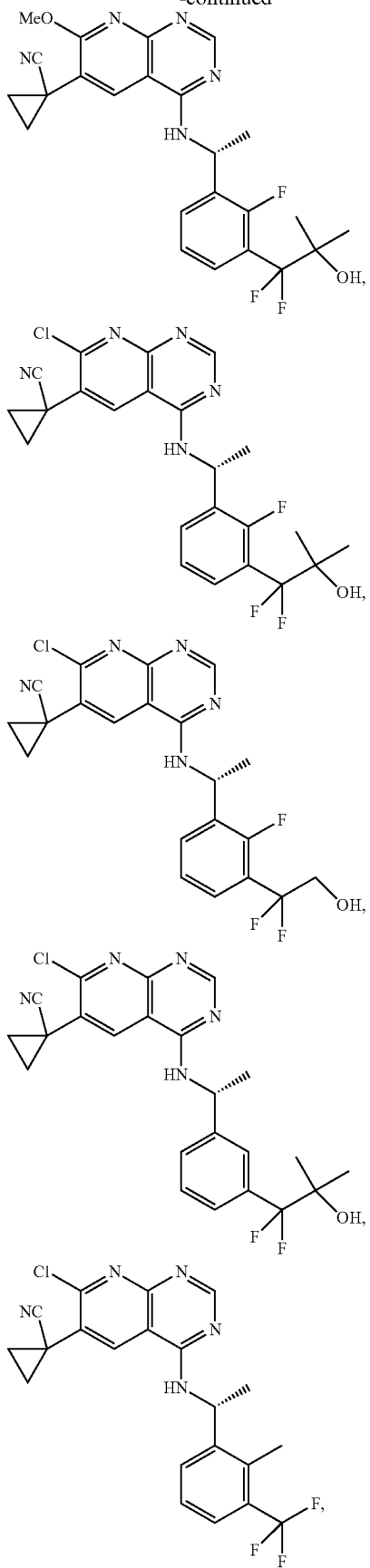

887
-continued
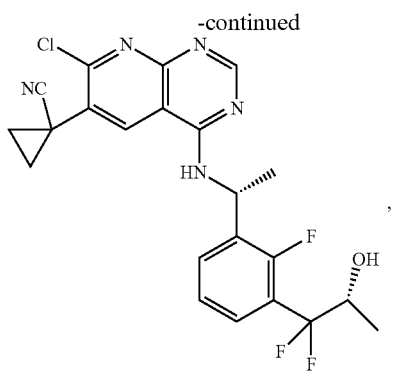
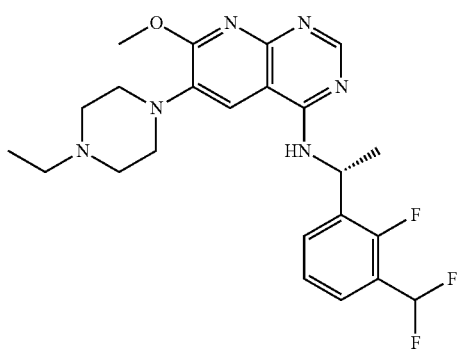
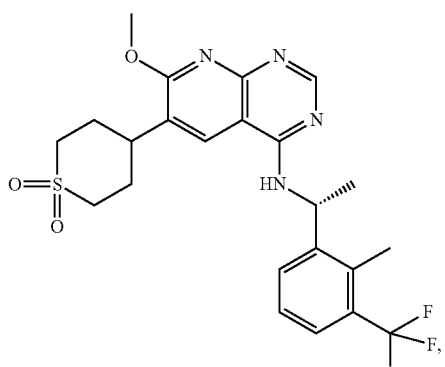
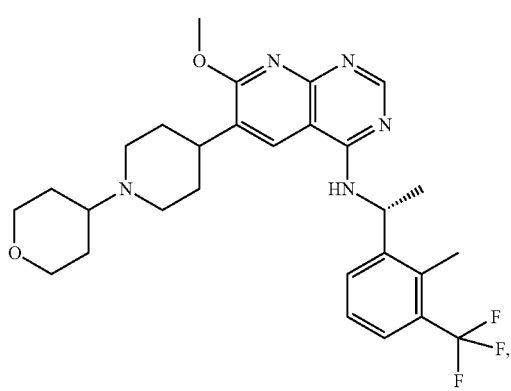
888
-continued
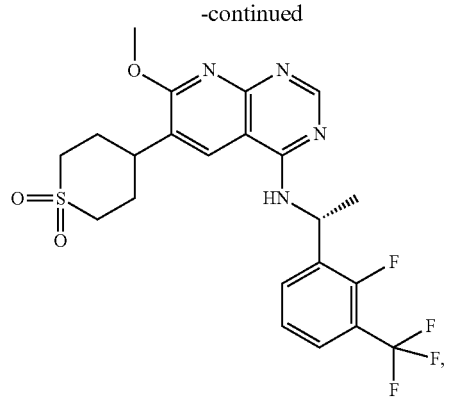
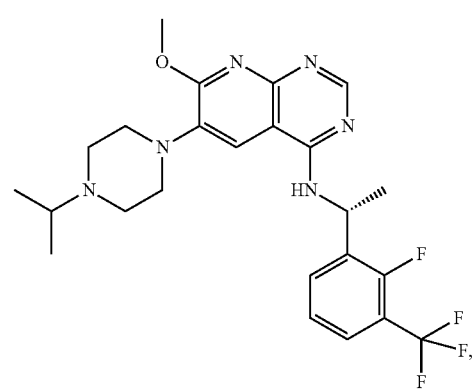
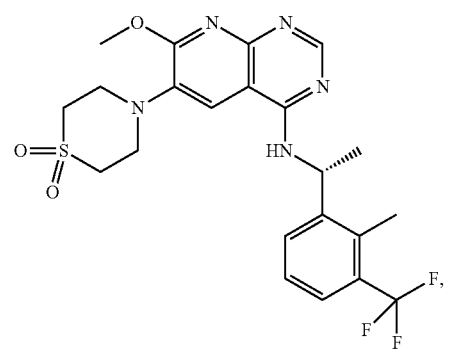
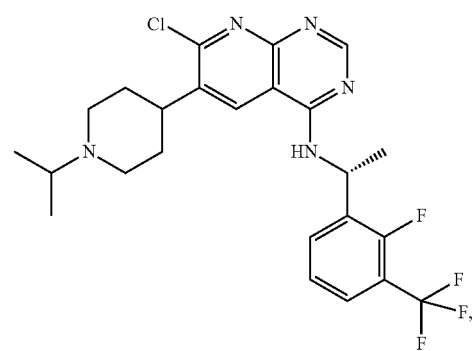 [SMILES: Cc1c([C@@H](C)Nc2ncnc3nc(Cl)c(C4CCN(C(C)C)CC4)cc23)cccc1C(F)(F)F]

889
-continued
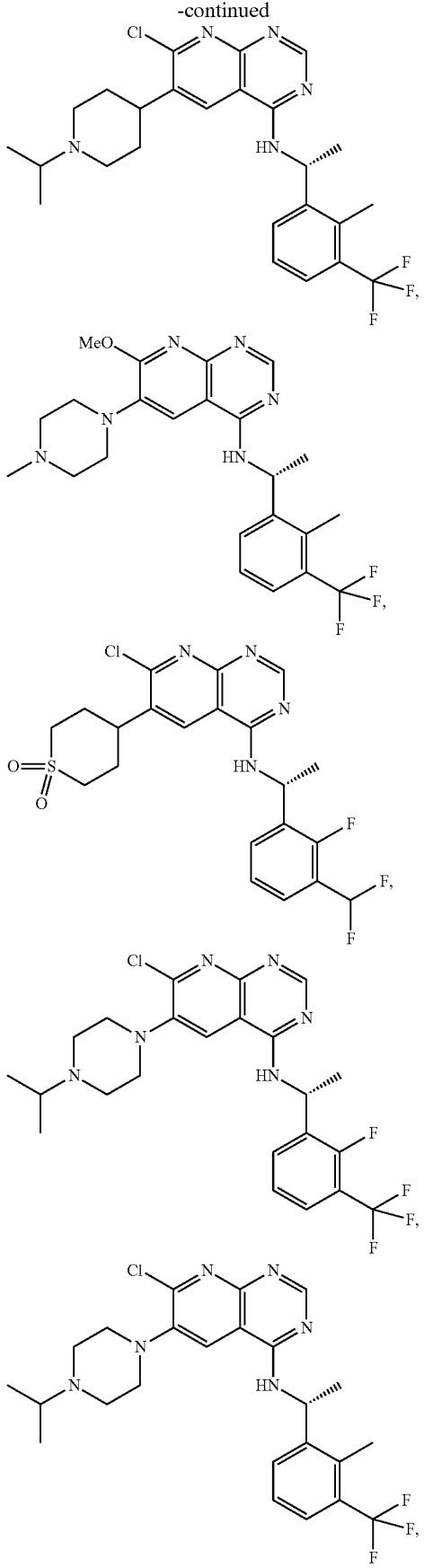
890
-continued
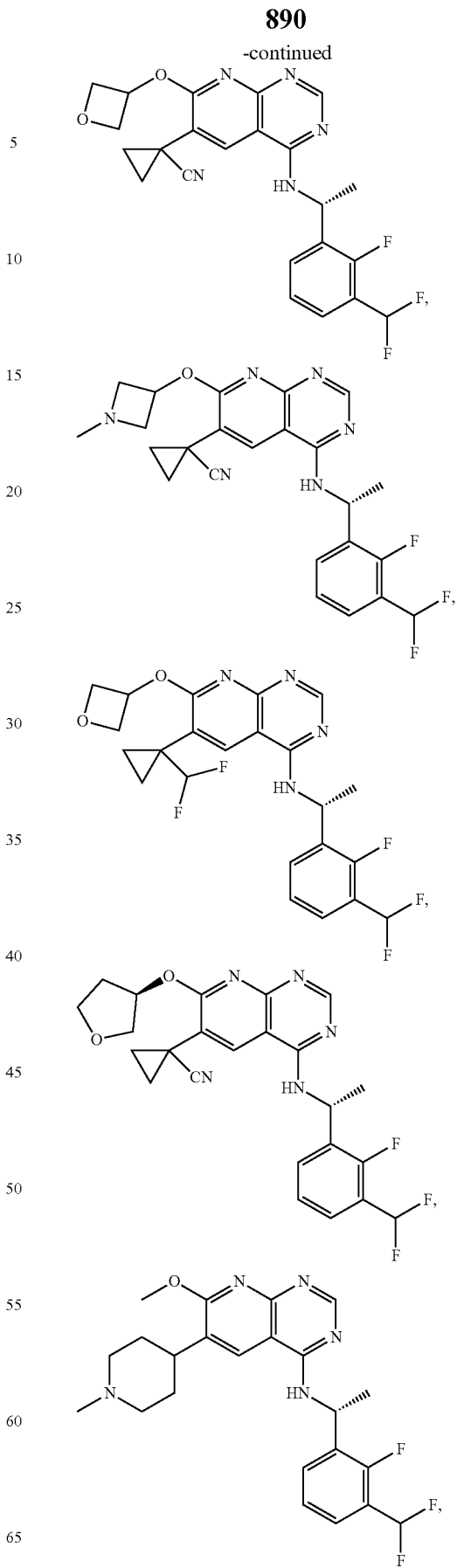

891
-continued

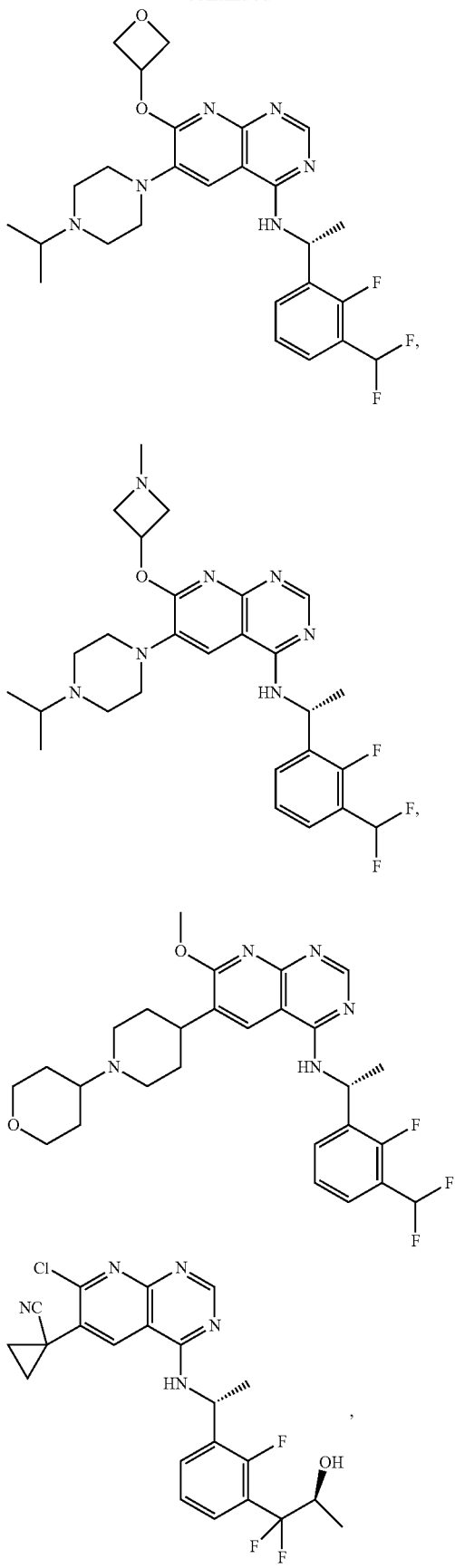

892
-continued

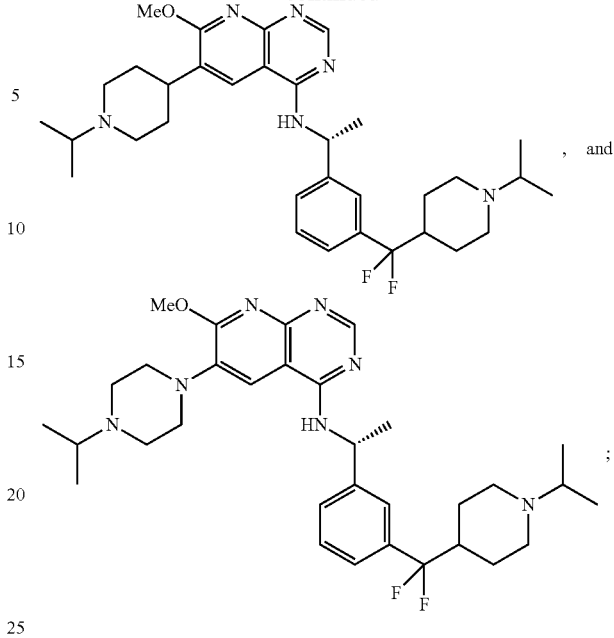

or a pharmaceutically acceptable salt or solvate thereof.

Embodiment 24. A pharmaceutical composition comprising a compound of any one of Embodiments 1-23, or a pharmaceutically acceptable salt or solvate thereof, and a pharmaceutically acceptable excipient.

Embodiment 25. A method of inhibiting cell growth, comprising administering a cell expressing SOS1 with an effective amount of a compound of any one of Embodiments 1-23, or a pharmaceutically acceptable salt or solvate thereof, thereby inhibiting growth of said cells.

Embodiment 26. The method of Embodiment 25, wherein the cell is a cancer cell.

Embodiment 27. The method of Embodiment 25, further comprising administering an additional agent to the cell.

Embodiment A1. A compound of Formula (I), or a pharmaceutically acceptable salt or solvate thereof:

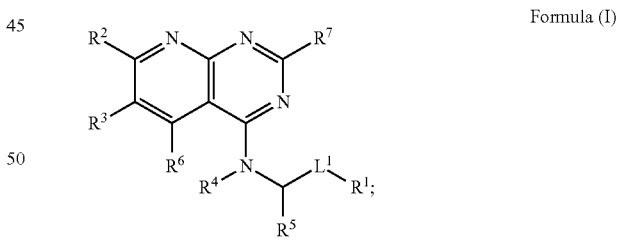

Formula (I)

wherein:
R$^1$ is a 3-12 membered cycloalkyl ring, 3-12 membered heterocycloalkyl ring, 6-10 membered aryl ring, or 5-10 membered heteroaryl ring, wherein the 3-12 membered cycloalkyl ring, 3-12 membered heterocycloalkyl ring, 6-10 membered aryl ring, and 5-10 membered heteroaryl ring are optionally substituted with one or more R$^{10}$;
L$^1$ is a bond or C$_{1-6}$alkyl;
R$^2$ is —OR$^{2a}$, —NR$^{2b}$R$^{2c}$, —SR$^{2g}$, —S(O)R$^{2h}$, —S(O)$_2$R$^{2h}$, —S(O)$_2$NR$^{2b}$R$^{2c}$, —C(R$^{2d}$)(R$^{2e}$)(R$^2$), C(O) NR$^{2b}$R$^{2c}$, —CN, or halogen;
R$^{2a}$ is selected from hydrogen, C$_{1-6}$alkyl, C$_{2-6}$alkenyl, C$_{2-6}$alkynyl, C$_{3-10}$cycloalkyl, C$_{2-9}$heterocycloalkyl, $C_{6-10}$aryl, $C_{1-9}$heteroaryl, —C(O)O$R^{12}$, —C(O)$R^{15}$, —C(O)N($R^{12}$)($R^{13}$), —S(O)$_2R^{15}$, —S(O)$_2$N($R^{12}$)($R^{13}$), wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20a}$;

$R^{2b}$ is selected from hydrogen, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —C(O)O$R^{12}$, —C(O)$R^{15}$, —C(O)N($R^{12}$)($R^{13}$), —S(O)$_2R^{15}$, and —S(O)$_2$N($R^{12}$)($R^{13}$), wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20a}$;

$R^{2c}$ is selected from hydrogen, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20a}$; or $R^{2b}$ and $R^{2c}$, together with the nitrogen to which they are attached, form a $C_{2-9}$heterocycloalkyl ring optionally substituted with one, two, or three $R^{20a}$;

$R^{2d}$ is selected from hydrogen, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —O$R^{12}$, —S$R^{12}$, —N($R^{12}$)($R^{13}$), —C(O)O$R^{12}$, —OC(O)N($R^{12}$)($R^{13}$), —N($R^{14}$)C(O)N($R^{12}$)($R^{13}$), —N($R^{14}$)C(O)O$R^{15}$, —N($R^{14}$)S(O)$_2R^{15}$, —C(O)$R^{15}$, —S(O)$R^{15}$, —OC(O)$R^{15}$, —C(O)N($R^{12}$)($R^{13}$), —C(O)C(O)N($R^{12}$)($R^{13}$), —N($R^{14}$)C(O)$R^{15}$, —S(O)$_2R^{15}$, —S(O)$_2$N($R^{12}$)($R^{13}$), —S(=O)(=NH)N($R^{12}$)($R^{13}$), —CH$_2$C(O)N($R^{12}$)($R^{13}$), —CH$_2$N($R^{14}$)C(O)$R^{15}$, —CH$_2$S(O)$_2R^{15}$, —CH$_2$S(O)$_2$N($R^{12}$)($R^{13}$), —CH$_2$N($R^{12}$)S(O)$_2$($R^{13}$), and —P(O)($R^{17}$)($R^{17a}$), wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20a}$;

$R^{2e}$ is selected from hydrogen, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20a}$;

$R^{2f}$ is selected from hydrogen, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20a}$;

$R^{2g}$ is selected from hydrogen, $C_{2-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —C(O)O$R^{12}$, —C(O)$R^{15}$, —C(O)N($R^{12}$)($R^{13}$), —S(O)$_2R^{15}$, —S(O)$_2$N($R^{12}$)($R^{13}$), wherein $C_{2-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20a}$;

$R^{2h}$ is selected from $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20a}$;

$R^3$ is selected from halogen, $C_{1-6}$alkyl, $C_{2-6}$alkenyl, $C_{2-6}$alkynyl, $C_{3-14}$cycloalkyl, $C_{2-9}$heterocycloalkyl, $C_{6-10}$aryl, $C_{1-9}$heteroaryl, —S$R^{12}$, —N($R^{12}$)($R^{13}$), —C(O)O$R^{12}$, —OC(O)N($R^{12}$)($R^{13}$), —N($R^{14}$)C(O)N($R^{12}$)($R^{13}$), —N($R^{14}$)C(O)O$R^{15}$, —N($R^{14}$)S(O)$_2R^{15}$, N($R^{14}$)S(O)$R^{15}$, —C(O)$R^{15}$, —S(O)$R^{15}$, —OC(O)$R^{15}$, —C(O)N($R^{12}$)($R^{13a}$), —C(O)C(O)N($R^{12}$)($R^{13}$), —N($R^{14}$)C(O)O$R^{15}$, —S(O)$_2R^{15}$, —S(O)$_2$N($R^{12}$)($R^{13}$) S(O)N($R^{12}$)($R^{13}$), —S(=O)(=NH)N($R^{12}$)($R^{13}$), —CH$_2$C(O)N($R^{12}$)($R^{13}$), —CH$_2$N($R^{14}$)C(O)$R^{15}$, —CH$_2$S(O)$_2R^{15}$, —CH$_2$S(O)$_2$N($R^{12}$)($R^{13}$), —CH$_2$N($R^{12}$)S(O)$_2$($R^{13}$), CH$_2$S(O)$R^{15}$, —CH$_2$S(O)N($R^{12}$)($R^{13}$), —CH$_2$N($R^{12}$)S(O)($R^{13}$) and —P(O)($R^{17}$)($R^{17a}$), wherein $C_{1-6}$alkyl, $C_{2-6}$alkenyl, $C_{2-6}$alkynyl, $C_{3-14}$cycloalkyl, $C_{2-9}$heterocycloalkyl, $C_{6-10}$aryl, and $C_{1-9}$heteroaryl are optionally substituted with one, two, or three $R^{20b}$;

$R^4$ is selected from hydrogen, $C_{1-6}$alkyl, and $C_{1-6}$haloalkyl;

$R^5$ is selected from hydrogen, $C_{1-6}$alkyl, and $C_{1-6}$haloalkyl;

$R^6$ is selected from hydrogen, halogen, —CN, $C_{1-6}$alkyl, $C_{2-6}$alkenyl, $C_{2-6}$alkynyl, $C_{3-10}$cycloalkyl, $C_{2-9}$heterocycloalkyl, —O$R^{12}$, —S$R^{12}$, —N($R^{12}$)($R^{13}$), —C(O)O$R^{12}$, —OC(O)N($R^{12}$)($R^{13}$), —N($R^{14}$)C(O)N($R^{12}$)($R^{13}$), —N($R^{14}$)C(O)O$R^{15}$, —N($R^{14}$)S(O)$_2R^{15}$, —C(O)$R^{15}$, —S(O)$R^{15}$, —OC(O)$R^{15}$, —C(O)N($R^{12}$)($R^{13}$), —C(O)C(O)N($R^{12}$)($R^{13}$), —N($R^{14}$)C(O)$R^{15}$, —S(O)$_2R^{15}$, —S(O)$_2$N($R^{12}$)($R^{13}$), —S(=O)(=NH)N($R^{12}$)($R^{13}$), —CH$_2$C(O)N($R^{12}$)($R^{13}$), —CH$_2$N($R^{14}$)C(O)$R^{15}$, —CH$_2$S(O)$_2R^{15}$, —CH$_2$S(O)$_2$N($R^{12}$)($R^{13}$), —CH$_2$N($R^{12}$)S(O)$_2$($R^{13}$), and —P(O)($R^{17}$)($R^{17a}$) wherein $C_{1-6}$alkyl, $C_{2-6}$alkenyl, $C_{2-6}$alkynyl, $C_{3-10}$cycloalkyl, and $C_{2-9}$heterocycloalkyl are optionally substituted with one, two, or three $R^{20c}$;

$R^7$ is selected from hydrogen, halogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{1-9}$heteroaryl, —O$R^{12}$, —S$R^{12}$, —N($R^{12}$)($R^{13}$), —C(O)O$R^{12}$, —OC(O)N($R^{12}$)($R^{13}$), —N($R^{14}$)C(O)N($R^{12}$)($R^{13}$), —N($R^{14}$)C(O)O$R^{15}$, —N($R^{14}$)S(O)$_2R^{15}$, —C(O)$R^{15}$, —S(O)$R^{15}$, —OC(O)$R^{15}$, —C(O)N($R^{12}$)($R^{13}$), —C(O)C(O)N($R^{12}$)($R^{13}$), —N($R^{14}$)C(O)$R^{15}$, —S(O)$_2R^{15}$, —S(O)$_2$N($R^{12}$)($R^{13}$), —S(=O)(=NH)N($R^{12}$)($R^{13}$), —CH$_2$C(O)N($R^{12}$)($R^{13}$), —CH$_2$N($R^{14}$)C(O)$R^{15}$, —CH$_2$S(O)$_2R^{15}$, —CH$_2$S(O)$_2$N($R^{12}$)($R^{13}$), —CH$_2$N($R^{12}$)S(O)$_2$($R^{13}$), and —P(O)($R^{17}$)($R^{17a}$), wherein $C_{1-6}$alkyl, $C_{2-6}$alkenyl, $C_{2-6}$alkynyl, $C_{3-10}$cycloalkyl, $C_{2-9}$heterocycloalkyl, and $C_{1-9}$heteroaryl are optionally substituted with one, two, or three $R^{20c}$;

each $R^{10}$ is independently selected from halogen, —CN, $C_{1-6}$alkyl, $C_{2-6}$alkenyl, $C_{2-6}$alkynyl, $C_{3-7}$cycloalkyl, $C_{2-9}$heterocycloalkyl, $C_{6-10}$aryl, $C_{1-9}$heteroaryl, —O$R^{12}$, —S$R^{12}$, —N($R^{12}$)($R^{13}$), —C(O)O$R^{12}$, —OC(O)N($R^{12}$)($R^{13}$), —N($R^{14}$)C(O)N($R^{12}$)($R^{13}$), —N($R^{14}$)C(O)O$R^{15}$, —N($R^{14}$)S(O)$_2R^{15}$, —C(O)$R^{15}$, —S(O)$R^{15}$, —OC(O)$R^{15}$, —C(O)N($R^{12}$)($R^{13}$), —C(O)C(O)N($R^{12}$)($R^{13}$), —N($R^{14}$)C(O)O$R^{15}$, —S(O)$_2R^{15}$, —S(O)$_2$N($R^{12}$)($R^{13}$), —S(=O)(=NH)N($R^{12}$)($R^{13}$), —CH$_2$C(O)N($R^{12}$)($R^{13}$), —CH$_2$N($R^{14}$)C(O)$R^{15}$, —CH$_2$S(O)$_2R^{15}$, —CH$_2$S(O)$_2$N($R^{12}$)($R^{13}$), —CH$_2$N($R^{12}$)S(O)$_2$($R^{13}$), and —P(O)($R^{17}$)($R^{17a}$), wherein $C_{1-6}$alkyl, $C_{2-6}$alkenyl, $C_{2-6}$alkynyl, $C_{3-7}$cycloalkyl, $C_{2-9}$heterocycloalkyl, $C_{6-10}$aryl, and $C_{1-9}$heteroaryl are optionally substituted with one, two, or three $R^{20a}$;

each $R^{12}$ is independently selected from hydrogen, $C_{1-6}$alkyl, $C_{1-6}$haloalkyl, $C_{2-6}$alkenyl, $C_{2-6}$alkynyl, $C_{3-7}$cycloalkyl, $C_{2-9}$heterocycloalkyl, $C_{6-10}$aryl, and $C_{1-9}$heteroaryl, wherein $C_{1-6}$alkyl, $C_{2-6}$alkenyl, $C_{2-6}$alkynyl, $C_{3-7}$cycloalkyl, $C_{2-9}$heterocycloalkyl, $C_{6-10}$aryl, and $C_{1-9}$heteroaryl are optionally substituted with one, two, or three $R^{20e}$;

each $R^{13}$ is independently selected from hydrogen, $C_{1-6}$alkyl, and $C_{1-6}$haloalkyl; or $R^{12}$ and $R^{13}$, together with the nitrogen to which they are attached, form a C$_{2-9}$heterocycloalkyl ring optionally substituted with one, two, or three R$^{20f}$;

R$^{13a}$ is selected from C$_{1-6}$alkyl and C$_{1-6}$haloalkyl; or R$^{12}$ and R$^{13a}$, together with the nitrogen to which they are attached, form a C$_{2-9}$heterocycloalkyl ring optionally substituted with one, two, or three R$^{20f}$;

each R$^{14}$ is independently selected from hydrogen, C$_{1-6}$alkyl, and C$_{1-6}$haloalkyl;

each R$^{15}$ is independently selected C$_{1-6}$alkyl, C$_{2-6}$alkenyl, C$_{2-6}$alkynyl, C$_{3-7}$cycloalkyl, C$_{2-9}$heterocycloalkyl, C$_{6-10}$aryl, and C$_{1-9}$ heteroaryl, wherein C$_{1-6}$alkyl, C$_{2-6}$alkenyl, C$_{2-6}$alkynyl, C$_{3-7}$cycloalkyl, C$_{2-9}$heterocycloalkyl, C$_{6-10}$aryl, and C$_{1-9}$heteroaryl are optionally substituted with one, two, or three R$^{20g}$;

each R$^{17}$ and each R$^{17a}$ are each independently selected from C$_{1-6}$alkyl and C$_{3-6}$cycloalkyl, wherein C$_{1-6}$alkyl and C$_{3-6}$cycloalkyl are optionally substituted with one, two or three of R$^{20h}$; or R$^{17}$ and R$^{17a}$ are combined to form a C$_{2-9}$heterocycloalkyl ring;

each R$^{20a}$, R$^{20b}$, R$^{20c}$, R$^{20d}$, R$^{20e}$, R$^{20f}$, R$^{20g}$, and R$^{20h}$ are each independently selected from halogen, oxo, =NH, —CN, C$_{1-6}$alkyl, C$_{2-6}$alkenyl, C$_{2-6}$alkynyl, C$_{3-10}$cycloalkyl, —CH$_2$—C$_{3-10}$cycloalkyl, C$_{2-9}$heterocycloalkyl, —CH$_2$—C$_{2-9}$heterocycloalkyl, C$_{6-10}$aryl, —CH$_2$—C$_{6-10}$aryl, C$_{1-9}$heteroaryl, —OR$^{21}$, —SR$^{21}$, —N(R$^{22}$)(R$^{23}$), —C(O)OR$^{22}$, —C(O)N(R$^{22}$)(R$^{23}$), —C(O)C(O)N(R$^{22}$)(R$^{23}$), —OC(O)N(R$^{22}$)(R$^{23}$), —N(R$^{24}$)C(O)N(R$^{22}$)(R$^{23}$), —N(R$^{24}$)C(O)OR$^{25}$, —N(R$^{24}$)C(O)R$^{25}$, —N(R$^{24}$)S(O)$_2$R$^{25}$, —C(O)R$^{25}$, —S(O)$_2$R$^{25}$, —S(O)$_2$N(R$^{22}$)(R$^{23}$), —OCH$_2$C(O)OR$^{22}$, and —OC(O)R$^{25}$, wherein C$_{1-6}$alkyl, C$_{2-6}$alkenyl, C$_{2-6}$alkynyl, C$_{3-10}$cycloalkyl, —CH$_2$—C$_{3-10}$cycloalkyl, C$_{2-9}$heterocycloalkyl, —CH$_2$—C$_{2-9}$heterocycloalkyl, C$_{6-10}$aryl, —CH$_2$—C$_{6-10}$aryl, and C$_{1-9}$heteroaryl are optionally substituted with one, two, or three groups independently selected from halogen, oxo, =NH, —CN, C$_{1-6}$alkyl, C$_{1-6}$haloalkyl, C$_{1-6}$alkoxy, C$_{1-6}$haloalkoxy, —OR$^{21}$, —SR$^{21}$, —N(R$^{22}$)(R$^{23}$), —C(O)OR$^{22}$, —C(O)N(R$^{22}$)(R$^{23}$), —C(O)C(O)N(R$^{22}$)(R$^{23}$), —OC(O)N(R$^{22}$)(R$^{23}$), —N(R$^{24}$)C(O)N(R$^{22}$)(R$^{23}$), —N(R$^{24}$)C(O)OR$^{25}$, —N(R$^{24}$)C(O)R$^{25}$, —N(R$^{24}$)S(O)$_2$R$^{25}$, —C(O)R$^{25}$, —S(O)$_2$R$^{25}$, —S(O)$_2$N(R$^{22}$)(R$^{23}$), and —OC(O)R$^{25}$;

each R$^{21}$ is independently selected from H, C$_{1-6}$alkyl, C$_{1-6}$haloalkyl, C$_{2-6}$alkenyl, C$_{2-6}$alkynyl, C$_{3-7}$cycloalkyl, C$_{2-9}$heterocycloalkyl, C$_{6-10}$aryl, and C$_{1-9}$heteroaryl, wherein C$_{3-7}$cycloalkyl, C$_{2-9}$heterocycloalkyl, C$_{6-10}$aryl, and C$_{1-9}$heteroaryl are optionally substituted with one, two, or three groups independently selected from halogen and C$_{1-6}$alkyl;

each R$^{22}$ is independently selected from H, C$_{1-6}$alkyl, C$_{1-6}$haloalkyl, C$_{2-6}$alkenyl, C$_{2-6}$alkynyl, C$_{3-7}$cycloalkyl, C$_{2-9}$heterocycloalkyl, C$_{6-10}$aryl, and C$_{1-9}$heteroaryl, wherein C$_{3-7}$cycloalkyl, C$_{2-9}$heterocycloalkyl, C$_{6-10}$aryl, and C$_{1-9}$heteroaryl are optionally substituted with one, two, or three groups independently selected from halogen and C$_{1-6}$alkyl;

each R$^{23}$ is independently selected from H and C$_{1-6}$alkyl;
each R$^{24}$ is independently selected from H and C$_{1-6}$alkyl; and each R$^{25}$ is selected from C$_{1-6}$alkyl, C$_{2-6}$alkenyl, C$_{2-6}$alkynyl, C$_{3-7}$cycloalkyl, C$_{2-9}$heterocycloalkyl, C$_{6-10}$aryl, and C$_{1-9}$heteroaryl, wherein C$_{1-6}$alkyl, C$_{3-7}$cycloalkyl, C$_{2-9}$heterocycloalkyl, C$_{6-10}$aryl, and C$_{1-9}$heteroaryl are optionally substituted with one, two, or three groups independently selected from halogen, C$_{1-6}$alkyl, C$_{1-6}$haloalkyl, C$_{1-6}$alkoxy, C$_{3-7}$cycloalkyl, C$_{2-9}$heterocycloalkyl, C$_{6-10}$aryl, and C$_{1-9}$heteroaryl.

Embodiment A2. The compound of Embodiment A1 having the structure of Formula (Ia), or a pharmaceutically acceptable salt or solvate thereof:

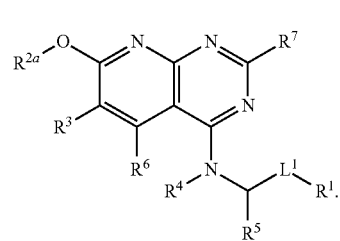

Formula (Ia)

Embodiment A3. The compound of Embodiment A1 or Embodiment A2, or a pharmaceutically acceptable salt or solvate thereof, wherein R$^{2a}$ is C$_{1-6}$alkyl optionally substituted with one, two, or three R$^{20a}$.

Embodiment A4. The compound of any one of Embodiments A1-A3, or a pharmaceutically acceptable salt or solvate thereof, wherein R$^{2a}$ is unsubstituted C$_{1-6}$alkyl.

Embodiment A5. The compound of any one of Embodiments A1-A3, or a pharmaceutically acceptable salt or solvate thereof, wherein R$^{2a}$ is —CH$_3$.

Embodiment A6. The compound of Embodiment A1 having the structure of Formula (Ib), or a pharmaceutically acceptable salt or solvate thereof:

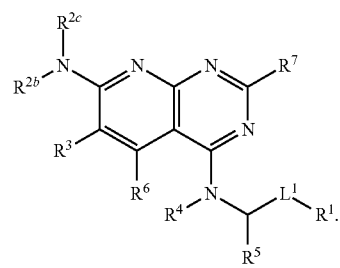

Formula (Ib)

Embodiment A7. The compound of Embodiment A6, or a pharmaceutically acceptable salt or solvate thereof, wherein R$^{2b}$ is C$_{1-6}$alkyl optionally substituted with one, two, or three R$^{20a}$.

Embodiment A8. The compound of Embodiment A6 or Embodiment A7, or a pharmaceutically acceptable salt or solvate thereof, wherein R$^{2e}$ is C$_{1-6}$alkyl optionally substituted with one, two, or three R$^{20a}$.

Embodiment A9. The compound of Embodiment A6 or Embodiment A7, or a pharmaceutically acceptable salt or solvate thereof, wherein R$^{2e}$ is hydrogen.

Embodiment A10. The compound of Embodiment A1 having the structure of Formula (Ic), or a pharmaceutically acceptable salt or solvate thereof:

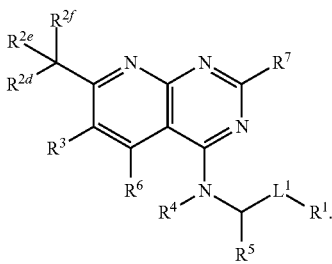

Formula (Ic)

Embodiment A11. The compound of Embodiment A10, or a pharmaceutically acceptable salt or solvate thereof, wherein $R^{2a}$ is hydrogen or $C_{1-6}$alkyl optionally substituted with one, two, or three $R^{20a}$.

Embodiment A12. The compound of Embodiment A10 or Embodiment A11, or a pharmaceutically acceptable salt or solvate thereof, wherein $R^{2e}$ is hydrogen.

Embodiment A13. The compound of any one of Embodiments A10-A12, or a pharmaceutically acceptable salt or solvate thereof, wherein $R^{21}$ is hydrogen.

Embodiment A14. The compound of Embodiment A1, or a pharmaceutically acceptable salt or solvate thereof, wherein $R^2$ is halogen.

Embodiment A15. A compound of Formula (II), or a pharmaceutically acceptable salt or solvate thereof:

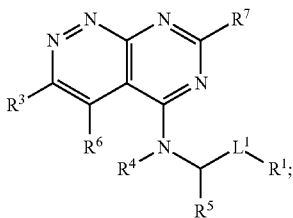

Formula (II)

wherein:
$R^1$ is a 3-12 membered cycloalkyl ring, 3-12 membered heterocycloalkyl ring, 6-10 membered aryl ring, or 5-10 membered heteroaryl ring, wherein the 3-12 membered cycloalkyl ring, 3-12 membered heterocycloalkyl ring, 6-10 membered aryl ring, and 5-10 membered heteroaryl ring are optionally substituted with one or more $R^{10}$;
$L^1$ is a bond or $C_{1-6}$alkyl;
$R^3$ is selected from hydrogen, halogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$ heteroaryl, —OR$^{12}$, —SR$^{12}$, —N(R$^{12}$)(R$^{13}$), —C(O)OR$^{12}$, —OC(O)N(R$^{12}$)(R$^{13}$), —N(R$^{14}$)C(O)N(R$^{12}$)(R$^{13}$), —N(R$^{14}$)C(O)OR$^{15}$, —N(R$^{14}$)S(O)$_2$R$^{15}$, N(R$^{14}$)S(O)R$^{15}$, —C(O)R$^{15}$, —S(O)R$^{15}$, —OC(O)R$^{15}$, —C(O)N(R$^{12}$)(R$^{13}$), —C(O)C(O)N(R$^{12}$)(R$^{13}$), —N(R$^{14}$)C(O)R$^{15}$, —S(O)$_2$R$^{15}$, —S(O)$_2$N(R$^{12}$)(R$^{13}$), —S(O)N(R$^{12}$)(R$^{13}$), —S(=O)(=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, —CH$_2$S(O)$_2$N(R$^{12}$)(R$^{13}$), —CH$_2$N(R$^{12}$)S(O)$_2$(R$^{13}$), CH$_2$S(O) R$^{15}$, —CH$_2$S(O)N(R$^{12}$)(R$^{13}$), —CH$_2$N(R$^{12}$)S(O)(R$^{13}$) and —P(O)(R$^{17}$)(R$^{17a}$), wherein $C_{1-6}$alkyl, $C_{2-6}$alkenyl, $C_{2-6}$alkynyl, $C_{3-14}$cycloalkyl, $C_{2-9}$heterocycloalkyl, $C_{6-10}$aryl, and $C_{1-9}$heteroaryl are optionally substituted with one, two, or three $R^{2b}$;
$R^4$ is selected from hydrogen, $C_{1-6}$alkyl, and $C_{1-6}$haloalkyl;
$R^5$ is selected from hydrogen, $C_{1-6}$alkyl, and $C_{1-6}$haloalkyl;

$R^6$ and $R^7$ are each independently selected from hydrogen, halogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{1-9}$heteroaryl, —OR$^{12}$, —SR$^{12}$, —N(R$^{12}$)(R$^{13}$), —C(O)OR$^{12}$, —OC(O)N(R$^{12}$)(R$^{13}$), —N(R$^{14}$)C(O)N(R$^{12}$)(R$^{13}$), —N(R$^{14}$)C(O)OR$^{15}$, —N(R$^{14}$)S(O)$_2$R$^{15}$, —C(O)R$^{15}$, —S(O)R$^{15}$, —OC(O)R$^{15}$, —C(O)N(R$^{12}$)(R$^{13}$), —C(O)C(O)N(R$^{12}$)(R$^{13}$), —N(R$^{14}$)C(O)R$^{15}$, —S(O)$_2$R$^{15}$, —S(O)$_2$N(R$^{12}$)(R$^{13}$), —S(=O)(=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, —CH$_2$S(O)$_2$N(R$^{12}$)(R$^{13}$), —CH$_2$N(R$^{12}$)S(O)$_2$(R$^{13}$), and —P(O)(R$^{17}$)(R$^{17a}$), wherein $C_{1-6}$alkyl, $C_{2-6}$alkenyl, $C_{2-6}$alkynyl, $C_{3-10}$cycloalkyl, $C_{2-9}$heterocycloalkyl, and $C_{1-9}$heteroaryl are optionally substituted with one, two, or three $R^{20c}$;
each $R^{10}$ is independently selected from halogen, —CN, $C_{1-6}$alkyl, $C_{2-6}$alkenyl, $C_{2-6}$alkynyl, $C_{3-7}$cycloalkyl, $C_{2-9}$heterocycloalkyl, $C_{6-10}$aryl, $C_{1-9}$heteroaryl, —OR$^{12}$, —SR$^{12}$, —N(R$^{12}$)(R$^{13}$), —C(O)OR$^{12}$, —OC(O)N(R$^{12}$)(R$^{13}$), —N(R$^{14}$)C(O)N(R$^{12}$)(R$^{13}$), —N(R$^{14}$)C(O)OR$^{15}$, —N(R$^{14}$)S(O)$_2$R$^{15}$, —C(O)R$^{15}$, —S(O)R$^{15}$, —OC(O)R$^{15}$, —C(O)N(R$^{12}$)(R$^{13}$), —C(O)C(O)N(R$^{12}$)(R$^{13}$), —N(R$^{14}$)C(O)R$^{15}$, —S(O)$_2$R$^{15}$, —S(O)$_2$N(R$^{12}$)(R$^{13}$), —S(=O)(=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, —CH$_2$S(O)$_2$N(R$^{12}$)(R$^{13}$), —CH$_2$N(R$^{12}$)S(O)$_2$(R$^{13}$), and —P(O)(R$^{17}$)(R$^{17a}$), wherein $C_{1-6}$alkyl, $C_{2-6}$alkenyl, $C_{2-6}$alkynyl, $C_{3-7}$cycloalkyl, $C_{2-9}$heterocycloalkyl, $C_{6-10}$aryl, and $C_{1-9}$heteroaryl are optionally substituted with one, two, or three $R^{20a}$;
each $R^{12}$ is independently selected from hydrogen, $C_{1-6}$alkyl, $C_{1-6}$ haloalkyl, $C_{2-6}$alkenyl, $C_{2-6}$alkynyl, $C_{3-7}$cycloalkyl, $C_{2-9}$heterocycloalkyl, $C_{6-10}$aryl, and $C_{1-9}$heteroaryl, wherein $C_{1-6}$alkyl, $C_{2-6}$alkenyl, $C_{2-6}$alkynyl, $C_{3-7}$cycloalkyl, $C_{2-9}$heterocycloalkyl, $C_{6-10}$aryl, and $C_{1-9}$heteroaryl are optionally substituted with one, two, or three $R^{20e}$;
each $R^{13}$ is independently selected from hydrogen, $C_{1-6}$alkyl, and $C_{1-6}$haloalkyl; or $R^{12}$ and $R^{13}$, together with the nitrogen to which they are attached, form a $C_{2-9}$heterocycloalkyl ring optionally substituted with one, two, or three $R^{20f}$;
each $R^{14}$ is independently selected from hydrogen, $C_{1-6}$alkyl, and $C_{1-6}$haloalkyl;
each $R^{15}$ is independently selected $C_{1-6}$alkyl, $C_{2-6}$alkenyl, $C_{2-6}$alkynyl, $C_{3-7}$cycloalkyl, $C_{2-9}$heterocycloalkyl, $C_{6-10}$aryl, and $C_{1-9}$heteroaryl, wherein $C_{1-6}$alkyl, $C_{2-6}$alkenyl, $C_{2-6}$alkynyl, $C_{3-7}$cycloalkyl, $C_{2-9}$heterocycloalkyl, $C_{6-10}$aryl, and $C_{1-9}$heteroaryl are optionally substituted with one, two, or three $R^{20g}$;
each $R^{17}$ and each $R^{17a}$ are each independently selected from $C_{1-6}$alkyl and $C_{3-6}$cycloalkyl, wherein $C_{1-6}$alkyl and $C_{3-6}$cycloalkyl are optionally substituted with one, two or three of $R^{20h}$; or $R^{17}$ and $R^{17a}$ form a $C_{2-9}$heterocycloalkyl ring;
each $R^{20a}$, $R^{20b}$, $R^{20c}$, $R^{20d}$, $R^{20e}$, $R^{20f}$, $R^{20g}$, and $R^{20h}$ are each independently selected from halogen, oxo, =NH, —CN, $C_{1-6}$alkyl, $C_{2-6}$alkenyl, $C_{2-6}$alkynyl, $C_{3-10}$cycloalkyl, —CH$_2$—C$_{3-10}$cycloalkyl, $C_{2-9}$heterocycloalkyl, —CH$_2$—C$_{2-9}$heterocycloalkyl, $C_{6-10}$aryl, —CH$_2$—C$_{6-10}$aryl, $C_{1-9}$heteroaryl, —OR$^{21}$, —SR$^{21}$, —N(R$^{22}$)(R$^{23}$), —C(O)OR$^{22}$, —C(O)N(R$^{22}$)(R$^{23}$), —C(O)C(O)N(R$^{22}$)(R$^{23}$), —OC(O)N(R$^{22}$)(R$^{23}$), —N(R$^{24}$)C(O)N(R$^{22}$)(R$^{23}$), —N(R$^{24}$)C(O)OR$^{25}$, —N(R$^{24}$)C(O)R$^{25}$, —N(R$^{24}$)S(O)$_2$R$^{25}$, —C(O)R$^{25}$, —S(O)$_2$R$^{25}$, —S(O)$_2$N(R$^{22}$)(R$^{23}$), —OCH$_2$C(O)OR$^{22}$, and —OC(O)R$^{25}$, wherein $C_{1-6}$alkyl, $C_{2-6}$alkenyl, $C_{2-6}$alkynyl, $C_{3-10}$cycloalkyl, —CH$_2$—C$_{3-10}$cycloalkyl, $C_{2-9}$heterocycloalkyl, —CH$_2$—C$_{2-9}$heterocycloalkyl, $C_{6-10}$aryl, —CH$_2$—C$_{6-10}$aryl, and $C_{1-9}$heteroaryl are optionally substituted with one, two, or three groups independently selected from halogen, oxo, =NH, —CN, $C_{1-6}$alkyl, $C_{1-6}$haloalkyl, $C_{1-6}$alkoxy, $C_{1-6}$haloalkoxy, —$OR^{21}$, —$SR^{21}$, —$N(R^{22})(R^{23})$, —$C(O)OR^{22}$, —$C(O)N(R^{22})(R^{23})$, —$C(O)C(O)N(R^{22})(R^{23})$, —$OC(O)N(R^{22})(R^{23})$, —$N(R^{24})C(O)N(R^{22})(R^{23})$, —$N(R^{24})C(O)OR^{25}$, —$N(R^{24})C(O)R^{25}$, —$N(R^{24})S(O)_2R^{25}$, —$C(O)R^{25}$, —$S(O)_2R^{25}$, —$S(O)_2N(R^{22})(R^{23})$, and —$OC(O)R^{25}$;

each $R^{21}$ is independently selected from H, $C_{1-6}$alkyl, $C_{1-6}$haloalkyl, $C_{2-6}$alkenyl, $C_{2-6}$alkynyl, $C_{3-7}$cycloalkyl, $C_{2-9}$heterocycloalkyl, $C_{6-10}$aryl, and $C_{1-9}$heteroaryl, wherein $C_{3-7}$cycloalkyl, $C_{2-9}$heterocycloalkyl, $C_{6-10}$aryl, and $C_{1-9}$heteroaryl are optionally substituted with one, two, or three groups independently selected from halogen and $C_{1-6}$alkyl;

each $R^{22}$ is independently selected from H, $C_{1-6}$alkyl, $C_{1-6}$haloalkyl, $C_{2-6}$alkenyl, $C_{2-6}$alkynyl, $C_{3-7}$cycloalkyl, $C_{2-9}$heterocycloalkyl, $C_{6-10}$aryl, and $C_{1-9}$heteroaryl, wherein $C_{3-7}$cycloalkyl, $C_{2-9}$heterocycloalkyl, $C_{6-10}$aryl, and $C_{1-9}$heteroaryl are optionally substituted with one, two, or three groups independently selected from halogen and $C_{1-6}$alkyl;

each $R^{23}$ is independently selected from H and $C_{1-6}$alkyl;
each $R^{24}$ is independently selected from H and $C_{1-6}$alkyl; and each $R^{25}$ is selected from $C_{1-6}$alkyl, $C_{2-6}$alkenyl, $C_{2-6}$alkynyl, $C_{3-7}$cycloalkyl, $C_{2-9}$heterocycloalkyl, $C_{6-10}$aryl, and $C_{1-9}$heteroaryl, wherein $C_{1-6}$alkyl, $C_{3-7}$cycloalkyl, $C_{2-9}$heterocycloalkyl, $C_{6-10}$aryl, and $C_{1-9}$heteroaryl are optionally substituted with one, two, or three groups independently selected from halogen, $C_{1-6}$alkyl, $C_{1-6}$haloalkyl, $C_{1-6}$alkoxy, $C_{3-7}$cycloalkyl, $C_{2-9}$heterocycloalkyl, $C_{6-10}$aryl, and $C_{1-9}$heteroaryl.

Embodiment A16. The compound of any one of Embodiments A1-15, or a pharmaceutically acceptable salt or solvate thereof, wherein $R^3$ is selected from —$N(R^{12})(R^{13})$, —$C(O)R^{15}$, —$C(O)N(R^{12})(R^{13})$, —$SO_2(R^{12})(R^{13})$, —$SO_2N(R^{12})(R^{13})$, —$P(O)(R^{17})(R^{17a})$, $C_{1-6}$alkyl, $C_{3-10}$cycloalkyl, $C_{2-9}$heterocycloalkyl, $C_{6-10}$aryl, and $C_{1-9}$heteroaryl, wherein $C_{1-6}$alkyl, $C_{3-10}$cycloalkyl, $C_{2-9}$heterocycloalkyl, $C_{6-10}$aryl, and $C_{1-9}$heteroaryl are optionally substituted with one, two, or three $R^{20b}$.

Embodiment A17. The compound of any one of Embodiments A1-A16, or a pharmaceutically acceptable salt or solvate thereof, wherein $R^3$ is selected from —$N(R^{12})(R^{13})$, $C_{1-6}$alkyl, $C_{3-10}$cycloalkyl, and $C_{2-9}$heterocycloalkyl, wherein $C_{1-6}$ alkyl, $C_{3-10}$cycloalkyl, and $C_{2-9}$heterocycloalkyl are optionally substituted with one, two, or three $R^{20b}$.

Embodiment A18. The compound of any one of Embodiments A1-A17, or a pharmaceutically acceptable salt or solvate thereof, wherein $R^3$ is $C_{2-9}$heterocycloalkyl optionally substituted with one, two, or three $R^{20b}$.

Embodiment A19. The compound of any one of Embodiments A1-A17, or a pharmaceutically acceptable salt or solvate thereof, wherein $R^3$ is $C_{3-10}$cycloalkyl optionally substituted with one, two, or three $R^{20b}$ Embodiment A20. The compound of any one of Embodiments A1-A17, or a pharmaceutically acceptable salt or solvate thereof, wherein $R^3$ is $C_{1-6}$alkyl optionally substituted with one, two, or three $R^{20b}$.

Embodiment A21. The compound of any one of Embodiments A1-A17, or a pharmaceutically acceptable salt or solvate thereof, wherein $R^3$ is —$N(R^{12})(R^{13})$.

Embodiment A22. A compound of Formula (III), or a pharmaceutically acceptable salt or solvate thereof:

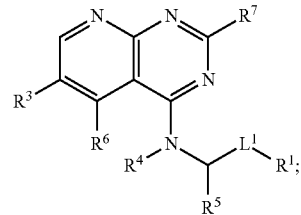

Formula (III)

wherein:

$R^1$ is a 3-12 membered cycloalkyl ring, 3-12 membered heterocycloalkyl ring, 6-10 membered aryl ring, or 5-10 membered heteroaryl ring, wherein the 3-12 membered cycloalkyl ring, 3-12 membered heterocycloalkyl ring, 6-10 membered aryl ring, and 5-10 membered heteroaryl ring are optionally substituted with one or more $R^{10}$;

$L^1$ is a bond or $C_{1-6}$alkyl;

$R^4$ is selected from hydrogen, $C_{1-6}$alkyl, and $C_{1-6}$haloalkyl;

$R^5$ is selected from hydrogen, $C_{1-6}$alkyl, and $C_{1-6}$haloalkyl;

$R^6$ is selected from hydrogen, halogen, —CN, $C_{1-6}$alkyl, $C_{2-6}$alkenyl, $C_{2-6}$alkynyl, $C_{3-10}$cycloalkyl, $C_{2-9}$heterocycloalkyl, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{15}$, —$S(O)_2R^{15}$, —$S(O)_2N(R^{12})(R^{13})$, —$S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, —$CH_2S(O)_2N(R^{12})(R^{13})$, —$CH_2N(R^{12})S(O)_2(R^{13})$, and —$P(O)(R^{17})(R^{17a})$, wherein $C_{1-6}$alkyl, $C_{2-6}$alkenyl, $C_{2-6}$alkynyl, $C_{3-10}$cycloalkyl, and $C_{2-9}$heterocycloalkyl are optionally substituted with one, two, or three $R^{20c}$;

$R^7$ is selected from hydrogen, halogen, —CN, $C_{1-6}$alkyl, $C_{2-6}$alkenyl, $C_{2-6}$alkynyl, $C_{3-10}$cycloalkyl, $C_{2-9}$heterocycloalkyl, $C_{1-9}$heteroaryl, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{15}$, —$S(O)_2R^{15}$, —$S(O)_2N(R^{12})(R^{13})$, —$S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, —$CH_2S(O)_2N(R^{12})(R^{13})$, —$CH_2N(R^{12})S(O)_2(R^{13})$, and —$P(O)(R^{17})(R^{17a})$, wherein $C_{1-6}$alkyl, $C_{2-6}$alkenyl, $C_{2-6}$alkynyl, $C_{3-10}$cycloalkyl, $C_{2-9}$heterocycloalkyl, and $C_{1-9}$heteroaryl are optionally substituted with one, two, or three $R^{20c}$;

$R^8$ is —$OR^{9a}$, —$NR^{9b}R^{9c}$, —$SR^{9b}$, —$S(O)R^{9d}$, —$S(O)_2R^{9d}$, —$S(O)_2NR^{9b}R^{9c}$, —$C(R^{9e})(R^{9f})(R^{9g})$, and $C(O)NR^{9b}R^{9c}$.

$R^{9a}$ is selected from hydrogen, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —$C(O)OR^{12}$, —$C(O)R^{15}$, —$C(O)N(R^{12})(R^{13})$, —$S(O)_2R^{15}$, —$S(O)_2N(R^{12})(R^{13})$, wherein $C_{1-6}$alkyl is substituted with one, two, or three $R^{20a}$, and wherein $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20a}$;

$R^{9b}$ is selected from hydrogen, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, $C_{1-9}$heteroaryl, —$C(O)OR^{12}$, —$C(O)R^{15}$, —$C(O)N(R^{12})(R^{13})$, —$S(O)_2R^{15}$, and —$S(O)_2N(R^{12})(R^{13})$, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20a}$;

$R^{9c}$ is selected from hydrogen, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20a}$; or $R^{9b}$ and $R^{9c}$, together with the nitrogen to which they are attached, form a $C_{2-9}$heterocycloalkyl ring optionally substituted with one, two, or three $R^{20a}$;

$R^{9d}$ is selected from hydrogen, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl, wherein $C_{1-6}$alkyl is substituted with one, two, or three $R^{20a}$, and wherein $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20a}$;

$R^{9e}$ is selected from hydrogen, $C_{1-6}$alkyl, $C_{2-6}$alkenyl, $C_{2-6}$alkynyl, $C_{3-10}$cycloalkyl, $C_{2-9}$heterocycloalkyl, $C_{1-9}$heteroaryl, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{15}$, —$S(O)_2R^{15}$, —$S(O)_2N(R^{12})(R^{13})$, —$S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, —$CH_2S(O)_2N(R^{12})(R^{13})$, —$CH_2N(R^{12})S(O)_2(R^{13})$, and —$P(O)(R^{17})(R^{17a})$, wherein $C_{1-6}$alkyl, $C_{2-6}$alkenyl, $C_{2-6}$alkynyl, $C_{3-10}$cycloalkyl, $C_{2-9}$heterocycloalkyl, and $C_{1-9}$heteroaryl are optionally substituted with one, two, or three $R^{20a}$;

$R^{9f}$ is selected from hydrogen, $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20a}$;

$R^{9g}$ is selected from $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl, wherein $C_{1-6}$alkyl, $C_{2-6}$alkenyl, $C_{2-6}$alkynyl, $C_{3-10}$cycloalkyl, $C_{2-9}$heterocycloalkyl, $C_{6-10}$aryl, and $C_{1-9}$heteroaryl are optionally substituted with one, two, or three $R^{20a}$;

each $R^{10}$ is independently selected from halogen, —CN, $C_{1-6}$alkyl, $C_{2-6}$alkenyl, $C_{2-6}$alkynyl, $C_{3-7}$cycloalkyl, $C_{2-9}$heterocycloalkyl, $C_{6-10}$aryl, $C_{1-9}$heteroaryl, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{15}$, —$S(O)_2R^{15}$, —$S(O)_2N(R^{12})(R^{13})$, —$S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, —$CH_2S(O)_2N(R^{12})(R^{13})$, —$CH_2N(R^{12})S(O)_2(R^{13})$, and —$P(O)(R^{17})(R^{17a})$, wherein $C_{1-6}$alkyl, $C_{2-6}$alkenyl, $C_{2-6}$alkynyl, $C_{3-7}$cycloalkyl, $C_{2-9}$heterocycloalkyl, $C_{6-10}$aryl, and $C_{1-9}$heteroaryl are optionally substituted with one, two, or three $R^{20a}$;

each $R^{12}$ is independently selected from hydrogen, $C_{1-6}$alkyl, $C_{1-6}$haloalkyl, $C_{2-6}$alkenyl, $C_{2-6}$alkynyl, $C_{3-7}$cycloalkyl, $C_{2-9}$heterocycloalkyl, $C_{6-10}$aryl, and $C_{1-9}$heteroaryl, wherein $C_{1-6}$alkyl, $C_{2-6}$alkenyl, $C_{2-6}$alkynyl, $C_{3-7}$cycloalkyl, $C_{2-9}$heterocycloalkyl, $C_{6-10}$aryl, and $C_{1-9}$heteroaryl are optionally substituted with one, two, or three $R^{20e}$;

each $R^{13}$ is independently selected from hydrogen, $C_{1-6}$alkyl, and $C_{1-6}$haloalkyl; or $R^{12}$ and $R^{13}$, together with the nitrogen to which they are attached, form a $C_{2-9}$heterocycloalkyl ring optionally substituted with one, two, or three $R^{20f}$; each $R^{14}$ is independently selected from hydrogen, $C_{1-6}$alkyl, and $C_{1-6}$haloalkyl;

each $R^{15}$ is independently selected $C_{1-6}$alkyl, $C_{2-6}$alkenyl, $C_{2-6}$alkynyl, $C_{3-7}$cycloalkyl, $C_{2-9}$heterocycloalkyl, $C_{6-10}$aryl, and $C_{1-9}$ heteroaryl, wherein $C_{1-6}$alkyl, $C_{2-6}$alkenyl, $C_{2-6}$alkynyl, $C_{3-7}$cycloalkyl, $C_{2-9}$heterocycloalkyl, $C_{6-10}$aryl, and $C_{1-9}$heteroaryl are optionally substituted with one, two, or three $R^{20g}$;

each $R^{17}$ and each $R^{17a}$ are each independently selected from $C_{1-6}$alkyl and $C_{3-6}$cycloalkyl, wherein $C_{1-6}$alkyl and $C_{3-6}$cycloalkyl are optionally substituted with one, two or three of $R^{20h}$; or $R^{17}$ and $R^{17a}$ are combined to form a $C_{2-9}$heterocycloalkyl ring;

each $R^{20a}$, $R^{20b}$, $R^{20c}$, $R^{20d}$, $R^{20e}$, $R^{20f}$, $R^{20g}$, and $R^{20h}$ are each independently selected from halogen, oxo, =NH, —CN, $C_{1-6}$alkyl, $C_{2-6}$alkenyl, $C_{2-6}$alkynyl, $C_{3-10}$cycloalkyl, —$CH_2$—$C_{3-10}$cycloalkyl, $C_{2-9}$heterocycloalkyl, —$CH_2$—$C_{2-9}$heterocycloalkyl, $C_{6-10}$aryl, —$CH_2$—$C_{6-10}$aryl, $C_{1-9}$heteroaryl, —$OR^{21}$, —$SR^{21}$, —$N(R^{22})(R^{23})$, —$C(O)OR^{22}$, —$C(O)N(R^{22})(R^{23})$, —$C(O)C(O)N(R^{22})(R^{23})$, —$OC(O)N(R^{22})(R^{23})$, —$N(R^{24})C(O)N(R^{22})(R^{23})$, —$N(R^{24})C(O)OR^{25}$, —$N(R^{24})C(O)R^{25}$, —$N(R^{24})S(O)_2R^{25}$, —$C(O)R^{25}$, —$S(O)_2R^{25}$, —$S(O)_2N(R^{22})(R^{23})$, —$OCH_2C(O)OR^{22}$, and —$OC(O)R^{25}$, wherein $C_{1-6}$alkyl, $C_{2-6}$alkenyl, $C_{2-6}$alkynyl, $C_{3-10}$cycloalkyl, —$CH_2$—$C_{3-10}$cycloalkyl, $C_{2-9}$heterocycloalkyl, —$CH_2$—$C_{2-9}$heterocycloalkyl, $C_{6-10}$aryl, —$CH_2$—$C_{6-10}$aryl, and $C_{1-9}$heteroaryl are optionally substituted with one, two, or three groups independently selected from halogen, oxo, =NH, —CN, $C_{1-6}$alkyl, $C_{1-6}$haloalkyl, $C_{1-6}$alkoxy, $C_{1-6}$haloalkoxy, —$OR^{21}$, —$SR^{21}$, —$N(R^{22})(R^{23})$, —$C(O)OR^{22}$, —$C(O)N(R^{22})(R^{23})$, —$C(O)C(O)N(R^{22})(R^{23})$, —$OC(O)N(R^{22})(R^{23})$, —$N(R^{24})C(O)N(R^{22})(R^{23})$, —$N(R^{24})C(O)OR^{25}$, —$N(R^{24})C(O)R^{25}$, —$N(R^{24})S(O)_2R^{25}$, —$C(O)R^{25}$, —$S(O)_2R^{25}$, —$S(O)_2N(R^{22})(R^{23})$, and —$OC(O)R^{25}$;

each $R^{21}$ is independently selected from H, $C_{1-6}$alkyl, $C_{1-6}$haloalkyl, $C_{2-6}$alkenyl, $C_{2-6}$alkynyl, $C_{3-7}$cycloalkyl, $C_{2-9}$heterocycloalkyl, $C_{6-10}$aryl, and $C_{1-9}$heteroaryl, wherein $C_{3-7}$cycloalkyl, $C_{2-9}$heterocycloalkyl, $C_{6-10}$aryl, and $C_{1-9}$heteroaryl are optionally substituted with one, two, or three groups independently selected from halogen and $C_{1-6}$alkyl;

each $R^{22}$ is independently selected from H, $C_{1-6}$alkyl, $C_{1-6}$haloalkyl, $C_{2-6}$alkenyl, $C_{2-6}$alkynyl, $C_{3-7}$cycloalkyl, $C_{2-9}$heterocycloalkyl, $C_{6-10}$aryl, and $C_{1-9}$heteroaryl, wherein $C_{3-7}$cycloalkyl, $C_{2-9}$heterocycloalkyl, $C_{6-10}$aryl, and $C_{1-9}$heteroaryl are optionally substituted with one, two, or three groups independently selected from halogen and $C_{1-6}$alkyl;

each $R^{23}$ is independently selected from H and $C_{1-6}$alkyl;

each $R^{24}$ is independently selected from H and $C_{1-6}$alkyl; and each $R^{25}$ is selected from $C_{1-6}$alkyl, $C_{2-6}$alkenyl, $C_{2-6}$alkynyl, $C_{3-7}$cycloalkyl, $C_{2-9}$heterocycloalkyl, $C_{6-10}$aryl, and $C_{1-9}$heteroaryl, wherein $C_{1-6}$alkyl, $C_{3-7}$cycloalkyl, $C_{2-9}$heterocycloalkyl, $C_{6-10}$aryl, and $C_{1-9}$heteroaryl are optionally substituted with one, two, or three groups independently selected from halogen, $C_{1-6}$alkyl, $C_{1-6}$haloalkyl, $C_{1-6}$alkoxy, $C_{3-7}$cycloalkyl, $C_{2-9}$heterocycloalkyl, $C_{6-10}$aryl, and $C_{1-9}$heteroaryl.

Embodiment A23. The compound of Embodiment A22, or a pharmaceutically acceptable salt or solvate thereof, wherein $R^8$ is —$OR^{9a}$.

Embodiment A24. The compound of Embodiment A22, or a pharmaceutically acceptable salt or solvate thereof, wherein $R^8$ is —$NR^{9b}R^{9c}$.

Embodiment A25. The compound of Embodiment A22, or a pharmaceutically acceptable salt or solvate thereof, wherein $R^8$ is —$C(R^{9e})(R^{9f})(R^{9g})$.

Embodiment A26. The compound of any one of Embodiments A1-A25, or a pharmaceutically acceptable salt or solvate thereof, wherein $R^6$ is selected from hydrogen, halogen, $C_{1-6}$alkyl, $C_{3-10}$cycloalkyl, $C_{2-9}$heterocycloalkyl, and $C_{1-9}$ heteroaryl, wherein $C_{1-6}$alkyl, $C_{3-10}$cycloalkyl, $C_{2-9}$heterocycloalkyl, and $C_{1-9}$heteroaryl are optionally substituted with one, two, or three $R^{20c}$.

Embodiment A27. The compound of any one of Embodiments A1-A26, or a pharmaceutically acceptable salt or solvate thereof, wherein $R^6$ is independently selected from hydrogen, halogen, and unsubstituted $C_{1-6}$alkyl.

Embodiment A28. The compound of any one of Embodiments A1-A27, or a pharmaceutically acceptable salt or solvate thereof, wherein $R^6$ is hydrogen.

Embodiment A29. The compound of any one of Embodiments A1-A28, or a pharmaceutically acceptable salt or solvate thereof, wherein $R^7$ is selected from hydrogen, halogen, $C_{1-6}$alkyl, $C_{3-10}$cycloalkyl, $C_{2-9}$heterocycloalkyl, and $C_{1-9}$ heteroaryl, wherein $C_{1-6}$alkyl, $C_{3-10}$cycloalkyl, $C_{2-9}$heterocycloalkyl, and $C_{1-9}$heteroaryl are optionally substituted with one, two, or three $R^{20c}$.

Embodiment A30. The compound of any one of Embodiments A1-A29, or a pharmaceutically acceptable salt or solvate thereof, wherein $R^7$ is independently selected from hydrogen, halogen, and unsubstituted $C_{1-6}$alkyl.

Embodiment A31. The compound of any one of Embodiments A1-A30, or a pharmaceutically acceptable salt or solvate thereof, wherein $R^7$ is unsubstituted $C_{1-6}$alkyl.

Embodiment A32. The compound of any one of Embodiments A1-A30, or a pharmaceutically acceptable salt or solvate thereof, wherein $R^7$ is hydrogen.

Embodiment A33. The compound of any one of Embodiments A1-A32, or a pharmaceutically acceptable salt or solvate thereof, wherein $R^5$ is selected from $C_{1-6}$alkyl and $C_{1-6}$haloalkyl.

Embodiment A34. The compound of any one of Embodiments A1-A33, or a pharmaceutically acceptable salt or solvate thereof, wherein $R^5$ is —$CH_3$.

Embodiment A35. The compound of any one of Embodiments A1-A34, or a pharmaceutically acceptable salt or solvate thereof, wherein $R^4$ is hydrogen.

Embodiment A36. The compound of any one of Embodiments A1-A35, or a pharmaceutically acceptable salt or solvate thereof, wherein $L^1$ is a bond.

Embodiment A37. The compound of any one of Embodiments A1-A36, or a pharmaceutically acceptable salt or solvate thereof, wherein $R^1$ is a 6-10 membered aryl ring substituted with one or more $R^{10}$.

Embodiment A38. The compound of any one of Embodiments A1-A37, or a pharmaceutically acceptable salt or solvate thereof, wherein $R^1$ is phenyl substituted with one or more $R^{10}$.

Embodiment A39. The compound of any one of Embodiments A1-A38, or a pharmaceutically acceptable salt or solvate thereof, wherein $R^1$ is phenyl substituted with one, two, or three $R^{10}$.

Embodiment A40. The compound of any one of Embodiments A1-A36, or a pharmaceutically acceptable salt or solvate thereof, wherein $R^1$ is a 5-10 membered heteroaryl ring are substituted with one or more $R^{10}$.

Embodiment A41. The compound of Embodiment A40, or a pharmaceutically acceptable salt or solvate thereof, wherein $R^1$ is a 5-10 membered heteroaryl ring are substituted with one, two, or three $R^{10}$.

Embodiment A42. The compound of any one of Embodiments A37-A41, or a pharmaceutically acceptable salt or solvate thereof, wherein each $R^{10}$ is independently selected from halogen, $C_{1-6}$alkyl, $C_{3-7}$cycloalkyl, $C_{2-9}$heterocycloalkyl, $C_{6-10}$aryl, $C_{1-9}$heteroaryl, —$OR^{12}$, and $N(R^{12})(R^{13})$, wherein $C_{1-6}$alkyl, $C_{3-7}$cycloalkyl, $C_{2-9}$heterocycloalkyl, $C_{6-10}$aryl, and $C_{1-9}$heteroaryl are optionally substituted with one, two, or three $R^{20d}$.

Embodiment A43. The compound of any one of Embodiments A37-A42, or a pharmaceutically acceptable salt or solvate thereof, wherein each $R^{10}$ is independently selected from halogen, $C_{1-6}$alkyl, and $N(R^{12})(R^{13})$, wherein $C_{1-6}$alkyl is optionally substituted with one, two, or three $R^{20d}$.

Embodiment A44. The compound of any one of Embodiments A37-A43, or a pharmaceutically acceptable salt or solvate thereof, wherein each $R^{10}$ is independently selected from halogen and $C_{1-6}$alkyl, wherein $C_{1-6}$alkyl is substituted with one, two, or three $R^{20d}$, and each $R^{20d}$ is halogen.

EXAMPLES

The following examples are provided for illustrative purposes only and not to limit the scope of the claims provided herein.

As used herein, the following abbreviations, unless otherwise indicated, shall be understood to have the following meanings:

ACN or MeCN acetonitrile
AcOH acetic acid
Ac acetyl
BINAP 2,2'-bis(diphenylphosphino)-1,1'-binaphthalene
Bn benzyl
BOC or Boc tert-butyl carbamate
i-Bu iso-butyl
t-Bu tert-butyl
DCM dichloromethane ($CH_2Cl_2$)
DIBAL-H diisobutylaluminum hydride
DIPEA or DIEA diisopropylethylamine
DMAP 4-(N,N-dimethylamino)pyridine
DME 1,2-dimethoxyethane
DMF N,N-dimethylformamide
DMA N,N-dimethylacetamide
DMSO dimethylsulfoxide
Dppf or dppf 1,1'-bis(diphenylphosphino)ferrocene
EDC or EDCI N-(3-dimethylaminopropyl)-N'-ethylcarbodiimide hydrochloride
eq equivalent(s)
Et ethyl
$Et_2O$ diethyl ether
EtOH ethanol
EtOAc ethyl acetate
HPLC high performance liquid chromatography
KHMDS potassium bis(trimethylsilyl)amide
NaHMDS sodium bis(trimethylsilyl)amide
LiHMDS lithium bis(trimethylsilyl)amide
LAH lithium aluminum anhydride
LCMS liquid chromatography mass spectrometry
Me methyl
MeOH methanol
MS mass spectroscopy
Ms mesyl
NMR nuclear magnetic resonance
Ph phenyl iPr/i-Pr iso-propyl
RP-HPLC reverse-phase high-pressure liquid chromatography
rt room temperature
TBS tert-butyldimethylsilyl
TEA triethylamine
TFA trifluoroacetic acid
THF tetrahydrofuran
TLC thin layer chromatography
TMS trimethylsilyl
TsOH/p-TsOH p-toluenesulfonic acid Example 1: Compound Synthesis Compound 101: Synthesis of 1-(4-((R)-1-(2-fluoro-3-(difluoromethyl)phenyl)ethylamino)-7-methoxy-2-methylpyrido[2,3-d]pyrimidin-6-yl)cyclopropanecarbonitrile

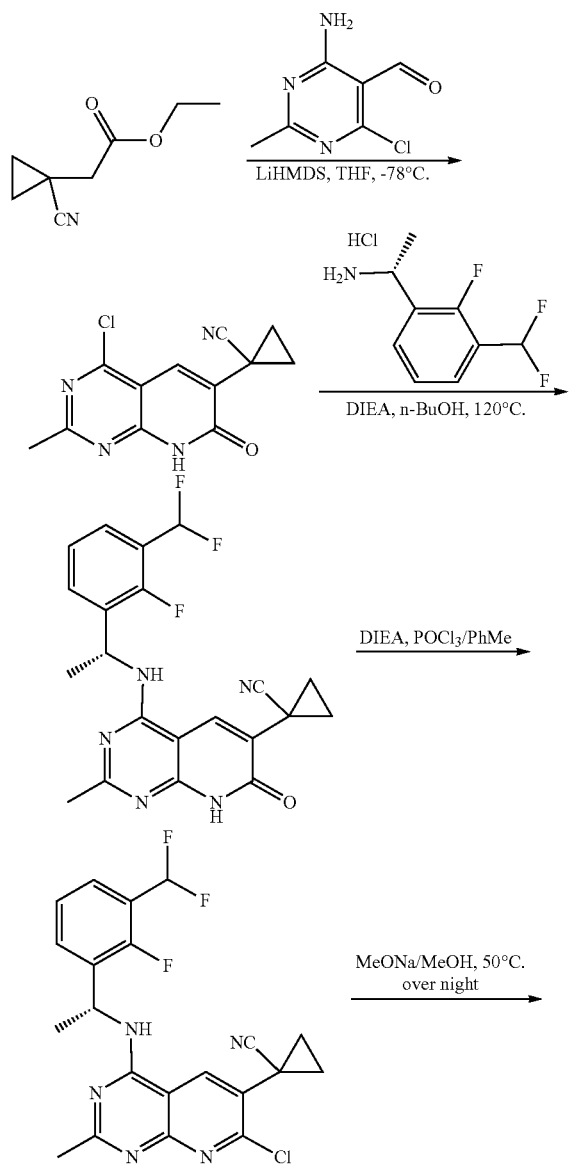

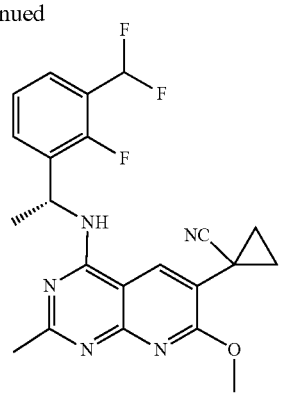

Compound 101

1-(4-chloro-7,8-dihydro-2-methyl-7-oxopyrido[2,3-d]pyrimidin-6-yl)cyclopropanecarbonitrile LiHMDS (1M, 7.8 mL, 4 eq., 7.8 mmol) was added to the solution of ethyl 2-(1-cyanocyclopropyl)acetate (300 mg, 1 eq., 1.96 mmol) in THF (20 mL) at −78° C. and stirred for 0.5 h at −78° C. Then a solution of 4-amino-6-chloro-2-methylpyrimidine-5-carbaldehyde (337 mg, 1 eq., 1.96 mmol) in THF (15 mL) was added at −78° C. and stirred at 0° C. for 0.5 hour. NH$_4$Cl (aq., 40 mL) was added to quench the reaction. The organic layer was collected and the aqueous layer was extracted with ethyl acetate (2×25 mL). The organic layers were combined and washed with brine and dried with Na$_2$SO$_4$. Solvent was removed under reduced pressure and the residue was purified on a silica gel column to obtain 1-(4-chloro-7,8-dihydro-2-methyl-7-oxopyrido[2,3-d]pyrimidin-6-yl)cyclopropanecarbonitrile. ESI-MS m/z: 261[M+H$^+$].

1-(4-((R)-1-(2-fluoro-3-(difluoromethyl)phenyl)ethylamino)-7,8-dihydro-2-methyl-7-oxopyrido[2,3-d]pyrimidin-6-yl)cyclopropanecarbonitrile 1-(4-chloro-7,8-dihydro-2-methyl-7-oxopyrido[2,3-d]pyrimidin-6-yl)cyclopropanecarbonitrile (380 mg, 1 eq. 1.46 mmol), (R)-1-(2-fluoro-3-(difluoromethyl)phenyl)ethanamine hydrochloride (330 mg, 1 eq. 1.46 mmol) and DIEA (2 mL) were dissolved in n-BuOH (9 mL) and the resulting mixture was stirred at 120° C. overnight in sealed tube. The reaction mixture was then cooled and concentrated. The residue was purified on a silica gel column to obtain 1-(4-((R)-1-(2-fluoro-3-(difluoromethyl)phenyl)ethylamino)-7,8-dihydro-2-methyl-7-oxopyrido[2,3-d]pyrimidin-6-yl)cyclopropanecarbonitrile. ESI-MS m/z: 415[M+H$^+$]. $^1$HNMR (400 MHz, DMSO-d$_6$): δ 12.12 (s, 1H), 8.34 (s, 1H), 8.25 (m, 1H), 7.65 (m, 1H), 7.50 (m, 1H), 7.40-7.06 (m, 2H), 5.71 (m, 1H), 2.26 (s, 3H), 1.61 (m, 2H), 1.56 (m, 3H), 1.37 (m, 2H).

1-(4-((R)-1-(2-fluoro-3-(difluoromethyl)phenyl)ethylamino)-7-chloro-2-methylpyrido[2,3-d]pyrimidin-6-yl)cyclopropanecarbonitrile 1-(4-((R)-1-(2-fluoro-3-(difluoromethyl)phenyl)ethylamino)-7,8-dihydro-2-methyl-7-oxopyrido[2,3-d]pyrimidin-6-yl)cyclopropanecarbonitrile (380 mg, 1 eq.) and 3 drops of DIEA were dissolved in POCl$_3$/toluene (1 mL/10 mL) and stirred at 100° C. overnight. The reaction mixture was cooled to room temperature and concentrated to provide 1-(4-((R)-1-(2-fluoro-3-(difluoromethyl)phenyl)ethylamino)-7-chloro-2-methylpyrido[2,3-d]pyrimidin-6-yl)cyclopropanecarbonitrile which was used directly in next reaction without further purification. ESI-MS m/z: 414 [M+H$^+$].

1-(4-((R)-1-(2-fluoro-3-(difluoromethyl)phenyl)ethylamino)-7-methoxy-2-methylpyrido[2,3-d]pyrimidin-6-yl)cyclopropanecarbonitrile 1-(4-((R)-1-(2-fluoro-3-(difluoromethyl)phenyl)ethylamino)-7-chloro-2-methylpyrido[2,3-d]pyrimidin-6-yl)cyclopropanecarbonitrile (100 mg) and sodium methoxide (300 mg) were dissolved in MeOH and stirred at 50° C. overnight under nitrogen. The reaction mixture was cooled, poured into water, and extracted with ethyl acetate (3×10 mL). The extracts were combined, washed with brine, and dried over sodium sulfate. The mixture was filtered and solvent was removed under reduced pressure. The residue was purified by preparative TLC to obtain the desired product 1-(4-((R)-1-(2-fluoro-3-(difluoromethyl)phenyl)ethylamino)-7-methoxy-2-methylpyrido[2,3-d]pyrimidin-6-yl)cyclopropanecarbonitrile (Compound 101). ESI-MS m/z: 428.9[M+H$^+$]. $^1$HNMR (400 MHz, DMSO-d$_6$): δ 8.73 (s, 1H), 8.58 (m, 1H), 7.68 (t, J=7.2 Hz, 1H), 7.51 (t, J=7.2 Hz, 1H), 7.29 (t, J=7.2 Hz, 1H), 7.23 (t, J=54.4 Hz, 1H), 5.78 (m, 1H), 4.06 (s, 3H), 2.53 (s, 3H), 1.73 (m, 2H), 1.59 (d, J=6.8 Hz, 3H), 1.498 (m, 2H).

Compound 102: Synthesis of (R)-4-(4-((1-(3-(difluoromethyl)-2-fluorophenyl)ethyl)amino)-7-methoxy-2-methylpyrido[2,3-d]pyrimidin-6-yl)tetrahydro-2H-thiopyran 1,1-dioxide

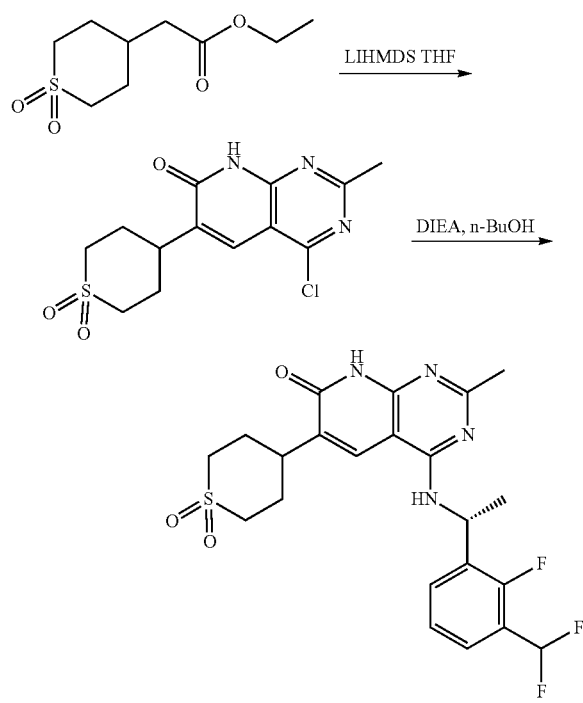

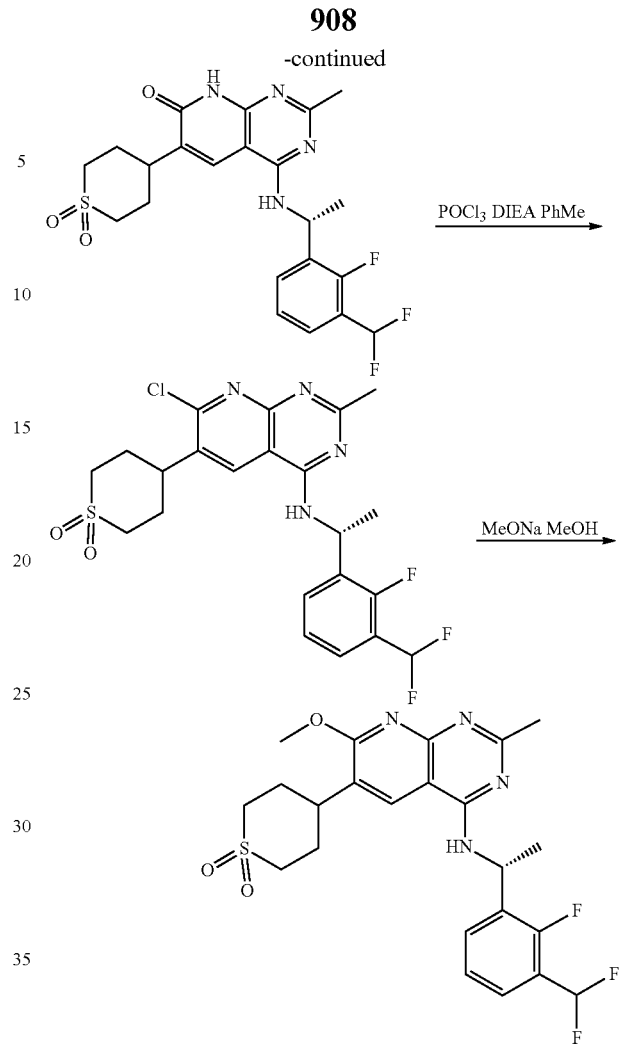

Compound 102

4-chloro-6-(1,1-dioxidotetrahydro-2H-thiopyran-4-yl)-2-methylpyrido[2,3-d]pyrimidin-7(8H)-one A solution of methyl ethyl 2-(1,1-dioxidotetrahydro-2H-thiopyran-4-yl)acetate (610 mg, 2.77 mmol) in THF (50 mL) was cooled to −78° C. under argon. LiHMDS (10 mL, 1 M in THF) was added dropwise and the resulting mixture was stirred for 2 hours at −78° C. to −45° C. Then 4-amino-6-chloro-2-methylpyrimidine-5-carbaldehyde (400 mg, 2.32 mmol) in THF (40 mL) was added dropwise at −78° C. The mixture was stirred at −78° C. and allowed to warm gradually to room temperature overnight. The reaction mixture was quenched with saturated NH$_4$Cl (20 mL). The mixture was extracted with ethyl acetate (30 mL×2). Organic extracts were combined, washed with brine, and dried over Na$_2$SO$_4$. The mixture was filtered and solvent was removed under reduced pressure. The residue was purified by flash chromatography on silica gel to afford 4-chloro-6-(1,1-dioxidotetrahydro-2H-thiopyran-4-yl)-2-methylpyrido[2,3-d]pyrimidin-7(8H)-one. ESI-MS m/z: 328 [M+H$^+$].

(R)-4-((1-(3-(difluoromethyl)-2-fluorophenyl)ethyl)amino)-6-(1,1-dioxidotetrahydro-2H-thiopyran-4-yl)-2-methylpyrido[2,3-d]pyrimidin-7(8H)-one To a solution of 4-chloro-6-(1,1-dioxidotetrahydro-2H-thiopyran-4-yl)-2-methylpyrido[2,3-d]pyrimidin-7(8H)-one (300 mg, 0.89 mmol) and (R)-1-(3-(difluoromethyl)-2-fluorophenyl)ethan-1-amine hydrochloride (260 mg, 1.16 mmol) in n-BuOH (8 mL) was added DIEA (1.42 g, 11.60 mmol). The resulting mixture was heated at 130° C. under argon and stirred overnight. The reaction mixture was cooled to room temperature and ethyl acetate (60 mL) was added. The organics were washed with brine and dried over $Na_2SO_4$. The mixture was filtered and solvent removed under reduced pressure. The residue was purified by flash chromatography on silica gel to afford (R)-4-((1-(3-(difluoromethyl)-2-fluorophenyl)ethyl)amino)-6-(1,1-dioxidotetrahydro-2H-thiopyran-4-yl)-2-methylpyrido[2,3-d]pyrimidin-7(8H)-one. ESI-MS m/z: 481 [M+H$^+$].

(R)-4-(7-chloro-4-((1-(3-(difluoromethyl)-2-fluorophenyl)ethyl)amino)-2-methylpyrido[2,3-d]pyrimidin-6-yl)tetrahydro-2H-thiopyran 1,1-dioxide To a solution of (R)-4-((1-(3-(difluoromethyl)-2-fluorophenyl)ethyl)amino)-6-(1,1-dioxidotetrahydro-2H-thiopyran-4-yl)-2-methylpyrido[2,3-d]pyrimidin-7(8H)-one (50 mg, 0.10 mmol) in toluene (15 mL) was added $POCl_3$ (1 mL) and DIEA (1.42 g, 11.60 mmol). The resulting mixture was heated at 100° C. under argon and stirred overnight. Then it was cooled to room temperature and concentrated to remove most of $POCl_3$ and toluene. The resulted residue was partitioned between 5 mL saturated $NaHCO_3$ and 20 mL dichloromethane. The aqueous layer was extracted with dichloromethane (20 mL×2). The organics were washed with brine, dried over $Na_2SO_4$, filtered, and concentrated under reduced pressure to give (R)-4-(7-chloro-4-((1-(3-(difluoromethyl)-2-fluorophenyl)ethyl)amino)-2-methylpyrido[2,3-d]pyrimidin-6-yl)tetrahydro-2H-thiopyran 1,1-dioxide. ESI-MS m/z: 499 [M+H$^+$].

(R)-4-(4-((1-(3-(difluoromethyl)-2-fluorophenyl)ethyl)amino)-7-methoxy-2-methylpyrido[2,3-d]pyrimidin-6-yl)tetrahydro-2H-thiopyran 1,1-dioxide To a solution of (R)-4-(7-chloro-4-((1-(3-(difluoromethyl)-2-fluorophenyl)ethyl)amino)-2-methylpyrido[2,3-d]pyrimidin-6-yl)tetrahydro-2H-thiopyran 1,1-dioxide (45 mg, 0.09 mmol) and sodium methoxide (40 mg, 0.75 mmol) in MeOH (20 mL) at 0° C. were added NaH (60%, 30 mg, 0.75 mmol). Then the resulting mixture was heated at 65° C. under argon and stirred for 3 hours. Then cooled to room temperature and concentrated to remove most of MeOH. The mixture was extracted with ethyl acetate (20 mL×2). Organic extracts were combined, washed with brine, and dried over $Na_2SO_4$. It was filtered and solvent was removed under reduced pressure to give a crude. The crude was purified by preparative TLC to afford (R)-4-(4-((1-(3-(difluoromethyl)-2-fluorophenyl)ethyl)amino)-7-methoxy-2-methylpyrido[2,3-d]pyrimidin-6-yl)tetrahydro-2H-thiopyran 1,1-dioxide (Compound 102) as a white solid. ESI-MS m/z: 495 [M+H$^+$]. $^1$HNMR (DMSO-$d_6$, 400 MHz): δ 8.97 (brs, 1H), 8.70 (s, 1H), 7.71 (t, J=7.2 Hz, 1H), 7.52 (t, J=6.8, 1H), 7.32 (t, J=7.2 Hz, 1H), 7.24 (t, J=53.4 Hz, 1H), 5.83-5.79 (m, 1H), 4.01 (s, 3H), 3.45-3.42 (m, 3H), 3.18-3.15 (m, 2H), 2.38 (s, 3H), 2.28-2.16 (m, 4H), 1.65-1.63 (d, J=7.2 Hz, 3H).

Compound 103: Synthesis of (R)—N-(1-(3-(difluoromethyl)-2-fluorophenyl)ethyl)-7-methoxy-2-methyl-6-(4-methylpiperazin-1-yl)pyrido[2,3-d]pyrimidin-4-amine

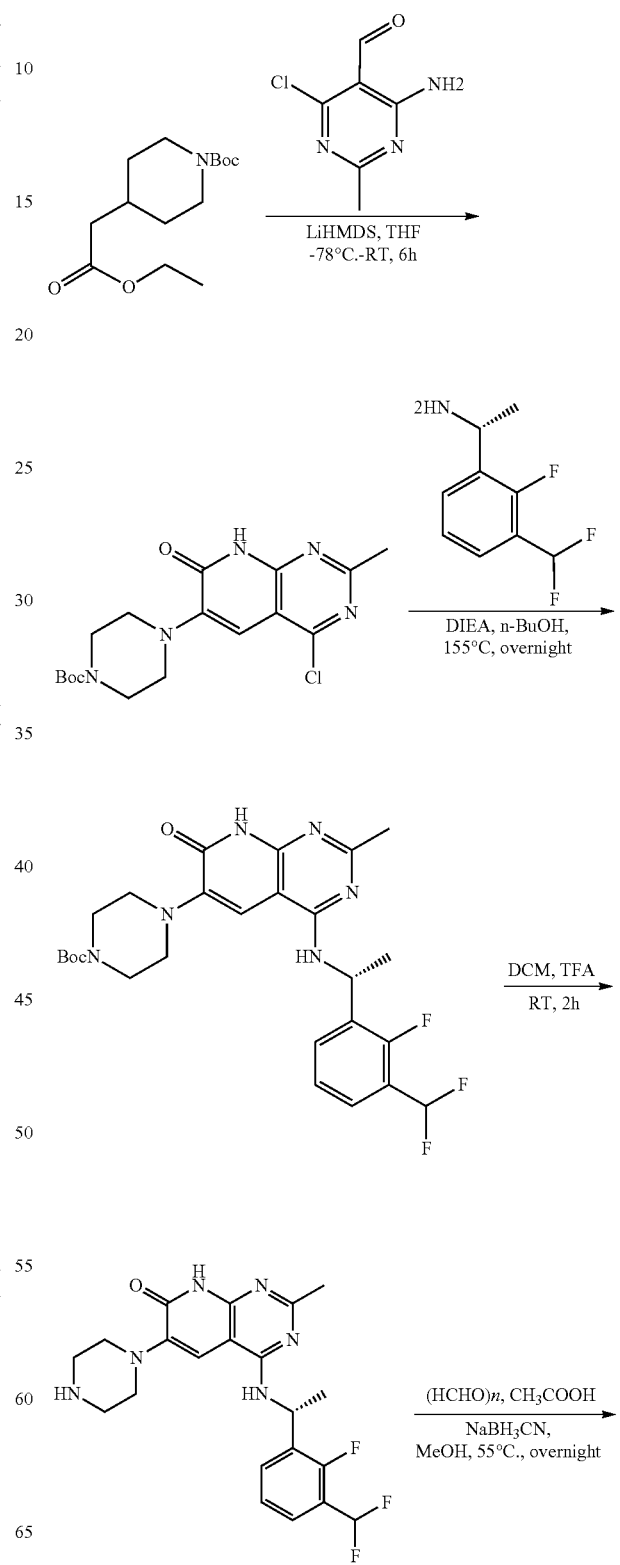

-continued

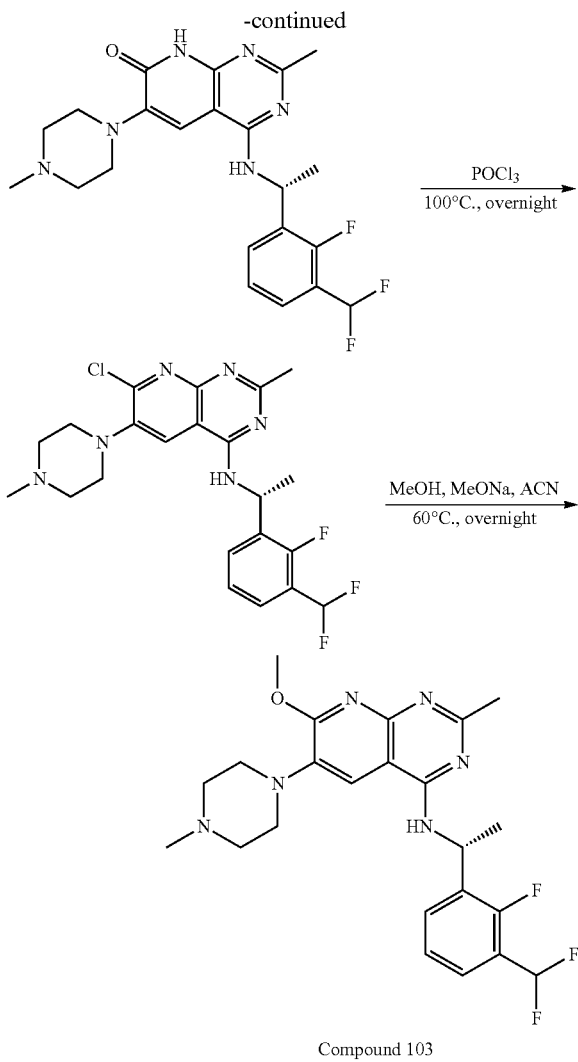

Compound 103 tert-Butyl 4-(4-chloro-2-methyl-7-oxo-7,8-dihydropyrido[2,3-d]pyrimidin-6-yl)piperazine-1-carboxylate To a stirred solution of tert-butyl 4-(2-ethoxy-2-oxoethyl)piperazine-1-carboxylate (500 mg, 1.83 mmol) in THF (10 mL) was added dropwise lithium diisopropylamide (5 ml, 1 M in THF) at −78° C. under argon. After 0.5 h, a solution of 4-amino-6-chloro-2-methylpyrimidine-5-carbaldehyde (282 mg, 1.52 mmol) in THF (5 mL) was added dropwise. The mixture was stirred at −78° C. and allowed to stir at room temperature for additional 6 hours. The reaction mixture was quenched with NH$_4$Cl (aq). It was then extracted with ethyl acetate (50 mL×2), washed with brine, dried over Na$_2$SO$_4$ and filtered. It was concentrated to provide a crude. The crude was purified by flash chromatography on silica gel (20%-30% petroleum and ethyl acetate) to afford the desired product tert-butyl 4-(4-chloro-2-methyl-7-oxo-7,8-dihydropyrido[2,3-d]pyrimidin-6-yl)piperazine-1-carboxylate as a white solid. ESI-MS m/z: 380.2 [M+H$^+$].

tert-Butyl(R)-4-(4-((1-(3-(difluoromethyl)-2-fluorophenyl)ethyl)amino)-2-methyl-7-oxo-7,8-dihydropyrido[2,3-d]pyrimidin-6-yl)piperazine-1-carboxylate To a stirred solution of tert-butyl 4-(4-chloro-2-methyl-7-oxo-7,8-dihydropyrido[2,3-d]pyrimidin-6-yl)piperazine-1-carboxylate (400 mg, 1.05 mmol), (R)-1-(3-(difluoromethyl)-2-fluorophenyl)ethan-1-amine (250 mg, 1.11 mmol), in n-BuOH (5 mL) was added DIEA (0.5 mL). The mixture was stirred at 155° C. overnight under argon. It was then cooled to room temperature and solvent was removed under reduced pressure. The reaction mixture was extracted with ethyl acetate (50 mL×2). The extracts was combined, washed with brine, dried over Na$_2$SO$_4$ and filtered. Solvent was removed under reduced pressure and the residue was purified by flash chromatography on silica gel to afford tert-butyl(R)-4-(4-((1-(3-(difluoromethyl)-2-fluorophenyl)ethyl)amino)-2-methyl-7-oxo-7,8-dihydropyrido[2,3-d]pyrimidin-6-yl)piperazine-1-carboxylate as a white solid. ESI-MS m/z: 533.2 [M+H$^+$].

(R)-4-((1-(3-(difluoromethyl)-2-fluorophenyl)ethyl)amino)-2-methyl-6-(piperazin-1-yl)pyrido[2,3-d]pyrimidin-7(8H)-one To a stirred solution of tert-butyl(R)-4-(4-((1-(3-(difluoromethyl)-2-fluorophenyl)ethyl)amino)-2-methyl-7-oxo-7,8-dihydropyrido[2,3-d]pyrimidin-6-yl)piperazine-1-carboxylate (400 mg, 0.751 mmol) in DCM (5 mL) was added TFA (0.5 mL) dropwise at room temperature. The mixture was stirred for 2 hours. The solvent was removed under reduced pressure to afford (R)-4-((1-(3-(difluoromethyl)-2-fluorophenyl)ethyl)amino)-2-methyl-6-(piperazin-1-yl)pyrido[2,3-d]pyrimidin-7(8H)-one which was used in the next step without further purification.

(R)-4-((1-(3-(difluoromethyl)-2-fluorophenyl)ethyl)amino)-2-methyl-6-(4-methylpiperazin-1-yl)pyrido[2,3-d]pyrimidin-7(8H)-one A solution of (R)-4-((1-(3-(difluoromethyl)-2-fluorophenyl)ethyl)amino)-2-methyl-6-(piperazin-1-yl)pyrido[2,3-d]pyrimidin-7(8H)-one (300 mg, 0.654 mmol) and paraformaldehyde (294 mg, 3.27 mmol), acetic acid (78 mg, 3.27 mmol) in MeOH (10 mL) was stirred at room temperature for 30 minutes. Sodium cyanoborohydride (392 mg, 6.54 mmol) was added. The mixture was stirred at 55° C. overnight under argon. It was then cooled to room temperature and solvent was removed under reduced pressure. It was extracted with ethyl acetate (50 mL×2). The organics was combined, washed with brine, dried over Na$_2$SO$_4$ and filtered. Solvent was removed under reduced pressure to give a crude. The crude was purified by flash chromatography on silica gel to afford (R)-4-((1-(3-(difluoromethyl)-2-fluorophenyl)ethyl)amino)-2-methyl-6-(4-methylpiperazin-1-yl)pyrido[2,3-d]pyrimidin-7(8H)-one as a white solid. ESI-MS m/z: 447.2 [M+H$^+$].

(R)-7-chloro-N-(1-(3-(difluoromethyl)-2-fluorophenyl)ethyl)-2-methyl-6-(4-methylpiperazin-1-yl)pyrido[2,3-d]pyrimidin-4-amine A solution of (R)-4-((1-(3-(difluoromethyl)-2-fluorophenyl)ethyl)amino)-2-methyl-6-(4-methylpiperazin-1-yl)pyrido[2,3-d]pyrimidin-7(8H)-one (200 mg, 0.448 mmol) in POCl$_3$ (5 mL) was stirred at 100° C. overnight under argon.

913

The reaction mixture was cooled to room temperature and solvent was removed under reduced pressure. The mixture was extracted with ethyl acetate (50 mL×2), washed with brine, dried over Na$_2$SO$_4$ and filtered. Solvent was removed under reduced pressure to give a crude. The crude was purified by flash chromatography on silica gel to afford (R)-7-chloro-N-(1-(3-(difluoromethyl)-2-fluorophenyl)ethyl)-2-methyl-6-(4-methylpiperazin-1-yl)pyrido[2,3-d]pyrimidin-4-amine as a yellow oil. ESI-MS m/z: 465.2 [M+H$^+$]

(R)—N-(1-(3-(difluoromethyl)-2-fluorophenyl)ethyl)-7-methoxy-2-methyl-6-(4-methylpiperazin-1-yl)pyrido[2,3-d]pyrimidin-4-amine To a solution of (R)-7-chloro-N-(1-(3-(difluoromethyl)-2-fluorophenyl)ethyl)-2-methyl-6-(4-methylpiperazin-1-yl)pyrido[2,3-d]pyrimidin-4-amine (100 mg, 0.215 mmol) in MeOH (10 mL) and ACN (5 mL) was added sodium methoxide (116 mg, 2.15 mmol) under argon. The mixture was stirred at 60° C. overnight. The mixture was cooled to room temperature and solvent was removed under reduced pressure. It was extracted with ethyl acetate (50 mL×2), washed with brine, dried over Na$_2$SO$_4$ and filtered. Solvent was removed under reduced pressure and the residue was purified by HPLC to afford (R)—N-(1-(3-(difluoromethyl)-2-fluorophenyl)ethyl)-7-methoxy-2-methyl-6-(4-methylpiperazin-1-yl)pyrido[2,3-d]pyrimidin-4-amine (Compound 103) as a white sold. ESI-MS m/z: 461.2 [M+H$^+$]. $^1$HNMR: (CDCl$_3$, 400 MHz): δ 7.76 (s, 1H), 7.63 (t, J=6.8 Hz, 1H), 7.44 (t, J=6.8 Hz, 1H), 7.13 (t, J=7.6 Hz, 1H), 6.90 (t, J=55.2 Hz, 1H), 5.83 (m, 1H), 4.12 (s, 3H), 3.40 (brs, 4H), 3.03 (brs, 4H), 2.62 (s, 3H), 2.54 (s, 3H), 1.72 (d, J=6.8 Hz).

Compound 104: Synthesis of (R)-7-chloro-N-(1-(3-(difluoromethyl)-2-fluorophenyl)ethyl)-6-(1-isopropylpiperidin-4-yl)-2-methylpyrido[2,3-d]pyrimidin-4-amine

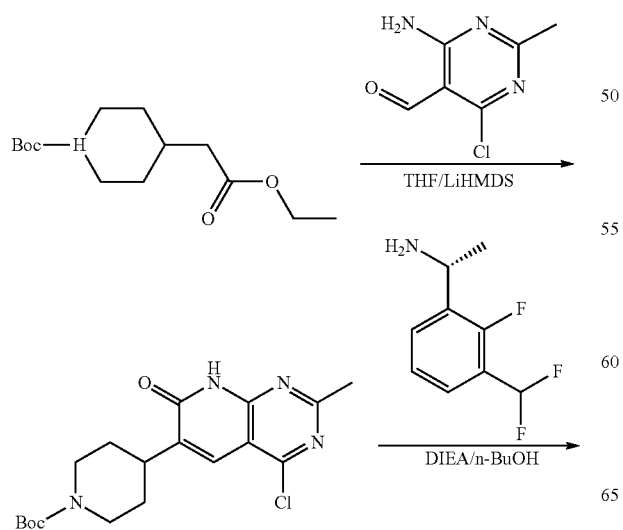

914

-continued

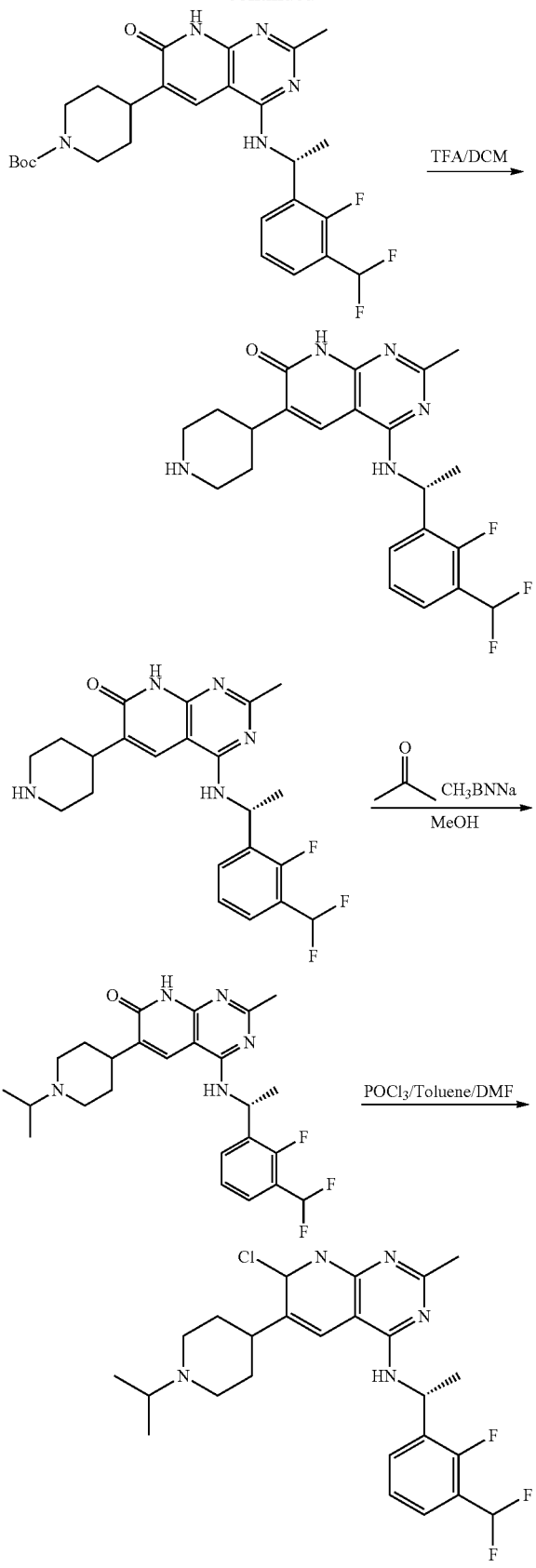

Compound 104 tert-Butyl 4-(4-chloro-2-methyl-7-oxo-7,8-dihydropyrido[2,3-d]pyrimidin-6-yl)piperidine-1-carboxylate A solution of tert-butyl 4-(2-ethoxy-2-oxoethyl)piperidine-1-carboxylate (500 mg, 1.85 mmol) in THF (10 ml) was cooled to −78° C. under argon. LiHMDS (7.4 mL, 1 M in THF) was added dropwise and the resulting mixture was stirred for 40 min at −78° C. to −45° C. Then 4-amino-6-chloro-2-methylpyrimidine-5-carbaldehyde (287 mg, 1.67 mmol) in THF (10 mL) was added dropwise at −78° C. The mixture was stirred at −78° C. and allowed to warm gradually to room temperature overnight. It was quenched with saturated NH$_4$Cl (10 mL). The mixture was extracted with ethyl acetate (30 mL×2). Organic extracts were combined, washed with brine, and dried over Na$_2$SO$_4$. It was filtered and solvent was removed under reduced pressure and the residue was purified by flash chromatography on silica gel to afford tert-butyl 4-(4-chloro-2-methyl-7-oxo-7,8-dihydropyrido[2,3-d]pyrimidin-6-yl)piperidine-1-carboxylate as a white solid. ESI-MS m/z: 379 [M+H$^+$].

tert-Butyl (R)-4-(4-((1-(3-(difluoromethyl)-2-fluorophenyl)ethyl)amino)-2-methyl-7-oxo-7,8-dihydropyrido[2,3-d]pyrimidin-6-yl)piperidine-1-carboxylate To a solution of tert-butyl 4-(4-chloro-2-methyl-7-oxo-7,8-dihydropyrido[2,3-d]pyrimidin-6-yl)piperidine-1-carboxylate (100 mg, 0.27 mmol) and (R)-1-(3-(difluoromethyl)-2-fluorophenyl)ethan-1-amine hydrochloride (72 mg, 0.27 mmol) in n-BuOH (8 mL) was added DIEA (176 mg, 1.35 mmol). The resulting mixture was heated at 125° C. under argon and stirred overnight. The mixture was cooled to room temperature and ethyl acetate (60 mL) was added. The organics were washed with brine, dried over Na$_2$SO$_4$. It was filtered and solvent was removed under reduced pressure and the residue was purified by flash chromatography on silica gel to afford tert-butyl (R)-4-(4-((1-(3-(difluoromethyl)-2-fluorophenyl)ethyl)amino)-2-methyl-7-oxo-7,8-dihydropyrido[2,3-d]pyrimidin-6-yl)piperidine-1-carboxylate as a yellow solid. ESI-MS m/z: 532 [M+H$^+$].

(R)-4-((1-(3-(difluoromethyl)-2-fluorophenyl)ethyl)amino)-2-methyl-6-(piperidin-4-yl)pyrido[2,3-d]pyrimidin-7(8H)-one To a solution of tert-butyl(R)-4-(4-((1-(3-(difluoromethyl)-2-fluorophenyl)ethyl)amino)-2-methyl-7-oxo-7,8-dihydropyrido[2,3-d]pyrimidin-6-yl)piperidine-1-carboxylate (80 mg, 0.15 mmol) in dichloromethane (10 mL) at 0° C. was added 2,2,2-trifluoroacetic acid (2 mL). The resulting mixture was heated at room temperature under argon and stirred for 1 hour. The reaction mixture was concentrated to remove most of the 2,2,2-trifluoroacetic acid, and the resulted residue was partitioned between 5 mL saturated NaHCO$_3$ and 20 mL dichloromethane. The aqueous layer was extracted with dichloromethane (20 mL×2). The organics were combined, were washed with brine, and dried over Na$_2$SO$_4$. It was filtered and solvent was removed under reduced pressure. The residue was purified by flash chromatography on silica gel to afford the desired product as a yellow solid. ESI-MS m/z: 432 [M+H$^+$].

(R)-4-((1-(3-(difluoromethyl)-2-fluorophenyl)ethyl)amino)-6-(1-isopropylpiperidin-4-yl)-2-methylpyrido[2,3-d]pyrimidin-7(8H)-one To a solution of (R)-4-((1-(3-(difluoromethyl)-2-fluorophenyl)ethyl)amino)-2-methyl-6-(piperidin-4-yl)pyrido[2,3-d]pyrimidin-7(8H)-one (70 mg, 0.17 mmol) and acetone (50 mg, 0.85 mmol) in MeOH (10 ml) at room temperature was added acetic acid (1.2 mg, 0.02 mmol). The mixture was stirred for 30 min and sodium cyanoborohydride (54 mg, 0.85 mmol) was added. Then the resulting mixture was stirred at 55° C. under argon overnight. Then it was cooled to room temperature and concentrated to remove most of MeOH. The mixture was extracted with ethyl acetate (15 mL×2). Organic extracts were combined, washed with brine, and dried over Na$_2$SO$_4$. It was filtered and solvent was removed under reduced pressure and the residue was purified by flash chromatography on silica gel to afford the desired product as a yellow solid. ESI-MS m/z: 474 [M+H$^+$].

(R)-7-chloro-N-(1-(3-(difluoromethyl)-2-fluorophenyl)ethyl)-6-(1-isopropylpiperidin-4-yl)-2-methylpyrido[2,3-d]pyrimidin-4-amine To a solution of (R)-4-((1-(3-(difluoromethyl)-2-fluorophenyl)ethyl)amino)-6-(1-isopropylpiperidin-4-yl)-2-methylpyrido[2,3-d]pyrimidin-7(8H)-one (51 mg, 0.11 mmol) and N,N-dimethylformamide (0.8 mg, 0.01 mmol) at 0° C. in toluene (10 mL) was added POCl$_3$ (2 mL). The resulting mixture was heated at 105° C. under argon and stirred overnight. Then it was cooled to room temperature and concentrated to remove most of POCl$_3$ and toluene. The resulted residue was partitioned between 5 mL saturated NaHCO$_3$ and 20 mL dichloromethane. The aqueous layer was extracted with dichloromethane (20 mL×2). The organics were washed with brine and dried over Na$_2$SO$_4$. The mixture was filtered and solvent was removed under reduced pressure. The residue was purified by preparative TLC to afford (R)-7-chloro-N-(1-(3-(difluoromethyl)-2-fluorophenyl)ethyl)-6-(1-isopropylpiperidin-4-yl)-2-methylpyrido[2,3-d]pyrimidin-4-amine (Compound 104) as a white solid. ESI-MS m/z: 492 [M+H$^+$]. $^1$H NMR (400 MHz, MeOD): δ 8.67 (s, 1H), 7.58 (t, J=7.2 Hz, 1H), 7.39 (t, J=7.2 Hz, 1H), 7.15 (t, J=7.2 Hz, 1H), 6.90 (t, J=55.6 Hz, 1H), 5.80-5.75 (m, 1H), 3.56-3.48 (m, 3H), 3.38-3.32 (m, 1H), 2.36 (s, 3H), 2.26-2.20 (d, 2H), 2.14-2.05 (m, 4H), 1.64-1.50 (m, 3H), 1.35-1.34 (d, 6H).

Compound 105: Synthesis of (R)—N-(1-(3-(difluoromethyl)-2-fluorophenyl)ethyl)-6-((4-isopropylpiperazin-1-yl)methyl)-7-methoxy-2-methylpyrido[2,3-d]pyrimidin-4-amine

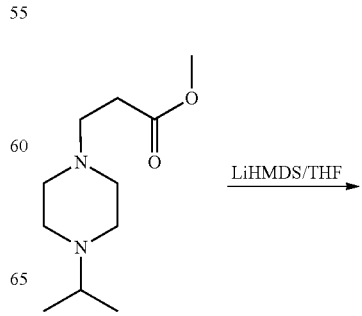

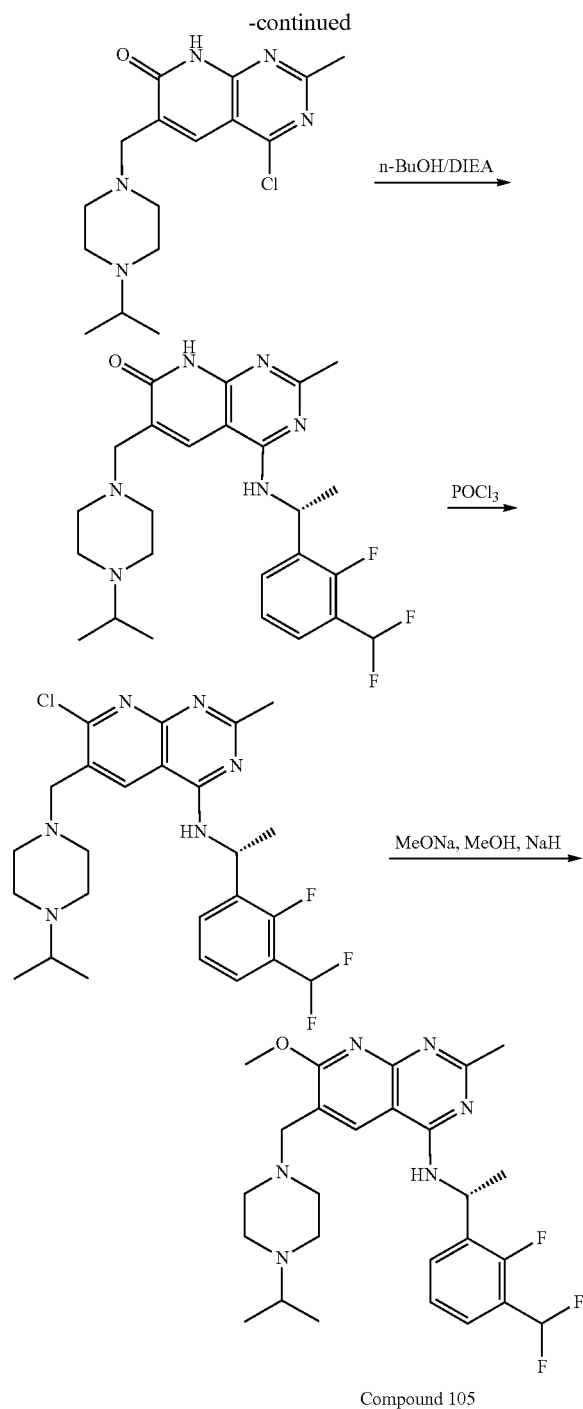

Compound 105

4-Chloro-6-((4-isopropylpiperazin-1-yl)methyl)-2-methylpyrido[2,3-d]pyrimidin-7(8H)-one A solution of methyl methyl 3-(4-isopropylpiperazin-1-yl)propanoate (1.0 g, 4.67 mmol) in THF (20 mL) was cooled to −78° C. under argon. LiHMDS (20 mL, 1M in THF) was added dropwise and the resulting mixture was stirred for 40 min at −78° C. to −45° C. Then 4-amino-6-chloro-2-methylpyrimidine-5-carbaldehyde (798 mg, 4.67 mmol) in THF (10 mL) was added dropwise at −78° C. The mixture was stirred at −78° C. and allowed to warm gradually to room temperature overnight. It was quenched with saturated $NH_4Cl$ (20 mL). The mixture was extracted with ethyl acetate (40 mL×2). Organic extracts were combined, washed with brine, and dried over $Na_2SO_4$. It was filtered, concentrated, and the residue was purified by flash chromatography on silica gel to afford the desired product as a yellow solid.

(R)-4-((1-(3-(difluoromethyl)-2-fluorophenyl)ethyl)amino)-6-((4-isopropylpiperazin-1-yl)methyl)-2-methylpyrido[2,3-d]pyrimidin-7(8H)-one To a solution of 4-chloro-6-((4-isopropylpiperazin-1-yl)methyl)-2-methylpyrido[2,3-d]pyrimidin-7(8H)-one (900 mg, 2.68 mmol) and (R)-1-(3-(difluoromethyl)-2-fluorophenyl)ethan-1-amine hydrochloride (507 mg, 2.68 mmol) in n-BuOH (20 mL) was added DIEA (2.07 g, 16.08 mmol). The resulting mixture was heated at 150° C. under argon and stirred overnight. It was cooled to room temperature and ethyl acetate (60 mL) was added. The organics were washed with brine, dried over $Na_2SO_4$. It was filtered and solvent was removed under reduced pressure. The residue was purified by flash chromatography on silica gel to afford the desired product as a yellow solid. ESI-MS m/z: 489 [M+H$^+$].

(R)-7-chloro-N-(1-(3-(difluoromethyl)-2-fluorophenyl)ethyl)-6-((4-isopropylpiperazin-1-yl)methyl)-2-methylpyrido[2,3-d]pyrimidin-4-amine To a solution of (R)-4-((1-(3-(difluoromethyl)-2-fluorophenyl)ethyl)amino)-6-((4-isopropylpiperazin-1-yl)methyl)-2-methylpyrido[2,3-d]pyrimidin-7(8H)-one (800 mg, 1.64 mmol) was added $POCl_3$ (10 mL). The resulting mixture was heated at 105° C. under argon and stirred overnight. Then it was cooled to room temperature and concentrated to remove most of $POCl_3$. The residue was partitioned between 10 mL saturated $NaHCO_3$ and 20 mL dichloromethane. It was extracted with dichloromethane (30 mL×2). The organics were washed with brine, dried over $Na_2SO_4$. It was filtered and solvent was removed under reduced pressure. The residue was purified by flash chromatography on silica gel to afford the desired product as a yellow solid. ESI-MS m/z: 507[M+H$^+$].

(R)—N-(1-(3-(difluoromethyl)-2-fluorophenyl)ethyl)-6-((4-isopropylpiperazin-1-yl)methyl)-7-methoxy-2-methylpyrido[2,3-d]pyrimidin-4-amine To a solution of (R)-7-chloro-N-(1-(3-(difluoromethyl)-2-fluorophenyl)ethyl)-6-((4-isopropylpiperazin-1-yl)methyl)-2-methylpyrido[2,3-d]pyrimidin-4-amine (700 mg, 1.38 mmol) and sodium methoxide (387 mg, 6.9 mmol) in MeOH (20 mL) was added NaH (60%, 166 mg, 6.9 mmol) at 0° C. Then the resulting mixture was heated at 65° C. under argon and stirred for 3 hours. It was then cooled to room temperature and concentrated to remove most of MeOH. The mixture was extracted with ethyl acetate (20 mL×2). Organic extracts were combined, washed with brine, and dried over $Na_2SO_4$. It was filtered and solvent was removed under reduced pressure to give a crude. The crude was purified by flash chromatography on silica gel to afford (R)—N-(1-(3-(difluoromethyl)-2-fluorophenyl)ethyl)-6-((4-isopropylpipemzin-1-yl)methyl)-7-methoxy-2-methylpyrido[2,3-d]pyrimidin-4-amine (Compound 105) as a yellow solid. ESI-MS m/z: 503[M+H$^+$]. $^1$HNMR (DMSO-d$_6$: 400 MHz): δ 8.61 (s, 1H), 8.52 (d, J=7.2 Hz, 1H), 7.68 (t, J=7.2 Hz, 1H), 7.50 (t, J=6.8 Hz, 1H), 7.29 (t, J=7.6 Hz, 1H), 7.23 (t, J=54.2 Hz, 1H), 5.77 (m, 1H), 3.95 (s, 3H), 3.53-3.48 (m, 2H), 3.35 (m, 9H), 2.33 (s, 3H), 1.59 (d, J=7.2 Hz, 3H), 1.01-0.96 (m, 6H).

Compound 106: Synthesis of (R)—N-(1-(3-(difluoromethyl)-2-fluorophenyl)ethyl)-7-methoxy-2-methyl-6-((4-methylpiperazin-1-yl)sulfonyl)pyrido[2,3-d]pyrimidin-4-amine

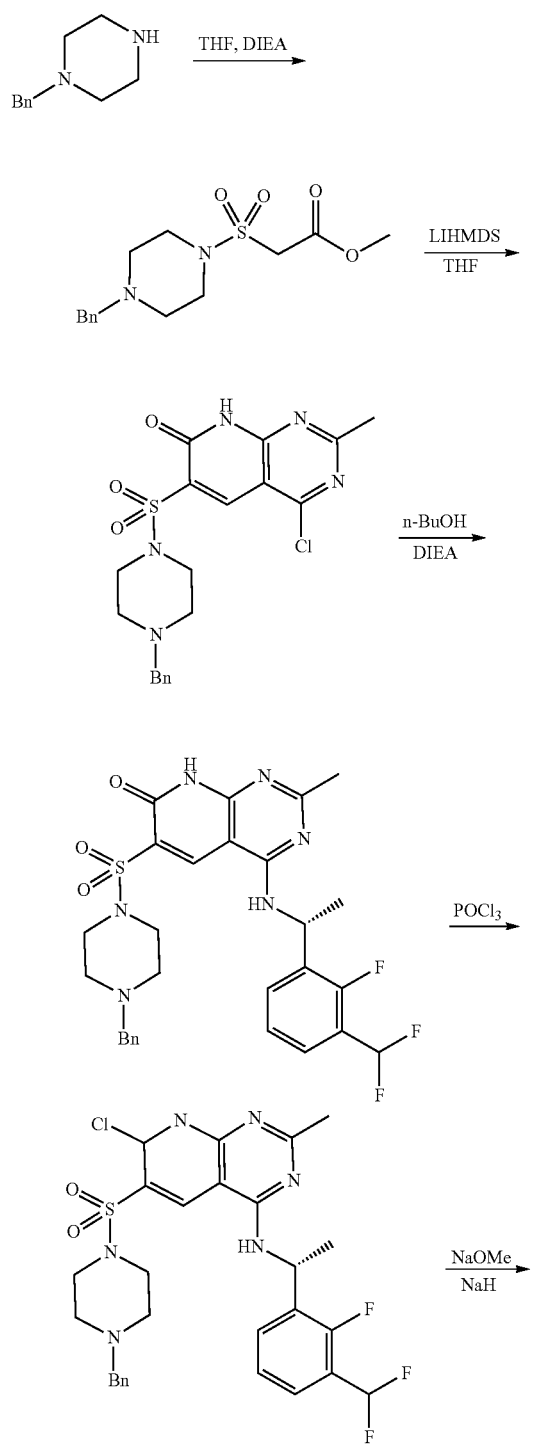

Compound 106

Methyl 2-((4-benzylpiperazin-1-yl)sulfonyl)acetate

To a stirred solution of 1-benzylpiperazine (300 mg, 1.70 mmol) and DIEA (1.1 g, 8.52 mmol) in dry THF (10 mL) at 0° C. were added ethyl 2-(chlorosulfonyl)acetate (381 mg, 2.05 mmol). The mixture was stirred for 16 hours at room temperature under argon. It was quenched with water and extracted with ethyl acetate (2×30 mL). The organic extracts were combined, washed with water, brine, and dried over Na$_2$SO$_4$. It was filtered and solvent was removed under reduced pressure to give the desired product as a colorless oil which was used in the next step without further purification. ESI-MS m/z: 313 [M+H$^+$].

((4-Benzylpiperazin-1-yl)sulfonyl)-4-chloro-2-methylpyrido[2,3-d]pyrimidin-7(8H)-one A solution of methyl 2-((4-benzylpiperazin-1-yl)sulfonyl)acetate (380 mg, 1.20 mmol) in THF (10 mL) was cooled to −78° C. under argon. LiHMDS (10 mL, 1 M in THF) was added dropwise and the resulting mixture was stirred for 40 min at −78° C. to −45° C. Then 4-amino-6-chloro-2-methylpyrimidine-5-carbaldehyde (209 mg, 1.20 mmol) in THF (10 mL) was added dropwise at −78° C. The mixture was stirred at −78° C. and allowed to warm gradually to room temperature overnight. It was quenched with saturated NH₄Cl (10 mL). The mixture was extracted with ethyl acetate (30 mL×2). Organic extracts were combined, washed with brine, and dried over Na₂SO₄. It was filtered and solvent was removed under reduced pressure. The residue was purified by flash chromatography on silica gel to afford the desired product as a yellow solid. ESI-MS m/z: 434 [M+H⁺].

(R)-6-((4-benzylpiperazin-1-yl)sulfonyl)-4-((1-(3-(difluoromethyl)-2-fluorophenyl)ethyl)amino)-2-methylpyrido[2,3-d]pyrimidin-7(8H)-one To a solution of 6-((4-benzylpiperazin-1-yl)sulfonyl)-4-chloro-2-methylpyrido[2,3-d]pyrimidin-7(8H)-one (180 mg, 0.42 mmol) and (R)-1-(3-(difluoromethyl)-2-fluorophenyl)ethan-1-amine hydrochloride (95 mg, 0.42 mmol) in n-BuOH (10 mL) was added DIEA (273 mg, 2.10 mmol). The resulting mixture was heated at 130° C. under argon and stirred overnight. It was cooled to room temperature and ethyl acetate (60 mL) was added. The organics were washed with brine and dried over Na₂SO₄. It was filtered and solvent was removed under reduced pressure. The residue was purified by flash chromatography on silica gel to afford the desired product as a yellow solid. ESI-MS m/z: 587 [M+H⁺].

(R)-6-((4-Benzylpiperazin-1-yl)sulfonyl)-7-chloro-N-(1-(3-(difluoromethyl)-2-fluorophenyl)ethyl)-2-methylpyrido[2,3-d]pyrimidin-4-amine To a solution of (R)-6-((4-benzylpiperazin-1-yl)sulfonyl)-4-((1-(3-(difluoromethyl)-2-fluorophenyl)ethyl)amino)-2-methylpyrido[2,3-d]pyrimidin-7(8H)-one (100 mg, 0.17 mmol) was added POCl₃ (5 mL). The resulting mixture was heated at 105° C. under argon and stirred overnight. It was then cooled to room temperature and concentrated to remove most of POCl₃. The residue was partitioned with 5 mL saturated NaHCO₃ and 20 mL dichloromethane. The aqueous layer was extracted with dichloromethane (20 mL×2). The organics were combined, washed with brine, and dried over Na₂SO₄. It was filtered and solvent was removed under reduced pressure. The residue was purified by flash chromatography on silica gel to afford the desired product as a yellow solid. ESI-MS m/z: 605[M+H⁺].

(R)-6-((4-benzylpiperazin-1-yl)sulfonyl)-N-(1-(3-(difluoromethyl)-2-fluorophenyl)ethyl)-7-methoxy-2-methylpyrido[2,3-d]pyrimidin-4-amine To a solution of (R)-6-((4-benzylpiperazin-1-yl)sulfonyl)-7-chloro-N-(1-(3-(difluoromethyl)-2-fluorophenyl)ethyl)-2-methylpyrido[2,3-d]pyrimidin-4-amine (90 mg, 0.15 mmol) and sodium methanolate (40 mg, 0.75 mmol) in MeOH (15 mL) at 0° C. were added NaH (60%, 30 mg, 0.75 mmol). Then the resulting mixture was heated at 65° C. under argon and stirred for 3 hours. It was then cooled to room temperature and concentrated to remove most of MeOH. The mixture was extracted with ethyl acetate (20 mL×2). Organic extracts were combined, washed with brine, and dried over Na₂SO₄. It was filtered and solvent was removed under reduced pressure. The residue was purified by flash chromatography on silica gel to afford the desired product as a yellow solid. ESI-MS m/z: 601[M+H⁺].

(R)—N-(1-(3-(difluoromethyl)-2-fluorophenyl)ethyl)-7-methoxy-2-methyl-6-(piperazin-1-ylsulfonyl)pyrido[2,3-d]pyrimidin-4-amine To a solution of (R)-6-((4-benzylpiperazin-1-yl)sulfonyl)-N-(1-(3-(difluoromethyl)-2-fluorophenyl)ethyl)-7-methoxy-2-methylpyrido[2,3-d]pyrimidin-4-amine (80 mg, 0.14 mmol) in MeOH (10 mL) at room temperature was added 10% Pd/C (42 mg, 0.40 mmol). Then the resulting mixture was stirred at room temperature under hydrogen and stirred for 16 hours. It was filtered through celite. The solvent was removed under reduced pressure. The residue was purified by preparative TLC to afford the desired product as a yellow solid. ESI-MS m/z: 511[M+H⁺]; ¹H NMR (400 MHz, MeOD): δ 9.27 (s, 1H), 7.65-7.61 (t, 1H), 7.51-7.48 (t, 1H), 7.27-7.23 (t, 1H), 7.16-6.88 (m, 1H), 5.88-5.83 (m, 1H), 4.18 (s, 3H), 3.47-3.45 (m, 4H), 3.11-3.08 (m, 4H), 2.26 (s, 3H), 1.70-1.68 (d, 3H).

(R)—N-(1-(3-(Difluoromethyl)-2-fluorophenyl)ethyl)-7-methoxy-2-methyl-6-((4-methylpiperazin-1-yl)sulfonyl)pyrido[2,3-d]pyrimidin-4-amine To a solution of (R)—N-(1-(3-(difluoromethyl)-2-fluorophenyl)ethyl)-7-methoxy-2-methyl-6-(piperazin-1-ylsulfonyl)pyrido[2,3-d]pyrimidin-4-amine (50 mg, 0.10 mmol) and paraformaldehyde (10 mg, 0.30 mmol) in MeOH (10 mL) at room temperature was added acetic acid (0.6 mg, 0.01 mmol). The reaction mixture was stirred for 30 min and sodium cyanoborohydride (19 mg, 0.30 mmol) was added. Then the resulting mixture was stirred at 55° C. under argon for overnight. Then it was cooled to room temperature and concentrated to remove most of MeOH. The mixture was extracted with ethyl acetate (15 mL×2). Organic extracts were combined, washed with brine, and dried over Na₂SO₄. It was filtered and solvent was removed under reduced pressure. The residue was purified by preparative TLC to afford (R)—N-(1-(3-(Difluoromethyl)-2-fluorophenyl)ethyl)-7-methoxy-2-methyl-6-((4-methylpiperazin-1-yl)sulfonyl)pyrido[2,3-d]pyrimidin-4-amine (Compound 106) as a yellow solid. ESI-MS m/z: 525 [M+H⁺]. ¹H NMR (400 MHz, MeOD): δ 9.25 (s, 1H), 7.63 (t, J=6.8 Hz, 1H), 7.50 (t, J=6.8 Hz, 1H), 7.26 (t, J=7.6 Hz, 1H), 7.01 (t, J=55.4 Hz, 1H), 5.89-5.83 (m, 1H), 4.17 (s, 3H), 3.39-3.37 (m, 4H), 2.59-2.56 (m, 4H), 2.46 (s, 3H), 2.36 (s, 3H), 1.70-1.68 (d, J=6.8 Hz, 3H).

Compound 107: Synthesis of (R)—N-(1-(2-fluoro-3-(trifluoromethyl)phenyl)ethyl)-3-(4-isopropylpiperazin-1-yl)-7-methylpyrimido[4,5-c]pyridazin-5-amine

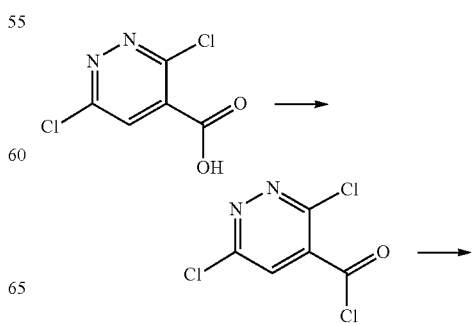

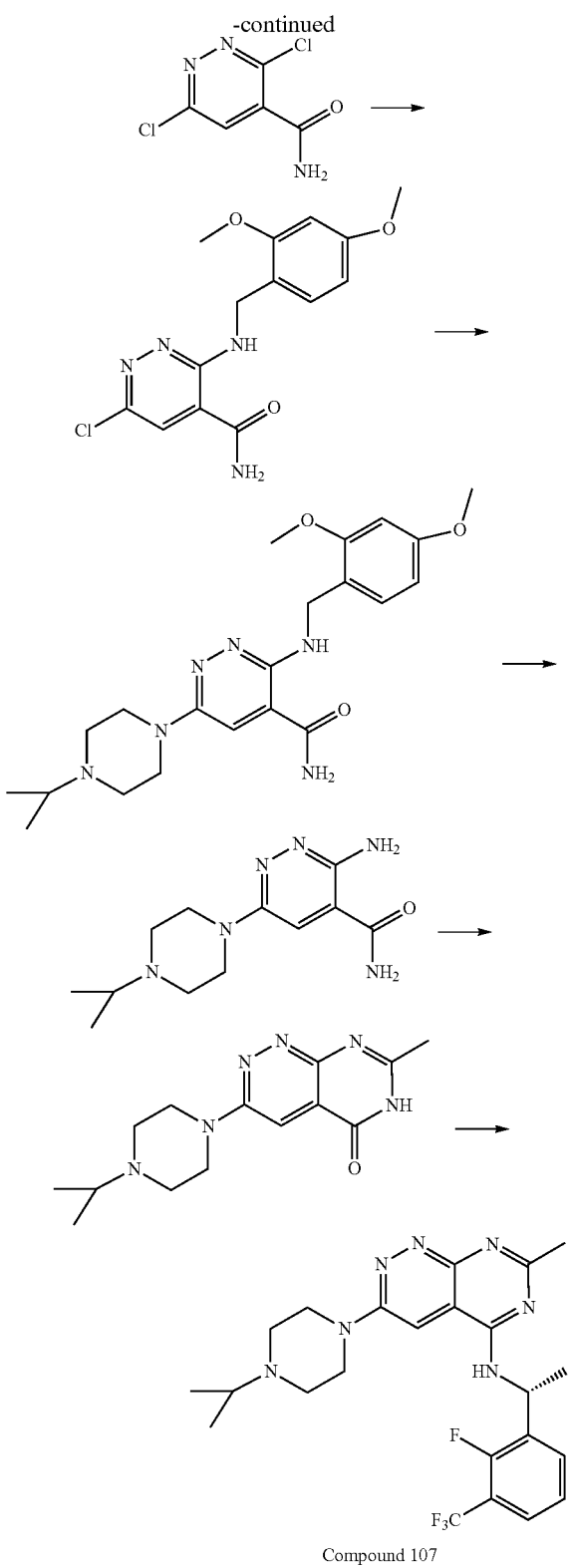

Compound 107

3,6-Dichloropyridazine-4-carbonyl chloride

To a suspension of 3,6-dichloropyridazine-4-carboxylic acid 1 (11.9 g, 61.7 mmol) in DCM (100 mL), was added a catalytic amount of DMF (0.1 mL), followed by addition of a solution of oxalyl chloride (2M in DCM, 68 mmol, 34 mL) at 0° C. over a period of 30 minutes. After addition, the reaction was stirred for additional 3 hours. The reaction was concentrated and the residue was used for next step without further purification.

3,6-Dichloropyridazine-4-carboxamide

To a cold solution of ammonium hydroxide (110 mL) was added 3,6-dichloropyridazine-4-carbonyl chloride in portions. The solid was collected, rinsed with $H_2O$ (20 mL) and dried for next step use.

6-Chloro-3-((2,4-dimethoxybenzyl)amino)pyridazine-4-carboxamide

To a solution of 3,6-dichloropyridazine-4-carboxamide (10.7 g, 55.7 mmol) in $CH_3CN$ (110 mL), (2,4-dimethoxyphenyl)methanamine (10.2 g, 61.3 mmol) was added, followed by DIPEA (8.6 g, 66.8 mmol). The mixture was heated at 50° C. overnight and then cooled to rt. The solid was collected and rinsed with cold acetonitrile (15 mL). The solid was dried for next use without further purification.

3-((2,4-Dimethoxybenzyl)amino)-6-(4-isopropylpiperazin-1-yl)pyridazine-4-carboxamide A suspension of 6-chloro-3-((2,4-dimethoxybenzyl)amino)pyridazine-4-carboxamide (1.5 g, 4.65 mmol) and 1-isopropylpiperazine (1.2 g, 9.3 mmol) in THF (10 mL) was heated at 100° C. for 10 minutes with microwave reactor, then gradually raised temperature to 170° C. and kept at that temperature for 6 hours. The reaction mixture was cooled to room temperature and the volatiles were evaporated. The residue was purified to give 3-((2,4-dimethoxybenzyl)amino)-6-(4-isopropylpiperazin-1-yl)pyridazine-4-carboxamide (1.34 g).

3-Amino-6-(4-isopropylpiperazin-1-yl)pyridazine-4-carboxamide 600 mg (1.45 mmol) of 3-((2,4-dimethoxybenzyl)amino)-6-(4-isopropylpiperazin-1-yl)pyridazine-4-carboxamide in TFA (5 mL) was stirred at room temperature. The volatiles were evaporated and the residue was treated with methanol. The solid was removed by filtration and rinsed with methanol (10 mL). The filtrate was concentrated and dried for next step use without further purification.

3-(4-Isopropylpiperazin-1-yl)-7-methylpyrimido[4,5-c]pyridazin-5(6H)-one

3-Amino-6-(4-isopropylpiperazin-1-yl)pyridazine-4-carboxamide (2.0 g, 7.56 mmol) was dissolved in ethyl acetate (4 mL) and methanol (4 mL). To the solution was added a solution of sodium methoxide in methanol (25% WT) (10 mL). The mixture was heated at 80° C. overnight. The reaction was cooled to room temperature, volatiles were evaporated, and the residue was neutralized with aqueous $NH_4Cl$. The mixture was evaporated to dryness. To the residue was added the dichloromethane-methanol (v/v 1:1, 50 mL). The mixture was filtered through a short pad of silica gel, rinsed with additional 50 mL of dichloromethane-methanol (v/v 1:1). The combined filtrate was evaporated to give 3-(4-isopropylpiperazin-1-yl)-7-methylpyrimido[4,5-c]pyridazin-5(6H)-one.

(R)—N-(1-(2-Fluoro-3-(trifluoromethyl)phenyl)ethyl)-3-(4-isopropylpiperazin-1-yl)-7-methylpyrimido[4,5-c]pyridazin-5-amine (Compound 107)

3-(4-Isopropylpiperazin-1-yl)-7-methylpyrimido[4,5-c]pyridazin-5(6H)-one (65 mg, 0.23 mmol) in CH₃CN was treated with BOP (112 mg, 0.25 mmol), followed by DBU (0.3 mmol). The mixture was stirred overnight. Then to the mixture was added (R)-1-(2-fluoro-3-(trifluoromethyl)phenyl)ethan-1-amine. HCl salt (56 mg, 0.23 mmol) was added in one portion, followed by DIPEA (0.35 mmol). The mixture was stirred for 2 hours at room temperature, then warmed at 50° C. for additional 2 hours. The volatile s were evaporated. The residue was diluted with dichloromethane (20 mL) and water (20 mL). The organic phase was separated from aqueous phase. The aqueous was extracted with DCM (15 mL×2). The combined dichloromethane extracts were washed with brine. The solution was concentrated and purified by preparative HPLC to give (R)—N-(1-(2-fluoro-3-(trifluoromethyl)phenyl)ethyl)-3-(4-isopropylpiperazin-1-yl)-7-methylpyrimido[4,5-c]pyridazin-5-amine (Compound 107). ¹HNMR (400 MHz, DMSO-d6): δ 8.98 (d, J=4 Hz, 1H), 7.95 (s, 1H), 7.80 (t, J=4 Hz, 1H), 7.66 (t, J=4 Hz, 1H), 7.37 (t, J=4 Hz, 1H), 5.74-5.68 (m, 1H), 3.67 (t, J=4 Hz, 4H), 2.74 (q, J=6 Hz, 1H), 2.65 (t, J=4 Hz, 4H), 2.33 (s, 3H), 1.63 (d, J=4 Hz, 3H), 1.03 (d, J=4 Hz, 6H). ESI-MS m/z: 478 [M+H⁺].

Compound 108: Synthesis of (R)—N-(1-(3-(difluoromethyl)-2-fluorophenyl)ethyl)-3-(4-isopropylpiperazin-1-yl)-7-methylpyrimido[4,5-c]pyridazin-5-amine

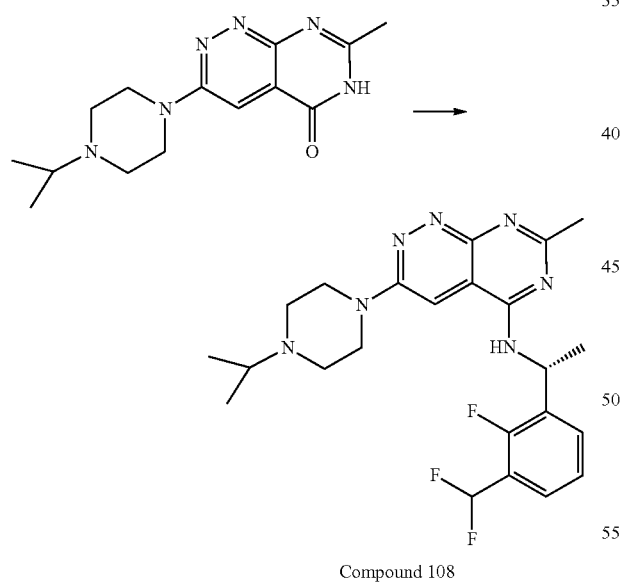

Compound 108

3-(4-Isopropylpiperazin-1-yl)-7-methylpyrimido[4,5-c]pyridazin-5(6H)-one (130 mg, 0.46 mmol) in CH₃CN was treated with BOP (224 mg, 0.50 mmol), followed by DBU (0.6 mmol). The mixture was stirred overnight. Then to the mixture was added in one portion (R)-1-(3-(difluoromethyl)-2-fluorophenyl)ethan-1-amine. HCl salt (104 mg, 0.46 mmol), followed by DIPEA (0.70 mmol). The mixture was stirred for 2 hours at room temperature, then warmed at 50° C. for additional 2 hours. The volatiles were evaporated. The residue was diluted with dichloromethane (20 mL) and water (20 mL). The organic phase was separated from aqueous phase. The aqueous phase was extracted with DCM (15 mL×2). The combined dichloromethane was washed with brine. The solution was concentrated and purified by preparative HPLC to give (R)—N-(1-(3-(difluoromethyl)-2-fluorophenyl)ethyl)-3-(4-isopropylpiperazin-1-yl)-7-methylpyrimido[4,5-c]pyridazin-5-amine (Compound 108). ¹HNMR (400 MHz, DMSO-d6): δ 8.92 (d, J=8 Hz, 1H), 7.95 (s, 1H), 7.67 (t, J=4 Hz, 1H), 7.52 (t, J=4 Hz, 1H), 7.32 (t, J=4 Hz, 1H), 7.24 (t, J=44 Hz, 1H), 5.78-5.72 (m, 1H), 3.67 (t, J=4 Hz, 4H), 2.74 (q, J=6 Hz, 1H), 2.65 (t, J=4 Hz, 4H), 2.35 (s, 3H), 1.63 (d, J=4 Hz, 3H), 1.03 (d, J=4 Hz, 6H). ESI-MS m/z: 460 [M+H⁺].

Compound 145: Synthesis of (R)-4-(4-((1-(3-(difluoromethyl)-2-fluorophenyl)-ethyl)amino)-7-(2-(dimethylamino)ethoxy)-2-methylpyrido[2,3-d]pyrimidin-6-yl)tetrahydro-2H-thiopyran 1,1-dioxide

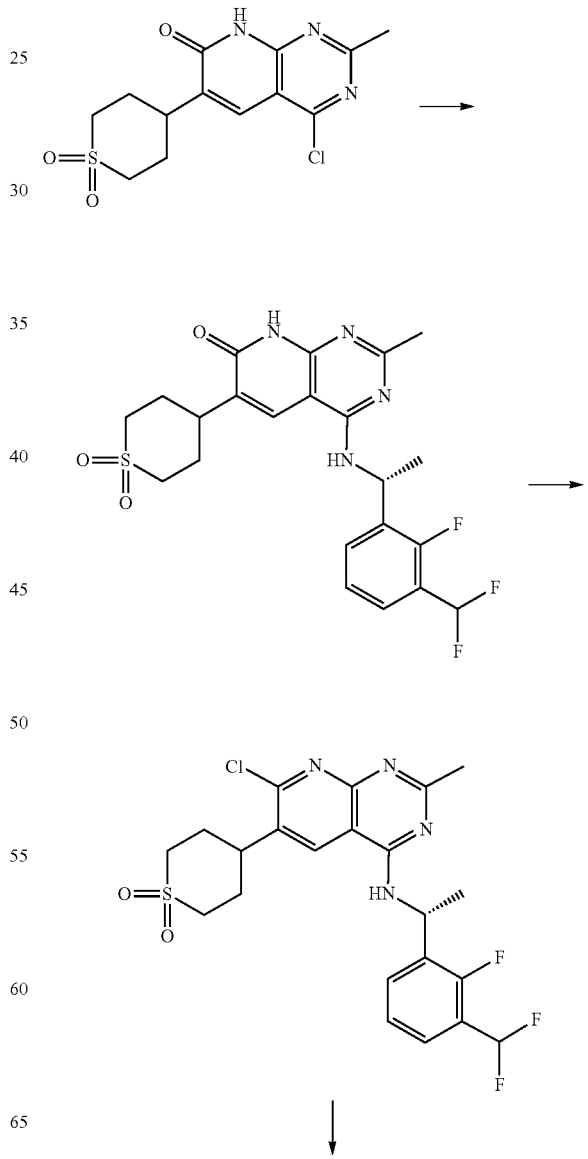

927

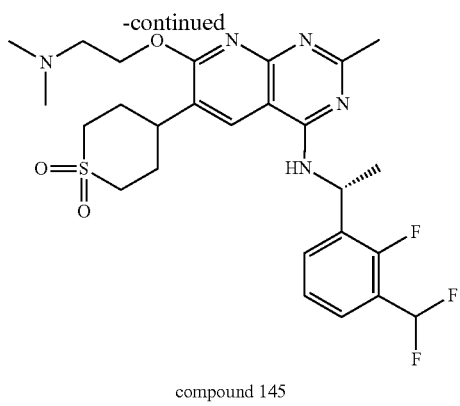

compound 145

(R)-4-((1-(3-(difluoromethyl)-2-fluorophenyl)ethyl) amino)-6-(1,1-dioxidotetrahydro-2H-thiopyran-4-yl)-2-methylpyrido[2,3-d]pyrimidin-7(8H)-one To a solution of 4-chloro-6-(1,1-dioxidotetrahydro-2H-thiopyran-4-yl)-2-methylpyrido[2,3-d]-pyrimidin-7(8H)-one (300 mg, 0.89 mmol) and (R)-1-(3-(difluoromethyl)-2-fluorophenyl)ethan-1-amine hydrochloride (260 mg, 1.16 mmol) in n-BuOH (8 ml) was added DIEA (1.42 g, 11.60 mmol). The resulting mixture was heated at 130° C. under argon and stirred for overnight. It was cooled to room temperature and ethyl acetate (60 mL) was added. The organics were washed with brine, dried over Na$_2$SO$_4$. It was filtered and solvent was removed under reduced pressure to give a crude. The crude was purified by flash chromatography on silica gel (dichloromethane:methyl alcohol=95:5) to afford the desired product (280 mg). ESI-MS m/z: 481[M+H]+;

(R)-4-(7-chloro-4-((1-(3-(difluoromethyl)-2-fluorophenyl)ethyl)amino)-2-methylpyrido[2,3-d]pyrimidin-6-yl)tetrahydro-2H-thiopyran 1,1-dioxide To a round bottom flask were added (R)-4-((1-(3-(difluoromethyl)-2-fluorophenyl)ethyl)amino)-6-(1,1-dioxidotetrahydro-2H-thiopyran-4-yl)-2-methylpyrido[2,3-d]pyrimidin-7(8H)-one (180 mg, 0.375 mmol) and POCl$_3$ (5 ml). The resulting mixture was heated at 100° C. under argon and stirred for overnight. Then it was cooled to RT and concentrated to remove most of POCl$_3$. It was quenched water (20 ml). The mixture was extracted with ethyl acetate (50 mL×3). Organic extracts were combined, washed with brine, and dried over Na$_2$SO$_4$. It was filtered and solvent was removed under reduced pressure to give a crude. ESI-MS m/z: 499[M+H]+;

(R)-4-(4-((1-(3-(difluoromethyl)-2-fluorophenyl) ethyl)amino)-7-(2-(dimethylamino)ethoxy)-2-methylpyrido[2,3-d]pyrimidin-6-yl)tetrahydro-2H-thiopyran 1,1-dioxide (compound 145)

To a solution of 2-(dimethylamino)ethan-1-ol (71 mg, 0.8 mmol) in THF (10 ml) was added NaH (60%) (48 mg, 1.2 mmol), Cs2CO3 (393 mg, 1.2 mmol) and (R)-4-(7-chloro-4-((1-(3-(difluoromethyl)-2-fluorophenyl)ethyl)amino)-2-methylpyrido[2,3-d]pyrimidin-6-yl)tetrahydro-2H-thiopyran 1,1-dioxide (200 mg, 0.4 mmol) in seal tube. The resulting mixture was heated at 100° C. under argon and stirred for 3.0 hours. It was then cooled to RT and concentrated to remove most of MeOH. The mixture was extracted with ethyl acetate (20 mL×2). Organic extracts were combined, washed with brine, and dried over Na$_2$SO$_4$. It was filtered and solvent was removed under reduced pressure to give a crude. The crude was purified by prep-TLC (dichloromethane:methyl alcohol=95:5) to afford the desired product. $^1$HNMR (DMSO-d6, 400 MHz): 8.35-8.34 (m, 1H), 8.20 (s, 1H), 7.67-7.63 (m, 1H), 7.52-7.49 (m, 1H), 7.37-7.10 (m, 2H), 5.75-5.72 (m, 1H), 4.44-4.36 (m, 2H), 3.23-3.12 (m, 4H), 2.51 (m, 2H), 2.31 (s, 3H), 2.21 (s, 6H), 2.17-2.14 (m, 5H), 1.60-1.58 (m, 3H) ppm.

Compound 326: Synthesis of 1-(4-(((R)-1-(3-(difluoromethyl)-2-fluorophenyl)ethyl)amino)-7-methoxy-2-(((S)-1-methylpyrrolidin-2-yl)methoxy) pyrido[2,3-d]pyrimidin-6-yl)cyclopropane-1-carbonitrile

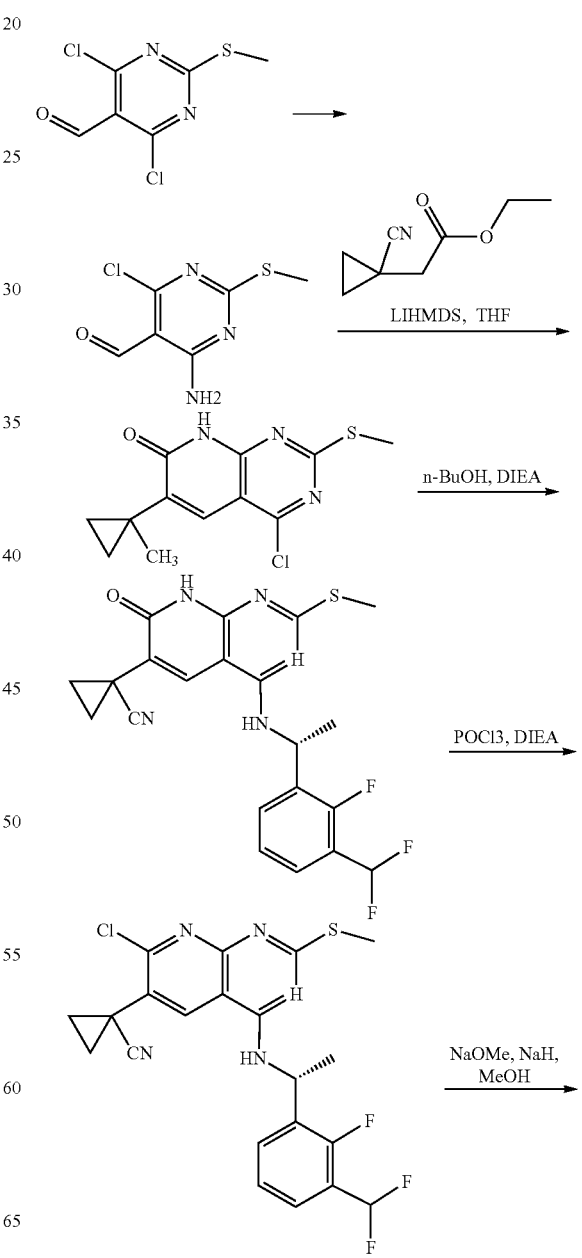

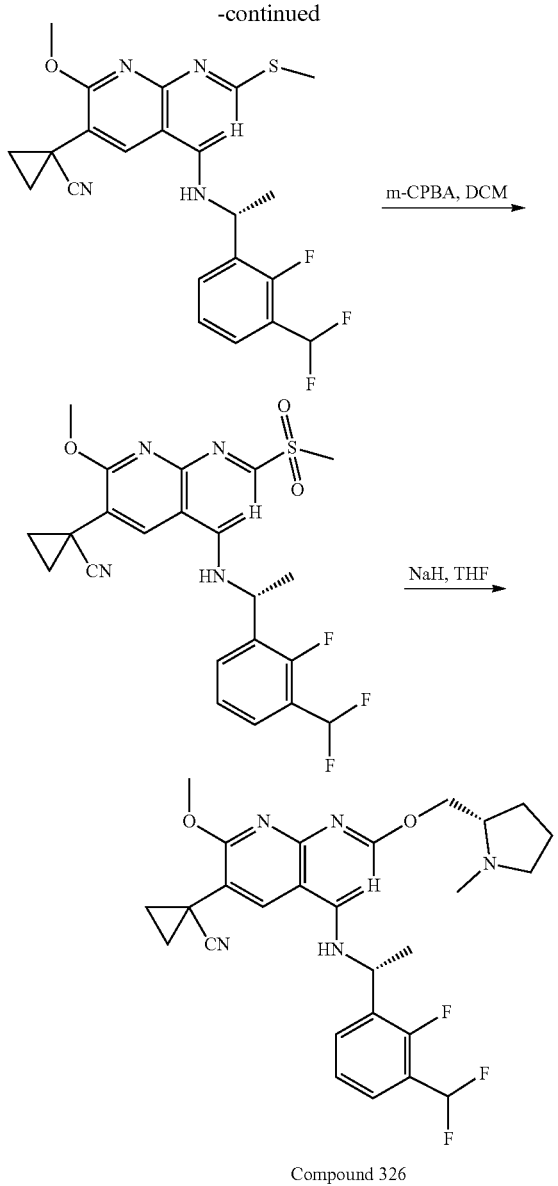

Compound 326

4-amino-6-chloro-2-(methylthio)pyrimidine-5-carbaldehyde

To a stirred solution of 4,6-dichloro-2-(methylthio)pyrimidine-5-carbaldehyde (10 g, 44.84 mmol) in DCM (100 mL) was added $NH_{3(aq)}$ (10 mL, 7M in MeOH, 70 mmol), and TEA (5 mL), then stirred for 2 hour at RT. The aqueous phase was concentrated. The residue was added MeOH (50 mL), filtered, the solid was washed by MeOH, dried to give desired product (7 g). ESI-MS m/z: 204.1 $[M+H]^+$.

1-(4-chloro-2-(methylthio)-7-oxo-7,8-dihydropyrido[2,3-d]pyrimidin-6-yl)cyclopropane-1-carbonitrile To a solution of 4-amino-6-chloro-2-(methylthio)pyrimidine-5-carbaldehyde (2.03 g, 10 mmol) and ethyl 2-(1-cyanocyclopropyl)acetate (2.295 g, 15 mmol) in THF (30 mL) was added LiHMDS (30 mL, 30 mmol) at −78° C. The mixture was warmed to RT and stirred for 16 hour and extracted with ethyl acetate and washed with $NH_4Cl$ solution. The organics was washed with brine, dried over $Na_2SO_4$ and concentrated. The residue was purified by flash column chromatography on silica gel (800 mg) ESI-MS m/z: 293.1 $[M+H]^+$.

(R)-1-(4-((1-(3-(difluoromethyl)-2-fluorophenyl)ethyl)amino)-2-(methylthio)-7-oxo-7,8-dihydropyrido[2,3-d]pyrimidin-6-yl)cyclopropane-1-carbonitrile To a solution of 1-(4-chloro-2-(methylthio)-7-oxo-7,8-dihydropyrido[2,3-d]pyrimidin-6-yl)cyclopropane-1-carbonitrile (800 mg, 2.733 mmol) and (R)-1-(3-(difluoromethyl)-2-fluorophenyl)ethan-1-amine (533 mg, 2.815 mmol) in n-BnOH (10 mL) was added DIEA (4 mL). The resulting mixture was heat to 130° C. for 3 hours. It was cooled to room temperature and concentrated, the residue was purified by flash column chromatography on silica gel (1.2 g). ESI-MS m/z: 446.2 $[M+H]^+$.

(R)-1-(7-chloro-4-((1-(3-(difluoromethyl)-2-fluorophenyl)ethyl)amino)-2-(methylthio)pyrido[2,3-d]pyrimidin-6-yl)cyclopropane-1-carbonitrile To a solution of (R)-1-(4-((1-(3-(difluoromethyl)-2-fluorophenyl)ethyl)amino)-2-(methylthio)-7-oxo-7,8-dihydropyrido[2,3-d]pyrimidin-6-yl)cyclopropane-1-carbonitrile (600 mg, 1.35 mmol) in $POCl_3$ (10 mL) was added DIEA (20 mg). It was then heated to 110° C. for 3 hours under nitrogen. It was cooled to room temperature and most of the solvent was removed. The residue was treated with ethyl acetate and $NaHCO_{3(aq)}$. The organics was washed with brine, dried over $Na_2SO_4$ and concentrated. The residue was used in next step without purification.

(R)-1-(4-((1-(3-(difluoromethyl)-2-fluorophenyl)ethyl)amino)-7-methoxy-2-(methylthio)pyrido[2,3-d]pyrimidin-6-yl)cyclopropane-1-carbonitrile To a solution of NaOMe (300 mg) in MeOH (15 mL) was added NaH (150 mg, 60%), then a solution of the product from last step (in 5 mL MeOH) was added. The resulting mixture was heated to 60° C. for 2 hours under nitrogen. It was cooled to room temperature and solvent was removed. The residue was treated with ethyl acetate and $NaHCO_{3(aq)}$. The organics were separated, washed with brine and dried over $Na_2SO_4$. It was filtered and concentrated to give a crude. The crude was purified by flash column chromatography on silica gel (280 mg) ESI-MS m/z: 460.2 $[M+H]^+$.

(R)-1-(4-((1-(3-(difluoromethyl)-2-fluorophenyl)ethyl)amino)-7-methoxy-2-(methylsulfonyl)pyrido[2,3-d]pyrimidin-6-yl)cyclopropane-1-carbonitrile To a solution of (R)-1-(4-((1-(3-(difluoromethyl)-2-fluorophenyl)ethyl)amino)-7-methoxy-2-(methylthio)pyrido[2,3-d]pyrimidin-6-yl)cyclopropane-1-carbonitrile (280 mg, 0.6 mmol) in DCM (20 ml) was added m-CPBA (412.8 mg, 2.4 mmol). The mixture was stirred at RT for 12 hours. TLC showed the reaction was completed. The mixture was concentrated in vacuo and the residue was purified by flash column chromatography on silica gel to afford the product (140 mg), ESI-MS m/z: 492.1 $[M+H]^+$.

1-(4-(((R)-1-(3-(difluoromethyl)-2-fluorophenyl)ethyl)amino)-7-methoxy-2-(((S)-1-methylpyrrolidin-2-yl)methoxy)pyrido[2,3-d]pyrimidin-6-yl)cyclopropane-1-carbonitrile (compound 326)

To a solution of (S)-(1-methylpyrrolidin-2-yl)methanol (17 mg, 0.15 mmol) in THF (10 ml) was added NaH (6.1 mg, 0.15 mmol) at 0° C., the reaction mixture was stirred at 0° C. for 30 min, then (R)-1-(4-((1-(3-(difluoromethyl)-2-fluorophenyl)ethyl) amino)-7-methoxy-2-(methylsulfonyl)pyrido[2,3-d]pyrimidin-6-yl)cyclopropane-1-carbonitrile (50 mg, 0.1 mmol) was added, the temperature was allowed to warm to RT and stirred for 1 hour. It was quenched the reaction by aq. NH$_4$Cl (10 ml) and extracted with ethyl acetate (20 ml×2). The organics was separated, dried over Na$_2$SO$_4$ and concentrated. The residue was purified by prep-HPLC to afford the product. [M+H]$^+$. $^1$HNMR (400 MHz, DMSO-d6): 8.69 (s, 1H), 8.62-8.60 (d, J=6.8, 1H), 7.67-7.63 (m, 1H), 7.53-7.50 (m, 1H), 7.35-7.08 (m, 2H), 5.69-5.65 (m, 1H), 4.12-4.09 (m, 2H), 4.05 (s, 3H), 2.94-2.90 (m, 1H), 2.46-0.44 (m, 1H), 2.28 (s, 3H), 2.18-2.11 (m, 1H), 1.90-1.85 (m, 1H), 1.72-1.59 (m, 7H), 1.55-1.45 (m, 3H) ppm.

Compound 276: Synthesis of (R)-1-(4-((1-(3-(difluoromethyl)-2-fluorophenyl)ethyl)amino)-2-ethynyl-7-methoxypyrido[2,3-d]pyrimidin-6-yl)cyclopropane-1-carbonitrile

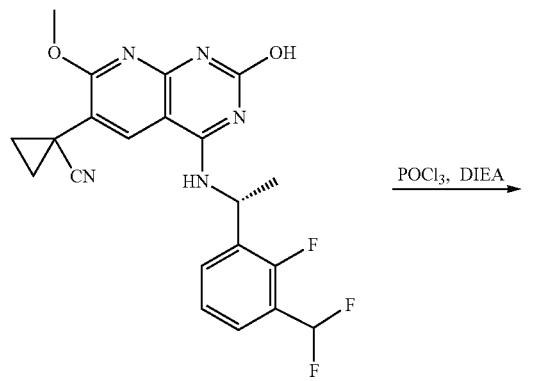

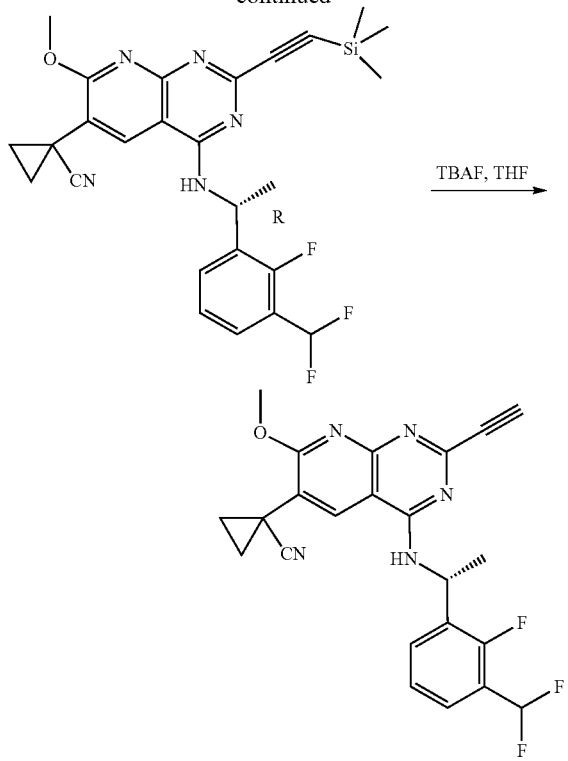

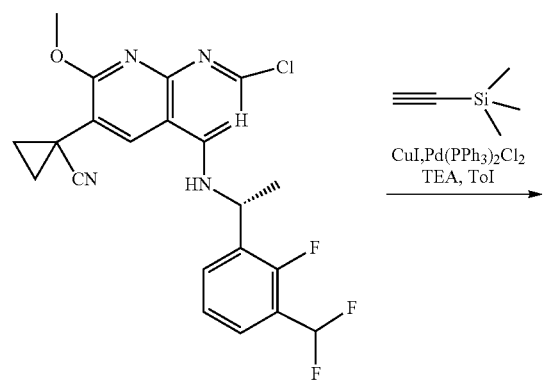

compound 276

(R)-1-(2-chloro-4-((1-(3-(difluoromethyl)-2-fluorophenyl)ethyl)amino)-7-methoxypyrido[2,3-d]pyrimidin-6-yl)cyclopropane-1-carbonitrile To a solution of (R)-1-(4-((1-(3-(difluoromethyl)-2-fluorophenyl)ethyl)amino)-2-hydroxy-7-methoxypyrido[2,3-d]pyrimidin-6-yl)cyclopropane-1-carbonitrile (120 mg, 0.27 mmol) in POCl$_3$ was added DIEA (18 mg, 0.14 mmol). The mixture was heated to 105° C. and stirred for 3 hours. Then POCl$_3$ was removed in vacuo, the residue was dissolved in ethyl acetate (20 ml). It was then neutralized by aq. NaHCO$_3$, the organic layer was separated, concentrated and purified by silica gel to afford the product (100 mg). ESI-MS m/z: 448.1 [M+H]$^+$.

(R)-1-(4-((1-(3-(difluoromethyl)-2-fluorophenyl)ethyl)amino)-7-methoxy-2-((trimethylsilyl)ethynyl)pyrido[2,3-d]pyrimidin-6-yl)cyclopropane-1-carbonitrile To a solution of (R)-1-(2-chloro-4-((1-(3-(difluoromethyl)-2-fluorophenyl)ethyl)amino)-7-methoxypyrido[2,3-d]pyrimidin-6-yl)cyclopropane-1-carbonitrile (100 mg, 0.22 mmol) in toluene (1 ml) was added ethynyltrimethylsilane(1 ml), Pd(PPh$_3$)$_2$Cl$_2$ (15 mg, 0.02 mmol) and TEA (1 ml). The mixture was stirred in a sealed tube at 100° C. for 10 hours. Then the mixture was cooled to room temperature, concentrated and purified by silica gel to afford the product (30 mg). ESI-MS m/z: 510.2 [M+H]$^+$.

(R)-1-(4-((1-(3-(difluoromethyl)-2-fluorophenyl)ethyl)amino)-2-ethynyl-7-methoxypyrido[2,3-d]pyrimidin-6-yl)cyclopropane-1-carbonitrile (compound 276)

To a solution of (R)-1-(4-((1-(3-(difluoromethyl)-2-fluorophenyl)ethyl)amino)-7-methoxy-2-((trimethylsilyl)ethynyl)pyrido[2,3-d]pyrimidin-6-yl)cyclopropane-1-carbonitrile (30 mg, 0.06 mmol) in THF (10 ml) was added TBAF (23 mg, 0.09 mmol). The mixture was stirred at RT for 30 min, then extracted by ethyl acetate (10 ml). The organics was washed with water (10 ml×2), dried over Na₂SO₄. It was filtered and concentrated to give a crude. The crude was purified by Prep-HPLC to afford the product. [M+H]⁺. ¹HNMR (DMSO-d₆, 400 MHz): 8.76 (s, 1H), 8.66-8.64 (d, J=7.2, 1H), 7.03-7.67 (m, 1H), 7.55-7.52 (m, 1H), 7.37-7.10 (m, 2H), 5.77-5.73 (m, 1H), 4.13-4.09 (m, 4H), 1.75-1.74 (m, 2H), 1.64-1.59 (m, 3H), 1.54-1.51 (m, 2H) ppm.

Compound 204: Synthesis of (R)-2,2-difluoro-2-(2-fluoro-3-(1-((6-(4-isopropylpiperazin-1-yl)-7-methoxypyrido[2,3-d]pyrimidin-4-yl)amino)ethyl)phenyl)ethan-1-ol

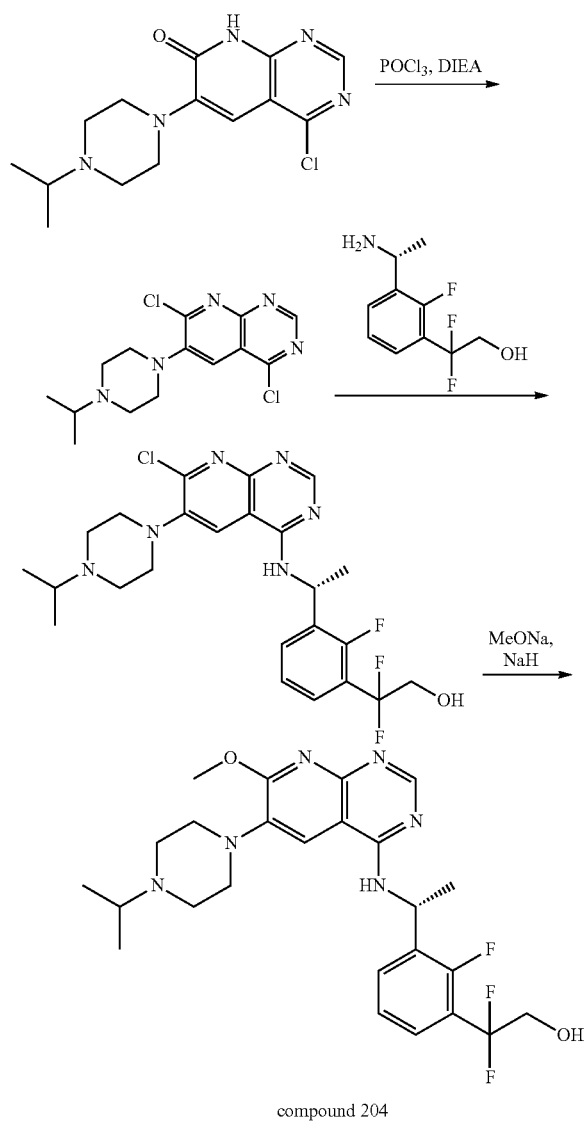

4,7-dichloro-6-(4-isopropylpiperazin-1-yl)pyrido[2,3-d]pyrimidine

To a solution of 4-chloro-6-(4-isopropylpiperazin-1-yl)pyrido[2,3-d]pyrimidin-7(8H)-one in POCl₃ (12.5 ml) was added diisopropylethylamine (DIPEA, 2.25 ml). The mixture was stirred at 100° C. for 5 hours. The mixture was allowed to cool to room temperature and concentrated in vacuo to remove POCl₃. The residue was extracted with ethyl acetate and NaHCO₃₍aq₎. The organics was washed with brine, dried over Na₂SO₄ and concentrated. The residue was purified by flash column chromatography on silica gel (50 mg). ESI-MS m/z: 326.2 [M+H]⁺.

(R)-2-(3-(1-((7-chloro-6-(4-isopropylpiperazin-1-yl)pyrido[2,3-d]pyrimidin-4-yl)amino)ethyl)-2-fluorophenyl)-2,2-difluoroethan-1-ol To a solution of 4,7-dichloro-6-(4-isopropylpiperazin-1-yl) pyrido[2,3-d]pyrimidine (50 mg, 0.153 mmol) and (R)-2-(3-(1-aminoethyl)-2-fluorophenyl)-2,2-difluoroethan-1-ol (48 mg, 0.219 mmol) in DMSO (5 mL) was added KF (53 mg, 0.913 mmol). The mixture was heated to 110° C. for 3 hours. It was cooled to room temperature and NaHCO₃₍aq₎ (40 mL) was added, extracted with ethyl acetate. The organics was washed with brine, dried over Na₂SO₄ and concentrated. The residue was purified by flash column chromatography on silica gel to give desired product (30 mg) ESI-MS m/z: 508.2 [M+H]⁺.

(R)-2,2-difluoro-2-(2-fluoro-3-(1-((6-(4-isopropylpiperazin-1-yl)-7-methoxypyrido[2,3-d]pyrimidin-4-yl)amino)ethyl)phenyl)ethan-1-ol (compound 204)

To a solution of NaOMe in MeOH (15 ml) was added NaH (0.2 g) and stirred at room temperature for 0.5 h. (R)-2-(3-(1-((7-chloro-6-(4-isopropylpiperazin-1-yl)-pyrido[2,3-d]pyrimidin-4-yl)amino)ethyl)-2-fluorophenyl)-2,2-difluoroethan-1-ol (30 mg, 0.059 mmol) was added to the mixture. The solution was stirred at 65° C. for 1 hour under nitrogen. It was cooled to room temperature and NaHCO₃ (aq 5 mL) was added. The mixture was then extracted with ethyl acetate. The organics was washed with brine, dried over Na₂SO₄ and concentrated. The residue was purified by flash column chromatography on silica gel provided desired product. ¹HNMR (400 MHz, DMSO-d6) 8.26-8.2 (m, 2H), 7.95-7.9 (s, 1H), 7.55-7.51 (m, 1H), 7.37-7.33 (m, 1H), 7.16-7.12 (m, 1H), 5.73-5.7 (m, 1H), 5.64-5.6 (m, 1H), 3.94-3.9 (s, 3H), 3.87-3.83 (m, 2H), 3.0-2.9 (m, 4H), 2.73-2.69 (m, 1H), 2.6-2.5 (m, 4H), 1.535-1.517 (d, J=3.6 Hz, 3H), 0.99-0.973 (d, J=3.4 Hz, 6H) ppm.

Compound 237: Synthesis of (R)-1-(4-((1-(3-(difluoromethyl)-2-fluorophenyl)ethyl)amino)-2-(3-(dimethylamino)azetidin-1-yl)-7-methoxypyrido[2,3-d]pyrimidin-6-yl)cyclopropane-1-carbonitrile

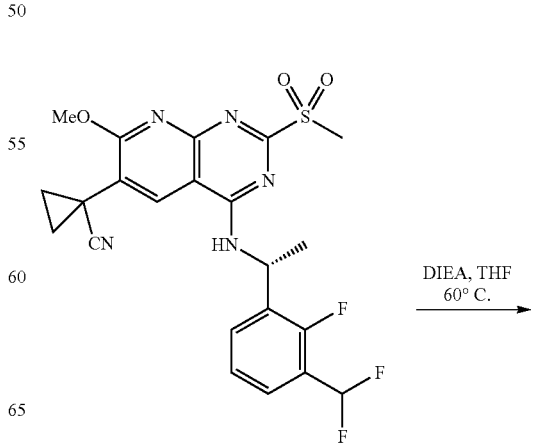

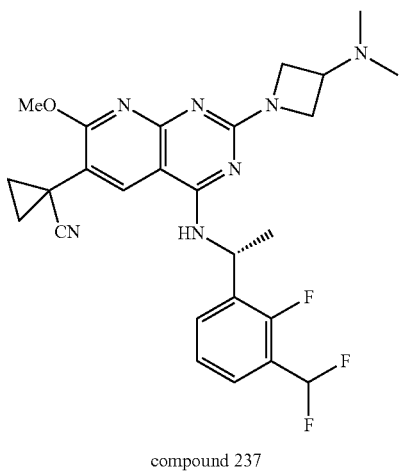

compound 237

(R)-1-(4-((1-(3-(difluoromethyl)-2-fluorophenyl)ethyl)amino)-2-(3-(dimethylamino)azetidin-1-yl)-7-methoxypyrido[2,3-d]pyrimidin-6-yl)cyclopropane-1-carbonitrile (compound 237)

To a solution of (R)-1-(4-((1-(3-(difluoromethyl)-2-fluorophenyl)ethyl)amino)-7-methoxy-2-(methylsulfonyl)pyrido[2,3-d]pyrimidin-6-yl)cyclopropane-1-carbonitrile (50 mg, 1.00 mmol) and N,N-dimethylazetidin-3-amine (17.4 mg, 1.00 mmol) in THF (10 ml) at room temperature were added DIEA (4 ml). The resulting mixture was heated at 60° C. under argon and stirred for 4 hours. The mixture was then cooled to room temperature and concentrated to remove most of solvent. The mixture was extracted with ethyl acetate (20 mL×3). Organic extracts were combined, washed with brine, and dried over $Na_2SO_4$. It was filtered and solvent was removed under reduced pressure to give a crude. The crude was purified by prep-TLC to afford the desired product. $^1$HNMR (400 MHz, MeOD): 8.33 (m, 1H), 7.46 (m, 1H), 7.37 (m, 1H), 7.11 (m, 1H), 6.90 (m, 1H), 5.47 (m, 1H), 4.44 (m, 2H), 4.02 (m, 3H), 3.06 (m, 1H), 2.10 (m, 6H), 1.55 (m, 5H), 1.33 (m, 2H), 1.31 (m, 2H) ppm.

Compound 201: Synthesis of (R)-7-chloro-6-(4-isopropylpiperazin-1-yl)-2-methyl-N-(1-(2-methyl-3-(trifluoromethyl)phenyl)ethyl)pyrido[2,3-d]pyrimidin-4-amine

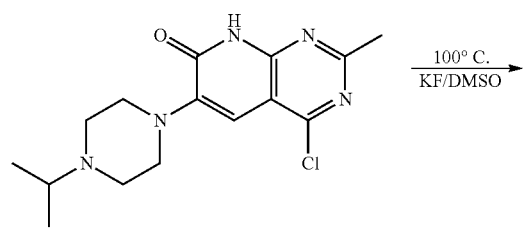

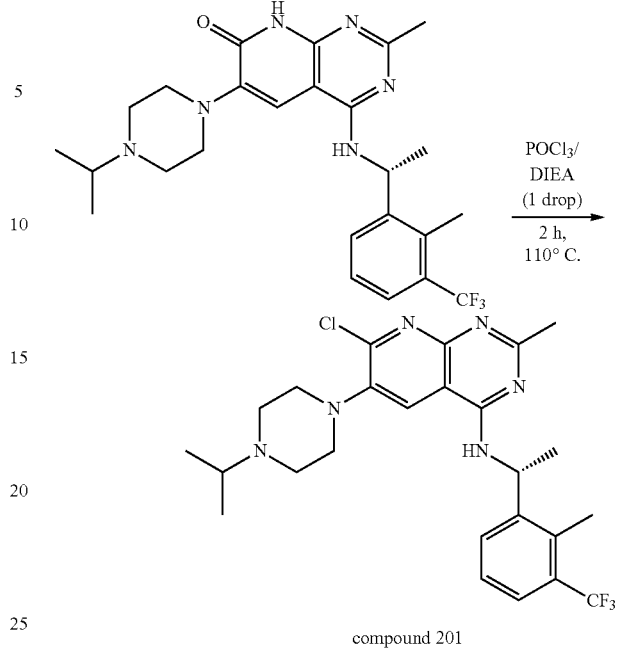

compound 201

(R)-6-(4-isopropylpiperazin-1-yl)-2-methyl-4-((1-(2-methyl-3-(trifluoromethyl)phenyl)ethyl)amino)pyrido[2,3-d]pyrimidin-7(8H)-one To a stirred solution of 4-chloro-6-(4-isopropylpiperazin-1-yl)-2-methylpyrido[2,3-d]pyrimidin-7(8H)-one (200 mg, 0.623 mmol) and (R)-1-(2-methyl-3-(trifluoromethyl)phenyl)ethan-1-amine (152 mg, 0.748 mmol) in DMSO (20 mL) was added KF (200 mg, 3.448 mmol). The mixture was heated to 110° C. and stirred for 3 hours. It was cooled to room temperature and $NaHCO_{3(aq)}$ (40 mL) was added. It was extracted with ethyl acetate. The organics were washed with brine, dried over $Na_2SO_4$ and concentrated. The residue was purified by flash column chromatography on silica gel (240 mg). ESI-MS m/z: 489.3 [M+H]$^+$.

(R)-7-chloro-6-(4-isopropylpiperazin-1-yl)-2-methyl-N-(1-(2-methyl-3-(trifluoromethyl)phenyl)ethyl)pyrido[2,3-d]pyrimidin-4-amine (compound 201)

To a solution of (R)-6-(4-isopropylpiperazin-1-yl)-2-methyl-4-((1-(2-methyl-3-(trifluoromethyl)phenyl)ethyl)amino)pyrido[2,3-d]pyrimidin-7(8H)-one (120 mg, 0.246 mmol) in $POCl_3$ (10 mL) was added DIEA (20 mg). The mixture was then heated to 110° C. and stirred for 2 hours. It was cooled to room temperature he solvent was removed. The residue was treated with ethyl acetate and $NaHCO_3$(aq). The organics were separated and washed with brine, dried over $Na_2SO_4$ and concentrated. The residue was purified by flash column chromatography on silica gel provided desired product. $^1$H NMR (400 MHz, DMSO-d6) 9.19 (m, 1H), 8.65 (s, 1H), 7.82 (d, J=7.6 Hz, 1H), 7.55 (d, J=7.6 Hz, 1H), 7.37 (t, J=7.6 Hz, 1H), 5.73 (m, 1H), 3.7-3.4 (m, 8H), 3.2 (m, 1H), 2.62 (s, 3H), 2.36 (s, 3H), 1.60 (d, J=6.8 Hz, 3H), 1.5-1.3 (m, 6H) ppm.

Synthesis of (R)-1-(3-(difluoro(1-isopropylpiperidin-4-yl)methyl-2-fluorophenyl)ethan-1-amine

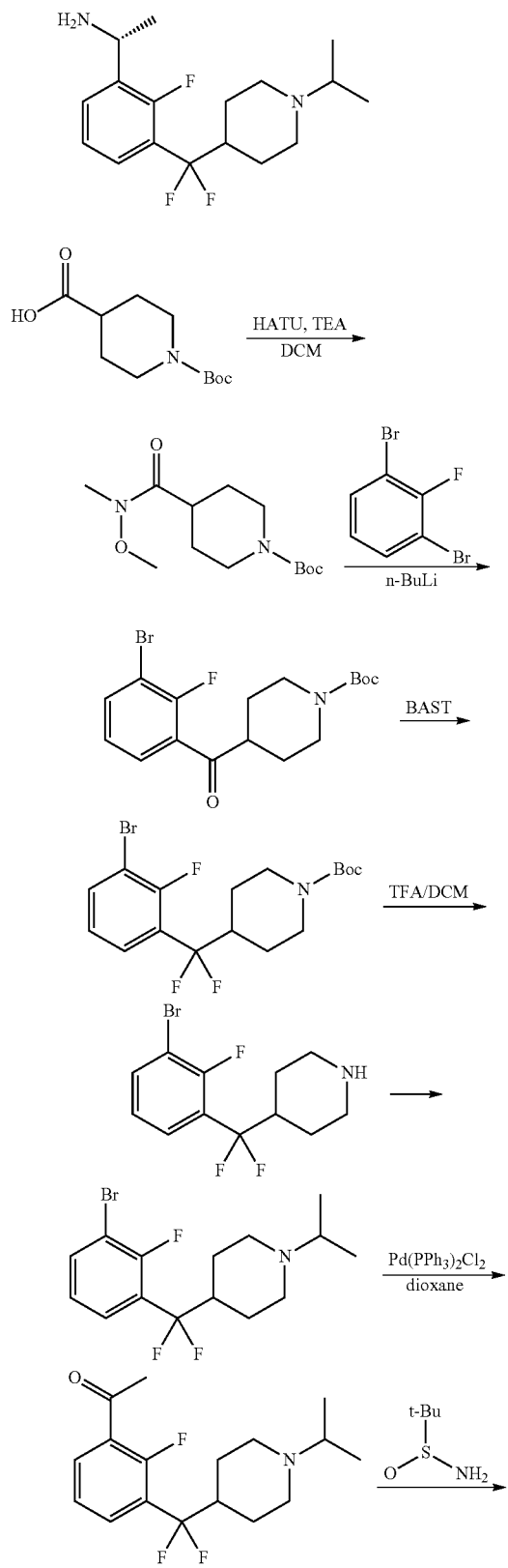

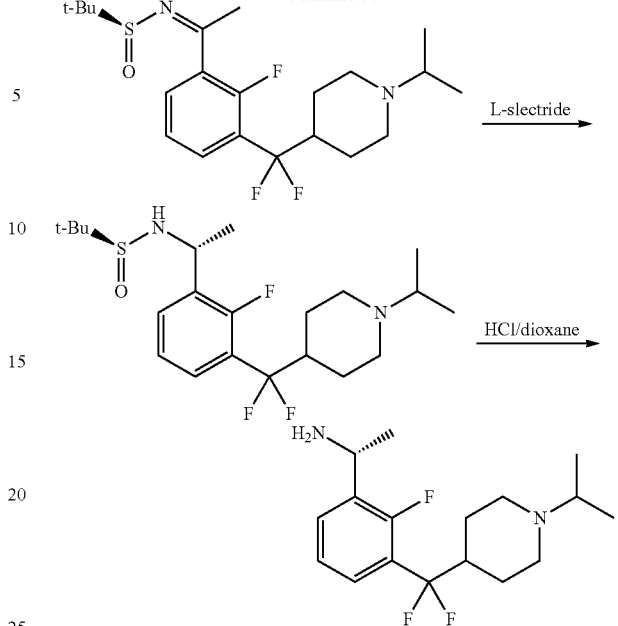

Synthesis of tert-butyl 4-(methoxy(methyl)carbamoyl)piperidine-1-carboxylate To a stirring solution of 1-(tert-butoxycarbonyl)piperidine-4-carboxylic acid (50 g, 218.2 mmol), 2-(7-Azabenzotriazol-1-yl)-N,N,N',N'-tetramethyluronium hexafluorophosphate (124.4 g, 327.3 mmol) in dichloromethane (350 mL) was added dropwise of triethylamine (66.2 g, 654.6 mmol) at 0° C. The mixture was stirred at room temperature for 16 hours. The mixture was diluted with DCM (300 mL) and H$_2$O (500 mL). The organic layer was separated and the inorganic layer was extracted with DCM (300 mL*2). The organic layer was combined and concentrated. The residue was purified by silica gel (petroleum ether:ethyl acetate=80:20) to give desired product as a colorless oil (56 g). LC-MS: (ESI, m/z): [M+H]$^+$=273.0

Synthesis of tert-butyl 4-(3-bromo-2-fluorobenzoyl)piperidine-1-carboxylate

To a solution of 1,3-dibromo-2-fluorobenzene (25.0 g, 98.4 mmol) in dried THF (150 mL) was added n-Butyllithium (67 mL, 1.6N in hexane, 107.2 mmol) slowly at −78° C. under nitrogen atmosphere. The reaction mixture was stirred for 1 hour at the same temperature and a solution of tert-butyl 4-(methoxy(methyl)carbamoyl)piperidine-1-carboxylate (24.2 g, 89.0 mmol) in THF (50 mL) was added. The reaction mixture was stirred at −78° C. under nitrogen atmosphere for 5 hours. The mixture was quenched with a saturated solution of ammonium chloride in water (20 mL). The residue was diluted with water (100 mL), and the solution was extracted with ethyl acetate (100 mL*3). The organic layer was combined and dried over sodium sulphate. It was filtered and concentrated in vacuo to give a crude residue. The residue was purified by silica gel (petroleum ether:ethyl acetate=85:15) to give desired product as a yellow oil (30.4 g). LC-MS: (ESI, m/z): [M+H]$^+$=372.9

Synthesis of tert-butyl 4-((3-bromo-2-fluorophenyl)-difluoromethyl)piperidine-1-carboxylate A solution of tert-butyl 4-(3-bromo-2-fluorobenzoyl)piperidine-1-carboxylate (30.4 g, 78.9 mmol) in BAST (45 g, 197.3 mmol) was stirred at 45° C. for 16 hours. The mixture was quenched with ice-water, adjusted pH=8 with a saturated solution of sodium bicarbonate in water and the solution was extracted with ethyl acetate (200 mL*3). The organic layer was combined and dried over sodium sulphate. It was filtered and concentrated in vacuo to give a crude residue. The crude was purified by silica gel (petroleum ether:ethyl acetate=85:15) to give desired product as a yellow oil (27.9 g). LC-MS: (ESI, m/z): [M+H]$^+$=394.9

Synthesis of 4-((3-bromo-2-fluorophenyl)difluoromethyl)piperidine

A solution of tert-butyl 4-((3-bromo-2-fluorophenyl)difluoromethyl)piperidine-1-carboxylate (26.0 g, 63.9 mmol) in TFA (30 mL) and DCM (100 mL) was stirred at r.t. for 2 hours. The mixture was concentrated under vacuo. The residue was washed with methanol (20 mL) to give product as a white solid (18 g). LC-MS: (ESI, m/z): [M+H]$^+$=307.9

Synthesis of 4-((3-bromo-2-fluorophenyl)difluoromethyl)-1-isopropylpiperidine

A mixture of 4-((3-bromo-2-fluorophenyl)difluoromethyl)piperidine (18.0 g, 58.4 mmol) and acetone (4.1 g, 70.2 mmol) in methanol (100 mL) was stirred at room temperature for 5 hours. Sodium cyanoborohydride (5.5 g, 87.6 mmol) was added and the mixture was stirred for another 16 hours. The reaction mixture was concentrated under in vacuo and the residue was purified by silica gel (dichloromethane:methanol=92:8) to give desired product as a yellow oil (14 g). LC-MS: (ESI, m/z): [M+H]$^+$=349.9

Synthesis of 1-(3-(difluoro(1-isopropylpiperidin-4-yl)methyl)-2-fluorophenyl)ethan-1-one A mixture of 4-((3-bromo-2-fluorophenyl)difluoromethyl)-1-isopropylpiperidine (16.0 g, 45.7 mmol), tributyl(1-ethoxyvinyl)stannane (33.0 g, 91.4 mmol) and Pd(PP$_3$)$_2$Cl$_2$ (0.8 g, 1.1 mmol) in dioxane (150 mL) was stirred at 100° C. under nitrogen atmosphere for 16 hours. After cooling to room temperature, hydrochloric acid (1 N) was added to adjust pH to 3 and the mixture was stirred for another 2 hours. After completion, the pH value was adjusted to 8 with a saturated solution of sodium bicarbonate in water and the solution was extracted with ethyl acetate (200 mL*3). The organic layer was combined and dried over sodium sulphate, filtered and concentrated under reduced pressure. The residue was purified by silica gel (dichloromethane:methanol=95:5) to give desired product as a brown oil (10.4 g). LC-MS: (ESI, m/z): [M+H]$^+$=314.0

Synthesis of (S,Z)—N-(1-(3-(difluoro(1-isopropylpiperidin-4-yl)methyl)-2-fluorophenyl)ethylidene)-2-methylpropane-2-sulfinamide A mixture of 1-(3-(difluoro(1-isopropylpiperidin-4-yl)methyl)-2-fluorophenyl)ethan-1-one (10.4 g, 33.2 mmol), (S)-2-methylpropane-2-sulfinamide (4.8 g, 39.6 mmol) and tetraethyl titanate (11.4 g, 49.8 mmol) in THF (70 mL) was stirred at 70° C. under nitrogen atmosphere for 16 hour. The mixture was diluted with a saturated solution of sodium bicarbonate in water and filtered. The filtrate was extracted with ethyl acetate (100 mL*3). The organic layer was combined and dried over sodium sulphate, filtered and concentrated under vacuo. The residue was purified by silica gel (dichloromethane:methanol=92:8) to give desired product as a yellow oil (7.6 g). LC-MS: (ESI, m/z): [M+H]$^+$=417.0

Synthesis of (S)—N—((R)-1-(3-(difluoro(1-isopropylpiperidin-4-yl)methyl)-2-fluorophenyl)ethyl)-2-methylpropane-2-sulfinamide To a solution of (S,Z)—N-(1-(3-(difluoro(1-isopropylpiperidin-4-yl)methyl)-2-fluorophenyl)ethylidene)-2-methylpropane-2-sulfinamide (7.6 g, 18.2 mmol) in THF (40 mL) was added L-selectride (1.0 N, 36.5 mL) at −78° C. under nitrogen atmosphere for 5 hours. The mixture was quenched with a saturated solution of ammonium chloride, and the solution was extracted with ethyl acetate (70 mL*3). The combined organic layer was dried over sodium sulphate, filtered and concentrated under vacuo. The residue was purified by silica gel (dichloromethane:methanol=92:8) to give desired product as a yellow oil (6.5 g). LC-MS: (ESI, m/z): [M+H]$^+$=419.0 1H NMR (400 MHz, DMSO) δ 7.62 (t, J=7.1 Hz, 1H), 7.36 (t, J=6.6 Hz, 1H), 7.29 (t, J=7.7 Hz, 1H), 5.51 (d, J=5.8 Hz, 1H), 4.77-4.60 (m, 1H), 2.80 (d, J=11.6 Hz, 2H), 2.68-2.61 (m, 1H), 2.11 (d, J=14.7 Hz, 1H), 2.03 (t, J=11.3 Hz, 2H), 1.55 (d, J=10.4 Hz, 2H), 1.50 (d, J=6.8 Hz, 3H), 1.33 (d, J=7.4 Hz, 2H), 1.08 (s, 9H), 0.92 (d, J=6.5 Hz, 6H).

Synthesis of (R)-1-(3-(difluoro(1-isopropylpiperidin-4-yl)methyl)-2-fluorophenyl)ethan-1-amine A solution of (S)—N—((R)-1-(3-(difluoro(1-isopropylpiperidin-4-yl)methyl)-2-fluorophenyl)ethyl)-2-methylpropane-2-sulfinamide (6.5 g, 15.6 mmol) in 50 mL of 1,4-dioxane and 10 mL of HCl/dioxane (4 N) was stirred at rt for 4 hours. The reaction mixture was concentrated to obtain the crude product. A solution of Sodium bicarbonate in water was added to adjust to pH=7-8. The aqueous layer was concentrated and the residue was purified by flash chromatography (bitotage, C-18, UV214, 120 g, acetonitrile in water (contain 0.1% ammonia) 5-95%) to obtain the desired product. $^1$H NMR (400 MHz, MeOD) δ 7.71 (t, J=6.7 Hz, 1H), 7.61 (t, J=6.8 Hz, 1H), 7.43 (t, J=7.8 Hz, 1H), 4.81 (dd, J=12.0, 5.1 Hz, 1H), 3.50 (dd, J=13.2, 6.8 Hz, 1H), 3.09 (t, J=12.4 Hz, 2H), 2.81-2.67 (m, 4H), 1.68 (d, J=6.9 Hz, 3H), 1.40-1.33 (m, 6H).

Compound 263: Synthesis of (R)—N-(1-(3-(difluoro(1-isopropylpiperidin-4-yl)methyl)-2-fluorophenyl)ethyl)-6-(4-isopropylpiperazin-1-yl)-7-methoxypyrido[2,3-d]pyrimidin-4-amine

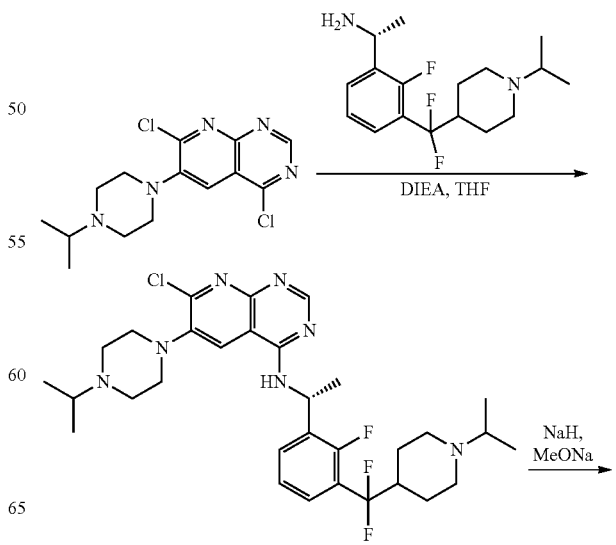

-continued

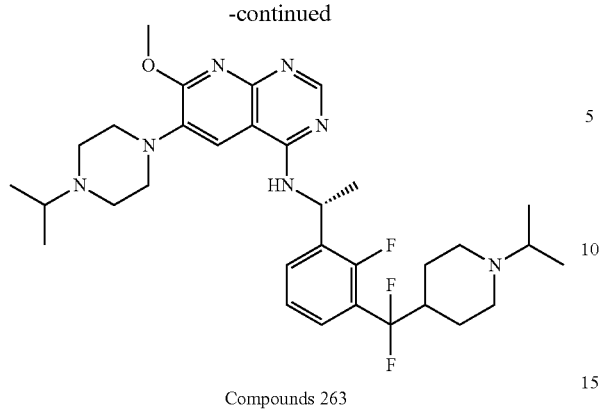

Compounds 263

(R)-7-chloro-N-(1-(3-(difluoro(1-isopropylpiperidin-4-yl)methyl)-2-fluorophenyl)ethyl)-6-(4-isopropylpiperazin-1-yl)pyrido[2,3-d]pyrimidin-4-amine To a solution of 4,7-dichloro-6-(4-isopropylpiperazin-1-yl)pyrido[2,3-d]-pyrimidine (60 mg, 0.18 mmol) and (R)-1-(3-(difluoro(1-isopropylpiperidin-4-yl)methyl) [00894]-2-fluorophenyl)ethan-1-amine (84.4 mg, 0.24 mmol) in THF (10 ml) was added diisopropyl ethyl amine (DIPEA, 1 ml). The mixture was stirred at 65° C. for overnight. The mixture was allowed to cool to room temperature and concentrated in vacuo to remove THF. The residue was treated with ethyl acetate and NaHCO$_{3(aq)}$. The organics were separated and washed with brine, dried over Na$_2$SO$_4$ and concentrated to give a crude residue. The residue was purified by flash column chromatography on silica gel (30 mg). ESI-MS m/z: 603.3 [M+H]$^+$.

(R)—N-(1-(3-(difluoro(1-isopropylpiperidin-4-yl)methyl)-2-fluorophenyl)ethyl)-6-(4-isopropylpiperazin-1-yl)-7-methoxypyrido[2,3-d]pyrimidin-4-amine (compound 263)

NaOMe (100 mg) in methanol (15 ml) was added sodium hydride (30 mg, 60%) and the resulting mixture was stirred at room temperature for 0.5 hour. (R)-7-chloro-N-(1-(3-(difluoro(1-isopropylpiperidin-4-yl)methyl)-2-fluorophenyl)ethyl)-6-(4-isopropylpiperazin-1-yl)pyrido[2,3-d]pyrimidin-4-amine (30 mg, 0.049 mmol) was added to the mixture. The solution was stirred at 65° C. for 1 hour. NaHCO$_3$(aq (5 mL) was added, and the mixture was extracted with ethyl acetate. The organic phase was separated and washed with brine, dried over Na$_2$SO$_4$ and concentrated to give a crude residue. The residue was purified by flash column chromatography on silica gel to give the desired product. $^1$HNMR (400 MHz, DMSO-d6) 8.3-8.2 (m, 2H), 7.99-7.9 (s, 1H), 7.61-7.6 (m, 1H), 7.33-7.32 (m, 1H), 7.27-7.25 (m, 1H), 5.75-5.74 (m, 1H), 3.11-3.1 (m, 3H), 3.13-3.12 (m, 5H), 2.84-2.8 (m, 2H), 2.74-2.71 (m, 1H), 2.67-2.64 (m, 4H), 2.08-2.0 (m, 1H), 1.91-1.9 (m, 2H), 1.61-1.6 (m, 3H), 1.37-1.34 (m, 2H), 1.26-1.24 (m, 2H), 1.045-1.029 (d, J=3.2 Hz, 6H), 0.955-0.939 (d, J=3.2 Hz, 6H) ppm.

Synthesis of (R)-1-(3-((R)-1-aminoethyl)-2-fluorophenyl)-1,1-difluoropropan-2-ol and (S)-1-(3-((R)-1-aminoethyl)-2-fluorophenyl)-1,1-difluoropropan-2-ol

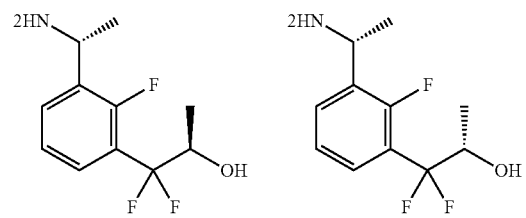

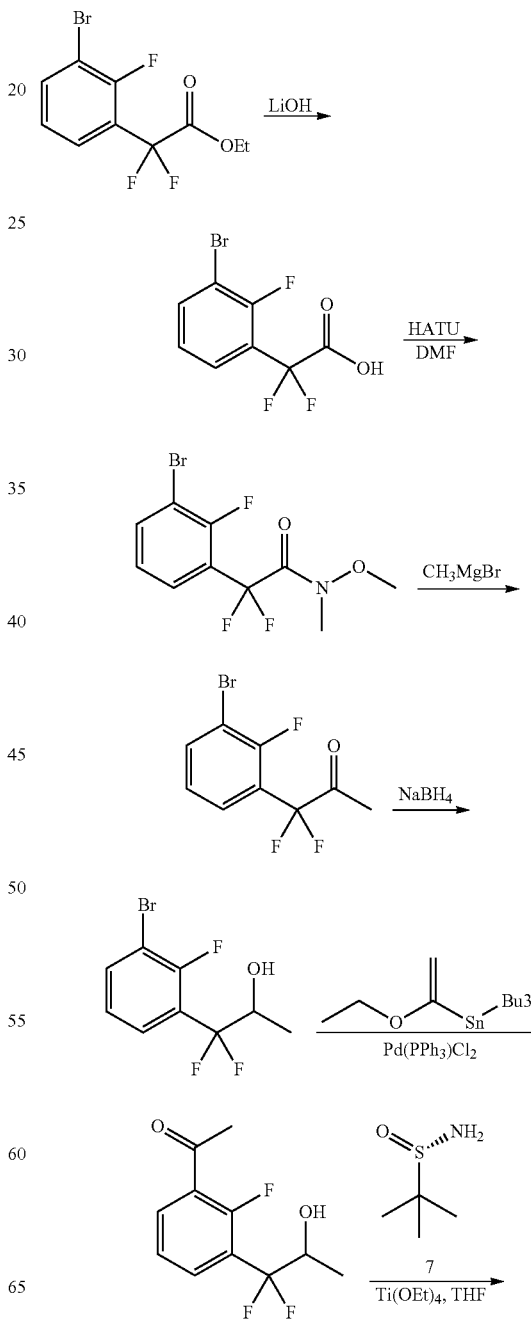

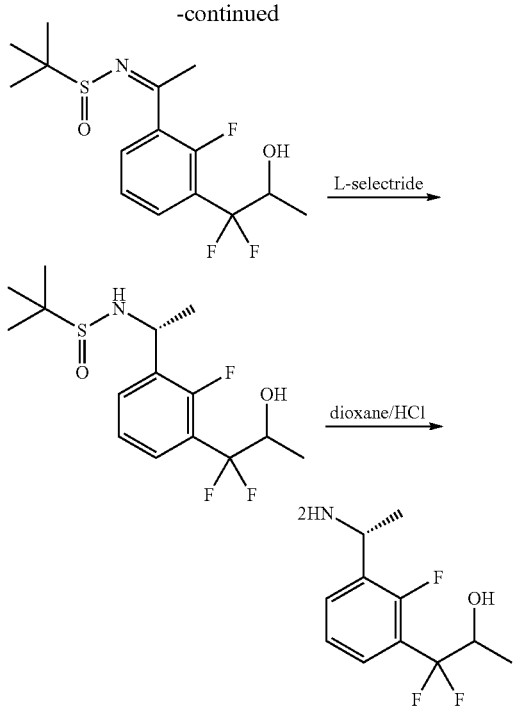

Synthesis of 2-(3-bromo-2-fluorophenyl)-2,2-difluoroacetic acid

To a solution of ethyl 2-(3-bromophenyl)-2,2-difluoroacetate (30 g, 101.69 mmol) in THF (200 mL) was added LiOH (4.88 g, 203.39 mmol) at 0-10° C. The mixture was stirred at room temperature for 1.5 hours. After removing most of THF, the mixture was poured into H₂O (200 mL), and the solution was adjusted pH≈3 with 6 N HCl. The solution was extracted with ethyl acetate (300 mL*3). The combined organic layers were washed with brine, dried over anhydrous Na₂SO₄, filtrated and concentrated to afford crude product (25 g) as a white semi-solid, which was used in next step without further purification.

Synthesis of 2-(3-bromo-2-fluorophenyl)-2,2-difluoro-N-methoxy-N-methylacetamide To a mixture of 2-(3-bromophenyl)-2,2-difluoroacetic acid (25 g, 92.94 mmol) and N,O-dimethylhydroxylamine hydrochloride (10.8 g, 111.52 mmol) in DCM (450 mL) was added DIEA (35.97 g, 278.81 mol) in an ice bath. Then HATU (42.4 g, 111.524 mmol) was added. The mixture was stirred at room temperature for overnight. Water (200 mL) was added and the solution was extracted with DCM (200 mL*2). The combine organic layers were washed with brine, dried over anhydrous Na₂SO₄, filtrated and concentrated. The residue was purified by flash chromatography eluting with PE/EA=10/1 to afford desired product (16.9 g) as a light yellow semi-solid. LC-MS: (ESI, m/z): [M+H]⁺=311.9; ¹H NMR (400 MHz, DMSO-d6) δ 7.86 (t, J=7.0 Hz, 1H), 7.59 (t, J=6.9 Hz, 1H), 7.36-7.13 (m, 1H), 3.69 (s, 3H), 2.59 (s, 3H) ppm.

Synthesis of 1-(3-bromo-2-fluorophenyl)-1,1-difluoropropan-2-one

To a solution of 2-(3-bromo-2-fluorophenyl)-2,2-difluoro-N-methoxy-N-methylacetamide (16.9 g, 54.34 mmol) in dry THF (150 mL) was added CH₃MgBr (3M in THF, 21.74 mL, 65.21 mmol) at −20° C. The mixture was stirred at room temperature for 1 hour. The mixture was quenched with aqueous NH₄Cl (300 mL) and the solution was extracted with ethyl acetate (300 mL*2). The combined organic layers were washed with brine, dried over anhydrous Na₂SO₄, filtrated and concentrated to afford the crude product (15 g) as a light yellow oil. The crude product was used for the next step directly without further purification. ¹H NMR (400 MHz, CDCl₃) δ 7.63 (t, J=7.2 Hz, 1H), 7.48 (t, J=7.0 Hz, 1H), 7.08 (t, J=7.9 Hz, 1H), 2.41 (s, 3H) ppm.

Synthesis of 1-(3-bromo-2-fluorophenyl)-1,1-difluoropropan-2-ol

To a solution of 1-(3-bromo-2-fluorophenyl)-1,1-difluoropropan-2-one (15.0 g, 56.18 mmol) in MeOH (150 mL) was added NaBH₄ (4.27 g, 112.36 mmol) at 0-10° C. The mixture was stirred at room temperature for 1 h. The mixture was quenched with aqueous NH₄Cl (300 mL) and the solution was extracted with ethyl acetate (400 mL*2). The combined organic layers were washed with brine, dried over anhydrous Na₂SO₄, filtrated and concentrated. The residue was purified by flash chromatography (PE/EA=3/1) to afford desired product (11 g) as a light yellow oil. LC-MS: (ESI, m/z): [M+H]⁺=270.1

Synthesis of 1-(3-(1,1-difluoro-2-hydroxypropyl)-2-fluorophenyl)ethan-1-one

To a solution of compound 5 (10 g, 38.91 mmol) in 120 mL of dioxane was added the butyl(1-ethoxyvinyl)-12-stannane-octane (16.86 g, 46.69 mmol) at rt. The solution was bubbled with nitrogen for 15 min at room temperature. Pd(PPh₃)₂Cl₂ (1.3 g, 1.94 mmol) was added and the reaction mixture was stirred at 100° C. overnight under N₂. The reaction mixture was cooled to room temperature and 3N HCl (80 mL) was added slowly. The resulting mixture was stirred for additional 10 mins. The reaction was checked by TLC, TLC showed the reaction was completed. Then saturated potassium fluoride aqueous solution (300 mL) was added to the solution and the solution was stirred for another 1 h at room temperature. It was filtered and the filtrate was separated and extracted with ethyl acetate (250 mL×3). The combined organic layer was washed with brine (600 mL), dried with Na₂SO₄, filtered and concentrated to obtain the crude. The crude was purified by flash chromatography (biotage, silica gel, 330 g UV254, EA in PE 0~40%) to afford the desired product (8.9 g) as a yellow oil. LC-MS: (ESI, m/z): [M+H]⁺=233.0

Synthesis of (S)—N—((Z)-1-(3-(1,1-difluoro-2-hydroxypropyl)-2-fluorophenyl)ethylidene)-2-methylpropane-2-sulfinamide To a solution of 1-(3-(1,1-difluoro-2-hydroxypropyl)-2-fluorophenyl)ethan-1-one (8.9 g, 38.36 mmol) in 50 mL of THF was added (S)-(−)-2-Methyl-2-propanesulfinamide (5.86 g, 47.95 mmol), followed by titanium tetraethoxide (10.93 g, 47.95 mmol) at room temperature. The reaction mixture was stirred at 70° C. overnight under N₂. The reaction mixture was cooled to room temperature and quenched with ice water (200 mL) and ethyl acetate (200 mL). The mixture was filtered through a celite pad and the filtrate was separated and extracted with ethyl acetate (300 mL×3). The combined organic layer was washed with brine (600 mL), dried with Na₂SO₄, filtered and purified by flash chromatography (biotage, silica gel, 80 g, UV254, EA in PE 0-25%) to afford the desired product (10.2 g) as a yellow oil. LC-MS: (ESI, m/z): [M+H]$^+$=336.0

Synthesis of (R)-1-(3-((R)-1-aminoethyl)-2-fluorophenyl)-1,1-difluoropropan-2-ol and (S)-1-(3-((R)-1-aminoethyl)-2-fluorophenyl)-1,1-difluoropropan-2-ol To a solution of compound 8 (10.2 g, 29.85 mmol) in THF (120 mL) was added L-selectride (59.7 ml, 59.7 mmol, 1M in THF) at −78° C. under N$_2$ and the mixture was stirred at −78° C. for 3 h. It was quenched with saturated NH$_4$Cl (aq, 30 mL) and the solution was extracted with ethyl acetate (100 mL*2). The combined organic layer was washed with brine (100 mL), dried over Na$_2$SO$_4$, filtered and concentrated in vacuo. It was dissolved in dioxane (60 mL) treated with 4N HCl in dioxane and stirred at room temperature for 4 hours. It was concentrated and Chiral separation using chiral column to provide desired product (ESI, m/z): [M+H]$^+$=338.1. as (R)-1-(3-((R)-1-aminoethyl)-2-fluorophenyl)-1,1-difluoropropan-2-ol and (S)-1-(3-((R)-1-aminoethyl)-2-fluorophenyl)-1,1-difluoropropan-2-ol Compound 295: Synthesis of (R)-1-(4-((1-(3-(difluoromethyl)-2-fluorophenyl)ethyl)amino)-2-methyl-7-(4-methylpiperazin-1-yl)pyrido[2,3-d]pyrimidin-6-yl)cyclopropanecarbonitrile

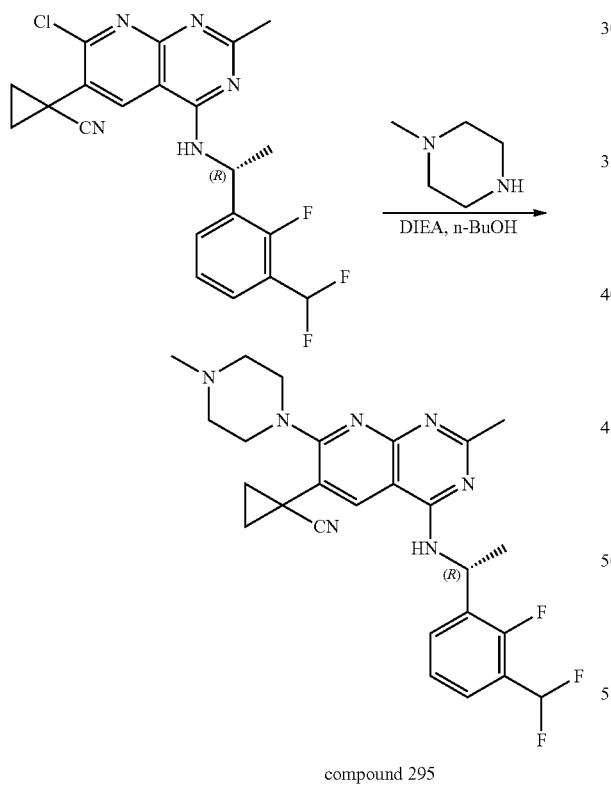

compound 295

(R)-1-(4-((1-(3-(difluoromethyl)-2-fluorophenyl)ethyl)amino)-2-methyl-7-(4-methylpiperazin-1-yl)pyrido[2,3-d]pyrimidin-6-yl)cyclopropanecarbonitrile (compound 295)

To a solution of (R)-1-(7-chloro-4-((1-(3-(difluoromethyl)-2-fluorophenyl)ethyl) amino)-2-methylpyrido[2,3-d]pyrimidin-6-yl)cyclopropanecarbonitrile (37 mg, 0.086 mmol) and 1-methylpiperazine (28 mg, 0.28 mmol) in n-BuOH (3 mL) was added DIEA (1 mL). The resulting mixture was heated at 125° C. under argon and stirred for 3 hour. It was cooled to room temperature and ethyl acetate (20 mL) was added. The organics were washed with brine, dried over Na$_2$SO$_4$. It was filtered and solvent was removed under reduced pressure to give a crude. The crude was purified by flash chromatography on silica gel (dichloromethane:methyl alcohol=95:5) to afford the desired product. $^1$HNMR (MeOD: 400 MHz): 8.72 (s, 1H), 7.64-7.60 (t, 1H), 7.51-7.48 (t, 1H), 7.27-7.24 (t, 1H), 7.15-6.88 (t, 1H), 5.86-5.81 (m, 1H), 3.79 (s, 4H), 2.85-2.82 (m, 4H), 2.48 (s, 3H), 2.43 (s, 3H), 1.88-1.86 (m, 2H), 1.70-1.67 (m, 5H) ppm.

Compound 356: Synthesis of (R)-1-(4-((1-(3-(1,1-difluoro-2-hydroxy-2-methylpropyl)-2-fluorophenyl)ethyl)amino)-7-methoxypyrido[2,3-d]pyrimidin-6-yl)cyclopropane-1-carbonitrile

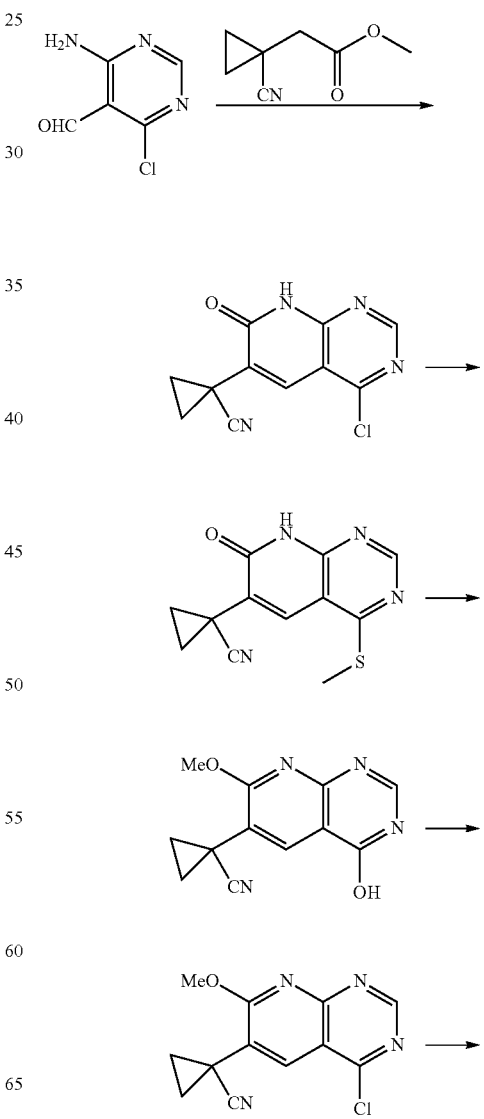

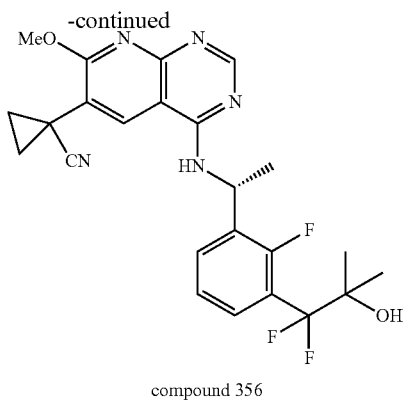

compound 356

1-(4-chloro-7-oxo-7,8-dihydropyrido[2,3-d]pyrimidin-6-yl)cyclopropane-1-carbonitrile To a solution of ethyl 1-cyanocyclopropane-1-carboxylate (1.74 g, 11.37 mmol) and 4-amino-6-chloropyrimidine-5-carbaldehyde (1.80 g, 11.37 mmol) in THF (50 mL) was cooled to −78° C. under argon. LiHMDS (20 mL, 1 M in THF) was added dropwise. The mixture was stirred at −78° C. and allowed to warm gradually to room temperature for 6 hours. It was quenched saturated NH$_4$Cl (20 mL). The mixture was extracted with ethyl acetate (50 mL×3). Organic extracts were combined, washed with brine, and dried over Na$_2$SO$_4$. It was filtered and solvent was removed under reduced pressure to give a crude. The crude was purified by flash chromatography on silica gel (dichloromethane:methyl alcohol=61:2) to afford the desired product (1.8 g). ESI-MS m/z: 247 [M+H]+.

(4-(methylthio)-7-oxo-7,8-dihydropyrido[2,3-d]pyrimidin-6-yl)cyclopropane-1-carbonitrile To a solution of 1-(4-chloro-7-oxo-7,8-dihydropyrido[2,3-d]pyrimidin-6-yl)cyclopropane-1-carbonitrile (2.47 g, 10.0 mmol) in THF (25 mL). Then NaSMe (4 mL, 1 M in MeOH) was added. The mixture was stirred at 60° C. for 3 h. The pH of reaction mixture was adjusted to 7-8 with NaHCO$_3$ solution. The mixture was extracted with ethyl acetate (50 mL×3). Organic extracts were combined, washed with brine, and dried over Na$_2$SO$_4$. It was filtered and solvent was removed under reduced pressure to give a crude (2.76 g). ESI-MS m/z: 259 [M+H]+.

1-(4-hydroxy-7-methoxypyrido[2,3-d]pyrimidin-6-yl)cyclopropane-1-carbonitrile To a solution of 1-(4-(methylthio)-7-oxo-7,8-dihydropyrido[2,3-d]pyrimidin-6-yl)cyclopropane-1-carbonitrile (6.16 g, 23.89 mmol) in POCl$_3$ (50 mL). The mixture was stirred at 105° C. for 3 h. The solvent was removed under reduced pressure. It was quenched with water (20 mL). The mixture was extracted with ethyl acetate (50 mL×3). Organic extracts were combined, washed with brine, and dried over Na$_2$SO$_4$. It was filtered and solvent was removed under reduced pressure to give a crude intermediate (5.5 g). ESI-MS m/z: 313 [M+H]+.

To a solution of the crude intermediate from above reaction (5.5 g) in DCM (100 ml) was added m-CPBA (15.2 g, 88.1 mmol). The mixture was stirred at room temperature for 16 hours. The solvent was removed under reduced pressure to give a crude. ESI-MS m/z: 283 [M+H]+.

To a solution of NaH (700 mg, 48.6 mmol) in MeOH (60 mL), then sodium methanolate (3.3 g, 61.6 mmol) and the crude from above reaction (3.3 g) were added. The mixture was stirred at 60° C. for 3 h. The solvent was removed under reduced pressure to give a crude. The crude was purified by flash chromatography on silica gel (dichloromethane:methyl alcohol=41:2) to afford the desired product (1.53 g). ESI-MS m/z: 243 [M+H]+.

(4-chloro-7-methoxypyrido[2,3-d]pyrimidin-6-yl)cyclopropane-1-carbonitrile

To a solution of 1-(4-hydroxy-7-methoxypyrido[2,3-d]pyrimidin-6-yl)cyclopropane-1-carbonitrile (800 mg, 3.306 mol) in sulfurous dichloride (15 mL). DMF (cat.) was added. The mixture was stirred at 85° C. for 4 hours. The solvent was removed under reduced pressure to afford the desired product (323 mg). ESI-MS m/z: 261 [M+H]+.

(R)-1-(4-((1-(3-(1,1-difluoro-2-hydroxy-2-methylpropyl)-2-fluorophenyl)ethyl)amino)-7-methoxypyrido[2,3-d]pyrimidin-6-yl)cyclopropane-1-carbonitrile (compound 356)

To a solution of (4-chloro-7-methoxypyrido[2,3-d]pyrimidin-6-yl)cyclopropane-1-carbonitrile (200 mg, 0.769 mol) and (R)-1-(3-(1-aminoethyl)-2-fluorophenyl)-1,1-difluoro-2-methylpropan-2-ol (239 mg, 0.847 mmol) in n-BuOH (20 mL) was added DIEA (1.42 g, 11.60 mmol). The resulting mixture was heated at 125° C. under argon and stirred for 2 hours. It was cooled to room temperature and ethyl acetate (60 mL) was added. The organics were washed with brine, dried over Na$_2$SO$_4$. It was filtered and solvent was removed under reduced pressure to give a crude. The crude was purified by flash chromatography on silica gel (dichloromethane:methyl alcohol=97:3) to afford the desired product. $^1$HNMR (DMSO-d6, 400 MHz): 8.85 (s, 1H), 8.64-8.62 (m, 1H), 8.46 (s, 1H), 7.63-7.60 (m, 1H), 7.34-7.33 (m, 1H), 7.25-7.21 (m, 1H), 5.79-5.76 (m, 1H), 5.33 (s, 1H), 4.11 (s, 3H), 1.76-1.75 (m, 2H), 1.61-1.60 (m, 3H), 1.55 (s, 2H), 1.23 (s, 6H) ppm.

Compound 303: Synthesis of ((R)-1,4-dioxan-2-yl)(4-(4-(((R)-1-(2-fluoro-3-(trifluoromethyl)-phenyl)ethyl)amino)-7-methoxy-2-methylpyrido[2,3-d]pyrimidin-6-yl)piperazin-1-yl)methanone

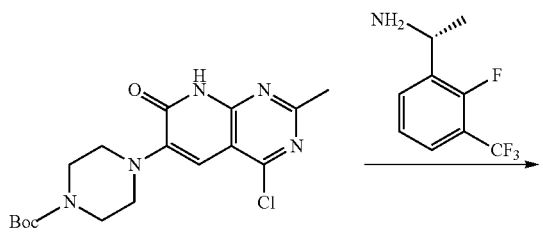

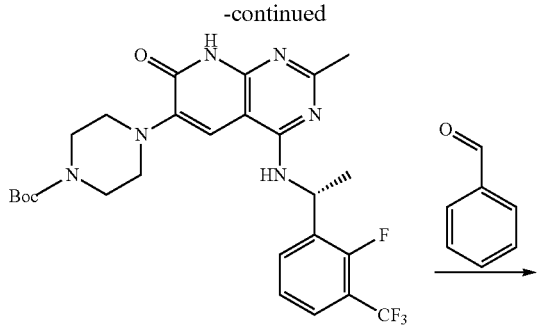

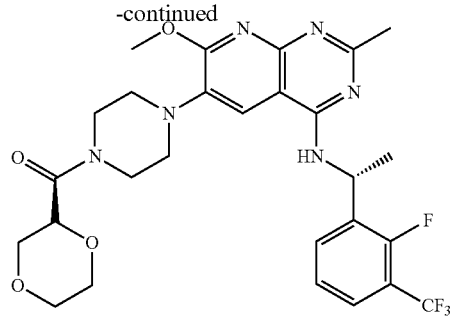

Compound 303

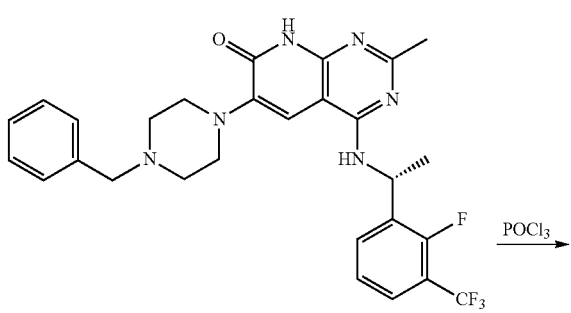

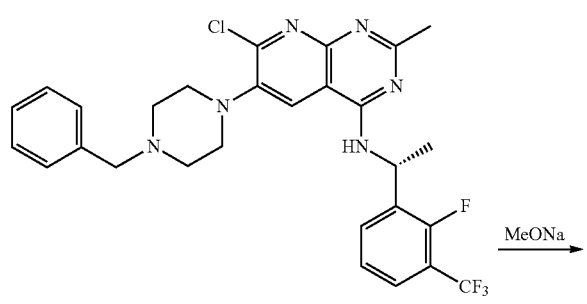

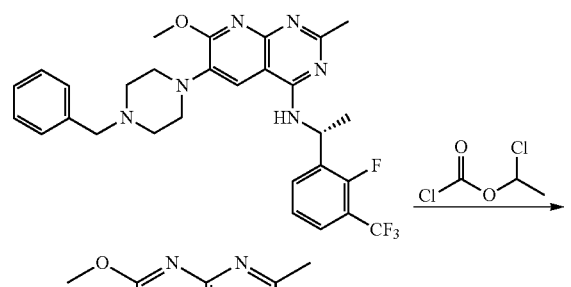

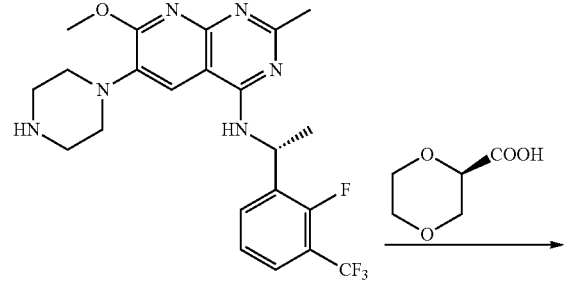

tert-butyl(R)-4-(4-((1-(2-fluoro-3-(trifluoromethyl) phenyl)ethyl)amino)-2-methyl-7-oxo-7,8-dihydropyrido[2,3-d]pyrimidin-6-yl)piperazine-1-carboxylate To a solution of tert-butyl 4-(4-chloro-2-methyl-7-oxo-7,8-dihydropyrido-[2,3-d]pyrimidin-6-yl)piperazine-1-carboxylate (1.5 g, 3.95 mmol) and (R)-1-(2-fluoro-3-(trifluoromethyl)phenyl)ethan-1-amine (1.15 g, 4.74 mmol) in DMSO (20 mL) was added KF (1.5 g, 39.5 mmol), then the reaction mixture was heated to 110° C. for 3 hours. It was cooled to room temperature and NaHCO$_3$(aq) (40 mL) was added. The mixture was extracted with ethyl acetate. The organic phase was washed with brine, dried over Na$_2$SO$_4$ and concentrated. The residue was purified by flash column chromatography on silica gel to give desired product (1 g) ESI-MS m/z: 380.1 [M+H]$^+$.

(R)-6-(4-benzylpiperazin-1-yl)-4-((1-(2-fluoro-3-(trifluoromethyl)phenyl)ethyl)amino)-2-methylpyrido[2,3-d]pyrimidin-7(8H)-one To a solution of tert-butyl (R)-4-(4-((1-(2-fluoro-3-(trifluoromethyl)phenyl)-ethyl)amino)-2-methyl-7-oxo-7,8-dihydropyrido[2,3-d]pyrimidin-6-yl)piperazine-1-carboxylate (1 g, 1.81 mmol) in DCM (8 mL) was added trifluoroacetic acid (2 mL). The mixture was stirred at room temperature for 1 hour. The volatiles were evaporated to afford the product (R)-4-((1-(2-fluoro-3-(trifluoromethyl)phenyl)ethyl) amino)-2-methyl-6-(piperazin-1-yl)pyrido[2,3-d]pyrimidin-7(8H)-one. Then, benzaldehyde (500 mg, 4.71 mmol) and excessive NaBH$_3$CN in methanol (15 mL) were added to the residue. The mixture was stirred at 60° C. overnight. NaHCO$_{3(aq)}$ (5 mL) was added, The mixture was extracted with ethyl acetate. The organic phase was washed with brine, dried over Na$_2$SO$_4$ and concentrated. The residue was purified by flash column chromatography on silica gel (850 mg, 86% yield) ESI-MS m/z: 541.2 [M+H]$^+$.

(R)-6-(4-benzylpiperazin-1-yl)-7-chloro-N-(1-(2-fluoro-3-(trifluoromethyl)phenyl)ethyl)-2-methylpyrido[2,3-d]pyrimidin-4-amine To a solution of (R)-6-(4-benzylpiperazin-1-yl)-4-((1-(2-fluoro-3-(trifluoromethyl)phenyl)ethyl)amino)-2-methylpyrido[2,3-d]pyrimidin-7(8H)-one in POCl$_3$ (30 mL) was added DIEA (20 mg), then the mixture was heated to 110° C. for 2 hours. The solvent was removed, the residue was extracted with ethyl acetate and NaHCO$_{3(aq)}$. The organic phase was washed with brine, dried over Na$_2$SO$_4$ and concentrated. The residue was purified by flash column chromatography on silica gel to give the desired product (810 mg) ESI-MS m/z: 559.2 [M+H]⁺.

(R)-6-(4-benzylpiperazin-1-yl)-N-(1-(2-fluoro-3-(trifluoromethyl)phenyl)ethyl)-7-methoxy-2-methylpyrido[2,3-d]pyrimidin-4-amine Excessive sodium methanolate and sodium hydride were added in methanol (15 mL) and stirred at room temperature for 0.5 hour. (R)-6-(4-benzylpiperazin-1-yl)-7-chloro-N-(1-(2-fluoro-3-(trifluoromethyl)phenyl)ethyl)-2-methylpyrido[2,3-d]pyrimidin-4-amine (810 mg, 1.45 mmol) was added to the mixture. The solution was stirred at 65° C. for 1 hour. It was cooled to room temperature and NaHCO₃(aq) (10 mL) was added. The mixture was extracted with ethyl acetate. The organic phase was combined and washed with brine, dried over Na₂SO₄ and concentrated. The residue was purified by flash column chromatography on silica gel (700 mg) ESI-MS m/z: 599.2 [M+H]⁺.

(R)—N-(1-(2-fluoro-3-(trifluoromethyl)phenyl)ethyl)-7-methoxy-2-methyl-6-(piperazin-1-yl)pyrido[2,3-d]pyrimidin-4-amine To a solution of (R)-6-(4-benzylpiperazin-1-yl)-N-(1-(2-fluoro-3-(trifluoromethyl)phenyl)ethyl)-7-methoxy-2-methylpyrido[2,3-d]pyrimidin-4-amine (700 mg, 1.26 mmol) in DCE (15 mL) was added 1-chloroethyl carbonochloridate (361 mg, 2.52 mmol). The mixture was stirred at 90° C. for 1 hour. The solvent was removed, the residue was dissolved in methanol (10 mL). The solution was stirred at 70° C. for 1 hour. The volatiles were evaporated to afford the product (450 mg). ESI-MS m/z: 465.2[M+H]⁺.

((R)-1,4-dioxan-2-yl)(4-(4-(((R)-1-(2-fluoro-3-(trifluoromethyl)phenyl)ethyl)amino)-7-methoxy-2-methylpyrido[2,3-d]pyrimidin-6-yl)piperazin-1-yl)methanone (compound 303)

To a solution of (R)—N-(1-(2-fluoro-3-(trifluoromethyl)phenyl)ethyl)-7-methoxy-2-methyl-6-(piperazin-1-yl)pyrido[2,3-d]pyrimidin-4-amine (120 mg, 0.25 mmol), BOP (342 mg, 0.75 mmol) and DIEA (100 mg, 0.75 mmol) in THF (5 mL) was added (R)-1,4-dioxane-2-carboxylic acid (68 mg. 0.5 mmol). The mixture was stirred at room temperature overnight. NaHCO₃₍ₐq₎ (5 mL) was added, and the mixture extracted with ethyl acetate. The organic phase was washed with brine, dried over Na₂SO₄ and concentrated. The residue was purified by flash column chromatography on silica gel to give desired product. ¹HNMR (400 MHz, DMSO-d6) 9.8-9.2 (m, 1H), 8.14-8.0 (s, 1H), 7.85-7.8 (m, 1H), 7.71-7.68 (m, 1H), 7.43-7.39 (m, 1H), 5.86-5.83 (m, 1H), 4.41-4.38 (m, 1H), 4.04-4.0 (s, 3H), 3.78-3.75 (m, 4H), 3.7-3.6 (m, 4H), 3.5-3.4 (m, 2H), 3.1-3.0 (m, 2H), 3.0-2.9 (m, 2H), 2.49-2.46 (m, 3H), 1.695-1.678 (d, J=3.4 Hz, 3H) ppm.

Synthesis of (R)-1-(3-(difluoro(1-isopropylazetidin-3-yl)methyl)-2-fluorophenyl)ethan-1-amine

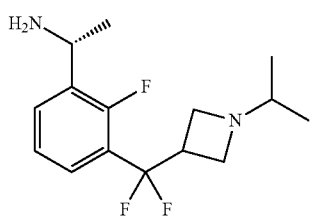

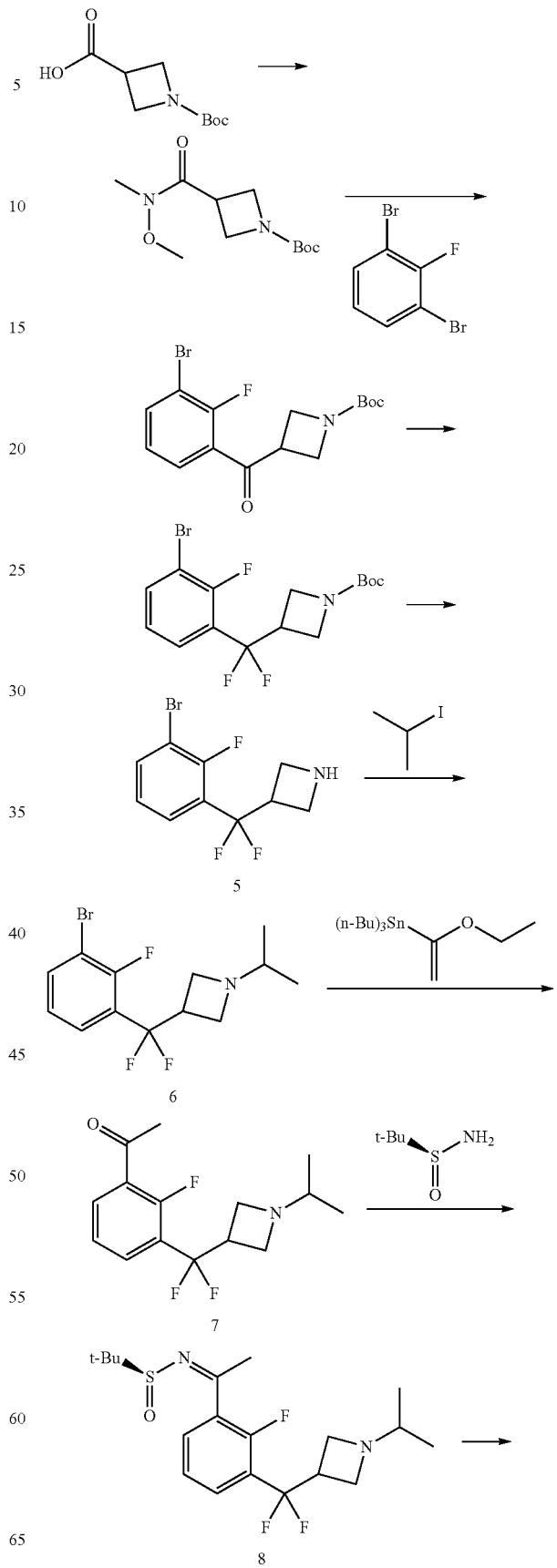

-continued

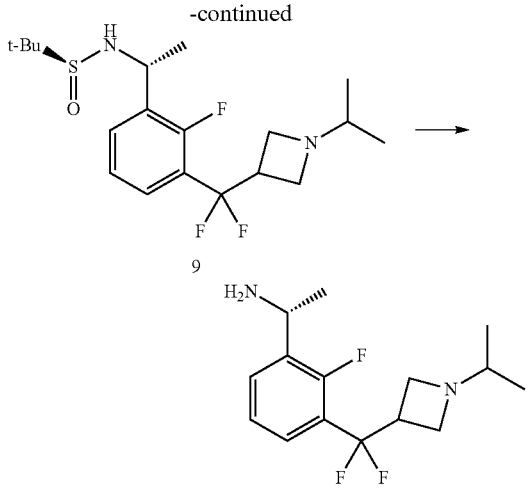

Tert-butyl 3-(methoxy(methyl)carbamoyl)azetidine-1-carboxylate

To a mixture of 1-(tert-butoxycarbonyl)azetidine-3-carboxylic acid (15 g, 74.55 mmol), N,O-dimethylhydroxylamine hydrogen chloride (8 g, 82.00 mmol) and HATU (34 g, 89.45 mmol) in DCM (150 mL) at 0° C. was added TEA (22.63 g, 223.6 mmol), and the result solution was stirred at room temperature for 16 h. The mixture was poured into water and extracted with DCM (100 mL×3). The combined organic layers were washed with brine, dried over $Na_2SO_4$, filtered and concentrated under reduced pressure to give a residue, which was purified by com-flash column (0%~15% ethyl acetate in petroleum) to give the desired product tert-butyl 3-(methoxy(methyl)carbamoyl)azetidine-1-carboxylate as a colorless oil. (ESI, m/z): $[M+H-tBu]^+$:189.0

Tert-butyl 3-(3-bromo-2-fluorobenzoyl)azetidine-1-carboxylate

To a stirred solution of 1,3-dibromo-2-fluorobenzene (25.4 g, 100 mmol) in dry THF (200 mL) was added dropwise n-BuLi (70 mL, 112 mmol, 1.6 M in hexane) at −78° C. under nitrogen. After completion of addition, the mixture was stirred at the same temperature for 2 h. A solution of tert-butyl 3-(methoxy(methyl)carbamoyl)azetidine-1-carboxylate (24.4 g, 100 mmol) in dry THF (40 mL) was added dropwise to the mixture at −78° C. The mixture was allowed to warm up to 0° C. and stirred for additional 2 h. The mixture was quenched with sat. aqueous $NH_4Cl$ and extracted with ethyl acetate (300 mL×3). The combined organic layers were dried over $Na_2SO_4$ and filtered. The filtrate was concentrated under reduced pressure to give a residue, which was purified by com-flash column (0%~15% ethyl acetate in petroleum) to give the desired product tert-butyl 3-(3-bromo-2-fluorobenzoyl)azetidine-1-carboxylate as a light yellow oil. (ESI, m/z): $[M+H-56]^+$:303.8 tert-butyl 3-((3-bromo-2-fluorophenyl)difluoromethyl)azetidine-1-carboxylate To a stirred solution of tert-butyl 3-(3-bromo-2-fluorobenzoyl)azetidine-1-carboxylate (7.5 g, 21 mmol) in BAST (9 mL) was added EtOH (0.05 mL) and the mixture was stirred at 45° C. for 3 days. LCMS showed compound 3 was completed consumed. The mixture was quenched with ice water and extracted with ethyl acetate (80 mL×3). The combined organic layers were dried over $Na_2SO_4$, filtered and concentrated under reduced pressure to give a residue, which was purified by com-flash column (0%~17% ethyl acetate in petroleum) to give the desired product tert-butyl 3-((3-bromo-2-fluorophenyl)difluoromethyl)azetidine-1-carboxylate (as a yellow oil. (ESI, m/z): $[M-tBu+H+ACN]^+$: 366.7

3-((3-bromo-2-fluorophenyl)difluoromethyl)azetidine

To a stirred solution of tert-butyl 3-((3-bromo-2-fluorophenyl)difluoromethyl)azetidine-1-carboxylate (4 g, 10.55 mmol) in DCM (20 mL) was added TFA (10 mL) and the mixture was stirred at room temperature for 16 h. The mixture was concentrated under reduced pressure to give crude product 3-((3-bromo-2-fluorophenyl)difluoromethyl)azetidine, which was used in the next step without further purification. (ESI, m/z): $[M+H]^+$:281.8

3-((3-bromo-2-fluorophenyl)difluoromethyl)-1-isopropylazetidine

A mixture of 3-((3-bromo-2-fluorophenyl)difluoromethyl)azetidine (3.0 g, 10.7 mmol), acetone (5 mL) and HOAc (two drops) in MeOH (15 mL) was stirred at room temperature for 1 h. $NaBH_3CN$ (1.0 g, 16.1 mmol) was added to the mixture and the result solution was stirred at room temperature for 16 h. The mixture was concentrated and purified by com-flash column (0%~7% MeOH in DCM) to give the desired product 3-((3-bromo-2-fluorophenyl)difluoromethyl)-1-isopropylazetidine as a yellow oil. (ESI, m/z): $[M+H]^+$:323.8

1-(3-(difluoro(1-isopropylazetidin-3-yl)methyl)-2-fluorophenyl)ethan-1-one

A mixture of 3-((3-bromo-2-fluorophenyl)difluoromethyl)-1-isopropylazetidine (3.0 g, 9.3 mmol), tributyl(1-ethoxyvinyl)stannane (6.73 g, 18.6 mmol) and $Pd(PPh_3)Cl_2$ (0.2 g, 0.28 mmol) in 1,4-dioxane (20 mL) was heated to 100° C. for 16 h under nitrogen. The mixture was treated with HCl (4N in dioxane) and stirred for another 1 h. It was concentrated and the residue was purified by com-flash column (0%~5% MeOH in DCM) to give the desired product 1-(3-(difluoro(1-isopropylazetidin-3-yl)methyl)-2-fluorophenyl)ethan-1-one as a light yellow oil.

(S)—N-(1-(3-(difluoro(1-isopropylazetidin-3-yl)methyl)-2-fluorophenyl)ethylidene)-2-methylpropane-2-sulfinamide A mixture of 1-(3-(difluoro(1-isopropylazetidin-3-yl)methyl)-2-fluorophenyl)ethan-1-one (1.5 g, 5.3 mmol), (S)-2-methylpropane-2-sulfinamide (766 mg, 6.3 mmol) and $Ti(OEt)_4$ (1.8 g, 7.9 mmol) in THF (10 mL) was heated to 80° C. for 4 h under nitrogen. The mixture was diluted with ethyl acetate/water, filtered and the aqueous was extracted with ethyl acetate (40 mL×3). The combined organic layers were dried over $Na_2SO_4$, filtered and concentrated under reduced pressure to give a residue, which was purified by com-flash column (0%~70% ethyl acetate in petroleum) to give the desired product (S)—N-(1-(3-(difluoro(1-isopropylazetidin-3-yl)methyl)-2-fluorophenyl)ethylidene)-2-methylpropane-2-sulfinamide as a yellow oil. (ESI, m/z): $[M+H]^+$: 389.1.

(S)—N—((R)-1-(3-(difluoro(1-isopropylazetidin-3-yl)methyl)-2-fluorophenyl)ethyl)-2-methylpropane-2-sulfinamide To a stirred solution of (S,Z)—N-(1-(3-(difluoro(1-isopropylazetidin-3-yl)methyl)-2-fluorophenyl)ethylidene)-2-methylpropane-2-sulfinamide (2.6 g, 6.7 mmol) in dry THF (30 mL) was added drop-wise L-slectride (13.4 mL, 13.4 mmol, 1M) at −78° C. under nitrogen and the mixture was stirred at −78° C. for 2 h. The mixture was quenched with sat. aqueous NH₄Cl and the solution was extracted with ethyl acetate (40 mL×3). The combined organic layers were washed with brine and dried over Na₂SO₄, filtered and concentrated under reduced pressure to give a residue, which was purified by com-flash column (0%~20% MeOH in DCM) to give the desired product (S)—N—((R)-1-(3-(difluoro(1-isopropylazetidin-3-yl)methyl)-2-fluorophenyl)ethyl)-2-methylpropane-2-sulfinamide as a yellow oil. (ESI, m/z): [M+H]⁺:390.9.

(R)-1-(3-(difluoro(1-isopropylazetidin-3-yl)methyl)-2-fluorophenyl)ethan-1-amine To a stirred solution of (S)—N—((R)-1-(3-(difluoro(1-isopropylazetidin-3-yl)methyl)-2-fluorophenyl)ethyl)-2-methylpropane-2-sulfinamide (500 mg, 1.2 mmol) in 1,4-dioxane (4 mL) was added HCl/dioxane (1 mL, 4N in dioxane) and the mixture was stirred at room temperature for 1 h. The mixture was concentrated under reduced pressure and the residue was purified by Prep-HPLC to give the desired product (R)-1-(3-(difluoro(1-isopropylazetidin-3-yl)methyl)-2-fluorophenyl)ethan-1-amine as a yellow oil. (ESI, m/z): [M+H]⁺=287.2

₁H NMR (400 MHz, MeOD) δ 7.62 (t, J=7.2 Hz, 1H), 7.43 (t, J=7.2 Hz, 1H), 7.26 (t, J=7.7 Hz, 1H), 4.38 (q, J=6.4 Hz, 1H), 3.41 (d, J=4.7 Hz, 2H), 3.31 (d, J=0.8 Hz, 2H), 3.28-3.16 (m, 2H), 2.42 (m, 1H), 1.41 (d, J=6.7 Hz, 2H), 0.94 (d, J=6.2 Hz, 6H).

Synthesis of (R)-2-(2-(3-(1-aminoethyl)-2-fluorophenyl)-2,2-difluoroethoxy)-N,N-dimethylethan-1-amine

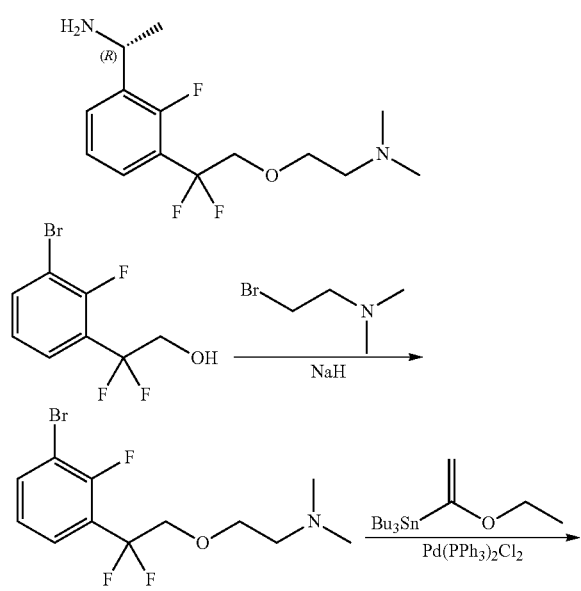

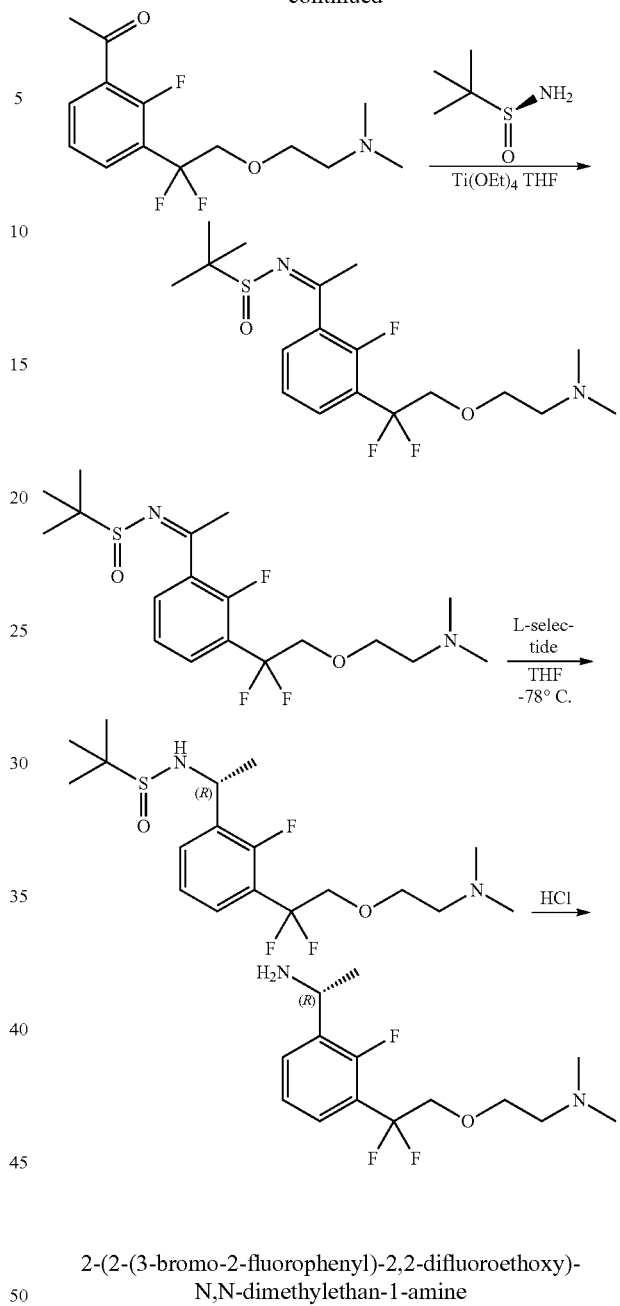

2-(2-(3-bromo-2-fluorophenyl)-2,2-difluoroethoxy)-N,N-dimethylethan-1-amine

To a stirred solution of 2-(3-bromo-2-fluorophenyl)-2,2-difluoroethan-1-ol (15 g, 55.05 mmol) in dry DMF (150 mL) was added NaH (2.64 g, 66.06 mmol, 60% in oil) at 0° C. under nitrogen and the mixture was stirred at 0° C. for 1 h. Then, a solution of 2-bromo-N,N-dimethylethan-1-amine (9.97 g, 66.06 mmol) in dry DMF (20 mL) was added to the mixture and the mixture was warmed to room temperature and stirred for 16 h. It was quenched with water and the mixture was extracted with ethyl acetate (200 mL×3). The combined organic layers were washed with brine, dried over Na₂SO₄, filtered and concentrated under reduced pressure to give a residue, which was purified by com-flash column (0%~30% ethyl acetate in petroleum) to give the desired product 2-(2-(3-bromo-2-fluorophenyl)-2,2-difluoroethoxy)-N,N-dimethylethan-1-amine as a yellow oil.

1-(3-(2-(2-(dimethylamino)ethoxy)-1,1-difluoroethyl)-2-fluorophenyl)ethan-1-one A mixture of -(2-(3-bromo-2-fluorophenyl)-2,2-difluoroethoxy)-N,N-dimethylethan-1-amine (4.9 g, 15.08 mmol), tributyl(1-ethoxyvinyl)stannane (6.55 g, 18.1 mmol) and Pd(PPh$_3$)Cl$_2$ (850 mg, 1.21 mmol) in 1,4-dioxane (50 mL) was heated to 100° C. for 16 h under nitrogen. The mixture was treated with sat. aqueous KF and stirred for another 1 h. It was filtered and treated with HCl solution (6N). The result solution was stirred at room temperature for 2 h. The mixture was neutralized with sat. aqueous NaHCO$_3$ and extracted with ethyl acetate (80 mL×3). The combined organic layers were concentrated. The residue was purified by com-flash column (0%-40% ethyl acetate in petroleum) to give the desired product 1-(3-(2-(2-(dimethylamino)ethoxy)-1,1-difluoroethyl)-2-fluorophenyl)ethan-1-one as a yellow oil.

N-(1-(3-(2-(2-(dimethylamino)ethoxy)-1,1-difluoroethyl)-2-fluorophenyl)ethylidene)-2-methylpropane-2-sulfinamide A mixture of 1-(3-(2-(2-(dimethylamino)ethoxy)-1,1-difluoroethyl)-2-fluorophenyl)ethan-1-one (3.7 g, 12.80 mmol), (S)-2-methylpropane-2-sulfinamide (1.86 g, 15.36 mmol) and Ti(OEt)$_4$ (8.7 g, 25.6 mmol) in THF (40 mL) was heated to 70° C. for 16 h under nitrogen. The mixture was diluted with EA/water, filtered and the aqueous layer was extracted with ethyl acetate (80 mL×3). The combined organic layers were dried over Na$_2$SO$_4$, filtered and the filtrate was concentrated under reduced pressure to give a residue, which was purified by com-flash column (0%~100% ethyl acetate in petroleum) to give the desired product N-(1-(3-(2-(2-(dimethylamino)ethoxy)-1,1-difluoroethyl)-2-fluorophenyl)ethylidene)-2-methylpropane-2-sulfinamide as a yellow oil.

N—((R)-1-(3-(2-(2-(dimethylamino)ethoxy)-1,1-difluoroethyl)-2-fluorophenyl)ethyl)-2-methylpropane-2-sulfinamide To a stirred solution of N-(1-(3-(2-(2-(dimethylamino)ethoxy)-1,1-difluoroethyl)-2-fluorophenyl)ethylidene)-2-methylpropane-2-sulfinamide (3.4 g, 8.67 mmol) in dry THF (30 mL) was added drop-wise L-slectride (17.34 mL, 17.34 mmol, 1M) at −78° C. under nitrogen and the mixture was stirred at −78° C. for 4 h. The mixture was quenched with sat. aqueous NH$_4$Cl and extracted with ethyl acetate (40 mL×3). The combined organic layers were washed with brine and dried over Na$_2$SO$_4$, filtered and the filtrate was concentrated under reduced pressure to give a residue, which was purified by com-flash column (0%~10% MeOH in DCM) to give the desired product N—((R)-1-(3-(2-(2-(dimethylamino)ethoxy)-1,1-difluoroethyl)-2-fluorophenyl)ethyl)-2-methylpropane-2-sulfinamide as yellow oil.

(R)-2-(2-(3-(1-aminoethyl)-2-fluorophenyl)-2,2-difluoroethoxy)-N,N-dimethylethan-1-amine To a stirred solution of N—((R)-1-(3-(2-(2-(dimethylamino)ethoxy)-1,1-difluoroethyl)-2-fluorophenyl)ethyl)-2-methylpropane-2-sulfinamide (2.1 g, 5.33 mmol) in 1,4-dioxane (20 mL) was added HCl/dioxane (20 mL, 4N) and the mixture was stirred for 2 h. The mixture was concentrated under reduced pressure to give a residue, which was purified by Prep-HPLC to get the desired product (R)-2-(2-(3-(1-aminoethyl)-2-fluorophenyl)-2,2-difluoroethoxy)-N, N-dimethylethan-1-amine as a colorless oil. (ESI, m/z): [M+H]$^+$: 291.2; $^1$H NMR (400 MHz, MeOD) δ 7.70 (q, J=7.4 Hz, 2H), 7.43 (t, J=7.8 Hz, 1H), 4.80 (dd, J=13.9, 7.0 Hz, 3H), 4.23-4.09 (m, 2H), 4.01-3.91 (m, 2H), 2.82 (s, 6H), 1.66 (d, J=6.9 Hz, 3H).

Synthesis of (R)-1-((3-(1-aminoethyl)-2-fluorophenyl)difluoromethyl)cyclopropan-1-ol

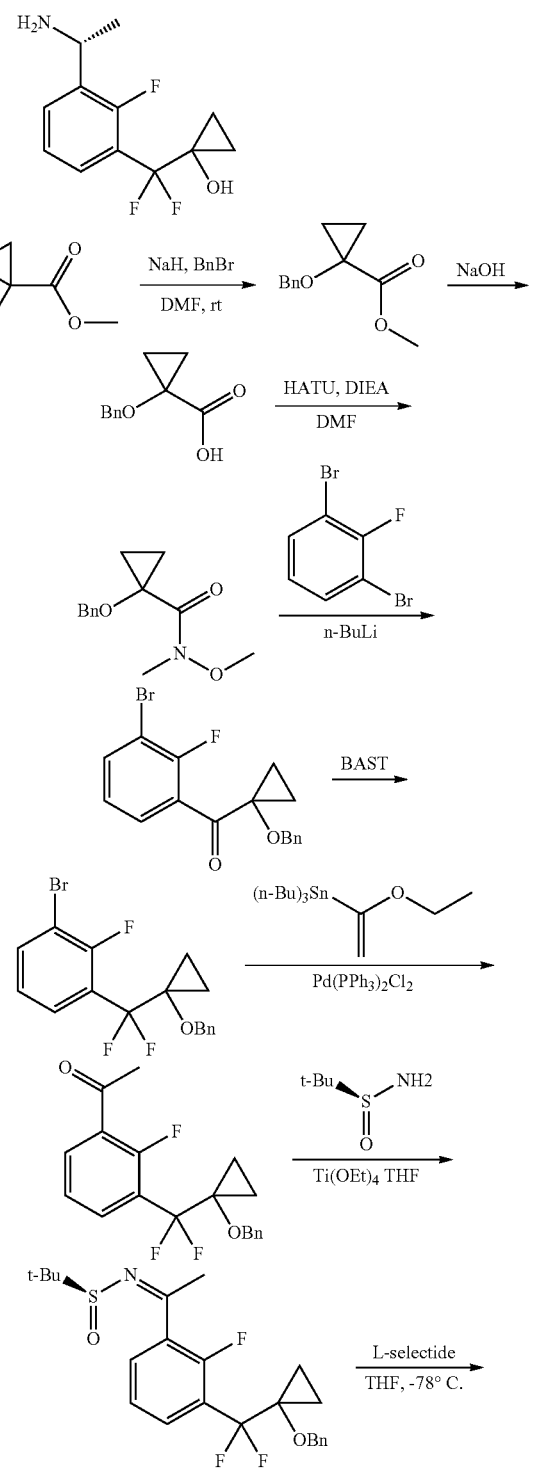

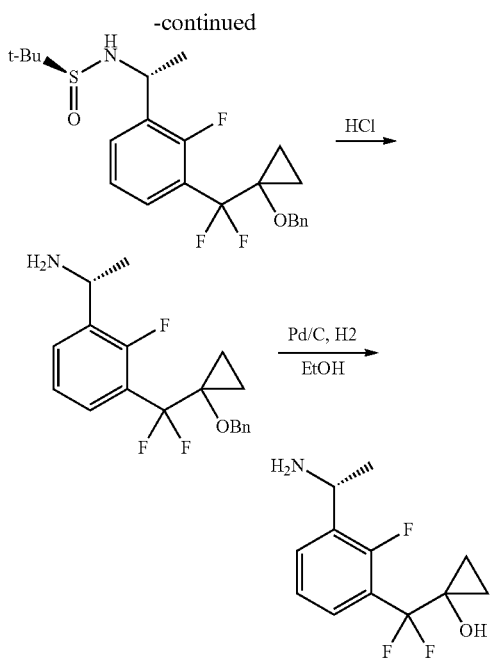

Methyl 1-(benzyloxy)cyclopropane-1-carboxylate

To a stirred solution of methyl 1-hydroxycyclopropane-1-carboxylate (5.0 g, 43.06 mmol) and BnBr (8.10 g, 47.37 mmol) in DMF (30 mL) was added NaH (2.23 g, 55.98 mmol, 60% in oil) and the mixture was stirred at room temperature for 3 h. The solution was quenched with water and extracted with ethyl acetate (30 mL×2). The combined organic layers were washed with brine, dried over $Na_2SO_4$, filtered and concentrated under reduced pressure to give crude product methyl 1-(benzyloxy)cyclopropane-1-carboxylate as a yellow oil, which was used for next step without further purification. (ESI, m/z): [M+H$_2$O]$^+$: 224.1

1-(benzyloxy)cyclopropane-1-carboxylic acid

A mixture of compound 2 (8.7 g, crude) and NaOH (3.44 g, 86.12 mmol) in MeOH/H$_2$O (20 mL/40 mL) was stirred at room temperature for 4 h. The mixture was acidified with HCl (6N). The resulting solution was extracted with ethyl acetate (80 mL×3). The combined organic layers were dried over $Na_2SO_4$, filtered and concentrated under reduced pressure to give a product 1-(benzyloxy)cyclopropane-1-carboxylic acid as a white solid. (ESI, m/z): [M+H$_2$O]$^+$: 210.1. The crude product was used for the next step directly.

1-(benzyloxy)-N-methoxy-N-methylcyclopropane-1-carboxamide

A mixture of 1-(benzyloxy)cyclopropane-1-carboxylic acid (7.2 g, 37.46 mmol), N,O-dimethylhydroxylamine hydrogen chloride (5.48 g, 56.19 mmol), HATU (21.35 g, 56.19 mmol) and DIEA (14.5 g, 112.38 mmol) in DMF (30 mL) was stirred at room temperature for 16 h. The mixture was poured into water and the solution was extracted with ethyl acetate (80 mL×3). The combined organic layers were washed with brine, dried over $Na_2SO_4$, filtered and concentrated under reduced pressure to give a residue, which was purified by com-flash column (0%~7% MeOH in DCM) to give the desired product 1-(benzyloxy)-N-methoxy-N-methylcyclopropane-1-carboxamide as a yellow oil.

(1-(benzyloxy)cyclopropyl)(3-bromo-2-fluorophenyl)methanone

To a stirred solution of 1,3-dibromo-2-fluorobenzene (11.49 g, 45.26 mmol) in dry THF (100 mL) was added drop-wise n-BuLi (18.1 mL, 45.26 mmol, 2.5M in hexane) at −78° C. under nitrogen and the mixture was stirred at same temperature for 1 h. A solution of 1-(benzyloxy)-N-methoxy-N-methylcyclopropane-1-carboxamide (7.1 g, 30.18 mmol) in dry THF (30 mL) was added dropwise to the above mixture at −78° C. The mixture was stirred for 4 h. It was quenched with sat. aqueous NH$_4$Cl and extracted with ethyl acetate (100 mL×3). The combined organic layers were dried over $Na_2SO_4$, filtered and concentrated under reduced pressure to give a residue, which was purified by com-flash column (0%~7% ethyl acetate in petroleum) to give the desired product (1-(benzyloxy)cyclopropyl)(3-bromo-2-fluorophenyl)methanone as a colorless oil. $^1$H NMR (400 MHz, CDCl3) δ 7.71-7.63 (m, 1H), 7.50-7.44 (m, 1H), 7.24-7.15 (m, 3H), 7.06 (td, J=7.9, 0.7 Hz, 1H), 7.01-6.87 (m, 2H), 4.32 (d, J=3.7 Hz, 2H), 1.62-1.54 (m, 2H), 1.42 (dt, J=12.7, 3.8 Hz, 2H).

1-((1-(benzyloxy)cyclopropyl)difluoromethyl)-3-bromo-2-fluorobenzene

A solution of (1-(benzyloxy)cyclopropyl)(3-bromo-2-fluorophenyl)methanone (2.7 g) in BAST (10 mL) was stirred at 50° C. for 3 days. LCMS showed the compound 5 was consumed. The mixture was quenched with ice water and extracted with ethyl acetate (80 mL×3). The combined organic layers were dried over $Na_2SO_4$, filtered and concentrated under reduced pressure to give a residue, which was purified by com-flash column (0%~5% ethyl acetate in petroleum) to give the desired product 1-((1-(benzyloxy)cyclopropyl)difluoromethyl)-3-bromo-2-fluorobenzene as a yellow oil. (ESI, m/z): [M+H$_2$O]$^+$: 388.0; $^1$H NMR (400 MHz, CDCl3) δ 7.70-7.60 (m, 1H), 7.60-7.56 (m, 1H), 7.31-7.18 (m, 3H), 7.14-7.01 (m, 3H), 4.61 (s, 2H), 1.32-1.23 (m, 2H), 1.15-1.07 (m, 2H).

1-(3-((1-(benzyloxy)cyclopropyl)difluoromethyl)-2-fluorophenyl)ethan-1-one

A mixture of 1-((1-(benzyloxy)cyclopropyl)difluoromethyl)-3-bromo-2-fluorobenzene (750 mg, 2.02 mmol), tributyl(1-ethoxyvinyl)stannane (950 mg, 2.63 mmol) and Pd(PPh$_3$)Cl$_2$ (140 mg, 0.2 mmol) in 1,4-dioxane (10 mL) was heated to 100° C. for 16 h under nitrogen. The mixture was treated with HCl (1N) and stirred for another 1 h. The mixture was extracted with ethyl acetate (80 mL×3). The combined organic layers were washed with brine and concentrated to give a residue, which was purified by com-flash column (0%~10% ethyl acetate in petroleum) to give the desired product 1-(3-((1-(benzyloxy)cyclopropyl)difluoromethyl)-2-fluorophenyl)ethan-1-one as a colorless oil.

(S)—N-(1-(3-((1-(benzyloxy)cyclopropyl)difluoromethyl)-2-fluorophenyl)ethylidene)-2-methylpropane-2-sulfinamide A mixture of 1-(3-((1-(benzyloxy)cyclopropyl)difluoromethyl)-2-fluorophenyl)ethan-1-one (600 mg, 1.79 mmol), (S)-2-methylpropane-2-sulfinamide (282 mg, 2.33 mmol)

and Ti(OEt)₄ (817 mg, 3.58 mmol) in THF (20 mL) was heated to 70° C. for 16 h under nitrogen. The mixture was diluted with EA/water, filtered and the aqueous was extracted with ethyl acetate (40 mL×3). The combined organic layers were dried over Na₂SO₄, filtered and concentrated under reduced pressure to give a crude product (S)—N-(1-(3-((1-(benzyloxy)cyclopropyl)difluoromethyl)-2-fluorophenyl)ethylidene)-2-methylpropane-2-sulfinamide as a yellow oil. (ESI, m/z): [M+H]⁺: 438.1. The crude product was used for the next step directly.

(S)—N—((R)-1-(3-((1-(benzyloxy)cyclopropyl)difluoromethyl)-2-fluorophenyl)ethyl)-2-methylpropane-2-sulfinamide To a stirred solution of (S)—N-(1-(3-((1-(benzyloxy)cyclopropyl)difluoromethyl)-2-fluorophenyl)ethylidene)-2-methylpropane-2-sulfinamide (720 mg crude, 1.65 mmol) in dry THF (20 mL) was added drop-wise L-slectride (2.5 mL, 2.47 mmol, 1M) at −78° C. under nitrogen and the mixture was stirred at −78° C. for 3 h. The mixture was quenched with sat. aqueous NH₄Cl and extracted with ethyl acetate (40 mL×3). The combined organic layers were washed with brine and dried over Na₂SO₄, filtered and concentrated under reduced pressure to give a residue, which was purified by com-flash column (0%~70% ethyl acetate in petroleum) to give the desired product (S)—N—((R)-1-(3-((1-(benzyloxy)cyclopropyl)difluoromethyl)-2-fluorophenyl)ethyl)-2-methylpropane-2-sulfinamide as a yellow oil. (ESI, m/z): [M+H]⁺=440.3

(R)-1-(3-((1-(benzyloxy)cyclopropyl)difluoromethyl)-2-fluorophenyl)ethan-1-amine To a stirred solution of (S)—N—((R)-1-(3-((1-(benzyloxy)cyclopropyl)difluoromethyl)-2-fluorophenyl)ethyl)-2-methylpropane-2-sulfinamide (480 mg) in MeOH (6 mL) was added HCl/MeOH (1 mL, 3M) and the mixture was stirred for 2 h. The mixture was concentrated under reduced pressure to give a residue, which was purified by Prep-HPLC to get the desired product (R)-1-(3-((1-(benzyloxy)cyclopropyl)difluoromethyl)-2-fluorophenyl)ethan-1-amine as a yellow oil. (ESI, m/z): [M+H]⁺=336.3

(R)-1-((3-(1-aminoethyl)-2-fluorophenyl)difluoromethyl)cyclopropan-1-ol

A mixture of (R)-1-(3-((1-(benzyloxy)cyclopropyl)difluoromethyl)-2-fluorophenyl)ethan-1-amine (310 mg) and Pd/C (100 mg) in EtOH (8 mL) was stirred at 50° C. for 16 h under hydrogen atmosphere. The mixture was filtered through Celite and the filtrate was concentrated under reduced pressure to give a residue, which was purified by Prep-HPLC to give the desired product (R)-1-((3-(1-aminoethyl)-2-fluorophenyl)difluoromethyl)cyclopropan-1-ol as a colorless oil. (ESI, m/z): [M+H]⁺=246.1, ¹H NMR (400 MHz, MeOD) δ 7.73-7.50 (m, 2H), 7.29 (dd, J=23.9, 16.1 Hz, 1H), 4.62-4.47 (m, 1H), 1.51 (d, J=6.8 Hz, 3H), 1.14-1.05 (m, 2H), 0.86 (q, J=5.4 Hz, 2H).

tert-butyl (R)-3-(3-(3-(1-aminoethyl)-2-fluorophenyl)-3,3-difluoropropyl)azetidine-1-carboxylate

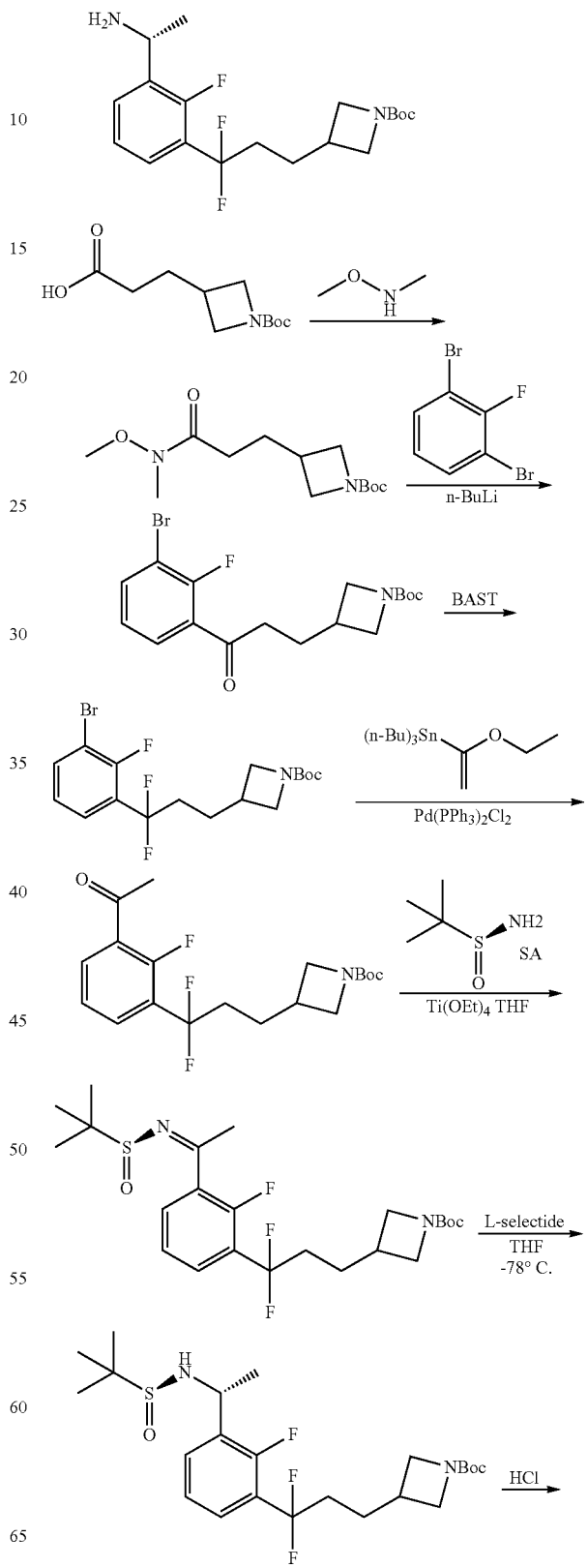

-continued

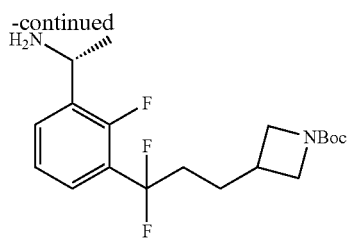

tert-butyl 3-(3-(methoxy(methyl)amino)-3-oxopropyl)azetidine-1-carboxylate Synthesis of compound 2

A mixture of 3-(1-(tert-butoxycarbonyl)azetidin-3-yl)propanoic acid (4 g, 17.45 mmol), N,O-dimethylhydroxylamine hydrogen chloride (2.04 g, 20.94 mmol), HATU (8.3 g, 21.81 mmol) and TEA (5.3 g, 52.34 mmol) in DCM (80 mL) was stirred at room temperature for 16 h. The mixture was poured into water and the solution was extracted with DCM (100 mL×3). The combined organic layers were washed with brine, dried over Na₂SO₄ filtered and concentrated under reduced pressure to give a residue, which was purified by com-flash column (0%~30% ethyl acetate in petroleum) to give the desired product tert-butyl 3-(3-(methoxy(methyl)amino)-3-oxopropyl)azetidine-1-carboxylate as a yellow oil. (ESI, m/z): [M+H-tBu]⁺=217.1 tert-butyl 3-(3-(3-bromo-2-fluorophenyl)-3-oxopropyl)azetidine-1-carboxylate To a stirred solution of 1,3-dibromo-2-fluorobenzene (5.5 g, 20.15 mmol) in dry THF (80 mL) was added drop-wise n-BuLi (10.1 mL, 25.2 mmol, 2.5M in hexane) at −78° C. under nitrogen and the mixture was stirred at same temperature for 1 h. A solution of tert-butyl 3-(3-(methoxy(methyl)amino)-3-oxopropyl)azetidine-1-carboxylate (5.63 g, 22.16 mmol) in dry THF (30 mL) was added dropwise to the mixture at −78° C. The mixture was allowed to warm up to 0° C. and stirred for 4 h. It was quenched with sat. aqueous NH₄Cl and extracted with ethyl acetate (80 mL×3). The combined organic layers were dried over Na₂SO₄, filtered and concentrated under reduced pressure to give a residue, which was purified by com-flash column (0%~20% ethyl acetate in petroleum) to give the desired product tert-butyl 3-(3-(3-bromo-2-fluorophenyl)-3-oxopropyl)azetidine-1-carboxylate as a light yellow oil. (ESI, m z): [M+H-tBu]⁺=330.0.

tert-butyl 3-(3-(3-bromo-2-fluorophenyl)-3,3-difluoropropyl)azetidine-1-carboxylate A solution of tert-butyl 3-(3-(3-bromo-2-fluorophenyl)-3-oxopropyl)azetidine-1-carboxylate (3.1 g) in BAST (6 mL) was stirred at room temperature for 7 days. LCMS showed Compound 3 was completed consumed. The mixture was quenched with ice water and extracted with DCM (50 mL×3). The combined organic layers were dried over Na₂SO₄, filtered and concentrated under reduced pressure to give a residue, which was purified by com-flash column (0%~20% ethyl acetate in petroleum) to give the desired product tert-butyl 3-(3-(3-bromo-2-fluorophenyl)-3,3-difluoropropyl)azetidine-1-carboxylate as a yellow oil. (ESI, m/z): [M+H-tBu]⁺=352.0 tert-butyl 3-(3-(3-acetyl-2-fluorophenyl)-3,3-difluoropropyl)azetidine-1-carboxylate A mixture of tert-butyl 3-(3-(3-bromo-2-fluorophenyl)-3,3-difluoropropyl)azetidine-1-carboxylate (3.0 g, 7.37 mmol), tributyl(1-ethoxyvinyl)stannane (3.2 g, 8.84 mmol) and Pd(PPh₃)Cl₂ (258 mg, 0.37 mmol) in 1,4-dioxane (20 mL) was heated to 100° C. for 16 h under nitrogen. The mixture was treated with HCl (1N) and stirred for another 1 h. The mixture was extracted with ethyl acetate (80 mL×3). The combined organic layers were concentrated and purified by com-flash column (0%~20% ethyl acetate in petroleum) to give the desired product tert-butyl 3-(3-(3-acetyl-2-fluorophenyl)-3,3-difluoropropyl)azetidine-1-carboxylate as a yellow oil. (ESI, m/z): [M-Boc+H]⁺=272.2 tert-butyl (S)-3-(3-(3-(1-((tert-butylsulfinyl)imino)ethyl)-2fluorophenyl)-3,3-difluoropropyl)azetidine-1-carboxylate A mixture of tert-butyl 3-(3-(3-acetyl-2-fluorophenyl)-3,3-difluoropropyl)azetidine-1-carboxylate (1.0 g, 2.695 mmol), (S)-2-methylpropane-2-sulfinamide (408 mg, 3.37 mmol) and Ti(OEt)₄ (799 mg, 3.504 mmol) in THF (20 mL) was heated to 70° C. for 16 h under nitrogen. The mixture was diluted with ethyl acetate/water, filtered and the aqueous was extracted with ethyl acetate (40 mL×3). The combined organic layers were dried over Na₂SO₄, filtered and concentrated under reduced pressure to give a residue, which was purified by com-flash column (0%~70% ethyl acetate in petroleum) to give the desired product tert-butyl (S)-3-(3-(3-(1-((tert-butylsulfinyl)imino)ethyl)-2-fluorophenyl)-3,3-difluoropropyl)azetidine-1-carboxylate as a yellow oil. (ESI, m/z): [M+H]⁺=475.2 tert-butyl 3-(3-(3-((R)-1-(((S)-tert-butylsulfinyl)amino)ethyl)-2-fluorophenyl)-3,3-difluoropropyl)azetidine-1-carboxylate To a stirred solution of tert-butyl (S)-3-(3-(3-(1-((tert-butylsulfinyl)imino)ethyl)-2-fluorophenyl)-3,3-difluoropropyl)azetidine-1-carboxylate (1.0 g, 2.11 mmol) in dry THF (20 mL) was added dropwise L-slectride (4.22 mL, 4.22 mmol, 1M) at −78° C. under nitrogen and the mixture was stirred at −78° C. for 4 h. The mixture was quenched with sat. aqueous NH₄Cl and extracted with ethyl acetate (40 mL×3). The combined organic layers were washed with brine and dried over Na₂SO₄, filtered and the filtrate was concentrated under reduced pressure to give a residue, which was purified by com-flash column (0%~10% MeOH in DCM) to give the desired product tert-butyl 3-(3-(3-((R)-1-(((S)-tert-butylsulfinyl)amino)ethyl)-2-fluorophenyl)-3,3-difluoropropyl)azetidine-1-carboxylate as yellow oil. (ESI, m/z): [M+H]⁺=477.1.

tert-butyl (R)-3-(3-(3-(1-aminoethyl)-2-fluorophenyl)-3,3-difluoropropyl)azetidine-1-carboxylate To a solution was product tert-butyl 3-(3-(3-((R)-1-(((S)-tert-butylsulfinyl)amino)ethyl)-2-fluorophenyl)-3,3-difluoropropyl)azetidine-1-carboxylate (1 g) in 1,4-dioxane (20 mL) at 0° C. was added HCl/dioxane (1 mL, 4M), and the mixture was stirred at rt for 2 h. The mixture was diluted with sat. aqueous NaHCO₃ and concentrated under reduced pressure to give a residue, which was purified by reverse phase and free base to get the desired product tert-butyl (R)-3-(3-(3-(1-aminoethyl)-2-fluorophenyl)-3,3-difluoropropyl)azetidine-1-carboxylate as a yellow oil. (ESI, m/z): [M+H]⁺=373.0, $^1$H NMR (400 MHz, MeOD) δ 7.61 (t, J=6.7 Hz, 1H), 7.45-7.39 (m, 1H), 7.26 (t, J=7.8 Hz, 1H), 4.37 (q, J=6.7 Hz, 1H), 3.97 (t, J=8.1 Hz, 2H), 3.53-3.41 (m, 2H), 2.60-2.48 (m, 1H), 2.35-2.15 (m, 2H), 1.76-1.61 (m, 2H), 1.41-1.40 (m, 12H).

Synthesis of 4-(7-chloro-4-hydroxy-2-methylpyrido[2,3-d]pyrimidin-6-yl)tetrahydro-2H-thiopyran 1,1-dioxide

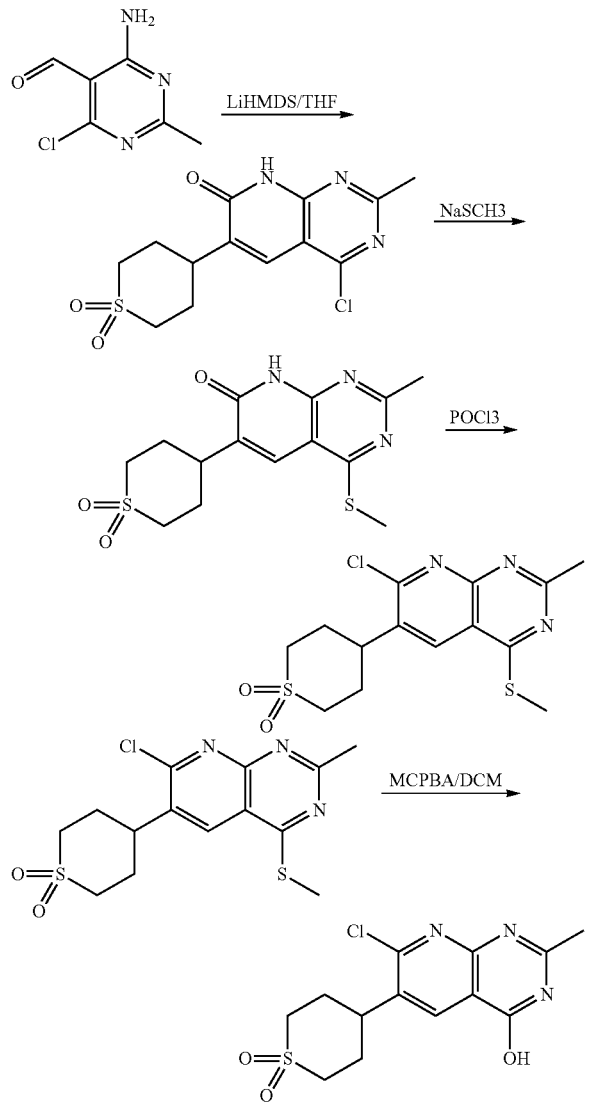

4-chloro-6-(1,1-dioxidotetrahydro-2H-thiopyran-4-yl)-2-methylpyrido[2,3-d]pyrimidin-7(8H)-one A solution of 2-(1,1-dioxidotetrahydro-2H-thiopyran-4-yl) acetate (9.3 g, 42.11 mmol) in THF (80 mL) was stirred at −78° C. under argon. LiHMDS (88 ml, 1 M in THF) was added dropwise and the resulting mixture was stirred for 40 min at −78° C. to −45° C. Then 4-amino-6-chloro-2-methylpyrimidine-5-carbaldehyde (6.0 g, 35.09 mmol) in THF (30 ml) was added dropwise at −78° C., and the mixture was stirred at −78° C. and allowed to warm gradually to room temperature overnight. It was quenched with saturated NH₄Cl (50 mL). The mixture was extracted with ethyl acetate (30 mL×2). Organic extracts were combined, washed with brine, and dried over Na₂SO₄. It was filtered and solvent was removed under reduced pressure to give a crude. The crude was purified by flash chromatography on silica gel (DCM:MeOH=20:1) to afford the desired product as a white solid. ESI-MS m/z: 328[M+H]⁺.

6-(1,1-dioxidotetrahydro-2H-thiopyran-4-yl)-2-methyl-4-(methylthio)pyrido[2,3-d]pyrimidin-7(8H)-one To a solution of 4-chloro-6-(1,1-dioxidotetrahydro-2H-thiopyran-4-yl)-2-methylpyrido[2,3-d]pyrimidin-7(8H)-one (5.0 g, 15.29 mmol) in THF (100 mL), sodium methanethiolate (10 mL, 20% water) was added. The mixture was stirred for 3.0 h at 65° C. under Ar. It was cooled to room temperature, quenched with water (30 mL), and extracted with ethyl acetate (50 mL). The organics were and filtered. Solvent was removed to give a solid. 1N HCl (15 mL) was added to aqueous phase to give precipitation. It was filtered and solid was collected. The aqueous phase was extracted with ethyl acetate (30 mL). The organic extracts were combined, dried over Na₂SO₄. It was filtered and solvent was removed under reduced pressure to provide solid. All solids were combined, dried to give the desired product which was used in the next step without further purification. ESI-MS m/z: 340[M+H]⁺.

(7-chloro-2-methyl-4-(methylthio)pyrido[2,3-d]pyrimidin-6-yl)tetrahydro-2H-thiopyran 1,1-dioxide A mixture of 6-(1,1-dioxidotetrahydro-2H-thiopyran-4-yl)-2-methyl-4-(methylthio)pyrido[2,3-d]pyrimidin-7(8H)-one (5.4 g, 16.23 mmol) in POCl₃ (50 mL) was stirred at 105° C. for 2.0 h. It was cooled and most of POCl₃ was removed under reduced pressure. The resulted residue was partitioned between saturated NaHCO₃ (100 mL) and dichloromethane (50 mL). The aqueous layer was extracted with dichloromethane (50 mL×2). The organics were combined, washed with brine, and dried over Na₂SO₄. It was filtered and solvent was removed under reduced pressure to give the desired product as a solid which was used in the next step without further purification. ESI-MS m/z: 358[M+H]⁺.

4-(7-chloro-4-hydroxy-2-methylpyrido[2,3-d]pyrimidin-6-yl)tetrahydro-2H-thiopyran 1,1-dioxide To solution of 4-(7-chloro-2-methyl-4-(methylthio)pyrido[2,3-d]pyrimidin-6-yl)tetrahydro-2H-thiopyran 1,1-dioxide (4.5 g, 12.61 mmol) in DCM (120 mL) was added m-CPBA (6.5 g, 37.82 mmol) and water (4 mL). The mixture was stirred for 16 h and then 3.0 h at 50° C. It was cooled and the solvent was removed under reduced pressure to give a crude. The crude was purified by flash chromatography on silica gel (petroleum:ethyl acetate=3:1 to 1:1 then dichloromethane:methyl alcohol=10:1) to afford the desired product as a solid. ESI-MS m/z: 328 [M+H]⁺.

Compound 148: Synthesis of 4-(4-((1-(3-(difluoro(tetrahydrofuran-3-yl)methyl)-2-fluorophenyl)ethyl)amino)-7-methoxy-2-methylpyrido[2,3-d]pyrimidin-6-yl)tetrahydro-2H-thiopyran 1,1-dioxide

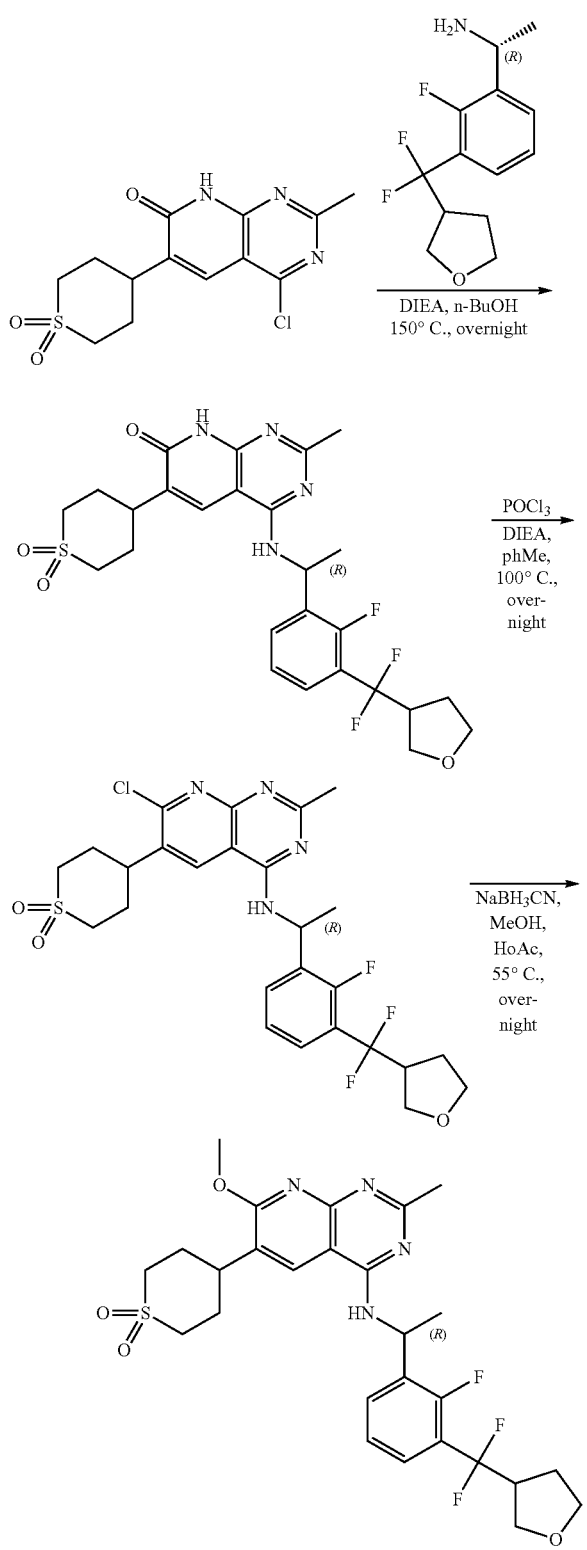

4-((1-(3-(difluoro(tetrahydrofuran-3-yl)methyl)-2-fluorophenyl)ethyl)amino)-6-(1,1-dioxidotetrahydro-2H-thiopyran-4-yl)-2-methylpyrido[2,3-d]pyrimidin-7(8H)-one To a solution of 4-chloro-6-(1,1-dioxidotetrahydro-2H-thiopyran-4-yl)-2-methylpyrido[2,3-d]pyrimidin-7(8H)-one (150 mg, 1 mmol) and (1R)-1-(3-(difluoro(tetrahydrofuran-3-yl)methyl)-2-fluorophenyl)ethan-1-amine (120 mg, 1 mmol) in n-BuOH (10 mL) was added DIEA (230 mg, 1.8 mmol). The resulting mixture was heated at 150° C. under argon and stirred for overnight. It was cooled to room temperature and ethyl acetate (60 mL) was added. The organics were washed with brine, dried over $Na_2SO_4$. It was filtered and solvent was removed under reduced pressure to give a crude. The crude was purified by flash chromatography on silica gel (dichloromethane:methyl alcohol=20:1) to afford the desired product as a solid. ESI-MS m/z: 551[M+H]$^+$;

4-(7-chloro-4-((1-(3-(difluoro(tetrahydrofuran-3-yl)methyl)-2-fluorophenyl)ethyl)amino)-2-methylpyrido[2,3-d]pyrimidin-6-yl)tetrahydro-2H-thiopyran 1,1-dioxide To a solution of 4-(7-chloro-4-((1-(3-(difluoro(tetrahydrofuran-3-yl)methyl)-2-fluorophenyl)ethyl)amino)-2-methylpyrido[2,3-d]pyrimidin-6-yl)tetrahydro-2H-thiopyran1,1-dioxide (140 mg, 1 mmol) was added $POCl_3$ (2 mL). Then DIEA (cat.) was added at room temperature. The resulting mixture was heated at 100° C. under argon and stirred for overnight. Then it was cooled to room temperature and concentrated to remove most of $POCl_3$, the resulted residue was partitioned between saturated $NaHCO_3$ (5 mL) and dichloromethane (20 mL). The aqueous layer was extracted with dichloromethane (20 mL×2). The organics were combined, washed with brine, and dried over $Na_2SO_4$. It was filtered and solvent was removed under reduced pressure to give a crude. The crude was purified by flash chromatography on silica gel (dichloromethane:methyl alcohol=20:1) to afford the desired product as a solid. ESI-MS m/z: 569[M+H]$^+$;

4-(4-((1-(3-(difluoro(tetrahydrofuran-3-yl)methyl)-2-fluorophenyl)ethyl)amino)-7-methoxy-2-methylpyrido[2,3-d]pyrimidin-6-yl)tetrahydro-2H-thiopyran 1,1-dioxide To a solution of 4-(4-((1-(3-(difluoro(tetrahydrofuran-3-yl)methyl)-2-fluorophenyl)ethyl)amino)-7-methoxy-2-methylpyrido[2,3-d]pyrimidin-6-yl)tetrahydro-2H-thiopyran 1,1-dioxide (100 mg, 1 mmol) and sodium methanolate (35 mg, 3 mmol) in MeOH (10 mL) at 0° C. was added NaH (60%, 35 mg, 5 mmol). Then the resulting mixture was heated at 55° C. under argon and stirred for overnight. Then cooled to room temperature and concentrated to remove most of MeOH. The mixture was extracted with ethyl acetate (20 mL×2). Organic extracts were combined, washed with brine, and dried over $Na_2SO_4$. It was filtered and solvent was removed under reduced pressure to give a crude. The crude was purified by prep-TLC (dichloromethane:methyl alcohol=20:1) to afford the desired product as a solid. ESI-MS m/z: 565[M+H]$^+$. $^1$HNMR (400 MHz, MeOD): δ 8.68 (s, 1H), 7.64 (t, J=6.8 Hz, 1H), 7.45 (t, J=6.8 Hz, 1H), 7.24 (t, J=7.6 Hz, 1H), 5.91 (m, 1H), 4.58 (m, 1H), 4.14 (s, 3H), 3.84 (m, 2H), 3.485-3.387 (m, 3H), 3.19 (m, 2H), 2.52 (s, 3H), 2.34 (m, 4H), 2.10 (m, 2H), 1.94 (m, 2H), 1.73 (d, J=6.8 Hz, 3H).

Compound 231: Synthesis of (R)-4-(4-((1-(3-(difluoromethyl)-2-fluorophenyl)ethyl)amino)-7-(oxetan-3-yloxy)pyrido[2,3-d]pyrimidin-6-yl)thiomorpholine 1,1-dioxide

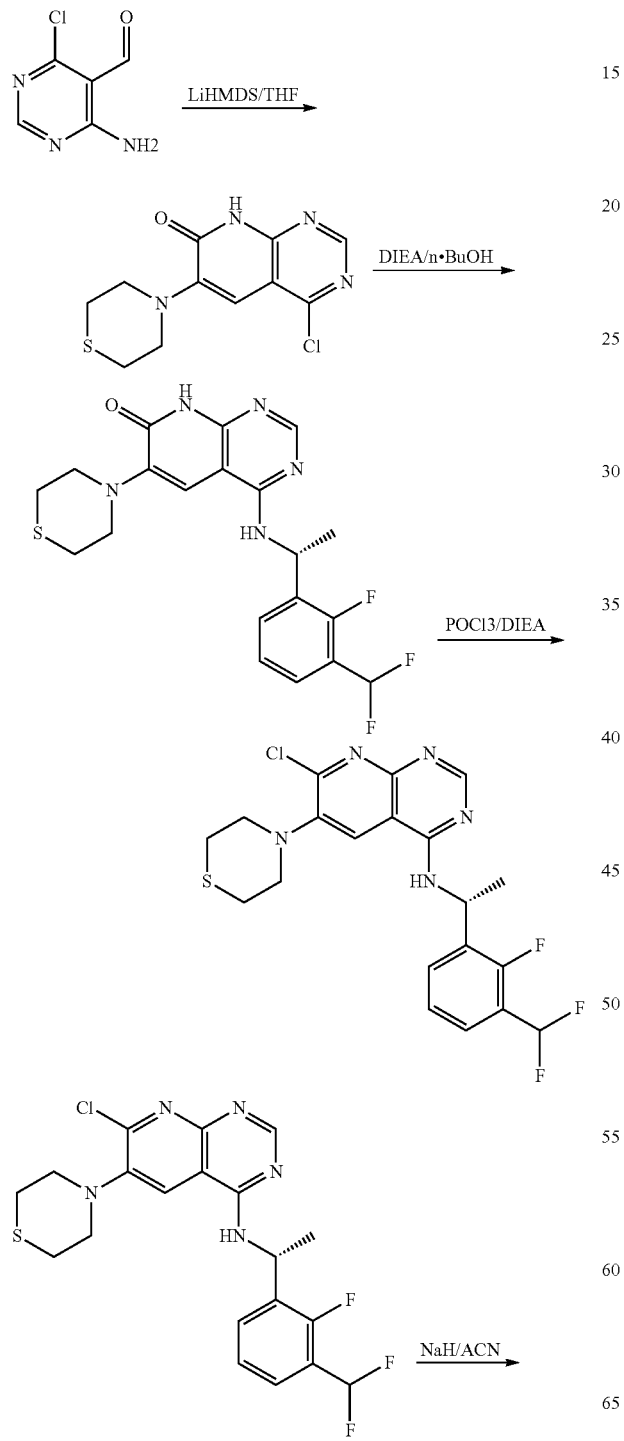

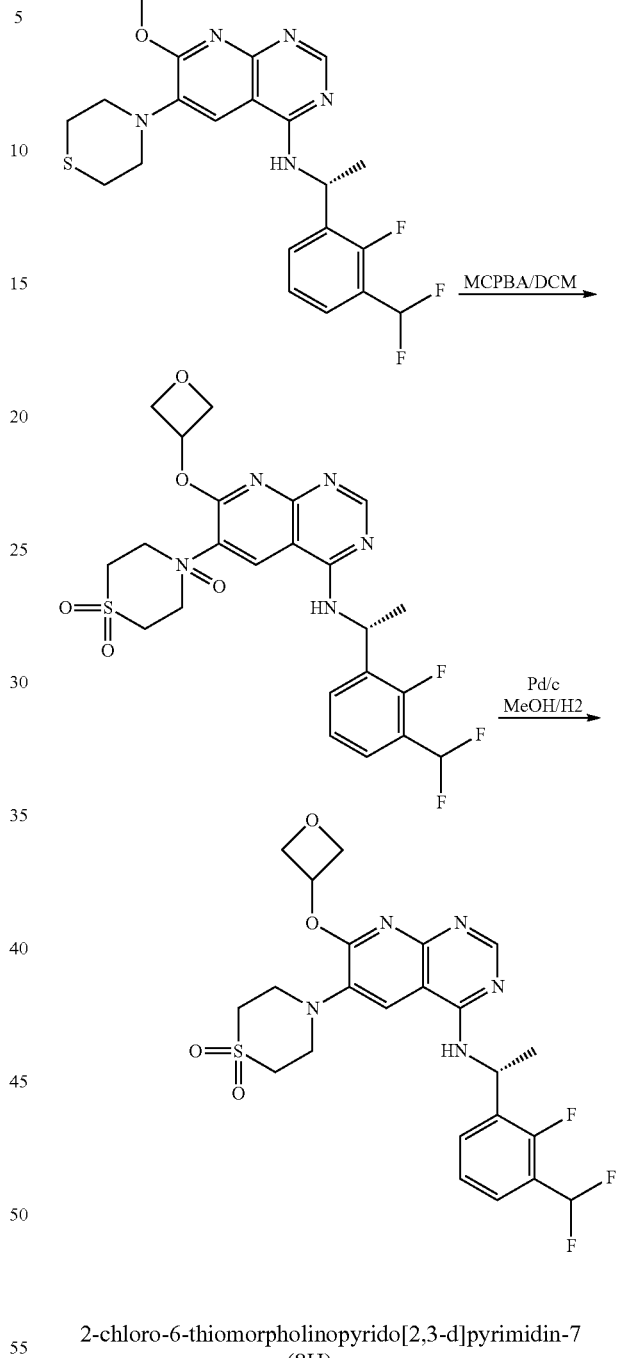

2-chloro-6-thiomorpholinopyrido[2,3-d]pyrimidin-7(8H)-one

A solution of ethyl 2-thiomorpholinoacetate (4.7 g, 24.84 mmol) in THF (10 mL) and 4-amino-6-chloropyrimidine-5-carbaldehyde (3.0 g, 19.11 mmol) was cooled to −78° C. under argon. LiHMDS (48 mL, 1 M in THF) was added dropwise and the resulting mixture was stirred for 16 hours at −78° C. and allowed to warm to room temperature. The reaction mixture was quenched with saturated NH$_4$Cl (40 mL) and extracted with ethyl acetate (30 mL×2). Organic extracts were combined, washed with brine, and dried over Na$_2$SO$_4$. It was filtered and solvent was removed under reduced pressure to give a crude. The crude was purified by flash chromatography on silica gel (dichloromethane methyl alcohol=96:4) to give the desired product as a solid. ESI-MS m/z: 283[M−H]⁺.

(R)-4-((1-(3-(difluoromethyl)-2-fluorophenyl)ethyl)amino)-6-thiomorpholinopyrido[2,3-d]pyrimidin-7(8H)-one To a solution of 4-chloro-6-thiomorpholinopyrido[2,3-d]pyrimidin-7(8H)-one (2.9 g, 10.25 mmol) and (R)-1-(3-(difluoromethyl)-2-fluorophenyl)ethan-1-amine hydrochloride (2.32 g, 10.25 mmol) in n-BuOH (25 mL) was added DIEA (6.61 g, 50.2 mmol). The resulting mixture was heated at 135° C. under argon and stirred for 16 h in sealed tube. It was cooled to room temperature and ethyl acetate (60 mL) was added. The organics were washed with brine, dried over Na₂SO₄. It was filtered and solvent was removed under reduced pressure to give a crude. The crude was purified by flash chromatography on silica gel (dichloromethane:methyl alcohol=20:1) to afford the desired product as a solid. ESI-MS m/z: 436[M+H]⁺;

(R)-7-chloro-N-(1-(3-(difluoromethyl)-2-fluorophenyl)ethyl)-6-thiomorpholinopyrido[2,3-d]pyrimidin-4-amine To a solution of (R)-4-((1-(3-(difluoromethyl)-2-fluorophenyl)ethyl)amino)-6-thiomorpholinopyrido[2,3-d]pyrimidin-7(8H)-one (500 mg, 1.15 mmol) was added POCl₃ (8 mL). Then DIEA (two drops) was added at room temperature. The resulting mixture was heated at 105° C. under argon and stirred for 5 h. Then it was cooled to room temperature and concentrated to remove most POCl₃. The resulted residue was partitioned between saturated NaHCO₃ (5 mL) and dichloromethane (20 mL). The aqueous layer was extracted with dichloromethane (20 mL×2). The organics were combined, washed with brine, and dried over Na₂SO₄. It was filtered and solvent was removed under reduced pressure to give a crude. The crude was purified by flash chromatography on silica gel (dichloromethane:methyl alcohol=20:1) to afford the desired product as a solid. ESI-MS m/z: 454[M+H]⁺;

(R)—N-(1-(3-(difluoromethyl)-2-fluorophenyl)ethyl)-7-(oxetan-3-yloxy)-6-thiomorpholinopyrido[2,3-d]pyrimidin-4-amine To a solution of oxetan-3-ol (106 mg, 1.43 mmol) in ACN (15 ml) at 0° C., NaH (60%, 58 mg, 1.43 mmol) was added and the resulting mixture was stirred for 30 min at 0° C. under argon. (R)-7-chloro-N-(1-(3-(difluoromethyl)-2-fluorophenyl)ethyl)-6-thiomorpholinopyrido[2,3-d]pyrimidin-4-amine (430 mg, 0.95 mmol) was added. Then the resulting mixture was heated at 65° C. under argon and stirred for 2 hours. Then it was cooled to room temperature. The mixture was extracted with ethyl acetate (30 mL×2). Organic extracts were combined, washed with brine, and dried over Na₂SO₄. It was filtered and solvent was removed under reduced pressure to give a crude. The crude was purified by flash chromatography on silica gel (dichloromethane:methyl alcohol=20:1) to afford the desired product as a solid. ESI-MS m/z: 492[M+H]⁺.

(R)-4-(4-((1-(3-(difluoromethyl)-2-fluorophenyl)ethyl)amino)-7-(oxetan-3-yloxy)pyrido[2,3-d]pyrimidin-6-yl)thiomorpholine 4-oxide 1,1-dioxide To a solution of (R)—N-(1-(3-(difluoromethyl)-2-fluorophenyl)ethyl)-7-(oxetan-3-yloxy)-6-thiomorpholinopyrido[2,3-d]pyrimidin-4-amine (350 mg, 0.72 mmol) in DCM (15 mL) at room temperature was added 3-chlorobenzoperoxoic acid (368 mg, 2.14 mmol). Then the resulting mixture was stirred for 5 hours at room temperature under argon. The reaction mixture was quenched with saturated NaHCO₃ (20 mL) and extracted with DCM (30 mL×2). Organic extracts were combined, washed with brine, and dried over Na₂SO₄. It was filtered and solvent was removed under reduced pressure to give a crude. The crude was purified by flash chromatography on silica gel (dichloromethane:methyl alcohol=10:1) to afford the desired product as a solid. ESI-MS m/z: 540[M+H]⁺.

(R)-4-(4-((1-(3-(difluoromethyl)-2-fluorophenyl)ethyl)amino)-7-(oxetan-3-yloxy)pyrido[2,3-d]pyrimidin-6-yl)thiomorpholine 1,1-dioxide To a solution of (R)-4-(4-((1-(3-(difluoromethyl)-2-fluorophenyl)ethyl)amino)-7-(oxetan-3-yloxy)pyrido[2,3-d]pyrimidin-6-yl)thiomorpholine 4-oxide 1,1-dioxide (240 mg, 0.45 mmol) in MeOH (10 ml) at room temperature was added Pd/C (10%, 40 mg, 0.05 mmol). Then the resulting mixture was stirred at room temperature under hydrogen and stirred for 2.5 hours. It was filtered and solvent was removed under reduced pressure to give a crude. The crude was purified by prep-TLC to afford the desired product as a solid. ESI-MS m/z: 524[M+H]⁺; ¹HNMR (CD3OD, 400 MHz): δ 8.26 (s, 1H), 8.12 (s, 1H), 7.50-7.46 (t, J=7.2 Hz, 1H), 7.40-7.36 (t, J=7.2 Hz, 1H), 7.14-7.11 (t, J=7.6 Hz, 1H), 7.04-6.76 (t, J=54.8 Hz, 1H), 5.74-5.67 (m, 2H), 5.02-4.99 (m, 2H), 4.72-4.65 (m, 2H), 3.66 (m, 4H), 3.24 (m, 4H), 1.58-1.56 (d, J=7.2 Hz, 3H).

Compound 175: Synthesis of (R)-1-(4-((1-(3-(1,1-difluoro-2-hydroxy-2-methylpropyl)phenyl)ethyl)amino)-7-methoxy-2-methylpyrido[2,3-d]pyrimidin-6-yl)cyclopropane-1-carbonitrile

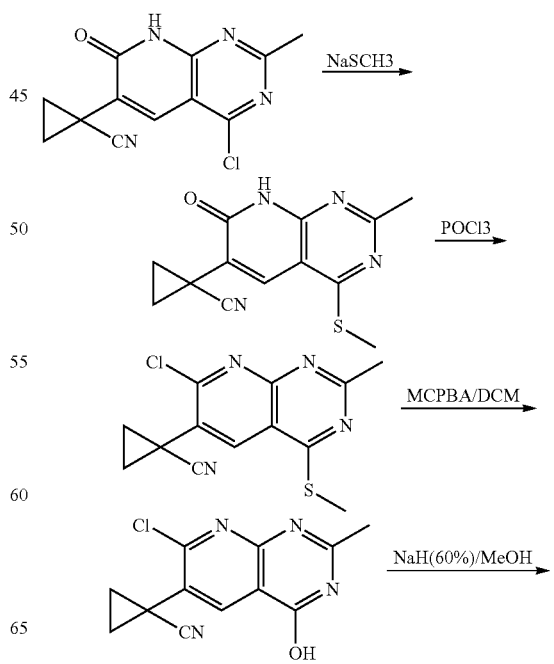

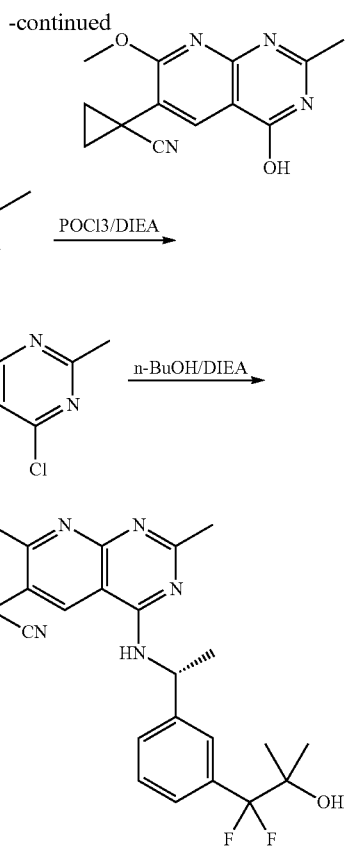

1-(2-methyl-4-(methylthio)-7-oxo-7,8-dihydropyrido[2,3-d]pyrimidin-6-yl)cyclopropane-1-carbonitrile To a solution of 1-(4-chloro-2-methyl-7-oxo-7,8-dihydropyrido[2,3-d]pyrimidin-6-yl)cyclopropane-1-carbonitrile (1.0 g, 3.85 mmol) in THF (15 mL) was added sodium methanethiolate (2.0 mL, 20% water). The mixture was stirred for 1.5 h at 65° C. under Ar. Then it was cooled to room temperature. 1N HCl (3 mL) was added to aqueous phase resulted in precipitation. It was filtered and solid was collected. Aqueous phase was extracted with ethyl acetate (10 mL×2). Then the organic extracts were combined, and solvent was removed under reduced pressure to give solid. The solid was combined to provide desired product as a solid which was used in the next step without further purification. ESI-MS m/z: 273 [M+H]$^+$.

1-(7-chloro-2-methyl-4-(methylthio)pyrido[2,3-d]pyrimidin-6-yl)cyclopropane-1-carbonitrile A mixture of 1-(2-methyl-4-(methylthio)-7-oxo-7,8-dihydropyrido[2,3-d]pyrimidin-6-yl)cyclopropane-1-carbonitrile (1.02 g, 3.75 mmol) in POCl$_3$ (10 mL) was stirred at 105° C. for 1.5 h. It was cooled to room temperature and most of POCl$_3$ was removed under reduced pressure. The resulted residue was partitioned between saturated NaHCO$_3$ (15 mL) and dichloromethane (15 mL). The aqueous layer was extracted with dichloromethane (20 mL×2). The organics were combined, washed with brine, and dried over Na$_2$SO$_4$. It was filtered and solvent was removed under reduced pressure to give the desired product as a solid which was used in the next step without further purification. ESI-MS m/z: 291[M+H]$^+$.

1-(7-chloro-4-hydroxy-2-methylpyrido[2,3-d]pyrimidin-6-yl)cyclopropane-1-carbonitrile A solution of 1-(7-chloro-2-methyl-4-(methylthio)pyrido[2,3-d]pyrimidin-6-yl)cyclopropane-1-carbonitrile (430 mg, 1.49 mmol) in DCM (10 mL) was added MCPBA (1.03 g, 5.96 mmol) and water (0.5 mL) was. The mixture was stirred for 16 h. The solvent was removed under reduced pressure to give a crude. The crude was purified by flash chromatography on silica gel (dichloromethane:methyl alcohol=10:1) to afford the desired product as a solid. ESI-MS m/z: 261 [M+H]$^+$.

1-(4-hydroxy-7-methoxy-2-methylpyrido[2,3-d]pyrimidin-6-yl)cycloropane-1-carbonitrile To a solution of 1-(7-chloro-4-hydroxy-2-methylpyrido[2,3-d]pyrimidin-6-yl)cyclopropane-1-carbonitrile (320 mg, 1.22 mmol) in MeOH (10 mL) was added sodium methanolate (267 mg, 4.88 mmol). Then NaH (60%, 124 mg, 3.05 mmol) was added at 0° C. The mixture was stirred at 60° C. for 2.0 h. It was cooled to room temperature, water (2.0 ml) was added. Most of MeOH was then removed under reduced pressure. Aqueous phase was extracted with ethyl acetate (20 mL). Then the organic extracts were combined, washed with brine, and dried over Na$_2$SO$_4$. It was filtered and solvent was removed under reduced pressure to give the desired product as a solid which was used in the next step without further purification. ESI-MS m/z: 257 [M+H]$^+$.

1-(4-chloro-7-methoxy-2-methylpyrido[2,3-d]pyrimidin-6-yl)cyclopropane-1-carbonitrile To a solution of 1-(4-hydroxy-7-methoxy-2-methylpyrido[2,3-d]pyrimidin-6-yl)cyclopropane-1-carbonitrile (300 mg, 1.18 mmol) was added POCl$_3$ (10 ml). Then DIEA (cat) was added at room temperature with stirring. The resulting mixture was heated at 105° C. under argon and stirred for 16 h. Then it was cooled to room temperature and concentrated to remove most of POCl$_3$. The resulted residue was partitioned between saturated NaHCO$_3$ (10 ml) and dichloromethane (10 mL). The aqueous layer was extracted with dichloromethane (20 mL×2). The organics were combined, washed with brine, and dried over Na$_2$SO$_4$. It was filtered and solvent was removed under reduced pressure to give a crude. The crude was purified by flash chromatography on silica gel (petroleum:ethyl acetate=3:1) to afford the desired product as a solid. ESI-MS m/z: 275[M+H]$^+$;

(R)-1-(4-((1-(3-(1,1-difluoro-2-hydroxy-2-methylpropyl)phenyl)ethyl)amino)-7-methoxy-2-methylpyrido[2,3-d]pyrimidin-6-yl)cyclopropane-1-carbonitrile To a solution of 1-(4-chloro-7-methoxy-2-methylpyrido[2,3-d]pyrimidin-6-yl)cyclopropane-1-carbonitrile (50 mg, 0.19 mmol) and (R)-1-(3-(1-aminoethyl)phenyl)-1,1-difluoro-2-methylpropan-2-ol hydrochloride (49 mg, 0.19 mmol) in n-BuOH (10 mL) was added DIEA (245 mg, 1.9 mmol). The resulting mixture was heated at 120° C. under argon and stirred for 4 h. It was cooled to room temperature and ethyl acetate (20 mL) was added. The organics were combined, washed with brine, and dried over Na$_2$SO$_4$. It was filtered and solvent was removed under reduced pressure to give a crude. The crude was purified by flash chromatography on silica gel (dichloromethane:methyl alcohol=20:1) to afford the desired product as a white solid. ESI-MS m/z:

468[M+H]⁺; ¹HNMR (DMSO-d6, 400 MHz): δ 9.11 (brs, 1H), 8.87 (s, 1H), 7.59-7.57 (m, 2H), 7.41 (t, J=7.6 Hz, 1H), 7.35 (d, J=7.6 Hz, 1H), 5.67-5.60 (m, 1H), 5.22 (s, 1H), 4.10 (s, 3H), 2.44 (s, 3H), 1.73-1.72 (m, 2H), 1.64-1.62 (d, J=7.2 Hz, 3H), 1.52-1.51 (m, 2H), 1.14 (s, 6H).

Compound 379: Synthesis of (R)-4-(4-((1-(3-(difluoro(1-isopropylpiperidin-4-yl)methyl)-2-fluorophenyl)ethyl)amino)-7-methoxy-2-methylpyrido[2,3-d]pyrimidin-6-yl)tetrahydro-2H-thiopyran 1,1-dioxide

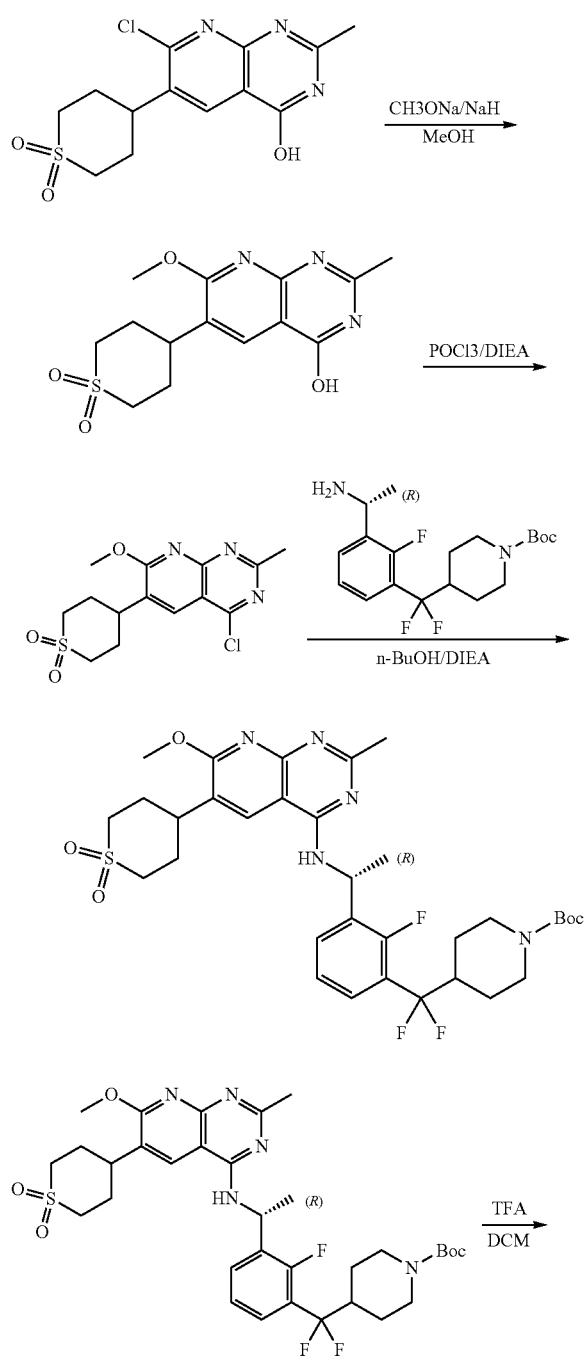

4-(4-hydroxy-7-methoxy-2-methylpyrido[2,3-d]pyrimidin-6-yl)tetrahydro-2H-thiopyran 1,1-dioxide To a solution of 4-(7-chloro-4-hydroxy-2-methylpyrido[2,3-d]pyrimidin-6-yl)tetrahydro-2H-thiopyran 1,1-dioxide (500 mg, 1.53 mmol) and CH₃ONa (413 mg, 7.65 mmol) in MeOH (20 mL) was cooled to −0° C. NaH (184 mg, 4.59 mmol) was added. The resulting mixture was heated at 60° C. and stirred for 2 h. It was cooled to room temperature and ethyl acetate (60 mL) was added. The organics were separated, washed with brine, and dried over Na₂SO₄. It was filtered and solvent was removed under reduced pressure to give a crude. The crude was purified by flash chromatography on silica gel (DCM:MeOH=20:1) to afford the desired product as a yellow solid. ESI-MS m/z: 324 [M+H]⁺;

(4-chloro-7-methoxy-2-methylpyrido[2,3-d]pyrimidin-6-yl)tetrahydro-2H-thiopyran 1,1-dioxide To a solution of 4-(4-hydroxy-7-methoxy-2-methylpyrido[2,3-d]pyrimidin-6-yl)tetrahydro-2H-thiopyran 1,1-dioxide (400 mg, 1.24 mmol) in POCl₃ (12 mL), DIEA (two drops) was added. The resulting mixture was heated at 105° C. and stirred for overnight. Then it was cooled to room temperature and concentrated to remove most POCl₃. The resulted residue was partitioned between saturated NaHCO₃ (5 mL) and dichloromethane (20 mL). the aqueous layer was extracted with dichloromethane (20 mL×2). The organics were combined, washed with brine, and dried over Na₂SO₄. The crude was purified by flash chromatography on silica gel (DCM:MeOH=20:1) to afford the desired product as a yellow solid. ESI-MS m/z: 342 [M+H]⁺;

tert-butyl (R)-4-((3-(1-((6-(1,1-dioxidotetrahydro-2H-thiopyran-4-yl)-7-methoxy-2-methylpyrido[2,3-d]pyrimidin-4-yl)amino)ethyl)-2-fluorophenyl)difluoromethyl)piperidine-1-carboxylate To a solution of 4-(4-chloro-7-methoxy-2-methylpyrido[2,3-d]pyrimidin-6-yl)tetrahydro-2H-thiopyran 1,1-dioxide (300 mg, 0.88 mmol) and tert-butyl (R)-4-((3-(1-aminoethyl)-2-fluorophenyl)difluoromethyl)piperidine-1-carboxylate (345 mg, 1.06 mmol) in n-BuOH (10 mL) was added DIEA (2 mL). The resulting mixture was heated at 125° C. under argon and stirred for overnight. It was cooled to room temperature and ethyl acetate (60 mL) was added. The organics were washed with brine, dried over $Na_2SO_4$. It was filtered and solvent was removed under reduced pressure to give a crude. The crude was purified by flash chromatography on silica gel (DCM:MeOH=15:1) to afford the desired product as a yellow solid. ESI-MS m/z: 678[M+H]$^+$;

4-(4-((1-(3-(difluoro(piperidin-4-yl)methyl)-2-fluorophenyl)ethyl)amino)-7-methoxy-2-methylpyrido[2,3-d]pyrimidin-6-yl)tetrahydro-2H-thiopyran 1,1-dioxide To a solution of tert-butyl (R)-4-((3-(1-((6-(1,1-dioxidotetrahydro-2H-thiopyran-4-yl)-7-methoxy-2-methylpyrido[2,3-d]pyrimidin-4-yl)amino)ethyl)-2-fluorophenyl)difluoromethyl)piperidine-1-carboxylate (220 mg, 0.33 mmol) in dichloromethane (10 mL) at 0° C. was added 2,2,2-trifluoroacetic acid (2 mL). The resulting mixture was heated at RT under argon and stirred for 1 hour. Then it was concentrated to remove most of 2,2,2-trifluoroacetic acid, the resulted residue was partitioned between saturated $NaHCO_3$ (5 mL) and dichloromethane (20 mL). The aqueous layer was extracted with dichloromethane (20 mL×2). The organics were combined, washed with brine, and dried over $Na_2SO_4$. It was filtered and solvent was removed under reduced pressure to give a crude. The crude was purified by flash chromatography on silica gel ((DCM:Me=15:1) to afford the desired product as a yellow solid. ESI-MS m/z: 578 [M+H]$^+$;

(R)-4-(4-((1-(3-(difluoro(1-isopropylpiperidin-4-yl)methyl)-2-fluorophenyl)ethyl)amino)-7-methoxy-2-methylpyrido[2,3-d]pyrimidin-6-yl)tetrahydro-2H-thiopyran 1,1-dioxide To a solution of (R)-4-(4-((1-(3-(difluoro(piperidin-4-yl)methyl)-2-fluorophenyl)ethyl)amino)-7-methoxy-2-methylpyrido[2,3-d]pyrimidin-6-yl)tetrahydro-2H-thiopyran 1,1-dioxide (250 mg crude, 0.44 mmol) and acetone (128 mg, 2.2 mmol) in MeOH (10 mL) at room temperature were added acetic acid (cat) and stirred for 30 min followed by the addition of sodium cyanoborohydride (138 mg, 2.2 mmol). Then the resulting mixture was stirred at 55° C. under argon and stirred for overnight. Then cooled to RT and concentrated to remove most MeOH. The mixture was extracted with ethyl acetate (15 mL×2). Organic extracts were combined, washed with brine, and dried over $Na_2SO_4$. It was filtered and solvent was removed under reduced pressure to give a crude. The crude was purified by prep-TLC to afford the desired product as a white solid. ESI-MS m/z: 620 [M+H]$^+$; $^1$HNMR (MeOD: 400 MHz): δ 8.74 (s, 1H), 7.72-7.68 (t, J=6.8 Hz, 1H), 7.48-7.4 (t, J=6.8 Hz, 1H), 7.32-7.28 (t, J=7.6 Hz, 1H), 6.00-5.95 (m, 1H), 4.16 (s, 3H), 3.55-3.51 (m, 3H), 3.44-3.35 (m, 2H), 3.19-3.07 (m, 4H), 2.77-2.72 (m, 1H), 2.58 (s, 3H), 2.42-2.31 (m, 4H), 2.09-1.93 (m, 5H), 1.76-1.74 (d, J=6.8 Hz, 3H), 1.41-1.33 (m, J=6.4 Hz, 6H).

Compound 209: Synthesis of (R)-1-(difluoro(2-fluoro-3-(1-((6-(4-isopropylpiperazin-1-yl)-7-methoxy-2-methylpyrido[2,3-d]pyrimidin-4-yl)amino)ethyl)phenyl)methyl)cyclopropan-1-ol

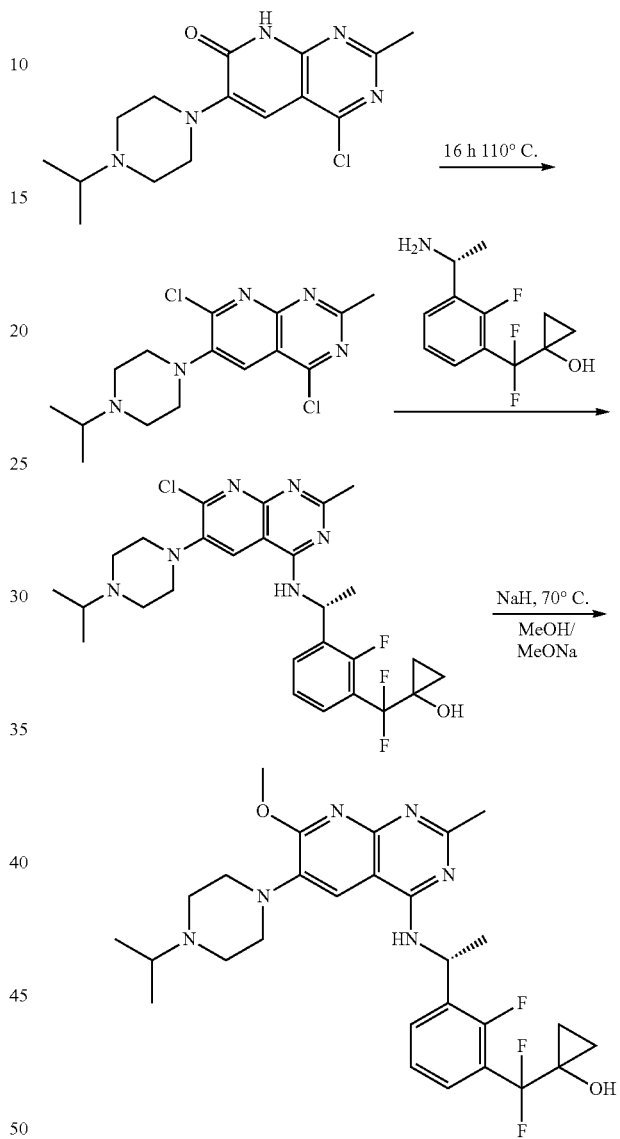

4,7-dichloro-6-(4-isopropylpiperazin-1-yl)-2-methylpyrido[2,3-d]pyrimidine

To a stirred solution of 4-chloro-6-(4-isopropylpiperazin-1-yl)-2-methylpyrido[2,3-d]pyrimidin-7(8H)-one (250 mg, 0.685 mmol) in POCl$_3$ (10 mL) was added DIEA (200 mg, 1.55 mmol), then the mixture was heated to 110° C. for 5 hour. It was cooled to room temperature and solvent was removed, the residue was extracted with DCM and washed with saturated $NaHCO_3$ solution. The organics was washed with brine, dried over $Na_2SO_4$. It was filtered and concentrated to give a residue. The residue was used for next step without farther purified ESI-MS m/z: 340.1 [M+H]$^+$.

(R)-1-((3-(1-((7-chloro-6-(4-isopropylpiperazin-1-yl)-2-methylpyrido[2,3-d]pyrimidin-4-yl)amino)ethyl)-2-fluorophenyl)difluoromethyl)cyclopropan-1-ol To a solution of 4,7-dichloro-6-(4-isopropylpiperazin-1-yl)-2-methylpyrido[2,3-d]pyrimidine (240 mg, crud) in DMSO (10 mL) was added KF (300 mg, 5.357 mmol) and (R)-1-((3-(1-aminoethyl)-2-fluorophenyl)difluoromethyl)cyclopropan-1-ol (60 mg, 0.264 mmol); and the mixture was heated to 100° C. for 1 hour. The mixture was extracted with ethyl acetate and washed with saturated NaHCO₃. The organics were combined, washed with brine, and dried over Na₂SO₄. It was filtered and solvent was removed under reduced pressure to give a residue. The residue was purified by flash column chromatography on silica gel to give desired product ESI-MS m/z: 549.3 [M+H]⁺.

(R)-1-(difluoro(2-fluoro-3-(1-((6-(4-isopropylpiperazin-1-yl)-7-methoxy-2-methylpyrido[2,3-d]pyrimidin-4-yl)amino)ethyl)phenyl)methyl)cyclopropan-1-ol To a solution of Sodium methoxide (100 mg, 1.85 mmol) in MeOH (10 mL) was added NaH (100 mg, 2.5 mmol), and the mixture was stirred for 5 min at rt. Then (R)-1-((3-(1-((7-chloro-6-(4-isopropylpiperazin-1-yl)-2-methylpyrido[2,3-d]pyrimidin-4-yl)amino)ethyl)-2-fluorophenyl)difluoromethyl)cyclopropan-1-ol (40 mg, 0.075 mmol, in 2 mL MeOH) was added to the reaction, and the resulting mixture was heated to 70° C. for 1 hour. The solvent was removed, the residue was extracted with ethyl acetate and washed with saturated NaHCO₃ solution. The organics were combined, washed with brine, and dried over Na₂SO₄. It was filtered and solvent was removed under reduced pressure to give a residue. The residue was purified by flash column chromatography on silica gel to give desired product ESI-MS m/z: 545.3 [M+H]⁺. ¹HNMR (CD3OD, 400 MHz): δ 7.86 (s, 1H), 7.46 (t, J=6.8 Hz, 1H), 7.4 (t, J=6.4 Hz, 1H), 7.08 (t, J=7.6 Hz, 1H), 5.76 (m, 1H), 4.45 (m, 1H), 4.08 (s, 3H), 3.2-3.0 (m, 4H), 2.8-2.6 (m, 5H), 2.32 (s, 3H), 1.57 (d, J=6.8 Hz, 3H), 1.3-1.15 (m, 4H), 1.08 (d, J=6.0 Hz, 6H).

Compound 274: Synthesis of (R)—N-(1-(3,3-difluoro-2,2-dimethyl-2,3-dihydrobenzofuran-7-yl)ethyl)-6-(4-isopropylpiperazin-1-yl)-2-methyl-7-(oxetan-3-ylmethoxy)pyrido[2,3-d]pyrimidin-4-amine

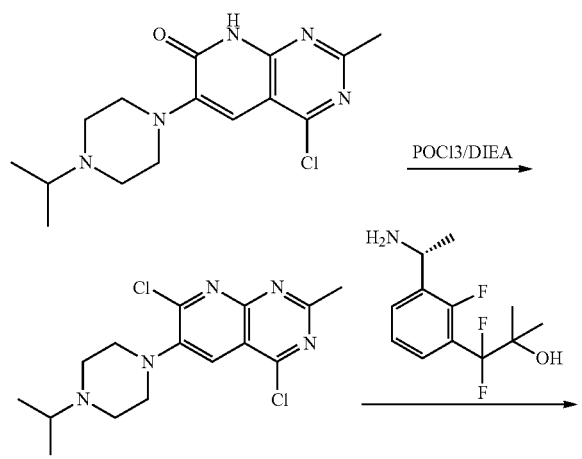

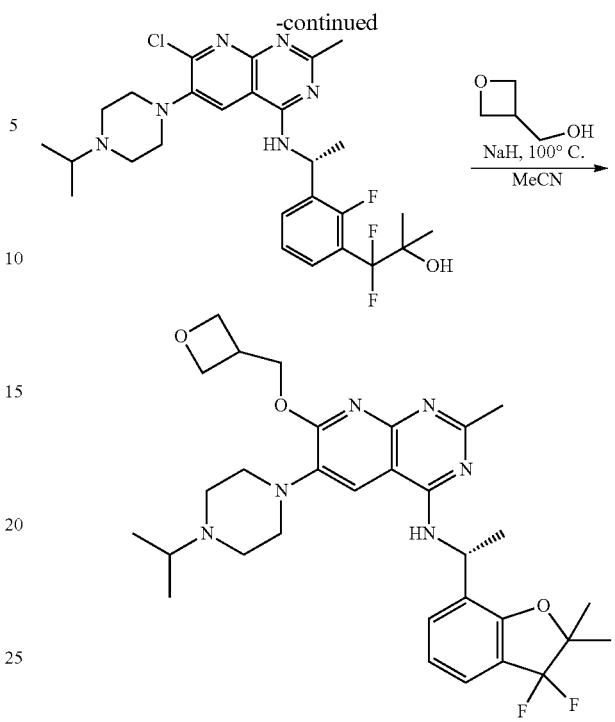

4,7-dichloro-6-(4-isopropylpiperazin-1-yl)-2-methylpyrido[2,3-d]pyrimidine

To a stirred solution of 4-chloro-6-(4-isopropylpiperazin-1-yl)-2-methylpyrido[2,3-d]pyrimidin-7(8H)-one (250 mg, 0.685 mmol) in POCl₃ (10 mL) was added DIEA (200 mg, 1.55 mmol). The mixture was then heated to 110° C. for 3 hours with stirring. It was cooled and the solvent was removed, the residue was extracted with DCM and washed with saturated NaHCO₃ solution. The organics were combined, washed with brine, dried over Na₂SO₄. It was filtered and solvent was removed under reduced pressure to give a residue. The residue was used for next step without farther purified ESI-MS m/z: 340.1 [M+H]⁺.

(R)-1-(3-(1-((7-chloro-6-(4-isopropylpiperazin-1-yl)-2-methylpyrido[2,3-d]pyrimidin-4-yl)amino)ethyl)-2-fluorophenyl)-1,1-difluoro-2-methylpropan-2-ol To a solution of 4,7-dichloro-6-(4-isopropylpiperazin-1-yl)-2-methylpyrido[2,3-d]pyrimidine (300 mg, from last step) in DMSO (20 mL) was added KF (300 mg, 5.35 mmol) and (R)-1-(3-(1-aminoethyl)-2-fluorophenyl)-1,1-difluoro-2-methylpropan-2-ol (100 mg, 0.405 mmol). The mixture was heated to 100° C. for 1 hour. It was cooled down to room temperature and was extracted with ethyl acetate, and saturated NaHCO₃ solution. The organics were combined, washed with brine, and dried over Na₂SO₄. It was filtered, and solvent was removed under reduced pressure to give a residue. The residue was purified by flash column chromatography on silica gel to provide the desired product ESI-MS m/z: 551.2 [M+H]⁺.

(R)—N-(1-(3,3-difluoro-2,2-dimethyl-2,3-dihydrobenzofuran-7-yl)ethyl)-6-(4-isopropylpiperazin-1-yl)-2-methyl-7-(oxetan-3-ylmethoxy)pyrido[2,3-d]pyrimidin-4-amine To a solution of oxetan-3-ylmethanol (100 mg, 1.136 mmol) in MeCN (10 mL) was added NaH (200 mg, 5 mmol), and the mixture was stirred for 30 min at rt. Then (R)-1-(3-(1-((7-chloro-6-(4-isopropylpiperazin-1-yl)-2-methylpyrido[2,3-d]pyrimidin-4-yl)amino)ethyl)-2-fluorophenyl)-1,1-difluoro-2-methylpropan-2-ol (30 mg, 0.054 mmol, in 2 mL THF) was added, and the resulting mixture was heated to 80° C. for 2 hours. It was cooled to room temperature and the solvent was removed. The residue was extracted with ethyl acetate and NaHCO$_3$(aq). The extracts were combined, washed with brine, and dried over Na$_2$SO$_4$. It was filtered and solvent was removed under reduced pressure to give a residue. The residue was purified by flash column chromatography on silica gel to afford the desired product ESI-MS m/z: 583.3 [M+H]$^+$. $^1$HNMR (400 MHz, MeOD): δ 8.12 (s, 1H), 7.51 (d, J=7.2 Hz, 1H), 7.37 (d, J=7.6 Hz, 1H), 7.01 (t, J=7.6 Hz, 1H), 5.76 (m, 1H), 4.93 (m, 2H), 4.73 (d, J=5.6 Hz, 2H), 4.68 (m, 2H), 4.6-4.4 (m, 2H), 3.7-3.3 (m, 8H), 2.46 (s, 3H), 1.67 (d, J=7.2 Hz, 3H), 1.55-1.4 (m, 6H), 1.4-1.35 (m, 6H).

Compound 333: Synthesis of 11-(7-chloro-4-(((R)-1-(3-((S)-1,1-difluoro-2-hydroxypropyl)-2-fluorophenyl)ethyl)amino)-2-methylpyrido[2,3-d]pyrimidin-6-yl)cyclopropane-1-carbonitrile

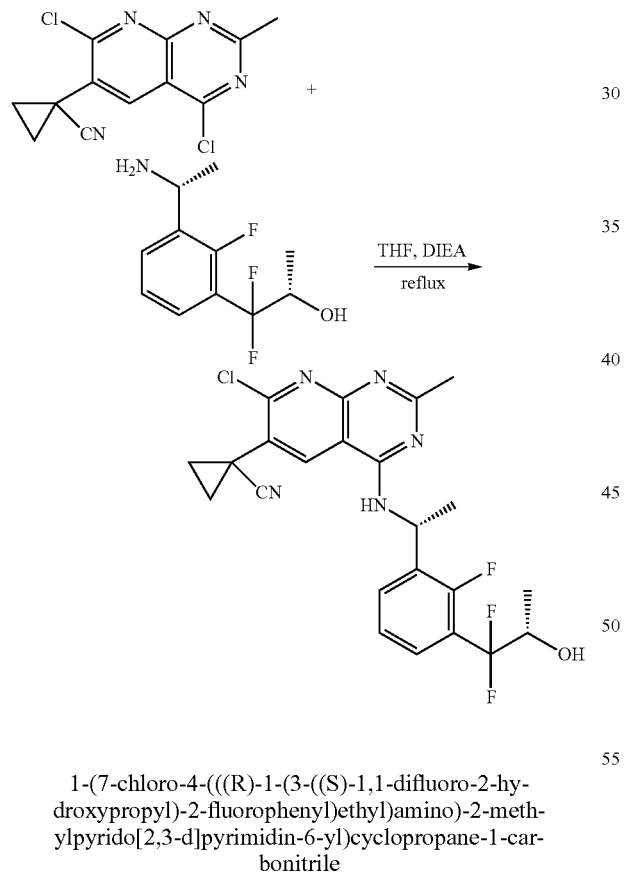

1-(7-chloro-4-(((R)-1-(3-((S)-1,1-difluoro-2-hydroxypropyl)-2-fluorophenyl)ethyl)amino)-2-methylpyrido[2,3-d]pyrimidin-6-yl)cyclopropane-1-carbonitrile To a solution of 1-(4,7-dichloro-2-methylpyrido[2,3-d]pyrimidin-6-yl)cyclopropane-1-carbonitrile (50 mg, 0.179 mmol) in THF (10 mL) and DIEA (1 mL) was added (S)-1-(3-((R)-1-aminoethyl)-2-fluorophenyl)-1,1-difluoropropan-2-ol (50 mg, 0.215 mmol). The resulting mixture was heated to 70° C. for 1 hour with stirring. It was cooled to room temperature and solvent was removed to give a crude. The crude was extracted with ethyl acetate and NaHCO$_{3(aq)}$. The organic extracts were combined, washed with brine, and dried over Na$_2$SO$_4$. It was filtered a nd solvent was removed under reduced pressure to give a residue. The residue was purified by flash column chromatography on silica gel to afford the desired product ESI-MS m/z: 476.2 [M+H]$^+$. $^1$H NMR (400 MHz, MeOD) 8.92 (s, 1H), 7.59 (t, J=6.8 Hz, 1H), 7.44 (t, J=7.2 Hz, 1H), 7.21 (t, J=7.6 Hz, 1H), 5.9-5.8 (m, 1H), 4.4-4.2 (m, 1H), 2.46 (s, 3H), 1.95-1.85 (m, 2H), 1.71 (d, J=7.2 Hz, 3H), 1.7-1.6 (m, 2H), 1.25 (d, J=6.5 Hz, 3H).

Compound 250: Synthesis of (R)-4-(4-((1-(3-(difluoromethyl)-2-fluorophenyl)ethyl)amino)-7-(2-(dimethylamino)ethoxy)-2-methylpyrido[2,3-d]pyrimidin-6-yl)-1-iminohexahydro-1l6-thiopyran 1-oxide

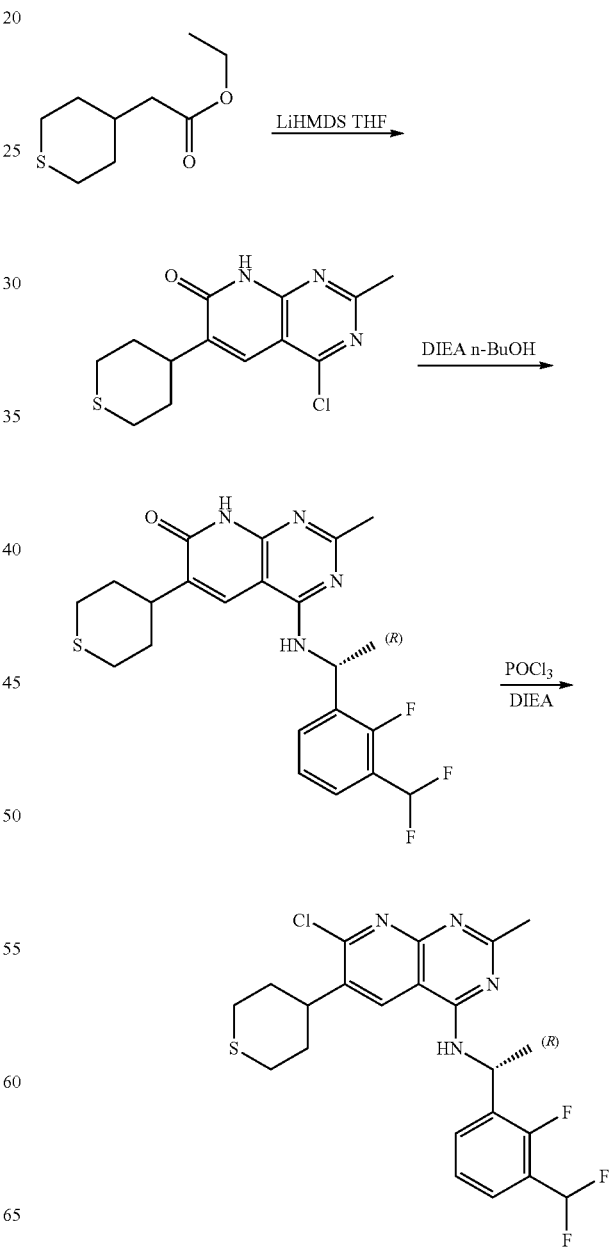

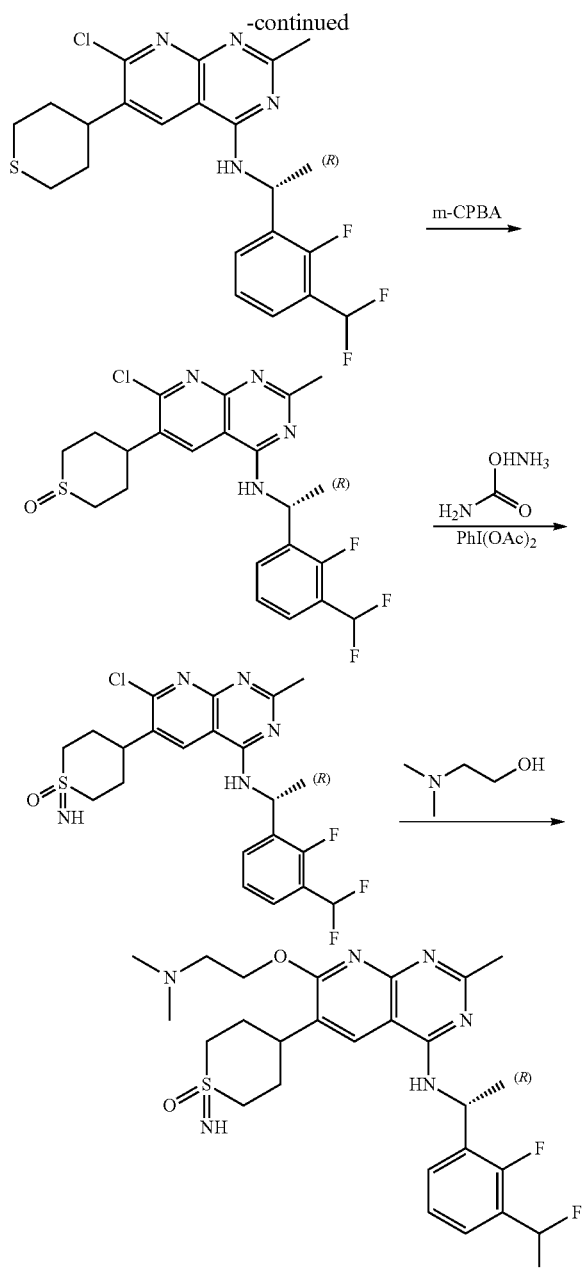

4-chloro-2-methyl-6-(tetrahydro-2H-thiopyran-4-yl)
pyrido[2,3-d]pyrimidin-7(8H)-one A solution of methylethyl 2-(tetrahydro-2H-thiopyran-4-yl)acetate (2.0 g, 10.64 mmol) in THF (1000 mL) was cooled to −78° C. under argon. LiHMDS (64 ml, 1 M in THF) was added dropwise and the resulting mixture was stirred for 2 h at −78° C. to −45° C. Then 4-amino-6-chloro-2-methylpyrimidine-5-carbaldehyde (1.83 g, 10.64 mmol) in THF (40 ml) was added dropwise at −78° C. The mixture was stirred at −78° C. and allowed to warm gradually to room temperature overnight. It was quenched with saturated NH$_4$Cl (40 mL). The mixture was extracted with ethyl acetate (60 mL×2). Organic extracts were combined, washed with brine, and dried over Na$_2$SO$_4$. It was filtered and solvent was removed under reduced pressure to give a crude.

The crude was purified by flash chromatography on silica gel (dichloromethane:methyl alcohol=98:2) to afford the desired product. ESI-MS m/z: 296 [M+H]$^+$.

4-((1-(3-(difluoromethyl)-2-fluorophenyl)ethyl)amino)-2-methyl-6-(tetrahydro-2H-thiopyran-4-yl)pyrido[2,3-d]pyrimidin-7(8H)-one To a solution of 4-chloro-2-methyl-6-(tetrahydro-2H-thiopyran-4-yl)pyrido[2,3-d]pyrimidin-7(8H)-one (2.19 g, 7.42 mmol) and (R)-1-(3-(difluoromethyl)-2-fluorophenyl)ethan-1-amine hydrochloride (2.18 g, 9.65 mmol) in n-BuOH (50 mL) was added DIEA (11.8 g, 96.5 mmol). The resulting mixture was heated at 130° C. under argon and stirred for overnight. It was cooled to room temperature and ethyl acetate (100 mL) was added. The organics were washed with brine, dried over Na$_2$SO$_4$. It was filtered and solvent was removed under reduced pressure to give a crude. The crude was purified by flash chromatography on silica gel (dichloromethane:methyl alcohol=95:5) to afford the desired product ESI-MS m/z: 449[M+H]$^+$;

7-chloro-N-(1-(3-(difluoromethyl)-2-fluorophenyl)ethyl)-2-methyl-6-(tetrahydro-2H-thiopyran-4-yl)pyrido[2,3-d]pyrimidin-4-amine To a mixture of (R)-4-((1-(3-(difluoromethyl)-2-fluorophenyl)ethyl)amino)-2-methyl-6-(tetrahydro-2H-thiopyran-4-yl)pyrido[2,3-d]pyrimidin-7(8H)-one (2.81 g, 6.27 mmol) in POCl$_3$ (60 ml) was added DIEA (1.42 g, 11.60 mmol). The resulting mixture was heated at 100° C. under argon and stirred for overnight. Then it was cooled to RT and concentrated to remove most POCl$_3$. The resulted residue was partitioned between saturated NaHCO$_3$ (5 mL) and dichloromethane (20 mL). It was extracted with dichloromethane (60 mL×2). The organics were combined, washed with brine, and dried over Na$_2$SO$_4$. It was filtered and solvent was removed under reduced pressure to give a crude ESI-MS m/z: 467[M+H]$^+$;

4-(7-chloro-4-((1-(3-(difluoromethyl)-2-fluorophenyl)ethyl)amino)-2-methylpyrido[2,3-d]pyrimidin-6-yl)tetrahydro-2H-thiopyran 1-oxide To a solution of (R)-7-chloro-N-(1-(3-(difluoromethyl)-2-fluorophenyl)ethyl)-2-methyl-6-(tetrahydro-2H-thiopyran-4-yl)pyrido[2,3-d]pyrimidin-4-amine (500 mg, 1.073 mmol) was added m-CPBA (180 mg, 1.609 mmol) in DCM (30 mL). The resulting mixture was stirred for 3 hours. It was filtered and solvent was removed under reduced pressure to give a crude. The crude was purified by flash chromatography on silica gel (dichloromethane:methyl alcohol=95:5) to afford the desired product ESI-MS m/z: 483 [M+H]$^+$;

4-(7-chloro-4-((1-(3-(difluoromethyl)-2-fluorophenyl)ethyl)amino)-2-methylpyrido[2,3-d]pyrimidin-6-yl)-1-iminohexahydro-1l6-thiopyran 1-oxide To a solution of (R)-4-(7-chloro-4-((1-(3-(difluoromethyl)-2-fluorophenyl)ethyl)amino)-2-methylpyrido[2,3-d]pyrimidin-6-yl)tetrahydro-2H-thiopyran 1-oxide (50 mg, 0.1073 mmol) in methanol (10 mL) was added carbamic acid, ammonia salt (50 mg, 0.64 mmol) and PhI(OAc)$_2$ (50 mg, 0.155 mmol). The resulting mixture was stirred for 3 hours. It was filtered and solvent was removed under reduced pressure to give a crude. The crude was purified by flash chromatography on silica gel (dichloromethane:methyl alcohol=95:5) to afford the desired product. ESI-MS m/z: 498[M+H]$^+$;

(R)-4-(4-((1-(3-(difluoromethyl)-2-fluorophenyl) ethyl)amino)-7-(2-(dimethylamino)ethoxy)-2-methylpyrido[2,3-d]pyrimidin-6-yl)-1-iminohexahydro-1l6-thiopyran 1-oxide To a solution of (R)-4-(7-chloro-4-((1-(3-(difluoromethyl)-2-fluorophenyl)ethyl)amino)-2-methylpyrido[2,3-d] pyrimidin-6-yl)-1-iminohexahydro-1l6-thiopyran 1-oxide (48 mg, 0.096 mmol) and 2-(dimethylamino)ethan-1-ol (26 mg, 0.29 mmol) in MeCN (10 mL) was added NaH (12 mg, 0.96 mmol). The resulting mixture was heated at 100° C. under argon and stirred for 4 h. It was cooled to room temperature and filtered. Solvent was removed under reduced pressure to give a crude. The crude was purified by flash chromatography on silica gel (dichloromethane methyl alcohol=95:5) to afford the desired product ESI-MS m/z: 551[M+H]$^+$; $^1$HNMR (400 MHz, MeOD): δ 8.65 (s, 1H), 7.66-7.62 (t, J=7.2 Hz, 1H), 7.49-7.46 (t, J=7.2 Hz, 1H), 7.26-7.22 (t, J=7.6 Hz, 1H), 7.13-6.86 (t, J=54.8 Hz, 1H), 5.88-5.83 (m, 1H), 4.88-4.85 (m, 2H), 3.65-3.53 (m, 5H), 3.38-3.35 (m, 2H), 3.31 (s, 3H), 2.97 (s, 6H), 2.35-2.45 (m, 2H), 2.29-2.25 (m, 2H), 1.71-1.69 (d, J=6.8 Hz, 3H).

Compound 327: 1-(4-(((R)-1-(3-((S)-1,1-difluoro-2-hydroxypropyl)-2-fluorophenyl)ethyl)amino)-7-methoxypyrido[2,3-d]pyrimidin-6-yl)cyclopropane-1-carbonitrile

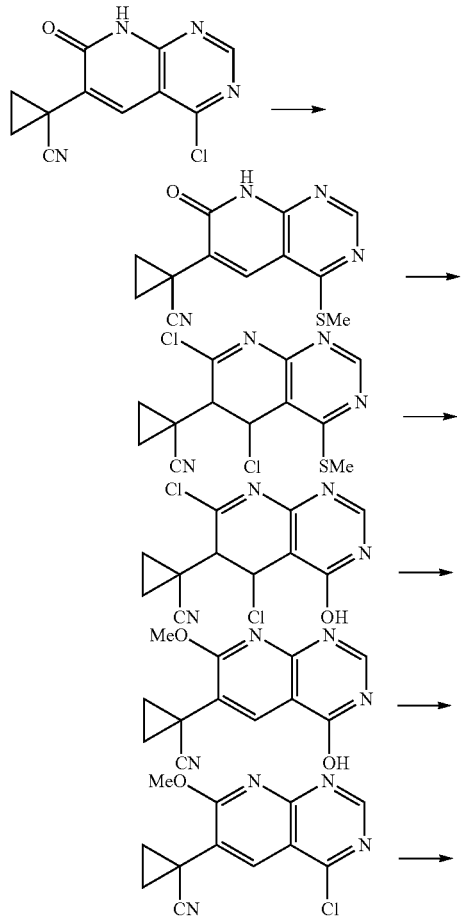

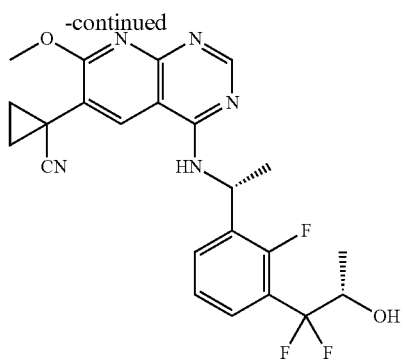

(4-(methylthio)-7-oxo-7,8-dihydropyrido[2,3-d]pyrimidin-6-yl)cyclopropane-1-carbonitrile To a solution of 1-(4-chloro-7-oxo-7,8-dihydropyrido[2,3-d]pyrimidin-6-yl)cyclopropane-1-carbonitrile (2.47 g, 10.0 mmol) in THF (25 mL) was added sodium methanethiolate (4 mL, 1 M in H$_2$O). The mixture was stirred at 60° C. for 3 h. The pH of the mixture was adjusted to 7-8 with NaHCO$_3$ solution. The mixture was extracted with ethyl acetate (50 mL×3). Organic extracts were combined, washed with brine, and dried over Na$_2$SO$_4$. It was filtered and solvent was removed under reduced pressure to give a crude which was used directly in the next step without further purification. ESI-MS m/z: 259 [M+H]$^+$.

1-(5,7-dichloro-4-(methylthio)-5,6-dihydropyrido[2,3-d]pyrimidin-6-yl)cyclopropane-1-carbonitrile A mixture of 1-(4-(methylthio)-7-oxo-7,8-dihydropyrido[2,3-d]pyrimidin-6-yl)cyclopropane-1-carbonitrile (6.16 g, 23.89 mmol) in POCl$_3$ (50 mL) was heated to 105° C. and stirred for 3 h. It was cooled to room temperature and the solvent was removed under reduced pressure to give a residue. It was quenched saturated H$_2$O (20 mL). The mixture was extracted with ethyl acetate (50 mL×3). The organic extracts were combined, washed with brine, and dried over Na$_2$SO$_4$. It was filtered and solvent was removed under reduced pressure to give a crude ESI-MS m/z: 313 [M+H]$^+$.

1-(5,7-dichloro-4-hydroxy-5,6-dihydropyrido[2,3-d] pyrimidin-6-yl)cyclopropane-1-carbonitrile To a solution of 1-(5,7-dichloro-4-(methylthio)-5,6-dihydropyrido[2,3-d]pyrimidin-6-yl)cyclopropane-1-carbonitrile (5.5 g, 17.6 mmol) in DCM (100 mL) was added m-CPBA (15.2 g, 88.1 mmol). The mixture was stirred for 16 h. The solvent was removed under reduced pressure to give a crude. The crude was purified by flash chromatography on silica gel (petroleum:ethyl acetate=80:20, dichloromethane:methyl alcohol=41:2) to afford the desired product ESI-MS m/z: 283 [M+H]$^+$.

1-(4-hydroxy-7-methoxypyrido[2,3-d]pyrimidin-6-yl)cyclopropane-1-carbonitrile

To a mixture of NaH (700 mg, 48.6 mmol) in MeOH (60 mL), sodium methanolate (3.3 g, 61.6 mmol) and 1-(5,7-dichloro-4-hydroxy-5,6-dihydropyrido[2,3-d]pyrimidin-6-yl)cyclopropane-1-carbonitrile (3.3 g, 11.7 mmol) was added. The mixture was stirred at 60° C. for 3 h. The solvent was removed under reduced pressure to give a crude. The crude was purified by flash chromatography on silica gel (dichloromethane:methyl alcohol=41:2) to afford the desired product ESI-MS m/z: 243 [M+H]$^+$.

(4-chloro-7-methoxypyrido[2,3-d]pyrimidin-6-yl) cyclopropane-1-carbonitrile

To a solution of 1-(4-hydroxy-7-methoxypyrido[2,3-d] pyrimidin-6-yl)cyclopropane-1-carbonitrile (800 mg, 3.306 mol) in sulfurous dichloride (15 mL) was added DMF (two drops). The mixture was stirred at 85° C. for 4 h. The solvent was removed under reduced pressure to afford the desired product which was used in the next step directly without further purification. ESI-MS m/z: 261 [M+H]$^+$.

1-(4-(((R)-1-(3-((S)-1,1-difluoro-2-hydroxypropyl)-2-fluorophenyl)ethyl)amino)-7-methoxypyrido[2,3-d]pyrimidin-6-yl)cyclopropane-1-carbonitrile To a solution of 1-(4-chloro-7-methoxypyrido[2,3-d]pyrimidin-6-yl)cyclopropane-1-carbonitrile (150 mg, 0.577 mol) and (S)-1-(3-((R)-1-aminoethyl)-2-fluorophenyl)-1,1-difluoropropan-2-ol (170 mg, 0.635 mmol) in n-BuOH (20 mL) was added DIEA (1.42 g, 11.60 mmol). The resulting mixture was heated at 125° C. under argon and stirred for 2 hours. It was cooled to room temperature and ethyl acetate (60 mL) was added. The organics were washed with brine, dried over Na$_2$SO$_4$. It was filtered and solvent was removed under reduced pressure to give a crude. The crude was purified by flash chromatography on silica gel (dichloromethane:methyl alcohol=97:3) to afford the desired product ESI-MS m/z: 458 [M+H]$^+$; $^1$HNMR (DMSO-d6,400 MHz): 8.79 (s, 1H), 8.56-8.54 (d, J=7.2 Hz, 1H), 8.45 (s, 1H), 7.62-7.59 (t, J=6.4 Hz, 1H), 7.41-7.37 (t, J=6.4 Hz, 1H), 7.26-7.22 (t, J=7.6 Hz, 1H), 5.77-5.74 (m, 1H), 5.57-5.56 (d, J=6.4 Hz, 1H), 4.22-4.17 (m, 1H), 4.10 (s, 3H), 1.76 (m, 2H), 1.61-1.59 (d, J=7.2 Hz, 3H), 1.52 (m, 2H), 1.18-1.16 (m, 3H).

Compound 419: Synthesis of (R)—N-(1-(3-(difluoro(1-isopropylpiperidin-4-yl)methyl)phenyl) ethyl)-6-(1-isopropylpiperidin-4-yl)-7-methoxypyrido[2,3-d]pyrimidin-4-amine

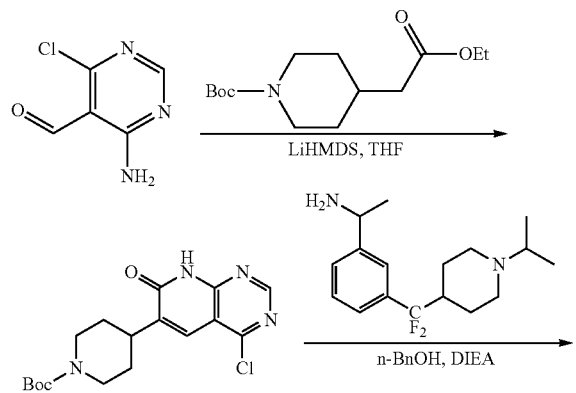

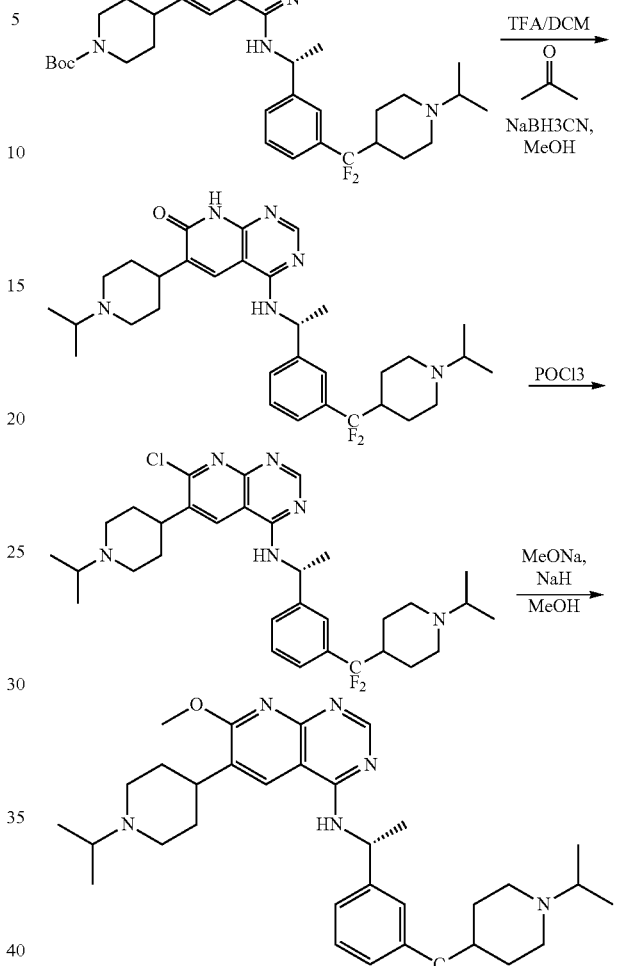

tert-butyl 4-(4-chloro-7-oxo-7,8-dihydropyrido[2,3-d]pyrimidin-6-yl)piperidine-1-carboxylate To a mixture of tert-butyl 4-(2-ethoxy-2-oxoethyl)piperidine-1-carboxylate (5.2 g, 19.1 mmol) in THF (30 mL) was added LiHMDS (51 mL, 50.8 mmol, 1 M in THF) slowly at −78° C. The mixture was stirred at −30° C. for 1 h. 4-amino-6-chloropyrimidine-5-carbaldehyde (2 g, 12.7 mmol) was added and the mixture was stirred for another 16 h at room temperature. It was extracted with ethyl acetate and washed with brine. The organics were dried over Na$_2$SO$_4$. It was filtered and solvent was removed under reduced pressure to give a residue. The residue was purified by column chromatography on silica gel (ethyl acetate/petroleum=1/2,1/1) to afford the desired product as a white solid tert-butyl (R)-4-(4-((1-(3-(difluoro(1-isopropylpiperidin-4-yl)methyl)phenyl)ethyl)amino)-7-oxo-7,8-dihydropyrido[2,3-d]pyrimidin-6-yl)piperidine-1-carboxylate A mixture of tert-butyl 4-(4-chloro-7-oxo-7,8-dihydropyrido[2,3-d]pyrimidin-6-yl)piperidine-1-carboxylate (1 g, 2.73 mmol), (R)-1-(3-(difluoro(1-isopropylpiperidin-4-yl) methyl)phenyl)ethan-1-amine (971 mg, 3.28 mmol) and in n-BnOH (20 mL) was added DIEA (1.4 mL, 8.19 mmol). The mixture was stirred at 120° C. under argon for 3 h. The mixture was allowed to cool to room temperature and concentrated in vacuo. The residue was purified by column chromatography on silica gel (MeOH/DCM=2/25) to afford the desired product (R)-4-((1-(3-(difluoro(1-isopropylpiperidin-4-yl) methyl)phenyl)ethyl)amino)-6-(1-isopropylpiperidin-4-yl)pyrido[2,3-d]pyrimidin-7(8H)-one To a solution of tert-butyl tert-butyl (R)-4-(4-((1-(3-(difluoro(1-isopropylpiperidin-4-yl)methyl)phenyl)ethyl) amino)-7-oxo-7,8-dihydropyrido[2,3-d]pyrimidin-6-yl)piperidine-1-carboxylate (2.1 g, 3.37 mmol) in DCM (6 ml) was added TFA (1.5 ml) at room temperature. The mixture was stirred for 1 h. It was concentrated in vacuo to afford the crude product without further purification which was used in the next step. The above mentioned crude was added to a mixture of AcOH (0.2 mL), NaBH3CN (1.1 g, 16.9 mmol) and acetone (586 mg, 10.1 mmol) in MeOH (10 mL). The resulting mixture was stirred at 60° C. for 3 h. It was then quenched with saturated NaHCO₃ solution, and then extracted with ethyl acetate. The organic extracts was combined, washed with saturated NaHCO₃ solution and brine, and dried over Na₂SO₄. It was filtered and solvent was removed under reduced pressure to give a crude. The crude was purified by column chromatography on silica gel (MeOH/DCM=1/20,1/10) to give the product.

(R)-7-chloro-N-(1-(3-(difluoro(1-isopropylpiperidin-4-yl)methyl)phenyl)ethyl)-6-(1-isopropylpiperidin-4-yl)pyrido[2,3-d]pyrimidin-4-amine To a mixture of (R)-4-((1-(3-(difluoro(1-isopropylpiperidin-4-yl)methyl)phenyl)ethyl)amino)-6-(1-isopropylpiperidin-4-yl)pyrido[2,3-d]pyrimidin-7(8H)-one (800 mg, 1.37 mmol) in POCl₃ (15 ml was stirred at 105° C. for 1 h. It was concentrated in vacuo to afford the crude product without further purification which was used directly in the next step.

(R)—N-(1-(3-(difluoro(1-isopropylpiperidin-4-yl) methyl)phenyl)ethyl)-6-(1-isopropylpiperidin-4-yl)-7-methoxypyrido[2,3-d]pyrimidin-4-amine To a solution of (R)-7-chloro-N-(1-(3-(difluoro(1-isopropylpiperidin-4-yl)methyl)phenyl)ethyl)-6-(1-isopropylpiperidin-4-yl)pyrido[2,3-d]pyrimidin-4-amine (341 mg, 0.58 mmol) in methanol (10 mL) was added MeONa (158 mg, 29.2 mmol). Then NaH (117 mg, 29.2 mmol, 60%) was added and the mixture was stirred at 60° C. for 3 h. It was extracted with ethyl acetate and washed with brine. The organics were combined and dried over Na₂SO₄. It was filtered and solvent was removed under reduced pressure to give a residue. The residue was purified by column chromatography on silica gel (MeOH/DCM=1/10) to afford the desired product ESI-MS m/z: 581.57 [M+H]⁺. ¹HNMR (MeOD: 400 MHz): δ 8.34 (s, 1H), 8.29 (s, 1H), 7.45-7.43 (d, J=7.2 Hz, 1H), 7.39 (s, 1H), 7.33-7.29 (t, J=7.6 Hz, 1H), 7.21-7.19 (d, J=8 Hz, 1H), 5.53-5.51 (m, 1H), 3.98 (s, 3H), 3.05-3.02 (m, 2H), 2.89-2.78 (m, 4H), 2.63-2.59 (m, 1H), 2.40-2.35 (m, 2H), 2.06-1.99 (m, 2H), 1.92-1.88 (m, 3H), 1.80-1.73 (m, 2H), 1.60-1.51 (m, 5H), 1.35-1.27 (m, 2H), 1.08-1.06 (d, J=6.4 Hz, 6H), 0.94-0.92 (d, J=6.4 Hz, 6H).

Compound 332: Synthesis of 1-(4-(((R)-1-(3-((R)-1,1-difluoro-2-hydroxypropyl)-2-fluorophenyl)ethyl) amino)-7-methoxy-2-methylpyrido[2,3-d]pyrimidin-6-yl)cyclopropane-1-carbonitrile

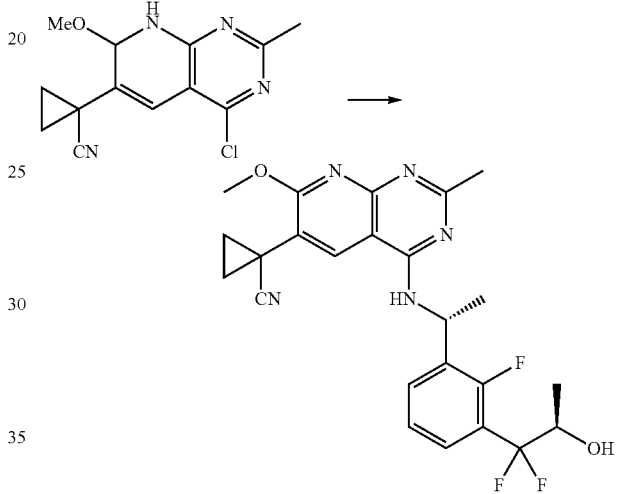

1-(4-(((R)-1-(3-((S)-1,1-difluoro-2-hydroxypropyl)-2-fluorophenyl)ethyl)amino)-7-methoxy-2-methylpyrido[2,3-d]pyrimidin-6-yl)cyclopropane-1-carbonitrile To a solution of 1-(4-chloro-7-methoxy-2-methylpyrido [2,3-d]pyrimidin-6-yl)cyclopropane-1-carbonitrile (110 mg, 0.4 mmol) and (R)-1-(3-((R)-1-aminoethyl)-2-fluorophenyl)-1,1-difluoropropan-2-ol (94 mg, 0.4 mmol) in n-BuOH (15 mL) was added DIEA (260 mg, 2.0 mmol). The resulting mixture was heated at 120° C. under argon and stirred for 4 h. It was cooled to room temperature and ethyl acetate (20 mL) was added. The organics were washed with brine, dried over Na2SO4. It was filtered and solvent was removed under reduced pressure to give a crude. The crude was purified by flash chromatography on silica gel (dichloromethane:methyl alcohol=20:1) to afford the desired product as a white solid. ESI-MS m/z: 472[M+H]⁺; ¹HNMR (400 MHz, DMSO-d6): δ 8.70 (s, 1H), 8.47-8.45 (d, J=6.8 Hz, 1H), 7.62-7.58 (t, J=6.8 Hz, 1H), 7.39-7.35 (t, J=6.8 Hz, 1H), 7.25-7.21 (t, J=7.6 Hz, 1H), 5.75-5.71 (m, 1H), 5.59-5.58 (d, J=6 Hz, 1H), 4.24-4.18 (m, 1H), 4.06 (s, 3H), 2.33 (s, 3H), 1.73-1.73 (m, 2H), 1.60-1.58 (d, J=7.2 Hz, 3H), 1.51-1.49 (m, 2H), 1.15-1.14 (d, J=6 Hz, 3H).

Compound 168: Synthesis of (R)-2-(azetidin-1-yl)-N-(1-(3-(difluoromethyl)-2-fluorophenyl)ethyl)-6-(4-isopropylpiperazin-1-yl)-7-methoxypyrido[2,3-d]pyrimidin-4-amine

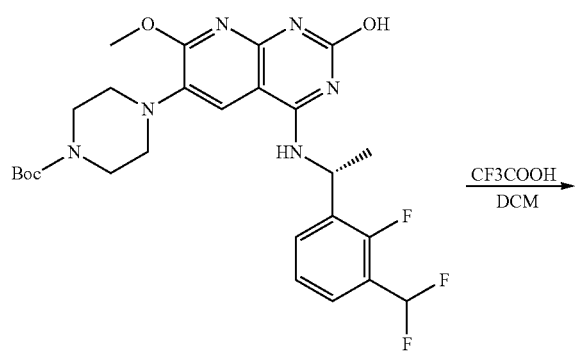

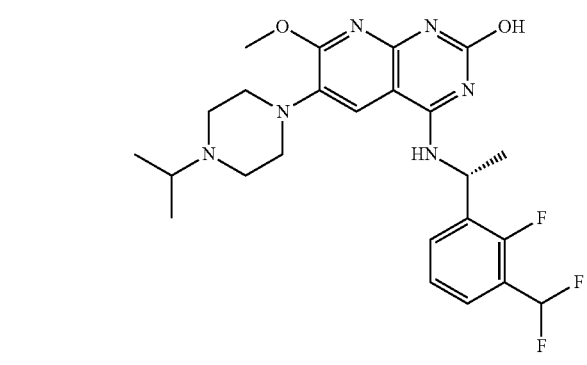

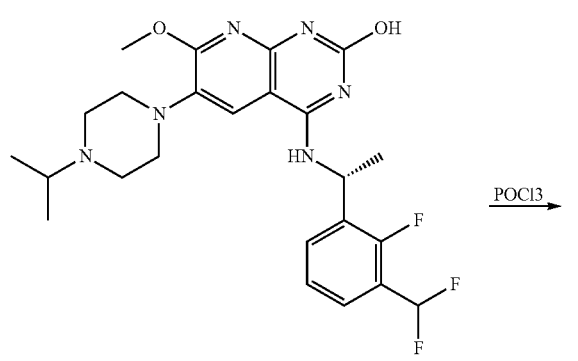

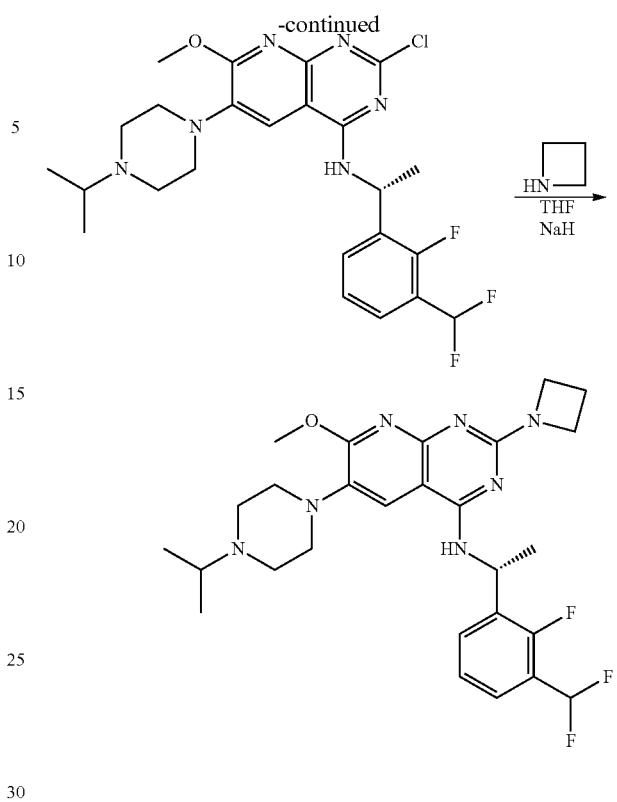

(R)-4-((1-(3-(difluoromethyl)-2-fluorophenyl)amino)-7-methoxy-6-(piperazin-1-yl)pyrido[2,3-d]pyrimidin-2-ol A solution of tert-butyl (R)-4-(4-((1-(3-(difluoromethyl)-2-fluorophenyl)ethyl)amino)-2-hydroxy-7-methoxypyrido[2,3-d]pyrimidin-6-yl)piperazine-1-carboxylate (150.0 mg, 0.274 mmol) in DCM (10 mL) was added TFA (2 mL). The mixture was stirred for 2 h at room temperature. Saturated sodium bicarbonate solution (20 ml) was added. The aqueous layer was extracted with DCM (20 mL×2). The organics were combined, washed with brine, and dried over Na$_2$SO$_4$. It was filtered and solvent was removed under reduced pressure to give the desired product as a solid which was used directly in the next step without further purification. ESI-MS m/z: 449[M+H]$^+$ (R)-4-((1-(3-(difluoromethyl)-2-fluorophenyl)ethyl)amino)-6-(4-isopropylpiperazin-1-yl)-7-methoxy-pyrido[2,3-d]pyrimidin-2-ol A solution of (R)-4-((1-(3-(difluoromethyl)-2-fluorophenyl)ethyl)amino)-7-methoxy-6-(piperazin-1-yl)pyrido[2,3-d]pyrimidin-2-ol (102 mg, 0.228 mmol) in DCM (10 mL), acetone (26 mg, 0.454 mmol) and two drops of HOAc were added. The mixture was stirred for 10 min at RT and NaBH$_3$CN (71 mg, 5 mmol) was added to the solution. The mixture was stirred overnight at RT under argon. The reaction was quenched with water. The aqueous layer was extracted with DCM (20 mL×2). The organics were washed with brine, dried over Na$_2$SO$_4$. It was filtered and solvent was removed under reduced pressure to give a crude. The crude was purified by flash chromatography on silica gel (dichloromethane:methyl alcohol=10:2) to afford the desired product as a solid. ESI-MS m/z: 491 [M+H]$^+$

993

(R)-2-chloro-N-(1-(3-(difluoromethyl)-2-fluorophenyl)ethyl)-6-(4-isopropylpiperazin-1-yl)-7-methoxypyrido[2,3-d]pyrimidin-4-amine A mixture of (R)-4-((1-(3-(difluoromethyl)-2-fluorophenyl)ethyl)amino)-6-(4-isopropylpiperazin-1-yl)-7-methoxypyrido[2,3-d]pyrimidin-2-ol (50 mg, 0.102 mmol) in POCl$_3$ (10 ml) was stirred at 105° C. for 1.5 h. It was cooled to room temperature and most of POCl$_3$ was removed under reduced pressure. The resulted residue was partitioned between saturated NaHCO$_3$ (20 ml) and dichloromethane (20 mL). The aqueous layer was extracted with dichloromethane (20 mL×2). The organics were combined, washed with brine, and dried over Na$_2$SO$_4$. It was filtered and solvent was removed under reduced pressure to give the desired product as a solid which was used in the next step without further purification. ESI-MS m/z: 509[M+H]+.

(R)-2-(azetidin-1-yl)-N-(1-(3-(difluoromethyl)-2-fluorophenyl)ethyl)-6-(4-isopropylpiperazin-1-yl)-7-methoxypyrido[2,3-d]pyrimidin-4-amine A solution of azetidine (5.8 mg, 0.103 mmol) in THF (10 mL) was added NaH (12.4 mg, 0.309 mmol) and stirred for 30 min at RT. (R)-2-chloro-N-(1-(3-(difluoromethyl)-2-fluorophenyl)ethyl)-6-(4-isopropylpiperazin-1-yl)-7-methoxypyrido[2,3-d]pyrimidin-4-amine (35 mg, 0.0689 mmol) was added to the solution. The mixture was stirred overnight at RT. The reaction was quenched with water. The aqueous layer was extracted with DCM (10 mL×2). The organics were combined, washed with brine, dried over Na$_2$SO$_4$. It was filtered and solvent was removed under reduced pressure to give a crude. The crude was purified by flash chromatography on silica gel (dichloromethane:methyl alcohol=10:2) to afford the desired product ESI-MS m/z: 530[M+H]$^+$, $^1$HNMR (CD3OD, 400 MHz): δ 8.00 (s, 1H), 7.52 (m, 1H), 7.37 (m, 1H), 7.16 (m, 1H), 6.89 (t, J=54.8 Hz, 1H), 5.57 (m, 1H), 4.15-4.05 (m, 2H), 3.99 (m, 5H), 3.25 (m, 5H), 3.18-3.08 (m, 4H), 2.29-2.20 (m, 2H), 1.59 (d, J=7.1 Hz, 3H), 1.26-1.24 (m, 6H).

Compound 342: Synthesis of (R)-4-(4-((1-(3-(difluoromethyl)-2-fluorophenyl)ethyl)amino)-7-methoxypyrido[2,3-d]pyrimidin-6-yl)tetrahydro-2H-thiopyran-4-carbonitrile 1,1-dioxide

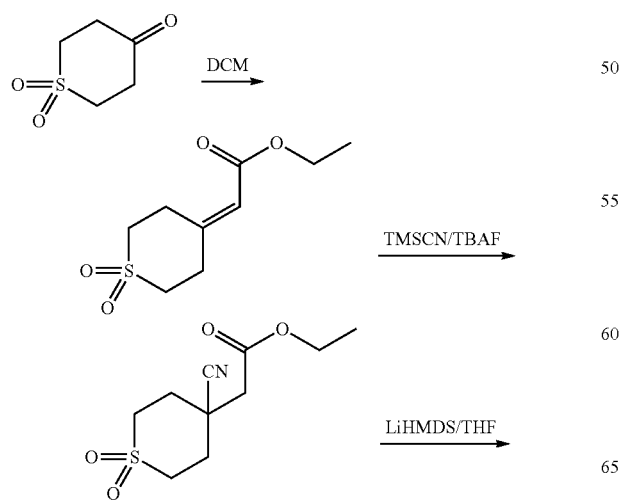

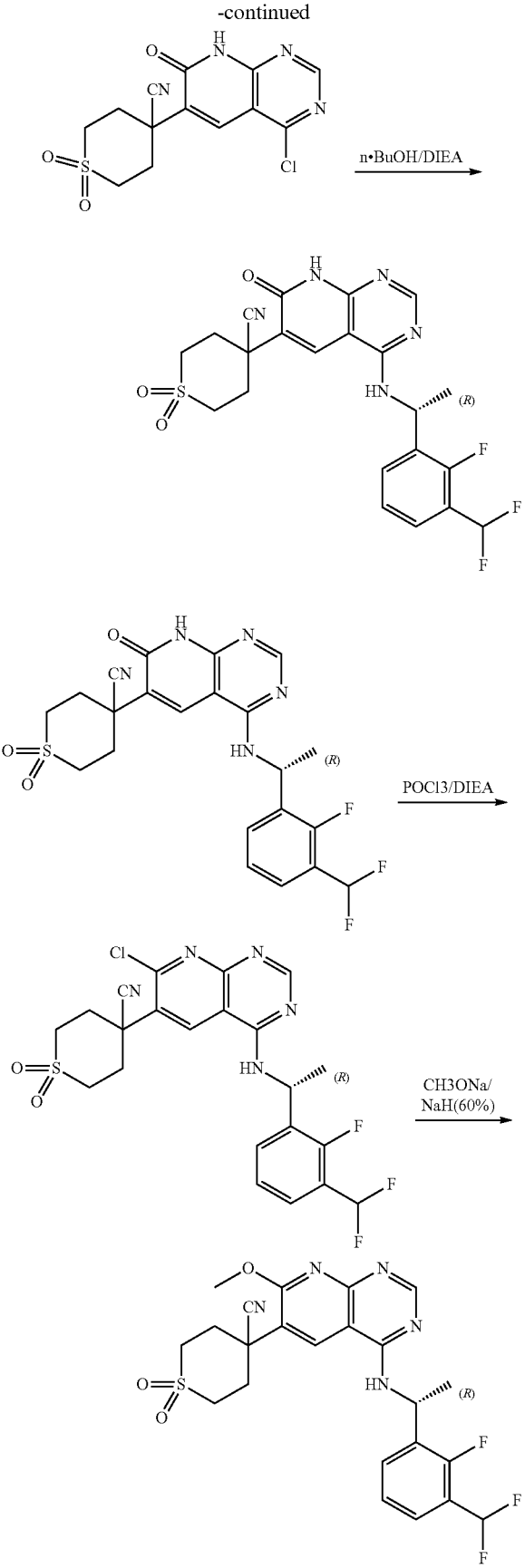

ethyl 2-(1,1-dioxidotetrahydro-4H-thiopyran-4-ylidene)acetate

A solution of tetrahydro-4H-thiopyran-4-one 1,1-dioxide (1.0 g, 6.75 mol) and ethyl (triphenylphosphoranylidene) acetate (3.5 g, 10.10 mol) in DCM (20 mL) was stirred for 16 hours at 50° C. under argon. Solvent was removed under reduced pressure to give a crude. The crude purified by flash chromatography on silica gel (petroleum:ethyl acetate=67:33) to give the desired product as a solid. ESI-MS m/z: 219 [M+H]$^+$.

ethyl 2-(4-cyano-1,1-dioxidotetrahydro-2H-thiopyran-4-yl)acetate

A solution of TMSCN (1.2 g, 12.10 mmol) was added into TBAF (1.0 M in THF, 4.7 ml, 18.11 mmol) at room temperature. The mixture was stirred for 0.5 hours at room temperature under argon. Then ethyl 2-(1,1-dioxidotetrahydro-4H-thiopyran-4-ylidene)acetate (880 mg, 4.03 mmol) was added. The mixture was stirred for 16 hours at room temperature under argon. It was quenched with water and extracted with ethyl acetate (30 mL×2). The organic extracts were combined, washed with water, brine, and dried over Na$_2$SO$_4$. The mixture was removed under reduced pressure to give a crude. The crude was purified by flash chromatography on silica gel (petroleum:ethyl acetate=71:29) to give the desired product as a solid. ESI-MS m/z: 246 [M+H]$^+$.

4-(4-chloro-7-oxo-7,8-dihydropyrido[2,3-d]pyrimidin-6-yl)tetrahydro-2H-thiopyran-4-carbonitrile 1,1-dioxide A solution of ethyl 2-(4-cyano-1,1-dioxidotetrahydro-2H-thiopyran-4-yl)acetate (300 mg, 1.23 mmol) in THF (10 mL) and 4-amino-6-chloropyrimidine-5-carbalddede (145 mg, 0.95 mmol) was cooled to −78° C. under argon. LiHMDS (3.7 ml, 1 M in THF) was added dropwise and the resulting mixture was stirred for 5.0 hours at −78° C. and allowed to warm RT. The reaction mixture was quenched saturated NH$_4$Cl (20 mL) and extracted with ethyl acetate (30 mL×2). Organic extracts were combined, washed with brine, and dried over Na$_2$SO$_4$. It was filtered and solvent was removed under reduced pressure to give a crude. The crude was purified by flash chromatography on silica gel (dichloromethane:methyl alcohol=96:4) to give the desired product as a solid. ESI-MS m/z: 337 [M+H]+.

(R)-4-(4-((1-(3-(difluoromethyl)-2-fluorophenyl)ethyl)amino)-7-oxo-7,8-dihydropyrido[2,3-d]pyrimidin-6-yl)tetrahydro-2H-thiopyran-4-carbonitrile 1,1-dioxide To a solution of 4-(4-chloro-7-oxo-7,8-dihydropyrido[2,3-d]pyrimidin-6-yl)tetrahydro-2H-thiopyran-4-carbonitrile 1,1-dioxide (60 mg, 0.18 mmol) and (R)-1-(3-(difluoromethyl)-2-fluorophenyl)ethan-1-amine hydrochloride (41 mg, 0.18 mmol) in n-BuOH (10 ml) was added DIEA (230 mg, 1.8 mmol). The resulting mixture was heated at 120° C. under argon and stirred for overnight. It was cooled to room temperature and ethyl acetate (60 mL) was added. The organics were separated, washed with brine, and dried over Na$_2$SO$_4$. It was filtered and solvent was removed under reduced pressure to give a crude. The crude was purified by flash chromatography on silica gel (dichloromethane:methyl alcohol=95:5) to afford the desired product as a solid. ESI-MS m/z: 492[M+H]$^+$;

(R)-4-(7-chloro-4-((1-(3-(difluoromethyl)-2-fluorophenyl)ethyl)amino)pyrido[2,3-d]pyrimidin-6-yl)tetrahydro-2H-thiopyran-4-carbonitrile 1,1-dioxide To a solution of (R)-4-(4-((1-(3-(difluoromethyl)-2-fluorophenyl)ethyl)amino)-7-oxo-7,8-dihydropyrido[2,3-d]pyrimidin-6-yl)tetrahydro-2H-thiopyran-4-carbonitrile 1,1-dioxide (50 mg, 0.11 mmol) in POCl$_3$ (5 mL) was added DIEA (cat) at room temperature. The resulting mixture was heated at 105° C. under argon and stirred for 5.0 h. Then it was cooled to room temperature and concentrated to remove most of POCl$_3$. The resulted residue was partitioned between Saturated NaHCO$_3$ (5 mL) and dichloromethane (20 mL). The aqueous layer was extracted with dichloromethane (20 mL×2). The organics were combined, washed with brine, and dried over Na$_2$SO$_4$. It was filtered and solvent was removed under reduced pressure to give a crude. The crude was purified by flash chromatography on silica gel (dichloromethane:methyl alcohol=95:5) to afford the desired product as a solid. ESI-MS m/z: 510[M+H]+;

(R)-4-(4-((1-(3-(difluoromethyl)-2-fluorophenyl)ethyl)amino)-7-methoxypyrido[2,3-d]pyrimidin-6-yl)tetrahydro-2H-thiopyran-4-carbonitrile 1,1-dioxide To a mixture of (R)-4-(7-chloro-4-((1-(3-(difluoromethyl)-2-fluorophenyl)ethyl)amino)pyrido[2,3-d]pyrimidin-6-yl)tetrahydro-2H-thiopyran-4-carbonitrile 1,1-dioxide (25 mg, 0.05 mmol) and sodium methanolate (14 mg, 0.25 mmol) in MeOH (10 mL) at 0° C. was added NaH (60%, 10 mg, 0.25 mmol). Then the resulting mixture was heated at 65° C. under argon and stirred for 2.0 hours. Then it was cooled to room temperature and concentrated to remove most of MeOH. The mixture was extracted with ethyl acetate (20 mL×2). Organic extracts were combined, washed with brine, and dried over Na$_2$SO$_4$. It was filtered and solvent was removed under reduced pressure to give a crude. The crude was purified by prep-TLC (dichloromethane:methyl alcohol=25:1) to afford the desired product as a solid. ESI-MS m/z: 506[M+H]$^+$. $^1$H NMR (400 MHz, DMSO-d6) δ: 8.78-8.77 (d, J=6.8 Hz, 1H), 8.74 (s, 1H), 8.49 (s, 1H), 7.67-7.63 (t, J=7.2 Hz, 1H), 7.53-7.50 (t, J=6.8 Hz, 1H), 7.29 (t, J=7.2 Hz), 7.24 (t, J=54 Hz, 1H), 5.81-5.75 (m, 1H), 4.10 (s, 3H), 3.55-3.52 (m, 2H), 3.42-3.35 (m, 2H), 2.91-2.87 (m, 2H), 2.66-2.59 (m, 2H), 1.63-1.61 (d, J=6.8 Hz, 3H).

Compound 186: Synthesis of (R)—N-(1-(3-(difluoromethyl)-2-fluorophenyl)ethyl)-6-(1-(difluoromethyl)cyclopropyl)-2-methyl-7-(oxetan-3-yloxy)pyrido[2,3-d]pyrimidin-4-amine

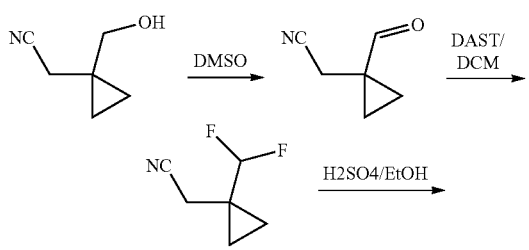

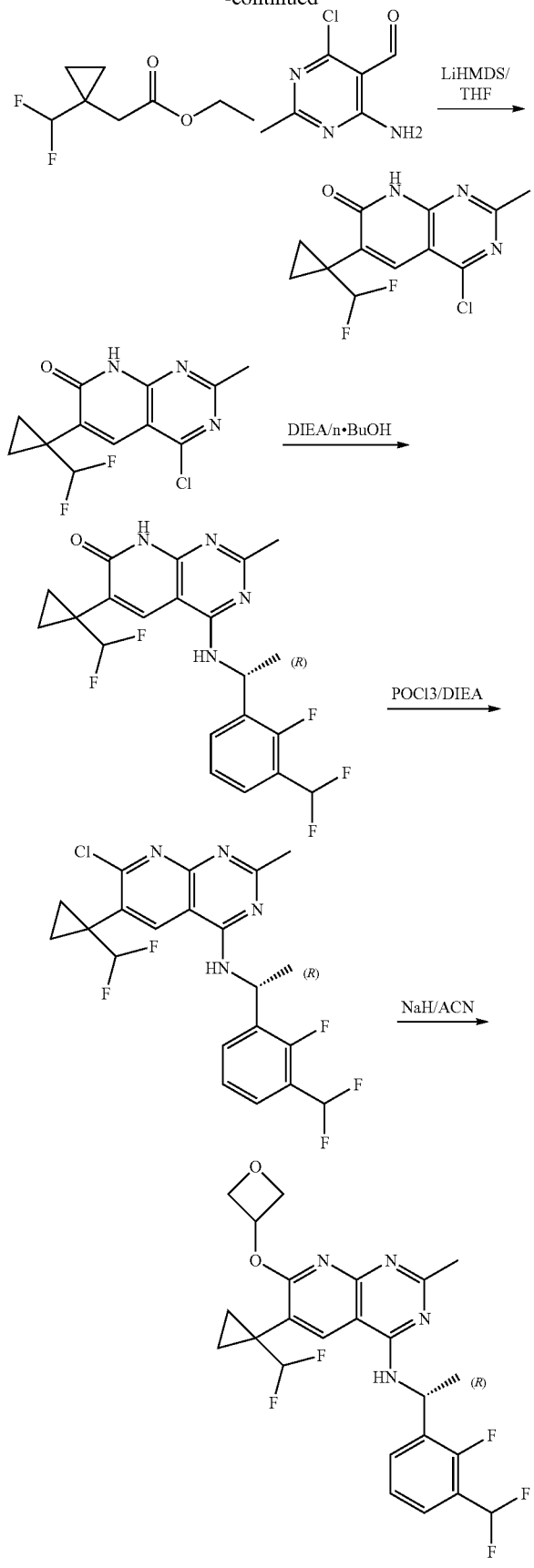

2-(1-formylcyclopropyl)acetonitrile

To a solution of oxalyl dichloride (2.75 g, 21.63 mmol) was added dry DCM (15 mL) at −78° C. under argon. DMSO (1.45 g, 19.82 mmol in dry DCM 5 mL) was added dropwise and the resulting mixture was stirred for 15 min at 78° C. 2-(1-(hydroxymethyl)cyclopropyl)acetonitrile (2.0 g, 18.02 mmol, in 5 mL DCM 5) was added dropwise and the resulting mixture was stirred for 25 min at −78° C., followed by the addition of triethylamine (9.1 g, 90.10 mmol) The resulting mixture was stirred −78° C. to 0° C. under argon for 2 hours. The reaction mixture was quenched water (30 mL) and extracted with DCM (30 mL×2). Organic extracts were combined, washed with brine, and dried over $Na_2SO_4$. It was filtered and solvent was removed under reduced pressure to give a crude. The crude was purified by flash chromatography on silica gel (petroleum:ethyl acetate=10:1) to give the desired product as an oil. ESI-MS m/z: 110[M+H]$^+$.

2-(1-(difluoromethyl)cyclopropyl)acetonitrile

To a solution of 2-(1-formylcyclopropyl)acetonitrile (1.3 g, 11.82 mmol) in DCM (15 mL) was added DAST (2.3 g, 14.19 mmol) dropwise at 0° C. under argon. Then the resulting mixture was stirred for 5 hours. The reaction mixture was quenched with water (30 mL) and extracted with DCM (30 mL×2). Organic extracts were combined, washed with brine, and dried over $Na_2SO_4$. It was filtered and solvent was removed under reduced pressure to give a crude. The crude was purified by flash chromatography on silica gel (petroleum:ethyl acetate=10:1) to give the desired product as an oil. ESI-MS m/z: 132[M−H]$^+$.

Ethyl 2-(1-(difluoromethyl)cyclopropyl)acetate

To a solution of 2-(1-(difluoromethyl)cyclopropyl)acetonitrile (1.0 g, 7.64 mmol) in EtOH (15 mL) was added $H_2SO_4$ (3 mL) dropwise. Then the resulting mixture was stirred at 95° C. under argon for 16.0 hours. It was quenched saturated $NaHCO_3$ (30 mL) and extracted with ethyl acetate (30 mL×2). Organic extracts were combined, washed with brine, and dried over $Na_2SO_4$. It was filtered and solvent was removed under reduced pressure to give a crude. The crude was purified by flash chromatography on silica gel (petroleum:ethyl acetate=10:1) to give the desired product as an oil. ESI-MS m/z: 179[M+H]$^+$.

4-chloro-6-(1-(difluoromethyl)cyclopropyl)-2-methylpyrido[2,3-d]pyrimidin-7(8H)-one A solution of ethyl 2-(1-(difluoromethyl)cyclopropyl)acetate (477 mg, 2.67 mmol) in THF (10 mL) and 4-amino-6-chloro-2-methylpyrimidine-5-carbaldehyde (350 mg, 2.05 mmol) was cooled to −78° C. under argon. LiHMDS (6.1 mL, 1 M in THF, 6.1 mmol) was added dropwise and the resulting mixture was stirred for 5 hours at −78° C. and allowed to warm room temperature. The reaction mixture was quenched saturated $NH_4Cl$ (20 mL) and extracted with ethyl acetate (30 mL×2). Organic extracts were combined, washed with brine, and dried over $Na_2SO_4$. It was filtered and solvent was removed under reduced pressure to give a crude. The crude was purified by flash chromatography on silica gel (dichloromethane:methyl alcohol=96:4) to give the desired product as a solid. ESI-MS m/z: 286[M−H]$^+$.

(R)-4-((1-(3-(difluoromethyl)-2-fluorophenyl)ethyl)amino)-6-(1-(difluoromethyl)cyclopropyl)-2-methylpteridine-7(8H)-one To a solution of 4-chloro-6-(1-(difluoromethyl)cyclopropyl)-2-methylpyrido[2,3-d]pyrimidin-7(8H)-one (260 mg, 0.92 mmol) and (R)-1-(3-(difluoromethyl)-2-fluorophenyl)ethan-1-amine hydrochloride (206 mg, 0.92 mmol) in n-BuOH (15 mL) was added DIEA (1.2 g, 9.2 mmol). The resulting mixture was heated at 120° C. under argon and stirred for 5 h. It was cooled to room temperature and ethyl acetate (60 mL) was added. The organics were washed with brine, dried over Na$_2$SO$_4$. It was filtered and solvent was removed under reduced pressure to give a crude. The crude was purified by flash chromatography on silica gel (dichloromethane:methyl alcohol=95:5) to afford the desired product as a solid. ESI-MS m/z: 440[M+H]$^+$;

(R)-7-chloro-N-(1-(3-(difluoromethyl)-2-fluorophenyl)ethyl)-6-(1-(difluoromethyl)cyclopropyl)-2-methylpyrido[2,3-d]pyrimidin-4-amine To a solution of (R)-4-((1-(3-(difluoromethyl)-2-fluorophenyl)ethyl)amino)-6-(1-(difluoromethyl)cyclopropyl)-2-methylpteridin-7(8H)-one (150 mg, 0.35 mmol) in POCl$_3$ (6 mL) was added DIEA (cat) at room temperature. The resulting mixture was heated at 105° C. under argon and stirred for 5 h. Then it was cooled to room temperature and concentrated to remove most POCl$_3$. The resulted residue was partitioned between saturated NaHCO$_3$ (5 mL) and dichloromethane (20 mL). The aqueous layer was extracted with dichloromethane (20 mL×2). The organics were combined, washed with brine, and dried over Na$_2$SO$_4$. It was filtered and solvent was removed under reduced pressure to give a crude. The crude was purified by flash chromatography on silica gel (dichloromethane:methyl alcohol=95:5) to afford the desired product as a solid. ESI-MS m/z: 457[M+H]$^+$;

N-(1-(3-(difluoromethyl)-2-fluorophenyl)ethyl)-6-(1-(difluoromethyl)cyclopropyl)-2-methyl-7-(oxetan-3-yloxy)pyrido[2,3-d]pyrimidin-4-amine To a solution of oxetan-3-ol (30 mg, 0.40 mmol) in ACN (10 mL) at 0° C. was added NaH (60%, 16 mg, 0.40 mmol), and the resulting mixture was stirred for 30 min at 0° C. under argon. (R)-7-chloro-N-(1-(3-(difluoromethyl)-2-fluorophenyl)ethyl)-6-(1-(difluoromethyl)cyclopropyl)-2-methylpyrido[2,3-d]pyrimidin-4-amine (120 mg, 0.27 mmol) was added. Then the resulting mixture was heated at 65° C. under argon and stirred for 2 hours. Then it was cooled to room temperature. The mixture was extracted with ethyl acetate (20 mL×2). Organic extracts were combined, washed with brine, and dried over Na$_2$SO$_4$. It was filtered and solvent was removed under reduced pressure to give a crude. The crude was purified by prep-TLC (dichloromethane:methyl alcohol=25:1) to afford the desired product as a solid. ESI-MS m/z: 495[M+H]$^+$. $^1$HNMR (MeOD, 400 MHz): δ 8.61 (s, 1H), 7.49-7.46 (t, J=6.8 Hz, 1H), 7.37-7.34 (m, 1H), 7.13-7.10 (t, J=7.6 Hz, 1H), 7.03-6.76 (t, J=54.8 Hz, 1H), 5.94 (t, J=58 Hz, 1H), 5.73-5.71 (m, 2H), 4.99 (m, 2H), 4.64 (m, 2H), 2.30 (s, 3H), 1.57-1.55 (d, J=6.8 Hz, 3H), 1.22 (m, 2H), 0.99 (m, 2H).

Compound 244: Synthesis of (R)-1-(4-((1-(3-(1,1-difluoro-2-hydroxy-2-methylpropyl)-2-fluorophenyl)ethyl)amino)-7-(4-isopropylpiperazin-1-yl)-2-methylpyrido[2,3-d]pyrimidin-6-yl)cyclopropane-1-carbonitrile

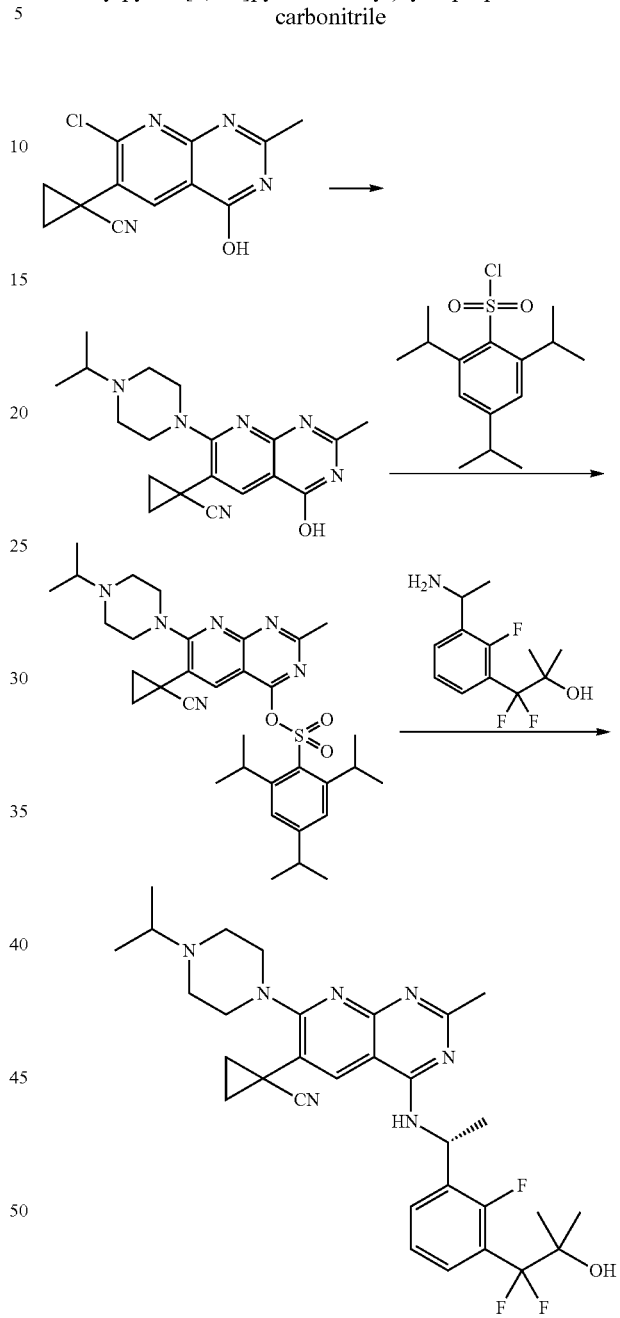

1-(4-hydroxy-7-(4-isopropylpiperazin-1-yl)-2-methylpyrido[2,3-d]pyrimidin-6-yl)cyclopropane-1-carbonitrile To a solution of 1-(7-chloro-4-hydroxy-2-methylpyrido[2,3-d]pyrimidin-6-yl)cyclopropane-1-carbonitrile (500 mg, 1.93 mmol) and 1-isopropylpiperazine (320 mg, 2.50 mmol) in n-BuOH (10 mL) was added DIEA (1.25 g, 9.65 mmol). The resulting mixture was heated at 100° C. under argon 5.0 h with stirring. It was cooled to room temperature and ethyl acetate (10 mL) was added. The organics were separated, washed with brine, and dried over Na₂SO₄. It was filtered and solvent was removed under reduced pressure to give a crude. The crude was purified by flash chromatography on silica gel (dichloromethane:methyl alcohol=20:1) to afford the desired product as a solid. ESI-MS m/z: 353[M+H]⁺;

(R)-1-(4-((1-(3-(1,1-difluoro-2-hydroxy-2-methyl-propyl)-2-fluorophenyl)ethyl)amino)-7-(4-isopropylpiperazin-1-yl)-2-methylpyrido[2,3-d]pyrimidin-6-yl)cyclopropane-1-carbonitrile To a stirred solution of 1-(4-hydroxy-7-(4-isopropylpiperazin-1-yl)-2-methylpyrido[2,3-d]pyrimidin-6-yl)cyclopropane-1-carbonitrile (200 mg) in THF was added DMAP ((30 mg, 0.257 mmol) and DIEA (40 mg, 3 mmol) at RT, followed by the addition of 2,4,6-triisopropylbenzenesulfonyl chloride (152 mg, 0.606 mmol). The mixture was stirred at RT for 16 h. Then (R)-1-(3-(1-aminoethyl)-2-fluorophenyl)-1,1-difluoro-2-methylpropan-2-ol added to the solution and allowed to stir for 2 h at 60° C. The reaction was quenched with water (50 mL), and the resulting mixture was extracted with ethyl acetate (20 mL×3). The combined organic extracts were combined, washed with brine, and dried over Na₂SO₄. It was filtered and solvent was removed under reduced pressure to give a residue. The residue was purified by flash column chromatography on silica gel (CH₃OH/DCM=0-5%), afford the desired product as a white solid. ESI-MS m/z: 581.31[M+H]⁺ ¹HNMR (400 MHz, MeOD) δ 8.59 (s, 1H), 7.46-7.43 (m, 1H), 7.29-7.25 (m, 1H), 7.09-7.05 (m, 1H), 5.76-5.71 (m, 1H), 3.72 (m, 4H), 2.97 (m, 4H), 2.32 (s, 3H), 1.83-1.70 (m, 2H), 1.60-1.52 (m, 4H), 1.28-1.25 (m, 2H), 1.20-1.18 (m, 6H), 1.15-1.14 (m, 6H)

Compound 283: Synthesis of (R)-4-(4-((1-(3-(difluoro(1-isopropylazetidin-3-yl)methyl)-2-fluorophenyl)ethyl)amino)-7-methoxypyrido[2,3-d]pyrimidin-6-yl)tetrahydro-2H-thiopyran-1,1-dioxide

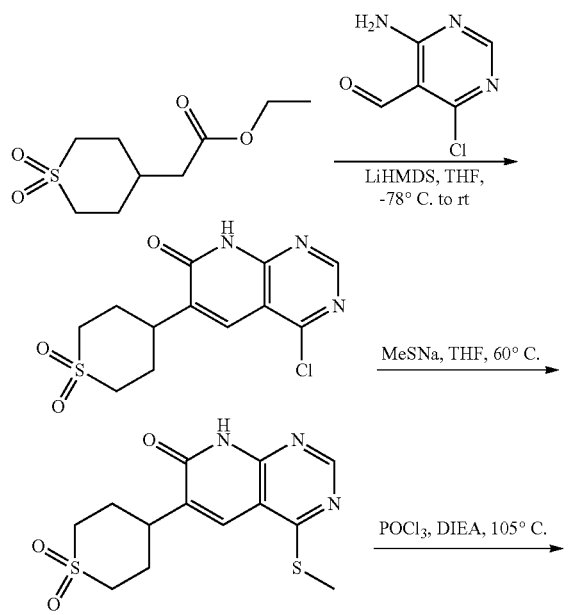

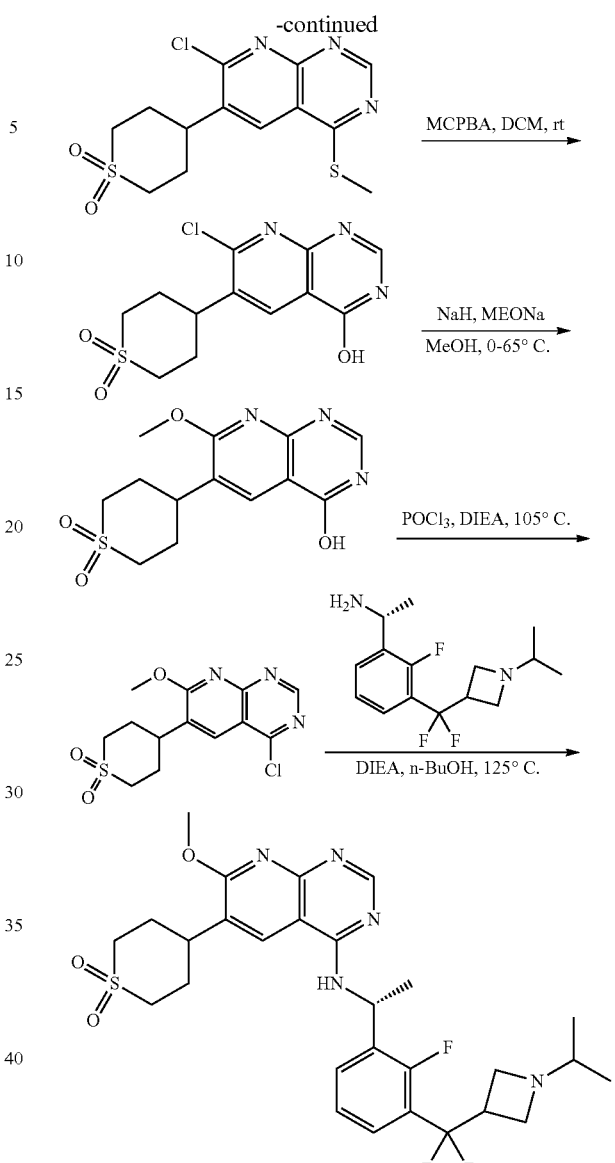

4-chloro-6-(1,1-dioxidotetrahydro-2H-thiopyran-4-yl)pyrido[2,3-d]pyrimidin-7(8H)-one LiHMDS (13.2 ml, 1.0 M THF) was added to ethyl 2-(1,1-dioxidotetrahydro-2H-thiopyran-4-yl)acetate (1.0 g, 4.54 mmol) in THF (80 mL) at −78° C. over 0.5 h, followed by the addition of 4-amino-6-chloropyrimidine-5-carbaldehyde (600 mg, 3.81 mmol) in THF (20 mL) at the same temperature. The reaction mixture was stirred and gradually warmed up to RT for 4 h. Saturated NH₄Cl (2 mL) was added, extracted with ethyl acetate. The organics were combined, washed with brine, and dried over Na₂SO₄. The mixture was purified by flash chromatography on silica gel (DCM:MeOH=20:1) to afford the desired product ESI-MS m/z: 314 [M+H]⁺.

6-(1,1-dioxidotetrahydro-2H-thiopyran-4-yl)-4-(methylthio)pyrido[2,3-d]pyrimidin-7(8H)-one MeSNa (2 mL) was added to a solution of 4-chloro-6-(1,1-dioxidotetrahydro-2H-thiopyran-4-yl) pyrido[2,3-d]pyrimidin-7(8H)-one (450 mg, 1.43 mmol) in THF (10 mL), then the mixture was stirred at 60° C. for 3 h. It was cooled to room temperature and quenched with sat. NaHCO³ solution. The mixture was extracted with ethyl acetate. The organic extracts were combined, washed with brine, and dried over $Na_2SO_4$. It was filtered and solvent was removed under reduced pressure to give a crude. The crude was purified by flash chromatography on silica gel (DCM:MeOH=20:1) to afford the desired product ESI-MS m/z: 326[M+H]$^+$.

4-(7-chloro-4-(methylthio) pyrido[2,3-d]pyrimidin-6-yl)tetrahydro-2H-thiopyran 1,1-dioxide DIEA (0.2 ml) was added to a solution of 6-(1,1-dioxidotetrahydro-2H-thiopyran-4-yl)-4-(methylthio)pyrido[2,3-d]pyrimidin-7(8H)-one (480 mg, 1.48 mmol) in $POCl_3$ (10 mL), then the mixture was stirred at 105° C. for 3 h. $POCl_3$ was evaporated under reduced pressure to give a residue. The residue was purified by flash chromatography on silica gel (DCM:MeOH=40:1) to afford the desired product ESI-MS m/z: 344[M+H]$^+$.

4-(7-chloro-4-hydroxypyrido[2,3-d]pyrimidin-6-yl)tetrahydro-2H-thiopyran 1,1-dioxide MCPBA (500 mg, 2.90 mmol) was added to a solution of 4-(7-chloro-4-(methylthio) pyrido[2,3-d]pyrimidin-6-yl)tetrahydro-2H-thiopyran 1,1-dioxide (200 mg, 0.58 mmol) in DCM (20 mL). The mixture was stirred at RT for 5 h. Ethyl acetate was added, and the mixture was washed with bine, dried over $Na_2SO_4$. It was filtered and solvent was removed under reduced pressure to give a crude. The crude was purified by flash chromatography on silica gel (DCM:MeOH=20:1) to afford the desired product ESI-MS m/z: 314[M+H]$^+$.

4-(4-hydroxy-7-methoxypyrido[2,3-d]pyrimidin-6-yl)tetrahydro-2H-thiopyran 1,1-dioxide NaH (108 mg, 2.7 mmol) was added to a mixture of 4-(7-chloro-4-hydroxypyrido[2,3-d]pyrimidin-6-yl)tetrahydro-2H-thiopyran 1,1-dioxide (170 mg, 0.54 mmol), MeONa (146 mg, 2.70 mmol) in MeOH (5 mL) at 0° C. Then the mixture was stirred at 65° C. for 3 h. It was cooled to room temperature and reaction was quenched by adding sat. $NaHCO_3$ solution. It was extracted with ethyl acetate. The organics were combined, washed with brine, and dried over $Na_2SO_4$. It was filtered and solvent was removed under reduced pressure to give a crude. The crude was purified by flash chromatography on silica gel (DCM:MeOH=20:1) to afford the desired product ESI-MS m/z: 310[M+H]$^+$.

4-(4-chloro-7-methoxypyrido[2,3-d]pyrimidin-6-yl)tetrahydro-2H-thiopyran 1,1-dioxide DIEA (2 drops) was added to a solution of 4-(4-hydroxy-7-methoxypyrido[2,3-d]pyrimidin-6-yl)tetrahydro-2H-thiopyran 1,1-dioxide (42 mg, 0.136 mmol) in $POCl_3$ (8 mL), then the mixture was stirred at 105° C. for 5 h. $POCl_3$ was evaporated under reduced pressure to give a residue, the residue was purified by preparative-TLC to give the desired product ESI-MS m/z: 328[M+H]$^+$.

(R)-4-(4-((1-(3-(difluoro(1-isopropylazetidin-3-yl)methyl)-2-fluorophenyl)ethyl)amino)-7-methoxypyrido[2,3-d]pyrimidin-6-yl)tetrahydro-2H-thiopyran-1,1-dioxide To a solution of 4-(4-chloro-7-methoxypyrido[2,3-d]pyrimidin-6-yl) tetrahydro-2H-thiopyran 1,1-dioxide (16 mg, 0.049 mmol) and (R)-1-(3-(difluoro(1-isopropylazetidin-3-yl)methyl)-2-fluorophenyl)ethanamine (20 mg, 0.070 mmol) in n-BuOH (3 ml) was added DIEA (1 mL). The resulting mixture was heated at 125° C. under argon and stirred for 5 h. It was cooled to room temperature and ethyl acetate (10 mL) was added. The organics were washed with brine, dried over $Na_2SO_4$. It was filtered and solvent was removed under reduced pressure to give a crude. The crude was purified by flash chromatography on silica gel (DCM:MeOH=20:1) to afford the desired product ESI-MS m/z: 578[M+H]$^+$. $^1$HNMR (400 MHz, MeOD): δ 8.68 (s, 1H), 8.52 (brs, 1H), 7.71-7.67 (m, 1H), 7.58-7.55 (m, 1H), 7.35-7.31 (m, 1H), 5.89-5.84 (m, 1H), 4.30-4.23 (m, 4H), 4.11 (s, 3H), 3.48-3.40 (m, 4H), 3.23-3.19 (m, 2H), 2.48-2.35 (m, 4H), 1.75-1.73 (d, J=6.8 Hz, 3H), 1.29-1.27 (d, J=6.8 Hz, 6H).

Compound 418: Synthesis of (R)—N-(1-(3-(difluoro(1-isopropylpiperidin-4-yl)methyl)phenyl)ethyl)-6-(4-isopropylpiperazin-1-yl)-7-methoxy-2-methylpyrido[2,3-d]pyrimidin-4-amine

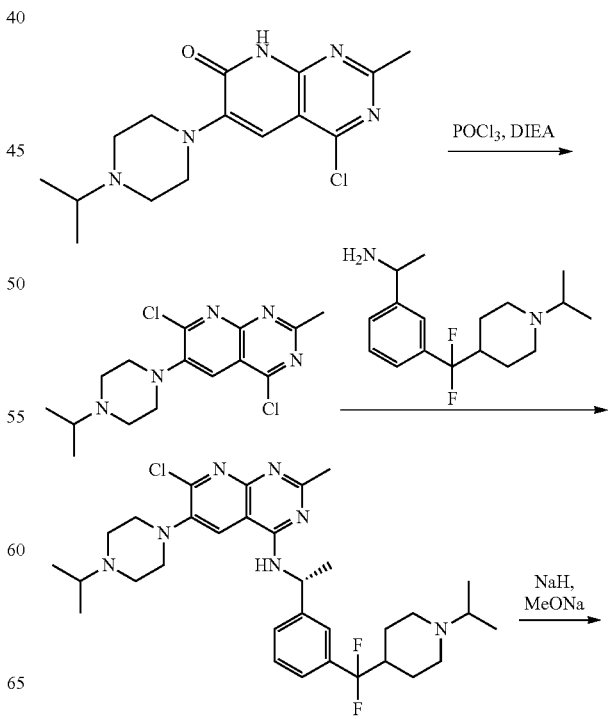

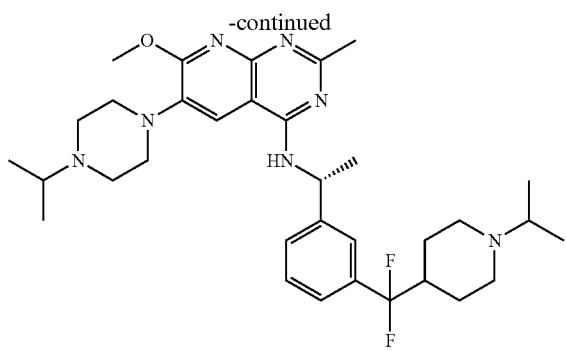

4,7-dichloro-6-(4-isopropylpiperazin-1-yl)-2-methylpyrido[2,3-d]pyrimidine

To a solution of 4,7-dichloro-6-(4-isopropylpiperazin-1-yl)-2-methylpyrido[2,3-d]pyrimidine (1 g, 3.11 mmol) in POCl₃ (33 mL) was added diisopropyl ethyl amine (5.5 mL). The mixture was stirred at 100° C. for 5 h. It was allowed to cool to room temperature and concentrated in vacuo to remove POCl₃. The residue was treated with ethyl acetate and sat.NaHCO₃ solution. The organic phase was separated, washed with brine, and dried over Na₂SO₄. It was filtered and solvent was removed under reduced pressure to give a residue. The residue was purified by flash column chromatography on silica gel to give desired product ESI-MS m/z: 340.2 [M+H]⁺.

(R)-7-chloro-N-(1-(3-(difluoro(1-isopropylpiperidin-4-yl)methyl)phenyl)ethyl)-6-(4-isopropylpiperazin-1-yl)-2-methylpyrido[2,3-d]pyrimidin-4-amine To a solution of 4,7-dichloro-6-(4-isopropylpiperazin-1-yl)-2-methylpyrido[2,3-d]pyrimidine (275 mg, 0.81 mmol) in DMSO (5 mL) was added KF (280 mg, 4.86 mmol) and (R)-1-(3-(difluoro(1-isopropylpiperidin-4-yl)methyl)phenyl)ethan-1-amine (288 mg, 0.97 mmol). The reaction mixture was heated to 110° C. for 3 hour and cooled to room temperature. Saturated NaHCO₃ solution (40 mL) was added, and the mixture was extracted with ethyl acetate. The extracts were combined, washed with brine, and dried over Na₂SO₄. It was filtered and solvent was removed under reduced pressure to give a residue. The residue was purified by flash column chromatography on silica gel to give desired product ESI-MS m/z: 600.2 [M+H]⁺.

(R)-N-(1-(3-(difluoro(1-isopropylpiperidin-4-yl)methyl)phenyl)ethyl)-6-(4-isopropylpiperazin-1-yl)-7-methoxy-2-methylpyrido[2,3-d]pyrimidin-4-amine MeSNa (2 mL) was added to methanol (15 mL) and the mixture was stirred at room temperature for 0.5 h. (R)-7-chloro-N-(1-(3-(difluoro(1-isopropylpiperidin-4-yl)methyl)phenyl)ethyl)-6-(4-isopropylpiperazin-1-yl)-2-methylpyrido[2,3-d]pyrimidin-4-amine (200 mg, 0.33 mmol) was added. The resulting mixture was stirred at 65° C. for 1 hour. It was cooled ot room temperature and sat. NaHCO₃ solution (5 mL) was added, and the mixture was extracted with ethyl acetate. The organics were combine, washed with brine, and dried over Na₂SO₄. It was filtered and solvent was removed under reduced pressure to give a residue. The residue was purified by flash column chromatography on silica gel to give desired product ¹HNMR (DMSO-d6:400 MHz): δ 8.18-8.16 (d, J=3.8 Hz, 1H), 7.92-7.9 (s, 1H), 7.56-7.54 (d, J=7.6 Hz, 1H), 7.49-7.45 (brs, 1H), 7.43-7.41 (t, J=7.6 Hz, 1H), 7.29-7.27 (d, J=8 Hz, 1H), 5.58-5.57 (m, 1H), 3.97-3.9 (s, 3H), 3.08-3.07 (m, 4H), 2.72-2.68 (m, 3H), 2.62-2.50 (m, 5H), 2.33-2.3 (s, 3H), 2.01-1.92 (m, 3H), 1.620-1.602 (d, J=7.2 Hz, 3H), 1.53-1.51 (m, 2H), 1.27-1.2 (m, 2H), 1.036-1.02 (d, J=6.4 Hz, 6H), 0.903-0.887 (d, J=6.4 Hz, 6H). ESI-MS m/z: 596.2 [M+H]⁺.

Compound 313: Synthesis of (R)-1-(4-(4-((1-(2-fluoro-3-(trifluoromethyl)phenyl)ethyl)amino)-7-methoxy-2-methylpyrido[2,3-d]pyrimidin-6-yl)piperazin-1-yl)-2-hydroxyethan-1-one

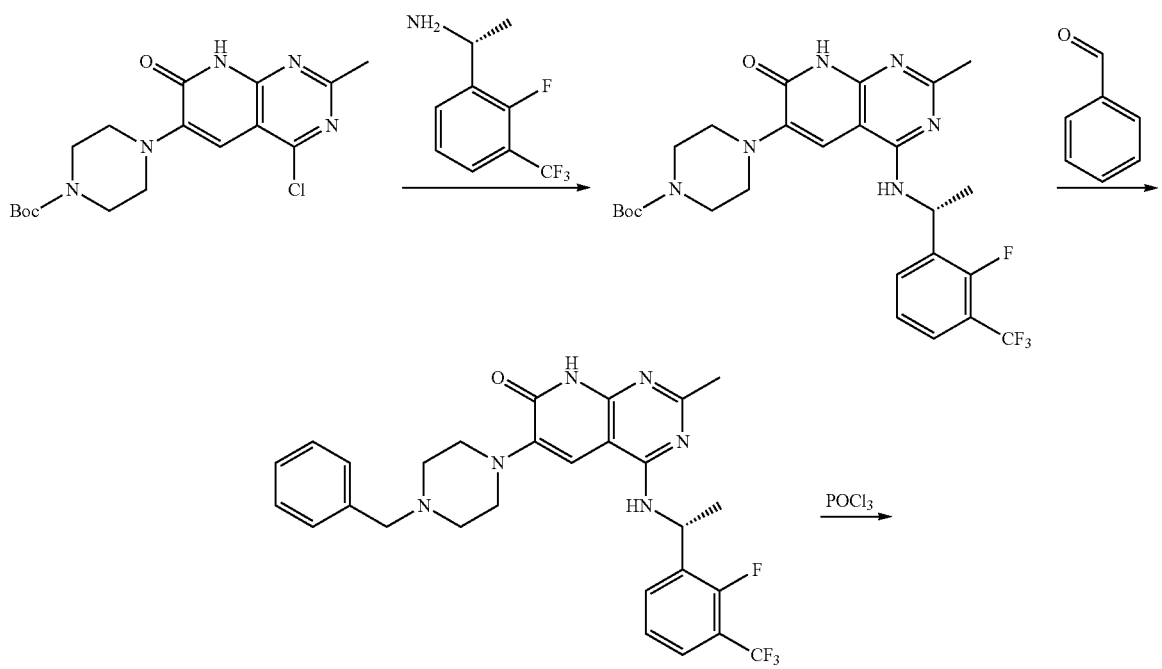

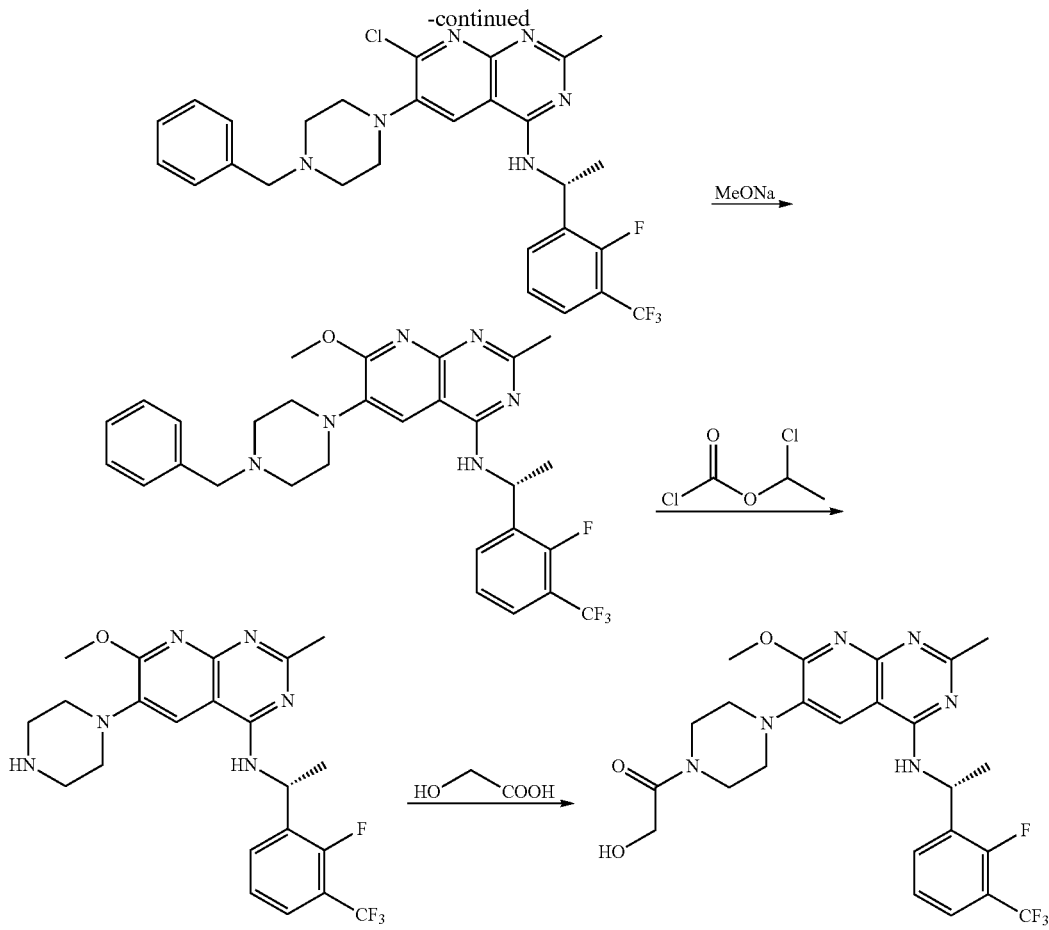

Tert-butyl(R)-4-(4-((1-(2-fluoro-3-(trifluoromethyl)phenyl)ethyl)amino)-2-methyl-7-oxo-7,8-dihydropyrido[2,3-d]pyrimidin-6-yl)piperazine-1-carboxylate To a solution of tert-butyl 4-(4-chloro-2-methyl-7-oxo-7,8-dihydropyrido[2,3-d]pyrimidin-6-yl)piperazine-1-carboxylate (1.5 g, 3.95 mmol) in DMSO (20 mL) was added KF (1.37 g, 23.7 mmol) and (R)-1-(2-fluoro-3-(trifluoromethyl)phenyl)ethan-1-amine (0.98 g, 4.74 mmol). The resulting mixture was heated to 110° C. for 3 hour. It was cooled down to room temperature and sat. NaHCO$_3$ solution (40 mL) was added. The mixture was extracted with ethyl acetate. The extracts were combined, washed with brine, and dried over Na$_2$SO$_4$. It was filtered and solvent was removed under reduced pressure to give a residue. The residue was purified by flash column chromatography on silica gel to give desired product ESI-MS m/z: 551.2 [M+H]$^+$.

(R)-6-(4-benzylpiperazin-1-yl)-4-((1-(2-fluoro-3-(trifluoromethyl)phenyl)ethyl)amino)-2-methylpyrido[2,3-d]pyrimidin-7(8H)-one To a solution of tert-butyl (R)-4-(4-((1-(2-fluoro-3-(trifluoromethyl)phenyl)ethyl)amino)-2-methyl-7-oxo-7,8-dihydropyrido[2,3-d]pyrimidin-6-yl)piperazine-1-carboxylate (700 mg, 1.27 mmol) in DCM (8 mL) was added trifluoroacetic acid (2 mL). The mixture was stirred at room temperature for 1 h. The volatiles were evaporated to afford the product (R)-4-((1-(2-fluoro-3-(trifluoromethyl)phenyl)ethyl)amino)-2-methyl-6-(piperazin-1-yl)pyrido[2,3-d]pyrimidin-7(8H)-one (570 mg, 1.27 mmol). The obtained intermediate was dissolved in methanol (15 ml) followed by the addition of excessive NaBH$_3$CN. The mixture was stirred at 60° C. for overnight. It was cooled to room temperature and quenched with NaHCO$_{3(aq)}$ (5 mL), and extracted with ethyl acetate. The extracts were combined, washed with brine, dried over Na$_2$SO$_4$. It was filtered and solvent was removed to give a residue. The residue was purified by flash column chromatography on silica gel to give desired product ESI-MS m/z: 541.2 [M+H]$^+$.

(R)-6-(4-benzylpiperazin-1-yl)-7-chloro-N-(1-(2-fluoro-3-(trifluoromethyl)phenyl)ethyl)-2-methylpyrido[2,3-d]pyrimidin-4-amine To a solution of (R)-6-(4-benzylpiperazin-1-yl)-4-((1-(2-fluoro-3-(trifluoromethyl)phenyl)ethyl)amino)-2-methylpyrido[2,3-d]pyrimidin-7(8H)-one (600 mg, 1.11 mmol) in POCl$_3$ (30 mL) was added DIEA (5 mL), and the resulting mixture was heated to 110° C. for 2 hour. It was cooled down to room temperature treated with ethyl acetate and NaHCO$_{3(aq)}$. The organics were separated, washed with brine, and dried over Na$_2$SO$_4$. It was filtered and solvent was removed under reduced pressure to give a residue. The residue was purified by flash column chromatography on silica gel to give desired product ESI-MS m/z: 559.2 [M+H]$^+$.

(R)-6-(4-benzylpiperazin-1-yl)-N-(1-(2-fluoro-3-(trifluoromethyl)phenyl)ethyl)-7-methoxy-2-methylpyrido[2,3-d]pyrimidin-4-amine MeSNa (3 mL) were dissolved in methanol (15 mL) and the mixture was stirred at room temperature for 0.5 h. (R)-6-(4-benzylpiperazin-1-yl)-7-chloro-N-(1-(2-fluoro-3-(trifluoromethyl)phenyl)ethyl)-2-methylpyrido[2,3-d]pyrimidin-4-amine (600 mg, 1.07 mmol) was added. The reaction mixture was stirred at 65° C. for 1 hour. It was cooled to room temperature and treated with NaHCO$_3$(aq) (10 mL) and ethyl acetate. The organics were separated, washed with brine, and dried over Na$_2$SO$_4$. It was filtered and solvent was removed under reduced pressure to give a crude. The crude was purified by flash column chromatography on silica gel to give desired product ESI-MS m/z: 555.2 [M+H]$^+$.

(R)—N-(1-(2-fluoro-3-(trifluoromethyl)phenyl)ethyl)-7-methoxy-2-methyl-6-(piperazin-1-yl)pyrido[2,3-d]pyrimidin-4-amine To a solution of (R)-6-(4-benzylpiperazin-1-yl)-N-(1-(2-fluoro-3-(trifluoromethyl)phenyl)ethyl)-7-methoxy-2-methylpyrido[2,3-d]pyrimidin-4-amine (500 mg, 0.9 mmol) in dichloroethane (15 ml) was added 1-chloroethyl carbonochloridate (258 mg, 1.8 mmol). The mixture was stirred at 90° C. for 1 hour. It was cooled to room temperature and solvent was removed. The residue was dissolved in methanol (10 ml). The mixture was stirred at 70° C. for 1 h. The volatiles were evaporated to afford the product which was used directly in the next step without further purification ESI-MS m/z: 465.2[M+H]$^+$.

(R)-1-(4-(4-((1-(2-fluoro-3-(trifluoromethyl)phenyl)ethyl)amino)-7-methoxy-2-methylpyrido[2,3-d]pyrimidin-6-yl)piperazin-1-yl)-2-hydroxyethan-1-one To a solution of (R)—N-(1-(2-fluoro-3-(trifluoromethyl)phenyl)ethyl)-7-methoxy-2-methyl-6-(piperazin-1-yl)pyrido[2,3-d]pyrimidin-4-amine (100 mg, 0.21 mmol), BOP (285 mg, 0.63 mmol) and DIEA (83 mg, 0.63 mmol) in THF (5 mL) was 2-hydroxyacetic acid (44 mg, 0.42 mmol). The mixture was stirred at room temperature for overnight. NaHCO$_{3(aq)}$ (5 mL) was added, and the mixture was extracted with ethyl acetate. The organics were combined, washed with brine, and dried over Na$_2$SO$_4$. It was filtered and solvent was removed under reduced pressure to give a crude. The crude was purified by flash column chromatography on silica gel to give desired product ESI-MS m/z: 523.2[M+H]$^+$. $^1$H NMR (400 MHz, DMSO) 8.78-8.74 (m, 1H), 8.016-8.0 (s, 1H), 7.792-7.828 (t, J=6.8 Hz, 1H), 7.676-7.641 (t, J=7.2 Hz, 1H), 7.399-7.36 (t, J=7.6 Hz 1H), 5.8-5.75 (m, 1H), 4.7-4.67 (m, 1H), 4.15-4.11 (m, 2H), 4.04-4.0 (s, 3H), 3.67-3.6 (m, 2H), 3.56-3.5 (m, 2H), 3.04-3.01 (m, 3H), 2.4-2.3 (s, 3H), 1.65-1.632 (d, J=7.2 Hz, 3H).

Compound 222: Synthesis of (R)-7-chloro-N-(1-(3-(difluoro(1-isopropylpiperidin-4-yl)methyl)-2-fluorophenyl)ethyl)-6-(1-isopropylpiperidin-4-yl)-2-methylpyrido[2,3-d]pyrimidin-4-amine

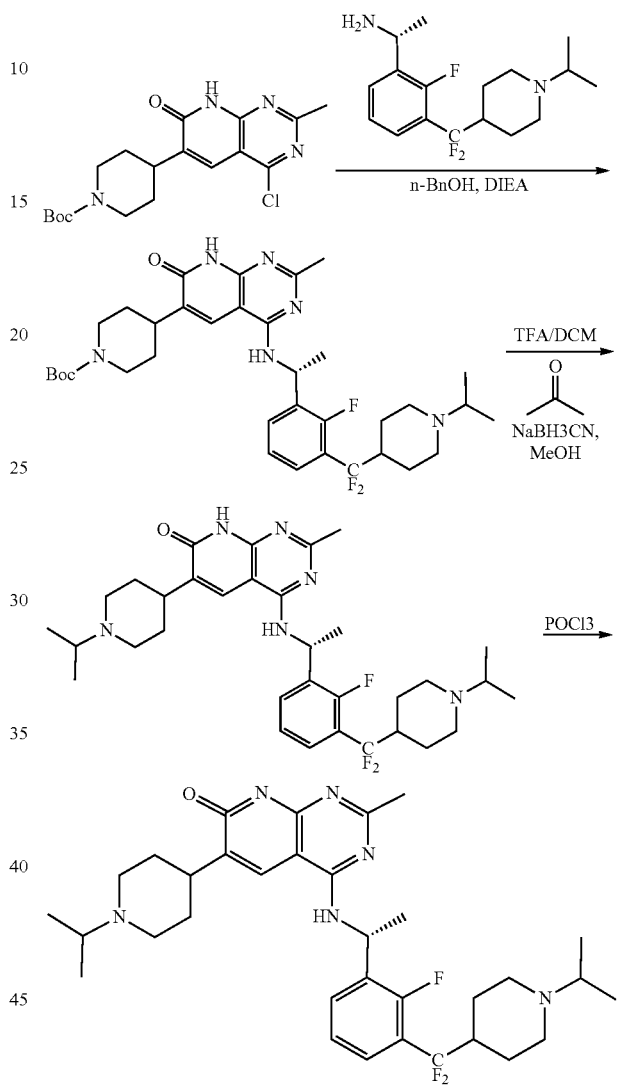

Tert-butyl (R)-4-(4-((1-(3-(difluoro(1-isopropylpiperidin-4-yl)methyl)-2-fluorophenyl)ethyl)amino)-2-methyl-7-oxo-7,8-dihydropyrido[2,3-d]pyrimidin-6-yl)piperidine-1-carboxylate A mixture of tert-butyl 4-(4-chloro-2-methyl-7-oxo-7,8-dihydropyrido[2,3-d]pyrimidin-6-yl)piperidine-1-carboxylate (450 mg, 1.19 mmol), (R)-1-(3-(difluoro(1-isopropylpiperidin-4-yl)methyl)-2-fluorophenyl)ethan-1-amine (500 mg, 1.42 mmol) and DIEA (0.6 mL, 3.57 mmol) were dissolved in n-BuOH (15 mL). It was stirred at 120° C. for 3 h under argon. The mixture was allowed to cool to RT and concentrated in vacuo. The residue was purified by column chromatography on silica gel (MeOH/DCM=3/50, 2/25) to afford the desired product

1011

(R)-4-((1-(3-(difluoro(1-isopropylpiperidin-4-yl)methyl)-2-fluorophenyl)ethyl)amino)-6-(1-isopropylpiperidin-4-yl)-2-methylpyrido[2,3-d]pyrimidin-7(8H)-one To a solution of tert-butyl (R)-4-(4-((1-(3-(difluoro(1-isopropylpiperidin-4-yl)methyl)-2-fluorophenyl)ethyl)amino)-2-methyl-7-oxo-7,8-dihydropyrido[2,3-d]pyrimidin-6-yl)piperidine-1-carboxylate (778 mg, 1.18 mmol) in DCM (6 mL) was added TFA (1.5 mL) at room temperature and the mixture was stirred for 1 h. It was concentrated in vacuo to afford the crude product without further purification which was used directly in the next step. AcOH (0.2 mL), NaBH$_3$CN (206 mg, 3.55 mmol), acetone (371 mg, 5.9 mmol) and the crude product from last step were dissolved in MeOH (15 mL). The mixture was stirred at 60° C. for 16 h. It was cooled down to room temperature, quenched with saturated NaHCO$_3$ solution, and then extracted with ethyl acetate. The organic layer was washed with saturated NaHCO$_3$ solution and brine, dried over Na$_2$SO$_4$. It was filtered and solvent was removed under reduced pressure to give a crude. The crude was purified by preparative-TLC (MeOH/DCM=1:20, to 1:10) to give the desired product

(R)-7-chloro-N-(1-(3-(difluoro(1-isopropylpiperidin-4yl)methyl)-2-fluorophenyl)ethyl)-6-(1-isopropylpiperidin-4yl)-2-methylpyrido[2,3-d]pyrimidin-4-amine A mixture of (R)-4-((1-(3-(difluoro(1-isopropylpiperidin-4-yl)methyl)-2-fluorophenyl)ethyl)amino)-6-(1-isopropylpiperidin-4-yl)-2-methylpyrido[2,3-d]pyrimidin-7(8H)-one (358 mg, 0.6 mmol) and POCl$_3$ (15 mL) was stirred for 1 h at 105° C. It was cooled and concentrated in vacuo to afford the crude product which was used in the next step without further purification. ESI-MS m/z: 617.23 [M+H]$^+$. $^1$HNMR (400 MHz, DMSO-d6) δ 8.66 (s, 1H), 7.56-7.53 (t, J=6.8, 1H), 7.29-7.26 (t, J=6.8 Hz, 1H), 7.13-7.10 (t, 7.6 Hz, 1H), 5.78-5.73 (m, 1H), 3.25 (s, 1H), 3.21-3.20 (m, 2H), 3.14-3.02 (m, 4H), 2.98-2.92 (m, 1H), 2.70-2.65 (m, 2H), 2.48-2.42 (m, 2H), 2.33 (s, 3H), 2.05-1.90 (m, 4H), 1.76-1.72 (m, 2H), 1.62-1.60 (m, 5H), 1.18-1.17 (d, J=6.4 Hz, 6H), 1.08-1.07 (d, J=6.4 Hz, 6H)

Compound 158: Synthesis of (R)-4-(4-((1-(3-(difluoromethyl)-2-(2-methoxyethoxy)phenyl)ethyl)amino)-7-(2-methoxyethoxy)-2-methylpyrido[2,3-d]pyrimidin-6-yl)tetrahydro-2H-thiopyran 1,1-dioxide

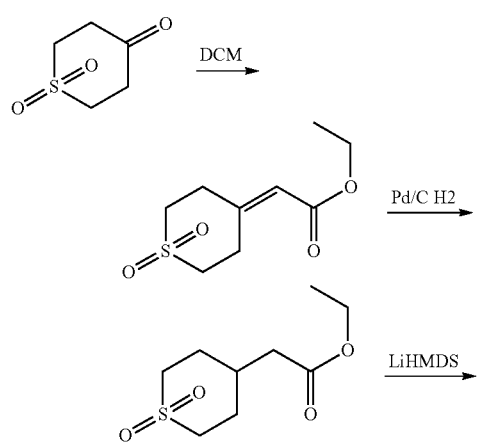

1012

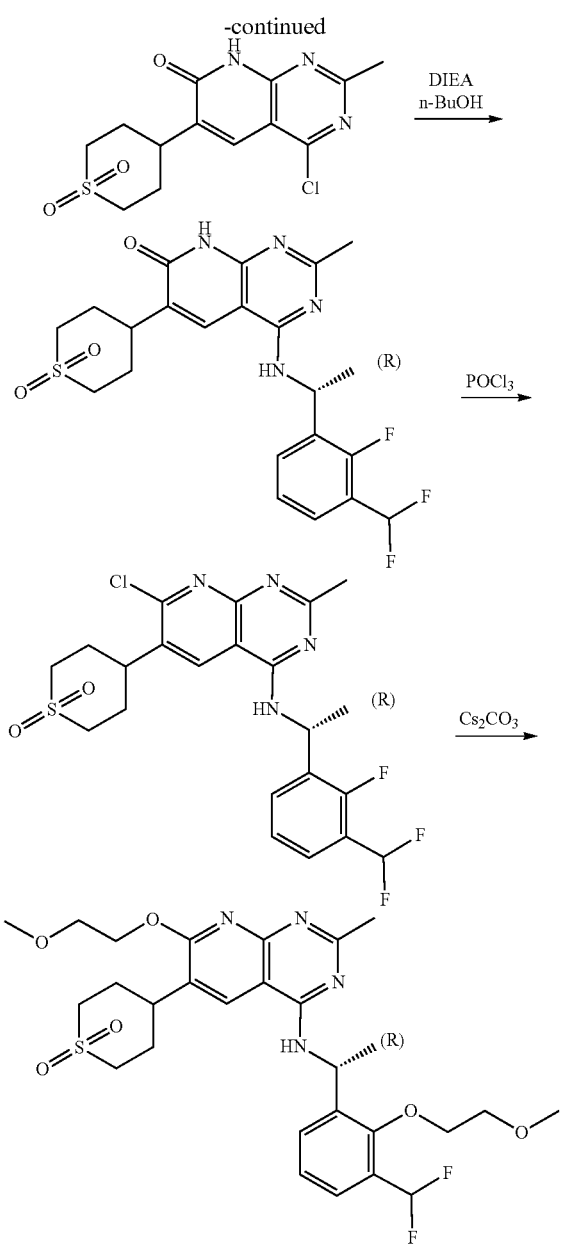

Ethyl 2-(1,1-dioxidotetrahydro-4H-thiopyran-4-ylidene)acetate

A solution of tetrahydro-4H-thiopyran-4-one 1,1-dioxide (12.5 g, 0.08 mol) and ethyl (triphenylphosphoranylidene)acetate (44 g, 0.12 mol) in DCM (100 mL) was stirred for 16 hours at 50° C. under argon. It was cooled down to room temperature and solvent was removed under reduced pressure to give a crude. The crude was purified by flash chromatography on silica gel (petroleum:ethyl acetate=67:33) to give the desired product ESI-MS m/z: 219 [M+H]$^+$.

Ethyl 2-(1,1-dioxidotetrahydro-2H-thiopyran-4-yl)acetate

To a solution of ethyl 2-(1,1-dioxidotetrahydro-4H-thiopyran-4-ylidene)acetate (7 g, 0.032 mol) in MeOH (60 mL) were added Pd/C (10%, 500 mg, 5.0 mmol). Then the resulting mixture was stirred at RT under hydrogen for 16 hours. It was filtered and solvent was removed under reduced pressure to give a crude which was used directly in the next step without purification. ESI-MS m/z: 221 [M+H]⁺.

4-chloro-6-(1,1-dioxidotetrahydro-2H-thiopyran-4-yl)-2-methylpyrido[2,3-d]pyrimidin-7(8H)-one A solution of methyl ethyl 2-(1,1-dioxidotetrahydro-2H-thiopyran-4-yl)acetate (7.2 g, 0.033 mol) in THF (50 mL) was cooled to −78° C. under argon. LiHMDS (40 mL, 1 M in THF) was added dropwise and the resulting mixture was stirred for 2 h at −78° C. to −45° C. Then 4-amino-6-chloro-2-methylpyrimidine-5-carbaldehyde (5.9 g, 0.033 mol) in THF (50 mL) was added dropwise at −78° C. The mixture was stirred at −78° C. and allowed to warm gradually to room temperature overnight. It was quenched with saturated NH₄Cl (40 mL). The mixture was extracted with ethyl acetate (50 mL×2). Organic extracts were combined, washed with brine, and dried over Na₂SO₄. It was filtered and solvent was removed under reduced pressure to give a crude. The crude was purified by flash chromatography on silica gel (dichloromethane:methyl alcohol=98:2) to afford the desired product ESI-MS m/z: 328 [M+H]⁺.

(R)-4-((1-(3-(difluoromethyl)-2-fluorophenyl)ethyl)amino)-6-(1,1-dioxidotetrahydro-2H-thiopyran-4-yl)-2-methylpyrido[2,3-d]pyrimidin-7(8H)-one To a solution of 4-chloro-6-(1,1-dioxidotetrahydro-2H-thiopyran-4-yl)-2-methylpyrido[2,3-d]pyrimidin-7(8H)-one (3.6 g, 0.011 mol) and (R)-1-(3-(difluoromethyl)-2-fluorophenyl)ethan-1-amine hydrochloride (3.2 g, 0.014 mol) in n-BuOH (50 ml) was added DIEA (1.42 g, 11.60 mmol). The resulting mixture was heated at 130° C. under argon and stirred for overnight. It was cooled to room temperature and ethyl acetate (60 mL) was added. The organics were washed with brine, dried over Na₂SO₄. It was filtered and solvent was removed under reduced pressure to give a crude. The crude was purified by flash chromatography on silica gel (dichloromethane:methyl alcohol=95:5) to afford the desired product ESI-MS m/z: 481[M+H]⁺;

4-(7-chloro-4-((1-(3-(difluoromethyl)-2-fluorophenyl)ethyl)amino)-2-methylpyrido[2,3-d]pyrimidin-6-yl)tetrahydro-2H-thiopyran 1,1-dioxide To a solution of (R)-4-((1-(3-(difluoromethyl)-2-fluorophenyl)ethyl)amino)-6-(1,1-dioxidotetrahydro-2H-thiopyran-4-yl)-2-methylpyrido[2,3-d]pyrimidin-7(8H)-one (6.2 g, 12.9 mmol) in PhMe (50 mL) was added POCl₃ (10 mL) and DIEA (1.42 g, 11.60 mmol). The resulting mixture was heated at 100° C. under argon and stirred for overnight. Then it was cooled to RT and concentrated to remove most of POCl₃ and PhMe. The resulted residue was partitioned between saturated NaHCO₃ (5 mL) and dichloromethane (20 mL). It was extracted with dichloromethane (20 mL×2). The organics were combined, washed with brine, and dried over Na₂SO₄. It was filtered and solvent was removed under reduced pressure to give a crude. The crude was used directly in the next step without further purification: ESI-MS m/z: 499[M+H]⁺;

(R)-4-(4-((1-(3-(difluoromethyl)-2-(2-methoxyethoxy)phenyl)ethyl)amino)-7-(2-methoxyethoxy)-2-methylpyrido[2,3-d]pyrimidin-6-yl)tetrahydro-2H-thiopyran 1,1-dioxide To a solution of (R)-4-(7-chloro-4-((1-(3-(difluoromethyl)-2-fluorophenyl)ethyl)amino)-2-methylpyrido[2,3-d]pyrimidin-6-yl)tetrahydro-2H-thiopyran 1,1-dioxide (300 mg, 0.6 mmol) and in 2-methoxyethan-1-ol (10 mL) was added Cs₂CO₃ (587 mg, 1.8 mmol). The mixture was stirred for 16 hours at 125° C. It was cooled to room temperature and solvent was removed under reduced pressure to give a crude. The crude was purified by preparative-TLC (petroleum:ethyl acetate=95:5) to give the desired product ESI-MS m/z: 595 [M+H]⁺. ¹HNMR(CDCl3,400 MHz): δ 8.36 (s, 1H), 7.83 (brs, 1H), 7.69-7.67 (d, J=3.6 Hz, 1H), 7.50-7.48 (d, J=3.6 Hz, 1H), 7.18-7.15 (t, J=3.6 Hz, 1H), 7.12-6.85 (t, J=54.8 Hz, 1H), 5.85-5.78 (m, 1H), 4.62-4.60 (m, 2H), 4.45-4.41 (m, 1H), 4.09-4.04 (m, 1H), 3.90-3.87 (m, 2H), 3.71-3.69 (m, 2H), 3.61 (s, 3H), 3.36 (s, 3H), 3.27-3.10 (m, 5H), 2.59 (s, 3H), 2.40-2.26 (m, 4H), 1.74-1.72 (d, J=7.2 Hz, 3H).

Compound 160: Synthesis of (R)-7-methoxy-N-(1-(2-methyl-3-(trifluoromethyl)phenyl)ethyl)-6-(4-(tetrahydro-2H-pyran-4-yl)piperazin-1-yl)pyrido[2,3-d]pyrimidin-4-amine

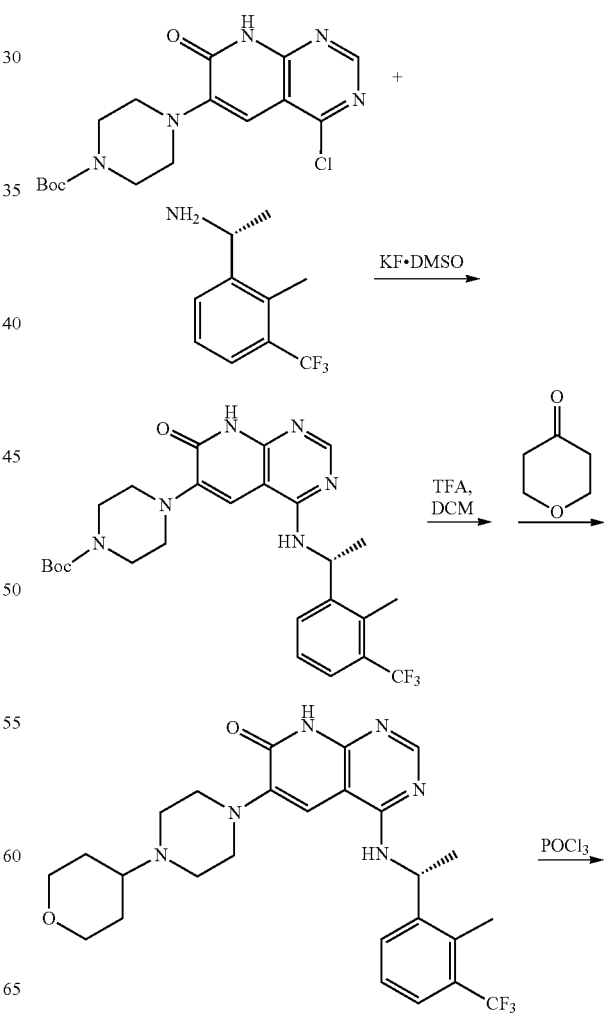

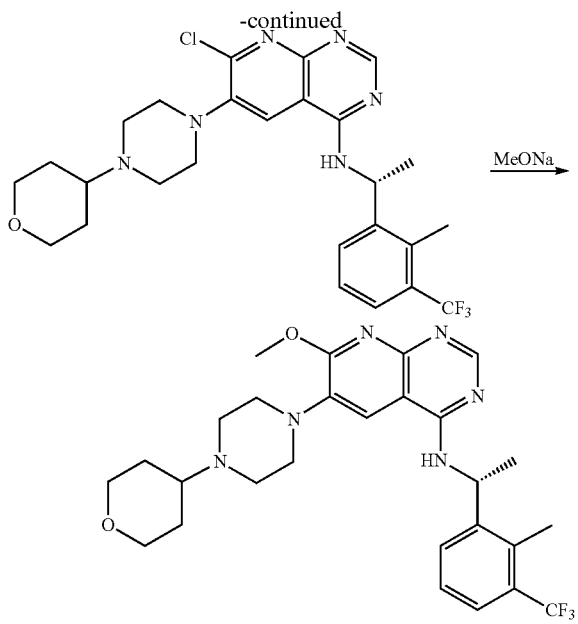

tert-butyl(R)-4-(4-((1-(2-methyl-3-(trifluoromethyl)
phenyl)ethyl)amino)-7-oxo-7,8-dihydropyrido[2,3-d]
pyrimidin-6-yl)piperazine-1-carboxylate To a solution of tert-butyl 4-(4-chloro-7-oxo-7,8-dihydro-pyrido[2,3-d]pyrimidin-6-yl)piperazine-1-carboxylate (200 mg, 0.54 mmol) in dimethyl sulfoxide (10 mL) was added (R)-1-(2-methyl-3-(trifluoromethyl)phenyl)ethan-1-amine (220 mg, 1.08 mmol) and KF (187 mg, 3.24 mmol). The mixture was stirred at 100° C. overnight. It was cooled down to room temperature and treated with NaHCO₃(aq) (5 mL). The mixture was extracted with ethyl acetate. The extracts were combined, washed with brine, and dried over Na₂SO₄. It was filtered and solvent was removed under reduced pressure to give a crude. The crude was purified by flash column chromatography on silica gel to give desired product ESI-MS m/z: 533.2[M+H]⁺.

(R)-4-((1-(2-methyl-3-(trifluoromethyl)phenyl)ethyl)
amino)-6-(4-(tetrahydro-2H-pyran-4-yl)piperazin-1-
yl)pyrido[2,3-d]pyrimidin-7(8H)-one To a solution of To a solution of tert-butyl (R)-4-(4-((1-(2-methyl-3-(trifluoromethyl)phenyl)ethyl)amino)-7-oxo-7,8-dihydropyrido[2,3-d]pyrimidin-6-yl)piperazine-1-carboxylate (200 mg, 0.37 mmol) in DCM (4 mL) was added trifluoroacetic acid (1 mL). The mixture was stirred at room temperature for 1 h. The volatiles were evaporated to afford (R)-4-((1-(2-methyl-3-(trifluoromethyl)phenyl)ethyl)amino)-6-(piperazin-1-yl)pyrido[2,3-d]pyrimidin-7(8H)-one (160 mg, 0.37 mmol). This product was added to a mixture of excessive NaBH₃CN and tetrahydro-4H-pyran-4-one in methanol (15 mL). The mixture was stirred at 60° C. for overnight. It was cooled to room temperature and treated with NaHCO₃(aq) (5 mL). It was extracted with ethyl acetate. The extracts were combined, washed with brine, and dried over Na₂SO₄. It was filtered and solvent was removed under reduced pressure to give a residue. The residue was purified by flash column chromatography on silica gel to give desired product ESI-MS m/z: 517.1[M+H]⁺.

(R)-7-chloro-N-(1-(2-methyl-3-(trifluoromethyl)
phenyl)ethyl)-6-(4-(tetrahydro-2H-pyran-4-yl)piper-
azin-1-yl)pyrido[2,3-d]pyrimidin-4-amine To a solution (R)-4-((1-(2-methyl-3-(trifluoromethyl)phenyl)ethyl)amino)-6-(4-(tetrahydro-2H-pyran-4-yl)piperazin-1-yl)pyrido[2,3-d]pyrimidin-7(8H)-one (110 mg, 0.21 mmol) in POCl₃ (4.5 mL) was added diisopropyl ethyl amine (DIPEA, 0.75 ml). The mixture was stirred at 100° C. for 5 h. The mixture was allowed to cool to room temperature and concentrated in vacuo to remove POCl₃. The residue was treated with ethyl acetate and NaHCO₃(aq). The organics were separated, washed with brine, and dried over Na₂SO₄. It was filtered and solvent was removed under reduced pressure to give a residue. The residue was purified by flash column chromatography on silica gel to give desired product ESI-MS m/z: 536.2 [M+H]⁺.

(R)-7-methoxy-N-(1-(2-methyl-3-(trifluoromethyl)
phenyl)ethyl)-6-(4-(tetrahydro-2H-pyran-4-yl)piper-
azin-1-yl)pyrido[2,3-d]pyrimidin-4-amine Excessive sodium methanolate and sodium hydride were dissolved in methanol (15 ml) and stirred at room temperature for 0.5 h. (R)-7-chloro-N-(1-(2-methyl-3-(trifluoromethyl)phenyl)ethyl)-6-(4-(tetrahydro-2H-pyran-4-yl)piperazin-1-yl)pyrido[2,3-d]pyrimidin-4-amine (56 mg, 0.1 mmol) was added to above mixture. The solution was stirred at 65° C. for 1 hour. It was cooled to room temperature and treated with NaHCO₃(aq) (5 mL). The mixture was extracted with ethyl acetate. The extracts were combined, washed with brine, and dried over Na₂SO₄. It was filtered and solvent was removed under reduced pressure to give a residue. The residue was purified by flash column chromatography on silica gel to give desired product ¹HNMR (DMSO-d6, 400 MHz): δ 8.35-8.3 (m, 2H), 8.0 (s, 1H), 7.77-7.75 (d, J=7.6 Hz, 1H), 7.57-7.55 (d, J=7.2 Hz, 1H), 7.39-7.35 (t, J=7.6 Hz, 1H), 5.76-5.73 (m, 1H), 4.0 (s, 3H), 3.92-3.9 (m, 2H), 3.3-3.2 (m, 2H), 3.13-3.1 (m, 4H), 2.69-2.68 (m, 4H), 2.54-2.5 (s, 3H), 2.01-1.9 (m, 1H), 1.78-1.75 (m, 2H), 1.56-1.54 (d, J=6.8 Hz, 3H), 1.5-1.4 (m, 2H). ESI-MS m/z: 531.2 [M+H]⁺.

Compound 203: Synthesis of (R)-1-(4-((1-(3-(dif-
luoromethyl)-2-fluorophenyl)ethyl)amino)-7-
methoxy-2-((1-methylazetidin-3-yl)methoxy)pyrido
[2,3-d]pyrimidin-6-yl)cyclopropane-1-carbonitrile

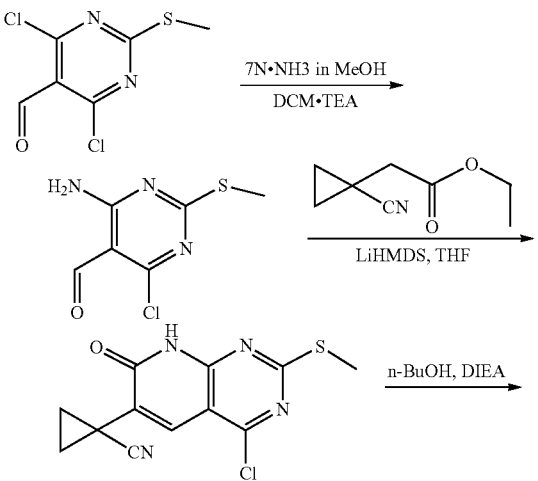

1017

-continued

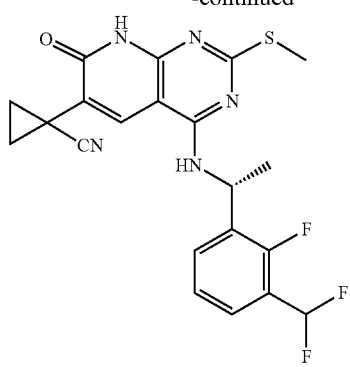

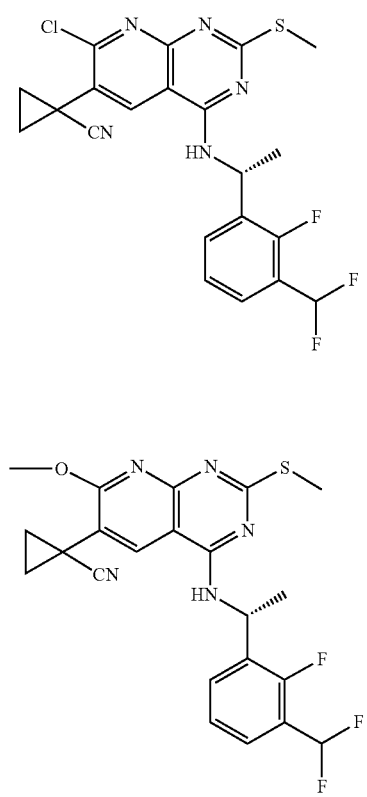

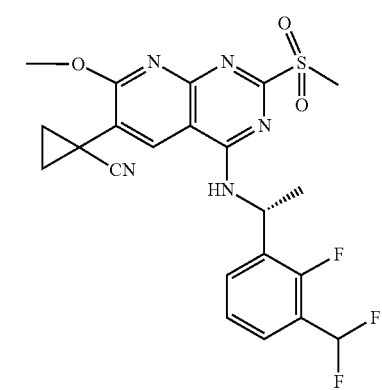

1018

-continued

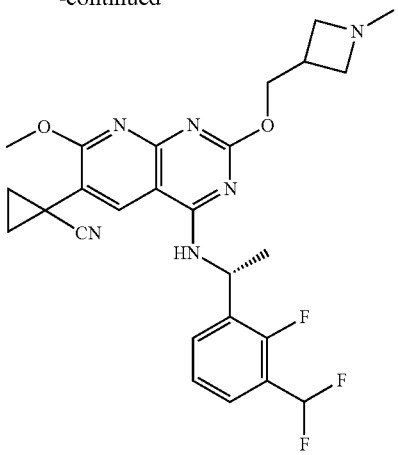

4-amino-6-chloro-2-(methylthio)pyrimidine-5-carbaldehyde

To a solution of 4,6-dichloro-2-(methylthio)pyrimidine-5-carbaldehyde (10 g, 44.8 mmol) in DCM (100 mL) was added 7 N of NH$_3$.MeOH (10 mL), followed by the addition of TEA (5 mL) for over 30 min. The mixture was stirred at room temperature for 2 hours. TLC showed the reaction was completed, and the solvent was removed in vacuo. MeOH (20 mL) was added to the residue. It was filtered and the filter cake was washed by MeOH (10 mL×2). The solid was dried to give the desired product as a solid. ESI-MS m/z: 204 [M+H]$^+$.

1-(4-chloro-2-(methylthio)-7-oxo-7,8-dihydropyrido[2,3-d]pyrimidin-6-yl)cyclopropane-1-carbonitrile A solution of ethyl ethyl 2-(1-cyanocyclopropyl)acetate (2.26 g, 14.8 mmol) and 4-amino-6-chloro-2-(methylthio)pyrimidine-5-carbaldehyde (2 g, 9.8 mmol) in THF (10 mL) was cooled to −78° C. under argon. LiHMDS (29.5 mL, 1 M in THF) was added dropwise, the resulting mixture was stirred for 5.0 hours at −78° C. and allowed to warm RT. The reaction mixture was quenched with saturated NH$_4$Cl (20 mL) and extracted with ethyl acetate (30 mL×2). Organic extracts were combined, washed with brine, and dried over Na$_2$SO$_4$. It was filtered and solvent was removed under reduced pressure to give a crude. The crude was purified by flash chromatography on silica gel (dichloromethane:methyl alcohol=96:4) to give the desired product as a solid. ESI-MS m/z: 293[M+H]$^+$.

(R)-1-(4-((1-(3-(difluoromethyl)-2-fluorophenyl)ethyl)amino)-2-(methylthio)-7-oxo-7,8-dihydropyrido[2,3-d]pyrimidin-6-yl)cyclopropane-1-carbonitrile To a solution of 1-(4-chloro-2-(methylthio)-7-oxo-7,8-dihydropyrido[2,3-d]pyrimidin-6-yl)cyclopropane-1-carbonitrile (800 mg, 2.7 mmol) and (R)-1-(3-(difluoromethyl)-2-fluorophenyl)ethan-1-amine (541 mg, 2.8 mmol) in n-BuOH (20 ml) was added DIEA (3.5 g, 27 mmol). The resulting mixture was heated at 120° C. under argon and stirred for overnight. It was cooled to room temperature and ethyl acetate (60 mL) was added. The organics were washed with brine, dried over Na$_2$SO$_4$. It was filtered and solvent was removed under reduced pressure to give a crude. The crude was purified by flash chromatography on silica gel (dichloromethane:methyl alcohol=95:5) to afford the desired product as a solid. ESI-MS m/z: 445[M+H]⁺;

(R)-1-(7-chloro-4-((1-(3-(difluoromethyl)-2-fluorophenyl)ethyl)amino)-2-(methylthio)pyrido[2,3-d]pyrimidin-6-yl)cyclopropane-1-carbonitrile To a mixture of (R)-1-(4-((1-(3-(difluoromethyl)-2-fluorophenyl)ethyl)amino)-2-(methylthio)-7-oxo-7,8-dihydropyrido[2,3-d]pyrimidin-6-yl)cyclopropane-1-carbonitrile (600 mg, 1.3 mmol) in POCl₃ (5 mL) was added DIEA (two drops) at room temperature. The resulting mixture was heated at 105° C. under argon and stirred for 5.0 h. It was then cooled to RT and concentrated to remove most of POCl₃, and the residue was partitioned between saturated NaHCO₃ (5 mL) and dichloromethane (20 mL). The aqueous layer was extracted with dichloromethane (20 mL×2). The organics were combined, washed with brine, and dried over Na₂SO₄. It was filtered and solvent was removed under reduced pressure to give a crude. The crude was purified by flash chromatography on silica gel (dichloromethane:methyl alcohol=95:5) to afford the desired product as a solid. ESI-MS m/z: 464[M+H]⁺;

(R)-1-(4-((1-(3-(difluoromethyl)-2-fluorophenyl)ethyl)amino)-7-methoxy-2-(methylthio)pyrido[2,3-d]pyrimidin-6-yl)cyclopropane-1-carbonitrile To a solution of (R)-1-(7-chloro-4-((1-(3-(difluoromethyl)-2-fluorophenyl)ethyl)amino)-2-(methylthio)pyrido[2,3-d]pyrimidin-6-yl)cyclopropane-1-carbonitrile (400 mg, 0.86 mmol) in MeOH (20 ml) was added sodium methanolate (232.2 mg, 4.3 mmol) and NaH (60%, 172 mg, 4.3 mmol) at 0° C. Then the resulting mixture was heated at 65° C. under argon and stirred for 2 hours. It was then cooled to RT and concentrated to remove most of MeOH. The mixture was extracted with ethyl acetate (20 mL×2). Organic extracts were combined, washed with brine, and dried over Na₂SO₄. It was filtered and solvent was removed under reduced pressure to give a crude. The crude was purified by flash chromatography on silica gel (dichloromethane:methyl alcohol=95:5) to afford the desired product as a solid. ESI-MS m/z: 460[M+H]⁺;

(R)-1-(4-((1-(3-(difluoromethyl)-2-fluorophenyl)ethyl)amino)-7-methoxy-2-(methylsulfonyl)pyrido[2,3-d]pyrimidin-6-yl)cyclopropane-1-carbonitrile To a solution of (R)-1-(4-((1-(3-(difluoromethyl)-2-fluorophenyl)ethyl)amino)-7-methoxy-2-(methylthio)pyrido[2,3-d]pyrimidin-6-yl)cyclopropane-1-carbonitrile (280 mg, 0.61 mmol) in DCM (10 mL) was added m-CPBA (262 mg, 1.5 mmol). Then the resulting mixture was stirred at room temperature for 2 hours, and TLC showed the reaction was completed. The mixture was treated with DCM (20 mL), washed with aq.NaHCO₃, and dried over Na₂SO₄. The solvent was removed under reduced pressure to give a crude. The crude was purified by flash chromatography on silica gel (dichloromethane:methyl alcohol=95:5) to afford the desired product as a solid. ESI-MS m/z: 492[M+H]⁺;

(R)-1-(4-((1-(3-(difluoromethyl)-2-fluorophenyl)ethyl)amino)-7-methoxy-2-((1-methylazetidin-3-yl)methoxy)pyrido[2,3-d]pyrimidin-6-yl)cyclopropane-1-carbonitrile To a solution of (1-methylazetidin-3-yl)methanol (12 mg, 0.12 mmol) in THF (10 mL) was added NaH (60%, 6.1 mg, 0.15 mmol) at 0° C. The mixture was stirred at 0° C. for 30 min, then (R)-1-(4-((1-(3-(difluoromethyl)-2-fluorophenyl)ethyl)amino)-7-methoxy-2-(methylsulfonyl)pyrido[2,3-d]pyrimidin-6-yl)cyclopropane-1-carbonitrile (50 mg, 0.1 mmol) was added. The resulting mixture was stirred at room temperature for 1 hours. It was extracted with ethyl acetate (20 mL×2). Organic extracts were combined, washed with brine, and dried over Na₂SO₄. It was filtered and solvent was removed under reduced pressure to give a crude. The crude was purified by preparative-TLC (dichloromethane:methyl alcohol=25:1) to afford the desired product as a solid. ESI-MS m/z: 513[M+H]⁺. ¹HNMR (MeOD, 400 MHz): 8.60 (s, 1H), 7.60-7.56 (t, J=7.2 Hz, 1H), 7.50-7.46 (t, J=6.4 Hz, 1H), 7.26-7.22 (t, J=7.6 Hz, 1H), 7.13-6.86 (t, J=54.8 Hz, 1H), 5.69-5.64 (m, 1H), 4.41-4.37 (m, 1H), 4.22-4.14 (m, 4H), 3.66-3.57 (m, 2H), 3.64-3.33 (m, 3H), 2.91-2.87 (m, 1H), 2.47 (s, 3H), 1.74-1.67 (m, 5H), 1.48-1.45 (m, 2H).

Compound 271: Synthesis of (R)-4-(4-((1-(3-(2-(2-(dimethylamino)ethoxy)-1,1-difluoroethyl)-2-fluorophenyl)ethyl)amino)-7-methoxy-2-methylpyrido[2,3-d]pyrimidin-6-yl)tetrahydro-2H-thiopyran 1,1-dioxide

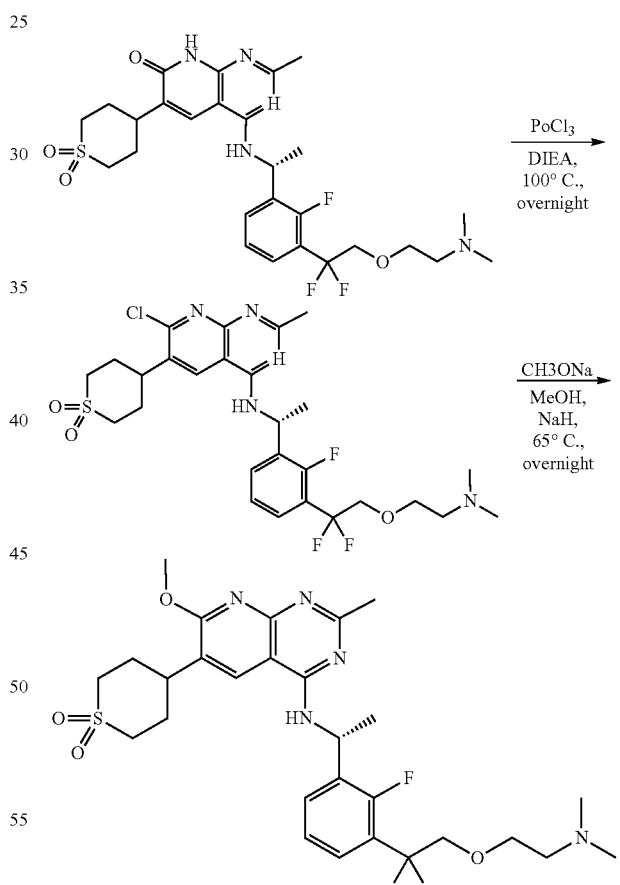

(R)-4-(7-chloro-4-((1-(3-(2-(2-(dimethylamino)ethoxy)-1,1-difluoroethyl)-2-fluorophenyl)ethyl)amino)-2-methylpyrido[2,3-d]pyrimidin-6-yl)tetrahydro-2H-thiopyran 1,1-dioxide To a mixture of (R)-4-((1-(3-(2-(2-(dimethylamino)ethoxy)-1,1-difluoroethyl)-2-fluorophenyl)ethyl)amino)-6-

(1,1-dioxidotetrahydro-2H-thiopyran-4-yl)-2-methylpyrido[2,3-d]pyrimidin-7(8H)-one (170 mg, 1.00 mmol) and POCl₃ (2 mL) was added DIEA (cat) at room temperature. The resulting mixture was heated at 100° C. under argon and stirred for overnight. Then it was cooled to RT and concentrated to remove most of POCl₃. The residue was partitioned between saturated NaHCO₃ (5 mL) and dichloromethane (20 mL). The aqueous layer was extracted with dichloromethane (20 mL×2). The organics were combined, washed with brine, dried over Na₂SO₄. It was filtered and solvent was removed under reduced pressure to give a crude. The crude was purified by flash chromatography on silica gel (dichloromethane:methyl alcohol=20:1) to afford the desired product as a solid. ESI-MS m/z: 600[M+H]⁺;

(R)-4-(4-((1-(3-(2-(2-(dimethylamino)ethoxy)-1,1-difluoroethyl)-2-fluorophenyl)ethyl)amino)-7-methoxy-2-methylpyrido[2,3-d]pyrimidin-6-yl)tetrahydro-2H-thiopyran 1,1-dioxide To a solution of (R)-4-(7-chloro-4-((1-(3-(2-(2-(dimethylamino)ethoxy)-1,1-difluoroethyl)-2-fluorophenyl)ethyl)amino)-2-methylpyrido[2,3-d]pyrimidin-6-yl)tetrahydro-2H-thiopyran 1,1-dioxide2,3-d]pyrimidin-6-yl)tetrahydro-2H-thiopyran1,1-dioxide (55 mg, 1.00 mmol) in MeOH (10 mL) was sodium methanolate (20 mg, 3.0 mmol) and NaH (60%, 18 mg, 5 mmol) at 0° C. The resulting mixture was heated at 65° C. under argon and stirred for overnight. It was cooled to RT and concentrated to remove most of MeOH. The mixture was extracted with ethyl acetate (20 mL×2). Organic extracts were combined, washed with brine, and dried over Na₂SO₄. It was filtered and solvent was removed under reduced pressure to give a crude. The crude was purified by preparative-TLC (dichloromethane:methyl alcohol=20:1) to afford the desired product as a solid. ESI-MS m/z: 596[M+H]⁺. ¹HNMR (400 MHz, MeOD): δ 8.55 (s, 1H), 7.62 (t, J=6.8 Hz, 1H), 7.50 (t, J=6.8 Hz, 1H), 7.23 (t, J=7.6 Hz, 1H), 5.85 (m, 1H), 4.17 (m, 2H), 4.14 (m, 3H), 3.88 (m, 2H), 3.41 (m, 3H), 3.32 (m, 4H), 2.67 (s, 6H), 2.38 (s, 3H), 2.35 (m, 4H), 1.61 (d, J=6.8 Hz, 3H).

Compound 225: Synthesis of (R)-1-(4-((1-(3-(difluoromethyl)-2-fluorophenyl)ethyl)amino)-2-methyl-7-(oxetan-3-ylamino)pyrido[2,3-d]pyrimidin-6-yl)cyclopropane-1-carbonitrile -continued

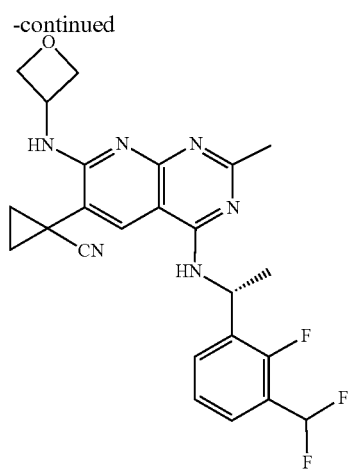

(R)-1-(4-((1-(3-(difluoromethyl)-2-fluorophenyl)ethyl)amino)-2-methyl-7-(oxetan-3-ylamino)pyrido[2,3-d]pyrimidin-6-yl)cyclopropane-1-carbonitrile To a solution of 1-methylazetidin-3-ol (19 mg, 0.22 mmol) in MeCN (5 mL) was added NaH (17 mg, 0.43 mmol). The mixture was stirred for 10 min, and 1-(5,7-dichloro-4-(((R)-1-(3-(difluoromethyl)-2-fluorophenyl)ethyl)amino)-2-methyl-5,6-dihydropyrido[2,3-d]pyrimidin-6-yl)cyclopropane-1-carbonitrile (20 mg, 0.086 mmol) was added. The mixture was heated for 100° C. under argon and stirred for 3.0 hours. It was cooled down to room temperature and extracted with ethyl acetate (20 mL×2). Organic extracts were combined, washed with brine, and dried over Na₂SO₄. It was filtered and solvent was removed under reduced pressure to give a crude. The crude was purified by preparative-TLC (dichloromethane:methyl alcohol=89:11) to afford the desired product ESI-MS m/z: 469[M+H]⁺; HNMR (CD3OD, 400 MHz): δ 8.24 (s, 1H), 7.68-7.65 (t, J=6.8 Hz, 1H), 7.52-7.48 (t, J=6.4 Hz, 1H), 7.28-7.24 (t, J=7.6 Hz, 1H), 7.17-6.90 (t, J=54.8, 1H), 5.86-5.84 (m, 1H), 5.74-5.71 (m, 1H), 5.39-5.36 (m, 2H), 5.09-5.03 (m, 2H), 3.61-3.52 (m, 1H), 2.48 (s, 3H), 2.23-2.20 (m, 2H), 1.75-1.65 (m, 2H), 1.71-1.69 (m, 3H).

Compound 157: Synthesis of (R)-4-(4-((1-(3-(difluoromethyl)-2-fluorophenyl)ethyl)amino)-7-(2-methoxyethoxy)-2-methylpyrido[2,3-d]pyrimidin-6-yl)tetrahydro-2H-thiopyran 1,1-dioxide

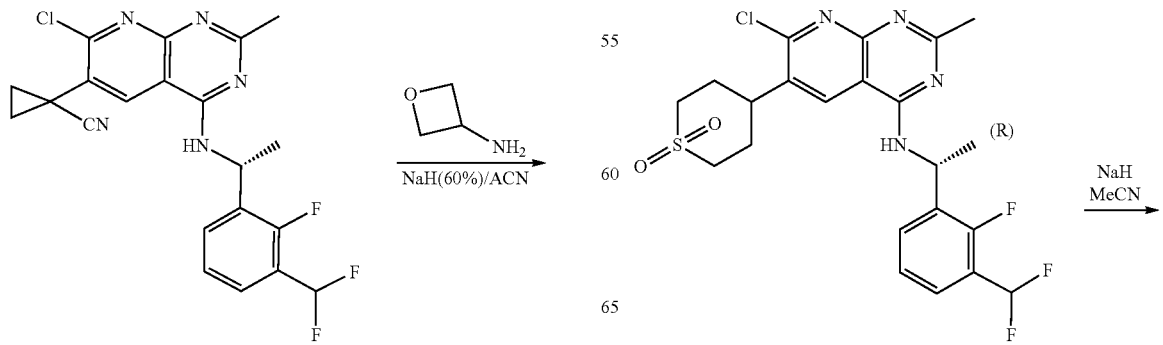

1023

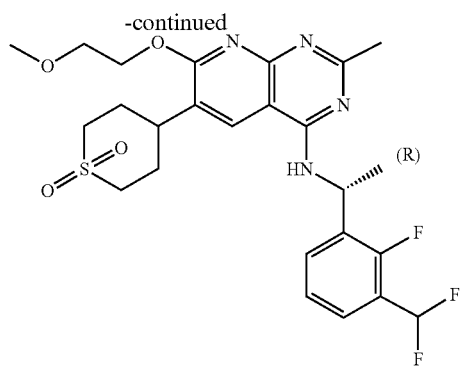

1024

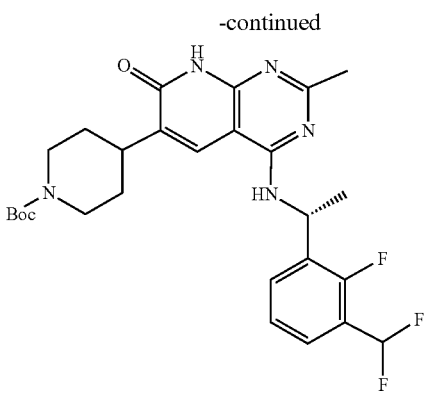

(R)-4-(4-(((1-(3-(difluoromethyl)-2-fluorophenyl)ethyl)amino)-7-(2-methoxyethoxy)-2-methylpyrido[2,3-d]pyrimidin-6-yl)tetrahydro-2H-thiopyran 1,1-dioxide To a solution of 2-methoxyethan-1-ol (106 mg, 1.2 mmol) in MeCN (10 mL) was added NaH (60%, 72 mg, 1.8 mmol), and (R)-4-(7-chloro-4-((1-(3-(difluoromethyl)-2-fluorophenyl)ethyl)amino)-2-methylpyrido[2,3-d]pyrimidin-6-yl)tetrahydro-2H-thiopyran 1,1-dioxide (300 mg, 0.6 mmol) in seal tube. in seal tube. The resulting mixture was heated at 100° C. under argon and stirred for 3.0 hours. It was cooled to room temperature and concentrated to remove most of MeOH. The mixture was extracted with ethyl acetate (50 mL×2). Organic extracts were combined, washed with brine, and dried over Na$_2$SO$_4$. It was filtered and solvent was removed under reduced pressure to give a crude. The crude was purified by preparative-TLC (dichloromethane:methyl alcohol=95:5) to afford the desired product. ESI-MS m/z: 539 [M+H]$^+$. $^1$HNMR (CDCl3, 400 MHz): δ 7.85 (s, 1H), 7.58-7.54 (t, J=7.2 Hz, 1H), 7.51-7.47 (t, J=6.8 Hz, 1H), 7.21-7.17 (t, J=7.6 Hz, 1H), 7.06-6.78 (t, J=54.8 Hz, 1H), 6.20-6.18 (d, J=7.2 Hz, 1H), 5.83-5.79 (m, 1H), 4.67-4.65 (t, J=4.4 Hz, 2H), 3.75-3.73 (t, J=4.4 Hz, 2H), 3.39 (s, 3H), 3.25-3.11 (m, 5H), 2.55 (s, 3H), 2.35-2.30 (m, 4H), 1.73-1.71 (d, J=7.2 Hz, 3H).

Compound 121: Synthesis of (R)—N-(1-(3-(difluoromethyl)-2-fluorophenyl)ethyl)-7-methoxy-2-methyl-6-(piperidin-4-yl)pyrido[2,3-d]pyrimidin-4-amine

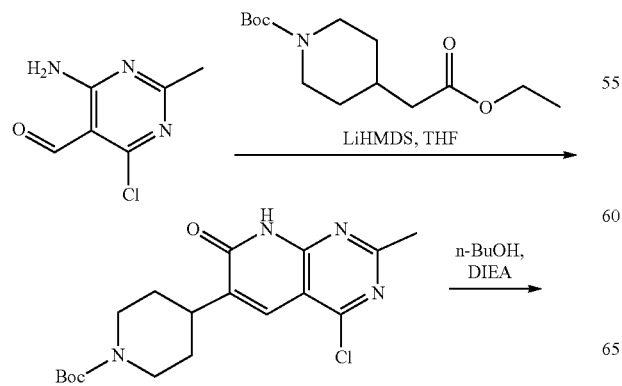

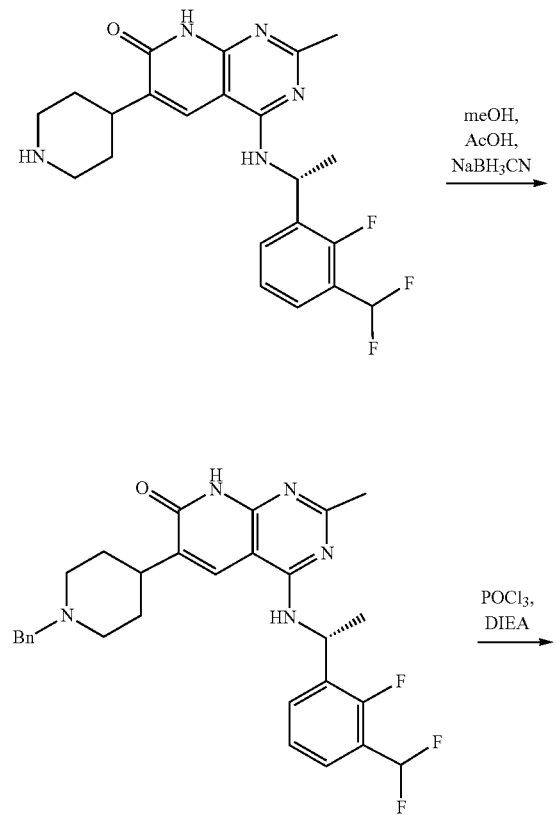

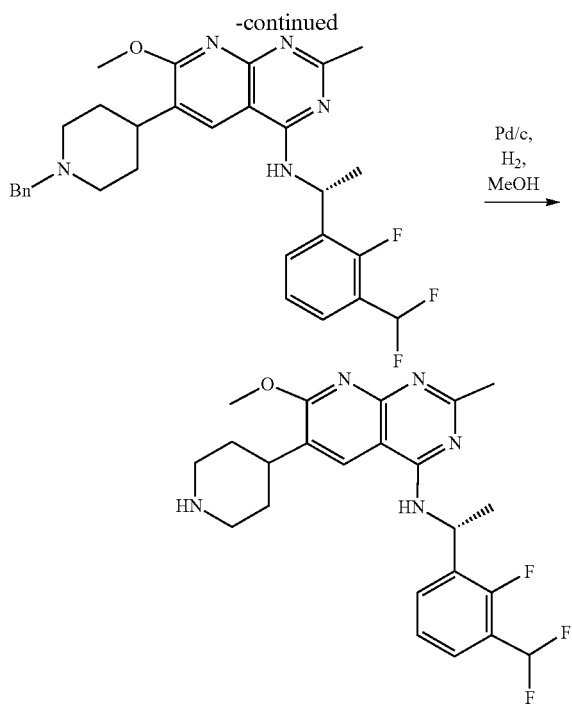

tert-butyl 4-(4-chloro-2-methyl-7-oxo-7,8-dihydropyrido[2,3-d]pyrimidin-6-yl)piperidine-1-carboxylate A solution of tert-butyl 4-(2-ethoxy-2-oxoethyl)piperidine-1-carboxylate (2 g, 7.4 mmol) in THF (20 mL) and 4-amino-6-chloro-2-methylpyrimidine-5-carbaldehyde (1.3 g, 7.4 mmol) was cooled to −78° C. under argon. LiHMDS (22 mL, 1 M in THF) was added dropwise and the resulting mixture was stirred for 5 hours at −78° C. and allowed to warm room temperature. The reaction mixture was quenched with saturated NH$_4$Cl (20 ml) and extracted with ethyl acetate (30 mL×2). Organic extracts were combined, washed with brine, and dried over Na$_2$SO$_4$. It was filtered and solvent was removed under reduced pressure to give a crude. The crude was purified by flash chromatography on silica gel (dichloromethane:methyl alcohol=96:4) to give the desired product as a solid. ESI-MS m/z: 379 [M+H]$^+$.

tert-butyl (R)-4-(4-((1-(3-(difluoromethyl)-2-fluorophenyl)ethyl) amino)-2-methyl-7-oxo-7,8-dihydropyrido[2,3-d]pyrimidin-6-yl)piperidine-1-carboxylate To a solution of tert-butyl 4-(4-chloro-2-methyl-7-oxo-7,8-dihydropyrido[2,3-d]pyrimidin-6-yl)piperidine-1-carboxylate (1.6 g, 4.2 mmol) and (R)-1-(3-(difluoromethyl)-2-fluorophenyl)ethan-1-amine (957 mg, 4.2 mmol) in n-BuOH (20 mL) was added DIEA (3.5 g, 27 mmol). The resulting mixture was heated at 120° C. under argon and stirred for overnight. It was cooled to room temperature and ethyl acetate (60 mL) was added. The organics were washed with brine, dried over Na$_2$SO$_4$. It was filtered and solvent was removed under reduced pressure to give a crude. The crude was purified by flash chromatography on silica gel (dichloromethane:methyl alcohol=95:5) to afford the desired product as a solid. ESI-MS m/z: 532 [M+H]$^+$;

(R)-4-((1-(3-(difluoromethyl)-2-fluorophenyl)ethyl) amino)-2-methyl-6-(piperidin-4-yl)pyrido[2,3-d] pyrimidin-7(8H)-one To a solution of tert-butyl (R)-4-(4-((1-(3-(difluoromethyl)-2-fluorophenyl)ethyl)amino)-2-methyl-7-oxo-7,8-dihydropyrido[2,3-d]pyrimidin-6-yl)piperidine-1-carboxylate (1.7 g, 3.2 mmol) in DCM (20 mL) was added TFA (5 mL). The mixture was stirred at room temperature for 1 hour, then the solvent was removed in vacuo. The residue was dissolved in DCM (20 mL), washed by aq.NaHCO$_3$ (30 mL), and dried over Na$_2$SO$_4$. It was filtered and the solvent was removed under reduced pressure to give a crude which was used in the next step without further purification as a yellow solid. ESI-MS m/z: 432 [M+H]$^+$

(R)-6-(1-benzylpiperidin-4-yl)-4-((1-(3-(difluoromethyl)-2-fluorophenyl)ethyl)amino)-2-methylpyrido[2,3-d]pyrimidin-7(8H)-one To a solution of (R)-4-((1-(3-(difluoromethyl)-2-fluorophenyl)ethyl)amino)-2-methyl-6-(piperidin-4-yl)pyrido[2,3-d]pyrimidin-7(8H)-one (900 mg, 2.1 mmol) in MeOH (20 mL) was added benzaldehyde (223 mg, 2.1 mmol) and AcOH (12.5 mg, 0.2 mmol). The mixture was stirred at room temperature for 30 min and then cooled to 0° C. NaBH$_3$CN (197 mg, 3.1 mmol) was added. It was allowed warmed to room temperature and stirred for overnight. The solvent was removed in vacuo to give a crude. The crude was purified by flash chromatography on silica gel (dichloromethane:methyl alcohol=95:5) to afford the desired product as a solid. ESI-MS m/z: 522[M+H]$^+$;

(R)-6-(1-benzylpiperidin-4-yl)-7-chloro-N-(1-(3-(difluoromethyl)-2-fluorophenyl)ethyl)-2-methylpyrido[2,3-d]pyrimidin-4-amine To a mixture of (R)-6-(1-benzylpiperidin-4-yl)-4-((1-(3-(difluoromethyl)-2-fluorophenyl)ethyl)amino)-2-methylpyrido[2,3-d]pyrimidin-7(8H)-one (740 mg, 1.3 mmol) and POCl$_3$ (10 mL) was added DIEA (two drops) at room temperature. The resulting mixture was heated at 105° C. under argon and stirred for 5 h. Then it was cooled to room temperature and concentrated to remove most of POCl$_3$. The resulting residue was partitioned between saturated NaHCO$_3$ (5 mL) and dichloromethane (20 mL). The aqueous layer was extracted with dichloromethane (20 mL×2). The organics were combined, washed with brine, and dried over Na$_2$SO$_4$. It was filtered and solvent was removed under reduced pressure to give a crude. The crude was purified by flash chromatography on silica gel (dichloromethane:methyl alcohol=95:5) to afford the desired product as a solid. ESI-MS m/z: 542[M+H]$^+$;

(R)-6-(1-benzylpiperidin-4-yl)-N-(1-(3-(difluoromethyl)-2-fluorophenyl)ethyl)-7-methoxy-2-methylpyrido[2,3-d]pyrimidin-4-amine To a solution of (R)-6-(1-benzylpiperidin-4-yl)-7-chloro-N-(1-(3-(difluoromethyl)-2-fluorophenyl)ethyl)-2-methylpyrido[2,3-d]pyrimidin-4-amine (400 mg, 0.74 mmol) in MeOH (20 mL) was added sodium methanolate (200 mg, 3.7 mmol) and NaH (60%, 147 mg, 3.7 mmol) at 0° C. Then the resulting mixture was heated at 65° C. under argon and stirred for 2 hours. It was then cooled to room temperature and concentrated to remove most of MeOH. The mixture was extracted with ethyl acetate (20 mL×2). Organic extracts were combined, washed with brine, and dried over Na₂SO₄. It was filtered and solvent was removed under reduced pressure to give a crude. The crude was purified by flash chromatography on silica gel (dichloromethane:methyl alcohol=95:5) to afford the desired product as a solid. ESI-MS m/z: 536[M+H]⁺;

(R)—N-(1-(3-(difluoromethyl)-2-fluorophenyl)ethyl)-7-methoxy-2-methyl-6-(piperidin-4-yl)pyrido[2,3-d]pyrimidin-4-amine To a solution of (R)-6-(1-benzylpiperidin-4-yl)-N-(1-(3-(difluoromethyl)-2-fluorophenyl)ethyl)-7-methoxy-2-methylpyrido[2,3-d]pyrimidin-4-amine (288 mg, 0.54 mmol) in MeOH (10 mL) was added Pd on carbon (10%, 28 mg). It was evacuated and back filled with hydrogen. This was repeated for 3 times and the resulting mixture stirred for 2 hours under hydrogen at room temperature. Then it filtered and concentrated to give a crude. The crude was purified by flash chromatography on silica gel (dichloromethane:methyl alcohol=90:10) to afford the desired product as a solid. ESI-MS m/z: 446[M+H]⁺, HNMR (MeOD, 400 Mhz): 8.71 (s, 1H), 7.75-7.71 (t, J=6.8 Hz, 1H), 7.53-7.49 (t, J=6.8 Hz, 1H), 7.31-7.26 (m, 1H), 7.15-6.88 (t, J=54.8 Hz, 1H), 5.97-5.92 (m, 1H), 4.14 (s, 3H), 3.59-3.56 (m, 2H), 3.28-3.17 (m, 3H), 2.52 (s, 3H), 2.22-2.07 (m, 4H), 1.76-1.74 (d, J=6.8 Hz, 3H).

Compound 124: Synthesis of (R)-4-(4-((1-(3-(difluoromethyl)-2-fluorophenyl)ethyl)amino)-7-methoxy-2-methylpyrido[2,3-d]pyrimidin-6-yl)-N-(1-methylazetidin-3-yl)piperidine-1-carboxamide

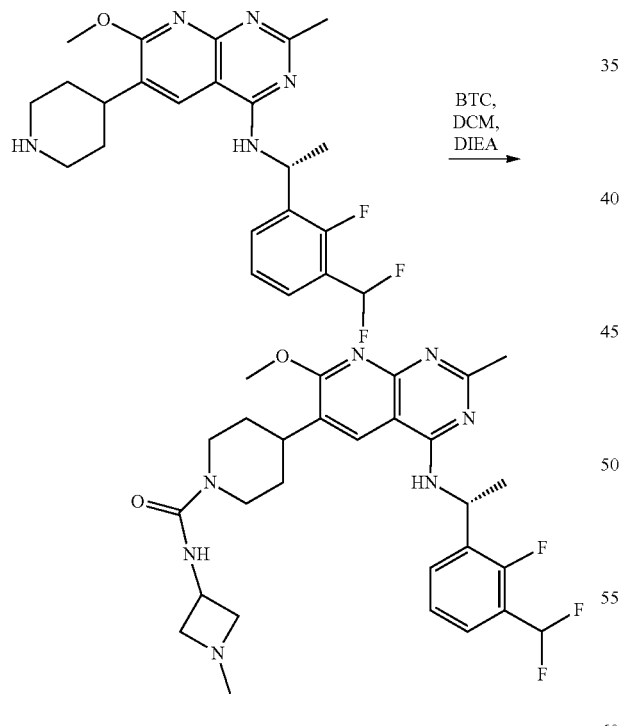

(R)-4-(4-((1-(3-(difluoromethyl)-2-fluorophenyl)ethyl)amino)-7-methoxy-2-methylpyrido[2,3-d]pyrimidin-6-yl)-N-(1-methylazetidin-3-yl)piperidine-1-carboxamide To a solution of 1-methylazetidin-3-amine (5.7 mg, 0.07 mmol) in DCM (10 mL) was added BTC (19.9 mg, 0.07 mmol) at 0° C. To this mixture was added DIEA (2 6 mg, 0.2 mmol). The reaction mixture was stirred at 0° C. for 30 min, then (R)—N-(1-(3-(difluoromethyl)-2-fluorophenyl)ethyl)-7-methoxy-2-methyl-6-(piperidin-4-yl)pyrido[2,3-d]pyrimidin-4-amine (30 mg, 0.07 mmol) in 5 mL of DCM was added. The temperature of reaction mixture was allowed to warm to room temperature and stirred for 30 min. The mixture was extracted with DCM (20 mL), washed with aq.NaHCO₃, and dried over Na₂SO₄. The solvent was removed under reduced pressure to give a crude. The crude was purified by preparative-TLC (dichloromethane:methyl alcohol=15:1) to afford the desired product as a solid. ESI-MS m/z: 558[M+H]⁺; HNMR (CD3OD, 400 MHz): δ 8.61 (s, 1H), 7.64 (t, 1H), 7.46-7.45 (t, 1H), 7.25-7.21 (t, J=7.6 Hz, 1H), 7.08-6.81 (t, J=54.8 Hz, 1H), 5.92-5.90 (m, 1H), 4.51-4.97 (m, 1H), 4.35-4.17 (m, 6H), 4.09 (s, 3H), 3.14 (m, 1H), 2.96-2.90 (m, 5H), 2.51 (s, 3H), 1.93-1.90 (m, 2H), 1.70-1.65 (m, 5H).

Compound 130: Synthesis of (R)-2-(4-(4-((1-(3-(difluoromethyl)-2-fluorophenyl)ethyl)amino)-7-methoxy-2-methylpyrido[2,3-d]pyrimidin-6-yl)piperidin-1-yl)ethan-1-ol

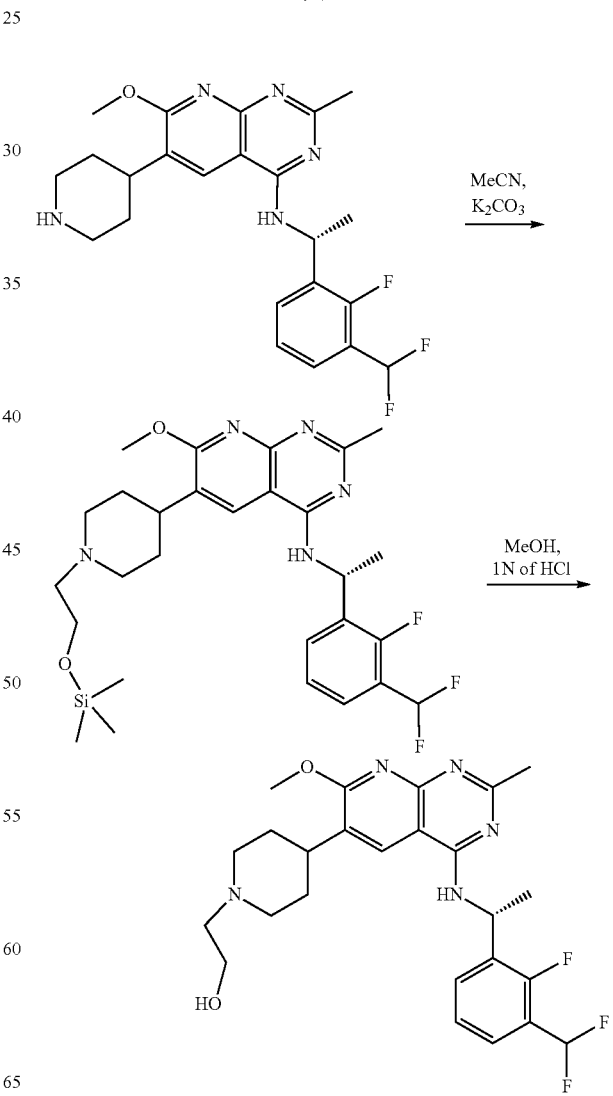

(R)—N-(1-(3-(difluoromethyl)-2-fluorophenyl)ethyl)-7-methoxy-2-methyl-6-(1-(2-((trimethylsilyl)oxy)ethyl)piperidin-4-yl)pyrido[2,3-d]pyrimidin-4-amine To a solution of (R)—N-(1-(3-(difluoromethyl)-2-fluorophenyl)ethyl)-7-methoxy-2-methyl-6-(piperidin-4-yl)pyrido[2,3-d]pyrimidin-4-amine (50 mg, 0.11 mmol) in MeCN (10 mL) was added (2-bromoethoxy)trimethylsilane (27 mg, 0.11 mmol) and K$_2$CO$_3$ (23 mg, 0.17 mmol). The mixture was heated to 80° C. and stirred for 10 hours. TLC showed the reaction was completed. It was cooled to room temperature, filtered and concentrated to give the desired product without further purification (60 mg) which was used directly in the next step. ESI-MS m/z: 562[M+H]$^+$;

(R)-2-(4-(4-((1-(3-(difluoromethyl)-2-fluorophenyl)ethyl)amino)-7-methoxy-2-methylpyrido[2,3-d]pyrimidin-6-yl)piperidin-1-yl)ethan-1-ol To a solution of (R)—N-(1-(3-(difluoromethyl)-2-fluorophenyl)ethyl)-7-methoxy-2-methyl-6-(1-(2-((trimethylsilyl)oxy)ethyl)piperidin-4-yl)pyrido[2,3-d]pyrimidin-4-amine (60 mg) in MeOH (5 mL) was added 1N of HCl (2 mL). The mixture was heated to 50° C. and stirred for 1 hour. It was cooled and solvent was removed under reduced pressure to give a crude. The crude was purified by preparative-TLC (dichloromethane:methyl alcohol=10:1) to afford the desired product as a solid. ESI-MS m/z: 490[M+H]$^+$; $^1$HNMR (DMSO-d6, 400 MHz): δ 8.67 (brs, 1H), 8.58 (brs, 1H), 7.75 (m, 1H), 7.59-7.55 (m, 1H), 7.43-7.16 (m, 2H), 5.87-5.84 (m, 1H), 4.05 (s, 3H), 3.83-3.57 (m, 5H), 3.32-3.10 (m, 5H), 2.40 (s, 3H), 2.10-2.05 (m, 4H), 1.69-1.67 (d, J=6.8 Hz, 3H).

Compound 143: Synthesis of (R)-4-(4-((1-(3-(difluoromethyl)-2-fluorophenyl)ethyl)amino)-7-(dimethylamino)-2-methylpyrido[2,3-d]pyrimidin-6-yl)tetrahydro-2H-thiopyran 1,1-dioxide

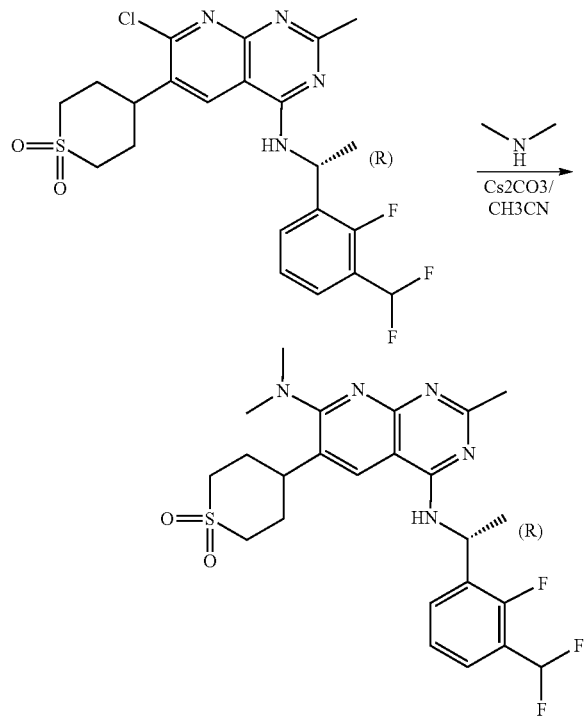

(R)-4-(4-((1-(3-(difluoromethyl)-2-fluorophenyl)ethyl)amino)-7-(dimethylamino)-2-methylpyrido[2,3-d]pyrimidin-6-yl)tetrahydro-2H-thiopyran 1,1-dioxide To a solution of (R)-4-(7-chloro-4-((1-(3-(difluoromethyl)-2-fluorophenyl)ethyl)amino)-2-methylpyrido[2,3-d]pyrimidin-6-yl)tetrahydro-2H-thiopyran 1,1-dioxide (50 mg, 0.10 mmol), dimethylamine (9 mg, 0.20 mmol) in CH$_3$CN (10 ml) was added Cs$_2$CO$_3$ (98 mg, 0.30 mmol). The resulting mixture was heated at 100° C. in seal tube and stirred for 3.0 hours. It was cooled to room temperature and extracted with ethyl acetate (15 mL×2). Organic extracts were combined, washed with brine, and dried over Na$_2$SO$_4$. It was filtered and solvent was removed under reduced pressure to give a crude. The crude was purified by prep-TLC to afford the desired product as a white solid. ESI-MS m/z: 508 [M+H]$^+$; 8.59 (s, 1H), 7.66-7.63 (t, J=7.2 Hz, 1H), 7.53-7.50 (t, J=6.8 Hz, 1H), 7.14 (t, J=7.6 Hz, 1H), 7.00 (t, J=54.8 Hz, 1H, 5.94-5.88 (m, 1H), 3.47-3.39 (m, 2H), 3.15-3.13 (m, 6H), 2.49 (s, 3H), 2.43-2.38 (m, 2H), 2.29-2.24 (m, 2H), 1.95 (s, 1H), 1.73-1.71 (d, J=7.2 Hz, 3H), 1.34-1.28 (m, 2H).

Compound 136: Synthesis of (R)-4-(4-((1-(3-(difluoromethyl)-2-fluorophenyl)ethyl)amino)-2-methyl-7-(methylamino)pyrido[2,3-d]pyrimidin-6-yl)tetrahydro-2H-thiopyran 1,1-dioxide

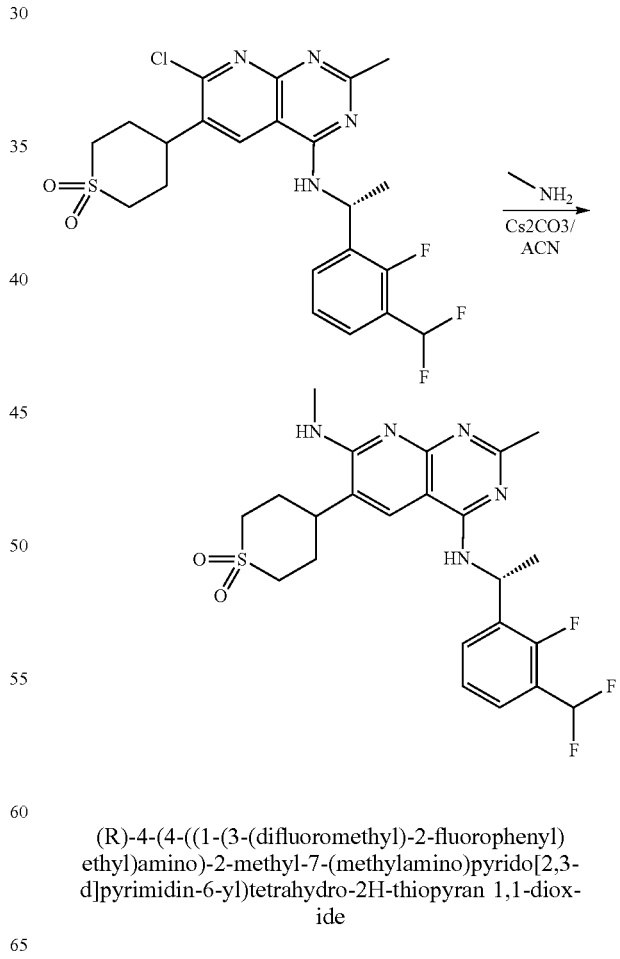

(R)-4-(4-((1-(3-(difluoromethyl)-2-fluorophenyl)ethyl)amino)-2-methyl-7-(methylamino)pyrido[2,3-d]pyrimidin-6-yl)tetrahydro-2H-thiopyran 1,1-dioxide To a solution of (R)-4-(7-chloro-4-((1-(3-(difluoromethyl)-2-fluorophenyl)ethyl)amino)-2-methylpyrido[2,3-d]

pyrimidin-6-yl)tetrahydro-2H-thiopyran 1,1-dioxide (120 mg, 0.30 mmol), methanamine (30 mg, 1.50 mmol) in CH₃CN (10 mL) was added Cs₂CO₃ (294 mg, 1.50 mmol)). The resulting mixture was heated at 100° C. in seal tube and stirred for 3.0 hours. The mixture was cooled to room temperature, extracted with ethyl acetate (15 mL×2). Organic extracts were combined, washed with brine, and dried over Na₂SO₄. It was filtered and solvent was removed under reduced pressure to give a crude. The crude was purified by prep-TLC to afford the desired product as a white solid. ESI-MS m/z: 494 [M+H]⁺. ¹HNMR (DMSO-d6, 400 MHz): δ 8.29 (s, 1H), 7.61-7.57 (m, 1H), 7.49-7.46 (m, 1H), 7.26-7.22 (m, 1H), 7.13-6.86 (t, J=54.8 Hz, 1H), 5.85-5.83 (m, 1H), 3.38-3.34 (m, 2H), 3.19-3.16 (m, 2H), 3.07 (s, 3H), 2.93-2.92 (m, 1H), 2.44-2.23 (m, 7H), 1.67-1.66 (d, J=7.2 Hz, 3H).

Compound 145: Synthesis of (R)-4-(4-((1-(3-(difluoromethyl)-2-fluorophenyl)ethyl)amino)-7-(2-(dimethylamino)ethoxy)-2-methylpyrido[2,3-d]pyrimidin-6-yl)tetrahydro-2H-thiopyran 1,1-dioxide-4-(4-((1-(3-(difluoromethyl)-2-fluorophenyl)ethyl) amino)-7-(2-(dimethylamino)ethoxy)-2-methylpyrido[2,3-d]pyrimidin-6-yl)tetrahydro-2H-thiopyran 1,1-dioxide

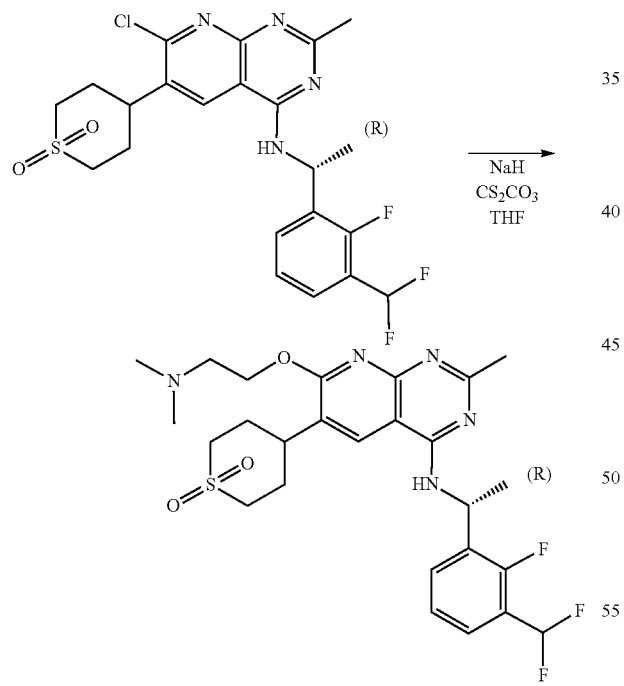

To a solution of 2-(dimethylamino)ethan-1-ol (71 mg, 0.8 mmol) in THF (10 mL), was added NaH (60%, 48 mg, 1.2 mmol), Cs₂CO₃ (393 mg, 1.2 mmol), and (R)-4-(7-chloro-4-((1-(3-(difluoromethyl)-2-fluorophenyl)ethyl)amino)-2-methylpyrido[2,3-d]pyrimidin-6-yl)tetrahydro-2H-thiopyran 1,1-dioxide (200 mg, 0.4 mmol) in seal tube. Then The resulting mixture was heated at 100° C. under argon and stirred for 3.0 hours. Then the reaction mixture was cooled to room temperature and concentrated to remove most of MeOH. The mixture was extracted with ethyl acetate (20 mL×2). Organic extracts were combined, washed with brine, and dried over Na₂SO₄. It was filtered and solvent was removed under reduced pressure to give a crude. The crude was purified by prep-TLC (dichloromethane:methyl alcohol=95:5) to afford the desired product ESI-MS m/z: 552 [M+H]⁺. ¹HNMR (DMSO-d6, 400 MHz): δ 8.35-8.34 (m, 1H), 8.20 (s, 1H), 7.67-7.63 (m, 1H), 7.52-7.49 (m, 1H), 7.37-7.10 (m, 2H), 5.75-5.72 (m, 1H), 4.44-4.36 (m, 2H), 3.23-3.12 (m, 4H), 2.51 (m, 2H), 2.31 (s, 3H), 2.21 (s, 6H), 2.17-2.14 (m, 5H), 1.60-1.58 (m, 3H)

Compound 191: Synthesis of (R)-4-(4-((1-(3-(difluoromethyl)-2-fluorophenyl)ethyl)amino)-2-methyl-7-((1-methylazetidin-3-yl)oxy)pyrido[2,3-d]pyrimidin-6-yl)tetrahydro-2H-thiopyran 1,1-dioxide

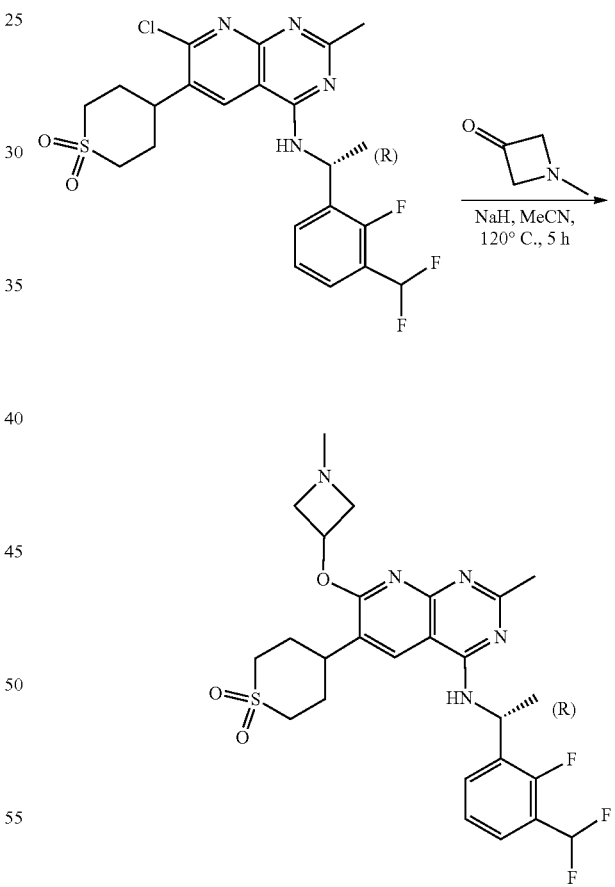

(R)-4-(4-((1-(3-(difluoromethyl)-2-fluorophenyl) ethyl)amino)-2-methyl-7-((1-methylazetidin-3-yl) oxy)pyrido[2,3-d]pyrimidin-6-yl)tetrahydro-2H-thiopyran 1,1-dioxide To a solution of (R)-4-(7-chloro-4-((1-(3-(difluoromethyl)-2-fluorophenyl)ethyl)amino)-2-methylpyrido[2,3-d]

pyrimidin-6-yl)tetrahydro-2H-thiopyran 1,1-dioxide (70 mg, 1.00 mmol) and 1-methylazetidin-3-ol (24 mg, 2.0 mmol) in MeCN (10 mL) was added NaH (60%, 28 mg, 5 mmol) at 0° C. Then the resulting mixture was heated at 120° C. under argon and stirred for 5 h. It was then cooled to RT and concentrated to remove most of MeCN. The mixture was extracted with ethyl acetate (20 mL×2). Organic extracts were combined, washed with brine, and dried over $Na_2SO_4$. It was filtered and solvent was removed under reduced pressure to give a crude. The crude was purified by preparative-TLC (dichloromethane:methyl alcohol=20:1) to afford the desired product as a solid. ESI-MS m/z: 550[M+H]$^+$. $^1$HNMR (CD3OD, 400 MHz): δ 8.71 (s, 1H), 7.62 (t, J=7.6 Hz, 1H), 7.48 (t, J=7.2 Hz, 1H), 7.24 (t, J=7.6 Hz, 1H), 7.00 (t, J=54.8, 1H), 5.85 (m, 1H), 5.58 (m, 1H), 4.70 (m, 2H), 4.37 (m, 2H), 3.45 (m, 3H), 3.19 (m, 2H), 3.02 (s, 3H), 2.42 (s, 3H), 2.40 (m, 4H), 1.68 (d, J=7.2 Hz, 3H).

Compound 234: Synthesis of (R)-1-(4-((1-(3-(difluoromethyl)-2-fluorophenyl)ethyl)amino)-2-methyl-7-((1-methylazetidin-3-1-(4-((1-(3-(difluoromethyl)-2-fluorophenyl)ethyl)amino)-2-methyl-7-((1-methylazetidin-3-yl)oxy)pyrido[2,3-d]pyrimidin-6-yl)cyclopropane-1-carbonitrile

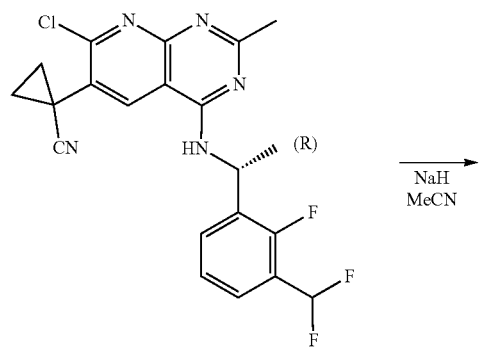

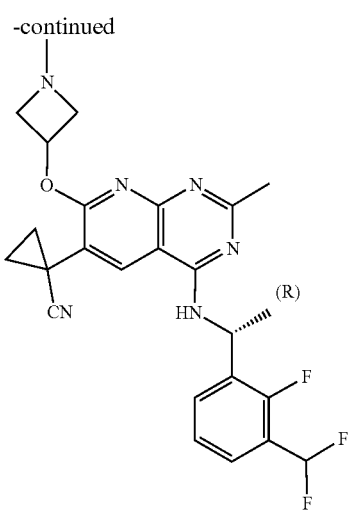

To a solution of 1-methylazetidin-3-ol (38 mg, 0.43 mmol) in MeCN (10 mL) was added NaH (34 mg, 0.86 mmol), and the mixture was stirred for 10 min. (R)-1-(7-chloro-4-((1-(3-(difluoromethyl)-2-fluorophenyl)ethyl)amino)-2-methylpyrido[2,3-d]pyrimidin-6-yl)cyclopropane-1-carbonitrile (40 mg, 0.086 mmol) was added. The mixture was heated at 100° C. under argon and stirred for 3 hours. The mixture was extracted with ethyl acetate (20 mL×2). Organic extracts were combined, washed with brine, and dried over $Na_2SO_4$. It was filtered and solvent was removed under reduced pressure to give a crude. The crude was purified by prep-TLC (dichloromethane:methyl alcohol=89:11) to afford the desired product ES-MS m/z: 483 [M+H]$^+$; $^1$HNMR (400 MHz, DMSO-d6) δ 8.92 (s, 1H), 8.76-8.75 (d, J=3.2 Hz, 1H), 7.74-7.71 (t, J=7.2 Hz, 1H), 7.52-7.48 (t, J=6.8 Hz, 1H), 7.28 (t, J=7.6 Hz, 1H), 7.23 (t, J=54 Hz, 1H), 5.78-5.75 (m, 1H), 5.52-5.49 (m, 1H), 4.43 (m, 2H), 3.89 (m, 2H), 2.78 (s, 3H), 2.34 (s, 3H), 1.78-1.75 (m, 2H), 1.63-1.59 (m, 5H).

The Compounds in Table 1 below were synthesized in the same or a similar manner as described for the preceding compounds above.

TABLE 1

| Compound | Structure | Name | [M + H]$^+$ |
|---|---|---|---|
| 109 | 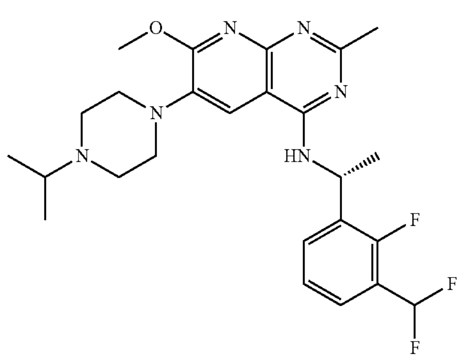 [SMILES: COc1nc2nc(C)nc(N[C@H](C)c3cccc(C(F)F)c3F)c2cc1N1CCN(C(C)C)CC1] | (R)-N-(1-(3-(difluoromethyl)-2-fluorophenyl)ethyl)-6-(4-isopropylpiperazin-1-yl)-7-methoxy-2-methylpyrido[2,3-d]pyrimidin-4-amine | 489.3 |

TABLE 1-continued

| Compound | Structure | Name | [M + H]+ |
|---|---|---|---|
| 110 | 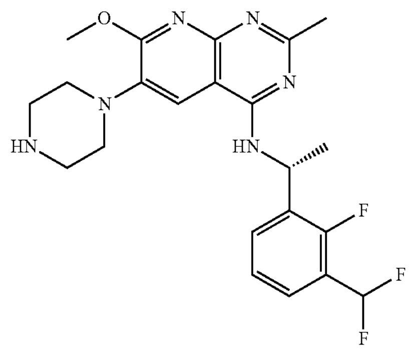 [SMILES: COc1nc2nc(C)nc(N[C@H](C)c3cccc(C(F)F)c3F)c2cc1N1CCNCC1] | (R)-N-(1-(3-(difluoromethyl)-2-fluorophenyl)ethyl)-7-methoxy-2-methyl-6-(piperazin-1-yl)pyrido[2,3-d]pyrimidin-4-amine | 447.4 |
| 111 | 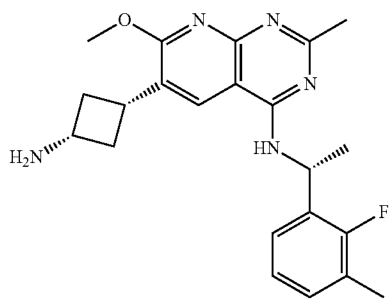 [SMILES: COc1nc2nc(C)nc(N[C@H](C)c3cccc(C)c3F)c2cc1[C@H]1C[C@@H](N)C1] | 6-((1s,3S)-3-aminocyclobutyl)-N-((R)-1-(2-fluoro-3-methylphenyl)ethyl)-7-methoxy-2-methylpyrido[2,3-d]pyrimidin-4-amine | 396.4 |
| 112 | 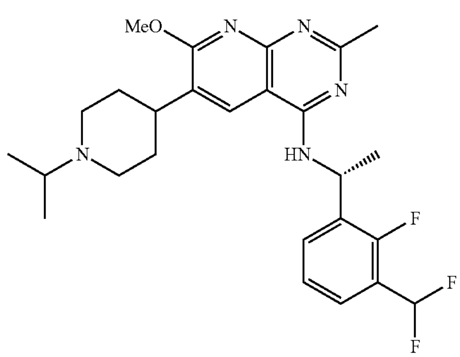 [SMILES: COc1nc2nc(C)nc(N[C@H](C)c3cccc(C(F)F)c3F)c2cc1C1CCN(C(C)C)CC1] | (R)-N-(1-(3-(difluoromethyl)-2-fluorophenyl)ethyl)-6-(1-isopropylpiperidin-4-yl)-7-methoxy-2-methylpyrido[2,3-d]pyrimidin-4-amine | 488.5 |
| 113 | 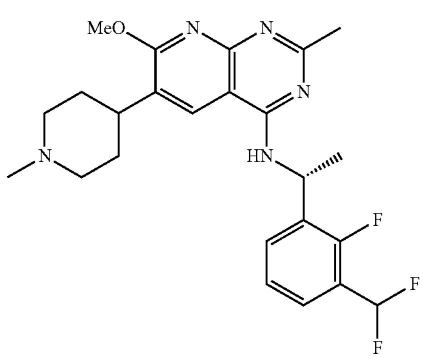 [SMILES: COc1nc2nc(C)nc(N[C@H](C)c3cccc(C(F)F)c3F)c2cc1C1CCN(C)CC1] | (R)-N-(1-(3-(difluoromethyl)-2-fluorophenyl)ethyl)-7-methoxy-2-methyl-6-(1-methylpiperidin-4-yl)pyrido[2,3-d]pyrimidin-4-amine | 460.4 |

TABLE 1-continued

| Compound | Structure | Name | [M + H]+ |
|---|---|---|---|
| 114 | 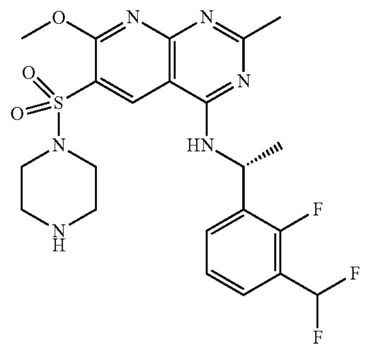 [SMILES: COc1nc2nc(C)nc(N[C@H](C)c3cccc(C(F)F)c3F)c2cc1S(=O)(=O)N1CCNCC1] | (R)-N-(1-(3-(difluoromethyl)-2-fluorophenyl)ethyl)-7-methoxy-2-methyl-6-(piperazin-1-ylsulfonyl)pyrido[2,3-d]pyrimidin-4-amine | 511.4 |
| 115 | 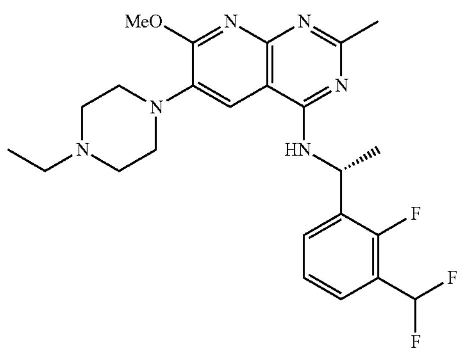 [SMILES: CCN1CCN(c2cc3c(N[C@H](C)c4cccc(C(F)F)c4F)nc(C)nc3nc2OC)CC1] | (R)-N-(1-(3-(difluoromethyl)-2-fluorophenyl)ethyl)-6-(4-ethylpiperazin-1-yl)-7-methoxy-2-methylpyrido[2,3-d]pyrimidin-4-amine | 475.4 |
| 116 | 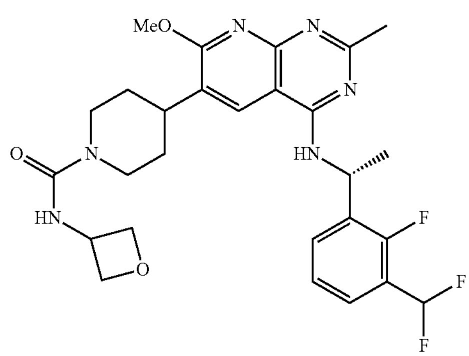 [SMILES: COc1nc2nc(C)nc(N[C@H](C)c3cccc(C(F)F)c3F)c2cc1C1CCN(C(=O)NC2COC2)CC1] | (R)-4-(4-((1-(3-(difluoromethyl)-2-fluorophenyl)ethyl)amino)-7-methoxy-2-methylpyrido[2,3-d]pyrimidin-6-yl)-N-(oxetan-3-yl)piperidine-1-carboxamide | 546.0 |
| 117 | 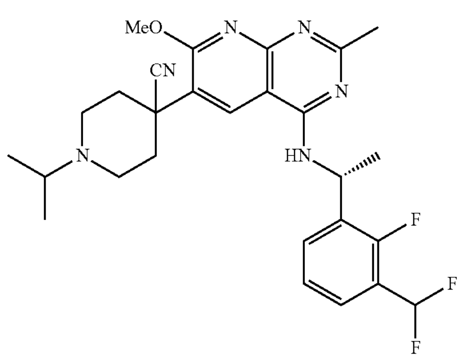 [SMILES: COc1nc2nc(C)nc(N[C@H](C)c3cccc(C(F)F)c3F)c2cc1C1(C#N)CCN(C(C)C)CC1] | (R)-4-(4-((1-(3-(difluoromethyl)-2-fluorophenyl)ethyl)amino)-7-methoxy-2-methylpyrido[2,3-d]pyrimidin-6-yl)-1-isopropylpiperidine-4-carbonitrile | 513.4 |

TABLE 1-continued

| Compound | Structure | Name | [M + H]+ |
|---|---|---|---|
| 118 | 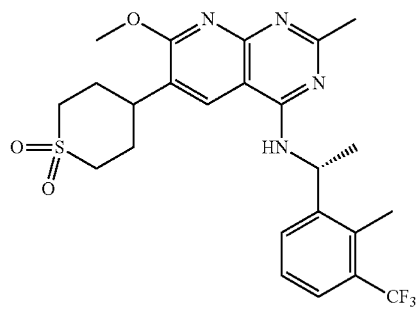 | (R)-4-(7-methoxy-2-methyl-4-((1-(2-methyl-3-(trifluoromethyl)phenyl)ethyl)amino)pyrido[2,3-d]pyrimidin-6-yl)tetrahydro-2H-thiopyran 1,1-dioxide | 509.9 |
| 119 | 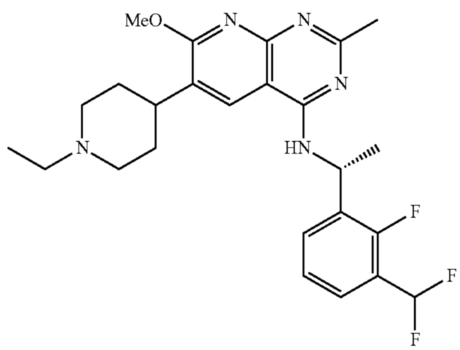 [SMILES: CCN1CCC(c2cc3c(N[C@H](C)c4cccc(C(F)F)c4F)nc(C)nc3nc2OC)CC1] | (R)-N-(1-(3-(difluoromethyl)-2-fluorophenyl)ethyl)-6-(1-ethylpiperidin-4-yl)-7-methoxy-2-methylpyrido[2,3-d]pyrimidin-4-amine | 474.5 |
| 120 | 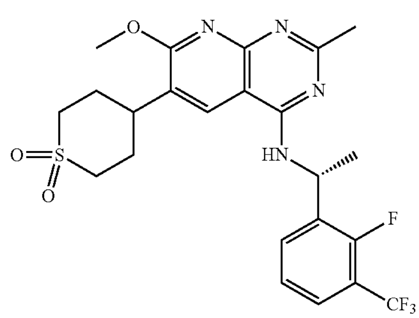 | (R)-4-(4-((1-(2-fluoro-3-(trifluoromethyl)phenyl)ethyl)amino)-7-methoxy-2-methylpyrido[2,3-d]pyrimidin-6-yl)tetrahydro-2H-thiopyran 1,1-dioxide | 513.8 |
| 121 | 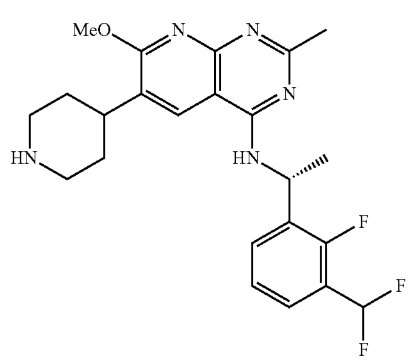 [SMILES: COc1nc2nc(C)nc(N[C@H](C)c3cccc(C(F)F)c3F)c2cc1C1CCNCC1] | (R)-N-(1-(3-(difluoromethyl)-2-fluorophenyl)ethyl)-7-methoxy-2-methyl-6-(piperidin-4-yl)pyrido[2,3-d]pyrimidin-4-amine | 446.4 |

TABLE 1-continued

| Compound | Structure | Name | [M + H]+ |
|---|---|---|---|
| 122 | 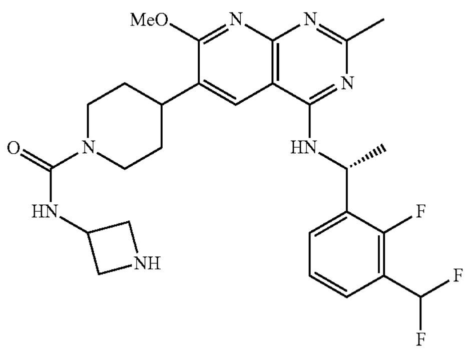 [SMILES: COc1nc2nc(C)nc(N[C@H](C)c3cccc(C(F)F)c3F)c2cc1C1CCN(C(=O)NC2CNC2)CC1] | (R)-N-(azetidin-3-yl)-4-(4-((1-(3-(difluoromethyl)-2-fluorophenyl)ethyl)amino)-7-methoxy-2-methylpyrido[2,3-d]pyrimidin-6-yl)piperidine-1-carboxamide | 544.6 |
| 123 | 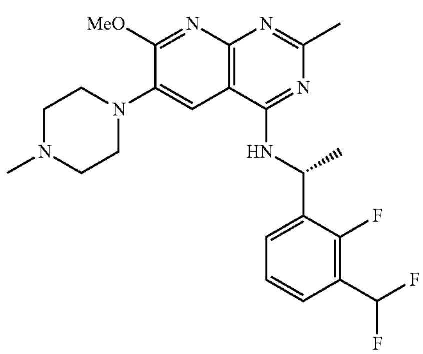 [SMILES: COc1nc2nc(C)nc(N[C@H](C)c3cccc(C(F)F)c3F)c2cc1N1CCN(C)CC1] | (R)-N-(1-(3-(difluoromethyl)-2-fluorophenyl)ethyl)-7-methoxy-2-methyl-6-(4-methylpiperazin-1-yl)pyrido[2,3-d]pyrimidin-4-amine | 475.9 |
| 124 | 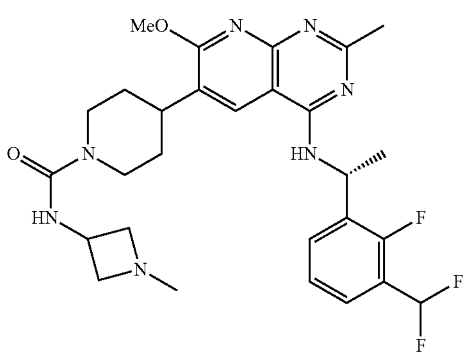 [SMILES: COc1nc2nc(C)nc(N[C@H](C)c3cccc(C(F)F)c3F)c2cc1C1CCN(C(=O)NC2CN(C)C2)CC1] | (R)-4-(4-((1-(3-(difluoromethyl)-2-fluorophenyl)ethyl)amino)-7-methoxy-2-methylpyrido[2,3-d]pyrimidin-6-yl)-N-(1-methylazetidin-3-yl)piperidine-1-carboxamide | 558.6 |
| 125 | 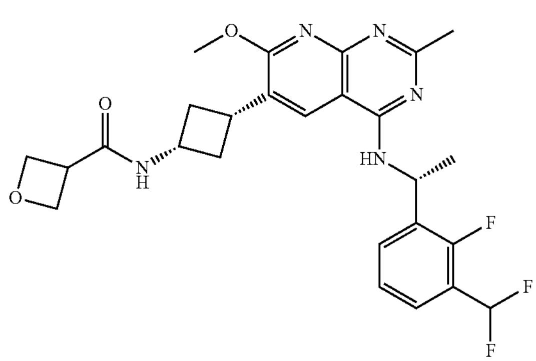 [SMILES: COc1nc2nc(C)nc(N[C@H](C)c3cccc(C(F)F)c3F)c2cc1[C@H]1C[C@@H](NC(=O)C2COC2)C1] | N-((1S,3s)-3-(4-(((R)-1-(3-(difluoromethyl)-2-fluorophenyl)ethyl)amino)-7-methoxy-2-methylpyrido[2,3-d]pyrimidin-6-yl)cyclobutyl)oxetane-3-carboxamide | 516.9 |

| Compound | Structure | Name | [M + H]+ |
|---|---|---|---|
| 126 | 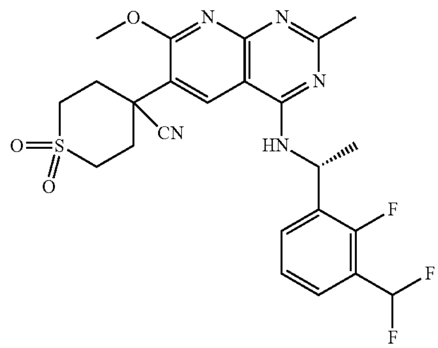 | (R)-4-(4-((1-(3-(difluoromethyl)-2-fluorophenyl)ethyl)amino)-7-methoxy-2-methylpyrido[2,3-d]pyrimidin-6-yl)tetrahydro-2H-thiopyran-4-carbonitrile 1,1-dioxide | 520.8 |
| 127 | 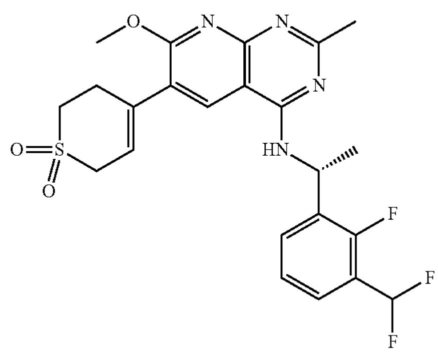 [SMILES: COc1nc2nc(C)nc(N[C@H](C)c3cccc(C(F)F)c3F)c2cc1C1=CCS(=O)(=O)CC1] | (R)-4-(4-((1-(3-(difluoromethyl)-2-fluorophenyl)ethyl)amino)-7-methoxy-2-methylpyrido[2,3-d]pyrimidin-6-yl)-3,6-dihydro-2H-thiopyran 1,1-dioxide | 493.8 |
| 128 | 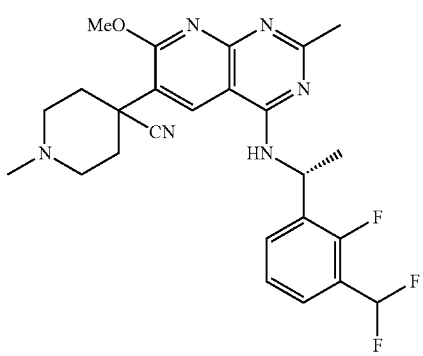 [SMILES: COc1nc2nc(C)nc(N[C@H](C)c3cccc(C(F)F)c3F)c2cc1C1(C#N)CCN(C)CC1] | (R)-4-(4-((1-(3-(difluoromethyl)-2-fluorophenyl)ethyl)amino)-7-methoxy-2-methylpyrido[2,3-d]pyrimidin-6-yl)-1-methylpiperidine-4-carbonitrile | 485.5 |
| 129 | 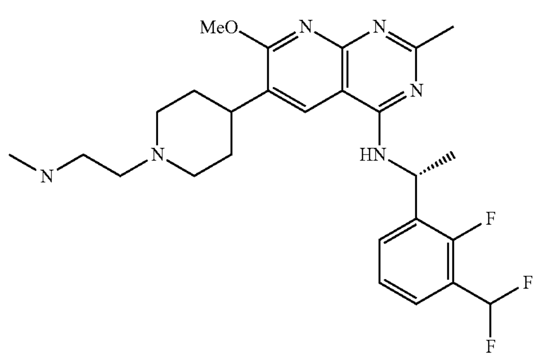 [SMILES: CNCCN1CCC(c2cc3c(N[C@H](C)c4cccc(C(F)F)c4F)nc(C)nc3nc2OC)CC1] | (R)-N-(1-(3-(difluoromethyl)-2-fluorophenyl)ethyl)-7-methoxy-2-methyl-6-(1-(2-(methyl-12-azaneyl)ethyl)piperidin-4-yl)pyrido[2,3-d]pyrimidin-4-amine | 503.5 |

TABLE 1-continued

| Compound | Structure | Name | [M + H]+ |
|---|---|---|---|
| 130 | 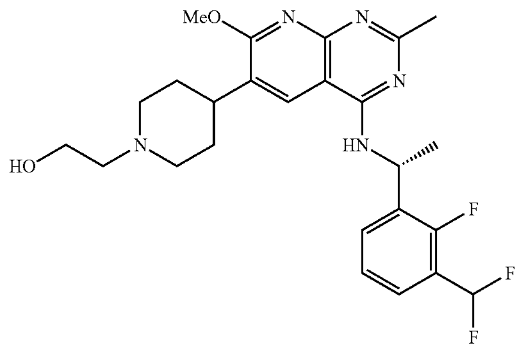 [SMILES: COc1nc2nc(C)nc(N[C@H](C)c3cccc(C(F)F)c3F)c2cc1C1CCN(CCO)CC1] | (R)-2-(4-(4-((1-(3-(difluoromethyl)-2-fluorophenyl)ethyl)amino)-7-methoxy-2-methylpyrido[2,3-d]pyrimidin-6-yl)piperidin-1-yl)ethan-1-ol | 490.4 |
| 131 | 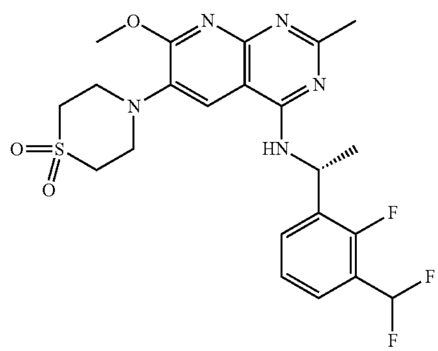 [SMILES: COc1nc2nc(C)nc(N[C@H](C)c3cccc(C(F)F)c3F)c2cc1N1CCS(=O)(=O)CC1] | (R)-4-(4-((1-(3-(difluoromethyl)-2-fluorophenyl)ethyl)amino)-7-methoxy-2-methylpyrido[2,3-d]pyrimidin-6-yl)thiomorpholine 1,1-dioxide | 496.8 |
| 132 | 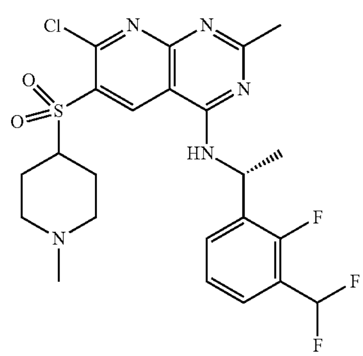 [SMILES: Cc1nc(N[C@H](C)c2cccc(C(F)F)c2F)c2cc(S(=O)(=O)C3CCN(C)CC3)c(Cl)nc2n1] | (R)-7-chloro-N-(1-(3-(difluoromethyl)-2-fluorophenyl)ethyl)-2-methyl-6-((1-methylpiperidin-4-yl)sulfonyl)pyrido[2,3-d]pyrimidin-4-amine | 528.9 |
| 133 | 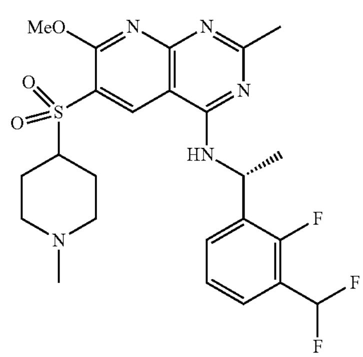 [SMILES: COc1nc2nc(C)nc(N[C@H](C)c3cccc(C(F)F)c3F)c2cc1S(=O)(=O)C1CCN(C)CC1] | (R)-N-(1-(3-(difluoromethyl)-2-fluorophenyl)ethyl)-7-methoxy-2-methyl-6-((1-methylpiperidin-4-yl)sulfonyl)pyrido[2,3-d]pyrimidin-4-amine | 524.4 |

TABLE 1-continued

| Compound | Structure | Name | [M + H]+ |
|---|---|---|---|
| 134 | 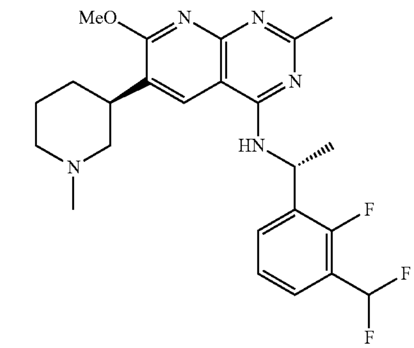 [SMILES: COc1nc2nc(C)nc(N[C@H](C)c3cccc(C(F)F)c3F)c2cc1[C@@H]1CCCN(C)C1] | N-((R)-1-(3-(difluoromethyl)-2-fluorophenyl)ethyl)-7-methoxy-2-methyl-6-((S)-1-methylpiperidin-3-yl)pyrido[2,3-d]pyrimidin-4-amine | 460.4 |
| 135 | 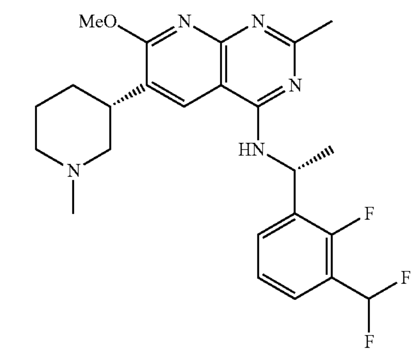 [SMILES: COc1nc2nc(C)nc(N[C@H](C)c3cccc(C(F)F)c3F)c2cc1[C@H]1CCCN(C)C1] | N-((R)-1-(3-(difluoromethyl)-2-fluorophenyl)ethyl)-7-methoxy-2-methyl-6-((R)-1-methylpiperidin-3-yl)pyrido[2,3-d]pyrimidin-4-amine | 460.4 |
| 136 | 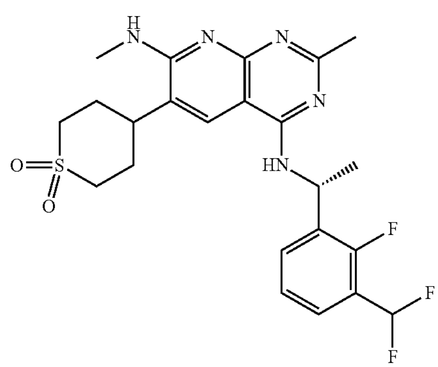 [SMILES: CNc1nc2nc(C)nc(N[C@H](C)c3cccc(C(F)F)c3F)c2cc1C1CCS(=O)(=O)CC1] | (R)-4-(4-((1-(3-(difluoromethyl)-2-fluorophenyl)ethyl)amino)-2-methyl-7-(methylamino)pyrido[2,3-d]pyrimidin-6-yl)tetrahydro-2H-thiopyran 1,1-dioxide | 494.8 |
| 137 | 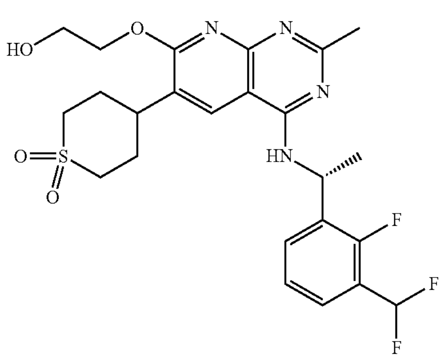 [SMILES: Cc1nc(N[C@H](C)c2cccc(C(F)F)c2F)c2cc(C3CCS(=O)(=O)CC3)c(OCCO)nc2n1] | (R)-4-(4-((1-(3-(difluoromethyl)-2-fluorophenyl)ethyl)amino)-7-(2-hydroxyethoxy)-2-methylpyrido[2,3-d]pyrimidin-6-yl)tetrahydro-2H-thiopyran 1,1-dioxide | 525.8 |

TABLE 1-continued

| Compound | Structure | Name | [M + H]+ |
|---|---|---|---|
| 138 | 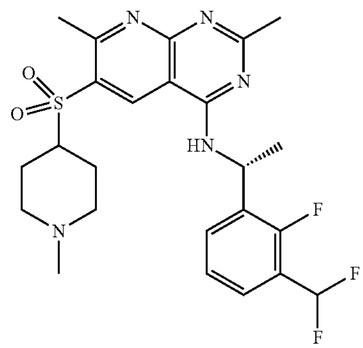 [SMILES: Cc1nc(N[C@H](C)c2cccc(C(F)F)c2F)c2cc(S(=O)(=O)C3CCN(C)CC3)c(C)nc2n1] | (R)-N-(1-(3-(difluoromethyl)-2-fluorophenyl)ethyl)-2,7-dimethyl-6-((1-methylpiperidin-4-yl)sulfonyl)pyrido[2,3-d]pyrimidin-4-amine | 494.4 |
| 139 | 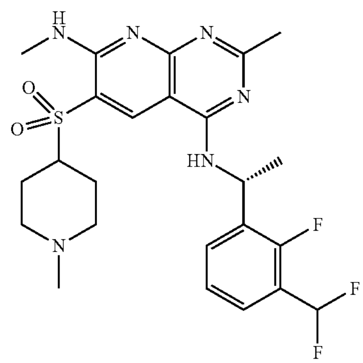 [SMILES: CNc1nc2nc(C)nc(N[C@H](C)c3cccc(C(F)F)c3F)c2cc1S(=O)(=O)C1CCN(C)CC1] | (R)-N4-(1-(3-(difluoromethyl)-2-fluorophenyl)ethyl)-N7,2-dimethyl-6-((1-methylpiperidin-4-yl)sulfonyl)pyrido[2,3-d]pyrimidine-4,7-diamine | 523.5 |
| 140 | 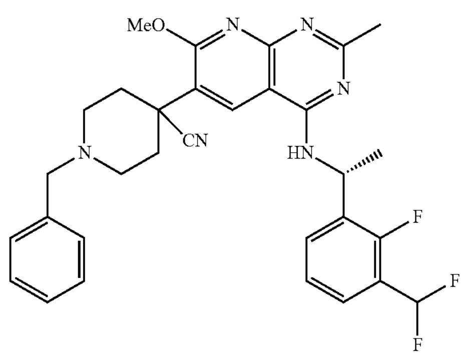 [SMILES: COc1nc2nc(C)nc(N[C@H](C)c3cccc(C(F)F)c3F)c2cc1C1(C#N)CCN(Cc2ccccc2)CC1] | (R)-1-benzyl-4-(4-((1-(3-(difluoromethyl)-2-fluorophenyl)ethyl)amino)-7-methoxy-2-methylpyrido[2,3-d]pyrimidin-6-yl)piperidine-4-carbonitrile | 561.5 |
| 141 | 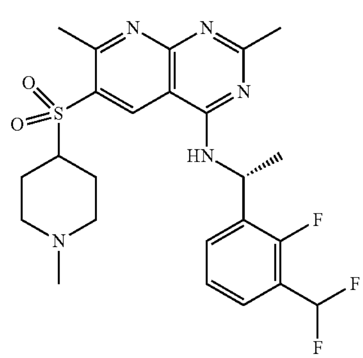 [SMILES: Cc1nc(N[C@H](C)c2cccc(C(F)F)c2F)c2cc(S(=O)(=O)C3CCN(C)CC3)c(C)nc2n1] | (R)-N-(1-(3-(difluoromethyl)-2-fluorophenyl)ethyl)-2,7-dimethyl-6-((1-methylpiperidin-4-yl)sulfonyl)pyrido[2,3-d]pyrimidin-4-amine | 508.4 |

TABLE 1-continued

| Compound | Structure | Name | [M + H]+ |
|---|---|---|---|
| 142 | 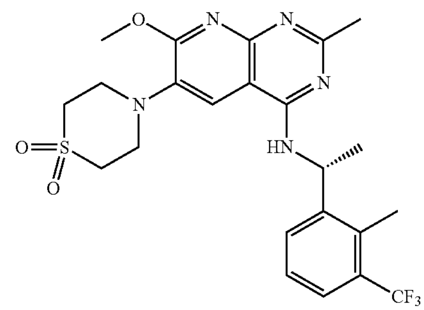 [SMILES: COc1nc2nc(C)nc(N[C@H](C)c3cccc(C(F)(F)F)c3C)c2cc1N1CCS(=O)(=O)CC1] | (R)-4-(7-methoxy-2-methyl-4-((1-(2-methyl-3-(trifluoromethyl)phenyl)ethyl)amino)pyrido[2,3-d]pyrimidin-6-yl)thiomorpholine 1,1-dioxide | 510.5 |
| 143 | 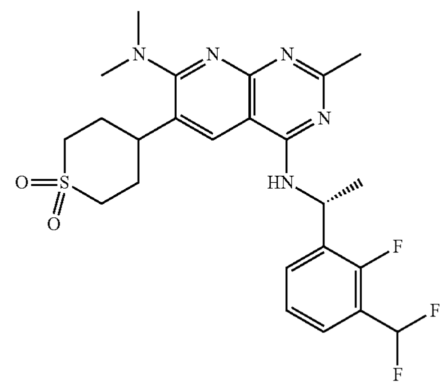 [SMILES: Cc1nc(N[C@H](C)c2cccc(C(F)F)c2F)c2cc(C3CCS(=O)(=O)CC3)c(N(C)C)nc2n1] | (R)-4-(4-((1-(3-(difluoromethyl)-2-fluorophenyl)ethyl)amino)-7-(dimethylamino)-2-methylpyrido[2,3-d]pyrimidin-6-yl)tetrahydro-2H-thiopyran 1,1-dioxide | 508.8 |
| 144 | 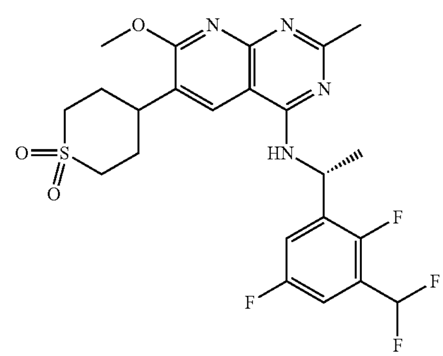 [SMILES: COc1nc2nc(C)nc(N[C@H](C)c3cc(F)cc(C(F)F)c3F)c2cc1C1CCS(=O)(=O)CC1] | (R)-4-(4-((1-(3-(difluoromethyl)-2,5-difluorophenyl)ethyl)amino)-7-methoxy-2-methylpyrido[2,3-d]pyrimidin-6-yl)tetrahydro-2H-thiopyran 1,1-dioxide | 513.9 |
| 145 | 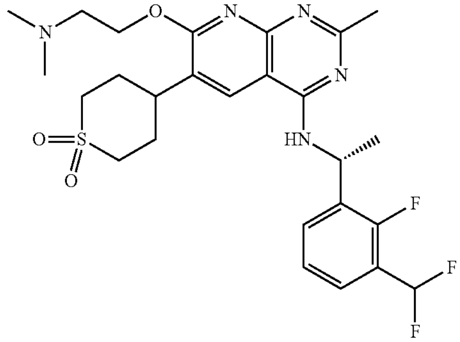 [SMILES: Cc1nc(N[C@H](C)c2cccc(C(F)F)c2F)c2cc(C3CCS(=O)(=O)CC3)c(OCCN(C)C)nc2n1] | (R)-4-(4-((1-(3-(difluoromethyl)-2-fluorophenyl)ethyl)amino)-7-(2-(dimethylamino)ethoxy)-2-methylpyrido[2,3-d]pyrimidin-6-yl)tetrahydro-2H-thiopyran 1,1-dioxide | 552.9 |

TABLE 1-continued

| Compound | Structure | Name | [M + H]+ |
|---|---|---|---|
| 146 | 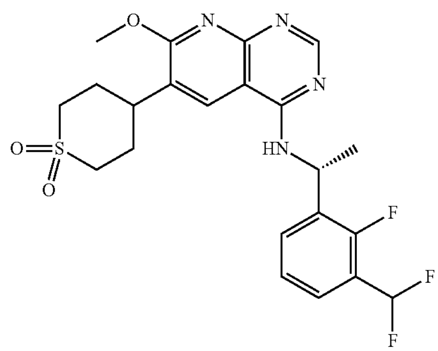 [SMILES: COc1nc2ncnc(N[C@H](C)c3cccc(C(F)F)c3F)c2cc1C1CCS(=O)(=O)CC1] | (R)-4-(4-((1-(3-(difluoromethyl)-2-fluorophenyl)ethyl)amino)-7-methoxypyrido[2,3-d]pyrimidin-6-yl)tetrahydro-2H-thiopyran 1,1-dioxide | 481.4 |
| 147 | 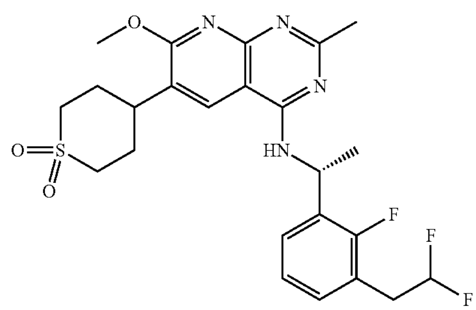 [SMILES: COc1nc2nc(C)nc(N[C@H](C)c3cccc(CC(F)F)c3F)c2cc1C1CCS(=O)(=O)CC1] | (R)-4-(4-((1-(3-(2,2-difluoroethyl)-2-fluorophenyl)ethyl)amino)-7-methoxy-2-methylpyrido[2,3-d]pyrimidin-6-yl)tetrahydro-2H-thiopyran 1,1-dioxide | 509.8 |
| 148 | 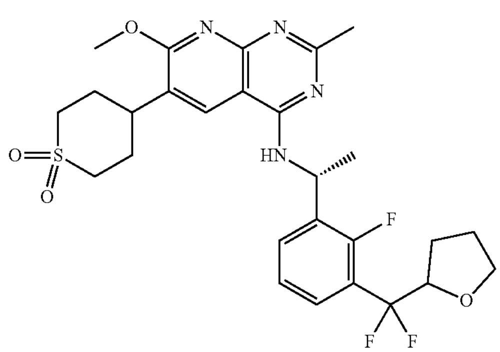 [SMILES: COc1nc2nc(C)nc(N[C@H](C)c3cccc(C(F)(F)C4CCCO4)c3F)c2cc1C1CCS(=O)(=O)CC1] | 4-(4-(((R)-1-(3-(difluoro((S)-tetrahydrofuran-2-yl)methyl)-2-fluorophenyl)ethyl)amino)-7-methoxy-2-methylpyrido[2,3-d]pyrimidin-6-yl)tetrahydro-2H-thiopyran 1,1-dioxide | 565.9 |
| 149 | 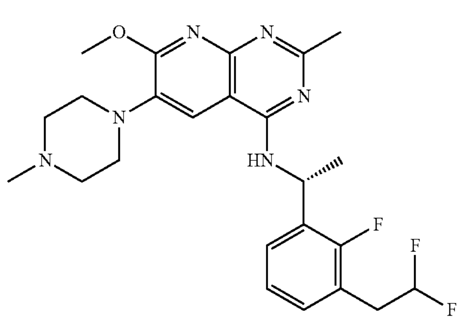 [SMILES: COc1nc2nc(C)nc(N[C@H](C)c3cccc(CC(F)F)c3F)c2cc1N1CCN(C)CC1] | (R)-N-(1-(3-(2,2-difluoroethyl)-2-fluorophenyl)ethyl)-7-methoxy-2-methyl-6-(4-methylpiperazin-1-yl)pyrido[2,3-d]pyrimidin-4-amine | 475.5 |

TABLE 1-continued

| Compound | Structure | Name | [M + H]+ |
|---|---|---|---|
| 150 | 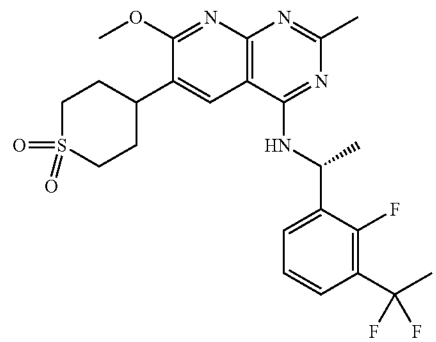 [SMILES: COc1nc2nc(C)nc(N[C@H](C)c3cccc(C(C)(F)F)c3F)c2cc1C1CCS(=O)(=O)CC1] | (R)-4-(4-((1-(3-(1,1-difluoroethyl)-2-fluorophenyl)ethyl)amino)-7-methoxy-2-methylpyrido[2,3-d]pyrimidin-6-yl)tetrahydro-2H-thiopyran 1,1-dioxide | 509.9 |
| 151 | 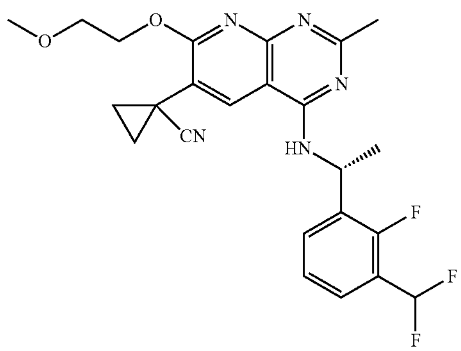 [SMILES: COCCOc1nc2nc(C)nc(N[C@H](C)c3cccc(C(F)F)c3F)c2cc1C1(C#N)CC1] | (R)-1-(4-((1-(3-(difluoromethyl)-2-fluorophenyl)ethyl)amino)-7-(2-methoxyethoxy)-2-methylpyrido[2,3-d]pyrimidin-6-yl)cyclopropane-1-carbonitrile | 472.9 |
| 152 | 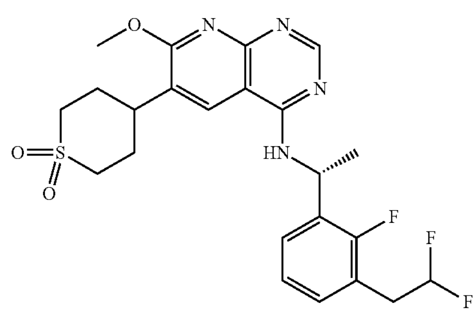 [SMILES: COc1nc2ncnc(N[C@H](C)c3cccc(CC(F)F)c3F)c2cc1C1CCS(=O)(=O)CC1] | (R)-4-(4-((1-(3-(2,2-difluoroethyl)-2-fluorophenyl)ethyl)amino)-7-methoxypyrido[2,3-d]pyrimidin-6-yl)tetrahydro-2H-thiopyran 1,1-dioxide | 495.8 |
| 153 | 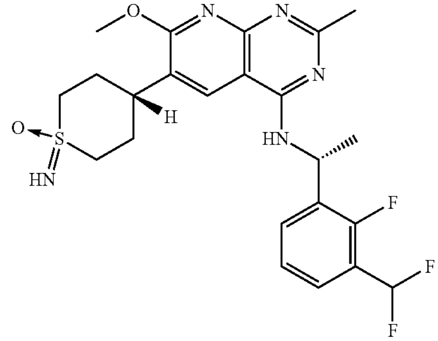 | 4-(4-(((R)-1-(3-(difluoromethyl)-2-fluorophenyl)ethyl)amino)-7-methoxy-2-methylpyrido[2,3-d]pyrimidin-6-yl)-1-iminohexahydro-1λ6-thiopyran 1-oxide | 494.8 |

TABLE 1-continued

| Compound | Structure | Name | [M + H]+ |
|---|---|---|---|
| 154 | 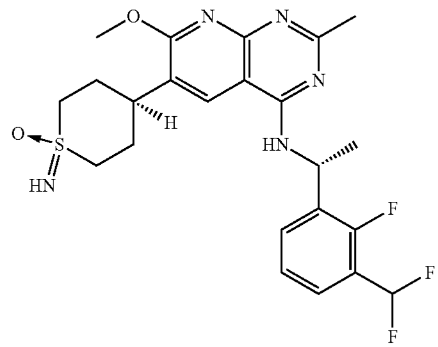 | (R)-4-(4-((1-(3-(difluoromethyl)-2-fluorophenyl)ethyl)amino)-7-methoxy-2-methylpyrido[2,3-d]pyrimidin-6-yl)-1-iminohexahydro-1λ6-thiopyran 1-oxide | 494.8 |
| 155 | 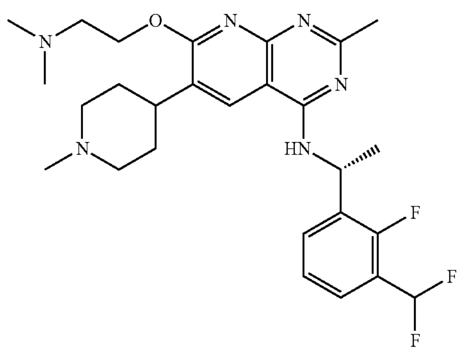 [SMILES: Cc1nc(N[C@H](C)c2cccc(C(F)F)c2F)c2cc(C3CCN(C)CC3)c(OCCN(C)C)nc2n1] | (R)-1-(4-((1-(3-(difluoromethyl)-2-fluorophenyl)ethyl)amino)-7-(2-(dimethylamino)ethoxy)-2-methylpyrido[2,3-d]pyrimidin-6-yl)cyclopropane-1-carbonitrile | 517.5 |
| 156 | 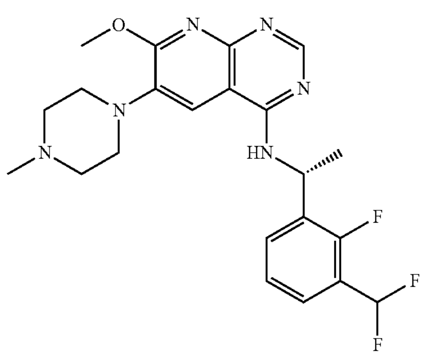 | (R)-N-(1-(3-(difluoromethyl)-2-fluorophenyl)ethyl)-7-methoxy-6-(4-methylpiperazin-1-yl)pyrido[2,3-d]pyrimidin-4-amine | 447.3 |
| 157 | 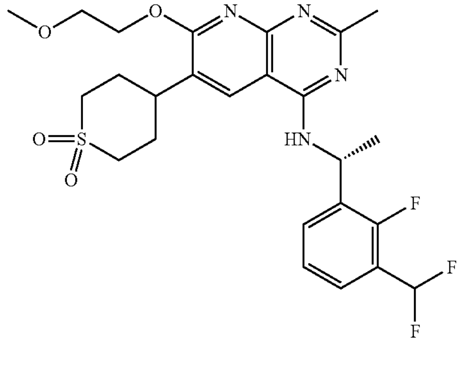 [SMILES: COCCOc1nc2nc(C)nc(N[C@H](C)c3cccc(C(F)F)c3F)c2cc1C1CCS(=O)(=O)CC1] | (R)-4-(4-((1-(3-(difluoromethyl)-2-fluorophenyl)ethyl)amino)-7-(2-methoxyethoxy)-2-methylpyrido[2,3-d]pyrimidin-6-yl)tetrahydro-2H-thiopyran 1,1-dioxide | 539.8 |

TABLE 1-continued

| Compound | Structure | Name | [M + H]+ |
|---|---|---|---|
| 158 | 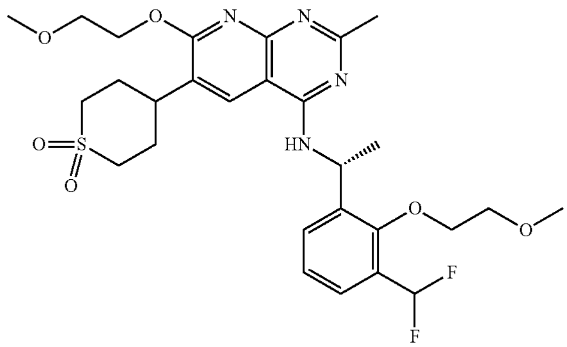 | (R)-4-(4-((1-(3-(difluoromethyl)-2-(2-methoxyethoxy)phenyl)ethyl)amino)-7-(2-methoxyethoxy)-2-methylpyrido[2,3-d]pyrimidin-6-yl)tetrahydro-2H-thiopyran 1,1-dioxide | 595.9 |
| 159 | 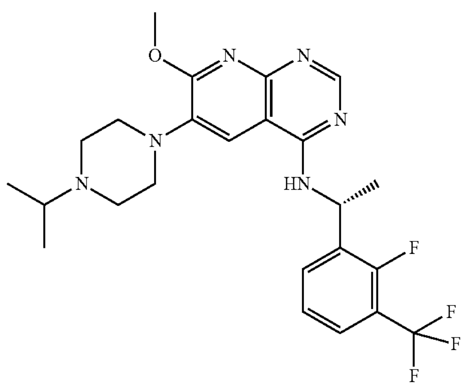 [SMILES: COc1nc2ncnc(N[C@H](C)c3cccc(C(F)(F)F)c3F)c2cc1N1CCN(C(C)C)CC1] | (R)-N-(1-(2-fluoro-3-(trifluoromethyl)phenyl)ethyl)-6-(4-isopropylpiperazin-1-yl)-7-methoxypyrido[2,3-d]pyrimidin-4-amine | 493.4 |
| 160 | 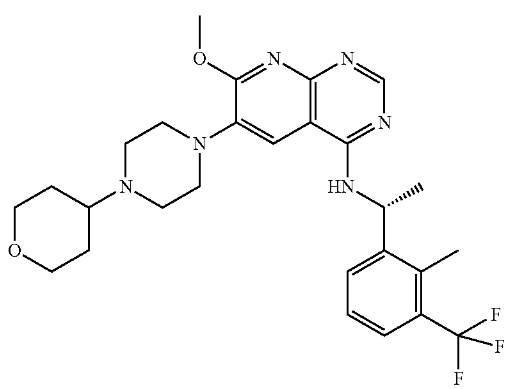 [SMILES: COc1nc2ncnc(N[C@H](C)c3cccc(C(F)(F)F)c3C)c2cc1N1CCN(C2CCOCC2)CC1] | (R)-7-methoxy-N-(1-(2-methyl-3-(trifluoromethyl)phenyl)ethyl)-6-(4-(tetrahydro-2H-pyran-4-yl)piperazin-1-yl)pyrido[2,3-d]pyrimidin-4-amine | 531.4 |
| 161 | 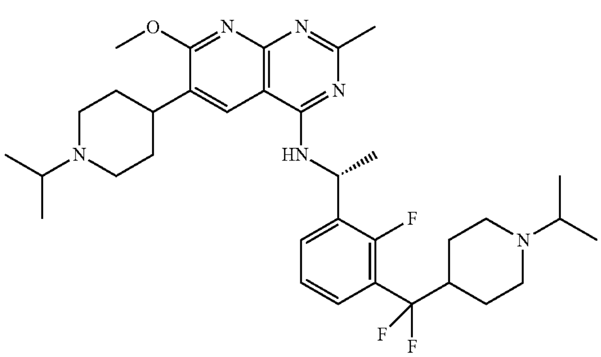 [SMILES: COc1nc2nc(C)nc(N[C@H](C)c3cccc(C(F)(F)C4CCN(C(C)C)CC4)c3F)c2cc1C1CCN(C(C)C)CC1] | (R)-N-(1-(3-(difluoro(1-isopropylpiperidin-4-yl)methyl)-2-fluorophenyl)ethyl)-6-(1-isopropylpiperidin-4-yl)-7-methoxy-2-methylpyrido[2,3-d]pyrimidin-4-amine | 613.6 |

TABLE 1-continued

| Compound | Structure | Name | [M + H]+ |
|---|---|---|---|
| 162 | 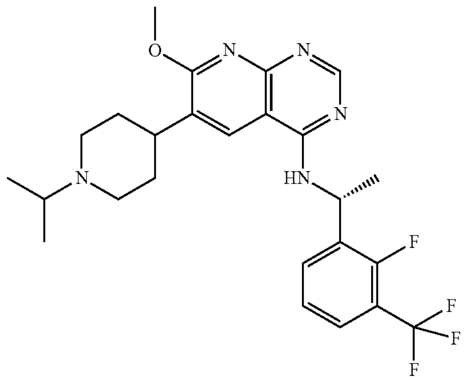 [SMILES: COc1nc2ncnc(N[C@H](C)c3cccc(C(F)(F)F)c3F)c2cc1C1CCN(C(C)C)CC1] | (R)-N-(1-(2-fluoro-3-(trifluoromethyl)phenyl)ethyl)-6-(1-isopropylpiperidin-4-yl)-7-methoxypyrido[2,3-d]pyrimidin-4-amine | 492.4 |
| 163 | 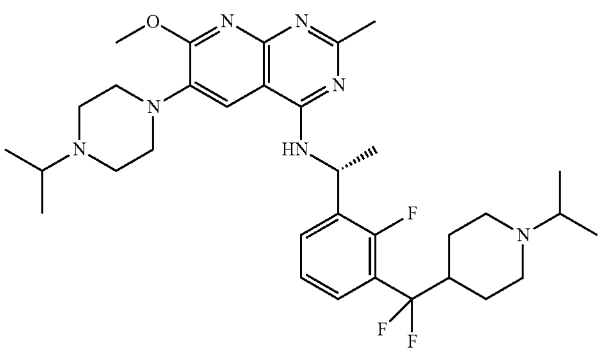 | (R)-N-(1-(3-(difluoro(1-isopropylpiperidin-4-yl)methyl)-2-fluorophenyl)ethyl)-6-(4-isopropylpiperazin-1-yl)-7-methoxy-2-methylpyrido[2,3-d]pyrimidin-4-amine | 614.5 |
| 164 | 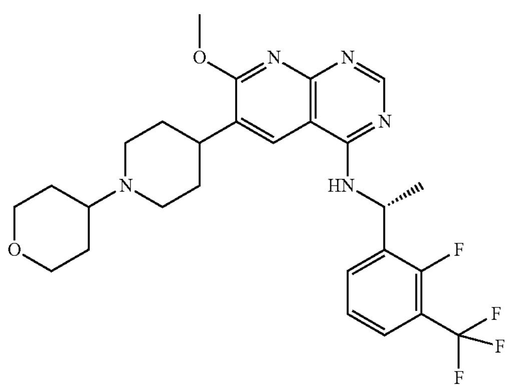 [SMILES: COc1nc2ncnc(N[C@H](C)c3cccc(C(F)(F)F)c3F)c2cc1C1CCN(C2CCOCC2)CC1] | (R)-N-(1-(2-fluoro-3-(trifluoromethyl)phenyl)ethyl)-7-methoxy-6-(1-(tetrahydro-2H-pyran-4-yl)piperidin-4-yl)pyrido[2,3-d]pyrimidin-4-amine | 534.5 |
| 165 | 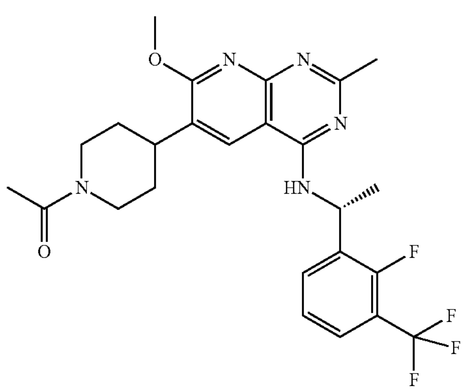 [SMILES: COc1nc2nc(C)nc(N[C@H](C)c3cccc(C(F)(F)F)c3F)c2cc1C1CCN(C(C)=O)CC1] | (R)-1-(4-(4-((1-(2-fluoro-3-(trifluoromethyl)phenyl)ethyl)amino)-7-methoxy-2-methylpyrido[2,3-d]pyrimidin-6-yl)piperidin-1-yl)ethan-1-one | 506.8 |

TABLE 1-continued

| Compound | Structure | Name | [M + H]+ |
|---|---|---|---|
| 166 | 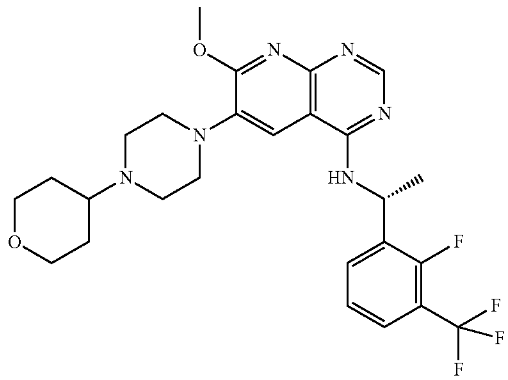 | (R)-N-(1-(2-fluoro-3-(trifluoromethyl)phenyl)ethyl)-7-methoxy-6-(4-(tetrahydro-2H-pyran-4-yl)piperazin-1-yl)pyrido[2,3-d]pyrimidin-4-amine | 535.4 |
| 167 | 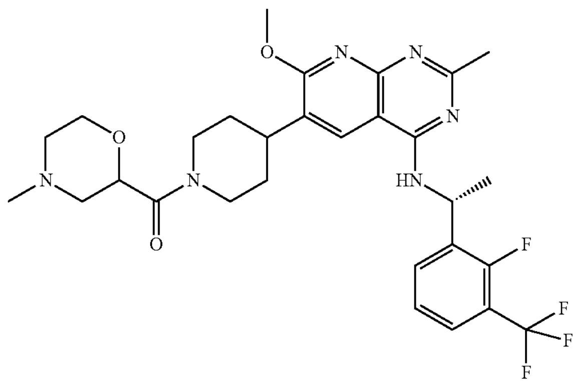 | (4-(4-(((R)-1-(2-fluoro-3-(trifluoromethyl)phenyl)ethyl)amino)-7-methoxy-2-methylpyrido[2,3-d]pyrimidin-6-yl)piperidin-1-yl)(4-methylmorpholin-2-yl)methanone | 591.4 |
| 168 | 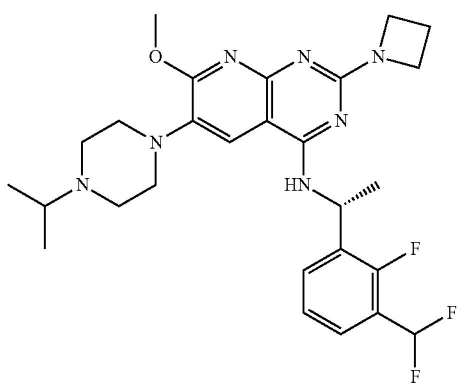 [SMILES: COc1nc2nc(N3CCC3)nc(N[C@H](C)c3cccc(C(F)F)c3F)c2cc1N1CCN(C(C)C)CC1] | (R)-2-(azetidin-1-yl)-N-(1-(3-(difluoromethyl)-2-fluorophenyl)ethyl)-6-(4-isopropylpiperazin-1-yl)-7-methoxypyrido[2,3-d]pyrimidin-4-amine | 530.45 |
| 169 | 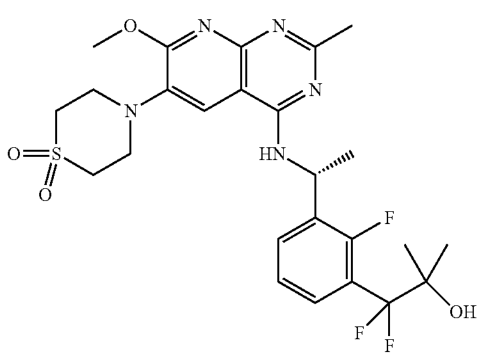 [SMILES: COc1nc2nc(C)nc(N[C@H](C)c3cccc(C(F)(F)C(C)(C)O)c3F)c2cc1N1CCS(=O)(=O)CC1] | (R)-4-(4-((1-(3-(1,1-difluoro-2-hydroxy-2-methylpropyl)-2-fluorophenyl)ethyl)amino)-7-methoxy-2-methylpyrido[2,3-d]pyrimidin-6-yl)thiomorpholine 1,1-dioxide | 554.4 |

TABLE 1-continued

| Compound | Structure | Name | [M + H]+ |
|---|---|---|---|
| 170 | 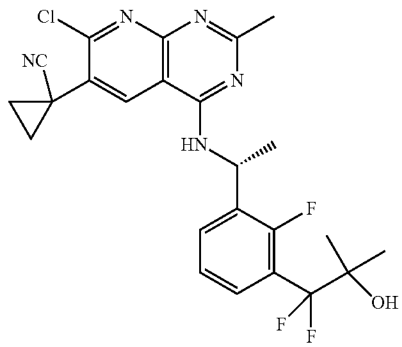 [SMILES: Cc1nc(N[C@H](C)c2cccc(C(F)(F)C(C)(C)O)c2F)c2cc(C3(C#N)CC3)c(Cl)nc2n1] | (R)-1-(7-chloro-4-((1-(3-(1,1-difluoro-2-hydroxy-2-methylpropyl)-2-fluorophenyl)ethyl)amino)-2-methylpyrido[2,3-d]pyrimidin-6-yl)cyclopropane-1-carbonitrile | 490.3 |
| 171 | 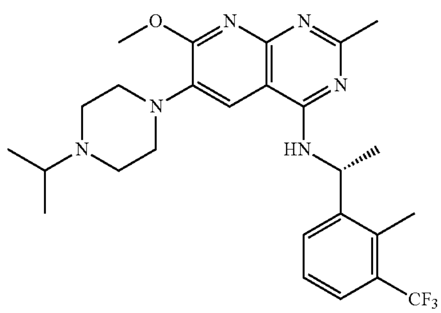 | (R)-6-(4-isopropylpiperazin-1-yl)-7-methoxy-2-methyl-N-(1-(2-methyl-3-(trifluoromethyl)phenyl)ethyl)pyrido[2,3-d]pyrimidin-4-amine | 503.3 |
| 172 | 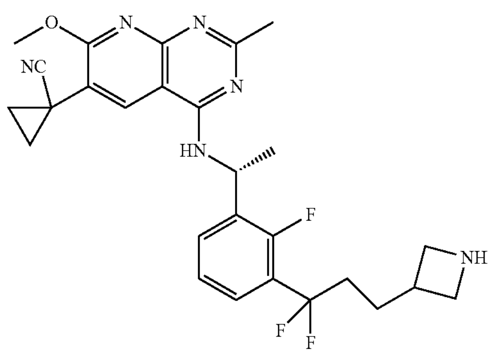 [SMILES: COc1nc2nc(C)nc(N[C@H](C)c3cccc(C(F)(F)CCC4CNC4)c3F)c2cc1C1(C#N)CC1] | (R)-1-(4-((1-(3-(3-(azetidin-3-yl)-1,1-difluoropropyl)-2-fluorophenyl)ethyl)amino)-7-methoxy-2-methylpyrido[2,3-d]pyrimidin-6-yl)cyclopropane-1-carbonitrile | 511.35 |
| 173 | 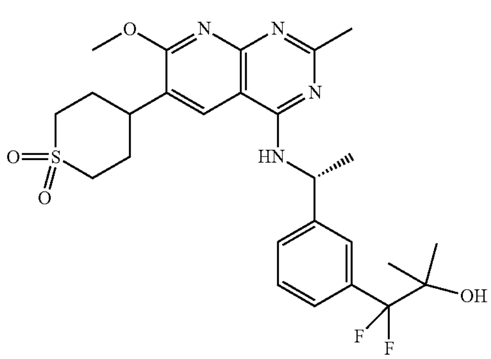 [SMILES: COc1nc2nc(C)nc(N[C@H](C)c3cccc(C(F)(F)C(C)(C)O)c3)c2cc1C1CCS(=O)(=O)CC1] | (R)-4-(4-((1-(3-(1,1-difluoro-2-hydroxy-2-methylpropyl)phenyl)ethyl)amino)-7-methoxy-2-methylpyrido[2,3-d]pyrimidin-6-yl)tetrahydro-2H-thiopyran 1,1-dioxide | 535.6 |

TABLE 1-continued

| Compound | Structure | Name | [M + H]+ |
|---|---|---|---|
| 174 | 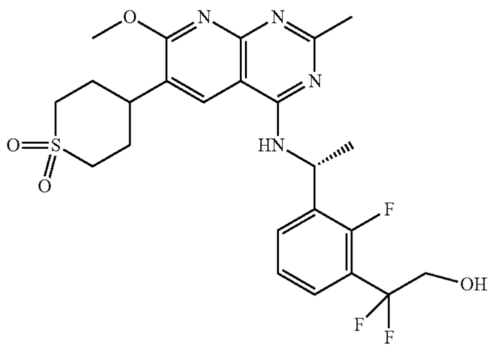 [SMILES: COc1nc2nc(C)nc(N[C@H](C)c3cccc(C(F)(F)CO)c3F)c2cc1C1CCS(=O)(=O)CC1] | (R)-4-(4-((1-(3-(1,1-difluoro-2-hydroxyethyl)-2-fluorophenyl)ethyl)amino)-7-methoxy-2-methylpyrido[2,3-d]pyrimidin-6-yl)tetrahydro-2H-thiopyran 1,1-dioxide | 525.6 |
| 175 | 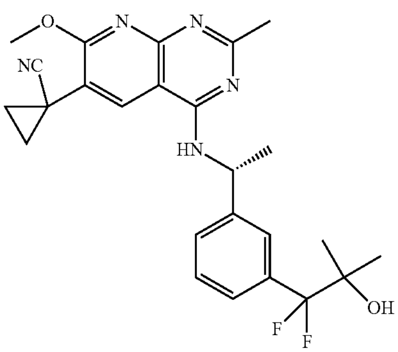 [SMILES: COc1nc2nc(C)nc(N[C@H](C)c3cccc(C(F)(F)C(C)(C)O)c3)c2cc1C1(C#N)CC1] | (R)-1-(4-((1-(3-(1,1-difluoro-2-hydroxy-2-methylpropyl)phenyl)ethyl)amino)-7-methoxy-2-methylpyrido[2,3-d]pyrimidin-6-yl)cyclopropane-1-carbonitrile | 468.6 |
| 176 | 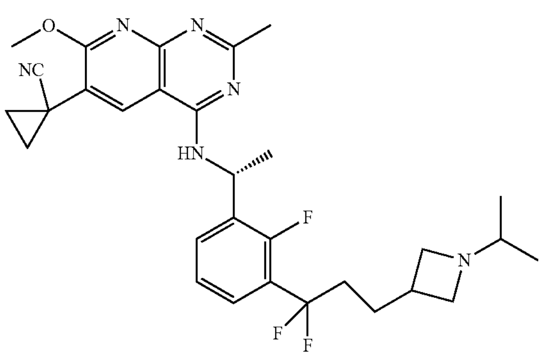 [SMILES: COc1nc2nc(C)nc(N[C@H](C)c3cccc(C(F)(F)CCC4CN(C(C)C)C4)c3F)c2cc1C1(C#N)CC1] | (R)-1-(4-((1-(3-(1,1-difluoro-3-(1-isopropylazetidin-3-yl)propyl)-2-fluorophenyl)ethyl)amino)-7-methoxy-2-methylpyrido[2,3-d]pyrimidin-6-yl)cyclopropane-1-carbonitrile | 553.4 |
| 177 | 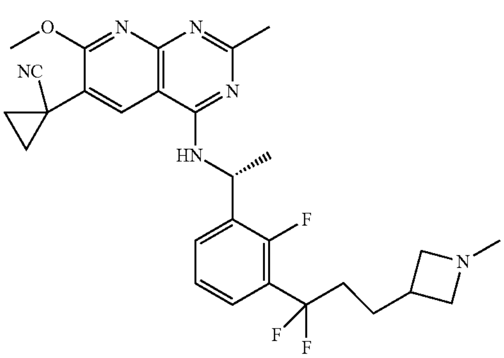 [SMILES: COc1nc2nc(C)nc(N[C@H](C)c3cccc(C(F)(F)CCC4CN(C)C4)c3F)c2cc1C1(C#N)CC1] | (R)-1-(4-((1-(3-(1,1-difluoro-3-(1-methylazetidin-3-yl)propyl)-2-fluorophenyl)ethyl)amino)-7-methoxy-2-methylpyrido[2,3-d]pyrimidin-6-yl)cyclopropane-1-carbonitrile | 525.3 |

TABLE 1-continued

| Compound | Structure | Name | [M + H]+ |
|---|---|---|---|
| 178 | 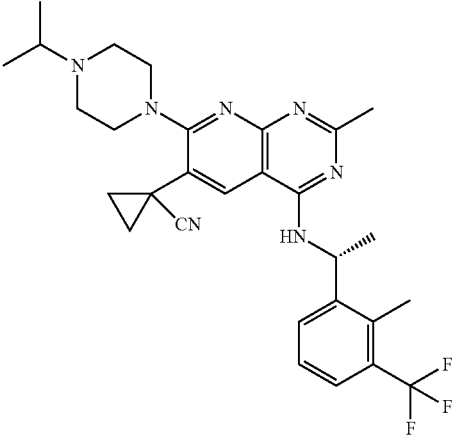 [SMILES: Cc1nc(N[C@H](C)c2cccc(C(F)(F)F)c2C)c2cc(C3(C#N)CC3)c(N3CCN(C(C)C)CC3)nc2n1] | (R)-1-(7-(4-isopropylpiperazin-1-yl)-2-methyl-4-((1-(2-methyl-3-(trifluoromethyl)phenyl)ethyl)amino)pyrido[2,3-d]pyrimidin-6-yl)cyclopropane-1-carbonitrile | 538.4 |
| 179 | 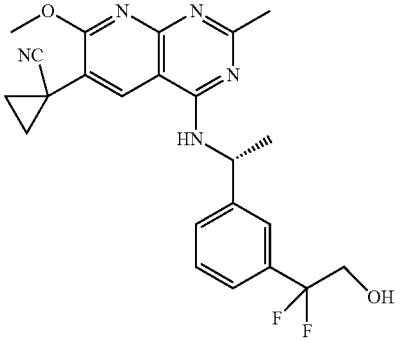 [SMILES: COc1nc2nc(C)nc(N[C@H](C)c3cccc(C(F)(F)CO)c3)c2cc1C1(C#N)CC1] | (R)-1-(4-((1-(3-(1,1-difluoro-2-hydroxyethyl)phenyl)ethyl)amino)-7-methoxy-2-methylpyrido[2,3-d]pyrimidin-6-yl)cyclopropane-1-carbonitrile | 440.6 |
| 180 | 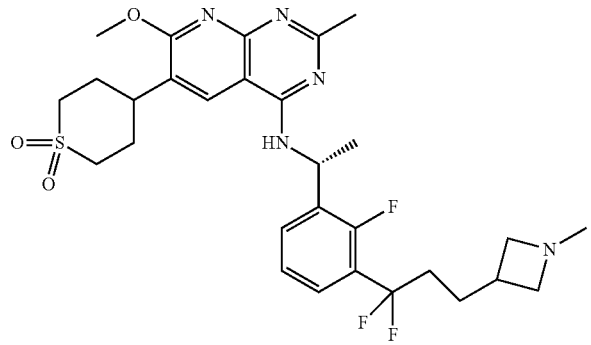 [SMILES: COc1nc2nc(C)nc(N[C@H](C)c3cccc(C(F)(F)CCC4CN(C)C4)c3F)c2cc1C1CCS(=O)(=O)CC1] | (R)-4-(4-((1-(3-(1,1-difluoro-3-(1-methylazetidin-3-yl)propyl)-2-fluorophenyl)ethyl)amino)-7-methoxy-2-methylpyrido[2,3-d]pyrimidin-6-yl)tetrahydro-2H-thiopyran 1,1-dioxide | 592.4 |
| 181 | 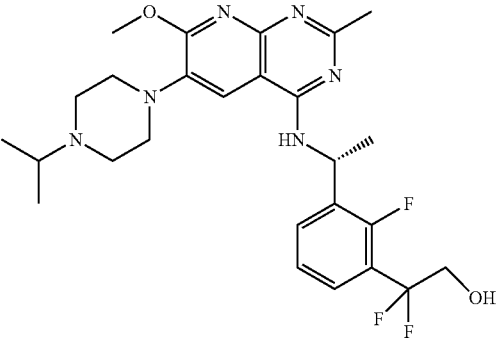 [SMILES: COc1nc2nc(C)nc(N[C@H](C)c3cccc(C(F)(F)CO)c3F)c2cc1N1CCN(C(C)C)CC1] | (R)-2,2-difluoro-2-(2-fluoro-3-(1-((6-(4-isopropylpiperazin-1-yl)-7-methoxy-2-methylpyrido[2,3-d]pyrimidin-4-yl)amino)ethyl)phenyl)ethan-1-ol | 519.3 |

TABLE 1-continued

| Compound | Structure | Name | [M + H]+ |
|---|---|---|---|
| 182 | 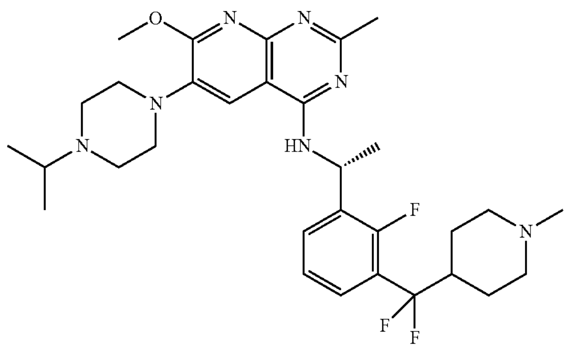 [SMILES: COc1nc2nc(C)nc(N[C@H](C)c3cccc(C(F)(F)C4CCN(C)CC4)c3F)c2cc1N1CCN(C(C)C)CC1] | (R)-N-(1-(3-(difluoro(1-methylpiperidin-4-yl)methyl)-2-fluorophenyl)ethyl)-6-(4-isopropylpiperazin-1-yl)-7-methoxy-2-methylpyrido[2,3-d]pyrimidin-4-amine | 586.5 |
| 183 | 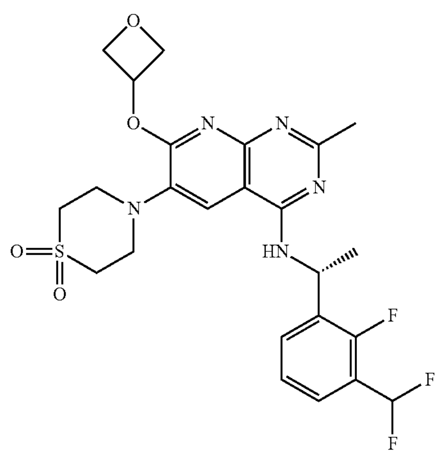 [SMILES: Cc1nc(N[C@H](C)c2cccc(C(F)F)c2F)c2cc(N3CCS(=O)(=O)CC3)c(OC3COC3)nc2n1] | (R)-4-(4-((1-(3-(difluoromethyl)-2-fluorophenyl)ethyl)amino)-2-methyl-7-(oxetan-3-yloxy)pyrido[2,3-d]pyrimidin-6-yl)thiomorpholine 1,1-dioxide | 538.4 |
| 184 | 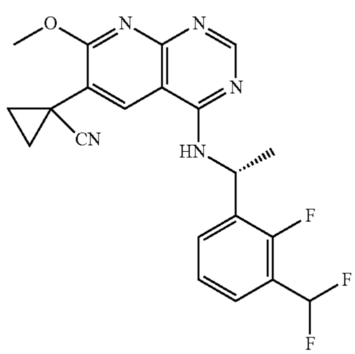 [SMILES: COc1nc2ncnc(N[C@H](C)c3cccc(C(F)F)c3F)c2cc1C1(C#N)CC1] | (R)-1-(4-((1-(3-(difluoromethyl)-2-fluorophenyl)ethyl)amino)-7-methoxypyrido[2,3-d]pyrimidin-6-yl)cyclopropane-1-carbonitrile | 414.7 |
| 185 | 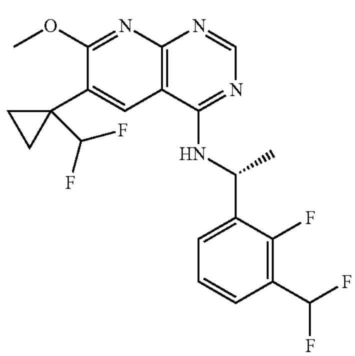 [SMILES: COc1nc2ncnc(N[C@H](C)c3cccc(C(F)F)c3F)c2cc1C1(C(F)F)CC1] | (R)-N-(1-(3-(difluoromethyl)-2-fluorophenyl)ethyl)-6-(1-(difluoromethyl)cyclopropyl)-7-methoxypyrido[2,3-d]pyrimidin-4-amine | 439.65 |

TABLE 1-continued

| Compound | Structure | Name | [M + H]+ |
|---|---|---|---|
| 186 | 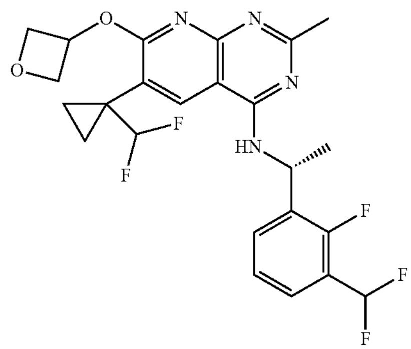 [SMILES: Cc1nc(N[C@H](C)c2cccc(C(F)F)c2F)c2cc(C3(C(F)F)CC3)c(OC3COC3)nc2n1] | (R)-N-(1-(3-(difluoromethyl)-2-fluorophenyl)ethyl)-6-(1-(difluoromethyl)cyclopropyl)-2-methyl-7-(oxetan-3-yloxy)pyrido[2,3-d]pyrimidin-4-amine | 495.8 |
| 187 | 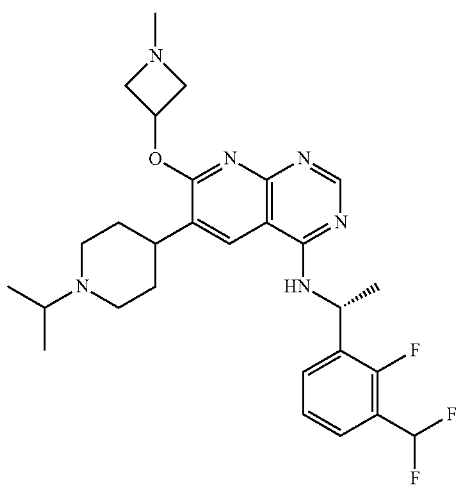 [SMILES: CC(C)N1CCC(c2cc3c(N[C@H](C)c4cccc(C(F)F)c4F)ncnc3nc2OC2CN(C)C2)CC1] | (R)-N-(1-(3-(difluoromethyl)-2-fluorophenyl)ethyl)-6-(1-isopropylpiperidin-4-yl)-7-((1-methylazetidin-3-yl)oxy)pyrido[2,3-d]pyrimidin-4-amine | 529.9 |
| 188 | 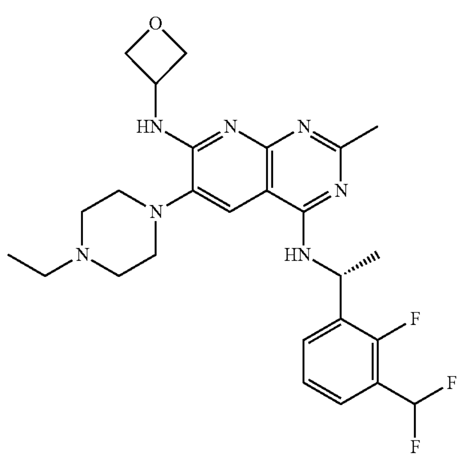 [SMILES: CCN1CCN(c2cc3c(N[C@H](C)c4cccc(C(F)F)c4F)nc(C)nc3nc2NC2COC2)CC1] | (R)-N4-(1-(3-(difluoromethyl)-2-fluorophenyl)ethyl)-6-(4-ethylpiperazin-1-yl)-2-methyl-N7-(oxetan-3-yl)pyrido[2,3-d]pyrimidine-4,7-diamine | 516.5 |

TABLE 1-continued

| Compound | Structure | Name | [M + H]+ |
|---|---|---|---|
| 189 | 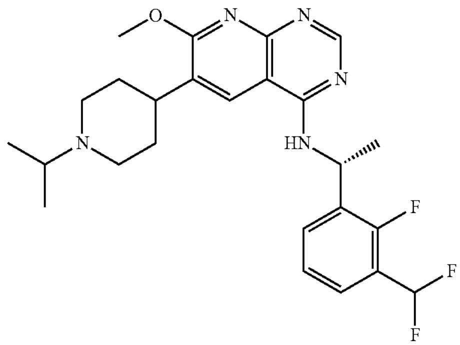 [SMILES: COc1nc2ncnc(N[C@H](C)c3cccc(C(F)F)c3F)c2cc1C1CCN(C(C)C)CC1] | (R)-N-(1-(3-(difluoromethyl)-2-fluorophenyl)ethyl)-6-(1-isopropylpiperidin-4-yl)-7-methoxypyrido[2,3-d]pyrimidin-4-amine | 474.5 |
| 190 | 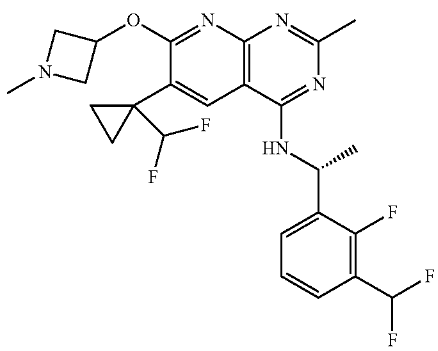 [SMILES: Cc1nc(N[C@H](C)c2cccc(C(F)F)c2F)c2cc(C3(C(F)F)CC3)c(OC3CN(C)C3)nc2n1] | (R)-N-(1-(3-(difluoromethyl)-2-fluorophenyl)ethyl)-6-(1-(difluoromethyl)cyclopropyl)-2-methyl-7-((1-methylazetidin-3-yl)oxy)pyrido[2,3-d]pyrimidin-4-amine | 508.3 |
| 191 | 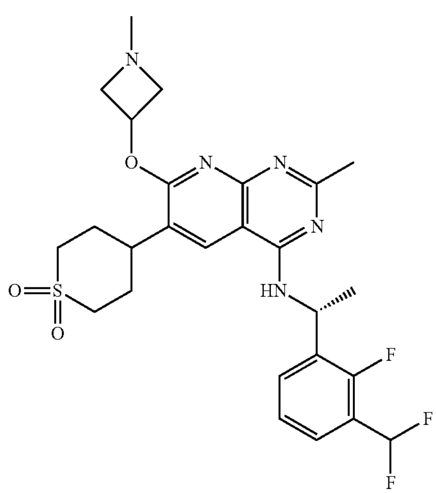 [SMILES: Cc1nc(N[C@H](C)c2cccc(C(F)F)c2F)c2cc(C3CCS(=O)(=O)CC3)c(OC3CN(C)C3)nc2n1] | (R)-4-(4-((1-(3-(difluoromethyl)-2-fluorophenyl)ethyl)amino)-2-methyl-7-((1-methylazetidin-3-yl)oxy)pyrido[2,3-d]pyrimidin-6-yl)tetrahydro-2H-thiopyran 1,1-dioxide | 550.4 |

TABLE 1-continued

| Compound | Structure | Name | [M + H]+ |
|---|---|---|---|
| 192 | 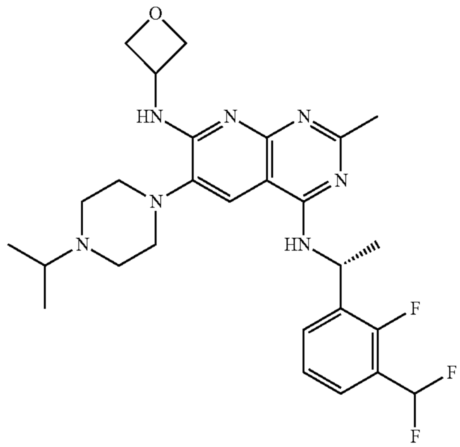 [SMILES: Cc1nc(N[C@H](C)c2cccc(C(F)F)c2F)c2cc(N3CCN(C(C)C)CC3)c(NC3COC3)nc2n1] | (R)-N4-(1-(3-(difluoromethyl)-2-fluorophenyl)ethyl)-6-(4-isopropylpiperazin-1-yl)-2-methyl-N7-(oxetan-3-yl)pyrido[2,3-d]pyrimidine-4,7-diamine | 530.5 |
| 193 | 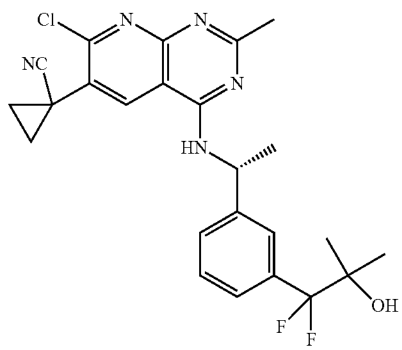 [SMILES: Cc1nc(N[C@H](C)c2cccc(C(F)(F)C(C)(C)O)c2)c2cc(C3(C#N)CC3)c(Cl)nc2n1] | (R)-1-(7-chloro-4-((1-(3-(1,1-difluoro-2-hydroxy-2-methylpropyl)phenyl)ethyl)amino)-2-methylpyrido[2,3-d]pyrimidin-6-yl)cyclopropane-1-carbonitrile | 472.3 |
| 194 | 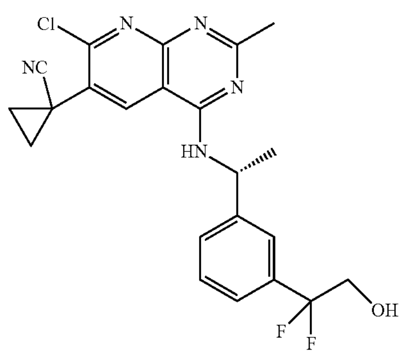 [SMILES: Cc1nc(N[C@H](C)c2cccc(C(F)(F)CO)c2)c2cc(C3(C#N)CC3)c(Cl)nc2n1] | (R)-1-(7-chloro-4-((1-(3-(1,1-difluoro-2-hydroxyethyl)phenyl)ethyl)amino)-2-methylpyrido[2,3-d]pyrimidin-6-yl)cyclopropane-1-carbonitrile | 444.2 |
| 195 | 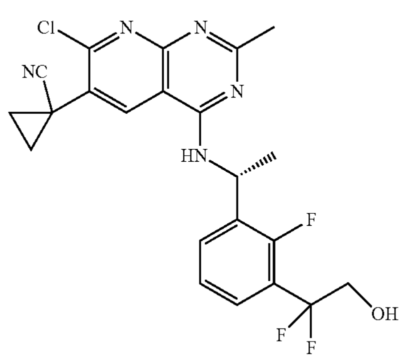 [SMILES: Cc1nc(N[C@H](C)c2cccc(C(F)(F)CO)c2F)c2cc(C3(C#N)CC3)c(Cl)nc2n1] | (R)-1-(7-chloro-4-((1-(3-(1,1-difluoro-2-hydroxyethyl)-2-fluorophenyl)ethyl)amino)-2-methylpyrido[2,3-d]pyrimidin-6-yl)cyclopropane-1-carbonitrile | 462.3 |

TABLE 1-continued

| Compound | Structure | Name | [M + H]+ |
|---|---|---|---|
| 196 | 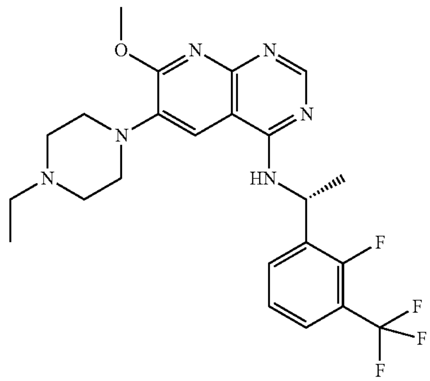 [SMILES: CCN1CCN(c2cc3c(N[C@H](C)c4cccc(C(F)(F)F)c4F)ncnc3nc2OC)CC1] | (R)-6-(4-ethylpiperazin-1-yl)-N-(1-(2-fluoro-3-(trifluoromethyl)phenyl)ethyl)-7-methoxypyrido[2,3-d]pyrimidin-4-amine | 479.3 |
| 197 | 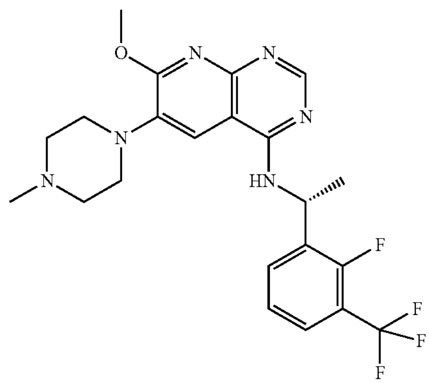 | (R)-N-(1-(2-fluoro-3-(trifluoromethyl)phenyl)ethyl)-7-methoxy-6-(4-methylpiperazin-1-yl)pyrido[2,3-d]pyrimidin-4-amine | 465.3 |
| 198 | 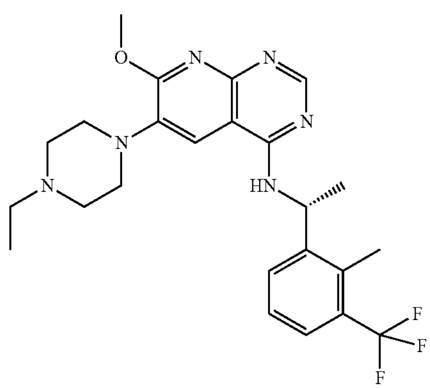 | (R)-6-(4-ethylpiperazin-1-yl)-7-methoxy-N-(1-(2-methyl-3-(trifluoromethyl)phenyl)ethyl)pyrido[2,3-d]pyrimidin-4-amine | 475.4 |
| 199 | 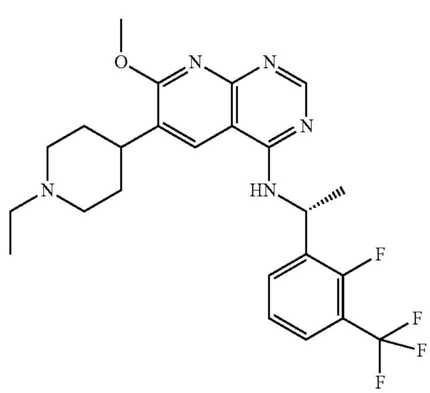 [SMILES: CCN1CCC(c2cc3c(N[C@H](C)c4cccc(C(F)(F)F)c4F)ncnc3nc2OC)CC1] | (R)-6-(1-ethylpiperidin-4-yl)-N-(1-(2-fluoro-3-(trifluoromethyl)phenyl)ethyl)-7-methoxypyrido[2,3-d]pyrimidin-4-amine | 478.4 |

TABLE 1-continued

| Compound | Structure | Name | [M + H]+ |
|---|---|---|---|
| 200 | 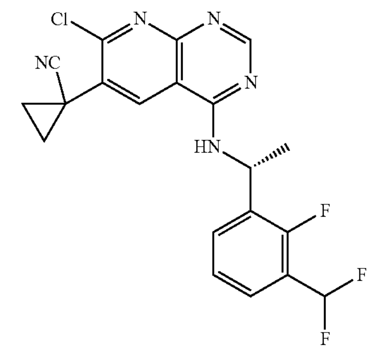 [SMILES: C[C@@H](Nc1ncnc2nc(Cl)c(C3(C#N)CC3)cc12)c1cccc(C(F)F)c1F] | (R)-1-(7-chloro-4-((1-(3-(difluoromethyl)-2-fluorophenyl)ethyl)amino)pyrido[2,3-d]pyrimidin-6-yl)cyclopropane-1-carbonitrile | 418.4 |
| 201 | 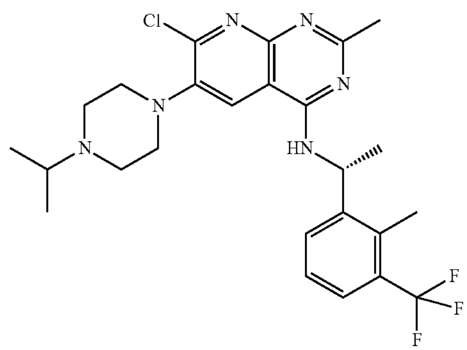 | (R)-7-chloro-6-(4-isopropylpiperazin-1-yl)-2-methyl-N-(1-(2-methyl-3-(trifluoromethyl)phenyl)ethyl)pyrido[2,3-d]pyrimidin-4-amine | 507.3 |
| 202 | 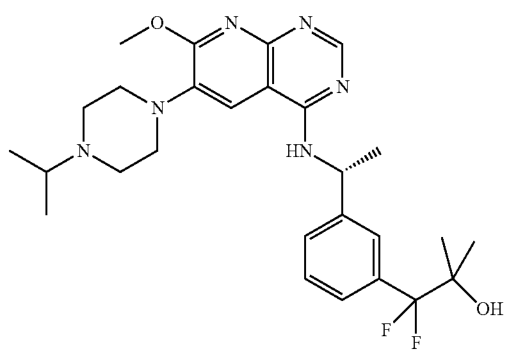 [SMILES: COc1nc2ncnc(N[C@H](C)c3cccc(C(F)(F)C(C)(C)O)c3)c2cc1N1CCN(C(C)C)CC1] | (R)-1,1-difluoro-1-(3-(1-((6-(4-isopropylpiperazin-1-yl)-7-methoxypyrido[2,3-d]pyrimidin-4-yl)amino)ethyl)phenyl)-2-methylpropan-2-ol | 515.5 |
| 203 | 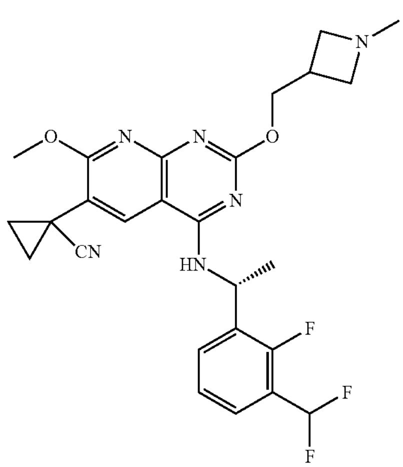 [SMILES: COc1nc2nc(OCC3CN(C)C3)nc(N[C@H](C)c3cccc(C(F)F)c3F)c2cc1C1(C#N)CC1] | (R)-1-(4-((1-(3-(difluoromethyl)-2-fluorophenyl)ethyl)amino)-7-methoxy-2-((1-methylazetidin-3-yl)methoxy)pyrido[2,3-d]pyrimidin-6-yl)cyclopropane-1-carbonitrile | 513.4 |

TABLE 1-continued

| Compound | Structure | Name | [M + H]+ |
|---|---|---|---|
| 204 | 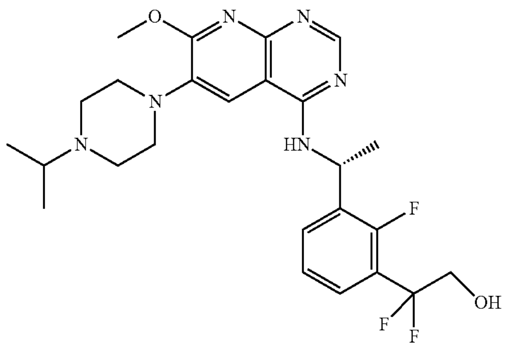 [SMILES: COc1nc2ncnc(N[C@H](C)c3cccc(C(F)(F)CO)c3F)c2cc1N1CCN(C(C)C)CC1] | (R)-2,2-difluoro-2-(2-fluoro-3-(1-((6-(4-isopropylpiperazin-1-yl)-7-methoxypyrido[2,3-d]pyrimidin-4-yl)amino)ethyl)phenyl)ethan-1-ol | 505.5 |
| 205 | 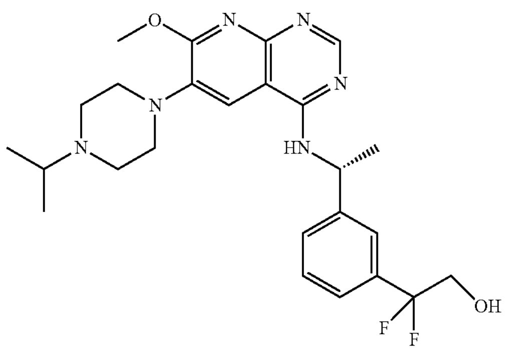 [SMILES: COc1nc2ncnc(N[C@H](C)c3cccc(C(F)(F)CO)c3)c2cc1N1CCN(C(C)C)CC1] | (R)-2,2-difluoro-2-(3-(1-((6-(4-isopropylpiperazin-1-yl)-7-methoxypyrido[2,3-d]pyrimidin-4-yl)amino)ethyl)phenyl)ethan-1-ol | 487.4 |
| 206 | 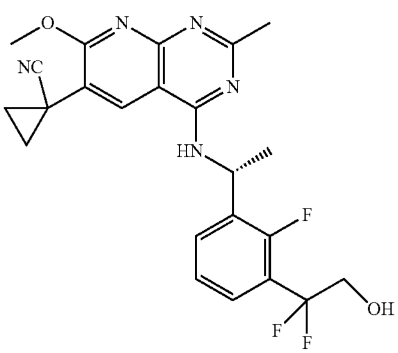 [SMILES: COc1nc2nc(C)nc(N[C@H](C)c3cccc(C(F)(F)CO)c3F)c2cc1C1(C#N)CC1] | (R)-1-(4-((1-(3-(1,1-difluoro-2-hydroxyethyl)-2-fluorophenyl)ethyl)amino)-7-methoxy-2-methylpyrido[2,3-d]pyrimidin-6-yl)cyclopropane-1-carbonitrile | 458.7 |
| 207 | 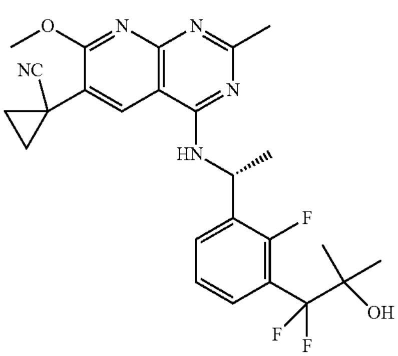 [SMILES: COc1nc2nc(C)nc(N[C@H](C)c3cccc(C(F)(F)C(C)(C)O)c3F)c2cc1C1(C#N)CC1] | (R)-1-(4-((1-(3-(1,1-difluoro-2-hydroxy-2-methylpropyl)-2-fluorophenyl)ethyl)amino)-7-methoxy-2-methylpyrido[2,3-d]pyrimidin-6-yl)cyclopropane-1-carbonitrile | 486.8 |

TABLE 1-continued

| Compound | Structure | Name | [M + H]+ |
|---|---|---|---|
| 208 | 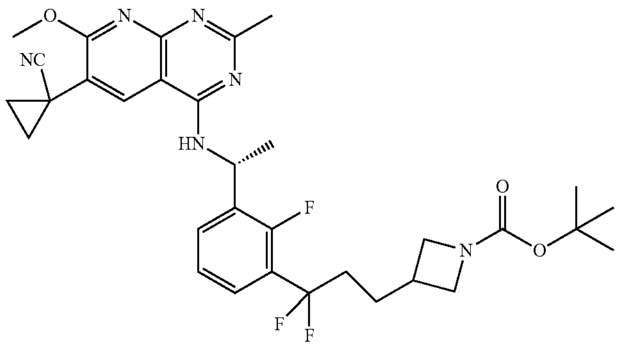 [SMILES: COc1nc2nc(C)nc(N[C@H](C)c3cccc(C(F)(F)CCC4CN(C(=O)OC(C)(C)C)C4)c3F)c2cc1C1(C#N)CC1] | tert-butyl (R)-3-(3-(3-(1-((6-(1-cyanocyclopropyl)-7-methoxy-2-methylpyrido[2,3-d]pyrimidin-4-yl)amino)ethyl)-2-fluorophenyl)-3,3-difluoropropyl)azetidine-1-carboxylate | 611.5 |
| 209 | 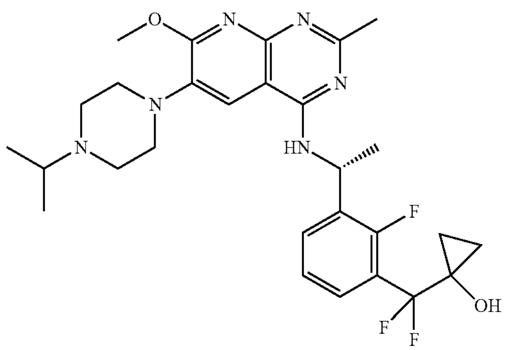 [SMILES: COc1nc2nc(C)nc(N[C@H](C)c3cccc(C(F)(F)C4(O)CC4)c3F)c2cc1N1CCN(C(C)C)CC1] | (R)-1-(difluoro(2-fluoro-3-(1-((6-(4-isopropylpiperazin-1-yl)-7-methoxy-2-methylpyrido[2,3-d]pyrimidin-4-yl)amino)ethyl)phenyl)methyl)cyclopropan-1-ol | 545.5 |
| 210 | 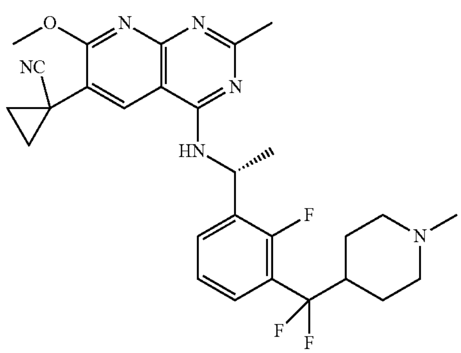 [SMILES: COc1nc2nc(C)nc(N[C@H](C)c3cccc(C(F)(F)C4CCN(C)CC4)c3F)c2cc1C1(C#N)CC1] | (R)-1-(4-((1-(3-(difluoro(1-methylpiperidin-4-yl)methyl)-2-fluorophenyl)ethyl)amino)-7-methoxy-2-methylpyrido[2,3-d]pyrimidin-6-yl)cyclopropane-1-carbonitrile | 525.5 |
| 211 | 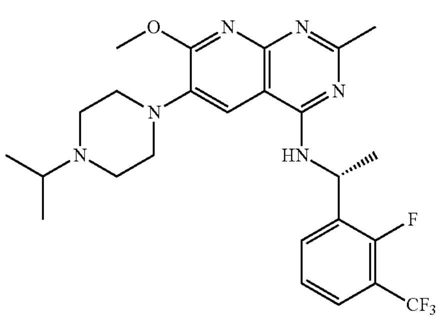 [SMILES: COc1nc2nc(C)nc(N[C@H](C)c3cccc(C(F)(F)F)c3F)c2cc1N1CCN(C(C)C)CC1] | (R)-N-(1-(2-fluoro-3-(trifluoromethyl)phenyl)ethyl)-6-(4-isopropylpiperazin-1-yl)-7-methoxy-2-methylpyrido[2,3-d]pyrimidin-4-amine | 507.4 |

TABLE 1-continued

| Compound | Structure | Name | [M + H]+ |
|---|---|---|---|
| 212 | 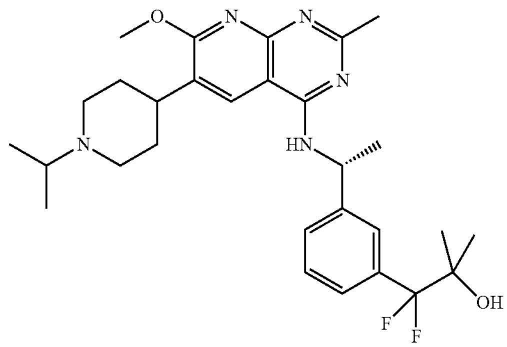 [SMILES: COc1nc2nc(C)nc(N[C@H](C)c3cccc(C(F)(F)C(C)(C)O)c3)c2cc1C1CCN(C(C)C)CC1] | (R)-1,1-difluoro-1-(3-(1-((6-(1-isopropylpiperidin-4-yl)-7-methoxy-2-methylpyrido[2,3-d]pyrimidin-4-yl)amino)ethyl)phenyl)-2-methylpropan-2-ol | 528.5 |
| 213 | 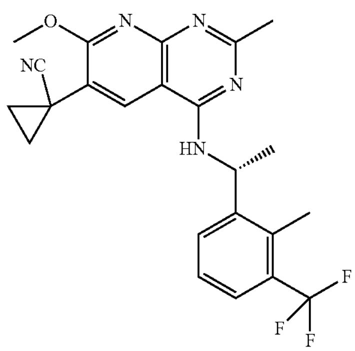 [SMILES: COc1nc2nc(C)nc(N[C@H](C)c3cccc(C(F)(F)F)c3C)c2cc1C1(C#N)CC1] | (R)-1-(7-methoxy-2-methyl-4-((1-(2-methyl-3-(trifluoromethyl)phenyl)ethyl)amino)pyrido[2,3-d]pyrimidin-6-yl)cyclopropane-1-carbonitrile | 442.7 |
| 214 | 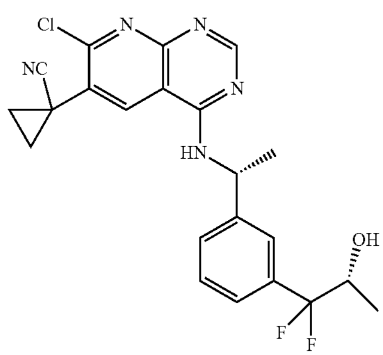 [SMILES: C[C@@H](Nc1ncnc2nc(Cl)c(C3(C#N)CC3)cc12)c1cccc(C(F)(F)[C@@H](C)O)c1] | 1-(7-chloro-4-(((R)-1-(3-((R)-1,1-difluoro-2-hydroxypropyl)phenyl)ethyl)amino)pyrido[2,3-d]pyrimidin-6-yl)cyclopropane-1-carbonitrile | 444.3 |
| 215 | 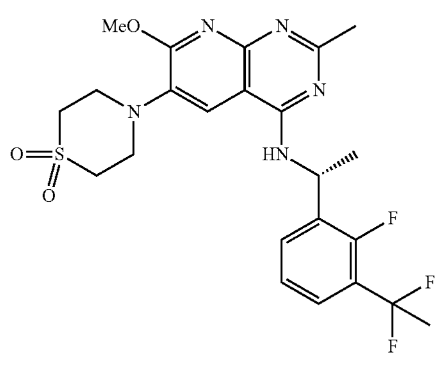 [SMILES: COc1nc2nc(C)nc(N[C@H](C)c3cccc(C(C)(F)F)c3F)c2cc1N1CCS(=O)(=O)CC1] | (R)-4-(4-((1-(3-(1,1-difluoroethyl)-2-fluorophenyl)ethyl)amino)-7-methoxy-2-methylpyrido[2,3-d]pyrimidin-6-yl)thiomorpholine 1,1-dioxide | 510.3 |

TABLE 1-continued

| Compound | Structure | Name | [M + H]+ |
|---|---|---|---|
| 216 | 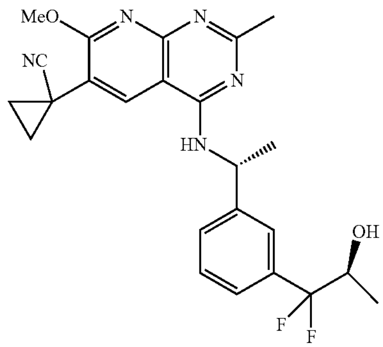 [SMILES: COc1nc2nc(C)nc(N[C@H](C)c3cccc(C(F)(F)[C@H](C)O)c3)c2cc1C1(C#N)CC1] | 1-(4-(((R)-1-(3-((S)-1,1-difluoro-2-hydroxypropyl)phenyl)ethyl)amino)-7-methoxy-2-methylpyrido[2,3-d]pyrimidin-6-yl)cyclopropane-1-carbonitrile | 454.3 |
| 217 | 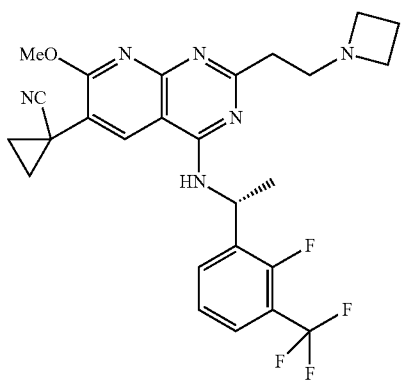 [SMILES: COc1nc2nc(CCN3CCC3)nc(N[C@H](C)c3cccc(C(F)(F)F)c3F)c2cc1C1(C#N)CC1] | (R)-1-(2-(2-(azetidin-1-yl)ethyl)-4-((1-(2-fluoro-3-(trifluoromethyl)phenyl)ethyl)amino)-7-methoxypyrido[2,3-d]pyrimidin-6-yl)cyclopropane-1-carbonitrile | 497.4 |
| 218 | 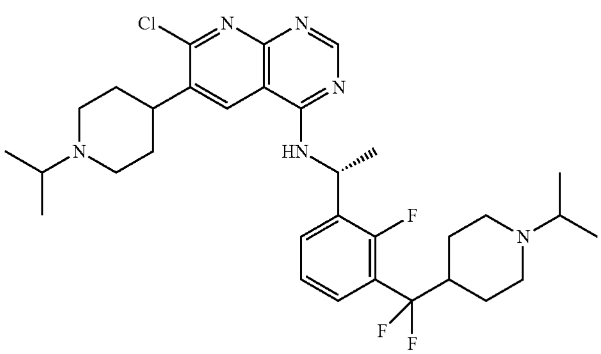 [SMILES: CC(C)N1CCC(c2cc3c(N[C@H](C)c4cccc(C(F)(F)C5CCN(C(C)C)CC5)c4F)ncnc3nc2Cl)CC1] | (R)-7-chloro-N-(1-(3-(difluoro(1-isopropylpiperidin-4-yl)methyl)-2-fluorophenyl)ethyl)-6-(1-isopropylpiperidin-4-yl)pyrido[2,3-d]pyrimidin-4-amine | 603.5 |
| 219 | 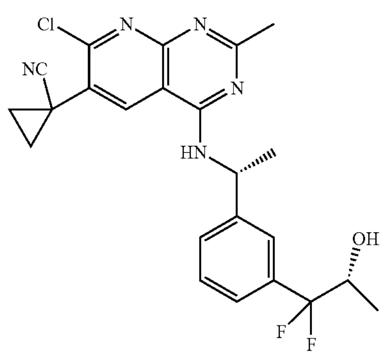 [SMILES: Cc1nc(N[C@H](C)c2cccc(C(F)(F)[C@@H](C)O)c2)c2cc(C3(C#N)CC3)c(Cl)nc2n1] | 1-(7-chloro-4-(((R)-1-(3-((R)-1,1-difluoro-2-hydroxypropyl)phenyl)ethyl)amino)-2-methylpyrido[2,3-d]pyrimidin-6-yl)cyclopropane-1-carbonitrile | 458.2 |

TABLE 1-continued

| Compound | Structure | Name | [M + H]+ |
|---|---|---|---|
| 220 | 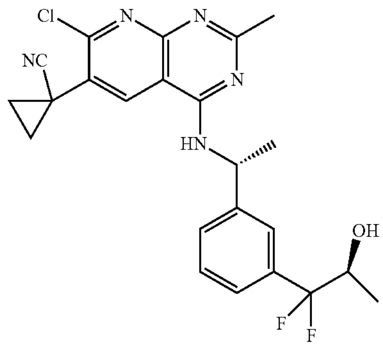 [SMILES: Cc1nc(N[C@H](C)c2cccc(C(F)(F)[C@H](C)O)c2)c2cc(C3(C#N)CC3)c(Cl)nc2n1] | 1-(7-chloro-4-(((R)-1-(3-((S)-1,1-difluoro-2-hydroxypropyl)phenyl)ethyl)amino)-2-methylpyrido[2,3-d]pyrimidin-6-yl)cyclopropane-1-carbonitrile | 458.2 |
| 221 | 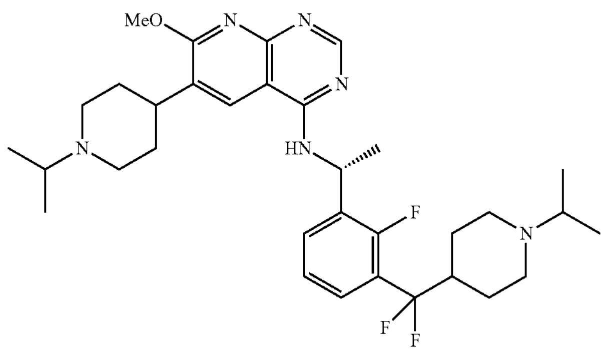 | (R)-N-(1-(3-(difluoro(1-isopropylpiperidin-4-yl)methyl)-2-fluorophenyl)ethyl)-6-(1-isopropylpiperidin-4-yl)-7-methoxypyrido[2,3-d]pyrimidin-4-amine | 599.5 |
| 222 | 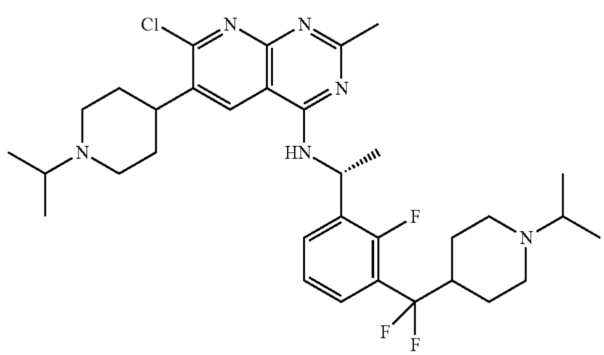 [SMILES: Cc1nc(N[C@H](C)c2cccc(C(F)(F)C3CCN(C(C)C)CC3)c2F)c2cc(C3CCN(C(C)C)CC3)c(Cl)nc2n1] | (R)-7-chloro-N-(1-(3-(difluoro(1-isopropylpiperidin-4-yl)methyl)-2-fluorophenyl)ethyl)-6-(1-isopropylpiperidin-4-yl)-2-methylpyrido[2,3-d]pyrimidin-4-amine | 617.6 |
| 223 | 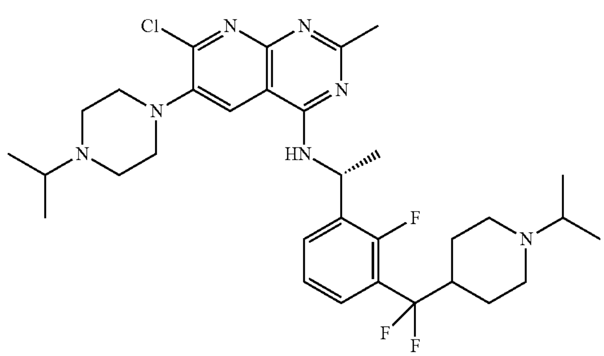 [SMILES: Cc1nc(N[C@H](C)c2cccc(C(F)(F)C3CCN(C(C)C)CC3)c2F)c2cc(N3CCN(C(C)C)CC3)c(Cl)nc2n1] | (R)-7-chloro-N-(1-(3-(difluoro(1-isopropylpiperidin-4-yl)methyl)-2-fluorophenyl)ethyl)-6-(4-isopropylpiperazin-1-yl)-2-methylpyrido[2,3-d]pyrimidin-4-amine | 618.6 |

TABLE 1-continued

| Compound | Structure | Name | [M + H]+ |
|---|---|---|---|
| 224 | 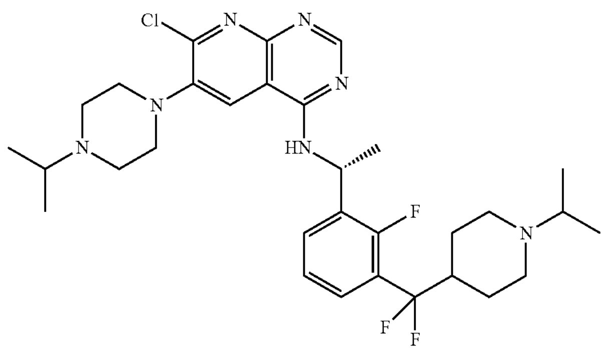 [SMILES: CC(C)N1CCC(C(F)(F)c2cccc([C@@H](C)Nc3ncnc4nc(Cl)c(N5CCN(C(C)C)CC5)cc34)c2F)CC1] | (R)-7-chloro-N-(1-(3-(difluoro(1-isopropylpiperidin-4-yl)methyl)-2-fluorophenyl)ethyl)-6-(4-isopropylpiperazin-1-yl)pyrido[2,3-d]pyrimidin-4-amine | 604.5 |
| 225 | 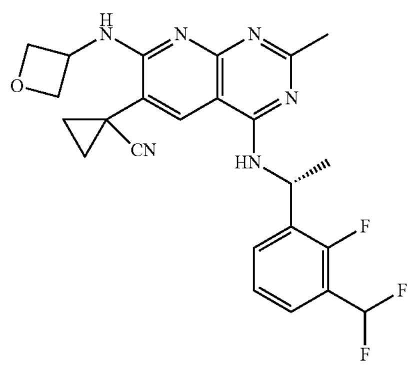 [SMILES: Cc1nc(N[C@H](C)c2cccc(C(F)F)c2F)c2cc(C3(C#N)CC3)c(NC3COC3)nc2n1] | (R)-1-(4-((1-(3-(difluoromethyl)-2-fluorophenyl)ethyl)amino)-2-methyl-7-(oxetan-3-ylamino)pyrido[2,3-d]pyrimidin-6-yl)cyclopropane-1-carbonitrile | 469.25 |
| 226 | 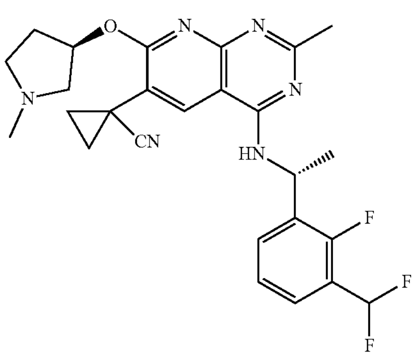 [SMILES: Cc1nc(N[C@H](C)c2cccc(C(F)F)c2F)c2cc(C3(C#N)CC3)c(O[C@@H]3CCN(C)C3)nc2n1] | 1-(4-(((R)-1-(3-(difluoromethyl)-2-fluorophenyl)ethyl)amino)-2-methyl-7-(((R)-1-methylpyrrolidin-3-yl)oxy)pyrido[2,3-d]pyrimidin-6-yl)cyclopropane-1-carbonitrile | 497.4 |
| 227 | 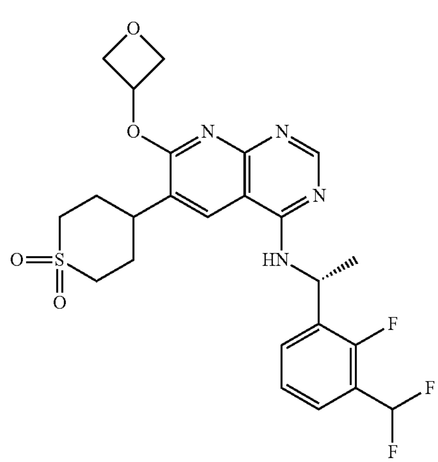 [SMILES: C[C@@H](Nc1ncnc2nc(OC3COC3)c(C3CCS(=O)(=O)CC3)cc12)c1cccc(C(F)F)c1F] | (R)-4-(4-((1-(3-(difluoromethyl)-2-fluorophenyl)ethyl)amino)-7-(oxetan-3-yloxy)pyrido[2,3-d]pyrimidin-6-yl)tetrahydro-2H-thiopyran 1,1-dioxide | 523.8 |

TABLE 1-continued

| Compound | Structure | Name | [M + H]+ |
|---|---|---|---|
| 228 | 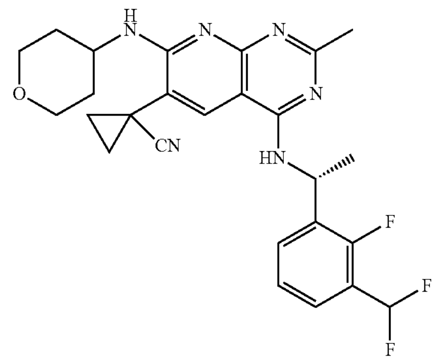 [SMILES: Cc1nc(N[C@H](C)c2cccc(C(F)F)c2F)c2cc(C3(C#N)CC3)c(NC3CCOCC3)nc2n1] | (R)-1-(4-((1-(3-(difluoromethyl)-2-fluorophenyl)ethyl)amino)-2-methyl-7-((tetrahydro-2H-pyran-4-yl)amino)pyrido[2,3-d]pyrimidin-6-yl)cyclopropane-1-carbonitrile | 497.3 |
| 229 | 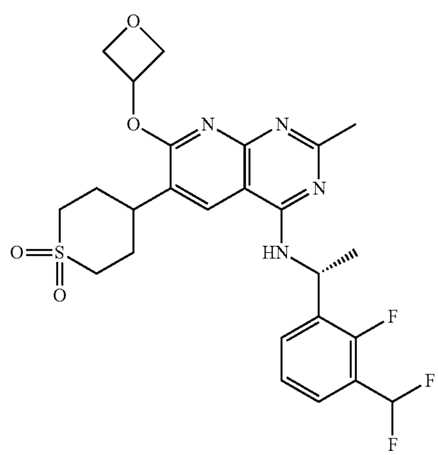 [SMILES: Cc1nc(N[C@H](C)c2cccc(C(F)F)c2F)c2cc(C3CCS(=O)(=O)CC3)c(OC3COC3)nc2n1] | (R)-4-(4-((1-(3-(difluoromethyl)-2-fluorophenyl)ethyl)amino)-2-methyl-7-(oxetan-3-yloxy)pyrido[2,3-d]pyrimidin-6-yl)tetrahydro-2H-thiopyran 1,1-dioxide | 537.3 |
| 230 | 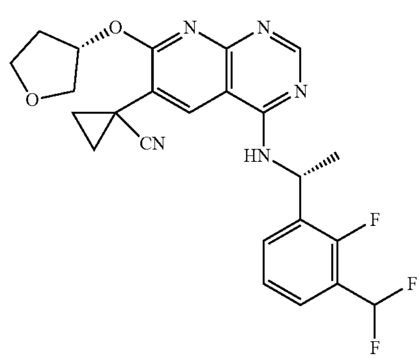 [SMILES: C[C@@H](Nc1ncnc2nc(O[C@H]3CCOC3)c(C3(C#N)CC3)cc12)c1cccc(C(F)F)c1F] | 1-(4-(((R)-1-(3-(difluoromethyl)-2-fluorophenyl)ethyl)amino)-7-(((S)-tetrahydrofuran-3-yl)oxy)pyrido[2,3-d]pyrimidin-6-yl)cyclopropane-1-carbonitrile | 470.7 |

TABLE 1-continued

| Compound | Structure | Name | [M + H]+ |
|---|---|---|---|
| 231 | 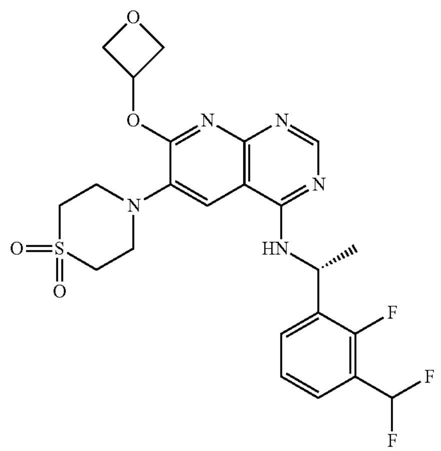 [SMILES: C[C@@H](Nc1ncnc2nc(OC3COC3)c(N3CCS(=O)(=O)CC3)cc12)c1cccc(C(F)F)c1F] | (R)-4-(4-((1-(3-(difluoromethyl)-2-fluorophenyl)ethyl)amino)-7-(oxetan-3-yloxy)pyrido[2,3-d]pyrimidin-6-yl)tetrahydro-2H-thiopyran 1,1-dioxide | 524.3 |
| 232 | 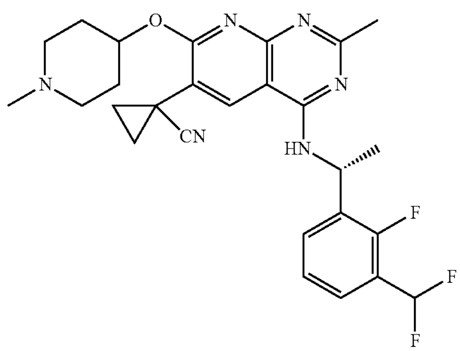 [SMILES: Cc1nc(N[C@H](C)c2cccc(C(F)F)c2F)c2cc(C3(C#N)CC3)c(OC3CCN(C)CC3)nc2n1] | (R)-1-(4-((1-(3-(difluoromethyl)-2-fluorophenyl)ethyl)amino)-2-methyl-7-((1-methylpiperidin-4-yl)oxy)pyrido[2,3-d]pyrimidin-6-yl)cyclopropane-1-carbonitrile | 511.3 |
| 233 | 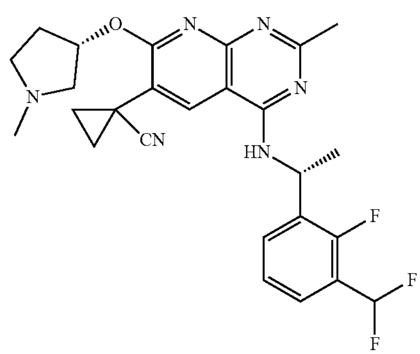 [SMILES: Cc1nc(N[C@H](C)c2cccc(C(F)F)c2F)c2cc(C3(C#N)CC3)c(O[C@H]3CCN(C)C3)nc2n1] | 1-(4-(((R)-1-(3-(difluoromethyl)-2-fluorophenyl)ethyl)amino)-2-methyl-7-(((S)-1-methylpyrrolidin-3-yl)oxy)pyrido[2,3-d]pyrimidin-6-yl)cyclopropane-1-carbonitrile | 497.4 |
| 234 | 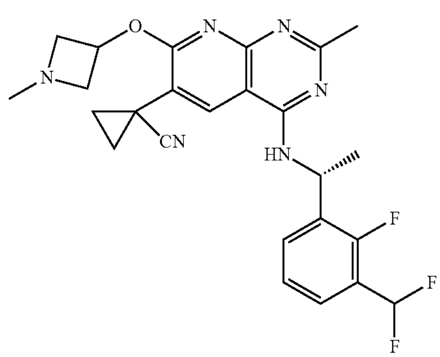 [SMILES: Cc1nc(N[C@H](C)c2cccc(C(F)F)c2F)c2cc(C3(C#N)CC3)c(OC3CN(C)C3)nc2n1] | (R)-1-(4-((1-(3-(difluoromethyl)-2-fluorophenyl)ethyl)amino)-2-methyl-7-((1-methylazetidin-3-yl)oxy)pyrido[2,3-d]pyrimidin-6-yl)cyclopropane-1-carbonitrile | 483.3 |

TABLE 1-continued

| Compound | Structure | Name | [M + H]+ |
|---|---|---|---|
| 235 | 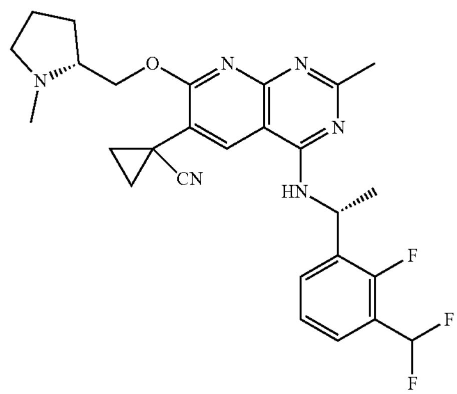 [SMILES: Cc1nc(N[C@H](C)c2cccc(C(F)F)c2F)c2cc(C3(C#N)CC3)c(OC[C@H]3CCCN3C)nc2n1] | 1-(4-(((R)-1-(3-(difluoromethyl)-2-fluorophenyl)ethyl)amino)-2-methyl-7-(((R)-1-methylpyrrolidin-2-yl)methoxy)pyrido[2,3-d]pyrimidin-6-yl)cyclopropane-1-carbonitrile | 511.4 |
| 236 | 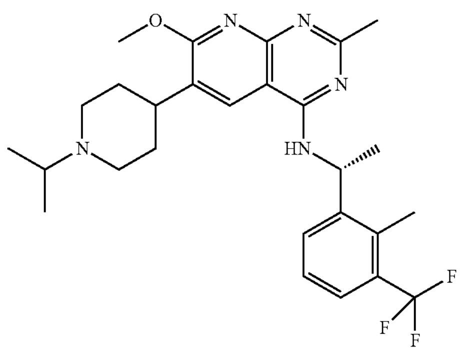 [SMILES: COc1nc2nc(C)nc(N[C@H](C)c3cccc(C(F)(F)F)c3C)c2cc1C1CCN(C(C)C)CC1] | (R)-6-(1-isopropylpiperidin-4-yl)-7-methoxy-2-methyl-N-(1-(2-methyl-3-(trifluoromethyl)phenyl)ethyl)pyrido[2,3-d]pyrimidin-4-amine | 502.3 |
| 237 | 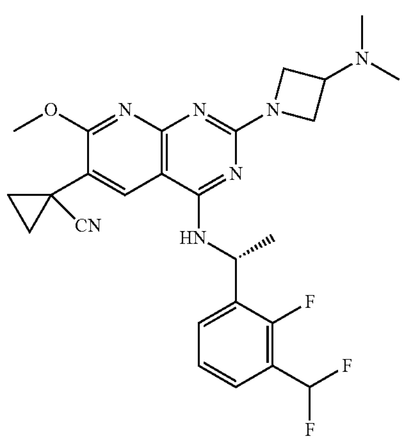 [SMILES: COc1nc2nc(N3CC(N(C)C)C3)nc(N[C@H](C)c3cccc(C(F)F)c3F)c2cc1C1(C#N)CC1] | (R)-1-(4-((1-(3-(difluoromethyl)-2-fluorophenyl)ethyl)amino)-2-(3-(dimethylamino)azetidin-1-yl)-7-methoxypyrido[2,3-d]pyrimidin-6-yl)cyclopropane-1-carbonitrile | 512.3 |
| 238 | 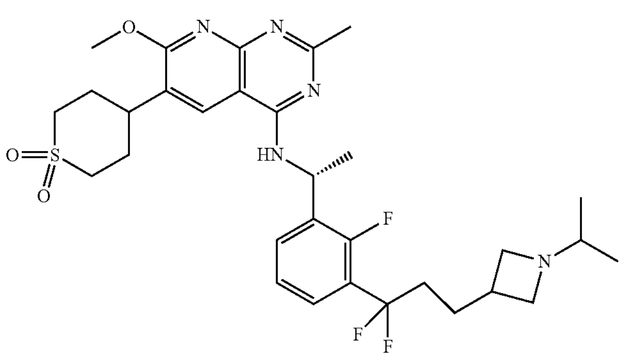 [SMILES: COc1nc2nc(C)nc(N[C@H](C)c3cccc(C(F)(F)CCC4CN(C(C)C)C4)c3F)c2cc1C1CCS(=O)(=O)CC1] | (R)-4-(4-((1-(3-(1,1-difluoro-3-(1-isopropylazetidin-3-yl)propyl)-2-fluorophenyl)ethyl)amino)-7-methoxy-2-methylpyrido[2,3-d]pyrimidin-6-yl)tetrahydro-2H-thiopyran 1,1-dioxide | 620.4 |

TABLE 1-continued

| Compound | Structure | Name | [M + H]+ |
|---|---|---|---|
| 239 | 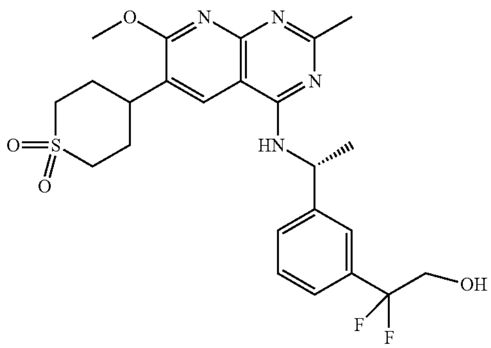 [SMILES: COc1nc2nc(C)nc(N[C@H](C)c3cccc(C(F)(F)CO)c3)c2cc1C1CCS(=O)(=O)CC1] | (R)-4-(4-((1-(3-(1,1-difluoro-2-hydroxyethyl)phenyl)ethyl)amino)-7-methoxy-2-methylpyrido[2,3-d]pyrimidin-6-yl)tetrahydro-2H-thiopyran 1,1-dioxide | 507.6 |
| 240 | 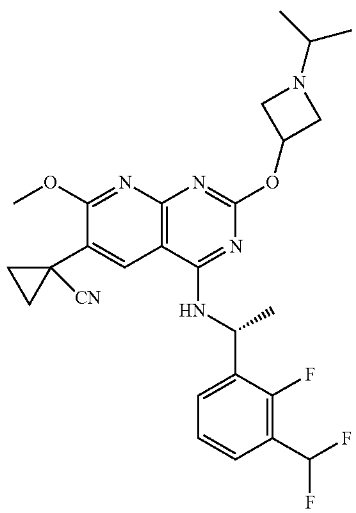 [SMILES: COc1nc2nc(OC3CN(C(C)C)C3)nc(N[C@H](C)c3cccc(C(F)F)c3F)c2cc1C1(C#N)CC1] | (R)-1-(4-((1-(3-(difluoromethyl)-2-fluorophenyl)ethyl)amino)-2-((1-isopropylazetidin-3-yl)oxy)-7-methoxypyrido[2,3-d]pyrimidin-6-yl)cyclopropane-1-carbonitrile | 527.3 |
| 241 | 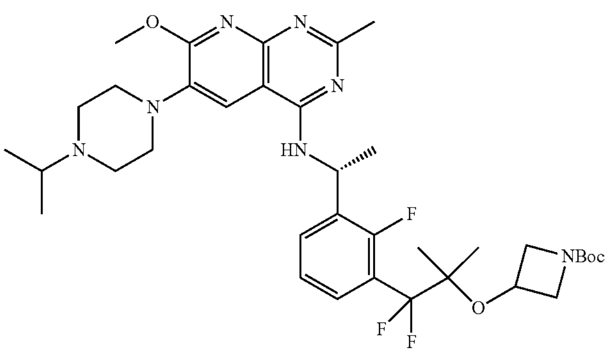 [SMILES: COc1nc2nc(C)nc(N[C@H](C)c3cccc(C(F)(F)C(C)(C)OC4CN(C(=O)OC(C)(C)C)C4)c3F)c2cc1N1CCN(C(C)C)CC1] | tert-butyl (R)-3-((1,1-difluoro-1-(2-fluoro-3-(1-((6-(4-isopropylpiperazin-1-yl)-7-methoxy-2-methylpyrido[2,3-d]pyrimidin-4-yl)amino)ethyl)phenyl)-2-methylpropan-2-yl)oxy)azetidine-1-carboxylate | 702.6 |
| 242 | 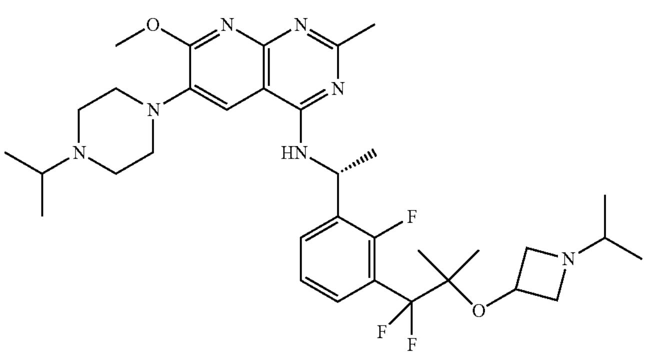 [SMILES: COc1nc2nc(C)nc(N[C@H](C)c3cccc(C(F)(F)C(C)(C)OC4CN(C(C)C)C4)c3F)c2cc1N1CCN(C(C)C)CC1] | (R)-N-(1-(3-(1,1-difluoro-2-((1-isopropylazetidin-3-yl)oxy)-2-methylpropyl)-2-fluorophenyl)ethyl)-6-(4-isopropylpiperazin-1-yl)-7-methoxy-2-methylpyrido[2,3-d]pyrimidin-4-amine | 644.5 |

TABLE 1-continued

| Compound | Structure | Name | [M + H]⁺ |
|---|---|---|---|
| 243 | 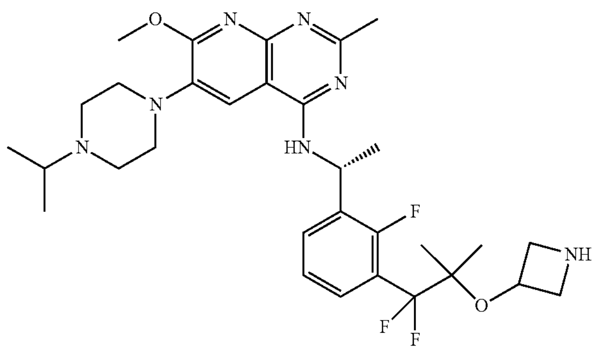 [SMILES: COc1nc2nc(C)nc(N[C@H](C)c3cccc(C(F)(F)C(C)(C)OC4CNC4)c3F)c2cc1N1CCN(C(C)C)CC1] | (R)-N-(1-(3-(2-(azetidin-3-yloxy)-1,1-difluoro-2-methylpropyl)-2-fluorophenyl)ethyl)-6-(4-isopropylpiperazin-1-yl)-7-methoxy-2-methylpyrido[2,3-d]pyrimidin-4-amine | 602.5 |
| 244 | 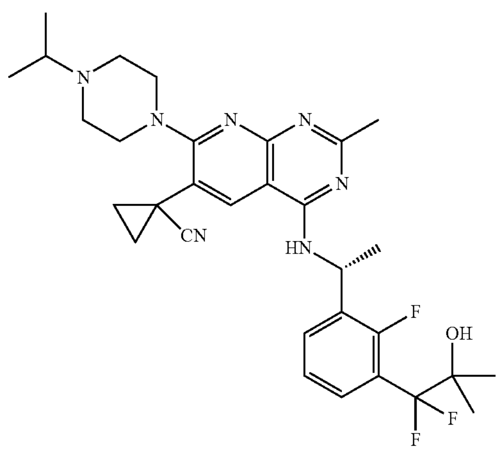 [SMILES: Cc1nc(N[C@H](C)c2cccc(C(F)(F)C(C)(C)O)c2F)c2cc(C3(C#N)CC3)c(N3CCN(C(C)C)CC3)nc2n1] | (R)-1-(4-((1-(3-(1,1-difluoro-2-hydroxy-2-methylpropyl)-2-fluorophenyl)ethyl)amino)-7-(4-isopropylpiperazin-1-yl)-2-methylpyrido[2,3-d]pyrimidin-6-yl)cyclopropane-1-carbonitrile | 582.5 |
| 245 | 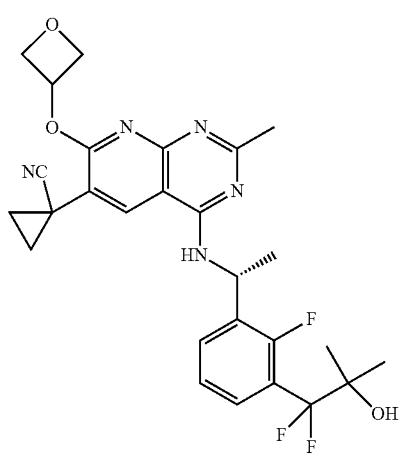 [SMILES: Cc1nc(N[C@H](C)c2cccc(C(F)(F)C(C)(C)O)c2F)c2cc(C3(C#N)CC3)c(OC3COC3)nc2n1] | (R)-1-(4-((1-(3-(1,1-difluoro-2-hydroxy-2-methylpropyl)-2-fluorophenyl)ethyl)amino)-2-methyl-7-(oxetan-3-yloxy)pyrido[2,3-d]pyrimidin-6-yl)cyclopropane-1-carbonitrile | 528.7 |

TABLE 1-continued

| Compound | Structure | Name | [M + H]+ |
|---|---|---|---|
| 246 | 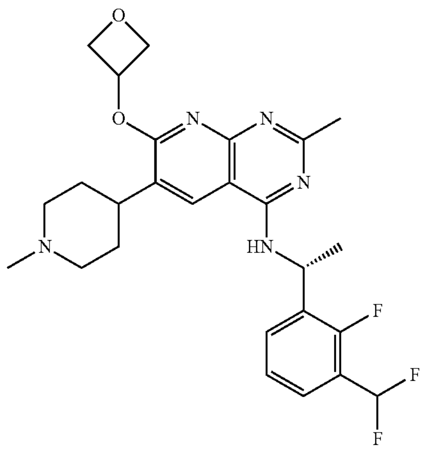 [SMILES: Cc1nc(N[C@H](C)c2cccc(C(F)F)c2F)c2cc(C3CCN(C)CC3)c(OC3COC3)nc2n1] | (R)-N-(1-(3-(difluoromethyl)-2-fluorophenyl)ethyl)-2-methyl-6-(1-methylpiperidin-4-yl)-7-(oxetan-3-yloxy)pyrido[2,3-d]pyrimidin-4-amine | 502.5 |
| 247 | 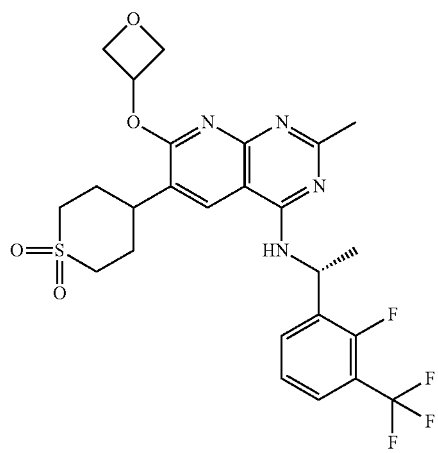 [SMILES: Cc1nc(N[C@H](C)c2cccc(C(F)(F)F)c2F)c2cc(C3CCS(=O)(=O)CC3)c(OC3COC3)nc2n1] | (R)-4-(4-((1-(2-fluoro-3-(trifluoromethyl)phenyl)ethyl)amino)-2-methyl-7-(oxetan-3-yloxy)pyrido[2,3-d]pyrimidin-6-yl)tetrahydro-2H-thiopyran 1,1-dioxide | 555.8 |
| 248 | 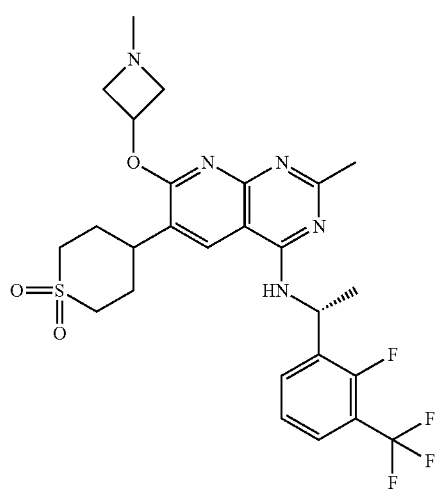 [SMILES: Cc1nc(N[C@H](C)c2cccc(C(F)(F)F)c2F)c2cc(C3CCS(=O)(=O)CC3)c(OC3CN(C)C3)nc2n1] | (R)-4-(4-((1-(2-fluoro-3-(trifluoromethyl)phenyl)ethyl)amino)-2-methyl-7-((1-methylazetidin-3-yl)oxy)pyrido[2,3-d]pyrimidin-6-yl)tetrahydro-2H-thiopyran 1,1-dioxide | 568.5 |

TABLE 1-continued

| Compound | Structure | Name | [M + H]+ |
|---|---|---|---|
| 249 | 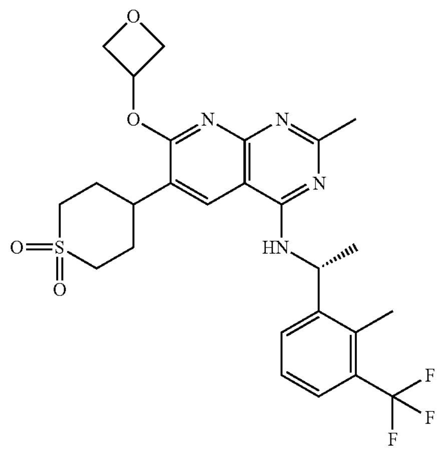 [SMILES: Cc1nc(N[C@H](C)c2cccc(C(F)(F)F)c2C)c2cc(C3CCS(=O)(=O)CC3)c(OC3COC3)nc2n1] | (R)-4-(2-methyl-4-((1-(2-methyl-3-(trifluoromethyl)phenyl)ethyl)amino)-7-(oxetan-3-yloxy)pyrido[2,3-d]pyrimidin-6-yl)tetrahydro-2H-thiopyran 1,1-dioxide | 551.5 |
| 250 | 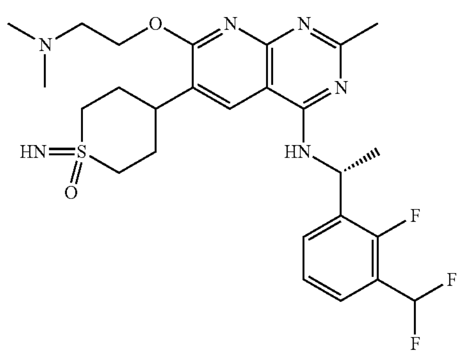 [SMILES: Cc1nc(N[C@H](C)c2cccc(C(F)F)c2F)c2cc(C3CCS(=N)(=O)CC3)c(OCCN(C)C)nc2n1] | (R)-4-(4-((1-(3-(difluoromethyl)-2-fluorophenyl)ethyl)amino)-7-(2-(dimethylamino)ethoxy)-2-methylpyrido[2,3-d]pyrimidin-6-yl)-1-iminohexahydro-1l6-thiopyran 1-oxide | 551.5 |
| 251 | 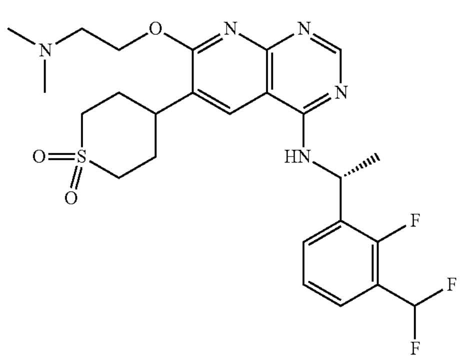 [SMILES: C[C@@H](Nc1ncnc2nc(OCCN(C)C)c(C3CCS(=O)(=O)CC3)cc12)c1cccc(C(F)F)c1F] | (R)-4-(4-((1-(3-(difluoromethyl)-2-fluorophenyl)ethyl)amino)-7-(2-(dimethylamino)ethoxy)pyrido[2,3-d]pyrimidin-6-yl)tetrahydro-2H-thiopyran 1,1-dioxide | 538.5 |

TABLE 1-continued

| Compound | Structure | Name | [M + H]+ |
|---|---|---|---|
| 252 | 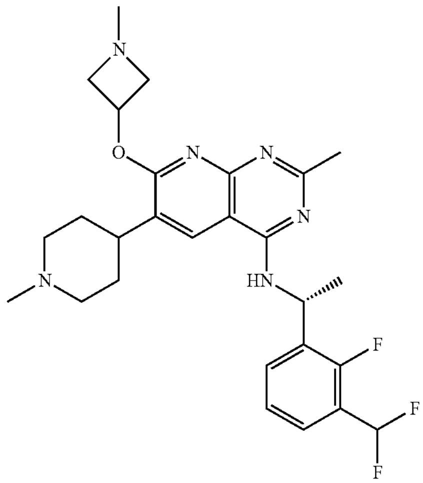 [SMILES: Cc1nc(N[C@H](C)c2cccc(C(F)F)c2F)c2cc(C3CCN(C)CC3)c(OC3CN(C)C3)nc2n1] | (R)-N-(1-(3-(difluoromethyl)-2-fluorophenyl)ethyl)-2-methyl-7-((1-methylazetidin-3-yl)oxy)-6-(1-methylpiperidin-4-yl)pyrido[2,3-d]pyrimidin-4-amine | 515.5 |
| 253 | 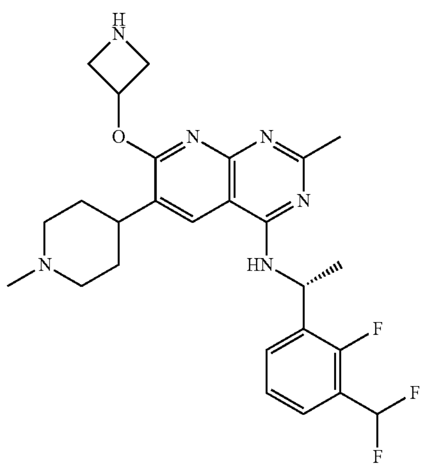 [SMILES: Cc1nc(N[C@H](C)c2cccc(C(F)F)c2F)c2cc(C3CCN(C)CC3)c(OC3CNC3)nc2n1] | (R)-7-(azetidin-3-yloxy)-N-(1-(3-(difluoromethyl)-2-fluorophenyl)ethyl)-2-methyl-6-(1-methylpiperidin-4-yl)pyrido[2,3-d]pyrimidin-4-amine | 501.5 |
| 254 | 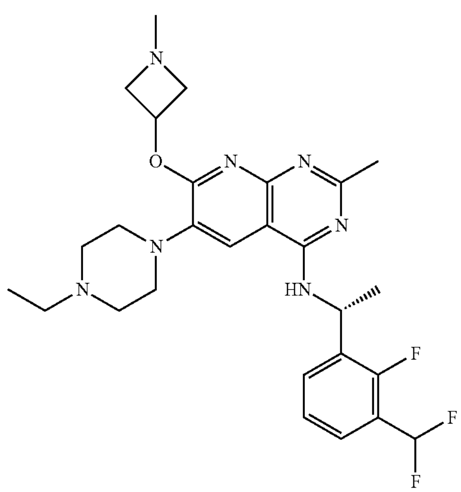 [SMILES: CCN1CCN(c2cc3c(N[C@H](C)c4cccc(C(F)F)c4F)nc(C)nc3nc2OC2CN(C)C2)CC1] | (R)-N-(1-(3-(difluoromethyl)-2-fluorophenyl)ethyl)-6-(4-ethylpiperazin-1-yl)-2-methyl-7-((1-methylazetidin-3-yl)oxy)pyrido[2,3-d]pyrimidin-4-amine | 530.5 |

TABLE 1-continued

| Compound | Structure | Name | [M + H]+ |
|---|---|---|---|
| 255 | 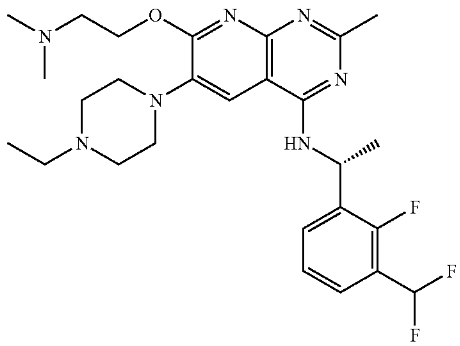 [SMILES: CCN1CCN(c2cc3c(N[C@H](C)c4cccc(C(F)F)c4F)nc(C)nc3nc2OCCN(C)C)CC1] | (R)-N-(1-(3-(difluoromethyl)-2-fluorophenyl)ethyl)-7-(2-(dimethylamino)ethoxy)-6-(4-ethylpiperazin-1-yl)-2-methylpyrido[2,3-d]pyrimidin-4-amine | 532.5 |
| 256 | 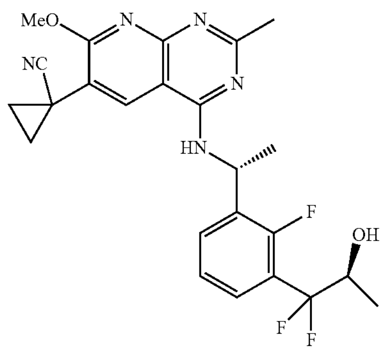 [SMILES: COc1nc2nc(C)nc(N[C@H](C)c3cccc(C(F)(F)[C@H](C)O)c3F)c2cc1C1(C#N)CC1] | 1-(4-(((R)-1-(3-((S)-1,1-difluoro-2-hydroxypropyl)-2-fluorophenyl)ethyl)amino)-7-methoxy-2-methylpyrido[2,3-d]pyrimidin-6-yl)cyclopropane-1-carbonitrile | 472.3 |
| 257 | 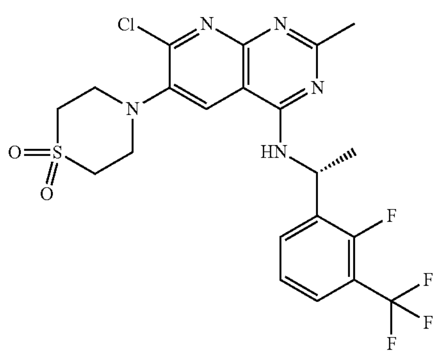 [SMILES: Cc1nc(N[C@H](C)c2cccc(C(F)(F)F)c2F)c2cc(N3CCS(=O)(=O)CC3)c(Cl)nc2n1] | (R)-4-(7-chloro-4-((1-(2-fluoro-3-(trtfluoromethyl)phenyl)ethyl)amino)-2-methylpyrido[2,3-d]pyrimidin-6-yl)thiomorpholine 1,1-dioxide | 518.3 |
| 258 | 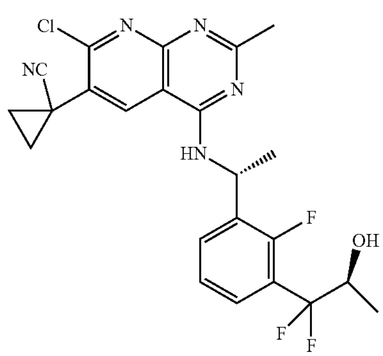 [SMILES: Cc1nc(N[C@H](C)c2cccc(C(F)(F)[C@H](C)O)c2F)c2cc(C3(C#N)CC3)c(Cl)nc2n1] | 1-(7-chloro-4-(((R)-1-(3-((S)-1,1-difluoro-2-hydroxypropyl)-2-fluorophenyl)ethyl)amino)-2-methylpyrido[2,3-d]pyrimidin-6-yl)cyclopropane-1-carbonitrile | 476.3 |

TABLE 1-continued

| Compound | Structure | Name | [M + H]⁺ |
|---|---|---|---|
| 259 | 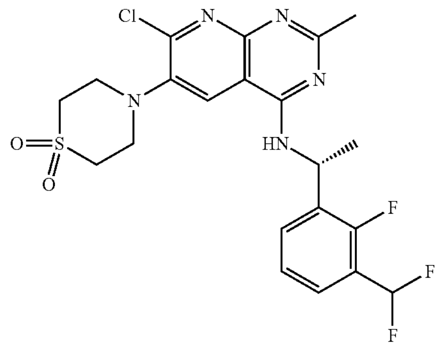 | (R)-4-(7-chloro-4-((1-(3-(difluoromethyl)-2-fluorophenyl)ethyl)amino)-2-methylpyrido[2,3-d]pyrimidin-6-yl)thiomorpholine 1,1-dioxide | 500.3 |
| 260 | 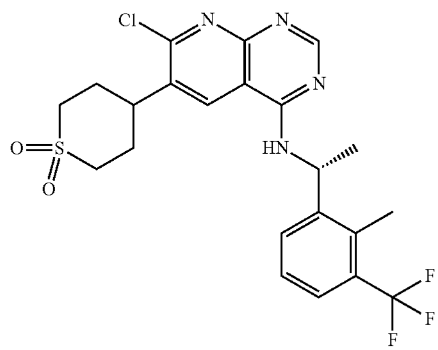 [SMILES: Cc1c([C@@H](C)Nc2ncnc3nc(Cl)c(C4CCS(=O)(=O)CC4)cc23)cccc1C(F)(F)F] | (R)-4-(7-chloro-4-((1-(2-methyl-3-(trifluoromethyl)phenyl)ethyl)amino)pyrido[2,3-d]pyrimidin-6-yl)tetrahydro-2H-thiopyran 1,1-dioxide | 499.3 |
| 261 | 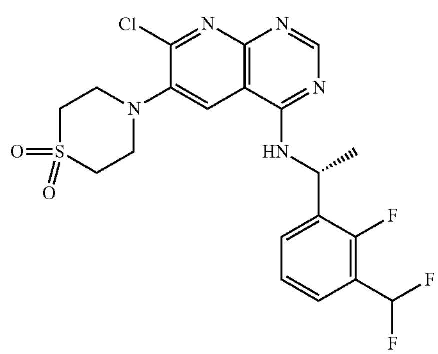 [SMILES: C[C@@H](Nc1ncnc2nc(Cl)c(N3CCS(=O)(=O)CC3)cc12)c1cccc(C(F)F)c1F] | (R)-4-(7-chloro-4-((1-(3-(difluoromethyl)-2-fluorophenyl)ethyl)amino)pyrido[2,3-d]pyrimidin-6-yl)thiomorpholine 1,1-dioxide | 486.2 |
| 262 | 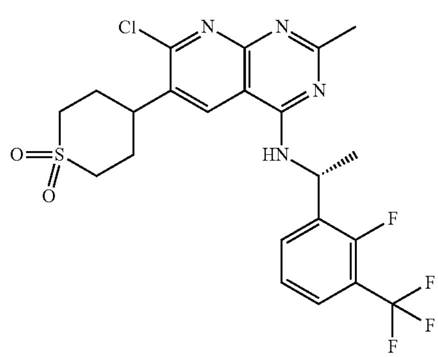 [SMILES: Cc1nc(N[C@H](C)c2cccc(C(F)(F)F)c2F)c2cc(C3CCS(=O)(=O)CC3)c(Cl)nc2n1] | (R)-4-(7-chloro-4-((1-(2-fluoro-3-(trifluoromethyl)phenyl)ethyl)amino)-2-methylpyrido[2,3-d]pyrimidin-6-yl)tetrahydro-2H-thiopyran 1,1-dioxide | 517.3 |

TABLE 1-continued

| Compound | Structure | Name | [M + H]+ |
|---|---|---|---|
| 263 | 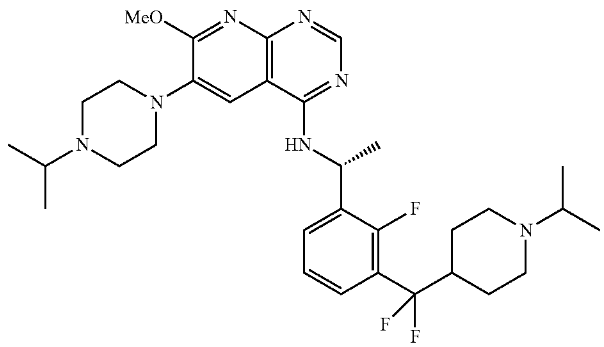 | (R)-N-(1-(3-(difluoro(1-isopropylpiperidin-4-yl)methyl)-2-fluorophenyl)ethyl)-6-(4-isopropylpiperazin-1-yl)-7-methoxypyrido[2,3-d]pyrimidin-4-amine | 600.3 |
| 264 | 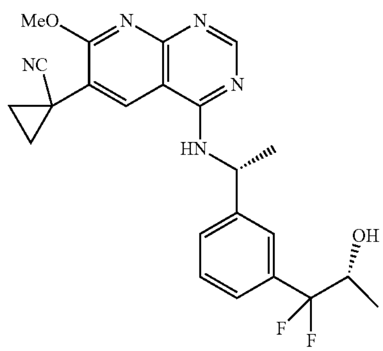 [SMILES: COc1nc2ncnc(N[C@H](C)c3cccc(C(F)(F)[C@@H](C)O)c3)c2cc1C1(C#N)CC1] | 1-(4-(((R)-1-(3-((R)-1,1-difluoro-2-hydroxypropyl)phenyl)ethyl)amino)-7-methoxypyrido[2,3-d]pyrimidin-6-yl)cyclopropane-1-carbonitrile | 440.3 |
| 265 | 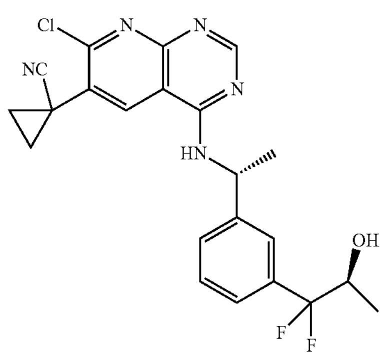 [SMILES: C[C@H](O)C(F)(F)c1cccc([C@@H](C)Nc2ncnc3nc(Cl)c(C4(C#N)CC4)cc23)c1] | 1-(7-chloro-4-(((R)-1-(3-((S)-1,1-difluoro-2-hydroxypropyl)phenyl)ethyl)amino)pyrido[2,3-d]pyrimidin-6-yl)cyclopropane-1-carbonitrile | 444. |
| 266 | 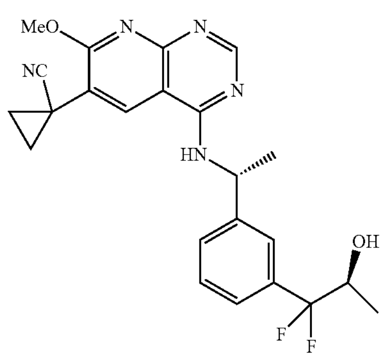 [SMILES: COc1nc2ncnc(N[C@H](C)c3cccc(C(F)(F)[C@H](C)O)c3)c2cc1C1(C#N)CC1] | 1-(4-(((R)-1-(3-((S)-1,1-difluoro-2-hydroxypropyl)phenyl)ethyl)amino)-7-methoxypyrido[2,3-d]pyrimidin-6-yl)cyclopropane-1-carbonitrile | 440.2 |

TABLE 1-continued

| Compound | Structure | Name | [M + H]+ |
|---|---|---|---|
| 267 | 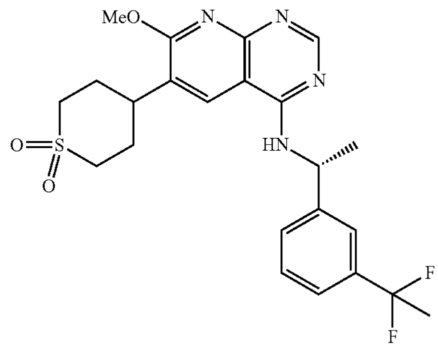 [SMILES: COc1nc2ncnc(N[C@H](C)c3cccc(C(C)(F)F)c3)c2cc1C1CCS(=O)(=O)CC1] | (R)-4-(4-((1-(3-(1,1-difluoroethyl)-2-fluorophenyl)ethyl)amino)-7-methoxypyrido[2,3-d]pyrimidin-6-yl)tetrahydro-2H-thiopyran 1,1-dioxide | 495.3 |
| 268 | 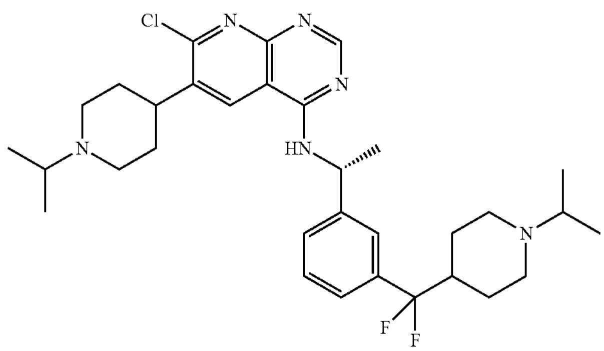 [SMILES: CC(C)N1CCC(c2cc3c(N[C@H](C)c4cccc(C(F)(F)C5CCN(C(C)C)CC5)c4)ncnc3nc2Cl)CC1] | (R)-7-chloro-N-(1-(3-(difluoro(1-isopropylpiperidin-4-yl)methyl)phenyl)ethyl)-6-(1-isopropylpiperidin-4-yl)pyrido[2,3-d]pyrimidin-4-amine | 585.3 |
| 269 | 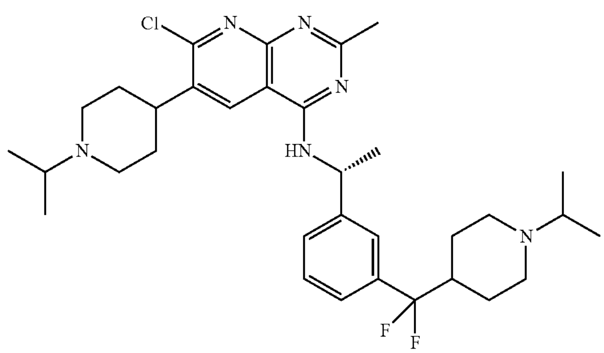 [SMILES: Cc1nc(N[C@H](C)c2cccc(C(F)(F)C3CCN(C(C)C)CC3)c2)c2cc(C3CCN(C(C)C)CC3)c(Cl)nc2n1] | (R)-7-chloro-N-(1-(3-(difluoro(1-isopropylpiperidin-4-yl)methyl)phenyl)ethyl)-6-(1-isopropylpiperidin-4-yl)-2-methylpyrido[2,3-d]pyrimidin-4-amine | 599.6 |
| 270 | 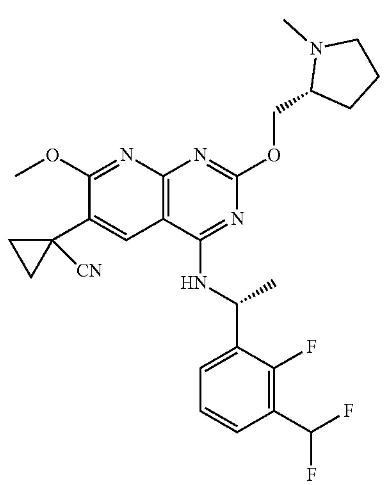 [SMILES: COc1nc2nc(OC[C@H]3CCCN3C)nc(N[C@H](C)c3cccc(C(F)F)c3F)c2cc1C1(C#N)CC1] | 1-(4-(((R)-1-(3-(difluoromethyl)-2-fluorophenyl)ethyl)amino)-7-methoxy-2-(((R)-1-methylpyrrolidin-2-yl)methoxy)pyrido[2,3-d]pyrimidin-6-yl)cyclopropane-1-carbonitrile | 527.5 |

TABLE 1-continued

| Compound | Structure | Name | [M + H]+ |
|---|---|---|---|
| 271 | 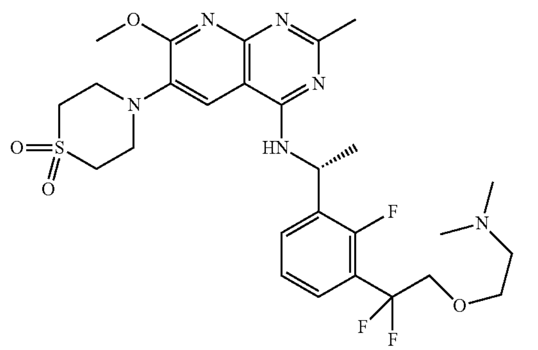 [SMILES: COc1nc2nc(C)nc(N[C@H](C)c3cccc(C(F)(F)COCCN(C)C)c3F)c2cc1N1CCS(=O)(=O)CC1] | (R)-4-(4-((1-(3-(2-(2-(dimethylamino)ethoxy)-1,1-difluoroethyl)-2-fluorophenyl)ethyl)amino)-7-methoxy-2-methylpyrido[2,3-d]pyrimidin-6-yl)thiomorpholine 1,1-dioxide | 596.5 |
| 272 | 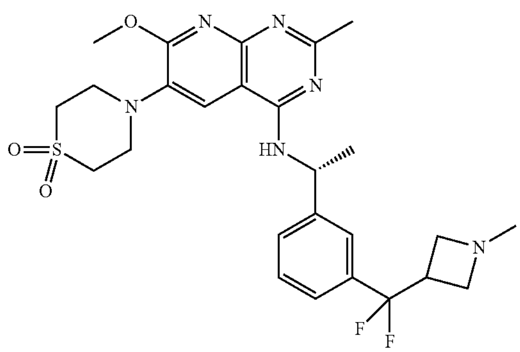 [SMILES: COc1nc2nc(C)nc(N[C@H](C)c3cccc(C(F)(F)C4CN(C)C4)c3)c2cc1N1CCS(=O)(=O)CC1] | (R)-4-(4-((1-(3-(difluoro(1-methylazetidin-3-yl)methyl)phenyl)ethyl)amino)-7-methoxy-2-methylpyrido[2,3-d]pyrimidin-6-yl)thiomorpholine 1,1-dioxide | 546.4 |
| 273 | 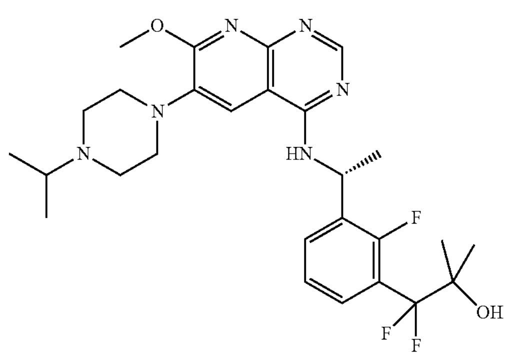 [SMILES: COc1nc2ncnc(N[C@H](C)c3cccc(C(F)(F)C(C)(C)O)c3F)c2cc1N1CCN(C(C)C)CC1] | (R)-1,1-difluoro-1-(2-fluoro-3-(1-((6-(4-isopropylpiperazin-1-yl)-7-methoxypyrido[2,3-d]pyrimidin-4-yl)amino)ethyl)phenyl)-2-methylpropan-2-ol | 533.5 |
| 274 | 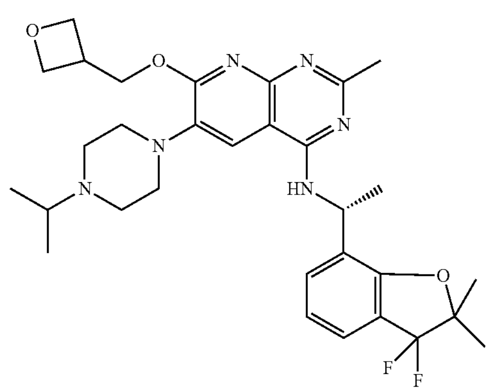 [SMILES: Cc1nc(N[C@H](C)c2cccc3c2OC(C)(C)C3(F)F)c2cc(N3CCN(C(C)C)CC3)c(OCC3COC3)nc2n1] | (R)-N-(1-(3,3-difluoro-2,2-dimethyl-2,3-dihydrobenzofuran-7-yl)ethyl)-6-(4-isopropylpiperazin-1-yl)-2-methyl-7-(oxetan-3-ylmethoxy)pyrido[2,3-d]pyrimidin-4-amine | 583.6 |

TABLE 1-continued

| Compound | Structure | Name | [M + H]+ |
|---|---|---|---|
| 275 | 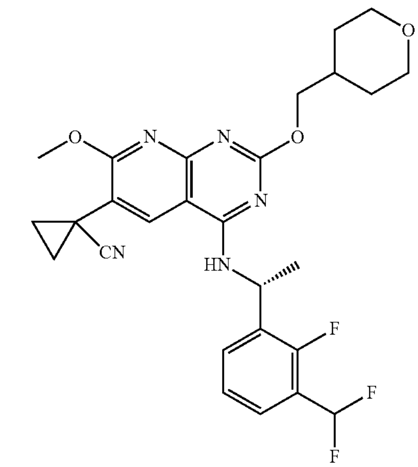 [SMILES: COc1nc2nc(OCC3CCOCC3)nc(N[C@H](C)c3cccc(C(F)F)c3F)c2cc1C1(C#N)CC1] | (R)-1-(4-((1-(3-(difluoromethyl)-2-fluorophenyl)ethyl)amino)-7-methoxy-2-((tetrahydro-2H-pyran-4-yl)methoxy)pyrido[2,3-d]pyrimidin-6-yl)cyclopropane-1-carbonitrile | 528.8 |
| 276 | 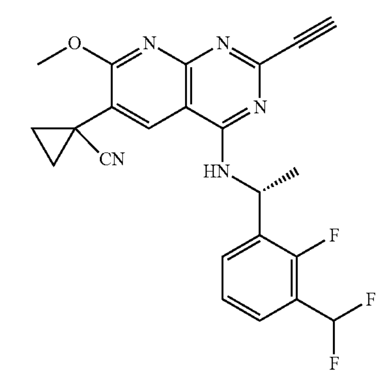 [SMILES: C#Cc1nc(N[C@H](C)c2cccc(C(F)F)c2F)c2cc(C3(C#N)CC3)c(OC)nc2n1] | (R)-1-(4-((1-(3-(difluoromethyl)-2-fluorophenyl)ethyl)amino)-2-ethynyl-7-methoxypyrido[2,3-d]pyrimidin-6-yl)cyclopropane-1-carbonitrile | 438.3 |
| 277 | 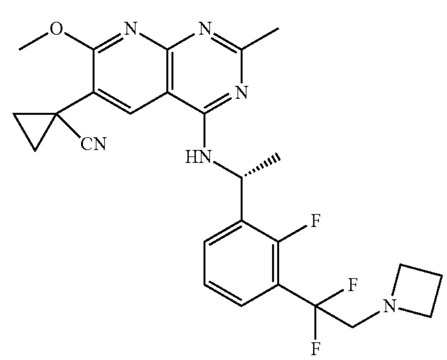 [SMILES: COc1nc2nc(C)nc(N[C@H](C)c3cccc(C(F)(F)CN4CCC4)c3F)c2cc1C1(C#N)CC1] | (R)-1-(4-((1-(3-(2-(azetidin-1-yl)-1,1-difluoroethyl)-2-fluorophenyl)ethyl)amino)-7-methoxy-2-methylpyrido[2,3-d]pyrimidin-6-yl)cyclopropane-1-carbonitrile | 497.4 |

TABLE 1-continued

| Compound | Structure | Name | [M + H]+ |
|---|---|---|---|
| 278 | 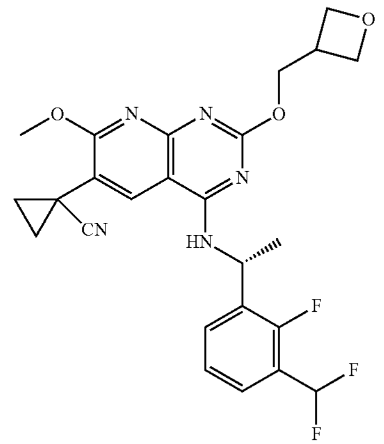 [SMILES: COc1nc2nc(OCC3COC3)nc(N[C@H](C)c3cccc(C(F)F)c3F)c2cc1C1(C#N)CC1] | (R)-1-(4-((1-(3-(difluoromethyl)-2-fluorophenyl)ethyl)amino)-7-methoxy-2-(oxetan-3-ylmethoxy)pyrido[2,3-d]pyrimidin-6-yl)cyclopropane-1-carbonitrile | 500.4 |
| 279 | 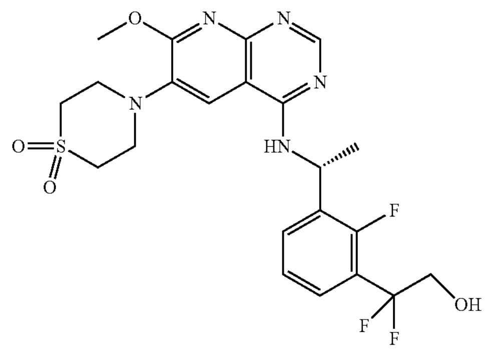 [SMILES: COc1nc2ncnc(N[C@H](C)c3cccc(C(F)(F)CO)c3F)c2cc1N1CCS(=O)(=O)CC1] | (R)-4-(4-((1-(3-(1,1-difluoro-2-hydroxyethyl)-2-fluorophenyl)ethyl)amino)-7-methoxypyrido[2,3-d]pyrimidin-6-yl)thiomorpholine 1,1-dioxide | 512.3 |
| 280 | 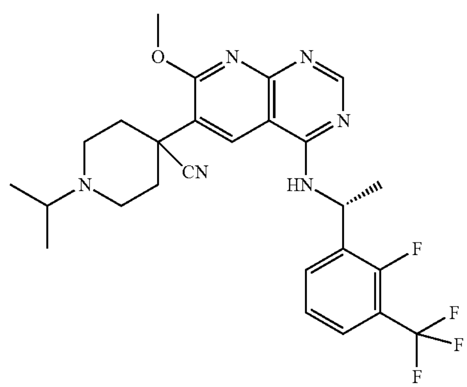 [SMILES: COc1nc2ncnc(N[C@H](C)c3cccc(C(F)(F)F)c3F)c2cc1C1(C#N)CCN(C(C)C)CC1] | (R)-4-(4-((1-(2-fluoro-3-(trifluoromethyl)phenyl)ethyl)amino)-7-methoxypyrido[2,3-d]pyrimidin-6-yl)-1-isopropylpiperidine-4-carbonitrile | 517.4 |
| 281 | 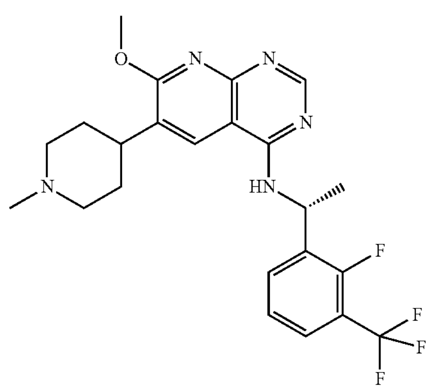 [SMILES: COc1nc2ncnc(N[C@H](C)c3cccc(C(F)(F)F)c3F)c2cc1C1CCN(C)CC1] | (R)-N-(1-(2-fluoro-3-(trifluoromethyl)phenyl)ethyl)-7-methoxy-6-(1-methylpiperidin-4-yl)pyrido[2,3-d]pyrimidin-4-amine | 464.3 |

TABLE 1-continued

| Compound | Structure | Name | [M + H]⁺ |
|---|---|---|---|
| 282 | 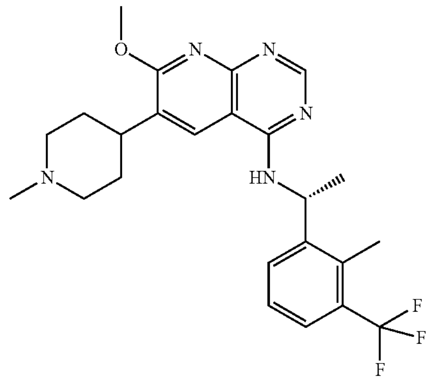 [SMILES: COc1nc2ncnc(N[C@H](C)c3cccc(C(F)(F)F)c3C)c2cc1C1CCN(C)CC1] | (R)-7-methoxy-N-(1-(2-methyl-3-(trifluoromethyl)phenyl)ethyl)-6-(1-methylpiperidin-4-yl)pyrido[2,3-d]pyrimidin-4-amine | 460.3 |
| 283 | 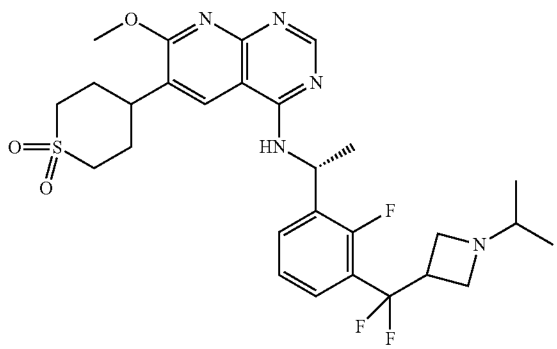 [SMILES: COc1nc2ncnc(N[C@H](C)c3cccc(C(F)(F)C4CN(C(C)C)C4)c3F)c2cc1C1CCS(=O)(=O)CC1] | (R)-4-(4-((1-(3-(difluoro(1-isopropylazetidin-3-yl)methyl)-2-fluorophenyl)ethyl)amino)-7-methoxypyrido[2,3-d]pyrimidin-6-yl)tetrahydro-2H-thiopyran 1,1-dioxide | 578.4 |
| 284 | 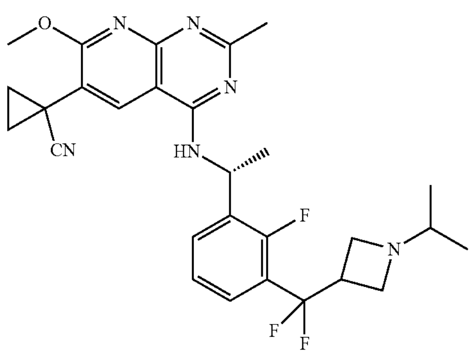 [SMILES: COc1nc2nc(C)nc(N[C@H](C)c3cccc(C(F)(F)C4CN(C(C)C)C4)c3F)c2cc1C1(C#N)CC1] | (R)-1-(4-((1-(3-(difluoro(1-isopropylazetidin-3-yl)methyl)-2-fluorophenyl)ethyl)amino)-7-methoxy-2-methylpyrido[2,3-d]pyrimidin-6-yl)cyclopropane-1-carbonitrile | 525.4 |
| 285 | 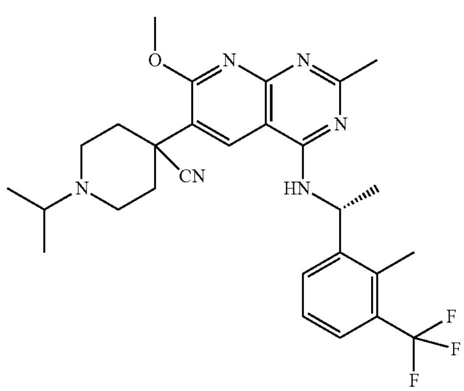 [SMILES: COc1nc2nc(C)nc(N[C@H](C)c3cccc(C(F)(F)F)c3C)c2cc1C1(C#N)CCN(C(C)C)CC1] | (R)-1-isopropyl-4-(7-methoxy-2-methyl-4-((1-(2-methyl-3-(trifluoromethyl)phenyl)ethyl)amino)pyrido[2,3-d]pyrimidin-6-yl)piperidine-4-carbonitrile | 527.4 |

TABLE 1-continued

| Compound | Structure | Name | [M + H]⁺ |
|---|---|---|---|
| 286 | 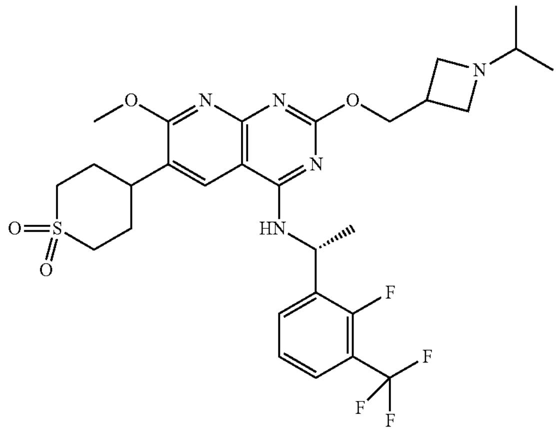 [SMILES: COc1nc2nc(OCC3CN(C(C)C)C3)nc(N[C@H](C)c3cccc(C(F)(F)F)c3F)c2cc1C1CCS(=O)(=O)CC1] | (R)-4-(4-((1-(2-fluoro-3-(trifluoromethyl)phenyl)ethyl)amino)-2-((1-isopropylazetidin-3-yl)methoxy)-7-methoxypyrido[2,3-d]pyrimidin-6-yl)tetrahydro-2H-thiopyran 1,1-dioxide | 626.4 |
| 287 | 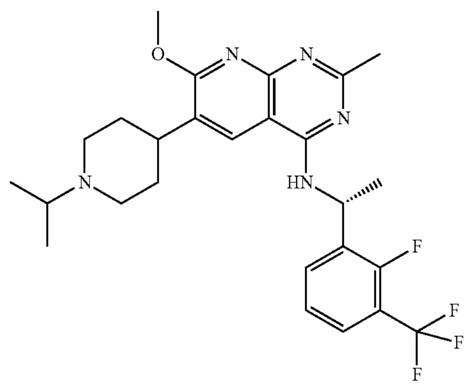 [SMILES: COc1nc2nc(C)nc(N[C@H](C)c3cccc(C(F)(F)F)c3F)c2cc1C1CCN(C(C)C)CC1] | (R)-N-(1-(2-fluoro-3-(trifluoromethyl)phenyl)ethyl)-6-(1-isopropylpiperidin-4-yl)-7-methoxy-2-methylpyrido[2,3-d]pyrimidin-4-amine | 506.5 |
| 288 | 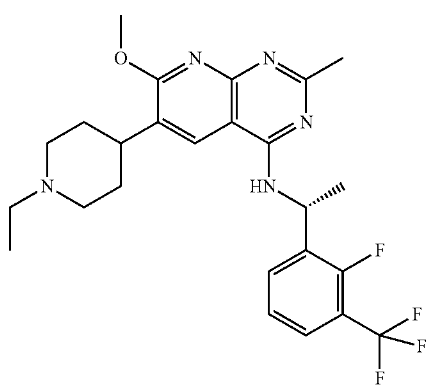 [SMILES: CCN1CCC(c2cc3c(N[C@H](C)c4cccc(C(F)(F)F)c4F)nc(C)nc3nc2OC)CC1] | (R)-6-(1-ethylpiperidin-4-yl)-N-(1-(2-fluoro-3-(trifluoromethyl)phenyl)ethyl)-7-methoxy-2-methylpyrido[2,3-d]pyrimidin-4-amine | 492.4 |
| 289 | 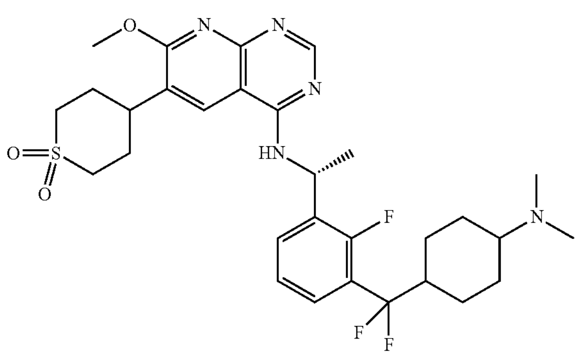 [SMILES: COc1nc2ncnc(N[C@H](C)c3cccc(C(F)(F)C4CCC(N(C)C)CC4)c3F)c2cc1C1CCS(=O)(=O)CC1] | (R)-4-(4-((1-(3-((4-(dimethylamino)cyclohexyl)difluoromethyl)-2-fluorophenyl)ethyl)amino)-7-methoxypyrido[2,3-d]pyrimidin-6-yl)tetrahydro-2H-thiopyran 1,1-dioxide | 606 |

TABLE 1-continued

| Compound | Structure | Name | [M + H]+ |
|---|---|---|---|
| 290 | 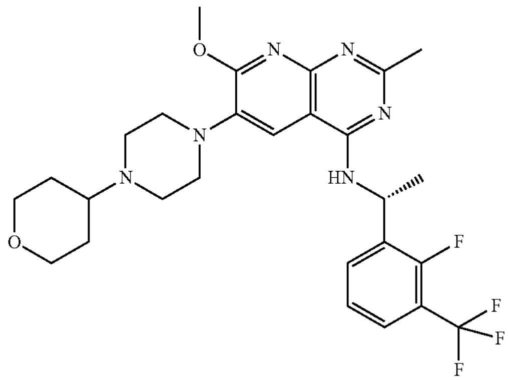 [SMILES: COc1nc2nc(C)nc(N[C@H](C)c3cccc(C(F)(F)F)c3F)c2cc1N1CCN(C2CCOCC2)CC1] | (R)-N-(1-(2-fluoro-3-(trifluoromethyl)phenyl)ethyl)-7-methoxy-2-methyl-6-(4-(tetrahydro-2H-pyran-4-yl)piperazin-1-yl)pyrido[2,3-d]pyrimidin-4-amine | 549.4 |
| 291 | 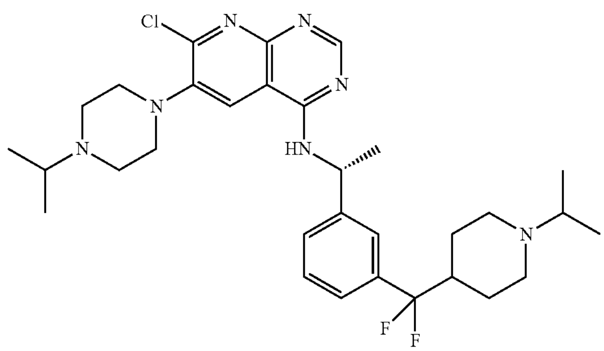 | (R)-7-chloro-N-(1-(3-(difluoro(1-isopropylpiperidin-4-yl)methyl)phenyl)ethyl)-6-(4-isopropylpiperazin-1-yl)pyrido[2,3-d]pyrimidin-4-amine | 586.5 |
| 292 | 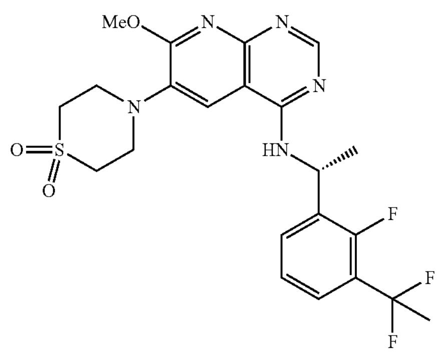 [SMILES: COc1nc2ncnc(N[C@H](C)c3cccc(C(C)(F)F)c3F)c2cc1N1CCS(=O)(=O)CC1] | (R)-4-(4-((1-(3-(1,1-difluoroethyl)-2-fluorophenyl)ethyl)amino)-7-methoxypyrido[2,3-d]pyrimidin-6-yl)thiomorpholine 1,1-dioxide | 496.4 |
| 293 | 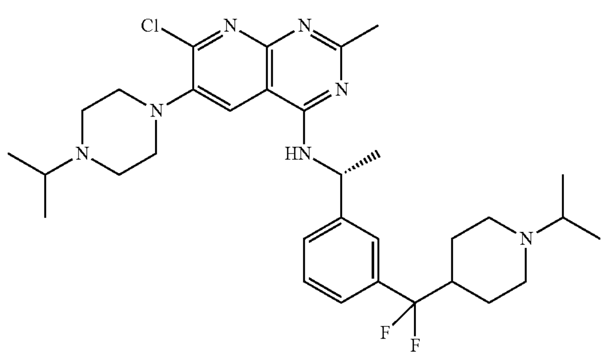 | (R)-7-chloro-N-(1-(3-(difluoro(1-isopropylpiperidin-4-yl)methyl)phenyl)ethyl)-6-(4-isopropylpiperazin-1-yl)-2-methylpyrido[2,3-d]pyrimidin-4-amine | 600.6 |

TABLE 1-continued

| Compound | Structure | Name | [M + H]+ |
|---|---|---|---|
| 294 | 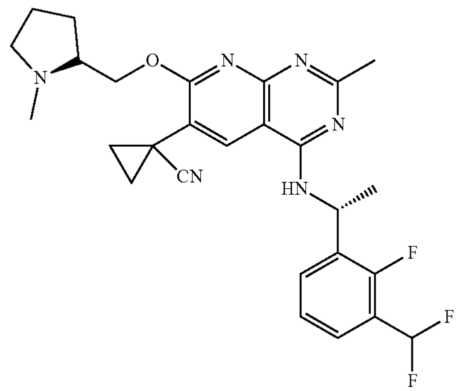 | (R)-1-(4-((1-(3-(difluoromethyl)-2-fluorophenyl)ethyl)amino)-7-((5-(dimethylamino)pentyl)oxy)-2-methylpyrido[2,3-d]pyrimidin-6-yl)cyclopropane-1-carbonitrile | 511.4 |
| 295 | 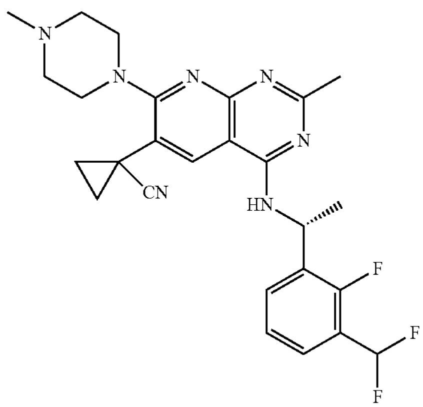 [SMILES: Cc1nc(N[C@H](C)c2cccc(C(F)F)c2F)c2cc(C3(C#N)CC3)c(N3CCN(C)CC3)nc2n1] | (R)-1-(4-((1-(3-(difluoromethyl)-2-fluorophenyl)ethyl)amino)-2-methyl-7-(4-methylpiperazin-1-yl)pyrido[2,3-d]pyrimidin-6-yl)cyclopropane-1-carbonitrile | 496.3 |
| 296 | 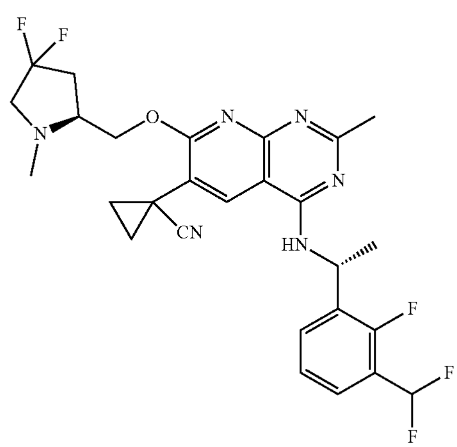 [SMILES: Cc1nc(N[C@H](C)c2cccc(C(F)F)c2F)c2cc(C3(C#N)CC3)c(OC[C@@H]3CC(F)(F)CN3C)nc2n1] | 1-(7-(((S)-4,4-difluoro-1-methylpyrrolidin-2-yl)methoxy)-4-(((R)-1-(3-(difluoromethyl)-2-fluorophenyl)ethyl)amino)-2-methylpyrido[2,3-d]pyrimidin-6-yl)cyclopropane-1-carbonitrile | 547.2 |
| 297 | 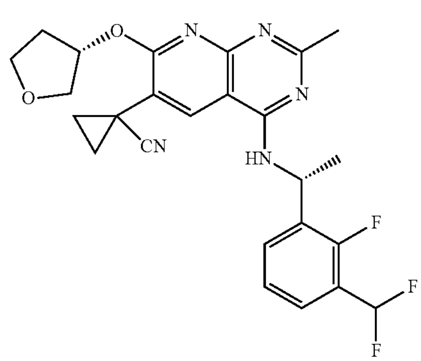 [SMILES: Cc1nc(N[C@H](C)c2cccc(C(F)F)c2F)c2cc(C3(C#N)CC3)c(O[C@H]3CCOC3)nc2n1] | 1-(4-(((R)-1-(3-(difluoromethyl)-2-fluorophenyl)ethyl)amino)-2-methyl-7-(((S)-tetrahydrofuran-3-yl)oxy)pyrido[2,3-d]pyrimidin-6-yl)cyclopropane-1-carbonitrile | 483.3 |

TABLE 1-continued

| Compound | Structure | Name | [M + H]+ |
|---|---|---|---|
| 298 | 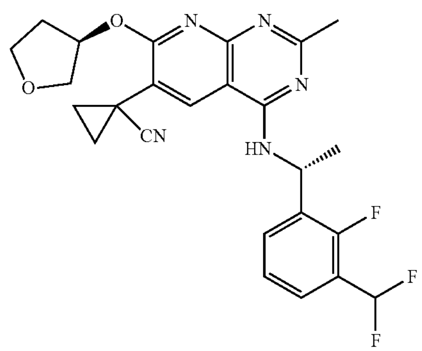 [SMILES: Cc1nc(N[C@H](C)c2cccc(C(F)F)c2F)c2cc(C3(C#N)CC3)c(O[C@@H]3CCOC3)nc2n1] | 1-(4-(((R)-1-(3-(difluoromethyl)-2-fluorophenyl)ethyl)amino)-2-methyl-7-(((R)-tetrahydrofuran-3-yl)oxy)pyrido[2,3-d]pyrimidin-6-yl)cyclopropane-1-carbonitrile | 483.3 |
| 299 | 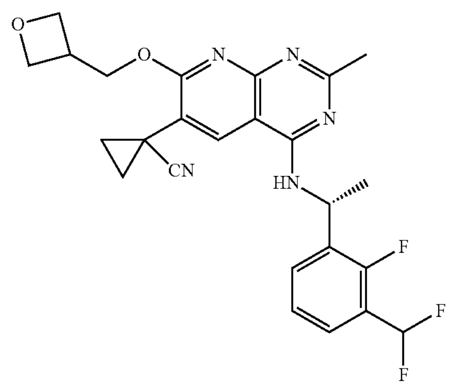 [SMILES: Cc1nc(N[C@H](C)c2cccc(C(F)F)c2F)c2cc(C3(C#N)CC3)c(OCC3COC3)nc2n1] | (R)-1-(4-((1-(3-(difluoromethyl)-2-fluorophenyl)ethyl)anrino)-2-methyl-7-(oxetan-3-ylmethoxy)pyrido[2,3-d]pyrimidin-6-yl)cyclopropane-1-carbonitrile | 484.7 |
| 300 | 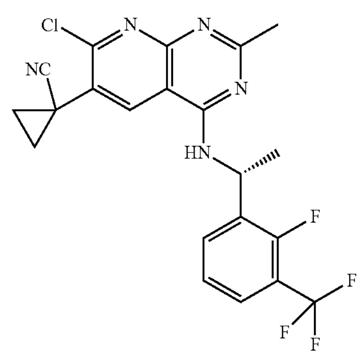 | (R)-1-(7-chloro-4-((1-(2-fluoro-3-(trifluoromethyl)phenyl)ethyl)amino)-2-methylpyrido[2,3-d]pyrimidin-6-yl)cyclopropane-1-carbonitrile | 450.5 |
| 301 | 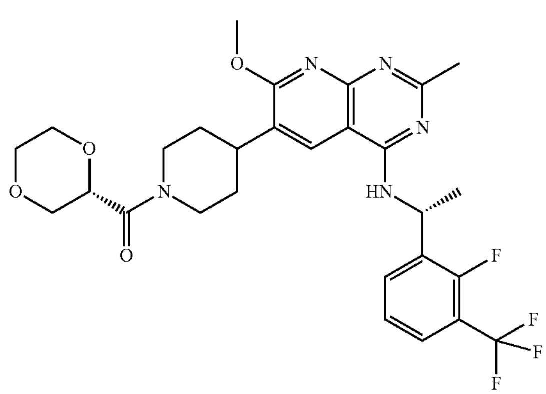 [SMILES: COc1nc2nc(C)nc(N[C@H](C)c3cccc(C(F)(F)F)c3F)c2cc1C1CCN(C(=O)[C@@H]2COCCO2)CC1] | ((S)-1,4-dioxan-2-yl)(4-(4-(((R)-1-(2-fluoro-3-(trifluoromethyl)phenyl)ethyl)amino)-7-methoxy-2-methylpyrido[2,3-d]pyrimidin-6-yl)piperidin-1-yl)methanone | 578.8 |

TABLE 1-continued

| Compound | Structure | Name | [M + H]+ |
|---|---|---|---|
| 302 | 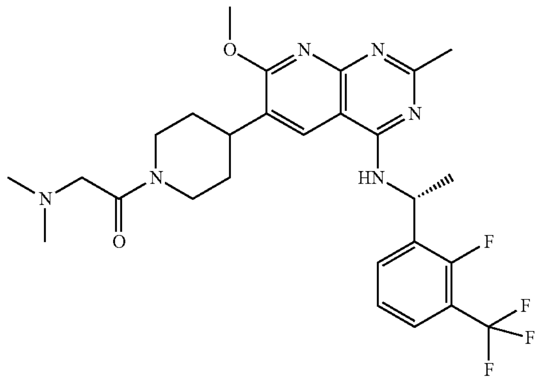 [SMILES: COc1nc2nc(C)nc(N[C@H](C)c3cccc(C(F)(F)F)c3F)c2cc1C1CCN(C(=O)CN(C)C)CC1] | (R)-2-(dimethylamino)-1-(4-(4-((1-(2-fluoro-3-(trifluoromethyl)phenyl)ethyl)amino)-7-methoxy-2-methylpyrido[2,3-d]pyrimidin-6-yl)piperidin-1-yl)ethan-1-one | 549.4 |
| 303 | 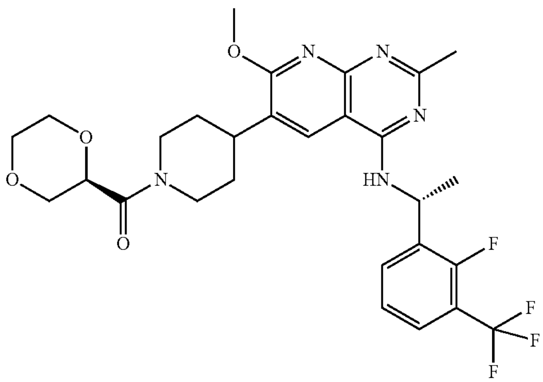 [SMILES: COc1nc2nc(C)nc(N[C@H](C)c3cccc(C(F)(F)F)c3F)c2cc1C1CCN(C(=O)[C@H]2COCCO2)CC1] | ((R)-1,4-dioxan-2-yl)(4-(4-(((R)-1-(2-fluoro-3-(trifluoromethyl)phenyl)ethyl)amino)-7-methoxy-2-methylpyrido[2,3-d]pyrimidin-6-yl)piperidin-1-yl)methanone | 578.4 |
| 304 | 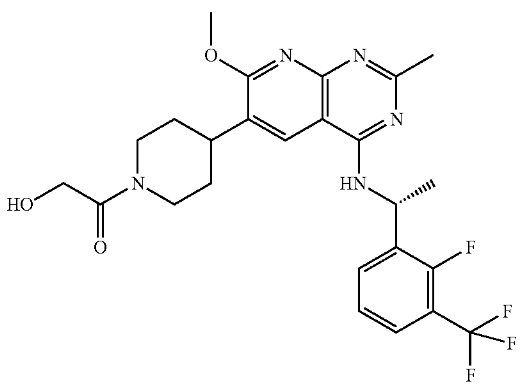 [SMILES: COc1nc2nc(C)nc(N[C@H](C)c3cccc(C(F)(F)F)c3F)c2cc1C1CCN(C(=O)CO)CC1] | (R)-1-(4-(4-((1-(2-fluoro-3-(trifluoromethyl)phenyl)ethyl)amino)-7-methoxy-2-methylpyrido[2,3-d]pyrimidin-6-yl)piperidin-1-yl)-2-hydroxyethan-1-one | 522.8 |
| 305 | 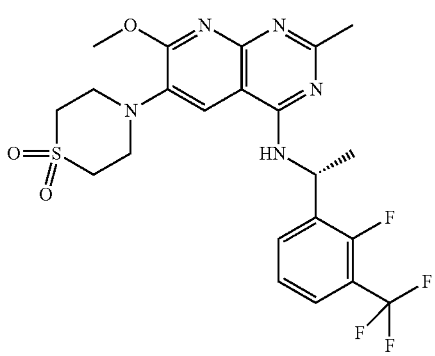 [SMILES: COc1nc2nc(C)nc(N[C@H](C)c3cccc(C(F)(F)F)c3F)c2cc1N1CCS(=O)(=O)CC1] | (R)-4-(4-((1-(2-fluoro-3-(trifluoromethyl)phenyl)ethyl)amino)-7-methoxy-2-methylpyrido[2,3-d]pyrimidin-6-yl)thiomorpholine 1,1-dioxide | 514.3 |

TABLE 1-continued

| Compound | Structure | Name | [M + H]+ |
|---|---|---|---|
| 306 | 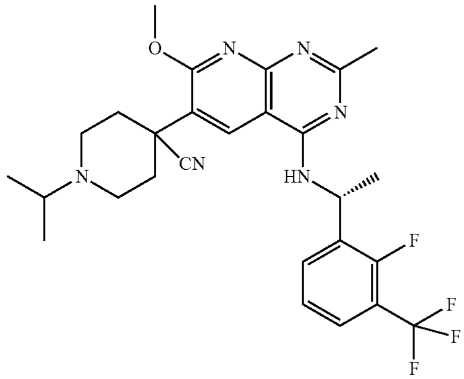 | (R)-4-(4-((1-(2-fluoro-3-(trifluoromethyl)phenyl)ethyl)amino)-7-methoxy-2-methylpyrido[2,3-d]pyrimidin-6-yl)-1-isopropylpiperidine-4-carbonitrile | 531.4 |
| 307 | 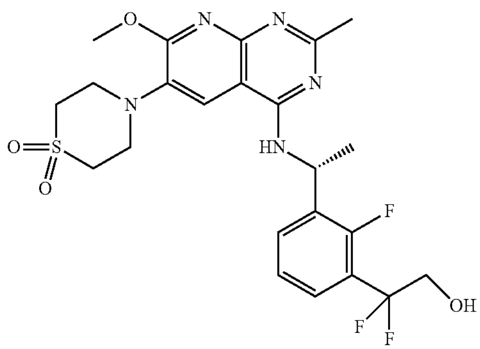 [SMILES: COc1nc2nc(C)nc(N[C@H](C)c3cccc(C(F)(F)CO)c3F)c2cc1N1CCS(=O)(=O)CC1] | (R)-4-(4-((1-(3-(1,1-difluoro-2-hydroxyethyl)-2-fluorophenyl)ethyl)amino)-7-methoxy-2-methylpyrido[2,3-d]pyrimidin-6-yl)thiomorpholine 1,1-dioxide | 526.7 |
| 308 | 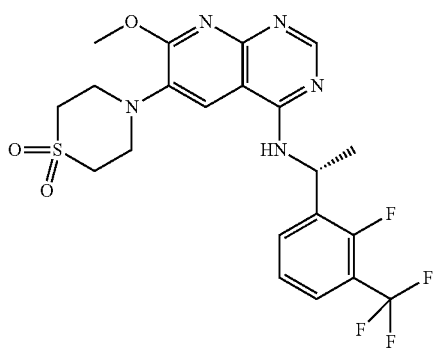 [SMILES: COc1nc2ncnc(N[C@H](C)c3cccc(C(F)(F)F)c3F)c2cc1N1CCS(=O)(=O)CC1] | (R)-4-(4-((1-(2-fluoro-3-(trifluoromethyl)phenyl)ethyl)amino)-7-methoxypyrido[2,3-d]pyrimidin-6-yl)thiomorpholine 1,1-dioxide | 500.6 |
| 309 | 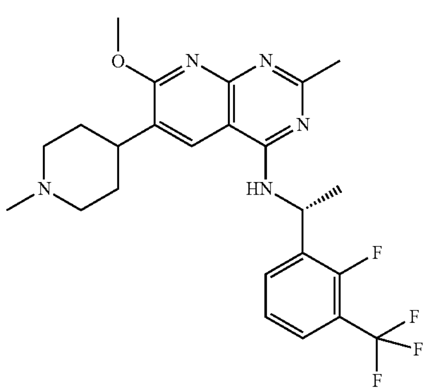 [SMILES: COc1nc2nc(C)nc(N[C@H](C)c3cccc(C(F)(F)F)c3F)c2cc1C1CCN(C)CC1] | (R)-N-(1-(2-fluoro-3-(trifluoromethyl)phenyl)ethyl)-7-methoxy-2-methyl-6-(1-methylpiperidin-4-yl)pyrido[2,3-d]pyrimidin-4-amine | 478.3 |

TABLE 1-continued

| Compound | Structure | Name | [M + H]+ |
|---|---|---|---|
| 310 | 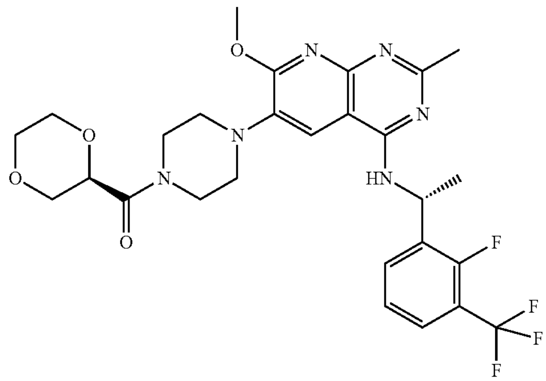 [SMILES: COc1nc2nc(C)nc(N[C@H](C)c3cccc(C(F)(F)F)c3F)c2cc1N1CCN(C(=O)[C@H]2COCCO2)CC1] | ((R)-1,4-dioxan-2-yl)(4-(4-(((R)-1-(2-fluoro-3-(trifluoromethyl)phenyl)ethyl)amino)-7-methoxy-2-methylpyrido[2,3-d]pyrimidin-6-yl)piperazin-1-yl)methanone | 579.4 |
| 311 | 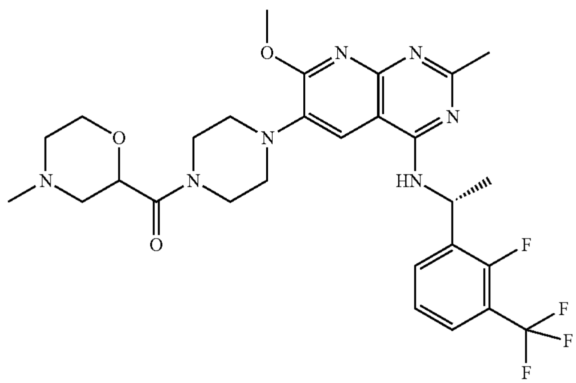 [SMILES: COc1nc2nc(C)nc(N[C@H](C)c3cccc(C(F)(F)F)c3F)c2cc1N1CCN(C(=O)C2CN(C)CCO2)CC1] | (4-(4-(((R)-1-(2-fluoro-3-(trifluoromethyl)phenyl)ethyl)amino)-7-methoxy-2-methylpyrido[2,3-d]pyrimidin-6-yl)piperazin-1-yl)(4-methylmorpholin-2-yl)methanone | 592.4 |
| 312 | 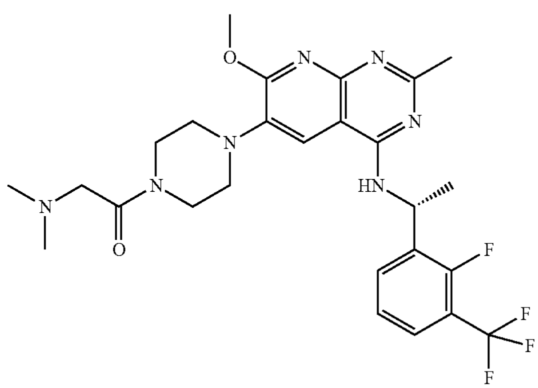 [SMILES: COc1nc2nc(C)nc(N[C@H](C)c3cccc(C(F)(F)F)c3F)c2cc1N1CCN(C(=O)CN(C)C)CC1] | (R)-2-(dimethylamino)-1-(4-(4-((1-(2-fluoro-3-(trifluoromethyl)phenyl)ethyl)amino)-7-methoxy-2-methylpyrido[2,3-d]pyrimidin-6-yl)piperazin-1-yl)ethan-1-one | 550.4 |
| 313 | 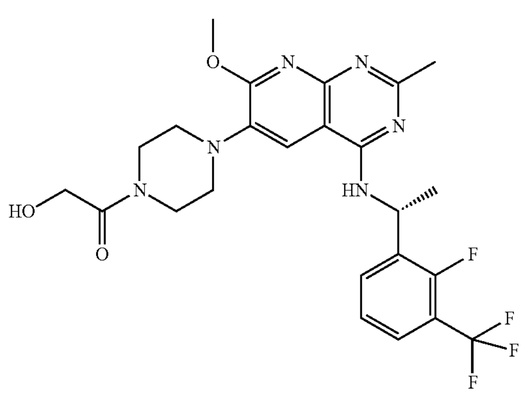 [SMILES: COc1nc2nc(C)nc(N[C@H](C)c3cccc(C(F)(F)F)c3F)c2cc1N1CCN(C(=O)CO)CC1] | (R)-1-(4-(4-((1-(2-fluoro-3-(trifluoromethyl)phenyl)ethyl)amino)-7-methoxy-2-methylpyrido[2,3-d]pyrimidin-6-yl)piperazin-1-yl)-2-hydroxyethan-1-one | 523.4 |

TABLE 1-continued

| Compound | Structure | Name | [M + H]+ |
|---|---|---|---|
| 314 | 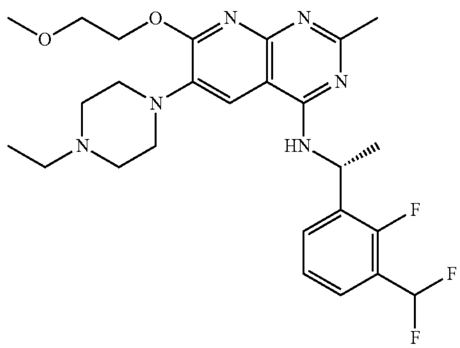 [SMILES: CCN1CCN(c2cc3c(N[C@H](C)c4cccc(C(F)F)c4F)nc(C)nc3nc2OCCOC)CC1] | (R)-N-(1-(3-(difluoromethyl)-2-fluorophenyl)ethyl)-6-(4-ethylpiperazin-1-yl)-7-(2-methoxyethoxy)-2-methylpyrido[2,3-d]pyrimidin-4-amine | 519.5 |
| 315 | 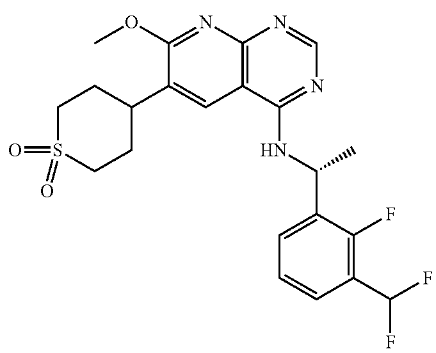 [SMILES: COc1nc2ncnc(N[C@H](C)c3cccc(C(F)F)c3F)c2cc1C1CCS(=O)(=O)CC1] | (R)-4-(4-((1-(3-(difluoromethyl)-2-fluorophenyl)ethyl)amino)-7-methoxypyrido[2,3-d]pyrimidin-6-yl)tetrahydro-2H-thiopyran 1,1-dioxide | 481.3 |
| 316 | 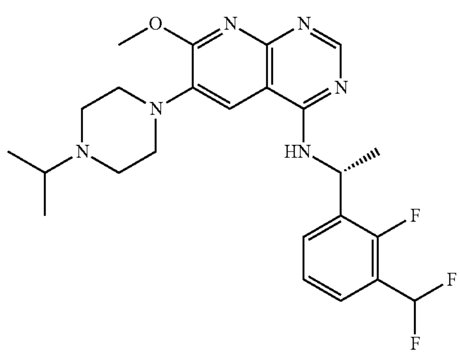 [SMILES: COc1nc2ncnc(N[C@H](C)c3cccc(C(F)F)c3F)c2cc1N1CCN(C(C)C)CC1] | (R)-N-(1-(3-(difluoromethyl)-2-fluorophenyl)ethyl)-6-(4-isopropylpiperazin-1-yl)-7-methoxypyrido[2,3-d]pyrimidin-4-amine | 475.4 |
| 317 | 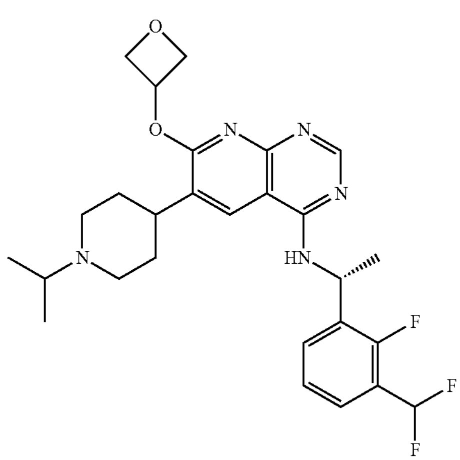 [SMILES: CC(C)N1CCC(c2cc3c(N[C@H](C)c4cccc(C(F)F)c4F)ncnc3nc2OC2COC2)CC1] | (R)-N-(1-(3-(difluoromethyl)-2-fluorophenyl)ethyl)-6-(1-isopropylpiperidin-4-yl)-7-(oxetan-3-yloxy)pyrido[2,3-d]pyrimidin-4-amine | 516.5 |

TABLE 1-continued

| Compound | Structure | Name | [M + H]+ |
|---|---|---|---|
| 318 | 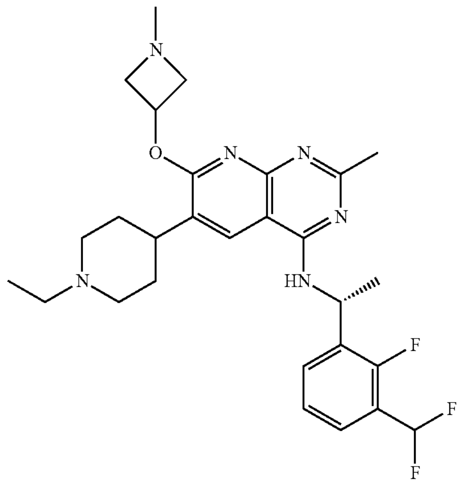 [SMILES: CCN1CCC(c2cc3c(N[C@H](C)c4cccc(C(F)F)c4F)nc(C)nc3nc2OC2CN(C)C2)CC1] | (R)-4-(4-((1-(3-(difluoromethyl)-2-fluorophenyl)ethyl)amino)-7-methoxypyrido[2,3-d]pyrimidin-6-yl)tetrahydro-2H-thiopyran 1,1-dioxide | 529.5 |
| 319 | 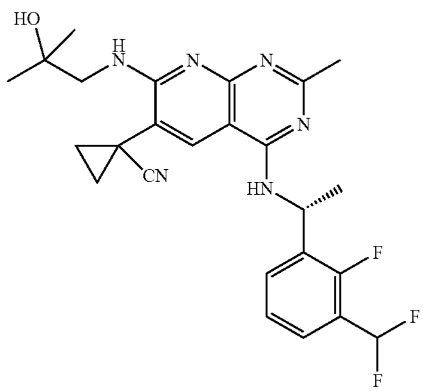 [SMILES: Cc1nc(N[C@H](C)c2cccc(C(F)F)c2F)c2cc(C3(C#N)CC3)c(NCC(C)(C)O)nc2n1] | (R)-1-(4-((1-(3-(difluoromethyl)-2-fluorophenyl)ethyl)amino)-7-((2-hydroxy-2-methylpropyl)amino)-2-methylpyrido[2,3-d]pyrimidin-6-yl)cyclopropane-1-carbonitrile | 485.3 |
| 320 | 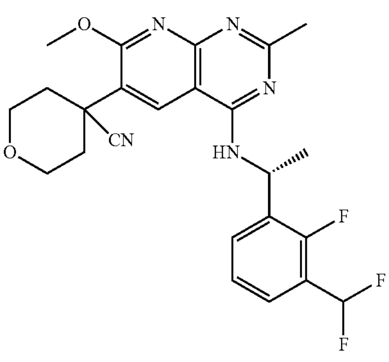 [SMILES: COc1nc2nc(C)nc(N[C@H](C)c3cccc(C(F)F)c3F)c2cc1C1(C#N)CCOCC1] | (R)-4-(4-((1-(3-(difluoromethyl)-2-fluorophenyl)ethyl)amino)-7-methoxy-2-methylpyrido[2,3-d]pyrimidin-6-yl)tetrahydro-2H-pyran-4-carbonitrile | 472.6 |
| 321 | 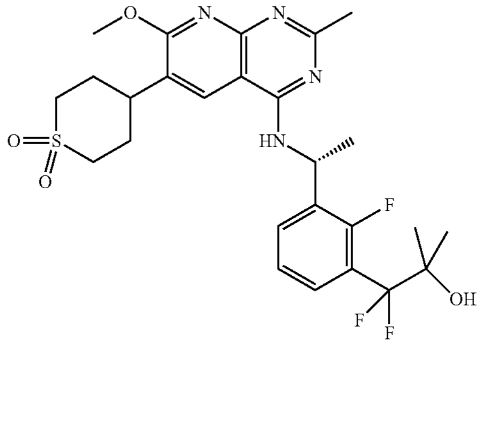 [SMILES: COc1nc2nc(C)nc(N[C@H](C)c3cccc(C(F)(F)C(C)(C)O)c3F)c2cc1C1CCS(=O)(=O)CC1] | (R)-4-(4-((1-(3-(1,1-difluoro-2-hydroxy-2-methylpropyl)-2-fluorophenyl)ethyl)amino)-7-methoxy-2-methylpyrido[2,3-d]pyrimidin-6-yl)tetrahydro-2H-thiopyran 1,1-dioxide | 553.3 |

TABLE 1-continued

| Compound | Structure | Name | [M + H]+ |
|---|---|---|---|
| 322 | 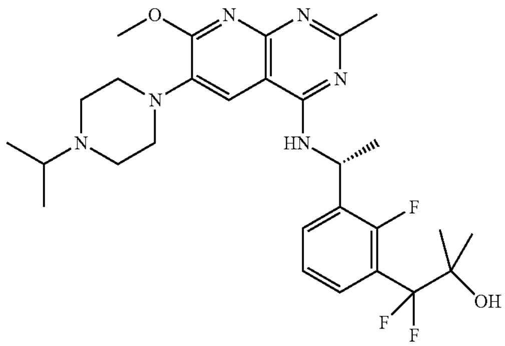 [SMILES: COc1nc2nc(C)nc(N[C@H](C)c3cccc(C(F)(F)C(C)(C)O)c3F)c2cc1N1CCN(C(C)C)CC1] | (R)-1,1-difluoro-1-(2-fluoro-3-(1-((6-(4-isopropylpiperazin-1-yl)-7-methoxy-2-methylpyrido[2,3-d]pyrimidin-4-yl)amino)ethyl)phenyl)-2-methylpropan-2-ol | 547.5 |
| 323 | 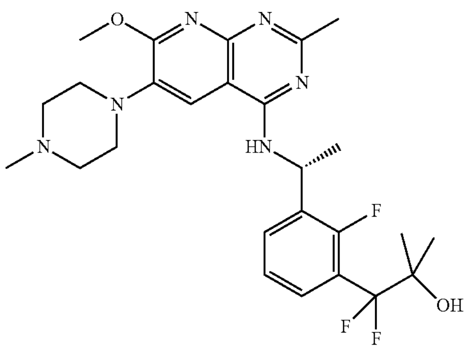 [SMILES: COc1nc2nc(C)nc(N[C@H](C)c3cccc(C(F)(F)C(C)(C)O)c3F)c2cc1N1CCN(C)CC1] | (R)-1,1-difluoro-1-(2-fluoro-3-(1-((7-methoxy-2-methyl-6-(4-methylpiperazin-1-yl)pyrido[2,3-d]pyrimidin-4-yl)amino)ethyl)phenyl)-2-methylpropan-2-ol | 519.4 |
| 324 | 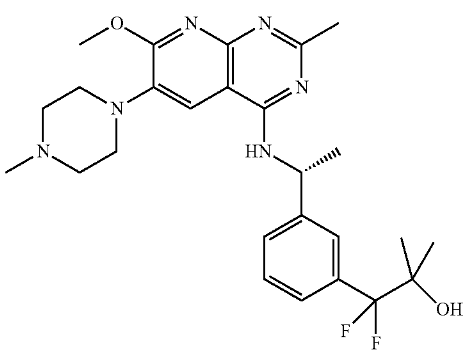 [SMILES: COc1nc2nc(C)nc(N[C@H](C)c3cccc(C(F)(F)C(C)(C)O)c3)c2cc1N1CCN(C)CC1] | (R)-1,1-difluoro-1-(3-(1-((7-methoxy-2-methyl-6-(4-methylpiperazin-1-yl)pyrido[2,3-d]pyrimidin-4-yl)amino)ethyl)phenyl)-2-methylpropan-2-ol | 501.5 |
| 325 | 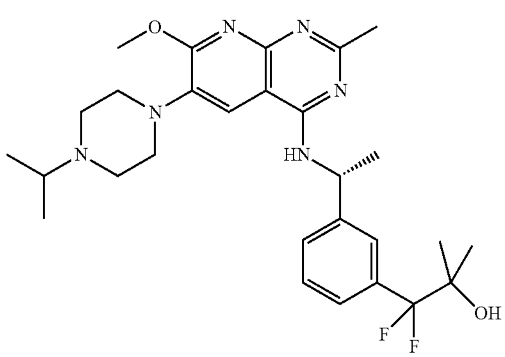 [SMILES: COc1nc2nc(C)nc(N[C@H](C)c3cccc(C(F)(F)C(C)(C)O)c3)c2cc1N1CCN(C(C)C)CC1] | (R)-1,1-difluoro-1-(3-(1-((6-(4-isopropylpiperazin-1-yl)-7-methoxy-2-methylpyrido[2,3-d]pyrimidin-4-yl)amino)ethyl)phenyl)-2-methylpropan-2-ol | 529.5 |

TABLE 1-continued

| Compound | Structure | Name | [M + H]+ |
|---|---|---|---|
| 326 | 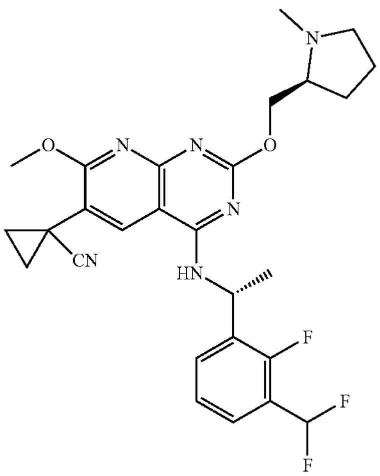 [SMILES: COc1nc2nc(OC[C@@H]3CCCN3C)nc(N[C@H](C)c3cccc(C(F)F)c3F)c2cc1C1(C#N)CC1] | 1-(4-(((R)-1-(3-(difluoromethyl)-2-fluorophenyl)ethyl)amino)-7-methoxy-2-(((S)-1-methylpyrrolidin-2-yl)methoxy)pyrido[2,3-d]pyrimidin-6-yl)cyclopropane-1-carbonitrile | 527.5 |
| 327 | 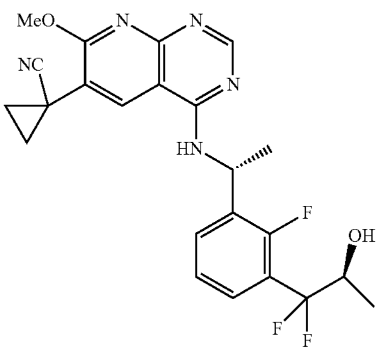 [SMILES: COc1nc2ncnc(N[C@H](C)c3cccc(C(F)(F)[C@H](C)O)c3F)c2cc1C1(C#N)CC1] | 1-(4-(((R)-1-(3((S)-1,1-difluoro-2-hydroxypropyl)-2-fluorophenyl)ethyl)amino)-7-methoxypyrido[2,3-d]pyrimidin-6-yl)cyclopropane-1-carbonitrile | 458.7 |
| 328 | 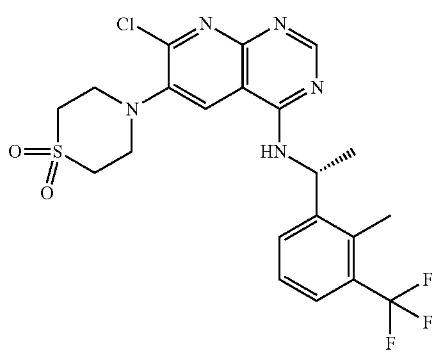 [SMILES: Cc1c([C@@H](C)Nc2ncnc3nc(Cl)c(N4CCS(=O)(=O)CC4)cc23)cccc1C(F)(F)F] | (R)-4-(7-chloro-4-((1-(2-methyl-3-(trifluoromethyl)phenyl)ethyl)amino)pyrido[2,3-d]pyrimidin-6-yl)thiomorpholine 1,1-dioxide | 500.2 |
| 329 | 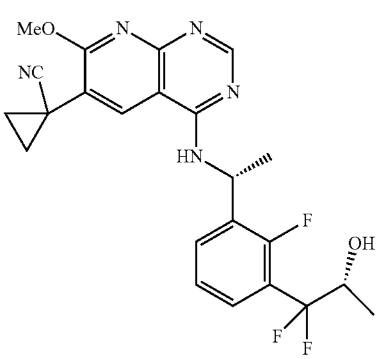 [SMILES: COc1nc2ncnc(N[C@H](C)c3cccc(C(F)(F)[C@@H](C)O)c3F)c2cc1C1(C#N)CC1] | 1-(4-(((R)-1-(3-((R)-1,1-difluoro-2-hydroxypropyl)-2-fluorophenyl)ethyl)amino)-7-methoxypyrido[2,3-d]pyrimidin-6-yl)cyclopropane-1-carbonitrile | 458.7 |

TABLE 1-continued

| Compound | Structure | Name | [M + H]+ |
|---|---|---|---|
| 330 | 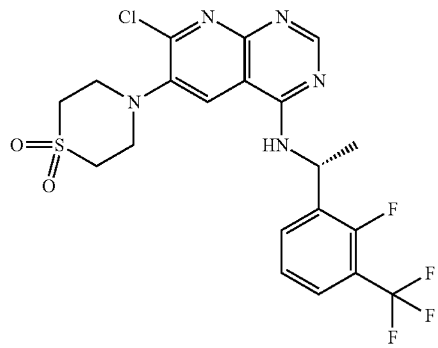 [SMILES: C[C@@H](Nc1ncnc2nc(Cl)c(N3CCS(=O)(=O)CC3)cc12)c1cccc(C(F)(F)F)c1F] | (R)-4-(7-chloro-4-((1-(2-fluoro-3-(trifluoromethyl)phenyl)ethyl)amino)pyrido[2,3-d]pyrimidin-6-yl)thiomorpholine 1,1-dioxide | 504.2 |
| 331 | 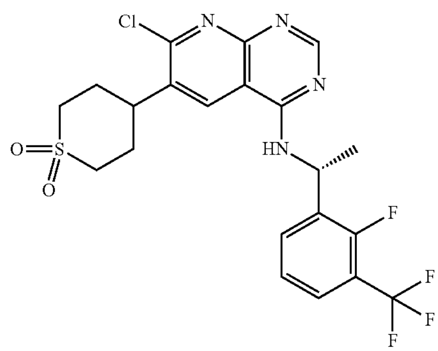 [SMILES: C[C@@H](Nc1ncnc2nc(Cl)c(C3CCS(=O)(=O)CC3)cc12)c1cccc(C(F)(F)F)c1F] | (R)-4-(7-chloro-4-((1-(2-fluoro-3-(trifluoromethyl)phenyl)ethyl)amino)pyrido[2,3-d]pyrimidin-6-yl)tetrahydro-2H-thiopyran 1,1-dioxide | 503.2 |
| 332 | 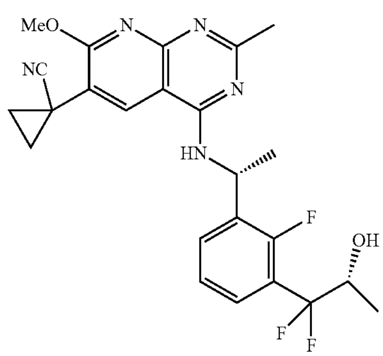 [SMILES: COc1nc2nc(C)nc(N[C@H](C)c3cccc(C(F)(F)[C@@H](C)O)c3F)c2cc1C1(C#N)CC1] | 1-(4-(((R)-1-(3-((R)-1,1-difluoro-2-hydroxypropyl)-2-fluorophenyl)ethyl)amino)-7-methoxy-2-methylpyrido[2,3-d]pyrimidin-6-yl)cyclopropane-1-carbonitrile | 472.3 |
| 333 | 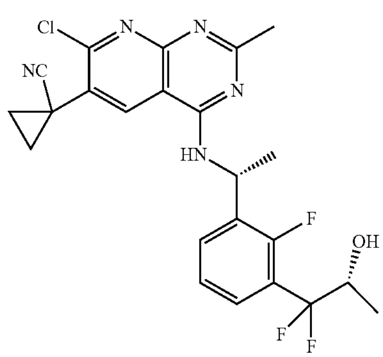 [SMILES: Cc1nc(N[C@H](C)c2cccc(C(F)(F)[C@@H](C)O)c2F)c2cc(C3(C#N)CC3)c(Cl)nc2n1] | 1-(7-chloro-4-(((R)-1-(3-((R)-1,1-difluoro-2-hydroxypropyl)-2-fluorophenyl)ethyl)amino)-2-methylpyrido[2,3-d]pyrimidin-6-yl)cyclopropane-1-carbonitrile | 476.3 |

TABLE 1-continued

| Compound | Structure | Name | [M + H]+ |
|---|---|---|---|
| 334 | 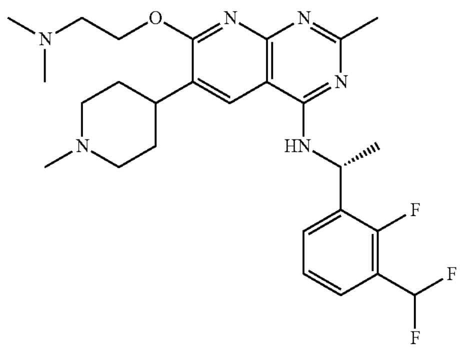 [SMILES: Cc1nc(N[C@H](C)c2cccc(C(F)F)c2F)c2cc(C3CCN(C)CC3)c(OCCN(C)C)nc2n1] | (R)-N-(1-(3-(difluoromethyl)-2-fluorophenyl)ethyl)-7-(2-(dimethylamino)ethoxy)-2-methyl-6-(1-methylpiperidin-4-yl)pyrido[2,3-d]pyrimidin-4-amine | 517.5 |
| 335 | 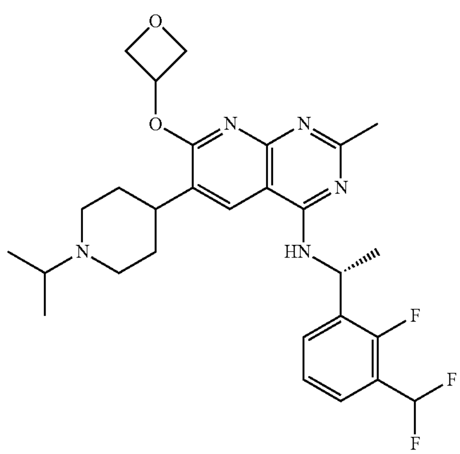 [SMILES: Cc1nc(N[C@H](C)c2cccc(C(F)F)c2F)c2cc(C3CCN(C(C)C)CC3)c(OC3COC3)nc2n1] | (R)-N-(1-(3-(difluoromethyl)-2-fluorophenyl)ethyl)-6-(1-isopropylpiperidin-4-yl)-2-methyl-7-(oxetan-3-yloxy)pyrido[2,3-d]pyrimidin-4-amine | 530.5 |
| 336 | 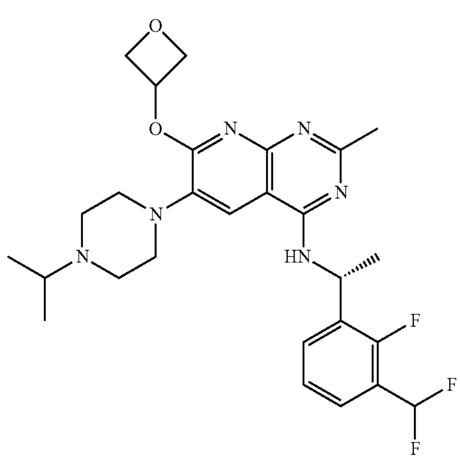 [SMILES: Cc1nc(N[C@H](C)c2cccc(C(F)F)c2F)c2cc(N3CCN(C(C)C)CC3)c(OC3COC3)nc2n1] | (R)-N-(1-(3-(difluoromethyl)-2-fluorophenyl)ethyl)-6-(4-isopropylpiperazin-1-yl)-2-methyl-7-(oxetan-3-yloxy)pyrido[2,3-d]pyrimidin-4-amine | 531.5 |

TABLE 1-continued

| Compound | Structure | Name | [M + H]+ |
|---|---|---|---|
| 337 | 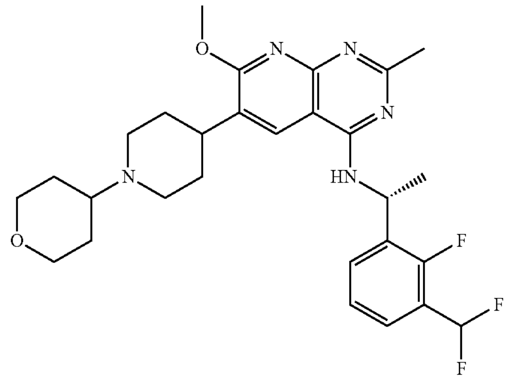 [SMILES: COc1nc2nc(C)nc(N[C@H](C)c3cccc(C(F)F)c3F)c2cc1C1CCN(C2CCOCC2)CC1] | (R)-N-(1-(3-(difluoromethyl)-2-fluorophenyl)ethyl)-7-methoxy-2-methyl-6-(1-(tetrahydro-2H-pyran-4-yl)piperidin-4-yl)pyrido[2,3-d]pyrimidin-4-amine | 530.5 |
| 338 | 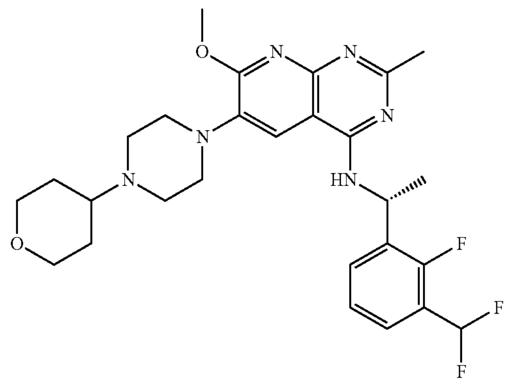 [SMILES: COc1nc2nc(C)nc(N[C@H](C)c3cccc(C(F)F)c3F)c2cc1N1CCN(C2CCOCC2)CC1] | (R)-N-(1-(3-(difluoromethyl)-2-fluorophenyl)ethyl)-7-methoxy-2-methyl-6-(4-(tetrahydro-2H-pyran-4-yl)piperazin-1-yl)pyrido[2,3-d]pyrimidin-4-amine | 531.5 |
| 339 | 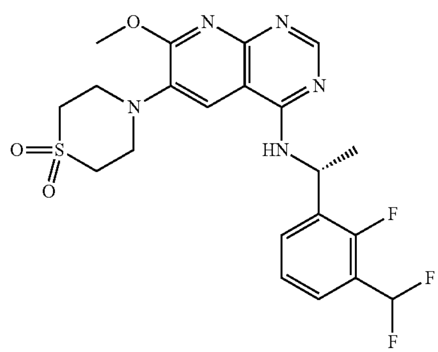 [SMILES: COc1nc2ncnc(N[C@H](C)c3cccc(C(F)F)c3F)c2cc1N1CCS(=O)(=O)CC1] | (R)-4-(4-((1-(3-(difluoromethyl)-2-fluorophenyl)ethyl)amino)-7-methoxypyrido[2,3-d]pyrimidin-6-yl)thiomorpholine 1,1-dioxide | 482.3 |
| 340 | 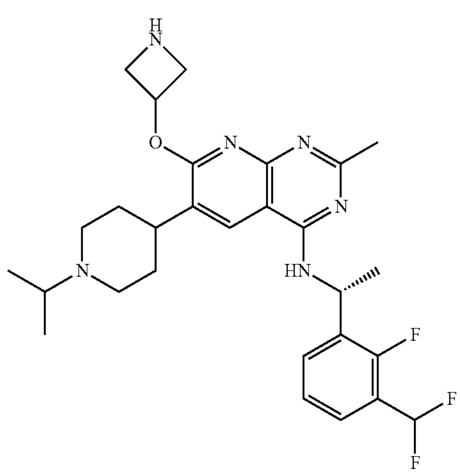 [SMILES: Cc1nc(N[C@H](C)c2cccc(C(F)F)c2F)c2cc(C3CCN(C(C)C)CC3)c(OC3CNC3)nc2n1] | (R)-7-(azetidin-3-yloxy)-N-(1-(3-(difluoromethyl)-2-fluorophenyl)ethyl)-6-(1-isopropylpiperidin-4-yl)-2-methylpyrido[2,3-d]pyrimidin-4-amine | 529.5 |

TABLE 1-continued

| Compound | Structure | Name | [M + H]+ |
|---|---|---|---|
| 341 | 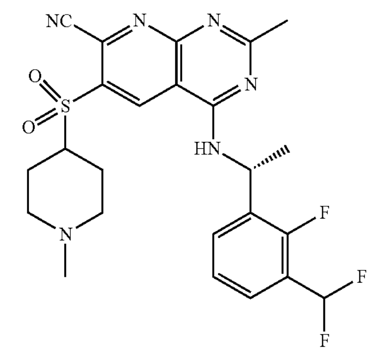 [SMILES: Cc1nc(N[C@H](C)c2cccc(C(F)F)c2F)c2cc(S(=O)(=O)C3CCN(C)CC3)c(C#N)nc2n1] | (R)-4-((1-(3-(difluoromethyl)-2-fluorophenyl)ethyl)amino)-2-methyl-6-((1-methylpiperidin-4-yl)sulfonyl)pyrido[2,3-d]pyrimidine-7-carbonitrile | 519.4 |
| 342 | 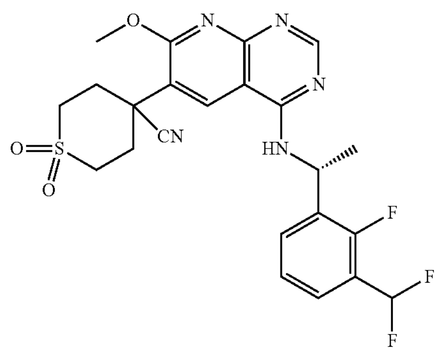 [SMILES: COc1nc2ncnc(N[C@H](C)c3cccc(C(F)F)c3F)c2cc1C1(C#N)CCS(=O)(=O)CC1] | (R)-4-(4-((1-(3-(difluoromethyl)-2-fluorophenyl)ethyl)amino)-7-methoxypyrido[2,3-d]pyrimidin-6-yl)tetrahydro-2H-thiopyran-4-carbonitrile 1,1-dioxide | 506.3 |
| 343 | 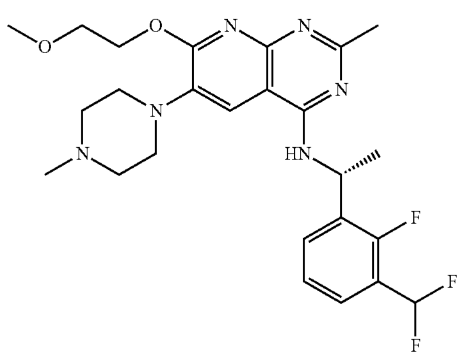 [SMILES: COCCOc1nc2nc(C)nc(N[C@H](C)c3cccc(C(F)F)c3F)c2cc1N1CCN(C)CC1] | (R)-N-(1-(3-(difluoromethyl)-2-fluorophenyl)ethyl)-7-(2-methoxyethoxy)-2-methyl-6-(4-methylpiperazin-1-yl)pyrido[2,3-d]pyrimidin-4-amine | 505.5 |
| 344 | 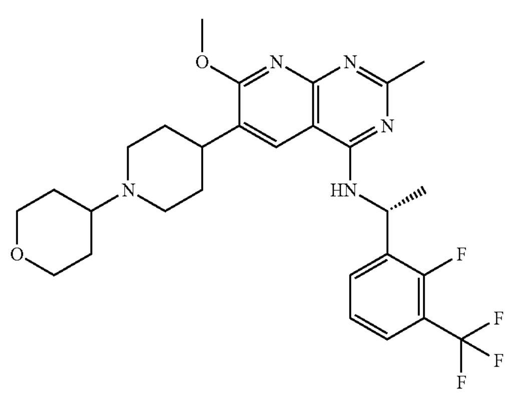 | (R)-N-(1-(2-fluoro-3-(trifluoromethyl)phenyl)ethyl)-7-methoxy-2-methyl-6-(1-(tetrahydro-2H-pyran-4-yl)piperidin-4-yl)pyrido[2,3-d]pyrimidin-4-amine | 548.5 |

TABLE 1-continued

| Compound | Structure | Name | [M + H]+ |
|---|---|---|---|
| 345 | 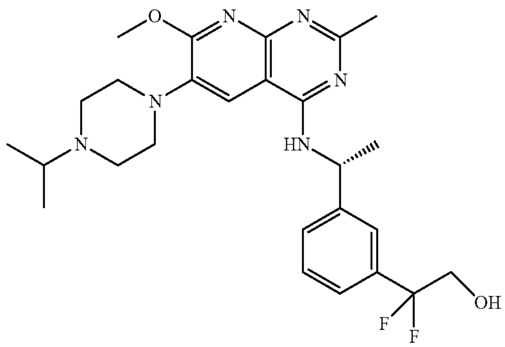 [SMILES: COc1nc2nc(C)nc(N[C@H](C)c3cccc(C(F)(F)CO)c3)c2cc1N1CCN(C(C)C)CC1] | (R)-2,2-difluoro-2-(3-(1-((6-(4-isopropylpiperazin-1-yl)-7-methoxy-2-methylpyrido[2,3-d]pyrimidin-4-yl)amino)ethyl)phenyl)ethan-1-ol | 501.4 |
| 346 | 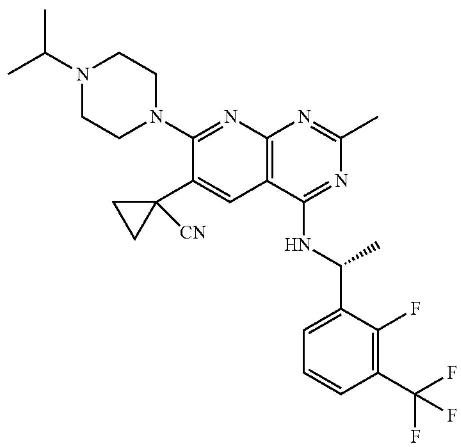 [SMILES: Cc1nc(N[C@H](C)c2cccc(C(F)(F)F)c2F)c2cc(C3(C#N)CC3)c(N3CCN(C(C)C)CC3)nc2n1] | (R)-1-(4-((1-(2-fluoro-3-(trifluoromethyl)phenyl)ethyl)amino)-7-(4-isopropylpiperazin-1-yl)-2-methylpyrido[2,3-d]pyrimidin-6-yl)cyclopropane-1-carbonitrile | 542.4 |
| 347 | 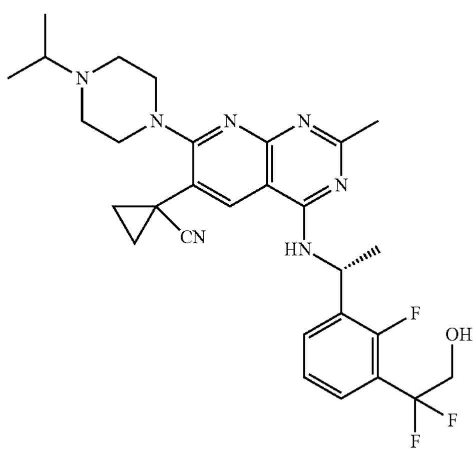 [SMILES: Cc1nc(N[C@H](C)c2cccc(C(F)(F)CO)c2F)c2cc(C3(C#N)CC3)c(N3CCN(C(C)C)CC3)nc2n1] | (R)-1-(4-((1-(3-(1,1-difluoro-2-hydroxyethyl)-2-fluorophenyl)ethyl)amino)-7-(4-isopropylpiperazin-1-yl)-2-methylpyrido[2,3-d]pyrimidin-6-yl)cyclopropane-1-carbonitrile | 554.4 |
| 348 | 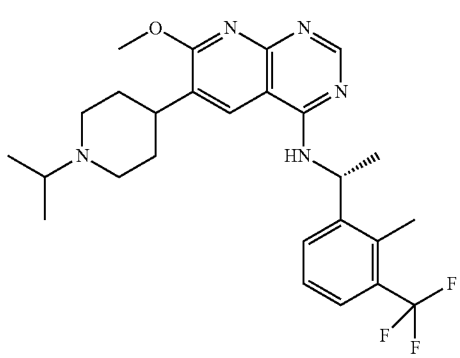 [SMILES: COc1nc2ncnc(N[C@H](C)c3cccc(C(F)(F)F)c3C)c2cc1C1CCN(C(C)C)CC1] | (R)-6-(1-isopropylpiperidin-4-yl)-7-methoxy-N-(1-(2-methyl-3-(trifluoromethyl)phenyl)ethyl)pyrido[2,3-d]pyrimidin-4-amine | 488.3 |

TABLE 1-continued

| Compound | Structure | Name | [M + H]⁺ |
|---|---|---|---|
| 349 | 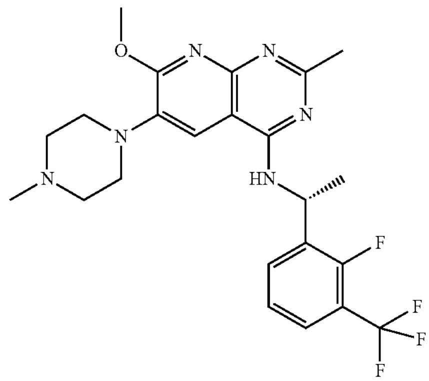 [SMILES: COc1nc2nc(C)nc(N[C@H](C)c3cccc(C(F)(F)F)c3F)c2cc1N1CCN(C)CC1] | (R)-N-(1-(2-fluoro-3-(trifluoromethyl)phenyl)ethyl)-7-methoxy-2-methyl-6-(4-methylpiperazin-1-yl)pyrido[2,3-d]pyrimidin-4-amine | 479.3 |
| 350 | 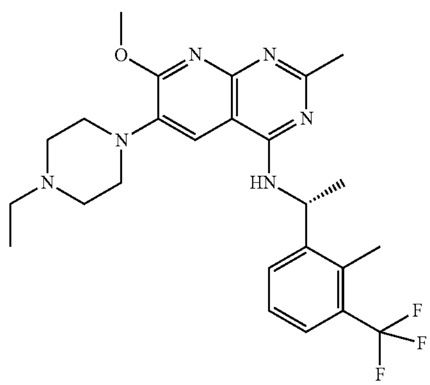 [SMILES: CCN1CCN(c2cc3c(N[C@H](C)c4cccc(C(F)(F)F)c4C)nc(C)nc3nc2OC)CC1] | (R)-6-(4-ethylpiperazin-1-yl)-7-methoxy-2-methyl-N-(1-(2-methyl-3-(trifluoromethyl)phenyl)ethyl)pyrido[2,3-d]pyrimidin-4-amine | 489.4 |
| 351 | 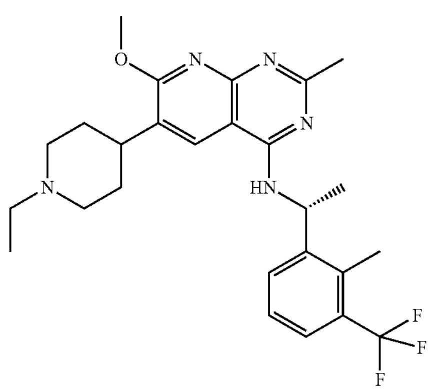 [SMILES: CCN1CCC(c2cc3c(N[C@H](C)c4cccc(C(F)(F)F)c4C)nc(C)nc3nc2OC)CC1] | (R)-6-(1-ethylpiperidin-4-yl)-7-methoxy-2-methyl-N-(1-(2-methyl-3-(trifluoromethyl)phenyl)ethyl)pyrido[2,3-d]pyrimidin-4-amine | 488.4 |
| 352 | 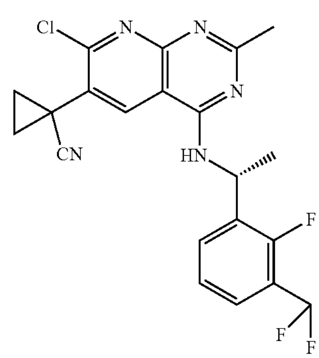 [SMILES: Cc1nc(N[C@H](C)c2cccc(C(F)F)c2F)c2cc(C3(C#N)CC3)c(Cl)nc2n1] | (R)-1-(7-chloro-4-((1-(3-(difluoromethyl)-2-fluorophenyl)ethyl)amino)-2-methylpyrido[2,3-d]pyrimidin-6-yl)cyclopropane-1-carbonitrile | 432.3 |

TABLE 1-continued

| Compound | Structure | Name | [M + H]+ |
|---|---|---|---|
| 353 | 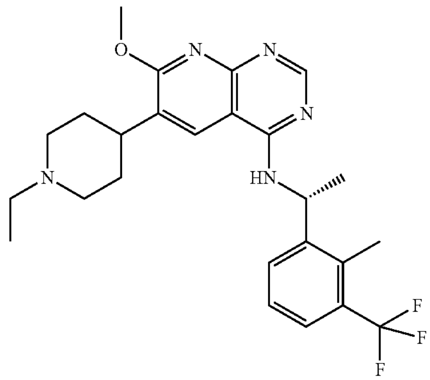 [SMILES: CCN1CCC(c2cc3c(N[C@H](C)c4cccc(C(F)(F)F)c4C)ncnc3nc2OC)CC1] | (R)-6-(1-ethylpiperidin-4-yl)-7-methoxy-N-(1-(2-methyl-3-(trifluoromethyl)phenyl)ethyl)pyrido[2,3-d]pyrimidin-4-amine | 474.3 |
| 354 | 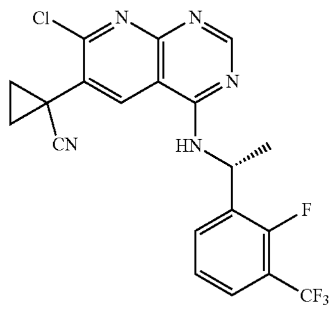 [SMILES: C[C@@H](Nc1ncnc2nc(Cl)c(C3(C#N)CC3)cc12)c1cccc(C(F)(F)F)c1F] | (R)-1-(7-chloro-4-((1-(2-fluoro-3-(trifluoromethyl)phenyl)ethyl)amino)pyrido[2,3-d]pyrimidin-6-yl)cyclopropane-1-carbonitrile | 436.5 |
| 355 | 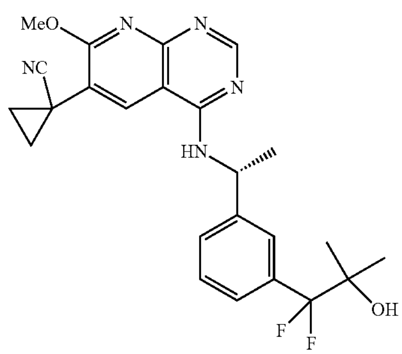 [SMILES: COc1nc2ncnc(N[C@H](C)c3cccc(C(F)(F)C(C)(C)O)c3)c2cc1C1(C#N)CC1] | (R)-1-(4-((1-(3-(1,1-difluoro-2-hydroxy-2-methylpropyl)phenyl)ethyl)amino)-7-methoxypyrido[2,3-d]pyrimidin-6-yl)cyclopropane-1-carbonitrile | 454.7 |
| 356 | 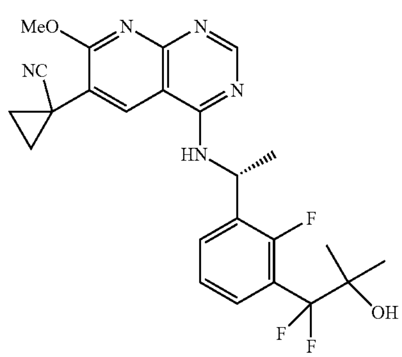 [SMILES: COc1nc2ncnc(N[C@H](C)c3cccc(C(F)(F)C(C)(C)O)c3F)c2cc1C1(C#N)CC1] | (R)-1-(4-((1-(3-(1,1-difluoro-2-hydroxy-2-methylpropyl)-2-fluorophenyl)ethyl)amino)-7-methoxypyrido[2,3-d]pyrimidin-6-yl)cyclopropane-1-carbonitrile | 472.7 |

TABLE 1-continued

| Compound | Structure | Name | [M + H]+ |
|---|---|---|---|
| 357 | 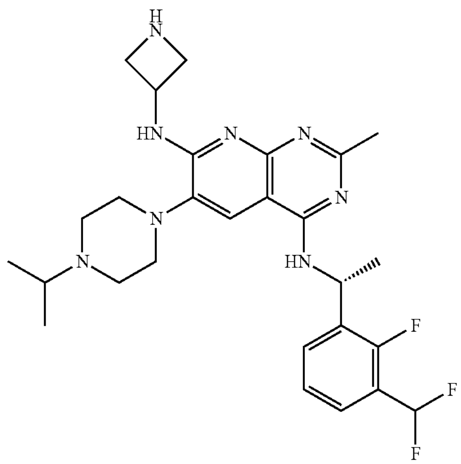 [SMILES: Cc1nc(N[C@H](C)c2cccc(C(F)F)c2F)c2cc(N3CCN(C(C)C)CC3)c(NC3CNC3)nc2n1] | (R)-N7-(azetidin-3-yl)-N4-(1-(3-(difluoromethyl)-2-fluorophenyl)ethyl)-6-(4-isopropylpiperazin-1-yl)-2-methylpyrido[2,3-d]pyrimidine-4,7-diamine | 529.3 |
| 358 | 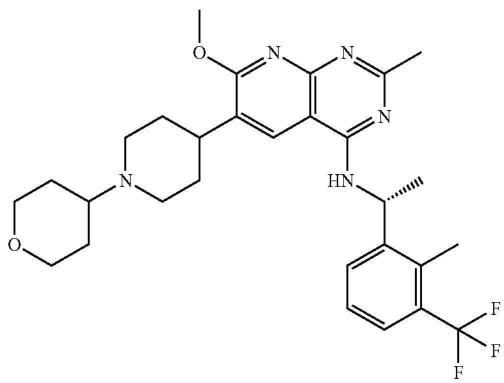 [SMILES: COc1nc2nc(C)nc(N[C@H](C)c3cccc(C(F)(F)F)c3C)c2cc1C1CCN(C2CCOCC2)CC1] | (R)-7-methoxy-2-methyl-N-(1-(2-methyl-3-(trifluoromethyl)phenyl)ethyl)-6-(1-(tetrahydro-2H-pyran-4-yl)piperidin-4-yl)pyrido[2,3-d]pyrimidin-4-amine | 544.5 |
| 359 | 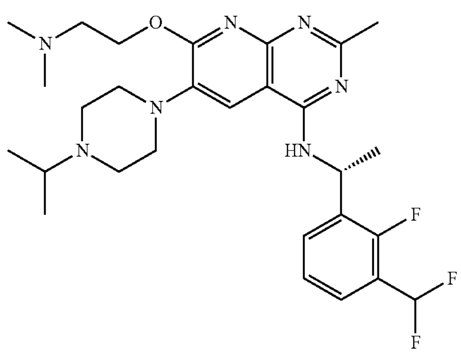 [SMILES: Cc1nc(N[C@H](C)c2cccc(C(F)F)c2F)c2cc(N3CCN(C(C)C)CC3)c(OCCN(C)C)nc2n1] | (R)-N-(1-(3-(difluoromethyl)-2-fluorophenyl)ethyl)-7-(2-(dimethylamino)ethoxy)-6-(4-isopropylpiperazin-1-yl)-2-methylpyrido[2,3-d]pyrimidin-4-amine | 546.3 |
| 360 | 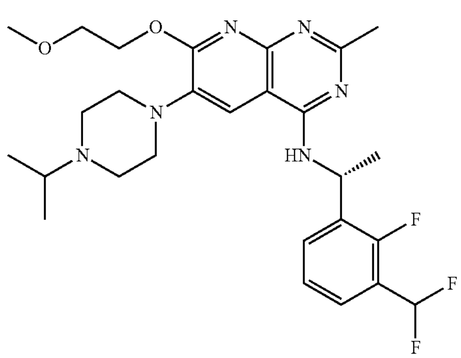 [SMILES: COCCOc1nc2nc(C)nc(N[C@H](C)c3cccc(C(F)F)c3F)c2cc1N1CCN(C(C)C)CC1] | (R)-N-(1-(3-(difluoromethyl)-2-fluorophenyl)ethyl)-6-(4-isopropylpiperazin-1-yl)-7-(2-methoxyethoxy)-2-methylpyrido[2,3-d]pyrimidin-4-amine | 533.5 |

TABLE 1-continued

| Compound | Structure | Name | [M + H]+ |
|---|---|---|---|
| 361 | 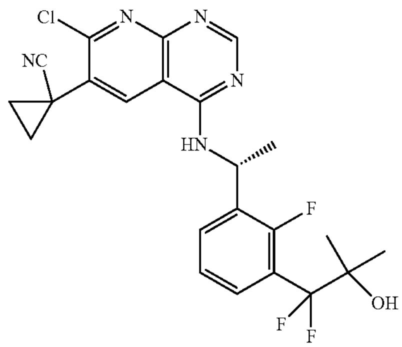 [SMILES: C[C@@H](Nc1ncnc2nc(Cl)c(C3(C#N)CC3)cc12)c1cccc(C(F)(F)C(C)(C)O)c1F] | (R)-1-(7-chloro-4-((1-(3-(1,1-difluoro-2-hydroxy-2-methylpropyl)-2-fluorophenyl)ethyl)amino)pyrido[2,3-d]pyrimidin-6-yl)cyclopropane-1-carbonitrile | 476.2 |
| 362 | 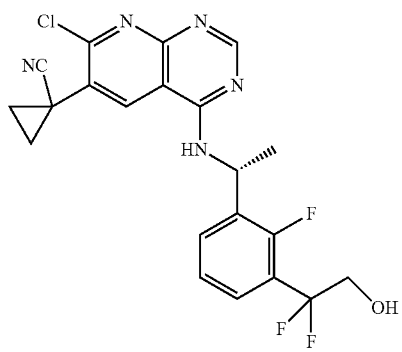 [SMILES: C[C@@H](Nc1ncnc2nc(Cl)c(C3(C#N)CC3)cc12)c1cccc(C(F)(F)CO)c1F] | (R)-1-(7-chloro-4-((1-(3-(1,1-difluoro-2-hydroxyethyl)-2-fluorophenyl)ethyl)amino)pyrido[2,3-d]pyrimidin-6-yl)cyclopropane-1-carbonitrile | 448.2 |
| 363 | 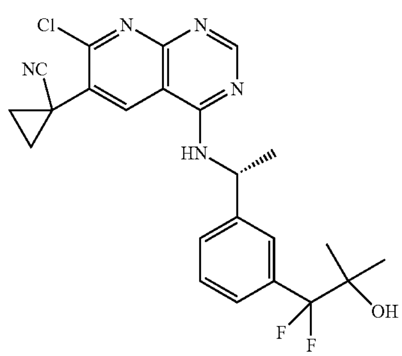 [SMILES: C[C@@H](Nc1ncnc2nc(Cl)c(C3(C#N)CC3)cc12)c1cccc(C(F)(F)C(C)(C)O)c1] | (R)-1-(7-chloro-4-((1-(3-(1,1-difluoro-2-hydroxy-2-methylpropyl)phenyl)ethyl)amino)pyrido[2,3-d]pyrimidin-6-yl)cyclopropane-1-carbonitrile | 458.3 |
| 364 | 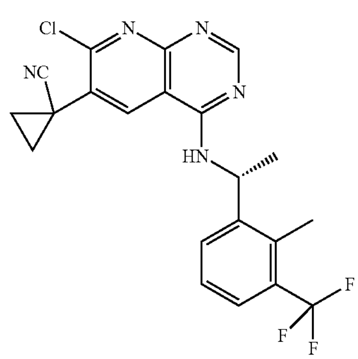 [SMILES: Cc1c([C@@H](C)Nc2ncnc3nc(Cl)c(C4(C#N)CC4)cc23)cccc1C(F)(F)F] | (R)-1-(7-chloro-4-((1-(2-methyl-3-(trifluoromethyl)phenyl)ethyl)amino)pyrido[2,3-d]pyrimidin-6-yl)cyclopropane-1-carbonitrile | 432.2 |

TABLE 1-continued

| Compound | Structure | Name | [M + H]+ |
|---|---|---|---|
| 365 | 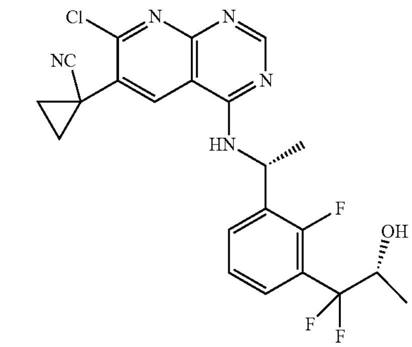 [SMILES: C[C@@H](Nc1ncnc2nc(Cl)c(C3(C#N)CC3)cc12)c1cccc(C(F)(F)[C@@H](C)O)c1F] | 1-(7-chloro-4-(((R)-1-(3-((R)-1,1-difluoro-2-hydroxypropyl)-2-fluorophenyl)ethyl)amino)pyrido[2,3-d]pyrimidin-6-yl)cyclopropane-1-carbonitrile | 462.2 |
| 366 | 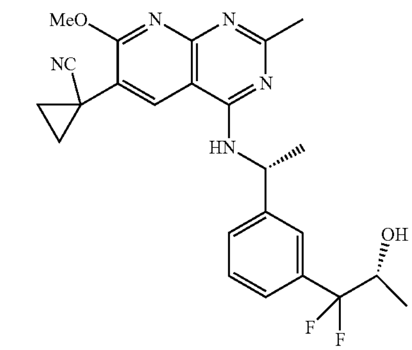 [SMILES: COc1nc2nc(C)nc(N[C@H](C)c3cccc(C(F)(F)[C@@H](C)O)c3)c2cc1C1(C#N)CC1] | 1-(4-(((R)-1-(3-((R)-1,1-difluoro-2-hydroxypropyl)phenyl)ethyl)amino)-7-methoxy-2-methylpyrido[2,3-d]pyrimidin-6-yl)cyclopropane-1-carbonitrile | 454.3 |
| 367 | 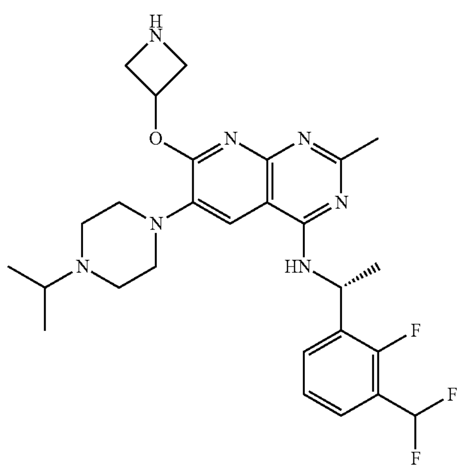 [SMILES: Cc1nc(N[C@H](C)c2cccc(C(F)F)c2F)c2cc(N3CCN(C(C)C)CC3)c(OC3CNC3)nc2n1] | (R)-7-(azetidin-3-yloxy)-N-(1-(3-(difluoromethyl)-2-fluorophenyl)ethyl)-6-(4-isopropylpiperazin-1-yl)-2-methylpyrido[2,3-d]pyrimidin-4-amine | 530.5 |
| 368 | 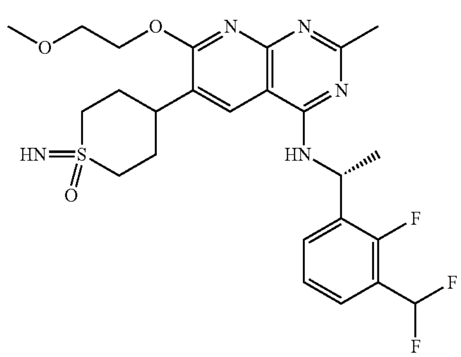 [SMILES: COCCOc1nc2nc(C)nc(N[C@H](C)c3cccc(C(F)F)c3F)c2cc1C1CCS(=N)(=O)CC1] | (R)-4-(4-((1-(3-(difluoromethyl)-2-fluorophenyl)ethyl)amino)-7-(2-methoxyethoxy)-2-methylpyrido[2,3-d]pyrimidin-6-yl)-1-iminohexahydro-1l6-thiopyran 1-oxide | 538.5 |

TABLE 1-continued

| Compound | Structure | Name | [M + H]+ |
|---|---|---|---|
| 369 | 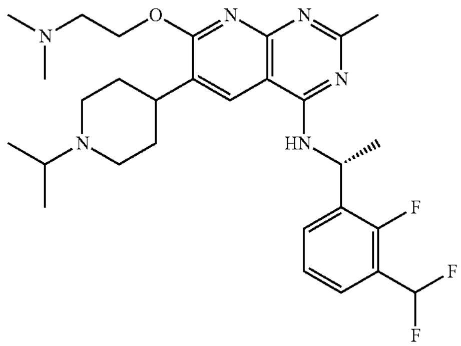 [SMILES: Cc1nc(N[C@H](C)c2cccc(C(F)F)c2F)c2cc(C3CCN(C(C)C)CC3)c(OCCN(C)C)nc2n1] | (R)-N-(1-(3-(difluoromethyl)-2-fluorophenyl)ethyl)-7-(2-(dimethylamino)ethoxy)-6-(1-isopropylpiperidin-4-yl)-2-methylpyrido[2,3-d]pyrimidin-4-amine | 545.6 |
| 370 | 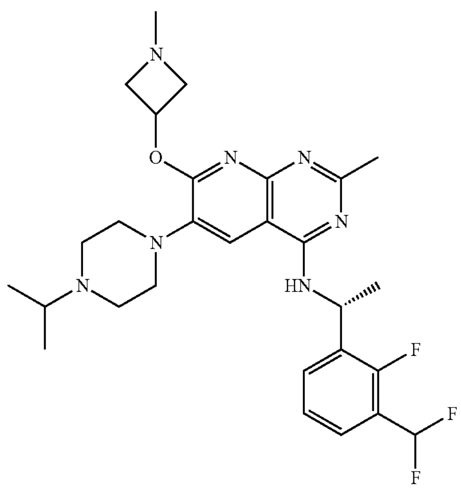 [SMILES: Cc1nc(N[C@H](C)c2cccc(C(F)F)c2F)c2cc(N3CCN(C(C)C)CC3)c(OC3CN(C)C3)nc2n1] | (R)-N-(1-(3-(difluoromethyl)-2-fluorophenyl)ethyl)-6-(4-isopropylpiperazin-1-yl)-2-methyl-7-((1-methylazetidin-3-yl)oxy)pyrido[2,3-d]pyrimidin-4-amine | 544.5 |
| 371 | 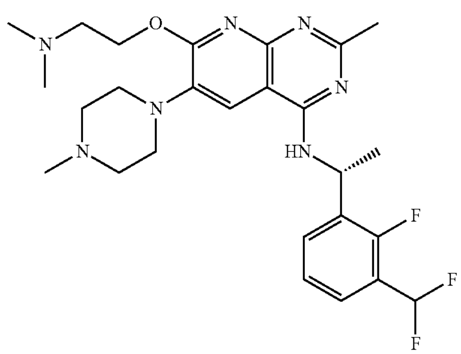 [SMILES: Cc1nc(N[C@H](C)c2cccc(C(F)F)c2F)c2cc(N3CCN(C)CC3)c(OCCN(C)C)nc2n1] | (R)-N-(1-(3-(difluoromethyl)-2-fluorophenyl)ethyl)-7-(2-(dimethylamino)ethoxy)-2-methyl-6-(4-methylpiperazin-1-yl)pyrido[2,3-d]pyrimidin-4-amine | 518.5 |
| 372 | 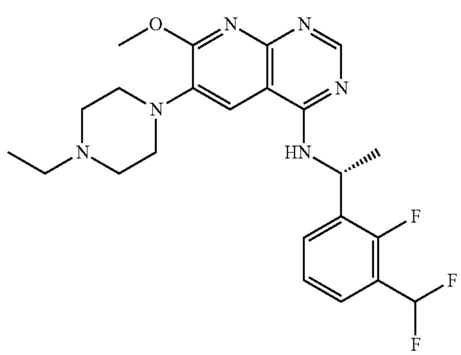 [SMILES: CCN1CCN(c2cc3c(N[C@H](C)c4cccc(C(F)F)c4F)ncnc3nc2OC)CC1] | (R)-N-(1-(3-(difluoromethyl)-2-fluorophenyl)ethyl)-6-(4-ethylpiperazin-1-yl)-7-methoxypyrido[2,3-d]pyrimidin-4-amine | 461.3 |

TABLE 1-continued

| Compound | Structure | Name | [M + H]+ |
|---|---|---|---|
| 373 | 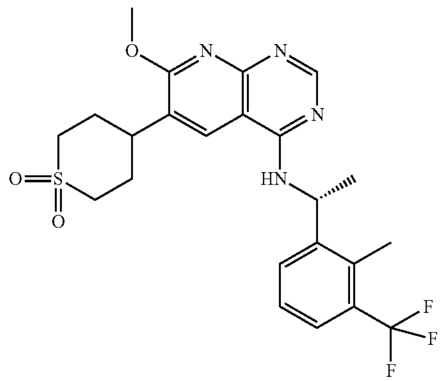 [SMILES: COc1nc2ncnc(N[C@H](C)c3cccc(C(F)(F)F)c3C)c2cc1C1CCS(=O)(=O)CC1] | (R)-4-(7-methoxy-4-((1-(2-methyl-3-(trifluoromethyl)phenyl)ethyl)amino)pyrido[2,3-d]pyrimidin-6-yl)tetrahydro-2H-thiopyran 1,1-dioxide | 530.4 |
| 374 | 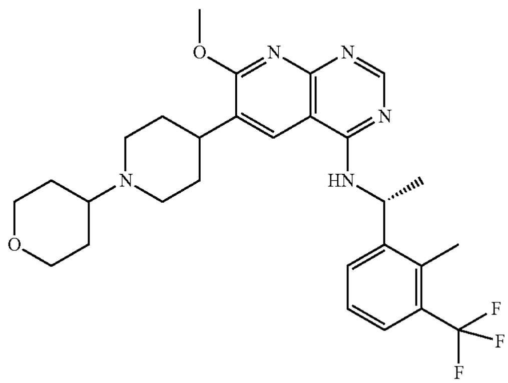 [SMILES: COc1nc2ncnc(N[C@H](C)c3cccc(C(F)(F)F)c3C)c2cc1C1CCN(C2CCOCC2)CC1] | (R)-7-methoxy-N-(1-(2-methyl-3-(trifluoromethyl)phenyl)ethyl)-6-(1-(tetrahydro-2H-pyran-4-yl)piperidin-4-yl)pyrido[2,3-d]pyrimidin-4-amine | 495.3 |
| 375 | 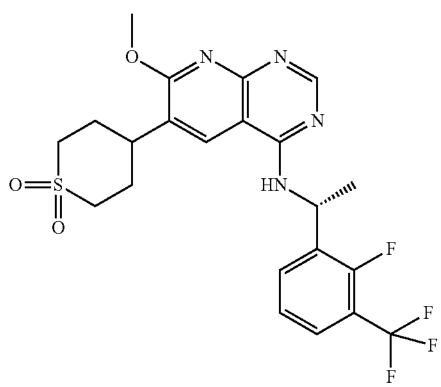 | (R)-4-(4-((1-(2-fluoro-3-(trifluoromethyl)phenyl)ethyl)amino)-7-methoxypyrido[2,3-d]pyrimidin-6-yl)tetrahydro-2H-thiopyran 1,1-dioxide | 499.3 |
| 376 | 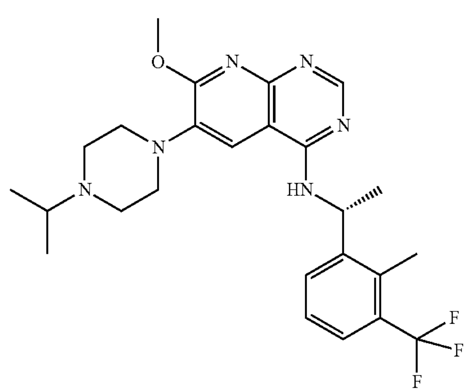 [SMILES: COc1nc2ncnc(N[C@H](C)c3cccc(C(F)(F)F)c3C)c2cc1N1CCN(C(C)C)CC1] | (R)-6-(4-isopropylpiperazin-1-yl)-7-methoxy-N-(1-(2-methyl-3-(trifluoromethyl)phenyl)ethyl)pyrido[2,3-d]pyrimidin-4-amine | 489.4 |

| Compound | Structure | Name | [M + H]+ |
|---|---|---|---|
| 377 | 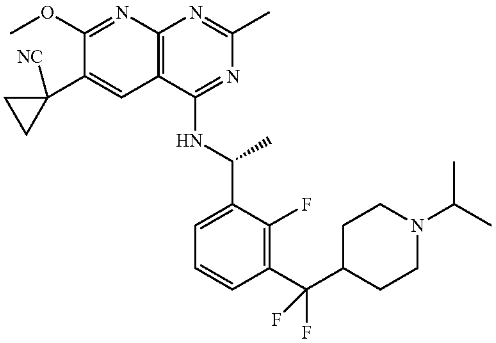 [SMILES: COc1nc2nc(C)nc(N[C@H](C)c3cccc(C(F)(F)C4CCN(C(C)C)CC4)c3F)c2cc1C1(C#N)CC1] | (R)-1-(4-((1-(3-(difluoro(1-isopropylpiperidin-4-yl)methyl)-2-fluorophenyl)ethyl)amino)-7-methoxy-2-methylpyrido[2,3-d]pyrimidin-6-yl)cyclopropane-1-carbonitrile | 533.4 |
| 378 | 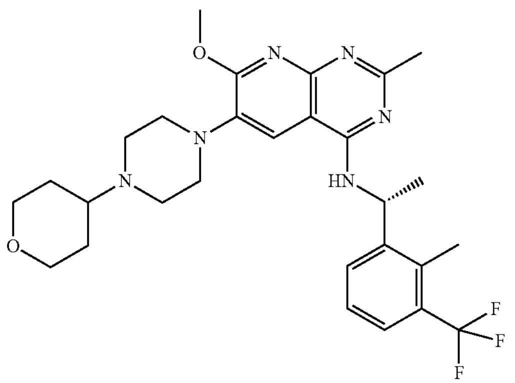 [SMILES: COc1nc2nc(C)nc(N[C@H](C)c3cccc(C(F)(F)F)c3C)c2cc1N1CCN(C2CCOCC2)CC1] | (R)-7-methoxy-2-methyl-N-(1-(2-methyl-3-(trifluoromethyl)phenyl)ethyl)-6-(4-(tetrahydro-2H-pyran-4-yl)piperazin-1-yl)pyrido[2,3-d]pyrimidin-4-amine | 545.4 |
| 379 | 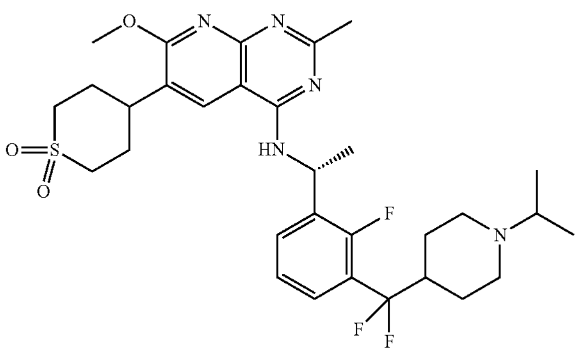 [SMILES: COc1nc2nc(C)nc(N[C@H](C)c3cccc(C(F)(F)C4CCN(C(C)C)CC4)c3F)c2cc1C1CCS(=O)(=O)CC1] | (R)-4-(4-((1-(3-(difluoro(1-isopropylpiperidin-4-yl)methyl)-2-fluorophenyl)ethyl)amino)-7-methoxy-2-methylpyrido[2,3-d]pyrimidin-6-yl)tetrahydro-2H-thiopyran 1,1-dioxide | 620.5 |
| 380 | 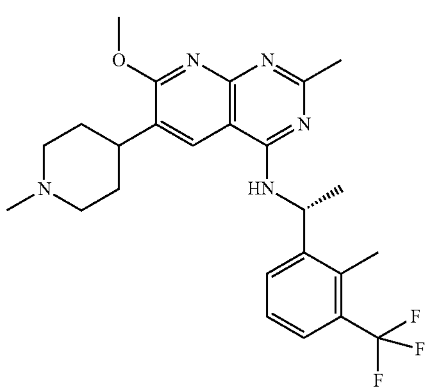 [SMILES: COc1nc2nc(C)nc(N[C@H](C)c3cccc(C(F)(F)F)c3C)c2cc1C1CCN(C)CC1] | (R)-7-methoxy-2-methyl-N-(1-(2-methyl-3-(trifluoromethyl)phenyl)ethyl)-6-(1-methylpiperidin-4-yl)pyrido[2,3-d]pyrimidin-4-amine | 474.4 |

| Compound | Structure | Name | [M + H]+ |
|---|---|---|---|
| 381 | 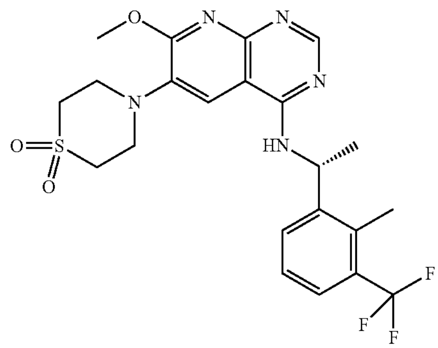 [SMILES: COc1nc2ncnc(N[C@H](C)c3cccc(C(F)(F)F)c3C)c2cc1N1CCS(=O)(=O)CC1] | (R)-4-(7-methoxy-4-((1-(2-methyl-3-(trifluoromethyl)phenyl)ethyl)amino)pyrido[2,3-d]pyrimidin-6-yl)thiomorpholine 1,1-dioxide | 496.7 |
| 382 | 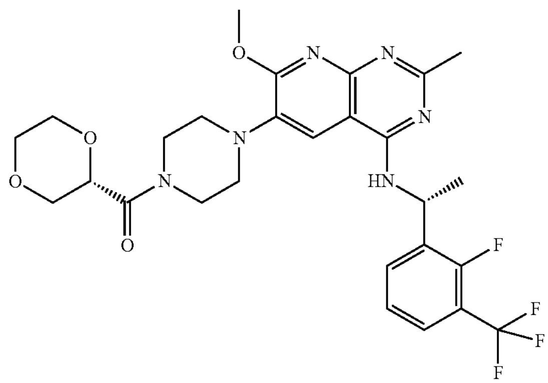 [SMILES: COc1nc2nc(C)nc(N[C@H](C)c3cccc(C(F)(F)F)c3F)c2cc1N1CCN(C(=O)[C@@H]2COCCO2)CC1] | ((S)-1,4-dioxan-2-yl)(4-(4-(((R)-1-(2-fluoro-3-(trifluoromethyl)phenyl)ethyl)amino)-7-methoxy-2-methylpyrido[2,3-d]pyrimidin-6-yl)piperazin-1-yl)methanone | 579.4 |
| 383 | 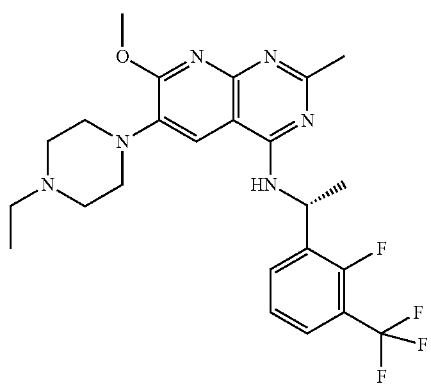 [SMILES: CCN1CCN(c2cc3c(N[C@H](C)c4cccc(C(F)(F)F)c4F)nc(C)nc3nc2OC)CC1] | (R)-6-(4-ethylpiperazin-1-yl)-N-(1-(2-fluoro-3-(trifluoromethyl)phenyl)ethyl)-7-methoxy-2-methylpyrido[2,3-d]pyrimidin-4-amine | 493.3 |
| 384 | 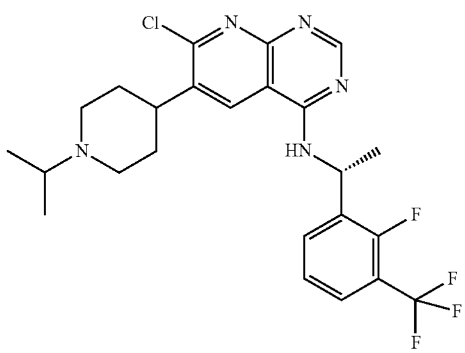 | (R)-7-chloro-N-(1-(2-fluoro-3-(trifluoromethyl)phenyl)ethyl)-6-(1-isopropylpiperidin-4-yl)pyrido[2,3-d]pyrimidin-4-amine | 496.4 |

TABLE 1-continued

| Compound | Structure | Name | [M + H]+ |
|---|---|---|---|
| 385 | 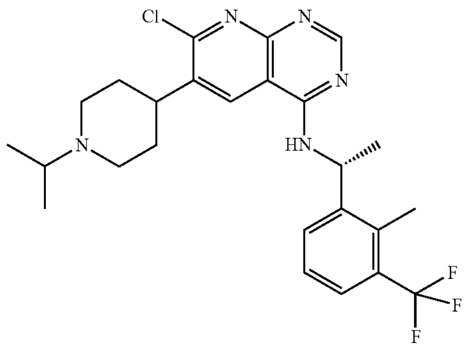 [SMILES: Cc1c([C@@H](C)Nc2ncnc3nc(Cl)c(C4CCN(C(C)C)CC4)cc23)cccc1C(F)(F)F] | (R)-7-chloro-6-(1-isopropylpiperidin-4-yl)-N-(1-(2-methyl-3-(trifluoromethyl)phenyl)ethyl)pyrido[2,3-d]pyrimidin-4-amine | 492.4 |
| 386 | 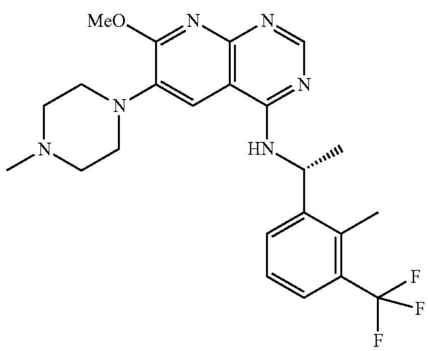 [SMILES: COc1nc2ncnc(N[C@H](C)c3cccc(C(F)(F)F)c3C)c2cc1N1CCN(C)CC1] | (R)-7-methoxy-N-(1-(2-methyl-3-(trifluoromethyl)phenyl)ethyl)-6-(4-methylpiperazin-1-yl)pyrido[2,3-d]pyrimidin-4-amine | 461.4 |
| 387 | 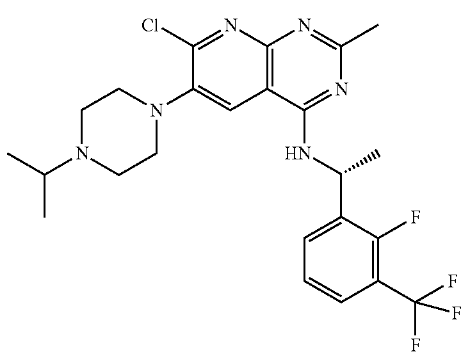 | (R)-7-chloro-N-(1-(2-fluoro-3-(trifluoromethyl)phenyl)ethyl)-6-(4-isopropylpiperazin-1-yl)-2-methylpyrido[2,3-d]pyrimidin-4-amine | 511.6 |
| 388 | 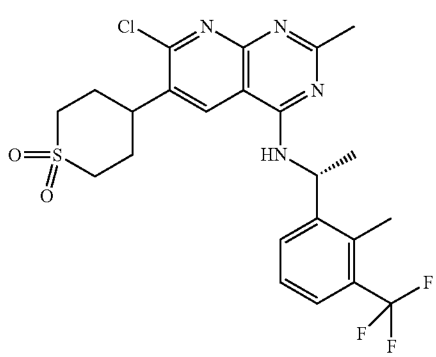 [SMILES: Cc1nc(N[C@H](C)c2cccc(C(F)(F)F)c2C)c2cc(C3CCS(=O)(=O)CC3)c(Cl)nc2n1] | (R)-4-(7-chloro-2-methyl-4-((1-(2-methyl-3-(trifluoromethyl)phenyl)ethyl)amino)pyrido[2,3-d]pyrimidin-6-yl)tetrahydro-2H-thiopyran 1,1-dioxide | 513.2 |

TABLE 1-continued

| Compound | Structure | Name | [M + H]+ |
|---|---|---|---|
| 389 | 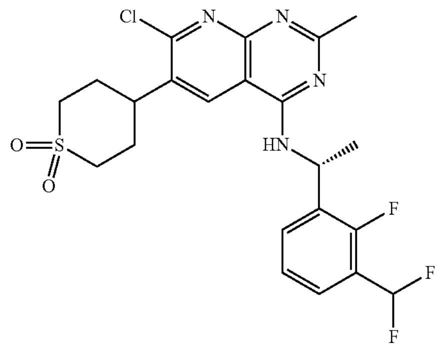 [SMILES: Cc1nc(N[C@H](C)c2cccc(C(F)F)c2F)c2cc(C3CCS(=O)(=O)CC3)c(Cl)nc2n1] | (R)-4-(7-chloro-4-((1-(3-(difluoromethyl)-2-fluorophenyl)ethyl)amino)-2-methylpyrido[2,3-d]pyrimidin-6-yl)tetrahydro-2H-thiopyran 1,1-dioxide | 499.3 |
| 390 | 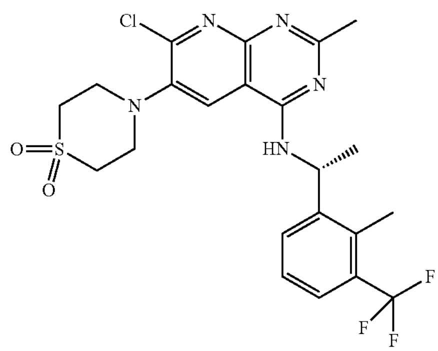 [SMILES: Cc1nc(N[C@H](C)c2cccc(C(F)(F)F)c2C)c2cc(N3CCS(=O)(=O)CC3)c(Cl)nc2n1] | (R)-4-(7-chloro-2-methyl-4-((1-(2-methyl-3-(trifluoromethyl)phenyl)ethyl)amino)pyrido[2,3-d]pyrimidin-6-yl)thiomorpholine 1,1-dioxide | 514.3 |
| 391 | 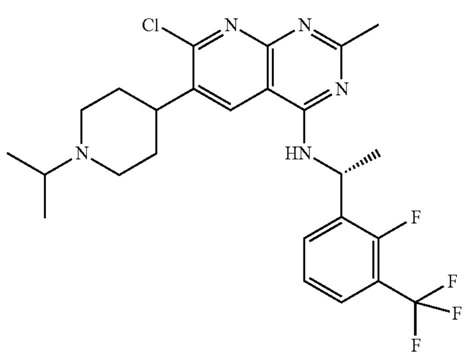 | (R)-7-chloro-N-(1-(2-fluoro-3-(trifluoromethyl)phenyl)ethyl)-6-(1-isopropylpiperidin-4-yl)-2-methylpyrido[2,3-d]pyrimidin-4-amine | 510.3 |
| 392 | 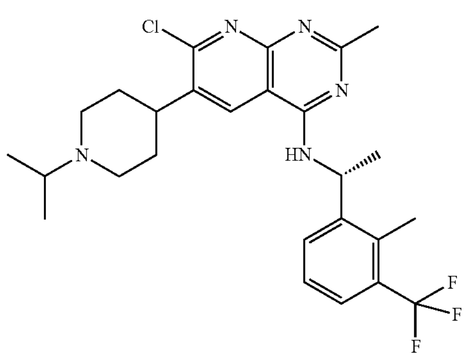 [SMILES: Cc1nc(N[C@H](C)c2cccc(C(F)(F)F)c2C)c2cc(C3CCN(C(C)C)CC3)c(Cl)nc2n1] | (R)-7-chloro-6-(1-isopropylpiperidin-4-yl)-2-methyl-N-(1-(2-methyl-3-(trifluoromethyl)phenyl)ethyl)pyrido[2,3-d]pyrimidin-4-amine | 506.4 |

TABLE 1-continued

| Compound | Structure | Name | [M + H]+ |
|---|---|---|---|
| 393 | 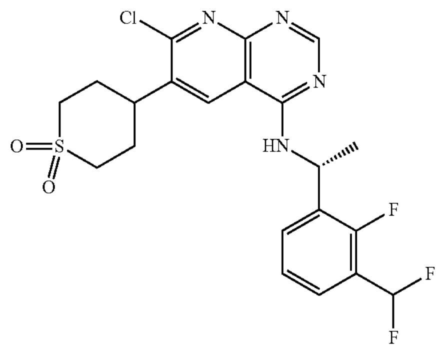 [SMILES: C[C@@H](Nc1ncnc2nc(Cl)c(C3CCS(=O)(=O)CC3)cc12)c1cccc(C(F)F)c1F] | (R)-4-(7-chloro-4-((1-(3-(difluoromethyl)-2-fluorophenyl)ethyl)amino)pyrido[2,3-d]pyrimidin-6-yl)tetrahydro-2H-thiopyran 1,1-dioxide | 485.2 |
| 394 | 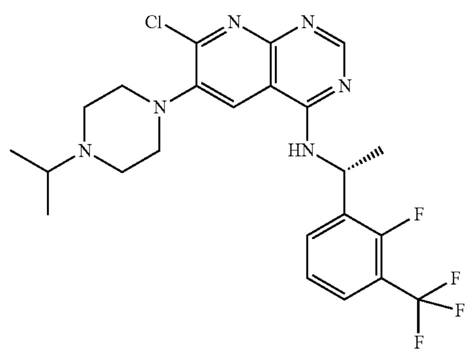 [SMILES: Cc1c([C@@H](C)Nc2ncnc3nc(Cl)c(N4CCN(C(C)C)CC4)cc23)cccc1C(F)(F)F] | (R)-7-chloro-N-(1-(2-fluoro-3-(trifluoromethyl)phenyl)ethyl)-6-(4-isopropylpiperazin-1-yl)pyrido[2,3-d]pyrimidin-4-amine | 497.4 |
| 395 | 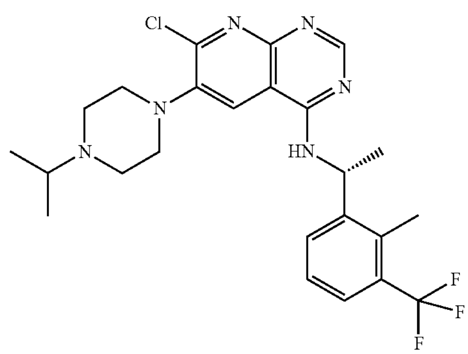 | (R)-7-chloro-6-(4-isopropylpiperazin-1-yl)-N-(1-(2-methyl-3-(trifluoromethyl)phenyl)ethyl)pyrido[2,3-d]pyrimidin-4-amine | 493.3 |
| 396 | 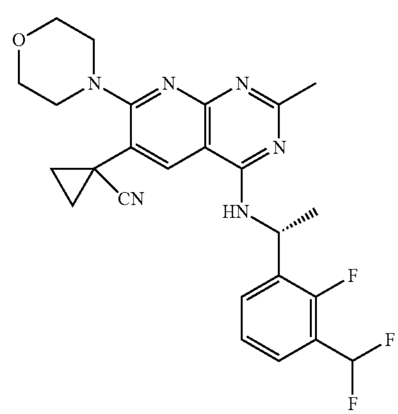 [SMILES: Cc1nc(N[C@H](C)c2cccc(C(F)F)c2F)c2cc(C3(C#N)CC3)c(N3CCOCC3)nc2n1] | (R)-1-(4-((1-(3-(difluoromethyl)-2-fluorophenyl)ethyl)amino)-2-methyl-7-morpholinopyrido[2,3-d]pyrimidin-6-yl)cyclopropane-1-carbonitrile | 483.7 |

TABLE 1-continued

| Compound | Structure | Name | [M + H]+ |
|---|---|---|---|
| 397 | 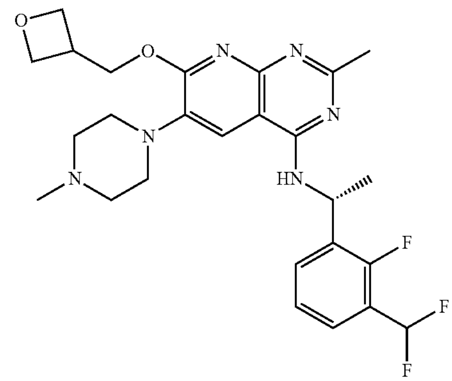 [SMILES: Cc1nc(N[C@H](C)c2cccc(C(F)F)c2F)c2cc(N3CCN(C)CC3)c(OCC3COC3)nc2n1] | (R)-N-(1-(3-(difluoromethyl)-2-fluorophenyl)ethyl)-2-methyl-6-(4-methylpiperazin-1-yl)-7-(oxetan-3-ylmethoxy)pyrido[2,3-d]pyrimidin-4-amine | 517.4 |
| 398 | 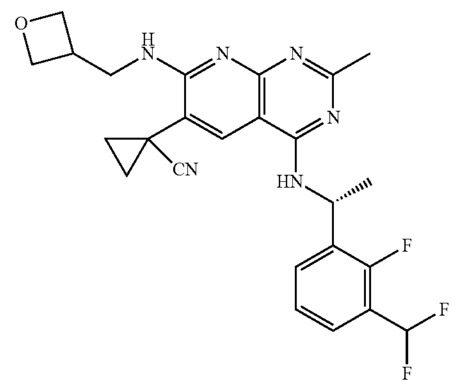 [SMILES: Cc1nc(N[C@H](C)c2cccc(C(F)F)c2F)c2cc(C3(C#N)CC3)c(NCC3COC3)nc2n1] | (R)-1-(4-((1-(3-(difluoromethyl)-2-fluorophenyl)ethyl)amino)-2-methyl-7-((oxetan-3-ylmethyl)amino)pyrido[2,3-d]pyrimidin-6-yl)cyclopropane-1-carbonitrile | 483.3 |
| 399 | 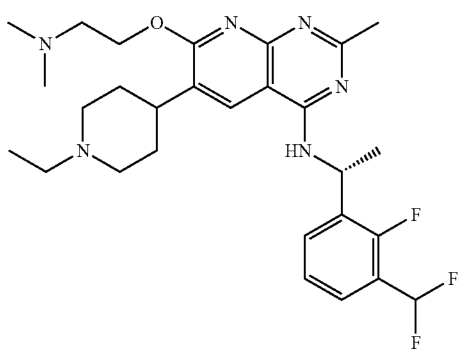 | (R)-N-(1-(3-(difluoromethyl)-2-fluorophenyl)ethyl)-7-(2-(dimethylamino)ethoxy)-6-(1-ethylpiperidin-4-yl)-2-methylpyrido[2,3-d]pyrimidin-4-amine | 531.5 |
| 400 | 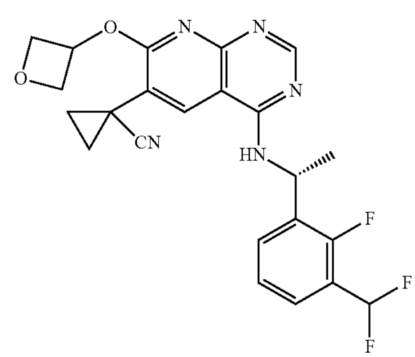 [SMILES: C[C@@H](Nc1ncnc2nc(OC3COC3)c(C3(C#N)CC3)cc12)c1cccc(C(F)F)c1F] | (R)-1-(4-((1-(3-(difluoromethyl)-2-fluorophenyl)ethyl)amino)-7-(oxetan-3-yloxy)pyrido[2,3-d]pyrimidin-6-yl)cyclopropane-1-carbonitrile | 456.7 |

TABLE 1-continued

| Compound | Structure | Name | [M + H]+ |
|---|---|---|---|
| 401 | 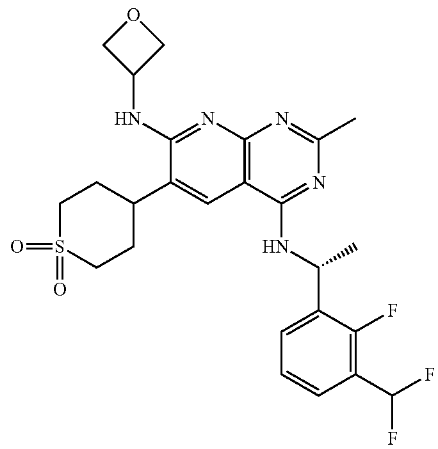 [SMILES: Cc1nc(N[C@H](C)c2cccc(C(F)F)c2F)c2cc(C3CCS(=O)(=O)CC3)c(NC3COC3)nc2n1] | (R)-4-(4-((1-(3-(difluoromethyl)-2-fluorophenyl)ethyl)amino)-2-methyl-7-(oxetan-3-ylamino)pyrido[2,3-d]pyrimidin-6-yl)tetrahydro-2H-thiopyran 1,1-dioxide | 536.5 |
| 402 | 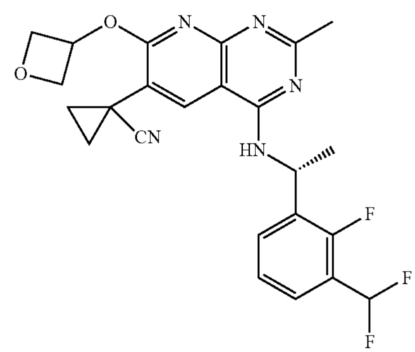 [SMILES: Cc1nc(N[C@H](C)c2cccc(C(F)F)c2F)c2cc(C3(C#N)CC3)c(OC3COC3)nc2n1] | (R)-1-(4-((1-(3-(difluoromethyl)-2-fluorophenyl)ethyl)amino)-2-methyl-7-(oxetan-3-yloxy)pyrido[2,3-d]pyrimidin-6-yl)cyclopropane-1-carbonitrile | 470.4 |
| 403 | 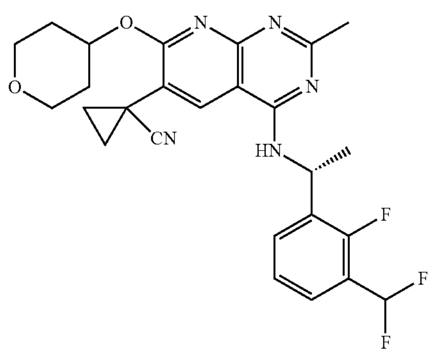 [SMILES: Cc1nc(N[C@H](C)c2cccc(C(F)F)c2F)c2cc(C3(C#N)CC3)c(OC3CCOCC3)nc2n1] | (R)-1-(4-((1-(3-(difluoromethyl)-2-fluorophenyl)ethyl)amino)-2-methyl-7-((tetrahydro-2H-pyran-4-yl)oxy)pyrido[2,3-d]pyrimidin-6-yl)cyclopropane-1-carbonitrile | 498.3 |
| 404 | 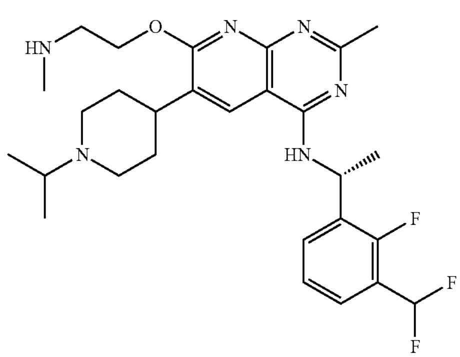 [SMILES: CNCCOc1nc2nc(C)nc(N[C@H](C)c3cccc(C(F)F)c3F)c2cc1C1CCN(C(C)C)CC1] | (R)-N-(1-(3-(difluoromethyl)-2-fluorophenyl)ethyl)-6-(1-isopropylpiperidin-4-yl)-2-methyl-7-(2-(methylamino)ethoxy)pyrido[2,3-d]pyrimidin-4-amine | 531.4 |

TABLE 1-continued

| Compound | Structure | Name | [M + H]+ |
|---|---|---|---|
| 405 | 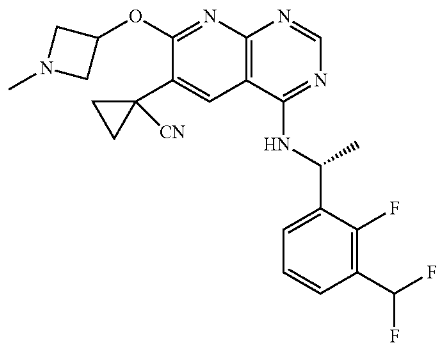 [SMILES: C[C@@H](Nc1ncnc2nc(OC3CN(C)C3)c(C3(C#N)CC3)cc12)c1cccc(C(F)F)c1F] | (R)-1-(4-((1-(3-(difluoromethyl)-2-fluorophenyl)ethyl)amino)-7-((1-methylazetidin-3-yl)oxy)pyrido[2,3-d]pyrimidin-6-yl)cyclopropane-1-carbonitrile | 469.3 |
| 406 | 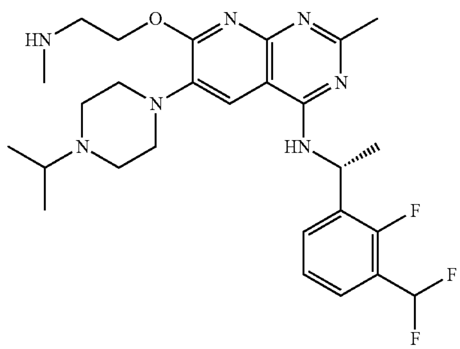 [SMILES: CNCCOc1nc2nc(C)nc(N[C@H](C)c3cccc(C(F)F)c3F)c2cc1N1CCN(C(C)C)CC1] | (R)-N-(1-(3-(difluoromethyl)-2-fluorophenyl)ethyl)-6-(4-isopropylpiperazin-1-yl)-2-methyl-7-(2-(methylamino)ethoxy)pyrido[2,3-d]pyrimidin-4-amine | 532.5 |
| 407 | 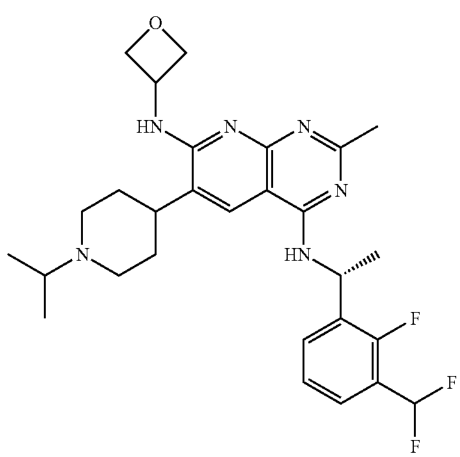 | (R)-N4-(1-(3-(difluoromethyl)-2-fluorophenyl)ethyl)-6-(1-isopropylpiperidin-4-yl)-2-methyl-N7-(oxetan-3-yl)pyrido[2,3-d]pyrimidine-4,7-diamine | 529.4 |
| 408 | 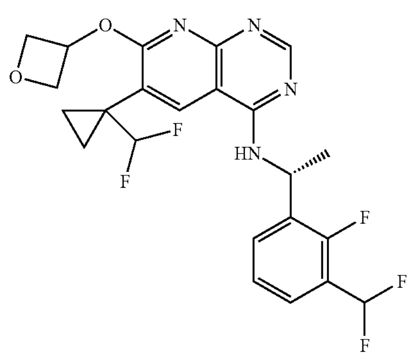 [SMILES: C[C@@H](Nc1ncnc2nc(OC3COC3)c(C3(C(F)F)CC3)cc12)c1cccc(C(F)F)c1F] | (R)-N-(1-(3-(difluoromethyl)-2-fluorophenyl)ethyl)-6-(1-(difluoromethyl)cyclopropyl)-7-(oxetan-3-yloxy)pyrido[2,3-d]pyrimidin-4-amine | 481.2 |

TABLE 1-continued

| Compound | Structure | Name | [M + H]+ |
|---|---|---|---|
| 409 | 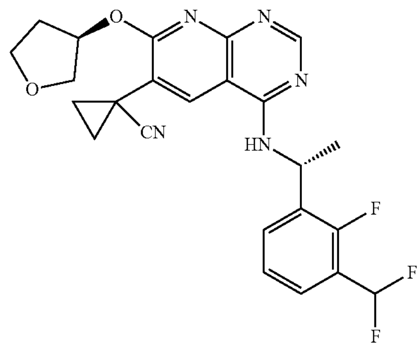 [SMILES: C[C@@H](Nc1ncnc2nc(O[C@@H]3CCOC3)c(C3(C#N)CC3)cc12)c1cccc(C(F)F)c1F] | 1-(4-(((R)-1-(3-(difluoromethyl)-2-fluorophenyl)ethyl)amino)-7-(((R)-tetrahydrofuran-3-yl)oxy)pyrido[2,3-d]pyrimidin-6-yl)cyclopropane-1-carbonitrile | 470.7 |
| 410 | 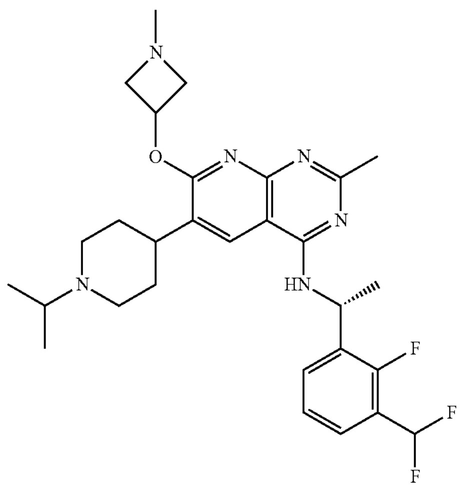 [SMILES: Cc1nc(N[C@H](C)c2cccc(C(F)F)c2F)c2cc(C3CCN(C(C)C)CC3)c(OC3CN(C)C3)nc2n1] | (R)-N-(1-(3-(difluoromethyl)-2-fluorophenyl)ethyl)-6-(1-isopropylpiperidin-4-yl)-2-methyl-7-((1-methylazetidin-3-yl)oxy)pyrido[2,3-d]pyrimidin-4-amine | 543.5 |
| 411 | 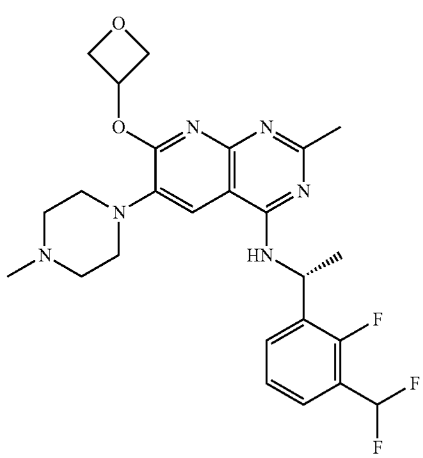 | (R)-N-(1-(3-(difluoromethyl)-2-fluorophenyl)ethyl)-2-methyl-6-(4-methylpiperazin-1-yl)-7-(oxetan-3-yloxy)pyrido[2,3-d]pyrimidin-4-amine | 503.5 |

TABLE 1-continued

| Compound | Structure | Name | [M + H]+ |
|---|---|---|---|
| 412 | 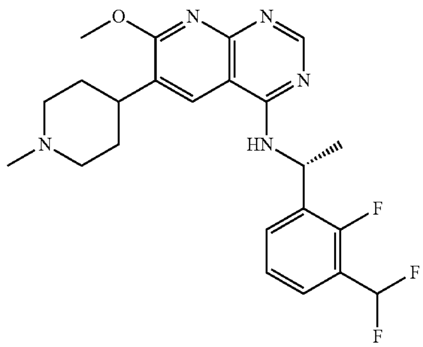 [SMILES: COc1nc2ncnc(N[C@H](C)c3cccc(C(F)F)c3F)c2cc1C1CCN(C)CC1] | (R)-N-(1-(3-(difluoromethyl)-2-fluorophenyl)ethyl)-7-methoxy-6-(1-methylpiperidin-4-yl)pyrido[2,3-d]pyrimidin-4-amine | 446.3 |
| 413 | 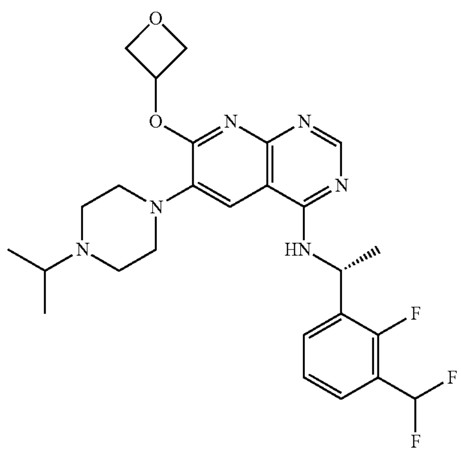 [SMILES: CC(C)N1CCN(c2cc3c(N[C@H](C)c4cccc(C(F)F)c4F)ncnc3nc2OC2COC2)CC1] | (R)-N-(1-(3-(difluoromethyl)-2-fluorophenyl)ethyl)-6-(4-isopropylpiperazin-1-yl)-7-(oxetan-3-yloxy)pyrido[2,3-d]pyrimidin-4-amine | 517.4 |
| 414 | 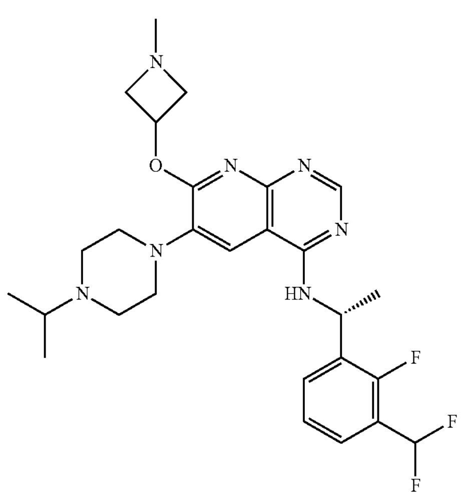 [SMILES: CC(C)N1CCN(c2cc3c(N[C@H](C)c4cccc(C(F)F)c4F)ncnc3nc2OC2CN(C)C2)CC1] | (R)-N-(1-(3-(difluoromethyl)-2-fluorophenyl)ethyl)-6-(4-isopropylpiperazin-1-yl)-7-((1-methylazetidin-3-yl)oxy)pyrido[2,3-d]pyrimidin-4-amine | 530.5 |

TABLE 1-continued

| Compound | Structure | Name | [M + H]+ |
|---|---|---|---|
| 415 | 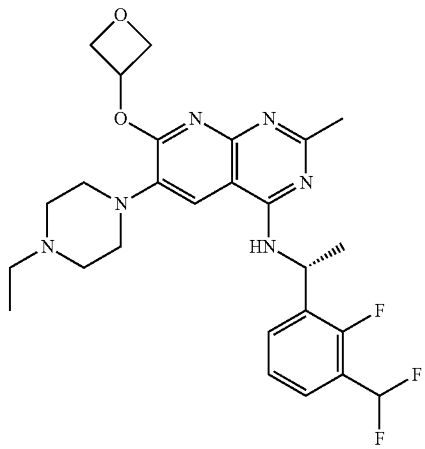 [SMILES: CCN1CCN(c2cc3c(N[C@H](C)c4cccc(C(F)F)c4F)nc(C)nc3nc2OC2COC2)CC1] | (R)-N-(1-(3-(difluoromethyl)-2-fluorophenyl)ethyl)-6-(4-ethylpiperazin-1-yl)-2-methyl-7-(oxetan-3-yloxy)pyrido[2,3-d]pyrimidin-4-amine | 517.5 |
| 416 | 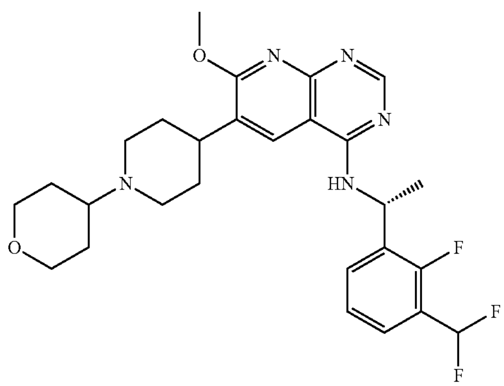 [SMILES: COc1nc2ncnc(N[C@H](C)c3cccc(C(F)F)c3F)c2cc1C1CCN(C2CCOCC2)CC1] | (R)-N-(1-(3-(difluoromethyl)-2-fluorophenyl)ethyl)-7-methoxy-6-(1-(tetrahydro-2H-pyran-4-yl)piperidin-4-yl)pyrido[2,3-d]pyrimidin-4-amine | 516.5 |
| 417 | 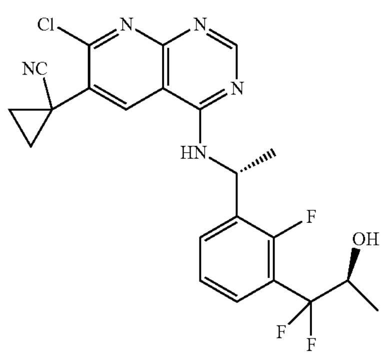 [SMILES: C[C@H](O)C(F)(F)c1cccc([C@@H](C)Nc2ncnc3nc(Cl)c(C4(C#N)CC4)cc23)c1F] | 1-(7-chloro-4-(((R)-1-(3-((S)-1,1-difluoro-2-hydroxypropyl)-2-fluorophenyl)ethyl)amino)pyrido[2,3-d]pyrimidin-6-yl)cyclopropane-1-carbonitrile | 462.3 |
| 418 | 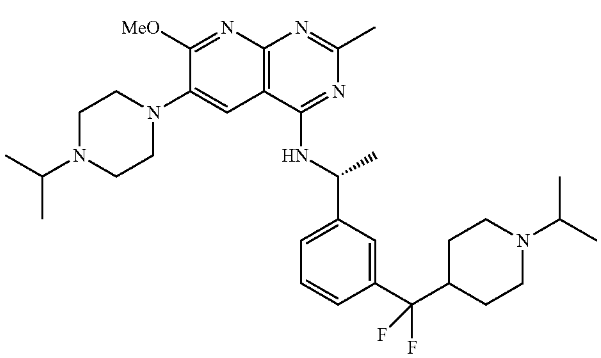 [SMILES: COc1nc2nc(C)nc(N[C@H](C)c3cccc(C(F)(F)C4CCN(C(C)C)CC4)c3)c2cc1N1CCN(C(C)C)CC1] | (R)-N-(1-(3-(difluoro(1-isopropylpiperidin-4-yl)methyl)phenyl)ethyl)-6-(4-isopropylpiperazin-1-yl)-7-methoxy-2-methylpyrido[2,3-d]pyrimidin-4-amine | 596 |

TABLE 1-continued

| Compound | Structure | Name | [M + H]+ |
|---|---|---|---|
| 419 | 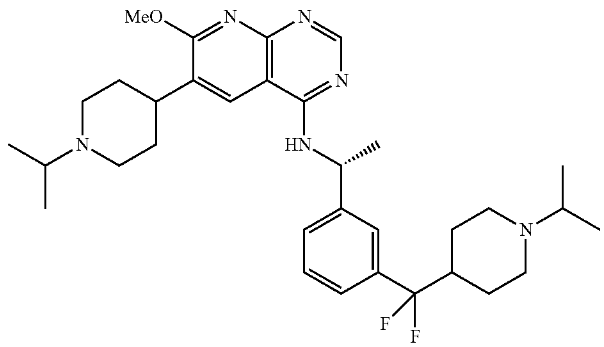 [SMILES: COc1nc2ncnc(N[C@H](C)c3cccc(C(F)(F)C4CCN(C(C)C)CC4)c3)c2cc1C1CCN(C(C)C)CC1] | (R)-N-(1-(3-(difluoro(1-isopropylpiperidin-4-yl)methyl)phenyl)ethyl)-6-(1-isopropylpiperidin-4-yl)-7-methoxypyrido[2,3-d]pyrimidin-4-amine | 580 |
| 420 | 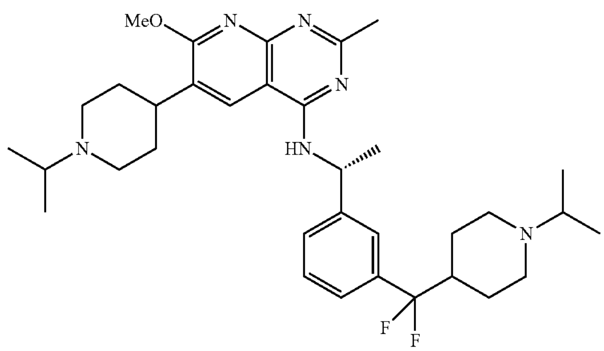 [SMILES: COc1nc2nc(C)nc(N[C@H](C)c3cccc(C(F)(F)C4CCN(C(C)C)CC4)c3)c2cc1C1CCN(C(C)C)CC1] | (R)-N-(1-(3-(difluoro(1-isopropylpiperidin-4-yl)methyl)phenyl)ethyl)-6-(1-isopropylpiperidin-4-yl)-7-methoxy-2-methylpyrido[2,3-d]pyrimidin-4-amine | 595 |
| 421 | 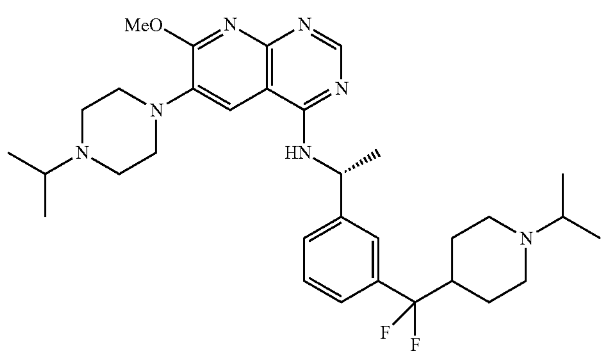 [SMILES: COc1nc2ncnc(N[C@H](C)c3cccc(C(F)(F)C4CCN(C(C)C)CC4)c3)c2cc1N1CCN(C(C)C)CC1] | (R)-N-(1-(3-(difluoro(1-isopropylpiperidin-4-yl)methyl)phenyl)ethyl)-6-(4-isopropylpiperazin-1-yl)-7-methoxypyrido[2,3-d]pyrimidin-4-amine | 582 |
| 422 | 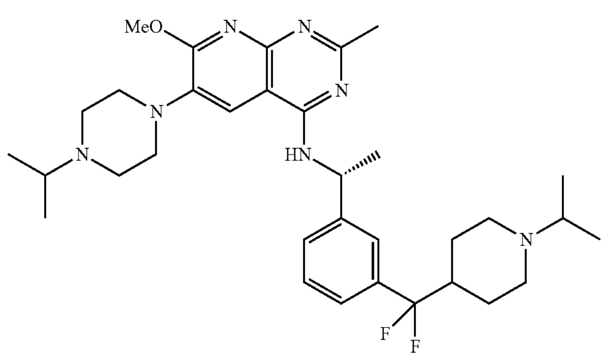 [SMILES: COc1nc2nc(C)nc(N[C@H](C)c3cccc(C(F)(F)C4CCN(C(C)C)CC4)c3)c2cc1N1CCN(C(C)C)CC1] | (R)-N-(1-(3-(difluoro(1-isopropylpiperidin-4-yl)methyl)phenyl)ethyl)-6-(4-isopropylpiperazin-1-yl)-7-methoxy-2-methylpyrido[2,3-d]pyrimidin-4-amine | 596 |

TABLE 1-continued

| Compound | Structure | Name | [M + H]+ |
|---|---|---|---|
| 423 | 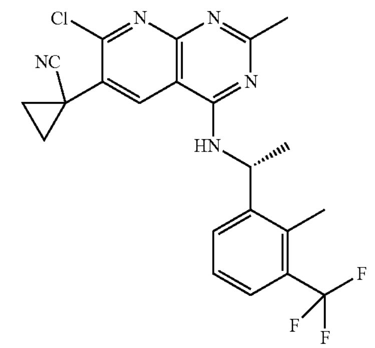 [SMILES: Cc1nc(N[C@H](C)c2cccc(C(F)(F)F)c2C)c2cc(C3(C#N)CC3)c(Cl)nc2n1] | (R)-1-(7-chloro-2-methyl-4-((1-(2-methyl-3-(trifluoromethyl)phenyl)ethyl)amino)pyrido[2,3-d]pyrimidin-6-yl)cyclopropane-1-carbonitrile | 446.2 |
| 424 | 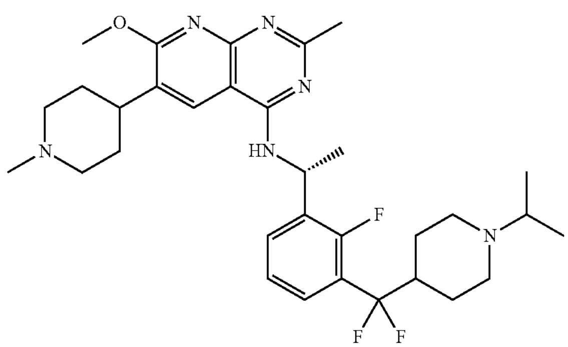 [SMILES: COc1nc2nc(C)nc(N[C@H](C)c3cccc(C(F)(F)C4CCN(C(C)C)CC4)c3F)c2cc1C1CCN(C)CC1] | (R)-N-(1-(3-(difluoro(1-isopropylpiperidin-4-yl)methyl)-2-fluorophenyl)ethyl)-7-methoxy-2-methyl-6-(1-methylpiperidin-4-yl)pyrido[2,3-d]pyrimidin-4-amine | 585.5 |
| 425 | 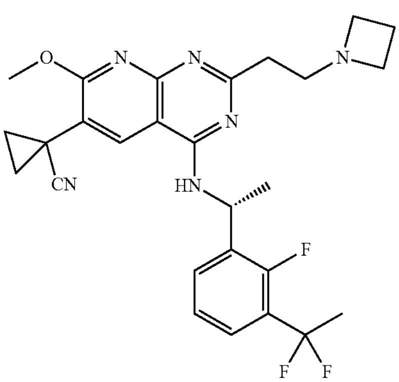 [SMILES: COc1nc2nc(CCN3CCC3)nc(N[C@H](C)c3cccc(C(C)(F)F)c3F)c2cc1C1(C#N)CC1] | (R)-1-(2-(2-(azetidin-1-yl)ethyl)-4-((1-(3-(1,1-difluoroethyl)-2-fluorophenyl)ethyl)amino)-7-methoxypyrido[2,3-d]pyrimidin-6-yl)cyclopropane-1-carbonitrile | 511.4 |
| 426 | 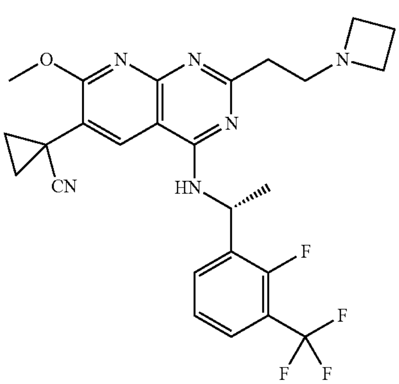 [SMILES: COc1nc2nc(CCN3CCC3)nc(N[C@H](C)c3cccc(C(F)(F)F)c3F)c2cc1C1(C#N)CC1] | (R)-1-(2-(2-(azetidin-1-yl)ethyl)-4-((1-(2-fluoro-3-(trifluoromethyl)phenyl)ethyl)amino)-7-methoxypyrido[2,3-d]pyrimidin-6-yl)cyclopropane-1-carbonitrile | 515.4 |

TABLE 1-continued

| Compound | Structure | Name | [M + H]+ |
|---|---|---|---|
| 427 | 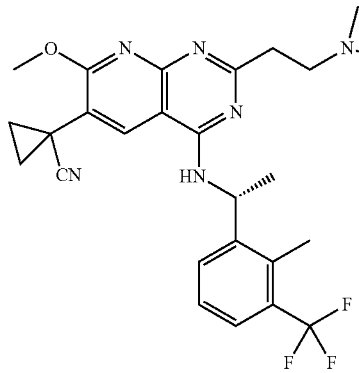 | (R)-1-(2-(2-(azetidin-1-yl)ethyl)-7-methoxy-4-((1-(2-methyl-3-(trifluoromethyl)phenyl)ethyl)amino)pyrido[2,3-d]pyrimidin-6-yl)cyclopropane-1-carbonitrile | 511.4 |

Example 2: Ras Sequence

```
Human K-Ras4b (SEQ ID NO. 1):
  1 MTEYKLVVVG AGGVGKSALT IQLIQNHFVD EYDPTIEDSY
    RKQVVIDGET
 51 CLLDILDTAG QEEYSAMRDQ YMRTGEGFLC VFAINNTKSF
    EDIHHYREQI
101 KRVKDSEDVP MVLVGNKCDL PSRTVDTKQA QDLARSYGIP
    FIETSAKTRQ
151 GVDDAFYTLV REIRKHKEKM SKDGKKKKKK SKTKCVIM
Human SOS1 (SEQ ID NO. 3):
  1 MQAQQLPYEF FSEENAPKWR GLLVPALKKV QGQVHPTLES
    NDDALQYVEE
 51 LILQLLNMLC QAQPRSASDV EERVQKSFPH PIDKWAIADA
    QSAIEKRKRR
101 NPLSLPVEKI HPLLKEVLGY KIDHQVSVYI VAVLEYISAD
    ILKLVGNYVR
151 NIRHYEITKQ DIKVAMCADK VLMDMFHQDV EDINILSLTD
    EEPSTSGEQT
201 YYDLVKAFMA EIRQYIRELN LIIKVFREPF VSNSKLFSAN
    DVENIFSRIV
251 DIHELSVKLL GHIEDTVEMT DEGSPHPLVG SCFEDLAEEL
    AFDPYESYAR
301 DILRPGFHDR FLSQLSKPGA ALYLQSIGEG FKEAVQYVLP
    RLLLAPVYHC
351 LHYFELLKQL EEKSEDQEDK ECLKQAITAL LNVQSGMEKI
    CSKSLAKRRL
401 SESACRFYSQ QMKGKQLAIK KMNEIQKNID GWEGKDIGQC
    CNEFIMEGTL
451 TRVGAKHERH IFLFDGLMIC CKSNHGQPRL PGASNAEYRL
    KEKFFMRKVQ
501 INDKDDTNEY KHAFEIILKD ENSVIFSAKS AEEKNNWMAA
    LISLQYRSTL
551 ERMLDVTMLQ EEKEEQMRLP SADVYRFAEP DSEENIIFEE
    NMQPKAGIPI
601 IKAGTVIKLI ERLTYHMYAD PNFVRTFLTT YRSFCKPQEL
    LSLIIERFEI
651 PEPEPTEADR IAIENGDQPL SAELKRFRKE YIQPVQLRVL
    NVCRHWVEHH
701 FYDFERDAYL QRMEEFIGT VRGKAMKKWV ESITKIIQRK
    KIARDNGPGH
751 NITFQSSPPT VEWHISRPGH IETFDLLTLH PIEIARQLTL
    LESDLYRAVQ
801 PSELVGSVWT KEDKEINSPN LLKMIRHTTN LTLWFEKCIV
    ETENLEERVA
851 VVSRIIEILQ VFQELNNFNG VLEVVSAMNS SPVYRLDHTF
    EQIPSRQKKI
901 LEEAHELSED HYKKYLAKLR SINPPCVPFF GIYLTNILKT
    EEGNPEVLKR
951 HGKELINFSK RRKVAEITGE IQQYQNQPYC LRVESDIKRF
    FENLNPMGNS
1001 MEKEFTDYLF NKSLEIEPRN PKPLPRFPKK YSYPLKSPGV
    RPSNPRPGTM
1051 RHPTPLQQEP RKISYSRIPE SETESTASAP NSPRTPLTPP
    PASGASSTTD
```

```
1101  VCSVFDSDHS SPFHSSNDTV FIQVTLPHGP RSASVSSISL
      TKGTDEVPVP
1151  PPVPPRRRPE SAPAESSPSK IMSKHLDSPP AIPPRQPTSK
      AYSPRYSISD
1201  RTSISDPPES PPLLPPREPV RTPDVFSSSP LHLQPPPLGK
      KSDHGNAFFP
1251  NSPSPFTPPP PQTPSPHGTR RHLPSPPLTQ EVDLHSIAGP
      PVPPRQSTSQ
1301  HIPKLPPKTY KREHTHPSMH RDGPPLLENA HSS
Human SOS2 (SEQ ID NO. 5):
   1  MQQAPQPYEF FSEENSPKWR GLLVSALRKV QEQVHPTLSA
      NEESLYYIEE
  51  LIFQLLNKLC MAQPRTVQDV EERVQKTFPH PIDKWAIADA
      QSAIEKRKRR
 101  NPLLLPVDKI HPSLKEVLGY KVDYHVSLYI VAVLEYISAD
      ILKLAGNYVF
 151  NIRHYEISQQ DIKVSMCADK VLMDMFDQDD IGLVSLCEDE
      PSSSGELNYY
 201  DLVRTEIAEE RQYLRELNMI IKVFREAFLS DRKLFKPSDI
      EKIFSNISDI
 251  HELTVKLLGL IEDTVEMTDE SSPHPLAGSC FEDLAEEQAF
      DPYETLSQDI
 301  LSPEFHEHFN KLMARPAVAL HFQSIADGFK EAVRYVLPRL
      MLVPVYHCWH
 351  YFELLKQLKA CSEEQEDREC LNQAITALMN LQGSMDRIYK
      QYSPRRRPGD
 401  PVCPFYSHQL RSKHLAIKKM NEIQKNIDGW EGKDIGQCCN
      EFIMEGPLTR
 451  IGAKHERHIF LFDGLMISCK PNHGQTRLPG YSSAEYRLKE
      KFVMRKIQIC
 501  DKEDTCEHKH AFELVSKDEN SIIFAAKSAE EKNNWMAALI
      SLHYRSTLDR
 551  MLDSVLLKEE NEQPLRLPSP EVYRFVVKDS EENIVFEDNL
      QSRSGIPIIK
 601  GGTVVKLIER LTYHMYADPN FVRTFLTTYR SFCKPQELLS
      LLIERFEIPE
 651  PEPTDADKLA IEKGEQPISA DLKRFRKEYV QPVQLRILNV
      FRHWVEHHFY
 701  DFERDLELLE RLESFISSVR GKAMKKWVES IAKIIRRKKQ
      AQANGVSHNI
 751  TFESPPPPIE WHISKPGQFE TFDLMTLHPI EIARQLTLLE
      SDLYRKVQPS
 801  ELVGSVWTKE DKEINSPNLL KMIRHTTNLT LWFEKCIVEA
      ENFEERVAVL
 851  SRIIEILQVF QDLNNFNGVL EIVSAVNSVS VYRLDHTFEA
      LQERKRKILD
 901  EAVELSQDHF KKYLVKLKSI NPPCVPFFGI YLTNILKTEE
      GNNDFLKKKG
 951  KDLINFSKRR KVAEITGEIQ QYQNQPYCLR IEPDMRRFFE
      NLNPMGSASE
1001  KEFTDYLFNK SLEIEPRNCK QPPRFPRKST FSLKSPGIRP
      NTGRHGSTSG
1051  TLRGHPTPLE REPCKISFSR IAETELESTV SAPTSPNTPS
      TPPVSASSDL
1101  SVFLDVDLNS SCGSNSIFAP VLLPHSKSFF SSCGSLHKLS
      EEPLIPPPLP
1151  PRKKFDHDAS NSKGNMKSDD DPPAIPPRQP PPPKVKPRVP
      VPTGAFDGPL
1201  HSPPPPPPRD PLPDTPPPVP LRPPEHFINC PFNLQPPPLG
      HLHRDSDWLR
1251  DISTCPNSPS TPPSTPSPRV PRRCYVLSSS QNNLAHPPAP
      PVPPRQNSSP
1301  HLPKLPPKTY KRELSHPPLY RLPLLENAET PQ
```

Example 3: Protein Expression

DNA expression constructs encoding one or more protein sequences of interest (e.g., Kras fragments thereof, mutant variants thereof, etc.) and its corresponding DNA sequences are optimized for expression in *E. coli* and synthesized by, for example, the GeneArt Technology at Life Technologies. In some cases, the protein sequences of interest are fused with a tag (e.g., glutathione S-transferase (GST), histidine (His), or any other affinity tags) to facilitate recombinant expression and purification of the protein of interest. Such tag can be cleaved subsequent to purification. Alternatively, such tag may remain intact to the protein of interest and may not interfere with activities (e.g., target binding and/or phosphorylation) of the protein of interest A resulting expression construct is additionally encoded with (i) att-site sequences at the 5' and 3' ends for subcloning into various destination vectors using, for example, the Gateway Technology, as well as (ii) a Tobacco Etch Virus (TEV) protease site for proteolytic cleavage of one or more tag sequences. The applied destination vectors can be a pET vector series from Novagen (e.g., with ampicillin resistance gene), which provides an N-terminal fusion of a GST-tag to the integrated gene of interest and/or a pET vector series (e.g., with ampicillin resistance gene), which provides a N-terminal fusion of a HIS-tag to the integrated gene. To generate the final expression vectors, the expression construct of the protein of interest is cloned into any of the applied destination ventors. The expression vectors are transformed into *E. coli* strain, e.g., BL21 (DE3). Cultivation of the transformed strains for expression is performed in 10 L and 1 L fermenter. The cultures are grown, for example, in Terrific Broth media (MP Biomedicals, Kat. #1 13045032) with 200 ug/mL ampicillin at a temperature of 37° C. to a density of 0.6 (OD600), shifted to a temperature of −27° C. (for K-Ras expression vectors) induced for expression with 100 mM IPTG, and further cultivated for 24 hours. After cultivation, the transformed *E. coli* cells are harvested by centrifugation and the resulting pellet is suspended in a lysis buffer, as provided below, and lysed by passing three-times through a high pressure device. The lysate is centrifuged (49000 g, 45 min, 4° C.) and the supernatant is used for further purification.

Example 4: Ras Protein Purification

A Ras (e.g., K-Ras wildtype or a mutant such as K-Ras G12D, K-Ras G12V or K-RasG12C) construct or a variant thereof is tagged with GST. *E. coli* culture from a 10 L fermenter is lysed in lysis buffer (50 mM Tris HCl 7.5, 500 mM NaCl, 1 mM DTT, 0,5% CHAPS, Complete Protease Inhibitor Cocktail-(Roche)). As a first chromatography step, the centrifuged lysate is incubated with 50 mL Glutathione Agarose 4B (Macherey-Nagel; 745500.100) in a spinner flask (16 h, 100). The Glutathione Agarose 4B loaded with protein is transferred to a chromatography column connected to a chromatography system, e.g., an Akta chromatography system. The column is washed with wash buffer (50 mM Tris HCl 7.5, 500 mM NaCl, 1 mM DTT) and the bound protein is eluted with elution buffer (50 mM Tris HCl 7.5, 500 mM NaCl, 1 mM DTT, 15 mM Glutathione). The main fractions of the elution peak (monitored by OD280) is pooled. For further purification by size-exclusion chromatography, the above eluate volume is applied to a column Superdex 200 HR prep grade (GE Healthcare) and the resulting peak fractions of the eluted fusion protein is collected. Native mass spectrometry analyses of the final purified protein construct can be performed to assess its homogeneous load with GDP.

Example 5: SOS Purification

A SOS construct or a variant thereof is His10-tagged (SEQ ID NO: 6). *E. coli* cultures is induced in a fermenter, harvested, and lysed in lysis buffer, for example, in 25 mM Tris HCl 7.5, 500 mM NaCl, 20 mM Imidazol, Complete EDTA-free (Roche)). For immobilized metal ion affinity chromatography (IMAC), the centrifuged lysate (50 000×g, 45 min, 40) is incubated with 30 mL Ni-NTA (Macherey-Nagel; #745400.100) in a spinner flask (16 h, 40) and subsequently transferred to a chromatography column connected to a chromatography system, e.g., an Akta chromatography system. The column is rinsed with wash buffer, e.g., in 25 mM Tris HCl 7.5, 500 mM NaCl, 20 mM Imidazol and the bound protein is eluted with a linear gradient (0-100%) of elution buffer (25 mM Tris HCl 7.5, 500 mM NaCl, 300 mM Imidazol). The main fractions of the elution peak (monitored by OD280) containing homogenous His10-hSOS is pooled.

Example 6: Ras-SOS Interaction Assay

The ability of any compound of the present disclosure to reduce a Ras protein signaling output by, e.g., interfering or disrupting interaction (or binding) between SOS1 and a Ras protein can be assessed in vitro. For example, the equilibrium interaction of human SOS1 (hSOS1) with human wildtype Kras or K-Ras mutant (e.g., hK-Ras G12C mutant, or hK-RasG12C) can be assessed as a proxy or an indication for a subject compound's ability to inhibit SOS. Detection of such interaction is achieved by measuring homogenous time-resolved fluorescence resonance energy transfer (HTRF) from (i) a fluorescence resonance energy transfer (FRET) donor (e.g., antiGST-Europium) that is bound to GST-tagged K-RasG12C to (ii) a FRET acceptor (e.g., anti-6His-XL665) bound to a His-tagged hSOS1.

The assay buffer can contain 5 mM HEPES pH 7.4, 150 mM NaCl, 10 mM EDTA, 1 mM DTT, 0.05% BSA, 0.0025% (v/v) Igepal and 100 mM KF. A Ras working solution is prepared in assay buffer containing typically 10 nM of the protein construct (e.g., GST-tagged hK-RasG12C) and 2 nM of the FRET donor (e.g., antiGST-Eu(K) from Cisbio, France). A SOS1 working solution is prepared in assay buffer containing typically 10 nM of the protein construct (e.g., His-hSOS1) and 10 nM of the FRET acceptor (e.g., anti-6His-XL665 from Cisbio, France). An inhibitor control solution is prepared in assay buffer containing 10 nM of the FRET acceptor without the SOS1 protein.

A fixed reaction mixture with or without test compound is transferred into a 384-well plate. Ras working solution is added to all wells of the test plate. SOS1 working solution is added to all wells except for those that are subsequently filled the inhibitor control solution. After approximately 60 min incubation, the fluorescence is measured with a M1000Pro plate reader (Tecan) using HTRF detection (excitation 337 nm, emission 1: 620 nm, emission 2: 665 nm). Compounds are tested in duplicates at different concentrations (for example, 10 µM, 2.5 µM, 0.63 µM, 0.16 µM, 0.04 µM, 0.01 µM test compound). The ratiometric data (i.e., emission 2 divided by emission 1) is used to calculate IC50 values against SOS1 using GraphPad Prism (GraphPad software).

Table 2 below shows the resulting IC50 values of the compounds exemplified in Table 1 against SOS1 using the Ras-SOS interaction assay as described above, wherein K-RasG13D is utilized. The results demonstrate that compounds disclosed herein are capable of reducing Ras protein signaling by inhibiting SOS1-mediated signaling. Many of the exemplified compounds are potent SOS inhibitors, exhibiting an IC50 value against SOS1 less than about 500 nM, 400 nM, 300 nM, 200 n, 100 nM, 80 nM, 60 nM, 50 nM, 40 nM, 30 nM, 20 nM, or even less than 10 nM. For example, compounds No. 102, 103, 104, 105, 109, 112, 113, 114, 115, 116, 117, 118, 119, 120, 121, 122, 123, 124, 125, 126, 127, 128, 129, 130, 131, 132, 133, 134, 135, 136, 137, 138, 139, 141, 142, 143, 145, 146, 147, 148, 149, 150, 151, 152, 153, 154, 155, 156, 157, 159, 160, 161, 162, 163, 164, 165, 166, 167, 169, 171, 172, 173, 174, 175, 176, 177, 178, 179, 180, 181, 182, 183, 187, 188, 190, 191, 192, 193, 194, 195, 196, 197, 198, 199, 200, 201, 202, 203, 204, 205, 206, 207, 209, 210, 211, 212, 214, 215, 216, 217, 218, 219, 220, 221, 222, 223, 224, 227, 229, 231, 232, 233, 234, 235, 236, 238, 239, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 277, 285, 287, 288, 289, 290, 291, 292, 293, 294, 295, 297, 299, 301, 302, 303, 304, 305, 307, 308, 309, 312, 313, 314, 316, 317, 318, 320, 321, 322, 323, 324, 325, 326, 327, 328, 329, 330, 331, 332, 333, 334, 336, 337, 338, 339, 340, 341, 342, 343, 344, 345, 346, 347, 348, 349, 350, 351, 352, 353, 355, 356, 357, 358, 359, 360, 361, 362, 363, 365, 366, 367, 368, 369, 370, 371, 373, 374, 375, 376, 378, 379, 380, 381, 382, 383, 384, 385, 386, 387, 388, 389, 390, 391, 392, 393, 394, 395, 396, 397, 399, 401, 404, 405, 406, 407, 410, 411, 412, 413, 414, 415, 416, 417, 418, 419, 420, 421, 424, 425, 426, and 427 exhibit IC10 values less than 50 nM, 40 nM, 30 nM, 20 nM, or 10 nM.

Table 2 below shows the resulting IC values of the compounds exemplified in Table 1 against SOS using the Ras-SOS interaction assay described herein.

TABLE 2

| Compound | IC50 inhibition of SOS |
|---|---|
| 101 | A |
| 102 | A |
| 103 | A |
| 104 | A |
| 105 | A |
| 106 | A |
| 107 | A |
| 108 | A |
| 109 | A |
| 110 | A |
| 111 | B |
| 112 | A |
| 113 | A |
| 114 | A |
| 115 | A |
| 116 | A |
| 117 | A |
| 118 | A |
| 119 | A |
| 120 | A |
| 121 | A |
| 122 | A |
| 123 | A |
| 124 | A |
| 125 | A |
| 126 | A |
| 127 | A |
| 128 | A |
| 129 | A |
| 130 | A |
| 131 | A |
| 132 | A |
| 133 | A |
| 134 | A |
| 135 | A |
| 136 | A |
| 137 | A |
| 138 | A |
| 139 | A |
| 140 | B |
| 141 | A |
| 142 | A |
| 143 | A |
| 144 | B |
| 145 | A |
| 146 | A |
| 147 | A |
| 148 | A |
| 149 | A |
| 150 | A |
| 151 | A |
| 152 | A |
| 153 | A |
| 154 | A |
| 155 | A |
| 156 | A |
| 157 | A |
| 158 | A |
| 159 | A |
| 160 | A |
| 161 | A |
| 162 | A |
| 163 | A |
| 164 | A |
| 165 | A |
| 166 | A |
| 167 | A |
| 168 | B |
| 169 | A |
| 170 | A |
| 171 | A |
| 172 | A |
| 173 | A |
| 174 | A |
| 175 | A |
| 176 | A |
| 177 | A |
| 178 | A |
| 179 | A |
| 180 | A |
| 181 | A |
| 182 | A |
| 183 | A |
| 184 | A |
| 185 | B |
| 186 | A |
| 187 | A |
| 188 | A |
| 189 | A |
| 190 | A |
| 191 | A |
| 192 | A |
| 193 | A |
| 194 | A |
| 195 | A |
| 196 | A |
| 197 | A |
| 198 | A |
| 199 | A |
| 200 | A |
| 201 | A |
| 202 | A |
| 203 | A |
| 204 | A |
| 205 | A |
| 206 | A |
| 207 | A |
| 208 | B |
| 209 | A |
| 210 | A |
| 211 | A |
| 212 | A |
| 213 | A |
| 214 | A |
| 215 | A |
| 216 | A |
| 217 | A |
| 218 | A |
| 219 | A |
| 220 | A |
| 221 | A |
| 222 | A |
| 223 | A |
| 224 | A |
| 225 | B |
| 226 | A |
| 227 | A |
| 228 | B |
| 229 | A |
| 230 | B |
| 231 | A |
| 232 | A |
| 233 | A |
| 234 | A |
| 235 | A |
| 236 | A |
| 237 | B |
| 238 | A |
| 239 | A |
| 240 | B |
| 241 | A |
| 242 | A |

TABLE 2-continued

| Compound | IC50 inhibition of SOS |
|---|---|
| 243 | A |
| 244 | A |
| 245 | A |
| 246 | A |
| 247 | A |
| 248 | A |
| 249 | A |
| 250 | A |
| 251 | A |
| 252 | A |
| 253 | A |
| 254 | A |
| 255 | A |
| 256 | A |
| 257 | A |
| 258 | A |
| 259 | A |
| 260 | A |
| 261 | A |
| 262 | A |
| 263 | A |
| 264 | A |
| 265 | A |
| 266 | A |
| 267 | A |
| 268 | A |
| 269 | A |
| 270 | A |
| 271 | A |
| 272 | A |
| 273 | A |
| 274 | B |
| 275 | B |
| 276 | A |
| 277 | A |
| 278 | A |
| 279 | B |
| 280 | B |
| 281 | B |
| 282 | B |
| 283 | A |
| 284 | A |
| 285 | A |
| 286 | B |
| 287 | A |
| 288 | A |
| 289 | A |
| 290 | A |
| 291 | A |
| 292 | A |
| 293 | A |
| 294 | A |
| 295 | A |
| 296 | A |
| 297 | A |
| 298 | B |
| 299 | A |
| 300 | A |
| 301 | A |
| 302 | A |
| 303 | A |
| 304 | A |
| 305 | A |
| 306 | B |
| 307 | A |
| 308 | A |
| 309 | A |
| 310 | A |
| 311 | B |
| 312 | A |
| 313 | A |
| 314 | A |
| 315 | A |
| 316 | A |
| 317 | A |
| 318 | A |
| 319 | B |
| 320 | A |
| 321 | A |
| 322 | A |
| 323 | A |
| 324 | A |
| 325 | A |
| 326 | A |
| 327 | A |
| 328 | A |
| 329 | A |
| 330 | A |
| 331 | A |
| 332 | A |
| 333 | A |
| 334 | A |
| 335 | A |
| 336 | A |
| 337 | A |
| 338 | A |
| 339 | A |
| 340 | A |
| 341 | A |
| 342 | A |
| 343 | A |
| 344 | A |
| 345 | A |
| 346 | A |
| 347 | A |
| 348 | A |
| 349 | A |
| 350 | A |
| 351 | A |
| 352 | A |
| 353 | A |
| 354 | A |
| 355 | A |
| 356 | A |
| 357 | A |
| 358 | A |
| 359 | A |
| 360 | A |
| 361 | A |
| 362 | A |
| 363 | A |
| 364 | B |
| 365 | A |
| 366 | A |
| 367 | A |
| 368 | A |
| 369 | A |
| 370 | A |
| 371 | A |
| 372 | A |
| 373 | A |
| 374 | A |
| 375 | A |
| 376 | A |
| 377 | A |
| 378 | A |
| 379 | A |
| 380 | A |
| 381 | A |
| 382 | A |
| 383 | A |
| 384 | A |
| 385 | A |
| 386 | A |
| 387 | A |
| 388 | A |
| 389 | A |
| 390 | A |
| 391 | A |
| 392 | A |
| 393 | A |
| 394 | A |

TABLE 2-continued

| Compound | IC50 inhibition of SOS |
|---|---|
| 395 | A |
| 396 | A |
| 397 | A |
| 398 | B |
| 399 | A |
| 400 | B |
| 401 | A |
| 402 | A |
| 403 | B |
| 404 | A |
| 405 | A |
| 406 | A |
| 407 | A |
| 408 | B |
| 409 | B |
| 410 | A |
| 411 | A |
| 412 | A |
| 413 | A |
| 414 | A |
| 415 | A |
| 416 | A |
| 417 | A |
| 418 | A |
| 419 | A |
| 420 | A |
| 421 | A |
| 422 | A |
| 423 | B |
| 424 | A |
| 425 | A |
| 426 | A |
| 427 | A | where 'A' means IC50 <100 nM, and 'B' means IC50 >100 nM but less than 1 uM.

Example 7: ERK Phosphorylation Assay

ERK phosphorylation assay is used to examine the potency with which compounds disclosed herein inhibit the SOS1-mediated signaling and hence Ras signaling output in a Kras mutant cancer cell line. MIA PaCa-2 cells (ATCC CRL-1420) expressing K-Ras G12C is grown in DMEM/Ham's F12 medium supplemented with 10% fetal calf serum, glutamine and ~2.5% horse serum. Alternatively, other cell lines with aberrant Ras signaling output can be utilized. Non-limiting exemplary cell lines include NCI-H358 and H1975. Cells are plated in 96-well plates at a concentration of 40,000 cells/well and allowed to attach for at least 8 hours. Following, diluted solutions of test inhibitor compounds are added to the cell culture. After ~2 hours of incubation, the medium is removed and lysis buffer from AlphaLISA® SureFire® Ultra™ p-ERK 1/2 (Thr202/Tyr204) assay kit (Perkin Elmer ALSU-PERK-A10K) is added to the cells. The plate is agitated for 10 min at room temperature and 10 µL of the lysate is transferred to a 384-well Optiplate™ (Perkin Elmer) for assay. Thereafter ~5 µL of Acceptor Mix from the p-ERK AlphaLISA assay kit is added to wells and plate is sealed with adhesive film. The samples are incubated for one hour at room temperature. Following, 5 µL of Donor Mix is added to the wells and plate is re-sealed with adhesive film, and incubated for one hour at room temperature. The plate is then read on a multimode microplate reader (e.g., SPARK©Tecan) equipped with Alpha detection module. The data can be fitted to four-parameter dose-response curve using Prism version 9 (GraphPad) to calculate an IC50 for the inhibition of ERK phosphorylation. Compounds disclosed herein when assessed in this ERK phosphorylation assay exhibit IC50 values less than about 1 uM, about 500 nM, about 200 nM, about 100 nM, or 50 nM. Non-limiting exemplary compounds from Table 1 that exhibit such low IC50 values include compound nos. 355, 332, 366, 216, 264, 356, 266, in an ERK phosphorylation assay utilizing either MIA PaCa-2 cells (ATCC CRL-1420) or EGFR mutant cell line (NCI-H1975 (ATCC CRL-5908)).

Example 8: Ras-SOS Cellular Growth Inhibition Assay

The ability of any compound of the present disclosure to inhibit SOS1-mediated signaling and hence Ras protein signaling can be demonstrated by inhibiting growth of a given Kras mutant cell line.
Growth of Cells with K-Ras G12C Mutation
MIA PaCa-2 (ATCC CRL-1420) and NCI-H1792 (ATCC CRL-5895) cell lines comprise a G12C mutation can be used to assess Ras cellular signaling in vitro, e.g., in response to a subject compound of the present disclosure. This cellular assay can also be used to discern selective inhibition of a subject compounds against certain types of Kras mutants, e.g., more potent inhibition against KrasG12D relative to KrasG12C mutant, by using MIA PaCa-2 (G12C driven tumor cell line) as a comparison. Cell culture medium (comprising, for example, MIA PaCa-2 cells) is prepared with DMEM/Ham's F12 (e.g., with stable Glutamine, 10% FCS, and 2.5% Horse Serum. NCI-H1792 culture medium is prepared with RPMI 1640 (e.g., with stable Glutamine) and 10% FCS. A CellTiter-Glo (CTG) luminescent based assay (Promega) is used to assess growth of the cells, as a measurement of the ability of the compounds herein to inhibit Ras signaling in the cells. The cells (e.g., 800-1200 per well) are seeded in their respective culture medium in standard tissue culture-treated ultra-low attachment surface 96-well format plates (Corning Costar #3474). The day after plating, cells are treated with a dilution series (e.g., a 9 point 3-fold dilution series) of the compounds herein (e.g., approximately 125 µl final volume per well). Cell viability can be monitored (e.g., approximately 5 days later) according to the manufacturer's recommended instructions, where the CellTiter-Glo reagent is added (e.g., approximately 65 µl), vigorously mixed, covered, and placed on a plate shaker (e.g., approximately for 20 min) to ensure sufficient cell lysis prior to assessment of luminescent signal. The IC50 values are determined using the four-parameter fit. The resulting IC50 value is a measurement of the ability of the compounds herein to reduce cell growth of Ras-driven cells as representative tumor cells. See Table 3. The results demonstrate that the subject compounds are effective in inhibiting growth of tumor cells including cells comprising one or more Kras mutations, e.g., Ras-driven tumor cells carrying KrasG12C mutation. Many of the exemplified compounds are potent SOS1 inhibitors, exhibiting SOS1-mediated signaling, capable of reducing cell growth with an IC50 value less than about 1 uM, 500 nM, 400 nM, 300 nM, 200 nM, 100 nM, 80 nM, 60 nM, 50 nM, 40 nM, 30 nM, 20 nM, 10 nM or even less. For example, compounds No. 102, 103, 104, 105, 109, 112, 113, 115, 118, 119, 120, 123, 125, 127, 128, 130, 131, 132, 133, 134, 136, 137, 138, 139, 141, 142, 143, 145, 146, 148, 149, 150, 153, 154, 156, 157, 159, 161, 163, 164, 166, 169, 170, 174, 175, 176, 177, 178, 179, 180, 181, 182, 190, 193, 194, 195, 196, 197, 198, 199, 202, 204, 205, 206, 209, 210, 211, 212, 214, 215, 216, 218, 219, 220, 221, 222, 223, 224, 232, 233, 236, 238, 239, 240, 242, 243, 244, 247, 248, 256, 257, 258, 259, 260, 261, 263, 264, 265, 266, 267, 268, 269, 270, 271, 273, 283, 287, 288, 289, 291, 292, 293, 294, 295, 304, 305, 307, 308, 312, 313, 314, 322, 324, 325, 327, 328, 329, 330, 331, 332, 333, 334, 336, 337, 341, 345, 346, 347, 349, 350, 351, 352, 353, 354, 355, 356, 359, 360, 363, 366, 372, 373, 374, 375, 376, 377, 378, 379, 380, 381, 383, 384, 385, 386, 387, 388, 389, 390, 391, 392, 393, 394, 395, 396, 397, 400, 402, 406, 410, 411, 412, 413, 415, 418, 419, 420, and 421 exhibit IC50 values less than 500 nM, 400 nM, 300 nM, 200 nM, 100 nM, 80 nM, 60 nM, 50 nM, 40 nM, 30 nM, 20 nM, or even less than 10 nM, in inhibiting MIA PaCa-2 cell growth.

Example 9: EGFR-SOS Cellular Inhibition Assay

The ability of any compound of the present disclosure to inhibit SOS1-mediated signaling and hence Ras protein signaling can be demonstrated by inhibiting growth of a given EGFR mutant cells.
Growth of Cells with EGFR T790ML858R Double Mutation NCI-H1975 (ATCC CRL-5908) cell line comprises an EGFR T790M L858R double mutation can be used to assess EGFR cellular signaling in vitro, e.g., in response to a subject compound of the present invention. NCI-H1975 culture medium is prepared with RPMI 1640 (e.g., with stable Glutamine) and 10% FCS. A CellTiter-Glo (CTG) luminescent based assay (Promega) is used to assess growth of the cells, as a measurement of the ability of the compounds herein to inhibit EGFR signaling in the cells. The cells (e.g., 800-1200 per well) are seeded in their respective culture medium in standard tissue culture-treated ultra-low attachment surface 96-well format plates (Corning Costar #3474). The day after plating, cells are treated with a dilution series (e.g., a 9 point 3-fold dilution series) of the compounds herein (e.g., approximately 125 µl final volume per well). Cell viability can be monitored (e.g., approximately 5 days later) according to the manufacturer's recommended instructions, where the CellTiter-Glo reagent is added (e.g., approximately 65 µl), vigorously mixed, covered, and placed on a plate shaker (e.g., approximately for 20 min) to ensure sufficient cell lysis prior to assessment of luminescent signal. The IC50 values are determined using the four-parameter fit. The resulting IC50 value is a measurement of the ability of the compounds herein to reduce growth of EGFR-driven tumor cells. See Table 3. Many of the exemplified compounds are potent SOS1 inhibitors, capable of reducing cell growth with an IC50 value less than about 1 uM, 500 nM, 400 nM, 300 nM, 200 nM, 100 nM, 80 nM, 60 nM, 50 nM, 40 nM, 30 nM, 20 nM, or even less than 10 nM. For example, compounds No. 102, 103, 104, 105, 109, 112, 113, 117, 118, 119, 120, 125, 126, 127, 130, 131, 132, 133, 134, 136, 138, 139, 141, 142, 143, 145, 146, 147, 148, 149, 150, 151, 153, 154, 156, 157, 159, 160, 161, 162, 163, 164, 165, 166, 169, 170, 171, 172, 173, 174, 175, 176, 177, 179, 180, 181, 182, 183, 184, 188, 190, 193, 196, 197, 198, 199, 200, 202, 204, 205, 206, 207, 209, 210, 211, 212, 214, 215, 216, 217, 218, 219, 220, 221, 222, 223, 224, 226, 232, 233, 234, 235, 236, 238, 239, 240, 242, 243, 244, 247, 248, 249, 251, 256, 257, 258, 259, 260, 261, 262, 263, 264, 265, 266, 267, 268, 269, 270, 271, 272, 273, 277, 283, 287, 288, 289, 291, 292, 293, 294, 295, 297, 301, 302, 303, 304, 305, 308, 309, 312, 313, 315, 316, 317, 320, 321, 322, 323, 324, 325, 326, 327, 328, 329, 330, 331, 332, 333, 334, 336, 337, 338, 339, 341, 342, 343, 345, 346, 347, 348, 349, 350, 351, 352, 353, 354, 355, 356, 359, 360, 361, 362, 363, 364, 365, 366, 367, 368, 372, 374, 375, 376, 377, 378, 379, 381, 383, 384, 385, 386, 387, 388, 389, 390, 391, 392, 393, 394, 395, 397, 405, 406, 409, 410, 411, 412, 413, 414, 415, 417, 418, 419, 420, and 421 exhibit IC50 values less than 500 nM, 400 nM, 300 nM, 200 nM, 100 nM, 80 nM, 60 nM, 50 nM, 40 nM, 30 nM, 20 nM, or even less than 10 nM, in inhibiting growth of NCI-H1975 (ATCC CRL-5908) cell line comprising an EGFR T790M L858R double mutation. Table 3 below shows the resulting IC50 values of the compounds exemplified in Table 1 against SOS1 using the cell proliferation assays described herein.

| CMPD | Bio-Cell-Prolif-3D (MiaPaca2 IC50) [nM] | Bio-Cell-Prolif-3D (H1975 IC50) [nM] |
| --- | --- | --- |
| 101 | +++ | +++ |
| 102 | +++ | +++ |
| 103 | +++ | +++ |
| 104 | +++ | +++ |
| 105 | +++ | +++ |
| 106 | ND | ND |
| 107 | ND | ND |
| 108 | ND | ND |
| 109 | +++ | +++ |
| 110 | +++ | +++ |
| 111 | ND | ND |
| 112 | +++ | +++ |
| 113 | +++ | +++ |
| 114 | +++ | +++ |
| 115 | +++ | +++ |
| 116 | +++ | +++ |
| 117 | +++ | +++ |
| 118 | +++ | +++ |
| 119 | +++ | +++ |
| 120 | +++ | +++ |
| 121 | ND | ND |
| 122 | ND | ND |
| 123 | +++ | +++ |
| 124 | ND | ND |
| 125 | +++ | +++ |
| 126 | +++ | +++ |
| 127 | +++ | +++ |
| 128 | +++ | +++ |
| 129 | +++ | ++ |
| 130 | +++ | +++ |
| 131 | +++ | +++ |
| 132 | +++ | +++ |
| 133 | +++ | +++ |
| 134 | +++ | +++ |
| 135 | +++ | +++ |
| 136 | +++ | +++ |
| 137 | +++ | +++ |
| 138 | +++ | +++ |
| 139 | +++ | +++ |
| 140 | ND | ND |
| 141 | +++ | +++ |
| 142 | +++ | +++ |
| 143 | +++ | +++ |
| 144 | ND | ND |
| 145 | +++ | +++ |
| 146 | +++ | +++ |
| 147 | +++ | +++ |
| 148 | +++ | +++ |
| 149 | +++ | +++ |
| 150 | +++ | +++ |
| 151 | +++ | +++ |
| 152 | +++ | +++ |
| 153 | +++ | +++ |
| 154 | +++ | +++ |
| 155 | +++ | +++ |
| 156 | +++ | +++ |
| 157 | +++ | +++ |
| 158 | +++ | ++ |
| 159 | +++ | +++ |
| 160 | +++ | +++ |
| 161 | +++ | +++ |
| 162 | +++ | +++ |
| 163 | +++ | +++ |
| 164 | +++ | +++ |

-continued

| CMPD | Bio-Cell-Prolif-3D (MiaPaca2 IC50) [nM] | Bio-Cell-Prolif-3D (H1975 IC50) [nM] |
|---|---|---|
| 165 | +++ | +++ |
| 166 | +++ | +++ |
| 167 | ++ | +++ |
| 168 | ND | ND |
| 169 | +++ | +++ |
| 170 | +++ | +++ |
| 171 | +++ | +++ |
| 172 | ++ | +++ |
| 173 | ++ | +++ |
| 174 | +++ | +++ |
| 175 | +++ | +++ |
| 176 | +++ | +++ |
| 177 | +++ | +++ |
| 178 | +++ | ++ |
| 179 | +++ | +++ |
| 180 | +++ | +++ |
| 181 | +++ | +++ |
| 182 | +++ | +++ |
| 183 | ++ | +++ |
| 184 | +++ | +++ |
| 185 | ++ | ++ |
| 186 | ND | ND |
| 187 | ++ | ++ |
| 188 | ++ | +++ |
| 189 | ++ | +++ |
| 190 | +++ | +++ |
| 191 | ++ | ++ |
| 192 | ++ | +++ |
| 193 | +++ | +++ |
| 194 | +++ | +++ |
| 195 | +++ | +++ |
| 196 | +++ | +++ |
| 197 | +++ | +++ |
| 198 | +++ | +++ |
| 199 | +++ | +++ |
| 200 | +++ | +++ |
| 201 | ND | ND |
| 202 | +++ | +++ |
| 203 | ++ | +++ |
| 204 | +++ | +++ |
| 205 | +++ | +++ |
| 206 | +++ | +++ |
| 207 | +++ | +++ |
| 208 | ND | ND |
| 209 | +++ | +++ |
| 210 | +++ | +++ |
| 211 | +++ | +++ |
| 212 | +++ | +++ |
| 213 | +++ | +++ |
| 214 | +++ | +++ |
| 215 | +++ | +++ |
| 216 | +++ | +++ |
| 217 | +++ | +++ |
| 218 | +++ | +++ |
| 219 | +++ | +++ |
| 220 | +++ | +++ |
| 221 | +++ | +++ |
| 222 | +++ | +++ |
| 223 | +++ | +++ |
| 224 | +++ | +++ |
| 225 | ND | ND |
| 226 | ++ | +++ |
| 227 | +++ | +++ |
| 228 | ND | ND |
| 229 | +++ | +++ |
| 230 | ND | ND |
| 231 | +++ | ++ |
| 232 | +++ | +++ |
| 233 | +++ | +++ |
| 234 | +++ | +++ |
| 235 | +++ | +++ |
| 236 | +++ | +++ |
| 237 | ND | ND |
| 238 | +++ | +++ |

-continued

| CMPD | Bio-Cell-Prolif-3D (MiaPaca2 IC50) [nM] | Bio-Cell-Prolif-3D (H1975 IC50) [nM] |
|---|---|---|
| 239 | +++ | +++ |
| 240 | +++ | +++ |
| 241 | ND | ND |
| 242 | +++ | +++ |
| 243 | +++ | +++ |
| 244 | +++ | +++ |
| 245 | ++ | ++ |
| 246 | ND | ND |
| 247 | +++ | +++ |
| 248 | +++ | +++ |
| 249 | ++ | +++ |
| 250 | + | ++ |
| 251 | ++ | +++ |
| 252 | ++ | +++ |
| 253 | ++ | ++ |
| 254 | ++ | ++ |
| 255 | ++ | +++ |
| 256 | +++ | +++ |
| 257 | +++ | +++ |
| 258 | +++ | +++ |
| 259 | +++ | +++ |
| 260 | +++ | +++ |
| 261 | +++ | +++ |
| 262 | +++ | +++ |
| 263 | +++ | +++ |
| 264 | +++ | +++ |
| 265 | +++ | +++ |
| 266 | +++ | +++ |
| 267 | +++ | +++ |
| 268 | +++ | +++ |
| 269 | +++ | +++ |
| 270 | +++ | +++ |
| 271 | +++ | +++ |
| 272 | +++ | +++ |
| 273 | +++ | +++ |
| 274 | ND | ND |
| 275 | ND | ND |
| 276 | ++ | ++ |
| 277 | +++ | +++ |
| 278 | + | ++ |
| 279 | ND | ND |
| 280 | ND | ND |
| 281 | ND | ND |
| 282 | ND | ND |
| 283 | +++ | +++ |
| 284 | ND | ND |
| 285 | ++ | +++ |
| 286 | ND | ND |
| 287 | +++ | +++ |
| 288 | +++ | +++ |
| 289 | +++ | +++ |
| 290 | ND | ND |
| 291 | +++ | +++ |
| 292 | +++ | +++ |
| 293 | +++ | +++ |
| 294 | +++ | +++ |
| 295 | +++ | +++ |
| 296 | ++ | +++ |
| 297 | ++ | +++ |
| 298 | +++ | +++ |
| 299 | ++ | +++ |
| 300 | +++ | +++ |
| 301 | ++ | +++ |
| 302 | +++ | +++ |
| 303 | +++ | +++ |
| 304 | +++ | +++ |
| 305 | +++ | +++ |
| 306 | ND | ND |
| 307 | +++ | +++ |
| 308 | +++ | +++ |
| 309 | +++ | +++ |
| 310 | ND | ND |
| 311 | ND | ND |
| 312 | +++ | +++ |

| CMPD | Bio-Cell-Prolif-3D (MiaPaca2 IC50) [nM] | Bio-Cell-Prolif-3D (H1975 IC50) [nM] |
| --- | --- | --- |
| 313 | +++ | +++ |
| 314 | +++ | +++ |
| 315 | ++ | +++ |
| 316 | ++ | +++ |
| 317 | ++ | +++ |
| 318 | +++ | +++ |
| 319 | ND | ND |
| 320 | +++ | +++ |
| 321 | +++ | +++ |
| 322 | +++ | +++ |
| 323 | +++ | +++ |
| 324 | +++ | +++ |
| 325 | +++ | +++ |
| 326 | +++ | +++ |
| 327 | +++ | +++ |
| 328 | +++ | +++ |
| 329 | +++ | +++ |
| 330 | +++ | +++ |
| 331 | +++ | +++ |
| 332 | +++ | +++ |
| 333 | +++ | +++ |
| 334 | ND | ND |
| 335 | +++ | +++ |
| 336 | +++ | +++ |
| 337 | +++ | +++ |
| 338 | +++ | +++ |
| 339 | +++ | +++ |
| 340 | ++ | ++ |
| 341 | +++ | +++ |
| 342 | +++ | +++ |
| 343 | +++ | +++ |
| 344 | ND | ND |
| 345 | +++ | +++ |
| 346 | +++ | +++ |
| 347 | +++ | +++ |
| 348 | +++ | +++ |
| 349 | +++ | +++ |
| 350 | +++ | +++ |
| 351 | +++ | +++ |
| 352 | +++ | +++ |
| 353 | +++ | +++ |
| 354 | +++ | +++ |
| 355 | +++ | +++ |
| 356 | +++ | +++ |
| 357 | ND | ND |
| 358 | ND | ND |
| 359 | +++ | +++ |
| 360 | +++ | +++ |
| 361 | ++ | +++ |
| 362 | ++ | +++ |
| 363 | +++ | +++ |
| 364 | ++ | +++ |
| 365 | +++ | +++ |
| 366 | +++ | +++ |
| 367 | ++ | +++ |
| 368 | ++ | +++ |
| 369 | ++ | +++ |
| 370 | +++ | +++ |
| 371 | ND | ND |
| 372 | +++ | +++ |
| 373 | +++ | +++ |
| 374 | +++ | +++ |
| 375 | +++ | +++ |
| 376 | +++ | +++ |
| 377 | +++ | +++ |
| 378 | +++ | +++ |
| 379 | +++ | +++ |
| 380 | ND | ND |
| 381 | +++ | +++ |
| 382 | ND | ND |
| 383 | +++ | +++ |
| 384 | +++ | +++ |
| 385 | +++ | +++ |
| 386 | +++ | +++ |
| 387 | +++ | +++ |
| 388 | +++ | +++ |
| 389 | +++ | +++ |
| 390 | +++ | +++ |
| 391 | +++ | +++ |
| 392 | +++ | +++ |
| 393 | +++ | +++ |
| 394 | +++ | +++ |
| 395 | +++ | +++ |
| 396 | +++ | +++ |
| 397 | +++ | +++ |
| 398 | ND | ND |
| 399 | ++ | +++ |
| 400 | +++ | +++ |
| 401 | ++ | +++ |
| 402 | +++ | +++ |
| 403 | ND | ND |
| 404 | ++ | ++ |
| 405 | +++ | +++ |
| 406 | +++ | +++ |
| 407 | ++ | ++ |
| 408 | ND | ND |
| 409 | +++ | +++ |
| 410 | +++ | +++ |
| 411 | +++ | +++ |
| 412 | +++ | +++ |
| 413 | +++ | +++ |
| 414 | +++ | +++ |
| 415 | +++ | +++ |
| 416 | ND | ND |
| 417 | +++ | +++ |
| 418 | +++ | +++ |
| 419 | +++ | +++ |
| 420 | +++ | +++ |
| 421 | +++ | +++ |
| 422 | ND | ND |
| 423 | ND | ND |
| 424 | ND | ND |
| 425 | ND | ND |
| 426 | ND | ND |
| 427 | ND | ND |

IC50 less than or equal to 1 μM +++; IC50 greater than 1 μM and less than or equal to 10 μM ++; IC50 greater than 10 μM +; ND not determined.

Example 10: In Vivo Ras Inhibition and Synergistic Reduction of Tumor Growth in a Ras-Driven Model The in vivo reduction in Ras signaling output by a subject compound alone and synergistic reduction of tumor growth in combination with another therapeutic agent are determined in a mouse tumor xenograft model.

Xenograft with K-Ras G12C Mutation

In an example, tumor xenografts are established by administration of tumor cells with K-Ras G12C mutation (e.g., MIA PaCa-2 cells) into mice, e.g., injection of the tumor cells into the right flanks of female BomTacNMRI-Foxn1nu mice with an age between 6 to 8 weeks. In case of the subcutaneous (s.c.) MIA PaCa-2 xenograft mouse models, MIA PaCa-2 cells are grown in cell culture flasks in appropriate medium. Cultures are incubated at 37° C. and 5% $CO_2$ in a humidified atmosphere, with medium change or subcultivation performed 2-3 times a week. For injection, the cultured tumor cells are mixed with PBS including 5% FCS and Matrigel in a 1:1 ratio. About 0.5×10E7 cells in a volume of 100 μL is injected s.c. in each mouse to establish tumors. Mice are randomized into treatment groups of 6-10 mice, once tumors reach a desirable size (e.g., between about 88 to about 504 mm3, or between about 103 to about 377 mm³). Treatment with a subject compound of the present disclosure or with a control (e.g., vehicle control) may start on the day of randomization and can be continued until end of the study (e.g., 18 days). The test samples are administered intragastrically using a gavage needle at an application volume of 10 mL/kg in a volume of 10 mL/kg per mouse daily twice with a 6 h difference.

Mice are housed under standardized conditions at 21.5±1.5° C. and 55±10% humidity. Standardized irradiated diet and autoclaved tap water is provided ad libitum. In some cases, tags (e.g., ear tags, microchips implanted subcutaneously under isoflurane anesthesia) are used to identify each mouse. The tumor diameter is measured two or three times a week with a caliper. The volume of each tumor (in mm³) is calculated according to the formula "tumor volume= (π*length*width2)/6." To monitor side effects of treatment, mice are inspected daily for abnormalities and body weight is determined, e.g., daily. Animals are sacrificed at the end of the study. Animals with necrotic tumors or tumor sizes exceeding 1500 mm³ are sacrificed early during the study for ethical reasons. FIG. 1 shows that compound A of Formula I as disclosed herein inhibits tumor growth alone at the indicated dose, and further synergistically inhibits tumor growth when administered in conjunction with a Kras G12C inhibitor, Example 11: In Vivo Ras Inhibition and Synergistic Reduction of Tumor Growth in an EGFR Mutation-Driven Model The in vivo reduction in Ras signaling output by a subject compound alone and synergistic reduction of tumor growth in combination with another therapeutic agent is determined in a mouse tumor xenograft model.
Xenograft with EGFR Mutations In an example, tumor xenografts are established by administration of tumor cells with NCI-H1975 (ATCC CRL-5908) into mice, e.g., injection of the tumor cells into the right flanks of female BomTacNMRI-Foxn1nu mice with an age between 6 to 8 weeks. In case of the subcutaneous (s.c.) NCI-H1975 xenograft mouse models, NCI-H1975 cells are grown in cell culture flasks in appropriate medium. Cultures are incubated at 37° C. and 5% $CO_2$ in a humidified atmosphere, with medium change or subcultivation performed 2-3 times a week. For injection, the cultured tumor cells are mixed with PBS including 5% FCS and Matrigel in a 1:1 ratio. About 0.5×10E7 cells in a volume of 100 µL is injected s.c. in each mouse to establish tumors. Mice are randomized into treatment groups of 6-10 mice, once tumors reach a desirable size (e.g., between about 88 to about 504 mm3, or between about 103 to about 377 mm³). Treatment with an inhibitor compound of the present disclosure or with a control (e.g., vehicle control) may start on the day of randomization and can be continued until end of the study (e.g., 18 days). The test samples are administered intragastrically using a gavage needle at an application volume of 10 mL/kg in a volume of 10 mL/kg per mouse daily twice with a 6 h difference.

Mice are housed under standardized conditions at 21.5±1.5° C. and 55±10% humidity. Standardized irradiated diet and autoclaved tap water is provided ad libitum. In some cases, tags (e.g., ear tags, microchips implanted subcutaneously under isoflurane anesthesia) are used to identify each mouse. The tumor diameter is measured two or three times a week with a caliper. The volume of each tumor (in mm³) is calculated according to the formula "tumor volume= (π*length*width2)/6." To monitor side effects of treatment, mice are inspected daily for abnormalities and body weight is determined, e.g., daily. Animals are sacrificed at the end of the study. Animals with necrotic tumors or tumor sizes exceeding 1500 mm³ are sacrificed early during the study for ethical reasons. FIG. 2 shows that compound B of Formula I as disclosed herein inhibits tumor growth alone at the indicated dose, and further synergistically inhibits tumor growth when administered in conjunction with an EGFR inhibitor, Osimertinib.

Example 12: Metabolic (Microsomal) Stability Assay

The metabolic stability of the test compound is assayed at 37° C. using pooled liver microsomes (mouse or human liver microsomes). An aliquot of 10 µL of 50 µM test compound is mixed with 490 µL of 0.611 mg/mL liver microsomes, and then, 50 µL of the mixtures are dispensed to the 96 well tubes and warmed at 37° C. for 10 minutes. The reactions are initiated by adding 50 µL of the pre-warmed NADPH regeneration system solution (add 1.2 µL solution, 240 µl solution B, mix with 10.56 ml KPBS) and then incubated at 37° C. The final incubation solution contains 100 mM potassium phosphate (pH 7.4), 1.3 mM NADP+, 3.3 mM glucose 6-phosphate, 0.4 Unit/mL of glucose 6-phosphate dehydrogenase, 3.3 mM magnesium chloride, 0.3 mg/mL liver microsomes and 0.5 µM test article. After 0, 15, 30 and 60 minutes in a shaking incubator, the reactions are terminated by adding 100 µL of acetonitrile containing 200 nM buspirone as an internal standard. All incubations are conducted in duplicate. Plates are vortexed vigorously by using Fisher Scientific microplate vortex mixer (Henry Troemner, US). Samples are then centrifuged at 3500 rpm for 10 minutes (4° C.) using Sorvall Legend XRT Centrifuge (Thermo Scientific, GE). Supernatants (40 µL) are transferred into clean 96-deep well plates. Each well is added with 160 µL of ultrapure water (Milli-Q, Millipore Corporation) with 0.1% (v/v) formic acid (Fisher Chemical), mixed thoroughly and subjected to LC/MS/MS analysis in MRM positive ionization mode.

All the samples are measured using a mass spectrometer (QTrap 5500 quadrupole/ion trap) coupled with a Shimadzu HPLC system. The HPLC system consisted of a Shimadzu series degasser, binary quaternary gradient pumps, column heater coupled to an autosampler, and a Phenomenex Gemini-NX, C18, 3.0 µm or Phenomenex Lunar, C8, 5.0 µM HPLC column (Phenomenex, Torrance, Calif.), and eluted with a mobile phase gradient consisting of Solution A (0.1% formic acid water) and Solution B (0.1% formic acid acetonitrile). The column temperature is maintained at 40° C. All the analytes are detected with positive-mode electrospray ionization (ES+).

The half-life for the metabolic degradation of the test compound is calculated by plotting the time-course disappearance of the test compound during the incubation with liver microsomes. Each plot is fitted to a first-order equation for the elimination of the test compound (% remaining compound) versus time using non-linear regression (Equation 1).

$$\frac{C_t}{C_0} = e^{-kt} \qquad \text{Equation 1}$$

where $C_t$ is the mean relative substrate concentration at time t and $C_0$ is the initial concentration (0.5 μM) at time 0. Note that the area ratio of the substrate peak to an internal standard peak is proportional to the analyte concentration and are used for regression analysis to derive a value of k.

The half-life $t_{1/2}$ for metabolic (microsome) stability is derived from the test compound elimination constant k using Equation 2 below.

$$t_{1/2} = \frac{0.693}{k} \quad \text{Equation 2}$$

Example 13: CYP2C19 Inhibition Assay

Some xenobiotics can inhibit cytochrome P450 (CYP) enzyme function, which alters their ability to metabolize drugs. Administration of a CYP inhibitor with a drug whose clearance is dependent on CYP metabolism can result in increased plasma concentrations of this concomitant drug, leading to potential toxicity. The inhibition of CYP2C19 by a test compound is assayed in human liver microsomes using S-Mephenytoin as a CYP2C19 substrate. The stock solution of the test compound or known CYP2C19 inhibitor as a positive control (10 mM) is diluted with KPBS to 40 μM. In a similar way, the stock solutions of the human liver microsomes and S-Mephenytoin are diluted with KPBS buffer. The pre-incubations are started by incubating a plate containing L human liver microsomes (final concentration of 0.2 mg/mL), 25 μL NADPH-generating system, and a 25 μL test compound (final concentration 10 μM) or the positive control for 30 min at 37±1° C. After the pre-incubation, 25 μL S-Mephenytoin (final concentration 200 μM) is added and incubated another 12 minutes at 37±1° C. for substrate metabolism. The reactions are terminated by addition of 100 μL of ice-cold acetonitrile containing an internal standard (buspirone). Precipitated proteins are removed by centrifugation at 3500 rpm for 10 minutes at 4° C. (Allegra 25R, Beckman Co. Fullerton, Calif.) and then aliquot of the supernatant is transferred to an assay plate.

All the samples are determined by a mass spectrometer (QTrap 5500 quadrupole/ion trap) coupled with a Shimadzu HPLC system, following the manufacturer's instructions. The metabolism of S-Mephenytoin in human liver microsomes is monitored by LC/MS/MS as representative of CYP2C19 inhibitory activity. The amount of metabolite formed is assessed by the peak area ratio (metabolite/IS) and % inhibition at 10 μM is expressed as a percentage of the metabolite signal reduced compared to the control (i.e. an incubation that contained no inhibitor and represented 100% enzyme activity): % inhibition=(1−A/B)×100%, where A is the metabolite peak area ratio formed in the presence of test compound or inhibitor at 10 μM and B is the metabolite peak area ratio formed without test compound or inhibitor in the incubation.

Example 14: Mouse and Human Protein Binding Assay to Assess Free Drug Concentration The assay is to determine the plasma protein binding of the test compound in the plasma of human and animal species using a Rapid Equilibrium Dialysis (RED) device for equilibrium dialysis and LC-MS/MS for sample analysis. Test compound is spiked in. The stock solution of the test compound is prepared at 5 mM concentration. One μL of 5 mM working solution into 1000 μl plasma. The final concentration is 5 μM. The spiked plasma is placed on a rocker, and gently agitated for approximately 20 minutes. A volume of 300 μL of the plasma sample containing 5 μM test compound from each species is added to designate RED device donor chambers followed by addition of 500 μL of potassium phosphate buffer to the corresponding receiver chambers in duplicate. The RED device is then sealed with sealing tape and shaken at 150 RPM for 4 hours at 37° C. Post-dialysis donor and receiver compartment samples are prepared for LC-MS/MS analysis, including spiking samples with an internal standard for the bioanalytical analysis. Warfarin and propranolol are purchased from Sigma-Aldrich (St. Louis, Mo.), and used as positive controls for low and high plasma protein binding, respectively.

All the samples are analyzed using an Agilent Technologies 6430 Triple Quad LC/MS system. The HPLC system consisted of Agilent 1290 Infinity Liquid Chromatograph coupled to an autosampler (Agilent 1290 Infinity LC Injector HTC), and a Phenomenex Gemini-NX, C18, 3.0 μm or Phenomenex Lunar, C8, 5.0 μM HPLC column (Phenomenex, Torrance, Calif.), and eluted with a mobile phase gradient consisting of Solution A (0.1% formic acid water) and Solution B (0.1% formic acid acetonitrile). The column temperature is maintained at 40° C. All the analytes are detected with positive-mode electrospray ionization (ES+). The percentage of the test compound bound to plasma is calculated following Equation 3 and 4.

$$\% \text{ Free test compound} = \frac{\text{Peak ratio}\left(\frac{\text{test compound}}{\text{Internal standard}}\right) \text{receiver compartment}}{\text{Peak ratio}\left(\frac{\text{test compound}}{\text{Internal standard}}\right) \text{donor compartment}} * 100 \quad \text{Equation 3}$$

$$\% \text{ Plasma protein bound test compound} = 100 - \% \text{ Free test compound} \quad \text{Equation 4}$$

Example 15: hERG (Automated Patch-Clamp) Assay

The human ether-a-go-go related gene (hERG) encodes the voltage gated potassium channel in the heart (IKr) which is involved in cardiac repolarization. Inhibition of the hERG causes QT interval prolongation and can lead to potential fatal events in humans. It is thus important to assess hERG inhibition early in drug discovery. A hERG automated patch-clamp assay is done using a hERG CHO-K1 cell line using an incubation time of 5 min. The degree of hERG inhibition (%) is obtained by measuring the tail current amplitude, which is induced by a one second test pulse to −40 mV after a two second pulse to +20 mV, before and after drug incubation (the difference current is normalized to control and multiplied by 100 to obtain the percent of inhibition). The percent hERG inhibition is measured in the presence of 10 μM test compound.

Example 16: Rat Oral Exposure (% F)

Pharmacokinetic profile for test compound is measured by single dosing in jugular vein cannulated male Sprague-Dawley rats. Animal weights are typically over 200 grams, and animals are allowed to acclimate to their new environment for at least 3 days prior to the initiation of any studies. One set of animals is dosed intravenous (IV) with test compound, 2 mg/kg in 20% HP-beta-CD or 20% Captisol, pH adjusted to ~4 by citric acid. IV dosing solution concentration is 0.4 mg/ml test compound. Time of blood sampling is 5 minutes, 15 minutes, 30 minutes, 90 minutes, 360 minutes, and 24 hours following IV dosing. Another set of animals is dosed oral (po) with test compound, 10 mg/kg in 20% HP-beta-CD or 20% Captisol, pH adjusted to ~4 by citric acid. Oral dosing solution concentration is 1 mg/ml test compound. Time of blood sampling is 15 minutes, 30 minutes, 90 minutes, 180 minutes, 360 minutes and 24 hours following oral (po) dosing. Blood samples (~0.2 mL/sample) is collected via jugular vein and placed in tubes containing EDTA-K2 and stored on ice until centrifuged. The blood samples are centrifuged at approximately 6800 g for 6 minutes at 2-8° C. and the resulting plasma will be separated and stored frozen at approximately −80° C.

All the plasma samples are analyzed using an Agilent Technologies 6430 Triple Quad LC/MS system, following the manufacture instructions. All the analytes are detected with positive-mode electrospray ionization (ES+). A standard curve for each test compound is generated and used to measure test compound concentrations in the rat plasma samples. Based on the time course sampling, an area under the curve is calculated for the oral dose group and the intravenous dose group. Percentage rat bioavailability is calculated based on equation 5.

$$\% \, F(\text{rat}) = \frac{AUC_{po} * \text{Dose}_{IV}}{AUC_{IV} * \text{Dose}_{po}}, \quad \text{Equation 5}$$

where F is bioavailability, $AUC_{po}$ is area under curve of oral drug, $AUC_{IV}$ is area under curve of intravenous drug, $\text{Dose}_{IV}$ is the intravenous dose and $\text{Dose}_{po}$ is the oral dose.

Example 17: Kinase Selectivity Assay

Eurofins DiscoverX (USA) commercially offers measurement on its KINOMEscan scanEDGE™ 97Panel comprising of 97 potential kinase off-targets. The KINOMEscan™ screening platform employs an active site-directed competition binding assay to quantitatively measure interactions between test compounds and kinases. Test compound is screened at 10 uM, and results for primary screen binding interactions are reported as 'Percent control', where lower numbers indicate stronger binding to a kinase being examined.

$$\text{Percent control} = \left( \frac{\text{test compound signal} - \text{positive control signal}}{\text{negative control signal} - \text{positive control signal}} \right) * 100$$

where the negative control=DMSO (100% Ctrl) and the positive control=control compound (0% Ctrl).

What is claimed is:

1. A compound of Formula (I-1):

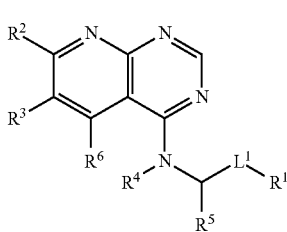

Formula (I-1)

or a pharmaceutically acceptable salt or stereoisomer thereof,
wherein:
  $L^1$ is a bond;
  $R^1$ is 6- to 10-membered aryl, wherein the 6- to 10-membered aryl is optionally substituted with one or more independently selected $R^{10}$ substituents;
  $R^2$ is halogen or $OR^{2a}$;
  $R^{2a}$ is $C_{1-6}$ alkyl, $C_{3-10}$ cycloalkyl, $C_{2-9}$ heterocycloalkyl, $C_{6-10}$ aryl, or $C_{1-9}$ heteroaryl, wherein the $C_{1-6}$ alkyl, $C_{3-10}$ cycloalkyl, $C_{2-9}$ heterocycloalkyl, $C_{6-10}$ aryl, or $C_{1-9}$ heteroaryl is optionally substituted with one, two, or three independently selected $R^{20a}$ substituents;
  $R^3$ is halogen, $C_{1-6}$ alkyl, $C_{3-14}$ cycloalkyl, $C_{2-9}$ heterocycloalkyl, $C_{6-10}$ aryl, or $C_{1-9}$ heteroaryl, wherein the $C_{1-6}$ alkyl, $C_{3-10}$ cycloalkyl, $C_{2-9}$ heterocycloalkyl, $C_{6-10}$ aryl, or $C_{1-9}$ heteroaryl is optionally substituted with one, two, or three independently selected $R^{20b}$ substituents;
  $R^4$ is H, $C_{1-6}$ alkyl, or $C_{1-6}$ haloalkyl;
  $R^5$ is H, $C_{1-6}$ alkyl, or $C_{1-6}$ haloalkyl;
  $R^6$ is H, halogen, CN, or $C_{1-6}$ alkyl, wherein the $C_{1-6}$ alkyl is optionally substituted with one, two, or three independently selected $R^{20c}$ substituents;
  each $R^{10}$ is independently halogen, CN, $C_{1-6}$ alkyl, $C_{3-7}$ cycloalkyl, $C_{2-9}$ heterocycloalkyl, $C_{6-10}$ aryl, or $C_{1-9}$ heteroaryl, wherein each $C_{1-6}$ alkyl, $C_{3-7}$ cycloalkyl, $C_{2-9}$ heterocycloalkyl, $C_{6-10}$ aryl, and $C_{1-9}$ heteroaryl is optionally and independently substituted with one, two, or three independently selected $R^{20d}$ substituents;
  each $R^{20a}$ is independently halogen, CN, $C_{1-6}$ alkyl, $CH_2C_{3-10}$ cycloalkyl, $CH_2C_{2-9}$ heterocycloalkyl, $CH_2C_{6-10}$ aryl, $C_{2-6}$ alkenyl, $C_{2-6}$ alkynyl, $C(O)R^{25}$, $C(O)C(O)NR^{22}R^{23}$, $C(O)NR^{22}R^{23}$, $C(O)OR^{22}$, $NR^{22}R^{23}$, $NR^{24}C(O)R^{25}$, $NR^{24}C(O)NR^{22}R^{23}$, $NR^{24}C(O)OR^{25}$, $NR^{24}S(O)_2R^{25}$, $=NH$, $OR^{21}$, $OCH_2C(O)OR^{22}$, $OC(O)R^{25}$, $OC(O)NR^{22}R^{23}$, $=O$, $SR^{21}$, $S(O)_2R^{25}$, $S(O)_2NR^{22}R^{23}$, $C_{3-10}$ cycloalkyl, $C_{2-9}$ heterocycloalkyl, $C_{6-10}$ aryl, or $C_{1-9}$ heteroaryl;
    wherein each $C_{1-6}$ alkyl, $C_{2-6}$ alkenyl, and $C_{2-6}$ alkynyl is optionally and independently substituted with one, two, or three substituents independently selected from the group consisting of halogen, CN, $C(O)R^{25}$, $C(O)C(O)NR^{22}R^{23}$, $C(O)NR^{22}R^{23}$, $C(O)OR^{22}$, $NR^{22}R^{23}$, $NR^{24}C(O)R^{25}$, $NR^{24}C(O)NR^{22}R^{23}$, $NR^{24}C(O)OR^{25}$, $NR^{24}S(O)_2R^{25}$, $=NH$, $OR^{21}$, $OC(O)R^{25}$, $OC(O)NR^{22}R^{23}$, $=O$, $SR^{21}$, $S(O)_2R^{25}$, and $S(O)_2NR^{22}R^{23}$; and
    wherein each $C_{3-10}$ cycloalkyl of $CH_2C_{3-10}$ cycloalkyl, $C_{2-9}$ heterocycloalkyl of $CH_2C_{2-9}$ heterocycloalkyl, $C_{6-10}$ aryl of $CH_2C_{6-10}$ aryl, $C_{3-10}$ cycloalkyl, $C_{2-9}$ heterocycloalkyl, $C_{6-10}$ aryl, and $C_{1-9}$ heteroaryl is optionally and independently substituted with one, two, or three substituents independently selected from the group consisting of halogen, CN, $C_{1-6}$ alkyl, $C_{1-6}$ haloalkyl, $C(O)R^{25}$, $C(O)C(O)NR^{22}R^{23}$, $C(O)NR^{22}R^{23}$, $C(O)OR^{22}$, $NR^{22}R^{23}$, $NR^{24}C(O)R^{25}$, $NR^{24}C(O)NR^{22}R^{23}$, $NR^{24}C(O)OR^{25}$, $NR^{24}S(O)_2R^{25}$, $=NH$, $OR^{21}$, $OC(O)R^{25}$, $OC(O)NR^{22}R^{23}$, $=O$, $SR^{21}$, $S(O)_2R^{25}$, and $S(O)_2NR^{22}R^{23}$;
  each $R^{20e}$ is independently halogen, CN, $C_{1-6}$ alkyl, $CH_2C_{3-10}$ cycloalkyl, $CH_2C_{2-9}$ heterocycloalkyl, $CH_2C_{6-10}$ aryl, $C_{2-6}$ alkenyl, $C_{2-6}$ alkynyl, $C(O)R^{25}$, $C(O)C(O)NR^{22}R^{23}$, $C(O)NR^{22}R^{23}$, $C(O)OR^{22}$, $NR^{22}R^{23}$, $NR^{24}C(O)R^{25}$, $NR^{24}C(O)NR^{22}R^{23}$, $NR^{24}C(O)OR^{25}$, $NR^{24}S(O)_2R^{25}$, $=NH$, $OR^{21}$, $OCH_2C(O)OR^{22}$, $OC(O)R^{25}$, $OC(O)NR^{22}R^{23}$, $=O$, $SR^{21}$, $S(O)_2R^{25}$, $S(O)_2NR^{22}R^{23}$, $C_{3-10}$ cycloalkyl, $C_{2-9}$ heterocycloalkyl, $C_{6-10}$ aryl, or $C_{1-9}$ heteroaryl;
    wherein each $C_{1-6}$ alkyl, $C_{2-6}$ alkenyl, and $C_{2-6}$ alkynyl is optionally and independently substituted with one, two, or three substituents independently selected from the group consisting of halogen, CN, $C(O)R^{25}$, $C(O)C(O)NR^{22}R^{23}$, $C(O)NR^{22}R^{23}$, $C(O)OR^{22}$, $NR^{22}R^{23}$, $NR^{24}C(O)R^{25}$, $NR^{24}C(O)NR^{22}R^{23}$, $NR^{24}C(O)OR^{25}$, $NR^{24}S(O)_2R^{25}$, $=NH$, $OR^{21}$, $OC(O)R^{25}$, $OC(O)NR^{22}R^{23}$, $=O$, $SR^{21}$, $S(O)_2R^{25}$, and $S(O)_2NR^{22}R^{23}$; and
    wherein each $C_{3-10}$ cycloalkyl of $CH_2C_{3-10}$ cycloalkyl, $C_{2-9}$ heterocycloalkyl of $CH_2C_{2-9}$ heterocycloalkyl, $C_{6-10}$ aryl of $CH_2C_{6-10}$ aryl, $C_{3-10}$ cycloalkyl, $C_{2-9}$ heterocycloalkyl, $C_{6-10}$ aryl, and $C_{1-9}$ heteroaryl is optionally and independently substituted with one, two, or three substituents independently selected from the group consisting of halogen, CN, $C_{1-6}$ alkyl, $C_{1-6}$ haloalkyl, $C(O)R^{25}$, $C(O)C(O)NR^{22}R^{23}$, $C(O)$ $NR^{22}R^{23}$, $C(O)OR^{22}$, $NR^{22}R^{23}$, $NR^{24}C(O)R^{25}$, $NR^{24}C(O)NR^{22}R^{23}$, $NR^{24}C(O)OR^{25}$, $NR^{24}S(O)_2$ $R^{25}$, =NH, $OR^{21}$, $OC(O)R^{25}$, $OC(O)NR^{22}R^{23}$, =O, $SR^{21}$, $S(O)_2R^{25}$, and $S(O)_2NR^{22}R^{23}$;

each $R^{20e}$ is independently halogen, CN, $C_{1-6}$ alkyl, $CH_2Cl_{3-10}$ cycloalkyl, $CH_2Cl_{2-9}$ heterocycloalkyl, $CH_2C_{6-10}$ aryl, $C_{2-6}$ alkenyl, $C_{2-6}$ alkynyl, $C(O)R^{25}$, $C(O)C(O)NR^{22}R^{23}$, $C(O)NR^{22}R^{23}$, $C(O)OR^{22}$, $NR^{22}R^{23}$, $NR^{24}C(O)R^{25}$, $NR^{24}C(O)NR^{22}R^{23}$, $NR^{24}C(O)OR^{25}$, $NR^{24}S(O)_2R^{25}$, =NH, $OR^{21}$, $OCH_2C(O)OR^{22}$, $OC(O)R^{25}$, $OC(O)NR^{22}R^{23}$, =O, $SR^{21}$, $S(O)_2R^{25}$, $S(O)_2NR^{22}R^{23}$, $C_{3-10}$ cycloalkyl, $C_{2-9}$ heterocycloalkyl, $C_{6-10}$ aryl, or $C_{1-9}$ heteroaryl;

wherein each $C_{1-6}$ alkyl, $C_{2-6}$ alkenyl, and $C_{2-6}$ alkynyl is optionally and independently substituted with one, two, or three substituents independently selected from the group consisting of halogen, CN, $C(O)R^{25}$, $C(O)C(O)NR^{22}R^{23}$, $C(O)NR^{22}R^{23}$, $C(O)OR^{22}$, $NR^{22}R^{23}$, $NR^{24}C(O)R^{25}$, $NR^{24}C(O)NR^{22}R^{23}$, $NR^{24}C(O)OR^{25}$, $NR^{24}S(O)_2R^{25}$, =NH, $OR^{21}$, $OC(O)R^{25}$, $OC(O)NR^{22}R^{23}$, =O, $SR^{21}$, $S(O)_2R^{25}$, and $S(O)_2NR^{22}R^{23}$; and wherein each $C_{3-10}$ cycloalkyl of $CH_2C_{3-10}$ cycloalkyl, $C_{2-9}$ heterocycloalkyl of $CH_2C_{2-9}$ heterocycloalkyl, $C_{6-10}$ aryl of $CH_2C_{6-10}$ aryl, $C_{3-10}$ cycloalkyl, $C_{2-9}$ heterocycloalkyl, $C_{6-10}$ aryl, and $C_{1-9}$ heteroaryl is optionally and independently substituted with one, two, or three substituents independently selected from the group consisting of halogen, CN, $C_{1-6}$ alkyl, $C_{1-6}$ haloalkyl, $C(O)R^{25}$, $C(O)C(O)NR^{22}R^{23}$, $C(O)NR^{22}R^{23}$, $C(O)OR^{22}$, $NR^{22}R^{23}$, $NR^{24}C(O)R^{25}$, $NR^{24}C(O)NR^{22}R^{23}$, $NR^{24}C(O)OR^{25}$, $NR^{24}S(O)_2R^{25}$, =NH, $OR^{21}$, $OC(O)R^{25}$, $OC(O)NR^{22}R^{23}$, =O, $SR^{21}$, $S(O)_2R^{25}$, and $S(O)_2NR^{22}R^{23}$;

each $R^{20d}$ is independently halogen, CN, $C_{1-6}$ alkyl, $CH_2Cl_{3-10}$ cycloalkyl, $CH_2Cl_{2-9}$ heterocycloalkyl, $CH_2C_{6-10}$ aryl, $C_{2-6}$ alkenyl, $C_{2-6}$ alkynyl, $C(O)R^{25}$, $C(O)C(O)NR^{22}R^{23}$, $C(O)NR^{22}R^{23}$, $C(O)OR^{22}$, $NR^{22}R^{23}$, $NR^{24}C(O)R^{25}$, $NR^{24}C(O)NR^{22}R^{23}$, $NR^{24}C(O)OR^{25}$, $NR^{24}S(O)_2R^{25}$, =NH, $OR^{21}$, $OCH_2C(O)OR^{22}$, $OC(O)R^{25}$, $OC(O)NR^{22}R^{23}$, =O, $SR^{21}$, $S(O)_2R^{25}$, $S(O)_2NR^{22}R^{23}$, $C_{3-10}$ cycloalkyl, $C_{2-9}$ heterocycloalkyl, Chao aryl, or $C_{1-9}$ heteroaryl;

wherein each $C_{1-6}$ alkyl, $C_{2-6}$ alkenyl, and $C_{2-6}$ alkynyl is optionally and independently substituted with one, two, or three substituents independently selected from the group consisting of halogen, CN, $C(O)R^{25}$, $C(O)C(O)NR^{22}R^{23}$, $C(O)NR^{22}R^{23}$, $C(O)OR^{22}$, $NR^{22}R^{23}$, $NR^{24}C(O)R^{25}$, $NR^{24}C(O)NR^{22}R^{23}$, $NR^{24}C(O)OR^{25}$, $NR^{24}S(O)_2R^{25}$, =NH, $OR^{21}$, $OC(O)R^{25}$, $OC(O)NR^{22}R^{23}$, =O, $SR^{21}$, $S(O)_2R^{25}$, and $S(O)_2NR^{22}R^{23}$; and wherein each $C_{3-10}$ cycloalkyl of $CH_2C_{3-10}$ cycloalkyl, $C_{2-9}$ heterocycloalkyl of $CH_2C_{2-9}$ heterocycloalkyl, $C_{6-10}$ aryl of $CH_2C_{6-10}$ aryl, $C_{3-10}$ cycloalkyl, $C_{2-9}$ heterocycloalkyl, $C_{6-10}$ aryl, and $C_{1-9}$ heteroaryl is optionally and independently substituted with one, two, or three substituents independently selected from the group consisting of halogen, CN, $C_{1-6}$ alkyl, $C_{1-6}$ haloalkyl, $C(O)R^{25}$, $C(O)C(O)NR^{22}R^{23}$, $C(O)NR^{22}R^{23}$, $C(O)OR^{22}$, $NR^{22}R^{23}$, $NR^{24}C(O)R^{25}$, $NR^{24}C(O)NR^{22}R^{23}$, $NR^{24}C(O)OR^{25}$, $NR^{24}S(O)_2R^{25}$, =NH, $OR^{21}$, $OC(O)R^{25}$, $OC(O)NR^{22}R^{23}$, =O, $SR^{21}$, $S(O)_2R^{25}$, and $S(O)_2NR^{22}R^{23}$;

each $R^{21}$ is independently H, $C_{1-6}$ alkyl, $C_{1-6}$ haloalkyl, $C_{2-6}$ alkenyl, $C_{2-6}$ alkynyl, $C_{3-7}$ cycloalkyl, $C_{2-9}$ heterocycloalkyl, $C_{6-10}$ aryl, or $C_{1-9}$ heteroaryl, wherein each $C_{3-7}$ cycloalkyl, $C_{2-9}$ heterocycloalkyl, $C_{6-10}$ aryl, and $C_{1-9}$ heteroaryl is optionally and independently substituted with one, two, or three substituents independently selected from the group consisting of halogen and $C_{1-6}$ alkyl;

each $R^{22}$ is independently H, $C_{1-6}$ alkyl, $C_{1-6}$ haloalkyl, $C_{2-6}$ alkenyl, $C_{2-6}$ alkynyl, $C_{3-7}$ cycloalkyl, $C_{2-9}$ heterocycloalkyl, $C_{6-10}$ aryl, or $C_{1-9}$ heteroaryl, wherein each $C_{3-7}$ cycloalkyl, $C_{2-9}$ heterocycloalkyl, $C_{6-10}$ aryl, and $C_{1-9}$ heteroaryl is optionally and independently substituted with one, two, or three substituents independently selected from the group consisting of halogen and $C_{1-6}$ alkyl;

each $R^{23}$ is independently H or $C_{1-6}$ alkyl;

each $R^{24}$ is independently H or $C_{1-6}$ alkyl; and each $R^{25}$ is independently $C_{1-6}$ alkyl, $C_{2-6}$ alkenyl, $C_{2-6}$ alkynyl, $C_{3-7}$ cycloalkyl, $C_{2-9}$ heterocycloalkyl, $C_{6-10}$ aryl, or $C_{1-9}$ heteroaryl, wherein each $C_{1-6}$ alkyl, $C_{3-7}$ cycloalkyl, $C_{2-9}$ heterocycloalkyl, $C_{6-10}$ aryl, and $C_{1-9}$ heteroaryl is optionally and independently substituted with one, two, or three substituents independently selected from the group consisting of halogen, $C_{1-6}$ alkyl, $C_{1-6}$ haloalkyl, $OC_{1-6}$ alkyl, $C_{3-7}$ cycloalkyl, $C_{2-9}$ heterocycloalkyl, $C_{6-10}$ aryl, and $C_{1-9}$ heteroaryl.

2. The compound of claim 1, or a pharmaceutically acceptable salt or stereoisomer thereof, wherein $R^1$ is phenyl, wherein the phenyl is substituted with one or more independently selected $R^{10}$ substituents.

3. The compound of claim 2, or a pharmaceutically acceptable salt or stereoisomer thereof, wherein each $R^{10}$ is independently halogen or $C_{1-6}$ alkyl, wherein each $C_{1-6}$ alkyl is optionally and independently substituted with one, two, or three independently selected $R^{20d}$.

4. The compound of claim 3, or a pharmaceutically acceptable salt or stereoisomer thereof, wherein each $R^{20d}$ is independently halogen or OH.

5. The compound of claim 3, or a pharmaceutically acceptable salt or stereoisomer thereof, wherein $R^1$ is:

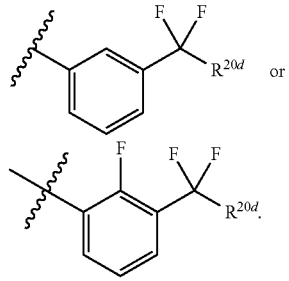

6. The compound of claim 5, or a pharmaceutically acceptable salt or stereoisomer thereof, wherein $R^{20d}$ is $C_{1-5}$ alkyl, wherein the $C_{1-5}$ alkyl is optionally substituted with one, two, or three substituents independently selected from the group consisting of F and OH.

7. The compound of claim 6, or a pharmaceutically acceptable salt or stereoisomer thereof, wherein $R^{20d}$ is $C_{1-3}$ alkyl, wherein the $C_{1-3}$ alkyl is substituted with one OH substituent.

8. The compound of claim 7, or a pharmaceutically acceptable salt or stereoisomer thereof, wherein $R^1$ is:

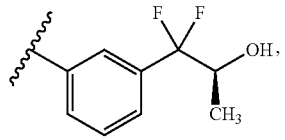

-continued

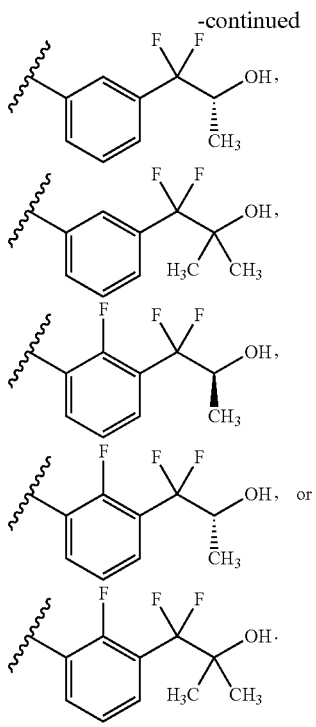

9. The compound of claim 1, wherein the compound is of Formula (Ia-1):

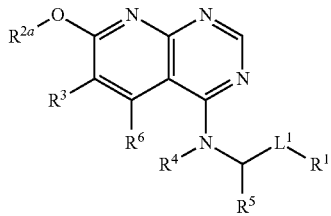

Formula (Ia-1)

or a pharmaceutically acceptable salt or stereoisomer thereof.

10. The compound of claim 9, or a pharmaceutically acceptable salt or stereoisomer thereof, wherein $R^{2a}$ is $C_{1-6}$ alkyl, wherein the $C_{1-6}$ alkyl is optionally substituted with one, two, or three independently selected $R^{20e}$ substituents.

11. The compound of claim 10, or a pharmaceutically acceptable salt or stereoisomer thereof, wherein $R^{2a}$ is $C_{1-6}$ alkyl.

12. The compound of claim 11, or a pharmaceutically acceptable salt or stereoisomer thereof, wherein $R^{2a}$ is $CH_3$.

13. The compound of claim 1, or a pharmaceutically acceptable salt or solvate stereoisomer thereof, wherein $R^3$ is $C_{3-10}$ cycloalkyl, wherein the $C_{3-10}$ cycloalkyl is optionally substituted with one, two, or three independently selected $R^{20b}$ substituents.

14. The compound of claim 13, or a pharmaceutically acceptable salt or stereoisomer thereof, wherein $R^3$ is $C_{3-4}$ cycloalkyl, wherein the $C_{3-4}$ cycloalkyl is optionally substituted with one $R^{20b}$ substituent.

15. The compound of claim 14, or a pharmaceutically acceptable salt or stereoisomer thereof, wherein $R^{20b}$ is halogen or CN.

16. The compound of claim 13, or a pharmaceutically acceptable salt or stereoisomer thereof, wherein $R^3$ is 1-cyanocyclopropyl or 1-(difluoromethyl)cyclopropyl.

17. The compound of claim 1, or a pharmaceutically acceptable salt or stereoisomer thereof, wherein $R^3$ is $C_{2-9}$ heterocycloalkyl, wherein the $C_{2-9}$ heterocycloalkyl is optionally substituted with one, two, or three independently selected $R^{20b}$ substituents.

18. The compound of claim 1, or a pharmaceutically acceptable salt or stereoisomer thereof, wherein $R^4$ is H.

19. The compound of claim 1, or a pharmaceutically acceptable salt or stereoisomer thereof, wherein $R^5$ is $C_{1-6}$ alkyl.

20. The compound of claim 19, or a pharmaceutically acceptable salt or stereoisomer thereof, wherein $R^5$ is $CH_3$.

21. The compound of claim 1, or a pharmaceutically acceptable salt or stereoisomer thereof, wherein $R^6$ is H, halogen, or $C_{1-6}$ alkyl.

22. The compound of claim 21, or a pharmaceutically acceptable salt or stereoisomer thereof, wherein $R^6$ is H.

23. A pharmaceutical composition comprising a pharmaceutically acceptable excipient and a compound of claim 1, or a pharmaceutically acceptable salt or stereoisomer thereof.

24. A method for inhibiting growth of a cell expressing Son of Sevenless homologue 1, wherein the method comprises contacting the cell expressing Son of Sevenless homologue 1 with a compound of claim 1, or a pharmaceutically acceptable salt or stereoisomer thereof.

25. The method of claim 24, wherein the cell expressing Son of Sevenless homologue 1 is a cancer cell expressing Son of Sevenless homologue 1.

26. The method of claim 24, wherein the method further comprises contacting the cell expressing Son of Sevenless homologue 1 with an additional active agent.

27. A method for inhibiting growth of a cell expressing Son of Sevenless homologue 1 in a subject in need thereof, wherein the method comprises administering to the subject a therapeutically effective amount of a compound of claim 1, or a pharmaceutically acceptable salt or stereoisomer thereof.

28. The method of claim 27, wherein the subject has cancer.

29. The method of claim 27, wherein the method further comprises administering to the subject a therapeutically effective amount of an additional therapeutic agent.

30. A compound selected from the group consisting of:

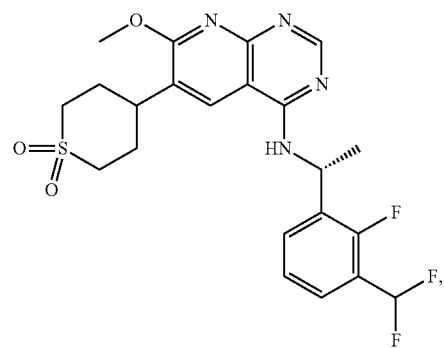

1243
-continued
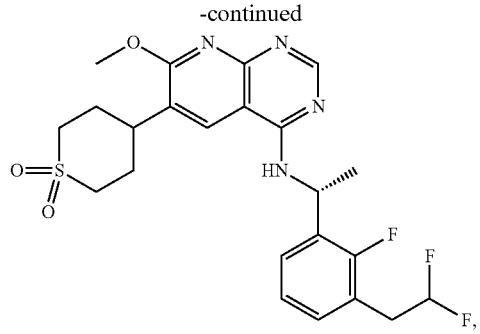
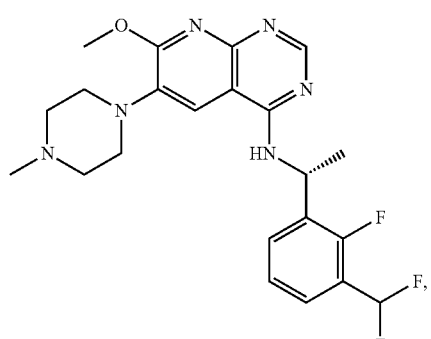
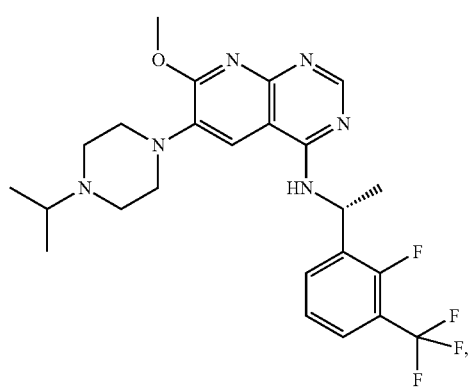
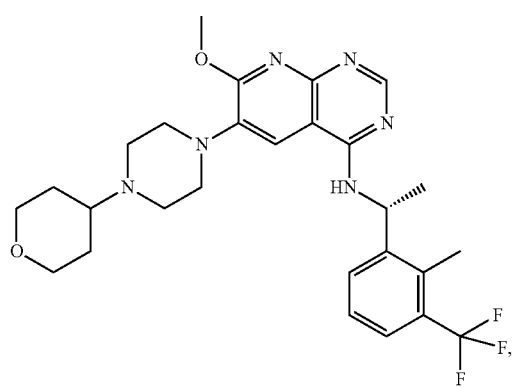
1244
-continued
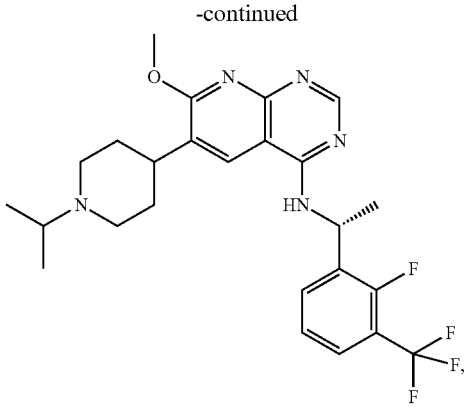
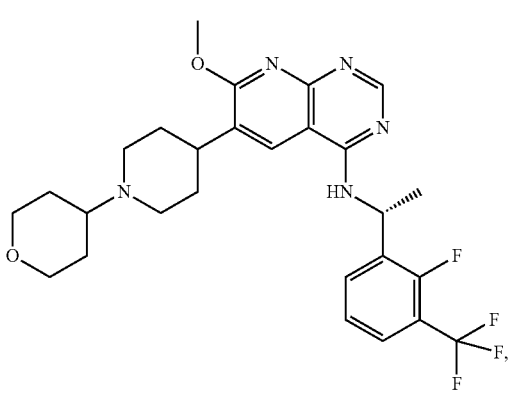
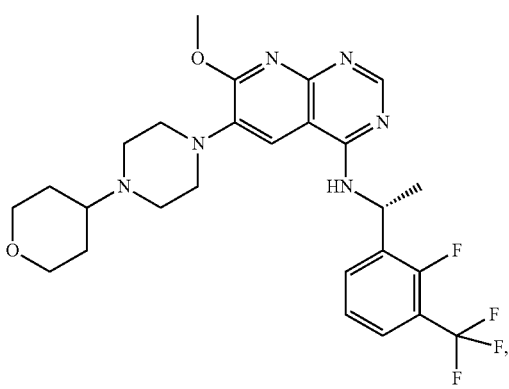
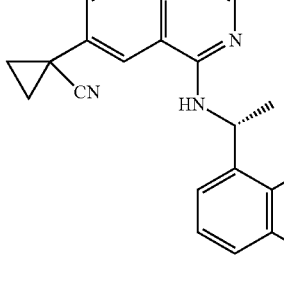

1245
-continued
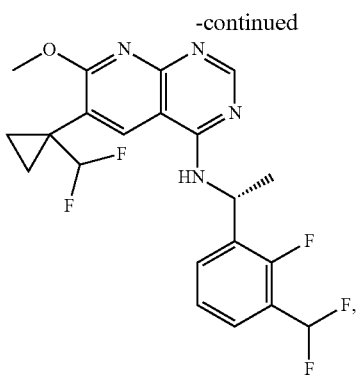
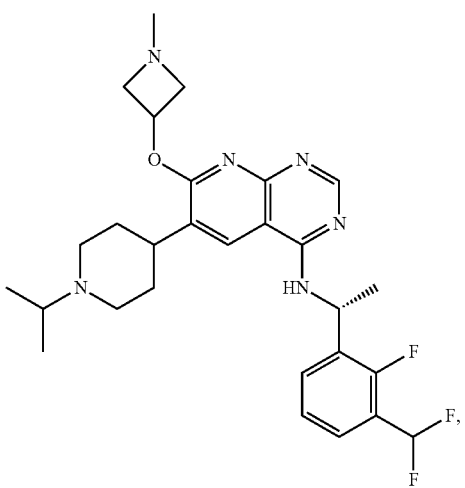
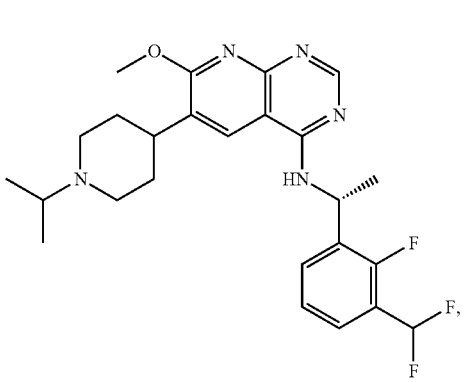
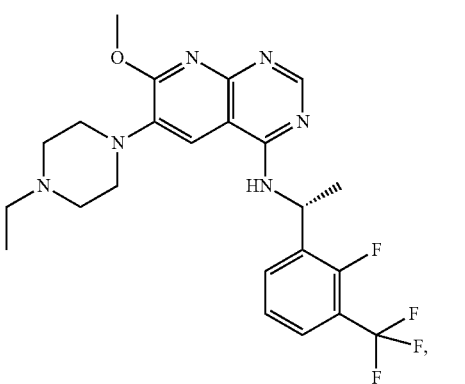
1246
-continued
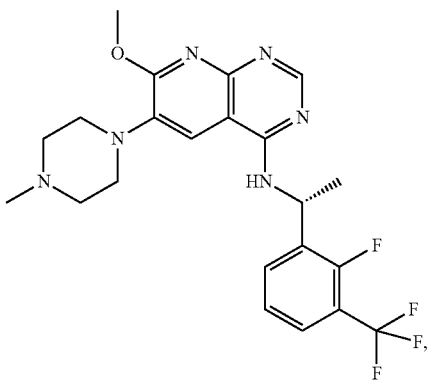
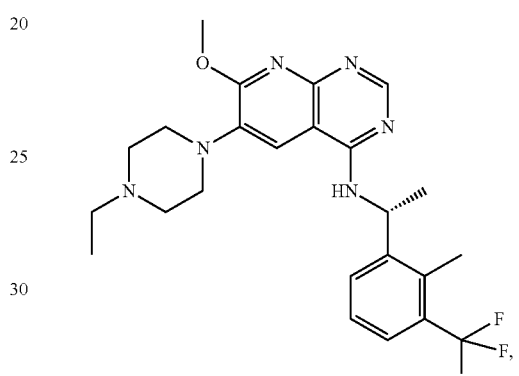
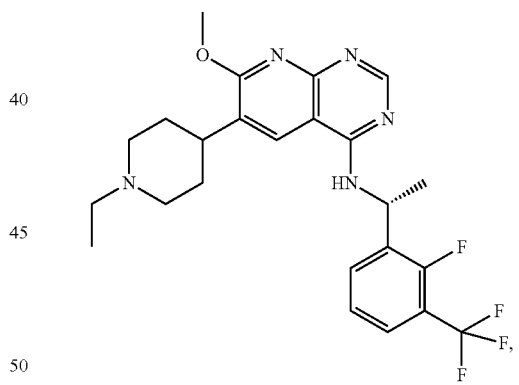
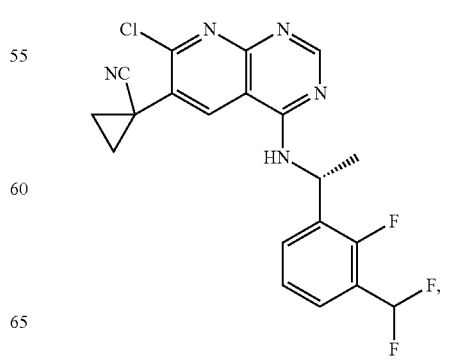

1247
-continued
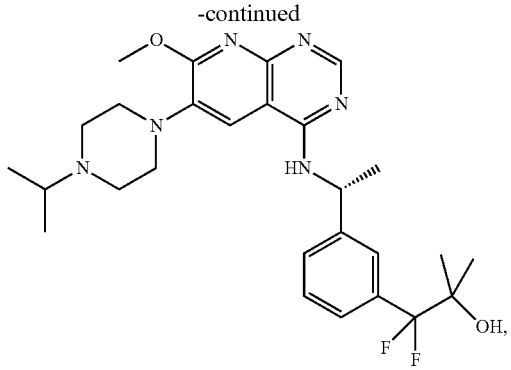
1248
-continued
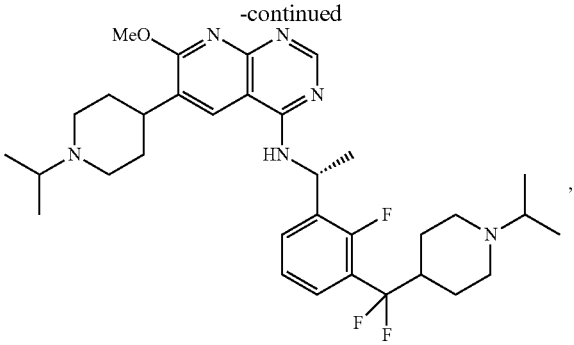
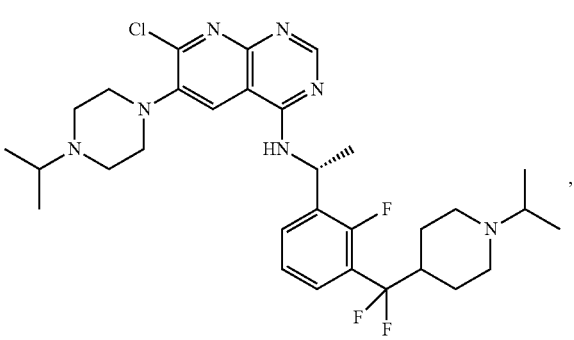
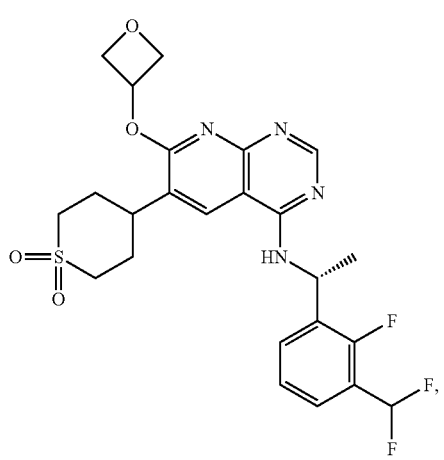
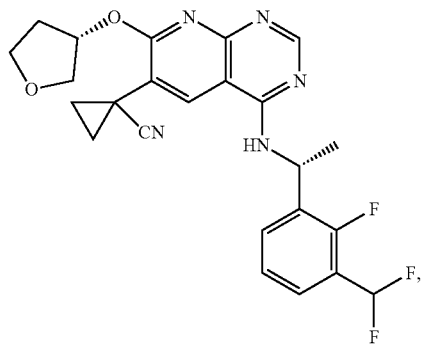

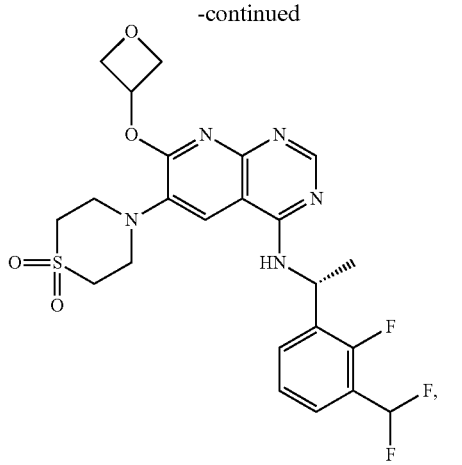
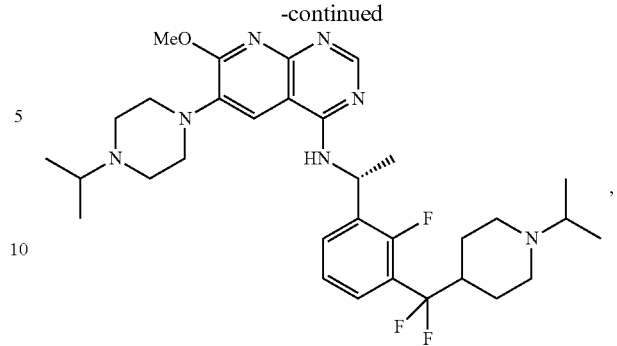
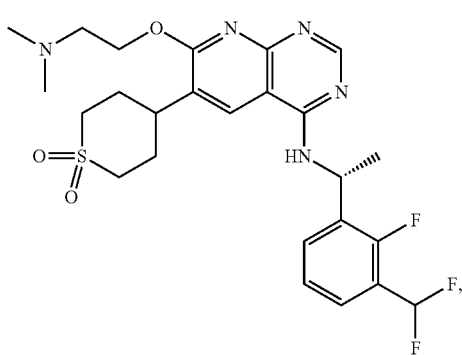
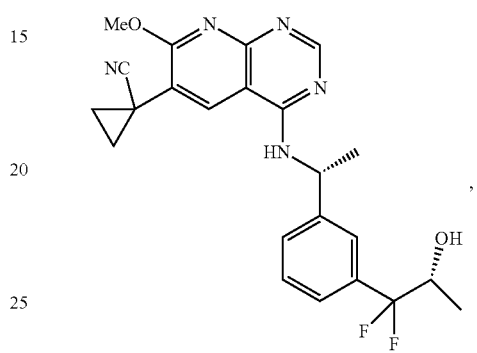
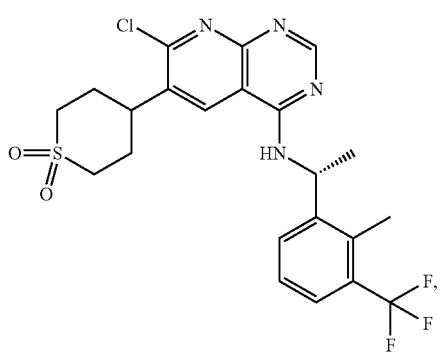
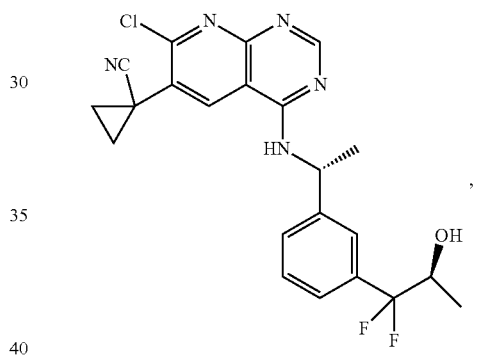
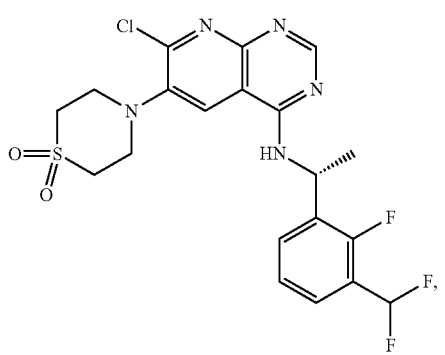
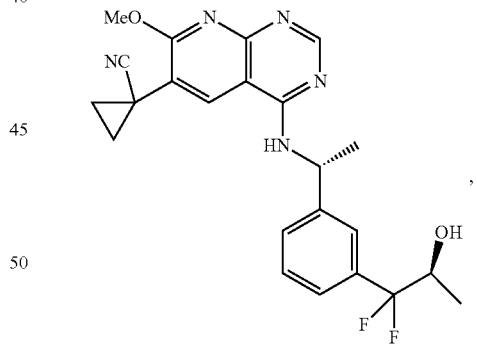
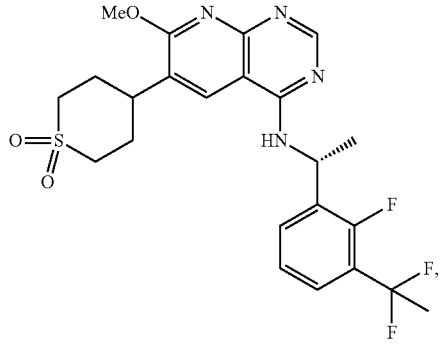

1251
-continued
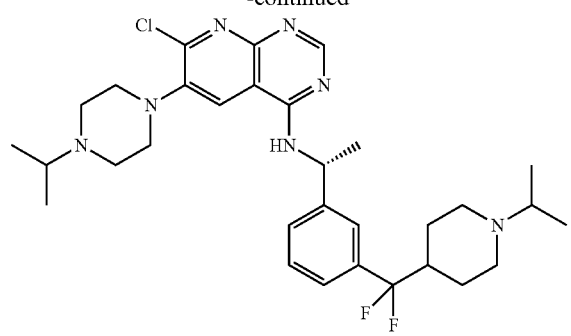
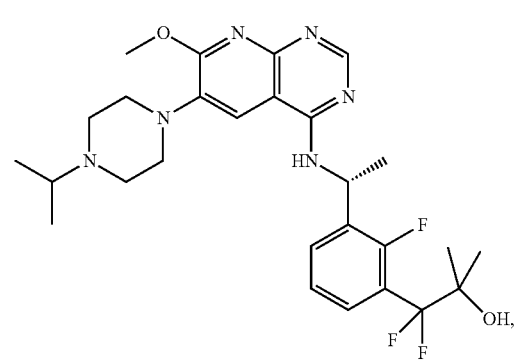
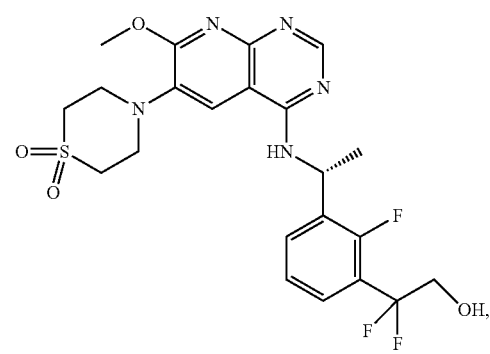
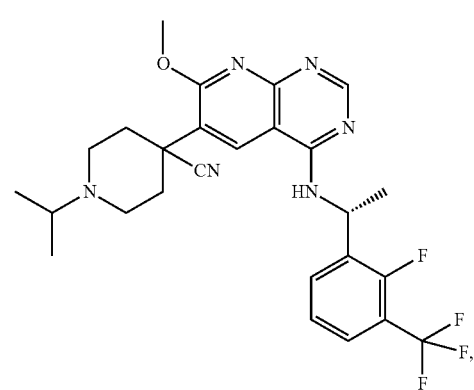
1252
-continued
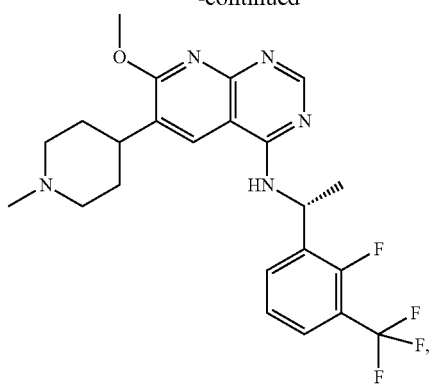
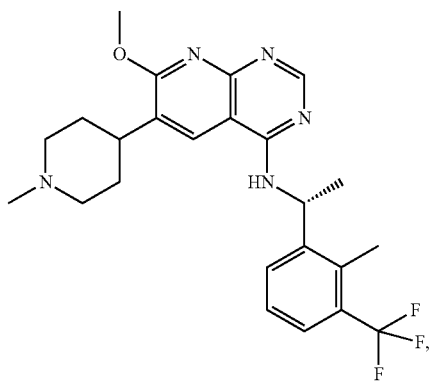
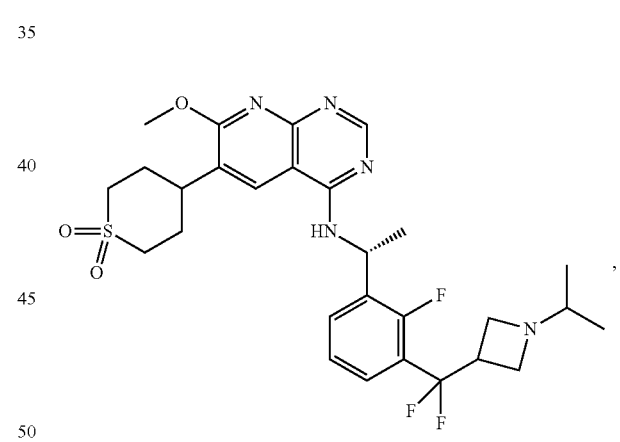
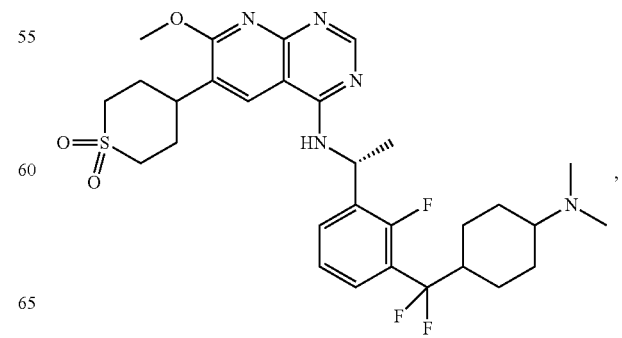

1253
-continued
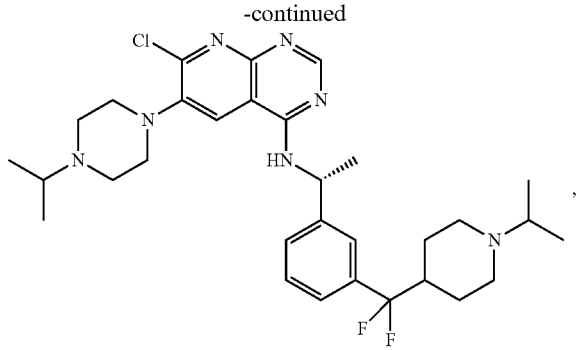
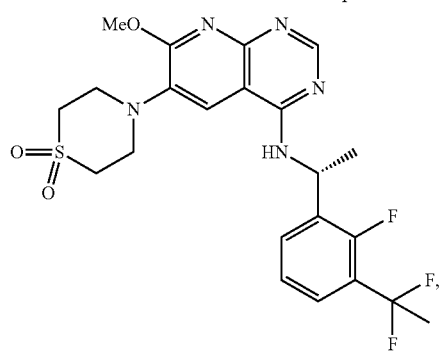
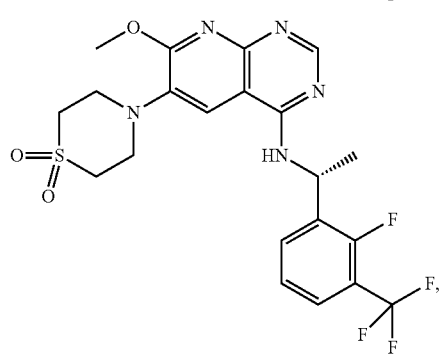
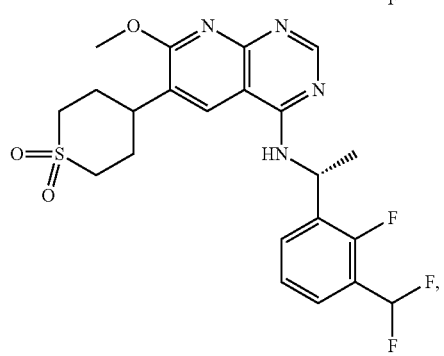
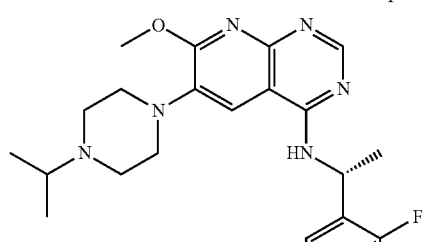
1254
-continued
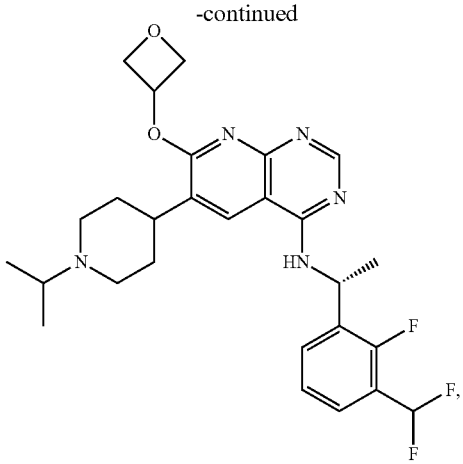
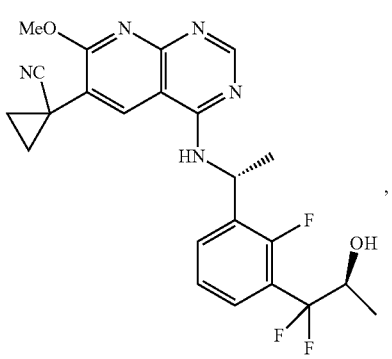
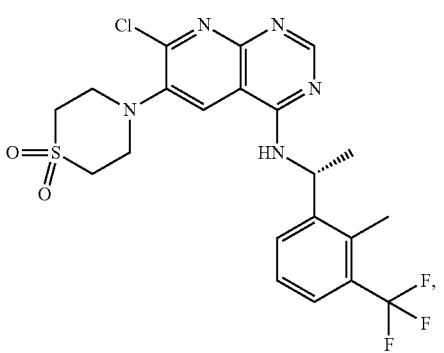
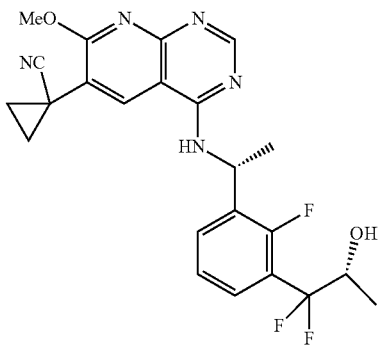

1255
-continued
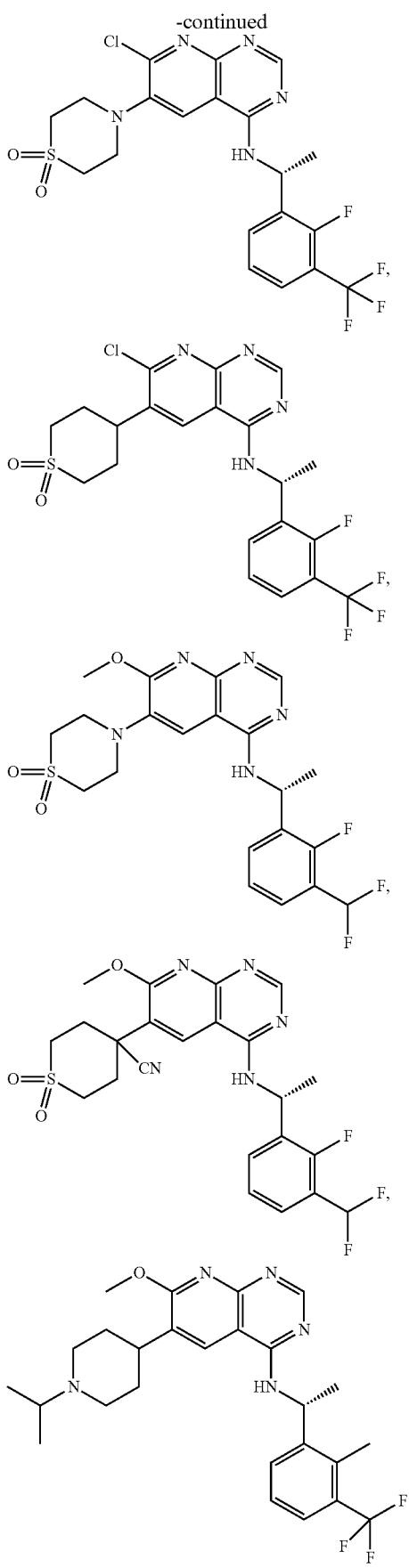
1256
-continued
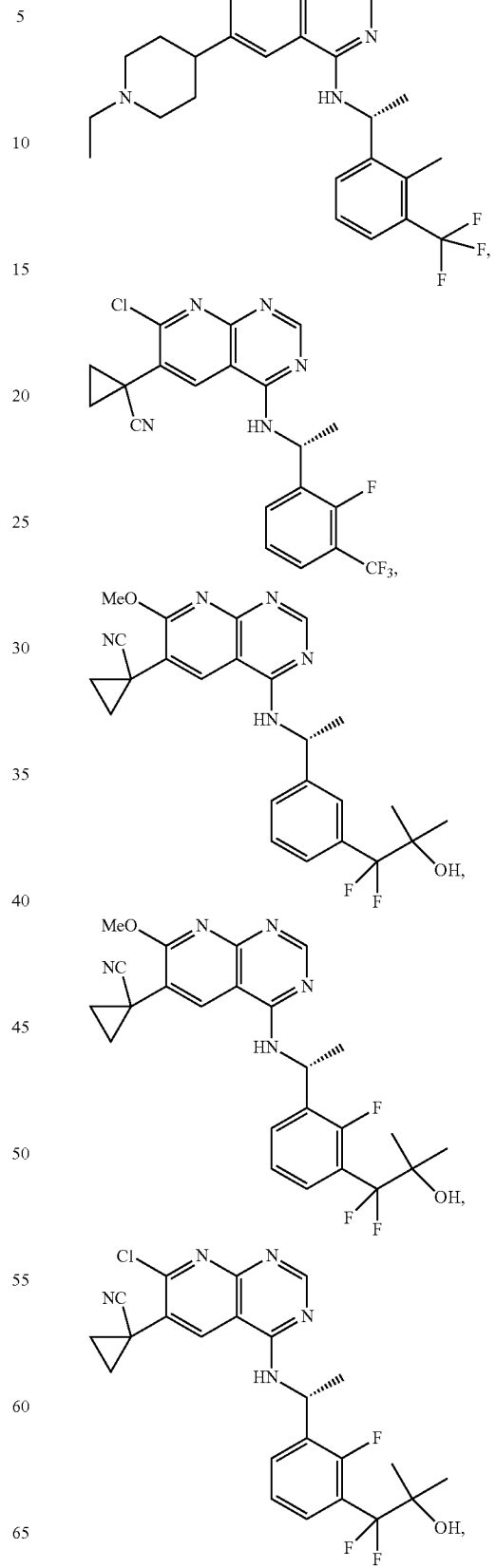

1257
-continued
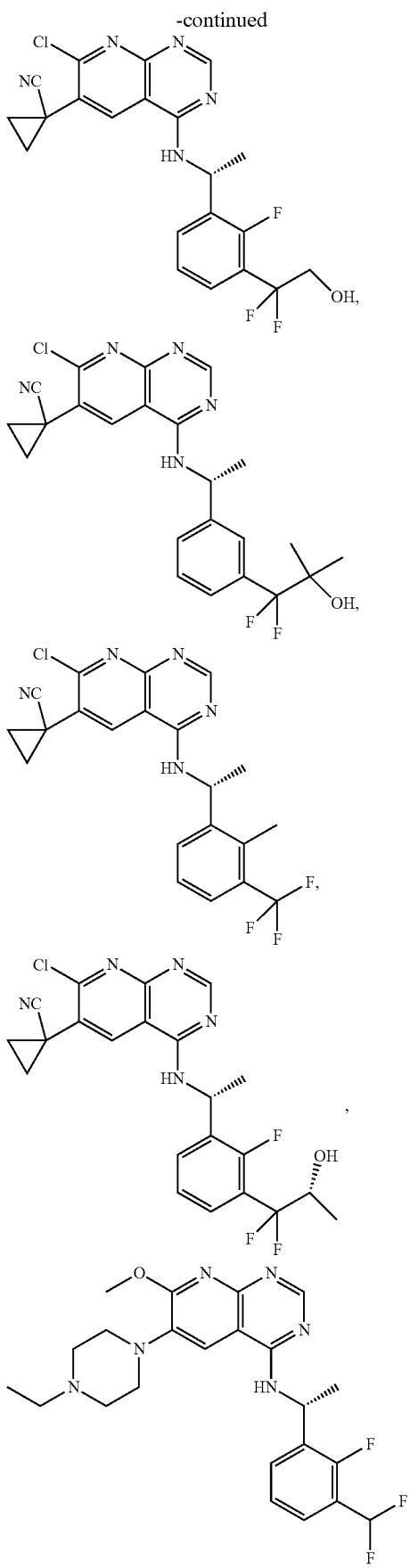
1258
-continued
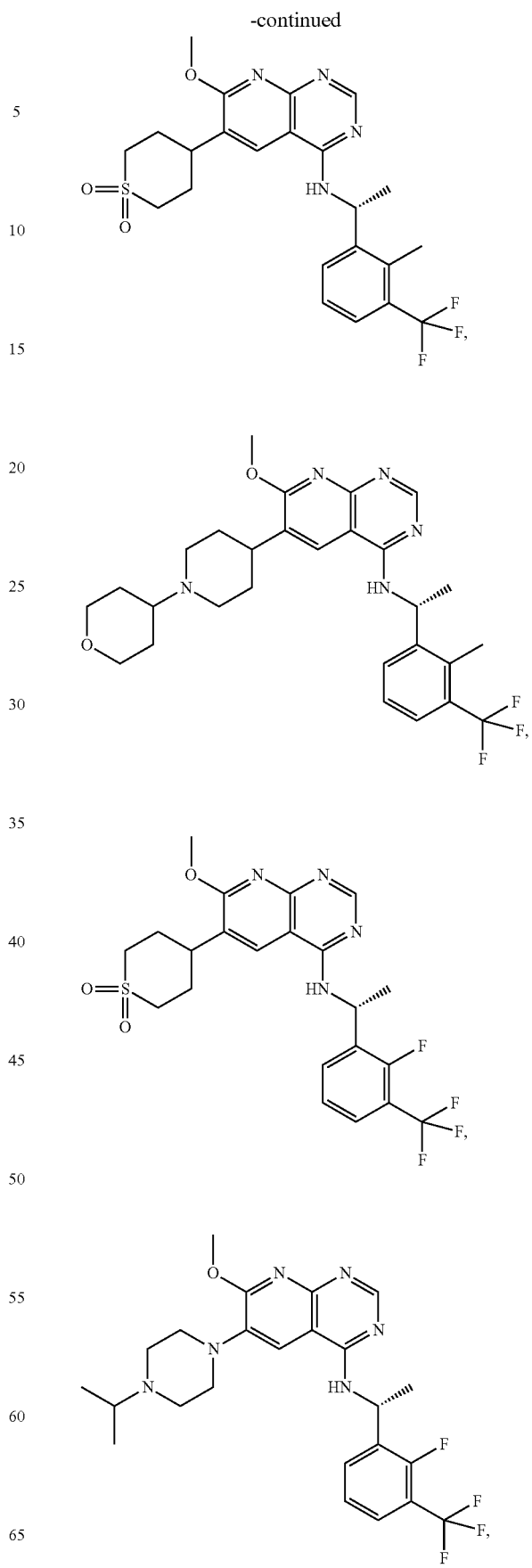

-continued
1259
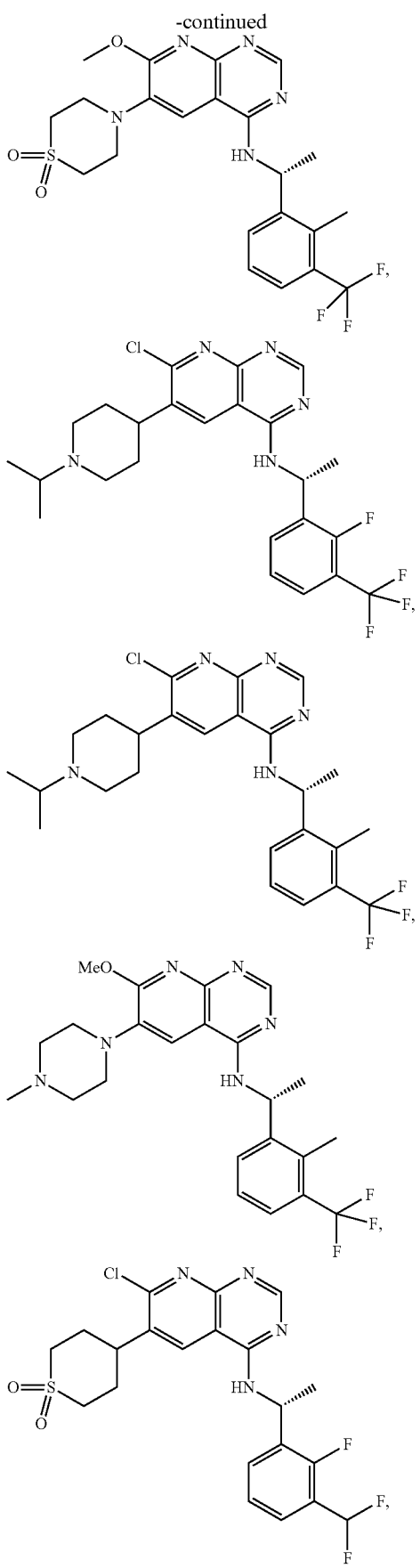
1260
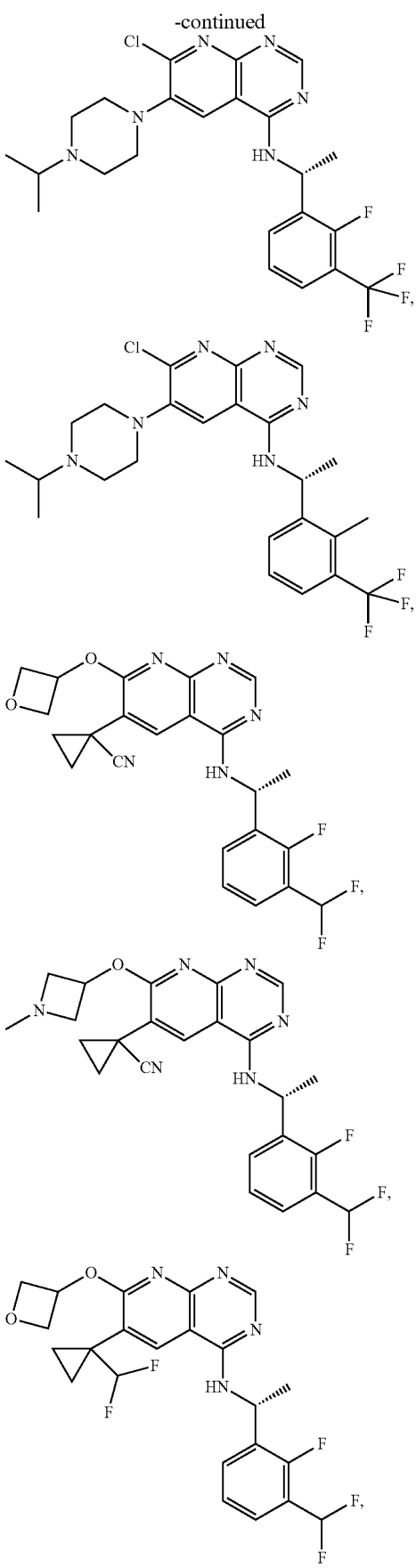

1261
-continued

1262
-continued or a pharmaceutically acceptable salt or stereoisomer thereof.

* * * * *

UNITED STATES PATENT AND TRADEMARK OFFICE
CERTIFICATE OF CORRECTION

PATENT NO. : 11,648,254 B2
APPLICATION NO. : 17/685370
DATED : May 16, 2023
INVENTOR(S) : Wu et al.

It is certified that error appears in the above-identified patent and that said Letters Patent is hereby corrected as shown below:

On the Title Page

Title, Item (54) and in the Specification, Column 1, Line 1, delete "SUBSTITUTED PYRIDO[2,3-D]PYRIMIDINES AS INHIBITORS OF RAS PATHWAY SIGNALING" and insert
-- SUBSTITUTED PYRIDO[2,3-d]PYRIMIDINES AS INHIBITORS OF RAS PATHWAY SIGNALING --.

In the Claims

Claim 1, Column 1237, Line 46, delete "$C_{3-10}$ cycloalkyl," and insert -- $C_{3-14}$ cycloalkyl, --.

Claim 1, Column 1237, Line 62, delete "$CH_2Cl_{3-10}$ cycloalkyl, $CH_2Cl_{2-9}$ heterocycloalkyl," and insert -- $CH_2C_{3-10}$ cycloalkyl, $CH_2C_{2-9}$ heterocycloalkyl, --.

Claim 1, Column 1238, Line 40, delete "each $R^{20e}$" and insert -- each $R^{20b}$ --.

Claim 1, Column 1239, Line 3, delete "each $R^{20e}$" and insert -- each $R^{20c}$ --.

Claim 1, Column 1239, Line 4, delete "$CH_2Cl_{3-10}$ cycloalkyl, $CH_2Cl_{2-9}$ heterocycloalkyl," and insert -- $CH_2C_{3-10}$ cycloalkyl, $CH_2C_{2-9}$ heterocycloalkyl, --.

Claim 1, Column 1239, Line 34, delete "$CH_2Cl_{3-10}$ cycloalkyl, $CH_2Cl_{2-9}$ heterocycloalkyl," and insert -- $CH_2C_{3-10}$ cycloalkyl, $CH_2C_{2-9}$ heterocycloalkyl, --.

Claim 1, Column 1239, Line 41, delete "Chao aryl," and insert -- $C_{6-10}$ aryl, --.

Claim 3, Column 1240, Line 30, delete "$R^{20d}$." and insert -- $R^{20d}$ substituents. --.

Claim 10, Column 1241, Line 50, delete "$R^{20e}$ substituents." and insert -- $R^{20a}$ substituents. --.

Signed and Sealed this
Eighth Day of August, 2023

Katherine Kelly Vidal
*Director of the United States Patent and Trademark Office*

Claim 13, Column 1241, Line 57, delete "solvate stereoisomer" and insert -- stereoisomer --.
Claim 30, Column 1251, Line 5, delete " 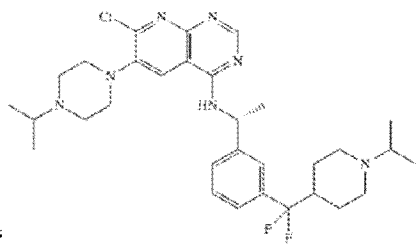 " and insert
-- 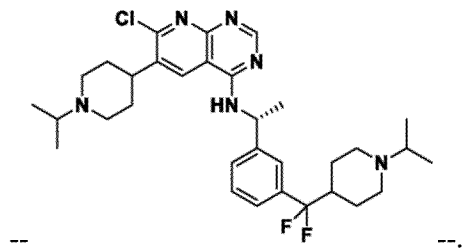 --.
Claim 30, Column 1258, Line 60, delete " 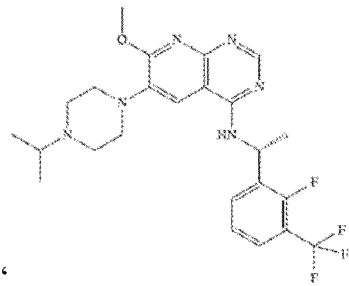 " and insert
-- 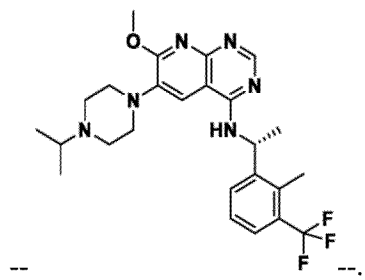 --.

SEQUENCE LISTING

```
<160> NUMBER OF SEQ ID NOS: 6

<210> SEQ ID NO 1
<211> LENGTH: 188
<212> TYPE: PRT
<213> ORGANISM: Homo sapiens

<400> SEQUENCE: 1

Met Thr Glu Tyr Lys Leu Val Val Gly Ala Gly Gly Val Gly Lys
1               5                   10                  15

Ser Ala Leu Thr Ile Gln Leu Ile Gln Asn His Phe Val Asp Glu Tyr
            20                  25                  30

Asp Pro Thr Ile Glu Asp Ser Tyr Arg Lys Gln Val Val Ile Asp Gly
        35                  40                  45

Glu Thr Cys Leu Leu Asp Ile Leu Asp Thr Ala Gly Gln Glu Glu Tyr
    50                  55                  60

Ser Ala Met Arg Asp Gln Tyr Met Arg Thr Gly Glu Gly Phe Leu Cys
65                  70                  75                  80

Val Phe Ala Ile Asn Asn Thr Lys Ser Phe Glu Asp Ile His His Tyr
                85                  90                  95

Arg Glu Gln Ile Lys Arg Val Lys Asp Ser Glu Asp Val Pro Met Val
            100                 105                 110

Leu Val Gly Asn Lys Cys Asp Leu Pro Ser Arg Thr Val Asp Thr Lys
        115                 120                 125

Gln Ala Gln Asp Leu Ala Arg Ser Tyr Gly Ile Pro Phe Ile Glu Thr
    130                 135                 140

Ser Ala Lys Thr Arg Gln Gly Val Asp Asp Ala Phe Tyr Thr Leu Val
145                 150                 155                 160

Arg Glu Ile Arg Lys His Lys Glu Lys Met Ser Lys Asp Gly Lys Lys
                165                 170                 175

Lys Lys Lys Lys Ser Lys Thr Lys Cys Val Ile Met
```

<210> SEQ ID NO 2

<400> SEQUENCE: 2

000

<210> SEQ ID NO 3
<211> LENGTH: 1333
<212> TYPE: PRT
<213> ORGANISM: Homo sapiens

<400> SEQUENCE: 3

```
Met Gln Ala Gln Gln Leu Pro Tyr Glu Phe Ser Glu Glu Asn Ala
1               5                   10                  15

Pro Lys Trp Arg Gly Leu Leu Val Pro Ala Leu Lys Lys Val Gln Gly
            20                  25                  30

Gln Val His Pro Thr Leu Glu Ser Asn Asp Asp Ala Leu Gln Tyr Val
                35                  40                  45

Glu Glu Leu Ile Leu Gln Leu Leu Asn Met Leu Cys Gln Ala Gln Pro
50                  55                  60

Arg Ser Ala Ser Asp Val Glu Glu Arg Val Gln Lys Ser Phe Pro His
65                  70                  75                  80

Pro Ile Asp Lys Trp Ala Ile Ala Asp Ala Gln Ser Ala Ile Glu Lys
                85                  90                  95

Arg Lys Arg Arg Asn Pro Leu Ser Leu Pro Val Glu Lys Ile His Pro
            100                 105                 110

Leu Leu Lys Glu Val Leu Gly Tyr Lys Ile Asp His Gln Val Ser Val
        115                 120                 125

Tyr Ile Val Ala Val Leu Glu Tyr Ile Ser Ala Asp Ile Leu Lys Leu
    130                 135                 140

Val Gly Asn Tyr Val Arg Asn Ile Arg His Tyr Glu Ile Thr Lys Gln
145                 150                 155                 160

Asp Ile Lys Val Ala Met Cys Ala Asp Lys Val Leu Met Asp Met Phe
                165                 170                 175

His Gln Asp Val Glu Asp Ile Asn Ile Leu Ser Leu Thr Asp Glu Glu
            180                 185                 190

Pro Ser Thr Ser Gly Glu Gln Thr Tyr Tyr Asp Leu Val Lys Ala Phe
        195                 200                 205

Met Ala Glu Ile Arg Gln Tyr Ile Arg Glu Leu Asn Leu Ile Ile Lys
    210                 215                 220

Val Phe Arg Glu Pro Phe Val Ser Asn Ser Lys Leu Phe Ser Ala Asn
225                 230                 235                 240

Asp Val Glu Asn Ile Phe Ser Arg Ile Val Asp Ile His Glu Leu Ser
                245                 250                 255

Val Lys Leu Leu Gly His Ile Glu Asp Thr Val Glu Met Thr Asp Glu
            260                 265                 270

Gly Ser Pro His Pro Leu Val Gly Ser Cys Phe Glu Asp Leu Ala Glu
        275                 280                 285

Glu Leu Ala Phe Asp Pro Tyr Glu Ser Tyr Ala Arg Asp Ile Leu Arg
    290                 295                 300

Pro Gly Phe His Asp Arg Phe Leu Ser Gln Leu Ser Lys Pro Gly Ala
305                 310                 315                 320

Ala Leu Tyr Leu Gln Ser Ile Gly Glu Gly Phe Lys Glu Ala Val Gln
                325                 330                 335
```

```
Tyr Val Leu Pro Arg Leu Leu Ala Pro Val Tyr His Cys Leu His
                340                 345                 350

Tyr Phe Glu Leu Leu Lys Gln Leu Glu Lys Ser Glu Asp Gln Glu
                355                 360                 365

Asp Lys Glu Cys Leu Lys Gln Ala Ile Thr Ala Leu Leu Asn Val Gln
370                 375                 380

Ser Gly Met Glu Lys Ile Cys Ser Lys Ser Leu Ala Lys Arg Leu
385                 390                 395                 400

Ser Glu Ser Ala Cys Arg Phe Tyr Ser Gln Gln Met Lys Gly Lys Gln
                405                 410                 415

Leu Ala Ile Lys Lys Met Asn Glu Ile Gln Lys Asn Ile Asp Gly Trp
                420                 425                 430

Glu Gly Lys Asp Ile Gly Gln Cys Cys Asn Glu Phe Ile Met Glu Gly
                435                 440                 445

Thr Leu Thr Arg Val Gly Ala Lys His Glu Arg His Ile Phe Leu Phe
                450                 455                 460

Asp Gly Leu Met Ile Cys Cys Lys Ser Asn His Gly Gln Pro Arg Leu
465                 470                 475                 480

Pro Gly Ala Ser Asn Ala Glu Tyr Arg Leu Lys Glu Lys Phe Phe Met
                485                 490                 495

Arg Lys Val Gln Ile Asn Asp Lys Asp Thr Asn Glu Tyr Lys His
                500                 505                 510

Ala Phe Glu Ile Ile Leu Lys Asp Glu Asn Ser Val Ile Phe Ser Ala
                515                 520                 525

Lys Ser Ala Glu Glu Lys Asn Asn Trp Met Ala Ala Leu Ile Ser Leu
                530                 535                 540

Gln Tyr Arg Ser Thr Leu Glu Arg Met Leu Asp Val Thr Met Leu Gln
545                 550                 555                 560

Glu Glu Lys Glu Glu Gln Met Arg Leu Pro Ser Ala Asp Val Tyr Arg
                565                 570                 575

Phe Ala Glu Pro Asp Ser Glu Glu Asn Ile Ile Phe Glu Glu Asn Met
                580                 585                 590

Gln Pro Lys Ala Gly Ile Pro Ile Ile Lys Ala Gly Thr Val Ile Lys
                595                 600                 605

Leu Ile Glu Arg Leu Thr Tyr His Met Tyr Ala Asp Pro Asn Phe Val
                610                 615                 620

Arg Thr Phe Leu Thr Thr Tyr Arg Ser Phe Cys Lys Pro Gln Glu Leu
625                 630                 635                 640

Leu Ser Leu Ile Ile Glu Arg Phe Glu Ile Pro Glu Pro Glu Pro Thr
                645                 650                 655

Glu Ala Asp Arg Ile Ala Ile Glu Asn Gly Asp Gln Pro Leu Ser Ala
                660                 665                 670

Glu Leu Lys Arg Phe Arg Lys Glu Tyr Ile Gln Pro Val Gln Leu Arg
                675                 680                 685

Val Leu Asn Val Cys Arg His Trp Val Glu His His Phe Tyr Asp Phe
                690                 695                 700

Glu Arg Asp Ala Tyr Leu Leu Gln Arg Met Glu Glu Phe Ile Gly Thr
705                 710                 715                 720

Val Arg Gly Lys Ala Met Lys Lys Trp Val Glu Ser Ile Thr Lys Ile
                725                 730                 735

Ile Gln Arg Lys Lys Ile Ala Arg Asp Asn Gly Pro Gly His Asn Ile
                740                 745                 750
```

```
Thr Phe Gln Ser Ser Pro Pro Thr Val Glu Trp His Ile Ser Arg Pro
            755                 760                 765

Gly His Ile Glu Thr Phe Asp Leu Leu Thr Leu His Pro Ile Glu Ile
    770                 775                 780

Ala Arg Gln Leu Thr Leu Leu Glu Ser Asp Leu Tyr Arg Ala Val Gln
785                 790                 795                 800

Pro Ser Glu Leu Val Gly Ser Val Trp Thr Lys Glu Asp Lys Glu Ile
                805                 810                 815

Asn Ser Pro Asn Leu Leu Lys Met Ile Arg His Thr Thr Asn Leu Thr
            820                 825                 830

Leu Trp Phe Glu Lys Cys Ile Val Glu Thr Glu Asn Leu Glu Glu Arg
        835                 840                 845

Val Ala Val Val Ser Arg Ile Ile Glu Ile Leu Gln Val Phe Gln Glu
850                 855                 860

Leu Asn Asn Phe Asn Gly Val Leu Glu Val Val Ser Ala Met Asn Ser
865                 870                 875                 880

Ser Pro Val Tyr Arg Leu Asp His Thr Phe Glu Gln Ile Pro Ser Arg
                885                 890                 895

Gln Lys Lys Ile Leu Glu Glu Ala His Glu Leu Ser Glu Asp His Tyr
            900                 905                 910

Lys Lys Tyr Leu Ala Lys Leu Arg Ser Ile Asn Pro Pro Cys Val Pro
        915                 920                 925

Phe Phe Gly Ile Tyr Leu Thr Asn Ile Leu Lys Thr Glu Glu Gly Asn
        930                 935                 940

Pro Glu Val Leu Lys Arg His Gly Lys Glu Leu Ile Asn Phe Ser Lys
945                 950                 955                 960

Arg Arg Lys Val Ala Glu Ile Thr Gly Glu Ile Gln Gln Tyr Gln Asn
                965                 970                 975

Gln Pro Tyr Cys Leu Arg Val Glu Ser Asp Ile Lys Arg Phe Phe Glu
            980                 985                 990

Asn Leu Asn Pro Met Gly Asn Ser Met Glu Lys Glu Phe Thr Asp Tyr
        995                 1000                1005

Leu Phe Asn Lys Ser Leu Glu Ile Glu Pro Arg Asn Pro Lys Pro
    1010                1015                1020

Leu Pro Arg Phe Pro Lys Lys Tyr Ser Tyr Pro Leu Lys Ser Pro
    1025                1030                1035

Gly Val Arg Pro Ser Asn Pro Arg Pro Gly Thr Met Arg His Pro
    1040                1045                1050

Thr Pro Leu Gln Gln Glu Pro Arg Lys Ile Ser Tyr Ser Arg Ile
    1055                1060                1065

Pro Glu Ser Glu Thr Glu Ser Thr Ala Ser Ala Pro Asn Ser Pro
    1070                1075                1080

Arg Thr Pro Leu Thr Pro Pro Ala Ser Gly Ala Ser Ser Thr
    1085                1090                1095

Thr Asp Val Cys Ser Val Phe Asp Ser Asp His Ser Ser Pro Phe
    1100                1105                1110

His Ser Ser Asn Asp Thr Val Phe Ile Gln Val Thr Leu Pro His
    1115                1120                1125

Gly Pro Arg Ser Ala Ser Val Ser Ser Ile Ser Leu Thr Lys Gly
    1130                1135                1140

Thr Asp Glu Val Pro Val Pro Pro Val Pro Pro Arg Arg Arg
    1145                1150                1155

Pro Glu Ser Ala Pro Ala Glu Ser Ser Pro Ser Lys Ile Met Ser
```

```
            1160                1165                1170

Lys His Leu Asp Ser Pro Pro Ala Ile Pro Pro Arg Gln Pro Thr
    1175                1180                1185

Ser Lys Ala Tyr Ser Pro Arg Tyr Ser Ile Ser Asp Arg Thr Ser
    1190                1195                1200

Ile Ser Asp Pro Pro Glu Ser Pro Pro Leu Leu Pro Pro Arg Glu
    1205                1210                1215

Pro Val Arg Thr Pro Asp Val Phe Ser Ser Pro Leu His Leu
    1220                1225                1230

Gln Pro Pro Pro Leu Gly Lys Lys Ser Asp His Gly Asn Ala Phe
    1235                1240                1245

Phe Pro Asn Ser Pro Ser Pro Phe Thr Pro Pro Pro Gln Thr
    1250                1255                1260

Pro Ser Pro His Gly Thr Arg Arg His Leu Pro Ser Pro Pro Leu
    1265                1270                1275

Thr Gln Glu Val Asp Leu His Ser Ile Ala Gly Pro Pro Val Pro
    1280                1285                1290

Pro Arg Gln Ser Thr Ser Gln His Ile Pro Lys Leu Pro Pro Lys
    1295                1300                1305

Thr Tyr Lys Arg Glu His Thr His Pro Ser Met His Arg Asp Gly
    1310                1315                1320

Pro Pro Leu Leu Glu Asn Ala His Ser Ser
    1325                1330

<210> SEQ ID NO 4

<400> SEQUENCE: 4

000

<210> SEQ ID NO 5
<211> LENGTH: 1332
<212> TYPE: PRT
<213> ORGANISM: Homo sapiens

<400> SEQUENCE: 5

Met Gln Gln Ala Pro Gln Pro Tyr Glu Phe Phe Ser Glu Glu Asn Ser
1               5                   10                  15

Pro Lys Trp Arg Gly Leu Leu Val Ser Ala Leu Arg Lys Val Gln Glu
            20                  25                  30

Gln Val His Pro Thr Leu Ser Ala Asn Glu Glu Ser Leu Tyr Tyr Ile
        35                  40                  45

Glu Glu Leu Ile Phe Gln Leu Leu Asn Lys Leu Cys Met Ala Gln Pro
    50                  55                  60

Arg Thr Val Gln Asp Val Glu Glu Arg Val Gln Lys Thr Phe Pro His
65                  70                  75                  80

Pro Ile Asp Lys Trp Ala Ile Ala Asp Ala Gln Ser Ala Ile Glu Lys
                85                  90                  95

Arg Lys Arg Arg Asn Pro Leu Leu Leu Pro Val Asp Lys Ile His Pro
            100                 105                 110

Ser Leu Lys Glu Val Leu Gly Tyr Lys Val Asp Tyr His Val Ser Leu
        115                 120                 125

Tyr Ile Val Ala Val Leu Glu Tyr Ile Ser Ala Asp Ile Leu Lys Leu
    130                 135                 140

Ala Gly Asn Tyr Val Phe Asn Ile Arg His Tyr Glu Ile Ser Gln Gln
145                 150                 155                 160
```

```
Asp Ile Lys Val Ser Met Cys Ala Asp Lys Val Leu Met Asp Met Phe
                165                 170                 175

Asp Gln Asp Asp Ile Gly Leu Val Ser Leu Cys Glu Asp Glu Pro Ser
            180                 185                 190

Ser Ser Gly Glu Leu Asn Tyr Tyr Asp Leu Val Arg Thr Glu Ile Ala
        195                 200                 205

Glu Glu Arg Gln Tyr Leu Arg Glu Leu Asn Met Ile Ile Lys Val Phe
    210                 215                 220

Arg Glu Ala Phe Leu Ser Asp Arg Lys Leu Phe Lys Pro Ser Asp Ile
225                 230                 235                 240

Glu Lys Ile Phe Ser Asn Ile Ser Asp Ile His Glu Leu Thr Val Lys
                245                 250                 255

Leu Leu Gly Leu Ile Glu Asp Thr Val Glu Met Thr Asp Glu Ser Ser
            260                 265                 270

Pro His Pro Leu Ala Gly Ser Cys Phe Glu Asp Leu Ala Glu Glu Gln
        275                 280                 285

Ala Phe Asp Pro Tyr Glu Thr Leu Ser Gln Asp Ile Leu Ser Pro Glu
    290                 295                 300

Phe His Glu His Phe Asn Lys Leu Met Ala Arg Pro Ala Val Ala Leu
305                 310                 315                 320

His Phe Gln Ser Ile Ala Asp Gly Phe Lys Glu Ala Val Arg Tyr Val
                325                 330                 335

Leu Pro Arg Leu Met Leu Val Pro Val Tyr His Cys Trp His Tyr Phe
            340                 345                 350

Glu Leu Leu Lys Gln Leu Lys Ala Cys Ser Glu Gln Glu Asp Arg
        355                 360                 365

Glu Cys Leu Asn Gln Ala Ile Thr Ala Leu Met Asn Leu Gln Gly Ser
    370                 375                 380

Met Asp Arg Ile Tyr Lys Gln Tyr Ser Pro Arg Arg Pro Gly Asp
385                 390                 395                 400

Pro Val Cys Pro Phe Tyr Ser His Gln Leu Arg Ser Lys His Leu Ala
                405                 410                 415

Ile Lys Lys Met Asn Glu Ile Gln Lys Asn Ile Asp Gly Trp Glu Gly
            420                 425                 430

Lys Asp Ile Gly Gln Cys Cys Asn Glu Phe Ile Met Glu Gly Pro Leu
        435                 440                 445

Thr Arg Ile Gly Ala Lys His Glu Arg His Ile Phe Leu Phe Asp Gly
    450                 455                 460

Leu Met Ile Ser Cys Lys Pro Asn His Gly Gln Thr Arg Leu Pro Gly
465                 470                 475                 480

Tyr Ser Ser Ala Glu Tyr Arg Leu Lys Glu Lys Phe Val Met Arg Lys
                485                 490                 495

Ile Gln Ile Cys Asp Lys Glu Asp Thr Cys Glu His Lys His Ala Phe
            500                 505                 510

Glu Leu Val Ser Lys Asp Glu Asn Ser Ile Ile Phe Ala Ala Lys Ser
        515                 520                 525

Ala Glu Glu Lys Asn Asn Trp Met Ala Ala Leu Ile Ser Leu His Tyr
    530                 535                 540

Arg Ser Thr Leu Asp Arg Met Leu Asp Ser Val Leu Leu Lys Glu Glu
545                 550                 555                 560

Asn Glu Gln Pro Leu Arg Leu Pro Ser Pro Glu Val Tyr Arg Phe Val
                565                 570                 575
```

Val Lys Asp Ser Glu Glu Asn Ile Val Phe Glu Asp Asn Leu Gln Ser
            580                 585                 590

Arg Ser Gly Ile Pro Ile Ile Lys Gly Gly Thr Val Val Lys Leu Ile
        595                 600                 605

Glu Arg Leu Thr Tyr His Met Tyr Ala Asp Pro Asn Phe Val Arg Thr
    610                 615                 620

Phe Leu Thr Thr Tyr Arg Ser Phe Cys Lys Pro Gln Glu Leu Leu Ser
625                 630                 635                 640

Leu Leu Ile Glu Arg Phe Glu Ile Pro Glu Pro Glu Pro Thr Asp Ala
                645                 650                 655

Asp Lys Leu Ala Ile Glu Lys Gly Glu Gln Pro Ile Ser Ala Asp Leu
            660                 665                 670

Lys Arg Phe Arg Lys Glu Tyr Val Gln Pro Val Gln Leu Arg Ile Leu
        675                 680                 685

Asn Val Phe Arg His Trp Val Glu His His Phe Tyr Asp Phe Glu Arg
    690                 695                 700

Asp Leu Glu Leu Glu Arg Leu Glu Ser Phe Ile Ser Ser Val Arg
705                 710                 715                 720

Gly Lys Ala Met Lys Lys Trp Val Glu Ser Ile Ala Lys Ile Ile Arg
                725                 730                 735

Arg Lys Lys Gln Ala Gln Ala Asn Gly Val Ser His Asn Ile Thr Phe
            740                 745                 750

Glu Ser Pro Pro Pro Ile Glu Trp His Ile Ser Lys Pro Gly Gln
        755                 760                 765

Phe Glu Thr Phe Asp Leu Met Thr Leu His Pro Ile Glu Ile Ala Arg
770                 775                 780

Gln Leu Thr Leu Leu Glu Ser Asp Leu Tyr Arg Lys Val Gln Pro Ser
785                 790                 795                 800

Glu Leu Val Gly Ser Val Trp Thr Lys Glu Asp Lys Glu Ile Asn Ser
                805                 810                 815

Pro Asn Leu Leu Lys Met Ile Arg His Thr Thr Asn Leu Thr Leu Trp
            820                 825                 830

Phe Glu Lys Cys Ile Val Glu Ala Glu Asn Phe Glu Glu Arg Val Ala
        835                 840                 845

Val Leu Ser Arg Ile Ile Glu Ile Leu Gln Val Phe Gln Asp Leu Asn
850                 855                 860

Asn Phe Asn Gly Val Leu Glu Ile Val Ser Ala Val Asn Ser Val Ser
865                 870                 875                 880

Val Tyr Arg Leu Asp His Thr Phe Glu Ala Leu Gln Glu Arg Lys Arg
                885                 890                 895

Lys Ile Leu Asp Glu Ala Val Glu Leu Ser Gln Asp His Phe Lys Lys
            900                 905                 910

Tyr Leu Val Lys Leu Lys Ser Ile Asn Pro Pro Cys Val Pro Phe Phe
        915                 920                 925

Gly Ile Tyr Leu Thr Asn Ile Leu Lys Thr Glu Glu Gly Asn Asn Asp
930                 935                 940

Phe Leu Lys Lys Lys Gly Lys Asp Leu Ile Asn Phe Ser Lys Arg Arg
945                 950                 955                 960

Lys Val Ala Glu Ile Thr Gly Glu Ile Gln Gln Tyr Gln Asn Gln Pro
                965                 970                 975

Tyr Cys Leu Arg Ile Glu Pro Asp Met Arg Arg Phe Phe Glu Asn Leu
            980                 985                 990

Asn Pro Met Gly Ser Ala Ser Glu  Lys Glu Phe Thr Asp  Tyr Leu Phe

-continued

```
              995                 1000                1005

Asn Lys Ser Leu Glu Ile Glu Pro Arg Asn Cys Lys Gln Pro Pro
        1010                1015                1020

Arg Phe Pro Arg Lys Ser Thr Phe Ser Leu Lys Ser Pro Gly Ile
        1025                1030                1035

Arg Pro Asn Thr Gly Arg His Gly Ser Thr Ser Gly Thr Leu Arg
        1040                1045                1050

Gly His Pro Thr Pro Leu Glu Arg Glu Pro Cys Lys Ile Ser Phe
        1055                1060                1065

Ser Arg Ile Ala Glu Thr Glu Leu Glu Ser Thr Val Ser Ala Pro
        1070                1075                1080

Thr Ser Pro Asn Thr Pro Ser Thr Pro Pro Val Ser Ala Ser Ser
        1085                1090                1095

Asp Leu Ser Val Phe Leu Asp Val Asp Leu Asn Ser Ser Cys Gly
        1100                1105                1110

Ser Asn Ser Ile Phe Ala Pro Val Leu Leu Pro His Ser Lys Ser
        1115                1120                1125

Phe Phe Ser Ser Cys Gly Ser Leu His Lys Leu Ser Glu Glu Pro
        1130                1135                1140

Leu Ile Pro Pro Pro Leu Pro Pro Arg Lys Lys Phe Asp His Asp
        1145                1150                1155

Ala Ser Asn Ser Lys Gly Asn Met Lys Ser Asp Asp Asp Pro Pro
        1160                1165                1170

Ala Ile Pro Pro Arg Gln Pro Pro Pro Lys Val Lys Pro Arg
        1175                1180                1185

Val Pro Val Pro Thr Gly Ala Phe Asp Gly Pro Leu His Ser Pro
        1190                1195                1200

Pro Pro Pro Pro Arg Asp Pro Leu Pro Asp Thr Pro Pro Pro
        1205                1210                1215

Val Pro Leu Arg Pro Pro Glu His Phe Ile Asn Cys Pro Phe Asn
        1220                1225                1230

Leu Gln Pro Pro Pro Leu Gly His Leu His Arg Asp Ser Asp Trp
        1235                1240                1245

Leu Arg Asp Ile Ser Thr Cys Pro Asn Ser Pro Ser Thr Pro Pro
        1250                1255                1260

Ser Thr Pro Ser Pro Arg Val Pro Arg Arg Cys Tyr Val Leu Ser
        1265                1270                1275

Ser Ser Gln Asn Asn Leu Ala His Pro Pro Ala Pro Pro Val Pro
        1280                1285                1290

Pro Arg Gln Asn Ser Ser Pro His Leu Pro Lys Leu Pro Pro Lys
        1295                1300                1305

Thr Tyr Lys Arg Glu Leu Ser His Pro Pro Leu Tyr Arg Leu Pro
        1310                1315                1320

Leu Leu Glu Asn Ala Glu Thr Pro Gln
        1325                1330
```

```
<210> SEQ ID NO 6
<211> LENGTH: 10
<212> TYPE: PRT
<213> ORGANISM: Artificial Sequence
<220> FEATURE:
<223> OTHER INFORMATION: Description of Artificial Sequence: Synthetic
      10xHis tag

<400> SEQUENCE: 6

His His His His His His His His His His
1               5                   10
```